(12) United States Patent
Tong et al.

(10) Patent No.: US 9,796,708 B2
(45) Date of Patent: Oct. 24, 2017

(54) PYRROLO [2,3-B] PYRIDINE CDK9 KINASE INHIBITORS

(71) Applicant: AbbVie Inc., North Chicago, IL (US)

(72) Inventors: Yunsong Tong, Libertyville, IL (US); Milan Bruncko, Green Oaks, IL (US); Richard F. Clark, Gurnee, IL (US); Michael Curtin, Pleasant Prairie, WI (US); Alan S. Florjancic, Kenosha, WI (US); Robin R. Frey, Libertyville, IL (US); Jianchun Gong, Deefield, IL (US); Todd M. Hansen, Grayslake, IL (US); Zhiqin Ji, Libertyville, IL (US); Chunqiu Lai, Libertyville, IL (US); Anthony Mastracchio, Vernon Hills, IL (US); Michael Michaelides, Libertyville, IL (US); Juliem Miyashiro, Morton Grove, IL (US); Roberto M. Risi, Kenosha, WI (US); Xiaohong Song, Grayslake, IL (US); Zhi-fu Tao, Vernon Hills, IL (US); Keith W. Woods, Lincolnshire, IL (US); Guidong Zhu, Gurnee, IL (US); Thomas Penning, Elmhurst, IL (US); Andrew Souers, Libertyville, IL (US); Rajeev Goswami, Dehradun (IN); Omprakash Reddy Iguturi, Guntur (IN); Madhu Babu Dabbeeru, Srikakulam (IN)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/780,018

(22) PCT Filed: Mar. 13, 2014

(86) PCT No.: PCT/CN2014/000265
§ 371 (c)(1),
(2) Date: Sep. 25, 2015

(87) PCT Pub. No.: WO2014/139328
PCT Pub. Date: Sep. 18, 2014

(65) Prior Publication Data
US 2016/0060257 A1    Mar. 3, 2016

Related U.S. Application Data

(60) Provisional application No. 61/904,842, filed on Nov. 15, 2013.

(30) Foreign Application Priority Data

Mar. 14, 2013  (IN) .............................. 745/DEL/2013

(51) Int. Cl.
C07D 401/02       (2006.01)
C07D 401/10       (2006.01)
(Continued)

(52) U.S. Cl.
CPC .......... *C07D 471/04* (2013.01); *A61K 31/437* (2013.01); *A61K 31/444* (2013.01);
(Continued)

(58) Field of Classification Search
CPC .. C07D 401/02; C07D 401/10; A61K 31/437; A61K 31/4353
(Continued)

(56) References Cited

U.S. PATENT DOCUMENTS 7,282,588 B2   10/2007   Dhanak et al.
7,511,013 B2    3/2009   Molino et al.
(Continued)

FOREIGN PATENT DOCUMENTS

CN          1615873 A       5/2005
CN          1665809 A       9/2005
(Continued)

OTHER PUBLICATIONS

Abdel-Mohsen S.A., et al., "A Convenient Synthesis of Pyrrolo[2,3-b]pyridines and Pyrido[2',3':5,4]pyrrolo[2,3-d] pyrimidines," Monatshefte fur Chemie, 2008, vol. 139 (10), pp. 1233-1240.
(Continued)

*Primary Examiner* — Niloofar Rahmani
(74) *Attorney, Agent, or Firm* — Changxia Sun

(57) ABSTRACT

Disclosed are compounds of Formula (IIa),

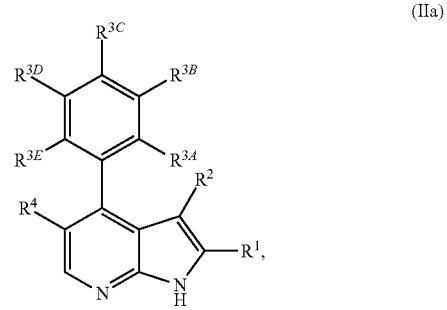

(IIa)

wherein $R^1$, $R^2$, $R^{3A}$, $R^{3B}$, $R^{3C}$, $R^{3D}$, $R^{3E}$, and $R^4$ are as defined in the specification, and pharmaceutically acceptable salts thereof. The compounds may be used as agents in the treatment of diseases, including cancer. Also provided are pharmaceutical compositions comprising one or more compounds of Formula (IIa).

11 Claims, No Drawings

(51) Int. Cl.
A61K 31/437 (2006.01)
A61K 31/4353 (2006.01)
C07D 471/04 (2006.01)
A61K 45/06 (2006.01)
A61K 31/444 (2006.01)
A61K 31/4545 (2006.01)
A61K 31/497 (2006.01)
A61K 31/5377 (2006.01)

(52) U.S. Cl.
CPC ........ *A61K 31/4545* (2013.01); *A61K 31/497* (2013.01); *A61K 31/5377* (2013.01); *A61K 45/06* (2013.01)

(58) Field of Classification Search
USPC .......................................... 514/300; 546/121
See application file for complete search history.

(56) References Cited

U.S. PATENT DOCUMENTS

| | | | |
|---|---|---|---|
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2008/0146606 | A1* | 6/2008 | Bamborough ....... C07D 471/04 514/300 |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |

FOREIGN PATENT DOCUMENTS

| | | | |
|---|---|---|---|
| CN | 102143746 | A | 8/2011 |
| WO | 9507271 | A1 | 3/1995 |
| WO | 9710223 | A1 | 3/1997 |
| WO | 03000695 | A1 | 1/2003 |
| WO | 2005099353 | A2 | 10/2005 |
| WO | 2006008754 | A1 | 1/2006 |
| WO | 2006017443 | A2 | 2/2006 |
| WO | 2008049856 | A2 | 5/2008 |
| WO | 2008079918 | A1 | 7/2008 |
| WO | 2008128072 | A2 | 10/2008 |
| WO | 2008145688 | A2 | 12/2008 |
| WO | 2009047359 | A1 | 4/2009 |
| WO | 2009112473 | A1 | 9/2009 |
| WO | 2010003133 | * | 1/2010 |
| WO | 2010003133 | A2 | 1/2010 |
| WO | 2010020675 | A1 | 2/2010 |
| WO | 2013026516 | A1 | 2/2013 |
| WO | 2013157021 | A1 | 10/2013 |

OTHER PUBLICATIONS

Berge S.M., et al., "Pharmaceutical Salts," Journal of Pharmaceutical Sciences, 1977, vol. 66 (1), pp. 1-19.
Beylot M. et al., "In Vivo Studies of Intrahepatic Metabolic Pathways," Diabetes Metabolism, 1997, vol. 23 (3), pp. 251-257.
Blagojevic N., et al., "Role of heavy water in Boron Neutron Capture Therapy," in: Dosimetry & Treatment Planning for Neutron Capture Therapy, Zamenhof R, et al., Edition, 1994, Advanced Medical Publishing, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Coley W., et al., "Novel HIV-1 Therapeutics Through Targeting Altered Host Cell Pathways.," Expert Opinion on Biological Therapy, 2009, vol. 9 (11), pp. 1369-1382.
Czajka D. M., et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Foster, A. B. et al., "Deuterium Isotope Effects in the Metabolism of Drugs and Xenobiotics: Implications for Drug Design," Advances in Drug Research, 1985, vol. 14, pp. 2-36.
Gamo F.J., et al., "Thousands of Chemical Starting Points for Antimalarial Lead Identification," Nature, 2010, vol. 465 (7296), pp. 305-310.
International Search Report and Written Opinion for Application No. PCT/US2014/025670 mailed on May 22, 2014.
International Search Report for Application No. PCT/CN2014/000265, mailed Jun. 27, 2014, 7 pages.
International Search Report for Application No. PCT/US2014/025740, mailed May 27, 2014, 3 pages.
"IUPAC 1974 Recommendations for Section E, Fundamental Stereochemistry," Pure and Applied Chemistry, 1976, vol. 45, pp. 10-13.
Kato, S. et al., "Synthesis of Deuterated Mosapride Citrate," Journal of Labelled Compounds and Radiopharmaceuticals, 1995, vol. 36 (10), pp. 927-932.
Krystof V., et al., "Pharmacological Targeting of CDK9 in Cardiac Hypertrophy.," Medicinal Research Reviews, 2010, vol. 30 (4), pp. 646-666.
Kushner, et al., "Pharmacological uses and perspectives of heavy water and deuterated compounds," Canadian Journal of Physiology and Pharmacology, 1999, vol. 77 (2), pp. 79-88.
Liddle J., et al., "4-Phenyl-7-azaindoles as Potent, Selective and Bioavailable IKK2 Inhibitors Demonstrating Good in vivo Efficacy,"Bioorganic and Medicinal Chemistry Letters, 2012, vol. 22 (16), pp. 5222-5226.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Malumbres M., et al., "Cell Cycle, CDKs and Cancer: a Changing Paradigm.," Nature Reviews Cancer, 2009, vol. 9 (3), pp. 153-166.
Miyaura N., et al., "Palladium-Catalyzed Cross-Coupling Reactions of Organoboron Compounds," Chemical Reviews, 1995, vol. 95 (7), pp. 2457-2483.
Prescott, Ed., Methods in Cell Biology, vol. XIV, Academic Press, New York, 1976, pp. 33.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suzuki A., "Recent Advances in the Cross-Coupling Reactions of Organoboron Derivates with Organic Electrophiles, 1995-1998," Journal of Organometallic Chemistry, 1999, vol. 576, pp. 147-168.
Thomson J.F. "Physiological Effects of D20 in Mammals," Annals of the New York Academy of Sciences, 1960, vol. 84, pp. 736-744.
Wang S., et al., "Cyclin-dependent kinase 9: a key Transcriptional Regulator and Potential Drug Target in Oncology, Virology and Cardiology.," Trends in Pharmacological Sciences, 2009, vol. 29 (6), pp. 302-312.

* cited by examiner

PYRROLO [2,3-B] PYRIDINE CDK9 KINASE INHIBITORS

BACKGROUND OF THE INVENTION

Cyclin-dependent kinases (CDKs) are serine/threonine protein kinases whose activity depends on binding and activation by cyclin partners. These heterodimeric complexes can phosphorylate various substrates involved in the control of transcription and cell-cycle progression in response to different stimuli. CDK8 and CDK9 have key roles in the control of transcription by RNA polymerase II. CDK9 responds specifically to several cytokines, including tumor necrosis factor and interleukin-6, indicating that it might have special roles in the regulation of a variety of physiological processes, especially immune responses, inflammation, cell activation, and differentiation.

Deregulated CDK activity is a hallmark of human cancer, and a variety of genetic and epigenetic events, such as over expression of cyclins, diminished levels of CDK inhibiting proteins or gain-of function mutations in CDK, have been described to cause increased activity of these enzymes and provide a selective growth advantage in tumor cells. CDK9 inhibition causes rapid depletion of short-lived mRNA transcripts and their associated protein products. Many genes encoding proteins involved in cell growth, proliferation, and tumor development (Myc, Cyclin D1, and Mcl-1) are characterized by short-lived mRNAs and proteins and hence the consequences of CDK9 inhibition include anti-proliferative and pro-apoptotic effects through loss of function at many cellular pathways. Tumor types that are dependent on labile pro-survival proteins (e.g., Mcl-1), which includes multiple myeloma, CLL, breast, melanoma and pancreatic cancers as well as the MYC-driven tumors (multiple cancer types) would be susceptible to CDK9 inhibition. CDK9 inhibitors might also be effective in combination with standard of care in tumors in which NF-κB is constitutively active and contributing to chemo resistance. This includes hematologic malignancies as well as solid tumors (breast, colorectal, prostate, melanoma and pancreatic). Thus, CDK9 inhibition targets multiple cancer-relevant pathways by inhibition of a single protein and thereby renders CDK9 as an attractive target for anti-cancer therapy. (Nature Reviews Cancer: 2009, 9, 153-166).

CDK9 inhibitors can also find therapeutic application in cardiology and virology as many viruses depend on the infected host for transcription of their genome. (Cyclin-dependent kinase 9: a key transcriptional regulator and potential drug target in oncology, virology and cardiology. Trends in Pharmacol. Sci. 2009, 29. 302-312; Pharmacological targeting of CDK9 in cardiac hypertrophy. Med Res. Rev. 2010 30:646-66; Novel HIV-1 therapeutics through targeting altered host cell pathways. Expert Opin Biol Ther. 2009 9:1369-82).

CDK9 inhibitors have also been reported as potential therapeutics for the treatment of chronic, inflammatory and neuropathic pain (WO2008/049856; WO2009/047359).

In view of the above, there is a need in the art for small molecule therapeutics that can inhibit the activity of CDK9. The present invention fulfills at least this need.

SUMMARY OF THE INVENTION

In one aspect, the present invention relates to compounds of Formula (IIa) or a pharmaceutically acceptable salt thereof,

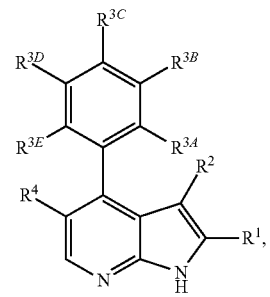

Formula (IIa)

wherein
$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, $C(O)H$, $C(O)OH$, $(O)$, $OH$, $CN$, $NO_2$, $F$, $Cl$, $Br$ and $I$;

$R^2$ is selected from the group consisting of hydrogen, $C_1$-$C_4$ alkyl, $NO_2$, $CN$, $C(O)NH_2$, $C(O)OR^{2A}$, $F$, $Cl$, $Br$ and $I$;

$R^{2A}$ is selected from the group consisting of $C_1$-$C_6$alkyl, and $C_2$-$C_6$alkenyl, and $C_2$—$C_6$alkynyl;

$R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, $F$, $Cl$, $Br$ and $I$;

$R^4$ is selected from the group consisting of $R^{4A}$, $OR^{4A}$, $C(O)NH_2$, $CN$, $F$, $Cl$, $Br$, and $I$;

$R^{4A}$ is selected from the group consisting of hydrogen, $C_1$-$C_6$ alkyl, $C_2$-$C_6$alkenyl, and $C_2$-$C_6$alkynyl;

$R^5$, at each occurrence, is independently selected from the group consisting of $C_1$-$C_6$ alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^5 C_1$-$C_6$ alkyl, $C_2$-$C_6$alkenyl, and $C_2$-$C_6$alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, B(OH)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I;

R$^6$, at each occurrence, is independently selected from the group consisting of C$_1$-C$_6$alkyl, C$_2$-C$_6$alkenyl, C$_2$-C$_6$alkynyl, phenyl, heteroaryl, heterocycloalkyl, heterocycloalkenyl, cycloalkyl, and cycloalkenyl; wherein each R$^6$C$_1$-C$_6$alkyl, C$_2$-C$_6$alkenyl, and C$_2$-C$_6$alkynyl is optionally substituted with one or more substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, CN, NO$_2$, F, Cl, Br and I; wherein each R$^6$ phenyl, cycloalkyl, cycloalkenyl, heteroaryl, heterocycloalkyl, and heterocycloalkenyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, (O), OH, CN, NO$_2$, F, Cl, Br and I;

R$^7$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^7$C$_1$-C$_6$ alkyl, C$_2$-C$_6$alkenyl, and C$_2$-C$_6$alkynyl is optionally substituted with one or more substituents independently selected from the group consisting of R$^{13}$, OR$^{13}$, NH$_2$, NHR$^{13}$, N(R$^{13}$)$_2$, C(O)H, C(O)OH, OH, CN, NO$_2$, F, Cl, Br and I; wherein each R$^7$ aryl, cycloalkyl, cycloalkenyl, heteroaryl, heterocycloalkyl, and heterocycloalkenyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, (O), OH, CN, NO$_2$, F, Cl, Br and I;

R$^8$, at each occurrence, is independently selected from the group consisting of C$_1$-C$_6$ alkyl, C$_2$-C$_6$alkenyl, C$_2$-C$_6$alkynyl, and heterocycloalkyl; wherein each R$^8$C$_1$-C$_6$ alkyl, C$_2$-C$_6$alkenyl, and C$_2$-C$_6$alkynyl is optionally substituted with one or more substituents independently selected from the group consisting of aryl, heteroaryl, SO$_2$R$^{8A}$, C(O)OR$^{8A}$, C(O)NH$_2$, C(O)NHR$^{8A}$, C(O)N(R$^{8A}$)$_2$, C(O)NHSO$_2$R$^{8A}$, C(O)NR$^{8A}$SO$_2$R$^{8A}$, NH$_2$, C(O)H, C(O)OH, OH, CN, NO$_2$, F, Cl, Br and I; wherein each R$^8$ heterocycloalkyl is optionally substituted with one or more substituents independently selected from the group consisting of NH$_2$, C(O)H, C(O)OH, OH, CN, NO$_2$, F, Cl, Br and I;

R$^{8A}$, at each occurrence, is independently selected from the group consisting of C$_1$-C$_6$ alkyl, C$_2$-C$_6$alkenyl, and C$_2$-C$_6$alkynyl;

R$^9$, at each occurrence, is independently selected from the group consisting of C$_1$-C$_6$alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^9$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I; wherein each R$^9$ aryl, cycloalkyl, cycloalkenyl, heteroaryl, heterocycloalkyl, and heterocycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, (O), OH, CN, NO$_2$, F, Cl, Br and I;

R$^{10}$, at each occurrence, is independently selected from the group consisting of C$_1$-C$_6$alkyl, C$_2$-C$_6$alkenyl, and C$_2$-C$_6$ alkynyl; wherein each R$^{10}$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I;

R$^{11}$, at each occurrence, is independently selected from the group consisting of C$_1$-C$_6$alkyl, C$_2$-C$_6$alkenyl, C$_2$-C$_6$alkynyl, aryl, and heteroaryl; wherein each R$^{11}$C$_1$-C$_6$alkyl, C$_2$-C$_6$alkenyl, and C$_2$-C$_6$alkynyl is optionally substituted with one or more substituents independently selected from the group consisting of OR$^{11A}$, NH$_2$, NHR$^{11A}$ N(R$^{11A}$)$_2$, C(O)H, C(O)OH, OH, CN, NO$_2$, F, Cl, Br and I; wherein each R$^{11}$ aryl and heteroaryl is optionally substituted with one or more substituents independently selected from the group consisting of C$_1$-C$_6$alkyl, C$_1$-C$_6$ haloalkyl, NH$_2$, C(O)H, C(O)OH, OH, CN, NO$_2$, F, Cl, Br and I;

R$^{11A}$, at each occurrence, is independently selected from the group consisting of C$_1$-C$_6$alkyl, C$_2$-C$_6$alkenyl, and C$_2$-C$_6$ alkynyl;

R$^{12}$, at each occurrence, is independently selected from the group consisting of C$_1$-C$_6$alkyl, C$_2$-C$_6$alkenyl, and C$_2$-C$_6$ alkynyl; wherein each R$^{12}$C$_1$-C$_6$alkyl, C$_2$-C$_6$alkenyl, and C$_2$-C$_6$alkynyl is optionally substituted with one or more substituents independently selected from the group consisting of $NH_2$, $NHR^{14}$, $N(R^{14})_2$, C(O)H, C(O)OH, OH, CN, $NO_2$, F, Cl, Br and I;

$R^{13}$, at each occurrence, is independently selected from the group consisting of $C_1$-$C_6$alkyl, $C_2$-$C_6$alkenyl, $C_2$-$C_6$ alkynyl, aryl, heteroaryl, cycloalkyl, cycloalkenyl, and heterocycloalkyl, heterocycloalkenyl; wherein each $R^{13}C_1$-$C_6$alkyl, $C_2$-$C_6$alkenyl, and $C_2$-$C_6$alkynyl is optionally substituted with one or more substituents independently selected from the group consisting of $R^{15}$, $OR^{15}$, C(O)H, C(O)OH, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, C(O)H, C(O)OH, (O), OH, CN, $NO_2$, F, Cl, Br and I;

$R^{14}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl;

$R^{15}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl; wherein each $R^{15}C_1$-$C_6$alkyl, $C_2$-$C_6$alkenyl, and $C_2$-$C_6$alkynyl is optionally substituted with one or more $OCH_3$; and $R^{16}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl.

In one embodiment of Formula (IIa), $R^2$ is hydrogen, and $R^4$ is hydrogen. In another embodiment of Formula (IIa), $R^2$ is hydrogen, $R^4$ is hydrogen; and $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)R^5$, $NR^5SO_2NHC(O)OR^5$, NHC(O)$NH_2$, $NHC(O)NHR^5$, $NHC(O)N(R^5)_2$, $NR^5C(O)NHR^5$, $NR^5C(O)N(R^5)_2$, OC(O)$NH_2$, OC(O)$NHR^5$, OC(O)$N(R^5)_2$, OC(O)$NHSO_2R^5$, OC(O)$NR^5SO_2R^5$, C(O)$NH_2$, C(O)$NHR^5$, C(O)$N(R^5)_2$, C(O)NHOH, C(O)$NHOR^5$, C(O)$NHSO_2R^5$, C(O)$NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, C(O)NHCN, C(O)$NR^5CN$, $S(O)NR^5$, $S(O)(N)R^5SO_2R^5$, C(O)H, C(O)OH, (O), OH, CN, $NO_2$, F, Cl, Br and I. In another embodiment of Formula (IIa), $R^2$ is hydrogen, $R^4$ is hydrogen; and $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted. In another embodiment of Formula (IIa), $R^2$ is hydrogen, and $R^4$ is hydrogen; wherein $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, C(O)H, C(O)OH, (O), OH, CN, $NO_2$, F, Cl, Br and I; and $R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl. In another embodiment of Formula (IIa), $R^2$ is hydrogen, $R^4$ is hydrogen; and $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, NHC$(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, C(O)H, C(O)OH, (O), OH, CN, $NO_2$, F, Cl, Br and I; and $R^{3A}$ is H, $R^{3D}$ is H, and $R^{3E}$ is $OCH_3$; and $R^{3B}$ and $R^{3C}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl. In another embodiment of Formula (IIa), $R^2$ is hydrogen, $R^4$ is hydrogen; and $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, $C(O)H$, $C(O)OH$, $(O)$, $OH$, $CN$, $NO_2$, $F$, $Cl$, $Br$ and $I$; and $R^{3A}$ is H, $R^{3B}$ is F, $R^{3C}$ is H, $R^{3D}$ is H, and $R^{3E}$ is $OR^6$. In another embodiment of Formula (IIa), $R^2$ is hydrogen, $R^4$ is hydrogen; and $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, $C(O)H$, $C(O)OH$, $(O)$, $OH$, $CN$, $NO_2$, $F$, $Cl$, $Br$ and $I$; $R^{3A}$ is H, $R^{3B}$ is F, $R^{3C}$ is H, $R^{3D}$ is H, and $R^{3E}$ is $OR^6$; and $R^6$, at each occurrence, is independently selected from the group consisting of $C_1$-$C_6$alkyl, phenyl, heteroaryl, heterocycloalkyl, heterocycloalkenyl, and cycloalkyl; wherein each $R^6C_1$-$C_6$alkyl, is optionally substituted with one or more substituents independently selected from the group consisting of $R^9$, $NH_2$, $NHR^9$, $NHS(O)_2R^9$, $CN$, and $F$; and wherein each $R^6$ phenyl, heteroaryl, heterocycloalkyl, heterocycloalkenyl, and cycloalkyl is optionally substituted with one or more substituents independently selected from the group consisting of $R^{10}$, $OR^{10}$, and F.

Still another embodiment pertains to compounds of Formula (IIa), selected from the group consisting of:

4-(5-fluoro-2-methoxyphenyl)-2-(piperidin-3-yl)-1H-pyrrolo[2,3-b]pyridine;

4-(4-fluoro-2-methoxyphenyl)-2-(piperidin-3-yl)-1H-pyrrolo[2,3-b]pyridine;

4-(5-fluoro-2-methoxyphenyl)-2-[(3S)-piperidin-3-yl]-1H-pyrrolo[2,3-b]pyridine;

4-(5-fluoro-2-methoxyphenyl)-2-[(3R)-piperidin-3-yl]-1H-pyrrolo[2,3-b]pyridine;

4-[5-(4,5-dihydro-1H-imidazol-2-yl)-2-methoxyphenyl]-2-(piperidin-3-yl)-1H-pyrrolo[2,3-b]pyridine;

4-(5-cyclopropyl-2-methoxyphenyl)-2-(piperidin-3-yl)-1H-pyrrolo[2,3-b]pyridine;

4-(4-fluoro-2-methoxyphenyl)-2-(1-methylpiperidin-3-yl)-1H-pyrrolo[2,3-b]pyridine;

4-(5-fluoro-2-methoxyphenyl)-2-(1-methylpiperidin-3-yl)-1H-pyrrolo[2,3-b]pyridine;

1-{3-[4-(5-fluoro-2-methoxyphenyl)-1H-pyrrolo[2,3-b]pyridin-2-yl]piperidin-1-yl}ethanone;

4-(5-fluoro-2-methoxyphenyl)-2-(piperidin-4-yl)-1H-pyrrolo[2,3-b]pyridine;

4-(4-fluoro-2-methoxyphenyl)-2-(piperidin-4-yl)-1H-pyrrolo[2,3-b]pyridine;

4-(4-chloro-2-methoxyphenyl)-2-(piperidin-4-yl)-1H-pyrrolo[2,3-b]pyridine;

4-(4,5-difluoro-2-methoxyphenyl)-2-(piperidin-4-yl)-1H-pyrrolo[2,3-b]pyridine;
4-(5-chloro-2-methoxyphenyl)-2-(piperidin-4-yl)-1H-pyrrolo[2,3-b]pyridine;
4-(2-methoxy-5-methylphenyl)-2-(piperidin-4-yl)-1H-pyrrolo[2,3-b]pyridine;
4-(3-chloro-2-methoxyphenyl)-2-(piperidin-4-yl)-1H-pyrrolo[2,3-b]pyridine;
4-(2-methoxyphenyl)-2-(piperidin-4-yl)-1H-pyrrolo[2,3-b]pyridine;
4-(5-fluoro-2-methoxyphenyl)-2-(1-methylpiperidin-4-yl)-1H-pyrrolo[2,3-b]pyridine;
4-(4-fluoro-2-methoxyphenyl)-2-(1-methylpiperidin-4-yl)-1H-pyrrolo[2,3-b]pyridine;
4-(2-methoxy-5-methylphenyl)-2-(1-methylpiperidin-4-yl)-1H-pyrrolo[2,3-b]pyridine;
N-{4-chloro-3-[2-(piperidin-4-yl)-1H-pyrrolo[2,3-b]pyridin-4-yl]phenyl}benzenesulfonamide;
N-benzyl-4-fluoro-3-[2-(piperidin-4-yl)-1H-pyrrolo[2,3-b]pyridin-4-yl]aniline;
N-benzyl-4-chloro-3-[2-(piperidin-4-yl)-1H-pyrrolo[2,3-b]pyridin-4-yl]aniline;
4-(5-fluoro-2-methoxyphenyl)-2-(pyrrolidin-3-yl)-1H-pyrrolo[2,3-b]pyridine;
4-(4-fluoro-2-methoxyphenyl)-2-(pyrrolidin-3-yl)-1H-pyrrolo[2,3-b]pyridine;
4-(5-fluoro-2-methoxyphenyl)-2-[(3S)-pyrrolidin-3-yl]-1H-pyrrolo[2,3-b]pyridine;
4-(5-fluoro-2-methoxyphenyl)-2-[(3R)-pyrrolidin-3-yl]-1H-pyrrolo[2,3-b]pyridine;
4-(5-fluoro-2-methoxyphenyl)-2-(1-methylpyrrolidin-3-yl)-1H-pyrrolo[2,3-b]pyridine;
4-(4-fluoro-2-methoxyphenyl)-2-(morpholin-2-yl)-1H-pyrrolo[2,3-b]pyridine;
4-(5-fluoro-2-methoxyphenyl)-2-(morpholin-2-yl)-1H-pyrrolo[2,3-b]pyridine;
4-(4-fluoro-2-methoxyphenyl)-2-(4-methylmorpholin-2-yl)-1H-pyrrolo[2,3-b]pyridine;
4-(5-fluoro-2-methoxyphenyl)-2-(4-methylmorpholin-2-yl)-1H-pyrrolo[2,3-b]pyridine;
2-(5,5-dimethylmorpholin-2-yl)-4-(5-fluoro-2-methoxyphenyl)-1H-pyrrolo[2,3-b]pyridine;
2-(5,5-dimethylmorpholin-2-yl)-4-(4-fluoro-2-methoxyphenyl)-1H-pyrrolo[2,3-b]pyridine;
4-(4-chloro-2-methoxyphenyl)-2-(5,5-dimethylmorpholin-2-yl)-1H-pyrrolo[2,3-b]pyridine;
trans-4-[4-(5-fluoro-2-methoxyphenyl)-1H-pyrrolo[2,3-b]pyridin-2-yl]cyclohexanamine;
3-[4-(5-fluoro-2-methoxyphenyl)-1H-pyrrolo[2,3-b]pyridin-2-yl]cyclohexanamine;
4-(5-fluoro-2-methoxyphenyl)-3-methyl-2-(piperidin-4-yl)-1H-pyrrolo[2,3-b]pyridine;
5-chloro-4-(3-fluorophenyl)-2-(piperidin-3-yl)-1H-pyrrolo[2,3-b]pyridine;
3-[5-chloro-4-(3-fluorophenyl)-1H-pyrrolo[2,3-b]pyridin-2-yl]cyclohexanamine;
4-(5-fluoro-2-methoxyphenyl)-2-(1,2,3,6-tetrahydropyridin-4-yl)-1H-pyrrolo[2,3-b]pyridine;
4-(5-fluoro-2-methoxyphenyl)-2-(pyrrolidin-2-yl)-1H-pyrrolo[2,3-b]pyridine;
2-cyclohexyl-4-(5-fluoro-2-methoxyphenyl)-1H-pyrrolo[2,3-b]pyridine;
1-{2-[4-(5-fluoro-2-methoxyphenyl)-1H-pyrrolo[2,3-b]pyridin-2-yl]pyrrolidin-1-yl}ethanone;
1-{4-[4-(5-fluoro-2-methoxyphenyl)-1H-pyrrolo[2,3-b]pyridin-2-yl]-3,6-dihydropyridin-1(2H)-yl}ethanone;
1-{4-[4-(5-fluoro-2-methoxyphenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-(1-methylpyrrolidin-2-yl)-1H-pyrrolo[2,3-b]pyridine;
1-{3-[4-(5-fluoro-2-methoxyphenyl)-1H-pyrrolo[2,3-b]pyridin-2-yl]pyrrolidin-1-yl}ethanone;
2-{3-[4-(5-fluoro-2-methoxyphenyl)-1H-pyrrolo[2,3-b]pyridin-2-yl]pyrrolidin-1-yl}ethanol;
4-(5-fluoro-2-methoxyphenyl)-2-[1-(tetrahydro-2H-pyran-4-yl)pyrrolidin-3-yl]-1H-pyrrolo[2,3-b]pyridine;
4-(5-fluoro-2-methoxyphenyl)-2-[1-(pyridin-2-ylmethyl)pyrrolidin-3-yl]-1H-pyrrolo[2,3-b]pyridine;
4-(5-fluoro-2-methoxyphenyl)-2-[1-(pyridin-3-ylmethyl)pyrrolidin-3-yl]-1H-pyrrolo[2,3-b]pyridine;
4-(5-fluoro-2-methoxyphenyl)-2-[1-(pyridin-4-ylmethyl)pyrrolidin-3-yl]-1H-pyrrolo[2,3-b]pyridine;
4-(5-fluoro-2-methoxyphenyl)-2-[1-(tetrahydro-2H-pyran-3-ylmethyl)pyrrolidin-3-yl]-1H-pyrrolo[2,3-b]pyridine;
tert-butyl (2-{3-[4-(5-fluoro-2-methoxyphenyl)-1H-pyrrolo[2,3-b]pyridin-2-yl]pyrrolidin-1-yl}ethyl)carbamate;
tert-butyl 3-[4-(5-fluoro-2-methoxyphenyl)-1H-pyrrolo[2,3-b]pyridin-2-yl]-1,3'-bipyrrolidine-1'-carboxylate;
4-(5-fluoro-2-methoxyphenyl)-2-[1-(tetrahydro-2H-pyran-4-ylmethyl)pyrrolidin-3-yl]-1H-pyrrolo[2,3-b]pyridine;
4-(5-fluoro-2-methoxyphenyl)-2-{1-[2-(morpholin-4-yl)ethyl]pyrrolidin-3-yl}-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine;
methyl 4-({trans-4-[4-(5-fluoro-2-methoxyphenyl)-1H-pyrrolo[2,3-b]pyridin-2-yl]cyclohexyl}amino)butanoate;
ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate;
trans-4-[4-(5-fluoro-2-methoxyphenyl)-1H-pyrrolo[2,3-b]pyridin-2-yl]-N-[2-(morpholin-4-yl)ethyl]cyclohexanamine;
3-({trans-4-[4-(5-fluoro-2-methoxyphenyl)-1H-pyrrolo[2,3-b]pyridin-2-yl]cyclohexyl}amino)propane-1,2-diol;
2-{3-[4-(5-fluoro-2-methoxyphenyl)-1H-pyrrolo[2,3-b]pyridin-2-yl]pyrrolidin-1-yl}ethanamine;
3-[4-(5-fluoro-2-methoxyphenyl)-1H-pyrrolo[2,3-b]pyridin-2-yl]-1,3'-bipyrrolidine;
4-[4-(5-fluoro-2-methoxyphenyl)-1H-pyrrolo[2,3-b]pyridin-2-yl]piperidin-4-ol;
benzyl (3-{3-[4-(5-fluoro-2-methoxyphenyl)-1H-pyrrolo[2,3-b]pyridin-2-yl]piperidin-1-yl}propyl)carbamate;
2-{3-[4-(5-fluoro-2-methoxyphenyl)-1H-pyrrolo[2,3-b]pyridin-2-yl]piperidin-1-yl}ethanol;
3-{3-[4-(5-fluoro-2-methoxyphenyl)-1H-pyrrolo[2,3-b]pyridin-2-yl]piperidin-1-yl}propan-1-amine;
4-(5-fluoro-2-methoxyphenyl)-2-[1-(2-methoxyethyl)piperidin-3-yl]-1H-pyrrolo[2,3-b]pyridine;
4-({trans-4-[4-(5-fluoro-2-methoxyphenyl)-1H-pyrrolo[2,3-b]pyridin-2-yl]cyclohexyl}amino)butanoic acid;
1-{4-[4-(5-fluoro-2-methoxyphenyl)-1H-pyrrolo[2,3-b]pyridin-2-yl]piperidin-1-yl}ethanone;
1-{4-[4-(5-fluoro-2-methoxyphenyl)-1H-pyrrolo[2,3-b]pyridin-2-yl]piperidin-1-yl}-2-hydroxyethanone;
3-methoxy-4-[2-(piperidin-3-yl)-1H-pyrrolo[2,3-b]pyridin-4-yl]benzonitrile;
2-[({trans-4-[4-(5-fluoro-2-methoxyphenyl)-1H-pyrrolo[2,3-b]pyridin-2-yl]cyclohexyl}amino)methyl]cyclopropanecarboxylic acid;
2-(azetidin-3-yl)-4-(5-fluoro-2-methoxyphenyl)-1H-pyrrolo[2,3-b]pyridine;

1-{4-[4-(5-fluoro-2-methoxyphenyl)-1H-pyrrolo[2,3-b]pyridin-2-yl]piperidin-1-yl}-2-(4-hydroxypiperidin-1-yl)ethanone;

4-(5-fluoro-2-methoxyphenyl)-2-[1-(methylsulfonyl)piperidin-4-yl]-1H-pyrrolo[2,3-b]pyridine;

3-{4-[4-(5-fluoro-2-methoxyphenyl)-1H-pyrrolo[2,3-b]pyridin-2-yl]piperidin-1-yl}propane-1,2-diol;

4-[4-(5-fluoro-2-methoxyphenyl)-1H-pyrrolo[2,3-b]pyridin-2-yl]tetrahydro-2H-pyran-4-ol;

4-(5-fluoro-2-methoxyphenyl)-2-[1-(pyridin-4-ylmethyl)azetidin-3-yl]-1H-pyrrolo[2,3-b]pyridine;

1-{3-[4-(5-fluoro-2-methoxyphenyl)-1H-pyrrolo[2,3-b]pyridin-2-yl]azetidin-1-yl}ethanone;

2-{3-[4-(5-fluoro-2-methoxyphenyl)-1H-pyrrolo[2,3-b]pyridin-2-yl]azetidin-1-yl}ethanamine;

4-(5-fluoro-2-methoxyphenyl)-2-[1-(tetrahydro-2H-pyran-4-ylmethyl)azetidin-3-yl]-1H-pyrrolo[2,3-b]pyridine;

4-(5-fluoro-2-methoxyphenyl)-2-{1-[2-(morpholin-4-yl)ethyl]azetidin-3-yl}-1H-pyrrolo[2,3-b]pyridine;

2-{3-[4-(5-fluoro-2-methoxyphenyl)-1H-pyrrolo[2,3-b]pyridin-2-yl]azetidin-1-yl}ethanol;

4-fluoro-3-[2-(1-methylpiperidin-4-yl)-1H-pyrrolo[2,3-b]pyridin-4-yl]-N-(tetrahydro-2H-pyran-4-ylmethyl)aniline;

1-{4-[4-(5-fluoro-2-methoxyphenyl)-1H-pyrrolo[2,3-b]pyridin-2-yl]piperidin-1-yl}-2-(piperidin-1-yl)ethanone;

1-{4-[4-(5-fluoro-2-methoxyphenyl)-1H-pyrrolo[2,3-b]pyridin-2-yl]piperidin-1-yl}-2-(morpholin-4-yl)ethanone;

1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone;

1-{4-[4-(5-fluoro-2-methoxyphenyl)-1H-pyrrolo[2,3-b]pyridin-2-yl]piperidin-1-yl}-2-[(2-hydroxyethyl)amino]ethanone;

4-(5-fluoro-2-methoxyphenyl)-2-(1-methylazetidin-3-yl)-1H-pyrrolo[2,3-b]pyridine;

4-(5-fluoro-2-methoxyphenyl)-2-[1-(methylsulfonyl)azetidin-3-yl]-1H-pyrrolo[2,3-b]pyridine;

3-{4-[4-(5-fluoro-2-methoxyphenyl)-1H-pyrrolo[2,3-b]pyridin-2-yl]-3,6-dihydropyridin-1(2H)-yl}propane-1,2-diol;

4-fluoro-3-[2-(piperidin-4-yl)-1H-pyrrolo[2,3-b]pyridin-4-yl]aniline;

4-fluoro-3-[2-(1-methylpiperidin-4-yl)-1H-pyrrolo[2,3-b]pyridin-4-yl]-N-(pyridin-4-ylmethyl)aniline;

4-fluoro-3-[2-(1-methylpiperidin-4-yl)-1H-pyrrolo[2,3-b]pyridin-4-yl]-N-[4-(methylsulfonyl)benzyl]aniline;

4-[({4-fluoro-3-[2-(1-methylpiperidin-4-yl)-1H-pyrrolo[2,3-b]pyridin-4-yl]phenyl}amino)methyl]benzamide;

2-(azepan-3-yl)-4-(5-fluoro-2-methoxyphenyl)-1H-pyrrolo[2,3-b]pyridine;

N-benzyl-3-[5-chloro-2-(piperidin-4-yl)-1H-pyrrolo[2,3-b]pyridin-4-yl]-4-fluoroaniline;

N-benzyl-4-chloro-3-[2-(piperidin-3-yl)-1H-pyrrolo[2,3-b]pyridin-4-yl]aniline;

4-(4,5-difluoro-2-methoxyphenyl)-2-(piperidin-3-yl)-1H-pyrrolo[2,3-b]pyridine;

N-benzyl-4-fluoro-3-[2-(piperidin-3-yl)-1H-pyrrolo[2,3-b]pyridin-4-yl]aniline;

4-fluoro-N-(3-fluorobenzyl)-3-[2-(piperidin-3-yl)-1H-pyrrolo[2,3-b]pyridin-4-yl]aniline;

4-[4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-3,6-dihydropyridine-1(2H)-sulfonamide;

N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide;

tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-ene-1-carboxylic acid;

4-(2,3-difluorophenyl)-2-[1-(methylsulfonyl)-1,2,3,6-tetrahydropyridin-4-yl]-1H-pyrrolo[2,3-b]pyridine;

3-{4-[4-(5-fluoro-2-methoxyphenyl)-1H-pyrrolo[2,3-b]pyridin-2-yl]-3,6-dihydropyridin-1(2H)-yl}-3-oxopropanenitrile;

4-[4-(2,3-difluorophenyl)-1H-pyrrolo[2,3-b]pyridin-2-yl]-N-methyl-3,6-dihydropyridine-1(2H)-carboxamide;

4-(5-fluoro-2-methoxyphenyl)-2-[8-(methylsulfonyl)-8-azabicyclo[3.2.1]oct-2-en-3-yl]-1H-pyrrolo[2,3-b]pyridine;

2-{4-[4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide;

{4-[4-(5-fluoro-2-methoxyphenyl)-1H-pyrrolo[2,3-b]pyridin-2-yl]-3,6-dihydropyridin-1(2H)-yl}acetic acid;

2-{4-[4-(5-fluoro-2-methoxyphenyl)-1H-pyrrolo[2,3-b]pyridin-2-yl]-3,6-dihydropyridin-1(2H)-yl}acetamide;

ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[5-chloro-4-(5-fluoro-2-methoxyphenyl)-1H-pyrrolo[2,3-b]pyridin-2-yl]-N-methyl-3,6-dihydropyridine-1(2H)-carboxamide;

4-(5-fluoro-2-methoxyphenyl)-2-[1-(S-methylsulfonimidoyl)-1,2,3,6-tetrahydropyridin-4-yl]-1H-pyrrolo[2,3-b]pyridine;

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(4,5-difluoro-2-methoxyphenyl)-1H-pyrrolo[2,3-b]pyridin-2-yl]-N-methyl-3,6-dihydropyridine-1(2H)-carboxamide;

2-{3-[4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{4-[4-(2,3-difluorophenyl)-1H-pyrrolo[2,3-b]pyridin-2-yl]-3,6-dihydropyridin-1(2H)-yl}-N,N-dimethylacetamide;

2-{4-[4-(5-fluoro-2-methoxyphenyl)-1H-pyrrolo[2,3-b]pyridin-2-yl]piperidin-1-yl}-N,N-dimethylacetamide;

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide;

ethyl ({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{4-[4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone;

N-{4-[4-(5-fluoro-2-methoxyphenyl)-1H-pyrrolo[2,3-b]pyridin-2-yl]cyclohex-3-en-1-yl}-D-valine;
1-{4-[4-(5-fluoro-2-methoxyphenyl)-1H-pyrrolo[2,3-b]pyridin-2-yl]cyclohex-3-en-1-yl}-L-proline;
N-cyano-4-[4-(5-fluoro-2-methoxyphenyl)-1H-pyrrolo[2,3-b]pyridin-2-yl]-3,6-dihydropyridine-1(2H)-carboxamide;
1-({4-[4-(5-fluoro-2-methoxyphenyl)-1H-pyrrolo[2,3-b]pyridin-2-yl]-3,6-dihydropyridin-1(2H)-yl}acetyl)-L-prolinamide;
2-{4-[4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]piperidin-1-yl}-N-methylacetamide;
2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile;
4-[3-cyano-4-(5-fluoro-2-methoxyphenyl)-1H-pyrrolo[2,3-b]pyridin-2-yl]-N-methyl-3,6-dihydropyridine-1(2H)-carboxamide;
ethyl ({4-[4-(5-fluoro-2-methoxyphenyl)-1H-pyrrolo[2,3-b]pyridin-2-yl]cyclohex-3-en-1-yl}sulfamoyl)carbamate;
2-{4-[4-(5-fluoro-2-methoxyphenyl)-1H-pyrrolo[2,3-b]pyridin-2-yl]piperidin-1-yl}-N-(2-hydroxyethyl)-N-methylacetamide;
2-{4-[4-(5-fluoro-2-methoxyphenyl)-1H-pyrrolo[2,3-b]pyridin-2-yl]piperidin-1-yl}-N-(3-hydroxycyclobutyl)acetamide;
2-{4-[4-(5-fluoro-2-methoxyphenyl)-1H-pyrrolo[2,3-b]pyridin-2-yl]piperidin-1-yl}-1-(3-hydroxyazetidin-1-yl)ethanone;
N-{4-[4-(5-fluoro-2-methoxyphenyl)-1H-pyrrolo[2,3-b]pyridin-2-yl]cyclohex-3-en-1-yl}-3-methyl-L-valine;
2-{4-[5-fluoro-4-(5-fluoro-2-methoxyphenyl)-1H-pyrrolo[2,3-b]pyridin-2-yl]piperidin-1-yl}-N,N-dimethylacetamide;
2-{4-[3-cyano-4-(5-fluoro-2-methoxyphenyl)-1H-pyrrolo[2,3-b]pyridin-2-yl]-3,6-dihydropyridin-1(2H)-yl}-N,N-dimethylacetamide;
2-{4-[4-(2-methoxyphenyl)-1H-pyrrolo[2,3-b]pyridin-2-yl]piperidin-1-yl}-N,N-dimethylacetamide;
4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;
2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone;
2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
4-(5-fluoro-2-methoxyphenyl)-2-((3aS,6aR)-2-(methylsulfonyl)-1,2,3,3a,4,6a-hexahydrocyclopenta[c]pyrrol-5-yl)-1H-pyrrolo[2,3-b]pyridine;
2-{4-[3-cyano-5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;
4-(5-fluoro-2-methoxyphenyl)-2-((3aR,6aS)-2-(methylsulfonyl)-1,2,3,3a,4,6a-hexahydrocyclopenta[c]pyrrol-5-yl)-1H-pyrrolo[2,3-b]pyridine;
5-fluoro-4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile;
4-[3-cyano-5-fluoro-4-(5-fluoro-2-methoxyphenyl)-1H-pyrrolo[2,3-b]pyridin-2-yl]-N-methyl-3,6-dihydropyridine-1(2H)-carboxamide;
5-fluoro-4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile;
5-fluoro-4-(5-fluoro-2-methoxyphenyl)-2-(1-{2-[(2R)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;
2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-{4-[4-(5-fluoro-2-methoxyphenyl)-1H-pyrrolo[2,3-b]pyridin-2-yl]-2,2-dimethyl-3,6-dihydropyridin-1(2H)-yl}-N,N-dimethylacetamide;
4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine;
2-{4-[5-cyano-4-(5-fluoro-2-methoxyphenyl)-1H-pyrrolo[2,3-b]pyridin-2-yl]piperidin-1-yl}-N,N-dimethylacetamide;
2-{4-[4-(5-fluoro-2-methoxyphenyl)-1H-pyrrolo[2,3-b]pyridin-2-yl]piperidin-1-yl}-N-(3-hydroxycyclobutyl)-N-methylacetamide;
4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
4-[5-fluoro-4-(5-fluoro-2-methoxyphenyl)-1H-pyrrolo[2,3-b]pyridin-2-yl]cyclohex-3-ene-1-carboxylic acid;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-hydroxyethanone;
3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-3-oxopropanenitrile;
5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile;
(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-methyl-2-oxoethanesulfonamide;
4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;
2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone;
2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone;
(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone;
{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone;
2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;
2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;
4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile;
2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;
2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;
2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide; and pharmaceutically acceptable salts thereof.
N-benzyl-4-fluoro-3-[2-(1-methylpiperidin-4-yl)-1H-pyrrolo[2,3-b]pyridin-4-yl]aniline;
4-[({4-fluoro-3-[2-(1-methylpiperidin-4-yl)-1H-pyrrolo[2,3-b]pyridin-4-yl]phenyl}amino)methyl]phenol;
4-fluoro-3-[2-(1-methylpiperidin-4-yl)-1H-pyrrolo[2,3-b]pyridin-4-yl]-N-(1H-1,2,4-triazol-5-ylmethyl)aniline;
4-fluoro-3-[2-(1-methylpiperidin-4-yl)-1H-pyrrolo[2,3-b]pyridin-4-yl]-N-(pyridin-2-ylmethyl)aniline;
N-[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;
N,N-bis[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;
N,N-bis(cyclopropylmethyl)-4-fluoro-3-[2-(1-methylpiperidin-4-yl)-1H-pyrrolo[2,3-b]pyridin-4-yl]aniline;
4-fluoro-3-[2-(1-methylpiperidin-4-yl)-1H-pyrrolo[2,3-b]pyridin-4-yl]-N-[3-(methylsulfonyl)benzyl]aniline;
2-[1-(cyclopropylsulfonyl)-1,2,3,6-tetrahydropyridin-4-yl]-4-(5-fluoro-2-methoxyphenyl)-1H-pyrrolo[2,3-b]pyridine;
4-[({4-fluoro-3-[2-(1-methylpiperidin-4-yl)-1H-pyrrolo[2,3-b]pyridin-4-yl]phenyl}amino)methyl]benzenesulfonamide;
3-[({4-fluoro-3-[2-(1-methylpiperidin-4-yl)-1H-pyrrolo[2,3-b]pyridin-4-yl]phenyl}amino)methyl]phenol;
N-(3-chlorobenzyl)-4-fluoro-3-[2-(1-methylpiperidin-4-yl)-1H-pyrrolo[2,3-b]pyridin-4-yl]aniline;
4-fluoro-N-(4-fluorobenzyl)-3-[2-(1-methylpiperidin-4-yl)-1H-pyrrolo[2,3-b]pyridin-4-yl]aniline;
4-fluoro-N-(2-fluorobenzyl)-3-[2-(1-methylpiperidin-4-yl)-1H-pyrrolo[2,3-b]pyridin-4-yl]aniline;
4-fluoro-N-(3-methoxybenzyl)-3-[2-(1-methylpiperidin-4-yl)-1H-pyrrolo[2,3-b]pyridin-4-yl]aniline;
{4-[({4-fluoro-3-[2-(1-methylpiperidin-4-yl)-1H-pyrrolo[2,3-b]pyridin-4-yl]phenyl}amino)methyl]phenoxy}acetic acid;
N-[(1,1-dioxidotetrahydro-2H-thiopyran-4-yl)methyl]-4-fluoro-3-[2-(1-methylpiperidin-4-yl)-1H-pyrrolo[2,3-b]pyridin-4-yl]aniline;
4-[4-(5-fluoro-2-methoxyphenyl)-1H-pyrrolo[2,3-b]pyridin-2-yl]tetrahydro-2H-thiopyran-4-ol 1,1-dioxide;
2-(1,1-dioxido-3,6-dihydro-2H-thiopyran-4-yl)-4-(5-fluoro-2-methoxyphenyl)-1H-pyrrolo[2,3-b]pyridine;
3-[4-(5-fluoro-2-methoxyphenyl)-1H-pyrrolo[2,3-b]pyridin-2-yl]pyrrolidin-3-ol;
2-(2,5-dihydro-1H-pyrrol-3-yl)-4-(5-fluoro-2-methoxyphenyl)-1H-pyrrolo[2,3-b]pyridine;
4-fluoro-N-(3-fluorobenzyl)-3-[2-(1-methylpiperidin-4-yl)-1H-pyrrolo[2,3-b]pyridin-4-yl]aniline;
N-(2,4-difluorobenzyl)-4-fluoro-3-[2-(1-methylpiperidin-4-yl)-1H-pyrrolo[2,3-b]pyridin-4-yl]aniline;
N-(2,6-difluorobenzyl)-4-fluoro-3-[2-(1-methylpiperidin-4-yl)-1H-pyrrolo[2,3-b]pyridin-4-yl]aniline;
2-{1-[(chloromethyl)sulfonyl]-1,2,3,6-tetrahydropyridin-4-yl}-4-(5-fluoro-2-methoxyphenyl)-1H-pyrrolo[2,3-b]pyridine;
4-(5-fluoro-2-methoxyphenyl)-2-[1-(propan-2-ylsulfonyl)-1,2,3,6-tetrahydropyridin-4-yl]-1H-pyrrolo[2,3-b]pyridine;
4-(5-fluoro-2-methoxyphenyl)-2-[1-(propylsulfonyl)-1,2,3,6-tetrahydropyridin-4-yl]-1H-pyrrolo[2,3-b]pyridine;
2-{1-[(1,1-dioxidotetrahydrothiophen-3-yl)sulfonyl]-1,2,3,6-tetrahydropyridin-4-yl}-4-(5-fluoro-2-methoxyphenyl)-1H-pyrrolo[2,3-b]pyridine;
N-(2,5-difluorobenzyl)-4-fluoro-3-[2-(1-methylpiperidin-4-yl)-1H-pyrrolo[2,3-b]pyridin-4-yl]aniline;
4-(5-fluoro-2-methoxyphenyl)-2-{1-[(2,2,2-trifluoroethyl)sulfonyl]-1,2,3,6-tetrahydropyridin-4-yl}-1H-pyrrolo[2,3-b]pyridine;
N-(2-chlorobenzyl)-4-fluoro-3-[2-(1-methylpiperidin-4-yl)-1H-pyrrolo[2,3-b]pyridin-4-yl]aniline;

3-[({4-fluoro-3-[2-(1-methylpiperidin-4-yl)-1H-pyrrolo[2,3-b]pyridin-4-yl]phenyl}amino)methyl]benzoic acid;
4-[({4-fluoro-3-[2-(1-methylpiperidin-4-yl)-1H-pyrrolo[2,3-b]pyridin-4-yl]phenyl}amino)methyl]benzonitrile;
2-[({4-fluoro-3-[2-(1-methylpiperidin-4-yl)-1H-pyrrolo[2,3-b]pyridin-4-yl]phenyl}amino)methyl]benzonitrile;
3-[({4-fluoro-3-[2-(1-methylpiperidin-4-yl)-1H-pyrrolo[2,3-b]pyridin-4-yl]phenyl}amino)methyl]benzonitrile;
trans-4-[4-(5-fluoro-2-methoxyphenyl)-1H-pyrrolo[2,3-b]pyridin-2-yl]-N-{[1-(methoxymethyl)-1H-1,2,3-triazol-4-yl]methyl}cyclohexanamine;
trans-4-[4-(5-fluoro-2-methoxyphenyl)-1H-pyrrolo[2,3-b]pyridin-2-yl]-N-{[1-(methoxymethyl)-1H-1,2,3-triazol-5-yl]methyl}cyclohexanamine;
2,4-difluoro-N-[(4-methyltetrahydro-2H-pyran-4-yl)methyl]-5-[2-(piperidin-4-yl)-1H-pyrrolo[2,3-b]pyridin-4-yl]aniline;
N-benzyl-2,4-difluoro-5-[2-(piperidin-4-yl)-1H-pyrrolo[2,3-b]pyridin-4-yl]aniline;
2,4-difluoro-5-[2-(piperidin-4-yl)-1H-pyrrolo[2,3-b]pyridin-4-yl]-N-(tetrahydro-2H-pyran-4-ylmethyl)aniline;
2,4-difluoro-N-(3-fluorobenzyl)-5-[2-(piperidin-4-yl)-1H-pyrrolo[2,3-b]pyridin-4-yl]aniline;
4-(5-fluoro-2-methoxyphenyl)-2-[1-(thiophen-2-ylsulfonyl)-1,2,3,6-tetrahydropyridin-4-yl]-1H-pyrrolo[2,3-b]pyridine;
N-[2-chloro-4-({4-[4-(5-fluoro-2-methoxyphenyl)-1H-pyrrolo[2,3-b]pyridin-2-yl]-3,6-dihydropyridin-1(2H)-yl}sulfonyl)phenyl]acetamide;
4-(5-fluoro-2-methoxyphenyl)-2-{1-[(2,4,5-trichlorophenyl)sulfonyl]-1,2,3,6-tetrahydropyridin-4-yl}-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}sulfonyl)-2,1,3-benzoxadiazole;
2-{1-[(3,5-dimethyl-1,2-oxazol-4-yl)sulfonyl]-1,2,3,6-tetrahydropyridin-4-yl}-4-(5-fluoro-2-methoxyphenyl)-1H-pyrrolo[2,3-b]pyridine;
N-(3-chlorobenzyl)-4-fluoro-3-[2-(piperidin-4-yl)-1H-pyrrolo[2,3-b]pyridin-4-yl]aniline;
4-fluoro-N-(3-fluorobenzyl)-3-[2-(piperidin-4-yl)-1H-pyrrolo[2,3-b]pyridin-4-yl]aniline;
4-[({4-fluoro-3-[2-(piperidin-4-yl)-1H-pyrrolo[2,3-b]pyridin-4-yl]phenyl}amino)methyl]benzonitrile;
4-fluoro-N-[4-(methylsulfonyl)benzyl]-3-[2-(piperidin-4-yl)-1H-pyrrolo[2,3-b]pyridin-4-yl]aniline;
4-fluoro-3-[2-(piperidin-4-yl)-1H-pyrrolo[2,3-b]pyridin-4-yl]-N-(pyridin-4-ylmethyl)aniline;
3-[4-(5-fluoro-2-methoxyphenyl)-1H-pyrrolo[2,3-b]pyridin-2-yl]azetidin-3-ol;
4-[4-(5-fluoro-2-methoxyphenyl)-1H-pyrrolo[2,3-b]pyridin-2-yl]-1-(methylsulfonyl)piperidin-4-ol;
2-(1-benzylpiperidin-4-yl)-4-(5-fluoro-2-methoxyphenyl)-1H-pyrrolo[2,3-b]pyridine;
4-(5-fluoro-2-methoxyphenyl)-2-(1-methyl-1,2,3,6-tetrahydropyridin-4-yl)-1H-pyrrolo[2,3-b]pyridine;
4-fluoro-3-{2-[1-(methylsulfonyl)-1,2,3,6-tetrahydropyridin-4-yl]-1H-pyrrolo[2,3-b]pyridin-4-yl}aniline;
4-fluoro-3-[2-(1-methylpiperidin-4-yl)-1H-pyrrolo[2,3-b]pyridin-4-yl]-N-(pyridin-3-ylmethyl)aniline;
4-fluoro-3-[2-(piperidin-4-yl)-1H-pyrrolo[2,3-b]pyridin-4-yl]-N-(pyridin-3-ylmethyl)aniline;
N-(3,5-difluorobenzyl)-4-fluoro-3-[2-(piperidin-4-yl)-1H-pyrrolo[2,3-b]pyridin-4-yl]aniline;
N-(2,4-difluorobenzyl)-4-fluoro-3-[2-(piperidin-4-yl)-1H-pyrrolo[2,3-b]pyridin-4-yl]aniline;
N-(2,5-difluorobenzyl)-4-fluoro-3-[2-(piperidin-4-yl)-1H-pyrrolo[2,3-b]pyridin-4-yl]aniline;
N-(2,6-difluorobenzyl)-4-fluoro-3-[2-(piperidin-4-yl)-1H-pyrrolo[2,3-b]pyridin-4-yl]aniline;
N-(3,5-difluorobenzyl)-4-fluoro-3-[2-(1-methylpiperidin-4-yl)-1H-pyrrolo[2,3-b]pyridin-4-yl]aniline;
4-fluoro-N-(4-fluorobenzyl)-3-[2-(piperidin-4-yl)-1H-pyrrolo[2,3-b]pyridin-4-yl]aniline;
4-[({4-fluoro-3-[2-(piperidin-4-yl)-1H-pyrrolo[2,3-b]pyridin-4-yl]phenyl}amino)methyl]benzenesulfonamide;
3-[({4-fluoro-3-[2-(piperidin-4-yl)-1H-pyrrolo[2,3-b]pyridin-4-yl]phenyl}amino)methyl]phenol;
4-fluoro-3-[2-(piperidin-4-yl)-1H-pyrrolo[2,3-b]pyridin-4-yl]-N-(pyridin-2-ylmethyl)aniline;
4-fluoro-N-[3-(methylsulfonyl)benzyl]-3-[2-(piperidin-4-yl)-1H-pyrrolo[2,3-b]pyridin-4-yl]aniline;
N-(4-fluoro-3-{2-[1-(methylsulfonyl)piperidin-4-yl]-1H-pyrrolo[2,3-b]pyridin-4-yl}phenyl)methanesulfonamide;
N-benzyl-4-fluoro-3-{2-[1-(methylsulfonyl)piperidin-4-yl]-1H-pyrrolo[2,3-b]pyridin-4-yl}aniline;
N-(3-chlorobenzyl)-4-fluoro-3-{2-[1-(methylsulfonyl)piperidin-4-yl]-1H-pyrrolo[2,3-b]pyridin-4-yl}aniline;
4-fluoro-N-(3-fluorobenzyl)-3-{2-[1-(methylsulfonyl)piperidin-4-yl]-1H-pyrrolo[2,3-b]pyridin-4-yl}aniline;
4-(5-fluoro-2-methoxyphenyl)-2-(2,2,6,6-tetramethyl-1,2,3,6-tetrahydropyridin-4-yl)-1H-pyrrolo[2,3-b]pyridine;
4-fluoro-3-{2-[1-(methylsulfonyl)piperidin-4-yl]-1H-pyrrolo[2,3-b]pyridin-4-yl}-N-(pyridin-4-ylmethyl)aniline;
4-{[(4-fluoro-3-{2-[1-(methylsulfonyl)piperidin-4-yl]-1H-pyrrolo[2,3-b]pyridin-4-yl}phenyl)amino]methyl}benzonitrile;
4-{2-fluoro-5-[(3-fluorobenzyl)oxy]phenyl}-2-(1,2,3,6-tetrahydropyridin-4-yl)-1H-pyrrolo[2,3-b]pyridine;
2-({4-[4-(5-fluoro-2-methoxyphenyl)-1H-pyrrolo[2,3-b]pyridin-2-yl]piperidin-1-yl}methyl)-1H-benzimidazole;
4-(5-fluoro-2-methoxyphenyl)-2-[1-(tetrahydrofuran-2-ylmethyl)piperidin-4-yl]-1H-pyrrolo[2,3-b]pyridine;
2-[1-(5,6-dihydro-2H-pyran-3-ylmethyl)piperidin-4-yl]-4-(5-fluoro-2-methoxyphenyl)-1H-pyrrolo[2,3-b]pyridine;
4-(5-fluoro-2-methoxyphenyl)-2-[1-(4-methoxybenzyl)piperidin-4-yl]-1H-pyrrolo[2,3-b]pyridine;
4-(5-fluoro-2-methoxyphenyl)-2-{1-[2-(morpholin-4-yl)ethyl]piperidin-4-yl}-1H-pyrrolo[2,3-b]pyridine;
4-({4-[4-(5-fluoro-2-methoxyphenyl)-1H-pyrrolo[2,3-b]pyridin-2-yl]piperidin-1-yl}methyl)benzonitrile;
1-(2-{4-[4-(5-fluoro-2-methoxyphenyl)-1H-pyrrolo[2,3-b]pyridin-2-yl]-3,6-dihydropyridin-1(2H)-yl}ethyl)-3-methylurea;
4-(5-fluoro-2-methoxyphenyl)-2-[1-(2-methylpropyl)piperidin-4-yl]-1H-pyrrolo[2,3-b]pyridine;
N-[4-({4-[4-(5-fluoro-2-methoxyphenyl)-1H-pyrrolo[2,3-b]pyridin-2-yl]piperidin-1-yl}methyl)phenyl]acetamide;
4-(5-fluoro-2-methoxyphenyl)-2-[1-(pyridin-2-ylmethyl)piperidin-4-yl]-1H-pyrrolo[2,3-b]pyridine;
4-({4-[4-(5-fluoro-2-methoxyphenyl)-1H-pyrrolo[2,3-b]pyridin-2-yl]piperidin-1-yl}methyl)-N,N-dimethylaniline;
2-{1-[(1-tert-butyl-1H-pyrazol-4-yl)methyl]piperidin-4-yl}-4-(5-fluoro-2-methoxyphenyl)-1H-pyrrolo[2,3-b]pyridine;
4-(5-fluoro-2-methoxyphenyl)-2-[1-(2-methoxyethyl)piperidin-4-yl]-1H-pyrrolo[2,3-b]pyridine;
4-(5-fluoro-2-methoxyphenyl)-2-[1-(pyridin-4-ylmethyl)piperidin-4-yl]-1H-pyrrolo[2,3-b]pyridine;
N,N-diethyl-2-[4-({4-[4-(5-fluoro-2-methoxyphenyl)-1H-pyrrolo[2,3-b]pyridin-2-yl]piperidin-1-yl}methyl)phenoxy]ethanamine;

4-chloro-5-({4-[4-(5-fluoro-2-methoxyphenyl)-1H-pyrrolo[2,3-b]pyridin-2-yl]piperidin-1-yl}methyl)-1,3-thiazol-2-amine;

2-[1-(1,3-benzodioxol-5-ylmethyl)piperidin-4-yl]-4-(5-fluoro-2-methoxyphenyl)-1H-pyrrolo[2,3-b]pyridine;

3-{[(4-fluoro-3-{2-[1-(methylsulfonyl)piperidin-4-yl]-1H-pyrrolo[2,3-b]pyridin-4-yl}phenyl)amino]methyl}phenol;

4-fluoro-N-[3-(methylsulfonyl)benzyl]-3-{2-[1-(methylsulfonyl)piperidin-4-yl]-1H-pyrrolo[2,3-b]pyridin-4-yl}aniline;

4-{[(4-fluoro-3-{2-[1-(methylsulfonyl)piperidin-4-yl]-1H-pyrrolo[2,3-b]pyridin-4-yl}phenyl)amino]methyl}benzamide;

4-{[(4-fluoro-3-{2-[1-(methylsulfonyl)piperidin-4-yl]-1H-pyrrolo[2,3-b]pyridin-4-yl}phenyl)amino]methyl}phenol;

4-(5-fluoro-2-methoxyphenyl)-2-{1-[2-(morpholin-4-yl)ethyl]-1,2,3,6-tetrahydropyridin-4-yl}-1H-pyrrolo[2,3-b]pyridine;

2-{1-[(3-chlorobenzyl)sulfonyl]-1,2,3,6-tetrahydropyridin-4-yl}-4-(5-fluoro-2-methoxyphenyl)-1H-pyrrolo[2,3-b]pyridine;

2,4-difluoro-5-{2-[1-(methylsulfonyl)-1,2,3,6-tetrahydropyridin-4-yl]-1H-pyrrolo[2,3-b]pyridin-4-yl}-N-(tetrahydro-2H-pyran-4-ylmethyl)aniline;

2,4-difluoro-N-(tetrahydro-2H-pyran-4-ylmethyl)-5-[2-(1,2,3,6-tetrahydropyridin-4-yl)-1H-pyrrolo[2,3-b]pyridin-4-yl]aniline;

2,4-difluoro-N-(3-fluorobenzyl)-5-[2-(1,2,3,6-tetrahydropyridin-4-yl)-1H-pyrrolo[2,3-b]pyridin-4-yl]aniline;

N-(3,5-difluorobenzyl)-4-fluoro-3-{2-[1-(methylsulfonyl)-1,2,3,6-tetrahydropyridin-4-yl]-1H-pyrrolo[2,3-b]pyridin-4-yl}aniline;

4-[4-(5-fluoro-2-methoxyphenyl)-1H-pyrrolo[2,3-b]pyridin-2-yl]-N-(propan-2-yl)-3,6-dihydropyridine-1(2H)-carboxamide;

2-(1-ethyl-1,2,3,6-tetrahydropyridin-4-yl)-4-(5-fluoro-2-methoxyphenyl)-1H-pyrrolo[2,3-b]pyridine;

2-(1-benzyl-1,2,3,6-tetrahydropyridin-4-yl)-4-(5-fluoro-2-methoxyphenyl)-1H-pyrrolo[2,3-b]pyridine;

4-fluoro-3-{2-[1-(methylsulfonyl)piperidin-4-yl]-1H-pyrrolo[2,3-b]pyridin-4-yl}-N-(pyridin-3-ylmethyl)aniline;

N-(3,5-difluorobenzyl)-4-fluoro-3-{2-[1-(methylsulfonyl)piperidin-4-yl]-1H-pyrrolo[2,3-b]pyridin-4-yl}aniline;

N-(3,4-difluorobenzyl)-4-fluoro-3-{2-[1-(methylsulfonyl)piperidin-4-yl]-1H-pyrrolo[2,3-b]pyridin-4-yl}aniline;

N-(3,4-difluorobenzyl)-4-fluoro-3-[2-(1-methylpiperidin-4-yl)-1H-pyrrolo[2,3-b]pyridin-4-yl]aniline;

1-[4-(4-{5-[(3,5-difluorobenzyl)amino]-2-fluorophenyl}-1H-pyrrolo[2,3-b]pyridin-2-yl)piperidin-1-yl]-2-hydroxyethanone;

3-[4-(4-{2-fluoro-5-[(pyridin-3-ylmethyl)amino]phenyl}-1H-pyrrolo[2,3-b]pyridin-2-yl)piperidin-1-yl]propane-1,2-diol;

3-[4-(4-{2-fluoro-5-[(pyridin-4-ylmethyl)amino]phenyl}-1H-pyrrolo[2,3-b]pyridin-2-yl)piperidin-1-yl]propane-1,2-diol;

4-{[(3-{2-[1-(2,3-dihydroxypropyl)piperidin-4-yl]-1H-pyrrolo[2,3-b]pyridin-4-yl}-4-fluorophenyl)amino]methyl}benzonitrile;

3-{[(3-{2-[1-(2,3-dihydroxypropyl)piperidin-4-yl]-1H-pyrrolo[2,3-b]pyridin-4-yl}-4-fluorophenyl)amino]methyl}benzonitrile;

3-{2-[1-(cyclopropylsulfonyl)piperidin-4-yl]-1H-pyrrolo[2,3-b]pyridin-4-yl}-4-fluoro-N-(pyridin-4-ylmethyl)aniline;

4-{[(3-{2-[1-(cyclopropylsulfonyl)piperidin-4-yl]-1H-pyrrolo[2,3-b]pyridin-4-yl}-4-fluorophenyl)amino]methyl}benzonitrile;

3-{2-[1-(cyclopropylsulfonyl)piperidin-4-yl]-1H-pyrrolo[2,3-b]pyridin-4-yl}-N-(3,5-difluorobenzyl)-4-fluoroaniline;

3-{2-[1-(cyclopropylsulfonyl)piperidin-4-yl]-1H-pyrrolo[2,3-b]pyridin-4-yl}-4-fluoro-N-[3-(methylsulfonyl)benzyl]aniline;

4-(4-{2-fluoro-5-[(3-fluorobenzyl)amino]phenyl}-1H-pyrrolo[2,3-b]pyridin-2-yl)piperidine-1-sulfonamide;

3-[4-(4-{2-fluoro-5-[(3-fluorobenzyl)amino]phenyl}-1H-pyrrolo[2,3-b]pyridin-2-yl)piperidin-1-yl]propane-1,2-diol;

4-(5-fluoro-2-methoxyphenyl)-2-[4-(pyrrolidin-1-yl)cyclohex-1-en-1-yl]-1H-pyrrolo[2,3-b]pyridine;

4-(5-fluoro-2-methoxyphenyl)-2-[1-(methylsulfonyl)-2,5-dihydro-1H-pyrrol-3-yl]-1H-pyrrolo[2,3-b]pyridine;

3-[4-(4-{2-fluoro-5-[(3-fluorobenzyl)oxy]phenyl}-1H-pyrrolo[2,3-b]pyridin-2-yl)-3,6-dihydropyridin-1(2H)-yl]propane-1,2-diol;

3-[4-(4-{2,4-difluoro-5-[(3-fluorobenzyl)amino]phenyl}-1H-pyrrolo[2,3-b]pyridin-2-yl)-3,6-dihydropyridin-1(2H)-yl]propane-1,2-diol;

2-({4-[4-(5-fluoro-2-methoxyphenyl)-1H-pyrrolo[2,3-b]pyridin-2-yl]-3,6-dihydropyridin-1(2H)-yl}methyl)-1H-benzimidazole;

2-[1-(5,6-dihydro-2H-pyran-3-ylmethyl)-1,2,3,6-tetrahydropyridin-4-yl]-4-(5-fluoro-2-methoxyphenyl)-1H-pyrrolo[2,3-b]pyridine;

4-({4-[4-(5-fluoro-2-methoxyphenyl)-1H-pyrrolo[2,3-b]pyridin-2-yl]-3,6-dihydropyridin-1(2H)-yl}methyl)-N,N-dimethylaniline;

N,N-diethyl-2-[4-({4-[4-(5-fluoro-2-methoxyphenyl)-1H-pyrrolo[2,3-b]pyridin-2-yl]-3,6-dihydropyridin-1(2H)-yl}methyl)phenoxy]ethanamine;

4-(5-fluoro-2-methoxyphenyl)-2-[1-(pyridin-4-ylmethyl)-1,2,3,6-tetrahydropyridin-4-yl]-1H-pyrrolo[2,3-b]pyridine;

4-({4-[4-(5-fluoro-2-methoxyphenyl)-1H-pyrrolo[2,3-b]pyridin-2-yl]-3,6-dihydropyridin-1(2H)-yl}methyl)benzonitrile;

4-chloro-5-({4-[4-(5-fluoro-2-methoxyphenyl)-1H-pyrrolo[2,3-b]pyridin-2-yl]-3,6-dihydropyridin-1(2H)-yl}methyl)-1,3-thiazol-2-amine;

4-(5-fluoro-2-methoxyphenyl)-2-[1-(tetrahydrofuran-2-ylmethyl)-1,2,3,6-tetrahydropyridin-4-yl]-1H-pyrrolo[2,3-b]pyridine;

4-chloro-3-[2-(2,5-dihydro-1H-pyrrol-3-yl)-1H-pyrrolo[2,3-b]pyridin-4-yl]-N-(pyridin-3-ylmethyl)aniline;

4-chloro-3-[2-(2,5-dihydro-1H-pyrrol-3-yl)-1H-pyrrolo[2,3-b]pyridin-4-yl]-N-(3-fluorobenzyl)aniline;

4-chloro-3-[2-(2,5-dihydro-1H-pyrrol-3-yl)-1H-pyrrolo[2,3-b]pyridin-4-yl]-N-(tetrahydro-2H-pyran-3-ylmethyl)aniline;

4-chloro-3-[2-(2,5-dihydro-1H-pyrrol-3-yl)-1H-pyrrolo[2,3-b]pyridin-4-yl]-N-(piperidin-4-ylmethyl)aniline;

5-fluoro-4-(5-fluoro-2-methoxyphenyl)-2-(piperidin-4-yl)-1H-pyrrolo[2,3-b]pyridine;

N-cyclohexyl-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(4-methoxybenzyl)-3,6-dihydropyridine-1(2H)-carboxamide;

4-[4-(5-fluoro-2-methoxyphenyl)-1H-pyrrolo[2,3-b]pyridin-2-yl]-N-phenyl-3,6-dihydropyridine-1(2H)-carboxamide;

4-(4-{2-fluoro-5-[(pyridin-4-ylmethyl)amino]phenyl}-1H-pyrrolo[2,3-b]pyridin-2-yl)piperidine-1-sulfonamide;
5-fluoro-4-(5-fluoro-2-methoxyphenyl)-2-[1-(methylsulfonyl)piperidin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]piperidin-1-yl}propane-1,2-diol;
1-{4-[5-fluoro-4-(5-fluoro-2-methoxyphenyl)-1H-pyrrolo[2,3-b]pyridin-2-yl]piperidin-1-yl}ethanone;
3-[4-(4-{5-[(3,5-difluorobenzyl)amino]-2-fluorophenyl}-1H-pyrrolo[2,3-b]pyridin-2-yl)piperidin-1-yl]propane-1,2-diol;
4-[4-(5-fluoro-2-methoxyphenyl)-1H-pyrrolo[2,3-b]pyridin-2-yl]-N-[2-(morpholin-4-yl)ethyl]-3,6-dihydropyridine-1(2H)-carboxamide;
4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine;
{4-[4-(5-fluoro-2-methoxyphenyl)-1H-pyrrolo[2,3-b]pyridin-2-yl]-3,6-dihydropyridin-1(2H)-yl}(pyridin-2-yl)methanone;
{4-[4-(5-fluoro-2-methoxyphenyl)-1H-pyrrolo[2,3-b]pyridin-2-yl]-3,6-dihydropyridin-1(2H)-yl}(pyridin-3-yl)methanone;
{4-[4-(5-fluoro-2-methoxyphenyl)-1H-pyrrolo[2,3-b]pyridin-2-yl]-3,6-dihydropyridin-1(2H)-yl}(pyridin-4-yl)methanone;
{4-[4-(5-fluoro-2-methoxyphenyl)-1H-pyrrolo[2,3-b]pyridin-2-yl]-3,6-dihydropyridin-1(2H)-yl}(pyrazin-2-yl)methanone;
4-(5-fluoro-2-methoxyphenyl)-2-[1-(pyrimidin-4-yl)-1,2,3,6-tetrahydropyridin-4-yl]-1H-pyrrolo[2,3-b]pyridine;
4-(5-fluoro-2-methoxyphenyl)-2-[1-(2-methylpyrimidin-4-yl)-1,2,3,6-tetrahydropyridin-4-yl]-1H-pyrrolo[2,3-b]pyridine;
4-(5-fluoro-2-methoxyphenyl)-2-{1-[6-(trifluoromethyl)pyrimidin-4-yl]-1,2,3,6-tetrahydropyridin-4-yl}-1H-pyrrolo[2,3-b]pyridine;
1-{4-[4-(5-fluoro-2-methoxyphenyl)-1H-pyrrolo[2,3-b]pyridin-2-yl]-3,6-dihydropyridin-1(2H)-yl}-3-(piperidin-1-yl)propan-1-one;
{4-[4-(5-fluoro-2-methoxyphenyl)-1H-pyrrolo[2,3-b]pyridin-2-yl]-3,6-dihydropyridin-1(2H)-yl}(1H-pyrazol-4-yl)methanone;
{4-[4-(5-fluoro-2-methoxyphenyl)-1H-pyrrolo[2,3-b]pyridin-2-yl]-3,6-dihydropyridin-1(2H)-yl}(1,3-thiazol-4-yl)methanone;
(3,5-dimethyl-1,2-oxazol-4-yl) {4-[4-(5-fluoro-2-methoxyphenyl)-1H-pyrrolo[2,3-b]pyridin-2-yl]-3,6-dihydropyridin-1(2H)-yl}methanone;
4-(2-chloro-5-methoxyphenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-(2,3,4-trifluorophenyl)-1H-pyrrolo[2,3-b]pyridine;
2-[1-(methylsulfonyl)-1,2,3,6-tetrahydropyridin-4-yl]-4-[3-(trifluoromethoxy)phenyl]-1H-pyrrolo[2,3-b]pyridine;
N-(2-{4-[4-(5-fluoro-2-methoxyphenyl)-1H-pyrrolo[2,3-b]pyridin-2-yl]-3,6-dihydropyridin-1(2H)-yl}ethyl)-$N^2,N^2$-dimethylglycinamide;
4-(4-methoxyphenyl)-2-[1-(methylsulfonyl)-1,2,3,6-tetrahydropyridin-4-yl]-1H-pyrrolo[2,3-b]pyridine;
4-(3,4-difluorophenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[2-(trifluoromethoxy)phenyl]-1H-pyrrolo[2,3-b]pyridine;
4-[5-fluoro-2-(propan-2-yloxy)phenyl]-2-[1-(methylsulfonyl)-1,2,3,6-tetrahydropyridin-4-yl]-1H-pyrrolo[2,3-b]pyridine;
4-[2-(cyclopropyloxy)-5-fluorophenyl]-2-[1-(methylsulfonyl)-1,2,3,6-tetrahydropyridin-4-yl]-1H-pyrrolo[2,3-b]pyridine;
4-(4-ethoxy-3-fluorophenyl)-2-[1-(methylsulfonyl)-1,2,3,6-tetrahydropyridin-4-yl]-1H-pyrrolo[2,3-b]pyridine;
4-(4-{5-[(3,5-difluorobenzyl)amino]-2-fluorophenyl}-1H-pyrrolo[2,3-b]pyridin-2-yl)piperidine-1-sulfonamide;
4-(4-chloro-3-methylphenyl)-2-[1-(methylsulfonyl)-1,2,3,6-tetrahydropyridin-4-yl]-1H-pyrrolo[2,3-b]pyridine;
4-(3-chloro-4-fluorophenyl)-2-[1-(methylsulfonyl)-1,2,3,6-tetrahydropyridin-4-yl]-1H-pyrrolo[2,3-b]pyridine;
N,N-dimethyl-3-{2-[1-(methylsulfonyl)-1,2,3,6-tetrahydropyridin-4-yl]-1H-pyrrolo[2,3-b]pyridin-4-yl}benzamide;
4-(4-fluoro-3-methylphenyl)-2-[1-(methylsulfonyl)-1,2,3,6-tetrahydropyridin-4-yl]-1H-pyrrolo[2,3-b]pyridine;
4-[3-fluoro-4-(propan-2-yloxy)phenyl]-2-[1-(methylsulfonyl)-1,2,3,6-tetrahydropyridin-4-yl]-1H-pyrrolo[2,3-b]pyridine;
4-(4-butoxy-3-fluorophenyl)-2-[1-(methylsulfonyl)-1,2,3,6-tetrahydropyridin-4-yl]-1H-pyrrolo[2,3-b]pyridine;
(3-{2-[1-(methylsulfonyl)-1,2,3,6-tetrahydropyridin-4-yl]-1H-pyrrolo[2,3-b]pyridin-4-yl}phenyl)(morpholin-4-yl)methanone;
N-(3,5-difluorobenzyl)-4-fluoro-3-[2-(1,2,3,6-tetrahydropyridin-4-yl)-1H-pyrrolo[2,3-b]pyridin-4-yl]aniline;
4-(5-fluoro-2-methoxyphenyl)-2-(1,2,5,6-tetrahydropyridin-3-yl)-1H-pyrrolo[2,3-b]pyridine;
4-(3,5-difluorophenyl)-2-[1-(methylsulfonyl)-1,2,3,6-tetrahydropyridin-4-yl]-1H-pyrrolo[2,3-b]pyridine;
4-(2,4-dichlorophenyl)-2-[1-(methylsulfonyl)-1,2,3,6-tetrahydropyridin-4-yl]-1H-pyrrolo[2,3-b]pyridine;
4-(2-ethylphenyl)-2-[1-(methylsulfonyl)-1,2,3,6-tetrahydropyridin-4-yl]-1H-pyrrolo[2,3-b]pyridine;
4-(2,4-dimethylphenyl)-2-[1-(methylsulfonyl)-1,2,3,6-tetrahydropyridin-4-yl]-1H-pyrrolo[2,3-b]pyridine;
4-(2,5-dichlorophenyl)-2-[1-(methylsulfonyl)-1,2,3,6-tetrahydropyridin-4-yl]-1H-pyrrolo[2,3-b]pyridine;
4-(3,4-dichlorophenyl)-2-[1-(methylsulfonyl)-1,2,3,6-tetrahydropyridin-4-yl]-1H-pyrrolo[2,3-b]pyridine;
N-(4-{2-[1-(methylsulfonyl)-1,2,3,6-tetrahydropyridin-4-yl]-1H-pyrrolo[2,3-b]pyridin-4-yl}phenyl)methanesulfonamide;
4-(5-chloro-2-methoxyphenyl)-2-[1-(methylsulfonyl)-1,2,3,6-tetrahydropyridin-4-yl]-1H-pyrrolo[2,3-b]pyridine;
4-[2-methoxy-5-(propan-2-yl)phenyl]-2-[1-(methylsulfonyl)-1,2,3,6-tetrahydropyridin-4-yl]-1H-pyrrolo[2,3-b]pyridine;
4-(2-methoxy-5-methylphenyl)-2-[1-(methylsulfonyl)-1,2,3,6-tetrahydropyridin-4-yl]-1H-pyrrolo[2,3-b]pyridine;
4-(4-methoxy-3-methylphenyl)-2-[1-(methylsulfonyl)-1,2,3,6-tetrahydropyridin-4-yl]-1H-pyrrolo[2,3-b]pyridine;
2-{2-[1-(methylsulfonyl)-1,2,3,6-tetrahydropyridin-4-yl]-1H-pyrrolo[2,3-b]pyridin-4-yl}benzonitrile;
4-(2-methoxyphenyl)-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}benzonitrile;
2-[1-(methylsulfonyl)-1,2,3,6-tetrahydropyridin-4-yl]-4-[2-(trifluoromethyl)phenyl]-1H-pyrrolo[2,3-b]pyridine;
4-(3-chlorophenyl)-2-[1-(methylsulfonyl)-1,2,3,6-tetrahydropyridin-4-yl]-1H-pyrrolo[2,3-b]pyridine;
4-(2-chlorophenyl)-2-[1-(methylsulfonyl)-1,2,3,6-tetrahydropyridin-4-yl]-1H-pyrrolo[2,3-b]pyridine;
4-[2-fluoro-5-(trifluoromethyl)phenyl]-2-[1-(methylsulfonyl)-1,2,3,6-tetrahydropyridin-4-yl]-1H-pyrrolo[2,3-b]pyridine;

4-(3-chloro-4-methoxyphenyl)-2-[1-(methylsulfonyl)-1,2,3,6-tetrahydropyridin-4-yl]-1H-pyrrolo[2,3-b]pyridine;
4-(2-fluoro-5-methylphenyl)-2-[1-(methylsulfonyl)-1,2,3,6-tetrahydropyridin-4-yl]-1H-pyrrolo[2,3-b]pyridine;
4-(5-chloro-2-fluoro-3-methylphenyl)-2-[1-(methylsulfonyl)-1,2,3,6-tetrahydropyridin-4-yl]-1H-pyrrolo[2,3-b]pyridine;
4-(5-chloro-2-propoxyphenyl)-2-[1-(methylsulfonyl)-1,2,3,6-tetrahydropyridin-4-yl]-1H-pyrrolo[2,3-b]pyridine;
4-(4-{5-[(3,5-difluorobenzyl)amino]-2-fluorophenyl}-1H-pyrrolo[2,3-b]pyridin-2-yl)-N-methyl-3,6-dihydropyridine-1(2H)-carboxamide;
3-[4-(4-{5-[(3,5-difluorobenzyl)amino]-2-fluorophenyl}-1H-pyrrolo[2,3-b]pyridin-2-yl)-3,6-dihydropyridin-1(2H)-yl]propane-1,2-diol;
ethyl 4-[4-(5-fluoro-2-methoxyphenyl)-1H-pyrrolo[2,3-b]pyridin-2-yl]cyclohex-3-ene-1-carboxylate;
4-(2-ethoxy-5-fluorophenyl)-2-[1-(methylsulfonyl)-1,2,3,6-tetrahydropyridin-4-yl]-1H-pyrrolo[2,3-b]pyridine;
4-(2,3-dichlorophenyl)-2-[1-(methylsulfonyl)-1,2,3,6-tetrahydropyridin-4-yl]-1H-pyrrolo[2,3-b]pyridine;
4-(3-chloro-4-methylphenyl)-2-[1-(methylsulfonyl)-1,2,3,6-tetrahydropyridin-4-yl]-1H-pyrrolo[2,3-b]pyridine;
2-methyl-5-{2-[1-(methylsulfonyl)-1,2,3,6-tetrahydropyridin-4-yl]-1H-pyrrolo[2,3-b]pyridin-4-yl}aniline;
4-(2-fluorobiphenyl-4-yl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[3-(propan-2-yloxy)phenyl]-1H-pyrrolo[2,3-b]pyridine;
4-(3-fluoro-4-propoxyphenyl)-2-[1-(methylsulfonyl)-1,2,3,6-tetrahydropyridin-4-yl]-1H-pyrrolo[2,3-b]pyridine;
4-[2-fluoro-5-(propan-2-yloxy)phenyl]-2-[1-(methylsulfonyl)-1,2,3,6-tetrahydropyridin-4-yl]-1H-pyrrolo[2,3-b]pyridine;
4-(4-butoxy-3-chlorophenyl)-2-[1-(methylsulfonyl)-1,2,3,6-tetrahydropyridin-4-yl]-1H-pyrrolo[2,3-b]pyridine;
4-[2-(2-methylpropoxy)phenyl]-2-[1-(methylsulfonyl)-1,2,3,6-tetrahydropyridin-4-yl]-1H-pyrrolo[2,3-b]pyridine;
4-{2-[1-(methylsulfonyl)-1,2,3,6-tetrahydropyridin-4-yl]-1H-pyrrolo[2,3-b]pyridin-4-yl}benzonitrile;
2-[1-(methylsulfonyl)-1,2,3,6-tetrahydropyridin-4-yl]-4-phenyl-1H-pyrrolo[2,3-b]pyridine;
(4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid;
4-(3-fluoro-4-methoxyphenyl)-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}aniline;
N-(2-{2-[1-(methylsulfonyl)-1,2,3,6-tetrahydropyridin-4-yl]-1H-pyrrolo[2,3-b]pyridin-4-yl}phenyl)methanesulfonamide;
3-{2-[1-(methylsulfonyl)-1,2,3,6-tetrahydropyridin-4-yl]-1H-pyrrolo[2,3-b]pyridin-4-yl}-N-(propan-2-yl)benzamide;
2-{4-[3-cyano-4-(5-fluoro-2-methoxyphenyl)-1H-pyrrolo[2,3-b]pyridin-2-yl]piperazin-1-yl}-N,N-dimethylacetamide;
(4-{2-[1-(methylsulfonyl)-1,2,3,6-tetrahydropyridin-4-yl]-1H-pyrrolo[2,3-b]pyridin-4-yl}phenyl)acetonitrile;
N-methyl-4-{2-[1-(methylsulfonyl)-1,2,3,6-tetrahydropyridin-4-yl]-1H-pyrrolo[2,3-b]pyridin-4-yl}benzamide;
N-(3-{2-[1-(methylsulfonyl)-1,2,3,6-tetrahydropyridin-4-yl]-1H-pyrrolo[2,3-b]pyridin-4-yl}phenyl)acetamide;
N-(4-{2-[1-(methylsulfonyl)-1,2,3,6-tetrahydropyridin-4-yl]-1H-pyrrolo[2,3-b]pyridin-4-yl}phenyl)acetamide;
4-[4-(5-fluoro-2-methoxyphenyl)-1H-pyrrolo[2,3-b]pyridin-2-yl]-N-methyl-3,6-dihydropyridine-1(2H)-sulfonamide;
4-(5-fluoro-2-methoxyphenyl)-2-[1-(pyridin-2-ylmethyl)-1,2,3,6-tetrahydropyridin-4-yl]-1H-pyrrolo[2,3-b]pyridine;
3-{5-[4-(5-fluoro-2-methoxyphenyl)-1H-pyrrolo[2,3-b]pyridin-2-yl]-3,6-dihydropyridin-1(2H)-yl}propane-1,2-diol;
5-[4-(5-fluoro-2-methoxyphenyl)-1H-pyrrolo[2,3-b]pyridin-2-yl]-N-methyl-3,6-dihydropyridine-1(2H)-carboxamide;
4-(5-fluoro-2-methoxyphenyl)-2-[1-(methylsulfonyl)-1,2,5,6-tetrahydropyridin-3-yl]-1H-pyrrolo[2,3-b]pyridine;
4-(5-fluoro-2-methylphenyl)-2-[1-(methylsulfonyl)-1,2,3,6-tetrahydropyridin-4-yl]-1H-pyrrolo[2,3-b]pyridine;
4-{5-[(3,5-difluorobenzyl)oxy]-2-fluorophenyl}-2-(1,2,3,6-tetrahydropyridin-4-yl)-1H-pyrrolo[2,3-b]pyridine;
4-{5-[(3,5-difluorobenzyl)oxy]-2-fluorophenyl}-2-(1-methyl-1,2,3,6-tetrahydropyridin-4-yl)-1H-pyrrolo[2,3-b]pyridine;
3-[4-(4-{5-[(3,5-difluorobenzyl)oxy]-2-fluorophenyl}-1H-pyrrolo[2,3-b]pyridin-2-yl)-3,6-dihydropyridin-1(2H)-yl]propane-1,2-diol;
4-{5-[(3,5-difluorobenzyl)oxy]-2-fluorophenyl}-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}benzamide;
4-(4-ethoxy-2-methylphenyl)-2-[1-(methylsulfonyl)-1,2,3,6-tetrahydropyridin-4-yl]-1H-pyrrolo[2,3-b]pyridine;
4-(4-chloro-3-(trifluoromethyl)phenyl)-2-[1-(methylsulfonyl)-1,2,3,6-tetrahydropyridin-4-yl]-1H-pyrrolo[2,3-b]pyridine;
N-butyl-3-{2-[1-(methylsulfonyl)-1,2,3,6-tetrahydropyridin-4-yl]-1H-pyrrolo[2,3-b]pyridin-4-yl}benzamide;
4-(3-fluorophenyl)-2-[1-(methylsulfonyl)-1,2,3,6-tetrahydropyridin-4-yl]-1H-pyrrolo[2,3-b]pyridine;
4-{3-chloro-4-[(3-chlorobenzyl)oxy]phenyl}-2-[1-(methylsulfonyl)-1,2,3,6-tetrahydropyridin-4-yl]-1H-pyrrolo[2,3-b]pyridine;
4-(4-fluoro-2-methoxyphenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[4-(trifluoromethoxy)phenyl]-1H-pyrrolo[2,3-b]pyridine;
4-[3-chloro-4-(propan-2-yloxy)phenyl]-2-[1-(methylsulfonyl)-1,2,3,6-tetrahydropyridin-4-yl]-1H-pyrrolo[2,3-b]pyridine;
4-(3,5-dichlorophenyl)-2-[1-(methylsulfonyl)-1,2,3,6-tetrahydropyridin-4-yl]-1H-pyrrolo[2,3-b]pyridine;
4-(4-fluoro-2-propoxyphenyl)-2-[1-(methylsulfonyl)-1,2,3,6-tetrahydropyridin-4-yl]-1H-pyrrolo[2,3-b]pyridine;
4-(5-fluoro-2-methoxyphenyl)-2-[1-(morpholin-4-ylsulfonyl)-1,2,3,6-tetrahydropyridin-4-yl]-1H-pyrrolo[2,3-b]pyridine;
2-fluoro-N-{4-methoxy-3-[2-(1,2,3,6-tetrahydropyridin-4-yl)-1H-pyrrolo[2,3-b]pyridin-4-yl]benzyl}aniline;
N-{4-methoxy-3-[2-(1,2,3,6-tetrahydropyridin-4-yl)-1H-pyrrolo[2,3-b]pyridin-4-yl]benzyl}tetrahydro-2H-pyran-4-amine;
4-[2-methoxy-5-(morpholin-4-ylmethyl)phenyl]-2-(1,2,3,6-tetrahydropyridin-4-yl)-1H-pyrrolo[2,3-b]pyridine;
N-benzyl-4-[4-(5-fluoro-2-methoxyphenyl)-1H-pyrrolo[2,3-b]pyridin-2-yl]cyclohex-3-ene-1-carboxamide;
N-(3-fluorobenzyl)-4-[4-(5-fluoro-2-methoxyphenyl)-1H-pyrrolo[2,3-b]pyridin-2-yl]cyclohex-3-ene-1-carboxamide;

N-(3,5-difluorobenzyl)-4-[4-(5-fluoro-2-methoxyphenyl)-1H-pyrrolo[2,3-b]pyridin-2-yl]cyclohex-3-ene-1-carboxamide;

N-(2,5-difluorobenzyl)-4-[4-(5-fluoro-2-methoxyphenyl)-1H-pyrrolo[2,3-b]pyridin-2-yl]cyclohex-3-ene-1-carboxamide;

N-(3-chlorobenzyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(pyridin-4-ylmethyl)cyclohex-3-ene-1-carboxamide;

4-[4-(5-fluoro-2-methoxyphenyl)-1H-pyrrolo[2,3-b]pyridin-2-yl]-N-[(3-methyl-1H-pyrazol-5-yl)methyl]cyclohex-3-ene-1-carboxamide;

4-[4-(5-fluoro-2-methoxyphenyl)-1H-pyrrolo[2,3-b]pyridin-2-yl]-N-(tetrahydro-2H-pyran-4-ylmethyl)cyclohex-3-ene-1-carboxamide;

4-[4-(5-fluoro-2-methoxyphenyl)-1H-pyrrolo[2,3-b]pyridin-2-yl]-N-(4-hydroxycyclohexyl)cyclohex-3-ene-1-carboxamide;

(3,3-difluoroazetidin-1-yl) {4-[4-(5-fluoro-2-methoxyphenyl)-1H-pyrrolo[2,3-b]pyridin-2-yl]cyclohex-3-en-1-yl}methanone;

2-(3,6-dihydro-2H-pyran-4-yl)-4-(5-fluoro-2-methoxyphenyl)-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}(tetrahydro-2H-pyran-3-yl)methanone;

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]-2-hydroxyethanone;

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]ethanone;

1-{5-[4-(5-fluoro-2-methoxyphenyl)-1H-pyrrolo[2,3-b]pyridin-2-yl]-3,6-dihydropyridin-1(2H)-yl}-2-hydroxyethanone;

1-{5-[4-(5-fluoro-2-methoxyphenyl)-1H-pyrrolo[2,3-b]pyridin-2-yl]-3,6-dihydropyridin-1(2H)-yl}ethanone;

N-[4-({5-[4-(5-fluoro-2-methoxyphenyl)-1H-pyrrolo[2,3-b]pyridin-2-yl]-3,6-dihydropyridin-1(2H)-yl}methyl)phenyl]acetamide;

4-(5-fluoro-2-methoxyphenyl)-2-[1-(tetrahydrofuran-2-ylmethyl)-1,2,5,6-tetrahydropyridin-3-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-methylpropan-2-ol;

4-[4-(5-fluoro-2-methoxyphenyl)-1H-pyrrolo[2,3-b]pyridin-2-yl]-N,N-dimethyl-3,6-dihydropyridine-1(2H)-carboxamide;

ethyl ({4-[4-(5-fluoro-2-methoxyphenyl)-1H-pyrrolo[2,3-b]pyridin-2-yl]piperidin-1-yl}sulfonyl)carbamate;

4-[4-(5-fluoro-2-methoxyphenyl)-1H-pyrrolo[2,3-b]pyridin-2-yl]-N-methylpiperidine-1-sulfonamide;

4-[4-(5-fluoro-2-methoxyphenyl)-1H-pyrrolo[2,3-b]pyridin-2-yl]-N,N-dimethylpiperidine-1-sulfonamide;

4-(5-fluoro-2-methoxyphenyl)-2-[4-(trifluoromethyl)cyclohex-1-en-1-yl]-1H-pyrrolo[2,3-b]pyridine;

4-[4-(5-fluoro-2-methoxyphenyl)-1H-pyrrolo[2,3-b]pyridin-2-yl]-N-(tetrahydro-2H-pyran-4-ylmethyl)cyclohex-3-en-1-amine;

2-{4-[4-(5-fluoro-2-methoxyphenyl)-1H-pyrrolo[2,3-b]pyridin-2-yl]piperidin-1-yl}ethanesulfonamide;

N-benzyl-4-[4-(5-fluoro-2-methoxyphenyl)-1H-pyrrolo[2,3-b]pyridin-2-yl]cyclohex-3-en-1-amine;

4-[4-(5-fluoro-2-methoxyphenyl)-1H-pyrrolo[2,3-b]pyridin-2-yl]-N-(pyridin-4-ylmethyl)cyclohex-3-en-1-amine;

4-[4-(5-fluoro-2-methoxyphenyl)-1H-pyrrolo[2,3-b]pyridin-2-yl]-N-(morpholin-2-ylmethyl)cyclohex-3-en-1-amine;

4-(5-fluoro-2-methoxyphenyl)-2-[1-(S-methylsulfonimidoyl)piperidin-4-yl]-1H-pyrrolo[2,3-b]pyridine;

N-ethyl-4-[4-(5-fluoro-2-methoxyphenyl)-1H-pyrrolo[2,3-b]pyridin-2-yl]piperidine-1-sulfonamide;

4-[3-(4-fluorophenoxy)phenyl]-2-(piperidin-4-yl)-1H-pyrrolo[2,3-b]pyridine;

4-(2,3-difluorophenyl)-2-(1,2,3,6-tetrahydropyridin-4-yl)-1H-pyrrolo[2,3-b]pyridine;

3-{4-[4-(2,3-difluorophenyl)-1H-pyrrolo[2,3-b]pyridin-2-yl]-3,6-dihydropyridin-1(2H)-yl}propane-1,2-diol;

N-[4-({4-[4-(2,3-difluorophenyl)-1H-pyrrolo[2,3-b]pyridin-2-yl]-3,6-dihydropyridin-1(2H)-yl}methyl)phenyl]acetamide;

1-{4-[4-(2,3-difluorophenyl)-1H-pyrrolo[2,3-b]pyridin-2-yl]-3,6-dihydropyridin-1(2H)-yl}-2-hydroxyethanone;

2-(8-azabicyclo[3.2.1]oct-2-en-3-yl)-4-(5-fluoro-2-methoxyphenyl)-1H-pyrrolo[2,3-b]pyridine;

N-(3,5-difluorobenzyl)-4-[4-(5-fluoro-2-methoxyphenyl)-1H-pyrrolo[2,3-b]pyridin-2-yl]cyclohex-3-en-1-amine;

3-[4-(5-fluoro-2-methoxyphenyl)-1H-pyrrolo[2,3-b]pyridin-2-yl]-N-methyl-8-azabicyclo[3.2.1]oct-2-ene-8-carboxamide;

3-{3-[4-(5-fluoro-2-methoxyphenyl)-1H-pyrrolo[2,3-b]pyridin-2-yl]-8-azabicyclo[3.2.1]oct-2-en-8-yl}propane-1,2-diol;

1-{3-[4-(5-fluoro-2-methoxyphenyl)-1H-pyrrolo[2,3-b]pyridin-2-yl]-8-azabicyclo[3.2.1]oct-2-en-8-yl}-2-hydroxyethanone;

3-[4-(5-fluoro-2-methoxyphenyl)-1H-pyrrolo[2,3-b]pyridin-2-yl]-N,N-dimethyl-8-azabicyclo[3.2.1]oct-2-ene-8-carboxamide;

N-[(2S)-2,3-dihydroxypropyl]-4-[4-(5-fluoro-2-methoxyphenyl)-1H-pyrrolo[2,3-b]pyridin-2-yl]piperidine-1-sulfonamide;

3-chloro-4-(5-fluoro-2-methoxyphenyl)-2-(piperidin-4-yl)-1H-pyrrolo[2,3-b]pyridine;

3-bromo-4-(5-fluoro-2-methoxyphenyl)-2-(piperidin-4-yl)-1H-pyrrolo[2,3-b]pyridine;

ethyl ({4-[3-bromo-4-(5-fluoro-2-methoxyphenyl)-1H-pyrrolo[2,3-b]pyridin-2-yl]piperidin-1-yl}sulfonyl)carbamate;

4-[4-(5-fluoro-2-methoxyphenyl)-1H-pyrrolo[2,3-b]pyridin-2-yl]-N-(2-hydroxyethyl)-3,6-dihydropyridine-1(2H)-carboxamide;

4-[4-(5-fluoro-2-methoxyphenyl)-1H-pyrrolo[2,3-b]pyridin-2-yl]-N-(methylsulfonyl)cyclohex-3-ene-1-carboxamide;

N-methyl-4-[2-(1,2,3,6-tetrahydropyridin-4-yl)-1H-pyrrolo[2,3-b]pyridin-4-yl]benzamide;

5-[4-(5-fluoro-2-methoxyphenyl)-1H-pyrrolo[2,3-b]pyridin-2-yl]-N,N-dimethyl-3,6-dihydropyridine-1(2H)-carboxamide;

4-[4-(5-fluoro-2-methoxyphenyl)-1H-pyrrolo[2,3-b]pyridin-2-yl]-N-(pyridin-3-ylmethyl)cyclohex-3-en-1-amine;

4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-[2-(pyrrolidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-[2-(4-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(tetrahydrofuran-2-ylmethyl)amino]ethyl}-3,6-dihydropyridine-1(2H)-carboxamide;

methyl 4-{2-[({4-[4-(5-fluoro-2-methoxyphenyl)-1H-pyrrolo[2,3-b]pyridin-2-yl]-3,6-dihydropyridin-1(2H)-yl}carbonyl)amino]ethyl}piperazine-1-carboxylate;

N-[2-(3,4-dihydroisoquinolin-2(1H)-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide;

1-{5-[4-(5-fluoro-2-methoxyphenyl)-1H-pyrrolo[2,3-b]pyridin-2-yl]-3,6-dihydropyridin-1(2H)-yl}-2-methylpropan-2-ol;

4-{2-[1-(2,3-dihydroxypropyl)-1,2,3,6-tetrahydropyridin-4-yl]-1H-pyrrolo[2,3-b]pyridin-4-yl}-N-methylbenzamide;

N-methyl-4-{4-[4-(methylcarbamoyl)phenyl]-1H-pyrrolo[2,3-b]pyridin-2-yl}-3,6-dihydropyridine-1(2H)-carboxamide;

4-{2-[1-(hydroxyacetyl)-1,2,3,6-tetrahydropyridin-4-yl]-1H-pyrrolo[2,3-b]pyridin-4-yl}-N-methylbenzamide;

4-[4-(5-fluoro-2-methoxyphenyl)-1H-pyrrolo[2,3-b]pyridin-2-yl]-N,N-dimethyl-3,6-dihydropyridine-1(2H)-sulfonamide;

3-bromo-4-(5-fluoro-2-methoxyphenyl)-2-(1,2,3,6-tetrahydropyridin-4-yl)-1H-pyrrolo[2,3-b]pyridine;

4-(2,4-dimethoxyphenyl)-2-(1,2,3,6-tetrahydropyridin-4-yl)-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}glycine;

4-[4-(5-fluoro-2-methoxyphenyl)-1H-pyrrolo[2,3-b]pyridin-2-yl]-N-methylcyclohex-3-ene-1-carboxamide;

4-[4-(5-fluoro-2-methoxyphenyl)-1H-pyrrolo[2,3-b]pyridin-2-yl]-N-[(3-hydroxyoxetan-3-yl)methyl]-3,6-dihydropyridine-1(2H)-carboxamide;

methyl {4-[4-(5-fluoro-2-methoxyphenyl)-1H-pyrrolo[2,3-b]pyridin-2-yl]-3,6-dihydropyridin-1(2H)-yl}acetate;

4-(4,5-difluoro-2-methoxyphenyl)-2-(1,2,3,6-tetrahydropyridin-4-yl)-1H-pyrrolo[2,3-b]pyridine;

4-[2-methoxy-4-(1H-pyrazol-1-yl)phenyl]-2-(1,2,3,6-tetrahydropyridin-4-yl)-1H-pyrrolo[2,3-b]pyridine;

4-(2,6-dimethoxyphenyl)-2-(1,2,3,6-tetrahydropyridin-4-yl)-1H-pyrrolo[2,3-b]pyridine;

4-(2-methoxyphenyl)-2-(1,2,3,6-tetrahydropyridin-4-yl)-1H-pyrrolo[2,3-b]pyridine;

4-(2-chloro-5-methoxyphenyl)-2-(1,2,3,6-tetrahydropyridin-4-yl)-1H-pyrrolo[2,3-b]pyridine;

4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile;

1-{4-[4-(2,3-difluorophenyl)-1H-pyrrolo[2,3-b]pyridin-2-yl]-3,6-dihydropyridin-1(2H)-yl}-2-methylpropan-2-ol;

4-(2,3-difluorophenyl)-2-[1-(pyridin-2-ylmethyl)-1,2,3,6-tetrahydropyridin-4-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-(5-fluoro-2-methoxyphenyl)-2-(1,2,3,6-tetrahydropyridin-4-yl)-1H-pyrrolo[2,3-b]pyridine-5-carbonitrile;

5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one;

2-{4-[4-(5-fluoro-2-methoxyphenyl)-1H-pyrrolo[2,3-b]pyridin-2-yl]-3,6-dihydropyridin-1(2H)-yl}-N-methylacetamide;

ethyl ({4-[3-bromo-4-(5-fluoro-2-methoxyphenyl)-1H-pyrrolo[2,3-b]pyridin-2-yl]-3,6-dihydropyridin-1(2H)-yl}sulfonyl)carbamate;

4-(5-fluoro-2-methoxyphenyl)-5-methyl-2-[1-(methylsulfonyl)-1,2,3,6-tetrahydropyridin-4-yl]-1H-pyrrolo[2,3-b]pyridine;

4-(5-fluoro-2-methoxyphenyl)-5-methyl-2-(1,2,3,6-tetrahydropyridin-4-yl)-1H-pyrrolo[2,3-b]pyridine;

N-[{4-[4-(5-fluoro-2-methoxyphenyl)-1H-pyrrolo[2,3-b]pyridin-2-yl]-3,6-dihydropyridin-1(2H)-yl}(methyl)oxido-$\lambda^6$-sulfanylidene]-4-methylbenzenesulfonamide;

4-(2-ethoxy-5-fluorophenyl)-2-(1,2,3,6-tetrahydropyridin-4-yl)-1H-pyrrolo[2,3-b]pyridine;

4-(2,5-dimethoxyphenyl)-2-(1,2,3,6-tetrahydropyridin-4-yl)-1H-pyrrolo[2,3-b]pyridine;

N-[(2S)-2,3-dihydroxypropyl]-4-[4-(5-fluoro-2-methoxyphenyl)-1H-pyrrolo[2,3-b]pyridin-2-yl]cyclohex-3-ene-1-carboxamide;

4-{4-[4-(5-fluoro-2-methoxyphenyl)-1H-pyrrolo[2,3-b]pyridin-2-yl]-3,6-dihydropyridin-1(2H)-yl}cyclohexanol;

1-({4-[4-(5-fluoro-2-methoxyphenyl)-1H-pyrrolo[2,3-b]pyridin-2-yl]-3,6-dihydropyridin-1(2H)-yl}carbonyl)piperidine-4-carboxylic acid;

4-[4-(5-fluoro-2-methoxyphenyl)-1H-pyrrolo[2,3-b]pyridin-2-yl]-N-[2-(4-oxopiperidin-1-yl)ethyl]-3,6-dihydropyridine-1(2H)-carboxamide;

N-[2-(3,3-difluoropiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-[2-(3-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypyrrolidin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(2-hydroxyethyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-[2-(3-oxopiperazin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypiperidin-1-yl]ethyl}-3,6-dihydropyridine-1(2H)-carboxamide;

4-methoxy-3-[2-(1,2,3,6-tetrahydropyridin-4-yl)-1H-pyrrolo[2,3-b]pyridin-4-yl]benzonitrile;

4-(2-chloro-5-fluorophenyl)-2-(1,2,3,6-tetrahydropyridin-4-yl)-1H-pyrrolo[2,3-b]pyridine;

4-(4-fluoro-2-methoxyphenyl)-2-(1,2,3,6-tetrahydropyridin-4-yl)-1H-pyrrolo[2,3-b]pyridine;

4-[2-(difluoromethoxy)-5-fluorophenyl]-2-(1,2,3,6-tetrahydropyridin-4-yl)-1H-pyrrolo[2,3-b]pyridine;

({4-[4-(5-fluoro-2-methoxyphenyl)-1H-pyrrolo[2,3-b]pyridin-2-yl]-3,6-dihydropyridin-1(2H)-yl}sulfonyl)acetic acid;

4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine;

5-chloro-4-(5-fluoro-2-methoxyphenyl)-2-(1,2,3,6-tetrahydropyridin-4-yl)-1H-pyrrolo[2,3-b]pyridine;

4-(5-fluoro-2-methoxyphenyl)-2-{1-[(tetrahydrofuran-2-ylmethyl)sulfonyl]-1,2,3,6-tetrahydropyridin-4-yl}-1H-pyrrolo[2,3-b]pyridine;

ethyl ({4-[4-(5-fluoro-2-methoxyphenyl)-5-methyl-1H-pyrrolo[2,3-b]pyridin-2-yl]-3,6-dihydropyridin-1(2H)-yl}sulfonyl)carbamate;

3-chloro-4-(5-fluoro-2-methoxyphenyl)-2-(1,2,3,6-tetrahydropyridin-4-yl)-1H-pyrrolo[2,3-b]pyridine;

ethyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate;

3-chloro-4-(5-fluoro-2-methoxyphenyl)-2-[1-(methylsulfonyl)-1,2,3,6-tetrahydropyridin-4-yl]-1H-pyrrolo[2,3-b]pyridine;

(cis-4-{4-[5-fluoro-4-(5-fluoro-2-methoxyphenyl)-1H-pyrrolo[2,3-b]pyridin-2-yl]piperidin-1-yl}cyclohexyl)acetic acid;

4-[4-(5-fluoro-2-methoxyphenyl)-1H-pyrrolo[2,3-b]pyridin-2-yl]-N-(pyridin-2-ylmethyl)cyclohex-3-en-1-amine;

4-[4-(5-fluoro-2-methoxyphenyl)-1H-pyrrolo[2,3-b]pyridin-2-yl]-N-(pyrazin-2-ylmethyl)cyclohex-3-en-1-amine;

4-[4-(5-fluoro-2-methoxyphenyl)-1H-pyrrolo[2,3-b]pyridin-2-yl]-N-(pyrimidin-5-ylmethyl)cyclohex-3-en-1-amine;

4-[4-(5-fluoro-2-methoxyphenyl)-1H-pyrrolo[2,3-b]pyridin-2-yl]-N-(tetrahydrofuran-2-ylmethyl)cyclohex-3-en-1-amine;

4-{5-fluoro-2-[($^2$H$_3$)methyloxy]phenyl}-2-(1,2,3,6-tetrahydropyridin-4-yl)-1H-pyrrolo[2,3-b]pyridine;

4-(4-{5-fluoro-2-[($^2$H$_3$)methyloxy]phenyl}-1H-pyrrolo[2,3-b]pyridin-2-yl)-N-methyl-3,6-dihydropyridine-1(2H)-carboxamide;

4-{5-fluoro-2-[($^2$H$_3$)methyloxy]phenyl}-2-[1-(methylsulfonyl)-1,2,3,6-tetrahydropyridin-4-yl]-1H-pyrrolo[2,3-b]pyridine;

methyl 2-{4-[4-(5-fluoro-2-methoxyphenyl)-1H-pyrrolo[2,3-b]pyridin-2-yl]-3,6-dihydropyridin-1(2H)-yl}propanoate;

5-chloro-4-(5-fluoro-2-methoxyphenyl)-2-[1-(methylsulfonyl)-1,2,3,6-tetrahydropyridin-4-yl]-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone;

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid;

{4-[4-(5-fluoro-2-methoxyphenyl)-1H-pyrrolo[2,3-b]pyridin-2-yl]-3,6-dihydropyridin-1(2H)-yl}[(4S)-2,2,5,5-tetramethyl-1,3-dioxolan-4-yl]methanone;

2-{4-[4-(5-fluoro-2-methoxyphenyl)-1H-pyrrolo[2,3-b]pyridin-2-yl]-3,6-dihydropyridin-1(2H)-yl}propanoic acid;

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid;

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid;

methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

methyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate;

2-fluoro-N-methyl-4-{2-[1-(methylsulfonyl)-1,2,3,6-tetrahydropyridin-4-yl]-1H-pyrrolo[2,3-b]pyridin-4-yl}benzamide;

(2S)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

(2R)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

4-(5-fluoro-2-methoxyphenyl)-2-[1-(hydroxyacetyl)-1,2,3,6-tetrahydropyridin-4-yl]-1H-pyrrolo[2,3-b]pyridine-5-carbonitrile;

4-[5-cyano-4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-N-[2-(piperazin-1-yl)ethyl]-3,6-dihydropyridine-1(2H)-carboxamide;

N-[2-(4-aminopiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

N-{2-[(1,3-dihydroxypropan-2-yl)amino]ethyl}-4-[4-(5-fluoro-2-methoxyphenyl)-1H-pyrrolo[2,3-b]pyridin-2-yl]-3,6-dihydropyridine-1(2H)-carboxamide;

3-ethoxy-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

5-fluoro-4-(5-fluoro-2-methoxyphenyl)-2-(1,2,3,6-tetrahydropyridin-4-yl)-1H-pyrrolo[2,3-b]pyridine;

4-[5-fluoro-4-(5-fluoro-2-methoxyphenyl)-1H-pyrrolo[2,3-b]pyridin-2-yl]-N-methyl-3,6-dihydropyridine-1(2H)-carboxamide;

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]-3,6-dihydropyridin-1(2H)-yl}propane-1,2-diol;

1-{4-[4-(5-fluoro-2-methoxyphenyl)-1H-pyrrolo[2,3-b]pyridin-2-yl]-3,6-dihydropyridin-1(2H)-yl}-2-(methylsulfonyl)ethanone;

ethyl 3-{4-[4-(5-fluoro-2-methoxyphenyl)-1H-pyrrolo[2,3-b]pyridin-2-yl]-3,6-dihydropyridin-1(2H)-yl}-3-oxopropanoate;

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}-3,6-dihydropyridine-1(2H)-carboxamide;

N-(2-{4-[4-(5-fluoro-2-methoxyphenyl)-1H-pyrrolo[2,3-b]pyridin-2-yl]-3,6-dihydropyridin-1(2H)-yl}-2-oxoethyl)methanesulfonamide;

4-[4-(2,3-difluorophenyl)-1H-pyrrolo[2,3-b]pyridin-2-yl]cyclohex-3-ene-1-carboxylic acid;

N-({4-[4-(5-fluoro-2-methoxyphenyl)-1H-pyrrolo[2,3-b]pyridin-2-yl]cyclohex-3-en-1-yl}carbonyl)glycine;

3-{4-[4-(5-fluoro-2-methoxyphenyl)-1H-pyrrolo[2,3-b]pyridin-2-yl]-3,6-dihydropyridin-1(2H)-yl}-3-oxopropanoic acid;

4-(4-chloro-2-methoxyphenyl)-2-(1,2,3,6-tetrahydropyridin-4-yl)-1H-pyrrolo[2,3-b]pyridine;

4-(2,4-dimethoxyphenyl)-2-[1-(methylsulfonyl)-1,2,3,6-tetrahydropyridin-4-yl]-1H-pyrrolo[2,3-b]pyridine;

3-{4-[4-(2,4-dimethoxyphenyl)-1H-pyrrolo[2,3-b]pyridin-2-yl]-3,6-dihydropyridin-1(2H)-yl}propane-1,2-diol;

4-(2,4-dimethoxyphenyl)-1H-pyrrolo[2,3-b]pyridin-2-yl]-N-methyl-3,6-dihydropyridine-1(2H)-carboxamide;

1-{4-[4-(2,4-dimethoxyphenyl)-1H-pyrrolo[2,3-b]pyridin-2-yl]-3,6-dihydropyridin-1(2H)-yl}-2-hydroxyethanone;

3-{4-[4-(2-methoxyphenyl)-1H-pyrrolo[2,3-b]pyridin-2-yl]-3,6-dihydropyridin-1(2H)-yl}propane-1,2-diol;

4-[4-(2-methoxyphenyl)-1H-pyrrolo[2,3-b]pyridin-2-yl]-N-methyl-3,6-dihydropyridine-1(2H)-carboxamide;

2-hydroxy-1-{4-[4-(2-methoxyphenyl)-1H-pyrrolo[2,3-b]pyridin-2-yl]-3,6-dihydropyridin-1(2H)-yl}ethanone;

3-{4-[4-(4-fluoro-2-methoxyphenyl)-1H-pyrrolo[2,3-b]pyridin-2-yl]-3,6-dihydropyridin-1(2H)-yl}propane-1,2-diol;

4-[4-(4-fluoro-2-methoxyphenyl)-1H-pyrrolo[2,3-b]pyridin-2-yl]-N-methyl-3,6-dihydropyridine-1(2H)-carboxamide;

1-{4-[4-(4-fluoro-2-methoxyphenyl)-1H-pyrrolo[2,3-b]pyridin-2-yl]-3,6-dihydropyridin-1(2H)-yl}-2-hydroxyethanone;

3-{4-[4-(4,5-difluoro-2-methoxyphenyl)-1H-pyrrolo[2,3-b]pyridin-2-yl]-3,6-dihydropyridin-1(2H)-yl}propane-1,2-diol;

1-{4-[4-(4,5-difluoro-2-methoxyphenyl)-1H-pyrrolo[2,3-b]pyridin-2-yl]-3,6-dihydropyridin-1(2H)-yl}-2-hydroxyethanone;

N-({4-[4-(5-fluoro-2-methoxyphenyl)-1H-pyrrolo[2,3-b]pyridin-2-yl]-3,6-dihydropyridin-1(2H)-yl}sulfonyl)acetamide;

4-(4,5-difluoro-2-methoxyphenyl)-2-[1-(methylsulfonyl)-1,2,3,6-tetrahydropyridin-4-yl]-1H-pyrrolo[2,3-b]pyridine;

4-(5-fluoro-2-methoxyphenyl)-3-methyl-2-(1,2,3,6-tetrahydropyridin-4-yl)-1H-pyrrolo[2,3-b]pyridine;

2-(8-azabicyclo[3.2.1]oct-2-en-3-yl)-4-(2,3-difluorophenyl)-1H-pyrrolo[2,3-b]pyridine;

{4-[5-cyano-4-(5-fluoro-2-methoxyphenyl)-1H-pyrrolo[2,3-b]pyridin-2-yl]-3,6-dihydropyridin-1(2H)-yl}acetic acid;

4-[4-(5-fluoro-2-methoxyphenyl)-1H-pyrrolo[2,3-b]pyridin-2-yl]-N-(2-{[2-(1H-imidazol-4-yl)ethyl]amino}ethyl)-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxypropyl)amino]ethyl}-3,6-dihydropyridine-1(2H)-carboxamide;

N-[2-(dimethylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(2-{[(3-methyloxetan-3-yl)methyl]amino}ethyl)-3,6-dihydropyridine-1(2H)-carboxamide;

4-[4-(5-fluoro-2-methoxyphenyl)-1H-pyrrolo[2,3-b]pyridin-2-yl]-N-[2-(oxetan-3-ylamino)ethyl]-3,6-dihydropyridine-1(2H)-carboxamide;

3-methoxy-N-methyl-4-[2-(1,2,3,6-tetrahydropyridin-4-yl)-1H-pyrrolo[2,3-b]pyridin-4-yl]benzamide;

3-methoxy-N-methyl-4-{2-[1-(methylsulfonyl)-1,2,3,6-tetrahydropyridin-4-yl]-1H-pyrrolo[2,3-b]pyridin-4-yl}benzamide;

4-{2-[1-(2,3-dihydroxypropyl)-1,2,3,6-tetrahydropyridin-4-yl]-1H-pyrrolo[2,3-b]pyridin-4-yl}-3-methoxy-N-methylbenzamide;

3-amino-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

4-(5-fluoro-2-methoxyphenyl)-2-(2,5,6,7-tetrahydro-14-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,75-tetrahydro-1H-azepin-4-yl)-1H-pyrrolo[2,3-b]pyridine;

4-(5-fluoro-2-methoxyphenyl)-2-[1-(methylsulfonyl)-2,5,6,7-tetrahydro-1H-azepin-4-yl]-1H-pyrrolo[2,3-b]pyridine and 4-(5-fluoro-2-methoxyphenyl)-2-(1-(methylsulfonyl)-2,3,6,7-tetrahydro-1H-azepin-4-yl)-1H-pyrrolo[2,3-b]pyridine;

5-[4-(5-fluoro-2-methoxyphenyl)-1H-pyrrolo[2,3-b]pyridin-2-yl]-N-methyl-2,3,4,7-tetrahydro-1H-azepine-1-carboxamide and 4-(4-(5-fluoro-2-methoxyphenyl)-1H-pyrrolo[2,3-b]pyridin-2-yl)-N-methyl-2,3,6,7-tetrahydro-1H-azepine-1-carboxamide;

1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(methylsulfonyl)acetamide;

2-{4-[4-(2,4-dimethoxyphenyl)-1H-pyrrolo[2,3-b]pyridin-2-yl]-3,6-dihydropyridin-1(2H)-yl}-N,N-dimethylacetamide;

2-{4-[4-(2-methoxyphenyl)-1H-pyrrolo[2,3-b]pyridin-2-yl]-3,6-dihydropyridin-1(2H)-yl}-N,N-dimethylacetamide;

2-{4-[4-(4-fluoro-2-methoxyphenyl)-1H-pyrrolo[2,3-b]pyridin-2-yl]-3,6-dihydropyridin-1(2H)-yl}-N,N-dimethylacetamide;

2-{4-[4-(4,5-difluoro-2-methoxyphenyl)-1H-pyrrolo[2,3-b]pyridin-2-yl]-3,6-dihydropyridin-1(2H)-yl}-N,N-dimethylacetamide;

tert-butyl {5-[4-(5-fluoro-2-methoxyphenyl)-1H-pyrrolo[2,3-b]pyridin-2-yl]-3,6-dihydropyridin-1(2H)-yl}acetate;

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)acetamide;

N-({4-[4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

2-{5-[4-(5-fluoro-2-methoxyphenyl)-1H-pyrrolo[2,3-b]pyridin-2-yl]-3,6-dihydropyridin-1(2H)-yl}-N,N-dimethylacetamide;

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

ethyl ({4-[4-(5-fluoro-2-methoxyphenyl)-3-methyl-1H-pyrrolo[2,3-b]pyridin-2-yl]-3,6-dihydropyridin-1(2H)-yl}sulfonyl)carbamate;

{5-[4-(5-fluoro-2-methoxyphenyl)-1H-pyrrolo[2,3-b]pyridin-2-yl]-3,6-dihydropyridin-1(2H)-yl}acetic acid;

ethyl 1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylate;

4-[4-(5-fluoro-2-methoxyphenyl)-3-methyl-1H-pyrrolo[2,3-b]pyridin-2-yl]-N-methyl-3,6-dihydropyridine-1(2H)-carboxamide;

4-(5-fluoro-2-methoxyphenyl)-3-methyl-2-[1-(methylsulfonyl)-1,2,3,6-tetrahydropyridin-4-yl]-1H-pyrrolo[2,3-b]pyridine;

2-(dimethylamino)-1-{4-[4-(5-fluoro-2-methoxyphenyl)-1H-pyrrolo[2,3-b]pyridin-2-yl]-3,6-dihydropyridin-1(2H)-yl}ethanone;

{4-[5-fluoro-4-(5-fluoro-2-methoxyphenyl)-1H-pyrrolo[2,3-b]pyridin-2-yl]-3,6-dihydropyridin-1(2H)-yl}acetic acid;

2-({4-[4-(5-fluoro-2-methoxyphenyl)-1H-pyrrolo[2,3-b]pyridin-2-yl]cyclohex-3-en-1-yl}amino)butanoic acid;

4-(2,3-difluorophenyl)-2-[1-(methylsulfonyl)-1,2,5,6-tetrahydropyridin-3-yl]-1H-pyrrolo[2,3-b]pyridine;

2-{5-[4-(2,3-difluorophenyl)-1H-pyrrolo[2,3-b]pyridin-2-yl]-3,6-dihydropyridin-1(2H)-yl}-N,N-dimethylacetamide;

1-{5-[4-(2,3-difluorophenyl)-1H-pyrrolo[2,3-b]pyridin-2-yl]-3,6-dihydropyridin-1(2H)-yl}-2-hydroxyethanone;

4-(5-fluoro-2-methoxyphenyl)-2-[1-(methylsulfonyl)azepan-4-yl]-1H-pyrrolo[2,3-b]pyridine;

{3-[4-(5-fluoro-2-methoxyphenyl)-1H-pyrrolo[2,3-b]pyridin-2-yl]-2,5-dihydro-1H-pyrrol-1-yl}acetic acid;

2-{4-[4-(5-fluoro-2-methoxyphenyl)-1H-pyrrolo[2,3-b]pyridin-2-yl]piperidin-1-yl}-N,N-dimethylethanesulfonamide;

{4-[4-(2,4-dimethoxyphenyl)-1H-pyrrolo[2,3-b]pyridin-2-yl]-3,6-dihydropyridin-1(2H)-yl}acetic acid;

{4-[4-(2-methoxyphenyl)-1H-pyrrolo[2,3-b]pyridin-2-yl]-3,6-dihydropyridin-1(2H)-yl}acetic acid;

{4-[4-(4,5-difluoro-2-methoxyphenyl)-1H-pyrrolo[2,3-b]pyridin-2-yl]-3,6-dihydropyridin-1(2H)-yl}acetic acid;

1-{4-[4-(5-fluoro-2-methoxyphenyl)-1H-pyrrolo[2,3-b]pyridin-2-yl]-3,6-dihydropyridin-1(2H)-yl}-2-(3-hydroxypyrrolidin-1-yl)ethanone;

methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate;

{4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetic acid;

N-(cyclopropylsulfonyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(phenylsulfonyl)-3,6-dihydropyridine-1(2H)-carboxamide;

5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one;

{4-[4-(5-fluoro-2-methoxyphenyl)-1H-pyrrolo[2,3-b]pyridin-2-yl]piperidin-1-yl}acetic acid;

{3-[4-(5-fluoro-2-methoxyphenyl)-1H-pyrrolo[2,3-b]pyridin-2-yl]pyrrolidin-1-yl}acetic acid;

4-[4-(5-fluoro-2-methoxyphenyl)-1H-pyrrolo[2,3-b]pyridin-2-yl]-2,5-dihydro-1H-pyrrole-2-carboxylic acid;

3-{4-[4-(2,3-difluorophenyl)-1H-pyrrolo[2,3-b]pyridin-2-yl]-3,6-dihydropyridin-1(2H)-yl}-3-oxopropanenitrile;

{4-[4-(5-fluoro-2-methoxyphenyl)-1H-pyrrolo[2,3-b]pyridin-2-yl]-3,6-dihydropyridin-1(2H)-yl}(1-hydroxycyclopropyl)methanone;

3-{5-[4-(2,3-difluorophenyl)-1H-pyrrolo[2,3-b]pyridin-2-yl]-3,6-dihydropyridin-1(2H)-yl}propane-1,2-diol;

1-{5-[4-(2,3-difluorophenyl)-1H-pyrrolo[2,3-b]pyridin-2-yl]-3,6-dihydropyridin-1(2H)-yl}-2-hydroxy-2-methylpropan-1-one;

{4-[4-(4-fluoro-2-methoxyphenyl)-1H-pyrrolo[2,3-b]pyridin-2-yl]-3,6-dihydropyridin-1(2H)-yl}acetic acid;

{3-[4-(5-fluoro-2-methoxyphenyl)-1H-pyrrolo[2,3-b]pyridin-2-yl]-8-azabicyclo[3.2.1]oct-2-en-8-yl}acetic acid;

1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylic acid;

1-{5-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-[4-(5-fluoro-2-methoxyphenyl)-1H-pyrrolo[2,3-b]pyridin-2-yl]-N-(propan-2-ylsulfonyl)cyclohex-3-ene-1-carboxamide;

2-{4-[4-(5-fluoro-2-methoxyphenyl)-1H-pyrrolo[2,3-b]pyridin-2-yl]-3,6-dihydropyridin-1(2H)-yl}-2-oxoethanesulfonamide;

2-{4-[4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;

tert-butyl {4-[4-(5-fluoro-2-methoxyphenyl)-1H-pyrrolo[2,3-b]pyridin-2-yl]-3,6-dihydropyridin-1(2H)-yl}acetate;

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}-3,6-dihydropyridine-1(2H)-carboxamide;

4-(5-fluoro-2-methoxyphenyl)-2-[1-(2H-tetrazol-5-ylmethyl)-1,2,3,6-tetrahydropyridin-4-yl]-1H-pyrrolo[2,3-b]pyridine;

6-[4-(5-fluoro-2-methoxyphenyl)-1H-pyrrolo[2,3-b]pyridin-2-yl]-2-azaspiro[3.3]heptan-6-ol;

{(2R)-4-[4-(5-fluoro-2-methoxyphenyl)-1H-pyrrolo[2,3-b]pyridin-2-yl]-2,5-dihydro-1H-pyrrol-2-yl}methanol;

{4-[4-(2,3-difluorophenyl)-1H-pyrrolo[2,3-b]pyridin-2-yl]-3,6-dihydropyridin-1(2H)-yl}acetic acid;

4-[4-(5-fluoro-2-methoxyphenyl)-1H-pyrrolo[2,3-b]pyridin-2-yl]cyclohex-3-en-1-ol;

2-{3-[4-(5-fluoro-2-methoxyphenyl)-1H-pyrrolo[2,3-b]pyridin-2-yl]pyrrolidin-1-yl}-N,N-dimethylacetamide;

3-[4-(5-fluoro-2-methoxyphenyl)-1H-pyrrolo[2,3-b]pyridin-2-yl]cyclopent-3-en-1-amine;

3-[4-(5-fluoro-2-methoxyphenyl)-1H-pyrrolo[2,3-b]pyridin-2-yl]cyclopent-2-en-1-amine;

2-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]-1H-isoindole-1,3(2H)-dione;

3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

4-[4-(5-fluoro-2-methoxyphenyl)-1H-pyrrolo[2,3-b]pyridin-2-yl]-N-(2-{[(1S,2S)-2-hydroxycyclohexyl]amino}ethyl)-3,6-dihydropyridine-1(2H)-carboxamide;

N-(2-{[2-(dimethylamino)ethyl]amino}ethyl)-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(2-methoxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(4-methylbenzoyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(methylsulfonyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-(2-{[3-(trifluoromethyl)benzyl]amino}ethyl)-3,6-dihydropyridine-1(2H)-carboxamide;

ethyl ({4-[4-(2,3-difluorophenyl)-1H-pyrrolo[2,3-b]pyridin-2-yl]-3,6-dihydropyridin-1(2H)-yl}sulfonyl)carbamate;

2,2,2-trifluoroethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-en-1-one;

2-(3,6-dihydro-2H-thiopyran-4-yl)-4-(5-fluoro-2-methoxyphenyl)-1H-pyrrolo[2,3-b]pyridine;

3-fluoro-N-methyl-4-[2-(1,2,3,6-tetrahydropyridin-4-yl)-1H-pyrrolo[2,3-b]pyridin-4-yl]benzamide;

N-({4-[4-(5-fluoro-2-methoxyphenyl)-1H-pyrrolo[2,3-b]pyridin-2-yl]-3,6-dihydropyridin-1(2H)-yl}carbonyl)alanine;

4-(5-fluoro-2-methoxyphenyl)-2-(1-oxido-3,6-dihydro-2H-thiopyran-4-yl)-1H-pyrrolo[2,3-b]pyridine;

4-[4-(5-fluoro-2-methoxyphenyl)-1H-pyrrolo[2,3-b]pyridin-2-yl]-N-[(1-methylcyclopropyl)sulfonyl]cyclohex-3-ene-1-carboxamide;

4-[4-(5-fluoro-2-methoxyphenyl)-1H-pyrrolo[2,3-b]pyridin-2-yl]-N-[(2-methylpropyl)sulfonyl]cyclohex-3-ene-1-carboxamide;

4-(2,3-difluorophenyl)-1H-pyrrolo[2,3-b]pyridin-2-yl]-N-(phenylsulfonyl)-3,6-dihydropyridine-1(2H)-carboxamide;

4-(5-fluoro-2-methoxyphenyl)-2-(1,2,3,6-tetrahydropyridin-4-yl)-1H-pyrrolo[2,3-b]pyridine-5-carboxamide;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-5-carbonitrile;

2-{4-[5-chloro-4-(5-fluoro-2-methoxyphenyl)-1H-pyrrolo[2,3-b]pyridin-2-yl]-3,6-dihydropyridin-1(2H)-yl}-N,N-dimethylacetamide;

{4-[5-chloro-4-(5-fluoro-2-methoxyphenyl)-1H-pyrrolo[2,3-b]pyridin-2-yl]-3,6-dihydropyridin-1(2H)-yl}acetic acid;

3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol;

{4-[4-(5-fluoro-2-methoxyphenyl)-1H-pyrrolo[2,3-b]pyridin-2-yl]-3,6-dihydropyridin-1(2H)-yl}[(2S,4S)-4-hydroxypyrrolidin-2-yl]methanone;

N-[2-(ethylamino)ethyl]-4-[4-(5-fluoro-2-methoxyphenyl)-1H-pyrrolo[2,3-b]pyridin-2-yl]-3,6-dihydropyridine-1(2H)-carboxamide;

N-[2-(cyclopropylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(pyridin-2-ylmethyl)amino]ethyl}-3,6-dihydropyridine-1(2H)-carboxamide;

3-amino-4-{4-[4-(2-{2-[(2-amino-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

tert-butyl 4-({4-[4-(5-fluoro-2-methoxyphenyl)-1H-pyrrolo[2,3-b]pyridin-2-yl]-3,6-dihydropyridin-1(2H)-yl}sulfonyl)piperidine-1-carboxylate;

4-[4-(5-fluoro-2-methoxyphenyl)-1H-pyrrolo[2,3-b]pyridin-2-yl]-1-(methylsulfonyl)-2,5-dihydro-1H-pyrrole-2-carboxylic acid;

4-(5-fluoro-2-methoxyphenyl)-2-[1-(piperidin-4-ylsulfonyl)-1,2,3,6-tetrahydropyridin-4-yl]-1H-pyrrolo[2,3-b]pyridine;

N,N-dimethyl-4-{2-[1-(methylsulfonyl)-1,2,3,6-tetrahydropyridin-4-yl]-1H-pyrrolo[2,3-b]pyridin-4-yl}benzamide;

2-{4-[4-(5-fluoro-2-methoxyphenyl)-1H-pyrrolo[2,3-b]pyridin-2-yl]-3,6-dihydropyridin-1(2H)-yl}-N,N-dimethylpropanamide;

4-(4-fluoro-2-methoxyphenyl)-2-[8-(methylsulfonyl)-8-azabicyclo[3.2.1]oct-2-en-3-yl]-1H-pyrrolo[2,3-b]pyridine;

4-(4,5-difluoro-2-methoxyphenyl)-2-[8-(methylsulfonyl)-8-azabicyclo[3.2.1]oct-2-en-3-yl]-1H-pyrrolo[2,3-b]pyridine;

4-(2-methoxyphenyl)-2-[8-(methylsulfonyl)-8-azabicyclo[3.2.1]oct-2-en-3-yl]-1H-pyrrolo[2,3-b]pyridine;

4-(3-fluoro-2-methoxyphenyl)-2-(1,2,3,6-tetrahydropyridin-4-yl)-1H-pyrrolo[2,3-b]pyridine;

ethyl ({4-[4-(4-fluoro-2-methoxyphenyl)-1H-pyrrolo[2,3-b]pyridin-2-yl]-3,6-dihydropyridin-1(2H)-yl}sulfonyl)carbamate;

ethyl ({4-[4-(2,4-dimethoxyphenyl)-1H-pyrrolo[2,3-b]pyridin-2-yl]-3,6-dihydropyridin-1(2H)-yl}sulfonyl)carbamate;

ethyl ({4-[4-(2-methoxyphenyl)-1H-pyrrolo[2,3-b]pyridin-2-yl]-3,6-dihydropyridin-1(2H)-yl}sulfonyl)carbamate;

ethyl ({4-[4-(4,5-difluoro-2-methoxyphenyl)-1H-pyrrolo[2,3-b]pyridin-2-yl]-3,6-dihydropyridin-1(2H)-yl}sulfonyl)carbamate;

{4-[4-(5-fluoro-2-methoxyphenyl)-1H-pyrrolo[2,3-b]pyridin-2-yl]-3,6-dihydropyridin-1(2H)-yl}[(2S,4R)-4-hydroxypyrrolidin-2-yl]methanone;

{4-[4-(5-fluoro-2-methoxyphenyl)-1H-pyrrolo[2,3-b]pyridin-2-yl]-3,6-dihydropyridin-1(2H)-yl}[(2R,4S)-4-hydroxypyrrolidin-2-yl]methanone;

4-[4-(5-fluoro-2-methoxyphenyl)-1H-pyrrolo[2,3-b]pyridin-2-yl]-N,N-dimethylcyclohex-3-ene-1-carboxamide;

N-{4-[4-(5-fluoro-2-methoxyphenyl)-1H-pyrrolo[2,3-b]pyridin-2-yl]cyclohex-3-en-1-yl}alanine;

2-({4-[4-(5-fluoro-2-methoxyphenyl)-1H-pyrrolo[2,3-b]pyridin-2-yl]-3,6-dihydropyridin-1(2H)-yl}sulfonyl)ethanamine;

4-{2-[1-(methylsulfonyl)-1,2,3,6-tetrahydropyridin-4-yl]-1H-pyrrolo[2,3-b]pyridin-4-yl}-N-propylbenzamide;

3-fluoro-N-methyl-4-{2-[1-(methylsulfonyl)-1,2,3,6-tetrahydropyridin-4-yl]-1H-pyrrolo[2,3-b]pyridin-4-yl}benzamide;

ethyl {[4-{4-[2-fluoro-4-(methylcarbamoyl)phenyl]-1H-pyrrolo[2,3-b]pyridin-2-yl}-3,6-dihydropyridin-1(2H)-yl]sulfonyl}carbamate;

[4-{4-[2-fluoro-4-(methylcarbamoyl)phenyl]-1H-pyrrolo[2,3-b]pyridin-2-yl}-3,6-dihydropyridin-1(2H)-yl]acetic acid;

4-(5-fluoro-2-methoxyphenyl)-2-(1,2,3,3a,4,6a-hexahydrocyclopenta[c]pyrrol-5-yl)-1H-pyrrolo[2,3-b]pyridine;

tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate;

tert-butyl 4-[4-(5-fluoro-2-methoxyphenyl)-1H-pyrrolo[2,3-b]pyridin-2-yl]-2-[(methylsulfonyl)carbamoyl]-2,5-dihydro-1H-pyrrole-1-carboxylate;

2-fluoro-N-methyl-4-[2-(1,2,3,6-tetrahydropyridin-4-yl)-1H-pyrrolo[2,3-b]pyridin-4-yl]benzamide;

4-{4-[3-fluoro-4-(methylcarbamoyl)phenyl]-1H-pyrrolo[2,3-b]pyridin-2-yl}-N-methyl-3,6-dihydropyridine-1(2H)-carboxamide;

4-(2-{1-[2-(dimethylamino)-2-oxoethyl]-1,2,3,6-tetrahydropyridin-4-yl}-1H-pyrrolo[2,3-b]pyridin-4-yl)-2-fluoro-N-methylbenzamide;

4-{2-[1-(2,3-dihydroxypropyl)-1,2,3,6-tetrahydropyridin-4-yl]-1H-pyrrolo[2,3-b]pyridin-4-yl}-2-fluoro-N-methylbenzamide;

4-(5-fluoro-2-methoxyphenyl)-5-methoxy-2-[1-(methylsulfonyl)-1,2,3,6-tetrahydropyridin-4-yl]-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}serine;

3-[4-(5-fluoro-2-methoxyphenyl)-1H-pyrrolo[2,3-b]pyridin-2-yl]cyclohex-3-ene-1-carboxylic acid;

{4-[4-(5-fluoro-2-methoxyphenyl)-1H-pyrrolo[2,3-b]pyridin-2-yl]-1,2,3,6-tetrahydropyridin-2-yl}methanol;

7-[4-(5-fluoro-2-methoxyphenyl)-1H-pyrrolo[2,3-b]pyridin-2-yl]-3-oxa-9-azabicyclo[3.3.1]non-6-ene;

7-[4-(5-fluoro-2-methoxyphenyl)-1H-pyrrolo[2,3-b]pyridin-2-yl]-9-(methylsulfonyl)-3-oxa-9-azabicyclo[3.3.1]non-6-ene;

ethyl ({7-[4-(5-fluoro-2-methoxyphenyl)-1H-pyrrolo[2,3-b]pyridin-2-yl]-3-oxa-9-azabicyclo[3.3.1]non-6-en-9-yl}sulfonyl)carbamate;
2-{7-[4-(5-fluoro-2-methoxyphenyl)-1H-pyrrolo[2,3-b]pyridin-2-yl]-3-oxa-9-azabicyclo[3.3.1]non-6-en-9-yl}-N,N-dimethylacetamide;
N-{4-[4-(5-fluoro-2-methoxyphenyl)-1H-pyrrolo[2,3-b]pyridin-2-yl]cyclohex-3-en-1-yl}-L-isoleucine;
ethyl {[4-{4-[3-fluoro-4-(methylcarbamoyl)phenyl]-1H-pyrrolo[2,3-b]pyridin-2-yl}-3,6-dihydropyridin-1(2H)-yl]sulfonyl}carbamate;
4-(3-fluoro-2-methoxyphenyl)-2-[1-(methylsulfonyl)-1,2,3,6-tetrahydropyridin-4-yl]-1H-pyrrolo[2,3-b]pyridine;
4-[4-(3-fluoro-2-methoxyphenyl)-1H-pyrrolo[2,3-b]pyridin-2-yl]-N-methyl-3,6-dihydropyridine-1(2H)-carboxamide;
methyl 4-[4-(5-fluoro-2-methoxyphenyl)-1H-pyrrolo[2,3-b]pyridin-2-yl]-2,5-dihydro-1H-pyrrole-2-carboxylate;
1-{4-[4-(5-fluoro-2-methoxyphenyl)-1H-pyrrolo[2,3-b]pyridin-2-yl]-3,6-dihydropyridin-1(2H)-yl}-3-(3-hydroxyazetidin-1-yl)propane-1,3-dione;
[(2S)-4-[4-(5-fluoro-2-methoxyphenyl)-1H-pyrrolo[2,3-b]pyridin-2-yl]-1-(methylsulfonyl)-2,5-dihydro-1H-pyrrol-2-yl]methanol;
ethyl {[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]sulfonyl}carbamate;
2-({4-[4-(5-fluoro-2-methoxyphenyl)-1H-pyrrolo[2,3-b]pyridin-2-yl]-3,6-dihydropyridin-1(2H)-yl}sulfonyl)-1-(3-hydroxyazetidin-1-yl)ethanone;
{(2S)-4-[4-(5-fluoro-2-methoxyphenyl)-1H-pyrrolo[2,3-b]pyridin-2-yl]-2,5-dihydro-1H-pyrrol-2-yl}methanol;
8-[4-(5-fluoro-2-methoxyphenyl)-1H-pyrrolo[2,3-b]pyridin-2-yl]-1,3-diazaspiro[4.5]dec-7-ene-2,4-dione;
1-amino-4-[4-(5-fluoro-2-methoxyphenyl)-1H-pyrrolo[2,3-b]pyridin-2-yl]cyclohex-3-ene-1-carboxylic acid;
2-(2-azaspiro[3.3]hept-6-yl)-4-(5-fluoro-2-methoxyphenyl)-1H-pyrrolo[2,3-b]pyridine;
4-(5-fluoro-2-methoxyphenyl)-5-methoxy-2-(1,2,3,6-tetrahydropyridin-4-yl)-1H-pyrrolo[2,3-b]pyridine;
ethyl 4-(5-fluoro-2-methoxyphenyl)-2-(1,2,3,6-tetrahydropyridin-4-yl)-1H-pyrrolo[2,3-b]pyridine-3-carboxylate;
4-(5-fluoro-2-methoxyphenyl)-2-(1-{[1-(methylsulfonyl)piperidin-4-yl]sulfonyl}-1,2,3,6-tetrahydropyridin-4-yl)-1H-pyrrolo[2,3-b]pyridine;
N-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]methanesulfonamide;
{4-[4-(5-fluoro-2-methoxyphenyl)-1H-pyrrolo[2,3-b]pyridin-2-yl]-1-(methylsulfonyl)-1,2,3,6-tetrahydropyridin-2-yl}methanol;
ethyl ({4-[4-(5-fluoro-2-methoxyphenyl)-1H-pyrrolo[2,3-b]pyridin-2-yl]-2-(hydroxymethyl)-3,6-dihydropyridin-1(2H)-yl}sulfonyl)carbamate;
2-{4-[4-(5-fluoro-2-methoxyphenyl)-1H-pyrrolo[2,3-b]pyridin-2-yl]-2-(hydroxymethyl)-3,6-dihydropyridin-1(2H)-yl}-N,N-dimethylacetamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-[4-(5-fluoro-2-methoxyphenyl)-1H-pyrrolo[2,3-b]pyridin-2-yl]-N,N-dimethyl-2,5-dihydro-1H-pyrrole-2-carboxamide;
2-(4-{4-[4-(5-fluoro-2-methoxyphenyl)-1H-pyrrolo[2,3-b]pyridin-2-yl]-3,6-dihydropyridin-1(2H)-yl}piperidin-1-yl)-N,N-dimethylacetamide;
N-{4-[4-(2,3-difluorophenyl)-1H-pyrrolo[2,3-b]pyridin-2-yl]cyclohex-3-en-1-yl}glycine;
1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone;
4-(5-fluoro-2-methoxyphenyl)-2-(1-{[1-(methylsulfonyl)azetidin-3-yl]sulfonyl}-1,2,3,6-tetrahydropyridin-4-yl)-1H-pyrrolo[2,3-b]pyridine;
ethyl 4-(5-fluoro-2-methoxyphenyl)-2-[1-(methylsulfonyl)-1,2,3,6-tetrahydropyridin-4-yl]-1H-pyrrolo[2,3-b]pyridine-3-carboxylate;
4-(5-fluoro-2-methoxyphenyl)-2-(2,3,6,7-tetrahydro-1H-azepin-4-yl)-1H-pyrrolo[2,3-b]pyridine;
3-(2-{4-[4-(5-fluoro-2-methoxyphenyl)-1H-pyrrolo[2,3-b]pyridin-2-yl]-3,6-dihydropyridin-1(2H)-yl}-2-oxoethyl)imidazolidine-2,4-dione;
({4-[4-(5-fluoro-2-methoxyphenyl)-1H-pyrrolo[2,3-b]pyridin-2-yl]-3,6-dihydropyridin-1(2H)-yl}sulfonyl)acetonitrile;
propan-2-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-(5-fluoro-2-methoxyphenyl)-2-[2-(methylsulfonyl)-2-azaspiro[3.3]hept-6-yl]-1H-pyrrolo[2,3-b]pyridine;
ethyl ({4-[5-cyano-4-(5-fluoro-2-methoxyphenyl)-1H-pyrrolo[2,3-b]pyridin-2-yl]-3,6-dihydropyridin-1(2H)-yl}sulfonyl)carbamate;
N-[2-(4-fluoro-2-{2-[1-(methylsulfonyl)-1,2,3,6-tetrahydropyridin-4-yl]-1H-pyrrolo[2,3-b]pyridin-4-yl}phenoxy)ethyl]methanesulfonamide;
2-{4-fluoro-2-[2-(1,2,3,6-tetrahydropyridin-4-yl)-1H-pyrrolo[2,3-b]pyridin-4-yl]phenoxy}ethanamine;
N-[4-({4-[4-(5-fluoro-2-methoxyphenyl)-1H-pyrrolo[2,3-b]pyridin-2-yl]-3,6-dihydropyridin-1(2H)-yl}methyl)phenyl]methanesulfonamide;
tert-butyl 4-{4-[5-fluoro-2-(methylamino)phenyl]-1H-pyrrolo[2,3-b]pyridin-2-yl}-3,6-dihydropyridine-1(2H)-carboxylate;
4-fluoro-N-methyl-2-[2-(1,2,3,6-tetrahydropyridin-4-yl)-1H-pyrrolo[2,3-b]pyridin-4-yl]aniline;
1-amino-4-[4-(5-fluoro-2-methoxyphenyl)-1H-pyrrolo[2,3-b]pyridin-2-yl]-N,N-dimethylcyclohex-3-ene-1-carboxamide;
4-(5-fluoro-2-methoxyphenyl)-2-(1,2,3,6-tetrahydropyridin-4-yl)-1H-pyrrolo[2,3-b]pyridine-3-carbonitrile;
1-(3-{4-[4-(5-fluoro-2-methoxyphenyl)-1H-pyrrolo[2,3-b]pyridin-2-yl]-3,6-dihydropyridin-1(2H)-yl}-3-oxopropanoyl)prolinamide;
N-ethoxy-4-[4-(5-fluoro-2-methoxyphenyl)-1H-pyrrolo[2,3-b]pyridin-2-yl]cyclohex-3-ene-1-carboxamide;
4-(5-fluoro-2-methoxyphenyl)-2-(1,2,3,6-tetrahydropyridin-4-yl)-1H-pyrrolo[2,3-b]pyridine-3-carboxamide;
ethyl ({3-[4-(5-fluoro-2-methoxyphenyl)-1H-pyrrolo[2,3-b]pyridin-2-yl]-8-azabicyclo[3.2.1]oct-2-en-8-yl}sulfonyl)carbamate;
4-[4-(5-fluoro-2-methoxyphenyl)-1H-pyrrolo[2,3-b]pyridin-2-yl]-N-(4-methoxybenzyl)cyclohex-3-ene-1-sulfonamide;
methyl 4-[4-(5-fluoro-2-methoxyphenyl)-1H-pyrrolo[2,3-b]pyridin-2-yl]-3,6-dihydro-2H-1,2'-bipyridine-3'-carboxylate;
1-({4-[4-(5-fluoro-2-methoxyphenyl)-1H-pyrrolo[2,3-b]pyridin-2-yl]piperidin-1-yl}acetyl)-L-prolinamide;

1-tert-butyl 2-methyl (2S)-4-{4-[4-(5-fluoro-2-methoxyphenyl)-1H-pyrrolo[2,3-b]pyridin-2-yl]-3,6-dihydropyridin-1(2H)-yl}pyrrolidine-1,2-dicarboxylate;

4-[4-(5-fluoro-2-methoxyphenyl)-1H-pyrrolo[2,3-b]pyridin-2-yl]-3,6-dihydro-2H-1,2'-bipyridine-3'-carboxylic acid;

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide;

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)methanesulfonamide;

3-{4-[4-(5-fluoro-2-methoxyphenyl)-1H-pyrrolo[2,3-b]pyridin-2-yl]-3,6-dihydropyridin-1(2H)-yl}-4-hydroxycyclobut-3-ene-1,2-dione;

methyl 4-{4-[4-(5-fluoro-2-methoxyphenyl)-1H-pyrrolo[2,3-b]pyridin-2-yl]-3,6-dihydropyridin-1(2H)-yl}-L-prolinate;

methyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-prolinate;

ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate;

4-(5-fluoro-2-methoxyphenyl)-2-[1-(hydroxyacetyl)-1,2,3,6-tetrahydropyridin-4-yl]-1H-pyrrolo[2,3-b]pyridine-3-carbonitrile;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carbonitrile;

ethyl ({4-[3-cyano-4-(5-fluoro-2-methoxyphenyl)-1H-pyrrolo[2,3-b]pyridin-2-yl]-3,6-dihydropyridin-1(2H)-yl}sulfonyl)carbamate;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carboxamide;

ethyl ({4-[3-carbamoyl-4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-ene-1-sulfonamide;

4-(5-fluoro-2-methoxyphenyl)-2-[1-(methylcarbamoyl)-1,2,3,6-tetrahydropyridin-4-yl]-1H-pyrrolo[2,3-b]pyridine-3-carboxamide;

ethyl ({6-[4-(5-fluoro-2-methoxyphenyl)-1H-pyrrolo[2,3-b]pyridin-2-yl]-2-azaspiro[3.3]hept-2-yl}sulfonyl)carbamate;

3-{6-[4-(5-fluoro-2-methoxyphenyl)-1H-pyrrolo[2,3-b]pyridin-2-yl]-2-azaspiro[3.3]hept-2-yl}propane-1,2-diol;

2-{6-[4-(5-fluoro-2-methoxyphenyl)-1H-pyrrolo[2,3-b]pyridin-2-yl]-2-azaspiro[3.3]hept-2-yl}-N,N-dimethylacetamide;

2-({4-[4-(5-fluoro-2-methoxyphenyl)-1H-pyrrolo[2,3-b]pyridin-2-yl]-3,6-dihydropyridin-1(2H)-yl}sulfonyl)-N-(3-hydroxycyclobutyl)acetamide;

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-proline;

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylic acid;

2-[1-(azetidin-1-ylsulfonyl)-1,2,3,6-tetrahydropyridin-4-yl]-4-(5-fluoro-2-methoxyphenyl)-1H-pyrrolo[2,3-b]pyridine;

1-({4-[4-(5-fluoro-2-methoxyphenyl)-1H-pyrrolo[2,3-b]pyridin-2-yl]-3,6-dihydropyridin-1(2H)-yl}sulfonyl)azetidine-3-carbonitrile;

2-{1-[(4,4-difluoropiperidin-1-yl)sulfonyl]-1,2,3,6-tetrahydropyridin-4-yl}-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}cyclohex-3-ene-1-carboxamide;

4-[4-(5-fluoro-2-methoxyphenyl)-1H-pyrrolo[2,3-b]pyridin-2-yl]-N-(1-methyl-1H-pyrazol-4-yl)cyclohex-3-ene-1-carboxamide;

4-[4-(5-fluoro-2-methoxyphenyl)-1H-pyrrolo[2,3-b]pyridin-2-yl]-N-(1H-tetrazol-5-ylmethyl)cyclohex-3-ene-1-carboxamide;

N-{4-[4-(5-fluoro-2-methoxyphenyl)-1H-pyrrolo[2,3-b]pyridin-2-yl]cyclohex-3-en-1-yl}-L-norvaline;

4-[4-(5-fluoro-2-methoxyphenyl)-1H-pyrrolo[2,3-b]pyridin-2-yl]-N-(1H-tetrazol-5-ylmethyl)cyclohex-3-ene-1-amine;

2-[4-({4-[4-(5-fluoro-2-methoxyphenyl)-1H-pyrrolo[2,3-b]pyridin-2-yl]-3,6-dihydropyridin-1(2H)-yl}sulfonyl)piperidin-1-yl]-N,N-dimethylacetamide;

2-{4-[4-(5-fluoro-2-methoxyphenyl)-1H-pyrrolo[2,3-b]pyridin-2-yl]-3,6-dihydropyridin-1(2H)-yl}-1-[(2R)-2-(hydroxymethyl)pyrrolidin-1-yl]ethanone;

4-(5-fluoro-2-methoxyphenyl)-2-[1-(methylsulfonyl)-2,3,6,7-tetrahydro-1H-azepin-4-yl]-1H-pyrrolo[2,3-b]pyridine;

4-[4-(5-fluoro-2-methoxyphenyl)-1H-pyrrolo[2,3-b]pyridin-2-yl]-N-methyl-2,3,6,7-tetrahydro-1H-azepine-1-carboxamide;

[1-({4-[4-(5-fluoro-2-methoxyphenyl)-1H-pyrrolo[2,3-b]pyridin-2-yl]-3,6-dihydropyridin-1(2H)-yl}carbonyl)-1,2,3,6-tetrahydropyridin-4-yl]boronic acid;

3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione;

N-{4-[4-(5-fluoro-2-methoxyphenyl)-1H-pyrrolo[2,3-b]pyridin-2-yl]cyclohex-3-en-1-yl}methanesulfonamide;

1-{4-[4-(5-fluoro-2-methoxyphenyl)-1H-pyrrolo[2,3-b]pyridin-2-yl]cyclohex-3-en-1-yl}-3-methylurea;

N-{4-[4-(5-fluoro-2-methoxyphenyl)-1H-pyrrolo[2,3-b]pyridin-2-yl]cyclohex-3-en-1-yl}-2-hydroxyacetamide;

2-cyano-N-{4-[4-(5-fluoro-2-methoxyphenyl)-1H-pyrrolo[2,3-b]pyridin-2-yl]cyclohex-3-en-1-yl}acetamide;

4-[4-(5-fluoro-2-methoxyphenyl)-1H-pyrrolo[2,3-b]pyridin-2-yl]-1,2,5,6-tetrahydropyridine-3-carbonitrile;

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetonitrile;

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}cyclohex-3-ene-1-carboxamide;

2-{4-[4-(5-fluoro-2-methoxyphenyl)-1H-pyrrolo[2,3-b]pyridin-2-yl]piperidin-1-yl}-1-(3-methoxyazetidin-1-yl)ethanone;

1-({4-[4-(5-fluoro-2-methoxyphenyl)-1H-pyrrolo[2,3-b]pyridin-2-yl]piperidin-1-yl}acetyl) azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-(3-hydroxy-3-methylazetidin-1-yl)ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]piperidin-1-yl}ethanone;

1-(3-fluoroazetidin-1-yl)-2-{4-[4-(5-fluoro-2-methoxyphenyl)-1H-pyrrolo[2,3-b]pyridin-2-yl]piperidin-1-yl}ethanone;

N-(3-fluorocyclobutyl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]piperidin-1-yl}-1-(3-hydroxypyrrolidin-1-yl)ethanone;

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid;

4-fluoro-2-{2-[1-(methylsulfonyl)-1,2,3,6-tetrahydropyridin-4-yl]-1H-pyrrolo[2,3-b]pyridin-4-yl}aniline;

methyl N-{4-[4-(5-fluoro-2-methoxyphenyl)-1H-pyrrolo[2,3-b]pyridin-2-yl]cyclohex-3-en-1-yl}-3-methyl-L-valinate;

N-cyano-4-[4-(5-fluoro-2-methoxyphenyl)-1H-pyrrolo[2,3-b]pyridin-2-yl]cyclohex-3-ene-1-carboxamide;

2-(3,3-dimethyl-1,2,3,6-tetrahydropyridin-4-yl)-4-(5-fluoro-2-methoxyphenyl)-1H-pyrrolo[2,3-b]pyridine;

2-(methylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-{[({4-[4-(5-fluoro-2-methoxyphenyl)-1H-pyrrolo[2,3-b]pyridin-2-yl]-3,6-dihydropyridin-1(2H)-yl}sulfonyl)carbamoyl]oxy}ethyl acetate;

2-(pyrrolidin-1-yl)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

azetidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-hydroxyethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

N-[2-(3-fluoro-5-{2-[1-(methylsulfonyl)-1,2,3,6-tetrahydropyridin-4-yl]-1H-pyrrolo[2,3-b]pyridin-4-yl}phenoxy)ethyl]methanesulfonamide;

4-[4-(5-fluoro-2-methoxyphenyl)-1H-pyrrolo[2,3-b]pyridin-2-yl]-5,6-dihydropyridin-2(1H)-one;

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)acetamide;

1-{4-[4-(5-fluoro-2-methoxyphenyl)-1H-pyrrolo[2,3-b]pyridin-2-yl]-3,6-dihydropyridin-1(2H)-yl}-3-[2-(hydroxymethyl)pyrrolidin-1-yl]propane-1,3-dione;

cyclopropyl({4-[4-(5-fluoro-2-methoxyphenyl)-1H-pyrrolo[2,3-b]pyridin-2-yl]cyclohex-3-en-1-yl}amino)acetic acid;

2-[3,3-dimethyl-1-(methylsulfonyl)-1,2,3,6-tetrahydropyridin-4-yl]-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N,3,3-trimethyl-3,6-dihydropyridine-1(2H)-carboxamide;

4-[4-(5-fluoro-2-methoxyphenyl)-1H-pyrrolo[2,3-b]pyridin-2-yl]cyclohex-3-en-1-amine;

4-(5-fluoro-2-methoxyphenyl)-2-[(6S)-6-methyl-1,2,3,6-tetrahydropyridin-4-yl]-1H-pyrrolo[2,3-b]pyridine;

N²-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N-methylglycinamide;

tert-butyl N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinate;

N²-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinamide;

N²-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N,N-dimethylglycinamide;

tert-butyl {4-[4-(4-fluoro-2-methoxyphenyl)-1H-pyrrolo[2,3-b]pyridin-2-yl]-3,6-dihydropyridin-1(2H)-yl}acetate;

{4-[4-(5-fluoro-2-methoxyphenyl)-1H-pyrrolo[2,3-b]pyridin-2-yl]-3,3-dimethyl-3,6-dihydropyridin-1(2H)-yl}acetic acid;

4-[4-(5-fluoro-2-methoxyphenyl)-1H-pyrrolo[2,3-b]pyridin-2-yl]cyclohex-3-ene-1-carbonitrile;

2-{4-[4-(5-fluoro-2-methoxyphenyl)-5-methoxy-1H-pyrrolo[2,3-b]pyridin-2-yl]-3,6-dihydropyridin-1(2H)-yl}-N,N-dimethylacetamide;

ethyl ({5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}sulfonyl)carbamate;

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}propane-1,2-diol;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

2-{4-[4-(4-fluoro-2-methoxyphenyl)-1H-pyrrolo[2,3-b]pyridin-2-yl]-3,6-dihydropyridin-1(2H)-yl}acetamide;

2-{4-[4-(4-fluoro-2-methoxyphenyl)-1H-pyrrolo[2,3-b]pyridin-2-yl]-3,6-dihydropyridin-1(2H)-yl}-N-methylacetamide;

N-{4-[4-(5-fluoro-2-methoxyphenyl)-1H-pyrrolo[2,3-b]pyridin-2-yl]cyclohexyl}-D-valine;

2-{4-[5-fluoro-4-(5-fluoro-2-methoxyphenyl)-1H-pyrrolo[2,3-b]pyridin-2-yl]piperidin-1-yl}acetamide;

4-(5-fluoro-2-methoxyphenyl)-2-{1-[2-(2-methoxyethoxy)ethyl]-1,2,3,6-tetrahydropyridin-4-yl}-1H-pyrrolo[2,3-b]pyridine;

4-[4-(5-fluoro-2-methoxyphenyl)-1H-pyrrolo[2,3-b]pyridin-2-yl]cyclohex-3-en-1-yl methylsulfamate;

2-{4-[4-(5-fluoro-2-methoxyphenyl)-1H-pyrrolo[2,3-b]pyridin-2-yl]-3,6-dihydropyridin-1(2H)-yl}-1-(3-methoxyazetidin-1-yl)ethanone;

1-({4-[4-(5-fluoro-2-methoxyphenyl)-1H-pyrrolo[2,3-b]pyridin-2-yl]-3,6-dihydropyridin-1(2H)-yl}acetyl)azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(hydroxymethyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-1-(3-hydroxy-3-methylazetidin-1-yl) ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

N-cyclobutyl-2-{4-[4-(5-fluoro-2-methoxyphenyl)-1H-pyrrolo[2,3-b]pyridin-2-yl]-3,6-dihydropyridin-1(2H)-yl}acetamide;

1-(3-fluoroazetidin-1-yl)-2-{4-[4-(5-fluoro-2-methoxyphenyl)-1H-pyrrolo[2,3-b]pyridin-2n-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

N-(3-fluorocyclobutyl)-2-{4-[4-(5-fluoro-2-methoxyphenyl)-1H-pyrrolo[2,3-b]pyridin-2-yl]-3,6-dihydropyridin-1(2H)-yl}acetamide;

2-{4-[4-(5-fluoro-2-methoxyphenyl)-1H-pyrrolo[2,3-b]pyridin-2-yl]-3,6-dihydropyridin-1(2H)-yl}-1-(3-hydroxypyrrolidin-1-yl)ethanone;

2-{4-[4-(5-fluoro-2-methoxyphenyl)-1H-pyrrolo[2,3-b]pyridin-2-yl]-3,3-dimethyl-3,6-dihydropyridin-1(2H)-yl}-N,N-dimethylacetamide;

3-{4-[4-(5-fluoro-2-methoxyphenyl)-1H-pyrrolo[2,3-b]pyridin-2-yl]-3,3-dimethyl-3,6-dihydropyridin-1(2H)-yl}propane-1,2-diol;

1-({4-[4-(5-fluoro-2-methoxyphenyl)-1H-pyrrolo[2,3-b]pyridin-2-yl]piperidin-1-yl}acetyl)-L-proline;

1-({4-[4-(5-fluoro-2-methoxyphenyl)-1H-pyrrolo[2,3-b]pyridin-2-yl]-3,6-dihydropyridin-1(2H)-yl}acetyl)-L-proline;

2-{4-[4-(5-fluoro-2-methoxyphenyl)-1H-pyrrolo[2,3-b]pyridin-2-yl]piperidin-1-yl}-N-(methylsulfonyl)acetamide;

1-[(3S,4S)-3,4-dihydroxypyrrolidin-1-yl]-2-{4-[4-(5-fluoro-2-methoxyphenyl)-1H-pyrrolo[2,3-b]pyridin-2-yl]piperidin-1-yl}ethanone;

1-[(3S,4S)-3,4-dihydroxypyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

N-{4-[4-(5-fluoro-2-methoxyphenyl)-1H-pyrrolo[2,3-b]pyridin-2-yl]cyclohex-3-en-1-yl}-L-serine;

5-[4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

4-(5-fluoro-2-methoxyphenyl)-2-[4-(piperazin-1-yl)cyclohex-1-en-1-yl]-1H-pyrrolo[2,3-b]pyridine;

N²-{4-[4-(5-fluoro-2-methoxyphenyl)-1H-pyrrolo[2,3-b]pyridin-2-yl]cyclohex-3-en-1-yl}-N,N-dimethyl-D-valinamide;

(4R)-1-{4-[4-(5-fluoro-2-methoxyphenyl)-1H-pyrrolo[2,3-b]pyridin-2-yl]cyclohex-3-en-1-yl}-4-hydroxy-L-proline;

N-{4-[4-(5-fluoro-2-methoxyphenyl)-1H-pyrrolo[2,3-b]pyridin-2-yl]cyclohex-3-en-1-yl}-L-valine;

2-{4-[4-(2-methoxyphenyl)-1H-pyrrolo[2,3-b]pyridin-2-yl]piperidin-1-yl}-N-methylacetamide;

{4-[4-(2-methoxyphenyl)-1H-pyrrolo[2,3-b]pyridin-2-yl]piperidin-1-yl}acetic acid;

2-[(6S)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;

4-(5-fluoro-2-methoxyphenyl)-2-[(6R)-6-methyl-1,2,3,6-tetrahydropyridin-4-yl]-1H-pyrrolo[2,3-b]pyridine;

4-(5-fluoro-2-methoxyphenyl)-2-[(2S)-2-methyl-1-(methylsulfonyl)piperidin-4-yl]-1H-pyrrolo[2,3-b]pyridine;

({4-[4-(5-fluoro-2-methoxyphenyl)-1H-pyrrolo[2,3-b]pyridin-2-yl]cyclohex-3-en-1-yl}oxy)acetic acid;

N-{4-[4-(5-fluoro-2-methoxyphenyl)-1H-pyrrolo[2,3-b]pyridin-2-yl]cyclohex-3-en-1-yl}-L-threonine;

2-{1-[(1,1-dioxidothiomorpholin-4-yl)sulfonyl]-1,2,3,6-tetrahydropyridin-4-yl}-4-(5-fluoro-2-methoxyphenyl)-1H-pyrrolo[2,3-b]pyridine;

4-(5-fluoro-2-methoxyphenyl)-2-{1-[(4-methylpiperazin-1-yl)sulfonyl]-1,2,3,6-tetrahydropyridin-4-yl}-1H-pyrrolo[2,3-b]pyridine;

ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-4-carboxylate;

ethyl 1-({4-[4-(5-fluoro-2-methoxyphenyl)-1H-pyrrolo[2,3-b]pyridin-2-yl]-3,6-dihydropyridin-1(2H)-yl}sulfonyl)prolinate;

ethyl {4-[4-(5-fluoro-2-methoxyphenyl)-1H-pyrrolo[2,3-b]pyridin-2-yl]-3,6-dihydropyridin-1(2H)-yl}acetate;

propan-2-yl {4-[4-(5-fluoro-2-methoxyphenyl)-1H-pyrrolo[2,3-b]pyridin-2-yl]-3,6-dihydropyridin-1(2H)-yl}acetate;

{4-[3-cyano-4-(5-fluoro-2-methoxyphenyl)-1H-pyrrolo[2,3-b]pyridin-2-yl]-3,6-dihydropyridin-1(2H)-yl}acetic acid;

4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;

4-(2-ethoxy-4,5-difluorophenyl)-2-(1,2,3,6-tetrahydropyridin-4-yl)-1H-pyrrolo[2,3-b]pyridine;

2-hydroxy-2-methylpropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

(2,2-dimethyl-1,3-dioxolan-4-yl)methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

tetrahydro-2H-pyran-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-(2-ethoxy-4,5-difluorophenyl)-2-[1-(methylsulfonyl)-1,2,3,6-tetrahydropyridin-4-yl]-1H-pyrrolo[2,3-b]pyridine;

4-[4-(2-ethoxy-4,5-difluorophenyl)-1H-pyrrolo[2,3-b]pyridin-2-yl]-N-methyl-3,6-dihydropyridine-1(2H)-carboxamide;

2-{4-[5-fluoro-4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;

{(2S)-4-[4-(5-fluoro-2-methoxyphenyl)-1H-pyrrolo[2,3-b]pyridin-2-yl]-1,2,3,6-tetrahydropyridin-2-yl}methanol;

{(2S)-4-[4-(5-fluoro-2-methoxyphenyl)-1H-pyrrolo[2,3-b]pyridin-2-yl]-1,2,5,6-tetrahydropyridin-2-yl}methanol;

2-{4-[4-(4,5-difluoro-2-methoxyphenyl)-1H-pyrrolo[2,3-b]pyridin-2-yl]piperidin-1-yl}-N-methylacetamide;

2-{4-[4-(4,5-difluoro-2-methoxyphenyl)-1H-pyrrolo[2,3-b]pyridin-2-yl]piperidin-1-yl}-N,N-dimethylacetamide;

2-{5-[4-(5-fluoro-2-methoxyphenyl)-1H-pyrrolo[2,3-b]pyridin-2-yl]-2,3,4,7-tetrahydro-1H-azepin-1-yl}acetamide;

2-{5-[4-(5-fluoro-2-methoxyphenyl)-1H-pyrrolo[2,3-b]pyridin-2-yl]-2,3,4,7-tetrahydro-1H-azepin-1-yl}-N,N-dimethylacetamide;

(1 S,2S,3R,4R)-3-[({4-[4-(4,5-difluoro-2-methoxyphenyl)-1H-pyrrolo[2,3-b]pyridin-2-yl]-3,6-dihydropyridin-1(2H)-yl}acetyl)amino]bicyclo[2.2.1]hept-5-ene-2-carboxamide;

{4-[4-(5-fluoro-2-methoxyphenyl)-1H-pyrrolo[2,3-b]pyridin-2-yl]cyclohex-3-en-1-yl}[(2S)-2-(hydroxymethyl)pyrrolidin-1-yl]methanone;

2-{4-[4-(4-fluoro-2-methoxyphenyl)-1H-pyrrolo[2,3-b]pyridin-2-yl]piperidin-1-yl}acetamide;

2-{4-[4-(4-fluoro-2-methoxyphenyl)-1H-pyrrolo[2,3-b]pyridin-2-yl]piperidin-1-yl}-N-methylacetamide;
4-(5-fluoro-2-methoxyphenyl)-2-(octahydrocyclopenta[c]pyrrol-5-yl)-1H-pyrrolo[2,3-b]pyridine;
1-{4-[5-fluoro-4-(5-fluoro-2-methoxyphenyl)-1H-pyrrolo[2,3-b]pyridin-2-yl]piperidin-1-yl}-2-hydroxyethanone;
pyrrolidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
piperidin-4-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
piperidin-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
pyrrolidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2,3-dihydroxypropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
methyl {4-[4-(2-methoxyphenyl)-1H-pyrrolo[2,3-b]pyridin-2-yl]piperidin-1-yl}acetate;
1-[(2S)-2-(hydroxymethyl)pyrrolidin-1-yl]-2-{4-[4-(2-methoxyphenyl)-1H-pyrrolo[2,3-b]pyridin-2-yl]piperidin-1-yl}ethanone;
(2R)-2-({4-[4-(5-fluoro-2-methoxyphenyl)-1H-pyrrolo[2,3-b]pyridin-2-yl]cyclohex-3-en-1-yl}amino)-1-(3-hydroxyazetidin-1-yl)-3-methylbutan-1-one;
1-{4-[4-(5-fluoro-2-methoxyphenyl)-1H-pyrrolo[2,3-b]pyridin-2-yl]cyclohex-3-en-1-yl}-N,N-dimethyl-L-prolinamide;
(2R)-({4-[4-(5-fluoro-2-methoxyphenyl)-1H-pyrrolo[2,3-b]pyridin-2-yl]cyclohex-3-en-1-yl}amino)(phenyl)acetic acid;
4-(5-fluoro-2-methoxyphenyl)-2-[3-(methylsulfonyl)-3-azabicyclo[4.1.0]hept-6-yl]-1H-pyrrolo[2,3-b]pyridine;
4-(5-fluoro-2-methoxyphenyl)-2-[4-(1H-tetrazol-5-yl)cyclohex-1-en-1-yl]-1H-pyrrolo[2,3-b]pyridine;
4-[4-(5-fluoro-2-methoxyphenyl)-1H-pyrrolo[2,3-b]pyridin-2-yl]cyclohex-3-en-1-yl tert-butylcarbamate;
2-{4-[4-(5-fluoro-2-methoxyphenyl)-5-methoxy-1H-pyrrolo[2,3-b]pyridin-2-yl]-3,6-dihydropyridin-1(2H)-yl}-1-[(2S)-2-(hydroxymethyl)pyrrolidin-1-yl]ethanone;
2-{4-[4-(4,5-difluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
2-{(2S)-4-[4-(5-fluoro-2-methoxyphenyl)-1H-pyrrolo[2,3-b]pyridin-2-yl]-2-methylpiperidin-1-yl}-N,N-dimethylacetamide;
4,4,4-trifluoro-2-{4-[4-(5-fluoro-2-methoxyphenyl)-1H-pyrrolo[2,3-b]pyridin-2-yl]-3,6-dihydropyridin-1(2H)-yl}butanoic acid;
2-{4-[4-(5-fluoro-2-methoxyphenyl)-1H-pyrrolo[2,3-b]pyridin-2-yl]-3,6-dihydropyridin-1(2H)-yl}-N,N-dimethyl-2-oxoethanesulfonamide;
2-{4-[4-(5-fluoro-2-methoxyphenyl)-1H-pyrrolo[2,3-b]pyridin-2-yl]piperidin-1-yl}-N-methyl-2-oxoethanesulfonamide;
2-{4-[4-(5-fluoro-2-methoxyphenyl)-1H-pyrrolo[2,3-b]pyridin-2-yl]piperidin-1-yl}-N,N-dimethyl-2-oxoethanesulfonamide;
1-{4-[4-(5-fluoro-2-methoxyphenyl)-1H-pyrrolo[2,3-b]pyridin-2-yl]-3,6-dihydropyridin-1(2H)-yl}-1-oxopropane-2-sulfonamide;
ethyl {4-[4-(5-fluoro-2-methoxyphenyl)-1H-pyrrolo[2,3-b]pyridin-2-yl]-3,6-dihydropyridin-1(2H)-yl}(phenyl)acetate;
ethyl 2-{4-[4-(5-fluoro-2-methoxyphenyl)-1H-pyrrolo[2,3-b]pyridin-2-yl]-3,6-dihydropyridin-1(2H)-yl}-1,3-thiazole-5-carboxylate;
tert-butyl 3-{4-[4-(5-fluoro-2-methoxyphenyl)-1H-pyrrolo[2,3-b]pyridin-2-yl]-3,6-dihydropyridin-1(2H)-yl}pyrrolidine-1-carboxylate;
ethyl {[(6S)-4-[4-(5-fluoro-2-methoxyphenyl)-1H-pyrrolo[2,3-b]pyridin-2-yl]-6-methyl-3,6-dihydropyridin-1(2H)-yl]sulfonyl}carbamate;
2-({4-[4-(5-fluoro-2-methoxyphenyl)-1H-pyrrolo[2,3-b]pyridin-2-yl]cyclohex-3-en-1-yl}oxy)ethanol;
2-{4-[4-(5-fluoro-2-methoxyphenyl)-1H-pyrrolo[2,3-b]pyridin-2-yl]piperidin-1-yl}propanoic acid;
{4-[4-(5-fluoro-2-methoxyphenyl)-1H-pyrrolo[2,3-b]pyridin-2-yl]-3,6-dihydropyridin-1(2H)-yl}(phenyl)acetic acid;
4-(5-fluoro-2-methoxyphenyl)-2-[1-(pyrrolidin-3-yl)-1,2,3,6-tetrahydropyridin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]piperidin-1-yl}-3-oxopropanenitrile;
5-fluoro-4-(5-fluoro-2-methoxyphenyl)-2-(1,2,3,6-tetrahydropyridin-4-yl)-1H-pyrrolo[2,3-b]pyridine-3-carbonitrile;
4-fluoro-2-[2-(1,2,3,6-tetrahydropyridin-4-yl)-1H-pyrrolo[2,3-b]pyridin-4-yl]benzamide;
{4-[3-cyano-5-fluoro-4-(5-fluoro-2-methoxyphenyl)-1H-pyrrolo[2,3-b]pyridin-2-yl]-3,6-dihydropyridin-1(2H)-yl}acetic acid;
2-aminoethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
azetidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2-(dimethylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2-(2,2-dimethyl-1,2,3,6-tetrahydropyridin-4-yl)-4-(5-fluoro-2-methoxyphenyl)-1H-pyrrolo[2,3-b]pyridine;
{4-[3-cyano-4-(5-fluoro-2-methoxyphenyl)-1H-pyrrolo[2,3-b]pyridin-2-yl]piperidin-1-yl}acetic acid;
4-(5-fluoro-2-methoxyphenyl)-2-(piperidin-4-yl)-1H-pyrrolo[2,3-b]pyridine-3-carbonitrile;
2-{4-[3-cyano-4-(5-fluoro-2-methoxyphenyl)-1H-pyrrolo[2,3-b]pyridin-2-yl]piperidin-1-yl}-N,N-dimethylacetamide;
5-({4-[4-(5-fluoro-2-methoxyphenyl)-1H-pyrrolo[2,3-b]pyridin-2-yl]piperidin-1-yl}methyl)-2,4-dihydro-3H-1,2,4-triazol-3-one;
4-(5-fluoro-2-methoxyphenyl)-2-{1-[1-(methylsulfonyl)pyrrolidin-3-yl]-1,2,3,6-tetrahydropyridin-4-yl}-1H-pyrrolo[2,3-b]pyridine;
2-{4-[4-(5-fluoro-2-methoxyphenyl)-1H-pyrrolo[2,3-b]pyridin-2-yl]piperidin-1-yl}-N-(propan-2-ylsulfonyl)acetamide;
ethyl 2-{4-[4-(5-fluoro-2-methoxyphenyl)-1H-pyrrolo[2,3-b]pyridin-2-yl]piperidin-1-yl}-1,3-thiazole-5-carboxylate;
methyl (4-{4-[4-(5-fluoro-2-methoxyphenyl)-1H-pyrrolo[2,3-b]pyridin-2-yl]-3,6-dihydropyridin-1(2H)-yl}cyclohexyl)acetate;
3-{4-[4-(5-fluoro-2-methoxyphenyl)-1H-pyrrolo[2,3-b]pyridin-2-yl]-3,6-dihydropyridin-1(2H)-yl}-1-methylpyrrolidin-2-one;

4-{4-[4-(5-fluoro-2-methoxyphenyl)-1H-pyrrolo[2,3-b]pyridin-2-yl]-3,6-dihydropyridin-1(2H)-yl}pyrrolidin-2-one;

2-{4-[4-(5-fluoro-2-methoxyphenyl)-1H-pyrrolo[2,3-b]pyridin-2-yl]piperidin-1-yl}-1,3-thiazole-5-carboxylic acid;

(2 S)-cyclohexyl({4-[4-(5-fluoro-2-methoxyphenyl)-1H-pyrrolo[2,3-b]pyridin-2-yl]cyclohex-3-en-1-yl}amino)acetic acid;

N-{4-[5-fluoro-4-(5-fluoro-2-methoxyphenyl)-1H-pyrrolo[2,3-b]pyridin-2-yl]cyclohex-3-en-1-yl}-D-valine;

N-{4-[5-fluoro-4-(5-fluoro-2-methoxyphenyl)-1H-pyrrolo[2,3-b]pyridin-2-yl]cyclohex-3-en-1-yl}-3-methyl-L-valine;

5-fluoro-4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;

4-(5-fluoro-2-methoxyphenyl)-2-[1-(methylsulfonyl)piperidin-4-yl]-1H-pyrrolo[2,3-b]pyridine-3-carbonitrile;

{4-[5-fluoro-4-(5-fluoro-2-methoxyphenyl)-1H-pyrrolo[2,3-b]pyridin-2-yl]piperidin-1-yl}acetic acid;

methyl 1-({4-[4-(5-fluoro-2-methoxyphenyl)-1H-pyrrolo[2,3-b]pyridin-2-yl]cyclohex-3-en-1-yl}carbonyl)prolinate;

N-cyano-4-[3-cyano-5-fluoro-4-(5-fluoro-2-methoxyphenyl)-1H-pyrrolo[2,3-b]pyridin-2-yl]-3,6-dihydropyridine-1(2H)-carboxamide;

(4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;

3-{4-[4-(5-fluoro-2-methoxyphenyl)-1H-pyrrolo[2,3-b]pyridin-2-yl]piperidin-1-yl}-1-methylpyrrolidin-2-one;

N-cyano-4-[5-fluoro-4-(5-fluoro-2-methoxyphenyl)-1H-pyrrolo[2,3-b]pyridin-2-yl]-3,6-dihydropyridine-1(2H)-carboxamide;

4-(5-fluoro-2-methoxyphenyl)-2-(1-{[2-(2-methoxyethoxy)ethyl]sulfonyl}-1,2,3,6-tetrahydropyridin-4-yl)-1H-pyrrolo[2,3-b]pyridine;

1-({4-[3-cyano-5-fluoro-4-(5-fluoro-2-methoxyphenyl)-1H-pyrrolo[2,3-b]pyridin-2-yl]-3,6-dihydropyridin-1(2H)-yl}acetyl)-L-prolinamide;

N-cyano-2-{4-[4-(5-fluoro-2-methoxyphenyl)-1H-pyrrolo[2,3-b]pyridin-2-yl]piperidin-1-yl}acetamide;

{(2R)-4-[4-(5-fluoro-2-methoxyphenyl)-1H-pyrrolo[2,3-b]pyridin-2-yl]-1,2,5,6-tetrahydropyridin-2-yl}methanol;

{(2R)-4-[4-(5-fluoro-2-methoxyphenyl)-1H-pyrrolo[2,3-b]pyridin-2-yl]-1,2,3,6-tetrahydropyridin-2-yl}methanol;

ethyl ({4-[5-fluoro-4-(5-fluoro-2-methoxyphenyl)-1H-pyrrolo[2,3-b]pyridin-2-yl]piperidin-1-yl}sulfonyl)carbamate;

2-{4-[5-fluoro-4-(5-fluoro-2-methoxyphenyl)-1H-pyrrolo[2,3-b]pyridin-2-yl]piperidin-1-yl}-N-(2-hydroxyethyl)-N-methylacetamide;

4-[4-(5-fluoro-2-methoxyphenyl)-1H-pyrrolo[2,3-b]pyridin-2-yl]cyclohex-3-en-1-yl[(3-hydroxyazetidin-1-yl)sulfonyl]carbamate;

4-(5-fluoro-2-methoxyphenyl)-2-{1-[(2-methoxyethyl)sulfonyl]-1,2,3,6-tetrahydropyridin-4-yl}-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}-2-(2-methoxyethoxy)ethanesulfonamide;

tert-butyl 3-{4-[4-(5-fluoro-2-methoxyphenyl)-1H-pyrrolo[2,3-b]pyridin-2-yl]-3,6-dihydropyridin-1(2H)-yl}cyclobutanecarboxylate;

3-{4-[4-(5-fluoro-2-methoxyphenyl)-1H-pyrrolo[2,3-b]pyridin-2-yl]-3,6-dihydropyridin-1(2H)-yl}cyclobutanecarboxylic acid;

4-(5-fluoro-2-methoxyphenyl)-2-[2-(methylsulfonyl)octahydrocyclopenta[c]pyrrol-5-yl]-1H-pyrrolo[2,3-b]pyridine;

[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]acetic acid;

$N^2$-{4-[4-(5-fluoro-2-methoxyphenyl)-1H-pyrrolo[2,3-b]pyridin-2-yl]cyclohex-3-en-1-yl}-N-methyl-D-valinamide;

N-{4-[4-(5-fluoro-2-methoxyphenyl)-1H-pyrrolo[2,3-b]pyridin-2-yl]cyclohex-3-en-1-yl}-L-phenylalanine;

N-{4-[4-(5-fluoro-2-methoxyphenyl)-1H-pyrrolo[2,3-b]pyridin-2-yl]cyclohex-3-en-1-yl}-L-tyrosine;

$N^2$-{4-[4-(5-fluoro-2-methoxyphenyl)-1H-pyrrolo[2,3-b]pyridin-2-yl]cyclohex-3-en-1-yl}-L-valinamide;

$N^2$-{4-[4-(5-fluoro-2-methoxyphenyl)-1H-pyrrolo[2,3-b]pyridin-2-yl]cyclohex-3-en-1-yl}-N,3-dimethyl-L-valinamide;

(2S)-({4-[4-(5-fluoro-2-methoxyphenyl)-1H-pyrrolo[2,3-b]pyridin-2-yl]cyclohex-3-en-1-yl}amino)(phenyl)acetic acid;

2-[1-(cyanoacetyl)-1,2,3,6-tetrahydropyridin-4-yl]-4-(5-fluoro-2-methoxyphenyl)-1H-pyrrolo[2,3-b]pyridine-5-carbonitrile;

4-(5-fluoro-2-methoxyphenyl)-2-[1-(methylsulfonyl)-1,2,3,6-tetrahydropyridin-4-yl]-3-nitro-1H-pyrrolo[2,3-b]pyridine;

4-(5-fluoro-2-methoxyphenyl)-2-(2-{[2-(2-methoxyethoxy)ethyl]sulfonyl}-1,2,3,3a,4,6a-hexahydrocyclopenta[c]pyrrol-5-yl)-1H-pyrrolo[2,3-b]pyridine;

(9aR)-8-[4-(5-fluoro-2-methoxyphenyl)-1H-pyrrolo[2,3-b]pyridin-2-yl]-1,6,7,9a-tetrahydropyrido[2,1-c][1,4]oxazin-3(4H)-one;

7-[4-(5-fluoro-2-methoxyphenyl)-1H-pyrrolo[2,3-b]pyridin-2-yl]-1,5,6,8a-tetrahydro[1,3]oxazolo[3,4-a]pyridin-3-one;

2-{4-[4-(5-fluoro-2-methoxyphenyl)-1H-pyrrolo[2,3-b]pyridin-2-yl]piperidin-1-yl}-N-(2-methoxyethyl)-N-methylacetamide;

{4-[4-(5-fluoro-2-methoxyphenyl)-1H-pyrrolo[2,3-b]pyridin-2-yl]piperidin-1-yl}(phenyl)acetic acid;

2-{4-[5-cyano-4-(5-fluoro-2-methoxyphenyl)-1H-pyrrolo[2,3-b]pyridin-2-yl]-3,6-dihydropyridin-1(2H)-yl}acetamide;

N-(3-fluorocyclobutyl)-4-[4-(5-fluoro-2-methoxyphenyl)-1H-pyrrolo[2,3-b]pyridin-2-yl]-2,5-dihydro-1H-pyrrole-2-carboxamide;

4-(5-fluoro-2-methoxyphenyl)-2-[(2R)-2-methyl-1,2,3,6-tetrahydropyridin-4-yl]-1H-pyrrolo[2,3-b]pyridine-4-(5-fluoro-2-methoxyphenyl)-2-[(6R)-6-methyl-1,2,3,6-tetrahydropyridin-4-yl]-1H-pyrrolo[2,3-b]pyridine (1:1);

2-{4-[4-(5-fluoro-2-methoxyphenyl)-1H-pyrrolo[2,3-b]pyridin-2-yl]-6,6-dimethyl-3,6-dihydropyridin-1(2H)-yl}-N,N-dimethylacetamide;

methyl 4-[4-(5-fluoro-2-methoxyphenyl)-1H-pyrrolo[2,3-b]pyridin-2-yl]-1-(methylcarbamoyl)-2,5-dihydro-1H-pyrrole-2-carboxylate;

4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile;

5-[5-cyano-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-2-{4-[4-(5-fluoro-2-methoxyphenyl)-1H-pyrrolo[2,3-b]pyridin-2-yl]-3,6-dihydropyridin-1(2H)-yl}acetamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}ethanone;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-3-carboxylate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxamide;
N-cyano-4-[4-(5-fluoro-2-methoxyphenyl)-1H-pyrrolo[2,3-b]pyridin-2-yl]piperidine-1-carboxamide;
2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide;
N-{5-[4-(5-fluoro-2-methoxyphenyl)-1H-pyrrolo[2,3-b]pyridin-2-yl]-1,2,3,3a,4,6a-hexahydropentalen-2-yl}-D-valine;
methyl 4-[4-(5-fluoro-2-methoxyphenyl)-1H-pyrrolo[2,3-b]pyridin-2-yl]-3,6-dihydropyridine-1(2H)-carboxylate;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine;
2-{4-[5-cyano-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;
2-({4-[4-(5-fluoro-2-methoxyphenyl)-1H-pyrrolo[2,3-b]pyridin-2-yl]cyclohex-3-en-1-yl}oxy)-N,N-dimethylacetamide;
2-({4-[4-(5-fluoro-2-methoxyphenyl)-1H-pyrrolo[2,3-b]pyridin-2-yl]cyclohex-3-en-1-yl}oxy)-1-(morpholin-4-yl)ethanone;
4-[5-fluoro-2-(methylsulfanyl)phenyl]-2-[1-(methylsulfonyl)-1,2,3,6-tetrahydropyridin-4-yl]-1H-pyrrolo[2,3-b]pyridine;
4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-5-carbonitrile;
2-{4-[5-cyano-4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;
2-{4-[5-cyano-4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;
2-{4-[4-(5-fluoro-2-methoxyphenyl)-1H-pyrrolo[2,3-b]pyridin-2-yl]-3,6-dihydropyridin-1(2H)-yl}-N-(2-methoxyethyl)-N-methylacetamide;
methyl (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl (trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl {4-[4-(5-fluoro-2-methoxyphenyl)-1H-pyrrolo[2,3-b]pyridin-2-yl]cyclohex-3-en-1-yl}acetate;
{4-[4-(5-fluoro-2-methoxyphenyl)-1H-pyrrolo[2,3-b]pyridin-2-yl]cyclohex-3-en-1-yl}acetic acid;
(4-{4-[4-(5-fluoro-2-methoxyphenyl)-1H-pyrrolo[2,3-b]pyridin-2-yl]piperidin-1-yl}cyclohexyl)acetic acid;
methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate;
N-{4-[4-(5-fluoro-2-methoxyphenyl)-1H-pyrrolo[2,3-b]pyridin-2-yl]cyclohex-3-en-1-yl}-L-leucine;
4-(5-fluoro-2-methoxyphenyl)-2-[(6R)-6-methyl-1-(methylsulfonyl)-1,2,3,6-tetrahydropyridin-4-yl]-1H-pyrrolo[2,3-b]pyridine;
2-[(6R)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(2R)-2-methyl-1-(methylsulfonyl)-1,2,3,6-tetrahydropyridin-4-yl]-1H-pyrrolo[2,3-b]pyridine;
2-[(2R)-4-[4-(5-fluoro-2-methoxyphenyl)-1H-pyrrolo[2,3-b]pyridin-2-yl]-2-methyl-3,6-dihydropyridin-1(2H)-yl]-N,N-dimethylacetamide;
{4-[4-(5-fluoro-2-methoxyphenyl)-1H-pyrrolo[2,3-b]pyridin-2-yl]cyclohex-3-en-1-yl}(3-hydroxyazetidin-1-yl)methanone;
2-{4-[5-fluoro-4-(5-fluoro-2-methoxyphenyl)-1H-pyrrolo[2,3-b]pyridin-2-yl]piperidin-1-yl}-N-methyl-2-oxoethanesulfonamide;
{4-[5-cyano-4-(5-fluoro-2-methoxyphenyl)-1H-pyrrolo[2,3-b]pyridin-2-yl]piperidin-1-yl}acetic acid;
2-[1-(cyanoacetyl)piperidin-4-yl]-4-(5-fluoro-2-methoxyphenyl)-1H-pyrrolo[2,3-b]pyridine-5-carbonitrile;
4-(5-fluoro-2-methoxyphenyl)-2-{1-[2-(3-hydroxyazetidin-1-yl)-2-oxoethyl]piperidin-4-yl}-1H-pyrrolo[2,3-b]pyridine-5-carbonitrile;
4-[5-fluoro-2-(methylsulfinyl)phenyl]-2-[1-(methylsulfonyl)-1,2,3,6-tetrahydropyridin-4-yl]-1H-pyrrolo[2,3-b]pyridine;
4-[3-cyano-5-fluoro-4-(5-fluoro-2-methoxyphenyl)-1H-pyrrolo[2,3-b]pyridin-2-yl]cyclohex-3-ene-1-carboxylic acid;
4-(5-fluoro-2-methoxyphenyl)-2-(1,2,3,3a,4,6a-hexahydrocyclopenta[c]pyrrol-5-yl)-5-hydroxy-1H-pyrrolo[2,3-b]pyridine-3-carbonitrile;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine-3-carbonitrile;
2-{4-[5-fluoro-4-(5-fluoro-2-methoxyphenyl)-1H-pyrrolo[2,3-b]pyridin-2-yl]piperidin-1-yl}-N-(3-hydroxycyclobutyl)-N-methylacetamide;
2-{4-[5-cyano-4-(5-fluoro-2-methoxyphenyl)-1H-pyrrolo[2,3-b]pyridin-2-yl]piperidin-1-yl}-N-(2-hydroxyethyl)-N-methylacetamide;
tert-butyl {4-[3-cyano-4-(5-fluoro-2-methoxyphenyl)-1H-pyrrolo[2,3-b]pyridin-2-yl]-3,6-dihydropyridin-1(2H)-yl}acetate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-oxoethanesulfonamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-oxopropane-2-sulfonamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethyl-2-oxoethanesulfonamide;
tert-butyl {5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetate;

2-{4-[4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-1-[(3S)-3-hydroxypyrrolidin-1-yl]ethanone;

4-({4-[4-(5-fluoro-2-methoxyphenyl)-1H-pyrrolo[2,3-b]pyridin-2-yl]-3,6-dihydropyridin-1(2H)-yl}carbonyl)benzoic acid;

3-({4-[4-(5-fluoro-2-methoxyphenyl)-1H-pyrrolo[2,3-b]pyridin-2-yl]-3,6-dihydropyridin-1(2H)-yl}carbonyl)benzoic acid;

tert-butyl (3aS,6aR)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;

tert-butyl (3aR,6aS)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;

(3-{4-[4-(5-fluoro-2-methoxyphenyl)-1H-pyrrolo[2,3-b]pyridin-2-yl]-3,6-dihydropyridin-1(2H)-yl}cyclobutyl)acetic acid;

2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoic acid;

ethyl 5-[4-(5-fluoro-2-methoxyphenyl)-1H-pyrrolo[2,3-b]pyridin-2-yl]-1,2,3,6-tetrahydropyridine-4-carboxylate;

{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

4-(5-fluoro-2-methoxyphenyl)-2-[1-(2,5,8,11-tetraoxatetradecan-14-yl)-1,2,3,6-tetrahydropyridin-4-yl]-1H-pyrrolo[2,3-b]pyridine;

5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-3-carbonitrile;

5-[3-cyano-5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

2-{4-[3-cyano-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

4-(5-fluoro-2-methoxyphenyl)-2-{2-[2-(3-hydroxyazetidin-1-yl)-2-oxoethyl]-1,2,3,3a,4,6a-hexahydrocyclopenta[c]pyrrol-5-yl}-1H-pyrrolo[2,3-b]pyridine-5-carbonitrile;

4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

(3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]ethanone;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-2-hydroxyethanone;

(3aR,5r,6aS)-N-cyano-5-[4-(5-fluoro-2-methoxyphenyl)-1H-pyrrolo[2,3-b]pyridin-2-yl]hexahydrocyclopenta[c]pyrrole-2(1H)-carboxamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N,N-dimethylacetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]propane-1,2-diol;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]acetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-3-oxopropanenitrile;

4-[4-(5-fluoro-2-methoxyphenyl)-1H-pyrrolo[2,3-b]pyridin-2-yl]cyclohexanecarboxylic acid;

(4-{4-[3-cyano-4-(5-fluoro-2-methoxyphenyl)-1H-pyrrolo[2,3-b]pyridin-2-yl]-3,6-dihydropyridin-1(2H)-yl}cyclohexyl)acetic acid;

(4-{4-[5-fluoro-4-(5-fluoro-2-methoxyphenyl)-1H-pyrrolo[2,3-b]pyridin-2-yl]piperidin-1-yl}cyclohexyl)acetic acid;

{4-[5-chloro-4-(5-fluoro-2-methoxyphenyl)-1H-pyrrolo[2,3-b]pyridin-2-yl]cyclohex-3-en-1-yl}acetic acid;

2-({4-[4-(5-fluoro-2-methoxyphenyl)-1H-pyrrolo[2,3-b]pyridin-2-yl]-3,6-dihydropyridin-1(2H)-yl}sulfonyl)ethanol;

(3-{4-[4-(5-fluoro-2-methoxyphenyl)-1H-pyrrolo[2,3-b]pyridin-2-yl]-3,6-dihydropyridin-1(2H)-yl}cyclobutyl)(3-hydroxyazetidin-1-yl)methanone;

2-{5-[3-cyano-5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

2-[(6R)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

{5-[4-(5-fluoro-2-methoxyphenyl)-1H-pyrrolo[2,3-b]pyridin-2-yl]-1,2,3,6-tetrahydropyridin-4-yl}methanol;

{4-[4-(5-fluoro-2-methoxyphenyl)-1H-pyrrolo[2,3-b]pyridin-2-yl]-3,6-dihydropyridin-1(2H)-yl}(3-hydroxycyclobutyl)methanone;

4-(5-fluoro-2-methoxyphenyl)-2-[(3R)-3-methyl-1,2,3,6-tetrahydropyridin-4-yl]-1H-pyrrolo[2,3-b]pyridine;

4-(5-fluoro-2-methoxyphenyl)-2-[(3S)-3-methyl-1,2,3,6-tetrahydropyridin-4-yl]-1H-pyrrolo[2,3-b]pyridine;

2-[(3R)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

2-[(3S)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

1-{4-[4-(5-fluoro-2-methoxyphenyl)-1H-pyrrolo[2,3-b]pyridin-2-yl]cyclohex-3-en-1-yl}-N-methyl-L-prolinamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone;

2-[(3aR,5S,6aS)-5-[4-(5-fluoro-2-methoxyphenyl)-1H-pyrrolo[2,3-b]pyridin-2-yl]hexahydrocyclopenta[c]pyrrol-2(1H)-yl]-1-[(2S)-2-(hydroxymethyl)pyrrolidin-1-yl]ethanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(2-hydroxyethyl)-N-methylacetamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(3-hydroxycyclobutyl)-N-methylacetamide;

[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl](3-hydroxycyclobutyl)methanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-methyl-2-oxoethanesulfonamide;

2-(8-azabicyclo[3.2.1]oct-2-en-3-yl)-4-(5-fluoro-2-methoxyphenyl)-1H-pyrrolo[2,3-b]pyridine-5-carbonitrile;

2-(8-azabicyclo[3.2.1]oct-2-en-3-yl)-5-fluoro-4-(5-fluoro-2-methoxyphenyl)-1H-pyrrolo[2,3-b]pyridine;

N-cyano-3-[5-fluoro-4-(5-fluoro-2-methoxyphenyl)-1H-pyrrolo[2,3-b]pyridin-2-yl]-8-azabicyclo[3.2.1]oct-2-ene-8-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

{3-[5-cyano-4-(5-fluoro-2-methoxyphenyl)-1H-pyrrolo[2,3-b]pyridin-2-yl]-8-azabicyclo[3.2.1]oct-2-en-8-yl}acetic acid;

{3-[5-fluoro-4-(5-fluoro-2-methoxyphenyl)-1H-pyrrolo[2,3-b]pyridin-2-yl]-8-azabicyclo[3.2.1]oct-2-en-8-yl}acetic acid;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}acetamide;

{4-[4-(5-fluoro-2-methoxyphenyl)-1H-pyrrolo[2,3-b]pyridin-2-yl]cyclohexyl}acetic acid;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

1-{4-[5-fluoro-4-(5-fluoro-2-methoxyphenyl)-1H-pyrrolo[2,3-b]pyridin-2-yl]cyclohex-3-en-1-yl}-N,N-dimethyl-L-prolinamide;

4-[3-cyano-4-(5-fluoro-2-methoxyphenyl)-1H-pyrrolo[2,3-b]pyridin-2-yl]cyclohex-3-ene-1-carboxylic acid;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

4-(5-fluoro-2-methoxyphenyl)-2-(8-{2-[(2S)-2-(hydroxymethyl)pyrrolidin-1-yl]-2-oxoethyl}-8-azabicyclo[3.2.1]oct-2-en-3-yl)-1H-pyrrolo[2,3-b]pyridine-5-carbonitrile;

4-(5-fluoro-2-methoxyphenyl)-2-{8-[2-(3-hydroxyazetidin-1-yl)-2-oxoethyl]-8-azabicyclo[3.2.1]oct-2-en-3-yl}-1H-pyrrolo[2,3-b]pyridine-5-carbonitrile;

{4-[5-cyano-4-(5-fluoro-2-methoxyphenyl)-1H-pyrrolo[2,3-b]pyridin-2-yl]cyclohex-3-en-1-yl}acetic acid;

2-(9-azabicyclo[3.3.1]non-2-en-3-yl)-4-(5-fluoro-2-methoxyphenyl)-1H-pyrrolo[2,3-b]pyridine;

4-(5-fluoro-2-methoxyphenyl)-2-[9-(methylsulfonyl)-9-azabicyclo[3.3.1]non-2-en-3-yl]-1H-pyrrolo[2,3-b]pyridine;

3-[4-(5-fluoro-2-methoxyphenyl)-1H-pyrrolo[2,3-b]pyridin-2-yl]-N-methyl-9-azabicyclo[3.3.1]non-2-ene-9-carboxamide;

2-{3-[4-(5-fluoro-2-methoxyphenyl)-1H-pyrrolo[2,3-b]pyridin-2-yl]-9-azabicyclo[3.3.1]non-2-en-9-yl}-N,N-dimethylacetamide;

3-{3-[4-(5-fluoro-2-methoxyphenyl)-1H-pyrrolo[2,3-b]pyridin-2-yl]-9-azabicyclo[3.3.1]non-2-en-9-yl}-3-oxopropanenitrile;

{3-[4-(5-fluoro-2-methoxyphenyl)-1H-pyrrolo[2,3-b]pyridin-2-yl]-9-azabicyclo[3.3.1]non-2-en-9-yl}(3-hydroxycyclobutyl)methanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(trans-4-hydroxycyclohexyl)acetamide;

4-[4-(4-fluoro-2-methoxyphenyl)-1H-pyrrolo[2,3-b]pyridin-2-yl]cyclohex-3-ene-1-carboxylic acid;

4-[4-(4,5-difluoro-2-methoxyphenyl)-1H-pyrrolo[2,3-b]pyridin-2-yl]cyclohex-3-ene-1-carboxylic acid;

4-[4-(2-methoxyphenyl)-1H-pyrrolo[2,3-b]pyridin-2-yl]cyclohex-3-ene-1-carboxylic acid;

4-[4-(5-fluoro-2-methoxyphenyl)-1H-pyrrolo[2,3-b]pyridin-2-yl]-1-methylcyclohex-3-ene-1-carboxylic acid;

2-{4-[4-(5-fluoro-2-methoxyphenyl)-1H-pyrrolo[2,3-b]pyridin-2-yl]-2,3,6,7-tetrahydro-1H-azepin-1-yl}-N,N-dimethylacetamide;

2-{4-[4-(5-fluoro-2-methoxyphenyl)-1H-pyrrolo[2,3-b]pyridin-2-yl]azepan-1-yl}-N,N-dimethylacetamide;

{4-[4-(5-fluoro-2-methoxyphenyl)-1H-pyrrolo[2,3-b]pyridin-2-yl]-2,3,6,7-tetrahydro-1H-azepin-1-yl}acetic acid;

2-{4-[4-(5-fluoro-2-methoxyphenyl)-1H-pyrrolo[2,3-b]pyridin-2-yl]-2,3,6,7-tetrahydro-1H-azepin-1-yl}-1-(3-hydroxyazetidin-1-yl)ethanone;

tert-butyl 3-{4-[4-(5-fluoro-2-methoxyphenyl)-1H-pyrrolo[2,3-b]pyridin-2-yl]-3,6-dihydropyridin-1(2H)-yl}azetidine-1-carboxylate;

tert-butyl 3-{4-[4-(5-fluoro-2-methoxyphenyl)-1H-pyrrolo[2,3-b]pyridin-2-yl]piperidin-1-yl}azetidine-1-carboxylate;

{4-[5-fluoro-4-(5-fluoro-2-methoxyphenyl)-1H-pyrrolo[2,3-b]pyridin-2-yl]cyclohex-3-en-1-yl}acetic acid;

2-[1-(azetidin-3-yl)-1,2,3,6-tetrahydropyridin-4-yl]-4-(5-fluoro-2-methoxyphenyl)-1H-pyrrolo[2,3-b]pyridine;

2-[1-(azetidin-3-yl)piperidin-4-yl]-4-(5-fluoro-2-methoxyphenyl)-1H-pyrrolo[2,3-b]pyridine;

[3-(benzyloxy)-1,2-oxazol-5-yl]{4-[4-(5-fluoro-2-methoxyphenyl)-1H-pyrrolo[2,3-b]pyridin-2-yl]-3,6-dihydropyridin-1(2H)-yl}methanone;

4-[5-cyano-4-(5-fluoro-2-methoxyphenyl)-1H-pyrrolo[2,3-b]pyridin-2-yl]cyclohex-3-ene-1-carboxylic acid;

tert-butyl 4-[4-(5-fluoro-2-methoxyphenyl)-3-nitro-1H-pyrrolo[2,3-b]pyridin-2-yl]piperazine-1-carboxylate;

4-(5-fluoro-2-methoxyphenyl)-3-nitro-2-(piperazin-1-yl)-1H-pyrrolo[2,3-b]pyridine;

4-[4-(5-fluoro-2-methoxyphenyl)-3-nitro-1H-pyrrolo[2,3-b]pyridin-2-yl]-N-methylpiperazine-1-carboxamide;

4-(5-fluoro-2-methoxyphenyl)-2-{1-[1-(methylsulfonyl)azetidin-3-yl]-1,2,3,6-tetrahydropyridin-4-yl}-1H-pyrrolo[2,3-b]pyridine;

4-(5-fluoro-2-methoxyphenyl)-2-{1-[1-(methylsulfonyl)azetidin-3-yl]piperidin-4-yl}-1H-pyrrolo[2,3-b]pyridine;

2-{4-[4-(5-fluoro-2-methoxyphenyl)-1H-pyrrolo[2,3-b]pyridin-2-yl]-2,3,6,7-tetrahydro-1H-azepin-1-yl}-N-(3-hydroxycyclobutyl)-N-methylacetamide;

2-{4-[4-(5-fluoro-2-methoxyphenyl)-1H-pyrrolo[2,3-b]
pyridin-2-yl]-2,3,6,7-tetrahydro-1H-azepin-1-yl}-N-(2-
hydroxyethyl)-N-methylacetamide;
2-{4-[4-(5-fluoro-2-methoxyphenyl)-1H-pyrrolo[2,3-b]
pyridin-2-yl]-2,3,6,7-tetrahydro-1H-azepin-1-yl}-1-
[(2S)-2-(hydroxymethyl)pyrrolidin-1-yl]ethanone;
4-(5-fluoro-2-methoxyphenyl)-5-methoxy-2-[2-(methylsul-
fonyl)-1,2,3,3a,4,6a-hexahydrocyclopenta[c]pyrrol-5-yl]-
1H-pyrrolo[2,3-b]pyridine;
2-{5-[4-(5-fluoro-2-methoxyphenyl)-5-methoxy-1H-pyr-
rolo[2,3-b]pyridin-2-yl]-3,3a,4,6a-tetrahydrocyclopenta
[c]pyrrol-2(1H)-yl}-N,N-dimethylacetamide;
4-[4-(4,5-difluoro-2-methoxyphenyl)-5-fluoro-1H-pyrrolo
[2,3-b]pyridin-2-yl]cyclohex-3-ene-1-carboxylic acid;
4-[5-fluoro-4-(4-fluoro-2-methoxyphenyl)-1H-pyrrolo[2,3-
b]pyridin-2-yl]cyclohex-3-ene-1-carboxylic acid;
(4-{4-[4-(5-fluoro-2-methoxyphenyl)-1H-pyrrolo[2,3-b]
pyridin-2-yl]cyclohex-3-en-1-yl}piperazin-1-yl)acetic
acid;
2-{4-[5-fluoro-4-(5-fluoro-2-methoxyphenyl)-1H-pyrrolo
[2,3-b]pyridin-2-yl]-3,6-dihydropyridin-1(2H)-yl}-N-(3-
hydroxycyclobutyl)-N-methylacetamide;
2-{4-[5-fluoro-4-(5-fluoro-2-methoxyphenyl)-1H-pyrrolo
[2,3-b]pyridin-2-yl]-3,6-dihydropyridin-1(2H)-yl}-N-(2-
hydroxyethyl)-N-methylacetamide;
2-{4-[5-fluoro-4-(5-fluoro-2-methoxyphenyl)-1H-pyrrolo
[2,3-b]pyridin-2-yl]-3,6-dihydropyridin-1(2H)-yl}-1-
[(2S)-2-(hydroxymethyl)pyrrolidin-1-yl]ethanone;
2-{4-[5-fluoro-4-(5-fluoro-2-methoxyphenyl)-1H-pyrrolo
[2,3-b]pyridin-2-yl]-3,6-dihydropyridin-1(2H)-yl}-N-
(trans-4-hydroxycyclohexyl)acetamide;
{4-[4-(5-fluoro-2-methoxyphenyl)-1H-pyrrolo[2,3-b]pyri-
din-2-yl]-3,6-dihydropyridin-1(2H)-yl}(3-hydroxy-1,2-
oxazol-5-yl)methanone;
3-{4-[4-(5-fluoro-2-methoxyphenyl)-1H-pyrrolo[2,3-b]
pyridin-2-yl]-3,6-dihydropyridin-1(2H)-yl}-N-methyl-
azetidine-1-carboxamide;
3-{4-[4-(5-fluoro-2-methoxyphenyl)-1H-pyrrolo[2,3-b]
pyridin-2-yl]piperidin-1-yl}-N-methylazetidine-1-car-
boxamide;
3-{4-[4-(5-fluoro-2-methoxyphenyl)-1H-pyrrolo[2,3-b]
pyridin-2-yl]-3,6-dihydropyridin-1(2H)-
yl}cyclobutanecarbonitrile;
3-{4-[4-(5-fluoro-2-methoxyphenyl)-1H-pyrrolo[2,3-b]
pyridin-2-yl]-3,6-dihydropyridin-1(2H)-
yl}cyclopentanecarboxylic acid;
9-[4-(5-fluoro-2-methoxyphenyl)-1H-pyrrolo[2,3-b]pyri-
din-2-yl]-3-azaspiro[5.5]undec-8-ene;
9-[4-(5-fluoro-2-methoxyphenyl)-1H-pyrrolo[2,3-b]pyri-
din-2-yl]-N-methyl-3-azaspiro[5.5]undec-8-ene-3-car-
boxamide;
9-[4-(5-fluoro-2-methoxyphenyl)-1H-pyrrolo[2,3-b]pyri-
din-2-yl]-3-(methylsulfonyl)-3-azaspiro[5.5]undec-8-
ene;
(3-{4-[4-(5-fluoro-2-methoxyphenyl)-1H-pyrrolo[2,3-b]
pyridin-2-yl]-3,6-dihydropyridin-1(2H)-yl}cyclobutyl)
methanol;
(trans-4-{4-[5-chloro-4-(5-fluoro-2-methoxyphenyl)-1H-
pyrrolo[2,3-b]pyridin-2-yl]-3,6-dihydropyridin-1(2H)-
yl}cyclohexyl)acetic acid;
(cis-4-{4-[5-chloro-4-(5-fluoro-2-methoxyphenyl)-1H-pyr-
rolo[2,3-b]pyridin-2-yl]-3,6-dihydropyridin-1(2H)-
yl}cyclohexyl)acetic acid;
N-(1,1-dioxidotetrahydrothiophen-3-yl)-2-{4-[4-(5-fluoro-
2-methoxyphenyl)-1H-pyrrolo[2,3-b]pyridin-2-yl]-3,6-
dihydropyridin-1(2H)-yl}acetamide;
N-(1,1-dioxidotetrahydrothiophen-3-yl)-2-{4-[4-(5-fluoro-
2-methoxyphenyl)-1H-pyrrolo[2,3-b]pyridin-2-yl]piperi-
din-1-yl}acetamide;
2-{4-[4-(5-fluoro-2-methoxyphenyl)-1H-pyrrolo[2,3-b]
pyridin-2-yl]-3,6-dihydropyridin-1(2H)-yl}-1-[3-(meth-
ylsulfonyl)azetidin-1-yl]ethanone;
2-{4-[4-(5-fluoro-2-methoxyphenyl)-1H-pyrrolo[2,3-b]
pyridin-2-yl]piperidin-1-yl}-1-[3-(methylsulfonyl)azeti-
din-1-yl]ethanone;
2-{4-[4-(5-fluoro-2-methoxyphenyl)-1H-pyrrolo[2,3-b]
pyridin-2-yl]-3,6-dihydropyridin-1(2H)-yl}-N-(1-
methyl-1H-pyrazol-4-yl)acetamide;
4-(4-fluoro-2-methoxyphenyl)-2-[2-(methylsulfonyl)-1,2,3,
3a,4,6a-hexahydrocyclopenta[c]pyrrol-5-yl]-1H-pyrrolo
[2,3-b]pyridine;
4-(4,5-difluoro-2-methoxyphenyl)-2-[2-(methylsulfonyl)-1,
2,3,3a,4,6a-hexahydrocyclopenta[c]pyrrol-5-yl]-1H-pyr-
rolo[2,3-b]pyridine;
2-{3-[4-(5-fluoro-2-methoxyphenyl)-1H-pyrrolo[2,3-b]
pyridin-2-yl]-9-azabicyclo[3.3.1]non-2-en-9-yl}-N-(2-
hydroxyethyl)-N-methylacetamide;
2-{3-[4-(5-fluoro-2-methoxyphenyl)-1H-pyrrolo[2,3-b]
pyridin-2-yl]-9-azabicyclo[3.3.1]non-2-en-9-yl}-1-(3-hy-
droxyazetidin-1-yl)ethanone;
2-{3-[4-(5-fluoro-2-methoxyphenyl)-1H-pyrrolo[2,3-b]
pyridin-2-yl]-9-azabicyclo[3.3.1]non-2-en-9-yl}-1-[(2S)-
2-(hydroxymethyl)pyrrolidin-1-yl]ethanone;
2-{3-[4-(5-fluoro-2-methoxyphenyl)-1H-pyrrolo[2,3-b]
pyridin-2-yl]-9-azabicyclo[3.3.1]non-2-en-9-yl}-N-(3-
hydroxycyclobutyl)-N-methylacetamide;
{3-[4-(5-fluoro-2-methoxyphenyl)-1H-pyrrolo[2,3-b]pyri-
din-2-yl]-9-azabicyclo[3.3.1]non-2-en-9-yl}acetic acid;
4-(2-methoxyphenyl)-2-[2-(methylsulfonyl)-1,2,3,3a,4,6a-
hexahydrocyclopenta[c]pyrrol-5-yl]-1H-pyrrolo[2,3-b]
pyridine;
4-(5-fluoro-2-methoxyphenyl)-2-(piperazin-1-yl)-1H-pyr-
rolo[2,3-b]pyridine-3-carbonitrile;
tert-butyl (2-{4-[4-(5-fluoro-2-methoxyphenyl)-1H-pyrrolo
[2,3-b]pyridin-2-yl]-3,6-dihydropyridin-1(2H)-yl}ethyl)
carbamate;
2-{4-[5-fluoro-4-(5-fluoro-2-methoxyphenyl)-1H-pyrrolo
[2,3-b]pyridin-2-yl]-3,6-dihydropyridin-1(2H)-yl}-1-
[(3R)-3-hydroxypyrrolidin-1-yl]ethanone;
4-{4-[5-fluoro-4-(5-fluoro-2-methoxyphenyl)-1H-pyrrolo
[2,3-b]pyridin-2-yl]-3,6-dihydropyridin-1(2H)-
yl}cyclohexanecarboxylic acid;
2-{4-[4-(5-fluoro-2-methoxyphenyl)-1H-pyrrolo[2,3-b]
pyridin-2-yl]azepan-1-yl}-1-(3-hydroxyazetidin-1-yl)
ethanone;
3-({4-[4-(5-fluoro-2-methoxyphenyl)-1H-pyrrolo[2,3-b]
pyridin-2-yl]cyclohex-3-en-1-yl}amino)bicyclo[1.1.1]
pentane-1-carboxylic acid;
2-{4-[4-(5-fluoro-2-methoxyphenyl)-1H-pyrrolo[2,3-b]
pyridin-2-yl]-3,6-dihydropyridin-1(2H)-yl}ethanamine;
N-(2-{4-[4-(5-fluoro-2-methoxyphenyl)-1H-pyrrolo[2,3-b]
pyridin-2-yl]-3,6-dihydropyridin-1(2H)-yl}ethyl)meth-
anesulfonamide;
N-(2-{4-[4-(5-fluoro-2-methoxyphenyl)-1H-pyrrolo[2,3-b]
pyridin-2-yl]-3,6-dihydropyridin-1(2H)-yl}ethyl)acet-
amide;
2-{4-[4-(5-fluoro-2-methoxyphenyl)-1H-pyrrolo[2,3-b]
pyridin-2-yl]-3,6-dihydropyridin-1(2H)-yl}-N,N-dim-
ethylethanesulfonamide;
4-(5-fluoro-2-methoxyphenyl)-2-[4-(methylsulfonyl)piper-
azin-1-yl]-3-nitro-1H-pyrrolo[2,3-b]pyridine;
4-(5-fluoro-2-methoxyphenyl)-2-[4-(methylsulfonyl)piper-
azin-1-yl]-1H-pyrrolo[2,3-b]pyridine-3-carbonitrile;

2-{3-[4-(5-fluoro-2-methoxyphenyl)-1H-pyrrolo[2,3-b]pyridin-2-yl]-2,5-dihydro-1H-pyrrol-1-yl}-1-(3-hydroxyazetidin-1-yl)ethanone;

(4-{4-[4-(5-fluoro-2-methoxyphenyl)-1H-pyrrolo[2,3-b]pyridin-2-yl]cyclohex-3-en-1-yl}piperidin-1-yl)acetic acid;

4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;

2-{3-[4-(5-fluoro-2-methoxyphenyl)-1H-pyrrolo[2,3-b]pyridin-2-yl]-2,5-dihydro-1H-pyrrol-1-yl}-N-(2-hydroxyethyl)-N-methylacetamide;

2-{3-[4-(5-fluoro-2-methoxyphenyl)-1H-pyrrolo[2,3-b]pyridin-2-yl]-2,5-dihydro-1H-pyrrol-1-yl}-N,N-dimethylacetamide;

2-{3-[4-(5-fluoro-2-methoxyphenyl)-1H-pyrrolo[2,3-b]pyridin-2-yl]-2,5-dihydro-1H-pyrrol-1-yl}-1-[(2S)-2-(hydroxymethyl)pyrrolidin-1-yl]ethanone;

2-(4-{4-[4-(5-fluoro-2-methoxyphenyl)-1H-pyrrolo[2,3-b]pyridin-2-yl]cyclohex-3-en-1-yl}piperidin-1-yl)-N,N-dimethylacetamide;

(4-{(1S)-4-[4-(5-fluoro-2-methoxyphenyl)-1H-pyrrolo[2,3-b]pyridin-2-yl]cyclohex-3-en-1-yl}piperidin-1-yl)acetic acid;

(4-{(1R)-4-[4-(5-fluoro-2-methoxyphenyl)-1H-pyrrolo[2,3-b]pyridin-2-yl]cyclohex-3-en-1-yl}piperidin-1-yl)acetic acid;

methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate;

(4-{(1S)-4-[4-(5-fluoro-2-methoxyphenyl)-1H-pyrrolo[2,3-b]pyridin-2-yl]cyclohex-3-en-1-yl}piperazin-1-yl)acetic acid;

(4-{(1R)-4-[4-(5-fluoro-2-methoxyphenyl)-1H-pyrrolo[2,3-b]pyridin-2-yl]cyclohex-3-en-1-yl}piperazin-1-yl)acetic acid;

(4-{4-[4-(5-fluoro-2-methoxyphenyl)-1H-pyrrolo[2,3-b]pyridin-2-yl]-3,6-dihydropyridin-1(2H)-yl}cyclohexylidene)acetic acid;

cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

trans-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

(cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

(trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

(1-{4-[4-(5-fluoro-2-methoxyphenyl)-1H-pyrrolo[2,3-b]pyridin-2-yl]cyclohex-3-en-1-yl}piperidin-4-yl)acetic acid;

methyl (4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetate;

cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetic acid;

(trans-4-{4-[5-fluoro-4-(5-fluoro-2-methoxyphenyl)-1H-pyrrolo[2,3-b]pyridin-2-yl]piperidin-1-yl}cyclohexyl)acetic acid;

2-(trans-4-{4-[4-(5-fluoro-2-methoxyphenyl)-1H-pyrrolo[2,3-b]pyridin-2-yl]-3,6-dihydropyridin-1(2H)-yl}cyclohexyl)-N-(propan-2-ylsulfonyl) acetamide;

trans-4-{4-[5-fluoro-4-(5-fluoro-2-methoxyphenyl)-1H-pyrrolo[2,3-b]pyridin-2-yl]-3,6-dihydropyridin-1(2H)-yl}-N-(propan-2-ylsulfonyl)cyclohexanecarboxamide;

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexyl)acetic acid;

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid; and pharmaceutically acceptable salts thereof.

In another aspect, the present invention relates to pharmaceutical compositions comprising a pharmaceutically acceptable excipient and a therapeutically effective amount of a compound of Formula (IIa) or a pharmaceutically acceptable salt thereof.

In another aspect, the present invention relates to methods of treating cancer in a patient, comprising administering to a patient suffering from a cancer a therapeutically effective amount of a compound of Formula (IIa), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated radical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of alkyls include methyl, ethyl, n-propyl, isopropyl, n-butyl, isobutyl, sec-butyl, tert-butyl, pentyl, iso-amyl, hexyl, pentan-3-y), 2,2-dimethylpropan-2-yl), heptan-4-yl, and 2,6-dimethylheptan-4-yl, and the like. The term "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms.

The term "alkenyl" (alone or in combination with another term(s)) means a straight- or branched 98-chain radical of an alkene containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4pentadienyl, -1,4-butadienyl, 1-butenyl, 2-butenyl, and 3-butenyl and the like. The term "$C_2$-$C_6$ alkenyl" means an alkenyl group containing 2-6 carbon atoms.

The term "alkynyl" (alone or in combination with another term(s)) means a straight- or branched-chain radical of an alkyne containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like. The term "$C_2$-$C_6$ alkynyl" means an alkynyl group of 2 to 6 carbon atoms.

The term "cycloalkyl" (alone or in combination with another term(s)) means a saturated cyclic hydrocarbyl substituent containing from 3 or more carbon ring atoms ("ring atoms" are the atoms bound together to form the ring or rings of a cyclic substituent). A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic (contain more than one ring). Examples of polycyclic cycloalkyls include bridged, fused, and spirocyclic cycloalkyls.

The term "$C_3$-$C_7$ cycloalkyl" (alone or in combination with another term(s)) means a saturated cyclic radical of a monocyclic cycloalkane containing from 3 to 7 carbon ring atoms. Examples of monocyclic cycloalkyl groups include, but are not limited to, cyclopropyl (cyclopropanyl), cyclobutyl (cyclobutanyl), cyclopentyl (cyclopentanyl), cyclopentenyl, cyclohexyl (cyclohexanyl), and cycloheptyl.

The term "cycloalkenyl" (alone or in combination with another term(s)) means a partially unsaturated cyclic hydrocarbyl substituent containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "$C_5$-$C_7$ cycloalkenyl" (alone or in combination with another term(s)) means a partially unsaturated monocyclic cycloalkane radical containing from 5 to 7 carbon ring atoms. Examples of single-ring cycloalkenyls include cyclopentenyl, cyclohexenyl, and cycloheptenyl.

The term "heterocycloalkyl" (alone or in combination with another term(s)) means a non-aromatic saturated monocyclic or polycyclic heterocycloalkane radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkyl may be a single carbon ring, which typically contains from 3 to 8 ring atoms and more typically from 3 to 6 ring atoms. Examples of single-ring heterocycloalkyls include oxetanyl, azetidinyl, thietanyl, tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, 3-pyrrolinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, trithianyl, azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl, azocanyl, thiocanyl, oxocanyl, tetrahydro-2H-thiopyranyl 1,1-dioxide and 3,4,5,6-tetrahydro-2H-oxocinyl. A heterocycloalkyl may alternatively be polycyclic (contain more than one ring). Examples of polycyclic heterocycloalkyls include bridged, fused, and spirocyclic heterocycloalkyls in which at least one ring is a heterocycloalkyl and the others are heterocycloalkyl, or cycloalkyl rings.

The term "heterocycloalkenyl" (alone or in combination with another term(s)) means a non-aromatic partially unsaturated monocyclic or polycyclic heterocycloalkene radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkenyl may be a single carbon ring, which typically contains from 3 to 8 ring atoms and more typically from 3 to 6 ring atoms. Examples of single-ring heterocycloalkenyls include 1,2,3,6-tetrahydropyridinyl, and 4,5-dihydro-1H-imidazolyl. A heterocycloalkenyl may alternatively be polycyclic (contain more than one ring). Examples of polycyclic heterocycloalkenyls include bridged, fused, and spirocyclic heterocycloalkenyls in which at least one ring is a heterocycloalkenyl and the others are heterocycloalkenyl, heterocycloalkyl, cycloalkenyl or cycloalkyl rings. Alternatively, a polycyclic heterocycloalkenyl may consist of one or more heterocycloalkyl rings and one or more cycloalkenyl rings. Examples of polycyclic heterocycloalkenyls include 8-azabicyclo[3.2.1]oct-2-enyl, and 1,2,3,3a,4,6a-hexahydrocyclopenta[c]pyrrolyl.

The term "5 to 7-membered heterocycloalkyl" (alone or in combination with another term(s)) means a non-aromatic monocyclic radical having carbon atoms and 1 to 3 heteroatoms independently selected from S, N or O, wherein when two O atoms or one O atom and one S atom are present, the two O atoms or one O atom and one S atom are not bonded to each other, respectively.

The term "4-membered monocyclic heterocycloalkyl" (alone or in combination with another term(s)) means a 4-membered, monocyclic radical having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

The term "5-membered monocyclic heterocycloalkyl" (alone or in combination with another term(s)) means a 5-membered, monocyclic radical having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

The term "6-membered monocyclic heterocycloalkyl" (alone or in combination with another term(s)) means a 6-membered, monocyclic radical having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

The term "7-membered monocyclic heterocycloalkyl" (alone or in combination with another term(s)) means a 7-membered, monocyclic radical having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 10; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

The term "8-membered monocyclic heterocycloalkyl" (alone or in combination with another term(s)) means a 8-membered, monocyclic radical having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The nitrogen and sulfur heteroatoms in the heterocycloalkyl rings may optionally be oxidized (e.g. 1,1-dioxido-tetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

The term "aryl" (alone or in combination with another term(s)) means an aromatic hydrocarbon radical. Furthermore, the term "aryl" includes polycyclic aryl groups, such as bicyclic, e.g., naphthyl. Typical aryl groups include phenyl, and naphthyl. The term aryl also includes a "9- to 12-membered bicyclic aryl," which is a ring structure formed by the fusion of a benzene ring to: (1) a cycloalkyl or cycloalkenyl (e.g., indanyl; 1,2,3,4-tetrahydro-naphthalenyl; 6,7,8,9-tetrahydro-5H-benzocycloheptenyl, etc.); (2) another benzene ring (e.g., naphthalenyl); wherein the fusion junctions are at adjacent carbons on the benzene ring; or (3) a heterocycloalkyl or heterocycloalkenyl (e.g., benzo[d][1,3]dioxolyl, isoindolinyl).

The term "heteroaryl" (alone or in combination with another term(s)) means a monocyclic 5 or 6 membered heteroaryl or a bicyclic heteroaryl.

The term "5-membered heteroaryl" (alone or in combination with another term(s)) means a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

The term "6-membered heteroaryl" (alone or in combination with another term(s)) means a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

The term "bicyclic heteroaryl" (alone or in combination with another term(s)) means a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a cycloalkyl or cycloalkenyl; (4) a heterocycloalkyl or heterocycloalkenyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK9 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to CDK9 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $R^1$, $R^2$, $R^3$, and $R^4$, in compounds of Formula (I), and $R^1$, $R^2$, $R^4$, $R^{3A}$, $R^{3B}$, $R^{3C}$, $R^{3D}$, and $R^{3E}$ in compounds of Formula (II), (IIa), (IIIa), and (IVa) are independently selected. The described embodiments of the present invention may be combined. Such combination is contemplated and within the scope of the present invention. For example, it is contemplated that embodiments for any of $R^1$, $R^2$, $R^{3A}$, $R^{3B}$, $R^{3C}$, $R^{3D}$, $R^{3E}$, and $R^4$ in compounds of Formula (IIa) can be combined with embodiments defined for any other of $R^1$, $R^2$, $R^{3A}$, $R^{3B}$, $R^{3C}$, $R^{3D}$, $R^{3E}$, and $R^4$ in compounds of Formula (IIa).

In one aspect, the present invention relates to compounds of Formula (I) or a pharmaceutically acceptable salt thereof, Formula (I)

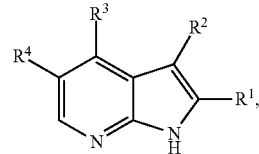

wherein $R^1$ is selected from the group consisting of $C_4$-$C_7$ cycloalkyl, $C_5$-$C_7$cycloalkenyl, a 5-7 membered heterocycloalkyl, and a 5-7 membered heterocycloalkenyl; each of which may be substituted with one, two, or three substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, F, Cl, Br and I;

$R^2$ is hydrogen or $C_1$-$C_4$ alkyl;

$R^3$ is selected from the group consisting of phenyl, pyridinyl, pyrazinyl, pyrimidinyl, and pyridazinyl; wherein the $R^3$ phenyl, pyridinyl, pyrazinyl, pyrimidinyl, and pyridazinyl are substituted with one, two, or three substituents independently selected from the group consisting of $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $OH$, $CN$, $NO_2$, F, Cl, Br and I;

$R^4$ is selected from the group consisting of hydrogen, CN, F, Cl, Br, and I;

$R^5$, at each occurrence, is independently selected from the group consisting of $C_1$-$C_8$alkyl, $C_2$-$C_6$alkenyl, $C_2$-$C_6$alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^5C_1$-$C_8$alkyl, $C_2$-$C_6$alkenyl, and $C_2$-$C_6$alkynyl is optionally substituted with one, two, or three substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $OH$, $CN$, $NO_2$, F, Cl, Br and I; wherein each $R^5$ aryl, $C_3$-$C_7$ cycloalkyl, $C_5$-$C_7$cycloalkenyl, heteroaryl, 5 to 7 membered heterocycloalkyl, and 5 to 7 membered heterocycloalkenyl is optionally substituted with one, two, or three substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $OH$, $CN$, $NO_2$, F, Cl, Br and I;

$R^6$, at each occurrence, is independently selected from the group consisting of $C_1$-$C_6$alkyl, $C_2$-$C_6$alkenyl, $C_2$-$C_6$alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^6C_1$-$C_6$alkyl, $C_2$-$C_6$alkenyl, and $C_2$-$C_6$alkynyl is optionally substituted with one, two, or three substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, F, Cl, Br and I; wherein each $R^6$ aryl, $C_4$-$C_7$ cycloalkyl, $C_5$-$C_7$cycloalkenyl, heteroaryl, heterocycloalkyl, and heterocycloalkenyl is optionally substituted with one, two, three, or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $OH$, $CN$, $NO_2$, F, Cl, Br and I;

$R^7$, at each occurrence, is independently selected from the group consisting of $C_1$-$C_6$alkyl, $C_2$-$C_6$alkenyl, $C_2$-$C_6$alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^7C_1$-$C_6$alkyl, $C_2$-$C_6$alkenyl, and $C_2$-$C_6$alkynyl is optionally substituted with one, two, or three substituents independently selected from the group consisting of aryl, heteroaryl, $C_3$-$C_7$ cycloalkyl, $C_5$-$C_7$ cycloalkenyl, 5 to 7 membered heterocycloalkyl, 5 to 7 membered heterocycloalkenyl, $NH_2$, $NHR^{13}$, $N(R^{13})_2$, $C(O)H$, $C(O)OH$, $OH$, $CN$, $NO_2$, F, Cl, Br and I; wherein each $R^7$ aryl, $C_3$-$C_7$ cycloalkyl, $C_5$-$C_7$cycloalkenyl, heteroaryl, 5 to 7 membered heterocycloalkyl, and 5 to 7 membered heterocycloalkenyl is optionally substituted with one, two, or three substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $OH$, $CN$, $NO_2$, F, Cl, Br and I;

$R^8$, at each occurrence, is independently selected from the group consisting of $C_1$-$C_6$alkyl, $C_2$-$C_6$alkenyl, and $C_2$-$C_6$alkynyl;

$R^9$, at each occurrence, is independently selected from the group consisting of $C_1$-$C_6$alkyl, $C_2$-$C_6$alkenyl, $C_2$-$C_6$alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^9$ aryl, $C_3$-$C_7$ cycloalkyl, $C_5$-$C_7$cycloalkenyl, heteroaryl, 5 to 7 membered heterocycloalkyl, and heterocycloalkenyl is optionally substituted with one, two, or three substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, NHC (O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, OH, CN, NO$_2$, F, Cl, Br and I;

R$^{10}$, at each occurrence, is independently selected from the group consisting of C$_1$-C$_6$alkyl, C$_2$-C$_6$alkenyl, and C$_2$-C$_6$ alkynyl;

R$^{11}$, at each occurrence, is independently selected from the group consisting of C$_1$-C$_6$alkyl, C$_2$-C$_6$alkenyl, and C$_2$-C$_6$alkynyl;

R$^{12}$, at each occurrence, is independently selected from the group consisting of C$_1$-C$_6$alkyl, C$_2$-C$_6$alkenyl, and C$_2$-C$_6$ alkynyl; wherein each R$^{12}$C$_1$-C$_6$alkyl, C$_2$-C$_6$alkenyl, and C$_2$-C$_6$alkynyl is optionally substituted with one, two, or three substituents independently selected from the group consisting of NH$_2$, NHR$^{13}$, N(R$^{13}$)$_2$, C(O)H, C(O)OH, OH, CN, NO$_2$, F, Cl, Br and I; and R$^{13}$, at each occurrence, is independently selected from the group consisting of C$_1$-C$_6$alkyl, C$_2$-C$_6$alkenyl, and C$_2$-C$_6$ alkynyl.

In certain embodiments, R$^2$ is hydrogen, and R$^4$ is hydrogen. In certain embodiments, R$^1$ is selected from the group consisting of azetidinyl, pyrrolidinyl, morpholinyl, tetrahydropyranyl, tetrahydropyridinyl, piperidinyl, cyclohexanyl, or azepanyl; wherein the R$^1$ azetidinyl, pyrrolidinyl, morpholinyl, tetrahydropyranyl, tetrahydropyridinyl, piperidinyl, cyclohexanyl, and azepanyl are optionally substituted with one, two, three, or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O) N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, OH, CN, NO$_2$, F, Cl, Br and I. In certain embodiments, R$^1$ is selected from the group consisting of azetidinyl, pyrrolidinyl, morpholinyl, tetrahydropyranyl, tetrahydropyridinyl, piperidinyl, cyclohexanyl, or azepanyl; wherein the R$^1$ azetidinyl, pyrrolidinyl, morpholinyl, tetrahydropyranyl, tetrahydropyridinyl, piperidinyl, cyclohexanyl, and azepanyl are optionally substituted with one or two substituents independently selected from the group consisting of R$^5$, SO$_2$R$^5$, C(O)R$^5$, CO(O)R$^5$, NH$_2$, NHR$^5$, C(O)NHR$^5$, SO$_2$NH$_2$, and OH. In certain embodiments, R$^1$ is selected from the group consisting of: azetidinyl, pyrrolidinyl, morpholinyl, tetrahydropyranyl, tetrahydropyridinyl, piperidinyl, cyclohexanyl, or azepanyl; wherein the R$^1$ azetidinyl, pyrrolidinyl, morpholinyl, tetrahydropyranyl, tetrahydropyridinyl, piperidinyl, cyclohexanyl, and azepanyl are unsubstituted. In certain embodiments, R$^3$ is selected from the group consisting of phenyl and pyridinyl; wherein the R$^3$ phenyl, and pyridinyl are substituted with one, two, or three substituents independently selected from the group consisting of: R$^6$, OR$^6$, SR$^6$, S(O) R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O) N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, C(O)H, C(O)OH, OH, CN, NO$_2$, F, Cl, Br and I. In certain embodiments, R$^3$ is selected from the group consisting of phenyl and pyridinyl; wherein the R$^3$ phenyl, and pyridinyl are substituted with one, two, or three substituents independently selected from the group consisting of R$^6$, OR$^6$, NH$_2$, NHR$^6$, N(R$^6$)$_2$, NHC(O)R$^6$, NHS(O)$_2$R$^6$, CN, F, Cl, Br and I. In certain embodiments, R$^3$ is selected from the group consisting of phenyl and pyridinyl; wherein the R$^3$ phenyl, and pyridinyl are substituted with one, or two substituents independently selected from the group consisting of OR$^6$, NHR$^6$, F, and Cl. In certain embodiments, R$^3$ is selected from the group consisting of:

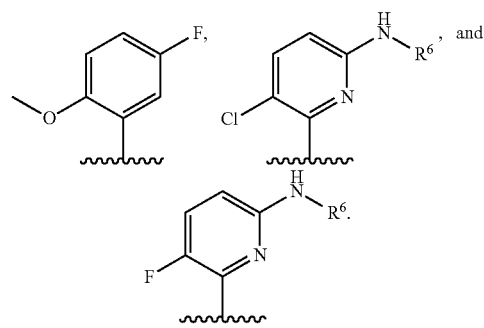

In certain embodiments, R$^6$, at each occurrence, is independently selected from the group consisting of C$_1$-C$_6$alkyl, aryl, heteroaryl, 5 to 7 membered heterocycloalkenyl, and C$_3$-C$_7$ cycloalkyl; wherein each R$^6$C$_1$-C$_6$alkyl is optionally substituted with one substituent independently selected from the group consisting of R$^9$, SR$^9$, and OH; wherein each R$^6$ aryl, C$_3$-C$_7$ cycloalkyl, and heteroaryl is optionally substituted with one or two substituents independently selected from the group consisting of NH$_2$, F, Cl, Br and I.

In certain embodiments, a compound of formula I is selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, and 216, or a pharmaceutically acceptable salt thereof.

Embodiments of Formula (I)

In one aspect, the present invention relates to compounds of Formula (I) or a pharmaceutically acceptable salt thereof,

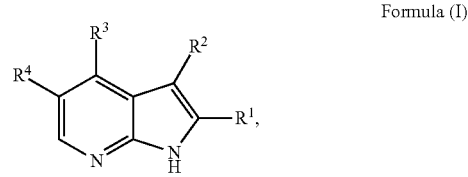

Formula (I)

wherein
R¹ is selected from the group consisting of cycloalkyl, cycloalkenyl, heterocycloalkyl, and heterocycloalkenyl; wherein the R¹ cycloalkyl, cycloalkenyl, heterocycloalkyl and heterocycloalkenyl are optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, SO₂NHC(O)R, SO₂NR⁵C(O)R, NHS(O)₂R, NR⁵S(O)₂R⁵, NHC(O)OR⁵, NR⁵C(O)OR⁵, SO₂NHC(O)OR, SO₂NR⁵C(O)OR⁵, NHSO₂NHC(O)OR, NHSO₂NR⁵C(O)OR, NR⁵SO₂NR⁵C(O)OR, NR⁵SO₂NHC(O)OR⁵, NHC(O)NH₂, NHC(O)NHR⁵, NHC(O)N(R⁵)₂, NR⁵C(O)NHR⁵, NR⁵C(O)N(R⁵)₂, OC(O)NH₂, OC(O)NHR⁵, OC(O)N(R⁵)₂, OC(O)NHSO₂R⁵, OC(O)NR⁵SO₂R⁵, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, OSO₂NH₂, OSO₂NHR⁵, OSO₂N(R⁵)₂, C(O)NHCN, C(O)NR⁵CN, S(O)(N)R⁵, C(O)H, C(O)OH, (O), OH, CN, NO₂, F, Cl, Br and I;

R² is selected from the group consisting of hydrogen, C₁-C₄ alkyl, NO₂, CN, C(O)NH₂, and C(O)OR²·⁴;

R²·⁴ is selected from the group consisting of alkyl, alkenyl, and alkynyl;

R³ is selected from the group consisting of phenyl, pyridinyl, pyrazinyl, pyrimidinyl, and pyridazinyl; wherein the R³ phenyl, pyridinyl, pyrazinyl, pyrimidinyl, and pyridazinyl are optionally substituted with one or more substituents independently selected from the group consisting of R⁶, OR⁶, SR⁶, S(O)R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, C(O)H, C(O)OH, (O), OH, CN, NO₂, F, Cl, Br and I;

R⁴ is selected from the group consisting of hydrogen, R⁴·⁴, OR⁴·⁴, C(O)NH₂, CN, F, Cl, Br, and I;

R⁴·⁴ is selected from the group consisting of haloalkyl, alkyl, alkenyl, and alkynyl;

R⁵, at each occurrence, is independently selected from the group consisting of C₁-C₈alkyl, C₂-C₆alkenyl, C₂-C₆alkynyl, aryl, heteroaryl, heterocycloalkyl, heterocycloalkenyl, cycloalkyl, and cycloalkenyl; wherein each R⁵C₁-C₈alkyl, C₂-C₆alkenyl, and C₂-C₆alkynyl is optionally substituted with one or more substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, C(O)H, C(O)OH, OH, CN, NO₂, F, Cl, Br and I; wherein each R⁵ aryl, cycloalkyl, cycloalkenyl, heteroaryl, heterocycloalkyl, and heterocycloalkenyl is optionally substituted with one or more substituents independently selected from the group consisting of R⁸, OR⁸, SR⁸, S(O)R⁸, SO₂R⁸, C(O)R⁸, CO(O)R⁸, OC(O)R⁸, OC(O)OR⁸, NH₂, NHR⁸, N(R⁸)₂, NHC(O)R⁸, NR⁸C(O)R⁸, NHS(O)₂R⁸, NR⁸S(O)₂R⁸, NHC(O)OR⁸, NR⁸C(O)OR⁸, NHC(O)NH₂, NHC(O)NHR⁸, NHC(O)N(R⁸)₂, NR⁸C(O)NHR⁸, NR⁸C(O)N(R⁸)₂, C(O)NH₂, C(O)NHR⁸, C(O)N(R⁸)₂, C(O)NHOH, C(O)NHOR⁸, C(O)NHSO₂R⁸, C(O)NR⁸SO₂R⁸, SO₂NH₂, SO₂NHR⁸, SO₂N(R⁸)₂, C(O)H, C(O)OH, (O), OH, CN, NO₂, F, Cl, Br and I;

R⁶, at each occurrence, is independently selected from the group consisting of C₁-C₆alkyl, C₂-C₆alkenyl, C₂-C₆alkynyl, aryl, heteroaryl, heterocycloalkyl, heterocycloalkenyl, cycloalkyl, and cycloalkenyl; wherein each R⁶C₁-C₆alkyl, C₂-C₆alkenyl, and C₂-C₆alkynyl is optionally substituted with one or more substituents independently selected from the group consisting of R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, OH, CN, NO₂, F, Cl, Br and I; wherein each R⁶ aryl, cycloalkyl, cycloalkenyl, heteroaryl, heterocycloalkyl, and heterocycloalkenyl is optionally substituted with one or more substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, (O), OH, CN, NO₂, F, Cl, Br and I;

R⁷, at each occurrence, is independently selected from the group consisting of C₁-C₆alkyl, C₂-C₆alkenyl, C₂-C₆alkynyl, aryl, heteroaryl, heterocycloalkyl, heterocycloalkenyl, cycloalkyl, and cycloalkenyl; wherein each R⁷C₁-C₆alkyl, C₂-C₆alkenyl, and C₂-C₆alkynyl is optionally substituted with one or more substituents independently selected from the group consisting of aryl, heteroaryl, cycloalkyl, cycloalkenyl, heterocycloalkyl, heterocycloalkenyl, NH₂, NHR¹³, N(R¹³)₂, C(O)H, C(O)OH, OH, CN, NO₂, F, Cl, Br and I; wherein each R⁷ aryl, cycloalkyl, cycloalkenyl, heteroaryl, heterocycloalkyl, and heterocycloalkenyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, (O), OH, CN, NO₂, F, Cl, Br and I;

R⁸, at each occurrence, is independently selected from the group consisting of C₁-C₆alkyl, C₂-C₆alkenyl, and C₂-C₆alkynyl; wherein each R⁸C₁-C₆alkyl, C₂-C₆alkenyl, and C₂-Calkynyl is optionally substituted with one or more substituents independently selected from the group consisting of NH₂, C(O)H, C(O)OH, OH, CN, NO₂, F, Cl, Br and I;

R⁹, at each occurrence, is independently selected from the group consisting of C₁-C₆alkyl, C₂-C₆alkenyl, C₂-C₆alkynyl, aryl, heteroaryl, heterocycloalkyl, heterocycloalkenyl, cycloalkyl, and cycloalkenyl; wherein each R⁹ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $(O)$, $OH$, $CN$, $NO_2$, F, Cl, Br and I;

$R^{10}$, at each occurrence, is independently selected from the group consisting of $C_1$-$C_6$alkyl, $C_2$-$C_6$alkenyl, and $C_2$-$C_6$ alkynyl; wherein each $R^{10}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I;

$R^{11}$, at each occurrence, is independently selected from the group consisting of $C_1$-$C_6$alkyl, $C_2$-$C_6$alkenyl, and $C_2$-$C_6$alkynyl; wherein each $R^{11}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I;

$R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{13}$, $N(R^{13})_2$, $C(O)H$, $C(O)OH$, OH, CN, $NO_2$, F, Cl, Br and I; and $R^{13}$, at each occurrence, is independently selected from the group consisting of $C_1$-$C_6$alkyl, $C_2$-$C_6$alkenyl, and $C_2$-$C_6$ alkynyl.

In one embodiment of Formula (I), $R^2$ is selected from the group consisting of hydrogen, $C_1$-$C_4$ alkyl, $NO_2$, CN, $C(O)NH_2$, and $C(O)OR^{2A}$; and $R^{2A}$ is selected from the group consisting of alkyl, alkenyl, and alkynyl. In another embodiment of Formula (I), $R^2$ is selected from the group consisting of hydrogen, $C_1$-$C_4$ alkyl, $NO_2$, CN, $C(O)NH_2$, and $C(O)OR^{2A}$; and $R^{2A}$ is alkyl. In another embodiment of Formula (I), $R^2$ is selected from the group consisting of hydrogen, $C_1$-$C_4$ alkyl, and CN. In another embodiment of Formula (I), $R^2$ is selected from the group consisting of hydrogen, $CH_3$, and CN. In another embodiment of Formula (I), $R^2$ is hydrogen. In another embodiment of Formula (I), $R^2$ is $CH_3$. In another embodiment of Formula (I), $R^2$ is CN.

In one embodiment of Formula (I), $R^4$ is selected from the group consisting of hydrogen, $R^{4A}$, $OR^{4A}$, $C(O)NH_2$, CN, F, Cl, Br, and I; and $R^{4A}$ is selected from the group consisting of haloalkyl, alkyl, alkenyl, and alkynyl. In another embodiment of Formula (I), $R^4$ is selected from the group consisting of hydrogen, $R^{4A}$, $OR^{4A}$, $C(O)NH_2$, CN, F, and Cl; and $R^{4A}$ is selected from the group consisting of haloalkyl and alkyl. In another embodiment of Formula (I), $R^4$ is selected from the group consisting of hydrogen, CN, F, and Cl. In another embodiment of Formula (I), $R^4$ is hydrogen. In another embodiment of Formula (I), $R^4$ is CN. In another embodiment of Formula (I), $R^4$ is F. In another embodiment of Formula (I), $R^4$ is Cl.

In one embodiment of Formula (I), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, $(O)$, OH, CN, $NO_2$, F, Cl, Br and I. In another embodiment of Formula (I), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (I), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (I), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (I), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (I), $R^1$ is heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (I), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR$, $NHSO_2NHC(O)OR$, $NHSO_2NR^5C(O)OR^5$, $NR^5SO_2NR^5C(O)OR$, $NR^5SO_2NHC(O)OR$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)$ NHR⁵, OC(O)N(R⁵)₂, OC(O)NHSO₂R⁵, OC(O)NR⁵SO₂R⁵, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, OSO₂NH₂, OSO₂NHR⁵, OSO₂N(R⁵)₂, C(O)NHCN, C(O)NR⁵CN, S(O)(N)R⁵, C(O)H, C(O)OH, (O), OH, CN, NO₂, F, Cl, Br and I. In another embodiment of Formula (I), R¹ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the R¹ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of R⁵, SO₂R⁵, C(O)R⁵, CO(O)R⁵, NH₂, NHR⁵, SO₂NHC(O)OR, NHSO₂NHC(O)OR, C(O)NHR⁵, SO₂NH₂, C(O)NHCN, S(O)(N)R⁵, C(O)OH, and OH. In another embodiment of Formula (I), R¹ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the R¹ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (I), R³ is selected from the group consisting of phenyl, pyridinyl, pyrazinyl, pyrimidinyl, and pyridazinyl; wherein the R³ phenyl, pyridinyl, pyrazinyl, pyrimidinyl, and pyridazinyl are optionally substituted with one or more substituents independently selected from the group consisting of R⁶, OR⁶, SR⁶, S(O)R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, C(O)H, C(O)OH, (O), OH, CN, NO₂, F, Cl, Br and I. In another embodiment of Formula (I), R³ is selected from the group consisting of phenyl and pyridinyl; wherein the R³ phenyl and pyridinyl are optionally substituted with one or more substituents independently selected from the group consisting of R⁶, OR⁶, SR⁶, S(O)R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, C(O)H, C(O)OH, (O), OH, CN, NO₂, F, Cl, Br and I. In another embodiment of Formula (I), R³ is selected from the group consisting of phenyl and pyridinyl; wherein the R³ phenyl and pyridinyl are optionally substituted with one or more substituents independently selected from the group consisting of R⁶, OR⁶, NH₂, NHR⁶, N(R⁶)₂, NHC(O)R⁶, NHS(O)₂R⁶, CN, F, Cl, Br and I. In another embodiment of Formula (I), R³ is selected from the group consisting of phenyl and pyridinyl; wherein the R³ phenyl and pyridinyl are optionally substituted with one or more substituents independently selected from the group consisting of R⁶, OR⁶, NH₂, NHR⁶, N(R⁶)₂, NHC(O)R⁶, NHS(O)₂R⁶, CN, F, and Cl. In another embodiment of Formula (I), R³ is selected from the group consisting of phenyl and pyridinyl; wherein the R³ phenyl, and pyridinyl are substituted with one, or two substituents independently selected from the group consisting of OR⁶, NHR⁶, F, and Cl. In another embodiment of Formula (I), R³ is selected from the group consisting of:

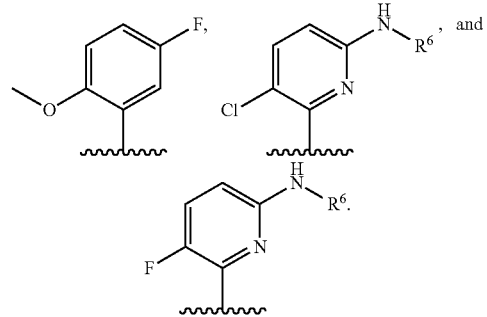

In one embodiment of Formula (I), R⁵, at each occurrence, is independently selected from the group consisting of C₁-C₈alkyl, C₂-C₆alkenyl, C₂-C₆alkynyl, aryl, heteroaryl, heterocycloalkyl, heterocycloalkenyl, cycloalkyl, and cycloalkenyl; wherein each R⁵C₁-C₈alkyl, C₂-C₆alkenyl, and C₂-C₆alkynyl is optionally substituted with one or more substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, C(O)H, C(O)OH, OH, CN, NO₂, F, Cl, Br and I; wherein each R⁵ aryl, cycloalkyl, cycloalkenyl, heteroaryl, heterocycloalkyl, and heterocycloalkenyl is optionally substituted with one or more substituents independently selected from the group consisting of R⁸, OR⁸, SR⁸, S(O)R⁸, SO₂R⁸, C(O)R⁸, CO(O)R⁸, OC(O)R⁸, OC(O)OR⁸, NH₂, NHR⁸, N(R⁸)₂, NHC(O)R⁸, NR⁸C(O)R⁸, NHS(O)₂R⁸, NR⁸S(O)₂R⁸, NHC(O)OR⁸, NR⁸C(O)OR⁸, NHC(O)NH₂, NHC(O)NHR⁸, NHC(O)N(R⁸)₂, NR⁸C(O)NHR⁸, NR⁸C(O)N(R⁸)₂, C(O)NH₂, C(O)NHR⁸, C(O)N(R⁸)₂, C(O)NHOH, C(O)NHOR⁸, C(O)NHSO₂R⁸, C(O)NR⁸SO₂R⁸, SO₂NH₂, SO₂NHR⁸, SO₂N(R⁸)₂, C(O)H, C(O)OH, (O), OH, CN, NO₂, F, Cl, Br and I. In another embodiment of Formula (I), R⁵, at each occurrence, is independently selected from the group consisting of C₁-C₈alkyl, heteroaryl, heterocycloalkyl, and cycloalkyl; wherein each R⁵C₁-C₈alkyl is optionally substituted with one or more substituents independently selected from the group consisting of R⁷, OR⁷, C(O)R⁷, CO(O)R⁷, NH₂, NHR⁷, NHC(O)OR⁷, C(O)NH₂, C(O)NHR⁷, C(O)N(R⁷)₂, SO₂NHR⁷, C(O)OH, OH, and CN; wherein each R⁵ cycloalkyl, heteroaryl, and heterocycloalkyl is optionally substituted with one or more substituents independently selected from the group consisting of R⁸, CO(O)R⁸, C(O)OH, and OH.

In one embodiment of Formula (I), R⁶, at each occurrence, is independently selected from the group consisting of C₁-C₆alkyl, C₂-C₆alkenyl, C₂-C₆alkynyl, aryl, heteroaryl, heterocycloalkyl, heterocycloalkenyl, cycloalkyl, and cycloalkenyl; wherein each R⁶C₁-C₆alkyl, C₂-C₆alkenyl, and C₂-C₆alkynyl is optionally substituted with one or more substituents independently selected from the group consisting of R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, CN, NO$_2$, F, Cl, Br and I; wherein each R$^6$ aryl, cycloalkyl, cycloalkenyl, heteroaryl, heterocycloalkyl, and heterocycloalkenyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, (O), OH, CN, NO$_2$, F, Cl, Br and I. In another embodiment of Formula (I), R$^6$, at each occurrence, is independently selected from the group consisting of C$_1$-C$_6$alkyl, aryl, heteroaryl, heterocycloalkenyl, and cycloalkyl; wherein each R$^6$C$_1$-C$_6$alkyl is optionally substituted with one or more substituents independently selected from the group consisting of R$^9$, SR$^9$, and OH; wherein each R$^6$ heteroaryl is optionally substituted with one or more substituents independently selected from the group consisting of NH$_2$, F, Cl, Br and I. In another embodiment of Formula (I), R$^6$, at each occurrence, is independently selected from the group consisting of C$_1$-C$_6$alkyl, aryl, heteroaryl, heterocycloalkenyl, and cycloalkyl; wherein each R$^6$C$_1$-C$_6$alkyl is optionally substituted with one or more substituents independently selected from the group consisting of R$^9$, SR$^9$, and OH; wherein each R$^6$ heteroaryl is optionally substituted with one or more substituents independently selected from the group consisting of NH$_2$, and Cl.

In one embodiment of Formula (I), R$^8$, at each occurrence, is independently selected from the group consisting of C$_1$-C$_6$alkyl, C$_2$-C$_6$alkenyl, and C$_2$-C$_6$alkynyl; wherein each R$^8$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I. In another embodiment of Formula (I), R$^8$, at each occurrence, is independently C$_1$-C$_6$alkyl; wherein each R$^8$C$_1$-C$_6$alkyl is optionally substituted with one or more C(O)OH.

In one embodiment of Formula (I), R$^9$, at each occurrence, is independently selected from the group consisting of C$_1$-C$_6$alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^9$ aryl, cycloalkyl, cycloalkenyl, heteroaryl, heterocycloalkyl, and heterocycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, (O), OH, CN, NO$_2$, F, Cl, Br and I. In another embodiment of Formula (I), R$^9$, at each occurrence, is independently selected from the group consisting of aryl, heteroaryl, heterocycloalkyl, and cycloalkyl; wherein each R$^9$ aryl, heteroaryl, and heterocycloalkyl is optionally substituted with one or more substituents independently selected from the group consisting of R$^{12}$, OR$^{12}$, SO$_2$R$^{12}$, C(O)R$^{12}$, CO(O)R$^{12}$, C(O)NH$_2$, SO$_2$NH$_2$, OH, CN, F, and Cl.

In one embodiment of Formula (I), R$^{11}$, at each occurrence, is independently selected from the group consisting of C$_1$-C$_6$alkyl, C$_2$-C$_6$alkenyl, and C$_2$-C$_6$alkynyl; wherein each R$^{11}$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I. In another embodiment of Formula (I), R$^{11}$, at each occurrence, is C$_1$-C$_6$alkyl; wherein each R$^{11}$C$_1$-C$_6$alkyl is optionally substituted with one or more OH.

In one embodiment of Formula (I), R$^{12}$, at each occurrence, is independently selected from the group consisting of C$_1$-C$_6$alkyl, C$_2$-C$_6$alkenyl, and C$_2$-C$_6$ alkynyl; wherein each R$^{12}$C$_1$-C$_6$alkyl, C$_2$-C$_6$alkenyl, and C$_2$-C$_6$alkynyl is optionally substituted with one or more substituents independently selected from the group consisting of NH$_2$, NHR$^{13}$, N(R$^{13}$)$_2$, C(O)H, C(O)OH, OH, CN, NO$_2$, F, Cl, Br and I. In another embodiment of Formula (I), R$^{12}$, at each occurrence, is C$_1$-C$_6$alkyl; wherein each R$^{12}$C$_1$-C$_6$alkyl is optionally substituted with one or more substituents independently selected from the group consisting of N(R$^{13}$)$_2$, and C(O)OH.

In one embodiment of Formula (I), R$^{13}$, at each occurrence, is independently selected from the group consisting of C$_1$-C$_6$alkyl, C$_2$-C$_6$alkenyl, and C$_2$-C$_6$ alkynyl. In another embodiment of Formula (I), R$^{13}$, at each occurrence, is C$_1$-C$_6$alkyl.

In one embodiment of Formula (I), R$^1$ is selected from the group consisting of cycloalkyl, cycloalkenyl, heterocycloalkyl, and heterocycloalkenyl; wherein the R$^1$ cycloalkyl, cycloalkenyl, heterocycloalkyl and heterocycloalkenyl are optionally substituted with one or more substituents independently selected from the group consisting of R$^5$, SO$_2$R$^5$, C(O)R$^5$, CO(O)R$^5$, NH$_2$, NHR$^5$, SO$_2$NHC(O)OR$^5$, NHSO$_2$NHC(O)OR$^5$, C(O)NHR$^5$, SO$_2$NH$_2$, C(O)NHCN, S(O)(N)R$^5$, C(O)OH, and OH; R$^2$ is selected from the group consisting of hydrogen, C$_1$-C$_4$ alkyl, and CN; R$^3$ is selected from the group consisting of phenyl, and pyridinyl; wherein the R$^3$ phenyl, and pyridinyl are optionally substituted with one or more substituents independently selected from the group consisting of R$^6$, OR$^6$, NH$_2$, NHR$^6$, N(R$^6$)$_2$, NHC(O)R$^6$, NHS(O)$_2$R$^6$, CN, F, and Cl; R$^4$ is selected from the group consisting of hydrogen, CN, F, and Cl; R$^5$, at each occurrence, is independently selected from the group consisting of C$_1$-C$_8$alkyl, heteroaryl, heterocycloalkyl, and cycloalkyl; wherein each R$^5$C$_1$-C$_8$alkyl, is optionally substituted with one or more substituents independently selected from the group consisting of R$^7$, OR$^7$, C(O)R$^7$, CO(O)R$^7$, NH$_2$, NHR$^7$, NHC(O)OR$^7$, C(O)NH$_2$, C(O)NHR$^7$, C(O)N(R$^7$)$_2$, SO$_2$NHR$^7$, C(O)OH, OH, and CN; wherein each R$^5$ cycloalkyl, heteroaryl, and heterocycloalkyl is optionally substituted with one or more substituents independently selected from the group consisting of R$^8$, CO(O)R$^8$, C(O)OH, and OH; R$^6$, at each occurrence, is independently selected from the group consisting of C$_1$-C$_6$alkyl, aryl, heteroaryl, heterocycloalkyl, and cycloalkyl; wherein each R$^6$C$_1$-C$_6$alkyl is optionally substituted with one or more substituents independently selected from the group consisting of R$^9$, SR$^9$, and OH; wherein each R$^6$ heteroaryl is optionally substituted with one or more substituents independently selected from the group consisting of NH$_2$, and Cl; R$^7$, at each occurrence, is independently selected from the group consisting of C$_1$-C$_6$alkyl, aryl, heteroaryl, heterocycloalkyl, and cycloalkyl; wherein each R$^7$C$_1$-C$_6$alkyl is optionally substituted with one or more substituents independently selected from the group consisting of aryl and OH; wherein each $R^7$ aryl, cycloalkyl, and heterocycloalkyl is optionally substituted with one or more substituents independently selected from the group consisting of $R^{11}$, CO(O)$R^{11}$, NHC(O)$R^{11}$, C(O)NH$_2$, C(O)OH, and OH; $R^8$, at each occurrence, is independently $C_1$-$C_6$alkyl; wherein each $R^8C_1$-$C_6$alkyl is optionally substituted with one or more C(O)OH; $R^9$, at each occurrence, is independently selected from the group consisting of aryl, heteroaryl, heterocycloalkyl, and cycloalkyl; wherein each $R^9$ aryl, cycloalkyl, heteroaryl, and heterocycloalkyl is optionally substituted with one or more substituents independently selected from the group consisting of $R^{12}$, O$R^{12}$, SO$_2R^{12}$, C(O)$R^{12}$, CO(O)$R^{12}$, C(O)NH$_2$, SO$_2$NH$_2$, OH, CN, F, and Cl; $R^{11}$, at each occurrence, is independently selected from the group consisting of $C_1$-$C_6$alkyl; wherein each $R^{11}C_1$-$C_6$alkyl is optionally substituted with one or more OH; $R^{12}$, at each occurrence, is independently $C_1$-$C_6$alkyl; wherein each $R^{12}C_1$-$C_6$alkyl is optionally substituted with one or more substituents independently selected from the group consisting of N($R^{13}$)$_2$, and C(O)OH; and $R^{13}$, at each occurrence, is $C_1$-$C_6$alkyl.

Still another embodiment pertains to compounds of Formula (I), selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, and pharmaceutically acceptable salts thereof.

Embodiments of Formula (II)

In another aspect, the present invention relates to compounds of Formula (II) or a pharmaceutically acceptable salt thereof,

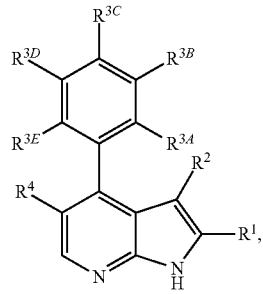

Formula (II)

wherein $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, O$R^5$, S$R^5$, S(O)$R^5$, SO$_2R^5$, C(O)$R^5$, CO(O)$R^5$, OC(O)$R^5$, OC(O)O$R^5$, NH$_2$, NH$R^5$, N($R^5$)$_2$, NHC(O)$R^5$, N$R^5$C(O)$R^5$, SO$_2$NHC(O)$R^5$, SO$_2$N$R^5$C(O)$R^5$, NHS(O)$_2R^5$, $NR^5$S(O)$_2R^5$, NHC(O)O$R^5$, $NR^5$C(O)O$R^5$, SO$_2$NHC(O)O$R^5$, SO$_2$N$R^5$C(O)O$R^5$, NHSO$_2$NHC(O)O$R^5$, NHSO$_2$N$R^5$C(O)O$R^5$, $NR^5$SO$_2$N$R^5$C(O)OR, N$R^5$SO$_2$NHC(O)O$R^5$, NHC(O)NH$_2$, NHC(O)NH$R^5$, NHC(O)N($R^5$)$_2$, $NR^5$C(O)NH$R^5$, $NR^5$C(O)N($R^5$)$_2$, OC(O)NH$_2$, OC(O)NH$R^5$, OC(O)N($R^5$)$_2$, OC(O)NHSO$_2R^5$, OC(O)N$R^5$SO$_2R^5$, C(O)NH$_2$, C(O)NH$R^5$, C(O)N($R^5$)$_2$, C(O)NHOH, C(O)NHO$R^5$, C(O)NHSO$_2R^5$, C(O)N$R^5$SO$_2R^5$, SO$_2$NH$_2$, SO$_2$NH$R^5$, SO$_2$N($R^5$)$_2$, OSO$_2$NH$_2$, OSO$_2$NH$R^5$, OSO$_2$N($R^5$)$_2$, C(O)NHCN, C(O)N$R^5$CN, S(O)(N)$R^5$, C(O)H, C(O)OH, (O), OH, CN, NO$_2$, F, Cl, Br and I;

$R^2$ is selected from the group consisting of hydrogen, $C_1$-$C_4$ alkyl, NO$_2$, CN, C(O)NH$_2$, and C(O)O$R^{2A}$;

$R^{2A}$ is selected from the group consisting of alkyl, alkenyl, and alkynyl;

$R^{3A}$, $R^{3B}$, $R^{3C}$, $R^{3D}$, and $R^{3E}$ are each independently selected from the group consisting of H, $R^6$, O$R^6$, S$R^6$, S(O)$R^6$, C(O)$R^6$, CO(O)$R^6$, OC(O)$R^6$, OC(O)O$R^6$, NH$_2$, NH$R^6$, N($R^6$)$_2$, NHC(O)$R^6$, $NR^6$C(O)$R^6$, NHS(O)$_2R^6$, $NR^6$S(O)$_2R^6$, NHC(O)O$R^6$, $NR^6$C(O)O$R^6$, NHC(O)NH$_2$, NHC(O)NH$R^6$, NHC(O)N($R^6$)$_2$, $NR^6$C(O)NH$R^6$, $NR^6$C(O)N($R^6$)$_2$, C(O)NH$_2$, C(O)NH$R^6$, C(O)N($R^6$)$_2$, C(O)NHOH, C(O)NHO$R^6$, C(O)NHSO$_2R^6$, C(O)N$R^6$SO$_2R^6$, C(O)H, C(O)OH, (O), OH, CN, NO$_2$, F, Cl, Br and I;

$R^4$ is selected from the group consisting of hydrogen, $R^{4A}$, O$R^{4A}$, C(O)NH$_2$, CN, F, Cl, Br, and I;

$R^{4A}$ is selected from the group consisting of haloalkyl, alkyl, alkenyl, and alkynyl;

$R^5$, at each occurrence, is independently selected from the group consisting of $C_1$-$C_8$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^5C_1$-$C_8$alkyl, $C_2$-$C_6$alkenyl, and $C_2$-$C_6$alkynyl is optionally substituted with one or more substituents independently selected from the group consisting of $R^7$, O$R^7$, S$R^7$, S(O)$R^7$, SO$_2R^7$, C(O)$R^7$, CO(O)$R^7$, OC(O)$R^7$, OC(O)O$R^7$, NH$_2$, NH$R^7$, N($R^7$)$_2$, NHC(O)$R^7$, $NR^7$C(O)$R^7$, NHS(O)$_2R^7$, $NR^7$S(O)$_2R^7$, NHC(O)O$R^7$, $NR^7$C(O)O$R^7$, NHC(O)NH$_2$, NHC(O)NH$R^7$, NHC(O)N($R^7$)$_2$, $NR^7$C(O)NH$R^7$, $NR^7$C(O)N($R^7$)$_2$, C(O)NH$_2$, C(O)NH$R^7$, C(O)N($R^7$)$_2$, C(O)NHOH, C(O)NHO$R^7$, C(O)NHSO$_2R^7$, C(O)N$R^7$SO$_2R^7$, SO$_2$NH$_2$, SO$_2$NH$R^7$, SO$_2$N($R^7$)$_2$, C(O)H, C(O)OH, OH, CN, NO$_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, O$R^8$, S$R^8$, S(O)$R^8$, SO$_2R^8$, C(O)$R^8$, CO(O)$R^8$, OC(O)$R^8$, OC(O)O$R^8$, NH$_2$, NH$R^8$, N($R^8$)$_2$, NHC(O)$R^8$, $NR^8$C(O)$R^8$, NHS(O)$_2R^8$, $NR^8$S(O)$_2R^8$, NHC(O)O$R^8$, $NR^8$C(O)O$R^8$, NHC(O)NH$_2$, NHC(O)NH$R^8$, NHC(O)N($R^8$)$_2$, $NR^8$C(O)NH$R^8$, $NR^8$C(O)N($R^8$)$_2$, C(O)NH$_2$, C(O)NH$R^8$, C(O)N($R^8$)$_2$, C(O)NHOH, C(O)NHO$R^8$, C(O)NHSO$_2R^8$, C(O)

$NR^8SO_2R^8$, $SO_2NH_2$, $SO_2NHR^8$, $SO_2N(R^8)_2$, $C(O)H$, $C(O)OH$, $(O)$, $OH$, $CN$, $NO_2$, $F$, $Cl$, $Br$ and $I$;

$R^6$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^6C_1$-$C_6$alkyl, $C_2$-$C_6$alkenyl, and $C_2$-$C_6$alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, $F$, $Cl$, $Br$ and $I$; wherein each $R^6$ aryl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $(O)$, $OH$, $CN$, $NO_2$, $F$, $Cl$, $Br$ and $I$;

$R^7$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^7C_1$-$C_6$alkyl, $C_2$-$C_6$alkenyl, and $C_2$-$C_6$alkynyl is optionally substituted with one or more substituents independently selected from the group consisting of aryl, heteroaryl, cycloalkyl, cycloalkenyl, heterocycloalkyl, heterocycloalkenyl, $NH_2$, $NHR^{13}$, $N(R^{13})_2$, $C(O)H$, $C(O)OH$, $OH$, $CN$, $NO_2$, $F$, $Cl$, $Br$ and $I$; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $(O)$, $OH$, $CN$, $NO_2$, $F$, $Cl$, $Br$ and $I$;

$R^8$, at each occurrence, is independently selected from the group consisting of $C_1$-$C_6$alkyl, $C_2$-$C_6$alkenyl, and $C_2$-$C_6$alkynyl; wherein each $R^8C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^9$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $(O)$, $OH$, $CN$, $NO_2$, $F$, $Cl$, $Br$ and $I$;

$R^{10}$, at each occurrence, is independently selected from the group consisting of $C_1$-$C_6$alkyl, $C_2$-$C_6$alkenyl, and $C_2$-$C_6$ alkynyl; wherein each $R^{10}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^{11}$, at each occurrence, is independently selected from the group consisting of $C_1$-$C_6$alkyl, $C_2$-$C_6$alkenyl, and $C_2$-$C_6$alkynyl; wherein each $R^{11}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{13}$, $N(R^{13})_2$, $C(O)H$, $C(O)OH$, $OH$, $CN$, $NO_2$, $F$, $Cl$, $Br$ and $I$; and $R^{13}$, at each occurrence, is independently selected from the group consisting of $C_1$-$C_6$alkyl, $C_2$-$C_6$alkenyl, and $C_2$-$C_6$ alkynyl.

In one embodiment of Formula (II), $R^2$ is selected from the group consisting of hydrogen, $C_1$-$C_4$ alkyl, $NO_2$, $CN$, $C(O)NH_2$, and $C(O)OR^{2A}$; and $R^{2A}$ is selected from the group consisting of alkyl, alkenyl, and alkynyl. In another embodiment of Formula (II), $R^2$ is selected from the group consisting of hydrogen, $C_1$-$C_4$ alkyl, $NO_2$, $CN$, $C(O)NH_2$, and $C(O)OR^{2A}$; and $R^{2A}$ is alkyl. In another embodiment of Formula (II), $R^2$ is selected from the group consisting of hydrogen, $C_1$-$C_4$ alkyl, and $CN$. In another embodiment of Formula (II), $R^2$ is selected from the group consisting of hydrogen, $CH_3$, and $CN$. In another embodiment of Formula (II), $R^2$ is hydrogen. In another embodiment of Formula (II), $R^2$ is $CH_3$. In another embodiment of Formula (II), $R^2$ is $CN$.

In one embodiment of Formula (II), $R^4$ is selected from the group consisting of hydrogen, $R^{4A}$, $OR^{4A}$, $C(O)NH_2$, $CN$, $F$, $Cl$, $Br$, and $I$; and $R^{4A}$ is selected from the group consisting of haloalkyl, alkyl, alkenyl, and alkynyl. In another embodiment of Formula (II), $R^4$ is selected from the group consisting of hydrogen, $R^{4A}$, $OR^{4A}$, $C(O)NH_2$, $CN$, $F$, and $Cl$; and $R^{4A}$ is selected from the group consisting of haloalkyl and alkyl. In another embodiment of Formula (II), $R^4$ is selected from the group consisting of hydrogen, $CN$, $F$, and $Cl$. In another embodiment of Formula (II), $R^4$ is hydrogen. In another embodiment of Formula (II), $R^4$ is $CN$. In another embodiment of Formula (II), $R^4$ is $F$. In another embodiment of Formula (II), $R^4$ is $Cl$.

In one embodiment of Formula (II), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)R^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, $(O)$, $OH$, $CN$, $NO_2$, $F$, $Cl$, $Br$ and $I$. In another embodiment of Formula (II), $R^1$ is selected from the group consisting of cycloalkyl, cycloalkenyl, heterocycloalkyl, and heterocycloalkenyl; wherein the R cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and $OH$. In another embodiment of Formula (II), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and $OH$. In another embodiment of Formula (II), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and $OH$. In another embodiment of Formula (II), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and $OH$. In another embodiment of Formula (II), $R^1$ is heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and $OH$. In another embodiment of Formula (II), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, $(O)$, $OH$, $CN$, $NO_2$, $F$, $Cl$, $Br$ and $I$. In another embodiment of Formula (II), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR$, $NHSO_2NHC(O)OR$, $C(O)NHR^5$, $SO_2NH_2$, $C(O)NHCN$, $S(O)(N)R^5$, $C(O)OH$, and $OH$. In another embodiment of Formula (II), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (II), $R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, $F$, $Cl$, $Br$ and $I$. In another embodiment of Formula (II), $R^{3A}$, $R^{3B}$, $R^{3C}$, $R^{3D}$, and $R^{3E}$ are each independently selected from the group consisting of H, $R^6$, $OR^6$, $NH_2$, $NHR^6$, $N(R^6)_2$, $NHC(O)R^6$, $NHS(O)_2R^6$, $CN$, $F$, $Cl$, $Br$ and $I$. In another embodiment of Formula (II), $R^{3A}$, $R^{3B}$, $R^{3C}$, $R^{3D}$, and $R^{3E}$ are each independently selected from the group consisting of H, $R^6$, $OR^6$, $NH_2$, $NHR^6$, $N(R^6)_2$, $NHC(O)R^6$, $NHS(O)_2R^6$, $CN$, $F$, and $Cl$. In another embodiment of Formula (II), $R^{3A}$, $R^{3B}$, $R^{3C}$, $R^{3D}$, and $R^{3E}$ are each independently selected from the group consisting of H, $R^6$, $OR^6$, $NH_2$, $NHR^6$, $N(R^6)_2$, $NHS(O)_2R^6$, $CN$, $F$, and $Cl$. In one embodiment of Formula (II), $R^{3A}$ is H, $R^{3B}$ is F, $R^{3C}$ is H, $R^{3D}$ is H, and $R^{3E}$ is $OR^6$. In another embodiment of Formula (II), $R^{3A}$ is H, $R^{3B}$ is F, $R^{3C}$ is H, $R^{3D}$ is H, and $R^{3E}$ is $OCH_3$.

In one embodiment of Formula (II), $R^5$, at each occurrence, is independently selected from the group consisting of $C_1$-$C_8$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^5C_1$-$C_8$alkyl, $C_2$-$C_6$alkenyl, and $C_2$-$C_6$alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N$ $(R^7)_2$, C(O)H, C(O)OH, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, OR, $SR^8$, $S(O)R^8$, $SO_2R$, $C(O)R^8$, $CO(O)R^8$, $OC(O)R^8$, OC(O)OR, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, C(O)NHOH, $C(O)NHOR^8$, $C(O)NHSO_2R^8$, $C(O)NR^8SO_2R^8$, $SO_2NH_2$, $SO_2NHR^8$, $SO_2N(R^8)_2$, C(O)H, C(O)OH, (O), OH, CN, $NO_2$, F, Cl, Br and I. In another embodiment of Formula (II), $R^5$, at each occurrence, is independently selected from the group consisting of $C_1$-$C_8$alkyl, heteroaryl, heterocycloalkyl, and cycloalkyl; wherein each $R^5C_1$-$C_8$alkyl is optionally substituted with one or more substituents independently selected from the group consisting of $R^7$, $OR^7$, $C(O)R^7$, $CO(O)R^7$, $NH_2$, $NHR^7$, $NHC(O)OR^7$, $C(O)NH_2$, $C(O)NHR^7$, $C(O)N(R^7)_2$, $SO_2NHR^7$, C(O)OH, OH, and CN; wherein each $R^5$ cycloalkyl, heteroaryl, and heterocycloalkyl is optionally substituted with one or more substituents independently selected from the group consisting of $R^8$, $CO(O)R^8$, C(O)OH, and OH.

In one embodiment of Formula (II), $R^6$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^6C_1$-$C_6$alkyl, $C_2$-$C_6$alkenyl, and $C_2$-$C_6$alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, C(O)NHOH, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, OC(O)$OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, C(O)NHOH, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, C(O)H, C(O)OH, (O), OH, CN, $NO_2$, F, Cl, Br and I. In another embodiment of Formula (II), $R^6$, at each occurrence, is independently selected from the group consisting of $C_1$-$C_6$alkyl, aryl, heteroaryl, heterocycloalkyl, and cycloalkyl; wherein each $R^6C_1$-$C_6$alkyl is optionally substituted with one or more substituents independently selected from the group consisting of $R^9$, $SR^9$, and OH; wherein each $R^6$ heteroaryl is optionally substituted with one or more substituents independently selected from the group consisting of $NH_2$, F, Cl, Br and I. In another embodiment of Formula (II), $R^6$, at each occurrence, is independently selected from the group consisting of $C_1$-$C_6$alkyl, aryl, heteroaryl, heterocycloalkyl, and cycloalkyl; wherein each $R^6C_1$-$C_6$alkyl is optionally substituted with one or more substituents independently selected from the group consisting of $R^9$, $SR^9$, and OH; wherein each $R^6$ heteroaryl is optionally substituted with one or more substituents independently selected from the group consisting of $NH_2$ and Cl.

In one embodiment of Formula (II), $R^8$, at each occurrence, is independently selected from the group consisting of $C_1$-$C_6$alkyl, $C_2$-$C_6$alkenyl, and $C_2$-$C_6$alkynyl; wherein each $R^8C_1$-$C_6$alkyl, $C_2$-$C_6$alkenyl, and $C_2$-$C_6$alkynyl is optionally substituted with one or more substituents independently selected from the group consisting of $NH_2$, C(O)H, C(O)OH, OH, CN, $NO_2$, F, Cl, Br and I. In another embodiment of Formula (II), $R^8$, at each occurrence, is independently $C_1$-$C_6$alkyl; wherein each $R^8C_1$-$C_6$alkyl is optionally substituted with one or more C(O)OH.

In one embodiment of Formula (II), $R^9$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, (O), OH, CN, $NO_2$, F, Cl, Br and I. In another embodiment of Formula (II), $R^9$, at each occurrence, is independently selected from the group consisting of aryl, heteroaryl, heterocycloalkyl, and cycloalkyl; wherein each $R^9$ aryl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, OH, CN, F, and Cl.

In one embodiment of Formula (II), $R^{11}$, at each occurrence, is independently selected from the group consisting of $C_1$-$C_6$alkyl, $C_2$-$C_6$alkenyl, and $C_2$-$C_6$alkynyl; wherein each $R^{11}C_1$-$C_6$alkyl, $C_2$-$C_6$alkenyl, and $C_2$-$C_6$alkynyl is optionally substituted with one or more substituents independently selected from the group consisting of $NH_2$, C(O)H, C(O)OH, OH, CN, $NO_2$, F, Cl, Br and I. In another embodiment of Formula (II), $R^{11}$, at each occurrence, is $C_1$-$C_6$alkyl; wherein each $R^{11}C_1$-$C_6$alkyl is optionally substituted with one or more OH.

In one embodiment of Formula (II), $R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{13}$, $N(R^{13})_2$, C(O)H, C(O)OH, OH, CN, $NO_2$, F, Cl, Br and I. In another embodiment of Formula (II), $R^{12}$, at each occurrence, is $C_1$-$C_6$alkyl; wherein each $R^{12}C_1$-$C_6$alkyl is optionally substituted with one or more substituents independently selected from the group consisting of $N(R^{13})_2$, and C(O)OH.

In one embodiment of Formula (II), $R^{13}$, at each occurrence, is independently selected from the group consisting of $C_1$-$C_6$alkyl, $C_2$-$C_6$alkenyl, and $C_2$-$C_6$ alkynyl. In another embodiment of Formula (II), $R^{13}$, at each occurrence, is $C_1$-$C_6$alkyl.

In one embodiment of Formula (II), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH; $R^2$ is selected from the group consisting of hydrogen, $C_1$-$C_4$ alkyl, and CN; $R^{3A}$, $R^{3B}$, $R^{3C}$, $R^{3D}$ and $R^{3E}$ are each independently selected from the group consisting of H, $R^6$, $OR^6$, $NH_2$, $NHR^6$, $N(R^6)_2$, $NHC(O)R^6$, $NHS(O)_2R^6$, F, and Cl; $R^4$ is selected from the group consisting of hydrogen, CN, F, and Cl; $R^5$, at each occurrence, is independently selected from the group consisting of $C_1$-$C_8$alkyl, heteroaryl, heterocycloalkyl, and cycloalkyl; wherein each $R^5C_1$-$C_8$alkyl, is optionally substituted with one or more substituents independently selected from the group consisting of $R^7$, $OR^7$, $C(O)R^7$, $CO(O)R^7$, $NH_2$, $NHR^7$, $NHC(O)OR^7$, $C(O)NH_2$, $C(O)NHR^7$, $C(O)N(R^7)_2$, $SO_2NHR^7$, $C(O)OH$, OH, and CN; wherein each $R^5$ cycloalkyl, heteroaryl, and heterocycloalkyl is optionally substituted with one or more substituents independently selected from the group consisting of $R^8$, $CO(O)R^8$, $C(O)OH$, and OH; $R^6$, at each occurrence, is independently selected from the group consisting of $C_1$-$C_6$alkyl, aryl, heteroaryl, heterocycloalkenyl, and cycloalkyl; wherein each $R^6C_1$-$C_6$alkyl is optionally substituted with one or more substituents independently selected from the group consisting of $R^9$, $SR^9$, and OH; wherein each $R^6$ heteroaryl is optionally substituted with one or more substituents independently selected from the group consisting of $NH_2$, and Cl; $R^7$, at each occurrence, is independently selected from the group consisting of $C_1$-$C_6$alkyl, aryl, heteroaryl, heterocycloalkyl, and cycloalkyl; wherein each $R^7C_1$-$C_6$alkyl is optionally substituted with one or more substituents independently selected from the group consisting of aryl and OH; wherein each $R^7$ aryl, cycloalkyl, and heterocycloalkyl is optionally substituted with one or more substituents independently selected from the group consisting of $R^{11}$, $CO(O)R^{11}$, $NHC(O)R^{11}$, $C(O)NH_2$, $C(O)OH$, and OH; $R^8$, at each occurrence, is independently $C_1$-$C_6$alkyl; wherein each $R^8C_1$-$C_6$alkyl is optionally substituted with one or more $C(O)OH$; $R^9$, at each occurrence, is independently selected from the group consisting of aryl, heteroaryl, heterocycloalkyl, and cycloalkyl; wherein each $R^9$ aryl, cycloalkyl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, OH, CN, F, and Cl; $R^{11}$, at each occurrence, is independently selected from the group consisting of $C_1$-$C_6$alkyl; wherein each $R^{11}C_1$-$C_6$alkyl is optionally substituted with one or more OH; $R^{12}$, at each occurrence, is independently $C_1$-$C_6$alkyl; wherein each $R^{12}C_1$-$C_6$alkyl is optionally substituted with one or more substituents independently selected from the group consisting of $N(R^{13})_2$, and $C(O)OH$; and $R^{13}$, at each occurrence, is $C_1$-$C_6$alkyl.

Still another embodiment pertains to compounds of Formula (II), selected from the group consisting of: Examples 1, 2, 3, 4, 6, 7, 8, 9, 10, 17, 18, 19, 22, 23, 24, 25, 27, 28, 29, 30, 50, 51, 53, 59, 60, 61, 62, 63, 66, 67, 68, 69, 71, 72, 73, 74, 75, 76, 78, 85, 87, 94, 98, 99, 100, 101, 103, 108, 109, 110, 111, 112, 113, 114, 115, 116, 117, 118, 119, 120, 121, 122, 123, 124, 125, 126, 127, 128, 129, 130, 131, 135, 136, 137, 145, 146, 147, 148, 149, 166, 167, 168, 169, 170, 171, 172, 179, 180, 181, 182, 183, 184, 185, 186, 187, 189, 190, 191, 193, 195, 199, 201, 206, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, and pharmaceutically acceptable salts thereof.

Embodiments of Formula (IIa)

In another aspect, the present invention relates to compounds of Formula (IIa) or a pharmaceutically acceptable salt thereof,

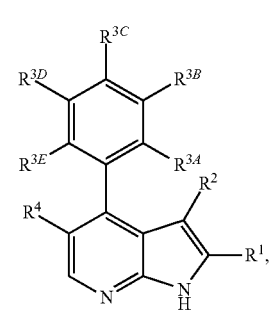

Formula (IIa)

wherein
$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR$, $SO_2NR^5C(O)OR^5$, $NHSO_2NHC(O)OR$, $NHSO_2NR^5C(O)OR$, $NR^5SO_2NR^5C(O)OR$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, $C(O)H$, $C(O)OH$, (O), OH, CN, $NO_2$, F, Cl, Br and I;
$R^2$ is selected from the group consisting of hydrogen, $C_1$-$C_4$ alkyl, $NO_2$, CN, $C(O)NH_2$, $C(O)OR^{2A}$, F, Cl, Br and I;
$R^{2A}$ is selected from the group consisting of $C_1$-$C_6$alkyl, $C_2$-$C_6$alkenyl, and $C_2$-$C_6$alkynyl;
$R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, (O), OH, CN, $NO_2$, F, Cl, Br and I;
$R^4$ is selected from the group consisting of $R^{4A}$, $OR^{4A}$, $C(O)NH_2$, CN, F, Cl, Br, and I;
$R^{4A}$ is selected from the group consisting of hydrogen, $C_1$-$C_6$ alkyl, $C_2$-$C_6$alkenyl, and $C_2$-$C_6$alkynyl;

$R^5$, at each occurrence, is independently selected from the group consisting of $C_1$-$C_6$ alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^5 C_1$-$C_6$ alkyl, $C_2$-$C_6$alkenyl, and $C_2$-$C_6$alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, $OH$, $CN$, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I;

$R^6$, at each occurrence, is independently selected from the group consisting of $C_1$-$C_6$alkyl, $C_2$-$C_6$alkenyl, $C_2$-$C_6$alkynyl, phenyl, heteroaryl, heterocycloalkyl, heterocycloalkenyl, cycloalkyl, and cycloalkenyl; wherein each $R^6 C_1$-$C_6$alkyl, $C_2$-$C_6$alkenyl, and $C_2$-$C_6$alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I;

$R^7$, at each occurrence, is independently selected from the group consisting of $C_1$-$C_6$ alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^7 C_1$-$C_6$ alkyl, $C_2$-$C_6$alkenyl, and $C_2$-$C_6$alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, (O), OH, CN, $NO_2$, F, Cl, Br and I;

$R^8$, at each occurrence, is independently selected from the group consisting of $C_1$-$C_6$ alkyl, $C_2$-$C_6$alkenyl, $C_2$-$C_6$alkynyl, and heterocycloalkyl; wherein each $R^8 C_1$-$C_6$ alkyl, $C_2$-$C_6$alkenyl, and $C_2$-$C_6$alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)OH$, OH, CN, $NO_2$, F, Cl, Br and I;

$R^{8A}$, at each occurrence, is independently selected from the group consisting of $C_1$-$C_6$ alkyl, $C_2$-$C_6$alkenyl, and $C_2$-$C_6$alkynyl;

$R^9$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^9 C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I;

$R^{10}$, at each occurrence, is independently selected from the group consisting of $C_1$-$C_6$alkyl, $C_2$-$C_6$alkenyl, and $C_2$-$C_6$ alkynyl; wherein each $R^{10} C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I;

$R^{11}$, at each occurrence, is independently selected from the group consisting of $C_1$-$C_6$alkyl, $C_2$-$C_6$alkenyl, $C_2$-$C_6$alkynyl, aryl, and heteroaryl; wherein each $R^{11} C_1$-$C_6$alkyl, $C_2$-$C_6$alkenyl, and $C_2$-$C_6$alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$alkyl, $C_1$-$C_6$ haloalkyl, $NH_2$, C(O)H, C(O)OH, OH, CN, $NO_2$, F, Cl, Br and I;

$R^{11A}$, at each occurrence, is independently selected from the group consisting of $C_1$-$C_6$alkyl, $C_2$-$C_6$alkenyl, and $C_2$-$C_6$ alkynyl;

$R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{14}$, $N(R^{14})_2$, C(O)H, C(O)OH, OH, CN, $NO_2$, F, Cl, Br and I;

$R^{13}$, at each occurrence, is independently selected from the group consisting of $C_1$-$C_6$alkyl, $C_2$-$C_6$alkenyl, $C_2$-$C_6$ alkynyl, aryl, heteroaryl, cycloalkyl, cycloalkenyl, heterocycloalkyl, and heterocycloalkenyl; wherein each $R^{13}C_1$-$C_6$alkyl, $C_2$-$C_6$alkenyl, and $C_2$-$C_6$alkynyl is optionally substituted with one or more substituents independently selected from the group consisting of $R^{15}$, $OR^{15}$, C(O)H, C(O)OH, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, C(O)H, C(O)OH, (O), OH, CN, $NO_2$, F, Cl, Br and I;

$R^{14}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl;

$R^{15}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl; wherein each $R^{15}C_1$-$C_6$alkyl, $C_2$-$C_6$alkenyl, and $C_2$-$C_6$alkynyl is optionally substituted with one or more $OCH_3$; and $R^{16}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl.

In one embodiment of Formula (IIa), $R^2$ is selected from the group consisting of hydrogen, $C_1$-$C_4$ alkyl, $NO_2$, CN, $C(O)NH_2$, $C(O)OR^{2A}$, F, Cl, Br and I; and $R^{2A}$ is selected from the group consisting of alkyl, alkenyl, and alkynyl. In another embodiment of Formula (IIa), $R^2$ is selected from the group consisting of hydrogen, $C_1$-$C_4$ alkyl, $NO_2$, CN, $C(O)NH_2$, $C(O)OR^{2A}$, Cl, and Br; and $R^{2A}$ is alkyl. In another embodiment of Formula (IIa), $R^2$ is selected from the group consisting of hydrogen, $C_1$-$C_4$ alkyl, and CN. In another embodiment of Formula (IIa), $R^2$ is selected from the group consisting of hydrogen, $CH_3$, and CN. In another embodiment of Formula (IIa), $R^2$ is hydrogen. In another embodiment of Formula (IIa), $R^2$ is $CH_3$. In another embodiment of Formula (IIa), $R^2$ is CN.

In one embodiment of Formula (IIa), $R^4$ is selected from the group consisting of $R^{4A}$, $OR^{4A}$, $C(O)NH_2$, CN, F, Cl, Br, and I; and $R^{4A}$ is selected from the group consisting of hydrogen, $C_1$-$C_6$ alkyl, $C_2$-$C_6$alkenyl, and $C_2$-$C_6$alkynyl. In another embodiment of Formula (IIa), $R^4$ is selected from the group consisting of $R^{4A}$, $OR^{4A}$, $C(O)NH_2$, CN, F, and Cl; and $R^{4A}$ is selected from the group consisting of hydrogen and $C_1$-$C_6$ alkyl. In another embodiment of Formula (IIa), $R^4$ is selected from the group consisting of $R^{4A}$, $OR^{4A}$, $C(O)NH_2$, CN, F, and Cl; and $R^{4A}$ is selected from the group consisting of hydrogen and $C_1$-alkyl. In another embodiment of Formula (IIa), $R^4$ is hydrogen. In another embodiment of Formula (IIa), $R^4$ is CN. In another embodiment of Formula (IIa), $R^4$ is F. In another embodiment of Formula (IIa), $R^4$ is Cl. In another embodiment of Formula (IIa), $R^4$ is OH. In another embodiment of Formula (IIa), $R^4$ is $OCH_3$. In another embodiment of Formula (IIa), $R^4$ is $CH_3$. In another embodiment of Formula (IIa), $R^4$ is $C(O)NH_2$.

In one embodiment of Formula (IIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R$, $SO_2NR^5C(O)R^5$, $NHS(O)_2R$, $NR^5S(O)_2R^5$, $NHC(O)OR^5$, $NR^5C(O)OR^5$, $SO_2NHC(O)OR$, $SO_2NR^5C(O)OR^5$, $NHSO_2NHC(O)OR^5$, $NHSO_2NR^5C(O)OR$, $NR^5SO_2NR^5C(O)OR$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, C(O)H, C(O)OH, (O), OH, CN, $NO_2$, F, Cl, Br and I. In another embodiment of Formula (IIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R^5$, $SO_2NHC(O)OR^5$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, C(O)OH, (O), OH, and CN. In another embodiment of Formula (IIa), $R^1$ is cycloalkyl; wherein the $R^1$ cycloalkyl is optionally substituted with one or more substituents independently selected from the group consisting of $R^5$, $OR^5$, $SO_2R$, $C(O)R^5$, $CO(O)R^5$, $NH_2$, $NHR^5$, $NHC(O)R^5$, $SO_2NHC(O)R$, $NHS(O)_2R^5$, $SO_2NHC(O)OR$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, C(O)OH, (O), OH, and CN. In another embodiment of Formula (IIa), $R^1$ is cycloalkenyl; wherein the $R^1$ cycloalkenyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, C(O)OH, (O), OH, and CN. In another embodiment of Formula (IIa), $R^1$ is heterocycloalkyl; wherein the $R^1$ heterocycloalkyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R$, C(O)OH, (O), OH, and CN. In another embodiment of Formula (IIa), $R^1$ is heterocycloalkenyl; wherein the $R^1$ heterocycloalkenyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R^5$, $SO_2NHC(O)OR^5$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, $(O)$, $OH$, and $CN$. In another embodiment of Formula (IIa), $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, $C(O)H$, $C(O)OH$, $(O)$, $OH$, $CN$, $NO_2$, $F$, $Cl$, $Br$ and $I$. In another embodiment of Formula (IIa), $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R^5$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, $(O)$, $OH$, and $CN$. In another embodiment of Formula (IIa), $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (IIa), $R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $CO(O)R^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, C(O)H, C(O)OH, (O), OH, CN, NO$_2$, F, Cl, Br and I. In another embodiment of Formula (IIa), R$^{3A}$, R$^{3B}$, R$^{3C}$, R$^{3D}$, and R$^{3E}$ are each independently selected from the group consisting of H, R$^6$, OR$^6$, SR$^6$, S(O)R$^6$, C(O)R$^6$, NH$_2$, NHR$^6$, N(R$^6$)$_2$, NHC(O)R$^6$, NHS(O)$_2$R$^6$, C(O)NH$_2$, C(O)NHR$^6$, C(O)N(R$^6$)$_2$, CN, F, and Cl. In another embodiment of Formula (IIa), R$^{3A}$, R$^{3B}$, R$^{3C}$, R$^{3D}$, and R$^{3E}$ are each independently selected from the group consisting of H, R$^6$, OR$^6$, NH$_2$, NHR$^6$, N(R$^6$)$_2$, NHC(O)R$^6$, NHS(O)$_2$R$^6$, CN, F, and Cl. In another embodiment of Formula (IIa), R$^{3A}$, R$^{3B}$, R$^{3C}$, R$^{3D}$, and R$^{3E}$ are each independently selected from the group consisting of H, R$^6$, OR$^6$, NH$_2$, NHR$^6$, N(R$^6$)$_2$, NHS(O)$_2$R$^6$, CN, F, and Cl. In one embodiment of Formula (IIa), R$^{3A}$ is H, R$^{3B}$ is F, R$^{3C}$ is H, R$^{3D}$ is H, and R$^{3E}$ is OR$^6$. In another embodiment of Formula (IIa), R$^{3A}$ is H, R$^{3B}$ is F, R$^{3C}$ is H, R$^{3D}$ is H, and R$^{3E}$ is OCH$_3$. In another embodiment of Formula (IIa), R$^{3A}$ is H, R$^{3D}$ is H, and R$^{3E}$ is OCH$_3$; and R$^{3B}$ and R$^{3C}$ are each independently selected from the group consisting of H, R$^6$, OR$^6$, SR$^6$, S(O)R$^6$, C(O)R$^6$, NH$_2$, NHR$^6$, N(R$^6$)$_2$, NHC(O)R$^6$, NHS(O)$_2$R$^6$, C(O)NH$_2$, C(O)NHR$^6$, C(O)N(R$^6$)$_2$, CN, F, and Cl.

In one embodiment of Formula (IIa), R$^5$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^5$C$_1$-C$_6$ alkyl, C$_2$-C$_6$alkenyl, and C$_2$-C$_6$alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, B(OH)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I. In another embodiment of Formula (IIa), R$^5$, at each occurrence, is independently selected from the group consisting of C$_1$-C$_6$ alkyl, aryl, heteroaryl, heterocycloalkyl, heterocycloalkenyl, cycloalkyl, and cycloalkenyl; wherein each R$^5$C$_1$-C$_6$ alkyl is optionally substituted with one or more substituents independently selected from the group consisting of R$^7$, OR$^7$, SO$_2$R$^7$, C(O)R$^7$, CO(O)R$^7$, OC(O)R$^7$, NH$_2$, NHR$^7$, N(R$^7$)$_2$, NHC(O)R$^7$, NHS(O)$_2$R$^7$, NHC(O)OR$^7$, NHC(O)NHR$^7$, C(O)NH$_2$, C(O)NHR$^7$, C(O)N(R$^7$)$_2$, C(O)NHSO$_2$R$^7$, SO$_2$NH$_2$, SO$_2$NHR$^7$, SO$_2$N(R$^7$)$_2$, B(OH)$_2$, C(O)OH, OH, CN, F, and Cl; wherein each R$^5$ aryl, cycloalkyl, heteroaryl, heterocycloalkyl, and heterocycloalkenyl is optionally substituted with one or more substituents independently selected from the group consisting of R$^8$, OR$^8$, SR$^8$, SO$_2$R$^8$, C(O)R$^8$, CO(O)R$^8$, NH$_2$, NHR$^8$, NHC(O)R$^8$, NHS(O)$_2$R$^8$, C(O)NHR$^8$, C(O)N(R$^8$)$_2$, C(O)NHSO$_2$R$^8$, C(O)OH, (O), OH, CN, NO$_2$, F, and Cl.

In one embodiment of Formula (IIa), R$^6$, at each occurrence, is independently selected from the group consisting of C$_1$-C$_6$alkyl, C$_2$-C$_6$alkenyl, C$_2$-C$_6$alkynyl, phenyl, heteroaryl, heterocycloalkyl, heterocycloalkenyl, cycloalkyl, and cycloalkenyl; wherein each R$^6$C$_1$-C$_6$alkyl, C$_2$-C$_6$alkenyl, and C$_2$-C$_6$alkynyl is optionally substituted with one or more substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, CN, NO$_2$, F, Cl, Br and I; wherein each R$^6$phenyl, cycloalkyl, cycloalkenyl, heteroaryl, heterocycloalkyl, and heterocycloalkenyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, (O), OH, CN, NO$_2$, F, Cl, Br and I. In another embodiment of Formula (IIa), R$^6$, at each occurrence, is independently selected from the group consisting of C$_1$-C$_6$alkyl, phenyl, heteroaryl, heterocycloalkyl, heterocycloalkenyl, and cycloalkyl; wherein each R$^6$C$_1$-C$_6$alkyl, is optionally substituted with one or more substituents independently selected from the group consisting of R$^9$, NH$_2$, NHR$^9$, NHS(O)$_2$R$^9$, CN, and F; and wherein each R$^6$ phenyl, heteroaryl, heterocycloalkyl, heterocycloalkenyl, and cycloalkyl is optionally substituted with one or more substituents independently selected from the group consisting of R$^{10}$, OR$^{10}$, and F.

In one embodiment of Formula (IIa), R$^7$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^7$C$_1$-C$_6$ alkyl, C$_2$-C$_6$alkenyl, and C$_2$-C$_6$alkynyl is optionally substituted with one or more substituents independently selected from the group consisting of R$^{13}$, OR$^{13}$, NH$_2$, NHR$^{13}$, N(R$^{13}$)$_2$, C(O)H, C(O)OH, OH, CN, NO$_2$, F, Cl, Br and I; wherein each R$^7$ aryl, cycloalkyl, cycloalkenyl, heteroaryl, heterocycloalkyl, and heterocycloalkenyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, (O), OH, CN, NO$_2$, F, Cl, Br and I. In another embodiment of Formula (IIa), R$^7$, at each occurrence, is independently selected from the group consisting of C$_1$-C$_6$ alkyl, aryl, heteroaryl, heterocycloalkyl, heterocycloalkenyl, and cycloalkyl; wherein each R$^7$C$_1$-C$_6$ alkyl is optionally substituted with one or more substituents independently selected from the group consisting of $R^{13}$, $OR^{13}$, $N(R^{13})_2$, and OH; wherein each $R^7$ aryl, heteroaryl, heterocycloalkyl, heterocycloalkenyl, and cycloalkyl is optionally substituted with one or more substituents independently selected from the group consisting of $R^{11}$, $OR^{11}$, $SO_2R^{11}$, $C(O)R^{11}$, $C(O)$ $R^{11}$, $NH_2$, $N(R^{11})_2$, $NHC(O)R^{11}$, $NHS(O)_2R^{11}$, $C(O)NH_2$, $C(O)OH$, (O), OH, CN, F, and Cl.

In one embodiment of Formula (IIa), $R^8$, at each occurrence, is independently selected from the group consisting of $C_1$-$C_6$ alkyl, $C_2$-$C_6$alkenyl, $C_2$-$C_6$alkynyl, and heterocycloalkyl; wherein each $R^8 C_1$-$C_6$ alkyl, $C_2$-$C_6$alkenyl, and $C_2$-$C_6$alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)$ $NR^{8A}SO_2R^{8A}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)$ OH, OH, CN, $NO_2$, F, Cl, Br and I; and $R^{8A}$, at each occurrence, is independently selected from the group consisting of $C_1$-$C_6$ alkyl, $C_2$-$C_6$alkenyl, and $C_2$-$C_6$alkynyl. In another embodiment of Formula (IIa), $R^8$, at each occurrence, is independently selected from the group consisting of $C_1$-$C_6$ alkyl, $C_2$-$C_6$alkenyl, and heterocycloalkyl; wherein each $R^8 C_1$-$C_6$ alkyl and $C_2$-$C_6$alkenyl is optionally substituted with one or more substituents independently selected from the group consisting of aryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)OH$, OH, CN, and F; wherein each $R^8$ heterocycloalkyl is optionally substituted with one or more OH; and $R^{8A}$, at each occurrence, is independently $C_1$-$C_6$ alkyl.

In one embodiment of Formula (IIa), $R^9$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^9 C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)$ $OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)$ $OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)$ $NHR^{12}$, $C(O)N(R^{12})_2$, $C(O)NHOH$, $C(O)NHOR^{12}$, $C(O)$ $NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I. In another embodiment of Formula (IIa), $R^9$, at each occurrence, is independently selected from the group consisting of $C_1$-$C_6$alkyl, aryl, heteroaryl, heterocycloalkyl, cycloalkyl, and cycloalkenyl; wherein each $R^9$aryl, heteroaryl, heterocycloalkyl, cycloalkyl, and cycloalkenyl is optionally substituted with one or more substituents independently selected from the group consisting of $R^{12}$, $OR^{12}$, $SO_2R^{12}$, $NH_2$, $C(O)NH_2$, $SO_2NH_2$, $C(O)OH$, (O), OH, CN, F, and Cl.

In one embodiment of Formula (IIa), $R^{10}$, at each occurrence, is independently selected from the group consisting of $C_1$-$C_6$alkyl, $C_2$-$C_6$alkenyl, and $C_2$-$C_6$ alkynyl; wherein each $R^{10}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)$ OH, OH, CN, $NO_2$, F, Cl, Br and I. In another embodiment of Formula (IIa), $R^{10}$, at each occurrence, is $C_1$-$C_6$alkyl.

In one embodiment of Formula (IIa), $R^{11}$, at each occurrence, is independently selected from the group consisting of $C_1$-$C_6$alkyl, $C_2$-$C_6$alkenyl, $C_2$-$C_6$alkynyl, aryl, and heteroaryl; wherein each $R^{11}C_1$-$C_6$alkyl, $C_2$-$C_6$alkenyl, and $C_2$-$C_6$alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$alkyl, $C_1$-$C_6$ haloalkyl, $NH_2$, $C(O)H$, $C(O)OH$, OH, CN, $NO_2$, F, Cl, Br and I; and $R^{11A}$, at each occurrence, is independently selected from the group consisting of $C_1$-$C_6$alkyl, $C_2$-$C_6$alkenyl, and $C_2$-$C_6$ alkynyl. In another embodiment of Formula (IIa), $R^{11}$, at each occurrence, is independently selected from the group consisting of $C_1$-$C_6$alkyl and aryl; wherein each $R^{11}C_1$-$C_6$alkyl is optionally substituted with one or more substituents independently selected from the group consisting of $OR^{11A}$, $N(R^{11A})_2$, $C(O)OH$, and OH; wherein each $R^{11}$ aryl is optionally substituted with one or more $C_1$-$C_6$alkyl; and $R^{11A}$, at each occurrence, is independently $C_1$-$C_6$alkyl.

In one embodiment of Formula (IIa), $R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{14}$, $N(R^{14})_2$, $C(O)H$, $C(O)OH$, OH, CN, $NO_2$, F, Cl, Br and I. In another embodiment of Formula (IIa), $R^{12}$, at each occurrence, is independently $C_1$-$C_6$alkyl; wherein each $R^{12}C_1$-$C_6$alkyl is optionally substituted with one or more $C(O)OH$.

In one embodiment of Formula (IIa), $R^{13}$, at each occurrence, is independently selected from the group consisting of $C_1$-$C_6$alkyl, $C_2$-$C_6$alkenyl, $C_2$-$C_6$ alkynyl, aryl, heteroaryl, cycloalkyl, cycloalkenyl, heterocycloalkyl, and heterocycloalkenyl; wherein each $R^{13}C_1$-$C_6$alkyl, $C_2$-$C_6$alkenyl, and $C_2$-$C_6$alkynyl is optionally substituted with one or more substituents independently selected from the group consisting of $R^{15}$, $OR^{15}$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, (O), OH, CN, $NO_2$, F, Cl, Br and I. In another embodiment of Formula (IIa), $R^{13}$, at each occurrence, is independently selected from the group consisting of $C_1$-$C_6$alkyl, aryl, heteroaryl, and heterocycloalkyl; wherein each $R^{13}C_1$-$C_6$alkyl is optionally substituted with one or more $OR^{15}$; wherein each $R^{13}$ aryl, heteroaryl, and heterocycloalkyl is optionally substituted with one or more $R^{16}$.

In one embodiment of Formula (IIa), $R^{15}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl; wherein each $R^{15}C_1$-$C_6$alkyl, $C_2$-$C_6$alkenyl, and $C_2$-$C_6$alkynyl is optionally substituted with one or more $OCH_3$. In another embodiment of Formula (IIa), $R^{15}$, at each occurrence, is independently $C_1$-$C_6$alkyl; wherein each $R^{15}C_1$-$C_6$alkyl is optionally substituted with one or more $OCH_3$.

In one embodiment of Formula (IIa), $R^{16}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl. In another embodiment of Formula (IIa), $R^{16}$, at each occurrence, is independently selected from the group consisting of $C_1$-$C_6$ haloalkyl and $C_1$-$C_6$alkyl.

In another embodiment of Formula (IIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR^5$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN;

$R^2$ is selected from the group consisting of hydrogen, $C_1$-$C_4$ alkyl, $NO_2$, CN, $C(O)NH_2$, $C(O)OR^{2A}$, Cl, and Br;

$R^{2A}$ is $C_1$-$C_6$alkyl;

$R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl;

$R^4$ is selected from the group consisting of $R^{4A}$, $OR^{4A}$, $C(O)NH_2$, CN, F, and Cl;

$R^{4A}$ is selected from the group consisting of hydrogen and $C_1$-$C_6$ alkyl;

$R^5$, at each occurrence, is independently selected from the group consisting of $C_1$-$C_6$ alkyl, aryl, heteroaryl, heterocycloalkyl, heterocycloalkenyl, cycloalkyl, and cycloalkenyl; wherein each $R^5C_1$-$C_6$ alkyl is optionally substituted with one or more substituents independently selected from the group consisting of $R^7$, $OR^7$, $SO_2R^7$, $C(O)R^7$, $CO(O)R^7$, $OC(O)R^7$, $NH_2$, $NHR^7$, $N(R^7)_2$, $NHC(O)R^7$, $NHS(O)_2R^7$, $NHC(O)OR^7$, $NHC(O)NHR^7$, $C(O)NH_2$, $C(O)NHR^7$, $C(O)N(R^7)_2$, $C(O)NHSO_2R^7$, $SO_2NH_2$, $SO_2NHR^7$, $SO_2N(R^7)_2$, $B(OH)_2$, $C(O)OH$, OH, CN, F, and Cl; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $SO_2R^8$, $C(O)R^8$, $CO(O)R^8$, $NH_2$, $NHR^8$, $NHC(O)R^8$, $NHS(O)_2R^8$, $C(O)NHR^8$, $C(O)N(R^8)_2$, $C(O)NHSO_2R^8$, $C(O)OH$, (O), OH, CN, F, and Cl;

$R^6$, at each occurrence, is independently selected from the group consisting of $C_1$-$C_6$alkyl, phenyl, heteroaryl, heterocycloalkyl, heterocycloalkenyl, cycloalkyl, and cycloalkenyl; wherein each $R^6C_1$-$C_6$alkyl is optionally substituted with one or more substituents independently selected from the group consisting of $R^9$, $NH_2$, $NHR^9$, $NHS(O)_2R^9$, CN, and F; wherein each $R^6$ phenyl, cycloalkyl, heteroaryl, heterocycloalkyl, and heterocycloalkenyl is optionally substituted with one or more substituents independently selected from the group consisting of $R^{10}$, $OR^{10}$, and F;

$R^7$, at each occurrence, is independently selected from the group consisting of $C_1$-$C_6$ alkyl, aryl, heteroaryl, heterocycloalkyl, heterocycloalkenyl, and cycloalkyl; wherein each $R^7C_1$-$C_6$ alkyl is optionally substituted with one or more substituents independently selected from the group consisting of $R^{13}$, $OR^{13}$, $N(R^{13})_2$, and OH; wherein each $R^7$aryl, heteroaryl, heterocycloalkyl, heterocycloalkenyl, and cycloalkyl is optionally substituted with one or more substituents independently selected from the group consisting of $R^{11}$, $OR^{11}$, $SO_2R^{11}$, $C(O)R^{11}$, $CO(O)R^{11}$, $NH_2$, $N(R^{11})_2$, $NHC(O)R^{11}$, $NHS(O)_2R^{11}$, $C(O)NH_2$, $C(O)OH$, (O), OH, CN, F, and Cl;

$R^8$, at each occurrence, is independently selected from the group consisting of $C_1$-$C_6$ alkyl, $C_2$-$C_6$alkenyl, and heterocycloalkyl; wherein each $R^8C_1$-$C_6$ alkyl and $C_2$-$C_6$alkenyl is optionally substituted with one or more substituents independently selected from the group consisting of aryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)OH$, OH, CN, and F; wherein each $R^8$ heterocycloalkyl is optionally substituted with one or more OH;

$R^{8A}$, at each occurrence, is independently $C_1$-$C_6$alkyl;

$R^9$, at each occurrence, is independently selected from the group consisting of $C_1$-$C_6$alkyl, aryl, heteroaryl, heterocycloalkyl, cycloalkyl, and cycloalkenyl; wherein each $R^9$aryl, heteroaryl, heterocycloalkyl, cycloalkyl, and cycloalkenyl is optionally substituted with one or more substituents independently selected from the group consisting of $R^{12}$, $OR^{12}$, $SO_2R^{12}$, $NH_2$, $C(O)NH_2$, $SO_2NH_2$, $C(O)OH$, (O), OH, CN, F, and Cl;

$R^{10}$, at each occurrence, is independently $C_1$-$C_6$alkyl;

$R^{11}$, at each occurrence, is independently selected from the group consisting of $C_1$-$C_6$alkyl, and aryl; wherein each $R^{11}C_1$-$C_6$alkyl is optionally substituted with one or more substituents independently selected from the group consisting of $OR^{11A}$, $N(R^{11A})_2$, $C(O)OH$, and OH; wherein each $R^{11}$ aryl is optionally substituted with one or more substituents independently selected from the group consisting of $C_1$-$C_6$alkyl;

$R^{11A}$, at each occurrence, is independently $C_1$-$C_6$alkyl;

$R^{12}$, at each occurrence, is independently $C_1$-$C_6$alkyl; wherein each $R^{12}C_1$-$C_6$alkyl is optionally substituted with one or more $C(O)OH$;

$R^{13}$, at each occurrence, is independently selected from the group consisting of $C_1$-$C_6$alkyl, aryl, heteroaryl, and heterocycloalkyl; wherein each $R^{13}C_1$-$C_6$alkyl is optionally substituted with one or more $OR^{15}$; wherein each $R^{13}$ aryl, heteroaryl, and heterocycloalkyl, and heterocycloalkenyl is optionally substituted with one or more $R^{16}$;

$R^{15}$, at each occurrence, is independently $C_1$-$C_6$alkyl; wherein each $R^{15}C_1$-$C_6$alkyl is optionally substituted with one or more $OCH_3$; and $R^{16}$, at each occurrence, is independently selected from the group consisting of $C_1$-$C_6$ haloalkyl, and $C_1$-$C_6$alkyl.

Still another embodiment pertains to compounds of Formula (IIa), selected from the group consisting of:

4-(5-fluoro-2-methoxyphenyl)-2-(piperidin-3-yl)-1H-pyrrolo[2,3-b]pyridine;

4-(4-fluoro-2-methoxyphenyl)-2-(piperidin-3-yl)-1H-pyrrolo[2,3-b]pyridine;

4-(5-fluoro-2-methoxyphenyl)-2-[(3S)-piperidin-3-yl]-1H-pyrrolo[2,3-b]pyridine;

4-(5-fluoro-2-methoxyphenyl)-2-[(3R)-piperidin-3-yl]-1H-pyrrolo[2,3-b]pyridine;

4-[5-(4,5-dihydro-1H-imidazol-2-yl)-2-methoxyphenyl]-2-(piperidin-3-yl)-1H-pyrrolo[2,3-b]pyridine;

4-(5-cyclopropyl-2-methoxyphenyl)-2-(piperidin-3-yl)-1H-pyrrolo[2,3-b]pyridine;

4-(4-fluoro-2-methoxyphenyl)-2-(1-methylpiperidin-3-yl)-1H-pyrrolo[2,3-b]pyridine;

4-(5-fluoro-2-methoxyphenyl)-2-(1-methylpiperidin-3-yl)-1H-pyrrolo[2,3-b]pyridine;

1-{3-[4-(5-fluoro-2-methoxyphenyl)-1H-pyrrolo[2,3-b]pyridin-2-yl]piperidin-1-yl}ethanone;
4-(5-fluoro-2-methoxyphenyl)-2-(piperidin-4-yl)-1H-pyrrolo[2,3-b]pyridine;
4-(4-fluoro-2-methoxyphenyl)-2-(piperidin-4-yl)-1H-pyrrolo[2,3-b]pyridine;
4-(4-chloro-2-methoxyphenyl)-2-(piperidin-4-yl)-1H-pyrrolo[2,3-b]pyridine;
4-(4,5-difluoro-2-methoxyphenyl)-2-(piperidin-4-yl)-1H-pyrrolo[2,3-b]pyridine;
4-(5-chloro-2-methoxyphenyl)-2-(piperidin-4-yl)-1H-pyrrolo[2,3-b]pyridine;
4-(2-methoxy-5-methylphenyl)-2-(piperidin-4-yl)-1H-pyrrolo[2,3-b]pyridine;
4-(3-chloro-2-methoxyphenyl)-2-(piperidin-4-yl)-1H-pyrrolo[2,3-b]pyridine;
4-(2-methoxyphenyl)-2-(piperidin-4-yl)-1H-pyrrolo[2,3-b]pyridine;
4-(5-fluoro-2-methoxyphenyl)-2-(1-methylpiperidin-4-yl)-1H-pyrrolo[2,3-b]pyridine;
4-(4-fluoro-2-methoxyphenyl)-2-(1-methylpiperidin-4-yl)-1H-pyrrolo[2,3-b]pyridine;
4-(2-methoxy-5-methylphenyl)-2-(1-methylpiperidin-4-yl)-1H-pyrrolo[2,3-b]pyridine;
N-{4-chloro-3-[2-(piperidin-4-yl)-1H-pyrrolo[2,3-b]pyridin-4-yl]phenyl}benzenesulfonamide;
N-benzyl-4-fluoro-3-[2-(piperidin-4-yl)-1H-pyrrolo[2,3-b]pyridin-4-yl]aniline;
N-benzyl-4-chloro-3-[2-(piperidin-4-yl)-1H-pyrrolo[2,3-b]pyridin-4-yl]aniline;
4-(5-fluoro-2-methoxyphenyl)-2-(pyrrolidin-3-yl)-1H-pyrrolo[2,3-b]pyridine;
4-(4-fluoro-2-methoxyphenyl)-2-(pyrrolidin-3-yl)-1H-pyrrolo[2,3-b]pyridine;
4-(5-fluoro-2-methoxyphenyl)-2-[(3S)-pyrrolidin-3-yl]-1H-pyrrolo[2,3-b]pyridine;
4-(5-fluoro-2-methoxyphenyl)-2-[(3R)-pyrrolidin-3-yl]-1H-pyrrolo[2,3-b]pyridine;
4-(5-fluoro-2-methoxyphenyl)-2-(1-methylpyrrolidin-3-yl)-1H-pyrrolo[2,3-b]pyridine;
4-(4-fluoro-2-methoxyphenyl)-2-(morpholin-2-yl)-1H-pyrrolo[2,3-b]pyridine;
4-(5-fluoro-2-methoxyphenyl)-2-(morpholin-2-yl)-1H-pyrrolo[2,3-b]pyridine;
4-(4-fluoro-2-methoxyphenyl)-2-(4-methylmorpholin-2-yl)-1H-pyrrolo[2,3-b]pyridine;
4-(5-fluoro-2-methoxyphenyl)-2-(4-methylmorpholin-2-yl)-1H-pyrrolo[2,3-b]pyridine;
2-(5,5-dimethylmorpholin-2-yl)-4-(5-fluoro-2-methoxyphenyl)-1H-pyrrolo[2,3-b]pyridine;
2-(5,5-dimethylmorpholin-2-yl)-4-(4-fluoro-2-methoxyphenyl)-1H-pyrrolo[2,3-b]pyridine;
4-(4-chloro-2-methoxyphenyl)-2-(5,5-dimethylmorpholin-2-yl)-1H-pyrrolo[2,3-b]pyridine;
trans-4-[4-(5-fluoro-2-methoxyphenyl)-1H-pyrrolo[2,3-b]pyridin-2-yl]cyclohexanamine;
3-[4-(5-fluoro-2-methoxyphenyl)-1H-pyrrolo[2,3-b]pyridin-2-yl]cyclohexanamine;
4-(5-fluoro-2-methoxyphenyl)-3-methyl-2-(piperidin-4-yl)-1H-pyrrolo[2,3-b]pyridine;
5-chloro-4-(3-fluorophenyl)-2-(piperidin-3-yl)-1H-pyrrolo[2,3-b]pyridine;
3-[5-chloro-4-(3-fluorophenyl)-1H-pyrrolo[2,3-b]pyridin-2-yl]cyclohexanamine;
4-(5-fluoro-2-methoxyphenyl)-2-(1,2,3,6-tetrahydropyridin-4-yl)-1H-pyrrolo[2,3-b]pyridine;

4-(5-fluoro-2-methoxyphenyl)-2-(pyrrolidin-2-yl)-1H-pyrrolo[2,3-b]pyridine;
2-cyclohexyl-4-(5-fluoro-2-methoxyphenyl)-1H-pyrrolo[2,3-b]pyridine;
1-{2-[4-(5-fluoro-2-methoxyphenyl)-1H-pyrrolo[2,3-b]pyridin-2-yl]pyrrolidin-1-yl}ethanone;
1-{4-[4-(5-fluoro-2-methoxyphenyl)-1H-pyrrolo[2,3-b]pyridin-2-yl]-3,6-dihydropyridin-1(2H)-yl}ethanone;
1-{4-[4-(5-fluoro-2-methoxyphenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-(1-methylpyrrolidin-2-yl)-1H-pyrrolo[2,3-b]pyridine;
1-{3-[4-(5-fluoro-2-methoxyphenyl)-1H-pyrrolo[2,3-b]pyridin-2-yl]pyrrolidin-1-yl}ethanone;
2-{3-[4-(5-fluoro-2-methoxyphenyl)-1H-pyrrolo[2,3-b]pyridin-2-yl]pyrrolidin-1-yl}ethanol;
4-(5-fluoro-2-methoxyphenyl)-2-[1-(tetrahydro-2H-pyran-4-yl)pyrrolidin-3-yl]-1H-pyrrolo[2,3-b]pyridine;
4-(5-fluoro-2-methoxyphenyl)-2-[1-(pyridin-2-ylmethyl)pyrrolidin-3-yl]-1H-pyrrolo[2,3-b]pyridine;
4-(5-fluoro-2-methoxyphenyl)-2-[1-(pyridin-3-ylmethyl)pyrrolidin-3-yl]-1H-pyrrolo[2,3-b]pyridine;
4-(5-fluoro-2-methoxyphenyl)-2-[1-(pyridin-4-ylmethyl)pyrrolidin-3-yl]-1H-pyrrolo[2,3-b]pyridine;
4-(5-fluoro-2-methoxyphenyl)-2-[1-(tetrahydro-2H-pyran-3-ylmethyl)pyrrolidin-3-yl]-1H-pyrrolo[2,3-b]pyridine;
tert-butyl (2-{3-[4-(5-fluoro-2-methoxyphenyl)-1H-pyrrolo[2,3-b]pyridin-2-yl]pyrrolidin-1-yl}ethyl)carbamate;
tert-butyl 3-[4-(5-fluoro-2-methoxyphenyl)-1H-pyrrolo[2,3-b]pyridin-2-yl]-1,3'-bipyrrolidine-1'-carboxylate;
4-(5-fluoro-2-methoxyphenyl)-2-[1-(tetrahydro-2H-pyran-4-ylmethyl)pyrrolidin-3-yl]-1H-pyrrolo[2,3-b]pyridine;
4-(5-fluoro-2-methoxyphenyl)-2-{1-[2-(morpholin-4-yl)ethyl]pyrrolidin-3-yl}-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine;
methyl 4-({trans-4-[4-(5-fluoro-2-methoxyphenyl)-1H-pyrrolo[2,3-b]pyridin-2-yl]cyclohexyl}amino)butanoate;
ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate;
trans-4-[4-(5-fluoro-2-methoxyphenyl)-1H-pyrrolo[2,3-b]pyridin-2-yl]-N-[2-(morpholin-4-yl)ethyl]cyclohexanamine;
3-({trans-4-[4-(5-fluoro-2-methoxyphenyl)-1H-pyrrolo[2,3-b]pyridin-2-yl]cyclohexyl}amino)propane-1,2-diol;
2-{3-[4-(5-fluoro-2-methoxyphenyl)-1H-pyrrolo[2,3-b]pyridin-2-yl]pyrrolidin-1-yl}ethanamine;
3-[4-(5-fluoro-2-methoxyphenyl)-1H-pyrrolo[2,3-b]pyridin-2-yl]-1,3'-bipyrrolidine;
4-[4-(5-fluoro-2-methoxyphenyl)-1H-pyrrolo[2,3-b]pyridin-2-yl]piperidin-4-ol;
benzyl (3-{3-[4-(5-fluoro-2-methoxyphenyl)-1H-pyrrolo[2,3-b]pyridin-2-yl]piperidin-1-yl}propyl)carbamate;
2-{3-[4-(5-fluoro-2-methoxyphenyl)-1H-pyrrolo[2,3-b]pyridin-2-yl]piperidin-1-yl}ethanol;
3-{3-[4-(5-fluoro-2-methoxyphenyl)-1H-pyrrolo[2,3-b]pyridin-2-yl]piperidin-1-yl}propan-1-amine;
4-(5-fluoro-2-methoxyphenyl)-2-[1-(2-methoxyethyl)piperidin-3-yl]-1H-pyrrolo[2,3-b]pyridine;
4-({trans-4-[4-(5-fluoro-2-methoxyphenyl)-1H-pyrrolo[2,3-b]pyridin-2-yl]cyclohexyl}amino)butanoic acid;
1-{4-[4-(5-fluoro-2-methoxyphenyl)-1H-pyrrolo[2,3-b]pyridin-2-yl]piperidin-1-yl}ethanone;
1-{4-[4-(5-fluoro-2-methoxyphenyl)-1H-pyrrolo[2,3-b]pyridin-2-yl]piperidin-1-yl}-2-hydroxyethanone;

3-methoxy-4-[2-(piperidin-3-yl)-1H-pyrrolo[2,3-b]pyridin-4-yl]benzonitrile;
2-[({trans-4-[4-(5-fluoro-2-methoxyphenyl)-1H-pyrrolo[2,3-b]pyridin-2-yl]cyclohexyl}amino)methyl]cyclopropanecarboxylic acid;
2-(azetidin-3-yl)-4-(5-fluoro-2-methoxyphenyl)-1H-pyrrolo[2,3-b]pyridine;
1-{4-[4-(5-fluoro-2-methoxyphenyl)-1H-pyrrolo[2,3-b]pyridin-2-yl]piperidin-1-yl}-2-(4-hydroxypiperidin-1-yl)ethanone;
4-(5-fluoro-2-methoxyphenyl)-2-[1-(methylsulfonyl)piperidin-4-yl]-1H-pyrrolo[2,3-b]pyridine;
3-{4-[4-(5-fluoro-2-methoxyphenyl)-1H-pyrrolo[2,3-b]pyridin-2-yl]piperidin-1-yl}propane-1,2-diol;
4-[4-(5-fluoro-2-methoxyphenyl)-1H-pyrrolo[2,3-b]pyridin-2-yl]tetrahydro-2H-pyran-4-ol;
4-(5-fluoro-2-methoxyphenyl)-2-[1-(pyridin-4-ylmethyl)azetidin-3-yl]-1H-pyrrolo[2,3-b]pyridine;
1-{3-[4-(5-fluoro-2-methoxyphenyl)-1H-pyrrolo[2,3-b]pyridin-2-yl]azetidin-1-yl}ethanone;
2-{3-[4-(5-fluoro-2-methoxyphenyl)-1H-pyrrolo[2,3-b]pyridin-2-yl]azetidin-1-yl}ethanamine;
4-(5-fluoro-2-methoxyphenyl)-2-[1-(tetrahydro-2H-pyran-4-ylmethyl)azetidin-3-yl]-1H-pyrrolo[2,3-b]pyridine;
4-(5-fluoro-2-methoxyphenyl)-2-{1-[2-(morpholin-4-yl)ethyl]azetidin-3-yl}-1H-pyrrolo[2,3-b]pyridine;
2-{3-[4-(5-fluoro-2-methoxyphenyl)-1H-pyrrolo[2,3-b]pyridin-2-yl]azetidin-1-yl}ethanol;
4-fluoro-3-[2-(1-methylpiperidin-4-yl)-1H-pyrrolo[2,3-b]pyridin-4-yl]-N-(tetrahydro-2H-pyran-4-ylmethyl)aniline;
1-{4-[4-(5-fluoro-2-methoxyphenyl)-1H-pyrrolo[2,3-b]pyridin-2-yl]piperidin-1-yl}-2-(piperidin-1-yl)ethanone;
1-{4-[4-(5-fluoro-2-methoxyphenyl)-1H-pyrrolo[2,3-b]pyridin-2-yl]piperidin-1-yl}-2-(morpholin-4-yl)ethanone;
1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone;
1-{4-[4-(5-fluoro-2-methoxyphenyl)-1H-pyrrolo[2,3-b]pyridin-2-yl]piperidin-1-yl}-2-[(2-hydroxyethyl)amino]ethanone;
4-(5-fluoro-2-methoxyphenyl)-2-(1-methylazetidin-3-yl)-1H-pyrrolo[2,3-b]pyridine;
4-(5-fluoro-2-methoxyphenyl)-2-[1-(methylsulfonyl)azetidin-3-yl]-1H-pyrrolo[2,3-b]pyridine;
3-{4-[4-(5-fluoro-2-methoxyphenyl)-1H-pyrrolo[2,3-b]pyridin-2-yl]-3,6-dihydropyridin-1(2H)-yl}propane-1,2-diol;
4-fluoro-3-[2-(piperidin-4-yl)-1H-pyrrolo[2,3-b]pyridin-4-yl]aniline;
4-fluoro-3-[2-(1-methylpiperidin-4-yl)-1H-pyrrolo[2,3-b]pyridin-4-yl]-N-(pyridin-4-ylmethyl)aniline;
4-fluoro-3-[2-(1-methylpiperidin-4-yl)-1H-pyrrolo[2,3-b]pyridin-4-yl]-N-[4-(methylsulfonyl)benzyl]aniline;
4-[({4-fluoro-3-[2-(1-methylpiperidin-4-yl)-1H-pyrrolo[2,3-b]pyridin-4-yl]phenyl}amino)methyl]benzamide;
2-(azepan-3-yl)-4-(5-fluoro-2-methoxyphenyl)-1H-pyrrolo[2,3-b]pyridine;
N-benzyl-3-[5-chloro-2-(piperidin-4-yl)-1H-pyrrolo[2,3-b]pyridin-4-yl]-4-fluoroaniline;
N-benzyl-4-chloro-3-[2-(piperidin-3-yl)-1H-pyrrolo[2,3-b]pyridin-4-yl]aniline;
4-(4,5-difluoro-2-methoxyphenyl)-2-(piperidin-3-yl)-1H-pyrrolo[2,3-b]pyridine;
N-benzyl-4-fluoro-3-[2-(piperidin-3-yl)-1H-pyrrolo[2,3-b]pyridin-4-yl]aniline;
4-fluoro-N-(3-fluorobenzyl)-3-[2-(piperidin-3-yl)-1H-pyrrolo[2,3-b]pyridin-4-yl]aniline;
4-[4-(5-fluoro-2-methoxyphenyl)-1H-pyrrolo[2,3-b]pyridin-2-yl]-N-methyl-3,6-dihydropyridine-1(2H)-carboxamide;
4-[4-(5-fluoro-2-methoxyphenyl)-1H-pyrrolo[2,3-b]pyridin-2-yl]-3,6-dihydropyridine-1(2H)-sulfonamide;
N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide;
tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-[4-(5-fluoro-2-methoxyphenyl)-1H-pyrrolo[2,3-b]pyridin-2-yl]cyclohex-3-ene-1-carboxylic acid;
4-(2,3-difluorophenyl)-2-[1-(methylsulfonyl)-1,2,3,6-tetrahydropyridin-4-yl]-1H-pyrrolo[2,3-b]pyridine;
3-{4-[4-(5-fluoro-2-methoxyphenyl)-1H-pyrrolo[2,3-b]pyridin-2-yl]-3,6-dihydropyridin-1(2H)-yl}-3-oxopropanenitrile;
4-[4-(2,3-difluorophenyl)-1H-pyrrolo[2,3-b]pyridin-2-yl]-N-methyl-3,6-dihydropyridine-1(2H)-carboxamide;
4-(5-fluoro-2-methoxyphenyl)-2-[8-(methylsulfonyl)-8-azabicyclo[3.2.1]oct-2-en-3-yl]-1H-pyrrolo[2,3-b]pyridine;
2-{4-[4-(5-fluoro-2-methoxyphenyl)-1H-pyrrolo[2,3-b]pyridin-2-yl]-3,6-dihydropyridin-1(2H)-yl}-N,N-dimethylacetamide;
4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide;
{4-[4-(5-fluoro-2-methoxyphenyl)-1H-pyrrolo[2,3-b]pyridin-2-yl]-3,6-dihydropyridin-1(2H)-yl}acetic acid;
2-{4-[4-(5-fluoro-2-methoxyphenyl)-1H-pyrrolo[2,3-b]pyridin-2-yl]-3,6-dihydropyridin-1(2H)-yl}acetamide;
ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-[5-chloro-4-(5-fluoro-2-methoxyphenyl)-1H-pyrrolo[2,3-b]pyridin-2-yl]-N-methyl-3,6-dihydropyridine-1(2H)-carboxamide;
4-(5-fluoro-2-methoxyphenyl)-2-[1-(S-methylsulfonimidoyl)-1,2,3,6-tetrahydropyridin-4-yl]-1H-pyrrolo[2,3-b]pyridine;
2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;
4-[4-(4,5-difluoro-2-methoxyphenyl)-1H-pyrrolo[2,3-b]pyridin-2-yl]-N-methyl-3,6-dihydropyridine-1(2H)-carboxamide;
2-{3-[4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;
2-{4-[4-(2,3-difluorophenyl)-1H-pyrrolo[2,3-b]pyridin-2-yl]-3,6-dihydropyridin-1(2H)-yl}-N,N-dimethylacetamide;
2-{4-[4-(5-fluoro-2-methoxyphenyl)-1H-pyrrolo[2,3-b]pyridin-2-yl]piperidin-1-yl}-N,N-dimethylacetamide;
2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide;
ethyl ({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate;
2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{4-[4-(5-fluoro-2-methoxyphenyl)-1H-pyrrolo[2,3-b]
pyridin-2-yl]-3,6-dihydropyridin-1(2H)-yl}-1-[(2S)-2-
(hydroxymethyl)pyrrolidin-1-yl]ethanone;
{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone;
N-{4-[4-(5-fluoro-2-methoxyphenyl)-1H-pyrrolo[2,3-b]
pyridin-2-yl]cyclohex-3-en-1-yl}-D-valine;
1-{4-[4-(5-fluoro-2-methoxyphenyl)-1H-pyrrolo[2,3-b]
pyridin-2-yl]cyclohex-3-en-1-yl}-L-proline;
N-cyano-4-[4-(5-fluoro-2-methoxyphenyl)-1H-pyrrolo[2,3-b]pyridin-2-yl]-3,6-dihydropyridine-1(2H)-carboxamide;
1-({4-[4-(5-fluoro-2-methoxyphenyl)-1H-pyrrolo[2,3-b]
pyridin-2-yl]-3,6-dihydropyridin-1(2H)-yl}acetyl)-L-prolinamide;
2-{4-[4-(5-fluoro-2-methoxyphenyl)-1H-pyrrolo[2,3-b]
pyridin-2-yl]piperidin-1-yl}acetamide;
2-{4-[4-(5-fluoro-2-methoxyphenyl)-1H-pyrrolo[2,3-b]
pyridin-2-yl]piperidin-1-yl}-N-methylacetamide;
2-{4-[4-(5-fluoro-2-methoxyphenyl)-1H-pyrrolo[2,3-b]
pyridin-2-yl]piperidin-1-yl}-1-[(2S)-2-(hydroxymethyl)
pyrrolidin-1-yl]ethanone;
4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile;
4-[3-cyano-4-(5-fluoro-2-methoxyphenyl)-1H-pyrrolo[2,3-b]pyridin-2-yl]-N-methyl-3,6-dihydropyridine-1(2H)-carboxamide;
ethyl ({4-[4-(5-fluoro-2-methoxyphenyl)-1H-pyrrolo[2,3-b]
pyridin-2-yl]cyclohex-3-en-1-yl}sulfamoyl)carbamate;
2-{4-[4-(5-fluoro-2-methoxyphenyl)-1H-pyrrolo[2,3-b]
pyridin-2-yl]piperidin-1-yl}-N-(2-hydroxyethyl)-N-methylacetamide;
2-{4-[4-(5-fluoro-2-methoxyphenyl)-1H-pyrrolo[2,3-b]
pyridin-2-yl]piperidin-1-yl}-N-(3-hydroxycyclobutyl)acetamide;
2-{4-[4-(5-fluoro-2-methoxyphenyl)-1H-pyrrolo[2,3-b]
pyridin-2-yl]piperidin-1-yl}-1-(3-hydroxyazetidin-1-yl)
ethanone;
N-{4-[4-(5-fluoro-2-methoxyphenyl)-1H-pyrrolo[2,3-b]
pyridin-2-yl]cyclohex-3-en-1-yl}-3-methyl-L-valine;
2-{4-[5-fluoro-4-(5-fluoro-2-methoxyphenyl)-1H-pyrrolo
[2,3-b]pyridin-2-yl]piperidin-1-yl}-N,N-dimethylacetamide;
2-{4-[3-cyano-4-(5-fluoro-2-methoxyphenyl)-1H-pyrrolo
[2,3-b]pyridin-2-yl]-3,6-dihydropyridin-1(2H)-yl}-N,N-dimethylacetamide;
2-{4-[4-(2-methoxyphenyl)-1H-pyrrolo[2,3-b]pyridin-2-yl]
piperidin-1-yl}-N,N-dimethylacetamide;
4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;
2-{4-[5-fluoro-4-(5-fluoro-2-methoxyphenyl)-1H-pyrrolo
[2,3-b]pyridin-2-yl]piperidin-1-yl}-1-(3-hydroxyazetidin-1-yl)ethanone;
2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
4-(5-fluoro-2-methoxyphenyl)-2-((3aS,6aR)-2-(methylsulfonyl)-1,2,3,3a,4,6a-hexahydrocyclopenta[c]pyrrol-5-yl)-1H-pyrrolo[2,3-b]pyridine;
2-{4-[3-cyano-5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;
4-(5-fluoro-2-methoxyphenyl)-2-((3aR,6aS)-2-(methylsulfonyl)-1,2,3,3a,4,6a-hexahydrocyclopenta[c]pyrrol-5-yl)-1H-pyrrolo[2,3-b]pyridine;
5-fluoro-4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile;
4-[3-cyano-5-fluoro-4-(5-fluoro-2-methoxyphenyl)-1H-pyrrolo[2,3-b]pyridin-2-yl]-N-methyl-3,6-dihydropyridine-1(2H)-carboxamide;
5-fluoro-4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile;
5-fluoro-4-(5-fluoro-2-methoxyphenyl)-2-(1-{2-[(2R)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;
2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-{4-[4-(5-fluoro-2-methoxyphenyl)-1H-pyrrolo[2,3-b]
pyridin-2-yl]-2,2-dimethyl-3,6-dihydropyridin-1(2H)-yl}-N,N-dimethylacetamide;
4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine;
2-{4-[5-cyano-4-(5-fluoro-2-methoxyphenyl)-1H-pyrrolo
[2,3-b]pyridin-2-yl]piperidin-1-yl}-N,N-dimethylacetamide;
2-{4-[4-(5-fluoro-2-methoxyphenyl)-1H-pyrrolo[2,3-b]
pyridin-2-yl]piperidin-1-yl}-N-(3-hydroxycyclobutyl)-N-methylacetamide;
4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
4-[5-fluoro-4-(5-fluoro-2-methoxyphenyl)-1H-pyrrolo[2,3-b]pyridin-2-yl]cyclohex-3-ene-1-carboxylic acid;
1-{5-[4-(5-fluoro-2-methoxyphenyl)-1H-pyrrolo[2,3-b]
pyridin-2-yl]-3,3a,4,6a-tetrahydrocyclopenta[c]pyrrol-2
(1H)-yl}-2-hydroxyethanone;
3-{5-[4-(5-fluoro-2-methoxyphenyl)-1H-pyrrolo[2,3-b]
pyridin-2-yl]-3,3a,4,6a-tetrahydrocyclopenta[c]pyrrol-2
(1H)-yl}-3-oxopropanenitrile;
5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile;
(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;

5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-methyl-2-oxoethanesulfonamide;
4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;
2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone;
2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone;
(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone;
{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone;
2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;
2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;
4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile;
2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;
2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;
2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide; and pharmaceutically acceptable salts thereof.

N-benzyl-4-fluoro-3-[2-(1-methylpiperidin-4-yl)-1H-pyrrolo[2,3-b]pyridin-4-yl]aniline;
4-[({4-fluoro-3-[2-(1-methylpiperidin-4-yl)-1H-pyrrolo[2,3-b]pyridin-4-yl]phenyl}amino)methyl]phenol;
4-fluoro-3-[2-(1-methylpiperidin-4-yl)-1H-pyrrolo[2,3-b]pyridin-4-yl]-N-(1H-1,2,4-triazol-5-ylmethyl)aniline;
4-fluoro-3-[2-(1-methylpiperidin-4-yl)-1H-pyrrolo[2,3-b]pyridin-4-yl]-N-(pyridin-2-ylmethyl)aniline;
N-[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;
N,N-bis[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;
N,N-bis(cyclopropylmethyl)-4-fluoro-3-[2-(1-methylpiperidin-4-yl)-1H-pyrrolo[2,3-b]pyridin-4-yl]aniline;
4-fluoro-3-[2-(1-methylpiperidin-4-yl)-1H-pyrrolo[2,3-b]pyridin-4-yl]-N-[3-(methylsulfonyl)benzyl]aniline;
2-[1-(cyclopropylsulfonyl)-1,2,3,6-tetrahydropyridin-4-yl]-4-(5-fluoro-2-methoxyphenyl)-1H-pyrrolo[2,3-b]pyridine;
4-[({4-fluoro-3-[2-(1-methylpiperidin-4-yl)-1H-pyrrolo[2,3-b]pyridin-4-yl]phenyl}amino)methyl]benzenesulfonamide;
3-[({4-fluoro-3-[2-(1-methylpiperidin-4-yl)-1H-pyrrolo[2,3-b]pyridin-4-yl]phenyl}amino)methyl]phenol;
N-(3-chlorobenzyl)-4-fluoro-3-[2-(1-methylpiperidin-4-yl)-1H-pyrrolo[2,3-b]pyridin-4-yl]aniline;
4-fluoro-N-(4-fluorobenzyl)-3-[2-(1-methylpiperidin-4-yl)-1H-pyrrolo[2,3-b]pyridin-4-yl]aniline;
4-fluoro-N-(2-fluorobenzyl)-3-[2-(1-methylpiperidin-4-yl)-1H-pyrrolo[2,3-b]pyridin-4-yl]aniline;
4-fluoro-N-(3-methoxybenzyl)-3-[2-(1-methylpiperidin-4-yl)-1H-pyrrolo[2,3-b]pyridin-4-yl]aniline;
{4-[({4-fluoro-3-[2-(1-methylpiperidin-4-yl)-1H-pyrrolo[2,3-b]pyridin-4-yl]phenyl}amino)methyl]phenoxy}acetic acid;
N-[(1,1-dioxidotetrahydro-2H-thiopyran-4-yl)methyl]-4-fluoro-3-[2-(1-methylpiperidin-4-yl)-1H-pyrrolo[2,3-b]pyridin-4-yl]aniline;
4-[4-(5-fluoro-2-methoxyphenyl)-1H-pyrrolo[2,3-b]pyridin-2-yl]tetrahydro-2H-thiopyran-4-ol 1,1-dioxide;
2-(1,1-dioxido-3,6-dihydro-2H-thiopyran-4-yl)-4-(5-fluoro-2-methoxyphenyl)-1H-pyrrolo[2,3-b]pyridine;
3-[4-(5-fluoro-2-methoxyphenyl)-1H-pyrrolo[2,3-b]pyridin-2-yl]pyrrolidin-3-ol;
2-(2,5-dihydro-1H-pyrrol-3-yl)-4-(5-fluoro-2-methoxyphenyl)-1H-pyrrolo[2,3-b]pyridine;
4-fluoro-N-(3-fluorobenzyl)-3-[2-(1-methylpiperidin-4-yl)-1H-pyrrolo[2,3-b]pyridin-4-yl]aniline;
N-(2,4-difluorobenzyl)-4-fluoro-3-[2-(1-methylpiperidin-4-yl)-1H-pyrrolo[2,3-b]pyridin-4-yl]aniline;
N-(2,6-difluorobenzyl)-4-fluoro-3-[2-(1-methylpiperidin-4-yl)-1H-pyrrolo[2,3-b]pyridin-4-yl]aniline;
2-{1-[(chloromethyl)sulfonyl]-1,2,3,6-tetrahydropyridin-4-yl}-4-(5-fluoro-2-methoxyphenyl)-1H-pyrrolo[2,3-b]pyridine;
4-(5-fluoro-2-methoxyphenyl)-2-[1-(propan-2-ylsulfonyl)-1,2,3,6-tetrahydropyridin-4-yl]-1H-pyrrolo[2,3-b]pyridine;
4-(5-fluoro-2-methoxyphenyl)-2-[1-(propylsulfonyl)-1,2,3,6-tetrahydropyridin-4-yl]-1H-pyrrolo[2,3-b]pyridine;
2-{1-[(1,1-dioxidotetrahydrothiophen-3-yl)sulfonyl]-1,2,3,6-tetrahydropyridin-4-yl}-4-(5-fluoro-2-methoxyphenyl)-1H-pyrrolo[2,3-b]pyridine;
N-(2,5-difluorobenzyl)-4-fluoro-3-[2-(1-methylpiperidin-4-yl)-1H-pyrrolo[2,3-b]pyridin-4-yl]aniline;

4-(5-fluoro-2-methoxyphenyl)-2-{1-[(2,2,2-trifluoroethyl)
sulfonyl]-1,2,3,6-tetrahydropyridin-4-yl}-1H-pyrrolo[2,
3-b]pyridine;
N-(2-chlorobenzyl)-4-fluoro-3-[2-(1-methylpiperidin-4-yl)-
1H-pyrrolo[2,3-b]pyridin-4-yl]aniline;
3-[({4-fluoro-3-[2-(1-methylpiperidin-4-yl)-1H-pyrrolo[2,
3-b]pyridin-4-yl]phenyl}amino)methyl]benzoic acid;
4-[({4-fluoro-3-[2-(1-methylpiperidin-4-yl)-1H-pyrrolo[2,
3-b]pyridin-4-yl]phenyl}amino)methyl]benzonitrile;
2-[({4-fluoro-3-[2-(1-methylpiperidin-4-yl)-1H-pyrrolo[2,
3-b]pyridin-4-yl]phenyl}amino)methyl]benzonitrile;
3-[({4-fluoro-3-[2-(1-methylpiperidin-4-yl)-1H-pyrrolo[2,
3-b]pyridin-4-yl]phenyl}amino)methyl]benzonitrile;
trans-4-[4-(5-fluoro-2-methoxyphenyl)-1H-pyrrolo[2,3-b]
pyridin-2-yl]-N-{[1-(methoxymethyl)-1H-1,2,3-triazol-
4-yl]methyl}cyclohexanamine;
trans-4-[4-(5-fluoro-2-methoxyphenyl)-1H-pyrrolo[2,3-b]
pyridin-2-yl]-N-{[1-(methoxymethyl)-1H-1,2,3-triazol-
5-yl]methyl}cyclohexanamine;
2,4-difluoro-N-[(4-methyltetrahydro-2H-pyran-4-yl)
methyl]-5-[2-(piperidin-4-yl)-1H-pyrrolo[2,3-b]pyridin-
4-yl]aniline;
N-benzyl-2,4-difluoro-5-[2-(piperidin-4-yl)-1H-pyrrolo[2,
3-b]pyridin-4-yl]aniline;
2,4-difluoro-5-[2-(piperidin-4-yl)-1H-pyrrolo[2,3-b]pyri-
din-4-yl]-N-(tetrahydro-2H-pyran-4-ylmethyl)aniline;
2,4-difluoro-N-(3-fluorobenzyl)-5-[2-(piperidin-4-yl)-1H-
pyrrolo[2,3-b]pyridin-4-yl]aniline;
4-(5-fluoro-2-methoxyphenyl)-2-[1-(thiophen-2-ylsulfo-
nyl)-1,2,3,6-tetrahydropyridin-4-yl]-1H-pyrrolo[2,3-b]
pyridine;
N-[2-chloro-4-({4-[4-(5-fluoro-2-methoxyphenyl)-1H-pyr-
rolo[2,3-b]pyridin-2-yl]-3,6-dihydropyridin-1(2H)-
yl}sulfonyl)phenyl]acetamide;
4-(5-fluoro-2-methoxyphenyl)-2-{1-[(2,4,5-trichlorophe-
nyl)sulfonyl]-1,2,3,6-tetrahydropyridin-4-yl}-1H-pyrrolo
[2,3-b]pyridine;
4-({4-[4-(5-fluoro-2-methoxyphenyl)-1H-pyrrolo[2,3-b]
pyridin-2-yl]-3,6-dihydropyridin-1(2H)-yl}sulfonyl)-2,1,
3-benzoxadiazole;
2-{1-[(3,5-dimethyl-1,2-oxazol-4-yl)sulfonyl]-1,2,3,6-tetra-
hydropyridin-4-yl}-4-(5-fluoro-2-methoxyphenyl)-1H-
pyrrolo[2,3-b]pyridine;
N-(3-chlorobenzyl)-4-fluoro-3-[2-(piperidin-4-yl)-1H-pyr-
rolo[2,3-b]pyridin-4-yl]aniline;
4-fluoro-N-(3-fluorobenzyl)-3-[2-(piperidin-4-yl)-1H-pyr-
rolo[2,3-b]pyridin-4-yl]aniline;
4-[({4-fluoro-3-[2-(piperidin-4-yl)-1H-pyrrolo[2,3-b]pyri-
din-4-yl]phenyl}amino)methyl]benzonitrile;
4-fluoro-N-[4-(methylsulfonyl)benzyl]-3-[2-(piperidin-4-
yl)-1H-pyrrolo[2,3-b]pyridin-4-yl]aniline;
4-fluoro-3-[2-(piperidin-4-yl)-1H-pyrrolo[2,3-b]pyridin-4-
yl]-N-(pyridin-4-ylmethyl)aniline;
3-[4-(5-fluoro-2-methoxyphenyl)-1H-pyrrolo[2,3-b]pyri-
din-2-yl]azetidin-3-ol;
4-[4-(5-fluoro-2-methoxyphenyl)-1H-pyrrolo[2,3-b]pyri-
din-2-yl]-1-(methylsulfonyl)piperidin-4-ol;
2-(1-benzylpiperidin-4-yl)-4-(5-fluoro-2-methoxyphenyl)-
1H-pyrrolo[2,3-b]pyridine;
4-(5-fluoro-2-methoxyphenyl)-2-(1-methyl-1,2,3,6-tetrahy-
dropyridin-4-yl)-1H-pyrrolo[2,3-b]pyridine;
4-fluoro-3-{2-[1-(methylsulfonyl)-1,2,3,6-tetrahydropyri-
din-4-yl]-1H-pyrrolo[2,3-b]pyridin-4-yl}aniline;
4-fluoro-3-[2-(1-methylpiperidin-4-yl)-1H-pyrrolo[2,3-b]
pyridin-4-yl]-N-(pyridin-3-ylmethyl)aniline;
4-fluoro-3-[2-(piperidin-4-yl)-1H-pyrrolo[2,3-b]pyridin-4-
yl]-N-(pyridin-3-ylmethyl)aniline;
N-(3,5-difluorobenzyl)-4-fluoro-3-[2-(piperidin-4-yl)-1H-
pyrrolo[2,3-b]pyridin-4-yl]aniline;
N-(2,4-difluorobenzyl)-4-fluoro-3-[2-(piperidin-4-yl)-1H-
pyrrolo[2,3-b]pyridin-4-yl]aniline;
N-(2,5-difluorobenzyl)-4-fluoro-3-[2-(piperidin-4-yl)-1H-
pyrrolo[2,3-b]pyridin-4-yl]aniline;
N-(2,6-difluorobenzyl)-4-fluoro-3-[2-(piperidin-4-yl)-1H-
pyrrolo[2,3-b]pyridin-4-yl]aniline;
N-(3,5-difluorobenzyl)-4-fluoro-3-[2-(1-methylpiperidin-4-
yl)-1H-pyrrolo[2,3-b]pyridin-4-yl]aniline;
4-fluoro-N-(4-fluorobenzyl)-3-[2-(piperidin-4-yl)-1H-pyr-
rolo[2,3-b]pyridin-4-yl]aniline;
4-[({4-fluoro-3-[2-(piperidin-4-yl)-1H-pyrrolo[2,3-b]pyri-
din-4-yl]phenyl}amino)methyl]benzenesulfonamide;
3-[({4-fluoro-3-[2-(piperidin-4-yl)-1H-pyrrolo[2,3-b]pyri-
din-4-yl]phenyl}amino)methyl]phenol;
4-fluoro-3-[2-(piperidin-4-yl)-1H-pyrrolo[2,3-b]pyridin-4-
yl]-N-(pyridin-2-ylmethyl)aniline;
4-fluoro-N-[3-(methylsulfonyl)benzyl]-3-[2-(piperidin-4-
yl)-1H-pyrrolo[2,3-b]pyridin-4-yl]aniline;
N-(4-fluoro-3-{2-[1-(methylsulfonyl)piperidin-4-yl]-1H-
pyrrolo[2,3-b]pyridin-4-yl}phenyl)methanesulfonamide;
N-benzyl-4-fluoro-3-{2-[1-(methylsulfonyl)piperidin-4-yl]-
1H-pyrrolo[2,3-b]pyridin-4-yl}aniline;
N-(3-chlorobenzyl)-4-fluoro-3-{2-[1-(methylsulfonyl)pip-
eridin-4-yl]-1H-pyrrolo[2,3-b]pyridin-4-yl}aniline;
4-fluoro-N-(3-fluorobenzyl)-3-{2-[1-(methylsulfonyl)pip-
eridin-4-yl]-1H-pyrrolo[2,3-b]pyridin-4-yl}aniline;
4-(5-fluoro-2-methoxyphenyl)-2-(2,2,6,6-tetramethyl-1,2,3,
6-tetrahydropyridin-4-yl)-1H-pyrrolo[2,3-b]pyridine;
4-fluoro-3-{2-[1-(methylsulfonyl)piperidin-4-yl]-1H-pyr-
rolo[2,3-b]pyridin-4-yl}-N-(pyridin-4-ylmethyl)aniline;
4-{[(4-fluoro-3-{2-[1-(methylsulfonyl)piperidin-4-yl]-1H-
pyrrolo[2,3-b]pyridin-4-yl}phenyl)amino]
methyl}benzonitrile;
4-{2-fluoro-5-[(3-fluorobenzyl)oxy]phenyl}-2-(1,2,3,6-tet-
rahydropyridin-4-yl)-1H-pyrrolo[2,3-b]pyridine;
2-({4-[4-(5-fluoro-2-methoxyphenyl)-1H-pyrrolo[2,3-b]
pyridin-2-yl]piperidin-1-yl}methyl)-1H-benzimidazole;
4-(5-fluoro-2-methoxyphenyl)-2-[1-(tetrahydrofuran-2-yl-
methyl)piperidin-4-yl]-1H-pyrrolo[2,3-b]pyridine;
2-[1-(5,6-dihydro-2H-pyran-3-ylmethyl)piperidin-4-yl]-4-
(5-fluoro-2-methoxyphenyl)-1H-pyrrolo[2,3-b]pyridine;
4-(5-fluoro-2-methoxyphenyl)-2-[1-(4-methoxybenzyl)pip-
eridin-4-yl]-1H-pyrrolo[2,3-b]pyridine;
4-(5-fluoro-2-methoxyphenyl)-2-{1-[2-(morpholin-4-yl)
ethyl]piperidin-4-yl}-1H-pyrrolo[2,3-b]pyridine;
4-({4-[4-(5-fluoro-2-methoxyphenyl)-1H-pyrrolo[2,3-b]
pyridin-2-yl]piperidin-1-yl}methyl)benzonitrile;
1-(2-{4-[4-(5-fluoro-2-methoxyphenyl)-1H-pyrrolo[2,3-b]
pyridin-2-yl]-3,6-dihydropyridin-1(2H)-yl}ethyl)-3-
methylurea;
4-(5-fluoro-2-methoxyphenyl)-2-[1-(2-methylpropyl)pip-
eridin-4-yl]-1H-pyrrolo[2,3-b]pyridine;
N-[4-({4-[4-(5-fluoro-2-methoxyphenyl)-1H-pyrrolo[2,3-b]
pyridin-2-yl]piperidin-1-yl}methyl)phenyl]acetamide;
4-(5-fluoro-2-methoxyphenyl)-2-[1-(pyridin-2-ylmethyl)pi-
peridin-4-yl]-1H-pyrrolo[2,3-b]pyridine;
4-({4-[4-(5-fluoro-2-methoxyphenyl)-1H-pyrrolo[2,3-b]
pyridin-2-yl]piperidin-1-yl}methyl)-N,N-dimethylani-
line;
2-{1-[(1-tert-butyl-1H-pyrazol-4-yl)methyl]piperidin-4-
yl}-4-(5-fluoro-2-methoxyphenyl)-1H-pyrrolo[2,3-b]
pyridine;
4-(5-fluoro-2-methoxyphenyl)-2-[1-(2-methoxyethyl)pip-
eridin-4-yl]-1H-pyrrolo[2,3-b]pyridine;

4-(5-fluoro-2-methoxyphenyl)-2-[1-(pyridin-4-ylmethyl)piperidin-4-yl]-1H-pyrrolo[2,3-b]pyridine;
N,N-diethyl-2-[4-({4-[4-(5-fluoro-2-methoxyphenyl)-1H-pyrrolo[2,3-b]pyridin-2-yl]piperidin-1-yl}methyl)phenoxy]ethanamine;
4-chloro-5-({4-[4-(5-fluoro-2-methoxyphenyl)-1H-pyrrolo[2,3-b]pyridin-2-yl]piperidin-1-yl}methyl)-1,3-thiazol-2-amine;
2-[1-(1,3-benzodioxol-5-ylmethyl)piperidin-4-yl]-4-(5-fluoro-2-methoxyphenyl)-1H-pyrrolo[2,3-b]pyridine;
3-{[(4-fluoro-3-{2-[1-(methylsulfonyl)piperidin-4-yl]-1H-pyrrolo[2,3-b]pyridin-4-yl}phenyl)amino]methyl}phenol;
4-fluoro-N-[3-(methylsulfonyl)benzyl]-3-{2-[1-(methylsulfonyl)piperidin-4-yl]-1H-pyrrolo[2,3-b]pyridin-4-yl}aniline;
4-{[(4-fluoro-3-{2-[1-(methylsulfonyl)piperidin-4-yl]-1H-pyrrolo[2,3-b]pyridin-4-yl}phenyl)amino]methyl}benzamide;
4-{[(4-fluoro-3-{2-[1-(methylsulfonyl)piperidin-4-yl]-1H-pyrrolo[2,3-b]pyridin-4-yl}phenyl)amino]methyl}phenol;
4-(5-fluoro-2-methoxyphenyl)-2-{1-[2-(morpholin-4-yl)ethyl]-1,2,3,6-tetrahydropyridin-4-yl}-1H-pyrrolo[2,3-b]pyridine;
2-{1-[(3-chlorobenzyl)sulfonyl]-1,2,3,6-tetrahydropyridin-4-yl}-4-(5-fluoro-2-methoxyphenyl)-1H-pyrrolo[2,3-b]pyridine;
2,4-difluoro-5-{2-[1-(methylsulfonyl)-1,2,3,6-tetrahydropyridin-4-yl]-1H-pyrrolo[2,3-b]pyridin-4-yl}-N-(tetrahydro-2H-pyran-4-ylmethyl)aniline;
2,4-difluoro-N-(tetrahydro-2H-pyran-4-ylmethyl)-5-[2-(1,2,3,6-tetrahydropyridin-4-yl)-1H-pyrrolo[2,3-b]pyridin-4-yl]aniline;
2,4-difluoro-N-(3-fluorobenzyl)-5-[2-(1,2,3,6-tetrahydropyridin-4-yl)-1H-pyrrolo[2,3-b]pyridin-4-yl]aniline;
N-(3,5-difluorobenzyl)-4-fluoro-3-{2-[1-(methylsulfonyl)-1,2,3,6-tetrahydropyridin-4-yl]-1H-pyrrolo[2,3-b]pyridin-4-yl}aniline;
4-[4-(5-fluoro-2-methoxyphenyl)-1H-pyrrolo[2,3-b]pyridin-2-yl]-N-(propan-2-yl)-3,6-dihydropyridine-1(2H)-carboxamide;
2-(1-ethyl-1,2,3,6-tetrahydropyridin-4-yl)-4-(5-fluoro-2-methoxyphenyl)-1H-pyrrolo[2,3-b]pyridine;
2-(1-benzyl-1,2,3,6-tetrahydropyridin-4-yl)-4-(5-fluoro-2-methoxyphenyl)-1H-pyrrolo[2,3-b]pyridine;
4-fluoro-3-{2-[1-(methylsulfonyl)piperidin-4-yl]-1H-pyrrolo[2,3-b]pyridin-4-yl}-N-(pyridin-3-ylmethyl)aniline;
N-(3,5-difluorobenzyl)-4-fluoro-3-{2-[1-(methylsulfonyl)piperidin-4-yl]-1H-pyrrolo[2,3-b]pyridin-4-yl}aniline;
N-(3,4-difluorobenzyl)-4-fluoro-3-{2-[1-(methylsulfonyl)piperidin-4-yl]-1H-pyrrolo[2,3-b]pyridin-4-yl}aniline;
N-(3,4-difluorobenzyl)-4-fluoro-3-[2-(1-methylpiperidin-4-yl)-1H-pyrrolo[2,3-b]pyridin-4-yl]aniline;
1-[4-(4-{5-[(3,5-difluorobenzyl)amino]-2-fluorophenyl}-1H-pyrrolo[2,3-b]pyridin-2-yl)piperidin-1-yl]-2-hydroxyethanone;
3-[4-(4-{2-fluoro-5-[(pyridin-3-ylmethyl)amino]phenyl}-1H-pyrrolo[2,3-b]pyridin-2-yl)piperidin-1-yl]propane-1,2-diol;
3-[4-(4-{2-fluoro-5-[(pyridin-4-ylmethyl)amino]phenyl}-1H-pyrrolo[2,3-b]pyridin-2-yl)piperidin-1-yl]propane-1,2-diol;
4-{[(3-{2-[1-(2,3-dihydroxypropyl)piperidin-4-yl]-1H-pyrrolo[2,3-b]pyridin-4-yl}-4-fluorophenyl)amino]methyl}benzonitrile;
3-{[(3-{2-[1-(2,3-dihydroxypropyl)piperidin-4-yl]-1H-pyrrolo[2,3-b]pyridin-4-yl}-4-fluorophenyl)amino]methyl}benzonitrile;
3-{2-[1-(cyclopropylsulfonyl)piperidin-4-yl]-1H-pyrrolo[2,3-b]pyridin-4-yl}-4-fluoro-N-(pyridin-4-ylmethyl)aniline;
4-{[(3-{2-[1-(cyclopropylsulfonyl)piperidin-4-yl]-1H-pyrrolo[2,3-b]pyridin-4-yl}-4-fluorophenyl)amino]methyl}benzonitrile;
3-{2-[1-(cyclopropylsulfonyl)piperidin-4-yl]-1H-pyrrolo[2,3-b]pyridin-4-yl}-N-(3,5-difluorobenzyl)-4-fluoroaniline;
3-{2-[1-(cyclopropylsulfonyl)piperidin-4-yl]-1H-pyrrolo[2,3-b]pyridin-4-yl}-4-fluoro-N-[3-(methylsulfonyl)benzyl]aniline;
4-(4-{2-fluoro-5-[(3-fluorobenzyl)amino]phenyl}-1H-pyrrolo[2,3-b]pyridin-2-yl)piperidine-1-sulfonamide;
3-[4-(4-{2-fluoro-5-[(3-fluorobenzyl)amino]phenyl}-1H-pyrrolo[2,3-b]pyridin-2-yl)piperidin-1-yl]propane-1,2-diol;
4-(5-fluoro-2-methoxyphenyl)-2-[4-(pyrrolidin-1-yl)cyclohex-1-en-1-yl]-1H-pyrrolo[2,3-b]pyridine;
4-(5-fluoro-2-methoxyphenyl)-2-[1-(methylsulfonyl)-2,5-dihydro-1H-pyrrol-3-yl]-1H-pyrrolo[2,3-b]pyridine;
3-[4-(4-{2-fluoro-5-[(3-fluorobenzyl)oxy]phenyl}-1H-pyrrolo[2,3-b]pyridin-2-yl)-3,6-dihydropyridin-1(2H)-yl]propane-1,2-diol;
3-[4-(4-{2,4-difluoro-5-[(3-fluorobenzyl)amino]phenyl}-1H-pyrrolo[2,3-b]pyridin-2-yl)-3,6-dihydropyridin-1(2H)-yl]propane-1,2-diol;
2-({4-[4-(5-fluoro-2-methoxyphenyl)-1H-pyrrolo[2,3-b]pyridin-2-yl]-3,6-dihydropyridin-1(2H)-yl}methyl)-1H-benzimidazole;
2-[1-(5,6-dihydro-2H-pyran-3-ylmethyl)-1,2,3,6-tetrahydropyridin-4-yl]-4-(5-fluoro-2-methoxyphenyl)-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)-N,N-dimethylaniline;
N,N-diethyl-2-[4-({4-[4-(5-fluoro-2-methoxyphenyl)-1H-pyrrolo[2,3-b]pyridin-2-yl]-3,6-dihydropyridin-1(2H)-yl}methyl)phenoxy]ethanamine;
4-(5-fluoro-2-methoxyphenyl)-2-[1-(pyridin-4-ylmethyl)-1,2,3,6-tetrahydropyridin-4-yl]-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)benzonitrile;
4-chloro-5-({4-[4-(5-fluoro-2-methoxyphenyl)-1H-pyrrolo[2,3-b]pyridin-2-yl]-3,6-dihydropyridin-1(2H)-yl}methyl)-1,3-thiazol-2-amine;
4-(5-fluoro-2-methoxyphenyl)-2-[1-(tetrahydrofuran-2-ylmethyl)-1,2,3,6-tetrahydropyridin-4-yl]-1H-pyrrolo[2,3-b]pyridine;
4-chloro-3-[2-(2,5-dihydro-1H-pyrrol-3-yl)-1H-pyrrolo[2,3-b]pyridin-4-yl]-N-(pyridin-3-ylmethyl)aniline;
4-chloro-3-[2-(2,5-dihydro-1H-pyrrol-3-yl)-1H-pyrrolo[2,3-b]pyridin-4-yl]-N-(3-fluorobenzyl)aniline;
4-chloro-3-[2-(2,5-dihydro-1H-pyrrol-3-yl)-1H-pyrrolo[2,3-b]pyridin-4-yl]-N-(tetrahydro-2H-pyran-3-ylmethyl)aniline;
4-chloro-3-[2-(2,5-dihydro-1H-pyrrol-3-yl)-1H-pyrrolo[2,3-b]pyridin-4-yl]-N-(piperidin-4-ylmethyl)aniline;
5-fluoro-4-(5-fluoro-2-methoxyphenyl)-2-(piperidin-4-yl)-1H-pyrrolo[2,3-b]pyridine;
N-cyclohexyl-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(4-methoxybenzyl)-3,6-dihydropyridine-1(2H)-carboxamide;

4-[4-(5-fluoro-2-methoxyphenyl)-1H-pyrrolo[2,3-b]pyridin-2-yl]-N-phenyl-3,6-dihydropyridine-1(2H)-carboxamide;

4-(4-{2-fluoro-5-[(pyridin-4-ylmethyl)amino]phenyl}-1H-pyrrolo[2,3-b]pyridin-2-yl)piperidine-1-sulfonamide;

5-fluoro-4-(5-fluoro-2-methoxyphenyl)-2-[1-(methylsulfonyl)piperidin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]piperidin-1-yl}propane-1,2-diol;

1-{4-[5-fluoro-4-(5-fluoro-2-methoxyphenyl)-1H-pyrrolo[2,3-b]pyridin-2-yl]piperidin-1-yl}ethanone;

3-[4-(4-{5-[(3,5-difluorobenzyl)amino]-2-fluorophenyl}-1H-pyrrolo[2,3-b]pyridin-2-yl)piperidin-1-yl]propane-1,2-diol;

4-[4-(5-fluoro-2-methoxyphenyl)-1H-pyrrolo[2,3-b]pyridin-2-yl]-N-[2-(morpholin-4-yl)ethyl]-3,6-dihydropyridine-1(2H)-carboxamide;

4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}(pyridin-2-yl)methanone;

{4-[4-(5-fluoro-2-methoxyphenyl)-1H-pyrrolo[2,3-b]pyridin-2-yl]-3,6-dihydropyridin-1(2H)-yl}(pyridin-3-yl)methanone;

{4-[4-(5-fluoro-2-methoxyphenyl)-1H-pyrrolo[2,3-b]pyridin-2-yl]-3,6-dihydropyridin-1(2H)-yl}(pyridin-4-yl)methanone;

{4-[4-(5-fluoro-2-methoxyphenyl)-1H-pyrrolo[2,3-b]pyridin-2-yl]-3,6-dihydropyridin-1(2H)-yl}(pyrazin-2-yl)methanone;

4-(5-fluoro-2-methoxyphenyl)-2-[1-(pyrimidin-4-yl)-1,2,3,6-tetrahydropyridin-4-yl]-1H-pyrrolo[2,3-b]pyridine;

4-(5-fluoro-2-methoxyphenyl)-2-[1-(2-methylpyrimidin-4-yl)-1,2,3,6-tetrahydropyridin-4-yl]-1H-pyrrolo[2,3-b]pyridine;

4-(5-fluoro-2-methoxyphenyl)-2-{1-[6-(trifluoromethyl)pyrimidin-4-yl]-1,2,3,6-tetrahydropyridin-4-yl}-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-3-(piperidin-1-yl)propan-1-one;

{4-[4-(5-fluoro-2-methoxyphenyl)-1H-pyrrolo[2,3-b]pyridin-2-yl]-3,6-dihydropyridin-1(2H)-yl}(1H-pyrazol-4-yl)methanone;

{4-[4-(5-fluoro-2-methoxyphenyl)-1H-pyrrolo[2,3-b]pyridin-2-yl]-3,6-dihydropyridin-1(2H)-yl}(1,3-thiazol-4-yl)methanone;

(3,5-dimethyl-1,2-oxazol-4-yl) {4-[4-(5-fluoro-2-methoxyphenyl)-1H-pyrrolo[2,3-b]pyridin-2-yl]-3,6-dihydropyridin-1(2H)-yl}methanone;

4-(2-chloro-5-methoxyphenyl)-2-[1-(methylsulfonyl)-1,2,3,6-tetrahydropyridin-4-yl]-1H-pyrrolo[2,3-b]pyridine;

2-[1-(methylsulfonyl)-1,2,3,6-tetrahydropyridin-4-yl]-4-(2,3,4-trifluorophenyl)-1H-pyrrolo[2,3-b]pyridine;

2-[1-(methylsulfonyl)-1,2,3,6-tetrahydropyridin-4-yl]-4-[3-(trifluoromethoxy)phenyl]-1H-pyrrolo[2,3-b]pyridine;

N-(2-{4-[4-(5-fluoro-2-methoxyphenyl)-1H-pyrrolo[2,3-b]pyridin-2-yl]-3,6-dihydropyridin-1(2H)-yl}ethyl)-N$^2$,N$^2$-dimethylglycinamide;

4-(4-methoxyphenyl)-2-[1-(methylsulfonyl)-1,2,3,6-tetrahydropyridin-4-yl]-1H-pyrrolo[2,3-b]pyridine;

4-(3,4-difluorophenyl)-2-[1-(methylsulfonyl)-1,2,3,6-tetrahydropyridin-4-yl]-1H-pyrrolo[2,3-b]pyridine;

2-[1-(methylsulfonyl)-1,2,3,6-tetrahydropyridin-4-yl]-4-[2-(trifluoromethoxy)phenyl]-1H-pyrrolo[2,3-b]pyridine;

4-[5-fluoro-2-(propan-2-yloxy)phenyl]-2-[1-(methylsulfonyl)-1,2,3,6-tetrahydropyridin-4-yl]-1H-pyrrolo[2,3-b]pyridine;

4-[2-(cyclopropyloxy)-5-fluorophenyl]-2-[1-(methylsulfonyl)-1,2,3,6-tetrahydropyridin-4-yl]-1H-pyrrolo[2,3-b]pyridine;

4-(4-ethoxy-3-fluorophenyl)-2-[1-(methylsulfonyl)-1,2,3,6-tetrahydropyridin-4-yl]-1H-pyrrolo[2,3-b]pyridine;

4-(4-{5-[(3,5-difluorobenzyl)amino]-2-fluorophenyl}-1H-pyrrolo[2,3-b]pyridin-2-yl)piperidine-1-sulfonamide;

4-(4-chloro-3-methylphenyl)-2-[1-(methylsulfonyl)-1,2,3,6-tetrahydropyridin-4-yl]-1H-pyrrolo[2,3-b]pyridine;

4-(3-chloro-4-fluorophenyl)-2-[1-(methylsulfonyl)-1,2,3,6-tetrahydropyridin-4-yl]-1H-pyrrolo[2,3-b]pyridine;

N,N-dimethyl-3-{2-[1-(methylsulfonyl)-1,2,3,6-tetrahydropyridin-4-yl]-1H-pyrrolo[2,3-b]pyridin-4-yl}benzamide;

4-(4-fluoro-3-methylphenyl)-2-[1-(methylsulfonyl)-1,2,3,6-tetrahydropyridin-4-yl]-1H-pyrrolo[2,3-b]pyridine;

4-[3-fluoro-4-(propan-2-yloxy)phenyl]-2-[1-(methylsulfonyl)-1,2,3,6-tetrahydropyridin-4-yl]-1H-pyrrolo[2,3-b]pyridine;

4-(4-butoxy-3-fluorophenyl)-2-[1-(methylsulfonyl)-1,2,3,6-tetrahydropyridin-4-yl]-1H-pyrrolo[2,3-b]pyridine;

(3-{2-[1-(methylsulfonyl)-1,2,3,6-tetrahydropyridin-4-yl]-1H-pyrrolo[2,3-b]pyridin-4-yl}phenyl)(morpholin-4-yl)methanone;

N-(3,5-difluorobenzyl)-4-fluoro-3-[2-(1,2,3,6-tetrahydropyridin-4-yl)-1H-pyrrolo[2,3-b]pyridin-4-yl]aniline;

4-(5-fluoro-2-methoxyphenyl)-2-(1,2,5,6-tetrahydropyridin-3-yl)-1H-pyrrolo[2,3-b]pyridine;

4-(3,5-difluorophenyl)-2-[1-(methylsulfonyl)-1,2,3,6-tetrahydropyridin-4-yl]-1H-pyrrolo[2,3-b]pyridine;

4-(2,4-dichlorophenyl)-2-[1-(methylsulfonyl)-1,2,3,6-tetrahydropyridin-4-yl]-1H-pyrrolo[2,3-b]pyridine;

4-(2-ethylphenyl)-2-[1-(methylsulfonyl)-1,2,3,6-tetrahydropyridin-4-yl]-1H-pyrrolo[2,3-b]pyridine;

4-(2,4-dimethylphenyl)-2-[1-(methylsulfonyl)-1,2,3,6-tetrahydropyridin-4-yl]-1H-pyrrolo[2,3-b]pyridine;

4-(2,5-dichlorophenyl)-2-[1-(methylsulfonyl)-1,2,3,6-tetrahydropyridin-4-yl]-1H-pyrrolo[2,3-b]pyridine;

4-(3,4-dichlorophenyl)-2-[1-(methylsulfonyl)-1,2,3,6-tetrahydropyridin-4-yl]-1H-pyrrolo[2,3-b]pyridine;

N-(4-{2-[1-(methylsulfonyl)-1,2,3,6-tetrahydropyridin-4-yl]-1H-pyrrolo[2,3-b]pyridin-4-yl}phenyl)methanesulfonamide;

4-(5-chloro-2-methoxyphenyl)-2-[1-(methylsulfonyl)-1,2,3,6-tetrahydropyridin-4-yl]-1H-pyrrolo[2,3-b]pyridine;

4-[2-methoxy-5-(propan-2-yl)phenyl]-2-[1-(methylsulfonyl)-1,2,3,6-tetrahydropyridin-4-yl]-1H-pyrrolo[2,3-b]pyridine;

4-(2-methoxy-5-methylphenyl)-2-[1-(methylsulfonyl)-1,2,3,6-tetrahydropyridin-4-yl]-1H-pyrrolo[2,3-b]pyridine;

4-(4-methoxy-3-methylphenyl)-2-[1-(methylsulfonyl)-1,2,3,6-tetrahydropyridin-4-yl]-1H-pyrrolo[2,3-b]pyridine;

2-{2-[1-(methylsulfonyl)-1,2,3,6-tetrahydropyridin-4-yl]-1H-pyrrolo[2,3-b]pyridin-4-yl}benzonitrile;

4-(2-methoxyphenyl)-2-[1-(methylsulfonyl)-1,2,3,6-tetrahydropyridin-4-yl]-1H-pyrrolo[2,3-b]pyridine;

3-{2-[1-(methylsulfonyl)-1,2,3,6-tetrahydropyridin-4-yl]-1H-pyrrolo[2,3-b]pyridin-4-yl}benzonitrile;

2-[1-(methylsulfonyl)-1,2,3,6-tetrahydropyridin-4-yl]-4-[2-(trifluoromethyl)phenyl]-1H-pyrrolo[2,3-b]pyridine;

4-(3-chlorophenyl)-2-[1-(methylsulfonyl)-1,2,3,6-tetrahydropyridin-4-yl]-1H-pyrrolo[2,3-b]pyridine;
4-(2-chlorophenyl)-2-[1-(methylsulfonyl)-1,2,3,6-tetrahydropyridin-4-yl]-1H-pyrrolo[2,3-b]pyridine;
4-[2-fluoro-5-(trifluoromethyl)phenyl]-2-[1-(methylsulfonyl)-1,2,3,6-tetrahydropyridin-4-yl]-1H-pyrrolo[2,3-b]pyridine;
4-(3-chloro-4-methoxyphenyl)-2-[1-(methylsulfonyl)-1,2,3,6-tetrahydropyridin-4-yl]-1H-pyrrolo[2,3-b]pyridine;
4-(2-fluoro-5-methylphenyl)-2-[1-(methylsulfonyl)-1,2,3,6-tetrahydropyridin-4-yl]-1H-pyrrolo[2,3-b]pyridine;
4-(5-chloro-2-fluoro-3-methylphenyl)-2-[1-(methylsulfonyl)-1,2,3,6-tetrahydropyridin-4-yl]-1H-pyrrolo[2,3-b]pyridine;
4-(5-chloro-2-propoxyphenyl)-2-[1-(methylsulfonyl)-1,2,3,6-tetrahydropyridin-4-yl]-1H-pyrrolo[2,3-b]pyridine;
4-(4-{5-[(3,5-difluorobenzyl)amino]-2-fluorophenyl}-1H-pyrrolo[2,3-b]pyridin-2-yl)-N-methyl-3,6-dihydropyridine-1(2H)-carboxamide;
3-[4-(4-{5-[(3,5-difluorobenzyl)amino]-2-fluorophenyl}-1H-pyrrolo[2,3-b]pyridin-2-yl)-3,6-dihydropyridin-1(2H)-yl]propane-1,2-diol;
ethyl 4-[4-(5-fluoro-2-methoxyphenyl)-1H-pyrrolo[2,3-b]pyridin-2-yl]cyclohex-3-ene-1-carboxylate;
4-(2-ethoxy-5-fluorophenyl)-2-[1-(methylsulfonyl)-1,2,3,6-tetrahydropyridin-4-yl]-1H-pyrrolo[2,3-b]pyridine;
4-(2,3-dichlorophenyl)-2-[1-(methylsulfonyl)-1,2,3,6-tetrahydropyridin-4-yl]-1H-pyrrolo[2,3-b]pyridine;
4-(3-chloro-4-methylphenyl)-2-[1-(methylsulfonyl)-1,2,3,6-tetrahydropyridin-4-yl]-1H-pyrrolo[2,3-b]pyridine;
2-methyl-5-{2-[1-(methylsulfonyl)-1,2,3,6-tetrahydropyridin-4-yl]-1H-pyrrolo[2,3-b]pyridin-4-yl}aniline;
4-(2-fluorobiphenyl-4-yl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[3-(propan-2-yloxy)phenyl]-1H-pyrrolo[2,3-b]pyridine;
4-(3-fluoro-4-propoxyphenyl)-2-[1-(methylsulfonyl)-1,2,3,6-tetrahydropyridin-4-yl]-1H-pyrrolo[2,3-b]pyridine;
4-[2-fluoro-5-(propan-2-yloxy)phenyl]-2-[1-(methylsulfonyl)-1,2,3,6-tetrahydropyridin-4-yl]-1H-pyrrolo[2,3-b]pyridine;
4-(4-butoxy-3-chlorophenyl)-2-[1-(methylsulfonyl)-1,2,3,6-tetrahydropyridin-4-yl]-1H-pyrrolo[2,3-b]pyridine;
4-[2-(2-methylpropoxy)phenyl]-2-[1-(methylsulfonyl)-1,2,3,6-tetrahydropyridin-4-yl]-1H-pyrrolo[2,3-b]pyridine;
4-{2-[1-(methylsulfonyl)-1,2,3,6-tetrahydropyridin-4-yl]-1H-pyrrolo[2,3-b]pyridin-4-yl}benzonitrile;
2-[1-(methylsulfonyl)-1,2,3,6-tetrahydropyridin-4-yl]-4-phenyl-1H-pyrrolo[2,3-b]pyridine;
(4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid;
4-(3-fluoro-4-methoxyphenyl)-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}aniline;
N-(2-{2-[1-(methylsulfonyl)-1,2,3,6-tetrahydropyridin-4-yl]-1H-pyrrolo[2,3-b]pyridin-4-yl}phenyl)methanesulfonamide;
3-{2-[1-(methylsulfonyl)-1,2,3,6-tetrahydropyridin-4-yl]-1H-pyrrolo[2,3-b]pyridin-4-yl}-N-(propan-2-yl)benzamide;
2-{4-[3-cyano-4-(5-fluoro-2-methoxyphenyl)-1H-pyrrolo[2,3-b]pyridin-2-yl]piperazin-1-yl}-N,N-dimethylacetamide;
(4-{2-[1-(methylsulfonyl)-1,2,3,6-tetrahydropyridin-4-yl]-1H-pyrrolo[2,3-b]pyridin-4-yl}phenyl)acetonitrile;
N-methyl-4-{2-[1-(methylsulfonyl)-1,2,3,6-tetrahydropyridin-4-yl]-1H-pyrrolo[2,3-b]pyridin-4-yl}benzamide;
N-(3-{2-[1-(methylsulfonyl)-1,2,3,6-tetrahydropyridin-4-yl]-1H-pyrrolo[2,3-b]pyridin-4-yl}phenyl)acetamide;
N-(4-{2-[1-(methylsulfonyl)-1,2,3,6-tetrahydropyridin-4-yl]-1H-pyrrolo[2,3-b]pyridin-4-yl}phenyl)acetamide;
4-[4-(5-fluoro-2-methoxyphenyl)-1H-pyrrolo[2,3-b]pyridin-2-yl]-N-methyl-3,6-dihydropyridine-1(2H)-sulfonamide;
4-(5-fluoro-2-methoxyphenyl)-2-[1-(pyridin-2-ylmethyl)-1,2,3,6-tetrahydropyridin-4-yl]-1H-pyrrolo[2,3-b]pyridine;
3-{5-[4-(5-fluoro-2-methoxyphenyl)-1H-pyrrolo[2,3-b]pyridin-2-yl]-3,6-dihydropyridin-1(2H)-yl}propane-1,2-diol;
5-[4-(5-fluoro-2-methoxyphenyl)-1H-pyrrolo[2,3-b]pyridin-2-yl]-N-methyl-3,6-dihydropyridine-1(2H)-carboxamide;
4-(5-fluoro-2-methoxyphenyl)-2-[1-(methylsulfonyl)-1,2,5,6-tetrahydropyridin-3-yl]-1H-pyrrolo[2,3-b]pyridine;
4-(5-fluoro-2-methylphenyl)-2-[1-(methylsulfonyl)-1,2,3,6-tetrahydropyridin-4-yl]-1H-pyrrolo[2,3-b]pyridine;
4-{5-[(3,5-difluorobenzyl)oxy]-2-fluorophenyl}-2-(1,2,3,6-tetrahydropyridin-4-yl)-1H-pyrrolo[2,3-b]pyridine;
4-{5-[(3,5-difluorobenzyl)oxy]-2-fluorophenyl}-2-(1-methyl-1,2,3,6-tetrahydropyridin-4-yl)-1H-pyrrolo[2,3-b]pyridine;
3-[4-(4-{5-[(3,5-difluorobenzyl)oxy]-2-fluorophenyl}-1H-pyrrolo[2,3-b]pyridin-2-yl)-3,6-dihydropyridin-1(2H)-yl]propane-1,2-diol;
4-{5-[(3,5-difluorobenzyl)oxy]-2-fluorophenyl}-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}benzamide;
4-(4-ethoxy-2-methylphenyl)-2-[1-(methylsulfonyl)-1,2,3,6-tetrahydropyridin-4-yl]-1H-pyrrolo[2,3-b]pyridine;
4-[4-chloro-3-(trifluoromethyl)phenyl]-2-[1-(methylsulfonyl)-1,2,3,6-tetrahydropyridin-4-yl]-1H-pyrrolo[2,3-b]pyridine;
N-butyl-3-{2-[1-(methylsulfonyl)-1,2,3,6-tetrahydropyridin-4-yl]-1H-pyrrolo[2,3-b]pyridin-4-yl}benzamide;
4-(3-fluorophenyl)-2-[1-(methylsulfonyl)-1,2,3,6-tetrahydropyridin-4-yl]-1H-pyrrolo[2,3-b]pyridine;
4-{3-chloro-4-[(3-chlorobenzyl)oxy]phenyl}-2-[1-(methylsulfonyl)-1,2,3,6-tetrahydropyridin-4-yl]-1H-pyrrolo[2,3-b]pyridine;
4-(4-fluoro-2-methoxyphenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[4-(trifluoromethoxy)phenyl]-1H-pyrrolo[2,3-b]pyridine;
4-[3-chloro-4-(propan-2-yloxy)phenyl]-2-[1-(methylsulfonyl)-1,2,3,6-tetrahydropyridin-4-yl]-1H-pyrrolo[2,3-b]pyridine;
4-(3,5-dichlorophenyl)-2-[1-(methylsulfonyl)-1,2,3,6-tetrahydropyridin-4-yl]-1H-pyrrolo[2,3-b]pyridine;
4-(4-fluoro-2-propoxyphenyl)-2-[1-(methylsulfonyl)-1,2,3,6-tetrahydropyridin-4-yl]-1H-pyrrolo[2,3-b]pyridine;
4-(5-fluoro-2-methoxyphenyl)-2-[1-(morpholin-4-ylsulfonyl)-1,2,3,6-tetrahydropyridin-4-yl]-1H-pyrrolo[2,3-b]pyridine;
2-fluoro-N-{4-methoxy-3-[2-(1,2,3,6-tetrahydropyridin-4-yl)-1H-pyrrolo[2,3-b]pyridin-4-yl]benzyl}aniline;
N-{4-methoxy-3-[2-(1,2,3,6-tetrahydropyridin-4-yl)-1H-pyrrolo[2,3-b]pyridin-4-yl]benzyl}tetrahydro-2H-pyran-4-amine;
4-[2-methoxy-5-(morpholin-4-ylmethyl)phenyl]-2-(1,2,3,6-tetrahydropyridin-4-yl)-1H-pyrrolo[2,3-b]pyridine;

N-benzyl-4-[4-(5-fluoro-2-methoxyphenyl)-1H-pyrrolo[2,3-b]pyridin-2-yl]cyclohex-3-ene-1-carboxamide;
N-(3-fluorobenzyl)-4-[4-(5-fluoro-2-methoxyphenyl)-1H-pyrrolo[2,3-b]pyridin-2-yl]cyclohex-3-ene-1-carboxamide;
N-(3,5-difluorobenzyl)-4-[4-(5-fluoro-2-methoxyphenyl)-1H-pyrrolo[2,3-b]pyridin-2-yl]cyclohex-3-ene-1-carboxamide;
N-(2,5-difluorobenzyl)-4-[4-(5-fluoro-2-methoxyphenyl)-1H-pyrrolo[2,3-b]pyridin-2-yl]cyclohex-3-ene-1-carboxamide;
N-(3-chlorobenzyl)-4-[4-(5-fluoro-2-methoxyphenyl)-1H-pyrrolo[2,3-b]pyridin-2-yl]cyclohex-3-ene-1-carboxamide;
4-[4-(5-fluoro-2-methoxyphenyl)-1H-pyrrolo[2,3-b]pyridin-2-yl]-N-(pyridin-4-ylmethyl)cyclohex-3-ene-1-carboxamide;
4-[4-(5-fluoro-2-methoxyphenyl)-1H-pyrrolo[2,3-b]pyridin-2-yl]-N-[(3-methyl-1H-pyrazol-5-yl)methyl]cyclohex-3-ene-1-carboxamide;
4-[4-(5-fluoro-2-methoxyphenyl)-1H-pyrrolo[2,3-b]pyridin-2-yl]-N-(tetrahydro-2H-pyran-4-ylmethyl)cyclohex-3-ene-1-carboxamide;
4-[4-(5-fluoro-2-methoxyphenyl)-1H-pyrrolo[2,3-b]pyridin-2-yl]-N-(4-hydroxycyclohexyl)cyclohex-3-ene-1-carboxamide;
(3,3-difluoroazetidin-1-yl) {4-[4-(5-fluoro-2-methoxyphenyl)-1H-pyrrolo[2,3-b]pyridin-2-yl]cyclohex-3-en-1-yl}methanone;
2-(3,6-dihydro-2H-pyran-4-yl)-4-(5-fluoro-2-methoxyphenyl)-1H-pyrrolo[2,3-b]pyridine;
{4-[4-(5-fluoro-2-methoxyphenyl)-1H-pyrrolo[2,3-b]pyridin-2-yl]-3,6-dihydropyridin-1(2H)-yl}(tetrahydro-2H-pyran-3-yl)methanone;
1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]-2-hydroxyethanone;
1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]ethanone;
1-{5-[4-(5-fluoro-2-methoxyphenyl)-1H-pyrrolo[2,3-b]pyridin-2-yl]-3,6-dihydropyridin-1(2H)-yl}-2-hydroxyethanone;
1-{5-[4-(5-fluoro-2-methoxyphenyl)-1H-pyrrolo[2,3-b]pyridin-2-yl]-3,6-dihydropyridin-1(2H)-yl}ethanone;
N-[4-({5-[4-(5-fluoro-2-methoxyphenyl)-1H-pyrrolo[2,3-b]pyridin-2-yl]-3,6-dihydropyridin-1(2H)-yl}methyl)phenyl]acetamide;
4-(5-fluoro-2-methoxyphenyl)-2-[1-(tetrahydrofuran-2-ylmethyl)-1,2,5,6-tetrahydropyridin-3-yl]-1H-pyrrolo[2,3-b]pyridine;
1-{4-[4-(5-fluoro-2-methoxyphenyl)-1H-pyrrolo[2,3-b]pyridin-2-yl]-3,6-dihydropyridin-1(2H)-yl}-2-methylpropan-2-ol;
4-[4-(5-fluoro-2-methoxyphenyl)-1H-pyrrolo[2,3-b]pyridin-2-yl]-N,N-dimethyl-3,6-dihydropyridine-1(2H)-carboxamide;
ethyl ({4-[4-(5-fluoro-2-methoxyphenyl)-1H-pyrrolo[2,3-b]pyridin-2-yl]piperidin-1-yl}sulfonyl)carbamate;
4-[4-(5-fluoro-2-methoxyphenyl)-1H-pyrrolo[2,3-b]pyridin-2-yl]-N-methylpiperidine-1-sulfonamide;
4-[4-(5-fluoro-2-methoxyphenyl)-1H-pyrrolo[2,3-b]pyridin-2-yl]-N,N-dimethylpiperidine-1-sulfonamide;
4-(5-fluoro-2-methoxyphenyl)-2-[4-(trifluoromethyl)cyclohex-1-en-1-yl]-1H-pyrrolo[2,3-b]pyridine;
4-[4-(5-fluoro-2-methoxyphenyl)-1H-pyrrolo[2,3-b]pyridin-2-yl]-N-(tetrahydro-2H-pyran-4-ylmethyl)cyclohex-3-en-1-amine;
2-{4-[4-(5-fluoro-2-methoxyphenyl)-1H-pyrrolo[2,3-b]pyridin-2-yl]piperidin-1-yl}ethanesulfonamide;
N-benzyl-4-[4-(5-fluoro-2-methoxyphenyl)-1H-pyrrolo[2,3-b]pyridin-2-yl]cyclohex-3-en-1-amine;
4-[4-(5-fluoro-2-methoxyphenyl)-1H-pyrrolo[2,3-b]pyridin-2-yl]-N-(pyridin-4-ylmethyl)cyclohex-3-en-1-amine;
4-[4-(5-fluoro-2-methoxyphenyl)-1H-pyrrolo[2,3-b]pyridin-2-yl]-N-(morpholin-2-ylmethyl)cyclohex-3-en-1-amine;
4-(5-fluoro-2-methoxyphenyl)-2-[1-(S-methylsulfonimidoyl)piperidin-4-yl]-1H-pyrrolo[2,3-b]pyridine;
N-ethyl-4-[4-(5-fluoro-2-methoxyphenyl)-1H-pyrrolo[2,3-b]pyridin-2-yl]piperidine-1-sulfonamide;
4-[3-(4-fluorophenoxy)phenyl]-2-(piperidin-4-yl)-1H-pyrrolo[2,3-b]pyridine;
4-(2,3-difluorophenyl)-2-(1,2,3,6-tetrahydropyridin-4-yl)-1H-pyrrolo[2,3-b]pyridine;
3-{4-[4-(2,3-difluorophenyl)-1H-pyrrolo[2,3-b]pyridin-2-yl]-3,6-dihydropyridin-1(2H)-yl}propane-1,2-diol;
N-[4-({4-[4-(2,3-difluorophenyl)-1H-pyrrolo[2,3-b]pyridin-2-yl]-3,6-dihydropyridin-1(2H)-yl}methyl)phenyl]acetamide;
1-{4-[4-(2,3-difluorophenyl)-1H-pyrrolo[2,3-b]pyridin-2-yl]-3,6-dihydropyridin-1(2H)-yl}-2-hydroxyethanone;
2-(8-azabicyclo[3.2.1]oct-2-en-3-yl)-4-(5-fluoro-2-methoxyphenyl)-1H-pyrrolo[2,3-b]pyridine;
N-(3,5-difluorobenzyl)-4-[4-(5-fluoro-2-methoxyphenyl)-1H-pyrrolo[2,3-b]pyridin-2-yl]cyclohex-3-en-1-amine;
3-[4-(5-fluoro-2-methoxyphenyl)-1H-pyrrolo[2,3-b]pyridin-2-yl]-N-methyl-8-azabicyclo[3.2.1]oct-2-ene-8-carboxamide;
3-{3-[4-(5-fluoro-2-methoxyphenyl)-1H-pyrrolo[2,3-b]pyridin-2-yl]-8-azabicyclo[3.2.1]oct-2-en-8-yl}propane-1,2-diol;
1-{3-[4-(5-fluoro-2-methoxyphenyl)-1H-pyrrolo[2,3-b]pyridin-2-yl]-8-azabicyclo[3.2.1]oct-2-en-8-yl}-2-hydroxyethanone;
3-[4-(5-fluoro-2-methoxyphenyl)-1H-pyrrolo[2,3-b]pyridin-2-yl]-N,N-dimethyl-8-azabicyclo[3.2.1]oct-2-ene-8-carboxamide;
N-[(2S)-2,3-dihydroxypropyl]-4-[4-(5-fluoro-2-methoxyphenyl)-1H-pyrrolo[2,3-b]pyridin-2-yl]piperidine-1-sulfonamide;
3-chloro-4-(5-fluoro-2-methoxyphenyl)-2-(piperidin-4-yl)-1H-pyrrolo[2,3-b]pyridine;
3-bromo-4-(5-fluoro-2-methoxyphenyl)-2-(piperidin-4-yl)-1H-pyrrolo[2,3-b]pyridine;
ethyl ({4-[3-bromo-4-(5-fluoro-2-methoxyphenyl)-1H-pyrrolo[2,3-b]pyridin-2-yl]piperidin-1-yl}sulfonyl)carbamate;
4-[4-(5-fluoro-2-methoxyphenyl)-1H-pyrrolo[2,3-b]pyridin-2-yl]-N-(2-hydroxyethyl)-3,6-dihydropyridine-1(2H)-carboxamide;
4-[4-(5-fluoro-2-methoxyphenyl)-1H-pyrrolo[2,3-b]pyridin-2-yl]-N-(methylsulfonyl)cyclohex-3-ene-1-carboxamide;
N-methyl-4-[2-(1,2,3,6-tetrahydropyridin-4-yl)-1H-pyrrolo[2,3-b]pyridin-4-yl]benzamide;
5-[4-(5-fluoro-2-methoxyphenyl)-1H-pyrrolo[2,3-b]pyridin-2-yl]-N,N-dimethyl-3,6-dihydropyridine-1(2H)-carboxamide;
4-[4-(5-fluoro-2-methoxyphenyl)-1H-pyrrolo[2,3-b]pyridin-2-yl]-N-(pyridin-3-ylmethyl)cyclohex-3-en-1-amine;

4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-[2-(pyrrolidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-[2-(4-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(tetrahydrofuran-2-ylmethyl)amino]ethyl}-3,6-dihydropyridine-1(2H)-carboxamide;

methyl 4-{2-[({4-[4-(5-fluoro-2-methoxyphenyl)-1H-pyrrolo[2,3-b]pyridin-2-yl]-3,6-dihydropyridin-1(2H)-yl}carbonyl)amino]ethyl}piperazine-1-carboxylate;

N-[2-(3,4-dihydroisoquinolin-2(1H)-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide;

1-{5-[4-(5-fluoro-2-methoxyphenyl)-1H-pyrrolo[2,3-b]pyridin-2-yl]-3,6-dihydropyridin-1(2H)-yl}-2-methylpropan-2-ol;

4-{2-[1-(2,3-dihydroxypropyl)-1,2,3,6-tetrahydropyridin-4-yl]-1H-pyrrolo[2,3-b]pyridin-4-yl}-N-methylbenzamide;

N-methyl-4-{4-[4-(methylcarbamoyl)phenyl]-1H-pyrrolo[2,3-b]pyridin-2-yl}-3,6-dihydropyridine-1(2H)-carboxamide;

4-{2-[1-(hydroxyacetyl)-1,2,3,6-tetrahydropyridin-4-yl]-1H-pyrrolo[2,3-b]pyridin-4-yl}-N-methylbenzamide;

4-[4-(5-fluoro-2-methoxyphenyl)-1H-pyrrolo[2,3-b]pyridin-2-yl]-N,N-dimethyl-3,6-dihydropyridine-1(2H)-sulfonamide;

3-bromo-4-(5-fluoro-2-methoxyphenyl)-2-(1,2,3,6-tetrahydropyridin-4-yl)-1H-pyrrolo[2,3-b]pyridine;

4-(2,4-dimethoxyphenyl)-2-(1,2,3,6-tetrahydropyridin-4-yl)-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}glycine;

4-[4-(5-fluoro-2-methoxyphenyl)-1H-pyrrolo[2,3-b]pyridin-2-yl]-N-methylcyclohex-3-ene-1-carboxamide;

4-[4-(5-fluoro-2-methoxyphenyl)-1H-pyrrolo[2,3-b]pyridin-2-yl]-N-[(3-hydroxyoxetan-3-yl)methyl]-3,6-dihydropyridine-1(2H)-carboxamide;

methyl {4-[4-(5-fluoro-2-methoxyphenyl)-1H-pyrrolo[2,3-b]pyridin-2-yl]-3,6-dihydropyridin-1(2H)-yl}acetate;

4-(4,5-difluoro-2-methoxyphenyl)-2-(1,2,3,6-tetrahydropyridin-4-yl)-1H-pyrrolo[2,3-b]pyridine;

4-[2-methoxy-4-(1H-pyrazol-1-yl)phenyl]-2-(1,2,3,6-tetrahydropyridin-4-yl)-1H-pyrrolo[2,3-b]pyridine;

4-(2,6-dimethoxyphenyl)-2-(1,2,3,6-tetrahydropyridin-4-yl)-1H-pyrrolo[2,3-b]pyridine;

4-(2-methoxyphenyl)-2-(1,2,3,6-tetrahydropyridin-4-yl)-1H-pyrrolo[2,3-b]pyridine;

4-(2-chloro-5-methoxyphenyl)-2-(1,2,3,6-tetrahydropyridin-4-yl)-1H-pyrrolo[2,3-b]pyridine;

4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile;

1-{4-[4-(2,3-difluorophenyl)-1H-pyrrolo[2,3-b]pyridin-2-yl]-3,6-dihydropyridin-1(2H)-yl}-2-methylpropan-2-ol;

4-(2,3-difluorophenyl)-2-[1-(pyridin-2-ylmethyl)-1,2,3,6-tetrahydropyridin-4-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-(5-fluoro-2-methoxyphenyl)-2-(1,2,3,6-tetrahydropyridin-4-yl)-1H-pyrrolo[2,3-b]pyridine-5-carbonitrile;

5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one;

2-{4-[4-(5-fluoro-2-methoxyphenyl)-1H-pyrrolo[2,3-b]pyridin-2-yl]-3,6-dihydropyridin-1(2H)-yl}-N-methylacetamide;

ethyl ({4-[3-bromo-4-(5-fluoro-2-methoxyphenyl)-1H-pyrrolo[2,3-b]pyridin-2-yl]-3,6-dihydropyridin-1(2H)-yl}sulfonyl)carbamate;

4-(5-fluoro-2-methoxyphenyl)-5-methyl-2-[1-(methylsulfonyl)-1,2,3,6-tetrahydropyridin-4-yl]-1H-pyrrolo[2,3-b]pyridine;

4-(5-fluoro-2-methoxyphenyl)-5-methyl-2-(1,2,3,6-tetrahydropyridin-4-yl)-1H-pyrrolo[2,3-b]pyridine;

N-[{4-[4-(5-fluoro-2-methoxyphenyl)-1H-pyrrolo[2,3-b]pyridin-2-yl]-3,6-dihydropyridin-1(2H)-yl}(methyl)oxido-$\lambda^6$-sulfanylidene]-4-methylbenzenesulfonamide;

4-(2-ethoxy-5-fluorophenyl)-2-(1,2,3,6-tetrahydropyridin-4-yl)-1H-pyrrolo[2,3-b]pyridine;

4-(2,5-dimethoxyphenyl)-2-(1,2,3,6-tetrahydropyridin-4-yl)-1H-pyrrolo[2,3-b]pyridine;

N-[(2S)-2,3-dihydroxypropyl]-4-[4-(5-fluoro-2-methoxyphenyl)-1H-pyrrolo[2,3-b]pyridin-2-yl]cyclohex-3-ene-1-carboxamide;

4-{4-[4-(5-fluoro-2-methoxyphenyl)-1H-pyrrolo[2,3-b]pyridin-2-yl]-3,6-dihydropyridin-1(2H)-yl}cyclohexanol;

1-({4-[4-(5-fluoro-2-methoxyphenyl)-1H-pyrrolo[2,3-b]pyridin-2-yl]-3,6-dihydropyridin-1(2H)-yl}carbonyl)piperidine-4-carboxylic acid;

4-[4-(5-fluoro-2-methoxyphenyl)-1H-pyrrolo[2,3-b]pyridin-2-yl]-N-[2-(4-oxopiperidin-1-yl)ethyl]-3,6-dihydropyridine-1(2H)-carboxamide;

N-[2-(3,3-difluoropiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-[2-(3-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypyrrolidin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(2-hydroxyethyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-[2-(3-oxopiperazin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypiperidin-1-yl]ethyl}-3,6-dihydropyridine-1(2H)-carboxamide;

4-methoxy-3-[2-(1,2,3,6-tetrahydropyridin-4-yl)-1H-pyrrolo[2,3-b]pyridin-4-yl]benzonitrile;

4-(2-chloro-5-fluorophenyl)-2-(1,2,3,6-tetrahydropyridin-4-yl)-1H-pyrrolo[2,3-b]pyridine;

4-(4-fluoro-2-methoxyphenyl)-2-(1,2,3,6-tetrahydropyridin-4-yl)-1H-pyrrolo[2,3-b]pyridine;

4-[2-(difluoromethoxy)-5-fluorophenyl]-2-(1,2,3,6-tetrahydropyridin-4-yl)-1H-pyrrolo[2,3-b]pyridine;

({4-[4-(5-fluoro-2-methoxyphenyl)-1H-pyrrolo[2,3-b]pyridin-2-yl]-3,6-dihydropyridin-1(2H)-yl}sulfonyl)acetic acid;

4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine;

5-chloro-4-(5-fluoro-2-methoxyphenyl)-2-(1,2,3,6-tetrahydropyridin-4-yl)-1H-pyrrolo[2,3-b]pyridine;

4-(5-fluoro-2-methoxyphenyl)-2-{1-[(tetrahydrofuran-2-ylmethyl)sulfonyl]-1,2,3,6-tetrahydropyridin-4-yl}-1H-pyrrolo[2,3-b]pyridine;

ethyl ({4-[4-(5-fluoro-2-methoxyphenyl)-5-methyl-1H-pyrrolo[2,3-b]pyridin-2-yl]-3,6-dihydropyridin-1(2H)-yl}sulfonyl)carbamate;

3-chloro-4-(5-fluoro-2-methoxyphenyl)-2-(1,2,3,6-tetrahydropyridin-4-yl)-1H-pyrrolo[2,3-b]pyridine;

ethyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate;

3-chloro-4-(5-fluoro-2-methoxyphenyl)-2-[1-(methylsulfonyl)-1,2,3,6-tetrahydropyridin-4-yl]-1H-pyrrolo[2,3-b]pyridine;

(cis-4-{4-[5-fluoro-4-(5-fluoro-2-methoxyphenyl)-1H-pyrrolo[2,3-b]pyridin-2-yl]piperidin-1-yl}cyclohexyl)acetic acid;

4-[4-(5-fluoro-2-methoxyphenyl)-1H-pyrrolo[2,3-b]pyridin-2-yl]-N-(pyridin-2-ylmethyl)cyclohex-3-en-1-amine;

4-[4-(5-fluoro-2-methoxyphenyl)-1H-pyrrolo[2,3-b]pyridin-2-yl]-N-(pyrazin-2-ylmethyl)cyclohex-3-en-1-amine;

4-[4-(5-fluoro-2-methoxyphenyl)-1H-pyrrolo[2,3-b]pyridin-2-yl]-N-(pyrimidin-5-ylmethyl)cyclohex-3-en-1-amine;

4-[4-(5-fluoro-2-methoxyphenyl)-1H-pyrrolo[2,3-b]pyridin-2-yl]-N-(tetrahydrofuran-2-ylmethyl)cyclohex-3-en-1-amine;

4-{5-fluoro-2-[($^2$H$_3$)methyloxy]phenyl}-2-(1,2,3,6-tetrahydropyridin-4-yl)-1H-pyrrolo[2,3-b]pyridine;

4-(4-{5-fluoro-2-[($^2$H$_3$)methyloxy]phenyl}-1H-pyrrolo[2,3-b]pyridin-2-yl)-N-methyl-3,6-dihydropyridine-1(2H)-carboxamide;

4-{5-fluoro-2-[($^2$H$_3$)methyloxy]phenyl}-2-[1-(methylsulfonyl)-1,2,3,6-tetrahydropyridin-4-yl]-1H-pyrrolo[2,3-b]pyridine;

methyl 2-{4-[4-(5-fluoro-2-methoxyphenyl)-1H-pyrrolo[2,3-b]pyridin-2-yl]-3,6-dihydropyridin-1(2H)-yl}propanoate;

5-chloro-4-(5-fluoro-2-methoxyphenyl)-2-[1-(methylsulfonyl)-1,2,3,6-tetrahydropyridin-4-yl]-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone;

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid;

{4-[4-(5-fluoro-2-methoxyphenyl)-1H-pyrrolo[2,3-b]pyridin-2-yl]-3,6-dihydropyridin-1(2H)-yl}[(4S)-2,2,5,5-tetramethyl-1,3-dioxolan-4-yl]methanone;

2-{4-[4-(5-fluoro-2-methoxyphenyl)-1H-pyrrolo[2,3-b]pyridin-2-yl]-3,6-dihydropyridin-1(2H)-yl}propanoic acid;

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid;

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid;

methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

methyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate;

2-fluoro-N-methyl-4-{2-[1-(methylsulfonyl)-1,2,3,6-tetrahydropyridin-4-yl]-1H-pyrrolo[2,3-b]pyridin-4-yl}benzamide;

(2S)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

(2R)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

4-(5-fluoro-2-methoxyphenyl)-2-[1-(hydroxyacetyl)-1,2,3,6-tetrahydropyridin-4-yl]-1H-pyrrolo[2,3-b]pyridine-5-carbonitrile;

4-[5-cyano-4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-N-[2-(piperazin-1-yl)ethyl]-3,6-dihydropyridine-1(2H)-carboxamide;

N-[2-(4-aminopiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

N-{2-[(1,3-dihydroxypropan-2-yl)amino]ethyl}-4-[4-(5-fluoro-2-methoxyphenyl)-1H-pyrrolo[2,3-b]pyridin-2-yl]-3,6-dihydropyridine-1(2H)-carboxamide;

3-ethoxy-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

5-fluoro-4-(5-fluoro-2-methoxyphenyl)-2-(1,2,3,6-tetrahydropyridin-4-yl)-1H-pyrrolo[2,3-b]pyridine;

4-[5-fluoro-4-(5-fluoro-2-methoxyphenyl)-1H-pyrrolo[2,3-b]pyridin-2-yl]-N-methyl-3,6-dihydropyridine-1(2H)-carboxamide;

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]-3,6-dihydropyridin-1(2H)-yl}propane-1,2-diol;

1-{4-[4-(5-fluoro-2-methoxyphenyl)-1H-pyrrolo[2,3-b]pyridin-2-yl]-3,6-dihydropyridin-1(2H)-yl}-2-(methylsulfonyl)ethanone;

ethyl 3-{4-[4-(5-fluoro-2-methoxyphenyl)-1H-pyrrolo[2,3-b]pyridin-2-yl]-3,6-dihydropyridin-1(2H)-yl}-3-oxopropanoate;

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}-3,6-dihydropyridine-1(2H)-carboxamide;

N-(2-{4-[4-(5-fluoro-2-methoxyphenyl)-1H-pyrrolo[2,3-b]pyridin-2-yl]-3,6-dihydropyridin-1(2H)-yl}-2-oxoethyl)methanesulfonamide;

4-[4-(2,3-difluorophenyl)-1H-pyrrolo[2,3-b]pyridin-2-yl]cyclohex-3-ene-1-carboxylic acid;

N-({4-[4-(5-fluoro-2-methoxyphenyl)-1H-pyrrolo[2,3-b]pyridin-2-yl]cyclohex-3-en-1-yl}carbonyl)glycine;

3-{4-[4-(5-fluoro-2-methoxyphenyl)-1H-pyrrolo[2,3-b]pyridin-2-yl]-3,6-dihydropyridin-1(2H)-yl}-3-oxopropanoic acid;

4-(4-chloro-2-methoxyphenyl)-2-(1,2,3,6-tetrahydropyridin-4-yl)-1H-pyrrolo[2,3-b]pyridine;

4-(2,4-dimethoxyphenyl)-2-[1-(methylsulfonyl)-1,2,3,6-tetrahydropyridin-4-yl]-1H-pyrrolo[2,3-b]pyridine;

3-{4-[4-(2,4-dimethoxyphenyl)-1H-pyrrolo[2,3-b]pyridin-2-yl]-3,6-dihydropyridin-1(2H)-yl}propane-1,2-diol;

4-[4-(2,4-dimethoxyphenyl)-1H-pyrrolo[2,3-b]pyridin-2-yl]-N-methyl-3,6-dihydropyridine-1(2H)-carboxamide;

1-{4-[4-(2,4-dimethoxyphenyl)-1H-pyrrolo[2,3-b]pyridin-2-yl]-3,6-dihydropyridin-1(2H)-yl}-2-hydroxyethanone;

3-{4-[4-(2-methoxyphenyl)-1H-pyrrolo[2,3-b]pyridin-2-yl]-3,6-dihydropyridin-1(2H)-yl}propane-1,2-diol;

4-[4-(2-methoxyphenyl)-1H-pyrrolo[2,3-b]pyridin-2-yl]-N-methyl-3,6-dihydropyridine-1(2H)-carboxamide;

2-hydroxy-1-{4-[4-(2-methoxyphenyl)-1H-pyrrolo[2,3-b]pyridin-2-yl]-3,6-dihydropyridin-1(2H)-yl}ethanone;

3-{4-[4-(4-fluoro-2-methoxyphenyl)-1H-pyrrolo[2,3-b]pyridin-2-yl]-3,6-dihydropyridin-1(2H)-yl}propane-1,2-diol;

4-[4-(4-fluoro-2-methoxyphenyl)-1H-pyrrolo[2,3-b]pyridin-2-yl]-N-methyl-3,6-dihydropyridine-1(2H)-carboxamide;

1-{4-[4-(4-fluoro-2-methoxyphenyl)-1H-pyrrolo[2,3-b]pyridin-2-yl]-3,6-dihydropyridin-1(2H)-yl}-2-hydroxyethanone;

3-{4-[4-(4,5-difluoro-2-methoxyphenyl)-1H-pyrrolo[2,3-b]pyridin-2-yl]-3,6-dihydropyridin-1(2H)-yl}propane-1,2-diol;

1-{4-[4-(4,5-difluoro-2-methoxyphenyl)-1H-pyrrolo[2,3-b]pyridin-2-yl]-3,6-dihydropyridin-1(2H)-yl}-2-hydroxyethanone;

N-({4-[4-(5-fluoro-2-methoxyphenyl)-1H-pyrrolo[2,3-b]pyridin-2-yl]-3,6-dihydropyridin-1(2H)-yl}sulfonyl)acetamide;

4-(4,5-difluoro-2-methoxyphenyl)-2-[1-(methylsulfonyl)-1,2,3,6-tetrahydropyridin-4-yl]-1H-pyrrolo[2,3-b]pyridine;

4-(5-fluoro-2-methoxyphenyl)-3-methyl-2-(1,2,3,6-tetrahydropyridin-4-yl)-1H-pyrrolo[2,3-b]pyridine;

2-(8-azabicyclo[3.2.1]oct-2-en-3-yl)-4-(2,3-difluorophenyl)-1H-pyrrolo[2,3-b]pyridine;

{4-[5-cyano-4-(5-fluoro-2-methoxyphenyl)-1H-pyrrolo[2,3-b]pyridin-2-yl]-3,6-dihydropyridin-1(2H)-yl}acetic acid;

4-[4-(5-fluoro-2-methoxyphenyl)-1H-pyrrolo[2,3-b]pyridin-2-yl]-N-(2-{[2-(1H-imidazol-4-yl)ethyl]amino}ethyl)-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxypropyl)amino]ethyl}-3,6-dihydropyridine-1(2H)-carboxamide;

N-[2-(dimethylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(2-{[(3-methyloxetan-3-yl)methyl]amino}ethyl)-3,6-dihydropyridine-1(2H)-carboxamide;

4-[4-(5-fluoro-2-methoxyphenyl)-1H-pyrrolo[2,3-b]pyridin-2-yl]-N-[2-(oxetan-3-ylamino)ethyl]-3,6-dihydropyridine-1(2H)-carboxamide;

3-methoxy-N-methyl-4-[2-(1,2,3,6-tetrahydropyridin-4-yl)-1H-pyrrolo[2,3-b]pyridin-4-yl]benzamide;

3-methoxy-N-methyl-4-{2-[1-(methylsulfonyl)-1,2,3,6-tetrahydropyridin-4-yl]-1H-pyrrolo[2,3-b]pyridin-4-yl}benzamide;

4-{2-[1-(2,3-dihydroxypropyl)-1,2,3,6-tetrahydropyridin-4-yl]-1H-pyrrolo[2,3-b]pyridin-4-yl}-3-methoxy-N-methylbenzamide;

3-amino-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

4-(5-fluoro-2-methoxyphenyl)-2-(2,5,6,7-tetrahydro-14-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,75-tetrahydro-1H-azepin-4-yl)-1H-pyrrolo[2,3-b]pyridine;

4-(5-fluoro-2-methoxyphenyl)-2-[1-(methylsulfonyl)-2,5,6,7-tetrahydro-1H-azepin-4-yl]-1H-pyrrolo[2,3-b]pyridine and 4-(5-fluoro-2-methoxyphenyl)-2-(1-(methylsulfonyl)-2,3,6,7-tetrahydro-1H-azepin-4-yl)-1H-pyrrolo[2,3-b]pyridine;

5-[4-(5-fluoro-2-methoxyphenyl)-1H-pyrrolo[2,3-b]pyridin-2-yl]-N-methyl-2,3,4,7-tetrahydro-1H-azepine-1-carboxamide and 4-(4-(5-fluoro-2-methoxyphenyl)-1H-pyrrolo[2,3-b]pyridin-2-yl)-N-methyl-2,3,6,7-tetrahydro-1H-azepine-1-carboxamide;

1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(methylsulfonyl)acetamide;

2-{4-[4-(2,4-dimethoxyphenyl)-1H-pyrrolo[2,3-b]pyridin-2-yl]-3,6-dihydropyridin-1(2H)-yl}-N,N-dimethylacetamide;

2-{4-[4-(2-methoxyphenyl)-1H-pyrrolo[2,3-b]pyridin-2-yl]-3,6-dihydropyridin-1(2H)-yl}-N,N-dimethylacetamide;

2-{4-[4-(4-fluoro-2-methoxyphenyl)-1H-pyrrolo[2,3-b]pyridin-2-yl]-3,6-dihydropyridin-1(2H)-yl}-N,N-dimethylacetamide;

2-{4-[4-(4,5-difluoro-2-methoxyphenyl)-1H-pyrrolo[2,3-b]pyridin-2-yl]-3,6-dihydropyridin-1(2H)-yl}-N,N-dimethylacetamide;

tert-butyl {5-[4-(5-fluoro-2-methoxyphenyl)-1H-pyrrolo[2,3-b]pyridin-2-yl]-3,6-dihydropyridin-1(2H)-yl}acetate;

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)acetamide;

N-({4-[4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

2-{5-[4-(5-fluoro-2-methoxyphenyl)-1H-pyrrolo[2,3-b]pyridin-2-yl]-3,6-dihydropyridin-1(2H)-yl}-N,N-dimethylacetamide;

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

ethyl ({4-[4-(5-fluoro-2-methoxyphenyl)-3-methyl-1H-pyrrolo[2,3-b]pyridin-2-yl]-3,6-dihydropyridin-1(2H)-yl}sulfonyl)carbamate;

{5-[4-(5-fluoro-2-methoxyphenyl)-1H-pyrrolo[2,3-b]pyridin-2-yl]-3,6-dihydropyridin-1(2H)-yl}acetic acid;

ethyl 1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylate;

4-[4-(5-fluoro-2-methoxyphenyl)-3-methyl-1H-pyrrolo[2,3-b]pyridin-2-yl]-N-methyl-3,6-dihydropyridine-1(2H)-carboxamide;

4-(5-fluoro-2-methoxyphenyl)-3-methyl-2-[1-(methylsulfonyl)-1,2,3,6-tetrahydropyridin-4-yl]-1H-pyrrolo[2,3-b]pyridine;

2-(dimethylamino)-1-{4-[4-(5-fluoro-2-methoxyphenyl)-1H-pyrrolo[2,3-b]pyridin-2-yl]-3,6-dihydropyridin-1(2H)-yl}ethanone;

{4-[5-fluoro-4-(5-fluoro-2-methoxyphenyl)-1H-pyrrolo[2,3-b]pyridin-2-yl]-3,6-dihydropyridin-1(2H)-yl}acetic acid;

2-({4-[4-(5-fluoro-2-methoxyphenyl)-1H-pyrrolo[2,3-b]pyridin-2-yl]cyclohex-3-en-1-yl}amino)butanoic acid;

4-(2,3-difluorophenyl)-2-[1-(methylsulfonyl)-1,2,5,6-tetrahydropyridin-3-yl]-1H-pyrrolo[2,3-b]pyridine;
2-{5-[4-(2,3-difluorophenyl)-1H-pyrrolo[2,3-b]pyridin-2-yl]-3,6-dihydropyridin-1(2H)-yl}-N,N-dimethylacetamide;
1-{5-[4-(2,3-difluorophenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-[1-(methylsulfonyl)azepan-4-yl]-1H-pyrrolo[2,3-b]pyridine;
{3-[4-(5-fluoro-2-methoxyphenyl)-1H-pyrrolo[2,3-b]pyridin-2-yl]-2,5-dihydro-1H-pyrrol-1-yl}acetic acid;
2-{4-[4-(5-fluoro-2-methoxyphenyl)-1H-pyrrolo[2,3-b]pyridin-2-yl]piperidin-1-yl}-N,N-dimethylethanesulfonamide;
{4-[4-(2,4-dimethoxyphenyl)-1H-pyrrolo[2,3-b]pyridin-2-yl]-3,6-dihydropyridin-1(2H)-yl}acetic acid;
{4-[4-(2-methoxyphenyl)-1H-pyrrolo[2,3-b]pyridin-2-yl]-3,6-dihydropyridin-1(2H)-yl}acetic acid;
{4-[4-(4,5-difluoro-2-methoxyphenyl)-1H-pyrrolo[2,3-b]pyridin-2-yl]-3,6-dihydropyridin-1(2H)-yl}acetic acid;
1-{4-[4-(5-fluoro-2-methoxyphenyl)-1H-pyrrolo[2,3-b]pyridin-2-yl]-3,6-dihydropyridin-1(2H)-yl}-2-(3-hydroxypyrrolidin-1-yl)ethanone;
methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate;
{4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetic acid;
N-(cyclopropylsulfonyl)-4-[4-(5-fluoro-2-methoxyphenyl)-1H-pyrrolo[2,3-b]pyridin-2-yl]cyclohex-3-ene-1-carboxamide;
4-[4-(5-fluoro-2-methoxyphenyl)-1H-pyrrolo[2,3-b]pyridin-2-yl]-N-(phenylsulfonyl)-3,6-dihydropyridine-1(2H)-carboxamide;
5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one;
{4-[4-(5-fluoro-2-methoxyphenyl)-1H-pyrrolo[2,3-b]pyridin-2-yl]piperidin-1-yl}acetic acid;
{3-[4-(5-fluoro-2-methoxyphenyl)-1H-pyrrolo[2,3-b]pyridin-2-yl]pyrrolidin-1-yl}acetic acid;
4-[4-(5-fluoro-2-methoxyphenyl)-1H-pyrrolo[2,3-b]pyridin-2-yl]-2,5-dihydro-1H-pyrrole-2-carboxylic acid;
3-{4-[4-(2,3-difluorophenyl)-1H-pyrrolo[2,3-b]pyridin-2-yl]-3,6-dihydropyridin-1(2H)-yl}-3-oxopropanenitrile;
{4-[4-(5-fluoro-2-methoxyphenyl)-1H-pyrrolo[2,3-b]pyridin-2-yl]-3,6-dihydropyridin-1(2H)-yl}(1-hydroxycyclopropyl)methanone;
3-{5-[4-(2,3-difluorophenyl)-1H-pyrrolo[2,3-b]pyridin-2-yl]-3,6-dihydropyridin-1(2H)-yl}propane-1,2-diol;
1-{5-[4-(2,3-difluorophenyl)-1H-pyrrolo[2,3-b]pyridin-2-yl]-3,6-dihydropyridin-1(2H)-yl}-2-hydroxy-2-methylpropan-1-one;
{4-[4-(4-fluorophenyl)-1H-pyrrolo[2,3-b]pyridin-2-yl]-3,6-dihydropyridin-1(2H)-yl}acetic acid;
{3-[4-(5-fluoro-2-methoxyphenyl)-1H-pyrrolo[2,3-b]pyridin-2-yl]-8-azabicyclo[3.2.1]oct-2-en-8-yl}acetic acid;
1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylic acid;
1-{5-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;
4-[4-(5-fluoro-2-methoxyphenyl)-1H-pyrrolo[2,3-b]pyridin-2-yl]-N-(propan-2-ylsulfonyl)cyclohex-3-ene-1-carboxamide;
2-{4-[4-(5-fluoro-2-methoxyphenyl)-1H-pyrrolo[2,3-b]pyridin-2-yl]-3,6-dihydropyridin-1(2H)-yl}-2-oxoethanesulfonamide;
2-{4-[4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;
tert-butyl {4-[4-(5-fluoro-2-methoxyphenyl)-1H-pyrrolo[2,3-b]pyridin-2-yl]-3,6-dihydropyridin-1(2H)-yl}acetate;
4-[4-(5-fluoro-2-methoxyphenyl)-1H-pyrrolo[2,3-b]pyridin-2-yl]-N-{1-[(2R)-2-hydroxypropyl]-1H-pyrazol-4-yl}-3,6-dihydropyridine-1(2H)-carboxamide;
4-(5-fluoro-2-methoxyphenyl)-2-[1-(2H-tetrazol-5-ylmethyl)-1,2,3,6-tetrahydropyridin-4-yl]-1H-pyrrolo[2,3-b]pyridine;
6-[4-(5-fluoro-2-methoxyphenyl)-1H-pyrrolo[2,3-b]pyridin-2-yl]-2-azaspiro[3.3]heptan-6-ol;
{(2R)-4-[4-(5-fluoro-2-methoxyphenyl)-1H-pyrrolo[2,3-b]pyridin-2-yl]-2,5-dihydro-1H-pyrrol-2-yl}methanol;
{4-[4-(2,3-difluorophenyl)-1H-pyrrolo[2,3-b]pyridin-2-yl]-3,6-dihydropyridin-1(2H)-yl}acetic acid;
4-[4-(5-fluoro-2-methoxyphenyl)-1H-pyrrolo[2,3-b]pyridin-2-yl]cyclohex-3-en-1-ol;
2-{3-[4-(5-fluoro-2-methoxyphenyl)-1H-pyrrolo[2,3-b]pyridin-2-yl]pyrrolidin-1-yl}-N,N-dimethylacetamide;
3-[4-(5-fluoro-2-methoxyphenyl)-1H-pyrrolo[2,3-b]pyridin-2-yl]cyclopent-3-en-1-amine;
3-[4-(5-fluoro-2-methoxyphenyl)-1H-pyrrolo[2,3-b]pyridin-2-yl]cyclopent-2-en-1-amine;
2-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]-1H-isoindole-1,3(2H)-dione;
3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;
4-[4-(5-fluoro-2-methoxyphenyl)-1H-pyrrolo[2,3-b]pyridin-2-yl]-N-(2-{[(1S,2S)-2-hydroxycyclohexyl]amino}ethyl)-3,6-dihydropyridine-1(2H)-carboxamide;
N-(2-{[2-(dimethylamino)ethyl]amino}ethyl)-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-{2-[(2-methoxyethyl)(methyl)amino]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[4-(4-methylbenzoyl)piperazin-1-yl]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[4-(methylsulfonyl)piperazin-1-yl]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide;
4-[4-(5-fluoro-2-methoxyphenyl)-1H-pyrrolo[2,3-b]pyridin-2-yl]-N-(2-{[3-(trifluoromethyl)benzyl]amino}ethyl)-3,6-dihydropyridine-1(2H)-carboxamide;
ethyl ({4-[4-(2,3-difluorophenyl)-1H-pyrrolo[2,3-b]pyridin-2-yl]-3,6-dihydropyridin-1(2H)-yl}sulfonyl)carbamate;
2,2,2-trifluoroethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-[4-(5-fluoro-2-methoxyphenyl)-1H-pyrrolo[2,3-b]pyridin-2-yl]cyclohex-3-en-1-one;
2-(3,6-dihydro-2H-thiopyran-4-yl)-4-(5-fluoro-2-methoxyphenyl)-1H-pyrrolo[2,3-b]pyridine;
3-fluoro-N-methyl-4-[2-(1,2,3,6-tetrahydropyridin-4-yl)-1H-pyrrolo[2,3-b]pyridin-4-yl]benzamide;

N-({4-[4-(5-fluoro-2-methoxyphenyl)-1H-pyrrolo[2,3-b]pyridin-2-yl]-3,6-dihydropyridin-1(2H)-yl}carbonyl)alanine;

4-(5-fluoro-2-methoxyphenyl)-2-(1-oxido-3,6-dihydro-2H-thiopyran-4-yl)-1H-pyrrolo[2,3-b]pyridine;

4-[4-(5-fluoro-2-methoxyphenyl)-1H-pyrrolo[2,3-b]pyridin-2-yl]-N-[(1-methylcyclopropyl)sulfonyl]cyclohex-3-ene-1-carboxamide;

4-[4-(5-fluoro-2-methoxyphenyl)-1H-pyrrolo[2,3-b]pyridin-2-yl]-N-[(2-methylpropyl)sulfonyl]cyclohex-3-ene-1-carboxamide;

4-[4-(2,3-difluorophenyl)-1H-pyrrolo[2,3-b]pyridin-2-yl]-N-(phenylsulfonyl)-3,6-dihydropyridine-1(2H)-carboxamide;

4-(5-fluoro-2-methoxyphenyl)-2-(1,2,3,6-tetrahydropyridin-4-yl)-1H-pyrrolo[2,3-b]pyridine-5-carboxamide;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-5-carbonitrile;

2-{4-[5-chloro-4-(5-fluoro-2-methoxyphenyl)-1H-pyrrolo[2,3-b]pyridin-2-yl]-3,6-dihydropyridin-1(2H)-yl}-N,N-dimethylacetamide;

{4-[5-chloro-4-(5-fluoro-2-methoxyphenyl)-1H-pyrrolo[2,3-b]pyridin-2-yl]-3,6-dihydropyridin-1(2H)-yl}acetic acid;

3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol;

{4-[4-(5-fluoro-2-methoxyphenyl)-1H-pyrrolo[2,3-b]pyridin-2-yl]-3,6-dihydropyridin-1(2H)-yl}[(2S,4S)-4-hydroxypyrrolidin-2-yl]methanone;

N-[2-(ethylamino)ethyl]-4-[4-(5-fluoro-2-methoxyphenyl)-1H-pyrrolo[2,3-b]pyridin-2-yl]-3,6-dihydropyridine-1(2H)-carboxamide;

N-[2-(cyclopropylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(pyridin-2-ylmethyl)amino]ethyl}-3,6-dihydropyridine-1(2H)-carboxamide;

3-amino-4-{4-[4-(2-{2-[(2-amino-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

tert-butyl 4-({4-[4-(5-fluoro-2-methoxyphenyl)-1H-pyrrolo[2,3-b]pyridin-2-yl]-3,6-dihydropyridin-1(2H)-yl}sulfonyl)piperidine-1-carboxylate;

4-[4-(5-fluoro-2-methoxyphenyl)-1H-pyrrolo[2,3-b]pyridin-2-yl]-1-(methylsulfonyl)-2,5-dihydro-1H-pyrrole-2-carboxylic acid;

4-(5-fluoro-2-methoxyphenyl)-2-[1-(piperidin-4-ylsulfonyl)-1,2,3,6-tetrahydropyridin-4-yl]-1H-pyrrolo[2,3-b]pyridine;

N,N-dimethyl-4-{2-[1-(methylsulfonyl)-1,2,3,6-tetrahydropyridin-4-yl]-1H-pyrrolo[2,3-b]pyridin-4-yl}benzamide;

2-{4-[4-(5-fluoro-2-methoxyphenyl)-1H-pyrrolo[2,3-b]pyridin-2-yl]-3,6-dihydropyridin-1(2H)-yl}-N,N-dimethylpropanamide;

4-(4-fluoro-2-methoxyphenyl)-2-[8-(methylsulfonyl)-8-azabicyclo[3.2.1]oct-2-en-3-yl]-1H-pyrrolo[2,3-b]pyridine;

4-(4,5-difluoro-2-methoxyphenyl)-2-[8-(methylsulfonyl)-8-azabicyclo[3.2.1]oct-2-en-3-yl]-1H-pyrrolo[2,3-b]pyridine;

4-(2-methoxyphenyl)-2-[8-(methylsulfonyl)-8-azabicyclo[3.2.1]oct-2-en-3-yl]-1H-pyrrolo[2,3-b]pyridine;

4-(3-fluoro-2-methoxyphenyl)-2-(1,2,3,6-tetrahydropyridin-4-yl)-1H-pyrrolo[2,3-b]pyridine;

ethyl ({4-[4-(4-fluoro-2-methoxyphenyl)-1H-pyrrolo[2,3-b]pyridin-2-yl]-3,6-dihydropyridin-1(2H)-yl}sulfonyl)carbamate;

ethyl ({4-[4-(2,4-dimethoxyphenyl)-1H-pyrrolo[2,3-b]pyridin-2-yl]-3,6-dihydropyridin-1(2H)-yl}sulfonyl)carbamate;

ethyl ({4-[4-(2-methoxyphenyl)-1H-pyrrolo[2,3-b]pyridin-2-yl]-3,6-dihydropyridin-1(2H)-yl}sulfonyl)carbamate;

ethyl ({4-[4-(4,5-difluoro-2-methoxyphenyl)-1H-pyrrolo[2,3-b]pyridin-2-yl]-3,6-dihydropyridin-1(2H)-yl}sulfonyl)carbamate;

{4-[4-(5-fluoro-2-methoxyphenyl)-1H-pyrrolo[2,3-b]pyridin-2-yl]-3,6-dihydropyridin-1(2H)-yl}[(2S,4R)-4-hydroxypyrrolidin-2-yl]methanone;

{4-[4-(5-fluoro-2-methoxyphenyl)-1H-pyrrolo[2,3-b]pyridin-2-yl]-3,6-dihydropyridin-1(2H)-yl}[(2R,4S)-4-hydroxypyrrolidin-2-yl]methanone;

4-[4-(5-fluoro-2-methoxyphenyl)-1H-pyrrolo[2,3-b]pyridin-2-yl]-N,N-dimethylcyclohex-3-ene-1-carboxamide;

N-{4-[4-(5-fluoro-2-methoxyphenyl)-1H-pyrrolo[2,3-b]pyridin-2-yl]cyclohex-3-en-1-yl}alanine;

2-({4-[4-(5-fluoro-2-methoxyphenyl)-1H-pyrrolo[2,3-b]pyridin-2-yl]-3,6-dihydropyridin-1(2H)-yl}sulfonyl)ethanamine;

4-{2-[1-(methylsulfonyl)-1,2,3,6-tetrahydropyridin-4-yl]-1H-pyrrolo[2,3-b]pyridin-4-yl}-N-propylbenzamide;

3-fluoro-N-methyl-4-{2-[1-(methylsulfonyl)-1,2,3,6-tetrahydropyridin-4-yl]-1H-pyrrolo[2,3-b]pyridin-4-yl}benzamide;

ethyl {[4-{4-[2-fluoro-4-(methylcarbamoyl)phenyl]-1H-pyrrolo[2,3-b]pyridin-2-yl}-3,6-dihydropyridin-1(2H)-yl]sulfonyl}carbamate;

[4-{4-[2-fluoro-4-(methylcarbamoyl)phenyl]-1H-pyrrolo[2,3-b]pyridin-2-yl}-3,6-dihydropyridin-1(2H)-yl]acetic acid;

4-(5-fluoro-2-methoxyphenyl)-2-(1,2,3,3a,4,6a-hexahydrocyclopenta[c]pyrrol-5-yl)-1H-pyrrolo[2,3-b]pyridine;

tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate;

tert-butyl 4-[4-(5-fluoro-2-methoxyphenyl)-1H-pyrrolo[2,3-b]pyridin-2-yl]-2-[(methylsulfonyl)carbamoyl]-2,5-dihydro-1H-pyrrole-1-carboxylate;

2-fluoro-N-methyl-4-[2-(1,2,3,6-tetrahydropyridin-4-yl)-1H-pyrrolo[2,3-b]pyridin-4-yl]benzamide;

4-{4-[3-fluoro-4-(methylcarbamoyl)phenyl]-1H-pyrrolo[2,3-b]pyridin-2-yl}-N-methyl-3,6-dihydropyridine-1(2H)-carboxamide;

4-(2-{1-[2-(dimethylamino)-2-oxoethyl]-1,2,3,6-tetrahydropyridin-4-yl}-1H-pyrrolo[2,3-b]pyridin-4-yl)-2-fluoro-N-methylbenzamide;

4-{2-[1-(2,3-dihydroxypropyl)-1,2,3,6-tetrahydropyridin-4-yl]-1H-pyrrolo[2,3-b]pyridin-4-yl}-2-fluoro-N-methylbenzamide;

4-(5-fluoro-2-methoxyphenyl)-5-methoxy-2-[1-(methylsulfonyl)-1,2,3,6-tetrahydropyridin-4-yl]-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}serine;

3-[4-(5-fluoro-2-methoxyphenyl)-1H-pyrrolo[2,3-b]pyridin-2-yl]cyclohex-3-ene-1-carboxylic acid;

{4-[4-(5-fluoro-2-methoxyphenyl)-1H-pyrrolo[2,3-b]pyridin-2-yl]-1,2,3,6-tetrahydropyridin-2-yl}methanol;

7-[4-(5-fluoro-2-methoxyphenyl)-1H-pyrrolo[2,3-b]pyridin-2-yl]-3-oxa-9-azabicyclo[3.3.1]non-6-ene;

7-[4-(5-fluoro-2-methoxyphenyl)-1H-pyrrolo[2,3-b]pyridin-2-yl]-9-(methylsulfonyl)-3-oxa-9-azabicyclo[3.3.1]non-6-ene;

ethyl ({7-[4-(5-fluoro-2-methoxyphenyl)-1H-pyrrolo[2,3-b]pyridin-2-yl]-3-oxa-9-azabicyclo[3.3.1]non-6-en-9-yl}sulfonyl)carbamate;

2-{7-[4-(5-fluoro-2-methoxyphenyl)-1H-pyrrolo[2,3-b]pyridin-2-yl]-3-oxa-9-azabicyclo[3.3.1]non-6-en-9-yl}-N,N-dimethylacetamide;

N-{4-[4-(5-fluoro-2-methoxyphenyl)-1H-pyrrolo[2,3-b]pyridin-2-yl]cyclohex-3-en-1-yl}-L-isoleucine;

ethyl {[4-{4-[3-fluoro-4-(methylcarbamoyl)phenyl]-1H-pyrrolo[2,3-b]pyridin-2-yl}-3,6-dihydropyridin-1(2H)-yl]sulfonyl}carbamate;

4-(3-fluoro-2-methoxyphenyl)-2-[1-(methylsulfonyl)-1,2,3,6-tetrahydropyridin-4-yl]-1H-pyrrolo[2,3-b]pyridine;

4-[4-(3-fluoro-2-methoxyphenyl)-1H-pyrrolo[2,3-b]pyridin-2-yl]-N-methyl-3,6-dihydropyridine-1(2H)-carboxamide;

methyl 4-[4-(5-fluoro-2-methoxyphenyl)-1H-pyrrolo[2,3-b]pyridin-2-yl]-2,5-dihydro-1H-pyrrole-2-carboxylate;

1-{4-[4-(5-fluoro-2-methoxyphenyl)-1H-pyrrolo[2,3-b]pyridin-2-yl]-3,6-dihydropyridin-1(2H)-yl}-3-(3-hydroxyazetidin-1-yl)propane-1,3-dione;

[(2S)-4-[4-(5-fluoro-2-methoxyphenyl)-1H-pyrrolo[2,3-b]pyridin-2-yl]-1-(methylsulfonyl)-2,5-dihydro-1H-pyrrol-2-yl]methanol;

ethyl {[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]sulfonyl}carbamate;

2-({4-[4-(5-fluoro-2-methoxyphenyl)-1H-pyrrolo[2,3-b]pyridin-2-yl]-3,6-dihydropyridin-1(2H)-yl}sulfonyl)-1-(3-hydroxyazetidin-1-yl)ethanone;

{(2S)-4-[4-(5-fluoro-2-methoxyphenyl)-1H-pyrrolo[2,3-b]pyridin-2-yl]-2,5-dihydro-1H-pyrrol-2-yl}methanol;

8-[4-(5-fluoro-2-methoxyphenyl)-1H-pyrrolo[2,3-b]pyridin-2-yl]-1,3-diazaspiro[4.5]dec-7-ene-2,4-dione;

1-amino-4-[4-(5-fluoro-2-methoxyphenyl)-1H-pyrrolo[2,3-b]pyridin-2-yl]cyclohex-3-ene-1-carboxylic acid;

2-(2-azaspiro[3.3]hept-6-yl)-4-(5-fluoro-2-methoxyphenyl)-1H-pyrrolo[2,3-b]pyridine;

4-(5-fluoro-2-methoxyphenyl)-5-methoxy-2-(1,2,3,6-tetrahydropyridin-4-yl)-1H-pyrrolo[2,3-b]pyridine;

ethyl 4-(5-fluoro-2-methoxyphenyl)-2-(1,2,3,6-tetrahydropyridin-4-yl)-1H-pyrrolo[2,3-b]pyridine-3-carboxylate;

4-(5-fluoro-2-methoxyphenyl)-2-(1-{[1-(methylsulfonyl)piperidin-4-yl]sulfonyl}-1,2,3,6-tetrahydropyridin-4-yl)-1H-pyrrolo[2,3-b]pyridine;

N-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]methanesulfonamide;

{4-[4-(5-fluoro-2-methoxyphenyl)-1H-pyrrolo[2,3-b]pyridin-2-yl]-1-(methylsulfonyl)-1,2,3,6-tetrahydropyridin-2-yl}methanol;

ethyl ({4-[4-(5-fluoro-2-methoxyphenyl)-1H-pyrrolo[2,3-b]pyridin-2-yl]-2-(hydroxymethyl)-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-2-(hydroxymethyl)-3,6-dihydropyridin-1(2H)-yl}-N,N-dimethylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

4-(3-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-[4-(5-fluoro-2-methoxyphenyl)-1H-pyrrolo[2,3-b]pyridin-2-yl]-N,N-dimethyl-2,5-dihydro-1H-pyrrole-2-carboxamide;

2-(4-{4-[4-(5-fluoro-2-methoxyphenyl)-1H-pyrrolo[2,3-b]pyridin-2-yl]-3,6-dihydropyridin-1(2H)-yl}piperidin-1-yl)-N,N-dimethylacetamide;

N-{4-[4-(2,3-difluorophenyl)-1H-pyrrolo[2,3-b]pyridin-2-yl]cyclohex-3-en-1-yl}glycine;

1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone;

4-(5-fluoro-2-methoxyphenyl)-2-(1-{[1-(methylsulfonyl)azetidin-3-yl]sulfonyl}-1,2,3,6-tetrahydropyridin-4-yl)-1H-pyrrolo[2,3-b]pyridine;

ethyl 4-(5-fluoro-2-methoxyphenyl)-2-[1-(methylsulfonyl)-1,2,3,6-tetrahydropyridin-4-yl]-1H-pyrrolo[2,3-b]pyridine-3-carboxylate;

4-(5-fluoro-2-methoxyphenyl)-2-(2,3,6,7-tetrahydro-1H-azepin-4-yl)-1H-pyrrolo[2,3-b]pyridine;

3-(2-{4-[4-(5-fluoro-2-methoxyphenyl)-1H-pyrrolo[2,3-b]pyridin-2-yl]-3,6-dihydropyridin-1(2H)-yl}-2-oxoethyl)imidazolidine-2,4-dione;

({4-[4-(5-fluoro-2-methoxyphenyl)-1H-pyrrolo[2,3-b]pyridin-2-yl]-3,6-dihydropyridin-1(2H)-yl}sulfonyl)acetonitrile;

propan-2-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-(5-fluoro-2-methoxyphenyl)-2-[2-(methylsulfonyl)-2-azaspiro[3.3]hept-6-yl]-1H-pyrrolo[2,3-b]pyridine;

ethyl ({4-[5-cyano-4-(5-fluoro-2-methoxyphenyl)-1H-pyrrolo[2,3-b]pyridin-2-yl]-3,6-dihydropyridin-1(2H)-yl}sulfonyl)carbamate;

N-[2-(4-fluoro-2-{2-[1-(methylsulfonyl)-1,2,3,6-tetrahydropyridin-4-yl]-1H-pyrrolo[2,3-b]pyridin-4-yl}phenoxy)ethyl]methanesulfonamide;

2-{4-fluoro-2-[2-(1,2,3,6-tetrahydropyridin-4-yl)-1H-pyrrolo[2,3-b]pyridin-4-yl]phenoxy}ethanamine;

N-[4-({4-[4-(5-fluoro-2-methoxyphenyl)-1H-pyrrolo[2,3-b]pyridin-2-yl]-3,6-dihydropyridin-1(2H)-yl}methyl)phenyl]methanesulfonamide;

tert-butyl 4-{4-[5-fluoro-2-(methylamino)phenyl]-1H-pyrrolo[2,3-b]pyridin-2-yl}-3,6-dihydropyridine-1(2H)-carboxylate;

4-fluoro-N-methyl-2-[2-(1,2,3,6-tetrahydropyridin-4-yl)-1H-pyrrolo[2,3-b]pyridin-4-yl]aniline;

1-amino-4-[4-(5-fluoro-2-methoxyphenyl)-1H-pyrrolo[2,3-b]pyridin-2-yl]-N,N-dimethylcyclohex-3-ene-1-carboxamide;

4-(5-fluoro-2-methoxyphenyl)-2-(1,2,3,6-tetrahydropyridin-4-yl)-1H-pyrrolo[2,3-b]pyridine-3-carbonitrile;

1-(3-{4-[4-(5-fluoro-2-methoxyphenyl)-1H-pyrrolo[2,3-b]pyridin-2-yl]-3,6-dihydropyridin-1(2H)-yl}-3-oxopropanoyl)prolinamide;

N-ethoxy-4-[4-(5-fluoro-2-methoxyphenyl)-1H-pyrrolo[2,3-b]pyridin-2-yl]cyclohex-3-ene-1-carboxamide;

4-(5-fluoro-2-methoxyphenyl)-2-(1,2,3,6-tetrahydropyridin-4-yl)-1H-pyrrolo[2,3-b]pyridine-3-carboxamide;

ethyl ({3-[4-(5-fluoro-2-methoxyphenyl)-1H-pyrrolo[2,3-b]pyridin-2-yl]-8-azabicyclo[3.2.1]oct-2-en-8-yl}sulfonyl)carbamate;

4-[4-(5-fluoro-2-methoxyphenyl)-1H-pyrrolo[2,3-b]pyridin-2-yl]-N-(4-methoxybenzyl)cyclohex-3-ene-1-sulfonamide;

methyl 4-[4-(5-fluoro-2-methoxyphenyl)-1H-pyrrolo[2,3-b]pyridin-2-yl]-3,6-dihydro-2H-1,2'-bipyridine-3'-carboxylate;

1-({4-[4-(5-fluoro-2-methoxyphenyl)-1H-pyrrolo[2,3-b]pyridin-2-yl]piperidin-1-yl}acetyl)-L-prolinamide;
1-tert-butyl 2-methyl (2S)-4-{4-[4-(5-fluoro-2-methoxyphenyl)-1H-pyrrolo[2,3-b]pyridin-2-yl]-3,6-dihydropyridin-1(2H)-yl}pyrrolidine-1,2-dicarboxylate;
4-[4-(5-fluoro-2-methoxyphenyl)-1H-pyrrolo[2,3-b]pyridin-2-yl]-3,6-dihydro-2H-1,2'-bipyridine-3'-carboxylic acid;
N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide;
N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)methanesulfonamide;
3-{4-[4-(5-fluoro-2-methoxyphenyl)-1H-pyrrolo[2,3-b]pyridin-2-yl]-3,6-dihydropyridin-1(2H)-yl}-4-hydroxycyclobut-3-ene-1,2-dione;
methyl 4-{4-[4-(5-fluoro-2-methoxyphenyl)-1H-pyrrolo[2,3-b]pyridin-2-yl]-3,6-dihydropyridin-1(2H)-yl}-L-prolinate;
methyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-prolinate;
ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate;
4-(5-fluoro-2-methoxyphenyl)-2-[1-(hydroxyacetyl)-1,2,3,6-tetrahydropyridin-4-yl]-1H-pyrrolo[2,3-b]pyridine-3-carbonitrile;
2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carbonitrile;
ethyl ({4-[3-cyano-4-(5-fluoro-2-methoxyphenyl)-1H-pyrrolo[2,3-b]pyridin-2-yl]-3,6-dihydropyridin-1(2H)-yl}sulfonyl)carbamate;
2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carboxamide;
ethyl ({4-[3-carbamoyl-4-(5-fluoro-2-methoxyphenyl)-1H-pyrrolo[2,3-b]pyridin-2-yl]-3,6-dihydropyridin-1(2H)-yl}sulfonyl)carbamate;
4-[4-(5-fluoro-2-methoxyphenyl)-1H-pyrrolo[2,3-b]pyridin-2-yl]cyclohex-3-ene-1-sulfonamide;
4-(5-fluoro-2-methoxyphenyl)-2-[1-(methylcarbamoyl)-1,2,3,6-tetrahydropyridin-4-yl]-1H-pyrrolo[2,3-b]pyridine-3-carboxamide;
ethyl ({6-[4-(5-fluoro-2-methoxyphenyl)-1H-pyrrolo[2,3-b]pyridin-2-yl]-2-azaspiro[3.3]hept-2-yl}sulfonyl)carbamate;
3-{6-[4-(5-fluoro-2-methoxyphenyl)-1H-pyrrolo[2,3-b]pyridin-2-yl]-2-azaspiro[3.3]hept-2-yl}propane-1,2-diol;
2-{6-[4-(5-fluoro-2-methoxyphenyl)-1H-pyrrolo[2,3-b]pyridin-2-yl]-2-azaspiro[3.3]hept-2-yl}-N,N-dimethylacetamide;
2-({4-[4-(5-fluoro-2-methoxyphenyl)-1H-pyrrolo[2,3-b]pyridin-2-yl]-3,6-dihydropyridin-1(2H)-yl}sulfonyl)-N-(3-hydroxycyclobutyl)acetamide;
4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-proline;
4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylic acid;
2-[1-(azetidin-1-ylsulfonyl)-1,2,3,6-tetrahydropyridin-4-yl]-4-(5-fluoro-2-methoxyphenyl)-1H-pyrrolo[2,3-b]pyridine;
1-({4-[4-(5-fluoro-2-methoxyphenyl)-1H-pyrrolo[2,3-b]pyridin-2-yl]-3,6-dihydropyridin-1(2H)-yl}sulfonyl)azetidine-3-carbonitrile;
2-{1-[(4,4-difluoropiperidin-1-yl)sulfonyl]-1,2,3,6-tetrahydropyridin-4-yl}-4-(5-fluoro-2-methoxyphenyl)-1H-pyrrolo[2,3-b]pyridine;
4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}cyclohex-3-ene-1-carboxamide;
4-[4-(5-fluoro-2-methoxyphenyl)-1H-pyrrolo[2,3-b]pyridin-2-yl]-N-(1-methyl-1H-pyrazol-4-yl)cyclohex-3-ene-1-carboxamide;
4-[4-(5-fluoro-2-methoxyphenyl)-1H-pyrrolo[2,3-b]pyridin-2-yl]-N-(1H-tetrazol-5-ylmethyl)cyclohex-3-ene-1-carboxamide;
N-{4-[4-(5-fluoro-2-methoxyphenyl)-1H-pyrrolo[2,3-b]pyridin-2-yl]cyclohex-3-en-1-yl}-L-norvaline;
4-[4-(5-fluoro-2-methoxyphenyl)-1H-pyrrolo[2,3-b]pyridin-2-yl]-N-(1H-tetrazol-5-ylmethyl)cyclohex-3-en-1-amine;
2-[4-({4-[4-(5-fluoro-2-methoxyphenyl)-1H-pyrrolo[2,3-b]pyridin-2-yl]-3,6-dihydropyridin-1(2H)-yl}sulfonyl)piperidin-1-yl]-N,N-dimethylacetamide;
2-{4-[4-(5-fluoro-2-methoxyphenyl)-1H-pyrrolo[2,3-b]pyridin-2-yl]-3,6-dihydropyridin-1(2H)-yl}-1-[(2R)-2-(hydroxymethyl)pyrrolidin-1-yl]ethanone;
4-(5-fluoro-2-methoxyphenyl)-2-[1-(methylsulfonyl)-2,3,6,7-tetrahydro-1H-azepin-4-yl]-1H-pyrrolo[2,3-b]pyridine;
4-[4-(5-fluoro-2-methoxyphenyl)-1H-pyrrolo[2,3-b]pyridin-2-yl]-N-methyl-2,3,6,7-tetrahydro-1H-azepine-1-carboxamide;
[1-({4-[4-(5-fluoro-2-methoxyphenyl)-1H-pyrrolo[2,3-b]pyridin-2-yl]-3,6-dihydropyridin-1(2H)-yl}carbonyl)-1,2,3,6-tetrahydropyridin-4-yl]boronic acid;
3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione;
N-{4-[4-(5-fluoro-2-methoxyphenyl)-1H-pyrrolo[2,3-b]pyridin-2-yl]cyclohex-3-en-1-yl}methanesulfonamide;
1-{4-[4-(5-fluoro-2-methoxyphenyl)-1H-pyrrolo[2,3-b]pyridin-2-yl]cyclohex-3-en-1-yl}-3-methylurea;
N-{4-[4-(5-fluoro-2-methoxyphenyl)-1H-pyrrolo[2,3-b]pyridin-2-yl]cyclohex-3-en-1-yl}-2-hydroxyacetamide;
2-cyano-N-{4-[4-(5-fluoro-2-methoxyphenyl)-1H-pyrrolo[2,3-b]pyridin-2-yl]cyclohex-3-en-1-yl}acetamide;
4-[4-(5-fluoro-2-methoxyphenyl)-1H-pyrrolo[2,3-b]pyridin-2-yl]-1,2,5,6-tetrahydropyridine-3-carbonitrile;
(3-{4-[4-(5-fluoro-2-methoxyphenyl)-1H-pyrrolo[2,3-b]pyridin-2-yl]-3,6-dihydropyridin-1(2H)-yl}oxetan-3-yl)acetonitrile;
4-[4-(5-fluoro-2-methoxyphenyl)-1H-pyrrolo[2,3-b]pyridin-2-yl]-N-{1-[(2R)-2-hydroxypropyl]-1H-pyrazol-4-yl}cyclohex-3-ene-1-carboxamide;
2-{4-[4-(5-fluoro-2-methoxyphenyl)-1H-pyrrolo[2,3-b]pyridin-2-yl]piperidin-1-yl}-1-(3-methoxyazetidin-1-yl)ethanone;
1-({4-[4-(5-fluoro-2-methoxyphenyl)-1H-pyrrolo[2,3-b]pyridin-2-yl]piperidin-1-yl}acetyl) azetidine-3-carbonitrile;
1-(3,3-difluoroazetidin-1-yl)-2-{4-[4-(5-fluoro-2-methoxyphenyl)-1H-pyrrolo[2,3-b]pyridin-2-yl]piperidin-1-yl}ethanone;
2-{4-[4-(5-fluoro-2-methoxyphenyl)-1H-pyrrolo[2,3-b]pyridin-2-yl]piperidin-1-yl}-1-(3-hydroxy-3-methylazetidin-1-yl)ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]piperidin-1-yl}ethanone;

1-(3-fluoroazetidin-1-yl)-2-{4-[4-(5-fluoro-2-methoxyphenyl)-1H-pyrrolo[2,3-b]pyridin-2-yl]piperidin-1-yl}ethanone;

N-(3-fluorocyclobutyl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]piperidin-1-yl}-1-(3-hydroxypyrrolidin-1-yl)ethanone;

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid;

4-fluoro-2-{2-[1-(methylsulfonyl)-1,2,3,6-tetrahydropyridin-4-yl]-1H-pyrrolo[2,3-b]pyridin-4-yl}aniline;

methyl N-{4-[4-(5-fluoro-2-methoxyphenyl)-1H-pyrrolo[2,3-b]pyridin-2-yl]cyclohex-3-en-1-yl}-3-methyl-L-valinate;

N-cyano-4-[4-(5-fluoro-2-methoxyphenyl)-1H-pyrrolo[2,3-b]pyridin-2-yl]cyclohex-3-ene-1-carboxamide;

2-(3,3-dimethyl-1,2,3,6-tetrahydropyridin-4-yl)-4-(5-fluoro-2-methoxyphenyl)-1H-pyrrolo[2,3-b]pyridine;

2-(methylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-{[({4-[4-(5-fluoro-2-methoxyphenyl)-1H-pyrrolo[2,3-b]pyridin-2-yl]-3,6-dihydropyridin-1(2H)-yl}sulfonyl)carbamoyl]oxy}ethyl acetate;

2-(pyrrolidin-1-yl)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

azetidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-hydroxyethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

N-[2-(3-fluoro-5-{2-[1-(methylsulfonyl)-1,2,3,6-tetrahydropyridin-4-yl]-1H-pyrrolo[2,3-b]pyridin-4-yl}phenoxy)ethyl]methanesulfonamide;

4-[4-(5-fluoro-2-methoxyphenyl)-1H-pyrrolo[2,3-b]pyridin-2-yl]-5,6-dihydropyridin-2(1H)-one;

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)acetamide;

1-{4-[4-(5-fluoro-2-methoxyphenyl)-1H-pyrrolo[2,3-b]pyridin-2-yl]-3,6-dihydropyridin-1(2H)-yl}-3-[2-(hydroxymethyl)pyrrolidin-1-yl]propane-1,3-dione;

cyclopropyl({4-[4-(5-fluoro-2-methoxyphenyl)-1H-pyrrolo[2,3-b]pyridin-2-yl]cyclohex-3-en-1-yl}amino)acetic acid;

2-[3,3-dimethyl-1-(methylsulfonyl)-1,2,3,6-tetrahydropyridin-4-yl]-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N,3,3-trimethyl-3,6-dihydropyridine-1(2H)-carboxamide;

4-[4-(5-fluoro-2-methoxyphenyl)-1H-pyrrolo[2,3-b]pyridin-2-yl]cyclohex-3-en-1-amine;

4-(5-fluoro-2-methoxyphenyl)-2-[(6S)-6-methyl-1,2,3,6-tetrahydropyridin-4-yl]-1H-pyrrolo[2,3-b]pyridine;

$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N-methylglycinamide;

tert-butyl N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinate;

$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinamide;

$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N,N-dimethylglycinamide;

tert-butyl {4-[4-(4-fluoro-2-methoxyphenyl)-1H-pyrrolo[2,3-b]pyridin-2-yl]-3,6-dihydropyridin-1(2H)-yl}acetate;

{4-[4-(5-fluoro-2-methoxyphenyl)-1H-pyrrolo[2,3-b]pyridin-2-yl]-3,3-dimethyl-3,6-dihydropyridin-1(2H)-yl}acetic acid;

4-[4-(5-fluoro-2-methoxyphenyl)-1H-pyrrolo[2,3-b]pyridin-2-yl]cyclohex-3-ene-1-carbonitrile;

2-{4-[4-(5-fluoro-2-methoxyphenyl)-5-methoxy-1H-pyrrolo[2,3-b]pyridin-2-yl]-3,6-dihydropyridin-1(2H)-yl}-N,N-dimethylacetamide;

ethyl ({5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}sulfonyl)carbamate;

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}propane-1,2-diol;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

2-{4-[4-(4-fluoro-2-methoxyphenyl)-1H-pyrrolo[2,3-b]pyridin-2-yl]-3,6-dihydropyridin-1(2H)-yl}acetamide;

2-{4-[4-(4-fluoro-2-methoxyphenyl)-1H-pyrrolo[2,3-b]pyridin-2-yl]-3,6-dihydropyridin-1(2H)-yl}-N-methylacetamide;

N-{4-[4-(5-fluoro-2-methoxyphenyl)-1H-pyrrolo[2,3-b]pyridin-2-yl]cyclohexyl}-D-valine;

2-{4-[5-fluoro-4-(5-fluoro-2-methoxyphenyl)-1H-pyrrolo[2,3-b]pyridin-2-yl]piperidin-1-yl}acetamide;

4-(5-fluoro-2-methoxyphenyl)-2-{1-[2-(2-methoxyethoxy)ethyl]-1,2,3,6-tetrahydropyridin-4-yl}-1H-pyrrolo[2,3-b]pyridine;

4-[4-(5-fluoro-2-methoxyphenyl)-1H-pyrrolo[2,3-b]pyridin-2-yl]cyclohex-3-en-1-yl methylsulfamate;

2-{4-[4-(5-fluoro-2-methoxyphenyl)-1H-pyrrolo[2,3-b]pyridin-2-yl]-3,6-dihydropyridin-1(2H)-yl}-1-(3-methoxyazetidin-1-yl)ethanone;

1-({4-[4-(5-fluoro-2-methoxyphenyl)-1H-pyrrolo[2,3-b]pyridin-2-yl]-3,6-dihydropyridin-1(2H)-yl}acetyl)azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(hydroxymethyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-1-(3-hydroxy-3-methylazetidin-1-yl) ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(methoxymethyl)-3-methylazetidin-1-yl]ethanone;
1-[3-fluoro-3-(methoxymethyl)pyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;
N-cyclobutyl-2-{4-[4-(5-fluoro-2-methoxyphenyl)-1H-pyrrolo[2,3-b]pyridin-2-yl]-3,6-dihydropyridin-1(2H)-yl}acetamide;
1-(3-fluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;
2-{4-[4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;
N-(3-fluorocyclobutyl)-2-{4-[4-(5-fluoro-2-methoxyphenyl)-1H-pyrrolo[2,3-b]pyridin-2-yl]-3,6-dihydropyridin-1(2H)-yl}acetamide;
2-{4-[4-(5-fluoro-2-methoxyphenyl)-1H-pyrrolo[2,3-b]pyridin-2-yl]-3,6-dihydropyridin-1(2H)-yl}-1-(3-hydroxypyrrolidin-1-yl)ethanone;
2-{4-[4-(5-fluoro-2-methoxyphenyl)-1H-pyrrolo[2,3-b]pyridin-2-yl]-3,3-dimethyl-3,6-dihydropyridin-1(2H)-yl}-N,N-dimethylacetamide;
3-{4-[4-(5-fluoro-2-methoxyphenyl)-1H-pyrrolo[2,3-b]pyridin-2-yl]-3,3-dimethyl-3,6-dihydropyridin-1(2H)-yl}propane-1,2-diol;
1-({4-[4-(5-fluoro-2-methoxyphenyl)-1H-pyrrolo[2,3-b]pyridin-2-yl]piperidin-1-yl}acetyl)-L-proline;
1-({4-[4-(5-fluoro-2-methoxyphenyl)-1H-pyrrolo[2,3-b]pyridin-2-yl]-3,6-dihydropyridin-1(2H)-yl}acetyl)-L-proline;
2-{4-[4-(5-fluoro-2-methoxyphenyl)-1H-pyrrolo[2,3-b]pyridin-2-yl]piperidin-1-yl}-N-(methylsulfonyl)acetamide;
1-[(3S,4S)-3,4-dihydroxypyrrolidin-1-yl]-2-{4-[4-(5-fluoro-2-methoxyphenyl)-1H-pyrrolo[2,3-b]pyridin-2-yl]piperidin-1-yl}ethanone;
1-[(3S,4S)-3,4-dihydroxypyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;
N-{4-[4-(5-fluoro-2-methoxyphenyl)-1H-pyrrolo[2,3-b]pyridin-2-yl]cyclohex-3-en-1-yl}-L-serine;
5-[4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
4-(5-fluoro-2-methoxyphenyl)-2-[4-(piperazin-1-yl)cyclohex-1-en-1-yl]-1H-pyrrolo[2,3-b]pyridine;
N²-{4-[4-(5-fluoro-2-methoxyphenyl)-1H-pyrrolo[2,3-b]pyridin-2-yl]cyclohex-3-en-1-yl}-N,N-dimethyl-D-valinamide;
(4R)-1-{4-[4-(5-fluoro-2-methoxyphenyl)-1H-pyrrolo[2,3-b]pyridin-2-yl]cyclohex-3-en-1-yl}-4-hydroxy-L-proline;
N-{4-[4-(5-fluoro-2-methoxyphenyl)-1H-pyrrolo[2,3-b]pyridin-2-yl]cyclohex-3-en-1-yl}-L-valine;
2-{4-[4-(2-methoxyphenyl)-1H-pyrrolo[2,3-b]pyridin-2-yl]piperidin-1-yl}-N-methylacetamide;
{4-[4-(2-methoxyphenyl)-1H-pyrrolo[2,3-b]pyridin-2-yl]piperidin-1-yl}acetic acid;
2-[(6S)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(6R)-6-methyl-1,2,3,6-tetrahydropyridin-4-yl]-1H-pyrrolo[2,3-b]pyridine;
4-(5-fluoro-2-methoxyphenyl)-2-[(2S)-2-methyl-1-(methylsulfonyl)piperidin-4-yl]-1H-pyrrolo[2,3-b]pyridine;
({4-[4-(5-fluoro-2-methoxyphenyl)-1H-pyrrolo[2,3-b]pyridin-2-yl]cyclohex-3-en-1-yl}oxy)acetic acid;
N-{4-[4-(5-fluoro-2-methoxyphenyl)-1H-pyrrolo[2,3-b]pyridin-2-yl]cyclohex-3-en-1-yl}-L-threonine;
2-{1-[(1,1-dioxidothiomorpholin-4-yl)sulfonyl]-1,2,3,6-tetrahydropyridin-4-yl}-4-(5-fluoro-2-methoxyphenyl)-1H-pyrrolo[2,3-b]pyridine;
4-(5-fluoro-2-methoxyphenyl)-2-{1-[(4-methylpiperazin-1-yl)sulfonyl]-1,2,3,6-tetrahydropyridin-4-yl}-1H-pyrrolo[2,3-b]pyridine;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-4-carboxylate;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)prolinate;
ethyl {4-[4-(5-fluoro-2-methoxyphenyl)-1H-pyrrolo[2,3-b]pyridin-2-yl]-3,6-dihydropyridin-1(2H)-yl}acetate;
propan-2-yl {4-[4-(5-fluoro-2-methoxyphenyl)-1H-pyrrolo[2,3-b]pyridin-2-yl]-3,6-dihydropyridin-1(2H)-yl}acetate;
{4-[3-cyano-4-(5-fluoro-2-methoxyphenyl)-1H-pyrrolo[2,3-b]pyridin-2-yl]-3,6-dihydropyridin-1(2H)-yl}acetic acid;
4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;
4-(2-ethoxy-4,5-difluorophenyl)-2-(1,2,3,6-tetrahydropyridin-4-yl)-1H-pyrrolo[2,3-b]pyridine;
2-hydroxy-2-methylpropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
(2,2-dimethyl-1,3-dioxolan-4-yl)methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
tetrahydro-2H-pyran-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-(2-ethoxy-4,5-difluorophenyl)-2-[1-(methylsulfonyl)-1,2,3,6-tetrahydropyridin-4-yl]-1H-pyrrolo[2,3-b]pyridine;
4-[4-(2-ethoxy-4,5-difluorophenyl)-1H-pyrrolo[2,3-b]pyridin-2-yl]-N-methyl-3,6-dihydropyridine-1(2H)-carboxamide;
2-{4-[5-fluoro-4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
{(2S)-4-[4-(5-fluoro-2-methoxyphenyl)-1H-pyrrolo[2,3-b]pyridin-2-yl]-1,2,3,6-tetrahydropyridin-2-yl}methanol;
{(2S)-4-[4-(5-fluoro-2-methoxyphenyl)-1H-pyrrolo[2,3-b]pyridin-2-yl]-1,2,5,6-tetrahydropyridin-2-yl}methanol;
2-{4-[4-(4,5-difluoro-2-methoxyphenyl)-1H-pyrrolo[2,3-b]pyridin-2-yl]piperidin-1-yl}-N-methylacetamide;
2-{4-[4-(4,5-difluoro-2-methoxyphenyl)-1H-pyrrolo[2,3-b]pyridin-2-yl]piperidin-1-yl}-N,N-dimethylacetamide;
2-{5-[4-(5-fluoro-2-methoxyphenyl)-1H-pyrrolo[2,3-b]pyridin-2-yl]-2,3,4,7-tetrahydro-1H-azepin-1-yl}acetamide;
2-{5-[4-(5-fluoro-2-methoxyphenyl)-1H-pyrrolo[2,3-b]pyridin-2-yl]-2,3,4,7-tetrahydro-1H-azepin-1-yl}-N,N-dimethylacetamide;
(1 S,2S,3R,4R)-3-[({4-[4-(4,5-difluoro-2-methoxyphenyl)-1H-pyrrolo[2,3-b]pyridin-2-yl]-3,6-dihydropyridin-1(2H)-yl}acetyl)amino]bicyclo[2.2.1]hept-5-ene-2-carboxamide;
{4-[4-(5-fluoro-2-methoxyphenyl)-1H-pyrrolo[2,3-b]pyridin-2-yl]cyclohex-3-en-1-yl}[(2S)-2-(hydroxymethyl)pyrrolidin-1-yl]methanone;

2-{4-[4-(4-fluoro-2-methoxyphenyl)-1H-pyrrolo[2,3-b]pyridin-2-yl]piperidin-1-yl}acetamide;
2-{4-[4-(4-fluoro-2-methoxyphenyl)-1H-pyrrolo[2,3-b]pyridin-2-yl]piperidin-1-yl}-N-methylacetamide;
4-(5-fluoro-2-methoxyphenyl)-2-(octahydrocyclopenta[c]pyrrol-5-yl)-1H-pyrrolo[2,3-b]pyridine;
1-{4-[5-fluoro-4-(5-fluoro-2-methoxyphenyl)-1H-pyrrolo[2,3-b]pyridin-2-yl]piperidin-1-yl}-2-hydroxyethanone;
pyrrolidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
piperidin-4-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
piperidin-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
pyrrolidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2,3-dihydroxypropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
methyl {4-[4-(2-methoxyphenyl)-1H-pyrrolo[2,3-b]pyridin-2-yl]piperidin-1-yl}acetate;
1-[(2S)-2-(hydroxymethyl)pyrrolidin-1-yl]-2-{4-[4-(2-methoxyphenyl)-1H-pyrrolo[2,3-b]pyridin-2-yl]piperidin-1-yl}ethanone;
(2R)-2-({4-[4-(5-fluoro-2-methoxyphenyl)-1H-pyrrolo[2,3-b]pyridin-2-yl]cyclohex-3-en-1-yl}amino)-1-(3-hydroxyazetidin-1-yl)-3-methylbutan-1-one;
1-{4-[4-(5-fluoro-2-methoxyphenyl)-1H-pyrrolo[2,3-b]pyridin-2-yl]cyclohex-3-en-1-yl}-N,N-dimethyl-L-prolinamide;
(2R)-({4-[4-(5-fluoro-2-methoxyphenyl)-1H-pyrrolo[2,3-b]pyridin-2-yl]cyclohex-3-en-1-yl}amino)(phenyl)acetic acid;
4-(5-fluoro-2-methoxyphenyl)-2-[3-(methylsulfonyl)-3-azabicyclo[4.1.0]hept-6-yl]-1H-pyrrolo[2,3-b]pyridine;
4-(5-fluoro-2-methoxyphenyl)-2-[4-(1H-tetrazol-5-yl)cyclohex-1-en-1-yl]-1H-pyrrolo[2,3-b]pyridine;
4-[4-(5-fluoro-2-methoxyphenyl)-1H-pyrrolo[2,3-b]pyridin-2-yl]cyclohex-3-en-1-yl tert-butylcarbamate;
2-{4-[4-(5-fluoro-2-methoxyphenyl)-5-methoxy-1H-pyrrolo[2,3-b]pyridin-2-yl]-3,6-dihydropyridin-1(2H)-yl}-1-[(2S)-2-(hydroxymethyl)pyrrolidin-1-yl]ethanone;
2-{4-[4-(4,5-difluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
2-{(2S)-4-[4-(5-fluoro-2-methoxyphenyl)-1H-pyrrolo[2,3-b]pyridin-2-yl]-2-methylpiperidin-1-yl}-N,N-dimethylacetamide;
4,4,4-trifluoro-2-{4-[4-(5-fluoro-2-methoxyphenyl)-1H-pyrrolo[2,3-b]pyridin-2-yl]-3,6-dihydropyridin-1(2H)-yl}butanoic acid;
2-{4-[4-(5-fluoro-2-methoxyphenyl)-1H-pyrrolo[2,3-b]pyridin-2-yl]-3,6-dihydropyridin-1(2H)-yl}-N,N-dimethyl-2-oxoethanesulfonamide;
2-{4-[4-(5-fluoro-2-methoxyphenyl)-1H-pyrrolo[2,3-b]pyridin-2-yl]piperidin-1-yl}-N-methyl-2-oxoethanesulfonamide;
2-{4-[4-(5-fluoro-2-methoxyphenyl)-1H-pyrrolo[2,3-b]pyridin-2-yl]piperidin-1-yl}-N,N-dimethyl-2-oxoethanesulfonamide;
1-{4-[4-(5-fluoro-2-methoxyphenyl)-1H-pyrrolo[2,3-b]pyridin-2-yl]-3,6-dihydropyridin-1(2H)-yl}-1-oxopropane-2-sulfonamide;
ethyl {4-[4-(5-fluoro-2-methoxyphenyl)-1H-pyrrolo[2,3-b]pyridin-2-yl]-3,6-dihydropyridin-1(2H)-yl}(phenyl)acetate;
ethyl 2-{4-[4-(5-fluoro-2-methoxyphenyl)-1H-pyrrolo[2,3-b]pyridin-2-yl]-3,6-dihydropyridin-1(2H)-yl}-1,3-thiazole-5-carboxylate;
tert-butyl 3-{4-[4-(5-fluoro-2-methoxyphenyl)-1H-pyrrolo[2,3-b]pyridin-2-yl]-3,6-dihydropyridin-1(2H)-yl}pyrrolidine-1-carboxylate;
ethyl {[(6S)-4-[4-(5-fluoro-2-methoxyphenyl)-1H-pyrrolo[2,3-b]pyridin-2-yl]-6-methyl-3,6-dihydropyridin-1(2H)-yl]sulfonyl}carbamate;
2-({4-[4-(5-fluoro-2-methoxyphenyl)-1H-pyrrolo[2,3-b]pyridin-2-yl]cyclohex-3-en-1-yl}oxy)ethanol;
2-{4-[4-(5-fluoro-2-methoxyphenyl)-1H-pyrrolo[2,3-b]pyridin-2-yl]piperidin-1-yl}propanoic acid;
{4-[4-(5-fluoro-2-methoxyphenyl)-1H-pyrrolo[2,3-b]pyridin-2-yl]-3,6-dihydropyridin-1(2H)-yl}(phenyl)acetic acid;
4-(5-fluoro-2-methoxyphenyl)-2-[1-(pyrrolidin-3-yl)-1,2,3,6-tetrahydropyridin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]piperidin-1-yl}-3-oxopropanenitrile;
5-fluoro-4-(5-fluoro-2-methoxyphenyl)-2-(1,2,3,6-tetrahydropyridin-4-yl)-1H-pyrrolo[2,3-b]pyridine-3-carbonitrile;
4-fluoro-2-[2-(1,2,3,6-tetrahydropyridin-4-yl)-1H-pyrrolo[2,3-b]pyridin-4-yl]benzamide;
{4-[3-cyano-5-fluoro-4-(5-fluoro-2-methoxyphenyl)-1H-pyrrolo[2,3-b]pyridin-2-yl]-3,6-dihydropyridin-1(2H)-yl}acetic acid;
2-aminoethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
azetidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2-(dimethylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2-(2,2-dimethyl-1,2,3,6-tetrahydropyridin-4-yl)-4-(5-fluoro-2-methoxyphenyl)-1H-pyrrolo[2,3-b]pyridine;
{4-[3-cyano-4-(5-fluoro-2-methoxyphenyl)-1H-pyrrolo[2,3-b]pyridin-2-yl]piperidin-1-yl}acetic acid;
4-(5-fluoro-2-methoxyphenyl)-2-(piperidin-4-yl)-1H-pyrrolo[2,3-b]pyridine-3-carbonitrile;
2-{4-[3-cyano-4-(5-fluoro-2-methoxyphenyl)-1H-pyrrolo[2,3-b]pyridin-2-yl]piperidin-1-yl}-N,N-dimethylacetamide;
5-({4-[4-(5-fluoro-2-methoxyphenyl)-1H-pyrrolo[2,3-b]pyridin-2-yl]piperidin-1-yl}methyl)-2,4-dihydro-3H-1,2,4-triazol-3-one;
4-(5-fluoro-2-methoxyphenyl)-2-{1-[1-(methylsulfonyl)pyrrolidin-3-yl]-1,2,3,6-tetrahydropyridin-4-yl}-1H-pyrrolo[2,3-b]pyridine;
2-{4-[4-(5-fluoro-2-methoxyphenyl)-1H-pyrrolo[2,3-b]pyridin-2-yl]piperidin-1-yl}-N-(propan-2-ylsulfonyl)acetamide;
ethyl 2-{4-[4-(5-fluoro-2-methoxyphenyl)-1H-pyrrolo[2,3-b]pyridin-2-yl]piperidin-1-yl}-1,3-thiazole-5-carboxylate;
methyl (4-{4-[4-(5-fluoro-2-methoxyphenyl)-1H-pyrrolo[2,3-b]pyridin-2-yl]-3,6-dihydropyridin-1(2H)-yl}cyclohexyl)acetate;
3-{4-[4-(5-fluoro-2-methoxyphenyl)-1H-pyrrolo[2,3-b]pyridin-2-yl]-3,6-dihydropyridin-1(2H)-yl}-1-methylpyrrolidin-2-one;

4-{4-[4-(5-fluoro-2-methoxyphenyl)-1H-pyrrolo[2,3-b]
  pyridin-2-yl]-3,6-dihydropyridin-1(2H)-yl}pyrrolidin-2-
  one;
2-{4-[4-(5-fluoro-2-methoxyphenyl)-1H-pyrrolo[2,3-b]
  pyridin-2-yl]piperidin-1-yl}-1,3-thiazole-5-carboxylic
  acid;
(2 S)-cyclohexyl({4-[4-(5-fluoro-2-methoxyphenyl)-1H-
  pyrrolo[2,3-b]pyridin-2-yl]cyclohex-3-en-1-yl}amino)
  acetic acid;
N-{4-[5-fluoro-4-(5-fluoro-2-methoxyphenyl)-1H-pyrrolo
  [2,3-b]pyridin-2-yl]cyclohex-3-en-1-yl}-D-valine;
N-{4-[5-fluoro-4-(5-fluoro-2-methoxyphenyl)-1H-pyrrolo
  [2,3-b]pyridin-2-yl]cyclohex-3-en-1-yl}-3-methyl-L-va-
  line;
5-fluoro-4-(5-fluoro-2-methoxyphenyl)-2-(1-{2-[(2S)-2-
  (hydroxymethyl)pyrrolidin-1-yl]-2-oxoethyl}-1,2,3,6-tet-
  rahydropyridin-4-yl)-1H-pyrrolo[2,3-b]pyridine-3-carbo-
  nitrile;
4-(5-fluoro-2-methoxyphenyl)-2-[1-(methylsulfonyl)piperi-
  din-4-yl]-1H-pyrrolo[2,3-b]pyridine-3-carbonitrile;
{4-[5-fluoro-4-(5-fluoro-2-methoxyphenyl)-1H-pyrrolo[2,
  3-b]pyridin-2-yl]piperidin-1-yl}acetic acid;
methyl 1-({4-[4-(5-fluoro-2-methoxyphenyl)-1H-pyrrolo[2,
  3-b]pyridin-2-yl]cyclohex-3-en-1-yl}carbonyl)prolinate;
N-cyano-4-[3-cyano-5-fluoro-4-(5-fluoro-2-methoxyphe-
  nyl)-1H-pyrrolo[2,3-b]pyridin-2-yl]-3,6-dihydropyri-
  dine-1(2H)-carboxamide;
(4-{4-[4-(5-fluoro-2-methoxyphenyl)-1H-pyrrolo[2,3-b]
  pyridin-2-yl]-3,6-dihydropyridin-1(2H)-yl}cyclohexyl)
  acetic acid;
3-{4-[4-(5-fluoro-2-methoxyphenyl)-1H-pyrrolo[2,3-b]
  pyridin-2-yl]piperidin-1-yl}-1-methylpyrrolidin-2-one;
N-cyano-4-[5-fluoro-4-(5-fluoro-2-methoxyphenyl)-1H-
  pyrrolo[2,3-b]pyridin-2-yl]-3,6-dihydropyridine-1(2H)-
  carboxamide;
4-(5-fluoro-2-methoxyphenyl)-2-(1-{[2-(2-methoxyethoxy)
  ethyl]sulfonyl}-1,2,3,6-tetrahydropyridin-4-yl)-1H-pyr-
  rolo[2,3-b]pyridine;
1-({4-[3-cyano-5-fluoro-4-(5-fluoro-2-methoxyphenyl)-
  1H-pyrrolo[2,3-b]pyridin-2-yl]-3,6-dihydropyridin-1
  (2H)-yl}acetyl)-L-prolinamide;
N-cyano-2-{4-[4-(5-fluoro-2-methoxyphenyl)-1H-pyrrolo
  [2,3-b]pyridin-2-yl]piperidin-1-yl}acetamide;
{(2R)-4-[4-(5-fluoro-2-methoxyphenyl)-1H-pyrrolo[2,3-b]
  pyridin-2-yl]-1,2,5,6-tetrahydropyridin-2-yl}methanol;
{(2R)-4-[4-(5-fluoro-2-methoxyphenyl)-1H-pyrrolo[2,3-b]
  pyridin-2-yl]-1,2,3,6-tetrahydropyridin-2-yl}methanol;
ethyl ({4-[5-fluoro-4-(5-fluoro-2-methoxyphenyl)-1H-pyr-
  rolo[2,3-b]pyridin-2-yl]piperidin-1-yl}sulfonyl)carbam-
  ate;
2-{4-[5-fluoro-4-(5-fluoro-2-methoxyphenyl)-1H-pyrrolo
  [2,3-b]pyridin-2-yl]piperidin-1-yl}-N-(2-hydroxyethyl)-
  N-methylacetamide;
4-[4-(5-fluoro-2-methoxyphenyl)-1H-pyrrolo[2,3-b]pyri-
  din-2-yl]cyclohex-3-en-1-yl[(3-hydroxyazetidin-1-yl)sul-
  fonyl]carbamate;
4-(5-fluoro-2-methoxyphenyl)-2-{1-[(2-methoxyethyl)sul-
  fonyl]-1,2,3,6-tetrahydropyridin-4-yl}-1H-pyrrolo[2,3-b]
  pyridine;
N-{4-[4-(5-fluoro-2-methoxyphenyl)-1H-pyrrolo[2,3-b]
  pyridin-2-yl]cyclohex-3-en-1-yl}-2-(2-methoxyethoxy)
  ethanesulfonamide;
tert-butyl 3-{4-[4-(5-fluoro-2-methoxyphenyl)-1H-pyrrolo
  [2,3-b]pyridin-2-yl]-3,6-dihydropyridin-1(2H)-
  yl}cyclobutanecarboxylate;
3-{4-[4-(5-fluoro-2-methoxyphenyl)-1H-pyrrolo[2,3-b]
  pyridin-2-yl]-3,6-dihydropyridin-1(2H)-
  yl}cyclobutanecarboxylic acid;
4-(5-fluoro-2-methoxyphenyl)-2-[2-(methylsulfonyl)octa-
  hydrocyclopenta[c]pyrrol-5-yl]-1H-pyrrolo[2,3-b]pyri-
  dine;
[(2S)-4-[4-(5-fluoro-2-methoxyphenyl)-1H-pyrrolo[2,3-b]
  pyridin-2-yl]-2-(hydroxymethyl)-2,5-dihydro-1H-pyrrol-
  1-yl]acetic acid;
$N^2$-{4-[4-(5-fluoro-2-methoxyphenyl)-1H-pyrrolo[2,3-b]
  pyridin-2-yl]cyclohex-3-en-1-yl}-N-methyl-D-valina-
  mide;
N-{4-[4-(5-fluoro-2-methoxyphenyl)-1H-pyrrolo[2,3-b]
  pyridin-2-yl]cyclohex-3-en-1-yl}-L-phenylalanine;
N-{4-[4-(5-fluoro-2-methoxyphenyl)-1H-pyrrolo[2,3-b]
  pyridin-2-yl]cyclohex-3-en-1-yl}-L-tyrosine;
$N^2$-{4-[4-(5-fluoro-2-methoxyphenyl)-1H-pyrrolo[2,3-b]
  pyridin-2-yl]cyclohex-3-en-1-yl}-L-valinamide;
$N^2$-{4-[4-(5-fluoro-2-methoxyphenyl)-1H-pyrrolo[2,3-b]
  pyridin-2-yl]cyclohex-3-en-1-yl}-N,3-dimethyl-L-val-
  inamide;
(2S)-({4-[4-(5-fluoro-2-methoxyphenyl)-1H-pyrrolo[2,3-b]
  pyridin-2-yl]cyclohex-3-en-1-yl}amino)(phenyl)acetic
  acid;
2-[1-(cyanoacetyl)-1,2,3,6-tetrahydropyridin-4-yl]-4-(5-
  fluoro-2-methoxyphenyl)-1H-pyrrolo[2,3-b]pyridine-5-
  carbonitrile;
4-(5-fluoro-2-methoxyphenyl)-2-[1-(methylsulfonyl)-1,2,3,
  6-tetrahydropyridin-4-yl]-3-nitro-1H-pyrrolo[2,3-b]pyri-
  dine;
4-(5-fluoro-2-methoxyphenyl)-2-(2-{[2-(2-methoxyethoxy)
  ethyl]sulfonyl}-1,2,3,3a,4,6a-hexahydrocyclopenta[c]
  pyrrol-5-yl)-1H-pyrrolo[2,3-b]pyridine;
(9aR)-8-[4-(5-fluoro-2-methoxyphenyl)-1H-pyrrolo[2,3-b]
  pyridin-2-yl]-1,6,7,9a-tetrahydropyrido[2,1-c][1,4]ox-
  azin-3(4H)-one;
7-[4-(5-fluoro-2-methoxyphenyl)-1H-pyrrolo[2,3-b]pyri-
  din-2-yl]-1,5,6,8a-tetrahydro[1,3]oxazolo[3,4-a]pyridin-
  3-one;
2-{4-[4-(5-fluoro-2-methoxyphenyl)-1H-pyrrolo[2,3-b]
  pyridin-2-yl]piperidin-1-yl}-N-(2-methoxyethyl)-N-
  methylacetamide;
{4-[4-(5-fluoro-2-methoxyphenyl)-1H-pyrrolo[2,3-b]pyri-
  din-2-yl]piperidin-1-yl}(phenyl)acetic acid;
2-{4-[5-cyano-4-(5-fluoro-2-methoxyphenyl)-1H-pyrrolo
  [2,3-b]pyridin-2-yl]-3,6-dihydropyridin-1(2H)-
  yl}acetamide;
N-(3-fluorocyclobutyl)-4-[4-(5-fluoro-2-methoxyphenyl)-
  1H-pyrrolo[2,3-b]pyridin-2-yl]-2,5-dihydro-1H-pyrrole-
  2-carboxamide;
4-(5-fluoro-2-methoxyphenyl)-2-[(2R)-2-methyl-1,2,3,6-
  tetrahydropyridin-4-yl]-1H-pyrrolo[2,3-b]pyridine-4-(5-
  fluoro-2-methoxyphenyl)-2-[(6R)-6-methyl-1,2,3,6-tetra-
  hydropyridin-4-yl]-1H-pyrrolo[2,3-b]pyridine (1:1);
2-{4-[4-(5-fluoro-2-methoxyphenyl)-1H-pyrrolo[2,3-b]
  pyridin-2-yl]-6,6-dimethyl-3,6-dihydropyridin-1(2H)-
  yl}-N,N-dimethylacetamide;
methyl 4-[4-(5-fluoro-2-methoxyphenyl)-1H-pyrrolo[2,3-b]
  pyridin-2-yl]-1-(methylcarbamoyl)-2,5-dihydro-1H-pyr-
  role-2-carboxylate;
4-(5-fluoro-2-methoxyphenyl)-2-(1,2,3,3a,4,6a-hexahydro-
  cyclopenta[c]pyrrol-5-yl)-1H-pyrrolo[2,3-b]pyridine-5-
  carbonitrile;
5-[5-cyano-4-(5-fluoro-2-methoxyphenyl)-1H-pyrrolo[2,3-
  b]pyridin-2-yl]-N-methyl-3,3a,4,6a-tetrahydrocyclopenta
  [c]pyrrole-2(1H)-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-2-{4-[4-(5-fluoro-2-methoxyphenyl)-1H-pyrrolo[2,3-b]pyridin-2-yl]-3,6-dihydropyridin-1(2H)-yl}acetamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}ethanone;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-3-carboxylate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxamide;
N-cyano-4-[4-(5-fluoro-2-methoxyphenyl)-1H-pyrrolo[2,3-b]pyridin-2-yl]piperidine-1-carboxamide;
2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide;
N-{5-[4-(5-fluoro-2-methoxyphenyl)-1H-pyrrolo[2,3-b]pyridin-2-yl]-1,2,3,3a,4,6a-hexahydropentalen-2-yl}-D-valine;
methyl 4-[4-(5-fluoro-2-methoxyphenyl)-1H-pyrrolo[2,3-b]pyridin-2-yl]-3,6-dihydropyridine-1(2H)-carboxylate;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine;
2-{4-[5-cyano-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;
2-({4-[4-(5-fluoro-2-methoxyphenyl)-1H-pyrrolo[2,3-b]pyridin-2-yl]cyclohex-3-en-1-yl}oxy)-N,N-dimethylacetamide;
2-({4-[4-(5-fluoro-2-methoxyphenyl)-1H-pyrrolo[2,3-b]pyridin-2-yl]cyclohex-3-en-1-yl}oxy)-1-(morpholin-4-yl)ethanone;
4-[5-fluoro-2-(methylsulfanyl)phenyl]-2-[1-(methylsulfonyl)-1,2,3,6-tetrahydropyridin-4-yl]-1H-pyrrolo[2,3-b]pyridine;
4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-5-carbonitrile;
2-{4-[5-cyano-4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;
2-{4-[5-cyano-4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;
2-{4-[4-(5-fluoro-2-methoxyphenyl)-1H-pyrrolo[2,3-b]pyridin-2-yl]-3,6-dihydropyridin-1(2H)-yl}-N-(2-methoxyethyl)-N-methylacetamide;
methyl (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl (trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl {4-[4-(5-fluoro-2-methoxyphenyl)-1H-pyrrolo[2,3-b]pyridin-2-yl]cyclohex-3-en-1-yl}acetate;
{4-[4-(5-fluoro-2-methoxyphenyl)-1H-pyrrolo[2,3-b]pyridin-2-yl]cyclohex-3-en-1-yl}acetic acid;
(4-{4-[4-(5-fluoro-2-methoxyphenyl)-1H-pyrrolo[2,3-b]pyridin-2-yl]piperidin-1-yl}cyclohexyl)acetic acid;
methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate;
N-{4-[4-(5-fluoro-2-methoxyphenyl)-1H-pyrrolo[2,3-b]pyridin-2-yl]cyclohex-3-en-1-yl}-L-leucine;
4-(5-fluoro-2-methoxyphenyl)-2-[(6R)-6-methyl-1-(methylsulfonyl)-1,2,3,6-tetrahydropyridin-4-yl]-1H-pyrrolo[2,3-b]pyridine;
2-[(6R)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(2R)-2-methyl-1-(methylsulfonyl)-1,2,3,6-tetrahydropyridin-4-yl]-1H-pyrrolo[2,3-b]pyridine;
2-[(2R)-4-[4-(5-fluoro-2-methoxyphenyl)-1H-pyrrolo[2,3-b]pyridin-2-yl]-2-methyl-3,6-dihydropyridin-1(2H)-yl]-N,N-dimethylacetamide;
{4-[4-(5-fluoro-2-methoxyphenyl)-1H-pyrrolo[2,3-b]pyridin-2-yl]cyclohex-3-en-1-yl}(3-hydroxyazetidin-1-yl)methanone;
2-{4-[5-fluoro-4-(5-fluoro-2-methoxyphenyl)-1H-pyrrolo[2,3-b]pyridin-2-yl]piperidin-1-yl}-N-methyl-2-oxoethanesulfonamide;
{4-[5-cyano-4-(5-fluoro-2-methoxyphenyl)-1H-pyrrolo[2,3-b]pyridin-2-yl]piperidin-1-yl}acetic acid;
2-[1-(cyanoacetyl)piperidin-4-yl]-4-(5-fluoro-2-methoxyphenyl)-1H-pyrrolo[2,3-b]pyridine-5-carbonitrile;
4-(5-fluoro-2-methoxyphenyl)-2-{1-[2-(3-hydroxyazetidin-1-yl)-2-oxoethyl]piperidin-4-yl}-1H-pyrrolo[2,3-b]pyridine-5-carbonitrile;
4-[5-fluoro-2-(methylsulfinyl)phenyl]-2-[1-(methylsulfonyl)-1,2,3,6-tetrahydropyridin-4-yl]-1H-pyrrolo[2,3-b]pyridine;
4-[3-cyano-5-fluoro-4-(5-fluoro-2-methoxyphenyl)-1H-pyrrolo[2,3-b]pyridin-2-yl]cyclohex-3-ene-1-carboxylic acid;
4-(5-fluoro-2-methoxyphenyl)-2-(1,2,3,3a,4,6a-hexahydrocyclopenta[c]pyrrol-5-yl)-5-hydroxy-1H-pyrrolo[2,3-b]pyridine-3-carbonitrile;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine-3-carbonitrile;
2-{4-[5-fluoro-4-(5-fluoro-2-methoxyphenyl)-1H-pyrrolo[2,3-b]pyridin-2-yl]piperidin-1-yl}-N-(3-hydroxycyclobutyl)-N-methylacetamide;
2-{4-[5-cyano-4-(5-fluoro-2-methoxyphenyl)-1H-pyrrolo[2,3-b]pyridin-2-yl]piperidin-1-yl}-N-(2-hydroxyethyl)-N-methylacetamide;
tert-butyl {4-[3-cyano-4-(5-fluoro-2-methoxyphenyl)-1H-pyrrolo[2,3-b]pyridin-2-yl]-3,6-dihydropyridin-1(2H)-yl}acetate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-oxoethanesulfonamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-oxopropane-2-sulfonamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethyl-2-oxoethanesulfonamide;
tert-butyl {5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetate;

2-{4-[4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;
2-{4-[4-(5-fluoro-2-methoxyphenyl)-1H-pyrrolo[2,3-b]pyridin-2-yl]-3,6-dihydropyridin-1(2H)-yl}-1-[(3S)-3-hydroxypyrrolidin-1-yl]ethanone;
4-({4-[4-(5-fluoro-2-methoxyphenyl)-1H-pyrrolo[2,3-b]pyridin-2-yl]-3,6-dihydropyridin-1(2H)-yl}carbonyl)benzoic acid;
3-({4-[4-(5-fluoro-2-methoxyphenyl)-1H-pyrrolo[2,3-b]pyridin-2-yl]-3,6-dihydropyridin-1(2H)-yl}carbonyl)benzoic acid;
tert-butyl (3aS,6aR)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;
tert-butyl (3aR,6aS)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;
(3-{4-[4-(5-fluoro-2-methoxyphenyl)-1H-pyrrolo[2,3-b]pyridin-2-yl]-3,6-dihydropyridin-1(2H)-yl}cyclobutyl)acetic acid;
2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoic acid;
ethyl 5-[4-(5-fluoro-2-methoxyphenyl)-1H-pyrrolo[2,3-b]pyridin-2-yl]-1,2,3,6-tetrahydropyridine-4-carboxylate;
{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;
4-(5-fluoro-2-methoxyphenyl)-2-[1-(2,5,8,11-tetraoxatetradecan-14-yl)-1,2,3,6-tetrahydropyridin-4-yl]-1H-pyrrolo[2,3-b]pyridine;
5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-3-carbonitrile;
5-[3-cyano-5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;
2-{4-[3-cyano-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;
4-(5-fluoro-2-methoxyphenyl)-2-{2-[2-(3-hydroxyazetidin-1-yl)-2-oxoethyl]-1,2,3,3a,4,6a-hexahydrocyclopenta[c]pyrrol-5-yl}-1H-pyrrolo[2,3-b]pyridine-5-carbonitrile;
4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;
(3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide;
1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]ethanone;
1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-2-hydroxyethanone;
(3aR,5r,6aS)-N-cyano-5-[4-(5-fluoro-2-methoxyphenyl)-1H-pyrrolo[2,3-b]pyridin-2-yl]hexahydrocyclopenta[c]pyrrole-2(1H)-carboxamide;
2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N,N-dimethylacetamide;
3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]propane-1,2-diol;
2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]acetamide;
3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-3-oxopropanenitrile;
4-[4-(5-fluoro-2-methoxyphenyl)-1H-pyrrolo[2,3-b]pyridin-2-yl]cyclohexanecarboxylic acid;
(4-{4-[3-cyano-4-(5-fluoro-2-methoxyphenyl)-1H-pyrrolo[2,3-b]pyridin-2-yl]-3,6-dihydropyridin-1(2H)-yl}cyclohexyl)acetic acid;
(4-{4-[5-fluoro-4-(5-fluoro-2-methoxyphenyl)-1H-pyrrolo[2,3-b]pyridin-2-yl]piperidin-1-yl}cyclohexyl)acetic acid;
{4-[5-chloro-4-(5-fluoro-2-methoxyphenyl)-1H-pyrrolo[2,3-b]pyridin-2-yl]cyclohex-3-en-1-yl}acetic acid;
2-({4-[4-(5-fluoro-2-methoxyphenyl)-1H-pyrrolo[2,3-b]pyridin-2-yl]-3,6-dihydropyridin-1(2H)-yl}sulfonyl)ethanol;
(3-{4-[4-(5-fluoro-2-methoxyphenyl)-1H-pyrrolo[2,3-b]pyridin-2-yl]-3,6-dihydropyridin-1(2H)-yl}cyclobutyl)(3-hydroxyazetidin-1-yl)methanone;
2-{5-[3-cyano-5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;
2-[(6R)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;
{5-[4-(5-fluoro-2-methoxyphenyl)-1H-pyrrolo[2,3-b]pyridin-2-yl]-1,2,3,6-tetrahydropyridin-4-yl}methanol;
{4-[4-(5-fluoro-2-methoxyphenyl)-1H-pyrrolo[2,3-b]pyridin-2-yl]-3,6-dihydropyridin-1(2H)-yl}(3-hydroxycyclobutyl)methanone;
4-(5-fluoro-2-methoxyphenyl)-2-[(3R)-3-methyl-1,2,3,6-tetrahydropyridin-4-yl]-1H-pyrrolo[2,3-b]pyridine;
4-(5-fluoro-2-methoxyphenyl)-2-[(3S)-3-methyl-1,2,3,6-tetrahydropyridin-4-yl]-1H-pyrrolo[2,3-b]pyridine;
2-[(3R)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;
2-[(3S)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;
1-{4-[4-(5-fluoro-2-methoxyphenyl)-1H-pyrrolo[2,3-b]pyridin-2-yl]cyclohex-3-en-1-yl}-N-methyl-L-prolinamide;
2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone;
2-[(3aR,5S,6aS)-5-[4-(5-fluoro-2-methoxyphenyl)-1H-pyrrolo[2,3-b]pyridin-2-yl]hexahydrocyclopenta[c]pyrrol-2(1H)-yl]-1-[(2S)-2-(hydroxymethyl)pyrrolidin-1-yl]ethanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(2-hydroxyethyl)-N-methylacetamide;
2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(3-hydroxycyclobutyl)-N-methylacetamide;
[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl](3-hydroxycyclobutyl)methanone;
2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-methyl-2-oxoethanesulfonamide;
2-(8-azabicyclo[3.2.1]oct-2-en-3-yl)-4-(5-fluoro-2-methoxyphenyl)-1H-pyrrolo[2,3-b]pyridine-5-carbonitrile;
2-(8-azabicyclo[3.2.1]oct-2-en-3-yl)-5-fluoro-4-(5-fluoro-2-methoxyphenyl)-1H-pyrrolo[2,3-b]pyridine;
N-cyano-3-[5-fluoro-4-(5-fluoro-2-methoxyphenyl)-1H-pyrrolo[2,3-b]pyridin-2-yl]-8-azabicyclo[3.2.1]oct-2-ene-8-carboxamide;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;
{3-[5-cyano-4-(5-fluoro-2-methoxyphenyl)-1H-pyrrolo[2,3-b]pyridin-2-yl]-8-azabicyclo[3.2.1]oct-2-en-8-yl}acetic acid;
{3-[5-fluoro-4-(5-fluoro-2-methoxyphenyl)-1H-pyrrolo[2,3-b]pyridin-2-yl]-8-azabicyclo[3.2.1]oct-2-en-8-yl}acetic acid;
2-{3-[5-cyano-4-(5-fluoro-2-methoxyphenyl)-1H-pyrrolo[2,3-b]pyridin-2-yl]-8-azabicyclo[3.2.1]oct-2-en-8-yl}acetamide;
{4-[4-(5-fluoro-2-methoxyphenyl)-1H-pyrrolo[2,3-b]pyridin-2-yl]cyclohexyl}acetic acid;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;
1-{4-[5-fluoro-4-(5-fluoro-2-methoxyphenyl)-1H-pyrrolo[2,3-b]pyridin-2-yl]cyclohex-3-en-1-yl}-N,N-dimethyl-L-prolinamide;
4-[3-cyano-4-(5-fluoro-2-methoxyphenyl)-1H-pyrrolo[2,3-b]pyridin-2-yl]cyclohex-3-ene-1-carboxylic acid;
2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;
4-(5-fluoro-2-methoxyphenyl)-2-(8-{2-[(2S)-2-(hydroxymethyl)pyrrolidin-1-yl]-2-oxoethyl}-8-azabicyclo[3.2.1]oct-2-en-3-yl)-1H-pyrrolo[2,3-b]pyridine-5-carbonitrile;
4-(5-fluoro-2-methoxyphenyl)-2-{8-[2-(3-hydroxyazetidin-1-yl)-2-oxoethyl]-8-azabicyclo[3.2.1]oct-2-en-3-yl}-1H-pyrrolo[2,3-b]pyridine-5-carbonitrile;
{4-[5-cyano-4-(5-fluoro-2-methoxyphenyl)-1H-pyrrolo[2,3-b]pyridin-2-yl]cyclohex-3-en-1-yl}acetic acid;
2-(9-azabicyclo[3.3.1]non-2-en-3-yl)-4-(5-fluoro-2-methoxyphenyl)-1H-pyrrolo[2,3-b]pyridine;
4-(5-fluoro-2-methoxyphenyl)-2-[9-(methylsulfonyl)-9-azabicyclo[3.3.1]non-2-en-3-yl]-1H-pyrrolo[2,3-b]pyridine;
3-[4-(5-fluoro-2-methoxyphenyl)-1H-pyrrolo[2,3-b]pyridin-2-yl]-N-methyl-9-azabicyclo[3.3.1]non-2-ene-9-carboxamide;
2-{3-[4-(5-fluoro-2-methoxyphenyl)-1H-pyrrolo[2,3-b]pyridin-2-yl]-9-azabicyclo[3.3.1]non-2-en-9-yl}-N,N-dimethylacetamide;
3-{3-[4-(5-fluoro-2-methoxyphenyl)-1H-pyrrolo[2,3-b]pyridin-2-yl]-9-azabicyclo[3.3.1]non-2-en-9-yl}-3-oxopropanenitrile;
{3-[4-(5-fluoro-2-methoxyphenyl)-1H-pyrrolo[2,3-b]pyridin-2-yl]-9-azabicyclo[3.3.1]non-2-en-9-yl}(3-hydroxycyclobutyl)methanone;
2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;
2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;
2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;
2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(trans-4-hydroxycyclohexyl)acetamide;
4-[4-(4-fluoro-2-methoxyphenyl)-1H-pyrrolo[2,3-b]pyridin-2-yl]cyclohex-3-ene-1-carboxylic acid;
4-[4-(4,5-difluoro-2-methoxyphenyl)-1H-pyrrolo[2,3-b]pyridin-2-yl]cyclohex-3-ene-1-carboxylic acid;
4-[4-(2-methoxyphenyl)-1H-pyrrolo[2,3-b]pyridin-2-yl]cyclohex-3-ene-1-carboxylic acid;
4-[4-(5-fluoro-2-methoxyphenyl)-1H-pyrrolo[2,3-b]pyridin-2-yl]-1-methylcyclohex-3-ene-1-carboxylic acid;
2-{4-[4-(5-fluoro-2-methoxyphenyl)-1H-pyrrolo[2,3-b]pyridin-2-yl]-2,3,6,7-tetrahydro-1H-azepin-1-yl}-N,N-dimethylacetamide;
2-{4-[4-(5-fluoro-2-methoxyphenyl)-1H-pyrrolo[2,3-b]pyridin-2-yl]azepan-1-yl}-N,N-dimethylacetamide;
{4-[4-(5-fluoro-2-methoxyphenyl)-1H-pyrrolo[2,3-b]pyridin-2-yl]-2,3,6,7-tetrahydro-1H-azepin-1-yl}acetic acid;
2-{4-[4-(5-fluoro-2-methoxyphenyl)-1H-pyrrolo[2,3-b]pyridin-2-yl]-2,3,6,7-tetrahydro-1H-azepin-1-yl}-1-(3-hydroxyazetidin-1-yl)ethanone;
tert-butyl 3-{4-[4-(5-fluoro-2-methoxyphenyl)-1H-pyrrolo[2,3-b]pyridin-2-yl]-3,6-dihydropyridin-1(2H)-yl}azetidine-1-carboxylate;
tert-butyl 3-{4-[4-(5-fluoro-2-methoxyphenyl)-1H-pyrrolo[2,3-b]pyridin-2-yl]piperidin-1-yl}azetidine-1-carboxylate;
{4-[5-fluoro-4-(5-fluoro-2-methoxyphenyl)-1H-pyrrolo[2,3-b]pyridin-2-yl]cyclohex-3-en-1-yl}acetic acid;
2-[1-(azetidin-3-yl)-1,2,3,6-tetrahydropyridin-4-yl]-4-(5-fluoro-2-methoxyphenyl)-1H-pyrrolo[2,3-b]pyridine;
2-[1-(azetidin-3-yl)piperidin-4-yl]-4-(5-fluoro-2-methoxyphenyl)-1H-pyrrolo[2,3-b]pyridine;
[3-(benzyloxy)-1,2-oxazol-5-yl]{4-[4-(5-fluoro-2-methoxyphenyl)-1H-pyrrolo[2,3-b]pyridin-2-yl]-3,6-dihydropyridin-1(2H)-yl}methanone;
4-[5-cyano-4-(5-fluoro-2-methoxyphenyl)-1H-pyrrolo[2,3-b]pyridin-2-yl]cyclohex-3-ene-1-carboxylic acid;
tert-butyl 4-[4-(5-fluoro-2-methoxyphenyl)-3-nitro-1H-pyrrolo[2,3-b]pyridin-2-yl]piperazine-1-carboxylate;
4-(5-fluoro-2-methoxyphenyl)-3-nitro-2-(piperazin-1-yl)-1H-pyrrolo[2,3-b]pyridine;
4-[4-(5-fluoro-2-methoxyphenyl)-3-nitro-1H-pyrrolo[2,3-b]pyridin-2-yl]-N-methylpiperazine-1-carboxamide;
4-(5-fluoro-2-methoxyphenyl)-2-{1-[1-(methylsulfonyl)azetidin-3-yl]-1,2,3,6-tetrahydropyridin-4-yl}-1H-pyrrolo[2,3-b]pyridine;
4-(5-fluoro-2-methoxyphenyl)-2-{1-[1-(methylsulfonyl)azetidin-3-yl]piperidin-4-yl}-1H-pyrrolo[2,3-b]pyridine;
2-{4-[4-(5-fluoro-2-methoxyphenyl)-1H-pyrrolo[2,3-b]pyridin-2-yl]-2,3,6,7-tetrahydro-1H-azepin-1-yl}-N-(3-hydroxycyclobutyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-N-(2-hydroxyethyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-1-[(2S)-2-(hydroxymethyl)pyrrolidin-1-yl]ethanone;

4-(5-fluoro-2-methoxyphenyl)-5-methoxy-2-[2-(methylsulfonyl)-1,2,3,3a,4,6a-hexahydrocyclopenta[c]pyrrol-5-yl]-1H-pyrrolo[2,3-b]pyridine;

2-{5-[4-(5-fluoro-2-methoxyphenyl)-5-methoxy-1H-pyrrolo[2,3-b]pyridin-2-yl]-3,3a,4,6a-tetrahydrocyclopenta[c]pyrrol-2(1H)-yl}-N,N-dimethylacetamide;

4-[4-(4,5-difluoro-2-methoxyphenyl)-5-fluoro-1H-pyrrolo[2,3-b]pyridin-2-yl]cyclohex-3-ene-1-carboxylic acid;

4-[5-fluoro-4-(4-fluoro-2-methoxyphenyl)-1H-pyrrolo[2,3-b]pyridin-2-yl]cyclohex-3-ene-1-carboxylic acid;

(4-{4-[4-(5-fluoro-2-methoxyphenyl)-1H-pyrrolo[2,3-b]pyridin-2-yl]cyclohex-3-en-1-yl}piperazin-1-yl)acetic acid;

2-{4-[5-fluoro-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-N-(trans-4-hydroxycyclohexyl)acetamide;

{4-[4-(5-fluoro-2-methoxyphenyl)-1H-pyrrolo[2,3-b]pyridin-2-yl]-3,6-dihydropyridin-1(2H)-yl}(3-hydroxy-1,2-oxazol-5-yl)methanone;

3-{4-[4-(5-fluoro-2-methoxyphenyl)-1H-pyrrolo[2,3-b]pyridin-2-yl]-3,6-dihydropyridin-1(2H)-yl}-N-methylazetidine-1-carboxamide;

3-{4-[4-(5-fluoro-2-methoxyphenyl)-1H-pyrrolo[2,3-b]pyridin-2-yl]piperidin-1-yl}-N-methylazetidine-1-carboxamide;

3-{4-[4-(5-fluoro-2-methoxyphenyl)-1H-pyrrolo[2,3-b]pyridin-2-yl]-3,6-dihydropyridin-1(2H)-yl}cyclobutanecarbonitrile;

3-{4-[4-(5-fluoro-2-methoxyphenyl)-1H-pyrrolo[2,3-b]pyridin-2-yl]-3,6-dihydropyridin-1(2H)-yl}cyclopentanecarboxylic acid;

9-[4-(5-fluoro-2-methoxyphenyl)-1H-pyrrolo[2,3-b]pyridin-2-yl]-3-azaspiro[5.5]undec-8-ene;

9-[4-(5-fluoro-2-methoxyphenyl)-1H-pyrrolo[2,3-b]pyridin-2-yl]-N-methyl-3-azaspiro[5.5]undec-8-ene-3-carboxamide;

9-[4-(5-fluoro-2-methoxyphenyl)-1H-pyrrolo[2,3-b]pyridin-2-yl]-3-(methylsulfonyl)-3-azaspiro[5.5]undec-8-ene;

(3-{4-[4-(5-fluoro-2-methoxyphenyl)-1H-pyrrolo[2,3-b]pyridin-2-yl]-3,6-dihydropyridin-1(2H)-yl}cyclobutyl)methanol;

(trans-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

(cis-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

N-(1,1-dioxidotetrahydrothiophen-3-yl)-2-{4-[4-(5-fluoro-2-methoxyphenyl)-1H-pyrrolo[2,3-b]pyridin-2-yl]-3,6-dihydropyridin-1(2H)-yl}acetamide;

N-(1,1-dioxidotetrahydrothiophen-3-yl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]-3,6-dihydropyridin-1(2H)-yl}-1-[3-(methylsulfonyl)azetidin-1-yl]ethanone;

2-{4-[4-(5-fluoro-2-methoxyphenyl)-1H-pyrrolo[2,3-b]pyridin-2-yl]piperidin-1-yl}-1-[3-(methylsulfonyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-N-(1-methyl-1H-pyrazol-4-yl)acetamide;

4-(4-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-(4,5-difluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

2-{3-[4-(5-fluoro-2-methoxyphenyl)-1H-pyrrolo[2,3-b]pyridin-2-yl]-9-azabicyclo[3.3.1]non-2-en-9-yl}-N-(2-hydroxyethyl)-N-methylacetamide;

2-{3-[4-(5-fluoro-2-methoxyphenyl)-1H-pyrrolo[2,3-b]pyridin-2-yl]-9-azabicyclo[3.3.1]non-2-en-9-yl}-1-(3-hydroxyazetidin-1-yl)ethanone;

2-{3-[4-(5-fluoro-2-methoxyphenyl)-1H-pyrrolo[2,3-b]pyridin-2-yl]-9-azabicyclo[3.3.1]non-2-en-9-yl}-1-[(2S)-2-(hydroxymethyl)pyrrolidin-1-yl]ethanone;

2-{3-[4-(5-fluoro-2-methoxyphenyl)-1H-pyrrolo[2,3-b]pyridin-2-yl]-9-azabicyclo[3.3.1]non-2-en-9-yl}-N-(3-hydroxycyclobutyl)-N-methylacetamide;

{3-[4-(5-fluoro-2-methoxyphenyl)-1H-pyrrolo[2,3-b]pyridin-2-yl]-9-azabicyclo[3.3.1]non-2-en-9-yl}acetic acid;

4-(2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-(5-fluoro-2-methoxyphenyl)-2-(piperazin-1-yl)-1H-pyrrolo[2,3-b]pyridine-3-carbonitrile;

tert-butyl (2-{4-[4-(5-fluoro-2-methoxyphenyl)-1H-pyrrolo[2,3-b]pyridin-2-yl]-3,6-dihydropyridin-1(2H)-yl}ethyl)carbamate;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;

4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

2-{4-[4-(5-fluoro-2-methoxyphenyl)-1H-pyrrolo[2,3-b]pyridin-2-yl]azepan-1-yl}-1-(3-hydroxyazetidin-1-yl)ethanone;

3-({4-[4-(5-fluoro-2-methoxyphenyl)-1H-pyrrolo[2,3-b]pyridin-2-yl]cyclohex-3-en-1-yl}amino)bicyclo[1.1.1]pentane-1-carboxylic acid;

2-{4-[4-(5-fluoro-2-methoxyphenyl)-1H-pyrrolo[2,3-b]pyridin-2-yl]-3,6-dihydropyridin-1(2H)-yl}ethanamine;

N-(2-{4-[4-(5-fluoro-2-methoxyphenyl)-1H-pyrrolo[2,3-b]pyridin-2-yl]-3,6-dihydropyridin-1(2H)-yl}ethyl)methanesulfonamide;

N-(2-{4-[4-(5-fluoro-2-methoxyphenyl)-1H-pyrrolo[2,3-b]pyridin-2-yl]-3,6-dihydropyridin-1(2H)-yl}ethyl)acetamide;

2-{4-[4-(5-fluoro-2-methoxyphenyl)-1H-pyrrolo[2,3-b]pyridin-2-yl]-3,6-dihydropyridin-1(2H)-yl}-N,N-dimethylethanesulfonamide;

4-(5-fluoro-2-methoxyphenyl)-2-[4-(methylsulfonyl)piperazin-1-yl]-3-nitro-1H-pyrrolo[2,3-b]pyridine;

4-(5-fluoro-2-methoxyphenyl)-2-[4-(methylsulfonyl)piperazin-1-yl]-1H-pyrrolo[2,3-b]pyridine-3-carbonitrile;

2-{3-[4-(5-fluoro-2-methoxyphenyl)-1H-pyrrolo[2,3-b]pyridin-2-yl]-2,5-dihydro-1H-pyrrol-1-yl}-1-(3-hydroxyazetidin-1-yl)ethanone;
(4-{4-[4-(5-fluoro-2-methoxyphenyl)-1H-pyrrolo[2,3-b]pyridin-2-yl]cyclohex-3-en-1-yl}piperidin-1-yl)acetic acid;
4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;
2-{3-[4-(5-fluoro-2-methoxyphenyl)-1H-pyrrolo[2,3-b]pyridin-2-yl]-2,5-dihydro-1H-pyrrol-1-yl}-N-(2-hydroxyethyl)-N-methylacetamide;
2-{3-[4-(5-fluoro-2-methoxyphenyl)-1H-pyrrolo[2,3-b]pyridin-2-yl]-2,5-dihydro-1H-pyrrol-1-yl}-N,N-dimethylacetamide;
2-{3-[4-(5-fluoro-2-methoxyphenyl)-1H-pyrrolo[2,3-b]pyridin-2-yl]-2,5-dihydro-1H-pyrrol-1-yl}-1-[(2S)-2-(hydroxymethyl)pyrrolidin-1-yl]ethanone;
2-(4-{4-[4-(5-fluoro-2-methoxyphenyl)-1H-pyrrolo[2,3-b]pyridin-2-yl]cyclohex-3-en-1-yl}piperidin-1-yl)-N,N-dimethylacetamide;
(4-{(1S)-4-[4-(5-fluoro-2-methoxyphenyl)-1H-pyrrolo[2,3-b]pyridin-2-yl]cyclohex-3-en-1-yl}piperidin-1-yl)acetic acid;
(4-{(1R)-4-[4-(5-fluoro-2-methoxyphenyl)-1H-pyrrolo[2,3-b]pyridin-2-yl]cyclohex-3-en-1-yl}piperidin-1-yl)acetic acid;
methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate;
(4-{(1S)-4-[4-(5-fluoro-2-methoxyphenyl)-1H-pyrrolo[2,3-b]pyridin-2-yl]cyclohex-3-en-1-yl}piperazin-1-yl)acetic acid;
(4-{(1R)-4-[4-(5-fluoro-2-methoxyphenyl)-1H-pyrrolo[2,3-b]pyridin-2-yl]cyclohex-3-en-1-yl}piperazin-1-yl)acetic acid;
(4-{4-[4-(5-fluoro-2-methoxyphenyl)-1H-pyrrolo[2,3-b]pyridin-2-yl]-3,6-dihydropyridin-1(2H)-yl}cyclohexylidene)acetic acid;
cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
trans-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
(cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
(1-{4-[4-(5-fluoro-2-methoxyphenyl)-1H-pyrrolo[2,3-b]pyridin-2-yl]cyclohex-3-en-1-yl}piperidin-4-yl)acetic acid;
methyl (4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetate;
cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
(4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetic acid;
(trans-4-{4-[5-fluoro-4-(5-fluoro-2-methoxyphenyl)-1H-pyrrolo[2,3-b]pyridin-2-yl]piperidin-1-yl}cyclohexyl)acetic acid;
2-(trans-4-{4-[4-(5-fluoro-2-methoxyphenyl)-1H-pyrrolo[2,3-b]pyridin-2-yl]-3,6-dihydropyridin-1(2H)-yl}cyclohexyl)-N-(propan-2-ylsulfonyl)acetamide;
trans-4-{4-[5-fluoro-4-(5-fluoro-2-methoxyphenyl)-1H-pyrrolo[2,3-b]pyridin-2-yl]-3,6-dihydropyridin-1(2H)-yl}-N-(propan-2-ylsulfonyl)cyclohexanecarboxamide;
(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexyl)acetic acid;
(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid; and pharmaceutically acceptable salts thereof.

Embodiments of Formula (IIIa)

In another aspect, the present invention relates to compounds of Formula (IIIa) or a pharmaceutically acceptable salt thereof,

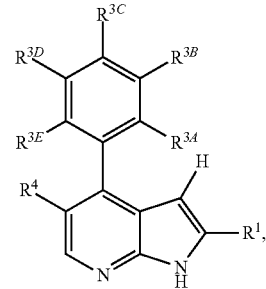

Formula (IIIa)

wherein
R$^1$ is selected from the group consisting of cycloalkyl, cycloalkenyl, heterocycloalkyl, and heterocycloalkenyl; wherein the R$^1$ cycloalkyl, cycloalkenyl, heterocycloalkyl and heterocycloalkenyl are optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, SO$_2$NHC(O)R$^5$, SO$_2$NR$^5$C(O)R$^5$, NHS(O)$_2$R$^5$, NR$^5$S(O)$_2$R$^5$, NHC(O)OR$^5$, NR$^5$C(O)OR$^5$, SO$_2$NHC(O)OR$^5$, SO$_2$NR$^5$C(O)OR$^5$, NHSO$_2$NHC(O)OR$^5$, NHSO$_2$NR$^5$C(O)OR$^5$, NR$^5$SO$_2$NR$^5$C(O)OR, NR$^5$SO$_2$NHC(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, OC(O)NH$_2$, OC(O)NHR$^5$, OC(O)N(R$^5$)$_2$, OC(O)NHSO$_2$R$^5$, OC(O)NR$^5$SO$_2$R$^5$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, OSO$_2$NH$_2$, OSO$_2$NHR$^5$, OSO$_2$N(R$^5$)$_2$, C(O)NHCN, C(O)NR$^5$CN, S(O)NR$^5$, S(O)(N)R$^5$SO$_2$R$^5$, C(O)H, C(O)OH, (O), OH, CN, NO$_2$, F, Cl, Br and I;
R$^{3A}$, R$^{3B}$, R$^{3C}$, R$^{3D}$, and R$^{3E}$ are each independently selected from the group consisting of H, R$^6$, OR$^6$, SR$^6$, S(O)R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, C(O)H, C(O)OH, (O), OH, CN, NO$_2$, F, Cl, Br and I;

R$^4$ is selected from the group consisting of R$^{4A}$, OR$^{4A}$, C(O)NH$_2$, CN, F, Cl, Br, and I;

R$^{4A}$ is selected from the group consisting of hydrogen, C$_1$-C$_6$ alkyl, C$_2$-C$_6$alkenyl, and C$_2$-C$_6$alkynyl;

R$^5$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^5$C$_1$-C$_6$ alkyl, C$_2$-C$_6$alkenyl, and C$_2$-C$_6$alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, B(OH)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I;

R$^6$, at each occurrence, is independently selected from the group consisting of C$_1$-C$_6$alkyl, C$_2$-C$_6$alkenyl, C$_2$-C$_6$alkynyl, phenyl, heteroaryl, heterocycloalkyl, heterocycloalkenyl, cycloalkyl, and cycloalkenyl; wherein each R$^6$C$_1$-C$_6$alkyl, C$_2$-C$_6$alkenyl, and C$_2$-C$_6$alkynyl is optionally substituted with one or more substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, CN, NO$_2$, F, Cl, Br and I; wherein each R$^6$ phenyl, cycloalkyl, cycloalkenyl, heteroaryl, heterocycloalkyl, and heterocycloalkenyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, (O), OH, CN, NO$_2$, F, Cl, Br and I;

R$^7$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^7$C$_1$-C$_6$ alkyl, C$_2$-C$_6$alkenyl, and C$_2$-C$_6$alkynyl is optionally substituted with one or more substituents independently selected from the group consisting of R$^{13}$, OR$^{13}$, NH$_2$, NHR$^{13}$, N(R$^{13}$)$_2$, C(O)H, C(O)OH, OH, CN, NO$_2$, F, Cl, Br and I; wherein each R$^7$ aryl, cycloalkyl, cycloalkenyl, heteroaryl, heterocycloalkyl, and heterocycloalkenyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, (O), OH, CN, NO$_2$, F, Cl, Br and I;

R$^8$, at each occurrence, is independently selected from the group consisting of C$_1$-C$_6$ alkyl, C$_2$-C$_6$alkenyl, C$_2$-C$_6$alkynyl, and heterocycloalkyl; wherein each R$^8$C$_1$-C$_6$ alkyl, C$_2$-C$_6$alkenyl, and C$_2$-C$_6$alkynyl is optionally substituted with one or more substituents independently selected from the group consisting of aryl, heteroaryl, SO$_2$R$^{8A}$, C(O)OR$^{8A}$, C(O)NH$_2$, C(O)NHR$^{8A}$, C(O)N(R$^{8A}$)$_2$, C(O)NHSO$_2$R$^{8A}$, C(O)NR$^{8A}$SO$_2$R$^{8A}$, NH$_2$, C(O)H, C(O)OH, OH, CN, NO$_2$, F, Cl, Br and I; wherein each R$^8$ heterocycloalkyl is optionally substituted with one or more substituents independently selected from the group consisting of NH$_2$, C(O)H, C(O)OH, OH, CN, NO$_2$, F, Cl, Br and I;

R$^{8A}$, at each occurrence, is independently selected from the group consisting of C$_1$-C$_6$ alkyl, C$_2$-C$_6$alkenyl, and C$_2$-C$_6$alkynyl;

R$^9$, at each occurrence, is independently selected from the group consisting of C$_1$-C$_6$alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^9$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I; wherein each R$^9$ aryl, cycloalkyl, cycloalkenyl, heteroaryl, heterocycloalkyl, and heterocycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, (O), OH, CN, NO$_2$, F, Cl, Br and I;

R$^{10}$, at each occurrence, is independently selected from the group consisting of C$_1$-C$_6$alkyl, C$_2$-C$_6$alkenyl, and C$_2$-C$_6$ alkynyl; wherein each R$^{10}$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I;

$R^{11}$, at each occurrence, is independently selected from the group consisting of $C_1$-$C_6$alkyl, $C_2$-$C_6$alkenyl, $C_2$-$C_6$alkynyl, aryl, and heteroaryl; wherein each $R^{11}C_1$-$C_6$alkyl, $C_2$-$C_6$alkenyl, and $C_2$-$C_6$alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$alkyl, $C_1$-$C_6$ haloalkyl, $NH_2$, $C(O)H$, $C(O)OH$, OH, CN, $NO_2$, F, Cl, Br and I;

$R^{11A}$, at each occurrence, is independently selected from the group consisting of $C_1$-$C_6$alkyl, $C_2$-$C_6$alkenyl, and $C_2$-$C_6$ alkynyl;

$R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{14}$, $N(R^{14})_2$, $C(O)H$, $C(O)OH$, OH, CN, $NO_2$, F, Cl, Br and I;

$R^{13}$, at each occurrence, is independently selected from the group consisting of $C_1$-$C_6$alkyl, $C_2$-$C_6$alkenyl, $C_2$-$C_6$ alkynyl, aryl, heteroaryl, cycloalkyl, cycloalkenyl, heterocycloalkyl, and heterocycloalkenyl; wherein each $R^{13}C_1$-$C_6$alkyl, $C_2$-$C_6$alkenyl, and $C_2$-$C_6$alkynyl is optionally substituted with one or more substituents independently selected from the group consisting of $R^{15}$, $OR^{15}$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, (O), OH, CN, $NO_2$, F, Cl, Br and I;

$R^{14}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl;

$R^{15}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl; wherein each $R^{15}C_1$-$C_6$alkyl, $C_2$-$C_6$alkenyl, and $C_2$-$C_6$alkynyl is optionally substituted with one or more $OCH_3$; and $R^{16}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl.

In one embodiment of Formula (IIIa), $R^4$ is selected from the group consisting of $R^{4A}$, $OR^{4A}$, $C(O)NH_2$, CN, F, Cl, Br, and I; and $R^{4A}$ is selected from the group consisting of hydrogen, $C_1$-$C_6$ alkyl, $C_2$-$C_6$alkenyl, and $C_2$-$C_6$alkynyl. In another embodiment of Formula (IIIa), $R^4$ is selected from the group consisting of $R^{4A}$, $OR^{4A}$, $C(O)NH_2$, CN, F, and Cl; and $R^{4A}$ is selected from the group consisting of hydrogen and $C_1$-$C_6$ alkyl. In another embodiment of Formula (IIIa), $R^4$ is selected from the group consisting of $R^{4A}$, $OR^{4A}$, $C(O)NH_2$, CN, F, and Cl; and $R^{4A}$ is selected from the group consisting of hydrogen and $C_1$-alkyl. In another embodiment of Formula (IIIa), $R^4$ is hydrogen. In another embodiment of Formula (IIIa), $R^4$ is CN. In another embodiment of Formula (IIIa), $R^4$ is F. In another embodiment of Formula (IIIa), $R^4$ is Cl. In another embodiment of Formula (IIIa), $R^4$ is OH. In another embodiment of Formula (IIIa), $R^4$ is $OCH_3$. In another embodiment of Formula (IIIa), $R^4$ is $CH_3$. In another embodiment of Formula (IIIa), $R^4$ is $C(O)NH_2$.

In one embodiment of Formula (IIIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R$, $C(O)H$, $C(O)OH$, (O), OH, CN, $NO_2$, F, Cl, Br and I. In another embodiment of Formula (IIIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SO_2R$, $C(O)R^5$, $CO(O)R^5$, $NH_2$, $NHR^5$, $NHC(O)R^5$, $SO_2NHC(O)R$, $NHS(O)_2R^5$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IIIa), $R^1$ is cycloalkyl; wherein the $R^1$ cycloalkyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IIIa), $R^1$ is cycloalkenyl; wherein the $R^1$ cycloalkenyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IIIa), $R^1$ is heterocycloalkyl; wherein the $R^1$ heterocycloalkyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IIIa), $R^1$ is heterocycloalkenyl; wherein the $R^1$ heterocycloalkenyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R$, $SO_2NHC$ (O)OR, NHSO₂NHC(O)OR, NHC(O)NHR⁵, OC(O)NHR⁵, OC(O)NHSO₂R⁵, C(O)NH₂, C(O)NHR⁵, C(O)N(R⁵)₂, C(O)NHOR⁵, C(O)NHSO₂R⁵, SO₂NH₂, SO₂NHR⁵, SO₂N(R⁵)₂, OSO₂NHR⁵, C(O)NHCN, S(O)NR⁵, S(O)(N)R⁵SO₂R⁵, C(O)OH, (O), OH, and CN. In another embodiment of Formula (IIIa), R¹ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the R¹ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, SO₂NHC(O)R⁵, SO₂NR⁵C(O)R⁵, NHS(O)₂R⁵, NR⁵S(O)₂R⁵, NHC(O)OR⁵, NR⁵C(O)OR⁵, SO₂NHC(O)OR⁵, SO₂NR⁵C(O)OR⁵, NHSO₂NHC(O)OR⁵, NHSO₂NR⁵C(O)OR⁵, NR⁵SO₂NR⁵C(O)OR⁵, NR⁵SO₂NHC(O)OR⁵, NHC(O)NH₂, NHC(O)NHR⁵, NHC(O)N(R⁵)₂, NR⁵C(O)NHR⁵, NR⁵C(O)N(R⁵)₂, OC(O)NH₂, OC(O)NHR⁵, OC(O)N(R⁵)₂, OC(O)NHSO₂R⁵, OC(O)NR⁵SO₂R⁵, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, OSO₂NH₂, OSO₂NHR⁵, OSO₂N(R⁵)₂, C(O)NHCN, C(O)NR⁵CN, S(O)NR⁵, S(O)(N)R⁵SO₂R⁵, C(O)H, C(O)OH, (O), OH, CN, NO₂, F, Cl, Br and I. In another embodiment of Formula (IIIa), R¹ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the R¹ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of R⁵, OR⁵, SO₂R⁵, C(O)R⁵, CO(O)R⁵, NH₂, NHR⁵, NHC(O)R⁵, SO₂NHC(O)R, NHS(O)₂R⁵, SO₂NHC(O)R⁵, NHSO₂NHC(O)OR, NHC(O)NHR⁵, OC(O)NHR⁵, OC(O)NHSO₂R⁵, C(O)NH₂, C(O)NHR⁵, C(O)N(R⁵)₂, C(O)NHOR⁵, C(O)NHSO₂R⁵, SO₂NH₂, SO₂NHR⁵, SO₂N(R⁵)₂, OSO₂NHR⁵, C(O)NHCN, S(O)NR⁵, S(O)(N)R⁵SO₂R, C(O)OH, (O), OH, and CN. In another embodiment of Formula (IIIa), R¹ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (IIIa), $R^{3A}$, $R^{3B}$, $R^{3C}$, $R^{3D}$, and $R^{3E}$ are each independently selected from the group consisting of H, R⁶, OR⁶, SR⁶, S(O)R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, C(O)H, C(O)OH, (O), OH, CN, NO₂, F, Cl, Br and I. In another embodiment of Formula (IIIa), $R^{3A}$, $R^{3B}$, $R^{3C}$, $R^{3D}$, and $R^{3E}$ are each independently selected from the group consisting of H, R⁶, OR⁶, SR⁶, S(O)R⁶, C(O)R⁶, NH₂, NHR⁶, N(R⁶)₂, NHC(O)R⁶, NHS(O)₂R⁶, C(O)NH₂, C(O)NHR⁶, C(O)N(R⁶)₂, CN, F, and Cl. In another embodiment of Formula (IIIa), $R^{3A}$, $R^{3B}$, $R^{3C}$, $R^{3D}$, and $R^{3E}$ are each independently selected from the group consisting of H, R⁶, OR⁶, NH₂, NHR⁶, N(R⁶)₂, NHC(O)R⁶, NHS(O)₂R⁶, CN, F, and Cl. In another embodiment of Formula (IIIa), $R^{3A}$, $R^{3B}$, $R^{3C}$, $R^{3D}$, and $R^{3E}$ are each independently selected from the group consisting of H, R⁶, OR⁶, NH₂, NHR⁶, N(R⁶)₂, NHS(O)₂R⁶, CN, F, and Cl. In one embodiment of Formula (IIIa), $R^{3A}$ is H, $R^{3B}$ is F, $R^{3C}$ is H, $R^{3D}$ is H, and $R^{3E}$ is OR⁶. In another embodiment of Formula (IIIa), $R^{3A}$ is H, $R^{3B}$ is F, $R^{3C}$ is H, $R^{3D}$ is H, and $R^{3E}$ is OCH₃. In another embodiment of Formula (IIIa), $R^{3A}$ is H, $R^{3D}$ is H, and $R^{3E}$ is OCH₃; and $R^{3B}$ and $R^{3C}$ are each independently selected from the group consisting of H, R⁶, OR⁶, SR⁶, S(O)R⁶, C(O)R⁶, NH₂, NHR⁶, N(R⁶)₂, NHC(O)R⁶, NHS(O)₂R⁶, C(O)NH₂, C(O)NHR⁶, C(O)N(R⁶)₂, CN, F, and Cl.

In one embodiment of Formula (IIIa), R⁵, at each occurrence, is independently selected from the group consisting of $C_1$-$C_6$ alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^5 C_1$-$C_6$ alkyl, $C_2$-$C_6$alkenyl, and $C_2$-$C_6$alkynyl is optionally substituted with one or more substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, B(OH)₂, C(O)H, C(O)OH, OH, CN, NO₂, F, Cl, Br and I; wherein each R⁵ aryl, cycloalkyl, cycloalkenyl, heteroaryl, heterocycloalkyl, and heterocycloalkenyl is optionally substituted with one or more substituents independently selected from the group consisting of R⁸, OR, SR⁸, S(O)R, SO₂R⁸, C(O)R⁸, CO(O)R, OC(O)R, OC(O)OR, NH₂, NHR⁵, N(R⁸)₂, NHC(O)R, NR⁸C(O)R⁸, NHS(O)₂R⁸, NR⁸S(O)₂R⁸, NHC(O)OR⁸, NR⁸C(O)OR⁸, NHC(O)NH₂, NHC(O)NHR⁸, NHC(O)N(R⁸)₂, NR⁸C(O)NHR⁸, NR⁸C(O)N(R⁸)₂, C(O)NH₂, C(O)NHR⁸, C(O)N(R⁸)₂, C(O)NHOH, C(O)NHOR⁸, C(O)NHSO₂R⁸, C(O)NR⁸SO₂R⁸, SO₂NH₂, SO₂NHR⁸, SO₂N(R⁸)₂, C(O)H, C(O)OH, (O), OH, CN, NO₂, F, Cl, Br and I. In another embodiment of Formula (IIIa), R⁵, at each occurrence, is independently selected from the group consisting of $C_1$-$C_6$ alkyl, aryl, heteroaryl, heterocycloalkyl, heterocycloalkenyl, cycloalkyl, and cycloalkenyl; wherein each $R^5 C_1$-$C_6$ alkyl is optionally substituted with one or more substituents independently selected from the group consisting of R⁷, OR⁷, SO₂R⁷, C(O)R⁷, CO(O)R⁷, OC(O)R⁷, NH₂, NHR⁷, N(R⁷)₂, NHC(O)R⁷, NHS(O)₂R⁷, NHC(O)OR⁷, NHC(O)NHR⁷, C(O)NH₂, C(O)NHR⁷, C(O)N(R⁷)₂, C(O)NHSO₂R⁷, SO₂NH₂, SO₂NHR⁷, SO₂N(R⁷)₂, B(OH)₂, C(O)OH, OH, CN, F, and Cl; wherein each R⁵ aryl, cycloalkyl, heteroaryl, heterocycloalkyl, and heterocycloalkenyl is optionally substituted with one or more substituents independently selected from the group consisting of R⁸, OR⁸, SR⁸, SO₂R⁸, C(O)R⁸, CO(O)R⁸, NH₂, NHR⁸, NHC(O)R⁸, NHS(O)₂R⁸, C(O)NHR⁸, C(O)N(R⁸)₂, C(O)NHSO₂R⁸, C(O)OH, (O), OH, CN, NO₂, F, and Cl.

In one embodiment of Formula (IIIa), R⁶, at each occurrence, is independently selected from the group consisting of $C_1$-$C_6$alkyl, $C_2$-$C_6$alkenyl, $C_2$-$C_6$alkynyl, phenyl, heteroaryl, heterocycloalkyl, heterocycloalkenyl, cycloalkyl, and cycloalkenyl; wherein each $R^6 C_1$-$C_6$alkyl, $C_2$-$C_6$alkenyl, and $C_2$-$C_6$alkynyl is optionally substituted with one or more substituents independently selected from the group consisting of R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, OH, CN, NO₂, F, Cl, Br and I; wherein each R⁶ phenyl, cycloalkyl, cycloalkenyl, heteroaryl, heterocycloalkyl, and heterocycloalkenyl is optionally substituted with one or more substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, (O), OH, CN, NO₂, F, Cl, Br and I. In another embodiment of Formula (IIIa), R⁶, at each occurrence, is independently selected from the group consisting of $C_1$-$C_6$alkyl, phenyl, heteroaryl, heterocycloalkyl, heterocycloalkenyl, and cycloalkyl; wherein each $R^6 C_1$-$C_6$alkyl, is optionally substituted with one or more substituents independently selected from the group consisting of R⁹, NH₂, NHR⁹, NHS(O)₂R⁹, CN, and F; and wherein each R⁶ phenyl, heteroaryl, heterocycloalkyl, heterocycloalkenyl, and cycloalkyl is optionally substituted with one or more substituents independently selected from the group consisting of R¹⁰, OR¹⁰, and F.

In one embodiment of Formula (IIIa), R⁷, at each occurrence, is independently selected from the group consisting of $C_1$-$C_6$ alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^7 C_1$-$C_6$ alkyl, $C_2$-$C_6$alkenyl, and $C_2$-$C_6$alkynyl is optionally substituted with one or more substituents independently selected from the group consisting of R¹³, OR¹³, NH₂, NHR¹³, N(R¹³)₂, C(O)H, C(O)OH, OH, CN, NO₂, F, Cl, Br and I; wherein each R⁷ aryl, cycloalkyl, cycloalkenyl, heteroaryl, heterocycloalkyl, and heterocycloalkenyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, (O), OH, CN, NO₂, F, Cl, Br and I. In another embodiment of Formula (IIIa), R⁷, at each occurrence, is independently selected from the group consisting of $C_1$-$C_6$ alkyl, aryl, heteroaryl, heterocycloalkyl, heterocycloalkenyl, and cycloalkyl; wherein each $R^7 C_1$-$C_6$ alkyl is optionally substituted with one or more substituents independently selected from the group consisting of R¹³, OR¹³, N(R¹³)₂, and OH; wherein each $R^7$ aryl, heteroaryl, heterocycloalkyl, heterocycloalkenyl, and cycloalkyl is optionally substituted with one or more substituents independently selected from the group consisting of $R^{11}$, $OR^{11}$, $SO_2R^{11}$, $C(O)R^{11}$, $CO(O)R^{11}$, $NH_2$, $N(R^{11})_2$, $NHC(O)R^{11}$, $NHS(O)_2R^{11}$, $C(O)NH_2$, $C(O)OH$, (O), OH, CN, F, and Cl.

In one embodiment of Formula (IIIa), $R^8$, at each occurrence, is independently selected from the group consisting of $C_1$-$C_6$ alkyl, $C_2$-$C_6$alkenyl, $C_2$-$C_6$alkynyl, and heterocycloalkyl; wherein each $R^8C_1$-$C_6$ alkyl, $C_2$-$C_6$alkenyl, and $C_2$-$C_6$alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)OH$, OH, CN, $NO_2$, F, Cl, Br and I; and $R^{8A}$, at each occurrence, is independently selected from the group consisting of $C_1$-$C_6$ alkyl, $C_2$-$C_6$alkenyl, and $C_2$-$C_6$alkynyl. In another embodiment of Formula (IIIa), $R^8$, at each occurrence, is independently selected from the group consisting of $C_1$-$C_6$ alkyl, $C_2$-$C_6$alkenyl, and heterocycloalkyl; wherein each $R^8C_1$-$C_6$ alkyl and $C_2$-$C_6$alkenyl is optionally substituted with one or more substituents independently selected from the group consisting of aryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)OH$, OH, CN, and F; wherein each $R^8$ heterocycloalkyl is optionally substituted with one or more OH; and $R^{8A}$, at each occurrence, is independently $C_1$-$C_6$ alkyl.

In one embodiment of Formula (IIIa), $R^9$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^9C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I. In another embodiment of Formula (IIIa), $R^9$, at each occurrence, is independently selected from the group consisting of $C_1$-$C_6$alkyl, aryl, heteroaryl, heterocycloalkyl, cycloalkyl, and cycloalkenyl; wherein each $R^9$ aryl, heteroaryl, heterocycloalkyl, cycloalkyl, and cycloalkenyl is optionally substituted with one or more substituents independently selected from the group consisting of $R^{12}$, $OR^{12}$, $SO_2R^{12}$, $NH_2$, $C(O)NH_2$, $SO_2NH_2$, $C(O)OH$, (O), OH, CN, F, and Cl.

In one embodiment of Formula (IIIa), $R^{10}$, at each occurrence, is independently selected from the group consisting of $C_1$-$C_6$alkyl, $C_2$-$C_6$alkenyl, and $C_2$-$C_6$ alkynyl; wherein each $R^{10}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)$ OH, OH, CN, $NO_2$, F, Cl, Br and I. In another embodiment of Formula (IIIa), $R^{10}$, at each occurrence, is $C_1$-$C_6$alkyl.

In one embodiment of Formula (IIIa), $R^{11}$, at each occurrence, is independently selected from the group consisting of $C_1$-$C_6$alkyl, $C_2$-$C_6$alkenyl, $C_2$-$C_6$alkynyl, aryl, and heteroaryl; wherein each $R^{11}C_1$-$C_6$alkyl, $C_2$-$C_6$alkenyl, and $C_2$-$C_6$alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$alkyl, $C_1$-$C_6$ haloalkyl, $NH_2$, $C(O)H$, $C(O)OH$, OH, CN, $NO_2$, F, Cl, Br and I; and $R^{11A}$, at each occurrence, is independently selected from the group consisting of $C_1$-$C_6$alkyl, $C_2$-$C_6$alkenyl, and $C_2$-$C_6$ alkynyl. In another embodiment of Formula (IIIa), $R^{11}$, at each occurrence, is independently selected from the group consisting of $C_1$-$C_6$alkyl and aryl; wherein each $R^{11}C_1$-$C_6$alkyl is optionally substituted with one or more substituents independently selected from the group consisting of $OR^{11A}$, $N(R^{11A})_2$, $C(O)OH$, and OH; wherein each $R^{11}$ aryl is optionally substituted with one or more $C_1$-$C_6$alkyl; and $R^{11A}$, at each occurrence, is independently $C_1$-$C_6$alkyl.

In one embodiment of Formula (IIIa), $R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{14}$, $N(R^{14})_2$, $C(O)H$, $C(O)OH$, OH, CN, $NO_2$, F, Cl, Br and I. In another embodiment of Formula (IIIa), $R^{12}$, at each occurrence, is independently $C_1$-$C_6$alkyl; wherein each $R^{12}C_1$-$C_6$alkyl is optionally substituted with one or more $C(O)OH$.

In one embodiment of Formula (IIIa), $R^{13}$, at each occurrence, is independently selected from the group consisting of $C_1$-$C_6$alkyl, $C_2$-$C_6$alkenyl, $C_2$-$C_6$ alkynyl, aryl, heteroaryl, cycloalkyl, cycloalkenyl, heterocycloalkyl, and heterocycloalkenyl; wherein each $R^{13}C_1$-$C_6$alkyl, $C_2$-$C_6$alkenyl, and $C_2$-$C_6$alkynyl is optionally substituted with one or more substituents independently selected from the group consisting of $R^{15}$, $OR^{15}$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, (O), OH, CN, $NO_2$, F, Cl, Br and I. In another embodiment of Formula (IIIa), $R^{13}$, at each occurrence, is independently selected from the group consisting of $C_1$-$C_6$alkyl, aryl, heteroaryl, and heterocycloalkyl; wherein each $R^{13}C_1$-$C_6$alkyl is optionally substituted with one or more $OR^{15}$; wherein each $R^{13}$ aryl, heteroaryl, and heterocycloalkyl is optionally substituted with one or more $R^{16}$.

In one embodiment of Formula (IIIa), $R^{15}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl; wherein each $R^{15}C_1$-$C_6$alkyl, $C_2$-$C_6$alkenyl, and $C_2$-$C_6$alkynyl is optionally substituted with one or more $OCH_3$. In another embodiment of Formula (IIIa), $R^{15}$, at each occurrence, is independently $C_1$-$C_6$alkyl; wherein each $R^{15}C_1$-$C_6$alkyl is optionally substituted with one or more $OCH_3$.

In one embodiment of Formula (IIIa), $R^{16}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl. In another embodiment of Formula (IIIa), $R^{16}$, at each occurrence, is independently selected from the group consisting of $C_1$-$C_6$ haloalkyl and $C_1$-$C_6$alkyl.

In another embodiment of Formula (IIIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R^5$, $SO_2NHC(O)OR^5$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN;

$R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl;

$R^4$ is selected from the group consisting of $R^{4A}$, $OR^{4A}$, $C(O)NH_2$, CN, F, and Cl;

$R^{4A}$ is selected from the group consisting of hydrogen and $C_1$-$C_6$ alkyl;

$R^5$, at each occurrence, is independently selected from the group consisting of $C_1$-$C_6$ alkyl, aryl, heteroaryl, heterocycloalkyl, heterocycloalkenyl, cycloalkyl, and cycloalkenyl; wherein each $R^5C_1$-$C_6$ alkyl is optionally substituted with one or more substituents independently selected from the group consisting of $R^7$, $OR^7$, $SO_2R^7$, $C(O)R^7$, $CO(O)R^7$, $OC(O)R^7$, $NH_2$, $NHR^7$, $N(R^7)_2$, $NHC(O)R^7$, $NHS(O)_2R^7$, $NHC(O)OR$, $NHC(O)NHR^7$, $C(O)NH_2$, $C(O)NHR^7$, $C(O)N(R^7)_2$, $C(O)NHSO_2R^7$, $SO_2NH_2$, $SO_2NHR^7$, $SO_2N(R^7)_2$, $B(OH)_2$, $C(O)OH$, OH, CN, F, and Cl; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $SO_2R^8$, $C(O)R^8$, $CO(O)R^8$, $NH_2$, $NHR^8$, $NHC(O)R^8$, $NHS(O)_2R^8$, $C(O)NHR^8$, $C(O)N(R^8)_2$, $C(O)NHSO_2R^8$, $C(O)OH$, (O), OH, CN, F, and Cl;

$R^6$, at each occurrence, is independently selected from the group consisting of $C_1$-$C_6$alkyl, phenyl, heteroaryl, heterocycloalkyl, heterocycloalkenyl, cycloalkyl, and cycloalkenyl; wherein each $R^6C_1$-$C_6$alkyl is optionally substituted with one or more substituents independently selected from the group consisting of $R^9$, $NH_2$, $NHR^9$, $NHS(O)_2R^9$, CN, and F; wherein each $R^6$ phenyl, cycloalkyl, heteroaryl, heterocycloalkyl, and heterocycloalkenyl is optionally substituted with one or more substituents independently selected from the group consisting of $R^{10}$, $OR^{10}$, and F;

$R^7$, at each occurrence, is independently selected from the group consisting of $C_1$-$C_6$ alkyl, aryl, heteroaryl, heterocycloalkyl, heterocycloalkenyl, and cycloalkyl; wherein each $R^7C_1$-$C_6$ alkyl is optionally substituted with one or more substituents independently selected from the group consisting of $R^{13}$, $OR^{13}$, $N(R^{13})_2$, and OH; wherein each $R^7$ aryl, heteroaryl, heterocycloalkyl, heterocycloalkenyl, and cycloalkyl is optionally substituted with one or more substituents independently selected from the group consisting of $R^{11}$, $OR^{11}$, $SO_2R^{11}$, $C(O)R^{11}$, $CO(O)R^{11}$, $NH_2$, $N(R^{11})_2$, $NHC(O)R^{11}$, $NHS(O)_2R^{11}$, $C(O)NH_2$, $C(O)OH$, (O), OH, CN, F, and Cl;

$R^8$, at each occurrence, is independently selected from the group consisting of $C_1$-$C_6$ alkyl, $C_2$-$C_6$alkenyl, and heterocycloalkyl; wherein each $R^8C_1$-$C_6$ alkyl and $C_2$-$C_6$alkenyl is optionally substituted with one or more substituents independently selected from the group consisting of aryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)OH$, OH, CN, and F; wherein each $R^8$ heterocycloalkyl is optionally substituted with one or more OH;

$R^{8A}$, at each occurrence, is independently $C_1$-$C_6$alkyl;

$R^9$, at each occurrence, is independently selected from the group consisting of $C_1$-$C_6$alkyl, aryl, heteroaryl, heterocycloalkyl, cycloalkyl, and cycloalkenyl; wherein each $R^9$ aryl, heteroaryl, heterocycloalkyl, cycloalkyl, and cycloalkenyl is optionally substituted with one or more substituents independently selected from the group consisting of $R^{12}$, $OR^{12}$, $SO_2R^{12}$, $NH_2$, $C(O)NH_2$, $SO_2NH_2$, $C(O)OH$, (O), OH, CN, F, and Cl;

$R^{10}$, at each occurrence, is independently $C_1$-$C_6$alkyl;

$R^{11}$, at each occurrence, is independently selected from the group consisting of $C_1$-$C_6$alkyl, and aryl; wherein each $R^{11}C_1$-$C_6$alkyl is optionally substituted with one or more substituents independently selected from the group consisting of $OR^{11A}$, $N(R^{11A})_2$, $C(O)OH$, and OH; wherein each $R^{11}$ aryl is optionally substituted with one or more substituents independently selected from the group consisting of $C_1$-$C_6$alkyl;

$R^{11A}$, at each occurrence, is independently $C_1$-$C_6$alkyl;

$R^{12}$, at each occurrence, is independently $C_1$-$C_6$alkyl; wherein each $R^{12}C_1$-$C_6$alkyl is optionally substituted with one or more $C(O)OH$;

$R^{13}$, at each occurrence, is independently selected from the group consisting of $C_1$-$C_6$alkyl, aryl, heteroaryl, and heterocycloalkyl; wherein each $R^{13}C_1$-$C_6$alkyl is optionally substituted with one or more $OR^{15}$; wherein each $R^{13}$ aryl, heteroaryl, and heterocycloalkyl, and heterocycloalkenyl is optionally substituted with one or more $R^{16}$;

$R^{15}$, at each occurrence, is independently $C_1$-$C_6$alkyl; wherein each $R^{15}C_1$-$C_6$alkyl is optionally substituted with one or more $OCH_3$; and $R^{16}$, at each occurrence, is independently selected from the group consisting of $C_1$-$C_6$ haloalkyl, and $C_1$-$C_6$alkyl.

Still another embodiment pertains to compounds of Formula (IIIa), selected from the group consisting of:

4-(5-fluoro-2-methoxyphenyl)-2-(piperidin-3-yl)-1H-pyrrolo[2,3-b]pyridine;

4-(4-fluoro-2-methoxyphenyl)-2-(piperidin-3-yl)-1H-pyrrolo[2,3-b]pyridine;

4-(5-fluoro-2-methoxyphenyl)-2-[(3S)-piperidin-3-yl]-1H-pyrrolo[2,3-b]pyridine;

4-(5-fluoro-2-methoxyphenyl)-2-[(3R)-piperidin-3-yl]-1H-pyrrolo[2,3-b]pyridine;

4-[5-(4,5-dihydro-1H-imidazol-2-yl)-2-methoxyphenyl]-2-(piperidin-3-yl)-1H-pyrrolo[2,3-b]pyridine;

4-(5-cyclopropyl-2-methoxyphenyl)-2-(piperidin-3-yl)-1H-pyrrolo[2,3-b]pyridine;

4-(4-fluoro-2-methoxyphenyl)-2-(1-methylpiperidin-3-yl)-1H-pyrrolo[2,3-b]pyridine;

4-(5-fluoro-2-methoxyphenyl)-2-(1-methylpiperidin-3-yl)-1H-pyrrolo[2,3-b]pyridine;

1-{3-[4-(5-fluoro-2-methoxyphenyl)-1H-pyrrolo[2,3-b]pyridin-2-yl]piperidin-1-yl}ethanone;

4-(5-fluoro-2-methoxyphenyl)-2-(piperidin-4-yl)-1H-pyrrolo[2,3-b]pyridine;

4-(4-fluoro-2-methoxyphenyl)-2-(piperidin-4-yl)-1H-pyrrolo[2,3-b]pyridine;
4-(4-chloro-2-methoxyphenyl)-2-(piperidin-4-yl)-1H-pyrrolo[2,3-b]pyridine;
4-(4,5-difluoro-2-methoxyphenyl)-2-(piperidin-4-yl)-1H-pyrrolo[2,3-b]pyridine;
4-(5-chloro-2-methoxyphenyl)-2-(piperidin-4-yl)-1H-pyrrolo[2,3-b]pyridine;
4-(2-methoxy-5-methylphenyl)-2-(piperidin-4-yl)-1H-pyrrolo[2,3-b]pyridine;
4-(3-chloro-2-methoxyphenyl)-2-(piperidin-4-yl)-1H-pyrrolo[2,3-b]pyridine;
4-(2-methoxyphenyl)-2-(piperidin-4-yl)-1H-pyrrolo[2,3-b]pyridine;
4-(5-fluoro-2-methoxyphenyl)-2-(1-methylpiperidin-4-yl)-1H-pyrrolo[2,3-b]pyridine;
4-(4-fluoro-2-methoxyphenyl)-2-(1-methylpiperidin-4-yl)-1H-pyrrolo[2,3-b]pyridine;
4-(2-methoxy-5-methylphenyl)-2-(1-methylpiperidin-4-yl)-1H-pyrrolo[2,3-b]pyridine;
N-{4-chloro-3-[2-(piperidin-4-yl)-1H-pyrrolo[2,3-b]pyridin-4-yl]phenyl}benzenesulfonamide;
N-benzyl-4-fluoro-3-[2-(piperidin-4-yl)-1H-pyrrolo[2,3-b]pyridin-4-yl]aniline;
N-benzyl-4-chloro-3-[2-(piperidin-4-yl)-1H-pyrrolo[2,3-b]pyridin-4-yl]aniline;
4-(5-fluoro-2-methoxyphenyl)-2-(pyrrolidin-3-yl)-1H-pyrrolo[2,3-b]pyridine;
4-(4-fluoro-2-methoxyphenyl)-2-(pyrrolidin-3-yl)-1H-pyrrolo[2,3-b]pyridine;
4-(5-fluoro-2-methoxyphenyl)-2-[(3S)-pyrrolidin-3-yl]-1H-pyrrolo[2,3-b]pyridine;
4-(5-fluoro-2-methoxyphenyl)-2-[(3R)-pyrrolidin-3-yl]-1H-pyrrolo[2,3-b]pyridine;
4-(5-fluoro-2-methoxyphenyl)-2-(1-methylpyrrolidin-3-yl)-1H-pyrrolo[2,3-b]pyridine;
4-(4-fluoro-2-methoxyphenyl)-2-(morpholin-2-yl)-1H-pyrrolo[2,3-b]pyridine;
4-(5-fluoro-2-methoxyphenyl)-2-(morpholin-2-yl)-1H-pyrrolo[2,3-b]pyridine;
4-(4-fluoro-2-methoxyphenyl)-2-(4-methylmorpholin-2-yl)-1H-pyrrolo[2,3-b]pyridine;
4-(5-fluoro-2-methoxyphenyl)-2-(4-methylmorpholin-2-yl)-1H-pyrrolo[2,3-b]pyridine;
2-(5,5-dimethylmorpholin-2-yl)-4-(5-fluoro-2-methoxyphenyl)-1H-pyrrolo[2,3-b]pyridine;
2-(5,5-dimethylmorpholin-2-yl)-4-(4-fluoro-2-methoxyphenyl)-1H-pyrrolo[2,3-b]pyridine;
4-(4-chloro-2-methoxyphenyl)-2-(5,5-dimethylmorpholin-2-yl)-1H-pyrrolo[2,3-b]pyridine;
trans-4-[4-(5-fluoro-2-methoxyphenyl)-1H-pyrrolo[2,3-b]pyridin-2-yl]cyclohexanamine;
3-[4-(5-fluoro-2-methoxyphenyl)-1H-pyrrolo[2,3-b]pyridin-2-yl]cyclohexanamine;
5-chloro-4-(3-fluorophenyl)-2-(piperidin-3-yl)-1H-pyrrolo[2,3-b]pyridine;
3-[5-chloro-4-(3-fluorophenyl)-1H-pyrrolo[2,3-b]pyridin-2-yl]cyclohexanamine;
4-(5-fluoro-2-methoxyphenyl)-2-(1,2,3,6-tetrahydropyridin-4-yl)-1H-pyrrolo[2,3-b]pyridine;
4-(5-fluoro-2-methoxyphenyl)-2-(pyrrolidin-2-yl)-1H-pyrrolo[2,3-b]pyridine;
2-cyclohexyl-4-(5-fluoro-2-methoxyphenyl)-1H-pyrrolo[2,3-b]pyridine;
1-{2-[4-(5-fluoro-2-methoxyphenyl)-1H-pyrrolo[2,3-b]pyridin-2-yl]pyrrolidin-1-yl}ethanone;
1-{4-[4-(5-fluoro-2-methoxyphenyl)-1H-pyrrolo[2,3-b]pyridin-2-yl]-3,6-dihydropyridin-1(2H)-yl}ethanone;
1-{4-[4-(5-fluoro-2-methoxyphenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-(1-methylpyrrolidin-2-yl)-1H-pyrrolo[2,3-b]pyridine;
1-{3-[4-(5-fluoro-2-methoxyphenyl)-1H-pyrrolo[2,3-b]pyridin-2-yl]pyrrolidin-1-yl}ethanone;
2-{3-[4-(5-fluoro-2-methoxyphenyl)-1H-pyrrolo[2,3-b]pyridin-2-yl]pyrrolidin-1-yl}ethanol;
4-(5-fluoro-2-methoxyphenyl)-2-[1-(tetrahydro-2H-pyran-4-yl)pyrrolidin-3-yl]-1H-pyrrolo[2,3-b]pyridine;
4-(5-fluoro-2-methoxyphenyl)-2-[1-(pyridin-2-ylmethyl)pyrrolidin-3-yl]-1H-pyrrolo[2,3-b]pyridine;
4-(5-fluoro-2-methoxyphenyl)-2-[1-(pyridin-3-ylmethyl)pyrrolidin-3-yl]-1H-pyrrolo[2,3-b]pyridine;
4-(5-fluoro-2-methoxyphenyl)-2-[1-(pyridin-4-ylmethyl)pyrrolidin-3-yl]-1H-pyrrolo[2,3-b]pyridine;
4-(5-fluoro-2-methoxyphenyl)-2-[1-(tetrahydro-2H-pyran-3-ylmethyl)pyrrolidin-3-yl]-1H-pyrrolo[2,3-b]pyridine;
tert-butyl (2-{3-[4-(5-fluoro-2-methoxyphenyl)-1H-pyrrolo[2,3-b]pyridin-2-yl]pyrrolidin-1-yl}ethyl)carbamate;
tert-butyl 3-[4-(5-fluoro-2-methoxyphenyl)-1H-pyrrolo[2,3-b]pyridin-2-yl]-1,3'-bipyrrolidine-1'-carboxylate;
4-(5-fluoro-2-methoxyphenyl)-2-[1-(tetrahydro-2H-pyran-4-ylmethyl)pyrrolidin-3-yl]-1H-pyrrolo[2,3-b]pyridine;
4-(5-fluoro-2-methoxyphenyl)-2-{1-[2-(morpholin-4-yl)ethyl]pyrrolidin-3-yl}-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine;
methyl 4-({trans-4-[4-(5-fluoro-2-methoxyphenyl)-1H-pyrrolo[2,3-b]pyridin-2-yl]cyclohexyl}amino)butanoate;
ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate;
trans-4-[4-(5-fluoro-2-methoxyphenyl)-1H-pyrrolo[2,3-b]pyridin-2-yl]-N-[2-(morpholin-4-yl)ethyl]cyclohexanamine;
3-({trans-4-[4-(5-fluoro-2-methoxyphenyl)-1H-pyrrolo[2,3-b]pyridin-2-yl]cyclohexyl}amino)propane-1,2-diol;
2-{3-[4-(5-fluoro-2-methoxyphenyl)-1H-pyrrolo[2,3-b]pyridin-2-yl]pyrrolidin-1-yl}ethanamine;
3-[4-(5-fluoro-2-methoxyphenyl)-1H-pyrrolo[2,3-b]pyridin-2-yl]-1,3'-bipyrrolidine;
4-[4-(5-fluoro-2-methoxyphenyl)-1H-pyrrolo[2,3-b]pyridin-2-yl]piperidin-4-ol;
benzyl (3-{3-[4-(5-fluoro-2-methoxyphenyl)-1H-pyrrolo[2,3-b]pyridin-2-yl]piperidin-1-yl}propyl)carbamate;
2-{3-[4-(5-fluoro-2-methoxyphenyl)-1H-pyrrolo[2,3-b]pyridin-2-yl]piperidin-1-yl}ethanol;
3-{3-[4-(5-fluoro-2-methoxyphenyl)-1H-pyrrolo[2,3-b]pyridin-2-yl]piperidin-1-yl}propan-1-amine;
4-(5-fluoro-2-methoxyphenyl)-2-[1-(2-methoxyethyl)piperidin-3-yl]-1H-pyrrolo[2,3-b]pyridine;
4-({trans-4-[4-(5-fluoro-2-methoxyphenyl)-1H-pyrrolo[2,3-b]pyridin-2-yl]cyclohexyl}amino)butanoic acid;
1-{4-[4-(5-fluoro-2-methoxyphenyl)-1H-pyrrolo[2,3-b]pyridin-2-yl]piperidin-1-yl}ethanone;
1-{4-[4-(5-fluoro-2-methoxyphenyl)-1H-pyrrolo[2,3-b]pyridin-2-yl]piperidin-1-yl}-2-hydroxyethanone;
3-methoxy-4-[2-(piperidin-3-yl)-1H-pyrrolo[2,3-b]pyridin-4-yl]benzonitrile;
2-[({trans-4-[4-(5-fluoro-2-methoxyphenyl)-1H-pyrrolo[2,3-b]pyridin-2-yl]cyclohexyl}amino)methyl]cyclopropanecarboxylic acid;

2-(azetidin-3-yl)-4-(5-fluoro-2-methoxyphenyl)-1H-pyrrolo[2,3-b]pyridine;

1-{4-[4-(5-fluoro-2-methoxyphenyl)-1H-pyrrolo[2,3-b]pyridin-2-yl]piperidin-1-yl}-2-(4-hydroxypiperidin-1-yl)ethanone;

4-(5-fluoro-2-methoxyphenyl)-2-[1-(methylsulfonyl)piperidin-4-yl]-1H-pyrrolo[2,3-b]pyridine;

3-{4-[4-(5-fluoro-2-methoxyphenyl)-1H-pyrrolo[2,3-b]pyridin-2-yl]piperidin-1-yl}propane-1,2-diol;

4-[4-(5-fluoro-2-methoxyphenyl)-1H-pyrrolo[2,3-b]pyridin-2-yl]tetrahydro-2H-pyran-4-ol;

4-(5-fluoro-2-methoxyphenyl)-2-[1-(pyridin-4-ylmethyl)azetidin-3-yl]-1H-pyrrolo[2,3-b]pyridine;

1-{3-[4-(5-fluoro-2-methoxyphenyl)-1H-pyrrolo[2,3-b]pyridin-2-yl]azetidin-1-yl}ethanone;

2-{3-[4-(5-fluoro-2-methoxyphenyl)-1H-pyrrolo[2,3-b]pyridin-2-yl]azetidin-1-yl}ethanamine;

4-(5-fluoro-2-methoxyphenyl)-2-[1-(tetrahydro-2H-pyran-4-ylmethyl)azetidin-3-yl]-1H-pyrrolo[2,3-b]pyridine;

4-(5-fluoro-2-methoxyphenyl)-2-{1-[2-(morpholin-4-yl)ethyl]azetidin-3-yl}-1H-pyrrolo[2,3-b]pyridine;

2-{3-[4-(5-fluoro-2-methoxyphenyl)-1H-pyrrolo[2,3-b]pyridin-2-yl]azetidin-1-yl}ethanol;

4-fluoro-3-[2-(1-methylpiperidin-4-yl)-1H-pyrrolo[2,3-b]pyridin-4-yl]-N-(tetrahydro-2H-pyran-4-ylmethyl)aniline;

1-{4-[4-(5-fluoro-2-methoxyphenyl)-1H-pyrrolo[2,3-b]pyridin-2-yl]piperidin-1-yl}-2-(piperidin-1-yl)ethanone;

1-{4-[4-(5-fluoro-2-methoxyphenyl)-1H-pyrrolo[2,3-b]pyridin-2-yl]piperidin-1-yl}-2-(morpholin-4-yl) ethanone;

1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone;

1-{4-[4-(5-fluoro-2-methoxyphenyl)-1H-pyrrolo[2,3-b]pyridin-2-yl]piperidin-1-yl}-2-[(2-hydroxyethyl)amino]ethanone;

4-(5-fluoro-2-methoxyphenyl)-2-(1-methylazetidin-3-yl)-1H-pyrrolo[2,3-b]pyridine;

4-(5-fluoro-2-methoxyphenyl)-2-[1-(methylsulfonyl)azetidin-3-yl]-1H-pyrrolo[2,3-b]pyridine;

3-{4-[4-(5-fluoro-2-methoxyphenyl)-1H-pyrrolo[2,3-b]pyridin-2-yl]-3,6-dihydropyridin-1(2H)-yl}propane-1,2-diol;

4-fluoro-3-[2-(piperidin-4-yl)-1H-pyrrolo[2,3-b]pyridin-4-yl]aniline;

4-fluoro-3-[2-(1-methylpiperidin-4-yl)-1H-pyrrolo[2,3-b]pyridin-4-yl]-N-(pyridin-4-ylmethyl)aniline;

4-fluoro-3-[2-(1-methylpiperidin-4-yl)-1H-pyrrolo[2,3-b]pyridin-4-yl]-N-[4-(methylsulfonyl)benzyl]aniline;

4-[({4-fluoro-3-[2-(1-methylpiperidin-4-yl)-1H-pyrrolo[2,3-b]pyridin-4-yl]phenyl}amino)methyl]benzamide;

2-(azepan-3-yl)-4-(5-fluoro-2-methoxyphenyl)-1H-pyrrolo[2,3-b]pyridine;

N-benzyl-3-[5-chloro-2-(piperidin-4-yl)-1H-pyrrolo[2,3-b]pyridin-4-yl]-4-fluoroaniline;

N-benzyl-4-chloro-3-[2-(piperidin-3-yl)-1H-pyrrolo[2,3-b]pyridin-4-yl]aniline;

4-(4,5-difluoro-2-methoxyphenyl)-2-(piperidin-3-yl)-1H-pyrrolo[2,3-b]pyridine;

N-benzyl-4-fluoro-3-[2-(piperidin-3-yl)-1H-pyrrolo[2,3-b]pyridin-4-yl]aniline;

4-fluoro-N-(3-fluorobenzyl)-3-[2-(piperidin-3-yl)-1H-pyrrolo[2,3-b]pyridin-4-yl]aniline;

4-[4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-3,6-dihydropyridine-1(2H)-sulfonamide;

N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide;

tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-ene-1-carboxylic acid;

4-(2,3-difluorophenyl)-2-[1-(methylsulfonyl)-1,2,3,6-tetrahydropyridin-4-yl]-1H-pyrrolo[2,3-b]pyridine;

3-{4-[4-(5-fluoro-2-methoxyphenyl)-1H-pyrrolo[2,3-b]pyridin-2-yl]-3,6-dihydropyridin-1(2H)-yl}-3-oxopropanenitrile;

4-[4-(2,3-difluorophenyl)-1H-pyrrolo[2,3-b]pyridin-2-yl]-N-methyl-3,6-dihydropyridine-1(2H)-carboxamide;

4-(5-fluoro-2-methoxyphenyl)-2-[8-(methylsulfonyl)-8-azabicyclo[3.2.1]oct-2-en-3-yl]-1H-pyrrolo[2,3-b]pyridine;

2-{4-[4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide;

{4-[4-(5-fluoro-2-methoxyphenyl)-1H-pyrrolo[2,3-b]pyridin-2-yl]-3,6-dihydropyridin-1(2H)-yl}acetic acid;

2-{4-[4-(5-fluoro-2-methoxyphenyl)-1H-pyrrolo[2,3-b]pyridin-2-yl]-3,6-dihydropyridin-1(2H)-yl}acetamide;

ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[5-chloro-4-(5-fluoro-2-methoxyphenyl)-1H-pyrrolo[2,3-b]pyridin-2-yl]-N-methyl-3,6-dihydropyridine-1(2H)-carboxamide;

4-(5-fluoro-2-methoxyphenyl)-2-[1-(S-methylsulfonimidoyl)-1,2,3,6-tetrahydropyridin-4-yl]-1H-pyrrolo[2,3-b]pyridine;

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(4,5-difluoro-2-methoxyphenyl)-1H-pyrrolo[2,3-b]pyridin-2-yl]-N-methyl-3,6-dihydropyridine-1(2H)-carboxamide;

2-{3-[4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{4-[4-(2,3-difluorophenyl)-1H-pyrrolo[2,3-b]pyridin-2-yl]-3,6-dihydropyridin-1(2H)-yl}-N,N-dimethylacetamide;

2-{4-[4-(5-fluoro-2-methoxyphenyl)-1H-pyrrolo[2,3-b]pyridin-2-yl]piperidin-1-yl}-N,N-dimethylacetamide;

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide;

ethyl ({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{4-[4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone;
N-{4-[4-(5-fluoro-2-methoxyphenyl)-1H-pyrrolo[2,3-b]pyridin-2-yl]cyclohex-3-en-1-yl}-D-valine;
1-{4-[4-(5-fluoro-2-methoxyphenyl)-1H-pyrrolo[2,3-b]pyridin-2-yl]cyclohex-3-en-1-yl}-L-proline;
N-cyano-4-[4-(5-fluoro-2-methoxyphenyl)-1H-pyrrolo[2,3-b]pyridin-2-yl]-3,6-dihydropyridine-1(2H)-carboxamide;
1-({4-[4-(5-fluoro-2-methoxyphenyl)-1H-pyrrolo[2,3-b]pyridin-2-yl]-3,6-dihydropyridin-1(2H)-yl}acetyl)-L-prolinamide;
2-{4-[4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]piperidin-1-yl}-N-methylacetamide;
2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
ethyl ({4-[4-(5-fluoro-2-methoxyphenyl)-1H-pyrrolo[2,3-b]pyridin-2-yl]cyclohex-3-en-1-yl}sulfamoyl)carbamate;
2-{4-[4-(5-fluoro-2-methoxyphenyl)-1H-pyrrolo[2,3-b]pyridin-2-yl]piperidin-1-yl}-N-(2-hydroxyethyl)-N-methylacetamide;
2-{4-[4-(5-fluoro-2-methoxyphenyl)-1H-pyrrolo[2,3-b]pyridin-2-yl]piperidin-1-yl}-N-(3-hydroxycyclobutyl)acetamide;
2-{4-[4-(5-fluoro-2-methoxyphenyl)-1H-pyrrolo[2,3-b]pyridin-2-yl]piperidin-1-yl}-1-(3-hydroxyazetidin-1-yl)ethanone;
N-{4-[4-(5-fluoro-2-methoxyphenyl)-1H-pyrrolo[2,3-b]pyridin-2-yl]cyclohex-3-en-1-yl}-3-methyl-L-valine;
2-{4-[5-fluoro-4-(5-fluoro-2-methoxyphenyl)-1H-pyrrolo[2,3-b]pyridin-2-yl]piperidin-1-yl}-N,N-dimethylacetamide;
2-{4-[4-(2-methoxyphenyl)-1H-pyrrolo[2,3-b]pyridin-2-yl]piperidin-1-yl}-N,N-dimethylacetamide;
4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;
2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone;
2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
4-(5-fluoro-2-methoxyphenyl)-2-((3aS,6aR)-2-(methylsulfonyl)-1,2,3,3a,4,6a-hexahydrocyclopenta[c]pyrrol-5-yl)-1H-pyrrolo[2,3-b]pyridine;
4-(5-fluoro-2-methoxyphenyl)-2-((3aR,6aS)-2-(methylsulfonyl)-1,2,3,3a,4,6a-hexahydrocyclopenta[c]pyrrol-5-yl)-1H-pyrrolo[2,3-b]pyridine;
2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-{4-[4-(5-fluoro-2-methoxyphenyl)-1H-pyrrolo[2,3-b]pyridin-2-yl]-2,2-dimethyl-3,6-dihydropyridin-1(2H)-yl}-N,N-dimethylacetamide;
4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine;
2-{4-[5-cyano-4-(5-fluoro-2-methoxyphenyl)-1H-pyrrolo[2,3-b]pyridin-2-yl]piperidin-1-yl}-N,N-dimethylacetamide;
2-{4-[4-(5-fluoro-2-methoxyphenyl)-1H-pyrrolo[2,3-b]pyridin-2-yl]piperidin-1-yl}-N-(3-hydroxycyclobutyl)-N-methylacetamide;
4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
4-[5-fluoro-4-(5-fluoro-2-methoxyphenyl)-1H-pyrrolo[2,3-b]pyridin-2-yl]cyclohex-3-ene-1-carboxylic acid;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-hydroxyethanone;
3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-3-oxopropanenitrile;
5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile;
(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-methyl-2-oxoethanesulfonamide;
4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;
2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone;

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile;

2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide; and pharmaceutically acceptable salts thereof.

N-benzyl-4-fluoro-3-[2-(1-methylpiperidin-4-yl)-1H-pyrrolo[2,3-b]pyridin-4-yl]aniline;

4-[({4-fluoro-3-[2-(1-methylpiperidin-4-yl)-1H-pyrrolo[2,3-b]pyridin-4-yl]phenyl}amino)methyl]phenol;

4-fluoro-3-[2-(1-methylpiperidin-4-yl)-1H-pyrrolo[2,3-b]pyridin-4-yl]-N-(1H-1,2,4-triazol-5-ylmethyl)aniline;

4-fluoro-3-[2-(1-methylpiperidin-4-yl)-1H-pyrrolo[2,3-b]pyridin-4-yl]-N-(pyridin-2-ylmethyl)aniline;

N-[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;

N,N-bis[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;

N,N-bis(cyclopropylmethyl)-4-fluoro-3-[2-(1-methylpiperidin-4-yl)-1H-pyrrolo[2,3-b]pyridin-4-yl]aniline;

4-fluoro-3-[2-(1-methylpiperidin-4-yl)-1H-pyrrolo[2,3-b]pyridin-4-yl]-N-[3-(methylsulfonyl)benzyl]aniline;

2-[1-(cyclopropylsulfonyl)-1,2,3,6-tetrahydropyridin-4-yl]-4-(5-fluoro-2-methoxyphenyl)-1H-pyrrolo[2,3-b]pyridine;

4-[({4-fluoro-3-[2-(1-methylpiperidin-4-yl)-1H-pyrrolo[2,3-b]pyridin-4-yl]phenyl}amino)methyl]benzenesulfonamide;

3-[({4-fluoro-3-[2-(1-methylpiperidin-4-yl)-1H-pyrrolo[2,3-b]pyridin-4-yl]phenyl}amino)methyl]phenol;

N-(3-chlorobenzyl)-4-fluoro-3-[2-(1-methylpiperidin-4-yl)-1H-pyrrolo[2,3-b]pyridin-4-yl]aniline;

4-fluoro-N-(4-fluorobenzyl)-3-[2-(1-methylpiperidin-4-yl)-1H-pyrrolo[2,3-b]pyridin-4-yl]aniline;

4-fluoro-N-(2-fluorobenzyl)-3-[2-(1-methylpiperidin-4-yl)-1H-pyrrolo[2,3-b]pyridin-4-yl]aniline;

4-fluoro-N-(3-methoxybenzyl)-3-[2-(1-methylpiperidin-4-yl)-1H-pyrrolo[2,3-b]pyridin-4-yl]aniline;

{4-[({4-fluoro-3-[2-(1-methylpiperidin-4-yl)-1H-pyrrolo[2,3-b]pyridin-4-yl]phenyl}amino)methyl]phenoxy}acetic acid;

N-[(1,1-dioxidotetrahydro-2H-thiopyran-4-yl)methyl]-4-fluoro-3-[2-(1-methylpiperidin-4-yl)-1H-pyrrolo[2,3-b]pyridin-4-yl]aniline;

4-[4-(5-fluoro-2-methoxyphenyl)-1H-pyrrolo[2,3-b]pyridin-2-yl]tetrahydro-2H-thiopyran-4-ol 1,1-dioxide;

2-(1,1-dioxido-3,6-dihydro-2H-thiopyran-4-yl)-4-(5-fluoro-2-methoxyphenyl)-1H-pyrrolo[2,3-b]pyridine;

3-[4-(5-fluoro-2-methoxyphenyl)-1H-pyrrolo[2,3-b]pyridin-2-yl]pyrrolidin-3-ol;

2-(2,5-dihydro-1H-pyrrol-3-yl)-4-(5-fluoro-2-methoxyphenyl)-1H-pyrrolo[2,3-b]pyridine;

4-fluoro-N-(3-fluorobenzyl)-3-[2-(1-methylpiperidin-4-yl)-1H-pyrrolo[2,3-b]pyridin-4-yl]aniline;

N-(2,4-difluorobenzyl)-4-fluoro-3-[2-(1-methylpiperidin-4-yl)-1H-pyrrolo[2,3-b]pyridin-4-yl]aniline;

N-(2,6-difluorobenzyl)-4-fluoro-3-[2-(1-methylpiperidin-4-yl)-1H-pyrrolo[2,3-b]pyridin-4-yl]aniline;

2-{1-[(chloromethyl)sulfonyl]-1,2,3,6-tetrahydropyridin-4-yl}-4-(5-fluoro-2-methoxyphenyl)-1H-pyrrolo[2,3-b]pyridine;

4-(5-fluoro-2-methoxyphenyl)-2-[1-(propan-2-ylsulfonyl)-1,2,3,6-tetrahydropyridin-4-yl]-1H-pyrrolo[2,3-b]pyridine;

4-(5-fluoro-2-methoxyphenyl)-2-[1-(propylsulfonyl)-1,2,3,6-tetrahydropyridin-4-yl]-1H-pyrrolo[2,3-b]pyridine;

2-{1-[(1,1-dioxidotetrahydrothiophen-3-yl)sulfonyl]-1,2,3,6-tetrahydropyridin-4-yl}-4-(5-fluoro-2-methoxyphenyl)-1H-pyrrolo[2,3-b]pyridine;

N-(2,5-difluorobenzyl)-4-fluoro-3-[2-(1-methylpiperidin-4-yl)-1H-pyrrolo[2,3-b]pyridin-4-yl]aniline;

4-(5-fluoro-2-methoxyphenyl)-2-{1-[(2,2,2-trifluoroethyl)sulfonyl]-1,2,3,6-tetrahydropyridin-4-yl}-1H-pyrrolo[2,3-b]pyridine;

N-(2-chlorobenzyl)-4-fluoro-3-[2-(1-methylpiperidin-4-yl)-1H-pyrrolo[2,3-b]pyridin-4-yl]aniline;

3-[({4-fluoro-3-[2-(1-methylpiperidin-4-yl)-1H-pyrrolo[2,3-b]pyridin-4-yl]phenyl}amino)methyl]benzoic acid;

4-[({4-fluoro-3-[2-(1-methylpiperidin-4-yl)-1H-pyrrolo[2,3-b]pyridin-4-yl]phenyl}amino)methyl]benzonitrile;

2-[({4-fluoro-3-[2-(1-methylpiperidin-4-yl)-1H-pyrrolo[2,3-b]pyridin-4-yl]phenyl}amino)methyl]benzonitrile;

3-[({4-fluoro-3-[2-(1-methylpiperidin-4-yl)-1H-pyrrolo[2,3-b]pyridin-4-yl]phenyl}amino)methyl]benzonitrile;

trans-4-[4-(5-fluoro-2-methoxyphenyl)-1H-pyrrolo[2,3-b]pyridin-2-yl]-N-{[1-(methoxymethyl)-1H-1,2,3-triazol-4-yl]methyl}cyclohexanamine;

trans-4-[4-(5-fluoro-2-methoxyphenyl)-1H-pyrrolo[2,3-b]pyridin-2-yl]-N-{[1-(methoxymethyl)-1H-1,2,3-triazol-5-yl]methyl}cyclohexanamine;

2,4-difluoro-N-[(4-methyltetrahydro-2H-pyran-4-yl)methyl]-5-[2-(piperidin-4-yl)-1H-pyrrolo[2,3-b]pyridin-4-yl]aniline;

N-benzyl-2,4-difluoro-5-[2-(piperidin-4-yl)-1H-pyrrolo[2,3-b]pyridin-4-yl]aniline;

2,4-difluoro-5-[2-(piperidin-4-yl)-1H-pyrrolo[2,3-b]pyridin-4-yl]-N-(tetrahydro-2H-pyran-4-ylmethyl)aniline;

2,4-difluoro-N-(3-fluorobenzyl)-5-[2-(piperidin-4-yl)-1H-pyrrolo[2,3-b]pyridin-4-yl]aniline;

4-(5-fluoro-2-methoxyphenyl)-2-[1-(thiophen-2-ylsulfonyl)-1,2,3,6-tetrahydropyridin-4-yl]-1H-pyrrolo[2,3-b]pyridine;

N-[2-chloro-4-({4-[4-(5-fluoro-2-methoxyphenyl)-1H-pyrrolo[2,3-b]pyridin-2-yl]-3,6-dihydropyridin-1(2H)-yl}sulfonyl)phenyl]acetamide;

4-(5-fluoro-2-methoxyphenyl)-2-{1-[(2,4,5-trichlorophenyl)sulfonyl]-1,2,3,6-tetrahydropyridin-4-yl}-1H-pyrrolo[2,3-b]pyridine;

4-({4-[4-(5-fluoro-2-methoxyphenyl)-1H-pyrrolo[2,3-b]pyridin-2-yl]-3,6-dihydropyridin-1(2H)-yl}sulfonyl)-2,1,3-benzoxadiazole;

2-{1-[(3,5-dimethyl-1,2-oxazol-4-yl)sulfonyl]-1,2,3,6-tetrahydropyridin-4-yl}-4-(5-fluoro-2-methoxyphenyl)-1H-pyrrolo[2,3-b]pyridine;

N-(3-chlorobenzyl)-4-fluoro-3-[2-(piperidin-4-yl)-1H-pyrrolo[2,3-b]pyridin-4-yl]aniline;

4-fluoro-N-(3-fluorobenzyl)-3-[2-(piperidin-4-yl)-1H-pyrrolo[2,3-b]pyridin-4-yl]aniline;

4-[({4-fluoro-3-[2-(piperidin-4-yl)-1H-pyrrolo[2,3-b]pyridin-4-yl]phenyl}amino)methyl]benzonitrile;

4-fluoro-N-[4-(methylsulfonyl)benzyl]-3-[2-(piperidin-4-yl)-1H-pyrrolo[2,3-b]pyridin-4-yl]aniline;

4-fluoro-3-[2-(piperidin-4-yl)-1H-pyrrolo[2,3-b]pyridin-4-yl]-N-(pyridin-4-ylmethyl)aniline;

3-[4-(5-fluoro-2-methoxyphenyl)-1H-pyrrolo[2,3-b]pyridin-2-yl]azetidin-3-ol;

4-[4-(5-fluoro-2-methoxyphenyl)-1H-pyrrolo[2,3-b]pyridin-2-yl]-1-(methylsulfonyl)piperidin-4-ol;

2-(1-benzylpiperidin-4-yl)-4-(5-fluoro-2-methoxyphenyl)-1H-pyrrolo[2,3-b]pyridine;

4-(5-fluoro-2-methoxyphenyl)-2-(1-methyl-1,2,3,6-tetrahydropyridin-4-yl)-1H-pyrrolo[2,3-b]pyridine;

4-fluoro-3-{2-[1-(methylsulfonyl)-1,2,3,6-tetrahydropyridin-4-yl]-1H-pyrrolo[2,3-b]pyridin-4-yl}aniline;

4-fluoro-3-[2-(1-methylpiperidin-4-yl)-1H-pyrrolo[2,3-b]pyridin-4-yl]-N-(pyridin-3-ylmethyl)aniline;

4-fluoro-3-[2-(piperidin-4-yl)-1H-pyrrolo[2,3-b]pyridin-4-yl]-N-(pyridin-3-ylmethyl)aniline;

N-(3,5-difluorobenzyl)-4-fluoro-3-[2-(piperidin-4-yl)-1H-pyrrolo[2,3-b]pyridin-4-yl]aniline;

N-(2,4-difluorobenzyl)-4-fluoro-3-[2-(piperidin-4-yl)-1H-pyrrolo[2,3-b]pyridin-4-yl]aniline;

N-(2,5-difluorobenzyl)-4-fluoro-3-[2-(piperidin-4-yl)-1H-pyrrolo[2,3-b]pyridin-4-yl]aniline;

N-(2,6-difluorobenzyl)-4-fluoro-3-[2-(piperidin-4-yl)-1H-pyrrolo[2,3-b]pyridin-4-yl]aniline;

N-(3,5-difluorobenzyl)-4-fluoro-3-[2-(1-methylpiperidin-4-yl)-1H-pyrrolo[2,3-b]pyridin-4-yl]aniline;

4-fluoro-N-(4-fluorobenzyl)-3-[2-(piperidin-4-yl)-1H-pyrrolo[2,3-b]pyridin-4-yl]aniline;

4-[({4-fluoro-3-[2-(piperidin-4-yl)-1H-pyrrolo[2,3-b]pyridin-4-yl]phenyl}amino)methyl]benzenesulfonamide;

3-[({4-fluoro-3-[2-(piperidin-4-yl)-1H-pyrrolo[2,3-b]pyridin-4-yl]phenyl}amino)methyl]phenol;

4-fluoro-3-[2-(piperidin-4-yl)-1H-pyrrolo[2,3-b]pyridin-4-yl]-N-(pyridin-2-ylmethyl)aniline;

4-fluoro-N-[3-(methylsulfonyl)benzyl]-3-[2-(piperidin-4-yl)-1H-pyrrolo[2,3-b]pyridin-4-yl]aniline;

N-(4-fluoro-3-{2-[1-(methylsulfonyl)piperidin-4-yl]-1H-pyrrolo[2,3-b]pyridin-4-yl}phenyl)methanesulfonamide;

N-benzyl-4-fluoro-3-{2-[1-(methylsulfonyl)piperidin-4-yl]-1H-pyrrolo[2,3-b]pyridin-4-yl}aniline;

N-(3-chlorobenzyl)-4-fluoro-3-{2-[1-(methylsulfonyl)piperidin-4-yl]-1H-pyrrolo[2,3-b]pyridin-4-yl}aniline;

4-fluoro-N-(3-fluorobenzyl)-3-{2-[1-(methylsulfonyl)piperidin-4-yl]-1H-pyrrolo[2,3-b]pyridin-4-yl}aniline;

4-(5-fluoro-2-methoxyphenyl)-2-(2,2,6,6-tetramethyl-1,2,3,6-tetrahydropyridin-4-yl)-1H-pyrrolo[2,3-b]pyridine;

4-fluoro-3-{2-[1-(methylsulfonyl)piperidin-4-yl]-1H-pyrrolo[2,3-b]pyridin-4-yl}-N-(pyridin-4-ylmethyl)aniline;

4-{[(4-fluoro-3-{2-[1-(methylsulfonyl)piperidin-4-yl]-1H-pyrrolo[2,3-b]pyridin-4-yl}phenyl)amino]methyl}benzonitrile;

4-{2-fluoro-5-[(3-fluorobenzyl)oxy]phenyl}-2-(1,2,3,6-tetrahydropyridin-4-yl)-1H-pyrrolo[2,3-b]pyridine;

2-({4-[4-(5-fluoro-2-methoxyphenyl)-1H-pyrrolo[2,3-b]pyridin-2-yl]piperidin-1-yl}methyl)-1H-benzimidazole;

4-(5-fluoro-2-methoxyphenyl)-2-[1-(tetrahydrofuran-2-ylmethyl)piperidin-4-yl]-1H-pyrrolo[2,3-b]pyridine;

2-[1-(5,6-dihydro-2H-pyran-3-ylmethyl)piperidin-4-yl]-4-(5-fluoro-2-methoxyphenyl)-1H-pyrrolo[2,3-b]pyridine;

4-(5-fluoro-2-methoxyphenyl)-2-[1-(4-methoxybenzyl)piperidin-4-yl]-1H-pyrrolo[2,3-b]pyridine;

4-(5-fluoro-2-methoxyphenyl)-2-{1-[2-(morpholin-4-yl)ethyl]piperidin-4-yl}-1H-pyrrolo[2,3-b]pyridine;

4-({4-[4-(5-fluoro-2-methoxyphenyl)-1H-pyrrolo[2,3-b]pyridin-2-yl]piperidin-1-yl}methyl)benzonitrile;

1-(2-{4-[4-(5-fluoro-2-methoxyphenyl)-1H-pyrrolo[2,3-b]pyridin-2-yl]-3,6-dihydropyridin-1(2H)-yl}ethyl)-3-methylurea;

4-(5-fluoro-2-methoxyphenyl)-2-[1-(2-methylpropyl)piperidin-4-yl]-1H-pyrrolo[2,3-b]pyridine;

N-[4-({4-[4-(5-fluoro-2-methoxyphenyl)-1H-pyrrolo[2,3-b]pyridin-2-yl]piperidin-1-yl}methyl)phenyl]acetamide;

4-(5-fluoro-2-methoxyphenyl)-2-[1-(pyridin-2-ylmethyl)piperidin-4-yl]-1H-pyrrolo[2,3-b]pyridine;

4-({4-[4-(5-fluoro-2-methoxyphenyl)-1H-pyrrolo[2,3-b]pyridin-2-yl]piperidin-1-yl}methyl)-N,N-dimethylaniline;

2-{1-[(1-tert-butyl-1H-pyrazol-4-yl)methyl]piperidin-4-yl}-4-(5-fluoro-2-methoxyphenyl)-1H-pyrrolo[2,3-b]pyridine;

4-(5-fluoro-2-methoxyphenyl)-2-[1-(2-methoxyethyl)piperidin-4-yl]-1H-pyrrolo[2,3-b]pyridine;

4-(5-fluoro-2-methoxyphenyl)-2-[1-(pyridin-4-ylmethyl)piperidin-4-yl]-1H-pyrrolo[2,3-b]pyridine;

N,N-diethyl-2-[4-({4-[4-(5-fluoro-2-methoxyphenyl)-1H-pyrrolo[2,3-b]pyridin-2-yl]piperidin-1-yl}methyl)phenoxy]ethanamine;

4-chloro-5-({4-[4-(5-fluoro-2-methoxyphenyl)-1H-pyrrolo[2,3-b]pyridin-2-yl]piperidin-1-yl}methyl)-1,3-thiazol-2-amine;

2-[1-(1,3-benzodioxol-5-ylmethyl)piperidin-4-yl]-4-(5-fluoro-2-methoxyphenyl)-1H-pyrrolo[2,3-b]pyridine;

3-{[(4-fluoro-3-{2-[1-(methylsulfonyl)piperidin-4-yl]-1H-pyrrolo[2,3-b]pyridin-4-yl}phenyl)amino]methyl}phenol;

4-fluoro-N-[3-(methylsulfonyl)benzyl]-3-{2-[1-(methylsulfonyl)piperidin-4-yl]-1H-pyrrolo[2,3-b]pyridin-4-yl}aniline;

4-{[(4-fluoro-3-{2-[1-(methylsulfonyl)piperidin-4-yl]-1H-pyrrolo[2,3-b]pyridin-4-yl}phenyl)amino]methyl}benzamide;

4-{[(4-fluoro-3-{2-[1-(methylsulfonyl)piperidin-4-yl]-1H-pyrrolo[2,3-b]pyridin-4-yl}phenyl)amino]methyl}phenol;

4-(5-fluoro-2-methoxyphenyl)-2-{1-[2-(morpholin-4-yl)ethyl]-1,2,3,6-tetrahydropyridin-4-yl}-1H-pyrrolo[2,3-b]pyridine;

2-{1-[(3-chlorobenzyl)sulfonyl]-1,2,3,6-tetrahydropyridin-4-yl}-4-(5-fluoro-2-methoxyphenyl)-1H-pyrrolo[2,3-b]pyridine;

2,4-difluoro-5-{2-[1-(methylsulfonyl)-1,2,3,6-tetrahydropyridin-4-yl]-1H-pyrrolo[2,3-b]pyridin-4-yl}-N-(tetrahydro-2H-pyran-4-ylmethyl)aniline;
2,4-difluoro-N-(tetrahydro-2H-pyran-4-ylmethyl)-5-[2-(1,2,3,6-tetrahydropyridin-4-yl)-1H-pyrrolo[2,3-b]pyridin-4-yl]aniline;
2,4-difluoro-N-(3-fluorobenzyl)-5-[2-(1,2,3,6-tetrahydropyridin-4-yl)-1H-pyrrolo[2,3-b]pyridin-4-yl]aniline;
N-(3,5-difluorobenzyl)-4-fluoro-3-{2-[1-(methylsulfonyl)-1,2,3,6-tetrahydropyridin-4-yl]-1H-pyrrolo[2,3-b]pyridin-4-yl}aniline;
4-[4-(5-fluoro-2-methoxyphenyl)-1H-pyrrolo[2,3-b]pyridin-2-yl]-N-(propan-2-yl)-3,6-dihydropyridine-1(2H)-carboxamide;
2-(1-ethyl-1,2,3,6-tetrahydropyridin-4-yl)-4-(5-fluoro-2-methoxyphenyl)-1H-pyrrolo[2,3-b]pyridine;
2-(1-benzyl-1,2,3,6-tetrahydropyridin-4-yl)-4-(5-fluoro-2-methoxyphenyl)-1H-pyrrolo[2,3-b]pyridine;
4-fluoro-3-{2-[1-(methylsulfonyl)piperidin-4-yl]-1H-pyrrolo[2,3-b]pyridin-4-yl}-N-(pyridin-3-ylmethyl)aniline;
N-(3,5-difluorobenzyl)-4-fluoro-3-{2-[1-(methylsulfonyl)piperidin-4-yl]-1H-pyrrolo[2,3-b]pyridin-4-yl}aniline;
N-(3,4-difluorobenzyl)-4-fluoro-3-{2-[1-(methylsulfonyl)piperidin-4-yl]-1H-pyrrolo[2,3-b]pyridin-4-yl}aniline;
N-(3,4-difluorobenzyl)-4-fluoro-3-[2-(1-methylpiperidin-4-yl)-1H-pyrrolo[2,3-b]pyridin-4-yl]aniline;
1-[4-(4-{5-[(3,5-difluorobenzyl)amino]-2-fluorophenyl}-1H-pyrrolo[2,3-b]pyridin-2-yl)piperidin-1-yl]-2-hydroxyethanone;
3-[4-(4-{2-fluoro-5-[(pyridin-3-ylmethyl)amino]phenyl}-1H-pyrrolo[2,3-b]pyridin-2-yl)piperidin-1-yl]propane-1,2-diol;
3-[4-(4-{2-fluoro-5-[(pyridin-4-ylmethyl)amino]phenyl}-1H-pyrrolo[2,3-b]pyridin-2-yl)piperidin-1-yl]propane-1,2-diol;
4-{[(3-{2-[1-(2,3-dihydroxypropyl)piperidin-4-yl]-1H-pyrrolo[2,3-b]pyridin-4-yl}-4-fluorophenyl)amino]methyl}benzonitrile;
3-{[(3-{2-[1-(2,3-dihydroxypropyl)piperidin-4-yl]-1H-pyrrolo[2,3-b]pyridin-4-yl}-4-fluorophenyl)amino]methyl}benzonitrile;
3-{2-[1-(cyclopropylsulfonyl)piperidin-4-yl]-1H-pyrrolo[2,3-b]pyridin-4-yl}-4-fluoro-N-(pyridin-4-ylmethyl)aniline;
4-{[(3-{2-[1-(cyclopropylsulfonyl)piperidin-4-yl]-1H-pyrrolo[2,3-b]pyridin-4-yl}-4-fluorophenyl)amino]methyl}benzonitrile;
3-{2-[1-(cyclopropylsulfonyl)piperidin-4-yl]-1H-pyrrolo[2,3-b]pyridin-4-yl}-N-(3,5-difluorobenzyl)-4-fluoroaniline;
3-{2-[1-(cyclopropylsulfonyl)piperidin-4-yl]-1H-pyrrolo[2,3-b]pyridin-4-yl}-4-fluoro-N-[3-(methylsulfonyl)benzyl]aniline;
4-(4-{2-fluoro-5-[(3-fluorobenzyl)amino]phenyl}-1H-pyrrolo[2,3-b]pyridin-2-yl)piperidine-1-sulfonamide;
3-[4-(4-{2-fluoro-5-[(3-fluorobenzyl)amino]phenyl}-1H-pyrrolo[2,3-b]pyridin-2-yl)piperidin-1-yl]propane-1,2-diol;
4-(5-fluoro-2-methoxyphenyl)-2-[4-(pyrrolidin-1-yl)cyclohex-1-en-1-yl]-1H-pyrrolo[2,3-b]pyridine;
4-(5-fluoro-2-methoxyphenyl)-2-[1-(methylsulfonyl)-2,5-dihydro-1H-pyrrol-3-yl]-1H-pyrrolo[2,3-b]pyridine;
3-[4-(4-{2-fluoro-5-[(3-fluorobenzyl)oxy]phenyl}-1H-pyrrolo[2,3-b]pyridin-2-yl)-3,6-dihydropyridin-1(2H)-yl]propane-1,2-diol;
3-[4-(4-{2,4-difluoro-5-[(3-fluorobenzyl)amino]phenyl}-1H-pyrrolo[2,3-b]pyridin-2-yl)-3,6-dihydropyridin-1(2H)-yl]propane-1,2-diol;

2-({4-[4-(5-fluoro-2-methoxyphenyl)-1H-pyrrolo[2,3-b]pyridin-2-yl]-3,6-dihydropyridin-1(2H)-yl}methyl)-1H-benzimidazole;
2-[1-(5,6-dihydro-2H-pyran-3-ylmethyl)-1,2,3,6-tetrahydropyridin-4-yl]-4-(5-fluoro-2-methoxyphenyl)-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)-N,N-dimethylaniline;
N,N-diethyl-2-[4-({4-[4-(5-fluoro-2-methoxyphenyl)-1H-pyrrolo[2,3-b]pyridin-2-yl]-3,6-dihydropyridin-1(2H)-yl}methyl)phenoxy]ethanamine;
4-(5-fluoro-2-methoxyphenyl)-2-[1-(pyridin-4-ylmethyl)-1,2,3,6-tetrahydropyridin-4-yl]-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)benzonitrile;
4-chloro-5-({4-[4-(5-fluoro-2-methoxyphenyl)-1H-pyrrolo[2,3-b]pyridin-2-yl]-3,6-dihydropyridin-1(2H)-yl}methyl)-1,3-thiazol-2-amine;
4-(5-fluoro-2-methoxyphenyl)-2-[1-(tetrahydrofuran-2-ylmethyl)-1,2,3,6-tetrahydropyridin-4-yl]-1H-pyrrolo[2,3-b]pyridine;
4-chloro-3-[2-(2,5-dihydro-1H-pyrrol-3-yl)-1H-pyrrolo[2,3-b]pyridin-4-yl]-N-(pyridin-3-ylmethyl)aniline;
4-chloro-3-[2-(2,5-dihydro-1H-pyrrol-3-yl)-1H-pyrrolo[2,3-b]pyridin-4-yl]-N-(3-fluorobenzyl)aniline;
4-chloro-3-[2-(2,5-dihydro-1H-pyrrol-3-yl)-1H-pyrrolo[2,3-b]pyridin-4-yl]-N-(tetrahydro-2H-pyran-3-ylmethyl)aniline;
4-chloro-3-[2-(2,5-dihydro-1H-pyrrol-3-yl)-1H-pyrrolo[2,3-b]pyridin-4-yl]-N-(piperidin-4-ylmethyl)aniline;
5-fluoro-4-(5-fluoro-2-methoxyphenyl)-2-(piperidin-4-yl)-1H-pyrrolo[2,3-b]pyridine;
N-cyclohexyl-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-(4-methoxybenzyl)-3,6-dihydropyridine-1(2H)-carboxamide;
4-[4-(5-fluoro-2-methoxyphenyl)-1H-pyrrolo[2,3-b]pyridin-2-yl]-N-phenyl-3,6-dihydropyridine-1(2H)-carboxamide;
4-(4-{2-fluoro-5-[(pyridin-4-ylmethyl)amino]phenyl}-1H-pyrrolo[2,3-b]pyridin-2-yl)piperidine-1-sulfonamide;
5-fluoro-4-(5-fluoro-2-methoxyphenyl)-2-[1-(methylsulfonyl)piperidin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]piperidin-1-yl}propane-1,2-diol;
1-{4-[5-fluoro-4-(5-fluoro-2-methoxyphenyl)-1H-pyrrolo[2,3-b]pyridin-2-yl]piperidin-1-yl}ethanone;
3-[4-(4-{5-[(3,5-difluorobenzyl)amino]-2-fluorophenyl}-1H-pyrrolo[2,3-b]pyridin-2-yl)piperidin-1-yl]propane-1,2-diol;
4-[4-(5-fluoro-2-methoxyphenyl)-1H-pyrrolo[2,3-b]pyridin-2-yl]-N-[2-(morpholin-4-yl)ethyl]-3,6-dihydropyridine-1(2H)-carboxamide;
4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine;
{4-[4-(5-fluoro-2-methoxyphenyl)-1H-pyrrolo[2,3-b]pyridin-2-yl]-3,6-dihydropyridin-1(2H)-yl}(pyridin-2-yl)methanone;
{4-[4-(5-fluoro-2-methoxyphenyl)-1H-pyrrolo[2,3-b]pyridin-2-yl]-3,6-dihydropyridin-1(2H)-yl}(pyridin-3-yl)methanone;

{4-[4-(5-fluoro-2-methoxyphenyl)-1H-pyrrolo[2,3-b]pyridin-2-yl]-3,6-dihydropyridin-1(2H)-yl}(pyridin-4-yl)methanone;

{4-[4-(5-fluoro-2-methoxyphenyl)-1H-pyrrolo[2,3-b]pyridin-2-yl]-3,6-dihydropyridin-1(2H)-yl}(pyrazin-2-yl)methanone;

4-(5-fluoro-2-methoxyphenyl)-2-[1-(pyrimidin-4-yl)-1,2,3,6-tetrahydropyridin-4-yl]-1H-pyrrolo[2,3-b]pyridine;

4-(5-fluoro-2-methoxyphenyl)-2-[1-(2-methylpyrimidin-4-yl)-1,2,3,6-tetrahydropyridin-4-yl]-1H-pyrrolo[2,3-b]pyridine;

4-(5-fluoro-2-methoxyphenyl)-2-{1-[6-(trifluoromethyl)pyrimidin-4-yl]-1,2,3,6-tetrahydropyridin-4-yl}-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-3-(piperidin-1-yl)propan-1-one;

{4-[4-(5-fluoro-2-methoxyphenyl)-1H-pyrrolo[2,3-b]pyridin-2-yl]-3,6-dihydropyridin-1(2H)-yl}(1H-pyrazol-4-yl)methanone;

{4-[4-(5-fluoro-2-methoxyphenyl)-1H-pyrrolo[2,3-b]pyridin-2-yl]-3,6-dihydropyridin-1(2H)-yl}(1,3-thiazol-4-yl)methanone;

(3,5-dimethyl-1,2-oxazol-4-yl) {4-[4-(5-fluoro-2-methoxyphenyl)-1H-pyrrolo[2,3-b]pyridin-2-yl]-3,6-dihydropyridin-1(2H)-yl}methanone;

4-(2-chloro-5-methoxyphenyl)-2-[1-(methylsulfonyl)-1,2,3,6-tetrahydropyridin-4-yl]-1H-pyrrolo[2,3-b]pyridine;

2-[1-(methylsulfonyl)-1,2,3,6-tetrahydropyridin-4-yl]-4-(2,3,4-trifluorophenyl)-1H-pyrrolo[2,3-b]pyridine;

2-[1-(methylsulfonyl)-1,2,3,6-tetrahydropyridin-4-yl]-4-[3-(trifluoromethoxy)phenyl]-1H-pyrrolo[2,3-b]pyridine;

N-(2-{4-[4-(5-fluoro-2-methoxyphenyl)-1H-pyrrolo[2,3-b]pyridin-2-yl]-3,6-dihydropyridin-1(2H)-yl}ethyl)-N$^2$,N$^2$-dimethylglycinamide;

4-(4-methoxyphenyl)-2-[1-(methylsulfonyl)-1,2,3,6-tetrahydropyridin-4-yl]-1H-pyrrolo[2,3-b]pyridine;

4-(3,4-difluorophenyl)-2-[1-(methylsulfonyl)-1,2,3,6-tetrahydropyridin-4-yl]-1H-pyrrolo[2,3-b]pyridine;

2-[1-(methylsulfonyl)-1,2,3,6-tetrahydropyridin-4-yl]-4-[2-(trifluoromethoxy)phenyl]-1H-pyrrolo[2,3-b]pyridine;

4-[5-fluoro-2-(propan-2-yloxy)phenyl]-2-[1-(methylsulfonyl)-1,2,3,6-tetrahydropyridin-4-yl]-1H-pyrrolo[2,3-b]pyridine;

4-[2-(cyclopropyloxy)-5-fluorophenyl]-2-[1-(methylsulfonyl)-1,2,3,6-tetrahydropyridin-4-yl]-1H-pyrrolo[2,3-b]pyridine;

4-(4-ethoxy-3-fluorophenyl)-2-[1-(methylsulfonyl)-1,2,3,6-tetrahydropyridin-4-yl]-1H-pyrrolo[2,3-b]pyridine;

4-(4-{5-[(3,5-difluorobenzyl)amino]-2-fluorophenyl}-1H-pyrrolo[2,3-b]pyridin-2-yl)piperidine-1-sulfonamide;

4-(4-chloro-3-methylphenyl)-2-[1-(methylsulfonyl)-1,2,3,6-tetrahydropyridin-4-yl]-1H-pyrrolo[2,3-b]pyridine;

4-(3-chloro-4-fluorophenyl)-2-[1-(methylsulfonyl)-1,2,3,6-tetrahydropyridin-4-yl]-1H-pyrrolo[2,3-b]pyridine;

N,N-dimethyl-3-{2-[1-(methylsulfonyl)-1,2,3,6-tetrahydropyridin-4-yl]-1H-pyrrolo[2,3-b]pyridin-4-yl}benzamide;

4-(4-fluoro-3-methylphenyl)-2-[1-(methylsulfonyl)-1,2,3,6-tetrahydropyridin-4-yl]-1H-pyrrolo[2,3-b]pyridine;

4-[3-fluoro-4-(propan-2-yloxy)phenyl]-2-[1-(methylsulfonyl)-1,2,3,6-tetrahydropyridin-4-yl]-1H-pyrrolo[2,3-b]pyridine;

4-(4-butoxy-3-fluorophenyl)-2-[1-(methylsulfonyl)-1,2,3,6-tetrahydropyridin-4-yl]-1H-pyrrolo[2,3-b]pyridine;

(3-{2-[1-(methylsulfonyl)-1,2,3,6-tetrahydropyridin-4-yl]-1H-pyrrolo[2,3-b]pyridin-4-yl}phenyl)(morpholin-4-yl)methanone;

N-(3,5-difluorobenzyl)-4-fluoro-3-[2-(1,2,3,6-tetrahydropyridin-4-yl)-1H-pyrrolo[2,3-b]pyridin-4-yl]aniline;

4-(5-fluoro-2-methoxyphenyl)-2-(1,2,5,6-tetrahydropyridin-3-yl)-1H-pyrrolo[2,3-b]pyridine;

4-(3,5-difluorophenyl)-2-[1-(methylsulfonyl)-1,2,3,6-tetrahydropyridin-4-yl]-1H-pyrrolo[2,3-b]pyridine;

4-(2,4-dichlorophenyl)-2-[1-(methylsulfonyl)-1,2,3,6-tetrahydropyridin-4-yl]-1H-pyrrolo[2,3-b]pyridine;

4-(2-ethylphenyl)-2-[1-(methylsulfonyl)-1,2,3,6-tetrahydropyridin-4-yl]-1H-pyrrolo[2,3-b]pyridine;

4-(2,4-dimethylphenyl)-2-[1-(methylsulfonyl)-1,2,3,6-tetrahydropyridin-4-yl]-1H-pyrrolo[2,3-b]pyridine;

4-(2,5-dichlorophenyl)-2-[1-(methylsulfonyl)-1,2,3,6-tetrahydropyridin-4-yl]-1H-pyrrolo[2,3-b]pyridine;

4-(3,4-dichlorophenyl)-2-[1-(methylsulfonyl)-1,2,3,6-tetrahydropyridin-4-yl]-1H-pyrrolo[2,3-b]pyridine;

N-(4-{2-[1-(methylsulfonyl)-1,2,3,6-tetrahydropyridin-4-yl]-1H-pyrrolo[2,3-b]pyridin-4-yl}phenyl)methanesulfonamide;

4-(5-chloro-2-methoxyphenyl)-2-[1-(methylsulfonyl)-1,2,3,6-tetrahydropyridin-4-yl]-1H-pyrrolo[2,3-b]pyridine;

4-[2-methoxy-5-(propan-2-yl)phenyl]-2-[1-(methylsulfonyl)-1,2,3,6-tetrahydropyridin-4-yl]-1H-pyrrolo[2,3-b]pyridine;

4-(2-methoxy-5-methylphenyl)-2-[1-(methylsulfonyl)-1,2,3,6-tetrahydropyridin-4-yl]-1H-pyrrolo[2,3-b]pyridine;

4-(4-methoxy-3-methylphenyl)-2-[1-(methylsulfonyl)-1,2,3,6-tetrahydropyridin-4-yl]-1H-pyrrolo[2,3-b]pyridine;

2-{2-[1-(methylsulfonyl)-1,2,3,6-tetrahydropyridin-4-yl]-1H-pyrrolo[2,3-b]pyridin-4-yl}benzonitrile;

4-(2-methoxyphenyl)-2-[1-(methylsulfonyl)-1,2,3,6-tetrahydropyridin-4-yl]-1H-pyrrolo[2,3-b]pyridine;

3-{2-[1-(methylsulfonyl)-1,2,3,6-tetrahydropyridin-4-yl]-1H-pyrrolo[2,3-b]pyridin-4-yl}benzonitrile;

2-[1-(methylsulfonyl)-1,2,3,6-tetrahydropyridin-4-yl]-4-[2-(trifluoromethyl)phenyl]-1H-pyrrolo[2,3-b]pyridine;

4-(3-chlorophenyl)-2-[1-(methylsulfonyl)-1,2,3,6-tetrahydropyridin-4-yl]-1H-pyrrolo[2,3-b]pyridine;

4-(2-chlorophenyl)-2-[1-(methylsulfonyl)-1,2,3,6-tetrahydropyridin-4-yl]-1H-pyrrolo[2,3-b]pyridine;

4-[2-fluoro-5-(trifluoromethyl)phenyl]-2-[1-(methylsulfonyl)-1,2,3,6-tetrahydropyridin-4-yl]-1H-pyrrolo[2,3-b]pyridine;

4-(3-chloro-4-methoxyphenyl)-2-[1-(methylsulfonyl)-1,2,3,6-tetrahydropyridin-4-yl]-1H-pyrrolo[2,3-b]pyridine;

4-(2-fluoro-5-methylphenyl)-2-[1-(methylsulfonyl)-1,2,3,6-tetrahydropyridin-4-yl]-1H-pyrrolo[2,3-b]pyridine;

4-(5-chloro-2-fluoro-3-methylphenyl)-2-[1-(methylsulfonyl)-1,2,3,6-tetrahydropyridin-4-yl]-1H-pyrrolo[2,3-b]pyridine;

4-(5-chloro-2-propoxyphenyl)-2-[1-(methylsulfonyl)-1,2,3,6-tetrahydropyridin-4-yl]-1H-pyrrolo[2,3-b]pyridine;

4-(4-{5-[(3,5-difluorobenzyl)amino]-2-fluorophenyl}-1H-pyrrolo[2,3-b]pyridin-2-yl)-N-methyl-3,6-dihydropyridine-1(2H)-carboxamide;

3-[4-(4-{5-[(3,5-difluorobenzyl)amino]-2-fluorophenyl}-1H-pyrrolo[2,3-b]pyridin-2-yl)-3,6-dihydropyridin-1(2H)-yl]propane-1,2-diol;

ethyl 4-[4-(5-fluoro-2-methoxyphenyl)-1H-pyrrolo[2,3-b]pyridin-2-yl]cyclohex-3-ene-1-carboxylate;

4-(2-ethoxy-5-fluorophenyl)-2-[1-(methylsulfonyl)-1,2,3,6-tetrahydropyridin-4-yl]-1H-pyrrolo[2,3-b]pyridine;

4-(2,3-dichlorophenyl)-2-[1-(methylsulfonyl)-1,2,3,6-tetrahydropyridin-4-yl]-1H-pyrrolo[2,3-b]pyridine;

4-(3-chloro-4-methylphenyl)-2-[1-(methylsulfonyl)-1,2,3,6-tetrahydropyridin-4-yl]-1H-pyrrolo[2,3-b]pyridine;

2-methyl-5-{2-[1-(methylsulfonyl)-1,2,3,6-tetrahydropyridin-4-yl]-1H-pyrrolo[2,3-b]pyridin-4-yl}aniline;
4-(2-fluorobiphenyl-4-yl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[3-(propan-2-yloxy)phenyl]-1H-pyrrolo[2,3-b]pyridine;
4-(3-fluoro-4-propoxyphenyl)-2-[1-(methylsulfonyl)-1,2,3,6-tetrahydropyridin-4-yl]-1H-pyrrolo[2,3-b]pyridine;
4-[2-fluoro-5-(propan-2-yloxy)phenyl]-2-[1-(methylsulfonyl)-1,2,3,6-tetrahydropyridin-4-yl]-1H-pyrrolo[2,3-b]pyridine;
4-(4-butoxy-3-chlorophenyl)-2-[1-(methylsulfonyl)-1,2,3,6-tetrahydropyridin-4-yl]-1H-pyrrolo[2,3-b]pyridine;
4-[2-(2-methylpropoxy)phenyl]-2-[1-(methylsulfonyl)-1,2,3,6-tetrahydropyridin-4-yl]-1H-pyrrolo[2,3-b]pyridine;
4-{2-[1-(methylsulfonyl)-1,2,3,6-tetrahydropyridin-4-yl]-1H-pyrrolo[2,3-b]pyridin-4-yl}benzonitrile;
2-[1-(methylsulfonyl)-1,2,3,6-tetrahydropyridin-4-yl]-4-phenyl-1H-pyrrolo[2,3-b]pyridine;
(4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid;
4-(3-fluoro-4-methoxyphenyl)-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}aniline;
N-(2-{2-[1-(methylsulfonyl)-1,2,3,6-tetrahydropyridin-4-yl]-1H-pyrrolo[2,3-b]pyridin-4-yl}phenyl)methanesulfonamide;
3-{2-[1-(methylsulfonyl)-1,2,3,6-tetrahydropyridin-4-yl]-1H-pyrrolo[2,3-b]pyridin-4-yl}-N-(propan-2-yl)benzamide;
(4-{2-[1-(methylsulfonyl)-1,2,3,6-tetrahydropyridin-4-yl]-1H-pyrrolo[2,3-b]pyridin-4-yl}phenyl)acetonitrile;
N-methyl-4-{2-[1-(methylsulfonyl)-1,2,3,6-tetrahydropyridin-4-yl]-1H-pyrrolo[2,3-b]pyridin-4-yl}benzamide;
N-(3-{2-[1-(methylsulfonyl)-1,2,3,6-tetrahydropyridin-4-yl]-1H-pyrrolo[2,3-b]pyridin-4-yl}phenyl)acetamide;
N-(4-{2-[1-(methylsulfonyl)-1,2,3,6-tetrahydropyridin-4-yl]-1H-pyrrolo[2,3-b]pyridin-4-yl}phenyl)acetamide;
4-[4-(5-fluoro-2-methoxyphenyl)-1H-pyrrolo[2,3-b]pyridin-2-yl]-N-methyl-3,6-dihydropyridine-1(2H)-sulfonamide;
4-(5-fluoro-2-methoxyphenyl)-2-[1-(pyridin-2-ylmethyl)-1,2,3,6-tetrahydropyridin-4-yl]-1H-pyrrolo[2,3-b]pyridine;
3-{5-[4-(5-fluoro-2-methoxyphenyl)-1H-pyrrolo[2,3-b]pyridin-2-yl]-3,6-dihydropyridin-1(2H)-yl}propane-1,2-diol;
5-[4-(5-fluoro-2-methoxyphenyl)-1H-pyrrolo[2,3-b]pyridin-2-yl]-N-methyl-3,6-dihydropyridine-1(2H)-carboxamide;
4-(5-fluoro-2-methoxyphenyl)-2-[1-(methylsulfonyl)-1,2,5,6-tetrahydropyridin-3-yl]-1H-pyrrolo[2,3-b]pyridine;
4-(5-fluoro-2-methylphenyl)-2-[1-(methylsulfonyl)-1,2,3,6-tetrahydropyridin-4-yl]-1H-pyrrolo[2,3-b]pyridine;
4-{5-[(3,5-difluorobenzyl)oxy]-2-fluorophenyl}-2-(1,2,3,6-tetrahydropyridin-4-yl)-1H-pyrrolo[2,3-b]pyridine;
4-{5-[(3,5-difluorobenzyl)oxy]-2-fluorophenyl}-2-(1-methyl-1,2,3,6-tetrahydropyridin-4-yl)-1H-pyrrolo[2,3-b]pyridine;
3-[4-(4-{5-[(3,5-difluorobenzyl)oxy]-2-fluorophenyl}-1H-pyrrolo[2,3-b]pyridin-2-yl)-3,6-dihydropyridin-1(2H)-yl]propane-1,2-diol;
4-{5-[(3,5-difluorobenzyl)oxy]-2-fluorophenyl}-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}benzamide;
4-(4-ethoxy-2-methylphenyl)-2-[1-(methylsulfonyl)-1,2,3,6-tetrahydropyridin-4-yl]-1H-pyrrolo[2,3-b]pyridine;
4-[4-chloro-3-(trifluoromethyl)phenyl]-2-[1-(methylsulfonyl)-1,2,3,6-tetrahydropyridin-4-yl]-1H-pyrrolo[2,3-b]pyridine;
N-butyl-3-{2-[1-(methylsulfonyl)-1,2,3,6-tetrahydropyridin-4-yl]-1H-pyrrolo[2,3-b]pyridin-4-yl}benzamide;
4-(3-fluorophenyl)-2-[1-(methylsulfonyl)-1,2,3,6-tetrahydropyridin-4-yl]-1H-pyrrolo[2,3-b]pyridine;
4-{3-chloro-4-[(3-chlorobenzyl)oxy]phenyl}-2-[1-(methylsulfonyl)-1,2,3,6-tetrahydropyridin-4-yl]-1H-pyrrolo[2,3-b]pyridine;
4-(4-fluoro-2-methoxyphenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[4-(trifluoromethoxy)phenyl]-1H-pyrrolo[2,3-b]pyridine;
4-[3-chloro-4-(propan-2-yloxy)phenyl]-2-[1-(methylsulfonyl)-1,2,3,6-tetrahydropyridin-4-yl]-1H-pyrrolo[2,3-b]pyridine;
4-(3,5-dichlorophenyl)-2-[1-(methylsulfonyl)-1,2,3,6-tetrahydropyridin-4-yl]-1H-pyrrolo[2,3-b]pyridine;
4-(4-fluoro-2-propoxyphenyl)-2-[1-(methylsulfonyl)-1,2,3,6-tetrahydropyridin-4-yl]-1H-pyrrolo[2,3-b]pyridine;
4-(5-fluoro-2-methoxyphenyl)-2-[1-(morpholin-4-ylsulfonyl)-1,2,3,6-tetrahydropyridin-4-yl]-1H-pyrrolo[2,3-b]pyridine;
2-fluoro-N-{4-methoxy-3-[2-(1,2,3,6-tetrahydropyridin-4-yl)-1H-pyrrolo[2,3-b]pyridin-4-yl]benzyl}aniline;
N-{4-methoxy-3-[2-(1,2,3,6-tetrahydropyridin-4-yl)-1H-pyrrolo[2,3-b]pyridin-4-yl]benzyl}tetrahydro-2H-pyran-4-amine;
4-[2-methoxy-5-(morpholin-4-ylmethyl)phenyl]-2-(1,2,3,6-tetrahydropyridin-4-yl)-1H-pyrrolo[2,3-b]pyridine;
N-benzyl-4-[4-(5-fluoro-2-methoxyphenyl)-1H-pyrrolo[2,3-b]pyridin-2-yl]cyclohex-3-ene-1-carboxamide;
N-(3-fluorobenzyl)-4-[4-(5-fluoro-2-methoxyphenyl)-1H-pyrrolo[2,3-b]pyridin-2-yl]cyclohex-3-ene-1-carboxamide;
N-(3,5-difluorobenzyl)-4-[4-(5-fluoro-2-methoxyphenyl)-1H-pyrrolo[2,3-b]pyridin-2-yl]cyclohex-3-ene-1-carboxamide;
N-(2,5-difluorobenzyl)-4-[4-(5-fluoro-2-methoxyphenyl)-1H-pyrrolo[2,3-b]pyridin-2-yl]cyclohex-3-ene-1-carboxamide;
N-(3-chlorobenzyl)-4-[4-(5-fluoro-2-methoxyphenyl)-1H-pyrrolo[2,3-b]pyridin-2-yl]cyclohex-3-ene-1-carboxamide;
4-[4-(5-fluoro-2-methoxyphenyl)-1H-pyrrolo[2,3-b]pyridin-2-yl]-N-(pyridin-4-ylmethyl)cyclohex-3-ene-1-carboxamide;
4-[4-(5-fluoro-2-methoxyphenyl)-1H-pyrrolo[2,3-b]pyridin-2-yl]-N-[(3-methyl-1H-pyrazol-5-yl)methyl]cyclohex-3-ene-1-carboxamide;
4-[4-(5-fluoro-2-methoxyphenyl)-1H-pyrrolo[2,3-b]pyridin-2-yl]-N-(tetrahydro-2H-pyran-4-ylmethyl)cyclohex-3-ene-1-carboxamide;
4-[4-(5-fluoro-2-methoxyphenyl)-1H-pyrrolo[2,3-b]pyridin-2-yl]-N-(4-hydroxycyclohexyl)cyclohex-3-ene-1-carboxamide;
(3,3-difluoroazetidin-1-yl) {4-[4-(5-fluoro-2-methoxyphenyl)-1H-pyrrolo[2,3-b]pyridin-2-yl]cyclohex-3-en-1-yl}methanone;
2-(3,6-dihydro-2H-pyran-4-yl)-4-(5-fluoro-2-methoxyphenyl)-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}(tetrahydro-2H-pyran-3-yl)methanone;

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]-2-hydroxyethanone;

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]ethanone;

1-{5-[4-(5-fluoro-2-methoxyphenyl)-1H-pyrrolo[2,3-b]pyridin-2-yl]-3,6-dihydropyridin-1(2H)-yl}-2-hydroxyethanone;

1-{5-[4-(5-fluoro-2-methoxyphenyl)-1H-pyrrolo[2,3-b]pyridin-2-yl]-3,6-dihydropyridin-1(2H)-yl}ethanone;

N-[4-({5-[4-(5-fluoro-2-methoxyphenyl)-1H-pyrrolo[2,3-b]pyridin-2-yl]-3,6-dihydropyridin-1(2H)-yl}methyl)phenyl]acetamide;

4-(5-fluoro-2-methoxyphenyl)-2-[1-(tetrahydrofuran-2-ylmethyl)-1,2,5,6-tetrahydropyridin-3-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-methylpropan-2-ol;

4-[4-(5-fluoro-2-methoxyphenyl)-1H-pyrrolo[2,3-b]pyridin-2-yl]-N,N-dimethyl-3,6-dihydropyridine-1(2H)-carboxamide;

ethyl ({4-[4-(5-fluoro-2-methoxyphenyl)-1H-pyrrolo[2,3-b]pyridin-2-yl]piperidin-1-yl}sulfonyl)carbamate;

4-[4-(5-fluoro-2-methoxyphenyl)-1H-pyrrolo[2,3-b]pyridin-2-yl]-N-methylpiperidine-1-sulfonamide;

4-[4-(5-fluoro-2-methoxyphenyl)-1H-pyrrolo[2,3-b]pyridin-2-yl]-N,N-dimethylpiperidine-1-sulfonamide;

4-(5-fluoro-2-methoxyphenyl)-2-[4-(trifluoromethyl)cyclohex-1-en-1-yl]-1H-pyrrolo[2,3-b]pyridine;

4-[4-(5-fluoro-2-methoxyphenyl)-1H-pyrrolo[2,3-b]pyridin-2-yl]-N-(tetrahydro-2H-pyran-4-ylmethyl)cyclohex-3-en-1-amine;

2-{4-[4-(5-fluoro-2-methoxyphenyl)-1H-pyrrolo[2,3-b]pyridin-2-yl]piperidin-1-yl}ethanesulfonamide;

N-benzyl-4-[4-(5-fluoro-2-methoxyphenyl)-1H-pyrrolo[2,3-b]pyridin-2-yl]cyclohex-3-en-1-amine;

4-[4-(5-fluoro-2-methoxyphenyl)-1H-pyrrolo[2,3-b]pyridin-2-yl]-N-(pyridin-4-ylmethyl)cyclohex-3-en-1-amine;

4-[4-(5-fluoro-2-methoxyphenyl)-1H-pyrrolo[2,3-b]pyridin-2-yl]-N-(morpholin-2-ylmethyl)cyclohex-3-en-1-amine;

4-(5-fluoro-2-methoxyphenyl)-2-[1-(S-methylsulfonimidoyl)piperidin-4-yl]-1H-pyrrolo[2,3-b]pyridine;

N-ethyl-4-[4-(5-fluoro-2-methoxyphenyl)-1H-pyrrolo[2,3-b]pyridin-2-yl]piperidine-1-sulfonamide;

4-[3-(4-fluorophenoxy)phenyl]-2-(piperidin-4-yl)-1H-pyrrolo[2,3-b]pyridine;

4-(2,3-difluorophenyl)-2-(1,2,3,6-tetrahydropyridin-4-yl)-1H-pyrrolo[2,3-b]pyridine;

3-{4-[4-(2,3-difluorophenyl)-1H-pyrrolo[2,3-b]pyridin-2-yl]-3,6-dihydropyridin-1(2H)-yl}propane-1,2-diol;

N-[4-({4-[4-(2,3-difluorophenyl)-1H-pyrrolo[2,3-b]pyridin-2-yl]-3,6-dihydropyridin-1(2H)-yl}methyl)phenyl]acetamide;

1-{4-[4-(2,3-difluorophenyl)-1H-pyrrolo[2,3-b]pyridin-2-yl]-3,6-dihydropyridin-1(2H)-yl}-2-hydroxyethanone;

2-(8-azabicyclo[3.2.1]oct-2-en-3-yl)-4-(5-fluoro-2-methoxyphenyl)-1H-pyrrolo[2,3-b]pyridine;

N-(3,5-difluorobenzyl)-4-[4-(5-fluoro-2-methoxyphenyl)-1H-pyrrolo[2,3-b]pyridin-2-yl]cyclohex-3-en-1-amine;

3-[4-(5-fluoro-2-methoxyphenyl)-1H-pyrrolo[2,3-b]pyridin-2-yl]-N-methyl-8-azabicyclo[3.2.1]oct-2-ene-8-carboxamide;

3-{3-[4-(5-fluoro-2-methoxyphenyl)-1H-pyrrolo[2,3-b]pyridin-2-yl]-8-azabicyclo[3.2.1]oct-2-en-8-yl}propane-1,2-diol;

1-{3-[4-(5-fluoro-2-methoxyphenyl)-1H-pyrrolo[2,3-b]pyridin-2-yl]-8-azabicyclo[3.2.1]oct-2-en-8-yl}-2-hydroxyethanone;

3-[4-(5-fluoro-2-methoxyphenyl)-1H-pyrrolo[2,3-b]pyridin-2-yl]-N,N-dimethyl-8-azabicyclo[3.2.1]oct-2-ene-8-carboxamide;

N-[(2S)-2,3-dihydroxypropyl]-4-[4-(5-fluoro-2-methoxyphenyl)-1H-pyrrolo[2,3-b]pyridin-2-yl]piperidine-1-sulfonamide;

4-[4-(5-fluoro-2-methoxyphenyl)-1H-pyrrolo[2,3-b]pyridin-2-yl]-N-(2-hydroxyethyl)-3,6-dihydropyridine-1(2H)-carboxamide;

4-[4-(5-fluoro-2-methoxyphenyl)-1H-pyrrolo[2,3-b]pyridin-2-yl]-N-(methylsulfonyl)cyclohex-3-ene-1-carboxamide;

N-methyl-4-[2-(1,2,3,6-tetrahydropyridin-4-yl)-1H-pyrrolo[2,3-b]pyridin-4-yl]benzamide;

5-[4-(5-fluoro-2-methoxyphenyl)-1H-pyrrolo[2,3-b]pyridin-2-yl]-N,N-dimethyl-3,6-dihydropyridine-1(2H)-carboxamide;

4-[4-(5-fluoro-2-methoxyphenyl)-1H-pyrrolo[2,3-b]pyridin-2-yl]-N-(pyridin-3-ylmethyl)cyclohex-3-en-1-amine;

4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-[2-(pyrrolidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-[2-(4-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(tetrahydrofuran-2-ylmethyl)amino]ethyl}-3,6-dihydropyridine-1(2H)-carboxamide;

methyl 4-{2-[({4-[4-(5-fluoro-2-methoxyphenyl)-1H-pyrrolo[2,3-b]pyridin-2-yl]-3,6-dihydropyridin-1(2H)-yl}carbonyl)amino]ethyl}piperazine-1-carboxylate;

N-[2-(3,4-dihydroisoquinolin-2(1H)-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide;

1-{5-[4-(5-fluoro-2-methoxyphenyl)-1H-pyrrolo[2,3-b]pyridin-2-yl]-3,6-dihydropyridin-1(2H)-yl}-2-methylpropan-2-ol;

4-{2-[1-(2,3-dihydroxypropyl)-1,2,3,6-tetrahydropyridin-4-yl]-1H-pyrrolo[2,3-b]pyridin-4-yl}-N-methylbenzamide;

N-methyl-4-{4-[4-(methylcarbamoyl)phenyl]-1H-pyrrolo[2,3-b]pyridin-2-yl}-3,6-dihydropyridine-1(2H)-carboxamide;

4-{2-[1-(hydroxyacetyl)-1,2,3,6-tetrahydropyridin-4-yl]-1H-pyrrolo[2,3-b]pyridin-4-yl}-N-methylbenzamide;

4-[4-(5-fluoro-2-methoxyphenyl)-1H-pyrrolo[2,3-b]pyridin-2-yl]-N,N-dimethyl-3,6-dihydropyridine-1(2H)-sulfonamide;

4-(2,4-dimethoxyphenyl)-2-(1,2,3,6-tetrahydropyridin-4-yl)-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}glycine;

4-[4-(5-fluoro-2-methoxyphenyl)-1H-pyrrolo[2,3-b]pyridin-2-yl]-N-methylcyclohex-3-ene-1-carboxamide;

4-[4-(5-fluoro-2-methoxyphenyl)-1H-pyrrolo[2,3-b]pyridin-2-yl]-N-[(3-hydroxyoxetan-3-yl)methyl]-3,6-dihydropyridine-1(2H)-carboxamide;

methyl {4-[4-(5-fluoro-2-methoxyphenyl)-1H-pyrrolo[2,3-b]pyridin-2-yl]-3,6-dihydropyridin-1(2H)-yl}acetate;

4-(4,5-difluoro-2-methoxyphenyl)-2-(1,2,3,6-tetrahydropyridin-4-yl)-1H-pyrrolo[2,3-b]pyridine;

4-[2-methoxy-4-(1H-pyrazol-1-yl)phenyl]-2-(1,2,3,6-tetrahydropyridin-4-yl)-1H-pyrrolo[2,3-b]pyridine;

4-(2,6-dimethoxyphenyl)-2-(1,2,3,6-tetrahydropyridin-4-yl)-1H-pyrrolo[2,3-b]pyridine;

4-(2-methoxyphenyl)-2-(1,2,3,6-tetrahydropyridin-4-yl)-1H-pyrrolo[2,3-b]pyridine;

4-(2-chloro-5-methoxyphenyl)-2-(1,2,3,6-tetrahydropyridin-4-yl)-1H-pyrrolo[2,3-b]pyridine;

4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile;

1-{4-[4-(2,3-difluorophenyl)-1H-pyrrolo[2,3-b]pyridin-2-yl]-3,6-dihydropyridin-1(2H)-yl}-2-methylpropan-2-ol;

4-(2,3-difluorophenyl)-2-[1-(pyridin-2-ylmethyl)-1,2,3,6-tetrahydropyridin-4-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-(5-fluoro-2-methoxyphenyl)-2-(1,2,3,6-tetrahydropyridin-4-yl)-1H-pyrrolo[2,3-b]pyridine-5-carbonitrile;

5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one;

2-{4-[4-(5-fluoro-2-methoxyphenyl)-1H-pyrrolo[2,3-b]pyridin-2-yl]-3,6-dihydropyridin-1(2H)-yl}-N-methylacetamide;

4-(5-fluoro-2-methoxyphenyl)-5-methyl-2-[1-(methylsulfonyl)-1,2,3,6-tetrahydropyridin-4-yl]-1H-pyrrolo[2,3-b]pyridine;

4-(5-fluoro-2-methoxyphenyl)-5-methyl-2-(1,2,3,6-tetrahydropyridin-4-yl)-1H-pyrrolo[2,3-b]pyridine;

N-[{4-[4-(5-fluoro-2-methoxyphenyl)-1H-pyrrolo[2,3-b]pyridin-2-yl]-3,6-dihydropyridin-1(2H)-yl}(methyl)oxido-λ$^6$-sulfanylidene]-4-methylbenzenesulfonamide;

4-(2-ethoxy-5-fluorophenyl)-2-(1,2,3,6-tetrahydropyridin-4-yl)-1H-pyrrolo[2,3-b]pyridine;

4-(2,5-dimethoxyphenyl)-2-(1,2,3,6-tetrahydropyridin-4-yl)-1H-pyrrolo[2,3-b]pyridine;

N-[(2S)-2,3-dihydroxypropyl]-4-[4-(5-fluoro-2-methoxyphenyl)-1H-pyrrolo[2,3-b]pyridin-2-yl]cyclohex-3-ene-1-carboxamide;

4-{4-[4-(5-fluoro-2-methoxyphenyl)-1H-pyrrolo[2,3-b]pyridin-2-yl]-3,6-dihydropyridin-1(2H)-yl}cyclohexanol;

1-({4-[4-(5-fluoro-2-methoxyphenyl)-1H-pyrrolo[2,3-b]pyridin-2-yl]-3,6-dihydropyridin-1(2H)-yl}carbonyl)piperidine-4-carboxylic acid;

4-[4-(5-fluoro-2-methoxyphenyl)-1H-pyrrolo[2,3-b]pyridin-2-yl]-N-[2-(4-oxopiperidin-1-yl)ethyl]-3,6-dihydropyridine-1(2H)-carboxamide;

N-[2-(3,3-difluoropiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-[2-(3-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypyrrolidin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(2-hydroxyethyl)piperazin-1-yl]ethyl}-3,6-dihydropyridine-1(2H) carboxamide;

4-[4-(5-fluoro-2-methoxyphenyl)-1H-pyrrolo[2,3-b]pyridin-2-yl]-N-[2-(3-oxopiperazin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypiperidin-1-yl]ethyl}-3,6-dihydropyridine-1(2H)-carboxamide;

4-methoxy-3-[2-(1,2,3,6-tetrahydropyridin-4-yl)-1H-pyrrolo[2,3-b]pyridin-4-yl]benzonitrile;

4-(2-chloro-5-fluorophenyl)-2-(1,2,3,6-tetrahydropyridin-4-yl)-1H-pyrrolo[2,3-b]pyridine;

4-(4-fluoro-2-methoxyphenyl)-2-(1,2,3,6-tetrahydropyridin-4-yl)-1H-pyrrolo[2,3-b]pyridine;

4-[2-(difluoromethoxy)-5-fluorophenyl]-2-(1,2,3,6-tetrahydropyridin-4-yl)-1H-pyrrolo[2,3-b]pyridine;

({4-[4-(5-fluoro-2-methoxyphenyl)-1H-pyrrolo[2,3-b]pyridin-2-yl]-3,6-dihydropyridin-1(2H)-yl}sulfonyl)acetic acid;

4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine;

5-chloro-4-(5-fluoro-2-methoxyphenyl)-2-(1,2,3,6-tetrahydropyridin-4-yl)-1H-pyrrolo[2,3-b]pyridine;

4-(5-fluoro-2-methoxyphenyl)-2-{1-[(tetrahydrofuran-2-ylmethyl)sulfonyl]-1,2,3,6-tetrahydropyridin-4-yl}-1H-pyrrolo[2,3-b]pyridine;

ethyl ({4-[4-(5-fluoro-2-methoxyphenyl)-5-methyl-1H-pyrrolo[2,3-b]pyridin-2-yl]-3,6-dihydropyridin-1(2H)-yl}sulfonyl)carbamate;

(cis-4-{4-[5-fluoro-4-(5-fluoro-2-methoxyphenyl)-1H-pyrrolo[2,3-b]pyridin-2-yl]piperidin-1-yl}cyclohexyl)acetic acid;

4-[4-(5-fluoro-2-methoxyphenyl)-1H-pyrrolo[2,3-b]pyridin-2-yl]-N-(pyridin-2-ylmethyl)cyclohex-3-en-1-amine;

4-[4-(5-fluoro-2-methoxyphenyl)-1H-pyrrolo[2,3-b]pyridin-2-yl]-N-(pyrazin-2-ylmethyl)cyclohex-3-en-1-amine;

4-[4-(5-fluoro-2-methoxyphenyl)-1H-pyrrolo[2,3-b]pyridin-2-yl]-N-(pyrimidin-5-ylmethyl)cyclohex-3-en-1-amine;

4-[4-(5-fluoro-2-methoxyphenyl)-1H-pyrrolo[2,3-b]pyridin-2-yl]-N-(tetrahydrofuran-2-ylmethyl)cyclohex-3-en-1-amine;

4-{5-fluoro-2-[($^2$H$_3$)methyloxy]phenyl}-2-(1,2,3,6-tetrahydropyridin-4-yl)-1H-pyrrolo[2,3-b]pyridine;

4-(4-{5-fluoro-2-[($^2$H$_3$)methyloxy]phenyl}-1H-pyrrolo[2,3-b]pyridin-2-yl)-N-methyl-3,6-dihydropyridine-1(2H)-carboxamide;

4-{5-fluoro-2-[($^2$H$_3$)methyloxy]phenyl}-2-[1-(methylsulfonyl)-1,2,3,6-tetrahydropyridin-4-yl]-1H-pyrrolo[2,3-b]pyridine;

methyl 2-{4-[4-(5-fluoro-2-methoxyphenyl)-1H-pyrrolo[2,3-b]pyridin-2-yl]-3,6-dihydropyridin-1(2H)-yl}propanoate;

5-chloro-4-(5-fluoro-2-methoxyphenyl)-2-[1-(methylsulfonyl)-1,2,3,6-tetrahydropyridin-4-yl]-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone;

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid;

{4-[4-(5-fluoro-2-methoxyphenyl)-1H-pyrrolo[2,3-b]pyridin-2-yl]-3,6-dihydropyridin-1(2H)-yl}[(4S)-2,2,5,5-tetramethyl-1,3-dioxolan-4-yl]methanone;

2-{4-[4-(5-fluoro-2-methoxyphenyl)-1H-pyrrolo[2,3-b]pyridin-2-yl]-3,6-dihydropyridin-1(2H)-yl}propanoic acid;

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid;

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid;

methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-fluoro-N-methyl-4-{2-[1-(methylsulfonyl)-1,2,3,6-tetrahydropyridin-4-yl]-1H-pyrrolo[2,3-b]pyridin-4-yl}benzamide;

(2S)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

(2R)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

4-(5-fluoro-2-methoxyphenyl)-2-[1-(hydroxyacetyl)-1,2,3,6-tetrahydropyridin-4-yl]-1H-pyrrolo[2,3-b]pyridine-5-carbonitrile;

4-[5-cyano-4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-N-[2-(piperazin-1-yl)ethyl]-3,6-dihydropyridine-1(2H)-carboxamide;

N-[2-(4-aminopiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

N-{2-[(1,3-dihydroxypropan-2-yl)amino]ethyl}-4-[4-(5-fluoro-2-methoxyphenyl)-1H-pyrrolo[2,3-b]pyridin-2-yl]-3,6-dihydropyridine-1(2H)-carboxamide;

3-ethoxy-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

5-fluoro-4-(5-fluoro-2-methoxyphenyl)-2-(1,2,3,6-tetrahydropyridin-4-yl)-1H-pyrrolo[2,3-b]pyridine;

4-[5-fluoro-4-(5-fluoro-2-methoxyphenyl)-1H-pyrrolo[2,3-b]pyridin-2-yl]-N-methyl-3,6-dihydropyridine-1(2H)-carboxamide;

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]-3,6-dihydropyridin-1(2H)-yl}propane-1,2-diol;

1-{4-[4-(5-fluoro-2-methoxyphenyl)-1H-pyrrolo[2,3-b]pyridin-2-yl]-3,6-dihydropyridin-1(2H)-yl}-2-(methylsulfonyl)ethanone;

ethyl 3-{4-[4-(5-fluoro-2-methoxyphenyl)-1H-pyrrolo[2,3-b]pyridin-2-yl]-3,6-dihydropyridin-1(2H)-yl}-3-oxopropanoate;

4-[4-(5-fluoro-2-methoxyphenyl)-1H-pyrrolo[2,3-b]pyridin-2-yl]-N-{1-[2-(methylsulfonyl)ethyl]-H-pyrazol-4-yl}-3,6-dihydropyridine-1(2H)-carboxamide;

N-(2-{4-[4-(5-fluoro-2-methoxyphenyl)-1H-pyrrolo[2,3-b]pyridin-2-yl]-3,6-dihydropyridin-1(2H)-yl}-2-oxoethyl)methanesulfonamide;

4-[4-(2,3-difluorophenyl)-1H-pyrrolo[2,3-b]pyridin-2-yl]cyclohex-3-ene-1-carboxylic acid;

N-({4-[4-(5-fluoro-2-methoxyphenyl)-1H-pyrrolo[2,3-b]pyridin-2-yl]cyclohex-3-en-1-yl}carbonyl)glycine;

3-{4-[4-(5-fluoro-2-methoxyphenyl)-1H-pyrrolo[2,3-b]pyridin-2-yl]-3,6-dihydropyridin-1(2H)-yl}-3-oxopropanoic acid;

4-(4-chloro-2-methoxyphenyl)-2-(1,2,3,6-tetrahydropyridin-4-yl)-1H-pyrrolo[2,3-b]pyridine;

4-(2,4-dimethoxyphenyl)-2-[1-(methylsulfonyl)-1,2,3,6-tetrahydropyridin-4-yl]-1H-pyrrolo[2,3-b]pyridine;

3-{4-[4-(2,4-dimethoxyphenyl)-1H-pyrrolo[2,3-b]pyridin-2-yl]-3,6-dihydropyridin-1(2H)-yl}propane-1,2-diol;

4-[4-(2,4-dimethoxyphenyl)-1H-pyrrolo[2,3-b]pyridin-2-yl]-N-methyl-3,6-dihydropyridine-1(2H)-carboxamide;

1-{4-[4-(2,4-dimethoxyphenyl)-1H-pyrrolo[2,3-b]pyridin-2-yl]-3,6-dihydropyridin-1(2H)-yl}-2-hydroxyethanone;

3-{4-[4-(2-methoxyphenyl)-1H-pyrrolo[2,3-b]pyridin-2-yl]-3,6-dihydropyridin-1(2H)-yl}propane-1,2-diol;

4-[4-(2-methoxyphenyl)-1H-pyrrolo[2,3-b]pyridin-2-yl]-N-methyl-3,6-dihydropyridine-1(2H)-carboxamide;

2-hydroxy-1-{4-[4-(2-methoxyphenyl)-1H-pyrrolo[2,3-b]pyridin-2-yl]-3,6-dihydropyridin-1(2H)-yl}ethanone;

3-{4-[4-(4-fluoro-2-methoxyphenyl)-1H-pyrrolo[2,3-b]pyridin-2-yl]-3,6-dihydropyridin-1(2H)-yl}propane-1,2-diol;

4-[4-(4-fluoro-2-methoxyphenyl)-1H-pyrrolo[2,3-b]pyridin-2-yl]-N-methyl-3,6-dihydropyridine-1(2H)-carboxamide;

1-{4-[4-(4-fluoro-2-methoxyphenyl)-1H-pyrrolo[2,3-b]pyridin-2-yl]-3,6-dihydropyridin-1(2H)-yl}-2-hydroxyethanone;

3-{4-[4-(4,5-difluoro-2-methoxyphenyl)-1H-pyrrolo[2,3-b]pyridin-2-yl]-3,6-dihydropyridin-1(2H)-yl}propane-1,2-diol;

1-{4-[4-(4,5-difluoro-2-methoxyphenyl)-1H-pyrrolo[2,3-b]pyridin-2-yl]-3,6-dihydropyridin-1(2H)-yl}-2-hydroxyethanone;

N-({4-[4-(5-fluoro-2-methoxyphenyl)-1H-pyrrolo[2,3-b]pyridin-2-yl]-3,6-dihydropyridin-1(2H)-yl}sulfonyl)acetamide;

4-(4,5-difluoro-2-methoxyphenyl)-2-[1-(methylsulfonyl)-1,2,3,6-tetrahydropyridin-4-yl]-1H-pyrrolo[2,3-b]pyridine;

2-(8-azabicyclo[3.2.1]oct-2-en-3-yl)-4-(2,3-difluorophenyl)-1H-pyrrolo[2,3-b]pyridine;

{4-[5-cyano-4-(5-fluoro-2-methoxyphenyl)-1H-pyrrolo[2,3-b]pyridin-2-yl]-3,6-dihydropyridin-1(2H)-yl}acetic acid;

4-[4-(5-fluoro-2-methoxyphenyl)-1H-pyrrolo[2,3-b]pyridin-2-yl]-N-(2-{[2-(1H-imidazol-4-yl)ethyl]amino}ethyl)-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxypropyl)amino]ethyl}-3,6-dihydropyridine-1(2H)-carboxamide;

N-[2-(dimethylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(2-{[(3-methyloxetan-3-yl)methyl]amino}ethyl)-3,6-dihydropyridine-1(2H)-carboxamide;

4-[4-(5-fluoro-2-methoxyphenyl)-1H-pyrrolo[2,3-b]pyridin-2-yl]-N-[2-(oxetan-3-ylamino)ethyl]-3,6-dihydropyridine-1(2H)-carboxamide;

3-methoxy-N-methyl-4-[2-(1,2,3,6-tetrahydropyridin-4-yl)-1H-pyrrolo[2,3-b]pyridin-4-yl]benzamide;

3-methoxy-N-methyl-4-{2-[1-(methylsulfonyl)-1,2,3,6-tetrahydropyridin-4-yl]-1H-pyrrolo[2,3-b]pyridin-4-yl}benzamide;

4-{2-[1-(2,3-dihydroxypropyl)-1,2,3,6-tetrahydropyridin-4-yl]-1H-pyrrolo[2,3-b]pyridin-4-yl}-3-methoxy-N-methylbenzamide;

3-amino-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

4-(5-fluoro-2-methoxyphenyl)-2-(2,5,6,7-tetrahydro-14-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,75-tetrahydro-1H-azepin-4-yl)-1H-pyrrolo[2,3-b]pyridine;

4-(5-fluoro-2-methoxyphenyl)-2-[1-(methylsulfonyl)-2,5,6,7-tetrahydro-1H-azepin-4-yl]-1H-pyrrolo[2,3-b]pyridine and 4-(5-fluoro-2-methoxyphenyl)-2-(1-(methylsulfonyl)-2,3,6,7-tetrahydro-1H-azepin-4-yl)-1H-pyrrolo[2,3-b]pyridine;

5-[4-(5-fluoro-2-methoxyphenyl)-1H-pyrrolo[2,3-b]pyridin-2-yl]-N-methyl-2,3,4,7-tetrahydro-1H-azepine-1-carboxamide and 4-(4-(5-fluoro-2-methoxyphenyl)-1H-pyrrolo[2,3-b]pyridin-2-yl)-N-methyl-2,3,6,7-tetrahydro-1H-azepine-1-carboxamide;

1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(methylsulfonyl)acetamide;

2-{4-[4-(2,4-dimethoxyphenyl)-1H-pyrrolo[2,3-b]pyridin-2-yl]-3,6-dihydropyridin-1(2H)-yl}-N,N-dimethylacetamide;

2-{4-[4-(2-methoxyphenyl)-1H-pyrrolo[2,3-b]pyridin-2-yl]-3,6-dihydropyridin-1(2H)-yl}-N,N-dimethylacetamide;

2-{4-[4-(4-fluoro-2-methoxyphenyl)-1H-pyrrolo[2,3-b]pyridin-2-yl]-3,6-dihydropyridin-1(2H)-yl}-N,N-dimethylacetamide;

2-{4-[4-(4,5-difluoro-2-methoxyphenyl)-1H-pyrrolo[2,3-b]pyridin-2-yl]-3,6-dihydropyridin-1(2H)-yl}-N,N-dimethylacetamide;

tert-butyl {5-[4-(5-fluoro-2-methoxyphenyl)-1H-pyrrolo[2,3-b]pyridin-2-yl]-3,6-dihydropyridin-1(2H)-yl}acetate;

N-({4-[4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

2-{5-[4-(5-fluoro-2-methoxyphenyl)-1H-pyrrolo[2,3-b]pyridin-2-yl]-3,6-dihydropyridin-1(2H)-yl}-N,N-dimethylacetamide;

{5-[4-(5-fluoro-2-methoxyphenyl)-1H-pyrrolo[2,3-b]pyridin-2-yl]-3,6-dihydropyridin-1(2H)-yl}acetic acid;

ethyl 1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylate;

2-(dimethylamino)-1-{4-[4-(5-fluoro-2-methoxyphenyl)-1H-pyrrolo[2,3-b]pyridin-2-yl]-3,6-dihydropyridin-1(2H)-yl}ethanone;

{4-[5-fluoro-4-(5-fluoro-2-methoxyphenyl)-1H-pyrrolo[2,3-b]pyridin-2-yl]-3,6-dihydropyridin-1(2H)-yl}acetic acid;

2-({4-[4-(5-fluoro-2-methoxyphenyl)-1H-pyrrolo[2,3-b]pyridin-2-yl]cyclohex-3-en-1-yl}amino)butanoic acid;

4-(2,3-difluorophenyl)-2-[1-(methylsulfonyl)-1,2,5,6-tetrahydropyridin-3-yl]-1H-pyrrolo[2,3-b]pyridine;

2-{5-[4-(2,3-difluorophenyl)-1H-pyrrolo[2,3-b]pyridin-2-yl]-3,6-dihydropyridin-1(2H)-yl}-N,N-dimethylacetamide;

1-{5-[4-(2,3-difluorophenyl)-1H-pyrrolo[2,3-b]pyridin-2-yl]-3,6-dihydropyridin-1(2H)-yl}-2-hydroxyethanone;

4-(5-fluoro-2-methoxyphenyl)-2-[1-(methylsulfonyl)azepan-4-yl]-1H-pyrrolo[2,3-b]pyridine;

{3-[4-(5-fluoro-2-methoxyphenyl)-1H-pyrrolo[2,3-b]pyridin-2-yl]-2,5-dihydro-1H-pyrrol-1-yl}acetic acid;

2-{4-[4-(5-fluoro-2-methoxyphenyl)-1H-pyrrolo[2,3-b]pyridin-2-yl]piperidin-1-yl}-N,N-dimethylethanesulfonamide;

{4-[4-(2,4-dimethoxyphenyl)-1H-pyrrolo[2,3-b]pyridin-2-yl]-3,6-dihydropyridin-1(2H)-yl}acetic acid;

{4-[4-(2-methoxyphenyl)-1H-pyrrolo[2,3-b]pyridin-2-yl]-3,6-dihydropyridin-1(2H)-yl}acetic acid;

{4-[4-(4,5-difluoro-2-methoxyphenyl)-1H-pyrrolo[2,3-b]pyridin-2-yl]-3,6-dihydropyridin-1(2H)-yl}acetic acid;

1-{4-[4-(5-fluoro-2-methoxyphenyl)-1H-pyrrolo[2,3-b]pyridin-2-yl]-3,6-dihydropyridin-1(2H)-yl}-2-(3-hydroxypyrrolidin-1-yl)ethanone;

methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate;

{4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetic acid;

N-(cyclopropylsulfonyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(phenylsulfonyl)-3,6-dihydropyridine-1(2H)-carboxamide;

5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one;

{4-[4-(5-fluoro-2-methoxyphenyl)-1H-pyrrolo[2,3-b]pyridin-2-yl]piperidin-1-yl}acetic acid;

{3-[4-(5-fluoro-2-methoxyphenyl)-1H-pyrrolo[2,3-b]pyridin-2-yl]pyrrolidin-1-yl}acetic acid;

4-[4-(5-fluoro-2-methoxyphenyl)-1H-pyrrolo[2,3-b]pyridin-2-yl]-2,5-dihydro-1H-pyrrole-2-carboxylic acid;

3-{4-[4-(2,3-difluorophenyl)-1H-pyrrolo[2,3-b]pyridin-2-yl]-3,6-dihydropyridin-1(2H)-yl}-3-oxopropanenitrile;

{4-[4-(5-fluoro-2-methoxyphenyl)-1H-pyrrolo[2,3-b]pyridin-2-yl]-3,6-dihydropyridin-1(2H)-yl}(1-hydroxycyclopropyl)methanone;

3-{5-[4-(2,3-difluorophenyl)-1H-pyrrolo[2,3-b]pyridin-2-yl]-3,6-dihydropyridin-1(2H)-yl}propane-1,2-diol;

1-{5-[4-(2,3-difluorophenyl)-1H-pyrrolo[2,3-b]pyridin-2-yl]-3,6-dihydropyridin-1(2H)-yl}-2-hydroxy-2-methylpropan-1-one;

{4-[4-(4-fluoro-2-methoxyphenyl)-1H-pyrrolo[2,3-b]pyridin-2-yl]-3,6-dihydropyridin-1(2H)-yl}acetic acid;

{3-[4-(5-fluoro-2-methoxyphenyl)-1H-pyrrolo[2,3-b]pyridin-2-yl]-8-azabicyclo[3.2.1]oct-2-en-8-yl}acetic acid;

1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylic acid;

1-{5-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-[4-(5-fluoro-2-methoxyphenyl)-1H-pyrrolo[2,3-b]pyridin-2-yl]-N-(propan-2-ylsulfonyl)cyclohex-3-ene-1-carboxamide;

2-{4-[4-(5-fluoro-2-methoxyphenyl)-1H-pyrrolo[2,3-b]pyridin-2-yl]-3,6-dihydropyridin-1(2H)-yl}-2-oxoethanesulfonamide;

2-{4-[4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;

tert-butyl {4-[4-(5-fluoro-2-methoxyphenyl)-1H-pyrrolo[2,3-b]pyridin-2-yl]-3,6-dihydropyridin-1(2H)-yl}acetate;
4-[4-(5-fluoro-2-methoxyphenyl)-1H-pyrrolo[2,3-b]pyridin-2-yl]-N-{1-[(2R)-2-hydroxypropyl]-1H-pyrazol-4-yl}-3,6-dihydropyridine-1(2H)-carboxamide;
4-(5-fluoro-2-methoxyphenyl)-2-[1-(2H-tetrazol-5-ylmethyl)-1,2,3,6-tetrahydropyridin-4-yl]-1H-pyrrolo[2,3-b]pyridine;
6-[4-(5-fluoro-2-methoxyphenyl)-1H-pyrrolo[2,3-b]pyridin-2-yl]-2-azaspiro[3.3]heptan-6-ol;
{(2R)-4-[4-(5-fluoro-2-methoxyphenyl)-1H-pyrrolo[2,3-b]pyridin-2-yl]-2,5-dihydro-1H-pyrrol-2-yl}methanol;
{4-[4-(2,3-difluorophenyl)-1H-pyrrolo[2,3-b]pyridin-2-yl]-3,6-dihydropyridin-1(2H)-yl}acetic acid;
4-[4-(5-fluoro-2-methoxyphenyl)-1H-pyrrolo[2,3-b]pyridin-2-yl]cyclohex-3-en-1-ol;
2-{3-[4-(5-fluoro-2-methoxyphenyl)-1H-pyrrolo[2,3-b]pyridin-2-yl]pyrrolidin-1-yl}-N,N-dimethylacetamide;
3-[4-(5-fluoro-2-methoxyphenyl)-1H-pyrrolo[2,3-b]pyridin-2-yl]cyclopent-3-en-1-amine;
3-[4-(5-fluoro-2-methoxyphenyl)-1H-pyrrolo[2,3-b]pyridin-2-yl]cyclopent-2-en-1-amine;
2-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]-1H-isoindole-1,3(2H)-dione;
3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;
4-[4-(5-fluoro-2-methoxyphenyl)-1H-pyrrolo[2,3-b]pyridin-2-yl]-N-(2-{[(1S,2S)-2-hydroxycyclohexyl]amino}ethyl)-3,6-dihydropyridine-1(2H)-carboxamide;
N-(2-{[2-(dimethylamino)ethyl]amino}ethyl)-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-{2-[(2-methoxyethyl)(methyl)amino]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[4-(4-methylbenzoyl)piperazin-1-yl]ethyl}-3,6-dihydropyridine-1(2H) carboxamide;
4-[4-(5-fluoro-2-methoxyphenyl)-1H-pyrrolo[2,3-b]pyridin-2-yl]-N-{2-[4-(methylsulfonyl)piperazin-1-yl]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide;
4-[4-(5-fluoro-2-methoxyphenyl)-1H-pyrrolo[2,3-b]pyridin-2-yl]-N-(2-{[3-(trifluoromethyl)benzyl]amino}ethyl)-3,6-dihydropyridine-1(2H)-carboxamide;
ethyl ({4-[4-(2,3-difluorophenyl)-1H-pyrrolo[2,3-b]pyridin-2-yl]-3,6-dihydropyridin-1(2H)-yl}sulfonyl)carbamate;
2,2,2-trifluoroethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-[4-(5-fluoro-2-methoxyphenyl)-1H-pyrrolo[2,3-b]pyridin-2-yl]cyclohex-3-en-1-one;
2-(3,6-dihydro-2H-thiopyran-4-yl)-4-(5-fluoro-2-methoxyphenyl)-1H-pyrrolo[2,3-b]pyridine;
3-fluoro-N-methyl-4-[2-(1,2,3,6-tetrahydropyridin-4-yl)-1H-pyrrolo[2,3-b]pyridin-4-yl]benzamide;
N-({4-[4-(5-fluoro-2-methoxyphenyl)-1H-pyrrolo[2,3-b]pyridin-2-yl]-3,6-dihydropyridin-1(2H)-yl}carbonyl)alanine;
4-(5-fluoro-2-methoxyphenyl)-2-(1-oxido-3,6-dihydro-2H-thiopyran-4-yl)-1H-pyrrolo[2,3-b]pyridine;
4-[4-(5-fluoro-2-methoxyphenyl)-1H-pyrrolo[2,3-b]pyridin-2-yl]-N-[(1-methylcyclopropyl)sulfonyl]cyclohex-3-ene-1-carboxamide;
4-[4-(5-fluoro-2-methoxyphenyl)-1H-pyrrolo[2,3-b]pyridin-2-yl]-N-[(2-methylpropyl)sulfonyl]cyclohex-3-ene-1-carboxamide;
4-[4-(2,3-difluorophenyl)-1H-pyrrolo[2,3-b]pyridin-2-yl]-N-(phenylsulfonyl)-3,6-dihydropyridine-1(2H)-carboxamide;
4-(5-fluoro-2-methoxyphenyl)-2-(1,2,3,6-tetrahydropyridin-4-yl)-1H-pyrrolo[2,3-b]pyridine-5-carboxamide;
2-[1-(2,3-dihydroxypropyl)-1,2,3,6-tetrahydropyridin-4-yl]-4-(5-fluoro-2-methoxyphenyl)-1H-pyrrolo[2,3-b]pyridine-5-carbonitrile;
2-{4-[5-chloro-4-(5-fluoro-2-methoxyphenyl)-1H-pyrrolo[2,3-b]pyridin-2-yl]-3,6-dihydropyridin-1(2H)-yl}-N,N-dimethylacetamide;
{4-[5-chloro-4-(5-fluoro-2-methoxyphenyl)-1H-pyrrolo[2,3-b]pyridin-2-yl]-3,6-dihydropyridin-1(2H)-yl}acetic acid;
3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol;
{4-[4-(5-fluoro-2-methoxyphenyl)-1H-pyrrolo[2,3-b]pyridin-2-yl]-3,6-dihydropyridin-1(2H)-yl}[(2S,4S)-4-hydroxypyrrolidin-2-yl]methanone;
N-[2-(ethylamino)ethyl]-4-[4-(5-fluoro-2-methoxyphenyl)-1H-pyrrolo[2,3-b]pyridin-2-yl]-3,6-dihydropyridine-1(2H)-carboxamide;
N-[2-(cyclopropylamino)ethyl]-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-{2-[(pyridin-2-ylmethyl)amino]ethyl}-3,6-dihydropyridine-1(2H)-carboxamide;
3-amino-4-{4-[4-(2-{2-[(2-amino-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;
tert-butyl 4-({4-[4-(5-fluoro-2-methoxyphenyl)-1H-pyrrolo[2,3-b]pyridin-2-yl]-3,6-dihydropyridin-1(2H)-yl}sulfonyl)piperidine-1-carboxylate;
4-[4-(5-fluoro-2-methoxyphenyl)-1H-pyrrolo[2,3-b]pyridin-2-yl]-1-(methylsulfonyl)-2,5-dihydro-1H-pyrrole-2-carboxylic acid;
4-(5-fluoro-2-methoxyphenyl)-2-[1-(piperidin-4-ylsulfonyl)-1,2,3,6-tetrahydropyridin-4-yl]-1H-pyrrolo[2,3-b]pyridine;
N,N-dimethyl-4-{2-[1-(methylsulfonyl)-1,2,3,6-tetrahydropyridin-4-yl]-1H-pyrrolo[2,3-b]pyridin-4-yl}benzamide;
2-{4-[4-(5-fluoro-2-methoxyphenyl)-1H-pyrrolo[2,3-b]pyridin-2-yl]-3,6-dihydropyridin-1(2H)-yl}-N,N-dimethylpropanamide;
4-(4-fluoro-2-methoxyphenyl)-2-[8-(methylsulfonyl)-8-azabicyclo[3.2.1]oct-2-en-3-yl]-1H-pyrrolo[2,3-b]pyridine;
4-(4,5-difluoro-2-methoxyphenyl)-2-[8-(methylsulfonyl)-8-azabicyclo[3.2.1]oct-2-en-3-yl]-1H-pyrrolo[2,3-b]pyridine;
4-(2-methoxyphenyl)-2-[8-(methylsulfonyl)-8-azabicyclo[3.2.1]oct-2-en-3-yl]-1H-pyrrolo[2,3-b]pyridine;
4-(3-fluoro-2-methoxyphenyl)-2-(1,2,3,6-tetrahydropyridin-4-yl)-1H-pyrrolo[2,3-b]pyridine;
ethyl ({4-[4-(4-fluoro-2-methoxyphenyl)-1H-pyrrolo[2,3-b]pyridin-2-yl]-3,6-dihydropyridin-1(2H)-yl}sulfonyl)carbamate;

ethyl ({4-[4-(2,4-dimethoxyphenyl)-1H-pyrrolo[2,3-b]pyridin-2-yl]-3,6-dihydropyridin-1(2H)-yl}sulfonyl)carbamate;
ethyl ({4-[4-(2-methoxyphenyl)-1H-pyrrolo[2,3-b]pyridin-2-yl]-3,6-dihydropyridin-1(2H)-yl}sulfonyl)carbamate;
ethyl ({4-[4-(4,5-difluoro-2-methoxyphenyl)-1H-pyrrolo[2,3-b]pyridin-2-yl]-3,6-dihydropyridin-1(2H)-yl}sulfonyl)carbamate;
{4-[4-(5-fluoro-2-methoxyphenyl)-1H-pyrrolo[2,3-b]pyridin-2-yl]-3,6-dihydropyridin-1(2H)-yl}[(2S,4R)-4-hydroxypyrrolidin-2-yl]methanone;
{4-[4-(5-fluoro-2-methoxyphenyl)-1H-pyrrolo[2,3-b]pyridin-2-yl]-3,6-dihydropyridin-1(2H)-yl}[(2R,4S)-4-hydroxypyrrolidin-2-yl]methanone;
4-[4-(5-fluoro-2-methoxyphenyl)-1H-pyrrolo[2,3-b]pyridin-2-yl]-N,N-dimethylcyclohex-3-ene-1-carboxamide;
N-{4-[4-(5-fluoro-2-methoxyphenyl)-1H-pyrrolo[2,3-b]pyridin-2-yl]cyclohex-3-en-1-yl}alanine;
2-({4-[4-(5-fluoro-2-methoxyphenyl)-1H-pyrrolo[2,3-b]pyridin-2-yl]-3,6-dihydropyridin-1(2H)-yl}sulfonyl)ethanamine;
4-{2-[1-(methylsulfonyl)-1,2,3,6-tetrahydropyridin-4-yl]-1H-pyrrolo[2,3-b]pyridin-4-yl}-N-propylbenzamide;
3-fluoro-N-methyl-4-{2-[1-(methylsulfonyl)-1,2,3,6-tetrahydropyridin-4-yl]-1H-pyrrolo[2,3-b]pyridin-4-yl}benzamide;
ethyl {[4-{4-[2-fluoro-4-(methylcarbamoyl)phenyl]-1H-pyrrolo[2,3-b]pyridin-2-yl}-3,6-dihydropyridin-1(2H)-yl]sulfonyl}carbamate;
[4-{4-[2-fluoro-4-(methylcarbamoyl)phenyl]-1H-pyrrolo[2,3-b]pyridin-2-yl}-3,6-dihydropyridin-1(2H)-yl]acetic acid;
4-(5-fluoro-2-methoxyphenyl)-2-(1,2,3,3a,4,6a-hexahydrocyclopenta[c]pyrrol-5-yl)-1H-pyrrolo[2,3-b]pyridine;
tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate;
tert-butyl 4-[4-(5-fluoro-2-methoxyphenyl)-1H-pyrrolo[2,3-b]pyridin-2-yl]-2-[(methylsulfonyl)carbamoyl]-2,5-dihydro-1H-pyrrole-1-carboxylate;
2-fluoro-N-methyl-4-[2-(1,2,3,6-tetrahydropyridin-4-yl)-1H-pyrrolo[2,3-b]pyridin-4-yl]benzamide;
4-{4-[3-fluoro-4-(methylcarbamoyl)phenyl]-1H-pyrrolo[2,3-b]pyridin-2-yl}-N-methyl-3,6-dihydropyridine-1(2H)-carboxamide;
4-(2-{1-[2-(dimethylamino)-2-oxoethyl]-1,2,3,6-tetrahydropyridin-4-yl}-1H-pyrrolo[2,3-b]pyridin-4-yl)-2-fluoro-N-methylbenzamide;
4-{2-[1-(2,3-dihydroxypropyl)-1,2,3,6-tetrahydropyridin-4-yl]-1H-pyrrolo[2,3-b]pyridin-4-yl}-2-fluoro-N-methylbenzamide;
4-(5-fluoro-2-methoxyphenyl)-5-methoxy-2-[1-(methylsulfonyl)-1,2,3,6-tetrahydropyridin-4-yl]-1H-pyrrolo[2,3-b]pyridine;
N-{4-[4-(5-fluoro-2-methoxyphenyl)-1H-pyrrolo[2,3-b]pyridin-2-yl]cyclohex-3-en-1-yl}serine;
3-[4-(5-fluoro-2-methoxyphenyl)-1H-pyrrolo[2,3-b]pyridin-2-yl]cyclohex-3-ene-1-carboxylic acid;
{4-[4-(5-fluoro-2-methoxyphenyl)-1H-pyrrolo[2,3-b]pyridin-2-yl]-1,2,3,6-tetrahydropyridin-2-yl}methanol;
7-[4-(5-fluoro-2-methoxyphenyl)-1H-pyrrolo[2,3-b]pyridin-2-yl]-3-oxa-9-azabicyclo[3.3.1]non-6-ene;
7-[4-(5-fluoro-2-methoxyphenyl)-1H-pyrrolo[2,3-b]pyridin-2-yl]-9-(methylsulfonyl)-3-oxa-9-azabicyclo[3.3.1]non-6-ene;
ethyl ({7-[4-(5-fluoro-2-methoxyphenyl)-1H-pyrrolo[2,3-b]pyridin-2-yl]-3-oxa-9-azabicyclo[3.3.1]non-6-en-9-yl}sulfonyl)carbamate;
2-{7-[4-(5-fluoro-2-methoxyphenyl)-1H-pyrrolo[2,3-b]pyridin-2-yl]-3-oxa-9-azabicyclo[3.3.1]non-6-en-9-yl}-N,N-dimethylacetamide;
N-{4-[4-(5-fluoro-2-methoxyphenyl)-1H-pyrrolo[2,3-b]pyridin-2-yl]cyclohex-3-en-1-yl}-L-isoleucine;
ethyl {[4-{4-[3-fluoro-4-(methylcarbamoyl)phenyl]-1H-pyrrolo[2,3-b]pyridin-2-yl}-3,6-dihydropyridin-1(2H)-yl]sulfonyl}carbamate;
4-(3-fluoro-2-methoxyphenyl)-2-[1-(methylsulfonyl)-1,2,3,6-tetrahydropyridin-4-yl]-1H-pyrrolo[2,3-b]pyridine;
4-[4-(3-fluoro-2-methoxyphenyl)-1H-pyrrolo[2,3-b]pyridin-2-yl]-N-methyl-3,6-dihydropyridine-1(2H)-carboxamide;
methyl 4-[4-(5-fluoro-2-methoxyphenyl)-1H-pyrrolo[2,3-b]pyridin-2-yl]-2,5-dihydro-1H-pyrrole-2-carboxylate;
1-{4-[4-(5-fluoro-2-methoxyphenyl)-1H-pyrrolo[2,3-b]pyridin-2-yl]-3,6-dihydropyridin-1(2H)-yl}-3-(3-hydroxyazetidin-1-yl)propane-1,3-dione;
[(2S)-4-[4-(5-fluoro-2-methoxyphenyl)-1H-pyrrolo[2,3-b]pyridin-2-yl]-1-(methylsulfonyl)-2,5-dihydro-1H-pyrrol-2-yl]methanol;
ethyl {[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]sulfonyl}carbamate;
2-({4-[4-(5-fluoro-2-methoxyphenyl)-1H-pyrrolo[2,3-b]pyridin-2-yl]-3,6-dihydropyridin-1(2H)-yl}sulfonyl)-1-(3-hydroxyazetidin-1-yl)ethanone;
{(2S)-4-[4-(5-fluoro-2-methoxyphenyl)-1H-pyrrolo[2,3-b]pyridin-2-yl]-2,5-dihydro-1H-pyrrol-2-yl}methanol;
8-[4-(5-fluoro-2-methoxyphenyl)-1H-pyrrolo[2,3-b]pyridin-2-yl]-1,3-diazaspiro[4.5]dec-7-ene-2,4-dione;
1-amino-4-[4-(5-fluoro-2-methoxyphenyl)-1H-pyrrolo[2,3-b]pyridin-2-yl]cyclohex-3-ene-1-carboxylic acid;
2-(2-azaspiro[3.3]hept-6-yl)-4-(5-fluoro-2-methoxyphenyl)-1H-pyrrolo[2,3-b]pyridine;
4-(5-fluoro-2-methoxyphenyl)-5-methoxy-2-(1,2,3,6-tetrahydropyridin-4-yl)-1H-pyrrolo[2,3-b]pyridine;
4-(5-fluoro-2-methoxyphenyl)-2-(1-{[1-(methylsulfonyl)piperidin-4-yl]sulfonyl}-1,2,3,6-tetrahydropyridin-4-yl)-1H-pyrrolo[2,3-b]pyridine;
N-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]methanesulfonamide;
{4-[4-(5-fluoro-2-methoxyphenyl)-1H-pyrrolo[2,3-b]pyridin-2-yl]-1-(methylsulfonyl)-1,2,3,6-tetrahydropyridin-2-yl}methanol;
ethyl ({4-[4-(5-fluoro-2-methoxyphenyl)-1H-pyrrolo[2,3-b]pyridin-2-yl]-2-(hydroxymethyl)-3,6-dihydropyridin-1(2H)-yl}sulfonyl)carbamate;
2-{4-[4-(5-fluoro-2-methoxyphenyl)-1H-pyrrolo[2,3-b]pyridin-2-yl]-2-(hydroxymethyl)-3,6-dihydropyridin-1(2H)-yl}-N,N-dimethylacetamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-[4-(5-fluoro-2-methoxyphenyl)-1H-pyrrolo[2,3-b]pyridin-2-yl]-N,N-dimethyl-2,5-dihydro-1H-pyrrole-2-carboxamide;
2-(4-{4-[4-(5-fluoro-2-methoxyphenyl)-1H-pyrrolo[2,3-b]pyridin-2-yl]-3,6-dihydropyridin-1(2H)-yl}piperidin-1-yl)-N,N-dimethylacetamide;

N-{4-[4-(2,3-difluorophenyl)-1H-pyrrolo[2,3-b]pyridin-2-yl]cyclohex-3-en-1-yl}glycine;
1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone;
4-(5-fluoro-2-methoxyphenyl)-2-(1-{[1-(methylsulfonyl)azetidin-3-yl]sulfonyl}-1,2,3,6-tetrahydropyridin-4-yl)-1H-pyrrolo[2,3-b]pyridine;
4-(5-fluoro-2-methoxyphenyl)-2-(2,3,6,7-tetrahydro-1H-azepin-4-yl)-1H-pyrrolo[2,3-b]pyridine;
3-(2-{4-[4-(5-fluoro-2-methoxyphenyl)-1H-pyrrolo[2,3-b]pyridin-2-yl]-3,6-dihydropyridin-1(2H)-yl}-2-oxoethyl)imidazolidine-2,4-dione;
({4-[4-(5-fluoro-2-methoxyphenyl)-1H-pyrrolo[2,3-b]pyridin-2-yl]-3,6-dihydropyridin-1(2H)-yl}sulfonyl)acetonitrile;
propan-2-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-(5-fluoro-2-methoxyphenyl)-2-[2-(methylsulfonyl)-2-azaspiro[3.3]hept-6-yl]-1H-pyrrolo[2,3-b]pyridine;
ethyl ({4-[5-cyano-4-(5-fluoro-2-methoxyphenyl)-1H-pyrrolo[2,3-b]pyridin-2-yl]-3,6-dihydropyridin-1(2H)-yl}sulfonyl)carbamate;
N-[2-(4-fluoro-2-{2-[1-(methylsulfonyl)-1,2,3,6-tetrahydropyridin-4-yl]-1H-pyrrolo[2,3-b]pyridin-4-yl}phenoxy)ethyl]methanesulfonamide;
2-{4-fluoro-2-[2-(1,2,3,6-tetrahydropyridin-4-yl)-1H-pyrrolo[2,3-b]pyridin-4-yl]phenoxy}ethanamine;
N-[4-({4-[4-(5-fluoro-2-methoxyphenyl)-1H-pyrrolo[2,3-b]pyridin-2-yl]-3,6-dihydropyridin-1(2H)-yl}methyl)phenyl]methanesulfonamide;
tert-butyl 4-{4-[5-fluoro-2-(methylamino)phenyl]-1H-pyrrolo[2,3-b]pyridin-2-yl}-3,6-dihydropyridine-1(2H)-carboxylate;
4-fluoro-N-methyl-2-[2-(1,2,3,6-tetrahydropyridin-4-yl)-1H-pyrrolo[2,3-b]pyridin-4-yl]aniline;
1-amino-4-[4-(5-fluoro-2-methoxyphenyl)-1H-pyrrolo[2,3-b]pyridin-2-yl]-N,N-dimethylcyclohex-3-ene-1-carboxamide;
1-(3-{4-[4-(5-fluoro-2-methoxyphenyl)-1H-pyrrolo[2,3-b]pyridin-2-yl]-3,6-dihydropyridin-1(2H)-yl}-3-oxopropanoyl)prolinamide;
N-ethoxy-4-[4-(5-fluoro-2-methoxyphenyl)-1H-pyrrolo[2,3-b]pyridin-2-yl]cyclohex-3-ene-1-carboxamide;
ethyl ({3-[4-(5-fluoro-2-methoxyphenyl)-1H-pyrrolo[2,3-b]pyridin-2-yl]-8-azabicyclo[3.2.1]oct-2-en-8-yl}sulfonyl)carbamate;
4-[4-(5-fluoro-2-methoxyphenyl)-1H-pyrrolo[2,3-b]pyridin-2-yl]-N-(4-methoxybenzyl)cyclohex-3-ene-1-sulfonamide;
methyl 4-[4-(5-fluoro-2-methoxyphenyl)-1H-pyrrolo[2,3-b]pyridin-2-yl]-3,6-dihydro-2H-1,2'-bipyridine-3'-carboxylate;
1-({4-[4-(5-fluoro-2-methoxyphenyl)-1H-pyrrolo[2,3-b]pyridin-2-yl]piperidin-1-yl}acetyl)-L-prolinamide;
1-tert-butyl 2-methyl (2S)-4-{4-[4-(5-fluoro-2-methoxyphenyl)-1H-pyrrolo[2,3-b]pyridin-2-yl]-3,6-dihydropyridin-1(2H)-yl}pyrrolidine-1,2-dicarboxylate;
4-[4-(5-fluoro-2-methoxyphenyl)-1H-pyrrolo[2,3-b]pyridin-2-yl]-3,6-dihydro-2H-1,2'-bipyridine-3'-carboxylic acid;
N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide;
N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)methanesulfonamide;
3-{4-[4-(5-fluoro-2-methoxyphenyl)-1H-pyrrolo[2,3-b]pyridin-2-yl]-3,6-dihydropyridin-1(2H)-yl}-4-hydroxycyclobut-3-ene-1,2-dione;
methyl 4-{4-[4-(5-fluoro-2-methoxyphenyl)-1H-pyrrolo[2,3-b]pyridin-2-yl]-3,6-dihydropyridin-1(2H)-yl}-L-prolinate;
methyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-prolinate;
ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate;
4-[4-(5-fluoro-2-methoxyphenyl)-1H-pyrrolo[2,3-b]pyridin-2-yl]cyclohex-3-ene-1-sulfonamide;
ethyl ({6-[4-(5-fluoro-2-methoxyphenyl)-1H-pyrrolo[2,3-b]pyridin-2-yl]-2-azaspiro[3.3]hept-2-yl}sulfonyl)carbamate;
3-{6-[4-(5-fluoro-2-methoxyphenyl)-1H-pyrrolo[2,3-b]pyridin-2-yl]-2-azaspiro[3.3]hept-2-yl}propane-1,2-diol;
2-{6-[4-(5-fluoro-2-methoxyphenyl)-1H-pyrrolo[2,3-b]pyridin-2-yl]-2-azaspiro[3.3]hept-2-yl}-N,N-dimethylacetamide;
2-({4-[4-(5-fluoro-2-methoxyphenyl)-1H-pyrrolo[2,3-b]pyridin-2-yl]-3,6-dihydropyridin-1(2H)-yl}sulfonyl)-N-(3-hydroxycyclobutyl)acetamide;
4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-proline;
4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylic acid;
2-[1-(azetidin-1-ylsulfonyl)-1,2,3,6-tetrahydropyridin-4-yl]-4-(5-fluoro-2-methoxyphenyl)-1H-pyrrolo[2,3-b]pyridine;
1-({4-[4-(5-fluoro-2-methoxyphenyl)-1H-pyrrolo[2,3-b]pyridin-2-yl]-3,6-dihydropyridin-1(2H)-yl}sulfonyl)azetidine-3-carbonitrile;
2-{1-[(4,4-difluoropiperidin-1-yl)sulfonyl]-1,2,3,6-tetrahydropyridin-4-yl}-4-(5-fluoro-2-methoxyphenyl)-1H-pyrrolo[2,3-b]pyridine;
4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}cyclohex-3-ene-1-carboxamide;
4-[4-(5-fluoro-2-methoxyphenyl)-1H-pyrrolo[2,3-b]pyridin-2-yl]-N-(1-methyl-1H-pyrazol-4-yl)cyclohex-3-ene-1-carboxamide;
4-[4-(5-fluoro-2-methoxyphenyl)-1H-pyrrolo[2,3-b]pyridin-2-yl]-N-(1H-tetrazol-5-ylmethyl)cyclohex-3-ene-1-carboxamide;
N-{4-[4-(5-fluoro-2-methoxyphenyl)-1H-pyrrolo[2,3-b]pyridin-2-yl]cyclohex-3-en-1-yl}-L-norvaline;
4-[4-(5-fluoro-2-methoxyphenyl)-1H-pyrrolo[2,3-b]pyridin-2-yl]-N-(1H-tetrazol-5-ylmethyl)cyclohex-3-en-1-amine;
2-[4-({4-[4-(5-fluoro-2-methoxyphenyl)-1H-pyrrolo[2,3-b]pyridin-2-yl]-3,6-dihydropyridin-1(2H)-yl}sulfonyl)piperidin-1-yl]-N,N-dimethylacetamide;
2-{4-[4-(5-fluoro-2-methoxyphenyl)-1H-pyrrolo[2,3-b]pyridin-2-yl]-3,6-dihydropyridin-1(2H)-yl}-1-[(2R)-2-(hydroxymethyl)pyrrolidin-1-yl]ethanone;
4-(5-fluoro-2-methoxyphenyl)-2-[1-(methylsulfonyl)-2,3,6,7-tetrahydro-1H-azepin-4-yl]-1H-pyrrolo[2,3-b]pyridine;

4-[4-(5-fluoro-2-methoxyphenyl)-1H-pyrrolo[2,3-b]pyridin-2-yl]-N-methyl-2,3,6,7-tetrahydro-1H-azepine-1-carboxamide;

[1-({4-[4-(5-fluoro-2-methoxyphenyl)-1H-pyrrolo[2,3-b]pyridin-2-yl]-3,6-dihydropyridin-1(2H)-yl}carbonyl)-1,2,3,6-tetrahydropyridin-4-yl]boronic acid;

3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione;

N-{4-[4-(5-fluoro-2-methoxyphenyl)-1H-pyrrolo[2,3-b]pyridin-2-yl]cyclohex-3-en-1-yl}methanesulfonamide;

1-{4-[4-(5-fluoro-2-methoxyphenyl)-1H-pyrrolo[2,3-b]pyridin-2-yl]cyclohex-3-en-1-yl}-3-methylurea;

N-{4-[4-(5-fluoro-2-methoxyphenyl)-1H-pyrrolo[2,3-b]pyridin-2-yl]cyclohex-3-en-1-yl}-2-hydroxyacetamide;

2-cyano-N-{4-[4-(5-fluoro-2-methoxyphenyl)-1H-pyrrolo[2,3-b]pyridin-2-yl]cyclohex-3-en-1-yl}acetamide;

4-[4-(5-fluoro-2-methoxyphenyl)-1H-pyrrolo[2,3-b]pyridin-2-yl]-1,2,5,6-tetrahydropyridine-3-carbonitrile;

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetonitrile;

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}cyclohex-3-ene-1-carboxamide;

2-{4-[4-(5-fluoro-2-methoxyphenyl)-1H-pyrrolo[2,3-b]pyridin-2-yl]piperidin-1-yl}-1-(3-methoxyazetidin-1-yl)ethanone;

1-({4-[4-(5-fluoro-2-methoxyphenyl)-1H-pyrrolo[2,3-b]pyridin-2-yl]piperidin-1-yl}acetyl) azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-(3-hydroxy-3-methylazetidin-1-yl)ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]piperidin-1-yl}ethanone;

1-(3-fluoroazetidin-1-yl)-2-{4-[4-(5-fluoro-2-methoxyphenyl)-1H-pyrrolo[2,3-b]pyridin-2-yl]piperidin-1-yl}ethanone;

N-(3-fluorocyclobutyl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]piperidin-1-yl}-1-(3-hydroxypyrrolidin-1-yl)ethanone;

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid;

4-fluoro-2-{2-[1-(methylsulfonyl)-1,2,3,6-tetrahydropyridin-4-yl]-1H-pyrrolo[2,3-b]pyridin-4-yl}aniline;

methyl N-{4-[4-(5-fluoro-2-methoxyphenyl)-1H-pyrrolo[2,3-b]pyridin-2-yl]cyclohex-3-en-1-yl}-3-methyl-L-valinate;

N-cyano-4-[4-(5-fluoro-2-methoxyphenyl)-1H-pyrrolo[2,3-b]pyridin-2-yl]cyclohex-3-ene-1-carboxamide;

2-(3,3-dimethyl-1,2,3,6-tetrahydropyridin-4-yl)-4-(5-fluoro-2-methoxyphenyl)-1H-pyrrolo[2,3-b]pyridine;

2-(methylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-{[({4-[4-(5-fluoro-2-methoxyphenyl)-1H-pyrrolo[2,3-b]pyridin-2-yl]-3,6-dihydropyridin-1(2H)-yl}sulfonyl)carbamoyl]oxy}ethyl acetate;

2-(pyrrolidin-1-yl)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

azetidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-hydroxyethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

N-[2-(3-fluoro-5-{2-[1-(methylsulfonyl)-1,2,3,6-tetrahydropyridin-4-yl]-1H-pyrrolo[2,3-b]pyridin-4-yl}phenoxy)ethyl]methanesulfonamide;

4-[4-(5-fluoro-2-methoxyphenyl)-1H-pyrrolo[2,3-b]pyridin-2-yl]-5,6-dihydropyridin-2(1H)-one;

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)acetamide;

1-{4-[4-(5-fluoro-2-methoxyphenyl)-1H-pyrrolo[2,3-b]pyridin-2-yl]-3,6-dihydropyridin-1(2H)-yl}-3-[2-(hydroxymethyl)pyrrolidin-1-yl]propane-1,3-dione;

cyclopropyl({4-[4-(5-fluoro-2-methoxyphenyl)-1H-pyrrolo[2,3-b]pyridin-2-yl]cyclohex-3-en-1-yl}amino)acetic acid;

2-[3,3-dimethyl-1-(methylsulfonyl)-1,2,3,6-tetrahydropyridin-4-yl]-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N,3,3-trimethyl-3,6-dihydropyridine-1(2H)-carboxamide;

4-[4-(5-fluoro-2-methoxyphenyl)-1H-pyrrolo[2,3-b]pyridin-2-yl]cyclohex-3-en-1-amine;

4-(5-fluoro-2-methoxyphenyl)-2-[(6S)-6-methyl-1,2,3,6-tetrahydropyridin-4-yl]-1H-pyrrolo[2,3-b]pyridine;

N²-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N-methylglycinamide;

tert-butyl N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinate;

N²-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinamide;

N²-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N,N-dimethylglycinamide;

tert-butyl {4-[4-(4-fluoro-2-methoxyphenyl)-1H-pyrrolo[2,3-b]pyridin-2-yl]-3,6-dihydropyridin-1(2H)-yl}acetate;

{4-[4-(5-fluoro-2-methoxyphenyl)-1H-pyrrolo[2,3-b]pyridin-2-yl]-3,3-dimethyl-3,6-dihydropyridin-1(2H)-yl}acetic acid;

4-[4-(5-fluoro-2-methoxyphenyl)-1H-pyrrolo[2,3-b]pyridin-2-yl]cyclohex-3-ene-1-carbonitrile;

2-{4-[4-(5-fluoro-2-methoxyphenyl)-5-methoxy-1H-pyrrolo[2,3-b]pyridin-2-yl]-3,6-dihydropyridin-1(2H)-yl}-N,N-dimethylacetamide;

ethyl ({5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}sulfonyl)carbamate;

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}propane-1,2-diol;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;
2-{4-[4-(4-fluoro-2-methoxyphenyl)-1H-pyrrolo[2,3-b]pyridin-2-yl]-3,6-dihydropyridin-1(2H)-yl}acetamide;
2-{4-[4-(4-fluoro-2-methoxyphenyl)-1H-pyrrolo[2,3-b]pyridin-2-yl]-3,6-dihydropyridin-1(2H)-yl}-N-methylacetamide;
N-{4-[4-(5-fluoro-2-methoxyphenyl)-1H-pyrrolo[2,3-b]pyridin-2-yl]cyclohexyl}-D-valine;
2-{4-[5-fluoro-4-(5-fluoro-2-methoxyphenyl)-1H-pyrrolo[2,3-b]pyridin-2-yl]piperidin-1-yl}acetamide;
4-(5-fluoro-2-methoxyphenyl)-2-{1-[2-(2-methoxyethoxy)ethyl]-1,2,3,6-tetrahydropyridin-4-yl}-1H-pyrrolo[2,3-b]pyridine;
4-[4-(5-fluoro-2-methoxyphenyl)-1H-pyrrolo[2,3-b]pyridin-2-yl]cyclohex-3-en-1-yl methylsulfamate;
2-{4-[4-(5-fluoro-2-methoxyphenyl)-1H-pyrrolo[2,3-b]pyridin-2-yl]-3,6-dihydropyridin-1(2H)-yl}-1-(3-methoxyazetidin-1-yl)ethanone;
1-({4-[4-(5-fluoro-2-methoxyphenyl)-1H-pyrrolo[2,3-b]pyridin-2-yl]-3,6-dihydropyridin-1(2H)-yl}acetyl)azetidine-3-carbonitrile;
1-(3,3-difluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;
2-{4-[4-(5-fluoro-2-methoxyphenyl)-1H-pyrrolo[2,3-b]pyridin-2-yl]-3,6-dihydropyridin-1(2H)-yl}-1-[3-(hydroxymethyl)azetidin-1-yl]ethanone;
2-{4-[4-(5-fluoro-2-methoxyphenyl)-1H-pyrrolo[2,3-b]pyridin-2-yl]-3,6-dihydropyridin-1(2H)-yl}-1-(3-hydroxy-3-methylazetidin-1-yl) ethanone;
1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;
2-{4-[4-(5-fluoro-2-methoxyphenyl)-1H-pyrrolo[2,3-b]pyridin-2-yl]-3,6-dihydropyridin-1(2H)-yl}-1-[3-(methoxymethyl)-3-methylazetidin-1-yl]ethanone;
1-[3-fluoro-3-(methoxymethyl)pyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;
N-cyclobutyl-2-{4-[4-(5-fluoro-2-methoxyphenyl)-1H-pyrrolo[2,3-b]pyridin-2-yl]-3,6-dihydropyridin-1(2H)-yl}acetamide;
1-(3-fluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;
2-{4-[4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;
N-(3-fluorocyclobutyl)-2-{4-[4-(5-fluoro-2-methoxyphenyl)-1H-pyrrolo[2,3-b]pyridin-2-yl]-3,6-dihydropyridin-1(2H)-yl}acetamide;
2-{4-[4-(5-fluoro-2-methoxyphenyl)-1H-pyrrolo[2,3-b]pyridin-2-yl]-3,6-dihydropyridin-1(2H)-yl}-1-(3-hydroxypyrrolidin-1-yl)ethanone;
2-{4-[4-(5-fluoro-2-methoxyphenyl)-1H-pyrrolo[2,3-b]pyridin-2-yl]-3,3-dimethyl-3,6-dihydropyridin-1(2H)-yl}-N,N-dimethylacetamide;
3-{4-[4-(5-fluoro-2-methoxyphenyl)-1H-pyrrolo[2,3-b]pyridin-2-yl]-3,3-dimethyl-3,6-dihydropyridin-1(2H)-yl}propane-1,2-diol;
1-({4-[4-(5-fluoro-2-methoxyphenyl)-1H-pyrrolo[2,3-b]pyridin-2-yl]piperidin-1-yl}acetyl)-L-proline;
1-({4-[4-(5-fluoro-2-methoxyphenyl)-1H-pyrrolo[2,3-b]pyridin-2-yl]-3,6-dihydropyridin-1(2H)-yl}acetyl)-L-proline;
2-{4-[4-(5-fluoro-2-methoxyphenyl)-1H-pyrrolo[2,3-b]pyridin-2-yl]piperidin-1-yl}-N-(methylsulfonyl)acetamide;
1-[(3S,4S)-3,4-dihydroxypyrrolidin-1-yl]-2-{4-[4-(5-fluoro-2-methoxyphenyl)-1H-pyrrolo[2,3-b]pyridin-2-yl]piperidin-1-yl}ethanone;
1-[(3S,4S)-3,4-dihydroxypyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;
N-{4-[4-(5-fluoro-2-methoxyphenyl)-1H-pyrrolo[2,3-b]pyridin-2-yl]cyclohex-3-en-1-yl}-L-serine;
5-[4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
4-(5-fluoro-2-methoxyphenyl)-2-[4-(piperazin-1-yl)cyclohex-1-en-1-yl]-1H-pyrrolo[2,3-b]pyridine;
$N^2$-{4-[4-(5-fluoro-2-methoxyphenyl)-1H-pyrrolo[2,3-b]pyridin-2-yl]cyclohex-3-en-1-yl}-N,N-dimethyl-D-valinamide;
(4R)-1-{4-[4-(5-fluoro-2-methoxyphenyl)-1H-pyrrolo[2,3-b]pyridin-2-yl]cyclohex-3-en-1-yl}-4-hydroxy-L-proline;
N-{4-[4-(5-fluoro-2-methoxyphenyl)-1H-pyrrolo[2,3-b]pyridin-2-yl]cyclohex-3-en-1-yl}-L-valine;
2-{4-[4-(2-methoxyphenyl)-1H-pyrrolo[2,3-b]pyridin-2-yl]piperidin-1-yl}-N-methylacetamide;
{4-[4-(2-methoxyphenyl)-1H-pyrrolo[2,3-b]pyridin-2-yl]piperidin-1-yl}acetic acid;
2-[(6S)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(6R)-6-methyl-1,2,3,6-tetrahydropyridin-4-yl]-1H-pyrrolo[2,3-b]pyridine;
4-(5-fluoro-2-methoxyphenyl)-2-[(2S)-2-methyl-1-(methylsulfonyl)piperidin-4-yl]-1H-pyrrolo[2,3-b]pyridine;
({4-[4-(5-fluoro-2-methoxyphenyl)-1H-pyrrolo[2,3-b]pyridin-2-yl]cyclohex-3-en-1-yl}oxy)acetic acid;
N-{4-[4-(5-fluoro-2-methoxyphenyl)-1H-pyrrolo[2,3-b]pyridin-2-yl]cyclohex-3-en-1-yl}-L-threonine;
2-{1-[(1,1-dioxidothiomorpholin-4-yl)sulfonyl]-1,2,3,6-tetrahydropyridin-4-yl}-4-(5-fluoro-2-methoxyphenyl)-1H-pyrrolo[2,3-b]pyridine;
4-(5-fluoro-2-methoxyphenyl)-2-{1-[(4-methylpiperazin-1-yl)sulfonyl]-1,2,3,6-tetrahydropyridin-4-yl}-1H-pyrrolo[2,3-b]pyridine;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-4-carboxylate;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)prolinate;
ethyl {4-[4-(5-fluoro-2-methoxyphenyl)-1H-pyrrolo[2,3-b]pyridin-2-yl]-3,6-dihydropyridin-1(2H)-yl}acetate;
propan-2-yl {4-[4-(5-fluoro-2-methoxyphenyl)-1H-pyrrolo[2,3-b]pyridin-2-yl]-3,6-dihydropyridin-1(2H)-yl}acetate;
4-(2-ethoxy-4,5-difluorophenyl)-2-(1,2,3,6-tetrahydropyridin-4-yl)-1H-pyrrolo[2,3-b]pyridine;
2-hydroxy-2-methylpropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
(2,2-dimethyl-1,3-dioxolan-4-yl)methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
tetrahydro-2H-pyran-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-(2-ethoxy-4,5-difluorophenyl)-2-[1-(methylsulfonyl)-1,2,3,6-tetrahydropyridin-4-yl]-1H-pyrrolo[2,3-b]pyridine;

4-[4-(2-ethoxy-4,5-difluorophenyl)-1H-pyrrolo[2,3-b]pyridin-2-yl]-N-methyl-3,6-dihydropyridine-1(2H)-carboxamide;

2-{4-[5-fluoro-4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;

{(2S)-4-[4-(5-fluoro-2-methoxyphenyl)-1H-pyrrolo[2,3-b]pyridin-2-yl]-1,2,3,6-tetrahydropyridin-2-yl}methanol;

{(2S)-4-[4-(5-fluoro-2-methoxyphenyl)-1H-pyrrolo[2,3-b]pyridin-2-yl]-1,2,5,6-tetrahydropyridin-2-yl}methanol;

2-{4-[4-(4,5-difluoro-2-methoxyphenyl)-1H-pyrrolo[2,3-b]pyridin-2-yl]piperidin-1-yl}-N-methylacetamide;

2-{4-[4-(4,5-difluoro-2-methoxyphenyl)-1H-pyrrolo[2,3-b]pyridin-2-yl]piperidin-1-yl}-N,N-dimethylacetamide;

2-{5-[4-(5-fluoro-2-methoxyphenyl)-1H-pyrrolo[2,3-b]pyridin-2-yl]-2,3,4,7-tetrahydro-1H-azepin-1-yl}acetamide;

2-{5-[4-(5-fluoro-2-methoxyphenyl)-1H-pyrrolo[2,3-b]pyridin-2-yl]-2,3,4,7-tetrahydro-1H-azepin-1-yl}-N,N-dimethylacetamide;

(1 S,2S,3R,4R)-3-[({4-[4-(4,5-difluoro-2-methoxyphenyl)-1H-pyrrolo[2,3-b]pyridin-2-yl]-3,6-dihydropyridin-1(2H)-yl}acetyl)amino]bicyclo[2.2.1]hept-5-ene-2-carboxamide;

{4-[4-(5-fluoro-2-methoxyphenyl)-1H-pyrrolo[2,3-b]pyridin-2-yl]cyclohex-3-en-1-yl][(2S)-2-(hydroxymethyl)pyrrolidin-1-yl]methanone;

2-{4-[4-(4-fluoro-2-methoxyphenyl)-1H-pyrrolo[2,3-b]pyridin-2-yl]piperidin-1-yl}acetamide;

2-{4-[4-(4-fluoro-2-methoxyphenyl)-1H-pyrrolo[2,3-b]pyridin-2-yl]piperidin-1-yl}-N-methylacetamide;

4-(5-fluoro-2-methoxyphenyl)-2-(octahydrocyclopenta[c]pyrrol-5-yl)-1H-pyrrolo[2,3-b]pyridine;

1-{4-[5-fluoro-4-(5-fluoro-2-methoxyphenyl)-1H-pyrrolo[2,3-b]pyridin-2-yl]piperidin-1-yl}-2-hydroxyethanone;

pyrrolidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

piperidin-4-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

piperidin-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

pyrrolidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2,3-dihydroxypropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

methyl {4-[4-(2-methoxyphenyl)-1H-pyrrolo[2,3-b]pyridin-2-yl]piperidin-1-yl}acetate;

1-[(2S)-2-(hydroxymethyl)pyrrolidin-1-yl]-2-{4-[4-(2-methoxyphenyl)-1H-pyrrolo[2,3-b]pyridin-2-yl]piperidin-1-yl}ethanone;

(2R)-2-({4-[4-(5-fluoro-2-methoxyphenyl)-1H-pyrrolo[2,3-b]pyridin-2-yl]cyclohex-3-en-1-yl}amino)-1-(3-hydroxyazetidin-1-yl)-3-methylbutan-1-one;

1-{4-[4-(5-fluoro-2-methoxyphenyl)-1H-pyrrolo[2,3-b]pyridin-2-yl]cyclohex-3-en-1-yl}-N,N-dimethyl-L-prolinamide;

(2R)-({4-[4-(5-fluoro-2-methoxyphenyl)-1H-pyrrolo[2,3-b]pyridin-2-yl]cyclohex-3-en-1-yl}amino)(phenyl)acetic acid;

4-(5-fluoro-2-methoxyphenyl)-2-[3-(methylsulfonyl)-3-azabicyclo[4.1.0]hept-6-yl]-1H-pyrrolo[2,3-b]pyridine;

4-(5-fluoro-2-methoxyphenyl)-2-[4-(1H-tetrazol-5-yl)cyclohex-1-en-1-yl]-1H-pyrrolo[2,3-b]pyridine;

4-[4-(5-fluoro-2-methoxyphenyl)-1H-pyrrolo[2,3-b]pyridin-2-yl]cyclohex-3-en-1-yl tert-butylcarbamate;

2-{4-[4-(5-fluoro-2-methoxyphenyl)-5-methoxy-1H-pyrrolo[2,3-b]pyridin-2-yl]-3,6-dihydropyridin-1(2H)-yl}-1-[(2S)-2-(hydroxymethyl)pyrrolidin-1-yl]ethanone;

2-{4-[4-(4,5-difluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;

2-{(2S)-4-[4-(5-fluoro-2-methoxyphenyl)-1H-pyrrolo[2,3-b]pyridin-2-yl]-2-methylpiperidin-1-yl}-N,N-dimethylacetamide;

4,4,4-trifluoro-2-{4-[4-(5-fluoro-2-methoxyphenyl)-1H-pyrrolo[2,3-b]pyridin-2-yl]-3,6-dihydropyridin-1(2H)-yl}butanoic acid;

2-{4-[4-(5-fluoro-2-methoxyphenyl)-1H-pyrrolo[2,3-b]pyridin-2-yl]-3,6-dihydropyridin-1(2H)-yl}-N,N-dimethyl-2-oxoethanesulfonamide;

2-{4-[4-(5-fluoro-2-methoxyphenyl)-1H-pyrrolo[2,3-b]pyridin-2-yl]piperidin-1-yl}-N-methyl-2-oxoethanesulfonamide;

2-{4-[4-(5-fluoro-2-methoxyphenyl)-1H-pyrrolo[2,3-b]pyridin-2-yl]piperidin-1-yl}-N,N-dimethyl-2-oxoethanesulfonamide;

1-{4-[4-(5-fluoro-2-methoxyphenyl)-1H-pyrrolo[2,3-b]pyridin-2-yl]-3,6-dihydropyridin-1(2H)-yl}-1-oxopropane-2-sulfonamide;

ethyl {4-[4-(5-fluoro-2-methoxyphenyl)-1H-pyrrolo[2,3-b]pyridin-2-yl]-3,6-dihydropyridin-1(2H)-yl}(phenyl)acetate;

ethyl 2-{4-[4-(5-fluoro-2-methoxyphenyl)-1H-pyrrolo[2,3-b]pyridin-2-yl]-3,6-dihydropyridin-1(2H)-yl}-1,3-thiazole-5-carboxylate;

tert-butyl 3-{4-[4-(5-fluoro-2-methoxyphenyl)-1H-pyrrolo[2,3-b]pyridin-2-yl]-3,6-dihydropyridin-1(2H)-yl}pyrrolidine-1-carboxylate;

ethyl {[(6S)-4-[4-(5-fluoro-2-methoxyphenyl)-1H-pyrrolo[2,3-b]pyridin-2-yl]-6-methyl-3,6-dihydropyridin-1(2H)-yl]sulfonyl}carbamate;

2-({4-[4-(5-fluoro-2-methoxyphenyl)-1H-pyrrolo[2,3-b]pyridin-2-yl]cyclohex-3-en-1-yl}oxy)ethanol;

2-{4-[4-(5-fluoro-2-methoxyphenyl)-1H-pyrrolo[2,3-b]pyridin-2-yl]piperidin-1-yl}propanoic acid;

{4-[4-(5-fluoro-2-methoxyphenyl)-1H-pyrrolo[2,3-b]pyridin-2-yl]-3,6-dihydropyridin-1(2H)-yl}(phenyl)acetic acid;

4-(5-fluoro-2-methoxyphenyl)-2-[1-(pyrrolidin-3-yl)-1,2,3,6-tetrahydropyridin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]piperidin-1-yl}-3-oxopropanenitrile;

4-fluoro-2-[2-(1,2,3,6-tetrahydropyridin-4-yl)-1H-pyrrolo[2,3-b]pyridin-4-yl]benzamide;

2-aminoethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

azetidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-(dimethylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-(2,2-dimethyl-1,2,3,6-tetrahydropyridin-4-yl)-4-(5-fluoro-2-methoxyphenyl)-1H-pyrrolo[2,3-b]pyridine;

5-({4-[4-(5-fluoro-2-methoxyphenyl)-1H-pyrrolo[2,3-b]pyridin-2-yl]piperidin-1-yl}methyl)-2,4-dihydro-3H-1,2,4-triazol-3-one;

4-(5-fluoro-2-methoxyphenyl)-2-{1-[1-(methylsulfonyl)pyrrolidin-3-yl]-1,2,3,6-tetrahydropyridin-4-yl}-1H-pyrrolo[2,3-b]pyridine;

2-{4-[4-(5-fluoro-2-methoxyphenyl)-1H-pyrrolo[2,3-b]pyridin-2-yl]piperidin-1-yl}-N-(propan-2-ylsulfonyl)acetamide;

ethyl 2-{4-[4-(5-fluoro-2-methoxyphenyl)-1H-pyrrolo[2,3-b]pyridin-2-yl]piperidin-1-yl}-1,3-thiazole-5-carboxylate;

methyl (4-{4-[4-(5-fluoro-2-methoxyphenyl)-1H-pyrrolo[2,3-b]pyridin-2-yl]-3,6-dihydropyridin-1(2H)-yl}cyclohexyl)acetate;

3-{4-[4-(5-fluoro-2-methoxyphenyl)-1H-pyrrolo[2,3-b]pyridin-2-yl]-3,6-dihydropyridin-1(2H)-yl}-1-methylpyrrolidin-2-one;

4-{4-[4-(5-fluoro-2-methoxyphenyl)-1H-pyrrolo[2,3-b]pyridin-2-yl]-3,6-dihydropyridin-1(2H)-yl}pyrrolidin-2-one;

2-{4-[4-(5-fluoro-2-methoxyphenyl)-1H-pyrrolo[2,3-b]pyridin-2-yl]piperidin-1-yl}-1,3-thiazole-5-carboxylic acid;

(2 S)-cyclohexyl({4-[4-(5-fluoro-2-methoxyphenyl)-1H-pyrrolo[2,3-b]pyridin-2-yl]cyclohex-3-en-1-yl}amino)acetic acid;

N-{4-[5-fluoro-4-(5-fluoro-2-methoxyphenyl)-1H-pyrrolo[2,3-b]pyridin-2-yl]cyclohex-3-en-1-yl}-D-valine;

N-{4-[5-fluoro-4-(5-fluoro-2-methoxyphenyl)-1H-pyrrolo[2,3-b]pyridin-2-yl]cyclohex-3-en-1-yl}-3-methyl-L-valine;

{4-[5-fluoro-4-(5-fluoro-2-methoxyphenyl)-1H-pyrrolo[2,3-b]pyridin-2-yl]piperidin-1-yl}acetic acid;

methyl 1-({4-[4-(5-fluoro-2-methoxyphenyl)-1H-pyrrolo[2,3-b]pyridin-2-yl]cyclohex-3-en-1-yl}carbonyl)prolinate;

(4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;

3-{4-[4-(5-fluoro-2-methoxyphenyl)-1H-pyrrolo[2,3-b]pyridin-2-yl]piperidin-1-yl}-1-methylpyrrolidin-2-one;

N-cyano-4-[5-fluoro-4-(5-fluoro-2-methoxyphenyl)-1H-pyrrolo[2,3-b]pyridin-2-yl]-3,6-dihydropyridine-1(2H)-carboxamide;

4-(5-fluoro-2-methoxyphenyl)-2-(1-{[2-(2-methoxyethoxy)ethyl]sulfonyl}-1,2,3,6-tetrahydropyridin-4-yl)-1H-pyrrolo[2,3-b]pyridine;

N-cyano-2-{4-[4-(5-fluoro-2-methoxyphenyl)-1H-pyrrolo[2,3-b]pyridin-2-yl]piperidin-1-yl}acetamide;

{(2R)-4-[4-(5-fluoro-2-methoxyphenyl)-1H-pyrrolo[2,3-b]pyridin-2-yl]-1,2,5,6-tetrahydropyridin-2-yl}methanol;

{(2R)-4-[4-(5-fluoro-2-methoxyphenyl)-1H-pyrrolo[2,3-b]pyridin-2-yl]-1,2,3,6-tetrahydropyridin-2-yl}methanol;

ethyl ({4-[5-fluoro-4-(5-fluoro-2-methoxyphenyl)-1H-pyrrolo[2,3-b]pyridin-2-yl]piperidin-1-yl}sulfonyl)carbamate;

2-{4-[5-fluoro-4-(5-fluoro-2-methoxyphenyl)-1H-pyrrolo[2,3-b]pyridin-2-yl]piperidin-1-yl}-N-(2-hydroxyethyl)-N-methylacetamide;

4-[4-(5-fluoro-2-methoxyphenyl)-1H-pyrrolo[2,3-b]pyridin-2-yl]cyclohex-3-en-1-yl)[(3-hydroxyazetidin-1-yl)sulfonyl]carbamate;

4-(5-fluoro-2-methoxyphenyl)-2-{1-[(2-methoxyethyl)sulfonyl]-1,2,3,6-tetrahydropyridin-4-yl}-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}-2-(2-methoxyethoxy)ethanesulfonamide;

tert-butyl 3-{4-[4-(5-fluoro-2-methoxyphenyl)-1H-pyrrolo[2,3-b]pyridin-2-yl]-3,6-dihydropyridin-1(2H)-yl}cyclobutanecarboxylate;

3-{4-[4-(5-fluoro-2-methoxyphenyl)-1H-pyrrolo[2,3-b]pyridin-2-yl]-3,6-dihydropyridin-1(2H)-yl}cyclobutanecarboxylic acid;

4-(5-fluoro-2-methoxyphenyl)-2-[2-(methylsulfonyl)octahydrocyclopenta[c]pyrrol-5-yl]-1H-pyrrolo[2,3-b]pyridine;

[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]acetic acid;

$N^2$-{4-[4-(5-fluoro-2-methoxyphenyl)-1H-pyrrolo[2,3-b]pyridin-2-yl]cyclohex-3-en-1-yl}-N-methyl-D-valinamide;

N-{4-[4-(5-fluoro-2-methoxyphenyl)-1H-pyrrolo[2,3-b]pyridin-2-yl]cyclohex-3-en-1-yl}-L-phenylalanine;

N-{4-[4-(5-fluoro-2-methoxyphenyl)-1H-pyrrolo[2,3-b]pyridin-2-yl]cyclohex-3-en-1-yl}-L-tyrosine;

$N^2$-{4-[4-(5-fluoro-2-methoxyphenyl)-1H-pyrrolo[2,3-b]pyridin-2-yl]cyclohex-3-en-1-yl}-L-valinamide;

$N^2$-{4-[4-(5-fluoro-2-methoxyphenyl)-1H-pyrrolo[2,3-b]pyridin-2-yl]cyclohex-3-en-1-yl}-N,3-dimethyl-L-valinamide;

(2S)-({4-[4-(5-fluoro-2-methoxyphenyl)-1H-pyrrolo[2,3-b]pyridin-2-yl]cyclohex-3-en-1-yl}amino)(phenyl)acetic acid;

2-[1-(cyanoacetyl)-1,2,3,6-tetrahydropyridin-4-yl]-4-(5-fluoro-2-methoxyphenyl)-1H-pyrrolo[2,3-b]pyridine-5-carbonitrile;

4-(5-fluoro-2-methoxyphenyl)-2-(2-{[2-(2-methoxyethoxy)ethyl]sulfonyl}-1,2,3,3a,4,6a-hexahydrocyclopenta[c]pyrrol-5-yl)-1H-pyrrolo[2,3-b]pyridine;

(9aR)-8-[4-(5-fluoro-2-methoxyphenyl)-1H-pyrrolo[2,3-b]pyridin-2-yl]-1,6,7,9a-tetrahydropyrido[2,1-c][1,4]oxazin-3(4H)-one;

7-[4-(5-fluoro-2-methoxyphenyl)-1H-pyrrolo[2,3-b]pyridin-2-yl]-1,5,6,8a-tetrahydro[1,3]oxazolo[3,4-a]pyridin-3-one;

2-{4-[4-(5-fluoro-2-methoxyphenyl)-1H-pyrrolo[2,3-b]pyridin-2-yl]piperidin-1-yl}-N-(2-methoxyethyl)-N-methylacetamide;

{4-[4-(5-fluoro-2-methoxyphenyl)-1H-pyrrolo[2,3-b]pyridin-2-yl]piperidin-1-yl}(phenyl)acetic acid;

2-{4-[5-cyano-4-(5-fluoro-2-methoxyphenyl)-1H-pyrrolo[2,3-b]pyridin-2-yl]-3,6-dihydropyridin-1(2H)-yl}acetamide;

N-(3-fluorocyclobutyl)-4-[4-(5-fluoro-2-methoxyphenyl)-1H-pyrrolo[2,3-b]pyridin-2-yl]-2,5-dihydro-1H-pyrrole-2-carboxamide;

4-(5-fluoro-2-methoxyphenyl)-2-[(2R)-2-methyl-1,2,3,6-tetrahydropyridin-4-yl]-1H-pyrrolo[2,3-b]pyridine-4-(5-fluoro-2-methoxyphenyl)-2-[(6R)-6-methyl-1,2,3,6-tetrahydropyridin-4-yl]-1H-pyrrolo[2,3-b]pyridine (1:1);

2-{4-[4-(5-fluoro-2-methoxyphenyl)-1H-pyrrolo[2,3-b]pyridin-2-yl]-6,6-dimethyl-3,6-dihydropyridin-1(2H)-yl}-N,N-dimethylacetamide;

methyl 4-[4-(5-fluoro-2-methoxyphenyl)-1H-pyrrolo[2,3-b]pyridin-2-yl]-1-(methylcarbamoyl)-2,5-dihydro-1H-pyrrole-2-carboxylate;

4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile;

5-[5-cyano-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-2-{4-[4-(5-fluoro-2-methoxyphenyl)-1H-pyrrolo[2,3-b]pyridin-2-yl]-3,6-dihydropyridin-1(2H)-yl}acetamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}ethanone;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-3-carboxylate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxamide;
N-cyano-4-[4-(5-fluoro-2-methoxyphenyl)-1H-pyrrolo[2,3-b]pyridin-2-yl]piperidine-1-carboxamide;
2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide;
N-{5-[4-(5-fluoro-2-methoxyphenyl)-1H-pyrrolo[2,3-b]pyridin-2-yl]-1,2,3,3a,4,6a-hexahydropentalen-2-yl}-D-valine;
methyl 4-[4-(5-fluoro-2-methoxyphenyl)-1H-pyrrolo[2,3-b]pyridin-2-yl]-3,6-dihydropyridine-1(2H)-carboxylate;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine;
2-{4-[5-cyano-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;
2-({4-[4-(5-fluoro-2-methoxyphenyl)-1H-pyrrolo[2,3-b]pyridin-2-yl]cyclohex-3-en-1-yl}oxy)-N,N-dimethylacetamide;
2-({4-[4-(5-fluoro-2-methoxyphenyl)-1H-pyrrolo[2,3-b]pyridin-2-yl]cyclohex-3-en-1-yl}oxy)-1-(morpholin-4-yl)ethanone;
4-[5-fluoro-2-(methylsulfanyl)phenyl]-2-[1-(methylsulfonyl)-1,2,3,6-tetrahydropyridin-4-yl]-1H-pyrrolo[2,3-b]pyridine;
4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-5-carbonitrile;
2-{4-[5-cyano-4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;
2-{4-[5-cyano-4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;
2-{4-[4-(5-fluoro-2-methoxyphenyl)-1H-pyrrolo[2,3-b]pyridin-2-yl]-3,6-dihydropyridin-1(2H)-yl}-N-(2-methoxyethyl)-N-methylacetamide;
methyl (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl (trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl {4-[4-(5-fluoro-2-methoxyphenyl)-1H-pyrrolo[2,3-b]pyridin-2-yl]cyclohex-3-en-1-yl}acetate;
{4-[4-(5-fluoro-2-methoxyphenyl)-1H-pyrrolo[2,3-b]pyridin-2-yl]cyclohex-3-en-1-yl}acetic acid;
(4-{4-[4-(5-fluoro-2-methoxyphenyl)-1H-pyrrolo[2,3-b]pyridin-2-yl]piperidin-1-yl}cyclohexyl)acetic acid;
methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate;
N-{4-[4-(5-fluoro-2-methoxyphenyl)-1H-pyrrolo[2,3-b]pyridin-2-yl]cyclohex-3-en-1-yl}-L-leucine;
4-(5-fluoro-2-methoxyphenyl)-2-[(6R)-6-methyl-1-(methylsulfonyl)-1,2,3,6-tetrahydropyridin-4-yl]-1H-pyrrolo[2,3-b]pyridine;
2-[(6R)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(2R)-2-methyl-1-(methylsulfonyl)-1,2,3,6-tetrahydropyridin-4-yl]-1H-pyrrolo[2,3-b]pyridine;
2-[(2R)-4-[4-(5-fluoro-2-methoxyphenyl)-1H-pyrrolo[2,3-b]pyridin-2-yl]-2-methyl-3,6-dihydropyridin-1(2H)-yl]-N,N-dimethylacetamide;
{4-[4-(5-fluoro-2-methoxyphenyl)-1H-pyrrolo[2,3-b]pyridin-2-yl]cyclohex-3-en-1-yl}(3-hydroxyazetidin-1-yl)methanone;
2-{4-[5-fluoro-4-(5-fluoro-2-methoxyphenyl)-1H-pyrrolo[2,3-b]pyridin-2-yl]piperidin-1-yl}-N-methyl-2-oxoethanesulfonamide;
{4-[5-cyano-4-(5-fluoro-2-methoxyphenyl)-1H-pyrrolo[2,3-b]pyridin-2-yl]piperidin-1-yl}acetic acid;
2-[1-(cyanoacetyl)piperidin-4-yl]-4-(5-fluoro-2-methoxyphenyl)-1H-pyrrolo[2,3-b]pyridine-5-carbonitrile;
4-(5-fluoro-2-methoxyphenyl)-2-{1-[2-(3-hydroxyazetidin-1-yl)-2-oxoethyl]piperidin-4-yl}-1H-pyrrolo[2,3-b]pyridine-5-carbonitrile;
4-[5-fluoro-2-(methylsulfinyl)phenyl]-2-[1-(methylsulfonyl)-1,2,3,6-tetrahydropyridin-4-yl]-1H-pyrrolo[2,3-b]pyridine;
2-{4-[5-fluoro-4-(5-fluoro-2-methoxyphenyl)-1H-pyrrolo[2,3-b]pyridin-2-yl]piperidin-1-yl}-N-(3-hydroxycyclobutyl)-N-methylacetamide;
2-{4-[5-cyano-4-(5-fluoro-2-methoxyphenyl)-1H-pyrrolo[2,3-b]pyridin-2-yl]piperidin-1-yl}-N-(2-hydroxyethyl)-N-methylacetamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-oxoethanesulfonamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-oxopropane-2-sulfonamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethyl-2-oxoethanesulfonamide;
tert-butyl {5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetate;
2-{4-[4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;
2-{4-[4-(5-fluoro-2-methoxyphenyl)-1H-pyrrolo[2,3-b]pyridin-2-yl]-3,6-dihydropyridin-1(2H)-yl}-1-[(3S)-3-hydroxypyrrolidin-1-yl]ethanone;
4-({4-[4-(5-fluoro-2-methoxyphenyl)-1H-pyrrolo[2,3-b]pyridin-2-yl]-3,6-dihydropyridin-1(2H)-yl}carbonyl)benzoic acid;

3-({4-[4-(5-fluoro-2-methoxyphenyl)-1H-pyrrolo[2,3-b]pyridin-2-yl]-3,6-dihydropyridin-1(2H)-yl}carbonyl)benzoic acid;

tert-butyl (3aS,6aR)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;

tert-butyl (3aR,6aS)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;

(3-{4-[4-(5-fluoro-2-methoxyphenyl)-1H-pyrrolo[2,3-b]pyridin-2-yl]-3,6-dihydropyridin-1(2H)-yl}cyclobutyl)acetic acid;

2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoic acid;

ethyl 5-[4-(5-fluoro-2-methoxyphenyl)-1H-pyrrolo[2,3-b]pyridin-2-yl]-1,2,3,6-tetrahydropyridine-4-carboxylate;

{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

4-(5-fluoro-2-methoxyphenyl)-2-[1-(2,5,8,11-tetraoxatetradecan-14-yl)-1,2,3,6-tetrahydropyridin-4-yl]-1H-pyrrolo[2,3-b]pyridine;

{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

4-(5-fluoro-2-methoxyphenyl)-2-{2-[2-(3-hydroxyazetidin-1-yl)-2-oxoethyl]-1,2,3,3a,4,6a-hexahydrocyclopenta[c]pyrrol-5-yl}-1H-pyrrolo[2,3-b]pyridine-5-carbonitrile;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

(3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]ethanone;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-2-hydroxyethanone;

(3aR,5r,6aS)-N-cyano-5-[4-(5-fluoro-2-methoxyphenyl)-1H-pyrrolo[2,3-b]pyridin-2-yl]hexahydrocyclopenta[c]pyrrole-2(1H)-carboxamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N,N-dimethylacetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]propane-1,2-diol;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]acetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-3-oxopropanenitrile;

4-[4-(5-fluoro-2-methoxyphenyl)-1H-pyrrolo[2,3-b]pyridin-2-yl]cyclohexanecarboxylic acid;

(4-{4-[5-fluoro-4-(5-fluoro-2-methoxyphenyl)-1H-pyrrolo[2,3-b]pyridin-2-yl]piperidin-1-yl}cyclohexyl)acetic acid;

{4-[5-chloro-4-(5-fluoro-2-methoxyphenyl)-1H-pyrrolo[2,3-b]pyridin-2-yl]cyclohex-3-en-1-yl}acetic acid;

2-({4-[4-(5-fluoro-2-methoxyphenyl)-1H-pyrrolo[2,3-b]pyridin-2-yl]-3,6-dihydropyridin-1(2H)-yl}sulfonyl)ethanol;

(3-{4-[4-(5-fluoro-2-methoxyphenyl)-1H-pyrrolo[2,3-b]pyridin-2-yl]-3,6-dihydropyridin-1(2H)-yl}cyclobutyl)(3-hydroxyazetidin-1-yl)methanone;

2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

2-[(6R)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

{5-[4-(5-fluoro-2-methoxyphenyl)-1H-pyrrolo[2,3-b]pyridin-2-yl]-1,2,3,6-tetrahydropyridin-4-yl}methanol;

{4-[4-(5-fluoro-2-methoxyphenyl)-1H-pyrrolo[2,3-b]pyridin-2-yl]-3,6-dihydropyridin-1(2H)-yl}(3-hydroxycyclobutyl)methanone;

4-(5-fluoro-2-methoxyphenyl)-2-[(3R)-3-methyl-1,2,3,6-tetrahydropyridin-4-yl]-1H-pyrrolo[2,3-b]pyridine;

4-(5-fluoro-2-methoxyphenyl)-2-[(3S)-3-methyl-1,2,3,6-tetrahydropyridin-4-yl]-1H-pyrrolo[2,3-b]pyridine;

2-[(3R)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

2-[(3S)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

1-{4-[4-(5-fluoro-2-methoxyphenyl)-1H-pyrrolo[2,3-b]pyridin-2-yl]cyclohex-3-en-1-yl}-N-methyl-L-prolinamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone;

2-[(3aR,5S,6aS)-5-[4-(5-fluoro-2-methoxyphenyl)-1H-pyrrolo[2,3-b]pyridin-2-yl]hexahydrocyclopenta[c]pyrrol-2(1H)-yl]-1-[(2S)-2-(hydroxymethyl)pyrrolidin-1-yl]ethanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(2-hydroxyethyl)-N-methylacetamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(3-hydroxycyclobutyl)-N-methylacetamide;

[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl](3-hydroxycyclobutyl)methanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-methyl-2-oxoethanesulfonamide;

2-(8-azabicyclo[3.2.1]oct-2-en-3-yl)-4-(5-fluoro-2-methoxyphenyl)-1H-pyrrolo[2,3-b]pyridine-5-carbonitrile;

2-(8-azabicyclo[3.2.1]oct-2-en-3-yl)-5-fluoro-4-(5-fluoro-2-methoxyphenyl)-1H-pyrrolo[2,3-b]pyridine;

N-cyano-3-[5-fluoro-4-(5-fluoro-2-methoxyphenyl)-1H-pyrrolo[2,3-b]pyridin-2-yl]-8-azabicyclo[3.2.1]oct-2-ene-8-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

{3-[5-cyano-4-(5-fluoro-2-methoxyphenyl)-1H-pyrrolo[2,3-b]pyridin-2-yl]-8-azabicyclo[3.2.1]oct-2-en-8-yl}acetic acid;

{3-[5-fluoro-4-(5-fluoro-2-methoxyphenyl)-1H-pyrrolo[2,3-b]pyridin-2-yl]-8-azabicyclo[3.2.1]oct-2-en-8-yl}acetic acid;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}acetamide;

{4-[4-(5-fluoro-2-methoxyphenyl)-1H-pyrrolo[2,3-b]pyridin-2-yl]cyclohexyl}acetic acid;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

1-{4-[5-fluoro-4-(5-fluoro-2-methoxyphenyl)-1H-pyrrolo[2,3-b]pyridin-2-yl]cyclohex-3-en-1-yl}-N,N-dimethyl-L-prolinamide;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

4-(5-fluoro-2-methoxyphenyl)-2-(8-{2-[(2S)-2-(hydroxymethyl)pyrrolidin-1-yl]-2-oxoethyl}-8-azabicyclo[3.2.1]oct-2-en-3-yl)-1H-pyrrolo[2,3-b]pyridine-5-carbonitrile;

4-(5-fluoro-2-methoxyphenyl)-2-{8-[2-(3-hydroxyazetidin-1-yl)-2-oxoethyl]-8-azabicyclo[3.2.1]oct-2-en-3-yl}-1H-pyrrolo[2,3-b]pyridine-5-carbonitrile;

{4-[5-cyano-4-(5-fluoro-2-methoxyphenyl)-1H-pyrrolo[2,3-b]pyridin-2-yl]cyclohex-3-en-1-yl}acetic acid;

2-(9-azabicyclo[3.3.1]non-2-en-3-yl)-4-(5-fluoro-2-methoxyphenyl)-1H-pyrrolo[2,3-b]pyridine;

4-(5-fluoro-2-methoxyphenyl)-2-[9-(methylsulfonyl)-9-azabicyclo[3.3.1]non-2-en-3-yl]-1H-pyrrolo[2,3-b]pyridine;

3-[4-(5-fluoro-2-methoxyphenyl)-1H-pyrrolo[2,3-b]pyridin-2-yl]-N-methyl-9-azabicyclo[3.3.1]non-2-ene-9-carboxamide;

2-{3-[4-(5-fluoro-2-methoxyphenyl)-1H-pyrrolo[2,3-b]pyridin-2-yl]-9-azabicyclo[3.3.1]non-2-en-9-yl}-N,N-dimethylacetamide;

3-{3-[4-(5-fluoro-2-methoxyphenyl)-1H-pyrrolo[2,3-b]pyridin-2-yl]-9-azabicyclo[3.3.1]non-2-en-9-yl}-3-oxopropanenitrile;

{3-[4-(5-fluoro-2-methoxyphenyl)-1H-pyrrolo[2,3-b]pyridin-2-yl]-9-azabicyclo[3.3.1]non-2-en-9-yl}(3-hydroxycyclobutyl)methanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(trans-4-hydroxycyclohexyl)acetamide;

4-[4-(4-fluoro-2-methoxyphenyl)-1H-pyrrolo[2,3-b]pyridin-2-yl]cyclohex-3-ene-1-carboxylic acid;

4-[4-(4,5-difluoro-2-methoxyphenyl)-1H-pyrrolo[2,3-b]pyridin-2-yl]cyclohex-3-ene-1-carboxylic acid;

4-[4-(2-methoxyphenyl)-1H-pyrrolo[2,3-b]pyridin-2-yl]cyclohex-3-ene-1-carboxylic acid;

4-[4-(5-fluoro-2-methoxyphenyl)-1H-pyrrolo[2,3-b]pyridin-2-yl]-1-methylcyclohex-3-ene-1-carboxylic acid;

2-{4-[4-(5-fluoro-2-methoxyphenyl)-1H-pyrrolo[2,3-b]pyridin-2-yl]-2,3,6,7-tetrahydro-1H-azepin-1-yl}-N,N-dimethylacetamide;

2-{4-[4-(5-fluoro-2-methoxyphenyl)-1H-pyrrolo[2,3-b]pyridin-2-yl]azepan-1-yl}-N,N-dimethylacetamide;

{4-[4-(5-fluoro-2-methoxyphenyl)-1H-pyrrolo[2,3-b]pyridin-2-yl]-2,3,6,7-tetrahydro-1H-azepin-1-yl}acetic acid;

2-{4-[4-(5-fluoro-2-methoxyphenyl)-1H-pyrrolo[2,3-b]pyridin-2-yl]-2,3,6,7-tetrahydro-1H-azepin-1-yl}-1-(3-hydroxyazetidin-1-yl)ethanone;

tert-butyl 3-{4-[4-(5-fluoro-2-methoxyphenyl)-1H-pyrrolo[2,3-b]pyridin-2-yl]-3,6-dihydropyridin-1(2H)-yl}azetidine-1-carboxylate;

tert-butyl 3-{4-[4-(5-fluoro-2-methoxyphenyl)-1H-pyrrolo[2,3-b]pyridin-2-yl]piperidin-1-yl}azetidine-1-carboxylate;

{4-[5-fluoro-4-(5-fluoro-2-methoxyphenyl)-1H-pyrrolo[2,3-b]pyridin-2-yl]cyclohex-3-en-1-yl}acetic acid;

2-[1-(azetidin-3-yl)-1,2,3,6-tetrahydropyridin-4-yl]-4-(5-fluoro-2-methoxyphenyl)-1H-pyrrolo[2,3-b]pyridine;

2-[1-(azetidin-3-yl)piperidin-4-yl]-4-(5-fluoro-2-methoxyphenyl)-1H-pyrrolo[2,3-b]pyridine;

[3-(benzyloxy)-1,2-oxazol-5-yl]{4-[4-(5-fluoro-2-methoxyphenyl)-1H-pyrrolo[2,3-b]pyridin-2-yl]-3,6-dihydropyridin-1(2H)-yl}methanone;

4-[5-cyano-4-(5-fluoro-2-methoxyphenyl)-1H-pyrrolo[2,3-b]pyridin-2-yl]cyclohex-3-ene-1-carboxylic acid;

4-(5-fluoro-2-methoxyphenyl)-2-{1-[1-(methylsulfonyl)azetidin-3-yl]-1,2,3,6-tetrahydropyridin-4-yl}-1H-pyrrolo[2,3-b]pyridine;

4-(5-fluoro-2-methoxyphenyl)-2-{1-[1-(methylsulfonyl)azetidin-3-yl]piperidin-4-yl}-1H-pyrrolo[2,3-b]pyridine;

2-{4-[4-(5-fluoro-2-methoxyphenyl)-1H-pyrrolo[2,3-b]pyridin-2-yl]-2,3,6,7-tetrahydro-1H-azepin-1-yl}-N-(3-hydroxycyclobutyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-N-(2-hydroxyethyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-1-[(2S)-2-(hydroxymethyl)pyrrolidin-1-yl]ethanone;

4-(5-fluoro-2-methoxyphenyl)-5-methoxy-2-[2-(methylsulfonyl)-1,2,3,3a,4,6a-hexahydrocyclopenta[c]pyrrol-5-yl]-1H-pyrrolo[2,3-b]pyridine;

2-{5-[4-(5-fluoro-2-methoxyphenyl)-5-methoxy-1H-pyrrolo[2,3-b]pyridin-2-yl]-3,3a,4,6a-tetrahydrocyclopenta[c]pyrrol-2(1H)-yl}-N,N-dimethylacetamide;

4-[4-(4,5-difluoro-2-methoxyphenyl)-5-fluoro-1H-pyrrolo[2,3-b]pyridin-2-yl]cyclohex-3-ene-1-carboxylic acid;

4-[5-fluoro-4-(4-fluoro-2-methoxyphenyl)-1H-pyrrolo[2,3-b]pyridin-2-yl]cyclohex-3-ene-1-carboxylic acid;

(4-{4-[4-(5-fluoro-2-methoxyphenyl)-1H-pyrrolo[2,3-b]pyridin-2-yl]cyclohex-3-en-1-yl}piperazin-1-yl)acetic acid;

2-{4-[5-fluoro-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-N-(trans-4-hydroxycyclohexyl)acetamide;

{4-[4-(5-fluoro-2-methoxyphenyl)-1H-pyrrolo[2,3-b]pyridin-2-yl]-3,6-dihydropyridin-1(2H)-yl}(3-hydroxy-1,2-oxazol-5-yl)methanone;

3-{4-[4-(5-fluoro-2-methoxyphenyl)-1H-pyrrolo[2,3-b]pyridin-2-yl]-3,6-dihydropyridin-1(2H)-yl}-N-methylazetidine-1-carboxamide;

3-{4-[4-(5-fluoro-2-methoxyphenyl)-1H-pyrrolo[2,3-b]pyridin-2-yl]piperidin-1-yl}-N-methylazetidine-1-carboxamide;

3-{4-[4-(5-fluoro-2-methoxyphenyl)-1H-pyrrolo[2,3-b]pyridin-2-yl]-3,6-dihydropyridin-1(2H)-yl}cyclobutanecarbonitrile;

3-{4-[4-(5-fluoro-2-methoxyphenyl)-1H-pyrrolo[2,3-b]pyridin-2-yl]-3,6-dihydropyridin-1(2H)-yl}cyclopentanecarboxylic acid;

9-[4-(5-fluoro-2-methoxyphenyl)-1H-pyrrolo[2,3-b]pyridin-2-yl]-3-azaspiro[5.5]undec-8-ene;

9-[4-(5-fluoro-2-methoxyphenyl)-1H-pyrrolo[2,3-b]pyridin-2-yl]-N-methyl-3-azaspiro[5.5]undec-8-ene-3-carboxamide;

9-[4-(5-fluoro-2-methoxyphenyl)-1H-pyrrolo[2,3-b]pyridin-2-yl]-3-(methylsulfonyl)-3-azaspiro[5.5]undec-8-ene;

(3-{4-[4-(5-fluoro-2-methoxyphenyl)-1H-pyrrolo[2,3-b]pyridin-2-yl]-3,6-dihydropyridin-1(2H)-yl}cyclobutyl)methanol;

(trans-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

(cis-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

N-(1,1-dioxidotetrahydrothiophen-3-yl)-2-{4-[4-(5-fluoro-2-methoxyphenyl)-1H-pyrrolo[2,3-b]pyridin-2-yl]-3,6-dihydropyridin-1(2H)-yl}acetamide;

N-(1,1-dioxidotetrahydrothiophen-3-yl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]-3,6-dihydropyridin-1(2H)-yl}-1-[3-(methylsulfonyl)azetidin-1-yl]ethanone;

2-{4-[4-(5-fluoro-2-methoxyphenyl)-1H-pyrrolo[2,3-b]pyridin-2-yl]piperidin-1-yl}-1-[3-(methylsulfonyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-N-(1-methyl-1H-pyrazol-4-yl)acetamide;

4-(4-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-(4,5-difluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

2-{3-[4-(5-fluoro-2-methoxyphenyl)-1H-pyrrolo[2,3-b]pyridin-2-yl]-9-azabicyclo[3.3.1]non-2-en-9-yl}-N-(2-hydroxyethyl)-N-methylacetamide;

2-{3-[4-(5-fluoro-2-methoxyphenyl)-1H-pyrrolo[2,3-b]pyridin-2-yl]-9-azabicyclo[3.3.1]non-2-en-9-yl}-1-(3-hydroxyazetidin-1-yl)ethanone;

2-{3-[4-(5-fluoro-2-methoxyphenyl)-1H-pyrrolo[2,3-b]pyridin-2-yl]-9-azabicyclo[3.3.1]non-2-en-9-yl}-1-[(2S)-2-(hydroxymethyl)pyrrolidin-1-yl]ethanone;

2-{3-[4-(5-fluoro-2-methoxyphenyl)-1H-pyrrolo[2,3-b]pyridin-2-yl]-9-azabicyclo[3.3.1]non-2-en-9-yl}-N-(3-hydroxycyclobutyl)-N-methylacetamide;

{3-[4-(5-fluoro-2-methoxyphenyl)-1H-pyrrolo[2,3-b]pyridin-2-yl]-9-azabicyclo[3.3.1]non-2-en-9-yl}acetic acid;

4-(2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

tert-butyl (2-{4-[4-(5-fluoro-2-methoxyphenyl)-1H-pyrrolo[2,3-b]pyridin-2-yl]-3,6-dihydropyridin-1(2H)-yl}ethyl)carbamate;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;

4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

2-{4-[4-(5-fluoro-2-methoxyphenyl)-1H-pyrrolo[2,3-b]pyridin-2-yl]azepan-1-yl}-1-(3-hydroxyazetidin-1-yl)ethanone;

3-({4-[4-(5-fluoro-2-methoxyphenyl)-1H-pyrrolo[2,3-b]pyridin-2-yl]cyclohex-3-en-1-yl}amino)bicyclo[1.1.1]pentane-1-carboxylic acid;

2-{4-[4-(5-fluoro-2-methoxyphenyl)-1H-pyrrolo[2,3-b]pyridin-2-yl]-3,6-dihydropyridin-1(2H)-yl}ethanamine;

N-(2-{4-[4-(5-fluoro-2-methoxyphenyl)-1H-pyrrolo[2,3-b]pyridin-2-yl]-3,6-dihydropyridin-1(2H)-yl}ethyl)methanesulfonamide;

N-(2-{4-[4-(5-fluoro-2-methoxyphenyl)-1H-pyrrolo[2,3-b]pyridin-2-yl]-3,6-dihydropyridin-1(2H)-yl}ethyl)acetamide;

2-{4-[4-(5-fluoro-2-methoxyphenyl)-1H-pyrrolo[2,3-b]pyridin-2-yl]-3,6-dihydropyridin-1(2H)-yl}-N,N-dimethylethanesulfonamide;

2-{3-[4-(5-fluoro-2-methoxyphenyl)-1H-pyrrolo[2,3-b]pyridin-2-yl]-2,5-dihydro-1H-pyrrol-1-yl}-1-(3-hydroxyazetidin-1-yl)ethanone;

(4-{4-[4-(5-fluoro-2-methoxyphenyl)-1H-pyrrolo[2,3-b]pyridin-2-yl]cyclohex-3-en-1-yl}piperidin-1-yl)acetic acid;

4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;

2-{3-[4-(5-fluoro-2-methoxyphenyl)-1H-pyrrolo[2,3-b]pyridin-2-yl]-2,5-dihydro-1H-pyrrol-1-yl}-N-(2-hydroxyethyl)-N-methylacetamide;

2-{3-[4-(5-fluoro-2-methoxyphenyl)-1H-pyrrolo[2,3-b]pyridin-2-yl]-2,5-dihydro-1H-pyrrol-1-yl}-N,N-dimethylacetamide;

2-{3-[4-(5-fluoro-2-methoxyphenyl)-1H-pyrrolo[2,3-b]pyridin-2-yl]-2,5-dihydro-1H-pyrrol-1-yl}-1-[(2S)-2-(hydroxymethyl)pyrrolidin-1-yl]ethanone;

2-(4-{4-[4-(5-fluoro-2-methoxyphenyl)-1H-pyrrolo[2,3-b]pyridin-2-yl]cyclohex-3-en-1-yl}piperidin-1-yl)-N,N-dimethylacetamide;

(4-{(1S)-4-[4-(5-fluoro-2-methoxyphenyl)-1H-pyrrolo[2,3-b]pyridin-2-yl]cyclohex-3-en-1-yl}piperidin-1-yl)acetic acid;

(4-{(1R)-4-[4-(5-fluoro-2-methoxyphenyl)-1H-pyrrolo[2,3-b]pyridin-2-yl]cyclohex-3-en-1-yl}piperidin-1-yl)acetic acid;

methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate;

(4-{(1S)-4-[4-(5-fluoro-2-methoxyphenyl)-1H-pyrrolo[2,3-b]pyridin-2-yl]cyclohex-3-en-1-yl}piperazin-1-yl)acetic acid;

(4-{(1R)-4-[4-(5-fluoro-2-methoxyphenyl)-1H-pyrrolo[2,3-b]pyridin-2-yl]cyclohex-3-en-1-yl}piperazin-1-yl)acetic acid;

(4-{4-[4-(5-fluoro-2-methoxyphenyl)-1H-pyrrolo[2,3-b]pyridin-2-yl]-3,6-dihydropyridin-1(2H)-yl}cyclohexylidene)acetic acid;

cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

trans-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
(cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
(1-{4-[4-(5-fluoro-2-methoxyphenyl)-1H-pyrrolo[2,3-b]pyridin-2-yl]cyclohex-3-en-1-yl}piperidin-4-yl)acetic acid;
methyl (4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetate;
cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
(4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetic acid;
(trans-4-{4-[5-fluoro-4-(5-fluoro-2-methoxyphenyl)-1H-pyrrolo[2,3-b]pyridin-2-yl]piperidin-1-yl}cyclohexyl)acetic acid;
2-(trans-4-{4-[4-(5-fluoro-2-methoxyphenyl)-1H-pyrrolo[2,3-b]pyridin-2-yl]-3,6-dihydropyridin-1(2H)-yl}cyclohexyl)-N-(propan-2-ylsulfonyl)acetamide;
trans-4-{4-[5-fluoro-4-(5-fluoro-2-methoxyphenyl)-1H-pyrrolo[2,3-b]pyridin-2-yl]-3,6-dihydropyridin-1(2H)-yl}-N-(propan-2-ylsulfonyl)cyclohexanecarboxamide;
(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexyl)acetic acid;
(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid; and pharmaceutically acceptable salts thereof.

Embodiments of Formula (IVa)

In another aspect, the present invention relates to compounds of Formula (IVa) or a pharmaceutically acceptable salt thereof,

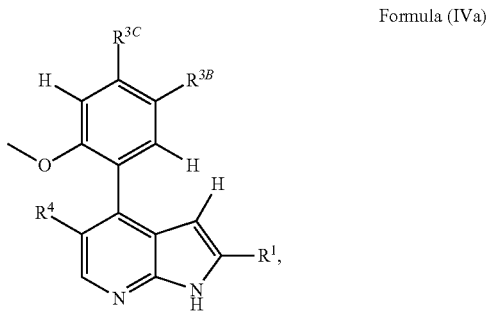

Formula (IVa)

wherein
R$^1$ is selected from the group consisting of cycloalkyl, cycloalkenyl, heterocycloalkyl, and heterocycloalkenyl; wherein the R$^1$ cycloalkyl, cycloalkenyl, heterocycloalkyl and heterocycloalkenyl are optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, SO$_2$NHC(O)R$^5$, SO$_2$NR$^5$C(O)R$^5$, NHS(O)$_2$R$^5$, NR$^5$S(O)$_2$R$^5$, NHC(O)OR$^5$, NR$^5$C(O)OR$^5$, SO$_2$NHC(O)OR$^5$, SO$_2$NR$^5$C(O)OR$^5$, NHSO$_2$NHC(O)OR$^5$, NHSO$_2$NR$^5$C(O)OR$^5$, NR$^5$SO$_2$NR$^5$C(O)OR, NR$^5$SO$_2$NHC(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, OC(O)NH$_2$, OC(O)NHR$^5$, OC(O)N(R$^5$)$_2$, OC(O)NHSO$_2$R$^5$, OC(O)NR$^5$SO$_2$R$^5$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, OSO$_2$NH$_2$, OSO$_2$NHR$^5$, OSO$_2$N(R$^5$)$_2$, C(O)NHCN, C(O)NR$^5$CN, S(O)NR$^5$, S(O)(N)R$^5$SO$_2$R$^5$, C(O)H, C(O)OH, (O), OH, CN, NO$_2$, F, Cl, Br and I;

R$^{3B}$, and R$^{3C}$ are each independently selected from the group consisting of H, R$^6$, OR$^6$, SR$^6$, S(O)R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, C(O)H, C(O)OH, (O), OH, CN, NO$_2$, F, Cl, Br and I;

R$^4$ is selected from the group consisting of R$^{4A}$, OR$^{4A}$, C(O)NH$_2$, CN, F, Cl, Br, and I;

R$^{4A}$ is selected from the group consisting of hydrogen, C$_1$-C$_6$ alkyl, C$_2$-C$_6$alkenyl, and C$_2$-C$_6$alkynyl;

R$^5$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^5$C$_1$-C$_6$ alkyl, C$_2$-C$_6$alkenyl, and C$_2$-C$_6$alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, B(OH)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I;

R$^6$, at each occurrence, is independently selected from the group consisting of C$_1$-C$_6$alkyl, C$_2$-C$_6$alkenyl, C$_2$-C$_6$alkynyl, phenyl, heteroaryl, heterocycloalkyl, heterocycloalkenyl, cycloalkyl, and cycloalkenyl; wherein each R$^6$C$_1$-C$_6$alkyl, C$_2$-C$_6$alkenyl, and C$_2$-C$_6$alkynyl is optionally substituted with one or more substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)R$^9$, NR$^9$C(O)OR$^9$, NHC(O) NH$_2$, NHC(O)NHR$^9$, NHC(O)N(R$^9$)$_2$, NR$^9$C(O) NHR$^9$, NR$^9$C(O)N(R$^9$)$_2$, C(O)NH$_2$, C(O)NHR$^9$, C(O) N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, CN, NO$_2$, F, Cl, Br and I; wherein each R$^6$ phenyl, cycloalkyl, cycloalkenyl, heteroaryl, heterocycloalkyl, and heterocycloalkenyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O) R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC (O)NH$_2$, NHC(O)NHR$^{10}$, NHC(O)N(R$^{10}$)$_2$, NR$^{10}$C(O) NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O) NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, (O), OH, CN, NO$_2$, F, Cl, Br and I;

R$^7$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^7$C$_1$-C$_6$ alkyl, C$_2$-C$_6$alkenyl, and C$_2$-C$_6$alkynyl is optionally substituted with one or more substituents independently selected from the group consisting of R$^{13}$, OR$^{13}$, NH$_2$, NHR$^{13}$, N(R$^{13}$)$_2$, C(O)H, C(O)OH, OH, CN, NO$_2$, F, Cl, Br and I; wherein each R$^7$ aryl, cycloalkyl, cycloalkenyl, heteroaryl, heterocycloalkyl, and heterocycloalkenyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C (O)OR$^{11}$, NHC(O)NH$_2$, NHC(O)NHR$^{11}$, NHC(O)N (R$^{11}$)$_2$, NR$^{11}$C(O)NHR$^{11}$, NR$^{11}$C(O)N(R$^{11}$)$_2$, C(O) NH$_2$, C(O)NHR$^{11}$, C(O)N(R$^{11}$)$_2$, C(O)NHOH, C(O) NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, (O), OH, CN, NO$_2$, F, Cl, Br and I;

R$^8$, at each occurrence, is independently selected from the group consisting of C$_1$-C$_6$ alkyl, C$_2$-C$_6$alkenyl, C$_2$-C$_6$alkynyl, and heterocycloalkyl; wherein each R$^8$C$_1$-C$_6$ alkyl, C$_2$-C$_6$alkenyl, and C$_2$-C$_6$alkynyl is optionally substituted with one or more substituents independently selected from the group consisting of aryl, heteroaryl, SO$_2$R$^{8A}$, C(O)OR$^{8A}$, C(O)NH$_2$, C(O) NHR$^{8A}$, C(O)N(R$^{8A}$)$_2$, C(O)NHSO$_2$R$^{8A}$, C(O) NR$^{8A}$SO$_2$R$^{8A}$, NH$_2$, C(O)H, C(O)OH, OH, CN, NO$_2$, F, Cl, Br and I; wherein each R$^8$ heterocycloalkyl is optionally substituted with one or more substituents independently selected from the group consisting of NH$_2$, C(O)H, C(O)OH, OH, CN, NO$_2$, F, Cl, Br and I;

R$^{8A}$, at each occurrence, is independently selected from the group consisting of C$_1$-C$_6$ alkyl, C$_2$-C$_6$alkenyl, and C$_2$-C$_6$alkynyl;

R$^9$, at each occurrence, is independently selected from the group consisting of C$_1$-C$_6$alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^9$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I; wherein each R$^9$ aryl, cycloalkyl, cycloalkenyl, heteroaryl, heterocycloalkyl, and heterocycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O) R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC (O)NH$_2$, NHC(O)NHR$^{12}$, NHC(O)N(R$^{12}$)$_2$, NR$^{12}$C(O) NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O) NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, (O), OH, CN, NO$_2$, F, Cl, Br and I;

R$^{10}$, at each occurrence, is independently selected from the group consisting of C$_1$-C$_6$alkyl, C$_2$-C$_6$alkenyl, and C$_2$-C$_6$ alkynyl; wherein each R$^{10}$C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I;

R$^{11}$, at each occurrence, is independently selected from the group consisting of C$_1$-C$_6$alkyl, C$_2$-C$_6$alkenyl, C$_2$-C$_6$alkynyl, aryl, and heteroaryl; wherein each R$^{11}$C$_1$-C$_6$alkyl, C$_2$-C$_6$alkenyl, and C$_2$-C$_6$alkynyl is optionally substituted with one or more substituents independently selected from the group consisting of OR$^{11A}$, NH$_2$, NHR$^{11A}$, N(R$^{11A}$)$_2$, C(O)H, C(O)OH, OH, CN, NO$_2$, F, Cl, Br and I; wherein each R$^{11}$ aryl and heteroaryl is optionally substituted with one or more substituents independently selected from the group consisting of C$_1$-C$_6$alkyl, C$_1$-C$_6$ haloalkyl, NH$_2$, C(O)H, C(O)OH, OH, CN, NO$_2$, F, Cl, Br and I;

R$^{11A}$, at each occurrence, is independently selected from the group consisting of C$_1$-C$_6$alkyl, C$_2$-C$_6$alkenyl, and C$_2$-C$_6$ alkynyl;

R$^{12}$, at each occurrence, is independently selected from the group consisting of C$_1$-C$_6$alkyl, C$_2$-C$_6$alkenyl, and C$_2$-C$_6$ alkynyl; wherein each R$^{12}$C$_1$-C$_6$alkyl, C$_2$-C$_6$alkenyl, and C$_2$-C$_6$alkynyl is optionally substituted with one or more substituents independently selected from the group consisting of NH$_2$, NHR$^{14}$, N(R$^{14}$)$_2$, C(O)H, C(O)OH, OH, CN, NO$_2$, F, Cl, Br and I;

R$^{13}$, at each occurrence, is independently selected from the group consisting of C$_1$-C$_6$alkyl, C$_2$-C$_6$alkenyl, C$_2$-C$_6$ alkynyl, aryl, heteroaryl, cycloalkyl, cycloalkenyl, heterocycloalkyl, and heterocycloalkenyl; wherein each R$^{13}$C$_1$-C$_6$alkyl, C$_2$-C$_6$alkenyl, and C$_2$-C$_6$alkynyl is optionally substituted with one or more substituents independently selected from the group consisting of R$^{15}$, OR$^{15}$, C(O)H, C(O)OH, OH, CN, NO$_2$, F, Cl, Br and I; wherein each R$^{13}$ aryl, cycloalkyl, cycloalkenyl, heteroaryl, heterocycloalkyl, and heterocycloalkenyl is optionally substituted with one or more substituents independently selected from the group consisting of R$^{16}$, OR$^{16}$, C(O)H, C(O)OH, (O), OH, CN, NO$_2$, F, Cl, Br and I;

R$^{14}$, at each occurrence, is independently selected from the group consisting of C$_1$-C$_6$ haloalkyl, C$_1$-C$_6$alkyl, C$_2$-C$_6$alkenyl, and C$_2$-C$_6$ alkynyl;

R$^{15}$, at each occurrence, is independently selected from the group consisting of C$_1$-C$_6$ haloalkyl, C$_1$-C$_6$alkyl, C$_2$-C$_6$alkenyl, and C$_2$-C$_6$ alkynyl; wherein each R$^{15}$C$_1$-C$_6$alkyl, C$_2$-C$_6$alkenyl, and C$_2$-C$_6$alkynyl is optionally substituted with one or more OCH$_3$; and R$^{16}$, at each occurrence, is independently selected from the group consisting of C$_1$-C$_6$ haloalkyl, C$_1$-C$_6$alkyl, C$_2$-C$_6$alkenyl, and C$_2$-C$_6$ alkynyl.

In one embodiment of Formula (IVa), $R^4$ is selected from the group consisting of $R^{4A}$, $OR^{4A}$, $C(O)NH_2$, CN, F, Cl, Br, and I; and $R^{4A}$ is selected from the group consisting of hydrogen, $C_1$-$C_6$ alkyl, $C_2$-$C_6$ alkenyl, and $C_2$-$C_6$ alkynyl. In another embodiment of Formula (IVa), $R^4$ is selected from the group consisting of $R^{4A}$, $OR^{4A}$, $C(O)NH_2$, CN, F, and Cl; and $R^{4A}$ is selected from the group consisting of hydrogen and $C_1$-$C_6$ alkyl. In another embodiment of Formula (IVa), $R^4$ is selected from the group consisting of $R^{4A}$, $OR^{4A}$, $C(O)NH_2$, CN, F, and Cl; and $R^{4A}$ is selected from the group consisting of hydrogen and $C_1$-alkyl. In another embodiment of Formula (IVa), $R^4$ is hydrogen. In another embodiment of Formula (IVa), $R^4$ is CN. In another embodiment of Formula (IVa), $R^4$ is F. In another embodiment of Formula (IVa), $R^4$ is Cl. In another embodiment of Formula (IVa), $R^4$ is OH. In another embodiment of Formula (IVa), $R^4$ is $OCH_3$. In another embodiment of Formula (IVa), $R^4$ is $CH_3$. In another embodiment of Formula (IVa), $R^4$ is $C(O)NH_2$.

In one embodiment of Formula (IVa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)NR^5$, $S(O)(N)R^5SO_2R^5$, $C(O)H$, $C(O)OH$, (O), OH, CN, $NO_2$, F, Cl, Br and I. In another embodiment of Formula (IVa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R^5$, $SO_2NHC(O)OR^5$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IVa), $R^1$ is cycloalkyl; wherein the $R^1$ cycloalkyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R^5$, $SO_2NHC(O)OR^5$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IVa), $R^1$ is cycloalkenyl; wherein the $R^1$ cycloalkenyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IVa), $R^1$ is heterocycloalkyl; wherein the $R^1$ heterocycloalkyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IVa), $R^1$ is heterocycloalkenyl; wherein the $R^1$ heterocycloalkenyl is optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R$, $NHS(O)_2R$, $SO_2NHC(O)OR$, $NHSO_2NHC(O)OR$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN. In another embodiment of Formula (IVa), $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)$ NR$^5$SO$_2$R$^5$, C(O)NH$_2$, C(O)NHR$^5$, C(O)N(R$^5$)$_2$, C(O)N-HOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, OSO$_2$NH$_2$, OSO$_2$NHR$^5$, OSO$_2$N(R$^5$)$_2$, C(O)NHCN, C(O)NR$^5$CN, S(O)NR$^5$, S(O)(N)R$^5$SO$_2$R, C(O)H, C(O)OH, (O), OH, CN, NO$_2$, F, Cl, Br and I. In another embodiment of Formula (IVa), R$^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the R$^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of R$^5$, OR$^5$, SO$_2$R$^5$, C(O)R$^5$, CO(O)R$^5$, NH$_2$, NHR$^5$, NHC(O)R$^5$, SO$_2$NHC(O)R, NHS(O)$_2$R$^5$, SO$_2$NHC(O)OR, NHSO$_2$NHC(O)OR, NHC(O)NHR$^5$, OC(O)NHR$^5$, OC(O)NHSO$_2$R$^5$, C(O)NH$_2$, C(O)NHR$^5$, C(O)N(R$^5$)$_2$, C(O)NHOR$^5$, C(O)NHSO$_2$R$^5$, SO$_2$NH$_2$, SO$_2$NHR$^5$, SO$_2$N(R$^5$)$_2$, OSO$_2$NHR$^5$, C(O)NHCN, S(O)NR$^5$, S(O)(N)R$^5$SO$_2$R, C(O)OH, (O), OH, and CN. In another embodiment of Formula (IVa), R$^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the R$^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (IVa), R$^{3B}$ and R$^{3C}$ are each independently selected from the group consisting of H, R$^6$, OR$^6$, SR$^6$, S(O)R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, C(O)H, C(O)OH, (O), OH, CN, NO$_2$, F, Cl, Br and I. In another embodiment of Formula (IVa), R$^{3B}$ and R$^{3C}$ are each independently selected from the group consisting of H, R$^6$, OR$^6$, SR$^6$, S(O)R$^6$, C(O)R$^6$, NH$_2$, NHR$^6$, N(R$^6$)$_2$, NHC(O)R$^6$, NHS(O)$_2$R$^6$, C(O)NH$_2$, C(O)NHR$^6$, C(O)N(R$^6$)$_2$, CN, F, and Cl. In another embodiment of Formula (IVa), R$^{3B}$ and R$^{3C}$ are each independently selected from the group consisting of H, R$^6$, OR$^6$, NH$_2$, NHR$^6$, N(R$^6$)$_2$, NHC(O)R$^6$, NHS(O)$_2$R$^6$, CN, F, and Cl. In another embodiment of Formula (IVa), R$^{3B}$ and R$^{3C}$ are each independently selected from the group consisting of H, R$^6$, OR$^6$, NH$_2$, NHR$^6$, N(R$^6$)$_2$, NHS(O)$_2$R$^6$, CN, F, and Cl. In one embodiment of Formula (IVa), R$^{3B}$ is F, and R$^{3C}$ is H. In another embodiment of Formula (IVa), R$^{3B}$ and R$^{3C}$ are each independently selected from the group consisting of H, R$^6$, OR$^6$, SR$^6$, S(O)R$^6$, C(O)R$^6$, NH$_2$, NHR$^6$, N(R$^6$)$_2$, NHC(O)R$^6$, NHS(O)$_2$R$^6$, C(O)NH$_2$, C(O)NHR$^6$, C(O)N(R$^6$)$_2$, CN, F, and Cl.

In one embodiment of Formula (IVa), R$^5$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^5$C$_1$-C$_6$ alkyl, C$_2$-C$_6$alkenyl, and C$_2$-C$_6$alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, B(OH)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^8$, OR, SR$^8$, S(O)R$^8$, SO$_2$R, C(O)R$^8$, CO(O)R$^8$, OC(O)R$^8$, OC(O)OR, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I. In another embodiment of Formula (IVa), R$^5$, at each occurrence, is independently selected from the group consisting of $C_1$-$C_6$ alkyl, aryl, heteroaryl, heterocycloalkyl, heterocycloalkenyl, cycloalkyl, and cycloalkenyl; wherein each $R^5C_1$-$C_6$ alkyl is optionally substituted with one or more substituents independently selected from the group consisting of $R^7$, $OR^7$, $SO_2R^7$, $C(O)R^7$, $CO(O)R^7$, $OC(O)R^7$, $NH_2$, $NHR^7$, $N(R^7)_2$, $NHC(O)R^7$, $NHS(O)_2R^7$, $NHC(O)OR^7$, $NHC(O)NHR^7$, $C(O)NH_2$, $C(O)NHR^7$, $C(O)N(R^7)_2$, $C(O)NHSO_2R^7$, $SO_2NH_2$, $SO_2NHR^7$, $SO_2N(R^7)_2$, $B(OH)_2$, $C(O)OH$, OH, CN, F, and Cl; wherein each $R^5$ aryl, cycloalkyl, heteroaryl, heterocycloalkyl, and heterocycloalkenyl is optionally substituted with one or more substituents independently selected from the group consisting of $R^8$, $OR^8$, $SR^8$, $SO_2R^8$, $C(O)R^8$, $CO(O)R^8$, $NH_2$, $NHR^8$, $NHC(O)R^8$, $NHS(O)_2R^8$, $C(O)NHR^8$, $C(O)N(R^8)_2$, $C(O)NHSO_2R^8$, $C(O)OH$, (O), OH, CN, $NO_2$, F, and Cl.

In one embodiment of Formula (IVa), $R^6$, at each occurrence, is independently selected from the group consisting of $C_1$-$C_6$alkyl, $C_2$-$C_6$alkenyl, $C_2$-$C_6$alkynyl, phenyl, heteroaryl, heterocycloalkyl, heterocycloalkenyl, cycloalkyl, and cycloalkenyl; wherein each $R^6C_1$-$C_6$alkyl, $C_2$-$C_6$alkenyl, and $C_2$-$C_6$alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I. In another embodiment of Formula (IVa), $R^6$, at each occurrence, is independently selected from the group consisting of $C_1$-$C_6$alkyl, phenyl, heteroaryl, heterocycloalkyl, heterocycloalkenyl, and cycloalkyl; wherein each $R^6C_1$-$C_6$alkyl, is optionally substituted with one or more substituents independently selected from the group consisting of $R^9$, $NH_2$, $NHR^9$, $NHS(O)_2R^9$, CN, and F; and wherein each $R^6$ phenyl, heteroaryl, heterocycloalkyl, heterocycloalkenyl, and cycloalkyl is optionally substituted with one or more substituents independently selected from the group consisting of $R^{10}$, $OR^{10}$, and F.

In one embodiment of Formula (IVa), $R^7$, at each occurrence, is independently selected from the group consisting of $C_1$-$C_6$ alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^7C_1$-$C_6$ alkyl, $C_2$-$C_6$alkenyl, and $C_2$-$C_6$alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, (O), OH, CN, $NO_2$, F, Cl, Br and I. In another embodiment of Formula (IVa), $R^7$, at each occurrence, is independently selected from the group consisting of $C_1$-$C_6$ alkyl, aryl, heteroaryl, heterocycloalkyl, heterocycloalkenyl, and cycloalkyl; wherein each $R^7C_1$-$C_6$ alkyl is optionally substituted with one or more substituents independently selected from the group consisting of $R^{13}$, $OR^{13}$, $N(R^{13})_2$, and OH; wherein each $R^7$ aryl, heteroaryl, heterocycloalkyl, heterocycloalkenyl, and cycloalkyl is optionally substituted with one or more substituents independently selected from the group consisting of $R^{11}$, $OR^{11}$, $SO_2R^{11}$, $C(O)R^{11}$, $CO(O)R^{11}$, $NH_2$, $N(R^{11})_2$, $NHC(O)R^{11}$, $NHS(O)_2R^{11}$, $C(O)NH_2$, $C(O)OH$, (O), OH, CN, F, and Cl.

In one embodiment of Formula (IVa), $R^8$, at each occurrence, is independently selected from the group consisting of $C_1$-$C_6$ alkyl, $C_2$-$C_6$alkenyl, $C_2$-$C_6$alkynyl, and heterocycloalkyl; wherein each $R^8C_1$-$C_6$ alkyl, $C_2$-$C_6$alkenyl, and $C_2$-$C_6$alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)OH$, OH, CN, $NO_2$, F, Cl, Br and I; and $R^{8A}$, at each occurrence, is independently selected from the group consisting of $C_1$-$C_6$ alkyl, $C_2$-$C_6$alkenyl, and $C_2$-$C_6$alkynyl. In another embodiment of Formula (IVa), $R^8$, at each occurrence, is independently selected from the group consisting of $C_1$-$C_6$ alkyl, $C_2$-$C_6$alkenyl, and heterocycloalkyl; wherein each $R^8C_1$-$C_6$ alkyl and $C_2$-$C_6$alkenyl is optionally substituted with one or more substituents independently selected from the group consisting of aryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)OH$, OH, CN, and F; wherein each $R^8$ heterocycloalkyl is optionally substituted with one or more OH; and $R^{8A}$, at each occurrence, is independently $C_1$-$C_6$ alkyl.

In one embodiment of Formula (IVa), $R^9$, at each occurrence, is independently selected from the group consisting of $C_1$-$C_6$alkyl, $C_2$-$C_6$alkenyl, $C_2$-$C_6$alkynyl, aryl, heteroaryl, heterocycloalkyl, heterocycloalkenyl, cycloalkyl, and cycloalkenyl; wherein each $R^9C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I. In another embodiment of Formula (IVa), $R^9$, at each occurrence, is independently selected from the group consisting of $C_1$-$C_6$alkyl, aryl, heteroaryl, heterocycloalkyl, cycloalkyl, and cycloalkenyl; wherein each $R^9$ aryl, heteroaryl, heterocycloalkyl, cycloalkyl, and cycloalkenyl is optionally substituted with one or more substituents independently selected from the group consisting of $R^{12}$, $OR^{12}$, $SO_2R^{12}$, $NH_2$, $C(O)NH_2$, $SO_2NH_2$, $C(O)OH$, (O), OH, CN, F, and Cl.

In one embodiment of Formula (IVa), $R^{10}$, at each occurrence, is independently selected from the group consisting of $C_1$-$C_6$alkyl, $C_2$-$C_6$alkenyl, and $C_2$-$C_6$ alkynyl; wherein each $R^{10}C_1$-$C_6$alkyl, $C_2$-$C_6$alkenyl, and $C_2$-$C_6$alkynyl is optionally substituted with one or more substituents independently selected from the group consisting of $NH_2$, $C(O)H$, $C(O)OH$, OH, CN, $NO_2$, F, Cl, Br and I. In another embodiment of Formula (IVa), $R^{10}$, at each occurrence, is $C_1$-$C_6$alkyl.

In one embodiment of Formula (IVa), $R^{11}$, at each occurrence, is independently selected from the group consisting of $C_1$-$C_6$alkyl, $C_2$-$C_6$alkenyl, $C_2$-$C_6$alkynyl, aryl, and heteroaryl; wherein each $R^{11}C_1$-$C_6$alkyl, $C_2$-$C_6$alkenyl, and $C_2$-$C_6$alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$alkyl, $C_1$-$C_6$ haloalkyl, $NH_2$, $C(O)H$, $C(O)OH$, OH, CN, $NO_2$, F, Cl, Br and I; and $R^{11A}$, at each occurrence, is independently selected from the group consisting of $C_1$-$C_6$alkyl, $C_2$-$C_6$alkenyl, and $C_2$-$C_6$ alkynyl. In another embodiment of Formula (IVa), $R^{11}$, at each occurrence, is independently selected from the group consisting of $C_1$-$C_6$alkyl and aryl; wherein each $R^{11}C_1$-$C_6$alkyl is optionally substituted with one or more substituents independently selected from the group consisting of $OR^{11A}$, $N(R^{11A})_2$, $C(O)OH$, and OH; wherein each $R^{11}$ aryl is optionally substituted with one or more $C_1$-$C_6$alkyl; and $R^{11A}$, at each occurrence, is independently $C_1$-$C_6$alkyl.

In one embodiment of Formula (IVa), $R^{12}$, at each occurrence, is independently selected from the group consisting of $C_1$-$C_6$alkyl, $C_2$-$C_6$alkenyl, and $C_2$-$C_6$ alkynyl; wherein each $R^{12}C_1$-$C_6$alkyl, $C_2$-$C_6$alkenyl, and $C_2$-$C_6$alkynyl is optionally substituted with one or more substituents independently selected from the group consisting of $NH_2$, $NHR^{14}$, $N(R^{14})_2$, $C(O)H$, $C(O)OH$, OH, CN, $NO_2$, F, Cl, Br and I. In another embodiment of Formula (IVa), $R^{12}$, at each occurrence, is independently $C_1$-$C_6$alkyl; wherein each $R^{12}C_1$-$C_6$alkyl is optionally substituted with one or more $C(O)OH$.

In one embodiment of Formula (IVa), $R^{13}$, at each occurrence, is independently selected from the group consisting of $C_1$-$C_6$alkyl, $C_2$-$C_6$alkenyl, $C_2$-$C_6$ alkynyl, aryl, heteroaryl, cycloalkyl, cycloalkenyl, heterocycloalkyl, and heterocycloalkenyl; wherein each $R^{13}C_1$-$C_6$alkyl, $C_2$-$C_6$alkenyl, and $C_2$-$C_6$alkynyl is optionally substituted with one or more substituents independently selected from the group consisting of $R^{15}$, $OR^{15}$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, (O), OH, CN, $NO_2$, F, Cl, Br and I. In another embodiment of Formula (IVa), $R^{13}$, at each occurrence, is independently selected from the group consisting of $C_1$-$C_6$alkyl, aryl, heteroaryl, and heterocycloalkyl; wherein each $R^{13}C_1$-$C_6$alkyl is optionally substituted with one or more $OR^{15}$; wherein each $R^{13}$ aryl, heteroaryl, and heterocycloalkyl is optionally substituted with one or more $R^{16}$.

In one embodiment of Formula (IVa), $R^{15}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl; wherein each $R^{15}C_1$-$C_6$alkyl, $C_2$-$C_6$alkenyl, and $C_2$-$C_6$alkynyl is optionally substituted with one or more $OCH_3$. In another embodiment of Formula (IVa), $R^{15}$, at each occurrence, is independently $C_1$-$C_6$alkyl; wherein each $R^{15}C_1$-$C_6$alkyl is optionally substituted with one or more $OCH_3$.

In one embodiment of Formula (IVa), $R^{16}$, at each occurrence, is independently selected from the group consisting of $C_1$-$C_6$ haloalkyl, $C_1$-$C_6$alkyl, $C_2$-$C_6$alkenyl, and $C_2$-$C_6$ alkynyl. In another embodiment of Formula (IVa), $R^{16}$, at each occurrence, is independently selected from the group consisting of $C_1$-$C_6$ haloalkyl and $C_1$-$C_6$alkyl.

In another embodiment of Formula (IVa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R^5$, $SO_2NHC(O)OR^5$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, (O), OH, and CN;

$R^{3B}$ and $R^{3C}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl;

$R^4$ is selected from the group consisting of $R^{4A}$, $OR^{4A}$, $C(O)NH_2$, CN, F, and Cl;

$R^{4A}$ is selected from the group consisting of hydrogen and $C_1$-$C_6$ alkyl;

$R^5$, at each occurrence, is independently selected from the group consisting of $C_1$-$C_6$ alkyl, aryl, heteroaryl, heterocycloalkyl, heterocycloalkenyl, cycloalkyl, and cycloalkenyl; wherein each $R^5C_1$-$C_6$ alkyl is optionally substituted with one or more substituents independently selected from the group consisting of $R^7$, $OR^7$, $SO_2R^7$, $C(O)R^7$, $CO(O)R^7$, $OC(O)R^7$, $NH_2$, $NHR^7$, $N(R^7)_2$, $NHC(O)R^7$, $NHS(O)_2R^7$, $NHC(O)OR^7$, $NHC(O)NHR^7$, $C(O)NH_2$, $C(O)NHR^7$, $C(O)N(R^7)_2$, $C(O)NHSO_2R^7$, $SO_2NH_2$, $SO_2NHR^7$, $SO_2N(R^7)_2$, $B(OH)_2$, $C(O)OH$, OH, CN, F, and Cl; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $SO_2R^8$, $C(O)R^8$, $CO(O)R^8$, $NH_2$, $NHR^8$, $NHC(O)R^8$, $NHS(O)_2R^8$, $C(O)NHR^8$, $C(O)N(R^8)_2$, $C(O)NHSO_2R^8$, $C(O)OH$, (O), OH, CN, F, and Cl;

$R^6$, at each occurrence, is independently selected from the group consisting of $C_1$-$C_6$alkyl, phenyl, heteroaryl, heterocycloalkyl, heterocycloalkenyl, cycloalkyl, and cycloalkenyl; wherein each $R^6C_1$-$C_6$alkyl is optionally substituted with one or more substituents independently selected from the group consisting of $R^9$, $NH_2$, $NHR^9$, $NHS(O)_2R^9$, CN, and F; wherein each $R^6$ phenyl, cycloalkyl, heteroaryl, heterocycloalkyl, and heterocycloalkenyl is optionally substituted with one or more substituents independently selected from the group consisting of $R^{10}$, $OR^{10}$, and F;

$R^7$, at each occurrence, is independently selected from the group consisting of $C_1$-$C_6$ alkyl, aryl, heteroaryl, heterocycloalkyl, heterocycloalkenyl, and cycloalkyl;

wherein each $R^7C_1$-$C_6$ alkyl is optionally substituted with one or more substituents independently selected from the group consisting of $R^{13}$, $OR^{13}$, $N(R^{13})_2$, and OH; wherein each $R^7$ aryl, heteroaryl, heterocycloalkyl, heterocycloalkenyl, and cycloalkyl is optionally substituted with one or more substituents independently selected from the group consisting of $R^{11}$, $OR^{11}$, $SO_2R^{11}$, $C(O)R^{11}$, $CO(O)R^{11}$, $NH_2$, $N(R^{11})_2$, $NHC(O)R^{11}$, $NHS(O)_2R^{11}$, $C(O)NH_2$, $C(O)OH$, (O), OH, CN, F, and Cl;

$R^8$, at each occurrence, is independently selected from the group consisting of $C_1$-$C_6$ alkyl, $C_2$-$C_6$alkenyl, and heterocycloalkyl; wherein each $R^8C_1$-$C_6$ alkyl and $C_2$-$C_6$alkenyl is optionally substituted with one or more substituents independently selected from the group consisting of aryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)OH$, OH, CN, and F; wherein each $R^8$ heterocycloalkyl is optionally substituted with one or more OH;

$R^{8A}$, at each occurrence, is independently $C_1$-$C_6$alkyl;

$R^9$, at each occurrence, is independently selected from the group consisting of $C_1$-$C_6$alkyl, aryl, heteroaryl, heterocycloalkyl, cycloalkyl, and cycloalkenyl; wherein each $R^9$ aryl, heteroaryl, heterocycloalkyl, cycloalkyl, and cycloalkenyl is optionally substituted with one or more substituents independently selected from the group consisting of $R^{12}$, $OR^{12}$, $SO_2R^{12}$, $NH_2$, $C(O)NH_2$, $SO_2NH_2$, $C(O)OH$, (O), OH, CN, F, and Cl;

$R^{10}$, at each occurrence, is independently $C_1$-$C_6$alkyl;

$R^{11}$, at each occurrence, is independently selected from the group consisting of $C_1$-$C_6$alkyl, and aryl; wherein each $R^{11}C_1$-$C_6$alkyl is optionally substituted with one or more substituents independently selected from the group consisting of $OR^{11A}$, $N(R^{11A})_2$, $C(O)OH$, and OH; wherein each $R^{11}$ aryl is optionally substituted with one or more substituents independently selected from the group consisting of $C_1$-$C_6$alkyl;

$R^{11A}$, at each occurrence, is independently $C_1$-$C_6$alkyl;

$R^{12}$, at each occurrence, is independently $C_1$-$C_6$alkyl; wherein each $R^{12}C_1$-$C_6$alkyl is optionally substituted with one or more C(O)OH;

$R^{13}$, at each occurrence, is independently selected from the group consisting of $C_1$-$C_6$alkyl, aryl, heteroaryl, and heterocycloalkyl; wherein each $R^{13}C_1$-$C_6$alkyl is optionally substituted with one or more $OR^{15}$; wherein each $R^{13}$ aryl, heteroaryl, and heterocycloalkyl, and heterocycloalkenyl is optionally substituted with one or more $R^{16}$;

$R^{15}$, at each occurrence, is independently $C_1$-$C_6$alkyl; wherein each $R^{15}C_1$-$C_6$alkyl is optionally substituted with one or more $OCH_3$; and $R^{16}$, at each occurrence, is independently selected from the group consisting of $C_1$-$C_6$ haloalkyl, and $C_1$-$C_6$alkyl.

Still another embodiment pertains to compounds of Formula (IVa), selected from the group consisting of:

4-(5-fluoro-2-methoxyphenyl)-2-(piperidin-3-yl)-1H-pyrrolo[2,3-b]pyridine;
4-(4-fluoro-2-methoxyphenyl)-2-(piperidin-3-yl)-1H-pyrrolo[2,3-b]pyridine;
4-(5-fluoro-2-methoxyphenyl)-2-[(3S)-piperidin-3-yl]-1H-pyrrolo[2,3-b]pyridine;
4-(5-fluoro-2-methoxyphenyl)-2-[(3R)-piperidin-3-yl]-1H-pyrrolo[2,3-b]pyridine;
4-[5-(4,5-dihydro-1H-imidazol-2-yl)-2-methoxyphenyl]-2-(piperidin-3-yl)-1H-pyrrolo[2,3-b]pyridine;
4-(5-cyclopropyl-2-methoxyphenyl)-2-(piperidin-3-yl)-1H-pyrrolo[2,3-b]pyridine;
4-(4-fluoro-2-methoxyphenyl)-2-(1-methylpiperidin-3-yl)-1H-pyrrolo[2,3-b]pyridine;
4-(5-fluoro-2-methoxyphenyl)-2-(1-methylpiperidin-3-yl)-1H-pyrrolo[2,3-b]pyridine;
1-{3-[4-(5-fluoro-2-methoxyphenyl)-1H-pyrrolo[2,3-b]pyridin-2-yl]piperidin-1-yl}ethanone;
4-(5-fluoro-2-methoxyphenyl)-2-(piperidin-4-yl)-1H-pyrrolo[2,3-b]pyridine;
4-(4-fluoro-2-methoxyphenyl)-2-(piperidin-4-yl)-1H-pyrrolo[2,3-b]pyridine;
4-(4-chloro-2-methoxyphenyl)-2-(piperidin-4-yl)-1H-pyrrolo[2,3-b]pyridine;
4-(4,5-difluoro-2-methoxyphenyl)-2-(piperidin-4-yl)-1H-pyrrolo[2,3-b]pyridine;
4-(5-chloro-2-methoxyphenyl)-2-(piperidin-4-yl)-1H-pyrrolo[2,3-b]pyridine;
4-(2-methoxy-5-methylphenyl)-2-(piperidin-4-yl)-1H-pyrrolo[2,3-b]pyridine;
4-(2-methoxyphenyl)-2-(piperidin-4-yl)-1H-pyrrolo[2,3-b]pyridine;
4-(5-fluoro-2-methoxyphenyl)-2-(1-methylpiperidin-4-yl)-1H-pyrrolo[2,3-b]pyridine;
4-(4-fluoro-2-methoxyphenyl)-2-(1-methylpiperidin-4-yl)-1H-pyrrolo[2,3-b]pyridine;
4-(2-methoxy-5-methylphenyl)-2-(1-methylpiperidin-4-yl)-1H-pyrrolo[2,3-b]pyridine;
4-(5-fluoro-2-methoxyphenyl)-2-(pyrrolidin-3-yl)-1H-pyrrolo[2,3-b]pyridine;
4-(4-fluoro-2-methoxyphenyl)-2-(pyrrolidin-3-yl)-1H-pyrrolo[2,3-b]pyridine;
4-(5-fluoro-2-methoxyphenyl)-2-[(3S)-pyrrolidin-3-yl]-1H-pyrrolo[2,3-b]pyridine;
4-(5-fluoro-2-methoxyphenyl)-2-[(3R)-pyrrolidin-3-yl]-1H-pyrrolo[2,3-b]pyridine;
4-(5-fluoro-2-methoxyphenyl)-2-(1-methylpyrrolidin-3-yl)-1H-pyrrolo[2,3-b]pyridine;
4-(4-fluoro-2-methoxyphenyl)-2-(morpholin-2-yl)-1H-pyrrolo[2,3-b]pyridine;
4-(5-fluoro-2-methoxyphenyl)-2-(morpholin-2-yl)-1H-pyrrolo[2,3-b]pyridine;
4-(4-fluoro-2-methoxyphenyl)-2-(4-methylmorpholin-2-yl)-1H-pyrrolo[2,3-b]pyridine;
4-(5-fluoro-2-methoxyphenyl)-2-(4-methylmorpholin-2-yl)-1H-pyrrolo[2,3-b]pyridine;
2-(5,5-dimethylmorpholin-2-yl)-4-(5-fluoro-2-methoxyphenyl)-1H-pyrrolo[2,3-b]pyridine;
2-(5,5-dimethylmorpholin-2-yl)-4-(4-fluoro-2-methoxyphenyl)-1H-pyrrolo[2,3-b]pyridine;
4-(4-chloro-2-methoxyphenyl)-2-(5,5-dimethylmorpholin-2-yl)-1H-pyrrolo[2,3-b]pyridine;
trans-4-[4-(5-fluoro-2-methoxyphenyl)-1H-pyrrolo[2,3-b]pyridin-2-yl]cyclohexanamine;
3-[4-(5-fluoro-2-methoxyphenyl)-1H-pyrrolo[2,3-b]pyridin-2-yl]cyclohexanamine;
4-(5-fluoro-2-methoxyphenyl)-2-(1,2,3,6-tetrahydropyridin-4-yl)-1H-pyrrolo[2,3-b]pyridine;
4-(5-fluoro-2-methoxyphenyl)-2-(pyrrolidin-2-yl)-1H-pyrrolo[2,3-b]pyridine;
2-cyclohexyl-4-(5-fluoro-2-methoxyphenyl)-1H-pyrrolo[2,3-b]pyridine;
1-{2-[4-(5-fluoro-2-methoxyphenyl)-1H-pyrrolo[2,3-b]pyridin-2-yl]pyrrolidin-1-yl}ethanone;
1-{4-[4-(5-fluoro-2-methoxyphenyl)-1H-pyrrolo[2,3-b]pyridin-2-yl]-3,6-dihydropyridin-1(2H)-yl}ethanone;

1-{4-[4-(5-fluoro-2-methoxyphenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-(1-methylpyrrolidin-2-yl)-1H-pyrrolo[2,3-b]pyridine;
1-{3-[4-(5-fluoro-2-methoxyphenyl)-1H-pyrrolo[2,3-b]pyridin-2-yl]pyrrolidin-1-yl}ethanone;
2-{3-[4-(5-fluoro-2-methoxyphenyl)-1H-pyrrolo[2,3-b]pyridin-2-yl]pyrrolidin-1-yl}ethanol;
4-(5-fluoro-2-methoxyphenyl)-2-[1-(tetrahydro-2H-pyran-4-yl)pyrrolidin-3-yl]-1H-pyrrolo[2,3-b]pyridine;
4-(5-fluoro-2-methoxyphenyl)-2-[1-(pyridin-2-ylmethyl)pyrrolidin-3-yl]-1H-pyrrolo[2,3-b]pyridine;
4-(5-fluoro-2-methoxyphenyl)-2-[1-(pyridin-3-ylmethyl)pyrrolidin-3-yl]-1H-pyrrolo[2,3-b]pyridine;
4-(5-fluoro-2-methoxyphenyl)-2-[1-(pyridin-4-ylmethyl)pyrrolidin-3-yl]-1H-pyrrolo[2,3-b]pyridine;
4-(5-fluoro-2-methoxyphenyl)-2-[1-(tetrahydro-2H-pyran-3-ylmethyl)pyrrolidin-3-yl]-1H-pyrrolo[2,3-b]pyridine;
tert-butyl (2-{3-[4-(5-fluoro-2-methoxyphenyl)-1H-pyrrolo[2,3-b]pyridin-2-yl]pyrrolidin-1-yl}ethyl)carbamate;
tert-butyl 3-[4-(5-fluoro-2-methoxyphenyl)-1H-pyrrolo[2,3-b]pyridin-2-yl]-1,3'-bipyrrolidine-1'-carboxylate;
4-(5-fluoro-2-methoxyphenyl)-2-[1-(tetrahydro-2H-pyran-4-ylmethyl)pyrrolidin-3-yl]-1H-pyrrolo[2,3-b]pyridine;
4-(5-fluoro-2-methoxyphenyl)-2-{1-[2-(morpholin-4-yl)ethyl]pyrrolidin-3-yl}-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine;
methyl 4-({trans-4-[4-(5-fluoro-2-methoxyphenyl)-1H-pyrrolo[2,3-b]pyridin-2-yl]cyclohexyl}amino)butanoate;
ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate;
trans-4-[4-(5-fluoro-2-methoxyphenyl)-1H-pyrrolo[2,3-b]pyridin-2-yl]-N-[2-(morpholin-4-yl)ethyl]cyclohexanamine;
3-({trans-4-[4-(5-fluoro-2-methoxyphenyl)-1H-pyrrolo[2,3-b]pyridin-2-yl]cyclohexyl}amino)propane-1,2-diol;
2-{3-[4-(5-fluoro-2-methoxyphenyl)-1H-pyrrolo[2,3-b]pyridin-2-yl]pyrrolidin-1-yl}ethanamine;
3-[4-(5-fluoro-2-methoxyphenyl)-1H-pyrrolo[2,3-b]pyridin-2-yl]-1,3'-bipyrrolidine;
4-[4-(5-fluoro-2-methoxyphenyl)-1H-pyrrolo[2,3-b]pyridin-2-yl]piperidin-4-ol;
benzyl (3-{3-[4-(5-fluoro-2-methoxyphenyl)-1H-pyrrolo[2,3-b]pyridin-2-yl]piperidin-1-yl}propyl)carbamate;
2-{3-[4-(5-fluoro-2-methoxyphenyl)-1H-pyrrolo[2,3-b]pyridin-2-yl]piperidin-1-yl}ethanol;
3-{3-[4-(5-fluoro-2-methoxyphenyl)-1H-pyrrolo[2,3-b]pyridin-2-yl]piperidin-1-yl}propan-1-amine;
4-(5-fluoro-2-methoxyphenyl)-2-[1-(2-methoxyethyl)piperidin-3-yl]-1H-pyrrolo[2,3-b]pyridine;
4-({trans-4-[4-(5-fluoro-2-methoxyphenyl)-1H-pyrrolo[2,3-b]pyridin-2-yl]cyclohexyl}amino)butanoic acid;
1-{4-[4-(5-fluoro-2-methoxyphenyl)-1H-pyrrolo[2,3-b]pyridin-2-yl]piperidin-1-yl}ethanone;
1-{4-[4-(5-fluoro-2-methoxyphenyl)-1H-pyrrolo[2,3-b]pyridin-2-yl]piperidin-1-yl}-2-hydroxyethanone;
3-methoxy-4-[2-(piperidin-3-yl)-1H-pyrrolo[2,3-b]pyridin-4-yl]benzonitrile;
2-[({trans-4-[4-(5-fluoro-2-methoxyphenyl)-1H-pyrrolo[2,3-b]pyridin-2-yl]cyclohexyl}amino)methyl]cyclopropanecarboxylic acid;
2-(azetidin-3-yl)-4-(5-fluoro-2-methoxyphenyl)-1H-pyrrolo[2,3-b]pyridine;
1-{4-[4-(5-fluoro-2-methoxyphenyl)-1H-pyrrolo[2,3-b]pyridin-2-yl]piperidin-1-yl}-2-(4-hydroxypiperidin-1-yl)ethanone;
4-(5-fluoro-2-methoxyphenyl)-2-[1-(methylsulfonyl)piperidin-4-yl]-1H-pyrrolo[2,3-b]pyridine;
3-{4-[4-(5-fluoro-2-methoxyphenyl)-1H-pyrrolo[2,3-b]pyridin-2-yl]piperidin-1-yl}propane-1,2-diol;
4-[4-(5-fluoro-2-methoxyphenyl)-1H-pyrrolo[2,3-b]pyridin-2-yl]tetrahydro-2H-pyran-4-ol;
4-(5-fluoro-2-methoxyphenyl)-2-[1-(pyridin-4-ylmethyl)azetidin-3-yl]-1H-pyrrolo[2,3-b]pyridine;
1-{3-[4-(5-fluoro-2-methoxyphenyl)-1H-pyrrolo[2,3-b]pyridin-2-yl]azetidin-1-yl}ethanone;
2-{3-[4-(5-fluoro-2-methoxyphenyl)-1H-pyrrolo[2,3-b]pyridin-2-yl]azetidin-1-yl}ethanamine;
4-(5-fluoro-2-methoxyphenyl)-2-[1-(tetrahydro-2H-pyran-4-ylmethyl)azetidin-3-yl]-1H-pyrrolo[2,3-b]pyridine;
4-(5-fluoro-2-methoxyphenyl)-2-{1-[2-(morpholin-4-yl)ethyl]azetidin-3-yl}-1H-pyrrolo[2,3-b]pyridine;
2-{3-[4-(5-fluoro-2-methoxyphenyl)-1H-pyrrolo[2,3-b]pyridin-2-yl]azetidin-1-yl}ethanol;
1-{4-[4-(5-fluoro-2-methoxyphenyl)-1H-pyrrolo[2,3-b]pyridin-2-yl]piperidin-1-yl}-2-(piperidin-1-yl)ethanone;
1-{4-[4-(5-fluoro-2-methoxyphenyl)-1H-pyrrolo[2,3-b]pyridin-2-yl]piperidin-1-yl}-2-(morpholin-4-yl)ethanone;
1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone;
1-{4-[4-(5-fluoro-2-methoxyphenyl)-1H-pyrrolo[2,3-b]pyridin-2-yl]piperidin-1-yl}-2-[(2-hydroxyethyl)amino]ethanone;
4-(5-fluoro-2-methoxyphenyl)-2-(1-methylazetidin-3-yl)-1H-pyrrolo[2,3-b]pyridine;
4-(5-fluoro-2-methoxyphenyl)-2-[1-(methylsulfonyl)azetidin-3-yl]-1H-pyrrolo[2,3-b]pyridine;
3-{4-[4-(5-fluoro-2-methoxyphenyl)-1H-pyrrolo[2,3-b]pyridin-2-yl]-3,6-dihydropyridin-1(2H)-yl}propane-1,2-diol;
2-(azepan-3-yl)-4-(5-fluoro-2-methoxyphenyl)-1H-pyrrolo[2,3-b]pyridine;
4-(4,5-difluoro-2-methoxyphenyl)-2-(piperidin-3-yl)-1H-pyrrolo[2,3-b]pyridine;
4-[4-(5-fluoro-2-methoxyphenyl)-1H-pyrrolo[2,3-b]pyridin-2-yl]-N-methyl-3,6-dihydropyridine-1(2H)-carboxamide;
4-[4-(5-fluoro-2-methoxyphenyl)-1H-pyrrolo[2,3-b]pyridin-2-yl]-3,6-dihydropyridine-1(2H)-sulfonamide;
N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide;
tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-[4-(5-fluoro-2-methoxyphenyl)-1H-pyrrolo[2,3-b]pyridin-2-yl]cyclohex-3-ene-1-carboxylic acid;
3-{4-[4-(5-fluoro-2-methoxyphenyl)-1H-pyrrolo[2,3-b]pyridin-2-yl]-3,6-dihydropyridin-1(2H)-yl}-3-oxopropanenitrile;
4-(5-fluoro-2-methoxyphenyl)-2-[8-(methylsulfonyl)-8-azabicyclo[3.2.1]oct-2-en-3-yl]-1H-pyrrolo[2,3-b]pyridine;
2-{4-[4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide;

{4-[4-(5-fluoro-2-methoxyphenyl)-1H-pyrrolo[2,3-b]pyridin-2-yl]-3,6-dihydropyridin-1(2H)-yl}acetic acid;

2-{4-[4-(5-fluoro-2-methoxyphenyl)-1H-pyrrolo[2,3-b]pyridin-2-yl]-3,6-dihydropyridin-1(2H)-yl}acetamide;

ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[5-chloro-4-(5-fluoro-2-methoxyphenyl)-1H-pyrrolo[2,3-b]pyridin-2-yl]-N-methyl-3,6-dihydropyridine-1(2H)-carboxamide;

4-(5-fluoro-2-methoxyphenyl)-2-[1-(S-methylsulfonimidoyl)-1,2,3,6-tetrahydropyridin-4-yl]-1H-pyrrolo[2,3-b]pyridine;

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(4,5-difluoro-2-methoxyphenyl)-1H-pyrrolo[2,3-b]pyridin-2-yl]-N-methyl-3,6-dihydropyridine-1(2H)-carboxamide;

2-{3-[4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{4-[4-(5-fluoro-2-methoxyphenyl)-1H-pyrrolo[2,3-b]pyridin-2-yl]piperidin-1-yl}-N,N-dimethylacetamide;

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide;

ethyl ({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{4-[4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone;

N-{4-[4-(5-fluoro-2-methoxyphenyl)-1H-pyrrolo[2,3-b]pyridin-2-yl]cyclohex-3-en-1-yl}-D-valine;

1-{4-[4-(5-fluoro-2-methoxyphenyl)-1H-pyrrolo[2,3-b]pyridin-2-yl]cyclohex-3-en-1-yl}-L-proline;

N-cyano-4-[4-(5-fluoro-2-methoxyphenyl)-1H-pyrrolo[2,3-b]pyridin-2-yl]-3,6-dihydropyridine-1(2H)-carboxamide;

1-({4-[4-(5-fluoro-2-methoxyphenyl)-1H-pyrrolo[2,3-b]pyridin-2-yl]-3,6-dihydropyridin-1(2H)-yl}acetyl)-L-prolinamide;

2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]piperidin-1-yl}-N-methylacetamide;

2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;

ethyl ({4-[4-(5-fluoro-2-methoxyphenyl)-1H-pyrrolo[2,3-b]pyridin-2-yl]cyclohex-3-en-1-yl}sulfamoyl)carbamate;

2-{4-[4-(5-fluoro-2-methoxyphenyl)-1H-pyrrolo[2,3-b]pyridin-2-yl]piperidin-1-yl}-N-(2-hydroxyethyl)-N-methylacetamide;

2-{4-[4-(5-fluoro-2-methoxyphenyl)-1H-pyrrolo[2,3-b]pyridin-2-yl]piperidin-1-yl}-N-(3-hydroxycyclobutyl)acetamide;

2-{4-[4-(5-fluoro-2-methoxyphenyl)-1H-pyrrolo[2,3-b]pyridin-2-yl]piperidin-1-yl}-1-(3-hydroxyazetidin-1-yl)ethanone;

N-{4-[4-(5-fluoro-2-methoxyphenyl)-1H-pyrrolo[2,3-b]pyridin-2-yl]cyclohex-3-en-1-yl}-3-methyl-L-valine;

2-{4-[5-fluoro-4-(5-fluoro-2-methoxyphenyl)-1H-pyrrolo[2,3-b]pyridin-2-yl]piperidin-1-yl}-N,N-dimethylacetamide;

2-{4-[4-(2-methoxyphenyl)-1H-pyrrolo[2,3-b]pyridin-2-yl]piperidin-1-yl}-N,N-dimethylacetamide;

4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;

2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone;

2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;

2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;

4-(5-fluoro-2-methoxyphenyl)-2-((3aS,6aR)-2-(methylsulfonyl)-1,2,3,3a,4,6a-hexahydrocyclopenta[c]pyrrol-5-yl)-1H-pyrrolo[2,3-b]pyridine;

4-(5-fluoro-2-methoxyphenyl)-2-((3aR,6aS)-2-(methylsulfonyl)-1,2,3,3a,4,6a-hexahydrocyclopenta[c]pyrrol-5-yl)-1H-pyrrolo[2,3-b]pyridine;

2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;

2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;

2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine;

2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine;

2-{4-[4-(5-fluoro-2-methoxyphenyl)-1H-pyrrolo[2,3-b]pyridin-2-yl]-2,2-dimethyl-3,6-dihydropyridin-1(2H)-yl}-N,N-dimethylacetamide;

4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine;

2-{4-[5-cyano-4-(5-fluoro-2-methoxyphenyl)-1H-pyrrolo[2,3-b]pyridin-2-yl]piperidin-1-yl}-N,N-dimethylacetamide;

2-{4-[4-(5-fluoro-2-methoxyphenyl)-1H-pyrrolo[2,3-b]pyridin-2-yl]piperidin-1-yl}-N-(3-hydroxycyclobutyl)-N-methylacetamide;

4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

4-[5-fluoro-4-(5-fluoro-2-methoxyphenyl)-1H-pyrrolo[2,3-b]pyridin-2-yl]cyclohex-3-ene-1-carboxylic acid;

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-hydroxyethanone;

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-3-oxopropanenitrile;

5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile;

(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;

(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;

5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;

(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;

4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-methyl-2-oxoethanesulfonamide;

4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone;

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile;

2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide; and pharmaceutically acceptable salts thereof.

2-[1-(cyclopropylsulfonyl)-1,2,3,6-tetrahydropyridin-4-yl]-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]tetrahydro-2H-thiopyran-4-ol 1,1-dioxide;

2-(1,1-dioxido-3,6-dihydro-2H-thiopyran-4-yl)-4-(5-fluoro-2-methoxyphenyl)-1H-pyrrolo[2,3-b]pyridine;

3-[4-(5-fluoro-2-methoxyphenyl)-1H-pyrrolo[2,3-b]pyridin-2-yl]pyrrolidin-3-ol;

2-(2,5-dihydro-1H-pyrrol-3-yl)-4-(5-fluoro-2-methoxyphenyl)-1H-pyrrolo[2,3-b]pyridine;

2-{1-[(chloromethyl)sulfonyl]-1,2,3,6-tetrahydropyridin-4-yl}-4-(5-fluoro-2-methoxyphenyl)-1H-pyrrolo[2,3-b]pyridine;

4-(5-fluoro-2-methoxyphenyl)-2-[1-(propan-2-ylsulfonyl)-1,2,3,6-tetrahydropyridin-4-yl]-1H-pyrrolo[2,3-b]pyridine;

4-(5-fluoro-2-methoxyphenyl)-2-[1-(propylsulfonyl)-1,2,3,6-tetrahydropyridin-4-yl]-1H-pyrrolo[2,3-b]pyridine;

2-{1-[(1,1-dioxidotetrahydrothiophen-3-yl)sulfonyl]-1,2,3,6-tetrahydropyridin-4-yl}-4-(5-fluoro-2-methoxyphenyl)-1H-pyrrolo[2,3-b]pyridine;

4-(5-fluoro-2-methoxyphenyl)-2-{1-[(2,2,2-trifluoroethyl)sulfonyl]-1,2,3,6-tetrahydropyridin-4-yl}-1H-pyrrolo[2,3-b]pyridine;

trans-4-[4-(5-fluoro-2-methoxyphenyl)-1H-pyrrolo[2,3-b]pyridin-2-yl]-N-{[1-(methoxymethyl)-1H-1,2,3-triazol-4-yl]methyl}cyclohexanamine;

trans-4-[4-(5-fluoro-2-methoxyphenyl)-1H-pyrrolo[2,3-b]pyridin-2-yl]-N-{[1-(methoxymethyl)-1H-1,2,3-triazol-5-yl]methyl}cyclohexanamine;

4-(5-fluoro-2-methoxyphenyl)-2-[1-(thiophen-2-ylsulfonyl)-1,2,3,6-tetrahydropyridin-4-yl]-1H-pyrrolo[2,3-b]pyridine;

N-[2-chloro-4-({4-[4-(5-fluoro-2-methoxyphenyl)-1H-pyrrolo[2,3-b]pyridin-2-yl]-3,6-dihydropyridin-1(2H)-yl}sulfonyl)phenyl]acetamide;

4-(5-fluoro-2-methoxyphenyl)-2-{1-[(2,4,5-trichlorophenyl)sulfonyl]-1,2,3,6-tetrahydropyridin-4-yl}-1H-pyrrolo[2,3-b]pyridine;

4-({4-[4-(5-fluoro-2-methoxyphenyl)-1H-pyrrolo[2,3-b]pyridin-2-yl]-3,6-dihydropyridin-1(2H)-yl}sulfonyl)-2,1,3-benzoxadiazole;

2-{1-[(3,5-dimethyl-1,2-oxazol-4-yl)sulfonyl]-1,2,3,6-tetrahydropyridin-4-yl}-4-(5-fluoro-2-methoxyphenyl)-1H-pyrrolo[2,3-b]pyridine;

3-[4-(5-fluoro-2-methoxyphenyl)-1H-pyrrolo[2,3-b]pyridin-2-yl]azetidin-3-ol;

4-[4-(5-fluoro-2-methoxyphenyl)-1H-pyrrolo[2,3-b]pyridin-2-yl]-1-(methylsulfonyl)piperidin-4-ol;

2-(1-benzylpiperidin-4-yl)-4-(5-fluoro-2-methoxyphenyl)-1H-pyrrolo[2,3-b]pyridine;

4-(5-fluoro-2-methoxyphenyl)-2-(1-methyl-1,2,3,6-tetrahydropyridin-4-yl)-1H-pyrrolo[2,3-b]pyridine;
4-(5-fluoro-2-methoxyphenyl)-2-(2,2,6,6-tetramethyl-1,2,3,6-tetrahydropyridin-4-yl)-1H-pyrrolo[2,3-b]pyridine;
2-({4-[4-(5-fluoro-2-methoxyphenyl)-1H-pyrrolo[2,3-b]pyridin-2-yl]piperidin-1-yl}methyl)-1H-benzimidazole;
4-(5-fluoro-2-methoxyphenyl)-2-[1-(tetrahydrofuran-2-ylmethyl)piperidin-4-yl]-1H-pyrrolo[2,3-b]pyridine;
2-[1-(5,6-dihydro-2H-pyran-3-ylmethyl)piperidin-4-yl]-4-(5-fluoro-2-methoxyphenyl)-1H-pyrrolo[2,3-b]pyridine;
4-(5-fluoro-2-methoxyphenyl)-2-[1-(4-methoxybenzyl)piperidin-4-yl]-1H-pyrrolo[2,3-b]pyridine;
4-(5-fluoro-2-methoxyphenyl)-2-{1-[2-(morpholin-4-yl)ethyl]piperidin-4-yl}-1H-pyrrolo[2,3-b]pyridine;
4-({4-[4-(5-fluoro-2-methoxyphenyl)-1H-pyrrolo[2,3-b]pyridin-2-yl]piperidin-1-yl}methyl)benzonitrile;
1-(2-{4-[4-(5-fluoro-2-methoxyphenyl)-1H-pyrrolo[2,3-b]pyridin-2-yl]-3,6-dihydropyridin-1(2H)-yl}ethyl)-3-methylurea;
4-(5-fluoro-2-methoxyphenyl)-2-[1-(2-methylpropyl)piperidin-4-yl]-1H-pyrrolo[2,3-b]pyridine;
N-[4-({4-[4-(5-fluoro-2-methoxyphenyl)-1H-pyrrolo[2,3-b]pyridin-2-yl]piperidin-1-yl}methyl)phenyl]acetamide;
4-(5-fluoro-2-methoxyphenyl)-2-[1-(pyridin-2-ylmethyl)piperidin-4-yl]-1H-pyrrolo[2,3-b]pyridine;
4-({4-[4-(5-fluoro-2-methoxyphenyl)-1H-pyrrolo[2,3-b]pyridin-2-yl]piperidin-1-yl}methyl)-N,N-dimethylaniline;
2-{1-[(1-tert-butyl-1H-pyrazol-4-yl)methyl]piperidin-4-yl}-4-(5-fluoro-2-methoxyphenyl)-1H-pyrrolo[2,3-b]pyridine;
4-(5-fluoro-2-methoxyphenyl)-2-[1-(2-methoxyethyl)piperidin-4-yl]-1H-pyrrolo[2,3-b]pyridine;
4-(5-fluoro-2-methoxyphenyl)-2-[1-(pyridin-4-ylmethyl)piperidin-4-yl]-1H-pyrrolo[2,3-b]pyridine;
N,N-diethyl-2-[4-({4-[4-(5-fluoro-2-methoxyphenyl)-1H-pyrrolo[2,3-b]pyridin-2-yl]piperidin-1-yl}methyl)phenoxy]ethanamine;
4-chloro-5-({4-[4-(5-fluoro-2-methoxyphenyl)-1H-pyrrolo[2,3-b]pyridin-2-yl]piperidin-1-yl}methyl)-1,3-thiazol-2-amine;
2-[1-(1,3-benzodioxol-5-ylmethyl)piperidin-4-yl]-4-(5-fluoro-2-methoxyphenyl)-1H-pyrrolo[2,3-b]pyridine;
4-(5-fluoro-2-methoxyphenyl)-2-{1-[2-(morpholin-4-yl)ethyl]-1,2,3,6-tetrahydropyridin-4-yl}-1H-pyrrolo[2,3-b]pyridine;
2-{1-[(3-chlorobenzyl)sulfonyl]-1,2,3,6-tetrahydropyridin-4-yl}-4-(5-fluoro-2-methoxyphenyl)-1H-pyrrolo[2,3-b]pyridine;
4-[4-(5-fluoro-2-methoxyphenyl)-1H-pyrrolo[2,3-b]pyridin-2-yl]-N-(propan-2-yl)-3,6-dihydropyridine-1(2H)-carboxamide;
2-(1-ethyl-1,2,3,6-tetrahydropyridin-4-yl)-4-(5-fluoro-2-methoxyphenyl)-1H-pyrrolo[2,3-b]pyridine;
2-(1-benzyl-1,2,3,6-tetrahydropyridin-4-yl)-4-(5-fluoro-2-methoxyphenyl)-1H-pyrrolo[2,3-b]pyridine;
4-(5-fluoro-2-methoxyphenyl)-2-[4-(pyrrolidin-1-yl)cyclohex-1-en-1-yl]-1H-pyrrolo[2,3-b]pyridine;
4-(5-fluoro-2-methoxyphenyl)-2-[1-(methylsulfonyl)-2,5-dihydro-1H-pyrrol-3-yl]-1H-pyrrolo[2,3-b]pyridine;
2-({4-[4-(5-fluoro-2-methoxyphenyl)-1H-pyrrolo[2,3-b]pyridin-2-yl]-3,6-dihydropyridin-1(2H)-yl}methyl)-1H-benzimidazole;
2-[1-(5,6-dihydro-2H-pyran-3-ylmethyl)-1,2,3,6-tetrahydropyridin-4-yl]-4-(5-fluoro-2-methoxyphenyl)-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)-N,N-dimethylaniline;
N,N-diethyl-2-[4-({4-[4-(5-fluoro-2-methoxyphenyl)-1H-pyrrolo[2,3-b]pyridin-2-yl]-3,6-dihydropyridin-1(2H)-yl}methyl)phenoxy]ethanamine;
4-(5-fluoro-2-methoxyphenyl)-2-[1-(pyridin-4-ylmethyl)-1,2,3,6-tetrahydropyridin-4-yl]-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)benzonitrile;
4-chloro-5-({4-[4-(5-fluoro-2-methoxyphenyl)-1H-pyrrolo[2,3-b]pyridin-2-yl]-3,6-dihydropyridin-1(2H)-yl}methyl)-1,3-thiazol-2-amine;
4-(5-fluoro-2-methoxyphenyl)-2-[1-(tetrahydrofuran-2-ylmethyl)-1,2,3,6-tetrahydropyridin-4-yl]-1H-pyrrolo[2,3-b]pyridine;
5-fluoro-4-(5-fluoro-2-methoxyphenyl)-2-(piperidin-4-yl)-1H-pyrrolo[2,3-b]pyridine;
N-cyclohexyl-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-(4-methoxybenzyl)-3,6-dihydropyridine-1(2H)-carboxamide;
4-[4-(5-fluoro-2-methoxyphenyl)-1H-pyrrolo[2,3-b]pyridin-2-yl]-N-phenyl-3,6-dihydropyridine-1(2H)-carboxamide;
5-fluoro-4-(5-fluoro-2-methoxyphenyl)-2-[1-(methylsulfonyl)piperidin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]piperidin-1-yl}propane-1,2-diol;
1-{4-[5-fluoro-4-(5-fluoro-2-methoxyphenyl)-1H-pyrrolo[2,3-b]pyridin-2-yl]piperidin-1-yl}ethanone;
4-[4-(5-fluoro-2-methoxyphenyl)-1H-pyrrolo[2,3-b]pyridin-2-yl]-N-[2-(morpholin-4-yl)ethyl]-3,6-dihydropyridine-1(2H)-carboxamide;
4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine;
{4-[4-(5-fluoro-2-methoxyphenyl)-1H-pyrrolo[2,3-b]pyridin-2-yl]-3,6-dihydropyridin-1(2H)-yl}(pyridin-2-yl)methanone;
{4-[4-(5-fluoro-2-methoxyphenyl)-1H-pyrrolo[2,3-b]pyridin-2-yl]-3,6-dihydropyridin-1(2H)-yl}(pyridin-3-yl)methanone;
{4-[4-(5-fluoro-2-methoxyphenyl)-1H-pyrrolo[2,3-b]pyridin-2-yl]-3,6-dihydropyridin-1(2H)-yl}(pyridin-4-yl)methanone;
{4-[4-(5-fluoro-2-methoxyphenyl)-1H-pyrrolo[2,3-b]pyridin-2-yl]-3,6-dihydropyridin-1(2H)-yl}(pyrazin-2-yl)methanone;
4-(5-fluoro-2-methoxyphenyl)-2-[1-(pyrimidin-4-yl)-1,2,3,6-tetrahydropyridin-4-yl]-1H-pyrrolo[2,3-b]pyridine;
4-(5-fluoro-2-methoxyphenyl)-2-[1-(2-methylpyrimidin-4-yl)-1,2,3,6-tetrahydropyridin-4-yl]-1H-pyrrolo[2,3-b]pyridine;
4-(5-fluoro-2-methoxyphenyl)-2-{1-[6-(trifluoromethyl)pyrimidin-4-yl]-1,2,3,6-tetrahydropyridin-4-yl}-1H-pyrrolo[2,3-b]pyridine;
1-{4-[4-(5-fluoro-2-methoxyphenyl)-1H-pyrrolo[2,3-b]pyridin-2-yl]-3,6-dihydropyridin-1(2H)-yl}-3-(piperidin-1-yl)propan-1-one;
{4-[4-(5-fluoro-2-methoxyphenyl)-1H-pyrrolo[2,3-b]pyridin-2-yl]-3,6-dihydropyridin-1(2H)-yl}(1H-pyrazol-4-yl)methanone;

{4-[4-(5-fluoro-2-methoxyphenyl)-1H-pyrrolo[2,3-b]pyridin-2-yl]-3,6-dihydropyridin-1(2H)-yl}(1,3-thiazol-4-yl)methanone;

(3,5-dimethyl-1,2-oxazol-4-yl) {4-[4-(5-fluoro-2-methoxyphenyl)-1H-pyrrolo[2,3-b]pyridin-2-yl]-3,6-dihydropyridin-1(2H)-yl}methanone;

N-(2-{4-[4-(5-fluoro-2-methoxyphenyl)-1H-pyrrolo[2,3-b]pyridin-2-yl]-3,6-dihydropyridin-1(2H)-yl}ethyl)-$N^2,N^2$-dimethylglycinamide;

2-[1-(methylsulfonyl)-1,2,3,6-tetrahydropyridin-4-yl]-4-[2-(trifluoromethoxy)phenyl]-1H-pyrrolo[2,3-b]pyridine;

4-[5-fluoro-2-(propan-2-yloxy)phenyl]-2-[1-(methylsulfonyl)-1,2,3,6-tetrahydropyridin-4-yl]-1H-pyrrolo[2,3-b]pyridine;

4-[2-(cyclopropyloxy)-5-fluorophenyl]-2-[1-(methylsulfonyl)-1,2,3,6-tetrahydropyridin-4-yl]-1H-pyrrolo[2,3-b]pyridine;

4-(5-fluoro-2-methoxyphenyl)-2-(1,2,5,6-tetrahydropyridin-3-yl)-1H-pyrrolo[2,3-b]pyridine;

4-(5-chloro-2-methoxyphenyl)-2-[1-(methylsulfonyl)-1,2,3,6-tetrahydropyridin-4-yl]-1H-pyrrolo[2,3-b]pyridine;

4-[2-methoxy-5-(propan-2-yl)phenyl]-2-[1-(methylsulfonyl)-1,2,3,6-tetrahydropyridin-4-yl]-1H-pyrrolo[2,3-b]pyridine;

4-(2-methoxy-5-methylphenyl)-2-[1-(methylsulfonyl)-1,2,3,6-tetrahydropyridin-4-yl]-1H-pyrrolo[2,3-b]pyridine;

4-(2-methoxyphenyl)-2-[1-(methylsulfonyl)-1,2,3,6-tetrahydropyridin-4-yl]-1H-pyrrolo[2,3-b]pyridine;

4-(5-chloro-2-propoxyphenyl)-2-[1-(methylsulfonyl)-1,2,3,6-tetrahydropyridin-4-yl]-1H-pyrrolo[2,3-b]pyridine;

ethyl 4-[4-(5-fluoro-2-methoxyphenyl)-1H-pyrrolo[2,3-b]pyridin-2-yl]cyclohex-3-ene-1-carboxylate;

4-(2-ethoxy-5-fluorophenyl)-2-[1-(methylsulfonyl)-1,2,3,6-tetrahydropyridin-4-yl]-1H-pyrrolo[2,3-b]pyridine;

4-[2-(2-methylpropoxy)phenyl]-2-[1-(methylsulfonyl)-1,2,3,6-tetrahydropyridin-4-yl]-1H-pyrrolo[2,3-b]pyridine;

(4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid;

4-[4-(5-fluoro-2-methoxyphenyl)-1H-pyrrolo[2,3-b]pyridin-2-yl]-N-methyl-3,6-dihydropyridine-1(2H)-sulfonamide;

4-(5-fluoro-2-methoxyphenyl)-2-[1-(pyridin-2-ylmethyl)-1,2,3,6-tetrahydropyridin-4-yl]-1H-pyrrolo[2,3-b]pyridine;

3-{5-[4-(5-fluoro-2-methoxyphenyl)-1H-pyrrolo[2,3-b]pyridin-2-yl]-3,6-dihydropyridin-1(2H)-yl}propane-1,2-diol;

5-[4-(5-fluoro-2-methoxyphenyl)-1H-pyrrolo[2,3-b]pyridin-2-yl]-N-methyl-3,6-dihydropyridine-1(2H)-carboxamide;

4-(5-fluoro-2-methoxyphenyl)-2-[1-(methylsulfonyl)-1,2,5,6-tetrahydropyridin-3-yl]-1H-pyrrolo[2,3-b]pyridine;

4-(4-fluoro-2-methoxyphenyl)-2-[1-(methylsulfonyl)-1,2,3,6-tetrahydropyridin-4-yl]-1H-pyrrolo[2,3-b]pyridine;

4-(4-fluoro-2-propoxyphenyl)-2-[1-(methylsulfonyl)-1,2,3,6-tetrahydropyridin-4-yl]-1H-pyrrolo[2,3-b]pyridine;

4-(5-fluoro-2-methoxyphenyl)-2-[1-(morpholin-4-ylsulfonyl)-1,2,3,6-tetrahydropyridin-4-yl]-1H-pyrrolo[2,3-b]pyridine;

2-fluoro-N-{4-methoxy-3-[2-(1,2,3,6-tetrahydropyridin-4-yl)-1H-pyrrolo[2,3-b]pyridin-4-yl]benzyl}aniline;

N-{4-methoxy-3-[2-(1,2,3,6-tetrahydropyridin-4-yl)-1H-pyrrolo[2,3-b]pyridin-4-yl]benzyl}tetrahydro-2H-pyran-4-amine;

4-[2-methoxy-5-(morpholin-4-ylmethyl)phenyl]-2-(1,2,3,6-tetrahydropyridin-4-yl)-1H-pyrrolo[2,3-b]pyridine;

N-benzyl-4-[4-(5-fluoro-2-methoxyphenyl)-1H-pyrrolo[2,3-b]pyridin-2-yl]cyclohex-3-ene-1-carboxamide;

N-(3-fluorobenzyl)-4-[4-(5-fluoro-2-methoxyphenyl)-1H-pyrrolo[2,3-b]pyridin-2-yl]cyclohex-3-ene-1-carboxamide;

N-(3,5-difluorobenzyl)-4-[4-(5-fluoro-2-methoxyphenyl)-1H-pyrrolo[2,3-b]pyridin-2-yl]cyclohex-3-ene-1-carboxamide;

N-(2,5-difluorobenzyl)-4-[4-(5-fluoro-2-methoxyphenyl)-1H-pyrrolo[2,3-b]pyridin-2-yl]cyclohex-3-ene-1-carboxamide;

N-(3-chlorobenzyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(pyridin-4-ylmethyl)cyclohex-3-ene-1-carboxamide;

4-[4-(5-fluoro-2-methoxyphenyl)-1H-pyrrolo[2,3-b]pyridin-2-yl]-N-[(3-methyl-1H-pyrazol-5-yl)methyl]cyclohex-3-ene-1-carboxamide;

4-[4-(5-fluoro-2-methoxyphenyl)-1H-pyrrolo[2,3-b]pyridin-2-yl]-N-(tetrahydro-2H-pyran-4-ylmethyl)cyclohex-3-ene-1-carboxamide;

4-[4-(5-fluoro-2-methoxyphenyl)-1H-pyrrolo[2,3-b]pyridin-2-yl]-N-(4-hydroxycyclohexyl)cyclohex-3-ene-1-carboxamide;

(3,3-difluoroazetidin-1-yl) {4-[4-(5-fluoro-2-methoxyphenyl)-1H-pyrrolo[2,3-b]pyridin-2-yl]cyclohex-3-en-1-yl}methanone;

2-(3,6-dihydro-2H-pyran-4-yl)-4-(5-fluoro-2-methoxyphenyl)-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}(tetrahydro-2H-pyran-3-yl)methanone;

1-{5-[4-(5-fluoro-2-methoxyphenyl)-1H-pyrrolo[2,3-b]pyridin-2-yl]-3,6-dihydropyridin-1(2H)-yl}-2-hydroxyethanone;

1-{5-[4-(5-fluoro-2-methoxyphenyl)-1H-pyrrolo[2,3-b]pyridin-2-yl]-3,6-dihydropyridin-1(2H)-yl}ethanone;

N-[4-({5-[4-(5-fluoro-2-methoxyphenyl)-1H-pyrrolo[2,3-b]pyridin-2-yl]-3,6-dihydropyridin-1(2H)-yl}methyl)phenyl]acetamide;

4-(5-fluoro-2-methoxyphenyl)-2-[1-(tetrahydrofuran-2-ylmethyl)-1,2,5,6-tetrahydropyridin-3-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-methylpropan-2-ol;

4-[4-(5-fluoro-2-methoxyphenyl)-1H-pyrrolo[2,3-b]pyridin-2-yl]-N,N-dimethyl-3,6-dihydropyridine-1(2H)-carboxamide;

ethyl ({4-[4-(5-fluoro-2-methoxyphenyl)-1H-pyrrolo[2,3-b]pyridin-2-yl]piperidin-1-yl}sulfonyl)carbamate;

4-[4-(5-fluoro-2-methoxyphenyl)-1H-pyrrolo[2,3-b]pyridin-2-yl]-N-methylpiperidine-1-sulfonamide;

4-[4-(5-fluoro-2-methoxyphenyl)-1H-pyrrolo[2,3-b]pyridin-2-yl]-N,N-dimethylpiperidine-1-sulfonamide;

4-(5-fluoro-2-methoxyphenyl)-2-[4-(trifluoromethyl)cyclohex-1-en-1-yl]-1H-pyrrolo[2,3-b]pyridine;

4-[4-(5-fluoro-2-methoxyphenyl)-1H-pyrrolo[2,3-b]pyridin-2-yl]-N-(tetrahydro-2H-pyran-4-ylmethyl)cyclohex-3-en-1-amine;

2-{4-[4-(5-fluoro-2-methoxyphenyl)-1H-pyrrolo[2,3-b]pyridin-2-yl]piperidin-1-yl}ethanesulfonamide;

N-benzyl-4-[4-(5-fluoro-2-methoxyphenyl)-1H-pyrrolo[2,3-b]pyridin-2-yl]cyclohex-3-en-1-amine;

4-[4-(5-fluoro-2-methoxyphenyl)-1H-pyrrolo[2,3-b]pyridin-2-yl]-N-(pyridin-4-ylmethyl)cyclohex-3-en-1-amine;
4-[4-(5-fluoro-2-methoxyphenyl)-1H-pyrrolo[2,3-b]pyridin-2-yl]-N-(morpholin-2-ylmethyl)cyclohex-3-en-1-amine;
4-(5-fluoro-2-methoxyphenyl)-2-[1-(S-methylsulfonimidoyl)piperidin-4-yl]-1H-pyrrolo[2,3-b]pyridine;
N-ethyl-4-[4-(5-fluoro-2-methoxyphenyl)-1H-pyrrolo[2,3-b]pyridin-2-yl]piperidine-1-sulfonamide;
2-(8-azabicyclo[3.2.1]oct-2-en-3-yl)-4-(5-fluoro-2-methoxyphenyl)-1H-pyrrolo[2,3-b]pyridine;
N-(3,5-difluorobenzyl)-4-[4-(5-fluoro-2-methoxyphenyl)-1H-pyrrolo[2,3-b]pyridin-2-yl]cyclohex-3-en-1-amine;
3-[4-(5-fluoro-2-methoxyphenyl)-1H-pyrrolo[2,3-b]pyridin-2-yl]-N-methyl-8-azabicyclo[3.2.1]oct-2-ene-8-carboxamide;
3-{3-[4-(5-fluoro-2-methoxyphenyl)-1H-pyrrolo[2,3-b]pyridin-2-yl]-8-azabicyclo[3.2.1]oct-2-en-8-yl}propane-1,2-diol;
1-{3-[4-(5-fluoro-2-methoxyphenyl)-1H-pyrrolo[2,3-b]pyridin-2-yl]-8-azabicyclo[3.2.1]oct-2-en-8-yl}-2-hydroxyethanone;
3-[4-(5-fluoro-2-methoxyphenyl)-1H-pyrrolo[2,3-b]pyridin-2-yl]-N,N-dimethyl-8-azabicyclo[3.2.1]oct-2-ene-8-carboxamide;
N-[(2S)-2,3-dihydroxypropyl]-4-[4-(5-fluoro-2-methoxyphenyl)-1H-pyrrolo[2,3-b]pyridin-2-yl]piperidine-1-sulfonamide;
4-[4-(5-fluoro-2-methoxyphenyl)-1H-pyrrolo[2,3-b]pyridin-2-yl]-N-(2-hydroxyethyl)-3,6-dihydropyridine-1(2H)-carboxamide;
4-[4-(5-fluoro-2-methoxyphenyl)-1H-pyrrolo[2,3-b]pyridin-2-yl]-N-(methylsulfonyl)cyclohex-3-ene-1-carboxamide;
5-[4-(5-fluoro-2-methoxyphenyl)-1H-pyrrolo[2,3-b]pyridin-2-yl]-N,N-dimethyl-3,6-dihydropyridine-1(2H)-carboxamide;
4-[4-(5-fluoro-2-methoxyphenyl)-1H-pyrrolo[2,3-b]pyridin-2-yl]-N-(pyridin-3-ylmethyl)cyclohex-3-en-1-amine;
4-[4-(5-fluoro-2-methoxyphenyl)-1H-pyrrolo[2,3-b]pyridin-2-yl]cyclohex-3-ene-1-carboxamide;
4-[4-(5-fluoro-2-methoxyphenyl)-1H-pyrrolo[2,3-b]pyridin-2-yl]-N-[2-(pyrrolidin-1-yl)ethyl]-3,6-dihydropyridine-1(2H)-carboxamide;
4-[4-(5-fluoro-2-methoxyphenyl)-1H-pyrrolo[2,3-b]pyridin-2-yl]-N-[2-(4-hydroxypiperidin-1-yl)ethyl]-3,6-dihydropyridine-1(2H)-carboxamide;
4-[4-(5-fluoro-2-methoxyphenyl)-1H-pyrrolo[2,3-b]pyridin-2-yl]-N-{2-[(tetrahydrofuran-2-ylmethyl)amino]ethyl}-3,6-dihydropyridine-1(2H)-carboxamide;
methyl 4-{2-[({4-[4-(5-fluoro-2-methoxyphenyl)-1H-pyrrolo[2,3-b]pyridin-2-yl]-3,6-dihydropyridin-1(2H)-yl}carbonyl)amino]ethyl}piperazine-1-carboxylate;
N-[2-(3,4-dihydroisoquinolin-2(1H)-yl)ethyl]-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide;
1-{5-[4-(5-fluoro-2-methoxyphenyl)-1H-pyrrolo[2,3-b]pyridin-2-yl]-3,6-dihydropyridin-1(2H)-yl}-2-methylpropan-2-ol;
4-[4-(5-fluoro-2-methoxyphenyl)-1H-pyrrolo[2,3-b]pyridin-2-yl]-N,N-dimethyl-3,6-dihydropyridine-1(2H)-sulfonamide;
4-(2,4-dimethoxyphenyl)-2-(1,2,3,6-tetrahydropyridin-4-yl)-1H-pyrrolo[2,3-b]pyridine;
N-{4-[4-(5-fluoro-2-methoxyphenyl)-1H-pyrrolo[2,3-b]pyridin-2-yl]cyclohex-3-en-1-yl}glycine;
4-[4-(5-fluoro-2-methoxyphenyl)-1H-pyrrolo[2,3-b]pyridin-2-yl]-N-methylcyclohex-3-ene-1-carboxamide;
4-[4-(5-fluoro-2-methoxyphenyl)-1H-pyrrolo[2,3-b]pyridin-2-yl]-N-[(3-hydroxyoxetan-3-yl)methyl]-3,6-dihydropyridine-1(2H)-carboxamide;
methyl {4-[4-(5-fluoro-2-methoxyphenyl)-1H-pyrrolo[2,3-b]pyridin-2-yl]-3,6-dihydropyridin-1(2H)-yl}acetate;
4-(4,5-difluoro-2-methoxyphenyl)-2-(1,2,3,6-tetrahydropyridin-4-yl)-1H-pyrrolo[2,3-b]pyridine;
4-[2-methoxy-4-(1H-pyrazol-1-yl)phenyl]-2-(1,2,3,6-tetrahydropyridin-4-yl)-1H-pyrrolo[2,3-b]pyridine;
4-(2-methoxyphenyl)-2-(1,2,3,6-tetrahydropyridin-4-yl)-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile;
1-{4-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;
4-(5-fluoro-2-methoxyphenyl)-2-(1,2,3,6-tetrahydropyridin-4-yl)-1H-pyrrolo[2,3-b]pyridine-5-carbonitrile;
5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one;
2-{4-[4-(5-fluoro-2-methoxyphenyl)-1H-pyrrolo[2,3-b]pyridin-2-yl]-3,6-dihydropyridin-1(2H)-yl}-N-methylacetamide;
4-(5-fluoro-2-methoxyphenyl)-5-methyl-2-[1-(methylsulfonyl)-1,2,3,6-tetrahydropyridin-4-yl]-1H-pyrrolo[2,3-b]pyridine;
4-(5-fluoro-2-methoxyphenyl)-5-methyl-2-(1,2,3,6-tetrahydropyridin-4-yl)-1H-pyrrolo[2,3-b]pyridine;
N-[{4-[4-(5-fluoro-2-methoxyphenyl)-1H-pyrrolo[2,3-b]pyridin-2-yl]-3,6-dihydropyridin-1(2H)-yl}(methyl)oxido-$\lambda^6$-sulfanylidene]-4-methylbenzenesulfonamide;
4-(2-ethoxy-5-fluorophenyl)-2-(1,2,3,6-tetrahydropyridin-4-yl)-1H-pyrrolo[2,3-b]pyridine;
4-(2,5-dimethoxyphenyl)-2-(1,2,3,6-tetrahydropyridin-4-yl)-1H-pyrrolo[2,3-b]pyridine;
N-[(2S)-2,3-dihydroxypropyl]-4-[4-(5-fluoro-2-methoxyphenyl)-1H-pyrrolo[2,3-b]pyridin-2-yl]cyclohex-3-ene-1-carboxamide;
4-{4-[4-(5-fluoro-2-methoxyphenyl)-1H-pyrrolo[2,3-b]pyridin-2-yl]-3,6-dihydropyridin-1(2H)-yl}cyclohexanol;
1-({4-[4-(5-fluoro-2-methoxyphenyl)-1H-pyrrolo[2,3-b]pyridin-2-yl]-3,6-dihydropyridin-1(2H)-yl}carbonyl)piperidine-4-carboxylic acid;
4-[4-(5-fluoro-2-methoxyphenyl)-1H-pyrrolo[2,3-b]pyridin-2-yl]-N-[2-(4-oxopiperidin-1-yl)ethyl]-3,6-dihydropyridine-1(2H)-carboxamide;
N-[2-(3,3-difluoropiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-[2-(3-hydroxypiperidin-1-yl)ethyl]-3,6-dihydropyridine-1(2H)-carboxamide;
4-[4-(5-fluoro-2-methoxyphenyl)-1H-pyrrolo[2,3-b]pyridin-2-yl]-N-{2-[(3S)-3-hydroxypyrrolidin-1-yl]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[(2-hydroxyethyl)(methyl)amino]ethyl}-3,6-dihydropyridine-1(2H)-carboxamide;
4-[4-(5-fluoro-2-methoxyphenyl)-1H-pyrrolo[2,3-b]pyridin-2-yl]-N-{2-[4-(2-hydroxyethyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-[2-(3-oxopiperazin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypiperidin-1-yl]ethyl}-3,6-dihydropyridine-1(2H)-carboxamide;

4-methoxy-3-[2-(1,2,3,6-tetrahydropyridin-4-yl)-1H-pyrrolo[2,3-b]pyridin-4-yl]benzonitrile;

4-(4-fluoro-2-methoxyphenyl)-2-(1,2,3,6-tetrahydropyridin-4-yl)-1H-pyrrolo[2,3-b]pyridine;

4-[2-(difluoromethoxy)-5-fluorophenyl]-2-(1,2,3,6-tetrahydropyridin-4-yl)-1H-pyrrolo[2,3-b]pyridine;

({4-[4-(5-fluoro-2-methoxyphenyl)-1H-pyrrolo[2,3-b]pyridin-2-yl]-3,6-dihydropyridin-1(2H)-yl}sulfonyl)acetic acid;

4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine;

5-chloro-4-(5-fluoro-2-methoxyphenyl)-2-(1,2,3,6-tetrahydropyridin-4-yl)-1H-pyrrolo[2,3-b]pyridine;

4-(5-fluoro-2-methoxyphenyl)-2-{1-[(tetrahydrofuran-2-ylmethyl)sulfonyl]-1,2,3,6-tetrahydropyridin-4-yl}-1H-pyrrolo[2,3-b]pyridine;

ethyl ({4-[4-(5-fluoro-2-methoxyphenyl)-5-methyl-1H-pyrrolo[2,3-b]pyridin-2-yl]-3,6-dihydropyridin-1(2H)-yl}sulfonyl)carbamate;

(cis-4-{4-[5-fluoro-4-(5-fluoro-2-methoxyphenyl)-1H-pyrrolo[2,3-b]pyridin-2-yl]piperidin-1-yl}cyclohexyl)acetic acid;

4-[4-(5-fluoro-2-methoxyphenyl)-1H-pyrrolo[2,3-b]pyridin-2-yl]-N-(pyridin-2-ylmethyl)cyclohex-3-en-1-amine;

4-[4-(5-fluoro-2-methoxyphenyl)-1H-pyrrolo[2,3-b]pyridin-2-yl]-N-(pyrazin-2-ylmethyl)cyclohex-3-en-1-amine;

4-[4-(5-fluoro-2-methoxyphenyl)-1H-pyrrolo[2,3-b]pyridin-2-yl]-N-(pyrimidin-5-ylmethyl)cyclohex-3-en-1-amine;

4-[4-(5-fluoro-2-methoxyphenyl)-1H-pyrrolo[2,3-b]pyridin-2-yl]-N-(tetrahydrofuran-2-ylmethyl)cyclohex-3-en-1-amine;

4-{5-fluoro-2-[($^2$H$_3$)methyloxy]phenyl}-2-(1,2,3,6-tetrahydropyridin-4-yl)-1H-pyrrolo[2,3-b]pyridine;

4-(4-{5-fluoro-2-[($^2$H$_3$)methyloxy]phenyl}-1H-pyrrolo[2,3-b]pyridin-2-yl)-N-methyl-3,6-dihydropyridine-1(2H)-carboxamide;

4-{5-fluoro-2-[($^2$H$_3$)methyloxy]phenyl}-2-[1-(methylsulfonyl)-1,2,3,6-tetrahydropyridin-4-yl]-1H-pyrrolo[2,3-b]pyridine;

methyl 2-{4-[4-(5-fluoro-2-methoxyphenyl)-1H-pyrrolo[2,3-b]pyridin-2-yl]-3,6-dihydropyridin-1(2H)-yl}propanoate;

5-chloro-4-(5-fluoro-2-methoxyphenyl)-2-[1-(methylsulfonyl)-1,2,3,6-tetrahydropyridin-4-yl]-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone;

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid;

{4-[4-(5-fluoro-2-methoxyphenyl)-1H-pyrrolo[2,3-b]pyridin-2-yl]-3,6-dihydropyridin-1(2H)-yl}[(4S)-2,2,5,5-tetramethyl-1,3-dioxolan-4-yl]methanone;

2-{4-[4-(5-fluoro-2-methoxyphenyl)-1H-pyrrolo[2,3-b]pyridin-2-yl]-3,6-dihydropyridin-1(2H)-yl}propanoic acid;

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid;

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid;

methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

(2S)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

(2R)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

4-(5-fluoro-2-methoxyphenyl)-2-[1-(hydroxyacetyl)-1,2,3,6-tetrahydropyridin-4-yl]-1H-pyrrolo[2,3-b]pyridine-5-carbonitrile;

4-[5-cyano-4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-N-[2-(piperazin-1-yl)ethyl]-3,6-dihydropyridine-1(2H)-carboxamide;

N-[2-(4-aminopiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

N-{2-[(1,3-dihydroxypropan-2-yl)amino]ethyl}-4-[4-(5-fluoro-2-methoxyphenyl)-1H-pyrrolo[2,3-b]pyridin-2-yl]-3,6-dihydropyridine-1(2H)-carboxamide;

3-ethoxy-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;

5-fluoro-4-(5-fluoro-2-methoxyphenyl)-2-(1,2,3,6-tetrahydropyridin-4-yl)-1H-pyrrolo[2,3-b]pyridine;

4-[5-fluoro-4-(5-fluoro-2-methoxyphenyl)-1H-pyrrolo[2,3-b]pyridin-2-yl]-N-methyl-3,6-dihydropyridine-1(2H)-carboxamide;

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]-3,6-dihydropyridin-1(2H)-yl}propane-1,2-diol;

1-{4-[4-(5-fluoro-2-methoxyphenyl)-1H-pyrrolo[2,3-b]pyridin-2-yl]-3,6-dihydropyridin-1(2H)-yl}-2-(methylsulfonyl)ethanone;

ethyl 3-{4-[4-(5-fluoro-2-methoxyphenyl)-1H-pyrrolo[2,3-b]pyridin-2-yl]-3,6-dihydropyridin-1(2H)-yl}-3-oxopropanoate;

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}-3,6-dihydropyridine-1(2H)-carboxamide;

N-(2-{4-[4-(5-fluoro-2-methoxyphenyl)-1H-pyrrolo[2,3-b]pyridin-2-yl]-3,6-dihydropyridin-1(2H)-yl}-2-oxoethyl)methanesulfonamide;

N-({4-[4-(5-fluoro-2-methoxyphenyl)-1H-pyrrolo[2,3-b]pyridin-2-yl]cyclohex-3-en-1-yl}carbonyl)glycine;

3-{4-[4-(5-fluoro-2-methoxyphenyl)-1H-pyrrolo[2,3-b]pyridin-2-yl]-3,6-dihydropyridin-1(2H)-yl}-3-oxopropanoic acid;

4-(4-chloro-2-methoxyphenyl)-2-(1,2,3,6-tetrahydropyridin-4-yl)-1H-pyrrolo[2,3-b]pyridine;

4-(2,4-dimethoxyphenyl)-2-[1-(methylsulfonyl)-1,2,3,6-tetrahydropyridin-4-yl]-1H-pyrrolo[2,3-b]pyridine;

3-{4-[4-(2,4-dimethoxyphenyl)-1H-pyrrolo[2,3-b]pyridin-2-yl]-3,6-dihydropyridin-1(2H)-yl}propane-1,2-diol;

4-[4-(2,4-dimethoxyphenyl)-1H-pyrrolo[2,3-b]pyridin-2-yl]-N-methyl-3,6-dihydropyridine-1(2H)-carboxamide;
1-{4-[4-(2,4-dimethoxyphenyl)-1H-pyrrolo[2,3-b]pyridin-2-yl]-3,6-dihydropyridin-1(2H)-yl}-2-hydroxyethanone;
3-{4-[4-(2-methoxyphenyl)-1H-pyrrolo[2,3-b]pyridin-2-yl]-3,6-dihydropyridin-1(2H)-yl}propane-1,2-diol;
4-[4-(2-methoxyphenyl)-1H-pyrrolo[2,3-b]pyridin-2-yl]-N-methyl-3,6-dihydropyridine-1(2H)-carboxamide;
2-hydroxy-1-{4-[4-(2-methoxyphenyl)-1H-pyrrolo[2,3-b]pyridin-2-yl]-3,6-dihydropyridin-1(2H)-yl}ethanone;
3-{4-[4-(4-fluoro-2-methoxyphenyl)-1H-pyrrolo[2,3-b]pyridin-2-yl]-3,6-dihydropyridin-1(2H)-yl}propane-1,2-diol;
4-[4-(4-fluoro-2-methoxyphenyl)-1H-pyrrolo[2,3-b]pyridin-2-yl]-N-methyl-3,6-dihydropyridine-1(2H)-carboxamide;
1-{4-[4-(4-fluoro-2-methoxyphenyl)-1H-pyrrolo[2,3-b]pyridin-2-yl]-3,6-dihydropyridin-1(2H)-yl}-2-hydroxyethanone;
3-{4-[4-(4,5-difluoro-2-methoxyphenyl)-1H-pyrrolo[2,3-b]pyridin-2-yl]-3,6-dihydropyridin-1(2H)-yl}propane-1,2-diol;
1-{4-[4-(4,5-difluoro-2-methoxyphenyl)-1H-pyrrolo[2,3-b]pyridin-2-yl]-3,6-dihydropyridin-1(2H)-yl}-2-hydroxyethanone;
N-({4-[4-(5-fluoro-2-methoxyphenyl)-1H-pyrrolo[2,3-b]pyridin-2-yl]-3,6-dihydropyridin-1(2H)-yl}sulfonyl)acetamide;
4-(4,5-difluoro-2-methoxyphenyl)-2-[1-(methylsulfonyl)-1,2,3,6-tetrahydropyridin-4-yl]-1H-pyrrolo[2,3-b]pyridine;
{4-[5-cyano-4-(5-fluoro-2-methoxyphenyl)-1H-pyrrolo[2,3-b]pyridin-2-yl]-3,6-dihydropyridin-1(2H)-yl}acetic acid;
4-[4-(5-fluoro-2-methoxyphenyl)-1H-pyrrolo[2,3-b]pyridin-2-yl]-N-(2-{[2-(1H-imidazol-4-yl)ethyl]amino}ethyl)-3,6-dihydropyridine-1(2H)-carboxamide;
4-[4-(5-fluoro-2-methoxyphenyl)-1H-pyrrolo[2,3-b]pyridin-2-yl]-N-{2-[(2-hydroxypropyl)amino]ethyl}-3,6-dihydropyridine-1(2H)-carboxamide;
N-[2-(dimethylamino)ethyl]-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-(2-{[(3-methyloxetan-3-yl)methyl]amino}ethyl)-3,6-dihydropyridine-1(2H)-carboxamide;
4-[4-(5-fluoro-2-methoxyphenyl)-1H-pyrrolo[2,3-b]pyridin-2-yl]-N-[2-(oxetan-3-ylamino)ethyl]-3,6-dihydropyridine-1(2H)-carboxamide;
3-methoxy-N-methyl-4-[2-(1,2,3,6-tetrahydropyridin-4-yl)-1H-pyrrolo[2,3-b]pyridin-4-yl]benzamide;
3-methoxy-N-methyl-4-{2-[1-(methylsulfonyl)-1,2,3,6-tetrahydropyridin-4-yl]-1H-pyrrolo[2,3-b]pyridin-4-yl}benzamide;
4-{2-[1-(2,3-dihydroxypropyl)-1,2,3,6-tetrahydropyridin-4-yl]-1H-pyrrolo[2,3-b]pyridin-4-yl}-3-methoxy-N-methylbenzamide;
3-amino-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;
4-(5-fluoro-2-methoxyphenyl)-2-(2,5,6,7-tetrahydro-14-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,75-tetrahydro-1H-azepin-4-yl)-1H-pyrrolo[2,3-b]pyridine;
4-(5-fluoro-2-methoxyphenyl)-2-[1-(methylsulfonyl)-2,5,6,7-tetrahydro-1H-azepin-4-yl]-1H-pyrrolo[2,3-b]pyridine and 4-(5-fluoro-2-methoxyphenyl)-2-(1-(methylsulfonyl)-2,3,6,7-tetrahydro-1H-azepin-4-yl)-1H-pyrrolo[2,3-b]pyridine;
5-[4-(5-fluoro-2-methoxyphenyl)-1H-pyrrolo[2,3-b]pyridin-2-yl]-N-methyl-2,3,4,7-tetrahydro-1H-azepine-1-carboxamide and 4-(4-(5-fluoro-2-methoxyphenyl)-1H-pyrrolo[2,3-b]pyridin-2-yl)-N-methyl-2,3,6,7-tetrahydro-1H-azepine-1-carboxamide;
1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone;
2-{4-[4-(5-fluoro-2-methoxyphenyl)-1H-pyrrolo[2,3-b]pyridin-2-yl]-3,6-dihydropyridin-1(2H)-yl}-N-(methylsulfonyl)acetamide;
2-{4-[4-(2,4-dimethoxyphenyl)-1H-pyrrolo[2,3-b]pyridin-2-yl]-3,6-dihydropyridin-1(2H)-yl}-N,N-dimethylacetamide;
2-{4-[4-(2-methoxyphenyl)-1H-pyrrolo[2,3-b]pyridin-2-yl]-3,6-dihydropyridin-1(2H)-yl}-N,N-dimethylacetamide;
2-{4-[4-(4-fluoro-2-methoxyphenyl)-1H-pyrrolo[2,3-b]pyridin-2-yl]-3,6-dihydropyridin-1(2H)-yl}-N,N-dimethylacetamide;
2-{4-[4-(4,5-difluoro-2-methoxyphenyl)-1H-pyrrolo[2,3-b]pyridin-2-yl]-3,6-dihydropyridin-1(2H)-yl}-N,N-dimethylacetamide;
tert-butyl {5-[4-(5-fluoro-2-methoxyphenyl)-1H-pyrrolo[2,3-b]pyridin-2-yl]-3,6-dihydropyridin-1(2H)-yl}acetate;
N-({4-[4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;
2-{5-[4-(5-fluoro-2-methoxyphenyl)-1H-pyrrolo[2,3-b]pyridin-2-yl]-3,6-dihydropyridin-1(2H)-yl}-N,N-dimethylacetamide;
{5-[4-(5-fluoro-2-methoxyphenyl)-1H-pyrrolo[2,3-b]pyridin-2-yl]-3,6-dihydropyridin-1(2H)-yl}acetic acid;
ethyl 1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylate;
2-(dimethylamino)-1-{4-[4-(5-fluoro-2-methoxyphenyl)-1H-pyrrolo[2,3-b]pyridin-2-yl]-3,6-dihydropyridin-1(2H)-yl}ethanone;
{4-[5-fluoro-4-(5-fluoro-2-methoxyphenyl)-1H-pyrrolo[2,3-b]pyridin-2-yl]-3,6-dihydropyridin-1(2H)-yl}acetic acid;
2-({4-[4-(5-fluoro-2-methoxyphenyl)-1H-pyrrolo[2,3-b]pyridin-2-yl]cyclohex-3-en-1-yl}amino)butanoic acid;
4-(5-fluoro-2-methoxyphenyl)-2-[1-(methylsulfonyl)azepan-4-yl]-1H-pyrrolo[2,3-b]pyridine;
{3-[4-(5-fluoro-2-methoxyphenyl)-1H-pyrrolo[2,3-b]pyridin-2-yl]-2,5-dihydro-1H-pyrrol-1-yl}acetic acid;
2-{4-[4-(5-fluoro-2-methoxyphenyl)-1H-pyrrolo[2,3-b]pyridin-2-yl]piperidin-1-yl}-N,N-dimethylethanesulfonamide;
{4-[4-(2,4-dimethoxyphenyl)-1H-pyrrolo[2,3-b]pyridin-2-yl]-3,6-dihydropyridin-1(2H)-yl}acetic acid;
{4-[4-(2-methoxyphenyl)-1H-pyrrolo[2,3-b]pyridin-2-yl]-3,6-dihydropyridin-1(2H)-yl}acetic acid;
{4-[4-(4,5-difluoro-2-methoxyphenyl)-1H-pyrrolo[2,3-b]pyridin-2-yl]-3,6-dihydropyridin-1(2H)-yl}acetic acid;
1-{4-[4-(5-fluoro-2-methoxyphenyl)-1H-pyrrolo[2,3-b]pyridin-2-yl]-3,6-dihydropyridin-1(2H)-yl}-2-(3-hydroxypyrrolidin-1-yl)ethanone;
methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate;

{4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetic acid;

N-(cyclopropylsulfonyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(phenylsulfonyl)-3,6-dihydropyridine-1(2H)-carboxamide;

5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one;

{4-[4-(5-fluoro-2-methoxyphenyl)-1H-pyrrolo[2,3-b]pyridin-2-yl]piperidin-1-yl}acetic acid;

{3-[4-(5-fluoro-2-methoxyphenyl)-1H-pyrrolo[2,3-b]pyridin-2-yl]pyrrolidin-1-yl}acetic acid;

4-[4-(5-fluoro-2-methoxyphenyl)-1H-pyrrolo[2,3-b]pyridin-2-yl]-2,5-dihydro-1H-pyrrole-2-carboxylic acid;

{4-[4-(5-fluoro-2-methoxyphenyl)-1H-pyrrolo[2,3-b]pyridin-2-yl]-3,6-dihydropyridin-1(2H)-yl}(1-hydroxycyclopropyl)methanone;

{4-[4-(4-fluoro-2-methoxyphenyl)-1H-pyrrolo[2,3-b]pyridin-2-yl]-3,6-dihydropyridin-1(2H)-yl}acetic acid;

{3-[4-(5-fluoro-2-methoxyphenyl)-1H-pyrrolo[2,3-b]pyridin-2-yl]-8-azabicyclo[3.2.1]oct-2-en-8-yl}acetic acid;

1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylic acid;

1-{5-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-[4-(5-fluoro-2-methoxyphenyl)-1H-pyrrolo[2,3-b]pyridin-2-yl]-N-(propan-2-ylsulfonyl)cyclohex-3-ene-1-carboxamide;

2-{4-[4-(5-fluoro-2-methoxyphenyl)-1H-pyrrolo[2,3-b]pyridin-2-yl]-3,6-dihydropyridin-1(2H)-yl}-2-oxoethanesulfonamide;

2-{4-[4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;

tert-butyl {4-[4-(5-fluoro-2-methoxyphenyl)-1H-pyrrolo[2,3-b]pyridin-2-yl]-3,6-dihydropyridin-1(2H)-yl}acetate;

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}-3,6-dihydropyridine-1(2H)-carboxamide;

4-(5-fluoro-2-methoxyphenyl)-2-[1-(2H-tetrazol-5-ylmethyl)-1,2,3,6-tetrahydropyridin-4-yl]-1H-pyrrolo[2,3-b]pyridine;

6-[4-(5-fluoro-2-methoxyphenyl)-1H-pyrrolo[2,3-b]pyridin-2-yl]-2-azaspiro[3.3]heptan-6-ol;

{(2R)-4-[4-(5-fluoro-2-methoxyphenyl)-1H-pyrrolo[2,3-b]pyridin-2-yl]-2,5-dihydro-1H-pyrrol-2-yl}methanol;

4-[4-(5-fluoro-2-methoxyphenyl)-1H-pyrrolo[2,3-b]pyridin-2-yl]cyclohex-3-en-1-ol;

2-{3-[4-(5-fluoro-2-methoxyphenyl)-1H-pyrrolo[2,3-b]pyridin-2-yl]pyrrolidin-1-yl}-N,N-dimethylacetamide;

3-[4-(5-fluoro-2-methoxyphenyl)-1H-pyrrolo[2,3-b]pyridin-2-yl]cyclopent-3-en-1-amine;

3-[4-(5-fluoro-2-methoxyphenyl)-1H-pyrrolo[2,3-b]pyridin-2-yl]cyclopent-2-en-1-amine;

2-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]-1H-isoindole-1,3(2H)-dione;

3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

4-[4-(5-fluoro-2-methoxyphenyl)-1H-pyrrolo[2,3-b]pyridin-2-yl]-N-(2-{[(1S,2S)-2-hydroxycyclohexyl]amino}ethyl)-3,6-dihydropyridine-1(2H)-carboxamide;

N-(2-{[2-(dimethylamino)ethyl]amino}ethyl)-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(2-methoxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(4-methylbenzoyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(methylsulfonyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-(2-{[3-(trifluoromethyl)benzyl]amino}ethyl)-3,6-dihydropyridine-1(2H)-carboxamide;

2,2,2-trifluoroethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-en-1-one;

2-(3,6-dihydro-2H-thiopyran-4-yl)-4-(5-fluoro-2-methoxyphenyl)-1H-pyrrolo[2,3-b]pyridine;

N-({4-[4-(5-fluoro-2-methoxyphenyl)-1H-pyrrolo[2,3-b]pyridin-2-yl]-3,6-dihydropyridin-1(2H)-yl}carbonyl)alanine;

4-(5-fluoro-2-methoxyphenyl)-2-(1-oxido-3,6-dihydro-2H-thiopyran-4-yl)-1H-pyrrolo[2,3-b]pyridine;

4-[4-(5-fluoro-2-methoxyphenyl)-1H-pyrrolo[2,3-b]pyridin-2-yl]-N-[(1-methylcyclopropyl)sulfonyl]cyclohex-3-ene-1-carboxamide;

4-[4-(5-fluoro-2-methoxyphenyl)-1H-pyrrolo[2,3-b]pyridin-2-yl]-N-[(2-methylpropyl)sulfonyl]cyclohex-3-ene-1-carboxamide;

4-(5-fluoro-2-methoxyphenyl)-2-(1,2,3,6-tetrahydropyridin-4-yl)-1H-pyrrolo[2,3-b]pyridine-5-carboxamide;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-5-carbonitrile;

2-{4-[5-chloro-4-(5-fluoro-2-methoxyphenyl)-1H-pyrrolo[2,3-b]pyridin-2-yl]-3,6-dihydropyridin-1(2H)-yl}-N,N-dimethylacetamide;

{4-[5-chloro-4-(5-fluoro-2-methoxyphenyl)-1H-pyrrolo[2,3-b]pyridin-2-yl]-3,6-dihydropyridin-1(2H)-yl}acetic acid;

3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol;

{4-[4-(5-fluoro-2-methoxyphenyl)-1H-pyrrolo[2,3-b]pyridin-2-yl]-3,6-dihydropyridin-1(2H)-yl}[(2S,4S)-4-hydroxypyrrolidin-2-yl]methanone;

N-[2-(ethylamino)ethyl]-4-[4-(5-fluoro-2-methoxyphenyl)-1H-pyrrolo[2,3-b]pyridin-2-yl]-3,6-dihydropyridine-1(2H)-carboxamide;

N-[2-(cyclopropylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(pyridin-2-ylmethyl)amino]ethyl}-3,6-dihydropyridine-1(2H)-carboxamide;

3-amino-4-{4-[4-(2-{2-[(2-amino-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

tert-butyl 4-({4-[4-(5-fluoro-2-methoxyphenyl)-1H-pyrrolo[2,3-b]pyridin-2-yl]-3,6-dihydropyridin-1(2H)-yl}sulfonyl)piperidine-1-carboxylate;

4-[4-(5-fluoro-2-methoxyphenyl)-1H-pyrrolo[2,3-b]pyridin-2-yl]-1-(methylsulfonyl)-2,5-dihydro-1H-pyrrole-2-carboxylic acid;

4-(5-fluoro-2-methoxyphenyl)-2-[1-(piperidin-4-ylsulfonyl)-1,2,3,6-tetrahydropyridin-4-yl]-1H-pyrrolo[2,3-b]pyridine;

2-{4-[4-(5-fluoro-2-methoxyphenyl)-1H-pyrrolo[2,3-b]pyridin-2-yl]-3,6-dihydropyridin-1(2H)-yl}-N,N-dimethylpropanamide;

4-(4-fluoro-2-methoxyphenyl)-2-[8-(methylsulfonyl)-8-azabicyclo[3.2.1]oct-2-en-3-yl]-1H-pyrrolo[2,3-b]pyridine;

4-(4,5-difluoro-2-methoxyphenyl)-2-[8-(methylsulfonyl)-8-azabicyclo[3.2.1]oct-2-en-3-yl]-1H-pyrrolo[2,3-b]pyridine;

4-(2-methoxyphenyl)-2-[8-(methylsulfonyl)-8-azabicyclo[3.2.1]oct-2-en-3-yl]-1H-pyrrolo[2,3-b]pyridine;

ethyl ({4-[4-(4-fluoro-2-methoxyphenyl)-1H-pyrrolo[2,3-b]pyridin-2-yl]-3,6-dihydropyridin-1(2H)-yl}sulfonyl)carbamate;

ethyl ({4-[4-(2,4-dimethoxyphenyl)-1H-pyrrolo[2,3-b]pyridin-2-yl]-3,6-dihydropyridin-1(2H)-yl}sulfonyl)carbamate;

ethyl ({4-[4-(2-methoxyphenyl)-1H-pyrrolo[2,3-b]pyridin-2-yl]-3,6-dihydropyridin-1(2H)-yl}sulfonyl)carbamate;

ethyl ({4-[4-(4,5-difluoro-2-methoxyphenyl)-1H-pyrrolo[2,3-b]pyridin-2-yl]-3,6-dihydropyridin-1(2H)-yl}sulfonyl)carbamate;

{4-[4-(5-fluoro-2-methoxyphenyl)-1H-pyrrolo[2,3-b]pyridin-2-yl]-3,6-dihydropyridin-1(2H)-yl}[(2S,4R)-4-hydroxypyrrolidin-2-yl]methanone;

{4-[4-(5-fluoro-2-methoxyphenyl)-1H-pyrrolo[2,3-b]pyridin-2-yl]-3,6-dihydropyridin-1(2H)-yl}[(2R,4S)-4-hydroxypyrrolidin-2-yl]methanone;

4-[4-(5-fluoro-2-methoxyphenyl)-1H-pyrrolo[2,3-b]pyridin-2-yl]-N,N-dimethylcyclohex-3-ene-1-carboxamide;

N-{4-[4-(5-fluoro-2-methoxyphenyl)-1H-pyrrolo[2,3-b]pyridin-2-yl]cyclohex-3-en-1-yl}alanine;

2-({4-[4-(5-fluoro-2-methoxyphenyl)-1H-pyrrolo[2,3-b]pyridin-2-yl]-3,6-dihydropyridin-1(2H)-yl}sulfonyl)ethanamine;

4-(5-fluoro-2-methoxyphenyl)-2-(1,2,3,3a,4,6a-hexahydrocyclopenta[c]pyrrol-5-yl)-1H-pyrrolo[2,3-b]pyridine;

tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate;

tert-butyl 4-[4-(5-fluoro-2-methoxyphenyl)-1H-pyrrolo[2,3-b]pyridin-2-yl]-2-[(methylsulfonyl)carbamoyl]-2,5-dihydro-1H-pyrrole-1-carboxylate;

4-(5-fluoro-2-methoxyphenyl)-5-methoxy-2-[1-(methylsulfonyl)-1,2,3,6-tetrahydropyridin-4-yl]-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}serine;

3-[4-(5-fluoro-2-methoxyphenyl)-1H-pyrrolo[2,3-b]pyridin-2-yl]cyclohex-3-ene-1-carboxylic acid;

{4-[4-(5-fluoro-2-methoxyphenyl)-1H-pyrrolo[2,3-b]pyridin-2-yl]-1,2,3,6-tetrahydropyridin-2-yl}methanol;

7-[4-(5-fluoro-2-methoxyphenyl)-1H-pyrrolo[2,3-b]pyridin-2-yl]-3-oxa-9-azabicyclo[3.3.1]non-6-ene;

7-[4-(5-fluoro-2-methoxyphenyl)-1H-pyrrolo[2,3-b]pyridin-2-yl]-9-(methylsulfonyl)-3-oxa-9-azabicyclo[3.3.1]non-6-ene;

ethyl ({7-[4-(5-fluoro-2-methoxyphenyl)-1H-pyrrolo[2,3-b]pyridin-2-yl]-3-oxa-9-azabicyclo[3.3.1]non-6-en-9-yl}sulfonyl)carbamate;

2-{7-[4-(5-fluoro-2-methoxyphenyl)-1H-pyrrolo[2,3-b]pyridin-2-yl]-3-oxa-9-azabicyclo[3.3.1]non-6-en-9-yl}-N,N-dimethylacetamide;

N-{4-[4-(5-fluoro-2-methoxyphenyl)-1H-pyrrolo[2,3-b]pyridin-2-yl]cyclohex-3-en-1-yl}-L-isoleucine;

1-{4-[4-(5-fluoro-2-methoxyphenyl)-1H-pyrrolo[2,3-b]pyridin-2-yl]-3,6-dihydropyridin-1(2H)-yl}-3-(3-hydroxyazetidin-1-yl)propane-1,3-dione;

[(2S)-4-[4-(5-fluoro-2-methoxyphenyl)-1H-pyrrolo[2,3-b]pyridin-2-yl]-1-(methylsulfonyl)-2,5-dihydro-1H-pyrrol-2-yl]methanol;

ethyl {[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]sulfonyl}carbamate;

2-({4-[4-(5-fluoro-2-methoxyphenyl)-1H-pyrrolo[2,3-b]pyridin-2-yl]-3,6-dihydropyridin-1(2H)-yl}sulfonyl)-1-(3-hydroxyazetidin-1-yl)ethanone;

{(2S)-4-[4-(5-fluoro-2-methoxyphenyl)-1H-pyrrolo[2,3-b]pyridin-2-yl]-2,5-dihydro-1H-pyrrol-2-yl}methanol;

8-[4-(5-fluoro-2-methoxyphenyl)-1H-pyrrolo[2,3-b]pyridin-2-yl]-1,3-diazaspiro[4.5]dec-7-ene-2,4-dione;

1-amino-4-[4-(5-fluoro-2-methoxyphenyl)-1H-pyrrolo[2,3-b]pyridin-2-yl]cyclohex-3-ene-1-carboxylic acid;

2-(2-azaspiro[3.3]hept-6-yl)-4-(5-fluoro-2-methoxyphenyl)-1H-pyrrolo[2,3-b]pyridine;

4-(5-fluoro-2-methoxyphenyl)-5-methoxy-2-(1,2,3,6-tetrahydropyridin-4-yl)-1H-pyrrolo[2,3-b]pyridine;

4-(5-fluoro-2-methoxyphenyl)-2-(1-{[1-(methylsulfonyl)piperidin-4-yl]sulfonyl}-1,2,3,6-tetrahydropyridin-4-yl)-1H-pyrrolo[2,3-b]pyridine;

N-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]methanesulfonamide;

{4-[4-(5-fluoro-2-methoxyphenyl)-1H-pyrrolo[2,3-b]pyridin-2-yl]-1-(methylsulfonyl)-1,2,3,6-tetrahydropyridin-2-yl}methanol;

ethyl ({4-[4-(5-fluoro-2-methoxyphenyl)-1H-pyrrolo[2,3-b]pyridin-2-yl]-2-(hydroxymethyl)-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-2-(hydroxymethyl)-3,6-dihydropyridin-1(2H)-yl}-N,N-dimethylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-[4-(5-fluoro-2-methoxyphenyl)-1H-pyrrolo[2,3-b]pyridin-2-yl]-N,N-dimethyl-2,5-dihydro-1H-pyrrole-2-carboxamide;

2-(4-{4-[4-(5-fluoro-2-methoxyphenyl)-1H-pyrrolo[2,3-b]pyridin-2-yl]-3,6-dihydropyridin-1(2H)-yl}piperidin-1-yl)-N,N-dimethylacetamide;

N-{4-[4-(2,3-difluorophenyl)-1H-pyrrolo[2,3-b]pyridin-2-yl]cyclohex-3-en-1-yl}glycine;

1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone;

4-(5-fluoro-2-methoxyphenyl)-2-(1-{[1-(methylsulfonyl)azetidin-3-yl]sulfonyl}-1,2,3,6-tetrahydropyridin-4-yl)-1H-pyrrolo[2,3-b]pyridine;

4-(5-fluoro-2-methoxyphenyl)-2-(2,3,6,7-tetrahydro-1H-azepin-4-yl)-1H-pyrrolo[2,3-b]pyridine;

3-(2-{4-[4-(5-fluoro-2-methoxyphenyl)-1H-pyrrolo[2,3-b]pyridin-2-yl]-3,6-dihydropyridin-1(2H)-yl}-2-oxoethyl)imidazolidine-2,4-dione;

({4-[4-(5-fluoro-2-methoxyphenyl)-1H-pyrrolo[2,3-b]pyridin-2-yl]-3,6-dihydropyridin-1(2H)-yl}sulfonyl)acetonitrile;

propan-2-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-(5-fluoro-2-methoxyphenyl)-2-[2-(methylsulfonyl)-2-azaspiro[3.3]hept-6-yl]-1H-pyrrolo[2,3-b]pyridine;

ethyl ({4-[5-cyano-4-(5-fluoro-2-methoxyphenyl)-1H-pyrrolo[2,3-b]pyridin-2-yl]-3,6-dihydropyridin-1(2H)-yl}sulfonyl)carbamate;

N-[2-(4-fluoro-2-{2-[1-(methylsulfonyl)-1,2,3,6-tetrahydropyridin-4-yl]-1H-pyrrolo[2,3-b]pyridin-4-yl}phenoxy)ethyl]methanesulfonamide;

2-{4-fluoro-2-[2-(1,2,3,6-tetrahydropyridin-4-yl)-1H-pyrrolo[2,3-b]pyridin-4-yl]phenoxy}ethanamine;

N-[4-({4-[4-(5-fluoro-2-methoxyphenyl)-1H-pyrrolo[2,3-b]pyridin-2-yl]-3,6-dihydropyridin-1(2H)-yl}methyl)phenyl]methanesulfonamide;

1-amino-4-[4-(5-fluoro-2-methoxyphenyl)-1H-pyrrolo[2,3-b]pyridin-2-yl]-N,N-dimethylcyclohex-3-ene-1-carboxamide;

1-(3-{4-[4-(5-fluoro-2-methoxyphenyl)-1H-pyrrolo[2,3-b]pyridin-2-yl]-3,6-dihydropyridin-1(2H)-yl}-3-oxopropanoyl)prolinamide;

N-ethoxy-4-[4-(5-fluoro-2-methoxyphenyl)-1H-pyrrolo[2,3-b]pyridin-2-yl]cyclohex-3-ene-1-carboxamide;

ethyl ({3-[4-(5-fluoro-2-methoxyphenyl)-1H-pyrrolo[2,3-b]pyridin-2-yl]-8-azabicyclo[3.2.1]oct-2-en-8-yl}sulfonyl)carbamate;

4-[4-(5-fluoro-2-methoxyphenyl)-1H-pyrrolo[2,3-b]pyridin-2-yl]-N-(4-methoxybenzyl)cyclohex-3-ene-1-sulfonamide;

methyl 4-[4-(5-fluoro-2-methoxyphenyl)-1H-pyrrolo[2,3-b]pyridin-2-yl]-3,6-dihydro-2H-1,2'-bipyridine-3'-carboxylate;

1-({4-[4-(5-fluoro-2-methoxyphenyl)-1H-pyrrolo[2,3-b]pyridin-2-yl]piperidin-1-yl}acetyl)-L-prolinamide;

1-tert-butyl 2-methyl (2S)-4-{4-[4-(5-fluoro-2-methoxyphenyl)-1H-pyrrolo[2,3-b]pyridin-2-yl]-3,6-dihydropyridin-1(2H)-yl}pyrrolidine-1,2-dicarboxylate;

4-[4-(5-fluoro-2-methoxyphenyl)-1H-pyrrolo[2,3-b]pyridin-2-yl]-3,6-dihydro-2H-1,2'-bipyridine-3'-carboxylic acid;

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide;

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)methanesulfonamide;

3-{4-[4-(5-fluoro-2-methoxyphenyl)-1H-pyrrolo[2,3-b]pyridin-2-yl]-3,6-dihydropyridin-1(2H)-yl}-4-hydroxycyclobut-3-ene-1,2-dione;

methyl 4-{4-[4-(5-fluoro-2-methoxyphenyl)-1H-pyrrolo[2,3-b]pyridin-2-yl]-3,6-dihydropyridin-1(2H)-yl}-L-prolinate;

methyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-prolinate;

ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate;

4-[4-(5-fluoro-2-methoxyphenyl)-1H-pyrrolo[2,3-b]pyridin-2-yl]cyclohex-3-ene-1-sulfonamide;

ethyl ({6-[4-(5-fluoro-2-methoxyphenyl)-1H-pyrrolo[2,3-b]pyridin-2-yl]-2-azaspiro[3.3]hept-2-yl}sulfonyl)carbamate;

3-{6-[4-(5-fluoro-2-methoxyphenyl)-1H-pyrrolo[2,3-b]pyridin-2-yl]-2-azaspiro[3.3]hept-2-yl}propane-1,2-diol;

2-{6-[4-(5-fluoro-2-methoxyphenyl)-1H-pyrrolo[2,3-b]pyridin-2-yl]-2-azaspiro[3.3]hept-2-yl}-N,N-dimethylacetamide;

2-({4-[4-(5-fluoro-2-methoxyphenyl)-1H-pyrrolo[2,3-b]pyridin-2-yl]-3,6-dihydropyridin-1(2H)-yl}sulfonyl)-N-(3-hydroxycyclobutyl)acetamide;

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-proline;

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylic acid;

2-[1-(azetidin-1-ylsulfonyl)-1,2,3,6-tetrahydropyridin-4-yl]-4-(5-fluoro-2-methoxyphenyl)-1H-pyrrolo[2,3-b]pyridine;

1-({4-[4-(5-fluoro-2-methoxyphenyl)-1H-pyrrolo[2,3-b]pyridin-2-yl]-3,6-dihydropyridin-1(2H)-yl}sulfonyl)azetidine-3-carbonitrile;

2-{1-[(4,4-difluoropiperidin-1-yl)sulfonyl]-1,2,3,6-tetrahydropyridin-4-yl}-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}cyclohex-3-ene-1-carboxamide;

4-[4-(5-fluoro-2-methoxyphenyl)-1H-pyrrolo[2,3-b]pyridin-2-yl]-N-(1-methyl-1H-pyrazol-4-yl)cyclohex-3-ene-1-carboxamide;

4-[4-(5-fluoro-2-methoxyphenyl)-1H-pyrrolo[2,3-b]pyridin-2-yl]-N-(1H-tetrazol-5-ylmethyl)cyclohex-3-ene-1-carboxamide;

N-{4-[4-(5-fluoro-2-methoxyphenyl)-1H-pyrrolo[2,3-b]pyridin-2-yl]cyclohex-3-en-1-yl}-L-norvaline;

4-[4-(5-fluoro-2-methoxyphenyl)-1H-pyrrolo[2,3-b]pyridin-2-yl]-N-(1H-tetrazol-5-ylmethyl)cyclohex-3-en-1-amine;

2-[4-({4-[4-(5-fluoro-2-methoxyphenyl)-1H-pyrrolo[2,3-b]pyridin-2-yl]-3,6-dihydropyridin-1(2H)-yl}sulfonyl)piperidin-1-yl]-N,N-dimethylacetamide;

2-{4-[4-(5-fluoro-2-methoxyphenyl)-1H-pyrrolo[2,3-b]pyridin-2-yl]-3,6-dihydropyridin-1(2H)-yl}-1-[(2R)-2-(hydroxymethyl)pyrrolidin-1-yl]ethanone;

4-(5-fluoro-2-methoxyphenyl)-2-[1-(methylsulfonyl)-2,3,6,7-tetrahydro-1H-azepin-4-yl]-1H-pyrrolo[2,3-b]pyridine;

4-[4-(5-fluoro-2-methoxyphenyl)-1H-pyrrolo[2,3-b]pyridin-2-yl]-N-methyl-2,3,6,7-tetrahydro-1H-azepine-1-carboxamide;

[1-({4-[4-(5-fluoro-2-methoxyphenyl)-1H-pyrrolo[2,3-b]pyridin-2-yl]-3,6-dihydropyridin-1(2H)-yl}carbonyl)-1,2,3,6-tetrahydropyridin-4-yl]boronic acid;

3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione;

N-{4-[4-(5-fluoro-2-methoxyphenyl)-1H-pyrrolo[2,3-b]pyridin-2-yl]cyclohex-3-en-1-yl}methanesulfonamide;

1-{4-[4-(5-fluoro-2-methoxyphenyl)-1H-pyrrolo[2,3-b]pyridin-2-yl]cyclohex-3-en-1-yl}-3-methylurea;

N-{4-[4-(5-fluoro-2-methoxyphenyl)-1H-pyrrolo[2,3-b]pyridin-2-yl]cyclohex-3-en-1-yl}-2-hydroxyacetamide;
2-cyano-N-{4-[4-(5-fluoro-2-methoxyphenyl)-1H-pyrrolo[2,3-b]pyridin-2-yl]cyclohex-3-en-1-yl}acetamide;
4-[4-(5-fluoro-2-methoxyphenyl)-1H-pyrrolo[2,3-b]pyridin-2-yl]-1,2,5,6-tetrahydropyridine-3-carbonitrile;
(3-{4-[4-(5-fluoro-2-methoxyphenyl)-1H-pyrrolo[2,3-b]pyridin-2-yl]-3,6-dihydropyridin-1(2H)-yl}oxetan-3-yl)acetonitrile;
4-[4-(5-fluoro-2-methoxyphenyl)-1H-pyrrolo[2,3-b]pyridin-2-yl]-N-{1-[(2R)-2-hydroxypropyl]-1H-pyrazol-4-yl}cyclohex-3-ene-1-carboxamide;
2-{4-[4-(5-fluoro-2-methoxyphenyl)-1H-pyrrolo[2,3-b]pyridin-2-yl]piperidin-1-yl}-1-(3-methoxyazetidin-1-yl)ethanone;
1-({4-[4-(5-fluoro-2-methoxyphenyl)-1H-pyrrolo[2,3-b]pyridin-2-yl]piperidin-1-yl}acetyl) azetidine-3-carbonitrile;
1-(3,3-difluoroazetidin-1-yl)-2-{4-[4-(5-fluoro-2-methoxyphenyl)-1H-pyrrolo[2,3-b]pyridin-2-yl]piperidin-1-yl}ethanone;
2-{4-[4-(5-fluoro-2-methoxyphenyl)-1H-pyrrolo[2,3-b]pyridin-2-yl]piperidin-1-yl}-1-(3-hydroxy-3-methylazetidin-1-yl)ethanone;
1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]piperidin-1-yl}ethanone;
2-{4-[4-(5-fluoro-2-methoxyphenyl)-1H-pyrrolo[2,3-b]pyridin-2-yl]piperidin-1-yl}-1-[3-(methoxymethyl)-3-methylazetidin-1-yl]ethanone;
1-[3-fluoro-3-(methoxymethyl)pyrrolidin-1-yl]-2-{4-[4-(5-fluoro-2-methoxyphenyl)-1H-pyrrolo[2,3-b]pyridin-2-yl]piperidin-1-yl}ethanone;
1-(3-fluoroazetidin-1-yl)-2-{4-[4-(5-fluoro-2-methoxyphenyl)-1H-pyrrolo[2,3-b]pyridin-2-yl]piperidin-1-yl}ethanone;
N-(3-fluorocyclobutyl)-2-{4-[4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]piperidin-1-yl}-1-(3-hydroxypyrrolidin-1-yl)ethanone;
(3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid;
methyl N-{4-[4-(5-fluoro-2-methoxyphenyl)-1H-pyrrolo[2,3-b]pyridin-2-yl]cyclohex-3-en-1-yl}-3-methyl-L-valinate;
N-cyano-4-[4-(5-fluoro-2-methoxyphenyl)-1H-pyrrolo[2,3-b]pyridin-2-yl]cyclohex-3-ene-1-carboxamide;
2-(3,3-dimethyl-1,2,3,6-tetrahydropyridin-4-yl)-4-(5-fluoro-2-methoxyphenyl)-1H-pyrrolo[2,3-b]pyridine;
2-(methylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2-{[({4-[4-(5-fluoro-2-methoxyphenyl)-1H-pyrrolo[2,3-b]pyridin-2-yl]-3,6-dihydropyridin-1(2H)-yl}sulfonyl)carbamoyl]oxy}ethyl acetate;
2-(pyrrolidin-1-yl)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
azetidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2-hydroxyethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-[4-(5-fluoro-2-methoxyphenyl)-1H-pyrrolo[2,3-b]pyridin-2-yl]-5,6-dihydropyridin-2(1H)-one;
2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)acetamide;
1-{4-[4-(5-fluoro-2-methoxyphenyl)-1H-pyrrolo[2,3-b]pyridin-2-yl]-3,6-dihydropyridin-1(2H)-yl}-3-[2-(hydroxymethyl)pyrrolidin-1-yl]propane-1,3-dione;
cyclopropyl({4-[4-(5-fluoro-2-methoxyphenyl)-1H-pyrrolo[2,3-b]pyridin-2-yl]cyclohex-3-en-1-yl}amino)acetic acid;
2-[3,3-dimethyl-1-(methylsulfonyl)-1,2,3,6-tetrahydropyridin-4-yl]-4-(5-fluoro-2-methoxyphenyl)-1H-pyrrolo[2,3-b]pyridine;
4-[4-(5-fluoro-2-methoxyphenyl)-1H-pyrrolo[2,3-b]pyridin-2-yl]-N,3,3-trimethyl-3,6-dihydropyridine-1(2H)-carboxamide;
4-[4-(5-fluoro-2-methoxyphenyl)-1H-pyrrolo[2,3-b]pyridin-2-yl]cyclohex-3-en-1-amine;
4-(5-fluoro-2-methoxyphenyl)-2-[(6S)-6-methyl-1,2,3,6-tetrahydropyridin-4-yl]-1H-pyrrolo[2,3-b]pyridine;
$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N-methylglycinamide;
tert-butyl N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinate;
$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinamide;
$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N,N-dimethylglycinamide;
tert-butyl {4-[4-(4-fluoro-2-methoxyphenyl)-1H-pyrrolo[2,3-b]pyridin-2-yl]-3,6-dihydropyridin-1(2H)-yl}acetate;
{4-[4-(5-fluoro-2-methoxyphenyl)-1H-pyrrolo[2,3-b]pyridin-2-yl]-3,3-dimethyl-3,6-dihydropyridin-1(2H)-yl}acetic acid;
4-[4-(5-fluoro-2-methoxyphenyl)-1H-pyrrolo[2,3-b]pyridin-2-yl]cyclohex-3-ene-1-carbonitrile;
2-{4-[4-(5-fluoro-2-methoxyphenyl)-5-methoxy-1H-pyrrolo[2,3-b]pyridin-2-yl]-3,6-dihydropyridin-1(2H)-yl}-N,N-dimethylacetamide;
ethyl ({5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}sulfonyl)carbamate;
3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}propane-1,2-diol;
{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;
2-{4-[4-(4-fluoro-2-methoxyphenyl)-1H-pyrrolo[2,3-b]pyridin-2-yl]-3,6-dihydropyridin-1(2H)-yl}acetamide;
2-{4-[4-(4-fluoro-2-methoxyphenyl)-1H-pyrrolo[2,3-b]pyridin-2-yl]-3,6-dihydropyridin-1(2H)-yl}-N-methylacetamide;
N-{4-[4-(5-fluoro-2-methoxyphenyl)-1H-pyrrolo[2,3-b]pyridin-2-yl]cyclohexyl}-D-valine;
2-{4-[5-fluoro-4-(5-fluoro-2-methoxyphenyl)-1H-pyrrolo[2,3-b]pyridin-2-yl]piperidin-1-yl}acetamide;
4-(5-fluoro-2-methoxyphenyl)-2-{1-[2-(2-methoxyethoxy)ethyl]-1,2,3,6-tetrahydropyridin-4-yl}-1H-pyrrolo[2,3-b]pyridine;
4-[4-(5-fluoro-2-methoxyphenyl)-1H-pyrrolo[2,3-b]pyridin-2-yl]cyclohex-3-en-1-yl methylsulfamate;

2-{4-[4-(5-fluoro-2-methoxyphenyl)-1H-pyrrolo[2,3-b]pyridin-2-yl]-3,6-dihydropyridin-1(2H)-yl}-1-(3-methoxyazetidin-1-yl)ethanone;

1-({4-[4-(5-fluoro-2-methoxyphenyl)-1H-pyrrolo[2,3-b]pyridin-2-yl]-3,6-dihydropyridin-1(2H)-yl}acetyl)azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(hydroxymethyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-1-(3-hydroxy-3-methylazetidin-1-yl) ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

N-cyclobutyl-2-{4-[4-(5-fluoro-2-methoxyphenyl)-1H-pyrrolo[2,3-b]pyridin-2-yl]-3,6-dihydropyridin-1(2H)-yl}acetamide;

1-(3-fluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

N-(3-fluorocyclobutyl)-2-{4-[4-(5-fluoro-2-methoxyphenyl)-1H-pyrrolo[2,3-b]pyridin-2-yl]-3,6-dihydropyridin-1(2H)-yl}acetamide;

2-{4-[4-(5-fluoro-2-methoxyphenyl)-1H-pyrrolo[2,3-b]pyridin-2-yl]-3,6-dihydropyridin-1(2H)-yl}-1-(3-hydroxypyrrolidin-1-yl)ethanone;

2-{4-[4-(5-fluoro-2-methoxyphenyl)-1H-pyrrolo[2,3-b]pyridin-2-yl]-3,3-dimethyl-3,6-dihydropyridin-1(2H)-yl}-N,N-dimethylacetamide;

3-{4-[4-(5-fluoro-2-methoxyphenyl)-1H-pyrrolo[2,3-b]pyridin-2-yl]-3,3-dimethyl-3,6-dihydropyridin-1(2H)-yl}propane-1,2-diol;

1-({4-[4-(5-fluoro-2-methoxyphenyl)-1H-pyrrolo[2,3-b]pyridin-2-yl]piperidin-1-yl}acetyl)-L-proline;

1-({4-[4-(5-fluoro-2-methoxyphenyl)-1H-pyrrolo[2,3-b]pyridin-2-yl]-3,6-dihydropyridin-1(2H)-yl}acetyl)-L-proline;

2-{4-[4-(5-fluoro-2-methoxyphenyl)-1H-pyrrolo[2,3-b]pyridin-2-yl]piperidin-1-yl}-N-(methylsulfonyl)acetamide;

1-[(3S,4S)-3,4-dihydroxypyrrolidin-1-yl]-2-{4-[4-(5-fluoro-2-methoxyphenyl)-1H-pyrrolo[2,3-b]pyridin-2-yl]piperidin-1-yl}ethanone;

1-[(3S,4S)-3,4-dihydroxypyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

N-{4-[4-(5-fluoro-2-methoxyphenyl)-1H-pyrrolo[2,3-b]pyridin-2-yl]cyclohex-3-en-1-yl}-L-serine;

5-[4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

4-(5-fluoro-2-methoxyphenyl)-2-[4-(piperazin-1-yl)cyclohex-1-en-1-yl]-1H-pyrrolo[2,3-b]pyridine;

N²-{4-[4-(5-fluoro-2-methoxyphenyl)-1H-pyrrolo[2,3-b]pyridin-2-yl]cyclohex-3-en-1-yl}-N,N-dimethyl-D-valinamide;

(4R)-1-{4-[4-(5-fluoro-2-methoxyphenyl)-1H-pyrrolo[2,3-b]pyridin-2-yl]cyclohex-3-en-1-yl}-4-hydroxy-L-proline;

N-{4-[4-(5-fluoro-2-methoxyphenyl)-1H-pyrrolo[2,3-b]pyridin-2-yl]cyclohex-3-en-1-yl}-L-valine;

2-{4-[4-(2-methoxyphenyl)-1H-pyrrolo[2,3-b]pyridin-2-yl]piperidin-1-yl}-N-methylacetamide;

{4-[4-(2-methoxyphenyl)-1H-pyrrolo[2,3-b]pyridin-2-yl]piperidin-1-yl}acetic acid;

2-[(6S)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;

4-(5-fluoro-2-methoxyphenyl)-2-[(6R)-6-methyl-1,2,3,6-tetrahydropyridin-4-yl]-1H-pyrrolo[2,3-b]pyridine;

4-(5-fluoro-2-methoxyphenyl)-2-[(2S)-2-methyl-1-(methylsulfonyl)piperidin-4-yl]-1H-pyrrolo[2,3-b]pyridine;

({4-[4-(5-fluoro-2-methoxyphenyl)-1H-pyrrolo[2,3-b]pyridin-2-yl]cyclohex-3-en-1-yl}oxy)acetic acid;

N-{4-[4-(5-fluoro-2-methoxyphenyl)-1H-pyrrolo[2,3-b]pyridin-2-yl]cyclohex-3-en-1-yl}-L-threonine;

2-{1-[(1,1-dioxidothiomorpholin-4-yl)sulfonyl]-1,2,3,6-tetrahydropyridin-4-yl}-4-(5-fluoro-2-methoxyphenyl)-1H-pyrrolo[2,3-b]pyridine;

4-(5-fluoro-2-methoxyphenyl)-2-{1-[(4-methylpiperazin-1-yl)sulfonyl]-1,2,3,6-tetrahydropyridin-4-yl}-1H-pyrrolo[2,3-b]pyridine;

ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-4-carboxylate;

ethyl 1-({4-[4-(5-fluoro-2-methoxyphenyl)-1H-pyrrolo[2,3-b]pyridin-2-yl]-3,6-dihydropyridin-1(2H)-yl}sulfonyl) prolinate;

ethyl {4-[4-(5-fluoro-2-methoxyphenyl)-1H-pyrrolo[2,3-b]pyridin-2-yl]-3,6-dihydropyridin-1(2H)-yl}acetate;

propan-2-yl {4-[4-(5-fluoro-2-methoxyphenyl)-1H-pyrrolo[2,3-b]pyridin-2-yl]-3,6-dihydropyridin-1(2H)-yl}acetate;

4-(2-ethoxy-4,5-difluorophenyl)-2-(1,2,3,6-tetrahydropyridin-4-yl)-1H-pyrrolo[2,3-b]pyridine;

2-hydroxy-2-methylpropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

(2,2-dimethyl-1,3-dioxolan-4-yl)methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

tetrahydro-2H-pyran-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-(2-ethoxy-4,5-difluorophenyl)-2-[1-(methylsulfonyl)-1,2,3,6-tetrahydropyridin-4-yl]-1H-pyrrolo[2,3-b]pyridine;

4-[4-(2-ethoxy-4,5-difluorophenyl)-1H-pyrrolo[2,3-b]pyridin-2-yl]-N-methyl-3,6-dihydropyridine-1(2H)-carboxamide;

2-{4-[5-fluoro-4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;

{(2S)-4-[4-(5-fluoro-2-methoxyphenyl)-1H-pyrrolo[2,3-b]pyridin-2-yl]-1,2,3,6-tetrahydropyridin-2-yl}methanol;

{(2S)-4-[4-(5-fluoro-2-methoxyphenyl)-1H-pyrrolo[2,3-b]pyridin-2-yl]-1,2,5,6-tetrahydropyridin-2-yl}methanol;

2-{4-[4-(4,5-difluoro-2-methoxyphenyl)-1H-pyrrolo[2,3-b]pyridin-2-yl]piperidin-1-yl}-N-methylacetamide;

2-{4-[4-(4,5-difluoro-2-methoxyphenyl)-1H-pyrrolo[2,3-b]pyridin-2-yl]piperidin-1-yl}-N,N-dimethylacetamide;

2-{5-[4-(5-fluoro-2-methoxyphenyl)-1H-pyrrolo[2,3-b]
pyridin-2-yl]-2,3,4,7-tetrahydro-1H-azepin-1-
yl}acetamide;
2-{5-[4-(5-fluoro-2-methoxyphenyl)-1H-pyrrolo[2,3-b]
pyridin-2-yl]-2,3,4,7-tetrahydro-1H-azepin-1-yl}-N,N-
dimethylacetamide;
(1 S,2S,3R,4R)-3-[({4-[4-(4,5-difluoro-2-methoxyphenyl)-
1H-pyrrolo[2,3-b]pyridin-2-yl]-3,6-dihydropyridin-1
(2H)-yl}acetyl)amino]bicyclo[2.2.1]hept-5-ene-2-car-
boxamide;
{4-[4-(5-fluoro-2-methoxyphenyl)-1H-pyrrolo[2,3-b]pyri-
din-2-yl]cyclohex-3-en-1-yl}[(2S)-2-(hydroxymethyl)
pyrrolidin-1-yl]methanone;
2-{4-[4-(4-fluoro-2-methoxyphenyl)-1H-pyrrolo[2,3-b]
pyridin-2-yl]piperidin-1-yl}acetamide;
2-{4-[4-(4-fluoro-2-methoxyphenyl)-1H-pyrrolo[2,3-b]
pyridin-2-yl]piperidin-1-yl}-N-methylacetamide;
4-(5-fluoro-2-methoxyphenyl)-2-(octahydrocyclopenta[c]
pyrrol-5-yl)-1H-pyrrolo[2,3-b]pyridine;
1-{4-[5-fluoro-4-(5-fluoro-2-methoxyphenyl)-1H-pyrrolo
[2,3-b]pyridin-2-yl]piperidin-1-yl}-2-hydroxyethanone;
pyrrolidin-3-ylmethyl ({4-[4-(5-fluoro-2-methoxyphenyl)-
1H-pyrrolo[2,3-b]pyridin-2-yl]-3,6-dihydropyridin-1
(2H)-yl}sulfonyl)carbamate;
piperidin-4-yl ({4-[4-(5-fluoro-2-methoxyphenyl)-1H-pyr-
rolo[2,3-b]pyridin-2-yl]-3,6-dihydropyridin-1(2H)-
yl}sulfonyl)carbamate;
piperidin-4-ylmethyl ({4-[4-(5-fluoro-2-methoxyphenyl)-
1H-pyrrolo[2,3-b]pyridin-2-yl]-3,6-dihydropyridin-1
(2H)-yl}sulfonyl)carbamate;
pyrrolidin-3-yl ({4-[4-(5-fluoro-2-methoxyphenyl)-1H-pyr-
rolo[2,3-b]pyridin-2-yl]-3,6-dihydropyridin-1(2H)-
yl}sulfonyl)carbamate;
2,3-dihydroxypropyl ({4-[4-(5-fluoro-2-methoxyphenyl)-
1H-pyrrolo[2,3-b]pyridin-2-yl]-3,6-dihydropyridin-1
(2H)-yl}sulfonyl)carbamate;
methyl {4-[4-(2-methoxyphenyl)-1H-pyrrolo[2,3-b]pyridin-
2-yl]piperidin-1-yl}acetate;
1-[(2S)-2-(hydroxymethyl)pyrrolidin-1-yl]-2-{4-[4-(2-
methoxyphenyl)-1H-pyrrolo[2,3-b]pyridin-2-yl]piperi-
din-1-yl}ethanone;
(2R)-2-({4-[4-(5-fluoro-2-methoxyphenyl)-1H-pyrrolo[2,3-
b]pyridin-2-yl]cyclohex-3-en-1-yl}amino)-1-(3-hy-
droxyazetidin-1-yl)-3-methylbutan-1-one;
1-{4-[4-(5-fluoro-2-methoxyphenyl)-1H-pyrrolo[2,3-b]
pyridin-2-yl]cyclohex-3-en-1-yl}-N,N-dimethyl-L-pro-
linamide;
(2R)-({4-[4-(5-fluoro-2-methoxyphenyl)-1H-pyrrolo[2,3-b]
pyridin-2-yl]cyclohex-3-en-1-yl}amino)(phenyl)acetic
acid;
4-(5-fluoro-2-methoxyphenyl)-2-[3-(methylsulfonyl)-3-
azabicyclo[4.1.0]hept-6-yl]-1H-pyrrolo[2,3-b]pyridine;
4-(5-fluoro-2-methoxyphenyl)-2-[4-(1H-tetrazol-5-yl)cy-
clohex-1-en-1-yl]-1H-pyrrolo[2,3-b]pyridine;
4-[4-(5-fluoro-2-methoxyphenyl)-1H-pyrrolo[2,3-b]pyri-
din-2-yl]cyclohex-3-en-1-yl tert-butylcarbamate;
2-{4-[4-(5-fluoro-2-methoxyphenyl)-5-methoxy-1H-pyr-
rolo[2,3-b]pyridin-2-yl]-3,6-dihydropyridin-1(2H)-yl}-1-
[(2S)-2-(hydroxymethyl)pyrrolidin-1-yl]ethanone;
2-{4-[4-(4,5-difluoro-2-methoxyphenyl)-1H-pyrrolo[2,3-b]
pyridin-2-yl]piperidin-1-yl}-1-[(2S)-2-(hydroxymethyl)
pyrrolidin-1-yl]ethanone;
2-{(2S)-4-[4-(5-fluoro-2-methoxyphenyl)-1H-pyrrolo[2,3-
b]pyridin-2-yl]-2-methylpiperidin-1-yl}-N,N-dimethyl-
acetamide;
4,4,4-trifluoro-2-{4-[4-(5-fluoro-2-methoxyphenyl)-1H-
pyrrolo[2,3-b]pyridin-2-yl]-3,6-dihydropyridin-1(2H)-
yl}butanoic acid;
2-{4-[4-(5-fluoro-2-methoxyphenyl)-1H-pyrrolo[2,3-b]
pyridin-2-yl]-3,6-dihydropyridin-1(2H)-yl}-N,N-dim-
ethyl-2-oxoethanesulfonamide;
2-{4-[4-(5-fluoro-2-methoxyphenyl)-1H-pyrrolo[2,3-b]
pyridin-2-yl]piperidin-1-yl}-N-methyl-2-oxoethanesulfo-
namide;
2-{4-[4-(5-fluoro-2-methoxyphenyl)-1H-pyrrolo[2,3-b]
pyridin-2-yl]piperidin-1-yl}-N,N-dimethyl-2-oxoethane-
sulfonamide;
1-{4-[4-(5-fluoro-2-methoxyphenyl)-1H-pyrrolo[2,3-b]
pyridin-2-yl]-3,6-dihydropyridin-1(2H)-yl}-1-oxopro-
pane-2-sulfonamide;
ethyl {4-[4-(5-fluoro-2-methoxyphenyl)-1H-pyrrolo[2,3-b]
pyridin-2-yl]-3,6-dihydropyridin-1(2H)-yl}(phenyl)ac-
etate;
ethyl 2-{4-[4-(5-fluoro-2-methoxyphenyl)-1H-pyrrolo[2,3-
b]pyridin-2-yl]-3,6-dihydropyridin-1(2H)-yl}-1,3-thiaz-
ole-5-carboxylate;
tert-butyl 3-{4-[4-(5-fluoro-2-methoxyphenyl)-1H-pyrrolo
[2,3-b]pyridin-2-yl]-3,6-dihydropyridin-1(2H)-
yl}pyrrolidine-1-carboxylate;
ethyl {[(6S)-4-[4-(5-fluoro-2-methoxyphenyl)-1H-pyrrolo
[2,3-b]pyridin-2-yl]-6-methyl-3,6-dihydropyridin-1(2H)-
yl]sulfonyl}carbamate;
2-({4-[4-(5-fluoro-2-methoxyphenyl)-1H-pyrrolo[2,3-b]
pyridin-2-yl]cyclohex-3-en-1-yl}oxy)ethanol;
2-{4-[4-(5-fluoro-2-methoxyphenyl)-1H-pyrrolo[2,3-b]
pyridin-2-yl]piperidin-1-yl}propanoic acid;
{4-[4-(5-fluoro-2-methoxyphenyl)-1H-pyrrolo[2,3-b]pyri-
din-2-yl]-3,6-dihydropyridin-1(2H)-yl}(phenyl)acetic
acid;
4-(5-fluoro-2-methoxyphenyl)-2-[1-(pyrrolidin-3-yl)-1,2,3,
6-tetrahydropyridin-4-yl]-1H-pyrrolo[2,3-b]pyridine;
3-{4-[5-fluoro-4-(5-fluoro-2-methoxyphenyl)-1H-pyrrolo
[2,3-b]pyridin-2-yl]piperidin-1-yl}-3-oxopropanenitrile;
2-aminoethyl ({4-[4-(5-fluoro-2-methoxyphenyl)-1H-pyr-
rolo[2,3-b]pyridin-2-yl]-3,6-dihydropyridin-1(2H)-
yl}sulfonyl)carbamate;
azetidin-3-ylmethyl ({4-[4-(5-fluoro-2-methoxyphenyl)-
1H-pyrrolo[2,3-b]pyridin-2-yl]-3,6-dihydropyridin-1
(2H)-yl}sulfonyl)carbamate;
2-(dimethylamino)ethyl ({4-[4-(5-fluoro-2-methoxyphe-
nyl)-1H-pyrrolo[2,3-b]pyridin-2-yl]-3,6-dihydropyridin-
1(2H)-yl}sulfonyl)carbamate;
2-(2,2-dimethyl-1,2,3,6-tetrahydropyridin-4-yl)-4-(5-
fluoro-2-methoxyphenyl)-1H-pyrrolo[2,3-b]pyridine;
5-({4-[4-(5-fluoro-2-methoxyphenyl)-1H-pyrrolo[2,3-b]
pyridin-2-yl]piperidin-1-yl}methyl)-2,4-dihydro-3H-1,2,
4-triazol-3-one;
4-(5-fluoro-2-methoxyphenyl)-2-{1-[1-(methylsulfonyl)
pyrrolidin-3-yl]-1,2,3,6-tetrahydropyridin-4-yl}-1H-pyr-
rolo[2,3-b]pyridine;
2-{4-[4-(5-fluoro-2-methoxyphenyl)-1H-pyrrolo[2,3-b]
pyridin-2-yl]piperidin-1-yl}-N-(propan-2-ylsulfonyl)ac-
etamide;
ethyl 2-{4-[4-(5-fluoro-2-methoxyphenyl)-1H-pyrrolo[2,3-
b]pyridin-2-yl]piperidin-1-yl}-1,3-thiazole-5-carboxy-
late;
methyl (4-{4-[4-(5-fluoro-2-methoxyphenyl)-1H-pyrrolo[2,
3-b]pyridin-2-yl]-3,6-dihydropyridin-1(2H)-
yl}cyclohexyl)acetate;
3-{4-[4-(5-fluoro-2-methoxyphenyl)-1H-pyrrolo[2,3-b]
pyridin-2-yl]-3,6-dihydropyridin-1(2H)-yl}-1-methylpyr-
rolidin-2-one;

4-{4-[4-(5-fluoro-2-methoxyphenyl)-1H-pyrrolo[2,3-b]pyridin-2-yl]-3,6-dihydropyridin-1(2H)-yl}pyrrolidin-2-one;

2-{4-[4-(5-fluoro-2-methoxyphenyl)-1H-pyrrolo[2,3-b]pyridin-2-yl]piperidin-1-yl}-1,3-thiazole-5-carboxylic acid;

(2 S)-cyclohexyl({4-[4-(5-fluoro-2-methoxyphenyl)-1H-pyrrolo[2,3-b]pyridin-2-yl]cyclohex-3-en-1-yl}amino)acetic acid;

N-{4-[5-fluoro-4-(5-fluoro-2-methoxyphenyl)-1H-pyrrolo[2,3-b]pyridin-2-yl]cyclohex-3-en-1-yl}-D-valine;

N-{4-[5-fluoro-4-(5-fluoro-2-methoxyphenyl)-1H-pyrrolo[2,3-b]pyridin-2-yl]cyclohex-3-en-1-yl}-3-methyl-L-valine;

{4-[5-fluoro-4-(5-fluoro-2-methoxyphenyl)-1H-pyrrolo[2,3-b]pyridin-2-yl]piperidin-1-yl}acetic acid;

methyl 1-({4-[4-(5-fluoro-2-methoxyphenyl)-1H-pyrrolo[2,3-b]pyridin-2-yl]cyclohex-3-en-1-yl}carbonyl)prolinate;

(4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;

3-{4-[4-(5-fluoro-2-methoxyphenyl)-1H-pyrrolo[2,3-b]pyridin-2-yl]piperidin-1-yl}-1-methylpyrrolidin-2-one;

N-cyano-4-[5-fluoro-4-(5-fluoro-2-methoxyphenyl)-1H-pyrrolo[2,3-b]pyridin-2-yl]-3,6-dihydropyridine-1(2H)-carboxamide;

4-(5-fluoro-2-methoxyphenyl)-2-(1-{[2-(2-methoxyethoxy)ethyl]sulfonyl}-1,2,3,6-tetrahydropyridin-4-yl)-1H-pyrrolo[2,3-b]pyridine;

N-cyano-2-{4-[4-(5-fluoro-2-methoxyphenyl)-1H-pyrrolo[2,3-b]pyridin-2-yl]piperidin-1-yl}acetamide;

{(2R)-4-[4-(5-fluoro-2-methoxyphenyl)-1H-pyrrolo[2,3-b]pyridin-2-yl]-1,2,5,6-tetrahydropyridin-2-yl}methanol;

{(2R)-4-[4-(5-fluoro-2-methoxyphenyl)-1H-pyrrolo[2,3-b]pyridin-2-yl]-1,2,3,6-tetrahydropyridin-2-yl}methanol;

ethyl ({4-[5-fluoro-4-(5-fluoro-2-methoxyphenyl)-1H-pyrrolo[2,3-b]pyridin-2-yl]piperidin-1-yl}sulfonyl)carbamate;

2-{4-[5-fluoro-4-(5-fluoro-2-methoxyphenyl)-1H-pyrrolo[2,3-b]pyridin-2-yl]piperidin-1-yl}-N-(2-hydroxyethyl)-N-methylacetamide;

4-[4-(5-fluoro-2-methoxyphenyl)-1H-pyrrolo[2,3-b]pyridin-2-yl]cyclohex-3-en-1-yl[(3-hydroxyazetidin-1-yl)sulfonyl]carbamate;

4-(5-fluoro-2-methoxyphenyl)-2-{1-[(2-methoxyethyl)sulfonyl]-1,2,3,6-tetrahydropyridin-4-yl}-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}-2-(2-methoxyethoxy)ethanesulfonamide;

tert-butyl 3-{4-[4-(5-fluoro-2-methoxyphenyl)-1H-pyrrolo[2,3-b]pyridin-2-yl]-3,6-dihydropyridin-1(2H)-yl}cyclobutanecarboxylate;

3-{4-[4-(5-fluoro-2-methoxyphenyl)-1H-pyrrolo[2,3-b]pyridin-2-yl]-3,6-dihydropyridin-1(2H)-yl}cyclobutanecarboxylic acid;

4-(5-fluoro-2-methoxyphenyl)-2-[2-(methylsulfonyl)octahydrocyclopenta[c]pyrrol-5-yl]-1H-pyrrolo[2,3-b]pyridine;

[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]acetic acid;

N²-{4-[4-(5-fluoro-2-methoxyphenyl)-1H-pyrrolo[2,3-b]pyridin-2-yl]cyclohex-3-en-1-yl}-N-methyl-D-valinamide;

N-{4-[4-(5-fluoro-2-methoxyphenyl)-1H-pyrrolo[2,3-b]pyridin-2-yl]cyclohex-3-en-1-yl}-L-phenylalanine;

N-{4-[4-(5-fluoro-2-methoxyphenyl)-1H-pyrrolo[2,3-b]pyridin-2-yl]cyclohex-3-en-1-yl}-L-tyrosine;

N²-{4-[4-(5-fluoro-2-methoxyphenyl)-1H-pyrrolo[2,3-b]pyridin-2-yl]cyclohex-3-en-1-yl}-L-valinamide;

N²-{4-[4-(5-fluoro-2-methoxyphenyl)-1H-pyrrolo[2,3-b]pyridin-2-yl]cyclohex-3-en-1-yl}-N,3-dimethyl-L-valinamide;

(2S)-({4-[4-(5-fluoro-2-methoxyphenyl)-1H-pyrrolo[2,3-b]pyridin-2-yl]cyclohex-3-en-1-yl}amino)(phenyl)acetic acid;

2-[1-(cyanoacetyl)-1,2,3,6-tetrahydropyridin-4-yl]-4-(5-fluoro-2-methoxyphenyl)-1H-pyrrolo[2,3-b]pyridine-5-carbonitrile;

4-(5-fluoro-2-methoxyphenyl)-2-(2-{[2-(2-methoxyethoxy)ethyl]sulfonyl}-1,2,3,3a,4,6a-hexahydrocyclopenta[c]pyrrol-5-yl)-1H-pyrrolo[2,3-b]pyridine;

(9aR)-8-[4-(5-fluoro-2-methoxyphenyl)-1H-pyrrolo[2,3-b]pyridin-2-yl]-1,6,7,9a-tetrahydropyrido[2,1-c][1,4]oxazin-3(4H)-one;

7-[4-(5-fluoro-2-methoxyphenyl)-1H-pyrrolo[2,3-b]pyridin-2-yl]-1,5,6,8a-tetrahydro[1,3]oxazolo[3,4-a]pyridin-3-one;

2-{4-[4-(5-fluoro-2-methoxyphenyl)-1H-pyrrolo[2,3-b]pyridin-2-yl]piperidin-1-yl}-N-(2-methoxyethyl)-N-methylacetamide;

{4-[4-(5-fluoro-2-methoxyphenyl)-1H-pyrrolo[2,3-b]pyridin-2-yl]piperidin-1-yl}(phenyl)acetic acid;

2-{4-[5-cyano-4-(5-fluoro-2-methoxyphenyl)-1H-pyrrolo[2,3-b]pyridin-2-yl]-3,6-dihydropyridin-1(2H)-yl}acetamide;

N-(3-fluorocyclobutyl)-4-[4-(5-fluoro-2-methoxyphenyl)-1H-pyrrolo[2,3-b]pyridin-2-yl]-2,5-dihydro-1H-pyrrole-2-carboxamide;

4-(5-fluoro-2-methoxyphenyl)-2-[(2R)-2-methyl-1,2,3,6-tetrahydropyridin-4-yl]-1H-pyrrolo[2,3-b]pyridine-4-(5-fluoro-2-methoxyphenyl)-2-[(6R)-6-methyl-1,2,3,6-tetrahydropyridin-4-yl]-1H-pyrrolo[2,3-b]pyridine (1:1);

2-{4-[4-(5-fluoro-2-methoxyphenyl)-1H-pyrrolo[2,3-b]pyridin-2-yl]-6,6-dimethyl-3,6-dihydropyridin-1(2H)-yl}-N,N-dimethylacetamide;

methyl 4-[4-(5-fluoro-2-methoxyphenyl)-1H-pyrrolo[2,3-b]pyridin-2-yl]-1-(methylcarbamoyl)-2,5-dihydro-1H-pyrrole-2-carboxylate;

4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile;

5-[5-cyano-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;

N-cyano-2-{4-[4-(5-fluoro-2-methoxyphenyl)-1H-pyrrolo[2,3-b]pyridin-2-yl]-3,6-dihydropyridin-1(2H)-yl}acetamide;

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}ethanone;

ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-3-carboxylate;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;

N-cyano-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxamide;

N-cyano-4-[4-(5-fluoro-2-methoxyphenyl)-1H-pyrrolo[2,3-b]pyridin-2-yl]piperidine-1-carboxamide;

2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide;

N-{5-[4-(5-fluoro-2-methoxyphenyl)-1H-pyrrolo[2,3-b]pyridin-2-yl]-1,2,3,3a,4,6a-hexahydropentalen-2-yl}-D-valine;

methyl 4-[4-(5-fluoro-2-methoxyphenyl)-1H-pyrrolo[2,3-b]pyridin-2-yl]-3,6-dihydropyridine-1(2H)-carboxylate;

5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine;

2-{4-[5-cyano-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

2-({4-[4-(5-fluoro-2-methoxyphenyl)-1H-pyrrolo[2,3-b]pyridin-2-yl]cyclohex-3-en-1-yl}oxy)-N,N-dimethylacetamide;

2-({4-[4-(5-fluoro-2-methoxyphenyl)-1H-pyrrolo[2,3-b]pyridin-2-yl]cyclohex-3-en-1-yl}oxy)-1-(morpholin-4-yl)ethanone;

4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-5-carbonitrile;

2-{4-[5-cyano-4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;

2-{4-[5-cyano-4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

2-{4-[4-(5-fluoro-2-methoxyphenyl)-1H-pyrrolo[2,3-b]pyridin-2-yl]-3,6-dihydropyridin-1(2H)-yl}-N-(2-methoxyethyl)-N-methylacetamide;

methyl (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate;

methyl (trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate;

methyl {4-[4-(5-fluoro-2-methoxyphenyl)-1H-pyrrolo[2,3-b]pyridin-2-yl]cyclohex-3-en-1-yl}acetate;

{4-[4-(5-fluoro-2-methoxyphenyl)-1H-pyrrolo[2,3-b]pyridin-2-yl]cyclohex-3-en-1-yl}acetic acid;

(4-{4-[4-(5-fluoro-2-methoxyphenyl)-1H-pyrrolo[2,3-b]pyridin-2-yl]piperidin-1-yl}cyclohexyl)acetic acid;

methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate;

N-{4-[4-(5-fluoro-2-methoxyphenyl)-1H-pyrrolo[2,3-b]pyridin-2-yl]cyclohex-3-en-1-yl}-L-leucine;

4-(5-fluoro-2-methoxyphenyl)-2-[(6R)-6-methyl-1-(methylsulfonyl)-1,2,3,6-tetrahydropyridin-4-yl]-1H-pyrrolo[2,3-b]pyridine;

2-[(6R)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;

4-(5-fluoro-2-methoxyphenyl)-2-[(2R)-2-methyl-1-(methylsulfonyl)-1,2,3,6-tetrahydropyridin-4-yl]-1H-pyrrolo[2,3-b]pyridine;

2-[(2R)-4-[4-(5-fluoro-2-methoxyphenyl)-1H-pyrrolo[2,3-b]pyridin-2-yl]-2-methyl-3,6-dihydropyridin-1(2H)-yl]-N,N-dimethylacetamide;

{4-[4-(5-fluoro-2-methoxyphenyl)-1H-pyrrolo[2,3-b]pyridin-2-yl]cyclohex-3-en-1-yl}(3-hydroxyazetidin-1-yl)methanone;

2-{4-[5-fluoro-4-(5-fluoro-2-methoxyphenyl)-1H-pyrrolo[2,3-b]pyridin-2-yl]piperidin-1-yl}-N-methyl-2-oxoethanesulfonamide;

{4-[5-cyano-4-(5-fluoro-2-methoxyphenyl)-1H-pyrrolo[2,3-b]pyridin-2-yl]piperidin-1-yl}acetic acid;

2-[1-(cyanoacetyl)piperidin-4-yl]-4-(5-fluoro-2-methoxyphenyl)-1H-pyrrolo[2,3-b]pyridine-5-carbonitrile;

4-(5-fluoro-2-methoxyphenyl)-2-{1-[2-(3-hydroxyazetidin-1-yl)-2-oxoethyl]piperidin-4-yl}-1H-pyrrolo[2,3-b]pyridine-5-carbonitrile;

2-{4-[5-fluoro-4-(5-fluoro-2-methoxyphenyl)-1H-pyrrolo[2,3-b]pyridin-2-yl]piperidin-1-yl}-N-(3-hydroxycyclobutyl)-N-methylacetamide;

2-{4-[5-cyano-4-(5-fluoro-2-methoxyphenyl)-1H-pyrrolo[2,3-b]pyridin-2-yl]piperidin-1-yl}-N-(2-hydroxyethyl)-N-methylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-oxoethanesulfonamide;

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-oxopropane-2-sulfonamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethyl-2-oxoethanesulfonamide;

tert-butyl {5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetate;

2-{4-[4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-1-[(3S)-3-hydroxypyrrolidin-1-yl]ethanone;

4-({4-[4-(5-fluoro-2-methoxyphenyl)-1H-pyrrolo[2,3-b]pyridin-2-yl]-3,6-dihydropyridin-1(2H)-yl}carbonyl)benzoic acid;

3-({4-[4-(5-fluoro-2-methoxyphenyl)-1H-pyrrolo[2,3-b]pyridin-2-yl]-3,6-dihydropyridin-1(2H)-yl}carbonyl)benzoic acid;

tert-butyl (3aS,6aR)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;

tert-butyl (3aR,6aS)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;

(3-{4-[4-(5-fluoro-2-methoxyphenyl)-1H-pyrrolo[2,3-b]pyridin-2-yl]-3,6-dihydropyridin-1(2H)-yl}cyclobutyl)acetic acid;

2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoic acid;

ethyl 5-[4-(5-fluoro-2-methoxyphenyl)-1H-pyrrolo[2,3-b]pyridin-2-yl]-1,2,3,6-tetrahydropyridine-4-carboxylate;

{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

4-(5-fluoro-2-methoxyphenyl)-2-[1-(2,5,8,11-tetraoxatetradecan-14-yl)-1,2,3,6-tetrahydropyridin-4-yl]-1H-pyrrolo[2,3-b]pyridine;

{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

4-(5-fluoro-2-methoxyphenyl)-2-{2-[2-(3-hydroxyazetidin-1-yl)-2-oxoethyl]-1,2,3,3a,4,6a-hexahydrocyclopenta[c]pyrrol-5-yl}-1H-pyrrolo[2,3-b]pyridine-5-carbonitrile;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

(3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]ethanone;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-2-hydroxyethanone;

(3aR,5r,6aS)-N-cyano-5-[4-(5-fluoro-2-methoxyphenyl)-1H-pyrrolo[2,3-b]pyridin-2-yl]hexahydrocyclopenta[c]pyrrole-2(1H)-carboxamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N,N-dimethylacetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]propane-1,2-diol;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]acetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-3-oxopropanenitrile;

4-[4-(5-fluoro-2-methoxyphenyl)-1H-pyrrolo[2,3-b]pyridin-2-yl]cyclohexanecarboxylic acid;

(4-{4-[5-fluoro-4-(5-fluoro-2-methoxyphenyl)-1H-pyrrolo[2,3-b]pyridin-2-yl]piperidin-1-yl}cyclohexyl)acetic acid;

{4-[5-chloro-4-(5-fluoro-2-methoxyphenyl)-1H-pyrrolo[2,3-b]pyridin-2-yl]cyclohex-3-en-1-yl}acetic acid;

2-({4-[4-(5-fluoro-2-methoxyphenyl)-1H-pyrrolo[2,3-b]pyridin-2-yl]-3,6-dihydropyridin-1(2H)-yl}sulfonyl)ethanol;

(3-{4-[4-(5-fluoro-2-methoxyphenyl)-1H-pyrrolo[2,3-b]pyridin-2-yl]-3,6-dihydropyridin-1(2H)-yl}cyclobutyl)(3-hydroxyazetidin-1-yl)methanone;

2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

2-[(6R)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

{5-[4-(5-fluoro-2-methoxyphenyl)-1H-pyrrolo[2,3-b]pyridin-2-yl]-1,2,3,6-tetrahydropyridin-4-yl}methanol;

{4-[4-(5-fluoro-2-methoxyphenyl)-1H-pyrrolo[2,3-b]pyridin-2-yl]-3,6-dihydropyridin-1(2H)-yl}(3-hydroxycyclobutyl)methanone;

4-(5-fluoro-2-methoxyphenyl)-2-[(3R)-3-methyl-1,2,3,6-tetrahydropyridin-4-yl]-1H-pyrrolo[2,3-b]pyridine;

4-(5-fluoro-2-methoxyphenyl)-2-[(3S)-3-methyl-1,2,3,6-tetrahydropyridin-4-yl]-1H-pyrrolo[2,3-b]pyridine;

2-[(3R)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

2-[(3S)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

1-{4-[4-(5-fluoro-2-methoxyphenyl)-1H-pyrrolo[2,3-b]pyridin-2-yl]cyclohex-3-en-1-yl}-N-methyl-L-prolinamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone;

2-[(3aR,5S,6aS)-5-[4-(5-fluoro-2-methoxyphenyl)-1H-pyrrolo[2,3-b]pyridin-2-yl]hexahydrocyclopenta[c]pyrrol-2(1H)-yl]-1-[(2S)-2-(hydroxymethyl)pyrrolidin-1-yl]ethanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(2-hydroxyethyl)-N-methylacetamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(3-hydroxycyclobutyl)-N-methylacetamide;

[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl](3-hydroxycyclobutyl)methanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-methyl-2-oxoethanesulfonamide;

2-(8-azabicyclo[3.2.1]oct-2-en-3-yl)-4-(5-fluoro-2-methoxyphenyl)-1H-pyrrolo[2,3-b]pyridine-5-carbonitrile;

2-(8-azabicyclo[3.2.1]oct-2-en-3-yl)-5-fluoro-4-(5-fluoro-2-methoxyphenyl)-1H-pyrrolo[2,3-b]pyridine;

N-cyano-3-[5-fluoro-4-(5-fluoro-2-methoxyphenyl)-1H-pyrrolo[2,3-b]pyridin-2-yl]-8-azabicyclo[3.2.1]oct-2-ene-8-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

{3-[5-cyano-4-(5-fluoro-2-methoxyphenyl)-1H-pyrrolo[2,3-b]pyridin-2-yl]-8-azabicyclo[3.2.1]oct-2-en-8-yl}acetic acid;

{3-[5-fluoro-4-(5-fluoro-2-methoxyphenyl)-1H-pyrrolo[2,3-b]pyridin-2-yl]-8-azabicyclo[3.2.1]oct-2-en-8-yl}acetic acid;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}acetamide;

{4-[4-(5-fluoro-2-methoxyphenyl)-1H-pyrrolo[2,3-b]pyridin-2-yl]cyclohexyl}acetic acid;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

1-{4-[5-fluoro-4-(5-fluoro-2-methoxyphenyl)-1H-pyrrolo[2,3-b]pyridin-2-yl]cyclohex-3-en-1-yl}-N,N-dimethyl-L-prolinamide;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

4-(5-fluoro-2-methoxyphenyl)-2-(8-{2-[(2S)-2-(hydroxymethyl)pyrrolidin-1-yl]-2-oxoethyl}-8-azabicyclo[3.2.1]oct-2-en-3-yl)-1H-pyrrolo[2,3-b]pyridine-5-carbonitrile;

4-(5-fluoro-2-methoxyphenyl)-2-{8-[2-(3-hydroxyazetidin-1-yl)-2-oxoethyl]-8-azabicyclo[3.2.1]oct-2-en-3-yl}-1H-pyrrolo[2,3-b]pyridine-5-carbonitrile;

{4-[5-cyano-4-(5-fluoro-2-methoxyphenyl)-1H-pyrrolo[2,3-b]pyridin-2-yl]cyclohex-3-en-1-yl}acetic acid;

2-(9-azabicyclo[3.3.1]non-2-en-3-yl)-4-(5-fluoro-2-methoxyphenyl)-1H-pyrrolo[2,3-b]pyridine;

4-(5-fluoro-2-methoxyphenyl)-2-[9-(methylsulfonyl)-9-azabicyclo[3.3.1]non-2-en-3-yl]-1H-pyrrolo[2,3-b]pyridine;

3-[4-(5-fluoro-2-methoxyphenyl)-1H-pyrrolo[2,3-b]pyridin-2-yl]-N-methyl-9-azabicyclo[3.3.1]non-2-ene-9-carboxamide;

2-{3-[4-(5-fluoro-2-methoxyphenyl)-1H-pyrrolo[2,3-b]pyridin-2-yl]-9-azabicyclo[3.3.1]non-2-en-9-yl}-N,N-dimethylacetamide;

3-{3-[4-(5-fluoro-2-methoxyphenyl)-1H-pyrrolo[2,3-b]pyridin-2-yl]-9-azabicyclo[3.3.1]non-2-en-9-yl}-3-oxopropanenitrile;

{3-[4-(5-fluoro-2-methoxyphenyl)-1H-pyrrolo[2,3-b]pyridin-2-yl]-9-azabicyclo[3.3.1]non-2-en-9-yl}(3-hydroxycyclobutyl)methanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(trans-4-hydroxycyclohexyl)acetamide;

4-[4-(4-fluoro-2-methoxyphenyl)-1H-pyrrolo[2,3-b]pyridin-2-yl]cyclohex-3-ene-1-carboxylic acid;

4-[4-(4,5-difluoro-2-methoxyphenyl)-1H-pyrrolo[2,3-b]pyridin-2-yl]cyclohex-3-ene-1-carboxylic acid;

4-[4-(2-methoxyphenyl)-1H-pyrrolo[2,3-b]pyridin-2-yl]cyclohex-3-ene-1-carboxylic acid;

4-[4-(5-fluoro-2-methoxyphenyl)-1H-pyrrolo[2,3-b]pyridin-2-yl]-1-methylcyclohex-3-ene-1-carboxylic acid;

2-{4-[4-(5-fluoro-2-methoxyphenyl)-1H-pyrrolo[2,3-b]pyridin-2-yl]-2,3,6,7-tetrahydro-1H-azepin-1-yl}-N,N-dimethylacetamide;

2-{4-[4-(5-fluoro-2-methoxyphenyl)-1H-pyrrolo[2,3-b]pyridin-2-yl]azepan-1-yl}-N,N-dimethylacetamide;

{4-[4-(5-fluoro-2-methoxyphenyl)-1H-pyrrolo[2,3-b]pyridin-2-yl]-2,3,6,7-tetrahydro-1H-azepin-1-yl}acetic acid;

2-{4-[4-(5-fluoro-2-methoxyphenyl)-1H-pyrrolo[2,3-b]pyridin-2-yl]-2,3,6,7-tetrahydro-1H-azepin-1-yl}-1-(3-hydroxyazetidin-1-yl)ethanone;

tert-butyl 3-{4-[4-(5-fluoro-2-methoxyphenyl)-1H-pyrrolo[2,3-b]pyridin-2-yl]-3,6-dihydropyridin-1(2H)-yl}azetidine-1-carboxylate;

tert-butyl 3-{4-[4-(5-fluoro-2-methoxyphenyl)-1H-pyrrolo[2,3-b]pyridin-2-yl]piperidin-1-yl}azetidine-1-carboxylate;

{4-[5-fluoro-4-(5-fluoro-2-methoxyphenyl)-1H-pyrrolo[2,3-b]pyridin-2-yl]cyclohex-3-en-1-yl}acetic acid;

2-[1-(azetidin-3-yl)-1,2,3,6-tetrahydropyridin-4-yl]-4-(5-fluoro-2-methoxyphenyl)-1H-pyrrolo[2,3-b]pyridine;

2-[1-(azetidin-3-yl)piperidin-4-yl]-4-(5-fluoro-2-methoxyphenyl)-1H-pyrrolo[2,3-b]pyridine;

[3-(benzyloxy)-1,2-oxazol-5-yl]{4-[4-(5-fluoro-2-methoxyphenyl)-1H-pyrrolo[2,3-b]pyridin-2-yl]-3,6-dihydropyridin-1(2H)-yl}methanone;

4-[5-cyano-4-(5-fluoro-2-methoxyphenyl)-1H-pyrrolo[2,3-b]pyridin-2-yl]cyclohex-3-ene-1-carboxylic acid;

4-(5-fluoro-2-methoxyphenyl)-2-{1-[1-(methylsulfonyl)azetidin-3-yl]-1,2,3,6-tetrahydropyridin-4-yl}-1H-pyrrolo[2,3-b]pyridine;

4-(5-fluoro-2-methoxyphenyl)-2-{1-[1-(methylsulfonyl)azetidin-3-yl]piperidin-4-yl}-1H-pyrrolo[2,3-b]pyridine;

2-{4-[4-(5-fluoro-2-methoxyphenyl)-1H-pyrrolo[2,3-b]pyridin-2-yl]-2,3,6,7-tetrahydro-1H-azepin-1-yl}-N-(3-hydroxycyclobutyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-N-(2-hydroxyethyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-1-[(2S)-2-(hydroxymethyl)pyrrolidin-1-yl]ethanone;

4-(5-fluoro-2-methoxyphenyl)-5-methoxy-2-[2-(methylsulfonyl)-1,2,3,3a,4,6a-hexahydrocyclopenta[c]pyrrol-5-yl]-1H-pyrrolo[2,3-b]pyridine;

2-{5-[4-(5-fluoro-2-methoxyphenyl)-5-methoxy-1H-pyrrolo[2,3-b]pyridin-2-yl]-3,3a,4,6a-tetrahydrocyclopenta[c]pyrrol-2(1H)-yl}-N,N-dimethylacetamide;

4-[4-(4,5-difluoro-2-methoxyphenyl)-5-fluoro-1H-pyrrolo[2,3-b]pyridin-2-yl]cyclohex-3-ene-1-carboxylic acid;

4-[5-fluoro-4-(4-fluoro-2-methoxyphenyl)-1H-pyrrolo[2,3-b]pyridin-2-yl]cyclohex-3-ene-1-carboxylic acid;

(4-{4-[4-(5-fluoro-2-methoxyphenyl)-1H-pyrrolo[2,3-b]pyridin-2-yl]cyclohex-3-en-1-yl}piperazin-1-yl)acetic acid;

2-{4-[5-fluoro-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-N-(trans-4-hydroxycyclohexyl)acetamide;

{4-[4-(5-fluoro-2-methoxyphenyl)-1H-pyrrolo[2,3-b]pyridin-2-yl]-3,6-dihydropyridin-1(2H)-yl}(3-hydroxy-1,2-oxazol-5-yl)methanone;

3-{4-[4-(5-fluoro-2-methoxyphenyl)-1H-pyrrolo[2,3-b]pyridin-2-yl]-3,6-dihydropyridin-1(2H)-yl}-N-methylazetidine-1-carboxamide;

3-{4-[4-(5-fluoro-2-methoxyphenyl)-1H-pyrrolo[2,3-b]pyridin-2-yl]piperidin-1-yl}-N-methylazetidine-1-carboxamide;

3-{4-[4-(5-fluoro-2-methoxyphenyl)-1H-pyrrolo[2,3-b]pyridin-2-yl]-3,6-dihydropyridin-1(2H)-yl}cyclobutanecarbonitrile;

3-{4-[4-(5-fluoro-2-methoxyphenyl)-1H-pyrrolo[2,3-b]pyridin-2-yl]-3,6-dihydropyridin-1(2H)-yl}cyclopentanecarboxylic acid;

9-[4-(5-fluoro-2-methoxyphenyl)-1H-pyrrolo[2,3-b]pyridin-2-yl]-3-azaspiro[5.5]undec-8-ene;

9-[4-(5-fluoro-2-methoxyphenyl)-1H-pyrrolo[2,3-b]pyridin-2-yl]-N-methyl-3-azaspiro[5.5]undec-8-ene-3-carboxamide;

9-[4-(5-fluoro-2-methoxyphenyl)-1H-pyrrolo[2,3-b]pyridin-2-yl]-3-(methylsulfonyl)-3-azaspiro[5.5]undec-8-ene;

(3-{4-[4-(5-fluoro-2-methoxyphenyl)-1H-pyrrolo[2,3-b]pyridin-2-yl]-3,6-dihydropyridin-1(2H)-yl}cyclobutyl)methanol;

(trans-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

(cis-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

N-(1,1-dioxidotetrahydrothiophen-3-yl)-2-{4-[4-(5-fluoro-2-methoxyphenyl)-1H-pyrrolo[2,3-b]pyridin-2-yl]-3,6-dihydropyridin-1(2H)-yl}acetamide;
N-(1,1-dioxidotetrahydrothiophen-3-yl)-2-{4-[4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]-3,6-dihydropyridin-1(2H)-yl}-1-[3-(methylsulfonyl)azetidin-1-yl]ethanone;
2-{4-[4-(5-fluoro-2-methoxyphenyl)-1H-pyrrolo[2,3-b]pyridin-2-yl]piperidin-1-yl}-1-[3-(methylsulfonyl)azetidin-1-yl]ethanone;
2-{4-[4-(5-fluoro-2-methoxyphenyl)-1H-pyrrolo[2,3-b]pyridin-2-yl]-3,6-dihydropyridin-1(2H)-yl}-N-(1-methyl-1H-pyrazol-4-yl)acetamide;
4-(4-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-(4,5-difluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
2-{3-[4-(5-fluoro-2-methoxyphenyl)-1H-pyrrolo[2,3-b]pyridin-2-yl]-9-azabicyclo[3.3.1]non-2-en-9-yl}-N-(2-hydroxyethyl)-N-methylacetamide;
2-{3-[4-(5-fluoro-2-methoxyphenyl)-1H-pyrrolo[2,3-b]pyridin-2-yl]-9-azabicyclo[3.3.1]non-2-en-9-yl}-1-(3-hydroxyazetidin-1-yl)ethanone;
2-{3-[4-(5-fluoro-2-methoxyphenyl)-1H-pyrrolo[2,3-b]pyridin-2-yl]-9-azabicyclo[3.3.1]non-2-en-9-yl}-1-[(2S)-2-(hydroxymethyl)pyrrolidin-1-yl]ethanone;
2-{3-[4-(5-fluoro-2-methoxyphenyl)-1H-pyrrolo[2,3-b]pyridin-2-yl]-9-azabicyclo[3.3.1]non-2-en-9-yl}-N-(3-hydroxycyclobutyl)-N-methylacetamide;
{3-[4-(5-fluoro-2-methoxyphenyl)-1H-pyrrolo[2,3-b]pyridin-2-yl]-9-azabicyclo[3.3.1]non-2-en-9-yl}acetic acid;
4-(2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
tert-butyl (2-{4-[4-(5-fluoro-2-methoxyphenyl)-1H-pyrrolo[2,3-b]pyridin-2-yl]-3,6-dihydropyridin-1(2H)-yl}ethyl)carbamate;
2-{4-[5-fluoro-4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;
4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
2-{4-[4-(5-fluoro-2-methoxyphenyl)-1H-pyrrolo[2,3-b]pyridin-2-yl]azepan-1-yl}-1-(3-hydroxyazetidin-1-yl)ethanone;
3-({4-[4-(5-fluoro-2-methoxyphenyl)-1H-pyrrolo[2,3-b]pyridin-2-yl]cyclohex-3-en-1-yl}amino)bicyclo[1.1.1]pentane-1-carboxylic acid;
2-{4-[4-(5-fluoro-2-methoxyphenyl)-1H-pyrrolo[2,3-b]pyridin-2-yl]-3,6-dihydropyridin-1(2H)-yl}ethanamine;
N-(2-{4-[4-(5-fluoro-2-methoxyphenyl)-1H-pyrrolo[2,3-b]pyridin-2-yl]-3,6-dihydropyridin-1(2H)-yl}ethyl)methanesulfonamide;
N-(2-{4-[4-(5-fluoro-2-methoxyphenyl)-1H-pyrrolo[2,3-b]pyridin-2-yl]-3,6-dihydropyridin-1(2H)-yl}ethyl)acetamide;
2-{4-[4-(5-fluoro-2-methoxyphenyl)-1H-pyrrolo[2,3-b]pyridin-2-yl]-3,6-dihydropyridin-1(2H)-yl}-N,N-dimethylethanesulfonamide;
2-{3-[4-(5-fluoro-2-methoxyphenyl)-1H-pyrrolo[2,3-b]pyridin-2-yl]-2,5-dihydro-1H-pyrrol-1-yl}-1-(3-hydroxyazetidin-1-yl)ethanone;
(4-{4-[4-(5-fluoro-2-methoxyphenyl)-1H-pyrrolo[2,3-b]pyridin-2-yl]cyclohex-3-en-1-yl}piperidin-1-yl)acetic acid;
4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;
2-{3-[4-(5-fluoro-2-methoxyphenyl)-1H-pyrrolo[2,3-b]pyridin-2-yl]-2,5-dihydro-1H-pyrrol-1-yl}-N-(2-hydroxyethyl)-N-methylacetamide;
2-{3-[4-(5-fluoro-2-methoxyphenyl)-1H-pyrrolo[2,3-b]pyridin-2-yl]-2,5-dihydro-1H-pyrrol-1-yl}-N,N-dimethylacetamide;
2-{3-[4-(5-fluoro-2-methoxyphenyl)-1H-pyrrolo[2,3-b]pyridin-2-yl]-2,5-dihydro-1H-pyrrol-1-yl}-1-[(2S)-2-(hydroxymethyl)pyrrolidin-1-yl]ethanone;
2-(4-{4-[4-(5-fluoro-2-methoxyphenyl)-1H-pyrrolo[2,3-b]pyridin-2-yl]cyclohex-3-en-1-yl}piperidin-1-yl)-N,N-dimethylacetamide;
(4-{(1S)-4-[4-(5-fluoro-2-methoxyphenyl)-1H-pyrrolo[2,3-b]pyridin-2-yl]cyclohex-3-en-1-yl}piperidin-1-yl)acetic acid;
(4-{(1R)-4-[4-(5-fluoro-2-methoxyphenyl)-1H-pyrrolo[2,3-b]pyridin-2-yl]cyclohex-3-en-1-yl}piperidin-1-yl)acetic acid;
methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate;
(4-{(1S)-4-[4-(5-fluoro-2-methoxyphenyl)-1H-pyrrolo[2,3-b]pyridin-2-yl]cyclohex-3-en-1-yl}piperazin-1-yl)acetic acid;
(4-{(1R)-4-[4-(5-fluoro-2-methoxyphenyl)-1H-pyrrolo[2,3-b]pyridin-2-yl]cyclohex-3-en-1-yl}piperazin-1-yl)acetic acid;
(4-{4-[4-(5-fluoro-2-methoxyphenyl)-1H-pyrrolo[2,3-b]pyridin-2-yl]-3,6-dihydropyridin-1(2H)-yl}cyclohexylidene)acetic acid;
cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
trans-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;
(cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;
(1-{4-[4-(5-fluoro-2-methoxyphenyl)-1H-pyrrolo[2,3-b]pyridin-2-yl]cyclohex-3-en-1-yl}piperidin-4-yl)acetic acid;
methyl (4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetate;
cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;
(4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetic acid;

(trans-4-{4-[5-fluoro-4-(5-fluoro-2-methoxyphenyl)-1H-pyrrolo[2,3-b]pyridin-2-yl]piperidin-1-yl}cyclohexyl) acetic acid;

2-(trans-4-{4-[4-(5-fluoro-2-methoxyphenyl)-1H-pyrrolo[2,3-b]pyridin-2-yl]-3,6-dihydropyridin-1(2H)-yl}cyclohexyl)-N-(propan-2-ylsulfonyl)acetamide;

trans-4-{4-[5-fluoro-4-(5-fluoro-2-methoxyphenyl)-1H-pyrrolo[2,3-b]pyridin-2-yl]-3,6-dihydropyridin-1(2H)-yl}-N-(propan-2-ylsulfonyl)cyclohexanecarboxamide;

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexyl)acetic acid;

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid; and pharmaceutically acceptable salts thereof.

In another aspect, the present invention relates to pharmaceutical compositions comprising a pharmaceutically acceptable excipient and a therapeutically effective amount of a compound of Formula (IIa) or a pharmaceutically acceptable salt thereof.

In another aspect, the present invention relates to methods of treating cancer in a patient, comprising administering to a patient suffering from a cancer a therapeutically effective amount of a compound of Formula (IIa), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a CDK9-mediated disorder or condition. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of formula I can be administered by injection, that is, intravenously, intramuscularly, intracutaneously, subcutaneously, intraduodenally, parentally, or intraperitoneally. In certain embodiments, a compound of formula I may be administered orally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. CDK9-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-$OCH_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLE- NOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG 132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA®(canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS®(trabectedin), ZD-6126, ZINECARD® (dexrazoxane), ZOMETA® (zolendronic acid), zorubicin and the like.

Schemes and Experimentals

The following abbreviations have the meanings indicated. ADDP means 1,1'-(azodicarbonyl)dipiperidine; AD-mix-13 means a mixture of (DHQD)$_2$PHAL, K$_3$Fe(CN)$_6$, K$_2$CO$_3$, and K$_2$SO$_4$; 9-BBN means 9-borabicyclo(3.3.1)nonane; Boc means tert-butoxycarbonyl; (DHQD)$_2$PHAL means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC•HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; and PPh$_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

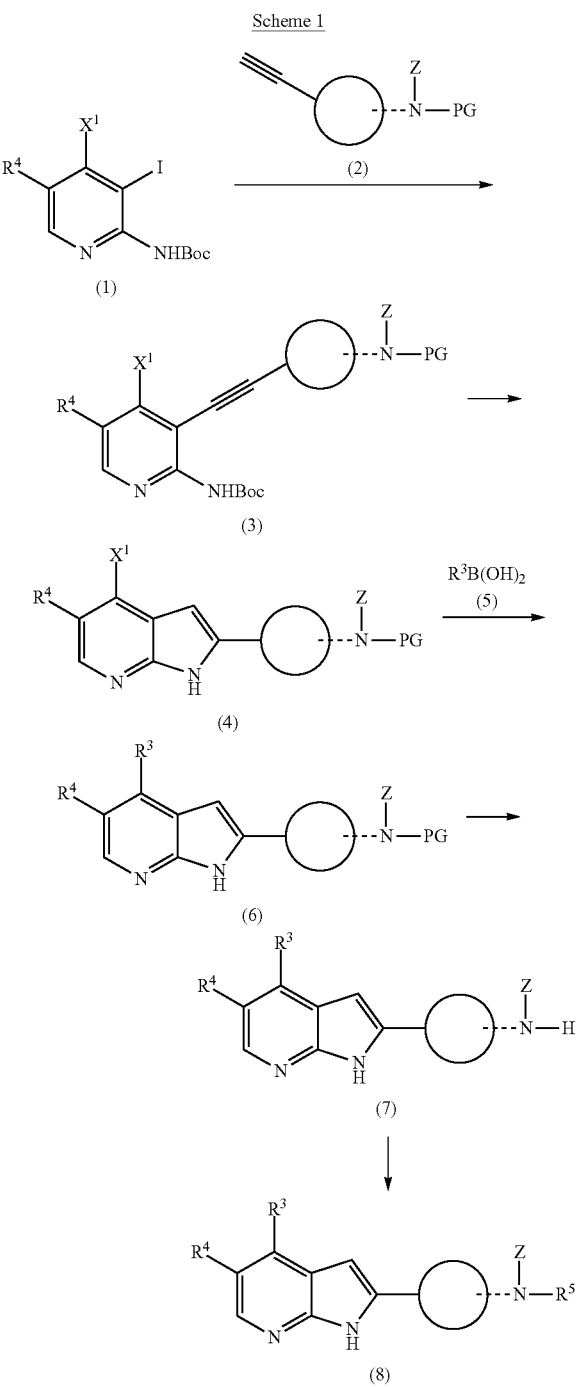

Scheme 1

As shown in Scheme 1, compounds of formula (3) can be prepared by reacting compounds of formula (1), wherein $X^1$ is Br or Cl, $R^4$ is as described for Formula (I) herein and BOC is tert-butoxycarbonyl, with compounds of formula (2), wherein

is a carbocycle or heterocycle with - - - indicating the N can be within the ring (Z is absent) or outside of the ring (Z is H) and PG is a suitable protecting group, in the presence of copper (I) iodide, a catalyst such as, but not limited to, bis(triphenylphosphine)palladium(II) chloride, and a base such as, but not limited to, triethylamine. The reaction is typically performed at room temperature in a solvent such as, but not limited to, tetrahydrofuran. Compounds of formula (3) can be reacted with potassium tert-butoxide in the presence of 18-crown-6 to provide compounds of formula (4). The reaction is typically performed at an elevated temperature (e.g., 60-110° C.) in a solvent such as, but not limited to, toluene. Compounds of formula (4) can be reacted with a boronic acid of formula (5), wherein $R^3$ is

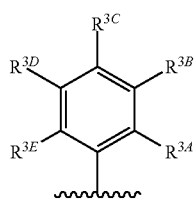

as described herein for Formula (IIa), under Suzuki coupling reaction conditions (N. Miyama and A. Suzuki, Chem. Rev. 1995, 95:2457-2483, J. Organomet. Chem. 1999, 576:147-148) to provide compounds of formula (6). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, acetates of sodium or potassium, and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl)ferrocene. Non-limiting examples of suitable solvent include methanol, ethanol, dimethoxyethane, N,N-dimethylformamide, dimethylsulfoxide, dioxane, tetrahydropyran, and water, or a mixture thereof.

Compounds of formula (7), which are representative of compounds of Formula (IIa), can be prepared by deprotecting compounds of formula (6) under conditions described herein (e.g. with an acid such as hydrochloric acid in a solvent such as ethanol or ethyl acetate or trifluoroacetic acid in a solvent such as dichloromethane). Compounds of formula (8), which are representative of compounds of Formula (IIa) and wherein $R^5$ is as described herein in Formula (IIa), can be prepared from compounds of formula (7) by various processes such as alkylation under reductive amination conditions using an appropriate ketone or aldehyde; acylation using an appropriate acid chloride or other activated carboxylic acid; sulfonation using an appropriate sulfonyl chloride; carboxamidation using an appropriate activated carbamate; and sulfonamidation using an appropriate sulfonylamide.

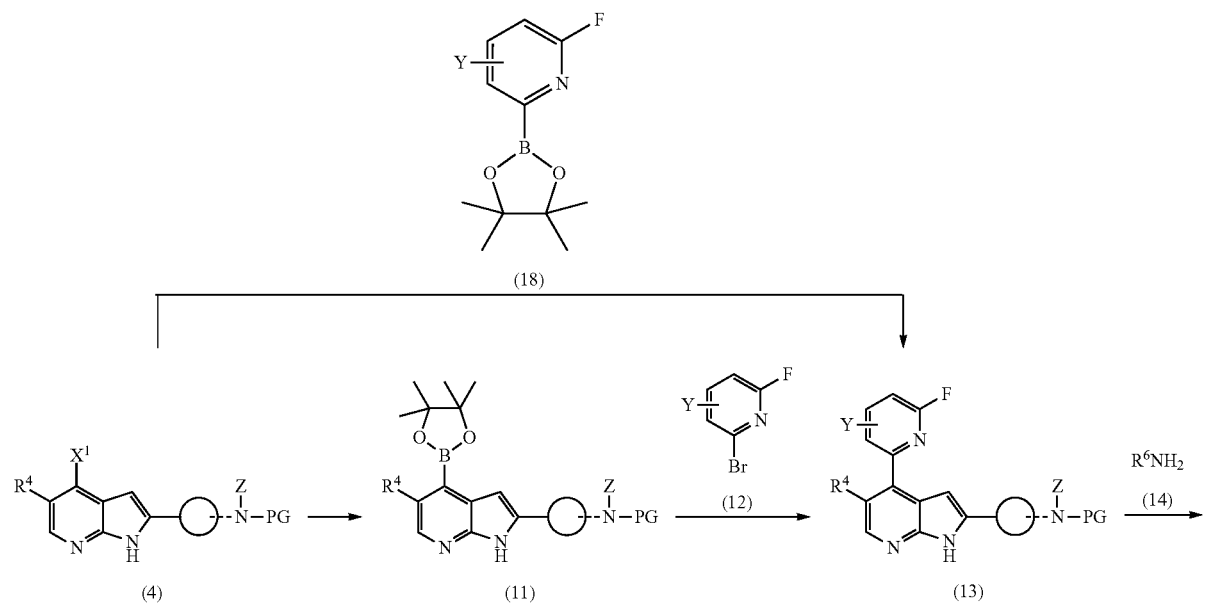

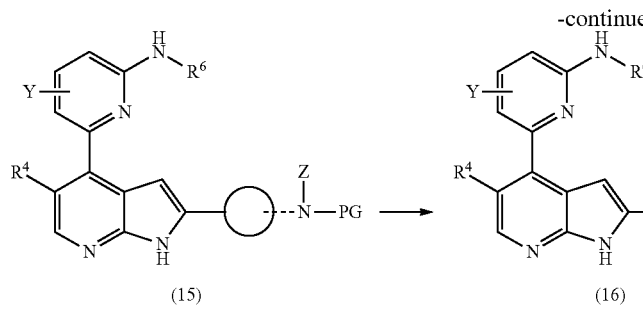
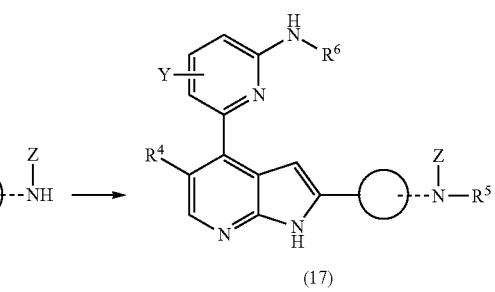

Compounds of formula (4) can be reacted with potassium acetate and 4,4,4',4',5,5,5',5'-octamethyl-2,2'-bi(1,3,2-dioxaborolane) in the presence of a catalyst such as, but not limited to, palladium acetate, and a ligand such as, but not limited to, 2-dicyclohexylphosphino)biphenyl to provide compounds of formula (11). The reaction is typically performed at an elevated temperature (e.g., 100-110° C.) in a solvent such as, but not limited to, 1,4-dioxane. Compounds of formula (13) can be prepared by reacting compounds of formula (11) with compounds of formula (12), wherein Y is as described in Formula (I) herein for substituents on $R^3$ when $R^3$ is pyridinyl, under Suzuki Coupling reaction conditions described above in Scheme 1. Alternatively, compounds of formula (4) can be reacted with compounds of formula (18) wherein Y is as described in Formula (I) herein for substituents on $R^3$ when $R^3$ is pyridinyl, under Suzuki Coupling reaction conditions to provide compounds of formula (13). Compounds of formula (15) can be prepared by reacting compounds of formula (13) with compounds of formula (14) wherein $R^6$ is as described herein for Formula (I). The reaction is typically performed at an elevated temperature (e.g., 100-110° C.). Compounds of formula (16), which are representative of compounds of Formula (I), can be prepared by deprotecting compounds of formula (15) under conditions described herein and known to those skilled in the art and readily available in the literature as described above in Scheme 1. Compounds of formula (17), which are representative of compounds of Formula (IIa) and wherein $R^5$ is as described herein in Formula (I), can be prepared from compounds of formula (16) as described above in Scheme 1.

Compounds of formula (11) can be reacted with compounds of formula (19), wherein $R^3$ is as described in Scheme 1, and $X^n$ is an appropriate halide or triflate, under Suzuki Coupling reaction conditions described above in Scheme 1 to provide compounds of formula (20). Compounds of formula (21), which are representative of compounds of Formula (IIa), can be prepared by deprotecting compounds of formula (20) under conditions described herein and as described above in Scheme 1. Compounds of formula (23), which are representative of compounds of Formula (IIa) and wherein $R^5$ is as described herein in Formula (IIa), can be prepared from compounds of formula (21) by various processes known to those skilled in the art and described herein.

Scheme 3

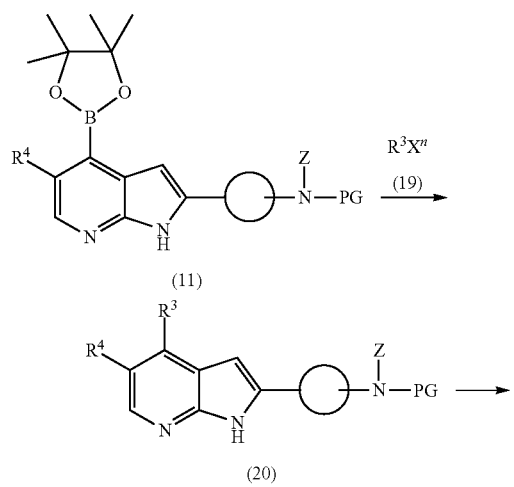

Scheme 4

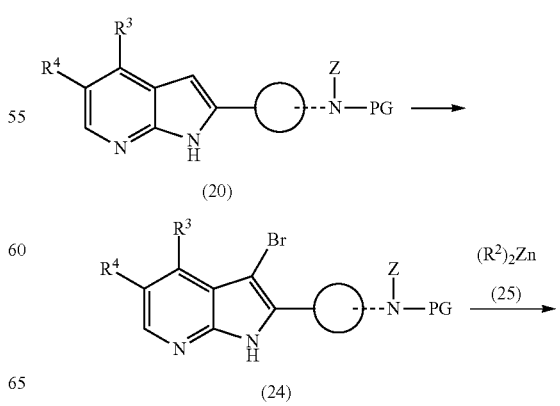

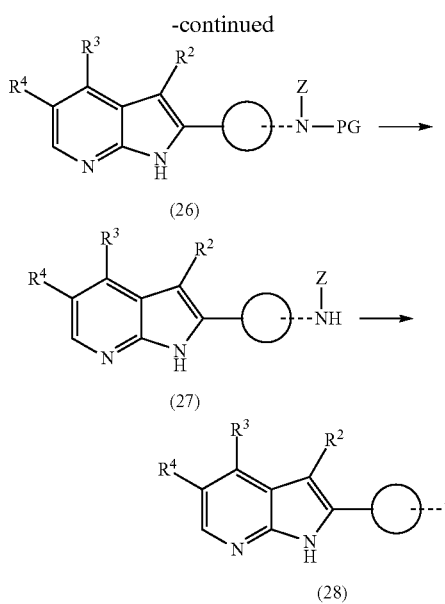

As shown in Scheme 4, compounds of formula (20), wherein $R^3$ is as described in Scheme 1, can be reacted with N-bromosuccinimide to provide compounds of formula (24). The addition is typically performed at low temperature before warming up to ambient temperature in a solvent such as, but not limited to, N,N-dimethylformamide. Compounds of formula (26) can be prepared reacting compounds of formula (24) with compounds of formula (25) wherein $R^2$ is as described herein, in the presence of a catalyst such as, but not limited to, [1,1'-bis(diphenylphosphino)ferrocene]dichloropalladium(II), dichloromethane adduct. The reaction is typically performed at an elevated temperature (e.g., 100° C.) in a solvent such as, but not limited to, 1,4-dioxane. Compounds of formula (27), which are representative of compounds of Formula (IIa), can be prepared can be prepared by deprotecting compounds of formula (26) as described above in Scheme 1. Compounds of formula (28), which are representative of compounds of Formula (IIa) and wherein $R^5$ is as described herein in Formula (IIa), can be prepared from compounds of formula (27) as described above in Scheme 1.

Scheme 5

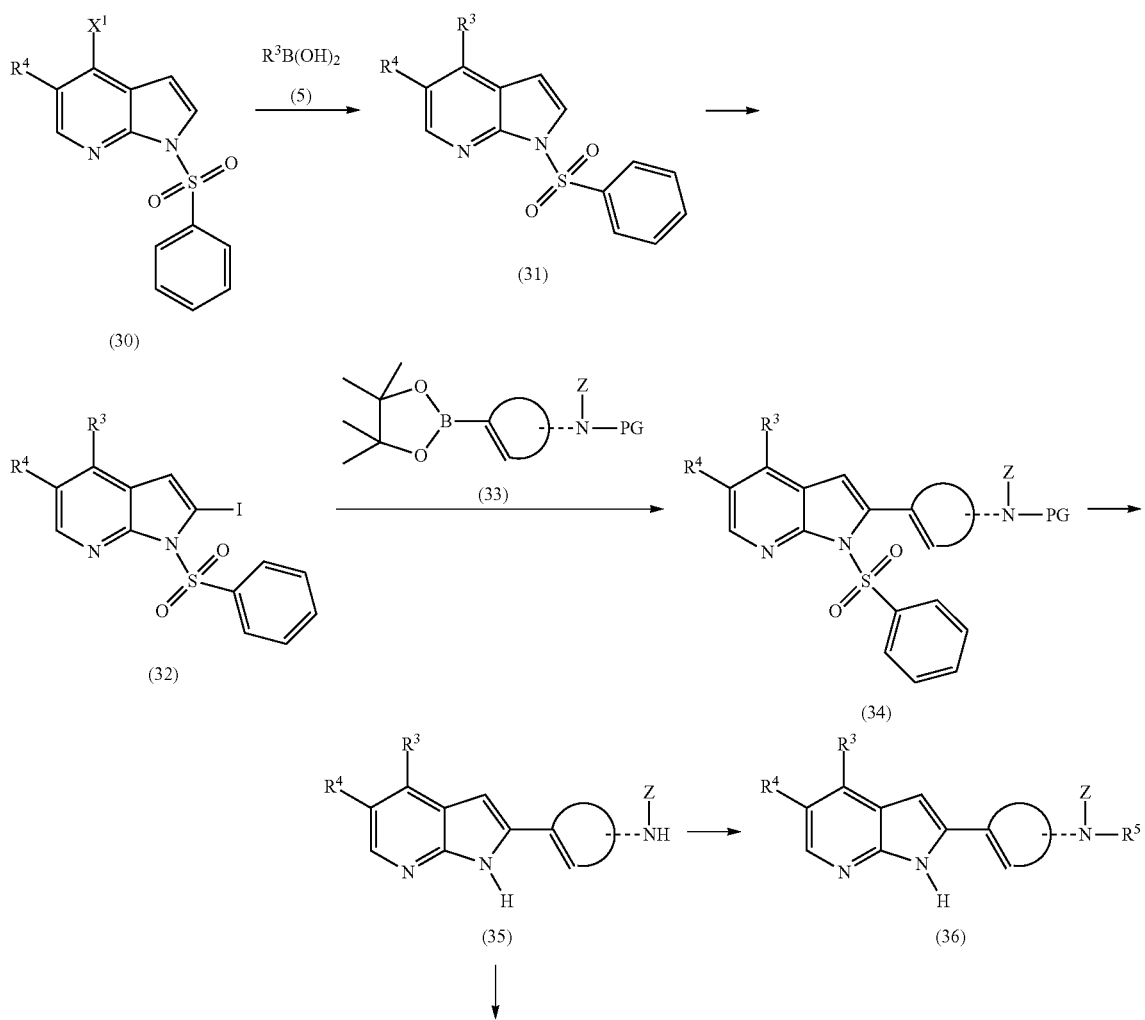

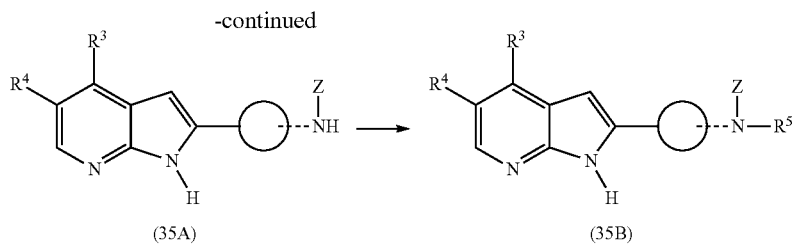

(35A) → (35B)

Compounds of formula (30), wherein $X^1$ is Cl or Br, $R^4$ is as described for Formula (IIa) herein, can be reacted with compounds of formula (5), wherein $R^3$ is as described in Scheme 1, under Suzuki Coupling reaction conditions described above in Scheme 1 to provide compounds of formula (31). Compounds of formula (31) can be treated with lithium diisopropylamide at low temperature followed by iodine to provide compounds of formula (32). The reaction is typically performed in a solvent such as, but not limited to, tetrahydrofuran, heptane, ethylbenzene, or mixtures thereof. Compounds of formula (32) can be reacted with compounds of formula (33) wherein

is a cycloalkenyl or heterocycloalkenyl ring with - - - indicating the N can be within the ring (Z is absent) or outside of the ring (Z is H) and PG is a suitable protecting group, under Suzuki Coupling reaction conditions described above in Scheme 1 to provide compounds of formula (34). Compounds of formula (34) can be reacted with sodium hydroxide in dioxane at an elevated temperature (e.g., 80-90° C.) followed by deprotection as described above in Scheme 1 to provide compounds of formula (35) which are representative of compounds of Formula (IIa). Compounds of formula (36), which are representative of compounds of Formula (IIa) and wherein $R^5$ is as described herein in Formula (IIa), can be prepared from compounds of formula (35) by various processes known to those skilled in the art and described herein.

Alternatively, as shown in Scheme 5, compounds of formula (35) can be treated with palladium hydroxide on carbon in the presence of hydrogen gas to provide compounds of formula (35A) which are representative of compounds of Formula (IIa). The reaction is typically performed at an elevated temperature (e.g., 50° C.) in a solvent such as but not limited to ethanol. Compounds of formula (35B), which are representative of compounds of Formula (IIa) and wherein $R^5$ is as described herein in Formula (IIa), can be prepared from compounds of formula (35A) by various processes known to those skilled in the art and described herein.

Scheme 6

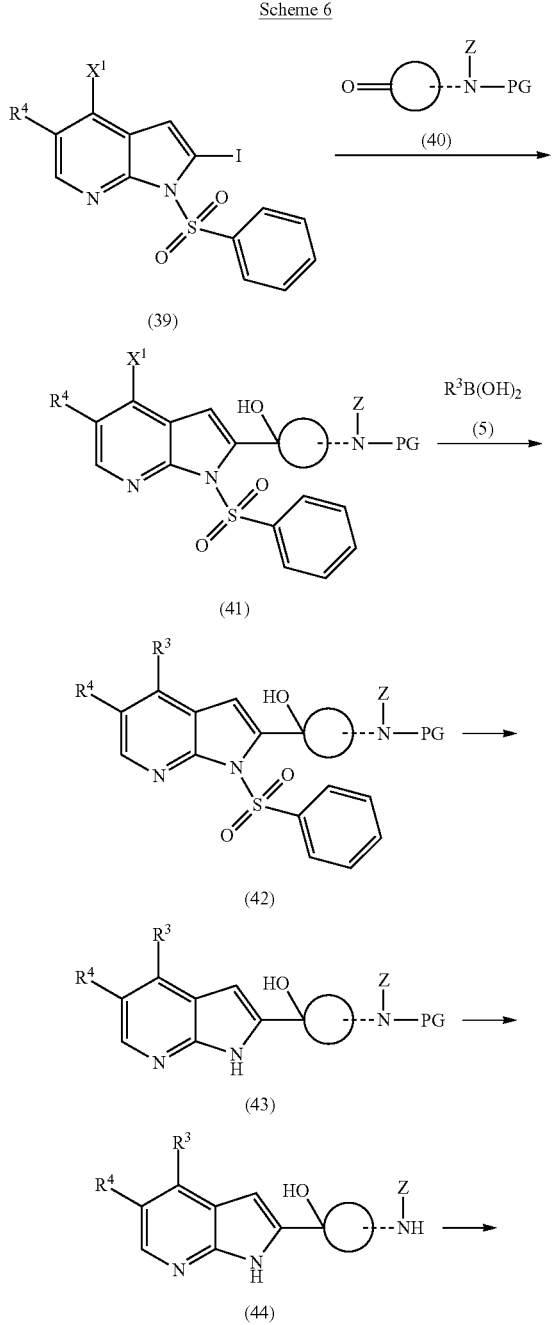

(39)

(40)

(41)

(42)

(43)

(44)

285

-continued

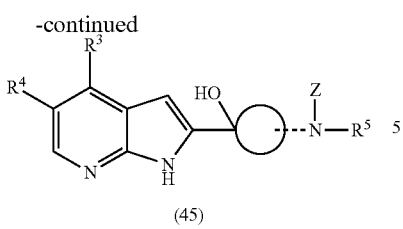

(45)

As shown in Scheme 6, compounds of formula (39) can be treated with n-butyllithium followed by compounds of formula (40), wherein

is a carbocycle or heterocycle with - - - indicating the N can be within the ring (X is absent) or outside of the ring (X is H) and PG is a suitable protecting group, to provide compounds of formula (41). The reaction is typically performed at low temperature in a solvent such as, but not limited to, tetrahydrofuran, hexanes, or mixtures thereof. Compounds of formula (42) can be prepared by reacting compounds of formula (41) with compounds of formula (5), wherein $R^3$ is as described in Scheme 1, under Suzuki Coupling reaction conditions described above in Scheme 1. Compounds of formula (42) can be treated with aqueous sodium hydroxide in a solvent such as dioxane to provide compounds of formula (43). Compounds of formula (44), which are representative of compounds of Formula (I), can be prepared can be prepared by deprotecting compounds of formula (43) as described above in Scheme 1. Compounds of formula (45), which are representative of compounds of Formula (IIa) and wherein $R^5$ is as described herein in Formula (IIa), can be prepared from compounds of formula (44) by various processes as described above in Scheme 1.

286

Compounds of formula (49), which are representative of compounds of Formula (IIa), can be prepared by reacting compounds of formula (27), wherein $R^3$ is as described in Scheme 1, with compounds of formula (47) or (48) under appropriate alkylation or reductive amination conditions. Compounds of formula (51), which are representative of compounds of Formula (IIa), can be prepared by reacting compounds of formula (27) with compounds of the formula (50) under appropriate reductive amination conditions. Compounds of formula (53), which are representative of compounds of Formula (IIa), can be prepared by reacting compounds of formula (27) with compounds of formula (52) under appropriate urea formation conditions. Compounds of formula (55), which are representative of compounds of Formula (IIa), can be prepared by reacting compounds of formula (27) with compounds of formula (54) under appropriate sulfonamidation conditions. Compounds of formula (58), which are representative of compounds of Formula (IIa), can be prepared by reacting compounds of formula (27) with compounds of formula (56) or formula (57) under appropriate acylation conditions.

Experimentals

The following examples are presented to provide what is believed to be the most useful and readily understood description of procedures and conceptual aspects of this invention. Each exemplified compound and intermediate was named using ACD/ChemSketch 2012 Release ((Build 59026, 3 Sep. 2012), Advanced Chemistry Development Inc., Toronto, Ontario), or ChemDraw® Ver. 9.0.7 (CambridgeSoft, Cambridge, Mass.).

Scheme 7

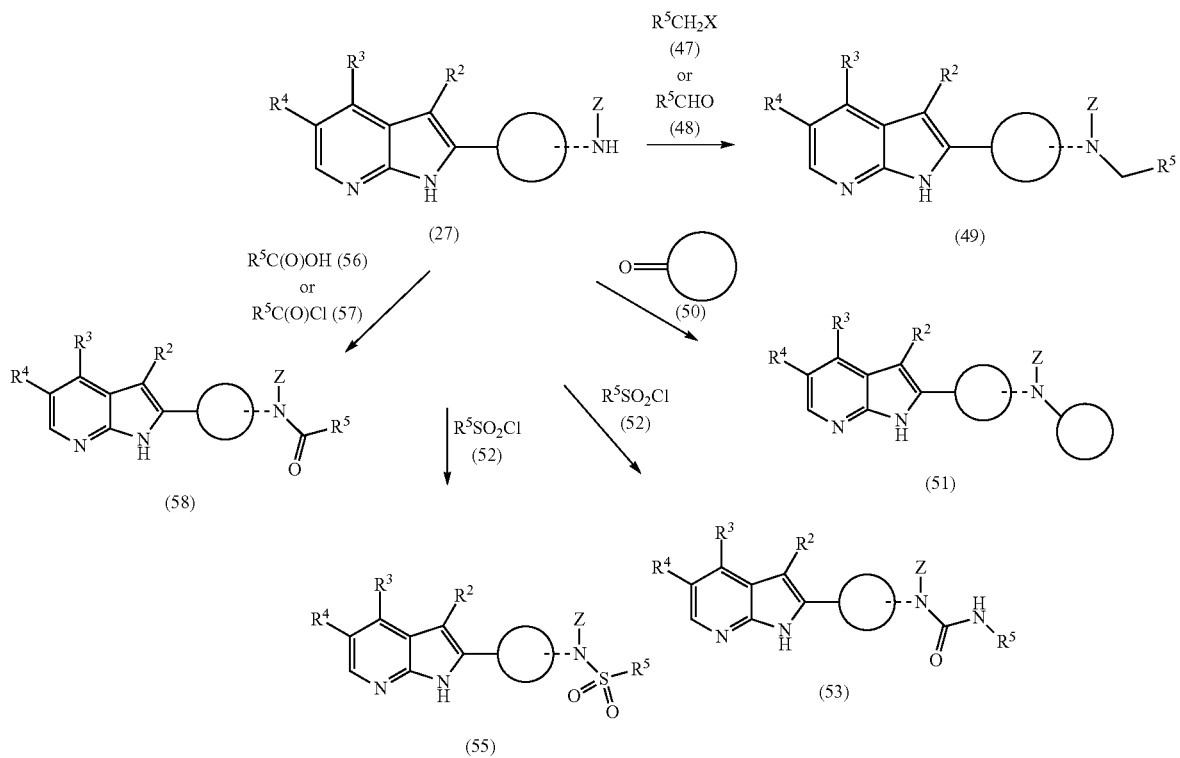

EXAMPLE 1

4-(5-fluoro-2-methoxyphenyl)-2-(piperidin-3-yl)-1H-pyrrolo[2,3-b]pyridine

EXAMPLE 1A tert-butyl (4-chloro-3-iodopyridin-2-yl)carbamate tert-Butyl (4-chloropyridin-2-yl)carbamate (10 g, 43.7 mmol) and tetramethylethylenediamine (12 mL) in anhydrous tetrahydrofuran (200 mL) was cooled to −70° C. and treated dropwise with a solution of 2.5M n-butyllithium (52 mL, 131 mmol) in hexane over a period of 30 minutes. The mixture was stirred at −70° C. for 1 hour and treated dropwise with a solution of iodine (27 g, 109 mmol) in anhydrous tetrahydrofuran at −70° C. After the addition, the mixture was stirred at the −70° C. for 30 minutes and was allowed to warm to room temperature. The mixture was treated with saturated sodium hydrogensulfite solution (200 mL) and stirred for 30 minutes. The mixture was extracted with ethyl acetate (100×3 mL) and the organic layer was washed with water and brine solution (200 mL each) and dried over anhydrous sodium sulfate. Filtration and concentration under vacuum and recrystallization with ethyl acetate-hexane afforded the title compound. LCMS: 298.9 (M+H-NCOOH)$^+$.

EXAMPLE 1B tert-butyl 3-(hydroxymethyl)piperidine-1-carboxylate

To a solution of piperidin-3-ylmethanol (5 g, 43.4 mmol) in dichloromethane (100 mL) was added di-tert-butyldicarbonate (11.09 mL, 47.8 mmol) at 0° C. and the mixture was stirred at room temperature for 12 hours. The mixture was concentrated under vacuum to afford the crude product which was purified by column chromatography (silica gel, 40% ethyl acetate in hexane) to afford the title compound.

EXAMPLE 1C tert-Butyl 3-formylpiperidine-1-carboxylate

To a solution of Example 1B (5 g, 23.22 mmol) in dichloromethane (50 mL) was added pyridinium chlorochromate (10.01 g, 46.4 mmol) and the mixture was stirred for 12 hours. The mixture was filtered and concentrated to afford crude product which was purified by column chromatography (silica gel, 40% ethyl acetate in hexane) to afford the title compound. $^1$H NMR (300 MHz, CDCl$_3$): δ 1.44 (s, 9H), 1.5-1.54 (m, 1H), 1.66-1.69 (m, 2H), 1.9-2.0 (m, 1H), 2.38-2.46 (m, 1H), 3.04-3.12 (m, 1H), 2.38-3.36 (m, 1H), 3.6-3.68 (m, 1H), 3.88-4.0 (m, 1H), 9.7 (s, 1H).

EXAMPLE 1D tert-Butyl 3-ethynylpiperidine-1-carboxylate

To solution of Example 1C (2 g, 9.38 mmol) in methanol (20 mL) was added potassium carbonate (3.89 g, 28.1 mmol) and the mixture was stirred for 30 minutes. Dimethyl 1-diazo-2-oxopropylphosphonate (3.60 g, 18.76 mmol) was added and the mixture was stirred for 12 hours. The mixture was filtered through diatomaceous earth and concentrated to afford crude material which was purified by column chromatography (silica gel, 15% ethyl acetate in hexane) to afford the title compound. $^1$H NMR (300 MHz, CDCl$_3$): δ 1.41 (s, 9H), 1.55-1.59 (m, 1H), 1.67-1.69 (m, 2H), 1.96-1.99 (m, 1H), 2.06-2.07 (m, 1H), 2.43-2.44 (m, 1H), 2.93-3.02 (m, 2H), 3.69-3.75 (m, 1H), 3.9-4.0 (m, 1H).

EXAMPLE 1E tert-Butyl 3-((2-((tert-butoxycarbonyl)amino)-4-chloropyridin-3-yl)ethynyl)piperidine-1-carboxylate To a degassed solution of product of Example 1A (2.033 g, 5.73 mmol) in tetrahydrofuran (15 mL) was added copper (I) iodide (46 mg, 0.239 mmol) and bis(triphenylphosphine)palladium(II) chloride (168 mg, 0.239 mmol) followed by triethylamine (1.998 mL, 14.33 mmol) and Example 1D (1 g, 4.78 mmol). The mixture was stirred for 12 hours at room temperature, filtered through diatomaceous earth, and washed with ethyl acetate. The combined organic layers were washed with water and brine (50 mL each) and were dried over sodium sulfate. Concentration afforded crude product which was purified by column chromatography (silica gel, 15% ethyl acetate in hexane) to afford the title compound. LCMS: 436.2 (M+H)

EXAMPLE 1F tert-butyl 3-(4-chloro-1H-pyrrolo[2,3-b]pyridin-2-yl)piperidine-1-carboxylate To a solution of Example 1E (250 mg, 0.573 mmol) in toluene (5 mL) was added potassium tert-butoxide (161 mg, 1.434 mmol) followed by 18-crown-6 (15 mg, 0.057 mmol) and the mixture was heated at 65° C. for 12 hours. The mixture was dissolved in ethyl acetate (25 mL), washed with water and brine, and dried over anhydrous sodium sulfate. Filtration followed by concentration of the filtrate afforded crude product which was purified by column chromatography (silica gel, 40% ethyl acetate in hexane) to afford the title compound. LCMS: 336.0 (M+H-Boc)$^+$.

EXAMPLE 1G tert-Butyl 3-(4-(5-fluoro-2-methoxyphenyl)-1H-pyrrolo[2,3-b]pyridin-2-yl)piperidine-1-carboxylate To Example 1F (150 mg, 0.447 mmol) in 1,4-dioxane (6 mL) was added cesium carbonate (437 mg, 1.340 mmol) followed by 5-fluoro-2-methoxyphenylboronic acid (114 mg, 0.670 mmol). The mixture was degassed with nitrogen and tricyclohexylphosphine (6.26 mg, 0.022 mmol) and bis(triphenylphosphine)palladium(II) chloride (16 mg, 0.022 mmol) were added. The mixture was heated at 100° C. for 2 hours, diluted with ethyl acetate, and filtered through diatomaceous earth. The organic layer was washed with water and brine (50 mL each) and dried over sodium sulfate. Filtration and concentration afforded crude product which was purified by column chromatography (silica gel, 40% ethyl acetate in hexane) to afford the title compound. LCMS: 514.2 (M+H)$^+$.

EXAMPLE 1H 4-(5-fluoro-2-methoxyphenyl)-2-(piperidin-3-yl)-1H-pyrrolo[2,3-b]pyridine To Example 1G (100 mg, 0.235 mmol) in dichloromethane (2 mL) was added hydrogen chloride in ethyl acetate (2 mL, 0.235 mmol) and the mixture was stirred for 2 hours. Concentration afforded crude product which was purified by preparative HPLC (Zorbax XDB C-18 (32) column with gradient elution from 0.1% trifluoroacetic acid in water to 1:1 methanol/acetonitrile) to afford the title compound as the trifluoroacetate salt. LCMS: 326.1 (M+H)$^+$. $^1$H NMR (400 MHz, DMSO-d$_6$): δ 1.74-1.76 (m, 2H), 1.92 (s, 1H), 2.12-2.16 (m, 1H), 3.13-3.20 (m, 2H), 3.55-3.57 (m, 3H), 3.76 (s, 1H), 6.13 (d, 1.6 Hz, 1H), 7.10 (d, J=4.8 Hz, 1H), 7.22-7.25 (m, 2H), 7.29-7.32 (m, 1H), 8.23 (d, J=5.2 Hz, 1H), 8.6-8.7 (m, 1H), 11.9 (s, 1H).

EXAMPLE 2

4-(4-fluoro-2-methoxyphenyl)-2-(piperidin-3-yl)-1H-pyrrolo[2,3-b]pyridine

EXAMPLE 2A tert-Butyl 3-(4-(4-fluoro-2-methoxyphenyl)-1H-pyrrolo[2,3-b]pyridin-2-yl)piperidine-1-carboxylate The title compound was prepared using the procedure described in Example 1G, using 4-fluoro-2-methoxyphenylboronic acid (114 mg, 0.670 mmol) in place of 5-fluoro-2-methoxyphenylboronic acid. LCMS: 426.0 (M+H)$^+$.

EXAMPLE 2B 4-(4-fluoro-2-methoxyphenyl)-2-(piperidin-3-yl)-1H-pyrrolo[2,3-b]pyridine The title compound was prepared using the procedure described in Example 1H, using Example 2A (100 mg, 0.235 mmol) in place of Example 1G. LCMS: 325.9 (M+H)$^+$. $^1$H NMR (400 MHz, DMSO-d$_6$): δ 1.73-1.77 (m, 1H), 2.17-2.20 (m, 1H), 2.86-2.89 (m, 1H), 3.18-3.21 (m, 1H), 3.31-3.41 (m, 2H), 3.47-3.58 (m, 2H), 3.84 (s, 3H), 6.32 (s, 1H), 7.01 (t, J=8.4 Hz, 1H), 7.22 (d, J=11.6 Hz, 1H), 7.34 (d, J=5.2 Hz, 1H), 7.52 (t, J=7.6 Hz, 1H), 8.35 (d, J=5.6 Hz, 1H), 9.31-9.35 (m, 1H), 12.7 (s, 1H).

EXAMPLE 3

4-(5-fluoro-2-methoxyphenyl)-2-[(3S)-piperidin-3-yl]-1H-pyrrolo[2,3-b]pyridine

The racemic product of Example 1H (100 mg, 0.307 mmol) was resolved using a Chiralpak AD-H HPLC column to afford the title compound. (Absolute stereochemistry was arbitrarily assigned.) LCMS: 325.9 (M+H)$^+$. $^1$H NMR (400 MHz, CD$_3$OD): δ 1.62-1.82 (m, 3H), 2.16-2.18 (m, 1H), 2.59-2.79 (m, 2H), 2.91-2.96 (m, 3H), 3.03-3.06 (m, 2H), 3.75 (s, 3H), 6.04 (s, 1H), 7.07 (dd, J=1.2, 5.2 Hz, 1H), 7.11-7.16 (m, 3H), 8.09 (d, J=5.2 Hz, 1H).

EXAMPLE 4

4-(5-fluoro-2-methoxyphenyl)-2-[(3R)-piperidin-3-yl]-1H-pyrrolo[2,3-b]pyridine

The racemic product of Example 1H (100 mg, 0.307 mmol) was resolved using a Chiralpak AD-H HPLC column to afford the title compound. (Absolute stereochemistry was arbitrarily assigned.) LCMS: 325.9 (M+H)$^+$. $^1$H NMR (400 MHz, CD$_3$OD): δ 1.63-1.71 (m, 2H), 1.78-1.81 (m, 1H), 2.15-2.18 (m, 1H), 2.60-2.79 (m, 2H), 2.93-3.06 (m, 2H), 3.33-3.61 (m, 1H), 3.75 (s, 3H), 6.03 (d, J=0.8 Hz, 1H), 7.06 (d, J=5.2 Hz, 1H), 7.12-7.15 (m, 3H), 8.09 (d, J=5.2 Hz, 1H).

EXAMPLE 5

5-methoxy-6-[2-(piperidin-3-yl)-1H-pyrrolo[2,3-b]pyridin-4-yl]pyridin-2-amine

EXAMPLE 5A tert-butyl 3-(4-(4,4,5,5-tetramethyl-1,3,2-dioxaborolan-2-yl)-1H-pyrrolo[2,3-b]pyridin-2-yl)piperidine-1-carboxylate To a solution of product of Example 1F (200 mg, 0.596 mmol) in 1,4-dioxane (10 mL) was added 4,4,4',4',5,5,5',5'-octamethyl-2,2'-bi(1,3,2-dioxaborolane) (227 mg, 0.893 mmol) and potassium acetate (175 mg, 1.787 mmol) and the mixture was degassed with nitrogen for 5 minutes. 2-Dicyclohexylphosphino)biphenyl (10.44 mg, 0.030 mmol) and palladium acetate (6.69 mg, 0.030 mmol) were added and the mixture was heated at 100° C. for 12 hours. The mixture was filtered through diatomaceous earth and concentrated. The crude product was dissolved in ethyl acetate, washed with water and brine, dried over anhydrous sodium sulfate, filtered, and concentrated to afford crude title compound. Purification by column chromatography (silica gel, 60% ethyl acetate in hexane) afforded the title compound. LCMS: 346.3 (M+H-Boc acid)$^+$.

EXAMPLE 5B tert-butyl 3-(4-(6-amino-3-methoxypyridin-2-yl)-1H-pyrrolo[2,3-b]pyridin-2-yl)piperidine-1-carboxylate The product of Example 5A (200 mg, 0.468 mmol) in N,N-dimethylformamide (8 mL) was treated with sodium bicarbonate (0.118 g, 1.404 mmol) in 0.5 mL water followed by the addition of 6-bromo-5-methoxypyridin-2-amine (170 mg, 0.86 mmol). The mixture was degassed with nitrogen and [1,1'-bis(di tert butyl phosphino)ferrocene]palladium(II) dichloride (21 mg, 0.033 mmol) was added. The mixture was heated at 100° C. for 12 hours, diluted with ethyl acetate and filtered through diatomaceous earth. The combined organic layers were washed with water and brine (25 mL each), dried over sodium sulfate, filtered, and concentrated to afford the crude product. Purification by column chromatography (silica gel, 60% ethyl acetate-hexane) afforded the title compound. LCMS: 424.0 (M+H)$^+$.

EXAMPLE 5C 5-methoxy-6-(2-(piperidin-3-yl)-1H-pyrrolo[2,3-b]pyridin-4-yl)pyridin-2-amine Example 5B (0.1 g, 0.236 mmol) was treated with hydrogen chloride in ethyl acetate (2 mL as described in Example 1H to afford the title compound as the trifluoroacetate salt. LCMS: 324.1 (M+H)$^+$. $^1$H NMR (400 MHz, DMSO-d$_6$): δ 1.69-1.77 (m, 2H), 1.90-1.93 (m, 1H), 2.12-2.15 (m, 1H), 2.84-2.87 (m, 1H), 3.04-3.23 (m, 2H), 3.32-3.38 (m, 2H), 3.53-3.56 (m, 2H), 3.74 (s, 3H), 6.29 (s, 1H), 6.98 (d, J=7.2 Hz, 1H), 7.26 (d, J=4.8 Hz, 1H), 7.95 (brs, 1H), 8.29 (d, J=4.8 Hz, 1H), 8.72 (m, 1H), 12.0 (s, 1H).

EXAMPLE 6

4-[5-(4,5-dihydro-1H-imidazol-2-yl)-2-methoxyphenyl]-2-(piperidin-3-yl)-1H-pyrrolo[2,3-b]pyridine

EXAMPLE 6A 2-(3-bromo-4-methoxyphenyl)-4,5-dihydro-1H-imidazole

To a solution of 3-bromo-4-methoxybenzonitrile (1 g, 4.72 mmol) in 10 mL of ethane-1,2-diamine was added sulfur (0.121 g, 3.77 mmol) and the mixture was heated at 110° C. overnight. The mixture was cooled, quenched with water and extracted with ethyl acetate. The organic layer was washed with water and brine (25 mL each), dried over sodium sulfate, filtered, and concentrated to afford the title compound. LCMS: 257 (M+2)$^+$.

EXAMPLE 6B tert-butyl 2-(3-bromo-4-methoxyphenyl)-4,5-dihydro-1H-imidazole-1-carboxylate A solution of Example 6A (700 mg, 2.74 mmol) in dichloromethane (10 mL) was cooled to 0° C. and triethylamine (833 mg, 8.23 mmol) and di-tert-butyl dicarbonate (898 mg, 4.12 mmol) were added. The mixture was stirred at room temperature for 2 hours and diluted with dichloromethane. The organic layer was washed with water and brine, dried over sodium sulfate, filtered, and concentrated to afford the crude product. Purification by column chromatography (silica gel, 15% ethyl acetate in hexane) afforded the title compound. LCMS: 357 (M+2)$^+$.

EXAMPLE 6C tert-butyl 2-(4-methoxy-3-(4,4,5,5-tetramethyl-1,3,2-dioxaborolan-2-yl)phenyl)-4,5-dihydro-1H-imidazole-1-carboxylate A mixture of Example 6B (500 mg, 1.408 mmol), potassium acetate (414 mg, 4.22 mmol) and 4,4,4',4',5,5,5',5'-octamethyl-2,2'-bi(1,3,2-dioxaborolane) (429 mg, 1.689 mmol) in 1,4-dioxane (5 mL) was degassed with nitrogen for 5 minutes and [1,1'-bis(diphenylphosphino)ferrocene]dichloropalladium(II) dichloromethane adduct (57.5 mg, 0.070 mmol) was added. The mixture was heated at 100° C. for 12 hours, cooled, and concentrated and the residue purified by column chromatography (silica gel, 30% ethyl acetate in hexane) to afford the title compound. LCMS: 403 (M+H)$^+$.

EXAMPLE 6D tert-butyl 3-(4-(5-(1-(tert-butoxycarbonyl)-4,5-dihydro-1H-imidazol-2-yl)-2-methoxyphenyl)-1H-pyrrolo[2,3-b]pyridin-2-yl)piperidine-1-carboxylate The title compound was prepared using the procedure described in Example 1 G, using Example 6C (270 mg, 0.670 mmol) in place of 5-fluoro-2-methoxyphenylboronic acid. LCMS: 476.3 (M+H-Boc)$^+$.

EXAMPLE 6E 4-(5-(4,5-dihydro-1H-imidazol-2-yl)-2-methoxyphenyl)-2-(piperidin-3-yl)-1H-pyrrolo[2,3-b]pyridine To Example 6D (150 mg, 0.261 mmol) in ethanol (2 mL) was added hydrogen chloride in ethanol (2 mL) and the mixture was stirred for 2 hours. Concentration and purification by preparative HPLC (Agilent AD/PP/C18-15/033 reversed phase column and gradient elution from water to 1:1 methanol/acetonitrile over 30 minutes) afforded the title compound as the hydrochloride salt. LCMS: 376.1 (M+H)$^+$. $^1$H NMR (400 MHz, DMSO-d$_6$): δ 1.69-1.87 (m, 4H), 2.12-2.15 (m, 1H), 2.82-2.83 (m, 1H), 3.10-3.13 (m, 2H), 3.27-3.29 (m, 2H), 3.41-3.52 (m, 3H), 3.98 (s, 3H), 6.16 (s, 1H), 7.16 (d, J=4.8 Hz, 1H), 7.50 (d, J=8.8 Hz, 1H), 8.08 (d, J=2.4 Hz, 1H), 8.99 (dd, J=2.4, 8.8 Hz, 1H), 8.28 (d, J=5.2 Hz, 1H), 9.28 (brs, 1H), 10.63 (s, 1H), 12.2 (s, 1H).

EXAMPLE 7

4-(5-cyclopropyl-2-methoxyphenyl)-2-(piperidin-3-yl)-1H-pyrrolo[2,3-b]pyridine

EXAMPLE 7A tert-butyl 3-(4-(5-cyclopropyl-2-methoxyphenyl)-1H-pyrrolo[2,3-b]pyridin-2-yl)piperidine-1-carboxylate Example 5A (200 mg, 0.468 mmol) in N,N-dimethylformamide (8 mL) was treated with sodium bicarbonate (0.118 g, 1.404 mmol) in 0.5 mL water followed by the addition of 2-bromo-4-cyclopropyl-1-methoxybenzene (158 mg, 0.702 mmol). The mixture was degassed with nitrogen and [1,1'-bis(di tert butyl phosphino)ferrocene]palladium(II) dichloride (21 mg, 0.033 mmol) was added. The mixture was subjected to microwave irradiation using a Biotage Initiator (model 355302) at 100° C. for 1 hour, diluted with ethyl acetate, and filtered through diatomaceous earth. The organic layer was washed with water and brine (25 mL each), dried over sodium sulfate, filtered, and concentrated to afford the crude product. Purification by column chromatography (silica gel, 40% ethyl acetate-hexane) afforded the title compound. LCMS: 448.0 (M+H)$^+$.

EXAMPLE 7B 4-(5-cyclopropyl-2-methoxyphenyl)-2-(piperidin-3-yl)-1H-pyrrolo[2,3-b]pyridine The title compound was prepared as the trifluoroacetate salt using the procedure described in Example 1H, using Example 7A (120 mg, 0.219 mmol) in place of Example 1G. LCMS: 348.6 (M+H)$^+$. $^1$H NMR (400 MHz, DMSO-d$_6$): δ 0.61-0.65 (m, 2H), 0.8-0.94 (m, 2H), 1.21-1.72 (m, 1H), 1.67-1.75 (m, 2H), 1.89-1.95 (m, 2H), 2.84-2.86 (m, 2H), 3.08-3.16 (m, 3H), 3.7 (s, 3H), 6.03 (s, 1H), 7.02-7.08 (m, 3H), 7.14 (dd, J=2, 8.8 Hz, 1H), 8.17 (d, J=5.2 Hz, 1H), 8.71 (brs, 1H), 11.8 (s, 1H).

EXAMPLE 8

4-(4-fluoro-2-methoxyphenyl)-2-(1-methylpiperidin-3-yl)-1H-pyrrolo[2,3-b]pyridine Example 2A (220 mg, 0.517 mmol) in 5 mL anhydrous tetrahydrofuran was cooled to 0° C. and 1M lithium aluminium hydride in tetrahydrofuran (2.068 mL, 2.068 mmol) was added under inert atmosphere. The mixture was warmed to room temperature and heated to 60° C. for 2 hours. The mixture was cooled to 0° C. and ethyl acetate and saturated ammonium chloride solution was added. After stirring for 30 minutes, the mixture was extracted with ethyl acetate and the organic layer was washed with water and brine (25 mL each). The organic layer was dried over sodium sulfate, filtered, and concentrated to afford the title compound. LCMS: 340.3 (M+H)$^+$. $^1$H NMR (400 MHz, DMSO-$d_6$): δ 1.58-1.72 (m, 2H), 1.88-2.0 (m, 2H), 2.2 (s, 3H), 2.73-2.76 (m, 2H), 2.92-3.02 (m, 3H), 3.78 (s, 3H), 5.95 (s, 1H), 6.89-6.99 (m, 2H), 7.08 (dd, J=2.4, 11.6 Hz, 1H), 7.38-7.42 (m, 1H), 8.12 (d, J=4.8 Hz, 1H), 11.6 (s, 1H).

EXAMPLE 9

4-(5-fluoro-2-methoxyphenyl)-2-(1-methylpiperidin-3-yl)-1H-pyrrolo[2,3-b]pyridine The title compound was prepared using the procedure described in Example 8, using Example 1G (150 mg, 0.353 mmol) in place of Example 2A. LCMS: 340.0 (M+H)$^+$. $^1$H NMR (400 MHz, DMSO-$d_6$): δ 1.55-1.58 (m, 2H), 1.88 (s, 1H), 1.96-2.01 (m, 2H), 2.17 (s, 3H), 2.66-2.73 (m, 2H), 2.9-3.0 (m. 2H), 3.72 (s, 3H), 5.95 (d, J=1.2 Hz, 1H), 6.9 (d, J=4.8 Hz, 1H), 7.15-7.28 (m, 3H), 8.12 (d, J=5.2 Hz, 1H), 11.6 (s, 1H).

EXAMPLE 10

1-{3-[4-(5-fluoro-2-methoxyphenyl)-1H-pyrrolo[2,3-b]pyridin-2-yl]piperidin-1-yl}ethanone

EXAMPLE 10A

3-ethynylpiperidine

To Example 1D (1 g, 4.78 mmol) in dichloromethane (20 mL) was added trifluoroacetic acid (1.841 mL, 23.89 mmol) and the mixture was stirred at room temperature for 12 hours. Concentration afforded the title compound.

EXAMPLE 10B

1-(3-ethynylpiperidin-1-yl)ethanone

To Example 10A (0.5 g, 4.58 mmol) in dichloromethane (10 mL) was added triethylamine (1.915 mL, 13.74 mmol) followed by acetic anhydride (0.519 mL, 5.50 mmol) and the mixture was stirred at room temperature for 4 hours. After concentration, the residue was dissolved in ethyl acetate, washed with water and brine, dried over anhydrous sodium sulfate, filtered, and concentrated to afford crude product. Purification by column chromatography (silica gel, 60% ethyl acetate in hexane) afforded the title compound. LCMS: 152.1 (M+H)$^+$.

EXAMPLE 10C tert-butyl (3-((1-acetylpiperidin-3-yl)ethynyl)-4-chloropyridin-2-yl)carbamate The title compound was prepared using the procedure described in Example 1E, using Example 10B (277 mg, 1.83 mmol) in place of Example 1D. LCMS: 378 (M+H)$^+$.

EXAMPLE 10D

1-(3-(4-chloro-1H-pyrrolo[2,3-b]pyridin-2-yl)piperidin-1-yl)ethanone

The title compound was prepared using the procedure described in Example 1F, using Example 10C (300 mg, 0.794 mmol) in place of Example 1E. LCMS: 278.4 (M+H)$^+$.

EXAMPLE 10E

1-(3-(4-(5-fluoro-2-methoxyphenyl)-1H-pyrrolo[2,3-b]pyridin-2-yl)piperidin-1-yl)ethanone The title compound was prepared as the trifluoroacetate salt using the procedure described in Example 1G, using Example 10D (150 mg, 0.54 mmol) in place of Example 1F. LCMS: 368 (M+H)$^+$. $^1$H NMR (400 MHz, DMSO-$d_6$): δ 1.2-1.5 (m, 2H), 1.71-1.77 (m, 2H), 2.05 (s, 3H), 2.8-2.9 (m, 2H), 3.08-3.17 (m, 1H), 3.73 (s, 3H), 4.02-4.05 (m, 1H), 4.32-4.35 (m. 1H), 6.09 (s, 1H), 7.09 (t, J=6 Hz, 1H), 7.18-7.30 (m, 3H), 8.19 (d, J=5.2 Hz, 1H), 11.8 (s, 1H).

EXAMPLE 11

N-benzyl-5-chloro-6-[2-(piperidin-3-yl)-1H-pyrrolo[2,3-b]pyridin-4-yl]pyridin-2-amine

EXAMPLE 11A

6-bromo-5-chloropyridin-2-amine

To a solution of 6-bromopyridin-2-amine (1 g, 5.78 mmol) in acetonitrile (10 mL) was added N-chlorosuccinimide (0.849 g, 6.36 mmol) and the mixture was heated at 80° C. for 12 hours. The mixture was filtered through diatomaceous earth and concentrated and the residue was dissolved in ethyl acetate and washed with water and brine. Drying over anhydrous sodium sulfate, filtration, concentration and purification by column chromatography (silica gel, 30% ethyl acetate in hexane) afforded the title compound. LCMS: 209.1 (M+2)$^+$.

EXAMPLE 11B

N-benzyl-6-bromo-5-chloropyridin-2-amine

A solution of Example 11A (500 mg, 2.410 mmol) in 1,2-dichloroethane (10 mL) and acetic acid (5 mL) was treated with benzaldehyde (281 mg, 2.65 mmol) and the mixture was stirred at room temperature for 2 hours. Sodium triacetoxyborohydride (2.043 g, 9.64 mmol) was added and the mixture was stirred at room temperature for 12 hours.

The mixture was diluted with water (25 mL), treated with saturated sodium bicarbonate solution, extracted with ethyl acetate, and washed with water and brine. The organic layer was dried over anhydrous sodium sulfate, filtered, and concentrated to afford the crude title compound. Purification by column chromatography (silica gel, 15% ethyl acetate in hexane) afforded the title compound.

EXAMPLE 11C tert-butyl 3-(4-(6-(benzylamino)-3-chloropyridin-2-yl)-1H-pyrrolo[2,3-b]pyridin-2-yl)piperidine-1-carboxylate Example 5A (200 mg, 0.468 mmol) in dioxane (8 mL) was treated with sodium bicarbonate (0.118 g, 1.404 mmol) in 0.5 mL water followed by the addition of Example 11B (0.167 g, 0.562 mmol). The mixture was degassed with nitrogen and [1,1'-bis(di tert butyl phosphino)ferrocene] palladium(II) dichloride (21 mg, 0.033 mmol) was added. The mixture was heated at 100° C. for 2 hours, diluted with ethyl acetate, and filtered through diatomaceous earth. The organic layer was washed with water and brine (25 mL each), dried over anhydrous sodium sulfate, filtered, and concentrated to afford the crude product. Purification by column chromatography (silica gel, 4% methanol in dichloromethane) afforded the title compound. LCMS: 418 $(M+H)^+$.

EXAMPLE 11D

N-benzyl-5-chloro-6-(2-(piperidin-3-yl)-1H-pyrrolo[2,3-b]pyridin-4-yl)pyridin-2-amine The title compound was prepared using the procedure described in Example 1H, using Example 11C (150 mg, 0.290 mmol) in place of Example 1G. LCMS: 417.9 $(M+H)^+$. $^1$H NMR (400 MHz, DMSO-$d_6$): δ 1.56-1.59 (m, 2H), 1.86-1.90 (m, 1H), 2.0-2.03 (m, 1H), 2.8-2.83 (m, 1H), 2.97-3.12 (m, 2H), 3.29-3.38 (m, 2H), 4.46 (s, 2H), 5.9 (s, 1H), 6.63 (d, J=9.2 Hz, 1H), 7.1 (d, J=4.8 Hz, 1H), 7.23-7.34 (m, 5H), 7.46 (brs, 1H), 7.60 (d, J=8.8 Hz, 1H), 8.21 (d, J=5.2 Hz, 1H), 8.55 (brs, 1H), 11.8 (s, 1H).

EXAMPLE 12

N-benzyl-5-chloro-6-[2-(1-methylpiperidin-3-yl)-1H-pyrrolo[2,3-b]pyridin-4-yl]pyridin-2-amine A solution of Example 11C (200 mg, 0.386 mmol) in tetrahydrofuran (5 mL) was cooled to −10° C. and 1M lithium aluminum hydride in tetrahydrofuran (2 mL) was added. The mixture was stirred at room temperature for 12 hours, cooled to 0° C. and quenched with aqueous ammonium chloride. The mixture was extracted with ethyl acetate and the organic layer was washed with water and brine (25 mL each). Drying over anhydrous sodium sulfate, filtration, concentration, and purification by preparative HPLC (Agilent AD/PP/C18-15/033 reversed phase column and gradient elution from 0.01% trifluoroacetic acid in water to 1:1 methanol/acetonitrile over 60 minutes) afforded the title compound as the trifluoroacetate salt. LCMS: 431.9 $(M+H)^+$. $^1$H NMR (400 MHz, CD$_3$OD): δ 1.31-1.35 (m, 2H), 1.63-1.67 (m, 1H), 1.91-2.22 (m, 3H), 2.93 (s, 3H), 3.06-3.15 (m, 1H), 3.58-3.61 (m, 1H), 3.73-3.76 (m, 1H), 4.57 (s, 2H), 6.27 (s, 1H), 6.66 (dd, J=3.6, 9.2 Hz, 1H), 7.33-7.37 (m, 5H), 7.60 (d, J=8.8 Hz, 1H), 8.28 (s, 2H).

EXAMPLE 13

N-benzyl-6-[2-(1-methylpiperidin-3-yl)-1H-pyrrolo[2,3-b]pyridin-4-yl]pyridin-2-amine The title compound was isolated as a trifluoroacetate salt as a byproduct from Example 12. LCMS: 398.3 (M+H). $^1$H NMR (400 MHz, CD$_3$OD): δ 1.70-1.73 (m, 1H), 1.96-1.99 (m, 2H), 2.14-2.27 (m, 2H), 2.96 (s, 3H), 3.01-3.02 (m, 1H), 3.12-3.18 (m, 1H), 3.62-3.65 (m, 1H), 3.79-3.82 (m, 1H), 4.76 (s, 2H), 6.78 (s, 1H), 7.01 (d, J=8.8 Hz, 1H), 7.35 (d, J=7.2 Hz, 2H), 7.40-7.48 (m, 4H), 7.56 (d, J=5.6 Hz, 1H), 7.92 (d, J=7.6 Hz, 1H), 8.37 (d, J=5.6 Hz, 1H).

EXAMPLE 14

N-benzyl-5-methoxy-6-[2-(piperidin-3-yl)-1H-pyrrolo[2,3-b]pyridin-4-yl]pyridin-2-amine

EXAMPLE 14A

N-benzyl-6-bromo-5-methoxypyridin-2-amine

The title compound was prepared using the procedure described in Example 11B, using 6-bromo-5-methoxypyridin-2-amine (800 mg, 3.94 mmol) in place of Example 11A. LCMS: 292.9 $(M+H)^+$.

EXAMPLE 14B tert-butyl 3-(4-(6-(benzylamino)-3-methoxypyridin-2-yl)-1H-pyrrolo[2,3-b]pyridin-2-yl)piperidine-1-carboxylate The title compound was prepared using the procedure described in Example 5B, using Example 14A (123 mg, 0.421 mmol) in place of 6-bromo-5-methoxypyridin-2-amine. LCMS: 514.2 $(M+H)^+$.

EXAMPLE 14C

N-benzyl-5-methoxy-6-(2-(piperidin-3-yl)-1H-pyrrolo[2,3-b]pyridin-4-yl)pyridin-2-amine The title compound was prepared as the trifluoroacetate salt using the procedure described in Example 1H, using Example 14B (80 mg, 0.156 mmol) in place of Example 1G. LCMS: 414.1 $(M+H)^+$. $^1$H NMR (400 MHz, DMSO-$d_6$): δ 1.57-1.59 (m, 1H), 1.7-1.78 (m, 1H), 1.89-2.04 (m, 2H), 2.82-2.99 (m, 2H), 3.10-3.13 (m, 1H), 3.33-3.42 (m, 1H), 3.49-3.52 (m, 1H), 3.71 (s, 3H), 4.54 (s, 2H), 6.27 (s, 1H), 6.71 (d, J=8.8 Hz, 1H), 7.28-7.37 (m, 6H), 7.54 (d, J=9.2 Hz, 1H), 8.21 (d, J=5.6 Hz, 1H), 8.73-8.88 (m, 2H), 11.8 (s, 1H).

EXAMPLE 15

N-benzyl-5-chloro-6-{2-[1-(propan-2-ylsulfonyl)piperidin-3-yl]-1H-pyrrolo[2,3-b]pyridin-4-yl}pyridin-2-amine

EXAMPLE 15A 3-ethynyl-1-(isopropylsulfonyl)piperidine

To a solution of Example 10A (500 mg, 4.58 mmol) in dichloromethane (10 mL) was added triethylamine (2.55 mL, 18.32 mmol) followed by propane-2-sulfonyl chloride (1.306 g, 9.16 mmol) and the mixture was stirred for 3 hours. The mixture was concentrated and the residue was dissolved in ethyl acetate, washed with water and brine, dried over anhydrous sodium sulfate, filtered, and concentrated. Purification by column chromatography (silica gel, 30% ethyl acetate in hexane) afforded the title compound. LCMS: 216.2 (M+H-Boc)$^+$.

EXAMPLE 15B tert-butyl (4-chloro-3-((1-(isopropylsulfonyl)piperidin-3-yl)ethynyl)pyridin-2-yl)carbamate The title compound was prepared using the procedure described in Example 1E, using Example 15A (395 mg, 1.833 mmol) in place of Example 1D. LCMS: 342.4 (M+H-Boc)$^+$.

EXAMPLE 15C 4-chloro-2-(1-(isopropylsulfonyl)piperidin-3-yl)-1H-pyrrolo[2,3-b]pyridine The title compound was prepared using the procedure described in Example 1F, using Example 15B (550 mg, 1.24 mmol) in place of Example 1E. LCMS: 341.8 (M+H)$^+$.

EXAMPLE 15D 2-(1-(isopropylsulfonyl)piperidin-3-yl)-4-(4,4,5,5-tetramethyl-1,3,2-dioxaborolan-2-yl)-1H-pyrrolo[2,3-b]pyridine The title compound was prepared using the procedure described in Example 5A, using Example 15C (200 mg, 0.585 mmol) in place of Example 1F. LCMS: 352.0 (M+H)$^+$.

EXAMPLE 15E

N-benzyl-5-chloro-6-(2-(1-(isopropylsulfonyl)piperidin-3-yl)-1H-pyrrolo[2,3-b]pyridin-4-yl)pyridin-2-amine The title compound was prepared using the procedure described in Example 5B, using Example 15D (200 mg, 0.461 mmol) in place of Example 5A and Example 11B (165 mg, 0.554 mmol in place of the 6-bromo-5-methoxypyridin-2-amine. LCMS: 524.1 (M+H)$^+$. $^1$H NMR (400 MHz, DMSO-d$_6$): δ 1.20 (dd, J=2.4, 6.8 Hz, 7H), 1.50-1.55 (m, 2H), 1.76-1.96 (m, 2H), 2.85-2.95 (m, 3H), 3.64-3.82 (m, 2H), 4.47 (d, J=5.2 Hz, 2H), 5.98 (s, 1H), 6.63 (d, J=8.8 Hz, 1H), 6.97 (s, 1H), 7.11 (d, J=4.8 Hz, 1H), 7.22-7.34 (m, 5H), 7.44-7.47 (m, 1H), 7.60 (d, J=8.8 Hz, 1H), 8.17 (d, J=4.8 Hz, 1H), 11.7 (s, 1H).

EXAMPLE 16 methyl 3-{4-[6-(benzylamino)-3-chloropyridin-2-yl]-1H-pyrrolo[2,3-b]pyridin-2-yl}piperidine-1-carboxylate

EXAMPLE 16A methyl 3-ethynylpiperidine-1-carboxylate

To a solution of Example 10A (500 mg, 4.58 mmol) in dichloromethane (10 mL) was added triethylamine (2.55 mL, 18.32 mmol) followed by methyl chloroformate (0.532 mL, 6.87 mmol) and the mixture was stirred at room temperature for 3 hours. The mixture was diluted with water and dichloromethane and the organic layer was separated and washed with water and brine. After drying over sodium sulfate, filtration, and concentration, the residue was purified by column chromatography (silica gel, 20% ethyl acetate in hexane) to afford the title compound. LCMS: 168.3 (M+H)$^+$.

EXAMPLE 16B methyl 3-((2-((tert-butoxycarbonyl)amino)-4-chloropyridin-3-yl)ethynyl)piperidine-1-carboxylate The title compound was prepared using the procedure described in Example 1E, using Example 16A (424 mg, 2.54 mmol) in place of Example 1D. LCMS: 294 (M+H-Boc)$^+$.

EXAMPLE 16C methyl 3-(4-chloro-1H-pyrrolo[2,3-b]pyridin-2-yl)piperidine-1-carboxylate The title compound was prepared using the procedure described in Example 1F, using Example 16B (800 mg, 2.031 mmol) in place of Example 1E. LCMS: 294 (M+H)$^+$.

EXAMPLE 16D methyl 3-(4-(4,4,5,5-tetramethyl-1,3,2-dioxaborolan-2-yl)-1H-pyrrolo[2,3-b]pyridin-2-yl)piperidine-1-carboxylate The title compound was prepared using the procedure described in Example 5A, using Example 16C (200 mg, 0.681 mmol) in place of Example 1F. LCMS: 304 (M+H-boronic acid)$^+$.

EXAMPLE 16E methyl 3-(4-(6-(benzylamino)-3-chloropyridin-2-yl)-1H-pyrrolo[2,3-b]pyridin-2-yl)piperidine-1-carboxylate The title compound was prepared using the procedure described in Example 5B, using Example 16D (150 mg, 0.389 mmol)) in place of Example 5A and Example 11B (139 mg, 0.467 mmol)) in place of the product of 6-bromo-5-methoxypyridin-2-amine. LCMS: 476.1 (M+H)$^+$. $^1$H NMR (400 MHz, DMSO-d$_6$): δ 1.44-1.69 (m, 3H), 1.94-1.97 (m, 1H), 2.77-2.80 (m, 3H), 3.59 (s, 3H), 3.91-3.94 (m, 2H), 4.48 (s, 2H), 6.0 (s, 1H), 6.66 (d, J=9.2 Hz, 1H), 7.18-7.31 (m, 6H), 7.62 (d, J=8.8 Hz, 2H), 8.22 (d, J=5.2 Hz, 1H), 11.8 (s, 1H).

EXAMPLE 17

4-(5-fluoro-2-methoxyphenyl)-2-(piperidin-4-yl)-1H-pyrrolo[2,3-b]pyridine

EXAMPLE 17A tert-butyl 4-(hydroxymethyl)piperidine-1-carboxylate

The title compound was prepared using the procedure described in Example 1B, using piperidin-4-ylmethanol (5 g, 43.4 mmol) in place of piperidin-3-ylmethanol.

EXAMPLE 17B tert-butyl 4-formylpiperidine-1-carboxylate

The title compound was prepared using the procedure described in Example 1C, using Example 17A (5 g, 23.22 mmol) in place of Example 1B. LCMS: 213.9 (M+H)$^+$.

EXAMPLE 17C tert-butyl 4-ethynylpiperidine-1-carboxylate

The title compound was prepared using the procedure described in Example 1D, using Example 17B (1 g, 4.69 mmol) in place of Example 1C. LCMS: 110 (M+H-Boc)$^+$.

EXAMPLE 17D tert-butyl 4-((2-((tert-butoxycarbonyl)amino)-4-chloropyridin-3-yl)ethynyl)piperidine-1-carboxylate The title compound was prepared using the procedure described in Example 1E, using Example 17C in place of Example 1D. LCMS: 335.9 (M+H-Boc)$^+$.

EXAMPLE 17E tert-butyl 4-(4-chloro-1H-pyrrolo[2,3-b]pyridin-2-yl)piperidine-1-carboxylate The title compound was prepared using the procedure described in Example 1F, using Example 17D (800 mg, 1.835 mmol) in place of Example 1E. LCMS: 335.8 (M+H)$^+$.

EXAMPLE 17F tert-butyl 4-(4-(5-fluoro-2-methoxyphenyl)-1H-pyrrolo[2,3-b]pyridin-2-yl)piperidine-1-carboxylate The title compound was prepared using the procedure described in Example 1 G, using Example 17E (300 mg, 0.893 mmol) in place of Example 1F. LCMS: 425.9 (M+H)$^+$.

EXAMPLE 17G 4-(5-fluoro-2-methoxyphenyl)-2-(piperidin-4-yl)-1H-pyrrolo[2,3-b]pyridine The title compound was prepared using the procedure described in Example 1H, using Example 17F (100 mg, 0.235 mmol) in place of Example 1G. LCMS: 326 (M+H)$^+$. $^1$H NMR (400 MHz, DMSO-d$_6$/D$_2$O): δ 1.77-1.80 (m, 2H), 2.20-2.23 (m, 2H), 3.0-3.06 (m, 3H), 3.33-3.36 (m, 2H), 3.73 (s, 3H), 6.02 (s, 1H), 7.07 (d, J=5.2 Hz, 1H), 7.18-7.22 (m, 2H), 7.25-7.28 (m, 1H), 8.19 (d, J=4.8 Hz, 1H).

EXAMPLE 18

4-(4-fluoro-2-methoxyphenyl)-2-(piperidin-4-yl)-1H-pyrrolo[2,3-b]pyridine

EXAMPLE 18A tert-Butyl 4-(4-(4-fluoro-2-methoxyphenyl)-1H-pyrrolo[2,3-b]pyridin-2-yl)piperidine-1-carboxylate The title compound was prepared using the procedure described in Example 1 G, using Example 17E (300 mg, 0.893 mmol) in place of Example 1F and 4-fluoro-2-methoxyphenylboronic acid (228 mg, 1.340 mmol) in place of 5-fluoro-2-methoxyphenylboronic acid. LCMS: 425.9 (M+H)$^+$.

EXAMPLE 18B 4-(4-fluoro-2-methoxyphenyl)-2-(piperidin-4-yl)-1H-pyrrolo[2,3-b]pyridine The title compound was prepared as the trifluoroacetate salt using the procedure described in Example 1H, using Example 18A (100 mg, 0.235 mmol) in place of Example 1G. LCMS: 341.9 (M+H)$^+$. $^1$H NMR (400 MHz, DMSO-d$_6$): δ 1.7-1.83 (m, 2H), 2.20-2.23 (m, 2H), 3.0-3.09 (m, 3H), 3.34-3.37 (m, 2H), 3.78 (s, 3H), 5.99 (d, J=1.6 Hz, 1H), 7.04 (d, J=4.8 Hz, 1H), 7.16 (dd, J=2, 8 Hz, 1H), 7.28 (d, J=2 Hz, 1H), 7.39 (d, J=8.4 Hz, 1H), 8.18 (d, J=4.8 Hz, 1H), 8.32 (brs, 1H), 11.80 (s, 1H).

EXAMPLE 19

4-(4-chloro-2-methoxyphenyl)-2-(piperidin-4-yl)-1H-pyrrolo[2,3-b]pyridine

EXAMPLE 19A tert-butyl 4-(4-(4-chloro-2-methoxyphenyl)-1H-pyrrolo[2,3-b]pyridin-2-yl)piperidine-1-carboxylate The title compound was prepared using the procedure described in Example 1 G, using Example 17E (200 mg, 0.596 mmol) in place of Example 1F and 4-chloro-2-methoxyphenylboronic acid (167 mg, 0.893 mmol) in place of 5-fluoro-2-methoxyphenylboronic acid. LCMS: 441.8 (M+H)$^+$.

EXAMPLE 19B 4-(4-chloro-2-methoxyphenyl)-2-(piperidin-4-yl)-1H-pyrrolo[2,3-b]pyridine To a solution of Example 19A (100 mg, 0.235 mmol) in 2 mL ethanol was added 2 mL ethanolic HCl at 0° C. and the mixture was stirred at ambient temperature for 2 hours. The mixture was concentrated and the crude material was purified by preparative HPLC (Zorbax XDB C-18 (32) analytical reversed phase column and gradient elution from 0.1% trifluoroacetic acid in water to 1:1 of methanol/acetonitrile over 20 minutes) to afford the title compound as the trifluoroacetate salt. LCMS: 341.9 (M+H)$^+$. $^1$H NMR (400 MHz, DMSO-d$_6$): δ 1.7-1.83 (m, 2H), 2.20-2.23 (m, 2H), 3.0-3.09 (m, 3H), 3.34-3.37 (m, 2H), 3.78 (s, 3H), 5.99 (d, J=1.6 Hz, 1H), 7.04 (d, J=4.8 Hz, 1H), 7.16 (dd, J=2, 8 Hz, 1H), 7.28 (d, J=2 Hz, 1H), 7.39 (d, J=8.4 Hz, 1H), 8.18 (d, J=4.8 Hz, 1H), 8.32 (brs, 1H), 11.80 (s, 1H).

EXAMPLE 20

4-(3-methoxypyridin-2-yl)-2-(piperidin-4-yl)-1H-pyrrolo[2,3-b]pyridine

EXAMPLE 20A tert-butyl 4-(4-(3-methoxypyridin-2-yl)-1H-pyrrolo[2,3-b]pyridin-2-yl)piperidine-1-carboxylate The title compound was prepared using the procedure described in Example 1 G, using Example 17E (200 mg, 0.596 mmol) in place of Example 1F and 4-methoxypyridin-3-ylboronic acid (137 mg, 0.893 mmol) in place of 5-fluoro-2-methoxyphenylboronic acid. LCMS: 308.9 (M+H)+.

EXAMPLE 20B 4-(3-methoxypyridin-2-yl)-2-(piperidin-4-yl)-1H-pyrrolo[2,3-b]pyridine The title compound was prepared as the acetate salt using the procedure described in Example 6E, using Example 20A (120 mg, 0.294 mmol) in place of Example 6D. LCMS: 308.9 (M+H)+. $^1$H NMR (400 MHz, DMSO-d$_6$): δ 1.62-1.72 (m, 2H), 2.04-2.08 (m, 2H), 2.72-2.8 (m, 2H), 2.9-2.94 (m, 1H), 3.14-3.17 (m, 2H), 3.83 (s, 3H), 5.95 (s, 1H), 7.04 (d, J=5.2 Hz, 1H), 7.24 (d, J=6 Hz, 1H), 8.16 (d, J=4.8 Hz, 1H), 8.42 (s, 1H), 8.52 (d, J=5.6 Hz, 1H), 11.62 (s, 1H).

EXAMPLE 21

5-methoxy-6-[2-(piperidin-4-yl)-1H-pyrrolo[2,3-b]pyridin-4-yl]pyridin-2-amine

EXAMPLE 21A tert-butyl 4-(4-(4,4,5,5-tetramethyl-1,3,2-dioxaborolan-2-yl)-1H-pyrrolo[2,3-b]pyridin-2-yl)piperidine-1-carboxylate The title compound was prepared using the procedure described in Example 5A, using Example 17E (100 mg, 0.298 mmol) in place of Example 1F. LCMS: 428.4 (M+H)+.

EXAMPLE 21B tert-butyl 4-(4-(6-amino-3-methoxypyridin-2-yl)-1H-pyrrolo[2,3-b]pyridin-2-yl)piperidine-1-carboxylate The title compound was prepared using the procedure described in Example 5B, using Example 21A (200 mg, 468 mmol) in place of Example 5A. LCMS: 424.3 (M+H)+.

EXAMPLE 21C 5-methoxy-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 21B (80 mg, 0.189 mmol) in place of Example 1G. LCMS: 324.2 (M+H)+. $^1$H NMR (400 MHz, DMSO-d$_6$): δ 1.76-1.86 (m, 2H), 2.22-2.25 (m, 2H), 2.97-3.20 (m, 3H), 3.36-3.39 (m, 2H), 3.75 (s, 3H), 6.19 (s, 1H), 7.02-7.02 (m, 1H), 7.24 (d, J=5.2 Hz, 1H), 8.01 (brs, 1H), 8.29 (d, J=5.2 Hz, 1H), 8.43 (brs, 1H), 12.0 (s, 1H).

EXAMPLE 22

4-(4,5-difluoro-2-methoxyphenyl)-2-(piperidin-4-yl)-1H-pyrrolo[2,3-b]pyridine

EXAMPLE 22A tert-butyl 4-(4-(4,5-difluoro-2-methoxyphenyl)-1H-pyrrolo[2,3-b]pyridin-2-yl)piperidine-1-carboxylate The title compound was prepared using the procedure described in Example 1 G, using Example 17E (250 mg, 0.744 mmol) in place of Example 1F and 4,5-difluoro-2-methoxyphenylboronic acid (210 mg, 1.117 mmol) in place of 5-fluoro-2-methoxyphenylboronic acid. LCMS: 444.2 (M+H)+.

EXAMPLE 22B 4-(4,5-difluoro-2-methoxyphenyl)-2-(piperidin-4-yl)-1H-pyrrolo[2,3-b]pyridine The title compound was prepared as the acetate salt using the procedure described in Example 6E, using Example 22A (150 mg, 0.338 mmol) in place of Example 6D. LCMS: 344.2 (M+H)+. $^1$H NMR (400 MHz, DMSO-d$_6$): δ 1.52-1.61 (m, 2H), 1.93-1.99 (m, 2H), 2.66-2.67 (m, 3H), 3.03-3.06 (m, 2H), 3.75 (s, 3H), 5.94 (s, 1H), 6.99 (dd, J=0.8, 4.8 Hz, 1H), 7.32-7.37 (m, 1H), 7.42-7.47 (m, 1H), 8.12 (d, J=4.8 Hz, 1H), 11.60 (s, 1H).

EXAMPLE 23

4-(5-chloro-2-methoxyphenyl)-2-(piperidin-4-yl)-1H-pyrrolo[2,3-b]pyridine

EXAMPLE 23A tert-butyl 4-(4-(5-chloro-2-methoxyphenyl)-1H-pyrrolo[2,3-b]pyridin-2-yl)piperidine-1-carboxylate The title compound was prepared using the procedure described in Example 1G, using Example 17E (250 mg, 0.744 mmol) in place of Example 1F and 5-chloro-2-methoxyphenylboronic acid (167 mg, 0.893 mmol) in place of 5-fluoro-2-methoxyphenylboronic acid. LCMS: 442.2 (M+H)+.

EXAMPLE 23B 4-(5-chloro-2-methoxyphenyl)-2-(piperidin-4-yl)-1H-pyrrolo[2,3-b]pyridine The title compound was prepared as the trifluoroacetate salt using the procedure described in Example 6E, using Example 23A (160 mg, 0.362 mmol) in place of Example 6D. LCMS: 342.2 (M+H)+. $^1$H NMR (400 MHz, DMSO-d$_6$): δ 1.76-1.82 (m, 2H), 2.19-2.22 (m, 2H), 2.98-3.08 (m, 3H), 3.33-3.36 (m, 2H), 3.74 (s, 3H), 5.98 (d, J=1.2 Hz, 1H), 7.06 (d, J=4.8 Hz, 1H), 7.21 (d, J=8.8 Hz, 1H), 7.36 (d, J=2.8 Hz, 1H), 7.48 (dd, J=2.8, 8.8 Hz, 1H), 8.19 (d, J=5.2 Hz, 1H), 8.66 (brs, 1H), 11.8 (s, 1H).

EXAMPLE 24

4-(2-methoxy-5-methylphenyl)-2-(piperidin-4-yl)-1H-pyrrolo[2,3-b]pyridine

EXAMPLE 24A tert-butyl 4-(4-(2-methoxy-5-methylphenyl)-1H-pyrrolo[2,3-b]pyridin-2-yl)piperidine-1-carboxylate The title compound was prepared using the procedure described in Example 1 G, using Example 17E (200 mg, 0.596 mmol) in place of Example 1F and 2-methoxy-5-methylphenylboronic acid (148 mg, 0.893 mmol) in place of 5-fluoro-2-methoxyphenylboronic acid. LCMS: 422.6 (M+H)+.

EXAMPLE 24B

4-(2-methoxy-5-methylphenyl)-2-(piperidin-4-yl)-1H-pyrrolo[2,3-b]pyridine

The title compound was prepared as the hydrochloride salt using the procedure described in Example 1H, using Example 24A (100 mg, 0.237 mmol) in place of Example 1G. LCMS: 322.3 (M+H)$^+$. $^1$H NMR (400 MHz, DMSO-$d_6$): δ 1.80-1.88 (m, 2H), 2.21-2.25 (m, 2H), 2.32 (s, 3H), 2.98-3.16 (m, H), 3.32-3.36 (m, H), 3.73 (s, 3H), 6.13 (s, 1H), 7.12 (d, J=8.4 Hz, 1H), 7.22-7.31 (m, 3H), 8.27 (d, J=5.6 Hz, 1H), 8.72 (m, 1H), 12.4 (s, 1H).

EXAMPLE 25

4-(3-chloro-2-methoxyphenyl)-2-(piperidin-4-yl)-1H-pyrrolo[2,3-b]pyridine

EXAMPLE 25A tert-butyl 4-(4-(3-chloro-2-methoxyphenyl)-1H-pyrrolo[2,3-b]pyridin-2-yl)piperidine-1-carboxylate The title compound was prepared using the procedure described in Example 1 G, using Example 17E (300 mg, 0.893 mmol) in place of Example 1F and 2-(3-chloro-2-methoxyphenyl)-4,4,5,5-tetramethyl-1,3,2-dioxaborolane (240 mg, 0.893 mmol) in place of 5-fluoro-2-methoxyphenylboronic acid. LCMS: 442.1 (M+H)$^+$.

EXAMPLE 25B

4-(3-chloro-2-methoxyphenyl)-2-(piperidin-4-yl)-1H-pyrrolo[2,3-b]pyridine

The title compound was prepared as the trifluoroacetate salt using the procedure described in Example 6E, using Example 25A (300 mg, 0.679 mmol) in place of Example 6D. LCMS: 342.1 (M+H)$^+$. $^1$H NMR (400 MHz, DMSO-$d_6$): δ 1.77-1.80 (m, 2H), 2.21-2.24 (m, 2H), 3.03-3.08 (m, 3H), 3.35-3.39 (m, 5H), 6.03 (d, J=1.6 Hz, 1H), 7.12 (d, J=5.2 Hz, 1H), 7.29 (t, J=8.0 Hz, 1H), 7.43 (dd, J=1.6, 7.6 Hz, 1H), 7.60 (dd, J=1.6, 8.0 Hz, 1H), 8.24 (d, J=5.2 Hz, 1H), 8.66 (brs, 1H), 11.8 (s, 1H).

EXAMPLE 26

4-(6-fluoro-3-methoxypyridin-2-yl)-2-(piperidin-4-yl)-1H-pyrrolo[2,3-b]pyridine

EXAMPLE 26A tert-butyl 4-(4-(6-fluoro-3-methoxypyridin-2-yl)-1H-pyrrolo[2,3-b]pyridin-2-yl)piperidine-1-carboxylate The title compound was prepared using the procedure described in Example 7A, using Example 21A (933 mg, 2.18 mmol) in place of Example 5A and 2-bromo-6-fluoro-3-methoxypyridine (300 mg, 1.456 mmol) in place of 2-bromo-4-cyclopropyl-1-methoxybenzene. LCMS: 427.3 (M+H)$^+$.

EXAMPLE 26B

4-(6-fluoro-3-methoxypyridin-2-yl)-2-(piperidin-4-yl)-1H-pyrrolo[2,3-b]pyridine The title compound was prepared as the acetate salt using the procedure described in Example 6E, using Example 26A (200 mg, 0.469 mmol) in place of Example 6D, and purified using preparative HPLC (Zorbax XDB C-18 column and elution with 77/23 10M ammonium acetate in water/acetonitrile). LCMS: 327.1 (M+H)$^+$. $^1$H NMR (400 MHz, CD$_3$OD): δ 1.97-1.98 (m, 2H), 2.32-2.35 (m, 2H), 3.10-3.18 (m, 3H), 3.46-3.49 (m, 2H), 3.90 (s, 3H), 6.45 (s, 1H), 7.13 (dd, J=3.6, 8.8 Hz, 1H), 7.45 (d, J=4.8 Hz, 1H), 7.81 (d, J=6.4 Hz, 1H), 8.20 (d, J=5.2 Hz, 1H).

EXAMPLE 27

4-(2-methoxyphenyl)-2-(piperidin-4-yl)-1H-pyrrolo[2,3-b]pyridine

EXAMPLE 27A tert-butyl 4-(4-(2-methoxyphenyl)-1H-pyrrolo[2,3-b]pyridin-2-yl)piperidine-1-carboxylate The title compound was prepared using the procedure described in Example 1 G, using Example 17E (100 mg, 0.298 mmol) in place of Example 1F and 2-methoxyphenylboronic acid (54.3 mg, 0.357 mmol) in place of the product of 5-fluoro-2-methoxyphenylboronic acid.

EXAMPLE 27B

4-(2-methoxyphenyl)-2-(piperidin-4-yl)-1H-pyrrolo[2,3-b]pyridine

The title compound was prepared as the trifluoroacetate salt using the procedure described in Example 6E, using Example 27A (120 mg, 0.294 mmol) in place of Example 6D, and purified using preparative HPLC (Zorbax XDB C-18 column with gradient elution from 0.1% trifluoroacetic acid in water to 1:1 methanol/acetonitrile) LCMS: 308.3 (M+H)$^+$. $^1$H NMR (400 MHz, DMSO-$d_6$): δ 1.74-1.79 (m, 2H), 2.18-2.22 (m, 2H), 3.01-3.06 (m, 3H), 3.32-3.35 (m, 2H), 3.73 (s, 3H), 5.95 (s, 1H), 7.02-7.09 (m, 2H), 7.18 (d, J=8 Hz, 1H), 7.35-7.44 (m, 2H), 8.15 (d, J=4.8 Hz, 1H), 8.23 (brs, 1H), 11.80 (s, 1H).

EXAMPLE 28

4-(5-fluoro-2-methoxyphenyl)-2-(1-methylpiperidin-4-yl)-1H-pyrrolo[2,3-b]pyridine The title compound was prepared using the procedure described in Example 8, using Example 17F (150 mg, 0.353 mmol) in place of Example 2A. LCMS: 340.0 (M+H)$^+$. $^1$H NMR (400 MHz, DMSO-$d_6$): δ 1.66-1.70 (m, 2H), 1.95-2.17 (m, 2H), 2.17 (s, 3H), 2.64-2.67 (m, 3H), 2.82-2.84 (m, 2H), 3.73 (s, 3H), 5.9 (d, J=1.2 Hz, 1H), 7.01 (d, J=4.8 Hz, 1H), 7.16-7.20 (m, 2H), 7.20-7.26 (m, 1H), 8.13 (d, J=4.8 Hz, 1H), 11.60 (s, 1H).

EXAMPLE 29

4-(4-fluoro-2-methoxyphenyl)-2-(1-methylpiperidin-4-yl)-1H-pyrrolo[2,3-b]pyridine The title compound was prepared as the trifluoroacetate salt using the procedure described in Example 8, using Example 18A (150 mg, 0.353 mmol) in place of Example 2A. LCMS: 340.2 (M+H)$^+$. $^1$H NMR (400 MHz, DMSO-d$_6$): δ 1.77-1.80 (m, 2H), 2.26-2.30 (m, 2H), 2.8 (d, J=4 Hz, 3H), 2.99-3.16 (m, 3H), 3.51-3.54 (m, 2H), 3.77 (s, 3H), 6.0 (s, 1H), 6.92 (t, J=7.2 Hz, 1H), 7.05-7.13 (m, 2H), 7.40 (d, J=7.2 Hz, 1H), 8.19 (d, J=4.4 Hz, 1H), 11.80 (s, 1H).

EXAMPLE 30

4-(2-methoxy-5-methylphenyl)-2-(1-methylpiperidin-4-yl)-1H-pyrrolo[2,3-b]pyridine The title compound was prepared using the procedure described in Example 8, using Example 24A (80 mg, 0.19 mmol) in place of Example 2A. LCMS: 336.2 (M+H)$^+$. $^1$H NMR (400 MHz, DMSO-d$_6$): δ 1.66-1.70 (m, 2H), 1.93-1.99 (m, 3H), 2.18 (s, 3H), 2.30 (s, 3H), 2.63-2.67 (m, 2H), 2.82-2.85 (m, 2H), 3.70 (s, 3H), 5.9 (s, 1H), 6.95 (d, J=4.8 Hz, 1H), 7.06 (d, J=8.4 Hz, 1H), 7.16 (d, J=1.6 Hz, 1H), 7.21 (dd, J=2, 8.4 Hz, 2H), 8.1 (d, J=5.2 Hz, 1H), 11.60 (s, 1H).

EXAMPLE 31

4-(4-methoxypyridin-3-yl)-2-(1-methylpiperidin-4-yl)-1H-pyrrolo[2,3-b]pyridine

EXAMPLE 31A tert-butyl 4-(4-(4-methoxypyridin-3-yl)-1H-pyrrolo[2,3-b]pyridin-2-yl)piperidine-1-carboxylate The title compound was prepared using the procedure described in Example 7A, using Example 17E (93 mg, 0.276 mmol) in place of 2-bromo-4-cyclopropyl-1-methoxybenzene and (4-methoxypyridin-3-yl)boronic acid (78 mg, 0.332 mmol) in place of Example 5A. LCMS: 409.2 (M+H)$^+$.

EXAMPLE 31B 4-(4-methoxypyridin-3-yl)-2-(1-methylpiperidin-4-yl)-1H-pyrrolo[2,3-b]pyridine The title compound was prepared as the acetate salt using the procedure described in Example 8, using Example 31A (100 mg, 0.24 mmol) in place of Example 2A. LCMS: 323.1 (M+H)$^+$. $^1$H NMR (400 MHz, CD$_3$OD): δ 1.87-1.90 (m, 2H), 2.17-2.19 (m, 2H), 2.47-2.51 (m, 5H), 2.99-3.16 (m, 1H), 3.14-3.19 (m, 2H), 3.93 (s, 3H), 6.09 (s, 1H), 7.13 (d, J=5.2 Hz, 1H), 7.28 (d, J=6 Hz, 1H), 8.17 (d, J=5.2 Hz, 1H), 8.45 (s, 1H), 8.51 (d, J=5.6 Hz, 1H).

EXAMPLE 32

N-benzyl-5-chloro-6-[2-(piperidin-4-yl)-1H-pyrrolo[2,3-b]pyridin-4-yl]pyridin-2-amine

EXAMPLE 32A tert-butyl 4-(4-(6-(benzylamino)-3-chloropyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 11B (167 mg, 0.562 mmol in place of 6-bromo-5-methoxypyridin-2-amine. LCMS: 418.1 (M+H)$^+$.

EXAMPLE 32B

N-benzyl-5-chloro-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 32A (100 mg, 0.193 mmol) in place of Example 1G. LCMS: 417.8 (M+H)$^+$. $^1$H NMR (400 MHz, DMSO-d$_6$): δ 1.65-1.75 (m, 2H), 2.11-2.14 (m, 2H), 2.97-3.06 (m, 3H), 3.32-3.38 (m, 2H), 4.47 (s, 2H), 5.99 (s, 1H), 6.64 (d, J=8.8 Hz, 1H), 7.12 (d, J=4.8 Hz, 1H), 7.24-7.34 (m, 5H), 7.46-7.61 (m, 2H), 8.19-8.31 (m, 2H), 11.70 (s, 1H).

EXAMPLE 33

5-chloro-N-(3-fluorobenzyl)-6-[2-(piperidin-4-yl)-1H-pyrrolo[2,3-b]pyridin-4-yl]pyridin-2-amine

EXAMPLE 33A 6-bromo-5-chloro-N-(3-fluorobenzyl)pyridin-2-amine

The title compound was prepared using the procedure described in Example 11B, using 3-fluorobenzaldehyde (329 mg, 2.65 mmol) in place of benzaldehyde. LCMS: 316.9 (M+H)$^+$.

EXAMPLE 33B tert-butyl 4-(4-(3-chloro-6-((3-fluorobenzyl)amino)pyridin-2-yl)-1H-pyrrolo[2,3-b]pyridin-2-yl)piperidine-1-carboxylate The title compound was prepared using the procedure described in Example 5B, using Example 33A (288 mg, 0.913 mmol) in place of 6-bromo-5-methoxypyridin-2-amine and Example 21A (300 mg, 0.702 mmol) in place of Example 5A. LCMS: 536.3 (M+H)$^+$.

EXAMPLE 33C 5-chloro-N-(3-fluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 33B (100 mg, 0.187 mmol) in place of Example 1G. LCMS: 436.2 (M+H)$^+$. $^1$H NMR (400 MHz, DMSO-d$_6$): δ 1.67-1.70 (m, 2H), 2.06-2.12 (m, 2H), 2.98-3.01 (m, 3H), 3.30-3.33 (m, 2H), 4.46 (s, 2H), 5.93 (s, 1H), 6.64 (d, J=8.8 Hz, 1H), 7.05-7.12 (m, 4H), 7.33-7.34 (m, 1H), 7.46-7.52 (m, 1H), 7.60 (d, J=8.8 Hz, 1H), 8.17 (d, J=5.2 Hz, 1H), 8.22-8.28 (m, 1H), 11.70 (s, 1H).

EXAMPLE 34

5-chloro-6-[2-(piperidin-4-yl)-1H-pyrrolo[2,3-b]pyridin-4-yl]-N-(pyridin-3-ylmethyl)pyridin-2-amine

EXAMPLE 34A 6-bromo-5-chloro-N-(pyridin-3-ylmethyl)pyridin-2-amine

The title compound was prepared using the procedure described in Example 11B, using nicotinaldehyde (568 mg, 5.30 mmol) in place of benzaldehyde. LCMS: 298 (M+2)$^+$.

EXAMPLE 34B tert-butyl 4-(4-(3-chloro-6-((pyridin-3-ylmethyl)amino)pyridin-2-yl)-1H-pyrrolo[2,3-b]pyridin-2-yl)piperidine-1-carboxylate The title compound was prepared using the procedure described in Example 7A, using Example 21A (644 mg, 1.507 mmol) in place of Example 5A and Example 34A (300 mg, 1.005 mmol in place of 2-bromo-4-cyclopropyl-1-methoxybenzene. LCMS: 519.3 (M+H)$^+$.

EXAMPLE 34C 5-chloro-6-(2-(piperidin-4-yl)-1H-pyrrolo[2,3-b]pyridin-4-yl)-N-(pyridin-3-ylmethyl)pyridin-2-amine The title compound was prepared as the trifluoroacetate salt using the procedure described in Example 6E, using Example 34B (200 mg, 0.385 mmol) in place of Example 6D, and purified using preparative HPLC (Zorbax XDB C-18 column with gradient elution from 0.1% trifluoroacetic acid in water to acetonitrile). LCMS: 418.8 (M+H)$^+$. $^1$H NMR (400 MHz, DMSO-d$_6$): δ 1.72-1.78 (m, 2H), 2.14-2.17 (m, 2H), 2.99-3.09 (m, 3H), 3.35-3.38 (m, 2H), 4.59 (s, 2H), 5.93 (s, 1H), 6.72 (d, J=8.8 Hz, 1H), 7.03 (d, J=5.2 Hz, 1H), 7.66 (d, J=8.8 Hz, 1H), 7.77-7.81 (m, 1H), 8.20-8.22 (m, 2H), 8.38-8.42 (m, 1H), 8.70-8.71 (m, 3H), 11.80 (s, 1H).

EXAMPLE 35

5-chloro-N-(4-chlorobenzyl)-6-[2-(piperidin-4-yl)-1H-pyrrolo[2,3-b]pyridin-4-yl]pyridin-2-amine

EXAMPLE 35A 6-bromo-5-chloro-N-(4-chlorobenzyl)pyridin-2-amine

The title compound was prepared using the procedure described in Example 11B, using 4-chlorobenzaldehyde (237 mg, 1.687 mmol) in place of benzaldehyde. LCMS: 332 (M+3)$^+$.

EXAMPLE 35B tert-butyl 4-(4-(3-chloro-6-((4-chlorobenzyl)amino)pyridin-2-yl)-1H-pyrrolo[2,3-b]pyridin-2-yl)piperidine-1-carboxylate The title compound was prepared using the procedure described in Example 5B, using Example 35A (200 mg, 0.602 mmol) in place of 6-bromo-5-methoxypyridin-2-amine and Example 21A (386 mg, 0.904 mmol) in place of Example 5A. LCMS: 554.2 (M+3)$^+$.

EXAMPLE 35C 5-chloro-N-(4-chlorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 35B (145 mg, 0.262 mmol) in place of Example 6D, and purified using preparative HPLC (Zorbax XDB C-18 column with gradient elution from 0.1% trifluoroacetic acid in water to acetonitrile) LCMS: 452.1 (M+H)$^+$. $^1$H NMR (400 MHz, DMSO-d$_6$): δ 1.69-1.72 (m, 2H), 2.09-2.14 (m, 2H), 2.67 (s, 1H), 4.46 (d, J=5.6 Hz, 2H), 5.93 (s, 1H), 6.65 (d, J=8.8 Hz, 1H), 7.11 (d, J=5.2 Hz, 1H), 7.32 (d, J=8.4 Hz, 2H), 7.39 (d, J=8.8 Hz, 2H), 7.51-7.52 (m, 1H), 7.62 (d, J=8.8 Hz, 1H), 8.2 (d, J=4.8 Hz, 1H), 8.3-8.34 (m, 1H), 11.80 (s, 1H).

EXAMPLE 36

5-chloro-N-(2,5-difluorobenzyl)-6-[2-(piperidin-4-yl)-1H-pyrrolo[2,3-b]pyridin-4-yl]pyridin-2-amine

EXAMPLE 36A 6-bromo-5-chloro-N-(2,5-difluorobenzyl)pyridin-2-amine

To Example 11A (350 mg, 1.687 mmol) and 2,5-difluorobenzaldehyde (288 mg, 2.028 mmol) was added titanium isopropoxide (1579 mg, 5.56 mmol) and the mixture was stirred at room temperature for 16 hours. Methanol was added, the mixture was cooled to 0° C. and sodium borohydride (354 mg, 8.45 mmol) was added in portions maintaining the 0° C. temperature. After stirring at room temperature for 3 hours, the mixture was cooled to 10° C. and quenched with saturated ammonium chloride solution. The solution was extracted with ethyl acetate (20 mL×2) and the combined organic layers washed with water and brine (25 mL each), dried over sodium sulfate, filtered, and concentrated to afford the crude title compound.

EXAMPLE 36B tert-butyl 4-(4-(3-chloro-6-((2,5-difluorobenzyl)amino)pyridin-2-yl)-1H-pyrrolo[2,3-b]pyridin-2-yl)piperidine-1-carboxylate The title compound was prepared using the procedure described in Example 5B, using Example 36A (100 mg, 0.299 mmol) in place of 6-bromo-5-methoxypyridin-2-amine and Example 21A (147 mg, 0.598 mmol) in place of Example 5A. LCMS: 454.2 (M+H)$^+$.

EXAMPLE 36C 5-chloro-N-(2,5-difluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 36B (120 mg, 0.216 mmol) in place of Example 6D, and purified using preparative HPLC (Zorbax XDB C-18 column with gradient elution from 0.1% trifluoroacetic acid in water to 1:1 methanol/acetonitrile). LCMS: 454.2 (M+H)⁺. ¹H NMR (400 MHz, DMSO-d₆): δ 1.66-1.74 (m, 2H), 2.11-2.14 (m, 2H), 2.97-3.06 (m, 3H), 3.31-3.34 (m, 2H), 4.47 (d, J=5.2 Hz, 2H), 5.92 (s, 1H), 6.69 (d, J=8.8 Hz, 1H), 7.06 (d, J=4.8 Hz, 1H), 7.11-7.24 (m, 3H), 7.48 (d, J=5.6 Hz, 1H), 7.63 (d, J=8.8 Hz, 1H), 8.18 (d, J=4.8 Hz, 1H), 8.69 (brs, 1H), 11.8 (s, 1H).

EXAMPLE 37

5-chloro-N-[(5-fluoropyridin-3-yl)methyl]-6-[2-(piperidin-4-yl)-1H-pyrrolo[2,3-b]pyridin-4-yl]pyridin-2-amine

EXAMPLE 37A 6-bromo-5-chloro-N-((5-fluoropyridin-3-yl)methyl)pyridin-2-amine The title compound was prepared using the procedure described in Example 36A, using 5-fluoro nicotinaldehyde (212 mg, 1.70 mmol) in place of 2,5-difluorobenzaldehyde.

EXAMPLE 37B tert-butyl 4-(4-(3-chloro-6-(((5-fluoropyridin-3-yl)methyl)amino)pyridin-2-yl)-1H-pyrrolo[2,3-b]pyridin-2-yl)piperidine-1-carboxylate The title compound was prepared using the procedure described in Example 5B, using Example 37A (192 mg, 0.556 mmol) in place of 6-bromo-5-methoxypyridin-2-amine and Example 21A (110 mg, 0.348 mmol) in place of Example 5A. LCMS: 437 (M+H-Boc)⁺.

EXAMPLE 37C 5-chloro-N-((5-fluoropyridin-3-yl)methyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 37B (130 mg, 0.242 mmol) in place of Example 6D, and purified using preparative HPLC (Zorbax XDB C-18 column with gradient elution from 0.1% trifluoroacetic acid in water to 1:1 methanol/acetonitrile). LCMS: 437.15 (M+H)⁺. ¹H NMR (400 MHz, CD₃OD): δ 1.91-1.97 (m, 2H), 2.30-2.33 (m, 2H), 3.17-3.23 (m, 3H), 3.51-3.54 (m, 2H), 4.62 (s, 2H), 6.23 (s, 1H), 6.71 (d, J=8.8 Hz, 1H), 7.34 (s, 1H), 7.63 (d, J=8.4 Hz, 2H), 8.29-8.38 (m, 3H).

EXAMPLE 38

5-chloro-N-(2-fluorobenzyl)-6-[2-(piperidin-4-yl)-1H-pyrrolo[2,3-b]pyridin-4-yl]pyridin-2-amine

EXAMPLE 38A 6-bromo-5-chloro-N-(2-fluorobenzyl)pyridin-2-amine

The title compound was prepared using the procedure described in Example 11B, using 2-fluorobenzaldehyde (197 mg, 1.591 mmol) in place of benzaldehyde. LCMS: 316.9 (M+H)⁺.

EXAMPLE 38B tert-butyl 4-(4-(3-chloro-6-((2-fluorobenzyl)amino)pyridin-2-yl)-1H-pyrrolo[2,3-b]pyridin-2-yl)piperidine-1-carboxylate The title compound was prepared using the procedure described in Example 7A, using Example 38A (200 mg, 0.634 mmol) in place of 2-bromo-4-cyclopropyl-1-methoxybenzene and Example 21A (406 mg, 0.951 mmol) in place of Example 5A. LCMS: 536.2 (M+H)⁺.

EXAMPLE 38C 5-chloro-N-(2-fluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 38B (125 mg, 0.233 mmol) in place of Example 6D, and purified using preparative HPLC (Zorbax XDB C-18 column with gradient elution from 0.1% trifluoroacetic acid in water to 1:1 methanol/acetonitrile). LCMS: 436.2 (M+H)⁺. ¹H NMR (400 MHz, DMSO-d₆): δ 1.65-1.76 (m, 2H), 2.12-2.15 (m, 2H), 2.99-3.08 (s, 3H), 3.34-3.37 (m, 2H), 4.52 (s, 2H), 5.97 (s, 1H), 6.68 (d, J=8.8 Hz, 1H), 7.12 (d, J=4.8 Hz, 1H), 7.15-7.20 (m, 2H), 7.29-7.39 (m, 2H), 7.46 (brs, 1H), 7.63 (d, J=8.8 Hz, 1H), 8.20 (d, J=5.2 Hz, 1H), 8.60-8.62 (m, 1H) 11.77 (s, 1H).

EXAMPLE 39

5-chloro-N-(3,4-difluorobenzyl)-6-[2-(piperidin-4-yl)-1H-pyrrolo[2,3-b]pyridin-4-yl]pyridin-2-amine

EXAMPLE 39A 6-bromo-5-chloro-N-(3,4-difluorobenzyl)pyridin-2-amine

The title compound was prepared using the procedure described in Example 11B, using 3,4-difluorobenzaldehyde (468 mg, 3.29 mmol) in place of benzaldehyde.

EXAMPLE 39B tert-butyl 4-(4-(3-chloro-6-((3,4-difluorobenzyl)amino)pyridin-2-yl)-1H-pyrrolo[2,3-b]pyridin-2-yl)piperidine-1-carboxylate The title compound was prepared using the procedure described in Example 7A, using Example 39A (150 mg, 0.45 mmol) in place of 2-bromo-4-cyclopropyl-1-methoxybenzene and Example 21A (380 mg, 0.89 mmol) in place of Example 5A.

EXAMPLE 39C 5-chloro-N-(3,4-difluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 39B (80 mg, 0.14 mmol) in place of Example 6D, and purified using preparative HPLC (Zorbax XDB C-18 column with gradient elution from 0.1% trifluoroacetic acid in water to 1:1 methanol/acetonitrile). LCMS: 454.1

(M+H)+. 1H NMR (400 MHz, CD3OD): δ 1.88-1.96 (m, 2H), 2.25-2.34 (m, 2H), 3.14-3.19 (m, 3H), 3.49-3.50 (m, 2H), 4.53 (s, 2H), 6.21 (s, 1H), 6.68 (d, J=8.8 Hz, 1H), 7.10-7.18 (m, 1H), 7.20-7.26 (m, 2H), 7.35 (d, J=5.2 Hz, 1H), 7.62 (d, J=8.8 Hz, 1H), 8.28 (d, J=5.6 Hz, 1H).

EXAMPLE 40

5-chloro-6-[2-(piperidin-4-yl)-1H-pyrrolo[2,3-b]pyridin-4-yl]-N-(pyridin-4-ylmethyl)pyridin-2-amine

EXAMPLE 40A 6-bromo-5-chloro-N-(pyridin-4-ylmethyl)pyridin-2-amine

The title compound was prepared using the procedure described in Example 11B, using isonicotinaldehyde (620 mg, 5.78 mmol) in place of benzaldehyde. LCMS: 299.9 (M+3)+.

EXAMPLE 40B tert-butyl 4-(4-(3-chloro-6-((pyridin-4-ylmethyl)amino)pyridin-2-yl)-1H-pyrrolo[2,3-b]pyridin-2-yl)piperidine-1-carboxylate The title compound was prepared using the procedure described in Example 7A, using Example 40A (200 mg, 0.67 mmol) in place of 2-bromo-4-cyclopropyl-1-methoxybenzene and Example 21A (380 mg, 0.89 mmol) in place of Example 5A. LCMS: 519.3 (M+H)+.

EXAMPLE 40C 5-chloro-6-(2-(piperidin-4-yl)-1H-pyrrolo[2,3-b]pyridin-4-yl)-N-(pyridin-4-ylmethyl)pyridin-2-amine The title compound was prepared as the trifluoroacetate salt using the procedure described in Example 1H, using Example 40B (70 mg, 0.113 mmol) in place of Example 1G. LCMS: 419.1 (M+H)+. 1H NMR (400 MHz, DMSO-d6/D2O): δ 1.66-1.69 (m, 2H), 2.08-2.11 (m, 2H), 2.97-3.04 (m, 3H), 3.33-3.38 (m, 2H), 4.69 (s, 2H), 5.82 (s, 1H), 6.77 (d, J=8.8 Hz, 1H), 6.92 (d, J=5.2 Hz, 1H), 7.69 (d, J=9.2 Hz, 1H), 7.82 (d, J=6.8 Hz, 2H), 8.14 (d, J=4.8 Hz, 1H), 8.73 (d, J=6.4 Hz, 2H).

EXAMPLE 41

5-chloro-N-[(1-oxidopyridin-3-yl)methyl]-6-[2-(piperidin-4-yl)-1H-pyrrolo[2,3-b]pyridin-4-yl]pyridin-2-amine

EXAMPLE 41A 3-(((6-bromo-5-chloropyridin-2-yl)amino)methyl)pyridine 1-oxide

The title compound was prepared using the procedure described in Example 11B, using 3-formylpyridine 1-oxide (653 mg, 5.30 mmol) in place of benzaldehyde. LCMS: 315.7 (M+H)+.

EXAMPLE 41B 3-(((6-(2-(1-(tert-butoxycarbonyl)piperidin-4-yl)-1H-pyrrolo[2,3-b]pyridin-4-yl)-5-chloropyridin-2-yl)amino)methyl)pyridine 1-oxide The title compound was prepared using the procedure described in Example 7A, using Example 41A (300 mg, 0.954 mmol) in place of 2-bromo-4-cyclopropyl-1-methoxybenzene and Example 21A (380 mg, 0.89 mmol) in place of Example 5A. LCMS: 535.1 (M+H)+.

EXAMPLE 41C 5-chloro-N-[(1-oxidopyridin-3-yl)methyl]-6-[2-(piperidin-4-yl)-1H-pyrrolo[2,3-b]pyridin-4-yl]pyridin-2-amine The title compound was prepared as the trifluoroacetate salt using the procedure described in Example 6E, using Example 41B (150 mg, 0.280 mmol) in place of Example 6D, and purified using preparative HPLC (Zorbax XDB C-18 column with gradient elution from 0.1% trifluoroacetic acid in water to 1:1 methanol/acetonitrile). LCMS: 435.1 (M+H)+. 1H NMR (400 MHz, DMSO-d6/D2O): δ 1.62-1.65 (m, 2H), 2.09-2.12 (m, 2H), 2.99-3.05 (m, 3H), 3.35-3.38 (m, 2H), 4.47 (s, 2H), 5.82 (s, 1H), 6.72 (d, J=8.8 Hz, 1H), 7.14 (d, J=5.2 Hz, 1H), 7.36-7.47 (m, 2H), 7.66 (d, J=8.8 Hz, 1H), 8.18-8.22 (m, 3H).

EXAMPLE 42

5-chloro-N-(piperidin-4-ylmethyl)-6-[2-(piperidin-4-yl)-1H-pyrrolo[2,3-b]pyridin-4-yl]pyridin-2-amine

EXAMPLE 42A tert-butyl 4-(((6-bromo-5-chloropyridin-2-yl)amino)methyl)piperidine-1-carboxylate The title compound was prepared using the procedure described in Example 11B, using tert-butyl 4-formylpiperidine-1-carboxylate (514 mg, 2.410 mmol) in place of benzaldehyde. LCMS: 304.9 (M+H-Boc)+.

EXAMPLE 42B tert-butyl 4-(((6-(2-(1-(tert-butoxycarbonyl)piperidin-4-yl)-1H-pyrrolo[2,3-b]pyridin-4-yl)-5-chloropyridin-2-yl)amino)methyl)piperidine-1-carboxylate The title compound was prepared using the procedure described in Example 5B, using Example 21A (200 mg, 0.468 mmol) in place of Example 5A and Example 42A (246 mg, 0.608 mmol in place of 6-bromo-5-methoxypyridin-2-amine. LCMS: 625.4 (M+H)+.

EXAMPLE 42C 5-chloro-N-(piperidin-4-ylmethyl)-6-[2-(piperidin-4-yl)-1H-pyrrolo[2,3-b]pyridin-4-yl]pyridin-2-amine The title compound was prepared as the trifluoroacetate salt using the procedure described in Example 1H, using Example 42B (120 mg, 0.192 mmol) in place of Example 1G. LCMS: 425.5 (M+H)+. 1H NMR (400 MHz, DMSO-d6): δ 1.24-1.32 (m, 2H), 1.74-1.82 (m, 2H), 2.21-2.24 (m, 2H), 2.78-2.89 (m, 2H), 3.01-3.10 (m, 4H), 3.16-3.17 (m, 2H), 3.24-3.27 (m, 2H), 3.35-3.38 (m, 2H), 3.96 (s, 2H), 6.06 (s, 1H), 6.60 (d, J=8.8 Hz, 1H), 7.07 (brs, 1H), 7.12 (d, J=4.8 Hz, 1H), 7.59 (d, J=8.8 Hz, 1H), 8.17 (brs, 1H), 8.22 (d, J=5.2 Hz, 1H), 8.52 (brs, 1H), 11.8 (s, 1H).

EXAMPLE 43

5-chloro-N-(piperidin-3-ylmethyl)-6-[2-(piperidin-4-yl)-1H-pyrrolo[2,3-b]pyridin-4-yl]pyridin-2-amine

EXAMPLE 43A tert-butyl 3-(((6-bromo-5-chloropyridin-2-yl)amino)methyl)piperidine-1-carboxylate The title compound was prepared using the procedure described in Example 11B, using tert-butyl 3-formylpiperidine-1-carboxylate (514 mg, 2.410 mmol) in place of benzaldehyde. LCMS: 306 (M+2-Boc)$^+$.

EXAMPLE 43B tert-butyl 3-(((6-(2-(1-(tert-butoxycarbonyl)piperidin-4-yl)-1H-pyrrolo[2,3-b]pyridin-4-yl)-5-chloropyridin-2-yl)amino)methyl)piperidine-1-carboxylate The title compound was prepared using the procedure described in Example 5B, using Example 21A (200 mg, 0.468 mmol) in place of Example 5A and Example 43A (246 mg, 0.608 mmol) in place of 6-bromo-5-methoxypyridin-2-amine. LCMS: 625.3 (M+H)$^+$.

EXAMPLE 43C 5-chloro-N-(piperidin-3-ylmethyl)-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 43B (120 mg, 0.192 mmol) in place of Example 1G. LCMS: 425.2 (M+H)$^+$. $^1$H NMR (400 MHz, DMSO-d$_6$/D$_2$O): δ 1.5-1.6 (m, 1H), 1.76-1.80 (m, 4H), 1.9-1.97 (m, 1H), 2.21-2.24 (m, 2H), 2.67-2.77 (m, 2H), 3.01-3.23 (m, 10H), 6.06 (s, 1H), 6.61 (d, J=8.8 Hz, 1H), 7.13 (d, J=4.8 Hz, 1H), 7.60 (d, J=8.8 Hz, 1H), 8.22 (d, J=4.8 Hz, 1H).

EXAMPLE 44

4-(3-chloro-6-phenylpyridin-2-yl)-2-(piperidin-4-yl)-1H-pyrrolo[2,3-b]pyridine

EXAMPLE 44A 2-bromo-3-chloro-6-phenylpyridine

To a degassed solution of 2-bromo-3-chloro-6-iodopyridine (350 mg, 1.099 mmol) and phenylboronic acid (134 mg, 1.099 mmol), saturated potassium carbonate solution (5.50 mL, 5.50 mmol) in acetonitrile (5 mL) was added tetrakistriphenylphosphine palladium (63.5 mg, 0.055 mmol) and the mixture heated at 70° C. for 2 hours. The mixture was cooled and filtered through diatomaceous earth. The filtrate was concentrated and the residue washed with diethyl ether to afford the crude title compound. LCMS: 267 (M+H)$^+$.

EXAMPLE 44B tert-butyl 4-(4-(3-chloro-6-phenylpyridin-2-yl)-1H-pyrrolo[2,3-b]pyridin-2-yl)piperidine-1-carboxylate The title compound was prepared using the procedure described in Example 5B, using Example 21A (300 mg, 0.468 mmol) in place of Example 5A and Example 44A (300 mg, 1.117 mmol in place of 6-bromo-5-methoxypyridin-2-amine. LCMS: 489 (M+H)$^+$.

EXAMPLE 44C 4-(3-chloro-6-phenylpyridin-2-yl)-2-(piperidin-4-yl)-1H-pyrrolo[2,3-b]pyridine The title compound was prepared as the trifluoroacetate salt using the procedure described in Example 6E, using Example 44B (150 mg, 0.306 mmol) in place of Example 6D, and purified using preparative HPLC (Zorbax XDB C-18 column with gradient elution from 0.1% trifluoroacetic acid in water to 1:1 methanol/acetonitrile). LCMS: 389.2 (M+H)$^+$. $^1$H NMR (400 MHz, DMSO-d$_6$): δ 1.77-1.80 (m, 2H), 2.22-2.26 (m, 2H), 3.03-3.1 (m, 3H) 3.35-3.36 (m, 2H), 6.12 (s, 1H), 7.28 (d, J=4.8 Hz, 1H), 7.48-7.53 (m, 3H), 8.11-8.13 (m, 3H), 8.20 (d, J=8.4 Hz, 1H), 8.30 (d, J=5.2 Hz, 1H), 8.6 (brs, 1H), 11.9 (s, 1H).

EXAMPLE 45

N-{5-chloro-6-[2-(piperidin-4-yl)-1H-pyrrolo[2,3-b]pyridin-4-yl]pyridin-2-yl}benzamide

EXAMPLE 45A

N-(6-bromo-5-chloropyridin-2-yl)benzamide

To a solution of Example 11A (400 mg, 1.928 mmol) in dichloromethane (20 mL) was added pyridine (0.468 mL, 5.78 mmol) followed by benzoyl chloride (0.325 g, 2.314 mmol) and the mixture was stirred for 2 hours. The mixture was concentrated and the residue was dissolved in ethyl acetate, washed with sodium bicarbonate solution, water and brine, and dried over anhydrous sodium sulfate. Filtration, concentration and purification by column chromatography (silica gel, 10% ethyl acetate in hexane) afforded the title compound. LCMS: 311 (M+H)$^+$.

EXAMPLE 45B tert-butyl 4-(4-(6-benzamido-3-chloropyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 45A (190 mg, 0.608 mmol in place of 6-bromo-5-methoxypyridin-2-amine. LCMS: 532.8 (M+H)$^+$.

EXAMPLE 45C

N-(5-chloro-6-(2-(piperidin-4-yl)-1H-pyrrolo[2,3-b]pyridin-4-yl)pyridin-2-yl)benzamide The title compound was prepared as the trifluoroacetate salt using the procedure described in Example 1H, using Example 45B (100 mg, 0.188 mmol) in place of Example 1G. LCMS: 432.4 (M+H)$^+$. $^1$H NMR (400 MHz, DMSO-d$_6$): δ 1.74-1.83 (m, 2H), 2.21-2.24 (m, 2H), 2.99-3.07 (m, 3H), 3.33-3.36 (m, 2H), 6.08 (s, 1H), 7.18 (d, J=4.4 Hz, 1H), 7.48-7.62 (m, 3H), 8.03 (d, J=7.6 Hz, 2H), 8.14 (d, J=8.8 Hz, 1H), 8.27-8.30 (m, 2H), 8.62 (brs, 1H), 11.0 (s, 1H), 11.8 (s, 1H).

EXAMPLE 46

N-benzyl-5-chloro-N-methyl-6-[2-(piperidin-4-yl)-1H-pyrrolo[2,3-b]pyridin-4-yl]pyridin-2-amine

EXAMPLE 46A

N-benzyl-6-bromo-5-chloro-N-methylpyridin-2-amine

To a solution of trifluoroacetic acid (1 mL) in dichloromethane (5 mL) was added sodium borohydride (185 mg, 4.40 mmol) at 0° C. and the mixture was stirred at 0° C. for 15 minutes. Example 11B (100 mg, 0.33 mmol) and paraformaldehyde (100 mg, 3.35 mmol) in dichloromethane were added and the mixture was stirred at room temperature for 1 hour. The mixture was quenched with sodium bicarbonate solution and the aqueous layer was extracted with dichloromethane, separated and concentrated. Purification by column chromatography (silica gel, 30% ethyl acetate in hexane) afforded the title compound. LCMS: 313 (M+3)$^+$.

EXAMPLE 46B tert-butyl 4-(4-(6-(benzyl(methyl)amino)-3-chloropyridin-2-yl)-1H-pyrrolo[2,3-b]pyridin-2-yl)piperidine-1-carboxylate In 20 mL microwave vial Example 46A (50 mg, 0.16 mmol) was dissolved in 0.5 mL water and 2 mL dioxane. Sodium carbonate (51 mg, 0.48 mmol) in 1 mL of water was added followed by the addition of Example 21A (83 mg, 0.241). The mixture was degassed with nitrogen for 10 minutes and tetrakistriphenylphosphine (6.1 mg, 0.005 mmol) was added. After heating at 100° C. overnight, the mixture was diluted with ethyl acetate (50 mL) and washed with water (50×3 mL) followed by brine solution (25 mL). The organic layer was dried over anhydrous sodium sulfate, filtered, and concentrated to afford the title compound. LCMS: 533 (M+2)$^+$.

EXAMPLE 46C

N-benzyl-5-chloro-N-methyl-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 46B (120 mg, 0.225 mmol) in place of Example 6D, and purified using preparative HPLC (AG/AD/PP/C-18 column with gradient elution from 0.1% trifluoroacetic acid in water to 1:1 methanol/acetonitrile). LCMS: 432.2 (M+H)$^+$. $^1$H NMR (400 MHz, DMSO-d$_6$): δ 1.62-1.68 (m, 2H), 2.06-2.12 (m, 2H), 2.99-3.05 (m, 8H), 3.8 (s, 2H), 6.03 (s, 1H), 6.78 (d, J=8.8 Hz, 1H), 7.17-7.21 (m, 3H), 7.22-7.25 (m, 1H), 7.31-7.33 (m, 2H), 7.73 (d, J=8.8 Hz, 1H), 8.2 (d, J=4.8 Hz, 2H), 8.5 (brs, 1H), 11.7 (s, 1H).

EXAMPLE 47

N-benzyl-5-chloro-N-ethyl-6-[2-(piperidin-4-yl)-1H-pyrrolo[2,3-b]pyridin-4-yl]pyridin-2-amine

EXAMPLE 47A

N-benzyl-6-bromo-5-chloro-N-ethylpyridin-2-amine

To a stirred solution of trifluoroacetic acid (1 mL) in dichloromethane (10 mL) was added sodium borohydride (185 mg, 4.40 mmol) at 0° C. and the mixture stirred at 0° C. for 15 minutes. Example 11B (100 mg, 0.33 mmol) and acetaldehyde (149 mg, 3.35 mmol) in dichloromethane were added and the mixture was stirred at room temperature for 1 hour. The mixture was quenched with sodium bicarbonate solution and the aqueous layer was extracted with dichloromethane. The organic layer was separated and concentrated and the residue was purified by column chromatography (silica gel, 30% ethyl acetate in hexane) to afford the title compound. LCMS: 327 (M+3)$^+$.

EXAMPLE 47B tert-butyl 4-(4-(6-(benzyl(ethyl)amino)-3-chloropyridin-2-yl)-1H-pyrrolo[2,3-b]pyridin-2-yl)piperidine-1-carboxylate The title compound was prepared using the procedure described in Example 46B using Example 47A (200 mg, 0.615 mmol) in place of Example 46A. LCMS: 546.3 (M+H)$^+$.

EXAMPLE 47C

N-benzyl-5-chloro-N-ethyl-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 47B (300 mg, 0.549 mmol) in place of Example 6D, and purified using preparative HPLC (Zorbax XDB C-18 column with gradient elution from 0.1% trifluoroacetic acid in water to acetonitrile). LCMS: 446.2 (M+H)$^+$. $^1$H NMR (400 MHz, CD$_3$OD): δ 1.20 (t, J=7.2 Hz, 3H), 1.81-1.84 (m, 2H), 2.22-2.25 (m, 2H), 3.11-3.18 (m, 3H), 3.45-3.49 (m, 2H), 3.58-3.63 (m, 2H), 4.91 (s, 2H), 6.28 (s, 1H), 6.72 (d, J=9.2 Hz, 1H), 7.26-7.28 (m, 3H), 7.32-7.36 (m, 3H), 7.64 (d, J=9.2 Hz, 1H), 8.23 (d, J=4 Hz, 1H).

EXAMPLE 48

5-chloro-6-[2-(piperidin-4-yl)-1H-pyrrolo[2,3-b]pyridin-4-yl]-N-(tetrahydro-2H-pyran-4-ylmethyl)pyridin-2-amine

EXAMPLE 48A 6-bromo-5-chloro-N-((tetrahydro-2H-pyran-4-yl)methyl)pyridin-2-amine The title compound was prepared using the procedure described in Example 11B, using tetrahydro-2H-pyran-4-carbaldehyde (132 mg, 1.157 mmol) in place of benzaldehyde. LCMS: 306.9 (M+H)$^+$.

EXAMPLE 48B tert-butyl 4-(4-(3-chloro-6-(((tetrahydro-2H-pyran-4-yl)methyl)amino)pyridin-2-yl)-1H-pyrrolo[2,3-b]pyridin-2-yl)piperidine-1-carboxylate The title compound was prepared using the procedure described in Example 5B, using Example 21A (100 mg, 0.234 mmol) in place of Example 5A and Example 48A (107 mg, 0.351 mmol in place of 6-bromo-5-methoxypyridin-2-amine. LCMS: 526.4 (M+H)$^+$.

EXAMPLE 48C 5-chloro-6-(2-(piperidin-4-yl)-1H-pyrrolo[2,3-b]pyridin-4-yl)-N-((tetrahydro-2H-pyran-4-yl)methyl)pyridin-2-amine The title compound as prepared as the trifluoroacetate salt using the procedure described in Example 1H, using Example 48B (80 mg, 0.152 mmol) in place of Example 1G. LCMS: 427.15 (M+H)$^+$. $^1$H NMR (400 MHz, DMSO-d$_6$/D$_2$O): δ 1.16-1.23 (m, 2H), 1.59-1.62 (m, 2H), 1.76-1.80 (m, 2H), 2.21-2.25 (m, 2H), 3.02-3.13 (m, 4H), 3.23-3.28 (m, 2H), 3.35-3.38 (m 2H), 3.57-3.59 (m, 2H), 3.83 (d, J=10 Hz, 2H), 6.11 (s, 1H), 6.61 (d, J=8.8 Hz, 1H), 7.16 (d, J=5.2 Hz, 1H), 7.57 (d, J=9.2 Hz, 1H), 8.23 (d, J=5.2 Hz, 1H).

EXAMPLE 49

5-chloro-6-[2-(piperidin-4-yl)-1H-pyrrolo[2,3-b]pyridin-4-yl]-N-(tetrahydro-2H-pyran-3-ylmethyl)pyridin-2-amine

EXAMPLE 49A 6-bromo-5-chloro-N-((tetrahydro-2H-pyran-3-yl)methyl)pyridin-2-amine The title compound was prepared using the procedure described in Example 11B, using tetrahydro-2H-pyran-3-carbaldehyde (303 mg, 2.65 mmol) in place of benzaldehyde. LCMS: 308 (M+3)$^+$.

EXAMPLE 49B tert-butyl 4-(4-(3-chloro-6-(((tetrahydro-2H-pyran-3-yl)methyl)amino)pyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 49A (215 mg, 0.702 mmol in place of 6-bromo-5-methoxypyridin-2-amine. LCMS: 527.1 (M+H)$^+$.

EXAMPLE 49C 5-chloro-6-[2-(piperidin-4-yl)-1H-pyrrolo[2,3-b]pyridin-4-yl]-N-(tetrahydro-2H-pyran-3-ylmethyl)pyridin-2-amine The title compound was prepared as the trifluoroacetate salt using the procedure described in Example 1H, using Example 49B (130 mg, 0.247 mmol) in place of Example 1G. LCMS: 426.3 (M+H)$^+$. $^1$H NMR (400 MHz, DMSO-d$_6$/D$_2$O): δ 1.16-1.33 (m, 2H), 1.39-1.57 (m, 2H), 1.75-1.82 (m, 4H), 2.22-2.25 (m, 2H), 3.02-3.11 (m, 5H), 3.26-3.37 (m, 3H), 3.69-3.79 (m, 2H), 6.10 (s, 1H), 6.59 (d, J=8.8 Hz, 1H), 7.15 (d, J=5.2 Hz, 1H), 7.57 (d, J=8.8 Hz, 1H), 8.23 (d, J=4.8 Hz, 1H).

EXAMPLE 50

N-{4-chloro-3-[2-(piperidin-4-yl)-1H-pyrrolo[2,3-b]pyridin-4-yl]phenyl}benzenesulfonamide

EXAMPLE 50A

N-(3-bromo-4-chlorophenyl)benzenesulfonamide

To a solution of 3-bromo-4-chloroaniline (200 mg, 0.969 mmol) in dichloromethane (5 mL) was added triethylamine (0.374 mL, 2.91 mmol). The solution was cooled to 0° C. and benzenesulfonyl chloride (188 mg, 1.066 mmol) was added dropwise. After stirring at room temperature for 12 hours, the mixture was extracted with dichloromethane and the organic layer washed with water and brine (25 mL each). Drying over sodium sulfate, filtration and concentration afforded the title compound. LCMS: 346.1 (M+H)$^+$.

EXAMPLE 50B tert-butyl 4-(4-(2-chloro-5-(phenylsulfonamido)phenyl)-1H-pyrrolo[2,3-b]pyridin-2-yl)piperidine-1-carboxylate The title compound was prepared using the procedure described in Example 7A, using Example 50A (200 mg, 0.577 mmol) in place of 2-bromo-4-cyclopropyl-1-methoxybenzene and Example 21A (370 mg, 0.865 mmol) in place of Example 5A. LCMS: 567.2 (M+H)$^+$.

EXAMPLE 50C

N-(4-chloro-3-(2-(piperidin-4-yl)-1H-pyrrolo[2,3-b]pyridin-4-yl)phenyl)benzenesulfonamide The title compound was prepared as the trifluoroacetate salt using the procedure described in Example 6E, using Example 50B (150 mg, 0.265 mmol) in place of Example 6D, and purified using preparative HPLC (Zorbax XDB C-18 column with gradient elution from 0.1% trifluoroacetic acid in water to 1:1 methanol/acetonitrile). LCMS: 467.2 (M+H)$^+$. $^1$H NMR (400 MHz, DMSO-d$_6$): δ 1.71-1.80 (m, 2H), 2.19-2.23 (m, 2H), 3.05-3.07 (m, 5H), 5.75 (s, 1H), 6.93 (d, J=4.8 Hz, 1H), 7.18-7.20 (m, 2H), 7.52 (d, J=9.2 Hz, 1H), 7.58-7.70 (m, 3H), 7.78 (d, J=8 Hz, 2H), 8.20 (d, J=5.2 Hz, 1H), 8.60 (brs, 1H), 10.6 (s, 1H), 11.8 (s, 1H).

EXAMPLE 51

N-benzyl-4-fluoro-3-[2-(piperidin-4-yl)-1H-pyrrolo[2,3-b]pyridin-4-yl]aniline

EXAMPLE 51A

N-benzyl-3-bromo-4-fluoroaniline

The title compound was prepared using the procedure described in Example 11B, using 2-bromo-4-fluoroaniline (2 g, 10.4 mmol) in place of the Example 11A. LCMS: 281.9 (M+3)$^+$.

EXAMPLE 51B

N-benzyl-4-fluoro-3-(4,4,5,5-tetramethyl-1,3,2-di-oxaborolan-2-yl)aniline

The title compound was prepared using the procedure described in Example 6C, using Example 51A (500 mg, 1.77 mmol) in place of the Example 6B. LCMS: 328.1 (M+H)$^+$.

EXAMPLE 51C tert-butyl 4-(4-(5-(benzylamino)-2-fluorophenyl)-1H-pyrrolo[2,3-b]pyridin-2-yl)piperidine-1-carboxylate The title compound was prepared using the procedure described in Example 1G, using Example 17E (250 mg, 0.71 mmol) in place of the Example 1F and Example 51B (351 mg, 1.06 mmol) in place of 5-fluoro-2-methoxyphenylboronic acid. LCMS: 501.4 (M+H)$^+$.

EXAMPLE 51D

N-benzyl-4-fluoro-3-(2-(piperidin-4-yl)-1H-pyrrolo[2,3-b]pyridin-4-yl)aniline

The title compound was prepared as the trifluoroacetate salt using the procedure described in Example 6E, using Example 51C (200 mg, 0.399 mmol) in place of Example 6D, and purified using preparative HPLC (SEMI C-18 column with gradient elution from 0.1% trifluoroacetic acid in water to acetonitrile). LCMS: 401 (M+H)$^+$. $^1$H NMR (400 MHz, CD$_3$OD): δ 1.92-1.96 (m, 2H), 2.31-2.34 (m, 1H), 3.17-3.23 (m, 3H), 3.52-3.55 (m, 2H), 4.39 (s, 2H), 6.27 (s, 1H), 6.82-6.89 (m, 2H), 7.09-7.14 (m, 1H), 7.28-7.42 (m, 6H), 8.27 (wd, J=5.2 Hz, 1H).

EXAMPLE 52

N-benzyl-5-chloro-4-[2-(piperidin-4-yl)-1H-pyrrolo[2,3-b]pyridin-4-yl]pyridin-2-amine

EXAMPLE 52A 4-bromo-5-chloropyridin-2-amine

To a solution of 4-bromopyridin-2-amine (500 mg, 2.89 mmol) in N,N-dimethylformamide (5 mL) was added N-chlorosuccinimide (463 mg, 3.47 mmol) and the mixture was stirred at room temperature for 12 hours. The mixture was filtered through diatomaceous earth and concentrated and the residue was dissolved in ethyl acetate. The solution was washed with water and brine, dried over anhydrous sodium sulfate, filtered, and concentrated to afford the crude title compound. Purification by column chromatography (silica gel, 30% ethyl acetate in hexane) afforded the title compound.

EXAMPLE 52B

N-benzyl-4-bromo-5-chloropyridin-2-amine

The title compound was prepared using the procedure described in Example 11B, using Example 52A (600 mg, 2.89 mmol) in place of Example 11A. LCMS: 298.9 (M+3)$^+$.

EXAMPLE 52C tert-butyl 4-(4-(2-(benzylamino)-5-chloropyridin-4-yl)-1H-pyrrolo[2,3-b]pyridin-2-yl)piperidine-1-carboxylate The title compound was prepared using the procedure described in Example 5B, using Example 52B (300 mg, 1.008 mmol) in place of 6-bromo-5-methoxypyridin-2-amine and Example 21A (200 mg, 0.468 mmol) in place of Example 5A. LCMS: 518.3 (M+H)$^+$.

EXAMPLE 52D

N-benzyl-5-chloro-4-(2-(piperidin-4-yl)-1H-pyrrolo[2,3-b]pyridin-4-yl)pyridin-2-amine The title compound was prepared as the trifluoroacetate salt using the procedure described in Example 6E, using Example 52C (160 mg, 0.309 mmol) in place of Example 6D, and purified using preparative HPLC (X-bridge C-18 column with gradient elution from 0.1% trifluoroacetic acid in water to 1:1 methanol/acetonitrile). LCMS: 417.9 (M+H)$^+$. $^1$H NMR (400 MHz, DMSO-d$_6$): δ 1.76-1.78 (m, 2H), 2.19-2.22 (m, 2H), 3.0-3.09 (m, 5H), 4.50 (d, J=5.6 Hz, 2H), 5.94 (s, 1H), 6.60 (s, 1H), 7.01 (d, J=4.8 Hz, 1H), 7.25-7.27 (m, 1H), 7.31-7.35 (m, 3H), 7.43-7.46 (m, 1H), 8.14 (s, 1H), 8.23 (d, J=4.8 Hz, 1H), 8.26-8.3 (m, 1H), 8.56-8.6 (m, 1H), 11.90 (s, 1H).

EXAMPLE 53

N-benzyl-4-chloro-3-[2-(piperidin-4-yl)-1H-pyrrolo[2,3-b]pyridin-4-yl]aniline

EXAMPLE 53A

N-benzyl-3-bromo-4-chloroaniline

The title compound was prepared using the procedure described in Example 11B, using 3-bromo-4-chloroaniline (600 mg, 2.91 mmol) in place of Example 11A. LCMS: 297 (M+3)$^+$.

EXAMPLE 53B tert-butyl 4-(4-(5-(benzylamino)-2-chlorophenyl)-1H-pyrrolo[2,3-b]pyridin-2-yl)piperidine-1-carboxylate The title compound was prepared using the procedure described in Example 5B, using Example 53A (300 mg, 1.01 mmol) in place of 6-bromo-5-methoxypyridin-2-amine and Example 21A (200 mg, 0.468 mmol) in place of Example 5A. LCMS: 517.3 (M+H)$^+$.

EXAMPLE 53C

N-benzyl-4-chloro-3-(2-(piperidin-4-yl)-1H-pyrrolo[2,3-b]pyridin-4-yl)aniline

The title compound was prepared as the trifluoroacetate salt using the procedure described in Example 6E, using Example 53B (110 mg, 0.213 mmol) in place of Example 6D, and purified using preparative HPLC (AG/AD/PP/C-18 column with gradient elution from 0.1% trifluoroacetic acid in water to 1:1 methanol/acetonitrile). LCMS: 417.1

(M+H)⁺. ¹H NMR (400 MHz, DMSO-d₆): δ 1.7-1.76 (m, 2H), 2.14-2.17 (m, 2H), 3.01-3.04 (m, 5H), 4.26 (s, 2H), 5.77 (s, 1H), 6.59-6.68 (m, 3H), 6.91 (d, J=4.8 Hz, 1H), 7.22-7.24 (m, 2H), 7.29-7.33 (m, 4H), 8.15-8.24 (m, 2H), 11.80 (s, 1H).

EXAMPLE 54

N-benzyl-5-chloro-6-[2-(1-methylpiperidin-4-yl)-1H-pyrrolo[2,3-b]pyridin-4-yl]pyridin-2-amine The title compound was prepared as the trifluoroacetate salt using the procedure described in Example 8, substituting Example 32A (100 mg, 0.193 mmol) in place of Example 2A, and purified using preparative HPLC (Zorbax XDB C-18 column with gradient elution from 0.1% trifluoroacetic acid in water to 1:1 methanol/acetonitrile). LCMS: 432.3 (M+H)⁺. ¹H NMR (400 MHz, DMSO-d₆): δ 1.7-1.73 (m, 2H), 2.16-2.19 (m, 2H), 2.8 (s, 3H), 2.9-3.0 (m, 2H), 3.06-3.09 (m, 2H), 3.49-3.52 (m, 1H), 4.47 (s, 2H), 5.97 (s, 1H), 6.64 (d, J=8.8 Hz, 1H), 7.12 (d, J=5.2 Hz, 1H), 7.25-7.26 (m, 1H), 7.31-7.32 (m, 4H), 7.5 (brs, 1H), 7.61 (d, J=8.8 Hz, 1H), 8.20 (d, J=5.2 Hz, 1H), 11.80 (s, 1H).

EXAMPLE 55

5-chloro-N-[(1S)-1-phenylethyl]-6-[2-(piperidin-4-yl)-1H-pyrrolo[2,3-b]pyridin-4-yl]pyridin-2-amine

EXAMPLE 55A (S)-6-bromo-N-(1-phenylethyl)pyridin-2-amine

A mixture of 2-bromo-6-fluoropyridine (500 mg, 2.84 mmol) and (S)-(−)-1-phenylethylamine (0.435 mL, 3.41 mmol) were heated at 100° C. for 12 hours. The mixture was cooled to room temperature, dissolved in ethyl acetate, washed with water and brine, dried over anhydrous sodium sulfate, filtered, and concentrated. Purification by column chromatography (silica gel, 6% ethyl acetate-hexane) afforded the title compound.

EXAMPLE 55B (S)-6-bromo-5-chloro-N-(1-phenylethyl)pyridin-2-amine

The title compound was prepared using the procedure described in Example 52A, using Example 55A (500 mg, 1.804 mmol) in place of 4-bromopyridin-2-amine.

EXAMPLE 55C (S)-tert-butyl 4-(4-(3-chloro-6-((1-phenylethyl)amino)pyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 55B (190 mg, 0.608 mmol in place of 6-bromo-5-methoxypyridin-2-amine.

EXAMPLE 55D 5-chloro-N-[(1S)-1-phenylethyl]-6-[2-(piperidin-4-yl)-1H-pyrrolo[2,3-b]pyridin-4-yl]pyridin-2-amine The title compound was prepared as the trifluoroacetate salt using the procedure described in Example 6E, using Example 55C (150 mg, 0.282 mmol) in place of Example 6D, and purified using preparative HPLC (Zorbax XDB C-18 column with gradient elution from 0.1% trifluoroacetic acid in water to 1:1 methanol/acetonitrile). LCMS: 432.2 (M+H)⁺. ¹H NMR (400 MHz, DMSO-d₆): δ 1.61 (d, J=6.8 Hz, 3H), 1.76-1.87 (m, 2H), 2.18-2.19 (m, 2H), 3.09-3.10 (m, 2H), 3.37-3.39 (m, 3H), 5.49 (t, J=7.6 Hz, 1H), 6.58 (s, 1H), 6.77 (d, J=8 Hz, 1H), 7.18-7.24 (m, 2H), 7.32 (t, J=7.2 Hz, 2H), 7.40 (d (J=5.2 Hz), 1H), 7.46 (d, J=7.6 Hz, 2H), 7.76 (d, J=8 Hz, 1H), 8.19 (d, J=5.2 Hz, 1H), 8.57 (brs, 1H), 11.80 (s, 1H).

EXAMPLE 56

N-benzyl-6-[2-(1-methylpiperidin-4-yl)-1H-pyrrolo[2,3-b]pyridin-4-yl]pyridin-2-amine The title compound was prepared as the trifluoroacetate salt using the procedure described in Example 8, using Example 32A (100 mg, 0.193 mmol) in place of Example 2A, and purified using preparative HPLC (Zorbax XDB C-18 column with gradient elution from 0.1% trifluoroacetic acid in water to 1:1 methanol/acetonitrile). Dechlorination occurred under the reaction conditions. LCMS: 398.2 (M+H)⁺. ¹H NMR (400 MHz, DMSO-d₆): δ 1.70-1.73 (m, 2H), 2.16-2.19 (m, 2H), 2.77-2.81 (m, 3H), 3.06-3.09 (m, 3H), 3.49-3.52 (m, 2H), 4.64 (s, 2H), 6.65-6.66 (m, 2H), 7.19-7.25 (m, 2H), 7.31-7.38 (m, 4H), 7.47 (d, J=5.2 Hz, 1H), 7.52-7.58 (m, 1H), 8.20 (d, J=5.2 Hz, 1H), 11.80 (s, 1H).

EXAMPLE 57

5-chloro-N-(3-fluorobenzyl)-6-[2-(1-methylpiperidin-4-yl)-1H-pyrrolo[2,3-b]pyridin-4-yl]pyridin-2-amine The title compound was prepared as the trifluoroacetate salt using the procedure described in Example 8, using Example 33B (100 mg, 0.187 mmol) in place of Example 2A, and purified using preparative HPLC (Zorbax XDB C-18 column with gradient elution from 0.1% trifluoroacetic acid in water to 1:1 methanol/acetonitrile). LCMS: 449.8 (M+H)⁺. ¹H NMR (400 MHz, DMSO-d₆): δ 1.68-1.71 (m, 2H), 2.06 (s, 3H), 2.14-2.18 (m, 2H), 2.76-2.79 (m, 2H), 3.04-3.08 (m, 2H), 3.47-3.50 (m, 1H), 4.46 (s, 2H), 5.91 (s, 1H), 6.64 (d, J=8.8 Hz, 1H), 7.05-7.13 (m, 3H), 7.33-7.34 (m, 1H), 7.5 (brs, 1H), 7.60 (d, J=8.8 Hz, 1H), 8.18 (d, J=5.2 Hz, 1H), 9.3 (brs, 1H), 11.70 (s, 1H).

EXAMPLE 58

4-[6-(benzyloxy)-3-chloropyridin-2-yl]-2-(piperidin-4-yl)-1H-pyrrolo[2,3-b]pyridine

EXAMPLE 58A 2-bromo-3-chloro-6-fluoropyridine

To a solution of 6-bromo-5-chloropyridin-2-amine (1 g, 4.82 mmol) in dichloromethane (10 mL) at 0° C. added tert-butylnitrite (1.145 mL, 9.64 mmol) followed by pyridine hydrofluoride (3 mL, 9.64 mmol) and the mixture was stirred at 0° C. for 30 minutes. The mixture was quenched with water and extracted with dichloromethane. The organic layer was washed with water and brine (25 mL each), dried over sodium sulfate, filtered, and concentrated to afford of the title compound. $^1$H NMR (400 MHz, CDCl$_3$): δ 6.90-6.93 (m, 1H), 7.80-7.84 (m, 1H).

EXAMPLE 58B 6-(benzyloxy)-2-bromo-3-chloropyridine

To a solution of benzyl alcohol (55.5 mg, 0.513 mmol) in tetrahydrofuran (5 mL) at 0° C. was added potassium tert-butoxide (57.6 mg, 0.513 mmol) and the mixture was stirred at 0° C. for 2 hours. The mixture was cooled to −78° C. and a solution of 2-bromo-3-chloro-6-fluoropyridine (120 mg, 0.570 mmol) in 2 mL tetrahydrofuran was added. After stirring at −78° C. for 1 hour the mixture was diluted with ethyl acetate and water. The organic layer was separated, washed with water and brine, dried over sodium sulfate and concentrated. Purification by column chromatography (silica gel, 20% ethyl acetate in hexane) afforded the title compound. LCMS: 299.9 (M+3)$^+$.

EXAMPLE 58C tert-butyl 4-(4-(6-(benzyloxy)-3-chloropyridin-2-yl)-1H-pyrrolo[2,3-b]pyridin-2-yl)piperidine-1-carboxylate The title compound was prepared using the procedure described in Example 7A, using Example 58B (100 mg, 0.335 mmol) in place of 2-bromo-4-cyclopropyl-1-methoxybenzene and Example 21A (215 mg, 0.502 mmol) in place of Example 5A. LCMS: 520.1 (M+H)$^+$.

EXAMPLE 58D 4-(6-(benzyloxy)-3-chloropyridin-2-yl)-2-(piperidin-4-yl)-1H-pyrrolo[2,3-b]pyridine The title compound was prepared as the trifluoroacetate salt using the procedure described in Example 6E, using Example 58C (100 mg, 0.193 mmol) in place of Example 6D, and purified using preparative HPLC (Zorbax XDB C-18 column with gradient elution from 0.1% trifluoroacetic acid in water to 1:1 methanol/acetonitrile). LCMS: 419.2 (M+H)$^+$. $^1$H NMR (400 MHz, DMSO-d$_6$): δ 1.76-1.81 (m, 2H), 2.19-2.22 (m, 2H), 3.0-3.09 (m, 4H), 3.35-3.37 (m, 1H), 5.35 (s, 2H), 6.09 (s, 1H), 7.05 (d, J=8.8 Hz, 1H), 7.22 (d, J=4.8 Hz, 1H), 7.32-7.45 (m, 5H), 8.02 (d, J=8.8 Hz, 1H), 8.60 (brs, 1H), 9.31-9.35 (m, 1H), 11.8 (s, 1H).

EXAMPLE 59

4-(5-fluoro-2-methoxyphenyl)-2-(pyrrolidin-3-yl)-1H-pyrrolo[2,3-b]pyridine

EXAMPLE 59A tert-butyl 3-ethynylpyrrolidine-1-carboxylate

The title compound was prepared using the procedure described in Example 1D, using tert-butyl 3-formylpyrrolidine-1-carboxylate (1.1 g, 5.52 mmol) in place of Example 1C.

EXAMPLE 59B tert-butyl 3-((2-((tert-butoxycarbonyl)amino)-4-chloropyridin-3-yl)ethynyl)pyrrolidine-1-carboxylate The title compound was prepared using the procedure described in Example 1E, using Example 59A (413 mg, 2.115 mmol) in place of Example 1A. LCMS: 422.1 (M+H).

EXAMPLE 59C tert-butyl 3-(4-chloro-1H-pyrrolo[2,3-b]pyridin-2-yl)pyrrolidine-1-carboxylate The title compound was prepared using the procedure described in Example 1F, using Example 59B (430 mg, 1.019 mmol) in place of Example 1E. LCMS: 322.1 (M+H).

EXAMPLE 59D tert-butyl 2-(1-(tert-butoxycarbonyl)pyrrolidin-3-yl)-4-chloro-1H-pyrrolo[2,3-b]pyridine-1-carboxylate N,N-Dimethylpyridin-4-amine (0.087 g, 0.715 mmol) was added to a solution of Example 59C (230 mg, 0.715 mmol) in 5 mL tetrahydrofuran at room temperature followed by the drop wise addition of di-tert-butyl dicarbonate (0.156 g, 0.715 mmol). After stirring at room temperature for 3 hours, the mixture was partitioned between ethyl acetate and water (20 mL each). The organic layer was dried over anhydrous sodium sulfate, filtered, and concentrated to afford the title compound. LCMS: 322.1 (M+H-Boc).

EXAMPLE 59E tert-butyl 2-(1-(tert-butoxycarbonyl)pyrrolidin-3-yl)-4-(5-fluoro-2-methoxyphenyl)-1H-pyrrolo[2,3-b]pyridine-1-carboxylate The title compound was prepared using the procedure described in Example 7A, using Example 59D (200 mg, 0.474 mmol) in place of Example 5A and 5-fluoro-2-methoxyphenylboronic acid (131 mg, 0.521 mmol) in place of 2-bromo-4-cyclopropyl-1-methoxybenzene. LCMS: 412.1 (M+H-Boc).

EXAMPLE 59F 4-(5-fluoro-2-methoxyphenyl)-2-(pyrrolidin-3-yl)-1H-pyrrolo[2,3-b]pyridine The title compound was prepared as the hydrochloride salt using the procedure described in Example 1H, using Example 59E (100 mg, 0.195 mmol) in place of Example 1G, and was purified by crystallization from acetonitrile/methanol. LCMS: 312.2 (M+H)$^+$. $^1$H NMR (400 MHz, DMSO-d$_6$/D$_2$O): δ 2.06-2.11 (m, 1H), 2.37-2.41 (m, 2H), 3.24-3.32 (m, 4H), 6.3 (s, 1H), 7.19-7.24 (m, 4H), 7.27-7.30 (m, 1H), 8.25 (d, J=5.2 Hz, 1H).

EXAMPLE 60

4-(4-fluoro-2-methoxyphenyl)-2-(pyrrolidin-3-yl)-1H-pyrrolo[2,3-b]pyridine

EXAMPLE 60A tert-butyl 2-(1-(tert-butoxycarbonyl)pyrrolidin-3-yl)-4-(4-fluoro-2-methoxyphenyl)-1H-pyrrolo[2,3-b]pyridine-1-carboxylate The title compound was prepared using the procedure described in Example 7A, using Example 59D (100 mg, 0.31 mmol) in place of Example 5A and 4-fluoro-2-methoxyphenylboronic acid (63 mg, 0.37 mmol) in place of 2-bromo-4-cyclopropyl-1-methoxybenzene. LCMS: 412.9 (M+H).

EXAMPLE 60B 4-(4-fluoro-2-methoxyphenyl)-2-(pyrrolidin-3-yl)-1H-pyrrolo[2,3-b]pyridine The title compound was prepared as the hydrochloride salt using the procedure described in Example 1H, using Example 60A (60 mg, 0.11 mmol) in place of Example 1G, and was purified by crystallization from acetonitrile/methanol. LCMS: 312.2 (M+H)$^+$. $^1$H NMR (400 MHz, DMSO-$d_6$/D$_2$O): δ 2.05-2.14 (m, 1H), 2.32-2.41 (m, 2H), 3.25-3.38 (m, 4H), 3.80 (s, 3H), 6.27 (s, 1H), 6.93 (t, J=8.4 Hz, 1H), 7.112-7.18 (m, 2H) 7.438 (t, J=7.6 Hz, 1H) 8.24 (d, J=5.2 Hz, 1H).

EXAMPLE 61

4-(5-fluoro-2-methoxyphenyl)-2-[(3S)-pyrrolidin-3-yl]-1H-pyrrolo[2,3-b]pyridine

The racemic product of Example 59F (100 mg, 0.321 mmol) was resolved using a Chiralpak AD-H HPLC column to afford the title compound. (absolute stereochemistry arbitrarily assigned). LCMS: 311.9 (M+H)$^+$. $^1$H NMR (400 MHz, CD$_3$OD): δ 2.01-2.06 (m, 1H), 2.32-2.36 (m, 1H), 3.0-3.19 (m, 3H), 3.39-3.42 (m, 1H), 3.50-3.56 (m, 1H), 3.78 (s, 3H), 6.15 (s, 1H), 7.09-7.19 (m, 4H), 8.13 (d, J=5.2 Hz, 1H).

EXAMPLE 62

4-(5-fluoro-2-methoxyphenyl)-2-[(3R)-pyrrolidin-3-yl]-1H-pyrrolo[2,3-b]pyridine

The racemic product of Example 59F (100 mg, 0.321 mmol) was resolved using Chiralpak AD-H HPLC column to afford the title compound. (Absolute stereochemistry was arbitrarily assigned.) LCMS: 311.9 (M+H)$^+$. $^1$H NMR (400 MHz, CD$_3$OD): δ 1.3-1.4 (m, 2H), 2.6-2.7 (m, 1H), 3.05 (brs, 1H), 3.5-3.6 (m, 2H), 3.89 (s, 3H), 3.92-3.98 (m, 1H), 6.66-6.7 (m, 1H), 7.24-7.38 (m, 3H), 7.62-7.68 (m, 1H), 8.38-8.42 (m, 1H).

EXAMPLE 63

4-(5-fluoro-2-methoxyphenyl)-2-(1-methylpyrrolidin-3-yl)-1H-pyrrolo[2,3-b]pyridine

EXAMPLE 63A tert-butyl 3-(4-(5-fluoro-2-methoxyphenyl)-1H-pyrrolo[2,3-b]pyridin-2-yl)pyrrolidine-1-carboxylate The title compound was prepared using the procedure described in Example 7A, using Example 59C (100 mg, 0.31 mmol) in place of Example 5A and 5-fluoro-2-methoxyphenylboronic acid (63 mg, 0.37 mmol) in place of 2-bromo-4-cyclopropyl-1-methoxybenzene. LCMS: 413.0 (M+H-Boc).

EXAMPLE 63B 4-(5-fluoro-2-methoxyphenyl)-2-(1-methylpyrrolidin-3-yl)-1H-pyrrolo[2,3-b]pyridine The title compound was prepared using the procedure described in Example 8, using Example 63A (50 mg, 0.12 mmol) in place of Example 2A. LCMS: 326.2 (M+H)$^+$. $^1$H NMR (400 MHz, DMSO-$d_6$): δ 2.86 (d, J=4.8 Hz, 2H), 3.23-3.47 (m, 3H), 3.60-3.70 (m, 3H), 3.76-3.79 (m, 5H), 6.37 (brs, 1H), 7.23-7.29 (m, 3H), 7.31-7.36 (m, 1H), 8.29 (d, J=5.2 Hz, 1H), 12.4 (s, 1H).

EXAMPLE 64

N-benzyl-5-chloro-6-[2-(pyrrolidin-3-yl)-1H-pyrrolo[2,3-b]pyridin-4-yl]pyridin-2-amine

EXAMPLE 64A tert-butyl 2-(1-(tert-butoxycarbonyl)pyrrolidin-3-yl)-4-(4,4,5,5-tetramethyl-1,3,2-dioxaborolan-2-yl)-1H-pyrrolo[2,3-b]pyridine-1-carboxylate The title compound was prepared using the procedure described in Example 5A, using Example 59D (160 mg, 0.379 mmol) in place of Example 1F. LCMS: 431.9 (M+H (boronic acid)).

EXAMPLE 64B tert-butyl 3-(4-(6-(benzylamino)-3-chloropyridin-2-yl)-1H-pyrrolo[2,3-b]pyridin-2-yl)pyrrolidine-1-carboxylate The title compound was prepared using the procedure described in Example 7A, using Example 64A (150 mg, 0.292 mmol) in place of Example 5A and Example 11B (96 mg, 0.321 mmol in place of 2-bromo-4-cyclopropyl-1-methoxybenzene. LCMS: 505.2 (M+H).

EXAMPLE 64C

N-benzyl-5-chloro-6-(2-(pyrrolidin-3-yl)-1H-pyrrolo[2,3-b]pyridin-4-yl)pyridin-2-amine The title compound was prepared as the hydrochloride salt using the procedure described in Example 1H, using Example 64B (100 mg, 0.166 mmol) in place of Example 1G. LCMS: 404.1 (M+H)$^+$. $^1$H NMR (400 MHz, DMSO-$d_6$): δ 1.03-1.10 (m, 1H), 1.99-2.03 (m, 1H), 3.2-3.3 (m, 1H), 2.9-3.0 (m, 2H), 3.06-3.09 (m, 2H), 3.36-3.45 (m, 3H), 4.46 (s, 2H), 6.13 (s, 1H), 6.67 (d, J=8.8 Hz, 1H), 7.18 (d, J=5.2 Hz, 1H), 7.18-7.25 (m, 2H), 7.29-7.33 (m, 4H), 7.62 (d, J=8.8 Hz, 1H), 8.26 (d, J=4.8 Hz, 1H), 9.12-9.2 (m, 2H), 12.0 (s, 1H).

EXAMPLE 65

5-chloro-6-[2-(pyrrolidin-3-yl)-1H-pyrrolo[2,3-b]pyridin-4-yl]-N-(tetrahydro-2H-pyran-4-ylmethyl)pyridin-2-amine

EXAMPLE 65A tert-butyl 3-(4-chloro-1-tosyl-1H-pyrrolo[2,3-b]pyridin-2-yl)pyrrolidine-1-carboxylate To a solution of Example 59C (0.5 g, 1.554 mmol) in 20 mL tetrahydrofuran, was added sodium hydroxide (0.249 g, 6.22 mmol) and the mixture was stirred at room temperature for 1 hour. p-Toluenesulfonyl chloride (0.355 g, 1.865 mmol) and benzyltriethylammonium chloride (0.018 g, 0.078 mmol) were added and the mixture was stirred for 12 hours. Water was added and the mixture was extracted with dichloromethane. The organic layer was washed with water and brine, dried over sodium sulfate, filtered, and concentrated to afford the crude product which was purified by column chromatography (100-200 silica-gel in hexane and eluted with 15% ethyl acetate-hexane) to afford the title compound. LCMS: 475.1 (M+H)+.

EXAMPLE 65B tert-butyl 3-(1-tosyl-4-(4,4,5,5-tetramethyl-1,3,2-dioxaborolan-2-yl)-1H-pyrrolo[2,3-b]pyridin-2-yl)pyrrolidine-1-carboxylate To Example 65A (0.25 g, 0.525 mmol) in 40 mL of 1,4-dioxane, was added 4,4,4',4',5,5,5',5'-octamethyl-2,2'-bi(1,3,2-dioxaborolane) (0.200 g, 0.788 mmol) and potassium acetate (0.155 g, 1.576 mmol). The mixture was purged with nitrogen for 5 minutes and 2-(dicyclohexylphosphino)biphenyl (0.018 g, 0.053 mmol) and palladium(II) acetate (0.012 g, 0.053 mmol) were added. After heating at 100° C. for 12 hours, the mixture was filtered through diatomaceous earth and concentrated. The residue was dissolved in ethyl acetate, washed with water and brine, dried over anhydrous sodium sulfate, filtered, and concentrated to afford the title compound, which was used without further purification.

EXAMPLE 65C tert-butyl 3-(4-(3-chloro-6-(((tetrahydro-2H-pyran-4-yl)methyl)amino)pyridin-2-yl)-1-tosyl-1H-pyrrolo[2,3-b]pyridin-2-yl)pyrrolidine-1-carboxylate The title compound was prepared using the procedure described in Example 7A, using Example 65B (297 mg, 0.524 mmol) in place of Example 5A and Example 48A (160 mg, 0.524 mmol in place of 2-bromo-4-cyclopropyl-1-methoxybenzene. LCMS: 666.8 (M+H)$^+$.

EXAMPLE 65D tert-butyl 3-(4-(3-chloro-6-(((tetrahydro-2H-pyran-4-yl)methyl)amino)pyridin-2-yl)-1H-pyrrolo[2,3-b]pyridin-2-yl)pyrrolidine-1-carboxylate A solution of Example 65C (150 mg, 0.225 mmol) in dioxane (3 mL) and 10N aqueous sodium hydroxide (0.225 mL) was heated in sealed tube at 100° C. for 3 hours. The mixture was diluted with water and ethyl acetate. The organic layer was washed with water and brine (25 mL each), dried over sodium sulfate, filtered and concentrated to afford the title compound. LCMS: 512.55 (M+H)$^+$.

EXAMPLE 65E 5-chloro-6-(2-(pyrrolidin-3-yl)-1H-pyrrolo[2,3-b]pyridin-4-yl)-N-((tetrahydro-2H-pyran-4-yl)methyl)pyridin-2-amine The title compound was prepared as the trifluoroacetate salt using the procedure described in Example 1H, using Example 65D (110 mg, 0.215 mmol) in place of Example 1G, and purified using preparative HPLC (X-bridge C-18 column with gradient elution from 0.1% trifluoroacetic acid in water to 1:1 methanol/acetonitrile). LCMS: 412.2 (M+H)$^+$. $^1$H NMR (400 MHz, DMSO-d$_6$/D$_2$O): δ 1.15-1.23 (m, 2H), 1.58-1.61 (m, 2H), 2.07-2.12 (m, 1H), 2.33-2.40 (m, 2H), 3.10 (d, J=6.8 Hz, 2H), 3.22-3.43 (m, 4H), 3.60-3.67 (m, 2H), 3.81-3.84 (m, 2H), 6.25 (s, 1H), 6.60 (d, J=8.8 Hz, 1H), 7.14 (d, J=4.8 Hz, 1H), 7.56 (d, J=9.2 Hz, 1H), 8.24 (d, J=4.8 Hz, 1H).

EXAMPLE 66

4-(4-fluoro-2-methoxyphenyl)-2-(morpholin-2-yl)-1H-pyrrolo[2,3-b]pyridine

EXAMPLE 66A tert-butyl 2-ethynylmorpholine-4-carboxylate

The title compound was prepared using the procedure described in Example 1D, using tert-butyl 2-formylmorpholine-4-carboxylate (300 mg, 1.394 mmol) in place of Example 1C. LCMS: 212.4 (M+H)$^+$.

EXAMPLE 66B tert-butyl 2-((2-((tert-butoxycarbonyl)amino)-4-chloropyridin-3-yl)ethynyl)morpholine-4-carboxylate The title compound was prepared using the procedure described in Example 1E, using Example 66A (1.192 g, 5.64 mmol) in place of Example 1A and N,N-dimethylformamide as the solvent instead of tetrahydrofuran. LCMS: 437.2 (M+H)$^+$.

EXAMPLE 66C tert-butyl 2-(4-chloro-1H-pyrrolo[2,3-b]pyridin-2-yl)morpholine-4-carboxylate The title compound was prepared using the procedure described in Example 1F, using Example 66B (400 mg, 0.913 mmol) in place of Example 1E. LCMS: 338 (M+H-Boc)$^+$.

EXAMPLE 66D tert-butyl 2-(4-(4-fluoro-2-methoxyphenyl)-1H-pyrrolo[2,3-b]pyridin-2-yl)morpholine-4-carboxylate The title compound was prepared using the procedure described in Example 7A, using 4-fluoro-2-methoxyphenylboronic acid (91 mg, 0.53 mmol) in place of Example 5A and Example 66C (180 mg, 0.53 mmol) in place of 2-bromo-4-cyclopropyl-1-methoxybenzene.

EXAMPLE 66E 4-(4-fluoro-2-methoxyphenyl)-2-(morpholin-2-yl)-1H-pyrrolo[2,3-b]pyridine The title compound was prepared as the hydrochloride salt using the procedure described in Example 1H, using Example 66D (90 mg, 0.21 mmol) in place of Example 1G, and was purified by crystallization from acetonitrile/methanol. LCMS: 328.1 (M+H)$^+$, $^1$H NMR (400 MHz, DMSO-d$_6$/D$_2$O): δ 3.06-3.08 (m, 1H), 3.27-3.38 (m, 2H), 3.5-3.58

(m, 1H), 3.76 (s, 3H), 4.08-4.11 (m, 2H), 4.89-4.92 (m, 1H), 6.29 (d, J=1.6 Hz, 1H), 6.89-6.94 (m, 1H), 7.06-7.13 (m, 2H), 7.37-7.41 (m, 1H), 8.2 (d, J=4.8 Hz, 1H).

EXAMPLE 67

4-(5-fluoro-2-methoxyphenyl)-2-(morpholin-2-yl)-1H-pyrrolo[2,3-b]pyridine

EXAMPLE 67A tert-butyl 2-(4-(5-fluoro-2-methoxyphenyl)-1H-pyrrolo[2,3-b]pyridin-2-yl)morpholine-4-carboxylate The title compound was prepared using the procedure described in Example 1G using Example 66C (150 mg, 0.45 mmol) in place of Example 1F. LCMS: 428.1 (M+H)$^+$.

EXAMPLE 67B 4-(5-fluoro-2-methoxyphenyl)-2-(morpholin-2-yl)-1H-pyrrolo[2,3-b]pyridine The title compound was prepared as the trifluoroacetate salt using the procedure described in Example 1H, using Example 67A (80 mg, 0.2 mmol) in place of Example 1G, and purified using preparative HPLC (Zorbax XDB C-18 column with gradient elution from 0.1% trifluoroacetic acid in water to 1:1 methanol/acetonitrile). LCMS: 328.1 (M+H)$^+$. $^1$H NMR (400 MHz, DMSO-d$_6$/D$_2$O): δ 3.05-3.15 (m, 2H), 3.25-3.36 (m, 2H), 3.72 (s, 3H), 3.9-3.95 (m, 1H), 4.06-4.12 (m, 1H), 4.97 (d, J=9.6 Hz, 1H), 6.37 (s, 1H), 7.17-7.30 (m, 4H), 8.29 (d, J=5.2 Hz, 1H).

EXAMPLE 68

4-(4-fluoro-2-methoxyphenyl)-2-(4-methylmorpholin-2-yl)-1H-pyrrolo[2,3-b]pyridine The title compound was prepared using the procedure described in Example 8, using Example 66D (50 mg, 0.117 mmol) in place of Example 2A. LCMS: 341.9 (M+H)$^+$. $^1$H NMR (400 MHz, DMSO-d$_6$): δ 2.1-2.14 (m, 2H), 2.24 (s, 3H), 2.64-2.67 (m, 1H), 2.94-2.97 (m, 1H), 3.63-3.69 (m, 1H), 3.76 (s, 3H), 3.87-3.90 (m, 1H), 4.65 (d, J=8.4 Hz, 1H), 6.11 (s, 1H), 6.88-6.93 (m, 1H), 7.01 (d, J=4.8 Hz, 1H), 7.08 (dd, J=2.4, 11.6 Hz, 1H), 7.39 (t, J=7.2 Hz, 1H), 8.17 (d, J=5.2 Hz, 1H), 11.7 (s, 1H).

EXAMPLE 69

4-(5-fluoro-2-methoxyphenyl)-2-(4-methylmorpholin-2-yl)-1H-pyrrolo[2,3-b]pyridine The title compound was prepared using the procedure described in Example 8, using Example 67B (80 mg, 0.187 mmol) in place of Example 2A. LCMS: 342.2 (M+H)$^+$. $^1$H NMR (400 MHz, DMSO-d$_6$): δ 2.02-2.15 (m, 2H), 2.2 (s, 3H), 2.6-2.68 (m, 2H), 2.9-2.97 (m, 1H), 3.72 (s, 3H), 3.82-3.90 (m, 1H), 4.6-4.66 (m, 1H), 6.13 (s, 1H), 7.0-7.2 (m, 1H), 7.15-7.3 (m, 3H), 8.19-8.2 (m, 1H), 11.8 (s, 1H).

EXAMPLE 70

N-benzyl-5-chloro-6-[2-(morpholin-2-yl)-1H-pyrrolo[2,3-b]pyridin-4-yl]pyridin-2-amine

EXAMPLE 70A tert-butyl 2-(4-(4,4,5,5-tetramethyl-1,3,2-dioxaborolan-2-yl)-1H-pyrrolo[2,3-b]pyridin-2-yl)morpholine-4-carboxylate The title compound was prepared using the procedure described in Example 5A, using Example 66C (100 mg, 0.296 mmol) in place of Example 1F.

EXAMPLE 70B tert-butyl 2-(4-(6-(benzylamino)-3-chloropyridin-2-yl)-1H-pyrrolo[2,3-b]pyridin-2-yl)morpholine-4-carboxylate The title compound was prepared using the procedure described in Example 7A, using Example 70A (72 mg, 0.14 mmol) in place of Example 5A and Example 11B (50 mg, 0.094 mmol) in place of 2-bromo-4-cyclopropyl-1-methoxybenzene.

EXAMPLE 70C

N-benzyl-5-chloro-6-(2-(morpholin-2-yl)-1H-pyrrolo[2,3-b]pyridin-4-yl)pyridin-2-amine The title compound was prepared using the procedure described in Example 1H, using Example 70B (90 mg, 0.17 mmol) in place of Example 1G. LCMS: 420.0 (M+H)$^+$. $^1$H NMR (400 MHz, CD$_3$OD): δ 3.36-3.41 (m, 2H), 3.58-3.62 (m, 2H), 4.08-4.1 (m, 2H), 4.25-4.32 (m, 1H), 4.58 (s, 2H), 5.06-5.1 (m, 1H), 6.57 (s, 1H), 6.85-6.88 (m, 1H), 7.3-7.34 (m, 1H), 7.35-7.37 (m, 4H), 7.63 (d, J=5.6 Hz, 1H), 7.75 (d, J=9.2 Hz, 1H), 8.47 (d, J=1.4 Hz, 1H)

EXAMPLE 71

2-(5,5-dimethylmorpholin-2-yl)-4-(5-fluoro-2-methoxyphenyl)-1H-pyrrolo[2,3-b]pyridine

EXAMPLE 71A tert-butyl 2-formyl-5,5-dimethylmorpholine-4-carboxylate

To as solution of tert-butyl 2-(hydroxymethyl)-5,5-dimethylmorpholine-4-carboxylate (2.0 g, 8.15 mmol) in dichloromethane (25 mL) was added Dess-Martin periodinane (4.15 g, 9.78 mmol) slowly over 10 minutes and the mixture was stirred at room temperature 3 hours. Saturated sodium bicarbonate solution was added and the mixture extracted with dichloromethane. The dichloromethane layer was washed with water and brine, dried over sodium sulfate, filtered, and concentrated to afford the title compound. LCMS: 144.0 (M+H-Boc).

EXAMPLE 71B tert-butyl 2-ethynyl-5,5-dimethylmorpholine-4-carboxylate

The title compound was prepared using the procedure described in Example 1D, using Example 71A (1.3 g, 5.34 mmol) in place of Example 1C. LCMS: 140.1 (M+H-Boc)+.

EXAMPLE 71C tert-butyl 2-((2-((tert-butoxycarbonyl)amino)-4-chloropyridin-3-yl)ethynyl)-5,5-dimethylmorpholine-4-carboxylate The title compound was prepared using the procedure described in Example 1E, using Example 71B (506 mg, 2.115 mmol) in place of Example 1D. LCMS: 140.1 (M+H-Boc)+.

EXAMPLE 71D tert-butyl 2-(4-chloro-1H-pyrrolo[2,3-b]pyridin-2-yl)-5,5-dimethylmorpholine-4-carboxylate The title compound was prepared using the procedure described in Example 1F, using Example 71C (500 mg, 1.367 mmol) in place of Example 1E.

EXAMPLE 71E tert-butyl 2-(4-(5-fluoro-2-methoxyphenyl)-1H-pyrrolo[2,3-b]pyridin-2-yl)-5,5-dimethylmorpholine-4-carboxylate The title compound was prepared using the procedure described in Example 1 G, using Example 71D (150 mg, 0.41 mmol) in place of Example 1F.

EXAMPLE 71F 2-(5,5-dimethylmorpholin-2-yl)-4-(5-fluoro-2-methoxyphenyl)-1H-pyrrolo[2,3-b]pyridine The title compound was prepared as the trifluoroacetate salt using the procedure described in Example 6E, using Example 71E (100 mg, 0.235 mmol) in place of Example 6D, and purified using preparative HPLC (Zorbax XDB C-18 column with gradient elution from 0.1% trifluoroacetic acid in water to acetonitrile). LCMS: 356.1 (M+H)+. 1H NMR (400 MHz, DMSO-d6): δ 1.23-1.27 (m, 5H), 1.47 (s, 3H), 3.74 (s, 3H), 3.79-3.82 (m, 2H), 4.83-4.86 (m, 1H), 6.42 (s, 1H), 7.1 (d, J=4.8 Hz, 1H), 7.20-7.23 (m, 2H), 7.28-7.31 (m, 1H), 8.28 (d, J=4.8 Hz, 1H), 9.04 (brs, 1H), 12.0 (brs, 1H).

EXAMPLE 72

2-(5,5-dimethylmorpholin-2-yl)-4-(4-fluoro-2-methoxyphenyl)-1H-pyrrolo[2,3-b]pyridine

EXAMPLE 72A tert-butyl 2-(4-(4-fluoro-2-methoxyphenyl)-1H-pyrrolo[2,3-b]pyridin-2-yl)-5,5-dimethylmorpholine-4-carboxylate The title compound was prepared using the procedure described in Example 1 G, using Example 71D (150 mg, 0.41 mmol) in place of Example 1F and 4-fluoro-2-methoxyphenylboronic acid (91 mg, 0.533 mmol) in place of 5-fluoro-2-methoxyphenylboronic acid. LCMS: 456.2 (M+H)+.

EXAMPLE 72B 2-(5,5-dimethylmorpholin-2-yl)-4-(4-fluoro-2-methoxyphenyl)-1H-pyrrolo[2,3-b]pyridine The title compound was prepared as the trifluoroacetate salt using the procedure described in Example 6E, using Example 72A (150 mg, 0.329 mmol) in place of Example 6D, and purified using preparative HPLC (Zorbax XDB C-18 column with gradient elution from 0.1% trifluoroacetic acid in water to 1:1 methanol/acetonitrile). LCMS: 356.15 (M+H)+. 1H NMR (400 MHz, CD3OD): δ 1.44 (s, 3H), 1.61 (s, 3H), 3.49-3.57 (m, 1H), 3.62-3.68 (m, 1H), 3.84 (s, 3H), 3.91-3.96 (m, 2H), 5.10 (dd, J=2.4, 10.8 Hz, 1H), 6.55 (s, 1H), 6.88 (t, J=8 Hz, 1H), 7.02 (dd, J=2.8, 11.2 Hz, 1H), 7.35-7.39 (m, 1H), 7.49-7.52 (m, 1H), 8.31 (d, J=5.6 Hz, 1H).

EXAMPLE 73

4-(4-chloro-2-methoxyphenyl)-2-(5,5-dimethylmorpholin-2-yl)-1H-pyrrolo[2,3-b]pyridine

EXAMPLE 73A tert-butyl 2-(4-(4-chloro-2-methoxyphenyl)-1H-pyrrolo[2,3-b]pyridin-2-yl)-5,5-dimethylmorpholine-4-carboxylate The title compound was prepared using the procedure described in Example 1 G, using Example 71D (200 mg, 0.547 mmol) in place of Example 1F and 4-chloro-2-methoxyphenylboronic acid (132 mg, 0.711 mmol) in place of 5-fluoro-2-methoxyphenylboronic acid. LCMS: 472.2 (M+H)+.

EXAMPLE 73B 4-(4-chloro-2-methoxyphenyl)-2-(5,5-dimethylmorpholin-2-yl)-1H-pyrrolo[2,3-b]pyridine The title compound was prepared as the acetate salt using the procedure described in Example 6E, using Example 73A (150 mg, 0.329 mmol) in place of Example 6D, and purified using preparative HPLC (Zorbax XDB C-18 column with gradient elution from 10M ammonium acetate in water to 1:1 methanol/acetonitrile). LCMS: 372.2 (M+H)+. 1H NMR (400 MHz, CD3OD): δ 1.21 (s, 3H), 1.44 (s, 3H), 3.1-3.2 (m, 2H), 3.62-3.63 (m, 1H), 3.79 (s, 1H), 3.82 (s, 3H), 4.72-4.76 (m, 1H), 6.31 (s, 1H), 7.10-7.14 (m, 2H), 7.21 (d, J=2 Hz, 1H), 7.41 (d, J=8 Hz, 1H), 8.21 (d, J=4.8 Hz,

EXAMPLE 74 trans-4-[4-(5-fluoro-2-methoxyphenyl)-1H-pyrrolo[2,3-b]pyridin-2-yl]cyclohexanamine

EXAMPLE 74A tert-butyl (trans-4-ethynylcyclohexyl)carbamate

The title compound was prepared using the procedure described in Example 1D, using tert-butyl trans-4-formylcyclohexylcarbamate (600 mg, 2.64 mmol) in place of Example 1C.

EXAMPLE 74B tert-butyl [trans-4-({2-[(tert-butoxycarbonyl)amino]-4-chloropyridin-3-yl}ethynyl)cyclohexyl]carbamate The title compound was prepared using the procedure described in Example 1E, using Example 74A (348 mg, 1.558 mmol) in place of Example 1D. LCMS: 349.9 $(M+H)^+$.

EXAMPLE 74C tert-butyl (trans-4-(4-chloro-1H-pyrrolo[2,3-b]pyridin-2-yl)cyclohexyl)carbamate A solution of Example 74B (150 mg, 0.429 mmol) in N,N-dimethylformamide (5 mL) was treated with potassium tert-butoxide (122 mg, 1.085 mmol) and the mixture was stirred at room temperature for 12 hours. The mixture was quenched with ice water and extracted into ethyl acetate (30 mL×2). The organic layer was washed with water and brine solution (25 mL each) and the organic layer was separated, dried over sodium sulfate, filtered, and concentrated to afford the title compound. LCMS: 250.1 $(M+H)^+$.

EXAMPLE 74D trans-4-[4-(5-fluoro-2-methoxyphenyl)-1H-pyrrolo[2,3-b]pyridin-2-yl]cyclohexanamine The title compound was prepared as the acetate salt using the procedure described in Example 7A, using Example 74C (100 mg, 0.286 mmol) in place of Example 5A and 5-fluoro-2-methoxyphenylboronic acid (73 mg, 0.429 mmol) in place of 2-bromo-4-cyclopropyl-1-methoxybenzene, and purified using preparative HPLC (Zorbax XDB C-18 column with gradient elution from 10M ammonium acetate in water to 1:1 methanol/acetonitrile). LCMS: 340.2 $(M+H)^+$. $^1$H NMR (400 MHz, DMSO-$d_6$): δ 1.14-1.23 (m, 2H), 1.46-1.55 (m, 2H), 1.84-1.89 (m, 2H), 1.99-2.02 (m, 2H), 3.17 (s, 2H), 3.73-3.74 (m, 5H), 5.93 (s, 1H), 6.99-7.01 (m, 1H), 7.16-7.21 (m, 2H), 7.24-7.29 (m, 1H), 8.12-8.14 (m, 1H), 11.5 (s, 1H).

EXAMPLE 75

3-[4-(5-fluoro-2-methoxyphenyl)-1H-pyrrolo[2,3-b]pyridin-2-yl]cyclohexanamine

EXAMPLE 75A tert-butyl (3-formylcyclohexyl)carbamate

To a solution of tert-butyl 3-(hydroxymethyl)cyclohexylcarbamate (1.4 g, 6.11 mmol) in dimethylsulfoxide (10 mL) was added triethylamine (1.853 g, 18.32 mmol) followed by the pyridine-sulfur trioxide (2.92 g, 18.32 mmol) in 5 mL of dimethylsulfoxide, and the mixture was stirred at room temperature for 1 hour. The mixture was quenched with ice water and extracted into ethyl acetate (30 mL×2). The organic layer was washed with water and brine solution (25 mL each), dried over sodium sulfate, filtered, and concentrated under reduced pressure to afford the title compound.

EXAMPLE 75B tert-butyl(3-ethynylcyclohexyl)carbamate

The title compound was prepared using the procedure described in Example 1D, using Example 75A (1.3 g, 5.72 mmol) in place of Example 1C. LCMS: 124 $(M+H-Boc)^+$.

EXAMPLE 75C tert-butyl[3-({2-[(tert-butoxycarbonyl)amino]-4-chloropyridin-3-yl}ethynyl)cyclohexyl]carbamate The title compound was prepared using the procedure described in Example 1E, using Example 75B (409 mg, 1.833 mmol) in place of Example 1D. LCMS: 450.2 $(M+H)^+$.

EXAMPLE 75D tert-butyl (3-(4-chloro-1H-pyrrolo[2,3-b]pyridin-2-yl)cyclohexyl)carbamate The title compound was prepared using the procedure described in Example 74C, using Example 75C (550 mg, 1.222 mmol) in place of Example 74B. LCMS: 350.1 $(M+H)^+$.

EXAMPLE 75E tert-butyl (3-(4-(5-fluoro-2-methoxyphenyl)-1H-pyrrolo[2,3-b]pyridin-2-yl)cyclohexyl)carbamate The title compound was prepared using the procedure described in Example 1H, using Example 75D (400 mg, 1.143 mmol) in place of Example 1G. LCMS: 340.2 $(M+H-Boc)^+$.

EXAMPLE 75F 3-(4-(5-fluoro-2-methoxyphenyl)-1H-pyrrolo[2,3-b]pyridin-2-yl)cyclohexanamine The title compound was prepared as the trifluoroacetate salt using the procedure described in Example 6E, using Example 75E (400 mg, 0.910 mmol) in place of Example 6D, and purified using preparative HPLC (Zorbax XDB C-18 column with gradient elution from 0.1% trifluoroacetic acid in water to 1:1 methanol/acetonitrile). LCMS: 340.2 $(M+H)^+$. $^1$H NMR (400 MHz, DMSO-$d_6$/$D_2O$): δ 1.21-1.54 (m, 4H), 1.84-2.03 (m, 3H), 2.21-2.24 (m, 1H), 2.84-2.90

(m, 1H), 3.13-3.18 (m, 1H), 3.72 (s, 3H), 6.02 (s, 1H), 7.14 (d, J=5.2 Hz, 1H), 7.19-7.23 (m, 2H), 7.26-7.31 (m, 1H), 8.20 (d, J=5.2 Hz, 1H).

EXAMPLE 76

4-(5-fluoro-2-methoxyphenyl)-3-methyl-2-(piperidin-4-yl)-1H-pyrrolo[2,3-b]pyridine

EXAMPLE 76A tert-butyl 4-(3-bromo-4-(5-fluoro-2-methoxyphenyl)-1H-pyrrolo[2,3-b]pyridin-2-yl)piperidine-1-carboxylate To a solution of Example 17F (300 mg, 0.705 mmol) in N,N-dimethylformamide (3 mL) at 0° C. was added N-bromosuccinimide (188 mg, 1.058 mmol) and the mixture was stirred at room temperature for 3 hours. The mixture was diluted with water and ethyl acetate and the ethyl acetate layer was washed with water and brine, dried over sodium sulfate, filtered, and concentrated. Purification by column chromatography (silica gel, 15% ethyl acetate in hexane) afforded the title compound. LCMS: 506 (M+3)$^+$.

EXAMPLE 76B tert-butyl 4-(4-(5-fluoro-2-methoxyphenyl)-3-methyl-1H-pyrrolo[2,3-b]pyridin-2-yl)piperidine-1-carboxylate To Example 76A (200 mg, 0.397 mmol) in 1,4-dioxane (6 mL) was added 1.2M dimethylzinc solution in toluene (0.991 ml, 1.190 mmol) followed by [1,1'-bis(diphenylphosphino)ferrocene]dichloropalladium(II), dichloromethane adduct (16.19 mg, 0.020 mmol) and the mixture was heated at 100° C. for 30 minutes. The mixture was cooled, quenched with ammonium chloride solution and extracted ethyl acetate. The organic layer was washed with water and brine, dried over sodium sulfate, filtered, and concentrated to afford the title compound. LCMS: 440.2 (M+H)$^+$.

EXAMPLE 76C 4-(5-fluoro-2-methoxyphenyl)-3-methyl-2-(piperidin-4-yl)-1H-pyrrolo[2,3-b]pyridine The title compound was prepared as the trifluoroacetate salt using the procedure described in Example 6E, using Example 76B (100 mg, 0.228 mmol) in place of Example 6D, and purified using preparative HPLC (Zorbax XDB C-18 column with gradient elution from 0.1% trifluoroacetic acid in water to 1:1 methanol/acetonitrile). LCMS: 340.2 (M+H)$^+$. $^1$H NMR (400 MHz, DMSO-d$_6$): δ 1.72 (s, 3H), 1.83-1.89 (m, 2H), 1.98-2.09 (m, 2H), 3.0-3.09 (m, 2H), 3.36-3.40 (m, 2H), 3.65 (s, 3H), 6.8 (d, J=4.8 Hz, 1H), 7.06 (dd, J=3.2, 8.8 Hz, 1H), 7.11-7.14 (m, 1H), 7.24-7.29 (m, 1H), 8.14 (d, J=4.8 Hz, 1H), 8.78 (d, J=8.4 Hz, 1H), 11.54 (s, 1H).

EXAMPLE 77

N-benzyl-6-[5-chloro-2-(piperidin-4-yl)-1H-pyrrolo[2,3-b]pyridin-4-yl]pyridin-2-amine

EXAMPLE 77A 4-bromo-5-chloro-3-iodopyridin-2-amine

A solution of Example 52A (3 g, 14.46 mmol) in N,N-dimethylformamide (60 mL) was heated to 40° C. and iodine chloride (2.82 g, 17.35 mmol) was added. After stirring at 40° C. for 3 hours, a second lot of iodine chloride (2.82 g, 17.35 mmol) was added and the mixture was stirred overnight at 40° C. The mixture was cooled to room temperature and quenched with ice cold water. The mixture was extracted with ethyl acetate (100 mL×2) and the organic layer was washed with water and brine, dried over sodium sulfate, filtered, and concentrated. Purification by column chromatography (silica gel, 20% ethyl acetate in hexane) afforded the title compound. LCMS: 334.6 (M+H)$^+$.

EXAMPLE 77B tert-butyl 4-((2-amino-4-bromo-5-chloropyridin-3-yl)ethynyl)piperidine-1-carboxylate The title compound was prepared using the procedure described in Example 1E, using Example 77A (1 g, 3.00 mmol) in place of Example 1A and Example 17C (942 mg, 4.50 mmol) in place of Example 1D. LCMS: 415.8 (M+H)$^+$.

EXAMPLE 77C tert-butyl 4-(4-bromo-5-chloro-1H-pyrrolo[2,3-b]pyridin-2-yl)piperidine-1-carboxylate The title compound was prepared using the procedure described in Example 1F, using Example 77B (800 mg, 1.929 mmol) in place of Example 1E. LCMS: 415.8 (M+H)$^+$.

EXAMPLE 77D tert-butyl 4-(5-chloro-4-(6-fluoropyridin-2-yl)-1H-pyrrolo[2,3-b]pyridin-2-yl)piperidine-1-carboxylate The title compound was prepared using the procedure described in Example 7A, using Example 77C (500 mg, 1.206 mmol) in place of 2-bromo-4-cyclopropyl-1-methoxybenzene and 2-fluoro-6-(4,4,5,5-tetramethyl-1,3,2-dioxaborolan-2-yl)pyridine (403 mg, 1.808 mmol) in place of Example 5A. LCMS: 331.0 (M+H).

EXAMPLE 77E tert-butyl 4-(4-(6-(benzylamino)pyridin-2-yl)-5-chloro-1H-pyrrolo[2,3-b]pyridin-2-yl)piperidine-1-carboxylate Example 77D (150 mg, 0.348 mmol) was heated at 100° C. for 12 hours in sealed tube with benzyl amine (1 mL). The mixture was diluted with water and ethyl acetate and the ethyl acetate layer was washed with water and brine, dried over sodium sulfate, filtered and concentrated to afford the title compound. LCMS: 519.7 (M+H)$^+$.

EXAMPLE 77F

N-benzyl-6-(5-chloro-2-(piperidin-4-yl)-1H-pyrrolo[2,3-b]pyridin-4-yl)pyridin-2-amine The title compound was prepared as the acetate salt using the procedure described in Example 1H, using Example 77E (160 mg, 0.309 mmol) in place of Example 1G. LCMS: 418.2 (M+H)$^+$. $^1$H NMR (400 MHz, DMSO-d$_6$/D$_2$O): δ 1.50-1.54 (m, 2H), 1.8-1.88 (m, 2H), 2.64-2.69 (m, 3H), 3.05-3.08 (m, 2H), 4.50 (s, 2H), 5.9 (s, 1H), 6.60 (d, J=8.4

Hz, 1H), 6.76 (d, J=7.2 Hz, 1H), 7.21 (brs, 1H), 7.30-7.31 (m, 4H), 7.54 (t, J=8 Hz, 1H), 8.16 (s, 1H).

EXAMPLE 78

5-chloro-4-(3-fluorophenyl)-2-(piperidin-3-yl)-1H-pyrrolo[2,3-b]pyridine

EXAMPLE 78A tert-butyl 3-((2-amino-4-bromo-5-chloropyridin-3-yl)ethynyl)piperidine-1-carboxylate The title compound was prepared using the procedure described in Example 1E, using Example 77A (286 mg, 0.858 mmol) in place of Example 1A. LCMS: 416 (M+H)$^+$.

EXAMPLE 78B tert-butyl 3-(4-bromo-5-chloro-1H-pyrrolo[2,3-b]pyridin-2-yl)piperidine-1-carboxylate The title compound was prepared using the procedure described in Example 1F, using Example 78A (400 mg, 0.98 mmol) in place of Example 1E. LCMS: 415.8 (M+H)$^+$.

EXAMPLE 78C tert-butyl 3-(5-chloro-4-(3-fluorophenyl)-1H-pyrrolo[2,3-b]pyridin-2-yl)piperidine-1-carboxylate To Example 78B (150 mg, 0.362 mmol) in 1 mL water and 4 mL dioxane was added potassium carbonate (125 mg, 0.904 mmol) in 1 mL of water followed by the addition of 3-fluorophenylboronic acid (55.7 mg, 0.398 mmol). The mixture was degassed with nitrogen for 10 minutes and tetrakistriphenylphosphine (20.90 mg, 0.018 mmol) was added. The mixture was heated overnight in a Biotage Initiator microwave (model 355302) at 100° C. The mixture was diluted with ethyl acetate (50 mL) and washed with water (50×3 mL) followed by brine solution (25 mL). The organic layer was dried over anhydrous sodium sulfate, filtered, and concentrated to afford the title compound. LCMS: 330.0 (M+H-Boc)$^+$.

EXAMPLE 78D 5-chloro-4-(3-fluorophenyl)-2-(piperidin-3-yl)-1H-pyrrolo[2,3-b]pyridine The title compound was prepared as the trifluoroacetate salt using the procedure described in Example 6E, using Example 78C (120 mg, 0.279 mmol) in place of Example 6D, and purified using preparative HPLC (Zorbax XDB C-18 column with gradient elution from 0.1% trifluoroacetic acid in water to 1:1 methanol/acetonitrile). LCMS: 330.0 (M+H)$^+$. $^1$H NMR (400 MHz, DMSO-d$_6$/D$_2$O): δ 1.67-1.70 (m, 2H), 1.86-1.9 (m, 1H), 2.05-2.1 (m, 1H), 2.8-2.84 (m, 1H), 3.07-3.10 (m, 2H), 3.27 (d, J=12 Hz, 1H), 3.47-3.50 (m, 1H), 6.05 (s, 1H), 7.32-7.36 (m, 3H), 7.59-7.61 (m, 1H), 8.29 (s, 1H).

EXAMPLE 79

5-chloro-4-(6-fluoropyridin-2-yl)-2-(piperidin-3-yl)-1H-pyrrolo[2,3-b]pyridine

EXAMPLE 79A tert-butyl 3-(5-chloro-4-(6-fluoropyridin-2-yl)-1H-pyrrolo[2,3-b]pyridin-2-yl)piperidine-1-carboxylate The title compound was prepared using the procedure described in Example 5B, using Example 78B (150 mg, 362 mmol) in place of 6-bromo-5-methoxypyridin-2-amine and 2-fluoro-6-(4,4,5,5-tetramethyl-1,3,2-dioxaborolan-2-yl) pyridine (121 mg, 0.543 mmol) in place of Example 5A. LCMS: 430.9 (M+H)$^+$.

EXAMPLE 79B 5-chloro-4-(6-fluoropyridin-2-yl)-2-(piperidin-3-yl)-1H-pyrrolo[2,3-b]pyridine The title compound was prepared using the procedure described in Example 1H, using Example 79A (100 mg, 0.232 mmol) in place of Example 1G. LCMS: 331 (M+H)$^+$. $^1$H NMR (400 MHz, DMSO-d$_6$): δ 1.66-1.85 (m, 3H), 2.08-2.12 (m, 1H), 2.81-2.83 (m, 1H), 3.07-3.16 (m, 1H), 3.22-3.28 (m, 2H), 3.48-3.51 (m, 1H), 6.15 (d, J=1.6 Hz, 1H), 7.33 (dd, J=2, 8 Hz, 1H), 7.65 (d, J=2, 7.2 Hz, 1H), 8.17-8.23 (m, 1H), 9.11-9.18 (m, 1H), 12.2 (s, 1H).

EXAMPLE 80

N-benzyl-6-[5-chloro-2-(piperidin-3-yl)-1H-pyrrolo[2,3-b]pyridin-4-yl]pyridin-2-amine

EXAMPLE 80A tert-butyl 3-(4-(6-(benzylamino)pyridin-2-yl)-5-chloro-1H-pyrrolo[2,3-b]pyridin-2-yl)piperidine-1-carboxylate The title compound was prepared using the procedure described in Example 77E, using Example 79A (80 mg, 0.186 mmol) in place of Example 77D. LCMS: 519 (M+H)$^+$.

EXAMPLE 80B

N-benzyl-6-(5-chloro-2-(piperidin-3-yl)-1H-pyrrolo[2,3-b]pyridin-4-yl)pyridin-2-amine The title compound was prepared using the procedure described in Example 1H, using Example 80A (80 mg, 0.154 mmol) in place of Example 1G. LCMS: 417.9 (M+H)$^+$. $^1$H NMR (400 MHz, DMSO-d$_6$): δ 1.61-1.85 (m, 2H), 2.04-2.08 (m, 1H), 2.78-2.80 (m, 1H), 3.22-3.30 (m, 2H), 3.36-3.47 (m, 2H), 4.61 (s, 2H), 6.10 (s, 1H), 6.93 (brs, 2H), 7.30-7.38 (m, 6H), 7.9 (brs, 1H), 8.31 (s, 1H), 9.24 (brs, 1H), 12.2 (s, 1H).

EXAMPLE 81

6-[5-chloro-2-(piperidin-3-yl)-1H-pyrrolo[2,3-b]pyridin-4-yl]-N-(tetrahydro-2H-pyran-4-ylmethyl)pyridin-2-amine

EXAMPLE 81A tert-butyl 3-(5-chloro-4-(6-(((tetrahydro-2H-pyran-4-yl)methyl)amino)pyridin-2-yl)-1H-pyrrolo[2,3-b]pyridin-2-yl)piperidine-1-carboxylate The title compound was prepared using the procedure described in Example 77E, using Example 79A (25 mg, 0.058 mmol) in place of Example 77D and (tetrahydro-2H-pyran-4-yl)methanamine (53 mg, 0.464 mmol) in place of benzyl amine. LCMS: 527 (M+H)$^+$.

EXAMPLE 81B 6-(5-chloro-2-(piperidin-3-yl)-1H-pyrrolo[2,3-b]pyridin-4-yl)-N-((tetrahydro-2H-pyran-4-yl)methyl)pyridin-2-amine The title compound was prepared as the hydrochloride salt using the procedure described in Example 1H, using Example 81A (15 mg, 0.029 mmol) in place of Example 1G. LCMS: 425.9 (M+H)$^+$. $^1$H NMR (400 MHz, DMSO-d$_6$/D$_2$O): δ 1.58-1.92 (m, 3H), 2.81-2.86 (m, 1H), 2.98-3.10 (m, 1H), 3.15-3.18 (m, 8H), 3.18-3.32 (m, 5H), 3.68-3.86 (m, 2H), 6.22 (s, 1H), 6.86 (d, J=6.8 Hz, 1H), 6.90-6.95 (m, 1H), 7.25-7.35 (m, 1H), 8.32 (s, 1H).

EXAMPLE 82

N-benzyl-6-[5-chloro-2-(1-methylpiperidin-3-yl)-1H-pyrrolo[2,3-b]pyridin-4-yl]pyridin-2-amine The title compound was prepared using the procedure described in Example 8, using Example 80A (100 mg, 0.193 mmol) in place of Example 2A. LCMS: 433.15 (M+H)$^+$. $^1$H NMR (400 MHz, DMSO-d$_6$): δ 1.44-1.47 (m, 1H), 1.72-1.75 (m, 1H), 1.92-2.07 (m, 2H), 2.78 (s, 3H), 3.03-3.15 (m, 3H), 3.45-3.62 (m, 2H), 4.50 (s, 2H), 6.02 (s, 1H), 6.65-6.76 (m, 2H), 7.22-7.32 (m, 5H), 7.57-7.60 (m, 1H), 8.23 (s, 1H), 9.65 (brs, 1H), 12.0 (s, 1H).

EXAMPLE 83 methyl 3-{4-[6-(benzylamino)pyridin-2-yl]-5-chloro-1H-pyrrolo[2,3-b]pyridin-2-yl}piperidine-1-carboxylate

EXAMPLE 83A methyl 3-((2-amino-4-bromo-5-chloropyridin-3-yl)ethynyl)piperidine-1-carboxylate The title compound was prepared using the procedure described in Example 1E, using Example 77A (200 mg, 0.600 mmol) in place Example 1A and Example 16A (130 mg, 0.780 mmol in place of Example 1D. LCMS: 373.8 (M+2)$^+$.

EXAMPLE 83B methyl 3-(4-bromo-5-chloro-1H-pyrrolo[2,3-b]pyridin-2-yl)piperidine-1-carboxylate The title compound was prepared using the procedure described in Example 1F, using Example 83A (200 mg, 0.537 mmol) in place of Example 1E. LCMS: 373.8 (M+2)$^+$.

EXAMPLE 83C methyl 3-(5-chloro-4-(6-fluoropyridin-2-yl)-1H-pyrrolo[2,3-b]pyridin-2-yl)piperidine-1-carboxylate The title compound was prepared using the procedure described in Example 5B, using Example 83B (100 mg, 0.268 mmol) in place of 6-bromo-5-methoxypyridin-2-amine and 2-fluoro-6-(4,4,5,5-tetramethyl-1,3,2-dioxaborolan-2-yl)pyridine (90 mg, 0.403 mmol) in place of Example 5A. LCMS: 389.1 (M+H)$^+$.

EXAMPLE 83D methyl 3-(4-(6-(benzylamino)pyridin-2-yl)-5-chloro-1H-pyrrolo[2,3-b]pyridin-2-yl)piperidine-1-carboxylate The title compound was prepared as the trifluoroacetate salt using the procedure described in Example 77E, using Example 83C (90 mg, 0.231 mmol) in place of Example 77D, and purified using preparative HPLC (Zorbax XDB C-18 column with gradient elution from 0.1% trifluoroacetic acid in water to 1:1 methanol/acetonitrile). LCMS: 475.8 (M+H)$^+$. $^1$H NMR (400 MHz, DMSO-d$_6$): δ 1.41-1.69 (m, 4H), 1.96-1.98 (m, 1H), 2.75-3.0 (m, 4H), 3.59 (s, 3H), 4.58 (s, 2H), 6.0 (s, 1H), 6.77-6.85 (m, 2H), 7.22-7.34 (m, 5H), 7.67 (brs, 1H), 8.22 (s, 1H), 12.0 (s, 1H).

EXAMPLE 84

N-benzyl-6-{5-chloro-2-[1-(propan-2-ylsulfonyl)piperidin-3-yl]-1H-pyrrolo[2,3-b]pyridin-4-yl}pyridin-2-amine

EXAMPLE 84A 4-bromo-5-chloro-3-((1-(isopropylsulfonyl)piperidin-3-yl)ethynyl)pyridin-2-amine The title compound was prepared using the procedure described in Example 1E, using Example 77A (200 mg, 0.600 mmol) in place Example 1A and Example 15A (581 mg, 2.70 mmol) in place of Example 1D. LCMS: 422 (M+H)$^+$.

EXAMPLE 84B 4-bromo-5-chloro-2-(1-(isopropylsulfonyl)piperidin-3-yl)-1H-pyrrolo[2,3-b]pyridine The title compound was prepared using the procedure described in Example 1F, using Example 84A (500 mg, 1.188 mmol) in place of Example 1E. LCMS: 421.0 (M+H)$^+$.

EXAMPLE 84C 5-chloro-4-(6-fluoropyridin-2-yl)-2-(1-(isopropylsulfonyl)piperidin-3-yl)-1H-pyrrolo[2,3-b]pyridine The title compound was prepared using the procedure described in Example 7A, using Example 84B (200 mg, 0.475 mmol) in place of 2-bromo-4-cyclopropyl-1-methoxybenzene and 2-fluoro-6-(4,4,5,5-tetramethyl-1,3,2-dioxaborolan-2-yl)pyridine (159 mg, 0.713 mmol) in place of Example 5A. LCMS: 437.1 (M+H)$^+$.

EXAMPLE 84D

N-benzyl-6-(5-chloro-2-(1-(isopropylsulfonyl)piperidin-3-yl)-1H-pyrrolo[2,3-b]pyridin-4-yl)pyridin-2-amine The title compound was prepared as the trifluoroacetate salt using the procedure described in Example 77E, using Example 84C (200 mg, 0.458 mmol) in place of Example 77D, and purified using preparative HPLC (AG/AD/PP/C-18 column with gradient elution from 0.1% trifluoroacetic acid in water to 1:1 methanol/acetonitrile). LCMS: 524.2 (M+H)$^+$. $^1$H NMR (400 MHz, DMSO-d$_6$): δ 1.20-1.22 (m, 7H), 1.5-1.51 (m, 2H), 1.76-1.77 (m, 1H), 1.98-2.0 (m, 1H), 2.87-2.94 (m, 2H), 3.64-3.67 (m. 2H), 3.79-3.81 (m, 1H), 4.54 (s, 2H), 6.02 (s, 1H), 6.63-6.72 (m, 1H), 6.82-6.86 (m, 1H), 7.2-7.3 (m, 2H), 7.3-7.38 (m, 4H), 7.6-7.64 (m, 1H), 8.22 (s, 1H), 12.0 (s, 1H).

EXAMPLE 85

3-[5-chloro-4-(3-fluorophenyl)-1H-pyrrolo[2,3-b]pyridin-2-yl]cyclohexanamine

EXAMPLE 85A tert-butyl (3-((2-amino-4-bromo-5-chloropyridin-3-yl)ethynyl)cyclohexyl)carbamate The title compound was prepared using the procedure described in Example 1E, using Example 77A (600 mg, 1.800 mmol) in place Example 1A and Example 75B (603 mg, 2.70 mmol) in place of Example 1D. LCMS: 374 (M+3-NCOOH)$^+$.

EXAMPLE 85B tert-butyl (3-(4-bromo-5-chloro-1H-pyrrolo[2,3-b]pyridin-2-yl)cyclohexyl)carbamate The title compound was prepared using the procedure described in Example 1F, using Example 85A (600 mg, 1.39 mmol) in place of Example 1E. LCMS: 329.7 (M+H-Boc)$^+$.

EXAMPLE 85C tert-butyl (3-(5-chloro-4-(3-fluorophenyl)-1H-pyrrolo[2,3-b]pyridin-2-yl)cyclohexyl)carbamate The title compound was prepared using the procedure described in Example 7A, using Example 85B (200 mg, 0.466 mmol) in place of 2-bromo-4-cyclopropyl-1-methoxybenzene and 3-fluorophenylboronic acid (98 mg, 0.700 mmol) in place of Example 5A. LCMS: 344 (M+H-Boc)$^+$.

EXAMPLE 85D 3-(5-chloro-4-(3-fluorophenyl)-1H-pyrrolo[2,3-b]pyridin-2-yl)cyclohexanamine The title compound was prepared as the trifluoroacetate salt using the procedure described in Example 6E, using Example 85C (200 mg, 0.451 mmol) in place of Example 6D, and purified using preparative HPLC (ECLIPSE XDB C-18 column with gradient elution from 0.1% trifluoroacetic acid in water to acetonitrile). LCMS: 343.9 (M+H)$^+$. $^1$H NMR (400 MHz, DMSO-d$_6$/D$_2$O): δ 1.24-1.31 (m, 1H), 1.43-1.55 (m, 1H), 1.84-1.88 (m, 2H), 1.96-2.02 (m, 2H), 2.16-2.24 (m, 2H), 2.84-2.90 (m, 1H), 3.12-3.19 (m, 1H), 7.29-7.34 (m, 4H), 7.57-7.60 (m, 1H), 8.24 (s, 1H).

EXAMPLE 86

6-[2-(3-aminocyclohexyl)-5-chloro-1H-pyrrolo[2,3-b]pyridin-4-yl]-N-benzylpyridin-2-amine

EXAMPLE 86A tert-butyl (3-(5-chloro-4-(6-fluoropyridin-2-yl)-1H-pyrrolo[2,3-b]pyridin-2-yl)cyclohexyl)carbamate The title compound was prepared using the procedure described in Example 7A, using Example 85B (200 mg, 0.466 mmol) in place of 2-bromo-4-cyclopropyl-1-methoxybenzene and 2-fluoro-6-(4,4,5,5-tetramethyl-1,3,2-dioxaborolan-2-yl)pyridine (156 mg, 0.700 mmol) in place of Example 5A. LCMS: 345 (M+H-Boc)$^+$.

EXAMPLE 86B tert-butyl (3-(4-(6-(benzylamino)pyridin-2-yl)-5-chloro-1H-pyrrolo[2,3-b]pyridin-2-yl)cyclohexyl)carbamate The title compound was prepared using the procedure described in Example 77E, using Example 86A (200 mg, 0.58 mmol) in place of Example 77D. LCMS: 432 (M+H-Boc)$^+$.

EXAMPLE 86C 6-(2-(3-aminocyclohexyl)-5-chloro-1H-pyrrolo[2,3-b]pyridin-4-yl)-N-benzylpyridin-2-amine The title compound was prepared as the trifluoroacetate salt using the procedure described in Example 6E, using Example 86B (250 mg, 0.470 mmol) in place of Example 6D. LCMS: 432.0 (M+H)$^+$. $^1$H NMR (400 MHz, DMSO-d$_6$/D$_2$O): δ 1.22-1.29 (m, 2H), 1.38-1.47 (m, 2H), 1.8-1.86 (m, 2H), 1.94-1.97 (m, 1H), 2.14-2.17 (m, 1H), 2.76-2.79 (m, 1H), 3.11-3.17 (m, 1H), 4.51 (s, 2H), 5.89 (s, 1H), 6.70 (d, J=7.6 Hz, 1H), 6.8 (d, J=6.8 Hz, 1H), 7.23-7.25 (m, 1H), 7.32 (d, J=4 Hz, 4H), 7.63 (t, J=8 Hz, 1H), 8.20 (s, 1H).

EXAMPLE 87

4-(5-fluoro-2-methoxyphenyl)-2-(1,2,3,6-tetrahydropyridin-4-yl)-1H-pyrrolo[2,3-b]pyridine

EXAMPLE 87A 4-(5-fluoro-2-methoxyphenyl)-1-(phenylsulfonyl)-1H-pyrrolo[2,3-b]pyridine A suspension of 4-bromo-1-(phenylsulfonyl)-1H-pyrrolo[2,3-b]pyridine (10.00 g, 29.7 mmol), 5-fluoro-2-methoxyphenylboronic acid (5.54 g, 32.6 mmol), 2M aqueous potassium carbonate (66.7 mL, 133 mmol), and [1,1'-bis(diphenylphosphino)ferrocene]dichloropalladium(II) dichloromethane adduct (1.453 g, 1.779 mmol) in 1,2-dimethoxyethane (250 mL) was degassed with nitrogen and heated at 100° C. for 1.5 hours. The mixture was diluted with ethyl acetate and washed with aqueous sodium bicarbonate (twice) and brine. The organic layer was dried over magnesium sulfate, filtered, concentrated, and purified on silica gel using an ISCO Companion flash system eluting with heptane/ethyl acetate (75:25 to 60:40) to afford the title compound. MS (ESI$^+$) m/z 383.1 (M+H)$^+$.

EXAMPLE 87B 4-(5-fluoro-2-methoxyphenyl)-2-iodo-1-(phenylsulfonyl)-1H-pyrrolo[2,3-b]pyridine To a solution of Example 87A (4.24 g, 11.09 mmol) in tetrahydrofuran at −78° C. was added dropwise 2M lithium diisopropylamide (8.32 mL, 16.63 mmol) in tetrahydrofuran/heptane/ethylbenzene. After 30 minutes, iodine (5.63 g, 22.18 mmol) in tetrahydrofuran (50 mL) was cannulated into the mixture. The mixture was stirred at −78° C. for 3 hours, quenched with aqueous sodium thiosulfate and extracted with ethyl acetate (twice). The combined organic layers were dried over magnesium sulfate, filtered, and concentrated until a precipitate formed. The solids were filtered, washed with ethyl acetate and dried under vacuum to afford the title compound. MS (ESI$^+$) m/z 508.9 (M+H)$^+$.

EXAMPLE 87C tert-butyl 4-(4-(5-fluoro-2-methoxyphenyl)-1-(phenylsulfonyl)-1H-pyrrolo[2,3-b]pyridin-2-yl)-5,6-dihydropyridine-1(2H)-carboxylate A mixture of Example 87B (1.600 g, 3.15 mmol), tert-butyl 4-(4,4,5,5-tetramethyl-1,3,2-dioxaborolan-2-yl)-5,6-dihydropyridine-1(2H)-carboxylate (1.071 g, 3.46 mmol), tetrakistriphenylphosphine palladium (0.182 g, 0.157 mmol), and aqueous sodium bicarbonate solution (15 mL) in N,N-dimethylformamide (60 mL) was degassed with nitrogen and heated at 80° C. for 3 hours. After cooling, the mixture was quenched with water and brine and extracted with ethyl acetate (twice). The combined organic layers were washed with brine, dried over magnesium sulfate, filtered, concentrated, and purified on silica gel using an ISCO Companion flash system eluting with heptane/ethyl acetate (65:35 to 5:5) to afford the title compound. MS (ESI$^+$) m/z 564.1 (M+H)$^+$.

EXAMPLE 87D 4-(5-fluoro-2-methoxyphenyl)-2-(1,2,3,6-tetrahydropyridin-4-yl)-1H-pyrrolo[2,3-b]pyridine A mixture of Example 87C (400.0 mg, 0.710 mmol) and 20% sodium hydroxide (0.7 mL) solution in dioxane (6 mL) was heated at 90° C. for 6 hours. The mixture was concentrated and the residue was treated with ethyl acetate and washed with water. The organic layer was dried over magnesium sulfate, filtered and concentrated until most of solvent was evaporated. The solids were filtered, washed with ethyl acetate/heptane, and dried under vacuum to afford the protected intermediate. The intermediate was dissolved in dichloromethane (8 mL) and treated with trifluoroacetic acid (0.547 mL, 7.10 mmol) and the mixture was stirred for 3 hours and concentrated. The residue was dissolved in 2.5 mL methanol and treated with 4 mL 1M hydrogen chloride in ether. After stirring for 15 minutes, the mixture was treated with ether. The solids were filtered, washed with ether, and dried under vacuum to afford the title compound as a hydrochloride salt. $^1$H NMR (400 MHz, CD$_3$OD) δ 2.93-2.83 (m, 2H), 3.50 (t, J=6.1 Hz, 2H), 3.83 (s, 3H), 4.01-3.96 (m, 2H), 6.65-6.59 (m, 1H), 6.74 (s, 1H), 7.38-7.21 (m, 3H), 7.58 (d, J=6.1 Hz, 1H), 8.36 (d, J=6.1 Hz, 1H). MS (ESI$^+$) m/z 324.1 (M+H)$^+$.

EXAMPLE 88

6-[2-(piperidin-4-yl)-1H-pyrrolo[2,3-b]pyridin-4-yl]-N-(tetrahydro-2H-pyran-4-ylmethyl)pyridin-2-amine

EXAMPLE 88A 2-fluoro-6-(4,4,5,5-tetramethyl-1,3,2-dioxaborolan-2-yl)pyridine To a solution of 2-bromo-6-fluoropyridine (5.0 g, 28.4 mmol) in 1,4-dioxane (150 mL) was added 4,4,4',4',5,5,5',5'-octamethyl-2,2'-bi(1,3,2-dioxaborolane) (8.6 g, 34.1 mmol), and potassium acetate (5.6 g, 56.8 mmol) followed by [1,1'-bis(diphenylphosphino)ferrocene]dichloropalladium(II) (1.2 g, 1.4 mmol) and the mixture was degassed with nitrogen. The mixture was heated at 110° C. for 10 hours, diluted with ethyl acetate and filtered through diatomaceous earth. The filtrate was concentrated and purified by column chromatography (silica gel, 20% ethyl acetate in hexane) to afford the title compound. LCMS: 224 (M+H)$^+$.

EXAMPLE 88B tert-butyl 4-(4-(6-fluoropyridin-2-yl)-1H-pyrrolo[2,3-b]pyridin-2-yl)piperidine-1-carboxylate To a mixture of Example 17E (500 mg, 1.5 mmol); Example 88A (400 mg, 1.8 mmol) and dichlorobis(triphenylphosphine)palladium (52 mg, 0.07 mmol) in 7/3/2 1,2-dimethoxyethane/water/ethanol (15 mL) was added 2M sodium carbonate solution (1.1 mL) and the mixture was heated in a microwave reactor (Biotage Initiator, model 355302) at 150° C. for 30 minutes. After cooling, the mixture was diluted with dichloromethane (100 mL) and filtered through diatomaceous earth. The filtrate was concentrated and purified by column chromatography (silica gel, 100% ethyl acetate) to afford the title compound. LCMS: 397 (M+H)$^+$.

EXAMPLE 88C 6-(2-(piperidin-4-yl)-1H-pyrrolo[2,3-b]pyridin-4-yl)-N-((tetrahydro-2H-pyran-4-yl)methyl)pyridin-2-amine A mixture of Example 88B (40 mg, 0.1 mmol) and (tetrahydro-2H-pyran-4-yl)methanamine (116 mg, 1.0 mmol) in dimethylsulfoxide (1 mL) was heated in a sealed tube at 110° C. for 30 minutes. The mixture was diluted with dichloromethane (20 mL) and washed with water. The organic phase was concentrated and purified by column chromatography (silica gel, 10% methanol in ethyl acetate) to afford the Boc-protected intermediate. To the intermediate in dichloromethane (5 mL) was added trifluoroacetic acid (0.5 mL) and the mixture was stirred at room temperature for 1 hour. Concentration and purification by HPLC (Zorbax C-18, using a 0-100% gradient of water/acetonitrile, containing 0.1% trifluoroacetic acid) afforded the title compound. $^1$H NMR (400 MHz, DMSO-$d_6$): δ 1.13-1.41 (m, 2 H), 1.63-1.73 (m, 2 H), 1.74-1.95 (m, 3 H), 2.28 (d, J=11.19 Hz, 2 H), 2.99-3.18 (m, 3 H), 3.20-3.35 (m, 4 H), 3.39 (d, J=12.55 Hz, 2 H), 3.88 (dd, J=11.19, 2.71 Hz, 2 H), 6.68 (d, J=8.48 Hz, 1 H), 6.79 (s, 1 H), 7.18 (d, J=7.12 Hz, 1 H), 7.50 (d, J=5.09 Hz, 1 H), 7.55-7.68 (m, 1 H), 8.26 (d, J=5.09 Hz, 1 H). LCMS: 392 (M+H)$^+$.

EXAMPLE 89

6-[2-(1-methylpiperidin-4-yl)-1H-pyrrolo[2,3-b]pyridin-4-yl]-N-(tetrahydro-2H-pyran-4-ylmethyl)pyridin-2-amine A solution of Example 88C (15 mg, 0.04 mmol) in methanol (2 mL) was treated with 37% formaldehyde in water (12 mg, 0.4 mmol) and the mixture was stirred at room temperature for 1 hour. Sodium cyanoborohydride (5 mg, 0.08 mmol) was added and the mixture was stirred at room temperature for 12 hours. The mixture was diluted with dichloromethane and washed with water. The organic phase was concentrated and purified by HPLC (Zorbax C-18, using a 0-100% gradient of water/acetonitrile, containing 0.1% trifluoroacetic acid) to afford the title compound. $^1$H NMR (400 MHz, DMSO-$d_6$): δ 1.17-1.38 (m, 2 H), 1.64-1.73 (m, 2 H), 1.77-1.96 (m, 4 H), 2.34 (d, J=13.56 Hz, 4 H), 2.83 (d, J=4.75 Hz, 3 H), 3.00-3.20 (m, 4 H), 3.56 (d, J=11.53 Hz, 2 H), 3.88 (dd, J=10.68, 3.22 Hz, 2 H), 6.68 (d, J=8.48 Hz, 1 H), 6.77-6.83 (m, 1 H), 7.18 (d, J=7.80 Hz, 1 H), 7.50 (d, J=5.09 Hz, 1 H), 7.58-7.63 (m, 1 H), 8.24-8.27 (m, 1 H). LCMS: 406 (M+H)$^+$.

EXAMPLE 90

6-[2-(1-methylpiperidin-4-yl)-1H-pyrrolo[2,3-b]pyridin-4-yl]-N-(3-phenylpropyl)pyridin-2-amine 4-(6-fluoropyridin-2-yl)-2-(piperidin-4-yl)-1H-pyrrolo[2,3-b]pyridine

EXAMPLE 90A

To a solution of Example 88B (136 mg, 0.34 mmol) in dichloromethane (15 ml) was added trifluoroacetic acid (1 mL) and the mixture was stirred at room temperature for 1 hour. Concentration and purification by HPLC (Zorbax C-18, using a 0-100% gradient of water/acetonitrile, containing 0.1% trifluoroacetic acid) afforded the title compound. LCMS: 297 (M+H)$^+$ 4-(6-fluoropyridin-2-yl)-2-(1-methylpiperidin-4-yl)-1H-pyrrolo[2,3-b]pyridine

EXAMPLE 90B

The title compound was prepared using the procedure described in Example 89, using Example 90A (89 mg, 0.3 mmol) in place of Example 88C. LCMS: 311 (M+H)$^+$

EXAMPLE 90C

6-[2-(1-methylpiperidin-4-yl)-1H-pyrrolo[2,3-b]pyridin-4-yl]-N-(3-phenylpropyl)pyridin-2-amine The title compound was prepared using the procedure described in Example 88C, using Example 90B (40 mg, 0.13 mmol) in place of Example 88B and 3-phenylpropan-1-amine (122 mg, 0.9 mmol) in place of (tetrahydro-2H-pyran-4-yl)methanamine. $^1$H NMR (400 MHz, DMSO-$d_6$): δ 1.74-2.00 (m, 4 H), 2.32 (d, J=13.56 Hz, 2 H), 2.65-2.74 (m, 2 H), 2.83 (d, J=4.75 Hz, 3 H), 2.96-3.21 (m, 3 H), 3.41 (t, J=6.95 Hz, 2 H), 3.54 (d, J=12.21 Hz, 2 H), 6.66 (d, J=8.48 Hz, 1 H), 6.76 (s, 1 H), 7.11-7.36 (m, 6 H), 7.49 (d, J=5.09 Hz, 1 H), 7.61 (t, J=7.80 Hz, 1 H), 8.25 (d, J=5.09 Hz, 1 H). LCMS: 426 (M+H)$^+$.

EXAMPLE 91

6-[2-(1-methylpiperidin-4-yl)-1H-pyrrolo[2,3-b]pyridin-4-yl]-N-(pyridin-3-ylmethyl)pyridin-2-amine The title compound was prepared using the procedure described in Example 88C, using Example 90B (40 mg, 0.13 mmol) in place of Example 88B and pyridin-3-ylmethanamine (139 mg, 1.3 mmol) in place of (tetrahydro-2H-pyran-4-yl)methanamine. $^1$H NMR (400 MHz, DMSO-$d_6$): δ 1.63-1.91 (m, 2 H), 2.16-2.29 (m, 2 H), 2.83 (s, 3 H), 2.96 (d, J=11.87 Hz, 1 H), 3.04-3.16 (m, 2 H), 3.53 (d, J=11.87 Hz, 2 H), 4.73 (s, 2 H), 6.59 (s, 1 H), 6.68 (d, J=8.14 Hz, 1 H), 7.24 (d, J=7.46 Hz, 1 H), 7.41-7.44 (m, 1 H), 7.57-7.64 (m, 1 H), 7.69 (dd, J=7.80, 5.09 Hz, 1 H), 8.16 (d, J=7.80 Hz, 1 H), 8.20 (d, J=5.09 Hz, 1 H), 8.62 (dd, J=5.43, 1.36 Hz, 1 H), 8.75 (s, 1 H). LCMS: 399 (M+H)$^+$.

EXAMPLE 92

6-[2-(1-methylpiperidin-4-yl)-1H-pyrrolo[2,3-b]pyridin-4-yl]-N-[2-(phenylsulfanyl)ethyl]pyridin-2-amine The title compound was prepared using the procedure as described in Example 88C, using Example 90B (35 mg, 0.11 mmol) in place of Example 88B and 2-(phenylthio)ethanamine (173 mg, 1 mmol) in place of (tetrahydro-2H-pyran-4-yl)methanamine. $^1$H NMR (400 MHz, DMSO-$d_6$): 1.66-1.87 (m, 2 H), 2.17-2.31 (m, 2 H), 2.83 (s, 3 H), 2.91-3.21 (m, 6 H), 3.30-3.43 (m, 1 H), 3.54 (d, J=11.87 Hz, 2 H), 6.59 (s, 1 H), 6.69 (d, J=8.14 Hz, 1 H), 7.26 (d, J=7.12 Hz, 1 H), 7.43 (d, J=5.09 Hz, 1 H), 7.58-7.65 (m, 2 H), 7.75 (dd, J=7.97, 5.26 Hz, 1 H), 8.21 (d, J=5.09 Hz, 2 H), 8.60-8.70 (m, 1 H), 8.78 (d, J=1.36 Hz, 1 H). LCMS: 444 (M+H)$^+$.

EXAMPLE 93

N-(cyclopropylmethyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.1 mmol) in place of Example 88B and cyclopropylmethanamine (69 mg, 1.0 mmol) in place of (tetrahydro-2H-pyran-4-yl)methanamine. $^1$H NMR (400 MHz, DMSO-$d_6$): δ 0.20-0.33 (m, 2 H), 0.43-0.57 (m, 2 H), 1.08-1.26 (m, 1 H), 1.74-1.95 (m, 2 H), 2.26-2.41 (m, 2 H), 2.83 (d, J=4.75 Hz, 3 H), 2.97-3.21 (m, 4 H), 3.30 (d, J=6.78 Hz, 2 H), 3.56 (d, J=11.87 Hz, 2 H), 6.68 (d, J=6.44 Hz, 1 H), 6.82 (s, 1 H), 7.19 (d, J=7.12 Hz, 1 H), 7.51 (d, J=5.09 Hz, 1 H), 7.57-7.66 (m, 1 H), 8.25 (d, J=5.09 Hz, 1 H). LCMS: 444 (M+H)+.

EXAMPLE 94

4-(5-fluoro-2-methoxyphenyl)-2-(pyrrolidin-2-yl)-1H-pyrrolo[2,3-b]pyridine

EXAMPLE 94A tert-butyl 2-((2-(tert-butoxycarbonylamino)-4-chloropyridin-3-yl)ethynyl)pyrrolidine-1-carboxylate The title compound was prepared using the procedure described in Example 1E, using tert-butyl 2-ethynylpyrrolidine-1-carboxylate (2.5 g, 12.80 mmol) in place of Example 1D. MS (ESI+) m/z 421.9 (M+H)+.

EXAMPLE 94B tert-butyl 2-(4-chloro-1H-pyrrolo[2,3-b]pyridin-2-yl)pyrrolidine-1-carboxylate The title compound was prepared using the procedure described in Example 1F, using Example 94A (2.5 g, 5.93 mmol) in place of Example 1E. MS (ESI+) m/z 321.9 (M+H)+.

EXAMPLE 94C tert-butyl 2-(4-(5-fluoro-2-methoxyphenyl)-1H-pyrrolo[2,3-b]pyridin-2-yl)pyrrolidine-1-carboxylate To Example 94B (200 mg, 0.622 mmol) in tetrahydrofuran (1.5 mL) and water (0.5 mL) was added potassium phosphate (400 mg, 1.884 mmol) followed by 5-fluoro-2-methoxyphenylboronic acid (140 mg, 0.824 mmol). The mixture was degassed with nitrogen and [1,3-bis(2,6-diisopropylphenyl)imidazol-2-ylidene]chloro[3-phenylallyl]palladium(II) (40 mg, 0.062 mmol) was added. The mixture was subjected to microwave irradiation (Biotage Initiator) at 60° C. for 90 minutes. After dilution with ethyl acetate and filtration through diatomaceous earth, the organic layer was washed with water and brine (50 mL each) and dried over sodium sulfate, filtered, and concentrated. The residue dissolved in dichloromethane and purified by flash chromatography using a Grace, SF25-40 g column, eluting with 0-100% ethyl acetate/hexane, to afford the title compound. LCMS: 412.2 (M+H)+.

EXAMPLE 94D 4-(5-fluoro-2-methoxyphenyl)-2-(pyrrolidin-2-yl)-1H-pyrrolo[2,3-b]pyridine To Example 94C (30 mg, 0.073 mmol) in dichloromethane (1 mL) was added trifluoroacetic acid (1 mL, 12.98 mmol) and the mixture was stirred for 15 hours. The mixture was concentrated and purified by reverse phase flash chromatography (SiO$_2$-C18, 0-100% acetonitrile/water/0.1% trifluoroacetic acid) to yield the title compound as the trifluoroacetate salt. $^1$H NMR (500 MHz, DMSO-d$_6$) δ 2.47-1.95 (m, 4H), 3.34-3.30 (m, 2H), 3.74 (s, 3H), 4.88-4.71 (m, 1H), 6.45 (d, J=1.7, 1H), 7.13 (d, J=4.9, 1H), 7.26-7.17 (m, 2H), 7.34-7.26 (m, 1H), 8.30 (d, J=4.9, 1H), 8.87 (br. s, 1H), 9.41 (br. s, 1H), 11.97 (br. s, 1H). MS (ESI+) m/z 312.2 (M+H)+.

EXAMPLE 95

N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine The title compound was prepared using the procedure described in Example 88C, using Example 90B (35 mg, 0.13 mmol) in place of Example 88B and (2,2-dimethyltetrahydro-2H-pyran-4-yl)methanamine (162 mg, 1.3 mmol) in place of (tetrahydro-2H-pyran-4-yl)methanamine. $^1$H NMR (400 MHz, DMSO-d$_6$): δ 0.99-1.11 (m, 2 H), 1.14 (s, 6 H), 1.67 (dd, J=13.22, 2.71 Hz, 2 H), 1.76-1.94 (m, 2 H), 1.95-2.11 (m, 1 H), 2.20-2.30 (m, 1 H), 2.35 (d, J=11.87 Hz, 2 H), 2.83 (d, J=4.75 Hz, 3 H), 2.97-3.21 (m, 4 H), 3.26 (t, J=6.95 Hz, 2 H), 3.56 (d, J=12.21 Hz, 2 H), 6.64 (d, J=7.80 Hz, 1 H), 6.78 (s, 1 H), 7.17 (d, J=7.12 Hz, 1 H), 7.50 (d, J=5.09 Hz, 1 H), 7.54-7.60 (m, 1 H), 8.24 (d, J=5.09 Hz, 1H). LCMS: 434 (M+H)+.

EXAMPLE 96

N-benzyl-N-methyl-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and N-methyl-1-phenylmethanamine (112 mg, 1.0 mmol) in place of (tetrahydro-2H-pyran-4-yl)methanamine. $^1$H NMR (400 MHz, DMSO-d$_6$): δ 1.52-1.80 (m, 2 H), 2.15 (d, J=13.90 Hz, 2 H), 2.67-2.77 (m, 1 H), 2.81 (d, J=4.75 Hz, 3 H), 2.95-3.10 (m, 4 H), 3.13 (s, 3 H), 4.95 (s, 2 H), 6.65 (s, 1 H), 6.74 (d, J=8.48 Hz, 1 H), 7.27 (dd, J=6.44, 3.05 Hz, 3 H), 7.33 (d, J=5.76 Hz, 2 H), 7.45 (s, 1 H), 7.49 (d, J=5.43 Hz, 1 H), 7.64-7.73 (m, 1 H), 8.20 (d, J=5.09 Hz, 1 H). LCMS: 412 (M+H)+.

EXAMPLE 97

N-(3-chlorobenzyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and (3-chlorophenyl)methanamine (137 mg, 1.0 mmol) in place of (tetrahydro-2H-pyran-4-yl)methanamine. $^1$H NMR (400 MHz, DMSO-d$_6$): δ 1.64-1.85 (m, 2 H), 2.22 (d, J=13.90 Hz, 2 H), 2.83 (d, J=4.75 Hz, 3 H), 2.91-3.02 (m, 1 H), 3.05-3.19 (m, 2 H), 3.53 (d, J=11.53 Hz, 2 H), 4.65 (s, 2 H), 6.64 (d, J=2.37 Hz, 1 H), 6.67 (s, 1 H), 7.22 (d, J=7.12 Hz, 1 H), 7.27-7.33 (m, 2 H), 7.33-7.39 (m, 3 H), 7.43 (s, 1 H), 7.47 (d, J=5.43 Hz, 1 H), 8.19-8.22 (m, 1H). LCMS: 412 (M+H)+.

EXAMPLE 98

2-cyclohexyl-4-(5-fluoro-2-methoxyphenyl)-1H-pyrrolo[2,3-b]pyridine

EXAMPLE 98A tert-butyl (4-chloro-3-(cyclohexylethynyl)pyridin-2-yl)carbamate tert-Butyl 4-chloro-3-iodopyridin-2-ylcarbamate (1.0 g, 2.82 mmol) in 10 mL tetrahydrofuran was treated with copper(I) iodide (0.027 g, 0.141 mmol) and bis(triphenylphosphine)palladium(II) chloride (0.099 g, 0.141 mmol) and the mixture was purged with nitrogen for 5 minutes. Ethynylcyclohexane (0.472 mL, 3.67 mmol) and triethylamine (1.179 mL, 8.46 mmol) were added and the mixture was stirred overnight under nitrogen. The mixture was filtered through diatomaceous earth and the filtrate washed with aqueous citric acid (once), water (twice), and brine (once), dried over magnesium sulfate, filtered, and concentrated. Purification by flash chromatography (20% ethyl acetate/hexane) provided the title compound. MS (DCI) m/e 335/337 (M+H)+.

EXAMPLE 98B 4-chloro-2-cyclohexyl-1H-pyrrolo[2,3-b]pyridine

A solution of Example 98A (870 mg, 2.60 mmol) in 20 mL toluene was treated with potassium tert-butoxide (729 mg, 6.50 mmol) and 18-crown-6 (68.7 mg, 0.260 mmol) and the mixture was heated at 65° C. for 6 hours and at 85° C. overnight. The cooled mixture was partitioned between ethyl acetate and water. The layers were separated and the aqueous layer was extracted with ethyl acetate (twice). The combined organic extracts were rinsed with water (once) and brine (twice), dried over magnesium sulfate, filtered, and concentrated. The residue was suspended in diethyl ether and the solids were collected and rinsed with diethyl ether to afford the title compound. MS (DCI) m/e 235/237 (M+H)+.

EXAMPLE 98C 2-cyclohexyl-4-(5-fluoro-2-methoxyphenyl)-1H-pyrrolo[2,3-b]pyridine A solution of Example 98B (200 mg, 0.852 mmol), (5-fluoro-2-methoxyphenyl)boronic acid (188 mg, 1.108 mmol), phenylallylchloro[1,3-bis(diisopropylphenyl)-2-imidazol-2-ylidene]palladium(II) (50 mg, 0.077 mmol) and potassium phosphate (543 mg, 2.56 mmol) in 8 mL 3:1 tetrahydrofuran:water was purged with nitrogen and heated under nitrogen at 60° C. for 4 hours. The cooled mixture was diluted with water and ethyl acetate and filtered through diatomaceous earth. The mixture was extracted into ethyl acetate (twice) and the combined extracts were rinsed with brine, dried over magnesium sulfate, filtered and concentrated. Purification by flash chromatography (1:1 ethyl acetate:hexanes) provided only a small amount of material. The column was washed with 10% methanol/dichloromethane and the remainder of the material eluted. The combined residue was suspended in diethyl ether and the solids were collected and rinsed with diethyl ether to afford the title compound. $^1$H NMR (300 MHz, DMSO-d$_6$) δ 1.20-1.48 (m, 5 H) 1.64-1.76 (m, 3 H) 1.99-2.02 (m, 2 H) 2.70-2.73 (m, 1H) 3.72 (s, 3 H) 5.92 (s, 1 H) 6.99 (d, J=5.08 Hz, 1 H) 7.15-7.27 (m, 3 H) 8.12 (d, J=4.75 Hz, 1 H) 11.50 (s, 1 H). MS (DCI) m/e 325 (M+H)+.

EXAMPLE 99

1-{2-[4-(5-fluoro-2-methoxyphenyl)-1H-pyrrolo[2,3-b]pyridin-2-yl]pyrrolidin-1-yl}ethanone To a solution of Example 94D (0.035 g, 0.112 mmol) and triethylamine (0.1 mL, 0.717 mmol) in dichloromethane (2 mL), was slowly added acetyl chloride (1M in dichloromethane, 0.11 mL, 0.11 mmol) and the mixture was stirred at room temperature for 5 minutes. The mixture was concentrated and purified by reverse phase flash chromatography (SiO$_2$-C18, 10-100% acetonitrile/water/0.1% trifluoroacetic acid) to afford the title compound as the trifluoroacetate salt. $^1$H NMR (400 MHz, DMSO-d$_6$) δ 2.36-1.73 (m, 7H), 3.81-3.31 (m, 6H), 5.18 (dd, J=8.1, 6.5, 1H), 6.00 (dd, J=21.8, 1.2, 1H), 7.12 (dd, J=10.1, 5.1, 1H), 7.35-7.16 (m, 3H), 8.23 (d, J=5.1, 1H), 11.85 (d, J=49.2, 1H). MS (ESI+) m/z 354.1 (M+H)+.

EXAMPLE 100

1-{4-[4-(5-fluoro-2-methoxyphenyl)-1H-pyrrolo[2,3-b]pyridin-2-yl]-3,6-dihydropyridin-1(2H)-yl}ethanone A mixture of Example 87D (30.0 mg, 0.076 mmol), (benzotriazol-1-yloxy)tripyrrolidinophosphonium hexafluorophosphate (47.3 mg, 0.091 mmol), triethylamine (0.042 mL, 0.303 mmol), and acetic acid (5.20 μl, 0.091 mmol) in N,N-dimethylformamide (1.2 mL) was stirred for 5 hours. The mixture was quenched with water and brine and extracted with ethyl acetate (twice). The combined organic layers were diluted with ethyl acetate until clear, washed with brine, dried over magnesium sulfate, filtered, and concentrated. The residue was triturated with ethyl acetate to afford the title compound. $^1$H NMR (400 MHz, DMSO) δ 1.17 (t, J=7.2 Hz, 2H), 2.04 (s, 1.5H), 2.07 (s, 1.5H), 3.67-3.58 (m, 2H), 3.74 (s, 3H), 4.22-4.11 (m, 2H), 6.25 (dd, J=6.4, 2.0 Hz, 1H), 6.51 (bs, 1H), 7.04 (d, J=4.9 Hz, 1H), 7.32-7.16 (m, 3H), 8.21 (d, J=5.0 Hz, 1H), 11.89-11.81 (m, 1H). MS (ESI+) m/z 366.1 (M+H)+.

EXAMPLE 101

1-{4-[4-(5-fluoro-2-methoxyphenyl)-1H-pyrrolo[2,3-b]pyridin-2-yl]-3,6-dihydropyridin-1(2H)-yl}-2-hydroxyethanone The title compound was prepared as described in Example 100, using 2-hydroxyacetic acid in place of acetic acid. Purification by reverse-phase HPLC performed on a Zorbax RX-C18 column (250×21.2 mm, 7 μm particle size) using a gradient of 15% to 100% methanol: 0.1% aqueous trifluoroacetic acid afforded the title compound as a trifluoroacetic acid salt. $^1$H NMR (400 MHz, CD$_3$OD) δ 2.69-2.58 (m, 2H), 3.79-3.62 (m, 1H), 3.86-3.82 (m, 4H), 4.37-4.16 (m, 4H), 6.64-6.50 (m, 2H), 7.34-7.19 (m, 3H), 7.52 (d, J=6.1 Hz, 1H), 8.29 (d, J=6.1 Hz, 1H). MS (ESI+) m/z 382.2 (M+H)+.

EXAMPLE 102

N-(2,6-difluorobenzyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and (2,6-difluorophenyl)methanamine (138 mg, 1.0 mmol) in place of (tetrahydro-2H-pyran-4-yl)methanamine. $^1$H NMR (400 MHz, DMSO-d$_6$): δ 1.65-1.85 (m, 2 H), 2.22 (d, J=13.22 Hz, 2 H), 2.83 (d, J=4.75 Hz, 3 H), 2.90-3.02 (m, 1 H), 3.04-3.18 (m, 2 H), 3.54 (d, J=12.21 Hz, 2 H), 4.67 (s, 2 H), 6.60 (d, J=1.36 Hz, 1 H), 6.68 (d, J=8.14 Hz, 1 H), 7.07-7.37 (m, 3 H), 7.45 (d, J=5.09 Hz, 1H), 7.55-7.64 (m, 1 H), 8.20 (d, J=5.09 Hz, 1 H), 8.19 (s, 1 H). LCMS: 434 (M+H)+.

EXAMPLE 103

4-(5-fluoro-2-methoxyphenyl)-2-(1-methylpyrrolidin-2-yl)-1H-pyrrolo[2,3-b]pyridine To a solution of Example 94D (0.07 g, 0.130 mmol) and triethylamine (0.1 mL, 0.717 mmol) in methanol (5 mL), was added formaldehyde (37% in water) (0.2 mL, 2.69 mmol) and the mixture was stirred at room temperature for 1 hour. Sodium cyanoborohydride (0.03 g, 0.477 mmol) was added and the mixture was stirred at room temperature for 15 hours. Trifluoroacetic acid (1 mL) was then added and the mixture was stirred for 1 hour. Concentration and purification by reverse phase flash chromatography ($SiO_2$-C18, 0-100% acetonitrile/water/0.1% trifluoroacetic acid) afforded the title compound as the trifluoroacetate salt. $^1$H NMR (400 MHz, DMSO-$d_6$) δ 2.46-1.99 (m, 4H).), 2.82 (d, J=4.8, 3H), 3.74 (s, 3H), 4.65-4.48 (m, 1H), 6.57 (d, J=2.0, 1H), 7.16 (d, J=5.0, 1H), 7.36-7.19 (m, 3H), 8.33 (d, J=4.9, 1H), 9.70 (br.s, 1H), δ 12.05 (br. s, 1H). MS (ESI+) m/z 326.0 (M+H)+.

EXAMPLE 104

6-[2-(1-methylpiperidin-4-yl)-1H-pyrrolo[2,3-b] pyridin-4-yl]-N-[(1S)-1-phenylethyl]pyridin-2-amine The title compound was prepared using the procedure described in Example 88C, using Example 90B (30 mg, 0.10 mmol) in place of Example 88B and (S)-1-phenylethanamine (117 mg, 1.0 mmol) in place of (tetrahydro-2H-pyran-4-yl)methanamine. $^1$H NMR (400 MHz, DMSO-$d_6$): δ 1.52 (d, J=7.02 Hz, 3 H), 1.77-1.93 (m, 2 H), 2.27 (d, J=14.34 Hz, 2 H), 2.84 (d, J=3.97 Hz, 3 H), 2.97-3.08 (m, 1 H), 3.13 (d, J=12.21 Hz, 2 H), 3.57 (d, J=11.60 Hz, 2 H), 5.22 (d, J=6.71 Hz, 1 H), 6.63 (s, 1 H), 6.71 (d, J=8.24 Hz, 1 H), 7.18-7.25 (m, 2 H), 7.34 (t, J=7.63 Hz, 2 H), 7.41-7.50 (m, 3 H), 7.63 (t, J=7.93 Hz, 1 H), 8.27 (d, J=5.49 Hz, 1 H). LCMS: 412 (M+H)+.

EXAMPLE 105

N-(1,3-benzodioxol-5-ylmethyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and benzo[d][1,3]dioxol-5-ylmethanamine (146 mg, 1.0 mmol) in place of (tetrahydro-2H-pyran-4-yl)methanamine. $^1$H NMR (400 MHz, DMSO-$d_6$): δ 1.69-1.90 (m, 2 H), 2.25 (d, J=13.12 Hz, 2 H), 2.81 (d, J=3.97 Hz, 3 H), 3.00 (t, J=12.05 Hz, 1 H), 3.06-3.15 (m, 2 H), 3.52 (d, J=11.90 Hz, 2 H), 4.53 (s, 2 H), 5.95 (s, 2 H), 6.65 (d, J=8.54 Hz, 1 H), 6.71 (s, 1 H), 6.86 (s, 1 H), 6.93 (s, 1 H), 7.16 (s, 1 H), 7.22 (t, J=6.87 Hz, 1 H), 7.50 (d, J=5.19 Hz, 1 H), 7.59 (t, J=7.78 Hz, 1 H), 8.23 (d, J=5.19 Hz, 1 H). LCMS: 442 (M+H)+.

EXAMPLE 106

5-chloro-6-[2-(piperidin-4-yl)-1H-pyrrolo[2,3-b] pyridin-4-yl]pyridin-2-amine

EXAMPLE 106A 6-bromo-5-chloropyridin-2-amine

To a solution of 6-bromopyridin-2-amine (10 g, 58 mmol) in acetonitrile (150 mL) was added 1-chloropyrrolidine-2, 5-dione (8.1 g, 60 mmol) and the mixture was heated at 80° C. for 10 hours. The mixture was diluted with ethyl acetate (200 mL) and washed with water. The organic phase was concentrated and purified by column chromatography (silica gel, 30% ethyl acetate in hexane) to afford the title compound. LCMS: 208 (M+H)+.

EXAMPLE 106B tert-butyl 6-bromo-5-chloropyridin-2-ylcarbamate

To a solution of Example 106A (7.1 g, 34.2 mmol) in dichloromethane (200 mL) was added di-tert-butyl dicarbonate (9 g, 68 mmol), triethylamine (6.9 g, 68 mmol), and 4-dimethylaminopyridine (1.04 g, 8.6 mmol) and the mixture was stirred at room temperature overnight.

The mixture was diluted with ethyl acetate (200 mL) and washed with water. The organic phase was concentrated and purified by column chromatography (silica gel, 10% ethyl acetate in hexane) to afford the title compound. LCMS: 308 (M+H)+.

EXAMPLE 106C 5-chloro-6-(2-(piperidin-4-yl)-1H-pyrrolo[2,3-b] pyridin-4-yl)pyridin-2-amine To a mixture of Example 21A (100 mg, 0.23 mmol); Example 106B (108 mg, 0.35 mmol), bis(triphenylphosphine)palladium(II)chloride (16 mg, 0.02 mmol), tricyclohexylphosphine (7 mg, 0.02 mmol) and cesium carbonate (230 mg, 0.7 mmol) was added dioxane (10 mL) and the mixture was degassed with nitrogen and heated at 110° C. for 10 hours. After cooling, the mixture was diluted with ethyl acetate (50 mL) and filtered through diatomaceous earth. The filtrate was concentrated and the residue was dissolved in dichloromethane (5 mL) and trifluoroacetic acid (0.5 mL). The mixture was stirred at room temperature for 2 hours, concentrated, and purified by HPLC (Zorbax C-18, using a 0-100% gradient of water/acetonitrile, containing 0.1% trifluoroacetic acid) to afford the title compound. $^1$H NMR (400 MHz, DMSO-$d_6$): δ 1.71-1.87 (m, 2 H) 2.22 (d, J=12.82 Hz, 2 H), 2.94-3.12 (m, 3 H), 3.36 (d, J=12.51 Hz, 2 H), 6.11 (s, 1 H), 6.73 (d, J=8.85 Hz, 1 H), 7.17 (d, J=4.88 Hz, 1 H), 7.75 (d, J=8.85 Hz, 1 H), 8.27 (d, J=4.88 Hz, 1 H). LCMS: 327 (M+H)+.

EXAMPLE 107

N-[2-(phenylsulfanyl)ethyl]-6-[2-(piperidin-4-yl)-1H-pyrrolo[2,3-b]pyridin-4-yl]pyridin-2-amine The title compound was prepared using the procedure described in Example 88C, using 2-(phenylthio)ethanamine (146 mg, 1.0 mmol) in place of (tetrahydro-2H-pyran-4-yl) methanamine. $^1$H NMR (400 MHz, DMSO-$d_6$): δ 1.75-1.92

(m, 2 H), 2.26 (d, J=12.21 Hz, 2 H), 2.98-3.15 (m, 3 H), 3.20-3.27 (m, 2 H), 3.38 (d, J=12.51 Hz, 2 H), 3.60-3.69 (m, 2 H), 6.64 (d, J=8.24 Hz, 1 H), 6.75 (s, 1 H), 7.16 (d, J=7.32 Hz, 1 H), 7.19-7.25 (m, 3 H), 7.37 (d, J=7.32 Hz, 2 H), 7.52 (d, J=5.19 Hz, 1 H), 7.62 (t, J=7.93 Hz, 1 H), 8.28 (d, J=5.19 Hz, 1 H). LCMS: 430 (M+H)$^+$.

EXAMPLE 108

1-{3-[4-(5-fluoro-2-methoxyphenyl)-1H-pyrrolo[2,3-b]pyridin-2-yl]pyrrolidin-1-yl}ethanone To a suspension of Example 59F (50 mg, 0.130 mmol) and triethylamine (0.091 mL, 0.651 mmol) in dichloromethane (2 mL) was added acetyl chloride (0.195 mL, 0.195 mmol) at room temperature. The mixture was stirred for 16 hours, concentrated, and purified by reverse phase flash chromatography (silica gel-C18, 15-60% acetonitrile/water/0.1% trifluoroacetic acid) to provide the title compound. $^1$H NMR (300 MHz, DMSO-$d_6$) δ 1.95 (d, J=4.1 Hz, 3H), 1.98-2.40 (m, 3H), 3.23-3.42 (m, 2H), 3.45-3.60 (m, 2H), 3.73 (s, 3H), 3.77-3.96 (m, 2H), 6.11 (dd, J=10.4, 1.7 Hz, 1H), 7.08 (dd, J=5.1, 1.6 Hz, 1H), 7.15-7.34 (m, 3H), 8.20 (d, J=5.1 Hz, 1H), 11.81 (s, 1H). MS (ESI$^+$) m/z 354.1 (M+H)$^+$.

EXAMPLE 109

2-{3-[4-(5-fluoro-2-methoxyphenyl)-1H-pyrrolo[2,3-b]pyridin-2-yl]pyrrolidin-1-yl}ethanol

EXAMPLE 109A 2-(1-(2-((tert-butyldimethylsilyl)oxy)ethyl)pyrrolidin-3-yl)-4-(5-fluoro-2-methoxyphenyl)-1H-pyrrolo[2,3-b]pyridine To a solution of Example 59F (50 mg, 0.130 mmol) in dichloromethane (1 mL)/methanol (1 mL) was added triethylamine (0.036 mL, 0.260 mmol) followed by acetic acid (0.037 mL, 0.651 mmol) and (t-butyldimethylsilyloxy)acetaldehyde (0.050 mL, 0.260 mmol). After stirring for 5 minutes, MP-cyanoborohydride (2.49 mmol/g, 209 mg, 0.52 mmol) was added and the mixture was shaken for 16 hours at room temperature. The resin was filtered off, and washed with methanol/dichloromethane (2×3 mL). The crude mixture was concentrated and used in the next step without further purification. LCMS: 470.3 (M+H)$^+$.

EXAMPLE 109B

2-{3-[4-(5-fluoro-2-methoxyphenyl)-1H-pyrrolo[2,3-b]pyridin-2-yl]pyrrolidin-1-yl}ethanol A solution of Example 109A (61.1 mg, 0.13 mmol) and trifluoroacetic acid (0.6 mL, 7.79 mmol) in dichloromethane (2 mL) was stirred at room temperature for 16 hours. The mixture was concentrated and purified by reverse phase flash chromatography (silica gel-C18, 15-60% acetonitrile/water/0.1% trifluoroacetic acid) to afford the title compound as the trifluoroacetate salt. $^1$H NMR (300 MHz, DMSO-$d_6$) δ 2.07-2.25 (m, 1H), 2.42 (d, J=7.7 Hz, 1H), 3.23-3.37 (m, 3H), 3.70 (d, J=5.2 Hz, 4H), 3.73 (s, 3H), 3.90 (dd, J=18.6, 7.5 Hz, 2H), 5.39 (s, 1H), 6.16-6.25 (m, 1H), 7.06 (d, J=5.0 Hz, 1H), 7.16-7.23 (m, 1H), 7.24-7.33 (m, 1H), 8.20 (d, J=5.0 Hz, 1H), 9.78 (s, 1H), 11.73 (s, 1H), 11.80 (s, 1H). MS (ESI$^+$) m/z 356.1 (M+H)$^+$.

EXAMPLE 110

4-(5-fluoro-2-methoxyphenyl)-2-[1-(tetrahydro-2H-pyran-4-yl)pyrrolidin-3-yl]-1H-pyrrolo[2,3-b]pyridine To a solution of Example 59F (50 mg, 0.130 mmol) in dichloromethane (1 mL)/methanol (1 mL) was added triethylamine (0.036 mL, 0.260 mmol) followed by acetic acid (0.037 mL, 0.651 mmol) and tetrahydro-4H-pyran-4-one (0.024 mL, 0.260 mmol). After stirring for 5 minute, MP-cyanoborohydride (2.49 mmol/g, 209 mg, 0.52 mmol) was added and the mixture was shaken for 16 hours at room temperature. The resin was filtered off and washed with methanol/dichloromethane (2×3 mL). The crude mixture was concentrated and purified by reverse phase flash chromatography (silica gel-C18, 15-60% acetonitrile/water/0.1% trifluoroacetic acid) to afford the title compound as the trifluoroacetate salt. $^1$H NMR (300 MHz, DMSO-$d_6$) δ 1.48-1.69 (m, 2H), 1.93-2.36 (m, 4H), 3.20-3.49 (m, 6H), 3.73 (s, 3H), 3.79-4.01 (m, 3H), 6.23 (dd, J=4.3, 1.9 Hz, 1H), 7.07 (d, J=4.9 Hz, 1H), 7.15-7.33 (m, 3H), 8.17-8.24 (m, 1H), 9.72-9.95 (m, 1H), 11.72-11.84 (m, 1H). MS (ESI$^+$) m/z 396.1 (M+H)$^+$.

EXAMPLE 111

4-(5-fluoro-2-methoxyphenyl)-2-[1-(pyridin-2-ylmethyl)pyrrolidin-3-yl]-1H-pyrrolo[2,3-b]pyridine The title compound was prepared as the trifluoroacetate salt using the procedure described in Example 110, using 2-pyridinecarboxaldehyde (0.025 mL, 0.260 mmol) in place of tetrahydro-4H-pyran-4-one. $^1$H NMR (300 MHz, DMSO-$d_6$) δ 2.16-2.32 (m, 1H), 3.73 (s, 3H), 3.75-3.90 (m, 3H), 4.65 (s, 2H), 6.21 (d, J=1.8 Hz, 1H), 7.07 (d, J=4.9 Hz, 1H), 7.16-7.25 (m, 2H), 7.23-7.34 (m, 1H), 7.44-7.55 (m, 2H), 7.93 (td, J=7.7, 1.8 Hz, 1H), 8.20 (d, J=4.9 Hz, 1H), 8.64-8.71 (m, 1H), 10.37-10.57 (m, 1H), 11.77 (bs, 1H). MS (ESI$^+$) m/z 403.0 (M+H)$^+$.

EXAMPLE 112

4-(5-fluoro-2-methoxyphenyl)-2-[1-(pyridin-3-ylmethyl)pyrrolidin-3-yl]-1H-pyrrolo[2,3-b]pyridine The title compound was prepared as the trifluoroacetate salt using the procedure described in Example 110, using 3-pyridinecarboxaldehyde (0.025 mL, 0.260 mmol) in place of tetrahydro-4H-pyran-4-one. $^1$H NMR (400 MHz, DMSO-$d_6$) δ 1.85-2.41 (m, 1H), 3.16-3.64 (m, 4H), 4.53 (m, 2H), 6.24 (bs, 1H), 7.11 (d, J=5.0 Hz, 1H), 7.16-7.26 (m, 2H), 7.29 (td, J=8.6, 3.1 Hz, 1H), 7.59 (dd, J=7.9, 4.9 Hz, 1H), 8.07 (dt, J=7.9, 1.9 Hz, 1H), 8.23 (d, J=5.0 Hz, 1H), 8.70 (dd, J=4.9, 1.6 Hz, 1H), 8.78 (d, J=2.1 Hz, 1H), 10.41 (bs, 1H), 11.87-11.92 (m, 1H). MS (ESI$^+$) m/z 403.0 (M+H)$^+$.

EXAMPLE 113

4-(5-fluoro-2-methoxyphenyl)-2-[1-(pyridin-4-ylmethyl)pyrrolidin-3-yl]-1H-pyrrolo[2,3-b]pyridine The title compound was prepared as the trifluoroacetate salt using the procedure described in Example 110, using 4-pyridinecarboxaldehyde (0.025 mL, 0.260 mmol) in place of tetrahydro-4H-pyran-4-one. $^1$H NMR (400 MHz, DMSO-$d_6$) δ 2.05-2.32 (m, 1H), 3.73 (s, 3H), 3.85-3.93 (m, 1H), 4.54 (s, 2H), 6.23 (s, 1H), 7.10 (d, J=5.0 Hz, 1H), 7.16-7.33 (m, 3H), 7.61-7.67 (m, 2H), 8.22 (d, J=5.0 Hz, 1H), 8.72-8.77 (m, 2H), 11.75-11.94 (m, 1H). MS (ESI$^+$) m/z 403.0 (M+H)$^+$.

EXAMPLE 114

4-(5-fluoro-2-methoxyphenyl)-2-[1-(tetrahydro-2H-pyran-3-ylmethyl)pyrrolidin-3-yl]-1H-pyrrolo[2,3-b]pyridine The title compound was prepared as the trifluoroacetate salt using the procedure described in Example 110, using tetrahydro-pyran-3-carbaldehyde (29.7 mg, 0.260 mmol) in place of tetrahydro-4H-pyran-4-one. $^1$H NMR (400 MHz, DMSO-d$_6$) δ 1.22-1.40 (m, 1H), 1.42-1.57 (m, 1H), 1.56-1.65 (m, 1H), 1.82-1.90 (m, 1H), 1.91-2.50 (m, 4H), 2.87-3.44 (m, 5H), 3.74 (m, 3H), 3.72-4.09 (m, 4H), 6.20-6.26 (m, 1H), 7.09 (d, J=5.0 Hz, 1H), 7.17-7.25 (m, 2H), 7.29 (td, J=8.6, 3.1 Hz, 1H), 8.18-8.25 (m, 1H), 9.65-9.83 (m, 1H), 11.78-11.88 (m, 1H). MS (ESI$^+$) m/z 410.1 (M+H)$^+$.

EXAMPLE 115 tert-butyl (2-{3-[4-(5-fluoro-2-methoxyphenyl)-1H-pyrrolo[2,3-b]pyridin-2-yl]pyrrolidin-1-yl}ethyl)carbamate The title compound was prepared as the trifluoroacetate salt using the procedure described in Example 110, using tert-butyl(2-oxoethyl)carbamate (83 mg, 0.520 mmol) in place of tetrahydro-4H-pyran-4-one. $^1$H NMR (400 MHz, DMSO-d$_6$) δ 1.35-1.42 (m, 9H), 2.01-2.28 (m, 1H), 3.25-3.32 (m, 5H), 3.73 (s, 3H), 3.75-4.34 (m, 4H), 6.18-6.25 (m, 1H), 7.05-7.11 (m, 2H), 7.16-7.25 (m, 2H), 7.29 (td, J=8.6, 3.1 Hz, 1H), 8.21 (dd, J=5.0, 1.8 Hz, 1H), 9.72-9.94 (m, 1H), 11.76-11.88 (m, 1H). MS (ESI$^+$) m/z 455.0 (M+H)$^+$.

EXAMPLE 116 tert-butyl 3-[4-(5-fluoro-2-methoxyphenyl)-1H-pyrrolo[2,3-b]pyridin-2-yl]-1,3'-bipyrrolidine-1'-carboxylate The title compound was prepared as the trifluoroacetate salt using the procedure described in Example 110, using tert-butyl 3-oxopyrrolidine-1-carboxylate (48.2 mg, 0.260 mmol) in place of tetrahydro-4H-pyran-4-one. $^1$H NMR (400 MHz, DMSO-d$_6$) δ 1.32-1.44 (m, 9H), 1.66-2.46 (m, 4H), 2.39-2.65 (m, 2H), 3.20-3.32 (m, 3H), 3.64-3.85 (m, 4H), 3.86-4.04 (m, 4H), 6.25 (s, 1H), 7.08 (d, J=4.9 Hz, 1H), 7.17-7.25 (m, 2H), 7.24-7.33 (m, 1H), 8.21 (d, J=4.9 Hz, 1H), 10.31 (d, J=48.4 Hz, 1H), 11.75-11.88 (m, 1H). MS (ESI$^+$) m/z 481.0 (M+H)$^+$.

EXAMPLE 117

4-(5-fluoro-2-methoxyphenyl)-2-[1-(tetrahydro-2H-pyran-4-ylmethyl)pyrrolidin-3-yl]-1H-pyrrolo[2,3-b]pyridine The title compound was prepared as the trifluoroacetate salt using the procedure described in Example 110, using tetrahydro-2H-pyran-4-carbaldehyde (29.7 mg, 0.260 mmol) in place of tetrahydro-4H-pyran-4-one. $^1$H NMR (400 MHz, DMSO-d$_6$) δ 1.10-1.34 (m, 2H), 1.34-1.81 (m, 2H), 1.86-2.35 (m, 2H), 2.37-2.60 (m, 1H), 3.15 (t, J=6.1 Hz, 2H), 3.27 (t, J=11.1, 9.2 Hz, 4H), 3.74 (s, 3H), 3.83-3.93 (m, 2H), 3.96-4.08 (m, 1H), 6.20-6.27 (m, 1H), 7.09 (d, J=5.0 Hz, 1H), 7.17-7.26 (m, 2H), 7.25-7.33 (m, 1H), 8.22 (d, J=5.0 Hz, 1H), 9.63-9.84 (m, 1H), 11.81-11.92 (m, 1H). MS (ESI$^+$) m/z 410.1 (M+H)$^+$.

EXAMPLE 118

4-(5-fluoro-2-methoxyphenyl)-2-{1-[2-(morpholin-4-yl)ethyl]pyrrolidin-3-yl}-1H-pyrrolo[2,3-b]pyridine The title compound was prepared as the trifluoroacetate salt using the procedure described in Example 110, using 2-morpholinoacetaldehyde hydrochloride hydrate (47.8 mg, 0.260 mmol) in place of tetrahydro-4H-pyran-4-one. $^1$H NMR (400 MHz, DMSO-d$_6$) δ 2.13-2.26 (m, 1H), 2.45-2.57 (m, 1H), 2.64-3.39 (m, 8H), 3.73 (s, 3H), 3.77-3.92 (m, 4H), 6.21 (s, 1H), 7.09 (d, J=4.9 Hz, 1H), 7.17-7.24 (m, 2H), 7.29 (td, J=8.6, 3.1 Hz, 1H), 8.22 (d, J=4.9 Hz, 1H), 11.77-11.93 (m, 1H). MS (ESI$^+$) m/z 425.0 (M+H)$^+$.

EXAMPLE 119

4-(5-fluoro-2-methoxyphenyl)-2-[1-(methylsulfonyl)-1,2,3,6-tetrahydropyridin-4-yl]-1H-pyrrolo[2,3-b]pyridine To a solution of Example 87D (35.0 mg, 0.088 mmol) in N,N-dimethylformamide (0.8 mL) was added methanesulfonyl chloride (0.011 mL, 0.141 mmol) and triethylamine (0.074 mL, 0.530 mmol). The mixture was stirred for 3 hours and treated with water. The solids were filtered, washed with water, and oven-dried to afford the title compound. $^1$H NMR (400 MHz, DMSO-d$_6$) δ 2.65-2.58 (m, 2H), 2.94 (s, 3H), 3.37 (t, J=5.7 Hz, 2H), 3.74 (s, 3H), 3.94-3.88 (m, 2H), 6.28 (d, J=2.0 Hz, 1H), 6.56-6.51 (m, 1H), 7.04 (d, J=4.9 Hz, 1H), 7.32-7.16 (m, 3H), 8.21 (d, J=4.9 Hz, 1H), 11.89-11.84 (m, 1H). MS (ESI$^+$) m/z 402.1 (M+H)$^+$.

EXAMPLE 120 methyl 4-({trans-4-[4-(5-fluoro-2-methoxyphenyl)-1H-pyrrolo[2,3-b]pyridin-2-yl]cyclohexyl}amino)butanoate Example 74 (50.5 mg, 0.15 mmol), 4-oxobutanoic acid methyl ester (17.6 mg, 0.15 mmol and acetic acid (0.08 mL, 1.4 mmol) were stirred in 2 mL methanol for 1 hour and sodium cyanoborohydride was added (15.9 mg, 0.25 mmol). The mixture was stirred at room temperature for 24 hours and was concentrated. The residue was purified by RP-HPLC using a gradient of 10:90 to 50:50 acetonitrile/0.1% trifluoroacetic acid in water to afford the title compound. $^1$H NMR (400 MHz, DMSO-d$_6$) δ 1.51 (m, 4H), 1.85 (m, 2H), 2.14 (m, 4H), 2.47 (t, 2H), 2.73 (m, 1H), 3.02 (m, 3H), 3.62 (s, 3H), 3.73 (s, 3H), 6.01 (s, 1H), 7.08 (d, 1H), 7.22 (m, 3H), 8.18 (d, 1H), 11.75 (br s, 1H). (ESI) m/e 440.1 (M+H)$^+$.

EXAMPLE 121 ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate The title compound was prepared using the procedure described in Example 120 using ethyl 2-formyl-1-cyclopropanecarboxylate in place of 4-oxobutanoic acid methyl ester. $^1$H NMR (400 MHz, DMSO-d$_6$) δ 1.07 (m, 2H), 1.20 (t, 3H), 1.53 (m, 5H), 1.79 (m, 1H), 2.14 (m, 4H), 2.75 (m, 1H), 2.99 (m, 3H), 3.73 (s, 3H), 4.09 (m, 2H), 6.02 (s, 1H), 7.08 (d, 1H), 7.22 (m, 3H), 8.18 (br d, 1H), 11.70 (br s, 1H). (ESI) m/e 466.1 (M+H)$^+$.

EXAMPLE 122 trans-4-[4-(5-fluoro-2-methoxyphenyl)-1H-pyrrolo [2,3-b]pyridin-2-yl]-N-[2-(morpholin-4-yl)ethyl] cyclohexanamine The title compound was prepared using the procedure described in Example 120 using morpholin-4-yl-acetaldehyde monohydrate hydrochloride in place of 4-oxobutanoic acid methyl ester. $^1$H NMR (400 MHz, DMSO-d$_6$) δ 1.54 (m, 4H), 2.16 (m, 4H), 2.75 (m, 1H), 3.22 (m, 12H), 3.73 (s, 3H), 3.80 (m, 1H), 6.00 (s, 1H), 7.05 (d, 1H), 7.25 (m, 3H), 8.16 (d, 1H), 11.69 (br s, 1H). (ESI) m/e 453.1 (M+H)$^+$.

EXAMPLE 123

3-({trans-4-[4-(5-fluoro-2-methoxyphenyl)-1H-pyrrolo[2,3-b]pyridin-2-yl]cyclohexyl}amino)propane-1,2-diol The title compound was prepared using the procedure described in Example 120 using DL-glyceraldehyde in place of 4-oxobutanoic acid methyl ester. $^1$H NMR (400 MHz, DMSO-d$_6$) δ 1.53 (m, 4H), 2.15 (m, 4H), 2.71 (m, 1H), 2.87 (m, 1H), 3.11 (m, 2H), 3.36 (m, 1H), 3.47 (m, 2H), 3.73 (s, 3H), 6.00 (s, 1H), 7.06 (d, 1H), 7.22 (m, 3H), 8.17 (d, 1H), 11.72 (br s, 1H). (ESI) m/e 414.1 (M+H)$^+$.

EXAMPLE 124

2-{3-[4-(5-fluoro-2-methoxyphenyl)-1H-pyrrolo[2,3-b]pyridin-2-yl]pyrrolidin-1-yl}ethanamine The title compound was prepared as the trifluoroacetate salt using the procedure described in Example 109B, using Example 115 (0.025 mL, 0.260 mmol) in place of Example 109A. $^1$H NMR (300 MHz, DMSO-d$_6$) δ 1.44-2.36 (m, 2H), 3.07-3.67 (m, 9H), 3.73 (s, 1H), 6.21 (s, 1H), 7.07 (d, J=5.0 Hz, 1H), 7.15-7.33 (m, 3H), 8.00 (bs, 3H), 8.21 (d, J=4.9 Hz, 1H), 10.19 (bs, 1H), 11.69-11.86 (m, 1H). MS (ESI$^+$) m/z 355.0 (M+H)$^+$.

EXAMPLE 125

3-[4-(5-fluoro-2-methoxyphenyl)-1H-pyrrolo[2,3-b] pyridin-2-yl]-1,3'-bipyrrolidine The title compound was prepared as the trifluoroacetate salt using the procedure described in Example 109B, using Example 116 (0.025 mL, 0.260 mmol) in place of Example 109A. $^1$H NMR (300 MHz, DMSO-d$_6$) δ 2.03-2.41 (m, 2H), 3.17-3.43 (m, 8H), 3.73 (s, 3H), 6.21 (s, 1H), 7.07 (d, J=4.9 Hz, 1H), 7.16-7.34 (m, 3H), 8.21 (d, J=4.9 Hz, 1H), 8.93-9.19 (m, 2H), 11.76-11.82 (m, 1H). MS (ESI$^+$) m/z 381.1 (M+H)$^+$.

EXAMPLE 126

4-[4-(5-fluoro-2-methoxyphenyl)-1H-pyrrolo[2,3-b] pyridin-2-yl]piperidin-4-ol

EXAMPLE 126A tert-butyl 4-(4-chloro-1-tosyl-1H-pyrrolo[2,3-b]pyridin-2-yl)-4-hydroxypiperidine-1-carboxylate To a solution of 4-chloro-2-iodo-1-tosyl-1H-pyrrolo[2,3-b]pyridine (200 mg, 0.462 mmol) in tetrahydrofuran (1.5 mL) at −78° C. was added 1.6 M n-butyllithium in hexanes (0.347 mL, 0.555 mmol) under nitrogen. The mixture was stirred for 10 minutes and tert-butyl 4-oxopiperidine-1-carboxylate (111 mg, 0.555 mmol) was added. The mixture was stirred at −78° C. for 1 hour and was slowly warmed to room temperature overnight. The mixture was quenched with water, extracted with ethyl acetate (2×5 mL) and the organic layer was dried over magnesium sulfate, filtered, and concentrated. Purification by flash chromatography (silica gel, 20-100% ethyl acetate/heptanes) afforded the title compound. MS (ESI$^+$) m/z 506.0 (M+H)$^+$.

EXAMPLE 126B tert-butyl 4-(4-(5-fluoro-2-methoxyphenyl)-1-tosyl-1H-pyrrolo[2,3-b]pyridin-2-yl)-4-hydroxypiperidine-1-carboxylate A suspension of potassium phosphate (154 mg, 0.723 mmol), phenylallylchloro[1,3-bis(diisopropylphenyl)-2-imidazol-2-ylidene]palladium(II) (15.61 mg, 0.024 mmol), Example 126A (122 mg, 0.241 mmol) and (5-fluoro-2-methoxyphenyl)boronic acid (53.3 mg, 0.313 mmol) in tetrahydrofuran (1.5 mL) was heated under nitrogen at 60° C. for 150 minutes. The mixture was diluted with ethyl acetate, the water layer was separated and the organic layer was dried over magnesium sulfate, filtered and concentrated. The crude product was used in the next step without further purification. LCMS: 596.2 (M+H)$^+$.

EXAMPLE 126C tert-butyl 4-(4-(5-fluoro-2-methoxyphenyl)-1H-pyrrolo[2,3-b]pyridin-2-yl)-4-hydroxypiperidine-1-carboxylate A suspension of Example 126B (0.144 g, 0.241 mmol) and 50% sodium hydroxide (0.064 mL, 1.205 mmol)/water (0.064 mL) in dioxane (1 mL) was heated at 80° C. for 4 hours. The mixture was diluted with ethyl acetate and dried over magnesium sulfate, filtered and concentrated. The crude mixture was used in the next step without further purification. LCMS: 442.2 (M+H)$^+$.

EXAMPLE 126D

4-[4-(5-fluoro-2-methoxyphenyl)-1H-pyrrolo[2,3-b] pyridin-2-yl]piperidin-4-ol

The title compound was prepared as the trifluoroacetate salt using the procedure described in Example 109B, using Example 126C (0.025 mL, 0.260 mmol) in place of Example 109A. $^1$H NMR (300 MHz, DMSO-d$_6$) δ 1.59-1.77 (m, 2H), 1.85-2.05 (m, 2H), 2.95-3.13 (m, 2H), 3.13-3.40 (m, 2H), 3.73 (s, 3H), 3.99-4.13 (m, 1H), 7.05 (d, J=2.1 Hz, 1H), 7.13

(d, J=4.8 Hz, 1H), 7.20-7.37 (m, 3H), 8.17-8.32 (m, 1H), 8.33-8.39 (m, 1H), 8.41-8.56 (m, 2H), 12.16-12.22 (m, 1H). MS (ESI$^+$) m/z 369.2 (M+H)$^+$.

EXAMPLE 127 benzyl (3-{3-[4-(5-fluoro-2-methoxyphenyl)-1H-pyrrolo[2,3-b]pyridin-2-yl]piperidin-1-yl}propyl)carbamate A solution of benzyl (3-oxopropyl)carbamate (153 mg, 0.738 mmol), Example 1H (80 mg, 0.246 mmol) and sodium triacetoxyborohydride (78 mg, 0.369 mmol) in dichloromethane (3 mL) was stirred overnight and the mixture was quenched with 5% aqueous sodium hydroxide (15 mL). The mixture was extracted with dichloromethane and the organic layer was dried over sodium sulfate, filtered, and concentrated. The residue was dissolved in a mixture of dimethylsulfoxide and methanol and loaded onto a C18 column, eluting with 40-80% acetonitrile in 0.1% trifluoroacetic acid/water to afford the title compound. LCMS: 517.24 (M+H)$^+$. $^1$H NMR (400 MHz, DMSO-d$_6$) δ 1.61 (m, 1 H) 1.75-1.92 (m, 3 H) 1.98 (d, 1 H) 2.16 (d, 1 H) 2.80-2.95 (m, 1 H) 3.01-3.17 (m, 5 H) 3.18-3.29 (m, 2 H) 3.41 (t, 2 H) 3.73 (s, 3 H) 5.02 (s, 2 H) 6.11 (d, 1 H) 7.09 (d, 1 H) 7.17-7.24 (m, 2 H) 7.25-7.43 (m, 7 H) 8.22 (d, 1 H) 9.51 (s, 1 H) 11.84 (s, 1 H).

EXAMPLE 128

2-{3-[4-(5-fluoro-2-methoxyphenyl)-1H-pyrrolo[2,3-b]pyridin-2-yl]piperidin-1-yl}ethanol

EXAMPLE 128A 2-(1-(2-(tert-butyldimethylsilyloxy)ethyl)piperidin-3-yl)-4-(5-fluoro-2-methoxyphenyl)-1H-pyrrolo[2,3-b]pyridine The title compound was prepared by using the procedure described in Example 127, using 2-((tert-butyldimethylsilyl)oxy)acetaldehyde (86 mg, 0.49 mmol) in place of benzyl (3-oxopropyl)carbamate.

EXAMPLE 128B 2-(3-(4-(5-fluoro-2-methoxyphenyl)-1H-pyrrolo[2,3-b]pyridin-2-yl)piperidin-1-yl)ethanol A solution of Example 128A (80 mg, 0.16 mmol)) in dichloromethane (2 mL) and methanol (2 mL) was treated with 37% hydrochloric acid (0.1 mL) for 10 minutes and concentrated. The residue was purified by reverse phase HPLC, and was eluted with 10-70% acetonitrile in 0.1% trifluoroacetic acid/water to afford the title compound. LCMS: 370.20 (M+H)$^+$. $^1$H NMR (400 MHz, DMSO-d$_6$) δ 1.56-1.69 (m, 1 H) 1.83-2.01 (m, 2 H) 2.16 (d, 1 H) 2.85-2.99 (m, 1 H) 3.14-3.23 (m, 3 H) 3.26-3.40 (m, 2 H) 3.74 (s, 3 H) 3.75-3.80 (m, 2 H) 6.11 (d, 1 H) 7.09 (d, 1 H) 7.18-7.24 (m, 2 H) 7.25-7.32 (m, 1 H) 8.22 (d, 1 H) 9.55 (s, 1 H) 11.88 (s, 1 H).

EXAMPLE 129

3-{3-[4-(5-fluoro-2-methoxyphenyl)-1H-pyrrolo[2,3-b]pyridin-2-yl]piperidin-1-yl}propan-1-amine To a solution of Example 127 (100 mg, 0.194 mmol) in tetrahydrofuran (20 mL) and methanol (10 mL) was added 20% palladium hydroxide on carbon (wet, 20 mg, 0.015 mmol). The mixture was heated under 50 psi hydrogen at 45° C. for 3 hours and cooled. The insoluble material was filtered off and the filtrate was concentrated. The residue was purified by reverse phase HPLC, and was eluted with 10-70% acetonitrile in 0.1% trifluoroacetic acid/water to afford the title compound. LCMS: 383.23 (M+H)$^+$. $^1$H NMR (400 MHz, DMSO-d$_6$) δ 1.58-1.74 (m, 3 H) 1.82-1.93 (m, 1 H) 1.95-2.07 (m, 2 H) 2.18 (d, 1 H) 2.81-2.97 (m, 4 H) 3.14-3.23 (m, 2 H) 3.48 (t, 2 H) 3.74 (s, 3 H) 6.10 (s, 1 H) 7.08 (d, 1 H) 7.17-7.23 (m, 2 H) 7.25-7.34 (m, 1 H) 8.22 (d, 1 H) 10.17 (s, 1 H) 11.88 (s, 1 H).

EXAMPLE 130

4-(5-fluoro-2-methoxyphenyl)-2-[1-(2-methoxyethyl)piperidin-3-yl]-1H-pyrrolo[2,3-b]pyridine The title compound was prepared using the procedure described in Example 127, using 2-methoxyacetaldehyde (27.3 mg, 0.37 mmol) in place of benzyl (3-oxopropyl)carbamate. LCMS: 384.21 (M+H)$^+$. $^1$H NMR (400 MHz, DMSO-d$_6$) δ 1.55-1.68 (m, 1 H) 1.80-1.99 (m, 2 H) 2.15 (d, 1 H) 2.84-3.00 (m, 1 H) 3.10-3.22 (m, 2 H) 3.25-3.31 (m, 2 H) 3.32 (s, 3 H) 3.41-3.60 (m, 2 H) 3.66-3.73 (m, 2 H) 3.74 (s, 3 H) 6.11 (d, 1 H) 7.10 (d, 1 H) 7.18-7.23 (m, 2 H) 7.26-7.32 (m, 1 H) 8.23 (d, 1 H) 9.67 (s, 1 H) 11.91 (s, 1 H).

EXAMPLE 131

4-({trans-4-[4-(5-fluoro-2-methoxyphenyl)-1H-pyrrolo[2,3-b]pyridin-2-yl]cyclohexyl}amino)butanoic acid Example 120 (31.4 mg, 0.07 mmol) and 1 mL 0.8 M lithium hydroxide were stirred in 2 mL tetrahydrofuran for 24 hours. The mixture was acidified to pH 2 with 2M hydrochloric acid, concentrated and purified by reverse phase HPLC using a gradient of 10:90 to 40:60 acetonitrile/0.1% trifluoroacetic acid in water to afford the title compound. $^1$H NMR (400 MHz, DMSO-d$_6$) δ 11.78 (s, 1H), 8.18 (d, 1H), 7.26 (m, 3H), 7.08 (d, 1H), 6.02 (s, 1H), 3.74 (s, 3H), 3.02 (m, 3H), 2.73 (m, 1H), 2.37 (t, 2H), 2.15 (m, 4H), 1.82 (m, 2H), 1.51 (m, 4H). (ESI) m/e 426.1 (M+H)$^+$.

EXAMPLE 132

5-chloro-6-[2-(1-methylpiperidin-4-yl)-1H-pyrrolo[2,3-b]pyridin-4-yl]pyridin-2-amine

EXAMPLE 132A 4-chloro-2-(1-methylpiperidin-4-yl)-1H-pyrrolo[2,3-b]pyridine

To a solution of Example 17E (200 mg, 0.6 mmol) in dichloromethane (10 mL) was added 0.5 mL trifluoroacetic acid and the mixture was stirred at room temperature for 2 hours. The mixture was concentrated, dissolved in dichloromethane (20 mL), washed with sodium bicarbonate solution and concentrated. The residue was dissolved in methanol (2 mL) and treated with formaldehyde (120 mg, 37% in water) and sodium cyanoborohydride (57 mg, 0.9 mmol). The mixture was stirred at room temperature for 2 hours, diluted with dichloromethane and the organic phase was washed with water and concentrated to afford the title compound. LCMS: 250 (M+H)+.

EXAMPLE 132B 2-(1-methylpiperidin-4-yl)-4-(4,4,5,5-tetramethyl-1,3,2-dioxaborolan-2-yl)-1H-pyrrolo[2,3-b]pyridine The title compound was prepared using the procedure described in Example 5A, using Example 132A (1.0 g, 4.0 mmol) in place of Example 1F. LCMS: 342 (M+H)+.

EXAMPLE 132C 5-chloro-6-(2-(1-methylpiperidin-4-yl)-1H-pyrrolo[2,3-b]pyridin-4-yl)pyridin-2-amine The title compound was prepared using the procedure described in Example 5B, using Example 132B (100 mg, 0.3 mmol) in place of Example 5A and Example 106A (94 mg, 0.45 mmol in place of 6-bromo-5-methoxypyridin-2-amine. $^1$H NMR (400 MHz, DMSO-$d_6$): δ 1.82 (t, J=13.05 Hz, 2 H), 2.20-2.33 (m, 2 H), 2.81 (d, J=4.75 Hz, 3 H), 2.91-3.19 (m, 3 H), 3.45-3.60 (m, 2 H), 6.04 (d, J=1.36 Hz, 1 H), 6.59 (d, J=8.82 Hz, 1 H), 7.08 (d, J=5.09 Hz, 1 H), 7.61 (d, J=8.82 Hz, 1 H), 8.22 (d, J=4.75 Hz, 1 H). LCMS: 342 (M+H)+.

EXAMPLE 133

3-chloro-N$^2$-{5-chloro-6-[2-(1-methylpiperidin-4-yl)-1H-pyrrolo[2,3-b]pyridin-4-yl]pyridin-2-yl}pyridine-2,6-diamine The title compound was obtained as a byproduct from the procedure described in Example 132C. $^1$H NMR (400 MHz, DMSO-$d_6$): δ 2.22-2.39 (m, 2 H), 2.80 (d, J=4.41 Hz, 3 H), 2.94-3.19 (m, 3 H), 3.51 (d, J=5.76 Hz, 2 H), 3.81-3.91 (m, 2 H), 6.06 (d, J=1.36 Hz, 1 H), 6.11 (d, J=8.48 Hz, 1 H), 7.17 (d, J=5.09 Hz, 1 H), 7.43 (d, J=8.82 Hz, 1 H), 7.92 (d, J=8.82 Hz, 1 H), 8.25 (d, J=4.75 Hz, 1 H), 8.31 (d, J=8.82 Hz, 1 H). LCMS: 469 (M+H)+.

EXAMPLE 134

5-chloro-6-[2-(1-methylpiperidin-4-yl)-1H-pyrrolo[2,3-b]pyridin-4-yl]-N-(tetrahydro-2H-pyran-4-ylmethyl)pyridin-2-amine The title compound was prepared using the procedure described in Example 11B, using Example 132 (20 mg, 0.06 mmol) in place of Example 11A and tetrahydro-2H-pyran-4-carbaldehyde (10 mg, 0.09 mmol) in place of benzaldehyde. $^1$H NMR (400 MHz, DMSO-$d_6$): δ 1.11-1.30 (m, 4 H), 1.61 (d, J=12.82 Hz, 2 H), 1.72-1.89 (m, 2 H), 2.29 (d, J=13.43 Hz, 2 H), 2.81 (d, J=3.36 Hz, 3 H), 3.06-3.17 (m, 4 H), 3.21-3.31 (m, 2 H), 3.54 (d, J=11.90 Hz, 2 H), 3.84 (dd, J=11.14, 2.90 Hz, 2 H), 6.10 (d, J=1.22 Hz, 1 H), 6.60 (d, J=8.85 Hz, 1 H), 7.14 (d, J=4.88 Hz, 1 H), 7.55 (d, J=8.85 Hz, 1 H), 8.22 (d, J=5.19 Hz, 1 H). LCMS: 440 (M+H)+.

EXAMPLE 135

1-{4-[4-(5-fluoro-2-methoxyphenyl)-1H-pyrrolo[2,3-b]pyridin-2-yl]piperidin-1-yl}ethanone

EXAMPLE 135A tert-butyl 4-(4-(5-fluoro-2-methoxyphenyl)-1H-pyrrolo[2,3-b]pyridin-2-yl)piperidine-1-carboxylate A solution of Example 87C (2.35 g, 4.17 mmol) in ethanol (40 mL) was added to 20% palladium hydroxide on carbon (wet, 2.35 g, 1.707 mmol) in a stainless steel pressure bottle and was stirred at 50° C. for several days at 50 psi hydrogen. The mixture was filtered through a nylon membrane and concentrated. The residue was dissolved in 30 mL 1,4-dioxane and treated with 2 mL 20% sodium hydroxide. The mixture was heated at 90° C. for 4 hours and was concentrated. The residue was treated with water and extracted with ethyl acetate (twice). The combined organic layers were dried over magnesium sulfate, filtered, concentrated, and purified using an ISCO Companion flash system on silica eluting with dichloromethane/ethyl acetate (5:5 to 4:6) to afford the title compound. MS (ESI+) m/z 425.9 (M+H)+.

EXAMPLE 135B 4-(5-fluoro-2-methoxyphenyl)-2-(piperidin-4-yl)-1H-pyrrolo[2,3-b]pyridine A solution of Example 135A (0.955 g, 2.24 mmol) in dichloromethane (20 mL) was treated with trifluoroacetic acid (1.73 mL, 22.4 mmol) and the mixture was stirred for 3 hours. After concentration, the residue was dissolved in 10 mL methanol and treated with 30 mL 1M hydrogen chloride in ether. After stirring for 15 minutes, the mixture was treated with ether and the solids were filtered, washed with ether and oven-dried to afford the title compound as a hydrochloride salt. MS (ESI+) m/z 326.1 (M+H)+.

EXAMPLE 135C

1-{4-[4-(5-fluoro-2-methoxyphenyl)-1H-pyrrolo[2,3-b]pyridin-2-yl]piperidin-1-yl}ethanone A mixture of Example 135B (50 mg, 0.126 mmol), (benzotriazol-1-yl-oxytripyrrolidinophosphonium hexafluorophosphate) (78 mg, 0.151 mmol), triethylamine (0.07 mL, 0.502 mmol), and acetic acid (8.62 µL, 0.151 mmol) in tetrahydrofuran (2 mL) was stirred for 5 hours. The mixture was quenched with water and brine and extracted with ethyl acetate (twice). The combined organic layers were diluted with ethyl acetate, washed with brine, dried over magnesium sulfate, filtered, concentrated and purified using an ISCO Companion flash system on silica eluting with methanol/ethyl acetate (gradient of 5:95 to 10:90) to afford the title compound. $^1$H NMR (500 MHz, CD$_3$OD) δ 1.65 (qd, J=12.5, 4.3 Hz, 2H), 2.05-2.16 (m, 5H), 2.79 (td, J=12.9, 2.9 Hz, 1H), 3.02-3.18 (m, 1H), 3.23.3.27 (m, 1H), 3.75 (s, 3H), 3.99-4.06 (m, 1H), 4.52-4.66 (m, 1H), 6.07 (d, J=0.8 Hz, 1H), 7.08 (d, J=5.0 Hz, 1H), 7.09-7.18 (m, 3H), 8.11 (d, J=5.0 Hz, 1H). MS (ESI+) m/z 368.1 (M+H)+.

EXAMPLE 136

1-{4-[4-(5-fluoro-2-methoxyphenyl)-1H-pyrrolo[2,3-b]pyridin-2-yl]piperidin-1-yl}-2-hydroxyethanone The title compound was prepared as described in Example 135C, using 2-hydroxyacetic acid (0.196 mmol, 70% in water, 14.89 mg) in place of acetic acid. Purification by reverse-phase HPLC on a Zorbax RX-C18 column using a gradient of 15% to 100% methanol/0.1% aqueous trifluoroacetic acid afforded the title compound as a trifluoroacetic acid salt. $^1$H NMR (400 MHz, CD$_3$OD) δ 1.61-1.84 (m, 2H), 2.09-2.18 (m, 2H), 2.82-2.93 (m, 1H), 3.11-3.25 (m, 2H), 3.80 (s, 3H), 3.83-3.92 (m, 1H), 4.26 (d, J=5.7 Hz, 2H), 4.57-4.66 (m, 1H), 6.37 (d, J=0.8 Hz, 1H), 7.18-7.31 (m, 3H), 7.47 (d, J=5.9 Hz, 1H), 8.26 (d, J=5.9 Hz, 1H). MS (ESI$^+$) m/z 384.1 (M+H)$^+$.

EXAMPLE 137

3-methoxy-4-[2-(piperidin-3-yl)-1H-pyrrolo[2,3-b]pyridin-4-yl]benzonitrile

EXAMPLE 137A tert-butyl 3-(4-(4-cyano-2-methoxyphenyl)-1H-pyrrolo[2,3-b]pyridin-2-yl)piperidine-1-carboxylate A mixture of Example 1F (100 mg, 0.298 mmol), 4-cyano-2-methoxyphenylboronic acid (86 mg, 0.447 mmol), bis(triphenylphosphine)palladium chloride (12.54 mg, 0.018 mmol), tricyclohexylphosphine (5.01 mg, 0.018 mmol) and cesium carbonate (291 mg, 0.893 mmol) in dioxane (3 mL) was heated at 110° C. for 24 hours. Additional tricyclohexylphosphine (5.01 mg, 0.018 mmol), bis(triphenylphosphine)palladium chloride (12.54 mg, 0.018 mmol) and 4-cyano-2-methoxyphenylboronic acid (60 mg) were added and the mixture was heated at 120° C. for 24 hours and cooled. Insoluble material was filtered off and the filtrate was concentrated. The residue was purified by flash chromatography, and was eluted with 0-100% ethyl acetate in heptanes to afford the title compound.

EXAMPLE 137B 3-methoxy-4-(2-(piperidin-3-yl)-1H-pyrrolo[2,3-b]pyridin-4-yl)benzonitrile A solution of Example 137A (75 mg, 0.17 mmol) in dichloromethane (3 mL) was treated with trifluoroacetic acid (1 mL) for 10 minutes and was concentrated. The residue was purified by reverse phase HPLC, eluted with 10-70% acetonitrile in 0.1% trifluoroacetic acid/water to afford the title compound. LCMS: 333.11 (M+H)$^+$. $^1$H NMR (400 MHz, DMSO-d$_6$) δ 1.63-1.80 (m, 2 H) 1.88 (d, 1 H) 2.11 (d, 1 H) 2.77-2.89 (m, 1 H) 3.02-3.12 (m, 1 H) 3.14-3.22 (m, 1 H) 3.29 (d, 1 H) 3.81 (s, 3 H) 6.05 (d, 1 H) 7.07 (d, 1 H) 7.54 (s, 2 H) 7.67 (s, 1 H) 8.21 (d, 1 H) 8.70 (d, 1 H) 8.87 (s, 1 H) 11.83 (s, 1 H).

EXAMPLE 138

N-(2-phenylethyl)-6-[2-(piperidin-4-yl)-1H-pyrrolo[2,3-b]pyridin-4-yl]pyridin-2-amine The title compound was prepared using the procedure described in Example 88C, using 2-phenylethanamine (54 mg, 0.44 mmol) in place of (tetrahydro-2H-pyran-4-yl)methanamine. $^1$H NMR (400 MHz, DMSO-d$_6$): δ 1.73-1.88 (m, 2 H), 2.21 (d, J=14.92 Hz, 2 H), 2.87-2.97 (m, 2 H), 3.00-3.12 (m, 3 H), 3.15 (d, J=9.16 Hz, 2 H), 3.58-3.65 (m, 2 H), 6.57 (d, J=8.14 Hz, 1 H), 6.80 (d, J=1.02 Hz, 1 H), 7.19 (d, J=7.12 Hz, 2 H), 7.26-7.31 (m, 5 H), 7.30-7.34 (m, 1 H), 7.52 (d, J=5.09 Hz, 1 H). LCMS: 398 (M+H)$^+$.

EXAMPLE 139

N-methyl-6-[2-(1-methylpiperidin-4-yl)-1H-pyrrolo[2,3-b]pyridin-4-yl]-N-(2-phenylethyl)pyridin-2-amine The title compound was obtained as a byproduct from Example 150. $^1$H NMR (400 MHz, DMSO-d$_6$): δ 1.74-1.92 (m, 2 H), 2.28 (d, J=13.22 Hz, 2 H), 2.82 (d, J=4.75 Hz, 3 H), 2.85-2.95 (m, 2 H), 2.96-3.03 (m, 1 H), 3.06 (s, 3 H), 3.11 (d, J=12.89 Hz, 2 H), 3.53 (d, J=11.87 Hz, 2 H), 3.78-3.90 (m, 2 H), 6.74 (d, J=8.48 Hz, 1 H), 6.80 (d, J=1.36 Hz, 1 H), 7.17-7.24 (m, 1 H), 7.24-7.31 (m, 5 H), 7.59 (d, J=5.43 Hz, 1 H), 7.64-7.73 (m, 1 H), 8.28 (d, J=5.43 Hz, 1 H). LCMS: 426 (M+H)$^+$.

EXAMPLE 140

N-(2-chlorobenzyl)-6-[2-(piperidin-4-yl)-1H-pyrrolo[2,3-b]pyridin-4-yl]pyridin-2-amine The title compound was prepared using the procedure described in Example 88C, using (2-chlorophenyl)methanamine (50 mg, 0.35 mmol) in place of (tetrahydro-2H-pyran-4-yl)methanamine. $^1$H NMR (400 MHz, DMSO-d$_6$): δ1.48-1.83 (m, 2 H), 2.12 (d, J=12.89 Hz, 2 H), 2.88-3.12 (m, 3 H), 3.36 (d, J=12.89 Hz, 2 H), 4.71 (s, 2 H), 6.57 (d, J=1.36 Hz, 1 H), 6.70 (d, J=8.48 Hz, 1 H), 7.22 (d, J=7.12 Hz, 1 H), 7.25-7.33 (m, 2 H), 7.41-7.54 (m, 3 H), 7.61 (t, J=7.97 Hz, 1 H), 8.21 (d, J=5.09 Hz, 1 H). LCMS: 417 (M+H)$^+$.

EXAMPLE 141

N-(2-chlorobenzyl)-6-[2-(1-methylpiperidin-4-yl)-1H-pyrrolo[2,3-b]pyridin-4-yl]pyridin-2-amine The title compound was prepared using the procedure described in Example 89, using Example 140 (20 mg, 0.05 mmol) in place of Example 88C. $^1$H NMR (400 MHz, DMSO-d$_6$): δ 1.60-1.80 (m, 2 H), 2.06-2.21 (m, 2 H), 2.83 (d, J=4.75 Hz, 3 H), 2.93-3.16 (m, 1 H), 3.36 (d, J=12.55 Hz, 2 H), 3.53 (d, J=11.87 Hz, 2 H), 4.71 (s, 2 H), 6.53 (d, J=1.36 Hz, 1 H), 6.69 (d, J=8.48 Hz, 1 H), 7.21 (d, J=7.46 Hz, 1 H), 7.28-7.33 (m, 2 H), 7.40-7.46 (m, 2 H), 7.46-7.54 (m, 1 H), 7.60 (t, J=7.80 Hz, 1 H), 8.20 (d, J=5.09 Hz, 1 H). LCMS: 432 (M+H)$^+$.

EXAMPLE 142

N-(2-chlorobenzyl)-N-methyl-6-[2-(1-methylpiperidin-4-yl)-1H-pyrrolo[2,3-b]pyridin-4-yl]pyridin-2-amine The title compound was obtained as a byproduct from Example 141. $^1$H NMR (400 MHz, DMSO-d$_6$): δ 1.51-1.77 (m, 2 H), 2.02-2.20 (m, 2 H), 2.83 (d, J=4.75 Hz, 3 H), 3.00-3.11 (m, 1 H), 3.19 (s, 3 H), 3.24-3.42 (m, 2 H), 3.52 (d, J=11.19 Hz, 2 H), 5.00 (s, 2 H), 6.50 (d, J=1.36 Hz, 1 H), 6.76 (d, J=8.48 Hz, 1 H), 7.07-7.15 (m, 1 H), 7.24-7.35 (m, 3 H), 7.44 (d, J=5.09 Hz, 1 H), 7.51-7.58 (m, 1 H), 7.67-7.77 (m, 1 H), 8.20 (d, J=5.09 Hz, 1 H). LCMS: 446 (M+H)$^+$.

EXAMPLE 143

1-[2-({6-[2-(piperidin-4-yl)-1H-pyrrolo[2,3-b]pyridin-4-yl]pyridin-2-yl}amino)ethyl]pyrrolidin-2-one The title compound was prepared using the procedure described in Example 88C, using 1-(2-aminoethyl)pyrrolidin-2-one (113 mg, 0.9 mmol) in place of (tetrahydro-2H-pyran-4-yl)methanamine. $^1$H NMR (400 MHz, DMSO-d$_6$): δ 1.79-1.98 (m, 4 H), 2.18 (t, J=7.97 Hz, 2 H), 2.27 (d, J=13.56 Hz, 2 H), 2.89-3.23 (m, 3 H), 3.29-3.49 (m, 6 H), 3.55 (t, J=6.27 Hz, 2 H), 6.62 (d, J=8.48 Hz, 1 H), 6.76 (s, 1 H), 7.21 (d, J=6.78 Hz, 1 H), 7.54 (d, J=5.09 Hz, 1 H), 7.60 (t, J=7.63 Hz, 1 H), 8.25 (d, J=5.09 Hz, 1 H). LCMS: 405 (M+H)$^+$.

EXAMPLE 144

1-[2-(methyl {6-[2-(1-methylpiperidin-4-yl)-1H-pyrrolo[2,3-b]pyridin-4-yl]pyridin-2-yl}amino)ethyl] pyrrolidin-2-one The title compound was obtained as a byproduct from Example 151. $^1$H NMR (400 MHz, DMSO-d$_6$): δ 1.62-1.73 (m, 2 H), 1.86 (dd, J=12.72, 2.54 Hz, 2 H), 2.03 (t, J=7.97 Hz, 2 H), 2.34 (d, J=13.56 Hz, 2 H), 2.83 (d, J=4.41 Hz, 3 H), 3.08 (s, 3 H), 3.10-3.21 (m, 3 H), 3.33 (t, J=6.95 Hz, 2 H), 3.42 (t, J=6.10 Hz, 2 H), 3.56 (d, J=11.87 Hz, 2 H), 3.81 (t, J=6.10 Hz, 2 H), 6.70 (d, J=8.48 Hz, 1 H), 6.75 (d, J=1.70 Hz, 1 H), 7.25 (d, J=7.12 Hz, 1 H), 7.56 (d, J=5.09 Hz, 1 H), 7.62-7.71 (m, 1 H), 8.24 (d, J=5.09 Hz, 1 H). LCMS: 433 (M+H)$^+$.

EXAMPLE 145

2-[({trans-4-[4-(5-fluoro-2-methoxyphenyl)-1H-pyrrolo[2,3-b]pyridin-2-yl]cyclohexyl}amino) methyl]cyclopropanecarboxylic acid The title compound was prepared using the procedure described in Example 131 using Example 121 in place of Example 120. $^1$H NMR (400 MHz, DMSO-d$_6$) δ 11.73 (br s, 1H), 8.18 (d, 1H), 7.25 (m, 3H), 7.08 (d, 1H), 6.01 (s, 1H), 3.97 (s, 3H), 3.05 (m, 2H), 2.95 (m, 1H), 2.73 (m, 1H), 2.14 (m, 4H), 1.66 (m, 1H), 1.03 (m, 5H), 1.08 (m, 1H), 0.97 (m, 1H). (ESI) m/e 438.1 (M+H)$^+$.

EXAMPLE 146

2-(azetidin-3-yl)-4-(5-fluoro-2-methoxyphenyl)-1H-pyrrolo[2,3-b]pyridine

EXAMPLE 146A tert-butyl 3-((2-((tert-butoxycarbonyl)amino)-4-chloropyridin-3-yl) ethynyl) azetidine-1-carboxylate The title compound was prepared using the procedure described in Example 1E, using tert-butyl-3-ethynylazetidine-1-carboxylate (2 g, 11.04 mmol) in place of Example 1D. MS (ESI$^+$) m/z 408.2 (M+H)$^+$.

EXAMPLE 146B tert-butyl 3-(4-chloro-1H-pyrrolo[2,3-b]pyridin-2-yl)azetidine-1-carboxylate The title compound was prepared using the procedure described in Example 1F, using Example 146A (2.98 g, 7.31 mmol) in place of Example 1E. MS (ESI$^+$) m/z 307.8 (M+H)$^+$.

EXAMPLE 146C tert-butyl 3-(4-(5-fluoro-2-methoxyphenyl)-1H-pyrrolo[2,3-b]pyridin-2-yl)azetidine-1-carboxylate The title compound was prepared using the procedure described in Example 94C, using Example 146B (68 mg, 0.221 mmol) in place of Example 94B. MS (ESI$^+$) m/z 397.9 (M+H)$^+$.

EXAMPLE 146D 2-(azetidin-3-yl)-4-(5-fluoro-2-methoxyphenyl)-1H-pyrrolo[2,3-b]pyridine The title compound was prepared as the trifluoroacetate salt using the procedure described in Example 94D, using Example 146C (68 mg, 0.171 mmol) in place of Example 94C. $^1$H NMR (300 MHz, DMSO-d$_6$) δ 3.73 (s, 3 H) 4.10-4.35 (m, 5 H) 6.37 (d, J=2.03 Hz, 1 H) 7.08 (d, J=4.75 Hz, 1 H) 7.15-7.36 (m, 3 H) 8.22 (d, J=5.09 Hz, 1 H) 11.80 (br. s, 1 H). MS (ESI$^+$) m/z 298.0 (M+H)$^+$.

EXAMPLE 147

1-{4-[4-(5-fluoro-2-methoxyphenyl)-1H-pyrrolo[2, 3-b]pyridin-2-yl]piperidin-1-yl}-2-(4-hydroxypiperidin-1-yl)ethanone

EXAMPLE 147A 2-chloro-1-(4-(4-(5-fluoro-2-methoxyphenyl)-1H-pyrrolo[2,3-b]pyridin-2-yl)piperidin-1-yl)ethanone The title compound was prepared as described in Example 135C, using 2-chloroacetic acid (0.241 mmol, 22.78 mg) in place of acetic acid. MS (ESI$^+$) m/z 402.2 (M+H)$^+$.

EXAMPLE 147B

1-{4-[4-(5-fluoro-2-methoxyphenyl)-1H-pyrrolo[2, 3-b]pyridin-2-yl]piperidin-1-yl}-2-(4-hydroxypiperidin-1-yl)ethanone A mixture of Example 147A (60.0 mg, 0.149 mmol), triethylamine (0.062 mL, 0.448 mmol) and piperidin-4-ol (22.65 mg, 0.224 mmol) in tetrahydrofuran (1.5 mL) was heated at 70° C. for 4 hours. The mixture was quenched with water and brine and extracted with ethyl acetate (twice). The combined organic layers were washed with brine, dried over magnesium sulfate, filtered, concentrated and purified by reverse-phase HPLC on a Zorbax RX-C18 column using a gradient of 15% to 100% methanol/0.1% aqueous trifluoroacetic acid to afford the title compound as a trifluoroacetic acid salt. $^1$H NMR (400 MHz, CD$_3$OD) δ 1.63-2.02 (m, 4H), 2.01-2.26 (m, 4H), 2.92 (td, J=13.0, 2.8 Hz, 1H), 3.03-3.26 (m, 2H), 3.35-3.51 (m, 3H), 3.60-3.70 (m, 1H), 3.81 (s, 3H), 3.82-3.90 (m, 1.5H), 4.10 (bs, 0.5H), 4.19-4.37 (m, 2H), 4.59-4.68 (m, 1H), 6.39 (s, 1H), 7.19-7.32 (m, 3H), 7.51 (d, J=6.0 Hz, 1H), 8.29 (d, J=6.0 Hz, 1H). MS (ESI$^+$) m/z 467.2 (M+H)$^+$.

EXAMPLE 148

4-(5-fluoro-2-methoxyphenyl)-2-[1-(methylsulfonyl) piperidin-4-yl]-1H-pyrrolo[2,3-b]pyridine To a solution of Example 135B (75 mg, 0.188 mmol) in N,N-dimethylformamide (1.5 mL) was added methanesulfonyl chloride (0.026 mL, 0.339 mmol) and triethylamine (0.157 mL, 1.130 mmol) and the mixture was stirred for 3 hours. The mixture was treated with water and brine and extracted with ethyl acetate (twice). The combined organic layers were dried over magnesium sulfate, filtered and concentrated. The residue was treated with ethyl acetate and ether (9:1) and sonicated. The suspension was filtered, washed with ether/ethyl acetate and oven-dried to afford the title compound. ¹H NMR (400 MHz, DMSO-d₆) δ 1.67-1.82 (m, 2H), 2.05-2.13 (m, 2H), 2.79-2.92 (m, 6H), 3.60-3.69 (m, 2H), 3.73 (s, 3H), 6.01 (d, J=2.0 Hz, 1H), 7.02 (d, J=4.9 Hz, 1H), 7.15-7.28 (m, 3H), 8.15 (d, J=4.9 Hz, 1H), 11.63 (bs, 1H). MS (ESI⁺) m/z 404.1 (M+H)⁺.

EXAMPLE 149

3-{4-[4-(5-fluoro-2-methoxyphenyl)-1H-pyrrolo[2,3-b]pyridin-2-yl]piperidin-1-yl}propane-1,2-diol To a mixture of Example 135B (60 mg, 0.151 mmol), triethylamine (0.046 mL, 0.331 mmol) and acetic acid (0.043 mL, 0.753 mmol) in dichloromethane (2.5 mL) was added 2,3-dihydroxypropanal(27.1 mg, 0.301 mmol) and MP-cyanoborohydride (2.49 mmol/g, 242 mg, 0.603 mmol) and the mixture was stirred for 5 hours. The solid material was filtered and rinsed with dichloromethane/methanol. The filtrate was concentrated and purified by reverse-phase HPLC on a Zorbax RX-C18 column using a gradient of 15% to 100% methanol/0.1% aqueous trifluoroacetic acid to afford the title compound as a trifluoroacetic acid salt. ¹H NMR (400 MHz, CD₃OD) δ ppm 1.95-2.25 (m, 2H), 2.23-2.48 (m, 2H), 3.12-3.27 (m, 4H), 3.40-3.65 (m, 3H), 3.78-3.85 (m, 5H), 3.96-4.13 (m, 1H), 6.42 (s, 1H), 7.19-7.33 (m, 3H), 7.50 (d, J=5.9 Hz, 1H), 8.31 (d, J=5.9 Hz, 1H). MS (ESI⁺) m/z 400.1 (M+H)⁺.

EXAMPLE 150

6-[2-(1-methylpiperidin-4-yl)-1H-pyrrolo[2,3-b]pyridin-4-yl]-N-(2-phenylethyl)pyridin-2-amine The title compound was prepared using the procedure described in Example 89, using Example 138 (25 mg, 0.06 mmol) in place of Example 88C. ¹H NMR (400 MHz, DMSO-d₆): δ 1.72-1.94 (m, 2 H), 2.28 (d, J=13.56 Hz, 2 H), 2.82 (d, J=4.75 Hz, 3 H), 2.90-2.96 (m, 2 H), 3.00-3.19 (m, 3 H), 3.52 (d, J=11.87 Hz, 2 H), 3.63 (t, J=7.46 Hz, 2 H), 6.63 (d, J=8.14 Hz, 1 H), 6.78 (s, 1 H), 7.17-7.25 (m, 2 H), 7.25-7.34 (m, 4 H), 7.52 (d, J=5.09 Hz, 1 H), 7.59 (t, J=7.80 Hz, 1 H), 8.25 (d, J=5.09 Hz, 1 H). LCMS: 412 (M+H)⁺.

EXAMPLE 151

1-[2-({6-[2-(1-methylpiperidin-4-yl)-1H-pyrrolo[2,3-b]pyridin-4-yl]pyridin-2-yl}amino)ethyl]pyrrolidin-2-one The title compound was prepared using the procedure described in Example 89, using Example 143 (30 mg, 0.07 mmol) in place of Example 88C. ¹H NMR (400 MHz, DMSO-d₆): δ 1.82-1.96 (m, 4 H), 2.13-2.22 (m, 4 H), 2.34 (d, J=13.73 Hz, 2 H), 2.83 (d, J=3.66 Hz, 3 H), 3.02-3.21 (m, 3 H), 3.39-3.43 (m, 2 H), 3.40-3.45 (m, 2 H), 3.56 (t, J=5.95 Hz, 2 H), 6.72 (d, J=7.93 Hz, 1 H), 6.79 (s, 1 H), 7.25 (d, J=7.32 Hz, 1 H), 7.58 (d, J=5.19 Hz, 1 H), 7.68 (t, J=7.63 Hz, 1 H), 8.31 (d, J=5.19 Hz, 1 H). LCMS: 419 (M+H)⁺.

EXAMPLE 152

5-chloro-N-(cyclopropylmethyl)-6-[2-(1-methylpiperidin-4-yl)-1H-pyrrolo[2,3-b]pyridin-4-yl]pyridin-2-amine The title compound was prepared using the procedure described in Example 11B, using Example 132 (20 mg, 0.06 mmol) in place of Example 11A and cyclopropanecarbaldehyde (10 mg, 0.09 mmol) in place of benzaldehyde. ¹H NMR (400 MHz, DMSO-d₆): δ 0.12-0.25 (m, 2 H), 0.37-0.47 (m, 2 H), 0.98-1.10 (m, 1 H), 1.73-1.88 (m, 2 H), 2.30 (d, J=13.73 Hz, 2 H), 2.81 (d, J=4.27 Hz, 3 H), 2.96-3.20 (m, 3 H), 3.09 (d, J=6.41 Hz, 2 H), 3.53 (d, J=11.60 Hz, 2 H), 6.11 (s, 1 H), 6.62 (d, J=8.85 Hz, 1 H), 7.17 (d, J=5.19 Hz, 1 H), 7.57 (d, J=8.85 Hz, 1 H), 8.23 (d, J=5.19 Hz, 1 H). LCMS: 396 (M+H)⁺.

EXAMPLE 153

N-{4-[2-(dimethylamino)ethoxy]benzyl}-6-[2-(1-methylpiperidin-4-yl)-1H-pyrrolo[2,3-b]pyridin-4-yl]pyridin-2-amine A solution of Example 90B (20 mg, 0.065 mmol) and 2-(4-(aminomethyl)phenoxy)-N,N-dimethylethanamine (88 mg, 0.45 mmol) in dimethylsulfoxide (1 mL) was heated in a sealed tube at 110° C. overnight. The mixture was diluted with dichloromethane (20 mL) and the organic phase was washed with water, concentrated and purified by HPLC (Zorbax XDB C-18 (32) using a gradient of 5-40% acetonitrile/water (containing 0.1% trifluoroacetic acid) to afford the title compound. ¹H NMR (400 MHz, DMSO-d₆): δ 1.71-1.95 (m, 2 H), 2.20-2.38 (m, 2 H), 2.83 (s, 3 H), 2.85 (s, 6 H), 2.96-3.24 (m, 3 H), 3.43-3.57 (m, 2 H), 4.22-4.35 (m, 4 H), 4.58 (s, 2 H), 6.69 (d, J=8.24 Hz, 1 H), 6.74 (s, 1 H), 6.96 (d, J=8.54 Hz, 2 H), 7.24 (d, J=7.32 Hz, 1 H), 7.35 (d, J=8.54 Hz, 2 H), 7.54 (d, J=5.19 Hz, 1 H), 7.61 (d, J=10.38 Hz, 1 H), 8.27 (d, J=5.19 Hz, 1 H). LCMS: 485 (M+H)⁺.

EXAMPLE 154

5-chloro-N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine The title compound was prepared using the procedure described in Example 11B, using Example 132 (20 mg, 0.06 mmol) in place of Example 11A and 2,2-dimethyltetrahydro-2H-pyran-4-carbaldehyde (10 mg, 0.09 mmol) in place of benzaldehyde. ¹H NMR (400 MHz, DMSO-d₆): δ 0.93-1.06 (m, 2 H), 1.11 (s, 6 H), 1.57 (dd, J=12.97, 2.90 Hz, 2 H), 1.73-1.88 (m, 2 H), 1.89-1.98 (m, 2 H), 2.30 (d, J=13.73 Hz, 2 H), 2.81 (d, J=4.27 Hz, 3 H), 2.95-3.20 (m, 4 H), 3.53 (d, J=12.21 Hz, 2 H), 3.56-3.64 (m, 2 H), 6.09 (s, 1 H), 6.61 (d, J=8.85 Hz, 1 H), 7.14 (d, J=4.88 Hz, 1 H), 7.56 (d, J=8.85 Hz, 1 H), 8.23 (d, J=4.88 Hz, 1 H). LCMS: 468 (M+H)⁺.

EXAMPLE 155

5-chloro-6-[2-(1-methylpiperidin-4-yl)-1H-pyrrolo[2,3-b]pyridin-4-yl]-N-(pyridin-4-ylmethyl)pyridin-2-amine The title compound was prepared using the procedure described in Example 11B, using Example 132 (20 mg, 0.06 mmol) in place of Example 11A and isonicotinaldehyde (10 mg, 0.09 mmol) in place of benzaldehyde. ¹H NMR (400 MHz, DMSO-d₆): δ 1.82-2.01 (m, 2 H), 2.34 (d, J=13.43 Hz, 2 H), 2.82 (s, 3 H), 3.05-3.21 (m, 3 H), 3.55 (t, J=12.82 Hz, 2 H), 4.73 (d, J=7.02 Hz, 2 H), 6.44 (s, 1 H), 6.79 (d, J=8.85 Hz, 1 H), 7.51 (d, J=5.19 Hz, 1 H), 7.69 (d, J=8.85 Hz, 1 H), 7.83 (d, J=6.41 Hz, 2 H), 8.34 (d, J=5.19 Hz, 1 H), 8.79 (d, J=6.10 Hz, 2 H). LCMS: 433 (M+H)+.

EXAMPLE 156

6-[2-(1-methylpiperidin-4-yl)-1H-pyrrolo[2,3-b]pyridin-4-yl]-N-(1H-pyrazol-3-ylmethyl)pyridin-2-amine The title compound was prepared using the procedure described in Example 153, using (1H-pyrazol-3-yl)methanamine (44 mg, 0.45 mmol) in place of 2-(4-(aminomethyl)phenoxy)-N,N-dimethylethanamine. $^1$H NMR (400 MHz, DMSO-d$_6$): δ 1.81 (d, J=10.38 Hz, 2 H), 2.29 (d, J=14.34 Hz, 2 H), 2.82 (d, J=3.97 Hz, 3 H), 2.98-3.18 (m, 3 H), 3.55 (d, J=12.21 Hz, 2 H), 4.62 (s, 2 H), 6.21 (d, J=2.14 Hz, 1 H), 6.34 (d, J=2.14 Hz, 1 H), 6.71 (d, J=8.24 Hz, 1 H), 7.21-7.25 (m, 1 H), 7.52 (d, J=5.19 Hz, 1 H), 7.59-7.62 (m, 1 H), 7.76 (d, J=2.44 Hz, 1 H), 8.25 (d, J=5.19 Hz, 1 H). LCMS: 388 (M+H)+.

EXAMPLE 157

N-(2,3-dihydro-1H-isoindol-5-ylmethyl)-6-[2-(1-methylpiperidin-4-yl)-1H-pyrrolo[2,3-b]pyridin-4-yl]pyridin-2-amine The title compound was prepared using the procedure described in Example 88C, using Example 90B (20 mg, 0.06 mmol) in place of Example 88B and using tert-butyl 5-(aminomethyl)isoindoline-2-carboxylate (112 mg, 0.45 mmol) in place of (tetrahydro-2H-pyran-4-yl)methanamine. $^1$H NMR (400 MHz, DMSO-d$_6$): δ 1.72-1.94 (m, 2 H), 2.18-2.35 (m, 2 H), 2.83 (d, J=4.41 Hz, 3 H), 2.93-3.16 (m, 3 H), 3.54 (d, J=12.21 Hz, 2 H), 4.47 (t, J=4.92 Hz, 4 H), 4.65 (s, 2 H), 6.59 (d, J=8.14 Hz, 1 H), 6.68 (d, J=1.36 Hz, 1 H), 7.20 (d, J=7.12 Hz, 1 H), 7.31-7.41 (m, 3 H), 7.47 (d, J=5.09 Hz, 1 H), 7.52-7.59 (m, 1 H), 8.20 (d, J=5.09 Hz, 1 H). LCMS: 439 (M+H)+.

EXAMPLE 158

6-[2-(1-methylpiperidin-4-yl)-1H-pyrrolo[2,3-b]pyridin-4-yl]-N-[(1-methylpyrrolidin-3-yl)methyl]pyridin-2-amine The title compound was prepared using the procedure described in Example 153, using (1-methylpyrrolidin-3-yl)methanamine (51 mg, 0.45 mmol) in place of 2-(4-(aminomethyl)phenoxy)-N,N-dimethylethanamine. $^1$H NMR (400 MHz, DMSO-d$_6$): δ 1.80-1.95 (m, 2 H), 2.03-2.20 (m, 1 H), 2.35 (d, J=12.21 Hz, 2 H), 2.54 (s, 3 H) 2.83 (d, J=4.07 Hz, 3 H), 2.85-2.95 (m, 3 H), 2.98-3.22 (m, 4 H), 3.32-3.46 (m, 2 H), 3.52-3.58 (m, 2 H), 3.93-4.05 (m, 2 H), 6.60 (d, J=3.05 Hz, 1 H), 6.63 (d, J=5.09 Hz, 1 H), 7.27 (d, J=6.10 Hz, 1 H), 7.54 (d, J=5.09 Hz, 1 H), 7.59-7.65 (m, 1 H), 8.24 (d, J=4.75 Hz, 1 H). LCMS: 405 (M+H)+.

EXAMPLE 159

N-(1H-indol-6-ylmethyl)-6-[2-(1-methylpiperidin-4-yl)-1H-pyrrolo[2,3-b]pyridin-4-yl]pyridin-2-amine The title compound was prepared using the procedure described in Example 153, using (1H-indol-6-yl)methanamine (65 mg, 0.45 mmol) in place of 2-(4-(aminomethyl)phenoxy)-N,N-dimethylethanamine. $^1$H NMR (400 MHz, DMSO-d$_6$): δ 1.69-1.83 (m, 2 H), 2.11-2.25 (m, 2 H), 2.80 (d, J=4.75 Hz, 3 H), 2.87-3.17 (m, 3 H), 3.47 (d, J=12.21 Hz, 2 H), 4.70 (s, 2 H), 6.38 (t, J=2.03 Hz, 1 H), 6.68-6.72 (m, 2 H), 7.13 (dd, J=8.31, 1.53 Hz, 1 H), 7.20 (d, J=7.12 Hz, 1 H), 7.30-7.33 (m, 1 H), 7.36 (d, J=8.48 Hz, 1 H), 7.48-7.52 (m, 1 H), 7.55 (s, 1 H), 7.59 (d, J=7.46 Hz, 1 H), 8.23 (d, J=5.09 Hz, 1 H). LCMS: 437 (M+H)+.

EXAMPLE 160

5-chloro-6-[2-(1-methylpiperidin-4-yl)-1H-pyrrolo[2,3-b]pyridin-4-yl]-N-[4-(methylsulfonyl)benzyl]pyridin-2-amine The title compound was prepared using the procedure described in Example 11B, using Example 132 (20 mg, 0.06 mmol) in place of Example 11A and 4-(methylsulfonyl)benzaldehyde (17 mg, 0.09 mmol) in place of benzaldehyde. $^1$H NMR (400 MHz, DMSO-d$_6$): δ 1.64-1.82 (m, 2 H), 2.18 (d, J=13.90 Hz, 2 H), 2.80 (d, J=4.75 Hz, 3 H), 2.84-2.97 (m, 1 H), 3.09 (d, J=12.55 Hz, 2 H), 3.19 (s, 3 H), 3.51 (d, J=11.87 Hz, 2 H), 4.59 (d, J=4.07 Hz, 2 H), 5.91 (d, J=1.36 Hz, 1 H), 6.68 (d, J=8.82 Hz, 1 H), 7.08 (d, J=4.75 Hz, 1 H), 7.55 (d, J=8.48 Hz, 2 H), 7.63 (d, J=8.82 Hz, 1 H), 7.88 (d, J=8.48 Hz, 2 H), 8.19 (d, J=4.75 Hz, 1 H). LCMS: 510 (M+H)+.

EXAMPLE 161

4-[({5-chloro-6-[2-(1-methylpiperidin-4-yl)-1H-pyrrolo[2,3-b]pyridin-4-yl]pyridin-2-yl}amino)methyl]benzenesulfonamide The title compound was prepared using the procedure described in Example 11B, using Example 132 (20 mg, 0.06 mmol) in place of Example 11A and 4-formylbenzenesulfonamide (16 mg, 0.09 mmol) in place of benzaldehyde. $^1$H NMR (400 MHz, DMSO-d$_6$): δ 1.62-1.83 (m, 2 H), 2.17 (d, J=12.21 Hz, 2 H), 2.80 (d, J=4.75 Hz, 3 H), 2.84-2.99 (m, 1 H), 3.09 (d, J=12.21 Hz, 2 H), 3.51 (d, J=11.19 Hz, 2 H), 4.56 (s, 2 H), 5.92 (d, J=1.36 Hz, 1 H), 6.67 (d, J=8.82 Hz, 1 H), 7.10 (d, J=5.09 Hz, 1 H), 7.47 (d, J=8.48 Hz, 2 H), 7.63 (d, J=8.82 Hz, 1 H), 7.77 (d, J=8.48 Hz, 2 H), 8.19 (d, J=4.75 Hz, 1 H). LCMS: 511 (M+H)+.

EXAMPLE 162

4-[({5-chloro-6-[2-(1-methylpiperidin-4-yl)-1H-pyrrolo[2,3-b]pyridin-4-yl]pyridin-2-yl}amino)methyl]benzamide The title compound was prepared using the procedure described in Example 11B, using Example 132 (20 mg, 0.06 mmol) in place of Example 11A and 4-formylbenzamide (13 mg, 0.09 mmol) in place of benzaldehyde. $^1$H NMR (400 MHz, DMSO-d$_6$): δ 1.58-1.80 (m, 2 H), 2.12 (d, J=14.58 Hz, 2 H), 2.81 (d, J=4.75 Hz, 3 H), 2.96-3.16 (m, 3 H), 3.50 (d, J=11.53 Hz, 2 H), 4.52 (s, 2 H), 5.80 (d, J=1.70 Hz, 1 H), 6.68 (d, J=8.82 Hz, 1 H), 7.11 (d, J=5.09 Hz, 1 H), 7.35 (d, J=8.48 Hz, 2 H), 7.62 (d, J=8.82 Hz, 1 H), 7.83 (d, J=8.48 Hz, 2 H), 8.19 (d, J=5.09 Hz, 1 H). LCMS: 475 (M+H)+.

EXAMPLE 163

6-[2-(1-methylpiperidin-4-yl)-1H-pyrrolo[2,3-b]pyridin-4-yl]-N-[2-(morpholin-4-yl)ethyl]pyridin-2-amine The title compound was prepared using the procedure described in Example 153, using 2-morpholinoethanamine (59 mg, 0.45 mmol) in place of 2-(4-(aminomethyl)phenoxy)-N,N-dimethylethanamine. $^1$H NMR (400 MHz, DMSO-$d_6$): δ 1.69-1.99 (m, 2 H), 2.20-2.40 (m, 2 H), 2.83 (s, 3 H), 2.96-3.07 (m, 1 H), 3.14 (d, J=16.62 Hz, 4 H), 3.32-3.68 (m, 6 H), 3.68-3.87 (m, 2 H), 3.89-4.07 (m, 2 H), 6.59 (s, 1 H), 6.80 (d, J=8.82 Hz, 1 H), 7.17-7.35 (m, 1 H), 7.51 (d, J=5.09 Hz, 1 H), 7.67-7.82 (m, 1 H), 8.25 (d, J=5.09 Hz, 1 H). LCMS: 421 (M+H)$^+$.

EXAMPLE 164

2-({6-[2-(1-methylpiperidin-4-yl)-1H-pyrrolo[2,3-b]pyridin-4-yl]pyridin-2-yl}amino)ethanol The title compound was prepared using the procedure described in Example 153, using 2-aminoethanol (28 mg, 0.45 mmol) in place of 2-(4-(aminomethyl)phenoxy)-N,N-dimethylethanamine. $^1$H NMR (400 MHz, DMSO-$d_6$): δ 1.77-1.97 (m, 2 H), 2.35 (d, J=14.34 Hz, 2 H), 2.83 (d, J=4.88 Hz, 3 H), 3.01-3.17 (m, 3 H), 3.47-3.52 (m, 2 H), 3.52-3.59 (m, 2 H), 3.62-3.66 (m, 2 H), 6.75 (s, 1 H), 6.76-6.81 (m, 1 H), 7.21 (d, J=7.32 Hz, 1 H), 7.50 (t, J=4.43 Hz, 1 H), 7.64-7.82 (m, 1 H), 8.28 (d, J=5.19 Hz, 1 H). LCMS: 352 (M+H)$^+$.

EXAMPLE 165

5-chloro-6-[2-(1-methylpiperidin-4-yl)-1H-pyrrolo[2,3-b]pyridin-4-yl]-N-(piperidin-4-ylmethyl)pyridin-2-amine A solution of Example 132 (30 mg, 0.09 mmol) in 1,2-dichloroethane (1 mL) and acetic acid (0.5 mL) was treated with tert-butyl 4-formylpiperidine-1-carboxylate (28.1 mg, 0.13 mmol) and stirred at room temperature for 2 hours. Sodium triacetoxyborohydride (28 mg, 0.13 mmol) was added and the mixture was stirred at room temperature for 12 hours. The mixture was diluted with dichloromethane (20 mL), treated with saturated sodium bicarbonate solution and the organic layer was concentrated. The residue was dissolved in dichloromethane (5 mL), trifluoroacetic acid (0.5 mL) was added and the mixture stirred at room temperature for 1 hour. Concentration and purification by HPLC (Zorbax XDB C-18 (32) using a gradient of 5-40% acetonitrile/water (containing 0.1% trifluoroacetic acid) afforded the title compound. $^1$H NMR (400 MHz, DMSO-$d_6$): δ 1.20-1.34 (m, 4 H), 1.75-1.83 (m, 4 H), 2.29 (d, J=13.73 Hz, 2 H), 2.81 (d, J=4.27 Hz, 3 H), 2.84-2.94 (m, 1 H), 2.98-3.06 (m, 1 H), 3.11 (d, J=12.51 Hz, 2 H), 3.14-3.20 (m, 2 H), 3.27 (d, J=6.10 Hz, 2 H), 3.54 (d, J=11.90 Hz, 2 H), 6.08 (s, 1 H), 6.62 (d, J=8.85 Hz, 1 H), 7.15 (d, J=4.88 Hz, 1 H), 7.58 (d, J=8.85 Hz, 1 H), 8.24 (d, J=5.19 Hz, 1 H). LCMS: 439 (M+H)$^+$.

EXAMPLE 166

4-[4-(5-fluoro-2-methoxyphenyl)-1H-pyrrolo[2,3-b]pyridin-2-yl]tetrahydro-2H-pyran-4-ol

EXAMPLE 166A 4-(4-(5-fluoro-2-methoxyphenyl)-1-tosyl-1H-pyrrolo[2,3-b]pyridin-2-yl)tetrahydro-2H-pyran-4-ol To a solution of Example 87A (200 mg, 0.504 mmol) in tetrahydrofuran (5 mL) at −78° C. was added 1.6M n-butyllithium in hexanes (0.473 mL, 0.757 mmol) under nitrogen. The mixture was stirred for 5 minutes and dihydro-2H-pyran-4(3H)-one (101 mg, 1.009 mmol) was added. Stirring was continued at −78° C. for 1 hour and the mixture was warmed to room temperature overnight. The mixture was quenched with water, extracted with ethyl acetate, dried over magnesium sulfate, filtered and purified by flash chromatography (silica gel, 20-100% ethyl acetate/heptanes to afford the title compound. MS (ESI$^+$) m/z 497.0 (M+H)$^+$.

EXAMPLE 166B

4-[4-(5-fluoro-2-methoxyphenyl)-1H-pyrrolo[2,3-b]pyridin-2-yl]tetrahydro-2H-pyran-4-ol The title compound was prepared as the trifluoroacetate salt using the procedure described in Example 126C, using Example 166A in place of Example 126B. $^1$H NMR (300 MHz, DMSO-$d_6$) δ 1.71-1.78 (m, 2H), 1.84-2.43 (m, 2H), 3.62-3.71 (m, 2H), 3.74 (s, 3H), 3.76-3.83 (m, 2H), 3.84 (bs, 1H), 6.15 (d, J=2.1 Hz, 1H), 7.08 (d, J=5.0 Hz, 1H), 7.15-7.33 (m, 3H), 8.16-8.22 (m, 1H), 11.69 (bs, 1H). MS (ESI$^+$) m/z 497.0 (M+H)$^+$.

EXAMPLE 167

4-(5-fluoro-2-methoxyphenyl)-2-[1-(pyridin-4-ylmethyl)azetidin-3-yl]-1H-pyrrolo[2,3-b]pyridine The title compound was prepared as the trifluoroacetate salt using the procedure described in Example 110, using Example 146D (0.11 g, 0.209 mmol) in place of Example 59F and isonicotinaldehyde (55 mg, 0.513 mmol) in place of tetrahydro-4H-pyran-4-one. $^1$H NMR (500 MHz, DMSO-$d_6$) δ 3.73 (s, 3 H) 4.23-4.46 (m, 5 H) 4.59 (s, 2 H) 6.44 (s, 1 H) 7.12 (d, J=4.88 Hz, 1 H) 7.19-7.25 (m, 2 H) 7.27-7.33 (m, 1 H) 7.59 (d, J=5.80 Hz, 2 H) 8.25 (d, J=4.88 Hz, 1 H) 8.74 (d, J=5.80 Hz, 2 H) 11.94 (br. s, 1 H). MS (ESI$^+$) m/z 389.0 (M+H)$^+$.

EXAMPLE 168

1-{3-[4-(5-fluoro-2-methoxyphenyl)-1H-pyrrolo[2,3-b]pyridin-2-yl]azetidin-1-yl}ethanone The title compound was prepared as the trifluoroacetate salt using the procedure described in Example 108, using Example 146D (0.05 g, 0.095 mmol) in place of Example 59F. $^1$H NMR (500 MHz, DMSO-$d_6$) δ 1.79 (s, 3 H) 3.74 (s, 3 H) 3.92-4.05 (m, 2 H) 4.16-4.31 (m, 2 H) 4.46 (t, J=8.54 Hz, 1 H) 6.29 (d, J=1.53 Hz, 1 H) 7.13 (d, J=4.88 Hz, 1 H) 7.18-7.25 (m, 2 H) 7.26-7.32 (m, 1 H) 8.23 (d, J=4.88 Hz, 1 H) 12.02 (br. s, 1 H).). MS (ESI$^+$) m/z 340.0 (M+H)$^+$.

EXAMPLE 169

2-{3-[4-(5-fluoro-2-methoxyphenyl)-1H-pyrrolo[2,3-b]pyridin-2-yl]azetidin-1-yl}ethanamine

EXAMPLE 169A tert-butyl (2-(3-(4-(5-fluoro-2-methoxyphenyl)-1H-pyrrolo[2,3-b]pyridin-2-yl)azetidin-1-yl)ethyl)carbamate The title compound was prepared using the procedure described in Example 110, using tert-butyl(2-oxoethyl)carbamate (50 mg, 0.314 mmol) in place of tetrahydro-4H- pyran-4-one and Example 146D (110 mg, 0.209 mmol) in place of Example 59F. MS (APCl⁺) m/z 440.5 (M+H)⁺.

EXAMPLE 169B

2-{3-[4-(5-fluoro-2-methoxyphenyl)-1H-pyrrolo[2,3-b]pyridin-2-yl]azetidin-1-yl}ethanamine The title compound was prepared as the trifluoroacetate salt using the procedure described in Example 109B, using Example 169A (92 mg, 0.209 mmol) in place of Example 109A. ¹H NMR (400 MHz, DMSO-d₆) δ 3.03-3.12 (m, 2 H) 3.46-3.55 (m, 2 H) 3.74 (s, 3 H) 4.17-4.60 (m, 5 H) 6.41 (s, 1 H) 7.12 (d, J=4.88 Hz, 1 H) 7.18-7.25 (m, 2 H) 7.26-7.34 (m, 1 H) 8.14 (s, 2 H) 8.25 (d, J=4.88 Hz, 1 H) 11.94 (s, 1 H). MS (ESI⁺) m/z 341.1 (M+H)⁺.

EXAMPLE 170

4-(5-fluoro-2-methoxyphenyl)-2-[1-(tetrahydro-2H-pyran-4-ylmethyl)azetidin-3-yl]-1H-pyrrolo[2,3-b]pyridine The title compound was prepared as the trifluoroacetate salt using the procedure described in Example 110, using tetrahydro-2H-pyran-4-carbaldehyde (58 mg, 0.508 mmol) in place of tetrahydro-4H-pyran-4-one and Example 146D (110 mg, 0.209 mmol) in place of Example 59F. ¹H NMR (500 MHz, DMSO-d₆) δ 1.15-1.28 (m, 2 H) 1.53-1.63 (m, 2 H) 1.80-1.91 (m, 1 H) 3.15-3.32 (m, 4 H) 3.73 (s, 3 H) 4.18-4.31 (m, 2 H) 4.39-4.53 (m, 2 H) 6.38-6.47 (m, 1 H) 7.10 (d, J=5.19 Hz, 1 H) 7.18-7.24 (m, 2 H) 7.26-7.32 (m, 1 H) 8.24 (d, J=4.88 Hz, 1 H) 9.62-10.28 (m, 1 H) 11.88-11.98 (m, 1 H). MS (ESI⁺) m/z 396.0 (M+H)⁺.

EXAMPLE 171

4-(5-fluoro-2-methoxyphenyl)-2-{1-[2-(morpholin-4-yl)ethyl]azetidin-3-yl}-1H-pyrrolo[2,3-b]pyridine The title compound was prepared as the trifluoroacetate salt using the procedure described in Example 110, using tetrahydro2-morpholinoacetaldehyde hydrochloride hydrate (50 mg, 0.387 mmol) in place of tetrahydro-4H-pyran-4-one and Example 146D (50 mg, 0.095 mmol) in place of Example 59F. ¹H NMR (500 MHz, DMSO-d₆) δ 3.00-3.27 (m, 4 H) 3.29-3.42 (m, 1 H) 3.59-3.68 (m, 2 H) 3.74 (s, 3 H) 3.76-3.83 (m, 2 H) 4.19-4.56 (m, 6 H) 6.36-6.51 (m, 1 H) 7.10-7.15 (m, 1 H) 7.18-7.26 (m, 2 H) 7.26-7.34 (m, 1 H) 8.26 (d, J=4.88 Hz, 1 H) 11.83-12.07 (m, 1 H). MS (ESI⁺) m/z 411.0 (M+H)⁺.

EXAMPLE 172

2-{3-[4-(5-fluoro-2-methoxyphenyl)-1H-pyrrolo[2,3-b]pyridin-2-yl]azetidin-1-yl}ethanol

EXAMPLE 172A 2-(1-(2-((tert-butyldimethylsilyl)oxy)ethyl)azetidin-3-yl)-4-(5-fluoro-2-methoxyphenyl)-1H-pyrrolo[2,3-b]pyridine The title compound was prepared as the trifluoroacetate salt using the procedure described in Example 109A, using Example 146D (50 mg, 0.095 mmol) in place of the product of Example 59F. MS (APCl⁺) m/z 456.5 (M+H)⁺.

EXAMPLE 172B

2-{3-[4-(5-fluoro-2-methoxyphenyl)-1H-pyrrolo[2,3-b]pyridin-2-yl]azetidin-1-yl}ethanol The title compound was prepared as the trifluoroacetate salt using the procedure described in Example 109B, using Example 172A (40 mg, 0.088 mmol) in place of Example 109A. ¹H NMR (500 MHz, DMSO-d₆) δ 3.27-3.41 (m, 2 H) 3.60-3.64 (m, 2 H) 3.73 (s, 3 H) 4.16-4.52 (m, 6 H) 6.34-6.48 (m, 1 H) 7.07-7.13 (m, 1 H) 7.17-7.25 (m, 2 H) 7.25-7.33 (m, 1 H) 8.23 (d, J=4.88 Hz, 1 H) 11.73-11.96 (m, 1 H). MS (ESI⁺) m/z 342.0 (M+H)⁺.

EXAMPLE 173 tert-butyl 3-[({5-chloro-6-[2-(1-methylpiperidin-4-yl)-1H-pyrrolo[2,3-b]pyridin-4-yl]pyridin-2-yl}amino)methyl]pyrrolidine-1-carboxylate The title compound was prepared using the procedure described in Example 11B, using Example 132 (20 mg, 0.06 mmol) in place of Example 11A and tert-butyl 3-formylpyrrolidine-1-carboxylate (18 mg, 0.09 mmol) in place of benzaldehyde. ¹H NMR (400 MHz, DMSO-d₆): δ 1.35 (s, 9 H), 1.50-1.68 (m, 2 H), 1.80 (d, J=12.21 Hz, 2 H), 1.93-2.09 (m, 1 H), 2.28 (d, J=13.12 Hz, 2 H), 2.80 (d, J=3.36 Hz, 3 H), 2.89-3.04 (m, 1 H), 3.10 (d, J=11.60 Hz, 2 H), 3.19-3.29 (m, 2 H), 3.26-3.40 (m, 2 H), 3.52 (d, J=11.90 Hz, 2 H), 3.78-3.98 (m, 2 H), 6.09 (s, 1 H), 6.61 (d, J=9.16 Hz, 1 H), 7.13-7.16 (m, 1 H), 7.57 (d, J=9.16 Hz, 1 H), 8.23 (d, J=4.88 Hz, 1 H). LCMS: 525 (M+H)⁺.

EXAMPLE 174

5-chloro-N-[(1,1-dioxidotetrahydro-2H-thiopyran-4-yl)methyl]-6-[2-(1-methylpiperidin-4-yl)-1H-pyrrolo[2,3-b]pyridin-4-yl]pyridin-2-amine The title compound was prepared using the procedure described in Example 11B, using Example 132 (20 mg, 0.06 mmol) in place of Example 11A and tetrahydro-2H-thiopyran-4-carbaldehyde 1,1-dioxide (15 mg, 0.09 mmol) in place of benzaldehyde. ¹H NMR (400 MHz, DMSO-d₆): δ 1.60 (d, J=11.90 Hz, 2 H), 1.72-1.90 (m, 2 H), 2.02 (d, J=13.12 Hz, 2 H), 2.28 (d, J=13.12 Hz, 2 H), 2.80 (s, 3 H), 2.94-3.15 (m, 6 H), 3.15-3.25 (m, 2 H), 3.52 (d, J=11.60 Hz, 2 H), 3.83-3.98 (m, 2 H), 6.11 (s, 1 H), 6.61 (d, J=8.85 Hz, 1 H), 7.17 (d, J=4.88 Hz, 1 H), 7.57 (d, J=8.85 Hz, 1 H), 8.23 (d, J=4.88 Hz, 1 H). LCMS: 488 (M+H)⁺.

EXAMPLE 175

{3-[({5-chloro-6-[2-(1-methylpiperidin-4-yl)-1H-pyrrolo[2,3-b]pyridin-4-yl]pyridin-2-yl}amino)methyl]phenoxy}acetic acid The title compound was prepared using the procedure described in Example 11B, using Example 132 (20 mg, 0.06 mmol) in place of Example 11A and 2-(3-formylphenoxy)acetic acid (16 mg, 0.09 mmol) in place of benzaldehyde. ¹H NMR (400 MHz, DMSO-d₆): δ 1.65-1.85 (m, 2 H), 2.20 (d, J=10.99 Hz, 2 H), 2.79 (s, 3 H), 2.89-2.97 (m, 1 H), 3.00-3.17 (m, 2 H), 3.51 (d, J=11.90 Hz, 2 H), 4.38 (s, 2 H), 4.63 (s, 2 H), 5.99 (s, 1 H), 6.58-6.64 (m, 1 H), 6.85 (d, J=8.54 Hz, 2 H), 7.09 (d, J=8.54 Hz, 1 H), 7.12-7.19 (m, 1 H), 7.21 (d, J=8.54 Hz, 1 H), 7.54-7.63 (m, 1 H), 8.21 (d, J=5.19 Hz, 1 H). LCMS: 506 (M+H)$^+$.

EXAMPLE 176

{4-[({5-chloro-6-[2-(1-methylpiperidin-4-yl)-1H-pyrrolo[2,3-b]pyridin-4-yl]pyridin-2-yl}amino) methyl]phenoxy}acetic acid The title compound was prepared using the procedure described in Example 11B, using Example 132 (20 mg, 0.06 mmol) in place of Example 11A and 2-(4-formylphenoxy) acetic acid (16 mg, 0.09 mmol) in place of benzaldehyde. $^1$H NMR (400 MHz, DMSO-d$_6$): δ 1.63-1.83 (m, 2 H), 2.20 (d, J=13.43 Hz, 2 H), 2.80 (s, 3 H), 2.94 (t, J=12.21 Hz, 1 H), 3.02-3.17 (m, 2 H), 3.50 (d, J=12.21 Hz, 2 H), 4.38 (s, 2 H), 4.63 (s, 2 H), 5.99 (s, 1 H), 6.63 (d, J=8.85 Hz, 1 H), 6.85 (d, J=8.54 Hz, 2 H), 7.15 (d, J=5.19 Hz, 1 H), 7.18-7.27 (d, J=8.54 Hz, 2 H), 7.58 (d, J=8.85 Hz, 1 H), 8.21 (d, J=4.88 Hz, 1 H). LCMS: 506 (M+H)$^+$.

EXAMPLE 177

1-{4-[({5-chloro-6-[2-(1-methylpiperidin-4-yl)-1H-pyrrolo[2,3-b]pyridin-4-yl]pyridin-2-yl}amino) methyl]piperidin-1-yl}ethanone To a solution of Example 165 (20 mg, 0.05 mmol) in N,N-dimethylformamide (1 mL) was added acetic acid (4 mg, 0.07 mmol) and triethylamine (0.1 mL) at room temperature. 1-Ethyl-3-(3-dimethylaminopropyl)carbodiimide hydrochloride (11 mg, 0.07 mmol) and N-hydroxybenzotriazole (10 mg, 0.07 mmol) were added and the mixture was stirred overnight. Purification by HPLC (Zorbax XDB C-18 (32) using a gradient of 5-40% acetonitrile/water (containing 0.1% trifluoroacetic acid) afforded the title compound. $^1$H NMR (400 MHz, DMSO-d$_6$): δ 1.57-1.93 (m, 5 H), 1.96 (s, 3 H), 2.28 (d, J=13.73 Hz, 2 H), 2.80 (d, J=3.97 Hz, 3 H), 2.87-3.01 (m, 2 H), 3.02-3.22 (m, 5 H), 3.52 (d, J=11.60 Hz, 2 H), 3.77 (d, J=13.12 Hz, 2 H), 4.34 (d, J=12.82 Hz, 2 H), 6.10 (s, 1 H), 6.61 (d, J=9.16 Hz, 1 H), 7.11-7.18 (m, 1 H), 7.56 (d, J=9.16 Hz, 1 H), 8.23 (d, J=5.19 Hz, 1 H). LCMS: 481 (M+H)$^+$.

EXAMPLE 178

5-chloro-6-[2-(1-methylpiperidin-4-yl)-1H-pyrrolo [2,3-b]pyridin-4-yl]-N-(4H-1,2,4-triazol-3-ylmethyl) pyridin-2-amine The title compound was prepared using the procedure described in Example 11B, using Example 132 (20 mg, 0.06 mmol) in place of Example 11A and 4H-1,2,4-triazole-3-carbaldehyde (9 mg, 0.09 mmol) in place of benzaldehyde. $^1$H NMR (400 MHz, DMSO-d$_6$): δ 1.66-1.90 (m, 2 H), 2.26 (d, J=13.73 Hz, 2 H), 2.82 (s, 3 H), 2.90-3.03 (m, 1 H), 3.04-3.15 (m, 2 H), 3.54 (d, J=12.21 Hz, 2 H), 4.55-4.63 (m, 2 H), 6.04 (s, 1 H), 6.74 (d, J=8.85 Hz, 1 H), 7.14-7.18 (m, 1 H), 7.66 (d, J=8.85 Hz, 1 H), 8.24 (d, J=4.88 Hz, 1 H), 8.38 (s, 1 H). LCMS: 423 (M+H)$^+$.

EXAMPLE 179

4-fluoro-3-[2-(1-methylpiperidin-4-yl)-1H-pyrrolo [2,3-b]pyridin-4-yl]-N-(tetrahydro-2H-pyran-4-ylmethyl)aniline

EXAMPLE 179A tert-butyl 3-bromo-4-fluorophenylcarbamate

A solution of 6-bromo-5-fluoropyridin-2-amine (5 g, 26 mmol) in dichloromethane (150 mL) was treated with di-tert-butyl dicarbonate (6 mL, 26 mmol), triethylamine (5.3 mL, 52 mmol) and 4-dimethylaminopyridine (0.8 g, 6.6 mmol) and the mixture was stirred at room temperature overnight.

The mixture was concentrated and purified by flash column (silica) using 30% ethyl acetate in hexane to afford the title compound. LCMS: 290 (M+H)$^+$.

EXAMPLE 179B tert-butyl 4-fluoro-3-(4,4,5,5-tetramethyl-1,3,2-dioxaborolan-2-yl)phenylcarbamate The title compound was prepared using the procedure described in Example 88A, using Example 179A (3 g, 10.3 mmol) in place of 2-bromo-6-fluoropyridine. LCMS: 338 (M+H)$^+$.

EXAMPLE 179C tert-butyl 4-fluoro-3-(2-(1-methylpiperidin-4-yl)-1H-pyrrolo[2,3-b]pyridin-4-yl)phenylcarbamate The title compound was prepared using the procedure described in Example 1 G, using Example 132A (200 mg, 0.8 mmol) in place of Example 1F and Example 179B (405 mg, 1.2 mmol in place of 5-fluoro-2-methoxyphenylboronic acid. LCMS: 425 (M+H)$^+$.

EXAMPLE 179D 4-fluoro-3-(2-(1-methylpiperidin-4-yl)-1H-pyrrolo [2,3-b]pyridin-4-yl)aniline To a solution of Example 179C (102 mg, 0.24 mmol) in dichloromethane (2 mL) was added trifluoroacetic acid (1 mL) and the mixture was stirred for 2 hours. Concentration and purification by HPLC (Zorbax XDB C-18 (32) using a gradient of 5-40% acetonitrile/water (containing 0.1% trifluoroacetic acid) afforded the title compound. LCMS: 325 (M+H)$^+$.

EXAMPLE 179E 4-fluoro-3-(2-(1-methylpiperidin-4-yl)-1H-pyrrolo [2,3-b]pyridin-4-yl)-N-((tetrahydro-2H-pyran-4-yl) methyl)aniline The title compound was prepared using the procedure described in Example 11B, using Example 179D (20 mg, 0.06 mmol) in place of Example 11A and tetrahydro-2H-pyran-4-carbaldehyde (10 mg, 0.09 mmol) in place of benzaldehyde. ¹H NMR (400 MHz, DMSO-d₆): δ 1.13-1.32 (m, 4 H), 1.53 (d, J=11.60 Hz, 2 H), 1.70-1.86 (m, 1 H), 1.93 (dd, J=7.17, 3.51 Hz, 2 H), 2.29 (d, J=13.73 Hz, 2 H), 2.82 (d, J=4.27 Hz, 3 H), 2.94-3.06 (m, 1 H), 3.06-3.14 (m, 2 H), 3.18-3.25 (m, 2 H), 3.54 (d, J=11.60 Hz, 2 H), 3.84 (dd, J=10.99, 2.75 Hz, 2 H), 6.13 (s, 1 H), 6.75-6.85 (m, 1 H), 7.00-7.29 (m, 3 H), 8.25 (d, J=4.88 Hz, 1 H). LCMS: 423 (M+H)⁺.

EXAMPLE 180

1-{4-[4-(5-fluoro-2-methoxyphenyl)-1H-pyrrolo[2,3-b]pyridin-2-yl]piperidin-1-yl}-2-(piperidin-1-yl)ethanone The title compound was prepared as described in Example 147B, using piperidine (0.299 mmol, 25.4 mg) in place of piperidin-4-ol. ¹H NMR (400 MHz, CD₃OD) δ 1.47-1.63 (m, 1H), 1.61-2.02 (m, 7H), 2.14-2.23 (m, 2H), 2.83-3.11 (m, 3H), 3.15-3.27 (m, 1H), 3.30-3.33 (m, 1H), 3.53-3.62 (m, 2H), 3.79-3.86 (m, 4H), 4.16-4.29 (m, 2H), 4.59-4.68 (m, 1H), 6.39 (s, 1H), 7.19-7.32 (m, 3H), 7.52 (d, J=6.0 Hz, 1H), 8.29 (d, J=6.0 Hz, 1H). MS (ESI⁺) m/z 451.2 (M+H)⁺.

EXAMPLE 181

1-{4-[4-(5-fluoro-2-methoxyphenyl)-1H-pyrrolo[2,3-b]pyridin-2-yl]piperidin-1-yl}-2-(morpholin-4-yl)ethanone The title compound was prepared as described in Example 147B, using morpholine (0.299 mmol, 26.0 mg) in place of piperidin-4-ol. ¹H NMR (400 MHz, CD₃OD) δ 1.63-1.90 (m, 2H), 2.13-2.25 (m, 2H), 2.92 (td, J=13.0, 2.9 Hz, 1H), 3.13-3.26 (m, 2H), 3.26-3.36 (m, 2H), 3.37-3.78 (m, 2H), 3.80 (s, 3H), 3.83-3.41 (m, 5H), 4.27-4.41 (m, 2H), 4.60-4.68 (m, 1H), 6.38 (s, 1H), 7.19-7.32 (m, 3H), 7.49 (d, J=6.0 Hz, 1H), 8.28 (d, J=6.0 Hz, 1H). MS (ESI⁺) m/z 453.2 (M+H)⁺.

EXAMPLE 182

1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone The title compound was prepared as described in Example 147B, using 4-aminocyclohexanol (3 eq., 0.597 mmol, 68.8 mg) in place of piperidin-4-ol. Heating overnight was also required. ¹H NMR (400 MHz, CD₃OD) δ 1.26-1.41 (m, 2H), 1.42-1.89 (m, 4H), 1.97-2.11 (m, 2H), 2.09-2.31 (m, 4H), 2.87-2.98 (m, 1H), 3.04-3.24 (m, 2H), 3.25-3.35 (m, 1H), 3.50-3.64 (m, 1H), 3.80 (s, 3H), 3.84-4.00 (m, 1H), 4.05-4.21 (m, 2H), 4.58-4.66 (m, 1H), 6.35 (s, 1H), 7.18-7.31 (m, 3H), 7.47 (d, J=5.9 Hz, 1H), 8.27 (d, J=5.9 Hz, 1H). MS (ESI⁺) m/z 481.1 (M+H)⁺.

EXAMPLE 183

1-{4-[4-(5-fluoro-2-methoxyphenyl)-1H-pyrrolo[2,3-b]pyridin-2-yl]piperidin-1-yl}-2-[(2-hydroxyethyl)amino]ethanone A mixture of Example 147A (80 mg, 0.199 mmol) and 2-aminoethanol (0.096 mL, 1.593 mmol) in tetrahydrofuran (2 mL) was heated at 70° C. for 4 hours. The mixture was quenched with water and brine and was extracted with ethyl acetate (twice). The combined organic layers were washed with brine, dried over magnesium sulfate, filtered, concentrated and purified by reverse-phase HPLC on a Zorbax RX-C18 column using a gradient of 15% to 100% methanol/0.1% aqueous trifluoroacetic acid to afford the title compound as a trifluoroacetic acid salt. ¹H NMR (400 MHz, CD₃OD) δ 1.63-1.89 (m, 2H), 2.13-2.24 (m, 2H), 2.93 (td, J=13.0, 2.8 Hz, 1H), 3.16-3.22 (m, 3H), 3.25-3.36 (m, 1H), 3.80 (s, 3H), 3.82-3.90 (m, 3H), 4.07-4.21 (m, 2H), 4.58-4.67 (m, 1H), 6.37 (s, 1H), 7.18-7.32 (m, 3H), 7.49 (d, J=6.0 Hz, 1H), 8.28 (d, J=6.0 Hz, 1H). MS (ESI⁺) m/z 427.1 (M+H)⁺.

EXAMPLE 184

4-(5-fluoro-2-methoxyphenyl)-2-(1-methylazetidin-3-yl)-1H-pyrrolo[2,3-b]pyridine The title compound was prepared as the trifluoroacetate salt using the procedure described in Example 110, using formaldehyde (37% in water) (200 mg, 2.465 mmol) in place of tetrahydro-4H-pyran-4-one and Example 146D (110 mg, 0.209 mmol) in place of Example 59F. ¹H NMR (400 MHz, DMSO-d₆) δ 2.87-2.96 (m, 3 H) 3.74 (s, 3 H) 4.14-4.54 (m, 5 H) 6.36-6.44 (m, 1 H) 7.07-7.13 (m, 1 H) 7.17-7.25 (m, 2 H) 7.25-7.34 (m, 1 H) 8.24 (d, J=4.88 Hz, 1 H) 11.78-11.99 (m, 1 H). MS (ESI⁺) m/z 311.9 (M+H)⁺.

EXAMPLE 185

4-(5-fluoro-2-methoxyphenyl)-2-[1-(methylsulfonyl)azetidin-3-yl]-1H-pyrrolo[2,3-b]pyridine The title compound was prepared as the trifluoroacetate salt using the procedure described in Example 108, using methanesulfonyl chloride (21 mg, 0.180 mmol) in place of acetyl chloride and Example 146D (93 mg, 0.177 mmol) in place of Example 59F. ¹H NMR (400 MHz, DMSO-d₆) δ 3.05 (s, 3 H) 3.74 (s, 3 H) 4.01-4.22 (m, 5 H) 6.32 (d, J=1.83 Hz, 1 H) 7.08 (d, J=4.88 Hz, 1 H) 7.17-7.24 (m, 2 H) 7.24-7.32 (m, 1 H) 8.21 (d, J=4.88 Hz, 1 H) 11.80 (s, 1 H). MS (ESI⁺) m/z 376.0 (M+H)⁺.

EXAMPLE 186

3-{4-[4-(5-fluoro-2-methoxyphenyl)-1H-pyrrolo[2,3-b]pyridin-2-yl]-3,6-dihydropyridin-1(2H)-yl}propane-1,2-diol The title compound was prepared as described in Example 149, using Example 87D (0.202 mmol, 80.0 mg) in place of Example 135B. The mixture was heated at 40° C. for 3 hours. ¹H NMR (400 MHz, CD₃OD) δ 2.91-2.99 (m, 2H), 3.25-3.51 (m, 3H), 3.59 (qd, J=11.3, 5.1 Hz, 2H), 3.78-3.89 (m, 1H), 3.79 (s, 3H), 3.89-4.30 (m, 3H), 6.47 (bs, 1H), 6.58 (s, 1H), 7.16-7.28 (m, 3H), 7.33 (d, J=5.5 Hz, 1H), 8.29 (d, J=5.5 Hz, 1H). MS (ESI⁺) m/z 397.9 (M+H)⁺.

EXAMPLE 187

4-fluoro-3-[2-(piperidin-4-yl)-1H-pyrrolo[2,3-b]pyridin-4-yl]aniline

EXAMPLE 187A tert-butyl 4-(4-(5-(tert-butoxycarbonylamino)-2-fluorophenyl)-1H-pyrrolo[2,3-b]pyridin-2-yl)piperidine-1-carboxylate The title compound was prepared using the procedure described in Example 1 G, using Example 17E (50 mg, 0.15 mmol) in place of Example 1F and Example 179B (75 mg, 0.22 mmol) in place of 5-fluoro-2-methoxyphenylboronic acid. LCMS: 511 (M+H)+.

EXAMPLE 187B 4-fluoro-3-(2-(piperidin-4-yl)-1H-pyrrolo[2,3-b]pyridin-4-yl)aniline The title compound was prepared using the procedure described in Example 179D, using Example 187A (38 mg, 0.07 mmol) in place of Example 179C. $^1$H NMR (400 MHz, DMSO-$d_6$): δ 1.13-1.32 (m, 4 H), 1.53 (d, J=11.60 Hz, 2 H), 1.70-1.86 (m, 1 H), 1.93 (dd, J=7.17, 3.51 Hz, 2 H), 2.29 (d, J=13.73 Hz, 2 H), 2.82 (d, J=4.27 Hz, 3 H), 2.94-3.06 (m, 1 H), 3.06-3.14 (m, 2 H), 3.18-3.25 (m, 2 H), 3.54 (d, J=11.60 Hz, 2 H), 3.84 (dd, J=10.99, 2.75 Hz, 2 H), 6.13 (s, 1 H), 6.75-6.85 (m, 1 H), 7.00-7.29 (m, 3 H), 8.25 (d, J=4.88 Hz, 1 H). LCMS: 311 (M+H)+.

EXAMPLE 188

5-chloro-6-[2-(1-methylpiperidin-4-yl)-1H-pyrrolo[2,3-b]pyridin-4-yl]-N-[3-(methylsulfonyl)benzyl]pyridin-2-amine The title compound was prepared using the procedure described in Example 11B, using Example 132 (25 mg, 0.07 mmol) in place of Example 11A and 3-(methylsulfonyl)benzaldehyde (27 mg, 0.14 mmol) in place of benzaldehyde. $^1$H NMR (400 MHz, DMSO-$d_6$): δ 1.62-1.82 (m, 2 H), 2.14-2.24 (m, 2 H), 2.81 (d, J=4.75 Hz, 3 H), 2.87-2.98 (m, 1 H), 2.99-3.11 (m, 2 H), 3.11 (s, 3 H), 3.51 (d, J=11.53 Hz, 2 H), 4.57 (d, J=3.39 Hz, 2 H), 5.95 (d, J=1.36 Hz, 1 H), 6.68 (d, J=8.82 Hz, 1 H), 7.09 (d, J=4.75 Hz, 1 H), 7.55-7.66 (m, 3 H), 7.78-7.83 (m, 1 H), 7.85 (s, 1 H), 8.19 (d, J=4.75 Hz, 1 H). LCMS: 510 (M+H)+.

EXAMPLE 189

4-fluoro-3-[2-(1-methylpiperidin-4-yl)-1H-pyrrolo[2,3-b]pyridin-4-yl]-N-(pyridin-4-ylmethyl)aniline The title compound was prepared using the procedure described in Example 11B, using Example 179D (25 mg, 0.08 mmol) in place of Example 11A and isonicotinaldehyde (17 mg, 0.15 mmol) in place of benzaldehyde. $^1$H NMR (400 MHz, DMSO-$d_6$): δ 1.72-1.81 (m, 2 H), 2.24 (d, J=13.73 Hz, 2 H), 2.83 (s, 3 H), 2.98 (t, J=12.21 Hz, 1 H), 3.12 (t, J=11.90 Hz, 2 H), 3.55 (d, J=11.90 Hz, 2 H), 4.62 (s, 2 H), 5.93 (s, 1 H), 6.69 (dd, J=5.95, 2.90 Hz, 2 H), 7.03 (d, J=3.97 Hz, 1 H), 7.07-7.20 (m, 1 H), 7.91 (d, J=6.10 Hz, 2 H), 8.21 (d, J=4.88 Hz, 1 H), 8.83 (d, J=6.10 Hz, 2 H). LCMS: 416 (M+H)+.

EXAMPLE 190

4-fluoro-3-[2-(1-methylpiperidin-4-yl)-1H-pyrrolo[2,3-b]pyridin-4-yl]-N-[4-(methylsulfonyl)benzyl]aniline The title compound was prepared using the procedure described in Example 11B, using Example 179D (20 mg, 0.06 mmol) in place of Example 11A and 4-(methylsulfonyl)benzaldehyde (17 mg, 0.09 mmol) in place of benzaldehyde. $^1$H NMR (400 MHz, DMSO-$d_6$): δ 1.74-1.86 (m, 2 H), 2.24 (d, J=13.73 Hz, 2 H), 2.82 (d, J=4.58 Hz, 3 H), 2.93-3.01 (m, 1 H), 3.06-3.15 (m, 2 H), 3.20 (s, 3 H), 3.54 (d, J=11.90 Hz, 2 H), 4.43 (s, 2 H), 5.94 (s, 1 H), 6.62-6.73 (m, 2 H), 7.01-7.04 (m, 1 H), 7.07-7.14 (m, 1 H), 7.63 (d, J=8.24 Hz, 2 H), 7.90 (d, J=8.54 Hz, 2 H), 8.21 (d, J=4.88 Hz, 1H). LCMS: 493 (M+H)+.

EXAMPLE 191

4-[({4-fluoro-3-[2-(1-methylpiperidin-4-yl)-1H-pyrrolo[2,3-b]pyridin-4-yl]phenyl}amino)methyl]benzamide The title compound was prepared using the procedure described in Example 11B, using Example 179D (20 mg, 0.06 mmol) in place of Example 11A and 4-formylbenzamide (14 mg, 0.09 mmol) in place of benzaldehyde. $^1$H NMR (400 MHz, DMSO-$d_6$): δ 1.70-1.84 (m, 2 H) 2.17 (d, J=13.73 Hz, 2 H) 2.84 (d, J=4.58 Hz, 3 H) 2.91 (t, J=12.21 Hz, 1 H) 3.05-3.16 (m, 2 H) 3.55 (d, J=11.60 Hz, 2 H) 4.36 (s, 2 H) 5.76 (s, 1 H) 6.62 (dd, J=6.10, 3.05 Hz, 1 H) 6.69-6.79 (m, 1 H) 7.04 (d, J=6.41 Hz, 1 H) 7.10 (t, J=9.46 Hz, 1 H) 7.44 (d, J=8.24 Hz, 2 H) 7.86 (d, J=8.24 Hz, 2 H) 8.20 (d, J=4.88 Hz, 1 H). LCMS: 458 (M+H)+.

EXAMPLE 192

(3S,5R)-5-[({5-chloro-6-[2-(piperidin-4-yl)-1H-pyrrolo[2,3-b]pyridin-4-yl]pyridin-2-yl}amino)methyl]pyrrolidin-3-ol

EXAMPLE 192A (2R,4S)-tert-butyl 2-(((6-bromo-5-chloropyridin-2-yl)amino)methyl)-4-hydroxypyrrolidine-1-carboxylate The title compound was prepared using the procedure described in Example 11B, using (2R,4S)-tert-butyl 2-formyl-4-hydroxypyrrolidine-1-carboxylate (500 mg, 2.32 mmol) in place of benzaldehyde. LCMS: 408.1 (M+3)+.

EXAMPLE 192B 4-(4-{6-[((2R,4S)-1-tert-butoxycarbonyl-4-hydroxy-pyrrolidin-2-ylmethyl)-amino]-3-chloro-pyridin-2-yl}-1H-pyrrolo[2,3-b]pyridin-2-yl)-piperidine-1-carboxylic acid tert-butyl ester The title compound was prepared using the procedure described in Example 42B, using Example 192A (286 mg, 0.702 mmol) in place of Example 42A. LCMS: 627.3 (M+H)+.

EXAMPLE 192C (3S,5R)-5-[({5-chloro-6-[2-(piperidin-4-yl)-1H-pyrrolo[2,3-b]pyridin-4-yl]pyridin-2-yl}amino)methyl]pyrrolidin-3-ol The title compound was prepared as the trifluoroacetate salt using the procedure described in Example 1H, using Example 192B (150 mg, 0.239 mmol) in place of Example 1G. LCMS: 427.2 (M+H)+. $^1$H NMR (400 MHz, DMSO-$d_6$/D$_2$O): δ 1.75-1.78 (m, 4H), 1.9-1.96 (m, 1H), 2.20-2.23 (m, 2H), 3.02-3.07 (m, 4H), 3.18-3.22 (m, 1H), 3.34-3.39 (m, 4H), 4.35 (brs, 1H), 6.06 (s, 1H), 6.70 (d, J=9.2 Hz, 1H), 7.11 (d, J=5.2 Hz, 1H), 7.22 (brs, 1H), 7.67 (d, J=8.8 Hz, 1H), 8.22 (d, J=4.8 Hz, 1H), 8.62-8.78 (m, 1H), 9.2-9.3 (m, 1H), 11.8 (s, 1H).

EXAMPLE 193

2-(azepan-3-yl)-4-(5-fluoro-2-methoxyphenyl)-1H-pyrrolo[2,3-b]pyridine

EXAMPLE 193A tert-butyl 3-ethynylazepane-1-carboxylate

The title compound was prepared using the procedure described in Example 1D, using tert-butyl 3-formylazepane-1-carboxylate (1.5 g, 6.6 mmol) in place of Example 1C. LCMS: 224.4 (M+H)$^+$.

EXAMPLE 193B tert-butyl 3-((2-((tert-butoxycarbonyl)amino)-4-chloropyridin-3-yl)ethynyl)azepane-1-carboxylate The title compound was prepared using the procedure described in Example 1E, using Example 193A (756 mg, 3.38 mmol) in place of Example 1D. LCMS: 450.2 (M+H)$^+$.

EXAMPLE 193C tert-butyl 3-(4-chloro-1H-pyrrolo[2,3-b]pyridin-2-yl)azepane-1-carboxylate The title compound was prepared using the procedure described in Example 1F, using Example 193B (1 g, 2.22 mmol) in place of Example 1E. LCMS: 352.2 (M+2)$^+$.

EXAMPLE 193D tert-butyl 3-(4-(5-fluoro-2-methoxyphenyl)-1H-pyrrolo[2,3-b]pyridin-2-yl)azepane-1-carboxylate The title compound was prepared using the procedure described in Example 1 G, using Example 193C (200 mg, 0.57 mmol) in place of Example 1F. LCMS: 440.2 (M+H)$^+$.

EXAMPLE 193E 2-(azepan-3-yl)-4-(5-fluoro-2-methoxyphenyl)-1H-pyrrolo[2,3-b]pyridine The title compound was prepared as the hydrochloride salt using the procedure described in Example 1H, using Example 193D (120 mg, 0.273 mmol) in place of Example 1G. LCMS: 340.2 (M+H)$^+$. $^1$H NMR (400 MHz, DMSO-d$_6$/D$_2$O): δ 1.6-1.7 (m, 1H), 1.81-1.84 (m, 4H), 2.08-2.14 (m, 1H), 3.1-3.2 (m, 4H), 3.73 (s, 3H), 6.23 (s, 1H), 7.20-7.26 (m, 3H), 7.29-7.34 (m, 1H), 8.27 (d, J=5.6 Hz, 1H).

EXAMPLE 194

N-benzyl-5-chloro-6-(2-cyclohexyl-1H-pyrrolo[2,3-b]pyridin-4-yl)pyridin-2-amine

EXAMPLE 194A tert-butyl (4-chloro-3-(cyclohexylethynyl)pyridin-2-yl)carbamate The title compound was prepared using the procedure described in Example 1E, using cyclohexyl acetylene (305 mg, 2.82 mmol) in place of Example 1D. LCMS: 335.1 (M+H)$^+$.

EXAMPLE 194B 4-chloro-2-cyclohexyl-1H-pyrrolo[2,3-b]pyridine

The title compound was prepared using the procedure described in Example 1F, using Example 194A (800 mg, 2.38 mmol) in place of Example 1E. LCMS: 235.1 (M+H)$^+$.

EXAMPLE 194C 2-cyclohexyl-4-(4,4,5,5-tetramethyl-1,3,2-dioxaborolan-2-yl)-1H-pyrrolo[2,3-b]pyridine The title compound was prepared using the procedure described in Example 5A, using Example 194B (200 mg, 0.852 mmol) in place of Example 1F. LCMS: 327.3 (M+H)$^+$.

EXAMPLE 194D

N-benzyl-5-chloro-6-(2-cyclohexyl-1H-pyrrolo[2,3-b]pyridin-4-yl)pyridin-2-amine

The title compound was prepared using the procedure described in Example 5B, using Example 194C (200 mg, 0.613 mmol) in place of product of Example 5A and Example 11B (274 mg, 0.92 mmol) in place of 6-bromo-5-methoxypyridin-2-amine. LCMS: 417.1 (M+H)$^+$. $^1$H NMR (400 MHz, DMSO-d$_6$): δ 1.16-1.22 (m, 1H), 1.29-1.31 (m, 4H), 1.65-1.73 (m, 2H), 1.87-1.88 (m, 2H), 2.58-2.66 (m, 2H), 4.47 (s, 2H), 5.90 (d, J=1.6 Hz, 1H), 6.64 (d, J=9.2 Hz, 1H), 7.17 (d, J=5.6 Hz, 1H), 7.21-7.24 (m, 1H), 7.27-7.33 (m, 4H), 7.48-7.52 (m, 1H), 7.60 (d, J=8.8 Hz, 1H), 8.17 (d, J=5.2 Hz, 1H), 11.8 (s, 1H).

EXAMPLE 195

N-benzyl-3-[5-chloro-2-(piperidin-4-yl)-1H-pyrrolo[2,3-b]pyridin-4-yl]-4-fluoroaniline

EXAMPLE 195A tert-butyl 4-(4-(5-(benzylamino)-2-fluorophenyl)-5-chloro-1H-pyrrolo[2,3-b]pyridin-2-yl)piperidine-1-carboxylate The title compound was prepared using the procedure described in Example 1 G, using Example 51B (133 mg, 0.407 mmol) in place of 5-fluoro-2-methoxyphenylboronic acid and Example 77C (130 mg, 0.313 mmol) in place of Example 1F. LCMS: 479.1 (M+H-NCOOH)$^+$.

EXAMPLE 195B

N-benzyl-3-[5-chloro-2-(piperidin-4-yl)-1H-pyrrolo[2,3-b]pyridin-4-yl]-4-fluoroaniline The title compound was prepared as the trifluoroacetate salt using the procedure described in Example 1H, using Example 195A (140 mg, 0.262 mmol) in place of Example 1G, and purified using preparative HPLC (Zorbax XDB C-18 column with gradient elution from 0.1% trifluoroacetic acid in water to 1:1 methanol/acetonitrile). LCMS: 435.4 (M+H)$^+$. $^1$H NMR (400 MHz, CD$_3$OD): δ 1.85-1.93 (m, 2H), 2.26-2.33 (m, 2H), 3.09-3.20 (m, 3H), 3.48-3.53 (m, 2H), 4.34 (s, 2H), 5.90 (s, 1H), 6.6-6.63 (m, 1H), 6.79-6.83 (m, 1H), 7.03 (t, J=9.2 Hz, 1H), 7.23-7.27 (m, 1H), 7.31-7.35 (m, 2H), 7.38-7.40 (m, 2H), 8.20 (s, 1H).

EXAMPLE 196

5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine

EXAMPLE 196A

(2R,4R)-tert-butyl 2-(((6-bromo-5-chloropyridin-2-yl)amino)methyl)-4-fluoropyrrolidine-1-carboxylate The title compound was prepared using the procedure described in Example 11B, using (2R,4R)-tert-butyl 4-fluoro-2-formylpyrrolidine-1-carboxylate (500 mg, 2.74 mmol) in place of benzaldehyde. LCMS: 410.3 (M+3)$^+$.

EXAMPLE 196B tert-butyl 4-(4-(6-((((2R,4R)-1-(tert-butoxycarbonyl)-4-fluoropyrrolidin-2-yl)methyl)amino)-3-chloropyridin-2-yl)-1H-pyrrolo[2,3-b]pyridin-2-yl)piperidine-1-carboxylate The title compound was prepared using the procedure described in Example 7A, using Example 21A (200 mg, 0.468 mmol) in place of Example 5A and Example 196A (128 mg, 0.312 mmol) in place of 2-bromo-4-cyclopropyl-1-methoxybenzene. LCMS: 629.6 (M+H)$^+$.

EXAMPLE 196C

5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine The title compound was prepared as trifluoroacetate salt using the procedure described in Example 1H, using Example 196B (150 mg, 0.238 mmol) in place of Example 1G, and purified using preparative HPLC (SEMI-C-18 column with gradient elution from 0.1% trifluoroacetic acid in water to 1:1 methanol/acetonitrile). LCMS: 429.2 (M+H)$^+$. $^1$H NMR (400 MHz, CD$_3$OD): δ 1.95-2.02 (m, 3H), 2.17-2.22 (m, 2H), 2.36-2.38 (m, 2H), 3.14-3.22 (m, 3H), 3.48-3.70 (m, 2H), 3.68-3.70 (m, 2H), 4.06-4.08 (m, 1H), 5.27 (brs, 1H), 5.40 (brs, 1H), 6.22 (s, 1H), 6.79 (d, J=9.2 Hz, 1H), 7.25 (d, J=5.2 Hz, 1H), 7.71 (d, J=8.8 Hz, 1H), 8.30 (d, J=5.2 Hz, 1H).

EXAMPLE 197

4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile

EXAMPLE 197A

4-(((5-chloro-4-iodopyridin-2-yl)amino)methyl)tetrahydro-2H-pyran-4-carbonitrile A solution of 5-chloro-2-fluoro-4-iodopyridine (1 g, 3.88 mmol) and 4-(aminomethyl)tetrahydro-2H-pyran-4-carbonitrile (1.634 g, 11.65 mmol) in 4 mL of dimethylsulfoxide was heated at 100° C. for 8 hours. The mixture was quenched with 100 mL of ice-cold water and was extracted with ethyl acetate (50 mL×2). The organic layer was washed with water and brine, dried over sodium sulfate, filtered, and concentrated. Purification by column chromatography (silica gel, 20% ethyl acetate in hexane) afforded the title compound.

EXAMPLE 197B

4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile To a solution of Example 197A (1 g, 2.65 mmol) and Example 21A (1.132 g, 2.65 mmol) in 10 mL ethanol was added potassium acetate (0.780 g, 7.94 mmol). The mixture was degassed for 5 minutes with nitrogen and bis(di-tert-butyl(4-dimethylaminophenyl)phosphine)dichloropalladium(II) (0.073 g, 0.132 mmol) was added. The mixture was heated at 80° C. for 2 hours and was cooled to room temperature. The mixture was quenched into ice-cold water and extracted with ethyl acetate (100 mL×3). The organic layer was washed with brine, concentrated and purified by preparative HPLC (Agilent AD/SP/C18-25/011 reversed phase column and gradient elution from 10 mM ammonium acetate to 1:1 methanol/acetonitrile) to afford the title compound as the acetate salt. LCMS: 452.1 (M+H)$^+$. $^1$H NMR (400 MHz, CD$_3$OD): δ 1.84-1.88 (m, 2H), 2.01-2.05 (m, 4H), 3.32-3.36 (m, 2H), 3.14-3.20 (m, 3H), 3.49-3.52 (m, 2H), 3.69-3.75 (m, 2H), 4.0-4.03 (m, 2H), 4.49 (s, 2H), 6.13 (s, 1H), 7.0 (s, 1H), 7.11 (d, J=5.2 Hz, 1H), 8.26 (d, J=4.8 Hz, 1H), 8.34 (s, 1H).

EXAMPLE 198

5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine

EXAMPLE 198A

(R)-tert-butyl 2-(((6-bromo-5-chloropyridin-2-yl)amino)methyl)-4,4-difluoropyrrolidine-1-carboxylate The title compound was prepared using the procedure described in Example 11B, using (R)-tert-butyl 4,4-difluoro- 2-formylpyrrolidine-1-carboxylate (200 mg, 0.850 mmol) in place of benzaldehyde. LCMS: 326 (M+H-Boc)+.

EXAMPLE 198B (R)-tert-butyl 4-(4-(6-(((1-(tert-butoxycarbonyl)-4,4-difluoropyrrolidin-2-yl)methyl)amino)-3-chloropyridin-2-yl)-1H-pyrrolo[2,3-b]pyridin-2-yl)piperidine-1-carboxylate The title compound was prepared using the procedure described in Example 7A, using Example 21A (400 mg, 0.936 mmol) in place of Example 5A and Example 198A (186 mg, 0.624 mmol) in place of 2-bromo-4-cyclopropyl-1-methoxybenzene. LCMS: 647.2 (M+H)+.

EXAMPLE 198C 5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine The title compound was prepared as the acetate salt using the procedure described in Example 6E, using Example 198B (400 mg, 0.618 mmol) in place of Example 6D, and purified using preparative HPLC (Zorbax XDB C-18 column with gradient elution from 10M ammonium acetate in water to 1:1 methanol/acetonitrile). LCMS: 447.4 (M+H)+. $^1$H NMR (400 MHz, CD$_3$OD): δ 1.95-1.97 (m, 2H), 2.33-2.37 (m, 3H), 3.14-3.23 (m, 3H), 3.34-3.36 (m, 3H), 3.47-3.51 (m, 4H), 3.58-3.61 (m, 1H), 6.21 (s, 1H), 6.61-6.63 (m, 1H), 7.19 (d, J=4.8 Hz, 1H), 7.57 (d, J=8.8 Hz, 1H), 8.22 (d, J=5.2 Hz, 1H).

EXAMPLE 199

N-benzyl-4-chloro-3-[2-(piperidin-3-yl)-1H-pyrrolo[2,3-b]pyridin-4-yl]aniline

EXAMPLE 199A tert-butyl 3-(4-(5-(benzylamino)-2-chlorophenyl)-1H-pyrrolo[2,3-b]pyridin-2-yl)piperidine-1-carboxylate The title compound was prepared using the procedure described in Example 7A, using Example 53A (200 mg, 0.677 mmol) in place of 2-bromo-4-cyclopropyl-1-methoxybenzene. LCMS: 517.6 (M+H)+.

EXAMPLE 199B

N-benzyl-4-chloro-3-[2-(piperidin-3-yl)-1H-pyrrolo[2,3-b]pyridin-4-yl]aniline

The title compound was prepared as the hydrochloride salt using the procedure described in Example 6E, using Example 199A (400 mg, 0.618 mmol) in place of Example 6D. LCMS: 417.2 (M+H)+. $^1$H NMR (400 MHz, CD$_3$OD): δ 1.88-2.0 (m, 2H), 2.10-2.13 (m, 1H), 2.28-2.31 (m, 1H), 3.06-3.11 (m, 1H), 3.47-3.50 (m, 2H), 3.68-3.71 (m, 1H), 4.58 (s, 2H), 6.49 (s, 1H), 7.30-7.32 (m, 2H), 7.38-7.47 (m, 5H), 7.60 (d, J=6 Hz, 1H), 7.65 (d, J=8.4 Hz, 1H), 8.48 (d, J=6 Hz, 1H).

EXAMPLE 200

N-benzyl-5-chloro-N-methyl-6-[2-(piperidin-3-yl)-1H-pyrrolo[2,3-b]pyridin-4-yl]pyridin-2-amine

EXAMPLE 200A tert-butyl 3-(4-(6-(benzyl(methyl)amino)-3-chloropyridin-2-yl)-1H-pyrrolo[2,3-b]pyridin-2-yl)piperidine-1-carboxylate The title compound was prepared using the procedure described in Example 5B, using Example 46A (219 mg, 0.702 mmol)) in place of 6-bromo-5-methoxypyridin-2-amine.

EXAMPLE 200B

N-benzyl-5-chloro-N-methyl-6-[2-(piperidin-3-yl)-1H-pyrrolo[2,3-b]pyridin-4-yl]pyridin-2-amine The title compound was prepared as trifluoroacetate salt using the procedure described in Example 1H, using Example 200A (100 mg, 0.188 mmol) in place of Example 1G, and purified using preparative HPLC (Zorbax XDB C-18 column with gradient elution from 0.1% trifluoroacetic acid in water to acetonitrile). LCMS: 432.2 (M+H)+. $^1$H NMR (400 MHz, DMSO-d$_6$): δ 1.5-1.6 (m, 1H), 1.68-1.74 (m, 1H), 1.85-1.9 (m, 1H), 1.98-2.02 (m, 1H), 2.78-2.82 (m, 1H), 2.9-3.0 (m, 1H), 3.05 (s, 3H), 3.28-3.31 (m, 1H), 3.45-3.48 (m, 2H), 4.80 (s, 2H), 6.06 (d, J=1.6 Hz, 1H), 6.78 (d, J=8.8 Hz, 1H), 7.18-7.21 (m, 3H), 7.24-7.27 (m, 1H), 7.32-7.35 (m, 2H), 7.73 (d, J=9.2 Hz, 1H), 8.22 (d, J=5.2 Hz, 1H), 8.60-8.62 (m, 1H), 11.8 (s, 1H).

EXAMPLE 201

4-(4,5-difluoro-2-methoxyphenyl)-2-(piperidin-3-yl)-1H-pyrrolo[2,3-b]pyridine

EXAMPLE 201A tert-butyl 3-(4-(4,5-difluoro-2-methoxyphenyl)-1H-pyrrolo[2,3-b]pyridin-2-yl)piperidine-1-carboxylate The title compound was prepared using the procedure described in Example 1G, using (4,5-difluoro-2-methoxyphenyl)boronic acid (95 mg, 0.503 mmol) in place of 5-fluoro-2-methoxyphenylboronic acid.

EXAMPLE 201B 4-(4,5-difluoro-2-methoxyphenyl)-2-(piperidin-3-yl)-1H-pyrrolo[2,3-b]pyridine The title compound was prepared as trifluoroacetate salt using the procedure described in Example 1H, using Example 201A (100 mg, 0.22 mmol) in place of Example 1G, and purified using preparative HPLC (Zorbax XDB C-18 column with gradient elution from 0.1% trifluoroacetic acid in water to 1:1 methanol/acetonitrile). LCMS: 344.1 (M+H)+. $^1$H NMR (400 MHz, DMSO-d$_6$/D$_2$O): δ 1.70-1.74 (m, 2H), 1.89-1.90 (m, 1H), 2.07-2.12 (m, 1H), 2.82-2.84

(m, 1H), 3.09-3.16 (m, 2H), 3.28-3.32 (m, 1H), 3.50-3.52 (m, 1H), 3.74 (s, 3H), 6.10 (s, 1H), 7.05 (d, J=5.2 Hz, 1H), 7.32-7.37 (m, 1H), 7.41-7.46 (m, 1H), 8.19 (s, 1H).

EXAMPLE 202

5-chloro-N-(3,4-difluorobenzyl)-6-[2-(piperidin-3-yl)-1H-pyrrolo[2,3-b]pyridin-4-yl]pyridin-2-amine

EXAMPLE 202A tert-butyl 3-(4-(3-chloro-6-((3,4-difluorobenzyl)amino)pyridin-2-yl)-1H-pyrrolo[2,3-b]pyridin-2-yl)piperidine-1-carboxylate The title compound was prepared using the procedure described in Example 7A, using Example 39A (200 mg, 0.60 mmol) in place of 2-bromo-4-cyclopropyl-1-methoxybenzene. LCMS: 454.5 (M+H)$^+$.

EXAMPLE 202B 5-chloro-N-(3,4-difluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 202A (150 mg, 0.271 mmol) in place of Example 1G, and purified using preparative HPLC (Zorbax XDB C-18 column with gradient elution from 0.1% trifluoroacetic acid in water to 1:1 methanol/acetonitrile). LCMS: 454.5 (M+H)$^+$. $^1$H NMR (400 MHz, DMSO-d$_6$/D$_2$O): δ 1.58-1.75 (m, 2H), 1.87-1.90 (m, 1H), 2.0-2.02 (m, 1H), 2.79-2.84 (m, 1H), 2.96-3.02 (m, 1H), 3.08-3.11 (m, 1H), 3.29-3.32 (m, 1H), 4.42 (s, 2H), 5.98 (s, 1H), 6.65 (d, J=8.8 Hz, 1H), 7.08-7.12 (m, 2H), 7.32-7.37 (m, 2H), 7.62 (d, J=8.8 Hz, 1H), 8.21 (d, J=5.2 Hz, 1H).

EXAMPLE 203

5-chloro-N-(3-fluorobenzyl)-6-[2-(piperidin-3-yl)-1H-pyrrolo[2,3-b]pyridin-4-yl]pyridin-2-amine

EXAMPLE 203A tert-butyl 3-(4-(3-chloro-6-((3-fluorobenzyl)amino)pyridin-2-yl)-1H-pyrrolo[2,3-b]pyridin-2-yl)piperidine-1-carboxylate The title compound was prepared using the procedure described in Example 7A, using Example 33A (49.2 mg, 0.156 mmol) in place of 2-bromo-4-cyclopropyl-1-methoxybenzene. LCMS: 536.5 (M+H)$^+$.

EXAMPLE 203B 5-chloro-N-(3-fluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 203A (75 mg, 0.14 mmol) in place of Example 1G, and purified using preparative HPLC (Zorbax XDB C-18 column with gradient elution from 0.1% trifluoroacetic acid in water to 1:1 methanol/acetonitrile). LCMS: 436.5 (M+H)$^+$. $^1$H NMR (400 MHz, DMSO-d$_6$/D$_2$O): δ 1.52-1.6 (m, 1H), 1.7-1.78 (m, 1H), 1.85-1.92 (m, 1H), 1.98-2.02 (m, 1H), 2.8-2.84 (m, 1H), 2.97-3.0 (m, 1H), 3.05-3.1 (m, 1H), 3.28-3.31 (m, 1H), 3.43-3.46 (m, 1H), 4.46 (s, 2H), 5.91 (s, 1H), 6.66 (d, J=9.2 Hz, 1H), 7.06-7.13 (m, 4H), 7.35-7.36 (m, 1H), 7.61 (d, J=8.8 Hz, 1H), 8.20 (d, J=4.8 Hz).

EXAMPLE 204

5-chloro-N-(4-fluorobenzyl)-6-[2-(piperidin-3-yl)-1H-pyrrolo[2,3-b]pyridin-4-yl]pyridin-2-amine

EXAMPLE 204A 6-bromo-5-chloro-N-(4-fluorobenzyl)pyridin-2-amine

The title compound was prepared using the procedure described in Example 11B, using 4-fluorobenzaldehyde (329 mg, 2.65 mmol) in place of benzaldehyde. LCMS: 316.85 (M+3)$^+$.

EXAMPLE 204B tert-butyl 3-(4-(3-chloro-6-((4-fluorobenzyl)amino)pyridin-2-yl)-1H-pyrrolo[2,3-b]pyridin-2-yl)piperidine-1-carboxylate The title compound was prepared using the procedure described in Example 5B, using Example 204A (222 mg, 0.702 mmol) in place of 6-bromo-5-methoxypyridin-2-amine. LCMS: 537.1 (M+2)$^+$.

EXAMPLE 204C 5-chloro-N-(4-fluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 204B (100 mg, 0.187 mmol) in place of Example 1G, and purified using preparative HPLC (Zorbax XDB C-18 column with gradient elution from 0.1% trifluoroacetic acid in water to 1:1 methanol/acetonitrile). LCMS: 436.1 (M+H)$^+$. $^1$H NMR (400 MHz, DMSO-d$_6$/D$_2$O): δ 1.57-1.60 (m, 1H), 1.71-1.75 (m, 1H), 1.87-1.90 (m, 1H), 2.0-2.03 (m, 1H), 2.79-2.85 (m, 1H), 2.97-3.03 (m, 1H), 3.09-3.12 (m, 1H), 3.29-3.38 (m, 1H), 3.48-3.51 (m, 1H), 4.43 (s, 2H), 6.03 (s, 1H), 6.64 (d, J=8.8 Hz, 1H), 7.11-7.16 (m, 3H), 7.30-7.34 (m, 2H), 7.61 (d, J=8.8 Hz, 1H), 8.23 (d, J=5.2 Hz, 1H).

EXAMPLE 205

N-benzyl-5-chloro-4-[2-(piperidin-3-yl)-1H-pyrrolo[2,3-b]pyridin-4-yl]pyridin-2-amine

EXAMPLE 205A tert-butyl 3-(4-(2-(benzylamino)-5-chloropyridin-4-yl)-1H-pyrrolo[2,3-b]pyridin-2-yl)piperidine-1-carboxylate The title compound was prepared using the procedure described in Example 5B, using Example 52B (150 mg, 0.504 mmol) in place of 6-bromo-5-methoxypyridin-2-amine. LCMS: 518.2 (M+H)+.

EXAMPLE 205B

N-benzyl-5-chloro-4-[2-(piperidin-3-yl)-1H-pyrrolo[2,3-b]pyridin-4-yl]pyridin-2-amine The title compound was prepared as trifluoroacetate salt using the procedure described in Example 1H, using Example 205A (180 mg, 0.34 mmol) in place of Example 1G, and purified using preparative HPLC (Zorbax XDB C-18 column with gradient elution from 0.1% trifluoroacetic acid in water to 1:1 methanol/acetonitrile). LCMS: 418.2 (M+H)+. $^1$H NMR (400 MHz, DMSO-$d_6$): δ 1.64-1.71 (m, 2H), 1.88-2.0 (m, 2H), 2.83-2.86 (m, 2H), 3.03-3.09 (m, 2H), 3.28-3.32 (m, 1H), 4.48 (s, 2H), 5.97 (s, 1H), 6.57 (s, 1H), 7.01 (d, J=5.2 Hz, 1H), 7.24-7.25 (m, 1H), 7.32-7.33 (m, 4H), 8.13 (s, 1H), 8.23 (d, J=4.8 Hz, 1H).

EXAMPLE 206

N-benzyl-4-fluoro-3-[2-(piperidin-3-yl)-1H-pyrrolo[2,3-b]pyridin-4-yl]aniline

EXAMPLE 206A tert-butyl 3-(4-(5-(benzylamino)-2-fluorophenyl)-1H-pyrrolo[2,3-b]pyridin-2-yl)piperidine-1-carboxylate The title compound was prepared using the procedure described in Example 1 G, using Example 51B (190 mg, 0.581 mmol) in place of 5-fluoro-2-methoxyphenylboronic acid. LCMS: 501.6 (M+H)+.

EXAMPLE 206B

N-benzyl-4-fluoro-3-[2-(piperidin-3-yl)-1H-pyrrolo[2,3-b]pyridin-4-yl]aniline

The title compound was prepared as trifluoroacetate salt using the procedure described in Example 1H, using Example 206A (150 mg, 0.30 mmol) in place of Example 1G, and purified using preparative HPLC (Zorbax XDB C-18 column with gradient elution from 0.1% trifluoroacetic acid in water to 1:1 methanol/acetonitrile). LCMS: 401.3 (M+H)+. $^1$H NMR (400 MHz, CD$_3$OD): δ 1.30-1.35 (m, 1H), 1.8-1.94 (m, 2H), 2.10-2.14 (m, 1H), 2.24-2.28 (m, 1H), 3.01-3.08 (m, 1H), 3.15-3.21 (m, 1H), 3.46-3.49 (m, 1H), 3.62-3.65 (m, 1H), 4.40 (s, 2H), 6.25 (s, 1H), 6.81-6.89 (m, 2H), 7.11 (t, J=9.2 Hz, 1H), 7.27-7.31 (m, 2H), 7.34-7.46 (m, 4H), 8.27 (d, J=5.6 Hz, 1H).

EXAMPLE 207

5-chloro-N-(2-fluorobenzyl)-6-[2-(piperidin-3-yl)-1H-pyrrolo[2,3-b]pyridin-4-yl]pyridin-2-amine

EXAMPLE 207A tert-butyl 3-(4-(3-chloro-6-((2-fluorobenzyl)amino)pyridin-2-yl)-1H-pyrrolo[2,3-b]pyridin-2-yl)piperidine-1-carboxylate The title compound was prepared using the procedure described in Example 5B, using Example 38A (222 mg, 0.702 mmol) in place of 6-bromo-5-methoxypyridin-2-amine. LCMS: 536.2 (M+H)+.

EXAMPLE 207B 5-chloro-N-(2-fluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 207A (100 mg, 0.187 mmol) in place of Example 1G, and purified using preparative HPLC (Zorbax XDB C-18 column with gradient elution from 0.1% trifluoroacetic acid in water to 1:1 methanol/acetonitrile). LCMS: 436.4 (M+H)+. $^1$H NMR (400 MHz, DMSO-$d_6$): δ 1.57-1.61 (m, 1H), 1.71-1.75 (m, 1H), 1.87-1.91 (m, 1H), 1.99-2.03 (m, 1H), 2.80-2.83 (m, 1H), 2.99-3.12 (m, 2H), 3.30-3.38 (m, 1H), 3.45-3.48 (m, 1H), 4.50 (s, 2H) 5.97 (s, 1H), 6.69 (d, J=8.8 Hz, 1H), 7.11-7.20 (m, 3H), 7.29-7.38 (m, 2H), 7.47 (brs, 1H), 7.61 (dd, J=1.6, 8.8 Hz, 1H), 8.62 (brs, 1H), 11.8 (s, 1H).

EXAMPLE 208

5-chloro-6-[2-(piperidin-3-yl)-1H-pyrrolo[2,3-b]pyridin-4-yl]-N-(pyridin-3-ylmethyl)pyridin-2-amine

EXAMPLE 208A tert-butyl 3-(4-(3-chloro-6-((pyridin-3-ylmethyl)amino)pyridin-2-yl)-1H-pyrrolo[2,3-b]pyridin-2-yl)piperidine-1-carboxylate The title compound was prepared using the procedure described in Example 7A, using Example 34A (200 mg, 0.67 mmol) in place of 2-bromo-4-cyclopropyl-1-methoxybenzene. LCMS: 519.4 (M+H)+.

EXAMPLE 208B 5-chloro-6-[2-(piperidin-3-yl)-1H-pyrrolo[2,3-b]pyridin-4-yl]-N-(pyridin-3-ylmethyl)pyridin-2-amine The title compound was prepared as the trifluoroacetate salt using the procedure described in Example 1H, using Example 208A (200 mg, 0.385 mmol) in place of Example 1G, and purified using preparative HPLC (Zorbax XDB C-18 column with gradient elution from 0.1% trifluoroacetic acid in water to 1:1 methanol/acetonitrile). LCMS: 419.1 (M+H)+. $^1$H NMR (400 MHz, CD$_3$OD): δ 1.82-1.95 (m, 2H), 2.08-2.12 (m, 1H), 2.26-2.29 (m, 1H), 3.02-3.09 (m, 1H), 3.17-3.23 (m, 1H), 3.46-3.49 (m, 2H), 4.73 (s, 2H), 6.33 (s, 1H), 6.77 (d, J=8.8 Hz, 1H), 7.23 (d, J=5.6 Hz, 1H), 7.65 (d, J=8.8 Hz, 1H), 7.93 (dd, J=5.6, 8.4 Hz, 1H), 8.30 (d, J=5.6 Hz, 1H), 8.49 (d, J=8 Hz, 1H), 8.67 (d, J=5.2 Hz, 1H), 8.72 (d, J=1.6 Hz, 1H).

EXAMPLE 209

4-[3-chloro-6-(pyridin-3-ylmethoxy)pyridin-2-yl]-2-(piperidin-3-yl)-1H-pyrrolo[2,3-b]pyridine

EXAMPLE 209A 2-bromo-3-chloro-6-(pyridin-3-ylmethoxy)pyridine 6-(benzyloxy)-2-bromo-3-chloropyridine The title compound was prepared using the procedure described in Example 58B, using pyridin-3-ylmethanol (352 mg, 3.26 mmol) in place of benzyl alcohol. LCMS: 300 (M+3)$^+$.

EXAMPLE 209B tert-butyl 3-(4-(3-chloro-6-(pyridin-3-ylmethoxy)pyridin-2-yl)-1H-pyrrolo[2,3-b]pyridin-2-yl)piperidine-1-carboxylate The title compound was prepared using the procedure described in Example 7A, using Example 209A (300 mg, 1.0 mmol) in place of 2-bromo-4-cyclopropyl-1-methoxybenzene. LCMS: 520.1 (M+H)$^+$.

EXAMPLE 209C

4-[3-chloro-6-(pyridin-3-ylmethoxy)pyridin-2-yl]-2-(piperidin-3-yl)-1H-pyrrolo[2,3-b]pyridine The title compound was prepared as the trifluoroacetate salt using the procedure described in Example 1H, using Example 209B (250 mg, 0.481 mmol) in place of Example 1G, and purified using preparative HPLC (Zorbax XDB C-18 column with gradient elution from 0.1% trifluoroacetic acid in water to 1:1 methanol/acetonitrile). LCMS: 420.15 (M+H)$^+$. $^1$H NMR (400 MHz, DMSO-d$_6$/D$_2$O): δ 1.65-1.75 (m, 2H), 1.88-1.91 (m, 1H), 2.07-2.10 (m, 1H), 2.80-2.87 (m, 1H), 3.04-3.15 (m, 2H), 3.29-3.32 (m, 1H), 3.50-3.52 (m, 1H), 5.41 (s, 2H), 6.08 (s, 1H), 7.07 (d, J=8.8 Hz, 1H), 7.18 (d, J=4.8 Hz, 1H), 7.60 (dd, J=5.6, 8 Hz, 1H), 8.02 (d, J=8.8 Hz, 1H), 8.07 (d, J=7.6 Hz, 1H), 8.27 (d, J=4.8 Hz, 1H), 8.64 (dd, J=1.2, 5.2 Hz, 1H), 8.72 (d, J=1.6 Hz, 1H).

EXAMPLE 210

5-chloro-N-[(5-fluoropyridin-3-yl)methyl]-6-[2-(piperidin-3-yl)-1H-pyrrolo[2,3-b]pyridin-4-yl]pyridin-2-amine

EXAMPLE 210A tert-butyl 3-(4-(3-chloro-6-(((5-fluoropyridin-3-yl)methyl)amino)pyridin-2-yl)-1H-pyrrolo[2,3-b]pyridin-2-yl)piperidine-1-carboxylate The title compound was prepared using the procedure described in Example 7A, using Example 37A (200 mg, 0.63 mmol) in place of 2-bromo-4-cyclopropyl-1-methoxybenzene. LCMS: 537.5 (M+H)$^+$.

EXAMPLE 210B 5-chloro-N-[(5-fluoropyridin-3-yl)methyl]-6-[2-(piperidin-3-yl)-1H-pyrrolo[2,3-b]pyridin-4-yl]pyridin-2-amine The title compound was prepared as trifluoroacetate salt using the procedure described in Example 1H, using Example 210A (200 mg, 0.458 mmol) in place of Example 1G, and purified using preparative HPLC (Agilent XDB C-18 column with gradient elution from 0.1% trifluoroacetic acid in water to 1:1 methanol/acetonitrile). LCMS: 437.1 (M+H)$^+$. $^1$H NMR (400 MHz, CD$_3$OD): δ 1.31-1.35 (m, 1H), 1.82-1.94 (m, 2H), 2.08-2.13 (m, 1H), 2.23-2.27 (m, 1H), 3.05-3.07 (m, 1H), 3.17-3.23 (m, 1H), 3.46-3.49 (m, 1H), 3.65-3.68 (m, 1H), 4.62 (s, 2H), 6.26 (s, 1H), 6.73 (d, J=8.8 Hz, 1H), 7.38 (d, J=6 Hz, 1H), 7.63 (d, J=9.2 Hz, 2H), 8.32 (d, J=5.2 Hz, 1H), 8.37-8.38 (m, 2H).

EXAMPLE 211

N-benzyl-5-fluoro-4-[2-(piperidin-3-yl)-1H-pyrrolo[2,3-b]pyridin-4-yl]pyridin-2-amine

EXAMPLE 211A tert-butyl 3-(4-(2,5-difluoropyridin-4-yl)-1H-pyrrolo[2,3-b]pyridin-2-yl)piperidine-1-carboxylate To a solution of Example 5A (100 mg, 0.234 mmol) and 2,5-difluoro-4-iodopyridine (200 mg, 0.830 mmol) in 3.5 mL of 1,2-dimethoxyethane was added 1.5 mL saturated sodium bicarbonate solution and the mixture was degassed with nitrogen. 1,1'-Bis(diphenylphosphino)ferrocene-palladium(II)dichloride dichloromethane complex (33.9 mg, 0.041 mmol) was added and the mixture was heated at 100° C. for 2 hours. The mixture was cooled to room temperature, diluted with ethyl acetate and filtered through diatomaceous earth. The combined organic layers were washed with water and brine (25 mL each) and dried over sodium sulfate. Filtration, concentration and purification by column chromatography (silica gel, 50% ethyl acetate-hexane) afforded the title compound. LCMS: 415.4 (M+H)$^+$.

EXAMPLE 211B tert-butyl 3-(4-(2-(benzylamino)-5-fluoropyridin-4-yl)-1H-pyrrolo[2,3-b]pyridin-2-yl)piperidine-1-carboxylate To Example 211A (120 mg, 0.290 mmol) and phenylmethanamine (62.1 mg, 0.579 mmol) in 2 mL dimethylsulfoxide was added N-ethyl-N-isopropylpropan-2-amine (0.076 ml, 0.434 mmol). The mixture was heated in sealed tube at 120° C. for 4 hours, cooled to room temperature and diluted with water. The mixture was extracted with ethyl acetate (50 mL×3), dried over sodium sulfate, filtered and concentrated to provide the crude product which was recrystallised from 1:10 ethyl acetate-hexane to afford the title compound. LCMS: 502.4 (M+H)$^+$.

EXAMPLE 211C

N-benzyl-5-fluoro-4-[2-(piperidin-3-yl)-1H-pyrrolo[2,3-b]pyridin-4-yl]pyridin-2-amine The title compound was prepared as the trifluoroacetate salt using the procedure described in Example 1H, using Example 211B (100 mg, 0.199 mmol) in place of Example 1G, and purified using preparative HPLC (AG/AD/PP/C-18 column with gradient elution from 0.1% trifluoroacetic acid in water to 1:1 methanol/acetonitrile). LCMS: 402.3 (M+H)$^+$. $^1$H NMR (400 MHz, CD$_3$OD): δ 1.31-1.35 (m, 1H), 1.83-1.95 (m, 2H), 2.10-2.13 (m, 1H), 2.25-2.29 (m, 1H), 3.01-3.07 (m, 1H), 3.16-3.22 (m, 1H), 3.47-3.50 (m, 1H), 3.64-3.68 (m, 1H), 4.61 (s, 2H), 6.29 (d, J=2 Hz, 1H), 7.02 (d, J=5.2 Hz, 1H), 7.27 (dd, J=1.2, 5.2 Hz, 1H), 7.34-7.44 (m, 5H), 8.12 (d, J=3.2 Hz, 1H), 8.32 (d, J=5.6 Hz, 1H).

EXAMPLE 212

N-benzyl-4-fluoro-6-[2-(piperidin-3-yl)-1H-pyrrolo[2,3-b]pyridin-4-yl]pyridin-2-amine

EXAMPLE 212A

N-benzyl-6-chloro-4-nitropyridin-2-amine

To a solution of 2,6-dichloro-4-nitropyridine (0.1 g, 0.518 mmol) and benzyl amine (0.062 mL, 0.570 mmol) in 10 mL toluene was added cesium carbonate (0.253 g, 0.777 mmol). The mixture was degassed with nitrogen and 2,2'-bis(diphenylphosphino)-1,1'-binaphthalene (0.016 g, 0.026 mmol) and palladium acetate (5.82 mg, 0.026 mmol) were added. The mixture was heated at 100° C. for 2 hours, filtered through diatomaceous earth and concentrated. The residue was dissolved in ethyl acetate, washed with water and brine, dried over sodium sulfate, filtered, and concentrated. Recrystallization from 1:10 ethyl acetate-hexane afforded the title compound.

EXAMPLE 212B

N-benzyl-6-chloro-4-fluoropyridin-2-amine

A solution of Example 212A (70 mg, 0.265 mmol) in 3 mL of N,N-dimethylformamide was treated with 1M tetra-n-butyl ammonium fluoride in tetrahydrofuran (0.531 mL, 0.531 mmol) and the mixture was heated at 65° C. for 12 hours. The mixture was poured into 30 mL 1:1 water/ethyl acetate and the organic layer was washed with water and brine, dried over sodium sulfate, filtered, and concentrated. Purification by column chromatography (silica, 5% ethyl acetate-hexane) afforded the title compound. LCMS: 236.8 (M+H)$^+$.

EXAMPLE 212C tert-butyl 3-(4-(6-(benzylamino)-4-fluoropyridin-2-yl)-1H-pyrrolo[2,3-b]pyridin-2-yl)piperidine-1-carboxylate The title compound was prepared using the procedure described in Example 5B, using Example 212B (61 mg, 0.257 mmol) in place of 6-bromo-5-methoxypyridin-2-amine. LCMS: 502.2 (M+H)$^+$.

EXAMPLE 212D

N-benzyl-4-fluoro-6-[2-(piperidin-3-yl)-1H-pyrrolo[2,3-b]pyridin-4-yl]pyridin-2-amine The title compound was prepared as the trifluoroacetate salt using the procedure described in Example 1H, using Example 212C (60 mg, 0.119 mmol) in place of Example 1G, and purified using preparative HPLC (Waters 'X'Bridge column with gradient elution from 0.1% trifluoroacetic acid in water to acetonitrile). LCMS: 402.2 (M+H)$^+$. $^1$H NMR (400 MHz, CD$_3$OD): δ 1.65-1.69 (m, 1H), 1.88-1.92 (m, 1H), 2.05-2.09 (m, 1H), 2.16-2.19 (m, 1H), 2.96-3.08 (m, 2H), 3.26-3.3.29 (m, 1H), 3.44-3.47 (m, 1H), 3.61-3.63 (m, 1H), 4.74 (s, 2H), 6.46 (dd, J=2, 11.2 Hz, 1H), 6.93 (s, 1H), 7.14 (dd, J=2, 9.2 Hz, 1H), 7.28-7.31 (m, 1H), 7.36-7.44 (m, 4H), 7.70 (d, J=5.6 Hz, 1H), 8.32 (d, J=5.6 Hz, 1H).

EXAMPLE 213

N-benzyl-4-[5-chloro-2-(piperidin-3-yl)-1H-pyrrolo[2,3-b]pyridin-4-yl]pyridin-2-amine

EXAMPLE 213A

N-benzyl-4-(4,4,5,5-tetramethyl-1,3,2-dioxaborolan-2-yl)pyridin-2-amine

The title compound was prepared using the procedure described in Example 6C, using N-benzyl-4-bromopyridin-2-amine (250 mg, 0.95 mmol) in place of Example 6B. LCMS: 296.7 (M+H)$^+$.

EXAMPLE 213B tert-butyl 3-(4-(2-(benzylamino)pyridin-4-yl)-5-chloro-1H-pyrrolo[2,3-b]pyridin-2-yl)piperidine-1-carboxylate The title compound was prepared using the procedure described in Example 7A, using Example 213A (292 mg, 0.940 mmol) in place of Example 5A and Example 78B (300 mg, 0.723 mmol) in place of 2-bromo-4-cyclopropyl-1-methoxybenzene. LCMS: 518.2 (M+H)$^+$.

EXAMPLE 213C

N-benzyl-4-[5-chloro-2-(piperidin-3-yl)-1H-pyrrolo[2,3-b]pyridin-4-yl]pyridin-2-amine The title compound was prepared as the acetate salt using the procedure described in Example 6E, using Example 213B (250 mg, 0.483 mmol) in place of Example 6D, and purified using preparative HPLC (AG/AD/PP/C-18 column with gradient elution from 10M ammonium acetate in water to 1:1 methanol/acetonitrile). LCMS: 418.1 (M+H)$^+$. $^1$H NMR (400 MHz, DMSO-d$_6$/D$_2$O): δ 1.50-1.52 (m, 2H), 1.6-1.66 (m, 1H), 1.98-2.05 (m, 1H), 2.55-2.66 (m, 2H), 2.82-2.84 (m, 1H), 2.92-2.95 (m, 1H), 3.13-3.15 (m, 1H), 4.48 (s, 2H), 5.82 (s, 1H), 6.53-6.56 (m, 2H), 7.1-7.22 (m, 1H), 7.28-7.35 (m, 4H), 8.07 (d, J=5.2 Hz, 1H), 8.17 (s, 1H).

EXAMPLE 214

4-fluoro-N-(3-fluorobenzyl)-3-[2-(piperidin-3-yl)-1H-pyrrolo[2,3-b]pyridin-4-yl]aniline

EXAMPLE 214A tert-butyl 3-(4-(2-fluoro-5-(((3-fluorobenzyl)amino)phenyl)-1H-pyrrolo[2,3-b]pyridin-2-yl)piperidine-1-carboxylate The title compound was prepared using the procedure described in Example 1 G, using Example 51B (308 mg, 0.893 mmol) in place of 5-fluoro-2-methoxyphenylboronic acid. LCMS: 519.4 (M+H)$^+$.

EXAMPLE 214B 4-fluoro-N-(3-fluorobenzyl)-3-[2-(piperidin-3-yl)-1H-pyrrolo[2,3-b]pyridin-4-yl]aniline The title compound was prepared as the trifluoroacetate salt using the procedure described in Example 1H, using Example 214A (150 mg, 0.28 mmol) in place of Example 1G, and purified using preparative HPLC (Agilent XDB C-18 column with gradient elution from 0.1% trifluoroacetic acid in water to 1:1 methanol/acetonitrile). LCMS: 419.55 (M+H)$^+$. $^1$H NMR (400 MHz, CD$_3$OD): δ 1.81-1.94 (m, 2H), 2.10-2.14 (m, 1H), 2.25-2.28 (m, 1H), 3.05-3.08 (m, 1H), 3.14-3.22 (m, 1H), 3.46-3.51 (m, 2H), 3.63-3.66 (m, 1H), 4.40 (s, 2H), 6.26 (d, J=2 Hz, 1H), 6.74-6.76 (m, 1H), 6.79-6.83 (m, 1H), 7.0-7.02 (m, 1H), 7.06-7.09 (m, 1H), 7.15 (d, J=10.4 Hz, 1H), 7.23 (d, J=7.6 Hz, 1H), 7.28 (dd, J=1.2, 5.2 Hz, 1H), 7.34-7.38 (m, 1H), 8.28 (d, J=5.6 Hz, 1H).

EXAMPLE 215

4-[4-(5-fluoro-2-methoxyphenyl)-1H-pyrrolo[2,3-b]pyridin-2-yl]-N-methyl-3,6-dihydropyridine-1(2H)-carboxamide To a suspension of Example 87D (70.0 mg, 0.177 mmol) in N,N-dimethylformamide (2 mL) was added n-succinimidyl-n-methylcarbamate (45.6 mg, 0.265 mmol) and triethylamine (0.148 mL, 1.06 mmol) and the mixture was stirred overnight. Water was slowly added and the solids were filtered, rinsed with water, and oven-dried to provide the title compound. $^1$H NMR (400 MHz, DMSO-d$_6$) δ 2.44 (bs, 2H), 2.59 (d, J=3.3 Hz, 3H), 3.50 (t, J=5.6 Hz, 2H), 3.74 (s, 3H), 3.97-4.03 (m, 2H), 6.22-6.27 (m, 1H), 6.41-6.54 (m, 2H), 7.04 (d, J=4.9 Hz, 1H), 7.15-7.31 (m, 3H), 8.20 (d, J=4.9 Hz, 1H), 11.81 (bs, 1H) MS (ESI$^+$) m/z 381.1 (M+H)$^+$.

EXAMPLE 216

4-[4-(5-fluoro-2-methoxyphenyl)-1H-pyrrolo[2,3-b]pyridin-2-yl]-3,6-dihydropyridine-1(2H)-sulfonamide

EXAMPLE 216A tert-butyl (4-(4-(5-fluoro-2-methoxyphenyl)-1H-pyrrolo[2,3-b]pyridin-2-yl)-5,6-dihydropyridin-1(2H)-yl)sulfonylcarbamate To a solution of Example 87 (235 mg, 0.727 mmol) in dichloromethane (10 mL) was added triethylamine (0.203 mL, 1.453 mmol) and (tert-butoxycarbonyl)((4-(dimethylamino)pyridin-1-ium-1-yl)sulfonyl)amide (219 mg, 727 mmol). The mixture was stirred at room temperature overnight and directly loaded onto a silica gel cartridge, eluting with a gradient of 0-15% methanol in dichloromethane to provide the title compound. MS (DCI/NH$_3$) m/z 503 (M+H)$^+$.

EXAMPLE 216B

4-[4-(5-fluoro-2-methoxyphenyl)-1H-pyrrolo[2,3-b]pyridin-2-yl]-3,6-dihydropyridine-1(2H)-sulfonamide To a solution of Example 216A (209 mg, 0.416 mmol) in dichloromethane (5 mL) was added trifluoroacetic acid (1 mL) and the solution was stirred at room temperature for 2 hours. After concentration, the residue was dissolved in methanol (3 mL) and the crystallized material that formed was collected by filtration. The filtrate was concentrated and the residue was purified by HPLC (Zorbax, C-18 column), eluting with a gradient of 0-100% 0.1% trifluoroacetic acid in water/acetonitrile. The combined material was suspended in 1:1 methanol/dichloromethane (10 mL), treated with 2M hydrogen chloride in ether and concentrated to provide the title compound as the hydrochloride salt. $^1$H NMR (400 MHz, DMSO-d$_6$): δ2.63 (m, 2 H), 3.21 (t, J=5.80 Hz, 2 H), 3.76 (s, 3 H), 6.43 (d, J=1.53 Hz, 1 H), 6.65 (s, 1H), 6.89 (s, 2 H), 7.21-7.38 (m, 4 H), 8.30 (d, J=5.49 Hz, 1 H), 12.56 (s, 1 H); MS (DCI/NH$_3$) m/z 403 (M+H)$^+$.

EXAMPLE 217

N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide To a mixture of Example 87 (80.0 mg, 0.202 mmol) and triethylamine (0.062 mL, 0.444 mmol) in dichloromethane (2 mL) and methanol (2 mL) was added acetic acid (0.058 mL, 1.009 mmol), N-(4-formylphenyl)acetamide (65.9 mg, 0.404 mmol), and MP-cyanoborohydride (Biotage, 324 mg, 2.49 mmol/g) and the mixture was stirred overnight. The solid was filtered and rinsed with dichloromethane/methanol. The filtrate was concentrated and purified by reverse-phase HPLC on a Zorbax RX-C18 column (250×21.2 mm, 7 μm particle size) using a gradient of 10-95% acetonitrile in 0.1% aqueous trifluoroacetic acid to provide the title compound as a trifluoroacetic acid salt. $^1$H NMR (400 MHz, Methanol-d$_4$) δ 2.15 (s, 3H), 2.93 (bs, 2H), 3.59-3.73 (m, 1H), 3.79 (s, 3H), 3.98 (s, 3H), 4.43 (s, 2H), 6.45-6.51 (m, 1H), 6.62 (s, 1H), 7.16-7.29 (m, 3H), 7.40 (d, J=5.7 Hz, 1H), 7.46-7.53 (m, 2H), 7.68-7.74 (m, 2H), 8.31 (d, J=5.7 Hz, 1H). MS (ESI$^+$) m/z 471.1 (M+H)$^+$.

EXAMPLE 218 tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate

EXAMPLE 218A (tert-butoxycarbonyl)((4-(dimethylamino)pyridin-1-ium-1-yl)sulfonyl)amide To a solution of tert-butanol (2.6 mL, 27.2 mmol) in dichloromethane (20 mL) was added dropwise with ice cooling chlorosulfonyl isocyanate (2.4 mL, 27.6 mL) over 15 minutes. After stirring for 15 minutes, 4-(dimethylamino)pyridine (6.9 g, 56.5 mmol) was added, the cooling bath was removed and dichloromethane (100 mL) was added. The mixture was stirred at room temperature for 1 hour and diluted with 130 mL of dichloromethane. The mixture was washed with water and brine, dried over sodium sulfate, filtered, and concentrated in vacuo to yield the title compound as a crystalline solid. MS (DCI/NH$_3$) m/z 301 (M+H)$^+$.

EXAMPLE 218B tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate To a solution of Example 87D (235 mg, 0.727 mmol) in dichloromethane (10 mL) was added triethylamine (0.203 mL, 1.453 mmol) and Example 218A (219 mg, 727 mmol). The mixture was stirred at room temperature overnight and directly loaded onto silica gel (Teledyne Combinflash Rf) eluting with a gradient of 0-15% methanol in dichloromethane to provide the title compound. $^1$H NMR (400 MHz, DMSO-d$_6$): δ1.39 (s, 9H), 2.57 (br s, 2 H), 3.46 (t, J=5.65 Hz, 2 H), 3.74 (s, 3 H), 4.02 (d, J=2.14 Hz, 2 H), 6.26 (d, J=1.83 Hz, 1 H), 6.51 (s, 1 H), 7.04 (d, J=4.88 Hz, 1 H), 7.17-7.31 (m, 3 H), 8.21 (d, J=4.88 Hz, 1 H), 11.07 (s, 1 H), 11.86 (d, J=1.83 Hz, 1 H). MS (DCI/NH$_3$) m/z 503 (M+H)$^+$.

EXAMPLE 219

4-[4-(5-fluoro-2-methoxyphenyl)-1H-pyrrolo[2,3-b]pyridin-2-yl]cyclohex-3-ene-1-carboxylic acid

EXAMPLE 219A 4-(5-fluoro-2-methoxyphenyl)-2-iodo-1H-pyrrolo[2,3-b]pyridine

To a solution of Example 87B (4 g, 7.87 mmol) in 75 mL dioxane was added 6M aqueous sodium hydroxide (13.12 mL, 79 mmol). The mixture was heated at 100° C. for 1 hour, cooled, and reduced to half volume in vacuo. The residue was diluted with 50 mL ethyl acetate, washed with saturated sodium bicarbonate and brine, dried over magnesium sulfate, filtered, and concentrated to provide the title compound. LCMS: 369.53 (M+H)$^+$.

EXAMPLE 219B ethyl 4-(4-(5-fluoro-2-methoxyphenyl)-1H-pyrrolo[2,3-b]pyridin-2-yl)cyclohex-3-enecarboxylate To a solution of Example 219A (500 mg, 1.358 mmol), ethyl 4-(4,4,5,5-tetramethyl-1,3,2-dioxaborolan-2-yl)cyclohex-3-enecarboxylate (495 mg, 1.766 mmol), and bis(triphenylphosphine)palladium(II) dichloride (95 mg, 0.136 mmol) in 30 mL 7:2:3 1,2-dimethoxyethane/ethanol/water was added sodium carbonate (432 mg, 4.07 mmol). The mixture was heated at 100° C. for 4 hours, cooled to room temperature, and diluted with 50 mL ethyl acetate. The mixture was washed with saturated sodium bicarbonate, water and brine, dried over magnesium sulfate, filtered, and concentrated. The residue was triturated with ethyl acetate and the solid was filtered and dried in vacuo to provide the title compound. MS (ESI): 395.2 (M+H)$^+$.

EXAMPLE 219C

4-[4-(5-fluoro-2-methoxyphenyl)-1H-pyrrolo[2,3-b]pyridin-2-yl]cyclohex-3-ene-1-carboxylic acid To a solution of Example 219B (350 mg, 0.887 mmol) in 10 mL dioxane was added 6M aqueous sodium hydroxide (1.479 mL, 8.87 mmol). The mixture was heated at 50° C. for 12 hours, cooled and diluted with 25 mL water. The basic aqueous layer was extracted with ethyl acetate (twice) and the organics were discarded. To the basic aqueous layer was added 25 mL ethyl acetate and the aqueous layer made slightly acidic with 2.5M hydrochloric acid. The aqueous layer was extracted with ethyl acetate (twice) and the combined organics were washed with brine, dried over magnesium sulfate, filtered and concentrated to provide the title compound. $^1$H NMR (400 MHz, DMSO-d$_6$) δ 1.60-1.77 (m, 1 H) 1.99-2.12 (m, 1 H) 2.28-2.46 (m, 3 H) 2.53 (dd, J=7.78, 2.90 Hz, 2 H) 3.62-3.89 (m, 3 H) 6.18 (d, J=1.83 Hz, 1 H) 6.53 (s, 1 H) 7.02 (d, J=4.88 Hz, 1 H) 7.08-7.42 (m, 3 H) 8.17 (d, J=4.88 Hz, 1 H) 11.73 (d, J=1.53 Hz, 1 H) 11.96-12.37 (m, J=2.44 Hz, 1 H); MS (ESI): 367.2 (M+H)$^+$.

EXAMPLE 220

4-(2,3-difluorophenyl)-2-[1-(methylsulfonyl)-1,2,3,6-tetrahydropyridin-4-yl]-1H-pyrrolo[2,3-b]pyridine

EXAMPLE 220A 4-bromo-1-tosyl-1H-pyrrolo[2,3-b]pyridine

To a suspension of 4-bromo-1H-pyrrolo[2,3-b]pyridine (15 g, 76 mmol) and p-toluenesulfonyl chloride (21.77 g, 114 mmol) in toluene (200 mL) was added a solution of tetrabutylammonium hydrogen sulfate (2.58 g, 7.61 mmol) in water (10 mL) and the mixture was cooled to 0° C. A solution of sodium hydroxide (9.13 g, 228 mmol) in water (30 mL) was added and the mixture was stirred at room temperature overnight. The mixture was diluted with ethyl acetate and the solution was washed with saturated sodium chloride. The organic layer was dried over sodium sulfate, filtered and concentrated to provide the title compound. MS (CI) m/z 352 (M+H)$^+$.

EXAMPLE 220B 4-bromo-2-iodo-1-tosyl-1H-pyrrolo[2,3-b]pyridine

To a solution of Example 220A (25 g, 71.2 mmol) in tetrahydrofuran (600 mL) at −78° C. was added slowly 2M lithium diisopropylamide (39.1 mL, 78 mmol) and the mixture was stirred at −78° C. for 1 hour. A solution of iodine (19.87 g, 78 mmol) in tetrahydrofuran (100 mL) was added slowly and the reaction was allowed to warm to room temperature gradually. The reaction mixture was stirred at room temperature for 3 hours and was quenched with saturated aqueous sodium thiosulfate, water and ethyl acetate. The aqueous layer was extracted with ethyl acetate and the combined organics were dried over sodium sulfate, filtered and concentrated to provide the title compound. MS (CI) m/z 477 (M+H)$^+$.

EXAMPLE 220C tert-butyl 4-(4-bromo-1-tosyl-1H-pyrrolo[2,3-b]pyridin-2-yl)-5,6-dihydropyridine-1(2H)-carboxylate To as solution of Example 220B (20 g, 41.9 mmol), tert-butyl 4-(4,4,5,5-tetramethyl-1,3,2-dioxaborolan-2-yl)-5,6-dihydropyridine-1(2H)-carboxylate (16.85 g, 54.5 mmol), and tetrakis(triphenylphosphine)palladium (4.84 g, 4.19 mmol) in N,N-dimethylformamide (500 mL) was added a solution of sodium bicarbonate (7.04 g, 84 mmol) in water (40 mL) and the mixture was stirred at 80° C. for 12 hours. The reaction was quenched by the addition of saturated aqueous sodium thiosulfate, water and ethyl acetate. The aqueous layer was extracted with ethyl acetate and the combined organics were dried over sodium sulfate, filtered and concentrated to provide the title compound. MS (CI) m/z 532 (M+H)$^+$.

EXAMPLE 220D 4-bromo-2-(1,2,3,6-tetrahydropyridin-4-yl)-1-tosyl-1H-pyrrolo[2,3-b]pyridine A mixture of Example 220C (8 g, 15.02 mmol) and trifluoroacetic acid (11.58 mL, 150 mmol) in dichloromethane (100 mL) was stirred at 20° C. for 12 hours. The mixture was concentrated to provide the title compound as a trifluoroacetate salt. MS (CI) m/z 432 (M+H)$^+$.

EXAMPLE 220E 4-bromo-2-(1-(methylsulfonyl)-1,2,3,6-tetrahydropyridin-4-yl)-1-tosyl-1H-pyrrolo[2,3-b]pyridine A mixture of Example 220D (6 g, 13.88 mmol) and triethylamine (9.67 mL, 69.4 mmol) in N,N-dimethylformamide (150 mL) was cooled to 0° C. in an ice bath. Methanesulfonyl chloride (2.16 mL, 27.8 mmol) was added and the mixture was stirred at 0° C. for 2 hours. The mixture was diluted with water and filtered and the precipitate was washed with water to provide the title compound. MS (CI) m/z 511 (M+H)$^+$.

EXAMPLE 220F 4-bromo-2-(1-(methylsulfonyl)-1,2,3,6-tetrahydropyridin-4-yl)-1H-pyrrolo[2,3-b]pyridine To a solution of Example 220E (6.5 g, 12.73 mmol) in 1,4-dioxane (50 mL) was added a solution of sodium hydroxide (1.528 g, 38.2 mmol) in water (5 mL) and the mixture was stirred at 60° C. for 12 hours. The mixture was concentrated and the residue was suspended in water and N,N-dimethylformamide. The mixture was filtered and the solid was washed with ethyl acetate to provide the title compound. MS (CI) m/z 356 (M+H)$^+$.

EXAMPLE 220G 4-(2,3-difluorophenyl)-2-[1-(methylsulfonyl)-1,2,3,6-tetrahydropyridin-4-yl]-1H-pyrrolo[2,3-b]pyridine A mixture of Example 220F (120 mg, 0.337 mmol), (2,3-difluorophenyl)boronic acid (53.2 mg, 0.337 mmol), sodium carbonate (89 mg, 0.842 mmol), and [1,1'-bis(diphenylphosphino)ferrocene]dichloropalladium(II)-dichloromethane adduct (27.5 mg, 0.034 mmol) in toluene (4 mL), water (1 mL), and butan-1-ol (2 mL) was degassed with nitrogen and the mixture was heated at 100° C. for 3 hours. The solvent was removed under reduced pressure and the residue was purified by reverse-phase HPLC on a SunFire C18 column using a gradient of 25-52% acetonitrile in 0.05% aqueous trifluoroacetic acid to provide the title compound as a trifluoroacetate salt. $^1$H NMR (400 MHz, DMSO-d$_6$) δ 2.63 (s, 2H), 2.95 (s, 3H), 3.36 (t, J=5.6 Hz, 2H), 3.92 (d, J=2.0 Hz, 2H), 6.42 (s, 1H), 6.58 (s, 1H), 7.14 (d, J=5.2 Hz, 1H), 7.38-7.41 (m, 1H), 7.44-7.47 (m, 1H), 7.55-7.58 (m, 1H), 8.29 (d, J=5.2 Hz, 1H), 12.07 (s, 1H). MS (ESI$^+$) m/z 390.1 (M+H)$^+$.

EXAMPLE 221

3-{4-[4-(5-fluoro-2-methoxyphenyl)-1H-pyrrolo[2,3-b]pyridin-2-yl]-3,6-dihydropyridin-1(2H)-yl}-3-oxopropanenitrile The title compound was prepared essentially as described in Example 100, substituting 2-cyanoacetic acid for acetic acid. The crude compound was purified by reverse-phase HPLC performed on a Zorbax RX-C18 column using a gradient of 15-100% methanol in 0.1% aqueous trifluoroacetic acid to afford the title compound as a trifluoroacetate salt. $^1$H NMR (400 MHz, DMSO-d$_6$) δ 2.46-2.49 (m, 1H), 2.60 (bs, 1H), 3.55 (t, J=5.7 Hz, 1H), 3.67 (t, J=5.7 Hz, 1H), 3.74 (d, J=1.3 Hz, 3H), 4.09 (s, 1H), 4.14-4.18 (m, 3H), 6.31 (dd, J=5.2, 2.0 Hz, 1H), 6.52 (dt, J=6.5, 3.5 Hz, 1H), 7.10 (dd, J=5.1, 3.5 Hz, 1H), 7.15-7.39 (m, 3H), 8.24 (d, J=5.0 Hz, 1H), 11.89-12.19 (m, 1H). MS (ESI$^+$) m/z 391.2 (M+H)$^+$.

EXAMPLE 222

4-[4-(2,3-difluorophenyl)-1H-pyrrolo[2,3-b]pyridin-2-yl]-N-methyl-3,6-dihydropyridine-1(2H)-carboxamide

EXAMPLE 222A tert-butyl 4-(4-(2,3-difluorophenyl)-1-tosyl-1H-pyrrolo[2,3-b]pyridin-2-yl)-5,6-dihydropyridine-1(2H)-carboxylate A mixture of Example 220C (750.0 mg, 1.409 mmol), (2,3-difluorophenyl)boronic acid (267 mg, 1.690 mmol), bis(triphenylphosphine)palladium(II)dichloride (39.5 mg, 0.056 mmol), and 1M sodium carbonate (1409 μL, 1.409 mmol) in 10 mL 1,2-dimethoxyethane/ethanol/water (7:2:3) was heated in a Biotage Initiator microwave reactor at 150° C. for 15 minutes. The mixture was concentrated, treated with ethyl acetate and washed with aqueous sodium bicarbonate. The organic layer was washed with water, dried over magnesium sulfate, filtered, concentrated and purified on silica gel using an ISCO Companion eluting with heptanes/ethyl acetate (7:3 to 6:4) to provide the title compound. MS (ESI$^+$) m/z 566.1 (M+H)$^+$.

EXAMPLE 222B tert-butyl 4-(4-(2,3-difluorophenyl)-1H-pyrrolo[2,3-b]pyridin-2-yl)-5,6-dihydropyridine-1(2H)-carboxylate A mixture Example 222A (0.820 g, 1.450 mmol) and 5M sodium hydroxide (1.015 mL, 5.07 mmol) in dioxane (10 mL) was heated at 90° C. for 7 hours. The mixture was concentrated and the residue was treated with ethyl acetate and washed with aqueous sodium bicarbonate. The organic layer was dried over magnesium sulfate, filtered, and concentrated until most of solvent was removed. The precipitate was filtered, washed with ethyl acetate/ether, and dried under vacuum to provide the title compound. MS (ESI$^+$) m/z 412.1 (M+H)$^+$.

EXAMPLE 222C 4-(2,3-difluorophenyl)-2-(1,2,3,6-tetrahydropyridin-4-yl)-1H-pyrrolo[2,3-b]pyridine A solution of Example 222B (0.255 g, 0.620 mmol) in dichloromethane (5 mL) was treated with trifluoroacetic acid (0.477 mL, 6.20 mmol) and the mixture was stirred for 3 hours and concentrated. The residue was dissolved in 2 mL methanol and treated slowly with 2 mL 2M hydrogen chloride in ether. The suspension was diluted with ether and stirred for 10 minutes. The solids were filtered, washed with

EXAMPLE 222D

4-[4-(2,3-difluorophenyl)-1H-pyrrolo[2,3-b]pyridin-2-yl]-N-methyl-3,6-dihydropyridine-1(2H)-carboxamide To a suspension of Example 222C (72.0 mg, 0.187 mmol) and N-succinimidyl-N-methylcarbamate (48.4 mg, 0.281 mmol) in N,N-dimethylformamide (2.5 mL) was added triethylamine (0.157 mL, 1.124 mmol) and the mixture was stirred for 3 hours and treated slowly with water. The precipitate was filtered, washed with water, dried over magnesium sulfate, filtered, and purified by HPLC (same protocol as Example 221) to provide the title compound as a trifluoroacetate salt. $^1$H NMR (400 MHz, Methanol-$d_4$) δ 2.56-2.62 (m, 2H), 2.76 (s, 3H), 3.63 (t, J=5.6 Hz, 2H), 4.13 (q, J=2.8 Hz, 2H), 6.48-6.54 (m, 1H), 6.57 (d, J=2.1 Hz, 1H), 7.29-7.53 (m, 4H), 8.31 (d, J=5.6 Hz, 1H). MS (ESI$^+$) m/z 369.1 (M+H)$^+$.

EXAMPLE 223

4-(5-fluoro-2-methoxyphenyl)-2-[8-(methylsulfonyl)-8-azabicyclo[3.2.1]oct-2-en-3-yl]-1H-pyrrolo[2,3-b]pyridine

EXAMPLE 223A tert-butyl 3-(((trifluoromethyl)sulfonyl)oxy)-8-azabicyclo[3.2.1]oct-3-ene-8-carboxylate To a solution of tert-butyl 3-oxo-8-azabicyclo[3.2.1]octane-8-carboxylate (10 g, 44.4 mmol) in tetrahydrofuran (100 mL) was added 2M lithium diisopropylamide (26.6 mL, 53.3 mmol) dropwise at −60° C. under argon and the mixture was stirred at −60° C. for 1 hour. A solution of 1,1,1-trifluoro-N-phenyl-N-((trifluoromethyl)sulfonyl) methanesulfonamide (17.44 g, 48.8 mmol) in tetrahydrofuran (100 mL) was added dropwise at −60° C. and the mixture was stirred at −60° C. for 30 minutes, and was allowed to warm to room temperature. The mixture was stirred under argon overnight, quenched with water (200 mL), and extracted with ethyl acetate (three times). The organic extracts were washed with 5% aqueous citric acid (twice) and stirred with 1M aqueous sodium hydroxide (200 mL) for 30 minutes. The wash process was repeated one additional time. The organic phase was dried over sodium sulfate, filtered, concentrated, and purified by flash chromatography on silica gel using an ISCO Companion eluting with ethyl acetate/petroleum ether (1:20) to provide the title compound.

EXAMPLE 223B tert-butyl 3-(4,4,5,5-tetramethyl-1,3,2-dioxaborolan-2-yl)-8-azabicyclo[3.2.1]oct-3-ene-8-carboxylate A mixture of Example 223A (10 g, 28.0 mmol), 4,4,4',4',5,5,5',5'-octamethyl-2,2'-bi(1,3,2-dioxaborolane) (7.82 g, 30.8 mmol), potassium acetate (7.42 g, 76 mmol), and [1,1'-bis(diphenylphosphino)ferrocene]dichloropalladium (II)-dichloromethane adduct (1.024 g, 1.399 mmol) in 1,4-dioxane (500 mL) was degassed with argon and the mixture was stirred at 80° C. under argon overnight. The mixture was cooled to room temperature and filtered. The filtrate was concentrated in vacuo and the residue was purified by flash chromatography on silica gel using an ISCO Companion eluting with ethyl acetate/petroleum ether (1:50 to 1:20) to provide the title compound. MS (DCI$^+$) m/z 336.2 (M+H)$^+$.

EXAMPLE 223C 2-(8-azabicyclo[3.2.1]oct-2-en-3-yl)-4-(5-fluoro-2-methoxyphenyl)-1H-pyrrolo[2,3-b]pyridine The title compound was prepared essentially as described in Example 87C and 87, substituting Example 223B for tert-butyl 4-(4,4,5,5-tetramethyl-1,3,2-dioxaborolan-2-yl)-5,6-dihydropyridine-1(2H)-carboxylate in Example 87C. MS (ESI$^+$) m/z 350.1 (M+H)$^+$.

EXAMPLE 223D 4-(5-fluoro-2-methoxyphenyl)-2-[8-(methylsulfonyl)-8-azabicyclo[3.2.1]oct-2-en-3-yl]-1H-pyrrolo[2,3-b]pyridine To a solution of Example 223C (80.0 mg, 0.189 mmol) in N,N-dimethylformamide (2 mL) was added methanesulfonyl chloride (0.030 mL, 0.379 mmol) and triethylamine (0.158 mL, 1.137 mmol) and the mixture was stirred for 3 hours. The mixture was treated with brine and aqueous sodium bicarbonate and extracted with ethyl acetate (twice). The combined organic layers were dried over magnesium sulfate, filtered, concentrated, and purified on silica gel using an ISCO Companion eluting with heptanes/ethyl acetate (1:9 to 0:10) to provide the title compound. $^1$H NMR (400 MHz, DMSO-$d_6$) δ 1.63-1.74 (m, 1H), 1.91-2.14 (m, 2H), 2.15-2.27 (m, 1H), 2.92-3.00 (m, 4H), 3.74 (s, 3H), 4.32-4.40 (m, 1H), 4.44 (t, J=5.8 Hz, 1H), 6.22 (s, 1H), 6.79 (d, J=6.0 Hz, 1H), 7.03 (d, J=4.9 Hz, 1H), 7.15-7.31 (m, 3H), 8.20 (d, J=4.9 Hz, 1H), 11.73-11.86 (m, 1H). MS (ESI$^+$) m/z 428.1 (M+H)$^+$.

EXAMPLE 224

2-{4-[4-(5-fluoro-2-methoxyphenyl)-1H-pyrrolo[2,3-b]pyridin-2-yl]-3,6-dihydropyridin-1(2H)-yl}-N,N-dimethylacetamide A suspension of Example 87 (0.05 g, 0.126 mmol) and triethylamine (0.088 mL, 0.631 mmol) in N,N-dimethylformamide (1.051 mL) was treated with 2-chloro-N,N-dimethylacetamide (0.018 g, 0.145 mmol) and the mixture was heated at 75° C. for 4 hours. The mixture was purified by reverse phase HPLC on a Phenomenex Luna C8(2) 5 um 100 Å AXIA column eluting with a gradient of 10-70% acetonitrile in 0.1% trifluoroacetic acid/water to afford the title compound as the trifluoroacetate salt. $^1$H NMR (400 MHz, CD$_3$OD) δ 2.94-3.07 (m, 8H), 3.42-3.77 (m, 2H), 3.82 (s, 3H), 4.02-4.25 (m, 2H), 4.36 (s, 2H), 6.48-6.57 (m, 1H), 6.70 (s, 1H), 7.17-7.34 (m, 3H), 7.48 (d, J=5.9 Hz, 1H), 8.34 (d, J=5.9 Hz, 1H). MS (ESI$^+$) m/z 409.0 (M+H)$^+$.

EXAMPLE 225

4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide A solution of 1-methyl-1H-pyrazol-4-amine (0.0105 g, 0.108 mmol), bis(2,5-dioxopyrrolidin-1-yl) carbonate (0.035 g, 0.135 mmol), and pyridine (8.73 µL, 0.108 mmol) in N,N-dimethylformamide (0.3 mL) was stirred at ambient temperature for 2 hours. N-ethyl-N-isopropylpropan-2-amine (0.056 mL, 0.324 mmol) was added and the solution was added to a suspension of Example 87 (0.043 g, 0.108 mmol) and N-ethyl-N-isopropylpropan-2-amine (0.075 mL, 0.432 mmol) in N,N-dimethylformamide (0.5 mL) dropwise over 3 minutes. The mixture was stirred for 16 hours at ambient temperature and purified by reverse phase HPLC on a Phenomenex Luna C8(2) 5 um 100 Å AXIA column eluting with a gradient of 10-70% acetonitrile in 0.1% trifluoroacetic acid/water to afford the title compound as the trifluoroacetate salt. $^1$H NMR (400 MHz, DMSO-$d_6$) δ 2.47-2.53 (m, 2H), 3.58-3.64 (m, 2H), 3.75 (s, 3H), 3.76 (s, 3H), 4.10-4.18 (m, 2H), 6.29-6.33 (m, 1H), 6.54-6.59 (m, 1H), 7.09 (d, J=5.0 Hz, 1H), 7.18-7.32 (m, 3H), 7.33-7.37 (m, 1H), 7.65-7.69 (m, 1H), 8.23 (d, J=5.1 Hz, 1H), 8.51-8.56 (m, 1H), 11.94-12.01 (m, 1H). MS (ESI$^+$) m/z 447.1 (M+H)$^+$.

EXAMPLE 226

{4-[4-(5-fluoro-2-methoxyphenyl)-1H-pyrrolo[2,3-b]pyridin-2-yl]-3,6-dihydropyridin-1(2H)-yl}acetic acid

EXAMPLE 226A tert-butyl 2-(4-(4-(5-fluoro-2-methoxyphenyl)-1H-pyrrolo[2,3-b]pyridin-2-yl)-5,6-dihydropyridin-1(2H)-yl)acetate A mixture of Example 87D (0.5 g, 1.262 mmol) and triethylamine (0.879 mL, 6.31 mmol) in N,N-dimethylformamide (12.62 mL) was treated with tert-butyl 2-bromoacetate (0.214 mL, 1.451 mmol) and the mixture was heated at 75° C. for 4 hours. The mixture was cooled to ambient temperature and poured into water. The suspension was filtered and the solid was washed with water (twice) and dried under vacuum. Purification by flash chromatography on silica gel (AnaLogix IntelliFlash 280) eluting with a gradient of 0-6% methanol in dichloromethane afforded the title compound. MS (ESI$^+$) m/z 438.1 (M+H)$^+$.

EXAMPLE 226B

{4-[4-(5-fluoro-2-methoxyphenyl)-1H-pyrrolo[2,3-b]pyridin-2-yl]-3,6-dihydropyridin-1(2H)-yl}acetic acid A solution of Example 226A (0.43 g, 0.983 mmol) and trifluoroacetic acid (1.817 mL, 23.59 mmol) in dichloromethane (9.83 mL) was stirred at ambient temperature for 24 hours. The mixture was concentrated, dissolved in 5 mL dichloromethane and 2N hydrogen chloride in ether (20 mL) was added. The suspension was stirred for 20 minutes, treated with ether (50 mL), and filtered. The solid was washed with ether and dried under vacuum to afford the title compound as a hydrochloride salt. $^1$H NMR (400 MHz, DMSO-$d_6$) δ 2.84-2.92 (m, 2H), 3.50-3.63 (m, 2H), 3.74 (s, 3H), 4.03-4.11 (m, 2H), 4.14 (s, 2H), 6.40 (s, 1H), 6.46-6.56 (m, 1H), 7.13 (d, J=5.2 Hz, 1H), 7.16-7.29 (m, 3H), 8.26 (d, J=5.1 Hz, 1H), 12.07 (bs, 1H). MS (ESI$^+$) m/z 382.1 (M+H)$^+$.

EXAMPLE 227

2-{4-[4-(5-fluoro-2-methoxyphenyl)-1H-pyrrolo[2,3-b]pyridin-2-yl]-3,6-dihydropyridin-1(2H)-yl}acetamide The title compound was prepared according to the procedure described in Example 224 substituting 2-bromoacetamide for 2-chloro-N,N-dimethylacetamide. $^1$H NMR (400 MHz, CD$_3$OD) δ 2.90-3.02 (m, 2H), 3.52-3.74 (m, 2H), 3.81 (s, 3H), 4.01-4.22 (m, 4H), 6.46-6.54 (m, 1H), 6.65 (s, 1H), 7.15-7.32 (m, 3H), 7.41 (d, J=5.8 Hz, 1H), 8.32 (d, J=5.7 Hz, 1H). MS (ESI$^+$) m/z 381.1 (M+H)$^+$.

EXAMPLE 228 ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for t-butanol in Example 218A. $^1$H NMR (400 MHz, DMSO-$d_6$): δ 1.15 (t, J=7.17 Hz, 3 H), 2.58 (s, 2 H), 3.47 (t, J=5.65 Hz, 2 H), 3.74 (s, 3 H), 4.02 (d, J=2.14 Hz, 2 H), 4.07 (q, J=7.22 Hz, 2 H), 6.26 (d, J=1.83 Hz, 1 H), 6.50 (s, 1 H), 7.04 (d, J=4.88 Hz, 1 H), 7.17-7.30 (m, 3 H), 8.21 (d, J=4.88 Hz, 1 H), 11.37 (s, 1 H), 11.86 (d, J=1.22 Hz, 1 H). MS (DCI/NH$_3$) m/z 475 (M+H)$^+$.

EXAMPLE 229

4-[5-chloro-4-(5-fluoro-2-methoxyphenyl)-1H-pyrrolo[2,3-b]pyridin-2-yl]-N-methyl-3,6-dihydropyridine-1(2H)-carboxamide

EXAMPLE 229A 4,5-dichloro-1-tosyl-1H-pyrrolo[2,3-b]pyridine

To 60% sodium hydride in mineral oil (1.390 g, 34.8 mmol) in N,N-dimethylformamide (60 mL) at 0° C. was added a solution of 4,5-dichloro-1H-pyrrolo[2,3-b]pyridine (Adesis, 5.0 g, 26.7 mmol) in N,N-dimethylformamide (20 mL) slowly over 5 minutes. The mixture was allowed to warm to room temperature and was stirred for 30 minutes. The mixture was cooled to 0° C. and a solution of p-toluenesulfonyl chloride (5.35 g, 28.1 mmol) in N,N-dimethylformamide (20 mL) was added. The mixture was allowed to warm to room temperature and stirred for 2 hours. Additional p-toluenesulfonyl chloride (500 mg, 2.62 mmol) was added, and the mixture was stirred another 1 hour at room temperature. The reaction was quenched with saturated aqueous ammonium chloride (25 mL) and extracted with ethyl acetate (twice). The combined organic layers were washed with water and brine, dried over sodium sulfate, filtered and concentrated. The residue was purified by flash chromatography on silica gel (AnaLogix IntelliFlash 280) eluting with a gradient of 40-70% ethyl acetate in hexanes to afford the title compound. MS (ESI$^+$) m/z 341.6 (M+H)$^+$.

EXAMPLE 229B 4,5-dichloro-2-iodo-1-tosyl-1H-pyrrolo[2,3-b]pyridine

To a solution of diisopropylamine (4.85 mL, 34.1 mmol) in tetrahydrofuran (50 mL) at −10° C. under nitrogen was added dropwise 2.5M n-butyllithium in hexane (13.62 mL, 34.1 mmol) and the mixture was stirred at −10° C. for 30 minutes. A solution of Example 229A (8.3 g, 24.33 mmol) in tetrahydrofuran (220 mL) cooled to −78° C. was treated with the lithium diisopropylamide solution dropwise over 20 minutes and the mixture was stirred for 50 minutes at −78° C. A solution of iodine (8.64 g, 34.1 mmol) in tetrahydrofuran (30 mL) was added and the mixture was stirred for 20 minutes at −78° C. and allowed to warm to room temperature. The reaction was quenched with saturated aqueous sodium thiosulfate and extracted with ethyl acetate (150 mL). The organic layer was washed with water and brine, dried over sodium sulfate, filtered, and concentrated. The residue was purified by flash chromatography on silica gel (AnaLogix IntelliFlash 280) eluting with a gradient of 30-60% ethyl acetate in hexanes. The solid was triturated with 100 mL 15% ethyl acetate/hexane, filtered and dried under vacuum to afford the title compound. MS (ESI$^+$) m/z 466.7 (M+H)$^+$.

EXAMPLE 229C tert-butyl 4-(4,5-dichloro-1-tosyl-1H-pyrrolo[2,3-b]pyridin-2-yl)-5,6-dihydropyridine-1(2H)-carboxylate A mixture of Example 229B (0.808 g, 1.730 mmol), tert-butyl 4-(4,4,5,5-tetramethyl-1,3,2-dioxaborolan-2-yl)-5,6-dihydropyridine-1(2H)-carboxylate (Frontier Scientific, 0.588 g, 1.903 mmol) and sodium hydrogencarbonate (0.436 g, 5.19 mmol) in degassed N,N-dimethylformamide (10.81 mL) and water (3.6 mL) was treated with bis(triphenylphosphine)palladium(II) chloride (0.121 g, 0.173 mmol) under nitrogen and the mixture was heated at 72° C. for 24 hours. The mixture was cooled to ambient temperature, suspended in 80 mL water, stirred for 30 minutes and filtered. Purification by flash chromatography on silica gel (AnaLogix IntelliFlash 280) eluting with a gradient of 0-20% ethyl acetate in hexanes afforded the title compound. MS (ESI$^+$) m/z 522.2 (M+H)$^+$.

EXAMPLE 229D tert-butyl 4-(5-chloro-4-(5-fluoro-2-methoxyphenyl)-1-tosyl-1H-pyrrolo[2,3-b]pyridin-2-yl)-5,6-dihydropyridine-1(2H)-carboxylate A mixture of Example 229C (0.16 g, 0.306 mmol), (5-fluoro-2-methoxyphenyl)boronic acid (0.062 g, 0.368 mmol) and sodium hydrogencarbonate (0.103 g, 1.225 mmol) in degassed N,N-dimethylformamide (2.55 mL) and water (0.851 mL) was treated with 1,1'-bis(di-t-butylphosphino)ferrocenepalladium dichloride (TCI, 0.014 g, 0.021 mmol) under nitrogen and the mixture was heated at 110° C. for 10 minutes in a Biotage Initiator microwave reactor. Water and ethyl acetate was added and the aqueous layer was extracted with ethyl acetate. The combined organic layers were washed with brine, dried over sodium sulfate, filtered, and concentrated. Purification by flash chromatography on silica gel (AnaLogix IntelliFlash 280) eluting with a gradient of 0-45% ethyl acetate in heptanes afforded the title compound. MS (ESI$^+$) m/z 612.2 (M+H)$^+$.

EXAMPLE 229E tert-butyl 4-(5-chloro-4-(5-fluoro-2-methoxyphenyl)-1H-pyrrolo[2,3-b]pyridin-2-yl)-5,6-dihydropyridine-1(2H)-carboxylate A mixture of Example 229D (0.16 g, 0.261 mmol) and 3N sodium hydroxide (0.261 mL, 0.784 mmol) in 1,4-dioxane (1.743 mL), ethanol (1.743 mL) and water (0.7 mL) was heated at 75° C. for 2.5 hours. The mixture was concentrated and the residue was partitioned in ethyl acetate and water. The organic layer was dried over sodium sulfate, filtered, and concentrated. Purification by flash chromatography on silica gel (AnaLogix IntelliFlash 280) eluting with a gradient of from 0-4% methanol in dichloromethane afforded the title compound. MS (ESI$^+$) m/z 458.1 (M+H)$^+$.

EXAMPLE 229F 5-chloro-2-(1-ethyl-1,2,3,6-tetrahydropyridin-4-yl)-4-(5-fluoro-2-methoxyphenyl)-1H-pyrrolo[2,3-b]pyridine A solution of Example 229E (0.072 g, 0.157 mmol) in dichloromethane (1.429 mL) was treated with 2,2,2-trifluoroacetic acid (0.121 mL, 1.572 mmol) and the mixture was stirred at room temperature for 8 hours. The mixture was concentrated and the residue was partitioned in ethyl acetate and saturated aqueous sodium bicarbonate. The aqueous layer was back-extracted with additional ethyl acetate and the combined organic layers were washed with brine, dried over sodium sulfate, filtered, and concentrated to provide the title compound. MS (ESI$^+$) m/z 358.1 (M+H)$^+$.

EXAMPLE 229G

4-[5-chloro-4-(5-fluoro-2-methoxyphenyl)-1H-pyrrolo[2,3-b]pyridin-2-yl]-N-methyl-3,6-dihydropyridine-1(2H)-carboxamide A solution of Example 229F (0.049 g, 0.137 mmol) and triethylamine (0.057 mL, 0.411 mmol) in N,N-dimethylformamide (1.4 mL) was treated with 2,5-dioxopyrrolidin-1-yl methylcarbamate (0.035 g, 0.205 mmol) and the mixture was stirred at room temperature for 16 hours. The mixture was poured into water and the solid was filtered and dried under vacuum to afford the title compound. $^1$H NMR (500 MHz, DMSO-d$_6$) δ 2.32-2.43 (m, 2H), 2.58 (d, J=4.3 Hz, 3H), 3.46 (t, J=5.7 Hz, 2H), 3.70 (s, 3H), 3.96-4.03 (m, 2H), 6.01-6.08 (m, 1H), 6.40-6.47 (m, 1H), 6.47-6.55 (m, 1H), 7.14 (dd, J=8.6, 3.1 Hz, 1H), 7.20 (dd, J=9.2, 4.5 Hz, 1H), 7.26-7.39 (m, 1H), 8.24 (s, 1H), 12.03 (bs, 1H). MS (ESI$^+$) m/z 415.1 (M+H)$^+$.

EXAMPLE 230

4-(5-fluoro-2-methoxyphenyl)-2-[1-(S-methylsulfonimidoyl)-1,2,3,6-tetrahydropyridin-4-yl]-1H-pyrrolo[2,3-b]pyridine

EXAMPLE 230A

N-[{4-[4-(5-fluoro-2-methoxyphenyl)-1H-pyrrolo[2,3-b]pyridin-2-yl]-3,6-dihydropyridin-1(2H)-yl}(methyl)oxido-λ$^6$-sulfanylidene]-4-methylbenzenesulfonamide To a solution of Example 87D (200 mg, 0.618 mmol) in dichloromethane (20 mL) was added triethylamine (0.259 mL, 0.188 mmol) and N-tosylmethanesulfonimidoyl chloride (SynChem, 331 mg, 1.237 mmol) at room temperature and the mixture was heated at 50° C. overnight. After cooling, the solid was filtered, washed with dichloromethane and dried in vacuo to provide the title compound. MS (DCI/NH$_3$) m/z 555 (M+H)$^+$.

EXAMPLE 230B 4-(5-fluoro-2-methoxyphenyl)-2-[1-(S-methylsulfonimidoyl)-1,2,3,6-tetrahydropyridin-4-yl]-1H-pyrrolo[2,3-b]pyridine To a suspension of sodium (140 mg, 6.09 mmol) in anhydrous 1,2-dimethoxyethane (10 mL) was added anthracene (1.08 g, 6.09 mmol) and the suspension was placed in an ultrasonic cleaner overnight to form a blue solution. A solution of Example 230A (220 mg, 0.395 mmol) in 1,2-dimethoxyethane (6 mL) was added dropwise to the freshly prepared sodium anthracenide solution at 0° C. After addition, the mixture was stirred at 0° C. for 30 minutes and quenched with water and 2N aqueous hydrochloric acid (5 mL) at 0° C. The cooling bath was removed, and the mixture was partitioned between ethyl acetate and brine. The aqueous phase was made basic with aqueous sodium hydroxide, extracted with ethyl acetate, and the combined organic phase was washed with water and concentrated. The residue was purified by flash chromatography (Teledyne Combinflash Rf) on silica (0-15% methanol in dichloromethane) and further purified by HPLC (Zorbax, C-18, eluting with a 0-100% gradient of 0.1% trifluoroacetic acid in water/0.1% trifluoroacetic acid in acetonitrile) to provide the title compound as the trifluoroacetate salt. $^1$H NMR (400 MHz, CD$_3$OD): δ 2.77 (s, 2 H), 3.34 (s, 3H), 3.60-3.66 (m, 1 H), 3.68-3.75 (m, 1 H), 3.81 (s, 3 H), 4.17-4.20 (m, J=3.05 Hz, 2 H), 6.56-6.58 (m, 2 H), 7.20-7.29 (m, 3 H), 7.42 (d, J=5.80 Hz, 1 H), 8.29 (d, J=5.80 Hz, 1 H). MS (DCI/NH$_3$) m/z 401 (M+H)$^+$.

EXAMPLE 231

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide

EXAMPLE 231A 4-chloro-5-fluoro-1-(phenylsulfonyl)-1H-pyrrolo[2,3-b]pyridine

To a solution of 4-chloro-5-fluoro-1H-pyrrolo[2,3-b]pyridine (Adesis, 4.60 g, 27.0 mmol) in N,N-dimethylformamide (70 mL) was added 60% sodium hydride in mineral oil (1.186 g, 29.7 mmol) at 0° C. and the mixture was warmed to room temperature and stirred for 30 minutes. Benzenesulfonyl chloride (3.79 mL, 29.7 mmol) was added and after stirring 3 hours, the mixture was quenched with water and aqueous sodium bicarbonate. The suspension was filtered, washed with aqueous sodium bicarbonate, water, and heptanes, and vacuum oven-dried to provide the title compound. MS (ESI$^+$) m/z 311.0 (M+H)$^+$.

EXAMPLE 231B 4-chloro-5-fluoro-2-iodo-1-(phenylsulfonyl)-1H-pyrrolo[2,3-b]pyridine To a solution of Example 231A (3.560 g, 11.46 mmol) in tetrahydrofuran (75 mL) at 78° C. was added dropwise 2M lithium diisopropylamide in tetrahydrofuran/heptane/ethylbenzene (11.46 mL, 22.91 mmol). The mixture was stirred at −78° C. for 30 minutes and iodine (5.82 g, 22.91 mmol) in tetrahydrofuran (25 mL) was added. After stirring at −78° C. for 3 hours, the reaction was quenched with aqueous sodium thiosulfate and extracted with ethyl acetate (twice). The combined organic layers were dried over magnesium sulfate, filtered, concentrated until most solvent was removed. The suspension was diluted with ethyl acetate and warmed with a heat gun. Heptanes were added to the suspension and the mixture was stirred for 1 hour. The solid was filtered, washed with heptanes/ethyl acetate (1:1), and vacuum oven-dried to provide the title compound. The filtrate was concentrated and triturated with heptanes/ethyl acetate (1:1) to give additional title compound. MS (ESI$^+$) m/z 436.9 (M+H)$^+$.

EXAMPLE 231C tert-butyl 4-(4-chloro-5-fluoro-1-(phenylsulfonyl)-1H-pyrrolo[2,3-b]pyridin-2-yl)-5,6-dihydropyridine-1(2H)-carboxylate A mixture of Example 231B (6.70 g, 15.34 mmol), tert-butyl 4-(4,4,5,5-tetramethyl-1,3,2-dioxaborolan-2-yl)-5,6-dihydropyridine-1(2H)-carboxylate (4.89 g, 15.81 mmol), tetrakis(triphenylphosphine)palladium (0.532 g, 0.460 mmol), and sodium bicarbonate solution (40 mL, 15.34 mmol) in N,N-dimethylformamide (160 mL) was degassed and heated at 80° C. overnight. The mixture was diluted with water and brine and extracted with ethyl acetate (twice). The combined organic layers were washed with water, dried over magnesium sulfate, filtered, concentrated, and purified on silica gel using an ISCO Companion eluting with heptanes/ethyl acetate (8:2 to 7:3) to provide the title compound. MS (ESI$^+$) m/z 492.0 (M+H)$^+$.

EXAMPLE 231D tert-butyl 4-(5-fluoro-4-(5-fluoro-2-methoxyphenyl)-1-(phenylsulfonyl)-1H-pyrrolo[2,3-b]pyridin-2-yl)-5,6-dihydropyridine-1(2H)-carboxylate A mixture of Example 231C (2000 mg, 4.07 mmol), (5-fluoro-2-methoxyphenyl)boronic acid (898 mg, 5.28 mmol), potassium phosphate tribasic (2589 mg, 12.20 mmol), and phenylallylchloro[1,3-bis(diisopropylphenyl)-2-imidazol-2-ylidene]palladium(II) (79 mg, 0.122 mmol) in tetrahydrofuran (60 mL) and water (20 mL) was degassed and heated at 60° C. for 3 hours. The mixture was treated with water and brine and extracted with ethyl acetate. The organic layer was washed with water, dried over magnesium sulfate, filtered, concentrated, and purified on silica gel using an ISCO Companion eluting with heptanes/ethyl acetate (7:3 to 6:4) to provide the title compound. MS (ESI$^+$) m/z 582.1 (M+H)$^+$.

EXAMPLE 231E 5-fluoro-4-(5-fluoro-2-methoxyphenyl)-2-(1,2,3,6-tetrahydropyridin-4-yl)-1H-pyrrolo[2,3-b]pyridine A mixture of Example 231D (2.00 g, 3.44 mmol) and 5M sodium hydroxide (2.407 mL, 12.04 mmol) in dioxane (20 mL) was heated at 90° C. for 8 hours. After concentration, the residue was treated with ethyl acetate and washed with water. The organic layer was dried over magnesium sulfate, filtered, concentrated, and purified on silica gel using an ISCO Companion eluting with heptanes/ethyl acetate (6:4 to 4:6) to give the protected intermediate. A solution of the intermediate in dichloromethane (25 mL) was treated with trifluoroacetic acid (2.27 mL, 29.4 mmol) and the mixture was stirred for 3 hours and concentrated. The residue was dissolved in 6 mL methanol and treated slowly with 5 mL 2M hydrogen chloride in ether. The suspension was sonicated, diluted with ether and stirred for 10 minutes. The solid was filtered, washed with ether and vacuum oven-dried to provide the title compound as a hydrochloride salt. MS (ESI$^+$) m/z 342.1 (M+H)$^+$.

EXAMPLE 231F

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide A mixture of Example 231E (80.0 mg, 0.193 mmol), 2-chloro-N,N-dimethylacetamide (0.023 mL, 0.222 mmol), and triethylamine (0.135 mL, 0.966 mmol) in N,N-dimethylformamide (1.5 mL) was heated at 75° C. for 4 hours. The mixture was treated with water and brine and extracted with ethyl acetate (twice). The combined organic layers were dried over magnesium sulfate, filtered, concentrated, and purified by HPLC (same protocol as Example 221) to provide the title compound as a trifluoroacetic acid salt. $^1$H NMR (500 MHz, Methanol-d$_4$) δ 2.83-3.00 (m, 2H), 3.01 (s, 6H), 3.35-3.49 (m, 1H), 3.67-3.81 (m, 1H), 3.77 (s, 3H), 3.87-4.30 (m, 2H), 4.34 (bs, 2H), 6.36 (s, 1H), 6.38 (bs, 1H), 7.09-7.29 (m, 3H), 8.16 (d, J=2.8 Hz, 1H). MS (ESI$^+$) m/z 427.0 (M+H)$^+$.

EXAMPLE 232

4-[4-(4,5-difluoro-2-methoxyphenyl)-1H-pyrrolo[2,3-b]pyridin-2-yl]-N-methyl-3,6-dihydropyridine-1(2H)-carboxamide

EXAMPLE 232A 4-(4,5-difluoro-2-methoxyphenyl)-2-(1,2,3,6-tetrahydropyridin-4-yl)-1H-pyrrolo[2,3-b]pyridine The title compound was prepared as described in Example 87, substituting 4,5-difluoro-2-methoxyphenylboronic acid for 5-fluoro-2-methoxyphenylboronic acid in Example 87A. MS (ESI$^+$) m/z 342 (M+H)$^+$.

EXAMPLE 232B 4-(4-(4,5-difluoro-2-methoxyphenyl)-1H-pyrrolo[2,3-b]pyridin-2-yl)-N-methyl-5,6-dihydropyridine-1(2H)-carboxamide The title compound was prepared using the procedure described in Example 215, using Example 232A in place of Example 87. $^1$H NMR (400 MHz, DMSO-d$_6$) δ 2.37-2.50 (m, 2H), 2.60 (s, 3H), 3.50 (t, J=5.7 Hz, 2H), 3.76 (s, 3H), 4.01 (q, J=2.8 Hz, 2H), 6.32 (d, J=2.0 Hz, 1H), 6.53 (d, J=3.7 Hz, 1H), 7.09 (d, J=5.1 Hz, 1H), 7.36 (dd, J=12.9, 6.9 Hz, 1H), 7.49 (dd, J=11.0, 9.2 Hz, 1H), 8.23 (d, J=5.1 Hz, 1H), 12.01 (d, J=2.7 Hz, 1H). MS (ESI$^+$) m/z 406 (M+H)$^+$.

EXAMPLE 233

2-{3-[4-(5-fluoro-2-methoxyphenyl)-1H-pyrrolo[2,3-b]pyridin-2-yl]-8-azabicyclo[3.2.1]oct-2-en-8-yl})-N,N-dimethylacetamide The title compound was prepared essentially as described in Example 231F, substituting Example 223C for Example 231E. $^1$H NMR (500 MHz, Methanol-d$_4$) δ 2.04-2.14 (m, 1H), 2.34-2.59 (m, 3H), 2.76-2.90 (m, 1H), 2.94-3.05 (m, 6H), 3.21-3.42 (m, 1H), 3.81 (s, 3H), 4.12-4.35 (m, 3H), 4.36-4.47 (m, 1H), 6.60-6.80 (m, 2H), 7.19-7.25 (m, 1H), 7.23-7.33 (m, 2H), 7.44 (d, J=5.7 Hz, 1H), 8.33 (d, J=5.7 Hz, 1H). MS (ESI$^+$) m/z 435.1 (M+H)$^+$.

EXAMPLE 234

2-{4-[4-(2,3-difluorophenyl)-1H-pyrrolo[2,3-b]pyridin-2-yl]-3,6-dihydropyridin-1(2H)-yl}-N,N-dimethylacetamide The title compound was prepared essentially as described in Example 231F, substituting Example 222C for Example 231E. $^1$H NMR (400 MHz, Methanol-d$_4$) δ 3.00-3.04 (m, 8H), 3.43-3.79 (m, 2H), 3.99-4.31 (m, 2H), 4.35 (s, 2H), 6.45-6.50 (m, 1H), 6.65 (d, J=2.3 Hz, 1H), 7.29-7.52 (m, 4H), 8.36 (d, J=5.3 Hz, 1H). MS (ESI$^+$) m/z 397.1 (M+H)$^+$.

EXAMPLE 235

2-{4-[4-(5-fluoro-2-methoxyphenyl)-1H-pyrrolo[2,3-b]pyridin-2-yl]piperidin-1-yl}-N,N-dimethylacetamide To a mixture of Example 17G (300 mg, 0.922 mmol), 2-chloro-N,N-dimethylacetamide (118 mg, 0.968 mmol) in N,N-dimethylformamide (2.5 mL) was added N-ethyl-N-isopropylpropan-2-amine (0.644 mL, 3.69 mmol) and the mixture was stirred at 70° C. for 2 hours. Water was added and the mixture was extracted with ethyl acetate. The combined organic layers were washed with brine, dried over sodium sulfate, filtered and concentrated. The residue was purified by flash chromatography (AnaLogix IntelliFlash 280) on silica gel, eluting with 5-15% methanol in dichloromethane (linear gradient) to afford the title compound. $^1$H NMR (400 MHz, DMSO-d$_6$) δ 1.61-1.80 (m, 2 H) 1.89-2.02 (m, 2 H) 2.09-2.22 (m, 2 H) 2.62-2.73 (m, 1 H) 2.81 (s, 3 H) 2.85-2.95 (m, 2 H) 3.03 (s, 3 H) 3.14 (s, 2 H) 3.73 (s, 3 H) 5.96 (d, J=1.83 Hz, 1 H) 7.00 (d, J=4.88 Hz, 1 H) 7.14-7.30 (m, 3 H) 8.13 (d, J=5.19 Hz, 1 H) 11.55 (s, 1 H). MS (ESI$^+$) m/z 411 (M+H)$^+$.

EXAMPLE 236

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide

EXAMPLE 236A 4-chloro-1-(phenylsulfonyl)-1H-pyrrolo[2,3-b]pyridine-5-carbonitrile 4-Chloro-1H-pyrrolo[2,3-b]pyridine-5-carbonitrile (2.6 g, 14.64 mmol) and triethylamine (3.06 mL, 21.96 mmol) in tetrahydrofuran (100 mL) was cooled to 0° C. and benzenesulfonyl chloride (2.253 mL, 17.57 mmol) was added dropwise. The mixture was stirred at 0° C. for 1 hour and at room temperature for 10 hours and the mixture was concentrated. Water was added and the mixture was extracted with dichloromethane (three times). The organic phase was washed with water and brine, dried over sodium sulfate, filtered and concentrated. The residue was triturated with diethyl ether to afford the title compound. MS (ESI(+)) m/e 318 (M+H)$^+$.

EXAMPLE 236B 4-(5-fluoro-2-methoxyphenyl)-1-(phenylsulfonyl)-1H-pyrrolo[2,3-b]pyridine-5-carbonitrile A mixture of Example 236A (2 g, 6.29 mmol), (5-fluoro-2-methoxyphenyl)boronic acid (1.284 g, 7.55 mmol), sodium hydrogencarbonate (1.586 g, 18.88 mmol) and [1,1'-bis(diphenylphosphino)ferrocene]-dichloropalladium(II)-dichloromethane adduct (0.276 g, 0.378 mmol) in 80 mL N,N-dimethylformamide and 20 mL water was degassed with nitrogen and heated at 100° C. for 3 hours. The mixture was cooled to room temperature, diluted with water, and extracted with ethyl acetate. The organic phase was washed with brine, dried over magnesium sulfate, filtered and concentrated. Purification by silica-gel flash chromatography (AnaLogix IntelliFlash 280) eluting with dichloromethane afforded the title compound. MS (ESI$^+$) m/z 408 (M+H)$^+$.

EXAMPLE 236C 4-(5-fluoro-2-methoxyphenyl)-2-iodo-1-(phenylsulfonyl)-1H-pyrrolo[2,3-b]pyridine-5-carbonitrile The title compound was prepared essentially as described in Example 87B, substituting Example 236B for Example 87A. MS (ESI$^+$) m/z 534 (M+H)$^+$.

Example 236D tert-butyl 4-(5-cyano-4-(5-fluoro-2-methoxyphenyl)-1-(phenylsulfonyl)-1H-pyrrolo[2,3-b]pyridin-2-yl)-5,6-dihydropyridine-1(2H)-carboxylate The title compound was prepared according to the procedure described in Example 87C, substituting Example 236C for Example 87B. MS (ESI$^+$) m/z 589 (M+H)$^+$.

EXAMPLE 236E tert-butyl 4-(5-cyano-4-(5-fluoro-2-methoxyphenyl)-1H-pyrrolo[2,3-b]pyridin-2-yl)-5,6-dihydropyridine-1(2H)-carboxylate To a solution of Example 236D (400 mg, 0.680 mmol) in 5 mL methanol and 5 mL tetrahydrofuran was added 1N aqueous sodium hydroxide (3398 μL, 3.40 mmol) and the mixture was stirred at room temperature overnight and at 70° C. for 1 hour. The mixture was diluted with water, neutralized to pH 5-6 and extracted with ethyl acetate. The organic phase was washed with water and brine, dried over magnesium sulfate, filtered and concentrated. The residue was purified by flash chromatography (AnaLogix IntelliFlash 280) eluting with 0-3% methanol in dichloromethane to afford the title compound. MS (ESI$^+$) m/z 449 (M+H)$^+$.

EXAMPLE 236F 4-(5-fluoro-2-methoxyphenyl)-2-(1,2,3,6-tetrahydropyridin-4-yl)-1H-pyrrolo[2,3-b]pyridine-5-carbonitrile To a solution of Example 236E (110 mg, 0.245 mmol) in dichloromethane (2 mL) was added trifluoroacetic acid (0.5 mL) and the mixture was stirred at room temperature for 3 hours and concentrated. The residue was triturated with diethyl ether and filtered to obtain the title compound as the trifluoroacetic acid salt. MS (ESI(+)) m/e 349 (M+H)$^+$.

EXAMPLE 236G

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide The title compound was prepared according to the procedure described in Example 235, substituting Example 236F for Example 17G. $^1$H NMR (400 MHz, DMSO-d$_6$) δ 2.40-2.50 (m, 2H), 2.65-2.72 (m, 2H), 2.82 (s, 3H), 3.01 (s, 3H), 3.19-3.24 (m, 4H), 3.76 (s, 3H), 6.25 (s, 1H), 6.56 (bs, 1H), 7.22-7.43 (m, 3H), 8.60 (s, 1H), 12.43 (bs, 1H). MS (ESI(+)) m/e 434 (M+H)$^+$.

EXAMPLE 237 ethyl ({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for tert-butanol in Example 218A and substituting Example 231E for Example 87 in Example 218B. The crude compound was purified by HPLC (same protocol as Example 217) to provide the title compound as a trifluoroacetic acid salt. $^1$H NMR (500 MHz, DMSO-d$_6$) δ 1.15 (t, J=7.1 Hz, 3H), 2.56 (bs, 2H), 3.42-3.49 (m, 2H), 3.73 (s, 3H), 3.99-4.04 (m, 2H), 4.07 (q, J=7.1 Hz, 2H), 6.20 (d, J=2.1 Hz, 1H), 6.51 (bs, 1H), 7.16-7.30 (m, 2H), 7.33 (td, J=8.6, 3.2 Hz, 1H), 8.21 (d, J=2.5 Hz, 1H), 11.37 (s, 1H), 11.97-12.02 (m, 1H). MS (ESI$^+$) m/z 493.1 (M+H)$^+$.

EXAMPLE 238

2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone A solution of Example 226B (2 g, 4.40 mmol), N-ethyl-N-isopropylpropan-2-amine (3.84 mL, 22.01 mmol) and azetidin-3-ol hydrochloride (0.555 g, 5.06 mmol) in N,N-dimethylformamide (33.9 mL) was treated with 1-[bis(dimethylamino)methylene]-1H-1,2,3-triazolo[4,5-b]pyridinium 3-oxide hexafluorophosphate (1.724 g, 4.53 mmol) and the mixture was stirred at room temperature for 20 hours. The mixture was concentrated under vacuum and the residue was purified by flash chromatography on silica gel (AnaLogix IntelliFlash 280) eluting with a gradient of 0-10% methanol in dichloromethane followed by a gradient of 0-10% methanol in dichloromethane containing 1% ammonium hydroxide to afford the title compound. $^1$H NMR (500 MHz, DMSO-d$_6$) δ 2.44-2.50 (m, 2H), 2.64-2.72 (m, 2H), 3.04-3.14 (m, 2H), 3.14-3.22 (m, 2H), 3.55-3.63 (m, 1H), 3.74 (s, 3H), 3.87-3.96 (m, 1H), 4.00-4.09 (m, 1H), 4.30-4.40 (m, 1H), 4.40-4.50 (m, 1H), 5.69 (d, J=6.1 Hz, 1H), 6.17-6.24 (m, 1H), 6.44-6.51 (m, 1H), 7.02 (d, J=4.9 Hz, 1H), 7.14-7.34 (m, 3H), 8.19 (d, J=4.9 Hz, 1H), 11.77 (bs, 1H). MS (ESI$^+$) m/z 437.0 (M+H)$^+$.

EXAMPLE 239

2-{4-[4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone The title compound was prepared according to the procedure described in Example 238 substituting (S)-pyrrolidin-2-ylmethanol for azetidin-3-ol hydrochloride. $^1$H NMR (400 MHz, CD$_3$OD) δ 1.84-2.10 (m, 4H), 2.56-2.65 (m, 2H), 2.78-2.90 (m, 2H), 3.33-3.36 (m, 3H), 3.38-3.71 (m, 5H), 3.76 (s, 3H), 4.03-4.28 (m, 1H), 6.26 (s, 1H), 6.33-6.42 (m, 1H), 7.07 (d, J=5.1 Hz, 1H), 7.11-7.21 (m, 3H), 8.14 (d, J=5.1 Hz, 1H). MS (ESI$^+$) m/z 465.1 (M+H)$^+$.

EXAMPLE 240

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone

EXAMPLE 240A (2R,4R)-tert-butyl 2-(4-(4-(5-fluoro-2-methoxyphenyl)-1H-pyrrolo[2,3-b]pyridin-2-yl)-1,2,3,6-tetrahydropyridine-1-carbonyl)-4-hydroxypyrrolidine-1-carboxylate A mixture of Example 87 (200 mg, 0.505 mmol), N-Boc-cis-4-hydroxy-D-proline (152 mg, 0.656 mmol), 1 (3-dimethylaminopropyl)-3-ethylcarbodiimide hydrochloride (126 mg, 0.656 mmol), 1H-benzo[d][1,2,3]triazol-1-ol hydrate (100 mg, 0.656 mmol) and triethylamine (0.35 mL) in 6 mL N,N-dimethylformamide was heated at 100° C. overnight. The mixture was diluted with water and extracted with dichloromethane. The organic phase was washed with water and brine, dried over magnesium sulfate, filtered and concentrated under reduced pressure. The residue was purified by silica-gel column chromatography (AnaLogix IntelliFlash 280) eluting with 0-5% methanol in dichloromethane to afford the title compound. MS (ESI(+)) m/e 537 (M+H)$^+$.

EXAMPLE 240B

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone To a solution of Example 240A (100 mg, 0.186 mmol) in dichloromethane (2 mL) was added trifluoroacetic acid (0.2 mL, 2.60 mmol) and the mixture was stirred at room temperature for 4 hours and concentrated. The residue was dissolved in dichloromethane (2 mL) and treated with 2M hydrogen chloride in ether (2.5 mL) and filtered. The solid was washed with diethyl ether and concentrated to obtain the title compound as the hydrochloride salt. $^1$H NMR (500 MHz, DMSO-d$_6$) δ1.70-1.80 (m, 1H), 2.53-2.79 (m, 2H), 3.09-3.32 (m, 2H), 4.60-4.06 (m, 7H) 4.37-4.43 (m, 2H), 4.44 (dd, J=38.4, 9.5 Hz, 1H), 4.57-4.77 (m, 1H), 6.44 (bs, 1H), 6.62-6.69 (m, 1H), 7.01-7.38 (m, 3H), 8.29 (d, J=5.3 Hz, 1H), 8.46-8.80 (m, 1H), 10.24 (bs, 1H), 12.57-12.65 (m, 1H). MS (ESI(+)) m/e 437 (M+H)$^+$.

EXAMPLE 241

N-{4-[4-(5-fluoro-2-methoxyphenyl)-1H-pyrrolo[2,3-b]pyridin-2-yl]cyclohex-3-en-1-yl}-D-valine

EXAMPLE 241A 4-(5-fluoro-2-methoxyphenyl)-2-(1,4-dioxaspiro[4.5]dec-7-en-8-yl)-1H-pyrrolo[2,3-b]pyridine The title compound was prepared essentially as described in Example 219B, substituting Example 219A with Example 87B and ethyl 4-(4,4,5,5-tetramethyl-1,3,2-dioxaborolan-2-yl)cyclohex-3-enecarboxylate with 4,4,5,5-tetramethyl-2-(1,4-dioxaspiro[4.5]dec-7-en-8-yl)-1,3,2-dioxaborolane. A solution of the crude material in 50 mL dioxane was treated with 6M aqueous sodium hydroxide (8.20 mL, 49.2 mmol) at 100° C. for 3 hours. The mixture was cooled, diluted with ethyl acetate, washed with saturated sodium bicarbonate, water, and brine, dried over magnesium sulfate, filtered and concentrated to provide the title compound as a solid which was used in the next step without further purification. MS (ESI): 381.2 (M+H)$^+$.

EXAMPLE 241B 4-(4-(5-fluoro-2-methoxyphenyl)-1H-pyrrolo[2,3-b]pyridin-2-yl)cyclohex-3-enone To a solution of Example 241A (3.7 g, 9.73 mmol) in 30 mL dichloromethane was added excess trifluoroacetic acid (6 mL). The mixture was stirred at room temperature overnight and the solvent was removed in vacuo. The residue was dissolved in 50 mL ethyl acetate and washed with saturated sodium bicarbonate, water, and brine, dried over magnesium sulfate, filtered and concentrated. The crude material was triturated with ethyl acetate and the solid was filtered and dried in vacuo to provide the title compound. MS (ESI): 337.2 (M+H)$^+$.

EXAMPLE 241C

N-{4-[4-(5-fluoro-2-methoxyphenyl)-1H-pyrrolo[2,3-b]pyridin-2-yl]cyclohex-3-en-1-yl}-D-valine To a mixture of Example 241B (125 mg, 0.372 mmol), triethylamine (0.114 mL, 0.818 mmol), acetic acid (0.106 mL, 1.858 mmol) and (R)-tert-butyl 2-amino-3-methylbutanoate hydrochloride (0.401 mL, 1.858 mmol) in 4 mL 1:1 dichloromethane/methanol was added Biotage MP-cyanoborohydride resin (2.17 mmol/g, 678 mg, 1.487 mmol) and the mixture was shaken at room temperature overnight. The mixture was diluted with dichloromethane and the resin was filtered off, rinsing with dichloromethane and methanol. The crude material was purified by flash chromatography (Analogix280, eluting with a 0-4% methanol/dichloromethane gradient). The tert-butyl ester in 5 mL dichloromethane was treated with excess trifluoroacetic acid for 10 hours. The solvent was removed and the residue was dissolved in 5 mL methanol and treated with 2M hydrogen chloride in diethyl ether for 1 hour. The mixture was diluted with 50 mL diethyl ether and the solid was filtered and dried in vacuo to provide the title compound as the hydrochloride salt. $^1$H NMR (400 MHz, DMSO-d$_6$) δ 0.87-1.16 (m, 6 H) 1.76-2.02 (m, 1 H) 2.09-2.40 (m, 2 H) 2.56-2.87 (m, 3 H) 3.20-3.45 (m, 1 H) 3.64-3.86 (m, 3 H) 4.05 (s, 1 H) 6.40 (s, 1 H) 6.60 (s, 1 H) 7.13-7.44 (m, 4 H) 8.22-8.33 (m, 1 H) 8.40 (d, J=1.83 Hz, 1 H) 8.65-9.88 (m, 2 H) 12.70 (d, J=3.97 Hz, 1 H). MS (ESI): 438.1 (M+H)$^+$.

EXAMPLE 242

1-{4-[4-(5-fluoro-2-methoxyphenyl)-1H-pyrrolo[2,3-b]pyridin-2-yl]cyclohex-3-en-1-yl}-L-proline The title compound was prepared essentially as described in Example 241C, substituting (R)-tert-butyl 2-amino-3-methylbutanoate hydrochloride with (S)-tert-butyl pyrrolidine-2-carboxylate. The material was purified by preparative HPLC on a Waters prep system using a Phenomenex Luna C8(2) 5 um 100 Å AXIA column using a 10-95% gradient of acetonitrile and 0.1% trifluoroacetic acid in water, to provide the title compound as the trifluoroacetate salt. $^1$H NMR (400 MHz, DMSO-d$_6$) δ1.66-1.94 (m, 2 H) 1.97-2.28 (m, 3 H) 2.33-2.49 (m, 2 H) 2.57-2.84 (m, 2 H) 3.35 (d, J=2.44 Hz, 1 H) 3.49-3.71 (m, 2 H) 3.70-3.79 (m, 3 H) 4.47-4.73 (m, 1 H) 6.14-6.35 (m, 1 H) 6.46 (s, 1 H) 7.09 (d, J=4.88 Hz, 1 H) 7.16-7.34 (m, 3 H) 8.24 (d, J=4.88 Hz, 1 H) 9.29-9.96 (m, 1 H) 11.98 (s, 1 H). MS (ESI): 436.1 (M+H)$^+$.

EXAMPLE 243

N-cyano-4-[4-(5-fluoro-2-methoxyphenyl)-1H-pyrrolo[2,3-b]pyridin-2-yl]-3,6-dihydropyridine-1(2H)-carboxamide To a solution of cyanamide (98 mg, 2.32 mmol) and N-ethyl-N-isopropylpropan-2-amine (0.5 mL, 5.73 mmol) in N,N-dimethylformamide (5 mL) at 0° C., was added 4-nitrophenyl carbonochloridate (450 mg, 2.24 mmol) and the mixture was stirred at room temperature for 2 hours. A solution of Example 87 (304 mg, 0.767 mmol) and N-ethyl-N-isopropylpropan-2-amine (1 mL, 5.73 mmol) in N,N-dimethylformamide (5 mL) was added and the mixture was stirred at room temperature overnight. The crude product was purified by HPLC using a SunFire, C8 column and eluting with a gradient of 30-100% acetonitrile/water containing 0.1% trifluoroacetic acid. The solid was suspended in water, adjusted to ~pH 9 with sodium hydroxide, and extracted with ethyl acetate. The organic phase was washed with saturated sodium carbonate, water and brine, dried over sodium sulfate, filtered, and concentrated. The residue was further purified by HPLC using a SunFire, C8 column and eluted with a gradient of 30-100% acetonitrile/water containing 0.1% trifluoroacetic acid. After concentration, the residue was dissolved in methanol and treated with 1M hydrogen chloride in ether (5 mL). Ether (100 mL) was added and the solid was filtered, washed with ether and dried under vacuum to afford the title compound as the hydrochloride salt. $^1$H NMR (500 MHz, methanol-d$_4$) δ 2.64 (m, 2 H) 3.74 (t, J=5.49 Hz, 2 H) 3.82 (s, 3 H) 4.26 (m, 2 H) 6.57 (m, 1 H) 6.62 (s, 1 H) 7.27 (m, 3 H) 7.52 (d, J=6.10 Hz, 1 H) 8.30 (d, J=6.10 Hz, 1 H). MS (ESI$^+$) m/z 392.1 (M+H)$^+$.

EXAMPLE 244

1-({4-[4-(5-fluoro-2-methoxyphenyl)-1H-pyrrolo[2,3-b]pyridin-2-yl]-3,6-dihydropyridin-1(2H)-yl}acetyl)-L-prolinamide The title compound was prepared according to the procedure described in Example 238 substituting (S)-pyrrolidine-2-carboxamide for azetidin-3-ol hydrochloride. $^1$H NMR (400 MHz, pyridine-d$_5$) δ 1.61-2.09 (m, 3H), 2.14-2.31 (m, 1H), 2.57-2.69 (m, 2H), 2.82-2.95 (m, 2H), 3.32-3.49 (m, 4H), 3.55-3.78 (m, 5H), 4.74-4.96 (m, 1H), 6.46-6.62 (m, 2H), 7.06 (dd, J=9.0, 4.6 Hz, 1H), 7.13-7.25 (m, 2H), 7.38 (dd, J=9.0, 3.2 Hz, 1H), 8.46 (d, J=5.0 Hz, 1H), 12.11-12.34 (m, 1H). MS (ESI$^+$) m/z 478.1 (M+H)$^+$.

EXAMPLE 245

2-{4-[4-(5-fluoro-2-methoxyphenyl)-1H-pyrrolo[2,3-b]pyridin-2-yl]piperidin-1-yl}acetamide A mixture of Example 135B (free base, 0.06 g, 0.184 mmol) and triethylamine (0.077 mL, 0.553 mmol) in N,N-dimethylformamide (1.537 mL) was treated with 2-bromoacetamide (0.029 g, 0.212 mmol) and the mixture was heated at 75° C. for 3.5 hours. The mixture was purified by reverse phase HPLC on a Phenomenex Luna C8(2) 5 um 100 Å AXIA column eluting with a gradient of 10-70% acetonitrile in 0.1% trifluoroacetic acid/water to afford the title compound. $^1$H NMR (400 MHz, CD$_3$OD) δ 2.02-2.28 (m, 2H), 2.32-2.46 (m, 2H), 3.18-3.35 (m, 3H), 3.64-3.85 (m, 2H), 3.82 (s, 3H), 4.00 (s, 2H), 6.47 (bs, 1H), 7.18-7.36 (m, 3H), 7.54 (d, J=6.1 Hz, 1H), 8.33 (d, J=6.1 Hz, 1H). MS (ESI$^+$) m/z 383.2 (M+H)$^+$.

EXAMPLE 246

2-{4-[4-(5-fluoro-2-methoxyphenyl)-1H-pyrrolo[2,3-b]pyridin-2-yl]piperidin-1-yl}-N-methylacetamide The title compound was prepared according to the procedure described in Example 245 substituting 2-bromo-N-methylacetamide (Oakwood Chemical) for 2-bromoacetamide. $^1$H NMR (500 MHz, CD$_3$OD) δ 2.03-2.25 (m, 2H), 2.33-2.44 (m, 2H), 2.81 (s, 3H), 3.15-3.34 (m, 3H), 3.62-3.78 (m, 2H), 3.81 (s, 3H), 3.96 (s, 2H), 6.41 (bs, 1H), 7.17-7.33 (m, 3H), 7.46 (d, J=5.9 Hz, 1H), 8.30 (d, J=5.8 Hz, 1H). MS (ESI$^+$) m/z 397.2 (M+H)$^+$.

EXAMPLE 247

2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone

EXAMPLE 247A tert-butyl 2-(4-(4-(5-fluoro-2-methoxyphenyl)-1H-pyrrolo[2,3-b]pyridin-2-yl)piperidin-1-yl)acetate The title compound was prepared according to the procedure described in Example 226A substituting Example 135B for Example 87. MS (ESI$^+$) m/z 440.1 (M+H)$^+$.

EXAMPLE 247B 2-(4-(4-(5-fluoro-2-methoxyphenyl)-1H-pyrrolo[2,3-b]pyridin-2-yl)piperidin-1-yl)acetic acid The title compound was prepared according to the procedure described in Example 226B substituting Example 247A for Example 226A. MS (ESI$^+$) m/z 384.1 (M+H)$^+$.

EXAMPLE 247C

2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone The title compound was prepared according to the procedure described in Example 238 substituting Example 247B for Example 226B and (S)-pyrrolidin-2-ylmethanol for azetidin-3-ol hydrochloride. $^1$H NMR (400 MHz, pyridine-$d_5$) δ 1.60-1.75 (m, 1H), 1.79-1.94 (m, 3H), 1.96-2.10 (m, 4H), 2.25-2.41 (m, 2H), 2.78-2.94 (m, 1H), 3.05-3.56 (m, 5H), 3.58-3.73 (m, 4H), 3.72-4.05 (m, 2H), 4.33-4.44 (m, 1H), 6.28-6.31 (m, 1H), 7.05 (dd, J=9.0, 4.6 Hz, 1H), 7.12-7.18 (m, 1H), 7.22 (d, J=4.9 Hz, 1H), 7.38 (dd, J=9.0, 3.2 Hz, 1H), 8.45 (d, J=4.9 Hz, 1H), 12.13 (bs, 1H). MS (ESI$^+$) m/z 467.2 (M+H)$^+$.

EXAMPLE 248

4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile

EXAMPLE 248A 4-chloro-1-((2-(trimethylsilyl)ethoxy)methyl)-1H-pyrrolo[2,3-b]pyridine-3-carbonitrile A solution of 4-chloro-1H-pyrrolo[2,3-b]pyridine-3-carbonitrile (2.5 g, 14.08 mmol) in tetrahydrofuran (200 mL) was cooled to 0° C. and treated with sodium hydride (0.5 g, 21.1 mmol). The mixture was stirred at 0° C. for 30 minutes and (2-(chloromethoxy)ethyl)trimethylsilane (2.8 g, 16.9 mmol) was added. After stirring at room temperature for 2 hours, the mixture was treated with brine and extracted with ethyl acetate (three times) and the organic layers were dried over sodium sulfate.

Filtration, concentration and purification by flash chromatography (Combi Flash Rf) (silica gel, 40% ethyl acetate in hexane) afforded the title compound. MS (ESI$^+$) m/z 308 (M+H)$^+$.

EXAMPLE 248B 4-(5-fluoro-2-methoxyphenyl)-1-((2-(trimethylsilyl)ethoxy)methyl)-1H-pyrrolo[2,3-b]pyridine-3-carbonitrile A mixture of Example 248A (3.0 g, 9.78 mmol), (5-fluoro-2-methoxyphenyl)boronic acid (2.5 g, 14.6 mmol), phenylallylchloro(1,3-bis(diisopropylphenyl)-2-imidazol-2-yliden)palladium(II) (0.19 g, 0.29 mmol) and potassium phosphate (4.1 g, 19.6 mmol) in tetrahydrofuran (60 mL) and water (18 mL) was purged with nitrogen and heated at 60° C. for 3 hours. The mixture was treated with brine, extracted with ethyl acetate (three times) and the organic layer was dried over sodium sulfate. Filtration, concentration and purification by flash chromatography (Combi Flash Rf) (silica gel, 30% ethyl acetate in hexane) afforded the title compound. MS (ESI$^+$) m/z 398 (M+H)$^+$.

EXAMPLE 248C 4-(5-fluoro-2-methoxyphenyl)-2-iodo-1-((2-(trimethylsilyl)ethoxy)methyl)-1H-pyrrolo[2,3-b]pyridine-3-carbonitrile A solution of Example 248B (0.7 g, 1.76 mmol) in tetrahydrofuran (50 mL) was cooled to −75° C. and treated dropwise with 2N lithium diisopropylamide in tetrahydrofuran (1.7 mL, 3.40 mmol). The mixture was stirred at −75° C. for 30 minutes and iodine (0.85 g, 3.52 mmol) in 2.5 mL tetrahydrofuran was added. The mixture was slowly brought to room temperature and quenched with aqueous ammonium chloride (100 mL) and extracted with ethyl acetate (twice). The organic layers were concentrated and purified by column chromatography (Combi Flash Rf) (silica gel, 30% ethyl acetate in hexane) to afford the title compound. MS (ESI$^+$) m/z 524 (M+H)$^+$.

EXAMPLE 248D tert-butyl 4-(3-cyano-4-(5-fluoro-2-methoxyphenyl)-1H-pyrrolo[2,3-b]pyridin-2-yl)-5,6-dihydropyridine-1(2H)-carboxylate The title compound was prepared using the procedure described in Example 87C, using Example 248C in place of Example 87B. MS (ESI$^+$) m/z 449 (M+H)$^+$.

EXAMPLE 248E 4-(5-fluoro-2-methoxyphenyl)-2-(1,2,3,6-tetrahydropyridin-4-yl)-1H-pyrrolo[2,3-b]pyridine-3-carbonitrile The title compound was prepared using the procedure described in Example 1H, using Example 248D in place of Example 1G. MS (ESI$^+$) m/z 449 (M+H)$^+$.

EXAMPLE 248F 4-(5-fluoro-2-methoxyphenyl)-2-(1-(methylsulfonyl)-1,2,3,6-tetrahydropyridin-4-yl)-1H-pyrrolo[2,3-b]pyridine-3-carbonitrile The title compound was prepared using the procedure described in Example 148, using Example 248E in place of Example 135B. $^1$H NMR (400 MHz, DMSO-$d_6$/$D_2$O): δ 2.76-2.91 (m, 2H), 3.48 (t, J=5.7 Hz, 2H), 3.78 (s, 3H), 3.96, 4.03 (q, J=3.0 Hz, 2H), 6.70-6.78 (m, 1H), 7.13-7.30 (m, 2H), 7.24 (dd, J=8.7, 3.1 Hz, 1H), 7.36 (td, J=8.6, 3.1 Hz, 1H), 8.46 (d, J=4.9 Hz, 1H), 12.94 (s, 1H). MS (ESI$^+$) m/z 427 (M+H)$^+$.

EXAMPLE 249

4-[3-cyano-4-(5-fluoro-2-methoxyphenyl)-1H-pyrrolo[2,3-b]pyridin-2-yl]-N-methyl-3,6-dihydropyridine-1(2H)-carboxamide The title compound was prepared using the procedure described in Example 215, using Example 248E in place of Example 87. $^1$H NMR (400 MHz, DMSO-$d_6$) δ 2.60 (s, 3H), 2.61-2.68 (m, 2H), 3.54 (t, J=5.6 Hz, 2H), 3.72 (s, 3H), 4.07 (q, J=3.0 Hz, 2H), 6.62-6.78 (m, 1H), 7.09-7.15 (m, 2H), 7.18 (dd, J=8.7, 3.2 Hz, 1H), 7.29 (td, J=8.7, 3.2 Hz, 1H), 8.39 (d, J=4.9 Hz, 1H). MS (ESI$^+$) m/z 406 (M+H)$^+$.

EXAMPLE 250 ethyl ({4-[4-(5-fluoro-2-methoxyphenyl)-1H-pyrrolo[2,3-b]pyridin-2-yl]cyclohex-3-en-1-yl}sulfamoyl)carbamate

EXAMPLE 250A 4-(4-(5-fluoro-2-methoxyphenyl)-1H-pyrrolo[2,3-b]pyridin-2-yl)cyclohex-3-enamine The title compound was prepared essentially as described in Example 223A-C, substituting tert-butyl(4-oxocyclohexyl)carbamate for tert-butyl 3-oxo-8-azabicyclo[3.2.1]octane-8-carboxylatein Example 223A. MS (DCI/NH₃) m/z 489 (M+H)⁺.

EXAMPLE 250B ethyl ({4-[4-(5-fluoro-2-methoxyphenyl)-1H-pyrrolo[2,3-b]pyridin-2-yl]cyclohex-3-en-1-yl}sulfamoyl)carbamate The title compound was prepared essentially as described in Example 218, substituting Example 250A for Example 87 in Example 218B and ethanol for tert-butanol in Example 218A. ¹H NMR (400 MHz, DMSO-d₆) δ 1.21 (t, J=7.02 Hz, 3 H), 1.59-1.68 (m, 1 H), 1.92-1.98 (m, 1 H), 2.17-2.25 (m, 1 H), 2.37-2.46 (m, 1 H), 2.55-2.61 (m, 1 H), 3.38-3.43 (m, 1 H), 3.73 (s, 3 H), 4.13 (q, J=7.02 Hz, 2 H), 6.18 (d, J=1.53 Hz, 1 H), 6.41 (s, 1 H), 7.02 (d, J=5.19 Hz, 1 H), 7.16-7.29 (m, 3 H), 7.86 (d, J=7.02 Hz, 1 H), 8.18 (d, J=4.88 Hz, 1 H), 11.12 (s, 1 H), 11.71 (s, 1 H). MS (DCI/NH₃) m/z 489 (M+H)⁺.

EXAMPLE 251

2-{4-[4-(5-fluoro-2-methoxyphenyl)-1H-pyrrolo[2,3-b]pyridin-2-yl]piperidin-1-yl}-N-(2-hydroxyethyl)-N-methylacetamide Stock solutions (in N,N-dimethylacetamide) of Example 247B (0.27M, 286 µL, 0.078 mmol), N,N-di-isopropylethylamine (0.81M, 0.234 mmol), 1-[bis(dimethylamino)methylene]-1H-1,2,3-triazolo[4,5-b]pyridinium 3-oxide hexafluorophosphate (0.32M, 286 µL, 0.094 mmol), and 2-(methylamino)ethanol (0.41M, 235 µL, 0.094 mmol) were mixed through a PFA mixing tube (0.2 mm inner diameter), and loaded into an injection loop. The reaction segment was described injected into a flow reactor (Hastelloy coil, 0.75 mm inner diameter, 1.8 mL internal volume) set at 100° C., and passed through the reactor at 180 µL min⁻¹ (10 minute residence time). Upon exiting the reactor, the reaction was loaded directly into an injection loop and purified by preparative HPLC on a Phenomenex Luna C8(2) 5 um 100 Å AXIA column, eluting with a 5-100% gradient of acetonitrile/0.1% ammonium acetate in water. ¹H NMR (400 MHz, DMSO-d₆) δ 1.63-1.82 (m, 2H), 1.91-2.12 (m, 2H), 2.24 (td, J=11.6, 2.5 Hz, 2H), 2.66-3.22 (m, 8H), 3.44 (s, 4H), 3.72 (s, 3H), 5.96 (s, 1H), 7.00 (d, J=5.0 Hz, 1H), 7.09-7.27 (m, 3H), 8.13 (d, J=5.0 Hz, 1H). MS (APCI) m/z 441.3 [M+H]⁺.

EXAMPLE 252

2-{4-[4-(5-fluoro-2-methoxyphenyl)-1H-pyrrolo[2,3-b]pyridin-2-yl]piperidin-1-yl}-N-(3-hydroxycyclobutyl)acetamide The title compound was prepared according to the procedure described in Example 251 substituting 3-aminocyclobutanol hydrochloride (Synthonix) for 2-(methylamino)ethanol. ¹H NMR (400 MHz, DMSO-d₆) δ 1.66-1.84 (m, 3H), 1.98 (d, J=12.9 Hz, 2H), 2.05-2.33 (m, 4H), 2.56 (ddd, J=7.0, 4.5, 2.6 Hz, 1H), 2.61-2.83 (m, 1H), 2.83-2.96 (m, 4H), 3.72 (s, 4H), 4.18-4.41 (m, 1H), 5.98 (s, 1H), 7.01 (d, J=5.0 Hz, 1H), 7.09-7.28 (m, 3H), 8.13 (d, J=4.9 Hz, 1H). MS (APCI) m/z 453.3 [M+H]⁺.

EXAMPLE 253

2-{4-[4-(5-fluoro-2-methoxyphenyl)-1H-pyrrolo[2,3-b]pyridin-2-yl]piperidin-1-yl}-1-(3-hydroxyazetidin-1-yl) ethanone The title compound was prepared according to the procedure described in Example 238 substituting Example 247B for Example 226B. ¹H NMR (400 MHz, DMSO-d₆) δ 1.65-1.78 (m, 2H), 1.90-2.00 (m, 2H), 2.07-2.20 (m, 2H), 2.62-2.71 (m, 1H), 2.84-2.92 (m, 2H), 2.92-3.03 (m, 2H), 3.52-3.62 (m, 1H), 3.73 (s, 3H), 3.87-3.96 (m, 1H), 3.96-4.08 (m, 1H), 4.25-4.50 (m, 2H), 5.96 (s, 1H), 7.00 (d, J=4.9 Hz, 1H), 7.12-7.32 (m, 3H), 8.13 (d, J=4.9 Hz, 1H), 11.57 (bs, 1H). MS (ESI⁺) m/z 439.2 (M+H)⁺.

EXAMPLE 254

N-{4-[4-(5-fluoro-2-methoxyphenyl)-1H-pyrrolo[2,3-b]pyridin-2-yl]cyclohex-3-en-1-yl}-3-methyl-L-valine The title compound was prepared essentially as described in Example 241C, substituting (R)-tert-butyl 2-amino-3-methylbutanoate hydrochloride with (S)-tert-butyl 2-amino-3,3-dimethylbutanoate hydrochloride to provide the title compound as the hydrochloride salt. ¹H NMR (500 MHz, DMSO-d₆) δ 1.02-1.24 (m, 9 H) 1.78-2.17 (m, 1 H) 2.31 (s, 1 H) 2.45 (d, J=12.82 Hz, 1 H) 2.54-2.88 (m, 3 H) 3.28 (s, 1 H) 3.65-3.85 (m, 3 H) 4.00 (d, J=10.68 Hz, 2 H) 6.41 (s, 1 H) 6.61 (s, 1 H) 7.07-7.53 (m, 4 H) 8.29 (d, J=5.49 Hz, 1 H) 8.87 (s, 1 H) 12.76 (d, J=13.43 Hz, 1 H). MS (ESI): 452.1 (M+H)⁺.

EXAMPLE 255

2-{4-[5-fluoro-4-(5-fluoro-2-methoxyphenyl)-1H-pyrrolo[2,3-b]pyridin-2-yl]piperidin-1-yl}-N,N-dimethylacetamide

EXAMPLE 255A tert-butyl 4-((4-chloro-5-fluoro-2-pivalamidopyridin-3-yl)ethynyl)piperidine-1-carboxylate A mixture of N-(4-chloro-5-fluoro-3-iodopyridin-2-yl) pivalamide (1 g, 2.80 mmol), tert-butyl 4-ethynylpiperidine-1-carboxylate (0.880 g, 4.21 mmol), copper(I) iodide (0.053 g, 0.28 mmol), and bis(triphenylphosphine)palladium(II) dichloride (0.197 g, 0.280 mmol) in 50 mL tetrahydrofuran was degassed with nitrogen. The mixture was stirred at room temperature for 48 hours and at 50° C. for 8 hours. The mixture was filtered and the filtrate was diluted with water and extracted with ethyl acetate. The organic phase was washed with brine, dried over sodium sulfate, filtered and concentrated. The residue was purified by silica-gel column chromatography eluting with 0-40% ethyl acetate in heptane to afford the title compound. MS (ESI(+)) m/e 438 (M+H)⁺.

EXAMPLE 255B tert-butyl 4-(4-chloro-5-fluoro-1H-pyrrolo[2,3-b]pyridin-2-yl)piperidine-1-carboxylate A mixture of Example 255A (1000 mg, 2.283 mmol), 18-crown-6 (302 mg, 1.142 mmol), and potassium 2-methylpropan-2-olate (512 mg, 4.57 mmol) in 15 mL t-butanol was heated under microwave (Biotage) conditions at 135° C. for 35 minutes. Water was added and the mixture was extracted with dichloromethane. The organic phase was washed with water and brine, dried over sodium sulfate, filtered and concentrated. The residue was triturated with diethyl ether and filtered to afford the title compound. MS (ESI(+)) m/e 354 (M+H)$^+$.

EXAMPLE 255C tert-butyl 4-(5-fluoro-4-(5-fluoro-2-methoxyphenyl)-1H-pyrrolo[2,3-b]pyridin-2-yl)piperidine-1-carboxylate A mixture of Example 255B (600 mg, 1.696 mmol), (5-fluoro-2-methoxyphenyl)boronic acid (403 mg, 2.374 mmol), phenylallylchloro[1,3-bis(diisopropylphenyl)-2-imidazol-2-ylidene]palladium(II) (110 mg, 0.170 mmol), and potassium phosphate (1080 mg, 5.09 mmol) in 12 mL tetrahydrofuran and 3 mL water was degassed with nitrogen and heated in a Biotage microwave for 40 minutes at 120° C. The mixture was extracted with ethyl acetate and purified by silica gel column chromatography eluting with 0-5% methanol in dichloromethane to afford the title compound. MS (ESI(+)) m/e 444 (M+H)$^+$.

EXAMPLE 255D 5-fluoro-4-(5-fluoro-2-methoxyphenyl)-2-(piperidin-4-yl)-1H-pyrrolo[2,3-b]pyridine The title compound was prepared using the procedure described in Example 236F, substituting Example 255C for Example 236D. MS (ESI(+)) m/e 344 (M+H)$^+$.

EXAMPLE 255E

2-{4-[5-fluoro-4-(5-fluoro-2-methoxyphenyl)-1H-pyrrolo[2,3-b]pyridin-2-yl]piperidin-1-yl}-N,N-dimethylacetamide The title compound was prepared using the procedure described in Example 235, substituting Example 255D for Example 17G. $^1$H NMR (400 MHz, DMSO-d$_6$) δ 0.85-1.83 (m, 2H), 1.93-2.03 (m, 2H), 2.15-2.25 (m, 2H), 2.66-2.81 (m, 1H), 2.86 (s, 3H), 2.91-2.99 (m, 2H), 3.08 (s, 3H), 3.19 (bs, 2H), 3.78 (s, 3H), 5.95 (bs, 1H), 7.22-7.29 (m, 2H), 7.37 (td, J=8.6, 3.2 Hz, 1H), 8.17 (d, J=2.5 Hz, 1H), 11.75 (bs, 1H). MS (ESI(+)) m/e 429 (M+H)$^+$.

EXAMPLE 256

2-{4-[3-cyano-4-(5-fluoro-2-methoxyphenyl)-1H-pyrrolo[2,3-b]pyridin-2-yl]-3,6-dihydropyridin-1(2H)-yl}-N,N-dimethylacetamide To a suspension of Example 248E (125 mg, 0.359 mmol) in N,N-dimethylformamide (6 mL) was added triethylamine (0.30 mL, 2.153 mmol) and 2-chloro-N,N-dimethylacetamide (56 mg, 0.466 mmol) and the mixture was heated at 70° C. for 3 hours. After cooling, the mixture was partitioned between ethyl acetate and sodium bicarbonate and the organic phase was washed with brine and concentrated. The residue was purified by flash chromatography (5-20% methanol in 2:1 ethyl acetate/hexane) to provide the title compound. $^1$H NMR (400 MHz, DMSO-d$_6$): δ 2.77-2.80 (m, 2 H), 2.86 (t, J=5.65 Hz, 2 H), 2.95 (s, 3 H), 3.11 (s, 3 H), 3.37 (q, J=2.75 Hz, 2 H), 3.77 (s, 3 H), 6.65-6.67 (m, 1 H), 7.04-7.12 (m, 3 H), 7.15-7.21 (m, 1 H), 8.34 (d, J=4.88 Hz, 1 H). MS (DCI/NH$_3$) m/z 434 (M+H)$^+$.

EXAMPLE 257

2-{4-[4-(2-methoxyphenyl)-1H-pyrrolo[2,3-b]pyridin-2-yl]piperidin-1-yl}-N,N-dimethylacetamide

EXAMPLE 257A tert-butyl 4-(4-(2-methoxyphenyl)-1-(phenylsulfonyl)-1H-pyrrolo[2,3-b]pyridin-2-yl)-5,6-dihydropyridine-1(2H)-carboxylate The title compound was prepared as described in Example 87A-C, substituting 2-methoxyphenylboronic acid for 5-fluoro-2-methoxyphenylboronic acid in Example 87A.

EXAMPLE 257B 4-(2-methoxyphenyl)-2-(piperidin-4-yl)-1H-pyrrolo[2,3-b]pyridine

The title compound was prepared as described in Example 135A-B, substituting Example 257A for Example 87C in Example 135A.

EXAMPLE 257C

2-{4-[4-(2-methoxyphenyl)-1H-pyrrolo[2,3-b]pyridin-2-yl]piperidin-1-yl}-N,N-dimethylacetamide The title compound was prepared as described in Example 224, substituting Example 257B for Example 87. $^1$H NMR (500 MHz, DMSO-d$_6$) δ 1.69 (qd, J=12.4, 3.7 Hz, 2H), 1.90-1.99 (m, 2H), 2.11-2.22 (m, 2H), 2.67 (tt, J=11.9, 3.8 Hz, 1H), 2.81 (s, 3H), 2.90 (dt, J=11.7, 3.1 Hz, 2H), 3.03 (s, 3H), 3.14 (s, 2H), 3.75 (s, 3H), 5.93 (d, J=2.1 Hz, 1H), 6.99 (d, J=4.9 Hz, 1H), 7.07 (t, J=7.4 Hz, 1H), 7.17 (d, J=8.2 Hz, 1H), 7.29-7.47 (m, 2H), 8.12 (d, J=4.9 Hz, 1H), 11.50 (d, J=2.2 Hz, 1H). MS (ESI$^+$) m/z 393 (M+H)$^+$.

EXAMPLE 258

4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine

EXAMPLE 258A (S)-tert-butyl 2-methyl-4-(((trifluoromethyl)sulfonyl)oxy)-5,6-dihydropyridine-1(2H)-carboxylate and (S)-tert-butyl 6-methyl-4-(((trifluoromethyl)sulfonyl)oxy)-5,6-dihydropyridine-1(2H)-carboxylate A solution of (S)-tert-butyl-2-methyl-4-oxopiperidine-1-carboxylate (5 g, 23.44 mmol) in tetrahydrofuran (100 mL) was cooled to −78° C. and lithium bis(trimethylsilyl)amide (1M in hexanes, 28.1 mL, 28.1 mmol) was added dropwise. The mixture was stirred at −78° C. for 30 minutes and a solution of 1,1,1-trifluoro-N-phenyl-N-((trifluoromethyl)sulfonyl) methanesulfonamide (10.89 g, 30.5 mmol) in tetrahydrofuran (25 mL) was added dropwise. The mixture was allowed to warm to room temperature and after 24 hours, the reaction was quenched with saturated ammonium chloride and extracted with ethyl acetate. The extracts were dried over sodium sulfate, filtered, and concentrated.

Purification by flash chromatography on silica gel eluting with 0-40% ethyl acetate-hexanes gave an oil as a mixture of enol isomers. This material also contained 25% by weight 1,1,1-trifluoro-N-phenylmethanesulfonamide. The mixture was carried on in the next step without any further purification. MS (ESI) m/e 246.0 (M-BOC)$^+$.

EXAMPLE 258B 4-(5-fluoro-2-methoxyphenyl)-1-tosyl-1H-pyrrolo[2,3-b]pyridine

To a mixture of 4-bromo-1-(4-methylphenylsulfonyl)-1H-pyrrolo[2,3-b]pyridine (100 g, 284.7 mmol) and (5-fluoro-2-methoxyphenyl)boronic acid (58.05 g, 341.6 mmol) in dimethoxyethane (1600 mL) and water (440 mL) was added potassium carbonate (106.2 g, 768.6 mmol). The mixture was purged with nitrogen and [1,1'-bis(diphenylphosphino) ferrocene]dichloropalladium(II)-dichloromethane adduct (13.95 g, 17.08 mmol) was added. The mixture was purged with nitrogen for 10 minutes and stirred at 100° C. for 1 hour. After concentration, the residue was diluted with ethyl acetate (1500 mL) and washed with aqueous sodium bicarbonate (twice) and brine. The organic layer was dried over sodium sulfate, filtered and concentrated under reduced pressure. The residue was purified by flash chromatography on silica gel eluting with 30-60% ethyl acetate in petroleum ether to afford the title compound.

EXAMPLE 258C 4-(5-fluoro-2-methoxyphenyl)-2-iodo-1-tosyl-1H-pyrrolo[2,3-b]pyridine To a solution of Example 258B (98 g, 247.2 mmol) in tetrahydrofuran (3528 mL) was added lithium diisopropylamide (1.8M in tetrahydrofuran/heptane/ethylbenzene, 233.4 mL, 420.2 mmol) at −78° C. The mixture was stirred for 20 minutes and a solution of iodine (116.07 g, 457.3 mmol) in tetrahydrofuran (392 mL) was added drop wise over 20 minutes, maintaining the temperature below −70° C. After 30 minutes, the mixture was poured into a saturated ammonium chloride (980 mL) and extracted with ethyl acetate (twice). The combined extracts were washed with saturated sodium thiosulfate (twice) and brine, dried over sodium sulfate, filtered, and concentrated. The residue was purified by flash chromatography on silica gel eluting with 0-11% ethyl acetate in 10% dichloromethane/petroleum ether to afford the title compound.

EXAMPLE 258D (S)-tert-butyl 4-(4-(5-fluoro-2-methoxyphenyl)-1-tosyl-1H-pyrrolo[2,3-b]pyridin-2-yl)-2-methyl-5,6-dihydropyridine-1(2H)-carboxylate and (S)-tert-butyl 4-(4-(5-fluoro-2-methoxyphenyl)-1-tosyl-1H-pyrrolo[2,3-b]pyridin-2-yl)-6-methyl-5,6-dihydropyridine-1(2H)-carboxylate (4:1)

A mixture of Example 258A (1.75 g, 6.89 mmol), bis(diphenylphosphino)ferrocene]dichloropalladium(II)-dichloromethane adduct (0.235 g, 0.287 mmol), 4,4,4',4',5,5,5',5'-octamethyl-2,2'-bi(1,3,2-dioxaborolane) (1.75 g, 28.7 mmol), and potassium acetate (2.82 g, 28.7 mmol) in dioxane (40 mL) was degassed and heated at reflux for 90 minutes. After cooling to room temperature, Example 258C (3 g, 5.74 mmol), additional bis(diphenylphosphino) ferrocene]dichloropalladium(II)-dichloromethane adduct (0.235 g, 0.287 mmol) and a solution of sodium carbonate (3.35 g, 31.6 mmol) in water (0.5 mL) was added and the mixture was heated to 65° C. for 24 hours. The mixture was partitioned between water and ethyl acetate and the organic layer was dried over sodium sulfate, filtered, and concentrated. Purification by flash chromatography on silica gel eluting with 0-30% ethyl acetate in heptanes over 50 minutes provided the title compound as a mixture of regioisomers which was used in the next step without any further purification. MS (ESI) m/e 592.1 (M+1)$^+$.

EXAMPLE 258E (S)-tert-butyl 4-(4-(5-fluoro-2-methoxyphenyl)-1H-pyrrolo[2,3-b]pyridin-2-yl)-2-methyl-5,6-dihydropyridine-1(2H)-carboxylate and (S)-tert-butyl 4-(4-(5-fluoro-2-methoxyphenyl)-1H-pyrrolo[2,3-b]pyridin-2-yl)-6-methyl-5,6-dihydropyridine-1(2H)-carboxylate (4:1)

To a solution of Example 258D (3.06 g, 5.17 mmol) in dioxane (29.6 mL) was added a solution of sodium hydroxide (0.724 g, 18.1 mmol) in water (3.62 mL) and the mixture was heated at 90° C. for 24 hours. The mixture was cooled to room temperature, diluted with saturated sodium bicarbonate and extracted with ethyl acetate. The combined extracts were dried over sodium sulfate, filtered, and concentrated. Purification by flash chromatography on silica gel eluting with 0-50% methanol in dichloromethane provided the title compound as a mixture of regioisomers which was used in the next step without any further purification. MS (ESI) m/e 438.1 (M+1)$^+$.

EXAMPLE 258F (S)-4-(5-fluoro-2-methoxyphenyl)-2-(6-methyl-1,2,3,6-tetrahydropyridin-4-yl)-1H-pyrrolo[2,3-b]pyridine To a solution of Example 258E (0.600 g, 1.37 mmol) in 4 mL 1:1 methanol:ethyl acetate was added 2M hydrogen chloride in diethyl ether (5 mL) and the mixture was stirred at 40° C. for 2 hours and concentrated. Purification by reverse phase-HPLC (Sunfire 5 µM, 50×250 mm) eluting with 5-40% acetonitrile in water (containing 0.1% trifluoroacetic acid), provided the title compound as trifluoroacetate salt. To a solution of this salt in methanol was added 2M hydrogen chloride in diethyl ether. Concentration afforded the title compound as the hydrochloride salt. MS (ESI) m/e 338.1 (M+1)$^+$.

EXAMPLE 258G 4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine Methanesulfonyl chloride (0.03 mL, 0.38 mmol) was added to Example 258F (96.4 mg, 0.235 mmol) and triethylamine (0.2 mL, 1.43 mmol) in N,N-dimethylformamide (2 mL). After stirring at room temperature for 24 hours, the mixture was concentrated. Purification by reverse phase-HPLC (Sunfire 5 µM, 50×250 mm) eluting with 5-50% acetonitrile in water (containing 0.1% trifluoroacetic acid)

provided the trifluoroacetate salt. The salt was dissolved in methanol and eluted from a SCX column with 0.5M ammonia in methanol to give the free base of the title compound. $^1$HNMR (500 MHz, DMSO-d$_6$) δ 1.31 (d, 3H), 2.53 (m, 2H), 2.93 (s, 3H), 3.22 (m, 1H), 3.74 (s, 3H), 3.77 (m, 1H), 4.44 (m, 1H), 6.28 (d, 1H), 6.51 (m, 1H), 7.04 (d, 1H), 7.25 (m, 3H), 8.21 (d, 1H), 11.83 (br s, 1H). MS (ESI) m/e 416.1 (M+1)$^+$.

EXAMPLE 259

2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone

EXAMPLE 259A tert-butyl 2-(4-(5-fluoro-4-(5-fluoro-2-methoxyphenyl)-1H-pyrrolo[2,3-b]pyridin-2-yl)piperidin-1-yl) acetate The title compound was prepared using the procedure described in Example 226A, substituting Example 255D for Example 87. MS (ESI(+)) m/e 458 (M+H)$^+$.

EXAMPLE 259B 2-(4-(5-fluoro-4-(5-fluoro-2-methoxyphenyl)-1H-pyrrolo[2,3-b]pyridin-2-yl)piperidin-1-yl)acetic acid The title compound was prepared using the procedure described in Example 226B, substituting Example 259A for Example 226A. MS (ESI(+)) m/e 402 (M+H)$^+$.

EXAMPLE 259C

2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone The title compound was prepared using the procedure described in Example 238, substituting Example 259B for 226B. $^1$H NMR (500 MHz, DMSO-d$_6$) δ 1.67-1.91 (m, 2H), 1.91-2.01 (m, 2H), 2.04-2.42 (m, 2H), 2.58-3.26 (m, 5H), 3.59 (dd, J=10.1, 4.3 Hz, 1H), 3.72 (s, 3H), 3.93 (dd, J=9.4, 4.3 Hz, 1H), 3.99-4.08 (m, 1H), 4.37 (d, J=8.7 Hz, 1H), 4.39-4.48 (m, 1H), 5.69 (d, J=6.0 Hz, 1H), 5.91 (d, J=2.0 Hz, 1H), 7.15-7.27 (m, 2H), 7.32 (td, J=8.6, 3.2 Hz, 1H), 8.13 (d, J=2.5 Hz, 1H), 11.73 (bs, 1H). MS (ESI(+)) m/e 457 (M+H)$^+$.

EXAMPLE 260

2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide

EXAMPLE 260A (2S)-tert-butyl 4-hydroxy-2-(hydroxymethyl)piperidine-1-carboxylate A solution of (S)-1-(tert-butoxycarbonyl)-4-oxopiperidine-2-carboxylic acid (5 g, 20.55 mmol) in tetrahydrofuran (100 mL) under nitrogen was cooled in an ice bath. 1N Borane-tetrahydrofuran in tetrahydrofuran (61.7 mL, 61.7 mmol) was added dropwise over 25 minutes and the mixture was stirred at room temperature for 3 hours, cooled to 0° C. and quenched with 10 mL water. Potassium carbonate (5 g) was added and the mixture was stirred overnight at room temperature, and partitioned between water and ether (three times). The ether extracts were dried over sodium sulfate, filtered, concentrated onto silica gel, and purified by flash chromatography (gradient of 0-100% ethyl acetate-heptanes) to provide the title compound as a mixture of diastereomers. MS (ESI+) m/z 231.9 (M+H)+.

EXAMPLE 260B (2S)-tert-butyl 4-hydroxy-2-(((triisopropylsilyl)oxy) methyl)piperidine-1-carboxylate Chlorotriisopropylsilane (2.284 g, 11.85 mmol) was added dropwise to a 0° C. solution of Example 260A (2.65 g, 10.77 mmol), triethylamine (1.253 g, 12.39 mmol) and 4-(dimethylamino)pyridine (0.263 g, 2.154 mmol) in dichloromethane (25 mL). The mixture was stirred at 0° C. for 20 minutes and at room temperature for 16 hours. Water (50 mL) was added and the layers were separated. The aqueous layer was extracted with dichloromethane (twice), and the combined extracts were dried over sodium sulfate, filtered, and concentrated. The residue was purified by flash chromatography on silica gel (gradient of 0-30% ethyl acetate/heptanes) to provide the title compound as a mixture of diastereomers. MS (ESI+) m/z 388.0 (M+H)+.

EXAMPLE 260C (S)-tert-butyl 4-oxo-2-(((triisopropylsilyl)oxy) methyl)piperidine-1-carboxylate To a solution of Example 260B (3.32 g, 8.56 mmol) in dichloromethane (28.5 mL) was added activated powdered 4 Å molecular sieves (9 g), tetrapropylammonium perruthenate (0.150 g, 0.428 mmol) and N-methylmorpholine-N-oxide (1.505 g, 12.85 mmol), and the mixture was stirred overnight at room temperature. The mixture was filtered through a pad of silica, rinsing with ethyl acetate. The filtrate was concentrated and purified by flash chromatography on silica gel (gradient from 0-20% ethyl acetate-heptanes) to provide the title compound. MS (ESI+) m/z 385.8 (M+H)+.

EXAMPLE 260D (S)-tert-butyl 4-(((trifluoromethyl)sulfonyl)oxy)-6-(((triisopropylsilyl)oxy)methyl)-5,6-dihydropyridine-1(2H)-carboxylate and (S)-tert-butyl 4-(((trifluoromethyl)sulfonyl)oxy)-2-(((triisopropylsilyl) oxy)methyl)-5,6-dihydropyridine-1(2H)-carboxylate A solution of Example 260C (2.27 g, 5.89 mmol) in tetrahydrofuran (24 mL) at −78° C. was treated dropwise with a 1M solution of sodium bis(trimethylsilyl)amide in tetrahydrofuran (7.06 ml, 7.06 mmol). The mixture was stirred for 30 minutes at −78° C. and a solution of 1,1,1-trifluoro-N-phenyl-N-((trifluoromethyl)sulfonyl)methanesulfonamide (2.73 g, 7.65 mmol) in tetrahydrofuran (6 mL) was added dropwise. The mixture allowed to warm to room temperature and stirred for 3 hours. The reaction was quenched with saturated aqueous ammonium chloride (50 mL) and extracted with ethyl acetate (three times). The organic extracts were dried over sodium sulfate, filtered, and concentrated and the residue was purified by flash chromatography on silica gel, eluting with a gradient from 0-40% ethyl acetate-heptanes to give a mixture of the two diastereomers, which was used in the next step without further purification. MS (ESI+) m/z 418.1 (M-Boc+H)+.

EXAMPLE 260E (S)-tert-butyl 4-(4-(5-fluoro-2-methoxyphenyl)-1H-pyrrolo[2,3-b]pyridin-2-yl)-6-(((triisopropylsilyl)oxy)methyl)-5,6-dihydropyridine-1(2H)-carboxylate The mixture of Example 260D (2.66 g, 4.62 mmol), bis(pinacolatodiboron) (1.173 g, 4.62 mmol), and potassium acetate (2.266 g, 23.09 mmol) in dioxane (25 mL) was degassed with nitrogen for 30 minutes. Bis(diphenylphosphino)ferrocene]dichloropalladium(II)-dichloromethane complex (0.189 g, 0.231 mmol) was added and the mixture was heated at reflux for 1.5 hours and cooled to room temperature. To this mixture was added Example 219A (1.7 g, 4.62 mmol), bis(diphenylphosphino)ferrocene]dichloropalladium(II)-dichloromethane complex (0.189 g, 0.231 mmol) and a degassed solution of sodium carbonate (2.69 g, 25.4 mmol) in water (12.5 mL). Nitrogen was bubbled through the mixture for 10 minutes, followed by heating at 75° C. for 16 hours. After cooling to room temperature, the mixture was partitioned between water and ethyl acetate (three times). The combined extracts were dried over sodium sulfate, filtered, and concentrated, and the residue was purified by flash chromatography on silica gel, eluting with a gradient from 0-5% methanol in dichloromethane, to provide the two diastereomers, Example 260E (eluting last) and Example 260F (eluting first). Example 260E: MS (ESI+) m/z 610.2 (M+H)+.; Example 260F: MS (ESI+) m/z 610.2 (M+H)+.

EXAMPLE 260F (S)-tert-butyl 4-(4-(5-fluoro-2-methoxyphenyl)-1H-pyrrolo[2,3-b]pyridin-2-yl)-2-(((triisopropylsilyl)oxy)methyl)-5,6-dihydropyridine-1(2H)-carboxylate The mixture of Example 260D (2.66 g, 4.62 mmol), bis(pinacolatodiboron) (1.173 g, 4.62 mmol), and potassium acetate (2.266 g, 23.09 mmol) in dioxane (25 mL) was degassed with nitrogen for 30 minutes. Bis(diphenylphosphino)ferrocene]dichloropalladium(II)-dichloromethane complex (0.189 g, 0.231 mmol) was added and the mixture was heated at reflux for 1.5 hours and cooled to room temperature. To this mixture was added Example 219A (1.7 g, 4.62 mmol), bis(diphenylphosphino)ferrocene]dichloropalladium(II)-dichloromethane complex (0.189 g, 0.231 mmol) and a degassed solution of sodium carbonate (2.69 g, 25.4 mmol) in water (12.5 mL). Nitrogen was bubbled through the mixture for 10 minutes, followed by heating at 75° C. for 16 hours. After cooling to room temperature, the mixture was partitioned between water and ethyl acetate (three times). The combined extracts were dried over sodium sulfate, filtered, and concentrated, and the residue was purified by flash chromatography on silica gel, eluting with a gradient from 0-5% methanol in dichloromethane, to provide the two diastereomers, Example 260E (eluting last) and Example 260F (eluting first). Example 260E: MS (ESI+) m/z 610.2 (M+H)+; Example 260F: MS (ESI+) m/z 610.2 (M+H)+.

EXAMPLE 260G (S)-tert-butyl 4-(4-(5-fluoro-2-methoxyphenyl)-1H-pyrrolo[2,3-b]pyridin-2-yl)-6-(hydroxymethyl)-5,6-dihydropyridine-1(2H)-carboxylate A solution of 1M tetrabutylammonium fluoride in tetrahydrofuran (3.1 mL, 3.10 mmol) was added to a solution of Example 260E (627 mg, 1.028 mmol) in tetrahydrofuran (5 mL) and the mixture was stirred at room temperature for 1 hour and concentrated. The residue was purified by flash chromatography on silica gel, eluting with a gradient of 0-7% methanol-dichloromethane to provide the title compound. MS (ESI+) m/z 454.1 (M+H)+.

EXAMPLE 260H (S)-(4-(4-(5-fluoro-2-methoxyphenyl)-1H-pyrrolo[2,3-b]pyridin-2-yl)-1,2,3,6-tetrahydropyridin-2-yl)methanol The title compound was prepared as the hydrochloride salt using the procedure described in Example 1H, using Example 260G (334 mg, 0.736 mmol) in place of Example 1G. MS (ESI+) m/z 354.0 (M+H)+.

EXAMPLE 260I

2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide To a solution of Example 260H (150 mg, 0.352 mmol) in N,N-dimethylformamide (1.8 mL) was added N-ethyl-N-isopropylpropan-2-amine (227 mg, 1.759 mmol) and 2-chloro-N,N-dimethylacetamide (39.9 µL, 0.387 mmol). The mixture was stirred for 3 days at room temperature and for 2 hours at 70° C., and partitioned between water and ethyl acetate (three times). The extracts were dried over sodium sulfate, filtered, and concentrated, and the residue was purified by flash chromatography on silica gel, eluting with a gradient of 0-8% methanol/dichloromethane to afford the title compound. $^1$H NMR (400 MHz, DMSO-$d_6$) δ 11.77 (s, 1H), 8.18 (d, J=5.0 Hz, 1H), 7.31-7.16 (m, 3H), 7.02 (d, J=5.0 Hz, 1H), 6.46 (s, 1H), 6.18 (d, J=1.8 Hz, 1H), 4.61 (t, J=5.3 Hz, 1H), 3.74 (s, 3H), 3.60-3.27 (m, 6H), 3.33 (s, 3H), 3.02 (s, 3H), 2.93 (dd, J=11.1, 5.7 Hz, 1H), 2.81 (s, 3H), 2.48-2.32 (m, 2H); MS (ESI+) m/z 439.0 (M+H)+.

EXAMPLE 261

2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide Example 261 was prepared essentially as described in Example 260, substituting Example 260F for Example 260E in Example 260G. $^1$H NMR (500 MHz, DMSO-$d_6$) δ 11.75 (s, 1H), 8.19 (d, J=4.9 Hz, 1H), 7.35-7.11 (m, 3H), 7.02 (d, J=5.0 Hz, 1H), 6.48-6.45 (m, 1H), 6.23 (d, J=1.8 Hz, 1H), 4.81 (t, J=5.3 Hz, 1H), 3.74 (s, 3H), 3.61 (d, J=15.0 Hz, 1H), 3.57-3.49 (m, 1H), 3.43 (dt, J=9.9, 5.0 Hz, 1H), 3.37 (dd, J=11.3, 4.2 Hz, 1H), 3.23 (s, 1H), 3.01 (s, 3H), 2.99-2.92 (m, 1H), 2.83 (s, 3H), 2.76-2.69 (m, 1H), 2.43 (d, J=17.2 Hz, 1H), 2.32 (d, J=17.2 Hz, 1H); MS (ESI+) m/z 439.0 (M+H)+.

EXAMPLE 262

4-(5-fluoro-2-methoxyphenyl)-2-((3 aS,6aR)-2-(methylsulfonyl)-1,2,3,3a,4,6a-hexahydrocyclopenta[c]pyrrol-5-yl)-1H-pyrrolo[2,3-b]pyridine

EXAMPLE 262A tert-butyl 5-(((trifluoromethyl)sulfonyl)oxy)-3,3a,6,6a-tetrahydrocyclopenta[c]pyrrole-2(1H)-carboxylate To a solution of sodium bis(trimethylsilyl)amide (1M in tetrahydrofuran, 14.65 mL, 14.65 mmol) in tetrahydrofuran (12 mL) at −78° C. was slowly added tert-butyl 5-oxohexahydrocyclopenta[c]pyrrole-2(1H)-carboxylate (3.00 g, 13.32 mmol) in tetrahydrofuran (7.5 mL). The mixture was stirred for 30 minutes and treated over 15 minutes with a solution of 1,1,1-trifluoro-N-phenyl-N-((trifluoromethyl)sulfonyl)methanesulfonamide (5.23 g, 14.65 mmol) in tetrahydrofuran (12 mL). The mixture was stirred at −78° C. for 90 minutes and allowed to warm to room temperature for 1 hour. The mixture was quenched with water (7.5 mL) and extracted with ethyl acetate. The organic layer was washed with brine, dried over sodium sulfate, filtered, and concentrated in vacuo. The residue was purified by flash chromatography on silica gel, eluting with a gradient of 10-80% ethyl acetate/hexanes to afford the title compound (~75% purity), which was used in the next step without further purification. MS (ESI$^+$) m/z 380 (M+Na)$^+$.

EXAMPLE 262B tert-butyl 5-(4,4,5,5-tetramethyl-1,3,2-dioxaborolan-2-yl)-3,3a,6,6a-tetrahydrocyclopenta[c]pyrrole-2(1H)-carboxylate A pressure vial was charged with Example 262A (2000 mg, ~4.20 mmol), 4,4,4',4',5,5,5',5'-octamethyl-2,2'-bi(1,3,2-dioxaborolane) (1173 mg, 4.62 mmol), potassium acetate (1236 mg, 12.59 mmol), [1,1'-bis(diphenylphosphino)ferrocene]dichloropalladium(II)-dichloromethane complex (171 mg, 0.210 mmol) and dioxane (16 mL). The vial was capped with a septa, flushed with nitrogen, stirred at 90° C. for 4 hours and used directly in the next step.

EXAMPLE 262C tert-butyl 5-(4-(5-fluoro-2-methoxyphenyl)-1-(phenylsulfonyl)-1H-pyrrolo[2,3-b]pyridin-2-yl)-3,3a,6,6a-tetrahydrocyclopenta[c]pyrrole-2(1H)-carboxylate To Example 262B (~4.20 mmol) was added Example 87B (2.14 g, 4.20 mmol), aqueous 2M sodium carbonate (10.50 mL, 21.0 mmol) and [1,1'-bis(diphenylphosphino)ferrocene]dichloropalladium(II)-dichloromethane complex (0.171 g, 0.210 mmol). The vial was capped with a septa, flushed with nitrogen and stirred at 65° C. for 6 hours. Water was added and the mixture was extracted with ethyl acetate. The combined organic layers were washed with brine, dried over sodium sulfate, filtered, and concentrated in vacuo. The residue was purified by flash chromatography on silica gel, eluting with a gradient of 0-5% methanol in dichloromethane to provide the title compound (~80% purity), which was used in the next step without further purification. MS (ESI$^+$) m/z 590 (M+H)$^+$.

EXAMPLE 262D tert-butyl 5-(4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate To a solution of Example 262C (~3.93 mmol) in tetrahydrofuran (28 mL) and methanol (20 mL) was added 1M aqueous sodium hydroxide (23.61 mL, 23.61 mmol) and the mixture was stirred at 60° C. for 3 hours. The mixture was extracted with ethyl acetate and the organic layer was washed with brine, dried over sodium sulfate, filtered and concentrated in vacuo. The residue was purified by flash chromatography on silica gel, eluting with a gradient of 6-15% methanol in dichloromethane to provide the title compound. LC-MS: 450 (M+H)$^+$.

EXAMPLE 262E 4-(5-fluoro-2-methoxyphenyl)-2-(1,2,3,3a,4,6a-hexahydrocyclopenta[c]pyrrol-5-yl)-1H-pyrrolo[2,3-b]pyridine To Example 262D (966 mg, 2.15 mmol) was added dichloromethane (6 mL) and trifluoroacetic acid (2 mL). The mixture was stirred at room temperature for 1 hour and concentrated in vacuo. The residue was diluted with ethyl acetate, washed with aqueous sodium bicarbonate and brine, and the organic layer was dried over sodium sulfate, filtered and concentrated in vacuo to provide the title compound. MS (ESI$^+$) m/z 350 (M+H)$^+$.

EXAMPLE 262F 4-(5-fluoro-2-methoxyphenyl)-2-(2-(methylsulfonyl)-1,2,3,3a,4,6a-hexahydrocyclopenta[c]pyrrol-5-yl)-1H-pyrrolo[2,3-b]pyridine To Example 262E (300 mg, 0.86 mmol) in N,N-dimethylformamide (3 mL) was added methanesulfonyl chloride (0.10 mL, 1.29 mmol) and triethylamine (0.36 mL, 2.57 mmol). The mixture was stirred at room temperature for 30 minutes and concentrated in vacuo. The residue was purified by reverse-phase HPLC on a Phenomenex Luna C8 AXIA column (30×75 mm, 100 Å) using a gradient of 10-95% acetonitrile:0.1% trifluoroacetic acid in water to afford the title compound as the trifluoroacetic acid salt. The salt was diluted with ethyl acetate and neutralized with aqueous sodium bicarbonate. The organic layer was washed with brine, dried over sodium sulfate, filtered, and concentrated in vacuo to afford the title compound as the free base. MS (ESI$^+$) m/z 428 (M+H)$^+$.

EXAMPLE 262G 4-(5-fluoro-2-methoxyphenyl)-2-((3 aS,6aR)-2-(methylsulfonyl)-1,2,3,3a,4,6a-hexahydrocyclopenta[c]pyrrol-5-yl)-1H-pyrrolo[2,3-b]pyridine Preparative SFC chiral separation of Example 262F (29 mg) was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase comprised of supercritical carbon dioxide supplied by a Dewar of bone-dry non-certified carbon dioxide pressurized to 350 psi with a modifier of methanol at a flow rate of 70 g/minutes. UV detection was set to collect at a wavelength of 220 nm, the column was at ambient temperature, and the backpressure regulator was set to maintain 100 bar. The sample was dissolved in methanol/dichloromethane (1/2) at a concentration of 20 mg/mL. The sample was loaded into the modifier stream in 1 mL (20 mg) injections. The mobile phase was held isocratically at 20% methanol: carbon dioxide. Fraction collection was time triggered. The instrument was fitted with a CHIRALPAK IC column (21 mm i.d.×250 mm length with 5 μm particles). The chiral separation afforded the title compound (which corresponded to the slower eluting enantiomer) and Example 264 (see below). For the title compound: $^1$H NMR (400 MHz, DMSO-$d_6$) δ 2.57-2.68 (m, 1 H) 2.87 (s, 3 H) 2.89-3.48 (m, 6 H) 3.55-3.67 (m, 1 H) 3.74 (s, 3 H) 6.19 (s, 1 H) 6.30 (s, 1 H) 7.04 (d, J=4.88 Hz, 1 H) 7.14-7.35 (m, 3 H) 8.21 (d, J=4.58 Hz, 1 H) 11.92 (s, 1 H). MS (ESI$^+$) m/z 428 (M+H)$^+$.

EXAMPLE 263

2-{4-[3-cyano-5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide

EXAMPLE 263A 4-chloro-5-fluoro-3-iodo-1H-pyrrolo[2,3-b]pyridine

To a solution of 4-chloro-5-fluoro-1H-pyrrolo[2,3-b]pyridine (1.8 g, 10.5 mmol) in N,N-dimethylformamide (25 mL) at 0° C. was added N-iodosuccinimide (2.37 g, 10.55 mmol). The mixture was slowly brought to room temperature, quenched with brine and extracted with ethyl acetate (twice). The organic phase was concentrated and purified by column chromatography (silica gel, 30% ethyl acetate in hexane) to afford the title compound. MS (ESI$^+$) m/z 297 (M+H)$^+$.

EXAMPLE 263B 4-chloro-5-fluoro-3-iodo-1-((2-(trimethylsilyl)ethoxy)methyl)-1H-pyrrolo[2,3-b]pyridine A solution of Example 263A (2.8 g, 9.44 mmol) in tetrahydrofuran (200 mL) was cooled to 0° C. and sodium hydride (0.34 g, 14.17 mmol) was added. The mixture was stirred at 0° C. for 30 minutes and (2-(chloromethoxy)ethyl)trimethylsilane (2.5 mL, 14.17 mmol) was added. The mixture was warmed to room temperature, stirred for 2 hours, quenched with brine and extracted with ethyl acetate (twice). The organic phase was concentrated and purified by flash chromatography (silica gel, 30% ethyl acetate in hexane) to afford the title compound. MS (ESI$^+$) m/z 427 (M+H)$^+$.

EXAMPLE 263C 4-chloro-5-fluoro-1-((2-(trimethylsilyl)ethoxy)methyl)-1H-pyrrolo[2,3-b]pyridine-3-carbonitrile A mixture of Example 263B (2.5 g, 5.86 mmol), zinc cyanide (0.8 g, 7.0 mmol), 1,1'-bis(diphenylphosphino)ferrocene (0.4 g, 0.7 mmol) and tris(dibenzylideneacetone)dipalladium(0) (0.27 g, 0.3 mmol) in N,N-dimethylformamide (50 mL) and water (0.5 mL) was flushed with nitrogen and heated at 80° C. overnight. The reaction was quenched with brine and extracted with ethyl acetate (twice). The organic phase was concentrated and purified by flash chromatography (silica gel, 30% ethyl acetate in hexane) to afford the title compound. MS (ESI$^+$) m/z 326 (M+H)$^+$.

EXAMPLE 263D 5-fluoro-4-(5-fluoro-2-methoxyphenyl)-1-((2-(trimethylsilyl)ethoxy)methyl)-1H-pyrrolo[2,3-b]pyridine-3-carbonitrile The title compound was prepared using the procedure described in Example 87A, using Example 263C (750 mg, 2.3 mmol) in place of 4-bromo-1-(phenylsulfonyl)-1H-pyrrolo[2,3-b]pyridine. LCMS: 416 (M+H)$^+$.

EXAMPLE 263E 5-fluoro-4-(5-fluoro-2-methoxyphenyl)-2-iodo-1-((2-(trimethylsilyl)ethoxy)methyl)-1H-pyrrolo[2,3-b]pyridine-3-carbonitrile A solution of Example 263D (0.72 g, 1.7 mmol) in tetrahydrofuran (50 mL) was cooled to −75° C. and 2N lithium diisopropylamide (2.6 mL, 5.2 mmol) was added dropwise. The mixture was stirred at −75° C. for 30 minutes and a solution of iodine (0.88 g, 3.47 mmol) in tetrahydrofuran (2.5 mL) was added. The mixture was slowly brought to room temperature, quenched with aqueous ammonium chloride (100 mL) and extracted with ethyl acetate (twice). The organic phase was concentrated and purified by flash chromatography (silica gel, 30% ethyl acetate in hexane) to afford the title compound. MS (ESI$^+$) m/z 542 (M+H)$^+$.

EXAMPLE 263F tert-butyl 4-(3-cyano-5-fluoro-4-(5-fluoro-2-methoxyphenyl)-1-((2-(trimethylsilyl)ethoxy)methyl)-1H-pyrrolo[2,3-b]pyridin-2-yl)-5,6-dihydropyridine-1(2H)-carboxylate The title compound was prepared using the procedure described in Example 87C, using Example 263E (0.5 mg, 0.9 mmol) in place of Example 87B. LCMS: 597 (M+H)$^+$.

EXAMPLE 263G 5-fluoro-4-(5-fluoro-2-methoxyphenyl)-2-(1,2,3,6-tetrahydropyridin-4-yl)-1H-pyrrolo[2,3-b]pyridine-3-carbonitrile To a solution of Example 263F (0.42 g, 0.7 mmol) in tetrahydrofuran (10 mL) was added 35% hydrochloric acid (6 mL) and the mixture was heated at 65° C. overnight. Concentration and purification by HPLC (Zorbax C-18, using a 0-100% gradient of water/acetonitrile, containing 0.1% trifluoroacetic acid) afforded the title compound. $^1$H NMR (400 MHz, Methanol-$d_4$) δ 3.00 (tq, J=6.2, 2.3 Hz, 2H), 3.58 (td, J=6.5, 2.8 Hz, 2H), 3.77 (s, 3H), 3.77 (s, 3H), 3.98 (q, J=2.7 Hz, 2H), 6.68 (tt, J=3.5, 1.7 Hz, 1H), 7.06-7.17 (m, 2H) 7.19-7.29 (m, 1H), 8.35 (d, J=2.3 Hz, 1H). MS (ESI$^+$) m/z 367 (M+H)$^+$.

EXAMPLE 263H

2-{4-[3-cyano-5-fluoro-4-(5-fluoro-2-methoxyphenyl)-1H-pyrrolo[2,3-b]pyridin-2-yl]-3,6-dihydropyridin-1(2H)-yl})-N,N-dimethylacetamide The title compound was prepared using the procedure described in Example 231F, using Example 263G (60 mg, 0.17 mmol) in place of Example 231E. ¹H NMR (500 MHz, Methanol-d₄) δ 3.02 (s, 6H), 3.13 (d, J=6.8 Hz, 2H), 3.46-3.73 (m, 2H), 3.77 (s, 3H), 4.15 (s, 2H), 4.37 (s, 2H), 6.67 (dt, J=3.5, 1.9 Hz, 1H), 7.02-7.18 (m, 2H), 7.24 (ddd, J=9.2, 8.2, 3.1 Hz, 1H), 8.36 (d, J=2.3 Hz, 1H). MS (ESI⁺) m/z 452 (M+H)⁺.

EXAMPLE 264

4-(5-fluoro-2-methoxyphenyl)-2-((3 aR,6aS)-2-(methylsulfonyl)-1,2,3,3a,4,6a-hexahydrocyclopenta[c]pyrrol-5-yl)-1H-pyrrolo[2,3-b]pyridine The title compound was prepared as described in Example 262G. The title compound corresponded to the faster eluting enantiomer under the SFC conditions described. ¹H NMR (400 MHz, DMSO-d₆) δ 2.57-2.66 (m, 1 H) 2.87 (s, 3 H) 2.88-3.49 (m, 6 H) 3.57-3.67 (m, 1 H) 3.74 (s, 3 H) 6.19 (s, 1 H) 6.31 (s, 1 H) 7.04 (d, J=4.88 Hz, 1 H) 7.14-7.33 (m, 3 H) 8.21 (d, J=4.88 Hz, 1 H) 11.92 (s, 1 H). MS (ESI⁺) m/z 428 (M+H)⁺.

EXAMPLE 265

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile The title compound was prepared using the procedure described in Example 148, using Example 263G (50 mg, 0.14 mmol) in place of Example 135B. ¹H NMR (400 MHz, Methanol-d₄) δ 2.82 (tt, J=5.8, 2.5 Hz, 2H), 2.92 (s, 3H), 3.54 (t, J=5.7 Hz, 2H), 3.78 (s, 3H), 4.05 (q, J=3.0 Hz, 2H), 6.69 (t, J=1.8 Hz, 1H), 7.11 (ddd, J=8.1, 6.0, 3.7 Hz, 2H), 7.23 (ddd, J=9.1, 8.2, 3.1 Hz, 1H), 8.30 (d, J=2.3 Hz, 1H). MS (ESI⁺) m/z 445 (M+H)⁺.

EXAMPLE 266

4-[3-cyano-5-fluoro-4-(5-fluoro-2-methoxyphenyl)-1H-pyrrolo[2,3-b]pyridin-2-yl]-N-methyl-3,6-dihydropyridine-1(2H)-carboxamide The title compound was prepared using the procedure described in Example 215, using Example 263G (50 mg, 0.14 mmol) in place of Example 87. ¹H NMR (400 MHz, Methanol-d₄) δ 2.67-2.74 (m, 2H), 2.77 (s, 3H), 3.63-3.68 (m, 2H), 3.78 (s, 3H), 4.14 (q, J=3.0 Hz, 2H), 6.64-6.70 (m, 1H), 7.11 (ddd, J=8.6, 5.2, 3.6 Hz, 2H), 7.23 (td, J=8.6, 3.1 Hz, 1H), 8.30 (d, J=2.4 Hz, 1H). MS (ESI⁺) m/z 424 (M+H)⁺.

EXAMPLE 267

5-fluoro-4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile

EXAMPLE 267A tert-butyl 2-(4-(3-cyano-5-fluoro-4-(5-fluoro-2-methoxyphenyl)-1H-pyrrolo[2,3-b]pyridin-2-yl)-5,6-dihydropyridin-1(2H)-yl)acetate The title compound was prepared using the procedure described in Example 226A, using Example 263G (50 mg, 0.14 mmol) in place of Example 87. MS (ESI⁺) m/z 481 (M+H)⁺.

EXAMPLE 267B 2-(4-(3-cyano-5-fluoro-4-(5-fluoro-2-methoxyphenyl)-1H-pyrrolo[2,3-b]pyridin-2-yl)-5,6-dihydropyridin-1(2H)-yl)acetic acid The title compound was prepared using the procedure described in Example 226B, using Example 267A (105 mg, 0.22 mmol) in place of Example 226A. MS (ESI⁺) m/z 425 (M+H)⁺.

EXAMPLE 267C 5-fluoro-4-(5-fluoro-2-methoxyphenyl)-2-(1-(2-(3-hydroxyazetidin-1-yl)-2-oxoethyl)-1,2,3,6-tetrahydropyridin-4-yl)-1H-pyrrolo[2,3-b]pyridine-3-carbonitrile The title compound was prepared using the procedure described in Example 238, using Example 267B (60 mg, 0.14 mmol) in place of Example 226B. ¹H NMR (500 MHz, Methanol-d₄) δ 3.03-3.18 (m, 2H), 3.53-3.69 (m, 2H), 3.77 (s, 3H), 3.86 (dd, J=10.6, 4.4 Hz, 1H), 3.99-4.05 (m, 1H), 4.13-4.17 (m, 2H), 4.28-4.34 (m, 1H), 4.44 (td, J=7.5, 3.7 Hz, 1H), 4.66 (ddd, J=6.8, 4.4, 2.5 Hz, 1H), 6.66 (dq, J=3.8, 2.0 Hz, 1H), 7.08-7.16 (m, 2H), 7.24 (td, J=8.6, 3.1 Hz, 1H), 8.36 (d, J=2.2 Hz, 1H). MS (ESI⁺) m/z 424 (M+H)⁺.

EXAMPLE 268

5-fluoro-4-(5-fluoro-2-methoxyphenyl)-2-(1-{2-[(2R)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile The title compound was prepared using the procedure described in Example 238, using Example 267B (50 mg, 0.11 mmol) in place of Example 226B and (R)-pyrrolidin-2-ylmethanol in place of azetidin-3-ol hydrochloride. ¹H NMR (400 MHz, DMSO-d₆) δ 1.77-2.03 (m, 4H), 2.93-3.13 (m, 2H), 3.17 (s, 2H), 3.33-3.48 (m, 2H), 3.49-3.56 (m, 1H), 3.74 (s, 3H), 3.95-4.09 (m, 2H), 4.33 (d, J=6.1 Hz, 2H), 4.46 (s, 1H), 6.68 (d, J=4.3 Hz, 1H), 7.21 (d, J=4.4 Hz, 1H), 7.29 (dd, J=8.6, 3.1 Hz, 1H), 7.33-7.41 (m, 1H), 8.48 (s, 1H). MS (ESI⁺) m/z 508 (M+H)⁺.

EXAMPLE 269

2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide The title compound was prepared essentially as described in Example 261, substituting (R)-1-(tert-butoxycarbonyl)-4-oxopiperidine-2-carboxylic acid for (S)-1-(tert-butoxycarbonyl)-4-oxopiperidine-2-carboxylic acid in the procedure described for Example 260A. ¹H NMR (400 MHz, DMSO-d₆) δ 11.73 (s, 1H), 8.18 (d, J=4.9 Hz, 1H), 7.36-7.07 (m, 3H), 7.02 (d, J=4.9 Hz, 1H), 6.46 (d, J=3.0 Hz, 1H), 6.23 (d, J=1.8 Hz, 1H), 4.79 (t, J=5.2 Hz, 1H), 3.74 (s, 3H), 3.61 (d, J=15.0 Hz, 1H), 3.57-3.48 (m, 1H), 3.43 (dt, J=10.8, 5.4 Hz, 1H), 3.37-3.27 (m, 1H), 3.23 (s, 1H), 3.01 (s, 3H), 2.96 (dd, J=12.5, 6.2 Hz, 1H), 2.82 (s, 3H), 2.77-2.68 (m, 1H), 2.43 (d, J=16.9 Hz, 1H), 2.31 (d, J=17.6 Hz, 1H); MS (ESI⁺) m/z 439.0 (M+H)⁺.

EXAMPLE 270

2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide The title compound was prepared essentially as described in Example 260, substituting (R)-1-(tert-butoxycarbonyl)-4-oxopiperidine-2-carboxylic acid for (S)-1-(tert-butoxycarbonyl)-4-oxopiperidine-2-carboxylic acid in the procedure described for Example 260A. $^1$H NMR (400 MHz, DMSO-$d_6$) δ 11.77 (d, J=1.5 Hz, 1H), 8.18 (d, J=5.0 Hz, 1H), 7.35-7.12 (m, 3H), 7.02 (d, J=4.9 Hz, 1H), 6.46 (s, 1H), 6.18 (d, J=1.9 Hz, 1H), 4.61 (t, J=5.4 Hz, 1H), 3.74 (s, 3H), 3.60-3.27 (m, 6H), 3.02 (s, 3H), 2.97-2.88 (m, 1H), 2.81 (s, 3H), 2.48-2.34 (m, 2H); MS (ESI$^+$) m/z 439.1 (M+H)$^+$.

EXAMPLE 271

2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine

EXAMPLE 271A tert-butyl 2,2-dimethyl-4-(((trifluoromethyl)sulfonyl)oxy)-5,6-dihydropyridine-1(2H)-carboxylate and tert-butyl 6,6-dimethyl-4-(((trifluoromethyl)sulfonyl)oxy)-5,6-dihydropyridine-1(2H)-carboxylate The title compound was prepared using the procedure described in Example 258A using tert-butyl 2,2-dimethyl-4-oxopiperidine-1-carboxylate (2.51 g, 11.04 mmol) in place of (S)-tert-butyl-2-methyl-4-oxopiperidine-1-carboxylate. Purification by flash chromatography on silica gel eluting with 1:1 dichloromethane:hexanes gave the title compound as a mixture of isomers. MS (ESI) m/e 260.0 (M-BOC)$^+$.

EXAMPLE 271B tert-butyl 4-(4-(5-fluoro-2-methoxyphenyl)-1-tosyl-1H-pyrrolo[2,3-b]pyridin-2-yl)-2,2-dimethyl-5,6-dihydropyridine-1(2H)-carboxylate and tert-butyl 4-(4-(5-fluoro-2-methoxyphenyl)-1-tosyl-1H-pyrrolo[2,3-b]pyridin-2-yl)-6,6-dimethyl-5,6-dihydropyridine-1(2H)-carboxylate (4:1)

The title compound was prepared as a mixture of regioisomers using the procedure described in Example 258D using Example 271A (0.848 mg, 2.36 mmol) in place of Example 258A. The mixture was used in the next step without further purification. MS (ESI) m/e 606.1 (M+1)$^+$.

EXAMPLE 271C tert-butyl 4-(4-(5-fluoro-2-methoxyphenyl)-1H-pyrrolo[2,3-b]pyridin-2-yl)-2,2-dimethyl-5,6-dihydropyridine-1(2H)-carboxylate The title compound was prepared using the procedure described in Example 258E using Example 271B (1.61 g, 2.66 mmol) in place of Example 258D. Purification by flash chromatography on silica gel eluting with 40% ethyl acetate in hexanes gave the single isomer title compound (the other regioisomer is described in Example 272A). MS (ESI) m/e 452.1 (M+1)$^+$.

EXAMPLE 271D 2-(6,6-dimethyl-1,2,3,6-tetrahydropyridin-4-yl)-4-(5-fluoro-2-methoxyphenyl)-1H-pyrrolo[2,3-b]pyridine A mixture of Example 271C (0.249 g, 0.551 mmol) and 2,2,2-trifluoroacetic acid (1 mL, 12.98 mmol) in dichloromethane (1 mL) was stirred for 24 hours at room temperature and concentrated. The hydrochloride salt was prepared by dissolving the resultant solid in methanol and adding 2M hydrogen chloride in diethyl ether. After concentrating under reduced pressure, the title compound was obtained. MS (ESI) m/e 352.1 (M+1)$^+$.

EXAMPLE 271E

2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine The title compound was prepared using the procedure described in Example 258G using Example 271D (0.101 g, 0.239 mmol) in place of Example 258F. $^1$HNMR (500 MHz, DMSO-$d_6$) δ 1.56 (s, 6H), 2.52 (m, 2H), 3.01 (s, 3H), 3.43 (t, 2H), 3.74 (s, 3H), 6.28 (m, 2H), 7.04 (d, 1H), 7.24 (m, 3H), 8.21 (d, 1H), 11.80 (br s, 1H). MS (ESI) m/e 430.1 (M+1)$^+$.

EXAMPLE 272

2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine

EXAMPLE 272A tert-butyl 4-(4-(5-fluoro-2-methoxyphenyl)-1H-pyrrolo[2,3-b]pyridin-2-yl)-6,6-dimethyl-5,6-dihydropyridine-1(2H)-carboxylate The title compound was prepared using the procedure described in Example 258E using Example 271B (1.61 g, 2.66 mmol) in place of Example 258D. Purification by flash chromatography on silica gel eluting with 40% ethyl acetate in hexanes gave the single isomer title compound (the other regioisomer is described in Example 271C). MS (ESI) m/e 452.1 (M+1)$^+$.

EXAMPLE 272B 2-(2,2-dimethyl-1,2,3,6-tetrahydropyridin-4-yl)-4-(5-fluoro-2-methoxyphenyl)-1H-pyrrolo[2,3-b]pyridine The title compound was prepared using the procedure described in Example 271D using Example 272A (0.600 g, 1.32 mmol) in place of Example 271C. MS (ESI) m/e 352.1 (M+1)$^+$.

EXAMPLE 272C 2-(2,2-dimethyl-1-(methylsulfonyl)-1,2,3,6-tetrahydropyridin-4-yl)-4-(5-fluoro-2-methoxyphenyl)-1H-pyrrolo[2,3-b]pyridine The title compound was prepared using the procedure described in Example 258G substituting Example 272B (0.106 g, 0.251 mmol) in place of Example 258F. $^1$HNMR (500 MHz, DMSO-d$_6$) δ 1.44 (s, 6H), 2.53 (m, 2H), 3.01 (s, 3H), 3.73 (s, 3H), 4.08 (m, 2H), 6.26 (d, 1H), 6.54 (m, 1H), 7.03 (d, 1H), 7.24 (m, 3H), 8.20 (d, 1H), 11.87 (br s, 1H). MS (ESI) m/e 430.2 (M+1)$^+$.

EXAMPLE 273

2-{4-[4-(5-fluoro-2-methoxyphenyl)-1H-pyrrolo[2,3-b]pyridin-2-yl]-2,2-dimethyl-3,6-dihydropyridin-1(2H)-yl}-N,N-dimethylacetamide A mixture of Example 272B (0.102 g, 0.241 mmol), 2-chloro-N,N-dimethylacetamide (0.047 g, 0.387 mmol) and triethylamine (0.2 mL, 1.43 mmol) was stirred in N,N-dimethylformamide (2 mL) at room temperature for 24 hours and concentrated under reduced pressure. Purification by reverse phase-HPLC (Sunfire 5 μM, 50×250 mm) eluting with 5-50% acetonitrile in water (containing 0.1% trifluoroacetic acid) provided the trifluoroacetate salt, which was dissolved in methanol and eluted from a SCX column with 0.5M ammonia in methanol to give the free base of the title compound. $^1$HNMR (500 MHz, DMSO-d$_6$) δ 1.12 (br s, 6H), 2.38 (br s, 2H), 2.88 (s, 3H), 3.13 (s, 3H), 3.25 (br s, 1H), 3.32 (br s, 1H), 3.44 (m, 2H), 3.79 (s, 3H), 6.24 (m, 1H), 6.51 (m, 1H), 7.07 (d, 1H), 7.29 (m, 3H), 8.24 (d, 1H), 11.84 (br s, 1H). MS (ESI) m/e 437.1 (M+1)$^+$.

EXAMPLE 274

4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine The title compound was prepared using the procedure described in Example 262F using 2-methoxyethanesulfonyl chloride in place of methanesulfonyl chloride. $^1$H NMR (400 MHz, DMSO-d$_6$) δ 2.60 (d, J=17.70 Hz, 1 H) 2.98 (m, 3 H) 3.21 (s, 3 H) 3.46 (m, 2 H) 3.61 (m, 3 H) 3.73 (s, 3 H) 6.18 (d, J=1.83 Hz, 1 H) 6.30 (d, J=1.53 Hz, 1 H) 7.04 (d, J=4.88 Hz, 1 H) 7.23 (m, 3 H) 8.21 (d, J=4.88 Hz, 1 H) 11.91 (s, 1 H). MS (ESI$^+$) m/z 471.2 (M+H)$^+$.

EXAMPLE 275

2-{4-[5-cyano-4-(5-fluoro-2-methoxyphenyl)-1H-pyrrolo[2,3-b]pyridin-2-yl]piperidin-1-yl}-N,N-dimethylacetamide A solution of Example 236G (80 mg, 0.185 mmol) in methanol (10 mL) was added to 20% palladium hydroxide on carbon (wet) (40 mg, 0.029 mmol) in a pressure bottle. The mixture was stirred at 50° C. under 30 psi hydrogen for 16 hours and filtered. The filtrate was concentrated and the residue was purified by reverse-phase HPLC on a Phenomenex Luna C8 AXIA column (100 Å) using a gradient of 10-95% acetonitrile/0.1% trifluoroacetic acid in water to afford the title compound. $^1$H NMR (400 MHz, DMSO-d$_6$) δ 2.00-2.20 (m, 2H), 2.21-2.30 (m, 2H), 2.90-2.98 (m, 6H), 2.98-3.45 (m, 5H), 3.75 (s, 3H), 4.21 (s, 2H), 6.09 (bs, 1H), 7.20 (dd, J=8.6, 3.1 Hz, 1H), 7.26 (dd, J=9.1, 4.5 Hz, 1H), 7.29-7.38 (m, 1H), 8.54 (s, 1H), 12.12 (bs, 1H). MS (ESI(+)) m/e 436 (M+H)$^+$

EXAMPLE 276

2-{4-[4-(5-fluoro-2-methoxyphenyl)-1H-pyrrolo[2,3-b]pyridin-2-yl]piperidin-1-yl}-N-(3-hydroxycyclobutyl)-N-methylacetamide The title compound was prepared according to the procedure described in Example 238 substituting Example 247B for Example 226B and 3-(methylamino)cyclobutanol hydrochloride (Enamine) for azetidin-3-ol hydrochloride. $^1$H NMR (500 MHz, CD$_3$OD) δ 1.83-2.30 (m, 6H), 2.39-2.65 (m, 4H), 2.78-2.91 (m, 1H), 2.91-3.04 (m, 3H), 3.09-3.23 (m, 2H), 3.41-3.53 (m, 2H), 3.76 (s, 3H), 3.91-4.43 (m, 2H), 6.07 (d, J=4.0 Hz, 1H), 7.08 (d, J=5.1 Hz, 1H), 7.10-7.20 (m, 3H), 8.11 (d, J=5.1 Hz, 1H). MS (ESI$^+$) m/z 467.2 (M+H)$^+$.

EXAMPLE 277

4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile

EXAMPLE 277A 4-(5-fluoro-2-methoxyphenyl)-2-iodo-1H-pyrrolo[2,3-b]pyridine-5-carbonitrile To a solution of Example 236C (3 g, 5.63 mmol) in 20 mL tetrahydrofuran and 20 mL methanol was added 2N lithium hydroxide (8.44 mL, 16.88 mmol) and the mixture was stirred at room temperature for 4 hours. The mixture was neutralized with 2N aqueous hydrochloric acid, extracted with ethyl acetate and purified by flash chromatography eluting with 0-50% ethyl acetate in heptane to afford the title compound. MS (ESI(+)) m/e 394 (M+H)$^+$.

EXAMPLE 277B tert-butyl 5-(5-cyano-4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate The title compound was prepared using the procedure described in Example 87C, substituting Example 277A for Example 87B and Example 262B in place of tert-butyl 4-(4,4,5,5-tetramethyl-1,3,2-dioxaborolan-2-yl)-5,6-dihydropyridine-1(2H)-carboxylate. MS (ESI$^+$) m/z 475 (M+H)$^+$.

EXAMPLE 277C 4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile The title compound was prepared as the procedure described in Example 236F, substituting Example 277B for Example 236E. MS (ESI$^+$) m/z 375 (M+H)$^+$.

EXAMPLE 277D 4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile The title compound was prepared using the procedure described in Example 262F, substituting Example 277C for Example 262E. $^1$H NMR (500 MHz, DMSO-d$_6$) δ 2.56-2.68 (m, 1H), 2.81-3.14 (m, 6H), 3.15-3.21 (m, 1H), 3.43 (dd, J=9.8, 8.1 Hz, 2H), 3.57-3.67 (m, 1H), 3.76 (s, 3H), 6.25 (dd, J=3.8, 1.9 Hz, 1H), 6.40 (d, J=2.3 Hz, 1H), 7.21-7.36 (m, 3H), 7.35-7.44 (m, 1H), 12.60 (bs, 1H). MS (ESI(+)) m/e 453 (M+H)$^+$.

EXAMPLE 278

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide The title compound was prepared using the procedure described in Example 235, substituting Example 277C for Example 17G. $^1$H NMR (400 MHz, DMSO-$d_6$) δ 2.40-2.50 (m, 3H), 2.55-2.64 (m, 2H), 2.77 (d, J=3.5 Hz, 3H), 2.82-2.99 (m, 5H), 3.16-3.21 (m, 2H), 3.40-3.50 (br, 1H), 3.75 (s, 3H), 6.17 (s, 1H), 6.40 (d, J=2.5 Hz, 1H), 7.23-7.34 (m, 2H), 7.39 (td, J=8.7, 3.2 Hz, 1H), 8.60 (d, J=0.7 Hz, 1H), 12.51 (bs, 1H). MS (ESI(+)) m/e 460 (M+H)$^+$.

EXAMPLE 279

4-[5-fluoro-4-(5-fluoro-2-methoxyphenyl)-1H-pyrrolo[2,3-b]pyridin-2-yl]cyclohex-3-ene-1-carboxylic acid

EXAMPLE 279A ethyl 4-(4-chloro-5-fluoro-1-(phenylsulfonyl)-1H-pyrrolo[2,3-b]pyridin-2-yl)cyclohex-3-enecarboxylate The title compound was prepared essentially as described in Example 219B, substituting Example 219A with Example 231B. MS (ESI): 463.1 (M+H)$^+$.

EXAMPLE 279B ethyl 4-(5-fluoro-4-(5-fluoro-2-methoxyphenyl)-1-(phenylsulfonyl)-1H-pyrrolo[2,3-b]pyridin-2-yl)cyclohex-3-enecarboxylate To a solution of Example 279A (1250 mg, 2.86 mmol) in 13.3 mL tetrahydrofuran/water (3:1) was added 5-fluoro-2-methoxyphenylboronic acid (1043 mg, 3.72 mmol), sodium carbonate (1214 mg, 11.45 mmol) and phenylallylchloro[1,3-bis(diisopropylphenyl)-2-imidazol-2-ylidene]palladium (II) (60.3 mg, 0.086 mmol) and the mixture was heated at 75° C. for 2 hours. The mixture was cooled to room temperature, and diluted with ethyl acetate, and the organics washed with saturated sodium bicarbonate, water, and brine, dried over magnesium sulfate, filtered, and concentrated. Purification by flash chromatography (Analogix280, SF 40-80 column, 10-60% ethyl acetate/hexane gradient) gave the title compound. MS (ESI): 553.1 (M+H)$^+$.

EXAMPLE 279C

4-[5-fluoro-4-(5-fluoro-2-methoxyphenyl)-1H-pyrrolo[2,3-b]pyridin-2-yl]cyclohex-3-ene-1-carboxylic acid A suspension of Example 279B (1.1 g, 1.991 mmol) in 20 mL dioxane was treated with 6M aqueous sodium hydroxide (4.98 mL, 29.9 mmol) at 80° C. for 1 hour and at 100° C. for 2 hours. The mixture was cooled and most solvent removed in vacuo. The residue was diluted with 15 mL water and the basic layer extracted with ethyl acetate (twice). The organic layer was discarded. The basic aqueous layer was adjusted to ~pH 7 with 1M hydrochloric acid, and extracted with ethyl acetate (twice) and dichloromethane (twice). The combined organics were washed with brine, dried over magnesium sulfate, filtered, and concentrated. Trituration with ethyl acetate, filtration and drying in vacuo gave the title compound. $^1$H NMR (500 MHz, DMSO-$d_6$) δ 1.60-1.78 (m, 1 H) 1.95-2.11 (m, 1 H) 2.27-2.48 (m, 3 H) 3.39-3.52 (m, 1 H) 3.53-3.62 (m, 1 H) 3.67-3.81 (m, 3 H) 6.12 (s, 1 H) 6.54 (s, 1 H) 7.07-7.44 (m, 3 H) 8.17 (d, J=2.14 Hz, 1 H) 11.86 (s, 1 H). MS (ESI): 385.2 (M+H)$^+$.

EXAMPLE 280

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-hydroxyethanone A mixture of Example 262E (60 mg, 0.172 mmol), 2-hydroxyacetic acid (22.39 mg, 0.206 mmol), 1-[bis(dimethylamino)methylene]-1H-1,2,3-triazolo[4,5-b]pyridinium 3-oxide hexafluorophosphate (78 mg, 0.206 mmol) and triethylamine (47.9 μL, 0.343 mmol) in dimethylformamide (2 mL) was stirred at room temperature overnight. The mixture was concentrated in vacuo and the residue was purified by reverse-phase HPLC on a Phenomenex Luna C8 AXIA column (100 Å) using a gradient of 10-95% acetonitrile/0.1% trifluoroacetic acid in water to afford the title compound as the trifluoroacetate salt. $^1$H NMR (500 MHz, DMSO-$d_6$) δ 2.58-3.16 (m, 4 H) 3.39-3.72 (m, 4 H) 3.74 (s, 3 H) 3.88-4.04 (m, 3 H) 6.17-6.31 (m, 1 H) 6.35 (s, 1 H) 7.14 (d, J=5.19 Hz, 1 H) 7.18-7.36 (m, 3 H) 8.26 (d, J=5.19 Hz, 1 H) 12.16 (s, 1 H). MS (ESI$^+$) m/z 408 (M+H)$^+$.

EXAMPLE 281

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-3-oxopropanenitrile The title compound was prepared as the trifluoroacetate salt using the procedure described in Example 280, substituting 2-hydroxyacetic acid with 2-cyanoacetic acid. $^1$H NMR (400 MHz, DMSO-$d_6$) δ 2.58-3.16 (m, 4 H) 3.46-3.64 (m, 4 H) 3.74 (s, 3 H) 3.89-3.95 (m, 2 H) 6.25 (dd, J=4.12, 1.98 Hz, 1 H) 6.34 (s, 1 H) 7.11 (d, J=4.88 Hz, 1 H) 7.18-7.34 (m, 3 H) 8.24 (d, J=5.19 Hz, 1 H) 12.10 (s, 1 H). MS (ESI$^+$) m/z 417 (M+H)$^+$.

EXAMPLE 282

5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine

EXAMPLE 282A 5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine The title compound was prepared essentially as described in Example 231C-E, substituting Example 262B for tert-butyl 4-(4,4,5,5-tetramethyl-1,3,2-dioxaborolan-2-yl)-5,6-dihydropyridine-1(2H)-carboxylate in Example 231C. MS (ESI$^+$) m/z 368.2 (M+H)$^+$.

EXAMPLE 282B 5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine To a solution of Example 282A in 1-methyl-2-pyrrolidinone (2 mL) was added triethylamine (0.177 mL, 1.267 mmol) and methanesulfonyl chloride (0.033 mL, 0.422 mmol) and the mixture was stirred for 3 hours. The mixture was treated with water and stirred for 10 minutes and the precipitate was filtered, washed with water, and vacuum oven-dried. The solid was suspended in 1 mL methanol and treated with 1 mL 2M hydrogen chloride in ether. The suspension was diluted with 4 mL ether, stirred for 10 minutes, filtered, washed with ether, and vacuum oven-dried to provide the title compound as a hydrochloride salt. $^1$H NMR (400 MHz, Methanol-$d_4$) δ 2.63-2.76 (m, 1H), 2.85 (s, 3H), 3.00-3.13 (m, 1H), 3.11-3.24 (m, 2H), 3.37-3.54 (m, 3H), 3.68-3.77 (m, 1H), 3.80 (s, 3H), 6.39-6.48 (m, 2H), 7.20-7.29 (m, 2H), 7.28-7.37 (m, 1H), 8.43 (d, J=3.9 Hz, 1H). MS (ESI$^+$) m/z 446.2 (M+H)$^+$.

EXAMPLE 283

4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile

EXAMPLE 283A tert-butyl 2-(4-(5-cyano-4-(5-fluoro-2-methoxyphenyl)-1H-pyrrolo[2,3-b]pyridin-2-yl)-5,6-dihydropyridin-1(2H)-yl)acetate The title compound was prepared using the procedure described in Example 226A, substituting Example 236F for Example 87. MS (ESI(+)) m/e 463 (M+H)$^+$.

EXAMPLE 283B 2-(4-(5-cyano-4-(5-fluoro-2-methoxyphenyl)-1H-pyrrolo[2,3-b]pyridin-2-yl)-5,6-dihydropyridin-1(2H)-yl)acetic acid The title compound was prepared using the procedure described in Example 226B, substituting Example 283A for Example 226A. MS (ESI(+)) m/e 407 (M+H)$^+$.

EXAMPLE 283C 4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile The title compound was prepared using the procedure described in Example 238, substituting Example 283B for Example 226B and (S)-pyrrolidin-2-ylmethanol for azetidin-3-ol hydrochloride. $^1$H NMR (400 MHz, DMSO-$d_6$) δ 1.72-1.95 (m, 4H), 2.40-2.77 (m, 4H), 3.16-3.42 (m, 7H), 3.76 (s, 3H), 4.18-4.2 (m, 3H), 6.25 (s, 1H), 6.56 (bs, 1H), 7.20-7.44 (m, 3H), 8.59 (s, 1H). MS (ESI(+)) m/e 490 (M+H)$^+$.

EXAMPLE 284

(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide

EXAMPLE 284A (3aS,6aR)-tert-butyl 5-(4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate Preparative SFC chiral separation of Example 262D (4.0 g) was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase comprised of supercritical carbon dioxide supplied by a Dewar of bone-dry non-certified carbon dioxide pressurized to 350 psi with a modifier of methanol at a flow rate of 70 g/min. UV detection was set to collect at a wavelength of 220 nm, the column was at ambient temperature, and the backpressure regulator was set to maintain 100 bar. The sample was dissolved in methanol at a concentration of 100 mg/mL. The sample was loaded into the modifier stream in 1 mL (100 mg) injections. The mobile phase was held isocraticly at 20% methanol:carbon dioxide. Fraction collection was time triggered. The instrument was fitted with a CHIRALPAK OD-H column (21 mm i.d.×250 mm length with 5 μm particles). The chiral separation afforded the title compound as the slower eluting enantiomer and Example 285A (see below, faster eluting enantiomer). Optical rotation for the title compound was obtained using an Autopol IV® automatic polarimeter (c=10 mg/mL in choloform at 24.8° C.) $[α]_D$=+165.20. LC-MS: 450 (M+H)$^+$.

EXAMPLE 284B (3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide To a solution of Example 284A (2.14 g, 4.76 mmol) in ethyl acetate (13 mL) was added methanol (13 mL) and 2M hydrogen chloride in diethyl ether (2 mL, 4.00 mmol). The mixture was stirred at 35° C. for 2 hours and cooled. Diethyl ether (50 mL) was added and the suspension was stirred vigorously at room temperature for 10 minutes and filtered. The solid was washed with 50 mL of diethyl ether and 50 mL of heptane and the solid was collected and dried under high vacuum to provide the deprotected intermediate as the hydrochloride salt. To a solution of this intermediate (100 mg, 0.237 mmol) in N,N-dimethylformamide (1.5 mL) was added 2,5-dioxopyrrolidin-1-yl methylcarbamate (44.8 mg, 0.260 mmol) and triethylamine (0.165 mL, 1.184 mmol) and the mixture was stirred at room temperature for 3 hours. Water was slowly added, and the precipitate was collected by filtration, washed with diethyl ether and dried in vacuo to provide the title compound. $^1$H NMR (500 MHz, DMSO-$d_6$) δ 2.51-2.60 (m, 4 H) 2.84-3.07 (m, 3 H) 3.35-3.40 (m, 2 H) 3.46-3.55 (m, 2 H) 3.73 (s, 3 H) 5.96-6.07 (m, 1 H) 6.15-6.20 (m, 1 H) 6.31 (s, 1 H) 7.03 (d, J=4.88 Hz, 1 H) 7.16-7.32 (m, 3 H) 8.21 (d, J=4.88 Hz, 1 H) 11.89 (d, J=1.53 Hz, 1 H). MS (ESI$^+$) m/z 407 (M+H)$^+$.

EXAMPLE 285

(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide

EXAMPLE 285A (3aR,6aS)-tert-butyl 5-(4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate The title compound was prepared in Example 284A, and corresponds to the faster eluting enantiomer under the SFC conditions described in Example 284A. Optical rotation was obtained using an Autopol IV® automatic polarimeter (c=10 mg/mL in choloform at 24.8° C.) $[\alpha]_D = -161.10$. LC-MS: 450 (M+H)$^+$.

EXAMPLE 285B (3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide The title compound was prepared using the condition described in Example 284B, substituting Example 284A with Example 285A. $^1$H NMR (500 MHz, DMSO-d$_6$) δ 2.51-2.58 (m, 4 H) 2.83-3.06 (m, 3 H) 3.35-3.40 (m, 2 H) 3.47-3.55 (m, 2 H) 3.73 (s, 3 H) 6.00-6.08 (m, 1 H) 6.15-6.20 (m, 1 H) 6.31 (s, 1 H) 7.03 (d, J=4.88 Hz, 1 H) 7.16-7.30 (m, 3 H) 8.21 (d, J=4.88 Hz, 1 H) 11.89 (d, J=1.22 Hz, 1 H). MS (ESI$^+$) m/z 407 (M+H)$^+$.

EXAMPLE 286

5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide To a suspension of Example 282A (80.0 mg, 0.182 mmol) and N-succinimidyl-N-methylcarbamate (46.9 mg, 0.273 mmol) in N,N-dimethylformamide (2.5 mL) was added triethylamine (0.152 mL, 1.090 mmol) and the mixture was stirred for 3 hours. The mixture was treated with water and brine and extracted with ethyl acetate (twice). The combined organic layers were washed with water and brine, dried over magnesium sulfate, filtered, and concentrated until most of the solvent was removed. The suspension was filtered, washed with ethyl acetate and vacuum oven-dried to provide the title compound. $^1$H NMR (400 MHz, Pyridine-d$_5$) δ 2.56-2.86 (m, 1H), 2.86-2.95 (m, 5H), 3.31-3.42 (m, 1H), 3.47 (bs, 1H), 3.61-3.75 (m, 4H), 3.73-3.91 (m, 2H), 6.40 (bs, 2H), 6.48 (d, J=2.0 Hz, 1H), 7.12 (dd, J=9.1, 4.5 Hz, 1H), 7.31 (td, J=8.5, 3.2 Hz, 1H), 7.48-7.54, (m, 1H), 8.53 (d, J=2.6 Hz, 1H), 13.12 (bs, 1H). MS (ESI$^+$) m/z 425.1 (M+H)$^+$.

EXAMPLE 287

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide A mixture of Example 282A (80.0 mg, 0.182 mmol), 2-chloro-N,N-dimethylacetamide (0.021 mL, 0.209 mmol), and triethylamine (0.127 mL, 0.908 mmol) in N,N-dimethylformamide (2 mL) was heated at 75° C. for 4 hours. The mixture was treated with water and brine and extracted with ethyl acetate (twice). The combined organic layers were washed with brine, dried over magnesium sulfate, filtered, concentrated, and purified by HPLC (same protocol as Example 221). The trifluoroacetic acid salt was flushed through an SCX column eluting with 2M ammonia in methanol to give the free base of the title compound. $^1$H NMR (400 MHz, Pyridine-d$_5$) δ 2.58-3.06 (m, 13H), 3.31 (d, J=5.4 Hz, 2H), 3.39-3.44 (m, 1H), 3.71 (s, 3H), 6.43 (bs, 1H), 6.48 (bs, 1H), 7.12 (dd, J=9.1, 4.5 Hz, 1H), 7.27-7.36 (m, 1H), 7.50 (d, J=8.8 Hz, 1H), 8.51 (d, J=2.6 Hz, 1H), 13.13 (bs, 1H). MS (ESI$^+$) m/z 453.2 (M+H)$^+$.

EXAMPLE 288

(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid

EXAMPLE 288A methyl cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate Example 87D (0.15 g, 0.379 mmol) and triethylamine (0.132 mL, 0.946 mmol) in dichloromethane (3.15 mL) and methanol (3.15 mL) was treated with methyl 2-(4-oxocyclohexyl)acetate (J&W PharmLab, 0.084 g, 0.492 mmol) and acetic acid (0.130 mL, 2.271 mmol) and the mixture was stirred at room temperature for 10 minutes. MP-cyanoborohydride (Biotage, 2.49 mmol/g, 0.608 g, 1.514 mmol) was added and the reaction mixture was stirred at room temperature for 20 hours. The reaction mixture was diluted with 40 mL 50% methanol in dichloromethane and filtered. The filtrate was concentrated and the residue was partitioned in ethyl acetate and saturated aqueous sodium bicarbonate. The organic layer was washed with brine, dried over sodium sulfate, filtered, and concentrated. Purification of the resulting mixture of methyl cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate and methyl trans-4-{4-[4-(5-fluoro-2-methoxyphenyl)-1H-pyrrolo[2,3-b]pyridin-2-yl]-3,6-dihydropyridin-1(2H)-yl})cyclohexyl)acetate by flash chromatography on silica gel (AnaLogix IntelliFlash 280) eluting with a gradient of 0-9% methanol in dichloromethane afforded the title compound. MS (ESI$^+$) m/z 478.1 (M+H)$^+$.

EXAMPLE 288B methyl trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate A solution of Example 87D (0.15 g, 0.379 mmol) and triethylamine (0.132 mL, 0.946 mmol) in dichloromethane (3.15 mL) and methanol (3.15 mL) was treated with methyl 2-(4-oxocyclohexyl)acetate (J&W PharmLab, 0.084 g, 0.492 mmol), acetic acid (0.130 mL, 2.271 mmol), and MP-cyanoborohydride (Biotage, 2.49 mmol/g, 0.608 g, 1.514 mmol) and the mixture was stirred at room temperature for 20 hours. The mixture was diluted with 40 mL 50% methanol in dichloromethane and filtered. The filtrate was concentrated and the residue was partitioned in ethyl acetate and saturated aqueous sodium bicarbonate. The organic layer was washed with brine, dried over sodium sulfate, filtered, and concentrated. Purification of the resulting mixture of methyl cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate and methyl trans-4-{4-[4-(5-fluoro-2-methoxyphenyl)-1H-pyrrolo[2,3-b]pyridin-2-yl]-3,6-dihydropyridin-1(2H)-yl})cyclohexyl)acetate by flash chromatography on silica gel (AnaLogix IntelliFlash 280) eluting with a gradient of 0-9% methanol in dichloromethane afforded the title compound. MS (ESI$^+$) m/z 478.1 (M+H)$^+$.

EXAMPLE 288C (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid A solution of Example 288A (0.025 g, 0.052 mmol) in tetrahydrofuran (0.262 mL) and methanol (0.262 mL) was treated with aqueous 2M lithium hydroxide (0.079 mL, 0.157 mmol) and the mixture was stirred at room temperature for 16 hours. The mixture was purified by reverse phase HPLC on a Phenomenex Luna C8(2) 5 um 100 Å AXIA column eluting with a gradient of 10-95% acetonitrile in 0.1% trifluoroacetic acid/water to afford the cis-isomer title compound (along with the trans-isomer described in Example 289) as the trifluoroacetate salt. $^1$H NMR (400 MHz, DMSO-d$_6$) δ 1.48-1.78 (m, 6H), 1.78-1.94 (m, 2H), 2.07-2.16 (m, 1H), 2.33 (d, J=7.6 Hz, 2H), 2.72-2.93 (m, 2H), 3.14-3.33 (m, 2H), 3.67-3.77 (m, 4H), 3.90-4.02 (m, 2H), 6.40 (d, J=1.9 Hz, 1H), 6.48-6.56 (m, 1H), 7.09 (d, J=5.0 Hz, 1H), 7.16-7.36 (m, 3H), 8.26 (d, J=5.0 Hz, 1H), 9.51 (bs, 1H), 12.07 (d, J=1.6 Hz, 1H). MS (ESI$^+$) m/z 464.0 (M+H)$^+$.

EXAMPLE 289

(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid The title compound was prepared as described in Example 288C, substituting Example 288B for Example 288A. $^1$H NMR (400 MHz, DMSO-d$_6$) δ 1.00-1.17 (m, 2H), 1.44-1.71 (m, 3H), 1.81-1.94 (m, 2H), 1.99-2.19 (m, 4H), 2.67-2.93 (m, 2H), 3.13-3.30 (m, 2H), 3.61-3.72 (m, 1H), 3.74 (s, 3H), 3.90-4.02 (m, 2H), 6.40 (d, J=1.9 Hz, 1H), 6.47-6.55 (m, 1H), 7.09 (d, J=5.0 Hz, 1H), 7.16-7.36 (m, 3H), 8.26 (d, J=5.0 Hz, 1H), 9.61 (bs, 1H), 12.06 (d, J=1.7 Hz, 1H). MS (ESI$^+$) m/z 464.0 (M+H)$^+$.

EXAMPLE 290

4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile

EXAMPLE 290A tert-butyl 2-(4-(5-cyano-4-(5-fluoro-2-methoxyphenyl)-1H-pyrrolo[2,3-b]pyridin-2-yl)piperidin-1-yl)acetate The title compound was prepared as described in Example 275, substituting Example 283A for Example 236G. MS (ESI(+)) m/e 465 (M+H)$^+$.

EXAMPLE 290B 2-(4-(5-cyano-4-(5-fluoro-2-methoxyphenyl)-1H-pyrrolo[2,3-b]pyridin-2-yl)piperidin-1-yl)acetic acid The title compound was prepared using the procedure described in Example 226B, substituting Example 290A for Example 226A. MS (ESI(+)) m/e 409 (M+H)$^+$.

EXAMPLE 290C 4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile The title compound was prepared using the procedure described in Example 238, substituting Example 290B for Example 226B and (S)-pyrrolidin-2-ylmethanol for azetidin-3-ol hydrochloride. $^1$H NMR (400 MHz, DMSO-d$_6$) δ 1.86 (s, 8H), 2.12-2.28 (m, 1H), 2.89-2.98 (m, 1H), 3.10 (d, J=9.1 Hz, 1H), 3.12-3.69 (m, 7H), 3.76 (s, 3H) 3.90-4.30 (m, 3H), 6.04 (d, J=2.9 Hz, 1H), 7.19-7.30 (m, 2H). 7.33-7.47 (m, 1H), MS (ESI(+)) m/e 492 (M+H)$^+$.

EXAMPLE 291

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl})-N-methyl-2-oxoethanesulfonamide The title compound was prepared using the conditions described in Example 280, substituting 2-hydroxyacetic acid with 2-(N-methylsulfamoyl)acetic acid. $^1$H NMR (400 MHz, DMSO-d$_6$) δ 2.55-2.69 (m, 5 H) 2.81-3.12 (m, 3 H) 3.47-3.66 (m, 2 H) 3.73 (s, 3 H) 3.74-3.97 (m, 2 H) 4.06-4.22 (m, 2 H) 6.32 (s, 1 H) 6.97-7.09 (m, J=5.49, 5.49 Hz, 2 H) 7.15-7.32 (m, 3 H) 8.21 (d, J=4.88 Hz, 1 H) 11.92 (dd, J=4.73, 1.68 Hz, 1 H). MS (ESI$^+$) m/z 485 (M+H)$^+$.

EXAMPLE 292

4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid

EXAMPLE 292A tert-butyl 4-(4-(4-(5-fluoro-2-methoxyphenyl)-1H-pyrrolo[2,3-b]pyridin-2-yl)-5,6-dihydropyridin-1(2H)-yl)cyclohexanecarboxylate The title compound was prepared according to the procedure described in Example 288A substituting tert-butyl 4-oxocyclohexanecarboxylate (Astatech) for methyl 2-(4-oxocyclohexyl)acetate. MS (ESI$^+$) m/z 506.1 (M+H)$^+$.

EXAMPLE 292B 4-(4-(4-(5-fluoro-2-methoxyphenyl)-1H-pyrrolo[2,3-b]pyridin-2-yl)-5,6-dihydropyridin-1(2H)-yl)cyclohexanecarboxylic acid The title compound was prepared according to the procedure described in Example 226B substituting Example 292A for Example 226A. $^1$H NMR (500 MHz, CD$_3$OD) δ 1.52-1.88 (m, 4H), 2.05-2.45 (m, 5H), 2.91-3.05 (m, 2H), 3.32-3.46 (m, 2H), 3.76-3.86 (m, 4H), 4.02-4.13 (m, 2H), 6.57-6.66 (m, 1H), 6.75 (d, J=6.1 Hz, 1H), 7.21-7.37 (m, 3H), 7.59 (dd, J=6.1, 0.9 Hz, 1H), 8.37 (d, J=6.0 Hz, 1H). MS (ESI$^+$) m/z 450.1 (M+H)$^+$.

EXAMPLE 293

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone

EXAMPLE 293A tert-butyl 2-(5-(5-fluoro-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetate A mixture of Example 282A (400 mg, 0.908 mmol), tert-butyl 2-bromoacetate (0.157 mL, 1.090 mmol), and triethylamine (0.633 mL, 4.54 mmol) in N,N-dimethylformamide (7 mL) was heated at 85° C. for 30 minutes in a Biotage Initiator microwave reactor. The mixture was treated with water and brine and extracted with ethyl acetate (twice). The combined organic layers were washed with water and brine, dried over magnesium sulfate, filtered, concentrated, and purified on silica gel using the ISCO Companion eluting with ethyl acetate/heptanes (7:3 to 8:2) to provide the title compound. MS (ESI$^+$) m/z 481.9 (M+H)$^+$.

EXAMPLE 293B 2-(5-(5-fluoro-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetic acid A solution of Example 293A (0.685 g, 1.423 mmol) and trifluoroacetic acid (2.74 mL, 35.6 mmol) in dichloromethane (12 mL) was stirred for 18 hours. The mixture was concentrated and the residue was dissolved in 5 mL dichloromethane and treated with 8 mL 2M hydrogen chloride in ether. The suspension was sonicated, diluted with ether, and stirred for 1 hour. The solid was filtered, washed with ether and vacuum oven-dried to provide the title compound as a hydrochloride salt. MS (trifluoroacetic acid salt via HPLC) (ESI$^+$) m/z 426.2 (M+H)$^+$.

EXAMPLE 293C

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone A mixture of Example 293B (0.100 g, 0.217 mmol), (benzotriazol-1-yl-oxytripyrrolidinophosphonium hexafluorophosphate (0.135 g, 0.260 mmol), triethylamine (0.151 mL, 1.083 mmol), and azetidin-3-ol•hydrochloride (0.028 g, 0.260 mmol) in N,N-dimethylformamide (2.5 mL) was stirred for 3 hours. The mixture was treated with water and brine and extracted with ethyl acetate (twice). The combined organic layers were washed with water and brine, dried over magnesium sulfate, filtered, concentrated, and purified on silica gel using the ISCO Companion eluting with dichloromethane/methanol/ammonium hydroxide (18:1:0.1 to 9:1: 0.1) to provide the title compound. $^1$H NMR (400 MHz, Methanol-d$_4$) δ 2.47-2.67 (m, 3H), 2.67-2.76 (m, 2H), 2.93-3.01 (m, 2H), 3.05-3.19 (m, 2H), 3.71-3.76 (m, 4H), 3.92-4.01 (m, 1H), 4.13-4.21 (m, 1H), 4.35-4.44 (m, 1H), 4.45-4.62 (m, 1H), 6.09 (s, 1H), 6.19 (bs, 1H), 6.99-7.24 (m, 3H), 8.07 (d, J=2.9 Hz, 1H). (ESI$^+$) m/z 481.2 (M+H)$^+$.

EXAMPLE 294

2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone

EXAMPLE 294A 2-(4-(5-fluoro-4-(5-fluoro-2-methoxyphenyl)-1H-pyrrolo[2,3-b]pyridin-2-yl)-5,6-dihydropyridin-1(2H)-yl)acetic acid The title compound was prepared essentially as described in Examples 293A and B, substituting Example 231E for Example 282A in Example 293A. MS (ESI$^+$) m/z 400.1 (M+H)$^+$.

EXAMPLE 294B

2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone A mixture of Example 294A (0.100 g, 0.229 mmol), (benzotriazol-1-yl-oxytripyrrolidinophosphonium hexafluorophosphate (0.143 g, 0.275 mmol), triethylamine (0.160 mL, 1.147 mmol), and azetidin-3-ol•hydrochloride (0.030 g, 0.275 mmol) in N,N-dimethylformamide (2.5 mL) was stirred for 3 hours and was treated slowly with water. The solid was filtered, washed with water, dried in a vacuum oven, heated in 6 mL ethyl acetate/heptanes (1:1) at 70° C. for 2 hours, filtered, washed with ethyl acetate/heptanes (1:1), and vacuum oven-dried to provide the title compound. $^1$H NMR (500 MHz, Methanol-d$_4$) δ 2.54-2.60 (m, 2H), 2.78 (t, J=5.7 Hz, 2H), 3.21 (d, J=2.9 Hz, 2H), 3.29 (d, J=3 Hz, 1H), 3.76 (s, 4H), 4.02-4.08 (m, 1H), 4.22 (dd, J=10.7, 6.8 Hz, 1H), 4.44-4.52 (m, 1H), 4.52-4.62 (m, 2H), 6.16 (s, 1H), 6.34-6.39 (m, 1H), 7.08-7.24 (m, 3H), 8.07 (d, J=2.8 Hz, 1H). MS (ESI$^+$) m/z 455.0 (M+H)$^+$.

EXAMPLE 295

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone The title compound was prepared essentially as described in Examples 293A-C, substituting Example 262E for Example 282A in Example 293A. The mixture was concentrated in vacuo and the residue was purified by reverse-phase HPLC on a Phenomenex Luna C8 AXIA column (100 Å) using a gradient of 10-95% acetonitrile/10 mM ammonium acetate in water to afford the title compound. $^1$H NMR (400 MHz, DMSO-d$_6$) δ 2.44-2.96 (m, 8 H) 3.00 (s, 2 H) 3.48-4.47 (m, 6 H) 3.73 (s, 3 H) 6.12 (s, 1 H) 6.30 (s, 1 H)

7.03 (d, J=4.88 Hz, 1 H) 7.13-7.33 (m, 3 H) 8.19 (d, J=4.88 Hz, 1 H) 11.84 (s, 1 H). (ESI+) m/z 463 (M+H)+.

EXAMPLE 296

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone The title compound was prepared essentially as described in Examples 293A-C, substituting Example 262E for Example 282A in Example 293A and azetidin-3-ol hydrochloride with (S)-pyrrolidin-2-ylmethanol. $^1$H NMR (400 MHz, DMSO-$d_6$) δ 1.66-1.84 (m, 4 H) 2.41-3.52 (m, 15 H) 3.73 (s, 3 H) 3.86-4.07 (m, 1 H) 6.11 (s, 1 H) 6.28-6.33 (m, 1 H) 7.03 (d, J=4.88 Hz, 1 H) 7.15-7.31 (m, 3 H) 8.19 (d, J=4.88 Hz, 1 H) 11.85 (s, 1 H). MS (ESI+) m/z 491 (M+H)+.

EXAMPLE 297

2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone A mixture of Example 294A (0.085 g, 0.195 mmol), (benzotriazol-1-yl-oxytripyrrolidinophosphonium hexafluorophosphate (0.122 g, 0.234 mmol), triethylamine (0.109 mL, 0.780 mmol), and piperidin-4-ol•hydrochloride (0.032 g, 0.234 mmol) in N,N-dimethylformamide (2 mL) was stirred for 3 hours. The mixture was treated with water and brine and extracted with ethyl acetate (twice). The combined organic layers were washed with brine, dried over magnesium sulfate, filtered, concentrated, and purified on silica gel using the ISCO Companion eluting with dichloromethane/methanol/ammonium hydroxide (18:1:0.1 to 9:1:0.1) to provide the title compound. $^1$H NMR (400 MHz, Methanol-$d_4$) δ 1.33-1.60 (m, 2H), 1.79-1.94 (m, 2H), 2.56 (bs, 2H), 2.73-2.80 (m, 2H), 3.06-3.18 (m, 1H), 3.27-3.30 (m, 2H), 3.32-3.43 (m, 2H), 3.76 (s, 3H), 3.78-3.98 (m, 2H), 4.03-4.12 (m, 1H), 4.56 (d, J=1.1 Hz, 1H), 6.16 (s, 1H), 6.34-6.40 (m, 1H), 6.99-7.24 (m, 3H), 8.06 (d, J=2.9 Hz, 1H). MS (ESI+) m/z 483.1 (M+H)+.

EXAMPLE 298

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid

EXAMPLE 298A methyl 2-(4-(4-(5-fluoro-4-(5-fluoro-2-methoxyphenyl)-1H-pyrrolo[2,3-b]pyridin-2-yl)-5,6-dihydropyridin-1(2H)-yl)cyclohexyl)acetate To a mixture of Example 231E (0.150 g, 0.362 mmol) and triethylamine (0.111 mL, 0.797 mmol) in dichloromethane (2 mL) and methanol (2 mL) was added acetic acid (0.104 mL, 1.810 mmol), methyl 2-(4-oxocyclohexyl)acetate (0.116 mL, 0.724 mmol) and MP-cyanoborohydride (Biotage, 582 mg, 2.49 mmol/g). The mixture was heated at 40° C. for 3 hours and the solid was filtered and rinsed with dichloromethane/methanol. The filtrate was concentrated and the residue was partitioned in ethyl acetate and saturated aqueous sodium bicarbonate. The organic layer was washed with brine, dried over anhydrous sodium sulfate, filtered and concentrated. The residue was purified on silica gel using the ISCO Companion eluting with methanol/ethyl acetate (5:95) to provide the title compound. MS (ESI+) m/z 496.1 (M+H)+.

EXAMPLE 298B (4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid A mixture of Example 298A (0.115 g, 0.232 mmol) and lithium hydroxide (0.011 g, 0.464 mmol) in tetrahydrofuran (3 mL), methanol (1.2 mL), and water (0.9 mL) was stirred overnight and concentrated. The residue was dissolved in 4 mL water and treated with 2M aqueous hydrogen chloride. The suspension was diluted with water, stirred for 15 minutes, filtered, washed with water, and vacuum oven-dried to provide the title compound as a hydrochloride salt. $^1$H NMR (400 MHz, Methanol-$d_4$) δ 1.13-1.28 (m, 1H), 1.55-1.95 (m, 4H), 1.95-2.07 (m, 2H), 2.17-2.27 (m, 3H), 2.43 (d, J=7.6 Hz, 1H), 2.87-2.95 (m, 2H), 3.30-3.38 (m, 2H), 3.77 (s, 4H), 4.00-4.08 (m, 2H), 6.33 (s, 1H), 6.41 (bs, 1H), 7.08-7.26 (m, 3H), 8.15 (d, J=2.8 Hz, 1H). MS (ESI+) m/z 482.0 (M+H)+.

EXAMPLE 299

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone

EXAMPLE 299A tert-butyl 2-(4-(4-(5-fluoro-2-methoxyphenyl)-1H-pyrrolo[2,3-b]pyridin-2-yl)-6,6-dimethyl-5,6-dihydropyridin-1(2H)-yl)acetate A mixture of Example 272B (0.388 g, 0.915 mmol), tert-butyl bromoacetate (0.264 g, 1.35 mmol) and triethylamine (0.7 mL, 5.02 mmol) in N,N-dimethylformamide (2 mL) was heated at 70° C. for 8 hours and was concentrated. The residue was partitioned between ethyl acetate and water and the organic layer was dried over sodium sulfate, filtered and concentrated. Purification by flash chromatography on silica gel eluting with 50% ethyl acetate in hexanes gave the title compound. MS (ESI) m/e 466.4 (M+1)+.

EXAMPLE 299B 2-(4-(4-(5-fluoro-2-methoxyphenyl)-1H-pyrrolo[2,3-b]pyridin-2-yl)-6,6-dimethyl-5,6-dihydropyridin-1(2H)-yl)acetic acid Example 299A (0.136 g, 0.294 mmol) and trifluoroacetic acid (2 mL, 26 mmol) were stirred in dichloromethane (2 mL) for 24 hours at room temperature and concentrated under reduced pressure. The hydrochloride salt was prepared by dissolving the solid in methanol and adding 2M hydrogen chloride in diethyl ether. After concentration, the title compound was obtained. MS (ESI) m/e 410.4 (M+1)+.

EXAMPLE 299C

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone A mixture of Example 299B (0.172 g, 0.357 mmol), 3-hydroxyazetidine hydrochloride (0.047 g, 0.429 mmol), 2-(3H-[1,2,3]triazolo[4,5-b]pyridin-3-yl)-1,1,3,3-tetramethylisouronium hexafluorophosphate(V) (0.164 g, 0.431 mmol) and triethylamine (0.3 mL, 2.15 mmol) in N,N-dimethylformamide (4 mL) was stirred for 24 hours at room temperature. The mixture was concentrated and purified by reverse phase-HPLC (Sunfire 5 µM, 50×250 mm) eluting with 5-40% acetonitrile in water (containing 0.1% trifluoroacetic acid). The trifluoroacetate salt was dissolved in methanol and eluted from a SCX column with 0.5M ammonia in methanol to provide the title compound. $^1$HNMR (500 MHz, DMSO-$d_6$) δ 1.03 (br s, 6H), 2.32 (br s, 2H), 3.11 (m, 4H), 3.57 (m, 1H), 3.73 (s, 3H), 3.95 (m, 1H), 4.04 (m, 1H), 4.39 (m, 2H), 6.54 (m, 1H), 6.19 (br s, 1H), 6.46 (m, 1H), 7.02 (d, 1H), 7.23 (m, 3H), 8.18 (d, 1H), 11.79 (br s, 1H). MS (ESI) m/e 465.0 (M+1)$^+$.

EXAMPLE 300

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone The title compound was prepared using the conditions described in Example 280, substituting 2-hydroxyacetic acid with 3-hydroxycyclobutanecarboxylic acid. $^1$H NMR (500 MHz, DMSO-$d_6$) δ 1.78-2.38 (m, 4 H) 2.53-3.13 (m, 5 H) 3.41-3.69 (m, 4 H) 3.73 (s, 3 H) 3.84-4.02 (m, 1 H) 5.03 (dd, J=9.16, 7.02 Hz, 1 H) 6.18 (dd, J=4.73, 1.68 Hz, 1 H) 6.30 (s, 1 H) 7.04 (d, J=4.88 Hz, 1 H) 7.15-7.33 (m, 3 H) 8.21 (d, J=4.88 Hz, 1 H) 11.90 (s, 1 H).). (ESI$^+$) m/z 462 (M+H)$^+$.

EXAMPLE 301

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide

EXAMPLE 301A tert-butyl 3-(5-cyano-4-(5-fluoro-2-methoxyphenyl)-1H-pyrrolo[2,3-b]pyridin-2-yl)-8-azabicyclo[3.2.1]oct-3-ene-8-carboxylate A mixture of Example 236C (0.4 g, 0.750 mmol), Example 223B (0.302 g, 0.900 mmol), sodium carbonate (0.238 g, 2.250 mmol), and [1,1'-bis(diphenylphosphino)ferrocene]dichloro-palladium(II) dichloromethane adduct (0.043 g, 0.053 mmol) in 10 mL tetrahydrofuran and 3 mL water was heated at 80° C. for 4 hours. The mixture was cooled to room temperature and treated with 2N lithium hydroxide (1.875 mL, 3.75 mmol) for 4 hours. The mixture was neutralized with 2N aqueous hydrochloric acid and extracted with ethyl acetate. The organic phase was washed with water and brine, dried over sodium sulfate, filtered and concentrated. The residue was purified by flash chromatography eluting with 0-5% methanol in dichloromethane to afford the title compound. MS (ESI(+)) m/e 475 (M+H)$^+$.

EXAMPLE 301B 2-(8-azabicyclo[3.2.1]oct-3-en-3-yl)-4-(5-fluoro-2-methoxyphenyl)-1H-pyrrolo[2,3-b]pyridine-5-carbonitrile To a solution of Example 301A (380 mg, 0.801 mmol) in dichloromethane (5 mL) was added trifluoroacetic acid (617 µL, 8.01 mmol) and the mixture was stirred at room temperature overnight and concentrated. The residue was triturated with diethyl ether, filtered, and dried under reduced pressure to afford the title compound as the trifluoroacetate salt. MS (ESI(+)) m/e 375 (M+H)$^+$.

EXAMPLE 301C

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide The title compound was prepared using the procedure described in Example 235, substituting Example 301B for Example 17G. $^1$H NMR (400 MHz, DMSO-$d_6$) δ 1.39-2.40 (m, 6H), 2.68-2.78 (m, 1H), 2.78-2.83 (m, 4H), 3.00 (d, J=3.3 Hz, 3H), 3.40-3.63 (m, 2H), 3.75 (s, 3H), 6.21 (bs, 1H), 6.67-6.73 (m, 1H), 7.21-7.34 (m, 2H), 7.38 (td, J=8.6, 3.2 Hz, 1H), 8.59 (s, 1H), 12.42 (bs, 1H). MS (ESI(+)) m/e 460 (M+H)$^+$.

EXAMPLE 302

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide

EXAMPLE 302A 2-(8-azabicyclo[3.2.1]oct-2-en-3-yl)-5-fluoro-4-(5-fluoro-2-methoxyphenyl)-1H-pyrrolo[2,3-b]pyridine hydrochloric acid The title compound was prepared essentially as described in Examples 231C-E, substituting Example 223B for tert-butyl 4-(4,4,5,5-tetramethyl-1,3,2-dioxaborolan-2-yl)-5,6-dihydropyridine-1(2H)-carboxylate in Example 231C. MS (ESI$^+$) m/z 368.0 (M+H)$^+$.

EXAMPLE 302B

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide A mixture of Example 302A (110.0 mg, 0.250 mmol), 2-chloro-N,N-dimethylacetamide (0.030 mL, 0.287 mmol), and triethylamine (0.174 mL, 1.249 mmol) in N,N-dimethylformamide (2.5 mL) was heated at 75° C. for 4 hours. The mixture was treated with water and brine and extracted with ethyl acetate (twice). The combined organic layers were washed with brine, dried over magnesium sulfate, filtered, concentrated, and purified on silica gel using the ISCO Companion eluting with dichloromethane methanol/ammonium hydroxide (18:1:0.1) to provide the title compound. $^1$H NMR (500 MHz, Methanol-$d_4$) δ 1.58-1.69 (m, 1H), 1.90-1.98 (m, 1H), 2.01-2.26 (m, 2H), 2.83-3.01 (m, 5H), 3.05 (d, J=2.8 Hz, 3H), 3.39-3.65 (m, 3H), 3.69 (t, J=5.7 Hz, 1H), 3.76 (s, 3H), 6.13 (s, 1H), 6.48-6.53 (m, 1H), 7.07-7.25 (m, 3H), 8.06 (d, J=2.8 Hz, 1H). MS (ESI$^+$) m/z 453.1 (M+H)$^+$.

EXAMPLE 303

4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile

EXAMPLE 303A tert-butyl 2-(5-(5-cyano-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetate The title compound was prepared using the procedure described in Example 226A, substituting Example 277C for Example 87. MS (ESI(+)) m/e 489.

EXAMPLE 303B 2-(5-(5-cyano-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetic acid The title compound was prepared using the procedure described in Example 226B, substituting Example 303A for Example 226A. MS (ESI(+)) m/e 433 (M+H)$^+$.

EXAMPLE 303C 4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile The title compound was prepared according to the procedure described in Example 238 substituting Example 303B for Example 226B and (S)-pyrrolidin-2-ylmethanol for azetidin-3-ol hydrochloride. $^1$H NMR (400 MHz, DMSO-d$_6$) δ 1.25 (s, 1H), 1.64-1.99 (m, 4H), 2.59-2.81 (m, 4H), 3.12-3.72 (m, 9H), 3.74 (s, 3H), 3.78-4.62 (m, 2H), 6.16 (s, 1H), 6.36 (bs, 1H), 7.15-7.29 (m, 3H), 7.33 (td, J=8.6, 3.1 Hz, 1H), 12.23 (bs, 1H). MS (ESI(+)) m/e 516 (M+H)$^+$.

EXAMPLE 304

2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone

EXAMPLE 304A 2-(3-(4-(5-fluoro-2-methoxyphenyl)-1H-pyrrolo[2,3-b]pyridin-2-yl)-8-azabicyclo[3.2.1]oct-2-en-8-yl)acetic acid The title compound was prepared essentially as described in Examples 293A and B, substituting Example 223C for Example 282A in Example 293A. MS (ESI$^+$) m/z 408.1 (M+H)$^+$.

EXAMPLE 304B

2-{3-[4-(5-fluoro-2-methoxyphenyl)-1H-pyrrolo[2,3-b]pyridin-2-yl]-8-azabicyclo[3.2.1]oct-2-en-8-yl})-1-(3-hydroxyazetidin-1-yl)ethanone A mixture of Example 304A (0.100 g, 0.225 mmol), (benzotriazol-1-yl-oxytripyrrolidinophosphonium hexafluorophosphate (0.141 g, 0.270 mmol), triethylamine (0.157 mL, 1.126 mmol), and azetidin-3-ol•hydrochloride (0.030 g, 0.270 mmol) in N,N-dimethylformamide (2.5 mL) was stirred for 3 hours. The mixture was treated with water and brine and extracted with ethyl acetate (twice). The combined organic layers were washed with brine, dried over magnesium sulfate, filtered, concentrated, and purified on silica gel using the ISCO Companion flash system eluting with dichloromethane/methanol/ammonium hydroxide (18:1:0.1 to 12:1:0.1) to provide the title compound. $^1$H NMR (500 MHz, Methanol-d$_4$) δ 1.60-1.70 (m, 1H), 1.91-1.99 (m, 1H), 2.06-2.17 (m, 2H), 2.16-2.27 (m, 1H), 2.82-2.91 (m, 1H), 3.26-3.34 (m, 1H), 3.51-3.58 (m, 1H), 3.63-3.70 (m, 1H), 3.76-3.78 (m, 4H), 4.00 (td, J=9.9, 4.3 Hz, 1H), 4.21 (dd, J=10.6, 6.9 Hz, 1H), 4.33-4.46 (m, 1H), 4.49-4.69 (m, 2H), 6.23 (s, 1H), 6.48-6.53 (m, 1H), 7.07 (d, J=5.1 Hz, 1H), 7.09-7.20 (m, 3H), 8.15 (d, J=5.1 Hz, 1H). MS (ESI$^+$) m/z 463.1 (M+H)$^+$.

EXAMPLE 305

2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone The title compound was prepared essentially as described in Example 304B, substituting (S)-pyrrolidin-2-ylmethanol for azetidin-3-ol hydrochloride. $^1$H NMR (400 MHz, Methanol-d$_4$) δ 1.60-1.72 (m, 1H), 1.79-2.07 (m, 5H), 2.05-2.31 (m, 3H), 2.85-2.94 (m, 1H), 3.41-3.67 (m, 7H), 3.76 (s, 4H), 4.05-4.20 (m, 1H), 6.24 (s, 1H), 6.48-6.54 (m, 1H), 7.07 (d, J=5.1 Hz, 1H), 7.10-7.20 (m, 3H), 8.14 (d, J=5.1 Hz, 1H). MS (ESI$^+$) m/z 491.2 (M+H)$^+$.

EXAMPLE 306

2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide The title compound was prepared essentially as described in Example 304B, substituting 2-(methylamino)ethanol for azetidin-3-ol hydrochloride. MS (ESI$^+$) m/z 408.1 (M+H)$^+$. $^1$H NMR (400 MHz, Methanol-d$_4$) δ 1.60-1.73 (m, 1H), 1.91-2.01 (m, 1H), 2.02-2.28 (m, 3H), 2.89-2.95 (m, 3H), 3.10 (s, 1H), 3.42-3.95 (m, 11H), 6.24 (s, 1H), 6.51 (d, J=5.5 Hz, 1H), 7.07 (d, J=5.1 Hz, 1H), 7.10-7.19 (m, 3H), 8.14 (d, J=5.1 Hz, 1H). MS (ESI$^+$) m/z 465.1 (M+H)$^+$.

EXAMPLE 307

N-benzyl-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A. $^1$H NMR (400 MHz, DMSO-d$_6$) δ 1.71-1.87 (m, 2H), 2.18-2.30 (m, 2H), 2.83 (d, J=4.3 Hz, 3H), 2.98 (tt, J=12.2, 3.5 Hz, 1H), 3.11 (dt, J=13.5, 10.7 Hz, 2H), 3.55 (d, J=12.0 Hz, 2H), 4.30 (s, 2H), 5.94 (s, 1H), 6.72 (dd, J=8.2, 4.3 Hz, 2H), 6.93-7.16 (m, 2H), 7.26 (t, J=6.8 Hz, 1H), 7.30-7.43 (m, 4H), 8.20 (d, J=5.1 Hz, 1H). MS (ESI$^+$) m/z 415 (M+H)$^+$.

EXAMPLE 308

4-[({4-fluoro-3-[2-(1-methylpiperidin-4-yl)-1H-pyrrolo[2,3-b]pyridin-4-yl]phenyl}amino)methyl]phenol The title compound was prepared essentially as described in Example 11B, substituting Example 179D (20 mg, 0.06 mmol) for Example 11A and 4-hydroxybenzaldehyde for benzaldehyde. $^1$H NMR (400 MHz, DMSO-$d_6$) δ 1.81 (qd, J=13.4, 3.8 Hz, 2H), 2.19-2.32 (m, 2H), 2.83 (d, J=4.3 Hz, 3H), 3.00 (ddt, J=12.2, 8.6, 3.5 Hz, 1H), 3.11 (dt, J=12.7, 9.7 Hz, 2H), 3.55 (d, J=12.0 Hz, 2H), 4.18 (s, 2H), 5.97 (s, 1H), 6.63-6.82 (m, 4H), 7.03-7.21 (m, 4H), 8.22 (d, J=5.0 Hz, 1H). MS (ESI$^+$) m/z 431 (M+H)$^+$.

EXAMPLE 309

4-fluoro-3-[2-(1-methylpiperidin-4-yl)-1H-pyrrolo[2,3-b]pyridin-4-yl]-N-(1H-1,2,4-triazol-5-ylmethyl)aniline The title compound was prepared essentially as described in Example 11B, substituting Example 179D (20 mg, 0.06 mmol) for Example 11A and 1H-1,2,4-triazole-5-carbaldehyde for benzaldehyde. $^1$H NMR (400 MHz, DMSO-$d_6$) δ 1.82 (qd, J=13.5, 7.0 Hz, 2H), 2.30 (dq, J=15.9, 5.9, 5.2 Hz, 2H), 2.83 (d, J=4.3 Hz, 3H), 2.92-3.03 (m, 1H), 3.12 (q, J=11.7 Hz, 2H), 3.55 (d, J=11.9 Hz, 2H), 4.82 (d, J=3.9 Hz, 2H), 6.09 (s, 1H), 6.72-6.86 (m, 2H), 6.99-7.21 (m, 3H), 8.22 (t, J=5.6 Hz, 1H). MS (ESI$^+$) m/z 406 (M+H)$^+$.

EXAMPLE 310

4-fluoro-3-[2-(1-methylpiperidin-4-yl)-1H-pyrrolo[2,3-b]pyridin-4-yl]-N-(pyridin-2-ylmethyl)aniline The title compound was prepared essentially as described in Example 11B, substituting Example 179D (20 mg, 0.06 mmol) for Example 11A and picolinaldehyde for benzaldehyde. $^1$H NMR (400 MHz, DMSO-$d_6$) δ 1.80 (qd, J=13.3, 3.7 Hz, 2H), 2.15-2.34 (m, 2H), 2.83 (d, J=4.3 Hz, 3H), 2.93-3.04 (m, 1H), 3.13 (ddt, J=18.7, 12.4, 7.4 Hz, 2H), 3.55 (d, J=12.0 Hz, 2H), 4.55 (s, 2H), 5.97 (d, J=2.3 Hz, 1H), 6.68-6.82 (m, 2H), 7.04 (d, J=5.0 Hz, 1H), 7.07-7.20 (m, 1H), 7.59 (dd, J=7.6, 5.1 Hz, 1H), 7.68 (d, J=7.9 Hz, 1H), 8.06-8.17 (m, 1H), 8.22 (d, J=5.0 Hz, 1H), 8.68 (d, J=5.2 Hz, 1H). MS (ESI$^+$) m/z 416 (M+H)$^+$.

EXAMPLE 311

N-[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 2,2-dimethyltetrahydro-2H-pyran-4-carbaldehyde for benzaldehyde. $^1$H NMR (400 MHz, DMSO-$d_6$) δ 0.94-1.09 (m, 2H), 1.14 (d, J=3.7 Hz, 6H), 1.65 (dt, J=13.3, 3.4 Hz, 2H), 1.83 (t, J=13.1 Hz, 2H), 1.96 (ddd, J=11.6, 8.2, 4.8 Hz, 1H), 2.30 (d, J=14.0 Hz, 2H), 2.82 (d, J=4.5 Hz, 3H), 2.87 (dd, J=6.6, 3.0 Hz, 2H), 2.92-3.21 (m, 3H), 3.45-3.66 (m, 4H), 6.10 (d, J=2.2 Hz, 1H), 6.71 (ddd, J=10.4, 7.7, 3.5 Hz, 2H), 7.03-7.16 (m, 2H), 8.23 (d, J=5.0 Hz, 1H). MS (ESI$^+$) m/z 451 (M+H)$^+$.

EXAMPLE 312

N,N-bis[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline The title compound was prepared as a by-product in Example 311. $^1$H NMR (400 MHz, DMSO-$d_6$) δ 0.97-1.05 (m, 4H), 1.10 (d, J=11.1 Hz, 12H), 1.51 (dd, J=13.1, 3.7 Hz, 4H), 1.83 (dd, J=12.7, 6.2 Hz, 2H), 2.10 (t, J=11.3 Hz, 3H), 2.29 (d, J=13.8 Hz, 2H), 2.82 (d, J=4.3 Hz, 3H), 2.92-3.22 (m, 6H), 3.39-3.68 (m, 6H), 6.09 (d, J=2.2 Hz, 1H), 6.77 (ddt, J=21.3, 5.6, 2.9 Hz, 2H), 7.08 (d, J=5.0 Hz, 1H), 7.12-7.20 (m, 1H), 8.24 (d, J=5.0 Hz, 1H). MS (ESI$^+$) m/z 577 (M+H)$^+$.

EXAMPLE 313

N,N-bis(cyclopropylmethyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and cyclopropanecarbaldehyde for benzaldehyde. $^1$H NMR (400 MHz, DMSO-$d_6$) δ 0.01 (d, J=5.0 Hz, 4H), 0.23 (d, J=7.9 Hz, 4H), 0.71 (p, J=6.4 Hz, 2H), 1.57 (qd, J=13.5, 3.8 Hz, 2H), 1.95-2.13 (m, 2H), 2.25 (dt, J=3.6, 1.8 Hz, 3H), 2.70-2.95 (m, 3H), 3.15 (d, J=6.6 Hz, 4H), 3.29 (d, J=12.1 Hz, 2H), 5.86 (s, 1H), 6.90 (d, J=5.1 Hz, 1H), 6.95-7.29 (m, 3H), 8.03 (d, J=5.0 Hz, 1H). MS (ESI$^+$) m/z 433 (M+H)$^+$.

EXAMPLE 314

4-fluoro-3-[2-(1-methylpiperidin-4-yl)-1H-pyrrolo[2,3-b]pyridin-4-yl]-N-[3-(methylsulfonyl)benzyl]aniline The title compound was prepared essentially as described in Example 11B, substituting Example 179D (20 mg, 0.06 mmol) for Example 11A and 3-(methylsulfonyl)benzaldehyde for benzaldehyde. $^1$H NMR (400 MHz, DMSO-$d_6$) δ 1.68-1.89 (m, 2H), 2.14-2.33 (m, 2H), 2.82 (d, J=4.1 Hz, 3H), 2.98 (tt, J=12.2, 3.4 Hz, 1H), 3.05-3.15 (m, 2H), 3.54 (d, J=12.1 Hz, 2H), 4.43 (s, 2H), 5.94 (t, J=2.1 Hz, 1H), 6.71 (dq, J=6.0, 3.4 Hz, 2H), 7.04 (d, J=4.9 Hz, 1H), 7.11 (dd, J=10.2, 8.4 Hz, 1H), 7.63 (t, J=7.7 Hz, 1H), 7.73 (d, J=7.7 Hz, 1H), 7.83 (dd, J=8.0, 1.9 Hz, 1H), 7.87-7.98 (m, 1H), 8.21 (d, J=5.1 Hz, 1H). MS (ESI$^+$) m/z 493 (M+H)$^+$.

The following compounds (concluding with Example 975) were prepared essentially as described in Example 119, substituting the appropriate amino intermediate and/or the appropriate sulfonyl chloride reagent. Either N,N-dimethylformamide or 1-methyl-2-pyrrolidinone was used as the solvent. Some products were purified by flash chromatography while others were purified by reverse-phase HPLC. Accordingly, some examples were isolated as trifluoroacetic acid salts. Some Examples (free base or trifluoroacetic acid salt) were converted into HCl salts.

EXAMPLE 315

2-[1-(cyclopropylsulfonyl)-1,2,3,6-tetrahydropyridin-4-yl]-4-(5-fluoro-2-methoxyphenyl)-1H-pyrrolo[2,3-b]pyridine $^1$H NMR (400 MHz, methanol-$d_4$) δ ppm 0.96-1.20 (m, 4H), 2.50-2.60 (m, 1H), 2.67-2.75 (m, 2H), 3.59 (t, J=5.7

Hz, 2H), 3.83 (s, 3H), 4.12 (q, J=2.9 Hz, 2H), 6.58-6.64 (m, 1H), 6.66 (s, 1H), 7.21-7.29 (m, 1H), 7.27-7.38 (m, 2H), 7.57 (d, J=6.2 Hz, 1H), 8.31 (d, J=6.2 Hz, 1H). MS (ESI⁺) m/z 428.2 (M+H)⁺.

EXAMPLE 331

2-{1-[(chloromethyl)sulfonyl]-1,2,3,6-tetrahydropyridin-4-yl}-4-(5-fluoro-2-methoxyphenyl)-1H-pyrrolo[2,3-b]pyridine ¹H NMR (400 MHz, DMSO-d₆) δ ppm 2.60 (q, J=4.3, 3.6 Hz, 2H), 3.56 (t, J=5.7 Hz, 2H), 3.74 (s, 3H), 4.07-4.13 (m, 2H), 5.14 (s, 2H), 6.31 (d, J=1.9 Hz, 1H), 6.54 (bs, 1H), 7.09 (d, J=5.0 Hz, 1H), 7.17-7.33 (m, 3H), 8.24 (d, J=5.0 Hz, 1H), 11.99 (bs, 1H). MS (ESI⁺) m/z 436.1 (M+H)⁺.

EXAMPLE 332

4-(5-fluoro-2-methoxyphenyl)-2-[1-(propan-2-ylsulfonyl)-1,2,3,6-tetrahydropyridin-4-yl]-1H-pyrrolo[2,3-b]pyridine ¹H NMR (400 MHz, methanol-d₄) δ ppm 1.34 (d, J=6.8 Hz, 6H), 2.62-2.68 (m, 2H), 3.37 (p, J=6.8 Hz, 1H), 3.61 (t, J=5.6 Hz, 2H), 3.81 (s, 3H), 4.11-4.16 (m, 2H), 6.49-6.56 (m, 2H), 7.16-7.31 (m, 3H), 7.41 (d, J=5.8 Hz, 1H), 8.26 (d, J=5.8 Hz, 1H). MS (ESI⁺) m/z 430.2 (M+H)⁺.

EXAMPLE 333

4-(5-fluoro-2-methoxyphenyl)-2-[1-(propylsulfonyl)-1,2,3,6-tetrahydropyridin-4-yl]-1H-pyrrolo[2,3-b]pyridine ¹H NMR (400 MHz, methanol-d₄) δ ppm 1.07 (t, J=7.4 Hz, 3H), 1.77-1.89 (m, 2H), 2.65-2.72 (m, 2H), 3.03-3.11 (m, 2H), 3.56 (t, J=5.7 Hz, 2H), 3.83 (s, 3H), 4.10 (q, J=2.9 Hz, 2H), 6.56-6.62 (m, 1H), 6.66 (s, 1H), 7.21-7.35 (m, 3H), 7.57 (d, J=6.2 Hz, 1H), 8.31 (d, J=6.2 Hz, 1H). MS (ESI⁺) m/z 430.2 (M+H)⁺.

EXAMPLE 334

2-{1-[(1,1-dioxidotetrahydrothiophen-3-yl)sulfonyl]-1,2,3,6-tetrahydropyridin-4-yl}-4-(5-fluoro-2-methoxyphenyl)-1H-pyrrolo[2,3-b]pyridine ¹H NMR (400 MHz, pyridine-d₅) δ ppm 2.65-2.81 (m, 4H), 3.29-3.41 (m, 1H), 3.51-3.61 (m, 1H), 3.70-3.72 (m, 5H), 3.79 (dd, J=13.4, 9.9 Hz, 1H), 3.96 (dd, J=13.4, 8.3 Hz, 1H), 4.28-4.33 (m, 2H), 4.56-4.69 (m, 1H), 6.62-6.71 (m, 2H), 7.11 (dd, J=9.0, 4.5 Hz, 1H), 7.26-7.35 (m, 2H), 7.49 (dd, J=8.9, 3.2 Hz, 1H), 8.60 (d, J=4.9 Hz, 1H), 12.98-13.04 (m, 1H). MS (ESI⁺) m/z 506.1 (M+H)⁺.

EXAMPLE 336

4-(5-fluoro-2-methoxyphenyl)-2-{1-[(2,2,2-trifluoroethyl)sulfonyl]-1,2,3,6-tetrahydropyridin-4-yl}-1H-pyrrolo[2,3-b]pyridine ¹H NMR (400 MHz, methanol-d4) δ ppm 2.67-2.72 (m, 2H), 3.61 (t, J=5.7 Hz, 2H), 3.80 (s, 3H), 4.14 (d, J=3.1 Hz, 2H), 4.22 (q, J=9.7 Hz, 2H), 6.48-6.54 (m, 1H), 6.53 (s, 1H), 7.16-7.29 (m, 3H), 7.38 (d, J=5.7 Hz, 1H), 8.26 (d, J=5.7 Hz, 1H). MS (ESI⁺) m/z 470.1 (M+H)⁺.

EXAMPLE 348

4-(5-fluoro-2-methoxyphenyl)-2-[1-(thiophen-2-ylsulfonyl)-1,2,3,6-tetrahydropyridin-4-yl]-1H-pyrrolo[2,3-b]pyridine ¹H NMR (400 MHz, DMSO-d₆) δ ppm 2.60 (q, J=4.6 Hz, 2H), 3.24 (t, J=5.7 Hz, 2H), 3.73 (s, 3H), 3.77-3.82 (m, 2H), 6.24 (d, J=2.0 Hz, 1H), 6.48 (bs, 1H), 7.05 (d, J=4.9 Hz, 1H), 7.16-7.25 (m, 2H), 7.23-7.33 (m, 2H), 7.72 (dd, J=3.7, 1.3 Hz, 1H), 8.05 (dd, J=5.0, 1.3 Hz, 1H), 8.21 (d, J=4.9 Hz, 1H), 11.86-11.90 (m, 1H). MS (ESI⁺) m/z 470.1 (M+H)⁺.

EXAMPLE 349

N-[2-chloro-4-({4-[4-(5-fluoro-2-methoxyphenyl)-1H-pyrrolo[2,3-b]pyridin-2-yl]-3,6-dihydropyridin-1(2H)-yl}sulfonyl)phenyl]acetamide ¹H NMR (400 MHz, methanol-d₄) δ ppm 2.21 (s, 3H), 2.62-2.67 (m, 2H), 3.39 (t, J=5.8 Hz, 2H), 3.80 (s, 3H), 3.87-3.93 (m, 2H), 6.42-6.49 (m, 1H), 6.52 (s, 1H), 7.19-7.29 (m, 3H), 7.44 (d, J=5.9 Hz, 1H), 7.76 (dd, J=8.6, 2.1 Hz, 1H), 7.91 (d, J=2.1 Hz, 1H), 8.21 (d, J=8.6 Hz, 1H), 8.26 (d, J=5.9 Hz, 1H). MS (ESI⁺) m/z 555.1 (M+H)⁺.

EXAMPLE 350

4-(5-fluoro-2-methoxyphenyl)-2-{1-[(2,4,5-trichlorophenyl)sulfonyl]-1,2,3,6-tetrahydropyridin-4-yl}-1H-pyrrolo[2,3-b]pyridine ¹H NMR (400 MHz, DMSO-d₆) δ ppm 2.56 (d, J=3.7 Hz, 2H), 3.57 (t, J=5.7 Hz, 2H), 3.75 (s, 3H), 4.03-4.08 (m, 2H), 6.28 (d, J=2.0 Hz, 1H), 6.52 (bs, 1H), 7.08 (d, J=5.0 Hz, 1H), 7.18-7.34 (m, 3H), 8.14-8.21 (m, 2H), 8.24 (d, J=5.0 Hz, 1H), 11.91-11.96 (m, 1H). MS (ESI⁺) m/z 566.0 (M+H)⁺.

EXAMPLE 351

4-({4-[4-(5-fluoro-2-methoxyphenyl)-1H-pyrrolo[2,3-b]pyridin-2-yl]-3,6-dihydropyridin-1(2H)-yl}sulfonyl)-2,1,3-benzoxadiazole ¹H NMR (400 MHz, DMSO-d₆) δ ppm 2.50-2.54 (m, 2H), 3.51-3.54 (m, 2H), 3.73 (s, 3H), 4.01-4.06 (m, 2H), 6.24 (d, J=1.9 Hz, 1H), 6.46 (bs, 1H), 7.08 (d, J=5.1 Hz, 1H), 7.15-7.25 (m, 2H), 7.28 (td, J=8.6, 3.2 Hz, 1H), 7.77 (dd, J=9.0, 6.8 Hz, 1H), 8.17 (d, J=6.8 Hz, 1H), 8.22 (d, J=5.0 Hz, 1H), 8.38 (d, J=9.0 Hz, 1H), 11.94 (bs, 1H). MS (ESI⁺) m/z 506.1 (M+H)⁺.

EXAMPLE 352

2-{1-[(3,5-dimethyl-1,2-oxazol-4-yl)sulfonyl]-1,2,3,6-tetrahydropyridin-4-yl}-4-(5-fluoro-2-methoxyphenyl)-1H-pyrrolo[2,3-b]pyridine ¹H NMR (400 MHz, methanol-d₄) δ ppm 2.41 (s, 3H), 2.64-2.69 (m, 5H), 3.48 (t, J=5.7 Hz, 2H), 3.79 (s, 3H), 3.94-3.99 (m, 2H), 6.45 (bs, 2H), 7.15-7.26 (m, 3H), 7.29 (d, J=5.5 Hz, 1H), 8.23 (d, J=5.5 Hz, 1H). MS (ESI⁺) m/z 483.1 (M+H)⁺.

EXAMPLE 405

2-{1-[(3-chlorobenzyl)sulfonyl]-1,2,3,6-tetrahydropyridin-4-yl}-4-(5-fluoro-2-methoxyphenyl)-1H-pyrrolo[2,3-b]pyridine $^1$H NMR (400 MHz, pyridine-d$_5$) δ ppm 2.58-2.66 (m, 2H), 3.60 (t, J=5.7 Hz, 2H), 3.72 (s, 3H), 4.19-4.25 (m, 2H), 4.67 (s, 2H), 6.61-6.66 (m, 2H), 7.11 (dd, J=9.0, 4.5 Hz, 1H), 7.27-7.35 (m, 2H), 7.36 (ddd, J=8.0, 2.1, 1.1 Hz, 1H), 7.50 (dd, J=8.9, 3.2 Hz, 1H), 7.54 (dt, J=7.6, 1.4 Hz, 1H), 7.74 (t, J=1.8 Hz, 1H), 8.60 (d, J=4.9 Hz, 1H), 12.99 (bs, 1H). MS (ESI$^+$) m/z 512.1 (M+H)$^+$.

EXAMPLE 537

4-(5-fluoro-2-methoxyphenyl)-2-[1-(methylsulfonyl)-1,2,5,6-tetrahydropyridin-3-yl]-1H-pyrrolo[2,3-b]pyridine $^1$H NMR (500 MHz, methanol-d$_4$) δ ppm 2.52-2.57 (m, 2H), 2.94 (s, 3H), 3.45 (t, J=5.8 Hz, 2H), 3.81 (s, 3H), 4.17 (d, J=2.6 Hz, 2H), 6.49 (s, 1H), 6.64-6.70 (m, 1H), 7.18-7.30 (m, 3H), 7.39 (d, J=5.7 Hz, 1H), 8.26 (d, J=5.7 Hz, 1H). MS (ESI$^+$) m/z 402.1 (M+H)$^+$.

EXAMPLE 675

4-{5-fluoro-2-[($^2$H$_3$)methyloxy]phenyl}-2-[1-(methylsulfonyl)-1,2,3,6-tetrahydropyridin-4-yl]-1H-pyrrolo[2,3-b]pyridine $^1$H NMR (500 MHz, methanol-d$_4$) δ ppm 2.69-2.75 (m, 2H), 2.92 (s, 3H), 3.52 (t, J=5.7 Hz, 2H), 4.03-4.08 (m, 2H), 6.58-6.63 (m, 1H), 6.67 (s, 1H), 7.21-7.28 (m, 1H), 7.26-7.36 (m, 2H), 7.59 (d, J=6.2 Hz, 1H), 8.32 (d, J=6.2 Hz, 1H). MS (ESI$^+$) m/z 405.2 (M+H)$^+$.

EXAMPLE 697

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 2.55-2.64 (m, 2H), 2.93 (s, 2H), 3.35 (dd, J=6.8, 5.0 Hz, 2H), 3.88-3.93 (m, 2H), 6.21 (d, J=2.1 Hz, 1H), 6.48-6.62 (m, 1H), 7.20-7.37 (m, 3H), 8.21 (d, J=2.6 Hz, 1H), 11.99 (d, J=2.3 Hz, 1H). MS (ESI$^+$) m/z 420.1 (M+H)$^+$.

EXAMPLE 730

3-methoxy-N-methyl-4-{2-[1-(methylsulfonyl)-1,2,3,6-tetrahydropyridin-4-yl]-1H-pyrrolo[2,3-b]pyridin-4-yl}benzamide $^1$H NMR (400 MHz, methanol-d$_4$) δ ppm 2.66-2.73 (m, 2H), 2.92 (s, 3H), 2.98 (s, 3H), 3.52 (t, J=5.7 Hz, 2H), 3.90 (s, 3H), 4.01-4.07 (m, 2H), 6.53-6.61 (m, 2H), 7.51 (d, J=6.0 Hz, 1H), 7.59 (s, 2H), 7.67 (s, 1H), 8.29 (d, J=6.0 Hz, 1H). MS (ESI$^+$) m/z 441.2 (M+H)$^+$.

EXAMPLE 975

2-[3,3-dimethyl-1-(methylsulfonyl)-1,2,3,6-tetrahydropyridin-4-yl]-4-(5-fluoro-2-methoxyphenyl)-1H-pyrrolo[2,3-b]pyridine $^1$H NMR (500 MHz, methanol-d$_4$) δ ppm 1.29 (s, 6H), 2.93 (s, 3H), 3.19 (s, 2H), 3.83 (s, 3H), 3.97 (d, J=3.5 Hz, 2H), 6.21 (t, J=3.5 Hz, 1H), 6.55 (s, 1H), 7.25 (dd, J=10.3, 4.1 Hz, 1H), 7.28-7.35 (m, 2H), 7.56 (d, J=6.1 Hz, 1H), 8.34 (d, J=6.1 Hz, 1H). MS (ESI$^+$) m/z 430.2 (M+H)$^+$.

EXAMPLE 316

4-[({4-fluoro-3-[2-(1-methylpiperidin-4-yl)-1H-pyrrolo[2,3-b]pyridin-4-yl]phenyl}amino)methyl]benzenesulfonamide The title compound was prepared essentially as described in Example 11B, substituting Example 179D (20 mg, 0.06 mmol) for Example 11A and 4-formylbenzenesulfonamide for benzaldehyde. $^1$H NMR (400 MHz, DMSO-d$_6$) δ 1.81 (qd, J=13.0, 12.3, 3.4 Hz, 2H), 2.13-2.33 (m, 2H), 2.82 (d, J=4.5 Hz, 3H), 2.98 (tt, J=12.1, 3.6 Hz, 1H), 3.05-3.19 (m, 2H), 3.55 (d, J=12.0 Hz, 2H), 4.39 (s, 2H), 5.95 (t, J=2.0 Hz, 1H), 6.99-7.15 (m, 2H), 7.30 (m, 2H), 7.55 (d, J=8.0 Hz, 2H), 7.80 (dd, J=8.4, 2.6 Hz, 2H), 8.21 (d, J=5.0 Hz, 1H). MS (ESI$^+$) m/z 494 (M+H)$^+$.

EXAMPLE 317

3-[({4-fluoro-3-[2-(1-methylpiperidin-4-yl)-1H-pyrrolo[2,3-b]pyridin-4-yl]phenyl}amino)methyl]phenol The title compound was prepared essentially as described in Example 11B, substituting Example 179D (20 mg, 0.06 mmol) for Example 11A and 3-hydroxybenzaldehyde for benzaldehyde. $^1$H NMR (400 MHz, DMSO-d$_6$) δ 1.70-1.88 (m, 2H), 2.24 (d, J=13.5 Hz, 2H), 2.83 (d, J=4.3 Hz, 3H), 2.90-3.03 (m, 1H), 3.03-3.22 (m, 2H), 3.55 (d, J=12.0 Hz, 2H), 4.21 (s, 2H), 5.95 (d, J=2.0 Hz, 1H), 6.60-6.73 (m, 2H), 6.78 (dd, J=4.7, 2.2 Hz, 2H), 6.99-7.15 (m, 3H), 7.31-7.47 (m, 1H), 8.20 (d, J=5.0 Hz, 1H). MS (ESI$^+$) m/z 431 (M+H)$^+$.

EXAMPLE 318

N-(3-chlorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 3-chlorobenzaldehyde for benzaldehyde. $^1$H NMR (400 MHz, DMSO-d$_6$) δ 1.75-1.87 (m, 2H), 2.20-2.29 (m, 2H), 2.82 (t, J=3.6 Hz, 3H), 2.98 (td, J=12.1, 10.4, 6.1 Hz, 1H), 3.12 (dt, J=12.9, 9.7 Hz, 2H), 3.55 (d, J=12.1 Hz, 2H), 4.32 (s, 2H), 5.93 (d, J=2.1 Hz, 1H), 6.70 (ddd, J=9.2, 6.6, 3.1 Hz, 2H), 6.98-7.16 (m, 2H), 7.28-7.46 (m, 4H), 8.21 (d, J=5.1 Hz, 1H). MS (ESI$^+$) m/z 449 (M+H)$^+$.

EXAMPLE 319

4-fluoro-N-(4-fluorobenzyl)-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 4-fluorobenzaldehyde for benzaldehyde. $^1$H NMR (400 MHz, DMSO-d$_6$) δ 1.80 (qd, J=13.4, 3.7 Hz, 2H), 2.21-2.30 (m, 2H), 2.82 (d, J=4.1 Hz, 3H), 2.92-3.21 (m, 3H), 3.54 (d, J=12.2 Hz, 2H), 4.28 (s, 2H), 5.96 (d, J=2.1 Hz, 1H), 6.70 (dd, J=7.4, 4.5 Hz, 2H), 6.98-7.22 (m, 4H), 7.35-7.46 (m, 2H), 8.21 (d, J=5.0 Hz, 1H). MS (ESI+) m/z 433 (M+H)+.

EXAMPLE 320

4-fluoro-N-(2-fluorobenzyl)-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 2-fluorobenzaldehyde for benzaldehyde. $^1$H NMR (400 MHz, DMSO-$d_6$) δ 1.79 (qd, J=13.5, 3.8 Hz, 2H), 2.20-2.35 (m, 2H), 2.82 (d, J=4.1 Hz, 3H), 2.92-3.23 (m, 3H), 3.55 (d, J=12.0 Hz, 2H), 4.34 (s, 2H), 5.97 (d, J=2.2 Hz, 1H), 6.73 (dd, J=7.9, 4.3 Hz, 2H), 7.02-7.24 (m, 4H), 7.33 (dtd, J=7.5, 5.6, 2.8 Hz, 1H), 7.39-7.48 (m, 1H), 8.21 (d, J=5.0 Hz, 1H). MS (ESI+) m/z 433 (M+H)+.

EXAMPLE 321

4-fluoro-N-(3-methoxybenzyl)-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 3-methoxybenzaldehyde for benzaldehyde. $^1$H NMR (400 MHz, DMSO-$d_6$) δ 1.80 (qd, J=13.6, 3.7 Hz, 2H), 2.25 (d, J=14.0 Hz, 2H), 2.83 (d, J=4.2 Hz, 3H), 2.99 (tt, J=12.3, 3.6 Hz, 1H), 3.11 (dt, J=14.1, 10.8 Hz, 2H), 3.50-3.59 (m, 2H), 3.72 (s, 3H), 4.27 (s, 2H), 5.97 (d, J=1.9 Hz, 1H), 6.67-6.76 (m, 2H), 6.82 (dd, J=8.1, 2.4 Hz, 1H), 6.91-6.98 (m, 2H), 6.99-7.17 (m, 2H), 7.25 (t, J=8.0 Hz, 1H), 8.21 (d, J=5.1 Hz, 1H). MS (ESI+) m/z 445 (M+H)+.

EXAMPLE 322

{4-[({4-fluoro-3-[2-(1-methylpiperidin-4-yl)-1H-pyrrolo[2,3-b]pyridin-4-yl]phenyl}amino)methyl]phenoxy}acetic acid The title compound was prepared essentially as described in Example 11B, substituting Example 179D (20 mg, 0.06 mmol) for Example 11A and 2-(4-formylphenoxy)acetic acid for benzaldehyde. $^1$H NMR (500 MHz, DMSO-$d_6$) δ 1.79 (qd, J=12.7, 11.9, 3.3 Hz, 2H), 2.23 (d, J=14.1 Hz, 2H), 2.80 (s, 3H), 2.97 (tt, J=12.3, 3.7 Hz, 1H), 3.04-3.20 (m, 2H), 3.53 (d, J=12.3 Hz, 2H), 4.21 (s, 2H), 4.63 (s, 2H), 5.92 (s, 1H), 6.67-6.75 (m, 2H), 6.88 (d, J=8.3 Hz, 2H), 7.00-7.20 (m, 2H), 7.23-7.30 (m, 2H), 8.19 (d, J=5.1 Hz, 1H). MS (ESI+) m/z 489 (M+H)+.

EXAMPLE 323

N-[(1,1-dioxidotetrahydro-2H-thiopyran-4-yl)methyl]-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and tetrahydro-2H-thiopyran-4-carbaldehyde 1,1-dioxide for benzaldehyde. $^1$H NMR (400 MHz, DMSO-$d_6$) δ 1.58-1.94 (m, 5H), 2.07-2.19 (m, 2H), 2.31 (d, J=14.2 Hz, 2H), 2.82 (d, J=4.5 Hz, 3H), 2.95-3.25 (m, 9H), 3.52 (s, 2H), 6.09 (s, 1H), 6.70 (td, J=8.5, 3.6 Hz, 2H), 7.03-7.15 (m, 2H), 8.22 (d, J=4.9 Hz, 1H). MS (ESI+) m/z 471 (M+H)+.

EXAMPLE 324

4-[4-(5-fluoro-2-methoxyphenyl)-1H-pyrrolo[2,3-b]pyridin-2-yl]tetrahydro-2H-thiopyran-4-ol 1,1-dioxide

EXAMPLE 324A 4-(4-(5-fluoro-2-methoxyphenyl)-1-tosyl-1H-pyrrolo[2,3-b]pyridin-2-yl)-4-hydroxytetrahydro-2H-thiopyran 1,1-dioxide To a solution of Example 258C (200 mg, 0.504 mmol) in tetrahydrofuran (1.5 mL) cooled to −78° C. was added n-butyllithium (0.473 mL, 0.757 mmol) under nitrogen. The reaction mixture was stirred for 10 minutes when dihydro-2H-thiopyran-4(3H)-one 1,1-dioxide (150 mg, 1.009 mmol) was added. The stirring was continued at −78° C. for 1 hour and then let slowly warm up to room temperature overnight. The reaction mixture was quenched with water and extracted with ethyl acetate. The organic layer was dried over magnesium sulfate, filtered and concentrated under vacuum. The crude material was purified by flash chromatography (silica gel, 20 to 100% ethyl acetate/heptanes) to provide the title compound.

EXAMPLE 324B

4-[4-(5-fluoro-2-methoxyphenyl)-1H-pyrrolo[2,3-b]pyridin-2-yl]tetrahydro-2H-thiopyran-4-ol 1,1-dioxide A suspension of Example 324A (113 mg, 0.207 mmol) and 50% NaOH (0.055 mL, 1.037 mmol)/water (0.064 mL) in dioxane (1 mL) was heated at 80° C. for 4 hours. The reaction mixture was diluted with ethyl acetate and dried over magnesium sulfate, filtered and concentrated under vacuum. The product was purified by reverse phase LC (C18, gradient 20 to 100% acetonitrile/water with 0.1% trifluoroacetic acid) providing the title compound which eluted as the first component. $^1$H NMR (300 MHz, DMSO-$d_6$) δ ppm 2.19-2.35 (m, 4H), 3.06 (d, J=13.3 Hz, 4H), 3.73 (s, 3H), 5.77 (s, 1H), 6.19 (d, J=2.1 Hz, 1H), 7.06 (d, J=5.1 Hz, 1H), 7.15-7.37 (m, 3H), 8.20 (d, J=5.0 Hz, 1H), 11.74 (s, 1H) MS (ESI+) m/z 391.1 (M+H)+.

EXAMPLE 325

2-(1,1-dioxido-3,6-dihydro-2H-thiopyran-4-yl)-4-(5-fluoro-2-methoxyphenyl)-1H-pyrrolo[2,3-b]pyridine A suspension of Example 324A (113 mg, 0.207 mmol) and 50% NaOH (0.055 mL, 1.037 mmol)/water (0.064 mL) in dioxane (1 mL) was heated at 80° C. for 4 hours. The reaction mixture was diluted with ethyl acetate and dried over magnesium sulfate, filtered and concentrated under vacuum. The crude material was purified by reverse phase LC (C18, gradient 20 to 100% acetonitrile/water with 0.1% trifluoroacetic acid), providing the title compound which eluted as the second component. $^1$H NMR (500 MHz, DMSO-$d_6$) δ ppm 3.07 (t, J=6.4 Hz, 2H), 3.35 (t, J=6.3 Hz, 2H), 3.75 (s, 3H), 3.97 (d, J=4.3 Hz, 2H), 6.36-6.46 (m, 2H), 7.09 (d, J=4.9 Hz, 1H), 7.16-7.34 (m, 3H), 8.25 (d, J=5.0 Hz, 1H), 11.99 (d, J=2.3 Hz, 1H). MS (ESI+) m/z 373.2 (M+H)⁺.

EXAMPLE 326

3-[4-(5-fluoro-2-methoxyphenyl)-1H-pyrrolo[2,3-b]pyridin-2-yl]pyrrolidin-3-ol

EXAMPLE 326A tert-butyl 3-(4-(5-fluoro-2-methoxyphenyl)-1-tosyl-1H-pyrrolo[2,3-b]pyridin-2-yl)-3-hydroxypyrrolidine-1-carboxylate The title compound was prepared according the procedure described in Example 324A, using 3-pyrrolidinone in place of dihydro-2H-thiopyran-4(3H)-one 1,1-dioxide.

EXAMPLE 326B tert-butyl 3-(4-(5-fluoro-2-methoxyphenyl)-1H-pyrrolo[2,3-b]pyridin-2-yl)-3-hydroxypyrrolidine-1-carboxylate The title compound was prepared according the procedure described in Example 324B, using Example 326A in place of Example 324A.

EXAMPLE 326C

3-[4-(5-fluoro-2-methoxyphenyl)-1H-pyrrolo[2,3-b]pyridin-2-yl]pyrrolidin-3-ol

A solution of Example 326B (2.77 g, 6.49 mmol) and trifluoroacetic acid (0.5 mL, 6.49 mmol) in dichloromethane (1 mL) was stirred at room temperature for 2 hours. The reaction mixture was concentrated and the product purified by RP HPLC (C18, gradient 0-50% acetonitrile/water with 0.1% trifluoroacetic acid). $^1$H NMR (300 MHz, DMSO-d$_6$) δ ppm 2.18-2.41 (m, 2H), 3.73 (s, 4H), 6.09 (s, 1H), 6.28 (d, J=2.0 Hz, 1H), 7.08 (d, J=4.7 Hz, 1H), 7.16-7.38 (m, 3H), 8.24 (d, J=5.1 Hz, 1H), 9.13 (d, J=53.8 Hz, 2H), 11.83 (d, J=2.4 Hz, 1H) MS (ESI⁺) m/z 327.9 (M+H)⁺.

EXAMPLE 327

2-(2,5-dihydro-1H-pyrrol-3-yl)-4-(5-fluoro-2-methoxyphenyl)-1H-pyrrolo[2,3-b]pyridine The title compound was isolated as a by-product in Example 326B. $^1$H NMR (500 MHz, DMSO-d$_6$) δ ppm 3.74 (s, 3H), 4.19 (d, J=4.8 Hz, 2H), 4.34 (d, J=5.9 Hz, 2H), 6.41 (d, J=2.0 Hz, 1H), 6.48-6.55 (m, 1H), 7.10 (d, J=5.0 Hz, 1H), 7.18-7.35 (m, 3H), 8.29 (d, J=4.9 Hz, 1H), 9.22-9.38 (m, 2H), 12.21 (d, J=2.3 Hz, 1H). MS (ESI⁺) m/z 310.1 (M+H)⁺.

EXAMPLE 328

4-fluoro-N-(3-fluorobenzyl)-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 3-fluorobenzaldehyde for benzaldehyde. $^1$H NMR (500 MHz, DMSO-d$_6$) δ 1.79 (dd, J=13.0, 3.6 Hz, 2H), 2.24 (d, J=14.1 Hz, 2H), 2.82 (d, J=4.5 Hz, 3H), 2.97 (m, 1H), 3.03-3.20 (m, 2H), 3.55 (d, J=12.1 Hz, 2H), 4.33 (s, 2H), 5.91 (s, 1H), 6.69 (ddd, J=9.4, 6.8, 3.1 Hz, 2H), 7.02 (dd, J=4.3, 1.9 Hz, 1H), 7.09 (ddd, J=14.6, 7.9, 4.0 Hz, 2H), 7.14-7.26 (m, 2H), 7.33-7.44 (m, 1H), 8.20 (d, J=4.8 Hz, 1H). MS (ESI⁺) m/z 433 (M+H)⁺.

EXAMPLE 329

N-(2,4-difluorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 2,4-difluorobenzaldehyde for benzaldehyde. $^1$H NMR (500 MHz, DMSO-d$_6$) δ 1.71-1.87 (m, 2H), 2.19-2.37 (m, 2H), 2.82 (d, J=4.3 Hz, 3H), 2.94-3.02 (m, 1H), 3.11 (dt, J=13.0, 9.8 Hz, 2H), 3.48-3.60 (m, 2H), 4.30 (s, 2H), 5.98 (q, J=4.1, 3.1 Hz, 1H), 6.71 (dd, J=6.3, 3.1 Hz, 2H), 6.97-7.19 (m, 2H), 7.20-7.29 (m, 2H), 7.46 (td, J=8.7, 6.7 Hz, 1H), 8.21 (d, J=5.0 Hz, 1H). MS (ESI⁺) m/z 451 (M+H)⁺.

EXAMPLE 330

N-(2,6-difluorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 2,6-difluorobenzaldehyde for benzaldehyde. $^1$H NMR (500 MHz, DMSO-d$_6$) δ 1.81 (qd, J=13.5, 3.8 Hz, 2H), 2.21-2.36 (m, 2H), 2.81 (d, J=4.4 Hz, 3H), 3.02 (ddt, J=12.1, 8.5, 3.6 Hz, 1H), 3.11 (dt, J=13.4, 10.1 Hz, 2H), 3.54 (d, J=12.1 Hz, 2H), 4.29 (s, 2H), 6.07 (t, J=2.2 Hz, 1H), 6.72-6.84 (m, 2H), 7.00-7.07 (m, 2H), 7.08-7.15 (m, 2H), 7.35-7.46 (m, 1H), 8.22 (d, J=5.0 Hz, 1H). MS (ESI⁺) m/z 451 (M+H)⁺.

EXAMPLE 335

N-(2,5-difluorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 2,5-difluorobenzaldehyde for benzaldehyde. $^1$H NMR (400 MHz, DMSO-d$_6$) δ 1.79 (ddq, J=17.0, 9.4, 3.8 Hz, 2H), 2.21-2.30 (m, 2H), 2.82 (d, J=4.3 Hz, 3H), 2.92-3.22 (m, 3H), 3.55 (d, J=12.1 Hz, 2H), 4.34 (s, 2H), 5.97 (q, J=3.2, 2.0 Hz, 1H), 6.72 (td, J=6.4, 5.6, 3.1 Hz, 2H), 6.98-7.34 (m, 5H), 8.21 (d, J=5.1 Hz, 1H). MS (ESI⁺) m/z 451 (M+H)⁺.

EXAMPLE 337

N-(2-chlorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 2-chlorobenzaldehyde for benzaldehyde. $^1$H NMR (400 MHz, DMSO-d$_6$) δ 1.71-1.85 (m, 2H), 2.18-2.27 (m, 2H), 2.82 (d, J=4.3 Hz, 3H), 2.91-3.20 (m, 3H), 3.55 (d, J=12.0 Hz, 2H), 4.36 (s, 2H), 5.94 (t, J=1.8 Hz, 1H), 6.62-6.74 (m, 2H), 6.99-7.17 (m, 2H), 7.25-7.39 (m, 2H), 7.46 (dt, J=7.2, 1.8 Hz, 2H), 8.20 (d, J=5.0 Hz, 1H). MS (ESI⁺) m/z 449 (M+H)⁺.

EXAMPLE 338

3-[({4-fluoro-3-[2-(1-methylpiperidin-4-yl)-1H-pyrrolo[2,3-b]pyridin-4-yl]phenyl}amino)methyl]benzoic acid The title compound was prepared essentially as described in Example 11B, substituting Example 179D (20 mg, 0.06 mmol) for Example 11A and 3-formylbenzoic acid for benzaldehyde. $^1$H NMR (400 MHz, DMSO-$d_6$) δ 1.71-1.87 (m, 2H), 2.11-2.31 (m, 2H), 2.82 (t, J=3.8 Hz, 3H), 2.90-3.20 (m, 3H), 3.54 (d, J=12.2 Hz, 2H), 4.37 (s, 2H), 5.92 (t, J=2.0 Hz, 1H), 6.71 (ddd, J=11.8, 6.6, 3.0 Hz, 2H), 6.97-7.15 (m, 2H), 7.47 (t, J=7.6 Hz, 1H), 7.62 (d, J=7.6 Hz, 1H), 7.84 (d, J=7.7 Hz, 1H), 7.98 (t, J=1.7 Hz, 1H), 8.20 (d, J=5.0 Hz, 1H). MS (ESI$^+$) m/z 459 (M+H)$^+$.

EXAMPLE 339

4-[({4-fluoro-3-[2-(1-methylpiperidin-4-yl)-1H-pyrrolo[2,3-b]pyridin-4-yl]phenyl}amino)methyl]benzonitrile The title compound was prepared essentially as described in Example 11B, substituting Example 179D (20 mg, 0.06 mmol) for Example 11A and 4-formylbenzonitrile for benzaldehyde. $^1$H NMR (400 MHz, DMSO-$d_6$) δ 1.80 (qd, J=13.5, 4.4 Hz, 2H), 2.19-2.32 (m, 2H), 2.83 (d, J=4.1 Hz, 3H), 2.99 (td, J=12.3, 10.3, 6.1 Hz, 1H), 3.05-3.21 (m, 2H), 3.56 (d, J=12.1 Hz, 2H), 4.41 (s, 2H), 5.93 (d, J=2.1 Hz, 1H), 6.68 (tt, J=7.8, 3.9 Hz, 2H), 6.98-7.20 (m, 2H), 7.57 (d, J=8.0 Hz, 2H), 7.76-7.89 (m, 2H), 8.22 (d, J=5.0 Hz, 1H). MS (ESI$^+$) m/z 440 (M+H)$^+$.

EXAMPLE 340

2-[({4-fluoro-3-[2-(1-methylpiperidin-4-yl)-1H-pyrrolo[2,3-b]pyridin-4-yl]phenyl}amino)methyl]benzonitrile The title compound was prepared essentially as described in Example 11B, substituting Example 179D (20 mg, 0.06 mmol) for Example 11A and 2-formylbenzonitrile for benzaldehyde. $^1$H NMR (400 MHz, DMSO-$d_6$) δ 1.73-1.92 (m, 2H), 2.26-2.34 (m, 2H), 2.83 (d, J=4.1 Hz, 3H), 3.00-3.20 (m, 3H), 3.50-3.58 (m, 2H), 5.32 (s, 2H), 6.21 (t, J=2.4 Hz, 1H), 7.19 (d, J=5.1 Hz, 1H), 7.66-7.79 (m, 2H), 7.77-8.01 (m, 4H), 8.31 (dd, J=13.5, 6.5 Hz, 2H). MS (ESI$^+$) m/z 440 (M+H)$^+$.

EXAMPLE 341

3-[({4-fluoro-3-[2-(1-methylpiperidin-4-yl)-1H-pyrrolo[2,3-b]pyridin-4-yl]phenyl}amino)methyl]benzonitrile The title compound was prepared essentially as described in Example 11B, substituting Example 179D (20 mg, 0.06 mmol) for Example 11A and 3-formylbenzonitrile for benzaldehyde. $^1$H NMR (400 MHz, DMSO-$d_6$) δ 1.70-1.88 (m, 2H), 2.14-2.34 (m, 2H), 2.83 (d, J=4.5 Hz, 3H), 2.92-3.23 (m, 3H), 3.55 (d, J=11.6 Hz, 2H), 4.38 (s, 2H), 5.94 (q, J=2.9, 2.1 Hz, 1H), 6.66-6.76 (m, 2H), 7.00-7.20 (m, 3H), 7.45-7.81 (m, 3H), 8.22 (d, J=5.0 Hz, 1H). MS (ESI$^+$) m/z 440 (M+H)$^+$.

EXAMPLE 342 trans-4-[4-(5-fluoro-2-methoxyphenyl)-1H-pyrrolo[2,3-b]pyridin-2-yl]-N-{[1-(methoxymethyl)-1H-1,2,3-triazol-4-yl]methyl}cyclohexanamine The title compound was prepared using the procedure described in Example 120 using a 1:1 mixture of 1-(methoxymethyl)-1H-1,2,3-triazole-4-carboxaldehyde and 1-(methoxymethyl)-1H-1,2,3-triazole-5-carboxaldehyde in place of 4-oxobutanoic acid methyl ester. A mixture of two regioisomers was separated by reverse phase-HPLC (Sunfire 5 μM, 50×250 mm) eluting with 5-50% acetonitrile in water (containing 0.1% trifluoroacetic acid) to provide the title compound as the trifluoroacetate salt. $^1$H NMR (400 MHz, DMSO-$d_6$) δ 1.55 (m, 4H), 2.15 (m, 2H), 2.26 (m, 2H), 2.75 (m, 1H), 3.13 (m, 1H), 3.30 (s, 3H), 3.74 (s, 3H), 4.38 (m, 2H), 5.74 (s, 2H), 6.02 (s, 1H), 7.07 (d, 1H), 7.25 (m, 3H), 8.17 (d, 1H), 8.38 (s, 1H), 11.72 (br s, 1H). (ESI) m/e 465.1 (M+H)$^+$.

EXAMPLE 343 trans-4-[4-(5-fluoro-2-methoxyphenyl)-1H-pyrrolo[2,3-b]pyridin-2-yl]-N-{[1-(methoxymethyl)-1H-1,2,3-triazol-5-yl]methyl}cyclohexanamine The title compound was prepared using the procedure described in Example 120 using 1-(methoxymethyl)-1H-1,2,3-triazole-4-carboxaldehyde in place of 4-oxobutanoic acid methyl ester. A mixture of two regioisomers was separated by reverse phase-HPLC (Sunfire 5 μM, 50×250 mm) eluting with 5-50% acetonitrile in water (containing 0.1% trifluoroacetic acid) to provide the title compound as the trifluoroacetate salt. $^1$H NMR (400 MHz, DMSO-$d_6$) δ 1.54 (m, 4H), 2.15 (m, 2H), 2.25 (m, 2H), 2.75 (m, 1H), 3.14 (m, 1H), 3.33 (s, 3H), 3.73 (s, 3H), 4.40 (m, 2H), 5.68 (s, 2H), 6.01 (s, 1H), 7.07 (d, 1H), 7.55 (m, 3H), 8.00 (s, 1H), 8.17 (d, 1H), 11.72 (br s, 1H). (ESI) m/e 465.1 (M+H)$^+$.

EXAMPLE 344

2,4-difluoro-N-[(4-methyltetrahydro-2H-pyran-4-yl)methyl]-5-[2-(piperidin-4-yl)-1H-pyrrolo[2,3-b]pyridin-4-yl]aniline

EXAMPLE 344A tert-butyl 4-(4-(5-amino-2,4-difluorophenyl)-1H-pyrrolo[2,3-b]pyridin-2-yl)piperidine-1-carboxylate A mixture of 5-bromo-2,4-difluoroaniline (335 mg, 1.61 mmol), 4,4,4',4',5,5,5',5'-octamethyl-2,2'-bi(1,3,2-dioxaborolane) (450 mg, 1.77 mmol) and potassium acetate (474 mg, 4.83 mmol) in dioxane (7 ml) was purged with nitrogen gas for 5 minutes and [1,1'-bis(diphenylphosphino)ferrocene]dichloropalladium(II) dichloromethane adduct (79 mg, 0.10 mmol) was added. The reaction mixture was heated at 100° C. overnight and cooled. To this mixture was added Example 17E (541 mg, 1.61 mmol), tricyclohexylphosphine (27.1 mg, 0.10 mmol), bis(triphenylphosphine)palladium(II) dichloride (67.8 mg, 0.097 mmol), cesium carbonate (1.57 g, 4.83 mmol), 8 mL of dioxane, and 1 mL of 1 M Na$_2$CO$_3$ in water solution added. The resulting mixture was heated at 100° C. overnight, cooled. diluted with ethyl acetate and washed with water. The organic layer was dried over Na$_2$SO$_4$, filtered, and concentrated. The residue was purified by flash chromatography, and was eluted with a gradient of 0%-100% ethyl acetate in hexanes to provide the title compound. LCMS: 429 (M+H)+.

EXAMPLE 344B tert-butyl 4-(4-(2,4-difluoro-5-(((4-methyltetrahydro-2H-pyran-4-yl)methyl)amino)phenyl)-1H-pyrrolo[2,3-b]pyridin-2-yl)piperidine-1-carboxylate To a mixture of Example 344A (50 mg, 0.12 mmol), 4-methyltetrahydro-2H-pyran-4-carbaldehyde (150 mg, 1.17 mmol) and MP-cyanoborohydride (2.49 mmol/g, 289 mg) in dichloromethane was added acetic acid (0.1 mL). The mixture was stirred at room temperature overnight and concentrated. The residue was purified by flash chromatography, and was eluted with a gradient of 0%-70% ethyl acetate in hexanes to provide the title compound. LCMS: 541 (M+H)+.

EXAMPLE 344C 2,4-difluoro-N-[(4-methyltetrahydro-2H-pyran-4-yl)methyl]-5-[2-(piperidin-4-yl)-1H-pyrrolo[2,3-b]pyridin-4-yl]aniline Example 344B (30 mg, 0.05 mmol) in dichloromethane (3 mL) was treated with trifluoroacetic acid (1 mL) for 10 minutes. The reaction mixture was concentrated and the residue was purified by reverse phase chromatography (C18 column), and was eluted with a gradient of 10%-70% acetonitrile in 0.1% trifluoroacetic acid water solution to provide the title compound. $^1$H NMR (400 MHz, DMSO-$d_6$) δ ppm 1.03 (s, 3 H) 1.25 (d, 2 H) 1.50-1.60 (m, 2 H) 1.72-1.85 (m, 2 H) 2.23 (d, 2 H) 2.97-3.13 (m, 5 H) 3.37 (d, 2 H) 3.45-3.55 (m, 2 H) 3.59-3.69 (m, 2 H) 6.07 (s, 1 H) 6.93 (dd, 1 H) 7.07 (d, 1 H) 7.27 (dd, 1 H) 8.23 (d, 1 H) 8.39 (s, 1 H) 8.69 (d, 1 H) 11.86 (s, 1 H); LCMS: 441 (M+H)+.

EXAMPLE 345

N-benzyl-2,4-difluoro-5-[2-(piperidin-4-yl)-1H-pyrrolo[2,3-b]pyridin-4-yl]aniline

EXAMPLE 345A tert-butyl 4-(4-(5-(benzylamino)-2,4-difluorophenyl)-1H-pyrrolo[2,3-b]pyridin-2-yl)piperidine-1-carboxylate The title compound was prepared using the procedure described in Example 344B, using benzaldehyde in place of 4-methyltetrahydro-2H-pyran-4-carbaldehyde. LCMS: 519 (M+H)+.

EXAMPLE 345B

N-benzyl-2,4-difluoro-5-[2-(piperidin-4-yl)-1H-pyrrolo[2,3-b]pyridin-4-yl]aniline The title compound was prepared as the trifluoroacetate salt using the procedure described in Example 344C, using Example 345A in place of Example 344B. $^1$H NMR (400 MHz, DMSO-$d_6$) δ ppm 1.60-1.84 (m, 2 H) 2.12 (d, 2 H) 2.91-3.12 (m, 3 H) 3.38 (d, 2 H) 4.38 (s, 2 H) 5.75 (s, 1 H) 6.66 (dd, 1 H) 6.95 (dd, 1 H) 7.18-7.40 (m, 6 H) 8.16 (d, 1 H) 8.35 (d, 1 H) 8.70 (d, 1 H) 11.79 (s, 1 H); LCMS: 419 (M+H)+.

EXAMPLE 346

2,4-difluoro-5-[2-(piperidin-4-yl)-1H-pyrrolo[2,3-b]pyridin-4-yl]-N-(tetrahydro-2H-pyran-4-ylmethyl)aniline

EXAMPLE 346A tert-butyl 4-(4-(2,4-difluoro-5-(((tetrahydro-2H-pyran-4-yl)methyl)amino)phenyl)-1H-pyrrolo[2,3-b]pyridin-2-yl)piperidine-1-carboxylate The title compound was prepared using the procedure described in Example 344B, using tetrahydro-2H-pyran-4-carbaldehyde in place of 4-methyltetrahydro-2H-pyran-4-carbaldehyde. LCMS: 527 (M+H)+.

EXAMPLE 346B 2,4-difluoro-5-[2-(piperidin-4-yl)-1H-pyrrolo[2,3-b]pyridin-4-yl]-N-(tetrahydro-2H-pyran-4-ylmethyl)aniline The title compound was prepared as the trifluoroacetate salt using the procedure described in Example 344C, using Example 346A in place of Example 344B. $^1$H NMR (400 MHz, DMSO-$d_6$) δ ppm 1.13-1.27 (m, 2 H) 1.61-1.68 (m, 2 H) 1.71-1.91 (m, 3 H) 2.24 (d, 2 H) 2.97-3.13 (m, 5 H) 3.26 (t, 2 H) 3.37 (d, 2 H) 6.09 (s, 1 H) 6.80 (dd, 1 H) 7.08 (d, 1 H) 7.26 (dd, 1 H) 8.22 (d, 1 H) 8.34 (d, 1 H) 8.64 (d, 1 H) 11.83 (s, 1 H); LCMS: 419 (M+H)+.

EXAMPLE 347

2,4-difluoro-N-(3-fluorobenzyl)-5-[2-(piperidin-4-yl)-1H-pyrrolo[2,3-b]pyridin-4-yl]aniline

EXAMPLE 347A tert-butyl 4-(4-(2,4-difluoro-5-((3-fluorobenzyl)amino)phenyl)-1H-pyrrolo[2,3-b]pyridin-2-yl)piperidine-1-carboxylate The title compound was prepared using the procedure described in Example 344B, using 3-fluorobenzaldehyde in place of 4-methyltetrahydro-2H-pyran-4-carbaldehyde. LCMS: 537 (M+H)+.

EXAMPLE 347B 2,4-difluoro-N-(3-fluorobenzyl)-5-[2-(piperidin-4-yl)-1H-pyrrolo[2,3-b]pyridin-4-yl]aniline The title compound was prepared as the trifluoroacetate salt using the procedure described in Example 344C, using Example 347A in place of Example 344B. $^1$H NMR (400 MHz, DMSO-$d_6$) δ ppm 1.64-1.82 (m, 2 H) 2.12 (d, 2 H) 2.92-3.14 (m, 3 H) 3.38 (d, 2 H) 4.40 (s, 2 H) 5.73 (s, 1 H) 6.66 (dd, 1 H) 6.95 (dd, 1 H) 7.05-7.24 (m, 3 H) 7.24-7.44 (m, 2 H) 8.16 (d, 1 H) 8.31 (d, 1 H) 8.66 (d, 1 H) 11.78 (s, 1 H); LCMS: 437 (M+H)+.

EXAMPLE 353

N-(3-chlorobenzyl)-4-fluoro-3-[2-(piperidin-4-yl)-1H-pyrrolo[2,3-b]pyridin-4-yl]aniline

EXAMPLE 353A tert-butyl 4-(4-(5-amino-2-fluorophenyl)-1H-pyrrolo[2,3-b]pyridin-2-yl)piperidine-1-carboxylate The title compound was prepared essentially as described in Examples 1 G, substituting 4-fluoro-3-(4,4,5,5-tetramethyl-1,3,2-dioxaborolan-2-yl)aniline (212 mg, 0.9 mmol) for 5-fluoro-2-methoxyphenylboronic acid and Example 17E (200 mg, 0.6 mmol) for Example 1F. MS (ESI+) m/z 411 (M+H)+.

EXAMPLE 353B

N-(3-chlorobenzyl)-4-fluoro-3-[2-(piperidin-4-yl)-1H-pyrrolo[2,3-b]pyridin-4-yl]aniline The title compound was prepared essentially as described in Examples 11B and 1H, substituting Example 353A (35 mg, 0.09 mmol) for Example 11A, and 3-chlorobenzaldehyde for benzaldehyde in Example 11B. The Boc-protected compound was then treated as described in Example 1H, to provide the title compound. $^1$H NMR (400 MHz, DMSO-$d_6$) δ 1.78 (qd, J=13.3, 12.8, 3.8 Hz, 2H), 2.19 (dd, J=14.5, 3.8 Hz, 2H), 3.06 (m, 3H), 3.39 (d, J=12.5 Hz, 2H), 4.32 (s, 2H), 5.96 (s, 1H), 6.71 (dd, J=6.8, 3.6 Hz, 2H), 6.99-7.17 (m, 2H), 7.21-7.45 (m, 4H), 8.22 (d, J=5.1 Hz, 1H). MS (ESI+) m/z 435 (M+H)+.

EXAMPLE 354

4-fluoro-N-(3-fluorobenzyl)-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 3-fluorobenzaldehyde for benzaldehyde in Example 11B. The Boc-protected compound was then treated as described in Example 1H, to provide the title compound. $^1$H NMR (400 MHz, DMSO-$d_6$) δ 1.73-1.81 (m, 2H), 2.17 (m, 2H), 3.01-3.09 (m, 3H), 3.37 (m, 2H), 4.32 (s, 2H), 5.95 (s, 1H), 6.69 (s, 2H), 7.02-7.11 (m, 3H), 7.20 (d, J=13.9 Hz, 2H), 7.37 (s, 1H), 8.21 (s, 1H). MS (ESI+) m/z 419 (M+H)+.

EXAMPLE 355

4-[({4-fluoro-3-[2-(piperidin-4-yl)-1H-pyrrolo[2,3-b]pyridin-4-yl]phenyl}amino)methyl]benzonitrile The title compound was prepared essentially as described in Examples 11B and 1H, substituting Example 353A (30 mg, 0.07 mmol) for Example 11A and 4-formylbenzonitrile for benzaldehyde in Example 11B. The Boc-protected compound was then treated as described in Example 1H, to provide the title compound. $^1$H NMR (400 MHz, DMSO-$d_6$) δ 1.64-1.92 (m, 2H), 2.02-2.29 (m, 2H), 3.05 (d, J=14.8 Hz, 3H), 3.38 (m, 2H), 4.40 (s, 2H), 5.89 (s, 1H), 6.66 (m, 1H), 7.07 (d, J=20.0 Hz, 3H), 7.55 (m, 2H), 7.81 (m, 2H), 8.21 (m, 1H). MS (ESI+) m/z 426 (M+H)+.

EXAMPLE 356

4-fluoro-N-[4-(methylsulfonyl)benzyl]-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 4-(methylsulfonyl)benzaldehyde for benzaldehyde in Example 11B. The Boc-protected compound was then treated as described in Example 1H, to provide the title compound. $^1$H NMR (400 MHz, DMSO-$d_6$) δ 1.77 (d, J=18.7 Hz, 2H), 2.16 (d, J=13.7 Hz, 2H), 2.49 (s, 3H), 2.84-3.23 (m, 3H), 3.37 (m, 2H), 4.61 (s, 2H), 5.92 (s, 1H), 6.68 (s, 1H), 7.06 (d, J=38.6 Hz, 2H), 7.90 (s, 1H), 8.06-8.34 (m, 1H), 8.82 (s, 4H). MS (ESI+) m/z 479 (M+H)+.

EXAMPLE 357

4-fluoro-3-[2-(piperidin-4-yl)-1H-pyrrolo[2,3-b]pyridin-4-yl]-N-(pyridin-4-ylmethyl)aniline The title compound was prepared essentially as described in Examples 11B and 1H, substituting Example 353A (30 mg, 0.07 mmol) for Example 11A and isonicotinaldehyde for benzaldehyde in Example 11B. The Boc-protected compound was then treated as described in Example 1H, to provide the title compound. $^1$H NMR (400 MHz, DMSO-$d_6$) δ 1.65-1.90 (m, 2H), 2.04-2.28 (m, 2H), 2.99-3.10 (m, 3H), 3.32-3.50 (m, 2H), 4.42 (s, 2H), 6.69 (s, 2H), 7.07 (d, J=20.3 Hz, 2H), 7.62 (s, 2H), 7.89 (s, 2H), 8.30 (d, J=72.8 Hz, 1H), 8.61-8.93 (m, 1H). MS (ESI+) m/z 402 (M+H)+.

EXAMPLE 358

3-[4-(5-fluoro-2-methoxyphenyl)-1H-pyrrolo[2,3-b]pyridin-2-yl]azetidin-3-ol

EXAMPLE 358A tert-butyl 3-(4-chloro-1H-pyrrolo[2,3-b]pyridin-2-yl)-3-hydroxyazetidine-1-carboxylate To a solution of 4-chloro-2-iodo-1-tosyl-1H-pyrrolo[2,3-b]pyridine (1 g, 2.311 mmol) in tetrahydrofuran (1.5 mL) cooled to −78° C. was added n-butyllithium (3.03 mL, 4.85 mmol) under nitrogen. The reaction mixture was stirred for 2 minutes and then tert-butyl 3-oxoazetidine-1-carboxylate (0.791 g, 4.62 mmol) was added. The stirring was continued at −78° C. for 1 hour and the mixture was warmed slowly to room temperature overnight. The reaction mixture was quenched with water and extracted with ethyl acetate. The organic layer was dried over magnesium sulfate, filtered and concentrated under vacuum to provide the title compound.

EXAMPLE 358B tert-butyl 3-(4-(5-fluoro-2-methoxyphenyl)-1H-pyrrolo[2,3-b]pyridin-2-yl)-3-hydroxyazetidine-1-carboxylate A suspension of potassium phosphate (325 mg, 1.529 mmol), phenylallylchloro[1,3-bis(diisopropylphenyl)-2-imidazol-2-ylidene]palladium(II) (33.0 mg, 0.051 mmol), Example 358A (165 mg, 0.510 mmol) and (5-fluoro-2-methoxyphenyl)boronic acid (113 mg, 0.662 mmol) in tetrahydrofuran (1.5 mL) was heated under microwave conditions (Biotag Initiator, model 355302) at 60° C. for 150 minutes. The reaction mixture was diluted with ethyl acetate, the aqueous layer was separated and the organic layer was dried over magnesium sulfate, filtered and concentrated. The crude material was purified by flash chromatography (silica 24 g, 20%-100% etac/hexanes) to provide the title compound.

EXAMPLE 358C

3-[4-(5-fluoro-2-methoxyphenyl)-1H-pyrrolo[2,3-b]pyridin-2-yl]azetidin-3-ol

A suspension of Example 358B (0.16 g, 0.387 mmol) and trifluoroacetic acid (0.5 mL, 6.49 mmol) in dichloromethane (1.5 mL) was stirred at room temperature for 2 hours. Purification by reverse phase chromatography (40 g C18, gradient 20 to 60% $CH_3CN$/water/0.1% trifluoroacetic acid) provided the title compound. $^1H$ NMR (400 MHz, DMSO-$d_6$) δ ppm 3.56 (s, 1H), 3.92 (s, 2H), 4.13 (ddd, J=11.8, 7.4, 4.9 Hz, 2H), 4.42 (ddd, J=11.6, 6.9, 4.1 Hz, 2H), 6.48 (d, J=1.8 Hz, 1H), 7.12 (d, J=5.0 Hz, 1H), 7.18-7.37 (m, 3H), 8.28 (d, J=4.9 Hz, 1H), 8.83 (s, 1H), 9.22 (s, 1H), 11.94 (d, J=2.3 Hz, 1H). MS (ESI$^+$) m/z 314.0 (M+H)$^+$.

EXAMPLE 359

4-[4-(5-fluoro-2-methoxyphenyl)-1H-pyrrolo[2,3-b]pyridin-2-yl]-1-(methylsulfonyl)piperidin-4-ol The title compound was prepared as described in Example 119, substituting Example 126 for Example 87D. $^1H$ NMR (400 MHz, DMSO-$d_6$) δ ppm 1.92 (d, J=13.4 Hz, 2H), 2.10 (td, J=12.9, 4.5 Hz, 2H), 2.89 (s, 3H), 3.12 (td, J=11.9, 2.7 Hz, 2H), 3.43 (dt, J=11.8, 3.7 Hz, 2H), 3.74 (s, 3H), 6.24 (d, J=1.9 Hz, 1H), 7.06-7.36 (m, 4H), 8.24 (d, J=5.2 Hz, 1H), 11.95 (d, J=2.3 Hz, 1H). MS (ESI$^+$) m/z 420.0 (M+H)$^+$.

EXAMPLE 360

2-(1-benzylpiperidin-4-yl)-4-(5-fluoro-2-methoxyphenyl)-1H-pyrrolo[2,3-b]pyridine In a 20 mL vial a solution of Example 135B (26 mg, 0.07 mmol) dissolved in dichloromethane:methanol (1:1, 1.0 mL) was added, followed by the addition of benzaldehyde (13.78 mg, 0.13 mmol) dissolved in dichloromethane:methanol (1:1, 0.4 mL), followed by acetic acid (19 μL, 0.33 mmol). The vial was capped and stirred at 50° C. for 15 minutes. After that, MP-cyanoborohydride resin (291 mg, 0.65 mmol) was added, and the mixture was shaken at 50° C. overnight. The reaction was filtered, concentrated to dryness, dissolved in 1:1 DMSO/methanol, and purified by preparative HPLC on a Phenomenex Luna C8(2) 5 um 100 Å AXIA column (30 mm×75 mm) to provide the title compound as a trifluoroacetic acid salt. A gradient of acetonitrile (A) and 0.1% trifluoroacetic acid in water (B) was used, at a flow rate of 50 mL/min (0-0.5 min 10% A, 0.5-6.0 min linear gradient 10-100% A, 6.0-7.0 min 100% A, 7.0-8.0 min linear gradient 100-10% A). $^1H$ NMR (400 MHz, pyridine-$d_5$) δ ppm 2.08-2.27 (m, 4H), 2.36 (t, J=11.2 Hz, 2H), 2.90-3.03 (m, 1H), 3.14 (d, J=11.4 Hz, 2H), 3.71 (s, 3H), 3.75 (s, 2H), 6.39 (s, 1H), 7.09 (dd, J=9.1, 4.5 Hz, 1H), 7.23-7.29 (m, 1H), 7.31-7.36 (m, 2H), 7.37-7.44 (m, 2H), 7.48 (dd, J=9.0, 3.2 Hz, 1H), 7.53 (d, J=7.2 Hz, 2H), 8.57 (d, J=4.9 Hz, 1H), 12.86 (s, 1H); MS (ESI) m/z 416 (M+H)$^+$.

EXAMPLE 361

4-(5-fluoro-2-methoxyphenyl)-2-(1-methyl-1,2,3,6-tetrahydropyridin-4-yl)-1H-pyrrolo[2,3-b]pyridine To a mixture of Example 87D (60.0 mg, 0.151 mmol), triethylamine (0.046 mL, 0.333 mmol), and acetic acid (0.043 mL, 0.757 mmol) in dichloromethane (3 mL) was added formaldehyde (37% in water) (0.022 mL, 0.757 mmol) and MP-cyanoborohydride (243 mg, 0.606 mmol). The reaction mixture was stirred for 5 hours. The solid material was filtered and rinsed with dichloromethane/methanol. The filtrate was concentrated and purified by reverse-phase HPLC performed on a Zorbax RX-C18 column using a gradient of 15-100% methanol in 0.1% aqueous trifluoroacetic acid at a flow rate of 15 mL/minute to afford the title compound as a trifluoroacetic acid salt. $^1H$ NMR (400 MHz, methanol-$d_4$) δ ppm 2.91-2.99 (m, 2H), 3.03 (s, 3H), 3.34-3.47 (m, 1H), 3.66-3.79 (m, 1H), 3.80 (s, 3H), 3.85-4.25 (m, 2H), 6.50 (bs, 1H), 6.63 (s, 1H), 7.18-7.31 (m, 3H), 7.41 (d, J=5.7 Hz, 1H), 8.32 (d, J=5.7 Hz, 1H). MS (ESI) m/z 338.1 (M+H)$^+$.

EXAMPLE 362

4-fluoro-3-{2-[1-(methylsulfonyl)-1,2,3,6-tetrahydropyridin-4-yl]-1H-pyrrolo[2,3-b]pyridin-4-yl}aniline

EXAMPLE 362A 4-chloro-2-(1-(methylsulfonyl)-1,2,3,6-tetrahydropyridin-4-yl)-1H-pyrrolo[2,3-b]pyridine The title compound was prepared essentially as described in Example 220A-F, substituting 4-chloro-1H-pyrrolo[2,3-b]pyridine for 4-bromo-1H-pyrrolo[2,3-b]pyridine in Example 220A. MS (APCI) m/z 312.0 (M+H)$^+$.

EXAMPLE 362B 4-fluoro-3-{2-[1-(methylsulfonyl)-1,2,3,6-tetrahydropyridin-4-yl]-1H-pyrrolo[2,3-b]pyridin-4-yl}aniline A mixture of Example 362A (40.0 mg, 0.128 mmol), 4-fluoro-3-(4,4,5,5-tetramethyl-1,3,2-dioxaborolan-2-yl)aniline (45.6 mg, 0.192 mmol), bis(triphenylphosphine)palladium(II) dichloride (9.00 mg, 0.013 mmol), tricyclohexylphosphine (3.60 mg, 0.013 mmol) and cesium carbonate (125 mg, 0.385 mmol) in dioxane (2 mL) was degassed and heated at 100° C. overnight. The mixture was concentrated, diluted with ethyl acetate and washed with water and brine. The organic layer was dried over $MgSO_4$, filtered, concentrated, and purified by HPLC (see protocol in Example 361) to provide the title compound as a trifluoroacetic acid salt. $^1H$ NMR (400 MHz, methanol-$d_4$) δ ppm 2.68-2.74 (m, 2H), 2.92 (s, 3H), 3.52 (t, J=5.6 Hz, 2H), 4.01-4.06 (m, 2H), 6.50-6.56 (m, 1H), 6.58 (d, J=1.8 Hz, 1H), 7.32 (dd, J=5.4, 1.5 Hz, 1H), 7.39-7.47 (m, 2H), 7.53 (d, J=4.6 Hz, 1H), 8.31 (d, J=5.4 Hz, 1H). MS (ESI$^+$) m/z 387.2 (M+H)$^+$.

EXAMPLE 363

4-fluoro-3-[2-(1-methylpiperidin-4-yl)-1H-pyrrolo[2,3-b]pyridin-4-yl]-N-(pyridin-3-ylmethyl)aniline The title compound was prepared essentially as described in Example 11B, substituting Example 179D (20 mg, 0.06 mmol) for Example 11A and nicotinaldehyde for benzaldehyde. $^1$H NMR (300 MHz, DMSO-d$_6$) δ 1.80 (dd, J=14.7, 11.2 Hz, 2H), 2.16-2.33 (m, 2H), 2.82 (d, J=2.8 Hz, 3H), 2.89-3.22 (m, 3H), 3.46-3.61 (m, 2H), 4.41 (s, 2H), 5.92 (t, J=2.0 Hz, 1H), 6.61-6.80 (m, 2H), 7.00 (dd, J=4.9, 1.4 Hz, 1H), 7.04-7.17 (m, 1H), 7.61 (dd, J=7.9, 5.1 Hz, 1H), 8.03 (d, J=7.9 Hz, 1H), 8.12-8.27 (m, 1H), 8.60 (dd, J=5.0, 1.6 Hz, 1H), 8.69 (d, J=2.1 Hz, 1H). MS (ESI$^+$) m/z 416 (M+H)$^+$.

EXAMPLE 364

4-fluoro-3-[2-(piperidin-4-yl)-1H-pyrrolo[2,3-b]pyridin-4-yl]-N-(pyridin-3-ylmethyl)aniline The title compound was prepared essentially as described in Examples 11B and 1H, substituting Example 353A (30 mg, 0.07 mmol) for Example 11A and nicotinaldehyde for benzaldehyde in Example 11B. The Boc-protected compound was then treated as described in Example 1H, to provide the title compound. $^1$H NMR (400 MHz, DMSO-d$_6$) δ 1.78 (dt, J=13.2, 6.2 Hz, 2H), 2.12-2.25 (m, 2H), 3.05 (ddd, J=15.3, 9.4, 3.8 Hz, 3H), 3.38 (d, J=12.5 Hz, 2H), 4.47 (s, 2H), 5.95 (t, J=2.0 Hz, 1H), 6.73 (dd, J=8.2, 4.3 Hz, 2H), 6.97-7.07 (m, 1H), 7.06-7.19 (m, 1H), 7.78 (dd, J=7.9, 5.3 Hz, 1H), 8.22 (dd, J=8.4, 6.1 Hz, 1H), 8.42 (d, J=11.3 Hz, 1H), 8.64-8.88 (m, 2H). MS (ESI$^+$) m/z 402 (M+H)$^+$.

EXAMPLE 365

N-(3,5-difluorobenzyl)-4-fluoro-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 3,5-difluorobenzaldehyde for benzaldehyde in Example 11B. The Boc-protected compound was then treated as described in Example 1H, to provide the title compound. $^1$H NMR (400 MHz, DMSO-d$_6$) δ 1.78 (qd, J=12.6, 3.8 Hz, 2H), 2.11-2.25 (m, 2H), 3.06 (ddd, J=14.8, 12.3, 6.7 Hz, 3H), 3.38 (d, J=13.2 Hz, 2H), 4.34 (s, 2H), 5.95 (t, J=1.9 Hz, 1H), 6.69 (dd, J=7.0, 4.3 Hz, 2H), 6.94-7.20 (m, 5H), 8.21 (d, J=5.0 Hz, 1H). MS (ESI$^+$) m/z 437 (M+H)$^+$.

EXAMPLE 366

N-(2,4-difluorobenzyl)-4-fluoro-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 2,4-difluorobenzaldehyde for benzaldehyde in Example 11B. The Boc-protected compound was then treated as described in Example 1H, to provide the title compound. $^1$H NMR (400 MHz, DMSO-d$_6$) δ 1.60-1.86 (m, 2H), 2.10 (dd, J=14.2, 3.7 Hz, 2H), 2.91-3.13 (m, 3H), 3.39 (d, J=12.4 Hz, 2H), 4.79 (s, 2H), 5.79 (s, 1H), 6.78 (dd, J=7.3, 4.3 Hz, 2H) 7.24-7.39 (m, 5H), 7.49-7.71 (m, 1H), 8.18 (d, J=5.0 Hz, 1H). MS (ESI$^+$) m/z 437 (M+H)$^+$.

EXAMPLE 367

N-(2,5-difluorobenzyl)-4-fluoro-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 2,5-difluorobenzaldehyde for benzaldehyde in Example 11B. The Boc-protected compound was then treated as described in Example 1H, to provide the title compound. $^1$H NMR (400 MHz, DMSO-d$_6$) δ 1.63-1.89 (m, 2H), 2.12-2.27 (m, 2H), 2.94-3.16 (m, 3H), 3.38 (d, J=12.9 Hz, 2H), 4.31 (s, 2H), 6.01 (d, J=2.0 Hz, 1H), 6.68-6.78 (m, 2H), 7.02-7.19 (m, 3H), 7.18-7.33 (m, 1H), 7.47 (td, J=8.6, 6.6 Hz, 1H), 8.23 (d, J=5.1 Hz, 1H). MS (ESI$^+$) m/z 437 (M+H)$^+$.

EXAMPLE 368

N-(2,6-difluorobenzyl)-4-fluoro-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 2,6-difluorobenzaldehyde for benzaldehyde in Example 11B. The Boc-protected compound was then treated as described in Example 1H, to provide the title compound. $^1$H NMR (400 MHz, DMSO-d$_6$) δ 1.81 (qd, J=13.1, 4.1 Hz, 2H), 2.16-2.30 (m, 2H), 2.95-3.18 (m, 3H), 3.38 (d, J=12.7 Hz, 2H), 4.30 (s, 2H), 6.11 (d, J=2.2 Hz, 1H), 6.69-6.89 (m, 2H), 7.03-7.20 (m, 4H), 7.41 (ddd, J=15.0, 8.4, 6.7 Hz, 1H), 8.25 (d, J=5.1 Hz, 1H). MS (ESI$^+$) m/z 437 (M+H)$^+$.

EXAMPLE 369

N-(3,5-difluorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 3,5-difluorobenzaldehyde for benzaldehyde. $^1$H NMR (500 MHz, DMSO-d$_6$) δ 1.81 (qd, J=13.5, 3.8 Hz, 2H), 2.21-2.36 (m, 2H), 2.81 (d, J=4.4 Hz, 3H), 3.02 (ddt, J=12.1, 8.5, 3.6 Hz, 1H), 3.11 (dt, J=13.4, 10.1 Hz, 2H), 3.54 (d, J=12.1 Hz, 2H), 4.29 (s, 2H), 5.95 (t, J=1.9 Hz, 1H), 6.69 (dd, J=7.0, 4.3 Hz, 2H), 6.94-7.20 (m, 5H), 8.21 (d, J=5.0 Hz, 1H). MS (ESI$^+$) m/z 451 (M+H)$^+$.

EXAMPLE 370

4-fluoro-N-(4-fluorobenzyl)-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 4-fluorobenzaldehyde for benzaldehyde in Example 11B. The Boc-protected compound was then treated as described in Example 1H, to provide the title compound. $^1$H NMR (300 MHz, DMSO-d$_6$) δ 1.67-1.83 (m, 2H), 2.10-2.26 (m, 2H), 2.91-3.16 (m, 3H), 3.37 (d, J=12.5 Hz, 2H), 4.28 (s, 2H), 5.93 (t, J=2.0 Hz, 1H), 6.64-6.75 (m, 2H), 7.02-7.22 (m, 4H), 7.35-7.49 (m, 2H), 8.20 (d, J=5.0 Hz, 1H). MS (ESI$^+$) m/z 419 (M+H)$^+$.

EXAMPLE 371

4-[({4-fluoro-3-[2-(piperidin-4-yl)-1H-pyrrolo[2,3-b]pyridin-4-yl]phenyl}amino)methyl]benzenesulfonamide The title compound was prepared essentially as described in Examples 11B and 1H, substituting Example 353A (30 mg, 0.07 mmol) for Example 11A and 4-formylbenzenesulfonamide for benzaldehyde in Example 11B. The Boc-protected compound was then treated as described in Example 1H, to provide the title compound. $^1$H NMR (300 MHz, DMSO-d$_6$) δ 1.67-1.88 (m, 2H), 2.17 (d, J=14.7 Hz, 2H), 2.96-3.20 (m, 3H), 3.38 (d, J=12.6 Hz, 2H), 4.38 (s, 2H), 5.90 (t, J=2.0 Hz, 1H), 6.61-6.74 (m, 2H), 7.28 (d, J=7.2 Hz, 2H), 7.49-7.60 (m, 2H), 7.74-7.85 (m, 2H), 8.19 (d, J=5.0 Hz, 1H). MS (ESI$^+$) m/z 480 (M+H)$^+$.

EXAMPLE 372

3-[({4-fluoro-3-[2-(piperidin-4-yl)-1H-pyrrolo[2,3-b]pyridin-4-yl]phenyl}amino)methyl]phenol The title compound was prepared essentially as described in Examples 11B and 1H, substituting Example 353A (30 mg, 0.07 mmol) for Example 11A and 3-hydroxybenzaldehyde for benzaldehyde in Example 11B. The Boc-protected compound was then treated as described in Example 1H, to provide the title compound. $^1$H NMR (300 MHz, DMSO-d$_6$) δ 1.79 (dt, J=13.2, 6.1 Hz, 2H), 2.09-2.27 (m, 2H), 2.91-3.16 (m, 3H), 3.38 (d, J=13.1 Hz, 2H), 4.21 (s, 2H), 5.96 (t, J=1.9 Hz, 1H), 6.64 (ddd, J=8.1, 2.5, 1.1 Hz, 1H), 6.71 (ddd, J=6.4, 4.2, 2.8 Hz, 2H), 6.78 (dt, J=4.0, 1.7 Hz, 2H), 7.00-7.07 (m, 1H), 7.07-7.18 (m, 2H), 8.20 (d, J=5.1 Hz, 1H). MS (ESI$^+$) m/z 417 (M+H)$^+$.

EXAMPLE 373

4-fluoro-3-[2-(piperidin-4-yl)-1H-pyrrolo[2,3-b]pyridin-4-yl]-N-(pyridin-2-ylmethyl)aniline The title compound was prepared essentially as described in Examples 11B and 1H, substituting Example 353A (30 mg, 0.07 mmol) for Example 11A and picolinaldehyde for benzaldehyde in Example 11B. The Boc-protected compound was then treated as described in Example 1H, to provide the title compound. $^1$H NMR (300 MHz, DMSO-d$_6$) δ 1.61-1.89 (m, 2H), 2.11-2.27 (m, 2H), 2.95-3.13 (m, 3H), 3.38 (d, J=12.5 Hz, 2H), 4.50 (s, 2H), 5.96 (t, J=2.0 Hz, 1H), 6.67-6.77 (m, 2H), 7.01 (dd, J=5.0, 1.4 Hz, 1H), 7.05-7.17 (m, 1H), 7.44-7.54 (m, 1H), 7.59 (d, J=7.9 Hz, 1H), 8.02 (td, J=7.7, 1.7 Hz, 1H), 8.20 (d, J=5.0 Hz, 1H), 8.58-8.67 (m, 1H). MS (ESI$^+$) m/z 402 (M+H)$^+$.

EXAMPLE 374

4-fluoro-N-[3-(methylsulfonyl)benzyl]-3-[2-(piperidin-4-yl)-1H-pyrrolo[2,3-b]pyridin-4-yl]aniline The title compound was prepared essentially as described in Examples 11B and 1H, substituting Example 353A (30 mg, 0.07 mmol) for Example 11A and 3-(methylsulfonyl)benzaldehyde for benzaldehyde in Example 11B. The Boc-protected compound was then treated as described in Example 1H, to provide the title compound. $^1$H NMR (300 MHz, DMSO-d$_6$) δ 1.67-1.85 (m, 2H), 2.17 (dd, J=13.2, 3.1 Hz, 2H), 3.05 (dd, J=11.5, 3.2 Hz, 3H), 3.18 (s, 3H), 3.38 (d, J=12.3 Hz, 2H), 4.42 (s, 2H), 5.93 (t, J=1.9 Hz, 1H), 6.62-6.78 (m, 2H), 7.02 (dd, J=5.1, 1.5 Hz, 1H), 7.05-7.18 (m, 1H), 7.63 (t, J=7.6 Hz, 1H), 7.72 (dt, J=7.8, 1.4 Hz, 1H), 7.83 (dt, J=7.7, 1.6 Hz, 1H), 7.94 (t, J=1.7 Hz, 1H), 8.20 (d, J=5.0 Hz, 1H). MS (ESI$^+$) m/z 479 (M+H)$^+$.

EXAMPLE 375

N-(4-fluoro-3-{2-[1-(methylsulfonyl)piperidin-4-yl]-1H-pyrrolo[2,3-b]pyridin-4-yl}phenyl)methanesulfonamide

EXAMPLE 375A 4-fluoro-3-(2-(piperidin-4-yl)-1H-pyrrolo[2,3-b]pyridin-4-yl)aniline The title compound was prepared essentially as described in Example 220D, substituting Example 353A (1.3 g, 3.2 mmol) for Example 220C. LC/MS m/z 311 (M+H)$^+$.

EXAMPLE 375B

N-(4-fluoro-3-{2-[1-(methylsulfonyl)piperidin-4-yl]-1H-pyrrolo[2,3-b]pyridin-4-yl}phenyl)methanesulfonamide The title compound was prepared essentially as described in Example 220E, substituting Example 375A (250 mg, 0.8 mmol) for Example 220D. $^1$H NMR (400 MHz, DMSO-d$_6$) δ 1.63-1.83 (m, 2H), 2.07-2.17 (m, 2H), 2.85 (dd, J=12.2, 2.5 Hz, 3H), 2.90 (s, 3H), 3.04 (s, 3H), 3.66 (dt, J=12.2, 3.2 Hz, 2H), 6.25 (t, J=1.6 Hz, 1H), 7.34 (ddd, J=6.1, 4.4, 2.2 Hz, 1H), 7.41 (t, J=9.4 Hz, 1H), 7.50 (dd, J=6.5, 2.7 Hz, 1H), 8.27 (d, J=5.1 Hz, 1H). MS (ESI$^+$) m/z 467 (M+H)$^+$.

EXAMPLE 376

N-benzyl-4-fluoro-3-{2-[1-(methylsulfonyl)piperidin-4-yl]-1H-pyrrolo[2,3-b]pyridin-4-yl}aniline

EXAMPLE 376A 4-fluoro-3-(2-(1-(methylsulfonyl)piperidin-4-yl)-1H-pyrrolo[2,3-b]pyridin-4-yl)aniline The title compound was prepared essentially as described in Example 220E, substituting Example 375A (250 mg, 0.8 mmol) for Example 220D. LC/MS m/z 389 (M+H)$^+$.

EXAMPLE 376B

N-benzyl-4-fluoro-3-{2-[1-(methylsulfonyl)piperidin-4-yl]-1H-pyrrolo[2,3-b]pyridin-4-yl})aniline The title compound was prepared essentially as described in Example 11B, substituting Example 376A (30 mg, 0.08 mmol) for Example 11A. $^1$H NMR (400 MHz, DMSO-d$_6$) δ 1.63-1.79 (m, 2H), 1.95-2.10 (m, 2H), 2.84 (tdd, J=11.3, 8.0, 3.0 Hz, 3H), 2.91 (s, 3H), 3.68 (dt, J=12.1, 3.1 Hz, 2H), 4.31 (s, 2H), 5.91 (s, 1H), 6.73 (td, J=8.8, 3.4 Hz, 2H), 7.07-7.15 (m, 2H), 7.21-7.32 (m, 1H), 7.30-7.44 (m, 4H), 8.21 (d, J=5.2 Hz, 1H). MS (ESI$^+$) m/z 479 (M+H)$^+$.

EXAMPLE 377

N-(3-chlorobenzyl)-4-fluoro-3-{2-[1-(methylsulfonyl)piperidin-4-yl]-1H-pyrrolo[2,3-b]pyridin-4-yl}aniline The title compound was prepared essentially as described in Example 11B, substituting Example 376A (30 mg, 0.08 mmol) for Example 11A and 3-chlorobenzaldehyde for benzaldehyde. $^1$H NMR (400 MHz, DMSO-d$_6$) δ 1.71 (td, J=12.5, 4.0 Hz, 2H), 1.98-2.11 (m, 2H), 2.85 (td, J=13.1, 12.7, 2.9 Hz, 3H), 2.91 (s, 3H), 3.68 (dt, J=12.2, 3.3 Hz, 2H), 4.32 (s, 2H), 5.87 (s, 1H), 6.61-6.75 (m, 2H), 7.00-7.17 (m, 2H), 7.28-7.47 (m, 5H), 8.19 (d, J=5.1 Hz, 1H). MS (ESI$^+$) m/z 514 (M+H)$^+$.

EXAMPLE 378

4-fluoro-N-(3-fluorobenzyl)-3-{2-[1-(methylsulfonyl)piperidin-4-yl]-1H-pyrrolo[2,3-b]pyridin-4-yl}aniline The title compound was prepared essentially as described in Example 11B, substituting Example 376A (30 mg, 0.08 mmol) for Example 11A and 3-fluorobenzaldehyde for benzaldehyde. $^1$H NMR (400 MHz, DMSO-d$_6$) δ 1.71 (tt, J=12.3, 6.2 Hz, 2H), 2.02 (dd, J=13.6, 3.6 Hz, 2H), 2.84 (dd, J=12.1, 2.6 Hz, 3H), 2.91 (s, 3H), 3.67 (dt, J=11.9, 3.2 Hz, 2H), 4.33 (s, 2H), 5.87 (s, 1H), 6.57-6.79 (m, 2H), 7.00-7.15 (m, 4H), 7.15-7.29 (m, 3H), 7.39 (td, J=7.9, 6.2 Hz, 1H), 8.18 (d, J=5.1 Hz, 1H). MS (ESI$^+$) m/z 497 (M+H)$^+$.

EXAMPLE 379

4-(5-fluoro-2-methoxyphenyl)-2-(2,2,6,6-tetramethyl-1,2,3,6-tetrahydropyridin-4-yl)-1H-pyrrolo[2,3-b]pyridine

EXAMPLE 379A 4-(5-fluoro-2-methoxyphenyl)-1-(phenylsulfonyl)-2-(2,2,6,6-tetramethyl-1,2,3,6-tetrahydropyridin-4-yl)-1H-pyrrolo[2,3-b]pyridine A mixture of Example 87B (800.0 mg, 1.574 mmol), 2,2,6,6-tetramethyl-4-(4,4,5,5-tetramethyl-1,3,2-dioxaborolan-2-yl)-1,2,3,6-tetrahydropyridine (501 mg, 1.889 mmol), tetrakis(triphenylphosphine)palladium(0) (72.7 mg, 0.063 mmol), and aqueous sodium bicarbonate solution (8 mL) in N,N-dimethylformamide (32 mL) was degassed and heated at 80° C. for 3 hours. After cooling, the reaction mixture was quenched with water and brine and extracted with ethyl acetate (twice). The combined organic layers were washed with brine, dried over MgSO$_4$, filtered, concentrated, and purified on a 40 g silica column using the ISCO Companion flash system eluting with methanol/ethyl acetate (5:95 to 10:90) to provide the title compound. MS (ESI$^+$) m/z 520.0 (M+H)$^+$.

EXAMPLE 379B 4-(5-fluoro-2-methoxyphenyl)-2-(2,2,6,6-tetramethyl-1,2,3,6-tetrahydropyridin-4-yl)-1H-pyrrolo[2,3-b]pyridine A mixture of Example 379A (750.0 mg, 1.443 mmol) and 20% aqueous sodium hydroxide (3 mL) solution in dioxane (22 mL) was heated at 95° C. for 16 hours. The solvent was evaporated. The residue was treated with ethyl acetate and washed with water. The organic layer was dried over MgSO$_4$, filtered, concentrated and purified on a 40 g silica column, pre-neutralized with triethylamine in ethyl acetate, using the ISCO Companion flash system eluting with ethyl acetate/methanol (100:0 to 90:10) to provide the title compound. $^1$H NMR (300 MHz, methanol-d$_4$) δ ppm 1.24 (s, 6H), 1.33 (s, 6H), 2.30 (d, J=1.6 Hz, 2H), 3.76 (s, 3H), 6.26 (s, 1H), 6.33-6.38 (m, 1H), 7.05-7.20 (m, 4H), 8.15 (d, J=5.1 Hz, 1H). MS (ESI$^+$) m/z 380.1 (M+H)$^+$.

EXAMPLE 380

4-fluoro-3-{2-[1-(methylsulfonyl)piperidin-4-yl]-1H-pyrrolo[2,3-b]pyridin-4-yl})-N-(pyridin-4-ylmethyl)aniline The title compound was prepared essentially as described in Example 11B, substituting Example 376A (30 mg, 0.08 mmol) for Example 11B and isonicotinaldehyde for benzaldehyde. $^1$H NMR (400 MHz, DMSO-d$_6$) δ 1.71 (qd, J=12.4, 4.0 Hz, 2H), 1.99-2.11 (m, 2H), 2.86 (td, J=12.3, 2.8 Hz, 3H), 2.91 (s, 3H), 3.67 (dt, J=12.3, 3.1 Hz, 2H), 4.59 (s, 2H), 5.93 (t, J=1.9 Hz, 1H), 6.61-6.74 (m, 2H), 7.11 (dd, J=10.3, 8.9 Hz, 2H), 7.85 (d, J=5.7 Hz, 2H), 8.17 (d, J=5.0 Hz, 1H), 8.78 (d, J=5.6 Hz, 2H). MS (ESI$^+$) m/z 480 (M+H)$^+$.

EXAMPLE 381

4-{[(4-fluoro-3-{2-[1-(methylsulfonyl)piperidin-4-yl]-1H-pyrrolo[2,3-b]pyridin-4-yl}phenyl)amino]methyl}benzonitrile The title compound was prepared essentially as described in Example 11B, substituting Example 376A (30 mg, 0.08 mmol) for Example 11A and 4-formylbenzonitrile for benzaldehyde. $^1$H NMR (400 MHz, DMSO-d$_6$) δ 1.70 (dd, J=12.6, 3.9 Hz, 2H), 2.03 (dd, J=13.4, 3.6 Hz, 2H), 2.85 (dd, J=12.1, 2.5 Hz, 3H), 2.91 (s, 3H), 3.68 (dt, J=12.3, 3.4 Hz, 2H), 4.37 (s, 2H), 5.86 (s, 1H), 6.69 (ddt, J=15.5, 6.2, 3.1 Hz, 2H), 7.13 (d, J=16.6 Hz, 2H), 7.58 (t, J=7.7 Hz, 1H), 7.73 (t, J=7.8 Hz, 2H), 7.81 (s, 1H), 8.18 (d, J=5.1 Hz, 1H). MS (ESI$^+$) m/z 504 (M+H)$^+$.

EXAMPLE 382

4-{2-fluoro-5-[(3-fluorobenzyl)oxy]phenyl}-2-(1,2,3,6-tetrahydropyridin-4-yl)-1H-pyrrolo[2,3-b]pyridine

EXAMPLE 382A tert-butyl 4-(4-(2-fluoro-5-hydroxyphenyl)-1-tosyl-1H-pyrrolo[2,3-b]pyridin-2-yl)-5,6-dihydropyridine-1(2H)-carboxylate A mixture of Example 220C (1.14 g, 2.14 mmol), 4-fluoro-3-(4,4,5,5-tetramethyl-1,3,2-dioxaborolan-2-yl) phenol (611 mg, 2.57 mmol), PdCl$_2$ (1,1'-bis(diphenylphosphino)ferrocene)-CH$_2$Cl$_2$ adduct (105 mg, 0.13 mmol), and 1 M sodium carbonate water solution (6.4 mL, 6.42 mmol) in dioxane (8 ml) was heated at 100° C. overnight, cooled and diluted with ethyl acetate. The mixture was washed with water and brine. The organic layer was dried over Na$_2$SO$_4$, filtered, and concentrated. The residue was purified by flash chromatography, and was eluted with a gradient of 0%-100% ethyl acetate in hexanes to provide the title compound. LCMS: 564 (M+H)$^+$.

EXAMPLE 382B tert-butyl 4-(4-(2-fluoro-5-((3-fluorobenzyl)oxy) phenyl)-1-tosyl-1H-pyrrolo[2,3-b]pyridin-2-yl)-5,6-dihydropyridine-1(2H)-carboxylate A solution of Example 382A (150 mg, 0.267 mmol), 2 (tributylphosphoranylidene)acetonitrile (96 mg, 0.40 mmol)

and (3-fluorophenyl)methanol (0.04 mL, 0.40 mmol) in toluene (5 mL) was heated at 75° C. overnight, cooled and loaded onto a silica gel column. The column was eluted with a gradient of 0%-35% ethyl acetate in heptanes to afford the title compound. LCMS: 672 (M+H)$^+$.

EXAMPLE 382C tert-butyl 4-(4-(2-fluoro-5-((3-fluorobenzyl)oxy)phenyl)-1H-pyrrolo[2,3-b]pyridin-2-yl)-5,6-dihydropyridine-1(2H)-carboxylate Example 382B (180 mg, 0.27 mmol) in dioxane (4 mL) and methanol (4 mL) was treated with 1 M aqueous NaOH (1.34 mL, 1.34 mmol) at 50° C. overnight, diluted with ethyl acetate and washed with water/brine. The organic layer was dried over $Na_2SO_4$, filtered, and concentrated to provide the title compound. LCMS: 518 (M+H)$^+$.

EXAMPLE 382D

4-{2-fluoro-5-[(3-fluorobenzyl)oxy]phenyl}-2-(1,2,3,6-tetrahydropyridin-4-yl)-1H-pyrrolo[2,3-b]pyridine The title compound was prepared as the trifluoroacetate salt using the procedure described in Example 344C, using Example 382C in place of Example 344B. $^1$H NMR (400 MHz, DMSO-$d_6$) δ ppm 2.70 (s, 2 H) 3.35 (d, 2 H) 3.85 (s, 2 H) 5.21 (s, 2 H) 6.41 (s, 1 H) 6.52 (s, 1 H) 7.10-7.23 (m, 4 H) 7.26-7.40 (m, 3 H) 7.41-7.52 (m, 1 H) 8.31 (d, 1 H) 9.03 (s, 2 H) 12.15 (s, 1 H); LCMS: 418 (M+H)$^+$.

The following compounds (concluding with Example 399) were prepared essentially as described in Example 360, substituting the appropriate aldehyde reagent.

EXAMPLE 383

2-({4-[4-(5-fluoro-2-methoxyphenyl)-1H-pyrrolo[2,3-b]pyridin-2-yl]piperidin-1-yl}methyl)-1H-benzimidazole $^1$H NMR (400 MHz, pyridine-$d_5$) δ ppm 1.85-1.98 (m, 2H), 2.09 (d, J=11.3 Hz, 2H), 2.36-2.44 (m, 2H), 2.87-2.98 (m, 1H), 3.14 (d, J=11.6 Hz, 2H), 3.71 (s, 3H), 4.16 (s, 2H), 6.28 (s, 1H), 7.11 (dd, J=9.1, 4.5 Hz, 1H), 7.25-7.31 (m, 1H), 7.31-7.39 (m, 3H), 7.47 (dd, J=9.0, 3.2 Hz, 1H), 7.84-7.92 (m, 2H), 8.56 (d, J=4.9 Hz, 1H), 12.81 (s, 1H); MS (ESI) m/z 456 (M+H)$^+$.

EXAMPLE 384

4-(5-fluoro-2-methoxyphenyl)-2-[1-(tetrahydrofuran-2-ylmethyl)piperidin-4-yl]-1H-pyrrolo[2,3-b]pyridine $^1$H NMR (400 MHz, pyridine-$d_5$) δ ppm 1.28-1.41 (m, 1H), 1.50-1.73 (m, 2H), 1.84-1.97 (m, 1H), 2.25-2.39 (m, 2H), 2.45-2.57 (m, 2H), 3.02-3.14 (m, 2H), 3.14-3.27 (m, 2H), 3.29-3.36 (m, 1H), 3.62-3.68 (m, 2H), 3.73 (s, 3H), 3.74-3.90 (m, 2H), 4.35-4.47 (m, 1H), 6.40 (s, 1H), 7.05-7.12 (m, 1H), 7.23-7.29 (m, 1H), 7.32 (d, J=4.9 Hz, 1H), 7.44 (dd, J=9.2, 4.6 Hz, 1H), 8.57 (d, J=4.9 Hz, 1H), 12.79 (s, 1H); MS (ESI) m/z 410 (M+H)$^+$.

EXAMPLE 385

2-[1-(5,6-dihydro-2H-pyran-3-ylmethyl)piperidin-4-yl]-4-(5-fluoro-2-methoxyphenyl)-1H-pyrrolo[2,3-b]pyridine $^1$H NMR (400 MHz, pyridine-$d_5$) δ ppm 2.04-2.11 (m, 2H), 2.13-2.31 (m, 4H), 2.33-2.46 (m, 2H), 2.97-3.08 (m, 1H), 3.22 (d, J=16.3 Hz, 4H), 3.69-3.73 (m, 5H), 4.38 (d, J=1.6 Hz, 2H), 5.86 (s, 1H), 6.40 (s, 1H), 7.09 (dd, J=9.1, 4.5 Hz, 1H), 7.22-7.29 (m, 1H), 7.33 (d, J=4.9 Hz, 1H), 7.47 (dd, J=9.0, 3.2 Hz, 1H), 8.57 (d, J=4.9 Hz, 1H), 12.86 (s, 1H); MS (ESI) m/z 422 (M+H)$^+$.

EXAMPLE 386

4-(5-fluoro-2-methoxyphenyl)-2-[1-(4-methoxybenzyl)piperidin-4-yl]-1H-pyrrolo[2,3-b]pyridine $^1$H NMR (400 MHz, pyridine-$d_5$) δ ppm 2.16-2.38 (m, 4H), 2.48-2.60 (m, 2H), 3.01-3.12 (m, 1H), 3.22-3.31 (m, 2H), 3.71 (d, J=6.6 Hz, 6H), 3.86 (s, 2H), 6.42 (s, 1H), 6.97-7.05 (m, 2H), 7.05-7.12 (m, 1H), 7.23-7.28 (m, 1H), 7.30-7.35 (m, 1H), 7.44-7.53 (m, 3H), 8.57 (d, J=4.9 Hz, 1H), 12.76-12.93 (m, 1H); MS (ESI) m/z 446 (M+H)$^+$.

EXAMPLE 387

4-(5-fluoro-2-methoxyphenyl)-2-{1-[2-(morpholin-4-yl)ethyl]piperidin-4-yl}-1H-pyrrolo[2,3-b]pyridine $^1$H NMR (400 MHz, pyridine-$d_5$) δ ppm 2.32 (d, J=11.7 Hz, 2H), 2.44-2.58 (m, 6H), 2.83 (t, J=6.2 Hz, 2H), 3.05 (t, J=11.0 Hz, 2H), 3.17-3.27 (m, 3H), 3.67-3.75 (m, 9H), 6.41 (s, 1H), 7.09 (dd, J=9.1, 4.5 Hz, 1H), 7.23-7.29 (m, 1H), 7.32 (d, J=4.9 Hz, 1H), 7.45 (dd, J=9.0, 3.2 Hz, 1H), 8.57 (d, J=5.0 Hz, 1H), 12.81 (s, 1H); MS (ESI) m/z 439 (M+H)$^+$.

EXAMPLE 388

4-({4-[4-(5-fluoro-2-methoxyphenyl)-1H-pyrrolo[2,3-b]pyridin-2-yl]piperidin-1-yl}methyl)benzonitrile $^1$H NMR (400 MHz, pyridine-$d_5$) δ ppm 2.05-2.13 (m, 6H), 2.82-2.97 (m, 3H), 3.50 (s, 2H), 3.71 (s, 3H), 6.40 (s, 1H), 7.10 (dd, J=9.1, 4.6 Hz, 1H), 7.24-7.31 (m, 1H), 7.35 (d, J=4.9 Hz, 1H), 7.47-7.52 (m, 3H), 7.70 (d, J=8.2 Hz, 2H), 8.59 (d, J=4.9 Hz, 1H), 12.89 (s, 1H); MS (ESI) m/z 441 (M+H)$^+$.

EXAMPLE 390

4-(5-fluoro-2-methoxyphenyl)-2-[1-(2-methylpropyl)piperidin-4-yl]-1H-pyrrolo[2,3-b]pyridine $^1$H NMR (400 MHz, pyridine-$d_5$) δ ppm 0.95 (d, J=6.6 Hz, 6H), 1.84-2.01 (m, 1H), 2.17-2.26 (m, 2H), 2.32-2.44 (m, 2H), 2.45-2.71 (m, 4H), 3.01-3.16 (m, 1H), 3.25-3.37 (m, 2H), 3.72 (s, 3H), 6.42 (d, J=6.4 Hz, 1H), 7.06-7.13 (m, 1H), 7.23-7.30 (m, 1H), 7.33 (d, J=4.1 Hz, 1H), 7.45-7.51 (m, 1H), 8.58 (d, J=4.9 Hz, 1H), 12.84 (s, 1H); MS (ESI) m/z 382 (M+H)$^+$.

EXAMPLE 391

N-[4-({4-[4-(5-fluoro-2-methoxyphenyl)-1H-pyrrolo[2,3-b]pyridin-2-yl]piperidin-1-yl}methyl)phenyl]acetamide $^1$H NMR (400 MHz, pyridine-$d_5$) δ ppm 2.08-2.37 (m, 9H), 2.91-3.06 (m, 1H), 3.15 (d, J=11.1 Hz, 2H), 3.71 (s, 5H), 6.39 (s, 1H), 7.08 (dd, J=9.1, 4.5 Hz, 1H), 7.23-7.28 (m, 1H), 7.33 (d, J=4.9 Hz, 1H), 7.44-7.53 (m, 3H), 8.04 (d, J=8.4 Hz, 2H), 8.57 (d, J=4.9 Hz, 1H), 10.83 (s, 1H), 12.86 (s, 1H); MS (ESI) m/z 473 (M+H)$^+$.

EXAMPLE 392

4-(5-fluoro-2-methoxyphenyl)-2-[1-(pyridin-2-ylmethyl)piperidin-4-yl]-1H-pyrrolo[2,3-b]pyridine $^1$H NMR (400 MHz, pyridine-$d_5$) δ ppm 2.14-2.36 (m, 4H), 2.61-2.77 (m, 2H), 3.00-3.11 (m, 1H), 3.35 (d, J=12.0 Hz, 2H), 3.71 (s, 3H), 4.17 (s, 2H), 6.39 (s, 1H), 7.04-7.11 (m, 1H), 7.15-7.20 (m, 1H), 7.23-7.29 (m, 1H), 7.33 (d, J=4.9 Hz, 1H), 7.44-7.50 (m, 1H), 7.65-7.68 (m, 2H), 8.57 (d, J=4.9 Hz, 1H), 8.67 (d, J=4.7 Hz, 1H), 12.89 (s, 1H); MS (ESI) m/z 417 (M+H)$^+$.

EXAMPLE 393

4-({4-[4-(5-fluoro-2-methoxyphenyl)-1H-pyrrolo[2,3-b]pyridin-2-yl]piperidin-1-yl}methyl)-N,N-dimethylaniline $^1$H NMR (400 MHz, pyridine-$d_5$) δ ppm 2.25-2.36 (m, 2H), 2.46-2.63 (m, 2H), 2.78 (s, 6H), 2.91-3.03 (m, 2H), 3.11-3.25 (m, 1H), 3.45-3.60 (m, 2H), 3.73 (s, 3H), 4.22 (s, 2H), 6.42 (s, 1H), 6.71 (d, J=8.7 Hz, 2H), 7.08 (dd, J=9.1, 4.5 Hz, 1H), 7.23-7.28 (m, 1H), 7.31 (d, J=4.9 Hz, 1H), 7.41-7.51 (m, 3H), 8.57 (d, J=4.9 Hz, 1H), 12.80 (s, 1H); MS (ESI) m/z 459 (M+H)$^+$.

EXAMPLE 394

2-{1-[(1-tert-butyl-1H-pyrazol-4-yl)methyl]piperidin-4-yl}-4-(5-fluoro-2-methoxyphenyl)-1H-pyrrolo[2,3-b]pyridine $^1$H NMR (400 MHz, pyridine-$d_5$) δ ppm 1.54 (s, 9H), 2.23-2.37 (m, 2H), 2.43-2.58 (m, 2H), 2.96-3.25 (m, 3H), 3.61 (s, 2H), 3.72 (s, 3H), 4.32 (s, 2H), 6.39 (s, 1H), 7.08 (dd, J=9.1, 4.5 Hz, 1H), 7.22-7.28 (m, 1H), 7.31 (d, J=4.9 Hz, 1H), 7.43 (dd, J=9.0, 3.2 Hz, 1H), 7.86 (s, 1H), 8.13 (s, 1H), 8.56 (d, J=4.9 Hz, 1H), 12.78 (s, 1H). MS (ESI) m/z 462 (M+H)$^+$.

EXAMPLE 395

4-(5-fluoro-2-methoxyphenyl)-2-[1-(2-methoxyethyl)piperidin-4-yl]-1H-pyrrolo[2,3-b]pyridine $^1$H NMR (400 MHz, pyridine-$d_5$) δ ppm 2.19-2.28 (m, 2H), 2.30-2.44 (m, 2H), 2.71-2.85 (m, 2H), 3.06-3.11 (m, 2H), 3.24 (s, 3H), 3.43-3.52 (m, 2H), 3.66-3.75 (m, 6H), 6.40 (s, 1H), 7.08 (dd, J=9.1, 4.5 Hz, 1H), 7.23-7.29 (m, 1H), 7.32 (d, J=4.9 Hz, 1H), 7.41-7.51 (m, 1H), 8.57 (d, J=4.9 Hz, 1H), 12.83 (s, 1H); MS (ESI) m/z 384 (M+H)$^+$.

EXAMPLE 396

4-(5-fluoro-2-methoxyphenyl)-2-[1-(pyridin-4-ylmethyl)piperidin-4-yl]-1H-pyrrolo[2,3-b]pyridine $^1$H NMR (400 MHz, pyridine-$d_5$) δ ppm 2.07-2.23 (m, 6H), 2.90-3.00 (m, 3H), 3.54 (s, 2H), 3.71 (s, 3H), 6.40 (s, 1H), 7.10 (dd, J=9.1, 4.5 Hz, 1H), 7.23-7.30 (m, 1H), 7.34 (d, J=5.0 Hz, 1H), 7.39 (d, J=5.8 Hz, 2H), 7.50 (dd, J=9.0, 3.2 Hz, 1H), 8.58 (d, J=4.9 Hz, 1H), 8.77 (dd, J=4.5, 1.4 Hz, 2H), 12.89 (s, 1H); MS (ESI) m/z 417 (M+H)$^+$.

EXAMPLE 397

N,N-diethyl-2-[4-({4-[4-(5-fluoro-2-methoxyphenyl)-1H-pyrrolo[2,3-b]pyridin-2-yl]piperidin-1-yl}methyl)phenoxy]ethanamine $^1$H NMR (400 MHz, pyridine-$d_5$) δ ppm 1.27 (t, J=7.2 Hz, 6H), 2.25-2.34 (m, 2H), 2.41-2.54 (m, 2H), 2.82-2.94 (m, 2H), 3.13-3.22 (m, 1H), 3.25 (q, J=7.3 Hz, 4H), 3.41-3.51 (m, 2H), 3.60-3.62 (m, 2H), 3.73 (s, 3H), 4.16 (s, 2H), 4.53 (t, J=5.0 Hz, 2H), 6.42 (s, 1H), 7.05-7.09 (m, 4H), 7.23-7.28 (m, 1H), 7.32 (d, J=4.9 Hz, 1H), 7.45 (dd, J=9.0, 3.2 Hz, 1H), 7.53-7.57 (m, 1H), 8.57 (d, J=4.9 Hz, 1H), 12.82 (s, 1H); MS (ESI) m/z 531 (M+H)$^+$.

EXAMPLE 398

4-chloro-5-({4-[4-(5-fluoro-2-methoxyphenyl)-1H-pyrrolo[2,3-b]pyridin-2-yl]piperidin-1-yl}methyl)-1,3-thiazol-2-amine $^1$H NMR (400 MHz, pyridine-$d_5$) δ ppm 1.99-2.21 (m, 6H), 2.85-2.94 (m, 1H), 3.07 (d, J=11.0 Hz, 2H), 3.64 (s, 2H), 3.70 (s, 3H), 6.36 (s, 1H), 7.09 (dd, J=9.1, 4.5 Hz, 1H), 7.24-7.29 (m, 1H), 7.33 (d, J=4.9 Hz, 1H), 7.36-7.42 (m, 1H), 7.49 (dd, J=9.0, 3.2 Hz, 1H), 8.50 (s, 1H), 8.57 (d, J=5.0 Hz, 1H), 12.92 (s, 1H); MS (ESI) m/z 472 (M+H)$^+$.

EXAMPLE 399

2-[1-(1,3-benzodioxol-5-ylmethyl)piperidin-4-yl]-4-(5-fluoro-2-methoxyphenyl)-1H-pyrrolo[2,3-b]pyridine $^1$H NMR (400 MHz, pyridine-$d_5$) δ ppm 1.99-2.21 (m, 6H), 2.85-2.94 (m, 1H), 3.07 (d, J=11.0 Hz, 2H), 3.64 (s, 2H), 3.70 (s, 3H), 6.36 (s, 1H), 7.09 (dd, J=9.1, 4.5 Hz, 1H), 7.24-7.29 (m, 1H), 7.33 (d, J=4.9 Hz, 1H), 7.36-7.42 (m, 1H), 7.49 (dd, J=9.0, 3.2 Hz, 1H), 8.50 (s, 1H), 8.57 (d, J=5.0 Hz, 1H), 12.92 (s, 1H); MS (ESI) m/z 472 (M+H)$^+$.

EXAMPLE 389

1-(2-{4-[4-(5-fluoro-2-methoxyphenyl)-1H-pyrrolo[2,3-b]pyridin-2-yl]-3,6-dihydropyridin-1(2H)-yl}ethyl)-3-methylurea The title compound was prepared essentially as described in Example 1333, substituting methanesulfonyl chloride with isocyanatomethane. $^1$H NMR (400 MHz, DMSO-$d_6$) δ ppm 11.77 (s, 1 H) 8.18 (d, J=4.88 Hz, 1 H) 7.10-7.39 (m, 3 H) 7.02 (d, J=4.88 Hz, 1 H) 6.49 (s, 1 H) 6.19 (d, J=1.83 Hz, 1 H) 5.62-5.94 (m, 2 H) 3.74 (s, 3 H) 3.06-3.23 (m, 4 H) 2.57-2.68 (m, 2 H) 2.37-2.56 (m, 7H). MS (ESI): 424.1 (M+H)$^+$.

EXAMPLE 400

3-{[(4-fluoro-3-{2-[1-(methylsulfonyl)piperidin-4-yl]-1H-pyrrolo[2,3-b]pyridin-4-yl}phenyl)amino]methyl}phenol The title compound was prepared essentially as described in Examples 11B, substituting Example 376A (30 mg, 0.08 mmol) for Example 11A and 3-hydroxybenzaldehyde for benzaldehyde. $^1$H NMR (300 MHz, DMSO-$d_6$) δ 1.65-1.79 (m, 2H), 2.03 (d, J=12.9 Hz, 2H), 2.85 (td, J=11.0, 9.9, 2.8 Hz, 3H), 2.91 (s, 3H), 3.58-3.73 (m, 2H), 4.22 (s, 2H), 5.92 (t, J=1.7 Hz, 1H), 6.56-6.74 (m, 3H), 6.77 (dd, J=4.6, 2.7 Hz, 2H), 7.01-7.17 (m, 3H), 8.18 (d, J=5.1 Hz, 1H). MS (ESI$^+$) m/z 495 (M+H)$^+$.

EXAMPLE 401

4-fluoro-N-[3-(methylsulfonyl)benzyl]-3-{2-[1-(methylsulfonyl)piperidin-4-yl]-1H-pyrrolo[2,3-b]pyridin-4-yl}aniline The title compound was prepared essentially as described in Example 11B, substituting Example 376A (30 mg, 0.08 mmol) for Example 11A and 3-(methylsulfonyl)benzaldehyde for benzaldehyde. $^1$H NMR (300 MHz, DMSO-$d_6$) δ 1.76 (dd, J=12.3, 3.9 Hz, 2H), 2.04 (d, J=12.9 Hz, 2H), 2.71-2.89 (m, 3H), 2.90 (s, 3H), 3.66 (d, J=11.9 Hz, 2H), 3.93 (s, 3H), 4.38 (s, 2H), 5.96 (t, J=1.9 Hz, 1H), 6.60-6.75 (m, 2H), 6.97-7.15 (m, 2H), 7.26 (d, J=7.7 Hz, 2H), 7.49-7.60 (m, 2H), 7.74-7.84 (m, 2H), 8.17 (d, J=5.0 Hz, 1H). MS (ESI$^+$) m/z 557 (M+H)$^+$.

EXAMPLE 402

4-{[(4-fluoro-3-{2-[1-(methylsulfonyl)piperidin-4-yl]-1H-pyrrolo[2,3-b]pyridin-4-yl}phenyl)amino]methyl})benzamide The title compound was prepared essentially as described in Example 11B, substituting Example 376A (30 mg, 0.08 mmol) for Example 11A and 4-formylbenzamide for benzaldehyde. $^1$H NMR (300 MHz, DMSO-$d_6$) δ 1.77 (td, J=12.6, 3.9 Hz, 2H), 1.93 (t, J=8.6 Hz, 2H), 2.79-2.89 (m, 3H), 2.92 (s, 3H), 3.62-3.72 (m, 2H), 4.36 (s, 2H), 5.70 (t, J=1.6 Hz, 1H), 6.57-6.76 (m, 2H), 7.05-7.09 (m, 2H), 7.40-7.45 (m, 2H), 7.82-7.89 (m, 2H), 8.16 (d, J=5.0 Hz, 1H). MS (ESI$^+$) m/z 522 (M+H)$^+$.

EXAMPLE 403

4-{[(4-fluoro-3-{2-[1-(methylsulfonyl)piperidin-4-yl]-1H-pyrrolo[2,3-b]pyridin-4-yl}phenyl)amino]methyl}phenol The title compound was prepared essentially as described in Example 11B, substituting Example 376A (30 mg, 0.08 mmol) for Example 11A and 4-hydroxybenzaldehyde for benzaldehyde. $^1$H NMR (300 MHz, DMSO-$d_6$) δ 1.63-1.89 (m, 2H), 2.04 (dd, J=13.5, 3.5 Hz, 2H), 2.84 (dt, J=12.0, 4.0 Hz, 3H), 2.90 (s, 3H), 3.61-3.73 (m, 2H), 4.18 (s, 2H), 5.95 (t, J=1.7 Hz, 1H), 6.66-6.80 (m, 4H), 6.98-7.20 (m, 4H), 8.18 (d, J=5.1 Hz, 1H). MS (ESI$^+$) m/z 495 (M+H)$^+$.

The following compounds (concluding with Example 1010) were prepared essentially as described in Example 361, substituting the appropriate amino intermediate and/or the appropriate aldehyde reagent. The reaction was run either at room temperature or at 40° C. In some examples, a trifluoroacetic acid salt of the title compound was converted into a free base.

EXAMPLE 404

4-(5-fluoro-2-methoxyphenyl)-2-{1-[2-(morpholin-4-yl)ethyl]-1,2,3,6-tetrahydropyridin-4-yl}-1H-pyrrolo[2,3-b]pyridine $^1$H NMR (400 MHz, methanol-$d_4$) δ ppm 2.86-2.99 (m, 2H), 3.09-3.15 (m, 4H), 3.36 (t, J=6.5 Hz, 2H), 3.50-3.58 (m, 4H), 3.81 (s, 3H), 3.84-3.90 (m, 4H), 4.01-4.06 (m, 2H), 6.52 (bs, 1H), 6.64 (s, 1H), 7.18-7.32 (m, 3H), 7.45 (d, J=5.8 Hz, 1H), 8.32 (d, J=5.8 Hz, 1H). MS (ESI) m/z 437.1 (M+H)$^+$.

EXAMPLE 509

3-[4-(4-{5-[(3,5-difluorobenzyl)amino]-2-fluorophenyl}-1H-pyrrolo[2,3-b]pyridin-2-yl)-3,6-dihydropyridin-1(2H)-yl]propane-1,2-diol $^1$H NMR (400 MHz, methanol-$d_4$) δ ppm 2.86-2.94 (m, 2H), 3.29-3.35 M, 1H), 3.37-3.85 (m, 4H), 3.79-3.93 (m, 1H), 3.98-4.32 (m, 3H), 4.39 (s, 2H), 6.47 (bs, 1H), 6.57 (d, J=2.0 Hz, 1H), 6.73-6.86 (m, 3H), 6.95-7.14 (m, 3H), 7.32 (d, J=6.0 Hz, 1H), 8.31 (d, J=5.6 Hz, 1H). MS (ESI) m/z 509.0 (M+H)$^+$.

EXAMPLE 534

4-(5-fluoro-2-methoxyphenyl)-2-[1-(pyridin-2-ylmethyl)-1,2,3,6-tetrahydropyridin-4-yl]-1H-pyrrolo[2,3-b]pyridine $^1$H NMR (400 MHz, methanol-$d_4$) δ ppm 2.94-3.02 (m, 2H), 3.64 (t, J=6.1 Hz, 2H), 3.81 (s, 3H), 4.11-4.17 (m, 2H), 4.63 (s, 2H), 6.48-6.54 (m, 1H), 6.65 (s, 1H), 7.18-7.31 (m, 3H), 7.40-7.52 (m, 2H), 7.54 (d, J=7.8 Hz, 1H), 7.93 (td, J=7.7, 1.8 Hz, 1H), 8.32 (d, J=5.7 Hz, 1H), 8.71 (d, J=5.1 Hz, 1H). MS (ESI) m/z 415.0 (M+H)$^+$.

EXAMPLE 535

3-{5-[4-(5-fluoro-2-methoxyphenyl)-1H-pyrrolo[2,3-b]pyridin-2-yl]-3,6-dihydropyridin-1(2H)-yl}propane-1,2-diol $^1$H NMR (400 MHz, methanol-$d_4$) δ ppm 2.68-2.89 (m, 2H), 3.28-3.45 (m, 4H), 3.54-3.64 (m, 2H), 3.80 (s, 3H), 4.09-4.55 (m, 3H), 6.56 (s, 1H), 6.72-6.78 (m, 1H), 7.17-7.29 (m, 3H), 7.38 (d, J=5.6 Hz, 1H), 8.31 (d, J=5.6 Hz, 1H). MS (ESI) m/z 398.2 (M+H)$^+$.

EXAMPLE 574

N-[4-({5-[4-(5-fluoro-2-methoxyphenyl)-1H-pyrrolo[2,3-b]pyridin-2-yl]-3,6-dihydropyridin-1(2H)-yl}methyl)phenyl]acetamide $^1$H NMR (400 MHz, methanol-$d_4$) δ ppm 2.15 (s, 3H), 2.71-2.78 (m, 2H), 3.41-3.69 (m, 2H), 3.78 (s, 3H), 4.08-4.36 (m, 2H), 4.43-4.49 (m, 2H), 6.48 (s, 1H), 6.71-6.77 (m, 1H), 7.17-7.31 (m, 3H), 7.39 (d, J=5.7 Hz, 1H), 7.47-7.54 (m, 2H), 7.67-7.74 (m, 2H), 8.31 (d, J=5.7 Hz, 1H). MS (ESI) m/z 471.1 (M+H)$^+$.

EXAMPLE 575

4-(5-fluoro-2-methoxyphenyl)-2-[1-(tetrahydrofuran-2-ylmethyl)-1,2,5,6-tetrahydropyridin-3-yl]-1H-pyrrolo[2,3-b]pyridine $^1$H NMR (400 MHz, pyridine-$d_5$) δ ppm 1.44 (dq, J=12.1, 8.1 Hz, 1H), 1.52-1.77 (m, 2H), 1.82-2.00 (m, 1H), 2.58-2.70 (m, 2H), 3.11 (dd, J=13.2, 8.4 Hz, 1H), 3.17-3.33 (m, 2H), 3.42 (dt, J=11.7, 5.8 Hz, 1H), 3.62 (td, J=8.0, 6.0 Hz, 1H), 3.69 (s, 3H), 3.73-3.85 (m, 1H), 4.18-4.35 (m, 2H), 4.41 (qd, J=8.0, 2.8 Hz, 1H), 6.68 (s, 1H), 6.74-6.88 (m, 1H), 7.07 (dd, J=9.1, 4.5 Hz, 1H), 7.18-7.31 (m, 2H), 7.45 (dd, J=8.9, 3.2 Hz, 1H), 8.58 (d, J=4.9 Hz, 1H), 13.09 (bs, 1H). MS (ESI) m/z 408.2 (M+H)$^+$.

EXAMPLE 591

3-{4-[4-(2,3-difluorophenyl)-1H-pyrrolo[2,3-b]pyridin-2-yl]-3,6-dihydropyridin-1(2H)-yl}propane-1,2-diol $^1$H NMR (500 MHz, methanol-$d_4$) δ ppm 2.90-3.04 (m, 2H), 3.28-3.35 (m, 1H), 3.36-3.53 (m, 2H), 3.55-3.64 (m, 2H), 3.79-4.31 (m, 4H), 6.48 (bs, 1H), 6.63 (d, J=2.2 Hz, 1H), 7.31 (d, J=5.8 Hz, 1H), 7.32-7.40 (m, 1H), 7.39-7.51 (m, 2H), 8.35 (d, J=5.3 Hz, 1H). MS (ESI) m/z 386.0 (M+H)$^+$.

EXAMPLE 592

N-[4-({4-[4-(2,3-difluorophenyl)-1H-pyrrolo[2,3-b]pyridin-2-yl]-3,6-dihydropyridin-1(2H)-yl}methyl)phenyl]acetamide $^1$H NMR (400 MHz, methanol-$d_4$) δ ppm 2.15 (s, 3H), 2.95 (bs, 2H), 3.31-3.46 (m, 1H), 3.66-3.84 (m, 1H), 3.98 (bs, 2H), 4.43 (s, 2H), 4.92-5.06 (m, 1H), 6.47 (bs, 1H), 6.64 (d, J=2.2 Hz, 1H), 7.30-7.57 (m, 6H), 7.68-7.75 (m, 2H), 8.36 (d, J=5.4 Hz, 1H). MS (ESI) m/z 459.1 (M+H)$^+$.

EXAMPLE 597

3-{3-[4-(5-fluoro-2-methoxyphenyl)-1H-pyrrolo[2,3-b]pyridin-2-yl]-8-azabicyclo[3.2.1]oct-2-en-8-yl}propane-1,2-diol $^1$H NMR (400 MHz, methanol-$d_4$) δ ppm 2.02-2.17 (m, 1H), 2.27-2.61 (m, 3H), 2.72-2.90 (m, 1H), 3.12-3.39 (m, 2H), 3.42-3.69 (m, 3H), 3.80 (s, 3H), 3.96-4.13 (m, 1H), 4.26-4.70 (m, 2H), 6.58-6.77 (m, 2H), 7.17-7.29 (m, 3H), 7.35-7.41 (m, 1H), 8.31 (d, J=5.6 Hz, 1H). MS (ESI) m/z 424.1 (M+H)$^+$.

EXAMPLE 617

4-{2-[1-(2,3-dihydroxypropyl)-1,2,3,6-tetrahydropyridin-4-yl]-1H-pyrrolo[2,3-b]pyridin-4-yl}-N-methylbenzamide $^1$H NMR (400 MHz, methanol-$d_4$) δ ppm 2.97 (s, 3H), 2.98-3.04 (m, 2H), 3.33-3.50 (m, 3H), 3.55-3.65 (m, 2H), 3.76-4.32 (m, 4H), 6.50-6.55 (m, 1H), 6.93 (s, 1H), 7.48 (d, J=5.7 Hz, 1H), 7.88-7.97 (m, 2H), 8.00-8.06 (m, 1H), 8.38 (d, J=5.7 Hz, 1H). MS (ESI) m/z 407.1 (M+H)$^+$.

EXAMPLE 634

4-(2,3-difluorophenyl)-2-[1-(pyridin-2-ylmethyl)-1,2,3,6-tetrahydropyridin-4-yl]-1H-pyrrolo[2,3-b]pyridine $^1$H NMR (400 MHz, methanol-$d_4$) δ ppm 2.99 (ddt, J=6.3, 3.9, 1.9 Hz, 2H), 3.65 (t, J=6.2 Hz, 2H), 4.14 (q, J=2.4 Hz, 2H), 4.63 (s, 2H), 6.51 (p, J=2.1 Hz, 1H), 6.68 (d, J=2.2 Hz, 1H), 7.31-7.74 (m, 6H), 7.93 (td, J=7.8, 1.8 Hz, 1H), 8.37 (d, J=5.5 Hz, 1H), 8.71 (dt, J=5.0, 1.1 Hz, 1H). MS (ESI) m/z 403.1 (M+H)$^+$.

EXAMPLE 698

3-{4-[5-fluoro-4-(5-fluoro-2-methoxyphenyl)-1H-pyrrolo[2,3-b]pyridin-2-yl]-3,6-dihydropyridin-1(2H)-yl}propane-1,2-diol $^1$H NMR (500 MHz, methanol-$d_4$) δ ppm 2.86-2.95 (m, 2H), 3.26-3.30 (m, 1H), 3.35-3.50 (m, 2H), 3.54-3.63 (m, 2H), 3.77 (s, 3H), 3.77-3.87 (m, 1H), 3.93-4.03 (m, 1H), 4.08-4.25 (m, 2H), 6.32-6.41 (m, 2H), 7.09-7.20 (m, 2H), 7.22 (td, J=8.5, 3.1 Hz, 1H), 8.16 (d, J=2.8 Hz, 1H). MS (ESI) m/z 416.0 (M+H)$^+$.

EXAMPLE 731

4-{2-[1-(2,3-dihydroxypropyl)-1,2,3,6-tetrahydropyridin-4-yl]-1H-pyrrolo[2,3-b]pyridin-4-yl}-3-methoxy-N-methylbenzamide $^1$H NMR (400 MHz, methanol-$d_4$) δ ppm 2.92-3.00 (m, 5H), 3.28-3.43 (m, 2H), 3.44-3.64 (m, 3H), 3.76-3.92 (m, 4H), 3.98-4.32 (m, 3H), 6.49-6.55 (m, 1H), 6.65 (s, 1H), 7.48 (d, J=5.8 Hz, 1H), 7.56-7.61 (m, 2H), 7.67 (s, 1H), 8.34 (d, J=5.8 Hz, 1H). MS (ESI) m/z 437.0 (M+H)$^+$.

EXAMPLE 851

4-{2-[1-(2,3-dihydroxypropyl)-1,2,3,6-tetrahydropyridin-4-yl]-1H-pyrrolo[2,3-b]pyridin-4-yl}-2-fluoro-N-methylbenzamide $^1$H NMR (400 MHz, pyridine-$d_5$) δ ppm 3.04, (bs, 2H), 3.16 (d, J=4.6 Hz, 3H), 3.57-3.86 (m, 4H), 4.00-4.16 (m, 2H), 4.24-4.45 (m, 2H), 4.73-4.82 (m, 1H), 6.74 (bs, 1H), 6.84 (s, 1H), 7.21-7.24 (m, 3H), 7.67-7.79 (m, 2H), 8.33 (t, J=7.8 Hz, 1H), 8.60 (d, J=4.9 Hz, 1H), 8.81 (t, J=4.9 Hz, 1H), 13.15-13.35 (m, 1H). MS (ESI$^+$) m/z 425.0 (M+H)$^+$.

EXAMPLE 1010

3-{4-[4-(5-fluoro-2-methoxyphenyl)-1H-pyrrolo[2,3-b]pyridin-2-yl]-3,3-dimethyl-3,6-dihydropyridin-1(2H)-yl}propane-1,2-diol $^1$H NMR (400 MHz, methanol-$d_4$) δ ppm 1.25 (s, 6H), 2.50 (s, 2H), 2.53-2.55 (m, 2H), 3.23 (t, J=3.0 Hz, 2H), 3.55 (dd, J=11.2, 5.6 Hz, 1H), 3.65 (dd, J=11.1, 4.6 Hz, 1H), 3.77 (s, 3H), 3.86 (p, J=5.7 Hz, 1H), 6.06 (t, J=3.5 Hz, 1H), 6.21 (s, 1H), 7.03-7.20 (m, 4H), 8.15 (d, J=5.1 Hz, 1H). MS (ESI$^+$) m/z 426.2 (M+H)$^+$.

EXAMPLE 406

2,4-difluoro-5-{2-[1-(methylsulfonyl)-1,2,3,6-tetrahydropyridin-4-yl]-1H-pyrrolo[2,3-b]pyridin-4-yl}-N-(tetrahydro-2H-pyran-4-ylmethyl)aniline

EXAMPLE 406A tert-butyl 4-(4-(5-amino-2,4-difluorophenyl)-1-tosyl-1H-pyrrolo[2,3-b]pyridin-2-yl)-5,6-dihydropyridine-1(2H)-carboxylate The title compound was prepared using the procedure described in Example 344A, using Example 220C in replace of Example 17E. LCMS: 581 (M+H)$^+$.

EXAMPLE 406B tert-butyl 4-(4-(2,4-difluoro-5-(((tetrahydro-2H-pyran-4-yl)methyl)amino)phenyl)-1-tosyl-1H-pyrrolo[2,3-b]pyridin-2-yl)-5,6-dihydropyridine-1(2H)-carboxylate The title compound was prepared using the procedure described in Example 344B, substituting tetrahydro-2H-pyran-4-carbaldehyde for 4-methyltetrahydro-2H-pyran-4-carbaldehyde and Example 406A for Example 344A. LCMS: 679 (M+H)$^+$.

EXAMPLE 406C 2,4-difluoro-N-((tetrahydro-2H-pyran-4-yl)methyl)-5-(2-(1,2,3,6-tetrahydropyridin-4-yl)-1-tosyl-1H-pyrrolo[2,3-b]pyridin-4-yl)aniline The title compound was prepared as the trifluoroacetate salt using the procedure described in Example 344C, using Example 406B in place of Example 344B. LCMS: 579 (M+H)$^+$.

EXAMPLE 406D 2,4-difluoro-5-(2-(1-(methylsulfonyl)-1,2,3,6-tetrahydropyridin-4-yl)-1-tosyl-1H-pyrrolo[2,3-b]pyridin-4-yl)-N-((tetrahydro-2H-pyran-4-yl)methyl)aniline To a solution of Example 406C (0.13 g, 0.22 mmol) in dichloromethane (3 mL) and dimethylformamide (1 mL) was added dropwise methanesulfonyl chloride (0.034 mL, 0.44 mmol). The mixture was stirred at room temperature for 10 minutes and the reaction was quenched with water. The resulting mixture was diluted with dichloromethane and washed with water and brine. The organic layer was dried over Na$_2$SO$_4$, filtered, and concentrated to provide the title compound. LCMS: 657 (M+H)$^+$.

EXAMPLE 406E 2,4-difluoro-5-{2-[1-(methylsulfonyl)-1,2,3,6-tetrahydropyridin-4-yl]-1H-pyrrolo[2,3-b]pyridin-4-yl}-N-(tetrahydro-2H-pyran-4-ylmethyl)aniline The title compound was prepared as the trifluoroacetate salt using the procedure described in Example 382C, using Example 406D in place of Example 382B. $^1$H NMR (400 MHz, DMSO-d$_6$) δ ppm 1.12-1.28 (m, 2 H) 1.58-1.69 (m, 2 H) 1.79-1.91 (m, 1 H) 2.55-2.65 (m, 2 H) 2.95 (s, 3 H) 3.00 (d, 2 H) 3.21-3.31 (m, 2 H) 3.32-3.44 (m, 2 H) 3.79-3.95 (m, 4 H) 6.39 (s, 1 H) 6.56 (d, 1 H) 6.83 (dd, 1 H) 7.01-7.17 (m, 1 H) 7.27 (dd, 1 H) 8.26 (t, 1 H) 12.05 (s, 1 H); LCMS: 503 (M+H)$^+$.

EXAMPLE 407

2,4-difluoro-N-(tetrahydro-2H-pyran-4-ylmethyl)-5-[2-(1,2,3,6-tetrahydropyridin-4-yl)-1H-pyrrolo[2,3-b]pyridin-4-yl]aniline

EXAMPLE 407A tert-butyl 4-(4-(2,4-difluoro-5-(((tetrahydro-2H-pyran-4-yl)methyl)amino)phenyl)-1H-pyrrolo[2,3-b]pyridin-2-yl)-5,6-dihydropyridine-1(2H)-carboxylate The title compound was prepared using the procedure described in Example 382C, using Example 406B in place of Example 382B. LCMS: 525 (M+H)$^+$.

EXAMPLE 407B 2,4-difluoro-N-(tetrahydro-2H-pyran-4-ylmethyl)-5-[2-(1,2,3,6-tetrahydropyridin-4-yl)-1H-pyrrolo[2,3-b]pyridin-4-yl]aniline The title compound was prepared as the trifluoroacetate salt using the procedure described in Example 344C, using Example 407A in place of Example 344B. $^1$H NMR (400 MHz, DMSO-d$_6$) δ ppm 1.10-1.30 (m, 2 H) 1.65 (dd, 2 H) 1.78-1.95 (m, 1 H) 2.63-2.78 (m, 2 H) 3.00 (d, 2 H) 3.16-3.42 (m, 4 H) 3.73-3.91 (m, 4 H) 6.44 (s, 1 H) 6.52 (s, 1 H) 6.82 (dd, 1 H) 7.11 (dd, 1 H) 7.27 (dd, 1 H) 8.29 (d, 1H) 8.93 (s, 2 H) 12.11 (s, 1 H); LCMS: 425 (M+H)$^+$.

EXAMPLE 408

2,4-difluoro-N-(3-fluorobenzyl)-5-[2-(1,2,3,6-tetrahydropyridin-4-yl)-1H-pyrrolo[2,3-b]pyridin-4-yl]aniline

EXAMPLE 408A tert-butyl 4-(4-(2,4-difluoro-5-((3-fluorobenzyl)amino)phenyl)-1-tosyl-1H-pyrrolo[2,3-b]pyridin-2-yl)-5,6-dihydropyridine-1(2H)-carboxylate The title compound was prepared using the procedure described in Example 344B, using 3-fluorobenzaldehyde in place of 4-methyltetrahydro-2H-pyran-4-carbaldehyde and Example 406A in place of Example 344A. LCMS: 689 (M+H)$^+$.

EXAMPLE 408B tert-butyl 4-(4-(2,4-difluoro-5-((3-fluorobenzyl)amino)phenyl)-1H-pyrrolo[2,3-b]pyridin-2-yl)-5,6-dihydropyridine-1(2H)-carboxylate The title compound was prepared using the procedure described in Example 382C, using Example 408A in place of Example 382B. LCMS: 535 (M+H)$^+$.

EXAMPLE 408C 2,4-difluoro-N-(3-fluorobenzyl)-5-[2-(1,2,3,6-tetra-hydropyridin-4-yl)-1H-pyrrolo[2,3-b]pyridin-4-yl]aniline The title compound was prepared as the trifluoroacetate salt using the procedure described in Example 344C, using Example 408B in place of Example 344B. $^1$H NMR (400 MHz, DMSO-$d_6$) δ ppm 2.16 (s, 2 H) 2.91 (t, 2 H) 3.41 (d, 2 H) 4.40 (d, 2 H) 5.93 (s, 1 H) 6.32-6.43 (m, 1 H) 6.47 (s, 1 H) 6.70 (dd, 1 H) 6.92 (dd, 1 H) 6.99-7.09 (m, 1 H) 7.13-7.20 (m, 2 H) 7.25-7.40 (m, 2 H) 8.15 (d, 1 H) 11.78 (s, 1 H); LCMS: 435 (M+H)$^+$.

EXAMPLE 409

N-(3,5-difluorobenzyl)-4-fluoro-3-{2-[1-(methylsulfonyl)-1,2,3,6-tetrahydropyridin-4-yl]-1H-pyrrolo[2,3-b]pyridin-4-yl}aniline

EXAMPLE 409A 4-fluoro-3-(2-(1-(methylsulfonyl)-1,2,3,6-tetrahydropyridin-4-yl)-1H-pyrrolo[2,3-b]pyridin-4-yl)aniline A mixture of Example 220F (140.0 mg, 0.393 mmol), 4-fluoro-3-(4,4,5,5-tetramethyl-1,3,2-dioxaborolan-2-yl)aniline (140 mg, 0.589 mmol), bis(triphenylphosphine)palladium(II) dichloride (13.79 mg, 0.020 mmol), and 1M aqueous sodium carbonate (550 μL, 0.550 mmol) in 5 mL of 1,2-dimethoxyethane/ethanol/water (7:2:3) was heated in a microwave reactor (Biotag Initiator, model 355302) at 160° C. for 15 minutes. The mixture was diluted with ethyl acetate and washed with water and brine. The organic layer was washed with water, dried over MgSO$_4$, filtered, concentrated, and purified on a 12 g silica column using the ISCO Companion flash system eluting with methanol/ethyl acetate (2:98 to 5:95) to provide the title compound. MS (ESI$^+$) m/z 387.2 (M+H)$^+$.

EXAMPLE 409B

N-(3,5-difluorobenzyl)-4-fluoro-3-{2-[1-(methylsulfonyl)-1,2,3,6-tetrahydropyridin-4-yl]-1H-pyrrolo[2,3-b]pyridin-4-yl}aniline A mixture of Example 409A (54.0 mg, 0.140 mmol), acetic acid (0.024 mL, 0.419 mmol), and 3,5-difluorobenzaldehyde (59.6 mg, 0.419 mmol) in ClCH$_2$CH$_2$Cl (4 mL) was stirred for 1 hour. To the mixture was added sodium triacetoxyborohydride (89 mg, 0.419 mmol). The reaction was stirred at 70° C. overnight. More triacetoxyborohydride (30 mg) was added. The reaction mixture was heated at 70° C. for 7 more hours, concentrated, and treated with methanol (1.5 mL), dimethyl sulfoxide (1.5 mL) and water (3 mL). The precipitate was filtered, washed with water, and purified by HPLC (see protocol in Example 361) to provide the title compound as a trifluoroacetic acid salt. $^1$H NMR (400 MHz, DMSO-$d_6$) δ ppm 2.52-2.58 (m, 2H), 2.95 (s, 3H), 3.38 (t, J=5.7 Hz, 2H), 3.88-3.96 (m, 2H), 4.35 (bs, 2H), 6.23 (bs, 1H), 6.50-6.56 (m, 1H), 6.65-6.77 (m, 2H), 7.00-7.16 (m, 5H), 8.24 (d, J=5.0 Hz, 1H), 11.99-12.04 (m, 1H). MS (ESI$^+$) m/z 513.2 (M+H)$^+$.

EXAMPLE 410

4-[4-(5-fluoro-2-methoxyphenyl)-1H-pyrrolo[2,3-b]pyridin-2-yl]-N-(propan-2-yl)-3,6-dihydropyridine-1(2H)-carboxamide To a suspension of Example 87D (70.0 mg, 0.177 mmol) in N,N-dimethylformamide (2 mL) was added 2-isocyanatopropane (0.026 mL, 0.265 mmol) and triethylamine (0.148 mL, 1.060 mmol). The reaction was stirred overnight. Water was slowly added to the reaction mixture. The solids formed were filtered, rinsed with water, and vacuum oven-dried to provide the title compound. $^1$H NMR (400 MHz, DMSO-$d_6$) δ ppm 1.07 (d, J=6.5 Hz, 6H), 2.40-2.48 (m, 27H), 3.50 (t, J=5.6 Hz, 2H), 3.74 (s, 3H), 3.74-3.85 (m, 1H), 3.98-4.04 (m, 2H), 6.18 (d, J=7.5 Hz, 1H), 6.24 (d, J=2.0 Hz, 1H), 6.48-6.54 (m, 1H), 7.03 (d, J=4.9 Hz, 1H), 7.16-7.31 (m, 3H), 8.20 (d, J=4.9 Hz, 1H), 11.79-11.84 (m, 1H). MS (ESI$^+$) m/z 409.1 (M+H)$^+$.

EXAMPLE 411

2-(1-ethyl-1,2,3,6-tetrahydropyridin-4-yl)-4-(5-fluoro-2-methoxyphenyl)-1H-pyrrolo[2,3-b]pyridine In a 2 mL vial was added 1.5 mL aqueous 1M ammonium acetate/acetic acid buffer in methanol (pH=4.6). Example 87D (20 mg, 0.062 mmol) and acetaldehyde (13.62 mg, 0.309 mmol) were added followed by the addition of 200 mg Si-cyanoborohydride (0.89 mmol/g, from Silicycle). The contents were allowed to react overnight at 40° C. The solid support was then filtered off and the crude mixture purified by reverse phase HPLC (see protocols in Example 360) to provide the title compound. $^1$H NMR (500 MHz, DMSO-D$_2$O) δ 12.06 (t, J=5.7 Hz, 1H), 9.91-9.69 (m, 1H), 8.26 (d, J=4.9 Hz, 1H), 7.39-7.14 (m, 3H), 7.09 (d, J=5.0 Hz, 1H), 6.54-6.43 (m, 1H), 6.39 (d, J=1.8 Hz, 1H), 4.14-4.05 (m, 2H), 3.74 (s, 4H), 3.70-3.61 (m, 2H), 3.28-3.17 (m, 3H), 2.97-2.66 (m, 2H), 1.41-1.21 (m, 3H). MS (ESI) m/z 352 [M+1]$^+$.

The following compounds (concluding with Example 439) were prepared essentially as described in Example 432, substituting the appropriate aldehyde reagent.

EXAMPLE 412

2-(1-benzyl-1,2,3,6-tetrahydropyridin-4-yl)-4-(5-fluoro-2-methoxyphenyl)-1H-pyrrolo[2,3-b]pyridine $^1$H NMR (400 MHz, pyridine-$d_5$) δ ppm 2.66-2.71 (m, 2H), 2.78 (t, J=5.6 Hz, 2H), 3.30 (q, J=2.8 Hz, 2H), 3.70 (s, 5H), 6.66 (s, 1H), 6.68-6.74 (m, 1H), 7.09 (dd, J=9.0, 4.5 Hz, 1H), 7.26-7.32 (m, 2H), 7.35-7.43 (m, 2H), 7.44-7.53 (m, 3H), 8.41-8.47 (m, 1H), 8.57 (d, J=4.9 Hz, 1H), 12.99 (bs, 1H). MS (ESI$^+$) m/z 414.2 (M+H)$^+$.

EXAMPLE 433

2-[1-(5,6-dihydro-2H-pyran-3-ylmethyl)-1,2,3,6-tetrahydropyridin-4-yl]-4-(5-fluoro-2-methoxyphenyl)-1H-pyrrolo[2,3-b]pyridine $^1$H NMR (400 MHz, pyridine-$d_5$) δ ppm 2.08 (dq, J=7.3, 3.5 Hz, 2H), 2.67 (td, J=5.6, 5.2, 2.8 Hz, 2H), 2.73 (t, J=5.4 Hz, 2H), 3.07 (d, J=1.7 Hz, 2H), 3.28 (q, J=2.7 Hz, 2H), 3.71 (s, 3H), 3.73 (t, J=5.5 Hz, 2H), 4.33 (q, J=2.3 Hz, 2H), 5.79 (dq, J=3.9, 2.1 Hz, 1H), 6.66 (s, 1H), 6.70-6.74 (m, 1H), 7.09

(dd, J=9.1, 4.5 Hz, 1H), 7.20-7.23 (m, 1H), 7.24-7.29 (m, 1H), 7.31 (d, J=4.9 Hz, 1H), 7.50 (dd, J=9.0, 3.2 Hz, 1H), 8.57 (d, J=5.0 Hz, 1H), 12.99 (s, 1H). MS (ESI$^+$) m/z 420.2 (M+H)$^+$.

EXAMPLE 434

4-({4-[4-(5-fluoro-2-methoxyphenyl)-1H-pyrrolo[2,3-b]pyridin-2-yl]-3,6-dihydropyridin-1(2H)-yl}methyl)-N,N-dimethylaniline $^1$H NMR (400 MHz, pyridine-d$_5$) δ ppm 2.78 (s, 6H), 2.86 (d, J=6.1 Hz, 2H), 3.16 (t, J=5.9 Hz, 2H), 3.69 (d, J=3.8 Hz, 2H), 3.70 (s, 3H), 4.04 (s, 2H), 6.66 (s, 1H), 6.68 (d, J=3.8 Hz, 1H), 6.73-6.78 (m, 2H), 7.09 (dd, J=9.1, 4.5 Hz, 1H), 7.23-7.29 (m, 1H), 7.30 (d, J=4.9 Hz, 1H), 7.48 (dt, J=8.8, 1.8 Hz, 3H), 8.58 (d, J=4.9 Hz, 1H). MS (ESI$^+$) m/z 457.3 (M+H)$^+$.

EXAMPLE 435

N,N-diethyl-2-[4-({4-[4-(5-fluoro-2-methoxyphenyl)-1H-pyrrolo[2,3-b]pyridin-2-yl]-3,6-dihydropyridin-1(2H)-yl}methyl)phenoxy]ethanamine $^1$H NMR (400 MHz, pyridine-d$_5$) δ ppm 1.26 (t, J=7.2 Hz, 6H), 2.84 (q, J=4.2, 2.9 Hz, 2H), 3.11 (t, J=5.9 Hz, 2H), 3.25 (q, J=7.2 Hz, 4H), 3.58-3.62 (m, 2H), 3.62-3.64 (m, 1H), 3.70 (s, 3H), 4.00 (s, 2H), 4.52 (t, J=5.0 Hz, 2H), 6.66 (s, 1H), 6.68-6.72 (m, 1H), 7.04-7.07 (m, 2H), 7.09 (dd, J=9.1, 4.5 Hz, 1H), 7.27 (ddd, J=9.1, 8.0, 3.2 Hz, 2H), 7.31 (d, J=4.9 Hz, 1H), 7.46-7.49 (m, 1H), 7.52-7.54 (m, 2H), 8.57 (d, J=4.9 Hz, 1H). MS (ESI$^+$) m/z 529.2 (M+H)$^+$.

EXAMPLE 436

4-(5-fluoro-2-methoxyphenyl)-2-[1-(pyridin-4-ylmethyl)-1,2,3,6-tetrahydropyridin-4-yl]-1H-pyrrolo[2,3-b]pyridine $^1$H NMR (400 MHz, pyridine-d$_5$) δ ppm 2.68 (d, J=1.9 Hz, 4H), 3.23 (d, J=3.4 Hz, 2H), 3.58 (s, 2H), 3.71 (s, 3H), 6.68 (d, J=1.9 Hz, 1H), 6.72 (t, J=3.7 Hz, 1H), 7.10 (dd, J=9.1, 4.5 Hz, 1H), 7.24-7.30 (m, 1H), 7.32 (d, J=5.0 Hz, 1H), 7.37-7.40 (m, 2H), 7.50 (dd, J=9.0, 3.2 Hz, 1H), 8.58 (d, J=4.9 Hz, 1H), 8.74-8.76 (m, 2H). MS (ESI$^+$) m/z 415.2 (M+H)$^+$.

EXAMPLE 437

4-({4-[4-(5-fluoro-2-methoxyphenyl)-1H-pyrrolo[2,3-b]pyridin-2-yl]-3,6-dihydropyridin-1(2H)-yl}methyl)benzonitrile $^1$H NMR (400 MHz, pyridine-d$_5$) δ ppm 2.65 (d, J=4.6 Hz, 2H), 2.74 (t, J=5.6 Hz, 2H), 3.28 (q, J=2.9 Hz, 2H), 3.70 (s, 3H), 3.83 (s, 2H), 6.64 (d, J=1.8 Hz, 1H), 6.69 (d, J=3.5 Hz, 1H), 7.09 (dd, J=9.1, 4.5 Hz, 1H), 7.23-7.29 (m, 1H), 7.31 (d, J=4.9 Hz, 2H), 7.48-7.55 (m, 3H), 7.61 (d, J=8.1 Hz, 1H), 7.70 (dd, J=7.7, 1.3 Hz, 1H), 8.57 (d, J=4.9 Hz, 1H). MS (ESI$^+$) m/z 439.2 (M+H)$^+$.

EXAMPLE 438

4-chloro-5-({4-[4-(5-fluoro-2-methoxyphenyl)-1H-pyrrolo[2,3-b]pyridin-2-yl]-3,6-dihydropyridin-1(2H)-yl}methyl)-1,3-thiazol-2-amine $^1$H NMR (400 MHz, pyridine-d$_5$) δ ppm 2.66 (t, J=4.1 Hz, 2H), 2.82 (t, J=5.6 Hz, 2H), 3.39 (q, J=2.7 Hz, 2H), 3.71 (s, 3H), 3.80 (s, 2H), 6.64 (s, 1H), 6.69-6.73 (m, 1H), 7.08 (dd, J=9.1, 4.5 Hz, 1H), 7.25 (ddd, J=9.1, 8.1, 3.3 Hz, 1H), 7.30 (d, J=5.0 Hz, 1H), 7.49 (dd, J=9.0, 3.2 Hz, 1H), 8.56 (d, J=4.9 Hz, 1H). MS (ESI$^+$) m/z 470.1 (M+H)$^+$.

EXAMPLE 439

4-(5-fluoro-2-methoxyphenyl)-2-[1-(tetrahydrofuran-2-ylmethyl)-1,2,3,6-tetrahydropyridin-4-yl]-1H-pyrrolo[2,3-b]pyridine $^1$H NMR (400 MHz, pyridine-d$_5$) δ ppm 1.41-1.53 (m, 1H), 1.57-1.76 (m, 2H), 1.85-1.95 (m, 1H), 2.83 (d, J=5.5 Hz, 2H), 2.94 (dd, J=13.1, 7.8 Hz, 1H), 3.05 (dd, J=13.1, 3.4 Hz, 1H), 3.18 (dt, J=11.8, 5.8 Hz, 1H), 3.28 (dt, J=11.8, 5.9 Hz, 1H), 3.63-3.69 (m, 1H), 3.70 (s, 3H), 3.74-3.90 (m, 3H), 4.32 (qd, J=7.6, 3.4 Hz, 1H), 6.65 (s, 1H), 6.67-6.71 (m, 1H), 7.10 (dd, J=9.1, 4.5 Hz, 1H), 7.27 (ddd, J=9.1, 8.0, 3.2 Hz, 1H), 7.31 (d, J=4.9 Hz, 1H), 7.48 (dd, J=9.0, 3.2 Hz, 1H), 8.58 (d, J=4.9 Hz, 1H). MS (ESI$^+$) m/z 408.2 (M+H)$^+$.

EXAMPLE 413

4-fluoro-3-{2-[1-(methylsulfonyl)piperidin-4-yl]-1H-pyrrolo[2,3-b]pyridin-4-yl}-N-(pyridin-3-ylmethyl)aniline The title compound was prepared essentially as described in Example 11B, substituting Example 376A (30 mg, 0.08 mmol) for Example 11A and nicotinaldehyde for benzaldehyde. $^1$H NMR (400 MHz, DMSO-d$_6$) δ 1.70 (dd, J=12.7, 4.0 Hz, 2H), 1.92-2.10 (m, 2H), 2.82-2.91 (m, 3H), 2.91 (s, 3H), 3.68 (dt, J=12.5, 3.2 Hz, 2H), 4.50 (s, 2H), 5.96 (t, J=1.8 Hz, 1H), 6.66-6.81 (m, 2H), 7.05 (dd, J=5.2, 1.6 Hz, 1H), 7.13 (dd, J=10.2, 8.4 Hz, 1H), 7.88 (dd, J=8.0, 5.4 Hz, 1H), 8.20 (d, J=5.1 Hz, 1H), 8.35 (dt, J=8.1, 1.7 Hz, 1H), 8.75 (dd, J=5.5, 1.5 Hz, 1H), 8.81 (d, J=2.0 Hz, 1H). MS (ESI$^+$) m/z 480 (M+H)$^+$.

EXAMPLE 414

N-(3,5-difluorobenzyl)-4-fluoro-3-{2-[1-(methylsulfonyl)piperidin-4-yl]-1H-pyrrolo[2,3-b]pyridin-4-yl}aniline The title compound was prepared essentially as described in Example 11B, substituting Example 376A (30 mg, 0.08 mmol) for Example 11A and 3,5-difluorobenzaldehyde for benzaldehyde. $^1$H NMR (400 MHz, DMSO-d$_6$) δ 1.70 (dd, J=12.5, 4.0 Hz, 2H), 1.94-2.09 (m, 2H), 2.85 (td, J=12.5, 11.9, 2.9 Hz, 3H), 2.91 (s, 3H), 3.64-3.72 (m, 2H), 4.34 (s, 2H), 5.88 (s, 1H), 6.59-6.79 (m, 2H), 7.00-7.18 (m, 5H), 8.19 (d, J=5.1 Hz, 1H). MS (ESI$^+$) m/z 515 (M+H)$^+$.

EXAMPLE 415

N-(3,4-difluorobenzyl)-4-fluoro-3-{2-[1-(methylsulfonyl)piperidin-4-yl]-1H-pyrrolo[2,3-b]pyridin-4-yl}aniline The title compound was prepared essentially as described in Example 11B, substituting Example 376A (30 mg, 0.08 mmol) for Example 11A and 3,4-difluorobenzaldehyde for benzaldehyde. $^1$H NMR (500 MHz, DMSO-d$_6$) δ 1.59-1.80 (m, 2H), 1.95-2.17 (m, 2H), 2.77-2.88 (m, 3H), 2.91 (s, 3H), 3.68 (dt, J=12.3, 3.2 Hz, 2H), 4.30 (s, 2H), 5.87-5.99 (m, 1H), 6.62-6.80 (m, 2H), 7.01-7.16 (m, 2H), 7.18-7.26 (m, 1H), 7.33-7.45 (m, 2H), 8.21 (d, J=5.1 Hz, 1H). MS (ESI$^+$) m/z 515 (M+H)$^+$.

EXAMPLE 416

N-(3,4-difluorobenzyl)-4-fluoro-3-[2-(1-methylpiperidin-4-yl)-1H-pyrrolo[2,3-b]pyridin-4-yl]aniline The title compound was prepared essentially as described in Example 11B, substituting Example 179D (20 mg, 0.06 mmol) for Example 11A and 3,4-difluorobenzaldehyde for benzaldehyde. $^1$H NMR (400 MHz, DMSO-d$_6$) δ 1.68-1.89 (m, 2H), 2.17-2.33 (m, 2H), 2.83 (d, J=4.2 Hz, 3H), 2.99-3.12 (m, 3H), 3.54 (d, J=11.4 Hz, 2H), 4.30 (s, 2H), 5.97 (d, J=2.2 Hz, 1H), 6.69 (dd, J=6.2, 3.2 Hz, 2H), 6.99-7.06 (m, 1H), 7.06-7.17 (m, 2H), 7.18-7.26 (m, 1H), 7.34-7.46 (m, 2H), 8.21 (d, J=5.0 Hz, 1H). MS (ESI$^+$) m/z 451 (M+H)$^+$.

EXAMPLE 417

1-[4-(4-{5-[(3,5-difluorobenzyl)amino]-2-fluorophenyl}-1H-pyrrolo[2,3-b]pyridin-2-yl)piperidin-1-yl]-2-hydroxyethanone A mixture of Example 365 (436 mg, 1.0 mmol), 2-hydroxyacetic acid (114 mg, 1.5 mmol), N-(3-dimethylaminopropyl)-N'-ethylcarbodiimide hydrochloride (285 mg, 1.5 mmol), 1-hydroxybenzotriazole hydrate (231 mg, 1.5 mmol) and triethylamine (152 mg, 1.5 mmol) in N,N-dimethylformamide (5 mL) was stirred at room temperature overnight. The mixture was concentrated in vacuo and the residue was purified by reverse-phase HPLC on Zorbax XDB C-18 (32) using a gradient of 5-40% acetonitrile/water (containing 0.1% trifluoroacetic acid) to afford the title compound as the trifluoroacetate salt. $^1$H NMR (500 MHz, DMSO-d$_6$) δ 1.53 (tt, J=12.7, 6.5 Hz, 1H), 1.64 (qd, J=12.6, 4.2 Hz, 1H), 1.92-2.05 (m, 2H), 2.75 (t, J=13.0 Hz, 1H), 2.99-3.18 (m, 2H), 3.81 (d, J=13.4 Hz, 1H), 4.13 (s, 2H), 4.38 (s, 2H), 4.48 (d, J=13.0 Hz, 1H), 6.10 (t, J=1.8 Hz, 1H), 6.75-6.92 (m, 2H), 7.00-7.18 (m, 3H), 7.22 (t, J=9.5 Hz, 1H), 7.36 (dd, J=5.7, 1.8 Hz, 1H), 8.35 (d, J=5.7 Hz, 1H). MS (ESI$^+$) m/z 495 (M+H)$^+$.

EXAMPLE 418

3-[4-(4-{2-fluoro-5-[(pyridin-3-ylmethyl)amino]phenyl}-1H-pyrrolo[2,3-b]pyridin-2-yl)piperidin-1-yl]propane-1,2-diol The title compound was prepared essentially as described in Examples 149, substituting Example 364 (30 mg, 0.08 mmol) for Example 135B. $^1$H NMR (400 MHz, DMSO-d$_6$) δ 1.71-2.07 (m, 2H), 2.13-2.36 (m, 2H), 2.98-3.24 (m, 4H), 3.28-3.50 (m, 2H), 3.63 (m, 2H), 3.96 (q, J=6.6, 5.5 Hz, 2H), 4.46 (s, 2H), 5.95 (t, J=2.2 Hz, 1H), 6.72 (dq, J=7.0, 3.4 Hz, 2H), 7.02 (dd, J=5.0, 1.3 Hz, 1H), 7.12 (dd, J=10.2, 8.6 Hz, 1H), 7.76 (dd, J=8.0, 5.2 Hz, 1H), 8.10-8.28 (m, 2H), 8.59-8.74 (m, 1H), 8.77 (d, J=2.2 Hz, 1H). MS (ESI$^+$) m/z 476 (M+H)$^+$.

EXAMPLE 419

3-[4-(4-{2-fluoro-5-[(pyridin-4-ylmethyl)amino]phenyl}-1H-pyrrolo[2,3-b]pyridin-2-yl)piperidin-1-yl]propane-1,2-diol The title compound was prepared essentially as described in Example 149, substituting Example 357 (30 mg, 0.08 mmol) for Example 135B. $^1$H NMR (400 MHz, DMSO-d$_6$) δ 1.68-2.09 (m, 1H), 2.12-2.36 (m, 2H), 2.92-3.25 (m, 5H), 3.34-3.52 (m, 2H), 3.61-3.73 (m, 2H), 3.96 (d, J=4.5 Hz, 2H), 4.59 (s, 2H), 5.94 (t, J=2.2 Hz, 1H), 6.62-6.75 (m, 2H), 6.96-7.04 (m, 1H), 7.07-7.17 (m, 1H), 7.84 (d, J=5.5 Hz, 2H), 8.20 (d, J=5.0 Hz, 1H), 8.78 (d, J=5.7 Hz, 2H). MS (ESI$^+$) m/z 476 (M+H)$^+$.

EXAMPLE 420

4-{[(3-{2-[1-(2,3-dihydroxypropyl)piperidin-4-yl]-1H-pyrrolo[2,3-b]pyridin-4-yl}-4-fluorophenyl)amino]methyl}benzonitrile The title compound was prepared essentially as described in Example 149, substituting Example 355 (30 mg, 0.07 mmol) for Example 135B. $^1$H NMR (400 MHz, DMSO-d$_6$) δ 1.71-2.08 (m, 1H), 2.13-2.37 (m, 2H), 2.91-3.25 (m, 5H), 3.25-3.51 (m, 2H), 3.64 (t, J=10.2 Hz, 2H), 3.97 (s, 2H), 4.41 (s, 2H), 5.92 (t, J=2.1 Hz, 1H), 6.62-6.71 (m, 2H), 6.97-7.04 (m, 1H), 7.09 (t, J=9.6 Hz, 1H), 7.56 (dd, J=8.4, 2.0 Hz, 2H), 7.83 (dd, J=8.0, 5.7 Hz, 2H), 8.19 (dd, J=5.0, 2.4 Hz, 1H). MS (ESI$^+$) m/z 500 (M+H)$^+$.

EXAMPLE 421

3-{[(3-{2-[1-(2,3-dihydroxypropyl)piperidin-4-yl]-1H-pyrrolo[2,3-b]pyridin-4-yl}-4-fluorophenyl)amino]methyl}benzonitrile

EXAMPLE 421A 3-(((4-fluoro-3-(2-(piperidin-4-yl)-1H-pyrrolo[2,3-b]pyridin-4-yl)phenyl)amino)methyl)benzonitrile The title compound was prepared essentially as described in Examples 11B and 1H, substituting Example 353A (60 mg, 0.16 mmol) for Example 11A and 3-formylbenzonitrile for benzaldehyde in Example 11B. The Boc-protected compound was then treated as described in Example 1H, to provide the title compound. MS (ESI$^+$) m/z 426 (M+H)$^+$.

EXAMPLE 421B

3-{[(3-{2-[1-(2,3-dihydroxypropyl)piperidin-4-yl]-1H-pyrrolo[2,3-b]pyridin-4-yl}-4-fluorophenyl)amino]methyl}benzonitrile The title compound was prepared essentially as described in Example 149, substituting Example 421A (30 mg, 0.07 mmol) for Example 135B. $^1$H NMR (500 MHz, DMSO-d$_6$) δ 1.70-2.09 (m, 1H), 2.22 (dt, J=25.8, 13.2 Hz, 2H), 2.88-3.26 (m, 5H), 3.27-3.50 (m, 2H), 3.63 (t, J=11.6 Hz, 3H), 3.93-4.05 (m, 2H), 4.37 (s, 2H), 5.91 (t, J=2.0 Hz, 1H), 6.69 (dd, J=7.2, 4.4 Hz, 2H), 7.01 (dd, J=4.9, 1.4 Hz, 1H), 7.10 (ddd, J=11.1, 8.3, 2.0 Hz, 1H), 7.57 (t, J=7.7 Hz, 1H), 7.74 (ddd, J=11.6, 7.8, 1.9 Hz, 2H), 7.81 (t, J=1.7 Hz, 1H), 8.20 (d, J=5.0 Hz, 1H). MS (ESI$^+$) m/z 500 (M+H)$^+$.

EXAMPLE 422

3-{2-[1-(cyclopropylsulfonyl)piperidin-4-yl]-1H-pyrrolo[2,3-b]pyridin-4-yl}-4-fluoro-N-(pyridin-4-ylmethyl)aniline

EXAMPLE 422A 3-(2-(1-(cyclopropylsulfonyl)piperidin-4-yl)-1H-pyrrolo[2,3-b]pyridin-4-yl)-4-fluoroaniline The title compound was prepared essentially as described in Example 220E, substituting Example 375A (250 mg, 0.8 mmol) for Example 220D and cyclopropanesulfonyl chloride for methylsulfonyl chloride. LC/MS m/z 415 (M+H)+.

EXAMPLE 422B

3-{2-[1-(cyclopropylsulfonyl)piperidin-4-yl]-1H-pyrrolo[2,3-b]pyridin-4-yl}-4-fluoro-N-(pyridin-4-ylmethyl)aniline The title compound was prepared essentially as described in Example 11B, substituting Example 422A (30 mg, 0.07 mmol) for Example 11A and isonicotinaldehyde for benzaldehyde. $^1$H NMR (400 MHz, Methanol-$d_4$) δ 1.05 (dddd, J=16.0, 8.7, 5.5, 2.0 Hz, 5H), 1.81 (dddd, J=23.7, 16.3, 11.8, 4.5 Hz, 2H), 2.05-2.21 (m, 2H), 2.51 (tdd, J=7.7, 5.3, 2.8 Hz, 2H), 2.80-2.99 (m, 1H), 3.05 (ddt, J=14.5, 10.3, 2.4 Hz, 2H), 3.86 (dt, J=12.6, 3.6 Hz, 2H), 5.94 (d, J=1.5 Hz, 1H), 6.68-6.72 (m, 2H), 7.05 (dd, J=5.1, 1.7 Hz, 2H), 7.46-7.48 (m, 2H), 7.64-7.66 (m, 2H), 7.91-7.96 (m, 1H), 8.10 (d, J=5.3 Hz, 1H). MS (ESI+) m/z 506 (M+H)+.

EXAMPLE 423

4-{[(3-{2-[1-(cyclopropylsulfonyl)piperidin-4-yl]-1H-pyrrolo[2,3-b]pyridin-4-yl}-4-fluorophenyl)amino]methyl}benzonitrile The title compound was prepared essentially as described in Example 11B, substituting Example 422A (30 mg, 0.07 mmol) for Example 11A and 4-formylbenzonitrile for benzaldehyde. $^1$H NMR (400 MHz, Methanol-$d_4$) δ 1.01-1.10 (m, 5H), 1.84 (td, J=12.4, 4.1 Hz, 2H), 2.07 (d, J=13.0 Hz, 2H), 2.18 (d, J=13.6 Hz, 1H), 2.51 (ddd, J=13.2, 8.0, 5.0 Hz, 1H), 2.77-2.91 (m, 1H), 3.09 (td, J=12.2, 2.6 Hz, 2H), 3.87 (d, J=11.9 Hz, 2H), 5.83 (s, 1H), 6.63-6.74 (m, 2H), 7.00 (d, J=9.5 Hz, 1H), 7.05 (dd, J=5.4, 2.0 Hz, 1H), 7.58 (d, J=8.0 Hz, 2H), 7.70-7.75 (m, 2H), 8.10 (d, J=5.1 Hz, 1H). MS (ESI+) m/z 530 (M+H)+.

EXAMPLE 424

3-{2-[1-(cyclopropylsulfonyl)piperidin-4-yl]-1H-pyrrolo[2,3-b]pyridin-4-yl}-N-(3,5-difluorobenzyl)-4-fluoroaniline The title compound was prepared essentially as described in Example 11B, substituting Example 422A (30 mg, 0.07 mmol) for Example 11A and 3,5-difluorobenzaldehyde for benzaldehyde. $^1$H NMR (400 MHz, Methanol-$d_4$) δ 0.99-1.13 (m, 5H), 1.30 (d, J=12.0 Hz, 1H), 1.78 (qd, J=12.3, 4.2 Hz, 2H), 2.10 (d, J=13.1 Hz, 2H), 2.51 (ddd, J=8.0, 5.4, 2.9 Hz, 1H), 2.81-2.93 (m, 1H), 3.03 (td, J=12.1, 2.6 Hz, 2H), 3.86 (dt, J=12.3, 3.5 Hz, 2H), 5.95 (s, 1H), 6.71 (dd, J=7.1, 4.3 Hz, 2H), 6.94-7.12 (m, 5H), 8.10 (d, J=5.1 Hz, 1H). MS (ESI+) m/z 541 (M+H)+.

EXAMPLE 425

3-{2-[1-(cyclopropylsulfonyl)piperidin-4-yl]-1H-pyrrolo[2,3-b]pyridin-4-yl}-4-fluoro-N-[3-(methylsulfonyl)benzyl]aniline The title compound was prepared essentially as described in Example 11B, substituting Example 422A (30 mg, 0.07 mmol) for Example 11A and 3-(methylsulfonyl)benzaldehyde for benzaldehyde. $^1$H NMR (400 MHz, Methanol-$d_4$) δ 0.98-1.11 (m, 5H), 1.66-1.80 (m, 2H), 1.98-2.09 (m, 2H), 2.10-2.19 (m, 1H), 2.49 (ddd, J=9.6, 7.0, 3.9 Hz, 1H), 2.86 (ddd, J=11.9, 8.2, 3.7 Hz, 1H), 3.00 (dd, J=12.1, 2.5 Hz, 2H), 3.05 (s, 3H), 3.79-3.88 (m, 2H), 5.93 (d, J=1.4 Hz, 1H), 6.72 (dd, J=8.4, 4.4 Hz, 2H), 6.95-7.08 (m, 2H), 7.60 (t, J=7.7 Hz, 1H), 7.70-7.74 (m, 1H), 7.86 (dt, J=7.9, 1.4 Hz, 1H), 7.99 (t, J=1.6 Hz, 1H), 8.09 (d, J=4.9 Hz, 1H). MS (ESI+) m/z 583 (M+H)+.

EXAMPLE 426

4-(4-{2-fluoro-5-[(3-fluorobenzyl)amino]phenyl}-1H-pyrrolo[2,3-b]pyridin-2-yl)piperidine-1-sulfonamide To a solution of Example 354 (50 mg, 0.119 mmol) in $CH_2Cl_2$ (5 mL) was added triethylamine (0.033 mL, 0.239 mmol) and Example 218A (36 mg, 0.119 mmol) at room temperature. The mixture was stirred at room temperature overnight and was concentrated. The residue was purified by HPLC (Zorbax, C-18, 250×2.54 column, Mobile phase A: 0.1% trifluoroacetic acid in $H_2O$; B: 0.1% trifluoroacetic acid in $CH_3CN$; 0-100% gradient) to provide the title compound. $^1$H NMR (400 MHz, $CD_3OD$): δ 1.70-1.81 (m, 2 H), 2.03-2.09 (m, 2 H), 2.90-2.96 (m, 1 H), 3.01-3.10 (m, 2 H), 3.91-3.98 (m, 2 H), 4.38 (s, 2 H), 6.13 (s, 1 H), 6.73 (dd, J=5.80, 3.05 Hz, 1 H), 6.82-6.86 (m, 1 H), 6.98-7.03 (m, 1 H), 7.06-7.15 (m, 2 H), 7.20 (d, J=7.63 Hz, 1 H), 7.33-7.41 (m, 2 H), 8.23 (d, J=5.80 Hz, 1 H); MS (DCI/$NH_3$) m/z 498 (M+H)+.

EXAMPLE 427

3-[4-(4-{2-fluoro-5-[(3-fluorobenzyl)amino]phenyl}-1H-pyrrolo[2,3-b]pyridin-2-yl)piperidin-1-yl]propane-1,2-diol To a solution of Example 354 (60 mg, 0.143) in methanol (5 mL) was added 2,3-dihydroxypropanal (19.37 mg, 0.215 mmol). This solution was stirred at room temperature for 1 hour and sodium cyanoborohydride (18 mg, 0.287 mmol) was then added. The mixture was stirred at 50° C. for 60 hours. The volatiles were removed, and the residue was purified by HPLC (Zorbax, C-18, 250×2.54 column, Mobile phase A: 0.1% trifluoroacetic acid in $H_2O$; B: 0.1% trifluoroacetic acid in $CH_3CN$; 0-100% gradient) to provide the title compound. $^1$H NMR (400 MHz, $CD_3OD$): δ2.00-2.11 (m, 2 H), 2.35 (t, J=14.50 Hz, 4 H), 3.14-3.28 (m, 4 H), 3.52-3.62 (m, 3 H), 3.76-3.86 (m, 2 H), 4.06-4.11 (m, 1 H), 4.39 (s, 2 H), 6.29 (s, 1 H), 6.75-6.78 (m, 1 H), 6.80-6.85 (m, 1 H), 6.96-7.02 (m, 1 H), 7.09 (d, J=10.07 Hz, 1 H), 7.11-7.15 (m, 1 H), 7.21 (d, J=7.63 Hz, 1 H), 7.32 (d, J=6.10 Hz, 1 H), 7.35-7.38 (m, 1 H), 8.29 (d, J=5.80 Hz, 1 H); MS (DCI/$NH_3$) m/z 493 (M+H)+.

EXAMPLE 428

4-(5-fluoro-2-methoxyphenyl)-2-[4-(pyrrolidin-1-yl)cyclohex-1-en-1-yl]-1H-pyrrolo[2,3-b]pyridine The title compound was prepared essentially as described in Example 219B, substituting ethyl 4-(4,4,5,5-tetramethyl-1,3,2-dioxaborolan-2-yl)cyclohex-3-enecarboxylate with 1-(4-(4,4,5,5-tetramethyl-1,3,2-dioxaborolan-2-yl)cyclohex-3-en-1-yl)pyrrolidine. $^1$H NMR (500 MHz, DMSO-$d_6$) δ ppm 11.72 (s, 1 H) 8.17 (d, J=4.88 Hz, 1 H) 7.13-7.32 (m, 3 H) 7.01 (d, J=4.88 Hz, 1 H) 6.46 (s, 1 H) 6.16 (s, 1 H) 3.73 (s, 3 H) 2.52-2.59 (m, J=5.19 Hz, 3 H) 2.38-2.46 (m, 1 H)

2.28-2.38 (m, 2 H) 2.19-2.27 (m, 1 H) 2.09-2.19 (m, 1 H) 2.04 (s, 1 H) 1.68 (s, 4 H) 1.42-1.55 (m, 1 H). MS (ESI): 392.1 (M+H)$^+$.

EXAMPLE 429

4-(5-fluoro-2-methoxyphenyl)-2-[1-(methylsulfonyl)-2,5-dihydro-1H-pyrrol-3-yl]-1H-pyrrolo[2,3-b]pyridine

EXAMPLE 429A tert-butyl 3-(4-(5-fluoro-2-methoxyphenyl)-1-(phenylsulfonyl)-1H-pyrrolo[2,3-b]pyridin-2-yl)-2,5-dihydro-1H-pyrrole-1-carboxylate A suspension of phenylallylchloro[1,3-bis(diisopropylphenyl)-2-imidazol-2-ylidene]palladium(II) (27.7 mg, 0.034 mmol), Example 87B (344 mg, 0.678 mmol), tert-butyl 3-(4,4,5,5-tetramethyl-1,3,2-dioxaborolan-2-yl)-2,5-dihydro-1H-pyrrole-1-carboxylate (200 mg, 0.678 mmol) and sodium carbonate (1.959 mL, 2.033 mmol) in dioxane (4 ml) was heated at 95° C. for 90 min. The reaction mixture was diluted with ethyl acetate, water layer separated and the organic layer dried over magnesium sulfate, filtered and concentrated. The crude product was purified by flash chromatography (24 g silica gel, gradient 20 to 100% ethyl acetate/heptanes) to give the title compound.

EXAMPLE 429B 2-(2,5-dihydro-1H-pyrrol-3-yl)-4-(5-fluoro-2-methoxyphenyl)-1-(phenylsulfonyl)-1H-pyrrolo[2,3-b]pyridine A suspension of Example 429A (0.143 g, 0.260 mmol) and trifluoroacetic acid (1 ml, 12.98 mmol) in dichloromethane (1.5 mL) was stirred at room temperature for 150 minutes. The reaction mixture was concentrated and used in next step without purification.

EXAMPLE 429C 4-(5-fluoro-2-methoxyphenyl)-2-(1-(methylsulfonyl)-2,5-dihydro-1H-pyrrol-3-yl)-1-(phenylsulfonyl)-1H-pyrrolo[2,3-b]pyridine The title compound was prepared according the procedure described in Example 119, using Example 429B in place of Example 87D.

EXAMPLE 429D 4-(5-fluoro-2-methoxyphenyl)-2-[1-(methylsulfonyl)-2,5-dihydro-1H-pyrrol-3-yl]-1H-pyrrolo[2,3-b]pyridine The title compound was prepared according the procedure described in Example 1280C, using Example 429C in place of Example 1280B. $^1$H NMR (400 MHz, DMSO-d$_6$) δ ppm 2.96 (s, 3H), 3.75 (s, 4H), 4.30 (q, J=3.5 Hz, 2H), 4.47 (td, J=4.3, 1.9 Hz, 2H), 6.32 (d, J=2.0 Hz, 1H), 6.49 (q, J=2.0 Hz, 1H), 7.10 (d, J=5.0 Hz, 1H), 7.17-7.40 (m, 3H), 8.26 (d, J=5.0 Hz, 1H), 12.14 (d, J=2.5 Hz, 1H) MS (ESI$^+$) m/z 388.1 (M+H)$^+$.

EXAMPLE 430

3-[4-(4-{2-fluoro-5-[(3-fluorobenzyl)oxy]phenyl}-1H-pyrrolo[2,3-b]pyridin-2-yl)-3,6-dihydropyridin-1(2H)-yl]propane-1,2-diol The title compound was prepared using the procedure described in Example 344B, using 2,3-dihydroxypropanal in place of 4-methyltetrahydro-2H-pyran-4-carbaldehyde and Example 382D in place of Example 344A. $^1$H NMR (400 MHz, DMSO-d$_6$) δ ppm 2.71-2.89 (m, 2 H) 3.07-3.19 (m, 1 H) 3.25-3.38 (m, 3 H) 3.41-3.49 (m, 1 H) 3.62-3.74 (m, 2 H) 4.01-4.19 (m, 2 H) 5.21 (s, 2 H) 6.41 (s, 1 H) 6.48 (s, 1 H) 7.12-7.22 (m, 4 H) 7.28-7.39 (m, 3 H) 7.40-7.49 (m, 1 H) 8.31 (d, 1 H) 9.69 (s, 1 H) 12.12 (s, 1 H); LCMS: 492 (M+H)$^+$.

EXAMPLE 431

3-[4-(4-{2,4-difluoro-5-[(3-fluorobenzyl)amino]phenyl}-1H-pyrrolo[2,3-b]pyridin-2-yl)-3,6-dihydropyridin-1(2H)-yl]propane-1,2-diol The title compound was prepared using the procedure described in Example 344B, using 2,3-dihydroxypropanal in place of 4-methyltetrahydro-2H-pyran-4-carbaldehyde and Example 408C in place of Example 344A. $^1$H NMR (400 MHz, DMSO-d$_6$) δ ppm 2.54-2.80 (m, 2 H) 3.08-3.20 (m, 1 H) 3.27-3.38 (m, 4 H) 3.47 (dd, 2 H) 4.04-4.17 (m, 2 H) 4.41 (s, 2 H) 6.12 (s, 1 H) 6.41 (s, 1 H) 6.69 (dd, 1 H) 6.97 (d, 1 H) 7.07 (t, 1 H) 7.12-7.24 (m, 2 H) 7.28-7.46 (m, 2 H) 8.23 (d, 1 H) 9.70 (s, 1 H) 12.06 (s, 1 H); LCMS: 509 (M+H)$^+$.

EXAMPLE 432

2-({4-[4-(5-fluoro-2-methoxyphenyl)-1H-pyrrolo[2,3-b]pyridin-2-yl]-3,6-dihydropyridin-1(2H)-yl}methyl)-1H-benzimidazole A 20 mL vial was charged with a 1.5 mL of ammonium acetate/acetic acid buffer solution (pH 4) in methanol. To this Example 87D (35.24 mg, 0.109 mmol) was added to form a suspension. 1H-benzo[d]imidazole-2-carbaldehyde (23.89 mg, 1.5 eq, 0.164 mmol) and Si—BH$_3$CN (from Silicycle, 0.88 mmol/g loading, 371.49 mg) were then added. The vial was capped and placed to stir at 40° C. overnight. Upon completion, the crude mixture was filtered, concentrated, and purified by HPLC (see Example 360 for protocols) to provide the title compound as a trifluoroacetic acid salt. $^1$H NMR (400 MHz, pyridine-d$_5$) δ ppm 2.57 (q, J=4.1, 3.2 Hz, 2H), 2.83 (t, J=5.7 Hz, 2H), 3.39 (q, J=2.8 Hz, 2H), 3.71 (s, 3H), 4.17 (s, 2H), 6.61 (s, 1H), 6.64-6.67 (m, 1H), 7.09 (dd, J=9.1, 4.5 Hz, 1H), 7.26 (ddd, J=9.1, 7.9, 3.2 Hz, 1H), 7.32 (d, J=4.9 Hz, 1H), 7.34-7.39 (m, 2H), 7.49 (dd, J=8.9, 3.2 Hz, 1H), 7.89 (dd, J=6.0, 3.2 Hz, 2H), 8.58 (d, J=5.0 Hz, 1H). MS (ESI$^+$) m/z 454.2 (M+H)$^+$.

EXAMPLE 429

4-(5-fluoro-2-methoxyphenyl)-2-[1-(methylsulfonyl)-2,5-dihydro-1H-pyrrol-3-yl]-1H-pyrrolo[2,3-b]pyridine

EXAMPLE 429A tert-butyl 3-(4-(5-fluoro-2-methoxyphenyl)-1-(phenylsulfonyl)-1H-pyrrolo[2,3-b]pyridin-2-yl)-2,5-dihydro-1H-pyrrole-1-carboxylate A suspension of phenylallylchloro[1,3-bis(diisopropylphenyl)-2-imidazol-2-ylidene]palladium(II) (27.7 mg, 0.034 mmol), Example 87B (344 mg, 0.678 mmol), tert-butyl 3-(4,4,5,5-tetramethyl-1,3,2-dioxaborolan-2-yl)-2,5-dihydro-1H-pyrrole-1-carboxylate (200 mg, 0.678 mmol) and sodium carbonate (1.959 mL, 2.033 mmol) in dioxane (4 ml) was heated at 95° C. for 90 minutes. The reaction mixture was diluted with ethyl acetate, the water layer was separated and the organic layer was dried over magnesium sulfate, filtered and concentrated. The crude material was purified by flash chromatography (24 g silica gel, gradient 20 to 100% ethyl acetate/heptanes).

EXAMPLE 429B 2-(2,5-dihydro-1H-pyrrol-3-yl)-4-(5-fluoro-2-methoxyphenyl)-1-(phenylsulfonyl)-1H-pyrrolo[2,3-b]pyridine A suspension of Example 429A (0.143 g, 0.260 mmol) and trifluoroacetic acid (1 ml, 12.98 mmol) in dichloromethane (1.5 mL) was stirred at room temperature for 150 minutes. The reaction mixture was concentrated and used in next step without purification.

EXAMPLE 440

4-chloro-3-[2-(2,5-dihydro-1H-pyrrol-3-yl)-1H-pyrrolo[2,3-b]pyridin-4-yl]-N-(pyridin-3-ylmethyl)aniline

EXAMPLE 440A tert-butyl 3-(4-chloro-1-tosyl-1H-pyrrolo[2,3-b]pyridin-2-yl)-2,5-dihydro-1H-pyrrole-1-carboxylate A suspension of phenylallylchloro[1,3-bis(diisopropylphenyl)-2-imidazol-2-ylidene]palladium(II) (66.4 mg, 0.081 mmol), 4-chloro-2-iodo-1-tosyl-1H-pyrrolo[2,3-b]pyridine (1.173 g, 2.71 mmol), tert-butyl 3-(4,4,5,5-tetramethyl-1,3,2-dioxaborolan-2-yl)-2,5-dihydro-1H-pyrrole-1-carboxylate (800 mg, 2.71 mmol) and sodium carbonate (8 mL, 8.30 mmol) in dioxane (20 mL) was heated at 95° C. for 90 minutes. The reaction mixture was diluted with ethyl acetate, the water layer was separated and the organic layer was dried over magnesium sulfate, filtered and concentrated. The crude material was purified by flash chromatography (24 g silica gel, 20-100% ethyl acetate/heptanes) to provide the title compound.

EXAMPLE 440B tert-butyl 3-(4-chloro-1H-pyrrolo[2,3-b]pyridin-2-yl)-2,5-dihydro-1H-pyrrole-1-carboxylate A suspension of Example 440A (0.497 g, 1.049 mmol) and sodium hydroxide (1 mL, 5.00 mmol) in dioxane (5 mL) was heated at 80° C. for 2 hours. The reaction mixture was diluted with ethyl acetate, water separated, dried over magnesium sulfate, filtered and concentrated. The crude product was used in next step without purification.

EXAMPLE 440C tert-butyl 3-(4-(5-amino-2-chlorophenyl)-1H-pyrrolo[2,3-b]pyridin-2-yl)-2,5-dihydro-1H-pyrrole-1-carboxylate A suspension of potassium phosphate (0.617 g, 2.91 mmol), phenylallylchloro[1,3-bis(diisopropylphenyl)-2-imidazol-2-ylidene]palladium(II) (0.038 g, 0.058 mmol), Example 440B (0.31 g, 0.969 mmol) and (5-amino-2-chlorophenyl)boronic acid (0.199 g, 1.163 mmol) in tetrahydrofuran (1.5 mL)/water (0.5 mL) was heated at 60° C. for 90 minutes. The reaction mixture was diluted with ethyl acetate, the water layer was separated and the organic layer was dried over magnesium sulfate, filtered and concentrated. The crude product was used in next step without purification.

EXAMPLE 440D tert-butyl 3-(4-(2-chloro-5-((pyridin-3-ylmethyl)amino)phenyl)-1H-pyrrolo[2,3-b]pyridin-2-yl)-2,5-dihydro-H-pyrrole-1-carboxylate To a solution of Example 440C (50 mg, 0.130 mmol) in dichloromethane (1 mL)/methanol (1 mL)/triethylamine (0.036 mL, 0.260 mmol) was added acetic acid (0.037 ml, 0.651 mmol) and nicotinaldehyde (0.016 ml, 0.170 mmol). To the reaction mixture, MP-cyanoborohydride (209 mg, 0.52 mmol) was added and the reaction mixture was shaken for 4 hours at room temperature. The reaction mixture was filtered and washed with 1:1 dichloromethane/methanol (2×3 mL). The product was used without purification.

EXAMPLE 440E 4-chloro-3-[2-(2,5-dihydro-1H-pyrrol-3-yl)-1H-pyrrolo[2,3-b]pyridin-4-yl]-N-(pyridin-3-ylmethyl)aniline A suspension of Example 440D (42.7 mg, 0.085 mmol) and trifluoroacetic acid (0.5 mL, 6.49 mmol) in dichloromethane (1.5 mL) was stirred at room temperature for 150 minutes. The reaction mixture was concentrated and purified by RP HPLC (20-100% $CH_3CN$/water/trifluoroacetic acid 0.1%) to provide the title compound. $^1$H NMR (400 MHz, DMSO-$d_6$) δ ppm 3.90-4.42 (m, 6H), 6.22 (d, J=1.9 Hz, 1H), 6.52 (t, J=2.3 Hz, 1H), 6.62-6.78 (m, 2H), 6.98 (d, J=4.9 Hz, 1H), 7.29 (d, J=8.7 Hz, 1H), 7.70 (dd, J=7.9, 5.3 Hz, 1H), 8.12 (dt, J=8.0, 1.7 Hz, 1H), 8.30 (d, J=4.9 Hz, 1H), 8.65 (dd, J=5.1, 1.5 Hz, 1H), 8.72 (d, J=2.0 Hz, 1H), 9.37-9.48 (m, 2H), 12.26 (d, J=2.2 Hz, 1H). MS (ESI$^+$) m/z 402.2 (M+H)$^+$.

EXAMPLE 441

4-chloro-3-[2-(2,5-dihydro-1H-pyrrol-3-yl)-1H-pyrrolo[2,3-b]pyridin-4-yl]-N-(3-fluorobenzyl)aniline

EXAMPLE 441A tert-butyl 3-(4-(2-chloro-5-((3-fluorobenzyl)amino)phenyl)-1H-pyrrolo[2,3-b]pyridin-2-yl)-2,5-dihydro-1H-pyrrole-1-carboxylate The title compound was prepared according the procedure described in Example 440D, using 3-fluorobenzaldehyde in place of nicotinaldehyde.

EXAMPLE 441B 4-chloro-3-[2-(2,5-dihydro-1H-pyrrol-3-yl)-1H-pyrrolo[2,3-b]pyridin-4-yl]-N-(3-fluorobenzyl)aniline The title compound was prepared according the procedure described in Example 440E, using Example 441A in place of Example 440D. ¹H NMR (400 MHz, DMSO-d₆) δ ppm 4.19 (d, J=5.0 Hz, 6H), 6.22 (d, J=1.9 Hz, 1H), 6.52 (t, J=2.2 Hz, 1H), 6.58-6.74 (m, 2H), 6.89-7.11 (m, 2H), 7.12-7.22 (m, 2H), 7.24-7.43 (m, 2H), 8.29 (d, J=4.9 Hz, 1H), 9.32-9.43 (m, 2H), 12.26 (d, J=2.3 Hz, 1H). MS (ESI⁺) m/z 419.2 (M+H)⁺.

EXAMPLE 442

4-chloro-3-[2-(2,5-dihydro-1H-pyrrol-3-yl)-1H-pyrrolo[2,3-b]pyridin-4-yl]-N-(tetrahydro-2H-pyran-3-ylmethyl)aniline

EXAMPLE 442A tert-butyl 3-(4-(2-chloro-5-(((tetrahydro-2H-pyran-3-yl)methyl)amino)phenyl)-1H-pyrrolo[2,3-b]pyridin-2-yl)-2,5-dihydro-1H-pyrrole-1-carboxylate The title compound was prepared according the procedure described in Example 440D, using tetrahydro-2H-pyran-3-carbaldehyde in place of nicotinaldehyde.

EXAMPLE 442B 4-chloro-3-[2-(2,5-dihydro-1H-pyrrol-3-yl)-1H-pyrrolo[2,3-b]pyridin-4-yl]-N-(tetrahydro-2H-pyran-3-ylmethyl)aniline The title compound was prepared according the procedure described in Example 440E, using Example 442A in place of Example 440D. ¹H NMR (400 MHz, DMSO-d₆) δ ppm 1.18-1.66 (m, 4H), 1.66-1.95 (m, 2H), 2.79-3.02 (m, 2H), 3.13 (dd, J=11.1, 8.9 Hz, 1H), 3.32 (td, J=10.6, 2.8 Hz, 2H), 4.32 (d, J=4.7 Hz, 2H), 6.33 (d, J=2.0 Hz, 1H), 6.53 (t, J=2.2 Hz, 1H), 6.60 (d, J=2.8 Hz, 1H), 6.67 (dd, J=8.8, 2.8 Hz, 1H), 7.02 (d, J=4.9 Hz, 1H), 7.27 (d, J=8.7 Hz, 1H), 8.31 (d, J=4.9 Hz, 1H), 9.34 (t, J=5.9 Hz, 2H), 12.26 (d, J=2.2 Hz, 1H). MS (ESI⁺) m/z 409.2 (M+H)⁺.

EXAMPLE 443

4-chloro-3-[2-(2,5-dihydro-1H-pyrrol-3-yl)-1H-pyrrolo[2,3-b]pyridin-4-yl]-N-(piperidin-4-ylmethyl)aniline

EXAMPLE 443A tert-butyl 4-(((3-(2-(1-(tert-butoxycarbonyl)-2,5-dihydro-1H-pyrrol-3-yl)-1H-pyrrolo[2,3-b]pyridin-4-yl)-4-chlorophenyl)amino)methyl)piperidine-1-carboxylate The title compound was prepared according the procedure described in Example 440D, using tert-butyl 4-formylpiperidine-1-carboxylate in place of nicotinaldehyde.

EXAMPLE 443B 4-chloro-3-[2-(2,5-dihydro-1H-pyrrol-3-yl)-1H-pyrrolo[2,3-b]pyridin-4-yl]-N-(piperidin-4-ylmethyl)aniline The title compound was prepared according the procedure described in Example 440E, using Example 443A in place of Example 440D. ¹H NMR (400 MHz, DMSO-d₆) δ ppm 1.07-1.38 (m, 2H), 1.68-1.95 (m, 3H), 2.90 (dd, J=39.7, 9.2 Hz, 4H), 3.16-3.44 (m, 2H), 3.16-4.44 (m, 4H), 6.33 (d, J=1.9 Hz, 1H), 6.53 (t, J=2.2 Hz, 1H), 6.62 (d, J=2.8 Hz, 1H), 6.69 (dd, J=8.8, 2.8 Hz, 1H), 7.01 (d, J=4.9 Hz, 1H), 7.28 (d, J=8.7 Hz, 1H), 8.31 (d, J=4.9 Hz, 2H), 8.61 (d, J=11.3 Hz, 1H), 9.49 (p, J=5.5 Hz, 2H), 12.27 (d, J=2.2 Hz, 1H) MS (ESI⁺) m/z 408.2 (M+H)⁺.

EXAMPLE 444

5-fluoro-4-(5-fluoro-2-methoxyphenyl)-2-(piperidin-4-yl)-1H-pyrrolo[2,3-b]pyridine

EXAMPLE 444A tert-butyl 4-((4-chloro-5-fluoro-2-pivalamidopyridin-3-yl)ethynyl)piperidine-1-carboxylate The title compound was prepared using the procedure described in Example 1E, using N-(4-chloro-5-fluoro-3-iodopyridin-2-yl)pivalamide (1 g, 2.80 mmol) in place of Example 1A, and using tert-butyl 4-ethynylpiperidine-1-carboxylate (0.6 g, 2.87 mmol) in place of Example 1D. LCMS: 438.4 (M+H)⁺.

EXAMPLE 444B tert-butyl 4-(4-chloro-5-fluoro-1H-pyrrolo[2,3-b]pyridin-2-yl)piperidine-1-carboxylate The mixture of Example 444A (0.92 g, 2.1 mmol), potassium tert-butoxide (0.154 g, 2.1 mmol) and 18-crown-6 (0.22 g, 0.83 mmol) was suspended in tert-butanol (3 mL) in a 5 mL microwave tube. The mixture was heated at 130° C. for 0.5 hours using a Biotage Initiator (model 355302). After filtration, the solvent was removed under vacuum. The crude product was purified by preparative reverse phase column (AnaLogix, C-18, 150 g) with gradient elution from 0-100% acetonitrile in water with 0.1% trifluoroacetic acid to afford the title compound as trifluoroacetate salt. LCMS: 354.09 (M+H)⁺.

EXAMPLE 444C tert-butyl 4-(5-fluoro-4-(5-fluoro-2-methoxyphenyl)-1H-pyrrolo[2,3-b]pyridin-2-yl)piperidine-1-carboxylate The title compound was prepared using the procedure described in Example 94C, using Example 444B (0.48 g, 1.34 mmol) in place of Example 94B. LC/MS: 444.4 (M+H)⁺.

EXAMPLE 444D 5-fluoro-4-(5-fluoro-2-methoxyphenyl)-2-(piperidin-4-yl)-1H-pyrrolo[2,3-b]pyridine Into a 20 mL vial was added Example 444C (0.54 g, 1.21 mmol) in dichloromethane (5 mL). HCl (4M in dioxane) (5 mL, 20.00 mmol) was added. The mixture was stirred at room temperature for two hours. After removing the solvents, the product was purified by reverse-phase HPLC on a Sunfire C8 column (30×100 mm, 5 μm particle size, flow rate 30 mL/minute) using a gradient of 20-100% acetonitrile in 0.1% aqueous trifluoroacetic acid to provide the title compound as the trifluoroacetic acid salt. ¹H NMR (400 MHz, DMSO-d₆): δ 1.47-1.61 (m, 2 H) 1.87-1.94 (m, 3 H)

2.54-2.63 (m, 2 H) 2.72-2.83 (m, 1 H) 2.97-3.05 (m, 2 H) 3.72 (s, 3 H) 5.86 (s, 1 H) 7.17-7.24 (m, 2 H) 7.27-7.35 (m, 1 H) 8.12 (d, J=2.75 Hz, 1 H) 11.70 (s, 1 H). MS (ESI+) m/z 344.2 (M+H)+.

The following compounds (concluding with Example 447) were prepared essentially as described in Example 410, substituting the appropriate isocyanate reagent.

EXAMPLE 445

N-cyclohexyl-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, DMSO-$d_6$) δ ppm 0.97-1.32 (m, 5H), 1.47-1.82 (m, 5H), 2.40-2.47 (m, 2H), 3.39-3.56 (m, 3H), 3.74 (s, 3H), 3.98-4.04 (m, 2H), 6.16 (d, J=7.7 Hz, 1H), 6.24 (d, J=2.0 Hz, 1H), 6.51 (bs, 1H), 7.03 (d, J=4.9 Hz, 1H), 7.16-7.31 (m, 3H), 8.20 (d, J=4.9 Hz, 1H), 11.79-11.84 (m, 1H). MS (ESI+) m/z 449.1 (M+H)+.

EXAMPLE 446

4-[4-(5-fluoro-2-methoxyphenyl)-1H-pyrrolo[2,3-b]pyridin-2-yl]-N-(4-methoxybenzyl)-3,6-dihydropyridine-1(2H)-carboxamide $^1$H NMR (400 MHz, DMSO-$d_6$) δ ppm 2.42-2.48 (m, 2H), 3.54 (t, J=5.5 Hz, 2H), 3.69-3.76 (m, 6H), 4.02-4.08 (m, 2H), 4.12-4.22 (m, 2H), 6.25 (d, J=2.0 Hz, 1H), 6.52 (bs, 1H), 6.82-6.90 (m, 2H), 7.00-7.06 (m, 2H), 7.13-7.32 (m, 5H), 8.20 (d, J=4.9 Hz, 1H), 11.78-11.83 (m, 1H). MS (ESI+) m/z 487.1 (M+H)+.

EXAMPLE 447

4-[4-(5-fluoro-2-methoxyphenyl)-1H-pyrrolo[2,3-b]pyridin-2-yl]-N-phenyl-3,6-dihydropyridine-1(2H)-carboxamide $^1$H NMR (400 MHz, DMSO-$d_6$) δ ppm 2.51-2.59 (m, 2H), 3.66 (t, J=5.6 Hz, 2H), 3.74 (s, 3H), 4.18-4.24 (m, 2H), 6.28 (d, J=2.0 Hz, 1H), 6.57 (bs, 1H), 6.90-6.98 (m, 1H), 7.04 (d, J=4.9 Hz, 1H), 7.16-7.32 (m, 5H), 7.45-7.51 (m, 2H), 8.21 (d, J=4.9 Hz, 1H), 8.52 (s, 1H), 11.83-11.88 (m, 1H). MS (ESI+) m/z 443.1 (M+H)+.

EXAMPLE 448

4-(4-{2-fluoro-5-[(pyridin-4-ylmethyl)amino]phenyl}-1H-pyrrolo[2,3-b]pyridin-2-yl)piperidine-1-sulfonamide The title compound was prepared essentially as described in Example 426, substituting Example 357 for Example 354. $^1$H NMR (400 MHz, CD$_3$OD): δ1.77-1.86 (m, 2 H), 2.16 (d, J=10.99 Hz, 2 H), 2.76-2.83 (m, 2 H), 2.92-3.00 (m, 1 H), 3.77 (d, J=11.90 Hz, 2 H), 4.74 (s, 2 H), 6.36 (s, 1 H), 6.73-6.77 (m, 1 H), 6.83 (dd, J=5.95, 2.90 Hz, 1 H), 7.09-7.16 (m, 1 H), 7.40 (d, J=6.10 Hz, 1 H), 8.07 (d, J=6.71 Hz, 2 H), 8.27 (d, J=6.10 Hz, 1 H), 8.76 (d, J=6.71 Hz, 2 H). MS (DCI/NH$_3$) m/z 481 (M+H)+.

EXAMPLE 449

5-fluoro-4-(5-fluoro-2-methoxyphenyl)-2-[1-(methylsulfonyl)piperidin-4-yl]-1H-pyrrolo[2,3-b]pyridine The title compound was prepared using the procedure described in Example 223D, using Example 444D (0.045 g, 0.13 mmol) in place of Example 223C. $^1$H NMR (400 MHz, DMSO-$d_6$): δ 1.67-1.78 (m, 2 H) 2.03-2.10 (m, 2 H) 2.79-2.91 (m, 6 H) 3.60-3.66 (m, 2 H) 3.72 (s, 3 H) 5.95 (d, J=1.53 Hz, 1 H) 7.18-7.25 (m, 2 H) 7.29-7.35 (m, 1 H) 8.14 (d, J=2.44 Hz, 1 H) 11.78 (s, 1 H). MS (ESI+) m/z 422.1 (M+H)+.

EXAMPLE 450

3-{4-[5-fluoro-4-(5-fluoro-2-methoxyphenyl)-1H-pyrrolo[2,3-b]pyridin-2-yl]piperidin-1-yl}propane-1,2-diol The title compound was prepared using the procedure described in Example 149, using Example 444D (0.045 g, 0.13 mmol) in place of Example 135B. $^1$H NMR (500 MHz, DMSO-$d_6$): δ 3.01-3.12 (m, 2 H) 3.13-3.41 (m, 4 H) 3.44-3.67 (m, 3 H) 3.72 (s, 3 H) 3.91-4.00 (m, 1 H) 5.95 (s, 1 H) 7.12-7.23 (m, 2 H) 7.23-7.30 (m, 1 H) 8.13 (d, J=2.75 Hz, 1 H) 11.54 (s, 1 H). MS (ESI+) m/z 418.2 (M+H)+.

EXAMPLE 451

1-{4-[5-fluoro-4-(5-fluoro-2-methoxyphenyl)-1H-pyrrolo[2,3-b]pyridin-2-yl]piperidin-1-yl}ethanone The title compound was prepared using the procedure described in Example 99, using Example 444D (0.045 g, 0.13 mmol) in place of Example 94D. $^1$H NMR (500 MHz, DMSO-$d_6$): δ 1.42-1.53 (m, 1 H) 1.59-1.71 (m, 1 H) 1.90-2.03 (m, 5 H) 2.58-2.66 (m, 1 H) 2.92-3.00 (m, 1 H) 3.09-3.17 (m, 1 H) 3.72 (s, 3 H) 3.84-3.92 (m, 1 H) 4.41-4.47 (m, 1 H) 5.91 (d, J=1.53 Hz, 1 H) 7.17-7.25 (m, 2 H) 7.28-7.34 (m, 1 H) 8.13 (d, J=2.44 Hz, 1 H) 11.74 (s, 1 H). MS (ESI+) m/z 386.2 (M+H)+.

EXAMPLE 452

3-[4-(4-{5-[(3,5-difluorobenzyl)amino]-2-fluorophenyl}-1H-pyrrolo[2,3-b]pyridin-2-yl)piperidin-1-yl]propane-1,2-diol The title compound was prepared essentially as described in Examples 149, substituting Example 365 (30 mg, 0.07 mmol) for Example 135B. $^1$H NMR (400 MHz, DMSO-$d_6$) δ 1.71-2.11 (m, 2H), 2.23 (ddd, J=21.0, 14.7, 4.0 Hz, 3H), 2.93-3.29 (m, 5H), 3.64 (dd, J=12.4, 5.3 Hz, 2H), 3.96 (d, J=4.0 Hz, 1H), 4.35 (s, 2H), 5.94 (t, J=2.1 Hz, 1H), 6.70 (dd, J=6.3, 3.2 Hz, 2H), 6.98-7.17 (m, 5H), 8.22 (d, J=5.0 Hz, 1H). MS (ESI+) m/z 511 (M+H)+.

EXAMPLE 453

4-[4-(5-fluoro-2-methoxyphenyl)-1H-pyrrolo[2,3-b]pyridin-2-yl]-N-[2-(morpholin-4-yl)ethyl]-3,6-dihydropyridine-1(2H)-carboxamide To a suspension of Example 87D (40.0 mg, 0.101 mmol) in N,N-dimethylformamide (1.5 mL) was added 1-chloro-2-isocyanatoethane (15.98 mg, 0.151 mmol) and triethylamine (0.084 mL, 0.606 mmol). The reaction was stirred overnight. Morpholine (0.035 mL, 0.404 mmol) was added and the reaction mixture was heated 50° C. for 7 hours. The reaction mixture was treated with water and brine and extracted with ethyl acetate. The combined organic layers were washed with water, dried over MgSO$_4$, filtered, concentrated, and purified by HPLC (see protocols in Example 361) to provide the title compound as a trifluoroacetic acid salt. ¹H NMR (400 MHz, methanol-d₄) δ ppm 2.59-2.64 (m, 2H), 3.11-3.22 (m, 2H), 3.27-3.29 (m, 2H), 3.56-3.70 (m, 6H), 3.71-3.84 (m, 5H), 4.02-4.12 (m, 2H), 4.19 (q, J=2.7 Hz, 2H), 6.49-6.60 (m, 2H), 7.18-7.34 (m, 3H), 7.45 (d, J=5.9 Hz, 1H), 8.28 (d, J=6.0 Hz, 1H). MS (ESI⁺) m/z 480.1 (M+H)⁺.

EXAMPLE 454

4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine

EXAMPLE 454A 4-(5-fluoro-2-methoxyphenyl)-2-(1-(vinylsulfonyl)-1,2,3,6-tetrahydropyridin-4-yl)-1H-pyrrolo[2,3-b]pyridine To a suspension of Example 87D (90.0 mg, 0.227 mmol) in tetrahydrofuran (4.5 mL) was added 2-chloroethanesulfonyl chloride (0.047 ml, 0.454 mmol) and triethylamine (0.190 mL, 1.363 mmol). The reaction was stirred for 4 hours. The reaction mixture was diluted with ethyl acetate and washed with brine. The organic layer was dried over MgSO₄, filtered, concentrated and purified on a 12 g silica column using the ISCO Companion flash system eluting with methanol/ethyl acetate (2:98 to 5:95) to provide the title compound. MS (ESI⁺) m/z 414.1 (M+H)⁺.

EXAMPLE 454B 4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine A mixture of Example 454A (19 mg, 0.046 mmol) and morpholine (0.016 mL, 0.184 mmol) in methanol (1 mL) was stirred at 50° C. for 3 hours. The suspension was filtered, washed with cold methanol and vacuum oven-dried to provide the title compound. ¹H NMR (500 MHz, DMSO-d₆) δ ppm 2.37-2.43 (m, 4H), 2.67 (t, J=7.2 Hz, 2H), 3.43 (t, J=5.7 Hz, 2H), 3.51-3.57 (m, 4H), 3.74 (s, 3H), 3.96-4.01 (m, 2H), 6.27 (d, J=2.0 Hz, 1H), 6.53 (bs, 1H), 7.04 (d, J=4.9 Hz, 1H), 7.16-7.26 (m, 2H), 7.28 (td, J=8.6, 3.2 Hz, 1H), 8.21 (d, J=4.9 Hz, 1H), 11.85-11.89 (m, 1H). MS (ESI⁺) m/z 501.1 (M+H)⁺.

EXAMPLE 455

{4-[4-(5-fluoro-2-methoxyphenyl)-1H-pyrrolo[2,3-b]pyridin-2-yl]-3,6-dihydropyridin-1(2H)-yl}(pyridin-2-yl)methanone In a 2 ml microwave vial with magnetic stirrer was added Example 219A (30 mg, 0.081 mmol) and pyridin-2-yl(4-(4,4,5,5-tetramethyl-1,3,2-dioxaborolan-2-yl)-5,6-dihydropyridin-1(2H)-yl)methanone (38.4 mg, 0.122 mmol) followed by the addition of 60 mg Si-DPP-Pd (0.015 mmol, 0.25 mmol/g, Silicycle Catalog number: R390). Ethanol (1.5 mL) was added followed by 200 uL of 1.0 M cesium carbonate. The vial was capped and reaction was heated at 120° C. for 15 minutes, filtered through a 0.45 μm frit, and purified by reverse phase HPLC (see protocols in Example 360) to provide the title compound. ¹H NMR (400 MHz, DMSO-D₂O) δ 8.63-8.56 (m, 1H), 8.22 (d, J=5.1 Hz, 1H), 7.93 (td, J=7.7, 1.7 Hz, 1H), 7.61-7.56 (m, 1H), 7.48 (ddd, J=7.6, 4.9, 1.2 Hz, 1H), 7.21 (tdd, J=9.2, 7.8, 2.8 Hz, 4H), 7.09 (d, J=5.1 Hz, 1H), 6.50 (s, 1H), 4.31 (s, 2H), 3.77-3.60 (m, 5H), 2.57 (d, J=15.6 Hz, 2H). MS (ESI) m/z 429 [M+1]⁺.

The title compounds (concluding with Example 455) were prepared essentially as described in Example 455, substituting the appropriate boronate.

EXAMPLE 456

{4-[4-(5-fluoro-2-methoxyphenyl)-1H-pyrrolo[2,3-b]pyridin-2-yl]-3,6-dihydropyridin-1(2H)-yl}(pyridin-3-yl)methanone ¹H NMR (400 MHz, DMSO-D₂O) δ 8.74-8.59 (m, 2H), 8.21 (d, J=5.0 Hz, 1H), 7.94-7.84 (m, 1H), 7.55-7.47 (m, 1H), 7.28-7.12 (m, 4H), 7.09-7.03 (m, 1H), 6.50 (br s, 1H), 4.26 (d, J=2.2 Hz, 2H), 3.83-3.65 (m, 2H), 3.73 (s, 3H), 2.60 (m, 2H). MS (ESI) m/z 429 [M+1]⁺.

EXAMPLE 457

{4-[4-(5-fluoro-2-methoxyphenyl)-1H-pyrrolo[2,3-b]pyridin-2-yl]-3,6-dihydropyridin-1(2H)-yl}(pyridin-4-yl)methanone ¹H NMR (400 MHz, DMSO-D₂O) δ 8.76-8.70 (m, 2H), 8.22 (dd, J=7.3, 5.1 Hz, 1H), 7.57-7.48 (m, 2H), 7.32-7.14 (m, 4H), 7.12 (dd, J=12.7, 5.1 Hz, 1H), 6.5 (br s, 1H), 4.44-4.06 (m, 2H), 4.00-3.73 (m, 2H), 3.73 (s, 3H), 3.70 (bs, 2H). MS (ESI) m/z 429 [M+1]⁺.

EXAMPLE 458

{4-[4-(5-fluoro-2-methoxyphenyl)-1H-pyrrolo[2,3-b]pyridin-2-yl]-3,6-dihydropyridin-1(2H)-yl}(pyrazin-2-yl)methanone ¹H NMR (400 MHz, DMSO-D₂O) δ 8.84 (d, J=1.5 Hz, 1H), 8.72 (d, J=2.6 Hz, 1H), 8.66 (dd, J=2.6, 1.5 Hz, 1H), 8.21 (dd, J=12.1, 4.9 Hz, 1H), 7.29-7.14 (m, 4H), 7.10 (d, J=5.1 Hz, 1H), 6.34 (t, J=64.0 Hz, 1H), 4.34 (s, 2H), 3.92-3.55 (m, 5H), 2.62 (s, 2H). MS (ESI) m/z 430 [M+1]⁺.

EXAMPLE 459

4-(5-fluoro-2-methoxyphenyl)-2-[1-(pyrimidin-4-yl)-1,2,3,6-tetrahydropyridin-4-yl]-1H-pyrrolo[2,3-b]pyridine ¹H NMR (400 MHz, DMSO-D₂O) δ 8.76 (t, J=4.9 Hz, 1H), 8.22 (dt, J=11.3, 3.3 Hz, 2H), 7.35-7.11 (m, 5H), 7.09 (t, J=5.0 Hz, 1H), 6.56 (t, J=3.6 Hz, 1H), 4.51 (d, J=3.2 Hz, 2H), 4.09 (t, J=5.8 Hz, 2H), 3.74 (d, J=5.6 Hz, 3H), 2.72 (d, J=1.5 Hz, 2H). MS (ESI) m/z 402 [M+1]⁺.

EXAMPLE 460

4-(5-fluoro-2-methoxyphenyl)-2-[1-(2-methylpyrimidin-4-yl)-1,2,3,6-tetrahydropyridin-4-yl]-1H-pyrrolo[2,3-b]pyridine ¹H NMR (400 MHz, DMSO-D₂O) δ 8.33-8.07 (m, 2H), 7.31-6.99 (m, 6H), 6.56 (br s, 1H), 4.52 (s, 1H), 4.09 (s, 1H), 3.93 (t, J=5.9 Hz, 1H), 3.79-3.67 (m, 5H), 2.70 (s, 1H), 2.63-2.53 (m, 3H). MS (ESI) m/z 416 [M+1]⁺.

EXAMPLE 461

4-(5-fluoro-2-methoxyphenyl)-2-{1-[6-(trifluoromethyl)pyrimidin-4-yl]-1,2,3,6-tetrahydropyridin-4-yl}-1H-pyrrolo[2,3-b]pyridine ¹H NMR (400 MHz, DMSO-D₂O) δ 8.68 (d, J=36.3 Hz, 1H), 8.20 (dd, J=14.7, 5.0 Hz, 1H), 7.28-7.08 (m, 5H), 7.06 (d, J=4.9 Hz, 1H), 6.56 (d, J=3.6 Hz, 1H), 4.37 (d, J=3.2 Hz, 1H), 3.97 (t, J=5.8 Hz, 1H), 3.92-3.80 (m, 1H), 3.78-3.65 (m, 5H), 2.65 (s, 1H). MS (ESI) m/z 470 [M+1]⁺.

EXAMPLE 462

1-{4-[4-(5-fluoro-2-methoxyphenyl)-1H-pyrrolo[2,3-b]pyridin-2-yl]-3,6-dihydropyridin-1(2H)-yl}-3-(piperidin-1-yl)propan-1-one ¹H NMR (400 MHz, DMSO-D₂O) δ 8.19 (dd, J=16.7, 5.0 Hz, 1H), 7.34-7.11 (m, 3H), 7.05 (t, J=4.2 Hz, 1H), 6.48 (s, 1H), 4.21 (s, 2H), 3.81-3.65 (m, 5H), 3.35 (dd, J=18.5, 11.5 Hz, 4H), 3.11-2.82 (m, 4H), 2.54 (d, J=10.9 Hz, 2H), 1.77 (s, 6H). MS (ESI) m/z 463 [M+1]⁺.

EXAMPLE 463

{4-[4-(5-fluoro-2-methoxyphenyl)-1H-pyrrolo[2,3-b]pyridin-2-yl]-3,6-dihydropyridin-1(2H)-yl}(1H-pyrazol-4-yl)methanone ¹H NMR (400 MHz, DMSO-D₂O) δ 8.21 (d, J=5.0 Hz, 1H), 7.90 (s, 2H), 7.23-7.17 (m, 4H), 7.06 (d, J=5.1 Hz, 1H), 6.49 (s, 1H), 6.32-6.25 (m, 1H), 4.34 (d, J=3.3 Hz, 2H), 3.84-3.79 (m, 2H), 3.73 (s, 3H), 2.57 (m, 2H). MS (ESI) m/z 418 [M+1]⁺.

EXAMPLE 464

{4-[4-(5-fluoro-2-methoxyphenyl)-1H-pyrrolo[2,3-b]pyridin-2-yl]-3,6-dihydropyridin-1(2H)-yl}(1,3-thiazol-4-yl)methanone ¹H NMR (400 MHz, DMSO-D₂O) δ 9.11 (d, J=2.1 Hz, 1H), 8.25-8.02 (m, 2H), 7.24-7.13 (m, 4H), 7.05 (d, J=5.0 Hz, 1H), 6.48 (s, 1H), 4.39 (s, 2H), 3.86 (t, J=5.8 Hz, 2H), 3.73 (s, 3H), 2.60 (s, 2H). MS (ESI) m/z 435 [M+1]⁺.

EXAMPLE 465

(3,5-dimethyl-1,2-oxazol-4-yl){4-[4-(5-fluoro-2-methoxyphenyl)-1H-pyrrolo[2,3-b]pyridin-2-yl]-3,6-dihydropyridin-1(2H)-yl}methanone ¹H NMR (400 MHz, DMSO-D₂O) δ 8.19 (dd, J=15.1, 5.0 Hz, 1H), 7.28-7.10 (m, 3H), 7.04 (dd, J=5.0, 1.8 Hz, 1H), 6.47 (s, 1H), 5.79 (s, 1H), 4.21 (s, 1H), 4.09 (s, 2H), 3.72 (s, J=4.6 Hz, 3H), 3.59 (t, J=5.7 Hz, 2H), 2.58 (d, J=7.7 Hz, 1H), 2.35 (s, 3H), 2.16 (s, 3H). MS (ESI) m/z 447 [M+1]⁺.

The title compounds (concluding with Example 553) were prepared essentially as described in Example 220G, substituting the appropriate boronic acid or boronate for (2,3-difluorophenyl)boronic acid.

EXAMPLE 466

4-(2-chloro-5-methoxyphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.59 (s, 2H), 2.94 (s, 3H), 3.35 (t, J=5.6 Hz, 2H), 3.80 (s, 3H), 3.90 (s, 2H), 6.24 (s, 1H), 6.56 (s, 1H), 7.02-7.09 (m, 3H), 7.54 (d, J=8.8 Hz, 1H), 8.28 (d, J=4.8 Hz, 1H), 12.02 (s, 1H). MS (ESI⁺) m/z 418.1 (M+H)⁺.

EXAMPLE 467

2-[1-(methylsulfonyl)-1,2,3,6-tetrahydropyridin-4-yl]-4-(2,3,4-trifluorophenyl)-1H-pyrrolo[2,3-b]pyridine ¹H NMR (400 MHz, CD₃OD) δ ppm 2.74 (s, 2H), 2.94 (s, 3H), 3.54 (t, J=5.8 Hz, 2H), 4.06 (s, 2H), 6.56 (s, 1H), 6.64 (s, 1H), 7.33-7.40 (m, 2H), 7.49-7.55 (m, 1H), 8.35 (d, J=5.6 Hz, 1H). MS (ESI⁺) m/z 408.1 (M+H)⁺.

EXAMPLE 468

2-[1-(methylsulfonyl)-1,2,3,6-tetrahydropyridin-4-yl]-4-[3-(trifluoromethoxy)phenyl]-1H-pyrrolo[2,3-b]pyridine ¹H NMR (400 MHz, DMSO-d₆) δ ppm 2.67 (s, 2H), 2.96 (s, 3H), 3.39 (t, J=5.8 Hz, 2H), 3.92 (s, 2H), 6.59 (s, 1H), 6.65 (s, 1H), 7.24 (d, J=4.8 Hz, 1H), 7.51 (d, J=8.4 Hz, 1H), 7.70 (t, J=8.0 Hz, 2H), 7.85 (t, J=7.6 Hz, 1H), 8.30 (d, J=4.8 Hz, 1H), 12.11 (s, 1H). MS (ESI⁺) m/z 438.1 (M+H)⁺.

EXAMPLE 470

4-(4-methoxyphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.67 (s, 2H), 2.96 (s, 3H), 3.39 (t, J=5.6 Hz, 2H), 3.84 (s, 3H), 3.93 (s, 2H), 6.57 (s, 1H), 6.69 (s, 1H), 7.14 (d, J=8.8 Hz, 2H), 7.19 (d, J=5.2 Hz, 1H), 7.77 (d, J=8.8 Hz, 2H), 8.25 (d, J=4.8 Hz, 1H), 12.09 (s, 1H). MS (ESI⁺) m/z 384.2 (M+H)⁺.

EXAMPLE 471

4-(3,4-difluorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.68 (s, 2H), 2.96 (s, 3H), 3.39 (t, J=5.8 Hz, 2H), 3.92 (s, 2H), 6.58 (s, 1H), 6.69 (s, 1H), 7.21 (d, J=4.8 Hz, 1H), 7.58-7.66 (m, 2H), 7.81-7.87 (m, 1H), 8.28 (d, J=4.8 Hz, 1H), 12.09 (s, 1H). MS (ESI⁺) m/z 390.1 (M+H)⁺.

EXAMPLE 472

2-[1-(methylsulfonyl)-1,2,3,6-tetrahydropyridin-4-yl]-4-[2-(trifluoromethoxy)phenyl]-1H-pyrrolo[2,3-b]pyridine ¹H NMR (400 MHz, DMSO-d₆) δ ppm 2.60 (s, 2H), 2.94 (s, 3H), 3.36 (t, J=5.6 Hz, 2H), 3.92 (s, 2H), 6.30 (s, 1H), 6.57 (s, 1H), 7.07 (d, J=4.8 Hz, 1H), 7.57-7.67 (m, 4H), 8.29 (d, J=4.8 Hz, 1H), 12.09 (s, 1H). MS (ESI⁺) m/z 438.1 (M+H)⁺.

EXAMPLE 477

4-(4-chloro-3-methylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.45 (s, 3H), 2.67 (s, 2H), 2.95 (s, 3H), 3.39 (t, J=5.8 Hz, 2H), 3.93 (s, 2H), 6.57 (s, 1H), 6.66 (s, 1H), 7.19 (d, J=5.2 Hz, 1H), 7.57-7.64 (m, 2H), 7.75 (s, 1H), 8.27 (d, J=5.2 Hz, 1H), 12.06 (s, 1H). MS (ESI⁺) m/z 402.1 (M+H)⁺.

EXAMPLE 478

4-(3-chloro-4-fluorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.67 (s, 2H), 2.95 (s, 3H), 3.39 (t, J=5.8 Hz, 2H), 3.92 (s, 2H), 6.57 (s, 1H), 6.64 (s, 1H), 7.19 (d, J=4.8 Hz, 1H), 7.60 (t, J=8.8 Hz, 1H), 7.78-7.82 (m, 1H), 7.92-7.95 (m, 1H), 8.27 (d, J=5.2 Hz, 1H), 12.05 (s, 1H). MS (ESI⁺) m/z 406.1 (M+H)⁺.

EXAMPLE 479

N,N-dimethyl-3-{2-[1-(methylsulfonyl)-1,2,3,6-tetrahydropyridin-4-yl]-1H-pyrrolo[2,3-b]pyridin-4-yl}benzamide ¹H NMR (400 MHz, DMSO-d₆) δ ppm 2.67 (s, 2H), 2.95 (s, 3H), 3.02 (d, J=9.6 Hz, 6H), 3.39 (t, J=5.4 Hz, 2H), 3.93 (d, J=2.0 Hz, 2H), 6.58 (s, 1H), 6.64 (s, 1H), 7.22 (d, J=5.2 Hz, 1H), 7.52 (d, J=7.6 Hz, 1H), 7.63 (t, J=7.8 Hz, 1H), 7.74 (s, 1H), 7.87 (d, J=7.6 Hz, 1H), 8.29 (d, J=4.8 Hz, 1H), 12.09 (s, 1H). MS (ESI⁺) m/z 425.2 (M+H)⁺.

EXAMPLE 480

4-(4-fluoro-3-methylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.35 (s, 3H), 2.66 (s, 2H), 2.95 (s, 3H), 3.39 (s, 2H), 3.92 (s, 2H), 6.56 (s, 1H), 6.64 (s, 1H), 7.14 (d, J=4.4 Hz, 1H), 7.32 (t, J=9.0 Hz, 1H), 7.62-7.70 (m, 2H), 8.25 (d, J=4.4 Hz, 1H), 12.99 (s, 1H). MS (ESI⁺) m/z 386.2 (M+H)⁺.

EXAMPLE 481

4-[3-fluoro-4-(propan-2-yloxy)phenyl]-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 1.35 (d, J=5.6 Hz, 6H), 2.69 (s, 2H), 2.96 (s, 3H), 3.39 (s, 2H), 3.93 (s, 2H), 4.75 (t, J=5.4 Hz, 1H), 6.57 (s, 1H), 6.69 (s, 1H), 7.17 (d, J=4.4 Hz, 1H), 7.35 (t, J=8.6 Hz, 1H), 7.56-7.65 (m, 2H), 8.24 (d, J=4.8 Hz, 1H), 12.01 (s, 1H). MS (ESI⁺) m/z 430.2 (M+H)⁺.

EXAMPLE 482

4-(4-butoxy-3-fluorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 0.96 (t, J=7.4 Hz, 3H), 1.44-1.51 (m, 2H), 1.72-1.79 (m, 2H), 2.68 (s, 2H), 2.96 (s, 3H), 3.39 (t, J=5.6 Hz, 2H), 3.93 (s, 2H), 4.15 (t, J=6.6 Hz, 2H), 6.58 (s, 1H), 6.70 (s, 1H), 7.19 (d, J=5.2 Hz, 1H), 7.34 (t, J=8.6 Hz, 1H), 7.58-7.66 (m, 2H), 8.25 (d, J=5.2 Hz, 1H), 12.09 (s, 1H). MS (ESI⁺) m/z 444.2 (M+H)⁺.

EXAMPLE 483

(3-{2-[1-(methylsulfonyl)-1,2,3,6-tetrahydropyridin-4-yl]-1H-pyrrolo[2,3-b]pyridin-4-yl}phenyl)(morpholin-4-yl)methanone ¹H NMR (400 MHz, DMSO-d₆) δ ppm 2.66 (s, 2H), 2.95 (s, 3H), 3.39 (t, J=5.6 Hz, 2H), 3.40-3.63 (br, 8H), 3.93 (s, 2H), 6.58 (s, 1H), 6.64 (s, J=1.2 Hz, 1H), 7.23 (d, J=4.8 Hz, 1H), 7.53 (t, J=8.0 Hz, 1H), 7.65 (t, J=7.6 Hz, 1H), 7.75 (s, 1H), 7.89 (d, J=8.0 Hz, 1H), 8.30 (d, J=5.2 Hz, 1H), 12.12 (s, 1H). MS (ESI⁺) m/z 467.2 (M+H)⁺.

EXAMPLE 486

4-(3,5-difluorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.69 (s, 2H), 2.96 (s, 3H), 3.39 (t, J=5.6 Hz, 2H), 3.93 (s, 2H), 6.59 (s, 1H), 6.70 (d, J=1.6 Hz, 1H), 7.24 (d, J=4.8 Hz, 1H), 7.35-7.39 (m, 1H), 7.50 (d, J=6.4 Hz, 1H), 8.28 (d, J=4.8 Hz, 1H), 12.10 (s, 1H). MS (ESI⁺) m/z 390.1 (M+H)⁺.

EXAMPLE 487

4-(2,4-dichlorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.58 (s, 2H), 2.94 (s, 3H), 3.35 (t, J=5.8 Hz, 2H), 3.91 (s, 2H), 6.23 (s, 1H), 6.56 (s, 1H), 7.03 (d, J=5.2 Hz, 1H), 7.52-7.60 (m, 2H), 7.82 (s, 1H), 8.27 (d, J=5.2 Hz, 1H), 12.04 (s, 1H). MS (ESI⁺) m/z 422.0 (M+H)⁺.

EXAMPLE 488

4-(2-ethylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 0.97 (t, J=7.0 Hz, 3H), 2.50 (s, 2H), 2.57 (s, 2H), 2.94 (s, 3H), 3.34 (s, 2H), 3.91 (s, 2H), 6.13 (s, 1H), 6.55 (s, 1H), 6.97 (d, J=4.4 Hz, 1H), 7.25 (d, J=6.4 Hz, 1H), 7.24-7.32 (m, 2H), 7.42 (s, 2H), 8.26 (d, J=3.6 Hz, 1H), 12.05 (s, 1H). MS (ESI⁺) m/z 382.2 (M+H)⁺.

EXAMPLE 489

4-(2,4-dimethylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.14 (s, 3H), 2.35 (s, 3H), 2.58 (s, 2H), 2.94 (s, 3H), 3.34 (t, J=5.4 Hz, 2H), 3.90 (s, 2H), 6.15 (s, 1H), 6.54 (s, 1H), 6.94 (d, J=4.4 Hz, 1H), 7.12 (d, J=7.2 Hz, 1H), 7.19 (t, J=3.8 Hz, 1H), 8.23 (d, J=5.2 Hz, 1H), 11.98 (s, 1H). MS (ESI⁺) m/z 382.1 (M+H)⁺.

EXAMPLE 490

4-(2,5-dichlorophenyl)-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 2.59 (s, 2H), 2.94 (s, 3H), 3.35 (t, J=5.6 Hz, 2H), 3.91 (s, 2H), 6.22 (d, J=1.6 Hz, 1H), 6.56 (s, 1H), 7.04 (d, J=4.8 Hz, 1H), 7.56-7.60 (m, 2H), 7.68 (d, J=8.4 Hz, 1H), 8.28 (d, J=4.8 Hz, 1H), 12.06 (s, 1H). MS (ESI⁺) m/z 422.1 (M+H)⁺.

EXAMPLE 491

4-(3,4-dichlorophenyl)-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 2.59 (s, 2H), 2.94 (s, 3H), 3.35 (t, J=5.6 Hz, 2H), 3.90 (s, 2H), 6.19 (s, 1H), 6.56 (s, 1H), 7.04 (d, J=4.8 Hz, 1H), 7.45-7.53 (m, 2H), 7.75-7.78 (dd, J1=1.6 Hz, J2=7.6 Hz, 1H), 8.28 (d, J=4.8 Hz, 1H), 12.05 (s, 1H). MS (ESI⁺) m/z 422.0 (M+H)⁺.

EXAMPLE 492

N-(4-{2-[1-(methylsulfonyl)-1,2,3,6-tetrahydropyridin-4-yl]-1H-pyrrolo[2,3-b]pyridin-4-yl}phenyl)methanesulfonamide $^1$H NMR (400 MHz, DMSO-$d_6$) δ ppm 2.68 (s, 2H), 2.96 (s, 3H), 3.08 (s, 3H), 3.39 (t, J=5.4 Hz, 2H), 3.91 (s, 2H), 6.57 (s, 1H), 6.72 (s, 1H), 7.19 (t, J=4.4 Hz, 1H), 7.38 (d, J=8.8 Hz, 1H), 7.79 (d, J=8.4 Hz, 1H), 8.25 (d, J=5.2 Hz, 1H), 10.03 (s, 1H), 12.06 (s, 1H). MS (ESI⁺) m/z 447.1 (M+H)⁺.

EXAMPLE 493

4-(5-chloro-2-methoxyphenyl)-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 2.61 (s, 2H), 2.94 (s, 3H), 3.36 (t, J=5.4 Hz, 2H), 3.76 (s, 3H), 3.91 (s, 2H), 6.26 (s, 1H), 6.55 (s, 1H), 7.06 (d, J=5.2 Hz, 1H), 7.21 (d, J=8.8 Hz, 1H), 7.39 (d, J=2.8 Hz, 1H), 7.48-7.52 (m, 1H), 8.23 (d, J=4.8 Hz, 1H), 11.97 (s, 1H). MS (ESI⁺) m/z 418.1 (M+H)⁺.

EXAMPLE 494

4-[2-methoxy-5-(propan-2-yl)phenyl]-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 1.22 (d, J=6.8 Hz, 6H), 2.60 (s, 2H), 2.86-2.95 (m, 4H), 3.37 (t, J=5.6 Hz, 2H), 3.73 (s, 3H), 3.91 (d, J=1.6 Hz, 2H), 6.27 (s, 1H), 6.54 (s, 1H), 7.07-7.13 (m, 2H), 7.25 (d, J=2.4 Hz, 1H), 7.29-7.33 (m, 1H), 8.22 (d, J=5.2 Hz, 1H), 11.97 (s, 1H). MS (ESI⁺) m/z 426.2 (M+H)⁺.

EXAMPLE 495

4-(2-methoxy-5-methylphenyl)-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 2.31 (s, 3H), 2.61 (s, 2H), 2.95 (s, 3H), 3.36 (t, J=5.6 Hz, 2H), 3.72 (s, 3H), 3.91 (s, 2H), 6.28 (s, 1H), 6.54 (s, 1H), 7.06-7.10 (m, 2H), 7.19 (s, 1H), 7.23-7.27 (m, 1H), 8.22 (d, J=5.2 Hz, 1H), 12.01 (s, 1H). MS (ESI⁺) m/z 398.2 (M+H)⁺.

EXAMPLE 496

4-(4-methoxy-3-methylphenyl)-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 2.06 (s, 3H), 2.68 (s, 2H), 2.96 (s, 3H), 3.39 (t, J=5.6 Hz, 2H), 3.88 (s, 3H), 3.93 (s, 2H), 6.57 (s, 1H), 6.71 (s, 1H), 7.12 (d, J=8.4 Hz, 1H), 7.19 (d, J=5.2 Hz, 1H), 7.60 (s, 1H), 7.63-7.66 (m, 1H), 8.25 (d, J=5.2 Hz, 1H), 12.15 (s, 1H). MS (ESI⁺) m/z 398.2 (M+H)⁺.

EXAMPLE 497

2-{2-[1-(methylsulfonyl)-1,2,3,6-tetrahydropyridin-4-yl]-1H-pyrrolo[2,3-b]pyridin-4-yl}benzonitrile $^1$H NMR (400 MHz, DMSO-$d_6$) δ ppm 2.61 (s, 2H), 2.95 (s, 3H), 3.37 (t, J=5.4 Hz, 2H), 3.92 (s, 2H), 6.37 (s, 1H), 6.59 (s, 1H), 7.18 (t, J=5.2 Hz, 1H), 7.69 (t, J=7.8 Hz, 1H), 7.76 (d, J=7.6 Hz, 1H), 7.88 (t, J=7.8 Hz, 1H), 8.05 (d, J=7.6 Hz, 1H), 8.33 (d, J=5.2 Hz, 1H), 12.15 (s, 1H). MS (ESI⁺) m/z 379.2 (M+H)⁺.

EXAMPLE 498

4-(2-methoxyphenyl)-2-[1-(methylsulfonyl)-1,2,3,6-tetrahydropyridin-4-yl]-1H-pyrrolo[2,3-b]pyridine $^1$H NMR (400 MHz, DMSO-$d_6$) δ ppm 2.60 (s, 2H), 2.94 (s, 3H), 3.36 (t, J=5.6 Hz, 2H), 3.76 (s, 3H), 3.91 (s, 2H), 6.28 (s, 1H), 6.54 (s, 1H), 7.07-7.11 (m, 2H), 7.21 (d, J=8.0 Hz, 1H), 7.39-7.47 (m, 2H), 8.22 (d, J=5.2 Hz, 1H), 11.97 (s, 1H). MS (ESI⁺) m/z 384.2 (M+H)⁺.

EXAMPLE 499

3-{2-[1-(methylsulfonyl)-1,2,3,6-tetrahydropyridin-4-yl]-1H-pyrrolo[2,3-b]pyridin-4-yl}benzonitrile $^1$H NMR (400 MHz, DMSO-$d_6$) δ ppm 2.68 (s, 2H), 2.96 (s, 3H), 3.39 (t, J=5.8 Hz, 2H), 3.93, (s, 2H), 6.59 (s, 1H), 6.71 (s, 1H), 7.26 (d, J=4.8 Hz, 1H), 7.77 (t, J=8.0 Hz, 1H), 7.96 (d, J=7.6 Hz, 1H), 8.13 (d, J=8.0 Hz, 1H), 8.20 (s, 1H), 8.31 (d, J=4.8 Hz, 1H), 12.10 (s, 1H). MS (ESI+) m/z 379.2 (M+H)+.

EXAMPLE 500

2-[1-(methylsulfonyl)-1,2,3,6-tetrahydropyridin-4-yl]-4-[2-(trifluoromethyl)phenyl]-1H-pyrrolo[2,3-b]pyridine ¹H NMR (400 MHz, DMSO-d₆) δ ppm 2.54 (s, 2H), 2.93 (s, 3H), 3.33 (t, J=5.6 Hz, 2H), 3.90 (s, 2H), 6.08 (s, 1H), 6.54 (s, 1H), 6.94 (d, J=4.8 Hz, 1H), 7.52 (d, J=7.6 Hz, 1H), 7.71 (t, J=7.8 Hz, 1H), 7.79 (t, J=7.6 Hz, 1H), 7.92 (d, J=7.6 Hz, 1H), 8.25 (d, J=4.8 Hz, 1H), 12.09 (s, 1H). MS (ESI+) m/z 422.1 (M+H)+.

EXAMPLE 501

4-(3-chlorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.67 (s, 2H), 2.95 (s, 3H), 3.39 (t, J=5.6 Hz, 2H), 3.93 (s, 2H), 6.58 (s, 1H), 6.65 (s, 1H), 7.22 (d, J=5.2 Hz, 1H), 7.53-7.61 (m, 2H), 7.75-7.78 (m, 2H), 8.29 (d, J=4.8 Hz, 1H), 12.09 (s, 1H). MS (ESI+) m/z 388.1 (M+H)+.

EXAMPLE 502

4-(2-chlorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.59 (s, 2H), 2.94 (s, 3H), 3.34 (t, J=5.6 Hz, 2H), 3.93 (s, 2H), 6.20 (s, 1H), 6.56 (s, 1H), 7.04 (d, J=5.2 Hz, 1H), 7.48-7.51 (m, 3H), 7.65 (t, J=3.6 Hz, 2H), 8.28 (d, J=4.8 Hz, 1H), 12.01 (s, 1H). MS (ESI+) m/z 388.1 (M+H)+.

EXAMPLE 503

4-[2-fluoro-5-(trifluoromethyl)phenyl]-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.61 (s, 2H), 2.94 (s, 3H), 3.37 (t, J=5.6 Hz, 2H), 3.92 (s, 2H), 6.35 (s, 1H), 6.58 (s, 1H), 7.17 (d, J=4.8 Hz, 1H), 7.67 (t, J=10.4 Hz, 1H), 7.97 (d, J=6.8 Hz, 2H), 8.32 (d, J=4.8 Hz, 1H), 12.09 (s, 1H). MS (ESI+) m/z 440.1 (M+H)+.

EXAMPLE 504

4-(3-chloro-4-methoxyphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.67 (s, 2H), 2.95 (s, 3H), 3.39 (t, J=5.6 Hz, 2H), 3.92-3.95 (m, 5H), 6.57 (s, 1H), 6.65 (s, 1H), 7.18 (d, J=4.8 Hz, 1H), 7.35 (t, J=8.4 Hz, 1H), 7.75-7.80 (m, 2H), 8.25 (d, J=4.8 Hz, 1H), 12.06 (s, 1H). MS (ESI+) m/z 418.1 (M+H)+.

EXAMPLE 505

4-(2-fluoro-5-methylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.38 (s, 3H), 2.62 (s, 2H), 2.95 (s, 3H), 3.37 (t, J=5.6 Hz, 2H), 3.91 (s, 2H), 6.36 (s, 1H), 6.56 (s, 1H), 7.08 (d, J=5.6 Hz, 1H), 7.25-7.34 (m, 2H), 7.42 (d, J=7.2 Hz, 1H), 8.27 (d, J=4.8 Hz, 1H), 11.99 (s, 1H). MS (ESI+) m/z 386.2 (M+H)+.

EXAMPLE 506

4-(5-chloro-2-fluoro-3-methylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.34 (s, 3H), 2.62 (s, 2H), 2.95 (s, 3H), 3.37 (t, J=5.6 Hz, 2H), 3.91 (s, 2H), 6.37 (s, 1H), 6.57 (s, 1H), 7.10 (d, J=4.4 Hz, 1H), 7.43-7.46 (m, 1H), 7.51-7.54 (m, 1H), 8.28 (d, J=4.8 Hz, 1H), 12.04 (s, 1H). MS (ESI+) m/z 420.1 (M+H)+.

EXAMPLE 507

4-(5-chloro-2-propoxyphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 0.78 (t, J=7.2 Hz, 3H), 1.52-1.57 (m, 2H), 1.72-1.79 (m, 2H), 2.60 (s, 2H), 2.94 (s, 3H), 3.36 (t, J=5.6 Hz, 2H), 3.91-3.97 (m, 4H), 6.30 (d, J=1.6 Hz, 1H), 6.55 (s, 1H), 7.08 (d, J=5.2 Hz, 1H), 7.20 (d, J=8.8 Hz, 1H), 7.40 (d, J=2.4 Hz, 1H), 7.45-7.48 (m, 1H), 8.24 (d, J=2.8 Hz, 1H), 12.00 (s, 1H). MS (ESI+) m/z 446.1 (M+H)+.

EXAMPLE 512

4-(2,3-dichlorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.67 (s, 2H), 2.95 (s, 3H), 3.39 (t, J=5.8 Hz, 2H), 3.93 (s, 2H), 6.58 (s, 1H), 6.65 (s, 1H), 7.21 (d, J=4.8 Hz, 1H), 7.76-7.83 (m, 2H), 7.98 (s, 1H), 8.28 (d, J=4.8 Hz, 1H), 12.07 (s, 1H). MS (ESI+) m/z 422.1 (M+H)+.

EXAMPLE 513

4-(3-chloro-4-methylphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.42 (s, 3H), 2.67 (s, 2H), 2.95 (s, 3H), 3.39 (t, J=5.6 Hz, 2H), 3.92 (s, 2H), 6.57 (s, 1H), 6.62 (s, 1H), 7.17 (d, J=4.8 Hz, 1H), 7.53 (d, J=8.0 Hz, 1H), 7.65-7.77 (m, 1H), 7.76 (s, 1H), 8.26 (d, J=4.8 Hz, 1H), 12.03 (s, 1H). MS (ESI$^+$) m/z 402.1 (M+H)$^+$.

EXAMPLE 514

2-methyl-5-{2-[1-(methylsulfonyl)-1,2,3,6-tetrahydropyridin-4-yl]-1H-pyrrolo[2,3-b]pyridin-4-yl}aniline $^1$H NMR (400 MHz, DMSO-d$_6$) δ ppm 2.12 (s, 3H), 2.66 (s, 2H), 2.95 (s, 3H), 3.39 (t, J=5.8 Hz, 2H), 3.92 (s, 2H), 5.03 (s, 2H), 6.54 (s, 1H), 6.63 (s, 1H), 6.84-6.87 (m, 1H), 7.04-7.09 (m, 3H), 8.20 (d, J=5.2 Hz, 1H), 11.88 (s, 1H). MS (ESI$^+$) m/z 383.2 (M+H)$^+$.

EXAMPLE 515

4-(2-fluorobiphenyl-4-yl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 2.70 (s, 2H), 2.96 (s, 3H), 3.40 (t, J=5.6 Hz, 2H), 3.93 (s, 2H), 6.59 (s, 1H), 6.74 (s, 1H), 7.26 (t, J=5.2 Hz, 1H), 7.45 (t, J=7.2 Hz, 1H), 7.54 (t, J=7.6 Hz, 1H), 7.64 (d, J=7.6 Hz, 1H), 7.69-7.76 (m, 3H), 8.29 (d, J=4.8 Hz, 1H), 12.06 (s, 1H). MS (ESI$^+$) m/z 448.2 (M+H)$^+$.

EXAMPLE 516

2-[1-(methylsulfonyl)-1,2,3,6-tetrahydropyridin-4-yl]-4-[3-(propan-2-yloxy)phenyl]-1H-pyrrolo[2,3-b]pyridine $^1$H NMR (400 MHz, DMSO-d$_6$) δ ppm 1.31 (d, J=6.0 Hz, 6H), 2.66 (s, 2H), 2.95 (s, 3H), 3.39 (t, J=5.4 Hz, 2H), 3.92 (s, 2H), 4.69-4.75 (m, 1H), 6.56 (s, 1H), 6.61 (s, 1H), 7.03 (d, J=8.0 Hz, 1H), 7.15 (d, J=4.8 Hz, 1H), 7.21 (s, 1H), 7.30 (d, J=7.2 Hz, 1H), 7.45 (t, J=7.8 Hz, 1H), 8.25 (d, J=4.8 Hz, 1H), 11.98 (br, 1H). MS (ESI$^+$) m/z 412.2 (M+H)$^+$.

EXAMPLE 517

4-(3-fluoro-4-propoxyphenyl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 1.01 (t, J=7.2 Hz, 3H), 1.76-1.82 (m, 2H), 2.68 (s, 2H), 2.96 (s, 3H), 3.39 (t, J=5.6 Hz, 2H), 3.92 (s, 2H), 4.10 (t, J=6.4 Hz, 2H), 6.57 (s, 1H), 6.67 (s, 1H), 7.14 (d, J=4.8 Hz, 1H), 7.33 (t, J=8.6 Hz, 1H), 7.56-7.64 (m, 2H), 8.23 (d, J=5.2 Hz, 1H), 11.98 (s, 1H). MS (ESI$^+$) m/z 430.2 (M+H)$^+$.

EXAMPLE 518

4-[2-fluoro-5-(propan-2-yloxy)phenyl]-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 1.28 (d, J=5.6 Hz, 6H), 2.62 (s, 2H), 2.95 (s, 3H), 3.37 (s, 2H), 3.92 (s, 2H), 4.60-4.67 (m, 1H), 6.35 (s, 1H), 6.56 (s, 1H), 7.03-7.10 (m, 3H), 7.30 (t, J=9.0 Hz, 1H), 8.26 (d, J=3.6 Hz, 1H), 11.99 (s, 1H). MS (ESI$^+$) m/z 430.2 (M+H)$^+$.

EXAMPLE 519

4-(4-butoxy-3-chlorophenyl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 0.97 (t, J=7.6 Hz, 3H), 1.49-1.53 (m, 2H), 1.76-1.79 (m, 2H), 2.67 (s, 2H), 2.95 (s, 3H), 3.39 (t, J=5.6 Hz, 2H), 3.92 (s, 2H), 4.15 (t, J=6.4 Hz, 2H), 6.56 (s, 1H), 6.63 (s, 1H), 7.14 (d, J=4.8 Hz, 1H), 7.31 (d, J=8.4 Hz, 1H), 7.72 (t, J=5.2 Hz, 1H), 7.78 (d, J=2 Hz, 1H), 8.23 (d, J=5.2 Hz, 1H), 11.99 (s, 1H). MS (ESI$^+$) m/z 460.1 (M+H)$^+$.

EXAMPLE 520

4-[2-(2-methylpropoxy)phenyl]-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 0.79 (d, J=6.8 Hz, 6H), 1.81-1.86 (m, 1H), 2.60 (s, 2H), 2.94 (s, 3H), 3.34 (t, J=5.6 Hz, 2H), 3.77 (d, J=6.4 Hz, 2H), 3.91 (s, 1H), 6.32 (s, 1H), 6.54 (s, 1H), 7.07-7.12 (m, 2H), 7.17 (d, J=8.8 Hz, 2H), 7.41-7.44 (m, 2H), 8.23 (d, J=5.2 Hz, 1H), 11.98 (s, 1H). MS (ESI$^+$) m/z 426.2 (M+H)$^+$.

EXAMPLE 521

4-{2-[1-(methylsulfonyl)-1,2,3,6-tetrahydropyridin-4-yl]-1H-pyrrolo[2,3-b]pyridin-4-yl}benzonitrile $^1$H NMR (400 MHz, DMSO-d$_6$) δ ppm 2.67 (s, 2H), 2.95 (s, 3H), 3.39 (t, J=5.2 Hz, 2H), 3.93 (s, 2H), 6.59 (s, 1H), 6.68 (s, 1H), 7.24 (d, J=4.8 Hz, 1H), 7.97-8.03 (m, 4H), 8.27 (d, J=3.2 Hz, 1H), 12.11 (s, 1H). MS (ESI$^+$) m/z 379.2 (M+H)$^+$.

EXAMPLE 522

2-[1-(methylsulfonyl)-1,2,3,6-tetrahydropyridin-4-yl]-4-phenyl-1H-pyrrolo[2,3-b]pyridine $^1$H NMR (400 MHz, DMSO-d$_6$) δ ppm 2.67 (s, 2H), 2.95 (s, 3H), 3.39 (t, J=5.6 Hz, 2H), 3.92 (s, 2H), 6.57 (s, 1H), 6.67 (s, 1H), 7.19 (d, J=4.8 Hz, 1H), 7.49 (d, J=7.2 Hz, 1H), 7.57 (t, J=6.8 Hz, H), 7.80 (d, J=4.2 Hz, 2H), 8.27 (d, J=5.2 Hz, 1H), 12.06 (s, 1H). MS (ESI$^+$) m/z 354.1 (M+H)$^+$.

EXAMPLE 524

4-(3-fluoro-4-methoxyphenyl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 2.67 (s, 2H), 2.96 (s, 3H), 3.39 (t, J=5.6 Hz, 2H), 3.93 (s, 5H), 6.57 (s, 1H), 6.68 (d, 1H), 7.17 (d, J=5.2 Hz, 1H), 7.36 (d, J=8.4 Hz, 1H), 7.61-7.65 (m, 2H), 8.27 (d, J=4.8 Hz, 1H), 12.03 (s, 1H). MS (ESI$^+$) m/z 402.1 (M+H)$^+$.

EXAMPLE 525

3-{2-[1-(methylsulfonyl)-1,2,3,6-tetrahydropyridin-4-yl]-1H-pyrrolo[2,3-b]pyridin-4-yl}aniline $^1$H NMR (400 MHz, DMSO-d$_6$) δ ppm 2.67 (s, 2H), 2.96 (s, 3H), 3.40 (t, J=5.6 Hz, 2H), 3.93 (s, 2H), 6.58 (s, 1H), 6.67 (s, 1H), 7.08 (d, J=8.0 Hz, 1H), 7.15 (d, J=5.2 Hz, 1H), 7.40 (s, 2H), 7.46 (t, J=8.4 Hz, 1H), 8.27 (d, J=5.2 Hz, 1H), 12.09 (s, 1H). MS (ESI$^+$) m/z 369.1 (M+H)$^+$.

EXAMPLE 526

N-(2-{2-[1-(methylsulfonyl)-1,2,3,6-tetrahydropyridin-4-yl]-1H-pyrrolo[2,3-b]pyridin-4-yl}phenyl)methanesulfonamide $^1$H NMR (400 MHz, DMSO-d$_6$) δ ppm 2.60 (s, 2H), 2.77 (s, 3H), 2.94 (s, 3H), 3.36 (t, J=5.6 Hz, 2H), 3.92 (s, 2H), 6.30 (d, 1H), 6.56 (s, 1H), 7.12 (d, J=5.2 Hz, 1H), 7.36-7.40 (m, 1H), 7.45-7.55 (m, 3H), 8.27 (d, J=4.8 Hz, 1H), 8.92 (s, 1H), 12.04 (s, 1H). MS (ESI$^+$) m/z 447.1 (M+H)$^+$.

EXAMPLE 527

3-{2-[1-(methylsulfonyl)-1,2,3,6-tetrahydropyridin-4-yl]-1H-pyrrolo[2,3-b]pyridin-4-yl}-N-(propan-2-yl)benzamide $^1$H NMR (400 MHz, DMSO-d$_6$) δ ppm 1.18 (d, J=6.8 Hz, 6H), 2.66 (s, 2H), 2.95 (s, 3H), 3.39 (t, J=5.6 Hz, 2H), 3.93 (s, 2H), 4.11-4.15 (m, 1H), 6.58 (s, 1H), 6.66 (s, 1H), 7.26 (d, J=5.2 Hz, 1H), 7.64 (t, J=8 Hz, 1H), 7.93 (d, J=7.6 Hz, 2H), 8.18 (s, 1H), 8.30 (d, J=4.8 Hz, 1H), 8.37 (d, J=7.6 Hz, 1H), 12.08 (s, 1H). MS (ESI$^+$) m/z 439.2 (M+H)$^+$.

EXAMPLE 529

(4-{2-[1-(methylsulfonyl)-1,2,3,6-tetrahydropyridin-4-yl]-1H-pyrrolo[2,3-b]pyridin-4-yl}phenyl)acetonitrile $^1$H NMR (400 MHz, DMSO-d$_6$) δ ppm 2.67 (s, 2H), 2.95 (s, 3H), 3.39 (t, J=5.6 Hz, 2H), 3.92 (s, 2H), 4.15 (s, 2H), 6.57 (s, 1H), 6.68 (s, 1H), 7.19 (d, J=4.8 Hz, 1H), 7.53 (d, J=8 Hz, 2H), 7.81 (d, J=8 Hz, 2H), 8.27 (d, J=4.8 Hz, 1H), 12.05 (s, 1H). MS (ESI$^+$) m/z 393.1 (M+H)$^+$.

EXAMPLE 530

N-methyl-4-{2-[1-(methylsulfonyl)-1,2,3,6-tetrahydropyridin-4-yl]-1H-pyrrolo[2,3-b]pyridin-4-yl}benzamide $^1$H NMR (400 MHz, DMSO-d$_6$) δ ppm 2.67 (s, 2H), 2.83 (d, J=5.6 Hz, 3H), 2.95 (s, 3H), 3.39 (t, J=5.6 Hz, 2H), 3.93 (s, 2H), 6.57 (s, 1H), 6.67 (s, 1H), 7.22 (d, J=4.8 Hz, 1H), 7.87 (d, J=8.4 Hz, 2H), 8.01 (d, J=8.4 Hz, 2H), 8.29 (d, J=5.2 Hz, 1H), 8.56 (d, J=4.8 Hz, 1H), 12.02 (s, 1H). MS (ESI$^+$) m/z 411.1 (M+H)$^+$.

EXAMPLE 531

N-(3-{2-[1-(methylsulfonyl)-1,2,3,6-tetrahydropyridin-4-yl]-1H-pyrrolo[2,3-b]pyridin-4-yl}phenyl)acetamide $^1$H NMR (400 MHz, DMSO-d$_6$) δ ppm 2.09 (s, 3H), 2.66 (s, 2H), 2.95 (s, 3H), 3.39 (t, J=5.6 Hz, 2H), 3.93 (s, 2H), 6.57 (s, 1H), 6.69 (s, 1H), 7.13 (d, J=4.8 Hz, 1H), 7.41-7.49 (m, 2H), 7.65 (d, J=8.0 Hz, 1H), 8.07 (s, 1H), 8.27 (d, J=4.8 Hz, 1H), 10.10 (s, 1H), 12.02 (s, 1H). MS (ESI$^+$) m/z 411.2 (M+H)$^+$.

EXAMPLE 532

N-(4-{2-[1-(methylsulfonyl)-1,2,3,6-tetrahydropyridin-4-yl]-1H-pyrrolo[2,3-b]pyridin-4-yl}phenyl)acetamide $^1$H NMR (400 MHz, DMSO-d$_6$) δ ppm 2.09 (s, 3H), 2.67 (s, 2H), 2.95 (s, 3H), 3.39 (t, J=5.6 Hz, 2H), 3.92 (s, 2H), 6.55 (s, 1H), 6.69 (s, 1H), 7.14 (d, J=5.2 Hz, 1H), 7.72-7.78 (m, 4H), 8.23 (d, J=5.2 Hz, 1H), 10.13 (s, 1H), 11.93 (s, 1H). MS (ESI$^+$) m/z 411.2 (M+H)$^+$.

EXAMPLE 543

3-{2-[1-(methylsulfonyl)-1,2,3,6-tetrahydropyridin-4-yl]-1H-pyrrolo[2,3-b]pyridin-4-yl}benzamide $^1$H NMR (400 MHz, DMSO-d$_6$) δ ppm 2.67 (s, 2H), 2.95 (s, 3H), 3.39 (t, J=5.4 Hz, 2H), 3.93 (s, 2H), 6.57 (s, 1H), 6.65 (s, 1H), 7.24 (d, J=5.2 Hz, 1H), 7.48 (s, 1H), 7.65 (t, J=7.8 Hz, 1H), 7.94 (t, J=8.8 Hz, 2H), 8.14 (s, 1H), 8.22 (s, 1H), 8.30 (d, J=4.8 Hz, 1H), 12.02 (s, 1H). MS (ESI$^+$) m/z 397.1 (M+H)$^+$.

EXAMPLE 544

4-(4-ethoxy-2-methylphenyl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 1.36 (t, J=7.0 Hz, 3H), 2.17 (s, 3H), 2.59 (s, 2H), 2.94 (s, 3H), 3.35 (t, J=5.6 Hz, 2H), 3.91 (s, 2H), 4.06-4.11 (m, 2H), 6.21 (s, 1H), 6.55 (s, 1H), 6.86-6.89 (m, 1H), 6.95 (s, 1H), 6.98 (d, J=4.8 Hz, 1H), 7.24 (d, J=8.4 Hz, 1H), 8.25 (t, J=5.2 Hz, 1H), 12.07 (s, 1H). MS (ESI$^+$) m/z 412.2 (M+H)+.

EXAMPLE 545

4-[4-chloro-3-(trifluoromethyl)phenyl]-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 2.66 (s, 2H), 2.95 (s, 3H), 3.39 (t, J=5.6 Hz, 2H), 3.93 (s, 2H), 6.59 (s, 1H), 6.66 (s, 1H), 7.27 (d, J=4.8 Hz, 1H), 7.92 (d, J=9.2 Hz, 1H), 8.11 (s, 2H), 8.31 (d, J=4.8 Hz, 1H), 12.10 (s, 1H). MS (ESI$^+$) m/z 456.1 (M+H)$^+$.

EXAMPLE 546

N-butyl-3-{2-[1-(methylsulfonyl)-1,2,3,6-tetrahydropyridin-4-yl]-1H-pyrrolo[2,3-b]pyridin-4-yl}benzamide $^1$H NMR (400 MHz, DMSO-d$_6$) δ ppm 0.91 (t, J=7.4 Hz, 3H), 1.30-1.39 (m, 2H), 1.49-1.57 (m, 2H), 2.66 (s, 2H), 2.95 (s, 3H), 3.27-3.32 (m, 2H), 3.39 (t, J=5.6 Hz, 2H), 3.93 (s, 2H), 6.57 (s, 1H), 6.65 (s, 1H), 7.25 (d, J=4.8 Hz, 1H), 7.65 (t, J=7.8 Hz, 1H), 7.94 (t, J=8.0 Hz, 1H), 8.20 (s, 1H), 8.31 (d, J=4.8 Hz, 1H), 8.59 (d, J=5.6 Hz, 1H), 12.05 (s, 1H). MS (ESI$^+$) m/z 453.2 (M+H)$^+$.

EXAMPLE 547

4-(3-fluorophenyl)-2-[1-(methylsulfonyl)-1,2,3,6-tetrahydropyridin-4-yl]-1H-pyrrolo[2,3-b]pyridine $^1$H NMR (400 MHz, DMSO-d$_6$) δ ppm 2.69 (s, 2H), 2.96 (s, 3H), 3.39 (t, J=5.6 Hz, 2H), 3.93 (s, 2H), 6.58 (s, 1H), 6.68 (s, 1H), 7.19 (d, J=4.8 Hz, 1H), 7.30-7.34 (m, 1H), 7.57-7.77 (m, 3H), 8.27 (d, J=5.2 Hz, 1H), 12.04 (s, 1H). MS (ESI⁺) m/z 372.1 (M+H)⁺.

EXAMPLE 548

4-{3-chloro-4-[(3-chlorobenzyl)oxy]phenyl}-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.67 (s, 2H), 2.95 (s, 3H), 3.39 (t, J=5.2 Hz, 2H), 3.92 (s, 2H), 5.34 (s, 2H), 6.57 (s, 1H), 6.63 (s, 1H), 7.15 (d, J=4.8 Hz, 1H), 7.38 (d, J=8.4 Hz, 1H), 7.43-7.49 (m, 3H), 7.59 (s, 1H), 7.74-7.77 (m, 1H), 7.84 (d, J=2 Hz, 1H), 8.23 (d, J=4.8 Hz, 1H), 12.0 (s, 1H). MS (ESI⁺) m/z 528.0 (M+H)⁺.

EXAMPLE 549

4-(4-fluoro-2-methoxyphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.60 (s, 2H), 2.94 (s, 3H), 3.35 (t, J=5.6 Hz, 2H), 3.78 (s, 3H), 3.91 (s, 2H), 6.27 (d, 1H), 6.54 (s, 1H), 6.90-6.94 (m, 1H), 7.04 (d, J=4.8 Hz, 1H), 7.10-7.13 (m, 1H), 7.41-7.45 (m, 1H), 8.20 (d, J=5.2 Hz, 1H), 11.93 (s, 1H). MS (ESI⁺) m/z 402.1 (M+H)⁺.

EXAMPLE 550

2-[1-(methylsulfonyl)-1,2,3,6-tetrahydropyridin-4-yl]-4-[4-(trifluoromethoxy)phenyl]-1H-pyrrolo[2,3-b]pyridine ¹H NMR (400 MHz, DMSO-d₆) δ ppm 2.67 (s, 2H), 2.95 (s, 3H), 3.39 (t, J=5.2 Hz, 2H), 3.93 (s, 2H), 6.58 (s, 1H), 6.67 (s, 1H), 7.19 (d, J=4.8 Hz, 1H), 7.54 (d, J=8.4 Hz, 2H), 7.90 (d, J=8.4 Hz, 2H), 8.28 (d, J=4.8 Hz, 1H), 12.04 (s, 1H). MS (ESI⁺) m/z 438.1 (M+H)⁺.

EXAMPLE 551

4-[3-chloro-4-(propan-2-yloxy)phenyl]-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 1.34 (d, J=6 Hz, 6H), 2.67 (s, 2H), 2.95 (s, 3H), 3.39 (t, J=5.2 Hz, 2H), 3.92 (s, 2H), 4.76-4.80 (m, 1H), 6.56 (s, 1H), 6.64 (s, 1H), 7.14 (d, J=4.8 Hz, 1H), 7.33 (d, J=8.8 Hz, 1H), 7.70-7.73 (m, 1H), 7.78 (d, J=2 Hz, 1H), 8.23 (d, J=5.2 Hz, 1H), 11.99 (s, 1H). MS (ESI⁺) m/z 446.1 (M+H)⁺.

EXAMPLE 552

4-(3,5-dichlorophenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 2.68 (s, 2H), 2.95 (s, 3H), 3.39 (t, J=5.6 Hz, 2H), 3.92 (s, 2H), 6.59 (s, 1H), 6.63 (s, 1H), 7.22 (d, J=5.2 Hz, 1H), 7.74 (t, J=2.2 Hz, 1H), 7.77 (d, J=2.0 Hz, 1H), 8.28 (d, J=5.2 Hz, 1H), 12.09 (s, 1H). MS (ESI⁺) m/z 422.1 (M+H)⁺.

EXAMPLE 553

4-(4-fluoro-2-propoxyphenyl)-2-[1-(methylsulfonyl)-1,2,3,6-tetrahydropyridin-4-yl]-1H-pyrrolo[2,3-b]pyridine ¹H NMR (400 MHz, DMSO-d₆) δ ppm 0.81 (t, J=7.4 Hz, 3H), 1.54-1.60 (m, 2H), 2.59 (s, 2H), 2.94 (s, 3H), 3.36 (t, J=5.6 Hz, 2H), 3.90 (s, 2H), 3.98 (t, J=6.4 Hz, 2H), 6.28 (s, 1H), 6.53 (s, 1H), 6.87-6.93 (m, 1H), 7.02 (d, J=5.2 Hz, 1H), 7.08 (dd, J1=2.0 Hz, J2=11.6 Hz, 1H), 7.43 (t, J=7.8 Hz, 1H), 8.20 (d, J=5.2 Hz, 1H), 11.84 (s, 1H). MS (ESI⁺) m/z 430.2 (M+H)⁺.

EXAMPLE 469

N-(2-{4-[4-(5-fluoro-2-methoxyphenyl)-1H-pyrrolo[2,3-b]pyridin-2-yl]-3,6-dihydropyridin-1(2H)-yl}ethyl)-N²,N²-dimethylglycinamide To a solution of Example 1332 (75 mg, 0.171 mmol) in 3 mL N,N-dimethylformamide was added triethylamine (0.095 ml, 0.683 mmol) followed by 1-(3-dimethylaminopropyl)-3-ethylcarbodiimide hydrochloride (87 mg, 0.455 mmol) and 1H-benzo[d][1,2,3]triazol-1-ol hydrate (69.7 mg, 0.455 mmol). The reaction was stirred at room temperature overnight. The reaction mixture was diluted with ethyl acetate and the solution was washed with saturated sodium bicarbonate, water and brine, dried over magnesium sulfate, filtered, and concentrated. The crude material was dissolved in 2 mL methanol, treated with 2M HCl/ether and stirred for 10 minutes. 20 mL diethyl ether was added and the solid filtered to give the title compound as the HCl salt. ¹H NMR (400 MHz, DMSO-d₆) δ ppm 12.96 (s, 1 H) 11.30 (s, 1 H) 10.17 (s, 1 H) 9.18 (t, J=5.65 Hz, 1 H) 8.31 (d, J=5.80 Hz, 1 H) 7.08-7.53 (m, 4 H) 6.67 (s, 1 H) 6.52 (s, 1 H) 4.16 (d, J=16.78 Hz, 1 H) 3.84-4.04 (m, 3 H) 3.75 (s, 3 H) 3.20-3.41 (m, 3 H) 2.91-3.07 (m, 1 H) 2.75-2.87 (m, 7 H). MS (ESI): 452.1 (M+H)⁺.

EXAMPLE 473

4-[5-fluoro-2-(propan-2-yloxy)phenyl]-2-[1-(methylsulfonyl)-1,2,3,6-tetrahydropyridin-4-yl]-1H-pyrrolo[2,3-b]pyridine

EXAMPLE 473A 4-bromo-2-(1-(methylsulfonyl)-1,2,3,6-tetrahydropyridin-4-yl)-1H-pyrrolo[2,3-b]pyridine 4-Bromo-2-(1-(methylsulfonyl)-1,2,3,6-tetrahydropyridin-4-yl)-1-tosyl-1H-pyrrolo[2,3-b]pyridine (1.61 g, 3.16 mmol) in a mixture of tetrahydrofuran (8 mL), methanol (8 mL) and water (5 mL) was treated with 1 M NaOH aqueous solution (6.32 mL) at 60° C. overnight. The suspension was filtered and the solid was dried with magnesium sulfate to provide the desired product. LCMS: 357 (M+H)⁺.

EXAMPLE 473B

4-[5-fluoro-2-(propan-2-yloxy)phenyl]-2-[1-(methylsulfonyl)-1,2,3,6-tetrahydropyridin-4-yl]-1H-pyrrolo[2,3-b]pyridine The title compound was prepared using the procedure described in Example 382A, using (5-fluoro-2-isopropoxyphenyl)boronic acid in place of 4-fluoro-3-(4,4,5,5-tetramethyl-1,3,2-dioxaborolan-2-yl)phenol and Example 473A in place of Example 220C. $^1$H NMR (400 MHz, DMSO-d$_6$) δ ppm 1.12 (d, 6 H) 2.62 (s, 2 H) 2.94 (s, 3 H) 3.37 (t, 2 H) 3.92 (d, 2 H) 4.43-4.57 (m, 1 H) 6.38 (d, 1 H) 6.56 (s, 1 H) 7.13 (d, 1 H) 7.18-7.22 (m, 1 H) 7.22-7.28 (m, 2 H) 8.25 (d, 1 H) 12.03 (s, 1 H); LCMS: 430 (M+H)$^+$.

EXAMPLE 474

4-[2-(cyclopropyloxy)-5-fluorophenyl]-2-[1-(methylsulfonyl)-1,2,3,6-tetrahydropyridin-4-yl]-1H-pyrrolo[2,3-b]pyridine The title compound was prepared using the procedure described in Example 382A, using 2-(2-cyclopropoxy-5-fluorophenyl)-4,4,5,5-tetramethyl-1,3,2-dioxaborolane in place of 4-fluoro-3-(4,4,5,5-tetramethyl-1,3,2-dioxaborolan-2-yl)phenol and Example 473A in place of Example 220C. $^1$H NMR (400 MHz, DMSO-d$_6$) δ ppm 0.55-0.64 (m, 2 H) 0.71-0.79 (m, 2 H) 2.60 (d, 2 H) 2.94 (s, 3 H) 3.37 (t, 2 H) 3.82-3.87 (m, 3 H) 6.26 (d, 1 H) 6.55 (s, 1 H) 7.04 (d, 1 H) 7.24 (dd, 1 H) 7.28-7.34 (m, 1 H) 7.48 (dd, 1 H) 8.22 (d, 1 H) 11.96 (s, 1 H); LCMS: 428 (M+H)$^+$.

EXAMPLE 475

4-(4-ethoxy-3-fluorophenyl)-2-[1-(methylsulfonyl)-1,2,3,6-tetrahydropyridin-4-yl]-1H-pyrrolo[2,3-b]pyridine The title compound was prepared using the procedure described in Example 382A, using (4-ethoxy-3-fluorophenyl)boronic acid in place of 4-fluoro-3-(4,4,5,5-tetramethyl-1,3,2-dioxaborolan-2-yl)phenol and Example 473A in place of Example 220C. $^1$H NMR (400 MHz, DMSO-d$_6$) δ ppm 1.40 (t, 3 H) 2.68 (s, 2 H) 2.96 (s, 3 H) 3.39 (t, 2 H) 3.93 (d, 2 H) 4.20 (q, 2 H) 6.58 (s, 1 H) 6.71 (d, 1 H) 7.20 (d, 1 H) 7.33 (t, 1 H) 7.53-7.69 (m, 2 H) 8.25 (d, 1 H); LCMS: 416 (M+H)$^+$.

EXAMPLE 476

4-(4-{5-[(3,5-difluorobenzyl)amino]-2-fluorophenyl}-1H-pyrrolo[2,3-b]pyridin-2-yl)piperidine-1-sulfonamide The title compound was prepared essentially as described in Example 426, substituting Example 365 for Example 354. $^1$H NMR (400 MHz, CD$_3$OD): δ1.76-1.86 (m, 2 H), 2.11 (d, J=11.90 Hz, 2 H), 2.75-2.81 (m, 2 H), 2.88-2.94 (m, 1 H), 3.79 (d, J=11.90 Hz, 2 H), 4.39 (s, 2 H), 6.22 (s, 1 H), 6.72 (dd, J=5.80, 3.05 Hz, 1 H), 6.82-6.87 (m, 2 H), 7.00 (d, J=6.41 Hz, 2 H), 7.10-7.15 (m, 1 H), 7.46 (dd, J=6.10, 1.53 Hz, 1 H), 8.26 (d, J=6.10 Hz, 1 H); MS (DCI/NH$_3$) m/z 516 (M+H)$^+$.

EXAMPLE 484

N-(3,5-difluorobenzyl)-4-fluoro-3-[2-(1,2,3,6-tetrahydropyridin-4-yl)-1H-pyrrolo[2,3-b]pyridin-4-yl]aniline

EXAMPLE 484A tert-butyl 4-(4-(5-amino-2-fluorophenyl)-1-tosyl-1H-pyrrolo[2,3-b]pyridin-2-yl)-5,6-dihydropyridine-1(2H)-carboxylate A mixture of Example 220C (600.0 mg, 1.127 mmol), 4-fluoro-3-(4,4,5,5-tetramethyl-1,3,2-dioxaborolan-2-yl) aniline (321 mg, 1.352 mmol), bis(triphenylphosphine)palladium(II) dichloride (39.5 mg, 0.056 mmol), and 1M sodium carbonate (1127 µl, 1.127 mmol) in 10 mL of 1,2-dimethoxyethane/ethanol/water (7:2:3) was heated in a Biotag Initiator (model 355302) microwave reactor at 150° C. for 15 minutes. The reaction mixture was concentrated, treated with ethyl acetate and washed with aqueous NaHCO$_3$. The organic layer was washed with water, dried over MgSO$_4$, filtered, concentrated, and purified on a 40 g silica column using the ISCO Companion flash system eluting with dichloromethane/ethyl acetate (2:8) to provide the title compound. MS (ESI$^+$) m/z 563.1 (M+H)$^+$.

EXAMPLE 484B tert-butyl 4-(4-(5-((3,5-difluorobenzyl)amino)-2-fluorophenyl)-1-tosyl-1H-pyrrolo[2,3-b]pyridin-2-yl)-5,6-dihydropyridine-1(2H)-carboxylate To a mixture of Example 484A (0.730 g, 1.297 mmol) and acetic acid (0.371 mL, 6.49 mmol) in dichloromethane (20 mL) and methanol (20 mL) was added 3,5-difluorobenzaldehyde (0.553 g, 3.89 mmol) and MP-cyanoborohydride (2392 mg, 5.19 mmol). The reaction mixture was stirred at room temperature for 6 hours. The solid material was filtered and rinsed with dichloromethane and methanol. The filtrate was concentrated. The residue was dissolved in dichloromethane and washed with aqueous NaHCO$_3$. The organic layer was dried over MgSO$_4$, filtered, concentrated, and purified on a 40 g silica column using the ISCO Companion flash system eluting with heptanes/ethyl acetate (7:3 to 6:4) to provide the title compound. MS (ESI$^+$) m/z 689.1 (M+H)$^+$.

EXAMPLE 484C tert-butyl 4-(4-(5-((3,5-difluorobenzyl)amino)-2-fluorophenyl)-1H-pyrrolo[2,3-b]pyridin-2-yl)-5,6-dihydropyridine-1(2H)-carboxylate A mixture of Example 484B (0.745 g, 1.082 mmol) and 20% sodium hydroxide (0.649 mL, 3.24 mmol) solution in dioxane (6 mL) was heated at 90° C. for 8 hours. The solvent was evaporated. The residue was treated with ethyl acetate and washed with aqueous. NaHCO$_3$. The organic layer was dried over MgSO$_4$, filtered, and concentrated, and purified on a 40 g silica column using the ISCO Companion flash system eluting with heptanes/ethyl acetate (4:6 to 3:7) to provide the title compound. MS (ESI$^+$) m/z 535.1 (M+H)$^+$.

EXAMPLE 484D

N-(3,5-difluorobenzyl)-4-fluoro-3-[2-(1,2,3,6-tetrahydropyridin-4-yl)-1H-pyrrolo[2,3-b]pyridin-4-yl]aniline A solution of Example 484C (350 mg, 0.655 mmol) in CH$_2$Cl$_2$ (10 mL) was treated with trifluoroacetic acid (0.504 mL, 6.55 mmol). The mixture was stirred overnight and concentrated. The residue was dissolved in 3 mL of methanol and treated with 4 mL of 2M HCl in ether slowly. The suspension was stirred for 15 minutes and diluted with ether. The solids were filtered, washed with ether, and vacuum-oven dried to provide the title compound as an HCl salt. $^1$H NMR (500 MHz, methanol-d$_4$) δ ppm 2.84-2.91 (m, 2H), 3.52 (t, J=6.1 Hz, 2H), 3.97-4.02 (m, 2H), 4.51 (bs, 2H), 6.65 (bs, 1H), 6.83 (d, J=1.8 Hz, 1H), 6.86-6.94 (m, 1H), 6.99-7.15 (m, 3H), 7.18 (d, J=3.6 Hz, 1H), 7.29 (t, J=9.4 Hz, 1H), 7.62 (dd, J=6.2, 1.4 Hz, 1H), 8.42 (d, J=6.2 Hz, 1H). MS (ESI$^+$) m/z 435.2 (M+H)$^+$.

EXAMPLE 485

4-(5-fluoro-2-methoxyphenyl)-2-(1,2,5,6-tetrahydropyridin-3-yl)-1H-pyrrolo[2,3-b]pyridine The title compound was prepared essentially as described in Example 87, substituting the appropriate boronate in Example 87C. $^1$H NMR (400 MHz, methanol-d$_4$) δ ppm 2.68-2.78 (m, 2H), 3.43 (t, J=6.1 Hz, 2H), 3.83 (s, 3H), 4.16 (d, J=2.5 Hz, 2H), 6.70 (s, 1H), 6.82-6.88 (m, 1H), 7.22-7.29 (m, 1H), 7.27-7.39 (m, 2H), 7.60 (d, J=6.1 Hz, 1H), 8.37 (d, J=6.1 Hz, 1H). MS (ESI$^+$) m/z 324.1 (M+H)$^+$.

The following compounds (concluding with Example 976) were prepared essentially as described in Example 215, substituting the appropriate amine for Example 87D. Some products were purified by flash chromatography while others were purified by reverse-phase HPLC. Accordingly, some examples were isolated as trifluoroacetic acid salts. Some examples (free base or trifluoroacetic acid salt) were converted into HCl salts.

EXAMPLE 508

4-(4-{5-[(3,5-difluorobenzyl)amino]-2-fluorophenyl}-1H-pyrrolo[2,3-b]pyridin-2-yl)-N-methyl-3,6-dihydropyridine-1(2H)-carboxamide $^1$H NMR (400 MHz, methanol-d$_4$) δ ppm 2.48-2.55 (m, 2H), 2.77 (s, 3H), 3.65 (t, J=5.6 Hz, 2H), 4.12-4.17 (m, 2H), 4.39 (bs, 2H), 6.48-6.54 (m, 2H), 6.74-6.87 (m, 3H), 6.96-7.04 (m, 2H), 7.09-7.17 (m, 1H), 7.46 (dd, J=6.1, 1.7 Hz, 1H), 8.28 (d, J=6.1 Hz, 1H). MS (ESI$^+$) m/z 492.1 (M+H)$^+$.

EXAMPLE 536

5-[4-(5-fluoro-2-methoxyphenyl)-1H-pyrrolo[2,3-b]pyridin-2-yl]-N-methyl-3,6-dihydropyridine-1(2H)-carboxamide $^1$H NMR (400 MHz, methanol-d$_4$) δ ppm 2.35-2.43 (m, 2H), 2.75 (s, 3H), 3.56 (t, J=5.7 Hz, 2H), 3.77 (s, 3H), 4.24 (d, J=2.6 Hz, 2H), 6.36 (s, 1H), 6.55-6.61 (m, 1H), 7.08-7.21 (m, 4H), 8.17 (d, J=5.1 Hz, 1H). MS (ESI$^+$) m/z 381.1 (M+H)$^+$.

EXAMPLE 596

3-[4-(5-fluoro-2-methoxyphenyl)-1H-pyrrolo[2,3-b]pyridin-2-yl]-N-methyl-8-azabicyclo[3.2.1]oct-2-ene-8-carboxamide $^1$H NMR (400 MHz, methanol-d$_4$) δ ppm 1.74-1.85 (m, 1H), 1.98-2.15 (m, 2H), 2.25-2.33 (m, 2H), 2.71 (s, 3H), 3.05-3.15 (m, 1H), 3.81 (s, 3H), 4.45-4.52 (m, 1H), 4.60 (t, J=5.4 Hz, 1H), 6.51 (s, 1H), 6.87 (d, J=5.4 Hz, 1H), 7.19-7.33 (m, 3H), 7.50 (d, J=6.1 Hz, 1H), 8.27 (d, J=6.1 Hz, 1H). MS (ESI$^+$) m/z 407.0 (M+H)$^+$.

EXAMPLE 618

N-methyl-4-{4-[4-(methylcarbamoyl)phenyl]-1H-pyrrolo[2,3-b]pyridin-2-yl}-3,6-dihydropyridine-1(2H)-carboxamide $^1$H NMR (400 MHz, methanol-d$_4$) δ ppm 2.59-2.65 (m, 2H), 2.76 (s, 3H), 2.97 (s, 3H), 3.65 (t, J=5.6 Hz, 2H), 4.12-4.17 (m, 2H), 6.52-6.57 (m, 1H), 6.85 (s, 1H), 7.51 (d, J=5.9 Hz, 1H), 7.89-7.96 (m, 2H), 8.01-8.06 (m, 2H), 8.32 (d, J=5.8 Hz, 1H). MS (ESI$^+$) m/z 390.1 (M+H)$^+$.

EXAMPLE 674

4-(4-{5-fluoro-2-[($^2$H$_3$)methyloxy]phenyl}-1H-pyrrolo[2,3-b]pyridin-2-yl)-N-methyl-3,6-dihydropyridine-1(2H)-carboxamide $^1$H NMR (500 MHz, methanol-d$_4$) δ ppm 2.56-2.62 (m, 2H), 2.76 (s, 3H), 3.64 (t, J=5.6 Hz, 2H), 4.13-4.18 (m, 2H), 6.57-6.62 (m, 1H), 6.65 (s, 1H), 7.22-7.28 (m, 1H), 7.27-7.43 (m, 2H), 7.60 (d, J=6.2 Hz, 1H), 8.31 (d, J=6.2 Hz, 1H). MS (ESI$^+$) m/z 384.1 (M+H)$^+$.

EXAMPLE 696

4-[5-fluoro-4-(5-fluoro-2-methoxyphenyl)-1H-pyrrolo[2,3-b]pyridin-2-yl]-N-methyl-3,6-dihydropyridine-1(2H)-carboxamide $^1$H NMR (400 MHz, DMSO-d$_6$) δ ppm 2.37-2.46 (m, 2H), 2.59 (d, J=4.2 Hz, 3H), 3.41-3.56 (m, 2H), 3.73 (s, 3H), 3.97-4.02 (m, 2H), 6.18 (d, J=2.0 Hz, 1H), 6.45 (q, J=4.4 Hz, 1H), 6.49-6.54 (m, 1H), 7.17-7.28 (m, 2H), 7.33 (td, J=8.6, 3.2 Hz, 1H), 8.19 (d, J=2.6 Hz, 1H), 11.90-11.95 (m, 1H). MS (ESI$^+$) m/z 399.1 (M+H)$^+$.

EXAMPLE 849

4-{4-[3-fluoro-4-(methylcarbamoyl)phenyl]-1H-pyrrolo[2,3-b]pyridin-2-yl}-N-methyl-3,6-dihydropyridine-1(2H)-carboxamide $^1$H NMR (400 MHz, methanol-d$_4$) δ ppm 2.58-2.66 (m, 2H), 2.76 (s, 3H), 2.97 (s, 3H), 3.64 (t, J=5.6 Hz, 2H), 4.10-4.16 (m, 2H), 6.50-6.55 (m, 1H), 6.81 (s, 1H), 7.44 (d, J=5.7 Hz, 1H), 7.67 (dd, J=11.5, 1.6 Hz, 1H), 7.74 (dd, J=7.9, 1.6 Hz, 1H), 7.95 (t, J=7.7 Hz, 1H), 8.31 (d, J=5.7 Hz, 1H). MS (ESI$^+$) m/z 408.1 (M+H)$^+$.

EXAMPLE 976

4-[4-(5-fluoro-2-methoxyphenyl)-1H-pyrrolo[2,3-b]pyridin-2-yl]-N,3,3-trimethyl-3,6-dihydropyridine-1(2H)-carboxamide $^1$H NMR (400 MHz, methanol-d$_4$) δ ppm 1.22 (s, 6H), 2.77 (s, 3H), 3.35 (d, J=1.1 Hz, 2H), 3.77 (s, 3H), 4.05 (d, J=3.4 Hz, 2H), 6.03 (t, J=3.4 Hz, 1H), 6.21 (s, 1H), 7.08 (d, J=5.0 Hz, 1H), 7.09-7.22 (m, 3H), 8.16 (d, J=5.0 Hz, 1H). MS (ESI$^+$) m/z 409.2 (M+H)$^+$.

EXAMPLE 510 ethyl 4-[4-(5-fluoro-2-methoxyphenyl)-1H-pyrrolo[2,3-b]pyridin-2-yl]cyclohex-3-ene-1-carboxylate The title compound was prepared as described in Example 219B. $^1$H NMR (400 MHz, DMSO-D$_6$) δ ppm 11.73 (s, 1H) 8.18 (d, J=4.88 Hz, 1H) 7.11-7.32 (m, 3H) 7.02 (d, J=4.88 Hz, 1H) 6.53 (s, 1H) 6.19 (d, J=1.83 Hz, 1H) 3.94-4.21 (m, 2H) 3.73 (s, 3H) 2.54-2.73 (m, 1H) 2.28-2.46 (m, 3H) 1.98-2.13 (m, 1H) 1.57-1.81 (m, 1H) 1.09-1.28 (m, 3H). MS (ESI): 395.2 (M+H)$^+$.

EXAMPLE 511

4-(2-ethoxy-5-fluorophenyl)-2-[1-(methylsulfonyl)-1,2,3,6-tetrahydropyridin-4-yl]-1H-pyrrolo[2,3-b]pyridine The title compound was prepared using the procedure described in Example 382A, using 2-(2-ethoxy-5-fluorophenyl)-4,4,5,5-tetramethyl-1,3,2-dioxaborolane in place of 4-fluoro-3-(4,4,5,5-tetramethyl-1,3,2-dioxaborolan-2-yl)phenol and Example 473A in place of Example 220C. $^1$H NMR (400 MHz, DMSO-d$_6$) δ ppm 1.16 (t, 3 H) 2.62 (s, 2 H) 2.94 (s, 3 H) 3.38 (t, 2 H) 3.92 (d, 2 H) 4.05 (q, 2 H) 6.37 (d, 1 H) 6.57 (s, 1 H) 7.14 (d, 1 H) 7.17-7.22 (m, 1 H) 7.23-7.32 (m, 2 H) 8.25 (d, 1 H) 12.06 (s, 1 H); LCMS: 416 (M+H)$^+$.

EXAMPLE 523

(4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid

EXAMPLE 523A tert-butyl 2-(4-(4-(4-(5-fluoro-2-methoxyphenyl)-1H-pyrrolo[2,3-b]pyridin-2-yl)-5,6-dihydropyridin-1(2H)-yl)piperidin-1-yl)acetate To a mixture of Example 87D (0.200 g, 0.505 mmol) and triethylamine (0.155 mL, 1.110 mmol), acetic acid (0.144 mL, 2.52 mmol) in dichloromethane (3 mL) and methanol (3 mL) was added tert-butyl 2-(4-oxopiperidin-1-yl)acetate (0.215 g, 1.009 mmol) and MP-cyanoborohydride (Biotage, 811 mg, 2.019 mmol). The reaction mixture was heated at 40° C. for 3 hours. The solid material was filtered and rinsed with dichloromethane and methanol. The filtrate was concentrated. The residue was partitioned in ethyl acetate and saturated aqueous sodium bicarbonate. The organic layer was washed with brine, dried over anhydrous sodium sulfate, filtered, and concentrated until most solvent was evaporated. The precipitates were filtered, washed with cold ethyl acetate, and vacuum oven-dried to provide the title compound. MS (ESI$^+$) m/z 521.1 (M+H)$^+$.

EXAMPLE 523B (4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid A solution of Example 523A (0.176 g, 0.338 mmol) and trifluoroacetic acid (0.651 mL, 8.45 mmol) in CH$_2$Cl$_2$ (2.5 mL) was stirred overnight. The reaction mixture was concentrated. The concentrate was dissolved in 2 mL of dichloromethane and treated with 1.5 mL of 2M HCl in ether. The suspension was sonicated, diluted with ether, and stirred for 0.5 hour. The solids were filtered, washed with ether, and vacuum oven-dried to provide the title compound as an HCl salt. $^1$H NMR (400 MHz, methanol-d$_4$) δ ppm 2.02-2.45 (m, 2H), 2.52-2.61 (m, 2H), 3.01-3.09 (m, 2H), 3.28-3.37 (m, 2H), 3.40-3.76 (m, 2H), 3.83 (s, 3H), 3.79-3.93 (m, 3H), 4.16-4.20 (m, 4H), 6.62 (bs, 1H), 6.77 (s, 1H), 7.21-7.37 (m, 3H), 7.59 (d, J=6.1 Hz, 1H), 8.37 (d, J=6.1 Hz, 1H). MS (ESI$^+$) m/z 465.0 (M+H)$^+$.

EXAMPLE 528

2-{4-[3-cyano-4-(5-fluoro-2-methoxyphenyl)-1H-pyrrolo[2,3-b]pyridin-2-yl]piperazin-1-yl}-N,N-dimethylacetamide The title compound was prepared as described in Example 231F, substituting Example 1326B for Example 231E. $^1$H NMR (400 MHz, DMSO-d$_6$) δ ppm 2.57-2.64 (m, 4 H) 2.81 (s, 3 H) 3.01 (s, 3 H) 3.21 (s, 2 H) 3.60-3.66 (m, 4 H) 3.72 (s, 3 H) 6.90 (d, J=5.19 Hz, 1 H) 7.03-7.12 (m, 2 H) 7.18-7.26 (m, 1 H) 8.02 (d, J=4.88 Hz, 1 H). MS (ESI$^+$) m/z: 437.1.1 (M+H)$^+$.

EXAMPLE 533

4-[4-(5-fluoro-2-methoxyphenyl)-1H-pyrrolo[2,3-b]pyridin-2-yl]-N-methyl-3,6-dihydropyridine-1(2H)-sulfonamide To a suspension of Example 87D (50 mg, 0.155 mmol) in methylene chloride (4 mL) was added methylsulfamoyl chloride (31 mg, 0.232 mmol) and triethyl amine (0.065 mL). The mixture was stirred at room temperature overnight, and was directly separated by flash chromatography (0-15% CH$_3$OH in CH$_2$Cl$_2$) to provide the title compound. $^1$H NMR (400 MHz, CD$_3$OD): δ2.65 (s, 4 H), 3.45 (t, J=5.80 Hz, 2 H), 3.77 (s, 3 H), 3.94 (d, J=3.05 Hz, 2 H), 4.56 (s, 1 H), 6.31 (s, 1 H), 6.42 (t, J=3.66 Hz, 1 H), 7.08 (d, J=4.88 Hz, 1 H), 7.13-7.17 (m, 3 H), 8.17 (d, J=4.88 Hz, 1 H); MS (DCI/NH$_3$) m/z 417 (M+H)$^+$.

EXAMPLE 538

4-(5-fluoro-2-methylphenyl)-2-[1-(methylsulfonyl)-1,2,3,6-tetrahydropyridin-4-yl]-1H-pyrrolo[2,3-b]pyridine The title compound was prepared using the procedure described in Example 382A, using (5-fluoro-2-methylphenyl)boronic acid in place of 4-fluoro-3-(4,4,5,5-tetramethyl-1,3,2-dioxaborolan-2-yl)phenol and Example 473A in place of Example 220C. $^1$H NMR (400 MHz, DMSO-d$_6$) δ ppm 2.12 (s, 3 H) 2.59 (d, 2 H) 2.88-2.99 (m, 3 H) 3.35 (t, 2 H) 3.91 (d, 2 H) 6.18 (d, 1 H) 6.55 (t, 1 H) 6.97 (d, 1 H) 7.12 (dd, 1 H) 7.17-7.24 (m, 1 H) 7.41 (dd, 1 H) 8.26 (d, 1 H) 12.00 (s, 1 H).; LCMS: 500 (M+H)$^+$.

EXAMPLE 539

4-{5-[(3,5-difluorobenzyl)oxy]-2-fluorophenyl}-2-(1,2,3,6-tetrahydropyridin-4-yl)-1H-pyrrolo[2,3-b]pyridine

EXAMPLE 539A tert-butyl 4-(4-(2-fluoro-5-hydroxyphenyl)-1-tosyl-1H-pyrrolo[2,3-b]pyridin-2-yl)-5,6-dihydropyridine-1(2H)-carboxylate A mixture of Example 220C (1139 mg, 2.139 mmol), 4-fluoro-3-(4,4,5,5-tetramethyl-1,3,2-dioxaborolan-2-yl)phenol (611 mg, 2.57 mmol), PdCl$_2$ (1,1'-bis(diphenylphosphino)ferrocene)-CH$_2$Cl$_2$ (105 mg, 0.128 mmol), sodium carbonate (6416 μL, 6.42 mmol) in dioxane (3 mL) was heated at 100° C. overnight. The reaction was diluted with ethyl acetate and washed with water. The organic phase was concentrated and purified by flash chromatography on silica gel using an ISCO Companion eluting with heptanes/ethyl acetate to provide the title compound. MS (ESI+) m/z 564 (M+H)+.

EXAMPLE 539B 4-(5-((3,5-difluorobenzyl)oxy)-2-fluorophenyl)-2-(1,2,3,6-tetrahydropyridin-4-yl)-1H-pyrrolo[2,3-b]pyridine A solution of Example 539A (350 mg, 0.6 mmol), (3,5-difluorophenyl)methanol (134 mg, 0.9 mmol) and 2-(tributylphosphoranylidene)acetonitrile (225 mg, 0.9 mmol) in toluene (10 mL) was heated at 75° C. overnight. The reaction was diluted with ethyl acetate and washed with water. The organic phase was concentrated and purified by flash chromatography on silica gel using an ISCO Companion eluting with heptanes/ethyl acetate (30%) to give the protected intermediate. The intermediate was dissolved in mixed solvent of dioxane (10 mL) and methanol (10 mL) and NaOH (50 mg, in 1 mL water) was added. The mixture was stirred at 50° C. for overnight. The reaction was treated with water and extracted with ethyl acetate. The organic phase was concentrated and dissolved in $CH_2Cl_2$ (10 mL) then treated with trifluoroacetic acid (1 mL). The mixture was stirred at room temperature for 5 hours and concentrated in vacuo and the residue was purified by reverse-phase HPLC on Zorbax XDB C-18 (32) using a gradient of 5-40% acetonitrile/water (containing 0.1% trifluoroacetic acid) to afford the title compound as the trifluoroacetate salt. $^1$H NMR (400 MHz, Methanol-$d_4$) δ 2.85 (ddt, J=6.2, 3.9, 2.0 Hz, 2H), 3.49 (t, J=6.2 Hz, 2H), 3.95 (q, J=2.6 Hz, 2H), 5.18 (s, 2H), 6.49 (tt, J=3.5, 1.6 Hz, 1H), 6.58 (d, J=2.0 Hz, 1H), 6.91 (tt, J=9.2, 2.4 Hz, 1H), 7.09 (dt, J=6.9, 2.0 Hz, 2H), 7.17 (dt, J=8.9, 3.6 Hz, 1H), 7.20-7.25 (m, 1H), 7.26-7.33 (m, 2H), 8.32 (d, J=5.5 Hz, 1H). MS (ESI+) m/z 436 (M+H)+.

EXAMPLE 540

4-{5-[(3,5-difluorobenzyl)oxy]-2-fluorophenyl}-2-(1-methyl-1,2,3,6-tetrahydropyridin-4-yl)-1H-pyrrolo[2,3-b]pyridine The title compound was prepared essentially as described in Example 89, substituting Example 539B for Example 88C. $^1$H NMR (400 MHz, Methanol-$d_4$) δ 2.94 (ddq, J=6.1, 3.9, 2.2 Hz, 2H), 3.03 (s, 3H), 3.40 (m, 1H), 3.94 (dd, J=92.7, 70.6 Hz, 3H), 5.17 (s, 2H), 6.46 (tt, J=3.4, 1.5 Hz, 1H), 6.59 (d, J=2.0 Hz, 1H), 6.91 (tt, J=9.2, 2.4 Hz, 1H), 7.09 (dt, J=6.6, 2.0 Hz, 2H), 7.17 (dt, J=9.0, 3.6 Hz, 1H), 7.21-7.28 (m, 2H), 7.28-7.33 (m, 1H), 8.33 (d, J=5.4 Hz, 1H). MS (ESI+) m/z 450 (M+H)+.

EXAMPLE 541

3-[4-(4-{5-[(3,5-difluorobenzyl)oxy]-2-fluorophenyl}-1H-pyrrolo[2,3-b]pyridin-2-yl)-3,6-dihydropyridin-1(2H)-yl]propane-1,2-diol The title compound was prepared essentially as described in Example 149, substituting Example 539B (30 mg, 0.08 mmol) for Example 135B. $^1$H NMR (400 MHz, Methanol-$d_4$) δ 2.95 (d, J=5.1 Hz, 2H), 3.33-3.45 (m, 2H), 3.60 (qd, J=11.3, 5.1 Hz, 2H), 3.74-4.32 (m, 5H), 5.18 (s, 2H), 6.42-6.56 (m, 1H), 6.64 (d, J=2.0 Hz, 1H), 6.82-6.96 (m, 1H), 7.09 (dt, J=6.7, 2.0 Hz, 2H), 7.19 (dt, J=9.0, 3.6 Hz, 1H), 7.23-7.34 (m, 2H), 7.37 (dd, J=5.6, 1.3 Hz, 1H), 8.35 (d, J=5.6 Hz, 1H). MS (ESI+) m/z 510 (M+H)+.

EXAMPLE 542

4-{5-[(3,5-difluorobenzyl)oxy]-2-fluorophenyl}-2-[1-(methylsulfonyl)-1,2,3,6-tetrahydropyridin-4-yl]-1H-pyrrolo[2,3-b]pyridine The title compound was prepared essentially as described in Examples 220E, substituting Example 539 (30 mg, 0.08 mmol) for Example 220D. $^1$H NMR (400 MHz, Methanol-$d_4$) δ 2.69 (dd, J=5.6, 3.4 Hz, 2H), 2.92 (s, 3H), 3.52 (t, J=5.8 Hz, 2H), 4.04 (q, J=2.9 Hz, 2H), 5.18 (s, 2H), 6.51 (d, J=4.3 Hz, 2H), 6.91 (tt, J=9.1, 2.4 Hz, 1H), 7.05-7.14 (m, 2H), 7.14-7.36 (m, 4H), 8.28 (d, J=5.6 Hz, 1H). MS (ESI+) m/z 514 (M+H)+.

EXAMPLE 554

4-(5-fluoro-2-methoxyphenyl)-2-[1-(morpholin-4-ylsulfonyl)-1,2,3,6-tetrahydropyridin-4-yl]-1H-pyrrolo[2,3-b]pyridine To a suspension of Example 87D (59 mg, 0.182 mmol) in methylene chloride (4 mL) was added morpholine-4-sulfonyl chloride (51 mg, 0.274 mmol) and triethyl amine (0.076 mL). The mixture was stirred at room temperature overnight and was directly separated by flash chromatography (0-15% $CH_3OH$ in $CH_2Cl_2$) to provide the title compound. $^1$H NMR (400 MHz, DMSO-$d_6$): δ2.57 (s, 2 H), 3.11-3.14 (m, 4 H), 3.45 (t, J=5.65 Hz, 2 H), 3.59-3.64 (m, 4 H), 3.74 (s, 3 H), 3.96 (d, J=2.75 Hz, 2 H), 6.27 (d, J=1.83 Hz, 1 H), 6.52 (s, 1 H), 7.04 (d, J=5.19 Hz, 1 H), 7.18-7.29 (m, 3 H), 8.21 (d, J=5.19 Hz, 1 H), 11.87 (d, J=1.22 Hz, 1 H); MS (DCI/NH$_3$) m/z 473 (M+H)+.

EXAMPLE 555

2-fluoro-N-{4-methoxy-3-[2-(1,2,3,6-tetrahydropyridin-4-yl)-1H-pyrrolo[2,3-b]pyridin-4-yl]benzyl}aniline

EXAMPLE 555A tert-butyl 4-(4-(5-formyl-2-methoxyphenyl)-1-tosyl-1H-pyrrolo[2,3-b]pyridin-2-yl)-5,6-dihydropyridine-1(2H)-carboxylate The title compound was prepared according the procedure described in Example 440C, using Example 220C in place of Example 440B and (5-formyl-2-methoxyphenyl)boronic acid in place of (5-amino-2-chlorophenyl)boronic acid.

EXAMPLE 555B tert-butyl 4-(4-(5-formyl-2-methoxyphenyl)-1H-pyrrolo[2,3-b]pyridin-2-yl)-5,6-dihydropyridine-1(2H)-carboxylate The title compound was prepared according the procedure described in Example 324B, using Example 555A in place of Example 324A.

EXAMPLE 555C tert-butyl 4-(4-(5-(((2-fluorophenyl)amino)methyl)-2-methoxyphenyl)-1H-pyrrolo[2,3-b]pyridin-2-yl)-5,6-dihydropyridine-1(2H)-carboxylate The title compound was prepared according the procedure described in Example 440D, using Example 555B in place of Example 440C and 2-fluoroaniline in place of nicotinaldehyde.

EXAMPLE 555D 2-fluoro-N-{4-methoxy-3-[2-(1,2,3,6-tetrahydropyridin-4-yl)-1H-pyrrolo[2,3-b]pyridin-4-yl]benzyl}aniline The title compound was prepared according the procedure described in Example 440E, using Example 555C in place of Example 440D. $^1$H NMR (400 MHz, DMSO-d$_6$) δ ppm 2.54 (q, J=4.7 Hz, 2H), 3.33 (p, J=6.3, 5.6 Hz, 2H), 3.74 (s, 2H), 3.83 (d, J=4.6 Hz, 2H), 4.36 (s, 3H), 6.19 (d, J=2.0 Hz, 1H), 6.26-6.58 (m, 2H), 6.58-6.71 (m, 1H), 6.90 (td, J=7.8, 1.4 Hz, 1H), 6.95-7.12 (m, 2H), 7.12-7.21 (m, 1H), 7.41-7.50 (m, 2H), 8.23 (d, J=5.0 Hz, 1H), 8.92 (d, J=6.4 Hz, 2H), 12.01 (d, J=2.3 Hz, 1H). MS (ESI$^+$) m/z 429.2 (M+H)$^+$.

EXAMPLE 556

N-{4-methoxy-3-[2-(1,2,3,6-tetrahydropyridin-4-yl)-1H-pyrrolo[2,3-b]pyridin-4-yl]benzyl}tetrahydro-2H-pyran-4-amine

EXAMPLE 556A tert-butyl 4-(4-(2-methoxy-5-(((tetrahydro-2H-pyran-4-yl)amino)methyl)phenyl)-1H-pyrrolo[2,3-b]pyridin-2-yl)-5,6-dihydropyridine-1(2H)-carboxylate The title compound was prepared according the procedure described in Example 440D, using Example 555B in place of Example 440C and tetrahydro-2H-pyran-4-amine in place of nicotinaldehyde.

EXAMPLE 556B

N-{4-methoxy-3-[2-(1,2,3,6-tetrahydropyridin-4-yl)-1H-pyrrolo[2,3-b]pyridin-4-yl]benzyl}tetrahydro-2H-pyran-4-amine The title compound was prepared according the procedure described in Example 440E, using Example 556A in place of Example 440D. $^1$H NMR (400 MHz, DMSO-d$_6$) δ ppm 1.62 (qd, J=12.2, 4.6 Hz, 2H), 1.96-2.29 (m, 2H), 2.69 (dt, J=6.4, 3.7 Hz, 2H), 3.25-3.39 (m, 4H), 3.80 (s, 3H), 3.87-4.17 (m, 2H), 4.22 (t, J=5.9 Hz, 2H), 6.37 (d, J=1.9 Hz, 1H), 6.51 (d, J=3.7 Hz, 1H), 6.55-7.53 (m, 6H), 7.53-7.65 (m, 2H), 8.28 (d, J=5.0 Hz, 1H), 8.83-9.17 (m, 3H), 12.12 (d, J=2.4 Hz, 1H). MS (ESI$^+$) m/z 419.2 (M+H)$^+$.

EXAMPLE 557

4-[2-methoxy-5-(morpholin-4-ylmethyl)phenyl]-2-(1,2,3,6-tetrahydropyridin-4-yl)-1H-pyrrolo[2,3-b]pyridine

EXAMPLE 557A tert-butyl 4-(4-(2-methoxy-5-(morpholinomethyl)phenyl)-1H-pyrrolo[2,3-b]pyridin-2-yl)-5,6-dihydropyridine-1(2H)-carboxylate The title compound was prepared according the procedure described in Example 440D, using Example 555B in place of Example 440C and morpholine in place of nicotinaldehyde.

EXAMPLE 557B

4-[2-methoxy-5-(morpholin-4-ylmethyl)phenyl]-2-(1,2,3,6-tetrahydropyridin-4-yl)-1H-pyrrolo[2,3-b]pyridine The title compound was prepared according the procedure described in Example 440E, using Example 557A in place of Example 440D. $^1$H NMR (400 MHz, DMSO-d$_6$) δ ppm 2.64-2.71 (m, 2H), 3.11 (d, J=10.3 Hz, 2H), 3.25-3.49 (m, 4H), 3.64 (t, J=12.6 Hz, 2H), 3.80 (s, 4H), 3.97 (d, J=14.3 Hz, 3H), 4.37 (s, 3H), 6.34 (d, J=2.0 Hz, 1H), 6.50 (d, J=3.5 Hz, 1H), 7.09 (d, J=5.0 Hz, 1H), 7.30 (d, J=8.4 Hz, 1H), 7.50-7.64 (m, 2H), 8.26 (d, J=4.9 Hz, 1H), 9.06 (d, J=6.8 Hz, 2H), 10.28 (s, 1H), 12.01 (d, J=2.4 Hz, 1H) MS (ESI$^+$) m/z 405.1 (M+H)$^+$.

EXAMPLE 558

N-benzyl-4-[4-(5-fluoro-2-methoxyphenyl)-1H-pyrrolo[2,3-b]pyridin-2-yl]cyclohex-3-ene-1-carboxamide To a solution of Example 219C (80 mg, 0.218 mmol) in N,N-dimethylformamide was added 1 (3-dimethylaminopropyl)-3-ethylcarbodiimide hydrochloride (54.4 mg, 0.284 mmol), 1H-benzo[d][1,2,3]triazol-1-ol hydrate (43.5 mg, 0.284 mmol), N-ethyl-N-isopropylpropan-2-amine (0.095 mL, 0.546 mmol) followed by phenylmethanamine (0.048 mL, 0.437 mmol). The reaction was held at room temperature overnight, and then diluted with ethyl acetate. The organics were washed with sodium bicarbonate, water, brine, and then dried over magnesium sulfate, filtered, and concentrated in vacuo. The crude material was triturated with ethyl acetate and the solid filtered to give the titled compound. $^1$H NMR (400 MHz, DMSO-d$_6$) δ ppm 11.74 (s, 1 H) 8.46 (t, J=5.95 Hz, 1 H) 8.18 (d, J=4.88 Hz, 1 H) 7.11-7.41 (m, 8 H) 7.02 (d, J=4.88 Hz, 1 H) 6.56 (s, 1 H) 6.19 (d, J=1.53 Hz, 1 H) 4.17-4.41 (m, 2 H) 3.74 (s, 3 H) 2.44-2.62 (m, 2 H) 2.26-2.44 (m, 3 H) 1.88-2.07 (m, 1 H) 1.58-1.77 (m, 1 H). MS (ESI): 456.2 (M+H)$^+$.

The following compounds (concluding with Example 963) were prepared essentially as described in Example 558, substituting the appropriate amine for phenylmethanamine. For Examples 605, 767, 781, 810 and 811, 1-(3-dimethylaminopropyl)-3-ethylcarbodiimide hydrochloride and 1H-benzo[d][1,2,3]triazol-1-ol hydrate were substituted with O-(7-azabenzotriazol-1-yl)-N,N'N'N'-tetramethyluronium hexafluorophosphate. Products were purified by trituration or flash chromatography.

EXAMPLE 559

N-(3-fluorobenzyl)-4-[4-(5-fluoro-2-methoxyphenyl)-1H-pyrrolo[2,3-b]pyridin-2-yl]cyclohex-3-ene-1-carboxamide $^1$H NMR (400 MHz, DMSO-d$_6$) δ ppm 11.73 (s, 1 H) 8.43 (t, J=5.95 Hz, 1 H) 8.18 (d, J=4.88 Hz, 1 H) 7.31-7.42 (m, 1 H) 7.14-7.31 (m, 3 H) 6.96-7.15 (m, 4 H) 6.55 (s, 1 H) 6.19 (d, J=1.83 Hz, 1 H) 4.17-4.43 (m, 2 H) 3.74 (s, 3 H) 2.44-2.62 (m, 2 H) 2.28-2.43 (m, 3 H) 1.90-2.05 (m, 1 H) 1.55-1.77 (m, 1 H)). MS (ESI): 474.2 (M+H)$^+$.

EXAMPLE 560

N-(3,5-difluorobenzyl)-4-[4-(5-fluoro-2-methoxyphenyl)-1H-pyrrolo[2,3-b]pyridin-2-yl]cyclohex-3-ene-1-carboxamide $^1$H NMR (400 MHz, DMSO-d$_6$) δ ppm 11.73 (s, 1 H) 8.46 (t, J=5.95 Hz, 1 H) 8.18 (d, J=5.19 Hz, 1 H) 7.15-7.32 (m, 3 H) 7.09 (t, J=9.46 Hz, 1 H) 7.02 (d, J=4.88 Hz, 1 H) 6.96 (d, J=6.71 Hz, 2 H) 6.56 (s, 1 H) 6.19 (s, 1 H) 4.16-4.46 (m, 2 H) 3.74 (s, 3 H) 2.45-2.61 (m, 2 H) 2.39 (d, J=3.05 Hz, 3 H) 1.87-2.08 (m, 1 H) 1.54-1.78 (m, 1H). MS (ESI): 492.2 (M+H)$^+$.

EXAMPLE 561

N-(2,5-difluorobenzyl)-4-[4-(5-fluoro-2-methoxyphenyl)-1H-pyrrolo[2,3-b]pyridin-2-yl]cyclohex-3-ene-1-carboxamide $^1$H NMR (400 MHz, DMSO-d$_6$) δ ppm 11.73 (d, J=1.22 Hz, 1 H) 8.42 (t, J=5.95 Hz, 1 H) 8.18 (d, J=4.88 Hz, 1 H) 7.05-7.34 (m, 6 H) 7.02 (d, J=4.88 Hz, 1 H) 6.55 (s, 1 H) 6.19 (d, J=1.83 Hz, 1 H) 4.20-4.42 (m, 2 H) 3.74 (s, 3 H) 2.45-2.63 (m, 2 H) 2.28-2.43 (m, 3 H) 1.88-2.06 (m, 1 H) 1.56-1.80 (m, 1 H). MS (ESI): 492.2 (M+H)$^+$.

EXAMPLE 562

N-(3-chlorobenzyl)-4-[4-(5-fluoro-2-methoxyphenyl)-1H-pyrrolo[2,3-b]pyridin-2-yl]cyclohex-3-ene-1-carboxamide $^1$H NMR (400 MHz, DMSO-d$_6$) δ ppm 11.73 (d, J=1.53 Hz, 1 H) 8.43 (t, J=6.10 Hz, 1 H) 8.18 (d, J=4.88 Hz, 1 H) 7.12-7.43 (m, 7 H) 7.02 (d, J=4.88 Hz, 1 H) 6.55 (s, 1 H) 6.19 (d, J=2.14 Hz, 1 H) 4.18-4.40 (m, 2 H) 3.74 (s, 3 H) 2.44-2.63 (m, 2 H) 2.28-2.44 (m, 3 H) 1.87-2.07 (m, 1 H) 1.55-1.80 (m, 1 H). MS (ESI): 490.2 (M+H)$^+$.

EXAMPLE 563

4-[4-(5-fluoro-2-methoxyphenyl)-1H-pyrrolo[2,3-b]pyridin-2-yl]-N-(pyridin-4-ylmethyl)cyclohex-3-ene-1-carboxamide $^1$H NMR (400 MHz, DMSO-d$_6$) δ ppm 11.75 (s, 1 H) 8.38-8.63 (m, 3 H) 8.18 (d, J=4.88 Hz, 1 H) 7.12-7.39 (m, 5 H) 7.02 (d, J=4.88 Hz, 1 H) 6.56 (s, 1 H) 6.20 (d, J=1.83 Hz, 1 H) 4.20-4.44 (m, 2 H) 3.74 (s, 3 H) 2.46-2.67 (m, 2 H) 2.28-2.45 (m, 3 H) 1.89-2.11 (m, 1 H) 1.56-1.82 (m, 1 H). MS (ESI): 457.2 (M+H)$^+$.

EXAMPLE 564

4-[4-(5-fluoro-2-methoxyphenyl)-1H-pyrrolo[2,3-b]pyridin-2-yl]-N-[(3-methyl-1H-pyrazol-5-yl)methyl]cyclohex-3-ene-1-carboxamide $^1$H NMR (500 MHz, DMSO-d$_6$) δ ppm 12.18 (s, 1 H) 11.72 (s, 1 H) 8.17 (d, J=4.88 Hz, 2 H) 7.12-7.35 (m, 3 H) 7.01 (d, J=4.88 Hz, 1 H) 6.54 (s, 1 H) 6.18 (s, 1 H) 5.85 (s, 1 H) 4.07-4.30 (m, 2 H) 3.74 (s, 3 H) 2.50 (s, 2 H) 2.24-2.47 (m, 3 H) 2.16 (s, 3 H) 1.92 (d, J=10.99 Hz, 1 H) 1.58-1.73 (m, 1 H). MS (ESI): 460.2 (M+H)$^+$.

EXAMPLE 565

4-[4-(5-fluoro-2-methoxyphenyl)-1H-pyrrolo[2,3-b]pyridin-2-yl]-N-(tetrahydro-2H-pyran-4-ylmethyl)cyclohex-3-ene-1-carboxamide $^1$H NMR (400 MHz, DMSO-d$_6$) δ ppm 11.73 (d, J=1.83 Hz, 1 H) 8.09-8.23 (m, 1 H) 7.85 (t, J=5.80 Hz, 1 H) 7.10-7.35 (m, 3 H) 7.01 (t, J=5.95 Hz, 1 H) 6.54 (d, J=4.58 Hz, 1 H) 6.18 (d, J=2.14 Hz, 1 H) 3.83 (dd, J=11.29, 2.75 Hz, 2 H) 3.65-3.79 (m, 3 H) 3.18-3.30 (m, 2 H) 2.88-3.05 (m, 2 H) 2.46-2.58 (m, 2 H) 2.22-2.46 (m, 3 H) 1.91 (d, J=11.90 Hz, 1 H) 1.58-1.72 (m, 2 H) 1.54 (d, J=12.82 Hz, 2 H) 1.05-1.24 (m, 2 H). MS (ESI): 464.3 (M+H)$^+$.

EXAMPLE 566

4-[4-(5-fluoro-2-methoxyphenyl)-1H-pyrrolo[2,3-b]pyridin-2-yl]-N-(4-hydroxycyclohexyl)cyclohex-3-ene-1-carboxamide $^1$H NMR (400 MHz, DMSO-d$_6$) δ ppm 11.71 (d, J=1.53 Hz, 1 H) 8.17 (d, J=5.19 Hz, 1 H) 7.63 (d, J=7.63 Hz, 1 H) 7.12-7.33 (m, 3 H) 7.01 (d, J=4.88 Hz, 1 H) 6.53 (d, J=3.97 Hz, 1 H) 6.17 (d, J=2.14 Hz, 1 H) 4.51 (d, J=4.58 Hz, 1 H) 3.73 (s, 3H) 3.48 (dd, J=7.17, 3.51 Hz, 1 H) 3.36 (dd, J=9.16, 4.88 Hz, 1 H) 2.44-2.58 (m, 2 H) 2.17-2.42 (m, 3 H) 1.68-1.95 (m, 5 H) 1.53-1.70 (m, 1 H) 1.04-1.29 (m, 4 H). MS (ESI): 464.2 (M+H)$^+$.

EXAMPLE 567

(3,3-difluoroazetidin-1-yl) {4-[4-(5-fluoro-2-methoxyphenyl)-1H-pyrrolo[2,3-b]pyridin-2-yl]cyclohex-3-en-1-yl}methanone $^1$H NMR (400 MHz, DMSO-d$_6$) δ ppm 11.74 (s, 1 H) 8.18 (d, J=4.88 Hz, 1 H) 7.10-7.34 (m, 3 H) 7.02 (d, J=5.19 Hz, 1 H) 6.54 (s, 1 H) 6.19 (d, J=1.83 Hz, 1 H) 4.56-4.83 (m, 2 H) 4.29 (t, J=12.51 Hz, 2 H) 3.59-3.87 (m, 3 H) 2.46-2.69 (m, 2 H) 2.22-2.47 (m, 3 H) 1.79-2.04 (m, 1 H) 1.47-1.71 (m, 1 H). MS (ESI): 444.2 (M+H)$^+$.

EXAMPLE 605

4-[4-(5-fluoro-2-methoxyphenyl)-1H-pyrrolo[2,3-b]pyridin-2-yl]-N-(methylsulfonyl)cyclohex-3-ene-1-carboxamide $^1$H NMR (500 MHz, DMSO-d$_6$) δ ppm 11.52-11.89 (m, 1 H) 8.05-8.30 (m, 1 H) 7.12-7.48 (m, 3 H) 7.02 (t, J=4.12

Hz, 1 H) 6.54 (d, J=2.14 Hz, 1 H) 6.19 (s, 1 H) 3.56-3.70 (m, 1 H) 3.15-3.25 (m, 2 H) 2.96-3.11 (m, 1 H) 2.84-2.95 (m, 3 H) 2.46-2.64 (m, 2 H) 2.26-2.46 (m, 2 H) 1.91-2.08 (m, 1 H) 1.53-1.83 (m, 2 H). MS (ESI): 444.2 (M+H)$^+$.

EXAMPLE 609

4-[4-(5-fluoro-2-methoxyphenyl)-1H-pyrrolo[2,3-b]pyridin-2-yl]cyclohex-3-ene-1-carboxamide $^1$H NMR (400 MHz, DMSO-d$_6$) δ ppm 11.71 (s, 1 H) 8.17 (d, J=4.88 Hz, 1 H) 7.12-7.36 (m, 4 H) 7.01 (d, J=4.88 Hz, 1 H) 6.79 (s, 1 H) 6.53 (s, 1 H) 6.18 (d, J=1.53 Hz, 1 H) 3.74 (s, 3 H) 2.50 (s, 2 H) 2.25-2.45 (m, 3 H) 1.87-2.01 (m, 1 H) 1.48-1.77 (m, 1 H). MS (ESI): 366.2 (M+H)$^+$.

EXAMPLE 624

4-[4-(5-fluoro-2-methoxyphenyl)-1H-pyrrolo[2,3-b]pyridin-2-yl]-N-methylcyclohex-3-ene-1-carboxamide $^1$H NMR (500 MHz, DMSO-d$_6$) δ ppm 11.72 (d, J=1.53 Hz, 1 H) 8.17 (d, J=4.88 Hz, 1 H) 7.78 (q, J=4.48 Hz, 1 H) 7.16-7.31 (m, 3 H) 7.01 (d, J=4.88 Hz, 1 H) 6.53 (d, J=4.58 Hz, 1 H) 6.18 (d, J=1.83 Hz, 1 H) 3.63-3.78 (m, 3 H) 2.55-2.64 (m, 3 H) 2.53-2.57 (m, 1 H) 2.26-2.41 (m, 4 H) 1.90 (d, J=1.53 Hz, 1H) 1.55-1.70 (m, 1H). MS (ESI): 380.2 (M+H)$^+$.

EXAMPLE 645

N-[(2S)-2,3-dihydroxypropyl]-4-[4-(5-fluoro-2-methoxyphenyl)-1H-pyrrolo[2,3-b]pyridin-2-yl]cyclohex-3-ene-1-carboxamide $^1$H NMR (500 MHz, DMSO-d$_6$) δ ppm 11.71 (d, J=1.53 Hz, 1 H) 8.17 (d, J=4.88 Hz, 1 H) 7.82 (t, J=5.65 Hz, 1 H) 7.13-7.32 (m, 3 H) 7.01 (d, J=4.88 Hz, 1 H) 6.54 (d, J=2.75 Hz, 1 H) 6.18 (d, J=1.83 Hz, 1 H) 4.73 (dd, J=4.88, 2.44 Hz, 1 H) 4.51 (t, J=5.80 Hz, 1 H) 3.74 (s, 3 H) 3.42-3.57 (m, 1 H) 3.13-3.31 (m, 3 H) 2.89-3.11 (m, 1 H) 2.48-2.58 (m, 2 H) 2.40-2.48 (m, 1 H) 2.24-2.40 (m, 2 H) 1.91 (d, J=10.99 Hz, 1 H) 1.56-1.72 (m, 1 H). MS (ESI): 440.2 (M+H)$^+$.

EXAMPLE 704

N-({4-[4-(5-fluoro-2-methoxyphenyl)-1H-pyrrolo[2,3-b]pyridin-2-yl]cyclohex-3-en-1-yl}carbonyl)glycine $^1$H NMR (400 MHz, DMSO-d$_6$) δ ppm 11.94 (s, 1 H) 7.96-8.37 (m, 2 H) 7.15-7.35 (m, 3 H) 7.10 (d, J=5.19 Hz, 1 H) 6.57 (s, 1 H) 6.25 (d, J=1.53 Hz, 1 H) 3.57-3.92 (m, 5 H) 2.42-2.63 (m, 3 H) 2.25-2.42 (m, 2 H) 1.83-2.05 (m, 1 H) 1.53-1.76 (m, 1 H). MS (ESI): 424.2 (M+H)$^+$.

EXAMPLE 767

N-(cyclopropylsulfonyl)-4-[4-(5-fluoro-2-methoxyphenyl)-1H-pyrrolo[2,3-b]pyridin-2-yl]cyclohex-3-ene-1-carboxamide $^1$H NMR (400 MHz, DMSO-d$_6$) δ ppm 11.74 (d, J=1.53 Hz, 1 H) 11.57 (s, 1 H) 8.18 (d, J=4.88 Hz, 1 H) 7.12-7.35 (m, 3 H) 7.02 (d, J=4.88 Hz, 1 H) 6.52 (d, J=3.05 Hz, 1 H) 6.20 (d, J=2.14 Hz, 3 H) 3.74 (s, 3 H) 3.55-3.71 (m, 1 H) 2.54-2.69 (m, 1 H) 2.27-2.47 (m, 2 H) 2.01 (d, J=12.21 Hz, 1 H) 1.57-1.78 (m, 1 H) 1.21-1.35 (m, 4 H). MS (ESI): 470.2 (M+H)$^+$.

EXAMPLE 781

4-[4-(5-fluoro-2-methoxyphenyl)-1H-pyrrolo[2,3-b]pyridin-2-yl]-N-(propan-2-ylsulfonyl)cyclohex-3-ene--carboxamide $^1$H NMR (400 MHz, DMSO-d$_6$) δ ppm 11.74 (d, J=1.53 Hz, 1 H) 11.57 (s, 1 H) 8.18 (d, J=4.88 Hz, 1 H) 7.12-7.35 (m, 3 H) 7.02 (d, J=4.88 Hz, 1 H) 6.52 (d, J=3.05 Hz, 1 H) 6.20 (d, J=2.14 Hz, 3 H) 3.74 (s, 3 H) 3.55-3.71 (m, 1 H) 2.54-2.69 (m, 1 H) 2.27-2.47 (m, 2 H) 2.01 (d, J=12.21 Hz, 1 H) 1.57-1.78 (m, 1 H) 1.21-1.35 (m, 6 H). MS (ESI): 472.2 (M+H)$^+$.

EXAMPLE 810

4-[4-(5-fluoro-2-methoxyphenyl)-1H-pyrrolo[2,3-b]pyridin-2-yl]-N-[(1-methylcyclopropyl)sulfonyl]cyclohex-3-ene-1-carboxamide $^1$H NMR (500 MHz, DMSO-d$_6$) δ ppm 11.75 (s, 1 H) 11.21 (s, 1 H) 7.91-8.56 (m, 2 H) 7.12-7.38 (m, 3 H) 7.02 (d, J=4.88 Hz, 1 H) 6.53 (d, J=3.66 Hz, 1 H) 6.12-6.28 (m, 1 H) 3.74 (s, 3 H) 2.58-2.70 (m, 1 H) 2.25-2.44 (m, 3 H) 2.01 (d, J=5.19 Hz, 1 H) 1.57-1.76 (m, 1 H) 1.31-1.41 (m, 3 H) 1.16-1.31 (m, 4 H). MS (ESI): 484.2 (M+H)$^+$.

EXAMPLE 811

4-[4-(5-fluoro-2-methoxyphenyl)-1H-pyrrolo[2,3-b]pyridin-2-yl]-N-[(2-methylpropyl)sulfonyl]cyclohex-3-ene-1-carboxamide $^1$H NMR (400 MHz, DMSO-d$_6$) δ ppm 11.74 (d, J=1.53 Hz, 1 H) 11.57 (s, 1 H) 8.18 (d, J=4.88 Hz, 1 H) 7.12-7.35 (m, 3 H) 7.02 (d, J=4.88 Hz, 1 H) 6.52 (d, J=3.05 Hz, 1 H) 6.20 (d, J=2.14 Hz, 3 H) 3.74 (s, 3 H) 3.5-3.64 (m, 2 H) 2.54-2.69 (m, 1 H) 2.27-2.47 (m, 2 H) 2.01 (d, J=12.21 Hz, 1 H) 1.57-1.78 (m, 1 H) 1.21-1.35 (m, 6 H). MS (ESI): 486.2 (M+H)$^+$.

EXAMPLE 838

4-[4-(5-fluoro-2-methoxyphenyl)-1H-pyrrolo[2,3-b]pyridin-2-yl]-N,N-dimethylcyclohex-3-ene-1-carboxamide $^1$H NMR (400 MHz, DMSO-d$_6$) δ ppm 11.73 (s, 1 H) 8.17 (d, J=4.88 Hz, 1 H) 7.13-7.33 (m, 3 H) 7.02 (d, J=4.88 Hz, 1 H) 6.56 (d, J=2.75 Hz, 1 H) 6.18 (d, J=1.53 Hz, 1 H) 3.74 (s, 3 H) 3.32 (s, 6 H) 2.83-2.95 (m, 2 H) 2.54 (s, 1 H) 2.19-2.47 (m, 2 H) 1.87 (d, J=12.51 Hz, 1 H) 1.47-1.70 (m, 1 H). MS (ESI): 394.2 (M+H)$^+$.

EXAMPLE 934

4-[4-(5-fluoro-2-methoxyphenyl)-1H-pyrrolo[2,3-b]pyridin-2-yl]-N-(1H-tetrazol-5-ylmethyl)cyclohex-3-ene-1-carboxamide $^1$H NMR (400 MHz, DMSO-d$_6$) δ ppm 11.94 (s, 1 H) 8.63 (t, J=5.65 Hz, 1 H) 8.21 (d, J=5.19 Hz, 1 H) 7.15-7.36 (m, 3 H) 7.10 (d, J=5.19 Hz, 1 H) 6.57 (s, 1 H) 6.25 (d, J=1.83

Hz, 1 H) 4.48-4.66 (m, 2 H) 3.75 (s, 3 H) 2.43-2.64 (m, 2 H) 2.26-2.45 (m, 3 H) 1.53-1.79 (m, 1 H). MS (ESI): 448.1 (M+H)+.

EXAMPLE 963

N-cyano-4-[4-(5-fluoro-2-methoxyphenyl)-1H-pyrrolo[2,3-b]pyridin-2-yl]cyclohex-3-ene-1-carboxamide $^1$H NMR (500 MHz, DMSO-$d_6$) δ ppm 11.48-12.11 (m, 2 H) 8.21 (d, J=5.19 Hz, 1 H) 7.15-7.32 (m, 3 H) 7.00-7.13 (m, 1 H) 6.54 (s, 1 H) 6.24 (d, J=1.83 Hz, 1 H) 3.70-3.81 (m, 3 H) 2.52-2.76 (m, 2 H) 2.24-2.49 (m, 3 H) 1.90-2.17 (m, 1 H) 1.44-1.80 (m, 1 H). MS (ESI): 391.1 (M+H)+.

EXAMPLE 568

2-(3,6-dihydro-2H-pyran-4-yl)-4-(5-fluoro-2-methoxyphenyl)-1H-pyrrolo[2,3-b]pyridine The title compound was prepared essentially as described in Example 219B, substituting ethyl 4-(4,4,5,5-tetramethyl-1,3,2-dioxaborolan-2-yl)cyclohex-3-enecarboxylate with 2-(3,6-dihydro-2H-pyran-4-yl)-4,4,5,5-tetramethyl-1,3,2-dioxaborolane. $^1$H NMR (400 MHz, DMSO-D6) δ ppm 11.84 (s, 1 H) 8.20 (d, J=4.88 Hz, 1 H) 7.13-7.32 (m, 3 H) 7.04 (d, J=4.88 Hz, 1 H) 6.56 (s, 1 H) 6.23 (d, J=1.83 Hz, 1 H) 4.26 (d, J=2.75 Hz, 2 H) 3.80 (t, J=5.49 Hz, 2 H) 3.74 (s, 3 H) 2.45 (d, J=1.53 Hz, 2 H). MS (ESI): 325.2 (M+H)+.

The following compounds (concluding with Example 774) were prepared essentially as described in Example 100, substituting the appropriate amine for Example 87D and the appropriate carboxylic acid for acetic acid. Some products were purified by flash chromatography while others were purified by reverse-phase HPLC. Accordingly, some Examples were isolated as trifluoroacetic acid salts. Some examples (free base or trifluoroacetic acid salt) were converted into HCl salts.

EXAMPLE 569

{4-[4-(5-fluoro-2-methoxyphenyl)-1H-pyrrolo[2,3-b]pyridin-2-yl]-3,6-dihydropyridin-1(2H)-yl}(tetrahydro-2H-pyran-3-yl)methanone $^1$H NMR (400 MHz, methanol-$d_4$) δ ppm 1.62-1.81 (m, 3H), 1.90-2.01 (m, 1H), 2.54-2.71 (m, 2H), 2.91-3.07 (m, 1H), 3.38-3.56 (m, 2H), 3.79-3.96 (m, 7H), 4.25-4.42 (m, 2H), 6.49-6.55 (m, 1H), 6.57 (s, 1H), 7.18-7.32 (m, 3H), 7.41-7.47 (m, 1H), 8.27 (d, J=5.9 Hz, 1H). MS (ESI+) m/z 436.2 (M+H)+.

EXAMPLE 572

1-{5-[4-(5-fluoro-2-methoxyphenyl)-1H-pyrrolo[2,3-b]pyridin-2-yl]-3,6-dihydropyridin-1(2H)-yl}-2-hydroxyethanone $^1$H NMR (400 MHz, methanol-$d_4$) δ ppm 2.40-2.56 (m, 2H), 3.60 (t, J=5.7 Hz, 1H), 3.75-3.84 (m, 4H), 4.30-4.37 (m, 3H), 4.45-4.50 (m, 1H), 6.54-6.74 (m, 2H), 7.18-7.31 (m, 3H), 7.42 (t, J=6.1 Hz, 1H), 8.27 (d, J=5.8 Hz, 1H). MS (ESI+) m/z 382.2 (M+H)+.

EXAMPLE 573

1-{5-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, methanol-$d_4$) δ ppm 2.19 (s, 3H), 2.41-2.57 (m, 2H), 3.62-3.80 (m, 2H), 3.82 (s, 3H), 4.45 (d, J=2.6 Hz, 2H), 6.55-6.63 (m, 1H), 6.67-6.77 (m, 1H), 7.19-7.33 (m, 3H), 7.46 (t, J=5.8 Hz, 1H), 8.28 (d, J=5.9 Hz, 1H). MS (ESI+) m/z 366.2 (M+H)+.

EXAMPLE 593

1-{4-[4-(2,3-difluorophenyl)-1H-pyrrolo[2,3-b]pyridin-2-yl]-3,6-dihydropyridin-1(2H)-yl}-2-hydroxyethanone $^1$H NMR (400 MHz, methanol-$d_4$) δ ppm 2.59-2.69 (m, 2H), 3.61-3.73 (m, 1.2H), 3.78-3.88 (m, 0.8H), 4.14-4.37 (m, 4H), 6.44-6.61 (m, 2H), 7.29-7.53 (m, 4H), 8.31 (d, J=5.5 Hz, 1H). MS (ESI+) m/z 370.1 (M+H)+.

EXAMPLE 598

1-{3-[4-(5-fluoro-2-methoxyphenyl)-1H-pyrrolo[2,3-b]pyridin-2-yl]-8-azabicyclo[3.2.1]oct-2-en-8-yl}-2-hydroxyethanone $^1$H NMR (400 MHz, methanol-$d_4$) δ ppm 1.76-2.55 (m, 5H), 3.04-3.16 (m, 1H), 3.81 (s, 3H), 3.98 (s, 0.5H), 4.12-4.35 (m, 2H), 4.56-4.71 (m, 1H), 5.00-5.04 (m, 0.5H), 6.53 (d, J=1.9 Hz, 1H), 6.81-6.86 (m, 1H), 7.18-7.32 (m, 3H), 7.47 (dd, J=6.0, 3.8 Hz, 1H), 8.27 (d, J=6.0 Hz, 1H). MS (ESI+) m/z 408.1 (M+H)+.

EXAMPLE 619

4-{2-[1-(hydroxyacetyl)-1,2,3,6-tetrahydropyridin-4-yl]-1H-pyrrolo[2,3-b]pyridin-4-yl}-N-methylbenzamide $^1$H NMR (400 MHz, methanol-$d_4$) δ ppm 2.62-2.72 (m, 2H), 2.97 (s, 3H), 3.67-3.87 (m, 2H), 4.18-4.35 (m, 4H), 6.49-6.59 (m, 1H), 6.87 (d, J=7.5 Hz, 1H), 7.52 (d, J=5.8 Hz, 1H), 7.89-7.95 (m, 2H), 8.01-8.07 (m, 2H), 8.33 (d, J=5.8 Hz, 1H). MS (ESI+) m/z 391.1 (M+H)+.

EXAMPLE 635

1-{4-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one $^1$H NMR (400 MHz, methanol-$d_4$) δ ppm 1.45 (s, 6H), 2.61 (bs, 2H), 3.76 (s, 3H), 3.82-4.78 (m, 4H), 6.30 (s, 1H), 6.40 (bs, 1H), 7.08 (d, J=5.1 Hz, 1H), 7.10-7.20 (m, 3H), 8.16 (d, J=5.1 Hz, 1H). MS (ESI+) m/z 410.1 (M+H)+.

EXAMPLE 773

3-{4-[4-(2,3-difluorophenyl)-1H-pyrrolo[2,3-b]pyridin-2-yl]-3,6-dihydropyridin-1(2H)-yl}-3-oxopropanenitrile $^1$H NMR (400 MHz, methanol-$d_4$) δ ppm 2.61-2.76 (m, 2H), 3.71 (t, J=5.7 Hz, 1.2H), 3.85 (t, J=5.8 Hz, 0.8H), 3.94

(s, 0.8H), 3.98 (s, 1.2H), 4.26-4.35 (m, 2H), 6.50-6.59 (m, 1H), 6.68 (dd, J=8.1, 2.2 Hz, 1H), 7.35-7.45 (m, 1H), 7.43-7.55 (m, 3H), 8.36 (d, J=5.8 Hz, 1H). MS (ESI$^+$) m/z 379.2 (M+H)$^+$.

EXAMPLE 774

{4-[4-(5-fluoro-2-methoxyphenyl)-1H-pyrrolo[2,3-b]pyridin-2-yl]-3,6-dihydropyridin-1(2H)-yl}(1-hydroxycyclopropyl)methanone $^1$H NMR (400 MHz, methanol-d$_4$) δ ppm 0.89-0.96 (m, 2H), 1.04-1.11 (m, 2H), 2.68 (bs, 2H), 3.83 (s, 3H), 3.87-4.66 (m, 4H), 6.58-6.68 (m, 2H), 7.22-7.40 (m, 3H), 7.58 (d, J=6.2 Hz, 1H), 8.31 (d, J=6.2 Hz, 1H). MS (ESI$^+$) m/z 408.2 (M+H)$^+$.

EXAMPLE 570

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]-2-hydroxyethanone The title compound was prepared essentially as described in Examples 417, substituting Example 539 (30 mg, 0.08 mmol) for Example 365. $^1$H NMR (500 MHz, DMSO-d$_6$) δ 2.50 (m, 2H), 3.40-3.75 (m, 2H), 4.07-4.14 (m, 2H), 4.17 (s, 2H), 5.22 (s, 2H), 6.31 (d, J=10.9 Hz, 1H), 6.45-6.61 (m, 1H), 7.11 (d, J=5.0 Hz, 1H), 7.18-7.25 (m, 5H), 7.36 (t, J=9.2 Hz, 1H), 8.27 (d, J=5.0 Hz, 1H). MS (ESI$^+$) m/z 494 (M+H)$^+$.

EXAMPLE 571

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]ethanone The title compound was prepared essentially as described in Examples 417, substituting Example 539 (30 mg, 0.08 mmol) for Example 365 and acetic acid for 2-hydroxyacetic acid. $^1$H NMR (500 MHz, DMSO-d$_6$) δ 2.06 (d, J=13.5 Hz, 3H), 2.37-2.60 (m, 2H), 3.63 (dt, J=13.6, 5.7 Hz, 2H), 4.09-4.23 (m, 2H), 5.22 (s, 2H), 6.31 (dt, J=10.7, 2.0 Hz, 1H), 6.54 (d, J=3.3 Hz, 1H), 7.04-7.26 (m, 7H), 7.36 (t, J=9.3 Hz, 1H), 8.27 (d, J=5.0 Hz, 1H). MS (ESI$^+$) m/z 450 (M+H)$^+$.

EXAMPLE 576

1-{4-[4-(5-fluoro-2-methoxyphenyl)-1H-pyrrolo[2,3-b]pyridin-2-yl]-3,6-dihydropyridin-1(2H)-yl}-2-methylpropan-2-ol To a mixture of Example 87D (60.0 mg, 0.151 mmol) in ethanol (2.5 mL) was added triethylamine (0.106 mL, 0.757 mmol) followed by 2,2-dimethyloxirane (0.040 mL, 0.454 mmol). The reaction mixture was heated at 110° C. for 45 minutes in a Biotage Initiator microwave reactor (model 355502). The reaction mixture was concentrated and purified by HPLC (see protocols in Example 361) to provide the title compound as a trifluoroacetic acid salt. $^1$H NMR (400 MHz, pyridine-d$_5$) δ ppm 1.50 (s, 6H), 2.84-2.91 (m, 2H), 3.11 (bs, 2H), 3.51 (t, J=5.9 Hz, 2H), 3.72 (s, 3H), 4.08-4.14 (m, 2H), 6.66 (s, 1H), 6.70 (bs, 1H), 7.11 (dd, J=9.0, 4.5 Hz, 1H), 7.27-7.35 (m, 2H), 7.49 (dd, J=8.9, 3.2 Hz, 1H), 8.60 (dd, J=4.9, 1.4 Hz, 1H), 12.97-13.16 (m, 1H). MS (ESI$^+$) m/z 396.0 (M+H)$^+$.

EXAMPLE 577

4-[4-(5-fluoro-2-methoxyphenyl)-1H-pyrrolo[2,3-b]pyridin-2-yl]-N,N-dimethyl-3,6-dihydropyridine-1(2H)-carboxamide To a mixture of Example 87D (75.0 mg, 0.189 mmol) in N,N-dimethylformamide (2.5 mL) was added triethylamine (132 µL, 0.946 mmol) followed by dimethylcarbamoyl chloride (26 µL, 0.00 mmol). The reaction mixture was stirred for 6 hours. Water was slowly added to the reaction mixture. The solids formed was filtered and washed with water. The filtrate was treated with brine and extracted with ethyl acetate. The organic layer was concentrated. The concentrate and the solids collected earlier were combined and purified by HPLC (see protocols in Example 361) to provide the title compound as a trifluoroacetic acid salt. $^1$H NMR (400 MHz, methanol-d$_4$) δ ppm 2.59-2.67 (m, 2H), 2.88 (s, 6H), 3.49 (t, J=5.6 Hz, 2H), 3.81 (s, 3H), 4.03 (q, J=2.9 Hz, 2H), 6.48-6.57 (m, 2H), 7.18-7.32 (m, 3H), 7.45 (d, J=5.9 Hz, 1H), 8.26 (d, J=5.9 Hz, 1H). MS (ESI$^+$) m/z 395.1 (M+H)$^+$.

EXAMPLE 578 ethyl ({4-[4-(5-fluoro-2-methoxyphenyl)-1H-pyrrolo[2,3-b]pyridin-2-yl]piperidin-1-yl}sulfonyl)carbamate

EXAMPLE 578A ((4-(dimethylamino)pyridin-1-ium-1-yl)sulfonyl)(ethoxycarbonyl)amide To a solution of ethanol (1.61 mL, 27.2 mmol) in anhydrous methylene chloride (100 mL) was added dropwise cooling with ice chlorosulfonyl isocyanate (2.4 mL, 27.6 mL) over 15 minutes. After stirring for 15 minutes, dimethylaminopyridine (6.9 g, 56.5 mmol) was then added. The cooling bath was removed, and the reaction mixture was stirred at room temperature for 1 hour. The reaction mixture was washed with water and brine. After drying with sodium sulfate, the organic layer was filtered and concentrated in vacuum to yield the provide the title compound. MS (DCI/NH$_3$) m/z 274 (M+H)$^+$.

EXAMPLE 578B ethyl ({4-[4-(5-fluoro-2-methoxyphenyl)-1H-pyrrolo[2,3-b]pyridin-2-yl]piperidin-1-yl}sulfonyl)carbamate To a solution of Example 17G (80 mg, 0.246 mmol) in CH$_2$Cl$_2$ (5 mL) was added triethylamine (0.069 mL, 0.492 mmol) and Example 578A (67 mg, 0.246 mmol) at room temperature. The reaction mixture was stirred at room temperature overnight and was directly separated by flash chromatography (0-15% CH$_3$OH in CH$_2$Cl$_2$) to provide the title compound. $^1$H NMR (400 MHz, DMSO-d$_6$): δ1.16-1.21 (m, 3 H), 1.65-1.77 (m, 2 H), 2.07 (d, J=10.68 Hz, 2 H), 2.84-2.91 (m, 1 H), 2.93-3.02 (m, 2 H), 3.73 (s, 3 H), 4.11 (q, J=7.22 Hz, 2 H), 5.98 (d, J=1.53 Hz, 1 H), 7.02 (d, J=5.19

Hz, 1 H), 7.16-7.27 (m, 3 H), 8.15 (d, J=4.88 Hz, 1 H), 11.28 (s, 1 H), 11.62 (s, 1 H); MS (DCI/NH$_3$) m/z 477 (M+H)$^+$.

EXAMPLE 579

4-[4-(5-fluoro-2-methoxyphenyl)-1H-pyrrolo[2,3-b]pyridin-2-yl]-N-methylpiperidine-1-sulfonamide To a solution of Example 17G (120 mg, 0.369 mmol) in methylene chloride (6 mL) was added methylsulfamoyl chloride (72 mg, 0.553 mmol) and triethyl amine (0.154 mL). The mixture was stirred at room temperature overnight, and was directly separated by flash chromatography (0-15% CH$_3$OH in CH$_2$Cl$_2$) to provide the title compound. $^1$H NMR (400 MHz, DMSO-d$_6$): δ1.66-1.77 (m, 2 H), 2.07 (d, J=10.99 Hz, 2 H), 2.54 (d, J=4.88 Hz, 3 H), 2.76-2.88 (m, 3 H), 3.59 (d, J=11.90 Hz, 2 H), 3.73 (s, 3 H), 6.00 (d, J=1.53 Hz, 1 H), 7.01-7.07 (m, 2 H), 7.17-7.27 (m, 3 H), 8.15 (d, J=4.88 Hz, 1 H), 11.61 (s, 1 H); MS (DCI/NH$_3$) m/z 419 (M+H)$^+$.

EXAMPLE 580

4-[4-(5-fluoro-2-methoxyphenyl)-1H-pyrrolo[2,3-b]pyridin-2-yl]-N,N-dimethylpiperidine-1-sulfonamide To a solution of Example 17G (120 mg, 0.369 mmol) in methylene chloride (6 mL) was added dimethylsulfamoyl chloride (79 mg, 0.553 mmol) and triethyl amine (0.154 mL). The mixture was stirred at room temperature overnight, and was directly separated by flash chromatography (0-15% CH$_3$OH in CH$_2$Cl$_2$) to provide the title compound. $^1$H NMR (400 MHz, DMSO-d$_6$): δ1.65-1.76 (m, 2 H), 2.05 (d, J=10.99 Hz, 2 H), 2.77 (s, 6 H), 2.84-2.91 (m, 1 H), 2.90-2.98 (m, 2 H), 3.65 (d, J=12.51 Hz, 2 H), 3.73 (s, 3 H), 6.00 (d, J=1.83 Hz, 1 H), 7.02 (d, J=5.19 Hz, 1 H), 7.15-7.29 (m, 3 H), 8.15 (d, J=4.88 Hz, 1 H), 11.63 (s, 1 H); MS (DCI/NH$_3$) m/z 433 (M+H)$^+$.

EXAMPLE 581

4-(5-fluoro-2-methoxyphenyl)-2-[4-(trifluoromethyl)cyclohex-1-en-1-yl]-1H-pyrrolo[2,3-b]pyridine The title compound was prepared essentially as described in Example 219B, substituting ethyl 4-(4,4,5,5-tetramethyl-1,3,2-dioxaborolan-2-yl)cyclohex-3-enecarboxylate with 4,4,5,5-tetramethyl-2-(4-(trifluoromethyl)cyclohex-1-en-1-yl)-1,3,2-dioxaborolane. $^1$H NMR (400 MHz, DMSO-d$_6$) δ ppm 11.80 (s, 1 H) 8.19 (t, J=4.42 Hz, 1 H) 7.12-7.32 (m, 3 H) 7.03 (d, J=4.88 Hz, 1 H) 6.53 (s, 1 H) 6.22 (d, J=1.83 Hz, 1 H) 3.69-3.80 (m, 3 H) 2.55-2.72 (m, 2 H) 2.36-2.48 (m, 2 H) 2.17-2.34 (m, 1 H) 1.97-2.11 (m, 1 H) 1.48-1.67 (m, 1 H). MS (ESI): 391.2 (M+H)$^+$.

The following compounds (concluding with Example 1331) were prepared essentially as described in Example 241C, substituting the appropriate amine for Example 241B. In some cases where the amine is an amino acid, a subsequent ester hydrolysis step was performed. Some compounds were purified by trituration or flash chromatography while others were purified by reverse-phase HPLC. Accordingly, some examples were isolated as hydrochloride or trifluoroacetic acid salts.

EXAMPLE 582

4-[4-(5-fluoro-2-methoxyphenyl)-1H-pyrrolo[2,3-b]pyridin-2-yl]-N-(tetrahydro-2H-pyran-4-ylmethyl)cyclohex-3-en-1-amine $^1$H NMR (400 MHz, DMSO-d$_6$) δ ppm 11.69 (s, 1 H) 7.99-8.33 (m, 1 H) 7.12-7.33 (m, 3 H) 7.00 (t, J=4.58 Hz, 1 H) 6.45 (s, 1 H) 6.16 (s, 1 H) 3.77-3.90 (m, 2 H) 3.66-3.77 (m, 3 H) 2.66-2.82 (m, 1 H) 2.40-2.58 (m, 4 H) 2.25-2.42 (m, 1 H) 1.85-2.06 (m, 2 H) 1.52-1.73 (m, 5 H) 1.33-1.51 (m, 1 H) 1.05-1.29 (m, 3 H). MS (ESI): 436.1 (M+H)$^+$.

EXAMPLE 584

N-benzyl-4-[4-(5-fluoro-2-methoxyphenyl)-1H-pyrrolo[2,3-b]pyridin-2-yl]cyclohex-3-en-1-amine $^1$H NMR (400 MHz, DMSO-d$_6$) δ ppm 11.69 (s, 1 H) 8.16 (d, J=4.88 Hz, 1 H) 7.09-7.42 (m, 8 H) 7.01 (d, J=5.19 Hz, 1 H) 6.46 (s, 1 H) 6.16 (d, J=1.53 Hz, 1 H) 3.63-3.86 (m, 5 H) 2.63-2.79 (m, 1 H) 2.40-2.59 (m, 2 H) 2.33 (d, J=3.66 Hz, 1 H) 1.87-2.08 (m, 2 H) 1.36-1.59 (m, 1 H). MS (ESI): 428.1 (M+H)$^+$.

EXAMPLE 585

4-[4-(5-fluoro-2-methoxyphenyl)-1H-pyrrolo[2,3-b]pyridin-2-yl]-N-(pyridin-4-ylmethyl)cyclohex-3-en-1-amine $^1$H NMR (400 MHz, DMSO-d$_6$) δ ppm 11.70 (s, 1 H) 8.36-8.61 (m, 2 H) 8.17 (d, J=4.88 Hz, 1 H) 7.38 (d, J=6.10 Hz, 2 H) 7.11-7.32 (m, 3 H) 7.01 (d, J=4.88 Hz, 1 H) 6.46 (s, 1 H) 6.16 (d, J=1.83 Hz, 1 H) 3.59-3.88 (m, 5 H) 2.61-2.79 (m, 1 H) 2.39-2.61 (m, 2 H) 2.21-2.40 (m, 1 H) 1.92-2.12 (m, 2 H) 1.36-1.58 (m, 1 H). MS (ESI): 429.1 (M+H)$^+$.

EXAMPLE 586

4-[4-(5-fluoro-2-methoxyphenyl)-1H-pyrrolo[2,3-b]pyridin-2-yl]-N-(morpholin-2-ylmethyl)cyclohex-3-en-1-amine $^1$H NMR (400 MHz, DMSO-d$_6$) δ ppm 12.08 (s, 1 H) 9.41 (s, 2 H) 8.69-9.26 (m, 2 H) 8.25 (d, J=5.19 Hz, 1 H) 7.16-7.36 (m, 3 H) 7.12 (d, J=5.19 Hz, 1 H) 6.47 (s, 1 H) 6.30 (s, 1 H) 3.97-4.21 (m, 2 H) 3.67-3.86 (m, 4 H) 3.21-3.47 (m, J=23.35, 12.36 Hz, 3 H) 2.98-3.22 (m, 2 H) 2.91 (d, J=10.38 Hz, 1 H) 2.60-2.76 (m, 2 H) 2.29-2.49 (m, 1 H) 2.22 (t, J=13.12 Hz, 1 H) 1.61-1.87 (m, 1 H). MS (ESI): 437.1 (M+H)$^+$.

EXAMPLE 595

N-(3,5-difluorobenzyl)-4-[4-(5-fluoro-2-methoxyphenyl)-1H-pyrrolo[2,3-b]pyridin-2-yl]cyclohex-3-en-1-amine $^1$H NMR (400 MHz, DMSO-d$_6$) δ ppm 11.70 (d, J=1.53 Hz, 1 H) 8.17 (d, J=4.88 Hz, 1 H) 6.94-7.34 (m, 7 H) 6.45 (s, 1 H) 6.16 (d, J=1.83 Hz, 1 H) 3.61-3.88 (m, 5 H) 2.61-2.79 (m, 1 H) 2.40-2.60 (m, 2 H) 2.22-2.40 (m, 2 H) 1.85-2.11 (m, 2 H) 1.32-1.57 (m, 1 H). MS (ESI): 437.1 (M+H)$^+$.

EXAMPLE 608

4-[4-(5-fluoro-2-methoxyphenyl)-1H-pyrrolo[2,3-b]pyridin-2-yl]-N-(pyridin-3-ylmethyl)cyclohex-3-en-1-amine $^1$H NMR (400 MHz, DMSO-d$_6$) δ ppm 11.70 (s, 1 H) 8.52-8.62 (m, 1 H) 8.44 (d, J=3.66 Hz, 1 H) 8.17 (d, J=4.88 Hz, 1 H) 7.78 (d, J=7.93 Hz, 1 H) 7.13-7.38 (m, 4 H) 7.01 (d, J=4.88 Hz, 1 H) 6.46 (s, 1 H) 6.16 (d, J=1.53 Hz, 1 H) 3.67-3.87 (m, 5 H) 2.64-2.83 (m, 1 H) 2.43-2.60 (m, 3 H) 2.22-2.41 (m, 1 H) 1.85-2.14 (m, 2 H) 1.29-1.61 (m, 1 H). MS (ESI): 429.1 (M+H)$^+$.

EXAMPLE 623

N-{4-[4-(5-fluoro-2-methoxyphenyl)-1H-pyrrolo[2,3-b]pyridin-2-yl]cyclohex-3-en-1-yl}glycine $^1$H NMR (400 MHz, DMSO-d$_6$) δ ppm 12.25 (s, 1H) 9.31 (s, 2 H) 8.25 (d, J=5.19 Hz, 2 H) 6.94-7.47 (m, 4 H) 6.51 (d, J=4.27 Hz, 1 H) 6.32 (s, 1 H) 3.69-3.81 (m, 3 H) 3.37 (s, 2 H) 2.68 (s, 2 H) 2.35-2.48 (m, 2 H) 2.24 (s, 1 H) 1.76 (dd, J=11.90, 5.19 Hz, 1 H). MS (ESI): 396.2 (M+H)$^+$.

EXAMPLE 669

4-[4-(5-fluoro-2-methoxyphenyl)-1H-pyrrolo[2,3-b]pyridin-2-yl]-N-(pyridin-2-ylmethyl)cyclohex-3-en-1-amine $^1$H NMR (400 MHz, DMSO-d$_6$) δ ppm 11.74 (s, 1 H) 8.56 (d, J=4.88 Hz, 1 H) 8.10-8.26 (m, 1 H) 7.76-7.88 (m, 1 H) 7.49 (d, J=7.93 Hz, 1 H) 7.11-7.41 (m, 5 H) 6.92-7.09 (m, 1 H) 6.46 (s, 1 H) 6.11-6.28 (m, 1 H) 4.10 (s, 3 H) 3.67-3.82 (m, 2 H) 2.98-3.09 (m, 2 H) 2.53-2.72 (m, 2 H) 2.01-2.47 (m, 2 H) 1.46-1.73 (m, 1 H). MS (ESI): 429.0 (M+H)$^+$.

EXAMPLE 670

4-[4-(5-fluoro-2-methoxyphenyl)-1H-pyrrolo[2,3-b]pyridin-2-yl]-N-(pyrazin-2-ylmethyl)cyclohex-3-en-1-amine $^1$H NMR (500 MHz, DMSO-d$_6$) δ ppm 11.74 (s, 1 H) 8.76 (d, J=1.22 Hz, 1 H) 8.62 (s, 1 H) 8.57 (d, J=2.14 Hz, 1 H) 8.18 (d, J=4.88 Hz, 1 H) 7.12-7.34 (m, 3 H) 7.02 (d, J=4.88 Hz, 1 H) 6.46 (s, 1 H) 6.19 (d, J=1.53 Hz, 1 H) 4.11 (s, 2 H) 3.60-3.81 (m, 3 H) 3.04 (q, J=6.92 Hz, 2 H) 2.58 (d, J=18.01 Hz, 2 H) 2.37 (d, J=2.14 Hz, 2 H) 2.05 (s, 2 H) 1.46-1.71 (m, 1 H). MS (ESI): 430.0 (M+H)$^+$.

EXAMPLE 671

4-[4-(5-fluoro-2-methoxyphenyl)-1H-pyrrolo[2,3-b]pyridin-2-yl]-N-(pyrimidin-5-ylmethyl)cyclohex-3-en-1-amine $^1$H NMR (500 MHz, DMSO-d$_6$) δ ppm 11.72 (s, 1 H) 9.07 (s, 1 H) 8.67-8.89 (m, 2 H) 8.17 (d, J=4.88 Hz, 1 H) 7.11-7.33 (m, 3 H) 7.02 (d, J=5.19 Hz, 1 H) 6.47 (s, 1 H) 6.18 (s, 1 H) 3.80-3.93 (m, 2 H) 3.67-3.80 (m, 3 H) 2.79 (s, 1 H) 2.51-2.63 (m, 2 H) 2.27-2.44 (m, 1 H) 1.96-2.15 (m, 2 H) 1.41-1.63 (m, 1 H). MS (ESI): 430.1 (M+H)$^+$.

EXAMPLE 672

4-[4-(5-fluoro-2-methoxyphenyl)-1H-pyrrolo[2,3-b]pyridin-2-yl]-N-(tetrahydrofuran-2-ylmethyl)cyclohex-3-en-1-amine $^1$H NMR (400 MHz, DMSO-d$_6$) δ ppm 11.74 (s, 1 H) 8.17 (t, J=4.88 Hz, 1 H) 7.13-7.32 (m, 3 H) 7.01 (t, J=4.73 Hz, 1 H) 6.45 (s, 1 H) 6.19 (d, J=1.53 Hz, 1 H) 3.87-4.09 (m, 2 H) 3.71-3.79 (m, 3 H) 3.02 (s, 2 H) 2.70-2.94 (m, 3 H) 2.57 (d, J=17.40 Hz, 2 H) 2.28-2.46 (m, 1 H) 2.07 (s, 2 H) 1.92-2.02 (m, 1 H) 1.75-1.89 (m, 2 H) 1.45-1.64 (m, 2 H). MS (ESI): 422.1 (M+H)$^+$.

EXAMPLE 754

2-({4-[4-(5-fluoro-2-methoxyphenyl)-1H-pyrrolo[2,3-b]pyridin-2-yl]cyclohex-3-en-1-yl}amino)butanoic acid $^1$H NMR (400 MHz, DMSO-d$_6$) δ ppm 11.74 (s, 1 H) 8.17 (d, J=4.88 Hz, 1 H) 7.09-7.35 (m, 3 H) 7.01 (d, J=4.88 Hz, 1 H) 6.44 (s, 1 H) 6.17 (s, 1 H) 3.73 (s, 3 H) 3.08 (t, J=5.80 Hz, 1 H) 2.89 (s, 1 H) 2.47-2.63 (m, 3 H) 2.25-2.41 (m, 1 H) 1.88-2.23 (m, 2 H) 1.42-1.70 (m, 3 H) 0.88 (t, J=7.32 Hz, 3 H). MS (ESI): 424.1 (M+H)$^+$.

EXAMPLE 839

N-{4-[4-(5-fluoro-2-methoxyphenyl)-1H-pyrrolo[2,3-b]pyridin-2-yl]cyclohex-3-en-1-yl}alanine $^1$H NMR (500 MHz, DMSO-d$_6$) δ ppm 11.78 (s, 1 H) 8.18 (d, J=4.27 Hz, 1 H) 7.09-7.38 (m, 3 H) 7.01 (d, J=3.97 Hz, 1 H) 6.44 (s, 1 H) 6.19 (s, 1 H) 3.73 (s, 3 H) 3.32 (s, 2 H) 3.11 (s, 2 H) 2.56 (s, 2 H) 2.39 (s, 1 H) 2.25 (s, 1 H) 2.07 (d, J=2.14 Hz, 1 H) 1.63 (s, 1 H) 1.26 (s, 3 H). MS (ESI): 410.1 (M+H)$^+$.

EXAMPLE 853

3-[4-(5-fluoro-2-methoxyphenyl)-1H-pyrrolo[2,3-b]pyridin-2-yl]cyclohex-3-ene-1-carboxylic acid $^1$H NMR (400 MHz, DMSO-d$_6$) δ ppm 11.75 (s, 1 H) 8.18 (d, J=4.88 Hz, 1 H) 7.11-7.35 (m, 3 H) 7.02 (d, J=4.88 Hz, 1 H) 6.43 (s, 1 H) 6.19 (d, J=1.53 Hz, 1 H) 3.60-3.85 (m, 7 H) 3.25 (s, 2 H) 2.59 (d, J=16.78 Hz, 2 H) 2.34 (d, J=8.85 Hz, 2 H) 2.12 (s, 1 H) 1.58-1.81 (m, 1 H). MS (ESI): 426.3 (M+H)$^+$.

EXAMPLE 860

N-{4-[4-(5-fluoro-2-methoxyphenyl)-1H-pyrrolo[2,3-b]pyridin-2-yl]cyclohex-3-en-1-yl}-L-isoleucine $^1$H NMR (400 MHz, DMSO-d$_6$) δ ppm 11.70 (s, 1 H) 8.15 (d, J=4.88 Hz, 1 H) 7.09-7.35 (m, 3 H) 6.99 (d, J=4.88 Hz, 1 H) 6.42 (s, 1 H) 6.14 (s, 1 H) 3.72 (s, 3 H) 2.84 (d, J=4.27 Hz, 1 H) 2.62-2.78 (m, 1 H) 2.49 (s, 1 H) 2.27 (s, 1 H) 1.80-2.12 (m, 2 H) 1.75 (s, 3 H) 1.34-1.63 (m, 3 H) 1.22 (s, 2 H) 1.02-1.17 (m, 1 H) 0.73-0.88 (m, 5 H). MS (ESI): 452.1 (M+H)$^+$.

EXAMPLE 896

N-[4-({4-[4-(5-fluoro-2-methoxyphenyl)-1H-pyrrolo[2,3-b]pyridin-2-yl]-3,6-dihydropyridin-1(2H)-yl}methyl)phenyl]methanesulfonamide $^1$H NMR (500 MHz, DMSO-d$_6$) δ ppm 11.78 (s, 1 H) 9.69 (s, 1 H) 8.19 (d, J=4.88 Hz, 1 H) 7.11-7.37 (m, 6 H) 7.02 (d, J=4.88 Hz, 1 H) 6.48 (s, 1 H) 6.19 (s, 1 H) 3.73 (s, 3 H) 3.57 (s, 2 H) 3.03-3.17 (m, 2 H) 2.98 (s, 3 H) 2.64 (s, 2 H) 2.41-2.56 (m, 1 H) 1.91 (s, 1 H). MS (ESI): 507.1 (M+H)$^+$.

EXAMPLE 935

N-{4-[4-(5-fluoro-2-methoxyphenyl)-1H-pyrrolo[2,3-b]pyridin-2-yl]cyclohex-3-en-1-yl}-L-norvaline $^1$H NMR (500 MHz, DMSO-d$_6$) δ ppm 13.05 (d, J=9.77 Hz, 1 H) 9.01-10.24 (m, 2 H) 8.32 (d, J=5.80 Hz, 1 H) 7.05-7.59 (m, 4 H) 6.66 (s, 1 H) 6.46 (d, J=2.14 Hz, 1 H) 4.11 (d, J=4.27 Hz, 1 H) 3.68-3.87 (m, 3 H) 3.28-3.47 (m, 1 H) 2.55-2.87 (m, 2 H) 2.38-2.54 (m, 2 H) 2.30 (dd, J=37.54, 11.29 Hz, 1 H) 1.77-2.08 (m, 3 H) 1.43-1.59 (m, 1 H) 1.24-1.43 (m, 1 H) 0.83-1.02 (m, 3 H). MS (ESI): 438.1 (M+H)$^+$.

EXAMPLE 936

4-[4-(5-fluoro-2-methoxyphenyl)-1H-pyrrolo[2,3-b]pyridin-2-yl]-N-(1H-tetrazol-5-ylmethyl)cyclohex-3-en-1-amine $^1$H NMR (400 MHz, DMSO-d$_6$) δ ppm 11.80 (s, 1 H) 8.19 (d, J=5.19 Hz, 1 H) 7.11-7.38 (m, 3 H) 7.03 (d, J=4.88 Hz, 1 H) 6.46 (s, 1 H) 6.22 (s, 1 H) 4.32 (s, 3 H) 4.13 (s, 2 H) 3.31 (s, 2 H) 2.56-2.87 (m, 3 H) 2.11-2.46 (m, 3 H) 1.58-1.82 (m, 1 H). MS (ESI): 420.1 (M+H)$^+$.

EXAMPLE 962 methyl N-{4-[4-(5-fluoro-2-methoxyphenyl)-1H-pyrrolo[2,3-b]pyridin-2-yl]cyclohex-3-en-1-yl}-3-methyl-L-valinate $^1$H NMR (400 MHz, DMSO-d$_6$) δ ppm 11.70 (s, 1 H) 8.18 (t, J=5.19 Hz, 1 H) 7.13-7.32 (m, 3 H) 7.02 (t, J=4.58 Hz, 1 H) 6.44 (d, J=10.68 Hz, 1 H) 6.17 (s, 1 H) 3.69-3.79 (m, 3 H) 3.60-3.71 (m, 3 H) 3.03 (d, J=7.32 Hz, 1 H) 2.15-2.73 (m, 3 H) 1.70-2.12 (m, 3 H) 1.31-1.61 (m, 1 H) 0.73-1.01 (m, 9 H). MS (ESI): 466.2 (M+H)$^+$.

EXAMPLE 974 cyclopropyl({4-[4-(5-fluoro-2-methoxyphenyl)-1H-pyrrolo[2,3-b]pyridin-2-yl]cyclohex-3-en-1-yl}amino)acetic acid $^1$H NMR (400 MHz, DMSO-d$_6$) δ ppm 11.78 (s, 1 H) 8.19 (d, J=4.88 Hz, 1 H) 7.13-7.36 (m, 3 H) 7.03 (d, J=4.88 Hz, 1 H) 6.43 (s, 1 H) 6.22 (d, J=1.53 Hz, 1 H) 3.64-3.80 (m, 3 H) 2.65 (d, J=16.78 Hz, 3 H) 2.32-2.54 (m, 3 H) 2.28 (t, J=7.32 Hz, 1 H) 1.67-1.84 (m, 1 H) 1.23 (s, 2 H) 1.05-1.20 (m, 1 H) 0.49-0.78 (m, 4 H). MS (ESI): 436.1 (M+H)$^+$.

EXAMPLE 1016

N-{4-[4-(5-fluoro-2-methoxyphenyl)-1H-pyrrolo[2,3-b]pyridin-2-yl]cyclohex-3-en-1-yl}-L-serine $^1$H NMR (400 MHz, DMSO-d$_6$) δ ppm 12.01 (s, 1 H) 8.23 (d, J=5.19 Hz, 2 H) 6.90-7.48 (m, 4 H) 6.49 (d, J=2.14 Hz, 1 H) 6.30 (s, 1 H) 3.66-3.80 (m, 4 H) 3.54 (d, J=13.12 Hz, 2 H) 2.62-2.86 (m, 2 H) 2.61 (s, 2 H) 2.23-2.41 (m, 1 H) 1.78-2.00 (m, 1 H). MS (ESI): 426.2 (M+H)$^+$.

EXAMPLE 1020

(4R)-1-{4-[4-(5-fluoro-2-methoxyphenyl)-1H-pyrrolo[2,3-b]pyridin-2-yl]cyclohex-3-en-1-yl}-4-hydroxy-L-proline $^1$H NMR (400 MHz, DMSO-d$_6$) δ ppm 12.54 (s, 1 H) 10.24 (s, 1 H) 8.12-8.41 (m, 1 H) 7.05-7.54 (m, 4 H) 6.58 (s, 1 H) 6.37 (s, 1 H) 4.68-4.87 (m, 1 H) 4.31-4.51 (m, 3 H) 3.85-4.12 (m, 1 H) 3.62-3.84 (m, 2 H) 3.25-3.50 (m, 1 H) 2.72 (d, J=12.82 Hz, 2 H) 2.40-2.64 (m, 2 H) 2.03-2.41 (m, 3 H) 1.63-1.96 (m, 1 H). MS (ESI): 452.1 (M+H)$^+$.

EXAMPLE 1021

N-{4-[4-(5-fluoro-2-methoxyphenyl)-1H-pyrrolo[2,3-b]pyridin-2-yl]cyclohex-3-en-1-yl}-L-valine $^1$H NMR (400 MHz, DMSO-d$_6$) δ ppm 12.70 (s, 1 H) 8.65-9.90 (m, 2 H) 8.29 (d, J=5.49 Hz, 1 H) 7.02-7.62 (m, 4 H) 6.60 (s, 1 H) 6.40 (s, 1 H) 4.05 (s, 2 H) 3.64-3.89 (m, 3 H) 3.17-3.47 (m, 1 H) 2.56-2.91 (m, 3 H) 2.40-2.56 (m, 2 H) 2.20-2.38 (m, 1 H) 1.73-2.02 (m, 1 H) 0.88-1.21 (m, 6 H). MS (ESI): 438.1 (M+H)$^+$.

EXAMPLE 1028

N-{4-[4-(5-fluoro-2-methoxyphenyl)-1H-pyrrolo[2,3-b]pyridin-2-yl]cyclohex-3-en-1-yl}-L-threonine $^1$H NMR (500 MHz, DMSO-d$_6$) δ ppm 12.79 (d, J=12.82 Hz, 1 H) 8.75-9.41 (m, 2 H) 8.30 (d, J=5.49 Hz, 1H) 7.05-7.50 (m, 4 H) 6.61 (s, 1 H) 6.41 (s, 1 H) 4.10-4.27 (m, 1 H) 4.01 (s, 2 H) 3.64-3.87 (m, 3 H) 3.28-3.45 (m, 1 H) 2.64-2.85 (m, 2 H) 2.37-2.59 (m, 2 H) 2.28 (s, 1 H) 1.69-2.03 (m, 1 H) 1.20-1.38 (m, 3 H). MS (ESI): 440.1 (M+H)$^+$.

EXAMPLE 1065

(2R)-({4-[4-(5-fluoro-2-methoxyphenyl)-1H-pyrrolo[2,3-b]pyridin-2-yl]cyclohex-3-en-1-yl}amino)(phenyl)acetic acid $^1$H NMR (400 MHz, DMSO-d$_6$) δ ppm 12.72 (s, 1 H) 9.51-10.70 (m, 2 H) 8.80-9.17 (m, 2 H) 8.28 (d, J=5.49 Hz, 1 H) 7.65-7.79 (m, 2 H) 7.41-7.59 (m, 3 H) 7.16-7.39 (m, 3 H) 6.55 (s, 1 H) 6.37 (dd, J=9.92, 1.37 Hz, 1 H) 3.58-3.84

(m, 3 H) 3.15 (d, J=15.56 Hz, 1 H) 2.97 (s, 1 H) 2.46-2.80 (m, 3 H) 2.21-2.44 (m, 2 H) 1.72-2.03 (m, 1 H). MS (ESI): 472.1 (M+H)$^+$.

EXAMPLE 1104

(2S)-cyclohexyl({4-[4-(5-fluoro-2-methoxyphenyl)-1H-pyrrolo[2,3-b]pyridin-2-yl]cyclohex-3-en-1-yl}amino)acetic acid $^1$H NMR (500 MHz, DMSO-d$_6$) δ ppm 12.64 (d, J=5.19 Hz, 1 H) 8.58-9.78 (m, 2 H) 8.28 (d, J=5.49 Hz, 1 H) 7.04-7.58 (m, 4 H) 6.58 (s, 1 H) 6.38 (s, 1 H) 4.00 (s, 3 H) 3.68-3.89 (m, 3 H) 3.18-3.45 (m, 2 H) 2.54-2.86 (m, 3 H) 2.38-2.55 (m, 1 H) 2.21-2.39 (m, 1 H) 1.96-2.20 (m, 2 H) 1.69-1.94 (m, 3 H) 1.63 (d, J=10.68 Hz, 1 H) 0.92-1.38 (m, 5 H). MS (ESI): 478.1 (M+H)$^+$.

EXAMPLE 1130

N-{4-[4-(5-fluoro-2-methoxyphenyl)-1H-pyrrolo[2,3-b]pyridin-2-yl]cyclohex-3-en-1-yl}-L-phenylalanine $^1$H NMR (500 MHz, DMSO-d$_6$) δ ppm 12.51 (s, 1 H) 10.13 (d, J=140.99 Hz, 1 H) 9.38 (s, 1 H) 8.47 (s, 2 H) 8.27 (d, J=5.19 Hz, 1 H) 7.11-7.45 (m, 7 H) 6.55 (d, J=2.14 Hz, 1 H) 6.18-6.47 (m, 1 H) 4.33 (s, 1 H) 4.09-4.22 (m, 2 H) 3.69-3.82 (m, 3 H) 3.43-3.53 (m, 1 H) 3.26-3.36 (m, 1 H) 3.07-3.22 (m, 1 H) 2.60-2.82 (m, 2 H) 2.46-2.59 (m, 2 H) 2.28-2.47 (m, 1 H) 2.19-2.29 (m, 1 H) 1.76-1.98 (m, 1 H). MS (ESI): 486.1 (M+H)$^+$.

EXAMPLE 1131

N-{4-[4-(5-fluoro-2-methoxyphenyl)-1H-pyrrolo[2,3-b]pyridin-2-yl]cyclohex-3-en-1-yl}-L-tyrosine $^1$H NMR (400 MHz, DMSO-d$_6$) δ ppm 12.45 (s, 1 H) 9.65-10.40 (m, 1 H) 9.29 (s, 1 H) 8.37 (s, 2 H) 8.26 (d, J=5.49 Hz, 1 H) 7.18-7.40 (m, 2 H) 7.00-7.17 (m, 2 H) 6.73 (d, J=8.54 Hz, 4 H) 6.54 (d, J=2.44 Hz, 1 H) 6.35 (dd, J=5.80, 1.53 Hz, 1 H) 4.24 (s, 1 H) 3.96-4.11 (m, 1 H) 3.71-3.82 (m, 3 H) 3.25-3.37 (m, 1 H) 2.94-3.17 (m, 3 H) 2.60-2.81 (m, 2 H) 2.11-2.47 (m, J=40.89 Hz, 2 H) 1.72-1.97 (m, 1 H). MS (ESI): 502.2 (M+H)$^+$.

EXAMPLE 1132

N$^2$-{4-[4-(5-fluoro-2-methoxyphenyl)-1H-pyrrolo[2,3-b]pyridin-2-yl]cyclohex-3-en-1-yl}-L-valinamide $^1$H NMR (400 MHz, DMSO-d$_6$) δ ppm 11.70 (s, 1 H) 8.17 (d, J=4.88 Hz, 1 H) 7.42 (s, 1 H) 7.14-7.32 (m, 3 H) 7.01 (d, J=4.88 Hz, 2 H) 6.36-6.54 (m, 1 H) 6.17 (d, J=1.53 Hz, 1 H) 3.59-3.81 (m, 3 H) 2.79-2.98 (m, 1 H) 2.53-2.73 (m, 2 H) 2.22-2.46 (m, 2 H) 1.66-2.14 (m, 3 H) 1.47 (s, 1 H) 0.76-0.98 (m, 6 H). MS (ESI): 437.1 (M+H)$^+$.

EXAMPLE 1133

N$^2$-{4-[4-(5-fluoro-2-methoxyphenyl)-1H-pyrrolo[2,3-b]pyridin-2-yl]cyclohex-3-en-1-yl}-N,3-dimethyl-L-valinamide $^1$H NMR (500 MHz, DMSO-d$_6$) δ ppm 13.12 (d, J=15.56 Hz, 1 H) 9.03-9.22 (m, 1 H) 8.54-8.95 (m, 2 H) 8.27-8.37 (m, 1 H) 7.20-7.42 (m, 4 H) 6.67 (d, J=2.44 Hz, 1 H) 6.47 (s, 1 H) 4.11 (dd, J=15.72, 9.61 Hz, 1 H) 3.71-3.85 (m, 3 H) 3.02-3.21 (m, 1 H) 2.82-2.98 (m, 1 H) 2.64-2.83 (m, 4 H) 2.53-2.65 (m, 1 H) 2.24-2.48 (m, 2 H) 1.79-2.16 (m, 1 H) 1.03-1.21 (m, 9 H). MS (ESI): 465.1 (M+H)$^+$.

EXAMPLE 1134

(2S)-({4-[4-(5-fluoro-2-methoxyphenyl)-1H-pyrrolo[2,3-b]pyridin-2-yl]cyclohex-3-en-1-yl})amino)(phenyl)acetic acid $^1$H NMR (400 MHz, DMSO-d$_6$) δ ppm 12.48 (s, 1 H) 9.51-10.57 (m, 2 H) 8.90 (d, J=3.66 Hz, 1 H) 8.26 (d, J=5.49 Hz, 1 H) 7.62-7.75 (m, 2 H) 7.42-7.55 (m, 3 H) 7.17-7.38 (m, 4 H) 6.50 (s, 1 H) 6.33 (dd, J=9.46, 1.53 Hz, 1 H) 5.34 (d, J=21.97 Hz, 1 H) 3.62-3.83 (m, 3 H) 2.89-3.26 (m, 1 H) 2.54-2.83 (m, 3 H) 2.34 (d, J=7.93 Hz, 2 H) 1.73-1.96 (m, 1 H). MS (ESI): 472.1 (M+H)$^+$.

EXAMPLE 1175

N-{4-[4-(5-fluoro-2-methoxyphenyl)-1H-pyrrolo[2,3-b]pyridin-2-yl]cyclohex-3-en-1-yl}-L-leucine $^1$H NMR (400 MHz, DMSO-d$_6$) δ ppm 12.52 (s, 1 H) 8.99-10.04 (m, 2 H) 7.08-7.50 (m, 4 H) 6.56 (s, 1 H) 6.37 (s, 1 H) 3.97 (d, J=23.19 Hz, 3 H) 3.71-3.89 (m, 2 H) 3.24-3.46 (m, 1 H) 2.37-2.85 (m, 4 H) 2.30 (d, J=12.21 Hz, 1 H) 1.69-1.99 (m, 4 H) 0.83-1.04 (m, 6 H). MS (ESI): 452.1 (M+H)$^+$.

EXAMPLE 1238

1-{4-[4-(5-fluoro-2-methoxyphenyl)-1H-pyrrolo[2,3-b]pyridin-2-yl]cyclohex-3-en-1-yl}-N-methyl-L-prolinamide $^1$H NMR (500 MHz, DMSO-d$_6$) δ ppm 11.78 (s, 1 H) 8.23 (d, J=4.88 Hz, 1 H) 7.75 (d, J=55.85 Hz, 1 H) 7.18-7.38 (m, 3 H) 7.07 (dd, J=4.88, 2.14 Hz, 1 H) 6.41-6.57 (m, 1 H) 6.22 (d, J=5.19 Hz, 1 H) 3.79 (d, J=1.53 Hz, 3 H) 3.27 (s, 1 H) 3.13 (q, J=7.32 Hz, 1 H) 2.59-2.76 (m, 4 H) 2.40 (d, J=17.40 Hz, 2 H) 2.11-2.32 (m, 1 H) 2.00-2.10 (m, 1 H) 1.42-1.93 (m, 4 H). MS (ESI): 449.1 (M+H)$^+$.

EXAMPLE 1331

3-({4-[4-(5-fluoro-2-methoxyphenyl)-1H-pyrrolo[2,3-b]pyridin-2-yl]cyclohex-3-en-1-yl})amino)bicyclo[1.1.1]pentane-1-carboxylic acid $^1$H NMR (501 MHz, DMSO-d$_6$) δ ppm 11.70 (d, J=1.83 Hz, 1 H) 8.17 (d, J=4.88 Hz, 1 H) 7.15-7.32 (m, 3 H) 7.02 (d, J=4.88 Hz, 1 H) 6.43 (s, 1 H) 6.17 (d, J=2.14 Hz, 1 H) 3.74 (s, 3 H) 2.88 (s, 2 H) 2.43-2.56 (m, 2 H) 2.37 (d, J=6.10 Hz, 1 H) 2.01 (s, 6 H) 1.82-1.95 (m, 1 H) 1.39-1.57 (m, 1 H). MS (ESI): 468.1 (M+H)$^+$.

EXAMPLE 583

2-{4-[4-(5-fluoro-2-methoxyphenyl)-1H-pyrrolo[2,3-b]pyridin-2-yl]piperidin-1-yl}ethanesulfonamide To a suspension of Example 17G (200 mg, 0.502 mmol) in N,N-dimethylformamide (5 mL) was added triethylamine (0.21 mL, 1.506 mmol) and ethenesulfonamide (65 mg, 0.603 mmol). The reaction mixture was heated at 60° C. for 3 days. After cooling, the reaction mixture was partitioned between ethyl acetate and brine. The organic phase was washed with brine, and concentrated. The residue was separated by flash chromatography (10-20% methanol in 2:1 ethyl acetate/heptane) to provide the title compound. $^1$H NMR (400 MHz, DMSO-d$_6$): δ1.63-1.74 (m, 2 H), 1.92-2.00 (m, 2 H), 2.05-2.14 (m, 2 H), 2.65-2.77 (m, 3 H), 2.93 (d, J=11.29 Hz, 2 H), 3.15-3.19 (m, 2 H), 3.73 (s, 3 H), 5.96 (d, J=1.53 Hz, 1 H), 6.74 (s, 2 H), 7.01 (d, J=4.88 Hz, 1 H), 7.14-7.28 (m, 3 H), 8.13 (d, J=4.88 Hz, 1 H), 11.56 (s, 1 H); MS (ESI) m/z 433 (M+H)$^+$, 431 (M−1)$^−$.

EXAMPLE 587

4-(5-fluoro-2-methoxyphenyl)-2-[1-(S-methylsulfon-imidoyl)piperidin-4-yl]-1H-pyrrolo[2,3-b]pyridine The title compound was prepared essentially as described in Example 230, substituting Example 17G for Example 87D in Example 230A. $^1$H NMR (400 MHz, DMSO-d$_6$): δ1.64-1.76 (m, 2 H), 2.10 (d, J=13.12 Hz, 2 H), 2.70-2.85 (m, 2 H), 2.76 (d, J=1.53 Hz, 3 H), 3.52 (s, 1 H), 3.73 (s, 3 H), 3.79 (d, J=12.21 Hz, 1 H), 3.79 (d, J=12.21 Hz, 1 H), 6.00 (d, J=1.53 Hz, 1 H), 7.02 (d, J=4.88 Hz, 1 H), 7.16-7.28 (m, 3 H), 8.15 (d, J=5.19 Hz, 1 H), 11.64 (s, 1 H); MS (DCI/NH$_3$) m/z 403 (M+H)$^+$.

EXAMPLE 588

N-ethyl-4-[4-(5-fluoro-2-methoxyphenyl)-1H-pyrrolo[2,3-b]pyridin-2-yl]piperidine-1-sulfonamide To a solution of Example 17G (80 mg, 0.246 mmol) in methylene chloride (6 mL) was added ethylsulfamoyl chloride (53 mg, 0.369 mmol) and triethyl amine (0.103 mL). The mixture was stirred at room temperature overnight, and was directly separated by flash chromatography (0-15% CH$_3$OH in CH$_2$Cl$_2$) to provide the title compound. $^1$H NMR (400 MHz, DMSO-d$_6$): δ1.07 (t, J=7.17 Hz, 3 H), 1.67-1.75 (m, 2 H), 2.07 (d, J=10.99 Hz, 2 H), 2.73-2.79 (m, 2 H), 2.82-2.88 (m, 1 H), 2.91-2.97 (m, 2 H), 3.59 (d, J=12.21 Hz, 2 H), 3.73 (s, 3 H), 5.99 (d, J=1.53 Hz, 1 H), 7.02 (d, J=4.88 Hz, 1 H), 7.15-7.21 (m, 2 H), 7.23-7.28 (m, 1 H), 8.15 (d, J=5.19 Hz, 1 H), 11.62 (s, 1 H); MS (DCI/NH$_3$) m/z 433 (M+H)$^+$.

EXAMPLE 589

4-[3-(4-fluorophenoxy)phenyl]-2-(piperidin-4-yl)-1H-pyrrolo[2,3-b]pyridine

EXAMPLE 589A tert-butyl 4-(4-(3-(4-fluorophenoxy)phenyl)-1H-pyrrolo[2,3-b]pyridin-2-yl)piperidine-1-carboxylate A mixture of 1-bromo-3-(4-fluorophenoxy)benzene (62.5 mg, 0.234 mmol), Example 21A (100 mg, 0.234 mmol), and dichlorobis(triphenylphosphine)palladium (II) (16.42 mg, 0.023 mmol) was suspended in a mixture of 7:3:2 dimethoxyethane/water/ethanol (3 mL). 0.293 mL of 2 M aqueous Na$_2$CO$_3$ solution was then added. The suspension was stirred at room temperature for a few seconds and was stirred in a microwave reactor (Biotage Initiator, model 355302) at 150° C. for 40 minutes. The reaction mixture was partitioned between ethyl acetate and brine. The organic phase was concentrated. The residue was separated by flash chromatography (50-100% ethyl acetate in hexane) to provide the title compound. MS (DCI/NH$_3$) m/z 488 (M+H)$^+$.

EXAMPLE 589B

4-[3-(4-fluorophenoxy)phenyl]-2-(piperidin-4-yl)-1H-pyrrolo[2,3-b]pyridine

A solution of Example 589A (35 mg, 0.072 mmol) in methylene chloride (5 mL) was treated with trifluoroacetic acid (1 mL) at room temperature for 1 hour. Volatiles were removed, and the residue was purified by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (400 MHz, DMSO-d$_6$): δ1.74-1.86 (m, 2 H), 2.23 (d, J=12.51 Hz, 2 H), 3.01-3.11 (m, 3 H), 3.39 (d, J=12.51 Hz, 2 H), 6.26 (s, 1 H), 7.12 (dd, J=8.09, 2.29 Hz, 1 H), 7.18-7.23 (m, 2 H), 7.26-7.32 (m, 3 H), 7.49-7.52 (m, 1 H), 7.56-7.62 (m, 1 H), 8.24 (d, J=4.88 Hz, 1 H), 8.45 (s, 1 H), 8.74 (s, 1 H), 11.96 (s, 1 H); MS (DCI/NH$_3$) m/z 388 (M+H)$^+$.

EXAMPLE 590

4-(2,3-difluorophenyl)-2-(1,2,3,6-tetrahydropyridin-4-yl)-1H-pyrrolo[2,3-b]pyridine The title compound was prepared as described in Example 222C. $^1$H NMR (400 MHz, methanol-d$_4$) δ ppm 2.85-2.96 (m, 2H), 3.51 (t, J=6.1 Hz, 2H), 3.97-4.03 (m, 2H), 6.65-6.71 (m, 1H), 6.87 (d, J=2.3 Hz, 1H), 7.39-7.49 (m, 1H), 7.49-7.61 (m, 2H), 7.65 (dd, J=6.1, 1.3 Hz, 1H), 8.47 (d, J=6.1 Hz, 1H). MS (ESI$^+$) m/z 312.1 (M+H)$^+$.

EXAMPLE 594

2-(8-azabicyclo[3.2.1]oct-2-en-3-yl)-4-(5-fluoro-2-methoxyphenyl)-1H-pyrrolo[2,3-b]pyridine The title compound was prepared as described in Example 223C. $^1$H NMR (400 MHz, methanol-d4) δ ppm 1.96-2.07 (m, 1H), 2.17-2.46 (m, 3H), 2.69-2.78 (m, 1H), 3.16-3.26 (m, 1H), 3.80 (s, 3H), 4.30-4.39 (m, 1H), 4.46-4.49 (m, 1H), 6.58 (d, J=1.9 Hz, 1H), 6.71-6.77 (m, 1H), 7.17-7.31 (m, 3H), 7.40 (dd, J=5.7, 2.8 Hz, 1H), 8.31 (d, J=6.0 Hz, 1H). MS (ESI$^+$) m/z 350.1 (M+H)$^+$.

The following two examples were prepared essentially as described in Example 577, substituting the appropriate amine for Example 87D.

EXAMPLE 599

3-[4-(5-fluoro-2-methoxyphenyl)-1H-pyrrolo[2,3-b]pyridin-2-yl]-N,N-dimethyl-8-azabicyclo[3.2.1]oct-2-ene-8-carboxamide $^1$H NMR (500 MHz, methanol-d$_4$) δ ppm 1.70-1.79 (m, 1H), 1.97-2.10 (m, 2H), 2.17-2.28 (m, 1H), 2.33-2.40 (m, 1H), 2.92 (s, 6H), 3.03-3.11 (m, 1H), 3.81 (s, 3H), 4.36-4.42 (m, 1H), 4.41-4.47 (m, 1H), 6.50 (s, 1H), 6.83 (d, J=5.8 Hz, 1H), 7.18-7.25 (m, 1H), 7.23-7.32 (m, 2H), 7.46 (d, J=6.0 Hz, 1H), 8.26 (d, J=6.0 Hz, 1H). MS (ESI$^+$) m/z 421.1 (M+H)$^+$.

EXAMPLE 607

5-[4-(5-fluoro-2-methoxyphenyl)-1H-pyrrolo[2,3-b]pyridin-2-yl]-N,N-dimethyl-3,6-dihydropyridine-1(2H)-carboxamide $^1$H NMR (400 MHz, methanol-d$_4$) δ ppm 2.42-2.46 (m, 2H), 2.88 (s, 6H), 3.41 (t, J=5.7 Hz, 2H), 3.77 (s, 3H), 4.12 (d, J=2.5 Hz, 2H), 6.26 (s, 1H), 6.52-6.58 (m, 1H), 7.08 (d, J=5.1 Hz, 1H), 7.10-7.20 (m, 3H), 8.16 (d, J=5.1 Hz, 1H). MS (ESI$^+$) m/z 395.2 (M+H)$^+$.

EXAMPLE 600

N-[(2S)-2,3-dihydroxypropyl]-4-[4-(5-fluoro-2-methoxyphenyl)-1H-pyrrolo[2,3-b]pyridin-2-yl]piperidine-1-sulfonamide

EXAMPLE 600A (S)-((2,2-dimethyl-1,3-dioxolan-4-yl)methyl)sulfamoyl chloride (2,2-Dimethyl-1,3-dioxolan-4-yl)methanamine (150 mg, 1.144 mmol) and 4-dimethylaminopyridine (150 mg, 1.228 mmol) in dry dichloromethane (2.5 mL) was added to a stirred solution of sulfuryl chloride (1 M solution in dichloromethane, 1.2 mL, 1.2 mmol) in methylene chloride (4 mL) at −78° C. This resulting mixture was stirred at the same temperature for 1 hour, at −50° C. for 2 hours, and at room temperature for 2 hours. The product formed was used for next step without work up, and was used as a 0.15 M solution in methylene chloride.

EXAMPLE 600B (S)—N-((2,2-dimethyl-1,3-dioxolan-4-yl)methyl)-4-(4-(5-fluoro-2-methoxyphenyl)-1H-pyrrolo[2,3-b]pyridin-2-yl)piperidine-1-sulfonamide To a solution of Example 17G (150 mg, 0.461 mmol) in methylene chloride (7 mL) was added the freshly prepared Example 600A (3.07 mL) and triethylamine (0.103 mL). The mixture was stirred at room temperature overnight, and was then partitioned between ethyl acetate and brine. The organic phase was washed with brine, and concentrated. The residue was separated by flash chromatography (0-15% CH$_3$OH in CH$_2$Cl$_2$) to provide the title compound. MS (DCI/NH$_3$) m/z 519 (M+H)$^+$.

EXAMPLE 600C

N-[(2S)-2,3-dihydroxypropyl]-4-[4-(5-fluoro-2-methoxyphenyl)-1H-pyrrolo[2,3-b]pyridin-2-yl]piperidine-1-sulfonamide Concentrated HCl (1 mL) was added to a stirred solution of Example 600B (80 mg, 0.154 mmol) in ethanol (4 mL) at room temperature. The solution was stirred at room temperature for 4 hours, and concentrated. The residue was purified by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (500 MHz, CD$_3$OD): δ1.82-1.91 (m, 2 H), 2.15 (d, J=11.29 Hz, 2 H), 2.90-2.96 (m, 2 H), 2.98-3.03 (m, 2 H), 3.15-3.18 (m, 1 H), 3.50-3.57 (m, 2 H), 3.71-3.76 (m, 1 H), 3.81 (s, 3 H), 6.40 (s, 1 H), 7.21-7.24 (m, 1 H), 7.26-7.31 (m, 2 H), 7.51 (d, J=6.10 Hz, 1 H), 8.28 (d, J=6.10 Hz, 1 H); MS (DCI/NH$_3$) m/z 479 (M+H)$^+$.

EXAMPLE 601

3-chloro-4-(5-fluoro-2-methoxyphenyl)-2-(piperidin-4-yl)-1H-pyrrolo[2,3-b]pyridine To a solution of Example 17G (100 mg, 0.307 mmol) in acetonitrile (7 mL) was added N-chlorosuccinimide (49 mg, 0.369 mmol). The solution was stirred at 50° C. overnight. The volatiles were removed, and the residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (500 MHz, CD$_3$OD): δ2.14-2.19 (m, 4 H), 3.16-3.23 (m, 2 H), 3.38-3.45 (m, 1 H), 3.55 (d, J=13.12 Hz, 2 H), 3.71 (s, 3 H), 7.02-7.07 (m, 1 H), 7.11 (s, 1 H), 7.17-7.22 (m, 1 H), 8.30 (d, J=5.49 Hz, 1 H); MS (DCI/NH$_3$) m/z 360 (M+H)$^+$.

EXAMPLE 602

3-bromo-4-(5-fluoro-2-methoxyphenyl)-2-(piperidin-4-yl)-1H-pyrrolo[2,3-b]pyridine To a solution of Example 17G (200 mg, 0.615 mmol) in acetonitrile (20 mL) was added N-bromosuccinimide (120 mg, 0.676 mmol), and the solution was stirred at 45° C. overnight. The volatiles were removed, and the residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (500 MHz, CD$_3$OD): δ2.11-2.22 (m, 4 H), 3.16-3.23 (m, 2 H), 3.39-3.45 (m, 1 H), 3.53-3.57 (m, 2 H), 3.70 (s, 3 H), 6.99-7.02 (m, 1 H), 7.05-7.09 (m, 2 H), 7.16-7.22 (m, 1 H), 8.29 (d, J=5.19 Hz, 1 H); MS (DCI/NH$_3$) m/z 404, 406 (M+H)$^+$.

EXAMPLE 603 ethyl ({4-[3-bromo-4-(5-fluoro-2-methoxyphenyl)-1H-pyrrolo[2,3-b]pyridin-2-yl]piperidin-1-yl}sulfonyl)carbamate To a suspension of Example 602 (155 mg, 0.299 mmol) in CH$_2$Cl$_2$ (6 mL) was added triethylamine (0.151 mL, 1.496 mmol) and Example 578A (98 mg, 0.359 mmol) at room temperature. The mixture was stirred at room temperature overnight, and was directly separated by flash chromatography (0-15% CH$_3$OH in CH$_2$Cl$_2$) to provide the title compound. $^1$H NMR (500 MHz, CD$_3$OD): δ 1.22 (t, J=7.17 Hz, 3 H), 1.77-1.84 (m, 2 H), 1.89-2.00 (m, 2 H), 2.93-2.98 (m, 2 H), 3.00-3.06 (m, 1 H), 3.66 (s, 3 H), 3.75-3.80 (m, 2 H), 4.13 (q, J=7.12 Hz, 2 H), 6.92 (d, J=4.88 Hz, 1 H), 7.06-7.10 (m, 2 H), 7.21-7.27 (m, 1 H), 8.23 (d, J=4.88 Hz, 1 H), 11.27 (s, 1 H), 12.11 (s, 1 H); MS (DCI/NH$_3$) m/z 555, 557 (M+H)$^+$.

EXAMPLE 604

4-[4-(5-fluoro-2-methoxyphenyl)-1H-pyrrolo[2,3-b]pyridin-2-yl]-N-(2-hydroxyethyl)-3,6-dihydropyridine-1(2H)-carboxamide In a 20 mL vial was added Example 87D (0.045 g, 0.11 mmol) and triethylamine (0.10 mL, 0.72 mmol) in N,N- dimethylformamide (1 mL). The mixture was cooled to 0° C. and 4-nitrophenyl carbonochloridate (0.03 g, 0.149 mmol) was added. The mixture was stirred at room temperature for 2 hours and 2-aminoethanol (0.395 g, 6.47 mmol) was added. The suspension was stirred at room temperature overnight. The product was purified by preparative reverse phase column (Analogix, C-18, 40 g) with gradient elution from 0-100% acetonitrile in water with 0.1% trifluoroacetic acid to afford the title compound as trifluoroacetate salt. $^1$H NMR (400 MHz, DMSO-$d_6$): δ 2.40-2.48 (m, 2 H) 3.09-3.14 (m, 2 H) 3.49-3.53 (m, 2 H) 3.74 (s, 3 H) 4.00-4.04 (m, 2 H) 6.27 (d, J=1.83 Hz, 1 H) 6.49-6.55 (m, 2 H) 7.06 (d, J=5.19 Hz, 1 H) 7.17-7.32 (m, 3 H) 8.21 (d, J=5.19 Hz, 1 H) 11.87 (s, 1 H). MS (ESI$^+$) m/z 411.1 (M+H)$^+$.

EXAMPLE 606

N-methyl-4-[2-(1,2,3,6-tetrahydropyridin-4-yl)-1H-pyrrolo[2,3-b]pyridin-4-yl]benzamide The title compound was prepared essentially as described in Example 222A-C, substituting the appropriate boronic acid in Example 222A. $^1$H NMR (400 MHz, methanol-$d_4$) δ ppm 2.89-3.02 (m, 5H), 3.53 (t, J=6.1 Hz, 2H), 4.00 (q, J=2.6 Hz, 2H), 6.62-6.71 (m, 1H), 7.07 (s, 1H), 7.70 (d, J=6.2 Hz, 1H), 7.98 (d, J=8.3 Hz, 2H), 8.03-8.13 (m, 2H), 8.44 (d, J=6.3 Hz, 1H). MS (ESI$^+$) m/z 333.1 (M+H)$^+$.

EXAMPLE 610

4-[4-(5-fluoro-2-methoxyphenyl)-1H-pyrrolo[2,3-b]pyridin-2-yl]-N-[2-(pyrrolidin-1-yl)ethyl]-3,6-dihydropyridine-1(2H)-carboxamide To a suspension of Example 87D (80 mg, 0.202 mmol) in N,N-dimethylformamide (2.0 mL) was added triethylamine (0.169 mL, 1.211 mmol) and 1-chloro-2-isocyanatoethane (0.026 mL, 0.303 mmol). The reaction mixture was stirred at room temperature overnight. To this mixture was added pyrrolidine (57.4 mg, 0.807 mmol). The reaction was heated to 50° C. for 7 hours. The reaction mixture was treated with water/brine/NaHCO$_3$ and extracted with ethyl acetate. The combined organic layers were washed with water, dried over MgSO$_4$, filtered, concentrated, and purified by reverse-phase HPLC performed on a XBridge Prep C18 OBD column (19×250 mm, 10 μm) using a gradient of 30-60% CH$_3$CN in 10 mmol/mL NH$_4$HCO$_3$ in water at a flow rate of 30 mL/minute to afford the title compound. $^1$H NMR (400 MHz, DMSO-$d_6$) δ ppm 1.65 (s, 4H), 2.42-2.50 (m, 8H), 3.12-3.17 (m, 2H), 3.50 (t, J=5.4 Hz, 2H), 3.74 (s, 3H), 4.00 (s, 2H), 6.24 (s, 1H), 6.47-6.51 (m, 2H), 7.03 (d, J=4.8 Hz, 1H), 7.17-7.30 (m, 3H), 8.20 (d, J=4.8 Hz, 1H), 11.83 (s, 1H). MS (ESI$^+$) m/z 464.3 (M+H)$^+$.

The following compounds (concluding with Example 821) were prepared essentially as described in Example 610, substituting the appropriate amine for pyrrolidine. K$_2$CO$_3$ and/or NaI was sometimes added in the heating stage of the reaction.

EXAMPLE 611

4-[4-(5-fluoro-2-methoxyphenyl)-1H-pyrrolo[2,3-b]pyridin-2-yl]-N-[2-(4-hydroxypiperidin-1-yl)ethyl]-3,6-dihydropyridine-1(2H)-carboxamide $^1$H NMR (400 MHz, DMSO-$d_6$) δ ppm 1.31-1.40 (m, 2H), 1.66-1.70 (m, 2H), 2.00 (t, J=10.2 Hz, 2H), 2.31 (t, J=6.8 Hz, 2H), 2.44 (s, 2H), 2.67-2.70 (m, 2H), 3.10-3.15 (m, 2H), 3.38-3.44 (m, 1H), 3.49 (t, J=9.4 Hz, 2H), 3.74 (s, 3H), 4.00 (s, 2H), 4.51 (d, J=4.0 Hz, 1H), 6.25 (s, 1H), 6.43 (t, J=5.2 Hz, 1H), 6.51 (s, 1H), 7.03 (d, J=4.8 Hz, 1H), 7.17-7.30 (m, 3H), 8.20 (d, J=5.2 Hz, 1H), 11.83 (s, 1H). MS (ESI$^+$) m/z 494.3 (M+H)$^+$.

EXAMPLE 612

4-[4-(5-fluoro-2-methoxyphenyl)-1H-pyrrolo[2,3-b]pyridin-2-yl]-N-{2-[(tetrahydrofuran-2-ylmethyl)amino]ethyl}-3,6-dihydropyridine-1(2H)-carboxamide $^1$H NMR (400 MHz, DMSO-$d_6$) δ ppm 1.45-1.52 (m, 1H), 1.71-1.80 (m, 2H), 1.84-1.89 (m, 1H), 2.41-2.43 (m, 2H), 2.51-2.55 (m, 2H), 2.58 (t, J=6.4 Hz, 2H), 3.09-3.12 (m, 2H), 3.50 (t, J=5.6 Hz, 2H), 3.54-3.59 (m, 1H), 3.67-3.75 (m, 5H), 3.80-3.84 (m, 1H), 4.01 (s, 2H), 6.24 (s, 1H), 6.47-6.51 (m, 2H), 7.03 (d, J=4.8 Hz, 1H), 7.17-7.30 (m, 3H), 8.20 (d, J=4.8 Hz, 1H), 11.83 (s, 1H). MS (ESI$^+$) m/z 494.3 (M+H)$^+$.

EXAMPLE 613 methyl 4-{2-[({4-[4-(5-fluoro-2-methoxyphenyl)-1H-pyrrolo[2,3-b]pyridin-2-yl]-3,6-dihydropyridin-1(2H)-yl}carbonyl)amino]ethyl}piperazine-1-carboxylate $^1$H NMR (400 MHz, CDCl$_3$) δ ppm 2.48 (m, 4H), 2.56-2.62 (m, 4H), 3.85-3.43 (m, 2H), 3.51 (s, 4H), 3.65-3.72 (m, 5H), 3.79 (s, 3H), 4.14 (d, J=2.4 Hz, 2H), 5.21 (brs, 1H), 6.32 (s, 1H), 6.37 (s, 1H), 6.98-7.02 (m, 1H), 7.08-7.21 (m, 3H), 8.27 (d, J=5.2 Hz, 1H), 11.87 (s, 1H). MS (ESI$^+$) m/z 537.3 (M+H)$^+$.

EXAMPLE 614

N-[2-(3,4-dihydroisoquinolin-2(1H)-yl)ethyl]-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CDCl$_3$) δ ppm 2.57 (s, 2H), 2.77 (t, J=5.4 Hz, 2H), 2.84 (t, J=5.4 Hz, 2H), 2.94 (t, J=5.4 Hz, 2H), 3.48-3.53 (m, 2H), 3.65 (t, J=5.6 Hz, 2H), 3.73 (s, 2H), 3.77 (s, 3H), 4.10 (s, 2H), 5.47 (brs, 1H), 6.23 (s, 1H), 6.33 (s, 1H), 6.97-7.03 (m, 2H), 7.04-7.20 (m, 6H), 8.25 (d, J=4.8 Hz, 1H), 10.43 (s, 1H). MS (ESI$^+$) m/z 526.3 (M+H)$^+$.

EXAMPLE 648

4-[4-(5-fluoro-2-methoxyphenyl)-1H-pyrrolo[2,3-b]pyridin-2-yl]-N-[2-(4-oxopiperidin-1-yl)ethyl]-3,6-dihydropyridine-1(2H)-carboxamide $^1$H NMR (400 MHz, DMSO-$d_6$) δ ppm 2.32 (t, J=5.8 Hz, 4H), 2.45 (s, 2H), 2.50 (s, 2H), 2.71 (t, J=6.0 Hz, 4H), 3.18-3.23 (m, 2H), 3.51 (t, J=5.6 Hz, 2H), 3.74 (s, 3H), 4.02 (s, 2H), 6.24 (s, 1H), 6.24-6.54 (m, 2H), 7.03 (d, J=4.8 Hz, 1H), 7.17-7.28 (m, 3H), 8.20 (d, J=5.2 Hz, 1H), 11.83 (s, 1H). MS (ESI$^+$) m/z 492.3 (M+H)$^+$.

EXAMPLE 649

N-[2-(3,3-difluoropiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CDCl$_3$) δ ppm 1.75-1.80 (m, 2H), 1.87-1.97 (m, 2H), 2.52 (t, J=4.6 Hz, 2H), 2.61-2.65 (m, 4H), 2.67-2.73 (m, 2H), 3.36-3.41 (m, 2H), 3.66 (t, J=2.6 Hz, 2H), 3.79 (s, 3H), 4.14 (s, 2H), 5.38 (t, J=4.2 Hz, 1H), 6.33 (s, 1H), 6.37 (s, 1H), 6.98-7.02 (m, 1H), 7.09-7.22 (m, 3H), 8.27 (d, J=5.2 Hz, 1H), 10.92 (s, 1H). MS (ESI$^+$) m/z 514.3 (M+H)$^+$.

EXAMPLE 650

4-[4-(5-fluoro-2-methoxyphenyl)-1H-pyrrolo[2,3-b]pyridin-2-yl]-N-[2-(3-hydroxypiperidin-1-yl)ethyl]-3,6-dihydropyridine-1(2H)-carboxamide $^1$H NMR (400 MHz, CDCl$_3$) δ ppm 1.51-1.55 (m, 2H), 1.66-1.84 (m, 2H), 2.41-2.59 (m, 8H), 3.36-2.41 (m, 2H), 3.65 (t, J=5.6 Hz, 2H), 3.77 (s, 3H), 3.84 (s, 1H), 4.12 (s, 2H), 5.28 (t, J=4.6 Hz, 1H), 6.32-6.34 (m, 2H), 6.37 (s, 1H), 6.97-7.00 (m, 1H), 7.07-7.20 (m, 3H), 8.26 (d, J=5.2 Hz, 1H), 11.10 (s, 1H). MS (ESI$^+$) m/z 494.3 (M+H)$^+$.

EXAMPLE 651

4-[4-(5-fluoro-2-methoxyphenyl)-1H-pyrrolo[2,3-b]pyridin-2-yl]-N-{2-[(3S)-3-hydroxypyrrolidin-1-yl]ethyl}-3,6-dihydropyridine-1(2H)-carboxamide $^1$H NMR (400 MHz, CDCl$_3$) δ ppm 1.78-1.83 (m, 1H), 2.16-2.24 (m, 1H), 2.36-2.41 (m, 1H), 2.57-2.61 (m, 3H), 2.67-2.76 (m, 2H), 2.87 (d, J=10.0 Hz, 1H), 3.00-3.06 (s, 1H), 3.40-3.43 (m, 2H), 3.63-3.67 (m, 2H), 3.77 (s, 3H), 4.12 (s, 2H), 4.39-4.43 (m, 1H), 5.43 (s, 1H), 6.28 (s, 1H), 6.33 (s, 1H), 6.96-7.00 (m, 1H), 7.07-7.13 (m, 2H), 7.16-7.19 (m, 1H), 8.26 (d, J=5.2 Hz, 1H), 10.75 (s, 1H). MS (ESI$^+$) m/z 480.3 (M+H)$^+$.

EXAMPLE 652

4-[4-(5-fluoro-2-methoxyphenyl)-1H-pyrrolo[2,3-b]pyridin-2-yl]-N-{2-[(2-hydroxyethyl)(methyl)amino]ethyl}-3,6-dihydropyridine-1(2H)-carboxamide $^1$H NMR (400 MHz, CDCl$_3$) δ ppm 2.32 (s, 3H), 2.57-2.63 (m, 6H), 3.39-3.44 (m, 2H), 3.63-3.69 (m, 4H), 3.77 (s, 3H), 4.12 (s, 2H), 5.27 (d, J=4.6 Hz, 1H), 6.26 (s, 1H), 6.32 (s, 1H), 6.96-6.99 (m, 1H), 7.07-7.18 (m, 3H), 8.24 (d, J=4.8 Hz, 1H), 10.83 (s, 1H). MS (ESI$^+$) m/z 468.3 (M+H)$^+$.

EXAMPLE 653

4-[4-(5-fluoro-2-methoxyphenyl)-1H-pyrrolo[2,3-b]pyridin-2-yl]-N-{2-[4-(2-hydroxyethyl)piperazin-1-yl]ethyl}-3,6-dihydropyridine-1(2H)-carboxamide $^1$H NMR (400 MHz, CDCl$_3$) δ ppm 2.53-2.63 (m, 14H), 3.36-3.41 (m, 2H), 3.61 (t, J=5.2 Hz, 2H), 3.68 (t, J=6.2 Hz, 2H), 3.79 (s, 3H), 4.15 (s, 2H), 5.29 (s, 1H), 6.26 (s, 1H), 6.37 (s, 2H), 6.98-7.02 (m, 1H), 7.09-7.16 (m, 2H), 7.18-7.22 (m, 1H), 8.26 (d, J=5.2 Hz, 1H), 11.26 (s, 1H). MS (ESI$^+$) m/z 523.3 (M+H)$^+$.

EXAMPLE 654

4-[4-(5-fluoro-2-methoxyphenyl)-1H-pyrrolo[2,3-b]pyridin-2-yl]-N-[2-(3-oxopiperazin-1-yl)ethyl]-3,6-dihydropyridine-1(2H)-carboxamide $^1$H NMR (400 MHz, CDCl$_3$) δ ppm 2.59-2.64 (m, 4H), 2.71 (t, J=5.2 Hz, 2H), 3.21 (s, 2H), 3.39-3.44 (m, 4H), 3.65 (t, J=5.6 Hz, 2H), 3.77 (s, 3H), 4.10 (s, 2H), 5.08 (t, J=4.8 Hz, 1H), 6.31 (s, 1H), 6.34 (s, 1H), 6.78 (s, 1H), 6.97-7.00 (m, 1H), 7.08-7.19 (m, 3H), 8.24 (d, J=4.8 Hz, 1H), 10.95 (s, 1H). MS (ESI$^+$) m/z 493.3 (M+H)$^+$.

EXAMPLE 655

4-[4-(5-fluoro-2-methoxyphenyl)-1H-pyrrolo[2,3-b]pyridin-2-yl]-N-{2-[(3S)-3-hydroxypiperidin-1-yl]ethyl}-3,6-dihydropyridine-1(2H)-carboxamide $^1$H NMR (400 MHz, CDCl$_3$) δ ppm 1.55-1.56 (m, 2H), 1.66-1.72 (m, 2H), 2.38-2.60 (m, 8H), 3.37-3.42 (m, 2H), 3.65 (t, J=5.6 Hz, 2H), 3.78 (s, 3H), 3.85 (s, 1H), 4.12 (s, 2H), 5.25 (s, 1H), 6.28 (s, 1H), 6.34 (s, 1H), 6.78 (s, 1H), 6.97-7.00 (m, 1H), 7.08-7.17 (m, 2H), 7.18-7.20 (m, 1H), 8.26 (d, J=4.8 Hz, 1H), 10.67 (s, 1H). MS (ESI$^+$) m/z 494.3 (M+H)$^+$.

EXAMPLE 691

4-[4-(5-fluoro-2-methoxyphenyl)-1H-pyrrolo[2,3-b]pyridin-2-yl]-N-[2-(piperazin-1-yl)ethyl]-3,6-dihydropyridine-1(2H)-carboxamide $^1$H NMR (400 MHz, CDCl$_3$) δ ppm 2.45 (s, 4H), 2.52 (t, J=6.0 Hz, 2H), 2.62 (s, 2H), 2.90 (t, J=4.6 Hz, 4H), 3.35-3.40 (m, 2H), 3.67 (t, J=5.4 Hz, 2H), 3.79 (s, 3H), 4.14 (s, 2H), 5.30 (t, J=4.4 Hz, 1H), 6.33-6.37 (m, 2H), 6.98-7.02 (m, 1H), 7.09-7.16 (m, 2H), 7.18-7.22 (m, 1H), 8.28 (d, J=5.2 Hz, 1H), 10.93 (s, 1H). MS (ESI$^+$) m/z 479.3 (M+H)$^+$.

EXAMPLE 692

N-[2-(4-aminopiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CDCl$_3$) δ ppm 1.35-1.45 (m, 2H), 1.82-1.86 (m, 2H), 2.05-2.12 (m, 2H), 2.53 (t, J=5.8 Hz, 2H), 2.60-2.62 (m, 2H), 2.72-2.77 (m, 1H), 2.85-2.89 (m, 2H), 3.34-3.38 (m, 2H), 3.66 (t, J=5.6 Hz, 2H), 3.79 (s, 3H), 5.37 (s, 1H), 6.28 (s, 1H), 6.36 (s, 1H), 6.98-7.01 (m, 1H), 7.08-7.15 (m, 2H), 7.18-7.21 (m, 1H), 8.27 (d, J=4.8 Hz, 1H), 10.31 (s, 1H). MS (ESI$^+$) m/z 493.3 (M+H)$^+$.

EXAMPLE 693

N-{2-[(1,3-dihydroxypropan-2-yl)amino]ethyl}-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CD$_3$OD) δ ppm 2.58 (s, 2H), 2.73-2.76 (m, 1H), 2.84 (t, J=6.0 Hz, 2H), 3.36 (t, J=6.2 Hz, 2H), 3.52-3.57 (m, 2H), 3.60-3.67 (m, 4H), 3.78 (s, 3H), 4.15 (s, 2H), 6.32 (s, 1H), 6.42 (s, 1H), 7.10 (d, J=5.2 Hz, 1H), 7.14-7.20 (m, 3H), 8.18 (d, J=5.2 Hz, 1H). MS (ESI$^+$) m/z 484.2 (M+H)$^+$.

EXAMPLE 724

4-[4-(5-fluoro-2-methoxyphenyl)-1H-pyrrolo[2,3-b]pyridin-2-yl]-N-(2-{[2-(1H-imidazol-4-yl)ethyl]amino}ethyl)-3,6-dihydropyridine-1(2H)-carboxamide $^1$H NMR (400 MHz, CD$_3$OD) δ ppm 2.46 (s, 2H), 2.69 (t, J=7.4 Hz, 4H), 2.81 (t, J=7.0 Hz, 2H), 3.24 (t, J=6.2 Hz, 2H), 3.52 (t, J=6.2 Hz, 2H), 3.67 (s, 3H), 4.00 (s, 2H), 6.21 (s, 1H), 6.30 (s, 1H), 6.75 (s, 1H), 6.98 (d, J=5.2 Hz, 1H), 7.04-7.08 (m, 3H), 7.47 (s, 1H), 8.06 (d, J=5.2 Hz, 1H). MS (ESI$^+$) m/z 504.3 (M+H)$^+$.

EXAMPLE 725

4-[4-(5-fluoro-2-methoxyphenyl)-1H-pyrrolo[2,3-b]pyridin-2-yl]-N-{2-[(2-hydroxypropyl)amino]ethyl}-3,6-dihydropyridine-1(2H)-carboxamide $^1$H NMR (400 MHz, CDCl$_3$) δ ppm 1.18 (d, J=6.0 Hz, 3H), 2.52 (s, 2H), 2.59-2.66 (m, 1H), 2.80-2.84 (m, 1H), 2.95 (d, J=4.8 Hz, 2H), 3.46-3.49 (m, 2H), 3.63 (t, J=5.4 Hz, 2H), 3.76-3.78 (m, 4H), 3.96-4.01 (m, 1H), 4.14 (s, 2H), 5.63 (s, 1H), 6.29 (s, 1H), 6.37 (s, 1H), 6.96-7.00 (m, 1H), 7.07-7.17 (m, 3H), 8.20 (d, J=4.8 Hz, 1H), 10.54 (s, 1H). MS (ESI$^+$) m/z 468.3 (M+H)$^+$.

EXAMPLE 726

N-[2-(dimethylamino)ethyl]-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CDCl$_3$) δ ppm 2.28 (s, 6H), 2.49 (t, J=5.8 Hz, 2H), 2.61 (s, 2H), 3.35-3.40 (m, 2H), 3.67 (t, J=5.6 Hz, 2H), 3.79 (s, 3H), 4.15 (s, 2H), 5.33 (s, 1H), 6.29 (s, 1H), 6.36 (s, 1H), 6.98-7.01 (m, 1H), 7.08-7.22 (m, 3H), 8.28 (d, J=5.2 Hz, 1H), 10.62 (s, 1H). MS (ESI$^+$) m/z 438.3 (M+H)$^+$.

EXAMPLE 727

4-[4-(5-fluoro-2-methoxyphenyl)-1H-pyrrolo[2,3-b]pyridin-2-yl]-N-(2-{[(3-methyloxetan-3-yl)methyl]amino}ethyl)-3,6-dihydropyridine-1(2H)-carboxamide $^1$H NMR (400 MHz, CD$_3$OD) δ ppm 1.22 (s, 3H), 2.46 (s, 2H), 2.67 (t, J=6.2 Hz, 2H), 2.74 (s, 2H), 3.25 (t, J=6.4 Hz, 2H), 3.53 (t, J=5.6 Hz, 2H), 3.67 (s, 3H), 4.02 (s, 2H), 4.24 (d, J=6.0 Hz, 2H), 4.38 (d, J=6.0 Hz, 2H), 6.20 (s, 1H), 6.30 (s, 1H), 6.98 (d, J=5.2 Hz, 1H), 7.04-7.08 (m, 3H), 8.06 (d, J=5.2 Hz, 1H). MS (ESI$^+$) m/z 494.2 (M+H)$^+$.

EXAMPLE 728

4-[4-(5-fluoro-2-methoxyphenyl)-1H-pyrrolo[2,3-b]pyridin-2-yl]-N-[2-(oxetan-3-ylamino)ethyl]-3,6-dihydropyridine-1(2H)-carboxamide $^1$H NMR (400 MHz, CDCl$_3$) δ ppm 2.61 (s, 2H), 2.76 (t, J=5.6 Hz, 2H), 3.35-3.40 (m, 2H), 3.67 (t, J=5.4 Hz, 2H), 3.79 (s, 3H), 3.94-4.02 (m, 1H), 4.14 (s, 2H), 4.45 (t, J=6.2 Hz, 2H), 4.84 (t, J=6.6 Hz, 2H), 5.12 (s, 1H), 6.32 (s, 1H), 6.36 (s, 1H), 6.98-7.01 (m, 1H), 7.08-7.21 (m, 3H), 8.27 (s, 1H), 10.96 (s, 1H). MS (ESI$^+$) m/z 466.2 (M+H)$^+$.

EXAMPLE 796

4-[4-(5-fluoro-2-methoxyphenyl)-1H-pyrrolo[2,3-b]pyridin-2-yl]-N-(2-{[(1S,2S)-2-hydroxycyclohexyl]amino}ethyl)-3,6-dihydropyridine-1(2H)-carboxamide $^1$H NMR (400 MHz, CD$_3$OD) δ ppm 1.00-1.17 (m, 1H), 1.22-1.33 (m, 3H), 1.73 (s, 2H), 1.95-2.05 (m, 2H), 2.39-2.45 (m, 1H), 2.58 (s, 2H), 2.71-2.78 (m, 1H), 2.88-2.95 (m, 1H), 3.26-3.29 (m, 1H), 3.37-3.40 (m, 2H), 3.66 (t, J=5.6 Hz, 2H), 3.79 (s, 3H), 4.14 (s, 2H), 6.32 (s, 1H), 6.42 (s, 1H), 7.10 (d, J=5.2 Hz, 1H), 7.16-7.20 (m, 3H), 8.18 (d, J=4.8 Hz, 1H). MS (ESI$^+$) m/z 508.3 (M+H)$^+$.

EXAMPLE 797

N-(2-{[2-(dimethylamino)ethyl]amino}ethyl)-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CDCl$_3$) δ ppm 2.22 (s, 6H), 2.43 (t, J=5.8 Hz, 2H), 2.59 (s, 2H), 2.72 (t, J=6.0 Hz, 2H), 2.83 (t, J=5.8 Hz, 2H), 3.37-3.42 (m, 2H), 3.66 (t, J=5.8 Hz, 2H), 3.78 (s, 3H), 4.14 (s, 3H), 5.37 (s, 1H), 6.29 (s, 1H), 6.35 (s, 1H), 6.98-7.01 (m, 1H), 7.07-7.15 (m, 2H), 7.17-7.21 (m, 1H), 8.27 (d, J=5.2 Hz, 1H), 10.58 (s, 1H). MS (ESI$^+$) m/z 481.3 (M+H)$^+$.

EXAMPLE 798

4-[4-(5-fluoro-2-methoxyphenyl)-1H-pyrrolo[2,3-b]pyridin-2-yl]-N-{2-[(2-methoxyethyl)(methyl)amino]ethyl}-3,6-dihydropyridine-1(2H)-carboxamide $^1$H NMR (400 MHz, CDCl$_3$) δ ppm 2.32 (s, 3H), 2.57-2.64 (m, 6H), 3.34-3.48 (m, 5H), 3.49 (t, J=5.4 Hz, 2H), 3.68 (t, J=5.8 Hz, 2H), 3.78 (s, 3H), 4.15 (s, 3H), 5.51 (s, 1H), 6.29 (s, 1H), 6.35 (s, 1H), 6.98-7.02 (m, 1H), 7.07-7.15 (m, 2H), 7.19-7.22 (m, 1H), 8.27 (d, J=4.8 Hz, 1H), 10.60 (s, 1H). MS (ESI+) m/z 482.2 (M+H)+.

EXAMPLE 799

4-[4-(5-fluoro-2-methoxyphenyl)-1H-pyrrolo[2,3-b]pyridin-2-yl]-N-{2-[4-(4-methylbenzoyl)piperazin-1-yl]ethyl}-3,6-dihydropyridine-1(2H)-carboxamide $^1$H NMR (400 MHz, CD$_3$OD) δ ppm 2.41 (s, 3H), 2.64 (s, 2H), 3.32-3.35 (m, 10H), 3.61 (t, J=5.2 Hz, 2H), 3.70 (t, J=5.8 Hz, 2H), 3.83 (s, 3H), 4.21 (s, 2H), 6.56 (s, 2H), 7.23-7.34 (m, 5H), 7.39-7.45 (m, 3H), 8.29 (d, J=5.6 Hz, 1H). MS (ESI$^+$) m/z 597.3 (M+H)$^+$.

EXAMPLE 800

4-[4-(5-fluoro-2-methoxyphenyl)-1H-pyrrolo[2,3-b]pyridin-2-yl]-N-{2-[4-(methylsulfonyl)piperazin-1-yl]ethyl}-3,6-dihydropyridine-1(2H)-carboxamide $^1$H NMR (400 MHz, CDCl$_3$) δ ppm 2.58-2.63 (m, 8H), 2.77 (s, 3H), 3.26 (t, J=4.4 Hz, 4H), 3.39-3.44 (m, 2H), 3.66 (t, J=5.6 Hz, 2H), 3.79 (s, 3H), 4.14 (s, 2H), 5.00 (s, 1H), 6.32 (s, 1H), 6.37 (s, 1H), 6.98-7.02 (m, 1H), 7.09-7.22 (m, 3H), 8.27 (d, J=5.2 Hz, 1H), 10.88 (s, 1H). MS (ESI$^+$) m/z 557.3 (M+H)$^+$.

EXAMPLE 801

4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide $^1$H NMR (400 MHz, CDCl$_3$) δ ppm 2.53 (s, 2H), 2.84-2.89 (m, 4H), 3.42 (t, J=5.2 Hz, 2H), 3.62 (t, J=5.4 Hz, 2H), 3.71-3.76 (m, 6H), 4.10 (s, 2H), 5.52 (s, 1H), 6.29 (s, 2H), 6.95-6.99 (m, 1H), 7.06-7.17 (m, 3H), 8.21 (d, J=5.2 Hz, 1H), 10.90 (s, 1H). MS (ESI$^+$) m/z 454.2 (M+H)$^+$.

EXAMPLE 802

4-[4-(5-fluoro-2-methoxyphenyl)-1H-pyrrolo[2,3-b]pyridin-2-yl]-N-(2-{[3-(trifluoromethyl)benzyl]amino}ethyl)-3,6-dihydropyridine-1(2H)-carboxamide $^1$H NMR (400 MHz, CD$_3$OD) δ ppm 2.57 (s, 2H), 2.75 (t, J=5.8 Hz, 2H), 3.38 (t, J=6.2 Hz, 2H), 3.64 (t, J=5.6 Hz, 2H), 3.78 (s, 3H), 3.87 (s, 2H), 4.13 (s, 2H), 6.31 (s, 1H), 6.42 (s, 1H), 7.10 (d, J=5.2 Hz, 1H), 7.15-7.20 (m, 3H), 7.51-7.63 (m, 3H), 7.70 (s, 1H), 8.18 (d, J=5.2 Hz, 1H). MS (ESI$^+$) m/z 568.2 (M+H)$^+$.

EXAMPLE 819

N-[2-(ethylamino)ethyl]-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CD$_3$OD) δ ppm 1.32 (t, J=7.2 Hz, 3H), 2.63 (s, 2H), 3.07-3.16 (m, 4H), 3.49-3.53 (m, 2H), 3.69 (t, J=5.8 Hz, 2H), 3.83 (s, 3H), 4.20 (s, 2H), 6.56 (s, 2H), 7.21-7.30 (m, 3H), 7.43 (d, J=5.2 Hz, 1H), 8.29 (d, J=4.8 Hz, 1H). MS (ESI$^+$) m/z 438.1 (M+H)$^+$.

EXAMPLE 820

N-[2-(cyclopropylamino)ethyl]-4-[4-(5-fluoro-2-methoxyphenyl)-1H-pyrrolo[2,3-b]pyridin-2-yl]-3,6-dihydropyridine-1(2H)-carboxamide $^1$H NMR (400 MHz, CD$_3$OD) δ ppm 0.87-0.94 (m, 4H), 2.63 (s, 2H), 2.79-2.85 (m, 1H), 3.26-3.30 (m, 2H), 3.53 (t, J=5.6 Hz, 2H), 3.69 (t, J=5.6 Hz, 2H), 3.83 (s, 3H), 4.20 (s, 2H), 6.57 (s, 2H), 7.22-7.31 (m, 3H), 7.45-7.48 (m, 1H), 8.30 (d, J=6.0 Hz, 1H). MS (ESI$^+$) m/z 450.2 (M+H)$^+$.

EXAMPLE 821

4-[4-(5-fluoro-2-methoxyphenyl)-1H-pyrrolo[2,3-b]pyridin-2-yl]-N-{2-[(pyridin-2-ylmethyl)amino]ethyl}-3,6-dihydropyridine-1(2H)-carboxamide $^1$H NMR (400 MHz, CDCl$_3$) δ ppm 2.58 (s, 2H), 2.78 (t, J=6.2 Hz, 2H), 3.38 (t, J=6.2 Hz, 2H), 3.65 (t, J=5.6 Hz, 2H), 3.80 (s, 3H), 3.92 (s, 2H), 4.14 (s, 2H), 6.32 (s, 1H), 6.43 (s, 1H), 7.11 (d, J=5.2 Hz, 1H), 7.16-7.20 (m, 3H), 7.27-7.31 (m, 1H), 7.46 (d, J=8.0 Hz, 1H), 7.77-7.82 (m, 1H), 8.18 (d, J=5.6 Hz, 1H), 8.50 (d, J=4.0 Hz, 1H). MS (ESI$^+$) m/z 501.3 (M+H)$^+$.

EXAMPLE 615

4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide

EXAMPLE 615A 4-nitrophenyl 4-(4-(5-fluoro-2-methoxyphenyl)-1H-pyrrolo[2,3-b]pyridin-2-yl)-5,6-dihydropyridine-1(2H)-carboxylate In a 100 mL round-bottomed flask Example 87D (0.8 g, 2.02 mmol) was mixed with triethylamine (1.5 mL, 10.76 mmol) in N,N-dimethylformamide (20 mL) to give a suspension. The mixture was cooled to 0° C. 4-Nitrophenyl carbonochloridate (0.45 g, 2.23 mmol) was added. The mixture stirred at room temperature for 2 hours. Water was added to the suspension. The solid product was filtered, washed with water and dried by vacuum. The crude title compound was used directly in the next step. MS (ESI$^+$) m/z 489.2 (M+H)$^+$.

EXAMPLE 615B

4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide In a 20 mL vial Example 615A (0.102 g, 0.209 mmol) was mixed with triethylamine (0.25 mL, 1.794 mmol) in N,N-dimethylformamide (2 mL) to give a solution. 4-Amino-2-methylbutan-2-ol (0.103 g, 0.998 mmol) was added. The mixture was stirred at room temperature overnight. The crude product was purified by preparative reverse phase column (Analogix, C-18, 80 g) with gradient elution from 20-100% acetonitrile in water with 0.1% trifluoroacetic acid to afford the title compound as trifluoroacetate salt. $^1$H NMR (400 MHz, DMSO-d$_6$): δ 1.06-1.13 (m, 6 H) 1.51-1.57 (m, 2 H) 2.40-2.46 (m, 2 H) 3.13 (t, J=7.93 Hz, 2 H) 3.49 (t, J=5.49 Hz, 2 H) 3.74 (s, 3 H) 3.98-4.02 (m, 2 H) 6.28 (d, J=1.83 Hz, 1 H) 6.44 (s, 1 H) 6.52 (s, 1 H) 7.08 (d, J=5.19 Hz, 1 H) 7.18-7.32 (m, 3 H) 8.22 (d, J=5.19 Hz, 1 H) 11.94 (s, 1 H). MS (ESI$^+$) m/z 453.1 (M+H)$^+$.

The following two examples were prepared essentially as described in Example 576, substituting the appropriate amine for Example 87D.

EXAMPLE 616

1-{5-[4-(5-fluoro-2-methoxyphenyl)-1H-pyrrolo[2,3-b]pyridin-2-yl]-3,6-dihydropyridin-1(2H)-yl}-2-methylpropan-2-ol $^1$H NMR (500 MHz, pyridine-d$_5$) δ ppm 1.45 (s, 6H), 2.50-2.56 (m, 2H), 2.87 (s, 2H), 3.17 (t, J=5.7 Hz, 2H), 3.68 (s, 3H), 4.11 (s, 2H), 6.67 (s, 1H), 6.83-6.84 (m, 1H), 7.05 (dd, J=9.0, 4.5 Hz, 1H), 7.22-7.26 (m, 1H), 7.29 (d, J=4.9 Hz, 1H), 7.45 (dd, J=8.8, 3.2 Hz, 1H), 8.58 (d, J=4.9 Hz, 1H), 13.06 (bs, 1H). MS (ESI$^+$) m/z 396.1 (M+H)$^+$.

EXAMPLE 633

1-{4-[4-(2,3-difluorophenyl)-1H-pyrrolo[2,3-b]pyridin-2-yl]-3,6-dihydropyridin-1(2H)-yl}-2-methylpropan-2-ol $^1$H NMR (400 MHz, pyridine-d$_5$) δ ppm 1.50 (s, 6H), 2.89 (d, J=6.0 Hz, 2H), 3.07 (bs, 2H), 3.48 (t, J=6.0 Hz, 2H), 4.09

(d, J=3.5 Hz, 2H), 6.72 (bs, 2H), 7.28 (dd, J=9.8, 6.0 Hz, 2H), 7.38 (ddd, J=10.8, 9.1, 7.4 Hz, 1H), 7.50 (dd, J=7.9, 6.1 Hz, 1H), 8.59 (d, J=4.9 Hz, 1H), 13.20 (s, 1H). MS (ESI$^+$) m/z 384.0 (M+H)$^+$.

EXAMPLE 620

4-[4-(5-fluoro-2-methoxyphenyl)-1H-pyrrolo[2,3-b]pyridin-2-yl]-N,N-dimethyl-3,6-dihydropyridine-1(2H)-sulfonamide To a suspension of Example 87D (60 mg, 0.151 mmol) in methylene chloride (5 mL) was added triethylamine (0.063 mL, 0.454 mmol) and dimethylsulfamoyl chloride (33 mg, 0.227 mmol). The mixture was stirred at room temperature overnight and was directly purified by flash chromatography (0-15% $CH_3OH$ in $CH_2Cl_2$) to provide the title compound. $^1H$ NMR (400 MHz, DMSO-$d_6$): δ2.54-2.58 (m, 3 H), 2.77 (s, 6 H), 3.41 (t, J=5.65 Hz, 1H), 3.74 (s, 3 H), 3.92 (d, J=2.44 Hz, 2 H), 6.27 (d, J=1.83 Hz, 1 H), 6.52 (s, 1 H), 7.04 (d, J=4.88 Hz, 1 H), 7.16-7.29 (m, 3 H), 8.21 (d, J=4.88 Hz, 1 H), 11.87 (s, 1 H); MS (DCI/NH$_3$) m/z 431 (M+H)$^+$.

EXAMPLE 621

3-bromo-4-(5-fluoro-2-methoxyphenyl)-2-(1,2,3,6-tetrahydropyridin-4-yl)-1H-pyrrolo[2,3-b]pyridine To a suspension of Example 87D (50 mg, 0.155 mmol) in acetonitrile (5 mL) was added N-bromosuccinimide (31 mg, 0.170 mmol). The solution was stirred at room temperature overnight.

Volatiles were removed, and the residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1H$ NMR (400 MHz, CD$_3$OD): δ2.95-2.99 (m, 2 H), 3.49 (t, J=6.10 Hz, 2 H), 3.70 (s, 3 H), 3.93 (d, J=2.75 Hz, 2 H), 6.46 (s, 1 H), 6.98-7.06 (m, 3 H), 7.14-7.20 (m, 1 H), 8.31 (d, J=4.88 Hz, 1 H); MS (DCI/NH$_3$) m/z 402, 404 (M+H)$^+$.

EXAMPLE 622

4-(2,4-dimethoxyphenyl)-2-(1,2,3,6-tetrahydropyridin-4-yl)-1H-pyrrolo[2,3-b]pyridine The title compound was prepared as described in Example 87, substituting 2,4-di-methoxyphenylboronic acid for 5-fluoro-2-methoxyphenylboronic acid in Example 87A. $^1H$ NMR (400 MHz, DMSO-$d_6$) δ 2.64-2.78 (m, 2H), 3.34 (p, J=6.9, 6.2 Hz, 2H), 3.76 (s, 3H), 3.85 (s, 5H), 6.36 (s, 1H), 6.48 (d, J=3.8 Hz, 1H), 6.68 (dd, J=8.6, 2.8 Hz, 1H), 6.75 (s, 1H), 7.06 (d, J=5.0 Hz, 1H), 7.35 (d, J=8.4 Hz, 1H), 8.21 (d, J=5.1 Hz, 1H), 8.91 (s, 2H), 12.00 (s, 1H). MS (ESI$^+$) m/z 336 (M+H)$^+$.

EXAMPLE 625

4-[4-(5-fluoro-2-methoxyphenyl)-1H-pyrrolo[2,3-b]pyridin-2-yl]-N-[(3-hydroxyoxetan-3-yl)methyl]-3,6-dihydropyridine-1(2H)-carboxamide In a 5 mL vial was mixed Example 615A (0.072 g, 0.147 mmol) with N-ethyl-N-isopropylpropan-2-amine (0.25 g, 1.934 mmol) in N,N-dimethylformamide (2 mL). 3-(aminomethyl)oxetan-3-ol (0.11 g, 1.067 mmol) was added. The mixture was stirred and heated at 70° C. for over night. The crude product was purified by preparative reverse phase column (Analogix, C-18, 150 g) with gradient elution from 20-100% acetonitrile in water with 0.1% trifluoroacetic acid to afford the title compound as trifluoroacetate salt. $^1H$ NMR (400 MHz, DMSO-$d_6$): δ 2.59-2.69 (m, 2 H) 3.14-3.21 (m, 1 H) 3.44 (s, 3 H) 3.73 (s, 4 H) 4.19-4.25 (m, 2 H) 4.29-4.35 (m, 1 H) 4.47 (d, J=10.99 Hz, 1 H) 6.34 (d, J=1.83 Hz, 1 H) 6.52 (s, 1 H) 7.06 (d, J=4.88 Hz, 1 H) 7.16-7.32 (m, 3 H) 8.23 (d, J=4.88 Hz, 1 H) 9.38 (s, 1 H) 11.93 (s, 1 H). MS (ESI$^+$) m/z 453.1 (M+H)$^+$.

EXAMPLE 626 methyl {4-[4-(5-fluoro-2-methoxyphenyl)-1H-pyrrolo[2,3-b]pyridin-2-yl]-3,6-dihydropyridin-1(2H)-yl}acetate The title compound was prepared essentially as described in Example 224 substituting methyl 2-bromoacetate for 2-chloro-N,N-dimethylacetamide. $^1H$ NMR (400 MHz, CD$_3$OD) δ ppm 2.93-3.04 (m, 2H), 3.58-3.76 (m, 2H), 3.80 (s, 3H), 3.88 (s, 3H), 4.09-4.26 (m, 2H), 4.30 (s, 2H), 6.43-6.54 (m, 1H), 6.64 (s, 1H), 7.15-7.33 (m, 3H), 7.39 (d, J=5.7 Hz, 1H), 8.32 (d, J=5.7 Hz, 1H). MS (ESI$^+$) m/z 396.1 (M+H)$^+$.

EXAMPLE 627

4-(4,5-difluoro-2-methoxyphenyl)-2-(1,2,3,6-tetrahydropyridin-4-yl)-1H-pyrrolo[2,3-b]pyridine The title compound was prepared as described in Example 87, substituting 4,5-difluoro-2-methoxyphenylboronic acid for 5-fluoro-2-methoxyphenylboronic acid in Example 87A. $^1H$ NMR (400 MHz, Methanol-$d_4$) δ 2.86-2.92 (m, 2H), 3.50 (t, J=6.1 Hz, 2H), 3.84 (s, 3H), 3.96-4.02 (m, 2H), 6.62-6.68 (m, 1H), 6.80 (s, 1H), 7.28 (dd, J=12.3, 6.6 Hz, 1H), 7.54 (dd, J=10.5, 8.7 Hz, 1H), 7.62 (d, J=6.2 Hz, 2H), 8.37 (d, J=6.2 Hz, 1H); MS (DCI$^+$) m/z 342 (M+H)$^+$.

EXAMPLE 628

4-[2-methoxy-4-(1H-pyrazol-1-yl)phenyl]-2-(1,2,3,6-tetrahydropyridin-4-yl)-1H-pyrrolo[2,3-b]pyridine The title compound was prepared as described in Example 87, substituting (2-methoxy-4-(1H-pyrazol-1-yl)phenyl)boronic acid for 5-fluoro-2-methoxyphenylboronic acid in Example 87A. $^1H$ NMR (400 MHz, DMSO-$d_6$) δ 2.67-2.74 (m, 2H), 3.30-3.37 (m, 2H), 3.79-3.82 (m, 2H), 3.87 (s, 3H), 6.40 (d, J=2.0 Hz, 1H), 6.50 (bs, 1H), 6.58-6.63 (m, 1H), 7.12 (d, J=5.0 Hz, 1H), 7.52 (d, J=8.2 Hz, 1H), 7.58 (dd, J=8.2, 2.0 Hz, 1H), 7.66 (d, J=2.0 Hz, 1H), 7.78-7.83 (m, 1H), 8.26 (d, J=5.0 Hz, 1H), 8.62-8.67 (m, 1H), 8.90 (bs, 2H), 11.99-12.04 (m, 1H); MS (ESI$^+$) m/z 372 (M+H)$^+$.

EXAMPLE 629

4-(2,6-dimethoxyphenyl)-2-(1,2,3,6-tetrahydropyridin-4-yl)-1H-pyrrolo[2,3-b]pyridine The title compound was prepared as described in Example 87, substituting (2,6-dimethoxyphenyl)boronic acid for 5-fluoro-2-methoxyphenylboronic acid in Example 87A. $^1H$ NMR (400 MHz, DMSO-$d_6$) δ 2.64 (d, J=6.6 Hz, 2H), 3.30 (hours, J=4.6, 3.9 Hz, 2H), 3.64 (s, 6H), 3.81 (d, J=5.0 Hz, 2H), 6.09 (d, J=2.1 Hz, 1H), 6.46 (t, J=3.4 Hz, 1H), 6.77-6.84 (m, 2H), 6.90 (d, J=5.0 Hz, 1H), 7.40 (t, J=8.4 Hz, 1H), 8.20 (d, J=5.0 Hz, 1H), 8.88 (d, J=7.0 Hz, 2H), 11.90 (s, 1H). MS (ESI$^+$) m/z 336 (M+H)$^+$.

EXAMPLE 630

4-(2-methoxyphenyl)-2-(1,2,3,6-tetrahydropyridin-4-yl)-1H-pyrrolo[2,3-b]pyridine The title compound was prepared as described in Example 87, substituting 2-methoxyphenylboronic acid for 5-fluoro-2-methoxyphenylboronic acid in Example 87A. $^1$H NMR (400 MHz, D$_2$O) δ 2.5-2.6 (m, 2H), 3.34-3.5 (m, 2H), 3.6 (s, 3H), 3.8-4.0 (m, 2H), 6.39 (d, J=43.9 Hz, 2H), 6.85-7.72 (m, 5H), 8.06 (d, J=6.2 Hz, 1H). MS (ESI$^+$) m/z 306 (M+H)$^+$.

EXAMPLE 631

4-(2-chloro-5-methoxyphenyl)-2-(1,2,3,6-tetrahydropyridin-4-yl)-1H-pyrrolo[2,3-b]pyridine The title compound was prepared as described in Example 87, substituting (2-chloro-5-methoxyphenyl)boronic acid for 5-fluoro-2-methoxyphenylboronic acid in Example 87A. $^1$H NMR (400 MHz, DMSO-d$_6$) δ 2.7-2.8 (m, 2H), 3.27-3.37 (m, 2H), 3.81 (s, 5H), 6.32 (d, J=2.0 Hz, 1H), 6.51 (t, J=3.7 Hz, 1H), 7.03-7.12 (m, 3H), 7.54 (d, J=8.8 Hz, 1H), 8.30 (d, J=4.9 Hz, 1H), 8.98 (s, 2H), 12.12 (d, J=2.5 Hz, 1H). MS (ESI$^+$) m/z 340 (M+H)$^+$.

EXAMPLE 632

4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile

EXAMPLE 632A

4-(5-fluoro-2-methoxyphenyl)-2-(1-(methylsulfonyl)-1,2,3,6-tetrahydropyridin-4-yl)-1-tosyl-1H-pyrrolo[2,3-b]pyridine-5-carbonitrile Example 236C (100 mg, 0.183 mmol), 1-(methylsulfonyl)-4-(4,4,5,5-tetramethyl-1,3,2-dioxaborolan-2-yl)-1,2,3,6-tetrahydropyridine (63.0 mg, 0.219 mmol) and sodium hydrogencarbonate (46.0 mg, 0.548 mmol) in 4 mL N,N-dimethylformamide and 1 mL water were degassed with nitrogen. Pd(1,1'-bis(diphenylphosphino)ferrocene)$_2$Cl$_2$ (13.37 mg, 0.018 mmol) was added. The reaction was stirred at 70° C. for 3 hours, diluted with water, and extracted with ethyl acetate. The organic phase was washed with brine, dried over magnesium sulfate and filtered. The filtrate was concentrated to dryness and the residue was purified by column chromatography (eluting with 0-30% ethyl acetate/heptane using Analogix purification system) to provide the title compound. MS (ESI$^+$) m/z 581 (M+H)$^+$.

EXAMPLE 632B

4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile To Example 632A (70 mg, 0.121 mmol) in 3 mL tetrahydrofuran and 1 mL methanol was added 1M aqueous sodium hydroxide (482 µl, 0.482 mmol). The reaction mixture was stirred at room temperature overnight, neutralized with 1N aqueous HCl to pH 5-6 and extracted with dichloromethane. The organic phase was washed with brine, dried with magnesium sulfate and filtered. The filtrate was concentrated to dryness. The residue was purified by column chromatography eluting with 0-10% methanol in dichloromethane using Analogix purification system to afford the title compound. $^1$H NMR (400 MHz, DMSO-d$_6$) δ 2.57-2.64 (m, 2H), 2.94 (s, 3H), 3.3-3.5 (m, 2H), 3.76 (s, 3H), 3.86-4.07 (m, 2H), 6.34 (s, 1H), 6.62 (bs, 1H), 7.24-7.34 (m, 2H), 7.39 (td, J=8.6, 3.2 Hz, 1H), 8.62 (s, 1H), 12.54 (bs, 1H). MS (ESI$^+$) m/z 427 (M+H)$^+$.

EXAMPLE 636

4-(5-fluoro-2-methoxyphenyl)-2-(1,2,3,6-tetrahydropyridin-4-yl)-1H-pyrrolo[2,3-b]pyridine-5-carbonitrile The title compound was prepared in Example 236F. $^1$H NMR (500 MHz, DMSO-d$_6$) δ 2.61-2.79 (m, 2H), 3.3-3.5 (m, 2H), 3.71-3.87 (m, 3H), 3.86-4.07 (m, 2H), 6.49 (d, J=74.6 Hz, 2H), 7.34 (d, J=50.7 Hz, 3H), 8.64 (s, 1H), 8.98 (s, 2H), 12.64 (s, 1H). MS (ESI$^+$) m/z 349 (M+H)$^+$.

EXAMPLE 637

5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one

EXAMPLE 637A

3-(chloromethyl)-1H-1,2,4-triazol-5(4H)-one

A mixture of semicarbazide hydrochloride (5 g, 44.8 mmol) and 2-chloro-1,1,1-trimethoxyethane (13.29 ml, 99 mmol) in methanol (50 ml) was stirred at room temperature for 3 days at which time the reaction became a homogenous solution. Additional 2-chloro-1,1,1-trimethoxyethane (4.3 ml, 32.3 mmol) was added and the reaction was stirred for 3 days longer. The reaction mixture was concentrated and the residue was partitioned in ethyl acetate (500 mL) and 1N aqueous HCl (75 mL). The organic layer was washed with additional 1N aqueous HCl (2×75 mL). The combined aqueous layers were back-extracted with additional ethyl acetate (5×100 mL). The organic extracts were combined, dried over anhydrous sodium sulfate, filtered, and concentrated to afford the title compound. MS (DCI$^+$) m/z 150.9 (M+NH$_4$)$^+$.

EXAMPLE 637B

5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one A mixture of Example 87D (0.05 g, 0.126 mmol) and N-ethyl-N-isopropylpropan-2-amine (0.132 ml, 0.757 mmol) in N,N-dimethylformamide (1 mL) was treated with Example 637A (0.020 g, 0.151 mmol) and the reaction was stirred at room temperature for 3 hours. Additional N-ethyl-N-isopropylpropan-2-amine (0.05 mL) and additional Example 637A (0.010 g, 0.076 mmol) were added and the mixture was stirred 3 hours longer. The reaction mixture was directly purified by reverse phase HPLC on a Phenomenex Luna C8(2) 5 um 100 Å AXIA column (30 mm×75 mm)

eluting with a gradient of 10-70% acetonitrile in 0.1% ammonium acetate/water to afford the title compound. ¹H NMR (500 MHz, DMSO-d₆) δ ppm 2.44-2.52 (m, 2H), 2.64 (t, J=5.8 Hz, 2H), 3.14 (q, J=2.7 Hz, 2H), 3.40 (s, 2H), 3.73 (s, 3H), 6.19 (d, J=2.1 Hz, 1H), 6.44-6.51 (m, 1H), 7.02 (d, J=4.9 Hz, 1H), 7.14-7.32 (m, 3H), 8.18 (d, J=4.9 Hz, 1H), 11.24 (s, 1H), 11.30-11.39 (m, 1H), 11.77 (d, J=2.2 Hz, 1H). MS (ESI⁺) m/z 421.1 (M+H)⁺.

EXAMPLE 638

2-{4-[4-(5-fluoro-2-methoxyphenyl)-1H-pyrrolo[2,3-b]pyridin-2-yl]-3,6-dihydropyridin-1(2H)-yl}-N-methylacetamide The title compound was prepared essentially as described in Example 224 substituting 2-bromo-N-methylacetamide for 2-chloro-N,N-dimethylacetamide. ¹H NMR (500 MHz, CD₃OD) δ ppm 2.83 (s, 3H), 2.92-3.01 (m, 2H), 3.51-3.73 (m, 2H), 3.80 (s, 3H), 4.06 (s, 2H), 4.08-4.17 (m, 2H), 6.47-6.51 (m, 1H), 6.64 (s, 1H), 7.16-7.32 (m, 3H), 7.41 (d, J=5.7 Hz, 1H), 8.32 (d, J=5.7 Hz, 1H). MS (ESI⁺) m/z 395.0 (M+H)⁺.

EXAMPLE 639 ethyl ({4-[3-bromo-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 603, substituting Example 621 for Example 602. ¹H NMR (400 MHz, DMSO-d₆): δ1.19 (t, J=7.02 Hz, 3 H), 2.67-2.72 (m, 2 H), 3.47 (t, J=5.65 Hz, 2 H), 3.66 (s, 3 H), 4.00 (d, J=2.75 Hz, 2 H), 4.10 (q, J=7.12 Hz, 2 H), 6.38 (s, 1 H), 6.93 (d, J=4.88 Hz, 1 H), 7.05-7.09 (m, 1 H), 7.22-7.28 (m, 1 H), 8.27 (d, J=4.58 Hz, 1 H), 11.40 (s, 1 H), 12.18 (s, 1 H); MS (DCI/NH₃) m/z 553, 555 (M+H)⁺.

EXAMPLE 640

4-(5-fluoro-2-methoxyphenyl)-5-methyl-2-[1-(methylsulfonyl)-1,2,3,6-tetrahydropyridin-4-yl]-1H-pyrrolo[2,3-b]pyridine To a solution of Example 641 as trifluoroacetic acid salt (53 mg, 0.094 mmol) in methylene chloride (5 mL) was added triethylamine (0.078 mL, 0.563 mmol) and methanesulfonyl chloride (16 mg, 0.141 mmol). The solution was stirred at room temperature overnight. Methanol (0.5 mL) was added and the solution was directly separated by flash chromatography (0-15% CH₃OH in CH₂Cl₂) to provide the title compound. ¹H NMR (500 MHz, DMSO-d₆): δ 2.09 (s, 3 H), 2.53-2.57 (m, 4 H), 2.92 (s, 3 H), 3.68 (s, 2 H), 3.89 (d, J=2.75 Hz, 2 H), 5.97 (d, J=2.14 Hz, 1 H), 6.48 (s, 1 H), 7.06 (dd, J=8.70, 3.20 Hz, 1 H), 7.18 (dd, J=9.16, 4.58 Hz, 1 H), 7.24-7.29 (m, 1 H), 8.10 (s, 1 H), 11.72 (s, 1 H); MS (DCI/NH₃) m/z 416 (M+H)⁺.

EXAMPLE 641

4-(5-fluoro-2-methoxyphenyl)-5-methyl-2-(1,2,3,6-tetrahydropyridin-4-yl)-1H-pyrrolo[2,3-b]pyridine

EXAMPLE 641A 4-chloro-5-methyl-1-tosyl-1H-pyrrolo[2,3-b]pyridine

To an ambient suspension of 4-chloro-5-methyl-1H-pyrrolo[2,3-b]pyridine (200 mg, 1.2 mmol) in toluene (3 mL) and tetrabutylammonium sulfate (0.05 mL, 50% wgt solution in water) was added a solution of NaOH in water (0.216 g NaOH in 1.5 mL H₂O) and p-toluenesulfonyl chloride (0.275 g, 1.441 mmol). The biphasic reaction was stirred vigorously for 16 hours, and was then partitioned between ethyl acetate and water. The layers were separated, and the aqueous was extracted with additional ethyl acetate. The combined organics were dried over anhydrous Na₂SO₄, filtered and concentrated under reduced pressure to provide the title compound. MS (DCI/NH₃) m/z 321 (M+H)⁺.

EXAMPLE 641B 4-chloro-2-iodo-5-methyl-1-tosyl-1H-pyrrolo[2,3-b]pyridine

To a cold (−78° C.) solution of Example 641A (0.5 g, 1.559 mmol) in tetrahydrofuran (15 mL) was added lithium diisopropylamide (2 M solution in tetrahydrofuran, 1.559 mL, 3.12 mmol). The reaction mixture was stirred at −78° C. for 1 hour, after which a solution of I₂ (0.791 g, 3.12 mmol) in tetrahydrofuran (5 mL) was added. The reaction mixture was stirred at room temperature for 1 hour, and the reaction was quenched by adding 1 M aqueous solution of Na₂S₂O₃. After warming to room temperature, the mixture was partitioned between ethyl acetate and brine. Insoluble solid was collected by filtration, and washed with ethyl acetate to provide the title compound. The organic layer was concentrated, and the residue was stirred with 10 mL of CH₂Cl₂. The solution was loaded onto flash chromatography that eluted with 10-60% ethyl acetate in hexane to provide additional title compound. MS (DCI/NH₃) m/z 447 (M+H)⁺.

EXAMPLE 641C tert-butyl 4-(4-chloro-5-methyl-1-tosyl-1H-pyrrolo[2,3-b]pyridin-2-yl)-5,6-dihydropyridine-1(2H)-carboxylate A mixture of Example 641B (240 mg, 0.537 mmol), tert-butyl 4-(4,4,5,5-tetramethyl-1,3,2-dioxaborolan-2-yl)-5,6-dihydropyridine-1(2H)-carboxylate (199 mg, 0.645 mmol), and tetrakis(triphenylphosphine)palladium(0) (31 mg, 0.027 mmol) was purged with nitrogen. N,N-dimethylformamide (10 mL) and saturated sodium bicarbonate solution (2.5 mL) were added. The mixture was purged with nitrogen again, and heated at 85° C. overnight. After cooling, the mixture was partitioned between ethyl acetate and brine. The organic phase was washed with brine, and concentrated. The residue was separated by flash chromatography (15-60% ethyl acetate in hexane) to provide the title compound. MS (DCI/NH₃) m/z 502 (M+H)⁺.

EXAMPLE 641D tert-butyl 4-(4-(5-fluoro-2-methoxyphenyl)-5-methyl-1-tosyl-1H-pyrrolo[2,3-b]pyridin-2-yl)-5,6-dihydropyridine-1(2H)-carboxylate A mixture of tert-butyl 4-(4-chloro-5-methyl-1-tosyl-1H-pyrrolo[2,3-b]pyridin-2-yl)-5,6-dihydropyridine-1(2H)-carboxylate (220 mg, 0.438 mmol), 5-fluoro-2-methoxyphenylboronic acid (112 mg, 0.657 mmol), phenylallylchloro[1,3-bis(diisopropylphenyl)-2-imidazol-2-ylidene]palladium (II) (Stem, 9 mg, 0.013 mmol) and potassium phosphate (279 mg, 1.315 mmol) was suspended in a mixture of tetrahydrofuran (7.5 mL) and water (2.5 mL). The suspension was purged with nitrogen, and heated at 60° C. for 4 hours. After cooling, the reaction mixture was partitioned between ethyl acetate and brine. The organic phase was washed with brine, and concentrated. The residue was separated by flash chromatography (10-70% ethyl acetate in hexane) to provide the title compound. MS (DCI/NH$_3$) m/z 592 (M+H)$^+$.

EXAMPLE 641E 4-(5-fluoro-2-methoxyphenyl)-5-methyl-2-(1,2,3,6-tetrahydropyridin-4-yl)-1H-pyrrolo[2,3-b]pyridine To a solution of Example 641D (250 mg, 0.423 mmol) in dioxane (9 mL) was added NaOH (50% solution in water, 169 mg, 2.113 mmol) in 3 mL of water. The mixture was heated at 90° C. for 4 hours. After cooling, the mixture was partitioned between ethyl acetate and brine. The organic phase was washed with water and concentrated. The residue was dissolved in methylene chloride (5 mL) and was treated with 1 mL of trifluoroacetic acid at room temperature for 0.5 hours. The volatiles were removed and the residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (500 MHz, CD$_3$OD): δ2.25 (s, 3 H), 2.78-2.81 (m, 2 H), 3.46 (t, J=6.10 Hz, 2 H), 3.75 (s, 3 H), 3.94 (d, J=2.75 Hz, 2 H), 6.37 (s, 1 H), 6.51 (s, 1 H), 7.06 (dd, J=8.24, 3.05 Hz, 1 H), 7.20-7.23 (m, 1 H), 7.26-7.31 (m, 1 H), 8.25 (s, 1 H); MS (DCI/NH$_3$) m/z 338 (M+H)$^+$.

EXAMPLE 642

N-[{4-[4-(5-fluoro-2-methoxyphenyl)-1H-pyrrolo[2, 3-b]pyridin-2-yl]-3,6-dihydropyridin-1(2H)-yl}(methyl)oxido-λ$^6$-sulfanylidene]-4-methylbenzenesulfonamide To a solution of Example 87D (200 mg, 0.618 mmol) in CH$_2$Cl$_2$ (20 mL) was added triethylamine (0.259 mL, 0.188 mmol) and N-tosylmethanesulfonimidoyl chloride (331 mg, 1.237 mmol) at room temperature. The mixture was heated at 50° C. overnight. After cooling, the precipitate was collected by filtration, washed with methylene chloride, and dried with magnesium sulfate to provide the title compound. $^1$H NMR (500 MHz, DMSO-d$_6$): δ 2.31 (s, 3 H), 2.52-2.55 (m, 2 H), 3.28 (s, 3 H), 3.35-3.47 (m, 2 H), 3.75 (s, 3 H), 3.89-3.99 (m, 2 H), 6.27 (d, J=1.83 Hz, 1 H), 6.48 (s, 1 H), 7.05 (d, J=4.88 Hz, 1 H), 7.19-7.34 (m, 5 H), 7.71 (d, J=8.24 Hz, 2 H), 8.22 (d, J=4.88 Hz, 1 H), 11.88 (d, J=1.53 Hz, 1 H); MS (DCI/NH$_3$) m/z 555 (M+H)$^+$.

EXAMPLE 643

4-(2-ethoxy-5-fluorophenyl)-2-(1,2,3,6-tetrahydropyridin-4-yl)-1H-pyrrolo[2,3-b]pyridine The title compound was prepared as described in Example 87, substituting 5-fluoro-2-ethoxyphenylboronic acid for 5-fluoro-2-methoxyphenylboronic acid in Example 87A. $^1$H NMR (500 MHz, DMSO-d$_6$) δ 1.17 (t, J=6.9 Hz, 3H), 2.71 (d, J=6.1 Hz, 2H), 3.34 (q, J=6.7 Hz, 2H), 3.88 (d, J=17.1 Hz, 2H), 4.05 (q, J=6.9 Hz, 2H), 6.40 (s, 1H), 6.50 (s, 1H), 7.10 (d, J=5.0 Hz, 1H), 7.16-7.33 (m, 3H), 8.26 (d, J=5.0 Hz, 1H), 8.93 (s, 2H), 12.02 (s, 1H). MS (ESI$^+$) m/z 338 (M+H)$^+$.

EXAMPLE 644

4-(2,5-dimethoxyphenyl)-2-(1,2,3,6-tetrahydropyridin-4-yl)-1H-pyrrolo[2,3-b]pyridine The title compound was prepared as described in Example 87, substituting 2,5-di-methoxyphenylboronic acid for 5-fluoro-2-methoxyphenylboronic acid in Example 87A. $^1$H NMR (500 MHz, DMSO-d$_6$) δ 2.60-2.8 (m, 2H), 3.33 (q, J=6.6 Hz, 2H), 3.69 (s, 3H), 3.76 (s, 3H), 3.83 (dd, J=5.5, 3.0 Hz, 2H), 6.35 (d, J=2.0 Hz, 1H), 6.49 (t, J=3.5 Hz, 1H), 6.95 (d, J=3.1 Hz, 1H), 7.02 (dd, J=9.0, 3.1 Hz, 1H), 7.07 (d, J=4.9 Hz, 1H), 7.13 (d, J=9.0 Hz, 1H), 8.24 (d, J=4.9 Hz, 1H), 8.87 (d, J=7.0 Hz, 2H), 11.98 (d, J=2.3 Hz, 1H). MS (ESI$^+$) m/z 336 (M+H)$^+$.

EXAMPLE 646

4-{4-[4-(5-fluoro-2-methoxyphenyl)-1H-pyrrolo[2, 3-b]pyridin-2-yl]-3,6-dihydropyridin-1(2H)-yl}cyclohexanol The title compound was prepared using the procedure described in Example 149, using Example 87D in place of Example 135B and 4-hydroxycyclohexanone in place of 2,3-dihydroxypropanal. $^1$H NMR (500 MHz, DMSO-d$_6$): δ 1.41-1.53 (m, 2 H) 1.74-1.90 (m, 5 H) 2.72-2.93 (m, 2 H) 3.20-3.32 (m, 2 H) 3.63-3.71 (m, 1 H) 3.74 (s, 3 H) 3.81-3.86 (m, 2 H) 6.39 (d, J=1.53 Hz, 1 H) 6.51 (s, 1 H) 7.09 (d, J=5.19 Hz, 1 H) 7.18-7.33 (m, 3 H) 8.26 (d, J=4.88 Hz, 1 H) 9.59 (s, 1 H) 12.05 (s, 1 H). MS (ESI$^+$) m/z 422.0 (M+H)$^+$.

EXAMPLE 647

1-({4-[4-(5-fluoro-2-methoxyphenyl)-1H-pyrrolo[2, 3-b]pyridin-2-yl]-3,6-dihydropyridin-1(2H)-yl}carbonyl)piperidine-4-carboxylic acid

EXAMPLE 647A

Methyl 1-(4-(4-(5-fluoro-2-methoxyphenyl)-1H-pyrrolo[2,3-b]pyridin-2-yl)-1,2,3,6-tetrahydropyridine-1-carbonyl)piperidine-4-carboxylate The title compound was prepared using the procedure described in Example 625, using methyl piperidine-4-carboxylate (0.194 g, 1.36 mmol) in place of 3-(aminomethyl)oxetan-3-ol. MS (ESI$^+$) m/z 493.1 (M+H)$^+$.

EXAMPLE 647B 1-({4-[4-(5-fluoro-2-methoxyphenyl)-1H-pyrrolo[2, 3-b]pyridin-2-yl]-3,6-dihydropyridin-1(2H)-yl}carbonyl)piperidine-4-carboxylic acid In a 5 mL vial was mixed Example 647A (0.072 g, 0.146 mmol) and lithium hydroxide hydrate (0.02 g, 0.477 mmol) in tetrahydrofuran/methanol/water (2/2/1) (1 mL) to give a solution. The mixture stirred at room temperature overnight. The solvent was dried by vacuum and the crude product was purified by preparative reverse phase column (Analogix, C-18, 40 g) with gradient elution from 30-100% acetonitrile in water with 0.1% trifluoroacetic acid to afford the title compound as trifluoroacetate salt. $^1$H NMR (500 MHz, DMSO-d$_6$): δ 1.45-1.56 (m, 2 H) 1.76-1.84 (m, 2 H) 2.35-2.45 (m, 1 H) 2.77-2.86 (m, 2 H) 3.32-3.36 (m, 2 H) 3.74 (s, 3 H) 3.88-3.93 (m, 2 H) 6.26 (d, J=1.83 Hz, 1 H)

6.50 (s, 1 H) 7.06 (d, J=5.19 Hz, 1 H) 7.18-7.31 (m, 3 H) 8.21 (d, J=5.19 Hz, 1 H) 11.88 (s, 1 H). MS (ESI$^+$) m/z 479.1 (M+H)$^+$.

EXAMPLE 656

4-methoxy-3-[2-(1,2,3,6-tetrahydropyridin-4-yl)-1H-pyrrolo[2,3-b]pyridin-4-yl]benzonitrile The title compound was prepared as described in Example 87, substituting 2-cyano-5-fluorophenylboronic acid for 5-fluoro-2-methoxyphenylboronic acid in Example 87A. $^1$H NMR (400 MHz, DMSO-d$_6$) δ 2.70 (t, J=6.3 Hz, 2H), 3.33 (dt, J=7.9, 3.9 Hz, 2H), 3.85 (s, 5H), 6.36 (d, J=2.0 Hz, 1H), 6.49 (d, J=3.6 Hz, 1H), 7.08 (d, J=4.9 Hz, 1H), 7.39 (d, J=8.7 Hz, 1H), 7.81 (d, J=2.1 Hz, 1H), 7.95 (dd, J=8.6, 2.2 Hz, 1H), 8.26 (d, J=4.9 Hz, 1H), 8.94 (s, 2H), 12.02 (d, J=2.3 Hz, 1H). MS (ESI$^+$) m/z 331 (M+H)$^+$.

EXAMPLE 657

4-(2-chloro-5-fluorophenyl)-2-(1,2,3,6-tetrahydropyridin-4-yl)-1H-pyrrolo[2,3-b]pyridine The title compound was prepared as described in Example 87, substituting 2-chloro-5-fluorophenylboronic acid for 5-fluoro-2-methoxyphenylboronic acid in Example 87A. $^1$H NMR (400 MHz, DMSO-d$_6$) δ 2.70 (t, J=6.3 Hz, 2H), 3.32 (dq, J=7.7, 5.0 Hz, 2H), 3.83 (d, J=5.0 Hz, 2H), 6.33 (d, J=1.9 Hz, 1H), 6.51 (d, J=3.6 Hz, 1H), 7.07 (d, J=4.9 Hz, 1H), 7.34-7.44 (m, 2H), 7.66-7.75 (m, 1H), 8.32 (d, J=4.9 Hz, 1H), 8.96 (s, 2H), 12.15 (d, J=2.2 Hz, 1H). MS (ESI$^+$) m/z 328 (M+H)$^+$.

EXAMPLE 658

4-(4-fluoro-2-methoxyphenyl)-2-(1,2,3,6-tetrahydropyridin-4-yl)-1H-pyrrolo[2,3-b]pyridine The title compound was prepared as described in Example 87, substituting 4-fluoro-2-methoxyphenylboronic acid for 5-fluoro-2-methoxyphenylboronic acid in Example 87A. $^1$H NMR (400 MHz, D$_2$O) δ 2.70 (t, J=6.3 Hz, 2H), 3.41 (d, J=6.1 Hz, 2H), 3.62 (s, 3H), 3.88 (s, 2H), 6.36 (d, J=1.6 Hz, 1H), 6.38 (d, J=1.6 Hz, 1H), 6.68 (dt, J=8.6, 2.6 Hz, 1H), 6.79 (t, J=2.7 Hz, 1H), 7.25 (dt, J=6.6, 2.6 Hz, 1H), 7.35 (d, J=2.3 Hz, 1H), 8.07 (d, J=1.5 Hz, 1H). MS (ESI$^+$) m/z 324 (M+H)$^+$.

EXAMPLE 659

4-[2-(difluoromethoxy)-5-fluorophenyl]-2-(1,2,3,6-tetrahydropyridin-4-yl)-1H-pyrrolo[2,3-b]pyridine

EXAMPLE 659A tert-butyl 4-(4-(2-(difluoromethoxy)-5-fluorophenyl)-1-tosyl-1H-pyrrolo[2,3-b]pyridin-2-yl)-5,6-dihydropyridine-1(2H)-carboxylate Example 673A (300 mg, 0.518 mmol), 2-bromo-1-(difluoromethoxy)-4-fluorobenzene (125 mg, 0.518 mmol) and sodium hydrogencarbonate (130 mg, 1.553 mmol) in 10 mL N,N-dimethylformamide and 2 mL water were degassed with nitrogen. Pd(1,1'-bis(diphenylphosphino)ferrocene)$_2$Cl$_2$ (37.9 mg, 0.052 mmol) was added. The reaction was stirred at 70° C. for 3 hours. The reaction mixture was diluted with water and extracted with ethyl acetate. The organic solution was washed with water and brine, dried with magnesium sulfate, and filtered. The filtrate was concentrated to dryness. The residue was pre-absorbed on silica gel and purified by column chromatography eluting with 0-30% ethyl acetate in heptane using Analogix purification system to obtain the title compound. MS (ESI$^+$) m/z 614 (M+H)$^+$.

EXAMPLE 659B tert-butyl 4-(4-(2-(difluoromethoxy)-5-fluorophenyl)-1H-pyrrolo[2,3-b]pyridin-2-yl)-5,6-dihydropyridine-1(2H)-carboxylate The title compound was prepared as described in Example 236E, substituting 659A for Example 236D. MS (ESI$^+$) m/z 460 (M+H)$^+$.

EXAMPLE 659C 4-(2-(difluoromethoxy)-5-fluorophenyl)-2-(1,2,3,6-tetrahydropyridin-4-yl)-1H-pyrrolo[2,3-b]pyridine The title compound was prepared as described in Example 236F, substituting Example 659B for Example 236E. $^1$H NMR (400 MHz, DMSO-d$_6$) δ 2.71 (d, J=6.3 Hz, 2H), 3.33 (dt, J=8.6, 5.4 Hz, 2H), 3.80-3.90 (m, 2H), 6.42 (d, J=2.1 Hz, 1H), 6.51 (d, J=4.0 Hz, 1H), 6.99-7.27 (m, 2H), 7.36-7.61 (m, 3H), 8.30 (d, J=5.0 Hz, 1H), 8.95 (s, 2H), 12.11 (d, J=2.5 Hz, 1H). MS (ESI$^+$) m/z 360 (M+H)$^+$.

EXAMPLE 660

({4-[4-(5-fluoro-2-methoxyphenyl)-1H-pyrrolo[2,3-b]pyridin-2-yl]-3,6-dihydropyridin-1(2H)-yl}sulfonyl)acetic acid

EXAMPLE 660A 4-(5-fluoro-2-methoxyphenyl)-1-(phenylsulfonyl)-2-(1,2,3,6-tetrahydropyridin-4-yl)-1H-pyrrolo[2,3-b]pyridine A mixture of Example 87C (2 g, 3.55 mmol) in dichloromethane (32.3 ml) was treated with trifluoroacetic acid (3.01 ml, 39.0 mmol) and the solution was stirred at room temperature for 16 hours. The reaction mixture was concentrated and the residue partitioned in 100 mL ethyl acetate and 30 mL saturated aqueous sodium bicarbonate. The aqueous layer was back-extracted with 30 mL additional ethyl acetate. The combined organic layers were washed with 25 mL brine, dried over anhydrous sodium sulfate, filtered, and concentrated to afford the title compound. MS (APCI$^+$) m/z 464.2 (M+H)$^+$.

EXAMPLE 660B 4-(5-fluoro-2-methoxyphenyl)-2-(1-(methylsulfonyl)-1,2,3,6-tetrahydropyridin-4-yl)-1-(phenylsulfonyl)-1H-pyrrolo[2,3-b]pyridine A solution of Example 660A (0.6 g, 1.294 mmol) and N-ethyl-N-isopropylpropan-2-amine (0.565 ml, 3.24 mmol) in tetrahydrofuran (10 ml) was treated with methanesulfonyl chloride (0.141 ml, 1.812 mmol) and the reaction mixture was stirred at room temperature for 3 hours. The reaction mixture was partitioned in 75 mL ethyl acetate and 30 mL saturated aqueous sodium bicarbonate. The organic layer was washed with 30 mL brine, dried over anhydrous sodium sulfate, filtered, and concentrated. The concentrate was purified by flash chromatography on silica gel (AnaLogix IntelliFlash 280 system) eluting with a gradient of from 5% to 65% ethyl acetate in heptanes to afford the title compound. MS (ESI$^+$) m/z 542.1 (M+H)$^+$.

EXAMPLE 660C tert-butyl 2-(4-(4-(5-fluoro-2-methoxyphenyl)-1-(phenylsulfonyl)-1H-pyrrolo[2,3-b]pyridin-2-yl)-5,6-dihydropyridin-1(2H)-ylsulfonyl)acetate A solution of Example 660B (0.43 g, 0.794 mmol) and di-tert-butyl dicarbonate (0.212 ml, 0.913 mmol) in tetrahydrofuran (4.41 ml) cooled to −78° C., was treated with lithium bis(trimethylsilyl)amide (1 M in tetrahydrofuran, 2.263 ml, 2.263 mmol) added dropwise over 5 minutes. The mixture was stirred at −78° C. for 40 minutes and then at 0° C. for 1.5 hours. The reaction mixture was recooled to −78° C. and saturated aqueous ammonium chloride (~3.5 mL) was added. The mixture was allowed to warm to room temperature and was partitioned in ethyl acetate and water. The organic layer was washed with saturated aqueous sodium bicarbonate and brine, dried over anhydrous sodium sulfate, filtered, and concentrated. The concentrate was purified by flash chromatography on silica gel (AnaLogix IntelliFlash 280 system) eluting with a gradient of from 0% to 3% methanol in dichloromethane to afford the title compound. MS (ESI$^+$) m/z 642.0 (M+H)$^+$.

EXAMPLE 660D ({4-[4-(5-fluoro-2-methoxyphenyl)-1H-pyrrolo[2,3-b]pyridin-2-yl]-3,6-dihydropyridin-1(2H)-yl}sulfonyl)acetic acid A mixture of Example 660C (0.285 g, 0.444 mmol), aqueous 3M sodium hydroxide (0.444 ml, 1.332 mmol), and water (1 ml) was stirred at room temperature for 1.5 hours and was then heated at 70° C. for 3 hours. The reaction mixture was concentrated. The residue was suspended in water (5 mL) and the mixture was neutralized to pH 4 with aqueous 3 N HCl. The resulting suspension was filtered and the solid collected was washed with water and dried under vacuum to provide the title compound. $^1$H NMR (400 MHz, DMSO-d$_6$) δ ppm 2.55-2.63 (m, 2H), 3.46 (t, J=5.7 Hz, 2H), 3.74 (s, 3H), 3.98-4.06 (m, 2H), 4.22 (s, 2H), 6.30 (d, J=2.0 Hz, 1H), 6.49-6.56 (m, 1H), 7.08 (d, J=5.0 Hz, 1H), 7.16-7.32 (m, 3H), 8.23 (d, J=5.0 Hz, 1H), 11.95 (d, J=2.3 Hz, 1H). MS (ESI$^+$) m/z 446.1 (M+H)$^+$.

EXAMPLE 661

4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine

EXAMPLE 661A 4-(5-fluoro-2-methoxyphenyl)-2-(1-(methylsulfonylmethylsulfonyl)-1,2,3,6-tetrahydropyridin-4-yl)-1-(phenylsulfonyl)-1H-pyrrolo[2,3-b]pyridine A 0° C. solution of Example 660A (0.06 g, 0.129 mmol) and N-ethyl-N-isopropylpropan-2-amine (0.034 ml, 0.194 mmol) in dichloromethane (1.2 mL) was treated with (methylsulfonyl)methanesulfonyl chloride (0.037 g, 0.194 mmol) added portionwise over 3 minutes. The mixture was allowed to stir at room temperature for 16 hours. The reaction mixture was diluted with dichloromethane (20 mL) and washed with saturated aqueous sodium bicarbonate (5 mL) and brine (5 mL). The organic layer was dried over anhydrous sodium sulfate, filtered, and concentrated. The concentrate was purified by flash chromatography on silica gel (AnaLogix IntelliFlash 280 system) eluting with a gradient of from 0% to 2% methanol in dichloromethane to afford the title compound. MS (APCI$^+$) m/z 620.2 (M+H)$^+$.

EXAMPLE 661B 4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine A mixture of Example 661A (0.073 g, 0.118 mmol) and aqueous 3N sodium hydroxide (0.118 ml, 0.353 mmol) in dioxane (0.8 ml), ethanol (0.8 ml) and water (0.4 mL) was heated at 75° C. for 2 hours. The reaction mixture was concentrated and the residue was partitioned in dichloromethane (30 mL) and water (10 mL). The organic layer was washed with brine (10 mL) and concentrated. The concentrate was purified by reverse phase HPLC on a Phenomenex Luna C8(2) 5 um 100 Å AXIA column (30 mm×75 mm) eluting with a gradient of 10-70% acetonitrile in 0.1% trifluoroacetic acid/water to afford the title compound as a trifluoroacetic acid salt. $^1$H NMR (400 MHz, DMSO-d$_6$) δ ppm 2.58-2.66 (m, 2H), 3.20 (s, 3H), 3.50 (t, J=5.7 Hz, 2H), 3.74 (s, 3H), 4.02-4.11 (m, 2H), 5.31 (s, 2H), 6.31 (d, J=2.0 Hz, 1H), 6.49-6.57 (m, 1H), 7.08 (d, J=5.0 Hz, 1H), 7.16-7.37 (m, 3H), 8.23 (d, J=5.0 Hz, 1H), 11.96 (d, J=2.3 Hz, 1H). MS (ESI$^+$) m/z 480.1 (M+H)$^+$.

EXAMPLE 662

5-chloro-4-(5-fluoro-2-methoxyphenyl)-2-(1,2,3,6-tetrahydropyridin-4-yl)-1H-pyrrolo[2,3-b]pyridine The title compound was prepared as described in Example 229F. $^1$H NMR (500 MHz, DMSO-d$_6$) δ ppm 2.19-2.32 (m, 2H), 2.86 (t, J=5.7 Hz, 2H), 3.37-3.46 (m, 2H), 3.70 (s, 3H), 5.97 (d, J=1.6 Hz, 1H), 6.51-6.58 (m, 1H), 7.14 (dd, J=8.6, 3.1 Hz, 1H), 7.20 (dd, J=9.1, 4.5 Hz, 1H), 7.31 (td, J=8.8, 3.2 Hz, 1H), 8.22 (s, 1H), 11.97 (s, 1H). MS (ESI$^+$) m/z 358.1 (M+H)$^+$.

EXAMPLE 663

4-(5-fluoro-2-methoxyphenyl)-2-{1-[(tetrahydrofuran-2-ylmethyl)sulfonyl]-1,2,3,6-tetrahydropyridin-4-yl}-1H-pyrrolo[2,3-b]pyridine The title compound was prepared essentially as described in Example 661, substituting (tetrahydrofuran-2-yl)methanesulfonyl chloride for (methylsulfonyl)methanesulfonyl chloride in Example 661A. $^1$H NMR (400 MHz, DMSO-d$_6$) δ ppm 1.56-1.74 (m, 1H), 1.74-1.95 (m, 2H), 1.95-2.14 (m, 1H), 2.53-2.65 (m, 2H), 3.22-3.37 (m, 2H), 3.42 (t, J=5.8 Hz, 2H), 3.58-3.83 (m, 5H), 3.86-4.08 (m, 2H), 4.08-4.25 (m, 1H), 6.27 (d, J=2.1 Hz, 1H), 6.48-6.55 (m, 1H), 7.04 (d, J=4.9 Hz, 1H), 7.12-7.34 (m, 3H), 8.21 (d, J=4.9 Hz, 1H), 11.85 (d, J=2.3 Hz, 1H). MS (ESI$^+$) m/z 472.1 (M+H)$^+$.

EXAMPLE 664 ethyl ({4-[4-(5-fluoro-2-methoxyphenyl)-5-methyl-1H-pyrrolo[2,3-b]pyridin-2-yl]-3,6-dihydropyridin-1(2H)-yl}sulfonyl)carbamate The title compound was prepared essentially as described in Example 603, substituting Example 641 for Example 602. $^1$H NMR (400 MHz, DMSO-$d_6$): δ1.07 (t, J=7.17 Hz, 1.5 H) 1.15 (t, J=7.02 Hz, 1.5 H), 2.09 (s, 3 H), 3.23 (s, 3 H), 3.43 (t, J=5.80 Hz, 2 H), 3.68 (s, 3 H), 3.82 (q, J=7.12 Hz, 1 H), 3.99 (d, J=2.44 Hz, 2 H), 4.06 (q, J=7.02 Hz, 1 H), 5.96 (d, J=2.14 Hz, 0.5 H), 6.45 (s, 0.5 H), 6.95-6.99 (m, 1 H), 7.03-7.06 (m, 0.5 H), 7.16-7.19 (m, 0.5 H), 7.24-7.30 (m, 0.5 H), 8.10 (s, 0.5 H), 8.45-8.49 (m, 1 H), 11.43-11.49 (m, 0.5 H), 11.71 (d, J=1.53 Hz, 0.5 H); MS (DCI/NH$_3$) m/z 488 (M+H)$^+$.

EXAMPLE 665

3-chloro-4-(5-fluoro-2-methoxyphenyl)-2-(1,2,3,6-tetrahydropyridin-4-yl)-1H-pyrrolo[2,3-b]pyridine

EXAMPLE 665A tert-butyl 4-(3-chloro-4-(5-fluoro-2-methoxyphenyl)-1H-pyrrolo[2,3-b]pyridin-2-yl)-5,6-dihydropyridine-1(2H)-carboxylate To a solution of Example 1066A (1 g, 2.36 mmol) in acetonitrile (100 mL) was added N-chlorosuccinimide (331 mg, 2.479 mmol). The reaction mixture was heated at 50° C. for 60 hours. The mixture was concentrated, and the residue was purified by flash chromatography (0-15% CH$_3$OH in CH$_2$Cl$_2$) to provide the title compound. MS (DCI/NH$_3$) m/z 458 (M+H)$^+$.

EXAMPLE 665B 3-chloro-4-(5-fluoro-2-methoxyphenyl)-2-(1,2,3,6-tetrahydropyridin-4-yl)-1H-pyrrolo[2,3-b]pyridine To a solution of Example 665A (1.36 g, 2.97 mmol) in methylene chloride (50 mL) was added trifluoroacetic acid (10 mL). The solution was stirred at room temperature for 1 hours. The volatiles were removed, and the residue was purified by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (400 MHz, DMSO-$d_6$): δ2.95-3.00 (m, 2 H), 3.49 (t, J=6.10 Hz, 2 H), 3.70 (s, 3 H), 3.93-3.95 (m, 2 H), 6.47-6.50 (m, 1 H), 7.00-7.06 (m, 3 H), 7.13-7.20 (m, 1 H), 8.31 (d, J=5.19 Hz, 1 H); MS (DCI/NH$_3$) m/z 358 (M+H)$^+$.

EXAMPLE 666 ethyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 603, substituting Example 665B for Example 602. $^1$H NMR (400 MHz, DMSO-$d_6$): δ1.18 (t, J=7.17 Hz, 3 H), 2.67-2.72 (m, 2 H), 3.48 (t, J=5.65 Hz, 2 H), 3.66 (s, 3 H), 4.02 (d, J=2.75 Hz, 2 H), 4.10 (q, J=7.02 Hz, 2 H), 6.43 (s, 1 H), 6.94 (d, J=4.88 Hz, 1 H), 7.08-7.11 (m, 2 H), 7.21-7.27 (m, 1 H), 8.28 (d, J=4.58 Hz, 1 H), 11.40 (s, 1 H), 12.08 (s, 1 H); MS (DCI/NH$_3$) m/z 509 (M+H)$^+$.

EXAMPLE 667

3-chloro-4-(5-fluoro-2-methoxyphenyl)-2-[1-(methylsulfonyl)-1,2,3,6-tetrahydropyridin-4-yl]-1H-pyrrolo[2,3-b]pyridine To a solution of Example 665B (100 mg, 0.171 mmol) in methylene chloride (6 mL) was added triethylamine (0.143 mL, 1.026 mmol) and methanesulfonyl chloride (30 mg, 0.256 mmol). The solution was stirred at room temperature overnight and was directly separated by flash chromatography (0-15% CH$_3$OH in CH$_2$Cl$_2$) to give title compound. $^1$H NMR (400 MHz, DMSO-$d_6$): δ2.71-2.74 (m, J=1.83 Hz, 2 H), 2.95 (s, 3 H), 3.38 (t, J=5.80 Hz, 2 H), 3.67 (s, 3 H), 3.90-3.93 (m, 2 H), 6.43-6.46 (m, 1 H), 6.94 (d, J=4.88 Hz, 1 H), 7.06-7.12 (m, 2 H), 7.22-7.28 (m, 1 H), 8.28 (d, J=4.58 Hz, 1 H), 12.09 (s, 1 H); MS (DCI/NH$_3$) m/z 436 (M+H)$^+$.

EXAMPLE 668

(cis-4-{4-[5-fluoro-4-(5-fluoro-2-methoxyphenyl)-1H-pyrrolo[2,3-b]pyridin-2-yl]piperidin-1-yl}cyclohexyl)acetic acid

EXAMPLE 668A methyl (cis-4-{4-[5-fluoro-4-(5-fluoro-2-methoxyphenyl)-1H-pyrrolo[2,3-b]pyridin-2-yl]piperidin-1-yl}cyclohexyl)acetate The title compound was prepared as described in Example 1357A, substituting Example 255D for Example 231E and methyl 2-(4-oxocyclohexyl)acetate for ethyl 4-oxocyclohexanecarboxylate. The title compound was the faster-eluting isomer under the described SFC conditions. MS (ESI$^+$) m/z 498.0 (M+H)$^+$.

EXAMPLE 668B (cis-4-{4-[5-fluoro-4-(5-fluoro-2-methoxyphenyl)-1H-pyrrolo[2,3-b]pyridin-2-yl]piperidin-1-yl}cyclohexyl)acetic acid The title compound was prepared using the procedure described in Example 1357B, using Example 1360A in place of Example 1357A. $^1$H NMR (400 MHz, DMSO-d6) δ 1.36-1.76 (m, 6H), 1.78-2.21 (m, 5H), 2.27 (d, J=13.8 Hz, 2H), 2.85-3.35 (m, 5H), 3.73 (s, 3H), 5.91 (s, 1H), 6.95-7.74 (m, 3H), 8.17 (s, 1H), 10.23 (dt, J=20.7, 10.3 Hz, 1H), 11.87 (d, J=6.3 Hz, 1H). MS (ESI$^+$) m/z 484 (M+H)$^+$.

EXAMPLE 673

4-{5-fluoro-2-[($^2$H$_3$)methyloxy]phenyl}-2-(1,2,3,6-tetrahydropyridin-4-yl)-1H-pyrrolo[2,3-b]pyridine

EXAMPLE 673A tert-butyl 4-(4-(4,4,5,5-tetramethyl-1,3,2-dioxaborolan-2-yl)-1-tosyl-1H-pyrrolo[2,3-b]pyridin-2-yl)-5,6-dihydropyridine-1(2H)-carboxylate A mixture of potassium acetate (5.53 g, 56.3 mmol), 1,1'-bis(diphenylphosphino)ferrocene-palladium(II)dichloride dichloromethane complex (0.920 g, 1.127 mmol), bis(pinacolato)diboron (11.92 g, 47.0 mmol), and Example 220C (10 g, 18.78 mmol) in 1,2-dimethoxyethane (200 mL) was stirred at 80° C. for 6 hours. The reaction mixture was diluted with water. The aqueous layer was extracted with ethyl acetate (3×200 mL). The combined organic layers were washed with water and brine, dried with $Na_2SO_4$, filtered, concentrated, and recrystallized with ethyl acetate/petroleum ether (1:4) to provide the title compound. MS (ESI$^+$) m/z 580.3 (M+H)$^+$.

EXAMPLE 673B tert-butyl 4-(4-(5-fluoro-2-(methoxy-d3)-phenyl)-1-tosyl-1H-pyrrolo[2,3-b]pyridin-2-yl)-5,6-dihydropyridine-1(2H)-carboxylate A mixture Example 673A (1.100 g, 1.898 mmol), 2-(methoxy-d3)-5-fluorobromobenzene (0.415 g, 1.993 mmol), 1,1'-bis(diphenylphosphino)ferrocene-palladium(II) dichloride dichloromethane complex (0.062 g, 0.076 mmol), and saturated sodium bicarbonate solution (5 mL) in N,N-dimethylformamide (20 mL) was degassed and then heated at 80° C. for 2 hours. The reaction mixture was treated with water and brine and extracted with ethyl acetate. The combined organic layers were washed with water, dried over $MgSO_4$, filtered, concentrated, and purified on an 80 g silica column using the ISCO Companion flash system eluting with heptanes/ethyl acetate (7:3 to 6:4) to provide the title compound. MS (ESI$^+$) m/z 581.1 (M+H)$^+$.

EXAMPLE 673C tert-butyl 4-(4-(5-fluoro-2-(methoxy-d3)-phenyl)-1H-pyrrolo[2,3-b]pyridin-2-yl)-5,6-dihydropyridine-1(2H)-carboxylate A mixture of Example 673B (0.615 g, 1.059 mmol) and 5M sodium hydroxide (0.741 mL, 3.71 mmol) solution in dioxane (6 mL) was heated at 90° C. overnight. The solvent was evaporated. The residue was treated with ethyl acetate and washed with water. The organic layer was dried over $MgSO_4$, filtered, and concentrated until most solvent was removed. The light suspension was sonicated and diluted with 3 mL of ethyl acetate and heptanes (10 mL) while it was stirred and gently heated. The suspension was stirred for 30 minutes, filtered, washed with ethyl acetate/heptanes (1:1), filtered, and vacuum oven-dried to provide the title compound. MS (ESI$^+$) m/z 427.1 (M+H)$^+$.

EXAMPLE 673D

4-{5-fluoro-2-[($^2H_3$)methyloxy]phenyl}-2-(1,2,3,6-tetrahydropyridin-4-yl)-1H-pyrrolo[2,3-b]pyridine A solution of Example 673C (0.316 g, 0.741 mmol) in $CH_2Cl_2$ (6 mL) was treated with trifluoroacetic acid (0.571 mL, 7.41 mmol). The mixture was stirred for 3 hours and concentrated. The residue was dissolved in 2 mL of methanol and treated with 2 mL of 2M HCl in ether slowly. The suspension was diluted with ether and stirred for 10 minutes. The solids were filtered, washed with ether, and vacuum oven-dried to provide the title compound as an HCl salt. $^1$H NMR (400 MHz, methanol-$d_4$) δ ppm 2.83-3.01 (m, 2H), 3.51 (t, J=6.1 Hz, 2H), 3.97-4.02 (m, 2H), 6.62-6.68 (m, 1H), 6.77 (s, 1H), 7.20-7.37 (m, 3H), 7.63 (d, J=6.2 Hz, 1H), 8.38 (d, J=6.2 Hz, 1H). MS (ESI$^+$) m/z 327.2 (M+H)$^+$.

EXAMPLE 676 methyl 2-{4-[4-(5-fluoro-2-methoxyphenyl)-1H-pyrrolo[2,3-b]pyridin-2-yl]-3,6-dihydropyridin-1(2H)-yl}propanoate A mixture of Example 87D (0.075 g, 0.189 mmol), and triethylamine (0.132 ml, 0.946 mmol) in N,N-dimethylformamide (1.893 ml) with methyl 2-bromopropanoate (0.036 g, 0.218 mmol) was heated at 75° C. for 9 hours. The reaction mixture was partitioned in ethyl acetate (30 mL) and water (15 mL). The aqueous layer was extracted with additional ethyl acetate (30 mL). The combined organic layers were washed with brine (2×15 mL), dried over anhydrous sodium sulfate, filtered and concentrated. The concentrate was purified by flash chromatography on silica gel (AnaLogix IntelliFlash 280 system) eluting with a gradient of from 0% to 6% methanol in dichloromethane to afford the title compound. $^1$H NMR (500 MHz, DMSO-$d_6$) δ ppm 1.25 (d, J=7.0 Hz, 3H), 2.38-2.50 (m, 1H), 2.64-2.74 (m, 1H), 2.74-2.85 (m, 1H), 3.28-3.38 (m, 3H), 3.48 (q, J=7.0 Hz, 1H), 3.64 (s, 3H), 3.73 (s, 3H), 6.18 (d, J=2.0 Hz, 1H), 6.44-6.51 (m, 1H), 7.02 (d, J=4.9 Hz, 1H), 7.14-7.32 (m, 3H), 8.18 (d, J=4.9 Hz, 1H), 11.76 (d, J=2.3 Hz, 1H) MS (ESI$^+$) m/z 410.1 (M+H)$^+$.

EXAMPLE 677

5-chloro-4-(5-fluoro-2-methoxyphenyl)-2-[1-(methylsulfonyl)-1,2,3,6-tetrahydropyridin-4-yl]-1H-pyrrolo[2,3-b]pyridine The title compound was prepared essentially as described in Example 119, substituting Example 229F for Example 87. $^1$H NMR (500 MHz, DMSO-$d_6$) δ ppm 2.54-2.62 (m, 2H), 2.93 (s, 3H), 3.28-3.37 (m, 2H), 3.70 (s, 3H), 3.87-3.94 (m, 2H), 6.08 (s, 1H), 6.51-6.61 (m, 1H), 7.14 (dd, J=8.7, 3.2 Hz, 1H), 7.21 (dd, J=9.1, 4.5 Hz, 1H), 7.32 (td, J=8.7, 3.2 Hz, 1H), 8.26 (s, 1H), 12.10 (s, 1H). MS (ESI$^+$) m/z 436.1 (M+H)$^+$.

EXAMPLE 678

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone

EXAMPLE 678A (R)-benzyl 2,3-dihydroxy-3-methylbutanoate

Methanesulfonamide (150 mg, 1.577 mmol), sodium bicarbonate (390 mg, 4.64 mmol) and AD-MIX-alpha (2.21 g, 1.577 mmol) were combined in 12 mL 1:1 tert-butanol:water then cooled to 0° C. Benzyl 3-methylbut-2-enoate (300 mg, 1.577 mmol) was added and the mixture was stirred at 0° C. while the ice bath gradually warmed to room temperature and was stirred for 60 hours. Sodium sulfite was added and the mixture was stirred at room temperature for 1 hour. The mixture was extracted with ethyl acetate. The combined extracts were rinsed with 2M aqueous KOH and brine, dried over $Na_2SO_4$, filtered, and concentrated to provide the title compound that was used in the next step without further purification.

EXAMPLE 678B (R)-benzyl 2,2,5,5-tetramethyl-1,3-dioxolane-4-carboxylate

To a solution of Example 678A (320 mg, 1.427 mmol) in 2 mL 2,2-dimethoxypropane was added p-toluenesulfonic acid monohydrate (20 mg, 0.105 mmol) and the mixture was stirred at room temperature for 3 hours. The mixture was partitioned between dichloromethane and water. The layers were separated and the aqueous layer was extracted with dichloromethane. The combined extracts were rinsed with water and brine, dried over $Na_2SO_4$, filtered, and concentrated. The product was purified by flash column chromatography on silica (5% ethyl acetate/hexanes) to provide the title compound.

EXAMPLE 678C (R)-2,2,5,5-tetramethyl-1,3-dioxolane-4-carboxylic acid

A solution of Example 678B (280 mg, 1.059 mmol) and 10% palladium on carbon (25 mg, 0.023 mmol) in 5 mL methanol was stirred under hydrogen for 3 hours. The mixture was filtered through diatomaceous earth and was concentrated to provide the title compound that was used without further purification.

EXAMPLE 678D

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone The title compound was prepared using the procedure described in Example 100, using Example 678C in place of acetic acid. $^1$H NMR (400 MHz, DMSO-$d_6$) δ 11.85 (s, 1H), 8.21 (d, J=5.0 Hz, 1H), 7.34-7.13 (m, 3H), 7.04 (dd, J=5.0, 1.7 Hz, 1H), 6.51 (dt, J=7.2, 3.5 Hz, 1H), 6.27 (d, J=2.0 Hz, 1H), 4.75 (d, J=9.8 Hz, 1H), 4.48-4.10 (m, 2H), 3.94-3.63 (m, 2H), 3.74 (s, 3H), 2.58-2.46 (m, 2H), 1.45-1.32 (m, 9H), 1.10 (d, J=17.0 Hz, 3H). MS (DCI) m/e 480 (M+H)$^+$.

EXAMPLE 679

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid

EXAMPLE 679A 1-tert-butyl 4-ethyl 3-(((trifluoromethyl)sulfonyl)oxy)-5,6-dihydropyridine-1,4(2H)-dicarboxylate A suspension of sodium hydride (0.059 g, 1.474 mmol) in ether (5 mL) under a nitrogen atmosphere was cooled to 0° C. A solution of 1-tert-butyl 4-ethyl 3-oxopiperidine-1,4-dicarboxylate (0.2 g, 0.737 mmol) in ether (3 mL) was added dropwise over 5 minutes and the reaction slurry was allowed to stir at room temperature for 1.5 hours. The mixture was then cooled to 0° C. and a solution of trifluoromethanesulfonic anhydride (0.139 ml, 0.826 mmol) in ether (3 mL) was added dropwise over 5 minutes followed by removal of the cooling bath. The reaction mixture was stirred at room temperature for 40 minutes and 10 mL saturated aqueous ammonium chloride was added. The layers were separated, the aqueous phase was extracted with dichloromethane (3×15 mL), and the combined organic phases were dried over anhydrous sodium sulfate, filtered, and concentrated to afford the title compound. MS (ESI$^+$) m/z 420.9 (M+NH$_4$)$^+$.

EXAMPLE 679B 1-tert-butyl 4-ethyl 3-(4,4,5,5-tetramethyl-1,3,2-dioxaborolan-2-yl)-5,6-dihydropyridine-1,4(2H)-dicarboxylate A solution of Example 679A (0.29 g, 0.719 mmol) and 4,4,4',4',5,5,5',5'-octamethyl-2,2'-bi(1,3,2-dioxaborolane) (0.201 g, 0.791 mmol) in 1,4-dioxane (4.23 ml) was treated with potassium acetate (0.212 g, 2.157 mmol) followed by 1,1'-bis(diphenylphosphino)ferrocene-palladium(II)dichloride dichloromethane complex (0.023 g, 0.029 mmol) under a nitrogen atmosphere. The mixture was heated at 85° C. for 15 hours. The reaction was allowed to cool to room temperature and was partitioned in ether (50 mL) and water (15 mL). The aqueous layer was extracted with additional ether (50 mL). The combined organic layers were washed with brine, dried over anhydrous sodium sulfate, filtered, and concentrated. The concentrate was purified by flash chromatography on silica gel (AnaLogix IntelliFlash 280 system) eluting with a gradient from 0% to 25% ethyl acetate in heptanes to afford the title compound. MS (ESI$^+$) m/z 382.1 (M+H)$^+$.

EXAMPLE 679C 1-tert-butyl 4-ethyl 3-(4-(5-fluoro-2-methoxyphenyl)-1-(phenylsulfonyl)-1H-pyrrolo[2,3-b]pyridin-2-yl)-5,6-dihydropyridine-1,4(2H)-dicarboxylate A mixture of Example 679B (0.225 g, 0.590 mmol), Example 87B (0.15 g, 0.295 mmol) and sodium hydrogencarbonate (0.099 g, 1.180 mmol) in degassed N,N-dimethylformamide (3 mL) and water (0.7 mL) was treated with bis(triphenylphosphine)palladium(II) chloride (6.21 mg, 8.85 μmol) and the mixture was heated at 80° C. under a nitrogen atmosphere for 4 hours. Additional Example 679B (0.169 g, 0.443 mmol) and bis(triphenylphosphine)palladium(II) chloride (6.21 mg, 8.85 μmol) were added and the reaction was heated at 80° C. for 5 hours. The reaction mixture was allowed to cool to room temperature and was partitioned in 15 mL water and 35 mL ethyl acetate. The aqueous layer was extracted with additional ethyl acetate (25 mL). The combined organic layers were washed with brine (2×20 mL), dried over anhydrous sodium sulfate, filtered, and concentrated. The concentrate was purified by flash chromatography on silica gel (AnaLogix IntelliFlash 280 system) eluting with a gradient of 0% to 40% ethyl acetate in heptanes to afford the title compound. MS (ESI$^+$) m/z 636.3 (M+H)$^+$.

EXAMPLE 679D ethyl 5-(4-(5-fluoro-2-methoxyphenyl)-1-(phenylsulfonyl)-1H-pyrrolo[2,3-b]pyridin-2-yl)-1,2,3,6-tetrahydropyridine-4-carboxylate A mixture of Example 679C (0.069 g, 0.109 mmol) in dichloromethane (1 ml) was treated with trifluoroacetic acid (0.084 ml, 1.085 mmol) and the solution was stirred at room temperature for 20 hours. The reaction mixture was concentrated and the residue was partitioned between 50 mL ethyl acetate and 15 mL saturated aqueous sodium bicarbonate. The aqueous layer was extracted with 20 mL additional ethyl acetate. The combined organic layers were washed with 15 mL brine, dried over anhydrous sodium sulfate, filtered, and concentrated to provide the title compound. MS (ESI+) m/z 536.1 (M+H)+.

EXAMPLE 679E ethyl 5-(4-(5-fluoro-2-methoxyphenyl)-1-(phenyl-sulfonyl)-1H-pyrrolo[2,3-b]pyridin-2-yl)-1-(methyl-sulfonyl)-1,2,3,6-tetrahydropyridine-4-carboxylate A 0° C. solution of Example 679D (0.056 g, 0.105 mmol) and N-ethyl-N-isopropylpropan-2-amine (0.055 ml, 0.314 mmol) in dichloromethane (0.8 mL) was treated with methanesulfonyl chloride (0.013 ml, 0.167 mmol) and the mixture was allowed to stir at room temperature for 3 hours. The reaction mixture was diluted with dichloromethane (40 mL) and washed with saturated aqueous sodium bicarbonate (10 mL) and brine (10 mL). The organic layer was dried over anhydrous sodium sulfate, filtered, and concentrated. The concentrate was purified by flash chromatography on silica gel (AnaLogix IntelliFlash 280 system) eluting with a gradient of from 0% to 50% ethyl acetate in heptanes to afford the title compound. MS (ESI+) m/z 614.0 (M+H)+.

EXAMPLE 679F

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid A mixture of Example 679E (0.03 g, 0.049 mmol) in 1,4-dioxane (0.5 ml), ethanol (0.2 ml) and water (0.3 ml) was treated with aqueous 3 N sodium hydroxide (0.081 ml, 0.244 mmol) and the reaction mixture was heated at 75° C. for 6 hours. The reaction mixture was concentrated and the residue was dissolved in 0.5 mL water. The solution was acidified to pH 4-5 with aqueous 3N HCl and a suspension formed. The mixture was extracted with dichloromethane (4×3 mL). The combined organic layers were dried over anhydrous sodium sulfate, filtered, and concentrated to provide the title compound. $^1$H NMR (400 MHz, DMSO-$d_6$, 90° C.) δ ppm 1.95-2.08 (m, 1H), 2.17-2.28 (m, 1H), 3.10 (s, 3H), 3.36-3.48 (m, 1H), 3.58-3.66 (m, 1H), 3.73 (s, 3H), 3.75-3.94 (m, 1H), 6.16 (s, 1H), 6.98 (d, J=5.0 Hz, 1H), 7.09-7.31 (m, 3H), 7.46 (s, 1H), 8.13 (d, J=5.0 Hz, 1H), 11.18-12.67 (m, 2H). MS (ESI+) m/z 446.1 (M+H)+.

EXAMPLE 680

{4-[4-(5-fluoro-2-methoxyphenyl)-1H-pyrrolo[2,3-b]pyridin-2-yl]-3,6-dihydropyridin-1(2H)-yl}[(4S)-2,2,5,5-tetramethyl-1,3-dioxolan-4-yl]methanone The title compound was prepared using the procedure described in Example 678, using AD-MIX-beta in place of AD-MIX-alpha in Example 678A. $^1$H NMR (400 MHz, DMSO-$d_6$) δ 11.85 (s, 1H), 8.21 (d, J=5.0 Hz, 1H), 7.34-7.13 (m, 3H), 7.04 (dd, J=5.0, 1.7 Hz, 1H), 6.51 (dt, J=7.2, 3.5 Hz, 1H), 6.27 (d, J=2.0 Hz, 1H), 4.75 (d, J=9.8 Hz, 1H), 4.48-4.10 (m, 2H), 3.94-3.63 (m, 2H), 3.74 (s, 3H), 2.58-2.46 (m, 2H), 1.45-1.32 (m, 9H), 1.10 (d, J=17.0 Hz, 3H). MS (DCI) m/e 480 (M+H)+.

EXAMPLE 681

2-{4-[4-(5-fluoro-2-methoxyphenyl)-1H-pyrrolo[2,3-b]pyridin-2-yl]-3,6-dihydropyridin-1(2H)-yl}propanoic acid A solution of Example 676 (0.045 g, 0.110 mmol) in tetrahydrofuran (0.3 ml) and methanol (0.3 ml) was treated with aqueous 2M lithium hydroxide (0.165 ml, 0.330 mmol) and the mixture was stirred at room temperature for 16 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (500 MHz, CD$_3$OD) δ ppm 1.69 (d, J=7.2 Hz, 3H), 2.95-3.01 (m, 2H), 3.56-3.73 (m, 2H), 3.80 (s, 3H), 4.03-4.12 (m, 1H), 4.14-4.24 (m, 1H), 4.28 (q, J=7.2 Hz, 1H), 6.45-6.52 (m, 1H), 6.60 (s, 1H), 7.15-7.28 (m, 3H), 7.35 (d, J=5.6 Hz, 1H), 8.30 (d, J=5.6 Hz, 1H). MS (APCI+) m/z 396.4 (M+H)+.

EXAMPLE 682

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid

EXAMPLE 682A methyl 4-oxocyclohex-1-enecarboxylate

To a stirred solution of (E)-((4-methoxybuta-1,3-dien-2-yl)oxy)trimethylsilane (5 g, 29.0 mmol) in benzene (20 mL) was added methyl acrylate (5.26 mL, 58.0 mmol) and the reaction mixture was heated at reflux for 48 hours. The solution was concentrated to give the crude methyl 2-methoxy-4-((trimethylsilyl)oxy)cyclohex-3-enecarboxylate which was dissolved in dichloromethane (58.0 mL) and cooled to 0° C. Next, boron trifluoride etherate (14.70 mL, 116 mmol) was slowly added and the reaction mixture was stirred for 15 minutes then concentrated. Ethyl acetate (100 mL) was added then the mixture was cooled to 0° C. and made basic by slowly adding an aqueous potassium carbonate (10% wt, 100 mL) solution. The organic layer was removed and the aqueous mixture was extracted with two 100 mL portions of ethyl acetate. The organic extracts were combined then dried over anhydrous magnesium sulfate, filtered and concentrated to afford the crude title compound which was carried through the next step without purification. MS (ESI+) m/z 155 (M+H)+.

EXAMPLE 682B methyl 4-(4-(4-(5-fluoro-2-methoxyphenyl)-1H-pyrrolo[2,3-b]pyridin-2-yl)-5,6-dihydropyridin-1(2H)-yl)cyclohex-1-enecarboxylate The title compound was prepared using the conditions described in Example 1305 using Example 682A in place of 3-oxocyclobutanecarbonitrile. MS (ESI+) m/z 462.1 (M+H)+.

EXAMPLE 682C

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid Example 682 B (121 mg, 0.262 mmol) was dissolved in a mixture of tetrahydrofuran (1200 μL) and methanol (800

μL). A 1 molar aqueous sodium hydroxide solution (787 μL, 0.787 mM) was added and the mixture was stirred at ambient temperature overnight. The mixture was concentrated to remove most of the organic solvent then the aqueous mixture was diluted with 1.5 mL of water to give a dark orange solution. The mixture was brought to pH ~6-7 by dropwise addition of a 1 molar aqueous hydrochloric acid solution (~0.8 mL) and a precipitate formed. The precipitate was filtered and washed with water (5 mL), diethylether (10 mL) then collected and dried under high vacuum to give the title compound. $^1$H NMR (400 MHz, DMSO-d$_6$) δ ppm 1.44-1.65 (m, 1H), 2.02-2.24 (m, 2H), 2.46 (d, J=19.4 Hz, 2H), 2.55-2.73 (m, 2H), 3.00-3.54 (m, 6H), 3.74 (s, 3H), 6.26 (s, 1H), 6.46-6.55 (m, 1H), 6.75-6.85 (m, 1H), 7.04 (d, J=4.9 Hz, 1H), 7.13-7.35 (m, 3H), 8.21 (d, J=4.9 Hz, 1H), 11.86 (s, 1H). MS (ESI$^+$) m/z 448.1 (M+H)$^+$.

EXAMPLE 683

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid

EXAMPLE 683A tert-butyl 2-(5-oxohexahydropentalen-2(1H)-ylidene)acetate

A mixture of (tert-butoxycarbonylmethylene)triphenylphosphorane (450 mg, 1.195 mmol) and tetrahydropentalene-2,5(1H,3H)-dione (330 mg, 2.391 mmol) in toluene (3601 μl) was stirred at 100° C. for 24 hours. After cooling to ambient the mixture was diluted with dichloromethane then concentrated onto silica gel. Silica gel flash chromatography (Isco®, Redi-Sep® column, 0-50% ethyl acetate/hexane linear gradient) afforded the title compound. $^1$H NMR (400 MHz, DMSO-d$_6$) δ ppm 1.41 (s, 9H), 1.87-2.07 (m, 2H), 2.29-2.46 (m, 3H), 2.46-2.60 (m, 1H), 2.63-2.88 (m, 3H), 2.92-3.09 (m, 1H), 5.59-5.74 (m, 1H).

EXAMPLE 683B tert-butyl 2-(5-oxooctahydropentalen-2-yl)acetate

In a 50 mL pressure bottle Example 683A (135 mg, 0.571 mmol) was dissolved in methanol (10 mL) and 5% Pd/C (wet) (13 mg, 0.122 mmol) was added. The mixture was stirred under 30 psi of hydrogen for 30 minutes at ambient temperature. Next, the mixture was filtered through a celite pad and the filter cake was washed with 20 mL of methanol. Concentration under vacuum afforded the title compound which was carried through the next step without purification. MS (ESI$^+$) m/z 239.1 (M+H)$^+$.

EXAMPLE 683C tert-butyl 2-((2s,3aR,5r,6aS)-5-(4-(4-(5-fluoro-2-methoxyphenyl)-1H-pyrrolo[2,3-b]pyridin-2-yl)-5,6-dihydropyridin-1(2H)-yl)octahydropentalen-2-yl)acetate The title compound was prepared using the conditions described in Example 1305 using Example 683B in place of 3-oxocyclobutanecarbonitrile. MS (ESI$^+$) m/z 546.3 (M+H)$^+$.

EXAMPLE 683D

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid The title compound was prepared as described in Example 1297B using Example 683C in place of Example 1297A. 1H NMR (400 MHz, DMSO-d6) δ ppm 0.94-1.34 (m, 2H), 1.45-1.80 (m, 2H), 2.00-2.13 (m, 1H), 2.13-2.49 (m, 6H), 2.71-3.00 (m, 2H), 3.07-3.27 (m, 1H), 3.52-3.68 (m, 2H), 3.76 (s, 3H), 3.80-3.93 (m, 1H), 3.92-4.07 (m, 1H), 6.48 (d, J=1.9 Hz, 1H), 6.58 (s, 1H), 7.18-7.39 (m, 4H), 8.31 (d, J=5.4 Hz, 1H), 10.82-11.47 (m, 1H), 12.47-12.93 (m, 1H). MS (ESI$^+$) m/z 490.2 (M+H)$^+$.

EXAMPLE 684 methyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 578, substituting methanol for ethanol in Example 578A and Example 87D for Example 17G in Example 578B. $^1$H NMR (400 MHz, DMSO-d$_6$): δ2.56-2.60 (m, 2 H), 3.47 (t, J=5.65 Hz, 2 H), 3.62 (s, 3 H), 3.74 (s, 3 H), 4.01 (d, J=2.14 Hz, 2 H), 6.26 (d, J=1.53 Hz, 0.5 H), 6.50 (s, 0.5 H), 6.97 (d, J=7.93 Hz, 0.5 H), 7.04 (d, J=4.88 Hz, 1 H), 7.16-7.31 (m, 3 H), 8.21 (d, J=5.19 Hz, 1 H), 8.47 (d, J=7.93 Hz, 0.5 H), 11.49 (s, 0.5 H), 11.86 (s, 0.5 H); MS (DCI/NH$_3$) m/z 461 (M+H)$^+$.

EXAMPLE 685 methyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 578, substituting methanol for ethanol in Example 578A and Example 665B for Example 17G in Example 578B. $^1$H NMR (400 MHz, DMSO-d$_6$): δ2.70 (s, 2 H), 3.48 (t, J=5.65 Hz, 2 H), 3.65 (s, 3 H), 3.66 (s, 3 H), 4.02 (d, J=2.75 Hz, 2 H), 6.43 (s, 1 H), 6.94 (d, J=4.88 Hz, 1H), 7.06-7.12 (m, 2 H), 7.22-7.28 (m, 1 H), 8.28 (d, J=4.88 Hz, 1 H), 11.50 (s, 1 H), 12.08 (s, 1 H); MS (DCI/NH$_3$) m/z 495 (M+H)$^+$.

EXAMPLE 686

2-fluoro-N-methyl-4-{2-[1-(methylsulfonyl)-1,2,3,6-tetrahydropyridin-4-yl]-1H-pyrrolo[2,3-b]pyridin-4-yl}benzamide A mixture of Example 220F (75.0 mg, 0.211 mmol), (3-fluoro-4-(methylcarbamoyl)phenyl)boronic acid (49.8 mg, 0.253 mmol), 1,1'-bis(diphenylphosphino)ferrocenepalladium(II)dichloride dichloromethane complex (8.60 mg, 10.53 μmol), and saturated sodium bicarbonate solution (0.40 mL) in N,N-dimethylformamide (1.6 mL) was degassed and heated at 80° C. for 2 hours. The reaction mixture was treated with water and brine and extracted with ethyl acetate. The suspension in the aqueous layer was filtered and combined with the organic layer. The mixture was purified by HPLC (see protocols in Example 361) to provide the title compound as a trifluoroacetic acid salt. $^1$H NMR (400 MHz, DMSO-d$_6$) δ ppm 2.65-2.72 (m, 2H), 2.82 (d, J=4.6 Hz, 3H), 2.95 (s, 3H), 3.40 (t, J=5.7 Hz, 2H), 3.91-3.97 (m, 2H), 6.60 (bs, 1H), 6.70 (bs, 1H), 7.25 (d, J=5.0 Hz, 1H), 7.64-7.73 (m, 2H), 7.80 (t, J=7.7 Hz, 1H), 8.25-8.38 (m, 2H), 12.11 (bs, 1H). MS (ESI$^+$) m/z 429.1 (M+H)$^+$.

EXAMPLE 687

(2S)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one Example 680 (103 mg, 0.215 mmol) was treated with 2 mL 1:1 trifluoroacetic acid:water and stirred at room temperature for 3 hours. The mixture was concentrated and the residue was eluted through a Varian Bond Elut SCX cation-exchange column to yield the free base of the title compound. $^1$H NMR (400 MHz, DMSO-d$_6$) δ 11.86 (s, 1H), 8.21 (s, 1H), 7.24 (m, 3H), 7.04 (d, J=4.8 Hz, 1H), 6.51 (s, 1H), 6.25 (s, 1H), 5.09 (bs, 2H), 4.23-4.15 (m, 2H), 3.87-3.61 (m, 3H), 3.66 (s, 3H), 2.58-2.42 (m, 2H), 1.18 (s, 3H), 1.05 (s, 3H). MS (ESI+) m/e 440 (M+H)$^+$.

EXAMPLE 688

(2R)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one The title compound was prepared using the procedure described in Example 687, using Example 678 in place of Example 680. $^1$H NMR (400 MHz, DMSO-d$_6$) δ 11.86 (s, 1H), 8.21 (s, 1H), 7.24 (m, 3H), 7.04 (d, J=4.8 Hz, 1H), 6.51 (s, 1H), 6.25 (s, 1H), 5.09 (bs, 2H), 4.23-4.15 (m, 2H), 3.87-3.61 (m, 3H), 3.66 (s, 3H), 2.58-2.42 (m, 2H), 1.18 (s, 3H), 1.05 (s, 3H). MS (ESI+) m/e 440 (M+H)$^+$.

EXAMPLE 689

4-(5-fluoro-2-methoxyphenyl)-2-[1-(hydroxyacetyl)-1,2,3,6-tetrahydropyridin-4-yl]-1H-pyrrolo[2,3-b]pyridine-5-carbonitrile

EXAMPLE 689A 4-(5-fluoro-2-methoxyphenyl)-1-(phenylsulfonyl)-2-(1,2,3,6-tetrahydropyridin-4-yl)-1H-pyrrolo[2,3-b]pyridine-5-carbonitrile The title compound was prepared as described in Example 236F, substituting Example 236D for Example 236E. MS (ESI$^+$) m/z 489 (M+H)$^+$.

EXAMPLE 689B 4-(5-fluoro-2-methoxyphenyl)-2-(1-(2-hydroxyacetyl)-1,2,3,6-tetrahydropyridin-4-yl)-1H-pyrrolo[2,3-b]pyridine-5-carbonitrile Example 689A (102 mg, 0.17 mmol), 2-hydroxyacetic acid (15.51 mg, 0.204 mmol), 1-(3-dimethylaminopropyl)-3-ethylcarbodiimide hydrochloride (39.1 mg, 0.204 mmol), 1H-benzo[d][1,2,3]triazol-1-ol hydrate (31.2 mg, 0.204 mmol) and N-ethyl-N-isopropylpropan-2-amine (89 μl, 0.510 mmol) in 2 mL N,N-dimethylformamide was stirred at room temperature overnight. The reaction mixture was diluted with water and extracted with dichloromethane. The organic solution was washed with brine, dried with magnesium sulfate, and filtered. The filtrate was concentrated to dryness and redissolved in 2 mL of 1:1 methanol:tetrahydrofuran. Sodium hydroxide solution (1M aqueous, 850 μl, 0.850 mmol) was added. The mixture was stirred at room temperature overnight, neutralized to pH 5 with 2N aqueous HCl, extracted with dichloromethane, and purified by column chromatography eluting with 0-5% methanol in dichloromethane using an Analogix purification system to afford the title compound. $^1$H NMR (400 MHz, DMSO-d$_6$) δ 2.38-2.76 (m, 2H), 3.45-3.73 (m, 2H), 3.76 (s, 3H), 3.99-4.38 (m, 4H), 6.32 (d, J=7.5 Hz, 1H), 6.46-6.85 (m, 1H), 7.10-7.66 (m, 3H), 8.62 (s, 1H), 12.53 (d, J=7.5 Hz, 1H). MS (ESI$^+$) m/z 407 (M+H)$^+$.

EXAMPLE 690

4-[5-cyano-4-(5-fluoro-2-methoxyphenyl)-1H-pyrrolo[2,3-b]pyridin-2-yl]-N-methyl-3,6-dihydropyridine-1(2H)-carboxamide Example 689A (100 mg, 0.166 mmol), 2,5-dioxopyrrolidin-1-yl methylcarbamate (42.9 mg, 0.249 mmol) and N-ethyl-N-isopropylpropan-2-amine (87 μl, 0.498 mmol) in 2 mL N,N-dimethylformamide was stirred at room temperature overnight. The reaction mixture was diluted with water and extracted with dichloromethane. The organic solution was washed with brine, dried with magnesium sulfate, filtered, and the filtrate was concentrated to dryness. The residue was dissolved in 2 mL methanol and 1M aqueous sodium hydroxide solution (830 μl, 0.830 mmol) was added. The mixture was stirred at room temperature overnight, neutralized to pH 5, extracted with dichloromethane and purified by column chromatography eluting with 0-8% methanol in dichloromethane using an Analogix purification system to obtained the title compound. $^1$H NMR (500 MHz, DMSO-d$_6$) δ 2.40-2.50 (br, 2H), 2.59 (d, J=4.2 Hz, 3H), 3.43-3.55 (m, 2H), 3.76 (s, 3H), 3.99-4.04 (m, 2H), 6.31 (s, 1H), 6.44-6.50 (m, 1H), 6.60 (bs, 1H), 7.22-7.35 (m, 2H), 7.39 (td, J=8.7, 3.2 Hz, 1H), 8.61 (s, 1H), 12.48 (bs, 1H). MS (ESI$^+$) m/z 406 (M+H)$^+$.

EXAMPLE 694

3-ethoxy-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione To a solution of Example 87D (100 mg, 0.252 mmol) and 3,4-diethoxycyclobut-3-ene-1,2-dione (129 mg, 0.757 mmol) in 2 mL ethanol in a microwave vial was added triethylamine (0.25 mL, 1.794 mmol). The mixture was subjected to microwave irradiation using a Biotage Initiator (model 355302) at 125° C. for 30 minutes. The mixture was concentrated and the residue was partitioned between water and dichloromethane. The aqueous layer was extracted with dichloromethane and the combined organics were dried over Na$_2$SO$_4$, filtered, and concentrated. The crude material was purified by flash column chromatography on silica (5% methanol/dichloromethane) to yield the title compound. $^1$H NMR (400 MHz, DMSO-d$_6$) δ 11.90 (s, 1H), 8.22 (d, J=4.9 Hz, 1H), 7.34-7.14 (m, 3H), 7.05 (d, J=4.9 Hz, 1H), 6.58-6.47 (m, 1H), 6.30 (d, J=2.0 Hz, 1H), 4.69 (q, J=7.2 Hz, 2H), 4.53-3.74 (m, 4H), 3.74 (s, 3H), 2.66 (m, 2H), 1.39 (t, J=7.0 Hz, 3H). MS (ESI+) m/e 448 (M+H)$^+$.

EXAMPLE 695

5-fluoro-4-(5-fluoro-2-methoxyphenyl)-2-(1,2,3,6-tetrahydropyridin-4-yl)-1H-pyrrolo[2,3-b]pyridine The title compound was prepared in Example 231E. $^1$H NMR (400 MHz, methanol-$d_4$) δ ppm 2.81-2.89 (m, 2H), 3.48 (t, J=6.1 Hz, 2H), 3.80 (s, 3H), 3.94-4.00 (m, 2H), 6.58-6.62 (m, 2H), 7.21-7.26 (m, 2H), 7.32 (td, J=8.6, 3.0 Hz, 1H), 8.44 (d, J=3.7 Hz, 1H). MS (ESI$^+$) m/z 342.1 (M+H)$^+$.

EXAMPLE 699

1-{4-[4-(5-fluoro-2-methoxyphenyl)-1H-pyrrolo[2,3-b]pyridin-2-yl]-3,6-dihydropyridin-1(2H)-yl}-2-(methylsulfonyl)ethanone A solution of Example 87D (0.06 g, 0.151 mmol) in N,N-dimethylformamide (1.5 ml) was treated with N-methylmorpholine (0.083 ml, 0.757 mmol), 1-(3-dimethylaminopropyl)-3-ethylcarbodiimide hydrochloride (0.044 g, 0.227 mmol), 1H-benzo[d][1,2,3]triazol-1-ol hydrate (0.014 g, 0.091 mmol) and 2-(methylsulfonyl)acetic acid (0.025 g, 0.182 mmol) and the reaction mixture was stirred at room temperature for 15 hours. The mixture was poured into 12 mL water and the resulting suspension was filtered. The solid collected was washed with water and dried under vacuum to provide the title compound. $^1$H NMR (400 MHz, DMSO-$d_6$) δ ppm 2.44-2.52 (m, 1H), 2.59 (m, 1H), 3.11 (s, 3H), 3.63-3.80 (m, 5H), 4.17-4.25 (m, 1H), 4.26-4.42 (m, 1H), 4.47-4.59 (m, 2H), 6.27 (dd, J=5.2, 2.1 Hz, 1H), 6.46-6.55 (m, 1H), 7.04 (d, J=4.9 Hz, 1H), 7.15-7.34 (m, 3H), 8.21 (d, 1H), 11.81-11.92 (m, 1H). MS (ESI$^+$) m/z 444.2 (M+H)$^+$.

The following compounds (concluding with Example 1076) were prepared essentially as described in Example 699, substituting the appropriate carboxylic acid for 2-(methylsulfonyl)acetic acid. Some of the products were purified by flash chromatography while others were purified by reverse-phase HPLC. Accordingly, some examples were isolated as trifluoroacetic acid salts.

EXAMPLE 700 ethyl 3-{4-[4-(5-fluoro-2-methoxyphenyl)-1H-pyrrolo[2,3-b]pyridin-2-yl]-3,6-dihydropyridin-1(2H)-yl}-3-oxopropanoate $^1$H NMR (400 MHz, DMSO-$d_6$) δ ppm 1.11-1.23 (m, 3H), 2.42-2.51 (m, 1H), 2.53-2.63 (m, 1H), 3.52-3.69 (m, 4H), 3.74 (s, 3H), 4.01-4.26 (m, 4H), 6.21-6.31 (m, 1H), 6.40-6.55 (m, 1H), 7.04 (d, J=4.9 Hz, 1H), 7.14-7.34 (m, 3H), 8.21 (d, J=5.1 Hz, 1H), 11.81-11.92 (m, 1H). MS (ESI$^+$) m/z 438.2 (M+H)$^+$.

EXAMPLE 702

N-(2-{4-[4-(5-fluoro-2-methoxyphenyl)-1H-pyrrolo[2,3-b]pyridin-2-yl]-3,6-dihydropyridin-1(2H)-yl}-2-oxoethyl)methanesulfonamide $^1$H NMR (400 MHz, DMSO-$d_6$) δ ppm 2.50-2.61 (m, 2H), 2.94 (s, 3H), 3.66 (t, J=5.9 Hz, 2H), 3.72 (s, 3H), 3.96 (d, J=5.6 Hz, 2H), 4.14-4.21 (m, 2H), 6.21-6.30 (m, 1H), 6.44-6.53 (m, 1H), 6.66-6.74 (m, 1H), 7.01 (d, J=5.0 Hz, 1H), 7.11-7.28 (m, 3H), 8.19 (d, J=4.9 Hz, 1H), 11.50-11.58 (m, 1H). MS (ESI$^+$) m/z 459.1 (M+H)$^+$.

EXAMPLE 752

2-(dimethylamino)-1-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-$d_6$) δ ppm 2.51-2.58 (m, 1H), 2.58-2.67 (m, 1H), 2.83 (d, J=3.9 Hz, 6H), 3.54 (t, J=5.8 Hz, 1H), 3.65-3.76 (m, 4H), 4.04-4.17 (m, 1H), 4.17-4.26 (m, 1H), 4.25-4.40 (m, 2H), 6.31 (dd, J=7.0, 2.1 Hz, 1H), 6.40-6.59 (m, 1H), 7.07 (dd, J=5.0, 1.5 Hz, 1H), 7.16-7.35 (m, 3H), 8.23 (d, J=4.9 Hz, 1H), 9.44-9.64 (m, 1H), 11.91-12.02 (m, 1H). MS (ESI$^+$) m/z 409.1 (M+H)$^+$.

EXAMPLE 764

1-{4-[4-(5-fluoro-2-methoxyphenyl)-1H-pyrrolo[2,3-b]pyridin-2-yl]-3,6-dihydropyridin-1(2H)-yl}-2-(3-hydroxypyrrolidin-1-yl)ethanone $^1$H NMR (400 MHz, CD$_3$OD-trifluoroacetic acid) δ ppm 1.95-2.41 (m, 2H), 2.61-2.77 (m, 2H), 3.13-3.30 (m, 2H), 3.37-3.78 (m, 2H), 3.79-3.96 (m, 5H), 4.18-4.28 (m, 1H), 4.32-4.62 (m, 4H), 6.54-6.73 (m, 2H), 7.19-7.38 (m, 3H), 7.59 (dd, J=6.3, 2.3 Hz, 1H), 8.33 (dd, J=6.3, 1.8 Hz, 1H). MS (ESI$^+$) m/z 451.1 (M+H)$^+$.

EXAMPLE 782

2-{4-[4-(5-fluoro-2-methoxyphenyl)-1H-pyrrolo[2,3-b]pyridin-2-yl]-3,6-dihydropyridin-1(2H)-yl}-2-oxoethanesulfonamide $^1$H NMR (400 MHz, DMSO-$d_6$) δ ppm 2.45-2.54 (m, 1H), 2.56-2.63 (m, 1H), 3.64-3.80 (m, 5H), 4.15-4.22 (m, 1H), 4.22-4.40 (m, 3H), 6.21-6.31 (m, 1H), 6.47-6.55 (m, 1H), 6.93-7.09 (m, 3H), 7.14-7.34 (m, 3H), 8.21 (dd, J=5.0, 0.9 Hz, 1H), 11.81-11.91 (m, 1H). MS (ESI$^+$) m/z 445.1 (M+H)$^+$.

EXAMPLE 783

2-{4-[4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide $^1$H NMR (400 MHz, DMSO-$d_6$) δ ppm 2.45-2.54 (m, 1H), 2.56-2.68 (m, 4H), 3.64-3.79 (m, 5H), 4.15-4.24 (m, 1H), 4.24-4.44 (m, 3H), 6.22-6.31 (m, 1H), 6.46-6.56 (m, 1H), 7.04 (d, J=5.0, 0.9 Hz, 1H), 7.07-7.34 (m, 4H), 8.21 (d, J=4.9, 0.9 Hz, 1H), 11.81-11.92 (m, 1H) MS (ESI$^+$) m/z 459.2 (M+H)$^+$.

EXAMPLE 1073

2-{4-[4-(5-fluoro-2-methoxyphenyl)-1H-pyrrolo[2,3-b]pyridin-2-yl]-3,6-dihydropyridin-1(2H)-yl}-N,N-dimethyl-2-oxoethanesulfonamide $^1$H NMR (400 MHz, DMSO-$d_6$) δ ppm 2.43-2.51 (m, 1H), 2.58-2.66 (m, 1H), 2.82 (s, 6H), 3.65-3.82 (m, 5H), 4.15-4.24 (m, 1H), 4.31-4.45 (m, 3H), 6.27 (d, J=2.0 Hz, 1H), 6.47-6.57 (m, 1H), 7.04 (dd, J=4.9, 1.4 Hz, 1H), 7.14-7.34 (m, 3H), 8.21 (dd, J=4.8, 1.1 Hz, 1H), 11.87 (dd, J=10.9, 2.3 Hz, 1H). MS (ESI$^+$) m/z 473.1 (M+H)$^+$.

EXAMPLE 1076

1-{4-[4-(5-fluoro-2-methoxyphenyl)-1H-pyrrolo[2,3-b]pyridin-2-yl]-3,6-dihydropyridin-1(2H)-yl}-1-oxopropane-2-sulfonamide $^1$H NMR (500 MHz, DMSO-d$_6$) δ 11.91-11.83 (m, 1H), 8.21 (d, J=5.0 Hz, 1H), 7.31-7.16 (m, 3H), 7.04 (d, J=4.9 Hz, 1H), 6.93-6.89 (m, 2H), 6.55-6.48 (m, 1H), 6.29-6.24 (m, 1H), 4.71-4.50 (m, 1H), 4.41-4.36 (m, 1H), 4.23-4.17 (m, 1H), 3.81-3.62 (m, 5H), 2.68-2.52 (m, 1H), 2.50-2.44 (m, 2H), 1.47-1.40 (m, 3H). MS (ESI$^+$) m/z 459.2 (M+H)$^+$.

EXAMPLE 701

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}-3,6-dihydropyridine-1(2H)-carboxamide A solution of 1-(2-(methylsulfonyl)ethyl)-1H-pyrazol-4-amine dihydrochloride (0.05 g, 0.191 mmol) and N-ethyl-N-isopropylpropan-2-amine (0.133 ml, 0.763 mmol) in N,N-dimethylformamide (0.8 mL) was treated with bis(2,5-dioxopyrrolidin-1-yl) carbonate (0.061 g, 0.238 mmol) and pyridine (0.015 ml, 0.191 mmol). After stirring at room temperature for 4 hours, the mixture was added to a stirring suspension of Example 87D (0.076 g, 0.191 mmol) and N-ethyl-N-isopropylpropan-2-amine (0.166 ml, 0.954 mmol) in N,N-dimethylformamide (1.4 mL) dropwise over 3 minutes. The reaction mixture was stirred at room temperature for 16 hours and was partitioned between ethyl acetate (75 mL) and water (20 mL). The aqueous layer was extracted with additional ethyl acetate (40 mL). The combined organic layers were washed with brine (25 mL), dried over anhydrous sodium sulfate, filtered, and concentrated. The residue was purified by flash chromatography on silica gel (AnaLogix IntelliFlash 280 system) eluting with a gradient of from 0% to 10% methanol in dichloromethane to afford the title compound. $^1$H NMR (400 MHz, DMSO-d$_6$) δ ppm 2.46-2.53 (m, 2H), 2.82 (s, 3H), 3.58-3.68 (m, 4H), 3.74 (s, 3H), 4.10-4.19 (m, 2H), 4.46 (t, J=6.8 Hz, 2H), 6.27 (d, J=2.0 Hz, 1H), 6.51-6.60 (m, 1H), 7.04 (d, J=5.0 Hz, 1H), 7.14-7.34 (m, 3H), 7.46 (d, J=0.7 Hz, 1H), 7.82 (s, 1H), 8.20 (d, J=5.0 Hz, 1H), 8.61 (s, 1H), 11.84 (d, J=2.2 Hz, 1H). MS (ESI$^+$) m/z 539.1 (M+H)$^+$.

EXAMPLE 703

4-[4-(2,3-difluorophenyl)-1H-pyrrolo[2,3-b]pyridin-2-yl]cyclohex-3-ene-1-carboxylic acid

EXAMPLE 703A 4-(2,3-difluorophenyl)-1-(phenylsulfonyl)-1H-pyrrolo[2,3-b]pyridine The title compound was prepared essentially as described in Example 87A, substituting 5-fluoro-2-methoxyphenylboronic acid with (2,3-difluorophenyl)boronic acid. LCMS (ESI): 371.2 (M+H)$^+$.

EXAMPLE 703B 4-(2,3-difluorophenyl)-2-iodo-1-(phenylsulfonyl)-1H-pyrrolo[2,3-b]pyridine Example 703A (20 g, 54.0 mmol) was dissolved in 300 mL tetrahydrofuran, stirred and cooled to about −60° C. for 15 minutes in a 500 mL round-bottomed flask under nitrogen gas atmosphere. Lithium diisopropylamide (29.7 mL, 59.4 mmol, 2.0M in tetrahydrofuran) was then added and the mixture was stirred at −60° C. for 2 hours, at which point iodine (20.56 g, 81 mmol) in tetrahydrofuran (100 mL) was added to dropwise. The resulting reaction was stirred at −65° C. for 3 hours. The reaction was quenched with aqueous sodium thiosulfate and extracted with ethyl acetate (2×50 mL). The combined organic layers were dried over magnesium sulfate, filtered, and concentrated. The residue was purified by silica gel column chromatography (petroleum ether/ethyl acetate: 5:1 to 1:1) to afford the title compound. LCMS (ESI): 497.2 (M+H)$^+$.

EXAMPLE 703C 4-(2,3-difluorophenyl)-2-iodo-1H-pyrrolo[2,3-b]pyridine

The title compound was prepared essentially as described in Example 219A, substituting Example 87B with Example 703B. MS (ESI): 357.1 (M+H)$^+$.

EXAMPLE 703D ethyl 4-(4-(2,3-difluorophenyl)-1H-pyrrolo[2,3-b]pyridin-2-yl)cyclohex-3-enecarboxylate The title compound was prepared essentially as described in Example 219B, substituting Example 219A with Example 703C. MS (ESI): 383.2 (M+H)$^+$.

EXAMPLE 703E

4-[4-(2,3-difluorophenyl)-1H-pyrrolo[2,3-b]pyridin-2-yl]cyclohex-3-ene-1-carboxylic acid The title compound was prepared essentially as described in Example 219C, substituting Example 219B with Example 703D. $^1$H NMR (400 MHz, DMSO-d$_6$) δ ppm 12.20 (s, 1 H) 11.90 (s, 1 H) 8.25 (d, J=5.19 Hz, 1 H) 7.28-7.69 (m, 3 H) 7.11 (d, J=4.88 Hz, 1 H) 6.57 (s, 1 H) 6.32 (s, 1 H) 2.47-2.60 (m, 2 H) 2.31-2.46 (m, 3 H) 2.00-2.14 (m, 1 H) 1.61-1.78 (m, 1 H). MS (ESI): 355.2 (M+H)$^+$.

EXAMPLE 705

3-{4-[4-(5-fluoro-2-methoxyphenyl)-1H-pyrrolo[2,3-b]pyridin-2-yl]-3,6-dihydropyridin-1(2H)-yl}-3-oxopropanoic acid The title compound was prepared essentially as described in Example 681, substituting Example 700 for Example 676. $^1$H NMR (400 MHz, DMSO-d$_6$) δ ppm 2.43-2.50 (m, 1H), 2.53-2.62 (m, 1H), 3.50 (d, J=11.7 Hz, 2H), 3.61 (t, J=5.7 Hz, 1H), 3.67 (t, J=5.8 Hz, 1H), 3.75 (s, 3H), 4.14-4.22 (m, 2H), 6.27-6.37 (m, 1H), 6.50-6.58 (m, 1H), 7.11 (dd, J=5.1, 3.6 Hz, 1H), 7.18-7.34 (m, 3H), 8.24 (d, J=5.1 Hz, 1H), 12.00-12.09 (m, 1H). MS (APCI$^+$) m/z 410.2 (M+H)$^+$.

EXAMPLE 706

4-(4-chloro-2-methoxyphenyl)-2-(1,2,3,6-tetrahydropyridin-4-yl)-1H-pyrrolo[2,3-b]pyridine The title compound was prepared as described in Example 87, substituting 2-methoxy-4-chlorophenylboronic acid for 5-fluoro-2-methoxyphenylboronic acid in Example 87A. $^1$H NMR (400 MHz, DMSO-$d_6$) δ 2.71 (br m, 2H), 3.24-3.52 (br m, 2H), 3.81 (apparent s, 5H), 6.47 (br s, 1H), 6.61 (br s, 1H), 7.07-7.27 (m, 2H), 7.32 (d, J=1.9 Hz, 1H), 7.46 (d, J=8.2 Hz, 1H), 8.30 (d, J=5.4 Hz, 1H), 9.48 (br s, 1H), 12.62 (br s, 1H); MS (ESI$^+$) m/z 340 (M+H)$^+$.

EXAMPLE 707

4-(2,4-dimethoxyphenyl)-2-[1-(methylsulfonyl)-1,2,3,6-tetrahydropyridin-4-yl]-1H-pyrrolo[2,3-b]pyridine The title compound was prepared essentially as described in Examples 220E, substituting Example 622 for Example 220D. $^1$H NMR (400 MHz, DMSO-$d_6$) δ 2.62 (td, J=6.4, 5.7, 3.1 Hz, 2H), 2.95 (s, 3H), 3.38 (t, J=5.7 Hz, 2H), 3.78 (s, 3H), 3.86 (s, 3H), 3.93 (q, J=2.7 Hz, 2H), 6.39 (d, J=1.8 Hz, 1H), 6.49 (s, 1H), 6.53-6.60 (m, 1H), 6.66-6.79 (m, 1H), 7.17 (d, J=5.4 Hz, 1H), 7.39 (d, J=8.4 Hz, 1H), 8.24 (d, J=5.4 Hz, 1H). MS (ESI$^+$) m/z 414 (M+H)$^+$.

EXAMPLE 708

3-{4-[4-(2,4-dimethoxyphenyl)-1H-pyrrolo[2,3-b]pyridin-2-yl]-3,6-dihydropyridin-1(2H)-yl}propane-1,2-diol The title compound was prepared essentially as described in Examples 149, substituting Example 622 for Example 135B. $^1$H NMR (400 MHz, DMSO-$d_6$) δ 2.75 (d, J=41.9 Hz, 2H), 3.03-3.39 (m, 4H), 3.46 (dd, J=10.9, 4.8 Hz, 1H), 3.69 (dd, J=28.6, 11.7 Hz, 1H), 3.77 (s, 3H), 3.85 (s, 3H), 3.88-4.17 (m, 3H), 6.39 (t, J=2.7 Hz, 1H), 6.45 (d, J=3.7 Hz, 1H), 6.69 (dd, J=8.4, 2.4 Hz, 1H), 6.76 (d, J=2.4 Hz, 1H), 7.08 (d, J=5.1 Hz, 1H), 7.36 (dd, J=8.4, 1.3 Hz, 1H), 8.23 (dd, J=5.1, 1.4 Hz, 1H). MS (ESI$^+$) m/z 410 (M+H)$^+$.

EXAMPLE 709

4-[4-(2,4-dimethoxyphenyl)-1H-pyrrolo[2,3-b]pyridin-2-yl]-N-methyl-3,6-dihydropyridine-1(2H)-carboxamide The title compound was prepared essentially as described in Examples 222D, substituting Example 622 for Example 222C. $^1$H NMR (400 MHz, DMSO-$d_6$) δ 2.45 (q, J=4.2 Hz, 2H), 2.60 (s, 3H), 3.51 (t, J=5.6 Hz, 2H), 3.78 (s, 3H), 3.85 (s, 3H), 4.02 (q, J=2.6 Hz, 2H), 6.36 (d, J=1.9 Hz, 1H), 6.47-6.61 (m, 1H), 6.70 (dd, J=8.5, 2.4 Hz, 1H), 6.76 (d, J=2.4 Hz, 1H), 7.16 (d, J=5.3 Hz, 1H), 7.39 (d, J=8.4 Hz, 1H), 8.22 (d, J=5.4 Hz, 1H).). MS (ESI$^+$) m/z 393 (M+H)$^+$.

EXAMPLE 710

1-{4-[4-(2,4-dimethoxyphenyl)-1H-pyrrolo[2,3-b]pyridin-2-yl]-3,6-dihydropyridin-1(2H)-yl}-2-hydroxyethanone The title compound was prepared essentially as described in Examples 417, substituting Example 622 for Example 365. $^1$H NMR (400 MHz, DMSO-$d_6$) δ 2.50 (p, J=1.9 Hz, 1H), 2.55 (m, 1H), 3.55 (t, J=5.8 Hz, 1H), 3.69 (t, J=5.8 Hz, 1H), 3.78 (s, 3H), 3.85 (s, 3H), 4.09-4.23 (m, 4H), 6.35 (s, 1H), 6.53 (d, J=12.9 Hz, 1H), 6.70 (dd, J=8.4, 2.4 Hz, 1H), 6.76 (d, J=2.4 Hz, 1H), 7.15 (dd, J=5.5, 2.5 Hz, 1H), 7.38 (d, J=8.4 Hz, 1H), 8.22 (d, J=5.3 Hz, 1H). MS (ESI$^+$) m/z 394 (M+H)$^+$.

EXAMPLE 711

3-{4-[4-(2-methoxyphenyl)-1H-pyrrolo[2,3-b]pyridin-2-yl]-3,6-dihydropyridin-1(2H)-yl}propane-1,2-diol The title compound was prepared essentially as described in Examples 149, substituting Example 630 for Example 135B. $^1$H NMR (400 MHz, DMSO-$d_6$) δ 2.80 (m, 2H), 3.16 (d, J=11.6 Hz, 1H), 3.33 (td, J=9.6, 8.1, 4.8 Hz, 3H), 3.46 (dd, J=11.0, 4.8 Hz, 1H), 3.68 (dd, J=28.0, 11.1 Hz, 1H), 3.77 (s, 3H), 3.91-4.05 (m, 2H), 4.10 (d, J=17.0 Hz, 1H), 6.36 (d, J=1.9 Hz, 1H), 6.47 (t, J=3.3 Hz, 1H), 7.04-7.15 (m, 2H), 7.21 (dd, J=8.3, 1.0 Hz, 1H), 7.34-7.51 (m, 2H), 8.26 (d, J=5.0 Hz, 1H). MS (ESI$^+$) m/z 380 (M+H)$^+$.

EXAMPLE 712

4-[4-(2-methoxyphenyl)-1H-pyrrolo[2,3-b]pyridin-2-yl]-N-methyl-3,6-dihydropyridine-1(2H)-carboxamide The title compound was prepared essentially as described in Examples 222D, substituting Example 630 for Example 222C. $^1$H NMR (500 MHz, DMSO-$d_6$) δ 2.45 (dt, J=6.9, 3.5 Hz, 2H), 2.60 (s, 3H), 3.50 (t, J=5.6 Hz, 2H), 3.77 (s, 3H), 4.02 (q, J=2.7 Hz, 2H), 6.32 (d, J=1.9 Hz, 1H), 6.50-6.64 (m, 1H), 7.11 (td, J=7.4, 1.1 Hz, 1H), 7.17 (d, J=5.3 Hz, 1H), 7.22 (d, J=8.3 Hz, 1H), 7.38-7.53 (m, 2H), 8.26 (d, J=5.3 Hz, 1H). MS (ESI$^+$) m/z 363 (M+H)$^+$.

EXAMPLE 713

2-hydroxy-1-{4-[4-(2-methoxyphenyl)-1H-pyrrolo[2,3-b]pyridin-2-yl]-3,6-dihydropyridin-1(2H)-yl}ethanone The title compound was prepared essentially as described in Examples 417, substituting Example 630 (120 mg, 0.4 mmol) for Example 365. $^1$H NMR (400 MHz, DMSO-$d_6$) δ 2.49-2.61 (m, 3H), 3.54 (t, J=5.7 Hz, 1H), 3.68 (t, J=5.9 Hz, 1H), 3.77 (s, 3H), 4.03-4.25 (m, 3H), 6.32 (d, J=3.8 Hz, 1H), 6.46-6.62 (m, 1H), 7.02-7.18 (m, 2H), 7.21 (dd, J=8.5, 1.0 Hz, 1H), 7.36-7.54 (m, 2H), 8.25 (d, J=5.2 Hz, 1H). MS (ESI$^+$) m/z 3964 (M+H)$^+$.

EXAMPLE 714

3-{4-[4-(4-fluoro-2-methoxyphenyl)-1H-pyrrolo[2,3-b]pyridin-2-yl]-3,6-dihydropyridin-1(2H)-yl}propane-1,2-diol The title compound was prepared essentially as described in Examples 149, substituting Example 658 for Example 135B. $^1$H NMR (400 MHz, DMSO-$d_6$) δ 2.80 (m, 2H), 3.15 (t, J=10.6 Hz, 1H), 3.25-3.41 (m, 3H), 3.46 (dd, J=10.9, 4.8 Hz, 1H), 3.69 (dd, J=27.5, 12.0 Hz, 1H), 3.78 (s, 3H), 3.95 (d, J=19.4 Hz, 2H), 4.09 (d, J=16.9 Hz, 1H), 6.35 (d, J=2.0 Hz, 1H), 6.46 (t, J=3.3 Hz, 1H), 6.92 (td, J=8.4, 2.5 Hz, 1H), 7.06 (d, J=5.0 Hz, 1H), 7.12 (dd, J=11.5, 2.5 Hz, 1H), 7.43 (dd, J=8.4, 6.9 Hz, 1H), 8.25 (d, J=5.0 Hz, 1H). MS (ESI$^+$) m/z 398 (M+H)$^+$.

EXAMPLE 715

4-[4-(4-fluoro-2-methoxyphenyl)-1H-pyrrolo[2,3-b]pyridin-2-yl]-N-methyl-3,6-dihydropyridine-1(2H)-carboxamide The title compound was prepared essentially as described in Examples 222D, substituting Example 658 for Example 222C. $^1$H NMR (400 MHz, DMSO-d$_6$) δ 2.35-2.50 (m, 2H), 2.60 (s, 3H), 3.50 (t, J=5.6 Hz, 2H), 3.79 (s, 3H), 4.01 (q, J=2.8 Hz, 2H), 6.29 (d, J=2.0 Hz, 1H), 6.53 (dt, J=3.9, 2.4 Hz, 1H), 6.93 (td, J=8.4, 2.5 Hz, 1H), 7.06-7.16 (m, 2H), 7.45 (dd, J=8.4, 6.9 Hz, 1H), 8.22 (d, J=5.2 Hz, 1H). MS (ESI$^+$) m/z 381 (M+H)$^+$.

EXAMPLE 716

1-{4-[4-(4-fluoro-2-methoxyphenyl)-1H-pyrrolo[2,3-b]pyridin-2-yl]-3,6-dihydropyridin-1(2H)-yl}-2-hydroxyethanone The title compound was prepared essentially as described in Examples 417, substituting Example 658 for Example 365. $^1$H NMR (400 MHz, DMSO-d$_6$) δ 2.45-2.57 (m, 2H), 3.54 (t, J=5.6 Hz, 1H), 3.68 (t, J=5.9 Hz, 1H), 3.79 (s, 3H), 4.08-4.21 (m, 4H), 6.27-6.33 (m, 1H), 6.49-6.57 (m, 1H), 6.93 (td, J=8.4, 2.5 Hz, 1H), 7.07-7.16 (m, 2H), 7.45 (dd, J=8.5, 6.8 Hz, 1H), 8.23 (d, J=5.2 Hz, 1H). MS (ESI$^+$) m/z 382 (M+H)$^+$.

EXAMPLE 717

3-{4-[4-(4,5-difluoro-2-methoxyphenyl)-1H-pyrrolo[2,3-b]pyridin-2-yl]-3,6-dihydropyridin-1(2H)-yl}propane-1,2-diol The title compound was prepared essentially as described in Examples 149, substituting Example 1046A for Example 135B. $^1$H NMR (400 MHz, DMSO-d$_6$) δ 2.81 (m, 2H), 3.05-3.22 (m, 1H), 3.24-3.41 (m, 3H), 3.46 (dd, J=10.9, 4.7 Hz, 1H), 3.60-3.74 (m, 1H), 3.77 (s, 3H), 3.97 (d, J=19.4 Hz, 2H), 4.10 (d, J=17.0 Hz, 1H), 6.40 (d, J=2.0 Hz, 1H), 6.47 (d, J=3.5 Hz, 1H), 7.08 (d, J=5.0 Hz, 1H), 7.37 (dd, J=12.9, 6.9 Hz, 1H), 7.49 (dd, J=10.9, 9.2 Hz, 1H), 8.26 (d, J=5.0 Hz, 1H). MS (ESI$^+$) m/z 415 (M+H)$^+$.

EXAMPLE 718

1-{4-[4-(4,5-difluoro-2-methoxyphenyl)-1H-pyrrolo[2,3-b]pyridin-2-yl]-3,6-dihydropyridin-1(2H)-yl}-2-hydroxyethanone The title compound was prepared essentially as described in Examples 417, substituting Example 1046A for Example 365. $^1$H NMR (400 MHz, DMSO-d$_6$) δ 2.53 (d, J=17.5 Hz, 2H), 3.55 (t, J=5.7 Hz, 1H), 3.69 (t, J=5.9 Hz, 1H), 3.77 (s, 3H), 4.05-4.24 (m, 4H), 6.34 (d, J=4.6 Hz, 1H), 6.45-6.61 (m, 1H), 7.10 (d, J=5.0 Hz, 1H), 7.37 (dd, J=12.9, 6.9 Hz, 1H), 7.49 (dd, J=11.0, 9.2 Hz, 1H), 8.24 (d, J=5.2 Hz, 1H). MS (ESI$^+$) m/z 400 (M+H)$^+$.

EXAMPLE 719

N-({4-[4-(5-fluoro-2-methoxyphenyl)-1H-pyrrolo[2,3-b]pyridin-2-yl]-3,6-dihydropyridin-1(2H)-yl}sulfonyl)acetamide

EXAMPLE 719A acetylsulfamoyl chloride

Acetic acid (1.973 mL, 34.5 mmol) was added slowly dropwise to chlorosulfonyl isocyanate (3 mL, 34.5 mmol) with ice/water bath cooling as required to maintain gentle gas evolution. After the addition was complete, the residue was recrystallized from refluxing benzene (10 mL), to provide the title compound. MS (DCI/NH$_3$) m/z 158 (M+H)$^+$.

EXAMPLE 719B

N-({4-[4-(5-fluoro-2-methoxyphenyl)-1H-pyrrolo[2,3-b]pyridin-2-yl]-3,6-dihydropyridin-1(2H)-yl}sulfonyl)acetamide To a suspension of Example 87D (100 mg, 0.252 mmol) in CH$_2$Cl$_2$ (7 mL) was added triethylamine (0.176 mL, 1.262 mmol) and Example 719A (40 mg, 0.252 mmol) at room temperature. The mixture was stirred at room temperature overnight, and the reaction mixture was directly separated by flash chromatography (0-15% CH$_3$OH in CH$_2$Cl$_2$) to give the crude product. This material was heated with 4 mL of methanol and stirred. After cooling, the solid was collected by filtration, washed with methanol, and dried with magnesium sulfate to provide the title compound. $^1$H NMR (400 MHz, DMSO-d$_6$): δ1.96-1.96 (m, 3 H), 2.55-2.60 (m, 2 H), 3.45 (t, J=5.65 Hz, 2 H), 3.74 (s, 3 H), 4.00 (d, J=2.75 Hz, 2 H), 6.26 (d, J=2.14 Hz, 1 H), 6.50 (s, 1 H), 7.04 (d, J=4.88 Hz, 1 H), 7.17-7.29 (m, 3 H), 8.21 (d, J=5.19 Hz, 1 H), 11.52 (s, 1 H), 11.85 (d, J=1.53 Hz, 1 H); MS (DCI/NH$_3$) m/z 445 (M+H)$^+$.

EXAMPLE 720

4-(4,5-difluoro-2-methoxyphenyl)-2-[1-(methylsulfonyl)-1,2,3,6-tetrahydropyridin-4-yl]-1H-pyrrolo[2,3-b]pyridine The title compound was prepared essentially as described in Examples 220E, substituting Example 1046A (100 mg, 0.3 mmol) for Example 220D. $^1$H NMR (500 MHz, DMSO-d$_6$) δ 2.62 (q, J=4.4 Hz, 2H), 2.95 (s, 3H), 3.37 (t, J=5.8 Hz, 2H), 3.77 (s, 3H), 3.92 (q, J=2.8 Hz, 2H), 6.35 (d, J=2.0 Hz, 1H), 6.56 (t, J=3.5 Hz, 1H), 7.10 (d, J=5.0 Hz, 1H), 7.37 (dd, J=12.9, 6.8 Hz, 1H), 7.50 (dd, J=10.9, 9.1 Hz, 1H), 8.25 (d, J=5.1 Hz, 1H). MS (ESI$^+$) m/z 420 (M+H)$^+$.

EXAMPLE 721

4-(5-fluoro-2-methoxyphenyl)-3-methyl-2-(1,2,3,6-tetrahydropyridin-4-yl)-1H-pyrrolo[2,3-b]pyridine

EXAMPLE 721A 4-chloro-3-methyl-1-(phenylsulfonyl)-1H-pyrrolo[2,3-b]pyridine

To a solution of 4-chloro-3-methyl-1H-pyrrolo[2,3-b]pyridine (1.1 g, 6.6 mmol) in N,N'-dimethylformamide (20 mL) was added NaH (166 mg, 6.93 mmol) at 0° C. The mixture was stirred at room temperature for 30 minutes and benzenesulfonyl chloride (1.2 g, 6.6 mmol) was added. After 2 hours, the reaction was complete and was partitioned between water and ethyl acetate. The organic phase was concentrated and was purified by flash chromatography on silica gel using an ISCO Companion eluting with heptanes/ethyl acetate to provide the title compound. LC/MS m/z 307 (M+H)$^+$.

EXAMPLE 721B 4-(5-fluoro-2-methoxyphenyl)-3-methyl-1-(phenylsulfonyl)-1H-pyrrolo[2,3-b]pyridine A mixture of Example 721A (1.66 g, 5.41 mmol), (5-fluoro-2-methoxyphenyl)boronic acid (1.4 g, 8.2 mmol), phenylallylchloro(1,3-bis(diisopropylphenyl)-2-imidazol-2-yliden)palladium(II) (105 mg, 0.16 mmol) and potassium phosphate (3.45 g, 16 mmol) was suspended in a mixture solvent of tetrahydrofuran (60 mL) and water (18 mL). The suspension was purged with N$_2$ and heated at 60° C. for 3 hours. The reaction was partitioned between water and ethyl acetate. The organic phase was concentrated and purified by flash chromatography on silica gel using an ISCO Companion eluting with heptanes/ethyl acetate to provide the title compound. LC/MS m/z 397 (M+H)$^+$.

EXAMPLE 721C 4-(5-fluoro-2-methoxyphenyl)-2-iodo-3-methyl-1-(phenylsulfonyl)-1H-pyrrolo[2,3-b]pyridine A solution of Example 721B (1.94 g, 4.9 mml) in tetrahydrofuran (50 mL) was cooled to −75° C., then lithium diisopropylamide (7.3 mL, 15 mmol) was added dropwise and the reaction was maintained below −75° C. The reaction mixture was stirred for another 30 minutes, and iodine (2.5 g, 9.8 mmol in 2.5 mL tetrahydrofuran) was added. The reaction mixture was slowly brought to room temperature. After the completion of the reaction, the reaction mixture was partitioned between water and ethyl acetate. The organic phase was concentrated and purified by flash chromatography on silica gel using an ISCO Companion eluting with heptanes/ethyl acetate to provide the title compound. LC/MS m/z 523 (M+H)$^+$.

EXAMPLE 721D 4-(5-fluoro-2-methoxyphenyl)-3-methyl-2-(1,2,3,6-tetrahydropyridin-4-yl)-1H-pyrrolo[2,3-b]pyridine A solution of Example 721C (800 mg, 1.5 mmol), tert-butyl 4-(4,4,5,5-tetramethyl-1,3,2-dioxaborolan-2-yl)-5,6-dihydropyridine-1(2H)-carboxylate (568 mg, 1.9 mmol) and bis(triphenylphosphine)palladium(II)chloride (107 mg, 0.15 mmol) in a mixed solvent of 1,2-dimethoxyethane/ethanol/water with ratio of 7/3/2 (100 mL) was purged with N$_2$ and heated at 100° C. overnight. The reaction was partitioned between water and ethyl acetate. The organic phase was concentrated and purified by flash chromatography on silica gel using an ISCO Companion eluting with heptanes/ethyl acetate to give the protected intermediate. The intermediate was dissolved in mixture of dioxane (20 mL) and methanol (10 mL) and NaOH (200 mg, in 2 mL water) was added. The mixture was stirred at 50° C. for overnight. The reaction was treated with water and extracted with ethyl acetate. The organic phase was concentrated and dissolved in dichloromethane (50 mL) then treated with trifluroacetic acid (2 mL). The mixture was stirred at room temperature for 5 hours and concentrated under vacuum and the residue was purified by reverse-phase HPLC on Zorbax XDB C-18 (32) using a gradient of 5-40% acetonitrile/water (containing 0.1% trifluoroacetic acid) to afford the title compound as the trifluoroacetate salt. $^1$H NMR (400 MHz, DMSO-d$_6$) δ 1.82 (s, 3H), 2.73 (dt, J=6.1, 3.4 Hz, 2H), 3.27-3.42 (m, 2H), 3.67 (s, 3H), 3.81 (dq, J=4.7, 2.4 Hz, 2H), 6.00 (td, J=3.3, 1.6 Hz, 1H), 6.87 (d, J=4.9 Hz, 1H), 7.02-7.21 (m, 2H), 7.29 (td, J=8.7, 3.2 Hz, 1H), 8.22 (d, J=5.0 Hz, 1H). MS (ESI$^+$) m/z 338 (M+H)$^+$.

EXAMPLE 722

2-(8-azabicyclo[3.2.1]oct-2-en-3-yl)-4-(2,3-difluorophenyl)-1H-pyrrolo[2,3-b]pyridine

EXAMPLE 722A tert-butyl 3-(4-bromo-1-tosyl-1H-pyrrolo[2,3-b]pyridin-2-yl)-8-azabicyclo[3.2.1]oct-2-ene-8-carboxylate The title compound was prepared as described in Example 87A, substituting Example 220B for 4-bromo-1-(phenylsulfonyl)-1H-pyrrolo[2,3-b]pyridine and Example 223B for 5-fluoro-2-methoxyphenylboronic acid. MS (ESI$^+$) m/z 558, 560 (M+H)$^+$.

EXAMPLE 722B tert-butyl 3-(4-(2,3-difluorophenyl)-1-tosyl-1H-pyrrolo[2,3-b]pyridin-2-yl)-8-azabicyclo[3.2.1]oct-2-ene-8-carboxylate The title compound was prepared as described in Example 87A, substituting Example 722A for 4-bromo-1-(phenylsulfonyl)-1H-pyrrolo[2,3-b]pyridine and 2,3-difluorophenylboronic acid for 5-fluoro-2-methoxyphenylboronic acid. MS (ESI$^+$) m/z 592 (M+H)$^+$.

EXAMPLE 722C 2-(8-azabicyclo[3.2.1]oct-2-en-3-yl)-4-(2,3-difluorophenyl)-1H-pyrrolo[2,3-b]pyridine The title compound was prepared as described in Example 87D, substituting Example 722B for Example 87C. $^1$H NMR (400 MHz, DMSO-d$_6$) δ 1.81 (dt, J=13.9, 7.4 Hz, 1H), 1.91-2.44 (m, 3H), 2.63 (d, J=17.7 Hz, 1H), 3.08 (dd, J=17.6, 4.5 Hz, 1H), 4.22 (q, J=4.8, 4.4 Hz, 1H), 4.40 (t, J=5.1 Hz, 2H), 6.47 (t, J=2.2 Hz, 1H), 6.77 (d, J=5.7 Hz, 1H), 7.19 (dd, J=5.0, 1.2 Hz, 1H), 7.34-7.51 (m, 2H), 7.51-7.64 (m, 1H), 8.34 (d, J=5.0 Hz, 1H), 9.16 (d, J=10.2 Hz, 1H), 9.58 (s, 1H), 12.30 (d, J=2.3 Hz, 1H); MS (ESI$^+$) m/z 338 (M+H)$^+$.

EXAMPLE 723

{4-[5-cyano-4-(5-fluoro-2-methoxyphenyl)-1H-pyrrolo[2,3-b]pyridin-2-yl]-3,6-dihydropyridin-1(2H)-yl}acetic acid Example 689A (102 mg, 0.17 mmol), methyl 2-bromoacetate (31.2 mg, 0.204 mmol) and N-ethyl-N-isopropylpropan-2-amine (89 µl, 0.510 mmol) in 2 mL N,N-dimethylformamide was stirred at room temperature overnight. The mixture was diluted with water and extracted with dichloromethane. The organic solution was washed with brine and dried with magnesium sulfate, and filtered. The organic layer was concentrated to dryness and then dissolved in 1 mL methanol and 1 mL tetrahydrofuran. Sodium hydroxide aqueous solution (1M, 850 µl, 0.850 mmol) was added. The mixture was heated at 50° C. for 3 hours. The crude product was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the trifluoroacetic acid salt. $^1$H NMR (400 MHz, DMSO-$d_6$) δ 2.70-3.05 (m, 2H), 3.54 (d, J=32.0 Hz, 2H), 3.76 (s, 3H), 4.02 (d, J=19.7 Hz, 2H), 4.20 (s, 2H), 6.32-6.67 (m, 2H), 7.19-7.60 (m, 3H), 8.67 (d, J=4.2 Hz, 1H), 12.68 (dd, J=18.0, 2.3 Hz, 1H). MS (ESI$^+$) m/z 407 (M+H)$^+$.

EXAMPLE 729

3-methoxy-N-methyl-4-[2-(1,2,3,6-tetrahydropyridin-4-yl)-1H-pyrrolo[2,3-b]pyridin-4-yl]benzamide The title compound was prepared essentially as described in Example 673, substituting the appropriate aryl bromide in Example 673B. $^1$H NMR (400 MHz, methanol-$d_4$) δ ppm 2.79-2.92 (m, 2H), 2.98 (s, 3H), 3.50 (t, J=6.1 Hz, 2H), 3.91 (s, 3H), 3.97-3.99 (m, 2H), 6.60 (bs, 1H), 6.71 (s, 1H), 7.60 (s, 3H), 7.68 (s, 1H), 8.41 (bs, 1H). MS (ESI$^+$) m/z 363.1 (M+H)$^+$.

EXAMPLE 732

3-amino-4-{4-[4-(5-fluoro-2-methoxyphenyl)-1H-pyrrolo[2,3-b]pyridin-2-yl]-3,6-dihydropyridin-1 (2H)-yl})cyclobut-3-ene-1,2-dione A solution of Example 694 (61 mg, 0.136 mmol) in 3 mL 7N ammonia in methanol was stirred in a capped vial overnight at room temperature and heated at 50° C. for 3 hours. The precipitate was collected and washed with ethanol to provide the title compound. $^1$H NMR (500 MHz, DMSO-$d_6$) δ 11.90 (s, 1H), 8.22 (s, 1H), 7.77 (s, 2H), 7.33-7.08 (m, 3H), 7.05 (s, 1H), 6.54 (s, 1H), 6.30 (s, 1H), 4.45 (s, 2H), 3.85 (s, 2H), 3.74 (s, 3H), 2.63 (s, 2H). MS (ESI+) m/e 419 (M+H)$^+$.

EXAMPLE 733

4-(5-fluoro-2-methoxyphenyl)-2-(2,5,6,7-tetrahydro-14-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,7-tetrahydro-1H-azepin-4-yl)-1H-pyrrolo[2,3-b]pyridine

EXAMPLE 733A tert-butyl 5-(4,4,5,5-tetramethyl-1,3,2-dioxaborolan-2-yl)-2,3,4,7-tetrahydro-1H-azepine-1-carboxylate and tert-butyl 4-(4,4,5,5-tetramethyl-1,3,2-dioxaborolan-2-yl)-2,3,6,7-tetrahydro-1H-azepine-1-carboxylate The title compound mixture was prepared as described in Example 223A-B, substituting tert-butyl 4-oxoazepane-1-carboxylate for tert-butyl 3-oxo-8-azabicyclo[3.2.1]octane-8-carboxylate in Example 223A. MS (ESI$^+$) m/z 324 (M+H)$^+$.

EXAMPLE 733B tert-butyl 5-(4-(5-fluoro-2-methoxyphenyl)-1-(phenylsulfonyl)-1H-pyrrolo[2,3-b]pyridin-2-yl)-2,3,4,7-tetrahydro-1H-azepine-1-carboxylate and tert-butyl 4-(4-(5-fluoro-2-methoxyphenyl)-1-(phenylsulfonyl)-1H-pyrrolo[2,3-b]pyridin-2-yl)-2,3,6,7-tetrahydro-1H-azepine-1-carboxylate The title compound was prepared as described in Example 87A, substituting Example 87B for 4-bromo-1-(phenylsulfonyl)-1H-pyrrolo[2,3-b]pyridine and Example 733A for 5-fluoro-2-methoxyphenylboronic acid. MS (ESI$^+$) m/z 578 (M+H)$^+$.

EXAMPLE 733C 4-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,7-tetrahydro-1H-azepin-4-yl)-1H-pyrrolo[2,3-b]pyridine The title compound was prepared as described in Example 87D, substituting Example 733B for Example 87C. $^1$H NMR (500 MHz, DMSO-$d_6$) δ 1.88 (p, J=5.4 Hz, 2H), 2.69 (q, J=5.7 Hz, 1H), 2.80-2.88 (m, 2H), 2.97 (dd, J=6.8, 3.6 Hz, 1H), 3.15 (ddt, J=14.9, 9.6, 5.0 Hz, 1H), 3.29 (p, J=4.8 Hz, 2H), 3.76 (s, 3H), 3.87 (q, J=5.2 Hz, 2H), 6.53 (br s, partial 1H), 6.60 (br s, partial 1H), 6.64 (t, J=6.4 Hz, partial 1H), 6.78 (t, J=6.4 Hz, partial 1H), 7.20-7.45 (m, 5H), 8.30 (d, J=5.4 Hz, partial 1H), 8.32 (d, J=5.4 Hz, partial 1H), 9.23 (br s, partial 1H), 9.50 (br s, partial 1H), 12.58 (br s, partial 1H), 12.65 (br s, partial 1H); MS (ESI$^+$) m/z 338 (M+H)$^+$.

EXAMPLE 734

4-(5-fluoro-2-methoxyphenyl)-2-[1-(methylsulfonyl)-2,5,6,7-tetrahydro-1H-azepin-4-yl]-1H-pyrrolo[2,3-b]pyridine and 4-(5-fluoro-2-methoxyphenyl)-2-(1-(methylsulfonyl)-2,3,6,7-tetrahydro-1H-azepin-4-yl)-1H-pyrrolo[2,3-b]pyridine The title compound was prepared as described in Example 119, substituting Example 733C for Example 87D. $^1$H NMR (500 MHz, DMSO-$d_6$) δ 1.84 (p, J=5.7 Hz, 2H), 2.59-2.84 (m, 2H), 2.88 (s, partial 3H), 2.89 (s, partial 3H), 3.50 (t, J=5.9 Hz, 2H), 3.74 (s, 3H), 4.02 (d, J=5.9 Hz, 2H), 6.30 (d, J=2.1 Hz, partial 1H), 6.34 (d, J=2.1 Hz, partial 1H), 6.57 (t, J=6.2 Hz, partial 1H), 6.66 (t, J=6.2 Hz, partial 1H), 7.03 (d, J=4.9 Hz, 1H), 7.15-7.32 (m, 3H), 8.20 (d, J=4.9 Hz, partial 1H), 8.21 (d, J=4.9 Hz, partial 1H), 11.74 (br s, partial 1H), 11.74 (br s, partial 1H); MS (ESI$^+$) m/z 416 (M+H)$^+$.

EXAMPLE 735

5-[4-(5-fluoro-2-methoxyphenyl)-1H-pyrrolo[2,3-b]pyridin-2-yl]-N-methyl-2,3,4,7-tetrahydro-1H-azepine-1-carboxamide and 4-(4-(5-fluoro-2-methoxyphenyl)-1H-pyrrolo[2,3-b]pyridin-2-yl)-N-methyl-2,3,6,7-tetrahydro-1H-azepine-1-carboxamide The title compound was prepared as described in Example 215, substituting Example 733C for Example 87D. $^1$H NMR (500 MHz, DMSO-d$_6$) δ 1.76 (m, 2H), 2.40 (m, 1H), 2.55 (d, J=4.2 Hz, partial 1H), 2.58 (d, J=4.2 Hz, partial 1H), 2.59-2.77 (m, 2H), 3.42-3.57 (m, 2H), 3.73 (s, 3H), 4.04 (d, J=5.3 Hz, 2H), 6.19-6.32 (m, 2H), 6.57 (t, J=5.8 Hz, partial 1H), 6.59 (t, J=5.8 Hz, partial 1H), 7.02 (d, J=4.9 Hz, 1H), 7.14-7.32 (m, 3H), 8.18 (m, 1H), 11.68 (br s, partial 1H), 11.70 (br s, partial 1H); MS (ESI$^+$) m/z 395 (M+H)$^+$.

The following compounds (concluding with Example 1317) were prepared essentially as described in Example 238, substituting the appropriate amine for azetidin-3-ol hydrochloride. The products were purified by reverse phase HPLC on a Phenomenex Luna C8(2) 5 um 100 Å AXIA column (30 mm×75 mm) eluting with a gradient of 10-95% acetonitrile in either 0.1% ammonium acetate/water or 0.1% trifluoroacetic acid/water. Accordingly, some examples were isolated as trifluoroacetic acid salts.

EXAMPLE 736

1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-d$_6$, 90° C.) δ ppm 2.45-2.53 (m, 2H), 2.73 (t, J=5.7 Hz, 2H), 3.24 (q, J=2.9 Hz, 2H), 3.27-3.45 (m, 4H), 3.72 (s, 3H), 3.90-4.10 (m, 2H), 4.42-4.85 (m, 2H), 6.19 (d, J=1.7 Hz, 1H), 6.44 (m, 1H), 7.00 (d, J=4.9 Hz, 1H), 7.13-7.25 (m, 3H), 8.17 (d, J=4.9 Hz, 1H), 11.44 (m, 1H). MS (ESI$^+$) m/z 485.1 (M+H)$^+$.

EXAMPLE 938

2-{4-[4-(5-fluoro-2-methoxyphenyl)-1H-pyrrolo[2,3-b]pyridin-2-yl]-3,6-dihydropyridin-1(2H)-yl}-1-[(2R)-2-(hydroxymethyl)pyrrolidin-1-yl]ethanone $^1$H NMR (400 MHz, CD$_3$OD) δ ppm 1.81-2.13 (m, 4H), 2.57-2.70 (m, 2H), 2.80-2.93 (m, 2H), 3.36 (s, 3H), 3.39-3.69 (m, 5H), 3.76 (s, 3H), 4.05-4.28 (m, 1H), 6.26 (s, 1H), 6.34-6.42 (m, 1H), 7.07 (d, J=5.2 Hz, 1H), 7.11-7.21 (m, 3H), 8.15 (d, J=5.1 Hz, 1H). MS (ESI$^+$) m/z 465.1 (M+H)$^+$.

EXAMPLE 972

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)acetamide $^1$H NMR (400 MHz, DMSO-d$_6$) δ ppm 1.70-1.86 (m, 2H), 1.99-2.24 (m, 1H), 2.39-2.54 (m, 3H), 2.59-2.71 (m, 2H), 2.93-3.05 (m, 2H), 3.07-3.24 (m, 2H), 3.63-3.87 (m, 5H), 4.90-5.04 (m, 1H), 6.21 (d, J=2.0 Hz, 1H), 6.44-6.53 (m, 1H), 7.03 (d, J=4.9 Hz, 1H), 7.13-7.34 (m, 3H), 7.78-7.97 (m, 1H), 8.19 (d, J=5.0 Hz, 1H), 11.77 (d, J=1.7 Hz, 1H). MS (ESI$^+$) m/z 451.1 (M+H)$^+$.

EXAMPLE 1015

1-[(3S,4S)-3,4-dihydroxypyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-d$_6$, 90° C.) δ ppm 2.42-2.54 (m, 2H), 2.75 (t, J=5.7 Hz, 2H), 3.17-3.34 (m, 5H), 3.35-3.50 (m, 2H), 3.60-3.78 (m, 4H), 3.83-4.04 (m, 2H), 4.65-4.97 (m, 2H), 6.18 (d, J=1.5 Hz, 1H), 6.36-6.50 (m, 1H), 7.00 (d, J=4.9 Hz, 1H), 7.11-7.31 (m, 3H), 8.17 (d, J=4.9 Hz, 1H), 11.38-11.52 (m, 1H). MS (ESI$^+$) m/z 467.1 (M+H)$^+$.

EXAMPLE 1167

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide $^1$H NMR (500 MHz, CD$_3$OD) δ 8.32 (d, J=5.7 Hz, 1H), 7.42 (d, J=5.7 Hz, 1H), 7.30-7.18 (m, 3H), 6.66 (s, 1H), 6.50 (bs, 1H), 4.61-3.89 (m, 6H), 3.86-3.37 (m, 5H), 3.07-2.92 (m, 5H), 2.88-2.03 (m, 4H). MS (ESI$^+$) m/z 465.1 (M+H)$^+$.

EXAMPLE 1168

2-{4-[4-(5-fluoro-2-methoxyphenyl)-1H-pyrrolo[2,3-b]pyridin-2-yl]-3,6-dihydropyridin-1(2H)-yl}-N-(2-methoxyethyl)-N-methylacetamide $^1$H NMR (400 MHz, CD$_3$OD) δ ppm 2.91-3.10 (m, 5H), 3.35 (m, 3H), 3.39-3.74 (m, 6H), 3.81 (s, 3H), 3.90-4.31 (m, 2H), 4.33-4.46 (m, 2H), 6.47-6.56 (m, 1H), 6.67 (d, J=1.7 Hz, 1H), 7.16-7.34 (m, 3H), 7.45 (dd, J=5.8, 1.6 Hz, 1H), 8.33 (d, J=5.8 Hz, 1H). MS (ESI$^+$) m/z 453.1 (M+H)$^+$.

EXAMPLE 1196

2-{4-[4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone $^1$H NMR (500 MHz, CD$_3$OD) δ ppm 1.87-2.16 (m, 2H), 2.73-2.80 (m, 2H), 3.12-3.22 (m, 2H), 3.42-3.82 (m, 10H), 4.40-4.62 (m, 2H), 6.34 (d, J=3.2 Hz, 1H), 6.36-6.40 (m, 1H), 7.10 (d, J=5.2 Hz, 1H), 7.12-7.19 (m, 3H), 8.18 (d, J=5.2 Hz, 1H). MS (ESI$^+$) m/z 451.1 (M+H)$^+$.

EXAMPLE 1197

2-{4-[4-(5-fluoro-2-methoxyphenyl)-1H-pyrrolo[2,3-b]pyridin-2-yl]-3,6-dihydropyridin-1(2H)-yl}-1-[(3S)-3-hydroxypyrrolidin-1-yl]ethanone $^1$H NMR (400 MHz, CD$_3$OD) δ ppm 1.86-2.18 (m, 2H), 2.71-2.80 (m, 2H), 3.09-3.24 (m, 2H), 3.41-3.70 (m, 6H), 3.73-3.85 (m, 4H), 4.36-4.65 (m, 2H), 6.34 (d, J=2.5 Hz, 1H), 6.38 (t, J=3.5 Hz, 1H), 7.09 (d, J=5.1 Hz, 1H), 7.12-7.21 (m, 3H), 8.18 (d, J=5.2 Hz, 1H). MS (ESI$^+$) m/z 451.1 (M+H)$^+$.

EXAMPLE 1313

N-(1,1-dioxidotetrahydrothiophen-3-yl)-2-{4-[4-(5-fluoro-2-methoxyphenyl)-1H-pyrrolo[2,3-b]pyridin-2-yl]-3,6-dihydropyridin-1(2H)-yl}acetamide $^1$H NMR (400 MHz, CD$_3$OD) δ ppm 2.14-2.32 (m, 1H), 2.49-2.64 (m, 1H), 2.93-3.02 (m, 2H), 3.06 (dd, J=13.7, 6.5 Hz, 1H), 3.18 (dt, J=13.6, 8.2 Hz, 1H), 3.24-3.33 (m, 1H), 3.49 (dd, J=13.7, 7.6 Hz, 1H), 3.55-3.69 (m, 2H), 3.80 (s, 3H), 4.06-4.21 (m, 4H), 4.58-4.73 (m, 1H), 6.43-6.53 (m, 1H), 6.63 (s, 1H), 7.15-7.33 (m, 3H), 7.39 (d, J=5.7 Hz, 1H), 8.31 (d, J=5.7 Hz, 1H). MS (ESI⁺) m/z 499.1 (M+H)⁺.

EXAMPLE 1315

2-{4-[4-(5-fluoro-2-methoxyphenyl)-1H-pyrrolo[2,3-b]pyridin-2-yl]-3,6-dihydropyridin-1(2H)-yl}-1-[3-(methylsulfonyl)azetidin-1-yl]ethanone ¹H NMR (400 MHz, CD₃OD) δ ppm 2.95-3.06 (m, 5H), 3.55-3.77 (m, 2H), 3.82 (s, 3H), 4.06-4.26 (m, 4H), 4.28-4.47 (m, 3H), 4.47-4.71 (m, 2H), 6.50-6.58 (m, 1H), 6.74 (s, 1H), 7.18-7.37 (m, 3H), 7.55 (d, J=6.0 Hz, 1H), 8.36 (d, J=6.1 Hz, 1H). MS (ESI⁺) m/z 499.0 (M+H)⁺.

EXAMPLE 1317

2-{4-[4-(5-fluoro-2-methoxyphenyl)-1H-pyrrolo[2,3-b]pyridin-2-yl]-3,6-dihydropyridin-1(2H)-yl}-N-(1-methyl-1H-pyrazol-4-yl)acetamide ¹H NMR (400 MHz, CD₃OD) δ ppm 2.95-3.05 (m, 2H), 3.59-3.73 (m, 2H), 3.82 (s, 3H), 3.87 (s, 3H), 4.14-4.22 (m, 2H), 4.23 (s, 2H), 6.48-6.58 (m, 1H), 6.70 (s, 1H), 7.17-7.35 (m, 3H), 7.47 (d, J=5.9 Hz, 1H), 7.55 (s, 1H), 7.92 (s, 1H), 8.34 (d, J=5.9 Hz, 1H). MS (ESI⁺) m/z 461.1 (M+H)⁺.

EXAMPLE 737

2-{4-[4-(5-fluoro-2-methoxyphenyl)-1H-pyrrolo[2,3-b]pyridin-2-yl]-3,6-dihydropyridin-1(2H)-yl}-N-(methylsulfonyl)acetamide A solution of Example 226B (0.05 g, 0.131 mmol) in N,N-dimethylformamide (1.639 ml) was treated with N-methylmorpholine (0.058 ml, 0.524 mmol), 1-(3-dimethylaminopropyl)-3-ethylcarbodiimide hydrochloride (0.038 g, 0.197 mmol), N,N-dimethylpyridin-4-amine (3.20 mg, 0.026 mmol) and methanesulfonamide (0.014 g, 0.151 mmol). The mixture was stirred at room temperature for 15 hours, and was heated at 60° C. for 2 hours. The reaction mixture was directly purified by reverse phase HPLC on a Phenomenex Luna C8(2) 5 um 100 Å AXIA column (30 mm×75 mm) eluting with a gradient of 10-95% acetonitrile in 0.1% ammonium acetate/water to afford the title compound as an ammonium salt. ¹H NMR (400 MHz, DMSO-d₆) δ ppm 2.63-2.75 (m, 2H), 2.92 (s, 3H), 3.25 (t, J=5.9 Hz, 2H), 3.57 (s, 2H), 3.72-3.82 (m, 5H), 6.31 (d, J=2.0 Hz, 1H), 6.40-6.49 (m, 1H), 7.05 (d, J=5.0 Hz, 1H), 7.14-7.32 (m, 3H), 8.23 (d, J=5.0 Hz, 1H), 11.90 (d, J=2.2 Hz, 1H). MS (ESI⁺) m/z 459.0 (M+H)⁺.

EXAMPLE 738

2-{4-[4-(2,4-dimethoxyphenyl)-1H-pyrrolo[2,3-b]pyridin-2-yl]-3,6-dihydropyridin-1(2H)-yl}-N,N-dimethylacetamide To Example 622 in 2 mL N,N-dimethylformamide was added 2-chloro-N,N-dimethylacetamide (34.2 mg, 0.282 mmol) and N-ethyl-N-isopropylpropan-2-amine (128 μl, 0.735 mmol). The mixture was heated at 70° C. for 4 hours, and then purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as trifluoroacetic acid salt. ¹H NMR (500 MHz, DMSO-d₆) δ 2.84 (d, J=6.2 Hz, 2H), 2.93 (s, 3H), 2.94 (s, 3H), 3.26-3.46 (m, 1H), 3.49-3.70 (m, 1H), 3.77 (s, 3H), 3.85 (d, J=4.4 Hz, 3H), 4.11 (d, J=17.0 Hz, 2H), 4.35 (s, 2H), 6.29-6.51 (m, 2H), 6.63-6.82 (m, 2H), 7.07 (d, J=5.1 Hz, 1H), 7.35 (d, J=8.0 Hz, 1H), 8.04-8.45 (m, 1H), 10.02 (s, 1H), 12.03 (s, 1H). MS (ESI⁺) m/z 421 (M+H)⁺.

EXAMPLE 739

2-{4-[4-(2-methoxyphenyl)-1H-pyrrolo[2,3-b]pyridin-2-yl]-3,6-dihydropyridin-1(2H)-yl}-N,N-dimethylacetamide The title compound was prepared as the procedure described in Example 738, substituting Example 630 for Example 622. ¹H NMR (500 MHz, DMSO-d₆) δ 2.80-2.90 (m, 2H), 2.925 (s, 3H), 2.945 (s, 3H), 3.34 (d, J=11.9 Hz, 1H), 3.61 (d, J=11.7 Hz, 1H), 3.77 (s, 3H), 3.86-3.96 (m, 1H), 4.03-4.21 (m, 1H), 4.35 (s, 2H), 6.36 (s, 1H), 6.45 (d, J=3.5 Hz, 1H), 7.06-7.15 (m, 2H), 7.21 (d, J=8.3 Hz, 1H), 7.38-7.51 (m, 2H), 8.10-8.54 (m, 1H), 10.03 (s, 1H), 12.08 (s, 1H). MS (ESI⁺) m/z 391 (M+H)⁺.

EXAMPLE 740

2-{4-[4-(4-fluoro-2-methoxyphenyl)-1H-pyrrolo[2,3-b]pyridin-2-yl]-3,6-dihydropyridin-1(2H)-yl}-N,N-dimethylacetamide The title compound was prepared as the procedure described in Example 738, substituting Example 658 for Example 622. ¹H NMR (500 MHz, DMSO-d₆) δ 2.84 (d, J=6.6 Hz, 2H), 2.94 (d, J=11.2 Hz, 6H), 3.35 (br, 1H), 3.62 (d, J=11.6 Hz, 1H), 3.78 (s, 3H), 3.87-4.04 (m, 1H), 4.04-4.20 (m, 1H), 4.35 (s, 2H), 6.35 (s, 1H), 6.44 (d, J=3.6 Hz, 1H), 6.93 (t, J=8.2 Hz, 1H), 7.02-7.19 (m, 2H), 7.38-7.55 (m, 1H), 8.25 (d, J=5.0 Hz, 1H), 10.03 (s, 1H), 12.04 (s, 1H). MS (ESI⁺) m/z 409 (M+H)⁺.

EXAMPLE 741

2-{4-[4-(4,5-difluoro-2-methoxyphenyl)-1H-pyrrolo[2,3-b]pyridin-2-yl]-3,6-dihydropyridin-1(2H)-yl}-N,N-dimethylacetamide The title compound was prepared as the procedure described in Example 738, substituting Example 627 for Example 622. ¹H NMR (500 MHz, DMSO-d₆) δ 2.85 (q, J=8.2, 7.3 Hz, 2H), 2.94 (d, J=10.8 Hz, 6H), 3.34 (s, 1H), 3.55-3.69 (m, 1H), 3.77 (s, 3H), 3.84-3.95 (m, 1H), 4.11 (d, J=16.7 Hz, 1H), 4.35 (s, 2H), 6.08-6.66 (m, 2H), 7.08 (d, J=4.6 Hz, 1H), 7.22-7.78 (m, 2H), 8.26 (d, J=4.3 Hz, 1H), 10.03 (s, 1H), 12.06 (s, 1H). MS (ESI⁺) m/z 427 (M+H)⁺.

EXAMPLE 742 tert-butyl {5-[4-(5-fluoro-2-methoxyphenyl)-1H-pyrrolo[2,3-b]pyridin-2-yl]-3,6-dihydropyridin-1(2H)-yl}acetate To a 5 mL microwave tube was added Example 485 (0.081 g, 0.204 mmol) and triethylamine (0.2 mL, 1.435 mmol) in N,N-dimethylformamide (1 mL) to give a suspension. tert-Butyl 2-bromoacetate (0.065 g, 0.333 mmol) was added. The mixture was heated at 80° C. for 30 minutes under microwave using a Biotage Initiator (model 355302). After the mixture cooled to room temperature, water was added. The solid product was filtered and washed with water and dried by vacuum to afford the title compound. $^1$H NMR (400 MHz, DMSO-$d_6$): δ 1.42 (s, 9 H) 2.26-2.35 (m, 2 H) 2.66-2.71 (m, 2 H) 3.28 (s, 2 H) 3.42 (s, 2 H) 3.73 (s, 3 H) 6.11 (d, J=2.14 Hz, 1 H) 6.53-6.57 (m, 1 H) 7.02 (d, J=4.88 Hz, 1 H) 7.15-7.30 (m, 3 H) 8.19 (d, J=5.19 Hz, 1 H) 11.79 (s, 1 H). MS (ESI$^+$) m/z 438.0 (M+H)$^+$.

EXAMPLE 743

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)acetamide The title compound was prepared essentially as described in Example 719, substituting Example 665B for Example 87D in Example 719B. $^1$H NMR (400 MHz, DMSO-$d_6$): δ1.98 (s, 3 H), 2.68-2.72 (m, 2 H), 3.46 (t, J=5.65 Hz, 2 H), 3.66 (s, 3 H), 4.01 (d, J=3.05 Hz, 2 H), 6.42 (s, 1 H), 6.95 (s, 1 H), 7.06-7.12 (m, 2 H), 7.21-7.28 (m, 1 H), 8.28 (d, J=4.88 Hz, 1 H), 11.55 (s, 1 H), 12.08 (s, 1 H); MS (DCI/NH$_3$) m/z 479 (M+H)$^+$.

EXAMPLE 744

N-({4-[4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide The title compound was prepared essentially as described in Example 719, substituting pivaloylsulfamoyl chloride for acetyl chloride in Example 719A. $^1$H NMR (400 MHz, DMSO-$d_6$): δ1.11 (s, 9 H), 2.54-2.59 (m, 2 H), 3.46 (t, J=5.65 Hz, 2 H), 3.73 (s, 3 H), 4.02 (d, J=2.44 Hz, 2 H), 6.25 (d, J=1.83 Hz, 1 H), 6.50 (s, 1 H), 7.04 (d, J=4.88 Hz, 1 H), 7.17-7.30 (m, 3 H), 8.21 (d, J=4.88 Hz, 1 H), 11.10 (s, 1 H), 11.84 (d, J=1.53 Hz, 1 H); MS (DCI/NH$_3$) m/z 479 (M+H)$^+$.

EXAMPLE 745

2-{5-[4-(5-fluoro-2-methoxyphenyl)-1H-pyrrolo[2,3-b]pyridin-2-yl]-3,6-dihydropyridin-1(2H)-yl}-N,N-dimethylacetamide The title compound was prepared using the procedure described in Example 742, using 2-chloro-N,N-dimethylacetamide in place of tert-butyl 2-bromoacetate. $^1$H NMR (400 MHz, DMSO-$d_6$): δ 2.57-2.78 (m, 2 H) 2.91 (s, 3 H) 2.95 (s, 3 H) 3.55-3.62 (m, 1 H) 3.75 (s, 3 H) 4.06-4.15 (m, 2 H) 4.36-4.44 (m, 2 H) 6.33 (s, 1 H) 6.82-6.88 (m, 1 H) 7.19-7.37 (m, 4 H) 8.31 (d, J=5.19 Hz, 1 H) 10.33 (s, 1 H) 12.66 (s, 1 H). MS (ESI$^+$) m/z 493.1 (M+H)$^+$.

EXAMPLE 746

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide The title compound was prepared essentially as described in Example 719, substituting pivaloylsulfamoyl chloride for acetyl chloride in Example 719A and Example 665B for Example 87D in Example 719B. $^1$H NMR (400 MHz, DMSO-$d_6$): δ1.13 (s, 9 H), 2.66-2.71 (m, 2 H), 3.46 (t, J=5.80 Hz, 2 H), 3.66 (s, 3 H), 4.02 (d, J=3.05 Hz, 2 H), 6.41-6.43 (m, 1 H), 6.94 (d, J=4.88 Hz, 1 H), 7.06-7.12 (m, 2 H), 7.21-7.29 (m, 1 H), 8.28 (d, J=4.88 Hz, 1 H), 11.14 (s, 1 H), 12.06 (s, 1 H); MS (DCI/NH$_3$) m/z 521 (M+H)$^+$.

EXAMPLE 747 ethyl ({4-[4-(5-fluoro-2-methoxyphenyl)-3-methyl-1H-pyrrolo[2,3-b]pyridin-2-yl]-3,6-dihydropyridin-1(2H)-yl}sulfonyl)carbamate The title compound was prepared essentially as described in Example 218, substituting ethanol for t-butanol in Example 218A and Example 721D for Example 87D in Example 218B. $^1$H NMR (400 MHz, DMSO-$d_6$) δ 1.18 (t, J=7.1 Hz, 3H), 1.78 (s, 3H), 2.61 (dq, J=5.6, 3.0 Hz, 2H), 3.47 (t, J=5.8 Hz, 2H), 3.66 (s, 3H), 3.98 (q, J=2.7 Hz, 2H), 4.09 (q, J=7.1 Hz, 2H), 5.98 (dt, J=3.9, 2.1 Hz, 1H), 6.79 (d, J=4.8 Hz, 1H), 7.03-7.15 (m, 2H), 7.26 (td, J=8.7, 3.2 Hz, 1H), 8.16 (d, J=4.8 Hz, 1H). MS (DCI/NH$_3$) m/z 489 (M+H)$^+$.

EXAMPLE 748

{5-[4-(5-fluoro-2-methoxyphenyl)-1H-pyrrolo[2,3-b]pyridin-2-yl]-3,6-dihydropyridin-1(2H)-yl}acetic acid To a 20 mL round-bottomed flask was added Example 742 (0.079 g, 0.181 mmol) and trifluoroacetic acid (1.4 mL, 18.1 mmol) in dichloromethane (2 mL) to give a suspension. The mixture was stirred at room temperature overnight. After removing the solvents, the residue was dissolved in methanol, treated with 2M HCl in ether (1 mL, 2 mmol) and a precipitate formed. Ether (100 mL) was added, and the solid was filtered and washed with ether to provide the title compound as a hydrochloride salt. $^1$H NMR (400 MHz, DMSO-$d_6$): δ 2.59-2.76 (m, 2 H) 3.34-3.42 (m, 2 H) 3.74 (s, 3 H) 4.23 (s, 2 H) 6.34 (d, J=1.53 Hz, 1 H) 6.76-6.82 (m, 1 H) 7.17 (d, J=5.19 Hz, 1 H) 7.20-7.37 (m, 3 H) 8.27 (d, J=5.19 Hz, 1 H) 10.85 (s, 1 H) 12.43 (s, 1 H). MS (ESI$^+$) m/z 382.1 (M+H)$^+$.

EXAMPLE 749 ethyl 1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylate The title compound was prepared using the procedure described in Example 625, using ethyl 4-hydroxypiperidine-4-carboxylate hydrochloride in place of 3-(aminomethyl) oxetan-3-ol. $^1$H NMR (400 MHz, DMSO-$d_6$): δ 1.20 (t, J=7.02 Hz, 3 H) 1.59 (d, J=13.12 Hz, 2 H) 1.78-1.89 (m, 2 H) 3.05-3.16 (m, 2 H) 3.30-3.39 (m, 4 H) 3.74 (s, 3 H) 3.89-3.94 (m, 4 H) 4.11 (q, J=7.02 Hz, 2 H) 6.28 (d, J=1.83 Hz, 1 H) 6.48-6.53 (m, 1 H) 7.08 (d, J=5.19 Hz, 1 H) 7.17-7.32 (m, 3 H) 8.22 (d, J=5.19 Hz, 1 H) 11.93 (s, 1 H). MS (ESI$^+$) m/z 523.1 (M+H)$^+$.

EXAMPLE 750

4-[4-(5-fluoro-2-methoxyphenyl)-3-methyl-1H-pyrrolo[2,3-b]pyridin-2-yl]-N-methyl-3,6-dihydropyridine-1(2H)-carboxamide The title compound was prepared essentially as described in Examples 222D, substituting Example 721D for Example 222C. $^1$H NMR (400 MHz, DMSO-$d_6$) δ 1.78 (s, 3H), 2.60

(d, J=4.2 Hz, 2H), 3.35 (s, 3H), 3.51 (t, J=5.6 Hz, 2H), 3.66 (s, 3H), 3.99 (q, J=2.8 Hz, 2H), 5.92-6.04 (m, 1H), 6.78 (d, J=4.8 Hz, 1H), 7.02-7.17 (m, 2H), 7.25 (td, J=8.7, 3.2 Hz, 1H), 8.14 (d, J=4.8 Hz, 1H). MS (DCI/NH$_3$) m/z 395 (M+H)$^+$.

EXAMPLE 751

4-(5-fluoro-2-methoxyphenyl)-3-methyl-2-[1-(methylsulfonyl)-1,2,3,6-tetrahydropyridin-4-yl]-1H-pyrrolo[2,3-b]pyridine The title compound was prepared essentially as described in Examples 220E, substituting Example 721D for Example 220D. $^1$H NMR (400 MHz, DMSO-d$_6$) δ 1.79 (s, 3H), 2.64 (dq, J=5.7, 3.0 Hz, 2H), 2.95 (s, 3H), 3.35 (d, J=22.4 Hz, 2H), 3.67 (s, 3H), 3.89 (q, J=2.8 Hz, 2H), 6.00 (dq, J=3.3, 1.7 Hz, 1H), 6.80 (d, J=4.8 Hz, 1H), 7.04-7.16 (m, 2H), 7.26 (td, J=8.7, 3.2 Hz, 1H), 8.16 (d, J=4.8 Hz, 1H). MS (DCI/NH$_3$) m/z 416 (M+H)$^+$.

The following compounds (concluding with Example 1250) were prepared essentially as described in Example 778, substituting the appropriate amine for 223C in Example 778A. Some examples were converted into HCl salts.

EXAMPLE 753

{4-[5-fluoro-4-(5-fluoro-2-methoxyphenyl)-1H-pyrrolo[2,3-b]pyridin-2-yl]-3,6-dihydropyridin-1(2H)-yl}acetic acid $^1$H NMR (500 MHz, methanol-d$_4$) δ ppm 2.90-2.97 (m, 2H), 3.37-3.76 (m, 2H), 3.77 (s, 3H), 3.95-4.14 (m, 2H), 4.20 (s, 2H), 6.36 (s, 1H), 6.38 (bs, 1H), 7.08-7.20 (m, 2H), 7.18-7.26 (m, 1H), 8.16 (d, J=2.8 Hz, 1H). MS (ESI$^+$) m/z 400.1 (M+H)$^+$.

EXAMPLE 789

{4-[4-(2,3-difluorophenyl)-1H-pyrrolo[2,3-b]pyridin-2-yl]-3,6-dihydropyridin-1(2H)-yl}acetic acid $^1$H NMR (400 MHz, DMSO-d$_6$) δ ppm 2.86 (d, J=5.9 Hz, 2H), 3.53 (bs, 2H), 4.06 (bs, 2H), 4.23 (s, 2H), 6.43-6.60 (m, 2H), 7.17 (dd, J=5.2, 1.3 Hz, 1H), 7.31-7.52 (m, 2H), 7.57 (dtd, J=10.1, 7.9, 1.8 Hz, 1H), 8.34 (d, J=4.9 Hz, 1H), 12.18 (d, J=2.3 Hz, 1H). MS (ESI$^+$) m/z 370.1 (M+H)$^+$.

EXAMPLE 984

{4-[4-(5-fluoro-2-methoxyphenyl)-1H-pyrrolo[2,3-b]pyridin-2-yl]-3,3-dimethyl-3,6-dihydropyridin-1(2H)-yl}acetic acid $^1$H NMR (500 MHz, methanol-d$_4$) δ ppm 1.44 (s, 6H), 3.49 (q, J=6.7 Hz, 2H), 3.83 (s, 3H), 4.09 (d, J=3.4 Hz, 2H), 4.26 (s, 2H), 6.23 (t, J=3.4 Hz, 1H), 6.63 (s, 1H), 7.20-7.37 (m, 3H), 7.56 (d, J=6.0 Hz, 1H), 8.39 (d, J=6.0 Hz, 1H). MS (ESI$^+$) m/z 410.2 (M+H)$^+$.

EXAMPLE 1205

{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}) acetic acid $^1$H NMR (400 MHz, methanol-d$_4$) δ ppm 2.70-2.83 (m, 1H), 3.01-3.19 (m, 1H), 3.28-3.40 (m, 2H), 3.42-3.72 (m, 2H), 3.76 (s, 3H), 3.81-3.96 (m, 2H), 4.10-4.15 (m, 2H), 6.19-6.25 (m, 2H), 7.07-7.26 (m, 3H), 8.13 (d, J=2.8 Hz, 1H). MS (ESI$^+$) m/z 426.2 (M+H)$^+$.

EXAMPLE 1250

{3-[5-fluoro-4-(5-fluoro-2-methoxyphenyl)-1H-pyrrolo[2,3-b]pyridin-2-yl]-8-azabicyclo[3.2.1]oct-2-en-8-yl}) acetic acid $^1$H NMR (500 MHz, methanol-d$_4$) δ ppm 2.07 (dd, J=7.5, 3.7 Hz, 1H), 2.33-2.55 (m, 3H), 2.68-2.88 (m, 1H), 3.09-3.17 (m, 0.5H), 3.30-3.38 (m, 0.5H), 3.78 (s, 3H), 4.09 (s, 1H), 4.15-4.30 (m, 1H), 4.31-4.38 (m, 1H), 4.49-4.63 (m, 1H), 6.41-6.44 (m, 1H), 6.54 (d, J=4.0 Hz, 0.4H), 6.73 (d, J=4.0 Hz, 0.6H), 7.12-7.22 (m, 2H), 7.25 (td, J=8.6, 3.1 Hz, 1H), 8.26 (t, J=3.1 Hz, 1H). MS (ESI$^+$) m/z 426.0 (M+H)$^+$.

EXAMPLE 755

4-(2,3-difluorophenyl)-2-[1-(methylsulfonyl)-1,2,5,6-tetrahydropyridin-3-yl]-1H-pyrrolo[2,3-b]yridine

EXAMPLE 755A tert-butyl 3-(4-(2,3-difluorophenyl)-1-(phenylsulfonyl)-1H-pyrrolo[2,3-b]pyridin-2-yl)-5,6-dihydropyridine-1(2H)-carboxylate Example 703B (1.06 g, 2.14 mmol), tert-butyl 3-(4,4,5,5-tetramethyl-1,3,2-dioxaborolan-2-yl)-5,6-dihydropyridine-1(2H)-carboxylate (0.795 g, 2.6 mmol), tetrakis(triphenylphosphine)palladium(0) (99 mg, 0.086 mmol) and a solution of sodium bicarbonate (2.2 mL, 1M) were combined in N,N-dimethylformamide (5 mL). The reaction was degassed and heated to 80° C. for 3 hours. After cooling to room temperature, the mixture was partitioned between water and ethyl acetate. The organic layer was dried over sodium sulfate, filtered, and concentrated. Purification by flash chromatography on silica gel eluting with 20% ethyl acetate-hexanes provided the title compound. (ESI) m/e 552.0 (M+H)$^+$.

EXAMPLE 755B tert-butyl 3-(4-(2,3-difluorophenyl)-1H-pyrrolo[2,3-b]pyridin-2-yl)-5,6-dihydropyridine-1(2H)-carboxylate A solution of Example 755A (718 mg, 1.3 mmol) and aqueous sodium hydroxide (2 mL, 2M) in dioxane (4 mL) was stirred at 90° C. for 12 hours. After cooling to room temperature and concentration, the mixture was partitioned between water and ethyl acetate. The layers were separated and the aqueous phase was extracted with ethyl acetate. The combined organic layers were dried over sodium sulfate, filtered, and concentrated to provide the title compound which was used without any further purification. (ESI) m/e 412.1 (M+H)$^+$.

EXAMPLE 755C 4-(2,3-difluorophenyl)-2-(1,2,5,6-tetrahydropyridin-3-yl)-1H-pyrrolo[2,3-b]pyridine Example 755B (460 mg, 1.1 mmol) and trifluoroacetic acid (0.8 mL) were stirred in dichloromethane (4 mL) for 3 hours at room temperature. The reaction mixture was concentrated. The HCl salt was prepared by dissolving the resultant solid in methanol and adding 2M HCl in diethyl ether. After concentrating, the title compound was used without any further purification. MS (ESI) m/e 312.1 (M+H)+.

EXAMPLE 755D 4-(2,3-difluorophenyl)-2-[1-(methylsulfonyl)-1,2,5,6-tetrahydropyridin-3-yl]-1H-pyrrolo[2,3-b]pyridine The title compound was prepared using the procedure described in Example 258G using Example 755C (92.3 mg, 0.24 mmol) in place of Example 258F. $^1$H NMR (400 MHz, DMSO-$d_6$) δ 2.49 (m, 2H), 3.03 (s, 3H), 3.39 (m, 2H), 4.13 (m, 2H), 6.45 (m, 1H), 6.77 (m, 1H), 7.19 (d, 1H), 7.53 (m, 3H), 8.35 (d, 1H), 12.14 (br s, 1H). (ESI) m/e 390.1 (M+H)+.

EXAMPLE 756

2-{5-[4-(2,3-difluorophenyl)-1H-pyrrolo[2,3-b]pyridin-2-yl]-3,6-dihydropyridin-1(2H)-yl}-N,N-dimethylacetamide Example 755C (96 mg, 0.25 mmol), triethylamine (0.18 mL, 1.29 mmol) and 2-chloro-N—N-dimethylacetamide (39 mg, 0.32 mmol) were dissolved in N,N-dimethylformamide (2 mL). After stirring at room temperature for 24 hours, the mixture was concentrated. Purification by reverse phase-HPLC (Sunfire 5 μM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to give the free base of the title compound. $^1$HNMR (400 MHz, DMSO-$d_6$) δ 2.33 (m, 2H), 2.70 (m, 2H), 2.82 (s, 3H), 3.01 (s, 3H), 3.41 (m, 2H), 3.45 (m, 2H), 6.22 (m, 1H), 6.61 (m, 1H), 7.11 (d, 1H), 7.41 (m, 2H), 7.56 (m, 1H), 8.76 (d, 1H), 1.98 (br s, 1H). (ESI) m/e 397.1 (M+H)+.

EXAMPLE 757

1-{5-[4-(2,3-difluorophenyl)-1H-pyrrolo[2,3-b]pyridin-2-yl]-3,6-dihydropyridin-1(2H)-yl}-2-hydroxyethanone Example 755C (94 mg, 0.24 mmol), glycolic acid (0.024 mL, 0.3 mmol), triethylamine (0.14 mmol, 1 mmol) and ((1H-benzo[d][1,2,3]triazol-1-yl)oxy)tri(pyrrolidin-1-yl)phosphonium hexafluorophosphate(V) (155 mg, 1.2 mmol) were stirred in tetrahydrofuran (2 mL) for 24 hours at room temperature. The reaction was concentrated. Purification by reverse phase-HPLC (Sunfire 5 μM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to give the free base of the title compound. $^1$HNMR (400 MHz, DMSO-$d_6$) δ 2.36 (m, 2H), 3.58 (m, 2H), 4.17 (s, 2H), 4.33 (br s, 2H), 6.37 (br s, 1H), 6.67 (m, 1H), 7.09 (d, 1H), 7.42 (m, 3H), 8.28 (d, 1H), 11.74 (br s, 1H). (ESI) m/e 370.2 (M+H)+.

EXAMPLE 758

4-(5-fluoro-2-methoxyphenyl)-2-[1-(methylsulfonyl)azepan-4-yl]-1H-pyrrolo[2,3-b]pyridine The title compound was prepared as described in Example 275, substituting Example 734 for Example 236G. $^1$H NMR (400 MHz, DMSO-$d_6$) δ 1.24 (m, 2H), 1.62-2.40 (complex series of m, 4H), 2.79 (s, 3H), 2.79-3.14 (m, 2H), 3.15-3.27 (m, 1H), 3.40-3.71 (m, 2H), 3.73 (s, 3H), 5.98 (d, J=2.1 Hz, 1H), 7.01 (d, J=5.0 Hz, 1H), 7.14-7.33 (m, 3H), 8.14 (d, J=5.0 Hz, 1H), 11.60 (br s, 1H); MS (ESI+) m/z 418 (M+H)+.

EXAMPLE 759

{3-[4-(5-fluoro-2-methoxyphenyl)-1H-pyrrolo[2,3-b]pyridin-2-yl]-2,5-dihydro-1H-pyrrol-1-yl}acetic acid

EXAMPLE 759A tert-butyl 3-(4-(5-fluoro-2-methoxyphenyl)-1-tosyl-1H-pyrrolo[2,3-b]pyridin-2-yl)-2,5-dihydro-1H-pyrrole-1-carboxylate A mixture of Example 258C (1.40 g, 2.68 mmol), tert-butyl 3-(4,4,5,5-tetramethyl-1,3,2-dioxaborolan-2-yl)-2,5-dihydro-1H-pyrrole-1-carboxylate (0.973 g, 3.30 mmol), Pd(1,1'-bis(diphenylphosphino)ferrocene)Cl$_2$CH$_2$Cl$_2$ (92.3 mg, 0.113 mmol) and aqueous sodium carbonate solution (3 M, 3 mL, 9.00 mmol) in dioxane was flushed with N$_2$ and stirred at 100° C. for 2 hours. The cooled reaction mixture was filtered through diatomaceous earth to remove the solids. The filtrate was concentrated and the residue was purified by flash chromatography on Analogix IntelliFlash$^{280}$ eluting with 40% ethyl acetate in hexanes to give the title compound. MS (ESI+) m/z 564 (M+H)+.

EXAMPLE 759B 2-(2,5-dihydro-1H-pyrrol-3-yl)-4-(5-fluoro-2-methoxyphenyl)-1H-pyrrolo[2,3-b]pyridine To a mixture of Example 759A (1.42 g, 2.52 mmol) in dioxane (4 mL) was added a solution of sodium hydroxide (0.333 g, 8.33 mmol) in 2 mL of water. The reaction mixture was stirred at 90° C. for 4.5 hours and concentrated in vacuo. The residue was partitioned between ethyl acetate and water. The aqueous phase was extracted with ethyl acetate. The combined organic phases were washed with brine, dried over magnesium sulfate, filtered, and concentrated to give the intermediate. The intermediate was dissolved in CH$_2$Cl$_2$ and then trifluoroacetic acid (4 mL, 51.9 mmol) was added. The mixture was stirred at room temperature for 24 hours and concentrated in vacuo. The residue was dissolved in methanol and a solution of 2 M hydrogen chloride in ether was added until the solution was cloudy. The mixture was concentrated in vacuo to provide the title compound as the bishydrochloride salt. MS (ESI+) m/z 310 (M+H)+.

EXAMPLE 759C

{3-[4-(5-fluoro-2-methoxyphenyl)-1H-pyrrolo[2,3-b]pyridin-2-yl]-2,5-dihydro-1H-pyrrol-1-yl}acetic acid A mixture of Example 759B (0.0283 g, 0.075 mmol), methyl 2-bromoacetate (8.09 μl, 0.078 mmol) and triethylamine (0.052 ml, 0.373 mmol) in dimethylformamide (0.5 mL) was stirred at room temperature for 2 hours. The reaction mixture was concentrated in vacuo. To the residue were added tetrahydrofuran/methanol (1/1, 0.2 mL) and lithium hydroxide (0.225 mL, 0.225 mmol). The reaction mixture was stirred at room temperature for 1 day and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the trifluoroacetate salt. $^1$H NMR (400 MHz, DMSO-d$_6$) δ ppm 3.74 (s, 3 H) 4.37 (s, 2 H) 4.44-5.04 (m, 4 H) 6.41 (d, J=2.14 Hz, 1 H) 6.50 (s, 1 H) 7.11 (d, J=4.88 Hz, 1 H) 7.18-7.26 (m, 2 H) 7.26-7.33 (m, 1 H) 8.29 (d, J=5.19 Hz, 1 H) 11.02 (s, 1 H) 12.24 (d, J=1.83 Hz, 1 H). MS (ESI$^+$) m/z 368 (M+H)$^+$.

EXAMPLE 760

2-{4-[4-(5-fluoro-2-methoxyphenyl)-1H-pyrrolo[2,3-b]pyridin-2-yl]piperidin-1-yl}-N,N-dimethyl-ethanesulfonamide To a suspension of Example 17G (200 mg, 0.502 mmol) in N,N-dimethylformamide (5 mL) was added triethylamine (0.21 mL, 1.506 mmol) and N,N-dimethylethenesulfonamide (81 mg, 0.603 mmol). The reaction mixture was heated at 60° C. for 3 days. After cooling, the mixture was partitioned between ethyl acetate and brine. The organic phase was washed with brine, and concentrated. The residue was separated by flash chromatography (10-20% methanol in 2:1 ethyl acetate/heptane) to provide the title compound. $^1$H NMR (400 MHz, DMSO-d$_6$): δ1.62-1.73 (m, 2 H), 1.99 (d, J=11.90 Hz, 2 H), 2.10 (t, J=10.68 Hz, 2 H), 2.66-2.71 (m, 2 H), 2.78 (s, 6 H), 2.96 (d, J=11.29 Hz, 2 H), 3.20-3.25 (m, 2 H), 3.73 (s, 3 H), 5.96 (d, J=1.53 Hz, 1 H), 7.01 (d, J=4.88 Hz, 1 H), 7.16-7.28 (m, 3 H), 8.14 (d, J=4.88 Hz, 1 H), 11.58 (s, 1 H); MS (ESI) m/z 461 (M+H)$^+$, 459 (M−1)$^−$.

EXAMPLE 761

{4-[4-(2,4-dimethoxyphenyl)-1H-pyrrolo[2,3-b]pyridin-2-yl]-3,6-dihydropyridin-1(2H)-yl}acetic acid To Example 622 and N-ethyl-N-isopropylpropan-2-amine (128 μl, 0.735 mmol) in 2 mL N,N-dimethylformamide was added methyl 2-bromoacetate (43.1 mg, 0.282 mmol). The reaction mixture was stirred at room temperature overnight. The reaction mixture was extracted with dichloromethane. The organics were washed with brine and dried with MgSO$_4$, and filtered. The filtrate was concentrated to dryness. The residue in 1 mL methanol was added 1N aqueous NaOH (1 mL, 1 mmol) and the mixture was stirred at room temperature overnight. The crude product was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as trifluoroacetic acid salt. $^1$NMR (400 MHz, DMSO-d$_6$) δ 2.83 (d, J=6.1 Hz, 2H), 3.58 (s, 2H), 3.77 (s, 3H), 3.85 (s, 3H), 4.03 (d, J=5.8 Hz, 2H), 4.21 (s, 2H), 6.38 (d, J=1.9 Hz, 1H), 6.44 (d, J=3.6 Hz, 1H), 6.68 (dd, J=8.5, 2.4 Hz, 1H), 6.75 (d, J=2.3 Hz, 1H), 7.06 (d, J=4.5 Hz, 1H), 7.35 (d, J=8.4 Hz, 1H), 8.22 (d, J=5.1 Hz, 1H), 12.02 (d, J=2.4 Hz, 1H). MS (ESI$^+$) m/z 394 (M+H)$^+$.

EXAMPLE 762

{4-[4-(2-methoxyphenyl)-1H-pyrrolo[2,3-b]pyridin-2-yl]-3,6-dihydropyridin-1(2H)-yl}acetic acid The title compound was prepared as the procedure described in Example 761, substituting Example 630 for Example 622. $^1$NMR (400 MHz, DMSO-d$_6$) δ 2.81 (d, J=6.5 Hz, 2H), 3.58 (s, 2H), 3.77 (s, 3H), 3.97 (s, 2H), 4.21 (s, 2H), 6.35 (d, J=1.9 Hz, 1H), 6.45 (d, J=3.7 Hz, 1H), 7.00-7.30 (m, 3H), 7.36-7.59 (m, 2H), 8.25 (d, J=5.0 Hz, 1H), 12.03 (d, J=2.4 Hz, 1H). MS (ESI$^+$) m/z 364 (M+H)$^+$.

EXAMPLE 763

{4-[4-(4,5-difluoro-2-methoxyphenyl)-1H-pyrrolo[2,3-b]pyridin-2-yl]-3,6-dihydropyridin-1(2H)-yl}acetic acid The title compound was prepared as the procedure described in Example 761, substituting Example 627 for Example 622. $^1$H NMR (400 MHz, DMSO-d$_6$) δ 2.82 (d, J=6.4 Hz, 2H), 3.58 (s, 2H), 3.77 (s, 3H), 4.03 (d, J=12.6 Hz, 2H), 4.21 (s, 2H), 6.39 (d, J=1.9 Hz, 1H), 6.45 (d, J=3.7 Hz, 1H), 7.07 (d, J=4.9 Hz, 1H), 7.30-7.56 (m, 2H), 8.25 (d, J=4.9 Hz, 1H), 12.06 (dd, J=18.0, 2.4 Hz, 1H). MS (ESI$^+$) m/z 400 (M+H)$^+$.

EXAMPLE 765 methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate

EXAMPLE 765A methyl 2-(4-nitro-1H-pyrazol-1-yl)acetate

A suspension of 4-nitro-1H-pyrazole (1 g, 8.84 mmol), methyl 2-bromoacetate (1.556 g, 10.17 mmol), and potassium carbonate (1.833 g, 13.27 mmol) in acetone (44 ml) was heated at reflux for 5 hours. The cooled reaction was filtered with acetone washes. The filtrate was concentrated and the residue was purified by flash chromatography on silica gel (AnaLogix IntelliFlash 280 system) eluting with a gradient of from 5% to 35% ethyl acetate in heptanes to afford the title compound. MS (DCI$^+$) m/z 185.9 (M+H)$^+$.

EXAMPLE 765B methyl 2-(4-amino-1H-pyrazol-1-yl)acetate

A mixture of Example 765A (1.628 g, 8.79 mmol) and 5% palladium on carbon (wet, 0.326 g) in methanol (60 mL) was stirred in a pressure bottle under 50 psi hydrogen gas for 16 hours. The mixture was filtered through a nylon membrane and concentrated. The residue was purified by flash chromatography on silica gel (AnaLogix IntelliFlash 280 system) eluting with a gradient of from 0% to 10% methanol in dichloromethane to afford the title compound. MS (DCI$^+$) m/z 156.0 (M+H)$^+$.

EXAMPLE 765C methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate The title compound was prepared essentially as described in Example 701, substituting Example 765B for 1-(2-(methylsulfonyl)ethyl)-1H-pyrazol-4-amine dihydrochloride. $^1$H NMR (500 MHz, DMSO-d$_6$) δ ppm 2.45-2.58 (m, 2H), 3.55-3.64 (m, 2H), 3.66 (s, 3H), 3.74 (s, 3H), 4.11-4.18 (m, 2H), 4.99 (s, 2H), 6.27 (d, J=2.1 Hz, 1H), 6.53-6.60 (m, 1H), 7.04 (d, J=4.9 Hz, 1H), 7.15-7.33 (m, 3H), 7.43 (s, 1H), 7.78 (s, 1H), 8.21 (d, J=5.0 Hz, 1H), 8.61 (s, 1H), 11.85 (d, J=2.2 Hz, 1H). MS (ESI$^+$) m/z 505.1 (M+H)$^+$.

EXAMPLE 766

{4-[({4-[4-(5-fluoro-2-methoxyphenyl)-1H-pyrrolo [2,3-b]pyridin-2-yl]-3,6-dihydropyridin-1(2H)-yl}carbonyl)amino]-1H-pyrazol-1-yl}acetic acid A mixture of Example 765 (0.078 g, 0.155 mmol) and aqueous 2 M lithium hydroxide (0.232 ml, 0.464 mmol in tetrahydrofuran (0.5 ml) and methanol (0.5 ml) was stirred at room temperature for 16 hours. The reaction mixture was treated with 0.3 mL water and 1 mL ether and the suspension was filtered. The solid collected was washed with ether and dried under vacuum to afford the title compound as a lithium carboxylate salt. $^1$H NMR (500 MHz, DMSO-d$_6$) δ ppm 2.45-2.58 (m, 2H), 3.61 (t, J=5.7 Hz, 2H), 3.74 (s, 3H), 4.10-4.17 (m, 2H), 4.25 (s, 2H), 6.26 (s, 1H), 6.52-6.59 (m, 1H), 7.03 (d, J=4.9 Hz, 1H), 7.15-7.33 (m, 4H), 7.57 (s, 1H), 8.20 (d, J=4.9 Hz, 1H), 8.48 (s, 1H), 11.85 (d, J=2.2 Hz, 1H). MS (ESI$^+$) m/z 491.1 (M+H)$^+$.

EXAMPLE 768

4-[4-(5-fluoro-2-methoxyphenyl)-1H-pyrrolo[2,3-b]pyridin-2-yl]-N-(phenylsulfonyl)-3,6-dihydropyridine-1(2H)-carboxamide To a solution Example 87D (250 mg, 0.631 mmol) in N,N-dimethylformamide was added benzenesulfonyl isocyanate (0.253 mL, 1.893 mmol), and N-ethyl-N-isopropylpropan-2-amine (0.551 mL, 3.15 mmol). The reaction mixture was stirred at room temperature for 3 hours, and then diluted with ethyl acetate. The organics were washed with sodium bicarbonate, water, and brine, dried over magnesium sulfate, filtered, and concentrated. The crude material was purified via flash chromatography, (Analogix280, 12 g silica column, 2% to 8% methanol/dichloromethane gradient over 30 minutes) to give the title compound. $^1$H NMR (400 MHz, DMSO-d$_6$) δ ppm 11.99 (s, 1 H) 11.05 (s, 1 H) 8.13-8.32 (m, 1 H) 7.89-8.00 (m, 2 H) 7.51-7.73 (m, 3 H) 7.15-7.34 (m, 3 H) 7.10 (d, J=4.88 Hz, 1 H) 6.48 (s, 1 H) 6.30 (d, J=1.53 Hz, 1 H) 4.06 (s, 2 H) 3.67-3.79 (m, 3 H) 3.46-3.62 (m, 2 H). MS (ESI): 507.0 (M+H)$^+$.

EXAMPLE 769

5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one

EXAMPLE 769A 4-(4-(5-fluoro-2-methoxyphenyl)-1H-pyrrolo[2,3-b]pyridin-2-yl)cyclohex-3-enecarbohydrazide A suspension of Example 219B (0.1 g, 0.254 mmol) and hydrazine hydrate (0.35 g, 3.8 mmol) was heated to 120° C. for 16 hours, cooled, and diluted with ethyl acetate. The organics were washed with water, and filtered. The aqueous layer was extracted with dichloromethane. The organics were dried over magnesium sulfate, filtered, and concentrated. This residue was combined with the filtered solid to give the titled compound. LCMS (APCI): 381.4 (M+H)$^+$.

EXAMPLE 769B

5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one A suspension of Example 769A (100 mg, 0.263 mmol), di(1H-imidazol-1-yl) methanone (63.9 mg, 0.394 mmol) and N-ethyl-N-isopropylpropan-2-amine (0.092 ml, 0.526 mmol) in tetrahydrofuran/water (4 mL/0.4 mL) was stirred at reflux overnight, at which point an additional equivalent of di(1H-imidazol-1-yl) methanone was added, and the reaction stirred at reflux for 6 hours more. The reaction was cooled, diluted with ethyl acetate, washed with sodium bicarbonate, water, brine, dried over magnesium sulfate, filtered, and concentrated. The crude material was triturated with ethyl acetate and the solid was filtered to give the titled compound. $^1$H NMR (400 MHz, DMSO-d$_6$) δ ppm 12.10 (s, 1 H) 11.77 (s, 1 H) 8.18 (d, J=4.88 Hz, 1 H) 7.12-7.34 (m, 3 H) 7.02 (d, J=4.88 Hz, 1 H) 6.54 (s, 1 H) 6.14-6.30 (m, 1 H) 3.74 (s, 3 H) 2.91-3.05 (m, 1 H) 2.36-2.67 (m, 4 H) 2.05-2.19 (m, 1 H) 1.68-1.86 (m, 1 H). MS (ESI): 407.2 (M+H)$^+$.

EXAMPLE 770

{4-[4-(5-fluoro-2-methoxyphenyl)-1H-pyrrolo[2,3-b]pyridin-2-yl]piperidin-1-yl}acetic acid The title compound was prepared as described in Example 759C, substituting Example 17G for Example 759B. $^1$H NMR (500 MHz, DMSO-d$_6$) δ ppm 1.87-2.12 (m, 2 H) 2.16-2.34 (m, 2 H) 2.99-3.13 (m, 1 H) 3.14-3.33 (m, 2 H) 3.49-3.69 (m, 2 H) 3.75 (s, 3 H) 4.16 (s, 2 H) 6.07 (s, 1 H) 7.09 (d, J=5.19 Hz, 1 H) 7.18-7.25 (m, 2 H) 7.25-7.33 (m, 1 H) 8.21 (d, J=5.19 Hz, 1 H) 9.93 (s, 1 H) 11.84 (s, 1 H). MS (ESI$^+$) m/z 384 (M+H)$^+$.

EXAMPLE 771

{3-[4-(5-fluoro-2-methoxyphenyl)-1H-pyrrolo[2,3-b]pyridin-2-yl]pyrrolidin-1-yl}acetic acid The title compound was prepared as described in Example 759C substituting Example 59F for Example 759B. $^1$H NMR (501 MHz, DMSO-d$_6$) δ ppm 2.20-2.30 (m, 1 H) 2.50-2.56 (m, 1 H) 3.47-3.62 (m, 3 H) 3.73 (s, 3 H) 3.79-3.95 (m, 2 H) 4.22 (s, 2 H) 6.21 (s, 1 H) 7.07 (d, J=5.14 Hz, 1 H) 7.11-7.30 (m, 3 H) 8.21 (d, J=4.95 Hz, 1 H) 8.39 (s, 1 H) 11.62 (s, 1 H). MS (ESI$^+$) m/z 370 (M+H)$^+$.

EXAMPLE 772

4-[4-(5-fluoro-2-methoxyphenyl)-1H-pyrrolo[2,3-b]pyridin-2-yl]-2,5-dihydro-1H-pyrrole-2-carboxylic acid

EXAMPLE 772A (R)-1-tert-butyl 2-methyl 4-(((trifluoromethyl)sulfonyl)oxy)-1H-pyrrole-1,2(2H,5H)-dicarboxylate To a stirred solution of sodium bis(trimethylsilyl)amide (4522 µL, 4.52 mmol) in 2.67 mL of dry tetrahydrofuran, at −78° C. was slowly added (R)-1-tert-butyl 2-methyl 4-oxopyrrolidine-1,2-dicarboxylate (1 g, 4.11 mmol) in 2 mL of tetrahydrofuran. The mixture was stirred for 30 minutes at −78° C. and a solution of N,N-bis(trifluoromethylsulfonyl) aniline (1.615 g, 4.52 mmol) in tetrahydrofuran (3.33 mL) was slowly added. The mixture was stirred at −78° C. for 90 minutes and slowly warmed to 0° C. The mixture was quenched with 5 mL water and was partitioned between water (20 mL) and diethyl ether (20 mL). The organic layer was removed and the aqueous layer was extracted with 20 mL of diethyl ether. The combined organic extracts were washed with brine, dried over magnesium sulfate, filtered and concentrated under vacuum. Purification by silica gel flash chromatography (Isco®, 80 G Redi-Sep® column, 0-70% ethyl acetate/hexane linear gradient) afforded the title compound. $^1$H NMR (400 MHz, dimethylsulfoxide-$d_6$) δ 12.60 (s, 1H), 11.01 (s, 1H), 9.40 (s, 1H), 8.34 (d, J=5.2 Hz, 1H), 7.38-7.16 (m, 4H), 6.70 (q, J=2.0 Hz, 1H), 6.63 (d, J=1.3 Hz, 1H), 5.33 (s, 1H), 4.53-4.37 (m, 2H), 3.76 (s, 3H).

EXAMPLE 772B (2R)-1-tert-butyl 2-methyl 4-(4-(5-fluoro-2-methoxyphenyl)-1H-pyrrolo[2,3-b]pyridin-2-yl)-1H-pyrrole-1,2(2H,5H)-dicarboxylate A mixture of Example 772A (100 mg, 0.266 mmol), 4,4,4',4',5,5,5',5'-octamethyl-2,2'-bi(1,3,2-dioxaborolane) (67.7 mg, 0.266 mmol), 1,1'-bis(diphenylphosphino)ferrocene-palladium(II)dichloride dichloromethane complex (13.06 mg, 0.016 mmol) and potassium acetate (131 mg, 1.332 mmol) in dioxane (1.3 mL) was evacuated and backfilled with nitrogen twice, and stirred at 120° C. for 30 minutes. After cooling to ambient temperature, Example 87B (135 mg, 0.266 mmol) was added followed by another portion of 1,1'-bis(diphenylphosphino)ferrocene-palladium (II)dichloride dichloromethane complex (13.06 mg, 0.016 mmol) and aqueous sodium carbonate (2 M, 733 μL, 1.465 mmol) and the mixture was stirred at 60 C for 3 hours. After cooling to ambient temperature, the mixture was diluted with 25 mL of ethyl acetate and was washed with 25 mL 1M aqueous phosphoric acid and 20 mL brine, dried over magnesium sulfate, filtered and concentrated. Purification by silica gel flash chromatography (Isco®, 12 G Redi-Sep® column, 2-60% ethyl acetate/hexane, linear gradient) afforded the title compound. MS (ESI$^+$) m/z 608.3 (M+H)$^+$.

EXAMPLE 772C

4-[4-(5-fluoro-2-methoxyphenyl)-1H-pyrrolo[2,3-b]pyridin-2-yl]-2,5-dihydro-1H-pyrrole-2-carboxylic acid To a solution of Example 772B (100 mg, 0.165 mmol) in dioxane (1.4 mL) was added 5M aqueous sodium hydroxide (296 μL, 1.481 mmol) and the mixture was heated at 90° C. for 3 hours. The mixture was poured into 25 mL 1M aqueous phosphoric acid and 25 mL ethyl acetate and the aqueous phase was removed. The organic layer was washed with brine, dried over magnesium sulfate, filtered and concentrated. Purification by silica gel flash chromatography (Isco®, 12 G Redi-Sep® column, 50-100% ethyl acetate/hexane (quick gradient) then 10% of a 2:1 mixture methanol:water in ethyl acetate) afforded the protected intermediate. The intermediate was dissolved in 1.5 mL 50% dichloromethane/ethyl acetate, and 3 mL 2M hydrogen chloride in diethyl ether was added and the mixture was stirred at 40° C. overnight. The mixture was cooled to 0° C., stirred for 5 minutes, filtered, washed with 10 mL diethyl ether and dried under high vacuum to yield the title compound. $^1$H NMR (400 MHz, dimethylsulfoxide-$d_6$) δ 12.60 (s, 1H), 11.01 (s, 1H), 9.40 (s, 1H), 8.34 (d, J=5.2 Hz, 1H), 7.38-7.18 (m, 4H), 6.70 (q, J=2.0 Hz, 1H), 6.63 (d, J=1.3 Hz, 1H), 5.33 (s, 1H), 4.52-4.38 (m, 2H), 3.76 (s, 3H). MS (ESI$^+$) m/z 354.3 (M+H)$^+$.

EXAMPLE 775

3-{5-[4-(2,3-difluorophenyl)-1H-pyrrolo[2,3-b]pyridin-2-yl]-3,6-dihydropyridin-1(2H)-yl}propane-1,2-diol Example 755C (91 mg, 0.24 mmol), triethylamine (0.07 mL, 0.5 mmol) and acetic acid (0.07 mL, 1.2 mmol) were dissolved in dichloromethane (4 mL) and the mixture was stirred for 15 minutes. To the reaction was added DL-glyceraldehyde (43 mg, 0.48 mmol) and polymer-bound sodium cyanoborohydride (400 mg, 2.49 mmol/g). After stirring for 24 hours at room temperature, the reaction was filtered and concentrated. Purification by flash chromatography on silica gel eluting with 10% methanol-dichloromethane provided the title compound. $^1$HNMR (400 MHz, DMSO-$d_6$) δ 2.32 (m, 2H), 2.45 (m, 2H), 2.64 (m, 2H), 3.37 (m, 2H), 3.75 (m, 1H), 4.51 (m, 2H), 6.31 (s, 1H), 6.60 (br s, 1H), 7.11 (d, 1H), 7.43 (m, 2H), 7.56 (m, 1H), 8.26 (d, 1H), 11.97 (br s, 1H). MS (ESI) m/e 386.2 (M+H)$^+$.

EXAMPLE 776

1-{5-[4-(2,3-difluorophenyl)-1H-pyrrolo[2,3-b]pyridin-2-yl]-3,6-dihydropyridin-1(2H)-yl})-2-hydroxy-2-methylpropan-1-one The title compound was prepared using the procedure described in Example 757 using 2-hydroxyisobutyric acid in place of glycolic acid. $^1$H NMR (400 MHz, DMSO-$d_6$) δ 1.33 (br s, 6H), 2.35 (m, 2H), 4.03 (m, 2H), 4.34 (m, 2H), 5.48 9br s, 1H), 6.31 (m, 1H), 6.70 (m, 1H), 7.13 (d, 1H), 7.46 (m, 3H), 8.29 (d, 1H), 12.06 (br s, 1H). MS (ESI) m/e 398.1 (M+H)$^+$.

EXAMPLE 777

{4-[4-(4-fluoro-2-methoxyphenyl)-1H-pyrrolo[2,3-b]pyridin-2-yl]-3,6-dihydropyridin-1(2H)-yl}acetic acid The title compound was prepared as the procedure described in Example 761, substituting Example 658 for Example 622. $^1$H NMR (400 MHz, DMSO-$d_6$) δ 2.83 (d, J=5.9 Hz, 2H), 3.56 (d, J=32.5 Hz, 2H), 3.78 (s, 3H), 4.10 (br, 2H), 4.22 (s, 2H), 6.35 (d, J=2.0 Hz, 1H), 6.45 (d, J=3.6 Hz, 1H), 6.84-7.23 (m, 3H), 7.38-7.51 (m, 1H), 8.24 (d, J=4.7 Hz, 1H), 12.01 (d, J=2.3 Hz, 1H). MS (ESI$^+$) m/z 382 (M+H)$^+$.

EXAMPLE 778

{3-[4-(5-fluoro-2-methoxyphenyl)-1H-pyrrolo[2,3-b]pyridin-2-yl]-8-azabicyclo[3.2.1]oct-2-en-8-yl}acetic acid

EXAMPLE 778A tert-butyl 2-(3-(4-(5-fluoro-2-methoxyphenyl)-1H-pyrrolo[2,3-b]pyridin-2-yl)-8-azabicyclo[3.2.1]oct-3-en-8-yl)acetate A mixture of Example 223C (100.0 mg, 0.237 mmol), tert-butyl 2-bromoacetate (0.041 mL, 0.284 mmol), and triethylamine (0.165 mL, 1.184 mmol) in N,N-dimethylformamide (2 mL) was heated at 80° C. for 30 minutes in a Biotage Initiator microwave reactor (model 355302). The reaction mixture was treated with water and brine and extracted with ethyl acetate. The combined organic layers were washed with water and brine, dried over MgSO$_4$, filtered, concentrated, and purified on a 12 g silica column using the ISCO Companion flash system eluting with heptanes/ethyl acetate (1:9 to 0:10) to provide the title compound. MS (ESI$^+$) m/z 464.0 (M+H)$^+$.

EXAMPLE 778B

{3-[4-(5-fluoro-2-methoxyphenyl)-1H-pyrrolo[2,3-b]pyridin-2-yl]-8-azabicyclo[3.2.1]oct-2-en-8-yl}acetic acid A solution of Example 778A (90.0 mg, 0.194 mmol) and trifluoroacetic acid (0.150 mL, 1.942 mmol) in CH$_2$Cl$_2$ (3 mL) was heated at 40° C. in a capped vial overnight. The reaction was concentrated and purified by HPLC (see protocols in Example 361) to provide the title compound as a trifluoroacetic acid salt. $^1$H NMR (500 MHz, methanol-d$_4$) δ ppm 2.04-2.14 (m, 1H), 2.33-2.56 (m, 3H), 2.82-2.86 (m, 1H), 3.13-3.41 (m, 1H), 3.80 (s, 3H), 4.03-4.30 (m, 2H), 4.34-4.40 (m, 1H), 4.47-4.66 (m, 1H), 6.57-6.83 (m, 2H), 7.18-7.30 (m, 3H), 7.40 (d, J=5.7 Hz, 1H), 8.32 (d, J=5.7 Hz, 1H). MS (ESI$^+$) m/z 408.0 (M+H)$^+$.

EXAMPLE 779

1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylic acid The title compound was prepared using the procedure described in Example 647B, using Example 749 (0.08 g, 0.11 mmol) in place of Example 647A. $^1$H NMR (400 MHz, DMSO-d$_6$): δ 1.52-1.60 (m, 1 H) 1.78-1.89 (m, 1 H) 3.01-3.14 (m, 2 H) 3.30-3.41 (m, 5 H) 3.73-3.76 (m, 5 H) 6.28 (d, J=1.83 Hz, 1 H) 6.49-6.54 (m, 1 H) 7.09 (d, J=4.88 Hz, 1 H) 7.18-7.33 (m, 3 H) 8.22 (d, J=4.88 Hz, 1 H) 11.95 (s, 1 H). MS (ESI$^+$) m/z 495.1 (M+H)$^+$.

EXAMPLE 780

1-{5-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one The title compound was prepared using the procedure described in Example 100, using Example 485 (0.082 g, 0.21 mmol) in place of Example 87D and 2-hydroxy-2-methylpropanoic acid in place of acetic acid. $^1$H NMR (400 MHz, DMSO-d$_6$): δ 1.33 (s, 6 H) 2.26-2.41 (m, 2 H) 3.75 (s, 3 H) 3.93-4.13 (m, 1 H) 4.21-4.44 (m, 1 H) 5.47 (s, 1 H) 6.17 (s, 1 H) 6.62-6.68 (m, 1 H) 7.04 (d, J=5.19 Hz, 1 H) 7.17-7.32 (m, 3 H) 8.22 (d, J=4.88 Hz, 1 H) 11.88 (s, 1 H). MS (ESI$^+$) m/z 410.2 (M+H)$^+$.

EXAMPLE 784 tert-butyl {4-[4-(5-fluoro-2-methoxyphenyl)-1H-pyrrolo[2,3-b]pyridin-2-yl]-3,6-dihydropyridin-1(2H)-yl}acetate The title compound was prepared as described in Example 226A. $^1$H NMR (500 MHz, DMSO-d$_6$) δ ppm 1.43 (s, 9H), 2.42-2.50 (m, 2H), 2.74 (t, J=5.7 Hz, 2H), 3.20-3.27 (m, 4H), 3.74 (s, 3H), 6.19 (d, J=1.9 Hz, 1H), 6.43-6.50 (m, 1H), 7.02 (d, J=4.9 Hz, 1H), 7.14-7.32 (m, 3H), 8.19 (d, J=4.9 Hz, 1H), 11.74-11.80 (m, 1H). MS (ESI$^+$) m/z 438.1 (M+H)$^+$.

EXAMPLE 785

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}-3,6-dihydropyridine-1(2H)-carboxamide The title compound was prepared essentially as described in Example 701, substituting (R)-1-(4-amino-1H-pyrazol-1-yl)propan-2-ol for 1-(2-(methylsulfonyl)ethyl)-1H-pyrazol-4-amine dihydrochloride. $^1$H NMR (400 MHz, DMSO-d$_6$) δ ppm 0.93-1.06 (m, 3H), 2.45-2.58 (m, 2H), 3.61 (t, J=5.6 Hz, 2H), 3.74 (s, 3H), 3.82-3.98 (m, 3H), 4.10-4.25 (m, 2H), 4.79-4.89 (m, 1H), 6.27 (d, J=2.0 Hz, 1H), 6.51-6.60 (m, 1H), 7.04 (d, J=4.9 Hz, 1H), 7.14-7.34 (m, 3H), 7.38 (d, J=0.6 Hz, 1H), 7.70 (s, 1H), 8.20 (d, J=4.9 Hz, 1H), 8.54 (s, 1H), 11.83 (d, J=2.3 Hz, 1H). MS (ESI$^+$) m/z 491.2 (M+H)$^+$.

EXAMPLE 786

4-(5-fluoro-2-methoxyphenyl)-2-[1-(2H-tetrazol-5-ylmethyl)-1,2,3,6-tetrahydropyridin-4-yl]-1H-pyrrolo[2,3-b]pyridine A mixture of Example 87D (0.065 g, 0.164 mmol) and N-ethyl-N-isopropylpropan-2-amine (0.172 ml, 0.984 mmol) in N,N-dimethylformamide (1 mL) was treated with potassium carbonate (0.045 g, 0.328 mmol) and 5-(chloromethyl)-2H-tetrazole (0.039 g, 0.328 mmol) and the mixture was stirred at room temperature for 16 hours. The reaction mixture was filtered and the filtrate was concentrated. The concentrate was purified by reverse phase HPLC on a Phenomenex Luna C8(2) 5 um 100 Å AXIA column (30 mm×75 mm) eluting with a gradient of 10-95% acetonitrile in 0.1% ammonium acetate/water to afford the title compound. $^1$H NMR (400 MHz, DMSO-d$_6$) δ ppm 2.50-2.61 (m, 2H), 2.80 (t, J=5.8 Hz, 2H), 3.26-3.34 (m, 2H), 3.73 (s, 3H), 4.01 (s, 2H), 6.21 (d, J=1.9 Hz, 1H), 6.38-6.50 (m, 1H), 7.02 (d, J=4.9 Hz, 1H), 7.13-7.45 (m, 3H), 8.19 (d, J=4.9 Hz, 1H), 11.79 (d, J=2.4 Hz, 1H). MS (APCI$^+$) m/z 406.3 (M+H)$^+$.

EXAMPLE 787

6-[4-(5-fluoro-2-methoxyphenyl)-1H-pyrrolo[2,3-b]pyridin-2-yl]-2-azaspiro[3.3]heptan-6-ol

EXAMPLE 787A tert-butyl 6-(4-chloro-1-tosyl-1H-pyrrolo[2,3-b]pyridin-2-yl)-6-hydroxy-2-azaspiro[3.3]heptane-2-carboxylate To a solution of 4-chloro-2-iodo-1-tosyl-1H-pyrrolo[2,3-b]pyridine (83 mg, 0.191 mmol) in tetrahydrofuran (500 mL), at −78° C. under nitrogen was added 1.6 M n-butyl lithium in hexane (251 μL, 0.401 mmol). The mixture was stirred for 2 minutes and a solution of tert-butyl 6-oxo-2-azaspiro[3.3]heptane-2-carboxylate (81 mg, 0.382 mmol) in tetrahydrofuran (250 μL) was added by syringe. The mixture was stirred at −78° C. for 1 hour and was slowly warmed to ambient temperature overnight. The mixture was poured into 15 mL saturated aqueous ammonium chloride and ethyl acetate was added (10 mL). The organic layer was washed with brine (10 mL), dried over magnesium sulfate, filtered and concentrated. Purification by silica gel flash chromatography (Isco®, Redi-Sep® column, 0-70% ethyl acetate/hexane, linear gradient) afforded the title compound. $^1$H NMR (500 MHz, dimethylsulfoxide-$d_6$) δ 8.29 (d, J=5.3 Hz, 1H), 8.20-8.13 (m, 2H), 7.44-7.35 (m, 3H), 6.88 (s, 1H), 5.83 (s, 1H), 3.96 (s, 2H), 3.80 (s, 2H), 3.05 (d, J=12.9 Hz, 2H), 2.65 (d, J=12.5 Hz, 2H), 2.34 (s, 3H), 1.37 (s, 9H). MS (ESI$^+$) m/z 518.3 (M+H)$^+$.

EXAMPLE 787B tert-butyl 6-(4-(5-fluoro-2-methoxyphenyl)-1-tosyl-1H-pyrrolo[2,3-b]pyridin-2-yl)-6-hydroxy-2-azaspiro[3.3]heptane-2-carboxylate A mixture of Example 787A (260 mg, 0.502 mmol), (5-fluoro-2-methoxyphenyl)boronic acid (111 mg, 0.652 mmol), potassium phosphate tribasic (320 mg, 1.506 mmol) and phenylallylchloro[1,3-bis(diisopropylphenyl)-2-imidazol-2-ylidene]palladium(II) (9.75 mg, 0.015 mmol) in tetrahydrofuran (7.38 mL) and water (2.46 mL) was degassed and heated at 60° C. for 3 hours. After cooling to ambient temperature, the mixture was poured into 25 mL of ethyl acetate and the organic layer was washed with water (1×20 mL) and brine (1×20 mL), dried over magnesium sulfate, filtered and concentrated. Purification by silica gel flash chromatography (Isco®, Redi-Sep® column, 15-100% ethyl acetate/hexane, linear gradient) afforded the title compound. MS (ESI$^+$) m/z 608.3 (M+H)$^+$.

EXAMPLE 787C 6-(4-(5-fluoro-2-methoxyphenyl)-1-tosyl-1H-pyrrolo[2,3-b]pyridin-2-yl)-2-azaspiro[3.3]heptan-6-ol A solution of Example 787B (146 mg, 0.240 mmol) in 1.5 mL dichloromethane was treated with 1 mL trifluoroacetic acid. After stirring at ambient temperature for 10 minutes the mixture was concentrated. The crude material was dissolved in 15 mL ethyl acetate, washed with saturated aqueous sodium bicarbonate (2×10 mL) and brine (1×10 mL), dried over sodium sulfate, filtered and concentrated to obtain the crude title compound. MS (ESI$^+$) m/z 508.3 (M+H)$^+$.

EXAMPLE 787D 6-(4-(5-fluoro-2-methoxyphenyl)-1H-pyrrolo[2,3-b]pyridin-2-yl)-2-azaspiro[3.3]heptan-6-ol To a solution of Example 787C (102 mg, 0.201 mmol) in dioxane (1.675 mL) was added 5M aqueous sodium hydroxide (362 µL, 1.809 mmol) and the mixture was heated at 90° C. for 3 hours. The mixture was concentrated and dissolved in 1.5 mL 1:1 methanol/water. The mixture was quenched by careful addition of trifluoroacetic acid and purified by reverse phase preparative HPLC (Phenomenex Luna C8(2) 100 Å AXIA column) eluting with a gradient of 5-100% acetonitrile/0.1% trifluoroacetic acid in water to provide the title compound as the bis-trifluoroacetate salt. $^1$H NMR (500 MHz, dimethylsulfoxide-$d_6$) δ 11.89 (s, 1H), 8.60 (s, 2H), 8.24 (d, J=5.1 Hz, 1H), 7.49 (d, J=7.8 Hz, 1H), 7.35-7.26 (m, 1H), 7.26-7.18 (m, 2H), 7.17-7.08 (m, 2H), 6.21 (d, J=1.9 Hz, 1H), 4.05 (t, J=6.2 Hz, 2H), 3.88 (t, J=6.1 Hz, 2H), 3.74 (s, 3H), 2.87-2.79 (m, 2H), 2.52-2.43 (m, 2H). MS (ESI$^+$) m/z 354.1 (M+H)$^+$.

EXAMPLE 788

{(2R)-4-[4-(5-fluoro-2-methoxyphenyl)-1H-pyrrolo[2,3-b]pyridin-2-yl]-2,5-dihydro-1H-pyrrol-2-yl}methanol

EXAMPLE 788A (2R)-tert-butyl 4-(4-(5-fluoro-2-methoxyphenyl)-1-(phenylsulfonyl)-1H-pyrrolo[2,3-b]pyridin-2-yl)-2-(hydroxymethyl)-2,5-dihydro-1H-pyrrole-1-carboxylate To a solution of Example 772B (70 mg, 0.115 mmol) in toluene (0.5 mL) at −78° C. under nitrogen was added slowly 1M diisobutylaluminum hydride in tetrahydrofuran (0.346 mL, 0.346 mmol) and the mixture was slowly warmed to 0° C. over 3 hours. An aqueous solution of Rochelle salt (potassium sodium tartrate) was added and the mixture was stirred at 0° C. for 10 minutes and diluted with 10 mL ethyl acetate. The organic layer was washed with brine, dried over magnesium sulfate, filtered and concentrated. Purification by silica gel flash chromatography (Isco®, Redi-Sep® column, 10-100% ethyl acetate/hexane) afforded the title compound. MS (ESI$^+$) m/z 580.0 (M+H)$^+$.

EXAMPLE 788B ((2R)-4-(4-(5-fluoro-2-methoxyphenyl)-1H-pyrrolo[2,3-b]pyridin-2-yl)-2,5-dihydro-1H-pyrrol-2-yl)methanol To a solution of Example 788A (126 mg, 0.217 mmol) in dioxane (1.81 mL) was added sodium hydroxide (391 µL, 1.956 mmol) and the mixture was heated at 90° C. for 3 hours. The mixture was poured into 25 mL 1M aqueous phosphoric acid and 25 mL ethyl acetate. The organic layer was washed with brine, dried over magnesium sulfate, filtered and concentrated to give the crude intermediate. Purification by silica gel phase chromatography (Isco®, Redi-Sep® column, 50-100% ethyl acetate hexane (quick gradient) then 10% 2:1 methanol:water in ethyl acetate) afforded the protected intermediate. The intermediate was dissolved in 1.5 mL 50% dichloromethane/ethyl acetate, 3 mL of 2M hydrogen chloride in diethyl ether was added and the mixture was stirred at 40° C. overnight. The mixture was cooled to 0° C., stirred for 5 minutes, and filtered. The solid was washed with 10 mL diethyl ether and dried under high vacuum to provide the title compound as a bis hydrochloride salt. $^1$H NMR (400 MHz, dimethylsulfoxide-$d_6$) δ 12.75 (s, 1H), 10.58-10.39 (m, 1H), 9.69-9.49 (m, 1H), 8.34 (d, J=5.3 Hz, 1H), 7.39-7.15 (m, 4H), 6.64-6.48 (m, 2H), 4.71-4.59 (m, 1H), 4.45-4.25 (m, 2H), 3.81 (dd, J=12.0, 3.8 Hz, 1H), 3.76 (s, 3H), 3.68 (dd, J=12.0, 5.8 Hz, 1H). MS (ESI$^+$) m/z 340.1 (M+H)$^+$.

EXAMPLE 790

4-[4-(5-fluoro-2-methoxyphenyl)-1H-pyrrolo[2,3-b]pyridin-2-yl]cyclohex-3-en-1-ol A mixture of Example 241B (60.0 mg, 0.178 mmol) and sodium borohydride (13.50 mg, 0.357 mmol) in methanol (2.5 mL) was stirred for 2 hours. The reaction mixture was concentrated and purified on a 12 g silica column using the ISCO Companion flash system eluting with heptanes/ethyl acetate (2:8 to 1:9) to provide the title compound. $^1$H NMR (500 MHz, pyridine-d₅) δ ppm 1.93-2.04 (m, 1H), 2.16-2.24 (m, 1H), 2.51-2.64 (m, 2H), 2.76-2.86 (m, 2H), 3.71 (s, 3H), 4.24-4.30 (m, 1H), 6.31 (d, J=4.3 Hz, 1H), 6.66 (d, J=2.0 Hz, 1H), 6.75-6.81 (m, 1H), 7.10 (dd, J=9.0, 4.5 Hz, 1H), 7.25-7.29 (m, 1H), 7.32 (d, J=5.0 Hz, 1H), 7.50-7.53 (m, 1H), 8.58 (d, J=4.9 Hz, 1H), 12.96 (bs, 1H). MS (ESI⁺) m/z 339.2 (M+H)⁺.

EXAMPLE 791

2-{3-[4-(5-fluoro-2-methoxyphenyl)-1H-pyrrolo[2,3-b]pyridin-2-yl]pyrrolidin-1-yl}-N,N-dimethylacetamide To a mixture of Example 59 (25.2 mg, 0.081 mmol), and 2-chloro-N,N-dimethylacetamide (10.34 mg, 0.085 mmol) in dimethylformamide (0.5 mL) was added N-ethyl-N-isopropylpropan-2-amine (0.071 ml, 0.405 mmol). The mixture was stirred at room temperature for 16 hours and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. ¹H NMR (400 MHz, DMSO-d₆) δ ppm 1.81-1.97 (m, 2 H) 2.15-2.29 (m, 1 H) 2.61-2.78 (m, 3 H) 2.80 (s, 3 H) 2.99 (s, 3 H) 3.21-3.53 (m, 3 H) 3.72 (s, 3 H) 6.02 (d, J=1.83 Hz, 1 H) 7.01 (d, J=4.88 Hz, 1 H) 7.12-7.33 (m, 3 H) 8.13 (d, J=5.19 Hz, 1 H) 11.54 (s, 1 H). MS (ESI⁺) m/z 397 (M+H)⁺.

EXAMPLE 792

3-[4-(5-fluoro-2-methoxyphenyl)-1H-pyrrolo[2,3-b]pyridin-2-yl]cyclopent-3-en-1-amine The title compound was prepared as described in Example 262A-E, substituting tert-butyl(3-oxocyclopentyl)carbamate for tert-butyl 5-oxohexahydrocyclopenta[c]pyrrole-2(1H)-carboxylate. The reaction mixture was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound and Example 793. ¹H NMR (400 MHz, DMSO-D6) δ ppm 2.52-2.59 (m, 1 H) 2.65-2.76 (m, 1 H) 2.89-3.01 (m, 1 H) 3.03-3.13 (m, 1 H) 3.74 (s, 3 H) 3.90-4.04 (m, 1 H) 6.24 (d, J=1.83 Hz, 1 H) 6.43 (s, 1 H) 7.09 (d, J=4.88 Hz, 1 H) 7.18-7.26 (m, 2 H) 7.26-7.33 (m, 1 H) 7.97 (s, 2 H) 8.25 (d, J=4.88 Hz, 1 H) 12.11 (s, 1 H). MS (ESI⁺) m/z 324 (M+H)⁺.

EXAMPLE 793

3-[4-(5-fluoro-2-methoxyphenyl)-1H-pyrrolo[2,3-b]pyridin-2-yl]cyclopent-2-en-1-amine The title compound was prepared as described in Example 792. ¹H NMR (400 MHz, DMSO-d₆) δ ppm 1.81-1.93 (m, 1 H) 2.32-2.44 (m, 1 H) 2.66-2.78 (m, 1 H) 2.87-2.99 (m, 1 H) 3.74 (s, 3 H) 4.37-4.46 (m, 1 H) 6.35-6.41 (m, 2 H) 7.09 (d, J=4.88 Hz, 1 H) 7.18-7.26 (m, 2 H) 7.26-7.34 (m, 1 H) 7.99 (s, 2 H) 8.28 (d, J=4.88 Hz, 1 H) 12.18 (d, J=1.53 Hz, 1 H). MS (ESI⁺) m/z 324 (M+H)⁺.

EXAMPLE 794

2-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]-1H-isoindole-1,3(2H)-dione To a solution of Example 87D (500 mg, 1.262 mmol) and 2-(1,3-dioxoisoindolin-2-yl)ethanesulfonyl chloride (345 mg, 1.262 mmol) in 10 mL N,N-dimethylformamide was added triethylamine (0.6 mL, 4.30 mmol) and the mixture was stirred overnight at room temperature. The mixture was diluted with water and the resulting precipitate was rinsed with water to yield the title compound. ¹H NMR (400 MHz, DMSO-d₆) δ 11.89 (s, 1H), 8.27 (d, J=5.0 Hz, 1H), 7.98-7.88 (m, 2H), 7.88-7.78 (m, 2H), 7.40-7.19 (m, 3H), 7.10 (d, J=4.9 Hz, 1H), 6.56 (s, 1H), 6.30 (d, J=2.0 Hz, 1H), 4.16-3.88 (m, 4H), 3.80 (s, 3H), 3.53 (dt, J=25.0, 6.2 Hz, 2H), 2.95 (s, 2H), 2.79 (s, 2H). MS (ESI+) m/e 561 (M+H)⁺.

EXAMPLE 795

3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione

EXAMPLE 795A tert-butyl (2-(2-bromo-4-fluorophenoxy)ethyl)carbamate

A solution of tert-butyl(2-hydroxyethyl)carbamate (376 mg, 2.333 mmol), 2-(tributylphosphoranylidene)acetonitrile (563 mg, 2.333 mmol) and 2-bromo-4-fluorophenol (446 mg, 2.333 mmol) in 15 mL toluene was heated overnight at 75° C. The cooled mixture was diluted with diethyl ether and rinsed with 2M aqueous NaOH, water and brine, dried over MgSO₄, filtered, and concentrated. The crude product was purified by flash column chromatography on silica (25% ethyl acetate/hexane) to yield the title compound.

EXAMPLE 795B tert-butyl 4-(4-(2-(2-((tert-butoxycarbonyl)amino)ethoxy)-5-fluorophenyl)-1-tosyl-1H-pyrrolo[2,3-b]pyridin-2-yl)-5,6-dihydropyridine-1(2H)-carboxylate The title compound was prepared using the procedure described in Example 7A, using Example 673A in place of Example 5A and Example 795A in place of 2-bromo-4-cyclopropyl-1-methoxybenzene.

EXAMPLE 795C tert-butyl 4-(4-(2-(2-((tert-butoxycarbonyl)amino)ethoxy)-5-fluorophenyl)-1H-pyrrolo[2,3-b]pyridin-2-yl)-5,6-dihydropyridine-1(2H)-carboxylate To a solution of Example 795B (385 mg, 0.545 mmol) in 4.5 mL dioxane was added 5M aqueous sodium hydroxide (0.5 mL, 2.5 mmol) and the mixture was heated at reflux for 7 hours and stirred overnight at room temperature. The mixture was partitioned between water and ethyl acetate and acidified with citric acid. The aqueous layer was extracted with ethyl acetate and the combined organics were rinsed with water and brine, dried over MgSO$_4$, filtered, and concentrated. The residue was purified by flash column chromatography on silica (2% methanol/dichloromethane) to yield the title compound.

EXAMPLE 795D 2-(4-fluoro-2-(2-(1,2,3,6-tetrahydropyridin-4-yl)-1H-pyrrolo[2,3-b]pyridin-4-yl)phenoxy)ethanamine To as solution of Example 795C (209 mg, 0.378 mmol) in 2 mL dichloromethane was added 2 mL trifluoroacetic acid and the mixture was stirred for 1 hour at room temperature. The mixture was concentrated and used in the next step without further purification.

EXAMPLE 795E 3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione To a mixture of Example 795D (125 mg, 0.355 mmol) and 3,4-diethoxycyclobut-3-ene-1,2-dione (340 mg, 1.998 mmol) in 2.5 mL ethanol in a microwave vial was added triethylamine (0.3 mL, 2.152 mmol) and the mixture was subjected to microwave irradiation using a Biotage Initiator (model 355302) at 125° C. for 30 minutes. The mixture was concentrated and the product was purified by flash column chromatography on silica (0-5% methanol/dichloromethane) to provide the title compound. $^1$H NMR (400 MHz, DMSO-d$_6$) δ 11.86 (s, 1H), 8.55 (d, J=90.4 Hz, 1H), 8.11 (d, J=4.9 Hz, 1H), 7.25 (m, 3H), 7.00 (m, 1H), 6.51 (s, 1H), 6.29 (d, J=21.4 Hz, 1H), 4.74-4.45 (m, 2H), 4.42-4.24 (m, 4H), 4.24-3.88 (m, 4H), 3.63-3.49 (m, 2H), 2.65 (m, 2H), 1.46-1.25 (m, 3H), 1.12-1.05 (m, 3H). MS (ESI$^+$) m/e 601 (M+H)$^+$.

EXAMPLE 803 ethyl ({4-[4-(2,3-difluorophenyl)-1H-pyrrolo[2,3-b]pyridin-2-yl]-3,6-dihydropyridin-1(2H)-yl}sulfonyl)carbamate The title compound was prepared essentially as described in Example 603, substituting Example 222C for Example 602. $^1$H NMR (400 MHz, DMSO-d$_6$): δ1.15 (t, J=7.02 Hz, 3 H), 2.57-2.63 (m, 2 H), 3.48 (t, J=5.65 Hz, 2 H), 4.01-4.10 (m, 4 H), 6.40 (s, 1 H), 6.55 (s, 1 H), 7.12-7.14 (m, 1 H), 7.36-7.46 (m, 2 H), 7.52-7.59 (m, 1 H), 8.29 (d, J=4.88 Hz, 1 H), 11.37 (s, 1 H), 12.03 (d, J=1.53 Hz, 1 H); MS (DCI/NH$_3$) m/z 463 (M+H)$^+$.

EXAMPLE 804

2,2,2-trifluoroethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 578, substituting 2,2,2-trifluoroethanol for ethanol in Example 578A and Example 87D for Example 17G in Example 578B. $^1$H NMR (400 MHz, DMSO-d$_6$): δ2.57-2.61 (m, 2 H), 3.49 (t, J=5.49 Hz, 2 H), 3.74 (s, 3 H), 4.03 (s, 2 H), 4.77 (q, J=9.05 Hz, 2 H), 6.27 (d, J=1.83 Hz, 1 H), 6.51 (s, 1 H), 7.05 (d, J=4.88 Hz, 1 H), 7.18-7.30 (m, 3 H), 8.22 (d, J=4.88 Hz, 1 H), 11.87 (d, J=1.22 Hz, 1 H), 11.99 (d, 1 H); MS (DCI/NH$_3$) m/z 529 (M+H)$^+$.

EXAMPLE 805

4-[4-(5-fluoro-2-methoxyphenyl)-1H-pyrrolo[2,3-b]pyridin-2-yl]cyclohex-3-en-1-one The title compound was prepared in as described in Example 241B. $^1$H NMR (400 MHz, DMSO-d$_6$) δ ppm 11.86 (d, J=2.2 Hz, 1H), 8.21 (d, J=4.9 Hz, 1H), 7.36-7.11 (m, 3H), 7.04 (d, J=5.0 Hz, 1H), 6.56 (t, J=4.0 Hz, 1H), 6.30 (d, J=2.0 Hz, 1H), 3.74 (s, 3H), 3.08 (dt, J=3.9, 1.8 Hz, 2H), 2.84 (td, J=7.1, 6.6, 1.6 Hz, 2H), 2.56-2.48 (m, 2H); MS (ESI(+)) m/e 337 (M+H).

EXAMPLE 806

2-(3,6-dihydro-2H-thiopyran-4-yl)-4-(5-fluoro-2-methoxyphenyl)-1H-pyrrolo[2,3-b]pyridine

EXAMPLE 806A 2-(3,6-dihydro-2H-thiopyran-4-yl)-4-(5-fluoro-2-methoxyphenyl)-1-(phenylsulfonyl)-1H-pyrrolo[2,3-b]pyridine The title compound was prepared using the procedure described in Example 87C, using 2-(3,6-dihydro-2H-thiopyran-4-yl)-4,4,5,5-tetramethyl-1,3,2-dioxaborolane (0.375 g, 1.66 mmol) in place of tert-butyl 4-(4,4,5,5-tetramethyl-1,3,2-dioxaborolan-2-yl)-5,6-dihydropyridine-1(2H)-carboxylate. LC/MS: 481.2 (M+H)$^+$.

EXAMPLE 806B 2-(3,6-dihydro-2H-thiopyran-4-yl)-4-(5-fluoro-2-methoxyphenyl)-1H-pyrrolo[2,3-b]pyridine The title compound was prepared using the procedure described in Example 632B, using Example 806A (0.54 g, 1.12 mmol) in place of Example 632A. $^1$H NMR (400 MHz, DMSO-d$_6$): δ 2.61-2.68 (m, 2 H) 2.82 (t, J=5.80 Hz, 2 H) 3.35 (d, J=4.27 Hz, 2 H) 3.74 (s, 3 H) 6.25 (d, J=2.14 Hz, 1 H) 6.67-6.73 (m, 1 H) 7.03 (d, J=4.88 Hz, 1 H) 7.16-7.30 (m, 3 H) 8.19 (d, J=4.88 Hz, 1 H) 11.79 (s, 1 H). MS (ESI$^+$) m/z: 341.1 (M+H)$^+$.

EXAMPLE 807

3-fluoro-N-methyl-4-[2-(1,2,3,6-tetrahydropyridin-4-yl)-1H-pyrrolo[2,3-b]pyridin-4-yl]benzamide

EXAMPLE 807A tert-butyl 4-(4-(2-fluoro-4-(methylcarbamoyl)phenyl)-1-tosyl-1H-pyrrolo[2,3-b]pyridin-2-yl)-5,6-dihydropyridine-1(2H)-carboxylate Into a 20 mL microwave tube was added Example 673A (1.2 g, 2.07 mmol), 4-bromo-3-fluoro-N-methylbenzamide (0.5 g, 2.16 mmol) and [1,1'-bis(diphenylphosphino)ferrocene]dichloropalladium(II)-dichloromethane complex (0.1 g, 0.122 mmol) in dioxane/water (3:1) (20 mL). Sodium carbonate (0.5 g, 4.72 mmol) was added. The mixture was heated at 80° C. using a Biotage Initiator (model 355302) for 5 minutes. After filtration through diatomaceous earth, the solvent was removed and the product was purified by flash chromatography on silica gel (AnaLogix IntelliFlash) eluting with a gradient of 20-100% ethyl acetate in heptanes to afford the title compound. MS (ESI$^+$) m/z 605.3 (M+H)$^+$.

EXAMPLE 807B tert-butyl 4-(4-(2-fluoro-4-(methylcarbamoyl)phenyl)-1H-pyrrolo[2,3-b]pyridin-2-yl)-5,6-dihydropyridine-1(2H)-carboxylate The title compound was prepared using the procedure described in Example 632B, using Example 807A (0.54 g, 1.12 mmol) in place of Example 632A. LCMS: 451.4 (M+H)$^+$.

EXAMPLE 807C 3-fluoro-N-methyl-4-[2-(1,2,3,6-tetrahydropyridin-4-yl)-1H-pyrrolo[2,3-b]pyridin-4-yl]benzamide Into a 20 mL round-bottomed flask was added Example 807B (0.54 g, 1.2 mmol) and trifluoroacetic acid (2 mL, 26.0 mmol) in dichloromethane (3 mL). The mixture was stirred at room temperature overnight. The solvent was dried under vacuum, and the crude product was purified by preparative reverse phase column (Analogix, C-18, 150 g) with gradient elution from 20-100% acetonitrile in water with 0.1% trifluoroacetic acid. After concentration, the material was dissolved in methanol. 2M HCl in ether (5 mL, 10 mmol) was added to the solution. A precipitate was formed, and 200 mL ether was added to the suspension. The mixture was filtered, washed with ether and dried under vacuum to provide the title compound as the hydrogen chloride salt. $^1$H NMR (400 MHz, DMSO-d$_6$): δ 2.74 (s, 2 H) 2.84 (d, J=3.97 Hz, 3 H) 3.29 (s, 2 H) 3.81 (s, 2 H) 6.52-6.57 (m, 1 H) 6.62 (s, 1 H) 7.28 (d, J=4.27 Hz, 1 H) 7.77 (t, J=7.63 Hz, 1 H) 7.85-7.93 (m, 2 H) 8.37 (d, J=4.58 Hz, 1 H) 8.78 (d, J=3.97 Hz, 1 H) 9.55 (s, 1 H) 12.61 (s, 1 H). MS (ESI$^+$) m/z 351.1 (M+H)$^+$.

EXAMPLE 808

N-({4-[4-(5-fluoro-2-methoxyphenyl)-1H-pyrrolo[2,3-b]pyridin-2-yl]-3,6-dihydropyridin-1(2H)-yl}carbonyl)alanine

EXAMPLE 808A 2,5-dioxopyrrolidin-1-yl 4-(4-(5-fluoro-2-methoxyphenyl)-1H-pyrrolo[2,3-b]pyridin-2-yl)-5,6-dihydropyridine-1(2H)-carboxylate The title compound was prepared using the procedure described in Example 615A, using bis(2,5-dioxopyrrolidin-1-yl) carbonate (0.17 g, 0.66 mmol) in place of 4-nitrophenyl carbonochloridate. LC/MS: 465.4 (M+H)$^+$.

EXAMPLE 808B

Methyl 2-(4-(4-(5-fluoro-2-methoxyphenyl)-1H-pyrrolo[2,3-b]pyridin-2-yl)-1,2,3,6-tetrahydropyridine-1-carboxamido)propanoate The title compound was prepared using the procedure described in Example 625, using Example 808A (0.048 g, 0.085 mmol) in place of Example 615A and using methyl 2-aminopropanoate hydrochloride in place of 3-(aminomethyl)oxetan-3-ol. LC/MS: 465.4 (M+H)$^+$.

EXAMPLE 808C

N-({4-[4-(5-fluoro-2-methoxyphenyl)-1H-pyrrolo[2,3-b]pyridin-2-yl]-3,6-dihydropyridin-1(2H)-yl}carbonyl)alanine The title compound was prepared using the procedure described in Example 647B, using Example 808B (0.048 g, 0.085 mmol) in place of Example 647A. $^1$H NMR (400 MHz, DMSO-d$_6$): δ 1.29 (d, J=7.32 Hz, 1 H) 2.43-2.49 (m, 2 H) 3.75 (s, 3 H) 4.02-4.16 (m, 3 H) 6.28 (d, J=2.14 Hz, 1 H) 6.50-6.56 (m, 1 H) 6.68 (d, J=7.02 Hz, 1 H) 7.06 (d, J=4.88 Hz, 1 H) 7.17-7.31 (m, 3 H) 8.21 (d, J=5.19 Hz, 1 H) 11.90 (s, 1 H). MS (ESI$^+$) m/z 439.1 (M+H)$^+$.

EXAMPLE 809

4-(5-fluoro-2-methoxyphenyl)-2-(1-oxido-3,6-dihydro-2H-thiopyran-4-yl)-1H-pyrrolo[2,3-b]pyridine In a 20 mL microwave tube was suspended Example 806B (0.16 g, 0.47 mmol) in acetic acid (5 mL). Hydrogen peroxide (30 μL, 0.979 mmol) was added and the mixture was stirred at room temperature for 2 hours. After dilution with 10 mL dichloromethane, the mixture was washed with saturated sodium sulfite solution, water and brine. The organic layer was dried over sodium sulfate. After filtration and removal of the solvent the product was purified by flash chromatography on silica gel (AnaLogix IntelliFlash) eluting with a gradient of 0-15% methanol in dichloromethane to afford the title compound. $^1$H NMR (400 MHz, DMSO-d$_6$): δ 2.71-2.80 (m, 1 H) 2.82-3.01 (m, 2 H) 3.08-3.17 (m, 1 H) 3.40-3.49 (m, 1 H) 3.65-3.73 (m, 1 H) 3.75 (s, 3 H) 6.36 (d, J=2.14 Hz, 1 H) 6.38-6.43 (m, 1 H) 7.05 (d, J=4.88 Hz, 1 H) 7.17-7.31 (m, 3 H) 8.22 (d, J=4.88 Hz, 1 H) 11.88 (s, 1 H). MS (ESI$^+$) m/z 357.0 (M+H)$^+$.

EXAMPLE 812

4-[4-(2,3-difluorophenyl)-1H-pyrrolo[2,3-b]pyridin-2-yl]-N-(phenylsulfonyl)-3,6-dihydropyridine-1(2H)-carboxamide The title compound was prepared essentially as described in Example 768, substituting Example 87D with Example 222C. $^1$H NMR (400 MHz, DMSO-d$_6$) δ ppm 12.07 (s, 1 H) 11.06 (s, 1 H) 8.30 (d, J=5.19 Hz, 1 H) 7.89-7.98 (m, 2 H) 7.50-7.72 (m, 4 H) 7.28-7.50 (m, 2 H) 7.06-7.22 (m, 1 H) 6.48-6.58 (m, 1 H) 6.42 (s, 1 H) 4.08 (s, 2 H) 3.45-3.66 (m, 2 H) 2.42-2.55 (m, 2 H). MS (ESI): 495.1 (M+H)$^+$.

EXAMPLE 813

4-(5-fluoro-2-methoxyphenyl)-2-(1,2,3,6-tetrahydropyridin-4-yl)-1H-pyrrolo[2,3-b]pyridine-5-carboxamide To Example 236E (40 mg, 0.089 mmol) in 2 mL dimethylsulfoxide was added potassium carbonate (37.0 mg, 0.268 mmol) and hydrogen peroxide (30%, 100 μL). The mixture was stirred at room temperature overnight when additional hydrogen peroxide (30%, 100 μl) was added. The reaction was stirred at room temperature for 8 hours and then diluted with water and extracted with dichloromethane. The combined organic layer was washed with water and brine, dried over magnesium sulfate, and filtered. The filtrate was concentrated to dryness and then purified by flash column chromatography eluting with 0-8% methanol in dichloromethane to afford the N-Boc intermediate which was treated with trifluoroacetic acid in dichloromethane to obtain the title compound as trifluoroacetic acid salt. $^1$H NMR (400 MHz, DMSO-$d_6$) δ 2.68 (t, J=6.0 Hz, 2H), 3.31 (t, J=6.1 Hz, 2H), 3.65 (s, 3H), 3.82 (d, J=3.5 Hz, 2H), 6.23 (s, 1H), 6.45-6.55 (m, 1H), 7.06-7.15 (m, 2H), 7.23 (td, J=8.7, 3.1 Hz, 1H), 8.41 (s, 1H). MS (ESI$^+$) m/z 367 (M+H)$^+$.

EXAMPLE 814

2-[1-(2,3-dihydroxypropyl)-1,2,3,6-tetrahydropyridin-4-yl]-4-(5-fluoro-2-methoxyphenyl)-1H-pyrrolo[2,3-b]pyridine-5-carbonitrile To a mixture of Example 689A (122 mg, 0.17 mmol), 2,3-dihydroxypropanal (30.6 mg, 0.340 mmol) and acetic acid (48.7 µl, 0.850 mmol) in 3 mL of methanol was added MP-cyanoborohydride 600 mg (1.25 mmol/g). The reaction was heated at 40° C. for 4 hours and filtered. The filtrate was concentrated to dryness, and the residue was dissolved in 2 mL methanol and then treated with 1N sodium hydroxide (1 mL). The mixture was stirred at room temperature for 4 hours and at 70° C. for 1 hour. The crude product was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to provide the title compound as a trifluoroacetic acid salt. $^1$H NMR (500 MHz, DMSO-$d_6$) δ 2.81 (d, J=14.2 Hz, 2H), 3.07-3.22 (m, 1H), 3.45 (dd, J=10.9, 4.8 Hz, 4H), 3.57-3.74 (m, 1H), 3.76 (s, 3H), 3.86-4.02 (m, 2H), 4.12 (t, J=18.7 Hz, 1H), 4.98 (s, 1H), 5.58 (s, 1H), 6.49 (d, J=50.3 Hz, 2H), 7.18-7.72 (m, 3H), 8.60 (s, 1H), 9.74 (d, J=11.7 Hz, 1H), 12.66 (s, 1H). MS (ESI$^+$) m/z 423 (M+H)$^+$.

EXAMPLE 815

2-{4-[5-chloro-4-(5-fluoro-2-methoxyphenyl)-1H-pyrrolo[2,3-b]pyridin-2-yl]-3,6-dihydropyridin-1(2H)-yl}-N,N-dimethylacetamide The title compound was prepared as the procedure described in Example 738, substituting Example 229F for Example 622. $^1$H NMR (400 MHz, DMSO-$d_6$) δ 2.73-2.82 (m, 2H), 2.93 (d, J=7.4 Hz, 6H), 3.22-3.37 (m, 2H), 3.70 (s, 3H), 3.84-4.28 (m, 2H), 4.32 (s, 2H), 6.18 (d, J=8.3 Hz, 1H), 6.44 (q, J=6.6, 5.1 Hz, 1H), 7.04-7.44 (m, 3H), 8.30 (d, J=3.7 Hz, 1H), 10.02 (s, 1H), 12.24 (d, J=17.3 Hz, 1H). MS (ESI$^+$) m/z 443 (M+H)$^+$.

EXAMPLE 816

{4-[5-chloro-4-(5-fluoro-2-methoxyphenyl)-1H-pyrrolo[2,3-b]pyridin-2-yl]-3,6-dihydropyridin-1(2H)-yl}acetic acid The title compound was prepared as described in Example 226, substituting Example 229F for Example 87D in Example 226A. $^1$H NMR (400 MHz, DMSO-$d_6$) δ 2.80 (d, J=6.2 Hz, 2H), 3.52 (s, 2H), 3.71 (s, 3H), 4.04 (s, 2H), 4.21 (s, 2H), 6.16 (s, 1H), 6.47 (d, J=3.7 Hz, 1H), 6.94-7.52 (m, 3H), 8.30 (s, 1H), 10.70 (s, 1H), 12.24 (s, 1H). MS (ESI$^+$) m/z 416 (M+H)$^+$.

EXAMPLE 817

3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol

EXAMPLE 817A 5-chloro-4-(5-fluoro-2-methoxyphenyl)-2-(1,2,3,6-tetrahydropyridin-4-yl)-1-tosyl-1H-pyrrolo[2,3-b]pyridine The title compound was prepared as described in Example 229F, substituting Example 229D for Example 229E. MS (ESI$^+$) m/z 512 (M+H)$^+$.

EXAMPLE 817B

3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol The title compound was prepared as described in Example 814, substituting Example 817A for Example 689A. $^1$H NMR (500 MHz, DMSO-$d_6$) δ 2.77 (s, 2H), 3.00-3.23 (m, 1H), 3.30-3.6 (m, 5H), 3.70 (d, J=3.4 Hz, 3H), 3.85-4.02 (m, 2H), 4.09 (t, J=18.3 Hz, 1H), 5.5 (s, 1H), 5.55 (s, 1H), 6.17 (s, 1H), 6.47 (s, 1H), 6.96-7.55 (m, 3H), 8.30 (s, 1H), 9.71 (s, 1H), 12.24 (d, J=19.3 Hz, 1H). MS (ESI$^+$) m/z 432 (M+H)$^+$.

EXAMPLE 818

{4-[4-(5-fluoro-2-methoxyphenyl)-1H-pyrrolo[2,3-b]pyridin-2-yl]-3,6-dihydropyridin-1(2H)-yl}[(2S,4S)-4-hydroxypyrrolidin-2-yl]methanone The title compound was prepared as described in Example 238, substituting Example 87D for Example 226B and (2S,4S)-4-hydroxyproline for azetidin-3-ol hydrochloride. $^1$H NMR (500 MHz, DMSO-$d_6$) δ 1.80 (ddt, J=19.0, 11.9, 5.9 Hz, 1H), 2.14 (dddq, J=21.4, 12.7, 8.8, 4.3, 3.7 Hz, 1H), 2.35-2.48 (m, 1H), 2.64 (s, 1H), 3.26 (d, J=10.8 Hz, 2H), 3.51-3.87 (m, 5H), 3.95-4.43 (m, 2H), 4.63-4.79 (m, 1H), 5.03 (s, 1H), 6.25 (d, J=14.0 Hz, 1H), 6.52 (dt, J=7.6, 3.5 Hz, 1H), 7.04 (d, J=5.1 Hz, 1H), 7.18-7.32 (m, 3H), 8.21 (d, J=4.9 Hz, 1H), 11.87 (dd, J=13.4, 7.6 Hz, 1H). MS (ESI$^+$) m/z 437 (M+H)$^+$.

EXAMPLE 822

3-amino-4-{4-[4-(2-{2-[(2-amino-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione A solution of Example 795E (117 mg, 0.195 mmol) in 7M ammonia in methanol (4 mL, 28.0 mmol) was stirred in a capped vial overnight at room temperature. The precipitate was rinsed with methanol and diethyl ether, and dried under vacuum to provide the title compound. $^1$H NMR (400 MHz, DMSO-$d_6$) δ 11.89 (s, 1H), 8.15 (d, J=5.0 Hz, 1H), 7.76 (s, 2H), 7.70-7.20 (m, 6H), 7.10 (d, J=5.0 Hz, 1H), 6.53 (s, 1H), 6.37 (s, 1H), 4.49-4.37 (m, 2H), 4.14 (m, 2H), 4.06-3.68 (m, 4H), 2.63 (m, 2H). MS (ESI$^+$) m/e 543 (M+H)$^+$.

EXAMPLE 823 tert-butyl 4-({4-[4-(5-fluoro-2-methoxyphenyl)-1H-pyrrolo[2,3-b]pyridin-2-yl]-3,6-dihydropyridin-1(2H)-yl}sulfonyl)piperidine-1-carboxylate To a mixture of Example 87D (500 mg, 1.262 mmol) and tert-butyl 4-(chlorosulfonyl)piperidine-1-carboxylate (400 mg, 1.410 mmol) in 10 mL N,N-dimethylformamide was added triethylamine (0.6 mL, 4.30 mmol) and the mixture was stirred overnight at room temperature. The mixture was diluted with water and the precipitate was rinsed with water. Recrystallization from ethyl acetate gave the title compound. $^1$H NMR (400 MHz, DMSO-$d_6$) δ 11.86 (s, 1H), 8.21 (d, J=4.9 Hz, 1H), 7.34-7.14 (m, 3H), 7.04 (d, J=4.9 Hz, 1H), 6.57-6.48 (m, 1H), 6.27 (d, J=2.0 Hz, 1H), 4.07-3.87 (m, 4H), 3.74 (s, 3H), 3.53-3.38 (m, 3H), 2.76 (s, 2H), 2.51-1.49 (m, 2H), 2.03-1.89 (m, 2H), 1.50-1.40 (m, 2H), 1.38 (s, 9H). LCMS (APCI+) m/e 571 (M+H)$^+$.

EXAMPLE 824

4-[4-(5-fluoro-2-methoxyphenyl)-1H-pyrrolo[2,3-b]pyridin-2-yl]-1-(methylsulfonyl)-2,5-dihydro-1H-pyrrole-2-carboxylic acid Example 772C (60 mg, 0.156 mmol) was dissolved in dimethylformamide (1.5 mL) and methanesulfonyl chloride (0.022 ml, 0.280 mmol) and triethylamine (0.108 ml, 0.778 mmol) were added. The mixture was stirred at room temperature for 1 hour and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the trifluoroacetate salt. $^1$H NMR (500 MHz, DMSO-$d_6$) δ ppm 3.05 (s, 3 H) 3.75 (s, 3 H) 4.47-4.57 (m, 1 H) 4.59-4.70 (m, 1 H) 5.16-5.31 (m, 1 H) 6.41 (d, J=1.83 Hz, 1 H) 6.47 (d, J=2.14 Hz, 1 H) 7.10 (t, J=5.34 Hz, 1 H) 7.17-7.34 (m, 3 H) 8.28 (d, J=4.88 Hz, 1 H) 12.14 (d, J=1.53 Hz, 1 H). MS (ESI$^+$) m/z 432 (M+H)$^+$.

EXAMPLE 825

4-(5-fluoro-2-methoxyphenyl)-2-[1-(piperidin-4-ylsulfonyl)-1,2,3,6-tetrahydropyridin-4-yl]-1H-pyrrolo[2,3-b]pyridine The title compound was prepared using the procedure described in Example 795D, using Example 823 in place of Example 795C. $^1$H NMR (400 MHz, DMSO-$d_6$) δ 11.94 (s, 1H), 8.71 (m, 1H), 8.37 (m, 1H), 8.23 (d, J=5.0 Hz, 1H), 7.35-7.15 (m, 3H), 7.07 (d, J=5.0 Hz, 1H), 6.58-6.50 (m, 1H), 6.30 (d, J=2.0 Hz, 1H), 3.92 (s, 2H), 3.74 (s, 3H), 3.65-3.46 (m, 3H), 3.41-3.34 (m, 2H), 2.91 (q, J=12.1 Hz, 2H), 2.16-2.08 (m, 2H), 2.62-2.56 (m, 2H), 1.81 (m, 2H). MS (ESI+) m/e 471 (M+H)$^+$.

EXAMPLE 826

N,N-dimethyl-4-{2-[1-(methylsulfonyl)-1,2,3,6-tetrahydropyridin-4-yl]-1H-pyrrolo[2,3-b]pyridin-4-yl}benzamide

EXAMPLE 826A methyl 4-(2-(1-(methylsulfonyl)-1,2,3,6-tetrahydropyridin-4-yl)-1H-pyrrolo[2,3-b]pyridin-4-yl)benzoate A mixture of Example 220F (700.0 mg, 1.965 mmol), (4-(methoxycarbonyl)phenyl)boronic acid (424 mg, 2.358 mmol), 1,1'-bis(diphenylphosphino)ferrocene-palladium(II) dichloride dichloromethane complex (80 mg, 0.098 mmol), and saturated sodium bicarbonate solution (4.0 mL) in N,N-dimethylformamide (16 mL) was degassed and heated at 80° C. for 2 hours. The reaction mixture was treated with water and brine and extracted with ethyl acetate. The suspension in the aqueous layer was filtered, washed with water and ether, and vacuum oven-dried to provide the title compound. MS (ESI$^+$) m/z 412.1 (M+H)$^+$.

EXAMPLE 826B 4-(2-(1-(methylsulfonyl)-1,2,3,6-tetrahydropyridin-4-yl)-1H-pyrrolo[2,3-b]pyridin-4-yl)benzoic acid A mixture of Example 826A (330.0 mg, 0.802 mmol) and lithium hydroxide (38.4 mg, 1.604 mmol) in tetrahydrofuran (12 mL), methanol (5 mL), and water (4 mL) was stirred overnight. The reaction mixture was filtered. The filtrate was acidified with 5% citric acid to pH 6. The precipitates were filtered, washed with water, and vacuum oven-dried to provide the title compound. MS (ESI$^+$) m/z 398.1 (M+H)$^+$.

EXAMPLE 826C

N,N-dimethyl-4-{2-[1-(methylsulfonyl)-1,2,3,6-tetrahydropyridin-4-yl]-1H-pyrrolo[2,3-b]pyridin-4-yl}benzamide A mixture of Example 826B (75.0 mg, 0.189 mmol), (benzotriazol-1-yloxy)tripyrrolidinophosphonium hexafluorophosphate (PyBOP, 137 mg, 0.264 mmol), and 2M dimethylamine in tetrahydrofuran (0.472 mL, 0.944 mmol) in N,N-dimethylformamide (2 mL) was stirred overnight. The reaction mixture was treated with water and brine and extracted with ethyl acetate. The combined organic layers were washed with water and brine, dried over MgSO$_4$, filtered, concentrated, and purified by HPLC (see protocols in Example 361) to give the title compound as a trifluoroacetic acid salt. $^1$H NMR (500 MHz, DMSO-$d_6$) δ ppm 2.68 (m, 2H), 2.95 (s, 3H), 2.97-3.05 (m, 6H), 3.39 (t, J=5.7 Hz, 2H), 3.91-3.96 (m, 2H), 6.59 (bs, 1H), 6.72 (d, J=2.0 Hz, 1H), 7.25 (d, J=5.1 Hz, 1H), 7.56-7.62 (m, 2H), 7.83-7.86 (m, 2H), 8.30 (d, J=5.1 Hz, 1H), 12.13 (bs, 1H). MS (ESI$^+$) m/z 425.2 (M+H)$^+$.

EXAMPLE 827

2-{4-[4-(5-fluoro-2-methoxyphenyl)-1H-pyrrolo[2,3-b]pyridin-2-yl]-3,6-dihydropyridin-1(2H)-yl}-N,N-dimethylpropanamide The title compound was prepared essentially as described in Example 224 substituting 2-chloro-N,N-dimethylpropanamide for 2-chloro-N,N-dimethylacetamide. $^1$H NMR (400 MHz, CD$_3$OD) δ ppm 1.60 (d, J=6.8 Hz, 3H), 2.88-3.00 (m, 2H), 3.04 (s, 3H), 3.13 (s, 3H), 3.29-3.33 (m, 1H), 3.48-3.74 (m, 1H), 3.81 (s, 3H), 3.90-4.26 (m, 2H), 4.61 (q, J=6.8 Hz, 1H), 6.48-6.56 (m, 1H), 6.67 (s, 1H), 7.16-7.35 (m, 3H), 7.46 (d, J=5.8 Hz, 1H), 8.34 (d, J=5.8 Hz, 1H). MS (APCI$^+$) m/z 423.0 (M+H)$^+$.

EXAMPLE 828

4-(4-fluoro-2-methoxyphenyl)-2-[8-(methylsulfonyl)-8-azabicyclo[3.2.1]oct-2-en-3-yl]-1H-pyrrolo[2,3-b]pyridine

EXAMPLE 828A tert-butyl 3-(4-(4-fluoro-2-methoxyphenyl)-1-tosyl-1H-pyrrolo[2,3-b]pyridin-2-yl)-8-azabicyclo[3.2.1]oct-3-ene-8-carboxylate The title compound was prepared as described in Example 87A, substituting Example 722A for 4-bromo-1-(phenylsulfonyl)-1H-pyrrolo[2,3-b]pyridine and 4-fluoro-2-methoxyphenylboronic acid for 5-fluoro-2-methoxyphenylboronic acid. MS (ESI$^+$) m/z 604 (M+H)$^+$.

EXAMPLE 828B 2-(8-azabicyclo[3.2.1]oct-3-en-3-yl)-4-(4-fluoro-2-methoxyphenyl)-1H-pyrrolo[2,3-b]pyridine The title compound was prepared as described in Example 87D, substituting Example 828A for Example 87C. MS (ESI$^+$) m/z 350 (M+H)$^+$.

EXAMPLE 828C 4-(4-fluoro-2-methoxyphenyl)-2-[8-(methylsulfonyl)-8-azabicyclo[3.2.1]oct-2-en-3-yl]-1H-pyrrolo[2,3-b]pyridine The title compound was prepared as described in Example 119, substituting Example 828B for Example 87D. $^1$H NMR (500 MHz, DMSO-d$_6$) δ 1.61-1.75 (m, 1H), 1.91-2.13 (m, 3H), 2.13-2.27 (m, 1H), 2.43 (d, J=17.1 Hz, 1H), 2.87-3.06 (m, 4H), 3.78 (s, 3H), 4.36 (m, 1H), 4.43 (m, 1H), 6.19 (d, J=2.1 Hz, 1H), 6.78 (dt, J=5.8, 1.5 Hz, 1H), 6.91 (td, J=8.4, 2.5 Hz, 1H), 7.00 (d, J=4.9 Hz, 1H), 7.10 (dd, J=11.5, 2.5 Hz, 1H), 7.41 (dd, J=8.5, 6.9 Hz, 1H), 8.19 (d, J=2.1 Hz, 1H), 11.77 (br s, 1H); MS (ESI$^+$) m/z 428 (M+H)$^+$.

EXAMPLE 829

4-(4,5-difluoro-2-methoxyphenyl)-2-[8-(methylsulfonyl)-8-azabicyclo[3.2.1]oct-2-en-3-yl]-1H-pyrrolo[2,3-b]pyridine

EXAMPLE 829A tert-butyl 3-(4-(4,5-difluoro-2-methoxyphenyl)-1-tosyl-1H-pyrrolo[2,3-b]pyridin-2-yl)-8-azabicyclo[3.2.1]oct-3-ene-8-carboxylate The title compound was prepared as described in Example 87A, substituting Example 722A for 4-bromo-1-(phenylsulfonyl)-1H-pyrrolo[2,3-b]pyridine and 4,5-difluoro-2-methoxyphenylboronic acid for 5-fluoro-2-methoxyphenylboronic acid. MS (ESI$^+$) m/z 622 (M+H)$^+$.

EXAMPLE 829B 2-(8-azabicyclo[3.2.1]oct-3-en-3-yl)-4-(4,5-difluoro-2-methoxyphenyl)-1H-pyrrolo[2,3-b]pyridine The title compound was prepared as described in Example 87D, substituting Example 829A for Example 87C. MS (ESI$^+$) m/z 368 (M+H)$^+$.

EXAMPLE 829C 4-(4,5-difluoro-2-methoxyphenyl)-2-[8-(methylsulfonyl)-8-azabicyclo[3.2.1]oct-2-en-3-yl]-1H-pyrrolo[2,3-b]pyridine The title compound was prepared as described in Example 119, substituting Example 829B for Example 87D. $^1$H NMR (500 MHz, DMSO-d$_6$) δ 1.68 (m, 1H), 1.95-1.99 (m, 1H), 2.02-2.10 (m, 1H), 2.21 (m, 1H), 2.43 (d, J=17.1 Hz, 1H), 2.98 (m, 4H), 3.76 (s, 3H), 4.32-4.40 (m, 1H), 4.44 (t, J=5.9 Hz, 1H), 6.23 (d, J=2.1 Hz, 1H), 6.78 (dt, J=6.2, 1.5 Hz, 1H), 7.02 (d, J=4.9 Hz, 1H), 7.35 (dd, J=12.9, 6.9 Hz, 1H), 7.47 (dd, J=11.0, 9.2 Hz, 1H), 8.20 (d, J=4.9 Hz, 1H), 11.81 (d, J=2.4 Hz, 1H); MS (ESI$^+$) m/z 446 (M+H)$^+$.

EXAMPLE 830

4-(2-methoxyphenyl)-2-[8-(methylsulfonyl)-8-azabicyclo[3.2.1]oct-2-en-3-yl]-1H-pyrrolo[2,3-b]pyridine

EXAMPLE 830A tert-butyl 3-(4-(2-methoxyphenyl)-1-tosyl-1H-pyrrolo[2,3-b]pyridin-2-yl)-8-azabicyclo[3.2.1]oct-3-ene-8-carboxylate The title compound was prepared as described in Example 87A, substituting Example 722A for 4-bromo-1-(phenylsulfonyl)-1H-pyrrolo[2,3-b]pyridine and 2-methoxyphenylboronic acid for 5-fluoro-2-methoxyphenylboronic acid. MS (ESI$^+$) m/z 586 (M+H)$^+$.

EXAMPLE 830B 2-(8-azabicyclo[3.2.1]oct-3-en-3-yl)-4-(2-methoxyphenyl)-1H-pyrrolo[2,3-b]pyridine The title compound was prepared as described in Example 87D, substituting Example 830A for Example 87C. MS (ESI$^+$) m/z 332 (M+H)$^+$.

EXAMPLE 830C 4-(2-methoxyphenyl)-2-[8-(methylsulfonyl)-8-azabicyclo[3.2.1]oct-2-en-3-yl]-1H-pyrrolo[2,3-b]pyridine The title compound was prepared as described in Example 119, substituting Example 830B for Example 87D. $^1$H NMR (400 MHz, DMSO-d$_6$) δ 1.62-1.80 (m, 1H), 1.91-2.13 (m, 2H), 2.13-2.28 (m, 1H), 2.39 (d, dt, J=17.1 Hz, 1H), 3.92 (s, 3H), 4.32-4.40 (m, 1H), 4.43 (t, J=5.9 Hz, 1H), 6.19 (d, J=1.7 Hz, 1H), 6.74 (dt, J=5.9, 1.5 Hz, 1H), 6.92-7.11 (m, 2H), 7.16 (dd, J=8.4, 1.1 Hz, 1H), 7.31-7.47 (m, 2H), 8.17 (d, J=4.9 Hz, 1H), 11.41 (br s, 1H); MS (ESI$^+$) m/z 410 (M+H)$^+$.

EXAMPLE 831

4-(3-fluoro-2-methoxyphenyl)-2-(1,2,3,6-tetrahydro-pyridin-4-yl)-1H-pyrrolo[2,3-b]pyridine The title compound was prepared as described in Example 87, substituting 2-methoxy-3-fluorophenylboronic acid for 5-fluoro-2-methoxyphenylboronic acid in Example 87A. $^1$H NMR (500 MHz, DMSO-$d_6$) δ 2.73 (p, J=4.4, 3.4 Hz, 2H), 3.28 (dt, J=7.6, 5.3 Hz, 2H), 3.67 (s, 3H), 3.78-3.84 (m, 2H), 6.51 (d, J=1.7 Hz, 1H), 6.61-6.66 (m, 1H), 7.24-7.35 (m, 3H), 7.44 (ddd, J=11.7, 7.9, 1.9 Hz, 1H), 8.35 (d, J=5.5 Hz, 1H), 9.57 (t, J=5.4 Hz, 2H), 12.76 (br s, 1H); MS (ESI$^+$) m/z 324 (M+H)$^+$.

EXAMPLE 832

4-(5-fluoro-2-methoxyphenyl)-2-(2,5,6,7-tetrahydro-1H-azepin-4-yl)-1H-pyrrolo[2,3-b]pyridine The title compound was prepared essentially as described in Example 218, substituting ethanol for tert-butanol in Example 218A and Example 658 for Example 87D in Example 218B. $^1$H NMR (400 MHz, DMSO-$d_6$) δ 1.13 (t, J=7.1 Hz, 3H), 2.54 (t, J=5.7 Hz, 2H), 3.17 (m, 2H), 3.77 (s, 3H), 3.94 (d, J=3.2 Hz, 2H), 4.00 (q, J=7.1 Hz, 2H), 6.22 (d, J=2.0 Hz, 1H), 6.45-6.52 (m, 1H), 6.91 (td, J=8.4, 2.5 Hz, 1H), 7.00 (d, J=4.9 Hz, 1H), 7.09 (dd, J=11.5, 2.5 Hz, 1H), 7.42 (dd, J=8.4, 6.9 Hz, 1H), 8.18 (d, J=5.0 Hz, 1H). MS (DCI/NH$_3$) m/z 489 (M+H)$^+$.

EXAMPLE 833

4-(5-fluoro-2-methoxyphenyl)-2-[1-(methylsulfonyl)-2,5,6,7-tetrahydro-1H-azepin-4-yl]-1H-pyrrolo[2,3-b]pyridine The title compound was prepared essentially as described in Example 218, substituting ethanol for tert-butanol in Example 218A and Example 622 for Example 87D in Example 218B. $^1$H NMR (500 MHz, DMSO-$d_6$) δ 1.15 (t, J=7.1 Hz, 3H), 2.52-2.61 (m, 2H), 3.48 (t, J=5.8 Hz, 2H), 3.75 (s, 3H), 3.84 (s, 3H), 3.96-4.03 (m, 2H), 4.07 (q, J=7.1 Hz, 2H), 6.25 (d, J=2.0 Hz, 1H), 6.38-6.56 (m, 1H), 6.67 (dd, J=8.4, 2.4 Hz, 1H), 6.73 (d, J=2.4 Hz, 1H), 7.00 (d, J=5.0 Hz, 1H), 7.33 (d, J=8.3 Hz, 1H), 8.16 (d, J=5.0 Hz, 1H). MS (DCI/NH$_3$) m/z 487 (M+H)$^+$.

EXAMPLE 834

5-[4-(5-fluoro-2-methoxyphenyl)-1H-pyrrolo[2,3-b]pyridin-2-yl]-N-methyl-2,3,4,7-tetrahydro-1H-azepine-1-carboxamide The title compound was prepared essentially as described in Example 218, substituting ethanol for tert-butanol in Example 218A and Example 630 for Example 87D in Example 218B. $^1$H NMR (500 MHz, DMSO-$d_6$) δ 1.15 (t, J=7.1 Hz, 3H), 2.57 (dt, J=7.0, 3.8 Hz, 2H), 3.47 (t, J=5.8 Hz, 2H), 3.75 (s, 3H), 4.01 (dd, J=4.0, 2.2 Hz, 2H), 4.07 (q, J=7.1 Hz, 2H), 6.24 (s, 1H), 6.47-6.53 (m, 1H), 7.03 (d, J=4.6 Hz, 1H), 7.09 (td, J=7.4, 1.0 Hz, 1H), 7.16-7.22 (m, 1H), 7.39 (dd, J=7.5, 1.8 Hz, 1H), 7.44 (ddd, J=8.6, 7.5, 1.7 Hz, 1H). MS (DCI/NH$_3$) m/z 457 (M+H)$^+$.

EXAMPLE 835

1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone The title compound was prepared essentially as described in Example 218, substituting ethanol for tert-butanol in Example 218A and Example 630 for Example 87D in Example 218B. $^1$H NMR (500 MHz, DMSO-$d_6$) δ 1.15 (t, J=7.1 Hz, 3H), 2.57 (dt, J=6.8, 3.5 Hz, 2H), 3.45 (t, J=5.7 Hz, 2H), 3.76 (s, 3H), 3.99 (d, J=3.1 Hz, 2H), 4.05 (q, J=7.1 Hz, 2H), 6.27 (d, J=2.0 Hz, 1H), 6.50 (dd, J=4.4, 2.8 Hz, 1H), 7.02 (d, J=4.9 Hz, 1H), 7.35 (dd, J=12.9, 6.9 Hz, 1H), 7.47 (dd, J=10.9, 9.2 Hz, 1H), 8.20 (d, J=4.9 Hz, 1H). MS (DCI/NH$_3$) m/z 493 (M+H)$^+$.

EXAMPLE 836

{4-[4-(5-fluoro-2-methoxyphenyl)-1H-pyrrolo[2,3-b]pyridin-2-yl]-3,6-dihydropyridin-1(2H)-yl}[(2S,4R)-4-hydroxypyrrolidin-2-yl]methanone The title compound was prepared as described in Example 238, substituting Example 87D for Example 226B and (2S,4R)-4-hydroxyproline for azetidin-3-ol hydrochloride. $^1$H NMR (400 MHz, DMSO-$d_6$) δ 1.81 (ddd, J=15.4, 12.3, 6.3 Hz, 1H), 2.15 (ddt, J=22.8, 13.6, 5.7 Hz, 1H), 2.46 (s, 1H), 2.55 (s, 1H), 3.26 (d, J=10.8 Hz, 1H), 3.59-3.78 (m, 5H), 3.96-4.35 (m, 3H), 4.71 (qd, J=8.3, 7.7, 5.0 Hz, 1H), 4.99-5.09 (m, 1H), 6.25 (dd, J=11.7, 2.1 Hz, 1H), 6.52 (dt, J=6.9, 3.6 Hz, 1H), 7.04 (d, J=5.0 Hz, 1H), 7.14-7.34 (m, 3H), 8.21 (d, J=5.0 Hz, 1H), 11.79-11.91 (m, 1H). MS (ESI$^+$) m/z 437 (M+H)$^+$.

EXAMPLE 837

{4-[4-(5-fluoro-2-methoxyphenyl)-1H-pyrrolo[2,3-b]pyridin-2-yl]-3,6-dihydropyridin-1(2H)-yl}[(2R,4S)-4-hydroxypyrrolidin-2-yl]methanone The title compound was prepared as described in Example 238, substituting Example 87D for Example 226B and (2R,4S)-4-hydroxyproline for azetidin-3-ol hydrochloride. $^1$H NMR (500 MHz, DMSO-$d_6$) δ 1.81 (tt, J=13.3, 6.0 Hz, 1H), 2.15 (dtd, J=23.3, 11.9, 10.0, 5.1 Hz, 1H), 2.24-2.49 (m, 1H), 2.56 (d, J=10.3 Hz, 1H), 3.26 (d, J=10.9 Hz, 1H), 3.41 (td, J=11.3, 4.6 Hz, 1H), 3.50-3.87 (m, 4H), 3.94-4.48 (m, 3H), 4.71 (p, J=6.6, 6.0 Hz, 1H), 4.97-5.19 (m, 1H), 6.25 (d, J=14.1 Hz, 1H), 6.52 (q, J=4.3, 3.5 Hz, 1H), 7.04 (d, J=4.9 Hz, 1H), 7.13-7.41 (m, 3H), 8.21 (d, J=4.7 Hz, 1H), 11.87 (dd, J=13.7, 7.5 Hz, 1H). MS (ESI$^+$) m/z 437 (M+H)$^+$.

EXAMPLE 840

2-({4-[4-(5-fluoro-2-methoxyphenyl)-1H-pyrrolo[2,3-b]pyridin-2-yl]-3,6-dihydropyridin-1(2H)-yl}sulfonyl)ethanamine To a suspension of Example 794 (366 mg, 0.653 mmol) in 6 mL ethanol was added hydrazine monohydrate (0.2 mL, 4.08 mmol) and the mixture was heated at reflux for 3 hours. The solids were removed by filtration of the warm mixture through a plug of cotton. The filtrate was concentrated and

EXAMPLE 840 (continued)

the residue was purified by RP-HPLC (Sunfire 5 μM, 50×250 mm) using a gradient of 10:90 to 50:50 acetonitrile/0.1% trifluoroacetic acid in water to afford of the title compound as the trifluoroacetate salt. $^1$H NMR (400 MHz, DMSO-$d_6$) δ 11.94 (m, 1H), 8.23 (d, J=5.0 Hz, 1H), 7.96 (bs, 2H), 7.34-7.15 (m, 3H), 7.07 (d, J=5.0 Hz, 1H), 6.52 (s, 1H), 6.30 (s, 1H), 4.05 (s, 2H), 3.75 (s, 3H), 3.52-3.47 (m, 2H), 3.46-3.41 (m, 2H), 3.24-3.15 (m, 2H), 2.61 (m, 2H). MS (ESI+) m/e 431 (M+H)$^+$.

EXAMPLE 841

4-{2-[1-(methylsulfonyl)-1,2,3,6-tetrahydropyridin-4-yl]-1H-pyrrolo[2,3-b]pyridin-4-yl}-N-propylbenzamide The title compound was prepared essentially as described in Example 826C, substituting n-propylamine for dimethylamine. $^1$H NMR (400 MHz, DMSO-$d_6$) δ ppm 0.92 (t, J=7.4 Hz, 3H), 1.57 (hours, J=7.4 Hz, 2H), 2.62-2.89 (m, 2H), 2.95 (s, 3H), 3.27 (q, J=6.5 Hz, 2H), 3.40 (t, J=5.7 Hz, 3H), 3.94 (d, J=3.4 Hz, 2H), 6.56-6.62 (m, 1H), 6.70 (d, J=1.9 Hz, 1H), 7.25 (d, J=5.1 Hz, 1H), 7.86 (s, 1H), 7.88 (s, 1H), 8.03 (s, 1H), 8.03 (s, 1H), 8.31 (d, J=5.0 Hz, 1H), 8.57 (t, J=5.6 Hz, 1H), 12.12 (bs, 1H). MS (ESI$^+$) m/z 439.1 (M+H)$^+$.

EXAMPLE 842

3-fluoro-N-methyl-4-{2-[1-(methylsulfonyl)-1,2,3,6-tetrahydropyridin-4-yl]-1H-pyrrolo[2,3-b]pyridin-4-yl}benzamide The title compound was prepared using the procedure described in Example 258G, using Example 807C (0.088 g, 0.21 mmol) in place of Example 258F. $^1$H NMR (400 MHz, DMSO-$d_6$): δ 2.58-2.65 (m, 2 H) 2.83 (d, J=4.58 Hz, 3 H) 2.94 (s, 3 H) 3.37 (t, J=5.80 Hz, 2 H) 3.92 (d, J=2.75 Hz, 2 H) 6.40 (s, 1 H) 6.55-6.60 (m, 1 H) 7.13-7.16 (m, 1 H) 7.70-7.87 (m, 3 H) 8.29 (d, J=4.88 Hz, 1 H) 8.63 (d, J=4.58 Hz, 1 H) 12.04 (s, 1 H). MS (ESI$^+$) m/z 429.1 (M+H)$^+$.

EXAMPLE 843 ethyl {[4-{4-[2-fluoro-4-(methylcarbamoyl)phenyl]-1H-pyrrolo[2,3-b]pyridin-2-yl}-3,6-dihydropyridin-1(2H)-yl]sulfonyl}carbamate The title compound was prepared essentially as described in Example 218, substituting ethanol for tert-butanol in Example 218A and Example 807C for Example 87D in Example 218B. $^1$H NMR (500 MHz, DMSO-$d_6$): δ 1.15 (t, J=7.02 Hz, 3 H) 2.83 (d, J=4.27 Hz, 3 H) 3.48 (t, J=5.80 Hz, 2 H) 4.01-4.04 (m, 2 H) 4.07 (q, J=7.32 Hz, 2 H) 6.38 (s, 1 H) 6.52-6.56 (m, 1 H) 7.13-7.16 (m, 1 H) 7.73 (t, J=7.63 Hz, 1 H) 7.80-7.85 (m, 2 H) 8.29 (d, J=4.88 Hz, 1 H) 8.61-8.66 (m, 1 H) 11.38 (s, 1 H) 12.03 (s, 1 H). MS (ESI$^+$) m/z: 502.1 (M+H)$^+$.

EXAMPLE 844

[4-{4-[2-fluoro-4-(methylcarbamoyl)phenyl]-1H-pyrrolo[2,3-b]pyridin-2-yl}-3,6-dihydropyridin-1(2H)-yl]acetic acid

EXAMPLE 844A tert-butyl 2-(4-(4-(2-fluoro-4-(methylcarbamoyl)phenyl)-1H-pyrrolo[2,3-b]pyridin-2-yl)-5,6-dihydropyridin-1(2H)-yl)acetate The title compound was prepared as described in Example 742, using Example 807C in place of Example 485. LC/MS: 465.1 (M+H)$^+$.

EXAMPLE 844B

[4-{4-[2-fluoro-4-(methylcarbamoyl)phenyl]-1H-pyrrolo[2,3-b]pyridin-2-yl}-3,6-dihydropyridin-1(2H)-yl]acetic acid The title compound was prepared using the procedure described in Example 748, using Example 844A in place of Example 742. $^1$H NMR (500 MHz, DMSO-$d_6$): δ 2.80-2.87 (m, 5 H) 3.95-4.14 (m, 2 H) 4.22 (s, 2 H) 6.48 (s, 2 H) 7.16-7.19 (m, 1 H) 7.74 (t, J=7.63 Hz, 1 H) 7.81-7.86 (m, 2 H) 8.33 (d, J=4.88 Hz, 1 H) 8.62-8.68 (m, 1 H) 12.16 (s, 1 H). MS (ESI$^+$) m/z: 409.1 (M+H)$^+$.

EXAMPLE 845

4-(5-fluoro-2-methoxyphenyl)-2-(1,2,3,3a,4,6a-hexahydrocyclopenta[c]pyrrol-5-yl)-1H-pyrrolo[2,3-b]pyridine The title compound was prepared as described in Example 262E. $^1$H NMR (500 MHz, DMSO-$d_6$) δ ppm 2.69 (dd, J=16.48, 1.53 Hz, 1 H) 2.93-3.04 (m, 2 H) 3.08-3.23 (m, 2 H) 3.27-3.44 (m, 2 H) 3.66-3.73 (m, 1 H) 3.74 (s, 3 H) 6.24 (d, J=2.14 Hz, 1 H) 6.28 (d, J=1.53 Hz, 1 H) 7.09 (d, J=4.88 Hz, 1 H) 7.18-7.24 (m, 2 H) 7.26-7.33 (m, 1 H) 8.25 (d, J=4.88 Hz, 1 H) 8.73 (d, J=5.19 Hz, 1 H) 8.89 (s, 1 H) 12.11 (s, 1 H). MS (ESI$^+$) m/z 350 (M+H)$^+$.

EXAMPLE 846 tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate

EXAMPLE 846A

4-[4-(5-fluoro-2-methoxyphenyl)-1H-pyrrolo[2,3-b]pyridin-2-yl]-2,5-dihydro-1H-pyrrole-2-carboxylic acid To a solution of Example 772B (100 mg, 0.165 mmol) in dioxane (1.4 mL) was added aqueous sodium hydroxide solution (5 M, 296 μl, 1.481 mmol). The mixture was heated at 90° C. for 3 hours. The mixture was poured into a 60 mL separatory funnel containing 25 mL of 1 molar aqueous phosphoric acid and 25 mL of ethyl acetate. The mixture was partitioned between the two phases and the aqueous phase was removed. The organic layer was washed with saturated aqueous brine, dried over anhydrous magnesium sulfate, filtered and concentrated in vacuo to give the crude acid.

Purification by silica gel flash chromatography (Isco®, 12 G Redi-Sep® column, 50-100% ethyl acetate/hexane (quick gradient) then 10% of a 2:1 mixture methanol:water in ethyl acetate) afforded the title compound. MS (ESI$^+$) m/z 454 (M+H)$^+$.

EXAMPLE 846B tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate To Example 846A (100 mg, 0.221 mmol) in dimethylformamide (1.2 mL) was added 1-ethyl-3-(3-dimethylaminopropyl)carbodiimide (63.4 mg, 0.331 mmol), hydroxybenzotriazole (50.7 mg, 0.331 mmol) and N-ethyl-N-isopropylpropan-2-amine (0.058 ml, 0.331 mmol). The mixture was stirred at room temperature for 30 minutes. Dimethylamine (0.068 ml, 1.103 mmol) was added. The mixture was stirred at room temperature overnight and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-d$_6$) δ ppm 1.35 (s, 6 H) 1.43 (s, 3 H) 2.85 (s, 1 H) 2.88 (s, 2 H) 3.14 (s, 2 H) 3.15 (s, 1 H) 3.73 (s, 1 H) 3.75 (s, 2 H) 4.42-4.51 (m, 2 H) 5.48-5.62 (m, 1 H) 6.27-6.55 (m, 2 H) 7.07 (t, J=5.04 Hz, 1 H) 7.16-7.33 (m, 3 H) 8.25 (d, J=4.88 Hz, 1 H) 11.99 (s, 1 H). MS (ESI$^+$) m/z 481 (M+H)$^+$.

EXAMPLE 847 tert-butyl 4-[4-(5-fluoro-2-methoxyphenyl)-1H-pyrrolo[2,3-b]pyridin-2-yl]-2-[(methylsulfonyl)carbamoyl]-2,5-dihydro-1H-pyrrole-1-carboxylate To Example 846A (50 mg, 0.110 mmol) in CH$_2$Cl$_2$ (2 mL) was added oxalyl chloride (11.58 µL, 0.132 mmol) and dimethylformamide (20 µL). The mixture was stirred at room temperature for 2 hours. The reaction mixture was concentrated and dissolved in anhydrous CH$_2$Cl$_2$ (2 mL). A solution of methanesulfonamide (10.49 mg, 0.110 mmol) in CH$_2$Cl$_2$ (2 mL) and dimethylformamide (0.3 mL) was added followed by triethylamine (30.7 µL, 0.221 mmol). The mixture was stirred at room temperature overnight and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-d$_6$) δ ppm 1.38 (s, 6 H) 1.44 (s, 3 H) 3.08 (s, 1 H) 3.10 (s, 2 H) 3.74 (s, 1 H) 3.75 (s, 2 H) 4.35-4.54 (m, 2 H) 4.86-5.02 (m, 1 H) 6.28-6.46 (m, 2 H) 7.03-7.09 (m, 1 H) 7.17-7.32 (m, 3 H) 8.25 (d, J=4.88 Hz, 1 H) 12.02-12.08 (m, 1 H). MS (ESI$^+$) m/z 531 (M+H)$^+$.

EXAMPLE 848

2-fluoro-N-methyl-4-[2-(1,2,3,6-tetrahydropyridin-4-yl)-1H-pyrrolo[2,3-b]pyridin-4-yl]benzamide

EXAMPLE 848A tert-butyl 4-(4-(3-fluoro-4-(methylcarbamoyl)phenyl)-1-tosyl-1H-pyrrolo[2,3-b]pyridin-2-yl)-5,6-dihydropyridine-1(2H)-carboxylate A mixture of Example 220C (2.200 g, 4.13 mmol), (3-fluoro-4-(methylcarbamoyl)phenyl)boronic acid (0.895 g, 4.55 mmol), 1,1'-bis(diphenylphosphino)ferrocene-palladium(II)dichloride dichloromethane complex (0.135 g, 0.165 mmol), and saturated sodium bicarbonate solution (10 mL) in N,N-dimethylformamide (40 mL) was degassed and heated at 80° C. for 2 hours. The reaction mixture was filtered, treated with water and brine and extracted with ethyl acetate. The combined organic layers were washed with water and brine, dried over MgSO$_4$, filtered, concentrated, and purified on an 80 g silica column using the ISCO Companion flash system eluting with heptanes/ethyl acetate (4:6 to 3:7) to provide the title compound. MS (ESI$^+$) m/z 605.1 (M+H)$^+$.

EXAMPLE 848B tert-butyl 4-(4-(3-fluoro-4-(methylcarbamoyl)phenyl)-1H-pyrrolo[2,3-b]pyridin-2-yl)-5,6-dihydropyridine-1(2H)-carboxylate A mixture of Example 848A (1.700 g, 2.81 mmol) and 5M aqueous sodium hydroxide (2.53 mL, 12.65 mmol) solution in dioxane (20 mL) was heated at 90° C. for 8 hours. The reaction mixture was cooled while stirring continued. Precipitate formed and the mixture was diluted with water (30 mL). The suspension was filtered, washed with water, and vacuum oven-dried to provide the title compound. MS (APCI$^+$) m/z 451.2 (M+H)$^+$.

EXAMPLE 848C 2-fluoro-N-methyl-4-[2-(1,2,3,6-tetrahydropyridin-4-yl)-1H-pyrrolo[2,3-b]pyridin-4-yl]benzamide A suspension of Example 848B (1.120 g, 2.486 mmol) in CH$_2$Cl$_2$ (20 mL) was treated with trifluoroacetic acid (2.298 mL, 29.8 mmol). The mixture was stirred for 6 hours at 35° C. and concentrated. The residue was dissolved in 6 mL of methanol and treated with 6 mL of 2M HCl in ether slowly. The suspension was sonicated, diluted with ether, and stirred for 10 minutes. The solids were filtered, washed with ether, and vacuum oven-dried to provide the title compound as an HCl salt. $^1$H NMR (400 MHz, methanol-d$_4$) δ ppm 2.89-3.04 (m, 5H), 3.53 (t, J=6.1 Hz, 2H), 3.98-4.04 (m, 2H), 6.66-6.71 (m, 1H), 7.07 (s, 1H), 7.65-7.83 (m, 3H), 7.99 (t, J=7.7 Hz, 1H), 8.45 (d, J=6.1 Hz, 1H). MS (ESI$^+$) m/z 351.1 (M+H)$^+$.

The following two examples were prepared essentially as described in Example 231F, substituting the appropriate amine for Example 231E.

EXAMPLE 850

4-(2-{1-[2-(dimethylamino)-2-oxoethyl]-1,2,3,6-tetrahydropyridin-4-yl}-1H-pyrrolo[2,3-b]pyridin-4-yl)-2-fluoro-N-methylbenzamide $^1$H NMR (400 MHz, methanol-d$_4$) δ ppm 2.97 (s, 3H), 3.02 (s, 8H), 3.64 (bs, 2H), 3.95-4.26 (m, 2H), 4.36 (s, 2H), 6.45-6.51 (m, 1H), 6.88 (s, 1H), 7.38 (d, J=5.4 Hz, 1H), 7.65 (dd, J=11.6, 1.6 Hz, 1H), 7.72 (dd, J=8.0, 1.6 Hz, 1H), 7.94 (t, J=7.7 Hz, 1H), 8.35 (d, J=5.4 Hz, 1H). MS (ESI$^+$) m/z 436.1 (M+H)$^+$.

EXAMPLE 1009

2-{4-[4-(5-fluoro-2-methoxyphenyl)-1H-pyrrolo[2,3-b]pyridin-2-yl]-3,3-dimethyl-3,6-dihydropyridin-1(2H)-yl}-N,N-dimethylacetamide $^1$H NMR (500 MHz, DMSO-d$_6$) δ ppm 1.28 (s, 6H), 2.46 (bs, 2H), 2.90 (s, 3H), 3.14 (s, 3H), 3.22 (d, J=3.5 Hz, 2H), 3.32 (s, 2H), 3.82 (s, 3H), 6.21-6.25 (m, 2H), 7.09 (d, J=4.9 Hz, 1H), 7.23-7.39 (m, 3H), 8.26 (d, J=4.9 Hz, 1H), 11.58-11.63 (m, 1H). MS (ESI$^+$) m/z 437.2 (M+H)$^+$.

EXAMPLE 852

4-(5-fluoro-2-methoxyphenyl)-5-methoxy-2-[1-(methylsulfonyl)-1,2,3,6-tetrahydropyridin-4-yl]-1H-pyrrolo[2,3-b]pyridine

EXAMPLE 852A 4-chloro-5-methoxy-1-(phenylsulfonyl)-1H-pyrrolo[2,3-b]pyridine 4-Chloro-5-methoxy-1H-pyrrolo[2,3-b]pyridine (2.6 g, 14.24 mmol) in 30 mL dimethylformamide was cooled with an ice-bath and treated with sodium hydride (0.683 g, 17.09 mmol). The mixture was stirred at room temperature for 30 minutes and benzenesulfonyl chloride (2.192 ml, 17.09 mmol) was added dropwise. The mixture was stirred at room temperature for 1 hour and then poured into 500 mL water. The suspension was filtered to provide the title compound. MS (ESI$^+$) m/z 323 (M+H)$^+$.

EXAMPLE 852B 4-(5-fluoro-2-methoxyphenyl)-5-methoxy-1-(phenylsulfonyl)-1H-pyrrolo[2,3-b]pyridine Example 852A (4.6 g, 14.25 mmol), (5-fluoro-2-methoxyphenyl)boronic acid (3.15 g, 18.53 mmol), K$_3$PO4 (9.08 g, 42.8 mmol), and phenylallylchloro[1,3-bis(diisopropylphenyl)-2-imidazol-2-ylidene]palladium(II) (0.831 g, 1.283 mmol) in 120 mL tetrahydrofuran and 40 mL water were degassed and stirred at 80° C. for 3 hour. The reaction mixture was diluted with water and extracted with ethyl acetate. The crude product was purified by silica-gel column chromatography eluting with dichloromethane using Analogix purification system to afford the title compound. MS (ESI$^+$) m/z 413 (M+H)$^+$.

EXAMPLE 852C 4-(5-fluoro-2-methoxyphenyl)-2-iodo-5-methoxy-1-(phenylsulfonyl)-1H-pyrrolo[2,3-b]pyridine The title compound was prepared essentially as described in Example 87B, substituting Example 852B for Example 87A. MS (ESI$^+$) m/z 539 (M+H)$^+$.

EXAMPLE 852D 4-(5-fluoro-2-methoxyphenyl)-5-methoxy-2-[1-(methylsulfonyl)-1,2,3,6-tetrahydropyridin-4-yl]-1H-pyrrolo[2,3-b]pyridine Example 852C (120 mg, 0.223 mmol), 1-(methylsulfonyl)-4-(4,4,5,5-tetramethyl-1,3,2-dioxaborolan-2-yl)-1,2,3,6-tetrahydropyridine (77 mg, 0.267 mmol), sodium hydrogencarbonate (56.2 mg, 0.669 mmol) in a mixture of tetrahydrofuran (2 mL), methanol (2 mL) and water (1.5 mL) were degassed with nitrogen, Pd(1,1'-bis(diphenylphosphino)ferrocene)$_2$Cl$_2$ (14.56 mg, 0.018 mmol) was added under nitrogen. The mixture was heated at 70° C. for 3 hours and then at 80° C. for 1 hour. The reaction mixture was treated with 1M sodium hydroxide solution (1115 μl, 1.115 mmol) at room temperature overnight and then neutralized to pH 6-7. The mixture was extracted with ethyl acetate. The organic solution was washed with water, brine, dried over MgSO$_4$ and filtered. The filtrate was concentrated to dryness and purified by column chromatography eluting with 0-5% methanol in dichloromethane using Analogix purification system to afford the title compound. $^1$H NMR (400 MHz, DMSO-d$_6$) δ 2.52-2.63 (m, 2H), 2.92 (s, 3H), 3.6-3.8 (m, 8H), 3.89 (d, J=3.1 Hz, 2H), 5.99 (d, J=2.1 Hz, 1H), 6.50 (s, 1H), 7.00-7.40 (m, 3H), 8.13 (s, 1H), 11.65 (s, 1H). MS (ESI$^+$) m/z 432 (M+H)$^+$.

EXAMPLE 854

3-[4-(5-fluoro-2-methoxyphenyl)-1H-pyrrolo[2,3-b]pyridin-2-yl]cyclohex-3-ene-1-carboxylic acid

EXAMPLE 854A ethyl 3-(4-(5-fluoro-2-methoxyphenyl)-1H-pyrrolo[2,3-b]pyridin-2-yl)cyclohex-3-enecarboxylate The title compound was prepared essentially as described in Example 219B, substituting ethyl 4-(4,4,5,5-tetramethyl-1,3,2-dioxaborolan-2-yl)cyclohex-3-enecarboxylate with ethyl 3-(4,4,5,5-tetramethyl-1,3,2-dioxaborolan-2-yl)cyclohex-3-enecarboxylate. MS (ESI): 395.2 (M+H)$^+$.

EXAMPLE 854B

3-[4-(5-fluoro-2-methoxyphenyl)-1H-pyrrolo[2,3-b]pyridin-2-yl]cyclohex-3-ene-1-carboxylic acid The title compound was prepared essentially as described in Example 219C, substituting Example 219B with Example 854A. $^1$H NMR (400 MHz, DMSO-d$_6$) δ ppm 11.74 (s, 1 H) 8.18 (d, J=4.88 Hz, 1 H) 7.11-7.40 (m, 3 H) 7.02 (d, J=5.19 Hz, 1 H) 6.54 (s, 1 H) 6.19 (d, J=1.83 Hz, 1 H) 3.74 (s, 3 H) 2.53-2.68 (m, 2 H) 2.39-2.53 (m, 2 H) 2.28 (s, 2 H) 1.93-2.05 (m, 1 H) 1.55-1.70 (m, 1 H). MS (ESI): 367.1 (M+H)$^+$.

EXAMPLE 855

{4-[4-(5-fluoro-2-methoxyphenyl)-1H-pyrrolo[2,3-b]pyridin-2-yl]-1,2,3,6-tetrahydropyridin-2-yl}methanol

EXAMPLE 855A 1-tert-butyl 2-methyl 4-(((trifluoromethyl)sulfonyl)oxy)-2,3-dihydropyridine-1,2(6H)-dicarboxylate and 1-tert-butyl 2-methyl 4-(((trifluoromethyl)sulfonyl)oxy)-5,6-dihydropyridine-1,2(2H)-dicarboxylate 1-tert-Butyl 2-methyl 4-oxopiperidine-1,2-dicarboxylate (10 g, 38.9 mmol) was dissolved in tetrahydrofuran (80 ml) under nitrogen atmosphere, and the solution was chilled in a dry ice-acetone bath. To the stirred solution was added dropwise a 1N solution of lithium bis(trimethylsilyl)amide in hexanes (42.8 ml, 42.8 mmol), and after the addition of base was completed, a solution of 1,1,1-trifluoro-N-phenyl-N-((trifluoromethyl)sulfonyl)methanesulfonamide (14.58 g, 40.8 mmol) in tetrahydrofuran (20 ml) was added dropwise. The reaction was allowed to warm to room temperature, quenched with saturated aqueous NH$_4$Cl (100 mL), and extracted with ethyl acetate (3×150 mL). The extracts were dried (Na$_2$SO$_4$), filtered, and concentrated. The crude material was purified by flash chromatography (Analogix system, Grace 120 g column, 60 mL/min, gradient from 0 to 20% ethyl acetate-heptanes over 60 minutes). The product was isolated as a mixture of the title compounds which was used without further purification in the subsequent reaction.

EXAMPLE 855B 1-tert-butyl 2-methyl 4-(4-(5-fluoro-2-methoxyphenyl)-1-(phenylsulfonyl)-1H-pyrrolo[2,3-b]pyridin-2-yl)-2,3-dihydropyridine-1,2(6H)-dicarboxylate The inseparable mixture of regioisomers from Example 855A (5.25 g, 9.44 mmol, combined mass of the two isomers, adjusted to account for the triflamide byproduct), bis(pinacolato)diboron (2.398 g, 9.44 mmol), $PdCl_2$ (1,1'-bis(diphenylphosphino)ferrocene), complex with $CH_2Cl_2$ (0.321 g, 0.393 mmol) and potassium acetate (3.86 g, 39.3 mmol) were combined in dioxane (40 ml). The mixture was degassed with nitrogen, and then heated to reflux for 1.5 hours. The mixture was cooled to room temperature and then Example 87B (4 g, 7.87 mmol), additional $PdCl_2$ (1,1'-bis(diphenylphosphino)ferrocene), complex with $CH_2Cl_2$ (0.321 g, 0.393 mmol), and a solution of sodium carbonate (4.59 g, 43.3 mmol) in water (0.5 mL) were added. The reaction was heated to 65° C. overnight, then cooled to room temperature and partitioned between water (100 mL) and ethyl acetate (3×75 mL). The solution was dried ($Na_2SO_4$), filtered, concentrated and purified by repeated flash chromatography (Analogix Intelliflash system, gradient from 0 to 40% ethyl acetate-heptanes over 45 minutes, Grace 80 g column, 60 mL/min) to provide the title compound.

EXAMPLE 855C tert-butyl 4-(4-(5-fluoro-2-methoxyphenyl)-1-(phenylsulfonyl)-1H-pyrrolo[2,3-b]pyridin-2-yl)-6-(hydroxymethyl)-5,6-dihydropyridine-1(2H)-carboxylate Example 855B (200 mg, 0.322 mmol) was dissolved in tetrahydrofuran (3.2 ml) and the solution was chilled to 0° C. A 1.0 M solution of $LiAlH_4$ in tetrahydrofuran (643 μl, 0.643 mmol) was added dropwise, over about 2 minutes. Following the addition, the reaction was stirred for 1 minute at 0° C., then quenched by careful addition of water (15 mL). The mixture was extracted with ethyl acetate (3×15 mL). The combined organic extracts were dried ($Na_2SO_4$), filtered and concentrated. The residue was purified by flash chromatography (Analogix Intelliflash system, gradient from 0 to 60% ethyl acetate-heptanes over 30 minutes, Grace 12 g column, 28 mL/min) to provide the title compound.

EXAMPLE 855D

{4-[4-(5-fluoro-2-methoxyphenyl)-1H-pyrrolo[2,3-b]pyridin-2-yl]-1,2,3,6-tetrahydropyridin-2-yl}methanol Example 855C (464 mg, 0.782 mmol) was dissolved in dioxane (7.8 mL) and 5N aqueous NaOH (547 μl, 2.74 mmol) was added. The mixture was heated to reflux overnight then diluted with water (50 mL) and adjusted to acidic pH by addition of 1N aqueous HCl (~5 mL) using stirring and sonication to ensure all solid material was dissolved. The mixture was washed with $CH_2Cl_2$ (3×20 mL), treated with 2N aqueous NaOH (5 mL) and extracted with ethyl acetate (3×20 mL). The combined organic extracts were dried ($Na_2SO_4$), filtered and concentrated to provide the title compound. $^1H$ NMR (500 MHz, DMSO-$d_6$) δ 11.76 (bs, 1H), 8.18 (d, J=4.9 Hz, 1H), 7.33-7.08 (m, 3H), 7.02 (d, J=4.9 Hz, 1H), 6.55 (bs, 1H), 6.16 (d, J=1.9 Hz, 1H), 4.64 (t, J=5.4 Hz, 1H), 3.73 (s, 3H), 3.50-3.42 (m, 3H), 3.41-3.36 (m, 1H), 2.81-2.70 (m, 1H), 2.38-2.30 (m, 1H), 2.27-2.10 (m, 1H), 2.00 (dd, J=13.5, 10.5 Hz, 1H); MS (ESI+) m/z 354.1 (M+H)$^+$.

EXAMPLE 856

7-[4-(5-fluoro-2-methoxyphenyl)-1H-pyrrolo[2,3-b]pyridin-2-yl]-3-oxa-9-azabicyclo[3.3.1]non-6-ene

EXAMPLE 856A tert-butyl 7-(((trifluoromethyl)sulfonyl)oxy)-3-oxa-9-azabicyclo[3.3.1]non-6-ene-9-carboxylate 9-Boc-7-oxa-9-azabicyclo[3.3.1]nonan-3-one (500 mg, 2.072 mmol) and 1,1,1-trifluoro-N-phenyl-N-((trifluoromethyl)sulfonyl)methanesulfonamide (740 mg, 2.072 mmol) were dissolved in tetrahydrofuran (10 ml) and the solution was chilled to −78° C. A 1.0 N solution of lithium bis(trimethylsilyl)amide in tetrahydrofuran (2.1 mL, 2.1 mmol) was added dropwise over about 5 minutes. The mixture was stirred 15 minutes at −78° C., and was allowed to warm to room temperature. The reaction was quenched with saturated aqueous $NH_4Cl$ (10 ml), extracted with ethyl acetate (3×20 mL), dried ($Na_2SO_4$), filtered, and concentrated. Purification by flash chromatography, eluting with ethyl acetate/heptanes, gave the title compound. MS (ESI+) m/z 274.1 (M-Boc+H)$^+$.

EXAMPLE 856B tert-butyl 7-(4-(5-fluoro-2-methoxyphenyl)-1-(phenylsulfonyl)-1H-pyrrolo[2,3-b]pyridin-2-yl)-3-oxa-9-azabicyclo[3.3.1]non-6-ene-9-carboxylate Example 856A (573 mg, 1.535 mmol), bis(pinacolato)diboron (390 mg, 1.535 mmol), $PdCl_2$ (1,1'-bis(diphenylphosphino)ferrocene), complex with $CH_2Cl_2$ (52.2 mg, 0.064 mmol) and potassium acetate (628 mg, 6.39 mmol) were combined in dioxane (12 ml). The mixture was briefly degassed, and then heated to reflux for 1.5 hours. The mixture was cooled to room temperature and Example 87B (650 mg, 1.279 mmol), additional $PdCl_2$ (1,1'-bis(diphenylphosphino)ferrocene) (52.2 mg, 0.064 mmol), and a solution of sodium carbonate (745 mg, 7.03 mmol) in water (0.5 mL) were added. The mixture was heated to 65° C. overnight, then cooled to room temperature and partitioned between water (25 mL) and ethyl acetate (3×25 mL). The combined organic extracts were dried ($Na_2SO_4$), filtered, and concentrated, then purified by flash chromatography (Grace 12 g column, gradient from 0 to 50% ethyl acetate-heptanes over 40 minutes, 30 mL/minutes) to provide the title compound. MS (ESI+) m/z 606.1 (M+H)$^+$.

EXAMPLE 856C tert-butyl 7-(4-(5-fluoro-2-methoxyphenyl)-1H-pyrrolo[2,3-b]pyridin-2-yl)-3-oxa-9-azabicyclo[3.3.1]non-6-ene-9-carboxylate 5N Aqueous sodium hydroxide (682 μl, 3.41 mmol) was added to a solution of Example 856B (648 mg, 0.974 mmol)

in dioxane (5563 µl) and the mixture was heated to reflux overnight, cooled to room temperature, diluted with saturated aqueous NaHCO$_3$ (30 mL) and extracted with ethyl acetate (3×25 mL). The extracts were dried (Na$_2$SO$_4$), filtered, and concentrated to provide the title compound. MS (LCMS, APCI+) m/z 466.4 (M+H)$^+$.

EXAMPLE 856D

7-[4-(5-fluoro-2-methoxyphenyl)-1H-pyrrolo[2,3-b]pyridin-2-yl]-3-oxa-9-azabicyclo[3.3.1]non-6-ene Example 856C (435 mg, 0.934 mmol) was suspended in CH$_2$Cl$_2$ (5 ml) and 4N HCl in dioxane (1.2 ml, 4.80 mmol). Methanol was added until all solid dissolved and the reaction was stirred at room temperature for 2 hours. The reaction mixture was concentrated to dryness to give a solid, which was triturated with ether to give the hydrochloride salt of the title compound. $^1$H NMR (400 MHz, DMSO-d$_6$) δ 12.67 (s, 1H), 10.26 (d, J=10.4 Hz, 1H), 9.56 (d, J=10.3 Hz, 1H), 8.33 (d, J=5.3 Hz, 1H), 7.40-7.21 (m, 4H), 6.67 (d, J=5.4 Hz, 1H), 6.51 (d, J=1.1 Hz, 1H), 4.24 (d, J=4.8 Hz, 1H), 4.02 (t, J=11.9 Hz, 2H), 3.91 (d, J=12.3 Hz, 1H), 3.71-3.64 (m, 1H), 3.57 (s, 3H), 3.53-3.45 (m, 1H), 3.07 (dd, J=18.3, 6.8 Hz, 1H), 2.85 (d, J=18.3 Hz, 1H); MS (ESI+) m/z 366.1 (M+H)$^+$.

EXAMPLE 857

7-[4-(5-fluoro-2-methoxyphenyl)-1H-pyrrolo[2,3-b]pyridin-2-yl]-9-(methylsulfonyl)-3-oxa-9-azabicyclo[3.3.1]non-6-ene Example 856 (65 mg, 0.15 mmol) was dissolved in N,N-dimethylformamide (0.75 ml). Triethylamine (75 mg, 0.74 mmol) was added and the reaction was chilled in an ice bath. Methanesulfonyl chloride (17 mg, 0.15 mmol) was then added and the reaction was allowed to stir overnight, slowly warming to room temperature. The reaction mixture was partitioned between water (5 mL) and ethyl acetate (3×5 mL). The combined organic extracts were dried (Na$_2$SO$_4$), filtered, concentrated and then purified by flash chromatography (0 to 8% methanol-CH$_2$Cl$_2$ over 30 minutes, 4 g column, 18 mL/minute) to provide the title compound. $^1$H NMR (500 MHz, DMSO-d$_6$) δ 11.87 (s, 1H), 8.22 (d, J=4.9 Hz, 1H), 7.31-7.17 (m, 3H), 7.05 (d, J=4.9 Hz, 1H), 6.60 (d, J=5.5 Hz, 1H), 6.30 (s, 1H), 4.33 (d, J=4.8 Hz, 1H), 4.00 (d, J=6.9 Hz, 1H), 3.87 (d, J=11.0 Hz, 1H), 3.74 (s, 3H), 3.70 (d, J=9.2 Hz, 1H), 3.68-3.61 (m, 2H), 2.98 (dd, J=18.2, 7.2 Hz, 1H), 2.92 (s, 3H), 2.58 (d, J=18.2 Hz, 1H); MS (ESI+) m/z 444.2 (M+H)$^+$.

EXAMPLE 858 ethyl ({7-[4-(5-fluoro-2-methoxyphenyl)-1H-pyrrolo[2,3-b]pyridin-2-yl]-3-oxa-9-azabicyclo[3.3.1]non-6-en-9-yl}sulfonyl)carbamate The title compound was prepared as described in Example 218, substituting ethanol for t-butanol in Example 218A and Example 856 for Example 87D in Example 218B. $^1$H NMR (500 MHz, DMSO-d$_6$) δ 11.86 (s, 1H), 11.26 (s, 1H), 8.21 (d, J=4.9 Hz, 1H), 7.28 (td, J=8.6, 3.2 Hz, 1H), 7.21 (ddd, J=9.2, 6.6, 3.9 Hz, 1H), 7.05 (d, J=4.9 Hz, 1H), 6.53 (d, J=5.6 Hz, 1H), 6.24 (d, J=1.9 Hz, 1H), 4.37 (d, J=4.8 Hz, 1H), 4.00 (d, J=7.1 Hz, 1H), 3.88 (dd, J=14.1, 7.3 Hz, 2H), 3.85 (d, J=11.6 Hz, 1H), 3.75 (s, 3H), 3.69 (dd, J=11.1, 1.9 Hz, 1H), 3.66-3.60 (m, 2H), 3.02 (dd, J=17.9, 7.2 Hz, 1H), 2.55-2.51 (m, 1H), 0.90 (t, J=7.1 Hz, 3H). MS (LCMS, APCI+) m/z 517.3 (M+H)$^+$.

EXAMPLE 859

2-{7-[4-(5-fluoro-2-methoxyphenyl)-1H-pyrrolo[2,3-b]pyridin-2-yl]-3-oxa-9-azabicyclo[3.3.1]non-6-en-9-yl}-N,N-dimethylacetamide Example 856 (65 mg, 0.15 mmol) was dissolved in dimethylformamide (0.75 ml) and triethylamine (75 mg, 0.74 mmol) was added, followed by 2-bromo-N,N-dimethylacetamide (0.017 ml, 0.156 mmol). The reaction was heated to 75° C. overnight, then diluted with water (15 mL) and extracted with ethyl acetate (3×10 mL). The combined organic extracts were dried (Na$_2$SO$_4$), filtered, and concentrated, then purified by flash chromatography (0 to 6% methanol-CH$_2$Cl$_2$) to provide the title compound. $^1$H NMR (500 MHz, DMSO-d$_6$) δ 11.82 (s, 1H), 8.20 (d, J=4.9 Hz, 1H), 7.31-7.22 (m, 2H), 7.20 (dd, J=9.0, 4.6 Hz, 1H), 7.04 (d, J=4.9 Hz, 1H), 6.48 (d, J=5.1 Hz, 1H), 6.25 (d, J=1.7 Hz, 1H), 3.75 (s, 3H), 3.73-3.63 (m, 3H), 3.53 (d, J=9.6 Hz, 1H), 3.25 (s, 2H), 3.03 (s, 3H), 2.97 (d, J=6.6 Hz, 1H), 2.81 (s, 3H), 2.74 (dd, J=18.2, 7.0 Hz, 1H), 2.28 (d, J=18.2 Hz, 1H); MS (ESI$^+$) m/z 451.1 (M+H)$^+$.

The following two Examples were prepared essentially as described in Example 218, substituting ethanol for tert-butanol in Example 218A and the appropriate amine for Example 87D in Example 218B.

EXAMPLE 861 ethyl {[4-{4-[3-fluoro-4-(methylcarbamoyl)phenyl]-1H-pyrrolo[2,3-b]pyridin-2-yl}-3,6-dihydropyridin-1(2H)-yl]sulfonyl}carbamate $^1$H NMR (400 MHz, DMSO-d$_6$) δ ppm 1.16 (t, J=7.1 Hz, 3H), 2.62-2.69 (m, 2H), 2.82 (d, J=4.6 Hz, 3H), 3.50 (t, J=5.7 Hz, 2H), 3.98-4.13 (m, 4H), 6.53-6.58 (m, 1H), 6.67 (d, J=2.0 Hz, 1H), 7.23 (d, J=5.0 Hz, 1H), 7.62-7.72 (m, 2H), 7.79 (t, J=7.7 Hz, 1H), 8.25-8.37 (m, 2H), 11.38 (bs, 1H), 12.02-12.07 (m, 1H). MS (ESI$^+$) m/z 502.1 (M+H)$^+$.

EXAMPLE 904 ethyl ({3-[4-(5-fluoro-2-methoxyphenyl)-1H-pyrrolo[2,3-b]pyridin-2-yl]-8-azabicyclo[3.2.1]oct-2-en-8-yl}sulfonyl)carbamate $^1$H NMR (400 MHz, DMSO-d$_6$) δ ppm 1.01 (t, J=7.0 Hz, 3H), 1.60-1.71 (m, 1H), 1.86-2.10 (m, 2H), 2.11-2.25 (m, 1H), 3.01 (dd, J=17.0, 4.4 Hz, 1H), 3.74 (s, 3H), 3.93-4.02 (m, 2H), 4.40 (q, J=5.4 Hz, 2H), 6.19 (d, J=2.0 Hz, 1H), 6.69-6.75 (m, 1H), 7.03 (d, J=4.9 Hz, 1H), 7.15-7.24 (m, 2H), 7.27 (td, J=8.6, 3.2 Hz, 1H), 8.20 (d, J=4.9 Hz, 1H), 11.22 (bs, 1H), 11.77-11.81 (m, 1H). MS (ESI$^+$) m/z 501.1 (M+H)$^+$.

EXAMPLE 862

4-(3-fluoro-2-methoxyphenyl)-2-[1-(methylsulfonyl)-1,2,3,6-tetrahydropyridin-4-yl]-1H-pyrrolo[2,3-b]pyridine The title compound was prepared as described in Example 119, substituting Example 831 for Example 87D. $^1$H NMR (400 MHz, DMSO-d$_6$) δ 2.61 (td, J=5.7, 2.8 Hz, 2H), 2.94 (s, 3H), 3.63 (s, 3H), 3.91 (q, J=2.8 Hz, 2H), 6.32 (d, J=2.0 Hz, 1H), 6.50-6.59 (m, 1H), 7.07 (d, J=5.0 Hz, 1H), 7.17-7.31 (m, 2H), 7.38 (ddd, J=11.6, 7.6, 2.3 Hz, 1H), 8.25 (d, J=4.9 Hz, 1H), 11.94 (br s, 1H); MS (ESI$^+$) m/z 402 (M+H)$^+$.

EXAMPLE 863

4-[4-(3-fluoro-2-methoxyphenyl)-1H-pyrrolo[2,3-b]pyridin-2-yl]-N-methyl-3,6-dihydropyridine-1(2H)-carboxamide The title compound was prepared as described in Example 215, substituting Example 831 for Example 87D. $^1$H NMR (400 MHz, DMSO-d$_6$) δ 2.44 (t, J=5.2 Hz, 2H), 2.59 (d, J=4.2 Hz, 3H), 3.49 (t, J=5.6 Hz, 2H), 3.62 (d, J=1.5 Hz, 3H), 4.00 (q, J=2.7 Hz, 2H), 6.29 (d, J=2.0 Hz, 1H), 6.48 (dt, J=32.2, 3.9 Hz, 2H), 7.05 (d, J=4.8 Hz, 1H), 7.17-7.32 (m, 2H), 7.37 (ddd, J=11.6, 7.6, 2.3 Hz, 1H), 8.24 (s, 1H), 11.87 (d, J=2.5 Hz, 1H); MS (ESI$^+$) m/z 381 (M+H)$^+$.

EXAMPLE 864 methyl 4-[4-(5-fluoro-2-methoxyphenyl)-1H-pyrrolo[2,3-b]pyridin-2-yl]-2,5-dihydro-1H-pyrrole-2-carboxylate

EXAMPLE 864A (S)-1-tert-butyl 2-methyl 4-(((trifluoromethyl)sulfonyl)oxy)-1H-pyrrole-1,2(2H,5H)-dicarboxylate To a −78° C., stirred solution of sodium hexamethyldisilazide (31.7 ml, 31.7 mmol, 1 M tetrahydrofuran) was added (S)-1-tert-butyl 2-methyl 4-oxopyrrolidine-1,2-dicarboxylate (7 g, 28.8 mmol), dissolved in about 25 ml tetrahydrofuran, dropwise via addition funnel. The reaction was stirred for 30 minutes at −78° C. and 1,1,1-trifluoro-N-phenyl-N((trifluoromethyl)sulfonyl)methanesulfonamide (11.31 g, 31.7 mmol) as a tetrahydrofuran solution (20 ml) was added via addition funnel. The reaction mixture was stirred at −78° C. for about 1 hour and warmed to room temperature. Water and dichloromethane were added, the layers were separated and the aqueous layer was extracted with dichloromethane. The combined organics was dried over anhydrous magnesium sulfate, filtered and concentrated by rotary evaporation. The residue was purified by flash column chromatography (220 g silica gel, 0-70% over 30 min) which gave the title compound.

EXAMPLE 864B (S)-1-tert-butyl 2-methyl 4-(4,4,5,5-tetramethyl-1,3,2-dioxaborolan-2-yl)-1H-pyrrole-1,2(2H,5H)-dicarboxylate Example 864A (7.23 g, 19.26 mmol), 4,4,4',4',5,5,5',5'-octamethyl-2,2'-bi(1,3,2-dioxaborolane) (5.87 g, 23.12 mmol) and oven dried potassium acetate (5.67 g, 57.8 mmol) were combined in dioxane (96 ml) and degassed with nitrogen for 15 minutes. PdCl$_2$ (1,1'-bis(diphenylphosphino)ferrocene)-dichloromethane adduct (0.944 g, 1.156 mmol) was added and the flask was flushed with nitrogen. The reaction mixture was heated at 70° C. overnight, cooled, concentrated down onto silica gel by rotary evaporation, and filtered, washing with diethyl ether and a small amount of ethyl acetate. The filtrate was concentrated onto silica gel by rotary evaporation and purified by regular phase flash column chromatography (Analogix, 330 g, 0-75% H:EA) to give the title compound.

EXAMPLE 864C (S)-1-tert-butyl 2-methyl 4-(4-(5-fluoro-2-methoxyphenyl)-1-(phenylsulfonyl)-1H-pyrrolo[2,3-b]pyridin-2-yl)-1H-pyrrole-1,2(2H,5H)-dicarboxylate Example 87B (672 mg, 1.321 mmol), Example 864B (700 mg, 1.982 mmol) and sodium carbonate (420 mg, 3.96 mmol) were combined in tetrahydrofuran (3964 μl), methanol (1982 μl) and water (661 μl). The mixture was degassed for about 5 minutes and PdCl$_2$ (1,1'-bis(diphenylphosphino)ferrocene)-dichloromethane adduct (64.7 mg, 0.079 mmol) was added and the mixture was degassed for 5 minutes. The vial was capped and placed in a microwave reactor (Biotage Initiator, model 355302) at 80° C. for 40 minutes. Water and ethyl acetate were added and the layers were separated. The organics were dried over anhydrous magnesium sulfate, filtered and concentrated by rotary evaporation. The residue was purified by regular phase flash column chromatography (Analogix, 80 g, 0-75% heptanes:ethyl acetate) to give the title compound.

EXAMPLE 864D 1-(tert-butoxycarbonyl)-4-(4-(5-fluoro-2-methoxyphenyl)-1H-pyrrolo[2,3-b]pyridin-2-yl)-2,5-dihydro-1H-pyrrole-2-carboxylic acid Example 864C (491 mg, 0.808 mmol) was combined with dioxane (8080 μl) in a 50 ml round bottom flask. Aqueous sodium hydroxide (5N, 1454 μl, 7.27 mmol) was added and the mixture was heated at 90° C. for 3 hours. The reaction was cooled to room temperature, water was added and the pH was adjusted to 6. The aqueous layer was extracted with ethyl acetate and dichloromethane. The combined organics were dried over anhydrous magnesium sulfate, filtered and concentrated by rotary evaporation to give the title compound.

EXAMPLE 864E methyl 4-(4-(5-fluoro-2-methoxyphenyl)-1H-pyrrolo[2,3-b]pyridin-2-yl)-2,5-dihydro-1H-pyrrole-2-carboxylate dihydrochloride Example 864D (124 mg, 0.273 mmol) was dissolved in tetrahydrofuran (1139 μl) and methanol (228 μl). HCl (4N, 342 μl, 1.367 mmol) in dioxane was added and the reaction was stirred for 2 hours. The solvents were removed to give the title compound as the hydrochloride salt. $^1$H NMR (500 MHz, DMSO-d$_6$) δ 12.91 (s, 1H), 11.47 (dd, J=2.6, 1.5 Hz, 1H), 9.83 (d, J=0.7 Hz, 1H), 8.37 (d, J=5.2 Hz, 1H), 7.43-7.15 (m, 5H), 6.74 (d, J=23.3 Hz, 2H), 5.45 (s, 1H), 3.81 (d, J=6.7 Hz, 3H), 3.76 (s, 3H); MS (ESI+) m/z 368.1 (M+H)$^+$.

EXAMPLE 865

1-{4-[4-(5-fluoro-2-methoxyphenyl)-1H-pyrrolo[2,3-b]pyridin-2-yl]-3,6-dihydropyridin-1(2H)-yl}-3-(3-hydroxyazetidin-1-yl)propane-1,3-dione A solution of Example 705 (HCl salt, 0.055 g, 0.123 mmol) and N-methylmorpholine (0.081 ml, 0.740 mmol) in N,N-dimethylformamide (1.2 ml) was treated with azetidin-3-ol hydrochloride (0.016 g, 0.148 mmol), 1-(3-dimethylaminopropyl)-3-ethylcarbodiimide hydrochloride (0.035 g, 0.185 mmol), and 1H-benzo[d][1,2,3]triazol-1-ol hydrate (0.011 g, 0.074 mmol). The reaction mixture was stirred at room temperature for 15 hours and was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (400 MHz, CD$_3$OD) δ ppm 2.56-2.73 (m, 2H), 3.71-3.90 (m, 6H), 3.99-4.08 (m, 1H), 4.15-4.27 (m, 1H), 4.27-4.41 (m, 2H), 4.41-4.51 (m, 1H), 4.51-4.67 (m, 1H), 6.48-6.65 (m, 2H), 7.17-7.38 (m, 3H), 7.51 (dd, J=6.1, 3.2 Hz, 1H), 8.29 (d, J=6.1 Hz, 1H). MS (ESI$^+$) m/z 465.1 (M+H)$^+$.

EXAMPLE 866

[(2S)-4-[4-(5-fluoro-2-methoxyphenyl)-1H-pyrrolo[2,3-b]pyridin-2-yl]-1-(methylsulfonyl)-2,5-dihydro-1H-pyrrol-2-yl]methanol

EXAMPLE 866A (S)-tert-butyl 4-(4-(5-fluoro-2-methoxyphenyl)-1-(phenylsulfonyl)-1H-pyrrolo[2,3-b]pyridin-2-yl)-2-(hydroxymethyl)-2,5-dihydro-1H-pyrrole-1-carboxylate Example 864C (169 mg, 0.278 mmol) and tetrahydrofuran (2781 µl) were combined in a dry round bottom flask. The reaction mixture was cooled to 0° C. and lithium aluminum hydride (584 µl, 0.584 mmol, 1M tetrahydrofuran) was added dropwise. After 5 minutes at 0° C., water was carefully added and the mixture was diluted with dichloromethane. The layers were separated and the organic layer was dried over anhydrous magnesium sulfate, filtered and concentrated by rotary evaporation. The residue was purified by regular phase flash column chromatography (Analogix, 12 g silica gel, 0-75% heptane:ethyl acetate) to give the title compound.

EXAMPLE 866B (S)-tert-butyl 4-(4-(5-fluoro-2-methoxyphenyl)-1H-pyrrolo[2,3-b]pyridin-2-yl)-2-(hydroxymethyl)-2,5-dihydro-1H-pyrrole-1-carboxylate Example 866A (400 mg, 0.690 mmol) was taken up in dioxane (6901 µl) and 5N sodium hydroxide (690 µl, 3.45 mmol). The reaction was heated at 90° C. for 3 hours. The reaction was cooled, diluted with water and ethyl acetate and the layers were separated. The aqueous layer was extracted with ethyl acetate and the combined organic layers were dried over anhydrous magnesium sulfate, filtered and concentrated by rotary evaporation. The residue was purified by regular phase flash column chromatography (Analogix, 40 g silica gel, 0-100% heptane:ethyl acetate) to give the title compound.

EXAMPLE 866C (S)-(4-(4-(5-fluoro-2-methoxyphenyl)-1H-pyrrolo[2,3-b]pyridin-2-yl)-2,5-dihydro-1H-pyrrol-2-yl)methanol dihydrochloride Example 866B (300 mg, 0.683 mmol) was taken up in tetrahydrofuran (6068 µl), methanol (758 µl) and 4N HCl (1195 µl, 4.78 mmol) in dioxane was added at room temperature; the reaction mixture was stirred for 12 hours and then filtered to give the title compound as a hydrochloride salt.

EXAMPLE 866D (S)-(4-(4-(5-fluoro-2-methoxyphenyl)-1H-pyrrolo[2,3-b]pyridin-2-yl)-1-(methylsulfonyl)-2,5-dihydro-1H-pyrrol-2-yl)methanol Example 866C (50 mg, 0.121 mmol) was taken up in dimethylformamide (1213 µl) and cooled to 0° C. under nitrogen. Triethylamine (85 µl, 0.606 mmol) was added followed by methanesulfonyl chloride (8.51 µl, 0.109 mmol) as a dimethylformamide solution via syringe. The reaction mixture was stirred for 10 minutes at 0° C. and then warmed to room temperature, quenched with water and extracted with ethyl acetate. The combined organic layers were dried over anhydrous magnesium sulfate, filtered and concentrated by rotary evaporation. The residue was purified by regular phase flash column chromatography (Analogix, 12 g silica gel, 0-100% heptane:ethyl acetate) to provide the title compound. $^1$H NMR (400 MHz, DMSO-d$_6$) δ 12.07 (d, J=1.6 Hz, 1H), 8.25 (d, J=4.9 Hz, 1H), 7.36-7.13 (m, 3H), 7.08 (d, J=5.0 Hz, 1H), 6.54 (d, J=1.9 Hz, 1H), 6.31 (d, J=1.9 Hz, 1H), 4.95 (t, J=5.6 Hz, 1H), 4.67-4.47 (m, 2H), 4.47-4.23 (m, 1H), 3.83-3.66 (m, 4H), 3.54-3.39 (m, 1H), 2.95 (s, 3H); MS (ESI+) m/z 418.1 (M+H)$^+$.

EXAMPLE 867 ethyl {[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]sulfonyl}carbamate Example 866C (125 mg, 0.303 mmol) was taken up in dichloromethane and cooled to 0° C. under nitrogen. Triethylamine (254 µl, 1.819 mmol) was added and then ((4-(dimethylamino)pyridin-1-ium-1-yl)sulfonyl)(ethoxycarbonyl)amide (91 mg, 0.334 mmol) was added as a solid, portion wise over 3 minutes. The reaction was stirred for 60 minutes at 0° C. and then warmed to room temperature. The reaction solution was concentrated by rotary evaporation and the residue was purified by regular phase flash column chromatography (Analogix, 12 g silica gel, 0-100% heptane:ethyl acetate) to give the title compound. $^1$H NMR (400 MHz, DMSO-d$_6$) δ ppm 12.07 (d, J=2.2 Hz, 1H), 11.37 (s, 1H), 8.25 (d, J=4.9 Hz, 1H), 7.33-7.16 (m, 3H), 7.08 (d, J=4.9 Hz, 1H), 6.52 (q, J=1.9 Hz, 1H), 6.29 (d, J=1.9 Hz, 1H), 4.96 (s, 1H), 4.85 (tq, J=5.4, 2.3 Hz, 1H), 4.69 (dt, J=13.8, 1.8 Hz, 1H), 4.45 (ddd, J=13.7, 4.9, 2.1 Hz, 1H), 4.03 (qd, J=7.1, 1.3 Hz, 2H), 3.75 (s, 4H), 3.48 (t, J=9.2 Hz, 1H), 1.26-1.08 (m, 3H); MS (ESI+) 491 (M+H)+, 513 (M+Na)$^+$.

EXAMPLE 868

2-({4-[4-(5-fluoro-2-methoxyphenyl)-1H-pyrrolo[2,3-b]pyridin-2-yl]-3,6-dihydropyridin-1(2H)-yl}sulfonyl)-1-(3-hydroxyazetidin-1-yl)ethanone A solution of Example 660D (0.047 g, 0.106 mmol) and N-methylmorpholine (0.058 ml, 0.528 mmol) in N,N-dimethylformamide (1 ml) was treated with 1H-benzo[d][1,2,3]triazol-1-ol hydrate (0.016 g, 0.106 mmol), 1-(3-dimethylaminopropyl)-3-ethylcarbodiimide hydrochloride (0.030 g, 0.158 mmol), and azetidin-3-ol hydrochloride (0.014 g, 0.127 mmol) and the reaction was stirred at room temperature for 15 hours. The mixture was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (400 MHz, CD$_3$OD) δ ppm 2.61-2.72 (m, 2H), 3.61 (t, J=5.7 Hz, 2H), 3.72-3.85 (m, 4H), 3.98-4.08 (m, 2H), 4.11-4.30 (m, 4H), 4.52-4.66 (m, 2H), 6.47-6.61 (m, 2H), 7.17-7.34 (m, 3H), 7.44 (d, J=5.9 Hz, 1H), 8.27 (d, J=6.0 Hz, 1H). MS (ESI$^+$) m/z 501.1 (M+H)$^+$.

EXAMPLE 869

{(2S)-4-[4-(5-fluoro-2-methoxyphenyl)-1H-pyrrolo[2,3-b]pyridin-2-yl]-2,5-dihydro-1H-pyrrol-2-yl}methanol The title compound was prepared as described in Example 866C. $^1$H NMR (400 MHz, DMSO-d$_6$) δ ppm 12.66 (s, 1H), 10.40 (dq, J=12.0, 6.1, 5.2 Hz, 1H), 9.53 (q, J=6.8 Hz, 1H), 8.33 (d, J=5.2 Hz, 1H), 7.41-7.17 (m, 6H), 6.60-6.51 (m, 2H), 3.85-3.37 (m, 8H); MS (ESI$^+$) m/z 240.1 (M+H)$^+$.

EXAMPLE 870

8-[4-(5-fluoro-2-methoxyphenyl)-1H-pyrrolo[2,3-b]pyridin-2-yl]-1,3-diazaspiro[4.5]dec-7-ene-2,4-dione To a solution of Example 241B (100 mg, 0.297 mmol) in ethanol (4.5 mL) and tetrahydrofuran (4.5 mL) was added a solution of ammonium carbonate (114 mg, 1.189 mmol) and ammonium chloride (31.8 mg, 0.595 mmol) in water (2.5 mL). The mixture was stirred at ambient temperature for 15 minutes, potassium cyanide (23.23 mg, 0.357 mmol) was added, and the mixture was stirred overnight. The solvent was removed under reduced pressure and the crude solid was treated with water, filtered and washed with water. Purification by reverse phase preparative HPLC (Phenomenex Luna C8(2) 100 Å AXIA column) eluting with a gradient of 5-100% acetonitrile/0.1% trifluoroacetic acid in water provided the title compound as the trifluoroacetate salt. $^1$H NMR (500 MHz, dimethylsulfoxide-d$_6$) δ 11.98 (s, 1H), 10.67 (s, 1H), 8.33 (d, J=1.7 Hz, 1H), 8.22 (d, J=5.1 Hz, 1H), 7.35-7.26 (m, 1H), 7.26-7.18 (m, 2H), 7.10 (d, J=5.1 Hz, 1H), 6.54-6.44 (m, 1H), 6.29 (d, J=2.0 Hz, 1H), 3.75 (m, 3H), 2.71-2.60 (m, 2H), 2.59-2.52 (m, 1H), 2.34-2.25 (m, 1H), 1.95-1.84 (m, 1H), 1.83-1.72 (m, 1H). MS (ESI$^+$) m/z 406.9 (M+H)$^+$.

EXAMPLE 871

1-amino-4-[4-(5-fluoro-2-methoxyphenyl)-1H-pyrrolo[2,3-b]pyridin-2-yl]cyclohex-3-ene-1-carboxylic acid To a solution of Example 870 (100 mg, 0.246 mmol) in dioxane (1 mL) was added 5M aqueous sodium hydroxide (0.984 mL, 4.92 mmol). The high pressure vessel was capped and the mixture was stirred at 120° C. overnight. After cooling to ambient temperature, the organic layer was decanted and the aqueous layer was washed with two portions of dioxane (0.5 mL). The organics were concentrated and 0.1 mL of trifluoroacetic acid was added. Purification by reverse phase preparative HPLC (Phenomenex Luna C8(2) 100 Å AXIA column) eluting with a gradient of 5-100% acetonitrile/0.1% trifluoroacetic acid in water provided the title compound as the trifluoroacetate salt. $^1$H NMR (500 MHz, dimethylsulfoxide-d$_6$) δ 11.93 (s, 1H), 8.42 (s, 3H), 8.22 (d, J=5.0 Hz, 1H), 7.33-7.26 (m, 1H), 7.26-7.18 (m, 2H), 7.07 (d, J=5.0 Hz, 1H), 6.53-6.43 (m, 1H), 6.29 (d, J=2.0 Hz, 1H), 3.74 (s, 3H), 2.93-2.81 (m, 1H), 2.70-2.57 (m, 1H), 2.54-2.45 (m, 2H), 2.23-2.11 (m, 1H), 2.11-1.99 (m, 1H). MS (ESI$^+$) m/z 382.0 (M+H)$^+$.

EXAMPLE 872

2-(2-azaspiro[3.3]hept-6-yl)-4-(5-fluoro-2-methoxyphenyl)-1H-pyrrolo[2,3-b]pyridine

EXAMPLE 872A tert-butyl 6-(4-(5-fluoro-2-methoxyphenyl)-1-tosyl-1H-pyrrolo[2,3-b]pyridin-2-yl)-6-(2,2,2-trifluoroacetoxy)-2-azaspiro[3.3]heptane-2-carboxylate To a solution of Example 787B (180 mg, 0.296 mmol) and pyridine (59.9 µL, 0.741 mmol) in tetrahydrofuran (3 mL) was slowly added trifluoroacetic anhydride (84 µL, 0.592 mmol). The mixture was stirred at ambient temperature for 45 minutes and quenched with 3 mL saturated aqueous sodium bicarbonate. The mixture was diluted with 10 mL ethyl acetate and the organic layer was washed with brine (1×10 mL), dried over sodium sulfate, filtered and concentrated. Purification by silica gel flash chromatography (Isco®, Redi-Sep® column, 0-75% ethyl acetate/hexane, linear gradient) afforded the title compound. MS (ESI$^+$) m/z 704.4 (M+H)$^+$.

EXAMPLE 872B tert-butyl 6-(4-(5-fluoro-2-methoxyphenyl)-1-tosyl-1H-pyrrolo[2,3-b]pyridin-2-yl)-2-azaspiro[3.3]heptane-2-carboxylate Tetrahydrofuran (0.50 mL) was added to Example 872A (5.0 mg, 7.11 µmol) along with wet 20% palladium hydroxide on carbon (2.4 mg, 0.017 mmol) in a 4 mL pressure bottle. The mixture was stirred under 60 psi of hydrogen at 50° C. for 16 hours. The mixture was filtered through diatomaceous earth and the filter cake was washed with methanol. The filtrate was concentrated to afford the crude title compound. MS (ESI$^+$) m/z 592.0 (M+H)$^+$.

EXAMPLE 872C 2-(2-azaspiro[3.3]hept-6-yl)-4-(5-fluoro-2-methoxyphenyl)-1H-pyrrolo[2,3-b]pyridine To a solution of Example 872B (1230 mg, 2.079 mmol) in dioxane (17.3 mL) was added 5M aqueous sodium hydroxide (3.74 mL, 18.71 mmol) and the mixture was stirred at 90° C. for 3 hours and cooled to ambient temperature. The mixture was concentrated and the solid was washed with heptane and dried under high vacuum. The solid was stirred in 4 mL dichloromethane and 4 mL of trifluoroacetic acid at ambient temperature for 30 minutes and concentrated. The solids were dissolved and passed through a 10G Bond-Elut® resin cartridge (SCX, prewashed with 50% dichloromethane/methanol solution) and washed with a solution of 2M ammonia methanol. The filtrate was concentrated to give to title compound. $^1$H NMR (400 MHz, dimethylsulfoxide-d$_6$) δ 11.59 (s, 1H), 8.13 (d, J=4.9 Hz, 1H), 7.30-7.13 (m, 3H), 7.00 (d, J=4.9 Hz, 1H), 5.99 (s, 1H), 3.72 (s, 3H), 3.61-3.40 (m, 4H), 2.56-2.45 (m, 2H), 2.39-2.27 (m, 2H). MS (ESI$^+$) m/z 338.0 (M+H)$^+$.

EXAMPLE 873

4-(5-fluoro-2-methoxyphenyl)-5-methoxy-2-(1,2,3,6-tetrahydropyridin-4-yl)-1H-pyrrolo[2,3-b]pyridine

EXAMPLE 873A tert-butyl 4-(4-(5-fluoro-2-methoxyphenyl)-5-methoxy-1-(phenylsulfonyl)-1H-pyrrolo[2,3-b]pyridin-2-yl)-5,6-dihydropyridine-1(2H)-carboxylate The title compound was prepared according to the procedure described in Example 87C, substituting Example 852C for Example 87B. MS (ESI$^+$) m/z 594 (M+H)$^+$.

EXAMPLE 873B tert-butyl 4-(4-(5-fluoro-2-methoxyphenyl)-5-methoxy-1H-pyrrolo[2,3-b]pyridin-2-yl)-5,6-dihydropyridine-1(2H)-carboxylate The title compound was prepared according to the procedure described in Example 236E, substituting Example 873A for Example 236D. MS (ESI$^+$) m/z 454 (M+H)$^+$.

EXAMPLE 873C 4-(5-fluoro-2-methoxyphenyl)-5-methoxy-2-(1,2,3,6-tetrahydropyridin-4-yl)-1H-pyrrolo[2,3-b]pyridine The title compound was prepared according to the procedure described in Example 236F, substituting Example 873B for Example 236E. $^1$H NMR (400 MHz, DMSO-d$_6$) δ 2.60-2.70 (br, 2H), 3.30 (dt, J=10.5, 5.5 Hz, 2H), 3.68 (s, 3H), 3.78 (s, 5H), 6.07 (d, J=2.0 Hz, 1H), 6.31-6.73 (m, 1H), 6.94-7.55 (m, 3H), 8.17 (s, 1H), 8.95 (s, 2H), 11.82 (d, J=2.2 Hz, 1H). MS (ESI$^+$) m/z 354 (M+H)$^+$.

EXAMPLE 874 ethyl 4-(5-fluoro-2-methoxyphenyl)-2-(1,2,3,6-tetrahydropyridin-4-yl)-1H-pyrrolo[2,3-b]pyridine-3-carboxylate

EXAMPLE 874A 4-chloro-3-iodo-1-((2-(trimethylsilyl)ethoxy)methyl)-1H-pyrrolo[2,3-b]pyridine An 100 mL 3-necked round bottom flask was charged with 4-chloro-3-iodo-1H-pyrrolo[2,3-b]pyridine (4.00 g, 14.36 mmol) at ambient temperature under nitrogen. The solid was dissolved in anhydrous tetrahydrofuran (50 mL), and solution was cooled to −5° C. To this was added portionwise solid 60% NaH in mineral oil (0.862 g, 21.55 mmol) at a rate such that the temperature was maintained at or below 0° C. The addition took about 10 minutes, and the resulting mixture was stirred an additional 30 minutes at −5° C. This was followed by dropwise addition of 2-(trimethylsilyl)ethoxymethyl chloride (3.06 mL, 17.24 mmol) over a period of 15 minutes. The reaction mixture was stirred for 30 minutes at −5° C., and then allowed to warm to ambient temperature and stir overnight. The reaction mixture was quenched with aqueous saturated ammonium chloride solution and diluted with ethyl acetate. The layers were separated, and organic layer was washed with brine, dried with Na$_2$SO$_4$, decanted, and concentrated. The residue was purified on an Analogix MPLC using an Analogix SF40-150 g silica gel column eluting with 3 to 5% ethyl acetate in heptane to provide the title compound. MS (DCI/NH$_3$) m/z 409 (M+H)$^+$.

EXAMPLE 874B ethyl 4-chloro-1-((2-(trimethylsilyl)ethoxy)methyl)-1H-pyrrolo[2,3-b]pyridine-3-carboxylate A solution of Example 874A (5.18 g, 12.67 mmol) in ethanol (50 mL) was added to PdCl$_2$ (1,1'-bis(diphenylphosphino)ferrocene)-CH$_2$Cl$_2$ (0.464 g, 0.634 mmol) and triethylamine (3.53 mL, 25.3 mmol) in a 250 mL pressure bottle. The mixture was pressurized with carbon monoxide (60 psi), and heated at 60° C. for 24 hours. After cooling, solid material was filtered off, and the filtrate was concentrated. The residue was purified on an Analogix MPLC using a Grace/Reveleris 120 g silica gel column eluting with 10-40% ethyl acetate in heptane to provide the title compound. MS (DCI/NH$_3$) m/z 355 (M+H)$^+$.

EXAMPLE 874C ethyl 4-chloro-2-iodo-1-((2-(trimethylsilyl)ethoxy)methyl)-1H-pyrrolo[2,3-b]pyridine-3-carboxylate To a cold (−78° C.) solution of Example 874B (0.8 g, 2.254 mmol) in tetrahydrofuran (20 mL) was added lithium diisopropylamide (2 M solution in tetrahydrofuran, 2.25 mL, 4.51 mmol). The reaction mixture was stirred at −78° C. for 1 hour, after which a solution of I$_2$ (1.14 g, 4.51 mmol) in tetrahydrofuran (5 mL) was added. The reaction mixture was stirred at the same temperature for 1 hour, and the reaction was quenched by adding 1M solution of Na$_2$S$_2$O$_3$. Ethyl acetate was then added and the mixture was partitioned between ethyl acetate and brine. The organic layer was concentrated, and the residue was separated by flash chromatography (10-30% ethyl acetate in hexane) to provide the title compound. MS (DCI/NH$_3$) m/z 481 (M+H)$^+$.

EXAMPLE 874D ethyl 2-(1-(tert-butoxycarbonyl)-1,2,3,6-tetrahydropyridin-4-yl)-4-chloro-1-((2-(trimethylsilyl)ethoxy)methyl)-1H-pyrrolo[2,3-b]pyridine-3-carboxylate A mixture of Example 874C (800 mg, 1.664 mmol), tert-butyl 4-(4,4,5,5-tetramethyl-1,3,2-dioxaborolan-2-yl)-5,6-dihydropyridine-1(2H)-carboxylate (669 mg, 2.16 mmol), and Pd(Ph$_3$P)$_4$ (192 mg, 0.166 mmol) was purged with nitrogen. N,N-Dimethylformamide (30 mL) and saturated sodium carbonate solution (7.5 mL) were added. The mixture was purged with nitrogen again, and heated at 85° C. for 8 hours. After cooling, the reaction mixture was partitioned between ethyl acetate and brine. The organic phase was washed with brine, and concentrated. The residue was separated by flash chromatography (5-30% ethyl acetate in hexane) to provide the title compound. MS (DCI/NH$_3$) m/z 536 (M+H)$^+$.

EXAMPLE 874E ethyl 2-(1-(tert-butoxycarbonyl)-1,2,3,6-tetrahydropyridin-4-yl)-4-(5-fluoro-2-methoxyphenyl)-1-((2-(trimethylsilyl)ethoxy)methyl)-1H-pyrrolo[2,3-b]pyridine-3-carboxylate A mixture of Example 874D (0.73 g, 1.36 mmol), 5-fluoro-2-methoxyphenylboronic acid (0.347 g, 2.04 mmol), phenylallylchloro[1,3-bis(diisopropylphenyl)-2-imidazol-2-ylidene]palladium (II) (26 mg, 0.041 mmol) and potassium phosphate (0.867 g, 4.08 mmol) was suspended in a mixture of tetrahydrofuran (15 mL) and water (5 mL). The suspension was purged with nitrogen, and heated at 60° C. for 2.5 hours. After cooling, the reaction mixture was partitioned between ethyl acetate and brine. The organic phase was washed with brine, and concentrated. The residue was separated by flash chromatography (20-60% ethyl acetate in hexane) to give the title compound. MS (DCI/NH$_3$) m/z 626 (M+H)$^+$.

EXAMPLE 874F ethyl 4-(5-fluoro-2-methoxyphenyl)-2-(1,2,3,6-tetrahydropyridin-4-yl)-1H-pyrrolo[2,3-b]pyridine-3-carboxylate To a solution of Example 874E (600 mg, 0.959 mmol) in tetrahydrofuran (24 mL) was added HCl (37%, 3.5 mL), and the mixture was heated at 60° C. overnight. The volatiles were removed, and the residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient). The desired fraction was concentrated, and the residue was partitioned between ethyl acetate and sodium bicarbonate solution. The organic phase was washed with water and concentrated to provide the title compound. $^1$H NMR (500 MHz, DMSO-d$_6$): δ0.84 (t, J=7.17 Hz, 3 H), 2.22-2.28 (m, 1 H), 2.38-2.43 (m, 1 H), 2.87-2.90 (m, 2 H), 3.37-3.46 (m, 3 H), 3.56 (s, 3 H), 3.73-3.79 (m, 2 H), 6.23 (s, 1 H), 6.98-7.04 (m, 2 H), 7.10-7.13 (m, 1 H), 7.18-7.23 (m, 1 H), 8.26 (d, J=4.88 Hz, 1 H), 12.10 (br s, 1 H); MS (DCI/NH$_3$) m/z 396 (M+H)$^+$.

EXAMPLE 875

4-(5-fluoro-2-methoxyphenyl)-2-(1-{[1-(methylsulfonyl)piperidin-4-yl]sulfonyl}-1,2,3,6-tetrahydropyridin-4-yl)-1H-pyrrolo[2,3-b]pyridine The title compound was prepared using the procedure described in Example 794, using Example 825 in place of Example 87D and methanesulfonyl chloride in place of 2-(1,3-dioxoisoindolin-2-yl)ethanesulfonyl chloride. $^1$H NMR (400 MHz, DMSO-d$_6$) δ 11.95 (s, 1H), 8.23 (d, J=5.1 Hz, 1H), 7.35-7.17 (m, 3H), 7.08 (d, J=5.0 Hz, 1H), 6.53 (d, J=3.6 Hz, 1H), 6.30 (d, J=2.0 Hz, 1H), 4.04 (s, 2H), 3.74 (s, 3H), 3.66-3.34 (m, 5H), 2.82 (s, 3H), 2.81-2.72 (m, 2H), 2.56 (s, 2H), 2.10-2.07 (m, 2H), 1.65 (qd, J=12.4, 4.3 Hz, 2H). MS (ESI+) m/e 549 (M+H)$^+$.

EXAMPLE 876

N-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]methanesulfonamide The title compound was prepared using the procedure described in Example 794, using Example 840 in place of Example 87D and methanesulfonyl chloride in place of 2-(1,3-dioxoisoindolin-2-yl)ethanesulfonyl chloride. $^1$H NMR (400 MHz, DMSO-d$_6$) δ 11.96 (s, 1H), 8.23 (d, J=5.0 Hz, 1H), 7.35-7.16 (m, 4H), 7.08 (d, J=4.9 Hz, 1H), 6.54 (s, 1H), 6.30 (s, 1H), 3.99 (d, J=3.5 Hz, 2H), 3.74 (s, 3H), 3.51-3.26 (m, 6H), 2.95 (s, 3H), 2.60 (s, 2H). MS (ESI+) m/e 509 (M+H)$^+$.

EXAMPLE 877

{4-[4-(5-fluoro-2-methoxyphenyl)-1H-pyrrolo[2,3-b]pyridin-2-yl]-1-(methylsulfonyl)-1,2,3,6-tetrahydropyridin-2-yl}methanol Methanesulfonyl chloride (16 mg, 0.14 mmol) was added to a 0° C. solution of Example 855 (50 mg, 0.14 mmol) and triethylamine (72 mg, 0.71 mmol) in N,N-dimethylformamide (0.70 mL) and the resulting mixture was stirred overnight, slowly warming to room temperature. The mixture was then partitioned between water (5 mL) and ethyl acetate (4×5 mL), and extracts were dried (Na$_2$SO$_4$), filtered, and concentrated then purified by flash (0 to 6% methanol-CH$_2$Cl$_2$ over 40 min, 4 g Grace column, 15 mL/min) to provide the title compound. $^1$H NMR (500 MHz, DMSO-d$_6$) δ 11.87 (s, 1H), 8.21 (d, J=4.9 Hz, 1H), 7.28 (td, J=8.6, 3.2 Hz, 1H), 7.25-7.18 (m, 2H), 7.04 (d, J=4.9 Hz, 1H), 6.50 (s, 1H), 6.25 (d, J=1.7 Hz, 1H), 5.00 (t, J=5.5 Hz, 1H), 4.21-4.09 (m, 2H), 3.84 (d, J=16.6 Hz, 1H), 3.74 (s, 3H), 3.53-3.45 (m, 1H), 3.43-3.37 (m, 1H), 2.99 (s, 3H), 2.66-2.54 (m, 2H); MS (ESI+) m/z 432.1 (M+H)$^+$.

EXAMPLE 878 ethyl ({4-[4-(5-fluoro-2-methoxyphenyl)-1H-pyrrolo[2,3-b]pyridin-2-yl]-2-(hydroxymethyl)-3,6-dihydropyridin-1(2H)-yl}sulfonyl)carbamate ((4-(Dimethylamino)pyridin-1-ium-1-yl)sulfonyl)(ethoxycarbonyl)amide (38.7 mg, 0.141 mmol) was added to a stirred, 0° C. solution of Example 855 (50 mg, 0.141 mmol) and triethylamine (71.6 mg, 0.707 mmol) in N,N-dimethylformamide (0.70 mL). The mixture was stirred at 0° C. for 1 hour then allowed to warm to room temperature and stirred for 24 hours. The mixture was diluted with water (5 mL) and extracted with ethyl acetate (3×5 mL). The combined organic extracts were dried (Na$_2$SO$_4$), filtered and concentrated, and purified by flash chromatography (0 to 7% methanol-CH$_2$Cl$_2$ over 30 min, 4 g Grace column, 15 mL/min) followed by trituration with ether to provide the title compound. $^1$H NMR (400 MHz, DMSO-d$_6$) δ 11.85 (s, 1H), 8.20 (d, J=4.9 Hz, 1H), 7.28 (td, J=8.6, 3.2 Hz, 1H), 7.24-7.16 (m, 2H), 7.03 (d, J=5.0 Hz, 1H), 6.48 (s, 1H), 6.25 (d, J=1.8 Hz, 1H), 4.25 (d, J=18.4 Hz, 1H), 4.11-3.94 (m, 3H), 3.90 (d, J=17.1 Hz, 1H), 3.73 (s, 3H), 3.48-3.35 (m, 2H), 2.65 (d, J=17.0 Hz, 1H), 2.58-2.48 (m, 1H), 1.08 (t, J=7.1 Hz, 3H); MS (ESI+) m/z 505.1 (M+H)$^+$.

EXAMPLE 879

2-{4-[4-(5-fluoro-2-methoxyphenyl)-1H-pyrrolo[2,3-b]pyridin-2-yl]-2-(hydroxymethyl)-3,6-dihydropyridin-1(2H)-yl}-N,N-dimethylacetamide 2-Bromo-N,N-dimethylacetamide (15 μl, 0.14 mmol) was added dropwise to a stirred solution of Example 855 (50 mg, 0.14 mmol) and triethylamine (72 mg, 0.71 mmol) in N,N-dimethylformamide (0.70 mL), and the mixture was warmed to 70° C. for 3 hours. The mixture was diluted with water (5 mL) and extracted with ethyl acetate (3×5 mL). The extracts were dried ($Na_2SO_4$), filtered, and concentrated, then purified by flash chromatography (0 to 7% methanol-dichloromethane over 30 minutes, 4 g Grace column, 15 mL/min) to provide the title compound. $^1H$ NMR (400 MHz, DMSO-$d_6$) δ 11.77 (s, 1H), 8.18 (d, J=4.9 Hz, 1H), 7.34-7.14 (m, 3H), 7.02 (d, J =4.9 Hz, 1H), 6.46 (s, 1H), 6.18 (d, J=1.7 Hz, 1H), 4.61 (t, J=5.4 Hz, 1H), 3.74 (s, 3H), 3.60-3.37 (m, 6H), 3.02 (s, 3H), 2.97-2.89 (m, 1H), 2.81 (s, 3H), 2.49-2.34 (m, 2H); MS (ESI+) m/z 439.0 $(M+H)^+$.

EXAMPLE 880

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide To a mixture of Example 845 (0.059 g, 0.17 mmol) and 2-chloro-N,N-dimethylacetamide (0.022 g, 0.179 mmol) in dimethylformamide (2 mL) was added N-ethyl-N-isopropylpropan-2-amine (0.148 mL, 0.850 mmol). The mixture was stirred at 70° C. for 2 hours, and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1H$ NMR (400 MHz, DMSO-$d_6$) δ ppm 2.60-2.84 (m, 1 H) 2.88 (s, 4 H) 2.89 (s, 2 H) 2.91 (s, 2 H) 2.98-3.47 (m, 3 H) 3.60-3.69 (m, 1 H) 3.74 (s, 3 H) 3.78-4.37 (m, 3 H) 6.25 (d, J=1.83 Hz, 1 H) 6.32 (d, J=33.57 Hz, 1 H) 7.09 (d, J=5.19 Hz, 1 H) 7.17-7.35 (m, 3 H) 8.25 (dd, J=5.04, 2.90 Hz, 1 H) 12.12 (d, J=9.16 Hz, 1 H). MS ($ESI^+$) m/z 435 $(M+H)^+$.

EXAMPLE 881

4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine The title compound was prepared as described in Example 262F. $^1H$ NMR (400 MHz, DMSO-$d_6$) δ ppm 2.56-2.66 (m, 1 H) 2.87 (s, 3 H) 2.90-3.12 (m, 3 H) 3.12-3.23 (m, 1 H) 3.34-3.48 (m, 2 H) 3.55-3.67 (m, 1 H) 3.74 (s, 3 H) 6.23 (d, J=1.83 Hz, 1 H) 6.33 (d, J=1.53 Hz, 1 H) 7.10 (d, J=5.19 Hz, 1 H) 7.15-7.34 (m, 3 H) 8.24 (d, J=5.19 Hz, 1 H) 12.05 (s, 1 H). MS ($ESI^+$) m/z 428 $(M+H)^+$.

EXAMPLE 882

4-[4-(5-fluoro-2-methoxyphenyl)-1H-pyrrolo[2,3-b]pyridin-2-yl]-N,N-dimethyl-2,5-dihydro-1H-pyrrole-2-carboxamide To Example 846 (6 mg, 0.012 mmol) was added $CH_2Cl_2$/trifluoroacetic acid (2/1, 0.4 mL). The mixture was stirred at room temperature for 1 hour and concentrated in vacuo to afford the title compound as the bis-trifluoroacetate salt. $^1H$ NMR (400 MHz, DMSO-$d_6$) δ ppm 2.96 (s, 3 H) 3.17 (s, 3 H) 3.74 (s, 3 H) 4.35-4.58 (m, 2 H) 5.67 (s, 1 H) 6.55 (d, J=1.53 Hz, 1 H) 6.68 (d, J=1.53 Hz, 1 H) 7.12 (d, J=4.88 Hz, 1 H) 7.16-7.36 (m, 3 H) 8.30 (d, J=4.88 Hz, 1 H) 9.12 (s, 1 H) 10.32 (s, 1 H) 12.16 (s, 1 H). MS ($ESI^+$) m/z 381 $(M+H)^+$.

EXAMPLE 883

2-(4-{4-[4-(5-fluoro-2-methoxyphenyl)-1H-pyrrolo[2,3-b]pyridin-2-yl]-3,6-dihydropyridin-1(2H)-yl}piperidin-1-yl)-N,N-dimethylacetamide A mixture of Example 523B (0.106 g, 0.197 mmol), benzotriazol-1-yloxy)tripyrrolidinophosphonium hexafluorophosphate (PyBOP, 0.123 g, 0.237 mmol), triethylamine (0.165 mL, 1.183 mmol), and dimethylamine•hydrochloride (0.035 g, 0.434 mmol) in N,N-dimethylformamide (2.5 mL) was stirred for 3 hours. The reaction mixture was treated with water and stirred for 15 minutes. The solids formed were filtered and purified on a 12 g column using the ISCO Companion flash system eluting with $CH_2Cl_2/CH_3OH/NH_4OH$ (18:1:0.1 to 12:1:0.1) to provide the title compound. $^1H$ NMR (400 MHz, methanol-$d_4$) δ ppm 1.59-1.75 (m, 2H), 1.88-2.01 (m, 2H), 2.08-2.18 (m, 2H), 2.36-2.47 (m, 1H), 2.59 (bs, 2H), 2.84 (t, J=5.7 Hz, 2H), 2.93 (s, 3H), 2.98-3.06 (m, 2H), 3.09 (s, 3H), 3.21 (s, 1H), 3.37-3.38 (m, 2H), 3.76 (s, 3H), 4.56, (bs, 1H), 6.26 (s, 1H), 6.37-6.43 (m, 1H), 7.07 (d, J=5.1 Hz, 1H), 7.10-7.20 (m, 3H), 8.15 (d, J=5.1 Hz, 1H). MS ($ESI^+$) m/z 492.2 $(M+H)^+$.

EXAMPLE 884

N-{4-[4-(2,3-difluorophenyl)-1H-pyrrolo[2,3-b]pyridin-2-yl]cyclohex-3-en-1-yl}glycine

EXAMPLE 884A

The title compound was prepared essentially as described in Example 241A, substituting Example 219A with Example 703C. LCMS (APCI): 369.0 $(M+H)^+$.

EXAMPLE 884B 4-(4-(2,3-difluorophenyl)-1H-pyrrolo[2,3-b]pyridin-2-yl)cyclohex-3-enone The title compound was prepared essentially as described in Example 241B, substituting Example 241A with Example 884A. MS (ESI): 325.2 $(M+H)^+$.

EXAMPLE 884C

N-{4-[4-(2,3-difluorophenyl)-1H-pyrrolo[2,3-b]pyridin-2-yl]cyclohex-3-en-1-yl}glycine The title compound was prepared essentially as described in Example 241C, substituting Example 241B with Example 884B and (R)-tert-butyl 2-amino-3-methylbutanoate hydrochloride with tert-butyl 2-aminoacetate. $^1H$ NMR (500 MHz, DMSO-$d_6$) δ ppm 12.45 (s, 1 H) 9.46 (d, J=39.06 Hz, 2 H) 8.33 (d, J=5.19 Hz, 1 H) 7.54-7.66 (m, 1 H) 7.48 (t, J=7.02 Hz, 1 H) 7.36-7.45 (m, 1 H) 7.25 (d, J=4.88 Hz, 1 H) 6.52-6.61 (m, 1 H) 6.46 (s, 1 H) 3.87-4.04 (m, 2 H) 3.26-3.45 (m, 1 H) 2.60-2.80 (m, 2 H) 2.37-2.48 (m, 2 H) 2.27 (d, J=10.07 Hz, 1 H) 1.69-1.90 (m, 1 H). MS (ESI): 384.1 $(M+H)^+$.

EXAMPLE 885

1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone

EXAMPLE 885A tert-butyl 3-((4-(4-(5-fluoro-2-methoxyphenyl)-1H-pyrrolo[2,3-b]pyridin-2-yl)-5,6-dihydropyridin-1(2H)-yl)sulfonyl)azetidine-1-carboxylate The title compound was prepared using the procedure described in Example 794, using tert-butyl 3-(chlorosulfonyl)azetidine-1-carboxylate in place of 2-(1,3-dioxoisoindolin-2-yl)ethanesulfonyl chloride.

EXAMPLE 885B 2-(1-(azetidin-3-ylsulfonyl)-1,2,3,6-tetrahydropyridin-4-yl)-4-(5-fluoro-2-methoxyphenyl)-1H-pyrrolo[2,3-b]pyridine The title compound was prepared using the procedure described in Example 795D, using Example 885A in place of Example 795C. MS (ESI+) m/e 443 (M+H)$^+$.

EXAMPLE 885C

1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone The title compound was prepared using the procedure described in Example 10B, using Example 885B in place of Example 10A. $^1$H NMR (500 MHz, DMSO-d$_6$) δ 11.99 (s, 1H), 8.24 (d, J =5.0 Hz, 1H), 7.34-7.12 (m, 3H), 7.12-7.05 (m, 1H), 6.52 (s, 1H), 6.30 (s, 1H), 4.43-4.26 (m, 2H), 4.16-4.06 (m, 1H), 4.04-3.84 (m, 4H), 3.74 (s, 3H), 3.48 (t, J=6.0 Hz, 2H), 2.58 (s, 2H), 1.77 (s, 3H). MS (ESI+) m/e 485 (M+H)$^+$.

EXAMPLE 886

4-(5-fluoro-2-methoxyphenyl)-2-(1-{[1-(methylsulfonyl)azetidin-3-yl]sulfonyl}-1,2,3,6-tetrahydropyridin-4-yl)-1H-pyrrolo[2,3-b]pyridine The title compound was prepared using the procedure described in Example 794, using Example 885B in place of Example 87D and methanesulfonyl chloride in place of 2-(1,3-dioxoisoindolin-2-yl)ethanesulfonyl chloride. $^1$H NMR (500 MHz, DMSO-d$_6$) δ 12.02 (s, 1H), 8.24 (d, J=5.1 Hz, 1H), 7.35-7.17 (m, 3H), 7.10 (d, J=5.0 Hz, 1H), 6.52 (d, J=3.7 Hz, 1H), 6.31 (s, 1H), 4.51-4.42 (m, 1H), 4.21-4.11 (m, 4H), 4.01 (s, 2H), 3.74 (s, 3H), 3.48 (t, J=5.9 Hz, 2H), 3.07 (s, 3H), 2.57 (s, 2H). MS (ESI+) m/e 521 (M+H)$^+$.

EXAMPLE 887 ethyl 4-(5-fluoro-2-methoxyphenyl)-2-[1-(methylsulfonyl)-1,2,3,6-tetrahydropyridin-4-yl]-1H-pyrrolo[2,3-b]pyridine-3-carboxylate To a solution of Example 874F (265.2 mg, 0.671 mmol) in methylene chloride (15 mL) was added triethylamine (0.374 mL, 2.68 mmol) and methanesulfonyl chloride (115 mg, 1.006 mmol). The solution was stirred at room temperature overnight, and was directly separated by flash chromatography (0-15% CH$_3$OH in CH$_2$Cl$_2$) to provide the title compound. $^1$H NMR (400 MHz, DMSO-d$_6$): δ0.82 (t, J=7.02 Hz, 3 H), 2.54-2.64 (m, 2 H), 2.97 (s, 3 H), 3.37 (t, J=5.80 Hz, 2 H), 3.44-3.48 (m, 1 H), 3.56 (s, 3 H), 3.76-3.82 (m, 1 H), 3.87-3.91 (m, 2 H), 6.22 (s, 1 H), 7.01-7.05 (m, 2 H), 7.13 (dd, J=9.00, 3.20 Hz, 1 H), 7.19-7.24 (m, 1 H), 8.30 (d, J=4.88 Hz, 1 H), 12.31 (s, 1 H); MS (DCI/NH$_3$) m/z 474 (M+H)$^+$.

EXAMPLE 888

4-(5-fluoro-2-methoxyphenyl)-2-(2,3,6,7-tetrahydro-1H-azepin-4-yl)-1H-pyrrolo[2,3-b]pyridine A mixture of 4-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,7-tetrahydro-1H-azepin-4-yl)-1H-pyrrolo[2,3-b]pyridine (Example 733C) was separated by HPLC (Luna C8(2) 5 um 100 Å AXIA column; gradient of acetonitrile with 0.1% trifluoroacetic acid and water, 10-95%) to provide the title compound. $^1$H NMR (500 MHz, DMSO-d$_6$) δ 2.62 (t, J=5.8 Hz, 2H), 2.71-2.92 (m, 2H), 3.17 (dq, J=15.3, 4.8 Hz, 4H), 3.64 (s, 2H), 3.74 (s, 3H), 6.37 (d, J=2.0 Hz, 1H), 6.67 (t, J=6.4 Hz, 1H), 7.06 (d, J=5.0 Hz, 1H), 7.16-7.24 (m, 2H), 7.27-7.34 (m, 1H), 8.22 (d, J=5.0 Hz, 1H), 8.84 (br s, 2H), 11.87 (br s, 1H); MS (ESI$^+$) m/z 336 (M+H)$^+$.

EXAMPLE 889

3-(2-{4-[4-(5-fluoro-2-methoxyphenyl)-1H-pyrrolo[2,3-b]pyridin-2-yl]-3,6-dihydropyridin-1(2H)-yl}-2-oxoethyl)imidazolidine-2,4-dione A suspension of Example 101 (free base, 0.048 g, 0.113 mmol), polymer bound triphenylphosphine (1.8 mmol/g, 0.076 g, 0.136 mmol) and imidazolidine-2,4-dione (0.014 g, 0.136 mmol) in tetrahydrofuran (1.2 mL) was treated with a solution of diisopropyl azodicarboxylate (0.027 g, 0.136 mmol) in 0.3 mL tetrahydrofuran added dropwise over 3 minutes. The reaction mixture was stirred at room temperature for 16 hours. Additional polymer bound triphenylphosphine (1.8 mmol/g, 0.031 g, 0.057 mmol), and diisopropyl azodicarboxylate (0.011 g, 0.057 mmol) were added and the reaction was stirred at room temperature for 14 hours. The reaction mixture was filtered and the filtrate was concentrated. The concentrate was purified by flash chromatography on silica gel (AnaLogix IntelliFlash 280 system) eluting with a gradient of from 0% to 8% methanol in dichloromethane to afford the title compound. $^1$H NMR (400 MHz, DMSO-d$_6$) δ ppm 2.44-2.51 (m, 1H), 2.56-2.65 (m, 1H), 3.60-3.80 (m, 5H), 3.99 (s, 2H), 4.07-4.18 (m, 1H), 4.24-4.38 (m, 3H), 6.27 (d, J=1.9 Hz, 1H), 6.48-6.57 (m, 1H), 7.04 (d, J=5.0, 1.0 Hz, 1H), 7.14-7.34 (m, 3H), 8.10 (s, 1H), 8.21 (d, J=5.0, 1.3 Hz, 1H), 11.82-11.94 (m, 1H). MS (ESI$^+$) m/z 464.1 (M+H)$^+$.

EXAMPLE 890

({4-[4-(5-fluoro-2-methoxyphenyl)-1H-pyrrolo[2,3-b]pyridin-2-yl]-3,6-dihydropyridin-1(2H)-yl}sulfonyl)acetonitrile The title compound was prepared essentially as described in Example 661 substituting cyanomethanesulfonyl chloride for (methylsulfonyl)methanesulfonyl chloride in Example 661A. $^1$H NMR (500 MHz, DMSO-d$_6$) δ ppm 2.61-2.71 (m, 2H), 3.50 (m, 2H), 3.74 (s, 3H), 4.07-4.13 (m, 2H), 4.94 (s, 2H), 6.31 (d, J=2.1 Hz, 1H), 6.51-6.57 (m, 1H), 7.08 (d, J=5.0 Hz, 1H), 7.14-7.34 (m, 3H), 8.24 (d, J=5.0 Hz, 1H), 11.98 (d, J=2.4 Hz, 1H). MS (ESI$^+$) m/z 427.1 (M+H)$^+$.

EXAMPLE 891 propan-2-yl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting isopropanol for ethanol in Example 218A. $^1$H NMR (400 MHz, DMSO-d$_6$): δ1.16 (d, J=6.41 Hz, 6 H), 2.56-2.60 (m, 2 H), 3.47 (t, J=5.80 Hz, 2 H), 3.73 (s, 3 H), 4.02 (d, J=2.44 Hz, 2 H), 4.76-4.82 (m, 1 H), 6.26 (d, J=1.83 Hz, 1 H), 6.51 (s, 1H), 7.04 (d, J=5.19 Hz, 1 H), 7.17-7.30 (m, 3 H), 8.21 (d, J=4.88 Hz, 1 H), 11.27 (s, 1 H), 11.85 (s, 1 H); MS (DCI/NH$_3$) m/z 489 (M+H)$^+$.

EXAMPLE 892

4-(5-fluoro-2-methoxyphenyl)-2-[2-(methylsulfonyl)-2-azaspiro[3.3]hept-6-yl]-1H-pyrrolo[2,3-b]pyridine The title compound was prepared as described in Example 119, substituting Example 872 for Example 87D. $^1$H NMR (400 MHz, DMSO-d$_6$) δ ppm 2.41-2.49 (m, 2 H) 2.54-2.63 (m, 2 H) 2.96 (s, 3 H) 3.46-3.60 (m, 1 H) 3.74 (s, 3 H) 3.81 (s, 2 H) 3.98 (s, 2 H) 6.16 (d, J=1.22 Hz, 1 H) 7.16 (d, J=5.49 Hz, 1 H) 7.19-7.26 (m, 2 H) 7.27-7.35 (m, 1 H) 8.23 (d, J=5.19 Hz, 1 H) 12.02 (s, 1 H). MS (ESI$^+$) m/z 416 (M+H)$^+$.

EXAMPLE 893 ethyl ({4-[5-cyano-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for tert-butanol in Example 218A and substituting Example 236F for Example 87D in Example 218B. $^1$H NMR (400 MHz, DMSO-d$_6$) δ 1.14 (t, J=7.1 Hz, 3H), 2.67 (s, 2H), 3.23 (s, 1H), 3.45 (q, J=7.9, 7.0 Hz, 2H), 3.76 (d, J=1.5 Hz, 3H), 3.93-4.14 (m, 3H), 6.32 (d, J=2.0 Hz, 1H), 6.47-6.80 (m, 1H), 7.11-7.62 (m, 3H), 8.62 (s, 1H), 11.38 (s, 1H), 12.53 (s, 1H). MS (ESI$^+$) m/z 500 (M+H)$^+$.

EXAMPLE 894

N-[2-(4-fluoro-2-{2-[1-(methylsulfonyl)-1,2,3,6-tetrahydropyridin-4-yl]-1H-pyrrolo[2,3-b]pyridin-4-yl}phenoxy)ethyl]methanesulfonamide The title compound was prepared using the procedure described in Example 794, using Example 795D in place of Example 87D and methanesulfonyl chloride in place of 2-(1,3-dioxoisoindolin-2-yl)ethanesulfonyl chloride. $^1$H NMR (500 MHz, DMSO-d$_6$) δ 12.04 (s, 1H), 8.24 (d, J=5.1 Hz, 1H), 7.38-7.15 (m, 4H), 7.06 (t, J=5.8 Hz, 1H), 6.55 (d, J=3.9 Hz, 1H), 6.38 (d, J=2.0 Hz, 1H), 4.05 (t, J=6.0 Hz, 2H), 3.92 (m, 2H), 3.37 (t, J=5.8 Hz, 2H), 3.17 (q, J=5.9 Hz, 2H), 2.94 (s, 3H), 2.67 (s, 3H), 2.67-2.63 (m, 2H). MS (ESI+) m/e 509 (M+H)$^+$.

EXAMPLE 895

2-{4-fluoro-2-[2-(1,2,3,6-tetrahydropyridin-4-yl)-1H-pyrrolo[2,3-b]pyridin-4-yl]phenoxy}) ethanamine The synthesis of this compound is described in Example 795D. $^1$H NMR (400 MHz, DMSO-d$_6$) δ 12.09 (s, 1H), 9.03 (s, 1H), 8.27 (d, J=5.0 Hz, 1H), 7.89 (s, 2H), 7.35-7.26 (m, 3H), 7.22 (d, J =5.0 Hz, 1H), 6.53 (s, 1H), 6.55 (s, 1H), 4.16 (t, J=5.4 Hz, 2H), 3.84 (d, J=5.3 Hz, 2H), 3.37-3.28 (m, 2H), 3.10-3.03 (m, 2H), 2.76-2.62 (m, 2H). MS (ESI$^+$) m/e 353 (M+H)$^+$.

EXAMPLE 897 tert-butyl 4-{4-[5-fluoro-2-(methylamino)phenyl]-1H-pyrrolo[2,3-b]pyridin-2-yl}-3,6-dihydropyridine-1(2H)-carboxylate

EXAMPLE 897A tert-butyl 4-(4-(5-fluoro-2-(methylamino)phenyl)-1-tosyl-1H-pyrrolo[2,3-b]pyridin-2-yl)-5,6-dihydropyridine-1(2H)-carboxylate A mixture of 2-bromo-4-fluoro-N-methylaniline hydrochloride (300 mg, 1.247 mmol), Example 673A (867 mg, 1.497 mmol), and dichlorobis(triphenylphosphine)palladium (II) (88 mg, 0.125 mmol) was suspended in a mixture of 7:3:2 dimethoxyethane/water/ethanol (12 mL). 2.18 mL of 2 M aqueous Na$_2$CO$_3$ solution was then added. The suspension was stirred at room temperature for a few seconds and was stirred in a microwave reactor (Biotage Initiator, model 355302) at 150° C. for 30 minutes. The mixture was partitioned between ethyl acetate and brine. The organic phase was washed with brine, and concentrated. The residue was separated by flash chromatography (15-70% ethyl acetate in hexane) to provide the title compound. MS (DCI/NH$_3$) m/z 577 (M+H)$^+$.

EXAMPLE 897B tert-butyl 4-{4-[5-fluoro-2-(methylamino)phenyl]-1H-pyrrolo[2,3-b]pyridin-2-yl}-3,6-dihydropyridine-1(2H)-carboxylate To a solution of Example 897A (1.2 g, 2.081 mmol) in dioxane (24 mL) was added NaOH (50% solution in water, 0.832 g, 10.40 mmol) in 8 mL of water. The mixture was at 90° C. overnight. After cooling, the mixture was partitioned between ethyl acetate and brine. The organic phase was washed with water and concentrated. The residue was purified by flash chromatography (50-80% ethyl acetate in hexane) to provide the title compound. $^1$H NMR (400 MHz, DMSO-d$_6$): δ1.42 (s, 9 H), 2.45 (s, 2 H), 2.65 (d, J=4.88 Hz, 3 H), 3.51 (t, J=5.49 Hz, 2 H), 4.04 (s, 2 H), 4.58 (q, J=4.88 Hz, 1 H), 6.20 (s, 1 H), 6.49 (s, 1 H), 6.66 (dd, J=9.00, 4.73 Hz, 1 H), 6.96 (dd, J=9.16, 3.05 Hz, 1 H), 7.02 (d, J=4.88 Hz, 1 H), 7.09-7.13 (m, 1 H), 8.23 (d, J=4.88 Hz, 1 H), 11.90 (s, 1 H); MS (DCI/NH$_3$) m/z 423 (M+H)$^+$.

EXAMPLE 898

4-fluoro-N-methyl-2-[2-(1,2,3,6-tetrahydropyridin-4-yl)-1H-pyrrolo[2,3-b]pyridin-4-yl]aniline To a solution of Example 897B (50 mg, 0.118 mmol) in methylene chloride (5 mL) was added trifluoroacetic acid (1 mL). The solution was stirred at room temperature for 30 minutes and was concentrated. The residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. $^1$H NMR (400 MHz, DMSO-d$_6$): δ2.65 (s, 3 H), 2.67-2.72 (m, 2 H), 3.29-3.35 (m, 2 H), 3.83 (s, 2 H), 6.32 (d, J=1.53 Hz, 1 H), 6.50 (s, 1 H), 6.69 (dd, J=9.16, 4.88 Hz, 1 H), 6.98 (dd, J=9.16, 3.05 Hz, 1 H), 7.08-7.16 (m, 2 H), 8.30 (d, J=4.88 Hz, 1 H), 8.91 (s, 1 H), 12.15 (s, 1 H); MS (DCI/NH$_3$) m/z 323 (M+H)$^+$.

EXAMPLE 899

1-amino-4-[4-(5-fluoro-2-methoxyphenyl)-1H-pyrrolo[2,3-b]pyridin-2-yl]-N,N-dimethylcyclohex-3-ene-1-carboxamide

EXAMPLE 899A 1-(tert-butoxycarbonylamino)-4-(4-(5-fluoro-2-methoxyphenyl)-1H-pyrrolo[2,3-b]pyridin-2-yl)cyclohex-3-enecarboxylic acid To a solution of Example 871 (657 mg, 1.722 mmol) in 10 mL dioxane was added di-tert-dicarbonate (800 μL, 3.44 mmol) and the mixture was stirred at ambient temperature for 2 hours. The mixture was diluted with 80 mL ethyl acetate and washed with 1M aqueous phosphoric acid (80 mL) and brine (60 mL), dried over magnesium sulfate, filtered and concentrated. Purification by silica gel flash chromatography (Isco®, Redi-Sep®, 50-100% ethyl acetate/hexane then 10% 2:1 methanol:water in ethyl acetate) provided the title compound. MS (ESI$^+$) m/z 482.2 (M+H)$^+$.

EXAMPLE 899B 1-amino-4-[4-(5-fluoro-2-methoxyphenyl)-1H-pyrrolo[2,3-b]pyridin-2-yl]-N,N-dimethylcyclohex-3-ene-1-carboxamide To a mixture of Example 899A (292 mg, 0.606 mmol), 1-hydroxybenzotriazole hydrate (139 mg, 0.910 mmol), diisopropylethyl amine (159 μL, 0.910 mmol) and 2M dimethyl amine in tetrahydrofuran (606 μL, 1.213 mmol) in N,N-dimethylformamide (3032 μL) was added 1-ethyl-3-(3-dimethylaminopropyl)carbodiimide (174 mg, 0.910 mmol) and the mixture was stirred at ambient temperature for 2 hours. The mixture was diluted with 50 mL ethyl acetate, washed with water (40 mL) and brine (40 mL), dried over magnesium sulfate, filtered and concentrated. The crude material was purified by silica gel flash chromatography (Isco®, Redi-Sep®, 50-100% ethyl acetate/hexane then 10% 2:1 methanol:water in ethyl acetate). To a solution of the product in ethyl acetate (2 mL) was added 2M hydrogen chloride in diethyl ether (4 mL) and the mixture was stirred at 45° C. for 2 hours. After cooling to ambient temperature the product was concentrated to afford the title compound as a bis hydrochloride salt. $^1$H NMR (400 MHz, dimethylsulfoxide-d$_6$) δ 12.73 (s, 1H), 8.37 (s, 3H), 8.29 (d, J=5.4 Hz, 1H), 7.42-7.19 (m, 4H), 6.71-6.62 (m, 1H), 6.48 (d, J=1.9 Hz, 1H), 3.77 (s, 3H), 3.18-2.94 (m, 7H), 2.79-2.65 (m, 1H), 2.65-2.43 (m, 2H), 2.40-2.26 (m, 1H), 2.15-2.04 (m, 1H). MS (ESI$^+$) m/z 409.2 (M+H)$^+$.

EXAMPLE 900

4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide The title compound was prepared as described in Example 248E. $^1$H NMR (400 MHz, DMSO-d$_6$) δ 2.85-2.93 (m, 2H), 3.39 (dt, J=9.4, 4.6 Hz, 2H), 3.73 (s, 3H), 3.91 (d, J=4.5 Hz, 2H), 6.65-6.72 (m, 1H), 7.10-7.24 (m, 3H), 7.31 (td, J=8.7, 3.2 Hz, 1H), 8.43 (d, J=4.9 Hz, 1H). MS (DCI/NH$_3$) m/z 349 (M+H)$^+$.

EXAMPLE 901

1-(3-{4-[4-(5-fluoro-2-methoxyphenyl)-1H-pyrrolo[2,3-b]pyridin-2-yl]-3,6-dihydropyridin-1(2H)-yl}-3-oxopropanoyl)prolinamide The title compound was prepared essentially as described in Example 865, substituting pyrrolidine-2-carboxamide hydrochloride for azetidin-3-ol hydrochloride. $^1$H NMR (500 MHz, CD$_3$OD) δ 8.28 (d, J=6.0 Hz, 1H), 7.52-7.45 (m, 1H), 7.35-7.24 (m, 2H), 7.26-7.19 (m, 1H), 6.61-6.56 (m, 1H), 6.56-6.48 (m, 1H), 4.52-4.41 (m, 1H), 4.36-4.29 (m, 2H), 3.94-3.78 (m, 4H), 3.80-3.47 (m, 4H), 2.72-2.58 (m, 2H), 2.32-1.88 (m, 4H). MS (ESI$^+$) m/z 506.2 (M+H)$^+$.

EXAMPLE 902

N-ethoxy-4-[4-(5-fluoro-2-methoxyphenyl)-1H-pyrrolo[2,3-b]pyridin-2-yl]cyclohex-3-ene-1-carboxamide The title compound was prepared essentially as described in Example 417, substituting Example 219C for Example 365 and O-ethylhydroxylamine for 2-hydroxyacetic acid. $^1$H NMR (400 MHz, DMSO-d$_6$) δ 1.15 (t, J=7.0 Hz, 3H), 1.58-1.73 (m, 1H), 1.88 (dq, J=9.7, 3.1 Hz, 1H), 2.20-2.41 m, 4H), 2.55 (dd, J=16.5, 4.7 Hz, 1H), 3.74 (s, 3H), 3.81 (q, J=7.0 Hz, 2H), 6.25 (d, J=2.0 Hz, 1H), 6.44-6.66 (m, 1H), 7.10 (d, J=5.1 Hz, 1H), 7.14-7.41 (m, 3H), 8.21 (d, J=5.2 Hz, 1H). MS (DCI/NH$_3$) m/z 410 (M+H)$^+$.

EXAMPLE 903

4-(5-fluoro-2-methoxyphenyl)-2-(1,2,3,6-tetrahydropyridin-4-yl)-1H-pyrrolo[2,3-b]pyridine-3-carboxamide A mixture of Example 900 (50 mg, 0.14 mmol) in polyphosphonic acid (100 mg) was stirred at 110° C. for overnight. The reaction mixture was purified by reverse-phase HPLC on Zorbax XDB C-18 (32) using a gradient of 5-40% acetonitrile/water (containing 0.1% trifluoroacetic acid) to afford the title compound as the trifluoroacetate salt. $^1$H NMR (500 MHz, DMSO-d$_6$) δ 2.76 (d, J=32.9 Hz, 2H), 3.30 (d, J=6.5 Hz, 2H), 3.59 (s, 3H), 3.80 (d, J=6.3 Hz, 2H), 6.34 (s, 1H), 6.82 (d, J=2.6 Hz, 1H), 6.92-7.08 (m, 3H), 7.17 (td, J=8.7, 3.2 Hz, 1H). MS (ESI$^+$) m/z 367 (M+H)$^+$.

EXAMPLE 905

4-[4-(5-fluoro-2-methoxyphenyl)-1H-pyrrolo[2,3-b]pyridin-2-yl]-N-(4-methoxybenzyl)cyclohex-3-ene-1-sulfonamide

EXAMPLE 905A

N-(4-methoxybenzyl)-4-oxocyclohexane-1-sulfonamide

To a solution of (4-methoxyphenyl)methanamine (1.06 g, 7.7 mmol) in N,N'-dimethylformamide (30 mL) was added 4-oxocyclohexane-1-sulfonyl chloride (1.02 g, 5.6 mmol) and triethylamine (1.05 g, 10 mmol). The mixture was stirred at room temperature for 3 hours. After the completion of the reaction, the reaction was partitioned between water and ethyl acetate. The organic phase was concentrated and purified by flash chromatography on silica gel using an ISCO Companion eluting with heptanes/ethyl acetate to provide the title compound. MS (ESI$^+$) m/z 298 (M+H)$^+$.

EXAMPLE 905B 4-(N-(4-methoxybenzyl)sulfamoyl)cyclohex-1-en-1-yl trifluoromethanesulfonate To a solution of N-(4-methoxybenzyl)-4-oxocyclohexane-1-sulfonamide (0.5 g, 1.68 mmol) in tetrahydrofuran (15 mL) was added lithium bis(trimethylsilyl)amide (3.36 mL, 3.36 mmol/1 M in tetrahydrofuran) at −78° C. The mixture was stirred at this temperature for 30 minutes then Example 905A (0.9 g, 2.5 mmol) in 0.5 mL tetrahydrofuran was added to the reaction. The reaction was warmed up to room temperature gradually. After the completion of the reaction, the reaction was partitioned between water and ethyl acetate. The organic phase was concentrated and purified by flush chromatography on silica gel using an ISCO Companion eluting with heptanes/ethyl acetate (20%) to provide the title compound. MS (ESI$^+$) m/z 430 (M+H)$^+$.

EXAMPLE 905C

N-(4-methoxybenzyl)-4-(4,4,5,5-tetramethyl-1,3,2-dioxaborolan-2-yl)cyclohex-3-ene-1-sulfonamide The title compound was prepared essentially as described in Example 223B, substituting Example 905B for Example 223A. LC/MS m/z 408 (M+H)$^+$.

EXAMPLE 905D

4-[4-(5-fluoro-2-methoxyphenyl)-1H-pyrrolo[2,3-b]pyridin-2-yl]-N-(4-methoxybenzyl)cyclohex-3-ene-1-sulfonamide The title compound was prepared essentially as described in Example 87C-D, substituting Example 905C (200 mg, 0.5 mmol) for tert-butyl 4-(4,4,5,5-tetramethyl-1,3,2-dioxaborolan-2-yl)-5,6-dihydropyridine-1(2H)-carboxylate. $^1$H NMR (500 MHz, DMSO-d$_6$) δ 1.65 (dt, J=12.1, 6.2 Hz, 1H), 2.17-2.26 (m, 1H), 2.27-2.46 (m, 3H), 2.64 (dd, J=16.9, 5.3 Hz, 1H), 3.04-3.15 (m, 1H), 3.72 (s, 3H), 3.74 (s, 3H), 4.13 (d, J=6.2 Hz, 2H), 6.20 (d, J=2.1 Hz, 1H), 6.50 (dt, J=4.7, 2.4 Hz, 1H), 6.88-6.92 (m, 2H), 7.03 (d, J=4.9 Hz, 1H), 7.16-7.24 (m, 2H), 7.27 (dq, J=8.1, 3.0 Hz, 2H), 7.65 (t, J=6.2 Hz, 1H), 8.19 (d, J=4.9 Hz, 1H). MS (ESI$^+$) m/z 522 (M+H)$^+$.

EXAMPLE 906 methyl 4-[4-(5-fluoro-2-methoxyphenyl)-1H-pyrrolo[2,3-b]pyridin-2-yl]-3,6-dihydro-2H-1,2'-bipyridine-3'-carboxylate Example 87D (106 mg, 0.26 mmol), 2-fluoronicotinic acid methy ester (52 mg, 0.34 mmol), and potassium carbonate (156 mg, 1.2 mmol) were dissolved in dimethylsulfoxide and heated to 90° C. for 18 hours. After cooling to room temperature, the reaction was filtered and concentrated. Purification by reverse phase-HPLC (Sunfire 5 μM, 50×250 mm) eluting with 5-50% acetonitrile in water (containing 0.1% trifluoroacetic acid) provided the trifluoroacetate salt. $^1$HNMR (500 MHz, DMSO-d$_6$) δ 2.62 (m, 2H), 3.60 (t, 2H), 3.76 (s, 3H), 3.85 (s, 3H), 4.01 (m, 2H), 6.30 (br s, 1H), 6.57 (m, 1H), 6.83 (m, 1H), 7.07 (d, 1H), 7.26 (m, 3H), 7.95 (dd, 1H), 8.22 (br d, 1H), 8.30 (dd, 1H), 11.94 (br s, 1H). MS (ESI) m/e 459.1 (M+H)$^+$.

The following compounds (concluding with Example 1316) were prepared essentially as described in Example 238, substituting Example 247B for Example 226B and the appropriate amine for azetidin-3-ol hydrochloride. The products were purified by reverse phase HPLC on a Phenomenex Luna C8(2) 5 um 100 Å AXIA column (30 mm×75 mm) eluting with a gradient of 10-95% acetonitrile in either 0.1% ammonium acetate/water or 0.1% trifluoroacetic acid/water. Accordingly, some examples were isolated as trifluoroacetic acid salts.

EXAMPLE 907

1-({4-[4-(5-fluoro-2-methoxyphenyl)-1H-pyrrolo[2,3-b]pyridin-2-yl]piperidin-1-yl}acetyl)-L-prolinamide $^1$H NMR (400 MHz, CD$_3$OD) δ 8.31 (d, J=5.9 Hz, 1H), 7.50 (d, J=5.9 Hz, 1H), 7.32-7.19 (m, 3H), 6.47-6.41 (m, 1H), 4.51-4.43 (m, 1H), 4.28-4.17 (m, 2H), 3.88-3.71 (m, 5H), 3.67-3.45 (m, 3H), 3.35-3.20 (m, 2H), 2.46-1.89 (m, 8H). MS (ESI$^+$) m/z 480.2 (M+H)$^+$.

EXAMPLE 1014

1-[(3S,4S)-3,4-dihydroxypyrrolidin-1-yl]-2-{4-[4-(5-fluoro-2-methoxyphenyl)-1H-pyrrolo[2,3-b]pyridin-2-yl]piperidin-1-yl}ethanone $^1$H NMR (500 MHz, CD$_3$OD) δ ppm 1.82-1.94 (m, 2H), 2.01-2.10 (m, 2H), 2.30-2.42 (m, 2H), 2.75-2.87 (m, 1H), 3.06-3.15 (m, 2H), 3.44-3.66 (m, 3H), 3.73-3.84 (m, 4H), 4.04-4.11 (m, 1H), 4.11-4.18 (m, 1H), 4.58 (s, 2H), 6.06 (s, 1H), 7.07 (d, J=5.0 Hz, 1H), 7.11-7.20 (m, 3H), 8.10 (d, J=5.1 Hz, 1H). MS (ESI$^+$) m/z 469.2 (M+H)$^+$. 2806.

EXAMPLE 1140

2-{4-[4-(5-fluoro-2-methoxyphenyl)-1H-pyrrolo[2,3-b]pyridin-2-yl]piperidin-1-yl}-N-(2-methoxyethyl)-N-methylacetamide $^1$H NMR (500 MHz, CD$_3$OD) δ ppm 1.79-1.95 (m, 2H), 2.00-2.09 (m, 2H), 2.25-2.36 (m, 2H), 2.74-2.85 (m, 1H), 2.91-3.16 (m, 5H), 3.28-3.43 (m, 5H), 3.48-3.60 (m, 3H), 3.61-3.67 (m, 1H), 3.76 (s, 3H), 6.05 (s, 1H), 7.07 (d, J=5.1 Hz, 1H), 7.11-7.21 (m, 3H), 8.10 (d, J=5.0 Hz, 1H). MS (ESI$^+$) m/z 455.2 (M+H)$^+$.

EXAMPLE 1314

N-(1,1-dioxidotetrahydrothiophen-3-yl)-2-{4-[4-(5-fluoro-2-methoxyphenyl)-1H-pyrrolo[2,3-b]pyridin-2-yl]piperidin-1-yl}acetamide $^1$H NMR (400 MHz, CD$_3$OD) δ ppm 2.03-2.29 (m, 3H), 2.34-2.46 (m, 2H), 2.50-2.63 (m, 1H), 3.04 (dd, J=13.6, 6.5 Hz, 1H), 3.12-3.37 (m, 5H), 3.48 (dd, J=13.5, 7.7 Hz, 1H), 3.60-3.85 (m, 5H), 3.92-4.09 (m, 2H), 4.56-4.71 (m, 1H), 6.43 (s, 1H), 7.17-7.35 (m, 3H), 7.49 (d, J=5.9 Hz, 1H), 8.31 (d, J=5.9 Hz, 1H). MS (ESI$^+$) m/z 501.2 (M+H)$^+$.

EXAMPLE 1316

2-{4-[4-(5-fluoro-2-methoxyphenyl)-1H-pyrrolo[2,3-b]pyridin-2-yl]piperidin-1-yl}-1-[3-(methylsulfonyl)azetidin-1-yl]ethanone $^1$H NMR (400 MHz, CD$_3$OD) δ ppm 1.95-2.31 (m, 2H), 2.31-2.45 (m, 2H), 3.01 (s, 3H), 3.20-3.36 (m, 2H), 3.62-3.86 (m, 5H), 4.02-4.19 (m, 2H), 4.26-4.46 (m, 3H), 4.46-4.64 (m, 2H), 4.81-4.91 (m, 1H), 6.50 (brs, 1H), 7.18-7.42 (m, 3H), 7.58 (d, J=6.2 Hz, 1H), 8.34 (d, J=6.1 Hz, 1H). MS (ESI$^+$) m/z 501.2 (M+H)$^+$.

EXAMPLE 908

1-tert-butyl 2-methyl (2S)-4-{4-[4-(5-fluoro-2-methoxyphenyl)-1H-pyrrolo[2,3-b]pyridin-2-yl]-3,6-dihydropyridin-1(2H)-yl}pyrrolidine-1,2-dicarboxylate A mixture of Example 87D (0.15 g, 0.379 mmol) and triethylamine (0.121 ml, 0.871 mmol) in dichloromethane (3 ml) and methanol (3 ml) was treated with (S)-1-tert-butyl 2-methyl 4-oxopyrrolidine-1,2-dicarboxylate (0.106 g, 0.435 mmol), acetic acid (0.130 ml, 2.271 mmol), and MP-cyanoborohydride (Biotage, 2.49 mmol/g, 0.608 g, 1.514 mmol) and the reaction was stirred at room temperature for 30 hours. The reaction mixture was diluted with 35 mL 50% methanol in dichloromethane and filtered. The filtrate was concentrated. The residue was partitioned in ethyl acetate and saturated aqueous sodium bicarbonate. The organic layer was washed with brine, dried over anhydrous sodium sulfate, filtered, and concentrated. The crude product was purified by flash chromatography on silica gel (AnaLogix IntelliFlash 280 system) eluting with a gradient of from 0% to 8% methanol in dichloromethane to afford the title compound. $^1$H NMR (400 MHz, DMSO-d$_6$) δ ppm 1.37 (s, 9H), 1.67-1.82 (m, 1H), 2.44-2.77 (m, 6H), 3.05-3.29 (m, 3H), 3.65 (s, 3H), 3.67-3.81 (m, 4H), 4.21 (t, J=8.4 Hz, 1H), 6.18 (s, 1H), 6.38-6.46 (m, 1H), 6.99 (d, J=4.9 Hz, 1H), 7.10-7.30 (m, 3H), 8.16 (d, J=4.9 Hz, 1H), 11.40-11.47 (m, 1H). MS (ESI$^+$) m/z 551.0 (M+H)$^+$.

EXAMPLE 909

4-[4-(5-fluoro-2-methoxyphenyl)-1H-pyrrolo[2,3-b]pyridin-2-yl]-3,6-dihydro-2H-1,2'-bipyridine-3'-carboxylic acid Example 906 (23 mg, 0.03 mmol) and a lithium hydroxide solution (0.25 mL, 1M) were dissolved in dimethylsulfoxide (3 mL) and the mixture was heated to 100° C. for 6 days. The reaction was cooled to room temperature and concentrated. Purification by reverse phase-HPLC (Sunfire 5 μM, 50×250 mm) eluting with 5-50% acetonitrile in water (containing 0.1% trifluoroacetic acid) provided the title compound as a trifluoroacetate salt. $^1$HNMR (500 MHz, DMSO-d$_6$) δ 2.64 (m, 2H), 3.63 (t, 2H), 3.75 (s, 3H), 4.02 (m, 2H), 6.30 (br s, 1H), 6.59 (m, 1H), 6.84 (dd, 1H), 7.07 (d, 1H), 7.26 (m, 3H), 7.98 (dd, 1H), 8.22 (br s, 1H), 8.27 (dd, 1H), 11.94 (br s, 1H). MS (ESI) m/e 445.0 (M+H)$^+$.

EXAMPLE 910

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide

EXAMPLE 910A 3-ethoxy-4-(4-(4-(5-fluoro-2-methoxyphenyl)-1H-pyrrolo[2,3-b]pyridin-2-yl)-5,6-dihydropyridin-1(2H)-yl)cyclobut-3-ene-1,2-dione Example 87D (1.02 g, 2.57 mmol), 3,4-diethoxycyclobut-3-ene-1,2-dione (1.31 g, 7.7 mmol and triethylamine (2.5 mL, 17.9 mmol were dissolved in ethanol (50 mL) and heated to 70° C. for 24 hours. After cooling to room temperature and concentrating, the mixture was partitioned between water and ethyl acetate. The layers were separated and the aqueous phase was extracted with ethyl acetate. The combined organic layers were dried over sodium sulfate, filtered, and concentrated to provide the title compound which was used without purification. MS (ESI) m/e 448.1 (M+H)$^+$.

EXAMPLE 910B 3-amino-4-(4-(4-(5-fluoro-2-methoxyphenyl)-1H-pyrrolo[2,3-b]pyridin-2-yl)-5,6-dihydropyridin-1(2H)-yl)cyclobut-3-ene-1,2-dione Example 910A (0.976 g, 2.2 mmol) and ammonia in methanol (5 mL, 7M) were heated to 50° C. for 18 hours. The reaction was cooled to room temperature and concentrated to provide the title compound which was used without purification. MS (ESI) m/e 419.1 (M+H)$^+$.

EXAMPLE 910C

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide Example 910B (59 mg, 0.14 mmol) and acetic anhydride (1 mL, 10.6 mmol) were dissolved in pyridine (2 mL). The reaction mixture was heated to 100° C. for 24 hours then a sodium hydroxide solution (2 mL, 1M) was added and the heating was continued for 2 hours. The reaction was cooled to room temperature and concentrated. Purification by reverse phase-HPLC (Sunfire 5 μM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to give the free base of the title compound. $^1$HNMR (400 MHz, DMSO-d$_6$) δ 2.17 (s, 3H), 2.71 (m, 2H), 3.76 (s, 3H), 3.95 (m, 2H), 4.50 (m, 2H), 6.32 (br s, 1H), 6.51 (m, 1H), 7.05 (d, 1H), 7.24 (m, 3H), 8.24 (d, 1H), 11.62 (br s, 1H). MS (ESI) m/e 461.2 (M+H)$^+$.

EXAMPLE 911

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)methanesulfonamide Example 910A (40 mg, 0.09 mmol), methanesulfonamide (36 mg, 4.23 mmol) and potassium carbonate (115 mg, 9.3 mmol) were dissolved in dimethylsulfoxide (1 mL) and heated to 90° C. for 24 hours. The reaction mixture was cooled to room temperature and concentrated. Purification by reverse phase-HPLC (Sunfire 5 μM, 50×250 mm) eluting with 5-50% acetonitrile in water (containing 0.1% trifluoroacetic acid) provided the trifluoroacetate salt. $^1$HNMR (400 MHz, DMSO-d$_6$) δ 2.54 (s, 3H), 2.62 (m, 2H), 3.74 (s, 3H), 3.98 (m, 2H), 4.51 (m, 2H), 6.31 (br s, 1H), 6.54 (m, 1H), 7.06 (d, 1H), 7.26 (m, 3H), 8.22 (br d, 1H), 11.61 (br s, 1H). MS (ESI) m/e 497.1 (M+H)$^+$.

EXAMPLE 912

3-{4-[4-(5-fluoro-2-methoxyphenyl)-1H-pyrrolo[2,3-b]pyridin-2-yl]-3,6-dihydropyridin-1(2H)-yl}-4-hydroxycyclobut-3-ene-1,2-dione The trifluoroacetate salt of the title compound was isolated as a side product from Example 911. $^1$HNMR (400 MHz, DMSO-d$_6$) δ 2.66 (m, 2H), 3.76 (s, 3H), 3.95 (m, 2H), 4.47 (m, 2H), 6.33 (br s, 1H), 6.55 (m, 1H), 7.07 (d, 1H), 7.24 (m, 3H), 8.24 (d, 1H), 11.66 (br s, 1H). MS (ESI) m/e 419.7 (M+H)$^+$.

EXAMPLE 913 methyl 4-{4-[4-(5-fluoro-2-methoxyphenyl)-1H-pyrrolo[2,3-b]pyridin-2-yl]-3,6-dihydropyridin-1(2H)-yl}-L-prolinate A solution of Example 908 (0.143 g, 0.260 mmol) and trifluoroacetic acid (0.500 ml, 6.49 mmol) in dichloromethane (2.89 ml) was stirred at room temperature for 24 hours. The reaction mixture was concentrated, dissolved in 1 mL methanol and treated with 2N HCl in ether (5 mL). The resulting suspension was stirred for 30 minutes, treated with ether (10 mL) and filtered. The solid was washed with ether and dried under vacuum to provide the title compound as a hydrochloric acid salt. $^1$H NMR (500 MHz, CD$_3$OD) δ ppm 2.59-2.72 (m, 1H), 2.96-3.15 (m, 3H), 3.57-3.79 (m, 2H), 3.83 (s, 3H), 3.87-3.96 (m, 4H), 3.96-4.05 (m, 1H), 4.16-4.23 (m, 2H), 4.28-4.45 (m, 1H), 4.64-4.74 (m, 1H), 6.56-6.63 (m, 1H), 6.78 (s, 1H), 7.21-7.38 (m, 3H), 7.62 (d, J=6.1 Hz, 1H), 8.38 (d, J=6.2 Hz, 1H). MS (ESI$^+$) m/z 451.0 (M+H)$^+$.

EXAMPLE 914 methyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-prolinate The title compound was prepared essentially as described in Example 119, substituting Example 913 for Example 87D. $^1$H NMR (400 MHz, DMSO-d$_6$, 90° C.) δ 11.43 (bs, 1H), 8.17 (d, J=4.9 Hz, 1H), 7.24-7.12 (m, 3H), 7.00 (d, J=4.9 Hz, 1H), 6.45-6.39 (m, 1H), 6.20-6.16 (m, 1H), 4.47-4.33 (m, 1H), 3.78-3.70 (m, 4H), 3.70-3.64 (m, 3H), 3.31-3.14 (m, 3H), 3.10-2.95 (m, 4H), 2.79-2.54 (m, 3H), 2.52-2.41 (m, 2H), 1.94-1.82 (m, 1H). MS (ESI$^+$) m/z 529.1 (M+H)$^+$.

EXAMPLE 915 ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate

EXAMPLE 915A 1-tert-butyl 3-ethyl 4-(4-(4-(5-fluoro-2-methoxyphenyl)-1H-pyrrolo[2,3-b]pyridin-2-yl)-5,6-dihydropyridin-1(2H)-yl)pyrrolidine-1,3-dicarboxylate The title compound was prepared essentially as described in Example 908, substituting 1-tert-butyl 3-ethyl 4-oxopyrrolidine-1,3-dicarboxylate for (S)-1-tert-butyl 2-methyl 4-oxopyrrolidine-1,2-dicarboxylate. MS (ESI$^+$) m/z 565.1 (M+H)$^+$.

EXAMPLE 915B ethyl 4-(4-(4-(5-fluoro-2-methoxyphenyl)-1H-pyrrolo[2,3-b]pyridin-2-yl)-5,6-dihydropyridin-1(2H)-yl)pyrrolidine-3-carboxylate The title compound was prepared essentially as described in Example 913, substituting Example 915A for Example 908. MS (ESI$^+$) m/z 465.0 (M+H)$^+$.

EXAMPLE 915C ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate The title compound was prepared essentially as described in Example 119, substituting Example 915B for Example 87D. $^1$H NMR (400 MHz, DMSO-d$_6$, 90° C.) δ 11.43 (brs, 1H), 8.17 (d, J =4.9 Hz, 1H), 7.27-7.13 (m, 3H), 6.99 (d, J=5.0 Hz, 1H), 6.45-6.36 (m, 1H), 6.18 (m, 1H), 4.16-4.04 (m, 2H), 3.72 (s, 3H), 3.61-3.14 (m, 8H), 2.97-2.87 (m, 4H), 2.60-2.50 (m, 1H), 2.49-2.37 (m, 2H), 1.19 (t, J=7.1 Hz, 3H). MS (ESI$^+$) m/z 543.1 (M+H)$^+$.

EXAMPLE 916

4-(5-fluoro-2-methoxyphenyl)-2-[1-(hydroxyacetyl)-1,2,3,6-tetrahydropyridin-4-yl]-1H-pyrrolo[2,3-b]pyridine-3-carbonitrile The title compound was prepared essentially as described in Example 417, substituting Example 900 for Example 365. $^1$H NMR (400 MHz, DMSO-d$_6$) δ 2.69 (d, J=29.8 Hz, 2H), 3.61 (q, J=7.9, 5.8 Hz, 1H), 3.72 (s, 3H), 3.90 (m, 1H), 4.12 (d, J=7.7 Hz, 1H), 4.16-4.24 (m, 3H), 6.68 (d, J=8.0 Hz, 1H), 7.13 (dd, J=8.4, 4.6 Hz, 2H), 7.18 (dd, J=8.7, 3.2 Hz, 1H), 7.30 (td, J=8.7, 3.2 Hz, 1H), 8.39 (d, J=4.9 Hz, 1H). MS (ESI$^+$) m/z 407 (M+H)$^+$.

EXAMPLE 917

2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carbonitrile The title compound was prepared essentially as described in Examples 149, substituting Example 900 for Example 135B. ¹H NMR (500 MHz, DMSO-d₆) δ 2.93 (t, J=11.4 Hz, 1H), 3.17 (d, J=4.1 Hz, 1H), 3.28-3.40 (m, 3H), 3.46 (dd, J=11.0, 4.8 Hz, 1H), 3.73 (s, 3H), 3.77 (m, 1H), 4.00 (m, 2H), 4.15 (m, 2H), 6.65 (dt, J=3.9, 2.1 Hz, 1H), 7.07-7.26 (m, 3H), 7.31 (td, J=8.7, 3.2 Hz, 1H), 8.44 (d, J=4.9 Hz, 1H). MS (ESI⁺) m/z 423 (M+H)⁺.

EXAMPLE 918 ethyl ({4-[3-cyano-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for tert-butanol in Example 218A and Example 900 for Example 87D in Example 218B. ¹H NMR (500 MHz, DMSO-d₆) δ 1.18 (t, J=7.1 Hz, 3H), 2.75 (tt, J=4.4, 2.4 Hz, 2H), 3.52 (t, J=5.7 Hz, 2H), 3.72 (s, 3H), 4.07-4.13 (m, 4H), 6.68 (dt, J=3.6, 2.1 Hz, 1H), 7.13 (dd, J=9.8, 4.6 Hz, 2H), 7.18 (dd, J=8.7, 3.2 Hz, 1H), 7.30 (td, J=8.7, 3.2 Hz, 1H), 8.40 (d, J=4.9 Hz, 1H). MS (DCI/NH₃) m/z 500 (M+H)⁺.

EXAMPLE 919

2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carboxamide The title compound was prepared essentially as described in Examples 149, substituting Example 903 for Example 135B. ¹H NMR (500 MHz, DMSO-d₆) δ 2.83 (m, 2H), 3.13 (t, J=11.8 Hz, 1H), 3.26-3.38 (m, 3H), 3.46 (dd, J=11.0, 4.8 Hz, 1H), 3.60 (s, 3H), 3.67 (t, J=18.4 Hz, 1H), 3.90 (m, 1H), 3.95-4.14 (m, 2H), 6.30 (d, J=4.6 Hz, 1H), 6.83 (s, 1H), 6.90-7.06 (m, 2H), 7.17 (td, J=8.7, 3.2 Hz, 1H), 8.27 (d, J=4.9 Hz, 1H). MS (ESI⁺) m/z 441 (M+H)⁺.

EXAMPLE 920 ethyl ({4-[3-carbamoyl-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for tert-butanol in Example 218A and Example 903 for Example 87D in Example 218B. ¹H NMR (500 MHz, DMSO-d₆) δ 1.20 (t, J=7.1 Hz, 3H), 2.64 (m, 2H), 3.43 (t, J=5.7 Hz, 2H), 3.59 (s, 3H), 3.96 (q, J=2.8 Hz, 2H), 4.12 (q, J=7.1 Hz, 2H), 6.26 (p, J=1.9 Hz, 1H), 6.80 (d, J=2.4 Hz, 1H), 6.92-7.05 (m, 2H), 7.16 (td, J=8.7, 3.2 Hz, 1H), 8.25 (d, J=4.9 Hz, 1H). MS (DCI/NH₃) m/z 518 (M+H)⁺.

EXAMPLE 921

4-[4-(5-fluoro-2-methoxyphenyl)-1H-pyrrolo[2,3-b]pyridin-2-yl]cyclohex-3-ene-1-sulfonamide A solution of Example 905D (180 mg, 0.35 mmol) in dichloromethane (2 mL) was treated with trifluroacetic acid (2 mL). The mixture was stirred at 50° C. for overnight and concentrated under vacuum. The residue was purified by reverse-phase HPLC on Zorbax XDB C-18 (32) using a gradient of 5-40% acetonitrile/water (containing 0.1% trifluoroacetic acid) to afford the title compound as the trifluoroacetate salt. ¹H NMR (500 MHz, DMSO-d₆) δ 2.23-2.35 (m, 1H), 2.39-2.51 (m, 3H), 2.55-2.77 (m, 2H), 3.12 (dddd, J=13.0, 10.5, 5.4, 2.6 Hz, 1H), 3.75 (s, 3H), 6.29 (d, J=2.0 Hz, 1H), 6.57 (d, J=4.9 Hz, 1H), 7.11 (d, J=5.1 Hz, 1H), 7.16-7.36 (m, 3H), 8.23 (d, J=5.2 Hz, 1H). MS (ESI⁺) m/z 402 (M+H)⁺.

EXAMPLE 922

4-(5-fluoro-2-methoxyphenyl)-2-[1-(methylcarbamoyl)-1,2,3,6-tetrahydropyridin-4-yl]-1H-pyrrolo[2,3-b]pyridine-3-carboxamide The title compound was prepared essentially as described in Example 222D, substituting Example 903 for Example 222C. ¹H NMR (500 MHz, DMSO-d₆) δ 2.50 (m, 1H), 2.60 (s, 3H), 3.10 (qd, J=7.3, 4.8 Hz, 1H), 3.47 (t, J=5.6 Hz, 2H), 3.60 (s, 3H), 3.97 (dd, J=5.4, 2.5 Hz, 2H), 6.28 (tt, J=3.1, 1.4 Hz, 1H), 6.90-7.08 (m, 3H), 7.16 (td, J=8.7, 3.2 Hz, 1H), 8.23 (d, J=5.0 Hz, 1H). MS (ESI⁺) m/z 423 (M+H)⁺.

EXAMPLE 923 ethyl ({6-[4-(5-fluoro-2-methoxyphenyl)-1H-pyrrolo[2,3-b]pyridin-2-yl]-2-azaspiro[3.3]hept-2-yl}sulfonyl)carbamate The title compound was prepared essentially as described in Example 218, substituting ethanol for tert-butanol in Example 218A and Example 872 for Example 87D in Example 218B. ¹H NMR (400 MHz, DMSO-d₆) δ ppm 1.21 (t, J=7.02 Hz, 3 H) 2.38-2.46 (m, 2 H) 2.51-2.56 (m, 2 H) 3.43-3.56 (m, 1 H) 3.72 (s, 3 H) 3.91 (s, 2 H) 4.09 (s, 2 H) 4.12 (q, J=7.02 Hz, 2 H) 6.00 (d, J=1.53 Hz, 1 H) 7.00 (d, J=4.88 Hz, 1 H) 7.14-7.21 (m, 2 H) 7.22-7.29 (m, 1 H) 8.13 (d, J=5.19 Hz, 1 H) 11.28 (s, 1 H) 11.59 (s, 1 H). MS (ESI⁺) m/z 489 (M+H)⁺.

EXAMPLE 924

3-{6-[4-(5-fluoro-2-methoxyphenyl)-1H-pyrrolo[2,3-b]pyridin-2-yl]-2-azaspiro[3.3]hept-2-yl}propane-1,2-diol The title compound was prepared essentially as described in Examples 149, substituting Example 872 for Example 135B. ¹H NMR (500 MHz, DMSO-d₆) δ ppm 2.22-2.47 (m, 6 H) 3.06-3.60 (m, 10 H) 3.72 (s, 3 H) 5.97 (s, 1 H) 6.99 (d, J=4.88 Hz, 1 H) 7.14-7.21 (m, 2 H) 7.22-7.29 (m, 1 H) 8.12 (d, J=5.19 Hz, 1 H) 11.56 (s, 1 H). MS (ESI⁺) m/z 412 (M+H)⁺.

EXAMPLE 925

2-{6-[4-(5-fluoro-2-methoxyphenyl)-1H-pyrrolo[2,3-b]pyridin-2-yl]-2-azaspiro[3.3]hept-2-yl}-N,N-dimethylacetamide The title compound was prepared using the condition described in Example 791, substituting Example 872 for Example 59. ¹H NMR (400 MHz, DMSO-d₆) δ ppm 2.24-2.37 (m, 2 H) 2.39-2.48 (m, 2 H) 2.76 (s, 3 H) 2.91 (s, 3 H) 3.12 (s, 2 H) 3.18 (s, 2 H) 3.30 (s, 2 H) 3.39-3.54 (m, 1 H) 3.72 (s, 3 H) 5.97 (d, J=1.83 Hz, 1 H) 6.99 (d, J=4.88 Hz, 1 H) 7.10-7.31 (m, 3 H) 8.12 (d, J=5.19 Hz, 1 H) 11.55 (s, 1 H). MS (ESI⁺) m/z 423 (M+H)⁺.

EXAMPLE 926

2-({4-[4-(5-fluoro-2-methoxyphenyl)-1H-pyrrolo[2,3-b]pyridin-2-yl]-3,6-dihydropyridin-1(2H)-yl}sulfonyl)-N-(3-hydroxycyclobutyl)acetamide The title compound was prepared essentially as described in Example 868, substituting 3-aminocyclobutanol hydrochloride for azetidin-3-ol hydrochloride. $^1$H NMR (500 MHz, CD$_3$OD) δ ppm 1.79-1.89 (m, 1H), 2.27 (t, J=6.3 Hz, 1H), 2.61-2.73 (m, 4H), 3.55-3.63 (m, 2H), 3.73-3.86 (m, 4H), 3.90-4.04 (m, 3H), 4.10-4.17 (m, 2H), 6.48-6.53 (m, 1H), 6.56 (s, 1H), 7.16-7.32 (m, 3H), 7.43 (d, J=5.8 Hz, 1H), 8.26 (d, J=5.8 Hz, 1H). MS (ESI$^+$) m/z 515.1 (M+H)$^+$.

EXAMPLE 927

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-proline The title compound was prepared essentially as described in Example 681, substituting Example 914 for Example 676. $^1$H NMR (500 MHz, CD$_3$OD) δ ppm 2.24-2.37 (m, 1H), 2.92-2.99 (m, 2H), 3.00-3.14 (m, 4H), 3.54-3.70 (m, 3H), 3.79 (s, 3H), 4.00-4.23 (m, 4H), 4.54 (t, J=8.1 Hz, 1H), 6.42-6.49 (m, 1H), 6.57 (s, 1H), 7.14-7.28 (m, 3H), 7.31 (d, J=5.5 Hz, 1H), 8.29 (d, J=5.5 Hz, 1H). MS (ESI$^+$) m/z 515.1 (M+H)$^+$.

EXAMPLE 928

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylic acid The title compound was prepared essentially as described in Example 681 substituting Example 915 for Example 676. $^1$H NMR (500 MHz, CD$_3$OD) δ ppm 2.94-2.99 (m, 2H), 3.00 (s, 3H), 3.57-3.73 (m, 3H), 3.73-3.92 (m, 7H), 4.11-4.18 (m, 2H), 4.45-4.55 (m, 1H), 6.46-6.52 (m, 1H), 6.59 (s, 1H), 7.15-7.30 (m, 3H), 7.35 (d, J=5.5 Hz, 1H), 8.30 (d, J=5.6 Hz, 1H). MS (ESI$^+$) m/z 515.1 (M+H)$^+$.

EXAMPLE 929

2-[1-(azetidin-1-ylsulfonyl)-1,2,3,6-tetrahydropyridin-4-yl]-4-(5-fluoro-2-methoxyphenyl)-1H-pyrrolo[2,3-b]pyridine The title compound was prepared using the procedure described in Example 794, using azetidine-1-sulfonyl chloride in place of 2-(1,3-dioxoisoindolin-2-yl)ethanesulfonyl chloride. $^1$H NMR (500 MHz, DMSO-d$_6$) δ 11.86 (s, 1H), 8.21 (s, 1H), 7.33-7.15 (m, 3H), 7.04 (d, J=4.9 Hz, 1H), 6.54 (s, 1H), 6.26 (s, 1H), 3.91 (s, 2H), 3.80 (t, J=7.6 Hz, 4H), 3.74 (s, 3H), 3.41-3.36 (m, 2H), 2.58-2.53 (m, 2H), 2.16 (p, J=7.6 Hz, 2H). MS (ESI+) m/e 443 (M+H)$^+$.

EXAMPLE 930

1-({4-[4-(5-fluoro-2-methoxyphenyl)-1H-pyrrolo[2,3-b]pyridin-2-yl]-3,6-dihydropyridin-1(2H)-yl}sulfonyl)azetidine-3-carbonitrile The title compound was prepared using the procedure described in Example 794, using 3-cyanoazetidine-1-sulfonyl chloride in place of 2-(1,3-dioxoisoindolin-2-yl)ethanesulfonyl chloride. $^1$H NMR (500 MHz, DMSO-d$_6$) δ 11.88 (s, 1H), 8.21 (d, J=4.9 Hz, 1H), 7.33-7.15 (m, 3H), 7.04 (d, J=4.9 Hz, 1H), 6.54 (s, 1H), 6.27 (s, 1H), 4.08 (t, J=8.5 Hz, 2H), 4.02-3.91 (m, 4H), 3.83-3.76 (m, 1H), 3.74 (s, 3H), 3.41 (t, J=5.7 Hz, 2H), 2.61-2.54 (m, 2H). MS (ESI+) m/e 468 (M+H)$^+$.

EXAMPLE 931

2-{1-[(4,4-difluoropiperidin-1-yl)sulfonyl]-1,2,3,6-tetrahydropyridin-4-yl}-4-(5-fluoro-2-methoxyphenyl)-1H-pyrrolo[2,3-b]pyridine The title compound was prepared using the procedure described in Example 794, using 4,4-difluoropiperidine-1-sulfonyl chloride in place of 2-(1,3-dioxoisoindolin-2-yl)ethanesulfonyl chloride. $^1$H NMR (500 MHz, DMSO-d$_6$) δ 11.88 (s, 1H), 8.21 (d, J=4.9 Hz, 1H), 7.33-7.16 (m, 3H), 7.04 (d, J=4.9 Hz, 1H), 6.51 (s, 1H), 6.27 (s, 1H), 3.94 (s, 2H), 3.74 (s, 3H), 3.42 (t, J=5.7 Hz, 2H), 3.34 (s, 4H), 2.60-2.55 (m, 2H), 2.05 (tt, J=14.1, 5.8 Hz, 4H). MS (ESI+) m/e 507 (M+H)$^+$.

EXAMPLE 932

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}cyclohex-3-ene-1-carboxamide Example 219C (50 mg, 0.114 mmol), 1-(2-(methylsulfonyl)ethyl)-1H-pyrazol-4-amine bishydrochloride (35.8 mg, 0.137 mmol), 1-(3-dimethylaminopropyl)-3-ethylcarbodiimide hydrochloride (28.4 mg, 0.148 mmol), 1H-benzo[d][1,2,3]triazol-1-ol hydrate (22.66 mg, 0.148 mmol), and N-ethyl-N-isopropylpropan-2-amine (119 µl, 0.683 mmol) in 2 mL dimethylformamide was stirred at 50° C. overnight. The crude product was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as trifluoroacetic acid salt. $^1$H NMR (500 MHz, DMSO-d$_6$) δ 1.71 (dq, J=11.8, 6.5 Hz, 1H), 2.01 (dd, J=12.9, 4.6 Hz, 1H), 2.40 (td, J=16.5, 14.5, 9.3 Hz, 3H), 2.72 (s, 2H), 2.86 (s, 3H), 3.75 (s, 5H), 4.49 (t, J=6.8 Hz, 2H), 6.24 (s, 1H), 6.58 (s, 1H), 7.08 (d, J=5.1 Hz, 1H), 7.14-7.42 (m, 3H), 7.50 (s, 1H), 8.00 (s, 1H), 8.20 (d, J=5.1 Hz, 1H), 10.00 (s, 1H), 11.88 (s, 1H). MS (ESI$^+$) m/z 538 (M+H)$^+$.

EXAMPLE 933

4-[4-(5-fluoro-2-methoxyphenyl)-1H-pyrrolo[2,3-b]pyridin-2-yl]-N-(1-methyl-1H-pyrazol-4-yl)cyclohex-3-ene-1-carboxamide The title compound was prepared according to the procedure described in Example 932, substituting 1-methyl-1H-pyrazol-4-amine for 1-(2-(methylsulfonyl)ethyl)-1H-pyrazol-4-amine. $^1$H NMR (500 MHz, DMSO-d$_6$) δ 1.71 (tq, J=12.2, 5.5 Hz, 1H), 1.89-2.13 (m, 1H), 2.40 (qd, J=12.1, 10.7, 4.4 Hz, 3H), 2.51-2.70 (m, 2H), 3.76 (d, J=13.4 Hz, 6H), 6.27 (d, J=2.0 Hz, 1H), 6.52-6.67 (m, 1H), 7.11 (d, J=5.2 Hz, 1H), 7.16-7.37 (m, 3H), 7.40 (s, 1H), 7.86 (s, 1H), 8.22 (d, J=5.2 Hz, 1H), 9.93 (s, 1H), 11.99 (s, 1H); MS (ESI$^+$) m/z 446 (M+H)$^+$.

EXAMPLE 937

2-[4-({4-[4-(5-fluoro-2-methoxyphenyl)-1H-pyrrolo[2,3-b]pyridin-2-yl]-3,6-dihydropyridin-1(2H)-yl}sulfonyl)piperidin-1-yl]-N,N-dimethylacetamide The title compound was prepared using the procedure described in Example 224, using Example 825 in place of Example 87D. $^1$H NMR (500 MHz, DMSO-d$_6$) δ 11.95 (s, 1H), 8.23 (d, J=5.0 Hz, 1H), 7.44-7.13 (m, 3H), 7.01 (s, 1H), 6.55 (s, 1H), 6.30 (s, 1H), 4.24-3.98 (m, 6H), 3.74 (s, 3H), 3.61-3.47 (m, 4H), 3.05-2.97 (m, 1H), 2.91 (s, 3H), 2.89 (s, 3H), 2.59-2.55 (m, 2H), 2.24-2.00 (m, 4H). MS (ESI+) m/e 556 (M+H)$^+$.

EXAMPLE 939

4-(5-fluoro-2-methoxyphenyl)-2-[1-(methylsulfonyl)-2,3,6,7-tetrahydro-1H-azepin-4-yl]-1H-pyrrolo[2,3-b]pyridine The title compound was prepared as described in Example 119, substituting Example 888 for Example 87D. $^1$H NMR (500 MHz, DMSO-d$_6$) δ 2.50-2.57 (m, 2H), 2.77-2.84 (m, 2H), 2.89 (s, 3H), 3.30-3.40 (m, 4H), 3.74 (s, 3H), 6.30 (d, J=2.3 Hz, 1H), 6.66 (t, J=6.4 Hz, 1H), 7.02 (d, J=5.0 Hz, 1H), 7.15-7.33 (m, 3H), 8.19 (d, J=5.0 Hz, 1H), 11.74 (br s, 1H); MS (ESI$^+$) m/z 416 (M+H)$^+$.

EXAMPLE 940

4-[4-(5-fluoro-2-methoxyphenyl)-1H-pyrrolo[2,3-b]pyridin-2-yl]-N-methyl-2,3,6,7-tetrahydro-1H-azepine-1-carboxamide The title compound was prepared as described in Example 215, substituting Example 888 for Example 87D. $^1$H NMR (500 MHz, DMSO-d$_6$) δ 2.47 (m, 2H), 2.58 (d, J=4.2 Hz, 3H), 2.69 (t, J=5.3 Hz, 2H), 3.47 (t, J=5.6 Hz, 2H), 3.50-3.57 (m, 2H), 3.74 (s, 3H), 6.22 (d, J=2.1 Hz, 1H), 6.27 (q, J=4.2 Hz, 1H), 6.55 (t, J=6.0 Hz, 1H), 7.02 (d, J=4.9 Hz, 1H), 7.23 (dddd, J=30.5, 13.7, 8.9, 3.8 Hz, 3H), 8.17 (d, J=5.0 Hz, 1H), 11.69 (br s, 1H); MS (ESI$^+$) m/z 395 (M+H)$^+$.

EXAMPLE 941

[1-({4-[4-(5-fluoro-2-methoxyphenyl)-1H-pyrrolo[2,3-b]pyridin-2-yl]-3,6-dihydropyridin-1(2H)-yl}carbonyl)-1,2,3,6-tetrahydropyridin-4-yl]boronic acid In a 5 mL microwave tube was added Example 615A (0.131 g, 0.268 mmol) and 4-(4,4,5,5-tetramethyl-1,3,2-dioxaborolan-2-yl)-1,2,3,6-tetrahydropyridine (0.082 g, 0.391 mmol) in N,N-dimethylformamide (2 mL) to give a suspension. N-Ethyl-N-isopropylpropan-2-amine (0.1 mL, 0.573 mmol) was added. The mixture was heated at 100° C. for 4.5 hours. The crude product was purified by preparative reverse phase column (Analogix, C-18, 40 g) with gradient elution from 20-100% acetonitrile in water with 0.1% trifluoroacetic acid to afford the title compound as trifluoroacetate salt. $^1$H NMR (400 MHz, DMSO-d$_6$): δ 2.13-2.21 (m, 2 H) 3.20 (t, J=5.49 Hz, 2 H) 3.34 (t, J=5.49 Hz, 2 H) 3.71-3.79 (m, 5 H) 3.87-3.93 (m, 2 H) 6.26 (d, J=1.83 Hz, 1 H) 6.32-6.38 (m, 1 H) 6.48-6.53 (m, 1 H) 7.05 (d, J=4.88 Hz, 1 H) 7.16-7.32 (m, 3 H) 8.20 (d, J=4.88 Hz, 1 H) 11.85 (s, 1 H). LC/MS: 477.2 (M+H)$^+$.

EXAMPLE 942

3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione

EXAMPLE 942A 3-(4-(4-(5-fluoro-2-methoxyphenyl)-1H-pyrrolo[2,3-b]pyridin-2-yl)-5,6-dihydropyridin-1(2H)-yl)-4-mercaptocyclobut-3-ene-1,2-dione Example 910A (98 mg, 0.22 mmol) and sodium hydrosulfide hydrate (307 mg, 4.2 mmol) were dissolved in ethanol (5 mL) and heated to 100° C. for 24 hours. After cooling to room temperature, the reaction mixture was filtered to collect the resultant solid. The solid was washed with ethanol and dried to provide the title compound which was used without purification. MS (ESI) m/e 420.1 (M−15)$^+$.

EXAMPLE 942B

3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione Example 942A (122 mg, 0.28 mmol), potassium carbonate (43 mg, 0.31 mmol) and dimethyl sulfate (0.03 mL. 0.32 mmol) were dissolved in acetone (5 mL) and heated to 40° C. for 4 hours. The reaction was concentrated. Purification by reverse phase-HPLC (Sunfire 5 μM, 50×250 mm) eluting with 5-50% acetonitrile in water (containing 0.1% trifluoroacetic acid) provided the trifluoroacetate salt. $^1$HNMR (400 MHz, DMSO-d$_6$) δ 2.73 (m, 2H), 3.79 (s, 3H), 3.94 (m, 2H), 4.33 (s, 3H), 4.71 (m, 2H), 6.77 (br s, 1H), 7.33 (m, 2H), 7.45 (m, 1H), 7.65 (m, 1H), 6.60 (d, 2H), 13.00 (br s, 1H). MS (ESI) m/e 448.1 (M+1)$^+$.

EXAMPLE 943

N-{4-[4-(5-fluoro-2-methoxyphenyl)-1H-pyrrolo[2,3-b]pyridin-2-yl]cyclohex-3-en-1-yl}methanesulfonamide Example 977E (62 mg, 0.15 mmol), methanesulfonyl chloride (0.02 mL, 0.26 mmol) and triethylamine (0.2 mL, 1.4 mmol) were dissolved in N,N-dimethylformamide (2 mL) and the mixture was stirred at room temperature for 24 hours. The reaction was concentrated. Purification by reverse phase-HPLC (Sunfire 5 μM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to give the free base of the title compound. $^1$HNMR (400 MHz, DMSO-d$_6$) δ 1.64 (m, 1H), 1.99 (m, 1H), 2.20 (m, 1H), 2.53 (m, 3H), 2.96 (s, 3H), 3.45 (m, 1H), 3.74 (s, 3H), 6.18 (br s, 1H), 6.44 (m, 1H), 7.01 (d, 1H), 7.11 (d, 1H), 7.24 (m, 3H), 8.17 (d, 1H), 11.73 (br s, 1H). MS (ESI) m/e 416.2 (M+1)$^+$.

EXAMPLE 944

1-{4-[4-(5-fluoro-2-methoxyphenyl)-1H-pyrrolo[2,3-b]pyridin-2-yl]cyclohex-3-en-1-yl}-3-methylurea Example 977E (60 mg, 0.14 mmol), N-succinimidyl-N-methylcarbamate (48 mg, 0.28 mmol) and triethylamine (0.12 mL, 5.9 mmol) were dissolved in N,N-dimethylformamide (1 mL) and the mixture was stirred at room temperature for 24 hours. The reaction mixture was filtered; and the resultant solid was washed with methanol and dried with magnesium sulfate to provide the title compound. $^1$HNMR (400 MHz, DMSO-$d_6$) δ 1.56 (m, 1H), 1.87 (m, 1H), 2.05 (m, 1H), 2.44 (m, 3H), 2.55 (d, 3H), 3.71 (m, 1H), 3.74 (s, 3H), 5.66 (m, 1H), 5.89 (d, 1H), 6.19 (br s, 1H), 6.46 (m, 1H), 7.02 (d, 1H), 7.24 (m, 3H), 8.17 (d, 1H), 11.72 br s, 1H). MS (ESI) m/e 395.1 (M+1)$^+$.

EXAMPLE 945

N-{4-[4-(5-fluoro-2-methoxyphenyl)-1H-pyrrolo[2,3-b]pyridin-2-yl]cyclohex-3-en-1-yl}-2-hydroxyacetamide Example 977E (64 mg, 0.16 mmol), glycolic acid (20 mg, 0.18 mmol), triethylamine (0.1 mL, 0.7 mmol) and ((1H-benzo[d][1,2,3]triazol-1-yl)oxy)tri(pyrrolidin-1-yl)phosphonium hexafluorophosphate(V) (108 mg, 0.2 mmol) were stirred in tetrahydrofuran (2 mL) for 24 hours at room temperature. The reaction mixture was concentrated and purified by reverse phase-HPLC (Sunfire 5 μM, 50×250 mm) eluting with 5-50% acetonitrile in water (containing 0.1% trifluoroacetic acid) tp provide the trifluoroacetate salt. The salt was dissolved in methanol and eluted from a SCX column with 0.5M ammonia in methanol to give the free base of the title compound. $^1$HNMR (400 MHz, DMSO-$d_6$) δ 1.76 (m, 1H), 1.93 (m, 1H), 2.29 (m, 1H), 2.49 (m, 3H), 3.79 (s, 3H), 3.86 (d, 2H), 3.99 (m, 1H), 5.50 (t, 1H), 6.25 (d, 1H), 6.52 (m, 1H), 7.07 (d, 1H), 7.27 (m, 3H), 7.64 (d, 1H), 8.23 (d, 1H), 11.79 (br s, 1H). MS (ESI) m/e 396.2 (M+1)$^+$.

EXAMPLE 946

2-cyano-N-{4-[4-(5-fluoro-2-methoxyphenyl)-1H-pyrrolo[2,3-b]pyridin-2-yl]cyclohex-3-en-1-yl}acetamide Example 977E (76 mg, 0.18 mmol), cyanoacetic acid (28 mg, 0.33 mmol), ((1H-benzo[d][1,2,3]triazol-1-yl)oxy)tri(pyrrolidin-1-yl)phosphonium hexafluorophosphate(V) (155 mg, 0.3 mmol) and triethylamine (0.2 mL, 1.4 mmol) were dissolved in N,N-dimethylformamide (2 mL) and the mixture was stirred at room temperature for 24 hours. The reaction mixture was concentrated and purified by reverse phase-HPLC (Sunfire 5 μM, 50×250 mm) eluting with 5-50% acetonitrile in water (containing 0.1% trifluoroacetic acid) to provide the trifluoroacetate salt. The salt was dissolved in methanol and eluted from a SCX column with 0.5M ammonia in methanol to give the free base of the title compound. $^1$HNMR (500 MHz, DMSO-$d_6$) δ 1.63 (m, 1H), 1.89 (m, 1H), 2.10 (m, 1H), 2.48 (m, 3H), 3.62 (s, 2H), 3.74 (s, 3H), 3.87 (m, 1H), 6.20 (d, 1H), 6.46 (m, 1H), 7.02 (d, 1H), 7.23 (m, 3H), 8.18 (d, 1H), 8.27 (d, 1H), 11.75 (br s, 1H). MS (ESI) m/e 405.2 (M+1)$^+$.

EXAMPLE 947

4-[4-(5-fluoro-2-methoxyphenyl)-1H-pyrrolo[2,3-b]pyridin-2-yl]-1,2,5,6-tetrahydropyridine-3-carbonitrile

EXAMPLE 947A 4-(5-fluoro-2-methoxyphenyl)-1-(phenylsulfonyl)-2-(trimethylstannyl)-1H-pyrrolo[2,3-b]pyridine A round bottom flask was charged with Example 87B (1000 mg, 1.967 mmol) and Pd(PPh$_3$)$_4$ (114 mg, 0.098 mmol) and purged with nitrogen. Anhydrous toluene (18 mL) and 1,1,1,2,2,2-hexamethyldistannane (0.490 ml, 2.361 mmol) were added via syringe. The solution was purged with nitrogen again and heated at 110° C. for 18 hours. The reaction mixture was purified by flash chromatography on Analogix IntelliFlash$^{280}$ eluting with 15 to 100% ethyl acetate/hexanes to provide the title compound. LC-MS: 546 (M+H)$^+$.

EXAMPLE 947B tert-butyl 3-cyano-4-(((trifluoromethyl)sulfonyl)oxy)-5,6-dihydropyridine-1(2H)-carboxylate To a stirred solution of sodium bis(trimethylsilyl)amide (1.0M in tetrahydrofuran) (5.89 mL, 5.89 mmol) in tetrahydrofuran (4 mL) at −78° C. was added slowly tert-butyl 3-cyano-4-oxopiperidine-1-carboxylate (1.2 g, 5.35 mmol) in tetrahydrofuran (3 mL). The reaction mixture was stirred for 30 minutes and then treated over 15 minutes with a solution of 1,1,1-trifluoro-N-phenyl-N-((trifluoromethyl)sulfonyl)methanesulfonamide (2.103 g, 5.89 mmol) in tetrahydrofuran (5 mL). The mixture was stirred at −78° C. for 1.5 hours, allowed to warm to room temperature for 30 minutes and quenched by the addition of water (12.5 mL). The mixture was extracted with ether, and the organic layer was washed with brine, dried over Na$_2$SO$_4$, filtered and concentrated in vacuo. The residue was purified by flash chromatography on Analogix IntelliFlash$^{280}$ eluting with 5-50% ethyl acetate/hexanes to afford the title compound (~85% pure). MS (ESI$^+$) m/z 374 (M+NH$_4$)$^+$.

EXAMPLE 947C tert-butyl 3-cyano-4-(4-(5-fluoro-2-methoxyphenyl)-1-(phenylsulfonyl)-1H-pyrrolo[2,3-b]pyridin-2-yl)-5,6-dihydropyridine-1(2H)-carboxylate A 20 ml pressure vial was charged with Example 947A (150 mg, 0.275 mmol), Example 947B (173 mg, ~0.413 mmol), tri-o-tolylphosphine (25.1 mg, 0.083 mmol), Pd$_2$(dibenzylideneacetone)$_3$ (25.2 mg, 0.028 mmol) and dimethylformamide (1.5 mL). The vial was capped with a septa and then evacuated and backfilled with nitrogen. After adding triethylamine (0.115 mL, 0.825 mmol), the reaction mixture was stirred at 60° C. for 2 days and was concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. LC-MS: 589 (M+H)$^+$.

EXAMPLE 947D

4-[4-(5-fluoro-2-methoxyphenyl)-1H-pyrrolo[2,3-b]pyridin-2-yl]-1,2,5,6-tetrahydropyridine-3-carbonitrile The title compound was prepared as described in Example 87D, substituting Example 947C for Example 87C. $^1$H NMR (500 MHz, DMSO-$d_6$) δ ppm 2.98-3.08 (m, 2 H) 3.34-3.44 (m, 2 H) 3.75 (s, 3 H) 4.05 (s, 2 H) 6.97 (s, 1 H) 7.18 (d, J=4.88 Hz, 1 H) 7.21-7.27 (m, 2 H) 7.28-7.37 (m, 1 H) 8.40 (d, J=4.88 Hz, 1 H) 9.29 (s, 2 H) 12.23 (s, 1 H). MS (ESI$^+$) m/z 349 (M+H)$^+$.

EXAMPLE 948

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetonitrile To a suspension of Example 87D (80.0 mg, 0.202 mmol) in N,N-dimethylformamide (2.5 mL) was added 2-(oxetan-3-ylidene)acetonitrile (0.025 mL, 0.323 mmol) and triethylamine (0.169 mL, 1.211 mmol). The mixture was heated at 100° C. for 1 day. The reaction mixture was diluted with water and brine and extracted with ethyl acetate. The combined organic layers were washed with brine, dried over MgSO$_4$, filtered, concentrated, and purified on a 12 g silica column using the ISCO Companion flash system eluting with ethyl acetate/methanol (97.5:2.5) followed by HPLC (see protocols in Example 361) to provide the title compound as a trifluoroacetic acid salt. $^1$H NMR (400 MHz, methanol-$d_4$) δ ppm 2.68-2.75 (m, 2H), 2.93 (t, J=5.7 Hz, 2H), 3.15 (s, 2H), 3.47-3.52 (m, 2H), 3.82 (s, 3H), 4.61 (d, J=6.9 Hz, 2H), 4.77 (d, J=7.0 Hz, 2H), 6.57 (t, J=3.5 Hz, 1H), 6.59 (s, 1H), 7.15-7.46 (m, 3H), 7.51 (d, J=6.0 Hz, 1H), 8.29 (d, J=6.1 Hz, 1H). MS (ESI$^+$) m/z 419.2 (M+H)$^+$.

EXAMPLE 949

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}cyclohex-3-ene-1-carboxamide The title compound was prepared according to the procedure described in Example 932, substituting (R)-1-(4-amino-1H-pyrazol-1-yl)propan-2-ol for 1-(2-(methylsulfonyl)ethyl)-1H-pyrazol-4-amine. $^1$H NMR (400 MHz, DMSO-$d_6$) δ 1.01 (d, J=5.5 Hz, 3H), 1.71 (tq, J=11.9, 5.6 Hz, 1H), 2.01 (dt, J=13.8, 3.8 Hz, 1H), 2.24-2.48 (m, 3H), 2.54 (ddd, J=7.6, 5.7, 2.7 Hz, 2H), 3.75 (s, 3H), 3.84-4.07 (m, 3H), 6.29 (d, J=2.0 Hz, 1H), 6.60 (t, J=3.4 Hz, 1H), 7.13 (d, J=5.2 Hz, 1H), 7.17-7.39 (m, 3H), 7.43 (s, 1H), 7.88 (s, 1H), 8.24 (d, J=5.2 Hz, 1H), 9.94 (s, 1H), 12.05 (d, J=2.3 Hz, 1H). MS (ESI$^+$) m/z 490 (M+H)$^+$.

The following compounds (concluding with Example 959) were prepared essentially as described in Example 251, substituting the appropriate amine for 2-(methylamino)ethanol.

EXAMPLE 950

2-{4-[4-(5-fluoro-2-methoxyphenyl)-1H-pyrrolo[2,3-b]pyridin-2-yl]piperidin-1-yl}-1-(3-methoxyazetidin-1-yl)ethanone $^1$H NMR (400 MHz, DMSO-$d_6$) δ 1.72 (dd, J=11.9, 3.7 Hz, 1H), 1.89-2.14 (m, 4H), 2.24 (td, J=11.6, 2.5 Hz, 2H), 2.74 (tt, J=11.7, 3.9 Hz, 1H), 2.91 (dt, J=11.8, 3.4 Hz, 2H), 3.03 (s, 2H), 3.73 (s, 3H), 4.21 (tt, J=6.2, 4.0 Hz, 6H), 5.98 (s, 1H), 7.02 (d, J=4.9 Hz, 1H), 7.10-7.29 (m, 3H), 8.14 (d, J=4.9 Hz, 1H). MS (APCI$^+$) m/z 453.2 (M+H)$^+$.

EXAMPLE 951

1-({4-[4-(5-fluoro-2-methoxyphenyl)-1H-pyrrolo[2,3-b]pyridin-2-yl]piperidin-1-yl}acetyl)azetidine-3-carbonitrile $^1$H NMR (400 MHz, DMSO-$d_6$) δ 1.67-1.75 (m, 1H), 1.91-2.15 (m, 2H), 2.21 (td, J=11.6, 2.5 Hz, 2H), 2.73 (tt, J=11.8, 3.9 Hz, 1H), 2.88 (dt, J=12.0, 3.3 Hz, 2H), 3.03 (s, 2H), 3.72 (s, 4H), 4.33 (s, 3H), 5.97 (s, 1H), 7.00 (d, J=5.0 Hz, 1H), 7.09-7.28 (m, 3H), 8.13 (d, J=5.0 Hz, 1H). MS (APCI$^+$) m/z 448.2 (M+H)$^+$.

EXAMPLE 952

1-(3,3-difluoroazetidin-1-yl)-2-{4-[4-(5-fluoro-2-methoxyphenyl)-1H-pyrrolo[2,3-b]pyridin-2-yl]piperidin-1-yl}ethanone $^1$H NMR (400 MHz, DMSO-$d_6$) δ 1.66-1.82 (m, 2H), 1.90-2.10 (m, 2H), 2.23 (td, J=11.7, 2.5 Hz, 2H), 2.73 (ddt, J=11.7, 8.0, 3.9 Hz, 1H), 2.89 (dt, J=11.7, 3.4 Hz, 2H), 3.11 (s, 2H), 3.72 (s, 3H), 4.47 (s, 4H), 5.98 (s, 1H), 7.01 (d, J=4.9 Hz, 1H), 7.09-7.28 (m, 3H), 8.13 (d, J=5.0 Hz, 1H). MS (APCI$^+$) m/z 459.2 (M+H)$^+$.

EXAMPLE 953

2-{4-[4-(5-fluoro-2-methoxyphenyl)-1H-pyrrolo[2,3-b]pyridin-2-yl]piperidin-1-yl}-1-(3-hydroxy-3-methylazetidin-1-yl)ethanone $^1$H NMR (400 MHz, DMSO-$d_6$) δ 1.38 (s, 3H), 1.64-1.79 (m, 2H), 1.96 (d, J=11.5 Hz, 2H), 2.22 (td, J=11.6, 2.5 Hz, 2H), 2.72 (ddt, J=11.7, 7.8, 3.9 Hz, 1H), 2.89 (dt, J=11.9, 3.2 Hz, 2H), 3.00 (s, 2H), 3.72 (s, 4H), 4.04 (s, 3H), 5.96 (s, 1H), 7.00 (d, J=5.0 Hz, 1H), 7.09-7.28 (m, 3H), 8.13 (d, J=4.9 Hz, 1H). MS (APCI$^+$) m/z 452.2 (M+H)$^+$.

EXAMPLE 954

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]piperidin-1-yl}ethanone $^1$H NMR (400 MHz, DMSO-$d_6$) δ 0.76-1.02 (m, 3H), 1.28-1.82 (m, 4H), 1.94-2.13 (m, 2H), 2.13-2.41 (m, 2H), 2.73 (tt, J=11.8, 3.9 Hz, 1H), 2.79-3.07 (m, 4H), 3.72 (s, 4H), 3.73-4.68 (m, 3H), 5.96 (s, 1H), 7.00 (d, J=4.9 Hz, 1H), 7.09-7.28 (m, 3H), 8.13 (d, J=4.9 Hz, 1H). MS (APCI$^+$) m/z 481.3 (M+H)$^+$.

EXAMPLE 955

2-{4-[4-(5-fluoro-2-methoxyphenyl)-1H-pyrrolo[2,3-b]pyridin-2-yl]piperidin-1-yl}-1-[3-(methoxymethyl)-3-methylazetidin-1-yl]ethanone $^1$H NMR (400 MHz, DMSO-$d_6$) δ 1.21 (s, 3H), 1.63-1.85 (m, 2H), 1.91-2.03 (m, 2H), 2.21 (td, J=11.6, 2.5 Hz, 2H), 2.72 (ddt, J=11.3, 7.4, 3.7 Hz, 1H), 2.83-3.03 (m, 5H), 3.32 (d, J=2.1 Hz, 5H), 3.36-3.64 (m, 2H), 3.72 (s, 4H), 3.92 (d, J=88.4 Hz, 2H), 5.96 (s, 1H), 7.00 (d, J=5.0 Hz, 1H), 7.09-7.27 (m, 3H), 8.13 (d, J=4.9 Hz, 1H). MS (APCI$^+$) m/z 481.3 (M+H)$^+$.

EXAMPLE 956

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]piperidin-1-yl}ethanone $^1$H NMR (400 MHz, DMSO-d$_6$) δ 1.74 (dd, J=13.8, 10.2 Hz, 2H), 1.94-2.38 (m, 6H), 2.64-2.81 (m, 1H), 2.92 (d, J=10.7 Hz, 2H), 3.03-3.22 (m, 3H), 3.33-3.69 (m, 8H), 3.72 (s, 4H), 5.96 (s, 1H), 7.00 (d, J=4.9 Hz, 1H), 7.09-7.27 (m, 3H), 8.13 (d, J=5.0 Hz, 1H). MS (APCI$^+$) m/z 499.2 (M+H)$^+$.

EXAMPLE 957

1-(3-fluoroazetidin-1-yl)-2-{4-[4-(5-fluoro-2-methoxyphenyl)-1H-pyrrolo[2,3-b]pyridin-2-yl]piperidin-1-yl}ethanone $^1$H NMR (400 MHz, DMSO-d$_6$) δ 1.65-1.84 (m, 2H), 1.94-2.15 (m, 2H), 2.22 (td, J=11.6, 2.5 Hz, 2H), 2.73 (tt, J=11.8, 4.0 Hz, 1H), 2.89 (dt, J=11.9, 3.5 Hz, 2H), 3.03 (s, 2H), 3.72 (s, 3H), 4.26 (s, 4H), 5.29 (tt, J=6.1, 3.2 Hz, 0H), 5.43 (tt, J=6.2, 3.2 Hz, 0H), 5.97 (s, 1H), 7.00 (d, J=4.9 Hz, 1H), 7.09-7.28 (m, 3H), 8.13 (d, J=4.9 Hz, 1H). MS (APCI$^+$) m/z 441.2 (M+H)$^+$.

EXAMPLE 958

N-(3-fluorocyclobutyl)-2-{4-[4-(5-fluoro-2-methoxyphenyl)-1H-pyrrolo[2,3-b]pyridin-2-yl]piperidin-1-yl}acetamide $^1$H NMR (400 MHz, DMSO-d$_6$) δ 1.80 (tdt, J=11.9, 8.2, 3.7 Hz, 2H), 1.88-2.08 (m, 2H), 2.08-2.45 (m, 4H), 2.62-2.81 (m, 2H), 2.81-2.97 (m, 4H), 3.72 (s, 3H), 3.79 (dd, J=8.7, 7.1 Hz, 1H), 4.38 (dd, J=8.5, 6.0 Hz, 0H), 4.80 (dt, J=56.4, 6.7 Hz, 0H), 5.14 (t, J=3.4 Hz, 0H), 5.28 (t, J =3.4 Hz, 0H), 5.98 (t, J=0.9 Hz, 1H), 7.01 (d, J=4.9 Hz, 1H), 7.09-7.28 (m, 3H), 8.13 (d, J=5.0 Hz, 1H). MS (APCI$^+$) m/z 455.2 (M+H)$^+$.

EXAMPLE 959

2-{4-[4-(5-fluoro-2-methoxyphenyl)-1H-pyrrolo[2,3-b]pyridin-2-yl]piperidin-1-yl}-1-(3-hydroxypyrrolidin-1-yl)ethanone $^1$H NMR (400 MHz, DMSO-d$_6$) δ 1.64-1.83 (m, 3H), 1.96 (dd, J=13.1, 3.1 Hz, 3H), 2.26 (td, J=11.6, 2.7 Hz, 2H), 2.73 (tt, J=11.8, 4.0 Hz, 1H), 2.93 (d, J=11.1 Hz, 2H), 3.11 (d, J=11.1 Hz, 2H), 3.34-3.50 (m, 2H), 3.60 (t, J=7.1 Hz, 2H), 3.72 (s, 3H), 4.29 (d, J=21.6 Hz, 1H), 5.96 (s, 1H), 7.00 (d, J=4.9 Hz, 1H), 7.09-7.27 (m, 3H), 8.13 (d, J=5.0 Hz, 1H). MS (APCI$^+$) m/z 453.2 (M+H)$^+$.

EXAMPLE 960

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid

EXAMPLE 960A ethyl 2-(3-(4-(4-(5-fluoro-2-methoxyphenyl)-1H-pyrrolo[2,3-b]pyridin-2-yl)-5,6-dihydropyridin-1(2H)-yl)oxetan-3-yl)acetate A mixture of Example 87D (750.0 mg, 1.893 mmol), ethyl 2-(oxetan-3-ylidene)acetate (0.263 mL, 2.271 mmol), and triethylamine (1.319 mL, 9.46 mmol) in N,N-dimethylformamide (10 mL) was heated at 100° C. for 2 days. The reaction mixture was concentrated, treated with ethyl acetate and a small amount of methanol, and washed with water and brine. The organic layer was dried over MgSO$_4$, filtered, concentrated, and purified on an 80 g silica column using the ISCO Companion flash system eluting with ethyl acetate/methanol (97.5:2.5 to 95:5) to provide the title compound. MS (ESI$^+$) m/z 466.1 (M+H)$^+$.

EXAMPLE 960B (3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid A mixture of Example 960A (50.0 mg, 0.107 mmol) and lithium hydroxide (5.14 mg, 0.215 mmol) in tetrahydrofuran (2 ml), methanol (0.8 ml), and water (0.6 ml) was stirred overnight. The reaction mixture was concentrated and purified by HPLC (see protocols in Example 361) to provide the title compound as a trifluoroacetic acid salt. $^1$H NMR (500 MHz, methanol-d$_4$) δ ppm 3.01 (dd, J =7.6, 4.6 Hz, 2H), 3.28 (s, 2H), 3.59 (t, J=6.0 Hz, 3H), 3.81 (s, 3H), 4.06-4.11 (m, 2H), 4.92 (s, 4H), 6.52-6.59 (m, 1H), 6.66 (s, 1H), 7.19-7.32 (m, 3H), 7.46 (d, J=5.8 Hz, 1H), 8.33 (d, J=5.8 Hz, 1H). MS (ESI$^+$) m/z 438.1 (M+H)$^+$.

EXAMPLE 961

4-fluoro-2-{2-[1-(methylsulfonyl)-1,2,3,6-tetrahydropyridin-4-yl]-1H-pyrrolo[2,3-b]pyridin-4-yl}aniline A mixture of Example 220F (500 mg, 1.404 mmol), 4-fluoro-2-(4,4,5,5-tetramethyl-1,3,2-dioxaborolan-2-yl)aniline (399 mg, 1.684 mmol), and dichlorobis(triphenylphosphine)palladium (II) (99 mg, 0.14 mmol) was suspended in a mixture of 7:3:2 dimethoxyethane/water/ethanol (14 mL). 2.45 mL of 2 M aqueous Na$_2$CO$_3$ solution was then added. The suspension was stirred at room temperature for a few seconds and was stirred in a microwave reactor (Biotage Initiator, model 355302) at 150° C. for 30 minutes. The mixture was partitioned between ethyl acetate and brine. The organic phase was concentrated and the residue was stirred in 2% methanol/methylene chloride. The insoluble material was collected by filtration to provide title compound. The mother liquor was separated by flash chromatography (0-15% CH$_3$OH in 2:1 ethyl acetate/hexane) to provide the second batch of title compound. $^1$H NMR (400 MHz, DMSO-d$_6$): δ2.01-2.09 (m, 1 H), 2.14-2.23 (m, 1 H), 2.94 (s, 3 H), 3.37 (t, J=5.65 Hz, 2 H), 3.91 (d, J=2.75 Hz, 2 H), 4.70 (s, 2 H), 6.29 (d, J=1.53 Hz, 1 H), 6.55 (s, 1 H), 6.82 (dd, J=8.85, 4.88 Hz, 1 H), 6.92-7.06 (m, 3 H), 8.25 (d, J=4.88 Hz, 1 H), 11.93 (s, 1 H); MS (DCI/NH$_3$) m/z 387 (M+H)$^+$.

EXAMPLE 964

2-(3,3-dimethyl-1,2,3,6-tetrahydropyridin-4-yl)-4-(5-fluoro-2-methoxyphenyl)-1H-pyrrolo[2,3-b]pyridine The title compound was prepared essentially as described in Example 87, substituting Example 87A with Example 258C in Example 87B and substituting the appropriate boronate in Example 87C. $^1$H NMR (400 MHz, DMSO-d$_6$) δ ppm 1.32 (s, 6H), 3.07-3.13 (m, 2H), 3.77 (s, 5H), 6.23-6.29 (m, 1H), 6.39 (d, J=1.8 Hz, 1H), 7.19-7.30 (m, 2H), 7.28-7.39 (m, 2H), 8.34 (d, J=5.4 Hz, 1H), 9.61 (bs, 2H), 12.45 (bs, 1H). MS (ESI$^+$) m/z 352.2 (M+H)$^+$.

EXAMPLE 965

2-(methylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate To a solution of tert-butyl(2-hydroxyethyl)(methyl)carbamate (0.526 g, 3.00 mmol) in dichloromethane (8.70 mL) was added dropwise with ice cooling sulfurisocyanatidic chloride (0.261 mL, 3 mmol) over 15 minutes. Dimethylaminopyridine (0.751 g, 6.14 mmol) was added, the cooling bath was removed, and the mixture was stirred for 1 hour. The ~0.33M solution of pyridinium sulfonylamide was used directly in the subsequent step. The solution (1.1 mL, 0.37 mmol) was added to a suspension of Example 87D (100 mg, 0.252 mmol) in 4 mL dichloromethane and triethylamine (176 μL, 1.262 mmol) and the mixture was stirred at room temperature for 16 hours. The mixture was dry loaded onto silica gel and purified by silica gel flash chromatography (Isco®, 12 G Redi-Sep®, 50-100% ethylacetate/hexane linear gradient then 10% of a 2:1 methanol:water in ethyl acetate) to afford the protected intermediate. To a solution of the intermediate in 2 mL 50% methanol/ethyl acetate was added 2M hydrogen chloride in diethyl ether (4 mL) and the mixture was stirred at 40° C. for 2 hours (a precipitate formed). After cooling to 0° C., the solid was filtered and washed with 5 mL diethyl ether and 5 mL heptane. The solid was dried under high vacuum to provide the title compound as a bis hydrochloride salt. $^1$H NMR (400 MHz, dimethylsulfoxide-d$_6$) δ 12.55 (s, 1H), 11.61 (s, 1H), 9.27-9.05 (m, 2H), 8.29 (d, J=5.3 Hz, 1H), 7.40-7.18 (m, 4H), 6.72-6.58 (m, 1H), 6.41 (d, J=1.8 Hz, 1H), 4.32 (t, J=5.3 Hz, 2H), 4.12-4.05 (m, 2H), 3.76 (s, 3H), 3.51 (t, J=5.7 Hz, 2H), 3.20-3.11 (m, 2H), 2.67-2.60 (m, 2H), 2.55 (t, J=5.3 Hz, 3H). MS (ESI$^+$) m/z 503.9 (M+H)$^+$.

EXAMPLE 966

2-{[({4-[4-(5-fluoro-2-methoxyphenyl)-1H-pyrrolo[2,3-b]pyridin-2-yl]-3,6-dihydropyridin-1(2H)-yl}sulfonyl)carbamoyl]oxy}ethyl acetate The title compound was prepared as described in Example 965, with the exception of the BOC removal step, using 2-hydroxyethyl acetate in place of tert-butyl(2-hydroxyethyl)(methyl)carbamate. $^1$H NMR (400 MHz, dimethylsulfoxide-d$_6$) δ 11.96-11.75 (m, 1H), 11.51 (s, 1H), 8.21 (d, J=5.0 Hz, 1H), 7.35-7.16 (m, 3H), 7.04 (d, J=4.9 Hz, 1H), 6.58-6.42 (m, 1H), 6.26 (d, J=2.0 Hz, 1H), 4.31-4.14 (m, 4H), 4.08-3.97 (m, 2H), 3.74 (s, 3H), 3.47 (t, J=5.7 Hz, 2H), 2.67-2.54 (m, 2H), 2.02-1.95 (m, 3H). MS (ESI$^+$) m/z 532.0 (M+H)$^+$.

EXAMPLE 967

2-(pyrrolidin-1-yl)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965, with the exception of the BOC removal step, using 2-(pyrrolidin-1-yl)ethanol in place of tert-butyl(2-hydroxyethyl)(methyl)carbamate. $^1$H NMR (500 MHz, dimethylsulfoxide-d$_6$) δ 12.06-11.91 (m, 1H), 11.68 (s, 1H), 9.89 (s, 1H), 8.24 (d, J=5.0 Hz, 1H), 7.40-7.16 (m, 3H), 7.09 (d, J=5.0 Hz, 1H), 6.57-6.48 (m, 1H), 6.30 (d, J=2.1 Hz, 1H), 4.33 (t, J=5.2 Hz, 2H), 4.09-4.02 (m, 2H), 3.74 (s, 3H), 3.61-3.38 (m, 6H), 3.07-2.91 (m, 2H), 2.64-2.57 (m, 2H), 2.05-1.72 (m, 4H). MS (ESI$^+$) m/z 544.2 (M+H)$^+$.

EXAMPLE 968 azetidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl 3-hydroxyazetidine-1-carboxylate in place of tert-butyl(2-hydroxyethyl)(methyl)carbamate. $^1$H NMR (400 MHz, dimethylsulfoxide-d$_6$) δ 12.60 (s, 1H), 11.87 (s, 1H), 9.56 (s, 1H), 9.30 (s, 1H), 8.30 (d, J =5.4 Hz, 1H), 7.41-7.19 (m, 4H), 6.72-6.57 (m, 1H), 6.43 (d, J=1.9 Hz, 1H), 5.24-5.15 (m, 1H), 4.32-4.16 (m, 2H), 4.09-4.03 (m, 2H), 4.02-3.91 (m, 2H), 3.51 (t, J=5.8 Hz, 2H), 2.62 (d, J=5.8 Hz, 2H). MS (ESI$^+$) m/z 502.0 (M+H)$^+$.

EXAMPLE 969

2-hydroxyethyl ({4-[4-(5-fluoro-2-methoxyphenyl)-1H-pyrrolo[2,3-b]pyridin-2-yl]-3,6-dihydropyridin-1(2H)-yl}sulfonyl)carbamate To a mixture of Example 966 (52 mg, 0.098 mmol) in tetrahydrofuran (488 μL) was added 5M aqueous sodium hydroxide (98 μL, 0.488 mmol). The mixture was stirred at ambient temperature for 2 hours and 5 mL 1M aqueous phosphoric acid was added. The mixture was extracted with ethyl acetate (4×1.5 mL) and the combined extracts were dried over magnesium sulfate, filtered and concentrated to afford the title compound. $^1$H NMR (400 MHz, dimethylsulfoxide-d$_6$) δ 12.06-11.86 (m, 1H), 11.43 (s, 1H), 8.23 (d, J=5.0 Hz, 1H), 7.36-7.15 (m, 3H), 7.07 (d, J=5.0 Hz, 1H), 6.58-6.47 (m, 1H), 6.29 (d, J=2.0 Hz, 1H), 4.12-3.99 (m, 4H), 3.74 (s, 3H), 3.58-3.53 (m, 2H), 3.52-3.45 (m, 2H), 2.65-2.54 (m, 2H). MS (ESI$^+$) m/z 491.0 (M+H)$^+$.

EXAMPLE 970

N-[2-(3-fluoro-5-{2-[1-(methylsulfonyl)-1,2,3,6-tetrahydropyridin-4-yl]-1H-pyrrolo[2,3-b]pyridin-4-yl}phenoxy)ethyl]methanesulfonamide

EXAMPLE 970A 2-(3-fluoro-5-(2-(1,2,3,6-tetrahydropyridin-4-yl)-1H-pyrrolo[2,3-b]pyridin-4-yl)phenoxy)ethanamine The title compound was prepared using the procedure described in Example 795A-D, using 3-bromo-5-fluorophenol in place of 2-bromo-4-fluorophenol in Example 795A.

EXAMPLE 970B

N-[2-(3-fluoro-5-{2-[1-(methylsulfonyl)-1,2,3,6-tetrahydropyridin-4-yl]-1H-pyrrolo[2,3-b]pyridin-4-yl}phenoxy)ethyl]methanesulfonamide The title compound was prepared using the procedure described in Example 119, using Example 970A in place of Example 87D. $^1$H NMR (500 MHz, DMSO-$d_6$) δ 12.03 (s, 1H), 8.27 (d, J =4.9 Hz, 1H), 7.31 (t, J=5.9 Hz, 1H), 7.23-7.10 (m, 3H), 6.97 (d, J=10.8, Hz, 1H), 6.64 (s, 1H), 6.57 (s, 1H), 4.17 (t, J=5.5 Hz, 2H), 3.93 (s, 2H), 3.41-3.34 (m, 4H), 2.97 (s, 3H), 2.94 (s, 3H), 2.71-2.66 (m, 2H). MS (ESI+) m/e 509 (M+H)$^+$.

EXAMPLE 971

4-[4-(5-fluoro-2-methoxyphenyl)-1H-pyrrolo[2,3-b]pyridin-2-yl]-5,6-dihydropyridin-2(1H)-one

EXAMPLE 971A tert-butyl 4-(4-(5-fluoro-2-methoxyphenyl)-1-(phenylsulfonyl)-1H-pyrrolo[2,3-b]pyridin-2-yl)-2-oxo-5,6-dihydropyridine-1(2H)-carboxylate A mixture of Example 87B (0.9 g, 1.771 mmol), tert-butyl 2-oxo-4-(4,4,5,5-tetramethyl-1,3,2-dioxaborolan-2-yl)-5,6-dihydropyridine-1(2H)-carboxylate (0.827 g, 2.302 mmol), Pd(PPh$_3$)$_4$ (0.205 g, 0.177 mmol) and sodium bicarbonate (0.446 g, 5.31 mmol) in N,N-dimethylformamide (10 mL) and H$_2$O (1 mL) was degassed and heated to 80° C. for 12 hours. The reaction mixture was diluted with ethyl acetate and washed with water and brine. The organic layer was dried over MgSO$_4$, filtered, concentrated, and purified by column chromatography on silica gel eluting with petroleum ether and ethyl acetate (10:1 to 3:1) to provide the title compound. LCMS (ESI) m/z 578.0 (M+H)$^+$.

EXAMPLE 971B 4-(4-(5-fluoro-2-methoxyphenyl)-1-(phenylsulfonyl)-1H-pyrrolo[2,3-b]pyridin-2-yl)-5,6-dihydropyridin-2(1H)-one A mixture of Example 971A (350 mg, 0.606 mmol) and trifluoroacetic acid (0.467 mL, 6.06 mmol) in CH$_2$Cl$_2$ (10 mL) was stirred at 25° C. for 2 hours. The solution was concentrated to provide the title compound as a trifluoroacetic acid salt. LCMS (ESI) m/z 478 (M+H)$^+$.

EXAMPLE 971C

4-[4-(5-fluoro-2-methoxyphenyl)-1H-pyrrolo[2,3-b]pyridin-2-yl]-5,6-dihydropyridin-2(1H)-one A mixture of NaOH (63.3 mg, 1.583 mmol), Example 971B (360 mg, 0.528 mmol) in H$_2$O (1 mL) and 1,4-dioxane (5 mL) was stirred at 60° C. for 12 hours. The solution was concentrated and purified by HPLC (see similar protocols in Example 220G) to provide the title compound. $^1$H NMR (400 MHz, DMSO-$d_6$) δ 2.71 (t, J=6.8 Hz, 2H), 3.75 (s, 3H), 6.47 (s, 1H), 6.65 (s, 1H), 7.10 (d, J=4.8 Hz, 1H), 7.20-7.30 (m, 3H), 7.49 (s, 1H), 8.31 (d, J=4.8 Hz, 1H), 12.13 (s, 1H). LCMS (ESI) m/z 338.1 (M+H)$^+$.

EXAMPLE 973

1-{4-[4-(5-fluoro-2-methoxyphenyl)-1H-pyrrolo[2,3-b]pyridin-2-yl]-3,6-dihydropyridin-1(2H)-yl}-3-[2-(hydroxymethyl)pyrrolidin-1-yl]propane-1,3-dione The title compound was prepared essentially as described in Example 865, substituting pyrrolidin-2-ylmethanol for azetidin-3-ol hydrochloride. The final product was purified by reverse phase HPLC on a Phenomenex Luna C8(2) 5 um 100 Å AXIA column (30 mm×75 mm) eluting with a gradient of 10-95% acetonitrile in 0.1% ammonium acetate/water. $^1$H NMR (400 MHz, DMSO-$d_6$) δ ppm 1.67-2.05 (m, 5H), 2.47-2.58 (m, 2H), 3.29-3.68 (m, 8H), 3.72 (s, 3H), 3.93-4.01 (m, 1H), 4.13-4.21 (m, 2H), 6.24 (s, 1H), 6.47 (t, J=3.5 Hz, 1H), 7.01 (d, J=4.9 Hz, 1H), 7.08-7.28 (m, 3H), 8.19 (d, J=4.9 Hz, 1H), 11.54 (brs, 1H). MS (ESI$^+$) m/z 493.1 (M+H)$^+$.

EXAMPLE 977

4-[4-(5-fluoro-2-methoxyphenyl)-1H-pyrrolo[2,3-b]pyridin-2-yl]cyclohex-3-en-1-amine

EXAMPLE 977A 4-((tert-butoxycarbonyl)amino)cyclohex-1-en-1-yl trifluoromethanesulfonate To a −78° C. stirred solution of lithium bis(trimethylsilylamide) (65 mL, 65 mmol, 1M in tetrahydrofuran) was added an additional 25 mL tetrahydrofuran followed by tert-butyl(4-oxocyclohexyl)carbamate (10.4 g, 48.8 mmol) in 25 mL tetrahydrofuran. After stirring or 30 minutes at −78° C., 1,1,1-trifluoro-N-phenyl-N-((trifluoromethyl)sulfonyl)methanesulfonamide (24.4 g, 68.3 mmol) was added as a tetrahydrofuran solution (30 mL) and the mixture was stirred at −78° C. for 1 hour then warmed to room temperature. After 24 hours, the reaction mixture was quenched with water and extracted with ethyl acetate. Purification by flash chromatography on silica gel eluting with 0-70% ethyl acetate-hexanes afforded the title compound.

EXAMPLE 977B tert-butyl (4-(4,4,5,5-tetramethyl-1,3,2-dioxaborolan-2-yl)cyclohex-3-en-1-yl)carbamate Example 977A (11.3 g, 33 mmol), [1,1'-bis(diphenylphosphino)ferrocene]dichloropalladium(II)-dichloromethane adduct (1.6 g, 1.9 mmol), potassium acetate (9.6 g, 98 mmol)

and 4,4,4',4',5,5,5',5'-octamethyl-2,2'-bi(1,3,2-dioxaborolane) (9.9 g, 39 mmol) were dissolved in dioxane (109 mL). The mixture was degassed and heated to 75° C. for 24 hours. The mixture was partitioned between water and ethyl acetate and the organic layer was dried over sodium sulfate, filtered, and concentrated. Purification by flash chromatography on silica gel eluting with 0-70% ethyl acetate in heptanes provided the title compound.

EXAMPLE 977C tert-butyl (4-(4-(5-fluoro-2-methoxyphenyl)-1-(phenylsulfonyl)-1H-pyrrolo[2,3-b]pyridin-2-yl)cyclohex-3-en-1-yl)carbamate Example 977B (0.95 g, 3 mmol), Example 87B (1 g, 2 mmol), (bis(diphenylphosphino)ferrocene]dichloropalladium(II)-dichloromethane adduct (96 mg, 0.11 mmol) and sodium carbonate (0.63 g, 6 mmol) were dissolved in 4:1 dioxane:water (10 mL), degassed and heated in a Biotage Initiator microwave reactor (model 355302) at 100° C. for 50 minutes After cooling to room temperature, the mixture was partitioned between water and ethyl acetate and the organic layer was dried over sodium sulfate, filtered, and concentrated. Purification by flash chromatography on silica gel eluting with 0-70% ethyl acetate in heptanes provided the title compound. MS (ESI) m/e 578.1 (M+1)$^+$.

EXAMPLE 977D tert-butyl (4-(4-(5-fluoro-2-methoxyphenyl)-1H-pyrrolo[2,3-b]pyridin-2-yl)cyclohex-3-en-1-yl)carbamate A solution of Example 977C (1.44 g, 2.5 mmol) and sodium hydroxide (4 mL, 2M) in dioxane (4 mL) was stirred at 90° C. for 24 hours. After cooling to room temperature and concentrating, the mixture was partitioned between water and ethyl acetate. The layers were separated and the aqueous phase was extracted with ethyl acetate. The combined organic layers were dried over sodium sulfate, filtered, and concentrated to provide the title compound which was used without any further purification. MS (ESI) m/e 438.1 (M+H)$^+$.

EXAMPLE 977E

4-[4-(5-fluoro-2-methoxyphenyl)-1H-pyrrolo[2,3-b]pyridin-2-yl]cyclohex-3-en-1-amine Example 977D (956 mg, 2.2 mmol) and trifluoroacetic acid (1 mL) were stirred in dichloromethane (5 mL) for 3 hours at room temperature. The reaction mixture was concentrated. The HCl salt of the title compound was prepared by dissolving the resultant solid in methanol, adding 2M HCl in diethyl ether and removing the solvents. $^1$HNMR (500 MHz, DMSO-d$_6$) δ 1.76 (m, 1H), 2.10 (m, 1H), 2.36 (m, 1H), 2.46 (m, 1H), 2.61 (m, 1H), 2.65 (m, 1H), 3.33 (m, 1H), 3.74 (s, 3H), 6.37 (s, 1H), 6.55 (br s, 1H), 7.29 (m, 4H), 8.28 (m, 1H), 12.48 (br s, 1H). MS (ESI) m/e 338.1 (M+H)$^+$.

EXAMPLE 978

4-(5-fluoro-2-methoxyphenyl)-2-[(6S)-6-methyl-1,2,3,6-tetrahydropyridin-4-yl]-1H-pyrrolo[2,3-b]pyridine The title compound was prepared as described in Example 258F. $^1$HNMR (400 MHz, DMSO-d$_6$) δ 1.38 (d, 3H), 2.70 (m, 2H), 3.25 (m, 1H), 3.49 (m, 1H), 3.74 (s, 3H), 4.14 (m, 1H), 6.39 (s, 1H), 6.44 (s, 1H), 7.09 (d, 1H), 7.25 (m, 3H), 8.25 (d, 1H), 12.00 (br s, 1H). MS (ESI) m/e 338.1 (M+H)$^+$.

EXAMPLE 979

N$^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N-methylglycinamide Example 910A (199 mg, 0.44 mmol), 2-amino-N-methylacetamide hydrochloride (48 mg, 0.38 mmol) and triethylamine (0.25 mL, 1.8 mmol) were stirred in ethanol (4 mL) at 70° C. for 24 hours. The reaction mixture was cooled and the resultant solid was washed with methanol, filtered and collected to provide the title compound. $^1$HNMR (400 MHz, DMSO-d$_6$) δ 2.62 (d, 3H), 2.64 (m, 2H), 3.74 (s, 3H), 3.92 (m, 2H), 4.16 (d, 2H), 4.45 (m, 2H), 6.31 (s, 1H), 6.56 (m, 1H), 7.05 (d, 1H), 7.25 (m, 3H), 7.96 (m, 1H), 8.06 (t, 1H), 8.22 (d, 1H), 11.91 (br s, 1H). (ESI) m/e 490.1 (M+H)$^+$.

EXAMPLE 980 tert-butyl N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinate The title compound was prepared using the procedure described in Example 979 using glycine tert-butyl ester hydrochloride in place of 2-amino-N-methylacetamide hydrochloride. $^1$HNMR (400 MHz, DMSO-d$_6$) δ 1.42 (s, 9H), 2.64 (m, 2H), 3.74 (s, 3H), 3.92 (m, 2H), 4.21 (d, 2H), 4.44 (m, 2H), 6.31 (s, 1H), 6.55 (m, 1H), 7.04 (d, 1H), 7.25 (m, 3H), 8.10 (t, 1H), 8.22 (d, 1H), 11.90 (br s, 1H). MS (ESI) m/e 533.1 (M+H)$^+$.

EXAMPLE 981

N$^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinamide The title compound was prepared using the procedure described in Example 979 using glycinamide hydrochloride in place of 2-amino-N-methylacetamide hydrochloride. $^1$HNMR (400 MHz, DMSO-d$_6$) 2.64 (m, 2H), 3.74 (s, 3H), 3.92 (m, 2H), 4.13 (d, 2H), 4.44 (m, 2H), 6.31 (br s, 1H), 6.55 (m, 1H), 7.04 (d, 1H), 7.25 (m, 3H), 7.51 (m, 1H), 8.02 (t, 1H), 8.22 (d, 1H), 11.91 (br s, 1H). (ESI) m/e 476.1 (M+H)$^+$.

EXAMPLE 982

N$^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N,N-dimethylglycinamide The title compound was prepared using the procedure described in Example 979 using 2-amino-N,N-dimethylacetamide in place of 2-amino-N-methylacetamide hydrochloride. $^1$HNMR (400 MHz, DMSO-d$_6$) δ 2.46 (m, 2H), 2.85 (s, 3H), 2.96 (s, 3H), 3.74 (s, 3H), 3.93 (m, 2H), 4.41 (d, 2H), 4.45 (m, 2H), 6.31 (m, 1H), 6.55 (m, 1H), 7.04 (d, 1H), 7.25 (m, 3H), 7.94 (t, 1H), 8.22 (d, 1H), 11.90 (br s, 1H). MS (ESI) m/e 504.1 (M+H)$^+$.

EXAMPLE 983 tert-butyl {4-[4-(4-fluoro-2-methoxyphenyl)-1H-pyrrolo[2,3-b]pyridin-2-yl]-3,6-dihydropyridin-1(2H)-yl}acetate

EXAMPLE 983A 4-(4-fluoro-2-methoxyphenyl)-2-(1,2,3,6-tetrahydro-pyridin-4-yl)-1H-pyrrolo[2,3-b]pyridine The title compound was prepared using the procedure described in Example 87, using 4-fluoro-2-methoxyphenylboronic acid in place of 5-fluoro-2-methoxyphenylboronic acid.

EXAMPLE 983B tert-butyl {4-[4-(4-fluoro-2-methoxyphenyl)-1H-pyrrolo[2,3-b]pyridin-2-yl]-3,6-dihydropyridin-1(2H)-yl}acetate The title compound was prepared using the procedure described in Example 224, using Example 983A in place of Example 87D and tert-butyl 2-bromoacetate in place of 2-chloro-N,N-dimethylacetamide. $^1$H NMR (400 MHz, DMSO-d$_6$) δ 11.72 (s, 1H), 8.17 (d, J=4.9 Hz, 1H), 7.42 (dd, J=8.5, 6.9 Hz, 1H), 7.09 (dd, J=11.4, 2.4 Hz, 1H), 6.99 (d, J=5.0 Hz, 1H), 6.90 (td, J=8.4, 2.5 Hz, 1H), 6.50-6.42 (m, 1H), 6.17 (d, J=2.0 Hz, 1H), 3.77 (s, 3H), 3.26-3.25 (m, 2H), 3.23 (s, 2H), 2.78-2.71 (m, 2H), 2.46-2.44 (m, 2H), 1.43 (s, 9H). MS (ESI+) m/e 438 (M+H)$^+$.

EXAMPLE 985

4-[4-(5-fluoro-2-methoxyphenyl)-1H-pyrrolo[2,3-b]pyridin-2-yl]cyclohex-3-ene-1-carbonitrile

EXAMPLE 985A 4-(4-(5-fluoro-2-methoxyphenyl)-1-tosyl-1H-pyrrolo[2,3-b]pyridin-2-yl)cyclohex-3-enecarbonitrile A mixture of Example 258C (150.0 mg, 0.287 mmol), 4-(4,4,5,5-tetramethyl-1,3,2-dioxaborolan-2-yl)cyclohex-3-enecarbonitrile (73.6 mg, 0.316 mmol), Pd(Ph$_3$P)$_4$ (13.27 mg, 0.011 mmol), and aqueous sodium bicarbonate solution (0.7 mL) in N,N-dimethylformamide (2.8 mL) was degassed and heated at 80° C. for 4 hours and at 90° C. for 1.5 hours. After cooling, the reaction mixture was quenched with water and brine and extracted with ethyl acetate. The combined organic layers were washed with brine, dried over MgSO$_4$, filtered, concentrated, and purified on a 12 g silica column using the ISCO Companion flash system eluting with ethyl acetate/heptanes (3:7 to 4:6) to provide the title compound. MS (ESI$^+$) m/z 502.1 (M+H)$^+$.

EXAMPLE 985B

4-[4-(5-fluoro-2-methoxyphenyl)-1H-pyrrolo[2,3-b]pyridin-2-yl]cyclohex-3-ene-1-carbonitrile A mixture of Example 985A (84.3 mg, 0.168 mmol) and 5M sodium hydroxide (0.134 mL, 0.672 mmol) solution in methanol (3 mL) was heated in a Biotage Initiator microwave reactor (model 355302) at 85° C. for 30 minutes. After cooling, the suspension was filtered, rinsed with cold methanol and water, and vacuum oven-dried to provide the title compound. $^1$H NMR (400 MHz, DMSO-d$_6$) δ ppm 1.87-2.07 (m, 2H), 2.43-2.64 (m, 2H), 3.09-3.19 (m, 1H), 3.74 (s, 3H), 6.24 (d, J =1.8 Hz, 1H), 6.49 (bs, 1H), 7.03 (d, J=4.9 Hz, 1H), 7.15-7.31 (m, 3H), 8.20 (d, J=4.9 Hz, 1H), 11.79 (bs, 1H). MS (ESI$^+$) m/z 348.2 (M+H)$^+$.

EXAMPLE 986

2-{4-[4-(5-fluoro-2-methoxyphenyl)-5-methoxy-1H-pyrrolo[2,3-b]pyridin-2-yl]-3,6-dihydropyridin-1(2H)-yl}-N,N-dimethylacetamide The title compound was prepared according to the procedure described in Example 235, substituting 873C for Example 17G. $^1$H NMR (400 MHz, DMSO-d$_6$) δ 2.40 (br, 2H), 2.66 (t, J=5.7 Hz, 2H), 2.81 (s, 3H), 3.01 (s, 3H), 3.15-3.20 (m, 2H), 3.25 (bs, 2H), 3.68 (s, 3H), 3.76 (s, 3H), 5.91 (d, J=2.0 Hz, 1H), 6.42 (bs, 1H), 7.07 (dd, J=8.8, 3.1 Hz, 1H), 7.14 (dd, J=9.1, 4.5 Hz, 1H), 7.23 (td, J=8.6, 3.2 Hz, 1H), 8.10 (s, 1H), 11.54-11.59 (m, 1H). MS (ESI$^+$) m/z 439 (M+H)$^+$.

EXAMPLE 987 ethyl ({5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}sulfonyl)carbamate The title compound was prepared using the condition described in Example 218, substituting ethanol for tert-butanol in Example 218A and Example 845 for Example 87D in Example 218B. $^1$H NMR (400 MHz, DMSO-d$_6$) δ ppm 1.10 (t, J=7.02 Hz, 3 H) 2.57-2.66 (m, 1 H) 2.83-2.95 (m, 1 H) 2.97-3.11 (m, 2 H) 3.47-3.64 (m, 4 H) 3.73 (s, 3 H) 4.00 (q, J=7.02 Hz, 2 H) 6.18 (d, J=1.83 Hz, 1 H) 6.29 (s, 1 H) 7.04 (d, J=4.88 Hz, 1 H) 7.13-7.32 (m, 3 H) 8.21 (d, J=4.88 Hz, 1 H) 11.19 (s, 1 H) 11.90 (d, J=1.53 Hz, 1 H). MS (ESI$^+$) m/z 501 (M+H)$^+$.

EXAMPLE 988

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}propane-1,2-diol The title compound was prepared using the conditions described in Example 149, substituting Example 845 for Example 135B. $^1$H NMR (400 MHz, DMSO-d$_6$) δ ppm 2.21-2.32 (m, 1 H) 2.41-2.49 (m, 5 H) 2.55-2.65 (m, 2 H) 2.78-2.98 (m, 2 H) 3.20-3.44 (m, 3 H) 3.48-3.59 (m, 1 H) 3.73 (s, 3 H) 6.11 (s, 1 H) 6.30 (s, 1 H) 6.97-7.08 (m, 1 H) 7.15-7.35 (m, 3 H) 8.19 (t, J=5.65 Hz, 1 H) 11.84 (s, 1 H). MS (ESI$^+$) m/z 424 (M+H)$^+$.

EXAMPLE 989

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}) acetic acid The title compound was prepared using the conditions described in Example 759C, substituting Example 845 for Example 759B. $^1$H NMR (400 MHz, DMSO-d$_6$) δ ppm 2.52-2.60 (m, 1 H) 2.66-2.84 (m, 2 H) 2.85-3.03 (m, 5 H) 3.19 (s, 2 H) 3.50 (s, 1 H) 3.73 (s, 3 H) 6.14 (s, 1 H) 6.30

(s, 1 H) 7.03 (d, J=4.88 Hz, 1 H) 7.13-7.36 (m, 3 H) 8.20 (d, J=4.88 Hz, 1 H) 11.89 (s, 1 H). MS (ESI$^+$) m/z 408 (M+H)$^+$.

EXAMPLE 990

2-{4-[4-(4-fluoro-2-methoxyphenyl)-1H-pyrrolo[2,3-b]pyridin-2-yl]-3,6-dihydropyridin-1(2H)-yl}acetamide The title compound was prepared using the procedure described in Example 224, substituting Example 983A for Example 87D and 2-bromoacetamide for 2-chloro-N,N-dimethylacetamide. $^1$H NMR (500 MHz, DMSO-d$_6$) δ 11.75 (s, 1H), 8.17 (d, J=5.0 Hz, 1H), 7.42 (dd, J=8.4, 6.9 Hz, 1H), 7.25-7.23 (m, 1H), 7.14-7.05 (m, 2H), 6.99 (d, J=4.9 Hz, 1H), 6.91 (td, J=8.4, 2.4 Hz, 1H), 6.47 (m, 1H), 6.18 (d, J=2.1 Hz, 1H), 3.78 (s, 3H), 3.35 (s, 2H), 3.20 (q, J=2.8 Hz, 2H), 2.99 (s, 2H), 2.66 (t, J=5.6 Hz, 2H). MS (ESI+) m/e 381 (M+H)$^+$.

EXAMPLE 991

2-{4-[4-(4-fluoro-2-methoxyphenyl)-1H-pyrrolo[2,3-b]pyridin-2-yl]-3,6-dihydropyridin-1(2H)-yl}-N-methylacetamide The title compound was prepared using the procedure described in Example 224, substituting Example 983A for Example 87D and 2-bromo-N-methylacetamide for 2-chloro-N,N-dimethylacetamide. $^1$H NMR (500 MHz, DMSO-d$_6$) δ 11.75 (s, 1H), 8.17 (d, J=4.9 Hz, 1H), 7.71 (q, J=4.7 Hz, 1H), 7.42 (t, J=8.4 Hz, 1H), 7.10 (dd, J=11.4, 2.5 Hz, 1H), 7.00 (d, J=4.9 Hz, 1H), 6.91 (td, J=8.4, 2.5 Hz, 1H), 6.48 (m, 1H), 6.18 (d, J=2.1 Hz, 1H), 3.78 (s, 3H), 3.19 (m, 2H), 3.03 (s, 2H), 2.67-2.63 (m, 2H), 2.63 (d, J=9.3 Hz, 3H), 2.54-2.48 (m, 2H). MS (ESI+) m/e 395 (M+H)$^+$.

EXAMPLE 992

N-{4-[4-(5-fluoro-2-methoxyphenyl)-1H-pyrrolo[2,3-b]pyridin-2-yl]cyclohexyl}-D-valine

EXAMPLE 992A (R)-tert-butyl 2-((4-(4-(5-fluoro-2-methoxyphenyl)-1H-pyrrolo[2,3-b]pyridin-2-yl)cyclohexyl)amino)-3-methylbutanoate To a mixture of Example 241B (125 mg, 0.372 mmol), triethylamine (0.114 mL, 0.818 mmol), acetic acid (0.106 mL, 1.858 mmol) and (R)-tert-butyl 2-amino-3-methylbutanoate, hydrochloric acid (0.401 mL, 1.858 mmol) in 4 mL (1:1 dichloromethane/methanol) was added Biotage MP-cyanoborohydride resin (2.17 mmol/g, 678 mg, 1.487 mmol). The reaction mixture was shaken at room temperature on an IKA Vibrax VXR shaker overnight. The reaction was diluted with dichloromethane and the resin was filtered off, and was rinsed with dichloromethane and methanol. The crude material was purified via flash chromatography, (Analogix280, SF 15-12 column, 0-4% methanol/dichloromethane over 30 minutes) to give the title compound. MS (ESI): 494.1 (M+H)$^+$.

EXAMPLE 992B

Example 992A (210 mg, 0.425 mmol) and methanol (20 ml) were added to 20% Pd(OH)$_2$/C, wet (100 mg, 0.073 mmol) in a 50 mL pressure bottle and the reaction mixture was stirred for 20 hours at 30 psi and 50° C. The solvent was removed to give the title compound. MS (ESI): 496.1 (M+H)$^+$.

EXAMPLE 992C

N-{4-[4-(5-fluoro-2-methoxyphenyl)-1H-pyrrolo[2,3-b]pyridin-2-yl]cyclohexyl}-D-valine To a solution of Example 992B (0.175 g, 0.357 mmol) in 5 mL dichloromethane was added excess trifluoroacetic acid. The solution was stirred at room temperature for 12 hours and the solvent was removed. The residue was dissolved in 5 mL methanol and was treated with excess 2M HCl/diethyl ether for 30 minutes. The reaction mixture was diluted with 35 mL diethyl ether and the solid was filtered to give the title compound as the HCl salt. $^1$H NMR (500 MHz, DMSO-d$_6$) δ ppm 12.84 (d, J=64.39 Hz, 1 H) 8.55-9.01 (m, 1 H) 6.94-7.66 (m, 4 H) 6.30 (d, J=52.80 Hz, 1 H) 3.86-4.06 (m, 3 H) 3.67-3.85 (m, 4 H) 3.28-3.46 (m, 2 H) 3.18 (s, 3 H) 2.73-2.88 (m, 1 H) 2.31-2.59 (m, 2 H) 2.06-2.32 (m, 2 H) 1.47-1.88 (m, 3 H) 0.81-1.19 (m, 4 H). MS (ESI): 440.2 (M+H)$^+$.

EXAMPLE 993

2-{4-[5-fluoro-4-(5-fluoro-2-methoxyphenyl)-1H-pyrrolo[2,3-b]pyridin-2-yl]piperidin-1-yl}acetamide The title compound was prepared according to the procedure described in Example 235, substituting Example 255D for Example 17G and 2-bromoacetamide for 2-chloro-N,N-dimethylacetamide. $^1$H NMR (500 MHz, DMSO-d$_6$) δ 1.75 (qt, J=12.2, 3.3 Hz, 2H), 1.89-1.96 (m, 2H), 2.17 (td, J=11.7, 2.4 Hz, 2H), 2.67 (tt, J=12.2, 4.0 Hz, 1H), 2.83-2.92 (m, 4H), 3.72 (s, 3H), 5.89 (d, J=1.9 Hz, 1H), 7.08-7.26 (m, 4H), 7.32 (td, J=8.6, 3.2 Hz, 1H), 8.12 (d, J=2.4 Hz, 1H), 11.71 (d, J=2.3 Hz, 1H). MS (ESI$^+$) m/z 401 (M+H)$^+$.

EXAMPLE 994

4-(5-fluoro-2-methoxyphenyl)-2-{1-[2-(2-methoxyethoxy)ethyl]-1,2,3,6-tetrahydropyridin-4-yl}-1H-pyrrolo[2,3-b]pyridine To a 5 mL microwave tube was added Example 87D (0.117 g, 0.295 mmol) and N-ethyl-N-isopropylpropan-2-amine (0.1 mL, 0.573 mmol) in N,N-dimethylformamide (2 mL) to give a suspension. 1-Bromo-2-(2-methoxyethoxy)ethane (0.064 g, 0.350 mmol) was added and the mixture was stirred at 120° C. for two hours under microwave irradiation using a Biotage Initiator (model 355302). After cooling to room temperature, the product was purified by reverse-phase HPLC on a Sunfire C8 column (30×100 mm, 5 μm particle size) using a gradient of 10-100% acetonitrile in 0.1% aqueous trifluoroacetic acid to provide the title compound as trifluoroacetic acid salt. $^1$H NMR (400 MHz, DMSO-d$_6$): δ 2.78-2.86 (m, 2 H) 3.28 (s, 3 H) 3.48-3.52 (m, 2 H) 3.59-3.63 (m, 2 H) 3.65-3.72 (m, 1 H) 3.74 (s, 3 H) 3.78-3.83 (m, 2 H) 3.86-3.96 (m, 1 H) 4.03-4.13 (m, 1 H) 6.38 (d, J=1.83 Hz, 1 H) 6.44-6.50 (m, 1 H) 7.08 (d, J=4.88 Hz, 1 H) 7.17-7.33 (m, 3 H) 8.25 (d, J=4.88 Hz, 1 H) 9.73-9.86 (m, 1 H) 12.00 (s, 1 H). MS (ESI$^+$) m/z: 426.1 (M+H)$^+$.

EXAMPLE 995

4-[4-(5-fluoro-2-methoxyphenyl)-1H-pyrrolo[2,3-b]pyridin-2-yl]cyclohex-3-en-1-yl methylsulfamate

EXAMPLE 995A 4-(5-fluoro-2-methoxyphenyl)-1-(phenylsulfonyl)-2-(1,4-dioxaspiro[4.5]dec-7-en-8-yl)-1H-pyrrolo[2,3-b]pyridine A 1000 mL flask was charged with Example 87B (19.94 g, 39.2 mmol), 4,4,5,5-tetramethyl-2-(1,4-dioxaspiro[4.5]dec-7-en-8-yl)-1,3,2-dioxaborolane (11.48 g, 43.2 mmol), sodium carbonate (12.47 g, 118 mmol) and bis(triphenylphosphine)palladium (II) (2.75 g, 3.92 mmol). The solids were sparged with argon for 30 minutes. Separately a mixture of dimethoxyethane (225 ml), water (96 mL) and ethanol (64.3 ml) was degassed with argon for 30 minutes. The mixed solvent was added to the sparged solids under a stream of argon and the resulting suspension was degassed with argon for an additional 5 minutes. The mixture was heated at 80° C. for 3 hours. After cooling, the reaction mixture was partitioned between ethyl acetate (700 mL), water (500 mL) and saturated sodium bicarbonate (300 mL). The layers were separated and the organic layer was washed with saturated sodium chloride (500 mL). The organic layer was dried over sodium sulfate along with a small amount of SiliaMetS® silica gel (Silicycle) added. The suspension was filtered and concentrated. The residue was dissolved in methylene chloride and purified on the CombiFlash RF chromatography system on a silica gel Gold Rf cartridge (220 g) and was eluted with a 5-60% ethyl acetate in heptanes gradient to provide the title compound. MS (DCI/NH$_3$) m/z 520 (M+H)$^+$.

EXAMPLE 995B 4-(4-(5-fluoro-2-methoxyphenyl)-1-(phenylsulfonyl)-1H-pyrrolo[2,3-b]pyridin-2-yl)cyclohex-3-enone A 500 mL flask was charged with Example 995A (6.8 g, 13.06 mmol) and dichloromethane (130 mL). To the resulting mixture was added trifluoroacetic acid (23 mL, 299 mmol) and the solution was stirred at room temperature overnight. More trifluoroacetic acid (5 mL, 65.0 mmol) was added and the solution was stirred for an additional 1.5 hours. The volatiles were removed and the residue was partitioned between methylene chloride (500 mL) and saturated sodium bicarbonate solution (500 mL). The layers were separated and the aqueous layer was extracted with methylene chloride (100 mL). The combined extracts were dried over sodium sulfate, filtered and concentrated. The residue was dissolved in methylene chloride and was purified on the CombiFlash RF chromatography system on a silica gel Gold Rf cartridge (120 g) and was eluted with a 0-60% ethyl acetate in heptanes gradient to provide the title compound. MS (DCI/NH$_3$) m/z 477 (M+H)$^+$.

EXAMPLE 995C 4-(4-(5-fluoro-2-methoxyphenyl)-1-(phenylsulfonyl)-1H-pyrrolo[2,3-b]pyridin-2-yl)cyclohex-3-enol A flask containing Example 995B (5.52 g, 11.58 mmol) was charged with methanol (100 ml). To this suspension was added sodium borohydride (1.753 g, 46.3 mmol) portionwise. After the addition, the reaction mixture was stirred at room temperature for 1 hour. The mixture was partitioned between methylene chloride and 50% saturated sodium bicarbonate solution. The layers were separated and the aqueous layer was extracted with methylene chloride. The combined organics were washed with brine, dried over sodium sulfate, filtered and concentrated. The residue was dissolved in methylene chloride and purified on the CombiFlash RF chromatography system on a silica gel Gold Rf cartridge (120 g) and was eluted with a 0-80% ethyl acetate in heptanes gradient to provide the title compound. MS (DCI/NH$_3$) m/z 477 (M+H)$^+$.

EXAMPLE 995D 4-(4-(5-fluoro-2-methoxyphenyl)-1-(phenylsulfonyl)-1H-pyrrolo[2,3-b]pyridin-2-yl)cyclohex-3-enyl methylsulfamate Into a 5 mL vial was added Example 995C (0.065 g, 0.136 mmol) in N,N-dimethylacetamide (2 mL). Methylsulfamoyl chloride (0.11 g, 0.85 mmol) was added. The mixture was stirred at room temperature overnight. The product was purified by reverse-phase HPLC on a Sunfire C8 column (30 ×100 mm, 5 μm particle size, flow rate 30 mL/minute) using a gradient of 30-80% acetonitrile in 0.1% aqueous trifluoroacetic acid to provide the title compound as trifluoroacetic acid salt. LC/MS: 571.9 (M+H)$^+$.

EXAMPLE 995E

4-[4-(5-fluoro-2-methoxyphenyl)-1H-pyrrolo[2,3-b]pyridin-2-yl]cyclohex-3-en-1-yl methylsulfamate The title compound was prepared using the procedure described in Example 236E, using Example 995D in place of Example 236D. $^1$H NMR (500 MHz, DMSO-d$_6$): δ 1.93-2.06 (m, 2 H) 2.39-2.57 (m, 2 H) 2.59 (d, J=4.88 Hz, 3 H) 2.63-2.72 (m, 1 H) 3.74 (s, 3 H) 4.68-4.75 (m, 1 H) 6.25 (d, J=2.14 Hz, 1 H) 6.41-6.44 (m, 1 H) 7.05 (d, J=4.88 Hz, 1 H) 7.18-7.31 (m, 3 H) 7.69 (q, J=4.88 Hz, 1 H) 8.20 (d, J=4.88 Hz, 1 H) 11.85 (s, 1 H). MS (ESI$^+$) m/z: 432.0 (M+H)$^+$.

The following compounds (concluding with Example 1008) were prepared essentially as described in Example 251, substituting Example 226B for Example 247B and the appropriate amine for 2-(methylamino)ethanol.

EXAMPLE 996

2-{4-[4-(5-fluoro-2-methoxyphenyl)-1H-pyrrolo[2,3-b]pyridin-2-yl]-3,6-dihydropyridin-1(2H)-yl}-1-(3-methoxyazetidin-1-yl)ethanone $^1$H NMR (400 MHz, DMSO-d$_6$) δ 8.18 (d, J=4.9 Hz, 1H), 7.34-7.10 (m, 3H), 7.02 (d, J=4.9 Hz, 1H), 6.46-6.39 (m, 1H), 6.20 (s, 1H), 4.35 (s, 1H), 4.20 (tt, J=6.3, 4.0 Hz, 1H), 4.14-3.90 (m, 4H), 3.73 (s, 3H), 3.22 (s, 4H), 3.13 (s, 2H), 2.72 (t, J=5.7 Hz, 2H), 2.49 (d, J=2.2 Hz, 2H). MS (APCI$^+$) m/z 451.1 (M+H)$^+$.

EXAMPLE 997

1-({4-[4-(5-fluoro-2-methoxyphenyl)-1H-pyrrolo[2,3-b]pyridin-2-yl]-3,6-dihydropyridin-1(2H)-yl}acetyl)azetidine-3-carbonitrile $^1$H NMR (400 MHz, DMSO-d$_6$) δ 8.18 (d, J=5.0 Hz, 1H), 7.28-7.11 (m, 3H), 7.02 (d, J=5.0 Hz, 1H), 6.45-6.39 (m, 1H), 6.20 (s, 1H), 4.32 (s, 3H), 3.72 (s, 3H), 3.25-3.17 (m, 3H), 3.15 (s, 2H), 2.71 (t, J=5.7 Hz, 2H), 2.49 (d, J=4.1 Hz, 2H), 2.02 (s, 1H). MS (APCI$^+$) m/z 446.1 (M+H)$^+$.

EXAMPLE 998

1-(3,3-difluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-d$_6$) δ 8.18 (d, J=5.0 Hz, 1H), 7.31-7.09 (m, 3H), 7.02 (d, J=5.0 Hz, 1H), 6.54-6.35 (m, 1H), 6.20 (s, 1H), 4.46 (s, 4H), 3.73 (s, 3H), 3.23 (d, J=2.1 Hz, 4H), 2.73 (t, J=5.7 Hz, 2H), 2.50-2.41 (m, 2H). MS (APCI$^+$) m/z 457.1 (M+H)$^+$.

EXAMPLE 999

2-{4-[4-(5-fluoro-2-methoxyphenyl)-1H-pyrrolo[2,3-b]pyridin-2-yl]-3,6-dihydropyridin-1(2H)-yl}-1-[3-(hydroxymethyl)azetidin-1-yl]ethanone $^1$H NMR (400 MHz, DMSO-d$_6$) δ 8.18 (d, J=5.0 Hz, 1H), 7.28-7.11 (m, 3H), 7.02 (d, J=5.0 Hz, 1H), 6.42 (s, 1H), 6.19 (s, 1H), 4.19 (s, 1H), 3.90 (s, 1H), 3.72 (s, 3H), 3.54 (d, J=6.2 Hz, 2H), 3.22 (s, 4H), 3.10 (s, 2H), 2.94-2.88 (m, 2H), 2.78-2.60 (m, 2H), 2.52-2.46 (m, 2H). MS (APCI$^+$) m/z 451.1 (M+H)$^+$.

EXAMPLE 1000

2-{4-[4-(5-fluoro-2-methoxyphenyl)-1H-pyrrolo[2,3-b]pyridin-2-yl]-3,6-dihydropyridin-1(2H)-yl}-1-(3-hydroxy-3-methylazetidin-1-yl)ethanone $^1$H NMR (400 MHz, DMSO-d$_6$) δ 8.18 (d, J=5.0 Hz, 1H), 7.29-7.12 (m, 3H), 7.02 (d, J=5.0 Hz, 1H), 6.47-6.39 (m, 1H), 6.19 (s, 1H), 4.03 (s, 2H), 3.86-3.63 (m, 5H), 3.22 (q, J=2.9 Hz, 2H), 3.12 (s, 2H), 2.72 (t, J=5.7 Hz, 2H), 2.50-2.44 (m, 2H), 1.38 (s, 3H). MS (APCI$^+$) m/z 451.1 (M+H)$^+$.

EXAMPLE 1001

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-d$_6$) δ 8.18 (d, J=5.0 Hz, 1H), 7.31-7.11 (m, 3H), 7.02 (d, J=4.9 Hz, 1H), 6.46-6.36 (m, 1H), 6.19 (s, 1H), 4.41 (s, 1H), 4.29-3.83 (m, 1H), 3.73 (s, 5H), 3.24 (d, J=3.1 Hz, 2H), 3.14 (s, 3H), 2.79-2.69 (m, 2H), 2.62 (s, 1H), 2.50-2.44 (m, 2H), 1.75-1.41 (m, 2H), 0.81 (t, J=7.4 Hz, 3H). MS (APCI$^+$) m/z 479.1 (M+H)$^+$.

EXAMPLE 1002

2-{4-[4-(5-fluoro-2-methoxyphenyl)-1H-pyrrolo[2,3-b]pyridin-2-yl]-3,6-dihydropyridin-1(2H)-yl}-1-[3-(methoxymethyl)-3-methylazetidin-1-yl]ethanone $^1$H NMR (400 MHz, DMSO-d$_6$) δ 8.18 (d, J=5.0 Hz, 1H), 7.29-7.09 (m, 3H), 7.02 (d, J=5.0 Hz, 1H), 6.48-6.38 (m, 1H), 6.19 (s, 1H), 4.02 (s, 4H), 3.89-3.62 (m, 4H), 3.49 (s, 1H), 3.33-3.31 (m, 6H), 3.26-3.18 (m, 2H), 3.10 (s, 2H), 2.71 (t, J=5.7 Hz, 2H), 2.50-2.42 (m, 2H), 1.21 (s, 3H). MS (APCI$^+$) m/z 479.1 (M+H)$^+$.

EXAMPLE 1003

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-d$_6$) δ 8.18 (d, J=5.0 Hz, 1H), 7.30-7.10 (m, 3H), 7.02 (d, J=4.9 Hz, 1H), 6.49-6.33 (m, 1H), 6.19 (s, 1H), 3.93-3.39 (m, 7H), 3.35 (s, 3H), 3.29-3.21 (m, 4H), 3.20 (s, 2H), 2.75 (s, 2H), 2.51-2.45 (m, 2H), 2.26-1.97 (m, 2H). MS (APCI$^+$) m/z 497.1 (M+H)$^+$.

EXAMPLE 1004

N-cyclobutyl-2-{4-[4-(5-fluoro-2-methoxyphenyl)-1H-pyrrolo[2,3-b]pyridin-2-yl]-3,6-dihydropyridin-1(2H)-yl}acetamide $^1$H NMR (400 MHz, DMSO-d$_6$) δ 8.18 (d, J=5.0 Hz, 1H), 7.31-7.12 (m, 3H), 7.03 (d, J=5.0 Hz, 1H), 6.49-6.36 (m, 1H), 6.21 (s, 1H), 4.22 (q, J=8.1 Hz, 1H), 3.73 (s, 3H), 3.28-3.19 (m, 2H), 3.03 (s, 2H), 2.71 (t, J=5.7 Hz, 2H), 2.51-2.45 (m, 2H), 2.29-2.11 (m, 2H), 2.03-1.86 (m, 2H), 1.65 (td, J=10.6, 7.9 Hz, 2H). MS (APCI$^+$) m/z 435.1 (M+H)$^+$.

EXAMPLE 1005

1-(3-fluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone $^1$H NMR (400 MHz, DMSO-d$_6$) δ 8.18 (d, J=5.0 Hz, 1H), 7.31-7.10 (m, 3H), 7.02 (d, J=5.0 Hz, 1H), 6.47-6.36 (m, 1H), 6.20 (s, 1H), 5.36 (ddt, J=57.2, 5.9, 2.9 Hz, 1H), 4.08 (d, J=142.4 Hz, 4H), 3.72 (s, 3H), 3.22 (d, J=3.2 Hz, 2H), 3.15 (s, 2H), 2.72 (t, J=5.7 Hz, 2H), 2.50-2.38 (m, 2H). MS (APCI$^+$) m/z 439.1 (M+H)$^+$.

EXAMPLE 1006

2-{4-[4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide $^1$H NMR (400 MHz, DMSO-d$_6$) δ 8.18 (d, J=5.0 Hz, 1H), 7.32-7.09 (m, 3H), 7.02 (d, J=5.0 Hz, 1H), 6.42 (s, 1H), 6.19 (s, 1H), 3.72 (s, 3H), 3.63-3.27 (m, 6H), 3.24 (d, J=3.2 Hz, 2H), 3.12-2.81 (m, 3H), 2.74 (t, J=5.7 Hz, 2H), 2.50-2.41 (m, 2H). MS (APCI$^+$) m/z 439.1 (M+H)$^+$.

EXAMPLE 1007

N-(3-fluorocyclobutyl)-2-{4-[4-(5-fluoro-2-methoxyphenyl)-1H-pyrrolo[2,3-b]pyridin-2-yl]-3,6-dihydropyridin-1(2H)-yl}acetamide $^1$H NMR (400 MHz, DMSO-d$_6$) δ 8.18 (d, J=5.0 Hz, 1H), 7.29-7.09 (m, 3H), 7.03 (d, J=5.0 Hz, 1H), 6.43 (q, J=2.9 Hz, 1H), 6.21 (s, 1H), 5.20 (dp, J=56.9, 3.4 Hz, 1H), 4.80 (dp, J=56.4, 6.7 Hz, 1H), 4.40 (td, J=6.0, 2.7 Hz, 1H), 3.87-3.76 (m, 1H), 3.73 (s, 3H), 3.24 (d, J=3.1 Hz, 2H), 3.06 (s, 2H), 2.71 (td, J=5.3, 2.4 Hz, 3H), 2.57-2.52 (m, 3H), 2.49-2.31 (m, 1H), 2.29-2.08 (m, 1H). MS (APCI$^+$) m/z 453.1 (M+H)$^+$.

EXAMPLE 1008

2-{4-[4-(5-fluoro-2-methoxyphenyl)-1H-pyrrolo[2,3-b]pyridin-2-yl]-3,6-dihydropyridin-1(2H)-yl}-1-(3-hydroxypyrrolidin-1-yl)ethanone $^1$H NMR (400 MHz, DMSO-d$_6$) δ 8.18 (d, J=5.0 Hz, 1H), 7.31-7.10 (m, 3H), 7.02 (d, J=4.9 Hz, 1H), 6.43 (t, J=1.6 Hz, 1H), 6.19 (s, 1H), 4.41-4.20 (m, 1H), 3.73 (s, 3H), 3.69-3.52 (m, 1H), 3.47-3.34 (m, 1H), 3.32-3.19 (m, 4H), 2.83-2.71 (m, 2H), 2.50-2.40 (m, 2H), 2.11-1.64 (m, 2H). MS (APCI$^+$) m/z 451.1 (M+H)$^+$.

EXAMPLE 1011

1-({4-[4-(5-fluoro-2-methoxyphenyl)-1H-pyrrolo[2,3-b]pyridin-2-yl]piperidin-1-yl}acetyl)-L-proline

EXAMPLE 1011A (2S)-methyl 1-(2-(4-(4-(5-fluoro-2-methoxyphenyl)-1H-pyrrolo[2,3-b]pyridin-2-yl)piperidin-1-yl)acetyl)pyrrolidine-2-carboxylate The title compound was prepared essentially as described in Example 238, substituting Example 247B for Example 226B and (S)-methyl pyrrolidine-2-carboxylate hydrochloride for azetidin-3-ol hydrochloride. MS (ESI$^+$) m/z 495.2 (M+H)$^+$.

EXAMPLE 1011B 1-({4-[4-(5-fluoro-2-methoxyphenyl)-1H-pyrrolo[2,3-b]pyridin-2-yl]piperidin-1-yl}acetyl)-L-proline A mixture of Example 1011A (0.04 g, 0.081 mmol) in 1,4-dioxane (0.3 ml), methanol (0.4 ml), and water (0.3 ml) was treated with aqueous 3 N sodium hydroxide (0.094 ml, 0.283 mmol) and the reaction was stirred at room temperature for 15 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (500 MHz, CD$_3$OD) δ 8.30 (d, J=5.8 Hz, 1H), 7.46 (d, J=5.8 Hz, 1H), 7.31-7.19 (m, 3H), 6.41 (bs, 1H), 4.63-4.47 (m, 1H), 4.32-4.20 (m, 2H), 3.99-3.70 (m, 5H), 3.68-3.46 (m, 3H), 3.31-3.18 (m, 2H), 2.48-1.94 (m, 8H). MS (ESI$^+$) m/z 481.2 (M+H)$^+$.

EXAMPLE 1012

1-({4-[4-(5-fluoro-2-methoxyphenyl)-1H-pyrrolo[2,3-b]pyridin-2-yl]-3,6-dihydropyridin-1(2H)-yl}acetyl)-L-proline

EXAMPLE 1012A (2S)-methyl 1-(2-(4-(4-(5-fluoro-2-methoxyphenyl)-1H pyrrolo[2,3-b]pyridin-2-yl)-5,6-dihydropyridin-1(2H)-yl)acetyl)pyrrolidine-2-carboxylate The title compound was prepared essentially as described in Example 238, substituting (S)-methyl pyrrolidine-2-carboxylate hydrochloride for azetidin-3-ol hydrochloride. MS (ESI$^+$) m/z 493.0 (M+H)$^+$.

EXAMPLE 1012B 1-({4-[4-(5-fluoro-2-methoxyphenyl)-1H-pyrrolo[2,3-b]pyridin-2-yl]-3,6-dihydropyridin-1(2H)-yl}acetyl)-L-proline The title compound was prepared essentially as described in Example 1011B, substituting Example 1012A for Example 1011A. $^1$H NMR (500 MHz, CD$_3$OD) δ ppm 1.93-2.15 (m, 3H), 2.23-2.43 (m, 1H), 2.95-3.05 (m, 2H), 3.44-3.75 (m, 4H), 3.80 (s, 3H), 4.02-4.20 (m, 2H), 4.27-4.42 (m, 2H), 4.53 (dd, J=8.6, 3.3 Hz, 1H), 6.41-6.52 (m, 1H), 6.58-6.66 (m, 1H), 7.16-7.31 (m, 3H), 7.34-7.45 (m, 1H), 8.31 (d, J=5.7 Hz, 1H). MS (ESI$^+$) m/z 479.0 (M+H)$^+$.

EXAMPLE 1013

2-{4-[4-(5-fluoro-2-methoxyphenyl)-1H-pyrrolo[2,3-b]pyridin-2-yl]piperidin-1-yl}-N-(methylsulfonyl)acetamide A solution of Example 247B (0.05 g, 0.110 mmol), methanesulfonamide (0.014 g, 0.142 mmol) and N-ethyl-N-isopropylpropan-2-amine (0.077 ml, 0.438 mmol) in N,N-dimethylformamide (1.370 ml) was treated with O-(7-azabenzotriazol-1-yl)-N,N'N'N'-tetramethyluronium hexafluorophosphate (0.044 g, 0.115 mmol) and the reaction mixture was stirred at room temperature for 16 hours. The reaction mixture was directly purified by reverse phase HPLC on a Phenomenex Luna C8(2) 5 um 100 Å AXIA column (30 mm×75 mm) eluting with a gradient of 10-95% acetonitrile in 0.1% ammonium acetate/water to afford the title compound. $^1$H NMR (500 MHz, DMSO-d$_6$) δ ppm 1.92-2.06 (m, 2H), 2.14-2.24 (m, 2H), 2.86 (s, 3H), 2.91-3.11 (m, 3H), 3.43-3.52 (m, 2H), 3.62 (s, 2H), 3.74 (s, 3H), 6.01 (d, J=1.9 Hz, 1H), 7.03 (d, J=4.9 Hz, 1H), 7.15-7.33 (m, 3H), 8.17 (d, J=4.9 Hz, 1H), 11.67 (d, J=2.3 Hz, 1H). MS (ESI$^+$) m/z 461.2 (M+H)$^+$.

EXAMPLE 1017

5-[4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide To a mixture of Example 845 (100 mg, 0.286 mmol) and triethylamine (0.080 mL, 0.572 mmol) in dimethylformamide (1.5 mL) at 0° C. was added dropwise a solution of isocyanatomethane (19.59 mg, 0.343 mmol) in dimethylformamide (0.5 mL). The mixture was stirred at 0° C. for 40 minutes. Water was added dropwise to the reaction mixture to form a precipitate. The solids were collected by filtration, washed with ether and dried at 50° C. in vacuo overnight to provide the title compound. $^1$H NMR (400 MHz, DMSO-d$_6$) δ ppm 2.53 (d, J=4.27 Hz, 3 H) 2.54-2.59 (m, 1 H) 2.83-3.00 (m, 3 H) 3.36-3.40 (m, 2 H) 3.45-3.55 (m, 2H) 3.73 (s, 3H) 6.03 (q, J=4.48 Hz, 1 H) 6.18 (d, J=1.83 Hz, 1 H) 6.31 (s, 1 H) 7.03 (d, J=4.88 Hz, 1 H) 7.15-7.32 (m, 3 H) 8.21 (d, J=4.88 Hz, 1 H) 11.89 (d, J=1.22 Hz, 1 H). MS (ESI$^+$) m/z 407 (M+H)$^+$.

EXAMPLE 1018

4-(5-fluoro-2-methoxyphenyl)-2-[4-(piperazin-1-yl)cyclohex-1-en-1-yl]-1H-pyrrolo[2,3-b]pyridine

EXAMPLE 1018A tert-butyl 4-(4-(4-(5-fluoro-2-methoxyphenyl)-1H-pyrrolo[2,3-b]pyridin-2-yl)cyclohex-3-enyl)piperazine-1-carboxylate To a mixture of Example 241B (300 mg, 0.892 mmol), triethylamine (0.273 ml, 1.962 mmol) and acetic acid (0.255 ml, 4.46 mmol) in dichloromethane (6 ml) was added tert-butyl piperazine-1-carboxylate (332 mg, 1.784 mmol) followed by the resin bound sodium cyanoborohydride (Biotage®, MP-cyanoborohydride, 2.17 mmol/g, 1.46 g, 3.57 mmol). The mixture was stirred at ambient temperature overnight. The resin was removed by filtration and the filtrate concentrated onto silica gel. Silica gel flash chromatography (Isco®, Redi-Sep® column, 0 to 10% of a 2:1 methanol:water solution in ethyl acetate) afforded the title compound. MS (ESI$^+$) m/z 507.1 (M+H)$^+$.

EXAMPLE 1018B 4-(5-fluoro-2-methoxyphenyl)-2-[4-(piperazin-1-yl)cyclohex-1-en-1-yl]-1H-pyrrolo[2,3-b]pyridine Example 1018A (0.226 g, 0.446 mmol) was dissolved in 2 mL of dichloromethane then hydrochloric acid (2 molar in diethylether, 5 mL) was added and the mixture was stirred at 40° C. for 2 hours. The precipitate that formed was stirred vigorously at 0° C. for 10 minutes and was filtered and washed with diethyl ether (10 mL) and heptane (10 mL) to provide the title compound as a bis hydrochloride acid salt. $^1$H NMR (400 MHz, DMSO-d$_6$) δ ppm 1.75-1.90 (m, 1H), 2.28-2.41 (m, 1H), 2.41-2.51 (m, 1H), 2.54-2.69 (m, 1H), 2.71-2.88 (m, 2H), 3.40-3.74 (m, 11H), 6.38-6.43 (m, 1H), 6.57-6.65 (m, 1H), 7.21-7.37 (m, 4H), 8.29 (d, J=5.5 Hz, 1H), 9.65-10.36 (m, 2H), 12.28 (s, 1H), 12.59 (s, 1H). MS (ESI$^+$) m/z 407.0 (M+H)$^+$.

EXAMPLE 1019

N$^2$-{4-[4-(5-fluoro-2-methoxyphenyl)-1H-pyrrolo[2,3-b]pyridin-2-yl]cyclohex-3-en-1-yl}-N,N-dimethyl-D-valinamide To a solution of Example 241C (125 mg, 0.264 mmol) in 3 mL dichloromethane was added dimethylamine hydrochloride (43.0 mg, 0.527 mmol), 1-(3-dimethylaminopropyl)-3-ethylcarbodiimide hydrochloride (76 mg, 0.396 mmol), 1H-benzo[d][1,2,3]triazol-1-ol hydrate (60.6 mg, 0.396 mmol) followed by N-ethyl-N-isopropylpropan-2-amine (0.230 mL, 1.319 mmol). The mixture was stirred at room temperature overnight, then diluted with 20 mL ethyl acetate. The organics were washed with saturated sodium bicarbonate, water and brine then dried over magnesium sulfate, filtered and concentrated. The crude material was purified by flash chromatography (Analogix280, 12 g silica column (0% to 4% methanol/dichloromethane gradient over 30 minutes). The resulting material was dissolved in methanol and treated with excess 2M HCl in ether, then diluted with 20 mL ether and the solid was filtered to give the titled compound. $^1$H NMR (400 MHz, DMSO-d$_6$) δ ppm 12.54 (s, 1 H) 8.46-9.58 (m, 2 H) 8.27 (d, J=5.49 Hz, 1 H) 7.01-7.48 (m, 4 H) 6.55 (s, 1 H) 6.36 (s, 1 H) 4.30-4.69 (m, 1 H) 3.76 (s, 3 H) 3.12 (s, 4 H) 2.94 (d, J=3.05 Hz, 3 H) 2.54-2.77 (m, 3 H) 2.36-2.54 (m, 1 H) 2.15-2.36 (m, 2 H) 1.70-2.02 (m, 1 H) 0.95-1.09 (m, 6 H). MS (ESI): 465.1 (M+H)$^+$.

EXAMPLE 1022

2-{4-[4-(2-methoxyphenyl)-1H-pyrrolo[2,3-b]pyridin-2-yl]piperidin-1-yl}-N-methylacetamide The title compound was prepared as described in Example 558, substituting Example 1023D for Example 219C and methylamine hydrochloride for phenylmethanamine. $^1$H NMR (500 MHz, DMSO-d$_6$) δ 1.75 (qd, J=12.3, 3.7 Hz, 2H), 1.88-2.01 (m, 2H), 2.18 (td, J=11.7, 2.4 Hz, 2H), 2.62 (d, J=4.7 Hz, 3H), 2.67 (tt, J=11.7, 3.8 Hz, 1H), 2.85 (dt, J=11.6, 3.2 Hz, 2H), 2.91 (s, 2H), 3.75 (s, 3H), 5.93 (d, J=2.1 Hz, 1H), 7.00 (d, J=4.9 Hz, 1H), 7.07 (td, J=7.4, 1.1 Hz, 1H), 7.18 (dd, J=8.5, 1.0 Hz, 1H), 7.37 (dd, J=7.4, 1.7 Hz, 1H), 7.39-7.47 (m, 1H), 7.66 (q, J=5.0, 4.6 Hz, 1H), 8.12 (d, J=4.9 Hz, 1H), 11.51 (br s, 1H); MS (ESI$^+$) m/z 379 (M+H)$^+$.

EXAMPLE 1023

{4-[4-(2-methoxyphenyl)-1H-pyrrolo[2,3-b]pyridin-2-yl]piperidin-1-yl}acetic acid

EXAMPLE 1023A 4-(2-methoxyphenyl)-2-(1,2,3,6-tetrahydropyridin-4-yl)-1H-pyrrolo[2,3-b]pyridine The title compound was prepared as described in Example 87, substituting 2-methoxyphenylboronic acid for 5-fluoro-2-methoxyphenylboronic acid in Example 87A. MS (ESI$^+$) m/z 306 (M+H)$^+$.

EXAMPLE 1023B tert-butyl 2-(4-(4-(2-methoxyphenyl)-1H-pyrrolo[2,3-b]pyridin-2-yl)-5,6-dihydropyridin-1(2H)-yl)acetate The title compound was prepared as described in Example 226A, substituting Example 1023A for Example 87D. MS (ESI$^+$) m/z 420 (M+H)$^+$.

EXAMPLE 1023C tert-butyl 2-(4-(4-(2-methoxyphenyl)-1H-pyrrolo[2,3-b]pyridin-2-yl)piperidin-1-yl)acetate The title compound was prepared as described in Example 275, substituting Example 1023B for Example 236G. MS (ESI$^+$) m/z 422 (M+H)$^+$.

EXAMPLE 1023D

{4-[4-(2-methoxyphenyl)-1H-pyrrolo[2,3-b]pyridin-2-yl]piperidin-1-yl}acetic acid The title compound was prepared as described in Example 226B, substituting Example 1023C for Example 226A. $^1$H NMR (400 MHz, DMSO-d$_6$) δ 2.09 (m, 2H), 2.24-2.40 (m, 2H), 3.29 (m, 2H), 3.65 (m, 1H), 3.81 (s, 2H), 6.27 (br s, 1H), 7.16 (td, J=7.5, 1.0 Hz, 1H), 7.28 (d, J=8.4 Hz, 1H), 7.46 (dd, J=11.5, 5.9 Hz, 2H), 7.55 (ddd, J=8.7, 7.4, 1.7 Hz, 1H), 8.36 (d, J=5.9 Hz, 1H), 10.42 (br s, 1H), 13.12 (br s, 1H); MS (ESI+) m/z 366 (M+H)+.

EXAMPLE 1024

2-[(6S)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide The title compound was prepared using the procedure described in Example 258G using 2-chloro-N,N-dimethylacetamide in place of methanesulfonyl chloride. $^1$HNMR (500 MHz, DMSO-d$_6$) δ 1.165 (d, 3H), 2.40 (m, 2H), 2.57 (m, 1H), 2.82 (s, 3H), 2.90 (m, 1H), 3.05 (s, 3H), 3.10 (br d, 1H), 3.31 (m, 1H), 3.57 (br d, 1H), 3.74 (s, 3H), 6.21 (s, 1H), 6.38 (m, 1H), 7.02 (d, 1H), 7.23 (m, 3H), 8.18 (d, 1H), 11.75 (br s, 1H). MS (ESI) m/e 423.0 (M+H)+.

EXAMPLE 1025

4-(5-fluoro-2-methoxyphenyl)-2-[(6R)-6-methyl-1,2,3,6-tetrahydropyridin-4-yl]-1H-pyrrolo[2,3-b]pyridine

EXAMPLE 1025A (R)-tert-butyl 2-methyl-4-(((trifluoromethyl)sulfonyl)oxy)-5,6-dihydropyridine-1(2H)-carboxylate and (R)-tert-butyl 6-methyl-4-(((trifluoromethyl)sulfonyl)oxy)-5,6-dihydropyridine-1(2H)-carboxylate The title compound was prepared using the procedure described in Example 258A using (R)-tert-butyl 2-methyl-4-oxopiperidine-1-carboxylate in place of (S)-tert-butyl-2-methyl-4-oxopiperidine-1-carboxylate. MS (ESI) m/e 246.0 (M–BOC)+.

EXAMPLE 1025B (R)-tert-butyl 4-(4-(5-fluoro-2-methoxyphenyl)-1-tosyl-1H-pyrrolo[2,3-b]pyridin-2-yl)-2-methyl-5,6-dihydropyridine-1(2H)-carboxylate and (R)-tert-butyl 4-(4-(5-fluoro-2-methoxyphenyl)-1-tosyl-1H-pyrrolo[2,3-b]pyridin-2-yl)-6-methyl-5,6-dihydropyridine-1(2H)-carboxylate (1:1)

The title compound was prepared using the procedure described in Example 258D using Example 1025A in place of Example 258A. MS (ESI) m/e 592.0 (M+H)+.

EXAMPLE 1025C (R)-tert-butyl 4-(4-(5-fluoro-2-methoxyphenyl)-1H-pyrrolo[2,3-b]pyridin-2-yl)-2-methyl-5,6-dihydropyridine-1(2H)-carboxylate and (R)-tert-butyl 4-(4-(5-fluoro-2-methoxyphenyl)-1H-pyrrolo[2,3-b]pyridin-2-yl)-6-methyl-5,6-dihydropyridine-1(2H)-carboxylate (1:1)

The title compound was prepared as described in Example 258E using Example 1025B in place of Example 258D. MS (ESI) m/e 438.1 (M+H)+.

EXAMPLE 1025D 4-(5-fluoro-2-methoxyphenyl)-2-[(6R)-6-methyl-1,2,3,6-tetrahydropyridin-4-yl]-1H-pyrrolo[2,3-b]pyridine The title compound was prepared as described in Example 258F using Example 1025C in place of Example 258E. $^1$HNMR (400 MHz, DMSO-d$_6$) δ 1.41 (d, 3H), 2.72 (m, 2H), 3.19 (m, 1H), 3.43 (m, 1H), 3.76 (s, 3H), 4.11 (m, 1H), 6.49 (s, 1H), 6.55 (br s, 1H), 7.32 (m, 4H), 8.30 (d, 1H), 12.55 (br s, 1H). MS (ESI) m/e 338.1 (M+H)+.

EXAMPLE 1026

4-(5-fluoro-2-methoxyphenyl)-2-[(2S)-2-methyl-1-(methylsulfonyl)piperidin-4-yl]-1H-pyrrolo[2,3-b]pyridine

EXAMPLE 1026A (2S)-tert-butyl 4-(4-(5-fluoro-2-methoxyphenyl)-1H-pyrrolo[2,3-b]pyridin-2-yl)-2-methylpiperidine-1-carboxylate The title compound was prepared using the procedure described in Example 275, using Example 258E (0.6 g, 1.37 mmol) in place of Example 236G. MS (ESI+) m/z: 438.3 (M–H)+.

EXAMPLE 1026B 4-(5-fluoro-2-methoxyphenyl)-2-((2S)-2-methylpiperidin-4-yl)-1H-pyrrolo[2,3-b]pyridine The title compound was prepared using the procedure described in Example 1H, using Example 1026A (0.22 g, 0.5 mmol) in place of Example 1G. LCMS: 339.6 (M+H)+.

EXAMPLE 1026C 4-(5-fluoro-2-methoxyphenyl)-2-[(2S)-2-methyl-1-(methylsulfonyl)piperidin-4-yl]-1H-pyrrolo[2,3-b]pyridine The title compound was prepared using the procedure described in Example 223D, using Example 1026B in place of Example 223C. $^1$H NMR (400 MHz, DMSO-d$_6$): δ 1.22-1.33 (m, 4 H) 1.59-2.17 (m, 4 H) 2.91-3.24 (m, 5 H) 3.75 (s, 3 H) 4.16-4.26 (m, 1 H) 6.12-6.19 (m, 1 H) 7.17-7.35 (m, 4 H) 8.24 (d, J=5.49 Hz, 1 H) 12.15 (s, 1 H). MS (ESI+) m/z: 418.2 (M+H)+.

EXAMPLE 1027

({4-[4-(5-fluoro-2-methoxyphenyl)-1H-pyrrolo[2,3-b]pyridin-2-yl]cyclohex-3-en-1-yl}oxy)acetic acid

EXAMPLE 1027A tert-butyl 2-(4-(4-(5-fluoro-2-methoxyphenyl)-1-(phenylsulfonyl)-1H-pyrrolo[2,3-b]pyridin-2-yl)cyclohex-3-enyloxy)acetate To a stirred solution of Example 995C (0.214 g, 0.447 mmol) and tert-butyl 2-bromoacetate (0.104 g, 0.533 mmol) in toluene (2 mL) at 0° C. was added tetrabutylammonium bromide (0.1 g, 0.31 mmol) and 12M aqueous sodium hydroxide (1 ml, 12 mmol). The reaction mixture was stirred at room temperature for 72 hours. After ethyl acetate was added, the mixture was washed with water, and brine. The organic layer was dried over sodium sulfate. After filtration and concentration, the residue was purified by flash chromatography on silica gel (AnaLogix IntelliFlash) eluting with a gradient of 0-50% ethyl acetate in heptanes to afford the title compound. MS (ESI+) m/z 593.1 (M+H)$^+$.

EXAMPLE 1027B ({4-[4-(5-fluoro-2-methoxyphenyl)-1H-pyrrolo[2,3-b]pyridin-2-yl]cyclohex-3-en-1-yl}oxy)acetic acid To a stirred solution of Example 1027A (0.14 g, 0.24 mmol) in methanol (2 mL) was added 1M sodium hydroxide (2 ml, 2 mmol). The mixture was heated at 80° C. under microwave (Biotage Initiator, model 355302) for 30 minutes. After cooling to room temperature, the mixture was neutralized by trifluoroacetic acid and treated with water. The solids were filtered, washed with water, and vacuum-dried to afford the title compound. $^1$H NMR (500 MHz, DMSO-$d_6$): δ 1.56-1.65 (m, 1 H) 1.91-1.99 (m, 1 H) 2.11-2.20 (m, 1 H) 2.28-2.38 (m, 1 H) 2.52-2.56 (m, 1 H) 3.60 (s, 2 H) 3.67-3.72 (m, 1 H) 3.74 (s, 3 H) 6.16 (d, J=1.83 Hz, 1 H) 6.40-6.44 (m, 1 H) 7.00 (d, J=4.88 Hz, 1 H) 7.16-7.29 (m, 3 H) 8.17 (d, J=4.88 Hz, 1 H) 11.72 (s, 1 H). MS (ESI+) m/z: 397.2 (M+H)$^+$.

EXAMPLE 1029

2-{1-[(1,1-dioxidothiomorpholin-4-yl)sulfonyl]-1,2,3,6-tetrahydropyridin-4-yl}-4-(5-fluoro-2-methoxyphenyl)-1H-pyrrolo[2,3-b]pyridine The title compound was prepared using the procedure described in Example 794, using thiomorpholine-4-sulfonyl chloride 1,1-dioxide in place of 2-(1,3-dioxoisoindolin-2-yl)ethanesulfonyl chloride. $^1$H NMR (500 MHz, DMSO-$d_6$) δ 11.89 (s, 1H), 8.22 (d, J=4.9 Hz, 1H), 7.33-7.15 (m, 3H), 7.05 (d, J=4.9 Hz, 1H), 6.52 (m, 1H), 6.27 (d, J=2.1 Hz, 1H), 3.95 (s, 2H), 3.74 (s, 3H), 3.71-3.64 (m, 4H), 3.43 (t, J=5.7 Hz, 2H), 3.28-3.19 (m, 4H), 2.59 (m, 2H). MS (ESI+) m/e 521 (M+H)$^+$.

EXAMPLE 1030

4-(5-fluoro-2-methoxyphenyl)-2-{1-[(4-methylpiperazin-1-yl)sulfonyl]-1,2,3,6-tetrahydropyridin-4-yl}-1H-pyrrolo[2,3-b]pyridine The title compound was prepared using the procedure described in Example 794, using 4-methylpiperazine-1-sulfonyl chloride in place of 2-(1,3-dioxoisoindolin-2-yl)ethanesulfonyl chloride. $^1$H NMR (400 MHz, DMSO-$d_6$) δ 11.86 (s, 1H), 8.21 (d, J=4.9 Hz, 1H), 7.34-7.14 (m, 3H), 7.04 (d, J=5.0 Hz, 1H), 6.56-6.47 (m, 1H), 6.27 (d, J=2.1 Hz, 1H), 3.93 (m, 2H), 3.74 (s, 3H), 3.41 (t, J=4.9 Hz, 2H), 3.15 (t, J=4.9 Hz, 4H), 2.58-2.53 (m, 2H), 2.34 (t, J=4.8 Hz, 4H), 2.17 (s, 3H). MS (ESI+) m/e 486 (M+H)$^+$.

EXAMPLE 1031 ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-4-carboxylate The title compound was prepared using the procedure described in Example 794, using ethyl 1-(chlorosulfonyl)piperidine-4-carboxylate in place of 2-(1,3-dioxoisoindolin-2-yl)ethanesulfonyl chloride. $^1$H NMR (400 MHz, DMSO-$d_6$) δ 11.86 (s, 1H), 8.21 (d, J=5.0 Hz, 1H), 7.34-7.09 (m, 3H), 7.04 (d, J=5.0 Hz, 1H), 6.51 (m, 1H), 6.26 (d, J=2.1 Hz, 1H), 4.06 (q, J=7.1 Hz, 2H), 3.91 (q, J=2.8 Hz, 2H), 3.74 (s, 3H), 3.52 (m 2H), 3.42-3.35 (m, 2H), 2.97-2.83 (m, 2H), 2.58-2.54 (m, 2H), 2.52-2.44 (m, 1H), 1.94-1.82 (m, 2H), 1.64-1.46 (m, 2H), 1.16 (t, J=7.1 Hz, 3H). MS (ESI+) m/e 543 (M+H)$^+$.

EXAMPLE 1032 ethyl 1-({4-[4-(5-fluoro-2-methoxyphenyl)-1H-pyrrolo[2,3-b]pyridin-2-yl]-3,6-dihydropyridin-1(2H)-yl}sulfonyl)prolinate The title compound was prepared using the procedure described in Example 794, using ethyl 1-(chlorosulfonyl)pyrrolidine-2-carboxylate in place of 2-(1,3-dioxoisoindolin-2-yl)ethanesulfonyl chloride. $^1$H NMR (500 MHz, DMSO-$d_6$) δ 11.87 (s, 1H), 8.21 (d, J=4.9 Hz, 1H), 7.33-7.16 (m, 3H), 7.04 (d, J=4.9 Hz, 1H), 6.56-6.49 (m, 1H), 6.27 (s, 1H), 4.25 (dd, J=8.7, 3.4 Hz, 1H), 4.10 (q, J=7.1 Hz, 2H), 3.92 (m, 2H), 3.74 (s, 3H), 3.54-3.39 (m, 2H), 2.60-2.54 (m, 2H), 2.33-2.18 (m, 2H), 1.90 (m, 4H), 1.18 (t, J=7.1 Hz, 3H). MS (ESI+) m/e 529 (M+H)$^+$.

EXAMPLE 1033 ethyl {4-[4-(5-fluoro-2-methoxyphenyl)-1H-pyrrolo[2,3-b]pyridin-2-yl]-3,6-dihydropyridin-1(2H)-yl}acetate A mixture of Example 87D (0.075 g, 0.189 mmol) and triethylamine (0.119 ml, 0.852 mmol) in N,N-dimethylformamide (1.721 ml) was treated with ethyl 2-bromoacetate (0.024 ml, 0.218 mmol) and the reaction was stirred at ambient temperature for 8 hours. The reaction mixture was poured into 50 mL water and the resulting suspension was filtered. The solid collected was purified by flash chromatography on silica gel (AnaLogix IntelliFlash 280 system) eluting with a gradient of from 0% to 5% methanol in dichloromethane to afford the title compound. $^1$H NMR (500 MHz, CD$_3$OD) δ ppm 1.28 (t, J=7.1 Hz, 3H), 2.57-2.65 (m, 2H), 2.86 (t, J=5.8 Hz, 2H), 3.34-3.43 (m, 4H), 3.76 (s, 3H), 4.19 (q, J=7.1 Hz, 2H), 6.27 (s, 1H), 6.33-6.41 (m, 1H), 7.07 (d, J=5.1 Hz, 1H), 7.12-7.20 (m, 3H), 8.15 (d, J=5.1 Hz, 1H). MS (ESI$^+$) m/z 410.1 (M+H)$^+$.

EXAMPLE 1034 propan-2-yl {4-[4-(5-fluoro-2-methoxyphenyl)-1H-pyrrolo[2,3-b]pyridin-2-yl]-3,6-dihydropyridin-1(2H)-yl}acetate The title compound was prepared essentially as described in Example 1033 substituting isopropyl 2-bromoacetate for ethyl 2-bromoacetate. $^1$H NMR (500 MHz, CD$_3$OD) δ ppm 1.26 (d, J=6.3 Hz, 6H), 2.57-2.64 (m, 2H), 2.85 (t, J=5.8 Hz, 2H), 3.32-3.40 (m, 4H), 3.76 (s, 3H), 5.06 (hept, J=6.3 Hz, 1H), 6.26 (s, 1H), 6.33-6.41 (m, 1H), 7.07 (d, J=5.1 Hz, 1H), 7.11-7.18 (m, 3H), 8.15 (d, J=5.1 Hz, 1H). MS (ESI$^+$) m/z 424.1 (M+H)$^+$.

EXAMPLE 1035

{4-[3-cyano-4-(5-fluoro-2-methoxyphenyl)-1H-pyrrolo[2,3-b]pyridin-2-yl]-3,6-dihydropyridin-1(2H)-yl}acetic acid

EXAMPLE 1035A 4-chloro-1-((2-(trimethylsilyl)ethoxy)methyl)-1H-pyrrolo[2,3-b]pyridine-3-carbonitrile A solution of 4-chloro-1H-pyrrolo[2,3-b]pyridine-3-carbonitrile (2.5 g, 14.08 mmol) in tetrahydrofuran (20 ml) was cooled to 0 C and NaH (0.507 g, 21.12 mmol) was added. The mixture was stirred at 0 C for 30 minutes then (2-(chloromethoxy)ethyl)trimethylsilane (2.82 g, 16.89 mmol) was added. The mixture was warmed to room temperature, stirred for 2 hours and partitioned between ethyl acetate and brine. The organic phase was concentrated and the residue was separated by flash chromatography (1:3 ethyl acetate/hexane) to provide the title compound. MS (DCI/NH$_3$) m/z 307 (M+H)$^+$.

EXAMPLE 1035B 4-(5-fluoro-2-methoxyphenyl)-1-((2-(trimethylsilyl)ethoxy)methyl)-1H-pyrrolo[2,3-b]pyridine-3-carbonitrile A mixture of Example 1035A (3 g, 9.78 mmol), (5-fluoro-2-methoxyphenyl)boronic acid (2.49 g, 14.66 mmol), phenylallylchloro(1,3-bis(diisopropylphenyl)-2-imidazol-2-yliden)palladium(II) (0.19 g, 0.293 mmol), and potassium phosphate (6.23 g, 29.3 mmol) was suspended in a mixture of tetrahydrofuran (60 mL) and water (18 mL). The suspension was purged with N$_2$ and heated at 60 C for 3 hours. The reaction mixture was then partitioned between ethyl acetate and brine. The organic phase was concentrated and the residue was purified by flash chromatography (1:5 ethyl acetate/hexane) to provide the title compound. MS (DCI/NH$_3$) m/z 397 (M+H)$^+$.

EXAMPLE 1035C 4-(5-fluoro-2-methoxyphenyl)-2-iodo-1-((2-(trimethylsilyl)ethoxy)methyl)-1H-pyrrolo[2,3-b]pyridine-3-carbonitrile To a cold (−78° C.) solution of Example 1035B (2.29 g, 5.76 mmol) in tetrahydrofuran (50 mL) was added lithium diisopropylamide (2 M solution in tetrahydrofuran, 5.76 mL, 11.52 mmol). The reaction mixture was stirred at −78° C. for 1 hour, after which a solution of iodine (2.92 g, 11.52 mmol) in tetrahydrofuran (8 mL) was added. The reaction mixture was stirred at the same temperature for 1 hour, and the reaction was quenched by adding 1M aqueous solution of Na$_2$S$_2$O$_3$. Ethyl acetate was then added and the mixture was partitioned between ethyl acetate and brine. The organic phase was concentrated, and the residue was separated by flash chromatography (10-60% ethyl acetate in hexane) to provide the title compound. MS (DCI/NH$_3$) m/z 524 (M+H)$^+$.

EXAMPLE 1035D tert-butyl 4-(3-cyano-4-(5-fluoro-2-methoxyphenyl)-1-((2-(trimethylsilyl)ethoxy)methyl)-1H-pyrrolo[2,3-b]pyridin-2-yl)-5,6-dihydropyridine-1(2H)-carboxylate A mixture of Example 1035C (1.53 g, 2.92 mmol), tert-butyl 4-(4,4,5,5-tetramethyl-1,3,2-dioxaborolan-2-yl)-5,6-dihydropyridine-1(2H)-carboxylate (1.085 g, 3.51 mmol), and dichlorobis(triphenylphosphine)palladium (II) (205 mg, 0.292 mmol) was suspended in a mixture of 7:3:2 dimethoxyethane/water/ethanol (80 mL). Aqueous Na$_2$CO$_3$ (5.12 mL of 2M solution) was then added. The suspension was purged with nitrogen and heated at 80° C. overnight. After cooling, the mixture was partitioned between ethyl acetate and brine. The organic phase was washed with brine, and concentrated. The residue was separated by flash chromatography (10-60% ethyl acetate in hexane) to provide the title compound. MS (DCI/NH$_3$) m/z 579 (M+H)$^+$.

EXAMPLE 1035E 4-(5-fluoro-2-methoxyphenyl)-2-(1,2,3,6-tetrahydropyridin-4-yl)-1H-pyrrolo[2,3-b]pyridine-3-carbonitrile To a solution of Example 1035D (1.22 g, 2.108 mmol) in tetrahydrofuran (50 mL) was added HCl (37% aqueous solution, 7 mL) and the solution was stirred at 60° C. for 4 hours. The mixture was concentrated and the residue was dissolved in methanol (5 mL). The solid was collected by filtration, washed with methanol and dried with magnesium sulfate to provide the title compound. MS (DCI/NH$_3$) m/z 348 (M+H)$^+$.

EXAMPLE 1035F tert-butyl 2-(4-(3-cyano-4-(5-fluoro-2-methoxyphenyl)-1H-pyrrolo[2,3-b]pyridin-2-yl)-5,6-dihydropyridin-1(2H)-yl)acetate To a suspension of Example 1035E (165 mg, 0.474 mmol) in anhydrous N,N-dimethylformamide (5 mL) was added triethylamine (0.396 mL, 2.84 mmol) and tert-butyl bromoacetate (120 mg, 0.616 mmol). The solution was stirred at room temperature overnight. The reaction mixture was partitioned between ethyl acetate and brine. The organic phase was washed with brine and concentrated. The residue was separated by flash chromatography (0-15% CH$_3$OH in 2:1 ethyl acetate/hexane) to provide the title compound. MS (DCI/NH$_3$) m/z 463 (M+H)$^+$.

EXAMPLE 1035G

{4-[3-cyano-4-(5-fluoro-2-methoxyphenyl)-1H-pyrrolo[2,3-b]pyridin-2-yl]-3,6-dihydropyridin-1(2H)-yl}acetic acid To a solution of Example 1035F (0.12 g, 0.259 mmol) in methylene chloride (3 mL) was added trifluoroacetic acid (6 mL), and the solution was stirred at room temperature for 5 hours. The volatiles were removed and the residue was separated by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as trifluoroacetic acid salt. The material was dissolved in a mixture of methylene chloride and methanol, and treated with HCl in ether. Concentration of the mixture provided the title compound as HCl salt. $^1$H NMR (400 MHz, CD$_3$OD): δ3.14-3.22 (m, 2 H), 3.54-3.69 (m, 2 H), 3.79 (s, 3 H), 4.14-4.34 (m, 4 H), 6.75 (s, 1 H), 7.11-7.18 (m, 2 H), 7.25-7.30 (m, 1 H), 7.41 (d, J=5.49 Hz, 1 H), 8.52 (d, J=5.49 Hz, 1 H); MS (DCI/NH$_3$) m/z 480 (M+H)$^+$.

EXAMPLE 1036

4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile To a solution of Example 1035G (84 mg, 0.175 mmol) and L-prolinol (36 mg, 0.35 mmol) in N,N-dimethylformamide (6 mL) was added triethylamine (0.147 mL, 1.051 mmol), hydroxybenzotriazole (54 mg, 0.35 mmol), and 1-(3-dimethylaminopropyl)-3-ethylcarbodiimide hydrochloride (67 mg, 0.35 mmol). The solution was stirred at room temperature overnight and was partitioned between ethyl acetate and sodium hydroxide solution. The organic phase was washed with sodium hydroxide solution and brine. The combined aqueous phases were extracted with ethyl acetate and the solution was washed with brine. The combined organic phases were concentrated and the residue was separated by flash chromatography (10-20% CH$_3$OH in 2:1 ethyl acetate/hexane) to provide the title compound. $^1$H NMR (400 MHz, CD$_3$OD): δ1.86-2.05 (m, 4 H), 2.77-2.81 (m, 2 H), 2.87-2.90 (m, 2 H), 3.35-3.41 (m, 4 H), 3.49-3.67 (m, 4 H), 3.77 (s, 3 H), 4.11-4.14 (m, 1 H), 6.67 (t, J=3.51 Hz, 1 H), 7.04-7.12 (m, 3 H), 7.16-7.20 (m, 1 H), 8.34 (d, J=4.88 Hz, 1 H); MS (DCI/NH$_3$) m/z 490 (M+H)$^+$.

EXAMPLE 1037

4-(2-ethoxy-4,5-difluorophenyl)-2-(1,2,3,6-tetrahydropyridin-4-yl)-1H-pyrrolo[2,3-b]pyridine The title compound was prepared as described in Example 87, substituting 2-ethoxyphenylboronic acid for 5-fluoro-2-methoxyphenylboronic acid in Example 87A. $^1$H NMR (500 MHz, DMSO-d$_6$) δ 1.18 (t, J=6.9 Hz, 3H), 2.71-2.78 (m, 2H), 3.29 (dt, J=7.2, 4.2 Hz, 2H), 3.78-3.85 (m, 2H), 4.10 (q, J=6.9 Hz, 2H), 6.57 (apparent s, 1H), 6.63-6.69 (m, 1H), 7.30 (d, J=5.5 Hz, 1H), 7.40 (dd, J=12.9, 6.8 Hz, 1H), 7.51-7.62 (m, 1H), 8.32 (d, J=5.5 Hz, 1H), 9.55 (br s, 2H), 12.83 (br s, 1H); MS (ESI$^+$) m/z 354 (M+H)$^+$.

EXAMPLE 1038

2-hydroxy-2-methylpropyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965, substituting 2-methylpropane-1,2-diol for tert-butyl(2-hydroxyethyl)(methyl)carbamate. $^1$H NMR (400 MHz, dimethylsulfoxide-d$_6$) δ 11.95-11.75 (m, 1H), 11.40 (s, 1H), 8.21 (d, J=4.9 Hz, 1H), 7.34-7.15 (m, 3H), 7.04 (d, J=4.9 Hz, 1H), 6.57-6.46 (m, 1H), 6.26 (d, J=2.1 Hz, 1H), 4.09-3.96 (m, 2H), 3.78 (d, J=35.4 Hz, 2H), 3.48 (t, J=5.6 Hz, 2H), 2.67-2.55 (m, 2H), 1.07 (s, 6H). MS (ESI$^+$) m/z 519.1 (M+H)$^+$.

EXAMPLE 1039

(2,2-dimethyl-1,3-dioxolan-4-yl)methyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965, substituting (2,2-dimethyl-1,3-dioxolan-4-yl)methanol for tert-butyl(2-hydroxyethyl)(methyl)carbamate. $^1$H NMR (400 MHz, dimethylsulfoxide-d$_6$) δ 11.96-11.76 (m, 1H), 11.52 (s, 1H), 8.21 (d, J=4.9 Hz, 1H), 7.34-7.17 (m, 3H), 7.04 (d, J=4.9 Hz, 1H), 6.57-6.45 (m, 1H), 6.26 (d, J=2.0 Hz, 1H), 4.25-4.11 (m, 2H), 4.09-3.88 (m, 4H), 3.74 (s, 3H), 3.62 (dd, J=8.4, 6.0 Hz, 1H), 3.48 (t, J=5.8 Hz, 2H), 2.67-2.54 (m, 2H), 1.29 (s, 3H), 1.20 (s, 3H). MS (ESI$^+$) m/z 561.1 (M+H)$^+$.

EXAMPLE 1040 tetrahydro-2H-pyran-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965, using (tetrahydro-2H-pyran-4-yl)methanol for tert-butyl(2-hydroxyethyl)(methyl)carbamate. $^1$H NMR (400 MHz, dimethylsulfoxide-d$_6$) δ 11.99-11.76 (m, 1H), 11.39 (s, 1H), 8.21 (d, J=5.0 Hz, 1H), 7.33-7.15 (m, 3H), 7.04 (d, J=5.0 Hz, 1H), 6.55-6.47 (m, 1H), 6.26 (d, J=2.0 Hz, 1H), 4.11-4.00 (m, 2H), 3.88 (d, J=6.5 Hz, 2H), 3.78-3.64 (m, 5H), 3.49 (t, J=5.8 Hz, 2H), 3.14 (td, J=11.7, 2.1 Hz, 2H), 2.64-2.55 (m, 2H), 1.82-1.67 (m, 1H), 1.51-1.38 (m, 2H), 1.25-1.07 (m, 2H). MS (ESI$^+$) m/z 545.0 (M+H)$^+$.

EXAMPLE 1041

4-(2-ethoxy-4,5-difluorophenyl)-2-[1-(methylsulfonyl)-1,2,3,6-tetrahydropyridin-4-yl]-1H-pyrrolo[2,3-b]pyridine The title compound was prepared as described in Example 119, substituting Example 1037 for Example 87D. $^1$H NMR (400 MHz, DMSO-d$_6$) δ 1.17 (t, J=7.0 Hz, 3H), 2.57-2.70 (m, 2H), 2.94 (s, 3H), 3.91 (q, J=2.7 Hz, 2H), 4.06 (q, J=6.9 Hz, 2H), 6.33 (d, J=2.0 Hz, 1H), 6.50-6.58 (m, 1H), 7.05 (d, J=5.0 Hz, 1H), 7.33 (dd, J=13.0, 7.0 Hz, 1H), 7.47 (dd, J=11.1, 9.2 Hz, 1H), 8.21 (d, J=5.0 Hz, 1H), 11.86 (s, 1H); MS (ESI$^+$) m/z 434 (M+H)$^+$.

EXAMPLE 1042

4-[4-(2-ethoxy-4,5-difluorophenyl)-1H-pyrrolo[2,3-b]pyridin-2-yl]-N-methyl-3,6-dihydropyridine-1(2H)-carboxamide The title compound was prepared as described in Example 215, substituting Example 1037 for Example 87D. $^1$H NMR (400 MHz, DMSO-d$_6$) δ 1.17 (t, J=6.9 Hz, 3H), 2.45 (q, J=4.2 Hz, 2H), 2.60 (d, J=4.2 Hz, 3H), 3.50 (t, J=5.6 Hz, 2H), 4.00 (q, J=2.6 Hz, 2H), 4.06 (q, J=6.9 Hz, 2H), 6.29 (d, J=2.0 Hz, 1H), 6.45 (q, J=4.3 Hz, 1H), 6.48-6.55 (m, 1H), 7.04 (d, J=5.0 Hz, 1H), 7.32 (dd, J=12.9, 6.9 Hz, 1H), 7.47 (dd, J=11.1, 9.3 Hz, 1H), 8.19 (d, J=4.9 Hz, 1H), 11.79 (d, J=2.4 Hz, 1H); MS (ESI$^+$) m/z 413 (M+H)$^+$.

EXAMPLE 1043

2-{4-[5-fluoro-4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone The title compound was prepared using the procedure described in Example 238, substituting Example 259B for Example 226B and (S)-pyrrolidin-2-ylmethanol for azetidin-3-ol hydrochloride. $^1$H NMR (400 MHz, DMSO-d$_6$) δ

1.54-1.98 (m, 8H), 2.19 (p, J=10.8, 9.7 Hz, 2H), 2.66 (ddt, J=11.7, 6.9, 3.6 Hz, 1H), 2.80-3.31 (m, 6H), 3.40-3.66 (m, 2H), 3.72 (s, 3H), 3.93 (tt, J=9.1, 4.6 Hz, 1H), 4.73 (t, J=5.6 Hz, 1H), 5.89 (t, J=2.3 Hz, 1H), 7.01-7.49 (m, 3H), 8.12 (d, J=2.6 Hz, 1H), 11.70 (d, J=2.4 Hz, 1H); MS (ESI$^+$) m/z 485 (M+H)$^+$.

EXAMPLE 1044

{(2S)-4-[4-(5-fluoro-2-methoxyphenyl)-1H-pyrrolo[2,3-b]pyridin-2-yl]-1,2,3,6-tetrahydropyridin-2-yl}methanol The title compound was prepared as described in Example 260H. $^1$H NMR (500 MHz, DMSO) δ 12.27 (s, 1H), 9.35-9.27 (m, 1H), 9.10-9.00 (m, 1H), 8.27 (d, J=5.1 Hz, 1H), 7.37-7.18 (m, 3H), 7.14 (d, J=5.1 Hz, 1H), 6.55 (s, 1H), 6.39 (d, J=1.7 Hz, 1H), 3.93-3.76 (m, 3H), 3.74 (s, 3H), 3.62 (dd, J=11.7, 6.3 Hz, 1H), 2.76 (d, J=15.6 Hz, 1H), 2.61-2.52 (m, 1H); MS (ESI+) m/z 354.0 (M+H)$^+$.

EXAMPLE 1045

{(2S)-4-[4-(5-fluoro-2-methoxyphenyl)-1H-pyrrolo[2,3-b]pyridin-2-yl]-1,2,5,6-tetrahydropyridin-2-yl}methanol

EXAMPLE 1045A (S)-tert-butyl 4-(4-(5-fluoro-2-methoxyphenyl)-1H-pyrrolo[2,3-b]pyridin-2-yl)-2-(hydroxymethyl)-5,6-dihydropyridine-1(2H)-carboxylate The title compound was prepared as described in Example 260G, substituting Example 260F for 260E. MS (ESI+) m/z 454 (M+H)$^+$.

EXAMPLE 1045B

{(2S)-4-[4-(5-fluoro-2-methoxyphenyl)-1H-pyrrolo[2,3-b]pyridin-2-yl]-1,2,5,6-tetrahydropyridin-2-yl}methanol The title compound was prepared using the procedure described for Example 1H, substituting Example 1045A for Example 1G. $^1$H NMR (500 MHz, DMSO-d$_6$) δ 12.70 (s, 1H), 9.80 (s, 1H), 9.07 (dd, J=17.3, 8.5 Hz, 1H), 8.33 (d, J=5.4 Hz, 1H), 7.41-7.18 (m, 4H), 6.59 (s, 1H), 6.53 (d, J=1.3 Hz, 1H), 4.03 (br s, 1H), 3.81-3.76 (m, 1H), 3.76 (s, 3H), 3.70 (dd, J=11.6, 7.1 Hz, 1H), 3.42 (dd, J =11.2, 4.9 Hz, 1H), 3.25-3.18 (m, 1H), 2.82-2.70 (m, 2H); MS (ESI+) m/z 354.1 (M+H)$^+$.

EXAMPLE 1046

2-{4-[4-(4,5-difluoro-2-methoxyphenyl)-1H-pyrrolo[2,3-b]pyridin-2-yl]piperidin-1-yl}-N-methylacetamide

EXAMPLE 1046A 4-(4,5-difluoro-2-methoxyphenyl)-2-(1,2,3,6-tetrahydropyridin-4-yl)-1H-pyrrolo[2,3-b]pyridine The title compound was prepared as described in Example 87, substituting 4,5-difluoro-2-methoxyphenylboronic acid for 5-fluoro-2-methoxyphenylboronic acid in Example 87A. MS (ESI$^+$) m/z 342 (M+H)$^+$.

EXAMPLE 1046B tert-butyl 2-(4-(4-(4,5-difluoro-2-methoxyphenyl)-1H-pyrrolo[2,3-b]pyridin-2-yl)-5,6-dihydropyridin-1(2H)-yl)acetate The title compound was prepared as described in Example 226A, substituting Example 1046A for Example 87D. MS (ESI$^+$) m/z 456 (M+H)$^+$.

EXAMPLE 1046C tert-butyl 2-(4-(4-(4,5-difluoro-2-methoxyphenyl)-1H-pyrrolo[2,3-b]pyridin-2-yl)piperidin-1-yl)acetate The title compound was prepared as described in Example 275, substituting Example 1046B for Example 236G. MS (ESI$^+$) m/z 458 (M+H)$^+$.

EXAMPLE 1046D 2-(4-(4-(4,5-difluoro-2-methoxyphenyl)-1H-pyrrolo[2,3-b]pyridin-2-yl)piperidin-1-yl)acetic acid The title compound was prepared as described in Example 226B, substituting Example 1046C for Example 226A. MS (ESI$^+$) m/z 402 (M+H)$^+$.

EXAMPLE 1046E

2-{4-[4-(4,5-difluoro-2-methoxyphenyl)-1H-pyrrolo[2,3-b]pyridin-2-yl]piperidin-1-yl}-N-methylacetamide The title compound was prepared as described in Example 238, substituting Example 1046D for Example 226B and methylamine hydrochloride for azetidin-3-ol hydrochloride. $^1$H NMR (400 MHz, DMSO-d$_6$) δ 1.76 (qd, J=12.2, 3.7 Hz, 2H), 1.91-2.03 (m, 2H), 2.18 (td, J=11.7, 2.4 Hz, 2H), 2.62 (d, J=4.7 Hz, 3H), 2.68 (ddt, J=11.5, 7.8, 3.9 Hz, 1H), 2.82-2.88 (m, 2H), 2.91 (s, 2H), 3.75 (s, 3H), 5.96 (d, J=2.1 Hz, 1H), 6.99 (d, J=4.9 Hz, 1H), 7.34 (dd, J=12.9, 7.0 Hz, 1H), 7.43 (dd, J=11.1, 9.2 Hz, 1H), 7.65 (q, J=4.5 Hz, 1H), 8.13 (d, J=5.0 Hz, 1H), 11.57 (br s, 1H); MS (ESI$^+$) m/z 415 (M+H)$^+$.

EXAMPLE 1047

2-{4-[4-(4,5-difluoro-2-methoxyphenyl)-1H-pyrrolo[2,3-b]pyridin-2-yl]piperidin-1-yl}-N,N-dimethylacetamide The title compound was prepared as described in Example 238, substituting Example 1046D for Example 226B and dimethylamine hydrochloride for azetidin-3-ol hydrochloride. $^1$H NMR (400 MHz, DMSO-d$_6$) δ 1.70 (qd, J=12.3, 3.6 Hz, 2H), 1.89-2.00 (m, 2H), 2.16 (td, J=11.7, 2.4 Hz, 2H), 2.61-2.75 (m, 1H), 2.81 (s, 3H), 2.86-2.95 (m, 2H), 3.03 (s, 3H), 3.75 (s, 3H), 5.97 (d, J=2.1 Hz, 1H), 6.99 (d, J=5.1 Hz, 1H), 7.33 (dd, J=12.9, 6.9 Hz, 1H), 7.43 (dd, J=11.2, 9.2 Hz, 1H), 8.12 (d, J=4.9 Hz, 1H), 11.56 (br s, 1H); MS (ESI$^+$) m/z 429 (M+H)$^+$.

EXAMPLE 1048

2-{5-[4-(5-fluoro-2-methoxyphenyl)-1H-pyrrolo[2,3-b]pyridin-2-yl]-2,3,4,7-tetrahydro-1H-azepin-1-yl}acetamide

EXAMPLE 1048A 4-(5-fluoro-2-methoxyphenyl)-2-(2,5,6,7-tetrahydro-1H-azepin-4-yl)-1H-pyrrolo[2,3-b]pyridine A mixture of 4-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,7-tetrahydro-1H-azepin-4-yl)-1H-pyrrolo[2,3-b]pyridine (Example 733) was separated by HPLC (Luna C8(2) 5 um 100 Å AXIA column; gradient of acetonitrile with 0.1% trifluoroacetic acid and water, 10-95%) to provide the title compound. MS (ESI$^+$) m/z 338 (M+H)$^+$.

EXAMPLE 1048B

2-{5-[4-(5-fluoro-2-methoxyphenyl)-1H-pyrrolo[2,3-b]pyridin-2-yl]-2,3,4,7-tetrahydro-1H-azepin-1-yl}acetamide The title compound was prepared as described in Example 224, substituting Example 1048A for Example 87D and 2-bromoacetamide for 2-chloro-N,N-dimethylacetamide. $^1$H NMR (400 MHz, DMSO-d$_6$) δ 1.68 (p, J=5.4 Hz, 2H), 2.61-2.71 (m, 2H), 2.89 (dd, J=6.9, 4.4 Hz, 2H), 3.01 (s, 2H), 3.37 (d, J=6.0 Hz, 2H), 3.74 (s, 3H), 6.28 (d, J=2.1 Hz, 1H), 6.50 (t, J=6.0 Hz, 1H), 7.01 (d, J=5.0 Hz, 1H), 7.12 (d, J=3.2 Hz, 2H), 7.16-7.34 (m, 3H), 8.18 (d, J=4.9 Hz, 1H), 11.68 (br s, 1H); MS (ESI$^+$) m/z 395 (M+H)$^+$.

EXAMPLE 1049

2-{5-[4-(5-fluoro-2-methoxyphenyl)-1H-pyrrolo[2,3-b]pyridin-2-yl]-2,3,4,7-tetrahydro-1H-azepin-1-yl})-N,N-dimethylacetamide The title compound was prepared as described in Example 231F, substituting Example 1048A for Example 231E. $^1$H NMR (500 MHz, DMSO-d$_6$) δ 1.69 (p, J=5.5 Hz, 2H), 2.56-2.69 (m, 2H), 2.81 (s, 3H), 2.89 (d, J=4.4 Hz, 4H), 3.00 (s, 3H), 3.41 (d, J=6.0 Hz, 2H), 3.74 (s, 3H), 6.27 (d, J=2.1 Hz, 1H), 6.47 (t, J=6.0 Hz, 1H), 7.01 (d, J=4.9 Hz, 1H), 7.14-7.36 (m, 3H), 8.18 (d, J=4.9 Hz, 1H), 11.68 (br s, J 1H); MS (ESI$^+$) m/z 423 (M+H)$^+$.

EXAMPLE 1050

(1 S,2S,3R,4R)-3-[({4-[4-(4,5-difluoro-2-methoxyphenyl)-1H-pyrrolo[2,3-b]pyridin-2-yl]-3,6-dihydropyridin-1(2H)-yl}acetyl)amino]bicyclo[2.2.1]hept-5-ene-2-carboxamide

EXAMPLE 1050A 2-(4-(4-(4,5-difluoro-2-methoxyphenyl)-1H-pyrrolo[2,3-b]pyridin-2-yl)-5,6-dihydropyridin-1(2H)-yl)acetic acid The title compound was prepared as described in Example 226B, substituting Example 1046B for Example 226A. MS (ESI$^+$) m/z 400 (M+H)$^+$.

EXAMPLE 1050B (1 S,2S,3R,4R)-3-[({4-[4-(4,5-difluoro-2-methoxyphenyl)-1H-pyrrolo[2,3-b]pyridin-2-yl]-3,6-dihydropyridin-1(2H)-yl}acetyl)amino]bicyclo[2.2.1]hept-5-ene-2-carboxamide The title compound was prepared as described in Example 238, substituting Example 1050A for Example 226B and (1S,2S,3R,4R)-3-aminobicyclo[2.2.1]hept-5-ene-2-carboxamide for azetidin-3-ol hydrochloride. $^1$H NMR (500 MHz, DMSO-d$_6$) δ 1.35 (d, J=8.8 Hz, 1H), 2.05 (d, J=8.6 Hz, 1H), 2.39 (d, J=8.5 Hz, 1H), 2.55 (d, J=12.2 Hz, 1H), 2.58-2.70 (m, 2H), 2.53-2.58 (m, 1H), 2.75 (d, J=2.6 Hz, 1H), 3.07 (d, J=16.3 Hz, 2H), 3.12-3.29 (m, 2H), 3.76 (s, 3H), 3.89 (td, J=8.9, 1.7 Hz, 1H), 6.24 (dtd, J=8.9, 5.6, 2.8 Hz, 3H), 6.46 (t, J=3.4 Hz, 1H), 7.01 (d, J=4.8 Hz, 2H), 7.35 (dd, J=12.9, 6.9 Hz, 1H), 7.48 (dd, J=10.9, 9.2 Hz, 1H), 7.55 (d, J=2.4 Hz, 1H), 8.12 (d, J=8.9 Hz, 1H), 8.19 (d, J=4.9 Hz, 1H), 11.78 (d, J=2.2 Hz, 1H); MS (ESI$^+$) m/z 534 (M+H)$^+$.

EXAMPLE 1051

{4-[4-(5-fluoro-2-methoxyphenyl)-1H-pyrrolo[2,3-b]pyridin-2-yl]cyclohex-3-en-1-yl}[(2S)-2-(hydroxymethyl)pyrrolidin-1-yl]methanone The title compound was prepared according to the procedure described in Example 932, substituting (S)-pyrrolidin-2-ylmethanol for 1-(2-(methylsulfonyl)ethyl)-1H-pyrazol-4-amine hydrochloride. $^1$H NMR (400 MHz, DMSO-d$_6$) δ 1.50-2.02 (m, 4H), 2.16-2.46 (m, 2H), 2.68 (q, J =9.1, 8.7 Hz, 2H), 3.27 (t, J=9.0 Hz, 4H), 3.50 (dd, J=9.1, 4.4 Hz, 2H), 3.74 (s, 3H), 3.96 (d, J=6.7 Hz, 1H), 4.76 (s, 1H), 6.19 (d, J=7.4 Hz, 1H), 6.57 (d, J=4.9 Hz, 1H), 7.02 (d, J=4.9 Hz, 1H), 7.12-7.32 (m, 3H), 8.18 (d, J=4.9 Hz, 1H), 11.73 (s, 1H); MS (ESI$^+$) m/z 450 (M+H)$^+$.

EXAMPLE 1052

2-{4-[4-(4-fluoro-2-methoxyphenyl)-1H-pyrrolo[2,3-b]pyridin-2-yl]piperidin-1-yl}acetamide To a solution of Example 990 (1 g, 2.466 mmol) in 20 mL methanol in a pressure bottle was added 0.5 g wet 20% Pd(OH)$_2$ on carbon and the mixture was shaken for 16 hours at 50° C. under 30 psi H$_2$. The mixture was filtered, concentrated, and purified by flash column chromatography on silica (0-10% methanol/dichloromethane) to provide the title compound. $^1$H NMR (400 MHz, DMSO-d$_6$) δ 11.51 (s, 1H), 8.12 (d, J=4.9 Hz, 1H), 7.39 (dd, J=8.4, 6.9 Hz, 1H), 7.18-6.83 (m, 5H), 5.93 (d, J=2.8 Hz, 1H), 3.77 (s, 3H), 2.99-2.83 (m, 2H), 2.68 (tt, J=11.8, 3.7 Hz, 1H), 2.18 (td, J=11.7, 2.4 Hz, 2H), 2.02-1.91 (m, 2H), 1.75 (qd, J=12.1, 3.7 Hz, 2H), 1.36 (s, 2H). MS (ESI+) m/e 383 (M+H)$^+$.

EXAMPLE 1053

2-{4-[4-(4-fluoro-2-methoxyphenyl)-1H-pyrrolo[2,3-b]pyridin-2-yl]piperidin-1-yl}-N-methylacetamide The title compound was prepared using the procedure described in Example 1052, using Example 991 in place of Example 990. $^1$H NMR (400 MHz, DMSO-d$_6$) δ 11.52 (s, 1H), 8.12 (d, J=4.9 Hz, 1H), 7.65 (m, 1H), 7.39 (dd, J=8.4, 6.9 Hz, 1H), 7.09 (dd, J=11.6, 2.5 Hz, 1H), 6.98 (d, J=4.9 Hz, 1H), 6.91 (td, J=8.4, 2.5 Hz, 1H), 5.93 (d, J=2.1 Hz, 1H), 3.77 (s, 3H), 2.95-2.80 (m, 4H), 2.74-2.64 (m, 1H), 2.64 (d, J=3.9 Hz, 3H), 2.18 (td, J=11.5, 2.3 Hz, 2H), 2.02-1.91 (m, 2H), 1.75 (qd, J=12.1, 3.7 Hz, 2H). MS (ESI+) m/e 397 (M+H)$^+$.

EXAMPLE 1054

4-(5-fluoro-2-methoxyphenyl)-2-(octahydrocyclopenta[c]pyrrol-5-yl)-1H-pyrrolo[2,3-b]pyridine Example 262D (150 mg, 0.334 mmol) in methanol (10 ml) was treated with 5% Pd/C (80 mg, 0.334 mmol) in a 50 ml pressure bottle. The mixture was stirred for 2 days at 30 psi of hydrogen and 50° C. The reaction mixture was filtered and the filtrate was concentrated to give the Boc-intermediate. To this intermediate (26.8 mg, 0.059 mmol) was added CH$_2$Cl$_2$/trifluoroacetic acid (3/1, 0.5 mL), and the mixture was stirred at room temperature for 1 hour. The reaction mixture was concentrated in vacuo and triturated with hexanes and dried in vacuo overnight to afford title compound as the bis-trifluoroacetate salt. $^1$H NMR (400 MHz, DMSO-d$_6$) δ ppm 1.53-1.67 (m, 2 H) 2.31-2.43 (m, 2 H) 2.84-2.95 (m, 2 H) 3.08-3.26 (m, 5 H) 3.73 (s, 3 H) 6.09 (d, J=1.22 Hz, 1 H) 7.13 (d, J=5.19 Hz, 1 H) 7.17-7.24 (m, 2 H) 7.25-7.33 (m, 1 H) 8.22 (d, J=5.19 Hz, 1 H) 8.79 (bs, 1 H) 8.96 (bs, 1 H) 11.90 (s, 1 H). MS (ESI$^+$) m/z 352 (M+H)$^+$.

EXAMPLE 1055

1-{4-[5-fluoro-4-(5-fluoro-2-methoxyphenyl)-1H-pyrrolo[2,3-b]pyridin-2-yl]piperidin-1-yl}-2-hydroxyethanone Example 255D (80 mg, 0.192 mmol), 2-hydroxyacetic acid (25 mg, 0.231 mmol), 1-(3-dimethylaminopropyl)-3-ethylcarbodiimide hydrochloride (44.2 mg, 0.231 mmol), 1H-benzo[d][1,2,3]triazol-1-ol hydrate (35.3 mg, 0.231 mmol) triethylamine (134 µl, 0.961 mmol) in 2 mL dimethylformamide was stirred at room temperature for 5 hours. The crude product was purified by reverse-phase HPLC performed on Waters PrepLC 4000 System with a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-d$_6$) δ 1.67 (dqd, J=50.1, 12.7, 4.1 Hz, 2H), 1.99-2.17 (m, 2H), 2.82 (t, J=12.4 Hz, 1H), 2.94-3.24 (m, 2H), 3.80 (s, 5H), 4.19 (s, 2H), 4.51 (d, J=13.1 Hz, 1H), 6.00 (s, 1H), 7.02-7.81 (m, 3H), 8.22 (d, J=2.5 Hz, 1H), 11.84 (s, 1H). MS (ESI$^+$) m/z 402 (M+H)$^+$.

EXAMPLE 1056 pyrrolidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl 3-hydroxyazetidine-1-carboxylate in place of tert-butyl(2-hydroxyethyl)(methyl)carbamate. $^1$H NMR (500 MHz, dimethylsulfoxide-d$_6$) δ 12.75 (s, 1H), 11.56 (s, 1H), 9.52-9.28 (m, 2H), 8.31 (d, J=5.5 Hz, 1H), 7.41-7.21 (m, 4H), 6.75-6.63 (m, 1H), 6.45 (d, J=2.0 Hz, 1H), 4.12-4.08 (m, 4H), 3.77 (s, 3H), 3.50 (t, J=5.8 Hz, 2H), 3.28-3.13 (m, 2H), 3.13-3.01 (m, 1H), 2.98-2.86 (m, 1H), 2.69-2.54 (m, 3H), 2.08-1.91 (m, 1H), 1.72-1.55 (m, 1H). MS (ESI$^+$) m/z 530.1 (M+H)$^+$.

EXAMPLE 1057 piperidin-4-yl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl 4-hydroxypiperidine-1-carboxylate in place of tert-butyl(2-hydroxyethyl)(methyl)carbamate. $^1$H NMR (500 MHz, dimethylsulfoxide-d$_6$) δ 12.77 (s, 1H), 11.54 (s, 1H), 9.18 (d, J=60.0 Hz, 2H), 8.31 (d, J=5.5 Hz, 1H), 7.41-7.22 (m, 4H), 6.74-6.65 (m, 1H), 6.46 (d, J=1.9 Hz, 1H), 4.90-4.81 (m, 1H), 4.10-4.04 (m, 2H), 3.77 (s, 3H), 3.50 (t, J=5.8 Hz, 2H), 3.16-2.93 (m, 4H), 2.67-2.57 (m, 2H), 2.04-1.92 (m, 2H), 1.84-1.71 (m, 2H). MS (ESI$^+$) m/z 530.1 (M+H)$^+$.

EXAMPLE 1058 piperidin-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl 4-(hydroxymethyl)piperidine-1-carboxylate in place of tert-butyl(2-hydroxyethyl)(methyl)carbamate. $^1$H NMR (500 MHz, dimethylsulfoxide-d$_6$) δ 12.92 (s, 1H), 11.53 (s, 1H), 9.33-9.15 (m, 1H), 9.01-8.83 (m, 1H), 8.32 (d, J=5.6 Hz, 1H), 7.42-7.22 (m, 4H), 6.79-6.66 (m, 1H), 6.48 (d, J=1.9 Hz, 1H), 4.10-4.03 (m, 2H), 3.94 (d, J=6.6 Hz, 2H), 3.77 (s, 3H), 3.49 (t, J=5.8 Hz, 2H), 3.24-3.15 (m, 2H), 2.85-2.72 (m, 2H), 2.66-2.59 (m, 2H), 1.94-1.82 (m, 1H), 1.79-1.71 (m, 2H), 1.47-1.33 (m, 2H). MS (ESI$^+$) m/z 544.3 (M+H)$^+$.

EXAMPLE 1059 pyrrolidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl 3-hydroxypyrrolidine-1-carboxylate in place of tert-butyl(2-hydroxyethyl)(methyl)carbamate. $^1$H NMR (400 MHz, dimethylsulfoxide-d$_6$) δ 12.71 (s, 1H), 11.66 (s, 1H), 9.74-9.53 (m, 2H), 8.29 (d, J=5.5 Hz, 1H), 7.38-7.20 (m, 4H), 6.70-6.60 (m, 1H), 6.43 (d, J=1.8 Hz, 1H), 5.27-5.16 (m, 1H), 4.09-4.01 (m, 2H), 3.75 (s, 3H), 3.55-3.42 (m, 3H), 3.30-3.01 (m, 3H), 2.65-2.55 (m, 2H), 2.17-1.92 (m, 2H). MS (ESI$^+$) m/z 516.4 (M+H)$^+$.

EXAMPLE 1060

2,3-dihydroxypropyl ({4-[4-(5-fluoro-2-methoxyphenyl)-1H-pyrrolo[2,3-b]pyridin-2-yl]-3,6-dihydropyridin-1(2H)-yl}sulfonyl)carbamate To a solution of Example 1039 (284 mg, 0.507 mmol) in tetrahydrofuran (1468 µL) was added 1M aqueous hydrochloric acid (507 µL, 0.507 mmol) and the mixture was stirred at 60° C. for 1 hour. After cooling to ambient temperature, the mixture was carefully neutralized with 2M aqueous sodium bicarbonate (precipitate formed). The mixture was extracted with ethyl acetate (3×2 mL) and the combined extracts were washed with brine, dried over magnesium sulfate, filtered and concentrated to provide the title compound. $^1$H NMR (400 MHz, dimethylsulfoxide-d$_6$)

δ 11.95-11.84 (m, 1H), 11.42 (s, 1H), 8.22 (dd, J=5.0, 1.1 Hz, 1H), 7.33-7.16 (m, 3H), 7.06 (d, J=5.0 Hz, 1H), 6.87 (s, 1H), 6.59-6.49 (m, 1H), 6.28 (d, J=1.9 Hz, 1H), 4.14-3.90 (m, 3H), 3.74 (s, 3H), 3.68-3.60 (m, 1H), 3.48 (t, J=5.8 Hz, 2H), 3.37-3.31 (m, 2H), 3.21 (t, J=5.7 Hz, 1H), 2.66-2.54 (m, 2H). MS (ESI+) m/z 521.4 (M+H)+.

EXAMPLE 1061 methyl {4-[4-(2-methoxyphenyl)-1H-pyrrolo[2,3-b]pyridin-2-yl]piperidin-1-yl}acetate

EXAMPLE 1061A methyl 2-(4-(4-(2-methoxyphenyl)-1H-pyrrolo[2,3-b]pyridin-2-yl)-5,6-dihydropyridin-1(2H)-yl)acetate The title compound was prepared as described in Example 226A, substituting Example 1023A for Example 87D and methyl 2-bromoacetate for tert-butyl 2-bromoacetate. MS (ESI+) m/z 378 (M+H)+.

EXAMPLE 1061B methyl 2-(4-(4-(2-methoxyphenyl)-1H-pyrrolo[2,3-b]pyridin-2-yl)-5,6-dihydropyridin-1(2H)-yl)acetate The title compound was prepared as described in Example 275, substituting Example 1061A for Example 236G. $^1$H NMR (500 MHz, DMSO-$d_6$) δ 1.69 (qd, J=12.3, 3.9 Hz, 2H), 1.88-1.99 (m, 2H), 2.29 (td, J=11.6, 2.4 Hz, 2H), 2.67 (tt, J=11.6, 3.7 Hz, 1H), 2.85-2.95 (m, 2H), 3.25 (s, 2H), 3.62 (s, 3H), 3.75 (s, 3H), 5.93 (d, J=2.1 Hz, 1H), 6.99 (d, J=4.9 Hz, 1H), 7.07 (td, J=7.4, 1.0 Hz, 1H), 7.17 (dd, J=8.4, 1.1 Hz, 1H), 7.37 (dd, J=7.5, 1.7 Hz, 1H), 7.42 (ddd, J=8.8, 7.5, 1.7 Hz, 1H), 8.12 (d, J=4.9 Hz, 1H), 11.50 (br s, 1H); MS (ESI+) m/z 380 (M+H)+.

EXAMPLE 1062

1-[(2S)-2-(hydroxymethyl)pyrrolidin-1-yl]-2-{4-[4-(2-methoxyphenyl)-1H-pyrrolo[2,3-b]pyridin-2-yl]piperidin-1-yl}ethanone The title compound was prepared as described in Example 238, substituting Example 1023D for Example 226B and (S)-pyrrolidin-2-ylmethanol for azetidin-3-ol hydrochloride. $^1$H NMR (500 MHz, DMSO-$d_6$) δ 1.62-1.98 (m, 7H), 2.11-2.26 (m, 2H), 2.67 (ddt, J=11.8, 8.1, 3.6 Hz, 1H), 2.86-2.97 (m, 2H), 2.99-3.16 (m, 2H), 3.16-3.28 (m, 1H), 3.50 (ddd, J=9.3, 7.0, 4.6 Hz, 1H), 3.75 (s, 3H), 3.93 (tt, J=7.3, 3.7 Hz, 1H), 4.74 (dd, J=6.2, 5.0 Hz, 1H), 5.76 (s, 1H), 5.89-5.97 (m, 1H), 6.99 (d, J=4.9 Hz, 1H), 7.07 (t, J=7.4 Hz, 1H), 7.17 (d, J=7.8 Hz, 1H), 7.37 (dd, J=7.4, 1.7 Hz, 1H), 7.42 (ddd, J=8.7, 7.4, 1.7 Hz, 1H), 8.11 (d, J=5.0 Hz, 1H), 11.50 (br s, 1H); MS (ESI+) m/z 449 (M+H)+.

EXAMPLE 1063

(2R)-2-({4-[4-(5-fluoro-2-methoxyphenyl)-1H-pyrrolo[2,3-b]pyridin-2-yl]cyclohex-3-en-1-yl}amino)-1-(3-hydroxyazetidin-1-yl)-3-methylbutan-1-one The title compound was prepared essentially as described in Example 558, substituting Example 219C with Example 241C and phenylmethanamine with azetidin-3-ol hydrochloric acid. $^1$H NMR (400 MHz, DMSO-$d_6$) δ ppm 12.71 (s, 1 H) 8.62-9.81 (m, 2 H) 8.29 (d, J=5.49 Hz, 1 H) 7.84 (dd, J=103.45, 8.24 Hz, 1 H) 7.18-7.59 (m, 5 H) 6.60 (s, 1 H) 6.41 (d, J=2.44 Hz, 1 H) 3.86-4.27 (m, 3 H) 3.50-3.73 (m, 2 H) 3.24 (s, 1 H) 3.03-3.18 (m, 1 H) 2.55-2.85 (m, 2 H) 2.14-2.45 (m, 3 H) 1.76-2.03 (m, 1 H) 0.92-1.42 (m, 7 H). MS (ESI): 493.1 (M+H)+.

EXAMPLE 1064

1-{4-[4-(5-fluoro-2-methoxyphenyl)-1H-pyrrolo[2,3-b]pyridin-2-yl]cyclohex-3-en-1-yl}-N,N-dimethyl-L-prolinamide To a solution of Example 242 (100 mg, 0.212 mmol) in 3 mL dichloromethane was added dimethylamine hydrochloride (34.6 mg, 0.424 mmol), 1 (3-dimethylaminopropyl)-3-ethylcarbodiimide hydrochloride (60.9 mg, 0.318 mmol), and 1H-benzo[d][1,2,3]triazol-1-ol hydrate (48.7 mg, 0.318 mmol) followed by N-ethyl-N-isopropylpropan-2-amine (0.222 mL, 1.271 mmol). The reaction was stirred at room temperature overnight. The solvent was removed and the residue was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/minute (0-0.5 min 10% A, 0.5-7.0 min linear gradient 10-95% A, 7.0-10.0 min 95% A, 10.0-12.0 min linear gradient 95-10% A) to give the title compound as the trifluoroacetic acid salt. $^1$H NMR (400 MHz, DMSO-$d_6$) δ ppm 11.96 (s, 1 H) 9.33 (d, J=21.36 Hz, 1 H) 8.23 (d, J=5.19 Hz, 1 H) 7.15-7.34 (m, 3 H) 7.08 (d, J=5.19 Hz, 1 H) 6.38-6.49 (m, 1 H) 6.26 (dd, J=5.80, 1.83 Hz, 1 H) 4.78-4.95 (m, 2 H) 3.64-3.79 (m, 4 H) 3.45-3.59 (m, 1 H) 3.23-3.39 (m, 1 H) 3.05 (s, 3 H) 2.58-2.78 (m, 2 H) 2.33-2.50 (m, 2 H) 1.57-2.25 (m, 5 H). MS (ESI): 463.2 (M+H)+.

EXAMPLE 1066

4-(5-fluoro-2-methoxyphenyl)-2-[3-(methylsulfonyl)-3-azabicyclo[4.1.0]hept-6-yl]-1H-pyrrolo[2,3-b]pyridine

EXAMPLE 1066A tert-butyl 4-(4-(5-fluoro-2-methoxyphenyl)-1H-pyrrolo[2,3-b]pyridin-2-yl)-5,6-dihydropyridine-1(2H)-carboxylate A solution of NaOH (5.32 g, 133 mmol) in water (60 mL) was added to Example 87C (30 g, 53.2 mmol) in 1,4-dioxane (600 mL). The reaction mixture was heated to 90° C. for 16 hours. The solvent was evaporated and the residue was treated with ethyl acetate and washed with water. The organic layer was dried over MgSO$_4$, filtered, and concentrated to provide the title compound. MS (ESI+) m/z 424 (M+H)+.

EXAMPLE 1066B

A mixture of Example 1066A (1.0 g, 2.361 mmol) and diiodomethane (0.953 ml, 11.81 mmol) in 1,2-dichloroethane (10 ml) was stirred at 70° C. for 30 minutes. Diethylzinc (1M in hexanes, 11.81 mL, 11.81 mmol) was added. The resulting mixture was stirred at 70° C. overnight. The mixture was concentrated. The concentrate was purified by HPLC (see protocols in Example 610) to provide the title compound. MS (ESI⁺) m/z 438 (M+H)⁺.

EXAMPLE 1066C 2-(3-azabicyclo[4.1.0]heptan-6-yl)-4-(5-fluoro-2-methoxyphenyl)-1H-pyrrolo[2,3-b]pyridine A solution of Example 1066B (76.0 mg, 0.174 mmol) in CH$_2$Cl$_2$ (1.5 mL) was treated with trifluoroacetic acid (0.134 mL, 1.737 mmol). The mixture was stirred for 3 hours and was concentrated. The residue was dissolved in 0.5 mL of methanol and treated with 0.5 mL of 2M HCl in ether slowly. The mixture was further treated with 1 mL of ether. The precipitate was filtered, washed with ether, and vacuum oven-dried to provide the title compound as an HCl salt. MS (APCI⁺) m/z 338.4 (M+H)⁺.

EXAMPLE 1066D 4-(5-fluoro-2-methoxyphenyl)-2-[3-(methylsulfonyl)-3-azabicyclo[4.1.0]hept-6-yl]-1H-pyrrolo[2,3-b]pyridine To a solution of Example 1066C (20.7 mg, 0.050 mmol) in 1-methyl-2-pyrrolidinone (0.7 mL) was added methanesulfonyl chloride (7.86 µL, 0.101 mmol) and triethylamine (0.042 mL, 0.303 mmol). The reaction mixture was stirred for 3 hours and was treated with water. The precipitate was filtered, washed with water, and purified by HPLC (see protocols in Example 361) to provide the title compound as a trifluoroacetic acid salt. ¹H NMR (400 MHz, pyridine-d$_5$) δ ppm 1.07-1.14 (m, 1H), 1.41 (dd, J=9.1, 4.9 Hz, 1H), 1.77-1.86 (m, 1H), 2.24 (ddd, J=13.8, 8.4, 5.4 Hz, 1H), 2.60 (dt, J=14.0, 5.7 Hz, 1H), 2.96 (s, 3H), 3.03-3.20 (m, 1H), 3.28-3.38 (m, 1H), 3.61-3.73 (m, 5H), 6.42 (d, J=6.42, 1H), 7.11 (dd, J=9.0, 4.5 Hz, 1H), 7.26-7.31 (m, 1H), 7.33 (d, J=4.9 Hz, 1H), 8.57 (d, J=4.9 Hz, 1H), 12.72-12.77 (m, 1H). MS (ESI⁺) m/z 416.1 (M+H)⁺.

EXAMPLE 1067

4-(5-fluoro-2-methoxyphenyl)-2-[4-(1H-tetrazol-5-yl)cyclohex-1-en-1-yl]-1H-pyrrolo[2,3-b]pyridine A mixture of sodium azide (162 mg, 2.492 mmol), ammonium chloride (133 mg, 2.492 mmol) and Example 985A (250.0 mg, 0.498 mmol) in N,N-dimethylformamide (5 mL) was stirred at 120° C. for 24 hours. The reaction mixture was diluted with brine and extracted with ethyl acetate. The aqueous layer was concentrated and the residue was triturated with ethyl acetate/methanol (9:1). The solution was decanted. The combined organic fractions were dried over MgSO$_4$, filtered, and concentrated to give the crude intermediate. The crude intermediate and 5M aqueous NaOH (0.4 mL) in methanol (4 mL) was heated at 85° C. for 30 minutes in a Biotage Initiator microwave reactor (model 355302). The reaction mixture was concentrated and purified by HPLC (see protocols in Example 361) to provide the title compound as a trifluoroacetic acid salt. The trifluoroacetic acid salt was suspended in 3 mL of methanol and treated with 2 mL of 2N HCl in ether followed by 4 mL of ether. The suspension was stirred for 15 minutes, filtered, washed with ether, and vacuum oven-dried to provide the title compound as an HCl salt. ¹H NMR (400 MHz, methanol-d$_4$) δ ppm 2.01-2.15 (m, 1H), 2.31-2.40 (m, 1H), 2.59-2.76 (m, 3H), 2.80-2.91 (m, 1H), 3.40-3.49 (m, 1H), 3.83 (s, 3H), 6.61 (s, 1H), 6.65-6.71 (m, 1H), 7.21-7.29 (m, 1H), 7.27-7.37 (m, 2H), 7.56 (d, J=6.2 Hz, 1H), 8.28 (d, J=6.2 Hz, 1H). MS (ESI⁺) m/z 391.1 (M+H)⁺.

EXAMPLE 1068

4-[4-(5-fluoro-2-methoxyphenyl)-1H-pyrrolo[2,3-b]pyridin-2-yl]cyclohex-3-en-1-yl tert-butylcarbamate The title compound was prepared using the procedure described in Example 604, using Example 790 (0.083 g, 0.25 mmol) in place of Example 87D and 2-methylpropan-2-amine in place of 2-aminoethanol. ¹H NMR (400 MHz, DMSO-d$_6$): δ 1.21 (s, 9 H) 1.72-1.97 (m, 2 H) 2.18-2.29 (m, 1 H) 2.53-2.64 (m, 2 H) 3.74 (s, 3 H) 4.75-4.86 (m, 1 H) 6.23 (d, J=1.83 Hz, 1 H) 6.41-6.46 (m, 1 H) 6.80 (s, 1 H) 7.05 (d, J=5.19 Hz, 1 H) 7.17-7.32 (m, 3 H) 8.19 (d, J=4.88 Hz, 1 H) 11.82 (s, 1 H). MS (ESI⁺) m/z: 438.1 (M+H)⁺.

EXAMPLE 1069

2-{4-[4-(5-fluoro-2-methoxyphenyl)-5-methoxy-1H-pyrrolo[2,3-b]pyridin-2-yl]-3,6-dihydropyridin-1(2H)-yl}-1-[(2S)-2-(hydroxymethyl)pyrrolidin-1-yl]ethanone

EXAMPLE 1069A tert-butyl 2-(4-(4-(5-fluoro-2-methoxyphenyl)-5-methoxy-1H-pyrrolo[2,3-b]pyridin-2-yl)-5,6-dihydropyridin-1(2H)-yl)acetate The title compound was prepared according to the procedure described in Example 226A, substituting Example 873C for Example 87D. MS (ESI⁺) m/z 468 (M+H)⁺.

EXAMPLE 1069B 2-(4-(4-(5-fluoro-2-methoxyphenyl)-5-methoxy-1H-pyrrolo[2,3-b]pyridin-2-yl)-5,6-dihydropyridin-1(2H)-yl)acetic acid The title compound was prepared according to the procedure described in Example 226B, substituting Example 1069A for Example 226A. MS (ESI⁺) m/z 412 (M+H)⁺.

EXAMPLE 1069C

2-{4-[4-(5-fluoro-2-methoxyphenyl)-5-methoxy-1H-pyrrolo[2,3-b]pyridin-2-yl]-3,6-dihydropyridin-1(2H)-yl}-1-[(2S)-2-(hydroxymethyl)pyrrolidin-1-yl]ethanone The title compound was prepared according to the procedure described in Example 238, substituting Example 1069B for Example 226B and (S)-pyrrolidin-2-ylmethanol for azetidin-3-ol hydrochloride. ¹H NMR (500 MHz, DMSO-d$_6$) δ 1.70-1.98 (m, 6H), 2.41 (q, J=7.2, 5.2 Hz, 2H), 2.68 (q, J=5.8 Hz, 2H), 3.15-3.35 (m, 4H), 3.34-3.57 (m, 3H), 3.68 (s, 3H), 3.76 (s, 3H), 5.91 (s, 1H), 6.43 (t, J=3.6 Hz, 1H), 6.88-7.57 (m, 3H), 8.10 (s, 1H), 11.58 (s, 1H). MS (ESI⁺) m/z 495 (M+H)⁺.

EXAMPLE 1070

2-{4-[4-(4,5-difluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone The title compound was prepared as described in Example 238, substituting Example 1046D for Example 226B and (S)-pyrrolidin-2-ylmethanol for azetidin-3-ol hydrochloride. $^1$H NMR (500 MHz, DMSO-$d_6$) δ 1.62-1.98 (m, 6H), 2.10-2.26 (m, 2H), 2.68 (tq, J=11.8, 4.1, 3.6 Hz, 1H), 2.87-2.98 (m, 2H), 3.10 (q, J=14.4 Hz, 2H), 3.26 (ddt, J=15.9, 9.1, 4.1 Hz, 2H), 3.41 (dt, J=11.0, 7.1 Hz, 1H), 3.45-3.54 (m, 2H), 3.75 (s, 3H), 3.94 (dp, J=7.2, 3.5 Hz, 1H), 4.75 (t, J=5.6 Hz, 1H), 5.76 (s, 1H), 5.97 (t, J=2.7 Hz, 1H), 6.99 (d, J=4.9 Hz, 1H), 7.33 (dd, J=12.9, 6.9 Hz, 1H), 7.43 (dd, J=11.0, 9.1 Hz, 1H), 8.13 (d, J=5.0 Hz, 1H), 11.57 (br s, 1H); MS (ESI$^+$) m/z 485 (M+H)$^+$.

EXAMPLE 1071

2-{(2S)-4-[4-(5-fluoro-2-methoxyphenyl)-1H-pyrrolo[2,3-b]pyridin-2-yl]-2-methylpiperidin-1-yl}-N,N-dimethylacetamide

EXAMPLE 1071A (2S)-tert-butyl 4-(4-(5-fluoro-2-methoxyphenyl)-1H-pyrrolo[2,3-b]pyridin-2-yl)-2-methylpiperidine-1-carboxylate The title compound was prepared using the procedure described in Example 275, using Example 258E (0.6 g, 1.37 mmol) in place of Example 236G. MS (ESI$^+$) m/z: 438.3 (M–H)$^+$.

EXAMPLE 1071B 4-(5-fluoro-2-methoxyphenyl)-2-((2S)-2-methylpiperidin-4-yl)-1H-pyrrolo[2,3-b]pyridine The title compound was prepared using the procedure described in Example 1H, using Example 1071A (0.22 g, 0.5 mmol) in place of Example 1G. LCMS: 339.6 (M+H)$^+$.

EXAMPLE 1071C

2-{(2S)-4-[4-(5-fluoro-2-methoxyphenyl)-1H-pyrrolo[2,3-b]pyridin-2-yl]-2-methylpiperidin-1-yl})-N,N-dimethylacetamide The title compound was prepared using the procedure described in Example 231F, using Example 1071B in place of Example 231E. $^1$H NMR (400 MHz, DMSO-$d_6$): δ 1.24-1.47 (m, 3 H) 1.94-2.40 (m, 4 H) 2.83-3.35 (m, 8 H) 3.73 (s, 3 H) 4.07-4.21 (m, 2 H) 6.00-6.13 (m, 1 H) 7.02-7.07 (m, 1 H) 7.13-7.26 (m, 3 H) 8.16-8.19 (m, 1 H) 11.43 (s, 1 H). MS (ESI$^+$) m/z: 425.2 (M+H)$^+$.

EXAMPLE 1072

4,4,4-trifluoro-2-{4-[4-(5-fluoro-2-methoxyphenyl)-1H-pyrrolo[2,3-b]pyridin-2-yl]-3,6-dihydropyridin-1(2H)-yl}butanoic acid

EXAMPLE 1072A ethyl 4,4,4-trifluoro-2-(4-(4-(5-fluoro-2-methoxyphenyl)-1H-pyrrolo[2,3-b]pyridin-2-yl)-5,6-dihydropyridin-1(2H)-yl)butanoate A mixture of Example 87D (0.075 g, 0.189 mmol) and triethylamine (0.132 ml, 0.946 mmol) in N,N-dimethylformamide (1.893 ml) and ethyl 2-bromo-4,4,4-trifluorobutanoate (0.066 g, 0.265 mmol) was heated at 80° C. for 20 hours. The reaction mixture was allowed to cool to room temperature, water (10 mL) was added, and the resulting suspension was stirred for 2 hours. The mixture was filtered and the solid collected was dried under vacuum. The crude product was purified by flash chromatography on silica gel (AnaLogix IntelliFlash 280 system) eluting with a gradient of from 0% to 4% methanol in dichloromethane to afford the title compound. MS (ESI$^+$) m/z 492.2 (M+H)$^+$.

EXAMPLE 1072B 4,4,4-trifluoro-2-{4-[4-(5-fluoro-2-methoxyphenyl)-1H-pyrrolo[2,3-b]pyridin-2-yl]-3,6-dihydropyridin-1(2H)-yl}butanoic acid A mixture of Example 1072A (0.059 g, 0.120 mmol) in tetrahydrofuran (0.600 ml) and methanol (0.600 ml) was treated with aqueous 2M lithium hydroxide (0.210 ml, 0.420 mmol). The reaction mixture was heated at 40° C. for 8 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the product as a trifluoroacetic acid salt. The purified material was dissolved in 0.3 mL dichloromethane and 1 mL 2M HCl in ether was added. The resulting suspension was stirred 5 minutes, treated with 3 mL ether and filtered. The solid collected was washed with ether and dried under vacuum to afford the title compound as a hydrochloric acid salt. $^1$H NMR (400 MHz, CD$_3$OD) δ 8.30 (d, J=6.3 Hz, 1H), 7.59 (d, J=6.3 Hz, 1H), 7.36-7.22 (m, 3H), 6.64-6.53 (m, 2H), 4.14-3.98 (m, 1H), 3.87-3.76 (m, 4H), 3.71-3.62 (m, 1H), 3.28-3.18 (m, 1H), 3.14-3.02 (m, 1H), 2.88 (dd, J=16.1, 8.9 Hz, 1H), 2.77-2.69 (m, 1H), 2.69-2.56 (m, 2H). MS (ESI$^+$) m/z 464.1 (M+H)$^+$.

EXAMPLE 1074

2-{4-[4-(5-fluoro-2-methoxyphenyl)-1H-pyrrolo[2,3-b]pyridin-2-yl]piperidin-1-yl}-N-methyl-2-oxoethanesulfonamide A mixture of Example 135B (0.070 g, 0.176 mmol) and 2-(N-methylsulfamoyl)acetic acid (0.032 g, 0.211 mmol) in N,N-dimethylformamide (1.5 ml) was treated with N-methylmorpholine (0.097 ml, 0.879 mmol) followed by 1 (3-dimethylaminopropyl)-3-ethylcarbodiimide hydrochloride (0.051 g, 0.264 mmol) and 1H-benzo[d][1,2,3]triazol-1-ol hydrate (0.016 g, 0.105 mmol) and the reaction was stirred at room temperature for 24 hours. The reaction was treated with water (10 mL) and the resulting suspension was filtered. The solid collected was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (500 MHz, CD$_3$OD) δ ppm 1.69 (qd, J=12.5, 4.2 Hz, 1H), 1.87 (qd, J=12.3, 4.1 Hz, 1H), 2.09-2.18 (m, 2H), 2.77 (s, 3H), 2.88 (td, J=12.9, 2.7 Hz, 1H), 3.09 (tt, J=11.8, 3.8 Hz, 1H), 3.29-3.38 (m, 1H), 3.75 (s, 3H), 4.15-4.23 (m, 1H), 4.23-4.36 (m, 2H), 4.60-4.68 (m, 1H), 6.06 (s, 1H), 7.08 (d, J=5.1 Hz, 1H), 7.10-7.20 (m, 3H), 8.12 (d, J=5.1 Hz, 1H). MS (ESI$^+$) m/z 461.1 (M+H)$^+$.

EXAMPLE 1075

2-{4-[4-(5-fluoro-2-methoxyphenyl)-1H-pyrrolo[2,3-b]pyridin-2-yl]piperidin-1-yl}-N,N-dimethyl-2-oxoethanesulfonamide The title compound was prepared essentially as described in Example 1074 substituting 2-(N,N-dimethylsulfamoyl) acetic acid for 2-(N-methylsulfamoyl)acetic acid. $^1$H NMR (400 MHz, DMSO-d$_6$) δ ppm 1.43-1.62 (m, 1H), 1.63-1.82 (m, 1H), 2.00-2.12 (m, 2H), 2.70-2.86 (m, 7H), 2.95-3.10 (m, 1H), 3.12-3.27 (m, 1H), 3.73 (s, 3H), 4.06-4.18 (m, 1H), 4.26-4.41 (m, 2H), 4.42-4.53 (m, 1H), 5.96 (d, J=2.2 Hz, 1H), 7.02 (d, J=4.9 Hz, 1H), 7.12-7.33 (m, 3H), 8.15 (d, J=5.0 Hz, 1H), 11.63 (d, J=2.3 Hz, 1H). MS (ESI$^+$) m/z 475.1 (M+H)$^+$.

EXAMPLE 1077 ethyl {4-[4-(5-fluoro-2-methoxyphenyl)-1H-pyrrolo[2,3-b]pyridin-2-yl]-3,6-dihydropyridin-1(2H)-yl}(phenyl)acetate A mixture of Example 87D (0.075 g, 0.189 mmol) and N-ethyl-N-isopropylpropan-2-amine (0.132 ml, 0.757 mmol) in N,N-dimethylformamide (1.9 ml) was treated with ethyl 2-bromo-2-phenylacetate (0.060 g, 0.246 mmol) and the reaction was heated at 80° C. for 30 minutes. The reaction mixture was allowed to cool to room temperature, water (15 mL) was added and the resulting suspension was stirred for 2 hours. The mixture was filtered and the solid collected was dried under vacuum. The crude product was purified by flash chromatography on silica gel (AnaLogix IntelliFlash 280 system) eluting with a gradient of from 0% to 4% methanol in dichloromethane to afford the title compound. $^1$H NMR (400 MHz, CD$_3$OD) δ ppm 1.18 (t, J=7.1 Hz, 3H), 2.48-2.66 (m, 2H), 2.74 (t, J=5.8 Hz, 2H), 3.10-3.29 (m, 2H), 3.75 (s, 3H), 4.03-4.27 (m, 3H), 6.24 (s, 1H), 6.30-6.37 (m, 1H), 7.06 (d, J=5.1 Hz, 1H), 7.10-7.21 (m, 3H), 7.28-7.41 (m, 3H), 7.41-7.54 (m, 2H), 8.14 (d, J=5.1 Hz, 1H). MS (ESI$^+$) m/z 486.0 (M+H)$^+$.

EXAMPLE 1078 ethyl 2-{4-[4-(5-fluoro-2-methoxyphenyl)-1H-pyrrolo[2,3-b]pyridin-2-yl]-3,6-dihydropyridin-1(2H)-yl}-1,3-thiazole-5-carboxylate A mixture of Example 87D (0.075 g, 0.189 mmol) and N-ethyl-N-isopropylpropan-2-amine (0.132 ml, 0.757 mmol) in N,N-dimethylformamide (1.893 ml) was treated with ethyl 2-bromothiazole-5-carboxylate (0.034 ml, 0.227 mmol) and the reaction was heated at 80° C. for 2 hours. The reaction was allowed to cool to room temperature and water (15 mL) was added. The resulting suspension was stirred for 30 minutes and filtered. The solid collected was washed with water and dried under vacuum. The crude product was purified by flash chromatography on silica gel (AnaLogix IntelliFlash 280 system) eluting with a gradient of from 0% to 4% methanol in dichloromethane to afford the title compound. $^1$H NMR (400 MHz, DMSO-d$_6$) δ ppm 1.26 (t, J=7.1 Hz, 3H), 2.62-2.71 (m, 2H), 3.74 (s, 3H), 3.81 (t, J=5.7 Hz, 2H), 4.15-4.29 (m, 4H), 6.31 (d, J=2.0 Hz, 1H), 6.54-6.63 (m, 1H), 7.05 (d, J=4.9 Hz, 1H), 7.14-7.35 (m, 3H), 7.90 (s, 1H), 8.22 (d, J=4.9 Hz, 1H), 11.91 (d, J=2.3 Hz, 1H). MS (ESI$^+$) m/z 479.1 (M+H)$^+$.

EXAMPLE 1079 tert-butyl 3-{4-[4-(5-fluoro-2-methoxyphenyl)-1H-pyrrolo[2,3-b]pyridin-2-yl]-3,6-dihydropyridin-1(2H)-yl}pyrrolidine-1-carboxylate The title compound was prepared essentially as described in Example 908 substituting tert-butyl 3-oxopyrrolidine-1-carboxylate for (S)-1-tert-butyl 2-methyl 4-oxopyrrolidine-1,2-dicarboxylate. $^1$H NMR (400 MHz, DMSO-d$_6$, 90° C.) δ ppm 1.41 (s, 9H), 1.67-1.86 (m, 1H), 1.99-2.13 (m, 1H), 2.42-2.54 (m, 2H), 2.56-2.77 (m, 2H), 2.87-3.01 (m, 1H), 3.01-3.30 (m, 4H), 3.33-3.45 (m, 1H), 3.53 (dd, J=10.4, 6.9 Hz, 1H), 3.72 (s, 3H), 6.18 (s, 1H), 6.38-6.49 (m, 1H), 6.99 (d, J=4.9 Hz, 1H), 7.10-7.27 (m, 3H), 8.17 (d, J=4.9 Hz, 1H), 11.40-11.47 (m, 1H). MS (ESI$^+$) m/z 493.1 (M+H)$^+$.

EXAMPLE 1080 ethyl {[(6S)-4-[4-(5-fluoro-2-methoxyphenyl)-1H-pyrrolo[2,3-b]pyridin-2-yl]-6-methyl-3,6-dihydropyridin-1(2H)-yl]sulfonyl}carbamate Example 258F (100 mg, 0.24 mmol), Example 578A (90 mg, 0.24 mmol) and triethylamine (0.2 mL, 1.4 mmol) were stirred in dichloromethane at room temperature for 24 hours then concentrated. Purification by reverse phase-HPLC (Sunfire 5 µM, 50×250 mm) eluting with 5-50% acetonitrile in water (containing 0.1% trifluoroacetic acid) provided the title compound as trifluoroacetate salt. To a solution of this salt in methanol was added 2M hydrogen chloride in diethyl ether. Concentration afforded the title compound as the hydrochloride salt. $^1$HNMR (400 MHz, DMSO-d$_6$) δ 1.07 (t, 3H), 1.30 (d, 3H), 2.45 (m, 2H), 3.27 (m, 1H), 3.76 (s, 3H), 3.99 (m, 3H), 4.60 (m, 1H), 6.42 (br s, 1H), 6.59 (m, 1H), 7.29 (m, 4H), 8.28 (d, 1H), 11.36 (s, 1H), 12.45 (br s, 1H). (ESI) m/e 489.1 (M+H)$^+$.

EXAMPLE 1081

2-({4-[4-(5-fluoro-2-methoxyphenyl)-1H-pyrrolo[2,3-b]pyridin-2-yl]cyclohex-3-en-1-yl}oxy)ethanol To a stirred suspension of Example 1027 (0.082 g, 0.21 mmol) in tetrahydrofuran (6 mL) was added lithium aluminum hydride (0.045 g, 1.2 mmol). The mixture was stirred at room temperature overnight. The mixture was treated with water, and ethyl acetate was added. The organic layer was washed with saturated NaHCO$_3$ solution, water and brine. The organic layer was dried over sodium sulfate. After filtration, the solvent was removed and the residue was purified by flash chromatography on silica gel (AnaLogix IntelliFlash) eluting with a gradient of 0-10% methanol in dichloromethane to afford the title compound. $^1$H NMR (400

MHz, DMSO-d$_6$): δ 1.59-1.73 (m, 1 H) 1.88-2.01 (m, 1 H) 2.09-2.22 (m, 1 H) 2.31-2.44 (m, 1 H) 2.53-2.59 (m, 1 H) 3.44-3.53 (m, 4 H) 3.58-3.67 (m, 1 H) 3.74 (s, 3 H) 4.53-4.58 (m, 1 H) 6.18 (d, J=1.83 Hz, 1 H) 6.39-6.44 (m, 1 H) 7.01 (d, J=4.88 Hz, 1 H) 7.15-7.31 (m, 3 H) 8.17 (d, J=4.88 Hz, 1 H) 11.71 (s, 1 H). MS (ESI+) m/z 383.2 (M+H)$^+$.

EXAMPLE 1082

2-{4-[4-(5-fluoro-2-methoxyphenyl)-1H-pyrrolo[2,3-b]pyridin-2-yl]piperidin-1-yl}propanoic acid

EXAMPLE 1082A methyl 2-(4-(4-(5-fluoro-2-methoxyphenyl)-1H-pyrrolo[2,3-b]pyridin-2-yl)piperidin-1-yl)propanoate The title compound was prepared essentially as described in Example 676 substituting Example 135B for Example 87. MS (ESI$^+$) m/z 412.2 (M+H)$^+$.

EXAMPLE 1082B

2-{4-[4-(5-fluoro-2-methoxyphenyl)-1H-pyrrolo[2,3-b]pyridin-2-yl]piperidin-1-yl}propanoic acid A mixture of Example 1082A (0.054 g, 0.131 mmol) in tetrahydrofuran (0.7 ml) and methanol (0.7 ml) was treated with aqueous 2M lithium hydroxide (0.197 ml, 0.394 mmol) and the reaction was allowed to stir at room temperature for 16 hours and then at 55° C. for 8 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the product as a trifluoroacetic acid salt. The purified material was dissolved in 0.3 mL dichloromethane and 1 mL 2M HCl in ether was added. The resulting suspension was stirred 5 minutes, treated with 3 mL ether and filtered. The solid collected was washed with ether and dried under vacuum to afford the title compound as a hydrochloric acid salt. $^1$H NMR (500 MHz, CD$_3$OD) δ ppm 1.68 (d, J=7.2 Hz, 3H), 2.02-2.28 (m, 2H), 2.38-2.51 (m, 2H), 3.30-3.54 (m, 3H), 3.58-3.80 (m, 2H), 3.82 (s, 3H), 4.19-4.28 (m, 1H), 6.47-6.53 (m, 1H), 7.20-7.37 (m, 3H), 7.59 (d, J=6.1 Hz, 1H), 8.35 (d, J=6.2 Hz, 1H). MS (ESI$^+$) m/z 398.2 (M+H)$^+$.

EXAMPLE 1083

{4-[4-(5-fluoro-2-methoxyphenyl)-1H-pyrrolo[2,3-b]pyridin-2-yl]-3,6-dihydropyridin-1(2H)-yl}(phenyl)acetic acid The title compound was prepared essentially as described in Example 1072B substituting Example 1077 for Example 1072A. $^1$H NMR (500 MHz, CD$_3$OD) δ 8.37 (d, J=6.1 Hz, 1H), 7.68-7.53 (m, 6H), 7.37-7.27 (m, 2H), 7.29-7.14 (m, 1H), 6.77 (s, 1H), 6.58-6.51 (m, 1H), 5.31 (s, 1H), 4.57-3.44 (m, 7H), 3.26-2.76 (m, 2H). MS (ESI$^+$) m/z 458.1 (M+H)$^+$.

EXAMPLE 1084

4-(5-fluoro-2-methoxyphenyl)-2-[1-(pyrrolidin-3-yl)-1,2,3,6-tetrahydropyridin-4-yl]-1H-pyrrolo[2,3-b]pyridine The title compound was prepared essentially as described in Example 913 substituting Example 1079 for Example 908. $^1$H NMR (400 MHz, CD$_3$OD) δ ppm 2.42-2.61 (m, 1H), 2.61-2.77 (m, 1H), 3.00-3.20 (m, 2H), 3.38-3.52 (m, 1H), 3.57-3.79 (m, 3H), 3.74-3.86 (m, 4H), 3.86-3.97 (m, 1H), 4.10-4.44 (m, 3H), 6.52-6.65 (m, 1H), 6.79 (s, 1H), 7.20-7.40 (m, 3H), 7.62 (d, J=6.2 Hz, 1H), 8.38 (d, J=6.2 Hz, 1H). MS (ESI$^+$) m/z 393.1 (M+H)$^+$.

EXAMPLE 1085

3-{4-[5-fluoro-4-(5-fluoro-2-methoxyphenyl)-1H-pyrrolo[2,3-b]pyridin-2-yl]piperidin-1-yl}-3-oxopropanenitrile The title compound was prepared according to the procedure described in Example 1055, substituting 2-cyanoacetic acid for 2-hydroxyacetic acid. $^1$H NMR (500 MHz, DMSO-d$_6$) δ 1.42-1.80 (m, 2H), 2.00 (dd, J=12.9, 7.9 Hz, 2H), 2.75 (td, J=12.9, 2.7 Hz, 1H), 2.91-3.23 (m, 3H), 3.72 (s, 3H), 4.04 (s, 2H), 4.38 (d, J=13.5 Hz, 1H), 5.91 (s, 1H), 6.94-7.49 (m, 3H), 11.76 (s, 1H). MS (ESI$^+$) m/z 411 (M+H)$^+$.

EXAMPLE 1086

5-fluoro-4-(5-fluoro-2-methoxyphenyl)-2-(1,2,3,6-tetrahydropyridin-4-yl)-1H-pyrrolo[2,3-b]pyridine-3-carbonitrile

EXAMPLE 1086A 4-chloro-5-fluoro-3-iodo-1H-pyrrolo[2,3-b]pyridine

A solution of 4-chloro-5-fluoro-1H-pyrrolo[2,3-b]pyridine (1.8 g, 10.5 mmol) in N,N-dimethylformamide (25 mL) was cooled in ice water and treated with N-iodosuccinimide (2.37 g, 10.55 mmol). The reaction was slowly brought to room temperature. After the completion of the reaction, it was quenched with brine (100 mL) and partitioned with ethyl acetate (2×100 mL). The organic phase was concentrated and purified by flash chromatography using an ISCO Companion eluting with heptanes/ethyl acetate (30%) to provide the title compound. MS (ESI$^+$) m/z 297 (M+H)$^+$.

EXAMPLE 1086B 4-chloro-5-fluoro-3-iodo-1-((2-(trimethylsilyl)ethoxy)methyl)-1H-pyrrolo[2,3-b]pyridine A solution of Example 1086A (2.8 g, 9.44 mmol) in tetrahydrofuran (200 mL) was cooled to 0° C. and treated with sodium hydride (0.34 g, 14.17 mmol). The mixture was stirred at 0° C. for 30 minutes and (2-(chloromethoxy)ethyl) trimethylsilane (2.5 mL, 14.17 mmol) was added. The mixture was warmed to room temperature, stirred for 2 hours, quenched with brine (100 mL) and extracted with ethyl acetate (2×100 mL). The organic phase was concentrated and purified by flash chromatography using an ISCO Companion eluting with heptanes/ethyl acetate (30%) to provide the title compound. MS (ESI$^+$) m/z 427 (M+H)$^+$.

EXAMPLE 1086C 4-chloro-5-fluoro-1-((2-(trimethylsilyl)ethoxy)methyl)-1H-pyrrolo[2,3-b]pyridine-3-carbonitrile A mixture of Example 1086B (2.5 g, 5.86 mmol), zinc cyanide (0.8 g, 7.0 mmol), 1,1'-bis(diphenylphosphino)ferrocene (0.4 g, 0.7 mmol) and tris(dibenzylideneacetone)dipalladium(0) (0.27 g, 0.3 mmol) in a mixed solvent of N,N-dimethylformamide (50 mL) and water (0.5 mL) was sparged with $N_2$ and stirred at 80° C. for overnight. The reaction was quenched with brine (100 mL) and extracted with ethyl acetate (2×100 mL). The organic phase was concentrated and purified by flash chromatography using an ISCO Companion eluting with heptanes/ethyl acetate (30%) to provide the title compound. MS (ESI$^+$) m/z 326 (M+H)$^+$.

EXAMPLE 1086D 5-fluoro-4-(5-fluoro-2-methoxyphenyl)-1-((2-(trimethylsilyl)ethoxy)methyl)-1H-pyrrolo[2,3-b]pyridine-3-carbonitrile The title compound was prepared essentially as described in Example 721B, substituting Example 1086C (2.8 g, 9.4 mmol) for Example 721A. MS (DCI/NH$_3$) m/z 416 (M+H)$^+$.

EXAMPLE 1086E 5-fluoro-4-(5-fluoro-2-methoxyphenyl)-2-iodo-1-((2-(trimethylsilyl)ethoxy)methyl)-1H-pyrrolo[2,3-b]pyridine-3-carbonitrile A solution of Example 1086D (0.72 g, 1.7 mmol) in tetrahydrofuran (50 mL) was cooled to −75° C. and treated with lithium diisopropylamide (2.6 mL, 5.2 mmol) dropwise. The reaction was stirred at −75° C. for 30 minutes, followed by addition of iodine (0.88 g in 2.5 mL tetrahydrofuran, 3.47 mmol). The reaction was slowly brought to room temperature. The mixture was quenched with saturated ammonium chloride (100 mL) solution and extracted with ethyl acetate (2×100 mL). The organic phase was concentrated and purified by flash chromatography using an ISCO Companion eluting with heptanes/ethyl acetate (30%) to provide the title compound. MS (ESI$^+$) m/z 542 (M+H)$^+$.

EXAMPLE 1086F tert-butyl 4-(3-cyano-5-fluoro-4-(5-fluoro-2-methoxyphenyl)-1-((2-(trimethylsilyl)ethoxy)methyl)-1H-pyrrolo[2,3-b]pyridin-2-yl)-5,6-dihydropyridine-1(2H)-carboxylate The title compound was prepared using the procedure described in Example 87C, substituting Example 1086E for Example 87B. MS (ESI$^+$) m/z 597 (M+H)$^+$.

EXAMPLE 1086G 5-fluoro-4-(5-fluoro-2-methoxyphenyl)-2-(1,2,3,6-tetrahydropyridin-4-yl)-1H-pyrrolo[2,3-b]pyridine-3-carbonitrile The title compound was prepared using the procedure described in Example 1H, substituting Example 1086F for Example 1G. $^1$H NMR (400 MHz, Methanol-d$_4$) δ 3.00 (ddq, J=6.3, 3.9, 2.1 Hz, 2H), 3.52 (t, J=6.1 Hz, 2H), 3.77 (s, 3H), 3.98 (q, J=2.7 Hz, 2H), 6.68 (tt, J=3.5, 1.7 Hz, 1H), 7.03-7.18 (m, 2H), 7.18-7.31 (m, 1H), 8.35 (d, J=2.3 Hz, 1H). MS (ESI$^+$) m/z 367 (M+H)$^+$.

EXAMPLE 1087

4-fluoro-2-[2-(1,2,3,6-tetrahydropyridin-4-yl)-1H-pyrrolo[2,3-b]pyridin-4-yl]benzamide The title compound was prepared essentially as described in Example 721D, substituting Example 673A (1.0 g, 1.7 mmol) for tert-butyl 4-(4,4,5,5-tetramethyl-1,3,2-dioxaborolan-2-yl)-5,6-dihydropyridine-1(2H)-carboxylate and 2-bromo-4-fluorobenzamide for 721C. $^1$H NMR (500 MHz, Methanol-d$_4$) δ 2.83 (q, J=4.5, 2.7 Hz, 2H), 3.47 (t, J=6.1 Hz, 2H), 3.94 (dd, J=3.8, 2.2 Hz, 2H), 6.49 (d, J=3.4 Hz, 1H), 6.60 (s, 1H), 7.14-7.45 (m, 3H), 7.80 (dd, J=8.4, 5.5 Hz, 1H), 8.35 (m, 1H). MS (ESI$^+$) m/z 337 (M+H)$^+$.

EXAMPLE 1088

{4-[3-cyano-5-fluoro-4-(5-fluoro-2-methoxyphenyl)-1H-pyrrolo[2,3-b]pyridin-2-yl]-3,6-dihydropyridin-1(2H)-yl}acetic acid

EXAMPLE 1088A tert-butyl 2-(4-(3-cyano-5-fluoro-4-(5-fluoro-2-methoxyphenyl)-1H-pyrrolo[2,3-b]pyridin-2-yl)-5,6-dihydropyridin-1(2H)-yl)acetate The title compound was prepared essentially as described in Examples 226A, substituting Example 1086 (320 mg, 0.9 mmol) for Example 87D. LC/MS m/z 481 (M+H)$^+$.

EXAMPLE 1088B 2-(4-(3-cyano-5-fluoro-4-(5-fluoro-2-methoxyphenyl)-1H-pyrrolo[2,3-b]pyridin-2-yl)-5,6-dihydropyridin-1(2H)-yl)acetic acid The title compound was prepared essentially as described in Examples 226B, substituting Example 1088A (105 mg, 0.2 mmol) for Example 226A. $^1$H NMR (400 MHz, Methanol-d$_4$) δ 3.12 (tq, J=5.7, 2.1 Hz, 2H), 3.69 (t, J=6.1 Hz, 2H), 3.77 (s, 3H), 4.18 (q, J=2.5 Hz, 2H), 4.22 (s, 2H), 6.66 (tt, J=3.5, 1.6 Hz, 1H), 7.01-7.17 (m, 2H), 7.24 (ddd, J=9.1, 8.2, 3.1 Hz, 1H), 8.35 (d, J=2.3 Hz, 1H). MS (ESI$^+$) m/z 425 (M+H)$^+$.

EXAMPLE 1089

2-aminoethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl(2-hydroxyethyl)carbamate in place of tert-butyl(2-hydroxyethyl)(methyl)carbamate. $^1$H NMR (500 MHz, dimethylsulfoxide-d$_6$) δ 12.88 (s, 1H), 11.60 (s, 1H), 8.41-8.24 (m, 4H), 7.40-7.21 (m, 4H), 6.77-6.66 (m, 1H), 6.48 (d, J=1.9 Hz, 1H), 4.27 (t, J=5.5 Hz, 2H), 4.10-4.05 (m, 2H), 3.77 (s, 3H), 3.51 (t, J=5.8 Hz, 2H), 3.11-3.02 (m, 2H), 2.70-2.57 (m, 2H). MS (ESI$^+$) m/z 490.3 (M+H)$^+$.

EXAMPLE 1090 azetidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using tert-butyl 3-(hydroxymethyl)azetidine-1-carboxylate in place of tert-butyl(2-hydroxyethyl)(methyl)carbamate. $^1$H NMR (500 MHz, dimethylsulfoxide-$d_6$) δ 12.46 (s, 1H), 11.60 (s, 1H), 9.34 (d, J=22.7 Hz, 2H), 8.27 (d, J=5.3 Hz, 1H), 7.39-7.17 (m, 4H), 6.70-6.58 (m, 1H), 6.39 (d, J=1.9 Hz, 1H), 4.22 (d, J=5.5 Hz, 2H), 4.08-3.96 (m, 4H), 3.76 (s, 3H), 3.74-3.65 (m, 2H), 3.50 (t, J=5.8 Hz, 2H), 3.06-2.96 (m, 1H), 2.67-2.57 (m, 2H). MS (ESI$^+$) m/z 516.3 (M+H)$^+$.

EXAMPLE 1091

2-(dimethylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared as described in Example 965 using 2-(dimethylamino)ethanol in place of tert-butyl (2-hydroxyethyl)(methyl)carbamate. $^1$H NMR (400 MHz, dimethylsulfoxide-$d_6$) δ 12.10-11.92 (m, 1H), 11.66 (s, 1H), 9.79 (s, 1H), 8.24 (d, J=5.0 Hz, 1H), 7.34-7.18 (m, 3H), 7.08 (d, J=5.0 Hz, 1H), 6.58-6.48 (m, 1H), 6.30 (d, J=1.9 Hz, 1H), 4.41-4.33 (m, 2H), 4.11-4.01 (m, 2H), 3.74 (s, 3H), 3.50 (t, J=5.7 Hz, 2H), 3.41-3.31 (m, 2H), 2.81 (s, 6H), 2.65-2.57 (m, 2H). MS (ESI$^+$) m/z 518.4 (M+H)$^+$.

EXAMPLE 1092

2-(2,2-dimethyl-1,2,3,6-tetrahydropyridin-4-yl)-4-(5-fluoro-2-methoxyphenyl)-1H-pyrrolo[2,3-b]pyridine The title compound was prepared using the procedure described in Example 271D using Example 272A in place of Example 271C. $^1$HNMR (500 MHz, DMSO-$d_6$) δ 1.36 (br s, 6H), 2.64 (s, 2H), 3.75 (s, 3H), 3.80 (br s, 2H), 6.46 (s, 1H), 6.59 (br s, 1H), 7.29 (m, 4H), 8.29 (d, 1H), 12.52 (br s, 1H). MS (ESI) m/e 352.1 (M+H)$^+$.

EXAMPLE 1093

{4-[3-cyano-4-(5-fluoro-2-methoxyphenyl)-1H-pyrrolo[2,3-b]pyridin-2-yl]piperidin-1-yl}acetic acid The title compound was prepared essentially as described in Example 1035F-G, substituting Example 1094E for Example 1035E in Example 1035F. $^1$H NMR (400 MHz, DMSO-$d_6$): δ 1.81-1.88 (m, 2 H), 2.00-2.12 (m, 2 H), 2.43-2.51 (m, 2 H), 2.94-3.02 (m, 2 H), 3.11 (d, J=11.60 Hz, 2 H), 3.22 (s, 2 H), 3.72 (s, 3 H), 7.11-7.18 (m, 3 H), 7.26-7.31 (m, 1 H), 8.35 (d, J=4.88 Hz, 1 H), 12.78 (s, 1 H); MS (ESI) m/z 409 (M+H)$^+$, 407 (M+H)$^-$.

EXAMPLE 1094

4-(5-fluoro-2-methoxyphenyl)-2-(piperidin-4-yl)-1H-pyrrolo[2,3-b]pyridine-3-carbonitrile

EXAMPLE 1094A tert-butyl 4-(4-chloro-3-iodo-1H-pyrrolo[2,3-b]pyridin-2-yl)piperidine-1-carboxylate To a suspension of Example 17E (2 g, 5.96 mmol) in acetonitrile (100 mL) was added N-iodosuccinimide (1.367 g, 6.07 mmol). The mixture was stirred at room temperature overnight. The volatiles were removed, and the residue was partitioned between ethyl acetate and brine. The residue was separated by flash chromatography to provide the title compound. MS (DCI/NH$_3$) m/z 462 (M+H)$^+$.

EXAMPLE 1094B tert-butyl 4-(4-chloro-3-iodo-1-((2-(trimethylsilyl)ethoxy)methyl)-1H-pyrrolo[2,3-b]pyridin-2-yl)piperidine-1-carboxylate A solution of Example 1094A (1.28 g, 2.77 mmol) in N,N-dimethylformamide (10 ml) was cooled to 0° C. and NaH (60% suspension in mineral oil, 122 mg, 3.05 mmol) was added. The mixture was stirred at the same temperature for 30 minutes then (2-(chloromethoxy)ethyl)trimethylsilane (0.555 g, 3.33 mmol) was added. The mixture was stirred at 0° C. for 1 hour, and was partitioned between ethyl acetate and brine. The organic phase was washed with brine, and concentrated. The residue was separated by flash chromatography (10-60% ethyl acetate/hexane) to provide the title compound. MS (DCI/NH$_3$) m/z 592 (M+H)$^+$.

EXAMPLE 1094C tert-butyl 4-(4-chloro-3-cyano-1-((2-(trimethylsilyl)ethoxy)methyl)-1H-pyrrolo[2,3-b]pyridin-2-yl)piperidine-1-carboxylate A mixture of Example 1094B (610 mg, 1.03 mmol), zinc cyanide (145 mg, 1.237 mmol), bis(dibenzylideneacetone)palladium (47.5 mg, 0.082 mmol) and 1,1'-bis(diphenylphosphine)ferrocene (68.5 mg, 0.124 mmol) was purged with nitrogen. N,N-Dimethylformamide (15 mL) and water (0.15 mL) were then added. The mixture was purged with nitrogen again and heated at 85° C. for 4 hours. After cooling, the reaction mixture was partitioned between ethyl acetate and brine. The organic phase was washed with brine and concentrated. The residue was separated by flash chromatography (20-70% ethyl acetate in hexane) to provide the title compound. MS (DCI/NH$_3$) m/z 491 (M+H)$^+$.

EXAMPLE 1094D tert-butyl 4-(3-cyano-4-(5-fluoro-2-methoxyphenyl)-1-((2-(trimethylsilyl)ethoxy)methyl)-1H-pyrrolo[2,3-b]pyridin-2-yl)piperidine-1-carboxylate A mixture of Example 1094C (330 mg, 0.672 mmol), 5-fluoro-2-methoxyphenylboronic acid (171 mg, 1.008 mmol), phenylallylchloro[1,3-bis(diisopropylphenyl)-2-imidazol-2-ylidene]palladium (II) (21 mg, 0.034 mmol) and potassium phosphate (428 mg, 2.016 mmol) was suspended in a mixture of tetrahydrofuran (9 mL) and water (3 mL). This suspension was purged with nitrogen, and heated at 60° C. for 1.5 hours. After cooling, the reaction mixture was partitioned between ethyl acetate and brine. The organic phase was washed with brine, and concentrated. The residue was separated by flash chromatography (50-90% ethyl acetate in hexane) to give the title compound. MS (DCI/NH$_3$) m/z 581 (M+H)$^+$.

EXAMPLE 1094E 4-(5-fluoro-2-methoxyphenyl)-2-(piperidin-4-yl)-1H-pyrrolo[2,3-b]pyridine-3-carbonitrile To a solution of Example 1094D (0.45 g, 0.775 mmol) in tetrahydrofuran (20 mL) was added HCl (37%, 4 mL), and the mixture was heated at 65° C. for 4 hours. The volatiles were removed, and the residue was purified by HPLC (Zorbax, C-18, 250×2.54 column, Mobile phase A: 0.1% trifluoroacetic acid in $H_2O$; B: 0.1% trifluoroacetic acid in $CH_3CN$; 0-100% gradient) to provide the title compound as trifluoroacetic acid salt. The material was partitioned between ethyl acetate and NaOH solution, and the organic phase was washed with water, and concentrated to provide title compound as free base. $^1$H NMR (400 MHz, $CD_3OD$): δ1.89-1.96 (m, 4 H), 2.71-2.81 (m, 2 H), 3.15-3.22 (m, 3 H), 3.77 (s, 3 H), 7.05-7.13 (m, 3 H), 7.15-7.22 (m, 1 H), 8.32 (d, J=4.88 Hz, 1 H); MS (ESI) m/z 351 (M+H)$^+$.

EXAMPLE 1095

2-{4-[3-cyano-4-(5-fluoro-2-methoxyphenyl)-1H-pyrrolo[2,3-b]pyridin-2-yl]piperidin-1-yl}-N,N-dimethylacetamide To a solution of Example 1094E (100 mg, 0.285 mmol) in N,N-dimethylformamide (7 mL) was added triethylamine (0.24 mL, 1.712 mmol) and 2-chloro-N,N-dimethylacetamide (42 mg, 0.342 mmol). The solution was heated at 70° C. for 3 hours. After cooling, the solution was partitioned between ethyl acetate and brine. The organic phase was washed with brine, and concentrated. The residue was purified by flash chromatography (5-20% $CH_3OH$ in 2:1 ethyl acetate/hexane) to provide the title compound. $^1$H NMR (400 MHz, DMSO-$d_6$): δ1.80 (d, J=11.29 Hz, 2 H), 1.94-2.07 (m, 2 H), 2.15-2.23 (m, 2 H), 2.82 (s, 3 H), 2.86-2.94 (m, 1 H), 2.98 (d, J=11.60 Hz, 2 H), 3.04 (s, 3 H), 3.18 (s, 2 H), 3.72 (s, 3 H), 7.10-7.18 (m, 3 H), 7.26-7.32 (m, 1 H), 8.34 (d, J=4.88 Hz, 1 H), 12.73 (s, 1 H); MS (ESI) m/z 436 (M+H)$^+$, 434 (M+H)$^-$.

EXAMPLE 1096

5-({4-[4-(5-fluoro-2-methoxyphenyl)-1H-pyrrolo[2,3-b]pyridin-2-yl]piperidin-1-yl}methyl)-2,4-dihydro-3H-1,2,4-triazol-3-one The title compound was prepared essentially as described in Example 637B substituting Example 135B for Example 87D. $^1$H NMR (500 MHz, DMSO-$d_6$) δ ppm 1.61-1.79 (m, 2H), 1.95-2.03 (m, 2H), 2.07-2.18 (m, 2H), 2.61-2.74 (m, 1H), 2.82-2.91 (m, 2H), 3.29 (s, 2H), 3.73 (s, 3H), 5.95 (d, J=2.0 Hz, 1H), 7.00 (d, J=4.9 Hz, 1H), 7.13-7.31 (m, 3H), 8.13 (d, J=4.9 Hz, 1H), 11.09-11.51 (m, 2H), 11.57 (d, J=2.2 Hz, 1H). MS (ESI$^+$) m/z 423.2 (M+H)$^+$.

EXAMPLE 1097

4-(5-fluoro-2-methoxyphenyl)-2-{1-[1-(methylsulfonyl)pyrrolidin-3-yl]-1,2,3,6-tetrahydropyridin-4-yl}-1H-pyrrolo[2,3-b]pyridine The title compound was prepared essentially as described in Example 119 substituting Example 1084 for Example 87D. $^1$H NMR (500 MHz, DMSO-$d_6$) δ ppm 1.74-1.88 (m, 1H), 2.04-2.20 (m, 1H), 2.43-2.49 (m, 2H), 2.56-2.74 (m, 2H), 2.91 (s, 3H), 2.92-3.31 (m, 6H), 3.53 (dd, J =9.6, 6.7 Hz, 1H), 3.74 (s, 3H), 6.19 (d, J=2.1 Hz, 1H), 6.44-6.51 (m, 1H), 7.02 (d, J=4.9 Hz, 1H), 7.14-7.32 (m, 3H), 8.19 (d, J=4.9 Hz, 1H), 11.78 (d, J=2.2 Hz, 1H). MS (ESI$^+$) m/z 471.1 (M+H)$^+$.

EXAMPLE 1098

2-{4-[4-(5-fluoro-2-methoxyphenyl)-1H-pyrrolo[2,3-b]pyridin-2-yl]piperidin-1-yl}-N-(propan-2-ylsulfonyl)acetamide A solution of Example 247B (0.055 g, 0.121 mmol) and N-ethyl-N-isopropylpropan-2-amine (0.053 ml, 0.301 mmol) in N,N-dimethylformamide (1 mL) was treated with 1,1'-carbonyldiimidazole (0.031 g, 0.193 mmol) and the reaction mixture was heated at 50° C. for 30 minutes. After cooling to room temperature, the reaction was treated with a solution of propane-2-sulfonamide (0.018 g, 0.145 mmol) and 1,8-diazabicyclo[5.4.0]undec-7-ene (0.051 ml, 0.339 mmol) in N,N-dimethylformamide (0.5 mL) and the mixture was stirred at room temperature for 22 hours. The reaction mixture was directly purified by reverse phase HPLC on a Phenomenex Luna C8(2) 5 um 100 Å AXIA column (30 mm×75 mm) eluting with a gradient of 10-95% acetonitrile in 0.1% ammonium acetate/water to afford the title compound. $^1$H NMR (400 MHz, DMSO-$d_6$) δ ppm 1.23 (d, J=6.9 Hz, 6H), 1.82-2.00 (m, 2H), 2.03-2.18 (m, 2H), 2.68-2.82 (m, 2H), 2.83-2.94 (m, 2H), 3.39 (s, 2H), 3.47-3.58 (m, 1H), 3.72 (s, 3H), 6.00 (s, 1H), 7.00 (d, J=4.9 Hz, 1H), 7.10-7.29 (m, 3H), 8.14 (d, J=4.9 Hz, 1H), 11.25-11.34 (m, 1H). MS (ESI$^+$) m/z 489.2 (M+H)$^+$.

EXAMPLE 1099 ethyl 2-{4-[4-(5-fluoro-2-methoxyphenyl)-1H-pyrrolo[2,3-b]pyridin-2-yl]piperidin-1-yl}-1,3-thiazole-5-carboxylate The title compound was prepared essentially as described in Example 1078 substituting Example 135B for Example 87D. $^1$H NMR (500 MHz, $CD_3OD$) δ ppm 1.32 (t, J=7.1 Hz, 3H), 1.79-1.96 (m, 2H), 2.13-2.22 (m, 2H), 3.04-3.17 (m, 1H), 3.25-3.36 (m, 2H), 3.75 (s, 3H), 4.11-4.21 (m, 2H), 4.27 (q, J=7.1 Hz, 2H), 6.09 (s, 1H), 7.08 (d, J=5.1 Hz, 1H), 7.10-7.19 (m, 3H), 7.81 (s, 1H), 8.12 (d, J=5.1 Hz, 1H). MS (ESI$^+$) m/z 481.2 (M+H)$^+$.

EXAMPLE 1100 methyl (4-{4-[4-(5-fluoro-2-methoxyphenyl)-1H-pyrrolo[2,3-b]pyridin-2-yl]-3,6-dihydropyridin-1(2H)-yl}cyclohexyl)acetate The title compound as the trifluoroacetic acid salt was obtained as a mixture of cis- and trans-isomers as described in Example 288A and Example 288B. $^1$H NMR (500 MHz, DMSO-$d_6$) δ ppm 0.92-1.06 (m, 1H), 1.20-1.33 (m, 1H), 1.35-1.53 (m, 3H), 1.55-1.99 (m, 4H), 2.19 (d, J=7.0 Hz, 1H), 2.23-2.38 (m, 2H), 2.38-2.47 (m, 2H), 2.60-2.72 (m, 2H), 3.15-3.27 (m, 2H), 3.58 (s, 3H), 3.73 (s, 3H), 6.17 (dd, J=8.2, 2.1 Hz, 1H), 6.45-6.53 (m, 1H), 7.02 (dd, J=4.9, 2.5 Hz, 1H), 7.14-7.32 (m, 3H), 8.18 (dd, J=5.0, 2.3 Hz, 1H), 11.75 (dd, J=9.5, 2.3 Hz, 1H). MS (ESI$^+$) m/z 478.1 (M+H)$^+$.

EXAMPLE 1101

3-{4-[4-(5-fluoro-2-methoxyphenyl)-1H-pyrrolo[2,3-b]pyridin-2-yl]-3,6-dihydropyridin-1(2H)-yl}-1-methylpyrrolidin-2-one A mixture of Example 87D (0.075 g, 0.189 mmol) and triethylamine (0.119 ml, 0.852 mmol) in N,N-dimethylformamide (1.721 ml) was treated with 3-bromo-1-methylpyrrolidin-2-one (0.084 g, 0.473 mmol) and the reaction was heated at 73° C. for 6 hours. The reaction mixture was poured into 10 mL water and the resulting oily suspension was allowed to stand at room temperature for 2 hours. The aqueous supernatant was separated away from the solid phase using a syringe. The solid was dissolved in 25 mL dichloromethane, dried over anhydrous sodium sulfate, filtered, and concentrated. The crude product was purified by flash chromatography on silica gel (AnaLogix IntelliFlash 280 system) eluting with a gradient of from 0% to 8% methanol in dichloromethane to afford the title compound. $^1$H NMR (400 MHz, CD$_3$OD) δ ppm 1.97-2.16 (m, 1H), 2.16-2.38 (m, 1H), 2.54-2.63 (m, 2H), 2.77 (dt, J=11.2, 5.6 Hz, 1H), 2.85 (s, 3H), 3.05 (dt, J=11.3, 5.7 Hz, 1H), 3.32-3.46 (m, 3H), 3.53-3.73 (m, 2H), 3.76 (s, 3H), 6.25 (s, 1H), 6.34-6.44 (m, 1H), 7.07 (d, J=5.1 Hz, 1H), 7.11-7.22 (m, 3H), 8.14 (d, J=5.1 Hz, 1H). MS (ESI$^+$) m/z 421.0 (M+H)$^+$.

EXAMPLE 1102

4-{4-[4-(5-fluoro-2-methoxyphenyl)-1H-pyrrolo[2,3-b]pyridin-2-yl]-3,6-dihydropyridin-1(2H)-yl}pyrrolidin-2-one The title compound was prepared essentially as described in Example 908 substituting pyrrolidine-2,4-dione for (S)-1-tert-butyl 2-methyl 4-oxopyrrolidine-1,2-dicarboxylate. $^1$H NMR (400 MHz, DMSO-d$_6$) δ ppm 2.10-2.26 (m, 1H), 2.26-2.36 (m, 1H), 2.42-2.48 (m, 2H), 2.56-2.66 (m, 2H), 3.05-3.24 (m, 4H), 3.27-3.46 (m, 1H), 3.73 (s, 3H), 6.19 (d, J=2.0 Hz, 1H), 6.44-6.52 (m, 1H), 7.02 (d, J=4.9 Hz, 1H), 7.13-7.33 (m, 3H), 7.60 (s, 1H), 8.19 (d, J=5.0 Hz, 1H), 11.77 (d, J=2.2 Hz, 1H). MS (ESI$^+$) m/z 407.2 (M+H)$^+$.

EXAMPLE 1103

2-{4-[4-(5-fluoro-2-methoxyphenyl)-1H-pyrrolo[2,3-b]pyridin-2-yl]piperidin-1-yl}-1,3-thiazole-5-carboxylic acid A mixture of Example 1099 (0.058 g, 0.121 mmol) in tetrahydrofuran (0.754 ml) and ethanol (0.754 ml) was treated with aqueous 2M lithium hydroxide (0.241 ml, 0.483 mmol) and the reaction was stirred at 50° C. for 7 hours. The mixture was concentrated. The residue was dissolved in 2 mL water and was extracted with 1 mL ethyl acetate. The aqueous layer was separated and was acidified with aqueous 2N HCl until a sticky precipitate formed (pH 6-7). The aqueous supernatant was decanted away from the solids using a syringe. The residual solids were triturated with 0.5 mL methanol and filtered to afford the title compound. $^1$H NMR (400 MHz, DMSO-d$_6$) δ ppm 1.69-1.87 (m, 2H), 2.01-2.15 (m, 2H), 2.98-3.10 (m, 1H), 3.13-3.35 (m, 2H), 3.73 (s, 3H), 3.99-4.14 (m, 2H), 6.02 (d, J=1.9 Hz, 1H), 7.02 (d, J=4.9 Hz, 1H), 7.08-7.32 (m, 3H), 7.77 (s, 1H), 8.15 (d, J=4.9 Hz, 1H), 11.64 (d, J=2.2 Hz, 1H). MS (ESI$^+$) m/z 453.2 (M+H)$^+$.

EXAMPLE 1105

N-{4-[5-fluoro-4-(5-fluoro-2-methoxyphenyl)-1H-pyrrolo[2,3-b]pyridin-2-yl]cyclohex-3-en-1-yl}-D-valine

EXAMPLE 1105A 4-chloro-5-fluoro-1-(phenylsulfonyl)-2-(1,4-dioxaspiro[4.5]dec-7-en-8-yl)-1H-pyrrolo[2,3-b]pyridine The title compound was prepared essentially as described in Example 87C, substituting Example 87B with Example 231B and tert-butyl 4-(4,4,5,5-tetramethyl-1,3,2-dioxaborolan-2-yl)-5,6-dihydropyridine-1(2H)-carboxylate with 4,4,5,5-tetramethyl-2-(1,4-dioxaspiro[4.5]dec-7-en-8-yl)-1,3,2-dioxaborolane. LCMS (APCI): 449.19 (M+H)$^+$.

EXAMPLE 1105B 5-fluoro-4-(5-fluoro-2-methoxyphenyl)-1-(phenylsulfonyl)-2-(1,4-dioxaspiro[4.5]dec-7-en-8-yl)-1H-pyrrolo[2,3-b]pyridine A solution of Example 1105A (250 mg, 0.557 mmol), phenylyallylchloro[1,3-bis(diisopropylphenyl)-2-imidazoyl-2-ylidene]palladium(II) (10.82 mg, 0.017 mmol), (5-fluoro-2-methoxyphenyl)boronic acid (123 mg, 0.724 mmol) and potassium phosphate (355 mg, 1.671 mmol) in tetrahydrofuran and water was stirred overnight at 65° C. The reaction mixture was cooled to room temperature, diluted with ethyl acetate and the organics were washed with sodium bicarbonate, water, and brine. The organics were dried over magnesium sulfate, filtered and concentrated. The material was purified by flash chromatography; (Analogix280 SF 12 g silica column, 10% to 60% ethyl acetate/hexanes, gradient over 30 minutes) to give the title compound. MS (ESI): 539.0 (M+H)$^+$.

EXAMPLE 1105C 5-fluoro-4-(5-fluoro-2-methoxyphenyl)-2-(1,4-dioxaspiro[4.5]dec-7-en-8-yl)-1H-pyrrolo[2,3-b]pyridine To a solution of Example 1105B (950 mg, 1.764 mmol) in 20 mL dioxane was added sodium hydroxide (2.94 ml, 17.64 mmol). The reaction was stirred at 100° C. for 6 hours, then cooled, diluted with 80 mL water, and stirred for 30 minutes. The solid was filtered and dried over high vacuum to give the title compound. MS (ESI): 339.2 (M+H)$^+$.

EXAMPLE 1105D 4-(5-fluoro-4-(5-fluoro-2-methoxyphenyl)-1H-pyrrolo[2,3-b]pyridin-2-yl)cyclohex-3-enone The title compound was prepared essentially as described in Example 241B, substituting Example 241A with Example 1105C. MS (ESI): 355.2 (M+H)$^+$.

EXAMPLE 1105E

N-{4-[5-fluoro-4-(5-fluoro-2-methoxyphenyl)-1H-pyrrolo[2,3-b]pyridin-2-yl]cyclohex-3-en-1-yl}-D-valine The title compound was prepared essentially as described in Example 241C, substituting Example 241B with Example 1105D. ¹H NMR (500 MHz, DMSO-d₆) δ ppm 11.95 (s, 1 H) 8.75-9.59 (m, 2 H) 8.20 (d, J=2.44 Hz, 1 H) 7.08-7.45 (m, 3 H) 6.46 (d, J=2.14 Hz, 1 H) 6.16 (s, 1 H) 4.04 (d, J=3.36 Hz, 1 H) 3.53-3.90 (m, 4 H) 3.23-3.38 (m, 1 H) 2.16-2.85 (m, 5 H) 1.71-1.96 (m, 1 H) 0.87-1.21 (m, 6 H). MS (ESI): 456.1 (M+H)⁺.

EXAMPLE 1106

N-{4-[5-fluoro-4-(5-fluoro-2-methoxyphenyl)-1H-pyrrolo[2,3-b]pyridin-2-yl]cyclohex-3-en-1-yl}-3-methyl-L-valine The title compound was prepared essentially as described in Example 241C, substituting Example 241B with Example 1105D and (R)-tert-butyl 2-amino-3-methylbutanoate hydrochloride with (S)-tert-butyl 2-amino-3,3-dimethylbutanoate, hydrochloric acid. ¹H NMR (400 MHz, DMSO-d₆) δ ppm 11.94 (s, 1 H) 8.41-9.18 (m, 2 H) 8.19 (d, J=2.44 Hz, 1 H) 7.06-7.47 (m, 3 H) 6.46 (s, 1 H) 6.16 (s, 1 H) 3.97 (d, J=9.77 Hz, 2 H) 3.67-3.80 (m, 3 H) 3.13-3.37 (m, 1 H) 2.65 (s, 2 H) 2.20-2.45 (m, 2 H) 1.71-2.08 (m, 1 H) 0.97-1.36 (m, 9 H). MS (ESI): 470.1 (M+H)⁺.

EXAMPLE 1107

5-fluoro-4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile The title compound was prepared according to the procedure described in Example 238, substituting Example 1088B for Example 226B and (S)-pyrrolidin-2-ylmethanol for azetidin-3-ol hydrochloride. ¹H NMR (400 MHz, Methanol-d₄) δ 1.89-2.14 (m, 4H), 3.01-3.23 (m, 3H), 3.35 (m, 2H), 3.42-3.57 (m, 2H), 3.62-3.75 (m, 2H), 3.77 (s, 3H), 4.03-4.21 (m, 2H), 4.23-4.40 (m, 2H), 6.68 (td, J=3.9, 2.1 Hz, 1H), 7.12 (td, J=8.7, 8.0, 3.7 Hz, 2H), 7.24 (ddd, J=9.2, 8.2, 3.2 Hz, 1H), 8.36 (d, J=2.3 Hz, 1H). MS (ESI⁺) m/z 508 (M+H)⁺.

EXAMPLE 1108

4-(5-fluoro-2-methoxyphenyl)-2-[1-(methylsulfonyl)piperidin-4-yl]-1H-pyrrolo[2,3-b]pyridine-3-carbonitrile To a suspension of Example 1094E (60 mg, 0.171 mmol) in anhydrous CH₂Cl₂ (5 mL) was added triethylamine (0.143 mL, 1.027 mmol) and methanesulfonyl chloride (30 mg, 0.257 mmol). The mixture was stirred at room temperature for 3 hours. The mixture was directly separated by flash chromatography (0-15% CH₃OH in 2:1 ethyl acetate/hexane) to provide the title compound. ¹H NMR (400 MHz, DMSO-d₆): δ 1.93-2.04 (m, 4 H), 2.86-2.93 (m, 3 H), 2.91 (s, 3 H), 3.07-3.15 (m, 1 H), 3.68-3.70 (m, 1 H), 3.72 (s, 3 H), 7.11-7.19 (m, 3 H), 7.27-7.31 (m, 1 H), 8.36 (d, J=4.88 Hz, 1 H), 12.82 (s, 1 H); MS (ESI) m/z 429 (M+H)⁺, 427 (M+H)⁻.

EXAMPLE 1109

{4-[5-fluoro-4-(5-fluoro-2-methoxyphenyl)-1H-pyrrolo[2,3-b]pyridin-2-yl]piperidin-1-yl}acetic acid The title compound was prepared as described in Example 259B. ¹H NMR (400 MHz, DMSO-d₆) δ 1.99 (q, J=12.4 Hz, 2H), 2.14-2.32 (m, 2H), 3.03 (tt, J=11.2, 3.7 Hz, 1H), 3.18 (td, J=12.3, 2.9 Hz, 2H), 3.52 (d, J=11.9 Hz, 2H), 3.73 (s, 3H), 4.08 (s, 2H), 5.97 (d, J=2.0 Hz, 1H), 6.62-7.78 (m, 3H), 8.17 (d, J=2.5 Hz, 1H), 11.83 (d, J=2.3 Hz, 1H). MS (ESI⁺) m/z 402 (M+H)⁺.

EXAMPLE 1110 methyl 1-({4-[4-(5-fluoro-2-methoxyphenyl)-1H-pyrrolo[2,3-b]pyridin-2-yl]cyclohex-3-en-1-yl}carbonyl)prolinate Example 219C (50 mg, 0.136 mmol), methyl pyrrolidine-2-carboxylate hydrochloride (33.9 mg, 0.205 mmol), O-(7-azabenzotriazol-1-yl)-N,N'N'N'-tetramethyluronium hexafluorophosphate (62.3 mg, 0.164 mmol), and triethylamine (57.1 μl, 0.409 mmol) in 2 mL dimethylformamide was stirred at room temperature overnight. The crude product was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as trifluoroacetic acid salt. ¹H NMR (500 MHz, DMSO-d₆) δ 1.52-2.08 (m, 5H), 2.08-2.66 (m, 5H), 2.77 (dddd, J=12.2, 9.1, 5.8, 2.8 Hz, 1H), 3.58-3.71 (m, 5H), 3.76 (s, 3H), 4.32 (dt, J=8.6, 4.2 Hz, 1H), 6.19-6.37 (m, 1H), 6.60 (dt, J=11.8, 6.6 Hz, 1H), 7.12-7.40 (m, 4H), 8.24 (d, J=5.2 Hz, 1H), 12.13 (d, J=3.6 Hz, 1H). MS (ESI⁺) m/z 478 (M+H)⁺.

EXAMPLE 1111

N-cyano-4-[3-cyano-5-fluoro-4-(5-fluoro-2-methoxyphenyl)-1H-pyrrolo[2,3-b]pyridin-2-yl]-3,6-dihydropyridine-1(2H)-carboxamide To a cooled to 0° C. solution of cyanamide (0.3 g, 7.02 mmol) and N-ethyl-N-isopropylpropan-2-amine (0.5 mL, 2.86 mmol) in N,N-dimethylformamide (2 mL), 4-nitrophenyl carbonochloridate (0.45 g, 2.23 mmol) was added. The mixture was stirred at room temperature overnight. Example 1086 (0.1 g, 0.232 mmol) was added to the mixture and the mixture was stirred overnight. The crude product was neutralized by trifluoroacetic acid and the product was purified by reverse-phase HPLC on a Sunfire C8 column (30×100 mm, 5 μm particle size, flow rate 30 mL/minute) using a gradient of 30-80% acetonitrile in 0.1% aqueous trifluoroacetic acid to provide the title compound as a trifluoroacetic acid salt. ¹H NMR (500 MHz, DMSO-d₆): δ 2.64-2.73 (m, 2 H) 3.60 (t, J=5.49 Hz, 2 H) 3.73 (s, 3 H) 4.16 (d, J=2.75 Hz, 2 H) 6.64-6.68 (m, 1 H) 7.16-7.21 (m, 1 H) 7.25-7.30 (m, 1 H) 7.32-7.38 (m, 1 H) 8.45 (d, J=2.14 Hz, 1 H) 10.64 (br.s, 1 H) 13.01 (s, 1 H). MS (ESI⁺) m/z: 435.0 (M+H)⁺.

EXAMPLE 1112

(4-{4-[4-(5-fluoro-2-methoxyphenyl)-1H-pyrrolo[2,3-b]pyridin-2-yl]-3,6-dihydropyridin-1(2H)-yl}cyclohexyl)acetic acid The title compound was prepared essentially as described in Example 681 substituting Example 1100 for Example 676. ¹H NMR (500 MHz, CD₃OD) δ ppm 1.14-1.26 (m, 1H), 1.55-1.89 (m, 4H), 1.94-2.08 (m, 2H), 2.12-2.32 (m, 3H), 2.43 (d, J=7.7 Hz, 1H), 2.87-3.01 (m, 2H), 3.32-3.43 (m, 2H), 3.77-3.90 (m, 4H), 4.04-4.14 (m, 2H), 6.49-6.56

(m, 1H), 6.62-6.68 (m, 1H), 7.17-7.32 (m, 3H), 7.40-7.46 (m, 1H), 8.19-8.48 (m, 1H). MS (ESI$^+$) m/z 464.0 (M+H)$^+$.

EXAMPLE 1113

3-{4-[4-(5-fluoro-2-methoxyphenyl)-1H-pyrrolo[2,3-b]pyridin-2-yl]piperidin-1-yl}-1-methylpyrrolidin-2-one The title compound was prepared essentially as described in Example 1101 substituting Example 135B for Example 87D. $^1$H NMR (400 MHz, DMSO-d$_6$) δ 11.54 (brs, 1H), 8.13 (d, J=4.9 Hz, 1H), 7.30-7.15 (m, 3H), 7.00 (d, J=4.8 Hz, 1H), 5.94 (d, J=1.9 Hz, 1H), 3.73 (s, 3H), 3.39-3.15 (m, 3H), 3.05-2.96 (m, 1H), 2.80-2.58 (m, 6H), 2.36-2.21 (m, 1H), 2.10-1.85 (m, 4H), 1.73-1.56 (m, 2H). MS (ESI$^+$) m/z 423.3 (M+H)$^+$.

EXAMPLE 1114

N-cyano-4-[5-fluoro-4-(5-fluoro-2-methoxyphenyl)-1H-pyrrolo[2,3-b]pyridin-2-yl]-3,6-dihydropyridine-1(2H)-carboxamide The title compound was prepared using the procedure described in Example 1111, using Example 695 in place of Example 1086. $^1$H NMR (500 MHz, DMSO-d$_6$): δ 3.73 (s, 3 H) 4.07-4.12 (m, 2 H) 6.22 (d, J=2.14 Hz, 1 H) 6.48-6.52 (m, 1 H) 7.18-7.27 (m, 2 H) 7.30-7.36 (m, 1 H) 8.20 (d, J=2.44 Hz, 1 H) 10.57 (br.s., 1 H) 11.98 (s, 1 H). MS (ESI$^+$) m/z: 410.1 (M+H)$^+$.

EXAMPLE 1115

4-(5-fluoro-2-methoxyphenyl)-2-(1-{[2-(2-methoxyethoxy)ethyl]sulfonyl}-1,2,3,6-tetrahydropyridin-4-yl)-1H-pyrrolo[2,3-b]pyridine The title compound was prepared using the procedure described in Example 258G, using 2-(2-methoxyethoxy)ethanesulfonyl chloride in place of methanesulfonyl chloride and Example 87D in place of Example 258F. $^1$H NMR (500 MHz, DMSO-d$_6$): δ 2.54-2.62 (m, 2 H) 3.20 (s, 3 H) 3.37-3.45 (m, 6 H) 3.52-3.57 (m, 2 H) 3.72-3.77 (m, 5 H) 3.97 (d, J=2.75 Hz, 2 H) 6.30 (d, J=1.83 Hz, 1 H) 6.52-6.56 (m, 1 H) 7.09 (d, J=4.88 Hz, 1 H) 7.18-7.32 (m, 3 H) 8.23 (d, J=5.19 Hz, 1 H) 11.98 (s, 1 H). MS (ESI$^+$) m/z: 490.2 (M+H)$^+$.

EXAMPLE 1116

1-({4-[3-cyano-5-fluoro-4-(5-fluoro-2-methoxyphenyl)-1H-pyrrolo[2,3-b]pyridin-2-yl]-3,6-dihydropyridin-1(2H)-yl}acetyl)-L-prolinamide The title compound was prepared according to the procedure described in Example 238 substituting Example 1088B for Example 226B and (S)-pyrrolidine-2-carboxamide for azetidin-3-ol hydrochloride. $^1$H NMR (400 MHz, Methanol-d$_4$) δ 1.88-2.18 (m, 3H), 2.27 (ddd, J=15.1, 9.6, 6.0 Hz, 1H), 2.99-3.26 (m, 2H), 3.45-3.70 (m, 3H), 3.77 (s, 3H), 3.78-4.00 (m, 1H), 4.06-4.29 (m, 2H), 4.35 (d, J=3.3 Hz, 2H), 4.49 (dd, J=8.8, 3.8 Hz, 1H), 6.68 (dt, J=4.1, 2.2 Hz, 1H), 7.12 (td, J =8.8, 8.1, 3.7 Hz, 2H), 7.24 (td, J=8.6, 3.1 Hz, 1H), 8.36 (d, J=2.3 Hz, 1H). MS (ESI$^+$) m/z 521 (M+H)$^+$.

EXAMPLE 1117

N-cyano-2-{4-[4-(5-fluoro-2-methoxyphenyl)-1H-pyrrolo[2,3-b]pyridin-2-yl]piperidin-1-yl}acetamide

EXAMPLE 1117A 2-chloro-N-cyanoacetamide

2-Chloroacetyl chloride (100 mg, 0.885 mmol) in 0.5 mL of dimethylformamide was added dropwise to a suspension of cyanamide (55.8 mg, 1.328 mmol) and N-ethyl-N-isopropylpropan-2-amine (232 µl, 1.328 mmol) in 2 mL of dimethylformamide at 0° C. with stirring. The reaction was allowed to proceed at room temperature overnight and directly used in the next step.

EXAMPLE 1117B

N-cyano-2-{4-[4-(5-fluoro-2-methoxyphenyl)-1H-pyrrolo[2,3-b]pyridin-2-yl]piperidin-1-yl}acetamide To a mixture of Example 17G (21.67 mg, 0.067 mmol) in dimethylformamide (0.5 ml) was added Example 1117A (0.5 mL, ~0.111 mmol) and triethylamine (0.031 ml, 0.222 mmol). The reaction mixture was stirred at room temperature for 2 days and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-d$_6$) δ ppm 1.71-1.85 (m, 3 H) 1.97-2.05 (m, 2 H) 2.41-2.48 (m, 2 H) 2.68-2.83 (m, 2 H) 3.12 (s, 2 H) 3.14 (s, 1 H) 3.73 (s, 3 H) 5.96 (s, 1 H) 7.01 (d, J=4.88 Hz, 1 H) 7.14-7.29 (m, 3 H) 8.14 (d, J=5.19 Hz, 1 H) 11.57 (s, 1 H). MS (ESI$^+$) m/z 408 (M+H)$^+$.

EXAMPLE 1118

{(2R)-4-[4-(5-fluoro-2-methoxyphenyl)-1H-pyrrolo[2,3-b]pyridin-2-yl]-1,2,5,6-tetrahydropyridin-2-yl}methanol

EXAMPLE 1118A (R)-tert-butyl 4-(4-(5-fluoro-2-methoxyphenyl)-1H-pyrrolo[2,3-b]pyridin-2-yl)-2-(((triisopropylsilyl)oxy)methyl)-5,6-dihydropyridine-1(2H)-carboxylate The title compound was prepared as described in Example 260A-D and 260F, substituting (R)-1-(tert-butoxycarbonyl)-4-oxopiperidine-2-carboxylic acid for (S)-1-(tert-butoxycarbonyl)-4-oxopiperidine-2-carboxylic acid in Example 260A. MS (ESI+) m/z 610.2 (M+H)+.

EXAMPLE 1118B (R)-tert-butyl 4-(4-(5-fluoro-2-methoxyphenyl)-1H-pyrrolo[2,3-b]pyridin-2-yl)-2-(hydroxymethyl)-5,6-dihydropyridine-1(2H)-carboxylate The title compound was prepared as described in Example 260G, substituting Example 1118A for Example 260E. MS (ESI+) m/z 454.1 (M+H)$^+$.

EXAMPLE 1118C

{(2R)-4-[4-(5-fluoro-2-methoxyphenyl)-1H-pyrrolo[2,3-b]pyridin-2-yl]-1,2,5,6-tetrahydropyridin-2-yl}methanol The title compound was prepared as the hydrochloride salt using the procedure described in Example 1H, using Example 1118B in place of Example 1G. $^1$H NMR (500 MHz, DMSO-$d_6$) δ 12.97 (s, 1H), 10.02-9.85 (m, 1H), 9.16 (dd, J=16.9, 8.3 Hz, 1H), 8.36 (d, J=5.6 Hz, 1H), 7.42-7.30 (m, 3H), 7.26 (dd, J=9.1, 4.5 Hz, 1H), 6.65 (s, 1H), 6.59 (s, 1H), 4.09 (br s, 1H), 3.82-3.77 (m, 1H), 3.77 (s, 3H), 3.73 (dd, J=11.6, 6.9 Hz, 1H), 3.42 (dd, J=11.0, 4.8 Hz, 1H), 3.26-3.17 (m, 1H), 2.83-2.71 (m, 2H); MS (ESI+) m/z 354.1 (M+H)$^+$.

EXAMPLE 1119

{(2R)-4-[4-(5-fluoro-2-methoxyphenyl)-1H-pyrrolo[2,3-b]pyridin-2-yl]-1,2,3,6-tetrahydropyridin-2-yl}methanol The title compound was prepared essentially as described in Example 260A-H, substituting (R)-1-(tert-butoxycarbonyl)-4-oxopiperidine-2-carboxylic acid for (S)-1-(tert-butoxycarbonyl)-4-oxopiperidine-2-carboxylic acid in the procedure described for Example 260A. $^1$H NMR (400 MHz, DMSO-$d_6$) δ 12.63 (s, 1H), 9.51 (d, J=9.2 Hz, 1H), 9.26 (mj, 1H), 8.31 (d, J=5.4 Hz, 1H), 7.39-7.16 (m, 4H), 6.62 (s, 1H), 6.46 (d, J=1.4 Hz, 1H), 3.93-3.76 (m, 2H), 3.76 (s, 3H), 3.65 (dd, J=11.6, 6.2 Hz, 1H), 3.47-3.36 (m, 1H), 2.77 (d, J=14.3 Hz, 1H), 2.64-2.53 (m, 1H); MS (ESI+) m/z 354.0 (M+H)$^+$.

EXAMPLE 1120 ethyl ({4-[5-fluoro-4-(5-fluoro-2-methoxyphenyl)-1H-pyrrolo[2,3-b]pyridin-2-yl]piperidin-1-yl}sulfonyl)carbamate The title compound was prepared essentially as described in Example 218, substituting ethanol for tert-butanol in Example 218A and substituting Example 255D for Example 87D in Example 218B. $^1$H NMR (400 MHz, DMSO-$d_6$) δ 1.19 (t, J=7.1 Hz, 3H), 1.69 (qd, J=12.3, 4.1 Hz, 2H), 1.94-2.16 (m, 2H), 2.75-3.06 (m, 3H), 3.72 (s, 5H), 4.10 (q, J=7.1 Hz, 2H), 5.92 (d, J=2.1 Hz, 1H), 7.01-7.64 (m, 3H), 8.14 (d, J=2.6 Hz, 1H), 11.25 (s, 1H), 11.75 (d, J=2.2 Hz, 1H). MS (ESI$^+$) m/z 495 (M+H)$^+$.

EXAMPLE 1121

2-{4-[5-fluoro-4-(5-fluoro-2-methoxyphenyl)-1H-pyrrolo[2,3-b]pyridin-2-yl]piperidin-1-yl}-N-(2-hydroxyethyl)-N-methylacetamide The title compound was prepared using the procedure described in Example 238, substituting Example 259B for Example 226B and 2-(methylamino)ethanol for azetidin-3-ol hydrochloride. $^1$H NMR (500 MHz, DMSO-$d_6$) δ 1.70 (p, J=14.0 Hz, 2H), 2.08 (d, J=123.7 Hz, 3H), 2.50 (s, 3H), 2.69 (q, J=19.4, 15.5 Hz, 1H), 2.81 (s, 2H), 2.87-3.02 (m, 2H), 3.05 (s, 1H), 3.11-3.32 (m, 1H), 3.50 (dt, J=43.4, 5.6 Hz, 3H), 3.72 (s, 3H), 5.90 (d, J=5.7 Hz, 1H), 6.99-7.65 (m, 3H), 8.13 (d, J=2.5 Hz, 1H), 11.72 (s, 1H). MS (ESI$^+$) m/z 459 (M+H)$^+$.

EXAMPLE 1122

4-[4-(5-fluoro-2-methoxyphenyl)-1H-pyrrolo[2,3-b]pyridin-2-yl]cyclohex-3-en-1-yl[(3-hydroxyazetidin-1-yl)sulfonyl]carbamate

EXAMPLE 1122A ((4-(dimethylamino)pyridin-1-ium-1-yl)sulfonyl)(((4-(4-(5-fluoro-2-methoxyphenyl)-1-(phenylsulfonyl)-1H-pyrrolo[2,3-b]pyridin-2-yl)cyclohex-3-en-1-yl)oxy)carbonyl)amide To a solution of Example 995C (1.5 g, 3.13 mmol) in anhydrous methylene chloride (40 mL) was added dropwise with cooling with ice chlorosulfonyl isocyanate (0.273 mL, 3.13 mL) over 15 minutes. After stirring for 30 minutes, 4-dimethylaminopyridine (0.766 g, 6.27 mmol) was added. The solution was stirred at 0° C. for 30 minutes and at room temperature for 1 hour before it was washed with water. The organic phase was dried over magnesium sulfate, filtered and concentrated to provide the title compound. MS (ESI) m/z 706 (M+H)$^+$.

EXAMPLE 1122B 4-(4-(5-fluoro-2-methoxyphenyl)-1-(phenylsulfonyl)-1H-pyrrolo[2,3-b]pyridin-2-yl)cyclohex-3-en-1-yl (3-hydroxyazetidin-1-yl)sulfonylcarbamate To a solution of Example 1122A (200 mg, 0.283 mg) in methylene chloride (7 mL) was added 3-hydroxyazetidine hydrochloride (31 mg, 0.283 mmol) and triethylamine (0.158 mL, 1.134 mmol). The mixture was stirred at room temperature overnight, and was directly separated by flash chromatography (0-15% $CH_3OH$ in methylene chloride) to provide the title compound. MS (APCI) m/z 656 (M+H)$^+$.

EXAMPLE 1122C

4-[4-(5-fluoro-2-methoxyphenyl)-1H-pyrrolo[2,3-b]pyridin-2-yl]cyclohex-3-en-1-yl[(3-hydroxyazetidin-1-yl)sulfonyl]carbamate To a solution of Example 1122B (180 mg, 0.274 mmol) in a mixture of dioxane (4.5 mL) and water (1.5 mL) was added NaOH (50% solution in water, 0.226 g, 2.83 mmol). The mixture was heated at 70° C. for 4 hours. After cooling, water was added and the mixture was acidified to a pH 4. The mixture was concentrated and the residue was separated by HPLC (Zorbax, C-18, 250×2.54 column, Mobile phase A: 0.1% trifluoroacetic acid in $H_2O$; B: 0.1% trifluoroacetic acid in $CH_3CN$; 0-100% gradient) to provide the title compound as trifluoroacetic acid salt. $^1$H NMR (400 MHz, DMSO-$d_6$): δ 1.88-2.00 (m, 2 H), 2.34-2.40 (m, 1 H), 2.52-2.57 (m, 1 H), 2.67 (d, J=18.62 Hz, 1 H), 2.95-3.04 (m, 2 H), 3.53 (dd, J=11.29, 5.49 Hz, 1 H), 3.65 (dd, J=11.14, 4.12 Hz, 1 H), 3.74-3.79 (m, 1 H), 3.77 (s, 3 H), 4.95-5.01 (m, 1 H), 6.43 (d, J=1.53 Hz, 1 H), 6.58 (s, 1 H), 7.22-7.38 (m, 4 H), 7.67-7.71 (m, 1 H), 8.30 (d, J=5.49 Hz, 1 H), 11.21 (s, 1 H), 12.70 (s, 1 H); MS (ESI) m/z 517 (M+H)$^+$, 515 (M+H)$^-$.

EXAMPLE 1123

4-(5-fluoro-2-methoxyphenyl)-2-{1-[(2-methoxyethyl)sulfonyl]-1,2,3,6-tetrahydropyridin-4-yl}-1H-pyrrolo[2,3-b]pyridine The title compound was prepared using the procedure described in Example 258G, using 2-methoxyethanesulfonyl chloride in place of methanesulfonyl chloride and Example 87D in place of Example 258F. $^1$H NMR (500 MHz, DMSO-$d_6$): δ 2.55-2.60 (m, 2 H) 3.26 (s, 3 H) 3.67 (t, J=6.10 Hz, 2 H) 3.74 (s, 3 H) 3.94 (d, J=2.75 Hz, 2 H) 6.28 (d, J=1.83 Hz, 1 H) 6.50-6.55 (m, 1 H) 7.06 (d, J=4.88 Hz, 1 H) 7.18-7.31 (m, 3 H) 8.22 (d, J=4.88 Hz, 1 H) 11.90 (s, 1 H). MS (ESI$^+$) m/z: 446.2 (M+H)$^+$.

EXAMPLE 1124

N-{4-[4-(5-fluoro-2-methoxyphenyl)-1H-pyrrolo[2,3-b]pyridin-2-yl]cyclohex-3-en-1-yl}-2-(2-methoxyethoxy)ethanesulfonamide The title compound was prepared using the procedure described in Example 943, using 2-(2-methoxyethoxy)ethanesulfonyl chloride in place of methanesulfonyl chloride. $^1$H NMR (500 MHz, DMSO-$d_6$): δ 1.56-1.69 (m, 1 H) 1.94-2.02 (m, 1 H) 2.14-2.24 (m, 1 H) 2.38-2.47 (m, 1 H) 2.52-2.61 (m, 2 H) 3.24 (s, 3 H) 3.33 (t, J=6.71 Hz, 2 H) 3.42-3.47 (m, 2 H) 3.52-3.56 (m, 2 H) 3.71-3.77 (m, 6 H) 6.21 (d, J=1.83 Hz, 1 H) 6.42-6.47 (m, 1 H) 7.04-7.09 (m, 2 H) 7.17-7.31 (m, 3 H) 8.20 (d, J=4.88 Hz, 1 H) 11.84 (s, 1 H). MS (ESI$^+$) m/z: 504.2 (M+H)$^+$.

EXAMPLE 1125 tert-butyl 3-{4-[4-(5-fluoro-2-methoxyphenyl)-1H-pyrrolo[2,3-b]pyridin-2-yl]-3,6-dihydropyridin-1(2H)-yl}cyclobutanecarboxylate The title compound was prepared essentially as described in Example 288A substituting tert-butyl 3-oxocyclobutanecarboxylate for methyl 2-(4-oxocyclohexyl)acetate. $^1$H NMR (500 MHz, CD$_3$OD) δ ppm 1.44 (s, 9H), 2.05-2.18 (m, 2H), 2.31-2.43 (m, 2H), 2.54-2.68 (m, 4H), 2.71-2.93 (m, 2H), 3.10-3.17 (m, 2H), 3.76 (s, 3H), 6.26 (s, 1H), 6.34-6.43 (m, 1H), 7.07 (d, J=5.0 Hz, 1H), 7.12-7.21 (m, 3H), 8.15 (d, J=5.1 Hz, 1H). MS (ESI$^+$) m/z 478.0 (M+H)$^+$.

EXAMPLE 1126

3-{4-[4-(5-fluoro-2-methoxyphenyl)-1H-pyrrolo[2,3-b]pyridin-2-yl]-3,6-dihydropyridin-1(2H)-yl})cyclobutanecarboxylic acid A solution of Example 1125 (0.045 g, 0.094 mmol) and trifluoroacetic acid (0.167 ml, 2.167 mmol) in dichloromethane (0.942 ml) was stirred at room temperature for 24 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% ammonium acetate/water to afford the title compound. $^1$H NMR (500 MHz, CD$_3$OD) δ ppm 2.42-2.55 (m, 2H), 2.62-2.77 (m, 2H), 2.83-2.96 (m, 2H), 2.96-3.07 (m, 1H), 3.16-3.37 (m, 1H), 3.46-4.28 (m, 7H), 6.41-6.48 (m, 1H), 6.54 (s, 1H), 7.14-7.26 (m, 3H), 7.28 (d, J=5.4 Hz, 1H), 8.28 (d, J=5.5 Hz, 1H). MS (ESI$^+$) m/z 422.0 (M+H)$^+$.

EXAMPLE 1127

4-(5-fluoro-2-methoxyphenyl)-2-[2-(methylsulfonyl)octahydrocyclopenta[c]pyrrol-5-yl]-1H-pyrrolo[2,3-b]pyridine Example 262G (34 mg, 0.080 mmol) and ethanol (10 ml) were added to 20% Pd(OH)$_2$/C (20 mg, 0.015 mmol) in a 100 mL pressure bottle. The mixture was stirred for 16 hours under 30 psi of hydrogen and 50° C. The reaction mixture was filtered. The filtrate was concentrated and purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (500 MHz, DMSO-$d_6$) δ ppm 1.48-1.61 (m, 2 H) 2.28-2.40 (m, 2 H) 2.74-2.83 (m, 2 H) 2.90 (s, 3 H) 3.07-3.13 (m, 2 H) 3.13-3.20 (m, 1 H) 3.21-3.27 (m, J=9.31, 7.17 Hz, 2 H) 3.72 (s, 3 H) 5.99 (d, J=1.22 Hz, 1 H) 7.00 (d, J=4.88 Hz, 1 H) 7.15-7.22 (m, 2 H) 7.21-7.28 (m, 1 H) 8.13 (d, J=4.88 Hz, 1 H) 11.64 (s, 1 H). MS (ESI$^+$) m/z 430 (M+H)$^+$.

EXAMPLE 1128

[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]acetic acid

EXAMPLE 1128A (S)-tert-butyl 2-(4-(4-(5-fluoro-2-methoxyphenyl)-1H-pyrrolo[2,3-b]pyridin-2-yl)-2-(hydroxymethyl)-2,5-dihydro-1H-pyrrol-1-yl)acetate The title compound was prepared using the procedure described in Example 224, using Example 869 in place of Example 87 and tert-butyl 2-bromoacetate in place of 2-chloro-N,N-dimethylacetamide.

EXAMPLE 1128B

[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]acetic acid The title compound was prepared using the procedure described in Example 226B, using Example 1128A in place of Example 226A. $^1$H NMR (400 MHz, DMSO-$d_6$) δ 12.24 (s, 1H), 8.30 (d, J=4.9 Hz, 1H), 7.36-7.18 (m, 3H), 7.11 (d, J=5.0 Hz, 1H), 6.43 (s, 1H), 6.42 (s, 1H), 4.70 (s, 2H), 4.52-4.43 (m, 1H), 4.37 (s, 2H), 3.86-3.77 (m, 2H), 3.74 (s, 3H). MS (ESI+) m/e 398 (M+H)$^+$.

EXAMPLE 1129

N$^2$-{4-[4-(5-fluoro-2-methoxyphenyl)-1H-pyrrolo[2,3-b]pyridin-2-yl]cyclohex-3-en-1-yl}-N-methyl-D-valinamide The title compound was prepared essentially as described in Example 1019, substituting dimethylamine hydrochloride with methanamine hydrochloride to provide the title compound. $^1$H NMR (500 MHz, DMSO-$d_6$) δ ppm 11.70 (s, 1 H) 8.17 (d, J=4.88 Hz, 1 H) 7.77-7.91 (m, 1 H) 7.10-7.33 (m, 3 H) 7.01 (d, J=4.88 Hz, 1 H) 6.44 (d, J=12.51 Hz, 1 H) 6.16 (d, J=1.83 Hz, 1 H) 3.73 (s, 3 H) 2.84 (dd, J=13.73, 6.41 Hz, 1 H) 2.59-2.67 (m, 3 H) 2.52-2.58 (m, 2 H) 2.21-2.41 (m, 2 H) 1.95-2.06 (m, 1 H) 1.84-1.96 (m, 1 H) 1.76-1.85 (m, 1 H) 1.66-1.77 (m, 1 H) 1.33-1.55 (m, 1 H) 0.77-0.93 (m, 6 H). MS (ESI): 451.1 (M+H)$^+$.

EXAMPLE 1135

2-[1-(cyanoacetyl)-1,2,3,6-tetrahydropyridin-4-yl]-4-(5-fluoro-2-methoxyphenyl)-1H-pyrrolo[2,3-b]pyridine-5-carbonitrile The title compound was prepared according to the procedure described in Example 1055, substituting 2-cyanoacetic acid for 2-hydroxyacetic acid and Example 236F for Example 255D. $^1$H NMR (500 MHz, DMSO-$d_6$) δ 2.46 (q, J=10.2, 7.9 Hz, 1H), 2.59 (t, J=6.8 Hz, 1H), 3.54 (t, J=5.9 Hz, 1H), 3.63 (td, J=13.3, 12.9, 5.8 Hz, 1H), 3.76 (s, 3H), 4.14-4.24 (m, 4H), 6.33 (d, J=10.2 Hz, 1H), 6.59 (d, J=6.1 Hz, 1H), 7.17-7.62 (m, 3H), 8.62 (s, 1H), 12.56 (d, J=10.8 Hz, 1H). MS (ESI$^+$) m/z 416 (M+H)$^+$.

EXAMPLE 1136

4-(5-fluoro-2-methoxyphenyl)-2-[1-(methylsulfonyl)-1,2,3,6-tetrahydropyridin-4-yl]-3-nitro-1H-pyrrolo[2,3-b]pyridine

EXAMPLE 1136A 4-bromo-2-(1-(methylsulfonyl)-1,2,3,6-tetrahydropyridin-4-yl)-3-nitro-1H-pyrrolo[2,3-b]pyridine Example 220F (0.15 g, 0.421 mmol) was added to fuming nitric acid (1 mL, 22.38 mmol) at (−78° C.). The mixture was stirred at −78° C. for 30 minutes and diluted with water. The mixture was neutralized with $K_2CO_3$ and extracted with dichloromethane. The organic layer was dried over sodium sulfate. After filtration and removal of the solvents, the residue was purified by flash chromatography on silica gel (AnaLogix IntelliFlash) eluting with a gradient of 0-20% methanol in dichloromethane to afford the title compound. MS (ESI+) m/z 401.0 (M+H)+.

EXAMPLE 1136B 4-(5-fluoro-2-methoxyphenyl)-2-[1-(methylsulfonyl)-1,2,3,6-tetrahydropyridin-4-yl]-3-nitro-1H-pyrrolo[2,3-b]pyridine The title compound was prepared using the procedure described in Example 94C, using Example 1136A in place of Example 94B. $^1$H NMR (500 MHz, DMSO-$d_6$): δ 2.54-2.61 (m, 2 H) 2.99 (s, 3 H) 3.38-3.43 (m, 2 H) 3.51 (s, 3 H) 3.86-4.00 (m, 2 H) 6.30-6.35 (m, 1 H) 6.98-7.04 (m, 1 H) 7.20-7.29 (m, 3 H) 8.45 (d, J=4.88 Hz, 1 H) 13.09 (s, 1 H). MS (ESI$^+$) m/z: 447.1 (M+H)$^+$.

EXAMPLE 1137

4-(5-fluoro-2-methoxyphenyl)-2-(2-{[2-(2-methoxyethoxy)ethyl]sulfonyl}-1,2,3,3a,4,6a-hexahydrocyclopenta[c]pyrrol-5-yl)-1H-pyrrolo[2,3-b]pyridine The title compound was prepared using the procedure described in Example 262F, using 2-(2-methoxyethoxy)ethanesulfonyl chloride in place of methanesulfonyl chloride. $^1$H NMR (500 MHz, DMSO-$d_6$): δ 2.57-2.63 (m, 1 H) 2.88-2.96 (m, 1 H) 2.98-3.07 (m, 2 H) 3.16 (s, 3 H) 3.19-3.25 (m, 2 H) 3.34-3.37 (m, 2 H) 3.42-3.63 (m, 6 H) 3.68-3.72 (m, 2 H) 3.73 (s, 3 H) 6.19 (d, J=1.83 Hz, 1 H) 6.30 (s, 1 H) 7.04 (d, J=4.88 Hz, 1 H) 7.17-7.30 (m, 3 H) 8.21 (d, J=4.88 Hz, 1 H) 11.92 (s, 1 H). MS (ESI$^+$) m/z: 516.3 (M+H)$^+$.

EXAMPLE 1138

(9aR)-8-[4-(5-fluoro-2-methoxyphenyl)-1H-pyrrolo[2,3-b]pyridin-2-yl]-1,6,7,9a-tetrahydropyrido[2,1-c][1,4]oxazin-3(4H)-one 2-Chloro-N,N-dimethylacetamide (45 mg, 0.37 mmol) was added to a stirred mixture of Example 1118 (150 mg, 0.35 mmol) and diisopropylethylamine (227 mg, 1.76 mmol) in dimethylformamide (1.5 mL) in a sealable reaction vessel. The vessel was closed and the mixture was heated to 210° C. for 20 minutes. After cooling to room temperature, the mixture was partitioned between water (5 mL) and ethyl acetate (3×5 mL). The organic layers were dried ($Na_2SO_4$), filtered and concentrated then purified by flash chromatography (0 to 8% $CH_3OH$—$CH_2Cl_2$ over 35 minutes, 4 g column, 18 mL/min) to provide the title compound. $^1$H NMR (400 MHz, DMSO-$d_6$) δ 11.86-11.83 (m, 1H), 8.22 (d, J=5.0 Hz, 1H), 7.32-7.16 (m, 3H), 7.04 (d, J=4.9 Hz, 1H), 6.31 (d, J=1.9 Hz, 1H), 6.29 (s, 1H), 4.43 (dd, J=10.3, 3.5 Hz, 1H), 4.04-3.97 (m, 1H), 3.74 (d, J=17.3 Hz, 1H), 3.74 (s, 3H), 3.35-3.29 (m, 1H), 3.20 (d, J=17.2 Hz, 1H), 3.00-2.93 (m, 1H), 2.56 (d, J=12.3 Hz, 2H), 2.38 (td, J=10.7, 4.7 Hz, 1H). MS (ESI+) m/z 394.2 (M+H)$^+$.

EXAMPLE 1139

7-[4-(5-fluoro-2-methoxyphenyl)-1H-pyrrolo[2,3-b]pyridin-2-yl]-1,5,6,8a-tetrahydro[1,3]oxazolo[3,4-a]pyridin-3-one

EXAMPLE 1139A 4-vinyloxazolidin-2-one 2-(N-tert-Butylcarbonylamino)-3-buten-1-ol (5 g, 160 mmol) was dissolved in tetrahydrofuran (200 ml). The solution was chilled in an ice bath and then thionyl chloride (12.47 ml, 171 mmol) was added dropwise via an addition funnel over about 20 minutes. The reaction was then allowed to warm to room temperature overnight then concentrated to dryness and purified by flash chromatography (0 to 90% ethyl acetate-heptane, 40 g Grace column, 30 mL/min) to provide the title compound. MS (ESI+) m/z 130.8 (M+NH$_4$)$^+$.

EXAMPLE 1139B 3-(but-3-yn-1-yl)-4-vinyloxazolidin-2-one

A solution of Example 1139A (1 g, 8.84 mmol) in toluene (30 ml) was treated with potassium carbonate (7.33 g, 53.0 mmol), tetrabutylammonium bromide (0.285 g, 0.884 mmol) and but-3-yn-1-yl 4-methylbenzenesulfonate (7.00 ml, 44.2 mmol). The mixture was heated to 110° C. for 48 hours. Additional but-3-yn-1-yl 4-methylbenzenesulfonate (7.00 ml, 44.2 mmol) and potassium carbonate (7.33 g, 53.0 mmol) were added and the mixture was stirred at 110 C another 48 hours. The mixture was cooled to room temperature and partitioned between water (50 mL) and ethyl acetate (3×75 mL). The extracts were dried ($Na_2SO_4$), filtered, and concentrated. The crude residue was purified by flash chromatography (0 to 40% ethyl acetate-heptanes over 30 minutes, 12 g Grace column, 28 L/min) to provide the title compound. MS (ESI+) m/z 166.0 (M+H)+.

EXAMPLE 1139C 3-(3-(4,4,5,5-tetramethyl-1,3,2-dioxaborolan-2-yl) but-3-en-1-yl)-4-vinyloxazolidin-2-one A 3-neck round bottomed flask was charged with copper (I) chloride (360 mg, 3.63 mmol) and lithium chloride (154 mg, 3.63 mmol), then degassed with nitrogen. Dimethylformamide (3 ml) was added via syringe and the mixture was stirred for 1 hour, and then potassium acetate (356 mg, 3.63 mmol) and 4,4,4',4',5,5,5',5'-octamethyl-2,2'-bi(1,3,2-dioxaborolane) (922 mg, 3.63 mmol) were added and the mixture was stirred for 5 minutes. A solution of Example 1139B (500 mg, 3.03 mmol) in N,N-dimethylformamide (1 mL) was added and the mixture was stirred overnight at room temperature and then 6 hours at 50° C. The reaction mixture was diluted with saturated aqueous NH$_4$Cl (15 mL) and ethyl acetate (20 mL). The layers were separated and the aqueous phase was extracted further with ethyl acetate (3×10 mL). The combined extracts were dried (Na$_2$SO$_4$), filtered, and concentrated then purified by flash chromatography (100% heptane for 5 minutes then 0 to 25% ethyl acetate-heptanes over 25 minutes, 28 mL/minute, 12 g Grace column) to provide the title compound. MS (ESI+) m/z 294.0 (M+H)+.

EXAMPLE 1139D 7-(4,4,5,5-tetramethyl-1,3,2-dioxaborolan-2-yl)-5,6-dihydro-1H-oxazolo[3,4-a]pyridin-3(8aH)-one Example 1139C (100 mg, 0.341 mmol) and benzylidene [1,3-bis(2,4,6-trimethylphenyl)-2-imidazolidinylidene]dichloro(tricyclohexyl-phosphine)ruthenium (8.69 mg, 10.23 µmol) were combined in a flask, which was then flushed with nitrogen. CH$_2$Cl$_2$ (65 mL) was added the flask and the reaction was stirred overnight at room temperature, and the flask was opened to air and 50 µL dimethylsulfoxide was added. The reaction mixture was stirred at room temperature overnight then concentrated onto silica and purified by flash chromatography (0 to 40% ethyl acetate-heptanes over 35 minutes, 4 g column, 18 mL/minute) to provide the title compound. MS (ESI+) m/z 266.1 (M+H)+.

EXAMPLE 1139E

7-[4-(5-fluoro-2-methoxyphenyl)-1H-pyrrolo[2,3-b] pyridin-2-yl]-1,5,6,8a-tetrahydro[1,3]oxazolo[3,4-a]pyridin-3-one Example 219A (82 mg, 0.223 mmol), Example 1139D (59 mg, 0.223 mmol), PdC$_2$(1,1'-bis(diphenylphosphino)ferrocene)-CH$_2$Cl$_2$ complex (9.09 mg, 0.011 mmol) and sodium carbonate (70.8 mg, 0.668 mmol) were combined in tetrahydrofuran (2 ml) and water (0.667 ml). The mixture was degassed with nitrogen for 30 minutes and heated to 75° C. for 4 hours then cooled to room temperature and partitioned between water (5 mL) and ethyl acetate (3×5 mL). The combined organic extracts were dried (Na$_2$SO$_4$), filtered, and concentrated, then purified by flash (0 to 8% methanol-CH$_2$Cl$_2$ over 30 minutes, 4 g column, 18 mL/minute) to provide the title compound. $^1$H NMR (500 MHz, DMSO) δ 11.89 (s, 1H), 8.23 (d, J=4.9 Hz, 1H), 7.32-7.17 (m, 3H), 7.05 (d, J=4.9 Hz, 1H), 6.49 (s, 1H), 6.33 (d, J=2.0 Hz, 1H), 4.67-4.61 (m, 1H), 4.55 (t, J=8.6 Hz, 1H), 4.04 (dd, J=8.4, 4.8 Hz, 1H), 3.84-3.78 (m, 1H), 3.74 (s, 3H), 3.20 (ddd, J=13.4, 10.1, 6.2 Hz, 1H), 2.54-2.43 (m, 2H); MS (ESI+) m/z 380.2 (M+H)+.

EXAMPLE 1141

{4-[4-(5-fluoro-2-methoxyphenyl)-1H-pyrrolo[2,3-b]pyridin-2-yl]piperidin-1-yl}(phenyl)acetic acid

EXAMPLE 1141A

5-[4-(5-fluoro-2-methoxyphenyl)-1H-pyrrolo[2,3-b] pyridin-2-yl]-1-(methylsulfonyl)-1,2,3,4-tetrahydropyridine-4-carboxylic acid The title compound was prepared essentially as described in Example 1077 substituting Example 135B for Example 87D. MS (ESI+) m/z 488.2 (M+H)+.

EXAMPLE 1141B

{4-[4-(5-fluoro-2-methoxyphenyl)-1H-pyrrolo[2,3-b]pyridin-2-yl]piperidin-1-yl}(phenyl)acetic acid A mixture of Example 1141A (0.052 g, 0.107 mmol) in tetrahydrofuran (0.533 ml) and methanol (0.533 ml) was treated with aqueous 2 M lithium hydroxide (0.213 ml, 0.427 mmol) and the reaction was stirred at 50° C. for 6 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (500 MHz, DMSO-d$_6$) δ ppm 1.88-2.45 (m, 4H), 2.91-3.26 (m, 5H), 3.74 (s, 3H), 5.29 (brs, 1H), 6.03 (brs, 1H), 7.07 (d, J=5.0 Hz, 1H), 7.15-7.33 (m, 3H), 7.50-7.60 (m, 5H), 8.19 (d, J=5.0 Hz, 1H), 11.76 (d, J=2.3 Hz, 1H). MS (ESI+) m/z 460.2 (M+H)+.

EXAMPLE 1142

2-{4-[5-cyano-4-(5-fluoro-2-methoxyphenyl)-1H-pyrrolo[2,3-b]pyridin-2-yl]-3,6-dihydropyridin-1 (2H)-yl}acetamide The title compound was prepared according to the procedure described in Example 235, substituting Example 236F for Example 17G and 2-bromoacetamide for 2-chloro-N,N-dimethylacetamide. $^1$H NMR (500 MHz, DMSO-d$_6$) δ 2.45-2.59 (m, 2H), 2.66 (t, J=5.9 Hz, 2H), 2.99 (s, 2H), 3.23 (d, J=3.8 Hz, 2H), 3.76 (s, 3H), 6.26 (s, 1H), 6.57 (t, J=3.5 Hz, 1H), 6.91-7.71 (m, 5H), 8.60 (s, 1H), 12.46 (s, 1H). MS (ESI+) m/z 406 (M+H)+.

EXAMPLE 1143

N-(3-fluorocyclobutyl)-4-[4-(5-fluoro-2-methoxyphenyl)-1H-pyrrolo[2,3-b]pyridin-2-yl]-2,5-dihydro-1H-pyrrole-2-carboxamide

EXAMPLE 1143A 1-(tert-butoxycarbonyl)-4-(4-(5-fluoro-2-methoxyphenyl)-1H-pyrrolo[2,3-b]pyridin-2-yl)-2,5-dihydro-1H-pyrrole-2-carboxylic acid Example 772B (313 mg, 0.67 mmol) was dissolved in 3:1 tetrahydrofuran:methanol (4 mL and 1M lithium hydroxide solution (3 mL) was added. After stirring at room temperature for 24 hours, the reaction was concentrated. The residue was suspended in water and acidified with 1M aqueous HCl. The aqueous phase was extracted with ethyl acetate and the organic layer was dried over sodium sulfate, filtered, and concentrated to provide the title compound. MS (ESI) m/e 454.0 (M+H)$^+$.

EXAMPLE 1143B 4-(4-(5-fluoro-2-methoxyphenyl)-1H-pyrrolo[2,3-b]pyridin-2-yl)-2,5-dihydro-1H-pyrrole-2-carboxylic acid Example 1143A (98 mg, 0.22 mmol), O-(7-azabenzotriazol-1-yl)-N,N'N'N'-tetramethyluronium hexafluorophosphate (107 mg, 0.27 mmol), triethylamine (0.2 mL, 1.4 mmol) and 3-fluorocyclobutanamine hydrochloride (34 mg, 0.27 mmol) were combined in N,N-dimethylformamide (2 mL) and the mixture was stirred at room temperature for 24 hours. The reaction was concentrated. Purification by reverse phase-HPLC (Sunfire 5 µM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to provide the title compound. $^1$HNMR (500 MHz, DMSO-$d_6$) δ 2.28 (m, 1H), 2.46 (m, 3H), 2.69 (m, 1H), 3.79 (s, 3H), 3.84 (m, 1H), 4.13 (m, 2H), 4.61 (m, 1H), 6.25 (br s, 1H), 6.53 (m, 1H), 7.10 (d, 1H), 7.29 (m, 3H), 8.28 (d, 1H), 12.02 (br s, 1H). MS (ESI) m/e 425.2 (M+H)$^+$.

EXAMPLE 1144

4-(5-fluoro-2-methoxyphenyl)-2-[(2R)-2-methyl-1,2,3,6-tetrahydropyridin-4-yl]-1H-pyrrolo[2,3-b]pyridine-4-(5-fluoro-2-methoxyphenyl)-2-[(6R)-6-methyl-1,2,3,6-etrahydropyridin-4-yl]-1H-pyrrolo[2,3-b]pyridine (1:1)

The title compound mixture was prepared as described in Example 258F using Example 1025C in place of Example 258E. MS (ESI) m/e 338.1 (M+H)$^+$.

EXAMPLE 1145

2-{4-[4-(5-fluoro-2-methoxyphenyl)-1H-pyrrolo[2,3-b]pyridin-2-yl]-6,6-dimethyl-3,6-dihydropyridin-1(2H)-yl}-N,N-dimethylacetamide Example 271D (127 mg, 0.30 mmol), 2-bromo-N,N-dimethylacetamide (71 mg, 0.42 mmol and triethylamine (0.3 mL, 2.1 mmol) were stirred in N,N-dimethylformamide (2 mL) for 24 hours. The reaction mixture was concentrated. Purification by reverse phase-HPLC (Sunfire 5 µM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to give the free base of the title compound. $^1$HNMR (400 MHz, DMSO-$d_6$) δ 1.22 (s, 6H), 2.42 (m, 2H), 2.71 (m, 2H), 2.88 (s, 3H), 3.14 (s, 3H), 3.34 (m, 2H), 3.79 (s, 3H), 6.25 (s, 1H), 6.37 (s, 1H), 7.07 (d, 1H), 7.29 (m, 3H), 8.23 (d, 1H), 11.76 (br s, 1H). MS (ESI) m/e 437.0 (M+H)$^+$.

EXAMPLE 1146 methyl 4-[4-(5-fluoro-2-methoxyphenyl)-1H-pyrrolo[2,3-b]pyridin-2-yl]-1-(methylcarbamoyl)-2,5-dihydro-1H-pyrrole-2-carboxylate To a solution of Example 864 (78 mg, 0.212 mmol) in 1.5 mL N,N-dimethylformamide was added triethylamine (100 µL, 0.717 mmol) followed by N-succinimidyl-N-methylcarbamate (50 mg, 0.290 mmol) and the mixture was stirred overnight at room temperature. The mixture was diluted with water and extracted with ethyl acetate. The combined extracts were rinsed with brine, dried over MgSO$_4$, filtered and concentrated. The residue was recrystallized from ethyl acetate to provide the title compound. $^1$H NMR (500 MHz, DMSO-$d_6$) δ 12.14 (s, 1H), 8.28 (d, J=4.9 Hz, 1H), 7.32-7.20 (m, 3H), 7.10 (d, J=4.9 Hz, 1H), 6.48 (d, J=2.1 Hz, 1H), 6.41-6.37 (m, 1H), 6.21 (d, J=2.0 Hz, 1H), 5.16 (m, 1H), 4.53-4.43 (m, 2H), 3.74 (s, 3H), 3.66 (s, 3H), 2.60 (d, J=4.3 Hz, 3H). MS (ESI+) m/e 425 (M+H)$^+$.

EXAMPLE 1147

4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile The title compound was prepared as described in Example 277C. $^1$H NMR (500 MHz, DMSO-$d_6$) δ 2.68 (dd, J=22.6, 16.9 Hz, 1H), 3.06 (dtd, J=93.3, 16.7, 15.8, 9.7 Hz, 4H), 3.26-3.53 (m, 2H), 3.67-3.81 (m, 4H), 6.02-6.50 (m, 2H), 7.16-7.62 (m, 3H), 8.36-9.10 (m, 3H), 12.66 (d, J=5.9 Hz, 1H). MS (ESI$^+$) m/z 375 (M+H)$^+$.

EXAMPLE 1148

5-[5-cyano-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide The title compound was prepared according to the procedure described in Example 215, substituting Example 1147 for Example 87D. $^1$H NMR (500 MHz, DMSO-$d_6$) δ 2.57 (d, J=15.6 Hz, 4H), 2.80-3.06 (m, 3H), 3.37 (s, 2H), 3.47-3.59 (m, 2H), 3.75 (s, 3H), 6.03 (t, J=4.8 Hz, 1H), 6.24 (s, 1H), 6.42 (s, 1H), 7.01-7.60 (m, 3H), 8.62 (s, 1H), 12.56 (s, 1H); MS (ESI$^+$) m/z 432 (M+H)$^+$.

EXAMPLE 1149

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide The title compound was prepared according to the procedure described in Example 235, substituting Example 1147 for Example 17G and 2-bromoacetamide for 2-chloro-N,N-dimethylacetamide. $^1$H NMR (500 MHz, DMSO-$d_6$) δ 1.86 (s, 2H), 2.40-2.57 (m, 2H), 2.65 (dt, J=11.8, 5.8 Hz, 2H), 2.81-3.04 (m, 3H), 3.39-3.50 (m, 1H), 3.76 (s, 3H), 6.18 (d, J=2.6 Hz, 1H), 6.41 (s, 1H), 6.79-7.13 (m, 2H), 7.15-7.69 (m, 3H), 8.61 (s, 1H). MS (ESI$^+$) m/z 432 (M+H)$^+$.

EXAMPLE 1150

N-cyano-2-{4-[4-(5-fluoro-2-methoxyphenyl)-1H-pyrrolo[2,3-b]pyridin-2-yl]-3,6-dihydropyridin-1(2H)-yl}acetamide The title compound was prepared using the condition described in Example 1117B substituting Example 87D for Example 17G. $^1$H NMR (400 MHz, DMSO-$d_6$) δ ppm 0.80-0.91 (m, 2 H) 1.27-1.55 (m, 2 H) 2.60-2.69 (m, 2 H) 3.15 (s, 2 H) 3.64-3.68 (s, 1 H) 3.74 (s, 3 H) 6.28 (d, J=1.53 Hz, 1 H) 6.44 (s, 1 H) 7.04 (d, J=4.88 Hz, 1 H) 7.15-7.33 (m, 3 H) 8.21 (d, J=4.88 Hz, 1 H) 11.86 (s, 1 H). MS (ESI$^+$) m/z 406 (M+H)$^+$.

EXAMPLE 1151

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}ethanone A mixture of Example 845 (60 mg, 0.172 mmol), 1-[bis(dimethylamino)methylene]-1H-1,2,3-triazolo[4,5-b]pyridinium 3-oxide hexafluorophosphate (78 mg, 0.206 mmol) and acetic acid (12.37 mg, 0.206 mmol) in dimethylformamide (2 mL) was stirred at room temperature overnight. The reaction mixture was concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the trifluoroacetate salt. $^1$H NMR (500 MHz, DMSO-$d_6$) δ ppm 1.90 (s, 2 H) 1.93 (s, 1 H) 2.58-2.67 (m, 1 H) 2.84-3.17 (m, 3 H) 3.39-3.77 (m, 4 H) 3.75 (s, 3 H) 6.28 (dd, J=4.73, 1.68 Hz, 1 H) 6.37 (d, J=7.32 Hz, 1 H) 7.16 (d, J=5.19 Hz, 1 H) 7.20-7.34 (m, 3 H) 8.27 (d, J=5.19 Hz, 1 H) 12.21 (s, 1 H). MS (ESI$^+$) m/z 392 (M+H)$^+$.

EXAMPLE 1152 ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-3-carboxylate The title compound was prepared using the procedure described in Example 794, using ethyl 1-(chlorosulfonyl)piperidine-3-carboxylate in place of 2-(1,3-dioxoisoindolin-2-yl)ethanesulfonyl chloride. $^1$H NMR (400 MHz, DMSO-$d_6$) δ 11.86 (s, 1H), 8.21 (d, J=4.9 Hz, 1H), 7.34-7.17 (m, 3H), 7.04 (d, J=4.9 Hz, 1H), 6.54-6.48 (m, 1H), 6.26 (d, J=2.1 Hz, 1H), 4.07 (qd, J=7.1, 1.6 Hz, 2H), 3.90 (m, 2H), 3.74 (s, 3H), 3.57 (dd, J=12.3, 3.9 Hz, 1H), 3.42-3.29 (m, 4H), 3.09 (dd, J=12.2, 9.2 Hz, 1H), 2.92 (ddd, J=12.5, 9.6, 3.1 Hz, 1H), 2.66-2.57 (m, 2H), 1.93-1.81 (m, 1H), 172-1.64 (m, 1H), 1.62-1.42 (m, 2H), 1.17 (t, J=7.1 Hz, 3H). MS (ESI+) m/e 543 (M+H)$^+$.

EXAMPLE 1153

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide A mixture of Example 845 (60 mg, 0.172 mmol), 2-bromoacetamide (0.019 ml, 0.180 mmol) and triethylamine (0.048 ml, 0.343 mmol) in dimethylformamide (0.8 ml) was stirred at room temperature overnight. The reaction mixture was concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 0.1% trifluoroacetic acid in water to afford the title compound as the bis-trifluoroacetate salt. $^1$H NMR (400 MHz, DMSO-$d_6$) δ ppm 2.62-3.29 (m, 10 H) 3.72 (s, 3 H) 6.23 (s, 1 H) 6.28 (s, 1 H) 7.04 (d, J=4.88 Hz, 1 H) 7.11-7.28 (m, 3 H) 7.49 (s, 2 H) 8.22 (d, J=4.88 Hz, 1 H) 11.73 (s, 1 H). MS (ESI$^+$) m/z 407 (M+H)$^+$.

EXAMPLE 1154

N-cyano-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxamide To a mixture of cyanamide (197 mg, 4.69 mmol) and N-ethyl-N-isopropylpropan-2-amine (1014 µl, 5.80 mmol) in dimethylformamide (10 mL) at 0° C. was added 4-nitrophenyl carbonochloridate (900 mg, 4.47 mmol). The reaction mixture was warmed up to room temperature for 2 hours. The mixture (1.5 mL, ~0.23 mmol) was then added to a solution of Example 845 (80 mg, 0.229 mmol) and N-ethyl-N-isopropylpropan-2-amine (40.0 µl, 0.229 mmol) in dimethylformamide (2 mL). The reaction mixture was stirred at room temperature for 2 days and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-$d_6$) δ ppm 2.54-3.06 (m, 5 H) 3.37-3.63 (m, 4 H) 3.73 (s, 3 H) 6.19 (d, J=2.14 Hz, 1 H) 6.30 (s, 1 H) 7.04 (d, J=4.88 Hz, 1 H) 7.15-7.33 (m, 3 H) 8.21 (d, J=4.88 Hz, 1 H) 11.89 (d, J=1.53 Hz, 1 H). MS (ESI$^+$) m/z 418 (M+H)$^+$.

EXAMPLE 1155

N-cyano-4-[4-(5-fluoro-2-methoxyphenyl)-1H-pyrrolo[2,3-b]pyridin-2-yl]piperidine-1-carboxamide The title compound was prepared using the condition described in Example 1154 substituting Example 17G for Example 845. $^1$H NMR (500 MHz, DMSO-$d_6$) δ ppm 1.35-1.53 (m, 2 H) 1.76-1.88 (m, 2 H) 2.57-2.86 (m, 3 H) 3.73 (s, 3 H) 4.19-4.29 (m, 2 H) 5.94 (s, 1 H) 7.00 (d, J=4.88 Hz, 1 H) 7.12-7.30 (m, 3 H) 8.13 (d, J=4.88 Hz, 1 H) 11.55 (s, 1 H). MS (ESI$^+$) m/z 394 (M+H)$^+$.

EXAMPLE 1156

2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide

EXAMPLE 1156A 4-(5-fluoro-2-methoxyphenyl)-2-(piperidin-4-yl)-1H-pyrrolo[2,3-b]pyridine-5-carbonitrile The title compound was prepared as described in Example 129, substituting Example 236F for Example 127. MS (ESI$^+$) m/z 483 (M+H)$^+$.

EXAMPLE 1156B

2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide The title compound was prepared using the conditions described in Example 280, substituting Example 1156A for Example 262E and 2-(N-methylsulfamoyl)acetic acid for 2-hydroxyacetic acid. $^1$H NMR (400 MHz, DMSO-d$_6$) δ 1.43-1.81 (m, 2H), 1.99-2.09 (m, 2H), 2.62 (d, J=4.1 Hz, 3H), 2.70-2.81 (m, 1H), 2.99-3.10 (m, 1H), 3.14-3.25 (m, 1H), 3.75 (s, 3H), 4.05-4.13 (m, 1H), 4.20-4.37 (m, 2H), 4.42-4.51 (m, 1H), 6.03 (s, 1H), 7.03-7.10 (m, 1H), 7.21-7.33 (m, 2H), 7.38 (td, J =8.6, 3.2 Hz, 1H), 8.57 (s, 1H), 12.32 (bs, 1H). MS (ESI$^+$) m/z 486 (M+H)$^+$.

EXAMPLE 1157

N-{5-[4-(5-fluoro-2-methoxyphenyl)-1H-pyrrolo[2,3-b]pyridin-2-yl]-1,2,3,3a,4,6a-hexahydropentalen-2-yl}-D-valine

EXAMPLE 1157A 4-(5-fluoro-2-methoxyphenyl)-2-(3',3a',4',6a'-tetrahydro-1'H-spiro[[1,3]dioxolane-2,2'-pentalen]-5'-yl)-1-tosyl-1H-pyrrolo[2,3-b]pyridine A mixture of Example 258C (250.0 mg, 0.479 mmol), 4,4,5,5-tetramethyl-2-(3',3a',4',6a'-tetrahydro-1'H-spiro[[1,3]dioxolane-2,2'-pentalen]-5'-yl)-1,3,2-dioxaborolane (154 mg, 0.526 mmol), bis(triphenylphosphine)palladium(II) dichloride (26.9 mg, 0.038 mmol), and 1M aqueous sodium carbonate (0.957 mL, 0.957 mmol) in 1,2-dimethoxyethane/ethanol/water (7:2:3) (6 mL) was degassed and heated at 90° C. for 2 hours. The reaction mixture was treated with brine and extracted with ethyl acetate. The combined organic layers were dried over MgSO$_4$, filtered, concentrated, and purified on a 12 g silica column using the ISCO Companion flash system eluting with heptanes/ethyl acetate (7:3 to 6:4) to provide the title compound. MS (ESI$^+$) m/z 561.1 (M+H)$^+$.

EXAMPLE 1157B 4-(5-fluoro-2-methoxyphenyl)-2-(3',3a',4',6a'-tetrahydro-1'H-spiro[[1,3]dioxolane-2,2'-pentalen]-5'-yl)-1H-pyrrolo[2,3-b]pyridine A mixture of Example 1157A (0.200 g, 0.357 mmol) and 5M sodium hydroxide (0.285 mL, 1.427 mmol) solution in methanol (4.5 mL) was heated in a Biotage Initiator microwave reactor (model 355302) at 85° C. for 30 minutes. After cooling, the suspension was filtered, rinsed with cold methanol and water, and vacuum oven-dried to provide the title compound. MS (ESI$^+$) m/z 407.2 (M+H)$^+$.

EXAMPLE 1157C

N-{5-[4-(5-fluoro-2-methoxyphenyl)-1H-pyrrolo[2,3-b]pyridin-2-yl]-1,2,3,3a,4,6a-hexahydropentalen-2-yl}-D-valine The title compound was prepared essentially as described in Example 241B-C, substituting Example 1157B for Example 241A in Example 241B. $^1$H NMR (500 MHz, methanol-d$_4$) δ ppm 1.00-1.18 (m, 6H), 1.44-1.70 (m, 2H), 2.27-2.69 (m, 4H), 2.85-3.17 (m, 2H), 3.42-3.64 (m, 2H), 3.81 (s, 3H), 3.83-3.97 (m, 1H), 6.46 (d, J=1.7 Hz, 1H), 6.46-6.50 (m, 1H), 7.18-7.31 (m, 3H), 7.45 (d, J=5.9 Hz, 1H), 8.27 (d, J=5.9 Hz, 1H). MS (ESI$^+$) m/z 464.2 (M+H)$^+$.

EXAMPLE 1158 methyl 4-[4-(5-fluoro-2-methoxyphenyl)-1H-pyrrolo[2,3-b]pyridin-2-yl]-3,6-dihydropyridine-1(2H)-carboxylate To a solution of Example 87D (80 mg, 0.202 mmol) in N,N-dimethylformamide (1.8 mL) was added triethylamine (0.169 mL, 1.211 mmol) and methyl chloroformate (0.031 mL, 0.404 mmol). The reaction was stirred for 2 hours. The reaction mixture was treated with water (5 mL) and stirred for 10 minutes. The precipitate was filtered, washed with water, and vacuum oven-dried. The free base was suspended in 1 mL of methanol and treated with 0.7 mL of 2M HCl in ether. The suspension was diluted with 1 mL of ether, stirred for 10 minutes, filtered, washed with ether, and vacuum oven-dried to provide the title compound as an HCl salt. $^1$H NMR (400 MHz, methanol-d$_4$) δ ppm 2.56-2.64 (m, 2H), 3.68-3.73 (m, 2H), 3.74 (s, 3H), 3.83 (s, 3H), 4.20-4.26 (m, 2H), 6.56 (bs, 1H), 6.65 (s, 1H), 7.21-7.29 (m, 1H), 7.27-7.38 (m, 2H), 7.58 (d, J=6.2 Hz, 1H), 8.30 (d, J=6.2 Hz, 1H). MS (ESI$^+$) m/z 382.2 (M+H)$^+$.

EXAMPLE 1159

5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine The title compound was prepared as described in Example 282A. $^1$H NMR (400 MHz, pyridine-d$_5$) δ ppm 2.66-2.75 (m, 1H), 2.91-3.05 (m, 1H), 3.12-3.42 (m, 2H), 3.49-3.57 (m, 1H), 3.68-3.84 (m, 6H), 6.41 (bs, 1H), 6.46 (d, J=1.6 Hz, 1H), 7.13-7.16 (m, 1H), 7.33 (td, J=8.5, 3.2 Hz, 1H), 7.47 (dd, J=8.6, 3.2 Hz, 1H), 8.54 (d, J=2.6 Hz, 1H), 13.16-13.24 (m, 1H). MS (ESI$^+$) m/z 368.2 (M+H)$^+$.

EXAMPLE 1160

2-{4-[5-cyano-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide The title compound was prepared using the procedure described in Example 238, substituting Example 283B for Example 226B and 2-(methylamino)ethanol for azetidin-3-ol hydrochloride. $^1$H NMR (400 MHz, DMSO-d$_6$) δ 1.87 (s, 3H), 2.45 (tq, J=7.3, 4.4, 3.7 Hz, 2H), 2.62-2.75 (m, 2H), 3.21 (dt, J=6.0, 3.4 Hz, 2H), 3.25-3.39 (m, 3H), 3.41-3.58 (m, 4H), 3.76 (s, 3H), 6.25 (s, 1H), 6.45-6.77 (m, 1H), 7.16-7.60 (m, 3H), 8.60 (s, 1H). MS (ESI$^+$) m/z 464 (M+H)$^+$.

EXAMPLE 1161

2-({4-[4-(5-fluoro-2-methoxyphenyl)-1H-pyrrolo[2,3-b]pyridin-2-yl]cyclohex-3-en-1-yl}oxy)-N,N-dimethylacetamide To a suspension of Example 1027 (0.091 g, 0.230 mmol) in dichloromethane (2 mL), thionyl chloride (0.06 mL, 0.822 mmol) was added. The resulting solution was heated at 100° C. in a microwave (Biotage Initiator, model 355302) for 30 minutes. Dimethylamine in tetrahydrofuran (2M, 2 mL, 4 mmol) was added. The mixture heated at 100° C. in the microwave for 30 minutes. The product was purified by reverse-phase HPLC on a Sunfire C8 column (30×100 mm, 5 µm particle size, flow rate 30 mL/minute) using a gradient of 30-70% acetonitrile in 0.1% aqueous trifluoroacetic acid to provide the title compound as trifluoroacetic acid salt. $^1$H NMR (500 MHz, DMSO-$d_6$): δ 1.65-1.76 (m, 1 H) 1.92-2.01 (m, 1 H) 2.16-2.26 (m, 1 H) 2.32-2.44 (m, 1 H) 2.53-2.59 (m, 2 H) 2.81 (s, 3 H) 2.94 (s, 3 H) 3.66-3.71 (m, 1 H) 3.74 (s, 3 H) 4.18 (d, J=2.75 Hz, 2 H) 6.21 (d, J=1.83 Hz, 1 H) 6.41-6.44 (m, 1 H) 7.05 (d, J=4.88 Hz, 1 H) 7.18-7.31 (m, 3 H) 8.19 (d, J=5.19 Hz, 1 H) 11.83 (s, 1 H). MS (ESI$^+$) m/z: 424.1 (M+H)$^+$.

EXAMPLE 1162

2-({4-[4-(5-fluoro-2-methoxyphenyl)-1H-pyrrolo[2,3-b]pyridin-2-yl]cyclohex-3-en-1-yl}oxy)-1-(morpholin-4-yl)ethanone The title compound was prepared using the procedure described in Example 1161, using morpholine in place of dimethylamine. $^1$H NMR (500 MHz, DMSO-$d_6$): δ 1.66-1.77 (m, 1 H) 1.91-2.00 (m, 1 H) 2.18-2.28 (m, 1 H) 2.33-2.44 (m, 1 H) 2.52-2.59 (m, 1 H) 3.39-3.46 (m, 4 H) 3.51-3.58 (m, 4 H) 3.67-3.73 (m, 1 H) 3.75 (s, 3 H) 4.20 (s, 2 H) 6.25 (d, J=1.83 Hz, 1 H) 6.42-6.46 (m, 1 H) 7.10 (d, J=5.19 Hz, 1 H) 7.17-7.33 (m, 3 H) 8.22 (d, J=5.19 Hz, 1 H) 11.96 (s, 1 H). MS (ESI$^+$) m/z: 466.1 (M+H)$^+$.

EXAMPLE 1163

4-[5-fluoro-2-(methylsulfanyl)phenyl]-2-[1-(methylsulfonyl)-1,2,3,6-tetrahydropyridin-4-yl]-1H-pyrrolo[2,3-b]pyridine The title compound was prepared using the procedure described in Example 255C, using Example 220F in place of Example 255B and (5-fluoro-2-(methylthio)phenyl)boronic acid in place of (5-fluoro-2-methoxyphenyl)boronic acid. $^1$H NMR (500 MHz, DMSO-$d_6$): δ 2.35 (s, 3 H) 2.55-2.61 (m, 2 H) 2.93 (s, 3 H) 3.33-3.37 (m, 2 H) 3.91 (d, J=2.44 Hz, 2 H) 6.19 (d, J=1.83 Hz, 1 H) 6.51-6.57 (m, 1 H) 7.01 (d, J=4.88 Hz, 1 H) 7.16-7.21 (m, 1 H) 7.30-7.37 (m, 1 H) 7.44-7.50 (m, 1 H) 8.25 (d, J=4.88 Hz, 1 H) 11.99 (s, 1 H). MS (ESI$^+$) m/z: 418.1 (M+H)$^+$.

EXAMPLE 1164

4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-5-carbonitrile The title compound was prepared using the procedure described in Example 238, substituting Example 283B for Example 226B. $^1$H NMR (500 MHz, DMSO-$d_6$) δ 2.45 (p, J=7.4, 6.5 Hz, 2H), 2.66 (t, J=5.8 Hz, 2H), 2.97-3.24 (m, 4H), 3.59 (dd, J=10.2, 4.4 Hz, 1H), 3.76 (s, 3H), 3.97 (ddd, J=72.7, 9.6, 5.5 Hz, 2H), 4.24-4.61 (m, 2H), 5.69 (s, 1H), 6.25 (s, 1H), 6.56 (t, J=3.6 Hz, 1H), 7.20-7.50 (m, 3H), 8.60 (s, 1H). MS (ESI$^+$) m/z 462 (M+H)$^+$.

EXAMPLE 1165

2-{4-[5-cyano-4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide The title compound was prepared using the conditions described in Example 280, substituting Example 236F for Example 262E and 2-(N-methylsulfamoyl)acetic acid for 2-hydroxyacetic acid. $^1$H NMR (400 MHz, DMSO-$d_6$) δ 2.40-2.54 (m, 1H), 2.62 (s, 4H), 3.60-3.80 (m, 5H), 4.21 (d, J=3.6 Hz, 1H), 4.34 (d, J=11.4 Hz, 3H), 6.33 (s, 1H), 6.60 (t, J=4.0 Hz, 1H), 7.10 (t, J=9.7 Hz, 1H), 7.22-7.46 (m, 3H), 8.60 (s, 1H), 12.40 (s, 1H). MS (ESI$^+$) m/z 484 (M+H)$^+$.

EXAMPLE 1166

2-{4-[5-cyano-4-(5-fluoro-2-methoxyphenyl)-1H-pyrrolo[2,3-b]pyridin-2-yl]piperidin-1-yl}acetamide The title compound was prepared according to the procedure described in Example 235, substituting Example 1156A for Example 17G and 2-bromoacetamide for 2-chloro-N,N-dimethylacetamide. $^1$H NMR (400 MHz, DMSO-$d_6$) δ 1.75 (q, J=12.1 Hz, 2H), 1.95 (d, J=12.8 Hz, 2H), 2.18 (t, J=11.5 Hz, 2H), 2.71 (t, J=11.7 Hz, 1H), 2.88 (d, J=9.8 Hz, 4H), 3.75 (s, 3H), 6.00 (s, 1H), 7.12 (d, J=13.0 Hz, 2H), 7.26 (dd, J=9.1, 4.2 Hz, 2H), 7.37 (t, J=8.8 Hz, 1H), 8.50 (s, 1H), 12.27 (s, 1H). MS (ESI$^+$) m/z 408 (M+H)$^+$.

EXAMPLE 1169 methyl (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate The title compound was prepared as described in Example 288A. $^1$H NMR (500 MHz, DMSO-$d_6$) δ ppm 1.34-1.52 (m, 6H), 1.52-1.84 (m, 2H), 1.89-2.02 (m, 1H), 2.23-2.33 (m, 3H), 2.39-2.48 (m, 2H), 2.65 (t, J=5.6 Hz, 2H), 3.15-3.27 (m, 2H), 3.58 (s, 3H), 3.74 (s, 3H), 6.18 (d, J=2.1 Hz, 1H), 6.46-6.53 (m, 1H), 7.02 (d, J=4.9 Hz, 1H), 7.14-7.32 (m, 3H), 8.18 (d, J=4.9 Hz, 1H), 11.76 (d, J=2.2 Hz, 1H). MS (ESI$^+$) m/z 478.1 (M+H)$^+$.

EXAMPLE 1170 methyl (trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate The title compound was prepared in Example 288B. $^1$H NMR (400 MHz, DMSO-$d_6$) δ ppm 0.91-1.08 (m, 2H), 1.20-1.35 (m, 2H), 1.51-1.70 (m, 1H), 1.70-1.88 (m, 4H), 2.19 (d, J=7.0 Hz, 2H), 2.25-2.37 (m, 1H), 2.38-2.47 (m, 2H), 2.62-2.74 (m, 2H), 3.15-3.26 (m, 2H), 3.58 (s, 3H), 3.73 (s, 3H), 6.16 (d, J=2.0 Hz, 1H), 6.44-6.53 (m, 1H), 7.01 (d, J=4.9 Hz, 1H), 7.13-7.33 (m, 3H), 8.17 (d, J=4.9 Hz, 1H), 11.73 (d, J=2.3 Hz, 1H). MS (ESI$^+$) m/z 478.1 (M+H)$^+$.

EXAMPLE 1171 methyl {4-[4-(5-fluoro-2-methoxyphenyl)-1H-pyrrolo[2,3-b]pyridin-2-yl]cyclohex-3-en-1-yl}acetate

EXAMPLE 1171A methyl 2-(4-(trifluoromethylsulfonyloxy)cyclohex-3-enyl)acetate

A solution of methyl 2-(4-oxocyclohexyl)acetate (0.5 g, 2.94 mmol) and 2,6-di-tert-butyl-4-methylpyridine (0.694 g, 3.38 mmol) in dichloromethane (14.69 ml) under a nitrogen atmosphere was treated with a solution of trifluoromethanesulfonic anhydride (0.521 ml, 3.08 mmol) in dichloromethane (2 mL) added dropwise over 5 minutes. The reaction was allowed to stir at room temperature for 2 hours during which time a suspension formed. The reaction mixture was filtered and the filtrate was concentrated. The concentrate was dissolved in 10 mL dichloromethane and filtered. The filtrate was concentrated to afford the title compound which was used directly in the next step.

EXAMPLE 1171B methyl 2-(4-(4,4,5,5-tetramethyl-1,3,2-dioxaborolan-2-yl)cyclohex-3-enyl)acetate A solution of Example 1171A (0.85 g, 2.109 mmol), 4,4,4',4',5,5,5',5'-octamethyl-2,2'-bi(1,3,2-dioxaborolane) (0.536 g, 2.109 mmol), potassium acetate (0.621 g, 6.33 mmol) and 1,1'-bis(diphenylphosphino)ferrocene-palladium (II)dichloride dichloromethane complex (0.069 g, 0.084 mmol) in dimethylsulfoxide (14 mL) was degassed by bubbling nitrogen gas through the mixture for 15 minutes. The reaction mixture was heated at 55 C under a nitrogen atmosphere for 2.5 hours, cooled to room temperature and partitioned between ethyl acetate (100 mL) and water (50 mL). The aqueous layer was extracted with additional ethyl acetate. The combined organic layers were washed with brine, dried over anhydrous sodium sulfate, filtered, and concentrated. The concentrate was purified by flash chromatography on silica gel (AnaLogix IntelliFlash 280 system) eluting with a gradient of from 0% to 25% ethyl acetate in heptanes to afford the title compound. MS (ESI$^+$) m/z 298.0 (M+NH$_4$)$^+$.

EXAMPLE 1171C methyl {4-[4-(5-fluoro-2-methoxyphenyl)-1H-pyrrolo[2,3-b]pyridin-2-yl]cyclohex-3-en-1-yl})acetate A mixture of Example 1171B (0.080 g, 0.285 mmol), Example 219A (0.075 g, 0.204 mmol) and sodium hydrogencarbonate (0.068 g, 0.815 mmol) in degassed N,N-dimethylformamide (1.9 mL) and degassed water (0.5 mL) was treated with bis(triphenylphosphine)palladium(II) chloride (8.58 mg, 0.012 mmol) and the reaction was heated under a nitrogen atmosphere at 80° C. for 5 hours. The reaction mixture was cooled to room temperature and partitioned in 20 mL water and 60 mL ethyl acetate. The organic layer was washed with brine, dried over anhydrous sodium sulfate, filtered and concentrated. The concentrate was purified by flash chromatography on silica gel (AnaLogix IntelliFlash 280 system) eluting with a gradient of from 0% to 70% ethyl acetate in heptanes to afford the title compound. $^1$H NMR (500 MHz, DMSO-d$_6$) δ ppm 1.30-1.45 (m, 1H), 1.79-2.03 (m, 3H), 2.29-2.42 (m, 4H), 2.43-2.50 (m, 1H), 3.61 (s, 3H), 3.73 (s, 3H), 6.17 (d, J=2.1 Hz, 1H), 6.46-6.52 (m, 1H), 7.01 (d, J=5.0 Hz, 1H), 7.14-7.32 (m, 3H), 8.17 (d, J=4.9 Hz, 1H), 11.71 (d, J=2.3 Hz, 1H). MS (ESI$^+$) m/z 395.3 (M+H)$^+$.

EXAMPLE 1172

{4-[4-(5-fluoro-2-methoxyphenyl)-1H-pyrrolo[2,3-b]pyridin-2-yl]cyclohex-3-en-1-yl}acetic acid The title compound was prepared essentially as described in Example 681, substituting Example 1171 for Example 676. $^1$H NMR (500 MHz, CD$_3$OD) δ ppm 1.42-1.57 (m, 1H), 1.95-2.19 (m, 3H), 2.34 (d, J=7.0 Hz, 2H), 2.42-2.62 (m, 3H), 3.81 (s, 3H), 6.48 (s, 1H), 6.51-6.59 (m, 1H), 7.17-7.33 (m, 3H), 7.45 (d, J=6.0 Hz, 1H), 8.23 (d, J=6.0 Hz, 1H). MS (ESI$^+$) m/z 381.2 (M+H)$^+$.

EXAMPLE 1173

(4-{4-[4-(5-fluoro-2-methoxyphenyl)-1H-pyrrolo[2,3-b]pyridin-2-yl]piperidin-1-yl}cyclohexyl)acetic acid

EXAMPLE 1173A methyl 2-(4-(4-(5-fluoro-2-methoxyphenyl)-1H-pyrrolo[2,3-b]pyridin-2-yl)piperidin-1-yl)cyclohexyl)acetate The title compound was prepared essentially as described in Example 288A, substituting Example 135B for Example 87D. The title compound was isolated as a mixture of cis- and trans-isomers. MS (ESI$^+$) m/z 480.3 (M+H)$^+$.

EXAMPLE 1173B (4-{4-[4-(5-fluoro-2-methoxyphenyl)-1H-pyrrolo[2,3-b]pyridin-2-yl]piperidin-1-yl}cyclohexyl)acetic acid The title compound was prepared essentially as described in Example 681, substituting Example 1173A for Example 676. $^1$H NMR (400 MHz, CD$_3$OD) δ ppm 1.11-1.32 (m, 1H), 1.56-2.12 (m, 9H), 2.13-2.39 (m, 3H), 2.39-2.50 (m, 3H), 3.14-3.31 (m, 3H), 3.57-3.76 (m, 2H), 3.80 (s, 3H), 6.37 (s, 1H), 7.16-7.34 (m, 3H), 7.44 (d, J=5.9 Hz, 1H), 8.29 (d, J=5.8 Hz, 1H). MS (ESI$^+$) m/z 466.3 (M+H)$^+$.

EXAMPLE 1174 methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate

EXAMPLE 1174A methyl 2-(4-nitro-1H-pyrazol-1-yl)propanoate

The title compound was prepared essentially as described in Example 765A, substituting methyl 2-bromopropanoate for methyl 2-bromoacetate. MS (DCI$^+$) m/z 199.9 (M+H)$^+$.

EXAMPLE 1174B methyl 2-(4-amino-1H-pyrazol-1-yl)propanoate

The title compound was prepared essentially as described in Example 765B, substituting Example 1174A for Example 765A. MS (DCI$^+$) m/z 170.0 (M+H)$^+$.

EXAMPLE 1174C methyl 2-(4-(4-oxopiperidin-1-yl)-1H-pyrazol-1-yl)propanoate

A mixture of Example 1174B (1.260 g, 7.45 mmol) in ethanol (7.50 ml) and water (1.596 ml) was heated at 90° C. and was treated with 1-benzyl-1-methyl-4-oxopiperidin-1- ium iodide (2.35 g, 7.10 mmol) added portionwise over 30 minutes. Stirring at 90° C. was continued for 1 hour. The reaction mixture was cooled to room temperature and was partitioned in dichloromethane and water. The organic layer was dried over anhydrous sodium sulfate, filtered and concentrated. The residue was purified by flash chromatography on silica gel (AnaLogix IntelliFlash 280 system) eluting with a gradient of from 0% to 3% methanol in dichloromethane to afford the title compound. MS (ESI$^+$) m/z 252.2 (M+H)$^+$.

EXAMPLE 1174D methyl 2-(4-(4-(trifluoromethylsulfonyloxy)-5,6-dihydropyridin-1(2H)-yl)-1H-pyrazol-1-yl)propanoate A −70° C. mixture of Example 1174C (0.428 g, 1.703 mmol) and 1,1,1-trifluoro-N-phenyl-N-((trifluoromethyl)sulfonyl)methanesulfonamide (0.663 g, 1.857 mmol) in tetrahydrofuran (6.81 ml) was treated with a 1M solution of sodium bis(trimethylsilyl)amide in tetrahydrofuran (1.959 ml, 1.959 mmol) added dropwise over 1 hour. The cooling bath was removed and the reaction mixture was stirred at room temperature for 30 minutes. The reaction mixture was partitioned in dichloromethane and half-saturated aqueous sodium bicarbonate solution. The aqueous layer was extracted with additional dichloromethane. The combined organic layers were washed with brine, dried over anhydrous sodium sulfate, filtered, and concentrated. The residue was purified by flash chromatography on silica gel (AnaLogix IntelliFlash 280 system) eluting with a gradient of from 0-70% ethyl acetate in heptanes to afford the title compound. MS (ESI$^+$) m/z 384.0 (M+H)$^+$.

EXAMPLE 1174E methyl 2-(4-(4-(4,4,5,5-tetramethyl-1,3,2-dioxaborolan-2-yl)-5,6-dihydropyridin-1(2H)-yl)-1H-pyrazol-1-yl)propanoate A solution of Example 1174D (0.098 g, 0.256 mmol), 4,4,4',4',5,5,5',5'-octamethyl-2,2'-bi(1,3,2-dioxaborolane) (0.071 g, 0.281 mmol), potassium acetate (0.100 g, 1.023 mmol) and 1,1'-bis(diphenylphosphino)ferrocene-palladium(II)dichloride dichloromethane complex (8.35 mg, 10.23 μmol) in anhydrous dimethyl sulfoxide (1.8 mL) was degassed by bubbling nitrogen gas through the mixture for 5 minutes. The reaction was then heated at 60° C. under a nitrogen atmosphere for 80 minutes. The reaction mixture was cooled to room temperature and partitioned in ethyl acetate (30 mL) and water (15 mL). The aqueous layer was extracted with additional ethyl acetate (20 mL). The combined organic layers were washed with brine (15 mL), dried over anhydrous sodium sulfate, filtered, and concentrated. The residue was purified by flash chromatography on silica gel (AnaLogix IntelliFlash 280 system) eluting with a gradient of from 0-50% ethyl acetate in heptanes to afford the title compound. MS (ESI$^+$) m/z 362.1 (M+H)$^+$.

EXAMPLE 1174F methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate The title compound was prepared essentially as described in Example 1171C, substituting Example 1174E for Example 1171B. The crude product was purified by flash chromatography on silica gel (AnaLogix IntelliFlash 280 system) eluting with a gradient of from 0% to 7% methanol in dichloromethane. $^1$H NMR (400 MHz, CD$_3$OD) δ ppm 1.73 (d, J=7.3 Hz, 3H), 2.64-2.73 (m, 2H), 3.26 (t, J=5.7 Hz, 2H), 3.71 (s, 3H), 3.77 (s, 3H), 4.51-4.60 (m, 2H), 5.08 (q, J=7.3 Hz, 1H), 6.30 (s, 1H), 6.44-6.52 (m, 1H), 7.09 (d, J=5.1 Hz, 1H), 7.12-7.23 (m, 3H), 7.38 (s, 1H), 7.45 (s, 1H), 8.16 (d, J=5.1 Hz, 1H). MS (ESI$^+$) m/z 476.1 (M+H)$^+$.

EXAMPLE 1176

4-(5-fluoro-2-methoxyphenyl)-2-[(6R)-6-methyl-1-(methylsulfonyl)-1,2,3,6-tetrahydropyridin-4-yl]-1H-pyrrolo[2,3-b]pyridine The title compound was prepared as described in Example 258G using Example 1025D in place of Example 258F. $^1$HNMR (500 MHz, DMSO-d$_6$) δ 1.31 (d, 3H), 2.53 (m, 2H), 3.93 (s, 3H), 3.22 (m, 1H), 3.74 (s, 3H), 3.77 (m, 1H), 4.44 (m, 1H), 6.28 (s, 1H), 6.51 (m, 1H), 7.04 (d, 1H), 7.25 (m, 3H), 8.20 (d, 1H), 11.82 (br s, 1H). MS (ESI) m/e 416.2 (M+H)$^+$.

EXAMPLE 1177

2-[(6R)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide The title compound was prepared as described Example 273, using Example 1025D in place of Example 272B. $^1$HNMR (500 MHz, DMSO-d$_6$) δ 3.17 (d, 3H), 2.40 (m, 2H), 2.59 (m, 1H), 2.82 (s, 3H), 2.91 (m, 1H), 3.04 (s, 3H), 3.10 (m, 1H), 3.32 (m, 1H), 3.74 (s, 3H), 3.56 (m, 1H), 6.21 (br s, 1H), 6.38 (m, 1H), 7.02 (d, 1H), 7.26 (m, 3H), 8.18 (d, 1H), 11.75 (br s, 1H). MS (ESI) m/e 423.0 (M+H)$^+$.

EXAMPLE 1178

4-(5-fluoro-2-methoxyphenyl)-2-[(2R)-2-methyl-1-(methylsulfonyl)-1,2,3,6-tetrahydropyridin-4-yl]-1H-pyrrolo[2,3-b]pyridine The title compound was prepared as described in Example 258G using Example 1144 in place of Example 258F; and separation of the regioisomers provided the title compound. $^1$HNMR (400 MHz, DMSO-d$_6$) δ 1.17 (d, 3H), 2.40 (m, 1H), 2.72 (m, 1H), 2.95 (s, 3H), 3.74 (s, 3H), 3.85 (m, 1H), 4.12 (m, 1H), 4.26 (m, 1H), 6.25 (br s, 1H), 6.52 (m, 1H), 7.03 (d, 1H), 7.26 (m, 3H), 8.20 (d, 1H), 11.87 (br s, 1H). MS (ESI) m/e 416.2 (M+H)$^+$.

EXAMPLE 1179

2-[(2R)-4-[4-(5-fluoro-2-methoxyphenyl)-1H-pyrrolo[2,3-b]pyridin-2-yl]-2-methyl-3,6-dihydropyridin-1(2H)-yl]-N,N-dimethylacetamide The title compound was prepared as described in Example 273 using Example 1144 in place of Example 272B; and separation of the regioisomers provided the title compound. $^1$HNMR (500 MHz, DMSO-d$_6$) δ 1.03 (d, 3H), 2.18 (m, 1H), 2.56 (m, 1H), 2.81 (s, 3H), 3.03 (s, 3H), 3.05 (m, 1H), 3.27 (m, 2H), 3.40 (m, 2H), 3.74 (s, 3H), 6.19 (s, 1H), 6.46

(m, 1H), 7.02 (d, 1H), 7.25 (m, 3H), 8.18 (d, 1H), 11.27 (m, 1H). MS (ESI) m/e 423.0 (M+H)+.

EXAMPLE 1180

{4-[4-(5-fluoro-2-methoxyphenyl)-1H-pyrrolo[2,3-b]pyridin-2-yl]cyclohex-3-en-1-yl}(3-hydroxyazetidin-1-yl)methanone Example 219C (60 mg, 0.164 mmol), azetidin-3-ol hydrochloride (21.53 mg, 0.197 mmol), O-(7-azabenzotriazol-1-yl)-N,N'N'N'-tetramethyluronium hexafluorophosphate (74.7 mg, 0.197 mmol), triethylamine (114 μl, 0.819 mmol) in 2 mL dimethylformamide were stirred at room temperature for 4 hours. The reaction mixture was added to water and filtered. The solid was purified by flash column chromatography with 0-5% $CH_3OH$ in dichloromethane using Analogix purification system. $^1$H NMR (500 MHz, DMSO-$d_6$) δ 1.57 (tq, J=12.0, 6.2, 5.8 Hz, 1H), 1.86 (dt, J =8.5, 3.9 Hz, 1H), 2.19-2.60 (m, 5H), 3.58 (dd, J=10.4, 4.3 Hz, 1H), 3.74 (s, 3H), 3.90 (tt, J=8.3, 4.2 Hz, 1H), 4.03 (dd, J=10.1, 6.9 Hz, 1H), 4.36 (td, J=9.4, 6.9 Hz, 1H), 4.45 (h, J=5.5, 5.1 Hz, 1H), 5.72 (d, J=5.1 Hz, 1H), 6.18 (d, J=1.9 Hz, 1H), 6.54 (d, J=4.0 Hz, 1H), 7.02 (d, J=4.9 Hz, 1H), 7.14-7.32 (m, 3H), 8.17 (d, J=4.9 Hz, 1H), 11.73 (d, J=2.3 Hz, 1H). MS (ESI+) m/z 422 (M+H)+.

EXAMPLE 1181

2-{4-[5-fluoro-4-(5-fluoro-2-methoxyphenyl)-1H-pyrrolo[2,3-b]pyridin-2-yl]piperidin-1-yl}-N-methyl-2-oxoethanesulfonamide The title compound was prepared using the conditions described in Example 280, substituting Example 255D for Example 262E and 2-(N-methylsulfamoyl)acetic acid for 2-hydroxyacetic acid. $^1$H NMR (400 MHz, DMSO-$d_6$) δ 1.43-1.88 (m, 2H), 1.96-2.13 (m, 2H), 2.62 (d, J=4.7 Hz, 3H), 2.67-3.28 (m, 4H), 3.72 (s, 3H), 3.93-4.17 (m, 1H), 4.19-4.40 (m, 2H), 4.46 (d, J=13.2 Hz, 1H), 5.89 (d, J=2.0 Hz, 1H), 6.90-7.54 (m, 4H), 8.15 (dd, J=8.5, 2.6 Hz, 1H), 11.76 (d, J=2.2 Hz, 1H). MS (ESI+) m/z 479 (M+H)+.

EXAMPLE 1182

{4-[5-cyano-4-(5-fluoro-2-methoxyphenyl)-1H-pyrrolo[2,3-b]pyridin-2-yl]piperidin-1-yl}acetic acid The title compound was prepared as described in Example 290B. $^1$H NMR (400 MHz, DMSO-$d_6$) δ 1.83-2.23 (m, 4H), 2.84-3.20 (m, 3H), 3.25-3.67 (m, 2H), 3.75 (s, 3H), 3.86 (s, 2H), 6.09 (s, 1H), 7.33 (ddd, J=41.5, 8.7, 3.4 Hz, 3H), 8.59 (s, 1H), 12.36 (s, 1H). MS (ESI+) m/z 409 (M+H)+.

EXAMPLE 1183

2-[1-(cyanoacetyl)piperidin-4-yl]-4-(5-fluoro-2-methoxyphenyl)-1H-pyrrolo[2,3-b]pyridine-5-carbonitrile The title compound was prepared according to the procedure described in Example 1055, substituting 2-cyanoacetic acid for 2-hydroxyacetic acid and Example 1156A for Example 255D. $^1$H NMR (400 MHz, DMSO-$d_6$) δ 1.45-1.85 (m, 2H), 2.01 (dd, J=10.4, 6.4 Hz, 2H), 2.76 (t, J=12.1 Hz, 1H), 3.03 (td, J=11.4, 5.6 Hz, 1H), 3.09-3.25 (m, 1H), 3.74 (m, 4H), 4.04 (s, 2H), 4.27-4.53 (m, 1H), 6.04 (s, 1H), 7.26 (dd, J=9.0, 4.0 Hz, 2H), 7.38 (td, J=8.9, 3.5 Hz, 1H), 8.57 (s, 1H), 12.31 (s, 1H). MS (ESI+) m/z 418 (M+H)+.

EXAMPLE 1184

4-(5-fluoro-2-methoxyphenyl)-2-{1-[2-(3-hydroxyazetidin-1-yl)-2-oxoethyl]piperidin-4-yl}-1H-pyrrolo[2,3-b]pyridine-5-carbonitrile The title compound was prepared using the procedure described in Example 238, substituting Example 290B for Example 226B. $^1$H NMR (400 MHz, DMSO-$d_6$) δ 1.58-2.26 (m, 6H), 2.55-3.12 (m, 5H), 3.44-3.67 (m, 1H), 3.75 (s, 3H), 3.84-4.21 (m, 2H), 4.21-4.59 (m, 2H), 5.67 (d, J=6.0 Hz, 1H), 6.04 (d, J=2.1 Hz, 1H), 7.20-7.32 (m, 2H), 7.37 (td, J=8.6, 3.2 Hz, 1H), 8.55 (s, 1H), 12.27 (d, J=2.2 Hz, 1H). MS (ESI+) m/z 464 (M+H)+.

EXAMPLE 1185

4-[5-fluoro-2-(methylsulfinyl)phenyl]-2-[1-(methylsulfonyl)-1,2,3,6-tetrahydropyridin-4-yl]-1H-pyrrolo[2,3-b]pyridine To a solution of Example 1163 (0.079 g, 0.19 mmol) in dichloromethane (3 mL) was added 3-chlorobenzoperoxoic acid (0.092 g, 0.53 mmol). The mixture was stirred at room temperature overnight. Dichloromethane (10 mL) and aqueous saturated $Na_2SO_3$ (10 mL) was added and the mixture was stirred for one hour. The organic layer was washed with saturated aqueous $Na_2CO_3$ and water. The combined organic layers were under vacuum. The product was purified by reverse-phase HPLC on a Sunfire C8 column (30×100 mm, 5 μm particle size, flow rate 30 mL/minute) using a gradient of 30-100% acetonitrile in 0.1% aqueous trifluoroacetic acid to provide the title compound as trifluoroacetic acid salt. $^1$H NMR (400 MHz, DMSO-$d_6$): δ 2.39 (s, 3 H) 2.55-2.62 (m, 2 H) 2.94 (s, 3 H) 3.35 (t, J=5.80 Hz, 2 H) 3.91 (d, J=2.75 Hz, 2 H) 6.27 (d, J=1.83 Hz, 1 H) 6.54-6.59 (m, 1 H) 7.06 (d, J=4.88 Hz, 1 H) 7.36-7.41 (m, 1 H) 7.59-7.66 (m, 1 H) 8.08-8.15 (m, 1 H) 8.28 (d, J=4.88 Hz, 1 H) 12.11 (s, 1 H). MS (ESI+) m/z: 434.1 (M+H)+.

EXAMPLE 1186

4-[3-cyano-5-fluoro-4-(5-fluoro-2-methoxyphenyl)-1H-pyrrolo[2,3-b]pyridin-2-yl]cyclohex-3-ene-1-carboxylic acid

EXAMPLE 1186A ethyl 4-(3-cyano-5-fluoro-4-(5-fluoro-2-methoxyphenyl)-1-((2-(trimethylsilyl)ethoxy)methyl)-1H-pyrrolo[2,3-b]pyridin-2-yl)cyclohex-3-enecarboxylate The title compound was prepared using the procedure described in Example 87C, substituting Example 1086E (300 mg, 0.55 mmol) for Example 87B and ethyl 4-(4,4,5,5-tetramethyl-1,3,2-dioxaborolan-2-yl)cyclohex-3-enecarboxylate for tert-butyl 4-(4,4,5,5-tetramethyl-1,3,2-dioxaborolan-2-yl)-5,6-dihydropyridine-1(2H)-carboxylate. MS (ESI+) m/z 568 (M+H)+.

EXAMPLE 1186B ethyl 4-(3-cyano-5-fluoro-4-(5-fluoro-2-methoxyphenyl)-1H-pyrrolo[2,3-b]pyridin-2-yl)cyclohex-3-enecarboxylate In a capped microwave vial under nitrogen a solution of Example 1186A (250 mg, 0.44 mmol), tetrabutylammonium fluoride (1.3 ml, 1.32 mmol/1M in tetrahydrofuran) and ethylenediamine (265 mg, 4.4 mmol) in tetrahydrofuran (2 ml) was heated at 90° C. for 30 minutes. After the completion of the reaction, the reaction was concentrated and purified on silica gel using an ISCO Companion eluting with heptanes/ethyl acetate (30%) to provide the title compound. MS (ESI$^+$) m/z 438 (M+H)$^+$.

EXAMPLE 1186C 4-(3-cyano-5-fluoro-4-(5-fluoro-2-methoxyphenyl)-1H-pyrrolo[2,3-b]pyridin-2-yl)cyclohex-3-enecarboxylic acid A solution of Example 1186B (80 mg, 0.18 mmol) in dioxane (5 mL) was added sodium hydroxide (36 mg in 0.5 mL water, 0.9 mmol) and the mixture was stirred at 50° C. for overnight. The reaction was purified by reverse-phase HPLC on Zorbax XDB C-18 (32) using a gradient of 5-40% acetonitrile/water (containing 0.1% trifluoroacetic acid) to afford the title compound as the trifluoroacetate salt. $^1$H NMR (400 MHz, DMSO-d$_6$) δ 1.69-1.88 (m, 1H), 2.11 (td, J=7.2, 5.6, 3.2 Hz, 1H), 2.45 (dtd, J=12.2, 5.9, 3.1 Hz, 1H), 2.54-2.79 (m, 3H), 3.65-3.74 (m, 1H), 3.76 (s, 3H), 6.79 (td, J=3.6, 2.0 Hz, 1H), 7.18 (dd, J=8.9, 4.5 Hz, 1H), 7.28 (tdt, J=9.2, 6.3, 3.2 Hz, 2H), 8.28 (dd, J=9.2, 3.2 Hz, 1H). MS (ESI$^+$) m/z 410 (M+H)$^+$.

EXAMPLE 1187

4-(5-fluoro-2-methoxyphenyl)-2-(1,2,3,3a,4,6a-hexahydrocyclopenta[c]pyrrol-5-yl)-5-hydroxy-1H-pyrrolo[2,3-b]pyridine-3-carbonitrile The title compound was isolated as a side-product of the procedure described in Example 1188A. $^1$H NMR (500 MHz, DMSO-d$_6$) δ 2.93 (dd, J=14.0, 2.7 Hz, 1H), 3.10 (dd, J=11.8, 4.8 Hz, 1H), 3.21 (m, 4H), 3.72 (s, 3H), 3.75 (m, 2H), 6.55 (s, 1H), 7.11 (ddd, J=19.6, 9.1, 3.9 Hz, 2H), 7.20 (td, J=8.7, 3.2 Hz, 1H), 7.86 (s, 1H). MS (ESI$^+$) m/z 391 (M+H)$^+$.

EXAMPLE 1188

5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine-3-carbonitrile

EXAMPLE 1188A tert-butyl 5-(3-cyano-5-fluoro-4-(5-fluoro-2-methoxyphenyl)-1-((2-(trimethylsilyl)ethoxy)methyl)-1H-pyrrolo[2,3-b]pyridin-2-yl)-3,3a,6,6a-tetrahydrocyclopenta[c]pyrrole-2(1H)-carboxylate The title compound was prepared using the procedure described in Example 87C, substituting Example 1086E for Example 87B and tert-butyl 5-(4,4,5,5-tetramethyl-1,3,2-dioxaborolan-2-yl)-3,3a,6,6a-tetrahydrocyclopenta[c]pyrrole-2(1H)-carboxylate for tert-butyl 4-(4,4,5,5-tetramethyl-1,3,2-dioxaborolan-2-yl)-5,6-dihydropyridine-1(2H)-carboxylate. MS (ESI$^+$) m/z 623 (M+H)$^+$.

EXAMPLE 1188B 5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine-3-carbonitrile The title compound was prepared using the procedure described in Example 1186B, substituting Example 1188A for Example 1186A, followed by a deprotection step as described in Example 1215B. $^1$H NMR (500 MHz, DMSO-d$_6$) δ 2.97 (ddt, J=14.0, 4.4, 2.5 Hz, 1H), 3.12 (dq, J=9.9, 4.6 Hz, 1H), 3.24 (m, 3H), 3.30-3.49 (m, 3H), 3.77 (s, 3H), 6.72 (d, J=2.5 Hz, 1H), 7.19 (dd, J=8.9, 4.7 Hz, 1H), 7.30 (ddt, J=11.9, 6.0, 3.1 Hz, 2H), 8.35 (d, J=9.1 Hz, 1H). MS (ESI$^+$) m/z 393 (M+H)$^+$.

EXAMPLE 1189

2-{4-[5-fluoro-4-(5-fluoro-2-methoxyphenyl)-1H-pyrrolo[2,3-b]pyridin-2-yl]piperidin-1-yl}-N-(3-hydroxycyclobutyl)-N-methylacetamide The title compound was prepared using the procedure described in Example 238, substituting Example 259B for Example 226B and 3-(methylamino)cyclobutanol hydrochloride for azetidin-3-ol, hydrochloric acid, respectively. $^1$H NMR (500 MHz, DMSO-d$_6$) δ 1.61-1.80 (m, 2H), 1.87 (s, 3H), 1.89-2.20 (m, 4H), 2.24-2.42 (m, 1H), 2.61-2.70 (m, 1H), 2.70-2.99 (m, 4H), 3.09-3.21 (m, 2H), 3.75 (s, 3H), 3.78-4.40 (m, 3H), 5.89 (d, J=3.8 Hz, 1H), 7.15-7.26 (m, 2H), 7.31 (td, J=8.7, 3.2 Hz, 1H), 8.12 (d, J=2.5 Hz, 1H), 11.71 (s, 1H). MS (ESI$^+$) m/z 485 (M+H)$^+$.

EXAMPLE 1190

2-{4-[5-cyano-4-(5-fluoro-2-methoxyphenyl)-1H-pyrrolo[2,3-b]pyridin-2-yl]piperidin-1-yl}-N-(2-hydroxyethyl)-N-methylacetamide The title compound was prepared using the procedure described in Example 238, substituting Example 290B for Example 226B and 2-(methylamino)ethanol for azetidin-3-ol hydrochloride. $^1$H NMR (400 MHz, DMSO-d$_6$) δ 1.71 (dp, J=13.0, 9.4, 8.7 Hz, 2H), 1.95 (ddt, J=12.0, 5.7, 3.2 Hz, 2H), 2.16 (td, J=11.7, 2.5 Hz, 2H), 2.73 (tq, J=10.8, 3.4 Hz, 1H), 2.82 (s, 2H), 2.85-2.99 (m, 2H), 3.07 (s, 1H), 3.15 (s, 1H), 3.20 (s, 1H), 3.25-3.68 (m, 4H), 3.76 (s, 3H), 6.04 (d, J=4.7 Hz, 1H), 7.07-7.36 (m, 3H), 7.38 (td, J=8.6, 3.1 Hz, 1H). MS (ESI$^+$) m/z 466 (M+H)$^+$.

EXAMPLE 1191 tert-butyl {4-[3-cyano-4-(5-fluoro-2-methoxyphenyl)-1H-pyrrolo[2,3-b]pyridin-2-yl]-3,6-dihydropyridin-1(2H)-yl}acetate The title compound was prepared as described in Example 742, substituting Example 248E for Example 485. $^1$H NMR (400 MHz, DMSO-d$_6$) δ 1.43 (s, 9H), 2.65 (tt, J=5.8, 2.7 Hz, 2H), 2.80 (t, J=5.6 Hz, 2H), 3.20-3.40 (m, 4H), 3.72 (s, 3H), 6.59-6.69 (m, 1H), 7.06-7.24 (m, 3H), 7.29 (td, J=8.7, 3.2 Hz, 1H), 8.37 (d, J=4.9 Hz, 1H), 12.76 (s, 1H). MS (ESI$^+$) m/z 463 (M+H)$^+$.

EXAMPLE 1192

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-oxoethanesulfonamide A mixture of Example 845 (60 mg, 0.172 mmol), 2-sulfamoylacetic acid (26.3 mg, 0.189 mmol), O-(7-azabenzotriazol-1-yl)-N,N'N'N'-tetramethyluronium hexafluorophosphate (71.8 mg, 0.189 mmol) and triethylamine (0.072 mL, 0.515 mmol) in dimethylformamide (1.6 mL) was stirred at room temperature overnight. The reaction mixture was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-$d_6$) δ ppm 2.56-3.29 (m, 4 H) 3.50-3.63 (m, 2 H) 3.73 (s, 3 H) 3.74-4.16 (m, 4 H) 6.19 (dd, J=4.43, 1.98 Hz, 1 H) 6.32 (s, 1 H) 6.90-6.98 (m, 2 H) 7.04 (d, J=4.88 Hz, 1 H) 7.16-7.31 (m, 3 H) 8.21 (d, J=4.88 Hz, 1H) 11.91 (s, 1 H). MS (ESI$^+$) m/z 471 (M+H)$^+$.

EXAMPLE 1193

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-oxopropane-2-sulfonamide The title compound was prepared as described in Example 1192, substituting 2-sulfamoylpropanoic acid for 2-sulfamoylacetic acid. $^1$H NMR (400 MHz, DMSO-$d_6$) δ ppm 1.32-1.43 (m, 3 H) 2.56-3.31 (m, 4 H) 3.42-3.71 (m, 2 H) 3.73 (s, 3 H) 3.75-4.30 (m, 3 H) 6.17-6.22 (m, 1 H) 6.33 (d, J=6.71 Hz, 1 H) 6.79-6.90 (m, 2 H) 7.04 (dd, J=5.19, 1.22 Hz, 1 H) 7.16-7.31 (m, 3 H) 8.21 (d, J=4.88 Hz, 1 H) 11.91 (s, 1 H). MS (ESI$^+$) m/z 485 (M+H)$^+$.

EXAMPLE 1194

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethyl-2-oxoethanesulfonamide The title compound was prepared as described in Example 1192, substituting 2-(N,N-dimethylsulfamoyl)acetic acid for 2-sulfamoylacetic acid. $^1$H NMR (400 MHz, DMSO-$d_6$) δ ppm 2.58-2.68 (m, 1 H) 2.77 (s, 3 H) 2.78 (s, 3 H) 2.81-3.15 (m, 3 H) 3.47-3.66 (m, 2 H) 3.73 (s, 3 H) 3.78-4.23 (m, 4 H) 6.19 (dd, J=3.51, 1.98 Hz, 1 H) 6.32 (d, J=7.32 Hz, 1 H) 7.04 (d, J=4.88 Hz, 1 H) 7.14-7.35 (m, 3 H) 8.21 (d, J=4.88 Hz, 1 H) 11.91 (dd, J=7.63, 1.53 Hz, 1 H). MS (ESI$^+$) m/z 499 (M+H)$^+$.

EXAMPLE 1195 tert-butyl {5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetate A mixture of Example 845 (700 mg, 2.003 mmol), tert-butyl 2-bromoacetate (0.311 ml, 2.104 mmol) and triethylamine (0.838 ml, 6.01 mmol) in dimethylformamide (6 ml) was stirred at room temperature for 16 hours. Water was added dropwise to the reaction mixture to form a precipitate which was collected by filtration, washed with hexanes and dried at 50° C. under vacuum overnight to afford the title compound. $^1$H NMR (400 MHz, DMSO-$d_6$) δ ppm 1.39 (s, 9 H) 2.56-3.21 (m, 8 H) 3.40 (s, 2 H) 3.73 (s, 3 H) 6.11 (d, J=1.83 Hz, 1 H) 6.29 (d, J=1.83 Hz, 1 H) 7.03 (d, J=4.88 Hz, 1 H) 7.11-7.33 (m, 3 H) 8.19 (d, J=4.88 Hz, 1 H) 11.84 (d, J=1.53 Hz, 1 H). MS (ESI$^+$) m/z 464 (M+H)$^+$.

EXAMPLE 1198

4-({4-[4-(5-fluoro-2-methoxyphenyl)-1H-pyrrolo[2,3-b]pyridin-2-yl]-3,6-dihydropyridin-1(2H)-yl}carbonyl)benzoic acid

EXAMPLE 1198A methyl 4-(4-(4-(5-fluoro-2-methoxyphenyl)-1H-pyrrolo[2,3-b]pyridin-2-yl)-1,2,3,6-tetrahydropyridine-1-carbonyl)benzoate The title compound was prepared essentially as described in Example 699, substituting 4-(methoxycarbonyl)benzoic acid for 2-(methylsulfonyl)acetic acid. MS (APCI$^+$) m/z 486.2 (M+H)$^+$.

EXAMPLE 1198B 4-({4-[4-(5-fluoro-2-methoxyphenyl)-1H-pyrrolo[2,3-b]pyridin-2-yl]-3,6-dihydropyridin-1(2H)-yl}carbonyl)benzoic acid The title compound was prepared essentially as described in Example 681, substituting Example 1198A for Example 676. $^1$H NMR (400 MHz, DMSO-$d_6$, 90° C.) δ ppm 2.53-2.63 (m, 2H), 3.58-3.68 (m, 2H), 3.72 (s, 3H), 4.09-4.26 (m, 2H), 6.26 (s, 1H), 6.44-6.53 (m, 1H), 7.03 (d, J=5.0 Hz, 1H), 7.13-7.28 (m, 3H), 7.48-7.54 (m, 2H), 7.91-8.08 (m, 2H), 8.20 (d, J=5.0 Hz, 1H), 11.48-11.63 (m, 1H). MS (ESI$^+$) m/z 472.2 (M+H)$^+$.

EXAMPLE 1199

3-({4-[4-(5-fluoro-2-methoxyphenyl)-1H-pyrrolo[2,3-b]pyridin-2-yl]-3,6-dihydropyridin-1(2H)-yl}carbonyl)benzoic acid

EXAMPLE 1199A methyl 3-(4-(4-(5-fluoro-2-methoxyphenyl)-1H-pyrrolo[2,3-b]pyridin-2-yl)-1,2,3,6-tetrahydropyridine-1-carbonyl)benzoate The title compound was prepared essentially as described in Example 699, substituting 3-(methoxycarbonyl)benzoic acid for 2-(methylsulfonyl)acetic acid. MS (APCI$^+$) m/z 486.2 (M+H)$^+$.

EXAMPLE 1199B 3-({4-[4-(5-fluoro-2-methoxyphenyl)-1H-pyrrolo[2,3-b]pyridin-2-yl]-3,6-dihydropyridin-1(2H)-yl}carbonyl)benzoic acid The title compound was prepared essentially as described in Example 681, substituting Example 1199A for Example 676. $^1$H NMR (400 MHz, DMSO-$d_6$, 90° C.) δ ppm 2.53-2.63 (m, 2H), 3.64-3.70 (m, 2H), 3.72 (s, 3H), 4.17-4.27 (m, 2H), 6.27 (s, 1H), 6.45-6.53 (m, 1H), 7.04 (d, J=5.0 Hz, 1H), 7.11-7.28 (m, 3H), 7.53-7.60 (m, 1H), 7.62-7.68 (m, 1H), 7.90-7.97 (m, 1H), 7.98-8.05 (m, 1H), 8.20 (d, J=5.0 Hz, 1H), 11.60 (m, 1H). MS (ESI$^+$) m/z 472.2 (M+H)$^+$.

EXAMPLE 1200 tert-butyl (3aS,6aR)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate Preparative SFC chiral separation of Example 262D (4.0 g) was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase comprised of supercritical carbon dioxide supplied by a Dewar of anhydrous, non-certified carbon dioxide pressurized to 350 psi with a modifier of methanol at a flow rate of 70 g/minute. UV detection was set to collect at a wavelength of 220 nm, the column was at ambient temperature, and the backpressure regulator was set to maintain 100 bar. The sample was dissolved in methanol at a concentration of 100 mg/mL. The sample was loaded into the modifier stream in 1 mL (100 mg) injections. The mobile phase was held isocraticly at 20% methanol:carbon dioxide. Fraction collection was time triggered. The instrument was fitted with a CHIRALPAK OD-H column (21 mm i.d.×250 mm length with 5 μm particles). The chiral separation afforded the title compound as the faster eluting enantiomer and Example 1201 (see below, slower eluting enantiomer). Optical rotation for the title compound was obtained using an Autopol IV® automatic polarimeter (c=10 mg/mL in choloform at 24.8° C.) $[\alpha]_D$=-165.20. $^1$H NMR (500 MHz, dimethylsulfoxide-$d_6$) δ ppm 1.36 (s, 9H), 2.59 (d, J=15.8 Hz, 1H), 2.80-2.90 (m, 1H), 2.91-3.03 (m, 2H), 3.36-3.61 (m, 4H), 3.74 (s, 3H), 6.19 (d, J=2.0 Hz, 1H), 6.31 (s, 1H), 7.04 (d, J=4.9 Hz, 1H), 7.15-7.33 (m, 3H), 8.21 (d, J=4.9 Hz, 1H), 11.90 (s, 1H). LC-MS: 450 (M+H)$^+$.

EXAMPLE 1201 tert-butyl (3aR,6aS)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate The title compound was prepared in Example 1200, and corresponds to the slower eluting enantiomer under the SFC conditions. Optical rotation was obtained using an Autopol IV® automatic polarimeter (c=10 mg/mL in choloform at 24.8° C.) $[\alpha]_D$=+161.10. $^1$H NMR (500 MHz, dimethylsulfoxide-$d_6$) δ ppm 1.36 (s, 9H), 2.59 (d, J=15.8 Hz, 1H), 2.80-2.90 (m, 1H), 2.90-3.01 (m, 2H), 3.35-3.61 (m, 4H), 3.74 (s, 3H), 6.19 (d, J=2.0 Hz, 1H), 6.31 (s, 1H), 7.04 (d, J=4.9 Hz, 1H), 7.15-7.33 (m, 3H), 8.21 (d, J=4.9 Hz, 1H), 11.90 (s, 1H). LC-MS: 450 (M+H)$^+$.

EXAMPLE 1202

(3-{4-[4-(5-fluoro-2-methoxyphenyl)-1H-pyrrolo[2,3-b]pyridin-2-yl]-3,6-dihydropyridin-1(2H)-yl}cyclobutyl)acetic acid

EXAMPLE 1202A methyl 2-(3-(4-(4-(5-fluoro-2-methoxyphenyl)-1H-pyrrolo[2,3-b]pyridin-2-yl)-5,6-dihydropyridin-1(2H)-yl)cyclobutyl)acetate The title compound was prepared essentially as described in Example 288A, substituting methyl 2-(3-oxocyclobutyl) acetate for methyl 2-(4-oxocyclohexyl)acetate. The product was isolated as a mixture of cis- and trans-isomers. MS (ESI$^+$) m/z 450.1 (M+H)$^+$.

EXAMPLE 1202B (3-{4-[4-(5-fluoro-2-methoxyphenyl)-1H-pyrrolo[2,3-b]pyridin-2-yl]-3,6-dihydropyridin-1(2H)-yl}cyclobutyl)acetic acid The title compound was prepared essentially as described in Example 681, substituting Example 1202A for Example 676. $^1$H NMR (500 MHz, DMSO-$d_6$) δ ppm 1.85-2.15 (m, 2H), 2.21-2.54 (m, 5H), 2.60-2.89 (m, 2H), 3.04-3.17 (m, 1H), 3.46-3.55 (m, 1H), 3.63-3.78 (m, 5H), 3.88-4.10 (m, 2H), 6.39 (d, J=2.0 Hz, 1H), 6.45-6.52 (m, 1H), 7.09 (d, J=4.9 Hz, 1H), 7.17-7.35 (m, 3H), 8.26 (d, J=5.0 Hz, 1H), 9.88-10.01 (m, 1H), 12.06 (d, J=2.3 Hz, 1H). MS (ESI$^+$) m/z 436.0 (M+H)$^+$.

EXAMPLE 1203

2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoic acid A mixture of Example 1174F (0.049 g, 0.103 mmol) in tetrahydrofuran (0.5 ml) and methanol (0.5 ml) was treated with aqueous 2 M lithium hydroxide (0.155 ml, 0.309 mmol) and the reaction was stirred at room temperature for 3 hours. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% ammonium hydroxide/water to afford the title compound. $^1$H NMR (500 MHz, DMSO-$d_6$) δ ppm 1.47 (d, J=7.2 Hz, 3H), 2.53-2.62 (m, 2H), 3.11 (t, J=5.7 Hz, 2H), 3.56-3.63 (m, 2H), 3.74 (s, 3H), 4.49 (q, J=7.2 Hz, 1H), 6.24 (s, 1H), 6.56-6.62 (m, 1H), 7.03 (d, J=4.9 Hz, 1H), 7.12 (s, 1H), 7.17-7.30 (m, 3H), 7.32 (s, 1H), 8.20 (d, J=4.9 Hz, 1H), 11.84 (brs, 1H). MS (ESI$^+$) m/z 462.2 (M+H)$^+$.

EXAMPLE 1204 ethyl 5-[4-(5-fluoro-2-methoxyphenyl)-1H-pyrrolo[2,3-b]pyridin-2-yl]-1,2,3,6-tetrahydropyridine-4-carboxylate

EXAMPLE 1204A 1-tert-butyl 4-ethyl 3-(4-(5-fluoro-2-methoxyphenyl)-1H-pyrrolo[2,3-b]pyridin-2-yl)-5,6-dihydropyridine-1,4(2H)-dicarboxylate The title compound was prepared essentially as described in Example 1171C, substituting Example 679B for Example 1171B. MS (ESI$^+$) m/z 496.1 (M+H)$^+$.

EXAMPLE 1204B ethyl 5-[4-(5-fluoro-2-methoxyphenyl)-1H-pyrrolo[2,3-b]pyridin-2-yl]-1,2,3,6-tetrahydropyridine-4-carboxylate The title compound was prepared essentially as described in Example 913, substituting Example 1204A for Example 908. $^1$H NMR (500 MHz, DMSO-$d_6$) δ ppm 0.93 (t, J=7.1

Hz, 3H), 2.65-2.73 (m, 2H), 3.24-3.31 (m, 2H), 3.74 (s, 3H), 4.03 (q, J=7.1 Hz, 2H), 4.07-4.14 (m, 2H), 6.40 (d, J=1.7 Hz, 1H), 7.12-7.28 (m, 3H), 7.28-7.39 (m, 1H), 8.32 (d, J=5.1 Hz, 1H), 9.53-9.63 (m, 2H), 12.16 (brs, 1H). MS (ESI$^+$) m/z 396.1 (M+H)$^+$.

EXAMPLE 1206

4-(5-fluoro-2-methoxyphenyl)-2-[1-(2,5,8,11-tetraoxatetradecan-14-yl)-1,2,3,6-tetrahydropyridin-4-yl]-1H-pyrrolo[2,3-b]pyridine The title compound was prepared using the procedure described in Example 110, using Example 87D in place of Example 59F and 2,5,8,11-tetraoxatetradecan-14-al in place of tetrahydro-4H-pyran-4-one. $^1$H NMR (500 MHz, DMSO-d$_6$): δ 1.93-2.01 (m, 2 H) 2.74-2.89 (m, 2 H) 3.21-3.27 (m, 5 H) 3.40-3.43 (m, 2 H) 3.47-3.55 (m, 12 H) 3.66-3.71 (m, 1 H) 3.74 (s, 3 H) 3.82-3.90 (m, 1 H) 4.07-4.15 (m, 1 H) 6.38 (d, J=2.14 Hz, 1 H) 6.45-6.49 (m, 1 H) 7.08 (d, J=4.88 Hz, 1 H) 7.18-7.32 (m, 3 H) 8.25 (d, J=4.88 Hz, 1 H) 9.56 (br. s, 1 H) 12.02 (s, 1 H). MS (ESI$^+$) m/z: 528.1 (M+H)$^+$.

EXAMPLE 1207

5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-3-carbonitrile The title compound was prepared essentially as described in Example 220E, substituting Example 1188 for Example 220D. $^1$H NMR (400 MHz, DMSO-d$_6$) δ 2.84-2.88 (m, 1H), 2.91 (s, 3H), 3.01-3.12 (m, 1H), 3.15-3.23 (m, 2H), 3.26 (dd, J=10.1, 2.9 Hz, 1H), 3.44 (dd, J=10.1, 8.1 Hz, 1H), 3.50 (dd, J=9.9, 7.7 Hz, 1H), 3.70 (tt, J=5.5, 2.7 Hz, 1H), 3.77 (s, 3H), 6.75 (q, J=1.8 Hz, 1H), 7.10-7.24 (m, 1H), 7.24-7.36 (m, 2H), 8.33 (d, J=9.1 Hz, 1H). MS (ESI$^+$) m/z (M+H)$^+$.

EXAMPLE 1208

5-[3-cyano-5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide The title compound was prepared essentially as described in Examples 222D, substituting Example 1188 for Example 222C. $^1$H NMR (400 MHz, DMSO-d$_6$) δ 2.60 (s, 3H), 2.85-2.95 (m, 1H), 3.05-3.25 (m, 3H), 3.48 (d, J=5.2 Hz, 2H), 3.58-3.71 (m, 2H), 3.82 (s, 3H), 6.81 (q, J=1.9 Hz, 1H), 7.24 (ddd, J=8.4, 4.6, 1.2 Hz, 1H), 7.35 (t, J=8.4 Hz, 2H), 8.37 (d, J=9.2 Hz, 1H). MS (ESI$^+$) m/z 423 (M+H)$^+$.

EXAMPLE 1209

{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}) acetic acid The title compound was prepared using the procedure described in Example 226, substituting Example 1147 for Example 87D in Example 226A. $^1$H NMR (500 MHz, DMSO-d$_6$) δ), 2.60-3.37 (m, 5H), 3.70-3.80 (m, 6H), 4.15 (s, 2H), 6.29 (d, J=9.5 Hz, 1H), 6.39 (s, 1H), 7.20-7.40 (m, 3H), 8.46 (m, 1H), 10.17 (s, 1H), 12.69 (d, J=5.2 Hz, 1H). MS (ESI$^+$) m/z 433 (M+H)$^+$.

EXAMPLE 1210

2-{4-[3-cyano-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide

EXAMPLE 1210A 2-(4-(3-cyano-4-(5-fluoro-2-methoxyphenyl)-1H-pyrrolo[2,3-b]pyridin-2-yl)-5,6-dihydropyridin-1(2H)-yl)acetic acid The title compound was prepared as described in Example 271D, substituting Example 1191 for Example 271C.

EXAMPLE 1210B

2-{4-[3-cyano-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide The title compound was prepared using the procedure described in Example 238, substituting Example 1210A for Example 226B and N-(3-hydroxycyclobutyl)-N-methylamine for azetidin-3-ol hydrochloride. $^1$H NMR (400 MHz, DMSO-d$_6$) δ 1.85-2.09 (m, 2H), 2.28-2.50 (m, 2H), 2.50-3.00 (m, 7H), 3.20-3.40 (m, 4H), 3.50-3.79 (m, 4H), 4.0-4.4 (m, 1H), 5.03 (dt, J=23.4, 5.2 Hz, 1H), 6.65 (t, J=3.5 Hz, 1H), 7.06-7.24 (m, 3H), 7.29 (td, J=8.7, 3.2 Hz, 1H), 8.37 (d, J=4.9 Hz, 1H), 12.75 (s, 1H). MS (ESI$^+$) m/z 490 (M+H)$^+$.

EXAMPLE 1211

4-(5-fluoro-2-methoxyphenyl)-2-{2-[2-(3-hydroxyazetidin-1-yl)-2-oxoethyl]-1,2,3,3a,4,6a-hexahydrocyclopenta[c]pyrrol-5-yl}-1H-pyrrolo[2,3-b]pyridine-5-carbonitrile The title compound was prepared using the procedure described in Example 238, substituting Example 1209 for Example 226B. $^1$H NMR (500 MHz, DMSO-d$_6$) δ 2.40-2.60 (m, 5H), 2.84-3.07 (m, 4H), 3.3-3.4 (m, 1H), 3.53 (dt, J=9.8, 4.4 Hz, 1H), 3.75 (s, 3H), 3.81 (dt, J=9.6, 4.5 Hz, 1H), 3.94-4.05 (m, 1H), 4.25 (q, J=7.5, 6.8 Hz, 1H), 4.36 (h, J=5.9 Hz, 1H), 5.62 (t, J=6.2 Hz, 1H), 6.17 (t, J=2.4 Hz, 1H), 6.40 (s, 1H), 7.28 (ddd, J=13.5, 8.8, 4.0 Hz, 2H), 7.39 (td, J=8.6, 3.2 Hz, 1H), 8.61 (s, 1H), 12.52 (s, 1H). MS (ESI$^+$) m/z 433 (M+H)$^+$.

EXAMPLE 1212

4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile The title compound was prepared using the procedure described in Example 238, substituting Example 1210A for Example 226B. $^1$H NMR (500 MHz, DMSO-d$_6$) δ 2.74 (d, J=53.1 Hz, 5H), 2.99-3.25 (m, 3H), 3.61 (dd, J=10.2, 4.3 Hz, 1H), 3.72 (s, 3H), 3.91 (dd, J=9.4, 4.4 Hz, 1H), 4.07 (dd, J=10.1, 6.8 Hz, 1H), 4.30-4.41 (m, 1H), 4.45 (h, J=6.0, 5.6 Hz, 1H), 5.72 (d, J=6.0 Hz, 1H), 6.65 (d, J=3.8 Hz, 1H), 7.08-7.24 (m, 3H), 7.24-7.40 (m, 1H), 8.38 (d, J=4.9 Hz, 1H), 12.79 (s, 1H). MS (ESI$^+$) m/z 462 (M+H)$^+$.

EXAMPLE 1213

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide A mixture of Example 989 (40.7 mg, 0.100 mmol), 2-(methylamino)ethanol (15.05 mg, 0.200 mmol), 1-[bis(dimethylamino)methylene]-1H-1,2,3-triazolo[4,5-b]pyridinium 3-oxide hexafluorophosphate (45.7 mg, 0.120 mmol) and triethylamine (69.8 μl, 0.501 mmol) in dimethylformamide (2 mL) was stirred at room temperature overnight. The reaction mixture was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-d$_6$) δ ppm 2.53-3.07 (m, 10 H) 3.35 (s, 3 H) 3.43-3.69 (m, 5 H) 3.73 (s, 3 H) 6.15 (s, 1 H) 6.30 (s, 1 H) 7.04 (d, J=4.88 Hz, 1 H) 7.15-7.33 (m, 3 H) 8.21 (d, J=4.88 Hz, 1 H) 11.90 (s, 1 H). MS (ESI$^+$) m/z 465 (M+H)$^+$.

EXAMPLE 1214

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide The title compound was prepared as described in Example 1213, substituting 3-(methylamino)cyclobutanol hydrochloride for 2-(methylamino)ethanol. $^1$H NMR (400 MHz, DMSO-d$_6$) δ ppm 1.80-2.43 (m, 8 H) 2.56-3.23 (m, 11 H) 3.73 (s, 3 H) 4.00-4.37 (m, 1 H) 6.11 (s, 1 H) 6.29 (s, 1 H) 7.02 (d, J=4.88 Hz, 1 H) 7.13-7.35 (m, 3 H) 8.19 (d, J=4.88 Hz, 1 H) 11.83 (s, 1 H). MS (ESI$^+$) m/z 491 (M+H)$^+$.

EXAMPLE 1215

(3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide

EXAMPLE 1215A (3aR,5r,6aS)-tert-butyl 5-(4-(5-fluoro-2-methoxyphenyl)-1H-pyrrolo[2,3-b]pyridin-2-yl)hexahydrocyclopenta[]pyrrole-2(1H)-carboxylate Example 262D (1.20 g, 2.67 mmol) and methanol (25 ml) were added to 20% Pd(OH)$_2$/C, (0.24 g, 0.174 mmol) in a 250 ml pressure bottle. The mixture was stirred for 32 hours at 30 psi of hydrogen and 50° C. The reaction mixture was filtered and the filtrate was concentrated to provide the title compound. $^1$H NMR (500 MHz, DMSO-d$_6$) δ ppm 1.38 (s, 9 H) 1.49-1.61 (m, 2 H) 2.25-2.35 (m, 2 H) 2.69 (br, 2 H) 3.18-3.29 (m, 3 H) 3.36-3.43 (m, 2 H) 3.72 (s, 3 H) 5.98 (d, 1 H) 6.99 (d, 1 H) 7.18 (d, 2 H) 7.25 (d, 1 H) 8.13 (d, J=4.88 Hz, 1 H) 11.61 (s, 1 H). The cis structure was confirmed by rotating frame nuclear Overhauser effect spectroscopy (ROESY). MS (ESI$^+$) m/z 452 (M+H)$^+$.

EXAMPLE 1215B 4-(5-fluoro-2-methoxyphenyl)-2-((3aR,5r,6aS)-octahydrocyclopenta[c]pyrrol-5-yl)-1H-pyrrolo[2,3-b]pyridine To Example 1215A (800 mg, 1.772 mmol) was added CH$_2$Cl$_2$/trifluoroacetic acid (2:1, 3 mL). The mixture was stirred at room temperature for 1 hour and concentrated in vacuo. The residue was dissolved in 2 ml of CH$_2$Cl$_2$ and HCl solution (2 M in ether, 3 mL) was added. The solid was collected by filtration to afford the title compound as the tri-hydrochloride salt. LC-MS: 352 (M+H)$^+$.

EXAMPLE 1215C (3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide To a mixture of Example 1215B (46.1 mg, 0.1 mmol) in dimethylformamide (0.75 mL) was added 2,5-dioxopyrrolidin-1-yl methylcarbamate (20.66 mg, 0.120 mmol) and triethylamine (0.070 mL, 0.500 mmol). The mixture was stirred at room temperature overnight and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-d$_6$) δ ppm 1.49-1.60 (m, 2 H) 2.26-2.38 (m, 2 H) 2.54 (s, 3 H) 2.64-2.75 (m, 2 H) 3.17-3.35 (m, 5 H) 3.72 (s, 3 H) 5.91-6.10 (m, 2 H) 7.04 (d, J=5.19 Hz, 1 H) 7.13-7.33 (m, 3 H) 8.15 (d, J=5.19 Hz, 1 H) 11.73 (s, 1 H). MS (ESI$^+$) m/z 409 (M+H)$^+$.

EXAMPLE 1216

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]ethanone A mixture of Example 1215B (46.1 mg, 0.1 mmol), acetic acid (7.21 mg, 0.120 mmol), 1-[bis(dimethylamino)methylene]-1H-1,2,3-triazolo[4,5-b]pyridinium 3-oxide hexafluorophosphate (45.6 mg, 0.120 mmol) and triethylamine (69.7 μl, 0.500 mmol) in dimethylformamide (1 mL) was stirred at room temperature overnight. The reaction mixture was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-d$_6$) δ ppm 1.46-1.70 (m, 2 H) 1.92 (s, 3 H) 2.20-2.39 (m, 2 H) 2.62-2.86 (m, 2 H) 3.21-3.62 (m, 5 H) 3.72 (s, 3 H) 6.01 (d, J=1.83 Hz, 1 H) 7.02 (d, J=5.19 Hz, 1 H) 7.15-7.31 (m, 3 H) 8.14 (d, J=5.19 Hz, 1 H) 11.68 (s, 1 H). MS (ESI$^+$) m/z 394 (M+H)$^+$.

EXAMPLE 1217

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-2-hydroxyethanone The title compound was prepared using the condition described in Example 1216, substituting 2-hydroxyacetic acid for acetic acid. $^1$H NMR (500 MHz, DMSO-$d_6$) δ ppm 1.49-1.65 (m, 2 H) 2.24-2.39 (m, 2 H) 2.63-2.85 (m, 2 H) 3.20-3.54 (m, 5 H) 3.72 (s, 3 H) 3.88-4.08 (m, 2 H) 4.44 (s, 1 H) 5.99 (d, J=1.53 Hz, 1 H) 6.99 (t, J=4.12 Hz, 1 H) 7.14-7.29 (m, 3 H) 8.10-8.16 (m, 1 H) 11.61 (s, 1 H). MS (ESI$^+$) m/z 410 (M+H)$^+$.

EXAMPLE 1218

(3aR,5r,6aS)-N-cyano-5-[4-(5-fluoro-2-methoxyphenyl)-1H-pyrrolo[2,3-b]pyridin-2-yl]hexahydrocyclopenta[c]pyrrole-2(1H)-carboxamide The title compound was prepared using the condition described in Example 1154, substituting Example 1215B for Example 845. $^1$H NMR (500 MHz, DMSO-$d_6$) δ ppm 1.44-1.66 (m, 2 H) 2.22-2.38 (m, 2 H) 2.63-2.77 (m, 2 H) 3.07-3.50 (m, 5 H) 3.72 (s, 3 H) 5.98 (d, J=1.53 Hz, 1 H) 6.99 (d, J=5.19 Hz, 1 H) 7.05-7.31 (m, 4 H) 8.12 (t, J=5.04 Hz, 1 H) 11.61 (s, 1 H). MS (ESI$^+$) m/z 420 (M+H)$^+$.

EXAMPLE 1219

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N,N-dimethylacetamide The title compound was prepared as described in Example 880, substituting Example 1215B for Example 845. $^1$H NMR (400 MHz, DMSO-$d_6$) δ ppm 1.35-1.51 (m, 2 H) 2.20-2.40 (m, 4 H) 2.55-2.69 (m, 4 H) 2.78 (s, 3 H) 3.01 (s, 3 H) 3.00-3.08 (m, 1 H) 3.23 (s, 2 H) 3.72 (s, 3 H) 5.92 (d, J=1.22 Hz, 1 H) 7.00 (d, J=4.88 Hz, 1 H) 7.12-7.32 (m, 3 H) 8.13 (d, J=4.88 Hz, 1 H) 11.57 (s, 1 H). MS (ESI$^+$) m/z 437 (M+H)$^+$.

EXAMPLE 1220

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]propane-1,2-diol The title compound was prepared using the condition described in Example 149, substituting Example 1215B for Example 135B. $^1$H NMR (400 MHz, DMSO-$d_6$) δ ppm 1.59-1.93 (m, 2 H) 2.26-2.44 (m, 2 H) 2.79-3.60 (m, 11 H) 3.71 (s, 3 H) 3.80-4.46 (m, 2 H) 6.05 (s, 1 H) 7.04 (d, J=5.19 Hz, 1 H) 7.09-7.25 (m, 3 H) 8.16 (d, J=5.19 Hz, 1 H) 11.40 (s, 1 H). MS (ESI$^+$) m/z 426 (M+H)$^+$.

EXAMPLE 1221

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]acetamide The title compound was prepared using the condition described in Example 1153, substituting Example 1215B for Example 845. $^1$H NMR (400 MHz, DMSO-$d_6$) δ ppm 1.57-1.69 (m, 2 H) 2.13-2.44 (m, 4 H) 2.53-3.23 (m, 7 H) 3.72 (s, 3 H) 5.99 (d, J=1.53 Hz, 1 H) 7.00 (d, J=4.88 Hz, 1 H) 7.13-7.40 (m, 5 H) 8.13 (d, J=4.88 Hz, 1 H) 11.62 (s, 1 H). MS (ESI$^+$) m/z 409 (M+H)$^+$.

EXAMPLE 1222

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-3-oxopropanenitrile The title compound was prepared using the condition described in Example 1216, substituting 2-cyanoacetic acid for acetic acid. $^1$H NMR (500 MHz, DMSO-$d_6$) δ ppm 1.51-1.65 (m, 2 H) 2.27-2.36 (m, 2 H) 2.66-2.84 (m, 2 H) 3.21-3.60 (m, 5 H) 3.72 (s, 3 H) 3.90 (d, J=1.83 Hz, 2 H) 6.02 (d, J=1.53 Hz, 1 H) 7.04 (d, J=5.19 Hz, 1 H) 7.14-7.32 (m, 3 H) 8.15 (d, J=5.19 Hz, 1 H) 11.70 (s, 1 H). MS (ESI$^+$) m/z 419 (M+H)$^+$.

EXAMPLE 1223

4-[4-(5-fluoro-2-methoxyphenyl)-1H-pyrrolo[2,3-b]pyridin-2-yl]cyclohexanecarboxylic acid The title compound was prepared essentially as described in Example 992B, substituting Example 992A with Example 219C. $^1$H NMR (500 MHz, DMSO-$d_6$) δ ppm 11.33-11.69 (m, 1 H) 8.12 (d, J=4.88 Hz, 1 H) 7.09-7.37 (m, 3 H) 6.90-7.09 (m, 1 H) 5.80-6.01 (m, 1 H) 3.65-3.76 (m, 3 H) 2.59-2.87 (m, 1 H) 2.28-2.40 (m, 1 H) 1.89-2.12 (m, 2 H) 1.70-1.86 (m, 3 H) 1.35-1.60 (m, 3 H). MS (ESI): 369.3 (M+H)$^+$.

EXAMPLE 1224

(4-{4-[3-cyano-4-(5-fluoro-2-methoxyphenyl)-1H-pyrrolo[2,3-b]pyridin-2-yl]-3,6-dihydropyridin-1(2H)-yl}cyclohexyl)acetic acid

EXAMPLE 1224A methyl 2-(4-(4-(3-cyano-4-(5-fluoro-2-methoxyphenyl)-1H-pyrrolo[2,3-b]pyridin-2-yl)-5,6-dihydropyridin-1(2H)-yl)cyclohexyl)acetate The title compound was prepared essentially as described in Example 288A, substituting Example 248E for Example 87D. The product was isolated as a mixture of cis- and trans-isomers. MS (ESI$^+$) m/z 503.1 (M+H)$^+$.

EXAMPLE 1224B (4-{4-[3-cyano-4-(5-fluoro-2-methoxyphenyl)-1H-pyrrolo[2,3-b]pyridin-2-yl]-3,6-dihydropyridin-1(2H)-yl}cyclohexyl)acetic acid The title compound was prepared essentially as described in Example 681, substituting Example 1224A for Example 676. $^1$H NMR (500 MHz, CD$_3$OD) δ ppm 1.13-1.27 (m, 1H), 1.60-1.88 (m, 4H), 1.92-2.08 (m, 2H), 2.12-2.33 (m, 3H), 2.43 (d, J=7.7 Hz, 1H), 3.07-3.16 (m, 2H), 3.32-3.46 (m, 2H), 3.76 (s, 3H), 3.78-3.94 (m, 1H), 4.04-4.16 (m, 2H), 6.66-6.73 (m, 1H), 7.03-7.12 (m, 2H), 7.12-7.26 (m, 2H), 8.42 (d, J=4.9 Hz, 1H). MS (ESI+) m/z 489.2 (M+H)+.

EXAMPLE 1225

(4-{4-[5-fluoro-4-(5-fluoro-2-methoxyphenyl)-1H-pyrrolo[2,3-b]pyridin-2-yl]piperidin-1-yl}cyclohexyl)acetic acid

EXAMPLE 1225A methyl 2-(4-(4-(5-fluoro-4-(5-fluoro-2-methoxyphenyl)-1H-pyrrolo[2,3-b]pyridin-2-yl)piperidin-1-yl)cyclohexyl)acetate The title compound was prepared essentially as described in Example 288A, substituting Example 255D for Example 87D. The product was isolated as a mixture of cis- and trans-isomers. MS (ESI+) m/z 498.3 (M+H)+.

EXAMPLE 1225B (4-{4-[5-fluoro-4-(5-fluoro-2-methoxyphenyl)-1H-pyrrolo[2,3-b]pyridin-2-yl]piperidin-1-yl}cyclohexyl)acetic acid The title compound was prepared essentially as described in Example 681, substituting Example 1225A for Example 676. $^1$H NMR (400 MHz, CD$_3$OD) δ ppm 1.10-1.31 (m, 1H), 1.55-1.88 (m, 5H), 1.88-2.09 (m, 4H), 2.10-2.34 (m, 3H), 2.34-2.47 (m, 3H), 3.04-3.28 (m, 3H), 3.58-3.71 (m, 2H), 3.76 (s, 3H), 6.04 (s, 1H), 7.05-7.28 (m, 3H), 8.09 (d, J=3.0 Hz, 1H). MS (ESI+) m/z 484.3 (M+H)+.

EXAMPLE 1226

{4-[5-chloro-4-(5-fluoro-2-methoxyphenyl)-1H-pyrrolo[2,3-b]pyridin-2-yl]cyclohex-3-en-1-yl}acetic acid

EXAMPLE 1226A 5-chloro-4-iodo-1-tosyl-1H-pyrrolo[2,3-b]pyridine

To a solution of 5-chloro-4-iodo-1H-pyrrolo[2,3-b]pyridine (5.0 g, 17.95 mmol) in N,N-dimethylformamide (80 mL) was added ground NaOH (0.862 g, 21.55 mmol) in a single portion. The reaction mixture was stirred for 30 minutes, and a solution of p-toluenesulfonyl chloride (4.11 g, 21.55 mmol) in N,N-dimethylformamide (10 mL) was added. The reaction mixture was stirred for 16 hours and poured into 150 mL of water with vigorous stirring. The solid was filtered, washed with water and dried under vacuum to provide the title compound. MS (ESI+) m/z 433 (M+H).

EXAMPLE 1226B 5-chloro-4-(5-fluoro-2-methoxyphenyl)-1-tosyl-1H-pyrrolo[2,3-b]pyridine The title compound was prepared essentially as described in Example 236B, substituting Example 1226A for Example 236A. MS (ESI+) m/z 431 (M+H).

EXAMPLE 1226C 5-chloro-4-(5-fluoro-2-methoxyphenyl)-2-iodo-1-tosyl-1H-pyrrolo[2,3-b]pyridine The title compound was prepared essentially as described in Example 229B, substituting Example 1226B for Example 229A. MS (ESI+) m/z 557 (M+H).

EXAMPLE 1226D 5-chloro-4-(5-fluoro-2-methoxyphenyl)-2-iodo-1H-pyrrolo[2,3-b]pyridine The title compound was prepared essentially as described in Example 229E, substituting Example 1226C for Example 229D. MS (ESI+) m/z 403 (M+H).

EXAMPLE 1226E methyl 2-(4-(5-chloro-4-(5-fluoro-2-methoxyphenyl)-1H-pyrrolo[2,3-b]pyridin-2-yl)cyclohex-3-enyl)acetate The title compound was prepared essentially as described in Example 1171C, substituting Example 1226D for Example 219A. MS (ESI+) m/z 429 (M+H)+.

EXAMPLE 1226F

{4-[5-chloro-4-(5-fluoro-2-methoxyphenyl)-1H-pyrrolo[2,3-b]pyridin-2-yl]cyclohex-3-en-1-yl}acetic acid The title compound was prepared essentially as described in Example 681, substituting Example 1226E for Example 676. $^1$H NMR (400 MHz, DMSO-d$_6$) δ ppm 1.26-1.43 (m, 1H), 1.72-2.05 (m, 3H), 2.14-2.44 (m, 5H), 3.70 (s, 3H), 5.92-6.01 (m, 1H), 6.46-6.55 (m, 1H), 7.13 (dd, J=8.7, 3.2 Hz, 1H), 7.20 (dd, J=9.1, 4.5 Hz, 1H), 7.31 (td, J=8.7, 3.2 Hz, 1H), 8.21 (s, 1H), 11.92 (d, J=2.3 Hz, 1H) MS (ESI+) m/z 415.2 (M+H)+.

EXAMPLE 1227

2-({4-[4-(5-fluoro-2-methoxyphenyl)-1H-pyrrolo[2,3-b]pyridin-2-yl]-3,6-dihydropyridin-1(2H)-yl}sulfonyl)ethanol

EXAMPLE 1227A 2-(4-(4-(5-fluoro-2-methoxyphenyl)-1-(phenylsulfonyl)-1H-pyrrolo[2,3-b]pyridin-2-yl)-5,6-dihydropyridin-1(2H)-ylsulfonyl)ethanol The title compound was prepared using the procedure described in Example 223D, using Example 660A in place of Example 223C and using 2-hydroxyethanesulfonyl chloride in place of methanesulfonyl chloride. MS (ESI+) m/z: 572.0 (M+H)+.

EXAMPLE 1227B 2-({4-[4-(5-fluoro-2-methoxyphenyl)-1H-pyrrolo[2,3-b]pyridin-2-yl]-3,6-dihydropyridin-1(2H)-yl}sulfonyl)ethanol The title compound was prepared using the procedure described in Example 236E, using Example 1227A in place of Example 236D. ¹H NMR (500 MHz, DMSO-d₆): δ 2.70-2.88 (m, 2 H) 2.97 (t, J=7.63 Hz, 2 H) 3.23-3.36 (m, 1 H) 3.42-3.52 (m, 2 H) 3.75 (s, 3 H) 3.86-3.97 (m, 2 H) 4.08-4.19 (m, 1 H) 6.38 (d, J=1.53 Hz, 1 H) 6.43-6.50 (m, 1 H) 7.09 (d, J=4.88 Hz, 1 H) 7.17-7.33 (m, 3 H) 8.26 (d, J=4.88 Hz, 1 H) 9.53 (br. s, 1 H) 12.03 (s, 1 H). MS (ESI⁺) m/z: 432.0 (M+H)⁺.

EXAMPLE 1228

(3-{4-[4-(5-fluoro-2-methoxyphenyl)-1H-pyrrolo[2,3-b]pyridin-2-yl]-3,6-dihydropyridin-1(2H)-yl}cyclobutyl)(3-hydroxyazetidin-1-yl)methanone The title compound was prepared essentially as described in Example 238, substituting Example 1126 for Example 226B. ¹H NMR (500 MHz, CD₃OD) δ ppm 2.37-2.50 (m, 2H), 2.59-2.68 (m, 2H), 2.87-3.09 (m, 3H), 3.26-3.34 (m, 1H), 3.72-3.89 (m, 6H), 3.92-3.99 (m, 1H), 4.16-4.24 (m, 1H), 4.36-4.46 (m, 1H), 4.54-4.65 (m, 1H), 4.77-4.95 (m, 2H), 6.46-6.53 (m, 1H), 6.63 (s, 1H), 7.16-7.31 (m, 3H), 7.40 (d, J=5.7 Hz, 1H), 8.31 (d, J=5.7 Hz, 1H). MS (ESI⁺) m/z 477.1 (M+H)⁺.

EXAMPLE 1229

2-{5-[3-cyano-5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide The title compound was prepared as described in Example 1145, substituting Example 1188 for Example 271D. ¹H NMR (500 MHz, DMSO-d₆) δ 2.90 (s, 4H), 2.93 (s, 2H), 2.98-3.11 (m, 2H), 3.14-3.34 (m, 1H), 3.36-3.59 (m, 2H), 3.62-3.77 (m, 1H), 3.77 (s, 3H), 3.86-3.97 (m, 2H), 4.30-4.41 (m, 2H), 6.76 (d, J=38.2 Hz, 1H), 7.20 (dd, J=8.9, 4.5 Hz, 1H), 7.30 (ddt, J=10.7, 6.4, 3.0 Hz, 2H), 8.36 (d, J=9.0 Hz, 1H). MS (ESI⁺) m/z 478 (M+H)⁺.

EXAMPLE 1230

2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone

EXAMPLE 1230A (S)-tert-butyl 2-(4-(4-(5-fluoro-2-methoxyphenyl)-1H-pyrrolo[2,3-b]pyridin-2-yl)-2-methyl-5,6-dihydropyridin-1(2H)-yl)acetate The title compound was prepared as described in Example 299A using Example 258F in place of Example 272B. MS (ESI) m/e 452.4 (M+H)⁺.

EXAMPLE 1230B (S)-2-(4-(4-(5-fluoro-2-methoxyphenyl)-1H-pyrrolo[2,3-b]pyridin-2-yl)-2-methyl-5,6-dihydropyridin-1(2H)-yl)acetic acid The title compound was prepared as described in Example 299B using Example 1230A in place of Example 299A. MS (ESI) m/e 396.3 (M+H)⁺.

EXAMPLE 1230C

2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone The title compound was prepared as described in Example 299C using Example 1230B in place of Example 299B. ¹HNMR (500 MHz, DMSO-d₆) δ 1.15 (d, 3H), 2.42 (m, 2H), 2.55 (m, 1H), 2.93 (m, 2H), 3.25 (m, 1H), 3.39 (m, 1H), 3.60 (m, 1H), 3.74 (s, 3H), 3.94 (m, 1H), 4.05 (m, 1H), 4.40 (m, 2H), 5.66 (br d, 1H), 6.21 (s, 1H), 6.37 (m, 1H), 7.02 (d, 1H), 7.25 (m, 3H), 8.18 (d, 1H), 11.75 (br s, 1H). MS (ESI) m/e 451.1 (M+H)⁺.

EXAMPLE 1231

2-[(6R)-4-[4-(5-fluoro-2-methoxyphenyl)-1H-pyrrolo[2,3-b]813cetate813-2-yl]-6-methyl-3,6-dihydropyridin-1(2H)-yl]-1-(3-hydroxyazetidin-1-yl)ethanone

EXAMPLE 1231A (R)-tert-butyl 2-(4-(4-(5-fluoro-2-methoxyphenyl)-1H-pyrrolo[2,3-b]pyridin-2-yl)-2-methyl-5,6-dihydropyridin-1(2H)-yl)acetate The title compound was prepared as described in Example 299A using Example 1025D in place of Example 272B. MS (ESI) m/e 452.1 (M+H)⁺.

EXAMPLE 1231B (R)-2-(4-(4-(5-fluoro-2-methoxyphenyl)-1H-pyrrolo[2,3-b]pyridin-2-yl)-2-methyl-5,6-dihydropyridin-1(2H)-yl)acetic acid The title compound was prepared as described in Example 299B using Example 1231A in place of Example 299A. MS (ESI) m/e 396.5 (M+H)⁺.

EXAMPLE 1231C

2-[(6R)-4-[4-(5-fluoro-2-methoxyphenyl)-1H-pyrrolo[2,3-b]cetate-2-yl]-6-methyl-3,6-dihydropyridin-1(2H)-yl]-1-(3-hydroxyazetidin-1-yl)ethanone The title compound was prepared as described in Example 299C using Example 1231B in place of Example 299B. ¹HNMR (400 MHz, DMSO-d₆) δ 1.15 (d, 3H), 2.42 (M, 2H), 2.54 (m, 1H), 2.95 (m, 2H), 3.25 (m, 1H), 3.37 (m, 1H), 3.58 (m, 1H), 3.74 (s, 3H), 3.94 (m, 1H), 4.05 (m, 1H), 4.38 (m, 2H), 5.65 (br d, 1H), 6.21 (br s, 1H), 6.36 (m, 1H), 7.02 (d, 1H), 7.23 (m, 3H), 8.18 (d, 1H), 11.74 (br s, 1H). MS (ESI) m/e 451.0 (M+H)⁺.

EXAMPLE 1232

{5-[4-(5-fluoro-2-methoxyphenyl)-1H-pyrrolo[2,3-b]pyridin-2-yl]-1,2,3,6-tetrahydropyridin-4-yl}methanol

EXAMPLE 1232A tert-butyl 3-(4-(5-fluoro-2-methoxyphenyl)-1H-pyrrolo[2,3-b]pyridin-2-yl)-4-(hydroxymethyl)-5,6-dihydropyridine-1(2H)-carboxylate A solution of Example 1204A (0.1 g, 0.202 mmol) in tetrahydrofuran (2.018 ml) under a nitrogen atmosphere was cooled to −78° C. and a solution of 1.0 M lithium aluminum hydride in tetrahydrofuran (0.202 mL, 0.202 mmol) was added dropwise over 10 minutes. The reaction mixture was stirred at −78° C. for 2.5 hours. The reaction mixture was quenched by addition of 2 mL half-saturated aqueous ammonium chloride. The cooling bath was removed and the mixture was stirred at room temperature for 20 minutes. The mixture was partitioned between ethyl acetate (75 mL) and water (20 mL). The organic layer was washed with brine (10 mL), dried over anhydrous sodium sulfate, filtered and concentrated. The residue was purified by flash chromatography on silica gel (AnaLogix IntelliFlash 280 system) eluting with a gradient of from 0% to 5% methanol in dichloromethane to afford the title compound. MS (ESI+) m/z 454.1 (M+H)+.

EXAMPLE 1232B

{5-[4-(5-fluoro-2-methoxyphenyl)-1H-pyrrolo[2,3-b]pyridin-2-yl]-1,2,3,6-tetrahydropyridin-4-yl}methanol Example 1232A (0.0175 g, 0.039 mmol) in dichloromethane (0.482 ml) was treated with trifluoroacetic acid (0.071 ml, 0.926 mmol) and the solution was stirred at room temperature for 20 hours. The reaction mixture was concentrated and dried under vacuum to constant weight. The residue was dissolved in 0.5 mL methanol and treated with aqueous 2 N lithium hydroxide (0.096 mL, 0.193 mmol). The mixture was stirred at room temperature for 1 hour and concentrated. The residue was purified by flash chromatography on silica gel (AnaLogix IntelliFlash 280 system) eluting with a gradient of from 0% to 10% methanol in dichloromethane containing 1% ammonium hydroxide to afford the title compound. $^1$H NMR (400 MHz, DMSO-$d_6$) δ ppm 2.18-2.26 (m, 2H), 2.83 (t, J=5.7 Hz, 2H), 3.49-3.55 (m, 2H), 3.75 (s, 3H), 4.01-4.08 (m, 2H), 4.87 (t, J=5.2 Hz, 1H), 6.20 (s, 1H), 7.05 (d, J=4.9 Hz, 1H), 7.13-7.33 (m, 3H), 8.19 (d, J=5.0 Hz, 1H), 11.49 (brs, 1H). MS (ESI+) m/z 354.2 (M+H)+.

EXAMPLE 1233

{4-[4-(5-fluoro-2-methoxyphenyl)-1H-pyrrolo[2,3-b]pyridin-2-yl]-3,6-dihydropyridin-1(2H)-yl}(3-hydroxycyclobutyl)methanone The title compound was prepared as described in Example 238, substituting Example 87D for Example 226B and 3-hydroxycyclobutanecarboxylic acid for azetidin-3-ol hydrochloride. $^1$H NMR (400 MHz, DMSO-$d_6$) δ 1.96 (qdd, J=8.9, 6.1, 3.0 Hz, 2H), 2.29-2.44 (m, 3H), 2.72-2.95 (m, 2H), 3.60 (dt, J=36.8, 5.7 Hz, 2H), 3.73 (s, 3H), 3.98 (dt, J=15.0, 7.6 Hz, 1H), 4.12 (dq, J=8.4, 2.4 Hz, 2H), 5.05 (dd, J=7.1, 1.5 Hz, 1H), 6.24 (dd, J=6.5, 2.1 Hz, 1H), 6.44-6.55 (m, 1H), 7.03 (d, J=4.9 Hz, 1H), 7.13-7.34 (m, 3H), 8.20 (d, J=4.9 Hz, 1H), 11.84 (dd, J=10.2, 2.4 Hz, 1H). MS (ESI+) m/z 422 (M+H)+.

EXAMPLE 1234

4-(5-fluoro-2-methoxyphenyl)-2-[(3R)-3-methyl-1,2,3,6-tetrahydropyridin-4-yl]-1H-pyrrolo[2,3-b]pyridine

EXAMPLE 1234A tert-butyl allyl(2-oxo-3-(triphenylphosphoranylidene)propyl)carbamate To an oven dried 250 mL round bottom flask under nitrogen was added tert-butyl allylcarbamate (6.81 g, 43.3 mmol) followed by tetrahydrofuran (80 ml). n-Butyl lithium (17.32 ml, 43.3 mmol) was added at room temperature, the mixture was stirred for 10 minutes and 1-chloro-3-(triphenylphosphoranylidene)propan-2-one (13.89 g, 39.4 mmol) was added. The reaction was stirred at room temperature overnight. The reaction was poured into water and extracted with ethyl acetate, and the organic layer was dried with magnesium sulfate, filtered and concentrated to give the title compound.

EXAMPLE 1234B (E)-tert-butyl allyl(2-oxopent-3-en-1-yl)carbamate

To a 250 mL round bottom flask under nitrogen containing crude Example 1234A (4.24 g, 8.95 mmol) was added tetrahydrofuran (45 mL) and the flask was cooled to 0° C. in an ice bath. Acetaldehyde (5.06 ml, 90 mmol) was added and the reaction was allowed to slowly warm up overnight and stir at room temperature for 2 days. The reaction was concentrated on the rotary evaporator and purified via flash column chromatography (0-100% ethyl acetate/heptane gradient) to give the title compound.

EXAMPLE 1234C tert-butyl 5-oxo-5,6-dihydropyridine-1(2H)-carboxylate

To a 1 L round bottom flask containing Example 1234B (1.44 g, 6.02 mmol) under nitrogen was added anhydrous dichloromethane (301 ml). Benzylidene[1,3-bis(2,4,6-trimethylphenyl)-2-imidazolidinylidene]dichloro(tricyclohexylphosphine)ruthenium (0.272 g, 0.320 mmol) was added as a solid in a single portion. The reaction was stirred at room temperature for 16 hours. The reaction mixture was passed through a 1 inch silica plug and concentrated. The residue was purified via flash column chromatography to give the title compound.

EXAMPLE 1234D tert-butyl 4-bromo-5-oxo-5,6-dihydropyridine-1(2H)-carboxylate

To a 500 mL round bottom flask under nitrogen was added Example 1234C (8.14 g, 41.3 mmol) and dichloromethane (200 mL), and the solution was cooled to 0° C. Bromine (2.339 ml, 45.4 mmol) in 43 ml dichloromethane was added dropwise via addition funnel. Once the addition was complete, the reaction mixture was stirred at 0° C. for 30 minutes, triethylamine (6.90 ml, 49.5 mmol) was added and the solution was stirred for another 30 minutes. The reaction was transferred to a separatory funnel and washed with water, saturated aqueous sodium bicarbonate, dried with magnesium sulfate, filtered and concentrated. The residue was purified via flash column chromatography (0-100% ethyl acetate/heptane) to give the title compound.

EXAMPLE 1234E (S)-tert-butyl 4-bromo-5-hydroxy-5,6-dihydropyridine-1(2H)-carboxylate To a 50 mL 3-neck oven dried round bottom flask under argon was added (R)-diphenyl(pyrrolidin-2-yl)methanol (0.045 g, 0.178 mmol), 2 mL tetrahydrofuran and trimethyl borate (0.050 ml, 0.447 mmol) and the mixture was stirred at room temperature for 1 hour. Then borane diethylaniline complex (0.270 ml, 1.521 mmol) was added and the reaction was cooled to −15° C. with an acetone/salt bath. An internal temperature probe was used to monitor the temperature (−16° C. during addition). A tetrahydrofuran (15.21 ml) solution of Example 1234D (0.420 g, 1.521 mmol) was slowly added via syringe pump over 45 minutes. The reaction temperature was maintained below 0° C. and stirred until judged complete by TLC (30% ethyl acetate/heptane). Once complete, the mixture was diluted with ethyl acetate and extracted with 0.5 M HCl, and the organic layer was dried with magnesium sulfate, filtered and concentrated. The residue was purified via flash column chromatography to give the title compound.

EXAMPLE 1234F (S)-tert-butyl 4-bromo-5-((diethoxyphosphoryl)oxy)-5,6-dihydropyridine-1(2H)-carboxylate To a 25 mL round bottom flask containing Example 1234E (0.710 g, 2.55 mmol) was added dimethylamino pyridine (0.031 g, 0.255 mmol), dichloromethane (20 ml) and triethylamine (1.779 ml, 12.76 mmol). The solution was cooled to 0° C. under an argon atmosphere and 0.1 mL diethyl chlorophosphate was added. The reaction was allowed to slowly warm to room temperature over 2 hours. Once complete, the mixture was partitioned between dichloromethane and brine. The layers were separated and the aqueous layer was extracted with dichloromethane. The organics were combined, dried with magnesium sulfate, filtered, concentrated and the residue purified via flash column chromatography to yield the title compound.

EXAMPLE 1234G (S)-tert-butyl 4-bromo-5-methyl-5,6-dihydropyridine-1(2H)-carboxylate To a 250 mL round bottom flask under a nitrogen atmosphere was added copper(I) bromide-dimethyl sulfide complex (3.87 g, 18.83 mmol) and tetrahydrofuran (40 ml). The solution was cooled to 0° C., methylmagnesium bromide (5.88 ml, 3.2M in tetrahydrofuran, 18.83 mmol) was added and the mixture was stirred for 30 minutes. The flask was then cooled to −40° C. and Example 1234F (1.30 g, 3.14 mmol) in 20 mL of tetrahydrofuran was added and the mixture was stirred for 2 hours at −40° C. Once complete, the reaction was quenched with saturated aqueous ammonium chloride, extracted with ethyl acetate, dried over magnesium sulfate, filtered and concentrated by rotary evaporation. The residue was purified via flash column chromatography to give the title compound.

EXAMPLE 1234H (R)-tert-butyl 4-(4-(5-fluoro-2-methoxyphenyl)-1H-pyrrolo[2,3-b]pyridin-2-yl)-5-methyl-5,6-dihydropyridine-1(2H)-carboxylate To a 100 mL oven dried round bottom flask under argon was added Example 1234G (0.533 g, 1.930 mmol), 1,4-dioxane (15 ml), bis(pinacalato)diboron (0.490 g, 1.930 mmol), and oven dried potassium acetate (0.517 g, 5.26 mmol). Argon was bubbled through the mixture for 20 minutes before PdCl$_2$ (1,1'-bis(diphenylphosphino)ferrocene)-dichloromethane adduct (0.072 g, 0.088 mmol) was added and the bubbling was continued for another 10 minutes. The reaction was heated to 80° C. overnight, cooled to room temperature, and Example 219A (0.646 g, 1.755 mmol), PdCl$_2$ (1,1'-bis(diphenylphosphino)ferrocene)-dichloromethane adduct (0.072 g, 0.088 mmol), and sodium carbonate (2.63 ml, 5.26 mmol) were added. Argon was bubbled through the reaction for 5 minutes. The reaction mixture was heated to 75° C. and stirred for 16 hours, cooled to room temperature and poured onto 50 mL of water, extracted with ethyl acetate, dried over magnesium sulfate, filtered and concentrated. The residue was purified via flash column chromatography to yield the title compound.

EXAMPLE 1234I (R)-4-(5-fluoro-2-methoxyphenyl)-2-(3-methyl-1,2,3,6-tetrahydropyridin-4-yl)-1H-pyrrolo[2,3-b]pyridine To a 50 mL flask was added Example 1234H (0.218 g, 0.498 mmol), dichloromethane (2.491 ml) and then trifluoroacetic acid (1 ml, 12.98 mmol). The reaction was stirred at room temperature until complete by TLC (50% ethyl acetate/heptane). Once complete the volatiles were removed by rotary evaporation. The solids obtained were dissolved in dichloromethane and washed with saturated aqueous sodium bicarbonate. The layers were separated and the aqueous layer was extracted with dichloromethane. The organics were combined, dried with magnesium sulfate, filtered and concentrated. The crude product was purified via flash column chromatography (5-10% methanol/dichloromethane) to yield the title compound. $^1$H NMR (400 MHz, CDCl$_3$) δ 8.25 (d, J=5.0 Hz, 1H), 7.20 (dd, J=8.8, 3.1 Hz, 1H), 7.14-7.07 (m, 2H), 6.99 (dd, J=9.0, 4.5 Hz, 1H), 6.33 (s, 1H), 6.24 (t, J=3.4 Hz, 1H), 3.78 (s, 3H), 3.63 (s, 2H), 3.23-3.03 (m, 1H), 2.97 (dd, J=12.8, 2.5 Hz, 1H), 2.74 (s, 1H), 1.78 (bs, 1H), 1.26 (d, J=6.9 Hz, 3H). MS (ESI+) m/z 338.1 (M+H)$^+$.

EXAMPLE 1235

4-(5-fluoro-2-methoxyphenyl)-2-[(3S)-3-methyl-1,2,3,6-tetrahydropyridin-4-yl]-1H-pyrrolo[2,3-b]pyridine The title compound was prepared as described in Example 1234, substituting (S)-diphenyl(pyrrolidin-2-yl)methanol for (R)-diphenyl(pyrrolidin-2-yl)methanol in Example 1234E. $^1$H NMR (400 MHz, DMSO-d$_6$) δ 11.66 (d, J=2.2 Hz, 1H), 8.17 (d, J=4.9 Hz, 1H), 7.36-7.08 (m, 3H), 7.01 (d, J=4.9 Hz, 1H), 6.42 (t, J=3.3 Hz, 1H), 6.18 (d, J=1.9 Hz, 1H), 3.74 (s, 3H), 2.83 (dd, J=12.3, 3.9 Hz, 1H), 2.74 (dd, J=12.3, 2.2 Hz, 1H), 2.60 (s, 1H), 1.15 (d, J=6.8 Hz, 3H). MS (ESI+) m/z 338.1 (M+H)$^+$.

EXAMPLE 1236

2-[(3R)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide To a 25 mL round bottom flask under nitrogen containing Example 1234I (0.0223 g, 0.066 mmol) was added potassium carbonate (10.9 mg, 0.079 mmol), dimethylformamide (0.5 ml) and 2-chloro-N,N-dimethylacetamide (7.48 µl, 0.073 mmol), successively. The reaction mixture was stirred at room temperature and diluted with dichloromethane (50 mL) and washed with water. The aqueous layer was extracted with dichloromethane, and the organic layers were combined, dried over magnesium sulfate, filtered and concentrated. The residue was purified via flash column chromatography (5-10% methanol/dichloromethane) to yield the title compound. $^1$H NMR (500 MHz, DMSO-d$_6$) δ 11.69 (d, J=2.3 Hz, 1H), 8.18 (d, J=4.9 Hz, 1H), 7.34-7.14 (m, 4H), 7.01 (d, J=4.9 Hz, 1H), 6.36 (dd, J=4.5, 2.6 Hz, 1H), 6.20 (d, J=2.0 Hz, 1H), 3.73 (s, 3H), 3.24 (s, 2H), 3.06 (s, 3H), 3.05-2.94 (m, 1H), 2.95-2.84 (m, 1H), 2.82 (s, 3H), 2.75-2.60 (m, 1H), 2.66-2.58 (m, 1H), 1.19 (d, J=6.7 Hz, 3H). MS (ESI+) m/z 423.5 (M+H)$^+$.

EXAMPLE 1237

2-[(3S)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide The title compound was prepared as described in Example 1236, substituting Example 1235 for 1234I. $^1$H NMR (500 MHz, DMSO-d$_6$) δ 11.70 (d, J=2.2 Hz, 1H), 8.18 (d, J=5.0 Hz, 1H), 7.32-7.16 (m, 4H), 7.02 (d, J=4.9 Hz, 1H), 6.37 (dd, J=4.6, 2.5 Hz, 1H), 6.20 (d, J=2.1 Hz, 1H), 3.74 (s, 3H), 3.39 (dd, J=17.9, 4.6 Hz, 1H), 3.24 (bs, 2H), 3.06 (s, 3H), 2.99-2.89 (m, 1H), 2.83 (s, 3H), 2.78 (s, 1H), 2.68-2.60 (m, 1H), 1.19 (d, J=6.8 Hz, 3H). MS (ESI$^+$) m/z 423.5 (M+H)$^+$.

EXAMPLE 1239

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone

EXAMPLE 1239A 2-((3aR,5r,6aS)-5-(4-(5-fluoro-2-methoxyphenyl)-1H-pyrrolo[2,3-b]pyridin-2-yl)hexahydrocyclopenta[c]pyrrol-2(1H)-yl)acetic acid A mixture Example 1215B (370 mg, 0.803 mmol), tert-butyl 2-bromoacetate (0.125 ml, 0.843 mmol) and triethylamine (0.560 ml, 4.01 mmol) in dimethylformamide (3 ml) was stirred at room temperature for 16 hours. Water was added dropwise to the reaction mixture to form the precipitates. The solids were collected by filtration, washed with hexanes and dried at 50° C. oven under vacuum overnight to give the Boc-intermediate. To the intermediate (317 mg, 0.681 mmol) was added CH$_2$C12/trifluoroacetic acid (1/1, 2.5 mL) and the mixture was stirred at room temperature for one day. The reaction mixture was concentrated in vacuo, triturated with ether and filtered to collect the title compound as the tri-trifluoroacetate salt. LC-MS: 410 (M+H)$^+$.

EXAMPLE 1239B

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone A mixture of Example 1239A (70 mg, 0.100 mmol), azetidin-3-ol hydrochloride (21.90 mg, 0.200 mmol), 1-[bis(dimethylamino)methylene]-1H-1,2,3-triazolo[4,5-b]pyridinium 3-oxide hexafluorophosphate (45.6 mg, 0.120 mmol) and triethylamine (69.6 µl, 0.500 mmol) in N,N-dimethylformamide (2 mL) was stirred at room temperature overnight. The reaction mixture was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-d$_6$) δ ppm 1.34-1.55 (m, 2 H) 2.14-2.25 (m, 2 H) 2.30-2.41 (m, 2 H) 2.54-2.66 (m, 4 H) 2.92-3.08 (m, 3 H) 3.55 (dd, J=10.07, 4.27 Hz, 1 H) 3.72 (s, 3 H) 3.87 (dd, J=9.31, 4.12 Hz, 1 H) 4.01 (dd, J=9.92, 6.87 Hz, 1 H) 4.24-4.44 (m, 2 H) 5.92 (s, 1 H) 7.00 (d, J=4.88 Hz, 1 H) 7.09-7.36 (m, 3 H) 8.13 (d, J=4.88 Hz, 1H) 11.57 (s, 1 H). MS (ESI$^+$) m/z 465 (M+H)$^+$.

EXAMPLE 1240

2-[(3aR,5S,6aS)-5-[4-(5-fluoro-2-methoxyphenyl)-1H-pyrrolo[2,3-b]pyridin-2-yl]hexahydrocyclopenta[c]pyrrol-2(1H)-yl]-1-[(2S)-2-(hydroxymethyl)pyrrolidin-1-yl]ethanone The title compound was prepared using the condition described in Example 1239B substituting (S)-pyrrolidin-2-ylmethanol for azetidin-3-ol hydrochloride. $^1$H NMR (400 MHz, DMSO-d$_6$) δ ppm 1.22-1.52 (m, 2 H) 1.62-1.82 (m, 4 H) 2.14-2.42 (m, 4 H) 2.52-2.72 (m, 4 H) 2.96-3.53 (m, 8 H) 3.72 (s, 3 H) 3.82-3.99 (m, 1 H) 5.84-6.02 (m, 1 H) 6.94-7.06 (m, 1 H) 7.09-7.33 (m, 3 H) 8.12 (d, J=4.88 Hz, 1 H) 11.36-11.71 (m, 1 H). MS (ESI$^+$) m/z 493 (M+H)$^+$.

EXAMPLE 1241

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(2-hydroxyethyl)-N-methylacetamide The title compound was prepared using the condition described in Example 1239B substituting 2-(methylamino)ethanol for azetidin-3-ol hydrochloride. $^1$H NMR (400 MHz, DMSO-d$_6$) δ ppm 1.30-1.56 (m, 2 H) 2.16-2.42 (m, 4 H) 2.55-2.90 (m, 5 H) 2.95-3.60 (m, 9 H) 3.72 (s, 3 H) 5.93 (d, J=14.04 Hz, 1 H) 7.00 (d, J=5.19 Hz, 1 H) 7.14-7.39 (m, 3 H) 8.12 (d, J=4.88 Hz, 1 H) 11.53 (s, 1 H). MS (ESI$^+$) m/z 467 (M+H)$^+$.

EXAMPLE 1242

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(3-hydroxycyclobutyl)-N-methylacetamide The title compound was prepared using the condition described in Example 1239B substituting 3-(methylamino)cyclobutanol hydrochloride for azetidin-3-ol hydrochloride. $^1$H NMR (500 MHz, DMSO-d$_6$) δ ppm 1.30-1.50 (m, 2 H) 1.76-2.04 (m, 2 H) 2.13-2.40 (m, 6 H) 2.53-3.22 (m, 12 H) 3.72 (s, 3 H) 4.09-4.32 (m, 1 H) 5.81-5.97 (m, 1 H) 7.00 (d, J=4.88 Hz, 1 H) 7.12-7.31 (m, 3 H) 8.13 (d, J=4.88 Hz, 1 H) 11.57 (s, 1 H). MS (ESI$^+$) m/z 493 (M+H)$^+$.

EXAMPLE 1243

[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl](3-hydroxycyclobutyl)methanone The title compound was prepared using the condition described in Example 1216, substituting 3-hydroxycyclobutanecarboxylic acid for acetic acid. $^1$H NMR (400 MHz, DMSO-$d_6$) δ ppm 1.32-1.63 (m, 2 H) 1.75-2.02 (m, 2 H) 2.15-2.39 (m, 4 H) 2.54-2.81 (m, 3 H) 3.17-3.54 (m, 5 H) 3.72 (s, 3 H) 3.83-4.00 (m, 1 H) 5.02 (d, J=7.02 Hz, 1 H) 5.97 (d, J=1.53 Hz, 1 H) 6.99 (d, J=4.88 Hz, 1 H) 7.08-7.33 (m, 3 H) 8.13 (d, J=4.88 Hz, 1 H) 11.60 (s, 1 H). MS (ESI$^+$) m/z 450 (M+H)$^+$.

EXAMPLE 1244

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-methyl-2-oxoethanesulfonamide The title compound was prepared using the condition described in Example 1216, substituting 2-(N-methylsulfamoyl)acetic acid for acetic acid. $^1$H NMR (400 MHz, DMSO-$d_6$) δ ppm 1.40-1.69 (m, 2 H) 2.27-2.38 (m, 2 H) 2.60 (d, J=4.88 Hz, 3 H) 2.67-2.92 (m, 2 H) 3.19-3.71 (m, 5 H) 3.72 (s, 3 H) 4.04-4.21 (m, 2 H) 5.98 (d, J=1.53 Hz, 1 H) 6.91-7.09 (m, 2 H) 7.14-7.34 (m, 3 H) 8.13 (d, J=4.88 Hz, 1 H) 11.59 (s, 1 H). MS (ESI$^+$) m/z 487 (M+H)$^+$.

EXAMPLE 1245

2-(8-azabicyclo[3.2.1]oct-2-en-3-yl)-4-(5-fluoro-2-methoxyphenyl)-1H-pyrrolo[2,3-b]pyridine-5-carbonitrile The title compound was prepared as described in Example 301B. $^1$H NMR (400 MHz, DMSO-$d_6$) δ 1.82 (dq, J=14.7, 7.2 Hz, 1H), 1.99-2.27 (m, 3H), 2.65 (d, J=18.7 Hz, 1H), 2.93-3.11 (m, 1H), 3.76 (s, 3H),), 4.25 (t, J=5.6 Hz, 1H), 4.44 (t, J=5.7 Hz, 1H), 6.38 (t, J=2.4 Hz, 1H), 6.75-6.82 (m, 1H), 7.23-7.33 (m, 2H), 7.40 (td, J=8.7, 3.2 Hz, 1H), 8.66 (s, 1H), 9.07 (bs, 2H), 12.64 (bs, 1H). MS (ESI$^+$) m/z 375 (M+H)$^+$.

EXAMPLE 1246

2-(8-azabicyclo[3.2.1]oct-2-en-3-yl)-5-fluoro-4-(5-fluoro-2-methoxyphenyl)-1H-pyrrolo[2,3-b]pyridine The title compound was prepared as described in Example 302A. $^1$H NMR (500 MHz, methanol-$d_4$) δ ppm 1.95-2.05 (m, 1H), 2.19-2.31 (m, 1H), 2.29-2.45 (m, 2H), 2.64-2.76 (m, 1H), 3.13-3.25 (m, 1H), 3.78 (s, 3H), 4.30-4.37 (m, 1H), 4.48 (t, J=5.9 Hz, 1H), 6.44 (s, 1H), 6.71-6.76 (m, 1H), 7.13-7.24 (m, 2H), 7.27 (td, J=8.6, 3.1 Hz, 1H), 8.32 (d, J=3.3 Hz, 1H). MS (ESI$^+$) m/z 368.0 (M+H)$^+$.

EXAMPLE 1247

N-cyano-3-[5-fluoro-4-(5-fluoro-2-methoxyphenyl)-1H-pyrrolo[2,3-b]pyridin-2-yl]-8-azabicyclo[3.2.1]oct-2-ene-8-carboxamide The title compound was prepared using the procedure described in Example 1111, using Example 302A in place of Example 1086. $^1$H NMR (500 MHz, DMSO-$d_6$): δ 1.63-1.74 (m, 1 H) 1.89-2.04 (m, 2 H) 2.12-2.24 (m, 1 H) 2.28-2.42 (m, 1 H) 2.86-3.01 (m, 1 H) 3.72 (s, 3 H) 4.44-4.50 (m, 1 H) 4.57-4.61 (m, 1 H) 6.16 (s, 1 H) 6.77-6.84 (m, 1 H) 7.19-7.28 (m, 2 H) 7.29-7.36 (m, 1 H) 8.18-8.22 (m, 1 H) 10.62 (br. s, 1 H) 11.95 (s, 1 H). MS (ESI$^+$) m/z: 436.1 (M+H)$^+$.

EXAMPLE 1248

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide The title compound was prepared using the procedure described in Example 238, substituting Example 1209 for Example 226B and 2-(methylamino)ethanol for azetidin-3-ol hydrochloride. $^1$H NMR (500 MHz, DMSO-$d_6$) δ 2.72 (s, 3H), 2.76-3.03 (m, 10H), 3.17 (s, 1H), 3.42-3.65 (m, 4H), 3.75 (s, 3H), 6.20 (s, 1H), 6.40 (s, 1H), 7.07-7.87 (m, 3H), 8.62 (s, 1H), 12.57 (s, 1H). MS (ESI$^+$) m/z 490 (M+H)$^+$.

EXAMPLE 1249

{3-[5-cyano-4-(5-fluoro-2-methoxyphenyl)-1H-pyrrolo[2,3-b]pyridin-2-yl]-8-azabicyclo[3.2.1]oct-2-en-8-yl}) acetic acid The title compound was prepared essentially as described in Example 226, substituting Example 1245 for Example 87D in Example 226A. $^1$H NMR (500 MHz, DMSO-$d_6$) δ 1.84-2.00 (m, 1H), 2.18 (q, J=11.7 Hz, 1H), 2.26-2.45 (m, 2H), 2.73 (dd, J=29.2, 18.2 Hz, 1H), 3.11 (dd, J=26.5, 17.9 Hz, 1H), 3.76 (s, 3H), 4.00-4.21 (m, 2H), 4.26 (t, J=5.8 Hz, 1H), 4.48 (t, J=5.7 Hz, 1H), 6.42 (s, 1H), 6.75 (s, 1H), 7.34 (dd, J=55.3, 7.7 Hz, 3H), 8.67 (s, 1H), 10.39 (s, 1H), 12.67 (s, 1H). MS (ESI$^+$) m/z 433 (M+H)$^+$.

EXAMPLE 1251

2-{3-[5-cyano-4-(5-fluoro-2-methoxyphenyl)-1H-pyrrolo[2,3-b]pyridin-2-yl]-8-azabicyclo[3.2.1]oct-2-en-8-yl}acetamide The title compound was prepared according to the procedure described in Example 224, substituting Example 1245 for Example 87D and 2-bromoacetamide for 2-chloro-N,N-dimethylacetamide. $^1$H NMR (500 MHz, DMSO-$d_6$) δ 1.89 (q, J=8.0, 7.4 Hz, 1H), 2.11-2.44 (m, 3H), 2.63-3.01 (m, 2H), 3.76 (s, 3H), 3.93 (d, J=32.2 Hz, 2H), 4.22 (d, J=25.3 Hz, 1H), 4.44 (t, J=5.6 Hz, 1H), 6.43 (s, 1H), 6.74 (dd, J=61.4, 10.1 Hz, 1H), 7.22-7.46 (m, 3H), 7.64-7.95 (m, 2H), 8.67 (s, 1H), 10.21 (d, J=76.6 Hz, 1H), 12.69 (d, J=11.7 Hz, 1H). MS (ESI$^+$) m/z 432 (M+H)$^+$.

EXAMPLE 1252

{4-[4-(5-fluoro-2-methoxyphenyl)-1H-pyrrolo[2,3-b]pyridin-2-yl]cyclohexyl}acetic acid

EXAMPLE 1252A methyl 2-(4-(4-(5-fluoro-2-methoxyphenyl)-1H-pyrrolo[2,3-b]pyridin-2-yl)cyclohexyl)acetate A mixture of Example 1171C (0.07 g, 0.177 mmol) and 20% palladium hydroxide on carbon (wet, 0.03 g) in methanol (3 ml) and tetrahydrofuran (1 ml) was stirred at 50° C. for 32 hours in a pressure bottle under 30 psi hydrogen gas. The mixture was filtered through a nylon membrane and concentrated to provide the title compound. MS (ESI$^+$) m/z 397.3 (M+H)$^+$.

EXAMPLE 1252B

{4-[4-(5-fluoro-2-methoxyphenyl)-1H-pyrrolo[2,3-b]pyridin-2-yl]cyclohexyl}acetic acid The title compound was prepared essentially as described in Example 681, substituting Example 1252A for Example 676. $^1$H NMR (500 MHz, DMSO-d$_6$) δ ppm 1.00-1.25 (m, 1H), 1.35-1.96 (m, 7H), 1.98-2.08 (m, 1H), 2.15 (d, J=6.9 Hz, 1H), 2.27 (d, J=7.3 Hz, 1H), 2.62-2.93 (m, 1H), 3.74 (d, J=2.8 Hz, 3H), 6.01-6.13 (m, 1H), 7.14 (d, J=5.2 Hz, 1H), 7.18-7.35 (m, 3H), 8.20 (d, J=5.0 Hz, 1H), 11.89 (m, 1H). MS (ESI$^+$) m/z 383.3 (M+H)$^+$.

EXAMPLE 1253

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide The title compound was prepared using the procedure described in Example 238, substituting Example 1209 for Example 226B and 3-(methylamino)cyclobutanol hydrochloride for azetidin-3-ol, hydrochloride. $^1$H NMR (500 MHz, DMSO-d$_6$) δ 1.88 (s, 5H), 2.29 (dtt, J=13.7, 9.8, 5.3 Hz, 2H), 2.60 (q, J=7.8 Hz, 1H), 2.74 (s, 1H), 2.84-2.97 (m, 3H), 3.17 (q, J=7.4 Hz, 2H), 3.41 (d, J=8.2 Hz, 2H), 3.62 (ddt, J=13.4, 9.6, 5.9 Hz, 2H), 3.75 (s, 3H), 4.02-4.34 (m, 2H), 6.16 (d, J=4.0 Hz, 1H), 6.39 (s, 1H), 7.11-7.69 (m, 3H), 8.60 (s, 1H). MS (ESI$^+$) m/z 516 (M+H)$^+$.

EXAMPLE 1254

1-{4-[5-fluoro-4-(5-fluoro-2-methoxyphenyl)-1H-pyrrolo[2,3-b]pyridin-2-yl]cyclohex-3-en-1-yl}-N,N-dimethyl-L-prolinamide The title compound was prepared essentially as described in Example 241C, substituting Example 241B with Example 1105D and (R)-tert-butyl 2-amino-3-methylbutanoate hydrochloride with (S)—N,N-dimethylpyrrolidine-2-carboxamide. $^1$H NMR (400 MHz, DMSO-d$_6$) δ ppm 11.84 (s, 1 H) 8.01-8.30 (m, 1 H) 7.09-7.52 (m, 3 H) 6.45 (d, J=1.83 Hz, 1 H) 6.09 (s, 1 H) 4.03 (dd, J=8.39, 6.56 Hz, 2 H) 3.77-3.88 (m, 1 H) 3.65-3.80 (m, 3 H) 3.01-3.13 (m, 6 H) 2.72-2.83 (m, 2 H) 2.21-2.40 (m, 2 H) 1.97-2.21 (m, 2 H) 1.87-1.97 (m, 2 H) 1.69-1.81 (m, 3 H). MS (ESI): 481.2 (M+H)$^+$.

EXAMPLE 1255

4-[3-cyano-4-(5-fluoro-2-methoxyphenyl)-1H-pyrrolo[2,3-b]pyridin-2-yl]cyclohex-3-ene-1-carboxylic acid

EXAMPLE 1255A ethyl 4-(3-cyano-4-(5-fluoro-2-methoxyphenyl)-1H-pyrrolo[2,3-b]pyridin-2-yl)cyclohex-3-enecarboxylate The title compound was prepared essentially as described in Example 219B, substituting Example 219A with Example 248C. The crude material was dissolved in 50 mL dichloromethane and treated with excess trifluoroacetic acid at room temperature for 12 hours. The solvent was removed and the crude material was purified via flash chromatography, (Analogix280 SF 25 g silica column, 0% to 4% methanol/dichloromethane gradient over 30 minutes) to give the title compound. MS (ESI): 420.2 (M+H)$^+$.

EXAMPLE 1255B

4-[3-cyano-4-(5-fluoro-2-methoxyphenyl)-1H-pyrrolo[2,3-b]pyridin-2-yl]cyclohex-3-ene-1-carboxylic acid The title compound was prepared essentially as described in Example 219C, substituting Example 219B with Example 1255A. $^1$H NMR (500 MHz, DMSO-d$_6$) δ ppm 12.75 (s, 1 H) 8.36 (d, J=4.88 Hz, 1 H) 6.98-7.48 (m, 4 H) 6.70 (s, 1 H) 3.72 (s, 3 H) 2.33-2.82 (m, 5 H) 2.00-2.14 (m, 1 H) 1.62-1.80 (m, 1 H). MS (ESI): 392.2 (M+H)$^+$.

EXAMPLE 1256

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide The title compound was prepared using the procedure described in Example 238, substituting Example 1249 for Example 226B and 2-(methylamino)ethanol for azetidin-3-ol hydrochloride. $^1$H NMR (500 MHz, DMSO-d$_6$) δ 1.51 (dq, J=13.9, 4.8, 4.3 Hz, 1H), 1.79 (t, J=10.1 Hz, 1H), 1.86 (s, 3H), 1.96-2.12 (m, 2H), 2.69-2.87 (m, 2H), 3.04 (d, J=4.7 Hz, 1H), 3.18 (s, 1H), 3.23-3.67 (m, 7H), 3.76 (s, 3H), 6.21 (s, 1H), 6.72 (d, J=5.3 Hz, 1H), 7.05-7.58 (m, 3H), 8.60 (s, 1H). MS (ESI$^+$) m/z 490 (M+H)$^+$.

EXAMPLE 1257

4-(5-fluoro-2-methoxyphenyl)-2-(8-{2-[(2S)-2-(hydroxymethyl)pyrrolidin-1-yl]-2-oxoethyl}-8-azabicyclo[3.2.1]oct-2-en-3-yl)-1H-pyrrolo[2,3-b]pyridine-5-carbonitrile The title compound was prepared using the procedure described in Example 238, substituting Example 1249 for Example 226B and (S)-pyrrolidin-2-ylmethanol for azetidin-3-ol hydrochloride. $^1$H NMR (500 MHz, DMSO-d$_6$) δ 1.49 (dtd, J=9.4, 5.8, 3.1 Hz, 1H), 1.79 (ddtd, J=20.4, 12.2, 8.2, 4.2 Hz, 4H), 1.88 (s, 3H), 1.91-2.14 (m, 3H), 2.74 (td, J=22.5, 19.8, 9.6 Hz, 2H), 3.17-3.70 (m, 4H), 3.75 (s, 3H), 3.92 (tt, J=6.5, 3.1 Hz, 3H), 6.21 (s, 1H), 6.70 (t, J=4.4 Hz, 1H), 7.28 (tt, J=9.1, 5.0 Hz, 2H), 7.38 (td, J=8.6, 3.1 Hz, 1H), 8.59 (s, 1H). MS (ESI$^+$) m/z 516 (M+H)$^+$.

EXAMPLE 1258

4-(5-fluoro-2-methoxyphenyl)-2-{8-[2-(3-hydroxyazetidin-1-yl)-2-oxoethyl]-8-azabicyclo[3.2.1]oct-2-en-3-yl}-1H-pyrrolo[2,3-b]pyridine-5-carbonitrile The title compound was prepared using the procedure described in Example 238, substituting Example 1249 for Example 226B. $^1$H NMR (500 MHz, DMSO-d$_6$) δ 1.49 (p, J=9.1 Hz, 1H), 1.73-1.85 (m, 1H), 1.87 (s, 2H), 1.91-2.15 (m, 2H), 2.62-2.82 (m, 1H), 3.02-3.18 (m, 2H), 3.42 (dt, J=7.8, 3.8 Hz, 1H), 3.56 (dt, J=11.1, 4.5 Hz, 2H), 3.75 (s, 3H), 3.83-4.10 (m, 2H), 4.25-4.47 (m, 2H), 6.21 (s, 1H), 6.69 (d, J=5.2 Hz, 1H), 7.20-7.46 (m, 3H), 8.59 (s, 1H). MS (ESI$^+$) m/z 488 (M+H)$^+$.

EXAMPLE 1259

{4-[5-cyano-4-(5-fluoro-2-methoxyphenyl)-1H-pyrrolo[2,3-b]pyridin-2-yl]cyclohex-3-en-1-yl}acetic acid Example 277A (50 mg, 0.127 mmol), methyl 2-(4-(4,4,5,5-tetramethyl-1,3,2-dioxaborolan-2-yl)cyclohex-3-en-1-yl)acetate (53 mg, 0.189 mmol), PdCl$_2$ (1,1'-bis(diphenylphosphino)ferrocene) CH$_2$Cl$_2$ (7.27 mg, 8.90 μmol), and sodium carbonate (40.4 mg, 0.382 mmol) in 1.5 mL tetrahydrofuran and 0.5 mL water was heated at 80° C. for 4 hours. The reaction mixture was extracted with ethyl acetate and was purified by column chromatography with 20-60% ethyl acetate in heptane. The solid was dissolved in 1 mL tetrahydrofuran and 1 mL methanol and was treated with lithium hydroxide (318 μl, 0.636 mmol) at room temperature overnight. The reaction mixture was neutralized with 2N aqueous HCl and the resulting suspension was filtered to collect the title compound. $^1$H NMR (500 MHz, DMSO-d$_6$) δ 1.30-1.41 (m, 1H), 1.79-2.16 (m, 3H), 2.16-2.42 (m, 5H), 3.75 (d, J=1.5 Hz, 3H), 6.22 (t, J=2.4 Hz, 1H), 6.59 (bs, 1H), 7.22-7.34 (m, 2H), 7.38 (td, J=8.7, 3.2 Hz, 1H), 8.58 (s, 1H), 12.09 (bs, 1H), 12.36-12.40 (m, 1H). MS (ESI$^+$) m/z 406 (M+H)$^+$.

EXAMPLE 1260

2-(9-azabicyclo[3.3.1]non-2-en-3-yl)-4-(5-fluoro-2-methoxyphenyl)-1H-pyrrolo[2,3-b]pyridine The title compound was prepared as bis-trifluoroacetate salt using the condition described in Example 262A-E, substituting tert-butyl 3-oxo-9-azabicyclo[3.3.1]nonane-9-carboxylate for oxohexahydrocyclopenta[c]pyrrole-2(1H)-carboxylate in Example 262A. $^1$H NMR (500 MHz, DMSO-D6) δ ppm 1.47-1.99 (m, 6 H) 2.69 (d, J=18.62 Hz, 1 H) 2.99 (dd, J=18.46, 7.48 Hz, 1 H) 3.75 (s, 3 H) 3.86-3.91 (m, 1 H) 4.25-4.30 (s, 1 H) 6.39 (d, J=1.83 Hz, 1 H) 6.50 (d, J=5.49 Hz, 1 H) 7.10 (d, J=4.88 Hz, 1 H) 7.19-7.37 (m, 3 H) 8.27 (d, J=4.88 Hz, 1 H) 8.74-8.88 (m, 1 H) 8.93-9.03 (m, 1 H) 12.07 (s, 1 H). MS (ESI$^+$) m/z 364 (M+H)$^+$.

EXAMPLE 1261

4-(5-fluoro-2-methoxyphenyl)-2-[9-(methylsulfonyl)-9-azabicyclo[3.3.1]non-2-en-3-yl]-1H-pyrrolo[2,3-b]pyridine To a solution of Example 1260 (60 mg, 0.108 mmol) and triethylamine (0.030 mL, 0.215 mmol) in dimethylformamide (0.8 mL) at 0° C. was added slowly methanesulfonyl chloride (9.20 μl, 0.118 mmol) in N,N-dimethylformamide (0.3 mL). The mixture was stirred at 0° C. for one hour. Water was added dropwise to the reaction mixture to form a precipitate. The solid was collected by filtration, washed with ether and dried at 50° C. under vacuum overnight to afford the title compound. $^1$H NMR (500 MHz, DMSO-d$_6$) δ ppm 1.46-1.82 (m, 6 H) 2.41 (d, J=18.62 Hz, 1 H) 2.87 (s, 3 H) 2.95 (dd, J=18.31, 7.63 Hz, 1 H) 3.74 (s, 3 H) 4.13-4.23 (m, 1 H) 4.39-4.53 (m, 1 H) 6.30 (d, J=1.83 Hz, 1 H) 6.55 (d, J=5.49 Hz, 1 H) 7.07 (d, J=5.19 Hz, 1 H) 7.15-7.37 (m, 3 H) 8.22 (d, J=4.88 Hz, 1 H) 11.89 (s, 1 H). MS (ESI$^+$) m/z 442 (M+H)$^+$.

EXAMPLE 1262

3-[4-(5-fluoro-2-methoxyphenyl)-1H-pyrrolo[2,3-b]pyridin-2-yl]-N-methyl-9-azabicyclo[3.3.1]non-2-ene-9-carboxamide To a mixture of Example 1260 (40 mg, 0.072 mmol) in N,N-dimethylformamide (0.75 mL) was added 2,5-dioxopyrrolidin-1-yl methylcarbamate (14.82 mg, 0.086 mmol) and triethylamine (0.050 mL, 0.359 mmol). The mixture was stirred at room temperature overnight and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (500 MHz, DMSO-d$_6$) δ ppm 1.40-1.70 (m, 6 H) 2.33 (d, J=17.40 Hz, 1 H) 2.57 (d, J=3.97 Hz, 3 H) 2.74 (dd, J=17.70, 7.32 Hz, 1 H) 3.74 (s, 3 H) 4.41 (s, 1 H) 4.72 (s, 1 H) 6.24 (t, J=2.90 Hz, 1 H) 6.45 (d, J=4.27 Hz, 1 H) 6.52 (d, J=5.49 Hz, 1 H) 7.04 (d, J=4.88 Hz, 1 H) 7.16-7.31 (m, 3 H) 8.20 (d, J=4.88 Hz, 1 H) 11.80 (s, 1 H). MS (ESI$^+$) m/z 421 (M+H)$^+$.

EXAMPLE 1263

2-{3-[4-(5-fluoro-2-methoxyphenyl)-1H-pyrrolo[2,3-b]pyridin-2-yl]-9-azabicyclo[3.3.1]non-2-en-9-yl}-N,N-dimethylacetamide The title compound was prepared using the conditions described in Example 880, substituting Example 1260 for Example 845. $^1$H NMR (500 MHz, DMSO-d$_6$) δ ppm 1.32-1.82 (m, 6 H) 2.05-2.17 (m, 1 H) 2.67-2.77 (m, 1 H) 2.81 (s, 3 H) 3.05 (s, 3 H) 3.09-3.28 (m, 3 H) 3.39-3.48 (m, 1 H) 3.74 (s, 3 H) 6.24 (d, J=1.83 Hz, 1 H) 6.45 (d, J=5.19 Hz, 1 H) 7.03 (d, J=5.19 Hz, 1 H) 7.15-7.32 (m, 3 H) 8.19 (d, J=4.88 Hz, 1 H) 11.79 (s, 1 H). MS (ESI$^+$) m/z 449 (M+H)$^+$.

EXAMPLE 1264

3-{3-[4-(5-fluoro-2-methoxyphenyl)-1H-pyrrolo[2,3-b]pyridin-2-yl]-9-azabicyclo[3.3.1]non-2-en-9-yl}-3-oxopropanenitrile A mixture of Example 1260 (60 mg, 0.108 mmol), 2-cyanoacetic acid (10.99 mg, 0.129 mmol), 1-[bis(dimethylamino)methylene]-1H-1,2,3-triazolo[4,5-b]pyridinium 3-oxide hexafluorophosphate (49.1 mg, 0.129 mmol) and triethylamine (75 μl, 0.538 mmol) in N,N-dimethylformamide (1 mL) was stirred at room temperature for 48 hours. The reaction mixture was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (501 MHz, DMSO-d$_6$) δ ppm 1.45-1.84 (m, 6 H) 2.41-3.00 (m, 2 H) 3.74 (s, 3 H) 4.07-5.14 (m, 4 H) 6.13-6.33 (m, 1 H) 6.41-6.61 (m, 1 H) 7.05 (d, J=4.88 Hz, 1 H) 7.13-7.39 (m, 3 H) 8.21 (d, J=4.88 Hz, 1 H) 11.77-11.91 (m, 1 H). MS (ESI$^+$) m/z 431 (M+H)$^+$.

EXAMPLE 1265

{3-[4-(5-fluoro-2-methoxyphenyl)-1H-pyrrolo[2,3-b]pyridin-2-yl]-9-azabicyclo[3.3.1]non-2-en-9-yl}(3-hydroxycyclobutyl)methanone The title compound was prepared using the condition described in Example 1264, substituting 3-hydroxycyclobutanecarboxylic acid for 2-cyanoacetic acid. $^1$H NMR (500 MHz, DMSO-d$_6$) δ ppm 1.36-2.10 (m, 8 H) 2.21-2.46 (m, 3 H) 2.65-2.84 (m, 2 H) 3.74 (s, 3 H) 3.91-4.04 (m, 1 H) 4.17-5.18 (m, 3 H) 6.25 (dd, J=6.71, 2.14 Hz, 1 H) 6.49 (d, J=5.49 Hz, 1 H) 7.04 (dd, J=4.88, 1.53 Hz, 1 H) 7.14-7.34 (m, 3 H) 8.20 (d, J=5.19 Hz, 1 H) 11.83 (s, 1 H). MS (ESI$^+$) m/z 462 (M+H)$^+$.

The following compounds (concluding with Example 1328) were prepared essentially as described in Example 293, substituting the appropriate amine in Example 293A and the appropriate amine in Example 293C.

EXAMPLE 1266

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone $^1$H NMR (500 MHz, methanol-d$_4$) δ ppm 1.58-1.69 (m, 1H), 1.89-1.98 (m, 1H), 2.01-2.16 (m, 2H), 2.15-2.26 (m, 1H), 2.77-2.90 (m, 1H), 3.24-3.33 (m, 2H), 3.50-3.56 (m, 1H), 3.59-3.68 (m, 1H), 3.76-3.77 (m, 4H), 3.95-4.03 (m, 1H), 4.16-4.24 (m, 1H), 4.37-4.46 (m, 1H), 4.50-4.75 (m, 2H), 6.13 (s, 1H), 6.50 (bs, 1H), 7.07-7.17 (m, 2H), 7.16-7.24 (m, 1H), 8.06 (d, J=2.8 Hz, 1H). MS (ESI$^+$) m/z 481.1 (M+H)$^+$.

EXAMPLE 1267

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone $^1$H NMR (500 MHz, methanol-d$_4$) δ ppm 1.60-1.70 (m, 1H), 1.81-2.28 (m, 8H), 2.81-2.97 (m, 1H), 3.35-3.68 (m, 7H), 3.68-3.80 (m, 4H), 4.07-4.13 (m, 1H), 6.14 (s, 1H), 6.48-6.54 (m, 1H), 7.07-7.17 (m, 2H), 7.16-7.24 (m, 1H), 8.06 (d, J=2.8 Hz, 1H). MS (ESI$^+$) m/z 509.1 (M+H)$^+$.

EXAMPLE 1268

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide $^1$H NMR (500 MHz, methanol-d$_4$) δ ppm 1.60-1.70 (m, 1H), 1.90-1.99 (m, 1H), 2.00-2.24 (m, 3H), 2.81-2.97 (m, 3H), 3.09 (d, J=3.2 Hz, 1H), 3.39-3.66 (m, 5H), 3.65-3.78 (m, 6H), 6.14 (s, 1H), 6.48-6.53 (m, 1H), 7.06-7.17 (m, 2H), 7.16-7.23 (m, 1H), 8.06 (d, J=2.8 Hz, 1H). MS (ESI$^+$) m/z 483.1 (M+H)$^+$.

EXAMPLE 1269

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(trans-4-hydroxycyclohexyl)acetamide $^1$H NMR (500 MHz, methanol-d$_4$) δ ppm 1.24-1.44 (m, 4H), 1.59-1.70 (m, 1H), 1.84-2.02 (m, 5H), 2.04-2.28 (m, 3H), 2.77-2.89 (m, 1H), 3.16-3.26 (m, 2H), 3.46 (t, J=5.5 Hz, 1H), 3.50-3.64 (m, 2H), 3.64-3.71 (m, 1H), 3.76 (s, 3H), 6.13 (s, 1H), 6.53 (d, J=5.5 Hz, 1H), 7.06-7.17 (m, 2H), 7.16-7.23 (m, 1H), 8.06 (d, J=2.8 Hz, 1H). MS (ESI$^+$) m/z 523.2 (M+H)$^+$.

EXAMPLE 1298

2-{4-[5-fluoro-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide $^1$H NMR (500 MHz, methanol-d$_4$) δ ppm 1.99-2.25 (m, 1H), 2.50-2.60 (m, 4H), 2.74-2.80 (m, 2H), 2.92-2.96 (m, 2H), 3.03 (bs, 2H), 3.26 (s, 1H), 3.36-3.38 (m, 2H), 3.76 (s, 3H), 3.88-4.01 (m, 1H), 4.14-4.41 (m, 1H), 6.15 (s, 1H), 6.36 (bs, 1H), 6.99-7.23 (m, 3H), 8.06 (d, J=2.8 Hz, 1H). MS (ESI$^+$) m/z 483.0 (M+H)$^+$.

EXAMPLE 1299

2-{4-[5-fluoro-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide $^1$H NMR (500 MHz, methanol-d$_4$) δ ppm 2.54-2.60 (m, 2H), 2.80 (t, J=5.8 Hz, 2H), 2.96 (s, 2H), 3.14 (s, 1H), 3.35 (s, 1H), 3.39 (s, 1H), 3.45 (s, 1H), 3.50 (t, J=5.7 Hz, 1H), 3.58 (t, J=5.2 Hz, 1H), 3.64-3.75 (m, 2H), 3.76 (s, 3H), 6.16 (s, 1H), 6.34-6.39 (m, 1H), 6.99-7.24 (m, 3H), 8.06 (d, J=2.8 Hz, 1H). MS (ESI$^+$) m/z 457.1 (M+H)$^+$.

EXAMPLE 1300

2-{4-[5-fluoro-4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone $^1$H NMR (500 MHz, methanol-d$_4$) δ ppm 1.83-2.09 (m, 4H), 2.54-2.60 (m, 2H), 2.81-2.83 (m, 2H), 3.34 (d, J=3.49 Hz, 4H), 3.48-3.68 (m, 4H), 3.76 (s, 3H), 4.08-4.25 (m, 1H), 6.16 (s, 1H), 6.37 (bs, 1H), 6.99-7.18 (m, 2H), 7.16-7.24 (m, 1H), 8.06 (d, J=2.8 Hz, 1H). MS (ESI$^+$) m/z 483.0 (M+H)$^+$.

EXAMPLE 1301

2-{4-[5-fluoro-4-(5-fluoro-2-methoxyphenyl)-1H-pyrrolo[2,3-b]pyridin-2-yl]-3,6-dihydropyridin-1(2H)-yl}-N-(trans-4-hydroxycyclohexyl)acetamide $^1$H NMR (500 MHz, methanol-d$_4$) δ ppm 1.25-1.42 (m, 4H), 1.84-2.01 (m, 4H), 2.56-2.62 (m, 2H), 2.76-2.82 (m, 2H), 3.17 (bs, 2H), 3.48-3.56 (m, 1H), 3.64-3.75 (m, 1H), 3.77 (s, 3H), 6.18 (s, 1H), 6.37 (bs, 1H), 7.08-7.18 (m, 2H), 7.16-7.24 (m, 1H), 8.07 (d, J=2.8 Hz, 1H). MS (ESI$^+$) m/z 497.0 (M+H)$^+$.

EXAMPLE 1328

2-{4-[5-fluoro-4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone $^1$H NMR (400 MHz, pyridine-d$_5$) δ ppm 1.84-2.15 (m, 2H), 2.59-2.66 (m, 2H), 2.87-2.96 (m, 2H), 3.36-3.51 (m, 4H), 3.62-4.04 (m, 7H), 4.54-4.67 (m, 1H), 6.51 (dd, J=4.9, 2.0 Hz, 1H), 6.68-6.74 (m, 2H), 7.12 (dd, J=9.1, 4.5 Hz, 1H), 7.31 (td, J=8.5, 3.2 Hz, 1H), 7.51 (dd, J=8.7, 3.2 Hz, 1H), 8.51 (dd, J=2.6, 1.5 Hz, 1H), 13.05 (bs, 1H). MS (ESI$^+$) m/z 469.0 (M+H)$^+$.

EXAMPLE 1270

4-[4-(4-fluoro-2-methoxyphenyl)-1H-pyrrolo[2,3-b]pyridin-2-yl]cyclohex-3-ene-1-carboxylic acid

EXAMPLE 1270A 4-(4-fluoro-2-methoxyphenyl)-2-iodo-1-(phenylsulfonyl)-1H-pyrrolo[2,3-b]pyridine The title compound was prepared as described in Example 87A-B, substituting 4-fluoro-2-methoxyphenylboronic acid for 5-fluoro-2-methoxyphenylboronic acid in Example 87A. LCMS (API) 509.0 (M+H)$^+$.

EXAMPLE 1270B 4-(4-fluoro-2-methoxyphenyl)-2-iodo-1H-pyrrolo[2,3-b]pyridine

The title compound was prepared essentially as described in Example 219A, substituting Example 87B with Example 1270A. MS (ESI): 369.1 (M+H)$^+$.

EXAMPLE 1270C ethyl 4-(4-(4-fluoro-2-methoxyphenyl)-1H-pyrrolo[2,3-b]pyridin-2-yl)cyclohex-3-enecarboxylate The title compound was prepared essentially as described in Example 219B, substituting Example 219A with Example 1270B. MS (ESI): 395.2 (M+H)$^+$.

EXAMPLE 1270D

4-[4-(4-fluoro-2-methoxyphenyl)-1H-pyrrolo[2,3-b]pyridin-2-yl]cyclohex-3-ene-1-carboxylic acid The title compound was prepared essentially as described in Example 219C, substituting Example 219B with Example 1270C. $^1$H NMR (400 MHz, DMSO-d$_6$) δ ppm 12.23 (s, 1 H) 11.73 (s, 1 H) 8.16 (d, J=4.88 Hz, 1 H) 7.42 (dd, J=8.54, 7.02 Hz, 1 H) 7.09 (dd, J=11.29, 2.44 Hz, 1 H) 6.99 (d, J=5.19 Hz, 1 H) 6.84-6.96 (m, 1 H) 6.53 (s, 1 H) 6.17 (d, J=1.53 Hz, 1 H) 3.66-3.88 (m, 3 H) 2.26-2.67 (m, 5 H) 1.92-2.16 (m, 1 H) 1.53-1.79 (m, 1 H). MS (ESI): 367.2 (M+H)$^+$.

EXAMPLE 1271

4-[4-(4,5-difluoro-2-methoxyphenyl)-1H-pyrrolo[2,3-b]pyridin-2-yl]cyclohex-3-ene-1-carboxylic acid

EXAMPLE 1271A 4-(4,5-difluoro-2-methoxyphenyl)-2-iodo-1-(phenylsulfonyl)-1H-pyrrolo[2,3-b]pyridine The title compound was prepared as described in Examples 87A-B substituting 4,5-difluoro-2-methoxyphenylboronic acid for 5-fluoro-2-methoxyphenylboronic acid in Example 87A. LCMS (API) 527.0 (M+H)$^+$.

EXAMPLE 1271B 4-(4,5-difluoro-2-methoxyphenyl)-2-iodo-1H-pyrrolo[2,3-b]pyridine

The title compound was prepared essentially as described in Example 219A, substituting Example 87B with Example 1271A. MS (ESI): 387.1 (M+H)$^+$.

EXAMPLE 1271C ethyl 4-(4,4,5,5-tetramethyl-1,3,2-dioxaborolan-2-yl)cyclohex-3-enecarboxylate The title compound was prepared essentially as described in Example 219B, substituting Example 219A with Example 1271B. MS (ESI): 413.2 (M+H)$^+$.

EXAMPLE 1271D

4-[4-(4,5-difluoro-2-methoxyphenyl)-1H-pyrrolo[2,3-b]pyridin-2-yl]cyclohex-3-ene-1-carboxylic acid The title compound was prepared essentially as described in Example 219C, substituting Example 219B with Example 1271C. $^1$H NMR (500 MHz, DMSO-d$_6$) δ ppm 12.12 (s, 1 H) 8.21 (d, J=5.19 Hz, 1 H) 7.43-7.56 (m, 1 H) 7.37 (dd, J=12.97, 6.87 Hz, 1 H) 7.11 (d, J=5.19 Hz, 1 H) 6.59 (s, 1 H) 6.28 (s, 1 H) 3.63-3.86 (m, 3 H) 2.30-2.73 (m, 5 H) 1.96-2.14 (m, 1 H) 1.61-1.80 (m, 1 H). MS (ESI): 385.2 (M+H)$^+$.

EXAMPLE 1272

4-[4-(2-methoxyphenyl)-1H-pyrrolo[2,3-b]pyridin-2-yl]cyclohex-3-ene-1-carboxylic acid

EXAMPLE 1272A 2-iodo-4-(2-methoxyphenyl)-1-(phenylsulfonyl)-1H-pyrrolo[2,3-b]pyridine The title compound was prepared as described in Examples 87A-B, substituting 2-methoxyphenylboronic acid for 5-fluoro-2-methoxyphenylboronic acid in Example 87A. LCMS (API) 491.0 (M+H)$^+$.

EXAMPLE 1272B 2-iodo-4-(2-methoxyphenyl)-1H-pyrrolo[2,3-b]pyridine

The title compound was prepared essentially as described in Example 219A, substituting Example 87B with Example 1272A. MS (ESI): 351.1 (M+H)$^+$.

EXAMPLE 1272C ethyl 4-(4,4,5,5-tetramethyl-1,3,2-dioxaborolan-2-yl)cyclohex-3-enecarboxylate The title compound was prepared essentially as described in Example 219B, substituting Example 219A with Example 1272B. MS (ESI): 377.2 (M+H)$^+$.

EXAMPLE 1272D

4-[4-(2-methoxyphenyl)-1H-pyrrolo[2,3-b]pyridin-2-yl]cyclohex-3-ene-1-carboxylic acid The title compound was prepared essentially as described in Example 219C, substituting Example 219B with Example 1272C. $^1$H NMR (500 MHz, DMSO-$d_6$) δ ppm 11.68 (s, 1 H) 7.30-7.52 (m, 2 H) 7.18 (d, J=7.93 Hz, 1 H) 7.08 (t, J=7.48 Hz, 1 H) 7.00 (d, J=5.19 Hz, 1 H) 6.51 (s, 1 H) 6.15 (d, J=1.83 Hz, 1 H) 3.75 (s, 3 H) 2.28-2.62 (m, 5 H) 1.97-2.13 (m, 1 H) 1.58-1.76 (m, 1 H). MS (ESI): 349.2 (M+H)$^+$.

EXAMPLE 1273

4-[4-(5-fluoro-2-methoxyphenyl)-1H-pyrrolo[2,3-b]pyridin-2-yl]-1-methylcyclohex-3-ene-1-carboxylic acid

EXAMPLE 1273A ethyl 4-(4-(5-fluoro-2-methoxyphenyl)-1H-pyrrolo[2,3-b]pyridin-2-yl)-1-methylcyclohex-3-enecarboxylate The title compound was prepared essentially as described in Example 219B, substituting ethyl 4-(4,4,5,5-tetramethyl-1,3,2-dioxaborolan-2-yl)cyclohex-3-enecarboxylate with ethyl 1-methyl-4-(4,4,5,5-tetramethyl-1,3,2-dioxaborolan-2-yl)cyclohex-3-enecarboxylate. MS (ESI): 395.3 (M+H)$^+$.

EXAMPLE 1273B

4-[4-(5-fluoro-2-methoxyphenyl)-1H-pyrrolo[2,3-b]pyridin-2-yl]-1-methylcyclohex-3-ene-1-carboxylic acid The title compound was prepared essentially as described in Example 219C, substituting Example 219B with Example 1273A. $^1$H NMR (501 MHz, DMSO-$d_6$) δ ppm 11.70 (d, J=1.53 Hz, 1 H) 8.16 (d, J=4.88 Hz, 1 H) 7.13-7.38 (m, 3 H) 7.01 (d, J=4.88 Hz, 1 H) 6.48 (s, 1 H) 6.16 (d, J=1.83 Hz, 1 H) 3.73 (s, 3 H) 2.67 (d, J=18.62 Hz, 1 H) 2.40 (d, J=6.10 Hz, 2 H) 1.91-2.11 (m, 2 H) 1.51-1.69 (m, 3 H) 1.11-1.17 (m, 3 H). MS (ESI): 381.2 (M+H)$^+$.

EXAMPLE 1274

2-{4-[4-(5-fluoro-2-methoxyphenyl)-1H-pyrrolo[2,3-b]pyridin-2-yl]-2,3,6,7-tetrahydro-1H-azepin-1-yl}-N,N-dimethylacetamide

EXAMPLE 1274A 4-(5-fluoro-2-methoxyphenyl)-2-(2,3,6,7-tetrahydro-1H-azepin-4-yl)-1H-pyrrolo[2,3-b]pyridine The title compound was prepared as described in Example 87, substituting tert-butyl 4-(4,4,5,5-tetramethyl-1,3,2-dioxaborolan-2-yl)-2,3,6,7-tetrahydro-1H-azepine-1-carboxylate for tert-butyl 4-(4,4,5,5-tetramethyl-1,3,2-dioxaborolan-2-yl)-5,6-dihydropyridine-1(2H)-carboxylate in Example 87C. $^1$H NMR (500 MHz, DMSO-$d_6$) δ 2.64-2.72 (m, 2H), 2.93-2.99 (m, 2H), 3.10-3.19 (m, 4H), 3.76 (s, 3H), 6.50 (d, J=1.9 Hz, 1H), 6.76 (t, J=6.4 Hz, 1H), 7.19-7.31 (m, 3H), 7.34 (td, J=8.6, 3.2 Hz, 1H), 8.28 (d, J=5.4 Hz, 1H), 9.43 (bs, 2H), 12.50 (bs, 1H). MS (ESI$^+$) m/z 338 (M+H)$^+$.

EXAMPLE 1274B

2-{4-[4-(5-fluoro-2-methoxyphenyl)-1H-pyrrolo[2,3-b]pyridin-2-yl]-2,3,6,7-tetrahydro-1H-azepin-1-yl}N,N-dimethylacetamide The title compound was prepared according to the procedure described in Example 235, substituting Example 1274A for Example 17G. $^1$H NMR (500 MHz, DMSO-$d_6$) δ 2.36-2.43 (m, 2H), 2.54-2.67 (m, 6H), 2.81 (s, 3H), 3.05 (s, 3H), 3.28 (s, 2H), 3.73 (s, 3H), 6.24 (d, J=2.1 Hz, 1H), 6.62-6.68 (m, 1H), 7.00 (d, J=4.9 Hz, 1H), 7.13-7.31 (m, 3H), 8.17 (d, J=4.9 Hz, 1H), 11.66 (bs, 1H). MS (ESI$^+$) m/z 423 (M+H)$^+$.

EXAMPLE 1275

2-{4-[4-(5-fluoro-2-methoxyphenyl)-1H-pyrrolo[2,3-b]pyridin-2-yl]azepan-1-yl}-N,N-dimethylacetamide The title compound was prepared according to the procedure described in Example 275, substituting Example 1274B for Example 236G. $^1$H NMR (500 MHz, DMSO-$d_6$) δ 1.64 (ddt, J=14.6, 10.0, 5.1 Hz, 1H), 1.72-1.93 (m, 3H), 2.00 (dq, J=13.9, 4.3 Hz, 2H), 2.63-2.82 (m, 7H), 3.02 (s, 3H), 3.28-3.40 (m, 3H), 3.73 (s, 3H), 5.95 (s, 1H), 7.00 (d, J=4.9 Hz, 1H), 7.14-7.31 (m, 3H), 8.12 (d, J=4.9 Hz, 1H), 11.55 (s, 1H). MS (ESI$^+$) m/z 425 (M+H)$^+$.

EXAMPLE 1276

{4-[4-(5-fluoro-2-methoxyphenyl)-1H-pyrrolo[2,3-b]pyridin-2-yl]-2,3,6,7-tetrahydro-1H-azepin-1-yl}acetic acid

EXAMPLE 1276A tert-butyl 2-(4-(4-(5-fluoro-2-methoxyphenyl)-1H-pyrrolo[2,3-b]pyridin-2-yl)-2,3,6,7-tetrahydro-1H-azepin-1-yl)acetate The title compound was prepared as described in Example 226A, substituting 1274A for Example 87D. MS (ESI$^+$) m/z 452 (M+H)$^+$.

EXAMPLE 1276B

{4-[4-(5-fluoro-2-methoxyphenyl)-1H-pyrrolo[2,3-b]pyridin-2-yl]-2,3,6,7-tetrahydro-1H-azepin-1-yl}acetic acid The title compound was prepared as described in Example 226B, substituting 1276A for Example 226A. $^1$H NMR (500 MHz, DMSO-$d_6$) δ 2.59-3.69 (m, 2H), 2.90-3.10 (m, 2H), 3.20-3.4 (m, 2H), 3.99 (d, J=90.3 Hz, 5H), 4.23 (s, 2H), 6.49 (s, 1H), 6.72 (t, J=6.1 Hz, 1H), 7.16-7.39 (m, 4H), 8.27 (d, J=5.1 Hz, 1H), 10.57 (s, 1H), 12.44 (s, 1H). MS (ESI$^+$) m/z 396 (M+H)$^+$.

EXAMPLE 1277

2-{4-[4-(5-fluoro-2-methoxyphenyl)-1H-pyrrolo[2,3-b]pyridin-2-yl]-2,3,6,7-tetrahydro-1H-azepin-1-yl}-1-(3-hydroxyazetidin-1-yl)ethanone The title compound was prepared according to the procedure described in Example 238, substituting Example 1276 for Example 226B. $^1$H NMR (500 MHz, DMSO-d$_6$) δ 2.30-2.50 (m, 2H), 2.59-3.02 (m, 6H), 3.01-3.26 (m, 2H), 3.60 (dd, J=10.1, 4.3 Hz, 1H), 3.73 (s, 3H), 3.93 (dd, J=9.4, 4.3 Hz, 1H), 4.06 (dd, J=10.1, 6.8 Hz, 1H), 4.38 (d, J=8.6 Hz, 1H), 4.41-4.49 (m, 1H), 5.72 (d, J=6.0 Hz, 1H), 6.26 (d, J=2.1 Hz, 1H), 6.65 (t, J=6.4 Hz, 1H), 7.01 (d, J=4.9 Hz, 1H), 7.15-7.25 (m, 2H), 7.27 (td, J=8.6, 3.2 Hz, 1H), 8.18 (d, J=4.9 Hz, 1H), 11.69 (bs, 1H). MS (ESI$^+$) m/z 451 (M+H)$^+$.

EXAMPLE 1278 tert-butyl 3-{4-[4-(5-fluoro-2-methoxyphenyl)-1H-pyrrolo[2,3-b]pyridin-2-yl]-3,6-dihydropyridin-1(2H)-yl}azetidine-1-carboxylate The title compound was prepared essentially as described in Example 908, substituting tert-butyl 3-oxoazetidine-1-carboxylate for (S)-1-tert-butyl 2-methyl 4-oxopyrrolidine-1,2-dicarboxylate. $^1$H NMR (400 MHz, DMSO-d$_6$) δ ppm 1.38 (s, 9H), 2.41-2.57 (m, 4H), 3.02-3.10 (m, 2H), 3.12-3.25 (m, 1H), 3.62-3.78 (m, 5H), 3.80-3.97 (m, 2H), 6.20 (d, J=2.1 Hz, 1H), 6.44-6.53 (m, 1H), 7.02 (d, J=5.0 Hz, 1H), 7.13-7.34 (m, 3H), 8.19 (d, J=4.9 Hz, 1H), 11.78 (d, J=2.3 Hz, 1H). MS (APCI$^+$) m/z 478.7 (M+H)$^+$.

EXAMPLE 1279 tert-butyl 3-{4-[4-(5-fluoro-2-methoxyphenyl)-1H-pyrrolo[2,3-b]pyridin-2-yl]piperidin-1-yl}azetidine-1-carboxylate The title compound was prepared essentially as described in Example 908, substituting Example 135B for Example 87D and tert-butyl 3-oxoazetidine-1-carboxylate for (S)-1-tert-butyl 2-methyl 4-oxopyrrolidine-1,2-dicarboxylate. $^1$H NMR (500 MHz, DMSO-d$_6$) δ ppm 1.38 (s, 9H), 1.60-1.75 (m, 2H), 1.83-1.93 (m, 2H), 1.93-2.03 (m, 2H), 2.65-2.77 (m, 1H), 2.79-2.88 (m, 2H), 2.98-3.10 (m, 1H), 3.55-3.69 (m, 2H), 3.73 (s, 3H), 3.77-3.94 (m, 2H), 3.87 (s, 2H), 5.96 (d, J=2.0 Hz, 1H), 7.01 (d, J=5.0 Hz, 1H), 7.13-7.31 (m, 3H), 8.13 (d, J=4.9 Hz, 1H), 11.56 (d, J=2.3 Hz, 1H). MS (APCI$^+$) m/z 480.6 (M+H)$^+$.

EXAMPLE 1280

{4-[5-fluoro-4-(5-fluoro-2-methoxyphenyl)-1H-pyrrolo[2,3-b]pyridin-2-yl]cyclohex-3-en-1-yl}acetic acid

EXAMPLE 1280A methyl 2-(4-(4-chloro-5-fluoro-1-(phenylsulfonyl)-1H-pyrrolo[2,3-b]pyridin-2-yl)cyclohex-3-enyl)acetate The title compound was prepared essentially as described in Example 1171C, substituting Example 231B for Example 219A. MS (ESI$^+$) m/z 463.0 (M+H)$^+$.

EXAMPLE 1280B

{4-[5-chloro-4-(5-fluoro-2-methoxyphenyl)-1H-pyrrolo[2,3-b]pyridin-2-yl]cyclohex-3-en-1-yl}acetic acid The title compound was prepared essentially as described in Example 229D, substituting Example 1280A for Example 229C. MS (ESI$^+$) m/z 553.1 (M+H)$^+$.

EXAMPLE 1280C

{4-[5-fluoro-4-(5-fluoro-2-methoxyphenyl)-1H-pyrrolo[2,3-b]pyridin-2-yl]cyclohex-3-en-1-yl}acetic acid A solution of Example 1280B (0.05 g, 0.090 mmol) in 1,4-dioxane (0.5 ml) was treated with sodium hydroxide (0.018 g, 0.452 mmol) and water (0.15 mL) and mixture was heated at 85° C. for 1 hour. The reaction mixture was concentrated and the residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (500 MHz, CD$_3$OD) δ ppm 1.41-1.53 (m, 1H), 1.93-2.06 (m, 2H), 2.06-2.15 (m, 1H), 2.33 (d, J=7.1 Hz, 2H), 2.37-2.59 (m, 3H), 3.78 (s, 3H), 6.19 (s, 1H), 6.41-6.49 (m, 1H), 7.11-7.28 (m, 3H), 8.12 (d, J=3.2 Hz, 1H). MS (ESI$^+$) m/z 399.2 (M+H)$^+$.

EXAMPLE 1281

2-[1-(azetidin-3-yl)-1,2,3,6-tetrahydropyridin-4-yl]-4-(5-fluoro-2-methoxyphenyl)-1H-pyrrolo[2,3-b]pyridine The title compound was prepared essentially as described in Example 913, substituting Example 1278 for Example 908. $^1$H NMR (500 MHz, CD$_3$OD) δ ppm 2.95-3.02 (m, 2H), 3.36-3.47 (m, 2H), 3.83 (s, 3H), 3.87-4.00 (m, 2H), 4.35-4.48 (m, 3H), 4.60-4.69 (m, 2H), 6.52-6.66 (m, 1H), 6.75 (s, 1H), 7.22-7.37 (m, 3H), 7.60 (d, J=6.2 Hz, 1H), 8.36 (d, J=6.1 Hz, 1H). MS (ESI$^+$) m/z 379.1 (M+H)$^+$.

EXAMPLE 1282

2-[1-(azetidin-3-yl)piperidin-4-yl]-4-(5-fluoro-2-methoxyphenyl)-1H-pyrrolo[2,3-b]pyridine The title compound was prepared essentially as described in Example 913, substituting Example 1279 for Example 908. $^1$H NMR (500 MHz, CD$_3$OD) δ ppm 2.19-2.33 (m, 2H), 2.36-2.45 (m, 2H), 3.11-3.22 (m, 2H), 3.26-3.37 (m, 1H), 3.53-3.70 (m, 2H), 3.83 (s, 3H), 4.34-4.50 (m, 3H), 4.67-4.76 (m, 2H), 6.53 (s, 1H), 7.20-7.37 (m, 3H), 7.59 (d, J=6.2 Hz, 1H), 8.34 (d, J=6.1 Hz, 1H). MS (ESI$^+$) m/z 381.2 (M+H)$^+$.

EXAMPLE 1283

[3-(benzyloxy)-1,2-oxazol-5-yl]{4-[4-(5-fluoro-2-methoxyphenyl)-1H-pyrrolo[2,3-b]pyridin-2-yl]-3,6-dihydropyridin-1(2H)-yl}methanone A solution of Example 87D (0.1 g, 0.252 mmol), N-ethyl-N-isopropylpropan-2-amine (0.220 ml, 1.262 mmol) and 3-(benzyloxy)isoxazole-5-carboxylic acid (0.066 g, 0.303 mmol) in N,N-dimethylformamide (1.941 ml) was treated with 1-[bis(dimethylamino)methylene]-1H-1,2,3-triazolo[4,5-b]pyridinium 3-oxide hexafluorophosphate (0.099 g, 0.260 mmol) and the reaction mixture was stirred at room temperature for 20 hours. The reaction mixture was poured into 12 mL water and the resulting suspension was filtered. The solid was washed with water and dried under vacuum. Purification by flash chromatography on silica gel (AnaLogix IntelliFlash 280 system) eluting with a gradient of from 0% to 4% methanol in dichloromethane afforded the title compound. $^1$H NMR (400 MHz, DMSO-$d_6$) δ ppm 2.58-2.69 (m, 2H), 3.72 (s, 3H), 3.74-3.86 (m, 2H), 4.26-4.35 (m, 2H), 5.31 (s, 2H), 6.27 (d, J=1.6 Hz, 1H), 6.41-6.54 (m, 1H), 6.69 (s, 1H), 7.02 (d, J=5.0 Hz, 1H), 7.11-7.28 (m, 3H), 7.29-7.54 (m, 5H), 8.20 (d, J=4.9 Hz, 1H), 11.57 (brs, 1H). MS (ESI$^+$) m/z 525.1 (M+H)$^+$.

EXAMPLE 1284

4-[5-cyano-4-(5-fluoro-2-methoxyphenyl)-1H-pyrrolo[2,3-b]pyridin-2-yl]cyclohex-3-ene-1-carboxylic acid

EXAMPLE 1284A 4-(5-fluoro-2-methoxyphenyl)-2-iodo-1H-pyrrolo[2,3-b]pyridine-5-carbonitrile The title compound was prepared essentially as described in Example 219A, substituting Example 87B with Example 236C. MS (ESI): 394.1 (M+H)$^+$.

EXAMPLE 1284B

4-[5-cyano-4-(5-fluoro-2-methoxyphenyl)-1H-pyrrolo[2,3-b]pyridin-2-yl]cyclohex-3-ene-1-carboxylic acid The title compound was prepared essentially as described in Example 219B, substituting Example 219A with Example 1284A. During the course of this reaction, the ethyl ester was hydrolyzed. The solvent was removed and to the residue was added 5 mL of 6M aqueous NaOH solution and 1 mL of water. The aqueous layer was extracted with ethyl acetate and the organic layer was discarded. To the aqueous layer was added 1M aqueous HCl until pH-7. The solid was filtered and dried over high-vacuum to give the title compound. $^1$H NMR (500 MHz, DMSO-$d_6$) δ ppm 12.40 (s, 1 H) 8.37-8.77 (m, 1 H) 7.14-7.53 (m, 3 H) 6.62 (s, 1 H) 6.20 (d, J=4.27 Hz, 1 H) 3.75 (s, 3 H) 2.24-2.48 (m, 5 H) 1.94-2.06 (m, 1 H) 1.62 (d, J=7.02 Hz, 1 H). MS (ESI): 392.2 (M+H)$^+$.

EXAMPLE 1285 tert-butyl 4-[4-(5-fluoro-2-methoxyphenyl)-3-nitro-1H-pyrrolo[2,3-b]pyridin-2-yl]piperazine-1-carboxylate

EXAMPLE 1285A 4-bromo-2-iodo-3-nitro-1H-pyrrolo[2,3-b]pyridine

To a solution of fuming nitric acid (10 mL, 224 mmol) in a 100 mL flask at about −78° C. was added Example 220B (2.0 g, 4.2 mmol) in portions. The reaction mixture was stirred at about −78° C. to allow adequate stirring for 4 hours. The reaction mixture was quenched with water (50 mL) carefully. The mixture was transferred to 200 mL of icy water and stirred for 15 minutes. The solids were filtered, washed with water, and dried by vacuum to afford the title compound as nitric acid salt. MS (ESI$^+$) m/z: 367.7 (M+H)$^+$.

EXAMPLE 1285B tert-butyl 4-(4-bromo-3-nitro-1H-pyrrolo[2,3-b]pyridin-2-yl)piperazine-1-carboxylate To a suspension of Example 1285A (0.228 g, 0.529 mmol) in 3 mL dioxane, tert-butyl piperazine-1-carboxylate (0.358 g, 1.92 mmol) was added. The mixture was stirred at room temperature for 2.5 hours. To the suspension was added dichloromethane and the product was purified by flash chromatography on silica gel (AnaLogix IntelliFlash) eluting with a gradient of 0-10% methanol in dichloromethane to afford the title compound. MS (ESI+) m/z 425.1 (M+H)+.

EXAMPLE 1285C tert-butyl 4-[4-(5-fluoro-2-methoxyphenyl)-3-nitro-1H-pyrrolo[2,3-b]pyridin-2-yl]piperazine-1-carboxylate The title compound was prepared using the procedure described in Example 301A, using Example 1285B in place of Example 236C. $^1$H NMR (501 MHz, DMSO-$d_6$): δ 1.42 (s, 9 H) 3.47-3.58 (m, 8 H) 3.55 (s, 3 H) 6.93-6.99 (m, 1 H) 7.11 (d, J=5.19 Hz, 1 H) 7.13-7.19 (m, 2 H) 8.18 (d, J=4.88 Hz, 1 H). MS (ESI$^+$) m/z: 471.2 (M+H)$^+$.

EXAMPLE 1286

4-(5-fluoro-2-methoxyphenyl)-3-nitro-2-(piperazin-1-yl)-1H-pyrrolo[2,3-b]pyridine The title compound was prepared using the procedure described in Example 444D, using Example 1285C in place of Example 444C. $^1$H NMR (501 MHz, DMSO-$d_6$): δ 3.31-3.38 (m, 4 H) 3.57 (s, 3 H) 6.95-7.02 (m, 1H) 7.14-7.23 (m, 3H) 8.23 (d, J=5.19 Hz, 1 H) 8.91 (s, 2 H). MS (ESI$^+$) m/z: 371.1 (M+H)$^+$.

EXAMPLE 1287

4-[4-(5-fluoro-2-methoxyphenyl)-3-nitro-1H-pyrrolo[2,3-b]pyridin-2-yl]-N-methylpiperazine-1-carboxamide The title compound was prepared using the procedure described in Example 229G, using Example 1286 in place of Example 229F. $^1$H NMR (501 MHz, DMSO-$d_6$): δ 2.60 (s, 3 H) 3.46-3.55 (m, 8 H) 3.57 (s, 3 H) 6.94-7.01 (m, 1 H) 7.12 (d, J=5.19 Hz, 1 H) 7.14-7.21 (m, 2 H) 8.18 (d, J=5.19 Hz, 1 H). MS (ESI$^+$) m/z: 429.2 (M+H)$^+$.

EXAMPLE 1288

4-(5-fluoro-2-methoxyphenyl)-2-{1-[1-(methylsulfonyl)azetidin-3-yl]-1,2,3,6-tetrahydropyridin-4-yl}-1H-pyrrolo[2,3-b]pyridine The title compound was prepared essentially as described in Example 119, substituting Example 1281 for Example 87D. $^1$H NMR (400 MHz, CD$_3$OD) δ ppm 2.91-3.00 (m, 2H), 3.01 (s, 3H), 3.51 (t, J=6.1 Hz, 2H), 3.80 (s, 3H), 3.94-4.08 (m, 2H), 4.20-4.32 (m, 5H), 6.46-6.55 (m, 1H), 6.64 (s, 1H), 7.15-7.34 (m, 3H), 7.41 (d, J=5.6 Hz, 1H), 8.32 (d, J=5.8 Hz, 1H). MS (ESI$^+$) m/z 457.1 (M+H)$^+$.

EXAMPLE 1289

4-(5-fluoro-2-methoxyphenyl)-2-{1-[1-(methylsulfonyl)azetidin-3-yl]piperidin-4-yl}-1H-pyrrolo[2,3-b]pyridine The title compound was prepared essentially as described in Example 119, substituting Example 1282 for Example 87D. $^1$H NMR (400 MHz, CD$_3$OD) δ ppm 2.04-2.21 (m, 2H), 2.36-2.48 (m, 2H), 3.01 (s, 3H), 3.07-3.23 (m, 2H), 3.22-3.35 (m, 1H), 3.57-3.76 (m, 2H), 3.81 (s, 3H), 4.14-4.29 (m, 5H), 6.45 (s, 1H), 7.17-7.36 (m, 3H), 7.52 (d, J=6.1 Hz, 1H), 8.32 (d, J=6.0 Hz, 1H). MS (ESI$^+$) m/z 459.2 (M+H)$^+$.

EXAMPLE 1290

2-{4-[4-(5-fluoro-2-methoxyphenyl)-1H-pyrrolo[2,3-b]pyridin-2-yl]-2,3,6,7-tetrahydro-1H-azepin-1-yl}-N-(3-hydroxycyclobutyl)-N-methylacetamide The title compound was prepared according to the procedure described in Example 238, substituting Example 1276 for Example 226B and 3-(methylamino)cyclobutanol for azetidin-3-ol hydrochloride. $^1$H NMR (400 MHz, DMSO-d$_6$) δ 1.91 (s, 3H), 2.0-3.0 (m, 10H), 3.17 (s, 3H), 3.73 (s, 4H), 3.86-4.41 (m, 2H), 4.90-5.18 (m, 1H), 6.25 (s, 1H), 6.65 (t, J=6.5 Hz, 1H), 7.01 (d, J=4.9 Hz, 1H), 7.13-7.33 (m, 3H), 8.17 (d, J=4.9 Hz, 1H), 11.67 (bs, 1H). MS (ESI$^+$) m/z 479 (M+H)$^+$.

EXAMPLE 1291

2-{4-[4-(5-fluoro-2-methoxyphenyl)-1H-pyrrolo[2,3-b]pyridin-2-yl]-2,3,6,7-tetrahydro-1H-azepin-1-yl}-N-(2-hydroxyethyl)-N-methylacetamide The title compound was prepared according to the procedure described in Example 238, substituting Example 1276 for Example 226B and 2-(methylamino)ethanol for azetidin-3-ol hydrochloride. $^1$H NMR (400 MHz, DMSO-d$_6$) δ 1.90 (s, 3H), 2.39 (q, J=5.7, 5.1 Hz, 2H), 2.53-2.78 (m, 4H), 2.81 (s, 2H), 3.23-3.40 (m, 2H), 3.39-3.65 (m, 4H), 3.73 (s, 3H), 6.25 (d, J=2.2 Hz, 1H), 6.65 (t, J=6.4 Hz, 1H), 7.01 (d, J=4.9 Hz, 1H), 7.14-7.33 (m, 3H), 8.17 (d, J=5.0 Hz, 1H), 10.73-12.47 (m, 1H). MS (ESI$^+$) m/z 453 (M+H)$^+$.

EXAMPLE 1292

2-{4-[4-(5-fluoro-2-methoxyphenyl)-1H-pyrrolo[2,3-b]pyridin-2-yl]-2,3,6,7-tetrahydro-1H-azepin-1-yl}-1-[(2S)-2-(hydroxymethyl)pyrrolidin-1-yl]thanone The title compound was prepared according to the procedure described in Example 238, substituting Example 1276 for Example 226B and (S)-pyrrolidin-2-ylmethanol for azetidin-3-ol hydrochloride. $^1$H NMR (400 MHz, DMSO-d$_6$) δ 1.76-2.03 (m, 5H), 2.60-2.72 (dt, J=11.2, 4.4 Hz, 2H), 2.85-3.29 (m, 4H), 3.38 (dt, J=12.0, 6.6 Hz, 3H), 3.45-3.66 (m, 3H), 3.74 (s, 3H), 4.23-4.50 (m, 2H), 6.37 (d, J=4.6 Hz, 1H), 6.58-6.66 (m, 1H), 7.06 (d, J=5.0 Hz, 1H), 7.09-7.34 (m, 3H), 8.22 (d, J=5.0 Hz, 1H), 9.93 (s, 1H), 11.87 (s, 1H). MS (ESI$^+$) m/z 479 (M+H)$^+$.

EXAMPLE 1293

4-(5-fluoro-2-methoxyphenyl)-5-methoxy-2-[2-(methylsulfonyl)-1,2,3,3a,4,6a-hexahydrocyclopenta[c]pyrrol-5-yl]-1H-pyrrolo[2,3-b]pyridine

EXAMPLE 1293A 4-(5-fluoro-2-methoxyphenyl)-2-(1,2,3,3a,4,6a-hexahydrocyclopenta[c]pyrrol-5-yl)-5-methoxy-1H-pyrrolo[2,3-b]pyridine The title compound was prepared according to the procedure described in Example 873, substituting tert-butyl 5-(4,4,5,5-tetramethyl-1,3,2-dioxaborolan-2-yl)-3,3a,6,6a-tetrahydrocyclopenta[c]pyrrole-2(1H)-carboxylate for tert-butyl 4-(4,4,5,5-tetramethyl-1,3,2-dioxaborolan-2-yl)-5,6-dihydropyridine-1(2H)-carboxylate in Example 873A. MS (ESI$^+$) m/z 380 (M+H)$^+$.

EXAMPLE 1293B 4-(5-fluoro-2-methoxyphenyl)-5-methoxy-2-[2-(methylsulfonyl)-1,2,3,3a,4,6a-hexahydrocyclopenta[c]pyrrol-5-yl]-1H-pyrrolo[2,3-b]pyridine The title compound was prepared using the procedure described in Example 262F, substituting Example 1293A for Example 262E. $^1$H NMR (400 MHz, DMSO-d$_6$) δ 2.56 (dd, J=15.9, 10.9 Hz, 1H), 2.86 (s, 3H), 2.89-3.22 (m, 4H), 3.39 (dt, J=22.6, 8.7 Hz, 2H), 3.68 (s, 4H), 3.77 (s, 3H), 5.92 (dd, J=3.8, 1.9 Hz, 1H), 6.24-6.29 (m, 1H), 7.04-7.28 (m, 3H), 8.14 (s, 1H), 11.77 (bs, 1H). MS (ESI$^+$) m/z 458 (M+H)$^+$.

EXAMPLE 1294

2-{5-[4-(5-fluoro-2-methoxyphenyl)-5-methoxy-1H-pyrrolo[2,3-b]pyridin-2-yl]-3,3a,4,6a-tetrahydrocyclopenta[c]pyrrol-2(1H)-yl}-N,N-dimethylacetamide The title compound was prepared according to the procedure described in Example 235, substituting Example 1293A for Example 17G. $^1$H NMR (400 MHz, DMSO-d$_6$) δ 2.57-2.76 (m, 1H), 2.75-3.09 (m, 8H), 3.07-3.29 (m, 2H), 3.31-3.52 (m, 1H), 3.68 (d, J=4.4 Hz, 3H), 3.75-3.80 (m, 4H), 3.85-4.05 (m, 1H), 4.18-4.37 (m, 2H), 5.92-5.98 (m, 1H), 6.20-6.34 (m, 1H), 6.99-7.12 (m, 1H), 7.16 (dd, J=9.1, 4.5 Hz, 1H), 7.21-7.30 (m, 1H), 8.16 (bs, 1H), 11.83-11.91 (m, 1H). MS (ESI$^+$) m/z 465 (M+H)$^+$.

EXAMPLE 1295

4-[4-(4,5-difluoro-2-methoxyphenyl)-5-fluoro-1H-pyrrolo[2,3-b]pyridin-2-yl]cyclohex-3-ene-1-carboxylic acid

EXAMPLE 1295A

The title compound was prepared essentially as described in Example 279B and Example 65D, substituting 5-fluoro-2-methoxyphenyl boronic acid with (4,5-difluoro-2-methoxyphenyl)boronic acid. LCMS (ESI) 571.2 (M+H)$^+$.

EXAMPLE 1295B

4-[4-(4,5-difluoro-2-methoxyphenyl)-5-fluoro-1H-pyrrolo[2,3-b]pyridin-2-yl]cyclohex-3-ene-1-carboxylic acid The title compound was prepared essentially as described in Example 219C, substituting Example 219B with Example 1295A. $^1$H NMR (400 MHz, DMSO-$d_6$) δ ppm 11.85 (s, 1 H) 8.15 (d, J=2.75 Hz, 1 H) 7.18-7.66 (m, 2 H) 6.53 (s, 1 H) 6.13 (s, 1 H) 3.70-3.80 (m, 3 H) 2.25-2.48 (m, 4 H) 1.93-2.08 (m, 1 H) 1.56-1.75 (m, 1 H). MS (ESI): 403.2 (M+H)$^+$.

EXAMPLE 1296

4-[5-fluoro-4-(4-fluoro-2-methoxyphenyl)-1H-pyrrolo[2,3-b]pyridin-2-yl]cyclohex-3-ene-1-carboxylic acid

EXAMPLE 1296A

The title compound was prepared essentially as described in Example 279B and Example 65D, substituting 5-fluoro-2-methoxyphenyl boronic acid with 4-fluoro-2-methoxyphenyl boronic acid. LCMS (APCI): 553.15 (M+H)$^+$.

EXAMPLE 1296B

4-[5-fluoro-4-(4-fluoro-2-methoxyphenyl)-1H-pyrrolo[2,3-b]pyridin-2-yl]cyclohex-3-ene-1-carboxylic acid The title compound was prepared essentially as described in Example 219C, substituting Example 219B with Example 1296A. $^1$H NMR (400 MHz, DMSO-$d_6$) δ ppm 11.82 (s, 1 H) 8.14 (d, J=2.75 Hz, 1 H) 7.29-7.53 (m, 1 H) 7.12 (dd, J=11.60, 2.44 Hz, 1 H) 6.80-7.04 (m, 1 H) 6.53 (s, 1 H) 6.07 (s, 1 H) 3.72-3.87 (m, 3 H) 2.24-2.48 (m, 4 H) 1.97-2.08 (m, 1 H) 1.65 (dd, J=10.07, 2.44 Hz, 1 H). MS (ESI): 385.2 (M+H)$^+$.

EXAMPLE 1297

(4-{4-[4-(5-fluoro-2-methoxyphenyl)-1H-pyrrolo[2,3-b]pyridin-2-yl]cyclohex-3-en-1-yl}piperazin-1-yl)acetic acid

EXAMPLE 1297A tert-butyl 2-(4-(4-(4-(5-fluoro-2-methoxyphenyl)-1H-pyrrolo[2,3-b]pyridin-2-yl)cyclohex-3-enyl)piperazin-1-yl)acetate To a mixture of Example 1018B (bis hydrochloride salt, 0.08 g, 0.167 mmol) and triethylamine (0.093 ml, 0.667 mmol) in N,N-dimethylformamide (1.517 mL) was added tert-butyl 2-bromoacetate (0.028 mL, 0.192 mmol). The reaction mixture was stirred at ambient temperature overnight. The mixture was poured into 10 mL of water and the resulting precipitate was stirred vigorously for 30 minutes then filtered and washed with water (10 mL) and heptane (5 mL). The solid was collected and dried under high vacuum to provide the title compound. MS (ESI$^+$) m/z 520.7 (M+H)$^+$.

EXAMPLE 1297B 2-(4-(4-(4-(5-fluoro-2-methoxyphenyl)-1H-pyrrolo[2,3-b]pyridin-2-yl)cyclohex-3-enyl)piperazin-1-yl)acetic acid Example 1297A (90 mg, 0.173 mmol) was dissolved in dichloromethane (1.5 mL) and trifluoroacetic acid (1 mL) was added. The reaction mixture was stirred at ambient temperature overnight. The mixture was then concentrated and dried under high vacuum. Next, the residue was dissolved in 1.0 mL of tetrahydrofuran and treated with 5 mL of a 2 M hydrochloric acid in diethyl ether. The precipitate that formed was stirred vigorously at 0° C. for 10 minutes then filtered and washed with diethyl ether (10 mL) and heptane (10 mL) to provide the title compound as a bis hydrochloride salt. $^1$H NMR (400 MHz, DMSO-$d_6$) δ ppm 1.76-1.95 (m, 1H), 2.31-2.42 (m, 1H), 2.41-2.51 (m, 1H), 2.58-2.72 (m, 1H), 2.72-2.90 (m, 2H), 3.43-3.73 (m, 8H), 3.77 (s, 3H), 4.19 (s, 2H), 6.44 (d, J=2.0 Hz, 1H), 6.60-6.71 (m, 1H), 7.20-7.40 (m, 4H), 8.30 (d, J=5.5 Hz, 1H), 12.29 (s, 1H), 12.76 (s, 1H). MS (ESI$^+$) m/z 465.1 (M+H)$^+$.

EXAMPLE 1302

{4-[4-(5-fluoro-2-methoxyphenyl)-1H-pyrrolo[2,3-b]pyridin-2-yl]-3,6-dihydropyridin-1(2H)-yl}(3-hydroxy-1,2-oxazol-5-yl)methanone A mixture of Example 1283 (0.043 g, 0.082 mmol) and 20% palladium hydroxide on carbon (wet, 10 mg) in methanol (2 ml) and tetrahydrofuran (2 ml) was stirred at 50° C. for 15 minutes in a pressure bottle under 30 psi hydrogen gas. The mixture was filtered through a nylon membrane and concentrated. The residue was purified by reverse phase HPLC on a Phenomenex Luna C8(2) 5 um 100 Å AXIA column (30 mm×75 mm) eluting with a gradient of 10-95% acetonitrile in 0.1% trifluoroacetic acid/water to afford the title compound as a trifluoroacetic acid salt. $^1$H NMR (400 MHz, CD$_3$OD) δ ppm 2.58-2.80 (m, 2H), 3.81 (s, 3H), 3.84-4.02 (m, 2H), 4.29-4.64 (m, 2H), 6.36-6.64 (m, 3H), 7.15-7.32 (m, 3H), 7.46 (d, J=5.9 Hz, 1H), 8.28 (d, J=6.0 Hz, 1H). MS (ESI$^+$) m/z 435.2 (M+H)$^+$.

EXAMPLE 1303

3-{4-[4-(5-fluoro-2-methoxyphenyl)-1H-pyrrolo[2,3-b]pyridin-2-yl]-3,6-dihydropyridin-1(2H)-yl}-N-methylazetidine-1-carboxamide The title compound was prepared essentially as described in Example 222D, substituting Example 1281 for Example 222C. $^1$H NMR (400 MHz, CD$_3$OD) δ ppm 2.71 (s, 3H), 2.92-3.03 (m, 2H), 3.42-3.66 (m, 2H), 3.80 (s, 3H), 3.94-4.08 (m, 2H), 4.11-4.42 (m, 5H), 6.48-6.56 (m, 1H), 6.65 (s, 1H), 7.15-7.34 (m, 3H), 7.43 (d, J=5.7 Hz, 1H), 8.33 (d, J=5.8 Hz, 1H). MS (ESI$^+$) m/z 436.0 (M+H)$^+$.

EXAMPLE 1304

3-{4-[4-(5-fluoro-2-methoxyphenyl)-1H-pyrrolo[2,3-b]pyridin-2-yl]piperidin-1-yl}-N-methylazetidine-1-carboxamide The title compound was prepared essentially as described in Example 222D, substituting Example 1282 for Example 222C. ¹H NMR (500 MHz CD₃OD) δ ppm 1.95-2.18 (m, 2H), 2.39-2.48 (m, 2H), 2.71 (s, 3H), 3.04-3.36 (m, 3H), 3.51-3.76 (m, 2H), 3.81 (s, 3H), 4.09-4.17 (m, 3H), 4.20-4.28 (m, 2H), 6.44 (s, 1H), 7.18-7.34 (m, 3H), 7.50 (d, J=6.0 Hz, 1H), 8.32 (d, J=5.9 Hz, 1H). MS (ESI⁺) m/z 438.2 (M+H)⁺.

EXAMPLE 1305

3-{4-[4-(5-fluoro-2-methoxyphenyl)-1H-pyrrolo[2,3-b]pyridin-2-yl]-3,6-dihydropyridin-1(2H)-yl}cyclobutanecarbonitrile Example 87D (0.06 g, 0.151 mmol) and triethylamine (0.053 ml, 0.379 mmol) in dichloromethane (1.262 ml) and methanol (1.262 ml) was treated with 3-oxocyclobutanecarbonitrile (0.022 g, 0.227 mmol) and acetic acid (0.052 ml, 0.908 mmol) followed by MP-cyanoborohydride (2.49 mmol/g, 0.243 g, 0.606 mmol). The reaction mixture was stirred at room temperature for 24 hours. The reaction mixture was diluted with 20 mL 50% methanol in dichloromethane and filtered. The filtrate was concentrated and the residue was purified by reverse phase HPLC on a Phenomenex Luna C8(2) 5 μm 100 Å AXIA column (30 mm×75 mm) eluting with a gradient of 10-95% acetonitrile in 0.1% trifluoroacetic acid/water to afford the title compound as a trifluoroacetic acid salt. ¹H NMR (500 MHz, DMSO-d₆) δ ppm 2.58-2.95 (m, 6H), 3.06-3.32 (m, 2H), 3.47-4.13 (m, 7H), 6.40 (d, J=2.1 Hz, 1H), 6.45-6.52 (m, 1H), 7.09 (d, J=4.9 Hz, 1H), 7.17-7.35 (m, 3H), 8.26 (d, J=5.0 Hz, 1H), 10.21 (brs, 1H), 12.07 (d, J=2.3 Hz, 1H). MS (APCI⁺) m/z 402.7 (M+H)⁺.

EXAMPLE 1306

3-{4-[4-(5-fluoro-2-methoxyphenyl)-1H-pyrrolo[2,3-b]pyridin-2-yl]-3,6-dihydropyridin-1(2H)-yl}cyclopentanecarboxylic acid

EXAMPLE 1306A methyl 3-(4-(4-(5-fluoro-2-methoxyphenyl)-1H-pyrrolo[2,3-b]pyridin-2-yl)-5,6-dihydropyridin-1(2H)-yl)cyclopentanecarboxylate The title compound was prepared essentially as described in Example 908, substituting methyl 3-oxocyclopentanecarboxylate for (S)-1-tert-butyl 2-methyl 4-oxopyrrolidine-1,2-dicarboxylate. MS (APCI⁺) m/z 450.1 (M+H)⁺.

EXAMPLE 1306B

3-{4-[4-(5-fluoro-2-methoxyphenyl)-1H-pyrrolo[2,3-b]pyridin-2-yl]-3,6-dihydropyridin-1(2H)-yl}cyclopentanecarboxylic acid A mixture of Example 1306A (0.108 g, 0.240 mmol) in tetrahydrofuran (1.201 ml) and methanol (1.201 ml) was treated with aqueous 2 M lithium hydroxide (0.360 ml, 0.721 mmol). The reaction was stirred at room temperature for 24 hours. The reaction mixture was concentrated and the residue was dissolved in 5 mL water. The solution was cooled in an ice bath at 0° C. and was neutralized (pH 6) with aqueous 3 N hydrochloric acid. The resulting suspension was filtered and the solid collected was washed with water and dried under vacuum to afford the title compound. ¹H NMR (400 MHz, DMSO-d₆, 90° C.) δ ppm 1.44-2.21 (m, 7H), 2.64-2.96 (m, 5H), 3.17-3.32 (m, 2H), 3.76 (s, 3H), 6.22 (d, J=1.6 Hz, 1H), 6.46-6.52 (m, 1H), 7.04 (d, J=5.0 Hz, 1H), 7.15-7.30 (m, 3H), 8.21 (d, J=5.0 Hz, 1H), 11.51 (brs, 1H). (ESI⁺) m/z 435.7 (M+H)⁺.

EXAMPLE 1307

9-[4-(5-fluoro-2-methoxyphenyl)-1H-pyrrolo[2,3-b]pyridin-2-yl]-3-azaspiro[5.5]undec-8-ene

EXAMPLE 1307A tert-butyl 9-(trifluoromethylsulfonyloxy)-3-azaspiro[5.5]undec-8-ene-3-carboxylate The title compound was prepared using the procedure described in Example 262A, using tert-butyl 9-oxo-3-azaspiro[5.5]undecane-3-carboxylate in place of tert-butyl 5-oxohexahydrocyclopenta[c]pyrrole-2(1H)-carboxylate.

EXAMPLE 1307B tert-butyl 9-(4,4,5,5-tetramethyl-1,3,2-dioxaborolan-2-yl)-3-azaspiro[5.5]undec-8-ene-3-carboxylate The title compound was prepared using the procedure described in Example 262B, using Example 1307A in place of Example 262A.

EXAMPLE 1307C tert-butyl 9-(4-(5-fluoro-2-methoxyphenyl)-1H-pyrrolo[2,3-b]pyridin-2-yl)-3-azaspiro[5.5]undec-8-ene-3-carboxylate The title compound was prepared using the procedure described in Example 219B, using Example 1307B in place of ethyl 4-(4,4,5,5-tetramethyl-1,3,2-dioxaborolan-2-yl)cyclohex-3-enecarboxylate. MS (ESI⁺) m/z: 492.1 (M+H)⁺.

EXAMPLE 1307D

9-[4-(5-fluoro-2-methoxyphenyl)-1H-pyrrolo[2,3-b]pyridin-2-yl]-3-azaspiro[5.5]undec-8-ene The title compound was prepared using the procedure described in Example 444D, using Example 1307C in place of Example 444C. ¹H NMR (500 MHz, DMSO-d₆): δ 1.45-1.83 (m, 5 H) 2.34-2.71 (m, 4 H) 2.83-3.31 (m, 4 H) 3.79 (s, 3 H) 6.40 (s, 1 H) 6.63 (s, 1 H) 7.12-7.51 (m, 4 H) 8.28 (s, 1 H) 9.07 (br. s, 2 H) 12.83 (s, 1 H). MS (ESI⁺) m/z: 392.3 (M+H)⁺.

Example 1308

9-[4-(5-fluoro-2-methoxyphenyl)-1H-pyrrolo[2,3-b]pyridin-2-yl]-N-methyl-3-azaspiro[5.5]undec-8-ene-3-carboxamide The title compound was prepared using the procedure described in Example 229G, using Example 1307D in place of Example 229F. ¹H NMR (500 MHz, DMSO-d₆): δ 1.26-1.38 (m, 4 H) 1.55-1.61 (m, 2 H) 2.10-2.16 (m, 2 H) 2.35-2.42 (m, 2 H) 2.55 (s, 3 H) 3.19-3.27 (m, 2 H) 3.30-3.39 (m, 2 H) 3.75 (s, 3 H) 6.25 (d, J=1.53 Hz, 1 H) 6.46-6.52 (m, 1 H) 7.10 (d, J=5.19 Hz, 1 H) 7.17-7.32 (m, 3 H) 8.21 (d, J=5.19 Hz, 1 H) 11.96 (s, 1 H). MS (ESI+) m/z: 449.3 (M+H)+.

EXAMPLE 1309

9-[4-(5-fluoro-2-methoxyphenyl)-1H-pyrrolo[2,3-b]pyridin-2-yl]-3-(methylsulfonyl)-3-azaspiro[5.5]undec-8-ene The title compound was prepared using the procedure described in Example 262F, using Example 1307D in place of Example 262E. $^1$H NMR (500 MHz, DMSO-d$_6$): δ 1.44-1.54 (m, 4 H) 1.61 (t, J=6.10 Hz, 1 H) 2.13-2.18 (m, 2 H) 2.36-2.42 (m, 2 H) 2.87 (s, 3 H) 3.06-3.13 (m, 2 H) 3.14-3.21 (m, 2 H) 3.74 (s, 3 H) 6.23 (d, J=1.83 Hz, 1 H) 6.47-6.51 (m, 1 H) 7.07 (d, J=4.88 Hz, 1 H) 7.18-7.31 (m, 3 H) 8.20 (d, J=4.88 Hz, 1 H) 11.89 (s, 1 H). MS (ESI+) m/z: 470.2 (M+H)+.

EXAMPLE 1310

(3-{4-[4-(5-fluoro-2-methoxyphenyl)-1H-pyrrolo[2,3-b]pyridin-2-yl]-3,6-dihydropyridin-1(2H)-yl}cyclobutyl)methanol The title compound was prepared essentially as described in Example 1305, substituting 3-(hydroxymethyl)cyclobutanone for 3-oxocyclobutanecarbonitrile. $^1$H NMR (500 MHz, CD$_3$OD) δ ppm 1.67-1.78 (m, 2H), 2.00-2.33 (m, 3H), 2.61-2.69 (m, 2H), 2.70-2.81 (m, 2H), 2.91-3.05 (m, 1H), 3.21-3.29 (m, 2H), 3.52 (d, J=5.8 Hz, 2H), 3.76 (s, 3H), 6.29 (s, 1H), 6.36-6.43 (m, 1H), 7.08 (d, J=5.0 Hz, 1H), 7.11-7.20 (m, 3H), 8.16 (d, J=5.1 Hz, 1H). MS (ESI+) m/z 408.1 (M+H)+.

EXAMPLE 1311

(trans-4-{4-[5-chloro-4-(5-fluoro-2-methoxyphenyl)-1H-pyrrolo[2,3-b]pyridin-2-yl]-3,6-dihydropyridin-1(2H)-yl})cyclohexyl)acetic acid

EXAMPLE 1311A methyl (trans-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetate The title compound was prepared essentially as described in Example 288B, substituting Example 229F for Example 87D. The trans-isomer was isolated from the cis isomer during purification. MS (ESI+) m/z 512.0 (M+H)+.

EXAMPLE 1311B (trans-4-{4-[5-chloro-4-(5-fluoro-2-methoxyphenyl)-1H-pyrrolo[2,3-b]pyridin-2-yl]-3,6-dihydropyridin-1(2H)-yl})cyclohexyl)acetic acid The title compound was prepared essentially as described in Example 288C, substituting Example 1311A for Example 288A. $^1$H NMR (500 MHz, CD$_3$OD) δ ppm 1.13-1.26 (m, 2H), 1.55-1.88 (m, 3H), 1.97-2.13 (m, 2H), 2.14-2.39 (m, 4H), 2.79-2.95 (m, 2H), 3.29-3.39 (m, 2H), 3.70-3.80 (m, 4H), 3.94-4.06 (m, 2H), 6.21 (s, 1H), 6.37-6.44 (m, 1H), 7.01 (dd, J=8.5, 3.0 Hz, 1H), 7.11-7.25 (m, 2H), 8.25 (s, 1H). MS (ESI+) m/z 497.9 (M+H)+.

EXAMPLE 1312

(cis-4-{4-[5-chloro-4-(5-fluoro-2-methoxyphenyl)-1H-pyrrolo[2,3-b]pyridin-2-yl]-3,6-dihydropyridin-1(2H)-yl})cyclohexyl)acetic acid

EXAMPLE 1312A methyl (cis-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetate The title compound was prepared essentially as described in Example 288A, substituting Example 229F for Example 87D. The cis-isomer was isolated from the trans isomer during purification. MS (ESI+) m/z 512.0 (M+H)+.

EXAMPLE 1312B (cis-4-{4-[5-chloro-4-(5-fluoro-2-methoxyphenyl)-1H-pyrrolo[2,3-b]pyridin-2-yl]-3,6-dihydropyridin-1(2H)-yl})cyclohexyl)acetic acid The title compound was prepared essentially as described in Example 288C, substituting Example 1312A for Example 288A. $^1$H NMR (400 MHz, CD$_3$OD) δ ppm 1.55-1.88 (m, 6H), 1.88-2.08 (m, 2H), 2.20-2.33 (m, 1H), 2.42 (d, J=7.7 Hz, 2H), 2.83-2.97 (m, 2H), 3.24-3.40 (m, 2H), 3.70-3.86 (m, 4H), 3.95-4.09 (m, 2H), 6.21 (s, 1H), 6.36-6.45 (m, 1H), 7.01 (dd, J=8.5, 3.1 Hz, 1H), 7.09-7.30 (m, 2H), 8.25 (s, 1H). MS (ESI+) m/z 498.0 (M+H)+.

EXAMPLE 1318

4-(4-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine

EXAMPLE 1318A tert-butyl 5-(4-(4-fluoro-2-methoxyphenyl)-1H-pyrrolo[2,3-b]pyridin-2-yl)-3,3a,6,6a-tetrahydrocyclopenta[c]pyrrole-2(1H)-carboxylate The title compound was prepared as described in Example 87A, substituting Example 1270B for 4-bromo-1-(phenylsulfonyl)-1H-pyrrolo[2,3-b]pyridine and tert-butyl 5-(4,4,5,5-tetramethyl-1,3,2-dioxaborolan-2-yl)-3,3a,6,6a-tetrahydrocyclopenta[c]pyrrole-2(1H)-carboxylate for 5-fluoro-2-methoxyphenylboronic acid.

EXAMPLE 1318B 4-(4-fluoro-2-methoxyphenyl)-2-(1,2,3,3a,4,6a-hexahydrocyclopenta[c]pyrrol-5-yl)-1H-pyrrolo[2,3-b]pyridine The title compound was prepared as described in Example 90A, substituting Example 1318A for Example 88B. MS (ESI+) m/z 350 (M+H)+.

EXAMPLE 1318C 4-(4-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine To Example 1318B (720 mg, 1.705 mmol), and triethylamine (1188 μl, 8.52 mmol) in 10 mL dimethylformamide at 0° C. was added methanesulfonyl chloride (146 μl, 1.875 mmol). The mixture was stirred at room temperature overnight and poured into water (150 mL). The suspension was filtered to collect the title compound. $^1$H NMR (400 MHz, DMSO-$d_6$) δ 2.55-2.75 (m, 1H), 2.82-3.14 (m, 6H), 3.17 (dd, J=9.8, 2.8 Hz, 1H), 3.38-3.48 (m, 2H), 3.57-3.65 (m, 1H), 3.78 (s, 3H), 6.16 (d, J=2.0 Hz, 1H), 6.29 (d, J=2.3 Hz, 1H), 6.91 (td, J=8.4, 2.5 Hz, 1H), 7.01 (d, J=4.9 Hz, 1H), 7.10 (dd, J=11.5, 2.5 Hz, 1H), 7.42 (dd, J=8.4, 6.9 Hz, 1H), 8.20 (d, J=4.9 Hz, 1H), 11.86-11.91 (m, 1H). MS (ESI$^+$) m/z 428 (M+H)$^+$.

EXAMPLE 1319

4-(4,5-difluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine

EXAMPLE 1319A tert-butyl 5-(4-(4,5-difluoro-2-methoxyphenyl)-1H-pyrrolo[2,3-b]pyridin-2-yl)-3,3a,6,6a-tetrahydrocyclopenta[c]pyrrole-2(1H)-carboxylate The title compound was prepared as described in Example 87A, substituting Example 1271B for 4-bromo-1-(phenylsulfonyl)-1H-pyrrolo[2,3-b]pyridine and tert-butyl 5-(4,4,5,5-tetramethyl-1,3,2-dioxaborolan-2-yl)-3,3a,6,6a-tetrahydrocyclopenta[c]pyrrole-2(1H)-carboxylate for 5-fluoro-2-methoxyphenylboronic acid.

EXAMPLE 1319B 4-(4,5-difluoro-2-methoxyphenyl)-2-(1,2,3,3a,4,6a-hexahydrocyclopenta[c]pyrrol-5-yl)-1H-pyrrolo[2,3-b]pyridine The title compound was prepared as described in Example 90A, substituting Example 1319A for Example 88B. MS (ESI$^+$) m/z 368 (M+H)$^+$.

EXAMPLE 1319C 4-(4,5-difluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine The title compound was prepared as described in Example 1318C, substituting Example 1319B for Example 1318B. $^1$H NMR (400 MHz, DMSO-$d_6$) δ 2.60-2.70 (m, 1H), 2.87 (s, 3H), 3.03-3.22 (m, 2H), 3.29-3.52 (m, 4H), 3.61 (d, J=6.0 Hz, 1H), 3.76 (s, 3H), 6.21 (s, 1H), 6.31 (bs, 1H), 7.03 (d, J=4.9 Hz, 1H), 7.35 (dd, J=12.9, 6.9 Hz, 1H), 7.43-7.52 (m, 1H), 8.21 (d, J=4.9 Hz, 1H), 11.93 (bs, 1H). MS (ESI$^+$) m/z 446 (M+H)$^+$.

EXAMPLE 1320

2-{3-[4-(5-fluoro-2-methoxyphenyl)-1H-pyrrolo[2,3-b]pyridin-2-yl]-9-azabicyclo[3.3.1]non-2-en-9-yl}-N-(2-hydroxyethyl)-N-methylacetamide

EXAMPLE 1320A

{3-[4-(5-fluoro-2-methoxyphenyl)-1H-pyrrolo[2,3-b]pyridin-2-yl]-9-azabicyclo[3.3.1]non-2-en-9-yl}acetic acid The title compound was prepared as described in Example 1239A, substituting Example 1260 for Example 1215B. MS (ESI$^+$) m/z 422 (M+H)$^+$.

EXAMPLE 1320B

2-{3-[4-(5-fluoro-2-methoxyphenyl)-1H-pyrrolo[2,3-b]pyridin-2-yl]-9-azabicyclo[3.3.1]non-2-en-9-yl}-N-(2-hydroxyethyl)-N-methylacetamide A mixture of Example 1320A (76 mg, 0.10 mmol), 2-(methylamino)ethanol (15.02 mg, 0.200 mmol), 1-[bis(dimethylamino)methylene]-1H-1,2,3-triazolo[4,5-b]pyridinium 3-oxide hexafluorophosphate (45.6 mg, 0.120 mmol) and triethylamine (69.7 μl, 0.500 mmol) in N,N-dimethylformamide (1.5 mL) was stirred at room temperature for 1 hour. The reaction mixture was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile: 10 mM ammonium acetate in water to afford the title compound. $^1$H NMR (400 MHz, DMSO-$d_6$) δ ppm 1.31-1.82 (m, 5 H) 2.05-2.17 (m, 1 H) 2.63-3.63 (m, 13 H) 3.74 (s, 3 H) 6.24 (s, 1 H) 6.45 (d, J=4.58 Hz, 1 H) 7.03 (d, J=4.88 Hz, 1 H) 7.11-7.32 (m, 3 H) 8.19 (d, J=4.88 Hz, 1 H) 11.78 (s, 1 H). MS (ESI$^+$) m/z 479 (M+H)$^+$.

EXAMPLE 1321

2-{3-[4-(5-fluoro-2-methoxyphenyl)-1H-pyrrolo[2,3-b]pyridin-2-yl]-9-azabicyclo[3.3.1]non-2-en-9-yl}-1-(3-hydroxyazetidin-1-yl)ethanone The title compound was prepared as described in Example 1320B, substituting azetidin-3-ol hydrochloride for 2-(methylamino)ethanol. $^1$H NMR (500 MHz, DMSO-$d_6$) δ ppm 1.21-1.84 (m, 6 H) 2.09 (d, J=18.01 Hz, 1 H) 2.60-3.63 (m, 6 H) 3.74 (s, 3 H) 3.86-4.09 (m, 3 H) 4.26-4.52 (m, 2 H) 6.23 (s, 1 H) 6.44 (d, J=3.66 Hz, 1 H) 7.03 (d, J=4.88 Hz, 1 H) 7.11-7.38 (m, 3 H) 8.19 (d, J=4.88 Hz, 1 H) 11.79 (s, 1 H). MS (ESI$^+$) m/z 477 (M+H)$^+$.

EXAMPLE 1322

2-{3-[4-(5-fluoro-2-methoxyphenyl)-1H-pyrrolo[2,3-b]pyridin-2-yl]-9-azabicyclo[3.3.1]non-2-en-9-yl}-1-[(2S)-2-(hydroxymethyl)pyrrolidin-1-yl]ethanone The title compound was prepared as described in Example 1320B, substituting (S)-pyrrolidin-2-ylmethanol for 2-(methylamino)ethanol. $^1$H NMR (500 MHz, DMSO-$d_6$) δ ppm 1.27-2.31 (m, 11H) 2.57-3.66 (m, 8 H) 3.74 (s, 3 H) 3.83-4.87 (m, 3 H) 6.18-6.32 (m, 1 H) 6.36-6.48 (m, 1 H)

6.90-7.13 (m, 1 H) 7.14-7.33 (m, 3 H) 8.10-8.29 (m, 1 H) 11.81 (s, 1 H). MS (ESI+) m/z 505 (M+H)+.

EXAMPLE 1323

2-{3-[4-(5-fluoro-2-methoxyphenyl)-1H-pyrrolo[2,3-b]pyridin-2-yl]-9-azabicyclo[3.3.1]non-2-en-9-yl}-N-(3-hydroxycyclobutyl)-N-methylacetamide The title compound was prepared using the condition described in Example 1320B, substituting 3-(methylamino)cyclobutanol hydrochloride for 2-(methylamino)ethanol. $^1$H NMR (400 MHz, DMSO-$d_6$) δ ppm 1.32-1.86 (m, 6 H) 1.94-2.47 (m, 5 H) 2.62-3.48 (m, 9 H) 3.74 (s, 3 H) 4.13-4.45 (m, 1 H) 4.84-5.34 (m, 1 H) 6.24 (s, 1 H) 6.44 (d, J=4.27 Hz, 1 H) 7.03 (d, J=4.88 Hz, 1 H) 7.15-7.47 (m, 3 H) 8.19 (d, J=4.88 Hz, 1 H) 11.78 (s, 1 H). MS (ESI+) m/z 505 (M+H)+.

EXAMPLE 1324

{3-[4-(5-fluoro-2-methoxyphenyl)-1H-pyrrolo[2,3-b]pyridin-2-yl]-9-azabicyclo[3.3.1]non-2-en-9-yl}acetic acid The title compound was prepared as described in Example 1320A. $^1$H NMR (400 MHz, DMSO-$d_6$) δ ppm 1.33-1.71 (m, 4 H) 1.93-2.42 (m, 2 H) 2.73-3.51 (m, 4 H) 3.74 (s, 3 H) 3.87 (s, 2 H) 6.29 (s, 1 H) 6.41 (d, J=5.49 Hz, 1 H) 7.05 (d, J=4.88 Hz, 1 H) 7.15-7.32 (m, 3 H) 8.21 (d, J=4.88 Hz, 1 H) 11.87 (s, 1 H). MS (ESI+) m/z 422 (M+H)+.

EXAMPLE 1325

4-(2-methoxyphenyl)-2-[2-(methylsulfonyl)-1,2,3,3a,4,6a-hexahydrocyclopenta[c]pyrrol-5-yl]-1H-pyrrolo[2,3-b]pyridine

EXAMPLE 1325A tert-butyl 5-(4-(2-methoxyphenyl)-1H-pyrrolo[2,3-b]pyridin-2-yl)-3,3a,6,6a-tetrahydrocyclopenta[c]pyrrole-2(1H)-carboxylate The title compound was prepared as described in Example 87A, substituting Example 1272B for 4-bromo-1-(phenylsulfonyl)-1H-pyrrolo[2,3-b]pyridine and tert-butyl 5-(4,4,5,5-tetramethyl-1,3,2-dioxaborolan-2-yl)-3,3a,6,6a-tetrahydrocyclopenta[c]pyrrole-2(1H)-carboxylate for 5-fluoro-2-methoxyphenylboronic acid.

EXAMPLE 1325B 4-(2-methoxyphenyl)-2-(1,2,3,3a,4,6a-hexahydrocyclopenta[c]pyrrol-5-yl)-1H-pyrrolo[2,3-b]pyridine The title compound was prepared as described in Example 90A, substituting Example 1325A for Example 88B. MS (ESI+) m/z 332 (M+H)+.

EXAMPLE 1325C 4-(2-methoxyphenyl)-2-[2-(methylsulfonyl)-1,2,3,3a,4,6a-hexahydrocyclopenta[c]pyrrol-5-yl]-1H-pyrrolo[2,3-b]pyridine The title compound was prepared as described in Example 1318C, substituting Example 1325B for Example 1318B. $^1$H NMR (400 MHz, DMSO-$d_6$) δ 2.57-2.77 (m, 1H), 2.82-3.12 (m, 6H), 3.17 (dd, J=9.9, 2.8 Hz, 1H), 3.39-3.50 (m, 2H), 3.61 (tt, J=8.0, 2.5 Hz, 1H), 3.75 (s, 3H), 6.16 (d, J=2.0 Hz, 1H), 6.29 (q, J=1.9 Hz, 1H), 6.98-7.13 (m, 2H), 7.19 (d, J=8.2 Hz, 1H), 7.34-7.50 (m, 2H), 8.20 (d, J=4.9 Hz, 1H), 11.86 (d, J=2.3 Hz, 1H). MS (ESI+) m/z 410 (M+H)+.

EXAMPLE 1326

4-(5-fluoro-2-methoxyphenyl)-2-(piperazin-1-yl)-1H-pyrrolo[2,3-b]pyridine-3-carbonitrile

EXAMPLE 1326A 4-(5-fluoro-2-methoxyphenyl)-2-iodo-1H-pyrrolo[2,3-b]pyridine-3-carbonitrile To a solution of Example 248C (0.19 g, 0.369 mmol) in 3 mL tetrahydrofuran, 12M aqueous hydrogen chloride acid (0.30 mL, 3.6 mmol) was added. The mixture was heated at 80° C. for one hour. After cooling to room temperature, the suspension was filtered and washed with 0.5 mL tetrahydrofuran to afford the title compound as a hydrogen chloride salt. LCMS: 393.9 (M+H)+.

EXAMPLE 1326B 4-(5-fluoro-2-methoxyphenyl)-2-(piperazin-1-yl)-1H-pyrrolo[2,3-b]pyridine-3-carbonitrile To a solution of Example 1326A (0.110 g, 0.280 mmol) and tert-butyl piperazine-1-carboxylate (0.095 g, 0.510 mmol) in tetrahydrofuran (3 mL), N-ethyl-N-isopropylpropan-2-amine (0.15 mL, 0.859 mmol) was added. The mixture was heated at 160° C. for 60 minutes. After removing the solvent, dichloromethane (3 mL) and trifluoroacetic acid (2 mL, 26.0 mmol) were added to the residue. The mixture was stirred at room temperature for two hours. The solvent was removed under vacuum and the crude product was purified by reverse-phase HPLC on a Sunfire C8 column (30×100 mm, 5 μm particle size, flow rate 30 mL/minute) using a gradient of 30-80% acetonitrile in 0.1% aqueous trifluoroacetic acid to provide the title compound as the trifluoroacetic acid salt. $^1$H NMR (400 MHz, CD$_3$OD): δ 3.42 (t, J=5.19 Hz, 4 H) 3.78 (s, 3 H) 3.94 (t, J=5.19 Hz, 4 H) 7.01-7.07 (m, 3 H) 7.12-7.19 (m, 1 H) 8.09 (d, J=5.49 Hz, 1 H). MS (ESI+) m/z: 352.2 (M+H)+.

EXAMPLE 1327 tert-butyl (2-{4-[4-(5-fluoro-2-methoxyphenyl)-1H-pyrrolo[2,3-b]pyridin-2-yl]-3,6-dihydropyridin-1(2H)-yl}ethyl)carbamate To a mixture of Example 87D (200 mg, 0.505 mmol) and triethylamine (0.155 mL, 1.110 mmol), acetic acid (152 mg, 2.52 mmol) in dichloromethane (3 mL) and methanol (3 mL) was added tert-butyl(2-oxoethyl)carbamate (161 mg, 1.009 mmol) and Biotage MP-cyanoborohydride resin (2.17 mmol/g, 700 mg, 2.019 mmol). The reaction mixture was shaken on an orbital shaker for 3 days. The reaction mixture was transferred to a 50 mL round bottom flask, 2 equivalents of tert-butyl(2-oxoethyl)carbamate (161 mg, 1.009 mmol) were added, and the reaction mixture was stirred at 50° C. for 16 hours. The reaction mixture was cooled to room temperature and diluted with dichloromethane. The resin was filtered, rinsed with dichloromethane and methanol and the organics were concentrated under vacuum. The crude material was purified by flash chromatography; (Analogix280, 12 g silica column, 1% to 7% methanol/dichloromethane gradient over 30 minutes) to give the title compound. $^1$H NMR (500 MHz, DMSO-d$_6$) δ ppm 11.80 (s, 1 H) 8.19 (d, J=4.88 Hz, 1 H) 7.12-7.42 (m, 3 H) 7.03 (d, J=5.19 Hz, 1 H) 6.74 (s, 1 H) 6.48 (s, 1 H) 6.21 (s, 1 H) 3.74 (s, 3 H) 3.20 (s, 2 H) 3.13 (s, 2 H) 2.62-2.83 (m, 2 H) 1.30-1.48 (m, 9 H). MS (ESI): 467.0 (M+H)$^+$.

EXAMPLE 1329

4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid

EXAMPLE 1329A ethyl 4-(4-(5-fluoro-4-(5-fluoro-2-methoxyphenyl)-1H-pyrrolo[2,3-b]pyridin-2-yl)-5,6-dihydropyridin-1(2H)-yl)cyclohexanecarboxylate To a mixture of Example 231E (0.150 g, 0.362 mmol) and triethylamine (0.111 mL, 0.797 mmol) in dichloromethane (2 mL) and methanol (2 mL) was added acetic acid (0.104 mL, 1.810 mmol), ethyl 4-oxocyclohexanecarboxylate (0.115 mL, 0.724 mmol) and MP-cyanoborohydride (582 mg, 2.49 mmol/g). The reaction mixture was heated at 40° C. for 3 hours. The solid material was filtered and rinsed with dichloromethane and methanol. The filtrate was concentrated and the residue was partitioned between ethyl acetate and saturated aqueous sodium bicarbonate. The organic layer was washed with brine, dried over anhydrous sodium sulfate, filtered and concentrated until most solvent was evaporated. The solids that precipitated out over 3 days were filtered, washed with ether and vacuum oven-dried to provide the title compound. The filtrate was purified on a 4 g column using the ISCO Companion flash system eluting with CH$_2$Cl$_2$/methanol/NH$_4$OH (18:1:0.1 to 12:1:0.1) to provide additional title compound. MS (ESI$^+$) m/z 496.0 (M+H)$^+$.

EXAMPLE 1329B

4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid A mixture of Example 1329A (0.160 g, 0.323 mmol) and lithium hydroxide (0.015 g, 0.646 mmol) in tetrahydrofuran (4 mL), methanol (1.6 mL), and water (1.2 mL) was stirred overnight. The reaction mixture was concentrated. The residue was dissolved in 3 mL of water and treated with 2M HCl in ether (0.32 mL). The mixture was concentrated and purified via HPLC (see protocols in Example 217) to provide the title compound as a trifluoroacetic acid salt. The trifluoroacetic acid salt was dissolved in 3 mL of dichloromethane and treated with 0.5 mL of 2N HCl in ether. The suspension was diluted with ether, filtered, washed with ether, and vacuum-oven dried to provide the title compound as an HCl salt. $^1$H NMR (400 MHz, DMSO-d$_6$) δ ppm 1.29-1.70 (m, 4H), 1.99-2.27 (m, 5H), 2.70-3.00 (m, 2H), 3.09-3.33 (m, 2H), 3.54-3.64 (m, 1H), 3.73 (s, 3H), 3.90 (bs, 2H), 6.29 (dd, J=5.4, 2.0 Hz, 1H), 6.48-6.54 (m, 1H), 7.16-7.38 (m, 3H), 8.24 (d, J=2.5 Hz, 1H), 10.80 (dd, J=98.1, 34.9 Hz, 1H), 12.14 (s, 1H). MS (ESI$^+$) m/z 468.0 (M+H)$^+$.

EXAMPLE 1330

2-{4-[4-(5-fluoro-2-methoxyphenyl)-1H-pyrrolo[2,3-b]pyridin-2-yl]azepan-1-yl}-1-(3-hydroxyazetidin-1-yl) ethanone

EXAMPLE 1330A tert-butyl 2-(4-(4-(5-fluoro-2-methoxyphenyl)-1H-pyrrolo[2,3-b]pyridin-2-yl)azepan-1-yl)acetate The title compound was prepared according to the procedure described in Example 275, substituting Example 1276A for Example 236G. MS (ESI$^+$) m/z 454 (M+H)$^+$.

EXAMPLE 1330B 2-(4-(4-(5-fluoro-2-methoxyphenyl)-1H-pyrrolo[2,3-b]pyridin-2-yl)azepan-1-yl)acetic acid The title compound was prepared according to the procedure described in Example 226B, substituting Example 1330A for Example 226A. MS (ESI$^+$) m/z 398 (M+H)$^+$.

EXAMPLE 1330C 2-(4-(4-(5-fluoro-2-methoxyphenyl)-1H-pyrrolo[2,3-b]pyridin-2-yl)azepan-1-yl)-1-(3-hydroxyazetidin-1-yl) ethanone The title compound was prepared according to the procedure described in Example 238, substituting Example 1330B for Example 226B. $^1$H NMR (400 MHz, DMSO-d$_6$) δ 1.54-1.89 (m, 4H), 2.01 (dp, J=13.7, 4.0 Hz, 2H), 2.59-2.83 (m, 4H), 3.01 (tt, J=9.5, 4.1 Hz, 1H), 3.10-3.17 (m, 2H), 3.58 (dd, J=10.1, 4.3 Hz, 2H), 3.73 (s, 3H), 3.98 (ddd, J=40.7, 9.6, 5.7 Hz, 2H), 4.36 (td, J=8.1, 6.5, 4.2 Hz, 1H), 4.44 (tq, J=7.2, 3.9 Hz, 1H), 5.94 (s, 1H), 6.99 (d, J=4.9 Hz, 1H), 7.10-7.51 (m, 3H), 8.12 (d, J=5.0 Hz, 1H), 11.54 (s, 1H). MS (ESI$^+$) m/z 453 (M+H)$^+$.

EXAMPLE 1332

2-{4-[4-(5-fluoro-2-methoxyphenyl)-1H-pyrrolo[2,3-b]pyridin-2-yl]-3,6-dihydropyridin-1(2H)-yl}ethanamine To a solution of Example 1327 (170 mg, 0.364 mmol) in 5 ml dichloromethane was added excess trifluoroacetic acid. The reaction was held at room temperature for 2 hours at which time the solvent was removed and the residue dissolved in 3 mL methanol. The solution was treated with excess 2M HCl/ether and then further diluted with 50 mL ether. The resulting solid was filtered and dried under high-vacuum to give the title compound as the HCL salt. $^1$H NMR (400 MHz, DMSO-d$_6$) δ ppm 12.78 (s, 1 H) 11.50 (s, 1 H) 8.45-8.73 (m, 3 H) 8.32 (d, J=5.49 Hz, 1 H) 7.08-7.51 (m, 4 H) 6.64 (s, 1 H) 6.53 (s, 1 H) 3.86-4.25 (m, 2 H) 3.76 (s, 4 H) 3.25-3.57 (m, 2 H) 2.74-3.07 (m, 2 H). MS (ESI): 367.0 (M+H)$^+$.

EXAMPLE 1333

N-(2-{4-[4-(5-fluoro-2-methoxyphenyl)-1H-pyrrolo[2,3-b]pyridin-2-yl]-3,6-dihydropyridin-1(2H)-yl}ethyl)methanesulfonamide To a solution of Example 1332 (75 mg, 0.171 mmol) in 3 mL N,N-dimethylformamide was added triethylamine (0.095 mL, 0.683 mmol) followed by methanesulfonyl chloride (0.020 mL, 0.256 mmol). The reaction mixture was stirred at room temperature for 12 hours. The reaction mixture was diluted with ethyl acetate and washed with sodium bicarbonate, water and brine. The resulting organic layer was dried over magnesium sulfate, filtered and concentrated. The crude material was purified by flash chromatography; (Analogix 280; 12 g silica column, 0% to 7% methanol/dichloromethane gradient over 30 minutes) to give the titled compound. $^1$H NMR (400 MHz, DMSO-$d_6$) δ ppm 11.77 (d, J=1.53 Hz, 1 H) 8.19 (d, J=5.19 Hz, 1 H) 7.13-7.32 (m, 3 H) 7.02 (d, J=4.88 Hz, 1 H) 6.90 (t, J=5.80 Hz, 1 H) 6.49 (s, 1 H) 6.20 (d, J=2.14 Hz, 1 H) 3.67-3.78 (m, 3 H) 3.04-3.22 (m, 3 H) 2.93 (s, 3 H) 2.65 (t, J=5.19 Hz, 2 H) 2.42-2.59 (m, 5 H). MS (ESI): 445.0 (M+H)$^+$.

EXAMPLE 1334

N-(2-{4-[4-(5-fluoro-2-methoxyphenyl)-1H-pyrrolo[2,3-b]pyridin-2-yl]-3,6-dihydropyridin-1(2H)-yl}ethyl)acetamide

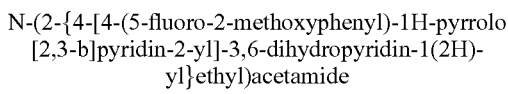

The title compound was prepared essentially as described in Example 1333, substituting methanesulfonyl chloride with acetic anhydride. $^1$H NMR (400 MHz, DMSO-$d_6$) δ ppm 11.77 (s, 1 H) 8.19 (d, J=5.19 Hz, 1 H) 7.78 (t, J=5.34 Hz, 1 H) 7.12-7.32 (m, 3 H) 7.02 (d, J=4.88 Hz, 1 H) 6.48 (s, 1 H) 6.19 (d, J=1.83 Hz, 1 H) 3.74 (s, 3 H) 3.17-3.26 (m, 2 H) 3.14 (q, J=2.44 Hz, 2 H) 2.62 (t, J=5.65 Hz, 2 H) 2.38-2.55 (m, 4 H) 1.80 (s, 3 H). MS (ESI): 409.0 (M+H)$^+$.

EXAMPLE 1335

2-{4-[4-(5-fluoro-2-methoxyphenyl)-1H-pyrrolo[2,3-b]pyridin-2-yl]-3,6-dihydropyridin-1(2H)-yl}-N,N-dimethylethanesulfonamide

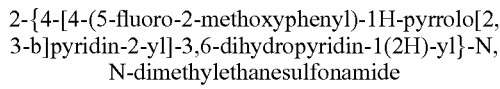

To a suspension of Example 87D (200 mg, 0.505 mmol) in N,N-dimethylformamide (5 mL) was added triethylamine (0.21 mL, 1.514 mmol) and N,N-dimethylethenesulfonamide (82 mg, 0.606 mmol). The reaction mixture was heated at 60° C. for 3 days. After cooling, the mixture was partitioned between ethyl acetate and brine. The organic phase was washed with brine, and concentrated. The residue was separated by flash chromatography (10-20% methanol in 2:1 ethyl acetate/heptane) to provide the title compound. $^1$H NMR (400 MHz, DMSO-$d_6$): δ2.46-2.50 (m, 2 H), 2.67 (t, J=5.65 Hz, 2 H), 2.77 (s, 6 H), 2.78-2.83 (m, 2 H), 3.17-3.20 (m, 2 H), 3.26-3.31 (m, 2 H), 3.74 (s, 3 H), 6.20 (d, J=1.53 Hz, 1 H), 6.49 (s, 1 H), 7.02 (d, J=4.88 Hz, 1 H), 7.17-7.29 (m, 3 H), 8.19 (d, J=4.88 Hz, 1 H), 11.78 (s, 1 H); MS (ESI) m/z 459 (M+H)$^+$, 457 (M−1)$^−$.

EXAMPLE 1336

4-(5-fluoro-2-methoxyphenyl)-2-[4-(methylsulfonyl)piperazin-1-yl]-3-nitro-1H-pyrrolo[2,3-b]pyridine

EXAMPLE 1336A 4-bromo-2-(4-(methylsulfonyl)piperazin-1-yl)-3-nitro-1H-pyrrolo[2,3-b]pyridine

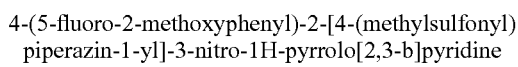

To a suspension of Example 1285A (0.091 g, 0.211 mmol) and 1-(methylsulfonyl)piperazine hydrochloride (0.057 g, 0.284 mmol) in 1,4-dioxane (1 mL), N-ethyl-N-isopropyl-propan-2-amine (0.2 mL, 1.145 mmol) was added. The mixture was stirred for 72 hours at room temperature. The solvent was removed and the product was purified by flash chromatography on silica gel (AnaLogix IntelliFlash) eluting with a gradient of 0-50% ethyl acetate in heptanes to afford the title compound. MS (ESI$^+$) m/z: 40.3.8 (M+H)$^+$.

EXAMPLE 1336B 4-(5-fluoro-2-methoxyphenyl)-2-[4-(methylsulfonyl)piperazin-1-yl]-3-nitro-1H-pyrrolo[2,3-b]pyridine

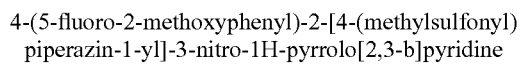

The title compound was prepared using the procedure described in Example 301A, using Example 1336A in place of Example 236C. $^1$H NMR (400 MHz, DMSO-$d_6$): δ 2.95 (s, 3 H) 3.32-3.38 (m, 4 H) 3.57 (s, 3 H) 3.59-3.80 (m, 4 H) 6.95-7.02 (m, 1 H) 7.10-7.22 (m, 3 H) 8.21 (s, 1 H). MS (ESI$^+$) m/z: 449.9 (M+H)$^+$.

EXAMPLE 1337

4-(5-fluoro-2-methoxyphenyl)-2-[4-(methylsulfonyl)piperazin-1-yl]-1H-pyrrolo[2,3-b]pyridine-3-carbonitrile

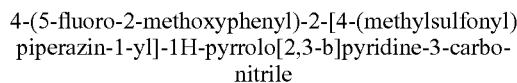

To a solution of Example 1326A (0.085 g, 0.216 mmol) and 1-(methylsulfonyl)piperazine hydrochloride (0.094 g, 0.468 mmol) in 3 mL N,N-dimethylacetamide, N-ethyl-N-isopropylpropan-2-amine (0.3 mL, 1.718 mmol) was added. The mixture was heated at 160° C. for 60 minutes under microwave using a Biotage Initiator (model 355302). The product was purified by reverse-phase HPLC on a Sunfire C8 column (30×100 mm, 5 μm particle size, flow rate 30 mL/minute) using a gradient of 30-100% acetonitrile in 0.1% aqueous trifluoroacetic acid to provide the title compound as the trifluoroacetic salt. $^1$H NMR (400 MHz, CD$_3$OD): δ 2.93 (s, 3 H) 3.25-3.31 (m, 4 H) 3.73 (s, 3 H) 3.73-3.78 (m, 4 H) 6.94 (d, J=5.19 Hz, 1 H) 7.05-7.12 (m, 2 H) 7.20-7.27 (m, 1 H) 8.06 (d, J=4.88 Hz, 1 H). MS (ESI+) m/z: 430.1 (M+H)$^+$.

EXAMPLE 1338

2-{3-[4-(5-fluoro-2-methoxyphenyl)-1H-pyrrolo[2,3-b]pyridin-2-yl]-2,5-dihydro-1H-pyrrol-1-yl}-1-(-hydroxyazetidin-1-yl)ethanone

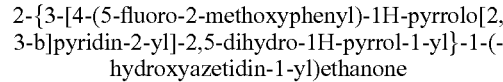

The title compound was prepared as described in Example 238, substituting Example 759 for Example 226B. $^1$H NMR (400 MHz, DMSO-$d_6$) δ 3.33 (br s, 2H), 3.58 (m, 1H), 3.71 (m, 2H), 3.73 (s, 3H), 3.86 (m, 3H), 4.05 (m, 1H), 4.32 (t, 1H), 4.45 (m, 1H), 5.68 (br d, 1H), 6.11 (d, 1H), 6.45 (br s, 1H), 7.04 (d, 1H), 7.25 (m, 3H), 8.21 (d, 1H), 11.96 (br s, 1H). MS (ESI) m/e 423.1 (M+H)$^+$.

EXAMPLE 1339

(4-{4-[4-(5-fluoro-2-methoxyphenyl)-1H-pyrrolo[2,3-b]pyridin-2-yl]cyclohex-3-en-1-yl}piperidin-1-yl)acetic acid

EXAMPLE 1339A 8-(pyridin-4-yl)-1,4-dioxaspiro[4.5]decan-8-ol

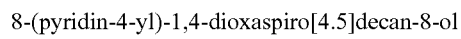

Butyllithium (102 mL, 256 mmol, 2.5 M) in tetrahydrofuran (200 ml) was cooled to −78° C. under nitrogen. Next, a solution of 4-bromopyridine (25.3 g, 160 mmol) in tetrahydrofuran (100 mL) was slowly added and after stirring for 1.5 hours a solution of 1,4-dioxaspiro[4.5]decan-8-one (20 g, 128 mmol) in tetrahydrofuran (100 mL) was added and stirring was carried out at −78° C. for 2 hours. The reaction mixture was then poured into 800 mL of water and the aqueous layer was extracted with three portions of ethyl acetate (500 mL each). The organic extracts were combined then washed with saturated aqueous brine (800 mL), dried over anhydrous magnesium sulfate, filtered and concentrated. The crude residue was purified by silica gel flash chromatography using ethyl acetate/petroleum ether (1/4) as an eluent to afford the title compound. $^1$H-NMR (400 MHz, CDCl$_3$) δ ppm 8.49 (d, J=4.8 Hz, 2 H), 7.45 (d, J=4.8 Hz, 2 H), 4.03-3.96 (m, 4 H), 3.09 (brs, 1 H), 2.17-2.07 (m, 4 H), 1.81-1.67 (m, 4 H). MS (ESI$^+$) m/z 236 (M+H)$^+$.

EXAMPLE 1339B 4-(1,4-dioxaspiro[4.5]dec-7-en-8-yl)pyridine

Thionyl chloride (9.31 ml, 128 mmol) was added dropwise at −15° C. to a solution of Example 1339A (10 g, 42.5 mmol) in 200 mL of dichloromethane (200 mL) with 80 mL of pyridine. After stirring for 15 minutes, the reaction solution was poured carefully onto ice then neutralized with aqueous saturated sodium bicarbonate and extracted with three 200 mL portions of dichloromethane. The organic layers were combined and washed with water (600 mL), saturated aqueous sodium chloride (500 mL), dried over anhydrous magnesium sulfate, filtered and concentrated. The crude residue was purified by silica gel flash chromatography using ethyl acetate/petroleum ether (1/6) as an eluent to afford the title compound. $^1$H-NMR (400 MHz, methanol-d$_4$) δ ppm 8.45 (d, J=4.4 Hz, 2H), 7.21 (d, J=3.2 Hz, 2H), 6.17 (t, J=4 Hz, 1H), 3.95 (s, 4H), 2.59-2.56 (m, 2H), 2.43 (d, J=1.6 Hz, 2H), 1.86 (t, J=6.4 Hz, 2H). MS (ESI$^+$) m/z 218 (M+H)$^+$.

EXAMPLE 1339C 4-(1,4-dioxaspiro[4.5]decan-8-yl)piperidine

To a solution of Example 1339B (5 g, 23.01 mmol) in methanol (100 ml) with acetic acid (50 mL), was added platinum(IV) oxide (0.78 g, 3.45 mmol). The reaction mixture was hydrogenated with approximately 6 Mpa of hydrogen for 54 hours. The reaction mixture was filtered through a one-quarter inch thin celite pad and the filter cake was washed with 20 mL of methanol. The filtrate was neutralized by addition of 1M aqueous sodium bicarbonate solution and was concentrated. The residue obtained was purified by silica gel flash chromatography using ethyl acetate/petroleum ether (7/1) as the eluent to afford the title compound. MS (ESI$^+$) m/z 226 (M+H)$^+$.

EXAMPLE 1339D tert-butyl 4-(4-oxocyclohexyl)piperidine-1-carboxylate

To a solution of Example 1339C (4 g, 17.75 mmol) in 120 mL of tetrahydrofuran was added 20 mL of a 1 M aqueous solution of sodium bicarbonate followed by di-tert-butyl dicarbonate (4.95 ml, 21.30 mmol). The resulting mixture was stirred at room temperature for 6 hours then concentrated. Next, water (200 mL) was added and the mixture was extracted with three 150 mL portions of ethyl acetate. The organic layers were combined then washed with saturated aqueous brine (200 mL), dried over anhydrous magnesium sulfate, filtered and concentrated. The crude residue was purified by silica gel flash chromatography using ethyl acetate/methanol (6/1) as an eluent to afford the title compound. $^1$H-NMR (400 MHz, CDCl3) δ ppm (4.27 g, 15.17 mmol, 85% yield). 4.16 (d, J=13.2 Hz, 2H), 2.65 (t, J=13.2 Hz, 2H), 2.42-2.27 (m, 4H), 2.43 (d, J=6 Hz, 2H), 1.56 (s, 9H), 1.69-1.54 (m, 4H), 1.51-1.32 (m, 4H). MS (ESI$^+$) m/z 226 226 (M-tBu+H).

EXAMPLE 1339E tert-butyl 4-(4-(trifluoromethylsulfonyloxy)cyclohex-3-enyl)piperidine-1-carboxylate The title compound was prepared as described in Example 772A using Example 1339D in place of (R)-1-tert-butyl 2-methyl 4-oxopyrrolidine-1,2-dicarboxylate. MS (ESI$^+$) m/z 414.1 (M+H)$^+$.

EXAMPLE 1339F tert-butyl 4-(4-(4-(5-fluoro-2-methoxyphenyl)-1H-pyrrolo[2,3-b]pyridin-2-yl)cyclohex-3-enyl)piperidine-1-carboxylate The title compound was prepared as described in Example 772B using Example 1339E in place of Example 772A and using Example 219A in place of Example 87B. MS (ESI$^+$) m/z 506.1 (M+H)$^+$.

EXAMPLE 1339G 4-(5-fluoro-2-methoxyphenyl)-2-(4-(piperidin-4-yl)cyclohex-1-enyl)-1H-pyrrolo[2,3-b]pyridine The title compound was prepared as described in Example 1018B using Example 1339F in place of Example 1018A. MS (ESI$^+$) m/z 406.2 (M+H)$^+$.

EXAMPLE 1339H tert-butyl 2-(4-(4-(4-(5-fluoro-2-methoxyphenyl)-1H-pyrrolo[2,3-b]pyridin-2-yl)cyclohex-3-enyl)piperidin-1-yl)acetate The title compound was prepared as described in Example 1297A using Example 1339G in place of Example 1018B. MS (ESI$^+$) m/z 520.0 (M+H)$^+$.

EXAMPLE 1339I (4-{4-[4-(5-fluoro-2-methoxyphenyl)-1H-pyrrolo[2,3-b]pyridin-2-yl]cyclohex-3-en-1-yl}piperidin-1-yl) acetic acid The title compound was prepared as described in Example 1297B using Example 1339H in place of Example 1297A. $^1$H NMR (400 MHz, DMSO-d$_6$) δ ppm 1.19-1.58 (m, 5H), 1.69-2.04 (m, 4H), 2.20-2.41 (m, 2H), 2.51-2.58 (m, 1H), 2.63 (t, J=12.2 Hz, 2H), 3.21-3.38 (m, 4H), 3.73 (s, 3H), 6.16 (d, J=2.0 Hz, 1H), 6.47-6.60 (m, 1H), 7.01 (d, J=4.9 Hz, 1H), 7.14-7.33 (m, 3H), 8.17 (d, J=5.0 Hz, 1H), 11.57-11.85 (m, 1H). MS (ESI$^+$) m/z 464.0 (M+H)$^+$.

EXAMPLE 1340

4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine

EXAMPLE 1340A 4-(5-fluoro-2-methoxyphenyl)-2-[(2S)-2-methyl-1,2,3,6-tetrahydropyridin-4-yl]-1H-pyrrolo[2,3-b]pyridine-4-(5-fluoro-2-methoxyphenyl)-2-[(6S)-6-methyl-1,2,3,6-tetrahydropyridin-4-yl]-1H-pyrrolo[2,3-b]pyridine The mixture of title compounds was isolated from the chromatography described in Example 258F. MS (ESI) m/e 338.1 (M+1)$^+$.

EXAMPLE 1340B 4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine The mixture of title compounds was prepared as described in Example 119, substituting Example 1340A for Example 87D. (Major regioisomer) $^1$H NMR (500 MHz, DMSO-d$_6$) δ 1.17 (d, 3H), 2.43 (br d, 1H), 2.74 (m, 1H), 2.96 (s, 3H), 3.76 (s, 3H), 3.87 (br d, 1H), 4.15 (m, 1H), 4.27 (m, 1H), 6.40 (br s, 1H), 6.63 (m, 1H), 7.28 (m, 4H), 8.29 (br d, 1H), 12.53 (br s, 1H). (ESI) m/e 416.2 (M+H)$^+$. (Minor regioisomer) $^1$H NMR (500 MHz, DMSO-d$_6$) δ 1.33 (d, 3H), 2.43 (br d, 1H), 2.74 (m, 1H), 2.94 (s, 3H), 3.76 (s, 3H), 3.88 (m, 1H), 4.15 (m, 1H), 4.28 (m, 1H), 6.43 (br s, 1H), 6.61 (m, 1H), 7.29 (m, 4H), 8.29 (d, 1H), 12.49 (br s, 1H).

EXAMPLE 1341

2-{3-[4-(5-fluoro-2-methoxyphenyl)-1H-pyrrolo[2,3-b]pyridin-2-yl]-2,5-dihydro-1H-pyrrol-1-yl}-N-(2-hydroxyethyl)-N-methylacetamide The title compound was prepared as described in Example 238, substituting Example 759 for Example 226B and 2-(aminomethyl)ethanol for azetidin-3-ol hydrochloride. $^1$H NMR (400 MHz, DMSO-d$_6$) δ 3.33 (br s, 3H), 3.40 (m, 1H), 3.52 (m, 5H), 3.73 (br s, 5H), 3.87 (m, 2H), 6.10 (br s, 1H), 6.45 (m, 1H), 7.04 (d, 1H), 7.24 (m, 3H), 8.21 (d, 1H), 11.96 (br s, 1H). MS (ESI) m/e 425.2 (M+H)$^+$.

EXAMPLE 1342

2-{3-[4-(5-fluoro-2-methoxyphenyl)-1H-pyrrolo[2,3-b]pyridin-2-yl]-2,5-dihydro-1H-pyrrol-1-yl}-N,N-dimethylacetamide The title compound was prepared as described in Example 238, substituting Example 759 for Example 226B and dimethylamine hydrochloride for azetidin-3-ol hydrochloride. $^1$H NMR (400 MHz, DMSO-d$_6$) δ 2.82 (s, 3H), 2.98 (s, 3H), 3.53 (br s, 2H), 3.73 (br s, 5H), 3.86 (m, 2H), 6.10 (br s, 1H), 6.46 (m, 1H), 7.04 (d, 1H), 7.24 (m, 3H), 8.21 (m, 1H), 11.96 (br s, 1H). MS (ESI) m/e 395.1 (M+H)$^+$.

EXAMPLE 1343

2-{3-[4-(5-fluoro-2-methoxyphenyl)-1H-pyrrolo[2,3-b]pyridin-2-yl]-2,5-dihydro-1H-pyrrol-1-yl}-1-[(2S)-2-(hydroxymethyl)pyrrolidin-1-yl]ethanone The title compound was prepared as described in Example 238, substituting Example 759 for Example 226B and (S)-pyrrolidin-2-ylmethanol for azetidin-3-ol hydrochloride. $^1$H NMR (400 MHz, DMSO-d$_6$) δ 1.82 (m, 4H), 3.25 (m, 2H), 3.50 (m, 4H), 3.73 (br s, 5H), 3.94 (m, 3H), 4.72 (br t, 1H), 6.10 (m, 1H), 6.46 (m, 1H), 7.04 (d, 1H), 7.23 (m, 3H), 8.21 (d, 1H), 11.95 (br s, 1H). MS (ESI) m/e 451.2 (M+H)$^+$.

EXAMPLE 1344

2-(4-{4-[4-(5-fluoro-2-methoxyphenyl)-1H-pyrrolo[2,3-b]pyridin-2-yl]cyclohex-3-en-1-yl}piperidin-1-yl)-N,N-dimethylacetamide The title compound was prepared as described in Example 899B using Example 1339I in place of Example 899A. $^1$H NMR (400 MHz, DMSO-d$_6$) δ ppm 1.19-1.50 (m, 3H), 1.49-1.68 (m, 2H), 1.84-2.05 (m, 4H), 2.23-2.41 (m, 2H), 2.52-2.60 (m, 1H), 2.86-2.96 (m, 7H), 3.19-3.31 (m, 1H), 3.51 (d, J=11.8 Hz, 2H), 3.74 (s, 3H), 4.21 (d, J=4.5 Hz, 2H), 6.22 (d, J=2.0 Hz, 1H), 6.48-6.62 (m, 1H), 7.08 (d, J=5.1 Hz, 1H), 7.17-7.35 (m, 3H), 8.21 (d, J=5.1 Hz, 1H), 9.33 (s, 1H), 11.67-12.09 (m, 1H). MS (ESI$^+$) m/z 491.1 (M+H)$^+$.

EXAMPLE 1345

(4-{(1S)-4-[4-(5-fluoro-2-methoxyphenyl)-1H-pyrrolo[2,3-b]pyridin-2-yl]cyclohex-3-en-1-yl}piperidin-1-yl)acetic acid

EXAMPLE 1345A tert-butyl 2-(4-((1S)-4-(4-(5-fluoro-2-methoxyphenyl)-1H-pyrrolo[2,3-b]pyridin-2-yl)cyclohex-3-enyl)piperidin-1-yl)acetate Preparative SFC chiral separation of Example 1339H was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase comprised of supercritical carbon dioxide supplied by a Dewar of anhydrous non-certified carbon dioxide pressurized to 350 psi with a modifier of methanol at a flow rate of 70 g/minute. UV detection was set to collect at a wavelength of 220 nm, the column was at ambient temperature, and the backpressure regulator was set to maintain 100 bar. The sample was dissolved in methanol at a concentration of 8 mg/mL. The sample was loaded into the modifier stream in 1 mL (100 mg) injections. The mobile phase was held isocraticly at 14.5% 2-propanol:carbon dioxide and the 2-propanol contained 0.1% of ammonium hydroxide. Fraction collection was time triggered. The instrument was fitted with a CHIRALPAK OJ-H column (21 mm i.d.×250 mm length with 5 μm particles). The chiral separation afforded the title com-

EXAMPLE 1345B (4-{(1S)-4-[4-(5-fluoro-2-methoxyphenyl)-1H-pyrrolo[2,3-b]pyridin-2-yl]cyclohex-3-en-1-yl}piperidin-1-yl)acetic acid The title compound was prepared as described in Example 1297B using Example 1345A in place of Example 1297A. $^1$H NMR (400 MHz, DMSO-$d_6$) δ ppm 1.23-1.51 (m, 3H), 1.51-1.74 (m, 2H), 1.79-2.11 (m, 4H), 2.25-2.43 (m, 2H), 2.52-2.63 (m, 1H), 2.94-3.13 (m, 2H), 3.50-3.62 (m, 2H), 3.76 (s, 3H), 4.09 (s, 2H), 6.32 (d, J=2.0 Hz, 1H), 6.61-6.74 (m, 1H), 7.19-7.41 (m, 4H), 8.25 (d, J=5.4 Hz, 1H), 10.03 (s, 1H), 12.45 (s, 1H). MS (ESI$^+$) m/z 464.0 (M+H)$^+$.

EXAMPLE 1346

(4-{(1R)-4-[4-(5-fluoro-2-methoxyphenyl)-1H-pyrrolo[2,3-b]pyridin-2-yl]cyclohex-3-en-1-yl}piperidin-1-yl)acetic acid

EXAMPLE 1346A tert-butyl 2-(4-((1R)-4-(4-(5-fluoro-2-methoxyphenyl)-1H-pyrrolo[2,3-b]pyridin-2-yl)cyclohex-3-enyl)piperidin-1-yl)acetate The title compound was prepared in Example 1345A, and corresponds to the slower eluting enantiomer under the SFC conditions. LC-MS: 520.0 (M+H)$^+$.

EXAMPLE 1346B (4-{(1R)-4-[4-(5-fluoro-2-methoxyphenyl)-1H-pyrrolo[2,3-b]pyridin-2-yl]cyclohex-3-en-1-yl}piperidin-1-yl)acetic acid The title compound was prepared as described in Example 1297B using Example 1346A in place of Example 1297A. $^1$H NMR (400 MHz, DMSO-$d_6$) δ ppm 1.23-1.51 (m, 3H), 1.51-1.74 (m, 2H), 1.79-2.11 (m, 4H), 2.25-2.43 (m, 2H), 2.52-2.63 (m, 1H), 2.94-3.13 (m, 2H), 3.50-3.62 (m, 2H), 3.76 (s, 3H), 4.09 (s, 2H), 6.32 (d, J=2.0 Hz, 1H), 6.61-6.74 (m, 1H), 7.19-7.41 (m, 4H), 8.25 (d, J=5.4 Hz, 1H), 10.03 (s, 1H), 12.45 (s, 1H). MS (ESI$^+$) m/z 464.0 (M+H)$^+$.

EXAMPLE 1347 methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate

EXAMPLE 1347A methyl 2-(4-oxocyclohexylidene)acetate

Cyclohexane-1,4-dione (134 g, 1196 mmol) and methyl 2-(triphenylphosphoranylidene)acetate (200 g, 598 mmol) were combined in toluene (1994 ml) and heated overnight at 100° C. The solvent was evaporated. The residue was slurried in 1:1 ether:heptane and filtered. The filtrate was concentrated and taken up in a minimal amount of 20% ethyl acetate in heptanes and passed through a large plug of silica gel to provide the title compound after concentration.

EXAMPLE 1347B methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate Example 87D (500 mg, 1.26 mmol) in 12 mL 1:1 dichloromethane:methanol was treated with triethylamine (0.45 mL, 3.23 mmol) and the mixture was sonicated for 5 minutes. Example 1347A (276 mg, 1.64 mmol) and acetic acid (0.45 mL, 7.86 mmol) were added and the mixture was stirred for 15 minutes. The MP-cyanoborohydride (2.1 g, 2.44 mmol/g) was added and the reaction was stirred under nitrogen for 40 hours. The reaction mixture was filtered and concentrated. The residue was partitioned between dichloromethane and saturated aqueous sodium bicarbonate solution. The aqueous layer was extracted with dichloromethane. The combined extracts were rinsed with brine, dried over sodium sulfate, filtered and concentrated. The crude material was purified by flash chromatography (4% methanol/dichloromethane) to yield the title compound. $^1$H NMR (500 MHz, DMSO-$d_6$) δ 11.75 (s, 1H), 8.18 (d, J=5.0 Hz, 1H), 7.32-7.14 (m, 3H), 7.02 (d, J=5.0 Hz, 1H), 6.49 (s, 1H), 6.17 (s, 1H), 5.66 (s, 1H), 3.73 (s, 3H), 3.60 (s, 3H), 3.59-3.56 (m, 1H), 3.25 (d, J=2.6 Hz, 2H), 2.69 (t, J=5.3 Hz, 2H), 2.66-2.56 (m, 1H), 2.47-2.33 (m, 2H), 2.24-2.16 (m, 1H), 2.14-2.03 (m, 1H), 1.98-1.88 (m, 2H), 1.54-1.34 (m, 2H). MS (DCI) m/e 476 (M+H)$^+$.

EXAMPLE 1348

(4-{(1S)-4-[4-(5-fluoro-2-methoxyphenyl)-1H-pyrrolo[2,3-b]pyridin-2-yl]cyclohex-3-en-1-yl}piperazin-1-yl)acetic acid

EXAMPLE 1348A tert-butyl 2-(4-((1S)-4-(4-(5-fluoro-2-methoxyphenyl)-1H-pyrrolo[2,3-b]pyridin-2-yl)cyclohex-3-enyl)piperazin--yl)acetate Preparative SFC chiral separation of Example 1297A was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase was comprised of supercritical carbon dioxide supplied by a Dewar of anhydrous non-certified carbon dioxide pressurized to 350 psi with a modifier of methanol at a flow rate of 70 g/minute. UV detection was set to collect at a wavelength of 220 nm, the column was at ambient temperature, and the back pressure regulator was set to maintain 100 bar. The sample was dissolved in methanol at a concentration of 8 mg/mL. The sample was loaded into the modifier stream in 1 mL (100 mg) injections. The mobile phase was held isocraticly at 30% 2-propanol:carbon dioxide and the 2-propanol contained 0.1% of ammonium hydroxide. Fraction collection was time triggered. The instrument was fitted with a CHIRALPAK IA column (21 mm i.d.×250 mm length with 5 μm particles). The chiral separation afforded the title compound as the faster eluting enantiomer and Example 1346A (see below, slower eluting enantiomer). LC-MS: 521.0 (M+H)$^+$.

EXAMPLE 1348B (4-{(1S)-4-[4-(5-fluoro-2-methoxyphenyl)-1H-pyrrolo[2,3-b]pyridin-2-yl]cyclohex-3-en-1-yl}piperazin-1-yl)acetic acid The title compound was prepared as described in Example 1297B using Example 1348A in place of Example 1297A. $^1$H NMR (500 MHz, DMSO-d$_6$) δ ppm 1.61-1.78 (m, 1H), 2.22-2.34 (m, 1H), 2.39-2.51 (m, 2H), 2.62-2.80 (m, 2H), 2.83-3.64 (m, 11H), 3.74 (s, 3H), 6.29 (d, J=2.1 Hz, 1H), 6.44-6.53 (m, 1H), 7.08 (d, J=5.0 Hz, 1H), 7.18-7.34 (m, 3H), 8.23 (d, J=5.0 Hz, 1H), 11.96 (s, 1H). MS (ESI$^+$) m/z 465.2 (M+H)$^+$.

EXAMPLE 1349

(4-{(1R)-4-[4-(5-fluoro-2-methoxyphenyl)-1H-pyrrolo[2,3-b]pyridin-2-yl]cyclohex-3-en-1-yl}piperazin-1-yl)acetic acid

EXAMPLE 1349A tert-butyl 2-(4-((1R)-4-(4-(5-fluoro-2-methoxyphenyl)-1H-pyrrolo[2,3-b]pyridin-2-yl)cyclohex-3-enyl)piperazin-1-yl)acetate The title compound was prepared in Example 1348A, and corresponds to the slower eluting enantiomer under the SFC conditions. LC-MS: 521.0 (M+H)$^+$.

EXAMPLE 1349B (4-{(1R)-4-[4-(5-fluoro-2-methoxyphenyl)-1H-pyrrolo[2,3-b]pyridin-2-yl]cyclohex-3-en-1-yl}piperazin-1-yl)acetic acid The title compound was prepared as described in Example 1297B using Example 1349A in place of Example 1297A. $^1$H NMR (500 MHz, DMSO-d$_6$) δ ppm 1.62-1.79 (m, 1H), 2.20-2.33 (m, 1H), 2.39-2.49 (m, 2H), 2.61-2.79 (m, 2H), 2.79-3.64 (m, 11H), 3.74 (s, 3H), 6.28 (d, J=2.1 Hz, 1H), 6.45-6.54 (m, 1H), 7.08 (d, J=5.0 Hz, 1H), 7.18-7.34 (m, 3H), 8.23 (d, J=5.0 Hz, 1H), 11.94 (s, 1H). MS (ESI$^+$) m/z 465.2 (M+H)$^+$.

EXAMPLE 1350

(4-{4-[4-(5-fluoro-2-methoxyphenyl)-1H-pyrrolo[2,3-b]pyridin-2-yl]-3,6-dihydropyridin-1(2H)-yl}cyclohexylidene)acetic acid Example 1347 was suspended in 4.5 mL 1:1:1 tetrahydrofuran:methanol:water and lithium hydroxide monohydrate (45 mg, 1.072 mmol) was added. The reaction was heated at 60° C. for 6 hours followed by 12 hours at room temperature. The reaction mixture was concentrated. The residue was suspended in water and made slightly acidic with 3M HCl (aqueous). The resulting precipitate was collected and rinsed with water. The solids were suspended in acetonitrile and stirred to give a solid which was collected and dried with magnesium sulfate to yield the title compound as the hydrochloride salt. $^1$H NMR (400 MHz, DMSO-d$_6$) δ 12.00 (s, 1H), 10.60 (s, 1H), 8.25 (d, J=5.0 Hz, 1H), 7.39-7.15 (m, 3H), 7.07 (d, J=4.9 Hz, 1H), 6.50 (s, 1H), 6.37 (s, 1H), 5.67 (s, 1H), 3.95 (s, 2H), 3.90-3.83 (m, 1H), 3.74 (s, 3H), 3.70-3.63 (m, 1H), 3.58-3.45 (m, 1H), 3.32-3.19 (m, 1H), 2.95-2.78 (m, 2H), 2.47-2.18 (m, 4H), 2.01-1.89 (m, 1H), 1.79-1.49 (m, 2H). MS (DCI) m/e 462 (M+H)$^+$.

EXAMPLE 1351 cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid

EXAMPLE 1351A ethyl cis-4-(4-(4-(5-fluoro-2-methoxyphenyl)-1H-pyrrolo[2,3-b]pyridin-2-yl)-5,6-dihydropyridin-1(2H)-yl)cyclohexanecarboxylate A suspension of Example 87D (1.5 g, 3.79 mmol) and triethylamine (1.319 ml, 9.46 mmol) in dichloromethane (25 ml) and methanol (25 ml) was treated with ethyl 4-oxocyclohexanecarboxylate (0.838 g, 4.92 mmol) and acetic acid (1.300 ml, 22.71 mmol). The reaction mixture was stirred at room temperature for 10 minutes. MP-cyanoborohydride (6.91 g, 15.14 mmol) was added and the reaction mixture was stirred at room temperature for 3 days. The reaction mixture was filtered, the filtrate was concentrated and the residue was partitioned between 150 mL 10% methanol in dichloromethane and saturated aqueous sodium bicarbonate (75 mL). The aqueous layer was back extracted with additional 10% methanol in dichloromethane (2×150 mL). The combined organic layers were dried over anhydrous sodium sulfate, filtered and concentrated. Preparative SFC purification of the residue was performed on a THAR/Waters SFC 80 system running under SuperChrom software control and equipped with a 8-way preparative column switcher, carbon dioxide pump, modifier pump, automated back pressure regulator, UV detector, and 6-position fraction collector. The mobile phase was comprised of supercritical carbon dioxide supplied by a Dewar of anhydrous non-certified carbon dioxide pressurized to 350 psi with a modifier of isopropanol buffered with 0.1% diethylamine at a flow rate of 70 g/minutes. UV detection was set to collect at a wavelength of 220 nm, the column was at ambient temperature, and the backpressure regulator was set to maintain 100 bar. The sample was dissolved in methanol at a concentration of 30 mg/mL. The sample was loaded into the modifier stream in 1 mL (30 mg) injections. The mobile phase was held isocratically at 20% isopropanol:carbon dioxide. Fraction collection was time triggered. The instrument was fitted with a LUX Cellulose 1 column with dimensions 21 mm i.d.×250 mm length with 5 μm particles. SFC purification afforded the cis-isomer title compound along with the trans-isomer described in Example 1351B. MS (ESI$^+$) m/z 478.0 (M+H)$^+$.

EXAMPLE 1351B ethyl trans-4-(4-(4-(5-fluoro-2-methoxyphenyl)-1H-pyrrolo[2,3-b]pyridin-2-yl)-5,6-dihydropyridin-1(2H)-yl)cyclohexanecarboxylate The trans-isomer title compound was obtained during the purification described in Example 1351A. MS (ESI$^+$) m/z 478.1 (M+H)$^+$.

EXAMPLE 1351C cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid A mixture of Example 1351A (0.18 g, 0.377 mmol) in tetrahydrofuran (1.885 ml) and methanol (1.885 ml) was treated with aqueous 2 M lithium hydroxide (0.565 ml, 1.131 mmol). The reaction mixture was stirred at room temperature for 16 hours and was concentrated. The residue was dissolved in 5 mL water and was neutralized to pH 6-7 with aqueous 3 M hydrochloric acid. The resulting thick suspension was treated with additional water (6 mL) and was filtered. The solid collected was washed with water (4×3 mL) and dried under vacuum. The material was purified by reverse phase-HPLC (Sunfire 5 μM, 50×250 mm) eluting with 5-50% acetonitrile in water (containing 0.1% trifluoroacetic acid) providing the desired product as the trifluoroacetate salt. The purified material was dissolved in 4 mL dichloromethane and 2 M hydrogen chloride in ether (2 mL) was added. The reaction mixture was stirred for 1 hour and ether (50 mL) was added. The suspension was allowed to settle and the liquid supernatant was then decanted away using a syringe. The residual solid was treated with additional ether (50 mL) and stirred for 5 minutes. The suspension was allowed to settle and the ether supernatant was again removed using a syringe. The trituration sequence was repeated twice more and the residual solid was then dried in a vacuum oven at 60° C. to provide the title compound as an HCl salt. $^1$H NMR (400 MHz, CD$_3$OD) δ ppm 1.61-1.92 (m, 4H), 2.05-2.19 (m, 2H), 2.28-2.42 (m, 2H), 2.67-2.77 (m, 1H), 2.93-3.00 (m, 2H), 3.32-3.47 (m, 2H), 3.75-3.86 (m, 4H), 4.00-4.18 (m, 2H), 6.46-6.64 (m, 1H), 6.73 (s, 1H), 7.19-7.38 (m, 3H), 7.56 (d, J=6.0 Hz, 1H), 8.36 (d, J=6.1 Hz, 1H). MS (ESI$^+$) m/z 450.0 (M+H)$^+$.

EXAMPLE 1352 trans-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid The title compound was prepared essentially as described in Example 1351C, substituting Example 1351B for Example 1351A. $^1$H NMR (400 MHz, CD$_3$OD) δ ppm 1.47-1.79 (m, 4H), 2.15-2.47 (m, 5H), 2.88-3.06 (m, 2H), 3.32-3.44 (m, 2H), 3.75-3.86 (m, 4H), 4.05-4.14 (m, 2H), 6.55-6.63 (m, 1H), 6.70 (s, 1H), 7.18-7.36 (m, 3H), 7.51 (d, J=5.9 Hz, 1H), 8.34 (d, J=6.0 Hz, 1H). MS (ESI$^+$) m/z 450.1 (M+H)$^+$.

EXAMPLE 1353

(cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid

EXAMPLE 1353A methyl (cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetate The title compound was prepared essentially as described in Example 1329A, substituting ethyl 4-oxocyclohexanecarboxylate with methyl 2-(4-oxocyclohexyl)acetate to give a mixture of cis and trans isomers. The isomers were separated via preparative SFC on a THAR/Waters SFC 80 system. The sample was dissolved in methanol at a concentration of 50 mg/mL, and was loaded into the modifier stream in 0.2 mL (10 mg) injections. The mobile phase was held isocratically at 20% methanol (0.1% diethylamine):CO$_2$. Fraction collection was time triggered. The instrument was fitted with a Chiralpak OD-H column with dimensions 21 mm i.d.×250 mm length with 5 μm particles. MS (ESI): 494.3 (M−H)$^−$.

EXAMPLE 1353B (cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid The title compound was prepared essentially as described in Example 1329B, substituting Example 1329A with Example 1353A. $^1$H NMR (400 MHz, DMSO-d$_6$) δ ppm 12.14 (s, 1 H) 10.56 (d, J=32.35 Hz, 1 H) 8.24 (d, J=2.44 Hz, 1 H) 7.05-7.48 (m, 3 H) 6.52 (s, 1 H) 6.30 (d, J=1.53 Hz, 1 H) 3.94 (s, 2 H) 3.67-3.86 (m, 3 H) 3.19 (d, J=38.76 Hz, 2H) 2.70-3.00 (m, 2 H) 2.33 (d, J=7.63 Hz, 2 H) 2.11 (s, 1 H) 1.83-2.02 (m, 2 H) 1.62-1.82 (m, 4 H) 1.55 (d, J=10.38 Hz, 2 H). MS (ESI): 482.1 (M+H)$^+$.

EXAMPLE 1354

(trans-4-{4-[5-fluoro-4-(5-fluoro-2-methoxyphenyl)-1H-pyrrolo[2,3-b]pyridin-2-yl]-3,6-dihydropyridin-1(2H)-yl})cyclohexyl)acetic acid

EXAMPLE 1354A methyl (trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetate The title compound was isolated from the chromatography described in Example 1353A. MS (ESI): 496.0 (M+H)$^+$.

EXAMPLE 1354B (trans-4-{4-[5-fluoro-4-(5-fluoro-2-methoxyphenyl)-1H-pyrrolo[2,3-b]pyridin-2-yl]-3,6-dihydropyridin-1(2H)-yl})cyclohexyl)acetic acid The title compound was prepared essentially as described in Example 1329B, substituting Example 1329A with Example 1354A. $^1$H NMR (501 MHz, DMSO-d$_6$) δ ppm 12.13 (s, 1 H) 9.78 (s, 1 H) 8.25 (d, J=2.57 Hz, 1 H) 7.29-7.45 (m, 1 H) 7.18-7.29 (m, 2 H) 6.51 (s, 1 H) 6.32 (s, 1 H) 3.97 (s, 2 H) 3.71-3.76 (m, 3 H) 3.66 (d, J=7.21 Hz, 1 H) 3.13-3.31 (m, 3 H) 2.69-2.94 (m, 2 H) 2.00-2.20 (m, 4 H) 1.86 (d, J=12.23 Hz, 2 H) 1.42-1.73 (m, 3 H) 1.06 (q, J=11.66 Hz, 2 H). MS (ESI): 482.0 (M+H)$^+$.

EXAMPLE 1355

(1-{4-[4-(5-fluoro-2-methoxyphenyl)-1H-pyrrolo[2,3-b]pyridin-2-yl]cyclohex-3-en-1-yl}piperidin-4-yl)acetic acid

EXAMPLE 1355A methyl 2-(1-(4-(4-(5-fluoro-2-methoxyphenyl)-1H-pyrrolo[2,3-b]pyridin-2-yl)cyclohex-3-enyl)piperidin-4-yl)acetate A mixture of Example 241B (0.5 g, 1.487 mmol) and methyl 2-(piperidin-4-yl)acetate (0.304 g, 1.932 mmol) in dichloromethane (7.43 ml) and methanol (7.43 ml) was treated with acetic acid (0.596 ml, 10.41 mmol), and the reaction was stirred for 10 minutes. MP-cyanoborohydride (2.388 g, 5.95 mmol) was added and the reaction mixture was stirred at room temperature for 7 days. The reaction mixture was filtered and the filtrate was concentrated. The residue was partitioned in 100 mL 10% methanol in dichloromethane and saturated aqueous sodium bicarbonate (40 mL). The aqueous layer was back extracted with additional 10% methanol in dichloromethane (75 mL). The combined organic layers were dried over anhydrous sodium sulfate, filtered, and concentrated. The concentrate was purified by flash chromatography on a 25 g silica gel column using an AnaLogix IntelliFlash 280 system eluting with a gradient of from 0% to 7% methanol in dichloromethane to provide the title compound. MS (ESI$^+$) m/z 478.2 (M+H)$^+$.

EXAMPLE 1355B

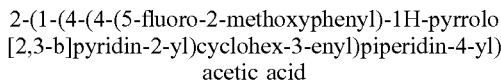

2-(1-(4-(4-(5-fluoro-2-methoxyphenyl)-1H-pyrrolo[2,3-b]pyridin-2-yl)cyclohex-3-enyl)piperidin-4-yl)acetic acid The title compound was prepared essentially as described in Example 1351C, substituting Example 1355A for Example 1351A. $^1$H NMR (400 MHz, CD$_3$OD) δ ppm 1.54-1.71 (m, 2H), 1.85-1.99 (m, 1H), 2.05-2.16 (m, 3H), 2.31-2.46 (m, 3H), 2.60-2.72 (m, 2H), 2.80-2.90 (m, 2H), 3.08-3.24 (m, 2H), 3.53-3.70 (m, 3H), 3.82 (s, 3H), 6.55-6.65 (m, 2H), 7.21-7.36 (m, 3H), 7.57 (d, J=6.2 Hz, 1H), 8.31 (d, J=6.2 Hz, 1H). MS (ESI$^+$) m/z 464.1 (M+H)$^+$.

EXAMPLE 1356

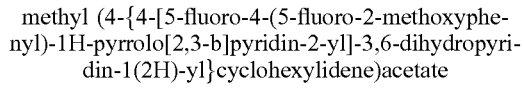

methyl (4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetate The title compound was prepared using the procedure described in Example 1347, using Example 231E in place of Example 87D. $^1$H NMR (400 MHz, DMSO-d$_6$) δ 11.87 (s, 1H), 8.17 (s, 1H), 7.39-7.15 (m, 3H), 6.49 (s, 1H), 6.10 (s, 1H), 5.65 (s, 1H), 3.73 (s, 3H), 3.60 (s, 3H), 3.59-3.56 (m, 1H), 3.25 (d, J=4.0 Hz, 2H), 2.71-2.57 (m, 3H), 2.43-2.31 (m, 3H), 2.24-2.16 (m, 1H), 2.14-2.03 (m, 1H), 1.98-1.88 (m, 2H), 1.54-1.34 (m, 2H). MS (DCI) m/e 494 (M+H)$^+$.

EXAMPLE 1357

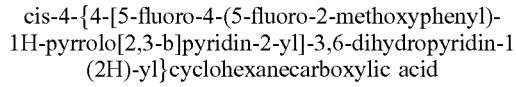

cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid

EXAMPLE 1357A

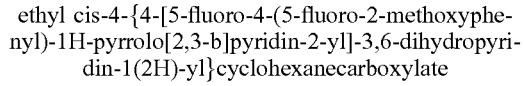

ethyl cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylate To a mixture of Example 231E (1.062 g, 2.56 mmol) and triethylamine (0.786 mL, 5.64 mmol) in dichloromethane (15 mL) and methanol (15 mL) was added acetic acid (0.734 mL, 12.82 mmol), ethyl 4-oxocyclohexanecarboxylate (0.817 mL, 5.13 mmol) and MP-cyanoborohydride (4.200 g, 10.25 mmol). The reaction mixture was heated at 40° C. for 3 hours. The solid material was filtered and rinsed with dichloromethane and methanol. The filtrate was concentrated. The residue was partitioned in ethyl acetate and saturated aqueous sodium bicarbonate. The organic layer was washed with aqueous sodium bicarbonate and brine, dried over anhydrous sodium sulfate, filtered and concentrated down to about 20 ml. Solids precipitated out overnight and were filtered, washed with ether, and vacuum oven-dried to give a mixture of the title compound as a mixture of cis and trans isomers. The filtrate was purified on an 80 g column using the ISCO Companion flash system eluting with dichloromethane/methanol (95:5 to 90:10) to give the same mixture of cis and trans isomers of the title compound. The isomers were separated by preparative SFC performed on a THAR/Waters SFC 80 system running under SuperChrom software control. A Chiralpak IA column (21 mm i.d.×250 mm length with 5 μm particles) was used. The mobile phase consisted of 30% MeOH (with 0.1% diethylamine) and CO$_2$. The SFC purification gave the title compound and, separately, the trans isomer (Example 1358A). MS (ESI$^+$) m/z 496.1 (M+H)$^+$.

EXAMPLE 1357B

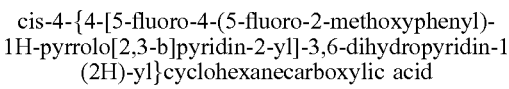

cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid A mixture of Example 1357A (0.236 g, 0.476 mmol) and lithium hydroxide (0.040 g, 1.667 mmol) in tetrahydrofuran (6 mL), methanol (2.4 mL), and water (1.8 mL) was stirred for 24 hours. The reaction mixture was concentrated. The residue was purified by HPLC (see protocols in Example 906) to give a trifluoroacetic acid salt of the title compound. The trifluoroacetic acid salt was dissolved in 5 mL of dichloromethane and 2N HCl in ether (3 mL) was added. The mixture was stirred for 5 minutes and ether (20 mL) was added. The suspension was sonicated, stirred for 20 minutes, allowed to settle, filtered, washed with ether, and vacuum oven-dried. The solids were suspended in dichloromethane (3 mL), sonicated, stirred for 1 hour, filtered, washed with dichloromethane, and vacuum oven-dried to give the title compound as an HCl salt. $^1$H NMR (400 MHz, pyridine-d$_5$) δ ppm 1.49-1.98 (m, 2H), 1.98-2.16 (m, 2H), 2.29-2.38 (m, 2H), 2.45-2.54 (m, 2H), 2.76 (bs, 1H), 3.17 (bs, 2H), 3.31-3.39 (m, 3H), 3.71 (s, 3H), 3.89-3.95 (m, 2H), 6.54 (s, 1H), 6.65 (bs, 1H), 7.12 (dd, J=9.1, 4.5 Hz, 1H), 7.27-7.36 (m, 1H), 7.49 (dd, J=8.6, 3.2 Hz, 1H), 8.53 (d, J=2.5 Hz, 1H), 13.23 (bs, 1H). MS (ESI$^+$) m/z 468.0 (M+H)$^+$.

EXAMPLE 1358

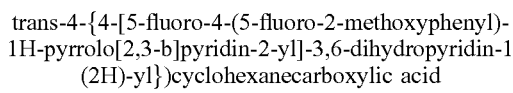

trans-4-{4-[5-fluoro-4-(5-fluoro-2-methoxyphenyl)-1H-pyrrolo[2,3-b]pyridin-2-yl]-3,6-dihydropyridin-1(2H)-yl})cyclohexanecarboxylic acid

EXAMPLE 1358A

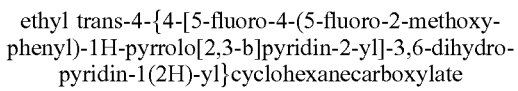

ethyl trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylate The title compound was prepared and isolated as described in Example 1357A. MS (ESI$^+$) m/z 496.0 (M+H)$^+$.

EXAMPLE 1358B

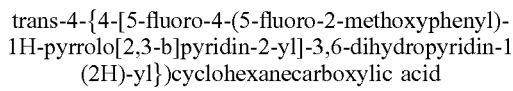

trans-4-{4-[5-fluoro-4-(5-fluoro-2-methoxyphenyl)-1H-pyrrolo[2,3-b]pyridin-2-yl]-3,6-dihydropyridin-1(2H)-yl})cyclohexanecarboxylic acid The title compound was prepared essentially as described in Example 1357B, substituting Example 1357A with Example 1358A. $^1$H NMR (400 MHz, pyridine-d$_5$) δ ppm 1.64-1.86 (m, 4H), 2.27-2.36 (m, 2H), 2.41-2.55 (m, 3H), 3.11-3.50 (m, 5H), 3.72 (s, 3H), 3.97-4.03 (m, 2H), 6.55 (s, 1H), 6.72 (bs, 1H), 7.10-7.16 (m, 1H), 7.33 (td, J=8.5, 3.2 Hz, 1H), 7.51 (dd, J=8.6, 3.2 Hz, 1H), 8.55 (d, J=2.5 Hz, 1H), 13.23 (bs, 1H). MS (ESI$^+$) m/z 468.0 (M+H)$^+$.

EXAMPLE 1359

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetic acid The title compound was prepared using the procedure described in Example 1350, using Example 1356 in place of Example 1347. $^1$H NMR (400 MHz, DMSO-d$_6$) δ 12.07 (s, 1H), 10.75 (bs, 1H), 8.22 (d, J=2.6 Hz, 1H), 7.45-6.79 (m, 3H), 6.50 (s, 1H), 6.26 (s, 1H), 5.65 (s, 1H), 3.89-3.78 (m, 4H), 3.73 (s, 3H), 3.30-3.18 (m, 2H), 2.84-2.68 (m, 2H), 2.47-2.38 (m, 2H), 2.31-2.14 (m, 2H), 2.03-1.92 (m, 1H), 1.74-1.45 (m, 2H). MS (DCI) m/e 480 (M+H)$^+$.

EXAMPLE 1360

(trans-4-{4-[5-fluoro-4-(5-fluoro-2-methoxyphenyl)-1H-pyrrolo[2,3-b]pyridin-2-yl]piperidin-1-yl}cyclohexyl)acetic acid

EXAMPLE 1360A methyl (trans-4-{4-[5-fluoro-4-(5-fluoro-2-methoxyphenyl)-1H-pyrrolo[2,3-b]pyridin-2-yl]piperidin-1-yl}cyclohexyl)acetate The title compound was prepared as described in Example 1357A, substituting Example 255D for Example 231E and methyl 2-(4-oxocyclohexyl)acetate for ethyl 4-oxocyclohexanecarboxylate. The title compound was the slower-eluting isomer under the described SFC conditions. MS (ESI$^+$) m/z 498.0 (M+H)$^+$.

EXAMPLE 1360B (trans-4-{4-[5-fluoro-4-(5-fluoro-2-methoxyphenyl)-1H-pyrrolo[2,3-b]pyridin-2-yl]piperidin-1-yl}cyclohexyl)acetic acid The title compound was prepared using the procedure described in Example 1357B, using Example 1360A in place of Example 1357A. $^1$H NMR (400 MHz, DMSO-d$_6$) δ 0.95 (q, J=12.1 Hz, 2H), 1.24 (q, J=12.4 Hz, 2H), 1.48-1.70 (m, 2H), 1.75 (d, J=11.6 Hz, 4H), 1.93 (d, J=12.5 Hz, 2H), 2.06 (d, J=6.9 Hz, 2H), 2.26 (q, J=11.6 Hz, 3H), 2.64 (t, J=12.0 Hz, 1H), 2.88 (d, J=11.0 Hz, 2H), 3.72 (s, 3H), 5.87 (s, 1H), 6.97-7.63 (m, 3H), 8.11 (s, 1H), 11.67 (s, 1H). MS (ESI$^+$) m/z 484 (M+H)$^+$.

EXAMPLE 1361

2-(trans-4-{4-[4-(5-fluoro-2-methoxyphenyl)-1H-pyrrolo[2,3-b]pyridin-2-yl]-3,6-dihydropyridin-1(2H)-yl}cyclohexyl)-N-(propan-2-ylsulfonyl)acetamide A suspension of Example 289 (free base, 0.155 g, 0.334 mmol) and N-ethyl-N-isopropylpropan-2-amine (0.175 ml, 1.003 mmol) in N,N-dimethylformamide (2.5 mL) was treated with 1,1'-carbonyldiimidazole (0.098 g, 0.602 mmol) and the reaction mixture was heated at 50° C. for 30 minutes. After cooling to room temperature, a solution of propane-2-sulfonamide (0.082 g, 0.669 mmol) and 1,8-diazabicyclo[5.4.0]undec-7-ene (0.202 ml, 1.338 mmol) in N,N-dimethylformamide (1 mL) was added dropwise over 3 minutes. The reaction mixture was stirred at room temperature for 16 hours and then was directly purified by reverse phase-HPLC (Sunfire 5 µM, 50×250 mm) eluting with 5-50% acetonitrile in water (containing 0.1% trifluoroacetic acid) to provide the title compound. $^1$H NMR (400 MHz, CD$_3$OD) δ ppm 1.14-1.32 (m, 2H), 1.37 (d, J=6.8 Hz, 6H), 1.57-1.78 (m, 2H), 1.80-1.96 (m, 1H), 1.96-2.08 (m, 2H), 2.16-2.36 (m, 4H), 2.94-3.01 (m, 2H), 3.28-3.44 (m, 2H), 3.59-3.78 (m, 1H), 3.78-3.88 (m, 4H), 4.03-4.14 (m, 2H), 6.56-6.64 (m, 1H), 6.74 (s, 1H), 7.19-7.38 (m, 3H), 7.57 (d, J=6.0 Hz, 1H), 8.36 (d, J=6.1 Hz, 1H). MS (ESI$^+$) m/z 569.1 (M+H)$^+$.

EXAMPLE 1362 trans-4-{4-[5-fluoro-4-(5-fluoro-2-methoxyphenyl)-1H-pyrrolo[2,3-b]pyridin-2-yl]-3,6-dihydropyridin-1(2H)-yl}-N-(propan-2-ylsulfonyl)cyclohexanecarboxamide A mixture of Example 1358B (0.050 g, 0.099 mmol), N,N-diisopropylethylamine (0.061 ml, 0.347 mmol), and 1,1'-carbonyldiimidazole (0.029 g, 0.179 mmol) in N,N-dimethylformamide (1.2 ml) was heated at 50° C. for 30 minutes. After cooling to room temperature, the homogeneous reaction solution was treated with a solution of propane-2-sulfonamide (0.024 g, 0.198 mmol) and 1,8-diazabicyclo[5.4.0]undec-7-ene (0.060 ml, 0.397 mmol) in N,N-dimethylformamide (0.4 mL). The reaction mixture was stirred overnight. The reaction mixture was purified by HPLC (see protocols in Example 217) to provide the title compound as a trifluoroacetic acid salt. $^1$H NMR (400 MHz, methanol-d$_4$) δ ppm 1.36 (d, J=6.8 Hz, 6H), 1.58-1.72 (m, 4H), 2.09-2.16 (m, 2H), 2.18-2.42 (m, 3H), 2.88-2.96 (m, 2H), 3.33-3.43 (m, 2H), 3.64-3.83 (m, 5H), 4.04 (s, 1H), 6.34 (s, 1H), 6.38-6.43 (m, 1H), 7.11-7.26 (m, 3H), 8.15 (d, J=2.8 Hz, 1H). MS (ESI$^+$) m/z 573.0 (M+H)$^+$.

EXAMPLE 1363

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexyl)acetic acid To a solution of Example 845 (80 mg, 0.229 mmol) in dichloromethane (1 mL) and methanol (1 mL) were added 2-(4-oxocyclohexyl)acetic acid (46.5 mg, 0.298 mmol) and acetic acid (68.7 mg, 1.145 mmol) and the reaction mixture was stirred for 10 minutes. MP-cyanoborohydride (418 mg, 0.916 mmol) was then added and the thick reaction mixture was stirred at room temperature for 1 day. The solid material was filtered and rinsed with a mixture of dichloromethane and methanol (1:1). The filtrate was concentrated and the residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (400 MHz, DMSO-D$_6$) δ ppm 0.92-2.29 (m, 11 H) 2.57-3.86 (m, 10 H) 3.72 (s, 3 H) 6.12-6.45 (m, 2 H) 7.04

(d, J=4.88 Hz, 1 H) 7.09-7.34 (m, 3 H) 8.22 (d, J=4.88 Hz, 1 H) 11.74 (s, 1 H). MS (ESI+) m/z 490 (M+H)+.

EXAMPLE 1364

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid

EXAMPLE 1364A tert-butyl 2-(4-oxocyclohexylidene)acetate

A mixture of tert-butyl 2-(triphenylphosphoranylidene)acetate (4.55 g, 12.09 mmol) and cyclohexane-1,4-dione (2.71 g, 24.17 mmol) in toluene (50 mL) was stirred at 100 C overnight. The mixture was concentrated in vacuo. Hexanes (10 mL) and ethyl acetate (10 mL) were added and a precipitate formed. The solids were filtered and rinsed with a mixture of hexanes and ethyl acetate (1:1). The filtrate was concentrated under vacuum and the residue was purified by flash chromatography on Analogix IntelliFlash$^{280}$ eluting with 0 to 50% ethyl acetate/hexanes to give the title compound. $^1$H NMR (400 MHz, DMSO-D$_6$) δ ppm 1.43 (s, 9 H) 2.30-2.45 (m, 4 H) 2.58-2.66 (m, 2 H) 2.92-3.10 (m, 2 H) 5.75 (s, 1 H).

EXAMPLE 1364B tert-butyl 2-(4-(5-(4-(5-fluoro-2-methoxyphenyl)-1H-pyrrolo[2,3-b]pyridin-2-yl)-3,3a,6,6a-tetrahydrocyclopenta[c]pyrrol-2(1H)-yl)cyclohexylidene)acetate The title compound as the bis-trifluoroacetate salt was prepared using the condition described in Example 1363 substituting Example 1364A for 2-(4-oxocyclohexyl)acetic acid. MS (ESI+) m/z 544 (M+H)+.

EXAMPLE 1364C (4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid A mixture of Example 1364B (100 mg, 0.130 mmol) in dichloromethane (0.3 mL) and trifluoroacetic acid (0.3 mL) was stirred at room temperature for 3 hours. The mixture was concentrated and dried in a 50 C oven under vacuum overnight to give the title compound as the bis-trifluoroacetate salt. $^1$H NMR (400 MHz, pyridine-D$_5$) δ ppm 1.77-3.41 (m, 13 H) 3.72 (s, 3 H) 3.75-4.37 (m, 4 H) 5.96 (s, 1 H) 6.44 (d, J=1.22 Hz, 1 H) 6.65 (s, 1 H) 7.11 (dd, J=9.16, 4.58 Hz, 1 H) 7.24-7.37 (m, 2 H) 7.49 (dd, J=9.00, 3.20 Hz, 1 H) 8.60 (d, J=4.88 Hz, 1 H) 13.11 (s, 1 H). MS (ESI+) m/z 488 (M+H)+.

BIOLOGICAL EXAMPLES

CDK9 Enzyme Protocol

CDK9 enzyme activities were measured using LANCE ULight TR-FRET kinase assay reagents (PerkinElmer, Waltham, Mass.). Compounds were directly added in 100% DMSO to white low volume assay plates (Perkin Elmer Proxiplate 6008289) using a Labcyte Echo acoustic dispenser. Assay reagents in serine/threonine kinase assay buffer containing 20 mM HEPES, 10 mM MgCl$_2$, 100 mM Na$_3$VO$_4$, and 0.0075% Triton X-100. were added for final reaction mixture concentrations of 1000 μM ATP, 100 nM U-light MBP peptide (Perkin Elmer TRF0109M) and reaction initiated with 4 nM CDK9/Cyclin T1 (Carna Biosciences 04-110). The kinase reaction was carried out for 30 minutes before addition of stopping buffer to a final of 20 mM EDTA and 0.5 nM of LANCE Ultra Europium anti-phospho-MBP antibody (PerkinElmer TRF0201M) in LANCE detection buffer (PerkinElmer CR97-100). The reaction was equilibrated for 1 hour and the signal read in the Perkin Elmer Envision in TR-FRET mode (excitation at 320 nm and emission at 615/665 nm).

Cell Viability Protocol

Cell viability assays were performed using A431 or H929 cells. A431 cells were seeded in 96-well plates at 10,000 cells/well and, after overnight incubation, treated with compounds at 2-times the final concentration to result in a dose response of 3-fold dilutions from 10 μM to 0.0005 μM (50 μL/well, 0.1% final DMSO concentration). H929 cells were seeded in 96-well plates at 10,000 cells/well and treated immediately with compounds as described above. After 24 hours at 37° C., cell viability was measured using Cell TiterGlo reagent (Promega) with a luminescence reader. Alternately, cell viability assays were performed in 384-well format. A431 cells were seeded in 384-well plates at 2500 cells/well and, after overnight incubation, treated with compounds in a dose response of 3-fold dilutions from 10 μM to 0.0005 μM (25 nL/well, 0.1% final DMSO concentration). For the H929 viability assay, 25 nL/well of the compounds was dispensed into 384-well plates in a dose response as described above and cells were immediately seeded in 384-well plates at 2500 cells/well. After 24 hours at 37° C., cell viability was measured using Cell TiterGlo reagent (Promega) with a luminescence reader. The results are reported in Table 1.

In-Cell Western

In-cell Western assays were used to measure phosphorylation of RNA polymerase II C-terminal domain Ser2. A431 cells were seeded in 96-well black plates at 15,000 cells/well, 50 μL/well and, after overnight incubation, treated with compounds at 2-times the final concentration to result in a dose response of 3-fold dilutions from 10 μM to 0.0005 μM. After 4 hours, cells were washed with PBS and fixed at room temperature for 1 hour with 4% paraformaldehyde in PBS. Cells were washed with PBST (PBS with 0.1% Triton X100), blocked in 5% BSA in 1×PBST, and incubated with rabbit anti-RNA Polymerase II CTD phosphorylated Ser 2 (Bethyl) overnight at 4° C. Cells were then washed with Delfia/Autodelfia wash buffer and incubated for 2 hours at room temperature in the dark with Delfia Eu-N1 anti-rabbit antibody diluted in Delfia Assay Buffer. Cells were washed with Delfia/Autodelfia wash buffer, incubated for 20 minutes at room temperature in the dark with Delfia Enhancement solution, and the plate was read at the Europium settings on a Victor plate reader. The Delfia signal was normalized for cell density using Hoechst staining.

Alternate In-Cell Western Protocol

In-cell Western assays were used to measure phosphorylation of RNA polymerase II C-terminal domain Ser2. A431 cells were seeded in 96-well black walled Viewplates (Perkin Elmer) at 10,000 cells/well 50 μl per well and, after overnight incubation, treated with compounds at 2 times the final concentration to result in a final dose response of 3-fold dilutions from 10 μM to 0.0005 μM. After 4 hours, cells were fixed at room temperature for 10 minutes with the addition of 100 μl of 4% paraformaldehyde in PBS. Cells were washed with PBST, blocked in 1% BSA in 1×PBST for 30 minutes, and incubated with rabbit anti-RNA Polymerase II CTD phosphorylated Ser 2 (Bethyl) overnight at 4° C. Cells were then washed with Delfia/Autodelfia wash buffer and incubated for 1 hour at room temperature in the dark with Alexa Fluor 488 conjugated goat anti-rabbit antibody and Hoechst (Invitrogen) diluted in blocking buffer. Cells were washed with Delfia/Autodelfia wash buffer, followed by the addition of 200 µl of PBS. The plates were read on a CellInsight high content instrument (Thermo Scientific). The Alexa Fluor 488 signal was normalized for by subtracting background staining and collecting images from 400 cells. The In-cell Western (ICW) $IC_{50}$ values are reported in Table 1.

TABLE 1

| EXAMPLE | CDK9/Cyclin T1 $IC_{50}$ (µM) | Cell Viability A-431 $IC_{50}$ (µM) | Cell Viability H929 $IC_{50}$ (µM) | ICW $IC_{50}$ (µM) |
|---|---|---|---|---|
| 1 | 0.016 | 0.089 | 0.28 | 0.085 |
| 2 | 0.022 | 0.18 | 0.17 | 0.22 |
| 3 | 0.023 | 0.11 | ND | 0.2 |
| 4 | 0.015 | 0.04 | ND | 0.076 |
| 5 | 6.9 | ND | ND | ND |
| 6 | >12.5 | >10 | ND | ND |
| 7 | 4.7 | ND | ND | ND |
| 8 | 0.049 | 0.3 | 1.08 | 0.47 |
| 9 | 0.035 | 0.17 | ND | 0.26 |
| 10 | 0.32 | 1 | ND | ND |
| 11 | 0.033 | 0.041 | 0.32 | 0.26 |
| 12 | 0.093 | ND | ND | ND |
| 13 | 0.13 | ND | ND | ND |
| 14 | 0.49 | 0.96 | ND | ND |
| 15 | 1.4 | 3.3 | ND | ND |
| 16 | 0.77 | 0.33 | ND | ND |
| 17 | 0.011 | 0.022 | 0.16 | 0.02 |
| 18 | 0.019 | 0.052 | ND | 0.052 |
| 19 | 0.019 | 0.076 | ND | 0.32 |
| 20 | 0.031 | 0.12 | ND | 0.52 |
| 21 | 6.6 | ND | ND | ND |
| 22 | 0.012 | 0.15 | ND | 0.076 |
| 23 | 0.077 | 0.45 | ND | 2.7 |
| 24 | 0.068 | 0.55 | ND | 1.6 |
| 25 | 0.3 | ND | ND | ND |
| 26 | 0.077 | ND | ND | ND |
| 27 | 0.027 | 0.2 | ND | 0.039 |
| 28 | 0.017 | 0.064 | 0.18 | 0.052 |
| 29 | 0.023 | 0.12 | ND | 0.074 |
| 30 | 0.12 | ND | ND | ND |
| 31 | 2.6 | ND | ND | ND |
| 32 | 0.021 | 0.025 | 0.077 | 0.17 |
| 33 | 0.015 | 0.016 | ND | 0.035 |
| 34 | 0.018 | 0.1 | ND | 0.66 |
| 35 | 0.021 | 0.14 | ND | 0.36 |
| 36 | 0.017 | 0.085 | ND | 0.17 |
| 37 | 0.01 | 0.19 | ND | 0.14 |
| 38 | 0.033 | 0.3 | ND | 0.45 |
| 39 | 0.019 | 0.035 | ND | 0.03 |
| 40 | 0.025 | 0.28 | ND | 0.15 |
| 41 | 0.06 | 7.2 | ND | >10 |
| 42 | 0.55 | ND | ND | ND |
| 43 | 0.17 | ND | ND | ND |
| 44 | 5.1 | ND | ND | ND |
| 45 | 19 | ND | ND | ND |
| 46 | 0.021 | 0.14 | ND | 0.76 |
| 47 | 0.048 | 1.1 | 0.64 | 0.89 |
| 48 | 0.081 | 4.8 | ND | 4.3 |
| 49 | 0.087 | 0.28 | ND | 0.74 |
| 50 | 0.57 | ND | ND | ND |
| 51 | 0.049 | 0.011 | 0.053 | 0.027 |
| 52 | 0.014 | 0.049 | ND | 0.085 |
| 53 | 0.025 | 0.46 | ND | 0.15 |
| 54 | 0.019 | 0.11 | ND | 0.11 |
| 55 | 0.049 | 2.1 | ND | 4.1 |
| 56 | 0.015 | 0.24 | ND | 0.19 |
| 57 | 0.015 | 0.019 | ND | 0.024 |
| 58 | 0.024 | 1.1 | ND | 0.89 |
| 59 | 0.017 | 0.075 | 0.2 | 0.042 |
| 60 | 0.025 | 0.12 | ND | 0.26 |
| 61 | 0.023 | 0.13 | ND | 0.27 |
| 62 | 0.015 | 0.048 | ND | 0.045 |
| 63 | 0.022 | 0.042 | ND | 0.06 |
| 64 | 0.025 | 0.089 | ND | 0.13 |
| 65 | 0.2 | ND | ND | ND |
| 66 | 0.042 | 0.65 | 0.51 | 0.54 |
| 67 | 0.037 | 0.63 | ND | 0.23 |
| 68 | 0.51 | ND | ND | ND |
| 69 | 0.25 | ND | ND | ND |
| 70 | 0.065 | 0.66 | ND | 0.48 |
| 71 | 0.063 | 0.76 | ND | 0.66 |
| 72 | 0.36 | ND | ND | ND |
| 73 | 0.12 | ND | ND | ND |
| 74 | 0.024 | 0.61 | 0.38 | 0.3 |
| 75 | 0.023 | 0.76 | ND | 0.52 |
| 76 | 0.017 | 0.089 | ND | 0.17 |
| 77 | 0.025 | 0.18 | ND | 0.14 |
| 78 | 0.063 | 0.32 | ND | 0.42 |
| 79 | 0.84 | 0.52 | ND | ND |
| 80 | 0.039 | 0.68 | 0.56 | 0.34 |
| 81 | 0.64 | 0.3 | ND | ND |
| 82 | 0.18 | ND | ND | ND |
| 83 | 1.3 | 3.3 | ND | ND |
| 84 | 0.6 | 0.89 | ND | ND |
| 85 | 0.1 | ND | ND | ND |
| 86 | 0.12 | ND | ND | ND |
| 87 | 0.01 | 0.014 | 0.034 | 0.025 |
| 88 | 0.03 | ND | 1 | ND |
| 89 | 0.034 | 0.15 | 0.39 | 0.16 |
| 90 | 0.035 | ND | 3.4 | ND |
| 91 | 0.029 | ND | 0.51 | ND |
| 92 | 0.051 | ND | 0.91 | ND |
| 93 | 0.034 | ND | 0.53 | ND |
| 94 | 0.58 | ND | ND | ND |
| 95 | 0.15 | ND | 1.1 | ND |
| 96 | 0.05 | 0.71 | 0.7 | 0.44 |
| 97 | 0.014 | 0.046 | 0.15 | 0.1 |
| 98 | 0.27 | ND | 4.1 | ND |
| 99 | 1.3 | ND | ND | ND |
| 100 | 0.033 | 0.09 | 0.11 | 0.033 |
| 101 | 0.036 | 0.055 | 0.13 | 0.072 |
| 102 | 0.012 | ND | 0.16 | ND |
| 103 | 0.43 | ND | ND | ND |
| 104 | 0.044 | ND | 1.5 | ND |
| 105 | 0.013 | ND | 0.36 | ND |
| 106 | 0.18 | ND | 3.7 | ND |
| 107 | 0.036 | ND | 2.1 | ND |
| 108 | 0.074 | ND | 0.79 | ND |
| 109 | 0.044 | ND | 0.55 | ND |
| 110 | 0.044 | ND | 1 | ND |
| 111 | 0.038 | ND | 0.72 | ND |
| 112 | 0.014 | ND | 0.79 | ND |
| 113 | 0.023 | ND | 1.1 | ND |
| 114 | 0.036 | ND | 0.76 | ND |
| 115 | 0.029 | ND | 1 | ND |
| 116 | 0.1 | ND | 3 | ND |
| 117 | 0.061 | ND | 0.89 | ND |
| 118 | 0.043 | ND | 0.86 | ND |
| 119 | 0.037 | 0.089 | 0.13 | 0.16 |
| 120 | 0.022 | 0.1 | 0.19 | 0.11 |
| 121 | 0.034 | ND | 0.26 | ND |
| 122 | 0.04 | ND | 0.29 | ND |
| 123 | 0.028 | ND | 0.79 | ND |
| 124 | 0.039 | ND | 1.1 | ND |
| 125 | 0.046 | ND | 2 | ND |
| 126 | 0.075 | ND | 0.9 | ND |
| 127 | 0.023 | ND | 1.2 | ND |
| 128 | 0.021 | ND | 1.4 | ND |
| 129 | 0.014 | ND | 1.8 | ND |
| 130 | 0.05 | ND | 1.2 | ND |
| 131 | 0.064 | ND | 2.3 | ND |
| 132 | 0.13 | ND | 2.7 | ND |

TABLE 1-continued

| EXAMPLE | CDK9/Cyclin T1 IC$_{50}$ (µM) | Cell Viability A-431 IC$_{50}$ (µM) | Cell Viability H929 IC$_{50}$ (µM) | ICW IC$_{50}$ (µM) |
| --- | --- | --- | --- | --- |
| 133 | 1.5 | ND | ND | ND |
| 134 | 0.12 | ND | 1.4 | ND |
| 135 | 0.044 | ND | 0.65 | ND |
| 136 | 0.023 | 0.29 | 0.23 | 0.14 |
| 137 | 0.039 | ND | 1.1 | ND |
| 138 | 0.033 | ND | 1.2 | ND |
| 139 | 0.12 | ND | 3.9 | ND |
| 140 | 0.02 | ND | 0.57 | ND |
| 141 | 0.024 | ND | 0.74 | ND |
| 142 | 0.069 | ND | 1.3 | ND |
| 143 | 0.32 | ND | >10 | ND |
| 144 | 0.37 | ND | ND | ND |
| 145 | 0.029 | ND | 2.6 | ND |
| 146 | 0.012 | ND | 0.6 | ND |
| 147 | 0.031 | ND | 1.27 | ND |
| 148 | 0.021 | ND | 0.77 | ND |
| 149 | 0.021 | 0.028 | 0.13 | 0.098 |
| 150 | 0.017 | ND | 1.3 | ND |
| 151 | 0.34 | ND | 4 | ND |
| 152 | 0.096 | ND | <3.3 | ND |
| 153 | 0.047 | ND | 1.1 | ND |
| 154 | 0.15 | ND | 0.47 | ND |
| 155 | 0.051 | 0.046 | 0.25 | 0.11 |
| 156 | 0.015 | ND | 0.96 | ND |
| 157 | 0.049 | ND | 2.4 | ND |
| 158 | 0.091 | ND | 4.2 | ND |
| 159 | 0.086 | ND | 0.62 | ND |
| 160 | 0.041 | 0.054 | 0.19 | 0.18 |
| 161 | 0.045 | 0.089 | 0.22 | 0.21 |
| 162 | 0.028 | ND | 0.49 | ND |
| 163 | 0.11 | ND | 2.9 | ND |
| 164 | 0.03 | ND | 1.8 | ND |
| 165 | 0.45 | 8.53 | 10 | >10 |
| 166 | 0.27 | ND | 3.8 | ND |
| 167 | 0.073 | ND | 1.5 | ND |
| 168 | 0.16 | ND | 3 | ND |
| 169 | 0.034 | ND | 0.76 | ND |
| 170 | 0.29 | ND | 5 | ND |
| 171 | 0.09 | ND | ND | ND |
| 172 | 0.076 | ND | 1.4 | ND |
| 173 | 0.075 | ND | 2.6 | ND |
| 174 | 0.025 | ND | 2.1 | ND |
| 175 | 0.1 | ND | 6.1 | ND |
| 176 | 0.035 | ND | 0.63 | ND |
| 177 | 0.055 | ND | 1.1 | ND |
| 178 | 0.078 | ND | 3.2 | ND |
| 179 | 0.052 | ND | 0.66 | ND |
| 180 | 0.023 | ND | 0.71 | ND |
| 181 | 0.019 | ND | 0.73 | ND |
| 182 | 0.022 | ND | 0.47 | ND |
| 183 | 0.022 | ND | 0.54 | ND |
| 184 | 0.03 | ND | 0.8 | ND |
| 185 | 0.14 | ND | 2.2 | ND |
| 186 | 0.004 | 0.017 | 0.047 | 0.026 |
| 187 | 0.067 | ND | 3.4 | ND |
| 188 | 0.046 | 0.068 | 0.28 | 0.15 |
| 189 | 0.023 | 0.007 | 0.061 | 0.016 |
| 190 | 0.008 | 0.021 | 0.057 | 0.044 |
| 191 | 0.025 | 0.055 | 0.25 | 0.077 |
| 192 | 0.81 | ND | ND | ND |
| 193 | 0.033 | 0.063 | 0.71 | 0.089 |
| 194 | ND | ND | ND | ND |
| 195 | 0.033 | 0.037 | 0.057 | 0.04 |
| 196 | 0.91 | ND | ND | ND |
| 197 | 0.73 | ND | ND | ND |
| 198 | 0.16 | ND | 7.27 | ND |
| 199 | 0.029 | 0.13 | 0.16 | 0.14 |
| 200 | 0.055 | 1.31 | 1.4 | 1.1 |
| 201 | 0.026 | 0.093 | 0.14 | 0.063 |
| 202 | 0.02 | 0.19 | 0.28 | 0.37 |
| 203 | 0.008 | 0.047 | 0.11 | 0.052 |
| 204 | 0.027 | 0.56 | 0.57 | 0.2 |
| 205 | 0.023 | 0.52 | 0.33 | 0.28 |
| 206 | 0.011 | 0.12 | 0.18 | 0.093 |
| 207 | 0.066 | 1.36 | 0.82 | ND |
| 208 | 0.043 | 0.063 | ND | 0.17 |
| 209 | 0.08 | 0.17 | ND | 0.29 |
| 210 | 0.017 | 0.024 | ND | 0.079 |
| 211 | 0.018 | 0.1 | ND | 0.033 |
| 212 | 0.021 | 0.048 | ND | 0.036 |
| 213 | 0.025 | 0.029 | ND | 0.093 |
| 214 | 0.021 | 0.021 | ND | 0.027 |
| 215 | 0.019 | 0.025 | 0.074 | 0.059 |
| 216 | 0.03 | 0.02 | 0.059 | 0.12 |
| 217 | 0.056 | 0.011 | 0.02 | ND |
| 218 | 0.064 | 0.07 | 0.066 | ND |
| 219 | 0.062 | 1.61 | 1.15 | 1.79 |
| 220 | 0.053 | ND | 0.463 | ND |
| 221 | 0.021 | 0.026 | 0.044 | ND |
| 222 | 0.084 | ND | 0.48 | ND |
| 223 | 0.038 | ND | 0.316 | ND |
| 224 | 0.039 | 0.053 | 0.151 | 0.028 |
| 225 | 0.037 | 0.044 | 0.073 | 0.123 |
| 226 | 0.033 | 0.187 | 0.243 | 0.087 |
| 227 | 0.028 | 0.13 | 0.2 | 0.105 |
| 228 | 0.019 | 0.145 | 0.206 | 0.47 |
| 229 | 0.101 | 0.096 | 0.105 | 0.244 |
| 230 | 0.022 | 0.046 | 0.148 | 0.176 |
| 231 | 0.045 | 0.015 | 0.073 | 0.03 |
| 232 | 0.023 | 0.018 | 0.059 | 0.108 |
| 233 | 0.114 | 0.056 | 0.084 | 0.073 |
| 234 | 0.047 | 0.139 | 0.098 | 0.154 |
| 235 | 0.038 | 0.046 | 0.06 | 0.035 |
| 236 | 0.126 | 0.07 | 0.057 | 0.124 |
| 237 | 0.13 | 0.162 | 0.105 | 0.333 |
| 238 | 0.062 | 0.213 | 0.212 | 0.177 |
| 239 | 0.053 | 0.038 | 0.026 | 0.032 |
| 240 | 0.056 | ND | 0.1 | ND |
| 241 | 0.08 | 0.333 | 0.076 | 0.371 |
| 242 | 0.07 | 1.83 | 0.341 | 1.32 |
| 243 | 0.027 | 0.077 | 0.045 | 0.17 |
| 244 | 0.118 | ND | 0.195 | ND |
| 245 | 0.032 | 0.127 | 0.089 | 0.09 |
| 246 | 0.039 | 0.139 | 0.094 | 0.12 |
| 247 | 0.045 | ND | 0.01 | ND |
| 248 | 0.023 | 0.025 | 0.014 | 0.035 |
| 249 | 0.028 | 0.031 | 0.019 | 0.048 |
| 250 | 0.047 | ND | 0.303 | ND |
| 251 | 0.056 | 0.024 | 0.029 | 0.022 |
| 252 | 0.045 | 0.176 | 0.119 | 0.092 |
| 253 | 0.077 | ND | 0.156 | ND |
| 254 | 0.095 | 0.054 | 0.048 | 0.091 |
| 255 | 0.09 | ND | 0.02 | ND |
| 256 | 0.045 | 0.041 | 0.029 | 0.056 |
| 257 | 0.082 | ND | 0.083 | ND |
| 258 | 0.085 | ND | 0.238 | ND |
| 259 | 0.102 | ND | 0.051 | ND |
| 260 | 0.111 | ND | 0.156 | ND |
| 261 | 0.093 | ND | 0.322 | ND |
| 262 | 0.091 | 0.138 | 0.138 | 0.168 |
| 263 | 0.101 | 0.014 | 0.015 | 0.029 |
| 264 | 0.07 | 0.028 | 0.026 | 0.043 |
| 265 | 0.049 | 0.014 | 0.017 | 0.034 |
| 266 | 0.085 | 0.016 | 0.012 | 0.046 |
| 267 | 0.135 | 0.141 | 0.049 | 0.184 |
| 268 | 0.149 | 0.119 | 0.037 | 0.199 |
| 269 | 0.115 | 0.182 | 0.144 | 0.156 |
| 270 | 0.082 | 0.242 | 0.133 | 0.172 |
| 271 | 0.104 | 0.39 | 0.252 | 0.555 |
| 272 | 0.122 | ND | 0.373 | ND |
| 273 | 0.081 | 0.09 | 0.023 | 0.041 |
| 274 | 0.078 | 0.055 | 0.044 | 0.055 |
| 275 | 0.09 | 0.043 | 0.041 | 0.088 |
| 276 | 0.066 | 0.05 | 0.023 | 0.03 |
| 277 | 0.087 | 0.083 | 0.057 | 0.198 |
| 278 | 0.086 | 0.126 | 0.117 | 0.305 |
| 279 | 0.124 | 0.707 | 0.433 | 1.09 |
| 280 | 0.071 | 0.037 | 0.03 | 0.106 |
| 281 | 0.077 | 0.036 | 0.03 | 0.161 |
| 282 | 0.117 | 0.028 | 0.032 | 0.088 |

TABLE 1-continued

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 283 | 0.172 | 0.093 | 0.057 | 0.18 |
| 284 | 0.071 | 0.024 | 0.019 | 0.105 |
| 285 | 0.093 | 0.069 | 0.072 | 0.144 |
| 286 | 0.201 | 0.014 | 0.023 | 0.047 |
| 287 | 0.104 | 0.043 | 0.051 | 0.101 |
| 288 | 0.071 | ND | 0.099 | ND |
| 289 | 0.057 | 0.229 | 0.111 | 0.379 |
| 290 | 0.078 | 0.046 | 0.035 | 0.113 |
| 291 | 0.093 | 0.06 | 0.055 | 0.196 |
| 292 | 0.139 | 0.236 | 0.129 | 0.277 |
| 293 | 0.07 | 0.117 | 0.096 | 0.241 |
| 294 | 0.042 | 0.118 | 0.131 | 0.176 |
| 295 | 0.119 | ND | 0.183 | ND |
| 296 | 0.125 | ND | 0.196 | ND |
| 297 | 0.083 | 0.042 | 0.042 | 0.06 |
| 298 | 0.099 | 0.093 | 0.059 | 0.302 |
| 299 | 0.083 | 0.298 | 0.206 | 0.142 |
| 300 | 0.115 | 0.063 | 0.081 | 0.164 |
| 301 | 0.12 | 0.043 | 0.057 | 0.083 |
| 302 | 0.09 | 0.013 | 0.027 | 0.024 |
| 303 | 0.138 | 0.294 | 0.194 | 0.421 |
| 304 | 0.131 | ND | 0.254 | ND |
| 305 | 0.061 | ND | 0.064 | ND |
| 306 | 0.114 | ND | 0.032 | ND |
| 307 | 0.057 | 0.015 | 0.098 | 0.031 |
| 308 | 0.036 | 0.023 | 0.087 | 0.049 |
| 309 | 0.092 | 0.79 | 3.5 | ND |
| 310 | 0.053 | ND | 0.71 | ND |
| 311 | 0.097 | ND | 0.52 | ND |
| 312 | 1.4 | ND | ND | ND |
| 313 | 0.42 | ND | ND | ND |
| 314 | 0.019 | 0.036 | 0.17 | 0.084 |
| 315 | 0.077 | 0.125 | 0.18 | 0.37 |
| 316 | 0.025 | 0.021 | 0.089 | 0.058 |
| 317 | 0.031 | 0.012 | 0.055 | 0.038 |
| 318 | 0.048 | 0.011 | 0.048 | 0.032 |
| 319 | 0.044 | 0.015 | 0.086 | 0.037 |
| 320 | 0.061 | ND | 0.39 | ND |
| 321 | 0.039 | ND | 0.38 | ND |
| 322 | 0.20 | ND | 1.1 | ND |
| 323 | 0.064 | ND | 1.3 | ND |
| 324 | 0.39 | ND | ND | ND |
| 325 | 0.024 | ND | 0.05 | ND |
| 326 | 0.11 | ND | 0.75 | ND |
| 327 | 0.016 | 0.006 | 0.041 | 0.006 |
| 328 | 0.043 | 0.008 | 0.042 | 0.014 |
| 329 | 0.059 | ND | 0.52 | ND |
| 330 | 0.076 | ND | 1.1 | ND |
| 331 | 0.091 | ND | 0.14 | ND |
| 332 | 0.094 | ND | 0.25 | ND |
| 333 | 0.07 | ND | 0.18 | ND |
| 334 | 0.046 | ND | 0.12 | ND |
| 335 | 0.038 | ND | 0.14 | ND |
| 336 | 0.13 | ND | 0.22 | ND |
| 337 | 0.10 | ND | 1.4 | ND |
| 338 | 0.38 | ND | ND | ND |
| 339 | 0.022 | 0.014 | 0.059 | 0.023 |
| 340 | 2.3 | ND | ND | ND |
| 341 | 0.037 | 0.011 | 0.09 | 0.022 |
| 342 | 0.034 | ND | 0.28 | ND |
| 343 | 0.048 | ND | 0.22 | ND |
| 344 | 0.021 | ND | 0.44 | ND |
| 345 | 0.014 | 0.010 | 0.042 | 0.017 |
| 346 | 0.042 | ND | 0.25 | ND |
| 347 | 0.022 | 0.007 | 0.018 | 0.010 |
| 348 | 3.4 | ND | ND | ND |
| 349 | 0.51 | ND | ND | ND |
| 350 | 1.9 | ND | ND | ND |
| 351 | 0.27 | ND | 0.31 | ND |
| 352 | 0.63 | ND | ND | ND |
| 353 | 0.051 | ND | 0.05 | 0.048 |
| 354 | 0.036 | ND | 0.057 | 0.028 |
| 355 | 0.032 | ND | 0.076 | 0.054 |
| 356 | 0.014 | ND | 0.21 | ND |
| 357 | 0.034 | ND | 0.089 | 0.055 |
| 358 | 0.13 | ND | 3.6 | ND |
| 359 | 0.46 | ND | 4.0 | ND |
| 360 | 0.035 | ND | 0.39 | ND |
| 361 | 0.042 | 0.018 | 0.10 | 0.030 |
| 362 | 0.15 | ND | 0.76 | ND |
| 363 | 0.045 | ND | 0.15 | ND |
| 364 | 0.044 | ND | 0.39 | ND |
| 365 | 0.034 | 0.006 | 0.022 | 0.011 |
| 366 | 0.053 | ND | 0.46 | ND |
| 367 | 0.024 | ND | 0.20 | ND |
| 368 | 0.056 | ND | 0.40 | ND |
| 369 | 0.027 | 0.005 | 0.039 | 0.010 |
| 370 | 0.009 | 0.010 | 0.046 | 0.028 |
| 371 | 0.015 | ND | 0.16 | ND |
| 372 | 0.017 | ND | 0.11 | ND |
| 373 | 0.071 | ND | 0.84 | ND |
| 374 | 0.015 | ND | 0.44 | ND |
| 375 | 0.47 | ND | ND | ND |
| 376 | 0.22 | ND | 0.38 | ND |
| 377 | 0.46 | ND | ND | ND |
| 378 | 0.26 | ND | 0.2 | ND |
| 379 | 0.066 | ND | 0.54 | ND |
| 380 | 0.091 | ND | 0.27 | ND |
| 381 | 0.23 | ND | 0.21 | ND |
| 382 | 0.027 | ND | 0.14 | ND |
| 383 | 0.054 | ND | 0.85 | ND |
| 384 | 0.049 | 0.026 | 0.064 | 0.042 |
| 385 | 0.062 | ND | 0.32 | ND |
| 386 | 0.092 | ND | 0.34 | ND |
| 387 | 0.05 | ND | 0.33 | ND |
| 388 | 0.22 | ND | 0.66 | ND |
| 389 | 0.1 | 0.078 | 0.11 | 0.15 |
| 390 | 0.076 | ND | 0.59 | ND |
| 391 | 0.032 | 0.010 | 0.048 | 0.021 |
| 392 | 0.028 | ND | 0.12 | ND |
| 393 | 0.10 | ND | 0.43 | ND |
| 394 | 0.076 | ND | 0.22 | ND |
| 395 | 0.066 | ND | 0.38 | ND |
| 396 | 0.094 | ND | 0.62 | ND |
| 397 | 0.076 | ND | 0.75 | ND |
| 398 | 0.1 | ND | 0.39 | ND |
| 399 | 0.061 | ND | 0.56 | ND |
| 400 | 0.27 | ND | ND | ND |
| 401 | 0.10 | ND | ND | ND |
| 402 | 0.19 | ND | ND | ND |
| 403 | 0.45 | ND | ND | ND |
| 404 | 0.064 | ND | 0.24 | ND |
| 405 | 0.64 | ND | ND | ND |
| 406 | 0.16 | ND | 0.20 | ND |
| 407 | 0.049 | 0.021 | 0.072 | 0.092 |
| 408 | 0.035 | 0.007 | 0.032 | 0.017 |
| 409 | 1.1 | ND | ND | ND |
| 410 | 0.023 | 0.093 | 0.11 | 0.24 |
| 411 | 0.022 | ND | 0.14 | ND |
| 412 | 0.17 | ND | 0.26 | ND |
| 413 | 0.14 | ND | 1.7 | ND |
| 414 | 0.095 | 0.077 | 0.069 | 0.18 |
| 415 | 0.11 | ND | 0.37 | ND |
| 416 | 0.037 | 0.014 | 0.022 | 0.055 |
| 417 | 0.089 | 0.028 | 0.048 | 0.12 |
| 418 | 0.031 | ND | 0.17 | ND |
| 419 | 0.052 | ND | 0.14 | ND |
| 420 | 0.039 | 0.031 | 0.061 | 0.077 |
| 421 | 0.027 | ND | 0.14 | ND |
| 422 | 0.048 | ND | 0.21 | ND |
| 423 | 0.21 | ND | 0.37 | ND |
| 424 | 0.31 | ND | 0.12 | ND |
| 425 | 0.14 | ND | 0.56 | ND |
| 426 | 0.096 | ND | 0.18 | ND |
| 427 | 0.009 | 0.011 | 0.019 | 0.013 |
| 428 | 0.079 | ND | 0.31 | ND |
| 429 | 0.033 | ND | 0.52 | ND |
| 430 | 0.07 | 0.067 | 0.072 | 0.17 |
| 431 | 0.018 | 0.010 | 0.021 | 0.029 |
| 432 | 0.063 | ND | 0.48 | ND |

TABLE 1-continued

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 433 | 0.055 | ND | 0.17 | ND |
| 434 | 0.096 | ND | 0.30 | ND |
| 435 | 0.055 | ND | 0.34 | ND |
| 436 | 0.059 | ND | 0.24 | ND |
| 437 | 0.18 | ND | 0.29 | ND |
| 438 | 0.18 | ND | 0.47 | ND |
| 439 | 0.042 | 0.039 | 0.078 | ND |
| 440 | 0.034 | ND | 0.13 | ND |
| 441 | 0.06 | 0.022 | 0.024 | 0.051 |
| 442 | 0.04 | ND | 0.17 | ND |
| 443 | 0.21 | ND | 1.51 | ND |
| 444 | 0.017 | 0.010 | 0.071 | ND |
| 445 | 0.18 | 0.12 | 0.10 | ND |
| 446 | 0.34 | ND | ND | ND |
| 447 | 0.16 | ND | 0.12 | ND |
| 448 | 0.021 | 0.55 | 0.097 | ND |
| 449 | 0.062 | ND | 0.31 | ND |
| 450 | 0.021 | 0.010 | 0.032 | ND |
| 451 | 0.032 | ND | 0.32 | ND |
| 452 | 0.041 | 0.013 | 0.020 | ND |
| 453 | 0.041 | ND | 0.31 | ND |
| 454 | 0.021 | ND | 0.40 | ND |
| 455 | 0.029 | ND | 0.23 | ND |
| 456 | 0.091 | ND | 0.16 | ND |
| 457 | 0.15 | ND | 0.45 | ND |
| 458 | 0.083 | ND | 0.13 | ND |
| 459 | 0.057 | ND | 0.37 | ND |
| 460 | 0.47 | ND | ND | ND |
| 461 | 0.60 | ND | ND | ND |
| 462 | 0.091 | ND | 0.26 | ND |
| 463 | 0.11 | ND | 0.33 | ND |
| 464 | 0.079 | ND | 0.16 | ND |
| 465 | 0.19 | ND | 0.56 | ND |
| 466 | 0.18 | ND | 0.93 | ND |
| 467 | 0.13 | ND | 1.39 | ND |
| 468 | 5 | ND | ND | ND |
| 469 | 0.09 | 0.12 | 0.16 | 0.24 |
| 470 | 0.14 | ND | 0.97 | ND |
| 471 | 0.18 | ND | 1.5 | ND |
| 472 | 8 | ND | ND | ND |
| 473 | 0.80 | ND | ND | ND |
| 474 | 0.23 | ND | 0.79 | ND |
| 475 | 0.47 | ND | ND | ND |
| 476 | 0.07 | 0.016 | 0.027 | ND |
| 477 | 1 | ND | ND | ND |
| 478 | 2.8 | ND | ND | ND |
| 479 | 1.9 | ND | ND | ND |
| 480 | 0.18 | ND | 1.6 | ND |
| 481 | 2.8 | ND | ND | ND |
| 482 | 1.6 | ND | ND | ND |
| 483 | 3.6 | ND | ND | ND |
| 484 | 0.017 | 0.005 | 0.027 | ND |
| 485 | 0.007 | 0.009 | 0.024 | ND |
| 486 | 0.24 | ND | 1.9 | ND |
| 487 | 0.72 | ND | ND | ND |
| 488 | 1.3 | ND | ND | ND |
| 489 | 2.1 | ND | ND | ND |
| 490 | 0.64 | ND | ND | ND |
| 491 | 1.8 | ND | ND | ND |
| 492 | 1.5 | ND | ND | ND |
| 493 | 0.17 | ND | 6.6 | ND |
| 494 | 9.1 | ND | ND | ND |
| 495 | 0.13 | ND | 8 | ND |
| 496 | 6.1 | ND | ND | ND |
| 497 | 0.83 | ND | ND | ND |
| 498 | 0.051 | ND | 0.38 | ND |
| 499 | 0.67 | ND | ND | ND |
| 500 | >12.5 | ND | ND | ND |
| 501 | 0.69 | ND | ND | ND |
| 502 | 0.17 | ND | 1.5 | ND |
| 503 | 4.7 | ND | ND | ND |
| 504 | 11.2 | ND | ND | ND |
| 505 | 0.16 | ND | 1.9 | ND |
| 506 | 7.9 | ND | ND | ND |
| 507 | >12.5 | ND | ND | ND |
| 508 | 0.30 | 0.031 | 0.042 | 0.10 |
| 509 | 0.037 | 0.011 | 0.052 | 0.055 |
| 510 | 0.47 | ND | ND | ND |
| 511 | 0.018 | ND | 0.34 | ND |
| 512 | 1.5 | ND | ND | ND |
| 513 | 4.8 | ND | ND | ND |
| 514 | 0.23 | ND | 1.5 | ND |
| 515 | 6.3 | ND | ND | ND |
| 516 | 0.44 | ND | ND | ND |
| 517 | 2.6 | ND | ND | ND |
| 518 | 0.76 | ND | ND | ND |
| 519 | 3.5 | ND | ND | ND |
| 520 | 4 | ND | ND | ND |
| 521 | 2 | ND | ND | ND |
| 522 | 0.13 | ND | 1.0 | ND |
| 523 | 0.093 | ND | 0.53 | ND |
| 524 | 0.12 | ND | 1.0 | ND |
| 525 | 0.13 | ND | 0.76 | ND |
| 526 | 6.2 | ND | ND | ND |
| 527 | 2.4 | ND | ND | ND |
| 528 | 0.098 | 0.064 | 0.056 | 0.14 |
| 529 | 1.5 | ND | ND | ND |
| 530 | 0.053 | ND | 2.0 | ND |
| 531 | 0.13 | ND | 2.6 | ND |
| 532 | 0.25 | ND | >10 | ND |
| 533 | 0.055 | ND | 0.17 | ND |
| 534 | 0.055 | ND | 0.36 | ND |
| 535 | 0.044 | ND | 0.24 | ND |
| 536 | 0.038 | ND | 0.15 | ND |
| 537 | 0.045 | ND | 0.84 | ND |
| 538 | 0.15 | ND | >10 | ND |
| 539 | 0.043 | 0.040 | 0.055 | 0.081 |
| 540 | 0.046 | ND | 0.12 | ND |
| 541 | 0.063 | 0.030 | 0.047 | 0.064 |
| 542 | 1.5 | ND | ND | ND |
| 543 | 0.49 | ND | ND | ND |
| 544 | 8.1 | ND | ND | ND |
| 545 | >12.5 | ND | ND | ND |
| 546 | >12.5 | ND | ND | ND |
| 547 | 0.13 | ND | 1.5 | ND |
| 548 | 7.6 | ND | ND | ND |
| 549 | 0.064 | ND | 0.22 | ND |
| 550 | >12.5 | ND | ND | ND |
| 551 | 0.36 | ND | ND | ND |
| 552 | 4.4 | ND | ND | ND |
| 553 | 0.67 | ND | ND | ND |
| 554 | 0.052 | ND | 0.25 | ND |
| 555 | 0.07 | ND | 0.51 | ND |
| 556 | 3.7 | ND | ND | ND |
| 557 | 1.2 | ND | ND | ND |
| 558 | 0.9 | ND | ND | ND |
| 559 | 0.49 | ND | 1.8 | ND |
| 560 | 0.67 | ND | ND | ND |
| 561 | 0.77 | ND | ND | ND |
| 562 | 0.96 | ND | ND | ND |
| 563 | 0.092 | ND | 0.44 | ND |
| 564 | 0.095 | ND | 0.49 | ND |
| 565 | 0.046 | ND | 0.85 | ND |
| 566 | 0.059 | ND | 0.44 | ND |
| 567 | 0.085 | ND | 0.87 | ND |
| 568 | 0.025 | ND | 0.46 | ND |
| 569 | 0.042 | ND | 0.28 | ND |
| 570 | 0.2 | ND | 0.23 | ND |
| 571 | 0.28 | ND | 0.14 | ND |
| 572 | 0.056 | ND | 0.46 | ND |
| 573 | 0.059 | ND | 0.35 | ND |
| 574 | 0.12 | ND | 0.63 | ND |
| 575 | 0.10 | ND | 0.68 | ND |
| 576 | 0.042 | ND | 0.13 | ND |
| 577 | 0.046 | ND | 0.27 | ND |
| 578 | 0.061 | 1.1 | 1.3 | ND |
| 579 | 0.047 | ND | 0.53 | ND |
| 580 | 0.081 | ND | 1.2 | ND |
| 581 | 6.6 | ND | ND | ND |
| 582 | 0.069 | ND | 0.23 | ND |

TABLE 1-continued

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 583 | 0.03 | 0.092 | 0.089 | 0.17 |
| 584 | 0.10 | ND | 0.26 | ND |
| 585 | 0.060 | 0.045 | 0.089 | 0.18 |
| 586 | 0.10 | ND | 0.80 | ND |
| 587 | 0.028 | ND | 0.53 | ND |
| 588 | 0.043 | ND | 0.83 | ND |
| 589 | 0.044 | ND | 0.83 | ND |
| 590 | 0.024 | ND | 0.18 | ND |
| 591 | 0.023 | ND | 0.33 | ND |
| 592 | 0.037 | ND | 0.27 | ND |
| 593 | 0.032 | ND | 0.25 | ND |
| 594 | 0.034 | ND | 0.41 | ND |
| 595 | 0.14 | ND | 0.36 | ND |
| 596 | 0.074 | ND | 0.57 | ND |
| 597 | 0.041 | ND | 0.70 | ND |
| 598 | 0.050 | ND | 0.59 | ND |
| 599 | 0.10 | ND | 0.85 | ND |
| 600 | 0.039 | ND | 1.3 | ND |
| 601 | 0.021 | ND | 0.15 | ND |
| 602 | 0.020 | ND | 0.23 | ND |
| 603 | 0.082 | 0.59 | 0.94 | ND |
| 604 | 0.027 | ND | 0.143 | ND |
| 605 | 0.080 | 0.45 | 1.1 | ND |
| 606 | 0.006 | ND | 2.8 | ND |
| 607 | 0.012 | ND | 1.3 | ND |
| 608 | 0.004 | ND | 0.11 | ND |
| 609 | 0.016 | ND | 0.38 | ND |
| 610 | 0.035 | ND | 0.23 | ND |
| 611 | 0.046 | ND | 0.70 | ND |
| 612 | 0.045 | ND | 0.28 | ND |
| 613 | 0.042 | ND | 0.18 | ND |
| 614 | 0.077 | ND | 0.30 | ND |
| 615 | 0.033 | ND | 0.16 | ND |
| 616 | 0.036 | ND | 0.67 | ND |
| 617 | 0.061 | ND | >3 | ND |
| 618 | 0.046 | ND | 3.5 | ND |
| 619 | 0.043 | ND | 1.8 | ND |
| 620 | 0.055 | ND | 0.27 | ND |
| 621 | 0.017 | ND | 0.15 | ND |
| 622 | 0.038 | ND | 0.27 | ND |
| 623 | 0.056 | 0.99 | 0.45 | 2.55 |
| 624 | 0.10 | ND | 0.50 | ND |
| 625 | 0.03 | ND | 2.6 | ND |
| 626 | 0.098 | ND | 0.12 | ND |
| 627 | 0.020 | ND | 0.069 | ND |
| 628 | 0.11 | ND | 2.4 | ND |
| 629 | 0.21 | ND | 2.3 | ND |
| 630 | 0.024 | ND | 3.0 | ND |
| 631 | 0.043 | ND | 0.87 | ND |
| 632 | 0.046 | ND | 0.58 | ND |
| 633 | 0.075 | ND | 0.81 | ND |
| 634 | 0.045 | ND | 1.5 | ND |
| 635 | 0.043 | 0.081 | 0.20 | 0.29 |
| 636 | 0.019 | ND | 0.20 | ND |
| 637 | 0.056 | ND | 0.64 | ND |
| 638 | 0.038 | ND | 0.41 | ND |
| 639 | 0.042 | ND | 0.17 | ND |
| 640 | 0.11 | ND | 2.1 | ND |
| 641 | 0.040 | ND | 0.49 | ND |
| 642 | 0.078 | ND | 0.25 | ND |
| 643 | 0.039 | ND | 0.67 | ND |
| 644 | 0.28 | ND | ND | ND |
| 645 | 0.065 | ND | 0.53 | ND |
| 646 | 0.019 | ND | 0.25 | ND |
| 647 | 0.020 | ND | 0.51 | ND |
| 648 | 0.035 | ND | 0.12 | ND |
| 649 | 0.056 | ND | 0.24 | ND |
| 650 | 0.031 | ND | 0.42 | ND |
| 651 | 0.023 | ND | 0.55 | ND |
| 652 | 0.034 | ND | 0.32 | ND |
| 653 | 0.043 | ND | 0.58 | ND |
| 654 | 0.036 | ND | 0.46 | ND |
| 655 | 0.026 | ND | 0.52 | ND |
| 656 | 0.15 | ND | 5.4 | ND |
| 657 | 0.059 | ND | 0.85 | ND |
| 658 | 0.016 | ND | 0.13 | ND |
| 659 | 0.068 | ND | 1.4 | ND |
| 660 | 0.020 | ND | 3.2 | ND |
| 661 | 0.028 | 0.043 | 0.10 | 0.15 |
| 662 | 0.028 | 0.030 | 0.083 | 0.070 |
| 663 | 0.082 | ND | 0.29 | ND |
| 664 | 0.13 | ND | 1.5 | ND |
| 665 | 0.010 | 0.024 | 0.069 | 0.023 |
| 666 | 0.028 | 0.042 | 0.13 | 0.11 |
| 667 | 0.026 | 0.060 | 0.081 | 0.13 |
| 668 | 0.038 | ND | 0.48 | ND |
| 669 | 0.044 | ND | 0.175 | ND |
| 670 | 0.017 | ND | 0.16 | ND |
| 671 | 0.017 | 0.057 | 0.11 | 0.17 |
| 672 | 0.024 | ND | 0.19 | ND |
| 673 | 0.019 | 0.014 | 0.1 | 0.027 |
| 674 | 0.029 | ND | 0.11 | ND |
| 675 | 0.025 | ND | 0.12 | ND |
| 676 | 0.077 | ND | 1.2 | ND |
| 677 | 0.074 | ND | 0.16 | ND |
| 678 | 0.061 | ND | 0.27 | ND |
| 679 | 4.3 | ND | ND | ND |
| 680 | 0.062 | ND | 0.12 | ND |
| 681 | 0.047 | ND | 0.48 | ND |
| 682 | 0.34 | ND | 0.81 | ND |
| 683 | 0.39 | ND | 2.0 | ND |
| 684 | 0.024 | ND | 0.3 | ND |
| 685 | 0.03 | ND | 0.15 | ND |
| 686 | 0.072 | ND | 0.52 | ND |
| 687 | 0.073 | ND | 0.19 | ND |
| 688 | 0.050 | ND | 0.21 | ND |
| 689 | 0.043 | ND | 0.27 | ND |
| 690 | 0.037 | ND | 0.37 | ND |
| 691 | 0.044 | ND | 0.72 | ND |
| 692 | 0.057 | ND | 1.7 | ND |
| 693 | 0.037 | ND | 0.57 | ND |
| 694 | 0.051 | ND | 0.13 | ND |
| 695 | 0.023 | ND | 0.032 | ND |
| 696 | 0.042 | ND | 0.11 | ND |
| 697 | 0.054 | 0.045 | 0.079 | 0.16 |
| 698 | 0.021 | 0.009 | 0.034 | 0.029 |
| 699 | 0.043 | 0.043 | 0.14 | 0.13 |
| 700 | 0.037 | ND | 0.095 | ND |
| 701 | 0.042 | ND | 0.24 | ND |
| 702 | 0.028 | 0.048 | 0.087 | 0.16 |
| 703 | 0.15 | ND | 2.2 | ND |
| 704 | 0.054 | ND | 7.5 | ND |
| 705 | 0.059 | ND | 1.3 | ND |
| 706 | 0.028 | ND | 0.22 | ND |
| 707 | 0.050 | ND | 0.53 | ND |
| 708 | 0.043 | ND | 0.42 | ND |
| 709 | 0.043 | ND | 0.49 | ND |
| 710 | 0.032 | ND | 0.22 | ND |
| 711 | 0.032 | ND | 0.20 | ND |
| 712 | 0.019 | ND | 0.12 | ND |
| 713 | 0.021 | ND | 0.14 | ND |
| 714 | 0.020 | 0.014 | 0.094 | 0.048 |
| 715 | 0.035 | ND | 0.19 | ND |
| 716 | 0.027 | 0.034 | 0.086 | 0.20 |
| 717 | 0.042 | 0.011 | 0.091 | 0.039 |
| 718 | 0.023 | 0.017 | 0.073 | 0.088 |
| 719 | 0.024 | ND | 0.36 | ND |
| 720 | 0.026 | ND | 0.18 | ND |
| 721 | 0.031 | ND | 0.23 | ND |
| 722 | 0.043 | ND | 1.0 | ND |
| 723 | 0.095 | ND | 1.5 | ND |
| 724 | 0.064 | ND | 1.2 | ND |
| 725 | 0.053 | ND | 0.70 | ND |
| 726 | 0.039 | ND | 0.49 | ND |
| 727 | 0.049 | ND | 0.39 | ND |
| 728 | 0.049 | ND | 0.48 | ND |
| 729 | 0.077 | ND | 0.93 | ND |
| 730 | 0.078 | ND | 0.76 | ND |
| 731 | 0.17 | ND | 1.9 | ND |
| 732 | 0.030 | ND | 0.36 | ND |

TABLE 1-continued

| EXAMPLE | CDK9/Cyclin T1 IC$_{50}$ (µM) | Cell Viability A-431 IC$_{50}$ (µM) | Cell Viability H929 IC$_{50}$ (µM) | ICW IC$_{50}$ (µM) |
|---|---|---|---|---|
| 733 | 0.038 | ND | 0.46 | ND |
| 734 | 0.047 | 0.054 | 0.20 | 0.25 |
| 735 | 0.057 | ND | 0.28 | ND |
| 736 | 0.094 | ND | 0.33 | ND |
| 737 | 0.085 | ND | 0.64 | ND |
| 738 | 0.21 | ND | 0.78 | ND |
| 739 | 0.14 | ND | 0.29 | ND |
| 740 | 0.054 | ND | 0.06 | ND |
| 741 | 0.082 | ND | 0.16 | ND |
| 742 | 0.25 | ND | 1.6 | ND |
| 743 | 0.047 | ND | 0.26 | ND |
| 744 | 0.078 | ND | 0.61 | ND |
| 745 | 0.13 | ND | 1.9 | ND |
| 746 | 0.15 | ND | 0.24 | ND |
| 747 | 0.091 | ND | 0.21 | ND |
| 748 | 0.11 | ND | 1.4 | ND |
| 749 | 0.11 | ND | 0.18 | ND |
| 750 | 0.077 | ND | 0.14 | ND |
| 751 | 0.064 | ND | 0.22 | ND |
| 752 | 0.10 | ND | 0.16 | ND |
| 753 | 0.11 | ND | 0.16 | ND |
| 754 | 0.11 | ND | 0.24 | ND |
| 755 | 0.54 | ND | 8.4 | ND |
| 756 | 0.29 | ND | 2.8 | ND |
| 757 | 0.30 | ND | 2.2 | ND |
| 758 | 0.16 | ND | 1.4 | ND |
| 759 | 0.062 | ND | 0.51 | ND |
| 760 | 0.067 | 0.094 | 0.11 | 0.24 |
| 761 | 0.17 | ND | 1.6 | ND |
| 762 | 0.097 | ND | 0.24 | ND |
| 763 | 0.089 | ND | 0.13 | ND |
| 764 | 0.11 | 0.078 | 0.11 | 0.13 |
| 765 | 0.12 | ND | 0.10 | ND |
| 766 | 0.059 | ND | 8.7 | ND |
| 767 | 0.34 | ND | 5.5 | ND |
| 768 | 0.081 | ND | 0.88 | ND |
| 769 | 0.25 | ND | 0.53 | ND |
| 770 | 0.1 | ND | 0.42 | ND |
| 771 | 0.16 | ND | 2.3 | ND |
| 772 | 0.081 | ND | 0.83 | ND |
| 773 | 0.053 | ND | 0.093 | ND |
| 774 | 0.095 | 0.11 | 0.14 | 0.33 |
| 775 | 0.11 | ND | 0.50 | ND |
| 776 | 0.79 | ND | 3.8 | ND |
| 777 | 0.092 | ND | 0.18 | ND |
| 778 | 0.14 | ND | 0.92 | ND |
| 779 | 0.066 | ND | 2.0 | ND |
| 780 | 0.1 | ND | 0.40 | ND |
| 781 | 0.15 | ND | 1.71 | ND |
| 782 | 0.065 | 0.076 | 0.084 | 0.32 |
| 783 | 0.056 | 0.042 | 0.045 | 0.18 |
| 784 | 0.24 | ND | 0.59 | ND |
| 785 | 0.058 | 0.43 | 0.096 | 1.06 |
| 786 | 0.034 | ND | 0.60 | ND |
| 787 | 0.9 | ND | >10 | ND |
| 788 | 0.023 | 0.039 | 0.073 | 0.028 |
| 789 | 0.027 | ND | 0.32 | ND |
| 790 | 0.025 | ND | 0.14 | ND |
| 791 | 0.067 | ND | 0.54 | ND |
| 792 | 0.035 | ND | 0.12 | ND |
| 793 | 0.019 | ND | 0.074 | ND |
| 794 | 0.19 | ND | 0.79 | ND |
| 795 | 2.0 | ND | >10 | ND |
| 796 | 0.031 | ND | 0.71 | ND |
| 797 | 0.034 | ND | 0.59 | ND |
| 798 | 0.045 | 0.053 | 0.10 | 0.14 |
| 799 | 0.14 | ND | 0.24 | ND |
| 800 | 0.043 | 0.14 | 0.095 | 0.32 |
| 801 | 0.029 | ND | 0.33 | ND |
| 802 | 0.18 | ND | 0.55 | ND |
| 803 | 0.067 | ND | 0.93 | ND |
| 804 | 0.03 | 0.051 | 0.097 | 0.18 |
| 805 | 0.059 | ND | 1.1 | ND |
| 806 | 0.11 | ND | 0.37 | ND |
| 807 | 0.06 | ND | 2.0 | ND |
| 808 | 0.025 | ND | 1.2 | ND |
| 809 | 0.024 | 0.044 | 0.040 | 0.13 |
| 810 | 0.2 | ND | 1.4 | ND |
| 811 | 0.19 | ND | 2.5 | ND |
| 812 | 0.11 | ND | 1.1 | ND |
| 813 | 8.9 | ND | >10 | ND |
| 814 | 0.13 | ND | 0.20 | ND |
| 815 | 0.12 | ND | 0.051 | ND |
| 816 | 0.11 | 0.27 | 0.11 | 0.28 |
| 817 | 0.076 | ND | 0.045 | ND |
| 818 | 0.087 | ND | 0.33 | ND |
| 819 | 0.17 | ND | 0.45 | ND |
| 820 | 0.11 | ND | 0.32 | ND |
| 821 | 0.14 | ND | 0.37 | ND |
| 822 | 0.54 | ND | >10 | ND |
| 823 | 1.95 | ND | 1.6 | ND |
| 824 | 0.30 | ND | 4.8 | ND |
| 825 | 0.13 | ND | 1.3 | ND |
| 826 | 0.32 | ND | 1.4 | ND |
| 827 | 0.16 | ND | 0.19 | ND |
| 828 | 0.35 | ND | 0.54 | ND |
| 829 | 0.21 | ND | 0.37 | ND |
| 830 | 0.17 | ND | 0.44 | ND |
| 831 | 0.34 | ND | 0.97 | ND |
| 832 | 0.11 | ND | 0.42 | ND |
| 833 | 0.15 | ND | 1.0 | ND |
| 834 | 0.085 | ND | 0.30 | ND |
| 835 | 0.050 | ND | 0.23 | ND |
| 836 | 0.14 | ND | 0.55 | ND |
| 837 | 0.11 | ND | 0.31 | ND |
| 838 | 0.27 | ND | 0.72 | ND |
| 839 | 0.21 | ND | 0.35 | ND |
| 840 | 0.078 | ND | 0.39 | ND |
| 841 | 0.24 | ND | 0.87 | ND |
| 842 | 0.19 | ND | 2.64 | ND |
| 843 | 0.27 | ND | >10 | ND |
| 844 | 0.13 | ND | >10 | ND |
| 845 | 0.052 | ND | 0.35 | ND |
| 846 | 0.16 | ND | 0.26 | ND |
| 847 | 0.21 | ND | 3.8 | ND |
| 848 | 0.13 | ND | 1.5 | ND |
| 849 | 0.11 | ND | 1.3 | ND |
| 850 | 0.14 | ND | 0.57 | ND |
| 851 | 0.12 | ND | >3 | ND |
| 852 | 0.62 | ND | 2.5 | ND |
| 853 | 0.065 | ND | 0.76 | ND |
| 854 | 0.16 | ND | 7.1 | ND |
| 855 | 0.043 | ND | 0.056 | ND |
| 856 | 0.038 | ND | 0.056 | ND |
| 857 | 0.35 | ND | 3.7 | ND |
| 858 | 0.45 | ND | 10 | ND |
| 859 | 0.28 | ND | 1.9 | ND |
| 860 | 0.21 | ND | 0.15 | ND |
| 861 | 0.20 | ND | 10 | ND |
| 862 | 0.53 | ND | 3.3 | ND |
| 863 | 0.46 | ND | >10 | ND |
| 864 | 0.077 | ND | 0.32 | ND |
| 865 | 0.060 | ND | 0.34 | ND |
| 866 | 0.19 | ND | 1.15 | ND |
| 867 | 0.15 | ND | 9.9 | ND |
| 868 | 0.047 | ND | 0.44 | ND |
| 869 | 0.061 | ND | 0.074 | ND |
| 870 | 0.079 | ND | 0.37 | ND |
| 871 | 0.073 | ND | 1.9 | ND |
| 872 | 0.093 | ND | 1.3 | ND |
| 873 | 0.12 | ND | 0.55 | ND |
| 874 | 0.054 | 0.015 | 0.10 | 0.045 |
| 875 | 0.15 | ND | 0.27 | ND |
| 876 | 0.068 | ND | 0.15 | ND |
| 877 | 0.069 | ND | 0.23 | ND |
| 878 | 0.110 | ND | 1.1 | ND |
| 879 | 0.071 | 0.33 | 0.13 | 0.29 |
| 880 | 0.068 | ND | 0.18 | ND |
| 881 | 0.085 | ND | 0.055 | ND |
| 882 | 0.042 | 0.22 | 0.14 | 0.18 |

TABLE 1-continued

| EXAMPLE | CDK9/Cyclin T1 IC$_{50}$ (µM) | Cell Viability A-431 IC$_{50}$ (µM) | Cell Viability H929 IC$_{50}$ (µM) | ICW IC$_{50}$ (µM) |
|---|---|---|---|---|
| 883 | 0.063 | 0.051 | 0.12 | 0.12 |
| 884 | 0.068 | ND | 1.1 | ND |
| 885 | 0.092 | ND | 0.67 | ND |
| 886 | 0.097 | ND | 0.17 | ND |
| 887 | 0.053 | 0.13 | 0.12 | 0.45 |
| 888 | 0.043 | 0.028 | 0.050 | 0.054 |
| 889 | 0.043 | 0.13 | 0.081 | 0.34 |
| 890 | 0.11 | 0.11 | 0.093 | 0.34 |
| 891 | 0.034 | 0.35 | 0.11 | 0.81 |
| 892 | 0.17 | ND | 1.15 | ND |
| 893 | 0.074 | ND | 0.24 | ND |
| 894 | 0.11 | ND | 1.6 | ND |
| 895 | 0.11 | ND | 3.3 | ND |
| 896 | 0.052 | 0.054 | 0.062 | 0.099 |
| 897 | 0.89 | ND | 2.1 | ND |
| 898 | 0.031 | 0.12 | 0.10 | 0.16 |
| 899 | 0.066 | ND | 0.30 | ND |
| 900 | 0.022 | ND | 0.008 | ND |
| 901 | 0.057 | ND | 0.20 | ND |
| 902 | 0.062 | ND | 0.080 | ND |
| 903 | 0.24 | ND | 2.7 | ND |
| 904 | 0.105 | ND | 0.40 | ND |
| 905 | 4.1 | ND | >10 | ND |
| 906 | 0.34 | ND | 0.52 | ND |
| 907 | 0.049 | 0.36 | 0.084 | 0.19 |
| 908 | 0.16 | ND | 0.30 | ND |
| 909 | 0.079 | ND | 0.55 | ND |
| 910 | 0.029 | 0.13 | 0.045 | 0.21 |
| 911 | 0.045 | ND | 0.28 | ND |
| 912 | 0.047 | ND | 0.25 | ND |
| 913 | 0.059 | ND | 0.19 | ND |
| 914 | 0.084 | ND | 0.19 | ND |
| 915 | 0.083 | ND | 0.092 | ND |
| 916 | 0.019 | 0.019 | 0.015 | 0.031 |
| 917 | 0.053 | 0.087 | 0.03 | 0.073 |
| 918 | 0.044 | ND | 0.16 | ND |
| 919 | 0.38 | ND | 2.5 | ND |
| 920 | 0.52 | ND | 6.8 | ND |
| 921 | 0.035 | 0.076 | 0.061 | 0.12 |
| 922 | 0.32 | ND | 2 | ND |
| 923 | 0.15 | ND | 2.8 | ND |
| 924 | 0.10 | ND | 0.58 | ND |
| 925 | 0.17 | ND | 0.44 | ND |
| 926 | 0.058 | ND | 0.32 | ND |
| 927 | 0.091 | ND | 6.7 | ND |
| 928 | 0.063 | ND | 5.3 | ND |
| 929 | 0.10 | ND | 0.23 | ND |
| 930 | 0.082 | ND | 0.22 | ND |
| 931 | 0.51 | ND | 0.84 | ND |
| 932 | 0.081 | ND | 0.2 | ND |
| 933 | 0.085 | ND | 0.14 | ND |
| 934 | 0.054 | ND | >10 | ND |
| 935 | 0.076 | ND | 0.073 | ND |
| 936 | 0.040 | ND | 2.6 | ND |
| 937 | 0.075 | ND | 0.16 | ND |
| 938 | 0.057 | ND | 0.065 | ND |
| 939 | 0.055 | ND | 0.24 | ND |
| 940 | 0.058 | ND | 0.14 | ND |
| 941 | 0.073 | 0.16 | 0.069 | 0.16 |
| 942 | 9.8 | ND | >10 | ND |
| 943 | 0.054 | ND | 0.13 | ND |
| 944 | 0.048 | ND | 0.21 | ND |
| 945 | 0.036 | ND | 0.14 | ND |
| 946 | 0.061 | 0.17 | 0.14 | 0.19 |
| 947 | 0.035 | ND | 0.23 | ND |
| 948 | 0.061 | ND | 0.13 | ND |
| 949 | 0.078 | ND | 0.16 | ND |
| 950 | 0.039 | ND | 0.18 | ND |
| 951 | 0.023 | ND | 0.31 | ND |
| 952 | 0.039 | ND | 0.20 | ND |
| 953 | 0.040 | 0.27 | 0.15 | 0.14 |
| 954 | 0.038 | ND | 0.051 | ND |
| 955 | 0.058 | ND | 0.16 | ND |
| 956 | 0.032 | ND | 0.075 | ND |
| 957 | 0.049 | ND | 0.16 | ND |
| 958 | 0.039 | ND | 0.088 | ND |
| 959 | 0.039 | 0.16 | 0.13 | 0.13 |
| 960 | 0.066 | 0.28 | 0.20 | 0.28 |
| 961 | 0.17 | ND | 2.3 | ND |
| 962 | 0.48 | ND | 1.1 | ND |
| 963 | 0.023 | ND | 6.2 | ND |
| 964 | 0.025 | ND | 0.27 | ND |
| 965 | 0.03 | ND | 0.26 | ND |
| 966 | 0.054 | ND | 0.38 | ND |
| 967 | 0.051 | ND | 0.25 | ND |
| 968 | 0.043 | 0.27 | 0.19 | 0.41 |
| 969 | 0.043 | ND | 0.26 | ND |
| 970 | 0.047 | ND | 0.91 | ND |
| 971 | 0.13 | ND | 0.40 | ND |
| 972 | 0.08 | ND | 0.13 | ND |
| 973 | 0.058 | ND | 0.12 | ND |
| 974 | 0.16 | ND | 0.47 | ND |
| 975 | 0.26 | ND | 1.1 | ND |
| 976 | 0.26 | ND | 0.71 | ND |
| 977 | 0.045 | ND | 0.060 | ND |
| 978 | 0.041 | ND | 0.013 | ND |
| 979 | 0.034 | ND | 0.96 | ND |
| 980 | 0.19 | ND | ND | ND |
| 981 | 0.036 | ND | 1.4 | ND |
| 982 | 0.046 | ND | 0.21 | ND |
| 983 | 0.023 | ND | 0.55 | ND |
| 984 | 0.2 | ND | 1.1 | ND |
| 985 | 0.11 | ND | 0.10 | ND |
| 986 | 0.42 | ND | 0.26 | ND |
| 987 | 0.075 | ND | 0.55 | ND |
| 988 | 0.066 | ND | 0.14 | ND |
| 989 | 0.071 | ND | 0.65 | ND |
| 990 | 0.072 | ND | 0.13 | ND |
| 991 | 0.10 | ND | 0.19 | ND |
| 992 | 0.30 | ND | 0.36 | ND |
| 993 | 0.049 | ND | 0.047 | ND |
| 994 | 0.061 | ND | 0.10 | ND |
| 995 | 0.12 | ND | 0.13 | ND |
| 996 | 0.11 | ND | 0.17 | ND |
| 997 | 0.12 | ND | 0.20 | ND |
| 998 | 0.088 | ND | 0.18 | ND |
| 999 | 0.014 | ND | 0.048 | ND |
| 1000 | 0.11 | ND | 0.20 | ND |
| 1001 | 0.12 | ND | 0.10 | ND |
| 1002 | 0.083 | ND | 0.20 | ND |
| 1003 | 0.06 | ND | 0.073 | ND |
| 1004 | 0.13 | ND | 0.097 | ND |
| 1005 | 0.095 | ND | 0.19 | ND |
| 4006 | 0.072 | ND | 0.032 | ND |
| 1007 | 0.063 | ND | 0.058 | ND |
| 1008 | 0.11 | ND | 0.17 | ND |
| 1009 | 0.15 | ND | 2.0 | ND |
| 1010 | 0.12 | ND | 0.38 | ND |
| 1011 | 0.098 | ND | 0.89 | ND |
| 1012 | 0.088 | ND | 2.0 | ND |
| 1013 | 0.083 | ND | 0.21 | ND |
| 1014 | 0.066 | ND | 0.65 | ND |
| 1015 | 0.075 | ND | 0.97 | ND |
| 1016 | 0.11 | ND | 0.50 | ND |
| 1017 | 0.084 | 0.043 | 0.03 | 0.082 |
| 1018 | 0.12 | ND | 0.15 | ND |
| 1019 | 0.24 | ND | 0.17 | ND |
| 1020 | 0.18 | ND | 1.9 | ND |
| 1021 | 0.095 | ND | 0.082 | ND |
| 1022 | 0.11 | ND | 0.18 | ND |
| 1023 | 0.11 | ND | 0.34 | ND |
| 1024 | 0.078 | ND | 0.050 | ND |
| 1025 | 0.057 | ND | 0.083 | ND |
| 1026 | 0.12 | ND | 1.2 | ND |
| 1027 | 0.066 | ND | 2.6 | ND |
| 1028 | 0.15 | ND | 0.82 | ND |
| 1029 | 0.11 | ND | 0.20 | ND |
| 1030 | 0.070 | ND | 0.28 | ND |
| 1031 | 0.85 | ND | 0.35 | ND |
| 1032 | 0.44 | ND | 0.37 | ND |

TABLE 1-continued

| EXAMPLE | CDK9/Cyclin T1 IC$_{50}$ (µM) | Cell Viability A-431 IC$_{50}$ (µM) | Cell Viability H929 IC$_{50}$ (µM) | ICW IC$_{50}$ (µM) |
|---|---|---|---|---|
| 1033 | 0.14 | ND | 0.008 | ND |
| 1034 | 0.19 | ND | 0.011 | ND |
| 1035 | 0.060 | ND | 0.13 | ND |
| 1036 | 0.097 | ND | 0.023 | ND |
| 1037 | 0.068 | ND | 0.15 | ND |
| 1038 | 0.084 | ND | 0.43 | ND |
| 1039 | 0.12 | ND | 0.31 | ND |
| 1040 | 0.10 | ND | 0.24 | ND |
| 1041 | 0.25 | ND | 0.60 | ND |
| 1042 | 0.15 | ND | 0.36 | ND |
| 1043 | 0.054 | 0.016 | 0.016 | 0.021 |
| 1044 | 0.056 | 0.033 | 0.034 | 0.048 |
| 1045 | 0.041 | 0.069 | 0.070 | 0.12 |
| 1046 | 0.14 | ND | 0.14 | ND |
| 1047 | 0.055 | ND | 0.037 | ND |
| 1048 | 0.049 | ND | 0.96 | ND |
| 1049 | 0.17 | ND | 0.37 | ND |
| 1050 | 0.15 | ND | 0.24 | ND |
| 1051 | 0.12 | ND | 0.24 | ND |
| 1052 | 0.078 | ND | 0.15 | ND |
| 1053 | 0.13 | ND | 0.17 | ND |
| 1054 | 0.24 | ND | 0.65 | ND |
| 1055 | 0.042 | ND | 0.091 | ND |
| 1056 | 0.056 | ND | 0.41 | ND |
| 1057 | 0.084 | ND | 0.74 | ND |
| 1058 | 0.087 | ND | 0.36 | ND |
| 1059 | 0.061 | ND | 0.48 | ND |
| 1060 | 0.041 | 0.096 | 0.095 | 0.30 |
| 1061 | 0.18 | ND | 0.22 | ND |
| 1062 | 0.088 | 0.026 | 0.025 | 0.020 |
| 1063 | 0.14 | ND | 0.14 | ND |
| 1064 | 0.13 | ND | 0.20 | ND |
| 1065 | 0.12 | ND | 0.56 | ND |
| 1066 | 0.077 | ND | 0.15 | ND |
| 1067 | 0.043 | ND | >10 | ND |
| 1068 | 0.37 | ND | 0.48 | ND |
| 1069 | 0.37 | ND | 0.19 | ND |
| 1070 | 0.067 | 0.025 | 0.028 | 0.027 |
| 1071 | 0.042 | 0.058 | 0.060 | 0.055 |
| 1072 | 0.16 | ND | 1.5 | ND |
| 1073 | 0.080 | 0.042 | 0.047 | 0.15 |
| 1074 | 0.080 | ND | 0.19 | ND |
| 1075 | 0.069 | ND | 0.16 | ND |
| 1076 | 0.068 | 0.050 | 0.056 | 0.13 |
| 1077 | 0.76 | ND | 2.9 | ND |
| 1078 | 9.8 | ND | ND | ND |
| 1079 | 0.30 | ND | 0.31 | ND |
| 1080 | 0.18 | ND | 0.52 | ND |
| 1081 | 0.091 | ND | 0.20 | ND |
| 1082 | 0.14 | ND | 0.27 | ND |
| 1083 | 0.097 | ND | 0.22 | ND |
| 1084 | 0.11 | ND | 0.19 | ND |
| 1085 | 0.058 | ND | 0.11 | ND |
| 1086 | 0.042 | 0.005 | 0.005 | 0.018 |
| 1087 | 9.8 | ND | ND | ND |
| 1088 | 0.15 | ND | 0.68 | ND |
| 1089 | 0.069 | ND | 0.32 | ND |
| 1090 | 0.088 | ND | 0.36 | ND |
| 1091 | 0.11 | ND | 0.29 | ND |
| 1092 | 0.058 | ND | 0.039 | ND |
| 1093 | 0.077 | ND | 3.1 | ND |
| 1094 | 0.037 | ND | 0.030 | ND |
| 1095 | 0.042 | 0.044 | 0.050 | 0.057 |
| 1096 | 0.054 | ND | 0.36 | ND |
| 1097 | 0.079 | 0.13 | 0.085 | 0.19 |
| 1098 | 0.13 | ND | 0.20 | ND |
| 1099 | 1.0 | ND | 0.95 | ND |
| 1100 | 0.056 | ND | 0.099 | ND |
| 1101 | 0.10 | ND | 0.36 | ND |
| 1102 | 0.11 | 0.18 | 0.17 | 0.26 |
| 1103 | 0.044 | ND | 2.7 | ND |
| 1104 | 0.15 | 0.18 | 0.069 | 0.35 |
| 1105 | 0.093 | 0.12 | 0.019 | 0.15 |
| 1106 | 0.12 | 0.033 | 0.013 | 0.046 |
| 1107 | 0.13 | 0.042 | 0.019 | 0.074 |
| 1108 | 0.053 | ND | 0.13 | ND |
| 1109 | 0.056 | 0.17 | 0.086 | 0.19 |
| 1110 | 0.187 | ND | 0.12 | ND |
| 1111 | 0.054 | ND | 0.20 | ND |
| 1112 | 0.092 | 0.34 | 0.14 | 0.48 |
| 1113 | 0.84 | ND | 6.8 | ND |
| 1114 | 0.056 | ND | 0.19 | ND |
| 1115 | 0.088 | ND | 0.26 | ND |
| 1116 | 0.115 | ND | 0.13 | ND |
| 1117 | 0.071 | ND | 0.34 | ND |
| 1118 | 0.024 | ND | 0.010 | ND |
| 1119 | 0.038 | ND | 0.010 | ND |
| 1120 | 0.034 | ND | 0.49 | ND |
| 1121 | 0.083 | 0.023 | 0.019 | 0.027 |
| 1122 | 0.032 | ND | 0.55 | ND |
| 1123 | 0.087 | ND | 0.16 | ND |
| 1124 | 0.13 | ND | 0.27 | ND |
| 1125 | 0.084 | ND | 0.40 | ND |
| 1126 | 0.079 | ND | 0.25 | ND |
| 1127 | 0.050 | 0.35 | 0.24 | 0.44 |
| 1128 | 0.17 | ND | 6.4 | ND |
| 1129 | 0.21 | 0.11 | 0.094 | 0.16 |
| 1130 | 0.13 | ND | 0.20 | ND |
| 1131 | 0.13 | ND | 0.26 | ND |
| 1132 | 0.16 | 0.10 | 0.099 | 0.16 |
| 1133 | 0.21 | ND | 0.15 | ND |
| 1134 | 0.063 | ND | 0.20 | ND |
| 1135 | 0.045 | 0.15 | 0.090 | 0.19 |
| 1136 | 0.068 | ND | 0.18 | ND |
| 1137 | 0.14 | ND | 0.13 | ND |
| 1138 | 0.11 | ND | 0.21 | ND |
| 1139 | 0.042 | 0.044 | 0.049 | 0.14 |
| 1140 | 0.062 | 0.051 | 0.036 | 0.048 |
| 1141 | 0.13 | ND | 0.21 | ND |
| 1142 | 0.085 | ND | 0.16 | ND |
| 1143 | 0.059 | ND | 0.037 | ND |
| 1144 | 0.063 | ND | 0.033 | ND |
| 1145 | 0.17 | ND | 0.42 | ND |
| 1146 | 0.18 | ND | 0.28 | ND |
| 1147 | 0.13 | ND | 0.25 | ND |
| 1148 | 0.065 | 0.085 | 0.044 | 0.18 |
| 1149 | 0.078 | ND | 0.19 | ND |
| 1150 | 0.59 | ND | 1.3 | ND |
| 1151 | 0.075 | 0.082 | 0.069 | 0.16 |
| 1152 | 0.38 | ND | 2.0 | ND |
| 1153 | 0.066 | ND | 0.17 | ND |
| 1154 | 0.061 | 0.24 | 0.15 | 0.74 |
| 1155 | 0.085 | ND | 1.34 | ND |
| 1156 | 0.11 | ND | 0.61 | ND |
| 1157 | 0.10 | ND | 0.18 | ND |
| 1158 | 0.15 | ND | 0.16 | ND |
| 1159 | 0.085 | ND | 0.070 | ND |
| 1160 | 0.090 | ND | 0.076 | ND |
| 1161 | 0.13 | ND | 0.25 | ND |
| 1162 | 0.16 | ND | 0.83 | ND |
| 1163 | 0.19 | ND | 1.56 | ND |
| 1164 | 0.20 | ND | 0.97 | ND |
| 1165 | 0.095 | ND | 0.21 | ND |
| 1166 | 0.056 | ND | 0.18 | ND |
| 1167 | 0.071 | 0.053 | 0.044 | 0.068 |
| 1168 | 0.077 | ND | 0.076 | ND |
| 1169 | 0.059 | ND | 0.12 | ND |
| 1170 | 0.062 | ND | 0.13 | ND |
| 1171 | 0.99 | ND | 1.3 | ND |
| 1172 | 0.096 | ND | 0.73 | ND |
| 1173 | 0.084 | ND | 0.55 | ND |
| 1174 | 0.055 | ND | 0.17 | ND |
| 1175 | 0.16 | ND | 0.085 | ND |
| 1176 | 0.14 | ND | 0.31 | ND |
| 1177 | 0.079 | ND | 0.20 | ND |
| 1178 | 0.13 | ND | 0.38 | ND |
| 1179 | 0.14 | ND | 0.027 | ND |
| 1180 | 0.096 | ND | 0.27 | ND |
| 1181 | 0.12 | ND | 0.12 | ND |
| 1182 | 0.13 | ND | 1.6 | ND |

TABLE 1-continued

| EXAMPLE | CDK9/Cyclin T1 IC$_{50}$ (µM) | Cell Viability A-431 IC$_{50}$ (µM) | Cell Viability H929 IC$_{50}$ (µM) | ICW IC$_{50}$ (µM) |
|---|---|---|---|---|
| 1183 | 0.08 | ND | 0.4 | ND |
| 1184 | 0.15 | ND | 0.33 | ND |
| 1185 | 9.8 | ND | ND | ND |
| 1186 | 5.0 | ND | ND | ND |
| 1187 | 9.8 | ND | >10 | ND |
| 1188 | 1.0 | ND | 0.17 | ND |
| 1189 | 0.077 | 0.034 | 0.031 | 0.040 |
| 1190 | 0.33 | 0.044 | 0.073 | 0.12 |
| 1191 | 0.18 | ND | 0.18 | ND |
| 1192 | 0.044 | 0.074 | 0.042 | 0.19 |
| 1193 | 0.090 | 0.044 | 0.034 | 0.13 |
| 1194 | 0.10 | 0.084 | 0.076 | 0.13 |
| 1195 | 0.21 | ND | 0.49 | ND |
| 1196 | 0.052 | 0.25 | 0.20 | 0.17 |
| 1197 | 0.13 | 0.17 | 0.15 | 0.14 |
| 1198 | 0.056 | ND | 4.3 | ND |
| 1199 | 0.044 | ND | 2.8 | ND |
| 1200 | 1.1 | ND | 0.84 | ND |
| 1201 | 0.87 | ND | 0.22 | ND |
| 1202 | 0.087 | ND | 0.18 | ND |
| 1203 | 0.13 | ND | 3.2 | ND |
| 1204 | 0.36 | ND | 5.1 | ND |
| 1205 | 0.13 | ND | 0.27 | ND |
| 1206 | 0.22 | ND | 0.095 | ND |
| 1207 | 2.3 | ND | 0.22 | ND |
| 1208 | 0.74 | ND | 0.14 | ND |
| 1209 | 0.13 | ND | 4.9 | ND |
| 1210 | 0.23 | ND | 0.17 | ND |
| 1211 | 0.092 | ND | 0.23 | ND |
| 1212 | 0.068 | ND | 0.26 | ND |
| 1213 | 0.093 | 0.092 | 0.095 | 0.21 |
| 1214 | 0.065 | ND | 0.18 | ND |
| 1215 | 0.030 | ND | 0.26 | ND |
| 1216 | 0.14 | ND | 1.1 | ND |
| 1217 | 0.13 | ND | 0.37 | ND |
| 1218 | 0.059 | ND | 7.3 | ND |
| 1219 | 0.15 | ND | 1.9 | ND |
| 1220 | 0.34 | ND | 0.90 | ND |
| 1221 | 0.24 | ND | 2.1 | ND |
| 1222 | 0.075 | ND | 0.46 | ND |
| 1223 | 0.34 | ND | 8.2 | ND |
| 1224 | 0.14 | ND | 0.16 | ND |
| 1225 | 0.050 | ND | 0.17 | ND |
| 1226 | 0.15 | ND | 0.40 | ND |
| 1227 | 0.096 | ND | 1.9 | ND |
| 1228 | 0.12 | ND | 0.17 | ND |
| 1229 | 7.4 | ND | 0.61 | ND |
| 1230 | 0.039 | 0.12 | 0.14 | 0.13 |
| 1231 | 0.22 | ND | 0.58 | ND |
| 1232 | 0.44 | ND | 0.88 | ND |
| 1233 | 0.089 | 0.063 | 0.094 | 0.20 |
| 1234 | 0.074 | ND | 0.32 | ND |
| 1235 | 0.044 | ND | 0.085 | ND |
| 1236 | 0.87 | ND | 3.050 | ND |
| 1237 | 0.16 | ND | 0.84 | ND |
| 1238 | 0.20 | 0.26 | 0.21 | 0.44 |
| 1239 | 0.29 | ND | 1.8 | ND |
| 1240 | 0.13 | ND | 0.90 | ND |
| 1241 | 0.12 | ND | 1.0 | ND |
| 1242 | 0.29 | ND | 1.3 | ND |
| 1243 | 0.16 | ND | 0.90 | ND |
| 1244 | 0.064 | ND | 0.57 | ND |
| 1245 | 0.12 | ND | 0.15 | ND |
| 1246 | 0.068 | ND | 0.047 | ND |
| 1247 | 0.12 | ND | 0.67 | ND |
| 1248 | 0.32 | ND | 0.34 | ND |
| 1249 | 0.057 | ND | 5.6 | ND |
| 1250 | 0.081 | ND | 0.28 | ND |
| 1251 | 0.12 | ND | 0.21 | ND |
| 1252 | 0.12 | ND | 3.4 | ND |
| 1253 | 0.12 | ND | 0.20 | ND |
| 1254 | 0.14 | ND | 0.15 | ND |
| 1255 | 0.084 | ND | 0.88 | ND |
| 1256 | 0.14 | ND | 0.039 | ND |
| 1257 | 0.25 | ND | 0.054 | ND |
| 1258 | 0.18 | ND | 0.49 | ND |
| 1259 | 0.10 | ND | 0.75 | ND |
| 1260 | 0.099 | ND | 0.037 | ND |
| 1261 | 0.15 | ND | 0.64 | ND |
| 1262 | 0.062 | ND | 0.18 | ND |
| 1263 | 0.19 | 0.060 | 0.048 | 0.043 |
| 1264 | 0.11 | ND | 0.18 | ND |
| 1265 | 0.080 | ND | 0.40 | ND |
| 1266 | 0.16 | 0.12 | 0.050 | 0.11 |
| 1267 | 0.12 | 0.016 | 0.010 | 0.019 |
| 1268 | 0.052 | 0.009 | 0.009 | 0.013 |
| 1269 | 0.090 | 0.10 | 0.077 | 0.078 |
| 1270 | 0.095 | ND | 2.4 | ND |
| 1271 | 0.058 | ND | 1.4 | ND |
| 1272 | 0.15 | ND | 1.4 | ND |
| 1273 | 0.21 | ND | 2.4 | ND |
| 1274 | 0.070 | ND | 0.12 | ND |
| 1275 | 0.16 | ND | 0.51 | ND |
| 1276 | 0.12 | ND | 0.56 | ND |
| 1277 | 0.084 | ND | 0.15 | ND |
| 1278 | 0.37 | ND | 0.98 | ND |
| 1279 | 1.51 | ND | ND | ND |
| 1280 | 0.078 | ND | 0.24 | ND |
| 1281 | 0.064 | ND | 0.18 | ND |
| 1282 | 0.19 | ND | 0.92 | ND |
| 1283 | 2.6 | ND | 0.75 | ND |
| 1284 | 0.11 | ND | 2.5 | ND |
| 1285 | 0.25 | ND | 1.1 | ND |
| 1286 | 0.095 | ND | 0.28 | ND |
| 1287 | 0.082 | ND | 0.79 | ND |
| 1288 | 0.11 | ND | 0.18 | ND |
| 1289 | 0.26 | ND | 1.4 | ND |
| 1290 | 0.13 | ND | 0.076 | ND |
| 1291 | 0.15 | ND | 0.14 | ND |
| 1292 | 0.12 | ND | 0.11 | ND |
| 1293 | 0.24 | ND | 0.26 | ND |
| 1294 | 1.15 | ND | 1.8 | ND |
| 1295 | 0.16 | ND | 1.3 | ND |
| 1296 | 0.12 | ND | 2.2 | ND |
| 1297 | 0.13 | ND | 0.33 | ND |
| 1298 | 0.071 | ND | 0.053 | ND |
| 1299 | 0.061 | ND | 0.016 | ND |
| 1300 | 0.076 | ND | 0.022 | ND |
| 1301 | 0.08 | ND | 0.10 | ND |
| 1302 | 0.058 | ND | 0.22 | ND |
| 1303 | 0.11 | ND | 0.13 | ND |
| 1304 | 0.11 | ND | 0.99 | ND |
| 1305 | 0.097 | ND | 0.11 | ND |
| 1306 | 0.065 | ND | 0.31 | ND |
| 1307 | 0.096 | ND | 0.34 | ND |
| 1308 | 0.44 | ND | 0.47 | ND |
| 1309 | 1.31 | ND | 0.55 | ND |
| 1310 | 0.091 | ND | 0.086 | ND |
| 1311 | 0.14 | ND | 0.058 | 0.16 |
| 1312 | 0.077 | ND | 0.064 | 0.16 |
| 1313 | 0.11 | ND | 0.10 | ND |
| 1314 | 0.14 | ND | 0.091 | ND |
| 1315 | 0.11 | ND | 0.19 | ND |
| 1316 | 0.080 | ND | 0.15 | ND |
| 1317 | 0.12 | ND | 0.086 | ND |
| 1318 | 0.087 | ND | 0.046 | ND |
| 1319 | 0.18 | ND | 0.025 | ND |
| 1320 | 0.17 | ND | 0.021 | ND |
| 1321 | 0.19 | ND | 0.14 | ND |
| 1322 | 0.12 | ND | 0.038 | ND |
| 1323 | 0.15 | ND | 0.073 | ND |
| 1324 | 0.13 | ND | 0.22 | ND |
| 1325 | 0.13 | ND | 0.050 | ND |
| 1326 | 0.085 | ND | 0.008 | ND |
| 1327 | 0.16 | ND | 0.25 | ND |
| 1328 | 0.12 | ND | 0.059 | ND |
| 1329 | 0.079 | ND | 0.028 | 0.069 |
| 1330 | 0.13 | ND | 0.35 | ND |
| 1331 | 0.078 | ND | 0.22 | 0.82 |
| 1332 | 0.11 | ND | 0.079 | ND |

TABLE 1-continued

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 1333 | 0.098 | ND | 0.041 | 0.067 |
| 1334 | 0.095 | 0.058 | 0.074 | 0.17 |
| 1335 | 0.055 | 0.066 | 0.056 | 0.24 |
| 1336 | 0.18 | ND | 0.19 | ND |
| 1337 | 0.25 | ND | 0.45 | ND |
| 1338 | 0.074 | ND | 0.23 | ND |
| 1339 | 0.15 | ND | 0.6 | ND |
| 1340 | 0.084 | ND | 0.22 | ND |
| 1341 | 0.11 | ND | 0.058 | ND |
| 1342 | 0.091 | ND | 0.48 | ND |
| 1343 | 0.095 | ND | 0.8 | ND |
| 1344 | 0.32 | ND | >10 | ND |
| 1345 | 0.22 | 3.7 | 4.7 | 8.8 |
| 1346 | 0.12 | 2.1 | 2.5 | 3 |
| 1347 | 0.28 | ND | 0.43 | ND |
| 1348 | 0.14 | ND | 2.5 | ND |
| 1349 | 0.13 | ND | 1.5 | ND |
| 1350 | 0.069 | ND | 0.11 | 0.28 |
| 1351 | 0.074 | ND | 0.099 | 0.3 |
| 1352 | 0.087 | ND | 0.11 | 0.31 |
| 1353 | 0.105 | ND | 0.048 | 0.19 |
| 1354 | 0.083 | ND | 0.057 | 0.14 |
| 1355 | 0.089 | ND | 0.24 | ND |
| 1356 | 0.093 | ND | 0.076 | ND |
| 1357 | 0.077 | ND | 0.036 | 0.14 |
| 1358 | 0.082 | ND | 0.036 | 0.14 |
| 1359 | 0.075 | ND | 0.028 | 0.11 |
| 1360 | 0.099 | ND | 0.15 | 1.1 |
| 1361 | 0.084 | ND | 0.14 | ND |
| 1362 | 0.082 | ND | 0.069 | ND |
| 1363 | 0.090 | ND | 0.14 | 1 |
| 1364 | 0.12 | ND | 0.12 | 0.58 |

ND = not determined

It is understood that the examples and embodiments described herein are for illustrative purposes only and that various modifications or changes in light thereof will be suggested to persons skilled in the art and are to be included within the spirit and purview of the appended claims. All publications, patents, and patent applications cited herein are hereby incorporated by reference in their entirety for all purposes.

Xenograft Tumor Growth Inhibition Assay

The effect of Examples 1, 32, 119, 186. 215 and 216 to inhibit the growth of H929 xenograft tumors implanted in mice was evaluated. NCI-H929 cells obtained from either tumor brei or culture were suspended in cell culture medium (MEM, no calcium, no glutamine, Life Technologies Corporation) and diluted 1:1 with a solution of Matrigel™ (BD Biosciences, Franklin Lakes, N.J.). Tumor cells 5 million per site were inoculated subcutaneously into the right hind flank of female nude or SCID-beige mice (Charles River Labs). Randomization into treatment and vehicle control groups (9-10/group) occurred when the mean tumor volume reached approximately 200 mm$^3$. Compounds were formulated in 2.5% DMSO, 2.5% Tween80, 25% PEG400, 70% phosphate-buffered saline or in 2% DMSO, 5% Tween80, 20% PEG400, 73% HPMC. Administration of compound or vehicle was initiated on the day following randomization and continued for the indicated time. Tumors were measured twice a week throughout the treatment period using a pair of calipers and tumor volumes were calculated according to the formula V=L×W$^2$/2 (V: volume, mm$^3$; L: length, mm. W: width, mm). Tumor growth inhibition was calculated based on the mean tumor volume measured at the end of the treatment period according to the formula % TGI=100−mean tumor volume of treatment group/mean tumor volume of control group×100. Results are given in Table 2.

TABLE 2

H929 human multiple myeloma cancer xenograft model.

| Example | Dose mg/kg | route, regimen | % TGI$^a$ | % TGD$^b$ | % removed from study$^c$ |
|---|---|---|---|---|---|
| 1 | 12.5 | IP, TW$^d$ × 2 | 72* | Nd$^e$ | 0 |
| 32 | 1.85 | IP, TW × 4 | 27* | Nd | 10 |
| 32 | 3.75 | IP, TW × 4 | 57*** | Nd | 0 |
| 32 | 5.00 | IP, TW × 4 | 66*** | Nd | 10 |
| 119 | 15 | IP, TW × 3 | 66** | 71*** | 0 |
| 119 | 30 | IP, TW × 3 | 65*** | 65*** | 11 |
| 186 | 1.875 | IP, TW × 3 | 63*** | 62*** | 0 |
| 186 | 3.75 | IP, TW × 3 | 70** | 103* | 44 |
| 215 | 15 | IP, TW × 3 | 63** | 55** | 11 |
| 215 | 30 | IP, TW × 3 | 83*** | 109*** | 33 |
| 216 | 3.75 | IP, TW × 3 | 29 | 3 | 11 |
| 216 | 7.5 | IP, TW × 3 | 16 | 2 | 11 |

$^a$The p values (as indicated by asterisks) are derived from Student's T test comparison of treatment group vs. control group: *p < 0.05, p < 0.01, *p < 0.001.
$^b$Tumor growth delay, % TGD = (T − C)/C × 100, where T = median time to reach 500 mm$^3$ of treatment group and C = median time to endpoint of control group. The p values (as indicated by asterisks) derived from Kaplan Meier log-rank comparison of treatment group vs. treatment control group based on an endpoint of 1000 mm$^3$. *p < 0.05, p < 0.01, *p < 0.001.
$^c$Percentage of treatment group that were removed from study due to morbidity or weight loss in excess of 20%.
$^d$Twice a week, 3 and 4 days apart.
$^e$Not determined. End point not achieved by end of study (day 27).

What is claimed is:

1. A compound of Formula (IIa), or a pharmaceutically acceptable salt thereof,

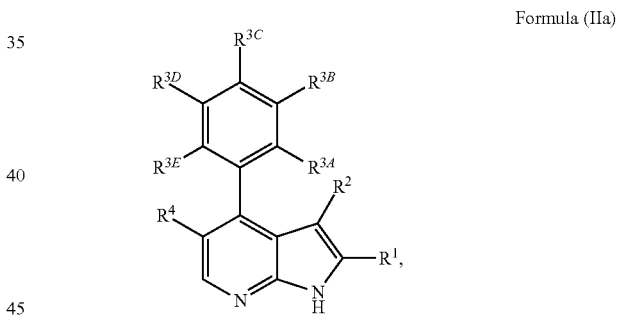

Formula (IIa)

wherein
R$^1$ is selected from the group consisting of cycloalkyl, cycloalkenyl, heterocycloalkyl, and heterocycloalkenyl; wherein the R$^1$ cycloalkyl, cycloalkenyl, heterocycloalkyl and heterocycloalkenyl are optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, SO$_2$NHC(O)R$^5$, SO$_2$NR$^5$C(O)R$^5$, NHS(O)$_2$R$^5$, NR$^5$S(O)$_2$R$^5$, NHC(O)OR$^5$, NR$^5$C(O)OR$^5$, SO$_2$NHC(O)OR$^5$, SO$_2$NR$^5$C(O)OR$^5$, NHSO$_2$NHC(O)OR$^5$, NHSO$_2$NR$^5$C(O)OR$^5$, NR$^5$SO$_2$NR$^5$C(O)OR$^5$, NR$^5$SO$_2$NHC(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, OC(O)NH$_2$, OC(O)NHR$^5$, OC(O)N(R$^5$)$_2$, OC(O)NHSO$_2$R$^5$, OC(O)NR$^5$SO$_2$R$^5$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, OSO$_2$NH$_2$, OSO$_2$NHR$^5$, OSO$_2$N(R$^5$)$_2$, C(O)NHCN, C(O)NR$^5$CN, S(O)NR$^5$, S(O)(N) R$^5$SO$_2$R$^5$, C(O)H, C(O)OH, (O), OH, CN, NO$_2$, F, Cl, Br and I;

R$^2$ is selected from the group consisting of hydrogen, C$_1$-C$_4$ alkyl, NO$_2$, CN, C(O)NH$_2$, C(O)OR$^{2A}$, F, Cl, Br and I;

R$^{2A}$ is selected from the group consisting of C$_1$-C$_6$alkyl, C$_2$-C$_6$alkenyl, and C$_2$-C$_6$alkynyl;

R$^{3A}$, R$^{3B}$, R$^{3C}$, R$^{3D}$, and R$^{3E}$ are each independently selected from the group consisting of H, R$^6$, OR$^6$, SR$^6$, S(O)R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, C(O)H, C(O)OH, (O), OH, CN, NO$_2$, F, Cl, Br and I;

R$^4$ is selected from the group consisting of R$^{4A}$, OR$^{4A}$, C(O)NH$_2$, CN, F, Cl, Br, and I;

R$^{4A}$ is selected from the group consisting of hydrogen, C$_1$-C$_6$ alkyl, C$_2$-C$_6$alkenyl, and C$_2$-C$_6$alkynyl;

R$^5$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^5$C$_1$-C$_6$ alkyl, C$_2$-C$_6$alkenyl, and C$_2$-C$_6$alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, B(OH)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I;

R$^6$, at each occurrence, is independently selected from the group consisting of C$_1$-C$_6$alkyl, C$_2$-C$_6$alkenyl, C$_2$-C$_6$alkynyl, phenyl, heteroaryl, heterocycloalkyl, heterocycloalkenyl, cycloalkyl, and cycloalkenyl; wherein each R$^6$ C$_1$-C$_6$alkyl, C$_2$-C$_6$alkenyl, and C$_2$-C$_6$alkynyl is optionally substituted with one or more substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, CN, NO$_2$, F, Cl, Br and I; wherein each R$^6$ phenyl, cycloalkyl, cycloalkenyl, heteroaryl, heterocycloalkyl, and heterocycloalkenyl is optionally substituted with one or more substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, (O), OH, CN, NO$_2$, F, Cl, Br and I;

R$^7$, at each occurrence, is independently selected from the group consisting of C$_1$-C$_6$ alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^7$C$_1$-C$_6$ alkyl, C$_2$-C$_6$alkenyl, and C$_2$-C$_6$alkynyl is optionally substituted with one or more substituents independently selected from the group consisting of R$^{13}$, OR$^{13}$, NH$_2$, NHR$^{13}$, N(R$^{13}$)$_2$, C(O)H, C(O)OH, OH, CN, NO$_2$, F, Cl, Br and I; wherein each R$^7$ aryl, cycloalkyl, cycloalkenyl, heteroaryl, heterocycloalkyl, and heterocycloalkenyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, (O), OH, CN, NO$_2$, F, Cl, Br and I;

R$^8$, at each occurrence, is independently selected from the group consisting of C$_1$-C$_6$ alkyl, C$_2$-C$_6$alkenyl, C$_2$-C$_6$alkynyl, and heterocycloalkyl; wherein each R$^8$ C$_1$-C$_6$alkyl, C$_2$-C$_6$alkenyl, and C$_2$-C$_6$alkynyl is optionally substituted with one or more substituents independently selected from the group consisting of aryl, heteroaryl, SO$_2$R$^{8A}$, C(O)OR$^{8A}$, C(O)NH$_2$, C(O)NHR$^{8A}$, C(O)N(R$^{8A}$)$_2$, C(O)NHSO$_2$R$^{8A}$, C(O)NR$^{8A}$SO$_2$R$^{8A}$, NH$_2$, C(O)H, C(O)OH, OH, CN, NO$_2$, F, Cl, Br and I; wherein each R$^8$ heterocycloalkyl is optionally substituted with one or more substituents independently selected from the group consisting of NH$_2$, C(O)H, C(O)OH, OH, CN, NO$_2$, F, Cl, Br and I;

R$^{8A}$, at each occurrence, is independently selected from the group consisting of C$_1$-C$_6$ alkyl, C$_2$-C$_6$alkenyl, and C$_2$-C$_6$alkynyl;

R$^9$, at each occurrence, is independently selected from the group consisting of C$_1$-C$_6$alkyl, C$_2$-C$_6$alkenyl, C$_2$-C$_6$alkynyl, aryl, heteroaryl, heterocycloalkyl, heterocycloalkenyl, cycloalkyl, and cycloalkenyl; wherein each R$^9$ C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I; wherein each R$^9$ aryl, cycloalkyl, cycloalkenyl, heteroaryl, heterocycloalkyl, and heterocycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC (O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, (O), OH, CN, NO$_2$, F, Cl, Br and I;

R$^{10}$, at each occurrence, is independently selected from the group consisting of C$_1$-C$_6$alkyl, C$_2$-C$_6$alkenyl, and C$_2$-C$_6$ alkynyl; wherein each R$^{10}$ C$_1$-C$_6$alkyl, C$_2$-C$_6$alkenyl, and C$_2$-C$_6$alkynyl is optionally substituted with one or more substituents independently selected from the group consisting of NH$_2$, C(O)H, C(O)OH, OH, CN, NO$_2$, F, Cl, Br and I;

R$^{11}$, at each occurrence, is independently selected from the group consisting of C$_1$-C$_6$alkyl, C$_2$-C$_6$alkenyl, C$_2$-C$_6$alkynyl, aryl, and heteroaryl; wherein each R$^{11}$C$_1$-C$_6$alkyl, C$_2$-C$_6$alkenyl, and C$_2$-C$_6$alkynyl is optionally substituted with one or more substituents independently selected from the group consisting of OR$^{11A}$, NH$_2$, NHR$^{11A}$, N(R$^{11A}$)$_2$, C(O)H, C(O)OH, OH, CN, NO$_2$, F, Cl, Br and I; wherein each R$^{11}$ aryl and heteroaryl is optionally substituted with one or more substituents independently selected from the group consisting of C$_1$-C$_6$alkyl, C$_1$-C$_6$ haloalkyl, NH$_2$, C(O)H, C(O)OH, OH, CN, NO$_2$, F, Cl, Br and I;

R$^{11A}$, at each occurrence, is independently selected from the group consisting of C$_1$-C$_6$alkyl, C$_2$-C$_6$alkenyl, and C$_2$-C$_6$ alkynyl;

R$^{12}$, at each occurrence, is independently selected from the group consisting of C$_1$-C$_6$alkyl, C$_2$-C$_6$alkenyl, and C$_2$-C$_6$ alkynyl; wherein each R$^{12}$C$_1$-C$_6$alkyl, C$_2$-C$_6$alkenyl, and C$_2$-C$_6$alkynyl is optionally substituted with one or more substituents independently selected from the group consisting of NH$_2$, NHR$^{14}$, N(R$^{14}$)$_2$, C(O)H, C(O)OH, OH, CN, NO$_2$, F, Cl, Br and I;

R$^{13}$, at each occurrence, is independently selected from the group consisting of C$_1$-C$_6$alkyl, C$_2$-C$_6$alkenyl, C$_2$-C$_6$ alkynyl, aryl, heteroaryl, cycloalkyl, cycloalkenyl, and heterocycloalkyl, heterocycloalkenyl; wherein each R$^{13}$ C$_1$-C$_6$alkyl, C$_2$-C$_6$alkenyl, and C$_2$-C$_6$alkynyl is optionally substituted with one or more substituents independently selected from the group consisting of R$^{15}$, OR$^{15}$, C(O)H, C(O)OH, OH, CN, NO$_2$, F, Cl, Br and I; wherein each R$^{13}$ aryl, cycloalkyl, cycloalkenyl, heteroaryl, heterocycloalkyl, and heterocycloalkenyl is optionally substituted with one or more substituents independently selected from the group consisting of R$^{16}$, OR$^{16}$, C(O)H, C(O)OH, (O), OH, CN, NO$_2$, F, Cl, Br and I;

R$^{14}$, at each occurrence, is independently selected from the group consisting of C$_1$-C$_6$ haloalkyl, C$_1$-C$_6$alkyl, C$_2$-C$_6$alkenyl, and C$_2$-C$_6$ alkynyl;

R$^{15}$, at each occurrence, is independently selected from the group consisting of C$_1$-C$_6$ haloalkyl, C$_1$-C$_6$alkyl, C$_2$-C$_6$alkenyl, and C$_2$-C$_6$ alkynyl; wherein each R$^{15}$ C$_1$-C$_6$alkyl, C$_2$-C$_6$alkenyl, and C$_2$-C$_6$alkynyl is optionally substituted with one or more OCH$_3$; and R$^{16}$, at each occurrence, is independently selected from the group consisting of C$_1$-C$_6$ haloalkyl, C$_1$-C$_6$alkyl, C$_2$-C$_6$alkenyl, and C$_2$-C$_6$ alkynyl.

2. The compound of claim 1, or a pharmaceutically acceptable salt thereof, wherein R$^2$ is hydrogen, and R$^4$ is hydrogen.

3. The compound of claim 2, or a pharmaceutically acceptable salt thereof, wherein R$^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the R$^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, SO$_2$NHC(O)R$^5$, SO$_2$NR$^5$C(O)R$^5$, NHS(O)$_2$R$^5$, NR$^5$S(O)$_2$R$^5$, NHC(O)OR$^5$, NR$^5$C(O)OR$^5$, SO$_2$NHC(O)OR$^5$, SO$_2$NR$^5$C(O)OR$^5$, NHSO$_2$NHC(O)OR$^5$, NHSO$_2$NR$^5$C(O)OR$^5$, NR$^5$SO$_2$NR$^5$C(O)OR$^5$, NR$^5$SO$_2$NHC(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, OC(O)NH$_2$, OC(O)NHR$^5$, OC(O)N(R$^5$)$_2$, OC(O)NHSO$_2$R$^5$, OC(O)NR$^5$SO$_2$R$^5$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, OSO$_2$NH$_2$, OSO$_2$NHR$^5$, OSO$_2$N(R$^5$)$_2$, C(O)NHCN, C(O)NR$^5$CN, S(O)NR$^5$, S(O)(N)R$^5$SO$_2$R$^5$, C(O)H, C(O)OH, (O), OH, CN, NO$_2$, F, Cl, Br and I.

4. The compound of claim 2, or a pharmaceutically acceptable salt thereof, wherein R$^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the R$^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SO_2R^5$, $C(O)R^5$, $CO(O)R^5$, $NH_2$, $NHR^5$, $NHC(O)R^5$, $SO_2NHC(O)R^5$, $NHS(O)_2R^5$, $SO_2NHC(O)OR^5$, $NHSO_2NHC(O)OR^5$, $NHC(O)NHR^5$, $OC(O)NHR^5$, $OC(O)NHSO_2R^5$, $C(O)NH_2$, $C(O)NHR^5$, $C(O)N(R^5)_2$, $C(O)NHOR^5$, $C(O)NHSO_2R^5$, $SO_2NH_2$, $SO_2NHR^5$, $SO_2N(R^5)_2$, $OSO_2NHR^5$, $C(O)NHCN$, $S(O)NR^5$, $S(O)(N)R^5SO_2R^5$, $C(O)OH$, $(O)$, $OH$, and $CN$.

5. The compound of claim 2, or a pharmaceutically acceptable salt thereof, wherein $R^1$ is selected from the group consisting of 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl; wherein the $R^1$ 2,5-dihydro-1H-pyrrolyl, cyclopentenyl, piperazinyl, 3,6-dihydro-2H-thiopyranyl, 3,6-dihydro-2H-pyranyl, 3,6-dihydro-2H-thiopyranyl 1-oxide, 3,6-dihydro-2H-thiopyranyl 1,1-dioxide, tetrahydro-2H-thiopyranyl 1,1-dioxide, 5,6-dihydropyridinyl-2(1H)-one, cyclohexyl-3-enone, 2,3,6,7-tetrahydro-1H-azepinyl, 2,3,4,7-tetrahydro-1H-azepinyl, 2-azaspiro[3.3]heptanyl, 3-azaspiro[5.5]undec-8-enyl, 3-azabicyclo[4.1.0]heptanyl, octahydrocyclopenta[c]pyrrolyl, 1,2,3,3a,4,6a-hexahydropentalenyl, 3-oxa-9-azabicyclo[3.3.1]non-6-enyl, 6,7-dihydro-1H-oxazolo[3,4-a]pyridin-3(5H)-onyl, 9-azabicyclo[3.3.1]non-3-enyl, 1,6,7,9a-tetrahydropyrido[2,1-c][1,4]oxazin-3(4H)-onyl, azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

6. The compound of claim 3, or a pharmaceutically acceptable salt thereof, wherein $R^{3A}$, $R^{3B}$, $R^{3C}$, $R^{3D}$, and $R^{3E}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl.

7. The compound of claim 3, or a pharmaceutically acceptable salt thereof, wherein $R^{3A}$ is H, $R^{3D}$ is H, and $R^{3E}$ is $OCH_3$; and $R^{3B}$ and $R^{3C}$ are each independently selected from the group consisting of H, $R^6$, $OR^6$, $SR^6$, $S(O)R^6$, $C(O)R^6$, $NH_2$, $NHR^6$, $N(R^6)_2$, $NHC(O)R^6$, $NHS(O)_2R^6$, $C(O)NH_2$, $C(O)NHR^6$, $C(O)N(R^6)_2$, CN, F, and Cl.

8. The compound of claim 3, or a pharmaceutically acceptable salt thereof, wherein $R^{3A}$ is H, $R^{3B}$ is F, $R^{3C}$ is H, $R^{3D}$ is H, and $R^{3E}$ is $OR^6$.

9. The compound of claim 8, or a pharmaceutically acceptable salt thereof, wherein $R^6$, at each occurrence, is independently selected from the group consisting of $C_1$-$C_6$alkyl, phenyl, heteroaryl, heterocycloalkyl, heterocycloalkenyl, and cycloalkyl; wherein each $R^6C_1$-$C_6$alkyl is optionally substituted with one or more substituents independently selected from the group consisting of $R^9$, $NH_2$, $NHR^9$, $NHS(O)_2R^9$, CN, and F; and wherein each $R^6$ phenyl, heteroaryl, heterocycloalkyl, heterocycloalkenyl, and cycloalkyl is optionally substituted with one or more substituents independently selected from the group consisting of $R^{10}$, $OR^{10}$, and F.

10. The compound of claim 1, selected from the group consisting of:
4-(5-fluoro-2-methoxyphenyl)-2-(piperidin-3-yl)-1H-pyrrolo[2,3-b]pyridine;
4-(4-fluoro-2-methoxyphenyl)-2-(piperidin-3-yl)-1H-pyrrolo[2,3-b]pyridine;
4-(5-fluoro-2-methoxyphenyl)-2-[(3S)-piperidin-3-yl]-1H-pyrrolo[2,3-b]pyridine;
4-(5-fluoro-2-methoxyphenyl)-2-[(3R)-piperidin-3-yl]-1H-pyrrolo[2,3-b]pyridine;
4-[5-(4,5-dihydro-1H-imidazol-2-yl)-2-methoxyphenyl]-2-(piperidin-3-yl)-1H-pyrrolo[2,3-b]pyridine;
4-(5-cyclopropyl-2-methoxyphenyl)-2-(piperidin-3-yl)-1H-pyrrolo[2,3-b]pyridine;
4-(4-fluoro-2-methoxyphenyl)-2-(1-methylpiperidin-3-yl)-1H-pyrrolo[2,3-b]pyridine;
4-(5-fluoro-2-methoxyphenyl)-2-(1-methylpiperidin-3-yl)-1H-pyrrolo[2,3-b]pyridine;
1-{3-[4-(5-fluoro-2-methoxyphenyl)-1H-pyrrolo[2,3-b]pyridin-2-yl]piperidin-1-yl}ethanone;
4-(5-fluoro-2-methoxyphenyl)-2-(piperidin-4-yl)-1H-pyrrolo[2,3-b]pyridine;
4-(4-fluoro-2-methoxyphenyl)-2-(piperidin-4-yl)-1H-pyrrolo[2,3-b]pyridine;
4-(4-chloro-2-methoxyphenyl)-2-(piperidin-4-yl)-1H-pyrrolo[2,3-b]pyridine;
4-(4,5-difluoro-2-methoxyphenyl)-2-(piperidin-4-yl)-1H-pyrrolo[2,3-b]pyridine;
4-(5-chloro-2-methoxyphenyl)-2-(piperidin-4-yl)-1H-pyrrolo[2,3-b]pyridine;
4-(2-methoxy-5-methylphenyl)-2-(piperidin-4-yl)-1H-pyrrolo[2,3-b]pyridine;
4-(3-chloro-2-methoxyphenyl)-2-(piperidin-4-yl)-1H-pyrrolo[2,3-b]pyridine;
4-(2-methoxyphenyl)-2-(piperidin-4-yl)-1H-pyrrolo[2,3-b]pyridine;
4-(5-fluoro-2-methoxyphenyl)-2-(1-methylpiperidin-4-yl)-1H-pyrrolo[2,3-b]pyridine;
4-(4-fluoro-2-methoxyphenyl)-2-(1-methylpiperidin-4-yl)-1H-pyrrolo[2,3-b]pyridine;
4-(2-methoxy-5-methylphenyl)-2-(1-methylpiperidin-4-yl)-1H-pyrrolo[2,3-b]pyridine;
N-{4-chloro-3-[2-(piperidin-4-yl)-1H-pyrrolo[2,3-b]pyridin-4-yl]phenyl}benzenesulfonamide;
N-benzyl-4-fluoro-3-[2-(piperidin-4-yl)-1H-pyrrolo[2,3-b]pyridin-4-yl]aniline;
N-benzyl-4-chloro-3-[2-(piperidin-4-yl)-1H-pyrrolo[2,3-b]pyridin-4-yl]aniline;

4-(5-fluoro-2-methoxyphenyl)-2-(pyrrolidin-3-yl)-1H-pyrrolo[2,3-b]pyridine;
4-(4-fluoro-2-methoxyphenyl)-2-(pyrrolidin-3-yl)-1H-pyrrolo[2,3-b]pyridine;
4-(5-fluoro-2-methoxyphenyl)-2-[(3S)-pyrrolidin-3-yl]-1H-pyrrolo[2,3-b]pyridine;
4-(5-fluoro-2-methoxyphenyl)-2-[(3R)-pyrrolidin-3-yl]-1H-pyrrolo[2,3-b]pyridine;
4-(5-fluoro-2-methoxyphenyl)-2-(1-methylpyrrolidin-3-yl)-1H-pyrrolo[2,3-b]pyridine;
4-(4-fluoro-2-methoxyphenyl)-2-(morpholin-2-yl)-1H-pyrrolo[2,3-b]pyridine;
4-(5-fluoro-2-methoxyphenyl)-2-(morpholin-2-yl)-1H-pyrrolo[2,3-b]pyridine;
4-(4-fluoro-2-methoxyphenyl)-2-(4-methylmorpholin-2-yl)-1H-pyrrolo[2,3-b]pyridine;
4-(5-fluoro-2-methoxyphenyl)-2-(4-methylmorpholin-2-yl)-1H-pyrrolo[2,3-b]pyridine;
2-(5,5-dimethylmorpholin-2-yl)-4-(5-fluoro-2-methoxyphenyl)-1H-pyrrolo[2,3-b]pyridine;
2-(5,5-dimethylmorpholin-2-yl)-4-(4-fluoro-2-methoxyphenyl)-1H-pyrrolo[2,3-b]pyridine;
4-(4-chloro-2-methoxyphenyl)-2-(5,5-dimethylmorpholin-2-yl)-1H-pyrrolo[2,3-b]pyridine;
trans-4-[4-(5-fluoro-2-methoxyphenyl)-1H-pyrrolo[2,3-b]pyridin-2-yl]cyclohexanamine;
3-[4-(5-fluoro-2-methoxyphenyl)-1H-pyrrolo[2,3-b]pyridin-2-yl]cyclohexanamine;
4-(5-fluoro-2-methoxyphenyl)-3-methyl-2-(piperidin-4-yl)-1H-pyrrolo[2,3-b]pyridine;
5-chloro-4-(3-fluorophenyl)-2-(piperidin-3-yl)-1H-pyrrolo[2,3-b]pyridine;
3-[5-chloro-4-(3-fluorophenyl)-1H-pyrrolo[2,3-b]pyridin-2-yl]cyclohexanamine;
4-(5-fluoro-2-methoxyphenyl)-2-(1,2,3,6-tetrahydropyridin-4-yl)-1H-pyrrolo[2,3-b]pyridine;
4-(5-fluoro-2-methoxyphenyl)-2-(pyrrolidin-2-yl)-1H-pyrrolo[2,3-b]pyridine;
2-cyclohexyl-4-(5-fluoro-2-methoxyphenyl)-1H-pyrrolo[2,3-b]pyridine;
1-{2-[4-(5-fluoro-2-methoxyphenyl)-1H-pyrrolo[2,3-b]pyridin-2-yl]pyrrolidin-1-yl}ethanone;
1-{4-[4-(5-fluoro-2-methoxyphenyl)-1H-pyrrolo[2,3-b]pyridin-2-yl]-3,6-dihydropyridin-1(2H)-yl}ethanone;
1-{4-[4-(5-fluoro-2-methoxyphenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-(1-methylpyrrolidin-2-yl)-1H-pyrrolo[2,3-b]pyridine;
1-{3-[4-(5-fluoro-2-methoxyphenyl)-1H-pyrrolo[2,3-b]pyridin-2-yl]pyrrolidin-1-yl}ethanone;
2-{3-[4-(5-fluoro-2-methoxyphenyl)-1H-pyrrolo[2,3-b]pyridin-2-yl]pyrrolidin-1-yl}ethanol;
4-(5-fluoro-2-methoxyphenyl)-2-[1-(tetrahydro-2H-pyran-4-yl)pyrrolidin-3-yl]-1H-pyrrolo[2,3-b]pyridine;
4-(5-fluoro-2-methoxyphenyl)-2-[1-(pyridin-2-ylmethyl)pyrrolidin-3-yl]-1H-pyrrolo[2,3-b]pyridine;
4-(5-fluoro-2-methoxyphenyl)-2-[1-(pyridin-3-ylmethyl)pyrrolidin-3-yl]-1H-pyrrolo[2,3-b]pyridine;
4-(5-fluoro-2-methoxyphenyl)-2-[1-(pyridin-4-ylmethyl)pyrrolidin-3-yl]-1H-pyrrolo[2,3-b]pyridine;
4-(5-fluoro-2-methoxyphenyl)-2-[1-(tetrahydro-2H-pyran-3-ylmethyl)pyrrolidin-3-yl]-1H-pyrrolo[2,3-b]pyridine;
tert-butyl (2-{3-[4-(5-fluoro-2-methoxyphenyl)-1H-pyrrolo[2,3-b]pyridin-2-yl]pyrrolidin-1-yl}ethyl)carbamate;
tert-butyl 3-[4-(5-fluoro-2-methoxyphenyl)-1H-pyrrolo[2,3-b]pyridin-2-yl]-1,3'-bipyrrolidine-1'-carboxylate;
4-(5-fluoro-2-methoxyphenyl)-2-[1-(tetrahydro-2H-pyran-4-ylmethyl)pyrrolidin-3-yl]-1H-pyrrolo[2,3-b]pyridine;
4-(5-fluoro-2-methoxyphenyl)-2-{1-[2-(morpholin-4-yl)ethyl]pyrrolidin-3-yl}-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine;
methyl 4-({trans-4-[4-(5-fluoro-2-methoxyphenyl)-1H-pyrrolo[2,3-b]pyridin-2-yl]cyclohexyl}amino)butanoate;
ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate;
trans-4-[4-(5-fluoro-2-methoxyphenyl)-1H-pyrrolo[2,3-b]pyridin-2-yl]-N-[2-(morpholin-4-yl)ethyl]cyclohexanamine;
3-({trans-4-[4-(5-fluoro-2-methoxyphenyl)-1H-pyrrolo[2,3-b]pyridin-2-yl]cyclohexyl}amino)propane-1,2-diol;
2-{3-[4-(5-fluoro-2-methoxyphenyl)-1H-pyrrolo[2,3-b]pyridin-2-yl]pyrrolidin-1-yl}ethanamine;
3-[4-(5-fluoro-2-methoxyphenyl)-1H-pyrrolo[2,3-b]pyridin-2-yl]-1,3'-bipyrrolidine;
4-[4-(5-fluoro-2-methoxyphenyl)-1H-pyrrolo[2,3-b]pyridin-2-yl]piperidin-4-ol;
benzyl (3-{3-[4-(5-fluoro-2-methoxyphenyl)-1H-pyrrolo[2,3-b]pyridin-2-yl]piperidin-1-yl}propyl)carbamate;
2-{3-[4-(5-fluoro-2-methoxyphenyl)-1H-pyrrolo[2,3-b]pyridin-2-yl]piperidin-1-yl}ethanol;
3-{3-[4-(5-fluoro-2-methoxyphenyl)-1H-pyrrolo[2,3-b]pyridin-2-yl]piperidin-1-yl}propan-1-amine;
4-(5-fluoro-2-methoxyphenyl)-2-[1-(2-methoxyethyl)piperidin-3-yl]-1H-pyrrolo[2,3-b]pyridine;
4-({trans-4-[4-(5-fluoro-2-methoxyphenyl)-1H-pyrrolo[2,3-b]pyridin-2-yl]cyclohexyl}amino)butanoic acid;
1-{4-[4-(5-fluoro-2-methoxyphenyl)-1H-pyrrolo[2,3-b]pyridin-2-yl]piperidin-1-yl}ethanone;
1-{4-[4-(5-fluoro-2-methoxyphenyl)-1H-pyrrolo[2,3-b]pyridin-2-yl]piperidin-1-yl}-2-hydroxyethanone;
3-methoxy-4-[2-(piperidin-3-yl)-1H-pyrrolo[2,3-b]pyridin-4-yl]benzonitrile;
2-[({trans-4-[4-(5-fluoro-2-methoxyphenyl)-1H-pyrrolo[2,3-b]pyridin-2-yl]cyclohexyl}amino)methyl]cyclopropanecarboxylic acid;
2-(azetidin-3-yl)-4-(5-fluoro-2-methoxyphenyl)-1H-pyrrolo[2,3-b]pyridine;
1-{4-[4-(5-fluoro-2-methoxyphenyl)-1H-pyrrolo[2,3-b]pyridin-2-yl]piperidin-1-yl}-2-(4-hydroxypiperidin-1-yl)ethanone;
4-(5-fluoro-2-methoxyphenyl)-2-[1-(methylsulfonyl)piperidin-4-yl]-1H-pyrrolo[2,3-b]pyridine;
3-{4-[4-(5-fluoro-2-methoxyphenyl)-1H-pyrrolo[2,3-b]pyridin-2-yl]piperidin-1-yl}propane-1,2-diol;
4-[4-(5-fluoro-2-methoxyphenyl)-1H-pyrrolo[2,3-b]pyridin-2-yl]tetrahydro-2H-pyran-4-ol;
4-(5-fluoro-2-methoxyphenyl)-2-[1-(pyridin-4-ylmethyl)azetidin-3-yl]-1H-pyrrolo[2,3-b]pyridine;
1-{3-[4-(5-fluoro-2-methoxyphenyl)-1H-pyrrolo[2,3-b]pyridin-2-yl]azetidin-1-yl}ethanone;
2-{3-[4-(5-fluoro-2-methoxyphenyl)-1H-pyrrolo[2,3-b]pyridin-2-yl]azetidin-1-yl}ethanamine;

4-(5-fluoro-2-methoxyphenyl)-2-[1-(tetrahydro-2H-pyran-4-ylmethyl)azetidin-3-yl]-1H-pyrrolo[2,3-b]pyridine;

4-(5-fluoro-2-methoxyphenyl)-2-{1-[2-(morpholin-4-yl)ethyl]azetidin-3-yl}-1H-pyrrolo[2,3-b]pyridine;

2-{3-[4-(5-fluoro-2-methoxyphenyl)-1H-pyrrolo[2,3-b]pyridin-2-yl]azetidin-1-yl}ethanol;

4-fluoro-3-[2-(1-methylpiperidin-4-yl)-1H-pyrrolo[2,3-b]pyridin-4-yl]-N-(tetrahydro-2H-pyran-4-ylmethyl)aniline;

1-{4-[4-(5-fluoro-2-methoxyphenyl)-1H-pyrrolo[2,3-b]pyridin-2-yl]piperidin-1-yl}-2-(piperidin-1-yl)ethanone;

1-{4-[4-(5-fluoro-2-methoxyphenyl)-1H-pyrrolo[2,3-b]pyridin-2-yl]piperidin-1-yl}-2-(morpholin-4-yl)ethanone;

1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone;

1-{4-[4-(5-fluoro-2-methoxyphenyl)-1H-pyrrolo[2,3-b]pyridin-2-yl]piperidin-1-yl}-2-[(2-hydroxyethyl)amino]ethanone;

4-(5-fluoro-2-methoxyphenyl)-2-(1-methylazetidin-3-yl)-1H-pyrrolo[2,3-b]pyridine;

4-(5-fluoro-2-methoxyphenyl)-2-[1-(methylsulfonyl)azetidin-3-yl]-1H-pyrrolo[2,3-b]pyridine;

3-{4-[4-(5-fluoro-2-methoxyphenyl)-1H-pyrrolo[2,3-b]pyridin-2-yl]-3,6-dihydropyridin-1(2H)-yl}propane-1,2-diol;

4-fluoro-3-[2-(piperidin-4-yl)-1H-pyrrolo[2,3-b]pyridin-4-yl]aniline;

4-fluoro-3-[2-(1-methylpiperidin-4-yl)-1H-pyrrolo[2,3-b]pyridin-4-yl]-N-(pyridin-4-ylmethyl)aniline;

4-fluoro-3-[2-(1-methylpiperidin-4-yl)-1H-pyrrolo[2,3-b]pyridin-4-yl]-N-[4-(methylsulfonyl)benzyl]aniline;

4-[({4-fluoro-3-[2-(1-methylpiperidin-4-yl)-1H-pyrrolo[2,3-b]pyridin-4-yl]phenyl}amino)methyl]benzamide;

2-(azepan-3-yl)-4-(5-fluoro-2-methoxyphenyl)-1H-pyrrolo[2,3-b]pyridine;

N-benzyl-3-[5-chloro-2-(piperidin-4-yl)-1H-pyrrolo[2,3-b]pyridin-4-yl]-4-fluoroaniline;

N-benzyl-4-chloro-3-[2-(piperidin-3-yl)-1H-pyrrolo[2,3-b]pyridin-4-yl]aniline;

4-(4,5-difluoro-2-methoxyphenyl)-2-(piperidin-3-yl)-1H-pyrrolo[2,3-b]pyridine;

N-benzyl-4-fluoro-3-[2-(piperidin-3-yl)-1H-pyrrolo[2,3-b]pyridin-4-yl]aniline;

4-fluoro-N-(3-fluorobenzyl)-3-[2-(piperidin-3-yl)-1H-pyrrolo[2,3-b]pyridin-4-yl]aniline;

4-[4-(5-fluoro-2-methoxyphenyl)-1H-pyrrolo[2,3-b]pyridin-2-yl]-N-methyl-3,6-dihydropyridine-1(2H)-carboxamide;

4-[4-(5-fluoro-2-methoxyphenyl)-1H-pyrrolo[2,3-b]pyridin-2-yl]-3,6-dihydropyridine-1(2H)-sulfonamide;

N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide;

tert-butyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-ene-1-carboxylic acid;

4-(2,3-difluorophenyl)-2-[1-(methylsulfonyl)-1,2,3,6-tetrahydropyridin-4-yl]-1H-pyrrolo[2,3-b]pyridine;

3-{4-[4-(5-fluoro-2-methoxyphenyl)-1H-pyrrolo[2,3-b]pyridin-2-yl]-3,6-dihydropyridin-1(2H)-yl}-3-oxopropanenitrile;

4-[4-(2,3-difluorophenyl)-1H-pyrrolo[2,3-b]pyridin-2-yl]-N-methyl-3,6-dihydropyridine-1(2H)-carboxamide;

4-(5-fluoro-2-methoxyphenyl)-2-[8-(methylsulfonyl)-8-azabicyclo[3.2.1]oct-2-en-3-yl]-1H-pyrrolo[2,3-b]pyridine;

2-{4-[4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide;

{4-[4-(5-fluoro-2-methoxyphenyl)-1H-pyrrolo[2,3-b]pyridin-2-yl]-3,6-dihydropyridin-1(2H)-yl}acetic acid;

2-{4-[4-(5-fluoro-2-methoxyphenyl)-1H-pyrrolo[2,3-b]pyridin-2-yl]-3,6-dihydropyridin-1(2H)-yl}acetamide;

ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[5-chloro-4-(5-fluoro-2-methoxyphenyl)-1H-pyrrolo[2,3-b]pyridin-2-yl]-N-methyl-3,6-dihydropyridine-1(2H)-carboxamide;

4-(5-fluoro-2-methoxyphenyl)-2-[1-(S-methylsulfonimidoyl)-1,2,3,6-tetrahydropyridin-4-yl]-1H-pyrrolo[2,3-b]pyridine;

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;

4-[4-(4,5-difluoro-2-methoxyphenyl)-1H-pyrrolo[2,3-b]pyridin-2-yl]-N-methyl-3,6-dihydropyridine-1(2H)-carboxamide;

2-{3-[4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{4-[4-(2,3-difluorophenyl)-1H-pyrrolo[2,3-b]pyridin-2-yl]-3,6-dihydropyridin-1(2H)-yl}-N,N-dimethylacetamide;

2-{4-[4-(5-fluoro-2-methoxyphenyl)-1H-pyrrolo[2,3-b]pyridin-2-yl]piperidin-1-yl}-N,N-dimethylacetamide;

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide;

ethyl ({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{4-[4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone;

N-{4-[4-(5-fluoro-2-methoxyphenyl)-1H-pyrrolo[2,3-b]pyridin-2-yl]cyclohex-3-en-1-yl}-D-valine;

1-{4-[4-(5-fluoro-2-methoxyphenyl)-1H-pyrrolo[2,3-b]pyridin-2-yl]cyclohex-3-en-1-yl}-L-proline;

N-cyano-4-[4-(5-fluoro-2-methoxyphenyl)-1H-pyrrolo[2,3-b]pyridin-2-yl]-3,6-dihydropyridine-1(2H)-carboxamide;

1-({4-[4-(5-fluoro-2-methoxyphenyl)-1H-pyrrolo[2,3-b]pyridin-2-yl]-3,6-dihydropyridin-1(2H)-yl}acetyl)-L-prolinamide;

2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]piperidin-1-yl}-N-methylacetamide;
2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile;
4-[3-cyano-4-(5-fluoro-2-methoxyphenyl)-1H-pyrrolo[2,3-b]pyridin-2-yl]-N-methyl-3,6-dihydropyridine-1(2H)-carboxamide;
ethyl ({4-[4-(5-fluoro-2-methoxyphenyl)-1H-pyrrolo[2,3-b]pyridin-2-yl]cyclohex-3-en-1-yl}sulfamoyl)carbamate;
2-{4-[4-(5-fluoro-2-methoxyphenyl)-1H-pyrrolo[2,3-b]pyridin-2-yl]piperidin-1-yl}-N-(2-hydroxyethyl)-N-methylacetamide;
2-{4-[4-(5-fluoro-2-methoxyphenyl)-1H-pyrrolo[2,3-b]pyridin-2-yl]piperidin-1-yl}-N-(3-hydroxycyclobutyl)acetamide;
2-{4-[4-(5-fluoro-2-methoxyphenyl)-1H-pyrrolo[2,3-b]pyridin-2-yl]piperidin-1-yl}-1-(3-hydroxyazetidin-1-yl)ethanone;
N-{4-[4-(5-fluoro-2-methoxyphenyl)-1H-pyrrolo[2,3-b]pyridin-2-yl]cyclohex-3-en-1-yl}-3-methyl-L-valine;
2-{4-[5-fluoro-4-(5-fluoro-2-methoxyphenyl)-1H-pyrrolo[2,3-b]pyridin-2-yl]piperidin-1-yl}-N,N-dimethylacetamide;
2-{4-[3-cyano-4-(5-fluoro-2-methoxyphenyl)-1H-pyrrolo[2,3-b]pyridin-2-yl]-3,6-dihydropyridin-1(2H)-yl}-N,N-dimethylacetamide;
2-{4-[4-(2-methoxyphenyl)-1H-pyrrolo[2,3-b]pyridin-2-yl]piperidin-1-yl}-N,N-dimethylacetamide;
4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;
2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone;
2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
4-(5-fluoro-2-methoxyphenyl)-2-((3aS,6aR)-2-(methylsulfonyl)-1,2,3,3a,4,6a-hexahydrocyclopenta[c]pyrrol-5-yl)-1H-pyrrolo[2,3-b]pyridine;
2-{4-[3-cyano-5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide;
4-(5-fluoro-2-methoxyphenyl)-2-((3aR,6aS)-2-(methylsulfonyl)-1,2,3,3a,4,6a-hexahydrocyclopenta[c]pyrrol-5-yl)-1H-pyrrolo[2,3-b]pyridine;
5-fluoro-4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile;
4-[3-cyano-5-fluoro-4-(5-fluoro-2-methoxyphenyl)-1H-pyrrolo[2,3-b]pyridin-2-yl]-N-methyl-3,6-dihydropyridine-1(2H)-carboxamide;
5-fluoro-4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile;
5-fluoro-4-(5-fluoro-2-methoxyphenyl)-2-(1-{2-[(2R)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;
2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide;
2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide;
2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine;
2-{4-[4-(5-fluoro-2-methoxyphenyl)-1H-pyrrolo[2,3-b]pyridin-2-yl]-2,2-dimethyl-3,6-dihydropyridin-1(2H)-yl}-N,N-dimethylacetamide;
4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine;
2-{4-[5-cyano-4-(5-fluoro-2-methoxyphenyl)-1H-pyrrolo[2,3-b]pyridin-2-yl]piperidin-1-yl}-N,N-dimethylacetamide;
2-{4-[4-(5-fluoro-2-methoxyphenyl)-1H-pyrrolo[2,3-b]pyridin-2-yl]piperidin-1-yl}-N-(3-hydroxycyclobutyl)-N-methylacetamide;
4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
4-[5-fluoro-4-(5-fluoro-2-methoxyphenyl)-1H-pyrrolo[2,3-b]pyridin-2-yl]cyclohex-3-ene-1-carboxylic acid;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-hydroxyethanone;
3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-3-oxopropanenitrile;
5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;
4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile;
(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide;
5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;
(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;

4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-methyl-2-oxoethanesulfonamide;

4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone;

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide;

4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile;

2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide; and pharmaceutically acceptable salts thereof, N-benzyl-4-fluoro-3-[2-(1-methylpiperidin-4-yl)-1H-pyrrolo[2,3-b]pyridin-4-yl]aniline;

4-[({4-fluoro-3-[2-(1-methylpiperidin-4-yl)-1H-pyrrolo[2,3-b]pyridin-4-yl]phenyl}amino)methyl]phenol;

4-fluoro-3-[2-(1-methylpiperidin-4-yl)-1H-pyrrolo[2,3-b]pyridin-4-yl]-N-(1H-1,2,4-triazol-5-ylmethyl)aniline;

4-fluoro-3-[2-(1-methylpiperidin-4-yl)-1H-pyrrolo[2,3-b]pyridin-4-yl]-N-(pyridin-2-ylmethyl)aniline;

N-[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;

N,N-bis[(2,2-dimethyltetrahydro-2H-pyran-4-yl)methyl]-4-fluoro-3-[2-(1-methylpiperidin-4-yl)-1H-pyrrolo[2,3-b]pyridin-4-yl]aniline;

N,N-bis(cyclopropylmethyl)-4-fluoro-3-[2-(1-methylpiperidin-4-yl)-1H-pyrrolo[2,3-b]pyridin-4-yl]aniline;

4-fluoro-3-[2-(1-methylpiperidin-4-yl)-1H-pyrrolo[2,3-b]pyridin-4-yl]-N-[3-(methylsulfonyl)benzyl]aniline;

2-[1-(cyclopropylsulfonyl)-1,2,3,6-tetrahydropyridin-4-yl]-4-(5-fluoro-2-methoxyphenyl)-1H-pyrrolo[2,3-b]pyridine;

4-[({4-fluoro-3-[2-(1-methylpiperidin-4-yl)-1H-pyrrolo[2,3-b]pyridin-4-yl]phenyl}amino)methyl]benzenesulfonamide;

3-[({4-fluoro-3-[2-(1-methylpiperidin-4-yl)-1H-pyrrolo[2,3-b]pyridin-4-yl]phenyl}amino)methyl]phenol;

N-(3-chlorobenzyl)-4-fluoro-3-[2-(1-methylpiperidin-4-yl)-1H-pyrrolo[2,3-b]pyridin-4-yl]aniline;

4-fluoro-N-(4-fluorobenzyl)-3-[2-(1-methylpiperidin-4-yl)-1H-pyrrolo[2,3-b]pyridin-4-yl]aniline;

4-fluoro-N-(2-fluorobenzyl)-3-[2-(1-methylpiperidin-4-yl)-1H-pyrrolo[2,3-b]pyridin-4-yl]aniline;

4-fluoro-N-(3-methoxybenzyl)-3-[2-(1-methylpiperidin-4-yl)-1H-pyrrolo[2,3-b]pyridin-4-yl]aniline;

{4-[({4-fluoro-3-[2-(1-methylpiperidin-4-yl)-1H-pyrrolo[2,3-b]pyridin-4-yl]phenyl}amino)methyl]phenoxy}acetic acid;

N-[(1,1-dioxidotetrahydro-2H-thiopyran-4-yl)methyl]-4-fluoro-3-[2-(1-methylpiperidin-4-yl)-1H-pyrrolo[2,3-b]pyridin-4-yl]aniline;

4-[4-(5-fluoro-2-methoxyphenyl)-1H-pyrrolo[2,3-b]pyridin-2-yl]tetrahydro-2H-thiopyran-4-ol 1,1-dioxide;

2-(1,1-dioxido-3,6-dihydro-2H-thiopyran-4-yl)-4-(5-fluoro-2-methoxyphenyl)-1H-pyrrolo[2,3-b]pyridine;

3-[4-(5-fluoro-2-methoxyphenyl)-1H-pyrrolo[2,3-b]pyridin-2-yl]pyrrolidin-3-ol;

2-(2,5-dihydro-1H-pyrrol-3-yl)-4-(5-fluoro-2-methoxyphenyl)-1H-pyrrolo[2,3-b]pyridine;

4-fluoro-N-(3-fluorobenzyl)-3-[2-(1-methylpiperidin-4-yl)-1H-pyrrolo[2,3-b]pyridin-4-yl]aniline;

N-(2,4-difluorobenzyl)-4-fluoro-3-[2-(1-methylpiperidin-4-yl)-1H-pyrrolo[2,3-b]pyridin-4-yl]aniline;

N-(2,6-difluorobenzyl)-4-fluoro-3-[2-(1-methylpiperidin-4-yl)-1H-pyrrolo[2,3-b]pyridin-4-yl]aniline;

2-{1-[(chloromethyl)sulfonyl]-1,2,3,6-tetrahydropyridin-4-yl}-4-(5-fluoro-2-methoxyphenyl)-1H-pyrrolo[2,3-b]pyridine;

4-(5-fluoro-2-methoxyphenyl)-2-[1-(propan-2-ylsulfonyl)-1,2,3,6-tetrahydropyridin-4-yl]-1H-pyrrolo[2,3-b]pyridine;

4-(5-fluoro-2-methoxyphenyl)-2-[1-(propylsulfonyl)-1,2,3,6-tetrahydropyridin-4-yl]-1H-pyrrolo[2,3-b]pyridine;

2-{1-[(1,1-dioxidotetrahydrothiophen-3-yl)sulfonyl]-1,2,3,6-tetrahydropyridin-4-yl}-4-(5-fluoro-2-methoxyphenyl)-1H-pyrrolo[2,3-b]pyridine;

N-(2,5-difluorobenzyl)-4-fluoro-3-[2-(1-methylpiperidin-4-yl)-1H-pyrrolo[2,3-b]pyridin-4-yl]aniline;

4-(5-fluoro-2-methoxyphenyl)-2-{1-[(2,2,2-trifluoroethyl)sulfonyl]-1,2,3,6-tetrahydropyridin-4-yl}-1H-pyrrolo[2,3-b]pyridine;

N-(2-chlorobenzyl)-4-fluoro-3-[2-(1-methylpiperidin-4-yl)-1H-pyrrolo[2,3-b]pyridin-4-yl]aniline;

3-[({4-fluoro-3-[2-(1-methylpiperidin-4-yl)-1H-pyrrolo[2,3-b]pyridin-4-yl]phenyl}amino)methyl]benzoic acid;

4-[({4-fluoro-3-[2-(1-methylpiperidin-4-yl)-1H-pyrrolo[2,3-b]pyridin-4-yl]phenyl}amino)methyl]benzonitrile;

2-[({4-fluoro-3-[2-(1-methylpiperidin-4-yl)-1H-pyrrolo[2,3-b]pyridin-4-yl]phenyl}amino)methyl]benzonitrile;

3-[({4-fluoro-3-[2-(1-methylpiperidin-4-yl)-1H-pyrrolo[2,3-b]pyridin-4-yl]phenyl}amino)methyl]benzonitrile;

trans-4-[4-(5-fluoro-2-methoxyphenyl)-1H-pyrrolo[2,3-b]pyridin-2-yl]-N-{[1-(methoxymethyl)-1H-1,2,3-triazol-4-yl]methyl}cyclohexanamine;

trans-4-[4-(5-fluoro-2-methoxyphenyl)-1H-pyrrolo[2,3-b]pyridin-2-yl]-N-{[1-(methoxymethyl)-1H-1,2,3-triazol-5-yl]methyl}cyclohexanamine;

2,4-difluoro-N-[(4-methyltetrahydro-2H-pyran-4-yl)methyl]-5-[2-(piperidin-4-yl)-1H-pyrrolo[2,3-b]pyridin-4-yl]aniline;

N-benzyl-2,4-difluoro-5-[2-(piperidin-4-yl)-1H-pyrrolo[2,3-b]pyridin-4-yl]aniline;

2,4-difluoro-5-[2-(piperidin-4-yl)-1H-pyrrolo[2,3-b]pyridin-4-yl]-N-(tetrahydro-2H-pyran-4-ylmethyl)aniline;

2,4-difluoro-N-(3-fluorobenzyl)-5-[2-(piperidin-4-yl)-1H-pyrrolo[2,3-b]pyridin-4-yl]aniline;

4-(5-fluoro-2-methoxyphenyl)-2-[1-(thiophen-2-ylsulfonyl)-1,2,3,6-tetrahydropyridin-4-yl]-1H-pyrrolo[2,3-b]pyridine;

N-[2-chloro-4-({4-[4-(5-fluoro-2-methoxyphenyl)-1H-pyrrolo[2,3-b]pyridin-2-yl]-3,6-dihydropyridin-1(2H)-yl}sulfonyl)phenyl]acetamide;

4-(5-fluoro-2-methoxyphenyl)-2-{1-[(2,4,5-trichlorophenyl)sulfonyl]-1,2,3,6-tetrahydropyridin-4-yl}-1H-pyrrolo[2,3-b]pyridine;

4-({4-[4-(5-fluoro-2-methoxyphenyl)-1H-pyrrolo[2,3-b]pyridin-2-yl]-3,6-dihydropyridin-1(2H)-yl}sulfonyl)-2,1,3-benzoxadiazole;

2-{1-[(3,5-dimethyl-1,2-oxazol-4-yl)sulfonyl]-1,2,3,6-tetrahydropyridin-4-yl}-4-(5-fluoro-2-methoxyphenyl)-1H-pyrrolo[2,3-b]pyridine;

N-(3-chlorobenzyl)-4-fluoro-3-[2-(piperidin-4-yl)-1H-pyrrolo[2,3-b]pyridin-4-yl]aniline;

4-fluoro-N-(3-fluorobenzyl)-3-[2-(piperidin-4-yl)-1H-pyrrolo[2,3-b]pyridin-4-yl]aniline;

4-[({4-fluoro-3-[2-(piperidin-4-yl)-1H-pyrrolo[2,3-b]pyridin-4-yl]phenyl}amino)methyl]benzonitrile;

4-fluoro-N-[4-(methylsulfonyl)benzyl]-3-[2-(piperidin-4-yl)-1H-pyrrolo[2,3-b]pyridin-4-yl]aniline;

4-fluoro-3-[2-(piperidin-4-yl)-1H-pyrrolo[2,3-b]pyridin-4-yl]-N-(pyridin-4-ylmethyl)aniline;

3-[4-(5-fluoro-2-methoxyphenyl)-1H-pyrrolo[2,3-b]pyridin-2-yl]azetidin-3-ol;

4-[4-(5-fluoro-2-methoxyphenyl)-1H-pyrrolo[2,3-b]pyridin-2-yl]-1-(methylsulfonyl)piperidin-4-ol;

2-(1-benzylpiperidin-4-yl)-4-(5-fluoro-2-methoxyphenyl)-1H-pyrrolo[2,3-b]pyridine;

4-(5-fluoro-2-methoxyphenyl)-2-(1-methyl-1,2,3,6-tetrahydropyridin-4-yl)-1H-pyrrolo[2,3-b]pyridine;

4-fluoro-3-{2-[1-(methylsulfonyl)-1,2,3,6-tetrahydropyridin-4-yl]-1H-pyrrolo[2,3-b]pyridin-4-yl}aniline;

4-fluoro-3-[2-(1-methylpiperidin-4-yl)-1H-pyrrolo[2,3-b]pyridin-4-yl]-N-(pyridin-3-ylmethyl)aniline;

4-fluoro-3-[2-(piperidin-4-yl)-1H-pyrrolo[2,3-b]pyridin-4-yl]-N-(pyridin-3-ylmethyl)aniline;

N-(3,5-difluorobenzyl)-4-fluoro-3-[2-(piperidin-4-yl)-1H-pyrrolo[2,3-b]pyridin-4-yl]aniline;

N-(2,4-difluorobenzyl)-4-fluoro-3-[2-(piperidin-4-yl)-1H-pyrrolo[2,3-b]pyridin-4-yl]aniline;

N-(2,5-difluorobenzyl)-4-fluoro-3-[2-(piperidin-4-yl)-1H-pyrrolo[2,3-b]pyridin-4-yl]aniline;

N-(2,6-difluorobenzyl)-4-fluoro-3-[2-(piperidin-4-yl)-1H-pyrrolo[2,3-b]pyridin-4-yl]aniline;

N-(3,5-difluorobenzyl)-4-fluoro-3-[2-(1-methylpiperidin-4-yl)-1H-pyrrolo[2,3-b]pyridin-4-yl]aniline;

4-fluoro-N-(4-fluorobenzyl)-3-[2-(piperidin-4-yl)-1H-pyrrolo[2,3-b]pyridin-4-yl]aniline;

4-[({4-fluoro-3-[2-(piperidin-4-yl)-1H-pyrrolo[2,3-b]pyridin-4-yl]phenyl}amino)methyl]benzenesulfonamide;

3-[({4-fluoro-3-[2-(piperidin-4-yl)-1H-pyrrolo[2,3-b]pyridin-4-yl]phenyl}amino)methyl]phenol;

4-fluoro-3-[2-(piperidin-4-yl)-1H-pyrrolo[2,3-b]pyridin-4-yl]-N-(pyridin-2-ylmethyl)aniline;

4-fluoro-N-[3-(methylsulfonyl)benzyl]-3-[2-(piperidin-4-yl)-1H-pyrrolo[2,3-b]pyridin-4-yl]aniline;

N-(4-fluoro-3-{2-[1-(methylsulfonyl)piperidin-4-yl]-1H-pyrrolo[2,3-b]pyridin-4-yl}phenyl)methanesulfonamide;

N-benzyl-4-fluoro-3-{2-[1-(methylsulfonyl)piperidin-4-yl]-1H-pyrrolo[2,3-b]pyridin-4-yl}aniline;

N-(3-chlorobenzyl)-4-fluoro-3-{2-[1-(methylsulfonyl)piperidin-4-yl]-1H-pyrrolo[2,3-b]pyridin-4-yl}aniline;

4-fluoro-N-(3-fluorobenzyl)-3-{2-[1-(methylsulfonyl)piperidin-4-yl]-1H-pyrrolo[2,3-b]pyridin-4-yl}aniline;

4-(5-fluoro-2-methoxyphenyl)-2-(2,2,6,6-tetramethyl-1,2,3,6-tetrahydropyridin-4-yl)-1H-pyrrolo[2,3-b]pyridine;

4-fluoro-3-{2-[1-(methylsulfonyl)piperidin-4-yl]-1H-pyrrolo[2,3-b]pyridin-4-yl}-N-(pyridin-4-ylmethyl)aniline;

4-{[(4-fluoro-3-{2-[1-(methylsulfonyl)piperidin-4-yl]-1H-pyrrolo[2,3-b]pyridin-4-yl}phenyl)amino]methyl}benzonitrile;

4-{2-fluoro-5-[(3-fluorobenzyl)oxy]phenyl}-2-(1,2,3,6-tetrahydropyridin-4-yl)-1H-pyrrolo[2,3-b]pyridine;

2-({4-[4-(5-fluoro-2-methoxyphenyl)-1H-pyrrolo[2,3-b]pyridin-2-yl]piperidin-1-yl}methyl)-1H-benzimidazole;

4-(5-fluoro-2-methoxyphenyl)-2-[1-(tetrahydrofuran-2-ylmethyl)piperidin-4-yl]-1H-pyrrolo[2,3-b]pyridine;

2-[1-(5,6-dihydro-2H-pyran-3-ylmethyl)piperidin-4-yl]-4-(5-fluoro-2-methoxyphenyl)-1H-pyrrolo[2,3-b]pyridine;

4-(5-fluoro-2-methoxyphenyl)-2-[1-(4-methoxybenzyl)piperidin-4-yl]-1H-pyrrolo[2,3-b]pyridine;

4-(5-fluoro-2-methoxyphenyl)-2-{1-[2-(morpholin-4-yl)ethyl]piperidin-4-yl}-1H-pyrrolo[2,3-b]pyridine;

4-({4-[4-(5-fluoro-2-methoxyphenyl)-1H-pyrrolo[2,3-b]pyridin-2-yl]piperidin-1-yl}methyl)benzonitrile;

1-(2-{4-[4-(5-fluoro-2-methoxyphenyl)-1H-pyrrolo[2,3-b]pyridin-2-yl]-3,6-dihydropyridin-1(2H)-yl}ethyl)-3-methylurea;

4-(5-fluoro-2-methoxyphenyl)-2-[1-(2-methylpropyl)piperidin-4-yl]-1H-pyrrolo[2,3-b]pyridine;

N-[4-({4-[4-(5-fluoro-2-methoxyphenyl)-1H-pyrrolo[2,3-b]pyridin-2-yl]piperidin-1-yl}methyl)phenyl]acetamide;

4-(5-fluoro-2-methoxyphenyl)-2-[1-(pyridin-2-ylmethyl)piperidin-4-yl]-1H-pyrrolo[2,3-b]pyridine;

4-({4-[4-(5-fluoro-2-methoxyphenyl)-1H-pyrrolo[2,3-b]pyridin-2-yl]piperidin-1-yl}methyl)-N,N-dimethylaniline;

2-{1-[(1-tert-butyl-1H-pyrazol-4-yl)methyl]piperidin-4-yl}-4-(5-fluoro-2-methoxyphenyl)-1H-pyrrolo[2,3-b]pyridine;

4-(5-fluoro-2-methoxyphenyl)-2-[1-(2-methoxyethyl)piperidin-4-yl]-1H-pyrrolo[2,3-b]pyridine;
4-(5-fluoro-2-methoxyphenyl)-2-[1-(pyridin-4-ylmethyl)piperidin-4-yl]-1H-pyrrolo[2,3-b]pyridine;
N,N-diethyl-2-[4-({4-[4-(5-fluoro-2-methoxyphenyl)-1H-pyrrolo[2,3-b]pyridin-2-yl]piperidin-1-yl}methyl)phenoxy]ethanamine;
4-chloro-5-({4-[4-(5-fluoro-2-methoxyphenyl)-1H-pyrrolo[2,3-b]pyridin-2-yl]piperidin-1-yl}methyl)-1,3-thiazol-2-amine;
2-[1-(1,3-benzodioxol-5-ylmethyl)piperidin-4-yl]-4-(5-fluoro-2-methoxyphenyl)-1H-pyrrolo[2,3-b]pyridine;
3-{[(4-fluoro-3-{2-[1-(methylsulfonyl)piperidin-4-yl]-1H-pyrrolo[2,3-b]pyridin-4-yl}phenyl)amino]methyl}phenol;
4-fluoro-N-[3-(methylsulfonyl)benzyl]-3-{2-[1-(methylsulfonyl)piperidin-4-yl]-1H-pyrrolo[2,3-b]pyridin-4-yl}aniline;
4-{[(4-fluoro-3-{2-[1-(methylsulfonyl)piperidin-4-yl]-1H-pyrrolo[2,3-b]pyridin-4-yl}phenyl)amino]methyl}benzamide;
4-{[(4-fluoro-3-{2-[1-(methylsulfonyl)piperidin-4-yl]-1H-pyrrolo[2,3-b]pyridin-4-yl}phenyl)amino]methyl}phenol;
4-(5-fluoro-2-methoxyphenyl)-2-{1-[2-(morpholin-4-yl)ethyl]-1,2,3,6-tetrahydropyridin-4-yl}-1H-pyrrolo[2,3-b]pyridine;
2-{1-[(3-chlorobenzyl)sulfonyl]-1,2,3,6-tetrahydropyridin-4-yl}-4-(5-fluoro-2-methoxyphenyl)-1H-pyrrolo[2,3-b]pyridine;
2,4-difluoro-5-{2-[1-(methylsulfonyl)-1,2,3,6-tetrahydropyridin-4-yl]-1H-pyrrolo[2,3-b]pyridin-4-yl}-N-(tetrahydro-2H-pyran-4-ylmethyl)aniline;
2,4-difluoro-N-(tetrahydro-2H-pyran-4-ylmethyl)-5-[2-(1,2,3,6-tetrahydropyridin-4-yl)-1H-pyrrolo[2,3-b]pyridin-4-yl]aniline;
2,4-difluoro-N-(3-fluorobenzyl)-5-[2-(1,2,3,6-tetrahydropyridin-4-yl)-1H-pyrrolo[2,3-b]pyridin-4-yl]aniline;
N-(3,5-difluorobenzyl)-4-fluoro-3-{2-[1-(methylsulfonyl)-1,2,3,6-tetrahydropyridin-4-yl]-1H-pyrrolo[2,3-b]pyridin-4-yl}aniline;
4-[4-(5-fluoro-2-methoxyphenyl)-1H-pyrrolo[2,3-b]pyridin-2-yl]-N-(propan-2-yl)-3,6-dihydropyridine-1(2H)-carboxamide;
2-(1-ethyl-1,2,3,6-tetrahydropyridin-4-yl)-4-(5-fluoro-2-methoxyphenyl)-1H-pyrrolo[2,3-b]pyridine;
2-(1-benzyl-1,2,3,6-tetrahydropyridin-4-yl)-4-(5-fluoro-2-methoxyphenyl)-1H-pyrrolo[2,3-b]pyridine;
4-fluoro-3-{2-[1-(methylsulfonyl)piperidin-4-yl]-1H-pyrrolo[2,3-b]pyridin-4-yl}-N-(pyridin-3-ylmethyl)aniline;
N-(3,5-difluorobenzyl)-4-fluoro-3-{2-[1-(methylsulfonyl)piperidin-4-yl]-1H-pyrrolo[2,3-b]pyridin-4-yl}aniline;
N-(3,4-difluorobenzyl)-4-fluoro-3-{2-[1-(methylsulfonyl)piperidin-4-yl]-1H-pyrrolo[2,3-b]pyridin-4-yl}aniline;
N-(3,4-difluorobenzyl)-4-fluoro-3-[2-(1-methylpiperidin-4-yl)-1H-pyrrolo[2,3-b]pyridin-4-yl]aniline;
1-[4-(4-{5-[(3,5-difluorobenzyl)amino]-2-fluorophenyl}-1H-pyrrolo[2,3-b]pyridin-2-yl)piperidin-1-yl]-2-hydroxyethanone;
3-[4-(4-{2-fluoro-5-[(pyridin-3-ylmethyl)amino]phenyl}-1H-pyrrolo[2,3-b]pyridin-2-yl)piperidin-1-yl]propane-1,2-diol;
3-[4-(4-{2-fluoro-5-[(pyridin-4-ylmethyl)amino]phenyl}-1H-pyrrolo[2,3-b]pyridin-2-yl)piperidin-1-yl]propane-1,2-diol;
4-{[(3-{2-[1-(2,3-dihydroxypropyl)piperidin-4-yl]-1H-pyrrolo[2,3-b]pyridin-4-yl}-4-fluorophenyl)amino]methyl}benzonitrile;
3-{[(3-{2-[1-(2,3-dihydroxypropyl)piperidin-4-yl]-1H-pyrrolo[2,3-b]pyridin-4-yl}-4-fluorophenyl)amino]methyl}benzonitrile;
3-{2-[1-(cyclopropylsulfonyl)piperidin-4-yl]-1H-pyrrolo[2,3-b]pyridin-4-yl}-4-fluoro-N-(pyridin-4-ylmethyl)aniline;
4-{[(3-{2-[1-(cyclopropylsulfonyl)piperidin-4-yl]-1H-pyrrolo[2,3-b]pyridin-4-yl}-4-fluorophenyl)amino]methyl}benzonitrile;
3-{2-[1-(cyclopropylsulfonyl)piperidin-4-yl]-1H-pyrrolo[2,3-b]pyridin-4-yl}-N-(3,5-difluorobenzyl)-4-fluoroaniline;
3-{2-[1-(cyclopropylsulfonyl)piperidin-4-yl]-1H-pyrrolo[2,3-b]pyridin-4-yl}-4-fluoro-N-[3-(methylsulfonyl)benzyl]aniline;
4-(4-{2-fluoro-5-[(3-fluorobenzyl)amino]phenyl}-1H-pyrrolo[2,3-b]pyridin-2-yl)piperidine-1-sulfonamide;
3-[4-(4-{2-fluoro-5-[(3-fluorobenzyl)amino]phenyl}-1H-pyrrolo[2,3-b]pyridin-2-yl)piperidin-1-yl]propane-1,2-diol;
4-(5-fluoro-2-methoxyphenyl)-2-[4-(pyrrolidin-1-yl)cyclohex-1-en-1-yl]-1H-pyrrolo[2,3-b]pyridine;
4-(5-fluoro-2-methoxyphenyl)-2-[1-(methylsulfonyl)-2,5-dihydro-1H-pyrrol-3-yl]-1H-pyrrolo[2,3-b]pyridine;
3-[4-(4-{2-fluoro-5-[(3-fluorobenzyl)oxy]phenyl}-1H-pyrrolo[2,3-b]pyridin-2-yl)-3,6-dihydropyridin-1(2H)-yl]propane-1,2-diol;
3-[4-(4-{2,4-difluoro-5-[(3-fluorobenzyl)amino]phenyl}-1H-pyrrolo[2,3-b]pyridin-2-yl)-3,6-dihydropyridin-1(2H)-yl]propane-1,2-diol;
2-({4-[4-(5-fluoro-2-methoxyphenyl)-1H-pyrrolo[2,3-b]pyridin-2-yl]-3,6-dihydropyridin-1(2H)-yl}methyl)-1H-benzimidazole;
2-[1-(5,6-dihydro-2H-pyran-3-ylmethyl)-1,2,3,6-tetrahydropyridin-4-yl]-4-(5-fluoro-2-methoxyphenyl)-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)-N,N-dimethylaniline;
N,N-diethyl-2-[4-({4-[4-(5-fluoro-2-methoxyphenyl)-1H-pyrrolo[2,3-b]pyridin-2-yl]-3,6-dihydropyridin-1(2H)-yl}methyl)phenoxy]ethanamine;
4-(5-fluoro-2-methoxyphenyl)-2-[1-(pyridin-4-ylmethyl)-1,2,3,6-tetrahydropyridin-4-yl]-1H-pyrrolo[2,3-b]pyridine;
4-({4-[4-(5-fluoro-2-methoxyphenyl)-1H-pyrrolo[2,3-b]pyridin-2-yl]-3,6-dihydropyridin-1(2H)-yl}methyl)benzonitrile;
4-chloro-5-({4-[4-(5-fluoro-2-methoxyphenyl)-1H-pyrrolo[2,3-b]pyridin-2-yl]-3,6-dihydropyridin-1(2H)-yl}methyl)-1,3-thiazol-2-amine;
4-(5-fluoro-2-methoxyphenyl)-2-[1-(tetrahydrofuran-2-ylmethyl)-1,2,3,6-tetrahydropyridin-4-yl]-1H-pyrrolo[2,3-b]pyridine;
4-chloro-3-[2-(2,5-dihydro-1H-pyrrol-3-yl)-1H-pyrrolo[2,3-b]pyridin-4-yl]-N-(pyridin-3-ylmethyl)aniline;
4-chloro-3-[2-(2,5-dihydro-1H-pyrrol-3-yl)-1H-pyrrolo[2,3-b]pyridin-4-yl]-N-(3-fluorobenzyl)aniline;
4-chloro-3-[2-(2,5-dihydro-1H-pyrrol-3-yl)-1H-pyrrolo[2,3-b]pyridin-4-yl]-N-(tetrahydro-2H-pyran-3-ylmethyl) aniline;

4-chloro-3-[2-(2,5-dihydro-1H-pyrrol-3-yl)-1H-pyrrolo[2,3-b]pyridin-4-yl]-N-(piperidin-4-ylmethyl)aniline;
5-fluoro-4-(5-fluoro-2-methoxyphenyl)-2-(piperidin-4-yl)-1H-pyrrolo[2,3-b]pyridine;
N-cyclohexyl-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-(4-methoxybenzyl)-3,6-dihydropyridine-1(2H)-carboxamide;
4-[4-(5-fluoro-2-methoxyphenyl)-1H-pyrrolo[2,3-b]pyridin-2-yl]-N-phenyl-3,6-dihydropyridine-1(2H)-carboxamide;
4-(4-{2-fluoro-5-[(pyridin-4-ylmethyl)amino]phenyl}-1H-pyrrolo[2,3-b]pyridin-2-yl)piperidine-1-sulfonamide;
5-fluoro-4-(5-fluoro-2-methoxyphenyl)-2-[1-(methylsulfonyl)piperidin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]piperidin-1-yl}propane-1,2-diol;
1-{4-[5-fluoro-4-(5-fluoro-2-methoxyphenyl)-1H-pyrrolo[2,3-b]pyridin-2-yl]piperidin-1-yl}ethanone;
3-[4-(4-{5-[(3,5-difluorobenzyl)amino]-2-fluorophenyl}-1H-pyrrolo[2,3-b]pyridin-2-yl)piperidin-1-yl]propane-1,2-diol;
4-[4-(5-fluoro-2-methoxyphenyl)-1H-pyrrolo[2,3-b]pyridin-2-yl]-N-[2-(morpholin-4-yl)ethyl]3,6-dihydropyridine-1(2H)-carboxamide;
4-(5-fluoro-2-methoxyphenyl)-2-(1-{[2-(morpholin-4-yl)ethyl]sulfonyl}-1,2,3,6-tetrahydropyridin-4-yl)-1H-pyrrolo[2,3-b]pyridine;
{4-[4-(5-fluoro-2-methoxyphenyl)-1H-pyrrolo[2,3-b]pyridin-2-yl]-3,6-dihydropyridin-1(2H)-yl}(pyridin-2-yl)methanone;
{4-[4-(5-fluoro-2-methoxyphenyl)-1H-pyrrolo[2,3-b]pyridin-2-yl]-3,6-dihydropyridin-1(2H)-yl}(pyridin-3-yl)methanone;
{4-[4-(5-fluoro-2-methoxyphenyl)-1H-pyrrolo[2,3-b]pyridin-2-yl]-3,6-dihydropyridin-1(2H)-yl}(pyridin-4-yl)methanone;
{4-[4-(5-fluoro-2-methoxyphenyl)-1H-pyrrolo[2,3-b]pyridin-2-yl]-3,6-dihydropyridin-1(2H)-yl}(pyrazin-2-yl)methanone;
4-(5-fluoro-2-methoxyphenyl)-2-[1-(pyrimidin-4-yl)-1,2,3,6-tetrahydropyridin-4-yl]-1H-pyrrolo[2,3-b]pyridine;
4-(5-fluoro-2-methoxyphenyl)-2-[1-(2-methylpyrimidin-4-yl)-1,2,3,6-tetrahydropyridin-4-yl]-1H-pyrrolo[2,3-b]pyridine;
4-(5-fluoro-2-methoxyphenyl)-2-{1-[6-(trifluoromethyl)pyrimidin-4-yl]-1,2,3,6-tetrahydropyridin-4-yl}-1H-pyrrolo[2,3-b]pyridine;
1-{4-[4-(5-fluoro-2-methoxyphenyl)-1H-pyrrolo[2,3-b]pyridin-2-yl]-3,6-dihydropyridin-1(2H)-yl}-3-(piperidin-1-yl)propan-1-one;
{4-[4-(5-fluoro-2-methoxyphenyl)-1H-pyrrolo[2,3-b]pyridin-2-yl]-3,6-dihydropyridin-1(2H)-yl}(1H-pyrazol-4-yl)methanone;
{4-[4-(5-fluoro-2-methoxyphenyl)-1H-pyrrolo[2,3-b]pyridin-2-yl]-3,6-dihydropyridin-1(2H)-yl}(1,3-thiazol-4-yl)methanone;
(3,5-dimethyl-1,2-oxazol-4-yl){4-[4-(5-fluoro-2-methoxyphenyl)-1H-pyrrolo[2,3-b]pyridin-2-yl]-3,6-dihydropyridin-1(2H)-yl}methanone;
4-(2-chloro-5-methoxyphenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-(2,3,4-trifluorophenyl)-1H-pyrrolo[2,3-b]pyridine;
2-[1-(methylsulfonyl)-1,2,3,6-tetrahydropyridin-4-yl]-4-[3-(trifluoromethoxy)phenyl]-1H-pyrrolo[2,3-b]pyridine;
N-(2-{4-[4-(5-fluoro-2-methoxyphenyl)-1H-pyrrolo[2,3-b]pyridin-2-yl]-3,6-dihydropyridin-1(2H)-yl}ethyl)-$N^2,N^2$-dimethylglycinamide;
4-(4-methoxyphenyl)-2-[1-(methylsulfonyl)-1,2,3,6-tetrahydropyridin-4-yl]-1H-pyrrolo[2,3-b]pyridine;
4-(3,4-difluorophenyl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[2-(trifluoromethoxy)phenyl]-1H-pyrrolo[2,3-b]pyridine;
4-[5-fluoro-2-(propan-2-yloxy)phenyl]-2-[1-(methylsulfonyl)-1,2,3,6-tetrahydropyridin-4-yl]-1H-pyrrolo[2,3-b]pyridine;
4-[2-(cyclopropyloxy)-5-fluorophenyl]-2-[1-(methylsulfonyl)-1,2,3,6-tetrahydropyridin-4-yl]-1H-pyrrolo[2,3-b]pyridine;
4-(4-ethoxy-3-fluorophenyl)-2-[1-(methylsulfonyl)-1,2,3,6-tetrahydropyridin-4-yl]-1H-pyrrolo[2,3-b]pyridine;
4-(4-{5-[(3,5-difluorobenzyl)amino]-2-fluorophenyl}-1H-pyrrolo[2,3-b]pyridin-2-yl)piperidine-1-sulfonamide;
4-(4-chloro-3-methylphenyl)-2-[1-(methylsulfonyl)-1,2,3,6-tetrahydropyridin-4-yl]-1H-pyrrolo[2,3-b]pyridine;
4-(3-chloro-4-fluorophenyl)-2-[1-(methylsulfonyl)-1,2,3,6-tetrahydropyridin-4-yl]-1H-pyrrolo[2,3-b]pyridine;
N,N-dimethyl-3-{2-[1-(methylsulfonyl)-1,2,3,6-tetrahydropyridin-4-yl]-1H-pyrrolo[2,3-b]pyridin-4-yl}benzamide;
4-(4-fluoro-3-methylphenyl)-2-[1-(methylsulfonyl)-1,2,3,6-tetrahydropyridin-4-yl]-1H-pyrrolo[2,3-b]pyridine;
4-[3-fluoro-4-(propan-2-yloxy)phenyl]-2-[1-(methylsulfonyl)-1,2,3,6-tetrahydropyridin-4-yl]-1H-pyrrolo[2,3-b]pyridine;
4-(4-butoxy-3-fluorophenyl)-2-[1-(methylsulfonyl)-1,2,3,6-tetrahydropyridin-4-yl]-1H-pyrrolo[2,3-b]pyridine;
(3-{2-[1-(methylsulfonyl)-1,2,3,6-tetrahydropyridin-4-yl]-1H-pyrrolo[2,3-b]pyridin-4-yl}phenyl)(morpholin-4-yl)methanone;
N-(3,5-difluorobenzyl)-4-fluoro-3-[2-(1,2,3,6-tetrahydropyridin-4-yl)-1H-pyrrolo[2,3-b]pyridin-4-yl]aniline;
4-(5-fluoro-2-methoxyphenyl)-2-(1,2,5,6-tetrahydropyridin-3-yl)-1H-pyrrolo[2,3-b]pyridine;
4-(3,5-difluorophenyl)-2-[1-(methylsulfonyl)-1,2,3,6-tetrahydropyridin-4-yl]-1H-pyrrolo[2,3-b]pyridine;
4-(2,4-dichlorophenyl)-2-[1-(methylsulfonyl)-1,2,3,6-tetrahydropyridin-4-yl]-1H-pyrrolo[2,3-b]pyridine;
4-(2-ethylphenyl)-2-[1-(methylsulfonyl)-1,2,3,6-tetrahydropyridin-4-yl]-1H-pyrrolo[2,3-b]pyridine;
4-(2,4-dimethylphenyl)-2-[1-(methylsulfonyl)-1,2,3,6-tetrahydropyridin-4-yl]-1H-pyrrolo[2,3-b]pyridine;
4-(2,5-dichlorophenyl)-2-[1-(methylsulfonyl)-1,2,3,6-tetrahydropyridin-4-yl]-1H-pyrrolo[2,3-b]pyridine;
4-(3,4-dichlorophenyl)-2-[1-(methylsulfonyl)-1,2,3,6-tetrahydropyridin-4-yl]-1H-pyrrolo[2,3-b]pyridine;

N-(4-{2-[1-(methylsulfonyl)-1,2,3,6-tetrahydropyridin-4-yl]-1H-pyrrolo[2,3-b]pyridin-4-yl}phenyl)methanesulfonamide;
4-(5-chloro-2-methoxyphenyl)-2-[1-(methylsulfonyl)-1,2,3,6-tetrahydropyridin-4-yl]-1H-pyrrolo[2,3-b]pyridine;
4-[2-methoxy-5-(propan-2-yl)phenyl]-2-[1-(methylsulfonyl)-1,2,3,6-tetrahydropyridin-4-yl]-1H-pyrrolo[2,3-b]pyridine;
4-(2-methoxy-5-methylphenyl)-2-[1-(methylsulfonyl)-1,2,3,6-tetrahydropyridin-4-yl]-1H-pyrrolo[2,3-b]pyridine;
4-(4-methoxy-3-methylphenyl)-2-[1-(methylsulfonyl)-1,2,3,6-tetrahydropyridin-4-yl]-1H-pyrrolo[2,3-b]pyridine;
2-{2-[1-(methylsulfonyl)-1,2,3,6-tetrahydropyridin-4-yl]-1H-pyrrolo[2,3-b]pyridin-4-yl}benzonitrile;
4-(2-methoxyphenyl)-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}benzonitrile;
2-[1-(methylsulfonyl)-1,2,3,6-tetrahydropyridin-4-yl]-4-[2-(trifluoromethyl)phenyl]-1H-pyrrolo[2,3-b]pyridine;
4-(3-chlorophenyl)-2-[1-(methylsulfonyl)-1,2,3,6-tetrahydropyridin-4-yl]-1H-pyrrolo[2,3-b]pyridine;
4-(2-chlorophenyl)-2-[1-(methylsulfonyl)-1,2,3,6-tetrahydropyridin-4-yl]-1H-pyrrolo[2,3-b]pyridine;
4-[2-fluoro-5-(trifluoromethyl)phenyl]-2-[1-(methylsulfonyl)-1,2,3,6-tetrahydropyridin-4-yl]-1H-pyrrolo[2,3-b]pyridine;
4-(3-chloro-4-methoxyphenyl)-2-[1-(methylsulfonyl)-1,2,3,6-tetrahydropyridin-4-yl]-1H-pyrrolo[2,3-b]pyridine;
4-(2-fluoro-5-methylphenyl)-2-[1-(methylsulfonyl)-1,2,3,6-tetrahydropyridin-4-yl]-1H-pyrrolo[2,3-b]pyridine;
4-(5-chloro-2-fluoro-3-methylphenyl)-2-[1-(methylsulfonyl)-1,2,3,6-tetrahydropyridin-4-yl]-1H-pyrrolo[2,3-b]pyridine;
4-(5-chloro-2-propoxyphenyl)-2-[1-(methylsulfonyl)-1,2,3,6-tetrahydropyridin-4-yl]-1H-pyrrolo[2,3-b]pyridine;
4-(4-{5-[(3,5-difluorobenzyl)amino]-2-fluorophenyl}-1H-pyrrolo[2,3-b]pyridin-2-yl)-N-methyl-3,6-dihydropyridine-1(2H)-carboxamide;
3-[4-(4-{5-[(3,5-difluorobenzyl)amino]-2-fluorophenyl}-1H-pyrrolo[2,3-b]pyridin-2-yl)-3,6-dihydropyridin-1(2H)-yl]propane-1,2-diol;
ethyl 4-[4-(5-fluoro-2-methoxyphenyl)-1H-pyrrolo[2,3-b]pyridin-2-yl]cyclohex-3-ene-1-carboxylate;
4-(2-ethoxy-5-fluorophenyl)-2-[1-(methylsulfonyl)-1,2,3,6-tetrahydropyridin-4-yl]-1H-pyrrolo[2,3-b]pyridine;
4-(2,3-dichlorophenyl)-2-[1-(methylsulfonyl)-1,2,3,6-tetrahydropyridin-4-yl]-1H-pyrrolo[2,3-b]pyridine;
4-(3-chloro-4-methylphenyl)-2-[1-(methylsulfonyl)-1,2,3,6-tetrahydropyridin-4-yl]-1H-pyrrolo[2,3-b]pyridine;
2-methyl-5-{2-[1-(methylsulfonyl)-1,2,3,6-tetrahydropyridin-4-yl]-1H-pyrrolo[2,3-b]pyridin-4-yl}aniline;
4-(2-fluorobiphenyl-4-yl)-2-[1-(methylsulfonyl)-1,2,3,6-tetrahydropyridin-4-yl]-1H-pyrrolo[2,3-b]pyridine;
2-[1-(methylsulfonyl)-1,2,3,6-tetrahydropyridin-4-yl]-4-[3-(propan-2-yloxy)phenyl]-1H-pyrrolo[2,3-b]pyridine;
4-(3-fluoro-4-propoxyphenyl)-2-[1-(methylsulfonyl)-1,2,3,6-tetrahydropyridin-4-yl]-1H-pyrrolo[2,3-b]pyridine;
4-[2-fluoro-5-(propan-2-yloxy)phenyl]-2-[1-(methylsulfonyl)-1,2,3,6-tetrahydropyridin-4-yl]-1H-pyrrolo[2,3-b]pyridine;
4-(4-butoxy-3-chlorophenyl)-2-[1-(methylsulfonyl)-1,2,3,6-tetrahydropyridin-4-yl]-1H-pyrrolo[2,3-b]pyridine;
4-[2-(2-methylpropoxy)phenyl]-2-[1-(methylsulfonyl)-1,2,3,6-tetrahydropyridin-4-yl]-1H-pyrrolo[2,3-b]pyridine;
4-{2-[1-(methylsulfonyl)-1,2,3,6-tetrahydropyridin-4-yl]-1H-pyrrolo[2,3-b]pyridin-4-yl}benzonitrile;
2-[1-(methylsulfonyl)-1,2,3,6-tetrahydropyridin-4-yl]-4-phenyl-1H-pyrrolo[2,3-b]pyridine;
(4-{4-[4-(5-fluoro-2-methoxyphenyl)-1H-pyrrolo[2,3-b]pyridin-2-yl]-3,6-dihydropyridin-1(2H)-yl}piperidin-1-yl)acetic acid;
4-(3-fluoro-4-methoxyphenyl)-2-[1-(methylsulfonyl)-1,2,3,6-tetrahydropyridin-4-yl]-1H-pyrrolo[2,3-b]pyridine;
3-{2-[1-(methylsulfonyl)-1,2,3,6-tetrahydropyridin-4-yl]-1H-pyrrolo[2,3-b]pyridin-4-yl}aniline;
N-(2-{2-[1-(methylsulfonyl)-1,2,3,6-tetrahydropyridin-4-yl]-1H-pyrrolo[2,3-b]pyridin-4-yl}phenyl)methanesulfonamide;
3-{2-[1-(methylsulfonyl)-1,2,3,6-tetrahydropyridin-4-yl]-1H-pyrrolo[2,3-b]pyridin-4-yl}-N-(propan-2-yl)benzamide;
2-{4-[3-cyano-4-(5-fluoro-2-methoxyphenyl)-1H-pyrrolo[2,3-b]pyridin-2-yl]piperazin-1-yl}-N,N-dimethylacetamide;
(4-{2-[1-(methylsulfonyl)-1,2,3,6-tetrahydropyridin-4-yl]-1H-pyrrolo[2,3-b]pyridin-4-yl}phenyl)acetonitrile;
N-methyl-4-{2-[1-(methylsulfonyl)-1,2,3,6-tetrahydropyridin-4-yl]-1H-pyrrolo[2,3-b]pyridin-4-yl}benzamide;
N-(3-{2-[1-(methylsulfonyl)-1,2,3,6-tetrahydropyridin-4-yl]-1H-pyrrolo[2,3-b]pyridin-4-yl}phenyl)acetamide;
N-(4-{2-[1-(methylsulfonyl)-1,2,3,6-tetrahydropyridin-4-yl]-1H-pyrrolo[2,3-b]pyridin-4-yl}phenyl)acetamide;
4-[4-(5-fluoro-2-methoxyphenyl)-1H-pyrrolo[2,3-b]pyridin-2-yl]-N-methyl-3,6-dihydropyridine-1(2H)-sulfonamide;
4-(5-fluoro-2-methoxyphenyl)-2-[1-(pyridin-2-ylmethyl)-1,2,3,6-tetrahydropyridin-4-yl]-1H-pyrrolo[2,3-b]pyridine;
3-{5-[4-(5-fluoro-2-methoxyphenyl)-1H-pyrrolo[2,3-b]pyridin-2-yl]-3,6-dihydropyridin-1(2H)-yl}propane-1,2-diol;
5-[4-(5-fluoro-2-methoxyphenyl)-1H-pyrrolo[2,3-b]pyridin-2-yl]-N-methyl-3,6-dihydropyridine-1(2H)-carboxamide;
4-(5-fluoro-2-methoxyphenyl)-2-[1-(methylsulfonyl)-1,2,5,6-tetrahydropyridin-3-yl]-1H-pyrrolo[2,3-b]pyridine;
4-(5-fluoro-2-methylphenyl)-2-[1-(methylsulfonyl)-1,2,3,6-tetrahydropyridin-4-yl]-1H-pyrrolo[2,3-b]pyridine;
4-{5-[(3,5-difluorobenzyl)oxy]-2-fluorophenyl}-2-(1,2,3,6-tetrahydropyridin-4-yl)-1H-pyrrolo[2,3-b]pyridine;
4-{5-[(3,5-difluorobenzyl)oxy]-2-fluorophenyl}-2-(1-methyl-1,2,3,6-tetrahydropyridin-4-yl)-1H-pyrrolo[2,3-b]pyridine;

3-[4-(4-{5-[(3,5-difluorobenzyl)oxy]-2-fluorophenyl}-1H-pyrrolo[2,3-b]pyridin-2-yl)-3,6-dihydropyridin-1(2H)-yl]propane-1,2-diol;

4-{5-[(3,5-difluorobenzyl)oxy]-2-fluorophenyl}-2-[1-(methylsulfonyl)-1,2,3,6-tetrahydropyridin-4-yl]-1H-pyrrolo[2,3-b]pyridine;

3-{2-[1-(methylsulfonyl)-1,2,3,6-tetrahydropyridin-4-yl]-1H-pyrrolo[2,3-b]pyridin-4-yl}benzamide;

4-(4-ethoxy-2-methylphenyl)-2-[1-(methylsulfonyl)-1,2,3,6-tetrahydropyridin-4-yl]-1H-pyrrolo[2,3-b]pyridine;

4-[4-chloro-3-(trifluoromethyl)phenyl]-2-[1-(methylsulfonyl)-1,2,3,6-tetrahydropyridin-4-yl]-1H-pyrrolo[2,3-b]pyridine;

N-butyl-3-{2-[1-(methylsulfonyl)-1,2,3,6-tetrahydropyridin-4-yl]-1H-pyrrolo[2,3-b]pyridin-4-yl}benzamide;

4-(3-fluorophenyl)-2-[1-(methylsulfonyl)-1,2,3,6-tetrahydropyridin-4-yl]-1H-pyrrolo[2,3-b]pyridine;

4-{3-chloro-4-[(3-chlorobenzyl)oxy]phenyl}-2-[1-(methylsulfonyl)-1,2,3,6-tetrahydropyridin-4-yl]-1H-pyrrolo[2,3-b]pyridine;

4-(4-fluoro-2-methoxyphenyl)-2-[1-(methylsulfonyl)-1,2,3,6-tetrahydropyridin-4-yl]-1H-pyrrolo[2,3-b]pyridine;

2-[1-(methylsulfonyl)-1,2,3,6-tetrahydropyridin-4-yl]-4-[4-(trifluoromethoxy)phenyl]-1H-pyrrolo[2,3-b]pyridine;

4-[3-chloro-4-(propan-2-yloxy)phenyl]-2-[1-(methylsulfonyl)-1,2,3,6-tetrahydropyridin-4-yl]-1H-pyrrolo[2,3-b]pyridine;

4-(3,5-dichlorophenyl)-2-[1-(methylsulfonyl)-1,2,3,6-tetrahydropyridin-4-yl]-1H-pyrrolo[2,3-b]pyridine;

4-(4-fluoro-2-propoxyphenyl)-2-[1-(methylsulfonyl)-1,2,3,6-tetrahydropyridin-4-yl]-1H-pyrrolo[2,3-b]pyridine;

4-(5-fluoro-2-methoxyphenyl)-2-[1-(morpholin-4-ylsulfonyl)-1,2,3,6-tetrahydropyridin-4-yl]-1H-pyrrolo[2,3-b]pyridine;

2-fluoro-N-{4-methoxy-3-[2-(1,2,3,6-tetrahydropyridin-4-yl)-1H-pyrrolo[2,3-b]pyridin-4-yl]benzyl}aniline;

N-{4-methoxy-3-[2-(1,2,3,6-tetrahydropyridin-4-yl)-1H-pyrrolo[2,3-b]pyridin-4-yl]benzyl}tetrahydro-2H-pyran-4-amine;

4-[2-methoxy-5-(morpholin-4-ylmethyl)phenyl]-2-(1,2,3,6-tetrahydropyridin-4-yl)-1H-pyrrolo[2,3-b]pyridine;

N-benzyl-4-[4-(5-fluoro-2-methoxyphenyl)-1H-pyrrolo[2,3-b]pyridin-2-yl]cyclohex-3-ene-1-carboxamide;

N-(3-fluorobenzyl)-4-[4-(5-fluoro-2-methoxyphenyl)-1H-pyrrolo[2,3-b]pyridin-2-yl]cyclohex-3-ene-1-carboxamide;

N-(3,5-difluorobenzyl)-4-[4-(5-fluoro-2-methoxyphenyl)-1H-pyrrolo[2,3-b]pyridin-2-yl]cyclohex-3-ene-1-carboxamide;

N-(2,5-difluorobenzyl)-4-[4-(5-fluoro-2-methoxyphenyl)-1H-pyrrolo[2,3-b]pyridin-2-yl]cyclohex-3-ene-1-carboxamide;

N-(3-chlorobenzyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(pyridin-4-ylmethyl)cyclohex-3-ene-1-carboxamide;

4-[4-(5-fluoro-2-methoxyphenyl)-1H-pyrrolo[2,3-b]pyridin-2-yl]-N-[(3-methyl-1H-pyrazol-5-yl)methyl]cyclohex-3-ene-1-carboxamide;

4-[4-(5-fluoro-2-methoxyphenyl)-1H-pyrrolo[2,3-b]pyridin-2-yl]-N-(tetrahydro-2H-pyran-4-ylmethyl)cyclohex-3-ene-1-carboxamide;

4-[4-(5-fluoro-2-methoxyphenyl)-1H-pyrrolo[2,3-b]pyridin-2-yl]-N-(4-hydroxycyclohexyl)cyclohex-3-ene-1-carboxamide;

(3,3-difluoroazetidin-1-yl){4-[4-(5-fluoro-2-methoxyphenyl)-1H-pyrrolo[2,3-b]pyridin-2-yl]cyclohex-3-en-1-yl}methanone;

2-(3,6-dihydro-2H-pyran-4-yl)-4-(5-fluoro-2-methoxyphenyl)-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}(tetrahydro-2H-pyran-3-yl)methanone;

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]-2-hydroxyethanone;

1-[4-(4-{5-[(3,5-difluorobenzyl)oxy]-2-fluorophenyl}-1H-pyrrolo[2,3-b]pyridin-2-yl)-3,6-dihydropyridin-1(2H)-yl]ethanone;

1-{5-[4-(5-fluoro-2-methoxyphenyl)-1H-pyrrolo[2,3-b]pyridin-2-yl]-3,6-dihydropyridin-1(2H)-yl}-2-hydroxyethanone;

1-{5-[4-(5-fluoro-2-methoxyphenyl)-1H-pyrrolo[2,3-b]pyridin-2-yl]-3,6-dihydropyridin-1(2H)-yl}ethanone;

N-[4-({5-[4-(5-fluoro-2-methoxyphenyl)-1H-pyrrolo[2,3-b]pyridin-2-yl]-3,6-dihydropyridin-1(2H)-yl}methyl)phenyl]acetamide;

4-(5-fluoro-2-methoxyphenyl)-2-[1-(tetrahydrofuran-2-ylmethyl)-1,2,5,6-tetrahydropyridin-3-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-methylpropan-2-ol;

4-[4-(5-fluoro-2-methoxyphenyl)-1H-pyrrolo[2,3-b]pyridin-2-yl]-N,N-dimethyl-3,6-dihydropyridine-1(2H)-carboxamide;

ethyl ({4-[4-(5-fluoro-2-methoxyphenyl)-1H-pyrrolo[2,3-b]pyridin-2-yl]piperidin-1-yl}sulfonyl)carbamate;

4-[4-(5-fluoro-2-methoxyphenyl)-1H-pyrrolo[2,3-b]pyridin-2-yl]-N-methylpiperidine-1-sulfonamide;

4-[4-(5-fluoro-2-methoxyphenyl)-1H-pyrrolo[2,3-b]pyridin-2-yl]-N,N-dimethylpiperidine-1-sulfonamide;

4-(5-fluoro-2-methoxyphenyl)-2-[4-(trifluoromethyl)cyclohex-1-en-1-yl]-1H-pyrrolo[2,3-b]pyridine;

4-[4-(5-fluoro-2-methoxyphenyl)-1H-pyrrolo[2,3-b]pyridin-2-yl]-N-(tetrahydro-2H-pyran-4-ylmethyl)cyclohex-3-en-1-amine;

2-{4-[4-(5-fluoro-2-methoxyphenyl)-1H-pyrrolo[2,3-b]pyridin-2-yl]piperidin-1-yl}ethanesulfonamide;

N-benzyl-4-[4-(5-fluoro-2-methoxyphenyl)-1H-pyrrolo[2,3-b]pyridin-2-yl]cyclohex-3-en-1-amine;

4-[4-(5-fluoro-2-methoxyphenyl)-1H-pyrrolo[2,3-b]pyridin-2-yl]-N-(pyridin-4-ylmethyl)cyclohex-3-en-1-amine;

4-[4-(5-fluoro-2-methoxyphenyl)-1H-pyrrolo[2,3-b]pyridin-2-yl]-N-(morpholin-2-ylmethyl)cyclohex-3-en-1-amine;

4-(5-fluoro-2-methoxyphenyl)-2-[1-(S-methylsulfonimidoyl)piperidin-4-yl]-1H-pyrrolo[2,3-b]pyridine;

N-ethyl-4-[4-(5-fluoro-2-methoxyphenyl)-1H-pyrrolo[2,3-b]pyridin-2-yl]piperidine-1-sulfonamide;

4-[3-(4-fluorophenoxy)phenyl]-2-(piperidin-4-yl)-1H-pyrrolo[2,3-b]pyridine;

4-(2,3-difluorophenyl)-2-(1,2,3,6-tetrahydropyridin-4-yl)-1H-pyrrolo[2,3-b]pyridine;

3-{4-[4-(2,3-difluorophenyl)-1H-pyrrolo[2,3-b]pyridin-2-yl]-3,6-dihydropyridin-1(2H)-yl}propane-1,2-diol;

N-[4-({4-[4-(2,3-difluorophenyl)-1H-pyrrolo[2,3-b]pyridin-2-yl]-3,6-dihydropyridin-1(2H)-yl}methyl)phenyl]acetamide;

1-{4-[4-(2,3-difluorophenyl)-1H-pyrrolo[2,3-b]pyridin-2-yl]-3,6-dihydropyridin-1(2H)-yl}-2-hydroxyethanone;

2-(8-azabicyclo[3.2.1]oct-2-en-3-yl)-4-(5-fluoro-2-methoxyphenyl)-1H-pyrrolo[2,3-b]pyridine;

N-(3,5-difluorobenzyl)-4-[4-(5-fluoro-2-methoxyphenyl)-1H-pyrrolo[2,3-b]pyridin-2-yl]cyclohex-3-en-1-amine;

3-[4-(5-fluoro-2-methoxyphenyl)-1H-pyrrolo[2,3-b]pyridin-2-yl]-N-methyl-8-azabicyclo[3.2.1]oct-2-ene-8-carboxamide;

3-{3-[4-(5-fluoro-2-methoxyphenyl)-1H-pyrrolo[2,3-b]pyridin-2-yl]-8-azabicyclo[3.2.1]oct-2-en-8-yl}propane-1,2-diol;

1-{3-[4-(5-fluoro-2-methoxyphenyl)-1H-pyrrolo[2,3-b]pyridin-2-yl]-8-azabicyclo[3.2.1]oct-2-en-8-yl}-2-hydroxyethanone;

3-[4-(5-fluoro-2-methoxyphenyl)-1H-pyrrolo[2,3-b]pyridin-2-yl]-N,N-dimethyl-8-azabicyclo[3.2.1]oct-2-ene-8-carboxamide;

N-[(2S)-2,3-dihydroxypropyl]-4-[4-(5-fluoro-2-methoxyphenyl)-1H-pyrrolo[2,3-b]pyridin-2-yl]piperidine-1-sulfonamide;

3-chloro-4-(5-fluoro-2-methoxyphenyl)-2-(piperidin-4-yl)-1H-pyrrolo[2,3-b]pyridine;

3-bromo-4-(5-fluoro-2-methoxyphenyl)-2-(piperidin-4-yl)-1H-pyrrolo[2,3-b]pyridine;

ethyl ({4-[3-bromo-4-(5-fluoro-2-methoxyphenyl)-1H-pyrrolo[2,3-b]pyridin-2-yl]piperidin-1-yl}sulfonyl)carbamate;

4-[4-(5-fluoro-2-methoxyphenyl)-1H-pyrrolo[2,3-b]pyridin-2-yl]-N-(2-hydroxyethyl)-3,6-dihydropyridine-1(2H)-carboxamide;

4-[4-(5-fluoro-2-methoxyphenyl)-1H-pyrrolo[2,3-b]pyridin-2-yl]-N-(methylsulfonyl)cyclohex-3-ene-1-carboxamide;

N-methyl-4-[2-(1,2,3,6-tetrahydropyridin-4-yl)-1H-pyrrolo[2,3-b]pyridin-4-yl]benzamide;

5-[4-(5-fluoro-2-methoxyphenyl)-1H-pyrrolo[2,3-b]pyridin-2-yl]-N,N-dimethyl-3,6-dihydropyridine-1(2H)-carboxamide;

4-[4-(5-fluoro-2-methoxyphenyl)-1H-pyrrolo[2,3-b]pyridin-2-yl]-N-(pyridin-3-ylmethyl)cyclohex-3-en-1-amine;

4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-[2-(pyrrolidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-[2-(4-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(tetrahydrofuran-2-ylmethyl)amino]ethyl}-3,6-dihydropyridine-1(2H)-carboxamide;

methyl 4-{2-[({4-[4-(5-fluoro-2-methoxyphenyl)-1H-pyrrolo[2,3-b]pyridin-2-yl]-3,6-dihydropyridin-1(2H)-yl}carbonyl)amino]ethyl}piperazine-1-carboxylate;

N-[2-(3,4-dihydroisoquinolin-2(1H)-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-(3-hydroxy-3-methylbutyl)-3,6-dihydropyridine-1(2H)-carboxamide;

1-{5-[4-(5-fluoro-2-methoxyphenyl)-1H-pyrrolo[2,3-b]pyridin-2-yl]-3,6-dihydropyridin-1(2H)-yl}-2-methylpropan-2-ol;

4-{2-[1-(2,3-dihydroxypropyl)-1,2,3,6-tetrahydropyridin-4-yl]-1H-pyrrolo[2,3-b]pyridin-4-yl}-N-methylbenzamide;

N-methyl-4-{4-[4-(methylcarbamoyl)phenyl]-1H-pyrrolo[2,3-b]pyridin-2-yl}-3,6-dihydropyridine-1(2H)-carboxamide;

4-{2-[1-(hydroxyacetyl)-1,2,3,6-tetrahydropyridin-4-yl]-1H-pyrrolo[2,3-b]pyridin-4-yl}-N-methylbenzamide;

4-[4-(5-fluoro-2-methoxyphenyl)-1H-pyrrolo[2,3-b]pyridin-2-yl]-N,N-dimethyl-3,6-dihydropyridine-1(2H)-sulfonamide;

3-bromo-4-(5-fluoro-2-methoxyphenyl)-2-(1,2,3,6-tetrahydropyridin-4-yl)-1H-pyrrolo[2,3-b]pyridine;

4-(2,4-dimethoxyphenyl)-2-(1,2,3,6-tetrahydropyridin-4-yl)-1H-pyrrolo[2,3-b]pyridine;

N-{4-[4-(5-fluoro-2-methoxyphenyl)-1H-pyrrolo[2,3-b]pyridin-2-yl]cyclohex-3-en-1-yl}glycine;

4-[4-(5-fluoro-2-methoxyphenyl)-1H-pyrrolo[2,3-b]pyridin-2-yl]-N-methylcyclohex-3-ene-1-carboxamide;

4-[4-(5-fluoro-2-methoxyphenyl)-1H-pyrrolo[2,3-b]pyridin-2-yl]-N-[(3-hydroxyoxetan-3-yl)methyl]-3,6-dihydropyridine-1(2H)-carboxamide;

methyl {4-[4-(5-fluoro-2-methoxyphenyl)-1H-pyrrolo[2,3-b]pyridin-2-yl]-3,6-dihydropyridin-1(2H)-yl}acetate;

4-(4,5-difluoro-2-methoxyphenyl)-2-(1,2,3,6-tetrahydropyridin-4-yl)-1H-pyrrolo[2,3-b]pyridine;

4-[2-methoxy-4-(1H-pyrazol-1-yl)phenyl]-2-(1,2,3,6-tetrahydropyridin-4-yl)-1H-pyrrolo[2,3-b]pyridine;

4-(2,6-dimethoxyphenyl)-2-(1,2,3,6-tetrahydropyridin-4-yl)-1H-pyrrolo[2,3-b]pyridine;

4-(2-methoxyphenyl)-2-(1,2,3,6-tetrahydropyridin-4-yl)-1H-pyrrolo[2,3-b]pyridine;

4-(2-chloro-5-methoxyphenyl)-2-(1,2,3,6-tetrahydropyridin-4-yl)-1H-pyrrolo[2,3-b]pyridine;

4-(5-fluoro-2-methoxyphenyl)-2-[1-(methylsulfonyl)-1,2,3,6-tetrahydropyridin-4-yl]-1H-pyrrolo[2,3-b]pyridine-5-carbonitrile;

1-{4-[4-(2,3-difluorophenyl)-1H-pyrrolo[2,3-b]pyridin-2-yl]-3,6-dihydropyridin-1(2H)-yl}-2-methylpropan-2-ol;

4-(2,3-difluorophenyl)-2-[1-(pyridin-2-ylmethyl)-1,2,3,6-tetrahydropyridin-4-yl]-1H-pyrrolo[2,3-b]pyridine;

1-{4-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-(5-fluoro-2-methoxyphenyl)-2-(1,2,3,6-tetrahydropyridin-4-yl)-1H-pyrrolo[2,3-b]pyridine-5-carbonitrile;

5-({4-[4-(5-fluoro-2-methoxyphenyl)-1H-pyrrolo[2,3-b]pyridin-2-yl]-3,6-dihydropyridin-1(2H)-yl}methyl)-2,4-dihydro-3H-1,2,4-triazol-3-one;

2-{4-[4-(5-fluoro-2-methoxyphenyl)-1H-pyrrolo[2,3-b]pyridin-2-yl]-3,6-dihydropyridin-1(2H)-yl}-N-methylacetamide;

ethyl ({4-[3-bromo-4-(5-fluoro-2-methoxyphenyl)-1H-pyrrolo[2,3-b]pyridin-2-yl]-3,6-dihydropyridin-1(2H)-yl}sulfonyl)carbamate;

4-(5-fluoro-2-methoxyphenyl)-5-methyl-2-[1-(methylsulfonyl)-1,2,3,6-tetrahydropyridin-4-yl]-1H-pyrrolo[2,3-b]pyridine;

4-(5-fluoro-2-methoxyphenyl)-5-methyl-2-(1,2,3,6-tetra-hydropyridin-4-yl)-1H-pyrrolo[2,3-b]pyridine;

N-[{4-[4-(5-fluoro-2-methoxyphenyl)-1H-pyrrolo[2,3-b]pyridin-2-yl]-3,6-dihydropyridin-1(2H)-yl}(methyl)oxido-λ⁶-sulfanylidene]-4-methylbenzenesulfonamide;

4-(2-ethoxy-5-fluorophenyl)-2-(1,2,3,6-tetrahydropyridin-4-yl)-1H-pyrrolo[2,3-b]pyridine;

4-(2,5-dimethoxyphenyl)-2-(1,2,3,6-tetrahydropyridin-4-yl)-1H-pyrrolo[2,3-b]pyridine;

N-[(2S)-2,3-dihydroxypropyl]-4-[4-(5-fluoro-2-methoxyphenyl)-1H-pyrrolo[2,3-b]pyridin-2-yl]cyclohex-3-ene-1-carboxamide;

4-{4-[4-(5-fluoro-2-methoxyphenyl)-1H-pyrrolo[2,3-b]pyridin-2-yl]-3,6-dihydropyridin-1(2H)-yl}cyclohexanol;

1-({4-[4-(5-fluoro-2-methoxyphenyl)-1H-pyrrolo[2,3-b]pyridin-2-yl]-3,6-dihydropyridin-1(2H)-yl}carbonyl)piperidine-4-carboxylic acid;

4-[4-(5-fluoro-2-methoxyphenyl)-1H-pyrrolo[2,3-b]pyridin-2-yl]-N-[2-(4-oxopiperidin-1-yl)ethyl]-3,6-dihydropyridine-1(2H)-carboxamide;

N-[2-(3,3-difluoropiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-[2-(3-hydroxypiperidin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypyrrolidin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(2-hydroxyethyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-[2-(3-oxopiperazin-1-yl)ethyl]-3,6-dihydropyridine-1(2H)-carboxamide;

4-[4-(5-fluoro-2-methoxyphenyl)-1H-pyrrolo[2,3-b]pyridin-2-yl]-N-{2-[(3S)-3-hydroxypiperidin-1-yl]ethyl}-3,6-dihydropyridine-1(2H)-carboxamide;

4-methoxy-3-[2-(1,2,3,6-tetrahydropyridin-4-yl)-1H-pyrrolo[2,3-b]pyridin-4-yl]benzonitrile;

4-(2-chloro-5-fluorophenyl)-2-(1,2,3,6-tetrahydropyridin-4-yl)-1H-pyrrolo[2,3-b]pyridine;

4-(4-fluoro-2-methoxyphenyl)-2-(1,2,3,6-tetrahydropyridin-4-yl)-1H-pyrrolo[2,3-b]pyridine;

4-[2-(difluoromethoxy)-5-fluorophenyl]-2-(1,2,3,6-tetrahydropyridin-4-yl)-1H-pyrrolo[2,3-b]pyridine;

({4-[4-(5-fluoro-2-methoxyphenyl)-1H-pyrrolo[2,3-b]pyridin-2-yl]-3,6-dihydropyridin-1(2H)-yl}sulfonyl)acetic acid;

4-(5-fluoro-2-methoxyphenyl)-2-(1-{[(methylsulfonyl)methyl]sulfonyl}-1,2,3,6-tetrahydropyridin-4-yl)-1H-pyrrolo[2,3-b]pyridine;

5-chloro-4-(5-fluoro-2-methoxyphenyl)-2-(1,2,3,6-tetrahydropyridin-4-yl)-1H-pyrrolo[2,3-b]pyridine;

4-(5-fluoro-2-methoxyphenyl)-2-{1-[(tetrahydrofuran-2-ylmethyl)sulfonyl]-1,2,3,6-tetrahydropyridin-4-yl}-1H-pyrrolo[2,3-b]pyridine;

ethyl ({4-[4-(5-fluoro-2-methoxyphenyl)-5-methyl-1H-pyrrolo[2,3-b]pyridin-2-yl]-3,6-dihydropyridin-1(2H)-yl}sulfonyl)carbamate;

3-chloro-4-(5-fluoro-2-methoxyphenyl)-2-(1,2,3,6-tetrahydropyridin-4-yl)-1H-pyrrolo[2,3-b]pyridine;

ethyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate;

3-chloro-4-(5-fluoro-2-methoxyphenyl)-2-[1-(methylsulfonyl)-1,2,3,6-tetrahydropyridin-4-yl]-1H-pyrrolo[2,3-b]pyridine;

(cis-4-{4-[5-fluoro-4-(5-fluoro-2-methoxyphenyl)-1H-pyrrolo[2,3-b]pyridin-2-yl]piperidin-1-yl}cyclohexyl)acetic acid;

4-[4-(5-fluoro-2-methoxyphenyl)-1H-pyrrolo[2,3-b]pyridin-2-yl]-N-(pyridin-2-ylmethyl)cyclohex-3-en-1-amine;

4-[4-(5-fluoro-2-methoxyphenyl)-1H-pyrrolo[2,3-b]pyridin-2-yl]-N-(pyrazin-2-ylmethyl)cyclohex-3-en-1-amine;

4-[4-(5-fluoro-2-methoxyphenyl)-1H-pyrrolo[2,3-b]pyridin-2-yl]-N-(pyrimidin-5-ylmethyl)cyclohex-3-en-1-amine;

4-[4-(5-fluoro-2-methoxyphenyl)-1H-pyrrolo[2,3-b]pyridin-2-yl]-N-(tetrahydrofuran-2-ylmethyl)cyclohex-3-en-1-amine;

4-{5-fluoro-2-[(²H₃)methyloxy]phenyl}-2-(1,2,3,6-tetrahydropyridin-4-yl)-1H-pyrrolo[2,3-b]pyridine;

4-(4-{5-fluoro-2-[(²H₃)methyloxy]phenyl}-1H-pyrrolo[2,3-b]pyridin-2-yl)-N-methyl-3,6-dihydropyridine-1(2H)-carboxamide;

4-{5-fluoro-2-[(²H₃)methyloxy]phenyl}-2-[1-(methylsulfonyl)-1,2,3,6-tetrahydropyridin-4-yl]-1H-pyrrolo[2,3-b]pyridine;

methyl 2-{4-[4-(5-fluoro-2-methoxyphenyl)-1H-pyrrolo[2,3-b]pyridin-2-yl]-3,6-dihydropyridin-1(2H)-yl}propanoate;

5-chloro-4-(5-fluoro-2-methoxyphenyl)-2-[1-(methylsulfonyl)-1,2,3,6-tetrahydropyridin-4-yl]-1H-pyrrolo[2,3-b]pyridine;

{4-[4-(5-fluoro-2-methoxyphenyl)-1H-pyrrolo[2,3-b]pyridin-2-yl]-3,6-dihydropyridin-1(2H)-yl}[(4R)-2,2,5,5-tetramethyl-1,3-dioxolan-4-yl]methanone;

5-[4-(5-fluoro-2-methoxyphenyl)-1H-pyrrolo[2,3-b]pyridin-2-yl]-1-(methylsulfonyl)-1,2,3,4-tetrahydropyridine-4-carboxylic acid;

{4-[4-(5-fluoro-2-methoxyphenyl)-1H-pyrrolo[2,3-b]pyridin-2-yl]-3,6-dihydropyridin-1(2H)-yl}[(4S)-2,2,5,5-tetramethyl-1,3-dioxolan-4-yl]methanone;

2-{4-[4-(5-fluoro-2-methoxyphenyl)-1H-pyrrolo[2,3-b]pyridin-2-yl]-3,6-dihydropyridin-1(2H)-yl}propanoic acid;

4-{4-[4-(5-fluoro-2-methoxyphenyl)-1H-pyrrolo[2,3-b]pyridin-2-yl]-3,6-dihydropyridin-1(2H)-yl}cyclohex-1-ene-1-carboxylic acid;

[(2s,3aR,5r,6aS)-5-{4-[4-(5-fluoro-2-methoxyphenyl)-1H-pyrrolo[2,3-b]pyridin-2-yl]-3,6-dihydropyridin-1(2H)-yl}octahydropentalen-2-yl]acetic acid;

methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

methyl ({4-[3-chloro-4-(5-fluoro-2-methoxyphenyl)-1H-pyrrolo[2,3-b]pyridin-2-yl]-3,6-dihydropyridin-1(2H)-yl}sulfonyl)carbamate;

2-fluoro-N-methyl-4-{2-[1-(methylsulfonyl)-1,2,3,6-tetrahydropyridin-4-yl]-1H-pyrrolo[2,3-b]pyridin-4-yl}benzamide;

(2S)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;

(2R)-1-{4-[4-(5-fluoro-2-methoxyphenyl)-1H-pyrrolo[2,3-b]pyridin-2-yl]-3,6-dihydropyridin-1(2H)-yl}-2,3-dihydroxy-3-methylbutan-1-one;
4-(5-fluoro-2-methoxyphenyl)-2-[1-(hydroxyacetyl)-1,2,3,6-tetrahydropyridin-4-yl]-1H-pyrrolo[2,3-b]pyridine-5-carbonitrile;
4-[5-cyano-4-(5-fluoro-2-methoxyphenyl)-1H-pyrrolo[2,3-b]pyridin-2-yl]-N-methyl-3,6-dihydropyridine-1(2H)-carboxamide;
4-[4-(5-fluoro-2-methoxyphenyl)-1H-pyrrolo[2,3-b]pyridin-2-yl]-N-[2-(piperazin-1-yl)ethyl]-3,6-dihydropyridine-1(2H)-carboxamide;
N-[2-(4-aminopiperidin-1-yl)ethyl]-4-[4-(5-fluoro-2-methoxyphenyl)-1H-pyrrolo[2,3-b]pyridin-2-yl]-3,6-dihydropyridine-1(2H)-carboxamide;
N-{2-[(1,3-dihydroxypropan-2-yl)amino]ethyl}-4-[4-(5-fluoro-2-methoxyphenyl)-1H-pyrrolo[2,3-b]pyridin-2-yl]-3,6-dihydropyridine-1(2H)-carboxamide;
3-ethoxy-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;
5-fluoro-4-(5-fluoro-2-methoxyphenyl)-2-(1,2,3,6-tetrahydropyridin-4-yl)-1H-pyrrolo[2,3-b]pyridine;
4-[5-fluoro-4-(5-fluoro-2-methoxyphenyl)-1H-pyrrolo[2,3-b]pyridin-2-yl]-N-methyl-3,6-dihydropyridine-1(2H)-carboxamide;
5-fluoro-4-(5-fluoro-2-methoxyphenyl)-2-[1-(methylsulfonyl)-1,2,3,6-tetrahydropyridin-4-yl]-1H-pyrrolo[2,3-b]pyridine;
3-{4-[5-fluoro-4-(5-fluoro-2-methoxyphenyl)-1H-pyrrolo[2,3-b]pyridin-2-yl]-3,6-dihydropyridin-1(2H)-yl}propane-1,2-diol;
1-{4-[4-(5-fluoro-2-methoxyphenyl)-1H-pyrrolo[2,3-b]pyridin-2-yl]-3,6-dihydropyridin-1(2H)-yl}-2-(methylsulfonyl)ethanone;
ethyl 3-{4-[4-(5-fluoro-2-methoxyphenyl)-1H-pyrrolo[2,3-b]pyridin-2-yl]-3,6-dihydropyridin-1(2H)-yl}-3-oxopropanoate;
4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}-3,6-dihydropyridine-1(2H)-carboxamide;
N-(2-{4-[4-(5-fluoro-2-methoxyphenyl)-1H-pyrrolo[2,3-b]pyridin-2-yl]-3,6-dihydropyridin-1(2H)-yl}-2-oxoethyl)methanesulfonamide;
4-[4-(2,3-difluorophenyl)-1H-pyrrolo[2,3-b]pyridin-2-yl]cyclohex-3-ene-1-carboxylic acid;
N-({4-[4-(5-fluoro-2-methoxyphenyl)-1H-pyrrolo[2,3-b]pyridin-2-yl]cyclohex-3-en-1-yl}carbonyl)glycine;
3-{4-[4-(5-fluoro-2-methoxyphenyl)-1H-pyrrolo[2,3-b]pyridin-2-yl]-3,6-dihydropyridin-1(2H)-yl}-3-oxopropanoic acid;
4-(4-chloro-2-methoxyphenyl)-2-(1,2,3,6-tetrahydropyridin-4-yl)-1H-pyrrolo[2,3-b]pyridine;
4-(2,4-dimethoxyphenyl)-2-[1-(methylsulfonyl)-1,2,3,6-tetrahydropyridin-4-yl]-1H-pyrrolo[2,3-b]pyridine;
3-{4-[4-(2,4-dimethoxyphenyl)-1H-pyrrolo[2,3-b]pyridin-2-yl]-3,6-dihydropyridin-1(2H)-yl}propane-1,2-diol;
4-[4-(2,4-dimethoxyphenyl)-1H-pyrrolo[2,3-b]pyridin-2-yl]-N-methyl-3,6-dihydropyridine-1(2H)-carboxamide;
1-{4-[4-(2,4-dimethoxyphenyl)-1H-pyrrolo[2,3-b]pyridin-2-yl]-3,6-dihydropyridin-1(2H)-yl}-2-hydroxyethanone;
3-{4-[4-(2-methoxyphenyl)-1H-pyrrolo[2,3-b]pyridin-2-yl]-3,6-dihydropyridin-1(2H)-yl}propane-1,2-diol;
4-[4-(2-methoxyphenyl)-1H-pyrrolo[2,3-b]pyridin-2-yl]-N-methyl-3,6-dihydropyridine-1(2H)-carboxamide;
2-hydroxy-1-{4-[4-(2-methoxyphenyl)-1H-pyrrolo[2,3-b]pyridin-2-yl]-3,6-dihydropyridin-1(2H)-yl}ethanone;
3-{4-[4-(4-fluoro-2-methoxyphenyl)-1H-pyrrolo[2,3-b]pyridin-2-yl]-3,6-dihydropyridin-1(2H)-yl}propane-1,2-diol;
4-[4-(4-fluoro-2-methoxyphenyl)-1H-pyrrolo[2,3-b]pyridin-2-yl]-N-methyl-3,6-dihydropyridine-1(2H)-carboxamide;
1-{4-[4-(4-fluoro-2-methoxyphenyl)-1H-pyrrolo[2,3-b]pyridin-2-yl]-3,6-dihydropyridin-1(2H)-yl}-2-hydroxyethanone;
3-{4-[4-(4,5-difluoro-2-methoxyphenyl)-1H-pyrrolo[2,3-b]pyridin-2-yl]-3,6-dihydropyridin-1(2H)-yl}propane-1,2-diol;
1-{4-[4-(4,5-difluoro-2-methoxyphenyl)-1H-pyrrolo[2,3-b]pyridin-2-yl]-3,6-dihydropyridin-1(2H)-yl}-2-hydroxyethanone;
N-({4-[4-(5-fluoro-2-methoxyphenyl)-1H-pyrrolo[2,3-b]pyridin-2-yl]-3,6-dihydropyridin-1(2H)-yl}sulfonyl)acetamide;
4-(4,5-difluoro-2-methoxyphenyl)-2-[1-(methylsulfonyl)-1,2,3,6-tetrahydropyridin-4-yl]-1H-pyrrolo[2,3-b]pyridine;
4-(5-fluoro-2-methoxyphenyl)-3-methyl-2-(1,2,3,6-tetrahydropyridin-4-yl)-1H-pyrrolo[2,3-b]pyridine;
2-(8-azabicyclo[3.2.1]oct-2-en-3-yl)-4-(2,3-difluorophenyl)-1H-pyrrolo[2,3-b]pyridine;
{4-[5-cyano-4-(5-fluoro-2-methoxyphenyl)-1H-pyrrolo[2,3-b]pyridin-2-yl]-3,6-dihydropyridin-1(2H)-yl}acetic acid;
4-[4-(5-fluoro-2-methoxyphenyl)-1H-pyrrolo[2,3-b]pyridin-2-yl]-N-(2-{[2-(1H-imidazol-4-yl)ethyl]amino}ethyl)-3,6-dihydropyridine-1(2H)-carboxamide;
4-[4-(5-fluoro-2-methoxyphenyl)-1H-pyrrolo[2,3-b]pyridin-2-yl]-N-{2-[(2-hydroxypropyl)amino]ethyl}-3,6-dihydropyridine-1(2H)-carboxamide;
N-[2-(dimethylamino)ethyl]-4-[4-(5-fluoro-2-methoxyphenyl)-1H-pyrrolo[2,3-b]pyridin-2-yl]-3,6-dihydropyridine-1(2H)-carboxamide;
4-[4-(5-fluoro-2-methoxyphenyl)-1H-pyrrolo[2,3-b]pyridin-2-yl]-N-(2-{[(3-methyloxetan-3-yl)methyl]amino}ethyl)-3,6-dihydropyridine-1(2H)-carboxamide;
4-[4-(5-fluoro-2-methoxyphenyl)-1H-pyrrolo[2,3-b]pyridin-2-yl]-N-[2-(oxetan-3-ylamino)ethyl]-3,6-dihydropyridine-1(2H)-carboxamide;
3-methoxy-N-methyl-4-[2-(1,2,3,6-tetrahydropyridin-4-yl)-1H-pyrrolo[2,3-b]pyridin-4-yl]benzamide;
3-methoxy-N-methyl-4-{2-[1-(methylsulfonyl)-1,2,3,6-tetrahydropyridin-4-yl]-1H-pyrrolo[2,3-b]pyridin-4-yl}benzamide;
4-{2-[1-(2,3-dihydroxypropyl)-1,2,3,6-tetrahydropyridin-4-yl]-1H-pyrrolo[2,3-b]pyridin-4-yl}-3-methoxy-N-methylbenzamide;
3-amino-4-{4-[4-(5-fluoro-2-methoxyphenyl)-1H-pyrrolo[2,3-b]pyridin-2-yl]-3,6-dihydropyridin-1(2H)-yl}cyclobut-3-ene-1,2-dione;
4-(5-fluoro-2-methoxyphenyl)-2-(2,5,6,7-tetrahydro-1H-azepin-4-yl)-1H-pyrrolo[2,3-b]pyridine and 4-(5-fluoro-2-methoxyphenyl)-2-(2,3,6,75-tetrahydro-1H-azepin-4-yl)-1H-pyrrolo[2,3-b]pyridine;

4-(5-fluoro-2-methoxyphenyl)-2-[1-(methylsulfonyl)-2,5,6,7-tetrahydro-1H-azepin-4-yl]-1H-pyrrolo[2,3-b]pyridine and 4-(5-fluoro-2-methoxyphenyl)-2-(1-(methylsulfonyl)-2,3,6,7-tetrahydro-1H-azepin-4-yl)-1H-pyrrolo[2,3-b]pyridine;

5-[4-(5-fluoro-2-methoxyphenyl)-1H-pyrrolo[2,3-b]pyridin-2-yl]-N-methyl-2,3,4,7-tetrahydro-1H-azepine-1-carboxamide and 4-(4-(5-fluoro-2-methoxyphenyl)-1H-pyrrolo[2,3-b]pyridin-2-yl)-N-methyl-2,3,6,7-tetrahydro-1H-azepine-1-carboxamide;

1-(1,1-dioxido-1,3-thiazolidin-3-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(methylsulfonyl)acetamide;

2-{4-[4-(2,4-dimethoxyphenyl)-1H-pyrrolo[2,3-b]pyridin-2-yl]-3,6-dihydropyridin-1(2H)-yl}-N,N-dimethylacetamide;

2-{4-[4-(2-methoxyphenyl)-1H-pyrrolo[2,3-b]pyridin-2-yl]-3,6-dihydropyridin-1(2H)-yl}-N,N-dimethylacetamide;

2-{4-[4-(4-fluoro-2-methoxyphenyl)-1H-pyrrolo[2,3-b]pyridin-2-yl]-3,6-dihydropyridin-1(2H)-yl}-N,N-dimethylacetamide;

2-{4-[4-(4,5-difluoro-2-methoxyphenyl)-1H-pyrrolo[2,3-b]pyridin-2-yl]-3,6-dihydropyridin-1(2H)-yl}-N,N-dimethylacetamide;

tert-butyl {5-[4-(5-fluoro-2-methoxyphenyl)-1H-pyrrolo[2,3-b]pyridin-2-yl]-3,6-dihydropyridin-1(2H)-yl}acetate;

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)acetamide;

N-({4-[4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

2-{5-[4-(5-fluoro-2-methoxyphenyl)-1H-pyrrolo[2,3-b]pyridin-2-yl]-3,6-dihydropyridin-1(2H)-yl}-N,N-dimethylacetamide;

N-({4-[3-chloro-4-(5-fluoro-2-methoxyphenyl)-1H-pyrrolo[2,3-b]pyridin-2-yl]-3,6-dihydropyridin-1(2H)-yl}sulfonyl)-2,2-dimethylpropanamide;

ethyl ({4-[4-(5-fluoro-2-methoxyphenyl)-3-methyl-1H-pyrrolo[2,3-b]pyridin-2-yl]-3,6-dihydropyridin-1(2H)-yl}sulfonyl)carbamate;

{5-[4-(5-fluoro-2-methoxyphenyl)-1H-pyrrolo[2,3-b]pyridin-2-yl]-3,6-dihydropyridin-1(2H)-yl}acetic acid;

ethyl 1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylate;

4-[4-(5-fluoro-2-methoxyphenyl)-3-methyl-1H-pyrrolo[2,3-b]pyridin-2-yl]-N-methyl-3,6-dihydropyridine-1(2H)-carboxamide;

4-(5-fluoro-2-methoxyphenyl)-3-methyl-2-[1-(methylsulfonyl)-1,2,3,6-tetrahydropyridin-4-yl]-1H-pyrrolo[2,3-b]pyridine;

2-(dimethylamino)-1-{4-[4-(5-fluoro-2-methoxyphenyl)-1H-pyrrolo[2,3-b]pyridin-2-yl]-3,6-dihydropyridin-1(2H)-yl}ethanone;

{4-[5-fluoro-4-(5-fluoro-2-methoxyphenyl)-1H-pyrrolo[2,3-b]pyridin-2-yl]-3,6-dihydropyridin-1(2H)-yl}acetic acid;

2-({4-[4-(5-fluoro-2-methoxyphenyl)-1H-pyrrolo[2,3-b]pyridin-2-yl]cyclohex-3-en-1-yl}amino)butanoic acid;

4-(2,3-difluorophenyl)-2-[1-(methylsulfonyl)-1,2,5,6-tetrahydropyridin-3-yl]-1H-pyrrolo[2,3-b]pyridine;

2-{5-[4-(2,3-difluorophenyl)-1H-pyrrolo[2,3-b]pyridin-2-yl]-3,6-dihydropyridin-1(2H)-yl}-N,N-dimethylacetamide;

1-{5-[4-(2,3-difluorophenyl)-1H-pyrrolo[2,3-b]pyridin-2-yl]-3,6-dihydropyridin-1(2H)-yl}-2-hydroxyethanone;

4-(5-fluoro-2-methoxyphenyl)-2-[1-(methylsulfonyl)azepan-4-yl]-1H-pyrrolo[2,3-b]pyridine;

{3-[4-(5-fluoro-2-methoxyphenyl)-1H-pyrrolo[2,3-b]pyridin-2-yl]-2,5-dihydro-1H-pyrrol-1-yl}acetic acid;

2-{4-[4-(5-fluoro-2-methoxyphenyl)-1H-pyrrolo[2,3-b]pyridin-2-yl]piperidin-1-yl}-N,N-dimethylethanesulfonamide;

{4-[4-(2,4-dimethoxyphenyl)-1H-pyrrolo[2,3-b]pyridin-2-yl]-3,6-dihydropyridin-1(2H)-yl}acetic acid;

{4-[4-(2-methoxyphenyl)-1H-pyrrolo[2,3-b]pyridin-2-yl]-3,6-dihydropyridin-1(2H)-yl}acetic acid;

{4-[4-(4,5-difluoro-2-methoxyphenyl)-1H-pyrrolo[2,3-b]pyridin-2-yl]-3,6-dihydropyridin-1(2H)-yl}acetic acid;

1-{4-[4-(5-fluoro-2-methoxyphenyl)-1H-pyrrolo[2,3-b]pyridin-2-yl]-3,6-dihydropyridin-1(2H)-yl}-2-(3-hydroxypyrrolidin-1-yl)ethanone;

methyl {4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetate;

{4-[({4-[4-(5-fluoro-2-methoxyphenyl)-1H-pyrrolo[2,3-b]pyridin-2-yl]-3,6-dihydropyridin-1(2H)-yl}carbonyl)amino]-1H-pyrazol-1-yl}acetic acid;

N-(cyclopropylsulfonyl)-4-[4-(5-fluoro-2-methoxyphenyl)-1H-pyrrolo[2,3-b]pyridin-2-yl]cyclohex-3-ene-1-carboxamide;

4-[4-(5-fluoro-2-methoxyphenyl)-1H-pyrrolo[2,3-b]pyridin-2-yl]-N-(phenylsulfonyl)-3,6-dihydropyridine-1(2H)-carboxamide;

5-{4-[4-(5-fluoro-2-methoxyphenyl)-1H-pyrrolo[2,3-b]pyridin-2-yl]cyclohex-3-en-1-yl}-1,3,4-oxadiazol-2(3H)-one;

{4-[4-(5-fluoro-2-methoxyphenyl)-1H-pyrrolo[2,3-b]pyridin-2-yl]piperidin-1-yl}acetic acid;

{3-[4-(5-fluoro-2-methoxyphenyl)-1H-pyrrolo[2,3-b]pyridin-2-yl]pyrrolidin-1-yl}acetic acid;

4-[4-(5-fluoro-2-methoxyphenyl)-1H-pyrrolo[2,3-b]pyridin-2-yl]-2,5-dihydro-1H-pyrrole-2-carboxylic acid;

3-{4-[4-(2,3-difluorophenyl)-1H-pyrrolo[2,3-b]pyridin-2-yl]-3,6-dihydropyridin-1(2H)-yl}-3-oxopropanenitrile;

{4-[4-(5-fluoro-2-methoxyphenyl)-1H-pyrrolo[2,3-b]pyridin-2-yl]-3,6-dihydropyridin-1(2H)-yl}(1-hydroxycyclopropyl)methanone;

3-{5-[4-(2,3-difluorophenyl)-1H-pyrrolo[2,3-b]pyridin-2-yl]-3,6-dihydropyridin-1(2H)-yl}propane-1,2-diol;

1-{5-[4-(2,3-difluorophenyl)-1H-pyrrolo[2,3-b]pyridin-2-yl]-3,6-dihydropyridin-1(2H)-yl}-2-hydroxy-2-methylpropan-1-one;

{4-[4-(4-fluoro-2-methoxyphenyl)-1H-pyrrolo[2,3-b]pyridin-2-yl]-3,6-dihydropyridin-1(2H)-yl}acetic acid;

{3-[4-(5-fluoro-2-methoxyphenyl)-1H-pyrrolo[2,3-b]pyridin-2-yl]-8-azabicyclo[3.2.1]oct-2-en-8-yl}acetic acid;

1-({4-[4-(5-fluoro-2-methoxyphenyl)-1H-pyrrolo[2,3-b]pyridin-2-yl]-3,6-dihydropyridin-1(2H)-yl}carbonyl)-4-hydroxypiperidine-4-carboxylic acid;

1-{5-[4-(5-fluoro-2-methoxyphenyl)-1H-pyrrolo[2,3-b]pyridin-2-yl]-3,6-dihydropyridin-1(2H)-yl}-2-hydroxy-2-methylpropan-1-one;

4-[4-(5-fluoro-2-methoxyphenyl)-1H-pyrrolo[2,3-b]pyridin-2-yl]-N-(propan-2-ylsulfonyl)cyclohex-3-ene-1-carboxamide;

2-{4-[4-(5-fluoro-2-methoxyphenyl)-1H-pyrrolo[2,3-b]pyridin-2-yl]-3,6-dihydropyridin-1(2H)-yl}-2-oxoethanesulfonamide;

2-{4-[4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;

tert-butyl {4-[4-(5-fluoro-2-methoxyphenyl)-1H-pyrrolo[2,3-b]pyridin-2-yl]-3,6-dihydropyridin-1(2H)-yl}acetate;

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}-3,6-dihydropyridine-1(2H)-carboxamide;

4-(5-fluoro-2-methoxyphenyl)-2-[1-(2H-tetrazol-5-ylmethyl)-1,2,3,6-tetrahydropyridin-4-yl]-1H-pyrrolo[2,3-b]pyridine;

6-[4-(5-fluoro-2-methoxyphenyl)-1H-pyrrolo[2,3-b]pyridin-2-yl]-2-azaspiro[3.3]heptan-6-ol;

{(2R)-4-[4-(5-fluoro-2-methoxyphenyl)-1H-pyrrolo[2,3-b]pyridin-2-yl]-2,5-dihydro-1H-pyrrol-2-yl}methanol;

{4-[4-(2,3-difluorophenyl)-1H-pyrrolo[2,3-b]pyridin-2-yl]-3,6-dihydropyridin-1(2H)-yl}acetic acid;

4-[4-(5-fluoro-2-methoxyphenyl)-1H-pyrrolo[2,3-b]pyridin-2-yl]cyclohex-3-en-1-ol;

2-{3-[4-(5-fluoro-2-methoxyphenyl)-1H-pyrrolo[2,3-b]pyridin-2-yl]pyrrolidin-1-yl}-N,N-dimethylacetamide;

3-[4-(5-fluoro-2-methoxyphenyl)-1H-pyrrolo[2,3-b]pyridin-2-yl]cyclopent-3-en-1-amine;

3-[4-(5-fluoro-2-methoxyphenyl)-1H-pyrrolo[2,3-b]pyridin-2-yl]cyclopent-2-en-1-amine;

2-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]-1H-isoindole-1,3(2H)-dione;

3-ethoxy-4-{4-[4-(2-{2-[(2-ethoxy-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

4-[4-(5-fluoro-2-methoxyphenyl)-1H-pyrrolo[2,3-b]pyridin-2-yl]-N-(2-{[(1S,2S)-2-hydroxycyclohexyl]amino}ethyl)-3,6-dihydropyridine-1(2H)-carboxamide;

N-(2-{[2-(dimethylamino)ethyl]amino}ethyl)-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(2-methoxyethyl)(methyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(4-methylbenzoyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[4-(methylsulfonyl)piperazin-1-yl]ethyl}-3,6-dihydropyridine-1(2H)-carboxamide;

4-[4-(5-fluoro-2-methoxyphenyl)-1H-pyrrolo[2,3-b]pyridin-2-yl]-N-{2-[(2-hydroxyethyl)amino]ethyl}-3,6-dihydropyridine-1(2H)-carboxamide;

4-[4-(5-fluoro-2-methoxyphenyl)-1H-pyrrolo[2,3-b]pyridin-2-yl]-N-(2-{[3-(trifluoromethyl)benzyl]amino}ethyl)-3,6-dihydropyridine-1(2H)-carboxamide;

ethyl ({4-[4-(2,3-difluorophenyl)-1H-pyrrolo[2,3-b]pyridin-2-yl]-3,6-dihydropyridin-1(2H)-yl}sulfonyl)carbamate;

2,2,2-trifluoroethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-en-1-one;

2-(3,6-dihydro-2H-thiopyran-4-yl)-4-(5-fluoro-2-methoxyphenyl)-1H-pyrrolo[2,3-b]pyridine;

3-fluoro-N-methyl-4-[2-(1,2,3,6-tetrahydropyridin-4-yl)-1H-pyrrolo[2,3-b]pyridin-4-yl]benzamide;

N-({4-[4-(5-fluoro-2-methoxyphenyl)-1H-pyrrolo[2,3-b]pyridin-2-yl]-3,6-dihydropyridin-1(2H)-yl}carbonyl)alanine;

4-(5-fluoro-2-methoxyphenyl)-2-(1-oxido-3,6-dihydro-2H-thiopyran-4-yl)-1H-pyrrolo[2,3-b]pyridine;

4-[4-(5-fluoro-2-methoxyphenyl)-1H-pyrrolo[2,3-b]pyridin-2-yl]-N-[(1-methylcyclopropyl)sulfonyl]cyclohex-3-ene-1-carboxamide;

4-[4-(5-fluoro-2-methoxyphenyl)-1H-pyrrolo[2,3-b]pyridin-2-yl]-N-[(2-methylpropyl)sulfonyl]cyclohex-3-ene-1-carboxamide;

4-[4-(2,3-difluorophenyl)-1H-pyrrolo[2,3-b]pyridin-2-yl]-N-(phenylsulfonyl)-3,6-dihydropyridine-1(2H)-carboxamide;

4-(5-fluoro-2-methoxyphenyl)-2-(1,2,3,6-tetrahydropyridin-4-yl)-1H-pyrrolo[2,3-b]pyridine-5-carboxamide;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-5-carbonitrile;

2-{4-[5-chloro-4-(5-fluoro-2-methoxyphenyl)-1H-pyrrolo[2,3-b]pyridin-2-yl]-3,6-dihydropyridin-1(2H)-yl}-N,N-dimethylacetamide;

{4-[5-chloro-4-(5-fluoro-2-methoxyphenyl)-1H-pyrrolo[2,3-b]pyridin-2-yl]-3,6-dihydropyridin-1(2H)-yl}acetic acid;

3-{4-[5-chloro-4-(5-fluoro-2-methoxyphenyl)-1H-pyrrolo[2,3-b]pyridin-2-yl]-3,6-dihydropyridin-1(2H)-yl}propane-1,2-diol;

{4-[4-(5-fluoro-2-methoxyphenyl)-1H-pyrrolo[2,3-b]pyridin-2-yl]-3,6-dihydropyridin-1(2H)-yl}[(2S,4S)-4-hydroxypyrrolidin-2-yl]methanone;

N-[2-(ethylamino)ethyl]-4-[4-(5-fluoro-2-methoxyphenyl)-1H-pyrrolo[2,3-b]pyridin-2-yl]-3,6-dihydropyridine-1(2H)-carboxamide;

N-[2-(cyclopropylamino)ethyl]-4-[4-(5-fluoro-2-methoxyphenyl)-1H-pyrrolo[2,3-b]pyridin-2-yl]-3,6-dihydropyridine-1(2H)-carboxamide;

4-[4-(5-fluoro-2-methoxyphenyl)-1H-pyrrolo[2,3-b]pyridin-2-yl]-N-{2-[(pyridin-2-ylmethyl)amino]ethyl}-3,6-dihydropyridine-1(2H)-carboxamide;

3-amino-4-{4-[4-(2-{2-[(2-amino-3,4-dioxocyclobut-1-en-1-yl)amino]ethoxy}-5-fluorophenyl)-1H-pyrrolo[2,3-b]pyridin-2-yl]-3,6-dihydropyridin-1(2H)-yl}cyclobut-3-ene-1,2-dione;

tert-butyl 4-({4-[4-(5-fluoro-2-methoxyphenyl)-1H-pyrrolo[2,3-b]pyridin-2-yl]-3,6-dihydropyridin-1(2H)-yl}sulfonyl)piperidine-1-carboxylate;

4-[4-(5-fluoro-2-methoxyphenyl)-1H-pyrrolo[2,3-b]pyridin-2-yl]-1-(methylsulfonyl)-2,5-dihydro-1H-pyrrole-2-carboxylic acid;

4-(5-fluoro-2-methoxyphenyl)-2-[1-(piperidin-4-ylsulfonyl)-1,2,3,6-tetrahydropyridin-4-yl]-1H-pyrrolo[2,3-b]pyridine;

N,N-dimethyl-4-{2-[1-(methylsulfonyl)-1,2,3,6-tetrahydropyridin-4-yl]-1H-pyrrolo[2,3-b]pyridin-4-yl}benzamide;

2-{4-[4-(5-fluoro-2-methoxyphenyl)-1H-pyrrolo[2,3-b]pyridin-2-yl]-3,6-dihydropyridin-1(2H)-yl}-N,N-dimethylpropanamide;
4-(4-fluoro-2-methoxyphenyl)-2-[8-(methylsulfonyl)-8-azabicyclo[3.2.1]oct-2-en-3-yl]-1H-pyrrolo[2,3-b]pyridine;
4-(4,5-difluoro-2-methoxyphenyl)-2-[8-(methylsulfonyl)-8-azabicyclo[3.2.1]oct-2-en-3-yl]-1H-pyrrolo[2,3-b]pyridine;
4-(2-methoxyphenyl)-2-[8-(methylsulfonyl)-8-azabicyclo[3.2.1]oct-2-en-3-yl]-1H-pyrrolo[2,3-b]pyridine;
4-(3-fluoro-2-methoxyphenyl)-2-(1,2,3,6-tetrahydropyridin-4-yl)-1H-pyrrolo[2,3-b]pyridine;
ethyl ({4-[4-(4-fluoro-2-methoxyphenyl)-1H-pyrrolo[2,3-b]pyridin-2-yl]-3,6-dihydropyridin-1(2H)-yl}sulfonyl)carbamate;
ethyl ({4-[4-(2,4-dimethoxyphenyl)-1H-pyrrolo[2,3-b]pyridin-2-yl]-3,6-dihydropyridin-1(2H)-yl}sulfonyl)carbamate;
ethyl ({4-[4-(2-methoxyphenyl)-1H-pyrrolo[2,3-b]pyridin-2-yl]-3,6-dihydropyridin-1(2H)-yl}sulfonyl)carbamate;
ethyl ({4-[4-(4,5-difluoro-2-methoxyphenyl)-1H-pyrrolo[2,3-b]pyridin-2-yl]-3,6-dihydropyridin-1(2H)-yl}sulfonyl)carbamate;
{4-[4-(5-fluoro-2-methoxyphenyl)-1H-pyrrolo[2,3-b]pyridin-2-yl]-3,6-dihydropyridin-1(2H)-yl}[(2S,4R)-4-hydroxypyrrolidin-2-yl]methanone;
{4-[4-(5-fluoro-2-methoxyphenyl)-1H-pyrrolo[2,3-b]pyridin-2-yl]-3,6-dihydropyridin-1(2H)-yl}[(2R,4S)-4-hydroxypyrrolidin-2-yl]methanone;
4-[4-(5-fluoro-2-methoxyphenyl)-1H-pyrrolo[2,3-b]pyridin-2-yl]-N,N-dimethylcyclohex-3-ene-1-carboxamide;
N-{4-[4-(5-fluoro-2-methoxyphenyl)-1H-pyrrolo[2,3-b]pyridin-2-yl]cyclohex-3-en-1-yl}alanine;
2-({4-[4-(5-fluoro-2-methoxyphenyl)-1H-pyrrolo[2,3-b]pyridin-2-yl]-3,6-dihydropyridin-1(2H)-yl}sulfonyl)ethanamine;
4-{2-[1-(methylsulfonyl)-1,2,3,6-tetrahydropyridin-4-yl]-1H-pyrrolo[2,3-b]pyridin-4-yl}-N-propylbenzamide;
3-fluoro-N-methyl-4-{2-[1-(methylsulfonyl)-1,2,3,6-tetrahydropyridin-4-yl]-1H-pyrrolo[2,3-b]pyridin-4-yl}benzamide;
ethyl {[4-{4-[2-fluoro-4-(methylcarbamoyl)phenyl]-1H-pyrrolo[2,3-b]pyridin-2-yl}-3,6-dihydropyridin-1(2H)-yl]sulfonyl}carbamate;
[4-{4-[2-fluoro-4-(methylcarbamoyl)phenyl]-1H-pyrrolo[2,3-b]pyridin-2-yl}-3,6-dihydropyridin-1(2H)-yl]acetic acid;
4-(5-fluoro-2-methoxyphenyl)-2-(1,2,3,3a,4,6a-hexahydrocyclopenta[c]pyrrol-5-yl)-1H-pyrrolo[2,3-b]pyridine;
tert-butyl 2-(dimethylcarbamoyl)-4-[4-(5-fluoro-2-methoxyphenyl)-1H-pyrrolo[2,3-b]pyridin-2-yl]-2,5-dihydro-1H-pyrrole-1-carboxylate;
tert-butyl 4-[4-(5-fluoro-2-methoxyphenyl)-1H-pyrrolo[2,3-b]pyridin-2-yl]-2-[(methylsulfonyl)carbamoyl]-2,5-dihydro-1H-pyrrole-1-carboxylate;
2-fluoro-N-methyl-4-[2-(1,2,3,6-tetrahydropyridin-4-yl)-1H-pyrrolo[2,3-b]pyridin-4-yl]benzamide;
4-{4-[3-fluoro-4-(methylcarbamoyl)phenyl]-1H-pyrrolo[2,3-b]pyridin-2-yl}-N-methyl-3,6-dihydropyridine-1(2H)-carboxamide;
4-(2-{1-[2-(dimethylamino)-2-oxoethyl]-1,2,3,6-tetrahydropyridin-4-yl}-1H-pyrrolo[2,3-b]pyridin-4-yl)-2-fluoro-N-methylbenzamide;
4-{2-[1-(2,3-dihydroxypropyl)-1,2,3,6-tetrahydropyridin-4-yl]-1H-pyrrolo[2,3-b]pyridin-4-yl}-2-fluoro-N-methylbenzamide;
4-(5-fluoro-2-methoxyphenyl)-5-methoxy-2-[1-(methylsulfonyl)-1,2,3,6-tetrahydropyridin-4-yl]-1H-pyrrolo[2,3-b]pyridine;
N-{4-[4-(5-fluoro-2-methoxyphenyl)-1H-pyrrolo[2,3-b]pyridin-2-yl]cyclohex-3-en-1-yl}serine;
3-[4-(5-fluoro-2-methoxyphenyl)-1H-pyrrolo[2,3-b]pyridin-2-yl]cyclohex-3-ene-1-carboxylic acid;
{4-[4-(5-fluoro-2-methoxyphenyl)-1H-pyrrolo[2,3-b]pyridin-2-yl]-1,2,3,6-tetrahydropyridin-2-yl}methanol;
7-[4-(5-fluoro-2-methoxyphenyl)-1H-pyrrolo[2,3-b]pyridin-2-yl]-3-oxa-9-azabicyclo[3.3.1]non-6-ene;
7-[4-(5-fluoro-2-methoxyphenyl)-1H-pyrrolo[2,3-b]pyridin-2-yl]-9-(methylsulfonyl)-3-oxa-9-azabicyclo[3.3.1]non-6-ene;
ethyl ({7-[4-(5-fluoro-2-methoxyphenyl)-1H-pyrrolo[2,3-b]pyridin-2-yl]-3-oxa-9-azabicyclo[3.3.1]non-6-en-9-yl}sulfonyl)carbamate;
2-{7-[4-(5-fluoro-2-methoxyphenyl)-1H-pyrrolo[2,3-b]pyridin-2-yl]-3-oxa-9-azabicyclo[3.3.1]non-6-en-9-yl}-N,N-dimethylacetamide;
N-{4-[4-(5-fluoro-2-methoxyphenyl)-1H-pyrrolo[2,3-b]pyridin-2-yl]cyclohex-3-en-1-yl}-L-isoleucine;
ethyl {[4-{4-[3-fluoro-4-(methylcarbamoyl)phenyl]-1H-pyrrolo[2,3-b]pyridin-2-yl}-3,6-dihydropyridin-1(2H)-yl]sulfonyl}carbamate;
4-(3-fluoro-2-methoxyphenyl)-2-[1-(methylsulfonyl)-1,2,3,6-tetrahydropyridin-4-yl]-1H-pyrrolo[2,3-b]pyridine;
4-[4-(3-fluoro-2-methoxyphenyl)-1H-pyrrolo[2,3-b]pyridin-2-yl]-N-methyl-3,6-dihydropyridine-1(2H)-carboxamide;
methyl 4-[4-(5-fluoro-2-methoxyphenyl)-1H-pyrrolo[2,3-b]pyridin-2-yl]-2,5-dihydro-1H-pyrrole-2-carboxylate;
1-{4-[4-(5-fluoro-2-methoxyphenyl)-1H-pyrrolo[2,3-b]pyridin-2-yl]-3,6-dihydropyridin-1(2H)-yl}-3-(3-hydroxyazetidin-1-yl)propane-1,3-dione;
[(2S)-4-[4-(5-fluoro-2-methoxyphenyl)-1H-pyrrolo[2,3-b]pyridin-2-yl]-1-(methylsulfonyl)-2,5-dihydro-1H-pyrrol-2-yl]methanol;
ethyl {[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]sulfonyl}carbamate;
2-({4-[4-(5-fluoro-2-methoxyphenyl)-1H-pyrrolo[2,3-b]pyridin-2-yl]-3,6-dihydropyridin-1(2H)-yl}sulfonyl)-1-(3-hydroxyazetidin-1-yl)ethanone;
{(2S)-4-[4-(5-fluoro-2-methoxyphenyl)-1H-pyrrolo[2,3-b]pyridin-2-yl]-2,5-dihydro-1H-pyrrol-2-yl}methanol;
8-[4-(5-fluoro-2-methoxyphenyl)-1H-pyrrolo[2,3-b]pyridin-2-yl]-1,3-diazaspiro[4.5]dec-7-ene-2,4-dione;
1-amino-4-[4-(5-fluoro-2-methoxyphenyl)-1H-pyrrolo[2,3-b]pyridin-2-yl]cyclohex-3-ene-1-carboxylic acid;
2-(2-azaspiro[3.3]hept-6-yl)-4-(5-fluoro-2-methoxyphenyl)-1H-pyrrolo[2,3-b]pyridine;
4-(5-fluoro-2-methoxyphenyl)-5-methoxy-2-(1,2,3,6-tetrahydropyridin-4-yl)-1H-pyrrolo[2,3-b]pyridine;
ethyl 4-(5-fluoro-2-methoxyphenyl)-2-(1,2,3,6-tetrahydropyridin-4-yl)-1H-pyrrolo[2,3-b]pyridine-3-carboxylate;

4-(5-fluoro-2-methoxyphenyl)-2-(1-{[1-(methylsulfonyl) piperidin-4-yl]sulfonyl}-1,2,3,6-tetrahydropyridin-4-yl)-1H-pyrrolo[2,3-b]pyridine;

N-[2-({4-[4-(5-fluoro-2-methoxyphenyl)-1H-pyrrolo[2,3-b]pyridin-2-yl]-3,6-dihydropyridin-1(2H)-yl}sulfonyl)ethyl]methanesulfonamide;

{4-[4-(5-fluoro-2-methoxyphenyl)-1H-pyrrolo[2,3-b]pyridin-2-yl]-1-(methylsulfonyl)-1,2,3,6-tetrahydropyridin-2-yl}methanol;

ethyl ({4-[4-(5-fluoro-2-methoxyphenyl)-1H-pyrrolo[2,3-b]pyridin-2-yl]-2-(hydroxymethyl)-3,6-dihydropyridin-1(2H)-yl}sulfonyl)carbamate;

2-{4-[4-(5-fluoro-2-methoxyphenyl)-1H-pyrrolo[2,3-b]pyridin-2-yl]-2-(hydroxymethyl)-3,6-dihydropyridin-1(2H)-yl}-N,N-dimethylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-[4-(5-fluoro-2-methoxyphenyl)-1H-pyrrolo[2,3-b]pyridin-2-yl]-N,N-dimethyl-2,5-dihydro-1H-pyrrole-2-carboxamide;

2-(4-{4-[4-(5-fluoro-2-methoxyphenyl)-1H-pyrrolo[2,3-b]pyridin-2-yl]-3,6-dihydropyridin-1(2H)-yl}piperidin-1-yl)-N,N-dimethylacetamide;

N-{4-[4-(2,3-difluorophenyl)-1H-pyrrolo[2,3-b]pyridin-2-yl]cyclohex-3-en-1-yl}glycine;

1-[3-({4-[4-(5-fluoro-2-methoxyphenyl)-1H-pyrrolo[2,3-b]pyridin-2-yl]-3,6-dihydropyridin-1(2H)-yl}sulfonyl)azetidin-1-yl]ethanone;

4-(5-fluoro-2-methoxyphenyl)-2-(1-{[1-(methylsulfonyl)azetidin-3-yl]sulfonyl}-1,2,3,6-tetrahydropyridin-4-yl)-1H-pyrrolo[2,3-b]pyridine;

ethyl 4-(5-fluoro-2-methoxyphenyl)-2-[1-(methylsulfonyl)-1,2,3,6-tetrahydropyridin-4-yl]-1H-pyrrolo[2,3-b]pyridine-3-carboxylate;

4-(5-fluoro-2-methoxyphenyl)-2-(2,3,6,7-tetrahydro-1H-azepin-4-yl)-1H-pyrrolo[2,3-b]pyridine;

3-(2-{4-[4-(5-fluoro-2-methoxyphenyl)-1H-pyrrolo[2,3-b]pyridin-2-yl]-3,6-dihydropyridin-1(2H)-yl}-2-oxoethyl)imidazolidine-2,4-dione;

({4-[4-(5-fluoro-2-methoxyphenyl)-1H-pyrrolo[2,3-b]pyridin-2-yl]-3,6-dihydropyridin-1(2H)-yl}sulfonyl)acetonitrile;

propan-2-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

4-(5-fluoro-2-methoxyphenyl)-2-[2-(methylsulfonyl)-2-azaspiro[3.3]hept-6-yl]-1H-pyrrolo[2,3-b]pyridine;

ethyl ({4-[5-cyano-4-(5-fluoro-2-methoxyphenyl)-1H-pyrrolo[2,3-b]pyridin-2-yl]-3,6-dihydropyridin-1(2H)-yl}sulfonyl)carbamate;

N-[2-(4-fluoro-2-{2-[1-(methylsulfonyl)-1,2,3,6-tetrahydropyridin-4-yl]-1H-pyrrolo[2,3-b]pyridin-4-yl}phenoxy)ethyl]methanesulfonamide;

2-{4-fluoro-2-[2-(1,2,3,6-tetrahydropyridin-4-yl)-1H-pyrrolo[2,3-b]pyridin-4-yl]phenoxy}ethanamine;

N-[4-({4-[4-(5-fluoro-2-methoxyphenyl)-1H-pyrrolo[2,3-b]pyridin-2-yl]-3,6-dihydropyridin-1(2H)-yl}methyl)phenyl]methanesulfonamide;

tert-butyl 4-{4-[5-fluoro-2-(methylamino)phenyl]-1H-pyrrolo[2,3-b]pyridin-2-yl}-3,6-dihydropyridine-1(2H)-carboxylate;

4-fluoro-N-methyl-2-[2-(1,2,3,6-tetrahydropyridin-4-yl)-1H-pyrrolo[2,3-b]pyridin-4-yl]aniline;

1-amino-4-[4-(5-fluoro-2-methoxyphenyl)-1H-pyrrolo[2,3-b]pyridin-2-yl]-N,N-dimethylcyclohex-3-ene-1-carboxamide;

4-(5-fluoro-2-methoxyphenyl)-2-(1,2,3,6-tetrahydropyridin-4-yl)-1H-pyrrolo[2,3-b]pyridine-3-carbonitrile;

1-(3-{4-[4-(5-fluoro-2-methoxyphenyl)-1H-pyrrolo[2,3-b]pyridin-2-yl]-3,6-dihydropyridin-1(2H)-yl}-3-oxopropanoyl)prolinamide;

N-ethoxy-4-[4-(5-fluoro-2-methoxyphenyl)-1H-pyrrolo[2,3-b]pyridin-2-yl]cyclohex-3-ene-1-carboxamide;

4-(5-fluoro-2-methoxyphenyl)-2-(1,2,3,6-tetrahydropyridin-4-yl)-1H-pyrrolo[2,3-b]pyridine-3-carboxamide;

ethyl ({3-[4-(5-fluoro-2-methoxyphenyl)-1H-pyrrolo[2,3-b]pyridin-2-yl]-8-azabicyclo[3.2.1]oct-2-en-8-yl}sulfonyl)carbamate;

4-[4-(5-fluoro-2-methoxyphenyl)-1H-pyrrolo[2,3-b]pyridin-2-yl]-N-(4-methoxybenzyl)cyclohex-3-ene-1-sulfonamide;

methyl 4-[4-(5-fluoro-2-methoxyphenyl)-1H-pyrrolo[2,3-b]pyridin-2-yl]-3,6-dihydro-2H-1,2'-bipyridine-3'-carboxylate;

1-({4-[4-(5-fluoro-2-methoxyphenyl)-1H-pyrrolo[2,3-b]pyridin-2-yl]piperidin-1-yl}acetyl)-L-prolinamide;

1-tert-butyl 2-methyl (2S)-4-{4-[4-(5-fluoro-2-methoxyphenyl)-1H-pyrrolo[2,3-b]pyridin-2-yl]-3,6-dihydropyridin-1(2H)-yl}pyrrolidine-1,2-dicarboxylate;

4-[4-(5-fluoro-2-methoxyphenyl)-1H-pyrrolo[2,3-b]pyridin-2-yl]-3,6-dihydro-2H-1,2'-bipyridine-3'-carboxylic acid;

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)acetamide;

N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)methanesulfonamide;

3-{4-[4-(5-fluoro-2-methoxyphenyl)-1H-pyrrolo[2,3-b]pyridin-2-yl]-3,6-dihydropyridin-1(2H)-yl}-4-hydroxycyclobut-3-ene-1,2-dione;

methyl 4-{4-[4-(5-fluoro-2-methoxyphenyl)-1H-pyrrolo[2,3-b]pyridin-2-yl]-3,6-dihydropyridin-1(2H)-yl}-L-prolinate;

methyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-prolinate;

ethyl 4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylate;

4-(5-fluoro-2-methoxyphenyl)-2-[1-(hydroxyacetyl)-1,2,3,6-tetrahydropyridin-4-yl]-1H-pyrrolo[2,3-b]pyridine-3-carbonitrile;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carbonitrile;

ethyl ({4-[3-cyano-4-(5-fluoro-2-methoxyphenyl)-1H-pyrrolo[2,3-b]pyridin-2-yl]-3,6-dihydropyridin-1(2H)-yl}sulfonyl)carbamate;

2-[1-(2,3-dihydroxypropyl)-1,2,3,6-tetrahydropyridin-4-yl]-4-(5-fluoro-2-methoxyphenyl)-1H-pyrrolo[2,3-b]pyridine-3-carboxamide;

ethyl ({4-[3-carbamoyl-4-(5-fluoro-2-methoxyphenyl)-1H-pyrrolo[2,3-b]pyridin-2-yl]-3,6-dihydropyridin-1(2H)-yl}sulfonyl)carbamate;

4-[4-(5-fluoro-2-methoxyphenyl)-1H-pyrrolo[2,3-b]pyridin-2-yl]cyclohex-3-ene-1-sulfonamide;

4-(5-fluoro-2-methoxyphenyl)-2-[1-(methylcarbamoyl)-1,2,3,6-tetrahydropyridin-4-yl]-1H-pyrrolo[2,3-b]pyridine-3-carboxamide;

ethyl ({6-[4-(5-fluoro-2-methoxyphenyl)-1H-pyrrolo[2,3-b]pyridin-2-yl]-2-azaspiro[3.3]hept-2-yl}sulfonyl)carbamate;

3-{6-[4-(5-fluoro-2-methoxyphenyl)-1H-pyrrolo[2,3-b]pyridin-2-yl]-2-azaspiro[3.3]hept-2-yl}propane-1,2-diol;

2-{6-[4-(5-fluoro-2-methoxyphenyl)-1H-pyrrolo[2,3-b]pyridin-2-yl]-2-azaspiro[3.3]hept-2-yl}-N,N-dimethylacetamide;

2-({4-[4-(5-fluoro-2-methoxyphenyl)-1H-pyrrolo[2,3-b]pyridin-2-yl]-3,6-dihydropyridin-1(2H)-yl}sulfonyl)-N-(3-hydroxycyclobutyl)acetamide;

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)-L-proline;

4-{4-[4-(5-fluoro-2-methoxyphenyl)-1H-pyrrolo[2,3-b]pyridin-2-yl]-3,6-dihydropyridin-1(2H)-yl}-1-(methylsulfonyl)pyrrolidine-3-carboxylic acid;

2-[1-(azetidin-1-ylsulfonyl)-1,2,3,6-tetrahydropyridin-4-yl]-4-(5-fluoro-2-methoxyphenyl)-1H-pyrrolo[2,3-b]pyridine;

1-({4-[4-(5-fluoro-2-methoxyphenyl)-1H-pyrrolo[2,3-b]pyridin-2-yl]-3,6-dihydropyridin-1(2H)-yl}sulfonyl)azetidine-3-carbonitrile;

2-{1-[(4,4-difluoropiperidin-1-yl)sulfonyl]-1,2,3,6-tetrahydropyridin-4-yl}-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N-{1-[2-(methylsulfonyl)ethyl]-1H-pyrazol-4-yl}cyclohex-3-ene-1-carboxamide;

4-[4-(5-fluoro-2-methoxyphenyl)-1H-pyrrolo[2,3-b]pyridin-2-yl]-N-(1-methyl-1H-pyrazol-4-yl)cyclohex-3-ene-1-carboxamide;

4-[4-(5-fluoro-2-methoxyphenyl)-1H-pyrrolo[2,3-b]pyridin-2-yl]-N-(1H-tetrazol-5-ylmethyl)cyclohex-3-ene-1-carboxamide;

N-{4-[4-(5-fluoro-2-methoxyphenyl)-1H-pyrrolo[2,3-b]pyridin-2-yl]cyclohex-3-en-1-yl}-L-norvaline;

4-[4-(5-fluoro-2-methoxyphenyl)-1H-pyrrolo[2,3-b]pyridin-2-yl]-N-(1H-tetrazol-5-ylmethyl)cyclohex-3-en-1-amine;

2-[4-({4-[4-(5-fluoro-2-methoxyphenyl)-1H-pyrrolo[2,3-b]pyridin-2-yl]-3,6-dihydropyridin-1(2H)-yl}sulfonyl)piperidin-1-yl]-N,N-dimethylacetamide;

2-{4-[4-(5-fluoro-2-methoxyphenyl)-1H-pyrrolo[2,3-b]pyridin-2-yl]-3,6-dihydropyridin-1(2H)-yl}-1-[(2R)-2-(hydroxymethyl)pyrrolidin-1-yl]ethanone;

4-(5-fluoro-2-methoxyphenyl)-2-[1-(methylsulfonyl)-2,3,6,7-tetrahydro-1H-azepin-4-yl]-1H-pyrrolo[2,3-b]pyridine;

4-[4-(5-fluoro-2-methoxyphenyl)-1H-pyrrolo[2,3-b]pyridin-2-yl]-N-methyl-2,3,6,7-tetrahydro-1H-azepine-1-carboxamide;

[1-({4-[4-(5-fluoro-2-methoxyphenyl)-1H-pyrrolo[2,3-b]pyridin-2-yl]-3,6-dihydropyridin-1(2H)-yl}carbonyl)-1,2,3,6-tetrahydropyridin-4-yl]boronic acid;

3-{4-[4-(5-fluoro-2-methoxyphenyl)-1H-pyrrolo[2,3-b]pyridin-2-yl]-3,6-dihydropyridin-1(2H)-yl}-4-(methylsulfanyl)cyclobut-3-ene-1,2-dione;

N-{4-[4-(5-fluoro-2-methoxyphenyl)-1H-pyrrolo[2,3-b]pyridin-2-yl]cyclohex-3-en-1-yl}methanesulfonamide;

1-{4-[4-(5-fluoro-2-methoxyphenyl)-1H-pyrrolo[2,3-b]pyridin-2-yl]cyclohex-3-en-1-yl}-3-methylurea;

N-{4-[4-(5-fluoro-2-methoxyphenyl)-1H-pyrrolo[2,3-b]pyridin-2-yl]cyclohex-3-en-1-yl}-2-hydroxyacetamide;

2-cyano-N-{4-[4-(5-fluoro-2-methoxyphenyl)-1H-pyrrolo[2,3-b]pyridin-2-yl]cyclohex-3-en-1-yl}acetamide;

4-[4-(5-fluoro-2-methoxyphenyl)-1H-pyrrolo[2,3-b]pyridin-2-yl]-1,2,5,6-tetrahydropyridine-3-carbonitrile;

(3-{4-[4-(5-fluoro-2-methoxyphenyl)-1H-pyrrolo[2,3-b]pyridin-2-yl]-3,6-dihydropyridin-1(2H)-yl}oxetan-3-yl) acetonitrile;

4-[4-(5-fluoro-2-methoxyphenyl)-1H-pyrrolo[2,3-b]pyridin-2-yl]-N-{1-[(2R)-2-hydroxypropyl]-1H-pyrazol-4-yl}cyclohex-3-ene-1-carboxamide;

2-{4-[4-(5-fluoro-2-methoxyphenyl)-1H-pyrrolo[2,3-b]pyridin-2-yl]piperidin-1-yl}-1-(3-methoxyazetidin-1-yl)ethanone;

1-({4-[4-(5-fluoro-2-methoxyphenyl)-1H-pyrrolo[2,3-b]pyridin-2-yl]piperidin-1-yl}acetyl) azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-(3-hydroxy-3-methylazetidin-1-yl)ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]piperidin-1-yl}ethanone;

2-{4-[4-(5-fluoro-2-methoxyphenyl)-1H-pyrrolo[2,3-b]pyridin-2-yl]piperidin-1-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]piperidin-1-yl}ethanone;

1-(3-fluoroazetidin-1-yl)-2-{4-[4-(5-fluoro-2-methoxyphenyl)-1H-pyrrolo[2,3-b]pyridin-2-yl]piperidin-1-yl}ethanone;

N-(3-fluorocyclobutyl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]piperidin-1-yl}-1-(3-hydroxypyrrolidin-1-yl)ethanone;

(3-{4-[4-(5-fluoro-2-methoxyphenyl)-1H-pyrrolo[2,3-b]pyridin-2-yl]-3,6-dihydropyridin-1(2H)-yl}oxetan-3-yl)acetic acid;

4-fluoro-2-{2-[1-(methylsulfonyl)-1,2,3,6-tetrahydropyridin-4-yl]-1H-pyrrolo[2,3-b]pyridin-4-yl}aniline;

methyl N-{4-[4-(5-fluoro-2-methoxyphenyl)-1H-pyrrolo[2,3-b]pyridin-2-yl]cyclohex-3-en-1-yl}-3-methyl-L-valinate;

N-cyano-4-[4-(5-fluoro-2-methoxyphenyl)-1H-pyrrolo[2,3-b]pyridin-2-yl]cyclohex-3-ene-1-carboxamide;

2-(3,3-dimethyl-1,2,3,6-tetrahydropyridin-4-yl)-4-(5-fluoro-2-methoxyphenyl)-1H-pyrrolo[2,3-b]pyridine;

2-(methylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-{[({4-[4-(5-fluoro-2-methoxyphenyl)-1H-pyrrolo[2,3-b]pyridin-2-yl]-3,6-dihydropyridin-1(2H)-yl}sulfonyl)carbamoyl]oxy}ethyl acetate;

2-(pyrrolidin-1-yl)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

azetidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-hydroxyethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

N-[2-(3-fluoro-5-{2-[1-(methylsulfonyl)-1,2,3,6-tetrahydropyridin-4-yl]-1H-pyrrolo[2,3-b]pyridin-4-yl}phenoxy)ethyl]methanesulfonamide;

4-[4-(5-fluoro-2-methoxyphenyl)-1H-pyrrolo[2,3-b]pyridin-2-yl]-5,6-dihydropyridin-2(1H)-one;

2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)acetamide;

1-{4-[4-(5-fluoro-2-methoxyphenyl)-1H-pyrrolo[2,3-b]pyridin-2-yl]-3,6-dihydropyridin-1(2H)-yl}-3-[2-(hydroxymethyl)pyrrolidin-1-yl]propane-1,3-dione;

cyclopropyl({4-[4-(5-fluoro-2-methoxyphenyl)-1H-pyrrolo[2,3-b]pyridin-2-yl]cyclohex-3-en-1-yl}amino)acetic acid;

2-[3,3-dimethyl-1-(methylsulfonyl)-1,2,3,6-tetrahydropyridin-4-yl]-4-(5-fluoro-2-methoxyphenyl)-1H-pyrrolo[2,3-b]pyridine;

4-[4-(5-fluoro-2-methoxyphenyl)-1H-pyrrolo[2,3-b]pyridin-2-yl]-N,3,3-trimethyl-3,6-dihydropyridine-1(2H)-carboxamide;

4-[4-(5-fluoro-2-methoxyphenyl)-1H-pyrrolo[2,3-b]pyridin-2-yl]cyclohex-3-en-1-amine;

4-(5-fluoro-2-methoxyphenyl)-2-[(6S)-6-methyl-1,2,3,6-tetrahydropyridin-4-yl]-1H-pyrrolo[2,3-b]pyridine;

$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N-methylglycinamide;

tert-butyl N-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinate;

$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)glycinamide;

$N^2$-(2-{4-[4-(5-fluoro-2-methoxyphenyl)-1H-pyrrolo[2,3-b]pyridin-2-yl]-3,6-dihydropyridin-1(2H)-yl}-3,4-dioxocyclobut-1-en-1-yl)-N,N-dimethylglycinamide;

tert-butyl {4-[4-(4-fluoro-2-methoxyphenyl)-1H-pyrrolo[2,3-b]pyridin-2-yl]-3,6-dihydropyridin-1(2H)-yl}acetate;

{4-[4-(5-fluoro-2-methoxyphenyl)-1H-pyrrolo[2,3-b]pyridin-2-yl]-3,3-dimethyl-3,6-dihydropyridin-1(2H)-yl}acetic acid;

4-[4-(5-fluoro-2-methoxyphenyl)-1H-pyrrolo[2,3-b]pyridin-2-yl]cyclohex-3-ene-1-carbonitrile;

2-{4-[4-(5-fluoro-2-methoxyphenyl)-5-methoxy-1H-pyrrolo[2,3-b]pyridin-2-yl]-3,6-dihydropyridin-1(2H)-yl}-N,N-dimethylacetamide;

ethyl ({5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}sulfonyl)carbamate;

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}propane-1,2-diol;

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

2-{4-[4-(4-fluoro-2-methoxyphenyl)-1H-pyrrolo[2,3-b]pyridin-2-yl]-3,6-dihydropyridin-1(2H)-yl}acetamide;

2-{4-[4-(4-fluoro-2-methoxyphenyl)-1H-pyrrolo[2,3-b]pyridin-2-yl]-3,6-dihydropyridin-1(2H)-yl}-N-methylacetamide;

N-{4-[4-(5-fluoro-2-methoxyphenyl)-1H-pyrrolo[2,3-b]pyridin-2-yl]cyclohexyl}-D-valine;

2-{4-[5-fluoro-4-(5-fluoro-2-methoxyphenyl)-1H-pyrrolo[2,3-b]pyridin-2-yl]piperidin-1-yl}acetamide;

4-(5-fluoro-2-methoxyphenyl)-2-{1-[2-(2-methoxyethoxy)ethyl]-1,2,3,6-tetrahydropyridin-4-yl}-1H-pyrrolo[2,3-b]pyridine;

4-[4-(5-fluoro-2-methoxyphenyl)-1H-pyrrolo[2,3-b]pyridin-2-yl]cyclohex-3-en-1-yl methylsulfamate;

2-{4-[4-(5-fluoro-2-methoxyphenyl)-1H-pyrrolo[2,3-b]pyridin-2-yl]-3,6-dihydropyridin-1(2H)-yl}-1-(3-methoxyazetidin-1-yl)ethanone;

1-({4-[4-(5-fluoro-2-methoxyphenyl)-1H-pyrrolo[2,3-b]pyridin-2-yl]-3,6-dihydropyridin-1(2H)-yl}acetyl)azetidine-3-carbonitrile;

1-(3,3-difluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(hydroxymethyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-1-(3-hydroxy-3-methylazetidin-1-yl) ethanone;

1-[(2S,3R)-3-ethyl-2-(hydroxymethyl)azetidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-1-[3-(methoxymethyl)-3-methylazetidin-1-yl]ethanone;

1-[3-fluoro-3-(methoxymethyl)pyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

N-cyclobutyl-2-{4-[4-(5-fluoro-2-methoxyphenyl)-1H-pyrrolo[2,3-b]pyridin-2-yl]-3,6-dihydropyridin-1(2H)-yl}acetamide;

1-(3-fluoroazetidin-1-yl)-2-{4-[4-(5-fluoro-2-methoxyphenyl)-1H-pyrrolo[2,3-b]pyridin-2-yl]-3,6-dihydropyridin-1(2H)-yl}ethanone;

2-{4-[4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

N-(3-fluorocyclobutyl)-2-{4-[4-(5-fluoro-2-methoxyphenyl)-1H-pyrrolo[2,3-b]pyridin-2-yl]-3,6-dihydropyridin-1(2H)-yl}acetamide;

2-{4-[4-(5-fluoro-2-methoxyphenyl)-1H-pyrrolo[2,3-b]pyridin-2-yl]-3,6-dihydropyridin-1(2H)-yl}-1-(3-hydroxypyrrolidin-1-yl)ethanone;

2-{4-[4-(5-fluoro-2-methoxyphenyl)-1H-pyrrolo[2,3-b]pyridin-2-yl]-3,3-dimethyl-3,6-dihydropyridin-1(2H)-yl}-N,N-dimethylacetamide;

3-{4-[4-(5-fluoro-2-methoxyphenyl)-1H-pyrrolo[2,3-b]pyridin-2-yl]-3,3-dimethyl-3,6-dihydropyridin-1(2H)-yl}propane-1,2-diol;

1-({4-[4-(5-fluoro-2-methoxyphenyl)-1H-pyrrolo[2,3-b]pyridin-2-yl]piperidin-1-yl}acetyl)-L-proline;

1-({4-[4-(5-fluoro-2-methoxyphenyl)-1H-pyrrolo[2,3-b]pyridin-2-yl]-3,6-dihydropyridin-1(2H)-yl}acetyl)-L-proline;

2-{4-[4-(5-fluoro-2-methoxyphenyl)-1H-pyrrolo[2,3-b]pyridin-2-yl]piperidin-1-yl}-N-(methylsulfonyl)acetamide;

1-[(3S,4S)-3,4-dihydroxypyrrolidin-1-yl]-2-{4-[4-(5-fluoro-2-methoxyphenyl)-1H-pyrrolo[2,3-b]pyridin-2-yl]piperidin-1-yl}ethanone;

1-[(3S,4S)-3,4-dihydroxypyrrolidin-1-yl]-2-{4-[4-(5-fluoro-2-methoxyphenyl)-1H-pyrrolo[2,3-b]pyridin-2-yl]-3,6-dihydropyridin-1(2H)-yl}ethanone;

N-{4-[4-(5-fluoro-2-methoxyphenyl)-1H-pyrrolo[2,3-b]pyridin-2-yl]cyclohex-3-en-1-yl}-L-serine;

5-[4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
4-(5-fluoro-2-methoxyphenyl)-2-[4-(piperazin-1-yl)cyclohex-1-en-1-yl]-1H-pyrrolo[2,3-b]pyridine;
$N^2$-{4-[4-(5-fluoro-2-methoxyphenyl)-1H-pyrrolo[2,3-b]pyridin-2-yl]cyclohex-3-en-1-yl}-N,N-dimethyl-D-valinamide;
(4R)-1-{4-[4-(5-fluoro-2-methoxyphenyl)-1H-pyrrolo[2,3-b]pyridin-2-yl]cyclohex-3-en-1-yl}-4-hydroxy-L-proline;
N-{4-[4-(5-fluoro-2-methoxyphenyl)-1H-pyrrolo[2,3-b]pyridin-2-yl]cyclohex-3-en-1-yl}-L-valine;
2-{4-[4-(2-methoxyphenyl)-1H-pyrrolo[2,3-b]pyridin-2-yl]piperidin-1-yl}-N-methylacetamide;
{4-[4-(2-methoxyphenyl)-1H-pyrrolo[2,3-b]pyridin-2-yl]piperidin-1-yl}acetic acid;
2-[(6S)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(6R)-6-methyl-1,2,3,6-tetrahydropyridin-4-yl]-1H-pyrrolo[2,3-b]pyridine;
4-(5-fluoro-2-methoxyphenyl)-2-[(2S)-2-methyl-1-(methylsulfonyl)piperidin-4-yl]-1H-pyrrolo[2,3-b]pyridine;
({4-[4-(5-fluoro-2-methoxyphenyl)-1H-pyrrolo[2,3-b]pyridin-2-yl]cyclohex-3-en-1-yl}oxy)acetic acid;
N-{4-[4-(5-fluoro-2-methoxyphenyl)-1H-pyrrolo[2,3-b]pyridin-2-yl]cyclohex-3-en-1-yl}-L-threonine;
2-{1-[(1,1-dioxidothiomorpholin-4-yl)sulfonyl]-1,2,3,6-tetrahydropyridin-4-yl}-4-(5-fluoro-2-methoxyphenyl)-1H-pyrrolo[2,3-b]pyridine;
4-(5-fluoro-2-methoxyphenyl)-2-{1-[(4-methylpiperazin-1-yl)sulfonyl]-1,2,3,6-tetrahydropyridin-4-yl}-1H-pyrrolo[2,3-b]pyridine;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-4-carboxylate;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)prolinate;
ethyl {4-[4-(5-fluoro-2-methoxyphenyl)-1H-pyrrolo[2,3-b]pyridin-2-yl]-3,6-dihydropyridin-1(2H)-yl}acetate;
propan-2-yl {4-[4-(5-fluoro-2-methoxyphenyl)-1H-pyrrolo[2,3-b]pyridin-2-yl]-3,6-dihydropyridin-1(2H)-yl}acetate;
{4-[3-cyano-4-(5-fluoro-2-methoxyphenyl)-1H-pyrrolo[2,3-b]pyridin-2-yl]-3,6-dihydropyridin-1(2H)-yl}acetic acid;
4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;
4-(2-ethoxy-4,5-difluorophenyl)-2-(1,2,3,6-tetrahydropyridin-4-yl)-1H-pyrrolo[2,3-b]pyridine;
2-hydroxy-2-methylpropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
(2,2-dimethyl-1,3-dioxolan-4-yl)methyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
tetrahydro-2H-pyran-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
4-(2-ethoxy-4,5-difluorophenyl)-2-[1-(methylsulfonyl)-1,2,3,6-tetrahydropyridin-4-yl]-1H-pyrrolo[2,3-b]pyridine;
4-[4-(2-ethoxy-4,5-difluorophenyl)-1H-pyrrolo[2,3-b]pyridin-2-yl]-N-methyl-3,6-dihydropyridine-1(2H)-carboxamide;
2-{4-[5-fluoro-4-(fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;
{(2S)-4-[4-(5-fluoro-2-methoxyphenyl)-1H-pyrrolo[2,3-b]pyridin-2-yl]-1,2,3,6-tetrahydropyridin-2-yl}methanol;
{(2S)-4-[4-(5-fluoro-2-methoxyphenyl)-1H-pyrrolo[2,3-b]pyridin-2-yl]-1,2,5,6-tetrahydropyridin-2-yl}methanol;
2-{4-[4-(4,5-difluoro-2-methoxyphenyl)-1H-pyrrolo[2,3-b]pyridin-2-yl]piperidin-1-yl}-N-methylacetamide;
2-{4-[4-(4,5-difluoro-2-methoxyphenyl)-1H-pyrrolo[2,3-b]pyridin-2-yl]piperidin-1-yl}-N,N-dimethylacetamide;
2-{5-[4-(5-fluoro-2-methoxyphenyl)-1H-pyrrolo[2,3-b]pyridin-2-yl]-2,3,4,7-tetrahydro-1H-azepin-1-yl}acetamide;
2-{5-[4-(5-fluoro-2-methoxyphenyl)-1H-pyrrolo[2,3-b]pyridin-2-yl]-2,3,4,7-tetrahydro-1H-azepin-1-yl}-N,N-dimethylacetamide;
(1S,2S,3R,4R)-3-[({4-[4-(4,5-difluoro-2-methoxyphenyl)-1H-pyrrolo[2,3-b]pyridin-2-yl]-3,6-dihydropyridin-1(2H)-yl}acetyl)amino]bicyclo[2.2.1]hept-5-ene-2-carboxamide;
{4-[4-(5-fluoro-2-methoxyphenyl)-1H-pyrrolo[2,3-b]pyridin-2-yl]cyclohex-3-en-1-yl}[(2S)-2-(hydroxymethyl)pyrrolidin-1-yl]methanone;
2-{4-[4-(4-fluoro-2-methoxyphenyl)-1H-pyrrolo[2,3-b]pyridin-2-yl]piperidin-1-yl}acetamide;
2-{4-[4-(4-fluoro-2-methoxyphenyl)-1H-pyrrolo[2,3-b]pyridin-2-yl]piperidin-1-yl}-N-methylacetamide;
4-(5-fluoro-2-methoxyphenyl)-2-(octahydrocyclopenta[c]pyrrol-5-yl)-1H-pyrrolo[2,3-b]pyridine;
1-{4-[5-fluoro-4-(5-fluoro-2-methoxyphenyl)-1H-pyrrolo[2,3-b]pyridin-2-yl]piperidin-1-yl}-2-hydroxyethanone;
pyrrolidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
piperidin-4-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
piperidin-4-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
pyrrolidin-3-yl ({4-[4-(5-fluoro-2-methoxyphenyl)-1H-pyrrolo[2,3-b]pyridin-2-yl]-3,6-dihydropyridin-1(2H)-yl}sulfonyl)carbamate;
2,3-dihydroxypropyl ({4-[4-(5-fluoro-2-methoxyphenyl)-1H-pyrrolo[2,3-b]pyridin-2-yl]-3,6-dihydropyridin-1(2H)-yl}sulfonyl)carbamate;
methyl {4-[4-(2-methoxyphenyl)-1H-pyrrolo[2,3-b]pyridin-2-yl]piperidin-1-yl}acetate;
1-[(2S)-2-(hydroxymethyl)pyrrolidin-1-yl]-2-{4-[4-(2-methoxyphenyl)-1H-pyrrolo[2,3-b]pyridin-2-yl]piperidin-1-yl}ethanone;
(2R)-2-({4-[4-(5-fluoro-2-methoxyphenyl)-1H-pyrrolo[2,3-b]pyridin-2-yl]cyclohex-3-en-1-yl}amino)-1-(3-hydroxyazetidin-1-yl)-3-methylbutan-1-one;
1-{4-[4-(5-fluoro-2-methoxyphenyl)-1H-pyrrolo[2,3-b]pyridin-2-yl]cyclohex-3-en-1-yl}-N,N-dimethyl-L-prolinamide;

(2R)-({4-[4-(5-fluoro-2-methoxyphenyl)-1H-pyrrolo[2,3-b]pyridin-2-yl]cyclohex-3-en-1-yl}amino)(phenyl)acetic acid;

4-(5-fluoro-2-methoxyphenyl)-2-[3-(methylsulfonyl)-3-azabicyclo[4.1.0]hept-6-yl]-1H-pyrrolo[2,3-b]pyridine;

4-(5-fluoro-2-methoxyphenyl)-2-[4-(1H-tetrazol-5-yl)cyclohex-1-en-1-yl]-1H-pyrrolo[2,3-b]pyridine;

4-[4-(5-fluoro-2-methoxyphenyl)-1H-pyrrolo[2,3-b]pyridin-2-yl]cyclohex-3-en-1-yl tert-butylcarbamate;

2-{4-[4-(5-fluoro-2-methoxyphenyl)-5-methoxy-1H-pyrrolo[2,3-b]pyridin-2-yl]-3,6-dihydropyridin-1(2H)-yl}-1-[(2S)-2-(hydroxymethyl)pyrrolidin-1-yl]ethanone;

2-{4-[4-(4,5-difluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone;

2-{(2S)-4-[4-(5-fluoro-2-methoxyphenyl)-1H-pyrrolo[2,3-b]pyridin-2-yl]-2-methylpiperidin-1-yl}-N,N-dimethylacetamide;

4,4,4-trifluoro-2-{4-[4-(5-fluoro-2-methoxyphenyl)-1H-pyrrolo[2,3-b]pyridin-2-yl]-3,6-dihydropyridin-1(2H)-yl}butanoic acid;

2-{4-[4-(5-fluoro-2-methoxyphenyl)-1H-pyrrolo[2,3-b]pyridin-2-yl]-3,6-dihydropyridin-1(2H)-yl}-N,N-dimethyl-2-oxoethanesulfonamide;

2-{4-[4-(5-fluoro-2-methoxyphenyl)-1H-pyrrolo[2,3-b]pyridin-2-yl]piperidin-1-yl}-N-methyl-2-oxoethanesulfonamide;

2-{4-[4-(5-fluoro-2-methoxyphenyl)-1H-pyrrolo[2,3-b]pyridin-2-yl]piperidin-1-yl}-N,N-dimethyl-2-oxoethanesulfonamide;

1-{4-[4-(5-fluoro-2-methoxyphenyl)-1H-pyrrolo[2,3-b]pyridin-2-yl]-3,6-dihydropyridin-1(2H)-yl}-1-oxopropane-2-sulfonamide;

ethyl {4-[4-(5-fluoro-2-methoxyphenyl)-1H-pyrrolo[2,3-b]pyridin-2-yl]-3,6-dihydropyridin-1(2H)-yl}(phenyl)acetate;

ethyl 2-{4-[4-(5-fluoro-2-methoxyphenyl)-1H-pyrrolo[2,3-b]pyridin-2-yl]-3,6-dihydropyridin-1(2H)-yl}-1,3-thiazole-5-carboxylate;

tert-butyl 3-{4-[4-(5-fluoro-2-methoxyphenyl)-1H-pyrrolo[2,3-b]pyridin-2-yl]-3,6-dihydropyridin-1(2H)-yl}pyrrolidine-1-carboxylate;

ethyl {[(6S)-4-[4-(5-fluoro-2-methoxyphenyl)-1H-pyrrolo[2,3-b]pyridin-2-yl]-6-methyl-3,6-dihydropyridin-1(2H)-yl]sulfonyl}carbamate;

2-({4-[4-(5-fluoro-2-methoxyphenyl)-1H-pyrrolo[2,3-b]pyridin-2-yl]cyclohex-3-en-1-yl}oxy)ethanol;

2-{4-[4-(5-fluoro-2-methoxyphenyl)-1H-pyrrolo[2,3-b]pyridin-2-yl]piperidin-1-yl}propanoic acid;

{4-[4-(5-fluoro-2-methoxyphenyl)-1H-pyrrolo[2,3-b]pyridin-2-yl]-3,6-dihydropyridin-1(2H)-yl}(phenyl)acetic acid;

4-(5-fluoro-2-methoxyphenyl)-2-[1-(pyrrolidin-3-yl)-1,2,3,6-tetrahydropyridin-4-yl]-1H-pyrrolo[2,3-b]pyridine;

3-{4-[5-fluoro-4-(5-fluoro-2-methoxyphenyl)-1H-pyrrolo[2,3-b]pyridin-2-yl]piperidin-1-yl}-3-oxopropanenitrile;

5-fluoro-4-(5-fluoro-2-methoxyphenyl)-2-(1,2,3,6-tetrahydropyridin-4-yl)-1H-pyrrolo[2,3-b]pyridine-3-carbonitrile;

4-fluoro-2-[2-(1,2,3,6-tetrahydropyridin-4-yl)-1H-pyrrolo[2,3-b]pyridin-4-yl]benzamide;

{4-[3-cyano-5-fluoro-4-(5-fluoro-2-methoxyphenyl)-1H-pyrrolo[2,3-b]pyridin-2-yl]-3,6-dihydropyridin-1(2H)-yl}acetic acid;

2-aminoethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

azetidin-3-ylmethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-(dimethylamino)ethyl ({4-[4-(5-fluoro-2-methoxyphenyl)-1H-pyrrolo[2,3-b]pyridin-2-yl]-3,6-dihydropyridin-1(2H)-yl}sulfonyl)carbamate;

2-(2,2-dimethyl-1,2,3,6-tetrahydropyridin-4-yl)-4-(5-fluoro-2-methoxyphenyl)-1H-pyrrolo[2,3-b]pyridine;

{4-[3-cyano-4-(5-fluoro-2-methoxyphenyl)-1H-pyrrolo[2,3-b]pyridin-2-yl]piperidin-1-yl}acetic acid;

4-(5-fluoro-2-methoxyphenyl)-2-(piperidin-4-yl)-1H-pyrrolo[2,3-b]pyridine-3-carbonitrile;

2-{4-[3-cyano-4-(5-fluoro-2-methoxyphenyl)-1H-pyrrolo[2,3-b]pyridin-2-yl]piperidin-1-yl}-N,N-dimethylacetamide;

5-({4-[4-(5-fluoro-2-methoxyphenyl)-1H-pyrrolo[2,3-b]pyridin-2-yl]piperidin-1-yl}methyl)-2,4-dihydro-3H-1,2,4-triazol-3-one;

4-(5-fluoro-2-methoxyphenyl)-2-{1-[1-(methylsulfonyl)pyrrolidin-3-yl]-1,2,3,6-tetrahydropyridin-4-yl}-1H-pyrrolo[2,3-b]pyridine;

2-{4-[4-(5-fluoro-2-methoxyphenyl)-1H-pyrrolo[2,3-b]pyridin-2-yl]piperidin-1-yl}-N-(propan-2-ylsulfonyl)acetamide;

ethyl 2-{4-[4-(5-fluoro-2-methoxyphenyl)-1H-pyrrolo[2,3-b]pyridin-2-yl]piperidin-1-yl}-1,3-thiazole-5-carboxylate;

methyl (4-{4-[4-(5-fluoro-2-methoxyphenyl)-1H-pyrrolo[2,3-b]pyridin-2-yl]-3,6-dihydropyridin-1(2H)-yl}cyclohexyl)acetate;

3-{4-[4-(5-fluoro-2-methoxyphenyl)-1H-pyrrolo[2,3-b]pyridin-2-yl]-3,6-dihydropyridin-1(2H)-yl}-1-methylpyrrolidin-2-one;

4-{4-[4-(5-fluoro-2-methoxyphenyl)-1H-pyrrolo[2,3-b]pyridin-2-yl]-3,6-dihydropyridin-1(2H)-yl}pyrrolidin-2-one;

2-{4-[4-(5-fluoro-2-methoxyphenyl)-1H-pyrrolo[2,3-b]pyridin-2-yl]piperidin-1-yl}-1,3-thiazole-5-carboxylic acid;

(2S)-cyclohexyl({4-[4-(5-fluoro-2-methoxyphenyl)-1H-pyrrolo[2,3-b]pyridin-2-yl]cyclohex-3-en-1-yl}amino)acetic acid;

N-{4-[5-fluoro-4-(5-fluoro-2-methoxyphenyl)-1H-pyrrolo[2,3-b]pyridin-2-yl]cyclohex-3-en-1-yl}-D-valine;

N-{4-[5-fluoro-4-(5-fluoro-2-methoxyphenyl)-1H-pyrrolo[2,3-b]pyridin-2-yl]cyclohex-3-en-1-yl}-3-methyl-L-valine;

5-fluoro-4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile;

4-(5-fluoro-2-methoxyphenyl)-2-[1-(methylsulfonyl)piperidin-4-yl]-1H-pyrrolo[2,3-b]pyridine-3-carbonitrile;

{4-[5-fluoro-4-(5-fluoro-2-methoxyphenyl)-1H-pyrrolo[2,3-b]pyridin-2-yl]piperidin-1-yl}acetic acid;

methyl 1-({4-[4-(5-fluoro-2-methoxyphenyl)-1H-pyrrolo[2,3-b]pyridin-2-yl]cyclohex-3-en-1-yl}carbonyl)prolinate;

N-cyano-4-[3-cyano-5-fluoro-4-(5-fluoro-2-methoxyphenyl)-1H-pyrrolo[2,3-b]pyridin-2-yl]-3,6-dihydropyridine-1(2H)-carboxamide;

(4-{4-[4-(5-fluoro-2-methoxyphenyl)-1H-pyrrolo[2,3-b]pyridin-2-yl]-3,6-dihydropyridin-1(2H)-yl}cyclohexyl)acetic acid;
3-{4-[4-(5-fluoro-2-methoxyphenyl)-1H-pyrrolo[2,3-b]pyridin-2-yl]piperidin-1-yl}-1-methylpyrrolidin-2-one;
N-cyano-4-[5-fluoro-4-(5-fluoro-2-methoxyphenyl)-1H-pyrrolo[2,3-b]pyridin-2-yl]-3,6-dihydropyridine-1(2H)-carboxamide;
4-(5-fluoro-2-methoxyphenyl)-2-(1-{[2-(2-methoxyethoxy)ethyl]sulfonyl}-1,2,3,6-tetrahydropyridin-4-yl)-1H-pyrrolo[2,3-b]pyridine;
1-({4-[3-cyano-5-fluoro-4-(5-fluoro-2-methoxyphenyl)-1H-pyrrolo[2,3-b]pyridin-2-yl]-3,6-dihydropyridin-1(2H)-yl}acetyl)-L-prolinamide;
N-cyano-2-{4-[4-(5-fluoro-2-methoxyphenyl)-1H-pyrrolo[2,3-b]pyridin-2-yl]piperidin-1-yl}acetamide;
{(2R)-4-[4-(5-fluoro-2-methoxyphenyl)-1H-pyrrolo[2,3-b]pyridin-2-yl]-1,2,5,6-tetrahydropyridin-2-yl}methanol;
{(2R)-4-[4-(5-fluoro-2-methoxyphenyl)-1H-pyrrolo[2,3-b]pyridin-2-yl]-1,2,3,6-tetrahydropyridin--yl}methanol;
ethyl ({4-[5-fluoro-4-(5-fluoro-2-methoxyphenyl)-1H-pyrrolo[2,3-b]pyridin-2-yl]piperidin-1-yl}sulfonyl)carbamate;
2-{4-[5-fluoro-4-(5-fluoro-2-methoxyphenyl)-1H-pyrrolo[2,3-b]pyridin-2-yl]piperidin-1-yl}-N-(2-hydroxyethyl)-N-methylacetamide;
4-[4-(5-fluoro-2-methoxyphenyl)-1H-pyrrolo[2,3-b]pyridin-2-yl]cyclohex-3-en-1-yl[(3-hydroxyazetidin-1-yl)sulfonyl]carbamate;
4-(5-fluoro-2-methoxyphenyl)-2-{1-[(2-methoxyethyl)sulfonyl]-1,2,3,6-tetrahydropyridin-4-yl}-1H-pyrrolo[2,3-b]pyridine;
N-{4-[4-(5-fluoro-2-methoxyphenyl)-1H-pyrrolo[2,3-b]pyridin-2-yl]cyclohex-3-en-1-yl}-2-(2-ethoxyethoxy)ethanesulfonamide;
tert-butyl 3-{4-[4-(5-fluoro-2-methoxyphenyl)-1H-pyrrolo[2,3-b]pyridin-2-yl]-3,6-dihydropyridin-1(2H)-yl}cyclobutanecarboxylate;
3-{4-[4-(5-fluoro-2-methoxyphenyl)-1H-pyrrolo[2,3-b]pyridin-2-yl]-3,6-dihydropyridin-1(2H)-yl}cyclobutanecarboxylic acid;
4-(5-fluoro-2-methoxyphenyl)-2-[2-(methylsulfonyl)octahydrocyclopenta[c]pyrrol-5-yl]-1H-pyrrolo[2,3-b]pyridine;
[(2S)-4-[4-(5-fluoro-2-methoxyphenyl)-1H-pyrrolo[2,3-b]pyridin-2-yl]-2-(hydroxymethyl)-2,5-dihydro-1H-pyrrol-1-yl]acetic acid;
$N^2$-{4-[4-(5-fluoro-2-methoxyphenyl)-1H-pyrrolo[2,3-b]pyridin-2-yl]cyclohex-3-en-1-yl}-N-methyl-D-valinamide;
N-{4-[4-(5-fluoro-2-methoxyphenyl)-1H-pyrrolo[2,3-b]pyridin-2-yl]cyclohex-3-en-1-yl}-L-phenylalanine;
N-{4-[4-(5-fluoro-2-methoxyphenyl)-1H-pyrrolo[2,3-b]pyridin-2-yl]cyclohex-3-en-1-yl}-L-tyrosine;
$N^2$-{4-[4-(5-fluoro-2-methoxyphenyl)-1H-pyrrolo[2,3-b]pyridin-2-yl]cyclohex-3-en-1-yl}-L-valinamide;
$N^2$-{4-[4-(5-fluoro-2-methoxyphenyl)-1H-pyrrolo[2,3-b]pyridin-2-yl]cyclohex-3-en-1-yl}-N,3-dimethyl-L-valinamide;
(2S)-({4-[4-(5-fluoro-2-methoxyphenyl)-1H-pyrrolo[2,3-b]pyridin-2-yl]cyclohex-3-en-1-yl}amino)(phenyl)acetic acid;
2-[1-(cyanoacetyl)-1,2,3,6-tetrahydropyridin-4-yl]-4-(5-fluoro-2-methoxyphenyl)-1H-pyrrolo[2,3-b]pyridine-5-carbonitrile;
4-(5-fluoro-2-methoxyphenyl)-2-[1-(methylsulfonyl)-1,2,3,6-tetrahydropyridin-4-yl]-3-nitro-1H-pyrrolo[2,3-b]pyridine;
4-(5-fluoro-2-methoxyphenyl)-2-(2-{[2-(2-methoxyethoxy)ethyl]sulfonyl}-1,2,3,3a,4,6a-hexahydrocyclopenta[c]pyrrol-5-yl)-1H-pyrrolo[2,3-b]pyridine;
(9aR)-8-[4-(5-fluoro-2-methoxyphenyl)-1H-pyrrolo[2,3-b]pyridin-2-yl]-1,6,7,9a-tetrahydropyrido[2,1-c][1,4]oxazin-3(4H)-one;
7-[4-(5-fluoro-2-methoxyphenyl)-1H-pyrrolo[2,3-b]pyridin-2-yl]-1,5,6,8a-tetrahydro[1,3]oxazolo[3,4-a]pyridin-3-one;
2-{4-[4-(5-fluoro-2-methoxyphenyl)-1H-pyrrolo[2,3-b]pyridin-2-yl]piperidin-1-yl}-N-(2-methoxyethyl)-N-methylacetamide;
{4-[4-(5-fluoro-2-methoxyphenyl)-1H-pyrrolo[2,3-b]pyridin-2-yl]piperidin-1-yl}(phenyl)acetic acid;
2-{4-[5-cyano-4-(5-fluoro-2-methoxyphenyl)-1H-pyrrolo[2,3-b]pyridin-2-yl]-3,6-dihydropyridin-1(2H)-yl}acetamide;
N-(3-fluorocyclobutyl)-4-[4-(5-fluoro-2-methoxyphenyl)-1H-pyrrolo[2,3-b]pyridin-2-yl]-2,5-dihydro-1H-pyrrole-2-carboxamide;
4-(5-fluoro-2-methoxyphenyl)-2-[(2R)-2-methyl-1,2,3,6-tetrahydropyridin-4-yl]-1H-pyrrolo[2,3-b]pyridine-4-(5-fluoro-2-methoxyphenyl)-2-[(6R)-6-methyl-1,2,3,6-tetrahydropyridin-4-yl]-1H-pyrrolo[2,3-b]pyridine (1:1);
2-{4-[4-(5-fluoro-2-methoxyphenyl)-1H-pyrrolo[2,3-b]pyridin-2-yl]-6,6-dimethyl-3,6-dihydropyridin-1(2H)-yl}-N,N-dimethylacetamide;
methyl 4-[4-(5-fluoro-2-methoxyphenyl)-1H-pyrrolo[2,3-b]pyridin-2-yl]-1-(methylcarbamoyl)-2,5-dihydro-1H-pyrrole-2-carboxylate;
4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile;
5-[5-cyano-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;
2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-2-{4-[4-(5-fluoro-2-methoxyphenyl)-1H-pyrrolo[2,3-b]pyridin-2-yl]-3,6-dihydropyridin-1(2H)-yl}acetamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}ethanone;
ethyl 1-({4-[4-(5-fluoro-2-methoxyphenyl)-1H-pyrrolo[2,3-b]pyridin-2-yl]-3,6-dihydropyridin-1(2H)-yl}sulfonyl)piperidine-3-carboxylate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetamide;
N-cyano-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxamide;
N-cyano-4-[4-(5-fluoro-2-methoxyphenyl)-1H-pyrrolo[2,3-b]pyridin-2-yl]piperidine-1-carboxamide;
2-{4-[5-cyano-4-(5-fluoro-2-methoxyphenyl)-1H-pyrrolo[2,3-b]pyridin-2-yl]piperidin-1-yl}-N-methyl-2-oxoethanesulfonamide;

N-{5-[4-(5-fluoro-2-methoxyphenyl)-1H-pyrrolo[2,3-b]pyridin-2-yl]-1,2,3,3a,4,6a-hexahydropentalen-2-yl}-D-valine;
methyl 4-[4-(5-fluoro-2-methoxyphenyl)-1H-pyrrolo[2,3-b]pyridin-2-yl]-3,6-dihydropyridine-1(2H)-carboxylate;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine;
2-{4-[5-cyano-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;
2-({4-[4-(5-fluoro-2-methoxyphenyl)-1H-pyrrolo[2,3-b]pyridin-2-yl]cyclohex-3-en-1-yl}oxy)-N,N-dimethylacetamide;
2-({4-[4-(5-fluoro-2-methoxyphenyl)-1H-pyrrolo[2,3-b]pyridin-2-yl]cyclohex-3-en-1-yl}oxy)-1-(morpholin-4-yl)ethanone;
4-[5-fluoro-2-(methylsulfanyl)phenyl]-2-[1-(methylsulfonyl)-1,2,3,6-tetrahydropyridin-4-yl]-1H-pyrrolo[2,3-b]pyridine;
4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-5-carbonitrile;
2-{4-[5-cyano-4-(5-fluoro-2-methoxyphenyl)-1H-pyrrolo[2,3-b]pyridin-2-yl]-3,6-dihydropyridin-1(2H)-yl}-N-methyl-2-oxoethanesulfonamide;
2-{4-[5-cyano-4-(5-fluoro-2-methoxyphenyl)-1H-pyrrolo[2,3-b]pyridin-2-yl]piperidin-1-yl}acetamide;
2-{4-[4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;
2-{4-[4-(5-fluoro-2-methoxyphenyl)-1H-pyrrolo[2,3-b]pyridin-2-yl]-3,6-dihydropyridin-1(2H)-yl}-N-(2-methoxyethyl)-N-methylacetamide;
methyl (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl (trans-4-{4-[4-(5-fluoro-2-methoxyphenyl)-1H-pyrrolo[2,3-b]pyridin-2-yl]-3,6-dihydropyridin-1(2H)-yl}cyclohexyl)acetate;
methyl {4-[4-(5-fluoro-2-methoxyphenyl)-1H-pyrrolo[2,3-b]pyridin-2-yl]cyclohex-3-en-1-yl}acetate;
{4-[4-(5-fluoro-2-methoxyphenyl)-1H-pyrrolo[2,3-b]pyridin-2-yl]cyclohex-3-en-1-yl}acetic acid;
(4-{4-[4-(5-fluoro-2-methoxyphenyl)-1H-pyrrolo[2,3-b]pyridin-2-yl]piperidin-1-yl}cyclohexyl)acetic acid;
methyl 2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoate;
N-{4-[4-(5-fluoro-2-methoxyphenyl)-1H-pyrrolo[2,3-b]pyridin-2-yl]cyclohex-3-en-1-yl}-L-leucine;
4-(5-fluoro-2-methoxyphenyl)-2-[(6R)-6-methyl-1-(methylsulfonyl)-1,2,3,6-tetrahydropyridin-4-yl]-1H-pyrrolo[2,3-b]pyridine;
2-[(6R)-4-[4-(5-fluoro-2-methoxyphenyl)-1H-pyrrolo[2,3-b]pyridin-2-yl]-6-methyl-3,6-dihydropyridin-1(2H)-yl]-N,N-dimethylacetamide;
4-(5-fluoro-2-methoxyphenyl)-2-[(2R)-2-methyl-1-(methylsulfonyl)-1,2,3,6-tetrahydropyridin-4-yl]-1H-pyrrolo[2,3-b]pyridine;
2-[(2R)-4-[4-(5-fluoro-2-methoxyphenyl)-1H-pyrrolo[2,3-b]pyridin-2-yl]-2-methyl-3,6-dihydropyridin-1(2H)-yl]-N,N-dimethylacetamide;
{4-[4-(5-fluoro-2-methoxyphenyl)-1H-pyrrolo[2,3-b]pyridin-2-yl]cyclohex-3-en-1-yl}(3-hydroxyazetidin-1-yl)methanone;
2-{4-[5-fluoro-4-(5-fluoro-2-methoxyphenyl)-1H-pyrrolo[2,3-b]pyridin-2-yl]piperidin-1-yl}-N-methyl-2-oxoethanesulfonamide;
{4-[5-cyano-4-(5-fluoro-2-methoxyphenyl)-1H-pyrrolo[2,3-b]pyridin-2-yl]piperidin-1-yl}acetic acid;
2-[1-(cyanoacetyl)piperidin-4-yl]-4-(5-fluoro-2-methoxyphenyl)-1H-pyrrolo[2,3-b]pyridine-5-carbonitrile;
4-(5-fluoro-2-methoxyphenyl)-2-{1-[2-(3-hydroxyazetidin-1-yl)-2-oxoethyl]piperidin-4-yl}-1H-pyrrolo[2,3-b]pyridine-5-carbonitrile;
4-[5-fluoro-2-(methylsulfinyl)phenyl]-2-[1-(methylsulfonyl)-1,2,3,6-tetrahydropyridin-4-yl]-1H-pyrrolo[2,3-b]pyridine;
4-[3-cyano-5-fluoro-4-(5-fluoro-2-methoxyphenyl)-1H-pyrrolo[2,3-b]pyridin-2-yl]cyclohex-3-ene-1-carboxylic acid;
4-(5-fluoro-2-methoxyphenyl)-2-(1,2,3,3a,4,6a-hexahydrocyclopenta[c]pyrrol-5-yl)-5-hydroxy-1H-pyrrolo[2,3-b]pyridine-3-carbonitrile;
5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine-3-carbonitrile;
2-{4-[5-fluoro-4-(5-fluoro-2-methoxyphenyl)-1H-pyrrolo[2,3-b]pyridin-2-yl]piperidin-1-yl}-N-(3-hydroxycyclobutyl)-N-methylacetamide;
2-{4-[5-cyano-4-(5-fluoro-2-methoxyphenyl)-1H-pyrrolo[2,3-b]pyridin-2-yl]piperidin-1-yl}-N-(2-hydroxyethyl)-N-methylacetamide;
tert-butyl {4-[3-cyano-4-(5-fluoro-2-methoxyphenyl)-1H-pyrrolo[2,3-b]pyridin-2-yl]-3,6-dihydropyridin-1(2H)-yl}acetate;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-oxoethanesulfonamide;
1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-oxopropane-2-sulfonamide;
2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethyl-2-oxoethanesulfonamide;
tert-butyl {5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetate;
2-{4-[4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;
2-{4-[4-(5-fluoro-2-methoxyphenyl)-1H-pyrrolo[2,3-b]pyridin-2-yl]-3,6-dihydropyridin-1(2H)-yl}-1-[(3S)-3-hydroxypyrrolidin-1-yl]ethanone;
4-({4-[4-(5-fluoro-2-methoxyphenyl)-1H-pyrrolo[2,3-b]pyridin-2-yl]-3,6-dihydropyridin-1(2H)-yl}carbonyl)benzoic acid;
3-({4-[4-(5-fluoro-2-methoxyphenyl)-1H-pyrrolo[2,3-b]pyridin-2-yl]-3,6-dihydropyridin-1(2H)-yl}carbonyl)benzoic acid;
tert-butyl (3aS,6aR)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;
tert-butyl (3aR,6aS)-5-[4-(5-fluoro-2-methoxyphenyl)-1H-pyrrolo[2,3-b]pyridin-2-yl]-3,3a,4,6a-tetrahydrocyclopenta[c]pyrrole-2(1H)-carboxylate;
(3-{4-[4-(5-fluoro-2-methoxyphenyl)-1H-pyrrolo[2,3-b]pyridin-2-yl]-3,6-dihydropyridin-1(2H)-yl}cyclobutyl)acetic acid;

2-(4-{4-[4-(5-fluoro-2-methoxyphenyl)-1H-pyrrolo[2,3-b]pyridin-2-yl]-3,6-dihydropyridin-1(2H)-yl}-1H-pyrazol-1-yl)propanoic acid;

ethyl 5-[4-(5-fluoro-2-methoxyphenyl)-1H-pyrrolo[2,3-b]pyridin-2-yl]-1,2,3,6-tetrahydropyridine-4-carboxylate;

{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

4-(5-fluoro-2-methoxyphenyl)-2-[1-(2,5,8,11-tetraoxatetradecan-14-yl)-1,2,3,6-tetrahydropyridin-4-yl]-1H-pyrrolo[2,3-b]pyridine;

5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-3-carbonitrile;

5-[3-cyano-5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide;

{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}acetic acid;

2-{4-[3-cyano-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

4-(5-fluoro-2-methoxyphenyl)-2-{2-[2-(3-hydroxyazetidin-1-yl)-2-oxoethyl]-1,2,3,3a,4,6a-hexahydrocyclopenta[c]pyrrol-5-yl}-1H-pyrrolo[2,3-b]pyridine-5-carbonitrile;

4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

(3aR,5r,6aS)-5-[4-(5-fluoro-2-methoxyphenyl)-1H-pyrrolo[2,3-b]pyridin-2-yl]-N-methylhexahydrocyclopenta[c]pyrrole-2(1H)-carboxamide;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]ethanone;

1-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-2-hydroxyethanone;

(3aR,5r,6aS)-N-cyano-5-[4-(5-fluoro-2-methoxyphenyl)-1H-pyrrolo[2,3-b]pyridin-2-yl]hexahydrocyclopenta[c]pyrrole-2(1H)-carboxamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N,N-dimethylacetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]propane-1,2-diol;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]acetamide;

3-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-3-oxopropanenitrile;

4-[4-(5-fluoro-2-methoxyphenyl)-1H-pyrrolo[2,3-b]pyridin-2-yl]cyclohexanecarboxylic acid;

(4-{4-[3-cyano-4-(5-fluoro-2-methoxyphenyl)-1H-pyrrolo[2,3-b]pyridin-2-yl]-3,6-dihydropyridin-1(2H)-yl}cyclohexyl)acetic acid;

(4-{4-[5-fluoro-4-(5-fluoro-2-methoxyphenyl)-1H-pyrrolo[2,3-b]pyridin-2-yl]piperidin-1-yl}cyclohexyl)acetic acid;

{4-[5-chloro-4-(5-fluoro-2-methoxyphenyl)-1H-pyrrolo[2,3-b]pyridin-2-yl]cyclohex-3-en-1-yl}acetic acid;

2-({4-[4-(5-fluoro-2-methoxyphenyl)-1H-pyrrolo[2,3-b]pyridin-2-yl]-3,6-dihydropyridin-1(2H)-yl}sulfonyl)ethanol;

(3-{4-[4-(5-fluoro-2-methoxyphenyl)-1H-pyrrolo[2,3-b]pyridin-2-yl]-3,6-dihydropyridin-1(2H)-yl}cyclobutyl)(3-hydroxyazetidin-1-yl)methanone;

2-{5-[3-cyano-5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide;

2-[(6S)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

2-[(6R)-4-[4-(5-fluoro-2-methoxyphenyl)-1H-pyrrolo[2,3-b]pyridin-2-yl]-6-methyl-3,6-dihydropyridin-1(2H)-yl]-1-(3-hydroxyazetidin-1-yl)ethanone;

{5-[4-(5-fluoro-2-methoxyphenyl)-1H-pyrrolo[2,3-b]pyridin-2-yl]-1,2,3,6-tetrahydropyridin-4-yl}methanol;

{4-[4-(5-fluoro-2-methoxyphenyl)-1H-pyrrolo[2,3-b]pyridin-2-yl]-3,6-dihydropyridin-1(2H)-yl}(3-hydroxycyclobutyl)methanone;

4-(5-fluoro-2-methoxyphenyl)-2-[(3R)-3-methyl-1,2,3,6-tetrahydropyridin-4-yl]-1H-pyrrolo[2,3-b]pyridine;

4-(5-fluoro-2-methoxyphenyl)-2-[(3S)-3-methyl-1,2,3,6-tetrahydropyridin-4-yl]-1H-pyrrolo[2,3-b]pyridine;

2-[(3R)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

2-[(3S)-4-[4-(5-fluoro-2-methoxyphenyl)-1H-pyrrolo[2,3-b]pyridin-2-yl]-3-methyl-3,6-dihydropyridin-1(2H)-yl]-N,N-dimethylacetamide;

1-{4-[4-(5-fluoro-2-methoxyphenyl)-1H-pyrrolo[2,3-b]pyridin-2-yl]cyclohex-3-en-1-yl}-N-methyl-L-prolinamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-1-(3-hydroxyazetidin-1-yl)ethanone;

2-[(3aR,5S,6aS)-5-[4-(5-fluoro-2-methoxyphenyl)-1H-pyrrolo[2,3-b]pyridin-2-yl]hexahydrocyclopenta[c]pyrrol-2(1H)-yl]-1-[(2S)-2-(hydroxymethyl)pyrrolidin-1-yl]ethanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(2-hydroxyethyl)-N-methylacetamide;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-(3-hydroxycyclobutyl)-N-methylacetamide;

[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl](3-hydroxycyclobutyl)methanone;

2-[(3aR,5r,6aS)-5-[4-(5-fluoro-2-methoxyphenyl)-1H-pyrrolo[2,3-b]pyridin-2-yl]hexahydrocyclopenta[c]pyrrol-2(1H)-yl]-N-methyl-2-oxoethanesulfonamide;

2-(8-azabicyclo[3.2.1]oct-2-en-3-yl)-4-(5-fluoro-2-methoxyphenyl)-1H-pyrrolo[2,3-b]pyridine-5-carbonitrile;

2-(8-azabicyclo[3.2.1]oct-2-en-3-yl)-5-fluoro-4-(5-fluoro-2-methoxyphenyl)-1H-pyrrolo[2,3-b]pyridine;

N-cyano-3-[5-fluoro-4-(5-fluoro-2-methoxyphenyl)-1H-pyrrolo[2,3-b]pyridin-2-yl]-8-azabicyclo[3.2.1]oct-2-ene-8-carboxamide;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(2-hydroxyethyl)-N-methylacetamide;

{3-[5-cyano-4-(5-fluoro-2-methoxyphenyl)-1H-pyrrolo[2,3-b]pyridin-2-yl]-8-azabicyclo[3.2.1]oct-2-en-8-yl}acetic acid;

{3-[5-fluoro-4-(5-fluoro-2-methoxyphenyl)-1H-pyrrolo[2,3-b]pyridin-2-yl]-8-azabicyclo[3.2.1]oct-2-en-8-yl}acetic acid;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}acetamide;

{4-[4-(5-fluoro-2-methoxyphenyl)-1H-pyrrolo[2,3-b]pyridin-2-yl]cyclohexyl}acetic acid;

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-(3-hydroxycyclobutyl)-N-methylacetamide;

1-{4-[5-fluoro-4-(5-fluoro-2-methoxyphenyl)-1H-pyrrolo[2,3-b]pyridin-2-yl]cyclohex-3-en-1-yl}-N,N-dimethyl-L-prolinamide;

4-[3-cyano-4-(5-fluoro-2-methoxyphenyl)-1H-pyrrolo[2,3-b]pyridin-2-yl]cyclohex-3-ene-1-carboxylic acid;

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

4-(5-fluoro-2-methoxyphenyl)-2-(8-{2-[(2S)-2-(hydroxymethyl)pyrrolidin-1-yl]-2-oxoethyl}-8-azabicyclo[3.2.1]oct-2-en-3-yl)-1H-pyrrolo[2,3-b]pyridine-5-carbonitrile;

4-(5-fluoro-2-methoxyphenyl)-2-{8-[2-(3-hydroxyazetidin-1-yl)-2-oxoethyl]-8-azabicyclo[3.2.1]oct-2-en-3-yl}-1H-pyrrolo[2,3-b]pyridine-5-carbonitrile;

{4-[5-cyano-4-(5-fluoro-2-methoxyphenyl)-1H-pyrrolo[2,3-b]pyridin-2-yl]cyclohex-3-en-1-yl}acetic acid;

2-(9-azabicyclo[3.3.1]non-2-en-3-yl)-4-(5-fluoro-2-methoxyphenyl)-1H-pyrrolo[2,3-b]pyridine;

4-(5-fluoro-2-methoxyphenyl)-2-[9-(methylsulfonyl)-9-azabicyclo[3.3.1]non-2-en-3-yl]-1H-pyrrolo[2,3-b]pyridine;

3-[4-(5-fluoro-2-methoxyphenyl)-1H-pyrrolo[2,3-b]pyridin-2-yl]-N-methyl-9-azabicyclo[3.3.1]non-2-ene-9-carboxamide;

2-{3-[4-(5-fluoro-2-methoxyphenyl)-1H-pyrrolo[2,3-b]pyridin-2-yl]-9-azabicyclo[3.3.1]non-2-en-9-yl}-N,N-dimethylacetamide;

3-{3-[4-(5-fluoro-2-methoxyphenyl)-1H-pyrrolo[2,3-b]pyridin-2-yl]-9-azabicyclo[3.3.1]non-2-en-9-yl}-3-oxopropanenitrile;

{3-[4-(5-fluoro-2-methoxyphenyl)-1H-pyrrolo[2,3-b]pyridin-2-yl]-9-azabicyclo[3.3.1]non-2-en-9-yl}(3-hydroxycyclobutyl)methanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide;

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N-(trans-4-hydroxycyclohexyl)acetamide;

4-[4-(4-fluoro-2-methoxyphenyl)-1H-pyrrolo[2,3-b]pyridin-2-yl]cyclohex-3-ene-1-carboxylic acid;

4-[4-(4,5-difluoro-2-methoxyphenyl)-1H-pyrrolo[2,3-b]pyridin-2-yl]cyclohex-3-ene-1-carboxylic acid;

4-[4-(2-methoxyphenyl)-1H-pyrrolo[2,3-b]pyridin-2-yl]cyclohex-3-ene-1-carboxylic acid;

4-[4-(5-fluoro-2-methoxyphenyl)-1H-pyrrolo[2,3-b]pyridin-2-yl]-1-methylcyclohex-3-ene-1-carboxylic acid;

2-{4-[4-(5-fluoro-2-methoxyphenyl)-1H-pyrrolo[2,3-b]pyridin-2-yl]-2,3,6,7-tetrahydro-1H-azepin--yl}-N,N-dimethylacetamide;

2-{4-[4-(5-fluoro-2-methoxyphenyl)-1H-pyrrolo[2,3-b]pyridin-2-yl]azepan-1-yl}-N,N-dimethylacetamide;

{4-[4-(5-fluoro-2-methoxyphenyl)-1H-pyrrolo[2,3-b]pyridin-2-yl]-2,3,6,7-tetrahydro-1H-azepin-1-yl}acetic acid;

2-{4-[4-(5-fluoro-2-methoxyphenyl)-1H-pyrrolo[2,3-b]pyridin-2-yl]-2,3,6,7-tetrahydro-1H-azepin-1-yl}-1-(3-hydroxyazetidin-1-yl)ethanone;

tert-butyl 3-{4-[4-(5-fluoro-2-methoxyphenyl)-1H-pyrrolo[2,3-b]pyridin-2-yl]-3,6-dihydropyridin-1(2H)-yl}azetidine-1-carboxylate;

tert-butyl 3-{4-[4-(5-fluoro-2-methoxyphenyl)-1H-pyrrolo[2,3-b]pyridin-2-yl]piperidin-1-yl}azetidine-1-carboxylate;

{4-[5-fluoro-4-(5-fluoro-2-methoxyphenyl)-1H-pyrrolo[2,3-b]pyridin-2-yl]cyclohex-3-en-1-yl}acetic acid;

2-[1-(azetidin-3-yl)-1,2,3,6-tetrahydropyridin-4-yl]-4-(5-fluoro-2-methoxyphenyl)-1H-pyrrolo[2,3-b]pyridine;

2-[1-(azetidin-3-yl)piperidin-4-yl]-4-(5-fluoro-2-methoxyphenyl)-1H-pyrrolo[2,3-b]pyridine;

[3-(benzyloxy)-1,2-oxazol-5-yl]{4-[4-(5-fluoro-2-methoxyphenyl)-1H-pyrrolo[2,3-b]pyridin-2-yl]-3,6-dihydropyridin-1(2H)-yl}methanone;

4-[5-cyano-4-(5-fluoro-2-methoxyphenyl)-1H-pyrrolo[2,3-b]pyridin-2-yl]cyclohex-3-ene-1-carboxylic acid;

tert-butyl 4-[4-(5-fluoro-2-methoxyphenyl)-3-nitro-1H-pyrrolo[2,3-b]pyridin-2-yl]piperazine-1-carboxylate;

4-(5-fluoro-2-methoxyphenyl)-3-nitro-2-(piperazin-1-yl)-1H-pyrrolo[2,3-b]pyridine;

4-[4-(5-fluoro-2-methoxyphenyl)-3-nitro-1H-pyrrolo[2,3-b]pyridin-2-yl]-N-methylpiperazine-1-carboxamide;

4-(5-fluoro-2-methoxyphenyl)-2-{1-[1-(methylsulfonyl)azetidin-3-yl]-1,2,3,6-tetrahydropyridin-4-yl}-1H-pyrrolo[2,3-b]pyridine;

4-(5-fluoro-2-methoxyphenyl)-2-{1-[1-(methylsulfonyl)azetidin-3-yl]piperidin-4-yl}-1H-pyrrolo[2,3-b]pyridine;

2-{4-[4-(5-fluoro-2-methoxyphenyl)-1H-pyrrolo[2,3-b]pyridin-2-yl]-2,3,6,7-tetrahydro-1H-azepin-1-yl}-N-(3-hydroxycyclobutyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-N-(2-hydroxyethyl)-N-methylacetamide;

2-{4-[4-(5-fluoro-2-methoxyphenyl)-1H-pyrrolo[2,3-b]pyridin-2-yl]-2,3,6,7-tetrahydro-1H-azepin-1-yl}-1-[(2S)-2-(hydroxymethyl)pyrrolidin-1-yl]ethanone;

4-(5-fluoro-2-methoxyphenyl)-5-methoxy-2-[2-(methylsulfonyl)-1,2,3,3a,4,6a-hexahydrocyclopenta[c]pyrrol-5-yl]-1H-pyrrolo[2,3-b]pyridine;

2-{5-[4-(5-fluoro-2-methoxyphenyl)-5-methoxy-1H-pyrrolo[2,3-b]pyridin-2-yl]-3,3a,4,6a-tetrahydrocyclopenta[c]pyrrol-2(1H)-yl}-N,N-dimethylacetamide;

4-[4-(4,5-difluoro-2-methoxyphenyl)-5-fluoro-1H-pyrrolo[2,3-b]pyridin-2-yl]cyclohex-3-ene-1-carboxylic acid;

4-[5-fluoro-4-(4-fluoro-2-methoxyphenyl)-1H-pyrrolo[2,3-b]pyridin-2-yl]cyclohex-3-ene-1-carboxylic acid;

(4-{4-[4-(5-fluoro-2-methoxyphenyl)-1H-pyrrolo[2,3-b]pyridin-2-yl]cyclohex-3-en-1-yl}piperazin-1-yl)acetic acid;

2-{4-[5-fluoro-4-(5-fluoro-2-methoxyphenyl)-1H-pyrrolo[2,3-b]pyridin-2-yl]-3,6-dihydropyridin-1(2H)-yl}-N-(3-hydroxycyclobutyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-N-(2-hydroxyethyl)-N-methylacetamide;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone;

2-{4-[5-fluoro-4-(5-fluoro-2-methoxyphenyl)-1H-pyrrolo[2,3-b]pyridin-2-yl]-3,6-dihydropyridin-1(2H)-yl}-N-(trans-4-hydroxycyclohexyl)acetamide;

{4-[4-(5-fluoro-2-methoxyphenyl)-1H-pyrrolo[2,3-b]pyridin-2-yl]-3,6-dihydropyridin-1(2H)-yl}(3-hydroxy-1,2-oxazol-5-yl)methanone;

3-{4-[4-(5-fluoro-2-methoxyphenyl)-1H-pyrrolo[2,3-b]pyridin-2-yl]-3,6-dihydropyridin-1(2H)-yl}-N-methylazetidine-1-carboxamide;

3-{4-[4-(5-fluoro-2-methoxyphenyl)-1H-pyrrolo[2,3-b]pyridin-2-yl]piperidin-1-yl}-N-methylazetidine-1-carboxamide;

3-{4-[4-(5-fluoro-2-methoxyphenyl)-1H-pyrrolo[2,3-b]pyridin-2-yl]-3,6-dihydropyridin-1(2H)-yl}cyclobutanecarbonitrile;

3-{4-[4-(5-fluoro-2-methoxyphenyl)-1H-pyrrolo[2,3-b]pyridin-2-yl]-3,6-dihydropyridin-1(2H)-yl}cyclopentanecarboxylic acid;

9-[4-(5-fluoro-2-methoxyphenyl)-1H-pyrrolo[2,3-b]pyridin-2-yl]-3-azaspiro[5.5]undec-8-ene;

9-[4-(5-fluoro-2-methoxyphenyl)-1H-pyrrolo[2,3-b]pyridin-2-yl]-N-methyl-3-azaspiro[5.5]undec-8-ene-3-carboxamide;

9-[4-(5-fluoro-2-methoxyphenyl)-1H-pyrrolo[2,3-b]pyridin-2-yl]-3-(methylsulfonyl)-3-azaspiro[5.5]undec-8-ene;

(3-{4-[4-(5-fluoro-2-methoxyphenyl)-1H-pyrrolo[2,3-b]pyridin-2-yl]-3,6-dihydropyridin-1(2H)-yl}cyclobutyl)methanol;

(trans-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

(cis-4-{4-[5-chloro-4-(5-fluoro-2-methoxyphenyl)-1H-pyrrolo[2,3-b]pyridin-2-yl]-3,6-dihydropyridin-1(2H)-yl}cyclohexyl)acetic acid;

N-(1,1-dioxidotetrahydrothiophen-3-yl)-2-{4-[4-(5-fluoro-2-methoxyphenyl)-1H-pyrrolo[2,3-b]pyridin-2-yl]-3,6-dihydropyridin-1(2H)-yl}acetamide;

N-(1,1-dioxidotetrahydrothiophen-3-yl)-2-{4-[4-(5-fluoro-2-methoxyphenyl)-1H-pyrrolo[2,3-b]pyridin-2-yl]piperidin-1-yl}acetamide;

2-{4-[4-(5-fluoro-2-methoxyphenyl)-1H-pyrrolo[2,3-b]pyridin-2-yl]-3,6-dihydropyridin-1(2H)-yl}-1-[3-(methylsulfonyl)azetidin-1-yl]ethanone;

2-{4-[4-(5-fluoro-2-methoxyphenyl)-1H-pyrrolo[2,3-b]pyridin-2-yl]piperidin-1-yl}-1-[3-(methylsulfonyl)azetidin-1-yl]ethanone;

2-{4-[4-(5-fluoro-2-methoxyphenyl)-1H-pyrrolo[2,3-b]pyridin-2-yl]-3,6-dihydropyridin-1(2H)-yl}-N-(1-methyl-1H-pyrazol-4-yl)acetamide;

4-(4-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-(4,5-difluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

2-{3-[4-(5-fluoro-2-methoxyphenyl)-1H-pyrrolo[2,3-b]pyridin-2-yl]-9-azabicyclo[3.3.1]non-2-en-9-yl}-N-(2-hydroxyethyl)-N-methylacetamide;

2-{3-[4-(5-fluoro-2-methoxyphenyl)-1H-pyrrolo[2,3-b]pyridin-2-yl]-9-azabicyclo[3.3.1]non-2-en-9-yl}-1-(3-hydroxyazetidin-1-yl)ethanone;

2-{3-[4-(5-fluoro-2-methoxyphenyl)-1H-pyrrolo[2,3-b]pyridin-2-yl]-9-azabicyclo[3.3.1]non-2-en-9-yl}-1-[(2S)-2-(hydroxymethyl)pyrrolidin-1-yl]ethanone;

2-{3-[4-(5-fluoro-2-methoxyphenyl)-1H-pyrrolo[2,3-b]pyridin-2-yl]-9-azabicyclo[3.3.1]non-2-en-9-yl}-N-(3-hydroxycyclobutyl)-N-methylacetamide;

{3-[4-(5-fluoro-2-methoxyphenyl)-1H-pyrrolo[2,3-b]pyridin-2-yl]-9-azabicyclo[3.3.1]non-2-en-9-yl}acetic acid;

4-(2-methoxyphenyl)-2-[2-(methylsulfonyl)-1,2,3,3a,4,6a-hexahydrocyclopenta[c]pyrrol-5-yl]-1H-pyrrolo[2,3-b]pyridine;

4-(5-fluoro-2-methoxyphenyl)-2-(piperazin-1-yl)-1H-pyrrolo[2,3-b]pyridine-3-carbonitrile;

tert-butyl (2-{4-[4-(5-fluoro-2-methoxyphenyl)-1H-pyrrolo[2,3-b]pyridin-2-yl]-3,6-dihydropyridin-1(2H)-yl}ethyl)carbamate;

2-{4-[5-fluoro-4-(5-fluoro-2-methoxyphenyl)-1H-pyrrolo[2,3-b]pyridin-2-yl]-3,6-dihydropyridin-1(2H)-yl}-1-[(3R)-3-hydroxypyrrolidin-1-yl]ethanone;

4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

2-{4-[4-(5-fluoro-2-methoxyphenyl)-1H-pyrrolo[2,3-b]pyridin-2-yl]azepan-1-yl}-1-(3-hydroxyazetidin-1-yl)ethanone;

3-({4-[4-(5-fluoro-2-methoxyphenyl)-1H-pyrrolo[2,3-b]pyridin-2-yl]cyclohex-3-en-1-yl}amino)bicyclo[1.1.1]pentane-1-carboxylic acid;

2-{4-[4-(5-fluoro-2-methoxyphenyl)-1H-pyrrolo[2,3-b]pyridin-2-yl]-3,6-dihydropyridin-1(2H)-yl}ethanamine;

N-(2-{4-[4-(5-fluoro-2-methoxyphenyl)-1H-pyrrolo[2,3-b]pyridin-2-yl]-3,6-dihydropyridin-1(2H)-yl}ethyl)methanesulfonamide;

N-(2-{4-[4-(5-fluoro-2-methoxyphenyl)-1H-pyrrolo[2,3-b]pyridin-2-yl]-3,6-dihydropyridin-1(2H)-yl}ethyl)acetamide;

2-{4-[4-(5-fluoro-2-methoxyphenyl)-1H-pyrrolo[2,3-b]pyridin-2-yl]-3,6-dihydropyridin-1(2H)-yl}-N,N-dimethylethanesulfonamide;

4-(5-fluoro-2-methoxyphenyl)-2-[4-(methylsulfonyl)piperazin-1-yl]-3-nitro-1H-pyrrolo[2,3-b]pyridine;

4-(5-fluoro-2-methoxyphenyl)-2-[4-(methylsulfonyl)piperazin-1-yl]-1H-pyrrolo[2,3-b]pyridine-3-carbonitrile;

2-{3-[4-(5-fluoro-2-methoxyphenyl)-1H-pyrrolo[2,3-b]pyridin-2-yl]-2,5-dihydro-1H-pyrrol-1-yl}-1-(3-hydroxyazetidin-1-yl)ethanone;

(4-{4-[4-(5-fluoro-2-methoxyphenyl)-1H-pyrrolo[2,3-b]pyridin-2-yl]cyclohex-3-en-1-yl}piperidin-1-yl)acetic acid;

4-(5-fluoro-2-methoxyphenyl)-2-[(2S)-2-methyl-1-(methylsulfonyl)-1,2,3,6-tetrahydropyridin-4-yl]-1H-pyrrolo[2,3-b]pyridine-4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine;

2-{3-[4-(5-fluoro-2-methoxyphenyl)-1H-pyrrolo[2,3-b]pyridin-2-yl]-2,5-dihydro-1H-pyrrol-1-yl}-N-(2-hydroxyethyl)-N-methylacetamide;

2-{3-[4-(5-fluoro-2-methoxyphenyl)-1H-pyrrolo[2,3-b]pyridin-2-yl]-2,5-dihydro-1H-pyrrol-1-yl}-N,N-dimethylacetamide;

2-{3-[4-(5-fluoro-2-methoxyphenyl)-1H-pyrrolo[2,3-b]pyridin-2-yl]-2,5-dihydro-1H-pyrrol-1-yl}-1-[(2S)-2-(hydroxymethyl)pyrrolidin-1-yl]ethanone;

2-(4-{4-[4-(5-fluoro-2-methoxyphenyl)-1H-pyrrolo[2,3-b]pyridin-2-yl]cyclohex-3-en-1-yl}piperidin-1-yl)-N,N-dimethylacetamide;

(4-{(1S)-4-[4-(5-fluoro-2-methoxyphenyl)-1H-pyrrolo[2,3-b]pyridin-2-yl]cyclohex-3-en-1-yl}piperidin-1-yl)acetic acid;

(4-{(1R)-4-[4-(5-fluoro-2-methoxyphenyl)-1H-pyrrolo[2,3-b]pyridin-2-yl]cyclohex-3-en-1-yl}piperidin-1-yl)acetic acid;

methyl (4-{4-[4-(5-fluoro-2-methoxyphenyl)-1H-pyrrolo[2,3-b]pyridin-2-yl]-3,6-dihydropyridin-1(2H)-yl}cyclohexylidene)acetate;

(4-{(1S)-4-[4-(5-fluoro-2-methoxyphenyl)-1H-pyrrolo[2,3-b]pyridin-2-yl]cyclohex-3-en-1-yl}piperazin-1-yl)acetic acid;

(4-{(1R)-4-[4-(5-fluoro-2-methoxyphenyl)-1H-pyrrolo[2,3-b]pyridin-2-yl]cyclohex-3-en-1-yl}piperazin-1-yl)acetic acid;

(4-{4-[4-(5-fluoro-2-methoxyphenyl)-1H-pyrrolo[2,3-b]pyridin-2-yl]-3,6-dihydropyridin-1(2H)-yl}cyclohexylidene)acetic acid;

cis-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

trans-4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid;

(cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

(trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid;

(1-{4-[4-(5-fluoro-2-methoxyphenyl)-1H-pyrrolo[2,3-b]pyridin-2-yl]cyclohex-3-en-1-yl}piperidin-4-yl)acetic acid;

methyl (4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetate;

cis-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

trans-4-{4-[5-fluoro-4-(5-fluoro-2-methoxyphenyl)-1H-pyrrolo[2,3-b]pyridin-2-yl]-3,6-dihydropyridin-1(2H)-yl}cyclohexanecarboxylic acid;

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexylidene)acetic acid;

(trans-4-{4-[5-fluoro-4-(5-fluoro-2-methoxyphenyl)-1H-pyrrolo[2,3-b]pyridin-2-yl]piperidin-1-yl}cyclohexyl)acetic acid;

2-(trans-4-{4-[4-(5-fluoro-2-methoxyphenyl)-1H-pyrrolo[2,3-b]pyridin-2-yl]-3,6-dihydropyridin-1(2H)-yl}cyclohexyl)-N-(propan-2-ylsulfonyl)acetamide;

trans-4-{4-[5-fluoro-4-(5-fluoro-2-methoxyphenyl)-1H-pyrrolo[2,3-b]pyridin-2-yl]-3,6-dihydropyridin-1(2H)-yl}-N-(propan-2-ylsulfonyl)cyclohexanecarboxamide;

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexyl)acetic acid;

(4-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}cyclohexylidene)acetic acid; and pharmaceutically acceptable salts thereof.

11. A pharmaceutical composition comprising a pharmaceutically acceptable excipient and a therapeutically effective amount of a compound of claim 1, or a pharmaceutically acceptable salt thereof.

\* \* \* \* \*